United States Patent
Kariyuki et al.

(10) Patent No.: US 12,415,835 B2
(45) Date of Patent: *Sep. 16, 2025

(54) PEPTIDE-COMPOUND CYCLIZATION METHOD

(71) Applicant: Chugai Seiyaku Kabushiki Kaisha, Tokyo (JP)

(72) Inventors: Shiori Kariyuki, Shizuoka (JP); Takeo Iida, Kanagawa (JP); Miki Kojima, Kanagawa (JP); Ryuichi Takeyama, Shizuoka (JP); Mikimasa Tanada, Shizuoka (JP); Tetsuo Kojima, Kanagawa (JP); Hitoshi Iikura, Shizuoka (JP); Atsushi Matsuo, Shizuoka (JP); Takuya Shiraishi, Shizuoka (JP); Takashi Emura, Shizuoka (JP); Kazuhiko Nakano, Shizuoka (JP); Koji Takano, Shizuoka (JP); Kousuke Asou, Shizuoka (JP); Takuya Torizawa, Shizuoka (JP); Ryusuke Takano, Shizuoka (JP); Nozomi Hisada, Shizuoka (JP); Naoaki Murao, Shizuoka (JP); Atsushi Ohta, Kanagawa (JP); Kaori Kimura, Kanagawa (JP); Yusuke Yamagishi, Kanagawa (JP); Tatsuya Kato, Tokyo (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/460,300

(22) Filed: Sep. 1, 2023

(65) Prior Publication Data

US 2024/0166689 A1 May 23, 2024

Related U.S. Application Data

(63) Continuation of application No. 17/011,815, filed on Sep. 3, 2020, now Pat. No. 11,891,457, which is a continuation of application No. 15/166,550, filed on May 27, 2016, now abandoned, which is a continuation of application No. 14/368,564, filed as application No. PCT/JP2012/084103 on Dec. 28, 2012, now Pat. No. 9,409,952.

(51) Int. Cl.
| | | |
|---|---|---|
| C07K 7/64 | (2006.01) | |
| A61K 38/00 | (2006.01) | |
| C07H 21/04 | (2006.01) | |
| C07K 1/113 | (2006.01) | |
| C07K 5/087 | (2006.01) | |
| C07K 5/103 | (2006.01) | |
| C07K 7/06 | (2006.01) | |
| C07K 7/08 | (2006.01) | |
| C07K 11/00 | (2006.01) | |
| C07K 11/02 | (2006.01) | |
| C07K 19/00 | (2006.01) | |
| C12P 21/02 | (2006.01) | |

(52) U.S. Cl.
CPC .............. *C07K 7/64* (2013.01); *C07H 21/04* (2013.01); *C07K 1/113* (2013.01); *C07K 5/0812* (2013.01); *C07K 5/1013* (2013.01); *C07K 7/06* (2013.01); *C07K 7/08* (2013.01); *C07K 11/00* (2013.01); *C07K 11/02* (2013.01); *C07K 19/00* (2013.01); *C12P 21/02* (2013.01); *A61K 38/00* (2013.01)

(58) Field of Classification Search
CPC ............ C07K 7/64; C12P 21/02; A61K 38/00
See application file for complete search history.

(56) References Cited

U.S. PATENT DOCUMENTS

| | | | |
|---|---|---|---|
| 4,859,736 A | 8/1989 | Rink | |
| 5,057,415 A | 10/1991 | Schuetz et al. | |
| 5,059,679 A | 10/1991 | Yajima et al. | |
| 6,057,289 A | 5/2000 | Mulye | |
| 6,207,684 B1 | 3/2001 | Aberg | |
| 6,977,083 B1 | 12/2005 | Huebler et al. | |
| 7,045,363 B2 * | 5/2006 | Takemura | C07K 14/003 435/402 |
| 7,288,372 B2 | 10/2007 | Olejnik et al. | |
| 7,439,222 B2 | 10/2008 | Guinn et al. | |
| 8,518,666 B2 | 8/2013 | Wang et al. | |
| 8,809,280 B2 | 8/2014 | Strom et al. | |
| 9,090,668 B2 | 7/2015 | Suga et al. | |
| 9,133,245 B2 | 9/2015 | Gao et al. | |

(Continued)

FOREIGN PATENT DOCUMENTS

| | | |
|---|---|---|
| EP | 1219636 A2 | 7/2002 |
| EP | 1277755 A1 | 1/2003 |

(Continued)

OTHER PUBLICATIONS

Akaji, K., "Combinatorialization of Intramolecular Cyclization Using Heck Reactions," Society of Synthetic Organic Chemistry, Japan, 60(5):505-514 (2002).

Byk, G., et al., "Fast and Versatile Microwave-Assisted Intramolecular Heck Reaction in Peptide Macrocyclization Using Microwave Energy," Biopolymers (Pept Sci), 84:274-282 (2006).

Chatterjee, et al., "N-Methylation of Peptides: A New Perspective in Medicinal Chemistry," Accounts of Chemical Research, 41(10):1331-1342 (2008).

Chen, et al., "Structurally Diverse Cyclisation Linkers Impose Different Backbone Conformations in Bicyclic Peptides," ChemBioChem, 13(7):1032-1038 (2012).

(Continued)

*Primary Examiner* — Amber D Steele
(74) *Attorney, Agent, or Firm* — Nixon & Vanderhye P.C.

(57) ABSTRACT

An object of the present invention is to provide methods of discovering drugs effective for tough targets, which have conventionally been discovered only with difficulty. The present invention relates to novel methods for cyclizing peptide compounds, and novel peptide compounds and libraries comprising the same, to achieve the above object.

21 Claims, 136 Drawing Sheets

Specification includes a Sequence Listing.

(56) References Cited

U.S. PATENT DOCUMENTS

| | | | |
|---|---|---|---|
| 9,409,952 B2* | 8/2016 | Kariyuki | C07K 11/00 |
| 9,701,993 B2 | 7/2017 | Suga et al. | |
| 10,711,268 B2 | 7/2020 | Murakami et al. | |
| 10,815,489 B2 | 10/2020 | Ohta et al. | |
| 11,492,369 B2 | 11/2022 | Nomura et al. | |
| 11,542,299 B2 | 1/2023 | Nomura et al. | |
| 11,732,002 B2 | 8/2023 | Iwasaki et al. | |
| 11,787,836 B2 | 10/2023 | Nomura et al. | |
| 11,891,457 B2* | 2/2024 | Kariyuki | C07K 11/00 |
| 12,071,396 B2 | 8/2024 | Wadamoto et al. | |
| 12,163,134 B2 | 12/2024 | Ohta et al. | |
| 2001/0051595 A1 | 12/2001 | Lyons et al. | |
| 2003/0219780 A1 | 11/2003 | Olejnik et al. | |
| 2005/0165217 A1 | 7/2005 | Guinn et al. | |
| 2008/0044854 A1 | 2/2008 | Wang et al. | |
| 2008/0221303 A1 | 9/2008 | Katzhendler et al. | |
| 2010/0137432 A1 | 6/2010 | Khopade et al. | |
| 2010/0137561 A1 | 6/2010 | Chen | |
| 2010/0168380 A1 | 7/2010 | Suga et al. | |
| 2010/0292435 A1 | 11/2010 | Chen et al. | |
| 2013/0035296 A1 | 2/2013 | Strom et al. | |
| 2013/0058999 A1 | 3/2013 | Foeger | |
| 2013/0217599 A1 | 8/2013 | Suga et al. | |
| 2014/0194369 A1 | 7/2014 | Gao et al. | |
| 2015/0080549 A1 | 3/2015 | Kariyuki et al. | |
| 2015/0218221 A1 | 8/2015 | Van Der Laan et al. | |
| 2016/0209421 A1 | 7/2016 | Suga | |
| 2016/0272964 A1 | 9/2016 | Murakami et al. | |
| 2016/0311858 A1 | 10/2016 | Kariyuki et al. | |
| 2018/0127761 A1 | 5/2018 | Ohta et al. | |
| 2019/0338050 A1 | 11/2019 | Nakano et al. | |
| 2019/0380958 A1 | 12/2019 | Tampo et al. | |
| 2020/0040372 A1 | 2/2020 | Tanaka et al. | |
| 2020/0049695 A1 | 2/2020 | Tavassoli et al. | |
| 2020/0131669 A1 | 4/2020 | Muraoka et al. | |
| 2020/0277327 A1 | 9/2020 | Nomura et al. | |
| 2020/0339623 A1 | 10/2020 | Nomura et al. | |
| 2021/0061860 A1 | 3/2021 | Kariyuki et al. | |
| 2021/0087572 A1 | 3/2021 | Ohta et al. | |
| 2022/0017456 A1 | 1/2022 | Ishizawa et al. | |
| 2022/0024972 A1 | 1/2022 | Iwasaki et al. | |
| 2022/0096379 A1 | 3/2022 | Tampo et al. | |
| 2022/0144762 A1 | 5/2022 | Wadamoto | |
| 2022/0205009 A1 | 6/2022 | Shinohara et al. | |
| 2022/0411462 A1 | 12/2022 | Hou et al. | |
| 2023/0026641 A1 | 1/2023 | Nomura et al. | |
| 2023/0056969 A1 | 2/2023 | Kondo et al. | |
| 2023/0069218 A1 | 3/2023 | Yoshii et al. | |
| 2023/0096766 A1 | 3/2023 | Muraoka et al. | |
| 2023/0108274 A1 | 4/2023 | Kagotani et al. | |
| 2023/0138226 A1 | 5/2023 | Nomura et al. | |
| 2023/0151060 A1 | 5/2023 | Tanada et al. | |
| 2023/0295221 A1 | 9/2023 | Iwasaki et al. | |
| 2023/0303619 A1 | 9/2023 | Iwasaki et al. | |
| 2023/0391818 A1 | 12/2023 | Nomura et al. | |
| 2023/0406879 A1 | 12/2023 | Nomura et al. | |
| 2024/0024245 A1 | 1/2024 | Goto et al. | |
| 2024/0052340 A1 | 2/2024 | Nishimura et al. | |
| 2024/0067674 A1 | 2/2024 | Sekita et al. | |
| 2024/0124517 A1 | 4/2024 | Morita et al. | |
| 2024/0148821 A1 | 5/2024 | Tanada et al. | |
| 2024/0158446 A1 | 5/2024 | Kawada et al. | |
| 2024/0239842 A1 | 7/2024 | Hayashi et al. | |
| 2024/0366711 A1 | 11/2024 | Ueto et al. | |
| 2024/0376044 A1 | 11/2024 | Wadamoto | |
| 2024/0400617 A1 | 12/2024 | Tanada et al. | |
| 2024/0409524 A1 | 12/2024 | Saito et al. | |

FOREIGN PATENT DOCUMENTS

| | | |
|---|---|---|
| EP | 1424395 A1 | 6/2004 |
| EP | 1964916 A1 | 9/2008 |
| EP | 2088202 A1 | 8/2009 |
| EP | 2141175 A1 | 1/2010 |
| EP | 2177533 A1 | 4/2010 |
| EP | 2380596 A1 | 10/2011 |
| EP | 2492344 A1 | 8/2012 |
| EP | 2610348 A1 | 7/2013 |
| EP | 2615455 A1 | 7/2013 |
| EP | 2088202 B1 | 8/2013 |
| EP | 2647720 A1 | 10/2013 |
| EP | 2813512 A1 | 12/2014 |
| EP | 3031915 A1 | 6/2016 |
| EP | 3031915 B1 | 3/2019 |
| EP | 2813512 B1 | 3/2021 |
| JP | S57159747 A | 10/1982 |
| JP | S60169451 A | 9/1985 |
| JP | S62289 A | 1/1987 |
| JP | S62143698 A | 6/1987 |
| JP | S63260946 A | 10/1988 |
| JP | H01222795 A | 9/1989 |
| JP | H01250396 A | 10/1989 |
| JP | H0259146 B2 | 12/1990 |
| JP | H6502143 A | 3/1994 |
| JP | H0681759 B2 | 10/1994 |
| JP | 2513775 B2 | 7/1996 |
| JP | 2001048866 A | 2/2001 |
| JP | 2002209593 A | 7/2002 |
| JP | 2003508408 A | 3/2003 |
| JP | 2003520788 A | 7/2003 |
| JP | 2003523929 A | 8/2003 |
| JP | 2003531199 A | 10/2003 |
| JP | 2005095013 A | 4/2005 |
| JP | 2007319064 A | 12/2007 |
| JP | 2008125396 A | 6/2008 |
| JP | 2008521807 A | 6/2008 |
| JP | 2009096791 A | 5/2009 |
| JP | 2009528824 A | 8/2009 |
| JP | 2009529003 A | 8/2009 |
| JP | 4490663 B2 | 6/2010 |
| JP | 4502293 B2 | 7/2010 |
| JP | 2011139667 A | 7/2011 |
| JP | 2012506909 A | 3/2012 |
| JP | 2012510486 A | 5/2012 |
| JP | 2012525348 A | 10/2012 |
| JP | 5200241 B2 | 6/2013 |
| JP | 5592893 B2 | 9/2014 |
| JP | 2017043615 A | 3/2017 |
| JP | 2018509172 A | 4/2018 |
| WO | WO9206680 A1 | 4/1992 |
| WO | WO98031700 A1 | 7/1998 |
| WO | WO9854577 A1 | 12/1998 |
| WO | WO01052833 A1 | 7/2001 |
| WO | WO0181325 A2 | 11/2001 |
| WO | WO02085923 A2 | 10/2002 |
| WO | WO03014354 A1 | 2/2003 |
| WO | WO03068990 A1 | 8/2003 |
| WO | WO03089454 A2 | 10/2003 |
| WO | WO2005063791 A2 | 7/2005 |
| WO | WO2006057903 A2 | 6/2006 |
| WO | WO2007066627 A1 | 6/2007 |
| WO | WO2007099537 A1 | 9/2007 |
| WO | WO2007103307 A2 | 9/2007 |
| WO | WO2007120614 A2 | 10/2007 |
| WO | WO2008117833 A1 | 10/2008 |
| WO | WO2010053050 A1 | 5/2010 |
| WO | WO2010063604 A1 | 6/2010 |
| WO | WO2010125079 A2 | 11/2010 |
| WO | WO2011049157 A1 | 4/2011 |
| WO | WO2011051692 A1 | 5/2011 |
| WO | WO2011058122 A1 | 5/2011 |
| WO | WO2011117583 A2 | 9/2011 |
| WO | WO2012026566 A1 | 3/2012 |
| WO | WO2012033154 A1 | 3/2012 |
| WO | WO2012074130 A1 | 6/2012 |
| WO | WO2012122059 A1 | 9/2012 |
| WO | WO2013100132 A1 | 7/2013 |
| WO | WO2014033466 A1 | 3/2014 |
| WO | WO2014181888 A1 | 11/2014 |
| WO | WO2015019192 A2 | 2/2015 |
| WO | WO2015019999 A1 | 2/2015 |
| WO | WO2015155676 A1 | 10/2015 |
| WO | WO2015162590 A1 | 10/2015 |
| WO | WO2015179434 A1 | 11/2015 |

(56) References Cited

FOREIGN PATENT DOCUMENTS

| | | |
|---|---|---|
| WO | WO2015185162 A1 | 12/2015 |
| WO | WO2015193380 A2 | 12/2015 |
| WO | WO2016115168 A1 | 7/2016 |
| WO | WO2016148044 A1 | 9/2016 |
| WO | WO2016154675 A1 | 10/2016 |
| WO | WO2017136708 A1 | 8/2017 |
| WO | WO2017150732 A1 | 9/2017 |
| WO | WO2017181061 A1 | 10/2017 |
| WO | WO2018100561 A1 | 6/2018 |
| WO | WO2018124162 A1 | 7/2018 |
| WO | WO2018143145 A1 | 8/2018 |
| WO | WO2018225851 A1 | 12/2018 |
| WO | WO2018225864 A1 | 12/2018 |
| WO | WO2019117274 A1 | 6/2019 |
| WO | WO2020095983 A1 | 5/2020 |
| WO | WO2020111238 A1 | 6/2020 |
| WO | WO2020122182 A1 | 6/2020 |
| WO | WO2020138336 A1 | 7/2020 |
| WO | WO2020189540 A1 | 9/2020 |
| WO | WO2021090855 A1 | 5/2021 |
| WO | WO2021090856 A1 | 5/2021 |
| WO | WO2021117848 A1 | 6/2021 |
| WO | WO2021132545 A1 | 7/2021 |
| WO | WO2021132546 A1 | 7/2021 |
| WO | WO2021246471 A1 | 12/2021 |
| WO | WO2021261577 A1 | 12/2021 |
| WO | WO2022097540 A1 | 5/2022 |
| WO | WO2022138598 A1 | 6/2022 |
| WO | WO2022138891 A1 | 6/2022 |
| WO | WO2022145444 A1 | 7/2022 |
| WO | WO2022234850 A1 | 11/2022 |
| WO | WO2022234851 A1 | 11/2022 |
| WO | WO2022234852 A1 | 11/2022 |
| WO | WO2022234853 A1 | 11/2022 |
| WO | WO2023054636 A1 | 4/2023 |
| WO | WO2023063376 A1 | 4/2023 |
| WO | WO2023127869 A1 | 7/2023 |
| WO | WO2023190283 A1 | 10/2023 |
| WO | WO2023195516 A1 | 10/2023 |
| WO | WO2023214509 A1 | 11/2023 |
| WO | WO2023214576 A1 | 11/2023 |
| WO | WO2023214577 A1 | 11/2023 |
| WO | WO2024080333 A1 | 4/2024 |

OTHER PUBLICATIONS

Dawson, et al., "Synthesis of Proteins by Native Chemical Ligation," Science, 266(5186):776-779 (1994).

Frankel, et al., "Encodamers: Unnatural Peptide Oligomers Encoded in RNA," Chemistry & Biology, 10(11):1043-1050 (2003).

Ganesan, A., "The impact of natural products upon modern drug discovery," Current Opinion in Chemical Biology, 12(3):306-317 (2008).

Goto, et al., "Ribosomal synthesis of combinatorial polypeptides containing unusual amino acid blocks," Kagaku Kogyo, 58(4):255-262 (2007)(relevance found in International Search Report of PCT/JP2012/084103).

Goto, et al., "Translation Initiation with Initiator tRNA Charged with Exotic Peptides," J Am Chem Soc., 131(14):5040-5041 (2009).

Goto, et al., "Flexizymes for genetic code reprogramming," Nature Protocols, 6(6):779-790 (2011).

Gracia, et al., "Synthesis of chemically modified bioactive peptides: recent advances, challenges and developments for medicinal chemistry," Future Med Chem., 1(7):1289-1310 (2009).

Hayashi, et al., "Ribosomal synthesis of nonstandard cyclic peptides and its application to drug discovery," Journal of Japanese Biochemical Society, 82(6):505-514 (2010)(relevance found in International Search Report of PCT/JP2012/084103).

Heinis, et al., "Phage-encoded combinatorial chemical libraries based on bicyclic peptides," Nature Chemical Biology, 5(7):502-507 (2009).

Higuchi, et al., "Programmed Synthesis of Natural Product-like Non-standard Peptides Using the Translation System and Its Application," Journal of Synthetic Organic Chemistry, Japan, 68(3):217-227 (2010), with English abstract on first page (relevance found in International Search Report of PCT/JP2012/084103).

Katoh, et al., "Ribosomal synthesis of backbone macrocyclic peptides," Chem Commun., 47(36):9946-9958 (2011).

Kato, et al., "2. Enzymes Involved in Drug Metabolism and Reaction Mechanisms Thereof," Yakubutsutaishagaku, $2^{nd}$ Edition, 9-13 (2000), with English translation.

Kawakami, et al., "Messenger RNA-Programmed Incorporation of Multiple N-Methyl-Amino Acids into Linear and Cyclic Peptides," Chemistry & Biology, 15(1):32-42 (2008).

Kawakami, et al., "Diverse backbone-cyclized peptides via codon reprogramming," Nature Chemical Biology, 5(12):888-890 (2009).

Kawakami, et al., "Sequential peptide ligation by using a controlled cysteinyl prolyl ester (CPE) autoactivating unit," Tetrahedron Letters, 48:1903-1905 (2007).

Kleineweischede, et al., "Chemoselective Peptide Cyclization by Traceless Staudinger Ligation," Angew Chem Int Ed., 47(32):5984-5988 (2008).

Laufer, et al., "The Impact of Amino Acid Side Chain Mutations in Conformational Design of Peptides and Proteins," Chem Eur J., 16(18):5385-5390 (2010).

Li, et al., "Salicylaldehyde Ester-Induced Chemoselective Peptide Ligations: Enabling Generation of Natural Peptidic Linkages at the Serine/Threonine Sites," Organic Letters, 12(8):1724-1727 (2010).

Li, et al., "In Vitro Selection of mRNA Display Libraries Containing an Unnatural Amino Acid," J Am Chem Soc., 124(34):9972-9973 (2002).

Mas-Moruno, et al., "Cilengitide: The First Anti-Angiogenic Small Molecule Drug Canditate, Design, Synthesis and Clinical Evaluation," Anti-Cancer Agents in Medicinal Chemistry, 10(10):753-768 (2010).

Merryman, et al., "Transformation of Aminoacyl tRNAs for the In Vitro Selection of "Drug-like" Molecules," Chemistry & Biology, 11(4):575-582 (2004).

Millward, et al., "Design of Cyclic Peptides That Bind Protein Surfaces with Antibody-Like Affinity," ACS Chemical Biology, 2(9):625-634 (2007).

Ohta, et al., "Synthesis of Polyester by Means of Genetic Code Reprogramming," Chemistry & Biology, 14(12):1315-1322 (2007).

Ovadia, et al., "Improvement of drug-like properties of peptides: the somatostatin paradigm," Expert Opin Drug Discov., 5(7):655-671 (2010).

Parthasarathy, et al., "Sortase A as a Novel Molecular 'Stapler' for Sequence-Specific Protein Conjugation," Bioconjugate Chem., 18(2):469-476 (2007).

Reddy, et al., "Synthesis of small cyclic peptides via intramolecular Heck reactions," Tetrahedron Letters, 44:353-356 (2003).

Rezai, et al., "Testing the Conformational Hypothesis of Passive Membrane Permeability Using Synthetic Cyclic Peptide Diastereomers," J Am Chem Soc., 128(8):2510-2511 (2006).

Satyanarayanajois, et al., "Medicinal chemistry for 2020," Future Med Chem., 3(14):1765-1786 (2011).

Shukla, et al., "Phage-Displayed Combinatorial Peptide Libraries in Fusion to Beta-Lactamase as Reporter for an Accelerated Clone Screening: Potential Uses of Selected Enzyme-Linked Affinity Reagents in Downstream Applications," Combinatorial Chemistry & High Throughput Screening, 13(1);75-87 (2010).

Subtelny, et al., "Ribosomal Synthesis of N-Methyl Peptides," J Am Chem Soc., 130(19):6131-6136 (2008).

Teraska, et al., "Construction of nonstandard peptide library by genetic code reprogramming and bioactive peptide discovery," Experimental Medicine, 29(7):1063-1070 (2011)(relevance found in International Search Report of PCT/JP2012/084103).

Tsukiji, et al., "Sortase-Mediated Ligation: A Gift from Gram-Positive Bacteria to Protein Engineering," ChemBioChem, 10(5):787-798 (2009).

Wells, et al., "Reaching for high-hanging fruit in drug discovery at protein-protein interfaces," Nature, 450(7172):1001-1009 (2007).

White, et al., "On-resin N-methylation of cyclic peptides for discovery of orally bioavailable scaffolds," Nature Chemical Biology, 7(11):810-817 (2011).

(56) References Cited

OTHER PUBLICATIONS

White, et al., "Contemporary strategies for peptide macrocyclization," Nature Chemistry, 3(7):509-524 (2011).
Yamagishi, et al., "Natural Product-Like Macrocyclic N-Methyl-Peptide Inhibitors against a Ubiquitin Ligase Uncovered from a Ribosome-Expressed De Novo Library," Chemistry & Biology, 18(12):1562-1570 (2011).
Zhang, et al., "Specificity of Translation for N-Alkyl Amino Acids," J Am Chem Soc., 129(37):11316-11317 (2007).
U.S. Appl. No. 15/557,432, filed Mar. 11, 2016, Ohta, et al., related application.
Beck, et al., "Intestinal Permeability of Cyclic Peptides: Common Key Backbone Motifs Identified," Journal of the American Chemical Society, 134(29):12125-12133 (2012).
Chen, et al., "Effect of Alanine-293 Replacement of the Activity, ATP Binding, and Editing of *Escherichia coli* Leucyl-tRNA Synthetase," Biochemistry, 40(5):1144-1149 (2001).
Cusack, et al., "The 2 A crystal structure of leucyl-tRNA synthetase and its complex with a leucyl-adenylate analogue," The EMBO Journal, 19(10):2351-2361 (2000).
Doublié, et al., "Tryptophanyl-tRNA synthetase crystal structure reveals an unexpected homology to tyrosyl-tRNA synthetase," Structure, 3(1):17-31 (1995).
Fukunaga, et al., "Structural Basis for Non-cognate Amino Acid Discrimination by the Valyl-tRNA Synthetase Editing Domain," The Journal of Biological Chemistry, 280(33):29937-29945 (2005)(epub Jun. 21, 2005).
Hartman, et al., "An Expanded Set of Amino Acid Analogs for the Ribosomal Translation of Unnatural Peptides," PLoS One, 10:e972 (2007), 17 pages.
Hartman, et al., "Enzymatic aminoacylation of tRNA with unnatural amino acids," PNAS, 103(12):4356-4361 (2006)(epub Mar. 13, 2006).
Hecht, et al., "Chemical Aminoacylation of tRNAs," The Journal of Biological Chemistry, 253(13):4517-4520 (1978).
Hoogenboom, H. R., "Selecting and screening recombinant antibody libraries," Nature Biotechnology, 23(9):1105-1116 (2005).
Hountondji, et al., "Crucial Role of Conserved Lysine 277 in the Fidelity of tRNA Aminoacylation by *Eschericia coli* Valyl-tRNA Synthetase," Biochemistry, 41(50):14856-14865 (2002).
Itoh, et al., "Crystallographic and mutational studies of seryl-tRNA synthetase from the archaeon *Pyrococcus horikoshii*," RNA Biology, 5(3):169-177 (2008)(epub Jul. 28, 2008).
Kawakami, et al., "In Vitro Selection of Multiple Libraries Created by Genetic Code Reprogramming to Discover Macrocyclic Peptides that Antagonize VEGFR2 Activity in Living Cells," ACS Chem Biol., 8(6):1205-1214 (2013)(epub Apr. 2, 2013).
Kobayashi, et al., "Recognition of Non-α-amino Substrates by Pyrrolysyl-tRNA Synthetase," J Mol Biol., 385(5):1342-1360 (2008)(epub Dec. 11, 2008).
Lee, et al., "Molecular Modeling Study of the Editing Active Site of *Escherichia coli* Leucyl-tRNA Synthetase: Two Amino Acid Binding Sites in the Editing Domain," Proteins, 54(4):693-704 (2004).
Mermershtain, et al., "Idiosyncrasy and identity in the prokaryotic phe-system: Crystal structure of *E. coli* phenylalanyl-tRNA synthetase complexed with phenylalanine and AMP," Protein Science, 20(1):160-167 (2011).
Millward, et al., "A General Route for Post-Translational Cyclization of mRNA Display Libraries," J Am Chem Soc., 127(41):14142-14143 (2005).
Peacock, et al., "Amino acid-dependent stability of the acyl linkage in aminoacyl-tRNA," RNA, 20(6):758-764 (2014)(epub Apr. 21, 2014).
Perona, et al., "Structural Diversity and Protein Engineering of the Aminoacyl-tRNA Synthetases," Biochemistry, 51(44):8705-8729 (2012)(epub Oct. 26, 2012).
Sankaranarayanan, et al., "The Structure of Threonyl-tRNA Synthetase-tRNA$^{Thr}$ Complex Enlightens Its Repressor Activity and Reveals an Essential Zinc Ion in the Active Site," 97(3):371-381 (1999).

Sever, et al., "*Escherichia coli* Tryptophanyl-tRNA Synthetase Mutants Selected for Tryptophan Auxotrophy Implicate the Dimer Interface in Optimizing Amino Acid Binding," Biochemistry, 35(1):32-40 (1996).
Subtelny, et al., "Optimal Codon Choice Can Improve the Efficiency and Fidelity of N-Methyl Amino Acid Incorporation into Peptides by In-Vitro Translation," Angew Chem Int Ed., 50:3164-3167 (2011)(epub Mar. 4, 2011).
Tan, et al., "Amino Acid Backbone Specificity of the *Escherichia coli* Translation Machinery," J Am Chem Soc., 126(40):12752-12753 (2004).
Wu, et al., "A Genetically Encoded Photocaged Amino Acid," J Am Chem Soc., 126(44):14306-14307 (2004).
Yanagisawa, et al., "Multistep Engineering of Pyrrolysyl-tRNA Synthetase to Genetically Encode N-(o-Azidobenzyloxycarbonyl)lysine for Site-Specific Protein Modification," Chemistry & Biology, 15(11):1187-1197 (2008).
Zhai, et al., "Two Conserved Threonines Collaborate in the *Escherichia coli* Leucyl-tRNA Synthetase Amino Acid Editing Mechanism," Biochemistry, 44(47):15437-15443 (2005).
Restriction Requirement dated Sep. 2, 2015 in parent application U.S. Appl. No. 14/368,564.
Terasaka, et al., "Recent Developments of Engineered Translational Machineries for the Incorporation of Non-Canonical Amino Acids into Polypeptides," Int J Mol Sci., 16(3):6513-6531 (2015).
Gilon, C., et al., "Backbone Cyclization: A New Method for Conferring Conformational Constraint on Peptides," Biopolymers, 31:745-750 (1991).
Hruby, V. J., et al., "Emerging approaches in the molecular design of receptor-selective peptide ligands: conformational, topographical and dynamic considerations," Biochem J., 268:249-262 (1990).
Abdalla, M.A., et al., "Natural Cyclic Peptides as an Attractive Modality for Therapeutics: A Mini Review," Molecules, 23(8):2080 (2018).
Afonso, A., et al., "Solid-Phase Synthesis of Biaryl Cyclic Peptides Containing a 3-Aryltyrosine," European Journal of Organic Chemistry, 2012(31):6204-6211 (2012).
Alakhov, Y.B., et al., "Butylation of the Tryptophan Indole Ring: A Side Reaction During the Removal of t-butyloxycarbonyl and t-butyl Protecting Groups in Peptide Synthesis," Journal of the Chemical Society D: Chemical Communications, 7:406b-407 (1970).
Albericio, F., et al., "Fmoc Methodology: Cleavage from the Resin and Final Deprotection," Amino Acids, Peptides and Proteins in Organic Chemistry, 3:349-369 (2011).
Alex, A., et al., "Intramolecular Hydrogen Bonding to Improve Membrane Permeability and Absorption in Beyond Rule of Five Chemical Space," Medicinal Chemistry Communication, 2(7):669-674 (2011).
Alvaro, et al., "A Novel Activity of Immobilized Penicillin G Acylase: Removal of Benzyloxycarbonyl Amino Protecting Group," Biocatalysis and Biotransformation, 18(3):253-258 (2000).
Bastiaans, et al., "Flexible and Convergent Total Synthesis of Cyclotheonamide B," The Journal of Organic Chemistry, 62(12):3880-3889 (1997).
Behrendt, R., et al., "Advances in Fmoc Solid-Phase Peptide Synthesis," Journal of Peptide Science 22(1):4-27 (2016).
Bock, J.E., et al., "Getting in Shape: Controlling Peptide Bioactivity and Bioavailability Using Conformational Constraints," ACS Chemical Biology 8(3):488-499 (2013).
Bockus, A.T., et al., "Form and Function in Cyclic Peptide Natural Products: A Pharmacokinetic Perspective," Current Topics in Medicinal Chemistry, 13(7):821-836 (2013).
Bolek, S. and Ignatowska, J., "Ring opening reactions of cyclic sulfamidates. Synthesis of β-fluoroaryl alanines and derivatives of 4,4-difluoroglutamic acid," Journal of Fluorine Chemistry, 27:13-21 (2019).
Brunner, J., "Biosynthetic Incorporation of Non-natural Amino Acids into Proteins," Chemical Society Reviews, 22(3):183-189 (1993).
Burkholder, T. P., et al., "Acid-catalyzed O-allylation of β-Hydroxy-α-Amino Acids: An Entry into Conformationally Constrained Dipeptide Surrogates," Bioorganic & Medicinal Chemistry Letters, 2(6):579-582 (1992).

(56) References Cited

OTHER PUBLICATIONS

Carpino, L.A., et al., "Dramatically Enhanced N-→O Acyl Migration During the Trifluoroacetic Acid-based Deprotection Step in Solid Phase Peptide Synthesis," Tetrahedron Letters, 46(8):1361-1364 (2005).
Chang, Y.-P. and Chu, Y.-H., "Using surface plasmon resonance to directly determine binding affinities of combinatorially selected cyclopeptides and their linear analogs to a streptavidin chip," Analytical Chem., 340:74-79 (2005).
Chen, C.C., et al., "A Mild Removal of Fmoc Group Using Sodium Azide," Amino Acids, 46(2):367-374 (2014).
CLOGP Reference Manual, Daylight Chemical Information Systems, Inc., Release Date Aug. 1, 2011.
Coppins, R.L., "Cyclic Antibiotic Peptide Design: Structure and Membrane Interaction," Cyclic Antibiotic Peptide Design: Structure and Membrane Interaction, 1-8 (2001).
Cornella, J., et al., "Practical Ni-Catalyzed Aryl-Alkyl Cross-Coupling of Secondary Redox-Active Esters," Journal of the American Chemical Society, 138(7):2174-2177 (2016).
Cox, A.D., et al., "Drugging the undruggable RAS: Mission possible?," Nature Reviews. Drug Discovery, 13(11):828-851 (2014).
Creighton, C.J., et al., "Mechanistic Studies of an Unusual Amide Bond Scission," Journal of the American Chemical Society, 121(29):6786-6791 (1999).
Cudic, M. and Fields, G.B., "Solid-Phase Peptide Synthesis," Molecular Biomethods Handbook, 515-546 (2008).
Dailler, et al., "Divergent Synthesis of Aeruginosas Based on a C(sp(3))-H Activation Strategy," Chemistry, 21(26):9370-9379 (2015).
Doedens, L., et al., "Multiple N-methylation of MT-II backbone amide bonds leads to melanocortin receptor subtype hMC1R selectivity; pharmacological and conformational studies," J Am Chem Soc., 132(23):8115-8128 (2010).
Doi, Y., et al., "Elongation Factor Tu Mutants Expand Amino Acid Tolerance of Protein Biosynthesis System," Journal of the American Chemical Society 129(46):14458-14462 (2007).
Eberhard, H. and Seitz, O., "N—O-Acyl Shift in Fmoc-Based Synthesis of Phosphopeptides," Organic & Biomolecular Chemistry 6(8):1349-1355 (2008).
Falanga, A., et al., "Cyclic Peptides as Novel Therapeutic Microbicides: Engineering of Human Defensin Mimetics," Molecules, 22(7):1217 (2017).
Fang, W.-J., et al., "Deletion of Ac-NMePhe(1) from [NMePhe(1)]Jarodyn Under Acidic Conditions, Part 1: Effects of Cleavage Conditions and N-terminal Functionality," Biopolymers 96(1):97-102 (2011).
Final Office Action mailed on Mar. 22, 2021 for U.S. Appl. No. 15/166,550, Kariyuki, S., et al. filed May 27, 2016.
Final Office Action mailed Apr. 6, 2022 for U.S. Appl. No. 16/619,014, Muraoka, T., et al. filed Dec. 3, 2019.
Fujii, N., et al., "Trimethylsilyl Trifluoromethanesulphonate as a Useful Deprotecting Reagent in Both Solution and Solid Phase Peptide Syntheses," Journal of the Chemical Society, Chemical Communications, 4:274-275 (1987).
Fujino, M., et al., "Further Studies on the Use of Multi-substituted Benzenesulfonyl Groups for Protection of the Guanidino Function of Arginine," Chemical and Pharmaceutical Bulletin, 29(10):2825-2831 (1981).
Fujino, T., et al., "Reevaluation of the D-Amino Acid Compatibility With the Elongation Event in Translation," Journal of the American Chemical Society 135(5):1830-1837 (2013).
Fujino, T., et al., "Ribosomal Synthesis of Peptides with Multiple beta-Amino Acids," Journal of the American Chemical Society 138(6):1962-1969 (2016).
Fukai, S., et al., "Mechanism of Molecular Interactions for tRNA(Val) Recognition by Valyl-tRNA Synthetase," RNA 9(1):100-111 (2003).
Fukai, S., et al., "Structural Basis for Double-Sieve Discrimination of L-Valine From L-Isoleucine and L-Threonine by the Complex of tRNA(Val) and Valyl-tRNA Synthetase," Cell 103(5):793-803 (2000).
GenBank, "Valine—tRNA ligase [Thermus thermophilus]," Accession No. P96142, accessed on Jan. 27, 2021.
Gravestock, et al., "Novel branched isocyanides as useful building blocks in the Passerini-amine deprotection-acyl migration (PADAM) synthesis of potential HIV-1 protease inhibitors," Tetrahedron Letters, 53(26):3225-3229 (2012).
Grosjean, H. and Bjork, G.R., "Enzymatic Conversion of Cytidine to Lysidine in Anticodon of Bacterial Isoleucyl-tRNA—an Alternative Way of RNA Editing," Trends in Biochemical Sciences, 29(4):165-168 (2004).
Hountondji, C., et al., "Valyl-tRNA Synthetase From *Escherichia coli* MALDI-MS Identification of the Binding Sites for L-Valine or for Noncognate Amino Acids Upon Qualitative Comparative Labeling With Reactive Amino-Acid Analogs," European Journal of Biochemistry 267(15):4789-4798 (2000).
Huihui, K.M.M., et al., "Decarboxylative Cross-Electrophile Coupling of N-Hydroxyphthalimide Esters With Aryl Iodides," Journal of the American Chemical Society, 138(15):5016-5019 (2016).
Ikeuchi, Y., et al., "Agmatine-conjugated Cytidine in a tRNA Anticodon Is Essential for AUA Decoding in Archaea," Nature Chemical Biology, 6(4):277-282 (2010).
Ikeuchi, Y., et al., "Molecular Mechanism of Lysidine Synthesis That Determines tRNA Identity and Codon Recognition," Molecular Cell, 19(2):235-246 (2005).
Isidro-Llobet, A., et al., "Amino Acid-Protecting Groups," Chemical Reviews, 109(6):2455-2504 (2009).
Iwane, Y., et al., "Expanding the Amino Acid Repertoire of Ribosomal Polypeptide Synthesis via the Artificial Division of Codon Boxes," Nature Chemistry, 8(4):317-325 (2016).
Jaradat, D.M.M., "Thirteen Decades of Peptide Synthesis: Key Developments in Solid Phase Peptide Synthesis and Amide Bond Formation Utilized in Peptide Ligation," Amino Acids, 50(1):39-68 (2018).
Jones, A.B., et al., "A Formal Synthesis of FK-506. Exploration of Some Alternatives to Macrolactamization," The Journal of Organic Chemistry, 55(9):2786-2797 (1990).
Josephson, K., et al., "mRNA Display: From Basic Principles to Macrocycle Drug Discovery," Drug Discovery Today 19(4):388-399 (2014).
Josephson, K., et al., "Ribosomal Synthesis of Unnatural Peptides," Journal of the American Chemical Society 127(33):11727-11735 (2005).
Kato, et al., Yakubutsutaishagaku, 3rd edition, 43-46. (2010).
Kawakami, T., et al., "Incorporation of Electrically Charged N-alkyl Amino Acids Into Ribosomally Synthesized Peptides via Post-translational Conversion," Chemical Science, 5(3):887-893 (2014).
Kawakami, T., et al., "Ribosomal Synthesis of Polypeptoids and Peptoid-Peptide Hybrids," Journal of the American Chemical Society 130(50):16861-16863 (2008).
Kiho, T., et al., "Total Synthesis of Pleofugin A, a Potent Inositol Phosphorylceramide Synthase Inhibitor," Organic Letters, 20(15):4637-4640 (2018).
Kopina, B.J. and Lauhon, C.T., "Efficient Preparation of 2,4-diaminopyrimidine Nucleosides: Total Synthesis of Lysidine and Agmatidine," Organic Letters, 14(16):4118-4121 (2012).
Kuhn, B., et al., "Intramolecular Hydrogen Bonding in Medicinal Chemistry," Journal of Medicinal Chemistry, 53(6):2601-2611 (2010).
Lajoie, M.J., et al., "Overcoming Challenges in Engineering the Genetic Code," Journal of Molecular Biology, 428(5 Pt B):1004-1021 (2016).
Lassak, J., et al., "Stall No More at Polyproline Stretches With the Translation Elongation Factors EF-P and IF-5A," Molecular Microbiology 99(2):219-235 (2016).
Lejeune, V., et al., "Towards a Selective Boc Deprotection on Acid Cleavable Wang Resin," Tetrahedron Letters, 44(25):4757-4759 (2003).
Lenzi, A., et al., "Synthesis of N-Boc-α-Amino Acids with Nucleobase Residues as Building Blocks for the Preparation of Chiral PNA (Peptide Nucleic Acids)," Tetrahedron Letters, 36(10):1713-1716 (1995).
Li, H., et al., "Ni-Catalyzed Electrochemical Decarboxylative C—C Couplings in Batch and Continuous Flow," Organic letters, 20(5):1338-1341 (2018).

(56) References Cited

OTHER PUBLICATIONS

Liniger, M., et al., "Total Synthesis and Characterization of 7-Hypoquinuclidonium Tetrafluoroborate and 7-Hypoquinuclidone BF3 Complex," Journal of the American Chemical Society, 138(3):969-974 (2016).
Liu, D.R., et al., "Engineering a tRNA and aminoacyl-tRNA Synthetase for the Site-Specific Incorporation of Unnatural Amino Acids Into Proteins in Vivo," Proceedings of the National Academy of Sciences of the United States of America 94(19):10092-10097 (1997).
Liu, T., et al., "Synthesis and Screening of a Cyclic Peptide Library: Discovery of Small-Molecule Ligands Against Human Prolactin Receptor," Bioorganic and Medicinal Chemistry, 17(3):1026-1033 (2009).
Liu, Z., et al., "N-Boc Deprotection and Isolation Method for Water-soluble Zwitterionic Compounds," The Journal of Organic Chemistry, 79(23):11792-11796 (2014).
Lodder, M., et al., "The N-Pentenoyl Protecting Group for Aminoacyl-tRNAs," Methods 36(3):245-251 (2005).
Loos, P., et al., "Unified Azoline and Azole Syntheses by Optimized Aza-Wittig Chemistry," European Journal of Organic Chemistry 2013(16):3290-3315 (2013).
Low, K.E., et al., "Rational Design of Calpain Inhibitors Based on Calpastatin Peptidomimetics," Journal of Medicinal Chemistry 59(11):5403-5415 (2016).
Lundquist, J.T. and Pelletier, J.C., "Improved Solid-Phase Peptide Synthesis Method Utilizing Alpha-Azide-Protected Amino Acids," Organic Letters 3(5):781-783 (2001).
Luo, D., et al., "Total Synthesis of the Potent Marine-Derived Elastase Inhibitor Lyngbyastatin 7 and in Vitro Biological Evaluation in Model Systems for Pulmonary Diseases," The Journal of Organic Chemistry, 81(2):532-544 (2016).
Maini, R., et al., "Protein Synthesis With Ribosomes Selected for the Incorporation of beta-Amino Acids," Biochemistry 54(23):3694-3706 (2015).
Maini, R., et al., "Ribosome-Mediated Synthesis of Natural Product-Like Peptides via Cell-Free Translation," Current Opinion in Chemical Biology 34:44-52 (2016).
Malhotra, R., et al., "Efficient Asymmetric Synthesis of N-Protected-B-Aryloxyamino Acids via Regioselective Ring Opening of Serine Sulfamidate Carboxylic Acid," Organic & Biomolecular Chemistry, 12(33):6507-6515 (2014).
Manfredini, S., et al., "Design and Synthesis of Phosphonoacetic Acid (PPA) Ester and Amide Bioisosters of Ribofuranosylnucleoside Diphosphates as Potential Ribonucleotide Reductase Inhibitors and Evaluation of Their Enzyme Inhibitory, Cytostatic and Antiviral Activity," Antiviral Chemistry and Chemotherapy, 14(4):183-194 (2003).
Mangold, S.L., et al., "Z-Selective Olefin Metathesis on Peptides: Investigation of Side-Chain Influence, Preorganization, and Guidelines in Substrate Selection," Journal of the American Chemical Society, 136(35):12469-12478 (2014).
Marcucci, E., et al., "Solid-Phase Synthesis of NMe-IB-01212, a Highly N-Methylated Cyclic Peptide," Organic letters 14(2):612-615 (2012).
Meinnel, T., et al., "Methionine as Translation Start Signal: A Review of the Enzymes of the Pathway in *Escherichia coli*," Biochimie 75(12):1061-1075 (1993).
Meldal, M. and Christensen, S. F., "Microparticle Matrix Encoding of Beads," Angew Chem., 122:3551-3554 (2010).
Miyake, A., et al., "Design and Synthesis of N-[N-[(S)-1-ethoxycarbonyl-3-phenylpropyl]-I-alanyl]-N-(Indan-2-yl)glycine (CV-3317), a New, Potent Angiotensin Converting Enzyme Inhibitor," Chemical and Pharmaceutical Bulletin, 34(7):2852-2858 (1986).
Montalbetti, C.A.G.N. and Falque, V., "Amide Bond Formation and Peptide Coupling," Tetrahedron 61(46):10827-10852 (2005).
Morieux, P., et al., "The Structure-Activity Relationship of the 3-Oxy Site in the Anticonvulsant (R)-N-Benzyl 2-Acetamido-3-Methoxypropionamide," Journal of Medicinal Chemistry, 53(15):5716-5726 (2010).

Muramatsu, T., et al., "A Novel Lysine-Substituted Nucleoside in The First Position of the Anticodon of Minor Isoleucine tRNA from *Escherichia coli*," The Journal of Biological Chemistry, 263(19):9261-9267 (1988).
Murashige, R., et al., "Asymmetric and efficient synthesis of homophenylalanine derivatives via Friedel-Crafts reaction with trifluoromethanesulfonic acid," Tetrahedron Letters, 49(46):6566-6568 (2008).
Navo, C.D., et al., "Oxygen by Carbon Replacement at the Glycosidic Linkage Modulates the Sugar Conformation in Tn Antigen Mimics," ACS Omega, 3(12):18142-18152 (2018).
Niida, A., et al., "Investigation of the Structural Requirements of K-Ras(G12D) Selective Inhibitory Peptide KRpep-2d Using Alanine Scans and Cysteine Bridging," Bioorganic & Medicinal Chemistry Letters, 27(12):2757-2761 (2017).
Office Action mailed Jul. 16, 2021 for U.S. Appl. No. 16/619,014, Muraoka, T. et al. filed Dec. 3, 2019.
Office Action mailed Aug. 27, 2020 for U.S. Appl. No. 15/166,550, Kariyuki, S., et al. filed May 27, 2016.
Ohtsuki, T., et al., "Phototriggered Protein Syntheses by Using (7-diethylaminocoumarin-4-yl) Methoxycarbonyl-Caged Aminoacyl tRNAs," Nature communications 7:12501 (2016).
Ohwada, T., et al., "On the Planarity of Amide Nitrogen. Intrinsic Pyramidal Nitrogen of N-acyl-7-azabicyclo[2.2.1 ]heptanes," Tetrahedron Letters, 39(8):865-868 (1998).
Orain, D., et al., "Protecting Groups in Solid-Phase Organic Synthesis," Journal of Combinatorial Chemistry, 4(1):1-16 (2002).
Osawa, T., et al., "Structural Basis of tRNA Agmatinylation Essential for AUA Codon Decoding," Nature Structural & Molecular Biology, 18(11):1275-1280 (2011).
Ostrem, J.M.L., et al., "Direct Small-Molecule Inhibitors of KRAS: From Structural Insights to Mechanism-Based Design," Nature reviews. Drug Discovery, 15(11):771-785 (2016).
Ovadia O., et al., "The Effect of Multiple N-Methylation on Intestinal Permeability of Cyclic Hexapeptides," Molecular Pharmaceutics 8(2):479-487 (2011).
Peschke, B., et al., "New Highly Potent Dipeptidic Growth Hormone Secretagogues with Low Molecular Weight," European Journal of Medicinal Chemistry, 35(6):599-618 (2000).
Piszkiewicz, D., et al., "Anomalous Cleavage of Aspartyl-Proline Peptide Bonds During Amino Acid Sequence Determinations," Biochemical and Biophysical Research Communications, 40(5):1173-1178 (1970).
Rader, A.F.B., et al., "Orally Active Peptides: Is There a Magic Bullet?," Angewandte Chemie, 57(44):14414-14438 (2018).
Rafi, S.B., et al., "Predicting and Improving The Membrane Permeability of Peptidic Small Molecules," Journal of Medicinal Chemistry, 55(7):3163-3169 (2012).
Rand, A.C., et al., "Optimizing PK Properties of Cyclic Peptides: the Effect of Side Chain Substitutions on Permeability and Clearance()," MedChemComm 3(10):1282-1289 (2012).
Restriction Requirement mailed Apr. 15, 2021 for U.S. Appl. No. 16/081,522, Nakano, K., et al. filed Jul. 8, 2019.
Restriction Requirement mailed Feb. 4, 2021 for U.S. Appl. No. 16/619,014, Muraoka, T. et al. filed Dec. 3, 2019.
Rivier, J. E., et al., "Design of Potent Dicyclic (4-10/5-8) Gonadotropin Releasing Hormone (GnRH) Antagonists," J Med Chem., 43:784-796 (2000).
Rodriguez, H., et al., "A Convenient Microwave-Enhanced Solid-phase Synthesis of Short Chain N-Methyl-Rich Peptides," Journal of Peptide Science 16(3):136-140 (2010).
Roodbeen, R., et al., "Microwave Heating in the Solid-Phase Synthesis of N-Methylated Peptides: When Is Room Temperature Better?," European Journal of Organic Chemistry 2012(36):7106-7111 (2012).
Sakai, H., et al., "Second basic pKa: An overlooked parameter in predicting phospholipidosis-inducing potential of diamines," Bioorg Med Chem Lett., 30:126933 (2020).
Sakamoto, K., et al., "K-Ras(G12D)-Selective Inhibitory Peptides Generated by Random Peptide T7 Phage Display Technology," Biochemical and Biophysical Research Communications, 484(3):605-611 (2017).

(56) References Cited

OTHER PUBLICATIONS

Salowe, S.P., et al., "The Catalytic Flexibility of Trnaile-Lysidine Synthetase can Generate Alternative tRNA Substrates for Isoleucyl-tRNA Synthetase," The Journal of Biological Chemistry, 284(15):9656-9662 (2009).
Samatar, A.A., et al., "Targeting RAS-ERK Signalling in Cancer: Promises and Challenges," Nature reviews. Drug Discovery, 13(12):928-942 (2014).
Sang-Aroon, W., et al., "Theoretical Study on Isomerization and Peptide Bond Cleavage at Aspartic Residue," Journal of Molecular Modeling, 19(9):3627-3636 (2013).
Schlippe, Y.V.G., et al., "In Vitro Selection of Highly Modified Cyclic Peptides That Act as Tight Binding Inhibitors," Journal of the American Chemical Society 134(25):10469-10477 (2012).
See, E., et al., "Physiochemical characterization of asulacrine towards the development of an anticancer liposomal formulation via active drug loading: Stability, solubility lipophilicity and ionization," Int J Pharm., 473:528-535 (2014).
Shimizu, Y., et al., "Cell-Free Translation Reconstituted With Purified Components," Nature Biotechnology 19(8):751-755 (2001).
Sogabe, S., et al., "Crystal Structure of a Human K-Ras G12D Mutant in Complex with GDP and the Cyclic Inhibitory Peptide KRpep-2d," ACS Medicinal Chemistry Letters, 8(7):732-736 (2017).
Starosta, A.L., et al., "A Conserved Proline Triplet in Val-tRNA Synthetase and the Origin of Elongation Factor P," Cell Reports 9(2):476-483 (2014).
Stetsenko, D.A., et al., "Removal of Acid-Labile Protecting or Anchoring Groups in the Presence of Polyfluorinated Alcohol: Application to Solid-Phase Peptide Synthesis," Russian Journal of Bioorganic Chemistry, 42(2):143-152 (2016).
Struck, A., et al., "An Enzyme Cascade for Selective Modification of Tyrosine Residues in Structurally Diverse Peptides and Proteins," Journal of the American Chemical Society, 138(9):3038-3045 (2016).
Suenaga, K., et al., "Aurilide, A Cytotoxic Depsipeptide From the Sea Hare *Dolabella auricularia*: Isolation, Structure Determination, Synthesis, and Biological Activity," Tetrahedron, 60(38):8509-8527 (2004).
Suenaga, K., et al., "Synthesis and Cytotoxicity of Aurilide Analogs," Bioorganic & Medicinal Chemistry Letters, 18(14):3902-3905 (2008).
Suzuki, T., et al., "Discovery and Characterization of tRNAIle Lysidine Synthetase (TilS)," FEBS Letters, 584(2):272-277 (2010).
Suzuki, T., "How to Decipher AUA Codon in Archaea," Kagaku to Seibutsu, 50(1):36-43 (2012).
Takahashi T., et al., "Solid Phase Library Synthesis of Cyclic Depsipeptides: Aurilide and Aurilide Analogues," Journal of Combinatorial Chemistry 5(4):414-428 (2003).
Tam, J.P., et al., "Cyclohexyl Ester as a New Protecting Group for Aspartyl Peptides to Minimize Aspartimide Formation in Acidic and Basic Treatments," Tetrahedron Letters, 20(42):4033-4036 (1979).
Teixido, M., et al., "Solid-Phase Synthesis and Characterization of N-Methyl-Rich Peptides," The Journal of Peptide Research 65(2):153-166 (2005).
Toriyama, F., et al., "Redox-Active Esters in Fe-catalyzed C—C Coupling," Journal of the American Chemical Society, 138(35):11132-11135 (2016).
Tsuda, et al., "Part Two—Amino Acid Coupling Chemistry," Amino Acids, Peptides and Proteins in Organic Chemistry, 3:201-406, 495-517, 549-569 (2011).
Urban, J., et al., "Lability of N-alkylated Peptides Towards TFA Cleavage," International Journal of Peptide and Protein Research 47(3):182-189 (1996).
Vaisar, T. and Urban, J., "Gas-Phase Fragmentation of Protonated Mono-n-Methylated Peptides. Analogy With Solution-Phase Acid-Catalyzed Hydrolysis," Journal of Mass Spectrometry, 33(6):505-524 (1998).
Van Der Auwera, C.V.D., et al., "Easy Cleavage of C'-Terminal Iminoacids from Peptide Acids through Acidic Hydrolysis," International Journal of Peptide and Protein Research, 31(2):186-191 (1988).

Villar, E. A., et al., "How Proteins Bind Macrocycles," Nature Chemical Biology 10(9):723-731 (2014).
Wang, S., et al., "Iridium/f-Amphox-Catalyzed Asymmetric Hydrogenation of Styrylglyoxylamides" Synlett., 29(16):2203-2207 (2018).
Wang, J., et al., "Kinetics of Ribosome-Catalyzed Polymerization Using Artificial Aminoacyl-tRNA Substrates Clarifies Inefficiencies and Improvements," ACS Chemical Biology 10(10):2187-2192 (2015).
Wang, T., et al., "Revisiting Oxytocin through the Medium of Isonitriles," Journal of the American Chemical Society, 134(32):13244-13247 (2012).
Watanabe, E., et al., "A Practical Method for Continuous Production of Sp3-Rich Compounds From (Hetero) Aryl Halides and Redox-Active Esters," Chemistry, 26(1):186-191 (2020).
Weber, F., et al., "A Potato Mitochondrial Isoleucine tRNA is Coded for by a Mitochondrial Gene Possessing a Methionine Anticodon," Nucleic Acids Research, 18(17):5027-5030 (1990).
Wenschuh, H., et al., "Stepwise Automated Solid Phase Synthesis of Naturally Occurring Peptaibols Using FMOC Amino Acid Fluorides," The Journal of Organic Chemistry 60(2):405-410, ACS Publications, United States of America (Jan. 1995).
Wermuth, C. G., editor, "The Practice of Medicinal Chemistry," 2nd Edition, Academic Press, pp. 52-53 (2003), English translation of Wermuth, C. G., editor, "The Practice of Medicinal Chemistry," 2nd Edition, vol. 1, P87 (2003).
Wu, J., et al., "Intrinsic Basicity of Oligomeric Peptides that Contain Glycine, Alanine, and Valine-the Effects of the Alkyl Side Chain on Proton Transfer Reactions," Journal of the American Society for Mass Spectrometry, 6(2):91-101 (1995).
Yajima, et al., "New Strategy for the Chemical Synthesis of Proteins," Tetrahedron, 44(3):805-819 (1988).
Yamanoi, K., et al., "Synthesis of Trans and cis-α-(carboxycyclopropyl)Glycines Novel Neuroinhibitory Amino Acids as L-Glutamate Analogue," Tetrahedron Letters, 29(10):1181-1184 (1988).
Yang, C., et al., "R-ketamine: a Rapid-onset and Sustained Antidepressant Without Psychotomimetic Side Effects," Translational Psychiatry, 5:e632 (2015).
Yang, Y., Side Reactions in Peptide Synthesis, 246 (2016).
Yao, G., et al., "Efficient Synthesis and Stereochemical Revision of Coibamide A," Journal of American Chemical Society, 137(42):13488-13491 (2015).
Zhang, K., et al., "Ab Initio Studies of Neutral and Protonated Triglycines: Comparison of Calculated and Experimental Gas-Phase Basicity," Journal of the American Chemical Society, 116(25):11512-11521 (1994).
Zhang, A.J., et al., "A Method for Removal of N-BOC Protecting Groups from Substrates on TFA-Sensitive Resins," Tetrahedron Letters, 39(41):7439-7442 (1998).
U.S. Appl. No. 07/251,176, filed Sep. 30, 1988, Schuetz, et al.
U.S. Appl. No. 10/345,664, filed Jan. 16, 2003, Olejnik, et al.
U.S. Appl. No. 11/682,272, filed Mar. 5, 2007, Wang, et al.
U.S. Appl. No. 13/505,625, filed Oct. 22, 2012, Strom, et al.
U.S. Appl. No. 13/816,911, filed Feb. 13, 2013, Suga, et al.
U.S. Appl. No. 14/125,906, filed Mar. 10, 2014, Gao, et al.
U.S. Appl. No. 14/368,564, filed Jun. 25, 2014, Kariyuki, et al., related application.
U.S. Appl. No. 14/428,804, filed Mar. 17, 2015, Van Der Laan, et al.
U.S. Appl. No. 14/889,868, filed Mar. 7, 2016, Murakami, et al.
U.S. Appl. No. 15/166,550, filed May 27, 2016, Kariyuki, et al., related application.
U.S. Appl. No. 15/557,532, filed Sep. 12, 2017, Ohta, et al., related application.
U.S. Appl. No. 16/081,522, filed Jul. 8, 2019, Nakano, et al., related application.
U.S. Appl. No. 16/471,837, filed Jun. 20, 2019, Tampo et al., related application.
U.S. Appl. No. 16/479,736, filed Jul. 22, 2019, Tanaka, et al., related application.
U.S. Appl. No. 16/619,014, filed Dec. 3, 2019, Muraoka, et al., related application.

(56) References Cited

OTHER PUBLICATIONS

U.S. Appl. No. 16/619,388, filed Dec. 4, 2019, Nomura, et al., related application.
U.S. Appl. No. 16/771,335, filed Jun. 10, 2020, Nomura, et al., related application.
U.S. Appl. No. 17/011,815, filed Sep. 3, 2023, Kariyuki et al., related application.
U.S. Appl. No. 17/024,944, filed Sep. 18, 2020, Ohta, et al., related application.
U.S. Appl. No. 17/291,099, filed Jun. 3, 2021, Ishizawa, related application.
U.S. Appl. No. 17/297,231, filed May 26, 2021, Iwasaki, et al., related application.
U.S. Appl. No. 17/312,296, filed Jun. 9, 2021, Muraoka, et al., related application.
U.S. Appl. No. 17/417,822, filed Jun. 24, 2021, Shinohara, et al., related application.
U.S. Appl. No. 17/437,535, filed Mar. 13, 2020, Wadamoto, related application.
U.S. Appl. No. 17/502,525, filed Oct. 15, 2021, Tampo et al., related application.
U.S. Appl. No. 17/738,283, filed May 6, 2022, Hou et al., related application.
U.S. Appl. No. 17/773,733, filed May 2, 2022, Tanada et al., related application.
U.S. Appl. No. 17/773,734, filed May 2, 2022, Nomura et al., related application.
U.S. Appl. No. 17/783,076, filed Jun. 7, 2022, Yoshii et al., related application.
U.S. Appl. No. 17/787,809, filed Jun. 21, 2022, Kagotani et al., related application.
U.S. Appl. No. 17/788,506, filed Jun. 23, 2022, Kondo et al., related application.
U.S. Appl. No. 17/928,759, filed Nov. 30, 2022, Iwasaki et al., related application.
U.S. Appl. No. 17/976,942, filed Oct. 31, 2022, Nomura et al., related application.
U.S. Appl. No. 18/010,608, filed Dec. 15, 2022, Nishimura et al., related application.
U.S. Appl. No. 18/034,424, filed Apr. 28, 2023, Nomura et al., related application.
U.S. Appl. No. 18/203,371, filed May 30, 2023, Iwasaki et al., related application.
U.S. Appl. No. 18/268,399, filed Jun. 20, 2023, Goto et al., related application.
U.S. Appl. No. 18/268,737, filed Jun. 21, 2023, Morita et al., related application.
U.S. Appl. No. 18/269,334, filed Jun. 23, 2023, Sekita et al., related application.
U.S. Appl. No. 18/289,071, filed Oct. 31, 2023, Hayashi et al., related application.
U.S. Appl. No. 18/289,392, filed Nov. 3, 2023, Ueto et al., related application.
U.S. Appl. No. 18/289,451, filed Nov. 3, 2023, Tanada et al., related application.
U.S. Appl. No. 18/289,592, filed Nov. 6, 2023, Kawada et al., related application.
U.S. Appl. No. 18/459,998, filed Sep. 1, 2023, Nomura et al., related application.
U.S. Appl. No. 18/695,400, filed Mar. 26, 2024, Saito et al., related application.
U.S. Appl. No. 18/699,488, filed Apr. 8, 2024, Nakae et al., related application.
Biron, E., et al., "Improving Oral Bioavailability of Peptides by Multiple N-Methylation: Somatostatin Analogues," Angew Chem Int Ed., 47:2595-2599 (2008).
Brondsted, H., et al., "Drug delivery studies in Caco-2 monolayers. III. Intestinal transport of various vasopressin analogues in the presence of lysophosphatidylcholine," Int J Pharm., 114:151-157 (1995).
Cardote, T. A. F. and Ciulli, A., "Cyclic and Macrocyclic Peptides as Chemical Tools to Recongnise Protein Surfaces and Probe Protein-Protein Interactions," ChemMedChem, 11(8):787-794 (2016).
Drewe, J., et al., "Enteral absorption of octreotide: absorption enhancement by polyoxyethylene-24-cholesterol ether," Br J Pharmacol., 108:298-303 (1993).
Foster, A. D., et al., "Methods for the Creation of Cyclic Peptide Libraries for Use in Lead Discovery," Journal of Biomolecular Screening, 20(5):563-576 (2015).
Frost, J. R., et al., "Ribosomal Synthesis of Macrocyclic Peptides in Vitro and in Vivo Mediated by Genetically Encoded Aminothiol Unnatural Amino Acids," ACS Chem Biol., 10:1805-1816 (2015).
Guo, J., et al., "Transport of leuprolide across rat intestine, rabbit intestine and Caco-2 cell monolayer," Int J Pharm., 278:415-422 (2004).
Jones, J., et al., "Protein arginine deiminase 4 (PAD4): current understanding and future therapeutic potential," Curr Opin Drug Discov Devel., 12(5):616-627 (2009).
Ma, C., et al. "Discovery of cyclosporine A and its analogs as broad-spectrum anti-influenza drugs with a high in vitro genetic barrier of drug resistance," Antiviral Res., 133:62-72 (2016).
Nevola, L., et al., "Light-Regulated Stapled Peptides to Inhibit Protein-Protein Interactions Involved in Clathrin-Mediated Endocytosis," Angew Chem Int Ed., 52:7704-7708 (2013).
O'Hagan, S. and Kell, D. B., "The apparent permeabilities of Caco-2 cells to marketed drugs: magnitude, and independence from both biophysical properties and endogenite similarities," PeerJ, 3:e1405 (2015).
Rafferty, J., et al., "Peptide Therapeutics and the Pharmaceutical Industry: Barriers Encountered Translating from the Laboratory to Patients," Curr Med Chem., 23:4231-4259 (2016).
Tavassoli, A., "Siclopps cyclic peptide libraries in drug discovery," Curr Opin Chem Biol., 38:30-35 (2017).
Wu, X., et al., "Inhibition of Ras-effector interactions by cyclic peptides," Med Chem Commun., 4:378-382 (2013).
Goto, Y., et al., "Initiating translation with D-amino acids," RNA, 14(7):1390-1398 (2008).
Goto, Y., et al., "Reprogramming the Translation Initiation for the Synthesis of Physiologically Stable Cyclic Peptides," ACS Chem Biol., 3(2):120-129 (2008).
Leonaviciute, G., et al., "Self-emulsifying drug delivery systems in oral (poly)peptide drug delivery," Expert Opin Drug Deliv., 12(11):1703-1716 (2015).
U.S. Appl. No. 18/723,993, filed Jun. 25, 2024, Komiya et al., related application.
U.S. Appl. No. 18/773,066, filed Jul. 15, 2024, Tanada et al., related application.
U.S. Appl. No. 18/781,112, filed Jul. 23, 2024, Wadamoto, related application.
U.S. Appl. No. 18/829,566, filed Sep. 10, 2024, Kawada et al., related application.
U.S. Appl. No. 18/847,785, filed Sep. 17, 2024, Takanashi et al., related application.
U.S. Appl. No. 18/851,191 filed Sep. 26, 2024, Nakae et al., related application.
U.S. Appl. No. 18/854,568, filed Oct. 7, 2024, Shinohara et al., related application.
U.S. Appl. No. 18/860,859, filed Oct. 28, 2024, Kage et al., related application.
U.S. Appl. No. 18/926,665, filed Oct. 25, 2024, Ohta et al., related application.
U.S. Appl. No. 19/027,445, filed Jan. 17, 2025, Nomura et al., related application.

* cited by examiner

Synthesized compound

| | Rex1 = Me | iPr | Et | tBu | Bn | Phenethyl | Phe |
|---|---|---|---|---|---|---|---|
| I ; n = 1 | I A | I B | I G | I C | I D | I E | I F |
| II ; n = 2 | II A | — | — | — | II D | — | II F |

Fig. 8-2

| Entry | Amine | Thioester | pH | Temperature | Time | Conversion rate |
|---|---|---|---|---|---|---|
| 1 | (HS-CH₂-CH(NH)-COOEt) | 5b-1 | 7.9 | 50°C | 3h | 67% (isolation yield) |
| 2 | (MeS-CH₂-CH(NH)-COOEt) | 5b-2 | 7.5 | 50°C | 3h | 88% (isolation yield) |
| 3 | (H₂N-CH₂-COO-Bn) | 5b-1 | 9 | 50°C | 3d | 5b-1: 5d-1:5d-1b =22:1:8 LCMS UV area |
| 4 | (H-CH₂-CH₂-COO-Bn) | 5b-2 | 8.8 | 50°C | 3d | 5b-2:5d-2=22:10 LCMS UV area |
| 5 | (H-CH₂-CH₂-COO-Bn) | 5e-2 | 8.3 | 50°C | 6h | 91% (isolation yield) |
| 6 | (H-CH₂-CH₂-COO-Bn) | 5f-2 | 7 | 50°C | 45m | 90% (isolation yield) |

By LC-MS

| | | | TM | TM without Bn | SM | hydrolysate of SM thioester |
|---|---|---|---|---|---|---|
| pH6.4 | 37°C | 1d | 4% | 9% | 87% | 0% |
| | 70°C | +3h | 4% | 13% | 83% | 0% |
| | 100°C | +6h | 1% | 31% | 64% | 3% |
| pH7.4 | 37°C | 1d | 1% | 18% | 81% | 0% |
| | 70°C | +3h | 1% | 23% | 77% | 0% |
| | 100°C | +6h | <1% | 46% | 49% | 5% |

Fig. 11
2m-A: Rex3=tBu, Rex4=H, Pex1= 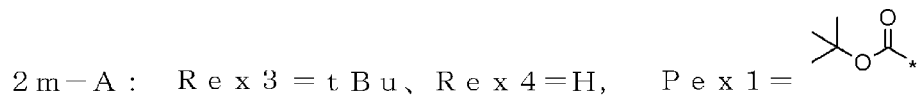
2n-A: Rex3=tBu, Rex4=H
2m-B: Rex3= tBu, Rex4=Me, Pex1= 
2n-B: Rex3= tBu, Rex4=Me
2m-C: Rex3=tBu, Rex4=H, Pex1= 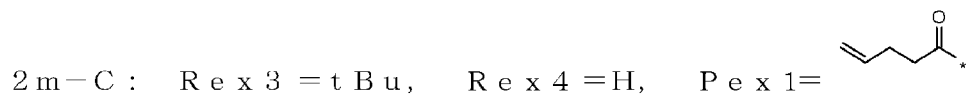
2m-D: Rex3=Me, Rex4=H, Pex1= 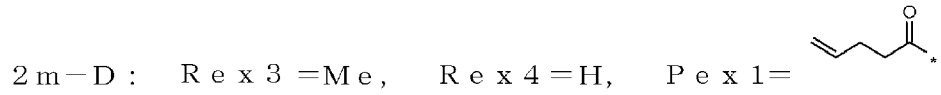
2m-E: Rex3= tBu, Rex4=H, Pex1= 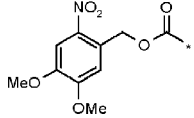
2m-F: Rex3=Et, Rex4=Me, Pex1= 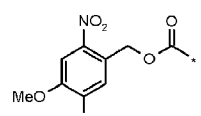
2m-G: Rex3=tBu, Rex4=Me, Pex1= 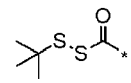

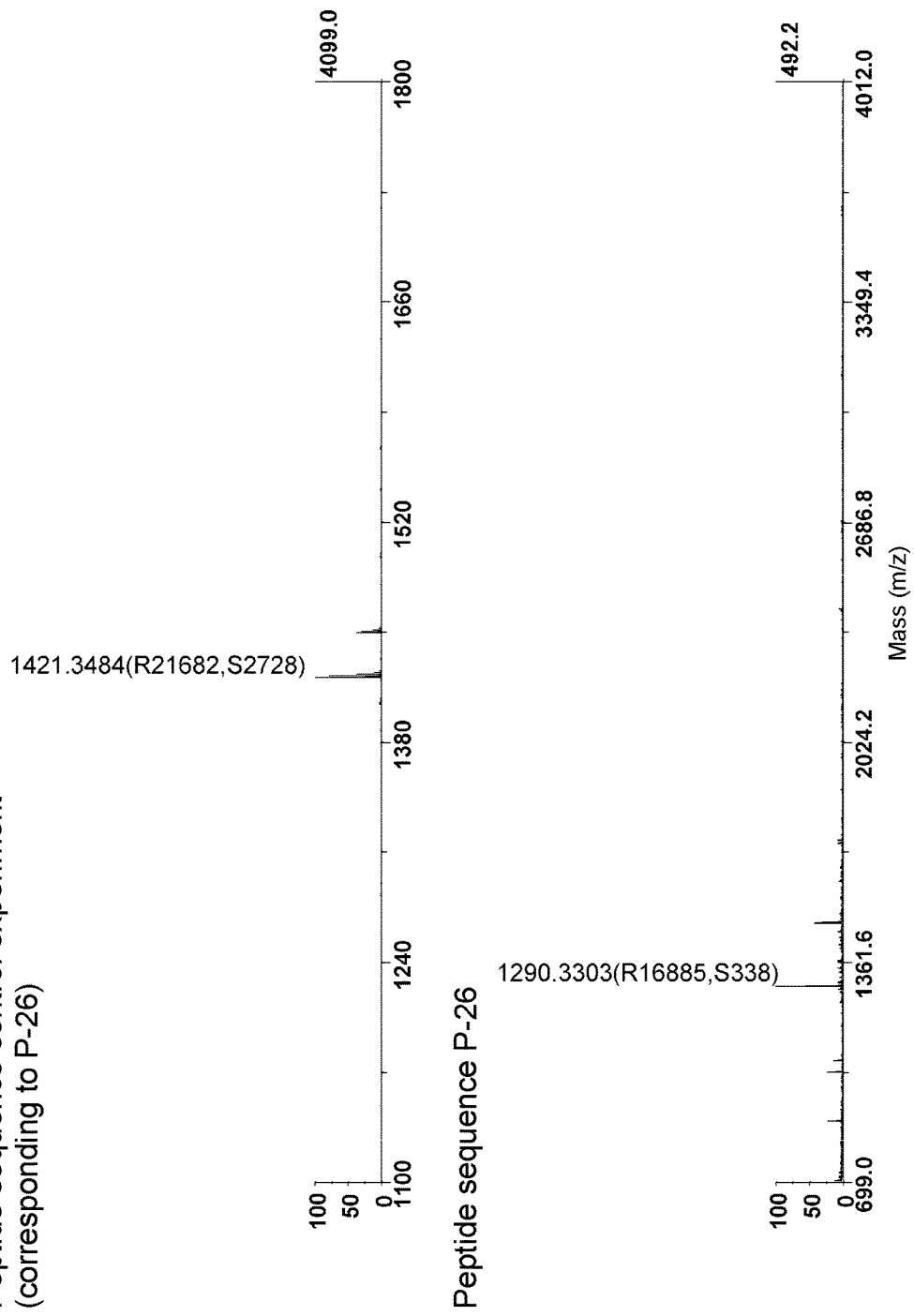

Peptide sequence control experiment (corresponding to P-27)

Peptide sequence P-27

Fig. 27
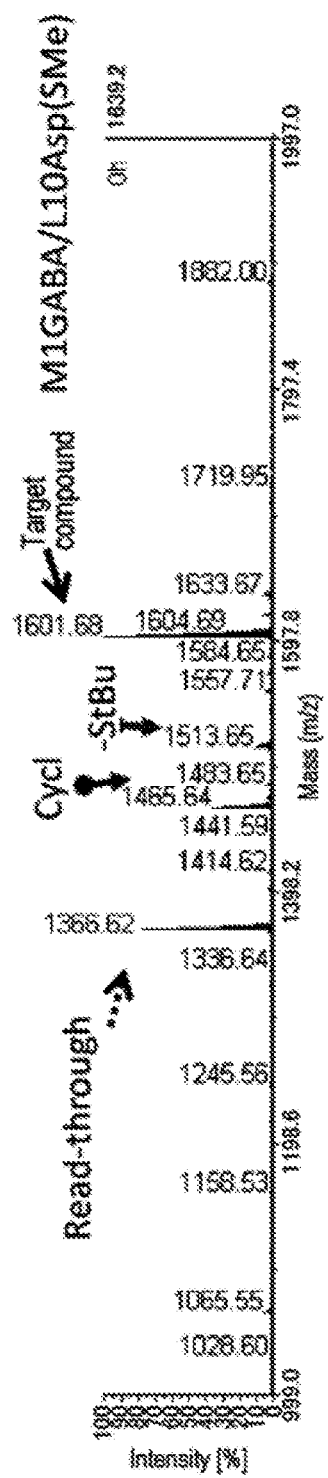
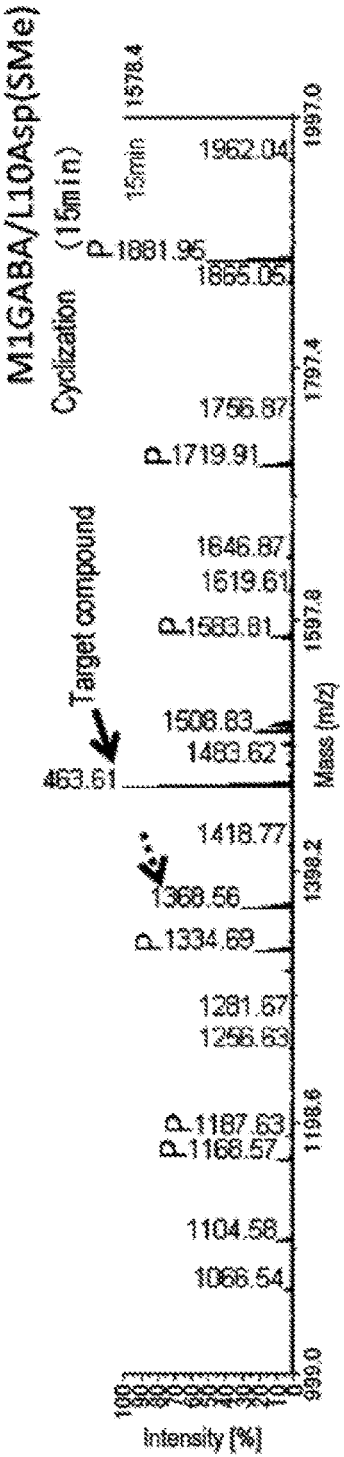

Fig. 32

| Entry | Method | SM mM | Solvent (2l) | RSH(mM) | TCEP(eq) | VA-044(eq) | Temperature | Time | Conversion rate (LC-MS UV area%) 3a:3b:3c:3d | Isolation yield |
|---|---|---|---|---|---|---|---|---|---|---|
| 1 | A | 30mM | DMF-H2O | tBuSH(90mM) | 4 | 1 | 50 | 1.5h | 0:1:0:0 | 97% |
| 2 | A | 30mM | DMF-H2O | Glutathione (90mM) | 4 | 1 | 50 | 3h | 0:1:0:0 | |
| 3 | A | 30mM | MeOH-H2O | Glutathione (90mM) | 4 | 1 | 50 | 1h | 0:1:0:0 | |
| 4 | A | 3mM | MeOH-H2O | 0 | 5 | 1 | 50 | 1h | 5:20:16:11 | |
| 5 | A | 3mM | MeOH-H2O | Glutathione (90mM) | 40 | 1 | 50 | 1h | 0:1:0:0 | |
| 6 | A | 3mM | MeOH-H2O | Glutathione (9mM) | 5 | 1 | 50 | 1h | 0:64:12:4 | |
| 7 | A | 30mM | MeOH-H2O | 0 | 5 | 1 | 50 | 1h | 0:24:33:19 | |
| 8 | B | 3mM | MeOH-H2O | 0 | 40 | 1 | 50 | 0.5h | 0:1:0:0 | |
| 9 | B | 3mM | MeOH-H2O | Glutathione (90mM) | 40 | 1 | 50 | 0.5h | 0:1:0:0 | |
| 10 | B | 3mM | MeOH-H2O | 0 | 40 | 1 | 40 | 0.5h | 0:1:0:0 | |
| 11 | B | 3mM | MeOH-H2O | Glutathione (90mM) | 40 | 1 | 40 | 0.5h | 0:1:0:0 | |
| 12 | B | 3mM | MeOH-H2O | 0 | 40 | 1 | 30 | 1.5h | 0:1:0:0 | |
| 13 | B | 3mM | MeOH-H2O | Glutathione (90mM) | 40 | 1 | 30 | 1.5h | 0:1:0:0 | |

Fig. 33
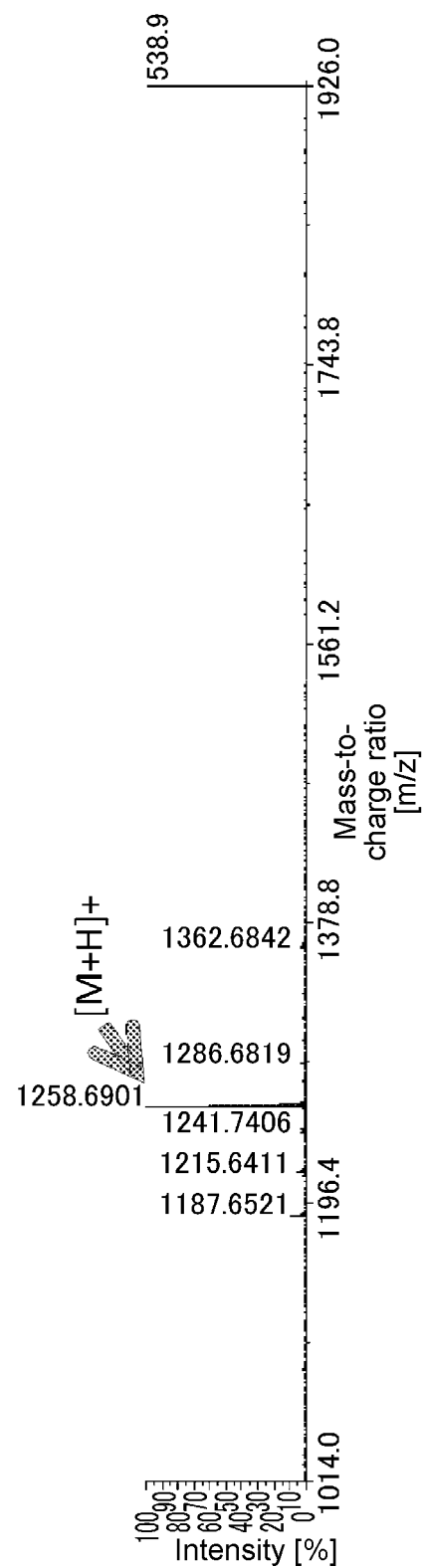

Fig. 34

| No. | Desulfurization reaction mix | DTT$^{OX}$(mM) | DMSO(%) | M-PBS(%) | hIL-6R (+) | hIL-6R (−) | S/N |
|---|---|---|---|---|---|---|---|
| 1 | − | 0 | 13.4 | 0.9 | 982411 | 2479 | 396 |
| 2 | − | 0 | 6.7 | 0.9 | 942626 | 1116 | 845 |
| 3 | − | 0 | 3.4 | 0.9 | 964610 | 727 | 1327 |
| 4 | − | 0 | 1.7 | 0.9 | 941804 | 596 | 1580 |
| 5 | − | 0 | 0.8 | 0.9 | 974132 | 1525 | 639 |
| 6 | − | 0 | 0.0 | 0.9 | 867860 | 2859 | 304 |
| 16 | − | 0 | 0.0 | 0.9 | 870240 | 602 | 1446 |
| 7 | + | 0 | 0.0 | 1.9 | 39421 | 802 | 49 |
| 8 | + | 0 | 0.0 | 3.7 | 72647 | 808 | 90 |
| 9 | + | 1000 | 13.4 | 0.9 | 799381 | 653 | 1224 |
| 10 | + | 500 | 6.7 | 0.9 | 814802 | 590 | 1381 |
| 11 | + | 250 | 3.4 | 0.9 | 847691 | 604 | 1403 |
| 12 | + | 125 | 1.7 | 0.9 | 684333 | 462 | 1481 |
| 13 | + | 63 | 0.8 | 0.9 | 503827 | 452 | 1115 |
| 14 | + | 0 | 0.0 | 0.9 | 42054 | 561 | 75 |
| 15 | + | 0 | 0.0 | 0.9 | 53989 | 619 | 87 |

※Concentration of DTT$^{OX}$ in desulfurization reaction mix

Retention time: 0.64 min (analysis condition SQDFA05)

| Time | Height | Area | Area ratio (%) |
|---|---|---|---|
| 0.51 | 1599625 | 26178.15 | 15.26 |
| 0.58 | 1282475 | 17927.23 | 10.45 |
| 0.64 | 9849150 | 127435.06 | 74.29 |

LCMS : m/z 1134.6 (M-H) -
Retention time: 0.63 min (analysis condition SQDFA05)

| Time | Height | Area | Area ratio (%) |
|---|---|---|---|
| 0.50 | 422808 | 6139.70 | 3.22 |
| 0.58 | 865058 | 14728.07 | 7.73 |
| 0.63 | 13056954 | 169755.59 | 89.05 |

LCMS : m/z 1417.0 (M−H) −
Retention time: 1.04 min (analysis condition SQDFA05)

| Time | Height | Area | Area ratio (%) |
|---|---|---|---|
| 0.68 | 542553 | 12872.79 | 27.53 |
| 1.04 | 788104 | 33889.73 | 72.47 |

| Entry | Thiol | Thiol concentration | SM: BocPhe-OH: Compound 10 (LC area%) |
|---|---|---|---|
| 1 | HS~SO₃Na | 0.1 M | 10 : 46 : 43 |
| 2 |  | 1.0 M | 16 : 24 : 60 |
| 3 | HS~N(Me)~·HCl | 0.8 M | 6 : 23 : 71 |
| 4 |  | 3 M | 1 : 15 : 84 |

LCMS (ESI) m/z = 1261 (M+H)+
Retention time: 0.87 min (analysis condition SQDFA05)

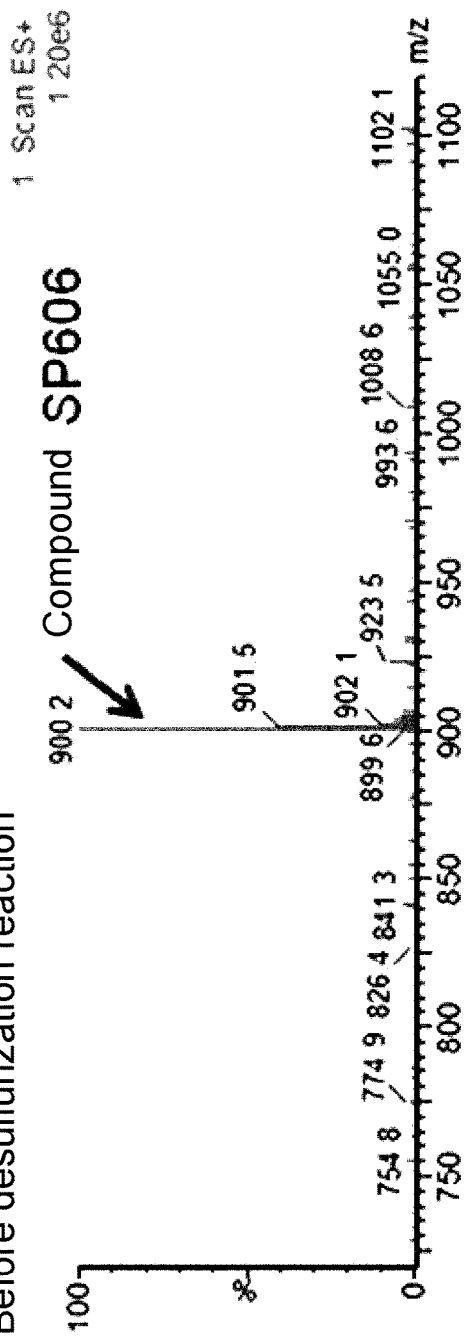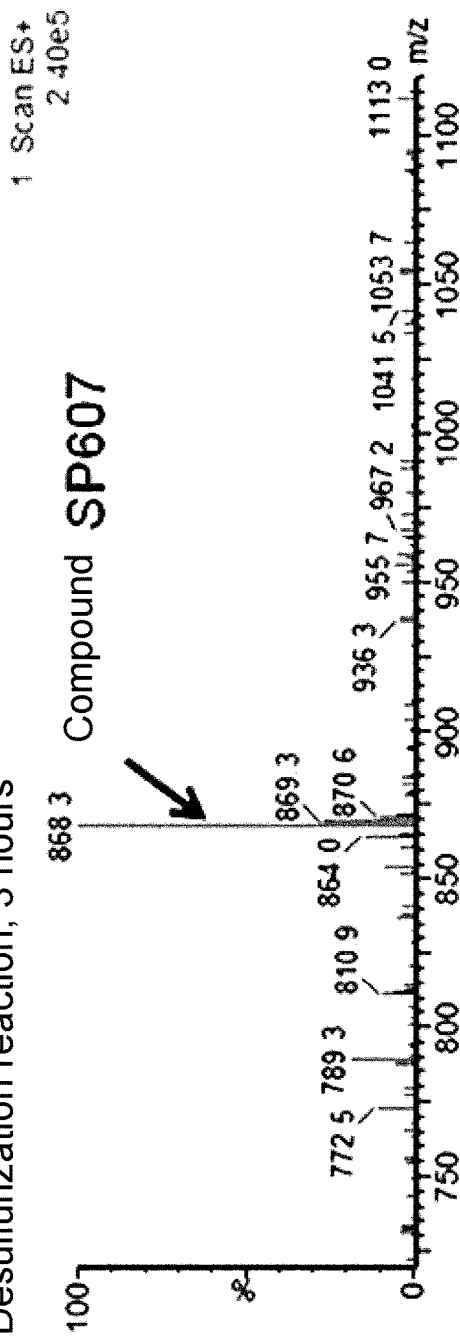
Fig. 56

Fig. 66
Initiation suppression library
Average CLogP 6.12
Average number of NMe amino acids 6.0
Average molecular weight 1719.2
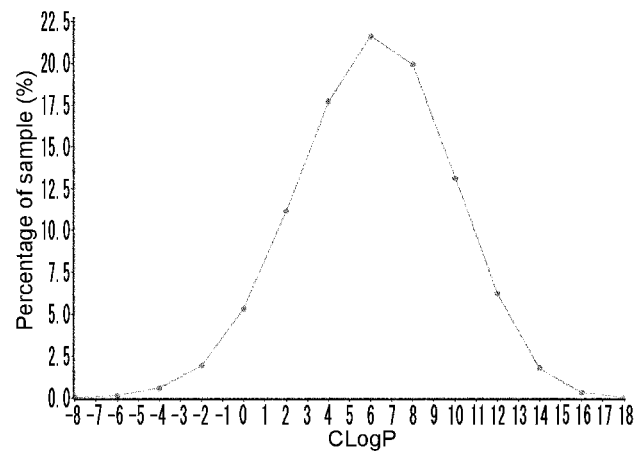
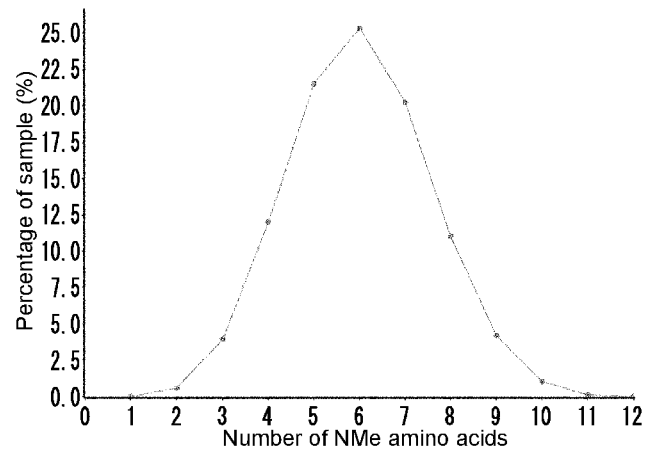
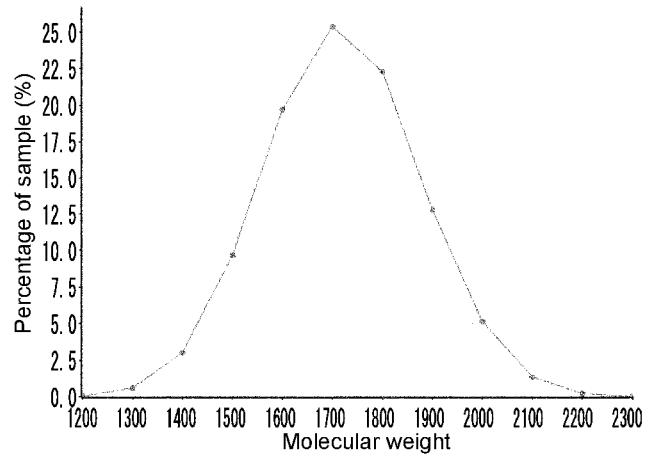

Fig. 67
Initiation read through library
Average CLogP 5.97
Average number of NMe amino acids 4.4
Average molecular weight 1678.7
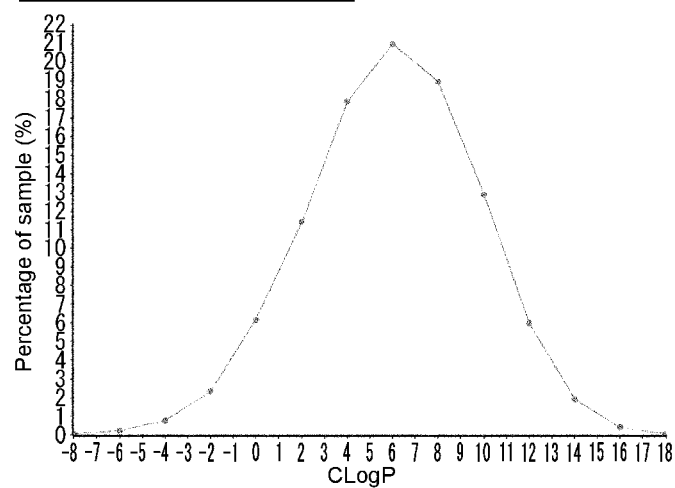
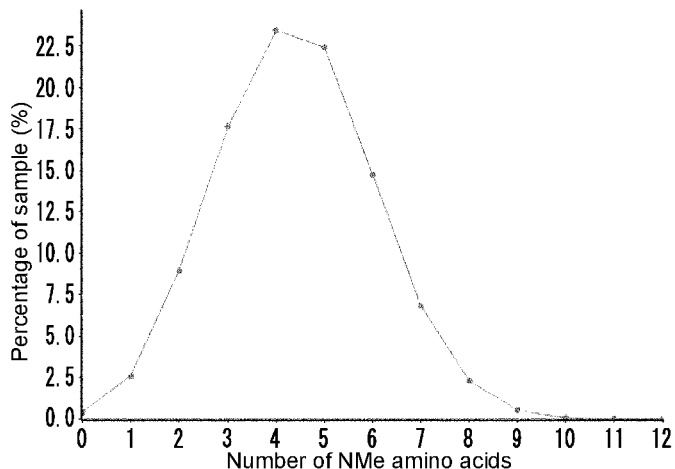
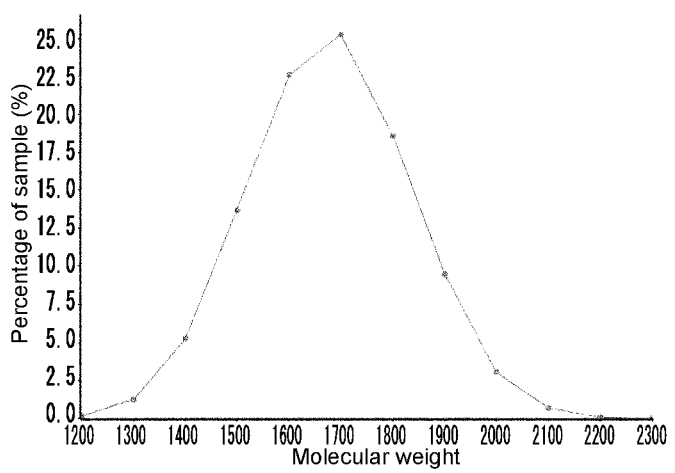

Fig. 84
Scheme A
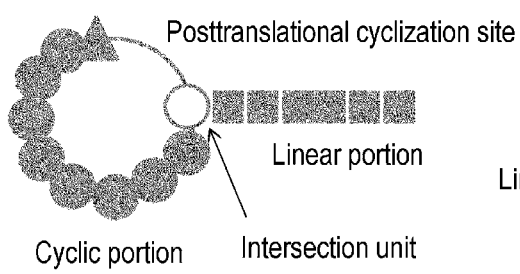
Cyclic portion   Intersection unit
Scheme A-1
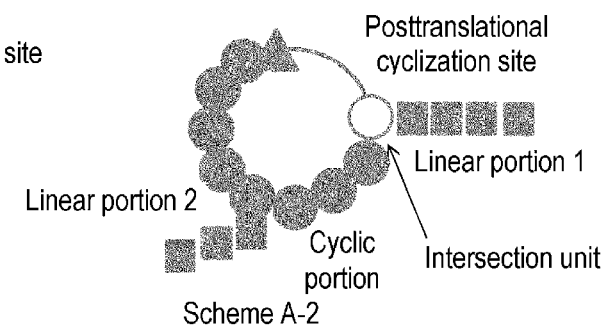
Scheme A-2

Scheme C

Scheme B

Cyclic portion

Scheme F3.

Scheme C-2.

Scheme G1.

Scheme x.

Scheme G3.

Scheme H.

Fig. 103-1
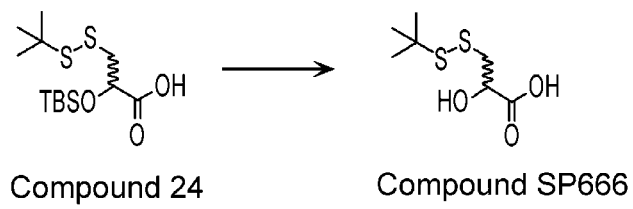
Compound 24    Compound SP666
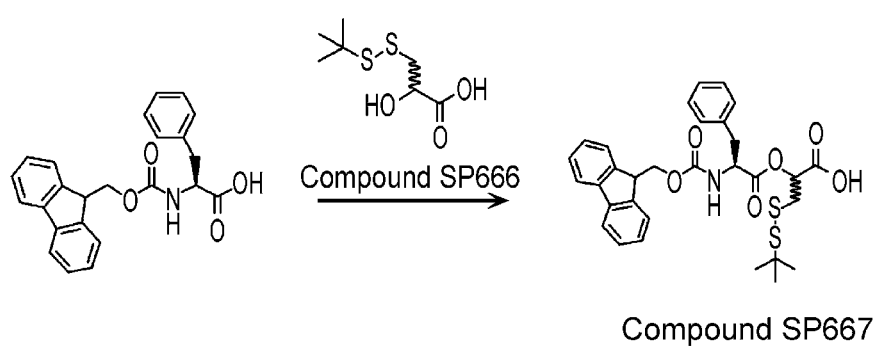
Compound SP667
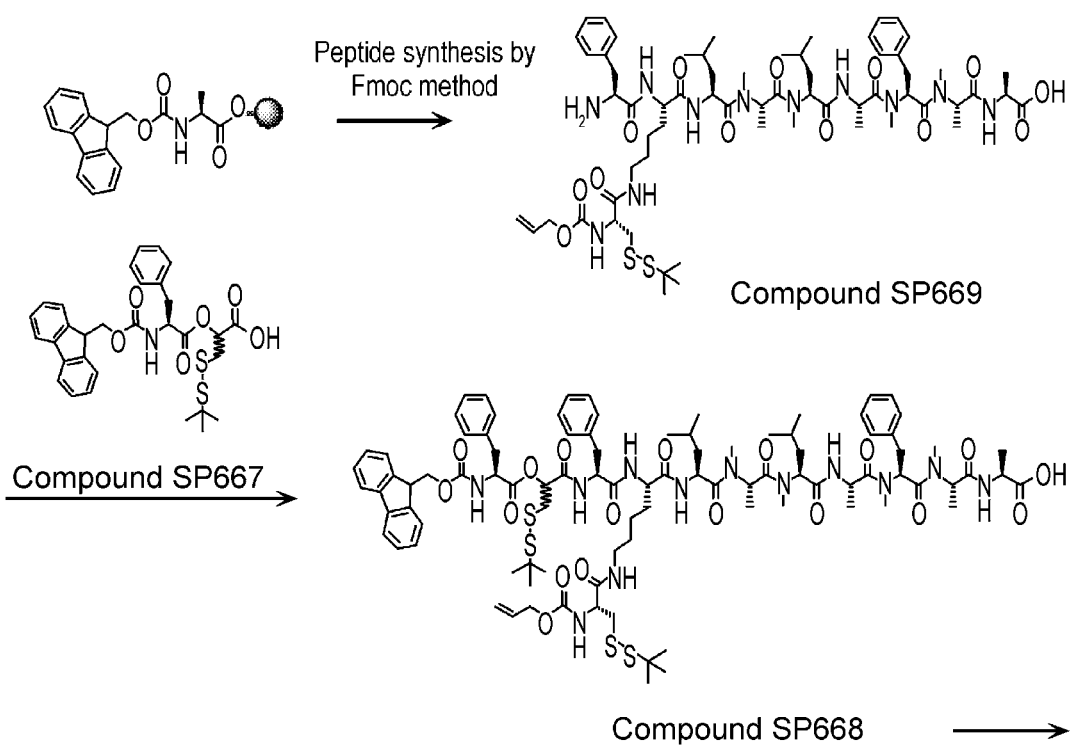

Fig. 103-2
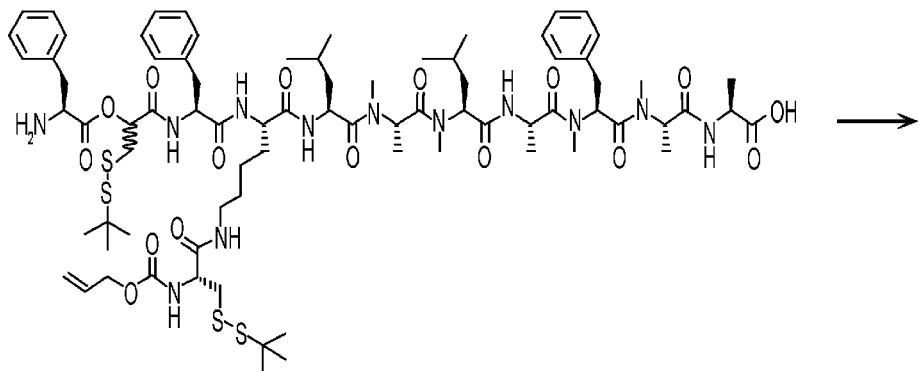
Compound SP670
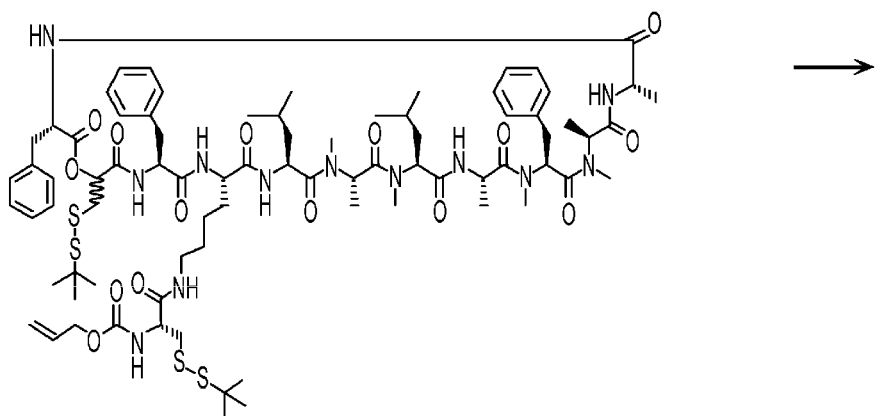
Compound SP671
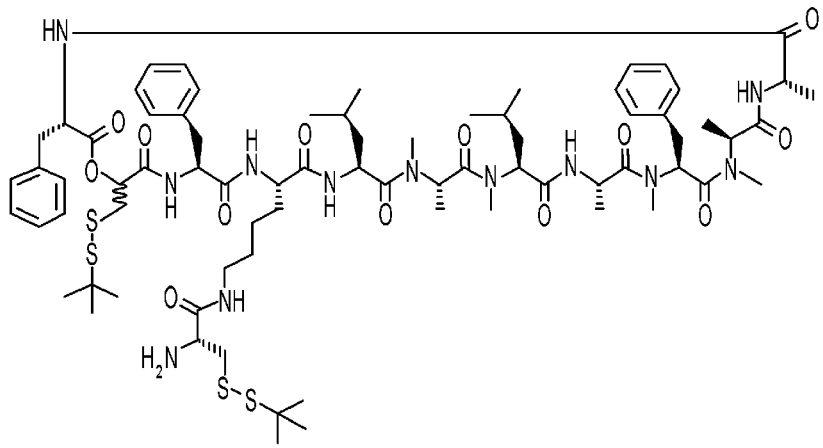
Compound SP665

Template synthesis

Solid supporting

Compound 74 + AcOH + ⬤—NH₂ —DMTMM→ Compound 75

Fig. 106
Peptide elongation
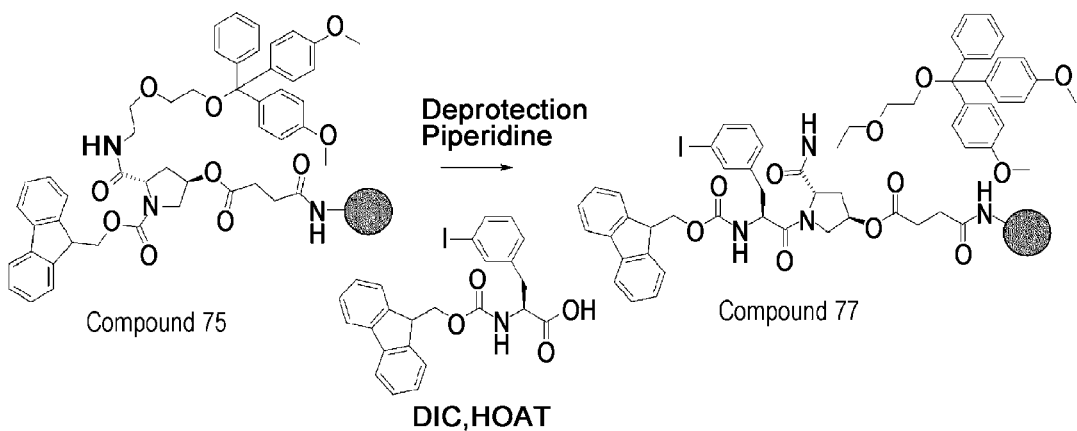
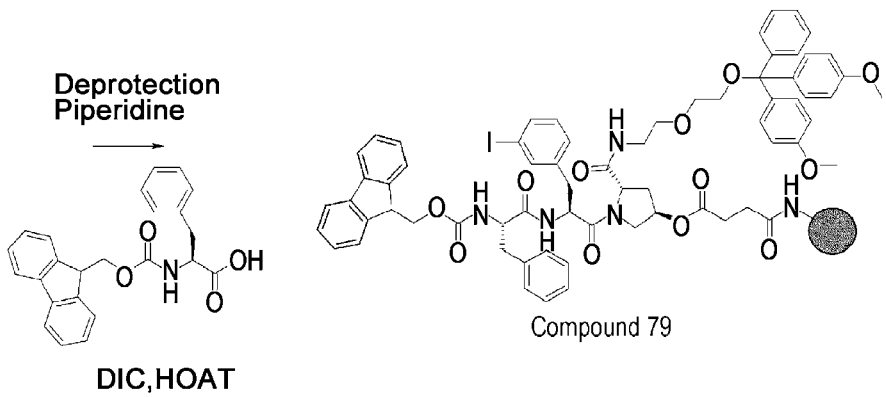
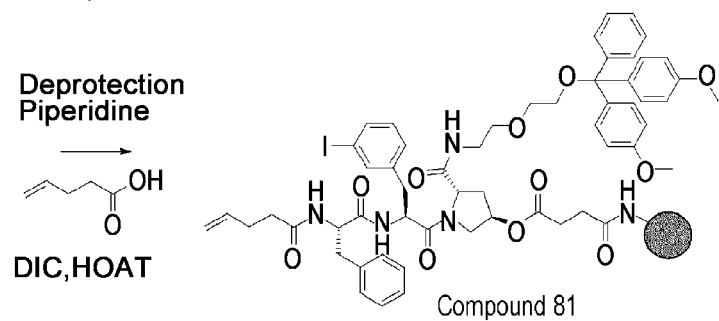

RNA synthesis and cleavage

Compound 71

Compound 72 dC-Puromycin CPG
SP802 dC-Puromycin
SP803 dC-Puromycin CPG
SP802

Fl-dC-Puromycin CPG
SP804

SEQUENCE LISTING

```
Sequence total quantity: 354
SEQ ID NO: 1            moltype = DNA  length = 95
FEATURE                 Location/Qualifiers
misc_feature            1..95
                        note = tRNA D-1
source                  1..95
                        mol_type = other DNA
                        organism = synthetic construct
SEQUENCE: 1
ggcgtaatac gactcactat aggctctgta gttcagtcgg tagaacggcg gactgagaat    60
ccgtatgtca ctggttcgag tccagtcaga gccgc                               95

SEQ ID NO: 2            moltype = DNA  length = 96
FEATURE                 Location/Qualifiers
misc_feature            1..96
                        note = template DNA D-2
source                  1..96
                        mol_type = other DNA
                        organism = synthetic construct
SEQUENCE: 2
gtaatacgac tcactatagg gttaacttta agaaggagat atacatatga ctacaacgcg    60
actttactac cgtcgtggcg gctaataaat agatag                              96

SEQ ID NO: 3            moltype = DNA  length = 93
FEATURE                 Location/Qualifiers
misc_feature            1..93
                        note = template DNA D-3
source                  1..93
                        mol_type = other DNA
                        organism = synthetic construct
SEQUENCE: 3
gtaatacgac tcactatagg gttaacttta agaaggagat atacatatga ctacaacgcg    60
actttactac cgtggcggct agtagataga tag                                 93

SEQ ID NO: 4            moltype = DNA  length = 91
FEATURE                 Location/Qualifiers
```

```
misc_feature            1..91
                        note = template DNA D-4
source                  1..91
                        mol_type = other DNA
                        organism = synthetic construct
SEQUENCE: 4
gtaatacgac tcactatagg gttaacttta agaaggagat atacatatga ctacaacggc    60
gggcggcctt tttttggcg gcaaataata a                                    91

SEQ ID NO: 5            moltype = DNA  length = 96
FEATURE                 Location/Qualifiers
misc_feature            1..96
                        note = template DNA D-5
source                  1..96
                        mol_type = other DNA
                        organism = synthetic construct
SEQUENCE: 5
ggcgtaatac gactcactat aggcggggtg gagcagcctg gtagctcgtc gggctcataa    60
cccgaagatc gtcggttcaa atccggcccc cgcaac                              96

SEQ ID NO: 6            moltype = DNA  length = 88
FEATURE                 Location/Qualifiers
misc_feature            1..88
                        note = template DNA D-6
source                  1..88
                        mol_type = other DNA
                        organism = synthetic construct
SEQUENCE: 6
gtaatacgac tcactatagg gttaacttta agaaggagat atacatatga ctagaactaa    60
ggcgtactgg agccttccgg gcggctaa                                       88

SEQ ID NO: 7            moltype = DNA  length = 94
FEATURE                 Location/Qualifiers
misc_feature            1..94
                        note = template DNA D-7
source                  1..94
                        mol_type = other DNA
                        organism = synthetic construct
SEQUENCE: 7
gtaatacgac tcactatagg gttaacttta agaaggagat atacatatga ctagaactgc    60
ctactggagc ctttgcggca gcggcagcgg cagc                                94

SEQ ID NO: 8            moltype = DNA  length = 96
FEATURE                 Location/Qualifiers
misc_feature            1..96
                        note = template DNA D-8
source                  1..96
                        mol_type = other DNA
                        organism = synthetic construct
SEQUENCE: 8
gtaatacgac tcactatagg gttaacttta agaaggagat atacatatgt gcactacaac    60
gcgtctttac taccgtggcg gctagtagat agatag                              96

SEQ ID NO: 9            moltype = DNA  length = 96
FEATURE                 Location/Qualifiers
misc_feature            1..96
                        note = template DNA D-9
source                  1..96
                        mol_type = other DNA
                        organism = synthetic construct
SEQUENCE: 9
gtaatacgac tcactatagg gttaacttta agaaggagat atacatatgt gctttactac    60
aacgctttac taccgtggcg gctagtagat agatag                              96

SEQ ID NO: 10           moltype = DNA  length = 96
FEATURE                 Location/Qualifiers
misc_feature            1..96
                        note = template DNA D-10
source                  1..96
                        mol_type = other DNA
                        organism = synthetic construct
SEQUENCE: 10
gtaatacgac tcactatagg gttaacttta agaaggagat atacatatgt gcttgactac    60
aacgctttac taccgtggcg gctagtagat agatag                              96

SEQ ID NO: 11           moltype = DNA  length = 96
FEATURE                 Location/Qualifiers
misc_feature            1..96
                        note = template DNA D-11
```

```
source                  1..96
                        mol_type = other DNA
                        organism = synthetic construct
SEQUENCE: 11
gtaatacgac tcactatagg gttaacttta agaaggagat atacatatgt gctacactac    60
aacgctttac taccgtggcg gctagtagat agatag                              96

SEQ ID NO: 12           moltype = DNA  length = 96
FEATURE                 Location/Qualifiers
misc_feature            1..96
                        note = template DNA D-12
source                  1..96
                        mol_type = other DNA
                        organism = synthetic construct
SEQUENCE: 12
gtaatacgac tcactatagg gttaacttta agaaggagat atacatatgt gctgcactac    60
aacgctttac taccgtggcg gctagtagat agatag                              96

SEQ ID NO: 13           moltype = DNA  length = 96
FEATURE                 Location/Qualifiers
misc_feature            1..96
                        note = template DNA D-13
source                  1..96
                        mol_type = other DNA
                        organism = synthetic construct
SEQUENCE: 13
gtaatacgac tcactatagg gttaacttta agaaggagat atacatatgt gctggactac    60
aacgctttac taccgtggcg gctagtagat agatag                              96

SEQ ID NO: 14           moltype = DNA  length = 96
FEATURE                 Location/Qualifiers
misc_feature            1..96
                        note = template DNA D-14
source                  1..96
                        mol_type = other DNA
                        organism = synthetic construct
SEQUENCE: 14
gtaatacgac tcactatagg gttaacttta agaaggagat atacatatgt gccttactac    60
aacgctttac taccgtggcg gctagtagat agatag                              96

SEQ ID NO: 15           moltype = DNA  length = 96
FEATURE                 Location/Qualifiers
misc_feature            1..96
                        note = template DNA D-15
source                  1..96
                        mol_type = other DNA
                        organism = synthetic construct
SEQUENCE: 15
gtaatacgac tcactatagg gttaacttta agaaggagat atacatatgt gcctaactac    60
aacgctttac taccgtggcg gctagtagat agatag                              96

SEQ ID NO: 16           moltype = DNA  length = 96
FEATURE                 Location/Qualifiers
misc_feature            1..96
                        note = template DNA D-16
source                  1..96
                        mol_type = other DNA
                        organism = synthetic construct
SEQUENCE: 16
gtaatacgac tcactatagg gttaacttta agaaggagat atacatatgt gcccgactac    60
aacgctttac taccgtggcg gctagtagat agatag                              96

SEQ ID NO: 17           moltype = DNA  length = 96
FEATURE                 Location/Qualifiers
misc_feature            1..96
                        note = template DNA D-17
source                  1..96
                        mol_type = other DNA
                        organism = synthetic construct
SEQUENCE: 17
gtaatacgac tcactatagg gttaacttta agaaggagat atacatatgt gccatactac    60
aacgctttac taccgtggcg gctagtagat agatag                              96

SEQ ID NO: 18           moltype = DNA  length = 96
FEATURE                 Location/Qualifiers
misc_feature            1..96
                        note = template DNA D-18
source                  1..96
                        mol_type = other DNA
```

```
                        organism = synthetic construct
SEQUENCE: 18
gtaatacgac tcactatagg gttaacttta agaaggagat atacatatgt gccagactac    60
aacgctttac taccgtggcg gctagtagat agatag                              96

SEQ ID NO: 19           moltype = DNA   length = 96
FEATURE                 Location/Qualifiers
misc_feature            1..96
                        note = template DNA D-19
source                  1..96
                        mol_type = other DNA
                        organism = synthetic construct
SEQUENCE: 19
gtaatacgac tcactatagg gttaacttta agaaggagat atacatatgt gccgtactac    60
aacgctttac taccgtggcg gctagtagat agatag                              96

SEQ ID NO: 20           moltype = DNA   length = 96
FEATURE                 Location/Qualifiers
misc_feature            1..96
                        note = template DNA D-20
source                  1..96
                        mol_type = other DNA
                        organism = synthetic construct
SEQUENCE: 20
gtaatacgac tcactatagg gttaacttta agaaggagat atacatatgt gccggactac    60
aacgctttac taccgtggcg gctagtagat agatag                              96

SEQ ID NO: 21           moltype = DNA   length = 96
FEATURE                 Location/Qualifiers
misc_feature            1..96
                        note = template DNA D-21
source                  1..96
                        mol_type = other DNA
                        organism = synthetic construct
SEQUENCE: 21
gtaatacgac tcactatagg gttaacttta agaaggagat atacatatgt gcattactac    60
aacgctttac taccgtggcg gctagtagat agatag                              96

SEQ ID NO: 22           moltype = DNA   length = 96
FEATURE                 Location/Qualifiers
misc_feature            1..96
                        note = template DNA D-23
source                  1..96
                        mol_type = other DNA
                        organism = synthetic construct
SEQUENCE: 22
gtaatacgac tcactatagg gttaacttta agaaggagat atacatatgt gcactactac    60
aacgctttac taccgtggcg gctagtagat agatag                              96

SEQ ID NO: 23           moltype = DNA   length = 96
FEATURE                 Location/Qualifiers
misc_feature            1..96
                        note = template DNA D-24
source                  1..96
                        mol_type = other DNA
                        organism = synthetic construct
SEQUENCE: 23
gtaatacgac tcactatagg gttaacttta agaaggagat atacatatgt gcaacactac    60
aacgctttac taccgtggcg gctagtagat agatag                              96

SEQ ID NO: 24           moltype = DNA   length = 96
FEATURE                 Location/Qualifiers
misc_feature            1..96
                        note = template DNA D-25
source                  1..96
                        mol_type = other DNA
                        organism = synthetic construct
SEQUENCE: 24
gtaatacgac tcactatagg gttaacttta agaaggagat atacatatgt gcagtactac    60
aacgctttac taccgtggcg gctagtagat agatag                              96

SEQ ID NO: 25           moltype = DNA   length = 96
FEATURE                 Location/Qualifiers
misc_feature            1..96
                        note = template DNA D-26
source                  1..96
                        mol_type = other DNA
                        organism = synthetic construct
SEQUENCE: 25
```

```
gtaatacgac tcactatagg gttaacttta agaaggagat atacatatgt gcaggactac    60
aacgctttac taccgtggcg gctagtagat agatag                              96

SEQ ID NO: 26              moltype = DNA   length = 96
FEATURE                    Location/Qualifiers
misc_feature               1..96
                           note = template DNA D-27
source                     1..96
                           mol_type = other DNA
                           organism = synthetic construct
SEQUENCE: 26
gtaatacgac tcactatagg gttaacttta agaaggagat atacatatgt gcgttactac    60
aacgctttac taccgtggcg gctagtagat agatag                              96

SEQ ID NO: 27              moltype = DNA   length = 96
FEATURE                    Location/Qualifiers
misc_feature               1..96
                           note = template DNA D-28
source                     1..96
                           mol_type = other DNA
                           organism = synthetic construct
SEQUENCE: 27
gtaatacgac tcactatagg gttaacttta agaaggagat atacatatgt gcgctactac    60
aacgctttac taccgtggcg gctagtagat agatag                              96

SEQ ID NO: 28              moltype = DNA   length = 88
FEATURE                    Location/Qualifiers
misc_feature               1..88
                           note = template DNA D-32
source                     1..88
                           mol_type = other DNA
                           organism = synthetic construct
SEQUENCE: 28
gtaatacgac tcactatagg gttaacttta agaaggagat atacatatgt gcactagaac    60
taaggcgtac tggagccttc cgggctaa                                       88

SEQ ID NO: 29              moltype = DNA   length = 95
FEATURE                    Location/Qualifiers
misc_feature               1..95
                           note = template DNA D-34
source                     1..95
                           mol_type = other DNA
                           organism = synthetic construct
SEQUENCE: 29
gtaatacgac tcactatagg gttaacttta agaaggagat atacatatgt gcactacaac    60
gcgtctttac taccgtggcg gctagtagat agata                               95

SEQ ID NO: 30              moltype = RNA   length = 74
FEATURE                    Location/Qualifiers
misc_feature               1..74
                           note = tRNA R-1
source                     1..74
                           mol_type = other RNA
                           organism = synthetic construct
SEQUENCE: 30
ggctctgtag ttcagtcggt agaacggcgg actgagaatc cgtatgtcac tggttcgagt    60
ccagtcagag ccgc                                                      74

SEQ ID NO: 31              moltype = RNA   length = 76
FEATURE                    Location/Qualifiers
misc_feature               1..76
                           note = tRNA R-1 + dCA
source                     1..76
                           mol_type = other RNA
                           organism = synthetic construct
SEQUENCE: 31
ggctctgtag ttcagtcggt agaacggcgg actgagaatc cgtatgtcac tggttcgagt    60
ccagtcagag ccgcca                                                    76

SEQ ID NO: 32              moltype = RNA   length = 75
FEATURE                    Location/Qualifiers
misc_feature               1..75
                           note = tRNA R-5
source                     1..75
                           mol_type = other RNA
                           organism = synthetic construct
SEQUENCE: 32
ggcggggtgg agcagcctgg tagctcgtcg ggctcataac ccgaagatcg tcggttcaaa    60
tccggccccc gcaac                                                     75
```

```
SEQ ID NO: 33            moltype = RNA   length = 77
FEATURE                  Location/Qualifiers
misc_feature             1..77
                         note = tRNA R-5 + dCA
source                   1..77
                         mol_type = other RNA
                         organism = synthetic construct
SEQUENCE: 33
ggcggggtgg agcagcctgg tagctcgtcg ggctcataac ccgaagatcg tcggttcaaa   60
tccggccccc gcaacca                                                  77

SEQ ID NO: 34            moltype = AA    length = 11
FEATURE                  Location/Qualifiers
REGION                   1..11
                         note = peptide P-3
MOD_RES                  6..7
                         note = aspartimide formation
source                   1..11
                         mol_type = protein
                         organism = synthetic construct
SEQUENCE: 34
MTTTRDYYRG G                                                        11

SEQ ID NO: 35            moltype = AA    length = 13
FEATURE                  Location/Qualifiers
REGION                   1..13
                         note = peptide P-6
MOD_RES                  8..9
                         note = aspartimide formation
source                   1..13
                         mol_type = protein
                         organism = synthetic construct
SEQUENCE: 35
MTTTAGGDFF GGK                                                      13

SEQ ID NO: 36            moltype = AA    length = 10
FEATURE                  Location/Qualifiers
REGION                   1..10
                         note = peptide P-11
source                   1..10
                         mol_type = protein
                         organism = synthetic construct
SEQUENCE: 36
TTTRLYYRGG                                                          10

SEQ ID NO: 37            moltype = AA    length = 15
FEATURE                  Location/Qualifiers
REGION                   1..15
                         note = peptide P-13
source                   1..15
                         mol_type = protein
                         organism = synthetic construct
SEQUENCE: 37
TRTAYWSLCG SGSGS                                                    15

SEQ ID NO: 38            moltype = AA    length = 11
FEATURE                  Location/Qualifiers
REGION                   1..11
                         note = peptide P-14
source                   1..11
                         mol_type = protein
                         organism = synthetic construct
SEQUENCE: 38
CTTTRLYYRG G                                                        11

SEQ ID NO: 39            moltype = AA    length = 11
FEATURE                  Location/Qualifiers
REGION                   1..11
                         note = peptide P-15
source                   1..11
                         mol_type = protein
                         organism = synthetic construct
SEQUENCE: 39
CFTTTLYYRG G                                                        11

SEQ ID NO: 40            moltype = AA    length = 11
FEATURE                  Location/Qualifiers
REGION                   1..11
```

```
                              note = peptide P-16
source                        1..11
                              mol_type = protein
                              organism = synthetic construct
SEQUENCE: 40
CLTTTLYYRG G                                                                    11

SEQ ID NO: 41                 moltype = AA   length = 11
FEATURE                       Location/Qualifiers
REGION                        1..11
                              note = peptide P-17
source                        1..11
                              mol_type = protein
                              organism = synthetic construct
SEQUENCE: 41
CYTTTLYYRG G                                                                    11

SEQ ID NO: 42                 moltype = AA   length = 11
FEATURE                       Location/Qualifiers
REGION                        1..11
                              note = peptide P-18
source                        1..11
                              mol_type = protein
                              organism = synthetic construct
SEQUENCE: 42
CCTTTLYYRG G                                                                    11

SEQ ID NO: 43                 moltype = AA   length = 11
FEATURE                       Location/Qualifiers
REGION                        1..11
                              note = peptide P-19
source                        1..11
                              mol_type = protein
                              organism = synthetic construct
SEQUENCE: 43
CWTTTLYYRG G                                                                    11

SEQ ID NO: 44                 moltype = AA   length = 11
FEATURE                       Location/Qualifiers
REGION                        1..11
                              note = peptide P-20
source                        1..11
                              mol_type = protein
                              organism = synthetic construct
SEQUENCE: 44
CLTTTLYYRG G                                                                    11

SEQ ID NO: 45                 moltype = AA   length = 11
FEATURE                       Location/Qualifiers
REGION                        1..11
                              note = peptide P-21
source                        1..11
                              mol_type = protein
                              organism = synthetic construct
SEQUENCE: 45
CLTTTLYYRG G                                                                    11

SEQ ID NO: 46                 moltype = AA   length = 11
FEATURE                       Location/Qualifiers
REGION                        1..11
                              note = peptide P-22
source                        1..11
                              mol_type = protein
                              organism = synthetic construct
SEQUENCE: 46
CPTTTLYYRG G                                                                    11

SEQ ID NO: 47                 moltype = AA   length = 11
FEATURE                       Location/Qualifiers
REGION                        1..11
                              note = peptide P-23
source                        1..11
                              mol_type = protein
                              organism = synthetic construct
SEQUENCE: 47
CHTTTLYYRG G                                                                    11

SEQ ID NO: 48                 moltype = AA   length = 11
FEATURE                       Location/Qualifiers
```

```
REGION                    1..11
                          note = peptide P-24
source                    1..11
                          mol_type = protein
                          organism = synthetic construct
SEQUENCE: 48
CQTTTLYYRG G                                                                      11

SEQ ID NO: 49             moltype = AA  length = 11
FEATURE                   Location/Qualifiers
REGION                    1..11
                          note = peptide P-25
source                    1..11
                          mol_type = protein
                          organism = synthetic construct
SEQUENCE: 49
CRTTTLYYRG G                                                                      11

SEQ ID NO: 50             moltype = AA  length = 11
FEATURE                   Location/Qualifiers
REGION                    1..11
                          note = peptide P-26
source                    1..11
                          mol_type = protein
                          organism = synthetic construct
SEQUENCE: 50
CRTTTLYYRG G                                                                      11

SEQ ID NO: 51             moltype = AA  length = 11
FEATURE                   Location/Qualifiers
REGION                    1..11
                          note = peptide P-27
source                    1..11
                          mol_type = protein
                          organism = synthetic construct
SEQUENCE: 51
CITTTLYYRG G                                                                      11

SEQ ID NO: 52             moltype = AA  length = 11
FEATURE                   Location/Qualifiers
REGION                    1..11
                          note = peptide P-28
source                    1..11
                          mol_type = protein
                          organism = synthetic construct
SEQUENCE: 52
CTTTTLYYRG G                                                                      11

SEQ ID NO: 53             moltype = AA  length = 11
FEATURE                   Location/Qualifiers
REGION                    1..11
                          note = peptide P-29
source                    1..11
                          mol_type = protein
                          organism = synthetic construct
SEQUENCE: 53
CNTTTLYYRG G                                                                      11

SEQ ID NO: 54             moltype = AA  length = 11
FEATURE                   Location/Qualifiers
REGION                    1..11
                          note = peptide P-30
source                    1..11
                          mol_type = protein
                          organism = synthetic construct
SEQUENCE: 54
CSTTTLYYRG G                                                                      11

SEQ ID NO: 55             moltype = AA  length = 11
FEATURE                   Location/Qualifiers
REGION                    1..11
                          note = peptide P-31
source                    1..11
                          mol_type = protein
                          organism = synthetic construct
SEQUENCE: 55
CRTTTLYYRG G                                                                      11

SEQ ID NO: 56             moltype = AA  length = 11
```

```
FEATURE                     Location/Qualifiers
REGION                      1..11
                            note = peptide P-32
source                      1..11
                            mol_type = protein
                            organism = synthetic construct
SEQUENCE: 56
CVTTTLYYRG G                                                                11

SEQ ID NO: 57               moltype = AA  length = 11
FEATURE                     Location/Qualifiers
REGION                      1..11
                            note = peptide P-33
source                      1..11
                            mol_type = protein
                            organism = synthetic construct
SEQUENCE: 57
CATTTLYYRG G                                                                11

SEQ ID NO: 58               moltype = AA  length = 11
FEATURE                     Location/Qualifiers
REGION                      1..11
                            note = peptide P-51
source                      1..11
                            mol_type = protein
                            organism = synthetic construct
SEQUENCE: 58
ATTTRLYYRG G                                                                11

SEQ ID NO: 59               moltype = AA  length = 11
FEATURE                     Location/Qualifiers
REGION                      1..11
                            note = peptide P-53
REGION                      1..6
                            note = CROSSLINK - isoaspartyl cysteine (Cys-Asp)
source                      1..11
                            mol_type = protein
                            organism = synthetic construct
SEQUENCE: 59
CTTTRDYYRG G                                                                11

SEQ ID NO: 60               moltype =     length =
SEQUENCE: 60
000

SEQ ID NO: 61               moltype = AA  length = 13
FEATURE                     Location/Qualifiers
REGION                      1..13
                            note = An artificially synthesized peptide sequence
source                      1..13
                            mol_type = protein
                            organism = synthetic construct
SEQUENCE: 61
MTRTKAYWSL PGG                                                              13

SEQ ID NO: 62               moltype = AA  length = 12
FEATURE                     Location/Qualifiers
REGION                      1..12
                            note = peptide DP-3
REGION                      1..12
                            note = CROSSLINK - isoaspartyl alanine (Ala-Asp)
SITE                        4
                            note = misc_feature - Xaa = MeVal
source                      1..12
                            mol_type = protein
                            organism = synthetic construct
SEQUENCE: 62
AALXLFFPIT GD                                                               12

SEQ ID NO: 63               moltype = AA  length = 10
FEATURE                     Location/Qualifiers
REGION                      1..10
                            note = peptide DP-330
REGION                      1..10
                            note = CROSSLINK - isoaspartyl alanine (Ala-Asp)
SITE                        3
                            note = misc_feature - Xaa = MeGly
source                      1..10
                            mol_type = protein
```

-continued

```
                         organism = synthetic construct
SEQUENCE: 63
AFXLFLITFD                                                               10

SEQ ID NO: 64            moltype = DNA  length = 95
FEATURE                  Location/Qualifiers
misc_feature             1..95
                         note = template DNA D-40
source                   1..95
                         mol_type = other DNA
                         organism = synthetic construct
SEQUENCE: 64
ggcgtaatac gactcactat agtccccttc gtctagaggc ccaggacacc gccctaagac     60
ggcggtaaca ggggttcgaa tcccctaggg gacgc                                95

SEQ ID NO: 65            moltype = RNA  length = 74
FEATURE                  Location/Qualifiers
misc_feature             1..74
                         note = tRNA R-40
source                   1..74
                         mol_type = other RNA
                         organism = synthetic construct
SEQUENCE: 65
gtccccttcg tctagaggcc caggacaccg ccctaagacg gcggtaacag gggttcgaat     60
cccctagggg acgc                                                       74

SEQ ID NO: 66            moltype = RNA  length = 76
FEATURE                  Location/Qualifiers
misc_feature             1..76
                         note = tRNA R-40 + dCA
source                   1..76
                         mol_type = other RNA
                         organism = synthetic construct
SEQUENCE: 66
gtccccttcg tctagaggcc caggacaccg ccctaagacg gcggtaacag gggttcgaat     60
cccctagggg acgcca                                                     76

SEQ ID NO: 67            moltype = RNA  length = 73
FEATURE                  Location/Qualifiers
misc_feature             1..73
                         note = template RNA R-41
source                   1..73
                         mol_type = other RNA
                         organism = synthetic construct
SEQUENCE: 67
gggttaactt taagaaggag atatacatat gggtactaca acgcgtcttc cgtaccgtgg     60
cggctaagct tcg                                                        73

SEQ ID NO: 68            moltype = AA  length = 11
FEATURE                  Location/Qualifiers
REGION                   1..11
                         note = peptide P-143
REGION                   1..6
                         note = CROSSLINK - isoaspartyl glycine (Gly-Asp)
source                   1..11
                         mol_type = protein
                         organism = synthetic construct
SEQUENCE: 68
GTTTRDPYRG G                                                             11

SEQ ID NO: 69            moltype = RNA  length = 10
FEATURE                  Location/Qualifiers
misc_feature             1..10
                         note = An artificially synthesized nucleotide sequence
source                   1..10
                         mol_type = other RNA
                         organism = synthetic construct
SEQUENCE: 69
agcttagtca                                                               10

SEQ ID NO: 70            moltype = RNA  length = 20
FEATURE                  Location/Qualifiers
misc_feature             1..20
                         note = An artificially synthesized nucleotide sequence
source                   1..20
                         mol_type = other RNA
                         organism = synthetic construct
SEQUENCE: 70
agcttagtca ccgtcagtca                                                    20
```

```
SEQ ID NO: 71              moltype = RNA    length = 79
FEATURE                    Location/Qualifiers
misc_feature               1..79
                           note = mRNA R-41
source                     1..79
                           mol_type = other RNA
                           organism = synthetic construct
SEQUENCE: 71
gggttaactt taagaaggag atatacatat gtttcttccg agcggctctg gctctggctc    60
ttagggcggc ggggacaaa                                                 79

SEQ ID NO: 72              moltype = RNA    length = 88
FEATURE                    Location/Qualifiers
misc_feature               1..88
                           note = mRNA R-42
source                     1..88
                           mol_type = other RNA
                           organism = synthetic construct
SEQUENCE: 72
gggttaactt taagaaggag atatacatat gactacaacg agcggctctg gctcttttct    60
tccgggctct tagggcggcg gggacaaa                                       88

SEQ ID NO: 73              moltype = RNA    length = 88
FEATURE                    Location/Qualifiers
misc_feature               1..88
                           note = mRNA R-43
source                     1..88
                           mol_type = other RNA
                           organism = synthetic construct
SEQUENCE: 73
gggttaactt taagaaggag atatacatat gaacaacaac aacaacacta caacgggcct    60
tccgggctct tagggcggcg gggacaaa                                       88

SEQ ID NO: 74              moltype = DNA    length = 124
FEATURE                    Location/Qualifiers
misc_feature               1..124
                           note = template DNA D-50
source                     1..124
                           mol_type = other DNA
                           organism = synthetic construct
SEQUENCE: 74
gtaatacgac tcactatagg gttaacttta agaaggagat atacatatga ctagaactaa    60
ggcgtactgg agccttccgg gcggcagcgg ctctggctct ggctcttagg gcggcgggga   120
caaa                                                                124

SEQ ID NO: 75              moltype = RNA    length = 106
FEATURE                    Location/Qualifiers
misc_feature               1..106
                           note = mRNA
source                     1..106
                           mol_type = other RNA
                           organism = synthetic construct
SEQUENCE: 75
gggttaactt taagaaggag atatacatat gactagaact aaggcgtact ggagccttcc    60
gggcggcagc ggctctggct ctggctctta gggcggcggg gacaaa                  106

SEQ ID NO: 76              moltype = DNA    length = 16
FEATURE                    Location/Qualifiers
misc_feature               1..16
                           note = linker sequence C-1
source                     1..16
                           mol_type = other DNA
                           organism = synthetic construct
SEQUENCE: 76
cccgtccccg ccgccc                                                    16

SEQ ID NO: 77              moltype = DNA    length = 39
FEATURE                    Location/Qualifiers
misc_feature               1..39
                           note = primer sequence C-2
source                     1..39
                           mol_type = other DNA
                           organism = synthetic construct
SEQUENCE: 77
tttgtccccg ccgccctaag agccagagcc agagccgct                           39

SEQ ID NO: 78              moltype = RNA    length = 73
FEATURE                    Location/Qualifiers
```

```
misc_feature           1..73
                       note = RNA sequence RM-D1
source                 1..73
                       mol_type = other RNA
                       organism = synthetic construct
SEQUENCE: 78
gggttaacttt taagaaggag atatacatat gtttactaca acgcgtcttc cgtaccgtgg    60
cggctaagct tcg                                                        73

SEQ ID NO: 79          moltype = RNA  length = 73
FEATURE                Location/Qualifiers
misc_feature           1..73
                       note = RNA sequence RM-D2
source                 1..73
                       mol_type = other RNA
                       organism = synthetic construct
SEQUENCE: 79
gggttaacttt taagaaggag atatacatat ggctactaca acgcgtcttc cgtaccgtgg    60
cggctaagct tcg                                                        73

SEQ ID NO: 80          moltype = AA  length = 11
FEATURE                Location/Qualifiers
REGION                 1..11
                       note = peptide P-D3
REGION                 1..6
                       note = CROSSLINK - isoaspartyl phenylalanine (Phe-Asp)
source                 1..11
                       mol_type = protein
                       organism = synthetic construct
SEQUENCE: 80
FTTTRDPYRG G                                                          11

SEQ ID NO: 81          moltype = AA  length = 11
FEATURE                Location/Qualifiers
REGION                 1..11
                       note = peptide P-D4
REGION                 1..6
                       note = CROSSLINK - isoaspartyl alanine (Ala-Asp)
source                 1..11
                       mol_type = protein
                       organism = synthetic construct
SEQUENCE: 81
ATTTRDPYRG G                                                          11

SEQ ID NO: 82          moltype = DNA  length = 104
FEATURE                Location/Qualifiers
misc_feature           1..104
                       note = DNA sequence DM-D1
source                 1..104
                       mol_type = other DNA
                       organism = synthetic construct
SEQUENCE: 82
gtaatacgac tcactatagg gttaacttta agaaggagat atacatatgg gtactacaac     60
gcgtcttccg taccgtagcg gctctggctc tggctctaaa aaaa                     104

SEQ ID NO: 83          moltype = DNA  length = 104
FEATURE                Location/Qualifiers
misc_feature           1..104
                       note = DNA sequence DM-D2
source                 1..104
                       mol_type = other DNA
                       organism = synthetic construct
SEQUENCE: 83
gtaatacgac tcactatagg gttaacttta agaaggagat atacatatgt ttactacaac     60
gcgtcttccg taccgtagcg gctctggctc tggctctaaa aaaa                     104

SEQ ID NO: 84          moltype = DNA  length = 104
FEATURE                Location/Qualifiers
misc_feature           1..104
                       note = DNA sequence DM-D3
source                 1..104
                       mol_type = other DNA
                       organism = synthetic construct
SEQUENCE: 84
gtaatacgac tcactatagg gttaacttta agaaggagat atacatatgg ctactacaac     60
gcgtcttccg taccgtagcg gctctggctc tggctctaaa aaaa                     104

SEQ ID NO: 85          moltype = RNA  length = 86
FEATURE                Location/Qualifiers
```

```
misc_feature          1..86
                      note = RNA sequence RM-D3
source                1..86
                      mol_type = other RNA
                      organism = synthetic construct
SEQUENCE: 85
gggttaactt taagaaggag atatacatat gggtactaca acgcgtcttc cgtaccgtag    60
cggctctggc tctggctcta aaaaaa                                         86

SEQ ID NO: 86         moltype = RNA  length = 86
FEATURE               Location/Qualifiers
misc_feature          1..86
                      note = RNA sequence RM-D4
source                1..86
                      mol_type = other RNA
                      organism = synthetic construct
SEQUENCE: 86
gggttaactt taagaaggag atatacatat gtttactaca acgcgtcttc cgtaccgtag    60
cggctctggc tctggctcta aaaaaa                                         86

SEQ ID NO: 87         moltype = RNA  length = 86
FEATURE               Location/Qualifiers
misc_feature          1..86
                      note = RNA sequence RM-D5
source                1..86
                      mol_type = other RNA
                      organism = synthetic construct
SEQUENCE: 87
gggttaactt taagaaggag atatacatat ggctactaca acgcgtcttc cgtaccgtag    60
cggctctggc tctggctcta aaaaaa                                         86

SEQ ID NO: 88         moltype = DNA  length = 95
FEATURE               Location/Qualifiers
misc_feature          1..95
                      note = DNA sequence DT-H2
source                1..95
                      mol_type = other DNA
                      organism = synthetic construct
SEQUENCE: 88
ggcgtaatac gactcactat agtcccttc gtctagaggc ccaggacacc gccctctgac    60
ggcggtaaca ggggttcgaa tcccctaggg gacgc                              95

SEQ ID NO: 89         moltype = RNA  length = 74
FEATURE               Location/Qualifiers
misc_feature          1..74
                      note = RNA sequence RT-H2
source                1..74
                      mol_type = other RNA
                      organism = synthetic construct
SEQUENCE: 89
gtcccttcg tctagaggcc caggacaccg ccctctgacg gcggtaacag gggttcgaat    60
cccctagggg acgc                                                      74

SEQ ID NO: 90         moltype = RNA  length = 76
FEATURE               Location/Qualifiers
misc_feature          1..76
                      note = tRNAGluCUG
source                1..76
                      mol_type = other RNA
                      organism = synthetic construct
SEQUENCE: 90
gtcccttcg tctagaggcc caggacaccg ccctctgacg gcggtaacag gggttcgaat    60
cccctagggg acgcca                                                    76

SEQ ID NO: 91         moltype = RNA  length = 87
FEATURE               Location/Qualifiers
misc_feature          1..87
                      note = RNA sequence RM-H1
source                1..87
                      mol_type = other RNA
                      organism = synthetic construct
SEQUENCE: 91
gggttaactt taagaaggag atatacatat gtgcactaca tggttccgtt ggtgcccaca    60
gttcaagtgg cttcctcgta gttaagg                                        87

SEQ ID NO: 92         moltype = DNA  length = 139
FEATURE               Location/Qualifiers
misc_feature          1..139
                      note = DNA sequence DM-H1
```

```
source              1..139
                    mol_type = other DNA
                    organism = synthetic construct
SEQUENCE: 92
ggcgtaatac gactcactat agggttaact ttaagaagga gatatacata tgtgcactac    60
atggttccgt tggtgcccac agttcaagtg cttcctcgt agtggctctg gctctggctc    120
ttagggcggc ggggacaaa                                                 139

SEQ ID NO: 93       moltype = RNA   length = 118
FEATURE             Location/Qualifiers
misc_feature        1..118
                    note = RNA sequence RM-H2
source              1..118
                    mol_type = other RNA
                    organism = synthetic construct
SEQUENCE: 93
gggttaactt taagaaggag atatacatat gtgcactaca tggttccgtt ggtgcccaca    60
gttcaagtgg cttcctcgta gtggctctgg ctctggctct tagggcggcg gggacaaa     118

SEQ ID NO: 94       moltype = DNA   length = 95
FEATURE             Location/Qualifiers
misc_feature        1..95
                    note = DNA sequence DT-H3
source              1..95
                    mol_type = other DNA
                    organism = synthetic construct
SEQUENCE: 94
ggcgtaatac gactcactat aggctctgta gttcagtcgg tagaacggcg gactgttaat    60
ccgtatgtca ctggttcgag tccagtcaga gccgc                               95

SEQ ID NO: 95       moltype = RNA   length = 74
FEATURE             Location/Qualifiers
misc_feature        1..74
                    note = RNA sequence RT-H3
source              1..74
                    mol_type = other RNA
                    organism = synthetic construct
SEQUENCE: 95
ggctctgtag ttcagtcggt agaacggcgg actgttaatc cgtatgtcac tggttcgagt    60
ccagtcagag ccgc                                                      74

SEQ ID NO: 96       moltype = RNA   length = 76
FEATURE             Location/Qualifiers
misc_feature        1..76
                    note = tRNAAsn-E2GUU
source              1..76
                    mol_type = other RNA
                    organism = synthetic construct
SEQUENCE: 96
ggctctgtag ttcagtcggt agaacggcgg actgttaatc cgtatgtcac tggttcgagt    60
ccagtcagag ccgcca                                                    76

SEQ ID NO: 97       moltype = RNA   length = 71
FEATURE             Location/Qualifiers
misc_feature        1..71
                    note = RNA sequence RM-H3
source              1..71
                    mol_type = other RNA
                    organism = synthetic construct
SEQUENCE: 97
gggttaactt taacaaggag aaaaacatgc gtaaccgtga ctacaaggac gacgacgaca    60
agtaagcttc g                                                         71

SEQ ID NO: 98       moltype = AA    length = 12
FEATURE             Location/Qualifiers
REGION              1..12
                    note = peptide P-H6
MOD_RES             1
                    note = FORMYLATION
source              1..12
                    mol_type = protein
                    organism = synthetic construct
SEQUENCE: 98
MRKRDYKDDD DK                                                        12

SEQ ID NO: 99       moltype = DNA   length = 95
FEATURE             Location/Qualifiers
misc_feature        1..95
                    note = DNA sequence DTL-1
```

```
                          -continued source                    1..95
                          mol_type = other DNA
                          organism = synthetic construct
SEQUENCE: 99
ggcgtaatac gactcactat agtccccttc gtctagaggc ccaggacacc gccctctgac    60
ggcggtaaca ggggttcgaa tcccctaggg gacgc                               95

SEQ ID NO: 100            moltype = DNA   length = 95
FEATURE                   Location/Qualifiers
misc_feature              1..95
                          note = DNA sequence DTL-2
source                    1..95
                          mol_type = other DNA
                          organism = synthetic construct
SEQUENCE: 100
ggcgtaatac gactcactat agtccccttc gtctagaggc ccaggacacc gccctacgac    60
ggcggtaaca ggggttcgaa tcccctaggg gacgc                               95

SEQ ID NO: 101            moltype = DNA   length = 95
FEATURE                   Location/Qualifiers
misc_feature              1..95
                          note = DNA sequence DTL-3
source                    1..95
                          mol_type = other DNA
                          organism = synthetic construct
SEQUENCE: 101
ggcgtaatac gactcactat agtccccttc gtctagaggc ccaggacacc gcccttttcac   60
ggcggtaaca ggggttcgaa tcccctaggg gacgc                               95

SEQ ID NO: 102            moltype = DNA   length = 95
FEATURE                   Location/Qualifiers
misc_feature              1..95
                          note = DNA sequence DTL-4
source                    1..95
                          mol_type = other DNA
                          organism = synthetic construct
SEQUENCE: 102
ggcgtaatac gactcactat agtccccttc gtctagaggc ccaggacacc gccctcctac    60
ggcggtaaca ggggttcgaa tcccctaggg gacgc                               95

SEQ ID NO: 103            moltype = DNA   length = 95
FEATURE                   Location/Qualifiers
misc_feature              1..95
                          note = DNA sequence DTL-5
source                    1..95
                          mol_type = other DNA
                          organism = synthetic construct
SEQUENCE: 103
ggcgtaatac gactcactat agtccccttc gtctagaggc ccaggacacc gccctcaaac    60
ggcggtaaca ggggttcgaa tcccctaggg gacgc                               95

SEQ ID NO: 104            moltype = DNA   length = 95
FEATURE                   Location/Qualifiers
misc_feature              1..95
                          note = DNA sequence DTL-6
source                    1..95
                          mol_type = other DNA
                          organism = synthetic construct
SEQUENCE: 104
ggcgtaatac gactcactat agtccccttc gtctagaggc ccaggacacc gcccttagac    60
ggcggtaaca ggggttcgaa tcccctaggg gacgc                               95

SEQ ID NO: 105            moltype = DNA   length = 95
FEATURE                   Location/Qualifiers
misc_feature              1..95
                          note = DNA sequence DTL-7
source                    1..95
                          mol_type = other DNA
                          organism = synthetic construct
SEQUENCE: 105
ggcgtaatac gactcactat agtccccttc gtctagaggc ccaggacacc gccctctaac    60
ggcggtaaca ggggttcgaa tcccctaggg gacgc                               95

SEQ ID NO: 106            moltype = DNA   length = 95
FEATURE                   Location/Qualifiers
misc_feature              1..95
                          note = DNA sequence DTL-8
source                    1..95
                          mol_type = other DNA
```

-continued

```
                        organism = synthetic construct
SEQUENCE: 106
ggcgtaatac gactcactat agtccccttc gtctagaggc ccaggacacc gccctccgac    60
ggcggtaaca ggggttcgaa tcccctaggg gacgc                              95

SEQ ID NO: 107          moltype = DNA   length = 95
FEATURE                 Location/Qualifiers
misc_feature            1..95
                        note = DNA sequence DTL-9
source                  1..95
                        mol_type = other DNA
                        organism = synthetic construct
SEQUENCE: 107
ggcgtaatac gactcactat agtccccttc gtctagaggc ccaggacacc gccctaagac    60
ggcggtaaca ggggttcgaa tcccctaggg gacgc                              95

SEQ ID NO: 108          moltype = DNA   length = 95
FEATURE                 Location/Qualifiers
misc_feature            1..95
                        note = DNA sequence DTL-10
source                  1..95
                        mol_type = other DNA
                        organism = synthetic construct
SEQUENCE: 108
ggcgtaatac gactcactat agtccccttc gtctagaggc ccaggacacc gccctgcaac    60
ggcggtaaca ggggttcgaa tcccctaggg gacgc                              95

SEQ ID NO: 109          moltype = DNA   length = 95
FEATURE                 Location/Qualifiers
misc_feature            1..95
                        note = DNA sequence DTL-11
source                  1..95
                        mol_type = other DNA
                        organism = synthetic construct
SEQUENCE: 109
ggcgtaatac gactcactat agtccccttc gtctagaggc ccaggacacc gccctcatac    60
ggcggtaaca ggggttcgaa tcccctaggg gacgc                              95

SEQ ID NO: 110          moltype = DNA   length = 95
FEATURE                 Location/Qualifiers
misc_feature            1..95
                        note = DNA sequence DTL-12
source                  1..95
                        mol_type = other DNA
                        organism = synthetic construct
SEQUENCE: 110
ggcgtaatac gactcactat aggctctgta gttcagtcgg tagaacggcg gactgttaat    60
ccgtatgtca ctggttcgag tccagtcaga gccgc                              95

SEQ ID NO: 111          moltype = DNA   length = 97
FEATURE                 Location/Qualifiers
misc_feature            1..97
                        note = DNA sequence DTL-13
source                  1..97
                        mol_type = other DNA
                        organism = synthetic construct
SEQUENCE: 111
ggcgtaatac gactcactat aggggctata gctcagctgg gagagcgcct gcttagcacg    60
caggaggtct gcggttcgat cccgcatagc tccacca                            97

SEQ ID NO: 112          moltype = DNA   length = 106
FEATURE                 Location/Qualifiers
misc_feature            1..106
                        note = DNA sequence DTL-14
source                  1..106
                        mol_type = other DNA
                        organism = synthetic construct
SEQUENCE: 112
ggcgtaatac gactcactat aggtggggtt cccgagcggc caaagggagc agactgtaaa    60
tctgccgtca tcgacttcga aggttcgaat ccttccccca ccacca                 106

SEQ ID NO: 113          moltype = RNA   length = 74
FEATURE                 Location/Qualifiers
misc_feature            1..74
                        note = RNA sequence MTL-1
source                  1..74
                        mol_type = other RNA
                        organism = synthetic construct
SEQUENCE: 113
```

```
gtccccttcg tctagaggcc caggacaccg ccctctgacg gcggtaacag gggttcgaat    60
cccctagggg acgc                                                      74

SEQ ID NO: 114         moltype = RNA   length = 74
FEATURE                Location/Qualifiers
misc_feature           1..74
                       note = RNA sequence MTL-2
source                 1..74
                       mol_type = other RNA
                       organism = synthetic construct
SEQUENCE: 114
gtccccttcg tctagaggcc caggacaccg ccctacgacg gcggtaacag gggttcgaat    60
cccctagggg acgc                                                      74

SEQ ID NO: 115         moltype = RNA   length = 74
FEATURE                Location/Qualifiers
misc_feature           1..74
                       note = RNA sequence MTL-3
source                 1..74
                       mol_type = other RNA
                       organism = synthetic construct
SEQUENCE: 115
gtccccttcg tctagaggcc caggacaccg ccctttcacg gcggtaacag gggttcgaat    60
cccctagggg acgc                                                      74

SEQ ID NO: 116         moltype = RNA   length = 74
FEATURE                Location/Qualifiers
misc_feature           1..74
                       note = RNA sequence MTL-4
source                 1..74
                       mol_type = other RNA
                       organism = synthetic construct
SEQUENCE: 116
gtccccttcg tctagaggcc caggacaccg ccctcctacg gcggtaacag gggttcgaat    60
cccctagggg acgc                                                      74

SEQ ID NO: 117         moltype = RNA   length = 74
FEATURE                Location/Qualifiers
misc_feature           1..74
                       note = RNA sequence MTL-5
source                 1..74
                       mol_type = other RNA
                       organism = synthetic construct
SEQUENCE: 117
gtccccttcg tctagaggcc caggacaccg ccctcaaacg gcggtaacag gggttcgaat    60
cccctagggg acgc                                                      74

SEQ ID NO: 118         moltype = RNA   length = 74
FEATURE                Location/Qualifiers
misc_feature           1..74
                       note = RNA sequence MTL-6
source                 1..74
                       mol_type = other RNA
                       organism = synthetic construct
SEQUENCE: 118
gtccccttcg tctagaggcc caggacaccg ccctttagacg gcggtaacag gggttcgaat   60
cccctagggg acgc                                                      74

SEQ ID NO: 119         moltype = RNA   length = 74
FEATURE                Location/Qualifiers
misc_feature           1..74
                       note = RNA sequence MTL-7
source                 1..74
                       mol_type = other RNA
                       organism = synthetic construct
SEQUENCE: 119
gtccccttcg tctagaggcc caggacaccg ccctctaacg gcggtaacag gggttcgaat    60
cccctagggg acgc                                                      74

SEQ ID NO: 120         moltype = RNA   length = 74
FEATURE                Location/Qualifiers
misc_feature           1..74
                       note = RNA sequence MTL-8
source                 1..74
                       mol_type = other RNA
                       organism = synthetic construct
SEQUENCE: 120
gtccccttcg tctagaggcc caggacaccg ccctccgacg gcggtaacag gggttcgaat    60
cccctagggg acgc                                                      74
```

-continued

```
SEQ ID NO: 121          moltype = RNA   length = 74
FEATURE                 Location/Qualifiers
misc_feature            1..74
                        note = RNA sequence MTL-9
source                  1..74
                        mol_type = other RNA
                        organism = synthetic construct
SEQUENCE: 121
gtccccttcg tctagaggcc caggacaccg ccctaagacg gcggtaacag gggttcgaat   60
cccctagggg acgc                                                    74

SEQ ID NO: 122          moltype = RNA   length = 74
FEATURE                 Location/Qualifiers
misc_feature            1..74
                        note = RNA sequence MTL-10
source                  1..74
                        mol_type = other RNA
                        organism = synthetic construct
SEQUENCE: 122
gtccccttcg tctagaggcc caggacaccg ccctgcaacg gcggtaacag gggttcgaat   60
cccctagggg acgc                                                    74

SEQ ID NO: 123          moltype = RNA   length = 74
FEATURE                 Location/Qualifiers
misc_feature            1..74
                        note = RNA sequence MTL-11
source                  1..74
                        mol_type = other RNA
                        organism = synthetic construct
SEQUENCE: 123
gtccccttcg tctagaggcc caggacaccg ccctcatacg gcggtaacag gggttcgaat   60
cccctagggg acgc                                                    74

SEQ ID NO: 124          moltype = RNA   length = 74
FEATURE                 Location/Qualifiers
misc_feature            1..74
                        note = RNA sequence MTL-12
source                  1..74
                        mol_type = other RNA
                        organism = synthetic construct
SEQUENCE: 124
ggctctgtag ttcagtcggt agaacggcgg actgttaatc cgtatgtcac tggttcgagt   60
ccagtcagag ccgc                                                    74

SEQ ID NO: 125          moltype = RNA   length = 76
FEATURE                 Location/Qualifiers
misc_feature            1..76
                        note = RNA sequence MTL-13
source                  1..76
                        mol_type = other RNA
                        organism = synthetic construct
SEQUENCE: 125
ggggctatag ctcagctggg agagcgcctg cttagcacgc aggaggtctg cggttcgatc   60
ccgcatagct ccacca                                                  76

SEQ ID NO: 126          moltype = RNA   length = 85
FEATURE                 Location/Qualifiers
misc_feature            1..85
                        note = RNA sequence MTL-14
source                  1..85
                        mol_type = other RNA
                        organism = synthetic construct
SEQUENCE: 126
ggtgggttc ccgagcggcc aaagggagca gactgtaaat ctgccgtcat cgacttcgaa    60
ggttcgaatc cttcccccac cacca                                        85

SEQ ID NO: 127          moltype = RNA   length = 76
FEATURE                 Location/Qualifiers
misc_feature            1..76
                        note = tRNAGluCUG
source                  1..76
                        mol_type = other RNA
                        organism = synthetic construct
SEQUENCE: 127
gtccccttcg tctagaggcc caggacaccg ccctctgacg gcggtaacag gggttcgaat   60
cccctagggg acgcca                                                  76

SEQ ID NO: 128          moltype = RNA   length = 76
```

```
                        FEATURE              Location/Qualifiers
                        misc_feature         1..76
                                             note = tRNAGluACG
                        source               1..76
                                             mol_type = other RNA
                                             organism = synthetic construct
SEQUENCE: 128
gtccccttcg tctagaggcc caggacaccg ccctacgacg gcggtaacag gggttcgaat    60
cccctagggg acgcca                                                    76

SEQ ID NO: 129          moltype = RNA   length = 76
FEATURE                 Location/Qualifiers
misc_feature            1..76
                        note = tRNAGluUUC
source                  1..76
                        mol_type = other RNA
                        organism = synthetic construct
SEQUENCE: 129
gtccccttcg tctagaggcc caggacaccg ccctttcacg gcggtaacag gggttcgaat    60
cccctagggg acgcca                                                    76

SEQ ID NO: 130          moltype = RNA   length = 76
FEATURE                 Location/Qualifiers
misc_feature            1..76
                        note = tRNAGluCCU
source                  1..76
                        mol_type = other RNA
                        organism = synthetic construct
SEQUENCE: 130
gtccccttcg tctagaggcc caggacaccg ccctcctacg gcggtaacag gggttcgaat    60
cccctagggg acgcca                                                    76

SEQ ID NO: 131          moltype = RNA   length = 76
FEATURE                 Location/Qualifiers
misc_feature            1..76
                        note = tRNAGluCAA
source                  1..76
                        mol_type = other RNA
                        organism = synthetic construct
SEQUENCE: 131
gtccccttcg tctagaggcc caggacaccg ccctcaaacg gcggtaacag gggttcgaat    60
cccctagggg acgcca                                                    76

SEQ ID NO: 132          moltype = RNA   length = 76
FEATURE                 Location/Qualifiers
misc_feature            1..76
                        note = tRNAGluUAG
source                  1..76
                        mol_type = other RNA
                        organism = synthetic construct
SEQUENCE: 132
gtccccttcg tctagaggcc caggacaccg cccttagacg gcggtaacag gggttcgaat    60
cccctagggg acgcca                                                    76

SEQ ID NO: 133          moltype = RNA   length = 76
FEATURE                 Location/Qualifiers
misc_feature            1..76
                        note = tRNAGluCUA
source                  1..76
                        mol_type = other RNA
                        organism = synthetic construct
SEQUENCE: 133
gtccccttcg tctagaggcc caggacaccg ccctctaacg gcggtaacag gggttcgaat    60
cccctagggg acgcca                                                    76

SEQ ID NO: 134          moltype = RNA   length = 76
FEATURE                 Location/Qualifiers
misc_feature            1..76
                        note = tRNAGluCCG
source                  1..76
                        mol_type = other RNA
                        organism = synthetic construct
SEQUENCE: 134
gtccccttcg tctagaggcc caggacaccg ccctccgacg gcggtaacag gggttcgaat    60
cccctagggg acgcca                                                    76

SEQ ID NO: 135          moltype = RNA   length = 76
FEATURE                 Location/Qualifiers
misc_feature            1..76
```

```
                        note = tRNAGluAAG
source                  1..76
                        mol_type = other RNA
                        organism = synthetic construct
SEQUENCE: 135
gtcccttcg tctagaggcc caggacaccg ccctaagacg gcggtaacag gggttcgaat    60
ccctaggggg acgcca                                                   76

SEQ ID NO: 136          moltype = RNA  length = 76
FEATURE                 Location/Qualifiers
misc_feature            1..76
                        note = tRNAGluGCA
source                  1..76
                        mol_type = other RNA
                        organism = synthetic construct
SEQUENCE: 136
gtcccttcg tctagaggcc caggacaccg ccctgcaacg gcggtaacag gggttcgaat    60
ccctaggggg acgcca                                                   76

SEQ ID NO: 137          moltype = RNA  length = 76
FEATURE                 Location/Qualifiers
misc_feature            1..76
                        note = tRNAGluCAU
source                  1..76
                        mol_type = other RNA
                        organism = synthetic construct
SEQUENCE: 137
gtcccttcg tctagaggcc caggacaccg ccctcatacg gcggtaacag gggttcgaat    60
ccctaggggg acgcca                                                   76

SEQ ID NO: 138          moltype = RNA  length = 76
FEATURE                 Location/Qualifiers
misc_feature            1..76
                        note = tRNAAsn-E2GUU
source                  1..76
                        mol_type = other RNA
                        organism = synthetic construct
SEQUENCE: 138
ggctctgtag ttcagtcggt agaacggcgg actgttaatc cgtatgtcac tggttcgagt    60
ccagtcagag ccgcca                                                   76

SEQ ID NO: 139          moltype = RNA  length = 77
FEATURE                 Location/Qualifiers
misc_feature            1..77
                        note = tRNAfMetCAU
source                  1..77
                        mol_type = other RNA
                        organism = synthetic construct
SEQUENCE: 139
ggcggggtgg agcagcctgg tagctcgtcg ggctcataac ccgaagatcg tcggttcaaa    60
tccggccccc gcaacca                                                  77

SEQ ID NO: 140          moltype = DNA  length = 69
FEATURE                 Location/Qualifiers
misc_feature            1..69
                        note = An artificially synthesized nucleotide sequence
misc_feature            19..21
                        note = nnn stands for ttt, att, gtt, agt, ccg, act, gct,
                        cat, tgg, ggt, tac, cag, aac, cgg, agg, ttg, ctt, cta,
                        tag, tgc or gaa
misc_feature            22..24
                        note = nnn stands for ttt, att, gtt, agt, ccg, act, gct,
                        cat, tgg, ggt, tac, cag, aac, cgg, agg, ttg, ctt, cta,
                        tag, tgc or gaa
misc_feature            25..27
                        note = nnn stands for ttt, att, gtt, agt, ccg, act, gct,
                        cat, tgg, ggt, tac, cag, aac, cgg, agg, ttg, ctt, cta,
                        tag, tgc or gaa
misc_feature            28..30
                        note = nnn stands for ttt, att, gtt, agt, ccg, act, gct,
                        cat, tgg, ggt, tac, cag, aac, cgg, agg, ttg, ctt, cta,
                        tag, tgc or gaa
misc_feature            31..33
                        note = nnn stands for ttt, att, gtt, agt, ccg, act, gct,
                        cat, tgg, ggt, tac, cag, aac, cgg, agg, ttg, ctt, cta,
                        tag, tgc or gaa
misc_feature            34..36
                        note = nnn stands for ttt, att, gtt, agt, ccg, act, gct,
                        cat, tgg, ggt, tac, cag, aac, cgg, agg, ttg, ctt, cta,
```

```
misc_feature          37..39
                      note = nnn stands for ttt, att, gtt, agt, ccg, act, gct,
                         cat, tgg, ggt, tac, cag, aac, cgg, agg, ttg, ctt, cta,
                         tag, tgc or gaa
misc_feature          43..45
                      note = nnn stands for ttt, ccg, gct, cat, aac, cgg, agg,
                         ttg, tag or gaa
misc_feature          46..48
                      note = nnn stands for ttt, att, gtt, agt, ccg, act, gct,
                         cat, tgg, ggt, tac, cag, aac, cgg, agg, ttg, ctt, cta,
                         tag, tgc or gaa
source                1..69
                      mol_type = other DNA
                      organism = synthetic construct
SEQUENCE: 140
gaaggagata tacatatgnn nnnnnnnnnn nnnnnnnnnc gtnnnnnnag cggctctggc    60
tctggctct                                                            69

SEQ ID NO: 141        moltype = DNA  length = 72
FEATURE               Location/Qualifiers
misc_feature          1..72
                      note = An artificially synthesized nucleotide sequence
misc_feature          19..21
                      note = nnn stands for ttt, att, gtt, agt, ccg, act, gct,
                         cat, tgg, ggt, tac, cag, aac, cgg, agg, ttg, ctt, cta,
                         tag, tgc or gaa
misc_feature          22..24
                      note = nnn stands for ttt, att, gtt, agt, ccg, act, gct,
                         cat, tgg, ggt, tac, cag, aac, cgg, agg, ttg, ctt, cta,
                         tag, tgc or gaa
misc_feature          25..27
                      note = nnn stands for ttt, att, gtt, agt, ccg, act, gct,
                         cat, tgg, ggt, tac, cag, aac, cgg, agg, ttg, ctt, cta,
                         tag, tgc or gaa
misc_feature          28..30
                      note = nnn stands for ttt, att, gtt, agt, ccg, act, gct,
                         cat, tgg, ggt, tac, cag, aac, cgg, agg, ttg, ctt, cta,
                         tag, tgc or gaa
misc_feature          31..33
                      note = nnn stands for ttt, att, gtt, agt, ccg, act, gct,
                         cat, tgg, ggt, tac, cag, aac, cgg, agg, ttg, ctt, cta,
                         tag, tgc or gaa
misc_feature          34..36
                      note = nnn stands for ttt, att, gtt, agt, ccg, act, gct,
                         cat, tgg, ggt, tac, cag, aac, cgg, agg, ttg, ctt, cta,
                         tag, tgc or gaa
misc_feature          37..39
                      note = nnn stands for ttt, att, gtt, agt, ccg, act, gct,
                         cat, tgg, ggt, tac, cag, aac, cgg, agg, ttg, ctt, cta,
                         tag, tgc or gaa
misc_feature          40..42
                      note = nnn stands for ttt, att, gtt, agt, ccg, act, gct,
                         cat, tgg, ggt, tac, cag, aac, cgg, agg, ttg, ctt, cta,
                         tag, tgc or gaa
misc_feature          46..48
                      note = nnn stands for ttt, ccg, gct, cat, aac, cgg, agg,
                         ttg, tag or gaa
misc_feature          49..51
                      note = nnn stands for ttt, att, gtt, agt, ccg, act, gct,
                         cat, tgg, ggt, tac, cag, aac, cgg, agg, ttg, ctt, cta,
                         tag, tgc or gaa
source                1..72
                      mol_type = other DNA
                      organism = synthetic construct
SEQUENCE: 141
gaaggagata tacatatgnn nnnnnnnnnn nnnnnnnnn nncgtnnnnn nagcggctct    60
ggctctggct ct                                                        72

SEQ ID NO: 142        moltype = DNA  length = 75
FEATURE               Location/Qualifiers
misc_feature          1..75
                      note = An artificially synthesized nucleotide sequence
misc_feature          19..21
                      note = nnn stands for ttt, att, gtt, agt, ccg, act, gct,
                         cat, tgg, ggt, tac, cag, aac, cgg, agg, ttg, ctt, cta,
                         tag, tgc or gaa
misc_feature          22..24
                      note = nnn stands for ttt, att, gtt, agt, ccg, act, gct,
```

-continued

|||
|---|---|
| | cat, tgg, ggt, tac, cag, aac, cgg, agg, ttg, ctt, cta, tag, tgc or gaa |
| misc_feature | 25..27 |
| | note = nnn stands for ttt, att, gtt, agt, ccg, act, gct, cat, tgg, ggt, tac, cag, aac, cgg, agg, ttg, ctt, cta, tag, tgc or gaa |
| misc_feature | 28..30 |
| | note = nnn stands for ttt, att, gtt, agt, ccg, act, gct, cat, tgg, ggt, tac, cag, aac, cgg, agg, ttg, ctt, cta, tag, tgc or gaa |
| misc_feature | 31..33 |
| | note = nnn stands for ttt, att, gtt, agt, ccg, act, gct, cat, tgg, ggt, tac, cag, aac, cgg, agg, ttg, ctt, cta, tag, tgc or gaa |
| misc_feature | 34..36 |
| | note = nnn stands for ttt, att, gtt, agt, ccg, act, gct, cat, tgg, ggt, tac, cag, aac, cgg, agg, ttg, ctt, cta, tag, tgc or gaa |
| misc_feature | 37..39 |
| | note = nnn stands for ttt, att, gtt, agt, ccg, act, gct, cat, tgg, ggt, tac, cag, aac, cgg, agg, ttg, ctt, cta, tag, tgc or gaa |
| misc_feature | 40..42 |
| | note = nnn stands for ttt, att, gtt, agt, ccg, act, gct, cat, tgg, ggt, tac, cag, aac, cgg, agg, ttg, ctt, cta, tag, tgc or gaa |
| misc_feature | 43..45 |
| | note = nnn stands for ttt, att, gtt, agt, ccg, act, gct, cat, tgg, ggt, tac, cag, aac, cgg, agg, ttg, ctt, cta, tag, tgc or gaa |
| misc_feature | 49..51 |
| | note = nnn stands for ttt, ccg, gct, cat, aac, cgg, agg, ttg, tag or gaa |
| misc_feature | 52..54 |
| | note = nnn stands for ttt, att, gtt, agt, ccg, act, gct, cat, tgg, ggt, tac, cag, aac, cgg, agg, ttg, ctt, cta, tag, tgc or gaa |
| source | 1..75 |
| | mol_type = other DNA |
| | organism = synthetic construct |

SEQUENCE: 142

```
gaaggagata tacatatgnn nnnnnnnnnn nnnnnnnnnn nnnncgtnn nnnnagcggc   60
tctggctctg gctct                                                  75
```

| SEQ ID NO: 143 | moltype = DNA  length = 72 |
|---|---|
| FEATURE | Location/Qualifiers |
| misc_feature | 1..72 |
| | note = An artificially synthesized nucleotide sequence |
| misc_feature | 22..24 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 25..27 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 28..30 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 31..33 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 34..36 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 37..39 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 40..42 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 46..48 |
| | note = nnn stands for ttt, att, atg, gtt, agt, ccg, act, gct, cat, tgg, ggt, tac, cag, aac, cgg, agg, ttg, ctt, |

```
                        cta, tag or gaa
misc_feature            49..51
                        note = nnn stands for ttt, att, atg, gtt, agt, ccg, act,
                        gct, cat, tgg, ggt, tac, cag, aac, cgg, agg, ttg, ctt,
                        cta, tag or gaa
source                  1..72
                        mol_type = other DNA
                        organism = synthetic construct
SEQUENCE: 143
gaaggagata tacatatgtg cnnnnnnnnn nnnnnnnnnn nncgtnnnnn nagcggctct      60
ggctctggct ct                                                         72

SEQ ID NO: 144          moltype = DNA  length = 75
FEATURE                 Location/Qualifiers
misc_feature            1..75
                        note = An artificially synthesized nucleotide sequence
misc_feature            22..24
                        note = nnn stands for ttt, att, atg, gtt, agt, ccg, act,
                        gct, cat, tgg, ggt, tac, cag, aac, cgg, agg, ttg, ctt,
                        cta, tag or gaa
misc_feature            25..27
                        note = nnn stands for ttt, att, atg, gtt, agt, ccg, act,
                        gct, cat, tgg, ggt, tac, cag, aac, cgg, agg, ttg, ctt,
                        cta, tag or gaa
misc_feature            28..30
                        note = nnn stands for ttt, att, atg, gtt, agt, ccg, act,
                        gct, cat, tgg, ggt, tac, cag, aac, cgg, agg, ttg, ctt,
                        cta, tag or gaa
misc_feature            31..33
                        note = nnn stands for ttt, att, atg, gtt, agt, ccg, act,
                        gct, cat, tgg, ggt, tac, cag, aac, cgg, agg, ttg, ctt,
                        cta, tag or gaa
misc_feature            34..36
                        note = nnn stands for ttt, att, atg, gtt, agt, ccg, act,
                        gct, cat, tgg, ggt, tac, cag, aac, cgg, agg, ttg, ctt,
                        cta, tag or gaa
misc_feature            37..39
                        note = nnn stands for ttt, att, atg, gtt, agt, ccg, act,
                        gct, cat, tgg, ggt, tac, cag, aac, cgg, agg, ttg, ctt,
                        cta, tag or gaa
misc_feature            40..42
                        note = nnn stands for ttt, att, atg, gtt, agt, ccg, act,
                        gct, cat, tgg, ggt, tac, cag, aac, cgg, agg, ttg, ctt,
                        cta, tag or gaa
misc_feature            43..45
                        note = nnn stands for ttt, att, atg, gtt, agt, ccg, act,
                        gct, cat, tgg, ggt, tac, cag, aac, cgg, agg, ttg, ctt,
                        cta, tag or gaa
misc_feature            49..51
                        note = nnn stands for ttt, att, atg, gtt, agt, ccg, act,
                        gct, cat, tgg, ggt, tac, cag, aac, cgg, agg, ttg, ctt,
                        cta, tag or gaa
misc_feature            52..54
                        note = nnn stands for ttt, att, atg, gtt, agt, ccg, act,
                        gct, cat, tgg, ggt, tac, cag, aac, cgg, agg, ttg, ctt,
                        cta, tag or gaa
source                  1..75
                        mol_type = other DNA
                        organism = synthetic construct
SEQUENCE: 144
gaaggagata tacatatgtg cnnnnnnnnn nnnnnnnnnn nnnncgtnn nnnnagcggc      60
tctggctctg gctct                                                      75

SEQ ID NO: 145          moltype = DNA  length = 78
FEATURE                 Location/Qualifiers
misc_feature            1..78
                        note = An artificially synthesized nucleotide sequence
misc_feature            22..24
                        note = nnn stands for ttt, att, atg, gtt, agt, ccg, act,
                        gct, cat, tgg, ggt, tac, cag, aac, cgg, agg, ttg, ctt,
                        cta, tag or gaa
misc_feature            25..27
                        note = nnn stands for ttt, att, atg, gtt, agt, ccg, act,
                        gct, cat, tgg, ggt, tac, cag, aac, cgg, agg, ttg, ctt,
                        cta, tag or gaa
misc_feature            28..30
                        note = nnn stands for ttt, att, atg, gtt, agt, ccg, act,
                        gct, cat, tgg, ggt, tac, cag, aac, cgg, agg, ttg, ctt,
                        cta, tag or gaa
```

| | |
|---|---|
| misc_feature | 31..33 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 34..36 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 37..39 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 40..42 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 43..45 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 46..48 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 52..54 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 55..57 |
| | note = nnn stands for ttt, att, atg, gtt, agt, ccg, act, gct, cat, tgg, ggt, tac, cag, aac, cgg, agg, ttg, ctt, cta, tag or gaa |
| source | 1..78 |
| | mol_type = other DNA |
| | organism = synthetic construct |

SEQUENCE: 145
```
gaaggagata tacatatgtg cnnnnnnnnn nnnnnnnnnn nnnnnnnncg tnnnnnnagc   60
ggctctggct ctggctct                                                 78
```

| | |
|---|---|
| SEQ ID NO: 146 | moltype = DNA   length = 39 |
| FEATURE | Location/Qualifiers |
| misc_feature | 1..39 |
| | note = DNA sequence DOL-1 |
| source | 1..39 |
| | mol_type = other DNA |
| | organism = synthetic construct |

SEQUENCE: 146
```
tttgtccccg ccgccctaag agccagagcc agagccgct                          39
```

| | |
|---|---|
| SEQ ID NO: 147 | moltype = DNA   length = 49 |
| FEATURE | Location/Qualifiers |
| misc_feature | 1..49 |
| | note = DNA sequence DOL-2 |
| source | 1..49 |
| | mol_type = other DNA |
| | organism = synthetic construct |

SEQUENCE: 147
```
gtaatacgac tcactatagg gttaacttta agaaggagat atacatatg              49
```

| | |
|---|---|
| SEQ ID NO: 148 | moltype = DNA   length = 118 |
| FEATURE | Location/Qualifiers |
| misc_feature | 1..118 |
| | note = DNA sequence DML-1 |
| misc_feature | 50..52 |
| | note = nnn stands for ttt, att, gtt, agt, ccg, act, gct, cat, tgg, ggt, tac, cag, aac, cgg, agg, ttg, ctt, cta, tag, tgc or gaa |
| misc_feature | 53..55 |
| | note = nnn stands for ttt, att, gtt, agt, ccg, act, gct, cat, tgg, ggt, tac, cag, aac, cgg, agg, ttg, ctt, cta, tag, tgc or gaa |
| misc_feature | 56..58 |
| | note = nnn stands for ttt, att, gtt, agt, ccg, act, gct, cat, tgg, ggt, tac, cag, aac, cgg, agg, ttg, ctt, cta, tag, tgc or gaa |
| misc_feature | 59..61 |
| | note = nnn stands for ttt, att, gtt, agt, ccg, act, gct, cat, tgg, ggt, tac, cag, aac, cgg, agg, ttg, ctt, cta, tag, tgc or gaa |

```
misc_feature      62..64
                  note = nnn stands for ttt, att, gtt, agt, ccg, act, gct,
                    cat, tgg, ggt, tac, cag, aac, cgg, agg, ttg, ctt, cta,
                    tag, tgc or gaa
misc_feature      65..67
                  note = nnn stands for ttt, att, gtt, agt, ccg, act, gct,
                    cat, tgg, ggt, tac, cag, aac, cgg, agg, ttg, ctt, cta,
                    tag, tgc or gaa
misc_feature      68..70
                  note = nnn stands for ttt, att, gtt, agt, ccg, act, gct,
                    cat, tgg, ggt, tac, cag, aac, cgg, agg, ttg, ctt, cta,
                    tag, tgc or gaa
misc_feature      74..76
                  note = nnn stands for ttt, ccg, gct, cat, aac, cgg, agg,
                    ttg, tag or gaa
misc_feature      77..79
                  note = nnn stands for ttt, att, gtt, agt, ccg, act, gct,
                    cat, tgg, ggt, tac, cag, aac, cgg, agg, ttg, ctt, cta,
                    tag, tgc or gaa
source            1..118
                  mol_type = other DNA
                  organism = synthetic construct
SEQUENCE: 148
gtaatacgac tcactatagg gttaacttta agaaggagat atacatatgn nnnnnnnnn     60
nnnnnnnnnn cgtnnnnnna gcggctctgg ctctggctct tagggcggcg gggacaaa     118

SEQ ID NO: 149    moltype = DNA  length = 121
FEATURE           Location/Qualifiers
misc_feature      1..121
                  note = DNA sequence DML-2
misc_feature      50..52
                  note = nnn stands for ttt, att, gtt, agt, ccg, act, gct,
                    cat, tgg, ggt, tac, cag, aac, cgg, agg, ttg, ctt, cta,
                    tag, tgc or gaa
misc_feature      53..55
                  note = nnn stands for ttt, att, gtt, agt, ccg, act, gct,
                    cat, tgg, ggt, tac, cag, aac, cgg, agg, ttg, ctt, cta,
                    tag, tgc or gaa
misc_feature      56..58
                  note = nnn stands for ttt, att, gtt, agt, ccg, act, gct,
                    cat, tgg, ggt, tac, cag, aac, cgg, agg, ttg, ctt, cta,
                    tag, tgc or gaa
misc_feature      59..61
                  note = nnn stands for ttt, att, gtt, agt, ccg, act, gct,
                    cat, tgg, ggt, tac, cag, aac, cgg, agg, ttg, ctt, cta,
                    tag, tgc or gaa
misc_feature      62..64
                  note = nnn stands for ttt, att, gtt, agt, ccg, act, gct,
                    cat, tgg, ggt, tac, cag, aac, cgg, agg, ttg, ctt, cta,
                    tag, tgc or gaa
misc_feature      65..67
                  note = nnn stands for ttt, att, gtt, agt, ccg, act, gct,
                    cat, tgg, ggt, tac, cag, aac, cgg, agg, ttg, ctt, cta,
                    tag, tgc or gaa
misc_feature      68..70
                  note = nnn stands for ttt, att, gtt, agt, ccg, act, gct,
                    cat, tgg, ggt, tac, cag, aac, cgg, agg, ttg, ctt, cta,
                    tag, tgc or gaa
misc_feature      71..73
                  note = nnn stands for ttt, att, gtt, agt, ccg, act, gct,
                    cat, tgg, ggt, tac, cag, aac, cgg, agg, ttg, ctt, cta,
                    tag, tgc or gaa
misc_feature      77..79
                  note = nnn stands for ttt, ccg, gct, cat, aac, cgg, agg,
                    ttg, tag or gaa
misc_feature      80..82
                  note = nnn stands for ttt, att, gtt, agt, ccg, act, gct,
                    cat, tgg, ggt, tac, cag, aac, cgg, agg, ttg, ctt, cta,
                    tag, tgc or gaa
source            1..121
                  mol_type = other DNA
                  organism = synthetic construct
SEQUENCE: 149
gtaatacgac tcactatagg gttaacttta agaaggagat atacatatgn nnnnnnnnn     60
nnnnnnnnnn nnncgtnnnn nnagcggctc tggctctggc tcttagggcg gcgggacaa    120
a                                                                   121

SEQ ID NO: 150    moltype = DNA  length = 124
FEATURE           Location/Qualifiers
```

| | |
|---|---|
| misc_feature | 1..124<br>note = DNA sequence DML-3 |
| misc_feature | 50..52<br>note = nnn stands for ttt, att, gtt, agt, ccg, act, gct, cat, tgg, ggt, tac, cag, aac, cgg, agg, ttg, ctt, cta, tag, tgc or gaa |
| misc_feature | 53..55<br>note = nnn stands for ttt, att, gtt, agt, ccg, act, gct, cat, tgg, ggt, tac, cag, aac, cgg, agg, ttg, ctt, cta, tag, tgc or gaa |
| misc_feature | 56..58<br>note = nnn stands for ttt, att, gtt, agt, ccg, act, gct, cat, tgg, ggt, tac, cag, aac, cgg, agg, ttg, ctt, cta, tag, tgc or gaa |
| misc_feature | 59..61<br>note = nnn stands for ttt, att, gtt, agt, ccg, act, gct, cat, tgg, ggt, tac, cag, aac, cgg, agg, ttg, ctt, cta, tag, tgc or gaa |
| misc_feature | 62..64<br>note = nnn stands for ttt, att, gtt, agt, ccg, act, gct, cat, tgg, ggt, tac, cag, aac, cgg, agg, ttg, ctt, cta, tag, tgc or gaa |
| misc_feature | 65..67<br>note = nnn stands for ttt, att, gtt, agt, ccg, act, gct, cat, tgg, ggt, tac, cag, aac, cgg, agg, ttg, ctt, cta, tag, tgc or gaa |
| misc_feature | 68..70<br>note = nnn stands for ttt, att, gtt, agt, ccg, act, gct, cat, tgg, ggt, tac, cag, aac, cgg, agg, ttg, ctt, cta, tag, tgc or gaa |
| misc_feature | 71..73<br>note = nnn stands for ttt, att, gtt, agt, ccg, act, gct, cat, tgg, ggt, tac, cag, aac, cgg, agg, ttg, ctt, cta, tag, tgc or gaa |
| misc_feature | 74..76<br>note = nnn stands for ttt, att, gtt, agt, ccg, act, gct, cat, tgg, ggt, tac, cag, aac, cgg, agg, ttg, ctt, cta, tag, tgc or gaa |
| misc_feature | 80..82<br>note = nnn stands for ttt, ccg, gct, cat, aac, cgg, agg, ttg, tag or gaa |
| misc_feature | 83..85<br>note = nnn stands for ttt, att, gtt, agt, ccg, act, gct, cat, tgg, ggt, tac, cag, aac, cgg, agg, ttg, ctt, cta, tag, tgc or gaa |
| source | 1..124<br>mol_type = other DNA<br>organism = synthetic construct |

SEQUENCE: 150

```
gtaatacgac tcactatagg gttaacttta agaaggagat atacatatgn nnnnnnnnn    60
nnnnnnnnnn nnnnncgtn nnnnagcgg ctctggctct ggctcttagg gcggcgggga   120
caaa                                                              124
```

| | |
|---|---|
| SEQ ID NO: 151<br>FEATURE | moltype = DNA  length = 121<br>Location/Qualifiers |
| misc_feature | 1..121<br>note = DNA sequence DML-4 |
| misc_feature | 53..55<br>note = nnn stands for ttt, att, atg, gtt, agt, ccg, act, gct, cat, tgg, ggt, tac, cag, aac, cgg, agg, ttg, ctt, cta, tag or gaa |
| misc_feature | 56..58<br>note = nnn stands for ttt, att, atg, gtt, agt, ccg, act, gct, cat, tgg, ggt, tac, cag, aac, cgg, agg, ttg, ctt, cta, tag or gaa |
| misc_feature | 59..61<br>note = nnn stands for ttt, att, atg, gtt, agt, ccg, act, gct, cat, tgg, ggt, tac, cag, aac, cgg, agg, ttg, ctt, cta, tag or gaa |
| misc_feature | 62..64<br>note = nnn stands for ttt, att, atg, gtt, agt, ccg, act, gct, cat, tgg, ggt, tac, cag, aac, cgg, agg, ttg, ctt, cta, tag or gaa |
| misc_feature | 65..67<br>note = nnn stands for ttt, att, atg, gtt, agt, ccg, act, gct, cat, tgg, ggt, tac, cag, aac, cgg, agg, ttg, ctt, cta, tag or gaa |
| misc_feature | 68..70<br>note = nnn stands for ttt, att, atg, gtt, agt, ccg, act, |

```
                            gct, cat, tgg, ggt, tac, cag, aac, cgg, agg, ttg, ctt,
                            cta, tag or gaa
misc_feature                71..73
                            note = nnn stands for ttt, att, atg, gtt, agt, ccg, act,
                            gct, cat, tgg, ggt, tac, cag, aac, cgg, agg, ttg, ctt,
                            cta, tag or gaa
misc_feature                77..79
                            note = nnn stands for ttt, att, atg, gtt, agt, ccg, act,
                            gct, cat, tgg, ggt, tac, cag, aac, cgg, agg, ttg, ctt,
                            cta, tag or gaa
misc_feature                80..82
                            note = nnn stands for ttt, att, atg, gtt, agt, ccg, act,
                            gct, cat, tgg, ggt, tac, cag, aac, cgg, agg, ttg, ctt,
                            cta, tag or gaa
source                      1..121
                            mol_type = other DNA
                            organism = synthetic construct
SEQUENCE: 151
gtaatacgac tcactatagg gttaacttta agaaggagat atacatatgt gcnnnnnnnn    60
nnnnnnnnnn nnncgtnnnn nnagcggctc tggctctggc tcttagggcg gcggggacaa   120
a                                                                   121

SEQ ID NO: 152              moltype = DNA  length = 124
FEATURE                     Location/Qualifiers
misc_feature                1..124
                            note = DNA sequence DML-5
misc_feature                53..55
                            note = nnn stands for ttt, att, atg, gtt, agt, ccg, act,
                            gct, cat, tgg, ggt, tac, cag, aac, cgg, agg, ttg, ctt,
                            cta, tag or gaa
misc_feature                56..58
                            note = nnn stands for ttt, att, atg, gtt, agt, ccg, act,
                            gct, cat, tgg, ggt, tac, cag, aac, cgg, agg, ttg, ctt,
                            cta, tag or gaa
misc_feature                59..61
                            note = nnn stands for ttt, att, atg, gtt, agt, ccg, act,
                            gct, cat, tgg, ggt, tac, cag, aac, cgg, agg, ttg, ctt,
                            cta, tag or gaa
misc_feature                62..64
                            note = nnn stands for ttt, att, atg, gtt, agt, ccg, act,
                            gct, cat, tgg, ggt, tac, cag, aac, cgg, agg, ttg, ctt,
                            cta, tag or gaa
misc_feature                65..67
                            note = nnn stands for ttt, att, atg, gtt, agt, ccg, act,
                            gct, cat, tgg, ggt, tac, cag, aac, cgg, agg, ttg, ctt,
                            cta, tag or gaa
misc_feature                68..70
                            note = nnn stands for ttt, att, atg, gtt, agt, ccg, act,
                            gct, cat, tgg, ggt, tac, cag, aac, cgg, agg, ttg, ctt,
                            cta, tag or gaa
misc_feature                71..73
                            note = nnn stands for ttt, att, atg, gtt, agt, ccg, act,
                            gct, cat, tgg, ggt, tac, cag, aac, cgg, agg, ttg, ctt,
                            cta, tag or gaa
misc_feature                74..76
                            note = nnn stands for ttt, att, atg, gtt, agt, ccg, act,
                            gct, cat, tgg, ggt, tac, cag, aac, cgg, agg, ttg, ctt,
                            cta, tag or gaa
misc_feature                80..82
                            note = nnn stands for ttt, att, atg, gtt, agt, ccg, act,
                            gct, cat, tgg, ggt, tac, cag, aac, cgg, agg, ttg, ctt,
                            cta, tag or gaa
misc_feature                83..85
                            note = nnn stands for ttt, att, atg, gtt, agt, ccg, act,
                            gct, cat, tgg, ggt, tac, cag, aac, cgg, agg, ttg, ctt,
                            cta, tag or gaa
source                      1..124
                            mol_type = other DNA
                            organism = synthetic construct
SEQUENCE: 152
gtaatacgac tcactatagg gttaacttta agaaggagat atacatatgt gcnnnnnnnn    60
nnnnnnnnnn nnnnncgtn nnnnagcgg ctctggctct ggctcttagg gcggcggga     120
caaa                                                                124

SEQ ID NO: 153              moltype = DNA  length = 127
FEATURE                     Location/Qualifiers
misc_feature                1..127
                            note = DNA sequence DML-6
misc_feature                53..55
```

|  |  |
|---|---|
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 56..58 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 59..61 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 62..64 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 65..67 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 68..70 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 71..73 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 74..76 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 77..79 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 83..85 |
| | note = nnn stands for ttt, att, atg, gtt, agt, ccg, act, gct, cat, tgg, ggt, tac, cag, aac, cgg, agg, ttg, ctt, cta, tag or gaa |
| misc_feature | 86..88 |
| | note = nnn stands for ttt, att, atg, gtt, agt, ccg, act, gct, cat, tgg, ggt, tac, cag, aac, cgg, agg, ttg, ctt, cta, tag or gaa |
| source | 1..127 |
| | mol_type = other DNA |
| | organism = synthetic construct |

SEQUENCE: 153
```
gtaatacgac tcactatagg gttaacttta agaaggagat atacatatgt gcnnnnnnnn   60
nnnnnnnnnn nnnnnnnnnc gtnnnnnnag cggctctggc tctggctctt agggcggcgg  120
ggacaaa                                                            127
```

|  |  |
|---|---|
| SEQ ID NO: 154 | moltype = RNA length = 100 |
| FEATURE | Location/Qualifiers |
| misc_feature | 1..100 |
| | note = RNA sequence MML-1 |
| misc_feature | 32..34 |
| | note = nnn stands for uuu, auu, guu, agu, ccg, acu, gcu, cau, ugg, ggu, uac, cag, aac, cgg, agg, uug, cuu, cua, uag, ugc or gaa |
| misc_feature | 35..37 |
| | note = nnn stands for uuu, auu, guu, agu, ccg, acu, gcu, cau, ugg, ggu, uac, cag, aac, cgg, agg, uug, cuu, cua, uag, ugc or gaa |
| misc_feature | 38..40 |
| | note = nnn stands for uuu, auu, guu, agu, ccg, acu, gcu, cau, ugg, ggu, uac, cag, aac, cgg, agg, uug, cuu, cua, uag, ugc or gaa |
| misc_feature | 41..43 |
| | note = nnn stands for uuu, auu, guu, agu, ccg, acu, gcu, cau, ugg, ggu, uac, cag, aac, cgg, agg, uug, cuu, cua, uag, ugc or gaa |
| misc_feature | 44..46 |
| | note = nnn stands for uuu, auu, guu, agu, ccg, acu, gcu, cau, ugg, ggu, uac, cag, aac, cgg, agg, uug, cuu, cua, uag, ugc or gaa |
| misc_feature | 47..49 |
| | note = nnn stands for uuu, auu, guu, agu, ccg, acu, gcu, cau, ugg, ggu, uac, cag, aac, cgg, agg, uug, cuu, cua, uag, ugc or gaa |

```
misc_feature          50..52
                      note = nnn stands for uuu, auu, guu, agu, ccg, acu, gcu,
                       cau, ugg, ggu, uac, cag, aac, cgg, agg, uug, cuu, cua,
                       uag, ugc or gaa
misc_feature          56..58
                      note = nnn stands for uuu, ccg, gcu, cau, aac, cgg, agg,
                       uug, uag or gaa
misc_feature          59..61
                      note = nnn stands for uuu, auu, guu, agu, ccg, acu, gcu,
                       cau, ugg, ggu, uac, cag, aac, cgg, agg, uug, cuu, cua,
                       uag, ugc or gaa
source                1..100
                      mol_type = other RNA
                      organism = synthetic construct
SEQUENCE: 154
gggttaacctt taagaaggag atatacatat gnnnnnnnnn nnnnnnnnnn nncgtnnnnn         60
nagcggctct ggctctggct cttagggcgg cggggacaaa                              100

SEQ ID NO: 155        moltype = RNA  length = 103
FEATURE               Location/Qualifiers
misc_feature          1..103
                      note = RNA sequence MML-2
misc_feature          32..34
                      note = nnn stands for uuu, auu, guu, agu, ccg, acu, gcu,
                       cau, ugg, ggu, uac, cag, aac, cgg, agg, uug, cuu, cua,
                       uag, ugc or gaa
misc_feature          35..37
                      note = nnn stands for uuu, auu, guu, agu, ccg, acu, gcu,
                       cau, ugg, ggu, uac, cag, aac, cgg, agg, uug, cuu, cua,
                       uag, ugc or gaa
misc_feature          38..40
                      note = nnn stands for uuu, auu, guu, agu, ccg, acu, gcu,
                       cau, ugg, ggu, uac, cag, aac, cgg, agg, uug, cuu, cua,
                       uag, ugc or gaa
misc_feature          41..43
                      note = nnn stands for uuu, auu, guu, agu, ccg, acu, gcu,
                       cau, ugg, ggu, uac, cag, aac, cgg, agg, uug, cuu, cua,
                       uag, ugc or gaa
misc_feature          44..46
                      note = nnn stands for uuu, auu, guu, agu, ccg, acu, gcu,
                       cau, ugg, ggu, uac, cag, aac, cgg, agg, uug, cuu, cua,
                       uag, ugc or gaa
misc_feature          47..49
                      note = nnn stands for uuu, auu, guu, agu, ccg, acu, gcu,
                       cau, ugg, ggu, uac, cag, aac, cgg, agg, uug, cuu, cua,
                       uag, ugc or gaa
misc_feature          50..52
                      note = nnn stands for uuu, auu, guu, agu, ccg, acu, gcu,
                       cau, ugg, ggu, uac, cag, aac, cgg, agg, uug, cuu, cua,
                       uag, ugc or gaa
misc_feature          53..55
                      note = nnn stands for uuu, auu, guu, agu, ccg, acu, gcu,
                       cau, ugg, ggu, uac, cag, aac, cgg, agg, uug, cuu, cua,
                       uag, ugc or gaa
misc_feature          59..61
                      note = nnn stands for uuu, ccg, gcu, cau, aac, cgg, agg,
                       uug, uag or gaa
misc_feature          62..64
                      note = nnn stands for uuu, auu, guu, agu, ccg, acu, gcu,
                       cau, ugg, ggu, uac, cag, aac, cgg, agg, uug, cuu, cua,
                       uag, ugc or gaa
source                1..103
                      mol_type = other RNA
                      organism = synthetic construct
SEQUENCE: 155
gggttaacctt taagaaggag atatacatat gnnnnnnnnn nnnnnnnnnn nnnncgtnn         60
nnnnagcggc tctggctctg gctcttaggg cggcggggac aaa                          103

SEQ ID NO: 156        moltype = RNA  length = 106
FEATURE               Location/Qualifiers
misc_feature          1..106
                      note = RNA sequence MML-3
misc_feature          32..34
                      note = nnn stands for uuu, auu, guu, agu, ccg, acu, gcu,
                       cau, ugg, ggu, uac, cag, aac, cgg, agg, uug, cuu, cua,
                       uag, ugc or gaa
misc_feature          35..37
                      note = nnn stands for uuu, auu, guu, agu, ccg, acu, gcu,
                       cau, ugg, ggu, uac, cag, aac, cgg, agg, uug, cuu, cua,
```

|  |  |
|---|---|
| misc_feature | 38..40 |
|  | note = nnn stands for uuu, auu, guu, agu, ccg, acu, gcu, cau, ugg, ggu, uac, cag, aac, cgg, agg, uug, cuu, cua, uag, ugc or gaa |
| misc_feature | 41..43 |
|  | note = nnn stands for uuu, auu, guu, agu, ccg, acu, gcu, cau, ugg, ggu, uac, cag, aac, cgg, agg, uug, cuu, cua, uag, ugc or gaa |
| misc_feature | 44..46 |
|  | note = nnn stands for uuu, auu, guu, agu, ccg, acu, gcu, cau, ugg, ggu, uac, cag, aac, cgg, agg, uug, cuu, cua, uag, ugc or gaa |
| misc_feature | 47..49 |
|  | note = nnn stands for uuu, auu, guu, agu, ccg, acu, gcu, cau, ugg, ggu, uac, cag, aac, cgg, agg, uug, cuu, cua, uag, ugc or gaa |
| misc_feature | 50..52 |
|  | note = nnn stands for uuu, auu, guu, agu, ccg, acu, gcu, cau, ugg, ggu, uac, cag, aac, cgg, agg, uug, cuu, cua, uag, ugc or gaa |
| misc_feature | 53..55 |
|  | note = nnn stands for uuu, auu, guu, agu, ccg, acu, gcu, cau, ugg, ggu, uac, cag, aac, cgg, agg, uug, cuu, cua, uag, ugc or gaa |
| misc_feature | 56..58 |
|  | note = nnn stands for uuu, auu, guu, agu, ccg, acu, gcu, cau, ugg, ggu, uac, cag, aac, cgg, agg, uug, cuu, cua, uag, ugc or gaa |
| misc_feature | 62..64 |
|  | note = nnn stands for uuu, ccg, gcu, cau, aac, cgg, agg, uug, uag or gaa |
| misc_feature | 65..67 |
|  | note = nnn stands for uuu, auu, guu, agu, ccg, acu, gcu, cau, ugg, ggu, uac, cag, aac, cgg, agg, uug, cuu, cua, uag, ugc or gaa |
| source | 1..106 |
|  | mol_type = other RNA |
|  | organism = synthetic construct |

SEQUENCE: 156

```
gggttaacutt taagaaggag atatacatat gnnnnnnnnn nnnnnnnnnn nnnnnnnncg    60
tnnnnnnagc ggctctggct ctggctctta gggcggcggg gacaaa                    106
```

| SEQ ID NO: 157 | moltype = RNA   length = 103 |
|---|---|
| FEATURE | Location/Qualifiers |
| misc_feature | 1..103 |
|  | note = RNA sequence MML-4 |
| misc_feature | 35..37 |
|  | note = nnn stands for uuu, auu, aug, guu, agu, ccg, acu, gcu, cau, ugg, ggu, uac, cag, aac, cgg, agg, uug, cuu, cua, uag or gaa |
| misc_feature | 38..40 |
|  | note = nnn stands for uuu, auu, aug, guu, agu, ccg, acu, gcu, cau, ugg, ggu, uac, cag, aac, cgg, agg, uug, cuu, cua, uag or gaa |
| misc_feature | 41..43 |
|  | note = nnn stands for uuu, auu, aug, guu, agu, ccg, acu, gcu, cau, ugg, ggu, uac, cag, aac, cgg, agg, uug, cuu, cua, uag or gaa |
| misc_feature | 44..46 |
|  | note = nnn stands for uuu, auu, aug, guu, agu, ccg, acu, gcu, cau, ugg, ggu, uac, cag, aac, cgg, agg, uug, cuu, cua, uag or gaa |
| misc_feature | 47..49 |
|  | note = nnn stands for uuu, auu, aug, guu, agu, ccg, acu, gcu, cau, ugg, ggu, uac, cag, aac, cgg, agg, uug, cuu, cua, uag or gaa |
| misc_feature | 50..52 |
|  | note = nnn stands for uuu, auu, aug, guu, agu, ccg, acu, gcu, cau, ugg, ggu, uac, cag, aac, cgg, agg, uug, cuu, cua, uag or gaa |
| misc_feature | 53..55 |
|  | note = nnn stands for uuu, auu, aug, guu, agu, ccg, acu, gcu, cau, ugg, ggu, uac, cag, aac, cgg, agg, uug, cuu, cua, uag or gaa |
| misc_feature | 59..61 |
|  | note = nnn stands for uuu, auu, aug, guu, agu, ccg, acu, gcu, cau, ugg, ggu, uac, cag, aac, cgg, agg, uug, cuu, cua, uag or gaa |

-continued

```
misc_feature          62..64
                      note = nnn stands for uuu, auu, aug, guu, agu, ccg, acu,
                      gcu, cau, ugg, ggu, uac, cag, aac, cgg, agg, uug, cuu,
                      cua, uag or gaa
source                1..103
                      mol_type = other RNA
                      organism = synthetic construct
SEQUENCE: 157
gggttaacttt taagaaggag atatacatat gtgcnnnnnn nnnnnnnnnn nnnncgtnn    60
nnnnagcggc tctggctctg gctcttaggg cggcgggac aaa                      103

SEQ ID NO: 158        moltype = RNA   length = 106
FEATURE               Location/Qualifiers
misc_feature          1..106
                      note = RNA sequence MML-5
misc_feature          35..37
                      note = nnn stands for uuu, auu, aug, guu, agu, ccg, acu,
                      gcu, cau, ugg, ggu, uac, cag, aac, cgg, agg, uug, cuu,
                      cua, uag or gaa
misc_feature          38..40
                      note = nnn stands for uuu, auu, aug, guu, agu, ccg, acu,
                      gcu, cau, ugg, ggu, uac, cag, aac, cgg, agg, uug, cuu,
                      cua, uag or gaa
misc_feature          41..43
                      note = nnn stands for uuu, auu, aug, guu, agu, ccg, acu,
                      gcu, cau, ugg, ggu, uac, cag, aac, cgg, agg, uug, cuu,
                      cua, uag or gaa
misc_feature          44..46
                      note = nnn stands for uuu, auu, aug, guu, agu, ccg, acu,
                      gcu, cau, ugg, ggu, uac, cag, aac, cgg, agg, uug, cuu,
                      cua, uag or gaa
misc_feature          47..49
                      note = nnn stands for uuu, auu, aug, guu, agu, ccg, acu,
                      gcu, cau, ugg, ggu, uac, cag, aac, cgg, agg, uug, cuu,
                      cua, uag or gaa
misc_feature          50..52
                      note = nnn stands for uuu, auu, aug, guu, agu, ccg, acu,
                      gcu, cau, ugg, ggu, uac, cag, aac, cgg, agg, uug, cuu,
                      cua, uag or gaa
misc_feature          53..55
                      note = nnn stands for uuu, auu, aug, guu, agu, ccg, acu,
                      gcu, cau, ugg, ggu, uac, cag, aac, cgg, agg, uug, cuu,
                      cua, uag or gaa
misc_feature          56..58
                      note = nnn stands for uuu, auu, aug, guu, agu, ccg, acu,
                      gcu, cau, ugg, ggu, uac, cag, aac, cgg, agg, uug, cuu,
                      cua, uag or gaa
misc_feature          62..64
                      note = nnn stands for uuu, auu, aug, guu, agu, ccg, acu,
                      gcu, cau, ugg, ggu, uac, cag, aac, cgg, agg, uug, cuu,
                      cua, uag or gaa
misc_feature          65..67
                      note = nnn stands for uuu, auu, aug, guu, agu, ccg, acu,
                      gcu, cau, ugg, ggu, uac, cag, aac, cgg, agg, uug, cuu,
                      cua, uag or gaa
source                1..106
                      mol_type = other RNA
                      organism = synthetic construct
SEQUENCE: 158
gggttaacttt taagaaggag atatacatat gtgcnnnnnn nnnnnnnnnn nnnnnnnncg    60
tnnnnnnagc ggctctggct ctggctctta gggcggcggg gacaaa                    106

SEQ ID NO: 159        moltype = RNA   length = 109
FEATURE               Location/Qualifiers
misc_feature          1..109
                      note = RNA sequence MML-6
misc_feature          35..37
                      note = nnn stands for uuu, auu, aug, guu, agu, ccg, acu,
                      gcu, cau, ugg, ggu, uac, cag, aac, cgg, agg, uug, cuu,
                      cua, uag or gaa
misc_feature          38..40
                      note = nnn stands for uuu, auu, aug, guu, agu, ccg, acu,
                      gcu, cau, ugg, ggu, uac, cag, aac, cgg, agg, uug, cuu,
                      cua, uag or gaa
misc_feature          41..43
                      note = nnn stands for uuu, auu, aug, guu, agu, ccg, acu,
                      gcu, cau, ugg, ggu, uac, cag, aac, cgg, agg, uug, cuu,
                      cua, uag or gaa
misc_feature          44..46
```

```
                       note = nnn stands for uuu, auu, aug, guu, agu, ccg, acu,
                              gcu, cau, ugg, ggu, uac, cag, aac, cgg, agg, uug, cuu,
                              cua, uag or gaa
misc_feature           47..49
                       note = nnn stands for uuu, auu, aug, guu, agu, ccg, acu,
                              gcu, cau, ugg, ggu, uac, cag, aac, cgg, agg, uug, cuu,
                              cua, uag or gaa
misc_feature           50..52
                       note = nnn stands for uuu, auu, aug, guu, agu, ccg, acu,
                              gcu, cau, ugg, ggu, uac, cag, aac, cgg, agg, uug, cuu,
                              cua, uag or gaa
misc_feature           53..55
                       note = nnn stands for uuu, auu, aug, guu, agu, ccg, acu,
                              gcu, cau, ugg, ggu, uac, cag, aac, cgg, agg, uug, cuu,
                              cua, uag or gaa
misc_feature           56..58
                       note = nnn stands for uuu, auu, aug, guu, agu, ccg, acu,
                              gcu, cau, ugg, ggu, uac, cag, aac, cgg, agg, uug, cuu,
                              cua, uag or gaa
misc_feature           59..61
                       note = nnn stands for uuu, auu, aug, guu, agu, ccg, acu,
                              gcu, cau, ugg, ggu, uac, cag, aac, cgg, agg, uug, cuu,
                              cua, uag or gaa
misc_feature           65..67
                       note = nnn stands for uuu, auu, aug, guu, agu, ccg, acu,
                              gcu, cau, ugg, ggu, uac, cag, aac, cgg, agg, uug, cuu,
                              cua, uag or gaa
misc_feature           68..70
                       note = nnn stands for uuu, auu, aug, guu, agu, ccg, acu,
                              gcu, cau, ugg, ggu, uac, cag, aac, cgg, agg, uug, cuu,
                              cua, uag or gaa
source                 1..109
                       mol_type = other RNA
                       organism = synthetic construct
SEQUENCE: 159
gggttaactt taagaaggag atatacatat gtgcnnnnnn nnnnnnnnnn nnnnnnnnnn    60
ncgtnnnnnn agcggctctg gctctggctc ttagggcggc ggggacaaa                109

SEQ ID NO: 160         moltype = DNA   length = 39
FEATURE                Location/Qualifiers
misc_feature           1..39
                       note = DNA sequence DOL-3
source                 1..39
                       mol_type = other DNA
                       organism = synthetic construct
SEQUENCE: 160
tttgtccccg ccgccctaag agccagagcc agagccgct                           39

SEQ ID NO: 161         moltype = DNA   length = 39
FEATURE                Location/Qualifiers
misc_feature           1..39
                       note = DNA sequence DOL-4
source                 1..39
                       mol_type = other DNA
                       organism = synthetic construct
SEQUENCE: 161
gtaatacgac tcactatagg gttaacttta agaaggaga                           39

SEQ ID NO: 162         moltype = DNA   length = 18
FEATURE                Location/Qualifiers
misc_feature           1..18
                       note = DNA sequence DOL-5
source                 1..18
                       mol_type = other DNA
                       organism = synthetic construct
SEQUENCE: 162
tttgtccccg ccgcccta                                                  18

SEQ ID NO: 163         moltype =   length =
SEQUENCE: 163
000

SEQ ID NO: 164         moltype = DNA   length = 109
FEATURE                Location/Qualifiers
misc_feature           1..109
                       note = DNA sequence DME-2
source                 1..109
                       mol_type = other DNA
                       organism = synthetic construct
```

```
SEQUENCE: 164
gtaatacgac tcactatagg gttaacttta agaaggagat atacatatgt gcccgattat    60
ttttatgccg aggtacgttc gtagtactag cggctctggc tctggctct              109

SEQ ID NO: 165          moltype = DNA   length = 109
FEATURE                 Location/Qualifiers
misc_feature            1..109
                        note = DNA sequence DME-3
source                  1..109
                        mol_type = other DNA
                        organism = synthetic construct
SEQUENCE: 165
gtaatacgac tcactatagg gttaacttta agaaggagat atacatatgt gcccgattat    60
ttggaggatg ccgaggtacc gtgtttacag cggctctggc tctggctct              109

SEQ ID NO: 166          moltype = DNA   length = 109
FEATURE                 Location/Qualifiers
misc_feature            1..109
                        note = DNA sequence DME-4
source                  1..109
                        mol_type = other DNA
                        organism = synthetic construct
SEQUENCE: 166
gtaatacgac tcactatagg gttaacttta agaaggagat atacatatgt gctacatttg    60
gatgagtatg agggtttttc gtactaggag cggctctggc tctggctct              109

SEQ ID NO: 167          moltype = DNA   length = 109
FEATURE                 Location/Qualifiers
misc_feature            1..109
                        note = DNA sequence DME-5
source                  1..109
                        mol_type = other DNA
                        organism = synthetic construct
SEQUENCE: 167
gtaatacgac tcactatagg gttaacttta agaaggagat atacatatgt gcccgttgat    60
tattgttagt cggcttcttc gtgaaactag cggctctggc tctggctct              109

SEQ ID NO: 168          moltype = DNA   length = 109
FEATURE                 Location/Qualifiers
misc_feature            1..109
                        note = DNA sequence DME-6
source                  1..109
                        mol_type = other DNA
                        organism = synthetic construct
SEQUENCE: 168
gtaatacgac tcactatagg gttaacttta agaaggagat atacatatgt gcccgttggt    60
tattactgtt cggcttagtc gtgctaggag cggctctggc tctggctct              109

SEQ ID NO: 169          moltype = DNA   length = 106
FEATURE                 Location/Qualifiers
misc_feature            1..106
                        note = DNA sequence DME-7
source                  1..106
                        mol_type = other DNA
                        organism = synthetic construct
SEQUENCE: 169
gtaatacgac tcactatagg gttaacttta agaaggagat atacatatga ctcttattga    60
atggtggcta tacaggcgtc cgttgagcgg ctctggctct ggctct                106

SEQ ID NO: 170          moltype = DNA   length = 109
FEATURE                 Location/Qualifiers
misc_feature            1..109
                        note = DNA sequence DME-8
source                  1..109
                        mol_type = other DNA
                        organism = synthetic construct
SEQUENCE: 170
gtaatacgac tcactatagg gttaacttta agaaggagat atacatatgt gcctatggtg    60
ggttttgggt ccgtagagtc gtcggatgag cggctctggc tctggctct              109

SEQ ID NO: 171          moltype = DNA   length = 109
FEATURE                 Location/Qualifiers
misc_feature            1..109
                        note = DNA sequence DME-9
source                  1..109
                        mol_type = other DNA
                        organism = synthetic construct
SEQUENCE: 171
gtaatacgac tcactatagg gttaacttta agaaggagat atacatatgt gcgaaattcc    60
```

```
ggtttggtgg ctaatggttc gttgggaaag cggctctggc tctggctct                 109

SEQ ID NO: 172          moltype = DNA   length = 109
FEATURE                 Location/Qualifiers
misc_feature            1..109
                        note = DNA sequence DME-10
source                  1..109
                        mol_type = other DNA
                        organism = synthetic construct
SEQUENCE: 172
gtaatacgac tcactatagg gttaacttta agaaggagat atacatatgt gcactattcc      60
gtactggtgg ctaatggttc gttgggaaag cggctctggc tctggctct                 109

SEQ ID NO: 173          moltype = DNA   length = 109
FEATURE                 Location/Qualifiers
misc_feature            1..109
                        note = DNA sequence DME-11
source                  1..109
                        mol_type = other DNA
                        organism = synthetic construct
SEQUENCE: 173
gtaatacgac tcactatagg gttaacttta agaaggagat atacatatgt gcacttggat      60
ttttctttgg cagctacttc gtgttactag cggctctggc tctggctct                 109

SEQ ID NO: 174          moltype =   length =
SEQUENCE: 174
000

SEQ ID NO: 175          moltype = DNA   length = 109
FEATURE                 Location/Qualifiers
misc_feature            1..109
                        note = DNA sequence DME-13
source                  1..109
                        mol_type = other DNA
                        organism = synthetic construct
SEQUENCE: 175
gtaatacgac tcactatagg gttaacttta agaaggagat atacatatgt gcccggttat      60
ttttatgccg agggttatgc gtccgttgag cggctctggc tctggctct                 109

SEQ ID NO: 176          moltype = DNA   length = 109
FEATURE                 Location/Qualifiers
misc_feature            1..109
                        note = DNA sequence DME-14
source                  1..109
                        mol_type = other DNA
                        organism = synthetic construct
SEQUENCE: 176
gtaatacgac tcactatagg gttaacttta agaaggagat atacatatgt gcattattga      60
atggccgagg atgtaccagc gtccgaggag cggctctggc tctggctct                 109

SEQ ID NO: 177          moltype = DNA   length = 106
FEATURE                 Location/Qualifiers
misc_feature            1..106
                        note = DNA sequence DME-15
source                  1..106
                        mol_type = other DNA
                        organism = synthetic construct
SEQUENCE: 177
gtaatacgac tcactatagg gttaacttta agaaggagat atacatatga ttgtttggag      60
gtgcccgagg tactgccgtg aagctagcgg ctctggctct ggctct                    106

SEQ ID NO: 178          moltype = RNA   length = 10
FEATURE                 Location/Qualifiers
misc_feature            1..10
                        note = an artificially synthesized RNA sequence
source                  1..10
                        mol_type = other RNA
                        organism = synthetic construct
SEQUENCE: 178
agcttagtca                                                             10

SEQ ID NO: 179          moltype = DNA   length = 95
FEATURE                 Location/Qualifiers
misc_feature            1..95
                        note = DNA sequence DT-E1
source                  1..95
                        mol_type = other DNA
                        organism = synthetic construct
SEQUENCE: 179
```

```
ggcgtaatac gactcactat agtccccttc gtctagaggc ccaggacacc gccctaagac    60
ggcggtaaca ggggttcgaa tcccctaggg gacgc                               95

SEQ ID NO: 180           moltype = RNA   length = 74
FEATURE                  Location/Qualifiers
misc_feature             1..74
                         note = RNA sequence RT-E1
source                   1..74
                         mol_type = other RNA
                         organism = synthetic construct
SEQUENCE: 180
gtccccttcg tctagaggcc caggacaccg ccctaagacg gcggtaacag ggggttcgaat   60
cccctagggg acgc                                                      74

SEQ ID NO: 181           moltype = RNA   length = 76
FEATURE                  Location/Qualifiers
misc_feature             1..76
                         note = tRNAGluAAG
source                   1..76
                         mol_type = other RNA
                         organism = synthetic construct
SEQUENCE: 181
gtccccttcg tctagaggcc caggacaccg ccctaagacg gcggtaacag ggggttcgaat   60
cccctagggg acgcca                                                    76

SEQ ID NO: 182           moltype = RNA   length = 73
FEATURE                  Location/Qualifiers
misc_feature             1..73
                         note = RNA sequence RM-E1
source                   1..73
                         mol_type = other RNA
                         organism = synthetic construct
SEQUENCE: 182
gggttaactt taagaaggag atatacatat gtgcactaca acgcgtcttc cgtaccgtgg    60
cggctaagct tcg                                                       73

SEQ ID NO: 183           moltype = AA    length = 12
FEATURE                  Location/Qualifiers
REGION                   1..12
                         note = peptide P-E1
MOD_RES                  1
                         note = FORMYLATION
CROSSLNK                 2..7
                         note = THIOLEST -
source                   1..12
                         mol_type = protein
                         organism = synthetic construct
SEQUENCE: 183
MCTTTRDPYR GG                                                        12

SEQ ID NO: 184           moltype = AA    length = 11
FEATURE                  Location/Qualifiers
REGION                   1..11
                         note = peptide P-E2
REGION                   1..6
                         note = CROSSLINK - isoaspartyl cysteine (Cys-Asp)
source                   1..11
                         mol_type = protein
                         organism = synthetic construct
SEQUENCE: 184
CTTTRDPYRG G                                                         11

SEQ ID NO: 185           moltype = RNA   length = 97
FEATURE                  Location/Qualifiers
misc_feature             1..97
                         note = RNA sequence RM-H4
source                   1..97
                         mol_type = other RNA
                         organism = synthetic construct
SEQUENCE: 185
gggttaactt taagaaggag atatacatat gtgcactaca acgcgtcttc cgtaccgtag    60
cggctctggc tctggctctt agggcggcgg ggacaaa                             97

SEQ ID NO: 186           moltype = AA    length = 12
FEATURE                  Location/Qualifiers
REGION                   1..12
                         note = An artificially synthesized sequence
SITE                     6
                         note = MISC_FEATURE - Xaa = Glu(SBn)
```

```
                            -continued source                  1..12
                        mol_type = protein
                        organism = synthetic construct
SEQUENCE: 186
MTTTRXYYRR GG                                                           12

SEQ ID NO: 187          moltype = AA  length = 11
FEATURE                 Location/Qualifiers
REGION                  1..11
                        note = An artificially synthesized sequence
SITE                    6
                        note = MISC_FEATURE - Xaa = Asp(SMe)
source                  1..11
                        mol_type = protein
                        organism = synthetic construct
SEQUENCE: 187
MTTTRXYYRG G                                                            11

SEQ ID NO: 188          moltype = AA  length = 13
FEATURE                 Location/Qualifiers
REGION                  1..13
                        note = An artificially synthesized sequence
SITE                    8
                        note = MISC_FEATURE - Xaa = Asp(SBn)
source                  1..13
                        mol_type = protein
                        organism = synthetic construct
SEQUENCE: 188
MTTTAGGXFF GGK                                                          13

SEQ ID NO: 189          moltype = AA  length = 12
FEATURE                 Location/Qualifiers
REGION                  1..12
                        note = An artificially synthesized sequence
SITE                    1
                        note = MISC_FEATURE - Xaa = MeOFlac
SITE                    6
                        note = MISC_FEATURE - Xaa = Asp(SBn)
source                  1..12
                        mol_type = protein
                        organism = synthetic construct
SEQUENCE: 189
XTTTRXYYRR GG                                                           12

SEQ ID NO: 190          moltype = AA  length = 13
FEATURE                 Location/Qualifiers
REGION                  1..13
                        note = An artificially synthesized sequence
SITE                    10
                        note = MISC_FEATURE - Xaa = Asp(SMe)
source                  1..13
                        mol_type = protein
                        organism = synthetic construct
SEQUENCE: 190
MTRTKAYWSX PGG                                                          13

SEQ ID NO: 191          moltype = AA  length = 12
FEATURE                 Location/Qualifiers
REGION                  1..12
                        note = An artificially synthesized sequence
SITE                    1
                        note = MISC_FEATURE - Xaa = MeOFlac
MOD_RES                 6..7
                        note = aspartimide formation
source                  1..12
                        mol_type = protein
                        organism = synthetic construct
SEQUENCE: 191
XTTTRDYYRR GG                                                           12

SEQ ID NO: 192          moltype = AA  length = 13
FEATURE                 Location/Qualifiers
REGION                  1..13
                        note = An artificially synthesized sequence
SITE                    10
                        note = MISC_FEATURE - Xaa = Asp(SBn)
SITE                    11
                        note = MISC_FEATURE - Xaa = MePhe
source                  1..13
```

```
                              mol_type = protein
                              organism = synthetic construct
SEQUENCE: 192
MTRTKAYWSX XGG                                                            13

SEQ ID NO: 193                moltype = AA   length = 11
FEATURE                       Location/Qualifiers
REGION                        1..11
                              note = An artificially synthesized sequence
SITE                          1
                              note = MISC_FEATURE - Xaa = Cys(StBu)
source                        1..11
                              mol_type = protein
                              organism = synthetic construct
SEQUENCE: 193
XTTTRLYYRG G                                                              11

SEQ ID NO: 194                moltype = AA   length = 16
FEATURE                       Location/Qualifiers
REGION                        1..16
                              note = An artificially synthesized sequence
SITE                          1
                              note = MISC_FEATURE - Xaa = Cys(StBu)
source                        1..16
                              mol_type = protein
                              organism = synthetic construct
SEQUENCE: 194
XTRTAYWSLC GSGSGS                                                         16

SEQ ID NO: 195                moltype = AA   length = 13
FEATURE                       Location/Qualifiers
REGION                        1..13
                              note = An artificially synthesized sequence
SITE                          1
                              note = MISC_FEATURE - Xaa = tBuSSEtGly, tBuSSEt betaAla,
                               tBuSSEtGABA, NVOC-Cys(StBu), PenCys(StBu) or Cys(StBu)
source                        1..13
                              mol_type = protein
                              organism = synthetic construct
SEQUENCE: 195
XTRTKAYWSL PGG                                                            13

SEQ ID NO: 196                moltype = AA   length = 16
FEATURE                       Location/Qualifiers
REGION                        1..16
                              note = An artificially synthesized sequence
SITE                          1
                              note = MISC_FEATURE - Xaa = tBuSSEtGly, tBuSSEt betaAla,
                               tBuSSEtGABA, NVOC-Cys(StBu), PenCys(StBu) or Cys(StBu)
source                        1..16
                              mol_type = protein
                              organism = synthetic construct
SEQUENCE: 196
XTRTAYWSLC GSGSGS                                                         16

SEQ ID NO: 197                moltype = AA   length = 13
FEATURE                       Location/Qualifiers
REGION                        1..13
                              note = An artificially synthesized sequence
SITE                          1
                              note = MISC_FEATURE - Xaa = tBuSSEtGABA
SITE                          10
                              note = MISC_FEATURE - Xaa = Asp(SMe)
source                        1..13
                              mol_type = protein
                              organism = synthetic construct
SEQUENCE: 197
XTRTKAYWSX PGG                                                            13

SEQ ID NO: 198                moltype = AA   length = 13
FEATURE                       Location/Qualifiers
REGION                        1..13
                              note = An artificially synthesized sequence
SITE                          1
                              note = MISC_FEATURE - Xaa = HSEtGABA
SITE                          10
                              note = MISC_FEATURE - Xaa = Asp(SMe)
source                        1..13
                              mol_type = protein
```

```
                        organism = synthetic construct
SEQUENCE: 198
XTRTKAYWSX PGG                                                            13

SEQ ID NO: 199          moltype = AA  length = 12
FEATURE                 Location/Qualifiers
REGION                  1..12
                        note = An artificially synthesized sequence
SITE                    6
                        note = MISC_FEATURE - Xaa = Lac
SITE                    10
                        note = MISC_FEATURE - Xaa = Asp(SRex2) (Rex2: benzyl,
                         methyl, ethyl, isopropyl, tert-butyl or phenethyl)
source                  1..12
                        mol_type = protein
                        organism = synthetic construct
SEQUENCE: 199
CTRTKXYWSX PG                                                             12

SEQ ID NO: 200          moltype = AA  length = 11
FEATURE                 Location/Qualifiers
REGION                  1..11
                        note = An artificially synthesized sequence
SITE                    6
                        note = MISC_FEATURE - Xaa = Asp(SMe)
source                  1..11
                        mol_type = protein
                        organism = synthetic construct
SEQUENCE: 200
CTTTRXYYRG G                                                              11

SEQ ID NO: 201          moltype = AA  length = 11
FEATURE                 Location/Qualifiers
REGION                  1..11
                        note = An artificially synthesized sequence
SITE                    1
                        note = MISC_FEATURE - Xaa = Cys(CH2CONH2)
REGION                  1..6
                        note = MOD_RES - Cyclization
source                  1..11
                        mol_type = protein
                        organism = synthetic construct
SEQUENCE: 201
XTTTRDYYRG G                                                              11

SEQ ID NO: 202          moltype =     length =
SEQUENCE: 202
000

SEQ ID NO: 203          moltype =     length =
SEQUENCE: 203
000

SEQ ID NO: 204          moltype =     length =
SEQUENCE: 204
000

SEQ ID NO: 205          moltype =     length =
SEQUENCE: 205
000

SEQ ID NO: 206          moltype =     length =
SEQUENCE: 206
000

SEQ ID NO: 207          moltype =     length =
SEQUENCE: 207
000

SEQ ID NO: 208          moltype =     length =
SEQUENCE: 208
000

SEQ ID NO: 209          moltype =     length =
SEQUENCE: 209
000

SEQ ID NO: 210          moltype =     length =
SEQUENCE: 210
```

```
SEQ ID NO: 211           moltype =    length =
SEQUENCE: 211
000

SEQ ID NO: 212           moltype =    length =
SEQUENCE: 212
000

SEQ ID NO: 213           moltype =    length =
SEQUENCE: 213
000

SEQ ID NO: 214           moltype =    length =
SEQUENCE: 214
000

SEQ ID NO: 215           moltype = AA   length = 8
FEATURE                  Location/Qualifiers
REGION                   1..8
                         note = An artificially synthesized sequence
SITE                     1
                         note = MISC_FEATURE - Xaa = Ac-Leu
REGION                   1..7
                         note = MOD_RES - Cyclization
SITE                     2
                         note = MISC_FEATURE - Xaa = MeAla
SITE                     3
                         note = MISC_FEATURE - Xaa = Cha
SITE                     8
                         note = MISC_FEATURE - Xaa = Cha-piperidine
source                   1..8
                         mol_type = protein
                         organism = synthetic construct
SEQUENCE: 215
XXXTTACX                                                                   8

SEQ ID NO: 216           moltype =    length =
SEQUENCE: 216
000

SEQ ID NO: 217           moltype =    length =
SEQUENCE: 217
000

SEQ ID NO: 218           moltype =    length =
SEQUENCE: 218
000

SEQ ID NO: 219           moltype =    length =
SEQUENCE: 219
000

SEQ ID NO: 220           moltype =    length =
SEQUENCE: 220
000

SEQ ID NO: 221           moltype =    length =
SEQUENCE: 221
000

SEQ ID NO: 222           moltype =    length =
SEQUENCE: 222
000

SEQ ID NO: 223           moltype =    length =
SEQUENCE: 223
000

SEQ ID NO: 224           moltype =    length =
SEQUENCE: 224
000

SEQ ID NO: 225           moltype =    length =
SEQUENCE: 225
000

SEQ ID NO: 226           moltype =    length =
```

```
SEQUENCE: 226
000

SEQ ID NO: 227         moltype =   length =
SEQUENCE: 227
000

SEQ ID NO: 228         moltype =   length =
SEQUENCE: 228
000

SEQ ID NO: 229         moltype =   length =
SEQUENCE: 229
000

SEQ ID NO: 230         moltype =   length =
SEQUENCE: 230
000

SEQ ID NO: 231         moltype = AA   length = 12
FEATURE                Location/Qualifiers
REGION                 1..12
                       note = An artificially synthesized sequence
SITE                   1
                       note = MISC_FEATURE - Xaa = Boc-Gly
SITE                   3
                       note = MISC_FEATURE - Xaa = MePhe
SITE                   5
                       note = MISC_FEATURE - Xaa = MeLeu
SITE                   10
                       note = MISC_FEATURE - Xaa = MeAla
SITE                   11
                       note = MISC_FEATURE - Xaa = Ser(tBu)
SITE                   12
                       note = MISC_FEATURE - Xaa = Gly-NH2
source                 1..12
                       mol_type = protein
                       organism = synthetic construct
SEQUENCE: 231
XAXGXAVFDX XX                                                            12

SEQ ID NO: 232         moltype = AA   length = 12
FEATURE                Location/Qualifiers
REGION                 1..12
                       note = An artificially synthesized sequence
SITE                   1
                       note = MISC_FEATURE - Xaa = Boc-Gly
SITE                   3
                       note = MISC_FEATURE - Xaa = MePhe
SITE                   5
                       note = MISC_FEATURE - Xaa = MeLeu
SITE                   9
                       note = MISC_FEATURE - Xaa = Asp(OBn)
SITE                   10
                       note = MISC_FEATURE - Xaa = MeAla
SITE                   11
                       note = MISC_FEATURE - Xaa = Ser(tBu)
SITE                   12
                       note = MISC_FEATURE - Xaa = Gly-NH2
source                 1..12
                       mol_type = protein
                       organism = synthetic construct
SEQUENCE: 232
XAXGXAVFXX XX                                                            12

SEQ ID NO: 233         moltype = AA   length = 12
FEATURE                Location/Qualifiers
REGION                 1..12
                       note = An artificially synthesized sequence
SITE                   1
                       note = MISC_FEATURE - Xaa = Boc-Gly
SITE                   3
                       note = MISC_FEATURE - Xaa = MePhe
SITE                   5
                       note = MISC_FEATURE - Xaa = MeLeu
SITE                   9
                       note = MISC_FEATURE - Xaa = Asp(SBn)
SITE                   10
                       note = MISC_FEATURE - Xaa = MeAla
```

```
SITE                    11
                        note = MISC_FEATURE - Xaa = Ser(tBu)
SITE                    12
                        note = MISC_FEATURE - Xaa = Gly-NH2
source                  1..12
                        mol_type = protein
                        organism = synthetic construct
SEQUENCE: 233
XAXGXAVFXX XX                                                                12

SEQ ID NO: 234          moltype = AA  length = 11
FEATURE                 Location/Qualifiers
REGION                  1..11
                        note = An artificially synthesized sequence
SITE                    6
                        note = MISC_FEATURE - Xaa = Asp(SBn)
source                  1..11
                        mol_type = protein
                        organism = synthetic construct
SEQUENCE: 234
FTTTRXPYRG G                                                                 11

SEQ ID NO: 235          moltype = AA  length = 11
FEATURE                 Location/Qualifiers
REGION                  1..11
                        note = An artificially synthesized sequence
SITE                    6
                        note = MISC_FEATURE - Xaa = Asp(SBn)
source                  1..11
                        mol_type = protein
                        organism = synthetic construct
SEQUENCE: 235
ATTTRXPYRG G                                                                 11

SEQ ID NO: 236          moltype = AA  length = 12
FEATURE                 Location/Qualifiers
REGION                  1..12
                        note = An artificially synthesized sequence
SITE                    3
                        note = MISC_FEATURE - Xaa = MePhe
SITE                    9
                        note = MISC_FEATURE - Xaa = Asp(SBn)
SITE                    10
                        note = MISC_FEATURE - Xaa = MeAla
SITE                    12
                        note = MISC_FEATURE - Xaa = Gly-NH2
source                  1..12
                        mol_type = protein
                        organism = synthetic construct
SEQUENCE: 236
FAXGLAVFXX SX                                                                12

SEQ ID NO: 237          moltype = AA  length = 12
FEATURE                 Location/Qualifiers
REGION                  1..12
                        note = An artificially synthesized sequence
SITE                    1
                        note = MISC_FEATURE - Xaa = MeAla
SITE                    3
                        note = MISC_FEATURE - Xaa = MeLeu
SITE                    5
                        note = MISC_FEATURE - Xaa = MePhe
SITE                    7
                        note = MISC_FEATURE - Xaa = MeLeu
SITE                    8
                        note = MISC_FEATURE - Xaa = MeVal
SITE                    10
                        note = MISC_FEATURE - Xaa = Asp(O(2-EtSS-6-Me-Ph))
SITE                    11
                        note = MISC_FEATURE - Xaa = MePhe
SITE                    12
                        note = MISC_FEATURE - Xaa = Ala-piperidine
source                  1..12
                        mol_type = protein
                        organism = synthetic construct
SEQUENCE: 237
XVXTXGXXFX XX                                                                12

SEQ ID NO: 238          moltype = AA  length = 12
```

```
                              -continued
FEATURE              Location/Qualifiers
REGION               1..12
                     note = An artificially synthesized sequence
SITE                 1
                     note = MISC_FEATURE - Xaa = fNle
SITE                 7
                     note = MISC_FEATURE - Xaa = Asp(SBn)
source               1..12
                     mol_type = protein
                     organism = synthetic construct
SEQUENCE: 238
XGTTTRXPYR GG                                                                   12

SEQ ID NO: 239       moltype =    length =
SEQUENCE: 239
000

SEQ ID NO: 240       moltype = AA   length = 10
FEATURE              Location/Qualifiers
REGION               1..10
                     note = An artificially synthesized sequence
SITE                 1
                     note = MISC_FEATURE - Xaa = Acbz-Cys(StBu)
SITE                 3
                     note = MISC_FEATURE - Xaa = Lys(Me2)
SITE                 5
                     note = MISC_FEATURE - Xaa = Cys(StBu)
SITE                 7
                     note = MISC_FEATURE - Xaa = HOGly
SITE                 8
                     note = MISC_FEATURE - Xaa = Lys(Acbz)
SITE                 10
                     note = MISC_FEATURE - Xaa = Pro-NH2
source               1..10
                     mol_type = protein
                     organism = synthetic construct
SEQUENCE: 240
XGXWXPXXDX                                                                      10

SEQ ID NO: 241       moltype = AA   length = 10
FEATURE              Location/Qualifiers
REGION               1..10
                     note = An artificially synthesized sequence
SITE                 1
                     note = MISC_FEATURE - Xaa = H-Cys(StBu)
SITE                 3
                     note = MISC_FEATURE - Xaa = Lys(Me2)
SITE                 5
                     note = MISC_FEATURE - Xaa = Cys(StBu)
SITE                 7
                     note = MISC_FEATURE - Xaa = HOGly
SITE                 9
                     note = MISC_FEATURE - Xaa = Asp(SBn)
SITE                 10
                     note = MISC_FEATURE - Xaa = Pro-NH2
source               1..10
                     mol_type = protein
                     organism = synthetic construct
SEQUENCE: 241
XGXWXPXKXX                                                                      10

SEQ ID NO: 242       moltype =    length =
SEQUENCE: 242
000

SEQ ID NO: 243       moltype = AA   length = 17
FEATURE              Location/Qualifiers
REGION               1..17
                     note = An artificially synthesized sequence
SITE                 10
                     note = MISC_FEATURE - Xaa = HOGly
SITE                 14
                     note = MISC_FEATURE - Xaa = Asp(SMe)
source               1..17
                     mol_type = protein
                     organism = synthetic construct
SEQUENCE: 243
CTTWFRWCPX FKWXPRS                                                              17
```

```
SEQ ID NO: 244          moltype = AA  length = 8
FEATURE                 Location/Qualifiers
REGION                  1..8
                        note = An artificially synthesized sequence
SITE                    1
                        note = MISC_FEATURE - Xaa = HOGly
SITE                    3
                        note = MISC_FEATURE - Xaa = Lys(Trp-Arg-Phe-Trp-Thr-Thr-Cys)
REGION                  3..4
                        note = MOD RES - Cyclization
source                  1..8
                        mol_type = protein
                        organism = synthetic construct
SEQUENCE: 244
XFXWDPRS                                                                   8

SEQ ID NO: 245          moltype = AA  length = 8
FEATURE                 Location/Qualifiers
REGION                  1..8
                        note = An artificially synthesized sequence
SITE                    1
                        note = MISC_FEATURE - Xaa = HOGly
SITE                    5
                        note = MISC_FEATURE - Xaa = Asn(Cys-Thr-Thr-Trp-Phe-Arg-Trp)
source                  1..8
                        mol_type = protein
                        organism = synthetic construct
SEQUENCE: 245
XFKWXPRS                                                                   8

SEQ ID NO: 246          moltype = AA  length = 10
FEATURE                 Location/Qualifiers
REGION                  1..10
                        note = An artificially synthesized sequence
SITE                    1
                        note = MISC_FEATURE - Xaa = H-Cys(StBu)
SITE                    3
                        note = MISC_FEATURE - Xaa = Lys(Me2)
SITE                    5
                        note = MISC_FEATURE - Xaa = Cys(StBu)
SITE                    7
                        note = MISC_FEATURE - Xaa = HOGly
SITE                    9
                        note = MISC_FEATURE - Xaa = Asp(SBn)
SITE                    10
                        note = MISC_FEATURE - Xaa = Pro-NH2
source                  1..10
                        mol_type = protein
                        organism = synthetic construct
SEQUENCE: 246
XGXWXPXKXX                                                                10

SEQ ID NO: 247          moltype =    length =
SEQUENCE: 247
000

SEQ ID NO: 248          moltype =    length =
SEQUENCE: 248
000

SEQ ID NO: 249          moltype =    length =
SEQUENCE: 249
000

SEQ ID NO: 250          moltype =    length =
SEQUENCE: 250
000

SEQ ID NO: 251          moltype =    length =
SEQUENCE: 251
000

SEQ ID NO: 252          moltype = AA  length = 8
FEATURE                 Location/Qualifiers
REGION                  1..8
                        note = An artificially synthesized sequence
REGION                  1..6
                        note = MOD RES - Cyclization
REGION                  1..7
```

```
                         note = MOD RES - Cyclization
SITE                     2
                         note = MISC_FEATURE - Xaa = Lys(Me2)
SITE                     4
                         note = MISC_FEATURE - Xaa = HOGly
SITE                     6
                         note = MISC_FEATURE - Xaa = Lys(H-Cys)
SITE                     8
                         note = MISC_FEATURE - Xaa = Pro-NH2
source                   1..8
                         mol_type = protein
                         organism = synthetic construct
SEQUENCE: 252
CXWXPXDX                                                                         8

SEQ ID NO: 253           moltype =    length =
SEQUENCE: 253
000

SEQ ID NO: 254           moltype =    length =
SEQUENCE: 254
000

SEQ ID NO: 255           moltype = AA   length = 8
FEATURE                  Location/Qualifiers
REGION                   1..8
                         note = An artificially synthesized sequence
REGION                   1..6
                         note = MOD RES - Cyclization
REGION                   1..7
                         note = MOD RES - Cyclization
SITE                     2
                         note = MISC_FEATURE - Xaa = Lys(Me2)
SITE                     4
                         note = MISC_FEATURE - Xaa = HOGly
SITE                     6
                         note = MISC_FEATURE - Xaa = Lys(H-Cys)
SITE                     8
                         note = MISC_FEATURE - Xaa = Pro-NH2
source                   1..8
                         mol_type = protein
                         organism = synthetic construct
SEQUENCE: 255
CXWXPXDX                                                                         8

SEQ ID NO: 256           moltype =    length =
SEQUENCE: 256
000

SEQ ID NO: 257           moltype =    length =
SEQUENCE: 257
000

SEQ ID NO: 258           moltype =    length =
SEQUENCE: 258
000

SEQ ID NO: 259           moltype =    length =
SEQUENCE: 259
000

SEQ ID NO: 260           moltype =    length =
SEQUENCE: 260
000

SEQ ID NO: 261           moltype =    length =
SEQUENCE: 261
000

SEQ ID NO: 262           moltype =    length =
SEQUENCE: 262
000

SEQ ID NO: 263           moltype =    length =
SEQUENCE: 263
000

SEQ ID NO: 264           moltype = AA   length = 10
FEATURE                  Location/Qualifiers
```

```
REGION              1..10
                    note = An artificially synthesized sequence
SITE                1
                    note = MISC_FEATURE - Xaa = Acbz-Cys(StBu)
SITE                3
                    note = MISC_FEATURE - Xaa = Lys(Me2)
SITE                5
                    note = MISC_FEATURE - Xaa = Cys(StBu)
SITE                7
                    note = MISC_FEATURE - Xaa = Lac
SITE                8
                    note = MISC_FEATURE - Xaa = Lys(Acbz-Thz)
SITE                10
                    note = MISC_FEATURE - Xaa = Pro-NH2
source              1..10
                    mol_type = protein
                    organism = synthetic construct
SEQUENCE: 264
XGXWXPXXDX                                                                          10

SEQ ID NO: 265      moltype =   length =
SEQUENCE: 265
000

SEQ ID NO: 266      moltype = AA  length = 10
FEATURE             Location/Qualifiers
REGION              1..10
                    note = An artificially synthesized sequence
REGION              1..9
                    note = MOD_RES - Cyclization
SITE                3
                    note = MISC_FEATURE - Xaa = Lys(Me2)
SITE                7
                    note = MISC_FEATURE - Xaa = Lac
SITE                8
                    note = MISC_FEATURE - Xaa = Lys(Thz)
SITE                10
                    note = MISC_FEATURE - Xaa = Pro-NH2
source              1..10
                    mol_type = protein
                    organism = synthetic construct
SEQUENCE: 266
CGXWCPXXDX                                                                          10

SEQ ID NO: 267      moltype = AA  length = 10
FEATURE             Location/Qualifiers
REGION              1..10
                    note = An artificially synthesized sequence
REGION              1..9
                    note = MOD_RES - Cyclization
SITE                3
                    note = MISC_FEATURE - Xaa = Lys(Me2)
SITE                7
                    note = MISC_FEATURE - Xaa = Lac
SITE                8
                    note = MISC_FEATURE - Xaa = Lys(H-Cys)
SITE                10
                    note = MISC_FEATURE - Xaa = Pro-NH2
source              1..10
                    mol_type = protein
                    organism = synthetic construct
SEQUENCE: 267
CGXWCPXXDX                                                                          10

SEQ ID NO: 268      moltype =   length =
SEQUENCE: 268
000

SEQ ID NO: 269      moltype = AA  length = 13
FEATURE             Location/Qualifiers
REGION              1..13
                    note = An artificially synthesized sequence
SITE                1
                    note = MISC_FEATURE - Xaa = HOGly
REGION              1..13
                    note = MOD_RES - Cyclization
SITE                3
                    note = MISC_FEATURE - Xaa = Lys(N3)
SITE                5
```

```
                        note = MISC_FEATURE - Xaa = MeAla
SITE                    6
                        note = MISC_FEATURE - Xaa = MeLeu
SITE                    8
                        note = MISC_FEATURE - Xaa = MePhe
SITE                    9
                        note = MISC_FEATURE - Xaa = MeAla
SITE                    12
                        note = MISC_FEATURE - Xaa = Cys(StBu)
source                  1..13
                        mol_type = protein
                        organism = synthetic construct
SEQUENCE: 269
XFXLXXAXXA FXP                                                                 13

SEQ ID NO: 270          moltype = AA  length = 12
FEATURE                 Location/Qualifiers
REGION                  1..12
                        note = An artificially synthesized sequence
SITE                    1
                        note = MISC_FEATURE - Xaa = ClAc-Phe
SITE                    2
                        note = MISC_FEATURE - Xaa = Lys(N3)
SITE                    4
                        note = MISC_FEATURE - Xaa = MeAla
SITE                    5
                        note = MISC_FEATURE - Xaa = MeLeu
SITE                    7
                        note = MISC_FEATURE - Xaa = MePhe
SITE                    8
                        note = MISC_FEATURE - Xaa = MeAla
SITE                    11
                        note = MISC_FEATURE - Xaa = Cys(StBu)
source                  1..12
                        mol_type = protein
                        organism = synthetic construct
SEQUENCE: 270
XXLXXAXXAF XP                                                                  12

SEQ ID NO: 271          moltype =   length =
SEQUENCE: 271
000

SEQ ID NO: 272          moltype = AA  length = 11
FEATURE                 Location/Qualifiers
REGION                  1..11
                        note = An artificially synthesized sequence
SITE                    1
                        note = MISC_FEATURE - Xaa = Fmoc- Phe
SITE                    2
                        note = MISC_FEATURE - Xaa = tBuSSlac
SITE                    4
                        note = MISC_FEATURE - Xaa = Lys(Alloc-Cys(StBu))
SITE                    6
                        note = MISC_FEATURE - Xaa = MeAla
SITE                    7
                        note = MISC_FEATURE - Xaa = MeLeu
SITE                    9
                        note = MISC_FEATURE - Xaa = MePhe
SITE                    10
                        note = MISC_FEATURE - Xaa = MeAla
source                  1..11
                        mol_type = protein
                        organism = synthetic construct
SEQUENCE: 272
XXFXLXXAXXX A                                                                  11

SEQ ID NO: 273          moltype = AA  length = 11
FEATURE                 Location/Qualifiers
REGION                  1..11
                        note = An artificially synthesized sequence
SITE                    1
                        note = MISC_FEATURE - Xaa = H-Phe
SITE                    2
                        note = MISC_FEATURE - Xaa = tBuSSlac
SITE                    4
                        note = MISC_FEATURE - Xaa = Lys(Alloc-Cys(StBu))
SITE                    6
                        note = MISC_FEATURE - Xaa = MeAla
```

| | |
|---|---|
| SITE | 7 |
| | note = MISC_FEATURE - Xaa = MeLeu |
| SITE | 9 |
| | note = MISC_FEATURE - Xaa = MePhe |
| SITE | 10 |
| | note = MISC_FEATURE - Xaa = MeAla |
| source | 1..11 |
| | mol_type = protein |
| | organism = synthetic construct |

SEQUENCE: 273
XXFXLXXAXX A                                                                11

| | |
|---|---|
| SEQ ID NO: 274 | moltype = AA  length = 11 |
| FEATURE | Location/Qualifiers |
| REGION | 1..11 |
| | note = An artificially synthesized sequence |
| REGION | 1..11 |
| | note = MOD_RES - Cyclization |
| SITE | 2 |
| | note = MISC_FEATURE - Xaa = tBuSSlac |
| SITE | 4 |
| | note = MISC_FEATURE - Xaa = Lys(Alloc-Cys(StBu)) |
| SITE | 6 |
| | note = MISC_FEATURE - Xaa = MeAla |
| SITE | 7 |
| | note = MISC_FEATURE - Xaa = MeLeu |
| SITE | 9 |
| | note = MISC_FEATURE - Xaa = MePhe |
| SITE | 10 |
| | note = MISC_FEATURE - Xaa = MeAla |
| source | 1..11 |
| | mol_type = protein |
| | organism = synthetic construct |

SEQUENCE: 274
FXFXLXXAXX A                                                                11

| | |
|---|---|
| SEQ ID NO: 275 | moltype = AA  length = 11 |
| FEATURE | Location/Qualifiers |
| REGION | 1..11 |
| | note = An artificially synthesized sequence |
| REGION | 1..11 |
| | note = MOD_RES - Cyclization |
| SITE | 2 |
| | note = MISC_FEATURE - Xaa = tBuSSlac |
| SITE | 4 |
| | note = MISC_FEATURE - Xaa = Lys(H-Cys(StBu)) |
| SITE | 6 |
| | note = MISC_FEATURE - Xaa = MeAla |
| SITE | 7 |
| | note = MISC_FEATURE - Xaa = MeLeu |
| SITE | 9 |
| | note = MISC_FEATURE - Xaa = MePhe |
| SITE | 10 |
| | note = MISC_FEATURE - Xaa = MeAla |
| source | 1..11 |
| | mol_type = protein |
| | organism = synthetic construct |

SEQUENCE: 275
FXFXLXXAXX A                                                                11

| | |
|---|---|
| SEQ ID NO: 276 | moltype = AA  length = 11 |
| FEATURE | Location/Qualifiers |
| REGION | 1..11 |
| | note = An artificially synthesized sequence |
| SITE | 1 |
| | note = MISC_FEATURE - Xaa = H-HSlac |
| SITE | 3 |
| | note = MISC_FEATURE - Xaa = Lys(Cys) |
| REGION | 3..11 |
| | note = MOD_RES - Cyclization |
| SITE | 5 |
| | note = MISC_FEATURE - Xaa = MeAla |
| SITE | 6 |
| | note = MISC_FEATURE - Xaa = MeLeu |
| SITE | 8 |
| | note = MISC_FEATURE - Xaa = MePhe |
| SITE | 9 |
| | note = MISC_FEATURE - Xaa = MeAla |
| source | 1..11 |

-continued

```
                        mol_type = protein
                        organism = synthetic construct
SEQUENCE: 276
XFXLXXAXXA F                                                                11

SEQ ID NO: 277          moltype = AA  length = 11
FEATURE                 Location/Qualifiers
REGION                  1..11
                        note = An artificially synthesized sequence
REGION                  1..11
                        note = MOD RES - Cyclization
SITE                    2
                        note = MISC_FEATURE - Xaa = tBuSSlac
SITE                    4
                        note = MISC_FEATURE - Xaa = Lys(H-Cys(StBu))
SITE                    6
                        note = MISC_FEATURE - Xaa = MeAla
SITE                    7
                        note = MISC_FEATURE - Xaa = MeLeu
SITE                    9
                        note = MISC_FEATURE - Xaa = MePhe
SITE                    10
                        note = MISC_FEATURE - Xaa = MeAla
source                  1..11
                        mol_type = protein
                        organism = synthetic construct
SEQUENCE: 277
FXFXLXXAXXX A                                                               11

SEQ ID NO: 278          moltype = AA  length = 11
FEATURE                 Location/Qualifiers
REGION                  1..11
                        note = An artificially synthesized sequence
SITE                    1
                        note = MISC_FEATURE - Xaa = H-lac
SITE                    3
                        note = MISC_FEATURE - Xaa = Lys(Ala)
REGION                  3..11
                        note = MOD RES - Cyclization
SITE                    5
                        note = MISC_FEATURE - Xaa = MeAla
SITE                    6
                        note = MISC_FEATURE - Xaa = MeLeu
SITE                    8
                        note = MISC_FEATURE - Xaa = MePhe
SITE                    9
                        note = MISC_FEATURE - Xaa = MeAla
source                  1..11
                        mol_type = protein
                        organism = synthetic construct
SEQUENCE: 278
XFXLXXAXXA F                                                                11

SEQ ID NO: 279          moltype = AA  length = 12
FEATURE                 Location/Qualifiers
REGION                  1..12
                        note = An artificially synthesized sequence
SITE                    1
                        note = MISC_FEATURE - Xaa = fMet
SITE                    3
                        note = MISC_FEATURE - Xaa = Ala(Tzm)
source                  1..12
                        mol_type = protein
                        organism = synthetic construct
SEQUENCE: 279
XRXRDYKDDD DK                                                               12

SEQ ID NO: 280          moltype = AA  length = 12
FEATURE                 Location/Qualifiers
REGION                  1..12
                        note = An artificially synthesized sequence
SITE                    1
                        note = MISC_FEATURE - Xaa = fMet
SITE                    3
                        note = MISC_FEATURE - Xaa = Orn
source                  1..12
                        mol_type = protein
                        organism = synthetic construct
SEQUENCE: 280
```

```
XRXRDYKDDD DK                                                            12

SEQ ID NO: 281           moltype = AA   length = 12
FEATURE                  Location/Qualifiers
REGION                   1..12
                         note = An artificially synthesized sequence
SITE                     1
                         note = MISC_FEATURE - Xaa = fMet
SITE                     3
                         note = MISC_FEATURE - Xaa = Orn(oAcbz)
source                   1..12
                         mol_type = protein
                         organism = synthetic construct
SEQUENCE: 281
XRXRDYKDDD DK                                                            12

SEQ ID NO: 282           moltype = AA   length = 12
FEATURE                  Location/Qualifiers
REGION                   1..12
                         note = An artificially synthesized sequence
SITE                     1
                         note = MISC_FEATURE - Xaa = fMet
SITE                     3
                         note = MISC_FEATURE - Xaa = Lys(Npys)
source                   1..12
                         mol_type = protein
                         organism = synthetic construct
SEQUENCE: 282
XRXRDYKDDD DK                                                            12

SEQ ID NO: 283           moltype = AA   length = 12
FEATURE                  Location/Qualifiers
REGION                   1..12
                         note = An artificially synthesized sequence
SITE                     1
                         note = MISC_FEATURE - Xaa = fMet
SITE                     3
                         note = MISC_FEATURE - Xaa = 5S-SSMe
source                   1..12
                         mol_type = protein
                         organism = synthetic construct
SEQUENCE: 283
XRXRDYKDDD DK                                                            12

SEQ ID NO: 284           moltype = AA   length = 11
FEATURE                  Location/Qualifiers
REGION                   1..11
                         note = An artificially synthesized sequence
SITE                     1
                         note = MISC_FEATURE - Xaa = PenteA
SITE                     3
                         note = MISC_FEATURE - Xaa = Phe(3-I)
source                   1..11
                         mol_type = protein
                         organism = synthetic construct
SEQUENCE: 284
XFXPSGSGSG S                                                             11

SEQ ID NO: 285           moltype = AA   length = 14
FEATURE                  Location/Qualifiers
REGION                   1..14
                         note = An artificially synthesized sequence
SITE                     1
                         note = MISC_FEATURE - Xaa = PenteA
SITE                     11
                         note = MISC_FEATURE - Xaa = Phe(3-I)
source                   1..14
                         mol_type = protein
                         organism = synthetic construct
SEQUENCE: 285
XTTTSGSGSF XPGS                                                          14

SEQ ID NO: 286           moltype = AA   length = 14
FEATURE                  Location/Qualifiers
REGION                   1..14
                         note = An artificially synthesized sequence
SITE                     1
                         note = MISC_FEATURE - Xaa = PenteA
SITE                     11
```

```
                        note = MISC_FEATURE - Xaa = Phe(3-I)
source                  1..14
                        mol_type = protein
                        organism = synthetic construct
SEQUENCE: 286
XNNNNNTTTG XPGS                                                               14

SEQ ID NO: 287          moltype = AA  length = 8
FEATURE                 Location/Qualifiers
REGION                  1..8
                        note = An artificially synthesized sequence
source                  1..8
                        mol_type = protein
                        organism = synthetic construct
SEQUENCE: 287
PSGSGSGS                                                                       8

SEQ ID NO: 288          moltype = AA  length = 21
FEATURE                 Location/Qualifiers
REGION                  1..21
                        note = An artificially synthesized sequence
SITE                    5
                        note = MISC_FEATURE - Xaa = MePhe
SITE                    6
                        note = MISC_FEATURE - Xaa = Met(O2)
SITE                    8
                        note = MISC_FEATURE - Xaa = MePhe(3-Cl)
SITE                    9
                        note = MISC_FEATURE - Xaa = DTyr
SITE                    21
                        note = MISC_FEATURE - Xaa = FlPu(urea)
source                  1..21
                        mol_type = protein
                        organism = synthetic construct
SEQUENCE: 288
APIIXXPXXV DSTSGSGSGS X                                                       21

SEQ ID NO: 289          moltype = AA  length = 21
FEATURE                 Location/Qualifiers
REGION                  1..21
                        note = An artificially synthesized sequence
SITE                    6
                        note = MISC_FEATURE - Xaa = MePhe(3-Cl)
SITE                    7
                        note = MISC_FEATURE - Xaa = Met(O2)
SITE                    9
                        note = MISC_FEATURE - Xaa = MePhe(3-Cl)
SITE                    10
                        note = MISC_FEATURE - Xaa = DTyr
SITE                    13
                        note = MISC_FEATURE - Xaa = DTyr
SITE                    21
                        note = MISC_FEATURE - Xaa = FlPu(urea)
source                  1..21
                        mol_type = protein
                        organism = synthetic construct
SEQUENCE: 289
APIIWXXPXX DVXSGSGSGS X                                                       21

SEQ ID NO: 290          moltype = AA  length = 21
FEATURE                 Location/Qualifiers
REGION                  1..21
                        note = An artificially synthesized sequence
SITE                    2
                        note = MISC_FEATURE - Xaa = DTyr
SITE                    5
                        note = MISC_FEATURE - Xaa = Met(O2)
SITE                    7
                        note = MISC_FEATURE - Xaa = Met(O2)
SITE                    8
                        note = MISC_FEATURE - Xaa = MePhe(3-Cl)
SITE                    10
                        note = MISC_FEATURE - Xaa = MePhe
SITE                    13
                        note = MISC_FEATURE - Xaa = MePhe(3-Cl)
SITE                    21
                        note = MISC_FEATURE - Xaa = FlPu(urea)
source                  1..21
                        mol_type = protein
```

```
                    organism = synthetic construct
SEQUENCE: 290
AXIWXSXXVX DTXSGSGSGS X                                     21

SEQ ID NO: 291        moltype = AA  length = 21
FEATURE               Location/Qualifiers
REGION                1..21
                      note = An artificially synthesized sequence
SITE                  3
                      note = MISC_FEATURE - Xaa = MeGly
SITE                  8
                      note = MISC_FEATURE - Xaa = MeSer
SITE                  9
                      note = MISC_FEATURE - Xaa = Phg
SITE                  10
                      note = MISC_FEATURE - Xaa = Phg
SITE                  12
                      note = MISC_FEATURE - Xaa = MeAla(4-Thz)
SITE                  21
                      note = MISC_FEATURE - Xaa = FlPu(urea)
source                1..21
                      mol_type = protein
                      organism = synthetic construct
SEQUENCE: 291
APXIIVSXXX DXTSGSGSGS X                                     21

SEQ ID NO: 292        moltype = AA  length = 21
FEATURE               Location/Qualifiers
REGION                1..21
                      note = An artificially synthesized sequence
SITE                  3
                      note = MISC_FEATURE - Xaa = MeGly
SITE                  8
                      note = MISC_FEATURE - Xaa = MeSer
SITE                  9
                      note = MISC_FEATURE - Xaa = Phg
SITE                  12
                      note = MISC_FEATURE - Xaa = MeAla
SITE                  13
                      note = MISC_FEATURE - Xaa = MePhe(3-Cl)
SITE                  21
                      note = MISC_FEATURE - Xaa = FlPu(urea)
source                1..21
                      mol_type = protein
                      organism = synthetic construct
SEQUENCE: 292
APXVITVXXS DXXSGSGSGS X                                     21

SEQ ID NO: 293        moltype = AA  length = 21
FEATURE               Location/Qualifiers
REGION                1..21
                      note = An artificially synthesized sequence
SITE                  1
                      note = MISC_FEATURE - Xaa = gamma EtAbu
SITE                  3
                      note = MISC_FEATURE - Xaa = Phg
SITE                  5
                      note = MISC_FEATURE - Xaa = MeAla(4-Thz)
SITE                  8
                      note = MISC_FEATURE - Xaa = Phe(4-CF3)
SITE                  9
                      note = MISC_FEATURE - Xaa = DTyr
SITE                  10
                      note = MISC_FEATURE - Xaa = MePhe(3-Cl)
SITE                  13
                      note = MISC_FEATURE - Xaa = MeGly
SITE                  21
                      note = MISC_FEATURE - Xaa = FlPu(urea)
source                1..21
                      mol_type = protein
                      organism = synthetic construct
SEQUENCE: 293
XTXIXWWXXX DPXSGSGSGS X                                     21

SEQ ID NO: 294        moltype = AA  length = 21
FEATURE               Location/Qualifiers
REGION                1..21
                      note = An artificially synthesized sequence
SITE                  2
```

```
                          note = MISC_FEATURE - Xaa = Phe(4-CF3)
SITE                      6
                          note = MISC_FEATURE - Xaa = MeGly
SITE                      9
                          note = MISC_FEATURE - Xaa = Hyp(Et)
SITE                      12
                          note = MISC_FEATURE - Xaa = MeSer
SITE                      13
                          note = MISC_FEATURE - Xaa = Met(O2)
SITE                      21
                          note = MISC_FEATURE - Xaa = FlPu(urea)
source                    1..21
                          mol_type = protein
                          organism = synthetic construct
SEQUENCE: 294
AXWWVXGPXS DXXSGSGSGS X                                              21

SEQ ID NO: 295            moltype = AA  length = 21
FEATURE                   Location/Qualifiers
REGION                    1..21
                          note = An artificially synthesized sequence
SITE                      2
                          note = MISC_FEATURE - Xaa = MeAla(4-Thz)
SITE                      8
                          note = MISC_FEATURE - Xaa = Phe(4-CF3)
SITE                      9
                          note = MISC_FEATURE - Xaa = Met(O2)
SITE                      13
                          note = MISC_FEATURE - Xaa = MeAla(4-Thz)
SITE                      21
                          note = MISC_FEATURE - Xaa = FlPu(urea)
source                    1..21
                          mol_type = protein
                          organism = synthetic construct
SEQUENCE: 295
AXIPVWWXXV DWXSGSGSGS X                                              21

SEQ ID NO: 296            moltype = AA  length = 21
FEATURE                   Location/Qualifiers
REGION                    1..21
                          note = An artificially synthesized sequence
SITE                      5
                          note = MISC_FEATURE - Xaa = DTyr
SITE                      8
                          note = MISC_FEATURE - Xaa = Phe(4-CF3)
SITE                      9
                          note = MISC_FEATURE - Xaa = Met(O2)
SITE                      13
                          note = MISC_FEATURE - Xaa = MeAla(4-Thz)
SITE                      21
                          note = MISC_FEATURE - Xaa = FlPu(urea)
source                    1..21
                          mol_type = protein
                          organism = synthetic construct
SEQUENCE: 296
ATIPXWWXXV DWXSGSGSGS X                                              21

SEQ ID NO: 297            moltype = AA  length = 21
FEATURE                   Location/Qualifiers
REGION                    1..21
                          note = An artificially synthesized sequence
SITE                      5
                          note = MISC_FEATURE - Xaa = MePhe
SITE                      6
                          note = MISC_FEATURE - Xaa = Phg
SITE                      8
                          note = MISC_FEATURE - Xaa = beta Ala
SITE                      9
                          note = MISC_FEATURE - Xaa = Phe(4-CF3)
SITE                      10
                          note = MISC_FEATURE - Xaa = Phg
SITE                      21
                          note = MISC_FEATURE - Xaa = FlPu(urea)
source                    1..21
                          mol_type = protein
                          organism = synthetic construct
SEQUENCE: 297
ATWIXXWXXX DVTSGSGSGS X                                              21
```

```
SEQ ID NO: 298          moltype = AA  length = 21
FEATURE                 Location/Qualifiers
REGION                  1..21
                        note = An artificially synthesized sequence
SITE                    5
                        note = MISC_FEATURE - Xaa = MePhe
SITE                    6
                        note = MISC_FEATURE - Xaa = Met(O2)
SITE                    8
                        note = MISC_FEATURE - Xaa = MePhe(3-Cl)
SITE                    10
                        note = MISC_FEATURE - Xaa = Met(O2)
SITE                    13
                        note = MISC_FEATURE - Xaa = MeGly
SITE                    21
                        note = MISC_FEATURE - Xaa = FlPu(urea)
source                  1..21
                        mol_type = protein
                        organism = synthetic construct
SEQUENCE: 298
APVIXXPXVX DPXSGSGSGS X                                                    21

SEQ ID NO: 299          moltype = AA  length = 21
FEATURE                 Location/Qualifiers
REGION                  1..21
                        note = An artificially synthesized sequence
SITE                    4
                        note = MISC_FEATURE - Xaa = MeAla(4-Thz)
SITE                    7
                        note = MISC_FEATURE - Xaa = MePhe(3-Cl)
SITE                    8
                        note = MISC_FEATURE - Xaa = Met(O2)
SITE                    9
                        note = MISC_FEATURE - Xaa = DTyr
SITE                    10
                        note = MISC_FEATURE - Xaa = beta Ala
SITE                    13
                        note = MISC_FEATURE - Xaa = MePhe(3-Cl)
SITE                    21
                        note = MISC_FEATURE - Xaa = FlPu(urea)
source                  1..21
                        mol_type = protein
                        organism = synthetic construct
SEQUENCE: 299
AIIXWPXXXX DPXSGSGSGS X                                                    21

SEQ ID NO: 300          moltype = AA  length = 21
FEATURE                 Location/Qualifiers
REGION                  1..21
                        note = An artificially synthesized sequence
SITE                    1
                        note = MISC_FEATURE - Xaa = gamma EtAbu
SITE                    5
                        note = MISC_FEATURE - Xaa = MePhe(3-Cl)
SITE                    6
                        note = MISC_FEATURE - Xaa = Met(O2)
SITE                    8
                        note = MISC_FEATURE - Xaa = MePhe(3-Cl)
SITE                    9
                        note = MISC_FEATURE - Xaa = DTyr
SITE                    10
                        note = MISC_FEATURE - Xaa = Met(O2)
SITE                    12
                        note = MISC_FEATURE - Xaa = MeAla(4-Thz)
SITE                    13
                        note = MISC_FEATURE - Xaa = MeAla
SITE                    21
                        note = MISC_FEATURE - Xaa = FlPu(urea)
source                  1..21
                        mol_type = protein
                        organism = synthetic construct
SEQUENCE: 300
XIVWXXPXXX DXXSGSGSGS X                                                    21

SEQ ID NO: 301          moltype = AA  length = 8
FEATURE                 Location/Qualifiers
REGION                  1..8
                        note = An artificially synthesized sequence
SITE                    8
```

```
                         note = MISC_FEATURE - Xaa = FlPu(urea)
source                   1..8
                         mol_type = protein
                         organism = synthetic construct
SEQUENCE: 301
SGSGSGSX                                                                   8

SEQ ID NO: 302           moltype = AA   length = 14
FEATURE                  Location/Qualifiers
REGION                   1..14
                         note = An artificially synthesized sequence
SITE                     1
                         note = MISC_FEATURE - Xaa = gamma EtAbu
REGION                   1..11
                         note = MOD RES - Cyclization
SITE                     3
                         note = MISC_FEATURE - Xaa = Phg
SITE                     5
                         note = MISC_FEATURE - Xaa = MeAla(4-Thz)
SITE                     8
                         note = MISC_FEATURE - Xaa = Phe(4-CF3)
SITE                     9
                         note = MISC_FEATURE - Xaa = DTyr
SITE                     10
                         note = MISC_FEATURE - Xaa = MePhe(3-Cl)
SITE                     13
                         note = MISC_FEATURE - Xaa = MeGly
source                   1..14
                         mol_type = protein
                         organism = synthetic construct
SEQUENCE: 302
XTXIXWWXXX DPXS                                                           14

SEQ ID NO: 303           moltype = AA   length = 14
FEATURE                  Location/Qualifiers
REGION                   1..14
                         note = An artificially synthesized sequence
REGION                   1..11
                         note = MOD RES - Cyclization
SITE                     2
                         note = MISC_FEATURE - Xaa = Phe(4-CF3)
SITE                     6
                         note = MISC_FEATURE - Xaa = MeGly
SITE                     9
                         note = MISC_FEATURE - Xaa = Hyp(Et)
SITE                     12
                         note = MISC_FEATURE - Xaa = MeSer
SITE                     13
                         note = MISC_FEATURE - Xaa = Met(O2)
source                   1..14
                         mol_type = protein
                         organism = synthetic construct
SEQUENCE: 303
AXWWVXGPXS DXXS                                                           14

SEQ ID NO: 304           moltype = AA   length = 14
FEATURE                  Location/Qualifiers
REGION                   1..14
                         note = An artificially synthesized sequence
REGION                   1..11
                         note = MOD RES - Cyclization
SITE                     2
                         note = MISC_FEATURE - Xaa = MeAla(4-Thz)
SITE                     8
                         note = MISC_FEATURE - Xaa = Phe(4-CF3)
SITE                     9
                         note = MISC_FEATURE - Xaa = Met(O2)
SITE                     13
                         note = MISC_FEATURE - Xaa = MeAla(4-Thz)
source                   1..14
                         mol_type = protein
                         organism = synthetic construct
SEQUENCE: 304
AXIPVWWXXV DWXS                                                           14

SEQ ID NO: 305           moltype = AA   length = 14
FEATURE                  Location/Qualifiers
REGION                   1..14
                         note = An artificially synthesized sequence
```

```
REGION              1..11
                    note = MOD_RES - Cyclization
SITE                5
                    note = MISC_FEATURE - Xaa = DTyr
SITE                8
                    note = MISC_FEATURE - Xaa = Phe(4-CF3)
SITE                9
                    note = MISC_FEATURE - Xaa = Met(O2)
SITE                13
                    note = MISC_FEATURE - Xaa = MeAla(4-Thz)
source              1..14
                    mol_type = protein
                    organism = synthetic construct
SEQUENCE: 305
ATIPXWWXXV DWXS                                                             14

SEQ ID NO: 306      moltype = AA  length = 14
FEATURE             Location/Qualifiers
REGION              1..14
                    note = An artificially synthesized sequence
REGION              1..11
                    note = MOD_RES - Cyclization
SITE                5
                    note = MISC_FEATURE - Xaa = MePhe
SITE                6
                    note = MISC_FEATURE - Xaa = Phg
SITE                8
                    note = MISC_FEATURE - Xaa = beta Ala
SITE                9
                    note = MISC_FEATURE - Xaa = Phe(4-CF3)
SITE                10
                    note = MISC_FEATURE - Xaa = Phg
source              1..14
                    mol_type = protein
                    organism = synthetic construct
SEQUENCE: 306
ATWIXXWXXX DVTS                                                             14

SEQ ID NO: 307      moltype = AA  length = 14
FEATURE             Location/Qualifiers
REGION              1..14
                    note = An artificially synthesized sequence
REGION              1..11
                    note = MOD_RES - Cyclization
SITE                5
                    note = MISC_FEATURE - Xaa = MePhe
SITE                6
                    note = MISC_FEATURE - Xaa = Met(O2)
SITE                8
                    note = MISC_FEATURE - Xaa = MePhe(3-Cl)
SITE                10
                    note = MISC_FEATURE - Xaa = Met(O2)
SITE                13
                    note = MISC_FEATURE - Xaa = MeGly
source              1..14
                    mol_type = protein
                    organism = synthetic construct
SEQUENCE: 307
APVIXXPXVX DPXS                                                             14

SEQ ID NO: 308      moltype = AA  length = 14
FEATURE             Location/Qualifiers
REGION              1..14
                    note = An artificially synthesized sequence
REGION              1..11
                    note = MOD_RES - Cyclization
SITE                4
                    note = MISC_FEATURE - Xaa = MeAla(4-Thz)
SITE                7
                    note = MISC_FEATURE - Xaa = MePhe(3-Cl)
SITE                8
                    note = MISC_FEATURE - Xaa = Met(O2)
SITE                9
                    note = MISC_FEATURE - Xaa = DTyr
SITE                10
                    note = MISC_FEATURE - Xaa = beta Ala
SITE                13
                    note = MISC_FEATURE - Xaa = MePhe(3-Cl)
source              1..14
```

```
                        mol_type = protein
                        organism = synthetic construct
SEQUENCE: 308
AIIXWPXXXX DPXS                                                              14

SEQ ID NO: 309          moltype = AA  length = 14
FEATURE                 Location/Qualifiers
REGION                  1..14
                        note = An artificially synthesized sequence
SITE                    1
                        note = MISC_FEATURE - Xaa = gamma EtAbu
REGION                  1..11
                        note = MOD_RES - Cyclization
SITE                    5
                        note = MISC_FEATURE - Xaa = MePhe(3-Cl)
SITE                    6
                        note = MISC_FEATURE - Xaa = Met(O2)
SITE                    8
                        note = MISC_FEATURE - Xaa = MePhe(3-Cl)
SITE                    9
                        note = MISC_FEATURE - Xaa = DTyr
SITE                    10
                        note = MISC_FEATURE - Xaa = Met(O2)
SITE                    12
                        note = MISC_FEATURE - Xaa = MeAla(4-Thz)
SITE                    13
                        note = MISC_FEATURE - Xaa = MeAla
source                  1..14
                        mol_type = protein
                        organism = synthetic construct
SEQUENCE: 309
XIVWXXPXXX DXXS                                                              14

SEQ ID NO: 310          moltype = AA  length = 14
FEATURE                 Location/Qualifiers
REGION                  1..14
                        note = An artificially synthesized sequence
REGION                  1..11
                        note = MOD_RES - Cyclization
SITE                    5
                        note = MISC_FEATURE - Xaa = MePhe
SITE                    6
                        note = MISC_FEATURE - Xaa = Met(O2)
SITE                    8
                        note = MISC_FEATURE - Xaa = MePhe(3-Cl)
SITE                    10
                        note = MISC_FEATURE - Xaa = Met(O2)
SITE                    13
                        note = MISC_FEATURE - Xaa = MeGly
SITE                    14
                        note = MISC_FEATURE - Xaa = Ser-NH(CH2)2NMe2
source                  1..14
                        mol_type = protein
                        organism = synthetic construct
SEQUENCE: 310
APVIXXPXVX DPXX                                                              14

SEQ ID NO: 311          moltype = AA  length = 14
FEATURE                 Location/Qualifiers
REGION                  1..14
                        note = An artificially synthesized sequence
REGION                  1..11
                        note = MOD_RES - Cyclization
SITE                    5
                        note = MISC_FEATURE - Xaa = MePhe
SITE                    6
                        note = MISC_FEATURE - Xaa = Met(O2)
SITE                    8
                        note = MISC_FEATURE - Xaa = MePhe(3-Cl)
SITE                    10
                        note = MISC_FEATURE - Xaa = Met(O2)
SITE                    13
                        note = MISC_FEATURE - Xaa = MeGly
SITE                    13
                        note = MISC_FEATURE - Xaa = MeGly
source                  1..14
                        mol_type = protein
                        organism = synthetic construct
SEQUENCE: 311
```

-continued

```
APVIXXPXVX DPXS                                                       14

SEQ ID NO: 312          moltype = AA  length = 13
FEATURE                 Location/Qualifiers
REGION                  1..13
                        note = An artificially synthesized sequence
SITE                    7
                        note = MISC_FEATURE - Xaa = Asp(SBn)
source                  1..13
                        mol_type = protein
                        organism = synthetic construct
SEQUENCE: 312
MTTTGGXFFR GGK                                                        13

SEQ ID NO: 313          moltype = AA  length = 13
FEATURE                 Location/Qualifiers
REGION                  1..13
                        note = An artificially synthesized sequence
SITE                    1
                        note = MISC_FEATURE - Xaa = HSEtGABA
REGION                  1..10
                        note = MOD_RES - Cyclization
source                  1..13
                        mol_type = protein
                        organism = synthetic construct
SEQUENCE: 313
XTRTKAYWSD PGG                                                        13

SEQ ID NO: 314          moltype = AA  length = 12
FEATURE                 Location/Qualifiers
REGION                  1..12
                        note = An artificially synthesized sequence
REGION                  1..10
                        note = MOD_RES - Cyclization
SITE                    6
                        note = MISC_FEATURE - Xaa = Lac
source                  1..12
                        mol_type = protein
                        organism = synthetic construct
SEQUENCE: 314
CTRTKXYWSD PG                                                         12

SEQ ID NO: 315          moltype =    length =
SEQUENCE: 315
000

SEQ ID NO: 316          moltype =    length =
SEQUENCE: 316
000

SEQ ID NO: 317          moltype =    length =
SEQUENCE: 317
000

SEQ ID NO: 318          moltype =    length =
SEQUENCE: 318
000

SEQ ID NO: 319          moltype =    length =
SEQUENCE: 319
000

SEQ ID NO: 320          moltype =    length =
SEQUENCE: 320
000

SEQ ID NO: 321          moltype =    length =
SEQUENCE: 321
000

SEQ ID NO: 322          moltype =    length =
SEQUENCE: 322
000

SEQ ID NO: 323          moltype = AA  length = 12
FEATURE                 Location/Qualifiers
REGION                  1..12
                        note = An artificially synthesized sequence
SITE                    1
```

```
                         note = MISC_FEATURE - Xaa = HOGly
SITE                     3
                         note = MISC_FEATURE - Xaa = MeLeu
REGION                   4..12
                         note = Cyclization - Cyclization
SITE                     5
                         note = MISC_FEATURE - Xaa = MeAla
SITE                     7
                         note = MISC_FEATURE - Xaa = MeLeu
SITE                     8
                         note = MISC_FEATURE - Xaa = MeLeu
SITE                     9
                         note = MISC_FEATURE - Xaa = Asp-piperidine
SITE                     10
                         note = MISC_FEATURE - Xaa = MeLeu
SITE                     11
                         note = MISC_FEATURE - Xaa = MePhe(3-Cl)
source                   1..12
                         mol_type = protein
                         organism = synthetic construct
SEQUENCE: 323
XPXKXLXXXX XI                                                              12

SEQ ID NO: 324           moltype = AA  length = 10
FEATURE                  Location/Qualifiers
REGION                   1..10
                         note = An artificially synthesized sequence
REGION                   1..10
                         note = MOD_RES - Cyclization
SITE                     2
                         note = MISC_FEATURE - Xaa = MeLeu
SITE                     3
                         note = MISC_FEATURE - Xaa = MeVal
SITE                     4
                         note = MISC_FEATURE - Xaa = MeGly
SITE                     6
                         note = MISC_FEATURE - Xaa = MeAla
SITE                     8
                         note = MISC_FEATURE - Xaa = MeLeu
SITE                     10
                         note = MISC_FEATURE - Xaa = Phe-piperidine
source                   1..10
                         mol_type = protein
                         organism = synthetic construct
SEQUENCE: 324
FXXXTXAXLX                                                                 10

SEQ ID NO: 325           moltype = AA  length = 10
FEATURE                  Location/Qualifiers
REGION                   1..10
                         note = An artificially synthesized sequence
SITE                     2
                         note = MISC_FEATURE - Xaa = MeLeu
SITE                     3
                         note = MISC_FEATURE - Xaa = MeVal
SITE                     4
                         note = MISC_FEATURE - Xaa = MeGly
SITE                     6
                         note = MISC_FEATURE - Xaa = MeAla
SITE                     8
                         note = MISC_FEATURE - Xaa = MeLeu
SITE                     10
                         note = MISC_FEATURE - Xaa = Phe(3-I)-piperidine
source                   1..10
                         mol_type = protein
                         organism = synthetic construct
SEQUENCE: 325
FXXXTXAXLX                                                                 10

SEQ ID NO: 326           moltype = AA  length = 12
FEATURE                  Location/Qualifiers
REGION                   1..12
                         note = An artificially synthesized sequence
SITE                     3
                         note = MISC_FEATURE - Xaa = MePhe
SITE                     5
                         note = MISC_FEATURE - Xaa = MeLeu
SITE                     9
                         note = MISC_FEATURE - Xaa = Asp(SBn)
```

```
SITE                    10
                        note = MISC_FEATURE - Xaa = MeAla
SITE                    12
                        note = MISC_FEATURE - Xaa = Gly-NH2
source                  1..12
                        mol_type = protein
                        organism = synthetic construct
SEQUENCE: 326
GAXGXAVFXX SX                                                                   12

SEQ ID NO: 327          moltype = AA  length = 12
FEATURE                 Location/Qualifiers
REGION                  1..12
                        note = An artificially synthesized sequence
SITE                    1
                        note = MISC_FEATURE - Xaa = Boc-Ala
SITE                    3
                        note = MISC_FEATURE - Xaa = MeLeu
SITE                    4
                        note = MISC_FEATURE - Xaa = Thr(Trt)
SITE                    5
                        note = MISC_FEATURE - Xaa = MePhe
SITE                    7
                        note = MISC_FEATURE - Xaa = MeLeu
SITE                    8
                        note = MISC_FEATURE - Xaa = MeVal
SITE                    11
                        note = MISC_FEATURE - Xaa = MePhe
SITE                    12
                        note = MISC_FEATURE - Xaa = Ala-piperidine
source                  1..12
                        mol_type = protein
                        organism = synthetic construct
SEQUENCE: 327
XVXXXGXXFD XX                                                                   12

SEQ ID NO: 328          moltype =    length =
SEQUENCE: 328
000

SEQ ID NO: 329          moltype =    length =
SEQUENCE: 329
000

SEQ ID NO: 330          moltype = AA  length = 12
FEATURE                 Location/Qualifiers
REGION                  1..12
                        note = An artificially synthesized sequence
SITE                    3
                        note = MISC_FEATURE - Xaa = MeLeu
SITE                    5
                        note = MISC_FEATURE - Xaa = MePhe
SITE                    7
                        note = MISC_FEATURE - Xaa = MeLeu
SITE                    8
                        note = MISC_FEATURE - Xaa = MeVal
SITE                    10
                        note = MISC_FEATURE - Xaa = Asp(SBn)
SITE                    11
                        note = MISC_FEATURE - Xaa = MePhe
SITE                    12
                        note = MISC_FEATURE - Xaa = Ala-piperidine
source                  1..12
                        mol_type = protein
                        organism = synthetic construct
SEQUENCE: 330
AVXTXGXXFX XX                                                                   12

SEQ ID NO: 331          moltype = AA  length = 12
FEATURE                 Location/Qualifiers
REGION                  1..12
                        note = An artificially synthesized sequence
SITE                    1
                        note = MISC_FEATURE - Xaa = Boc-Ala
SITE                    3
                        note = MISC_FEATURE - Xaa = MePhe
SITE                    10
                        note = MISC_FEATURE - Xaa = MeAla
SITE                    11
```

```
                        note = MISC_FEATURE - Xaa = Ser(tBu)
SITE                    12
                        note = MISC_FEATURE - Xaa = Gly-NH2
source                  1..12
                        mol_type = protein
                        organism = synthetic construct
SEQUENCE: 331
XAXGLAVFDX XX                                                                12

SEQ ID NO: 332          moltype = AA  length = 12
FEATURE                 Location/Qualifiers
REGION                  1..12
                        note = An artificially synthesized sequence
SITE                    1
                        note = MISC_FEATURE - Xaa = Boc-Ala
SITE                    3
                        note = MISC_FEATURE - Xaa = MePhe
SITE                    9
                        note = MISC_FEATURE - Xaa = Asp(OBn)
SITE                    10
                        note = MISC_FEATURE - Xaa = MeAla
SITE                    11
                        note = MISC_FEATURE - Xaa = Ser(tBu)
SITE                    12
                        note = MISC_FEATURE - Xaa = Gly-NH2
source                  1..12
                        mol_type = protein
                        organism = synthetic construct
SEQUENCE: 332
XAXGLAVFXX XX                                                                12

SEQ ID NO: 333          moltype = AA  length = 12
FEATURE                 Location/Qualifiers
REGION                  1..12
                        note = An artificially synthesized sequence
SITE                    1
                        note = MISC_FEATURE - Xaa = Boc-Ala
SITE                    3
                        note = MISC_FEATURE - Xaa = MePhe
SITE                    9
                        note = MISC_FEATURE - Xaa = Asp(SBn)
SITE                    10
                        note = MISC_FEATURE - Xaa = MeAla
SITE                    11
                        note = MISC_FEATURE - Xaa = Ser(tBu)
SITE                    12
                        note = MISC_FEATURE - Xaa = Gly-NH2
source                  1..12
                        mol_type = protein
                        organism = synthetic construct
SEQUENCE: 333
XAXGLAVFXX XX                                                                12

SEQ ID NO: 334          moltype = AA  length = 12
FEATURE                 Location/Qualifiers
REGION                  1..12
                        note = An artificially synthesized sequence
SITE                    3
                        note = MISC_FEATURE - Xaa = MePhe
SITE                    9
                        note = MISC_FEATURE - Xaa = Asp(SBn)
SITE                    10
                        note = MISC_FEATURE - Xaa = MeAla
SITE                    12
                        note = MISC_FEATURE - Xaa = Gly-NH2
source                  1..12
                        mol_type = protein
                        organism = synthetic construct
SEQUENCE: 334
AAXGLAVFXX SX                                                                12

SEQ ID NO: 335          moltype = AA  length = 12
FEATURE                 Location/Qualifiers
REGION                  1..12
                        note = An artificially synthesized sequence
SITE                    1
                        note = MISC_FEATURE - Xaa = Boc-Phe
SITE                    3
                        note = MISC_FEATURE - Xaa = MePhe
```

```
SITE             10
                 note = MISC_FEATURE - Xaa = MeAla
SITE             11
                 note = MISC_FEATURE - Xaa = Ser(tBu)
SITE             12
                 note = MISC_FEATURE - Xaa = Gly-NH2
source           1..12
                 mol_type = protein
                 organism = synthetic construct
SEQUENCE: 335
XAXGLAVFDX XX                                                                      12

SEQ ID NO: 336   moltype = AA  length = 12
FEATURE          Location/Qualifiers
REGION           1..12
                 note = An artificially synthesized sequence
SITE             1
                 note = MISC_FEATURE - Xaa = Boc-Phe
SITE             3
                 note = MISC_FEATURE - Xaa = MePhe
SITE             9
                 note = MISC_FEATURE - Xaa = Asp(OBn)
SITE             10
                 note = MISC_FEATURE - Xaa = MeAla
SITE             11
                 note = MISC_FEATURE - Xaa = Ser(OtBu)
SITE             12
                 note = MISC_FEATURE - Xaa = Gly-NH2
source           1..12
                 mol_type = protein
                 organism = synthetic construct
SEQUENCE: 336
XAXGLAVFXX XX                                                                      12

SEQ ID NO: 337   moltype = AA  length = 12
FEATURE          Location/Qualifiers
REGION           1..12
                 note = An artificially synthesized sequence
SITE             1
                 note = MISC_FEATURE - Xaa = Boc-Phe
SITE             3
                 note = MISC_FEATURE - Xaa = MePhe
SITE             9
                 note = MISC_FEATURE - Xaa = Asp(SBn)
SITE             10
                 note = MISC_FEATURE - Xaa = MeAla
SITE             11
                 note = MISC_FEATURE - Xaa = Ser(tBu)
SITE             12
                 note = MISC_FEATURE - Xaa = Gly-NH2
source           1..12
                 mol_type = protein
                 organism = synthetic construct
SEQUENCE: 337
XAXGLAVFXX XX                                                                      12

SEQ ID NO: 338   moltype = AA  length = 12
FEATURE          Location/Qualifiers
REGION           1..12
                 note = An artificially synthesized sequence
SITE             3
                 note = MISC_FEATURE - Xaa = MePhe
SITE             9
                 note = MISC_FEATURE - Xaa = Asp(SBn)
SITE             10
                 note = MISC_FEATURE - Xaa = MeAla
SITE             12
                 note = MISC_FEATURE - Xaa = Gly-NH2
source           1..12
                 mol_type = protein
                 organism = synthetic construct
SEQUENCE: 338
FAXGLAVFXX SX                                                                      12

SEQ ID NO: 339   moltype = AA  length = 11
FEATURE          Location/Qualifiers
REGION           1..11
                 note = An artificially synthesized sequence
SITE             6
```

| | | |
|---|---|---|
| | note = MISC_FEATURE - Xaa = Asp(SBn) | |
| source | 1..11 | |
| | mol_type = protein | |
| | organism = synthetic construct | |
| SEQUENCE: 339 | | |
| GTTTRXPYRG G | | 11 |
| | | |
| SEQ ID NO: 340 | moltype = AA  length = 10 | |
| FEATURE | Location/Qualifiers | |
| REGION | 1..10 | |
| | note = An artificially synthesized sequence | |
| SITE | 5 | |
| | note = MISC_FEATURE - Xaa = Asp(SBn) | |
| source | 1..10 | |
| | mol_type = protein | |
| | organism = synthetic construct | |
| SEQUENCE: 340 | | |
| TTTRXPYRGG | | 10 |
| | | |
| SEQ ID NO: 341 | moltype = AA  length = 12 | |
| FEATURE | Location/Qualifiers | |
| REGION | 1..12 | |
| | note = An artificially synthesized sequence | |
| SITE | 1 | |
| | note = MISC_FEATURE - Xaa = Boc-MeAla | |
| SITE | 3 | |
| | note = MISC_FEATURE - Xaa = MeLeu | |
| SITE | 4 | |
| | note = MISC_FEATURE - Xaa = Thr(Trt) | |
| SITE | 5 | |
| | note = MISC_FEATURE - Xaa = MePhe | |
| SITE | 7 | |
| | note = MISC_FEATURE - Xaa = MeLeu | |
| SITE | 8 | |
| | note = MISC_FEATURE - Xaa = MeVal | |
| SITE | 11 | |
| | note = MISC_FEATURE - Xaa = MePhe | |
| SITE | 12 | |
| | note = MISC_FEATURE - Xaa = Ala-piperidine | |
| source | 1..12 | |
| | mol_type = protein | |
| | organism = synthetic construct | |
| SEQUENCE: 341 | | |
| XVXXXGXXFD XX | | 12 |
| | | |
| SEQ ID NO: 342 | moltype =   length = | |
| SEQUENCE: 342 | | |
| 000 | | |
| | | |
| SEQ ID NO: 343 | moltype =   length = | |
| SEQUENCE: 343 | | |
| 000 | | |
| | | |
| SEQ ID NO: 344 | moltype = AA  length = 12 | |
| FEATURE | Location/Qualifiers | |
| REGION | 1..12 | |
| | note = An artificially synthesized sequence | |
| SITE | 1 | |
| | note = MISC_FEATURE - Xaa = MeAla | |
| SITE | 3 | |
| | note = MISC_FEATURE - Xaa = MeLeu | |
| SITE | 5 | |
| | note = MISC_FEATURE - Xaa = MePhe | |
| SITE | 7 | |
| | note = MISC_FEATURE - Xaa = MeLeu | |
| SITE | 8 | |
| | note = MISC_FEATURE - Xaa = MeVal | |
| SITE | 10 | |
| | note = MISC_FEATURE - Xaa = Asp(SBn) | |
| SITE | 11 | |
| | note = MISC_FEATURE - Xaa = MePhe | |
| SITE | 12 | |
| | note = MISC_FEATURE - Xaa = Ala-piperidine | |
| source | 1..12 | |
| | mol_type = protein | |
| | organism = synthetic construct | |
| SEQUENCE: 344 | | |
| XVXTXGXXFX XX | | 12 |

```
SEQ ID NO: 345          moltype =     length =
SEQUENCE: 345
000

SEQ ID NO: 346          moltype =     length =
SEQUENCE: 346
000

SEQ ID NO: 347          moltype =     length =
SEQUENCE: 347
000

SEQ ID NO: 348          moltype =     length =
SEQUENCE: 348
000

SEQ ID NO: 349          moltype =     length =
SEQUENCE: 349
000

SEQ ID NO: 350          moltype =     length =
SEQUENCE: 350
000

SEQ ID NO: 351          moltype =     length =
SEQUENCE: 351
000

SEQ ID NO: 352          moltype =     length =
SEQUENCE: 352
000

SEQ ID NO: 353          moltype =     length =
SEQUENCE: 353
000

SEQ ID NO: 354          moltype = AA  length = 11
FEATURE                 Location/Qualifiers
REGION                  1..11
                        note = An artificially synthesized sequence
SITE                    1
                        note = MISC_FEATURE - Xaa = Fmoc-Phe
SITE                    2
                        note = MISC_FEATURE - Xaa = tBuSSlac
SITE                    4
                        note = MISC_FEATURE - Xaa = Lys(Alloc-Cys(StBu))
SITE                    6
                        note = MISC_FEATURE - Xaa = MeAla
SITE                    7
                        note = MISC_FEATURE - Xaa = MeLeu
SITE                    9
                        note = MISC_FEATURE - Xaa = MePhe
SITE                    10
                        note = MISC_FEATURE - Xaa = MeAla
source                  1..11
                        mol_type = protein
                        organism = synthetic construct
SEQUENCE: 354
XXFXLXXAXX A                                                                      11
```

PEPTIDE-COMPOUND CYCLIZATION METHOD

CROSS-REFERENCE TO RELATED APPLICATIONS

This application is a continuation of U.S. patent application Ser. No. 17/011,815, filed Sep. 3, 2020, which is a continuation of U.S. patent application Ser. No. 15/166,550, filed May 27, 2016, now abandoned, which is a continuation of U.S. patent application Ser. No. 14/368,564, filed Jun. 25, 2014, now U.S. Pat. No. 9,409,952, issued Aug. 9, 2016, which is a U.S. National Phase of PCT Application No. PCT/JP2012/084103, filed Dec. 28, 2012, which claims the benefit of Japanese Patent Application Nos. 2011-288865, filed Dec. 28, 2011, and 2012-156943, filed Jul. 12, 2012, each of which is incorporated herein by reference in its entirety.

REFERENCE TO SEQUENCE LISTING SUBMITTED ELECTRONICALLY

The content of the electronically submitted sequence listing (Name: 6663_0264 Sequence Listing.xml; Size: 635 kilobytes; and Date of Creation: Aug. 29, 2023) filed with the application is incorporated herein by reference in its entirety.

TECHNICAL FIELD

The present invention relates to novel methods for cyclizing peptide compounds, novel peptide compounds and libraries comprising the same.

BACKGROUND ART

In recent years, attention has been given to the development of drug discovery technologies using medium sized molecules (molecular weight: 500 to 2000) which have potentials to achieve drug discovery for tough targets represented by inhibitors of protein-protein interaction, agonists and molecular chaperons (Non Patent Literature 1). The possibility has been discussed that such tough targets, which have previously been regarded as difficult-to-address targets in non-antibody-based drug discovery, are also inhibited effectively using compounds having a molecular weight of 500 to 2000 (Non Patent Literature 2). Some medium sized molecules, mainly natural products, have been reported to provide for oral formulations or inhibition of intracellular targets, even if these compounds fall outside the rule of 5 proposed by Lipinski (most of which have a molecular weight exceeding 500) (Non Patent Literature 3). These medium sized molecules are highly valuable molecular species in terms of their potential to make the infeasibility of small molecules feasible by means of their accessibility to the tough targets and even to make the infeasibility of antibodies feasible by means of their ability to be internalized by cells (to provide for drug discovery against intracellular targets and oral formulations).

The conventional small-molecule drug discovery has been practiced within a molecular weight range less than 500 in most cases. The great majority of medium sized molecules for tough targets (generic name for drug targets against which Hit compounds are difficult to obtain from the conventional small-molecule compounds using high-throughput screening (HTS); the feature of the tough targets is to lack a deep cavity to which a small molecule can bind. Examples of the tough targets include protein-protein interaction inhibition typified by inhibition of the binding between IL-6 and IL-6R and additionally include RNA-protein interaction inhibition and nucleic acid-nucleic acid interaction inhibition) are therefore limited to natural products. The natural product-derived drugs still account for 30% of first in class (FIC) compounds according to analysis and serve as effective approaches. Known compounds, however, even all together, have only diversity of approximately $10^6$ compounds and are therefore limited by targets against which active compounds can be obtained. In addition, such active compounds often have poor membrane permeability or metabolic stability. Accordingly, the number of membrane-permeable molecular species that achieve drug discovery in a realm that is infeasible by small molecules or antibodies probably falls far below $10^6$. Alternatively, Hit natural products, if enhanced membrane permeability or metabolic stability is desired, are often difficult to improve by chemical modification due to necessary complicated chemical synthesis. For this reason, most of natural medicines have been launched without being chemically modified.

A set of novel compounds of large molecular weights having high diversity can be created in a short period by exploiting in vitro display techniques practically used in biotechnology-based drug discovery. Nonetheless, there are still various limitations to the expansion of this technology to drug discovery against tough targets using medium sized molecules. These limitations may be easily understood in comparison with antibody drug discovery, which is biotechnology-based drug discovery already put in practical use. Antibodies, which permit production of molecules against every target from a large-scale library, serve as large protein scaffolds having long variable regions and can further form three-dimensionally structurally diverse binding sites for forming secondary or tertiary structures. Accordingly, compounds strongly binding or inhibiting many extracellular proteins can be created with a library of approximately $10^{10}$ species. On the other hand, medium sized cyclic peptides obtained by biotechnology should have membrane permeability that is infeasible by antibodies and are therefore limited by chain length (molecular weight). Moreover, the biotechnology-based cyclic peptides are limited to be constructed by natural amino acids and therefore, also have a ceiling in three-dimensional diversity.

The creation of technologies are highly valuable, which are capable of producing in a short time a large number of easily synthesizable and chemically modifiable structurally diverse medium sized molecules having membrane permeability and metabolic stability and being possible to evaluate easily these molecules for their drug efficacy. One candidate for such technologies is the display library technologies (which is capable of synthesizing $10^{12}$ species of compounds at once and evaluating these compounds) described above. The compounds that can be obtained by the display library are currently limited to peptides. But peptide drugs are highly valuable chemical species that have already been launched with 40 or more types (Non Patent Literature 4). A typical example of such peptide drugs is cyclosporine A, which is an 11-residue peptide produced by a microbe. This peptide inhibits an intracellular target (cyclophilin) and can be orally administered. In general, peptides had been regarded as having low metabolic stability or membrane permeability. But examples of improving such properties by cyclization, N-methylation or the like have also been reported (Non Patent Literature 5).

Because the modification of natural amino acid parts to form unnatural amino acids, particularly, main chain conversion (e.g., N-methylation), structurally changes the natural peptides, the resulting unnatural peptides significantly decreased drug efficacy even when they have both membrane permeability and metabolic stability. According to a reported successful example, an integrin-inhibiting peptide was cyclized and further unnaturally modified and is now under clinical trial as an oral formulation (Non Patent Literature 6). Such drug development is one of the very few cases that follow long-term research. The previous development of highly valuable oral formulations has ended unsuccessfully for, for example, pharmaceutical injections of insulin, glucagon-like peptide-1 (GLP-1), parathyroid hormone (PTH), calcitonin or the like.

In response to the report showing the ribosomal synthesis of peptides containing unnatural amino acids or hydroxycarboxylic acid derivatives (Non Patent Literature 22), a display library containing unnatural amino acids has become more likely to be realized in recent years. A string of reports state that, particularly, peptides containing N-methylamino acids can be ribosomally synthesized by utilizing a cell-free translation system such as PureSystem® and tRNAs bound with unnatural amino acids (Non Patent Literatures 7, 8, 9, 10 and 11). An attempt to develop a display library containing one unnatural amino acid has also been reported (Non Patent Literatures 12 and 13). Another example of display of peptides containing N-methylamino acids has also been reported (Non Patent Literature 23).

Also, elucidation of the key factors for compatibilities of obtaining membrane permeability and metabolic stability is underway of medium sized peptides. Lokey et al. have used a proline-containing or N-methylated cyclic peptide composed of 6 amino acids to identify factors affecting membrane permeation by parallel artificial membrane permeation assay (PAMPA) (Non Patent Literature 14) and to further create peptides having bioavailability (BA) of 28% in rats (Non Patent Literature 15). Kessler et al. have reported a review of the finding factors for obtaining membrane permeation and metabolic stability by the N-methylation of 5- or 6-amino acid cyclic peptides (Non Patent Literatures 16 and 17). Meanwhile, to our knowledge, none of the previous reports discuss in general terms a peptide that attains the compatibilities of membrane permeability and metabolic stability or key druglikeness factors for medium sized peptides having a larger molecular weight (the number of amino acids: 7 or more) expected to produce a higher rate of hit compounds because of higher diversity.

Cyclization methods are also susceptible to improvement for obtaining medium sized hit compounds from a display library. For example, the cyclization of peptides in conventional phage display is limited to peptides having the S—S bond cycliztion between two Cys residues (Non Patent Literature 18). The cyclic peptides made by the cyclization method based on the S—S bond still require various improvements as drug-like medium sized peptides due to their problems such as a short half-life in blood attributed to metabolic instability as well as reduction and cleavage in intracellular weak-acidic environments resulting in degradation, difficult oral absorption, and possible onset of toxicity due to the random formation of covalent bonds between SH groups generated by cleavage and proteins in the body. A cyclization by two Cys residues of a peptides with amesitylene-unit has been reported in recent years as a technologies of solving these problems (Non Patent Literature 19). Although use of this approach achieves more stable cyclization through thioether, the approach produces only limited effects and still remains to be improved. For example, thioether is widely known to be susceptible to oxidative metabolism. Reportedly, thioether is degraded into $RSCH_2R' \rightarrow RSH+R'CHO$ by cytochrome P450 or metabolized into sulfoxide by flavin-containing monooxygenase (Non Patent Literature 20). The former reaction yields a reactive metabolite, leading to the onset of toxicity.

Meanwhile, groundbreaking reports have been made, which said that amide cyclization, a drug-like cyclization method, was successfully realized as a method for cyclizing peptides (Non Patent Literatures 21, 25, 26 and 27). All of these cyclization methods disclosed therein cannot be applied directly to display libraries, because the methods generate structures by the chemical reaction of active species resulting from the cleavage of main chain amide bonds with the main chain amino groups of amino acids. These approaches are useful in cyclocondensing the main chain carboxylic acids and main chain amino groups of many natural products such as cyclosporine A. These approaches, however, which involve generating active species by the degradation of main chain amide bonds, cannot be used for display libraries that require a main chain carboxylic acid terminal to bind to mRNA.

As for mRNA display, two novel cyclization methods have been proposed so far. Nonetheless, a display approach improved in these respects still remains to be established. Even use of a cyclization method which involves crosslinking the amino group of N-terminal methionine with the amino group of lysine located downstream (on the C-terminal side) by disuccinimidyl glutarate (DSG) (Non Patent Literature 12) or a cyclization method which involves introducing an amino acid derivative having a chloroacetyl group as an N-terminal translation initiation amino acid, locating Cys downstream, and forming thioether by intramolecular cyclization reaction (Non Patent Literature 11 and Patent Literature 1) is insufficient for the improvement in these respects. Thus, there has been a demand for the development of a novel cyclization method that substitutes as these methods. For example, the S—S cyclization method based on two cysteine residues requires specifying amino acids at two positions (cysteine). By contrast, the cyclization method by crosslink using DSG must fix amino acids at 3 positions including lysine, resulting in reduced structural diversity in a peptide library with the given number of residues.

According to the report, structural change in cyclization site largely reduces the activity (intensity of drug efficacy) of a peptide having the cyclization site (Non Patent Literature 24). This report indicates that the cyclization site is difficult to modify in order to convert the obtained peptide having the cyclization site to a peptide excellent in membrane permeability and metabolic stability.

There has been a demand for a library of cyclic site-containing peptides that are excellent in membrane permeability and metabolic stability and available in pharmaceutical development. The establishment of such a peptide library still remains to be improved in various respects.

CITATION LIST

Patent Literature

Patent Literature 1: International Publication No. WO 2008/117833

Non Patent Literature

Non Patent Literature 1: Satyanarayanajois, S. D., Hill, R. A. Medicinal chemistry for 2020, Future Med. Chem. 2011, 3, 1765

Non Patent Literature 2: Wells, J. A., McClendon, C. L., Reaching for high-hanging fruit in drug discovery at protein-protein interfaces. Nature, 2007, 450, 1001

Non Patent Literature 3: Ganesan, A. The impact of natural products upon modern drug discovery. Curr. Opin. Chem. Bio. 2008, 12, 306.

Non Patent Literature 4: Gracia, S. R., Gaus, K., Sewald, N. Synthesis of chemically modified bioactive peptides: recent advances, challenges and developments for medicinal chemistry. Future Med. Chem. 2009, 1, 1289

Non Patent Literature 5: Chatterjee, J., Gilon, C., Hoffman, A., Kessler, H., N-Methylation of peptides: A new perspective in medicinal chemistry. 2008, 41, 1331.

Non Patent Literature 6: Kessler, H. et. al., Cilengitide: The first anti-angiogenic small molecule drug candidate. Design, synthesis and clinical evaluation. Anti-cancer Agents in Medicinal Chemistry 2010, 10, 753

Non Patent Literature 7: Roberts, R. W., et al. Encodamers: Unnatural peptide oligomers encoded in RNA. Chem. Bio. 2003, 10, 1043.

Non Patent Literature 8: Forster, A. C. et. al., Specificity of translation for N-alkyl amino acids. J. Am. Chem. Soc. 2007, 129, 11316.

Non Patent Literature 9: Merryman, C., Green, R. Transformation of aminoacyl tRNAs for the in vitro selection of "Drug-like" molecules. Chem. Bio. 2004, 11, 575.

Non Patent Literature 10: Szostak, J. W. et al. Ribosomal synthesis of N-methyl peptides. J. Am. Chem. Soc. 2008, 130, 6131.

Non Patent Literature 11: Suga, H. et. al., Messenger RNA-programmed incorporation of multiple N-methylamino acids into linear and cyclic peptides. Chem. Bio. 2008, 15, 32.

Non Patent Literature 12: Roberts, R. et. al., In vitro selection of mRNA display libraries containing an unnatural amino acid. J. Am. Chem. Soc. 2002, 124, 9972

Non Patent Literature 13: Roberts, R. et. al. Design of cyclic peptides that bind protein surfaces with antibody-like affinity. ACS chem. Bio. 2007, 9, 625.

Non Patent Literature 14: Lokey, R. S. et. al., Testing the conformational hypothesis of passive membrane permeability using synthetic cyclic peptide diastereomers. J. Am. Chem. Soc. 2006, 128, 2510

Non Patent Literature 15: Lokey, R. S. et. al., On-resin N-methylation of cyclic peptides for discovery of orally bioavailable scaffolds. Nature Chem. Bio. 2011, 7, 810

Non Patent Literature 16: Kessler, H. et. al., Improvement of drug-like properties of peptides: the somatostatin paradigm. Expert Opin. Drug Discov. 2010, 5, 655.

Non Patent Literature 17: Kessler, H. et. al., The impact of amino acid side chain mutations in conformational design of peptides and proteins. Chem. Eur. J. 2010, 16, 5385.

Non Patent Literature 18: Comb Chem High Throughput Screen. 2010; 13:75-87Phage-displayed combinatorial peptide libraries in fusion to beta-lactamase as reporter for an accelerated clone screening: Potential uses of selected enzyme-linked affinity reagents in downstream applications. Shukla G S, Krag D N.

Non Patent Literature 19: Heinis, C., Rutherford, T. Freund, S. Winter, G., Phage-encoded combinatorial chemical libraries based on bicyclic peptides. Nature Chem. Bio. 2009, 5, 502.

Non Patent Literature 20: Yakubutsu taishagaku: Iryo yakugaku/dokuseigaku no kiso to shite (Drug Metabolomics: As the Basis of Medical Pharmacy/Toxicology in English), 2nd edition, Ryuichi Kato and Tetsuya Kamataki, ed.

Non Patent Literature 21: Kawakami T, Diverse backbone-cyclized peptides via codon reprogramming. Nat Chem Biol. 2009, 5, 888-90.

Non Patent Literature 22: Ohta A, et al., Synthesis of polyester by means of genetic code reprogramming. Chem Biol., 2007, 14, 1315-22. Goto Y, et al., Flexizymes for genetic code reprogramming. Nat Protoc. 2011, 6, 779-90.

Non Patent Literature 23: Yamagishi Y. et al., Natural product-like macrocyclic N-methyl-peptide inhibitors against a ubiquitin ligase uncovered from a ribosome-expressed de novo library. Chem Biol. 2011, 18, 1562-70.

Non Patent Literature 24: Chen S, et al. Structurally diverse cyclisation linkers impose different backbone conformations in bicyclic peptides. Chembiochem. 2012, 13, 1032-8

Non Patent Literature 25: Parthasarathy, R. Subramanian, S., Boder, E. T. Bioconjugate Chem., 2007, 18, 469-476.

Non Patent Literature 26: Tsukiji S., Nagamune T., ChemBioChem, 2009, 10, 787-798.

Non Patent Literature 27: Katoh, Takayuki; Goto, Yuki; Reza, Md. Shamim; Suga, Hiroaki. Chemical Communications (Cambridge, United Kingdom) (2011), 47(36), 9946-9958)

SUMMARY OF INVENTION

Technical Problem

The realization of a display library technology which involves designing peptides that possess membrane permeability and metabolic stability, displaying compounds group thereof, and selecting peptides having drug efficacy from the compound groups may be effective for obtaining clinically developed peptide compounds that possess all of drug efficacy, membrane permeability, and metabolic stability. If hit compounds having membrane permeability and metabolic stability to some extent beforehand can be obtained, the hit compounds can be structurally optimized with small structural change, as in the conventional small-molecule drug discovery within the rule of 5, because these compounds, unlike natural products, are easily synthesizable and chemically modifiable. This can be expected to lead to relatively easy creation of clinically developed compounds. The present inventors have considered two requisites for the establishment of such a drug discovery technologies or approach: the elucidation of key factors for satisfying the druglikeness (preferably, which refers to the compatibility of membrane permeability and metabolic stability in the present specification) of medium sized peptides that fall outside the rule of 5; and the construction of unnatural amino acid-containing display libraries consisting of molecules that meet the conditions.

For the effective utilization of the limited-space (which refers to limitation to peptide chain length in consideration of druglikeness) medium sized peptide display, it is essential that the library should contain a large number of diversified peptides (unnatural amino acid-containing peptides) having distinct structures. Not only the introduction of amino acids differing in side chain property but the expansion of variable regions with minimized fixed sites within the limited range of molecular weights and the inclusion of peptides differing in main chain structure are more likely to give peptides binding to various targets and are thus valuable. Examples of methods effective from this viewpoint include the display of peptides having various cyclization sites and branched peptides.

The present invention has been made in light of such situations. An object of the present invention is to provide novel methods for cyclizing peptide compounds and methods for synthesizing branched peptides, for construction of peptide display libraries. Another object of the present invention is to provide drug-like display libraries and drug-like peptide compounds using these methods.

Solution to Problem

The present inventors have conducted studies to attain the objects and consequently have revealed the key factors for the first time required for drug-like cyclic peptides. The present inventors have also found methods for synthesizing display libraries with highly diversity and method for cyclization of the resulting peptide compounds that meet the conditions. Specifically, the present inventors have found methods for synthesizing cyclized peptides libraries by the combination of a novel method for translation and posttranslational chemical modification. Furthermore, methods for synthesizing libraries of peptide compounds further having a linear portion that increases the potential for obtaining drug-like peptides having the activity of interest have also found. These methods provide for discovery of compounds that exhibit binding and inhibition against target molecules. On the basis of these findings, the present invention has been completed.

Specifically, the present invention includes the following:

[1]

A method for preparing a peptide compound having a cyclic portion, the method comprising the steps of:
1) translationally synthesizing a noncyclic peptide compound composed of amino acid residues and/or amino acid analog residues or of amino acid residues and/or amino acid analog residues and an N-terminal carboxylic acid analog from a nucleic acid sequence encoding the peptide compound,
   wherein the noncyclic peptide compound contains an amino acid residue or amino acid analog residue having a single reactive site at a side chain on the C-terminal side thereof, and an amino acid residue, amino acid analog residue or the N-terminal carboxylic acid analog having another reactive site on the N-terminal side; and
2) forming an amide bond or a carbon-carbon bond between the reactive site of the amino acid residue, amino acid analog residue or the N-terminal carboxylic acid analog on the N-terminal side and reactive site of the amino acid residue or amino acid analog residue at the side chain on the C-terminal side.

[2]

The method according to [1], comprising the steps of:
1) translationally synthesizing a noncyclic peptide compound composed of amino acid residues and/or amino acid analog residues or of amino acid residues and/or amino acid analog residues and an N-terminal carboxylic acid analog from a nucleic acid sequence encoding the peptide compound,
   wherein the noncyclic peptide compound contains an amino acid residue or amino acid analog residue having an active ester group at the side chain, and an amino acid residue, amino acid analog residue or the N-terminal carboxylic acid analog having a reaction promoting group near the amine; and
2) providing a cyclic compound by forming an amide bond between the amino acid residue, amino acid analog residue or the N-terminal carboxylic acid analog having the reaction promoting group and the amino acid residue or amino acid analog residue having the active ester group at the side chain.

[3]

The method according to [2], wherein the active ester is a thioester.

[4]

The method according to [2] or [3], wherein the reaction promoting group is an SH group.

[5]

The method according to [3] or [4], further comprising a step of removing the reaction promoting group following the step of providing the cyclic compound.

[6]

The method according to any of [2] to [5], wherein the amino acid, amino acid analog or the N-terminal carboxylic acid analog having a reaction promoting group near the amine is Compounds N-1 or N-2 represented by the following general formulas:

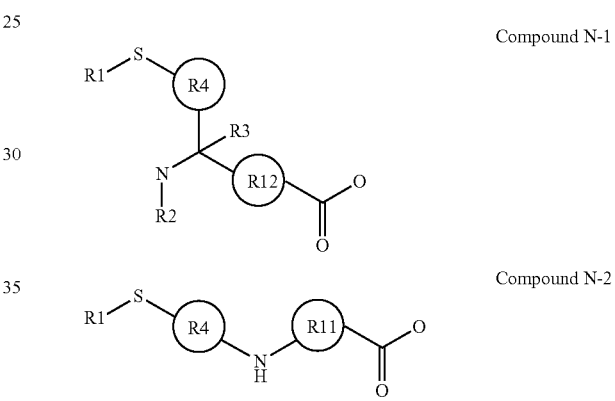

(wherein R1 represents a hydrogen atom, S—R23 (wherein R23 represents an alkyl group, an aryl group or an aralkyl group which optionally has a substituent), or a protecting group for the HS group;

R2 and R3 each independently represent a hydrogen atom, or an alkyl group, an alkenyl group, an alkynyl group, an aryl group, a heteroaryl group, an aralkyl group or a cycloalkyl group which optionally has a substituent; or represent a substituent in which R2 and R3 form a ring, or a substituent in which R2 or R3 and R4 form a ring;

R4 represents an alkylene group which optionally has a substituent, an arylene group which optionally has a substituent or a divalent aralkyl group which optionally has a substituent; and R11 and R12 each independently represent a single bond, an alkylene group which optionally has a substituent, an arylene group which optionally has a substituent or a divalent aralkyl group which optionally has a substituent).

[7]

The method according to any of [2] to [6], wherein the amino acid or amino acid analog having an active ester group at the side chain is Compounds C-1 represented by the following general formula:

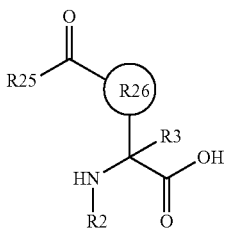

Compound C-1

(wherein R25 represents OH, a halogen atom, OR or SR1 (wherein R represents Bt, At, NSu or Pfp, and R1 represents a hydrogen atom, an alkyl group which optionally has a substituent, an aryl group which optionally has a substituent, an aralkyl group which optionally has a substituent, a cycloalkyl group which optionally has a substituent, a heteroaryl group which optionally has a substituent, an alkenyl group which optionally has a substituent or an alkylene group which optionally has a substituent);
R26 represents an alkylene group which optionally has a substituent, an arylene group which optionally has a substituent or a divalent aralkyl group which optionally has a substituent; and
R2 and R3 each independently represent a hydrogen atom, or an alkyl group which optionally has a substituent).

[8]
The method according to any of [1] to [7], wherein the cyclic portion of the peptide compound having a cyclic portion is composed of 5 to 12 amino acid residues and/or amino acid analog residues, or amino acid residues and/or amino acid analog residues and an N-terminal carboxylic acid analog in total.

[9]
The method according to any of [1] to [8], wherein the peptide compound having a cyclic portion is composed of 9 to 13 amino acid residues and/or amino acid analog residues, or amino acid residues and/or amino acid analog residues and a N-terminal carboxylic acid analog in total.

[10]
The method according to [1], comprising the steps of:
1) translationally synthesizing a noncyclic peptide compound composed of amino acid residues and/or amino acid analog residues or of amino acid residues and/or amino acid analog residues and an N-terminal carboxylic acid analog from a nucleic acid sequence encoding the peptide compound,
wherein the noncyclic peptide compound contains an amino acid residue or amino acid analog residue having an active ester group at the side chain, and an amino acid residue having an N-terminal main chain amino group or an amino acid analog residue or N-terminal carboxylic acid analog having an amino group in the main chain or the side chain; and
2) providing a cyclic compound by forming an amide bond between the N-terminal amino acid residue, N-terminal amino acid analog residue or N-terminal carboxylic acid analog and the amino acid residue or amino acid analog having an active ester group at the side chain.

[11]
The method according to [10], wherein the active ester group is an alkylthioester group or an aralkylthioester group, and wherein the method comprises a step of converting the group to a more active ester group by adding an activating agent after the translational synthesis of Step 1).

[12]
The method according to [11], wherein the activating agent is an arylthiol or N-hydroxysuccinimide.

[13]
The method according to [12], wherein the conversion step is a step of converting the active ester group to a still more active ester group by adding an activating agent highly reactive with the translated thioester and an activating agent highly reactive with the amine to be cyclized.

[14]
The method according to claim 13, wherein the conversion step is a step of converting the active ester group to another active ester group by an arylthioester and then converting the group to a yet more active ester group by an oxime and a derivative thereof.

[15]
The method according to any of [1] to [14], wherein the translational synthesis at the N-terminal site in Step 1) is carried out by a method comprising introducing a translatable amino acid, a translatable amino acid analog or a translatable N-terminal carboxylic acid analog other than formylmethionine by using an acylated translation initiation tRNA.

[16]
The method according to any of [10] to [14], wherein the translational synthesis at the N-terminal site in Step 1) is carried out by a method comprising skipping the initiation codon and introducing a translatable amino acid, a translatable amino acid analog or a translatable N-terminal carboxylic acid analog other than Met into the N-terminal.

[17]
The method according to any of [10] to [14], wherein the translational synthesis at the N-terminal site in Step 1) is carried out by a method comprising cleaving an amino acid, amino acid analog or carboxylic acid analog at the N-terminal with aminopeptidase.

[18]
The method according to [17], wherein the translational synthesis at the N-terminal site is carried out by a method comprising removing the N-terminal formyl Met by treatment with methionine aminopeptidase and introducing another translatable amino acid, translatable amino acid analog or translatable N-terminal carboxylic acid analog into the N-terminal.

[19]
The method according to any of [10] to [14], wherein the translational synthesis at the N-terminal site is carried out by a method comprising removing the N-terminal formylnorleucine translated in a translation system including norleucine in place of Met by treatment with methionine aminopeptidase and introducing another translatable amino acid, translatable amino acid analog or translatable N-terminal carboxylic acid analog into the N-terminal.

[20]
The method according to any of [17] to [19], wherein the step of removing the amino acid, amino acid analog or carboxylic acid analog at the N-terminal further comprising being exposed to peptide deformylase.

[21]
The method according to any of [1] to [20], wherein the peptide compound having a cyclic portion further has a linear portion.

[22]
The method according to any of [1] to [21], wherein the noncyclic peptide compound contains α-hydroxycarboxylic acids, and amino acids or amino acid analogs having an optionally protected amino group at the side chain, and wherein the method comprises Step 3) of forming a branched site by chemically reacting the α-hydroxycarboxylic acid site with the amino acid or amino acid analog site having the optionally protected amino group at the side chain following Step 2) of forming the cyclic compound.

[23]

A method for preparing a peptide compound having a cyclic portion and a linear portion, the method comprising the steps of:
1) translationally synthesizing a noncyclic peptide compound composed of amino acid residues and/or amino acid analog residues or of amino acid residues and/or amino acid analog residues, an N-terminal carboxylic acid analog and α-hydroxycarboxylic acids from a nucleic acid sequence encoding the peptide compound, wherein the noncyclic peptide compound
    i) contains an amino acid residue (or amino acid analog residue) having a single reactive site at a side chain on the C-terminal side thereof and an amino acid residue, amino acid analog residue or the N-terminal carboxylic acid analog having another reactive site on the N-terminal side, and
    ii) contains an α-hydroxycarboxylic acid having Rf5 at the α-position between the two reaction points described in i) above (wherein Rf5 is selected from a hydrogen atom and optionally substituted alkyl, aralkyl, heteroaryl, cycloalkyl, alkenyl and alkynyl groups), and an amino acid residue or amino acid analog residue having, at the side chain, an amino group optionally protected in the noncyclic peptide compound;
2) carrying out cyclization reaction by forming a bond between the reactive site of the amino acid residue, amino acid analog residue or the N-terminal carboxylic acid analog on the N-terminal side and the reactive site of the amino acid residue or the amino acid analog residue at the side chain on the C-terminal side;
3) generating a thioester group by cleaving the ester bond of the α-hydroxycarboxylic acid described in ii) of Step 1); and
4) carrying out cyclization reaction by forming a bond between the thioester group generated in Step 3) and the amino group described in ii) of Step 1).

[24]

The method according to [23], wherein the number of the amino acid residues and/or the amino acid analog residues contained between the α-hydroxycarboxylic acid and the amino acid residue or the amino acid analog residue having an amino group at the side chain as described in ii) of Step 1) is 7 or less.

[25]

The method according to [23] or [24], wherein the α-hydroxycarboxylic acid described in ii) of Step 1) is contained as Cys-Pro-α-hydroxycarboxylic acid in the noncyclic peptide compound.

[26]

The method according to any of [23] to [25], wherein the amino acid residue, amino acid analog residue or the N-terminal carboxylic acid analog having another reactive site on the N-terminal side as described in i) of Step 1) have a reaction promoting group.

[27]

The method according to any of [23] to [26], wherein the amino acid residue, amino acid analog residue or N-terminal carboxylic acid analog having another reactive site on the N-terminal side as described in i) of Step 1) do not have a reaction promoting group, wherein the amino group of the amino acid residues or amino acid analog residues having an amino group at the side chain as described in ii) have a protecting group, wherein the cyclization reaction of Step 2) is carried out by adding an activating agent, and wherein the method comprises a step of removing the protecting group for the amino group of the amino acid residues or the amino acid analog residues having the amino group at the side chain as described in ii) above after the cyclization reaction of Step 2) and before the cyclization reaction of Step 3).

[28]

The method according to [1], comprising the steps of:
1) translationally synthesizing a noncyclic peptide compound composed of amino acid residues and/or amino acid analog residues or of amino acid residues and/or amino acid analog residues and an N-terminal carboxylic acid analog from a nucleic acid sequence encoding the peptide compound,
    wherein the noncyclic peptide compound contains an amino acid residue or amino acid analog residue having a single reactive site at the side chain and an amino acid, amino acid analog residue or the N-terminal carboxylic acid analog having another reactive site at the N-terminal; and
2) forming a carbon-carbon bond between the reactive site of the N-terminal amino acid residue, the N-terminal amino acid analog residue or the N-terminal carboxylic acid analog and the reactive site of the amino acid residue or amino acid analog having a single reactive site at the side chain.

[29]

The method according to [28], wherein a carbon-carbon double bond is selected as the reactive site of the N-terminal amino acid residue, the N-terminal amino acid analog residue or the N-terminal carboxylic acid analog, wherein an aryl halide is selected as the reactive site of the amino acid residue or the amino acid analog residue having a single reactive site at the side chain, and wherein the method comprises a step of carrying out cyclization reaction by carbon-carbon bond reaction using a transition metal as a catalyst.

[30]

The method according to [29], wherein the carbon-carbon bond reaction using a transition metal as a catalyst is a Heck chemical reaction using Pd as a catalyst.

[31]

The method according to any of [1] to [30], wherein a reactive site for carrying out cyclization reaction is placed at a position where the cyclic portion of the peptide compound having a cyclic portion is formed by 5 to 12 amino acids or amino acid analogs in total.

[32]

The method according to [31], wherein the peptide compound having a cyclic portion has 9 to 13 amino acids and amino acid analog residues in total.

[33]

The method according to any of [1] to [32], wherein a peptide compound-nucleic acid complex is prepared in which the C-terminal of the peptide compound links to a template used for translational synthesis through a spacer.

[34]

The method according to [33], wherein the peptide compound-nucleic acid complex is synthesized using a nucleic acid sequence encoding the noncyclic peptide compound used for translational synthesis in which puromycin conjugates to the 3'-end of the nucleic acid through a linker.

[35]
The method according to [33] or [34], wherein the spacer is a peptide, RNA, DNA or hexaethylene glycol polymer, or a combination thereof.

[36]
The method according to any of [1] to [35], wherein the peptide compound is prepared by translating a nucleic acid library comprising a plurality of nucleic acids having sequences different from each other.

[37]
A peptide compound or a peptide compound-nucleic acid complex made by the preparation method according to any of [1] to [36].

[38]
A library comprising a plurality of the peptide compounds or the peptide compound-nucleic acid complexes according to [37] which have different structures.

[39]
A peptide compound having a cyclic portion, wherein:
(i) the peptide compound contains a cyclic portion composed of 5 to 12 amino acids and amino acid analog residues in total, and has 9 to 13 amino acids and amino acid analogs in total,
(ii) the peptide compound contains at least two N-substituted amino acids and at least one N-unsubstituted amino acid,
(iii) the peptide compound has a ClogP value of 6 or more, and
(iv) the bond of the amino acids or the amino acid analogs forming the cyclic portion has at least one bond formed between an active ester group at the side chain of the amino acid or the amino acid analog and an amine group of another amino acid or amino acid analog.

[40]
The peptide compound according to [39], wherein the amino acids and the amino acid analogs contained in the peptide compound are amino acids or amino acid analogs selected from amino acids or amino acid analogs that can be translationally synthesized, or amino acids or amino acid derivatives obtained by chemically modifying the side chain or the N-substitution site of translatable amino acids or amino acid analogs.

[41]
The peptide compound according to [39] or [40], wherein the compound further comprises at least one linear portion composed of 1 to 8 amino acids and amino acid analog residues in total.

[42]
The peptide compound according to any of [39] to [41], wherein the bond of the amino acids or the amino acid analogs forming the cyclic portion is an amide bond or a carbon-carbon bond.

[43]
The peptide compound according to any of [39] to [42], wherein the cyclic portion includes an intersection unit represented by the following general formula (I):

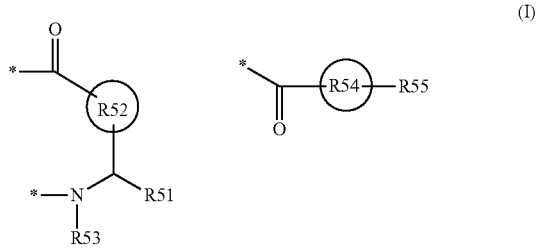

(I)

(wherein
R51 is a C1-C6 alkyl group, a C5-C10 aryl group, an aralkyl group or an ester group which optionally has a substituent, or an amide represented by the formula 1,
R52 is a C1-C6 alkyl group, an aryl group or an aralkyl group which optionally has a substituent,
R53 is a C1-C6 alkyl group which optionally has a substituent, or a hydrogen atom, or R53 and R51 optionally be bonded to each other to form a C3-C5 alkylene group and form a 5- to 7-membered ring containing a nitrogen atom,
R54 is a peptide composed of 0 to 8 amino acid residues,
R55 is a C1-C6 alkyl group, a C5-C10 aryl group, an aralkyl group or an ester group which optionally has a substituent, or an amido group which optionally has a substituent, and
* represents a binding site in the cyclic portion).

[44]
A pharmaceutical composition comprising the peptide compound according to any of [39] to [43].

[45]
The pharmaceutical composition according to [44], wherein the pharmaceutical composition is an oral formulation.

[46]
A method for preparing the peptide compound according to any of [39] to [45], wherein the method comprises the steps of:
(i) translationally synthesizing a noncyclic peptide compound having 9 to 13 amino acids and amino acid analogs in total to form a noncyclic peptide compound-nucleic acid complex in which the noncyclic peptide compound links to a nucleic acid sequence encoding the noncyclic peptide compound through a linker;
(ii) cyclizing the noncyclic peptide compound of the complex translationally synthesized in Step (i) by an amide bond or a carbon-carbon bond to form a cyclic compound having a cyclic portion with 5 to 12 amino acid and amino acid analog residues in total; and
(iii) bringing a library of the peptide compound-nucleic acid complexes having cyclic portions as provided in Step (ii) into contact with a biomolecule to select a complex having binding activity to the biomolecule.

[47]
The method according to [46], further comprising the steps of:
(iv) obtaining sequence information of the peptide compound from the nucleic acid sequence of the complex selected in Step (iii) above, and
(v) chemically synthesizing the peptide compound based on the sequence information obtained in Step (iv) above.

[48]
The method according to [46] or [47], wherein the noncyclic peptide compound contains an α-hydroxycarboxylic acid, and an amino acid or amino acid analog having an optionally protected amino group at the side chain, and wherein the method comprises the step of forming a branched site by chemically reacting the α-hydroxycarboxylic acid site with the amino acid or amino acid analog site having an amino group at the side chain following Step (ii) of forming the cyclic compound.

[49]
The method according to any of [46] to [48], wherein the biomolecule is a molecule not having a region to which a compound having a molecular weight of less than 500 can bind.

[50]

The method according to any of [46] to [49], wherein the complex having binding activity to the biomolecule further has activity to inhibit binding of the biomolecule to another biomolecule.

[51]

The method according to any of [46] to [50], wherein the amino acid or amino acid analog on the N-terminal side subjected to cyclization reaction is an amino acid or amino acid analog selected from compounds represented by the above Compounds N-1 or N-2, wherein the amino acid or amino acid analog on the C-terminal side subjected to cyclization reaction is an amino acid or amino acid analog selected from compounds represented by the above Compounds C-1, and wherein the method comprises a step of removing a reaction promoting group following Step (ii) of providing the cyclic compound.

[52]

The method according to any of [46] to [51], wherein the nucleic acid sequence has a spacer at the 3'-end, and wherein the C-terminal of the peptide compound to be translationally synthesized forms a complex with the nucleic acid sequence through the spacer.

[53]

The method according to [52], wherein the peptide compound-nucleic acid complex is synthesized using a nucleic acid sequence encoding the noncyclic peptide compound used for translational synthesis in which puromycin conjugates to the 3'-end of the nucleic acid through a linker.

[54]

The method according to [52] or [53], wherein the spacer is a peptide, RNA, DNA or hexaethylene glycol polymer.

Advantageous Effects of Invention

The present invention provides translationally synthesizable drug-like (excellent in membrane permeability and metabolic stability) peptide compounds having a cyclic portion or peptide compounds having a cyclic portion and linear portions, and display libraries of the compounds. The display library of the present invention is rich in diversity and as such, can yield hit compounds against desired target molecules with high probability. The hit compounds obtained from the display libraries of the present invention already has excellent membrane permeability and metabolic stability and as such, can be efficiently optimized as a pharmaceutical agent without large structural conversion, as in the concept of conventional small-molecule compounds. Thus, the present invention provides a novel scaffold for pharmaceutical agents different from previously known small-molecule compounds or antibody drugs and provides a novel drug discovery system for efficient creation of pharmaceutical agents.

BRIEF DESCRIPTION OF DRAWINGS

FIG. 8-1 is a diagram showing the comparison of the chemical reactivity of thioester with a glycine derivative or a cysteine derivative.

FIG. 8-2 is a diagram showing a sequel to FIG. 8-1.

FIG. 11 is a diagram showing a synthesis example of aminoacylated pdCpAs of cysteine derivatives.

FIG. 14 is a diagram showing the efficient translational incorporation of N-terminal Cys through the active use of initiation read-through.

FIG. 15-1 is a diagram showing the mass spectrum of a translation product containing a distinct amino acid encoded at the third codon immediately following Cys (P-15: Phe).

FIG. 15-2 is a diagram showing the mass spectrum of a translation product containing a distinct amino acid encoded at the third codon immediately following Cys (P-16: Leu).

FIG. 16-1 is a diagram showing the mass spectrum of a translation product containing a distinct amino acid encoded at the third codon immediately following Cys (P-17: Tyr).

FIG. 16-2 is a diagram showing the mass spectrum of a translation product containing a distinct amino acid encoded at the third codon immediately following Cys (P-18: Cys).

FIG. 17-1 is a diagram showing the mass spectrum of a translation product containing a distinct amino acid encoded at the third codon immediately following Cys (P-19: Trp).

FIG. 17-2 is a diagram showing the mass spectrum of a translation product containing a distinct amino acid encoded at the third codon immediately following Cys (P-20: Leu).

FIG. 18-1 is a diagram showing the mass spectrum of a translation product containing a distinct amino acid encoded at the third codon immediately following Cys (P-21: Leu).

FIG. 18-2 is a diagram showing the mass spectrum of a translation product containing a distinct amino acid encoded at the third codon immediately following Cys (P-22: Pro).

FIG. 19-1 is a diagram showing the mass spectrum of a translation product containing a distinct amino acid encoded at the third codon immediately following Cys (P-23: His).

FIG. 19-2 is a diagram showing the mass spectrum of a translation product containing a distinct amino acid encoded at the third codon immediately following Cys (P-24: Gln).

FIG. 20-1 is a diagram showing the mass spectrum of a translation product containing a distinct amino acid encoded at the third codon immediately following Cys (P-25: Arg).

FIG. 20-2 is a diagram showing the mass spectrum of a translation product containing a distinct amino acid encoded at the third codon immediately following Cys (P-26: Arg).

FIG. 21-1 is a diagram showing the mass spectrum of a translation product containing a distinct amino acid encoded at the third codon immediately following Cys (P-27: Ile).

FIG. 21-2 is a diagram showing the mass spectrum of a translation product containing a distinct amino acid encoded at the third codon immediately following Cys (P-29: Asn).

FIG. 23-1 is a diagram showing the mass spectrum of a translation product containing a distinct amino acid encoded at the third codon immediately following Cys (P-32: Val).

FIG. 23-2 is a diagram showing the mass spectrum of a translation product containing a distinct amino acid encoded at the third codon immediately following Cys (P-33: Ala).

FIG. 27 is a diagram showing translational synthesis using a method for introducing an amino acid, an amino acid analog or an N-terminal carboxylic acid analog other than methionine into the N-terminal, and the mass spectrum of an amide-cyclized peptide.

FIG. 30-1 is a diagram showing translation using initiation read-through and results of MS and MS/MS analyses for structural determination of an amide-cyclized peptide.

FIG. 30-2 is a diagram showing a sequel to FIG. 30-1.

FIG. 32 is a diagram showing the examination of conditions for the radical desulfurization reaction using a model substrate.

FIG. 33 is a diagram showing desulfurization reaction conditions of translated peptide P-50 and the mass spectrum of the obtained peptide P-51.

FIG. 34 is a diagram showing results of evaluating the influence of desulfurization reaction on proteins.

FIG. 35-1 is a diagram showing the mass chromatogram of a metabolite.

FIG. 35-2 is a diagram showing the MS/MS spectrum of Peak 1.

FIG. 35-3 is a diagram showing the MS/MS spectrum of Peak 2.

FIG. 35-4 is a diagram showing the MS/MS spectrum of Peak 3.

FIG. 35-5 is a diagram showing the MS/MS spectrum of Peak 4.

FIG. 56 is a diagram showing a mass chromatogram (upper) before desulfurization reaction (compound SP606) and a mass chromatogram (lower) obtained by integrating and averaging mass chromatograms of retention times from 0.34 minutes to 0.39 minutes after desulfurization reaction for 3 hours (analysis condition SQD FA05). Since the integration within this range should give the observable molecular weights of the intended compound or reaction starting materials as well as by-products, if any, having similar structures, the overall reaction selectivity may be accurately evaluated. FIG. 56 and other figures which involve integration within a predetermined time range in mass spectra abide by this concept.

FIG. 66 is diagram showing the estimation of the mean values and the distributions of the CLOGP values, the numbers of NMe amino acids and the molecular weights by a virtual library utilizing simulation by a computer.

FIG. 67 is diagram showing the estimation of the mean values and the distributions of the CLOGP values, the numbers of NMe amino acids and the molecular weights by a virtual library utilizing simulation by a computer.

FIG. 82-1 is a diagram showing the protein interaction of a 13-residue peptide having a cyclic portion formed by 10 amino acids and a 3-amino acid branch.

FIG. 82-2 is a diagram (left) showing the protein interaction of a 13-residue peptide having a cyclic portion formed by 10 amino acids and a 3-amino acid branch. FIG. 82-2 is also a diagram (right) showing the protein interaction of a cyclic peptide composed of 13 amino acids.

FIG. 84 is a diagram showing Scheme A.

FIGS. 103-1 and 103-2 are diagrams showing the synthesis of a translated peptide model compound 665.

FIG. 105 is a diagram showing the synthesis of RNA-peptide conjugate model reaction starting materials (Solid supporting).

FIG. 106 is a diagram showing the synthesis of RNA-peptide conjugate model reaction starting materials (Peptide elongation).

FIG. 107 is a diagram showing the synthesis of RNA-peptide conjugate model reaction starting materials (RNA synthesis and cleavage).

FIG. 108 is a diagram showing the synthesis of Compound 72.

FIG. 109 is a diagram showing the synthesis of Compound 76.

FIG. 110 is a diagram showing the synthesis of Compound 78.

FIG. 111 is a diagram showing the synthesis of Compound 80.

FIG. 112 is a diagram showing the synthesis of Compound 81.

FIG. 113 is a diagram showing the synthesis of Compound 70a.

FIG. 114 is a diagram showing the synthesis of Compound 70b.

FIG. 115 is a diagram showing the synthesis of Compound 70c.

FIG. 116 is a diagram showing the synthesis of Compound SP802.

Figure 117:
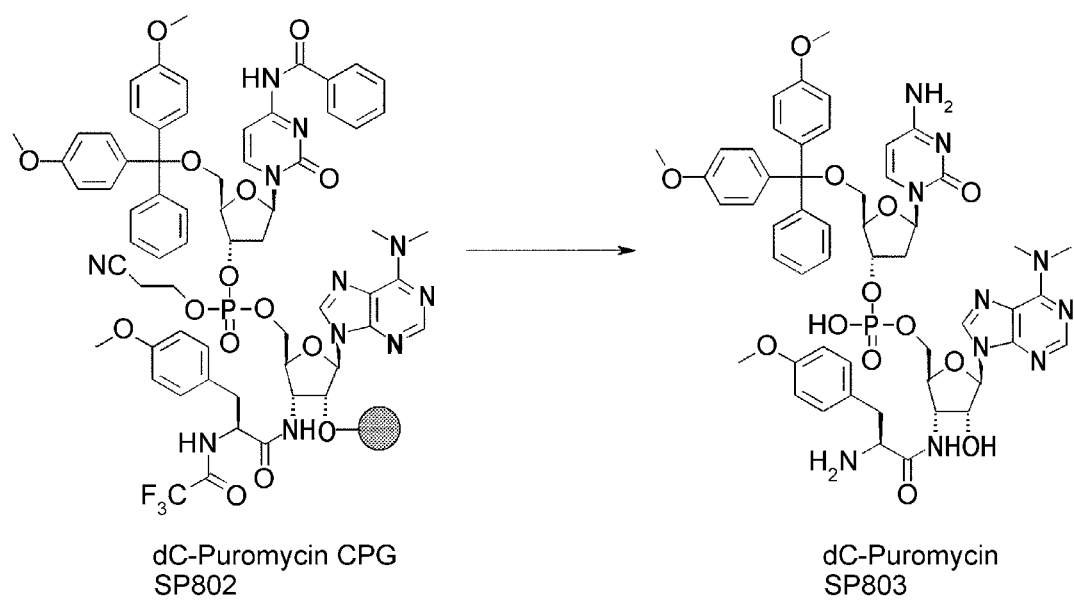

FIG. 117 is a diagram showing the synthesis of Compound SP803.

Figure 118:
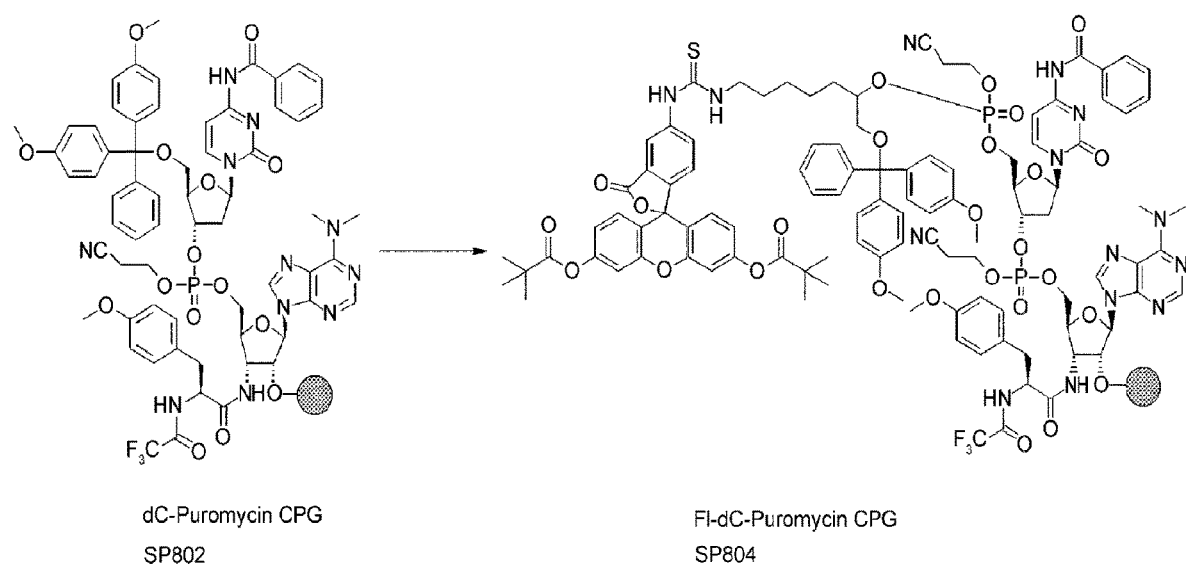

FIG. 118 is a diagram showing the synthesis of Compound SP804.

Figure 119:
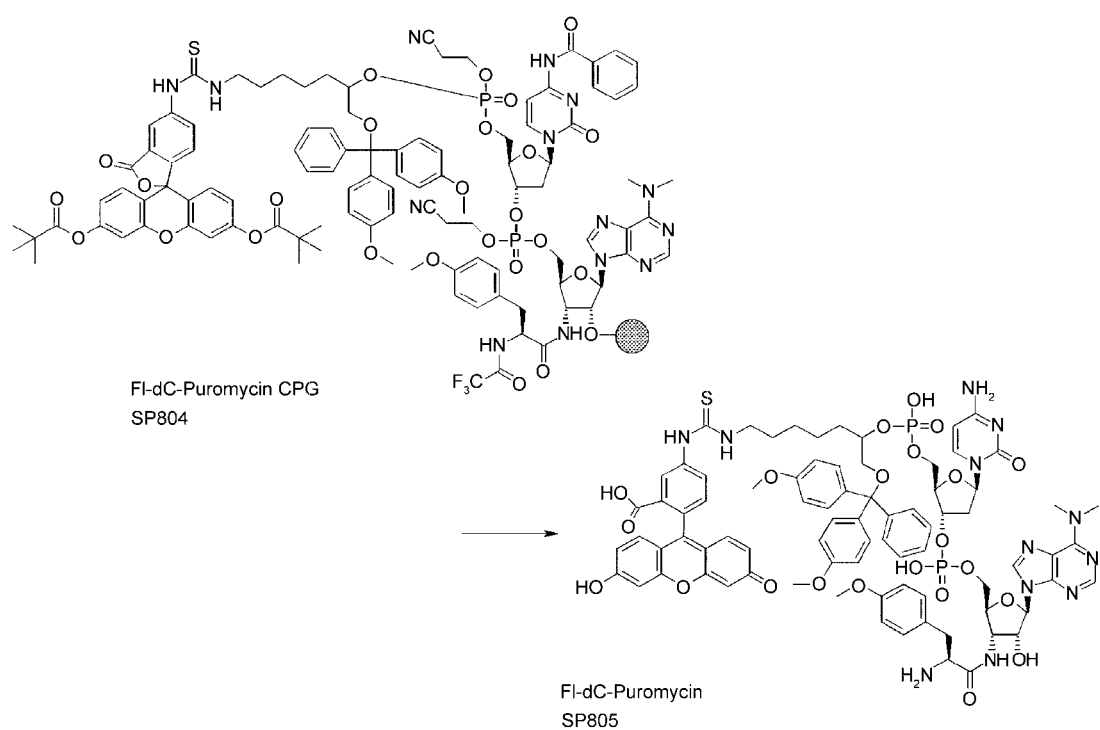

FIG. 119 is a diagram showing the synthesis of Compound SP805.

Figure 120:
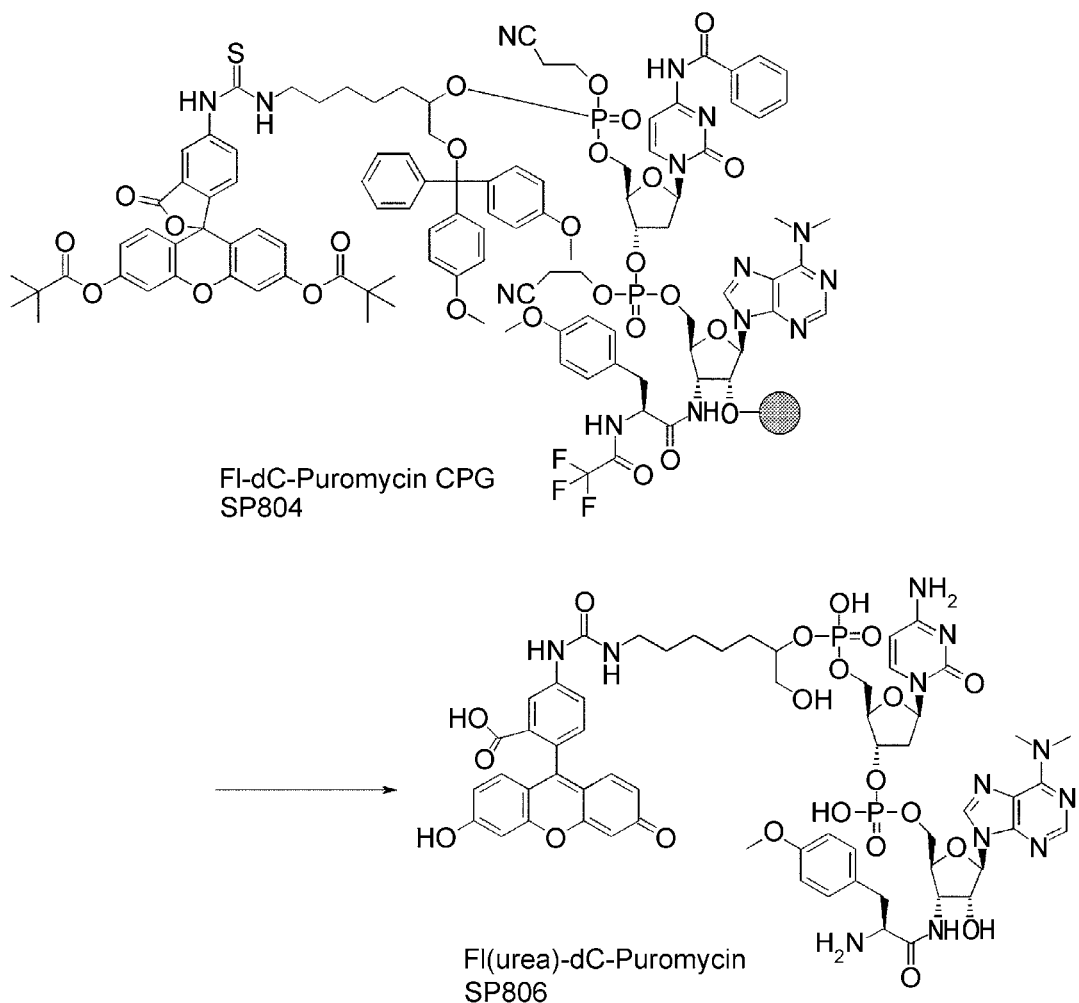

FIG. 120 is a diagram showing the synthesis of Compound SP806.

DESCRIPTION OF EMBODIMENTS

<Peptide Compound>
Peptide Compounds Having Cyclic Portion

The peptide compound having a cyclic portion according to the present invention refers to a compound formed by the amide bonds or ester bonds of amino acids and/or amino acid analogs and has a cyclic portion resulting from covalent bond-mediated cyclization such as amide bond or carbon-carbon bond formation reaction. Compounds obtained by further chemically modifying the compound are also included in the peptide compound of the present invention. The peptide compound of the present invention may have a linear portion and can be represented by, for example, Scheme A (Scheme A-1 or A-2). The peptide compound having a cyclic portion may further have linear portions. The number of amide bonds or ester bonds (the number or length of amino acids and/or amino acid analogs) is not particularly limited. The peptide compound further having a linear portion is preferably composed of 30 or less residues in total of the cyclic portion and the linear portion. The total number of amino acids in the cyclic site and the linear site is more preferably 13 or less residues for obtaining high membrane permeability. The total number of amino acids is more preferably 9 or more for obtaining high metabolic stability. In addition, the cyclic portion is preferably composed of 5 to 12 amino acids and/or amino acid analogs in consideration of the compatibility of membrane permeability and metabolic stability (druglikeness). In addition to the above description, the cyclic portion is more preferably composed of 5 to 11 amino acids and/or amino acid analogs, further preferably 7 to 11 residues, particularly preferably 9 to 11 residues. The number of amino acids and/or amino acid analogs (the number of units) in the linear portion is preferably 0 to 8, more preferably 0 to 3. In the present application, the amino acid may include the amino acid analog, unless otherwise specified. In this context, the term "druglikeness" or "drug-like" means that the peptide compound has at least membrane permeability and metabolic stability to the extent that permits its pharmaceutical use when used in oral formulations or targeting intracellular proteins, nucleic acids, intracellular regions of membrane proteins or transmembrane domains of membrane proteins.

The peptide compound having a cyclic portion according to the present invention is not particularly limited as long as the peptide is cyclized at the cyclic site. The posttranslational cyclization site is required to be a cyclization unit that forms functional groups providing for the compatibility of membrane permeability and metabolic stability (druglikeness). Any such cyclization method can be used without particular limitations. Examples of such methods include amide bond formation from carboxylic acid and amine and carbon-carbon bond formation using a transition metal as a catalyst, such as Suzuki reaction, Heck reaction and Sonogashira reaction. Thus, the peptide compound of the present invention contains at least one set of functional groups capable of such bond formation reaction. Particularly preferably, the peptide compound of the present invention contains functional groups forming an amide bond by the bond formation reaction, from the viewpoint of metabolic stability.

The cyclic portion in the peptide compound of the present invention is preferably, for example, a cyclic portion formed by cyclization by chemical reaction after translational synthesis as described in Scheme A. Also, the cyclic portion is preferably a cyclic portion that can be formed even under reaction conditions not influencing nucleic acids such as RNA or DNA after translation.

The formation of the cyclic portion is preferably drug-like cyclization. The drug-like cyclization means that the resulting bond is a drug-like bond. Preferably, the bond contains, for example, a heteroatom susceptible to oxidation and does not interfere with metabolic stability. The bond formed by cyclization includes, for example, an amide bond between active ester and amine and a bond formed by a Heck reaction product from a carbon-carbon double bond and aryl halide. Since these bonds require a triangle unit (unit on the N-terminal side in the cyclized portion) or an intersection unit also described in Scheme A to have reactive functional groups, an amino acid suitable for druglikeness is not always selected for the triangle unit or the intersection unit. The peptide compound, however, is converted to a compound having drug-like functional groups after posttranslational modification. In the present invention, such bonds are also included in the bond formed by drug-like cyclization.

The curved line in Scheme A represents a site to be cyclized after translation (posttranslational cyclization site). This portion forms a bond by any of various chemical reactions of posttranslational modification typified by amide bond or carbon-carbon bond formation reaction (e.g., Heck reaction) to form a cyclic portion. In the present specification, the "translational synthesis" means that the peptide compound is translationally synthesized from a nucleic acid (e.g., DNA or RNA) sequence encoding the peptide compound. The translation is a process of producing a linear peptide by repetitive amide bond or ester bond reaction using mRNA as a template by the action of ribosome.

The posttranslational modification refers to chemical reaction that is caused in a manner other than the action of ribosome either automatically or by the addition of other reagents after translation. Examples thereof can include cyclization reaction and deprotection reaction.

The posttranslational cyclization refers to posttranslational modification involving ring formation reaction. (Scheme A: scheme for describing the peptide compound of the present invention. The open circle unit, the filled circle unit, the triangle unit and the square unit each denote an amino acid or amino acid analog. The amino acids or amino acid analogs represented by these units are the same with or different from each other. The triangle unit could also include an N-terminal carboxylic acid analog. For example, 8 filled circle units may be amino acids or amino acid analogs of types different from each other, or some or all of them may be the same with each other. Each amino acid or amino acid analog may be chemically converted or backbone-converted to a compound having another backbone by chemical modification that can be carried out posttranslationally. In this context, one unit corresponds to an amino acid or amino acid analog at the end of posttranslational modification and also includes the compound having another backbone chemically converted or backbone-converted by posttranslational modification from an amino acid or amino acid analog translated by one tRNA. The number of units is also calculated similarly. In the present application, the amino acid may include the amino acid analog, unless otherwise specified. In the present specification, the posttranslational cyclization is also referred to as cyclization simply.

For example, the cyclic portion is a site, in Scheme A-1, composed of 1 (filled) triangle unit (residue) (unit on the N-terminal side in the cyclized portion), 8 filled circle units (main chain units in the cyclic portion) and 1 open circle unit (intersection unit). The linear portion is a site, in Scheme A-1, composed of 6 (filled) square units (main chain units in the linear portion). Alternatively, the cyclic portion is a site, in Scheme A-2, composed of 1 triangle unit, 8 filled circle units and 1 intersection unit. The linear portions are sites, in Scheme A-2, composed of 4 square and 3 square units, respectively.

In the present invention, the intersection unit refers to an amino acid or amino acid analog having, at its side chain, a functional group at which a posttranslationally formed peptide compound before cyclization (uncyclized peptide compound) is cyclized by chemical reaction with a functional group carried by the amino acid or amino acid analog of the triangle unit or with a functional group carried by the N-terminal carboxylic acid analog of the triangle unit. The intersection unit is not particularly limited as long as this unit has the functional group necessary for the cyclization with the triangle unit. This unit corresponds to the open circle unit in Scheme A. The intersection unit is selected from the amino acid and amino acid analog described above and preferably, can be translated from a nucleic acid. The translation of the intersection unit itself is not essential provided that a derivative thereof can be translated instead of the intersection unit difficult to translate. For example, in the case of the translation of Asp(SBn), a compound in which the side chain methylene chain of Asp is arbitrarily substituted is also acceptable as the intersection unit (e.g., R28 or R29 in compound C-3 may be untranslatable). The intersection unit must have a total of three or more functional groups, because the main chain amino and carboxyl groups are used in covalent bond formation for translational synthesis and the third functional group is required for posttranslational cyclization. Among these groups, the functional group at the side chain site of the intersection unit is utilized for cyclization at the posttranslational cyclization site.

In this context, the amino acid or amino acid analog or the N-terminal carboxylic acid analog having the functional group for the cyclization with the intersection unit is not particularly limited as long as the functional group achieves the cyclization with the intersection unit. This amino acid or amino acid analog or N-terminal carboxylic acid analog corresponds to the triangle unit in Scheme A. The triangle unit is located, for example, at the N-terminal as shown in Scheme A. In such a case, a main chain amino group in the amino acid selected as the triangle unit can be used as the functional group for the cyclization. For example, active ester utilized in the intersection unit provides for posttranslational cyclization by an amide bond with the main chain amino group in the triangle unit. When the main chain amino group is thus utilized as the reactive functional group, the side chain of the triangle unit may not have an additional reactive functional group. A reaction promoting group such as an SH group (thiol group) may be introduced into the side chain. In the amino acid analog used as the triangle unit, the main chain hydroxyl group may be used as the reactive functional group, or a reactive functional group located at the side chain may be used. Alternatively, in the N-terminal carboxylic acid analog used as the triangle unit, the amino group or hydroxyl group may be used as the reactive functional group in the same way as above, while various functional groups may be introduced as arbitrary reactive units not having an amino group or hydroxyl group. The triangle unit is selected from the amino acid or amino acid analog or the N-terminal carboxylic acid analog described above and preferably, can be translated. As with the intersection unit, the translation of the triangle unit itself is not essential provided that a derivative thereof can be translated instead of the triangle unit difficult to translate.

The intersection unit and the triangle unit may be incorporated at any desired position that permits cyclization in the uncyclized peptide compound. These units are preferably incorporated at positions that allow the cyclic site after cyclization or after posttranslational modification following cyclization to be composed of 5 to 12 amino acids or amino acid analogs or N-terminal carboxylic acid analog in total. These units are more preferably incorporated at positions that allow the cyclic portion after cyclization or after posttranslational modification following cyclization to be composed of 5 to 11 amino acids or amino acid analogs or N-terminal carboxylic acid analog in total.

Although the triangle unit is located at the N-terminal in Scheme A, this unit may be located at a position other than the N-terminal. In this case, the position must be located on the N-terminal side with respect to the intersection unit. The triangle unit located at the position other than N-terminal is selected from the amino acid and amino acid analog and has, at the side chain, a functional group for the cyclization reaction with the intersection unit.

The filled circle units and the square units are selected from amino acids and amino acid analogs. These units also include chemical structures that can be formed by posttranslational modification of translated amino acids or amino acid analogs (e.g., the structure of linear portion 2). The filled circle units selected from amino acids are not particularly limited and are preferably selected from drug-like amino acids and amino acids having reactive functional groups that are converted to drug-like functional groups by chemical reaction of posttranslational modification (examples of amino acid residues in linear portion 2 include lysine). The filled circle units selected from amino acid analogs are not particularly limited and are preferably selected from drug-like amino acid analogs and amino acid analogs having, at their side chains, various reactive functional groups that are chemically modified by posttranslational modification to convert the amino acid analogs to drug-like amino acid analogs.

The number of linear portions (the number of branches) is not particularly limited and may be 1 as shown in Scheme A-1 or may be 2 or more as shown in Scheme A-2. Alternatively, the peptide compound of the present invention may be a compound of Scheme A-1 free from the square units or may be a compound of Scheme A-2 free from the square units of linear portion 1. The presence of the linear portion(s) can enhance the functions of the peptide compound having a cyclic portion according to the present invention. For example, the peptide compound of the present invention may be used for inhibiting the binding between a certain receptor and its ligand. In such a case, the peptide compound having the linear portion(s) can have higher binding activity against the receptor or ligand than that of the peptide compound not having the linear portion. Such potentiation of the binding activity can enhance the receptor-ligand binding inhibitory effect of the peptide compound. Particularly, the linear portion of the present invention can be added to a desired position in the cyclic portion, for example, according to a method described later. The peptide compound having a linear portion added to a position most suitable for producing higher functions can be obtained (hereinafter, this linear portion is referred to as linear portion 2).

These linear portions are also preferred for efficiently obtaining a peptide compound having desired activity from a library of peptide compounds having a cyclic portion. Examples of the peptide compound having desired activity include peptide compounds having binding activity against target substances, peptide compounds having the effect of inhibiting the functions of target substances, peptide compounds having the effect of activating the functions of target substances, and peptide compounds having the effect of changing the functions of target substances. The functional peptide compound of interest can be selected from among those described above. When the peptide compound having a cyclic portion according to the present invention has binding activity against a target substance, not only the in vivo distribution but intracellular distribution of the target substance can be monitored in real time, for example, by labeling the peptide compound, because of the excellent membrane permeability and lipid stability of this peptide compound. In addition, the peptide compound having binding activity against a target substance that is a causative agent of a disease may be used in the diagnosis of the disease. When the peptide compound having a cyclic portion according to the present invention has the effect of inhibiting, activating or changing the function of a target substance that is, for example, a causative agent of a disease, this peptide compound can be used as a therapeutic drug for the disease. For example, an inhibitory compound can be obtained at a higher rate from the peptide compound of the present invention having a cyclic portion and further having linear portion 2 than the peptide compound having a cyclic portion and not having linear portion 2. In the case of a peptide compound having a 13-residue cyclic portion and inhibiting protein-protein interaction between protein A and protein B by binding to the protein A, a peptide contact site in the protein A bound with the peptide compound is shown on the right side of FIG. 82-2. The peptide contact region of the protein A can be approximated by circle to the cyclic compound and thereby confirmed to have a diameter corresponding to approximately 3 to 5 residues. The protein-protein interaction between protein A and protein B can be effectively inhibited if the protein B binds to this contact region. On the other hand, such effective inhibition may not be obtained if the protein B binds, at a site other than this contact region, to protein A (only a few cases of so-called allosteric inhibition have been reported as to protein-protein interaction inhibition).

Figure 1:
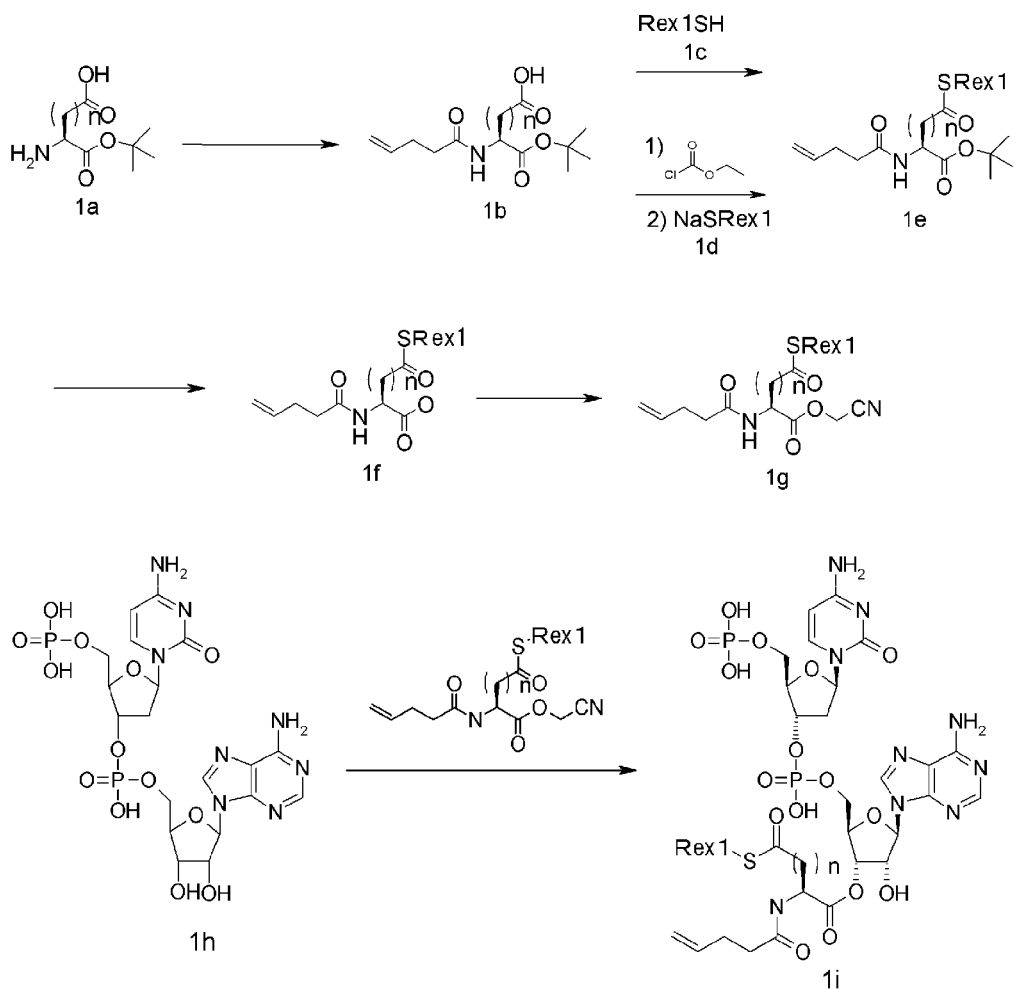
FIG. 1 is a diagram showing a general method for synthesizing an aminoacylated pdCpA compound group having side chain carboxylic acid converted to active ester.
Figures 1, 82:
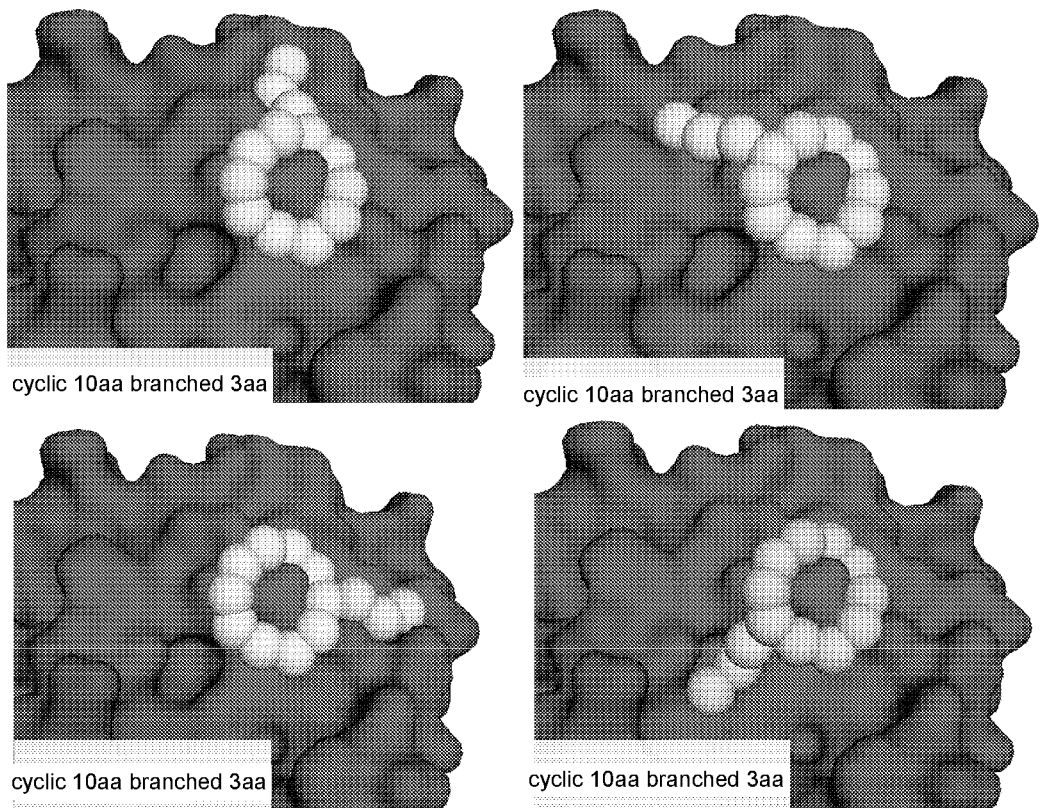
Figures 2, 82:
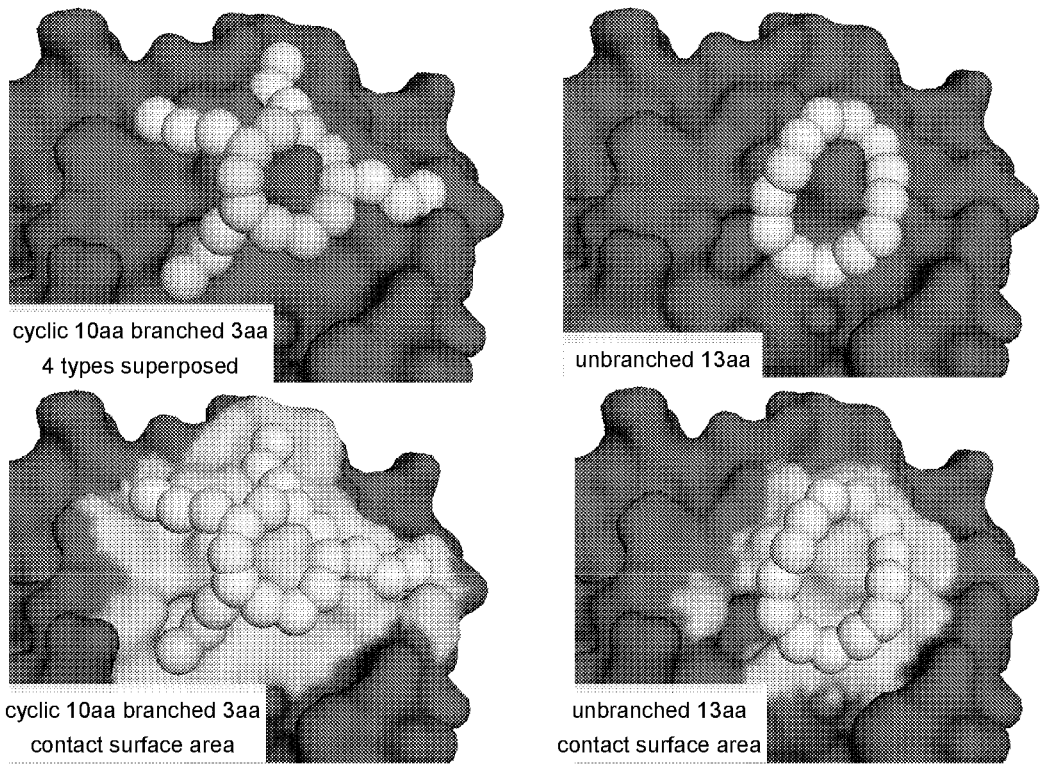

Based on this concept, it is important to obtain a peptide compound binding to a protein to give a contact region as wide as possible. Nonetheless, the total number of membrane-permeable amino acids is limited. Hence, linear portions are effective. For example, a 13-residue cyclic peptide, as in the preceding example, is shown in FIG. 82-1, and this peptide has a cyclic portion composed of 10 residues and a branch composed of the remaining 3 residues. Since linear portion 2, in particular, can be added to any position in the peptide compound according to an approach described later, not only 4 branching points shown in FIG. 82-1 but more branching points can be obtained. If these 4 linear portions are combined, the contact region is expanded to a region shown on the left side of FIG. 82-2. A peptide compound having the function of an inhibitor or the like can be obtained at a higher rate by overlapping the contact region with the binding region between protein A and protein B, even though the peptide compound acts on the same site (cavity) as in the preceding example.

In the present specification, the "amino acids" and the "amino acid analogs" constituting the peptide compound are also referred to as "amino acid residues" and "amino acid analog residues", respectively.

The amino acid refers to α-, β- and γ-amino acids. The amino acid is not limited to a natural amino acid (in the present application, the natural amino acid refers to 20 types of amino acids contained in proteins and specifically refers to Gly, Ala, Ser, Thr, Val, Leu, Ile, Phe, Tyr, Trp, His, Glu, Asp, Gln, Asn, Cys, Met, Lys, Arg and Pro) and may be an unnatural amino acid. The α-amino acid may be an L-amino acid or a D-amino acid and may be an α,α-dialkylamino acid. The amino acid is not particularly limited by its side chain, and the side chain is arbitrarily selected from a hydrogen atom as well as, for example, an alkyl group, an alkenyl group, an alkynyl group, an aryl group, a heteroaryl group, an aralkyl group and a cycloalkyl group. A substituent may be added to each of these groups. The substituent is also arbitrarily selected from any functional group containing, for example, a N atom, an O atom, a S atom, a B atom, a Si atom or a P atom (i.e., an optionally substituted alkyl group, alkenyl group, alkynyl group, aryl group, heteroaryl group, aralkyl group, cycloalkyl group or the like).

Each "amino acid" or "amino acid analog" constituting the peptide compound may contain all compatible isotopes. The isotope in the "amino acid" or "amino acid analog" refers to at least one atom replaced with an atom of the same atomic number (number of protons) and different mass number (total number of protons and neutrons). Examples of the isotope contained in the "amino acid" or "amino acid analog" constituting the peptide compound of the present invention include a hydrogen atom, a carbon atom, a nitrogen atom, an oxygen atom, a phosphorus atom, a sulfur atom, a fluorine atom and a chlorine atom including 2H, 3H, 13C, 14C, 15N, 17O, 18O, 31P, 32P, 35S, 18F and 36Cl.

Examples of the substituent include halogen-derived substituents such as fluoro (—F), chloro (—Cl), bromo (—Br) and iodo (—I). Further examples of the substituent include an alkyl group, a cycloalkyl group, an alkenyl group, an alkynyl group, an aryl group, a heteroaryl group and an aralkyl group, each of which optionally has one or more halogen-derived substituents selected from those described above.

As for O atom-derived substituents, examples of substituents for forming an ether include an alkoxy group (—OR). The alkoxy group is selected from among an alkylalkoxy group, a cycloalkylalkoxy group, an alkenylalkoxy group, an alkynylalkoxy group, an arylalkoxy group, a heteroarylalkoxy group, an aralkylalkoxy group and the like. Examples of substituents for forming an alcohol moiety include a hydroxyl group (—OH). Examples of substituents for forming a carbonyl group include a carbonyl group (—C=O—R). The carbonyl group is selected from among a hydrocarbonyl group (—C=O—H; aldehyde is obtained as a compound), an alkylcarbonyl group (ketone is obtained as a compound), a cycloalkylcarbonyl group, an alkenylcarbonyl group, an alkynylcarbonyl group, an arylcarbonyl group, a heteroarylcarbonyl group, an aralkylcarbonyl group and the like. Examples of substituents for forming a carboxylic acid (—CO$_2$H) include a carboxyl group. Examples of substituents for forming an ester group include an oxycarbonyl group (—O—C=O—R) and a carbonylalkoxy group (—C=O—OR). The carbonylalkoxy group is selected from among an alkyloxycarbonyl group, a cycloalkyloxycarbonyl group, an alkenyloxycarbonyl group, an alkynyloxycarbonyl group, an aryloxycarbonyl group, a heteroaryloxycarbonyl group, an aralkyloxycarbonyl group and the like. The oxycarbonyl group is selected from among an alkylcarbonyloxy group, a cycloalkylcarbonyloxy group, an alkenylcarbonyloxy group, an alkynylcarbonyloxy group, an arylcarbonyloxy group, a heteroarylcarbonyloxy group, an aralkylcarbonyloxy group and the like.

Examples of substituents for forming a thioester include a mercaptocarbonyl group (—S—C=O—R) and a carbonylalkylmercapto group (—C=O—SR). These substituents are selected from among a mercaptoalkylcarbonyl group, a mercaptocycloalkylcarbonyl group, a mercaptoalkenylcarbonyl group, a mercaptoalkynylcarbonyl group, a mercaptoarylcarbonyl group, a mercaptoheteroarylcarbonyl group, a mercaptoaralkylcarbonyl group and the like. Alternative examples thereof include a carbonylalkylmercapto group, a carbonylcycloalkylmercapto group, a carbonylalkenylmercapto group, a carbonylalkynylmercapto group, a carbonylarylmercapto group, a carbonylheteroarylmercapto group and a carbonylaralkylmercapto group.

Examples of substituents for forming an amide group include an aminoalkylcarbonyl group (—NH—CO—R), an aminocycloalkylcarbonyl group, an aminoalkenylcarbonyl group, an aminoalkynylcarbonyl group, an aminocycloalkylcarbonyl group, an aminoarylcarbonyl group, an aminoheteroarylcarbonyl group and an aminoaralkylcarbonyl group. Alternative examples thereof include a carbonylalkylamino group (—CO—NHR), a carbonylcycloalkylamino group, a carbonylalkenylamino group, a carbonylalkynylamino group, a carbonylarylamino group, a carbonylheteroarylamino group and a carbonylaralkylamino group. Further examples thereof include compounds in which the H atom bonded to the N atom is replaced with an alkyl group, a cycloalkyl group, an alkenyl group, an alkynyl group, an aryl group, a heteroaryl group or an aralkyl group.

Examples of substituents for forming a carbamate group include an aminoalkyl carbamate group (—NH—CO—OR), an aminocycloalkyl carbamate group, an aminoalkenyl carbamate group, an aminoalkynyl carbamate group, an aminocycloalkyl carbamate group, an aminoaryl carbamate group, an aminoheteroaryl carbamate group and an aminoaralkyl carbamate group. Further examples thereof include compounds in which the H atom bonded to the N atom is replaced with an alkyl group, a cycloalkyl group, an alkenyl group, an alkynyl group, an aryl group, a heteroaryl group or an aralkyl group.

Examples of substituents for forming a sulfonamide group include an aminoalkylsulfonyl group (—NH—SO$_2$—R), an aminocycloalkylsulfonyl group, an aminoalkenylsulfonyl group, an aminoalkynylsulfonyl group, an aminocycloalkylsulfonyl group, an aminoarylsulfonyl group, an aminoheteroarylsulfonyl group and an aminoaralkylsulfonyl group. Alternative examples thereof include a sulfonylalkylamino group (—SO$_2$—NHR), a sulfonylcycloalkylamino group, a sulfonylalkenylamino group, a sulfonylalkynylamino group, a sulfonylarylamino group, a sulfonylheteroarylamino group and a sulfonylaralkylamino group. Further examples thereof include compounds in which the H atom bonded to the N atom is replaced with an alkyl group, a cycloalkyl group, an alkenyl group, an alkynyl group, an aryl group, a heteroaryl group or an aralkyl group.

Examples of substituents for forming a sulfamide group include an aminoalkylsulfamoyl group (—NH—SO2-NHR), an aminocycloalkylsulfamoyl group, an aminoalkenylsulfamoyl group, an aminoalkynylsulfamoyl group, an aminocycloalkylsulfamoyl group, an aminoarylsulfamoyl group, an aminoheteroarylsulfamoyl group and an aminoaralkylsulfamoyl group. Further examples thereof include compounds in which the H atom bonded to the N atom is replaced with two arbitrary identical or different substituents selected from among an alkyl group, a cycloalkyl group, an alkenyl group, an alkynyl group, an aryl group, a heteroaryl group and an aralkyl group or with optionally ring-forming substituents selected from these groups.

Examples of substituents for forming a thiocarboxylic acid include a thiocarboxylic acid group (—C(═O)—SH). Examples of functional groups for forming a keto acid include a keto acid group (—C(═O)—CO$_2$H).

As for S atom-derived substituents, examples of substituents for forming a thiol group include a thiol group (—SH). The substituent forms alkylthiol, cycloalkylthiol, alkenylthiol, alkynylthiol, arylthiol, heteroarylthiol or aralkylthiol. Substituents for forming a thioether (—S—R) are selected from among an alkylmercapto group, a cycloalkylmercapto group, an alkenylmercapto group, an alkynylmercapto group, an arylmercapto group, a heteroarylmercapto group, an aralkylmercapto group and the like. Substituents for forming a sulfoxide group (—S═O—R) are selected from among an alkyl sulfoxide group, a cycloalkyl sulfoxide group, an alkenyl sulfoxide group, an alkynyl sulfoxide group, an aryl sulfoxide group, a heteroaryl sulfoxide group, an aralkyl sulfoxide group and the like. Substituents for forming a sulfone group (—S(O)$_2$—R) are selected from among an alkylsulfone group, a cycloalkylsulfone group, an alkenylsulfone group, an alkynylsulfone group, an arylsulfone group, a heteroarylsulfone group, an aralkylsulfone group and the like. Examples of substituents for forming a sulfonic acid include a sulfonic acid group (—SO$_3$H).

As for N atom-derived substituents, examples thereof include an azide group (—N$_3$) and a nitrile group (—CN). Examples of substituents for forming a primary amine include an amino group (—NH$_2$). Examples of substituents for forming a secondary amine (—NH—R) include an alkylamino group, a cycloalkylamino group, an alkenylamino group, an alkynylamino group, an arylamino group, a heteroarylamino group and an aralkylamino group. Examples of substituents for forming a tertiary amine (—NR (R')) include substituents, for example, an alkyl(aralkyl) amino group, wherein R and R' are two arbitrary or two identical substituents selected from among an alkyl group, a cycloalkyl group, an alkenyl group, an alkynyl group, an aryl group, a heteroaryl group, an aralkyl group and the like or are optionally ring-forming substituents selected from these substituents. Examples of substituents for forming an amidino group (—C(═NR)—NR'R'') include: an amidino group (—C(═NH)—NH$_2$); and substituents, for example, an alkyl(aralkyl)(aryl)amidino group, wherein 3 substituents on the N atom are substituted by 3 arbitrary identical or different substituents selected from an alkyl group, a cycloalkyl group, an alkenyl group, an alkynyl group, an aryl group, a heteroaryl group and an aralkyl group. Examples of substituents for forming a guanidino group (—NR—C(═NR''')—NR'R'') include: a guanidine group (—NH—C(═NH)—NH$_2$); and substituents wherein R, R', R'' and R''' are 4 arbitrary identical or different substituents selected from among an alkyl group, a cycloalkyl group, an alkenyl group, an alkynyl group, an aryl group, a heteroaryl group and an aralkyl group or are optionally ring-forming substituents selected from these substituents.

Examples of substituents for forming an urea group include an aminocarbamoyl group (—NR—CO—NR'R''). Further examples thereof include: substituents wherein R, R' and R'' are 3 arbitrary identical or different substituents selected from a hydrogen atom, an alkyl group, a cycloalkyl group, an alkenyl group, an alkynyl group, an aryl group, a heteroaryl group and an aralkyl group or are optionally ring-forming substituents selected from these substituents.

Examples of B atom-derived functional groups include alkylborane (—BR(R')) and alkoxyborane (—B(OR)(OR')). Further examples thereof include substituents wherein these two substituents (R and R') are two arbitrary or two identical substituents selected from among an alkyl group, a cycloalkyl group, an alkenyl group, an alkynyl group, an aryl group, a heteroaryl group, an aralkyl group and the like or are optionally ring-forming substituents selected from these substituents.

Thus, one or two or more of various functional groups containing an O atom, a N atom, a S atom, a B atom, a P atom, a Si atom or a halogen atom as used in ordinary small-molecule compounds, such as a halogen group, may be added to the amino acid or amino acid analog side chain. This means that the alkyl group, cycloalkyl group, alkenyl group, alkynyl group, aryl group, heteroaryl group or aralkyl group shown as one of these substituents may be further substituted by one or more substituents. Conditions under which a functional group satisfies all of the factors described herein are defined as the arbitrary selection of the substituent. Any conformation is acceptable for the β- or γ-amino acid, as in the α-amino acid. Its side chain can be selected without particular limitations, as in the α-amino acid. The main chain amino group site of the amino acid may be in a free form (NH$_2$ group) or may undergo N-alkylation such as N-methylation (NHR group wherein R arbitrarily represents an optionally substituted alkyl group, alkenyl group, alkynyl group, aryl group, heteroaryl group, aralkyl group or cycloalkyl group, or the carbon atom coming from the N atom and the carbon atom at the α-position optionally form a ring, as in proline; the substituent can be arbitrarily selected, and examples thereof include a halogen group, an ether group and a hydroxyl group).

In the present specification, the "translation amino acid" or "translatable amino acid" refers to an "amino acid" having a side chain that enables translation. As described herein below, the "translation amino acid" or "translatable amino acid" includes, for example: L-α-amino acids having an alkyl group, an alkenyl group, an alkynyl group, an aralkyl group, an aryl group, a heteroaryl group or a cycloalkyl group optionally substituted by one or more substituents such as a halogen group, a hydroxyl group (—OH), an alkoxy group (—OR), an ester group (—C(═O)—OR), a thioester group (—C(═O)—SR), a carboxyl group (—CO$_2$H), an amide group (—CO—NRR'' or —NR—CO—R'), a thiol group (—SH), an alkylthio group (—SR), a sulfoxide group (—S(═O)—R), a sulfone group (—SO$_2$—R), an amino group (—NH$_2$), a mono-substituted amino group (—NHR), a di-substituted amino group (—NRR'), an azide group (—N$_3$), a nitrile group (—CN) or an amidino group (—N═C(═N)—NH$_2$); N-methylated L-α-amino acids; glycine derivatives substituted by C1-C4 alkyl such as N-ethyl or N-propyl or substituted by N-aralkyl such as N-benzyl; and L-α-amino acids having a substituent having a reaction promoting group such as a thiol group, or various highly reactive functional groups that can be utilized in the triangle unit or the intersection unit, such as an amino group. The "translation amino acid" or "translatable amino acid" also includes some D-α-amino acids such as D-tyrosine, β-amino acids such as β-alanine, α,α-dialkylamino acids such as α-methyl-alanine (Aib), and the like.

In the present specification, the "drug-like amino acid" has a backbone identical to that of the "amino acid", i.e., is an α-, β- or γ-amino acid in which one of two hydrogen atoms in the main chain amino group (NH$_2$ group) and one or two of two hydrogen atoms in the methylene group (—CH$_2$— group) are each optionally replaced with an alkyl group, a cycloalkyl group, an alkenyl group, an alkynyl group, an aryl group, a heteroaryl group, an aralkyl group or the like. The drug-like amino acid has, as the side chain, a group in which a hydrogen atom in the CH$_2$ group is replaced with any of these groups. These substituents include those further substituted by a substituent that functions as a component for the drug-like peptide compound. These are optionally substituted by one or more substituents that are preferably selected from among the substituents otherwise defined above and selected from among, for example, a hydroxyl group (—OH), an alkoxy group (—OR), an amide group (—NR—CO—R' or —CO—NRR'), a sulfone group (—SO$_2$—R), a sulfoxide group (—SO—R), a halogen group, a hydroxylamino group (—NR—OR') and an aminohydroxy group (—O—NRR'). The drug-like amino acid may correspond to any of an L-amino acid, D-amino acid and α,α-dialkylamino acid. The drug-like amino acid is not necessarily required to be translatable. The drug-like amino acids includes all amino acids that can be chemically synthesized by the structural optimization of a side chain portion in a peptide obtained from "translation amino acids" (e.g., when a hit compound is obtained at D-tyrosine, a D-amino acid chemically modified therefrom; or when a hit compound is obtained at β-alanine, a β-amino acid chemically modified therefrom) or a N-substituted portion resulting from the chemical conversion of N-methylamino acid. These amino acids function as components for the drug-like peptide compound and are therefore selected from within the range where a peptide compound obtained by chemical modification carried out after translation becomes drug-like. As mentioned below, for example, lysine having an aminoalkyl group is not included in the drug-like amino acid, if its amino group is not involved in posttranslational modification. However, in the case of utilizing the amino group of lysine as a reactive functional group (e.g., in the intersection unit) in posttranslational modification, this lysine unit is included as a drug-like amino acid unit. Thus, whether an amino acid corresponds to the "drug-like amino acid" is determined depending on its functional group after conversion by posttranslational modification. Examples of substituents having such potentials include an ester group (—CO—OR), a thioester group (—CO—SR), a thiol group (—SH), a protected thiol group, an amino group (—NH$_2$), a mono-substituted amino group (—NH—R) or di-substituted amino group (—NRR'), a protected amino group, a substituted sulfonylamino group (—NH—SO$_2$—R), an alkylborane group (—BRR'), an alkoxyborane group (—B(OR)(OR')), an azide group (—N$_3$), a keto acid group (—CO—CO$_2$H), a thiocarboxylic acid group (—CO—SH), a phosphoryl ester group (—CO—PO(R)(R')) and an acylhydroxylamino group (—NH—O—CO—R), among the substituents otherwise defined above.

The amino acid analog of the present invention preferably means an α-hydroxycarboxylic acid. The side chain of the α-hydroxycarboxylic acid optionally has various substituents including a hydrogen atom (optionally has an arbitrary substituent), as in the amino acid. The conformation of the α-hydroxycarboxylic acid may correspond to the L- or D-conformation of the amino acid. The α-hydroxycarboxylic acid is not particularly limited by its side chain, and the side chain is arbitrarily selected from among, for example, an optionally substituted alkyl group, alkenyl group, alkynyl group, aryl group, heteroaryl group, aralkyl group and cycloalkyl group. The number of substituents is not limited to 1 and may be 2 or more. The α-hydroxycarboxylic acid has, for example, a S atom and may further have a functional group such as an amino group or a halogen group.

In the present specification, the "translation amino acid analog" or "translatable amino acid analog" means an "amino acid analog" that can be translated. Specific examples thereof include compounds in which the main chain amino group of an L-amino acid is replaced with a hydroxyl group. Examples of such compounds include L-lactic acid, α-hydroxyacetic acid and L- or D-phenyllactic acid. The "drug-like amino acid analog" is not particularly limited as long as the "amino acid analog" functions as a component for the drug-like peptide compound. This range is as defined in the side chain or N-substituted portion of the drug-like amino acid. Specific examples thereof include: L- or D-lactic acid and compounds in which various drug-like substituents (e.g., a halogen group, a hydroxyl group and an optionally substituted alkyl group, alkenyl group, alkynyl group, cycloalkyl group, aralkyl group, aryl group and heteroaryl group) are added to its side chain methyl group; α-hydroxyacetic acid; and L or D-phenyllactic acid and compounds in which various drug-like substituents (e.g., a halogen group, a hydroxyl group and an optionally substituted alkyl group, alkenyl group, alkynyl group, cycloalkyl group, aralkyl group, aryl group and heteroaryl group) are added to its side chain benzyl group. The drug-like amino acid analog is not necessarily required to be translatable. "Translation amino acid analogs" that give a drug-like peptide compound by posttranslational chemical modification are also included in the "drug-like amino acid analog". Examples of such amino acid analogs include α-hydroxycarboxylic acid having an SH group added to the side chain and α-hydroxycarboxylic acid having an amino group or protected amine site added to the side chain. For example, the SH group can be removed by desulfurization reaction after posttranslational modification. The amino group can be converted to amide or the like by posttranslational modification. A particular example thereof includes R-2-hydroxy-3-sulfanylpropanoic acid.

The N-terminal carboxylic acid analog of the present invention may be a compound having both amino and carboxyl groups between which 3 or more atoms are present, any of various carboxylic acid derivatives not having an amino group, a peptide formed by 2 residues to 4 residues, or an amino acid having a main chain amino group chemically modified by an amide bond or the like with carboxylic acid. Also, the N-terminal carboxylic acid analog may have a boric acid or boric acid ester site that can be used in cyclization at the curved line. Alternatively, the N-terminal carboxylic acid analog may be a carboxylic acid having a double bond site or a triple bond site or may be a carboxylic acid having ketone or halide. For these compounds as well, portions other than the functional groups thus specified are widely selected from arbitrary substituents such as an optionally substituted alkyl group, aralkyl group, aryl group, cycloalkyl group, heteroaryl group, alkenyl group and alkynyl group.

In the present specification, the "translation N-terminal carboxylic acid analog" or "translatable N-terminal carboxylic acid analog" means an "N-terminal carboxylic acid analog" that can be translated. Specific examples thereof include: compounds in which a double bond and a carboxylic acid are connected by an alkyl group (but-3-enoic acid, pent-4-enoic acid, etc.); L-amino acids having an N-terminal amidated by acetylation or the like (Ac-Phe, Ac-Ala, Ac-Leu, etc.); α-hydroxycarboxylic acid derivatives having an alkylated OH group; and dipeptide or tripeptide. The "drug-like N-terminal carboxylic acid analog" is not particularly limited as long as the "N-terminal carboxylic acid analog" functions as a component for the drug-like peptide compound. The drug-like N-terminal carboxylic acid analog contains the same substituent as that defined in the side chain of the drug-like amino acid. Specific examples of the drug-like N-terminal carboxylic acid analog include: compounds in which a double bond and a carboxylic acid are connected by an alkyl group (but-3-enoic acid, pent-4-enoic acid, etc.) wherein a substituent is added to a carbon atom in a drug-like range; L-amino acids having an N-terminal amidated by acetylation or the like (Ac-Phe, Ac-Ala, Ac-Leu, etc.) wherein a hydrogen atom in the acetyl group or at the side chain or the α-position is substituted in a drug-like range; α-hydroxycarboxylic acid derivatives having an alkylated OH group wherein a hydrogen atom or the like in the alkyl group of the OH group or at the side chain or the α-position of the hydroxycarboxylic acid is substituted in a drug-like range; and dipeptide or tripeptide substituted in a drug-like range. The drug-like N-terminal carboxylic acid analog is not necessarily required to be translatable. "Translation N-terminal carboxylic acid analogs" that give a drug-like peptide compound by posttranslational chemical modification are also included in the "drug-like N-terminal carboxylic acid analog". Examples of such N-terminal carboxylic acid analogs include dipeptide having an amino group remaining at the N-terminal, γ-aminocarboxylic acid and δ-aminocarboxylic acid.

Membrane Permeability of Peptide Compound

The peptide compound of the present invention preferably contains 13 or less amino acids in total, for its favorable membrane permeability.

Each unit (amino acid residue) is selected without particular limitations and is preferably selected such that the resulting molecule has CLogP (which refers to a computed distribution coefficient calculated by using Daylight Version 4.9 (Daylight Chemical Information Systems, Inc.) exceeding 6 in terms of a complete modified form (main chain structure) by chemistry after translation. For securing particularly favorable membrane permeability, each unit is preferably selected such that CLogP exceeds 8 and does not exceed 15.

For securing membrane permeability, each amino acid side chain is more preferably selected from among drug-like substituents. The amino acid side chain is preferably selected from among, for example, an optionally substituted alkyl group, cycloalkyl group, alkenyl group, alkynyl group, aralkyl group, aryl group and heteroaryl group and has an added substituent, for example, a halogen group, a hydroxy group (—OH), an amide group (—CO—NRR' or —NR—CO—R'), a sulfone group (—SO$_2$—R) or an ether group (—OR) (wherein R and R' are each selected from among an alkyl group, cycloalkyl group, alkenyl group, alkynyl group, aryl group, heteroaryl group, aralkyl group also optionally substituted by these substituents). In addition to a phenyl group, basic groups such as a pyridine group, groups containing two or more heteroatoms such as a thiazole group, hydrogen atom donors such as an imidazole group, condensed aromatic rings such as an indole group and the like are acceptable as the aryl group or the aryl group site of the aralkyl group.

Examples of polar functional groups not preferred for obtaining membrane permeability include functional groups that are excessively ionized in vivo (pH=around 7), such as an alkylamino group and an alkylguanidino group. It is preferred that these functional groups should not be contained therein.

For the purpose of obtaining membrane permeability, an amino acid or amino acid analog that has undergone N-alkylation such as N-methylation or cyclization with a carbon atom at the α-position as found in proline may be used to constitute the peptide compound. The number of such amino acids or amino acid analogs is preferably 2 or more per peptide molecule. It is also preferred that at least one non-N-alkylated amide bond should be present per peptide molecule. Desirably, one peptide molecule contains 3 or more N-alkylated amino acids or amino acid analogs and 3 or more non-N-alkylated amino acids or amino acid analogs. This N-alkylation includes all chemical modifications except for NH and is thus carried out with a group selected from among an optionally substituted (the substituent is selected in the same way as in the selection of the substituent for the amino acid side chain described above for securing membrane permeability) alkyl group, cycloalkyl group, alkenyl group, alkynyl group, aryl group, heteroaryl group and aralkyl group. The N-alkylation also includes the formation of a ring structure between a N atom and α-carbon as found in proline.

The C-terminal site of the peptide compound is more preferable to be modified chemically than being carboxylic acid. For example, the carboxylic acid site is preferably converted to amide compound, for example of the piperidine amide by the reaction of carboxylic acid and piperidine. Various other amide is preferable like an optionally substituted alkyl group, alkenyl group, alkynyl group, cycloalkyl group, aryl group, heteroaryl group or aralkyl group-containing amide compound (—CO—NRR' wherein one of R and R' may be a hydrogen atom and the other may be chemically modified, both of R and R' may be chemically modified, R and R' may be chemically modified (e.g., piperidinamide) by forming a ring, or both of R and R' may be hydrogen atoms) such as piperidinamide by reaction with piperidine or the like. Or the carboxylic acid group is preferably converted to various nonionic functional groups such as an optionally substituted alkyl group (e.g., a methyl ester or a trifluoromethyl ester), alkenyl group, alkynyl group, aryl group, heteroaryl group or aralkyl group. The substituent is selected in the same way as in the selection of the substituent for the amino acid side chain described above for securing membrane permeability. The amino acid constituting the peptide compound may help optimize a translationally synthesized compound. The amino acid constituting the obtained peptide compound is not limited to a translationally synthesized amino acid.

In this context, the optimization means that each amino acid in a compound translationally synthesized from "translation amino acids" is chemically modified by structural conversion in a range of a drug-like peptide compound, chemically modified to give a peptide compound having stronger activity against a drug target, and/or chemically modified to give a peptide compound with avoiding its toxicity. In this context, examples of the toxicity that should be or can be avoided include hERG inhibition (toxicity to the heart), AMES test (carcinogenicity test), CYP inhibition (drug-drug interaction test), CYP induction and GSH binding ability assay test (peptide or peptide metabolite covalent bond formation test using glutathione). The peptide compound itself serving as an active ingredient and its metabolite are considered to participate in these tests. Particularly, in the AMES test, CYP induction or GSH binding ability assay test, the metabolite, which may generate a covalent bond, is preferably avoided for securing negative results. For this reason, it is preferred that the cyclization sites contained in all peptide compounds in a display library should be constracted by cyclization reaction that does not form functional groups having such potentials and is resistant to, particularly, oxidation reaction, to some extent. As practiced for many small-molecule compounds, for example, a phenyl group in phenylalanine identified as a translation amino acid can be subjected to various chemical modifications such as alkyl substitution or halogen substitution. Such conversion can be carried out without largely impairing the three-dimensional structure of the translationally synthesized compound and largely differs in this respect from the conventional chemical modification by N-methylation or cyclization of natural peptides. In addition, in most natural peptides, excessively ionized arginine or lysine residues contribute to their activity. These residues are therefore difficult to convert to drug-like functional groups. By contrast, a clinical candidate compound chemically modified as usually carried out in small-molecule chemistry can be obtained with accuracy and success rate equivalent to those of small-molecule chemistry by putting the technique of the present invention to full use, because the functional groups confined to drug-like functional groups beforehand produce activity against a drug target and are cyclized by a drug-like cyclization method. On the other hand, the CLogP value serving as an index for lipid solubility can be easily adjusted in the process of optimization. Also, the binding activity against a target can be enhanced by alkylation or halogenation that is also usually carried out in the optimization of small-molecule compounds. Typically, 10-fold to 50-fold improvement in activity can be expected. Such usual conversion can increase the CLogP value at the same time. For example, the CLogP value can be increased by approximately 0.7 by chlorination and can be increased by approximately 0.5 by methylation. Such increase in CLogP value in the process of optimization is not enough for a peptide compound having an excessively ionized functional group to obtain excellent membrane permeability. In the absence of excessively ionized functional groups, however, a CLogP value sufficient for membrane permeation can be obtained in the process of optimization. Thus, it can be judged as being feasible that, for example, when a hit compound having a CLogP value of 5 is obtained from a display library having a CLogP value of approximately 6 on average, this compound can be optimized by further increasing its CLogP value to the range of 8 to 15 that is most suitable for membrane permeation.

The membrane permeability of the peptide compound of the present invention can be confirmed by using a method known in the art, for example, a rat intestinal method, cultured cell (Caco-2, MDCK, HT-29, LLC-PK1, etc.) monolayer method, immobilized artificial membrane chromatography, method using distribution coefficients, ribosome membrane method or parallel artificial membrane permeation assay (PAMPA). Specifically, in the case of using, for example, the PAMPA method, the membrane permeability of the peptide compound can be confirmed according to the description of the literature of Holger Fischer et al. (Non Patent Literature: H. Fischer et al., Permeation of permanently positive charged molecules through artificial membranes-influence of physic-chemical properties. Eur J. Pharm. Sci. 2007, 31, 32-42). More specifically, the membrane permeability can be confirmed according to a method described in Example 19-2.

The membrane permeability of oral drugs hydrochlorothiazide, furosemide and metoprolol having membrane permeability is determined by the PAMPA method to have iPAMPA Pe values of $0.6 \times 10^{-6}$, $1.5 \times 10^{-6}$ and $2.9 \times 10^{-5}$, respectively. The membrane permeability of the peptide compound of the present invention can be usually regarded as being membrane permeability that makes the peptide compound usable as a pharmaceutical agent, when having an iPAMPA Pe value of $1.0 \times 10^{-6}$ or higher determined by, for example, the PAMPA method. The iPAMPA Pe value is preferably $1.0 \times 10^{-6}$ or higher, more preferably $1.0 \times 10^{-5}$ or higher, particularly more preferably $1.5 \times 10^{-5}$ or higher, still more preferably $2.0 \times 10^{-5}$ or higher.

Metabolic Stability of Peptide Compound

The peptide compound of the present invention preferably contains 9 or more amino acids in total, more preferably 11 or more amino acids in total, for its favorable metabolic stability. The conditions under which the peptide compound has membrane permeability as mentioned above do not influence the metabolic stability of the peptide compound as long as the peptide compound contains 9 or more amino acids in total.

The metabolic stability of the peptide compound of the present invention can be confirmed by using a method known in the art, for example, hepatocytes, small intestinal cells, liver microsomes, small intestinal microsomes or liver S9. Specifically, the stability of the peptide compound, for example, in the liver microsome can be confirmed by assay according to the description of the literature of LL von Moltke et al. (Midazolam hydroxylation by human liver microsomes in vitro: inhibition by fluoxetine, norfluoxetine, and by azole antifungal agents. J Clin Pharmacol, 1996, 36 (9), 783-791). More specifically, the stability of the peptide compound can be confirmed according to a method described in Example 18-2.

The metabolic stability can be regarded as being metabolically stable that makes the peptide compound pharmaceutically usable as an oral formulation, when having an intrinsic hepatic clearance (CLh int (µL/min/mg protein)) value of 150 or lower determined according to the method mentioned above, for example, in the liver microsome. The intrinsic hepatic clearance value is preferably 100 or lower. A drug that is metabolized by CYP3A4 has a value of preferably 78 or lower (Non Patent Literature: M. Kato et al., The intestinal first-pass metabolism of substances of CYP3A4 and P-glycoprotein-quantitative analysis based on information from the literature. Drug Metab. Pharmacokinet. 2003, 18 (6), 365-372) for avoiding its metabolism in the small intestine of a human, more preferably 35 or lower (assuming FaFg=1 and protein binding rate of 0%) for exhibiting approximately 30% or more bioavailability in humans.

See FIG. 84.

Method for Preparing Peptide Compound Having Cyclic Portion

The peptide compound having a cyclic portion according to the present invention can be prepared by using a method described below.

Examples of the preparation method can include a preparation method comprising the steps of:
1) translationally synthesizing a noncyclic peptide compound composed of amino acid residues and/or amino acid analog residues or of amino acid residues and/or amino acid analog residues and an N-terminal carboxylic acid analog from a nucleic acid sequence encoding the peptide compound,
   wherein the noncyclic peptide compound contains an amino acid residue or amino acid analog residue having a single reactive site at a side chain on the C-terminal side thereof, and an amino acid residue, amino acid analog residue or the N-terminal carboxylic acid analog having another reactive site on the N-terminal side; and 2) forming an amide bond or a carbon-carbon bond between the reactive site of the amino acid residue, amino acid analog residue or the N-terminal carboxylic acid analog on the N-terminal side and reactive site of the amino acid residue or amino acid analog residue at the side chain on the C-terminal side.

A method known in the art can be used for the translational synthesis of the present invention.

Introduction of Translatable Amino Acid, Translatable Amino Acid Analog or Translatable N-Terminal Carboxylic Acid Analog into N-Terminal In general, methionine is known as the initial (first) amino acid by translation, as the result methionine is located at N-terminal. Alternative amino acids could also translated as the N-terminal by using an aminoacylated tRNA of desired amino acid instead of that of methionine. The N-terminal introduction of an unnatural amino acid is known to have higher amino acid tolerance than that during elongation and utilize an amino acid or amino acid analog largely structurally different from a natural amino acid (Non Patent Literature: J Am Chem Soc. 2009 Apr. 15; 131 (14): 5040-1. Translation initiation with initiator tRNA charged with exotic peptides. Goto Y, Suga H.). In the present invention, a translatable amino acid, translatable amino acid analog or translatable N-terminal carboxylic acid derivative other than methionine can be introduced into the N-terminal by, for example, a method described below. A triangle unit-acylated tRNA is added as a translation initiation tRNA to a translation system except for methionine, a formyl donor or methionyl transferase so that the triangle unit is encoded and translated at a translation initiation codon (e.g., ATG) to construct an uncyclized peptide compound or a peptide compound library having the terminal triangle unit. Various combinations of a translation initiation tRNA having an anticodon other than CAU and a codon corresponding to the anticodon can be used as the combination of the translation initiation tRNA and the initiation codon to diversify the N-terminal. That is, the desired amino acid, amino acid analog or N-terminal carboxylic acid analog is aminoacylated to each of plural types of translation initiation tRNAs differing in anticodon. mRNAs or mRNA libraries having initiation codons corresponding thereto can be translated to make uncyclized peptide compounds or peptide compound libraries having various types of N-terminal residues. Specifically, the uncyclized peptide compounds or peptide compound libraries can be made by a method described in, for example, Mayer C, et al., Anticodon sequence mutants of *Escherichia coli* initiator tRNA: effects of overproduction of aminoacyl-tRNA synthetases, methionyl-tRNA formyltransferase, and initiation factor 2 on activity in initiation. Biochemistry. 2003, 42, 4787-99 (translation initiation from an amino acid other than f-Met by variant *E. coli* initiation tRNA having anticodon other than CAU and protein expression involving the corresponding codon midstream).

Examples of the method for forming a bond between the reactive site of the amino acid residue, amino acid analog residue or the N-terminal carboxylic acid analog on the N-terminal side and reactive site of the amino acid residue or amino acid analog residue at the side chain on the C-terminal side include a method of providing a cyclic compound by forming an amide bond between an amino acid residue, amino acid analog residue or N-terminal carboxylic acid analog having an amino group and a reaction promoting group at the side chain on the N-terminal side and an amino acid residue or amino acid analog residue having an active ester group at the side chain, a method of providing a cyclic compound by forming an amide bond between an N-terminal amino acid residue, amino acid analog residue or N-terminal carboxylic acid analog having an amino group and an amino acid residue or amino acid residue having an active ester group at the side chain, and a method of forming a carbon-carbon bond between the reactive site of the N-terminal amino acid residue, N-terminal amino acid analog residue or N-terminal carboxylic acid analog and reactive site of the amino acid residue or amino acid analog having a single reactive site at the side chain. The method is not limited to the examples described above and may be achieved by locating the functional groups at opposite positions, for example, by forming an amide bond between an N-terminal amino acid residue, N-terminal amino acid analog or N-terminal carboxylic acid having an active ester group and an amino acid or amino acid analog having an amino group at the side chain on the C-terminal side (which may have a reaction promoting group).

Hereinafter, a reaction design will be described by taking use of amide cyclization as an example. For obtaining reaction selectivity between an amino group to be reacted and basic functional groups to be not reacted in the triangle unit, it may be required to improve the reactivity of the amine to be reacted with respect to the reactivity of the other functional groups. An approach of activating the reactivity of the amine to be reacted than a common amine can usually involve introducing, for example, a reaction promoting group vicinally oriented to the target amine. The reaction promoting group is not particularly limited as long as the reaction promoting group can activate the amine without causing the reaction of RNA. For example, a mercaptoethyl group or mercaptopropyl group may be introduced to the terminal amine, or a thiol site may be introduced from the α-position of the amine as found in cysteine (see Scheme C). These thiol groups may or may not be protected in the process of translational incorporation and are generated by deprotection reaction, if necessary, during or prior to reaction. The amine thus activated can be reacted with carboxylic acid active ester to give a peptide amide-cyclized at the desired position. The SH group of the obtained cyclic peptide can be desulfurized under mild reaction conditions (which do not cause the reaction of RNA) where reagents such as TCEP (tris(2-carboxylethyl)phosphine) and VA-044 (2,2'-azobis-2-(2-imidazolin-2-yl)propane) are added.

In the case of creating a display library by translation, a thioester is preferred as active ester in the intersection unit to be translationally incorporated. The translational synthesis is carried out using, for example, an SH group as the reaction promoting group and a combination as described below. For the translational synthesis using an unprotected SH group, an aspartic acid derivative is preferably used as the thioester in the intersection unit. In this case, all of the filled circle units and the square units can be arbitrarily selected from among translation amino acids and translation amino acid analogs. On the other hand, for the translational synthesis using an SH group having a protecting group, the square unit flanking the C-terminal side of the aspartic acid thioester is preferably selected from among N-alkylated amino acids (e.g., proline and N-methylalanine).

Figure 85:
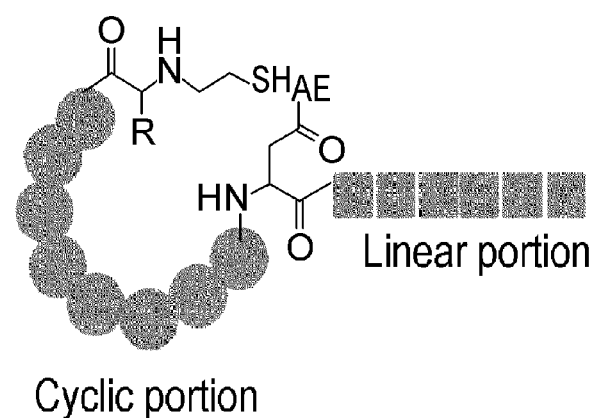
FIG. 85 is a diagram showing Scheme C. Scheme C shows an example of an uncyclized translated compound having activated amine at the triangle unit and aspartic acid or active ester at the intersection unit. This is a specific example of A-1. R represents an amino acid side chain, and AE represents OH or active ester.

See FIG. 85.

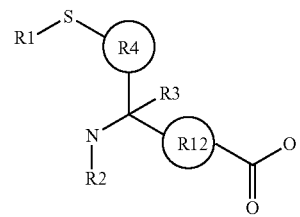

Compound N-1

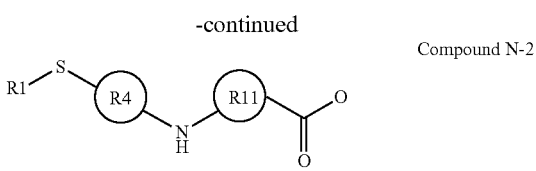

Compound N-2

The amino acid or N-terminal carboxylic acid analog, for example, N-terminal amino acid, having a reaction promoting group vicinally oriented to the amine as the triangle unit can be represented by, for example, Compound N-1 or N-2 of the above general formulas. In these Compounds N-1 and N-2, substituents represented by R except for protecting groups (R1, R23 or a trityl group, etc.) are preferably as defined above in the side chain of the drug-like amino acid. The substituents are more preferably substituents that provide for translational synthesis of a compound obtained as a result of introduction thereof. The substituents also include substituents wherein even if the derivatives themselves are not translationally synthesized, analogs thereof are translationally synthesized (see paragraphs described later (e.g., the third later paragraph)).

R1 is selected from among a hydrogen atom, and a protecting group for the SH group represented by a S—R23 group or C(Phe)3 group (trityl group). R23 is selected from: alkyl groups such as a methyl group, ethyl group, isopropyl group and tert-butyl group; aryl groups such as a phenyl group, p-trifluoromethylphenyl group and p-fluorophenyl group; aralkyl groups such as a benzyl group and phenethyl group; and other groups including a heteroaryl group, an alkenyl group and an alkynyl group. These groups are selected from among substituents that provide for translational synthesis of the resulting Compound N-1 or N-2. For example, a N,N-dimethylaminoethylmercapto group in which an ethyl group of R23 is substituted by a dimethylamino group may be used. When R1 has a protecting group (R1 is a group other than a H atom), the protecting group can be selected without particular limitations as long as the protecting group is selected from among protecting groups that provide for translational synthesis and deprotected in a translational synthesis solution to form a hydrogen atom before cyclization. The protecting group such as a S—R23 group is slowly deprotected in a translational synthesis solution and therefore, can be deprotected without the need of otherwise actively specifying deprotection conditions. If necessary, a deprotecting agent can be added under various reaction conditions described herein (described in the protecting group for the SH group).

R2 and R3 are as defined in the side chain of the drug-like amino acid. Preferably, R2 and R3 each represent, for example, a hydrogen atom, or an alkyl group, an alkenyl group, an alkynyl group, an aryl group, a heteroaryl group, an aralkyl group or a cycloalkyl group which optionally has a substituent; or represent a substituent in which R2 and R3 form a ring, or a substituent in which R2 or R3 and R4 form a ring. More preferably, R2 and R3 are each selected from, for example, a hydrogen atom, and a C1-C4 alkyl group optionally substituted by a C1-C4 alkyl group, an alkoxy group, a halogen group or the like. Both conformations compatible to L- and D-amino acids are acceptable for the R3 group. Preferably, the R3 group has a conformation compatible to an L-amino acid, provided that the R3 group is a hydrogen atom.

R4 is a unit that links the S (sulfur) atom and the amino acid site. Hereinafter, a typical structure thereof will be shown. Both the units can be linked by any of C1-C6 units including an optionally substituted methylene group (partial structure N-3, C1 unit), an optionally substituted ethylene group (partial structure N-4, C2 unit) and an optionally substituted propylene group (partial structure N-5, C3 unit). Examples of the substituents in the optionally substituted methylene group, ethylene group and propylene group include Compound N-1 wherein R13 is methylated (R14=H) and dimethylated Compound N-1 wherein R13=R14=Me. This definition includes all of the cases where any of the derivatives are translationally synthesized, even if the other derivatives are not translationally synthesized. For example, when a derivative wherein R13=R14=H is translationally synthesized, a derivative wherein R13=R14=Me may not be translationally synthesized. In such a case, these substituents are included in the definition of the drug-like amino acid side chain and can therefore be contained in the triangle unit. R13, R14, R15, R16, R17, R18, R19, R20, R21, R22 and the like are as defined in R4 and are each selected from, for example, a hydrogen atom and a C1-C4 alkyl group optionally substituted by a C1-C4 alkyl group, alkoxy group, halogen atom or the like. A ring structure may be formed between these groups. Particularly preferably, these groups are each selected from a hydrogen atom and a methyl group. Alternatively, direct linkage may be formed from the aryl carbon of an aromatic compound (partial structure N-6). Alternatively, the linkage may be formed by an aralkyl structure (partial structures N-7 and N-8). In the partial structure N-7, either atom of the divalent moiety may be located on the nitrogen atom side or may be located on the sulfur atom side. In a scheme shown below, the linking position is limited to the ortho-position, but may be, for example, the meta- or para-position without being limited to the ortho-position. Although a phenyl group will be shown as an example of the aryl group, the phenyl group is optionally substituted by a substituent such as a halogen group, alkoxy group or trifluoromethyl group. Alternatively, aryl groups other than the phenyl group (i.e., various aromatic rings including heteroaryl groups) may be used.

Partial structure N-3

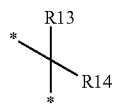

Partial structure N-4

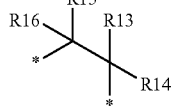

Partial structure N-5

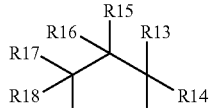

Partial structure N-6

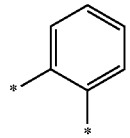

Partial structure N-7

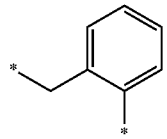

Partial structure N-8

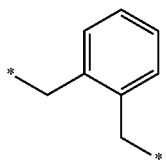

R11 and R12 are also selected from partial structures similar to R4. For example, R11 and R12 can each be selected from among partial structures N-3, N-4, N-5, N-6, N-7 and N-8. R12 can also contain a C0 unit (in the case of direct linkage at the linking site).

Preferred structural formulas of the compound structure N-1 and compound structure N-2 are shown in compound structures N-9, N-10, N-11 and N-12. In Compound N-9, the R12 site of Compound N-1 forms direct linkage at the linking site as a C0 unit. In Compound N-10, the R11 site of Compound N-2 forms linkage as a C1 unit (corresponding to partial structure N-3). In Compound N-11, the R11 site of Compound N-2 forms linkage as a C2 unit (corresponding to partial structure N-4). In Compound N-12, the R11 site of Compound N-2 forms linkage as a C3 unit (corresponding to partial bond N-5).

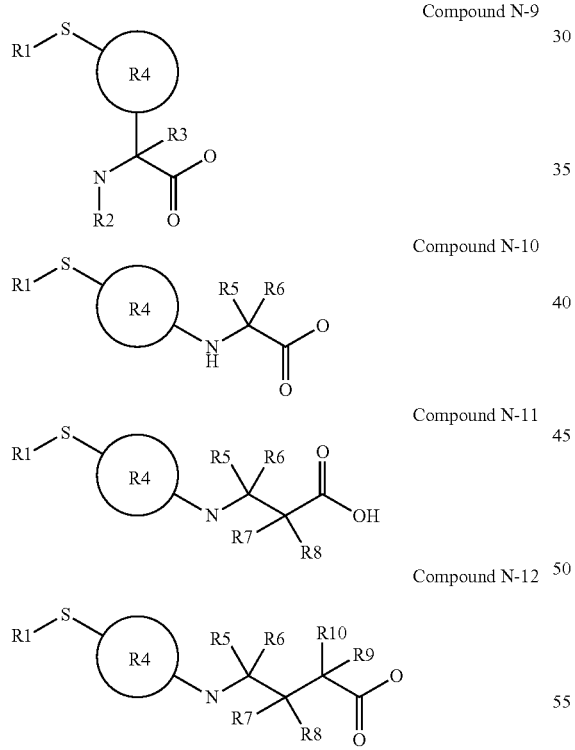

R5 to R10 are as defined above in R13 to R18.

The more desirable structural formulas thereof are shown below in Compounds N-13, N-14, N-15, N-16, N-17, N-18, N-19 and N-20. In Compound N-13, the R4 site of Compound N-9 forms linkage as a C1 unit (corresponding to partial structure N-3). In Compound N-14, the R4 site of Compound N-10 forms linkage as a C2 unit (corresponding to partial structure N-4). In Compound N-15, the R4 site of Compound N-11 forms linkage as a C2 unit (corresponding to partial structure N-4). In Compound N-16, the R4 site of Compound N-12 forms linkage as a C2 unit (corresponding to partial structure N-4). In Compound N-17, the R4 site of Compound N-9 forms linkage as a C2 unit (corresponding to partial structure N-4). In Compound N-18, the R4 site of Compound N-10 forms linkage as a C3 unit (corresponding to partial structure N-5). In Compound N-19, the R4 site of Compound N-11 forms linkage as a C3 unit (corresponding to partial structure N-5). In Compound N-20, the R4 site of Compound N-12 forms linkage as a C3 unit (corresponding to partial structure N-5).

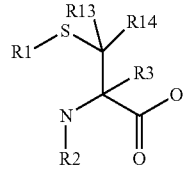

Compound N-13

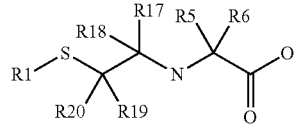

Compound N-14

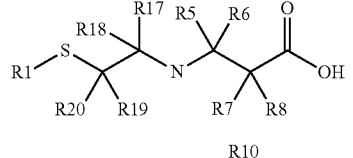

Compound N-15

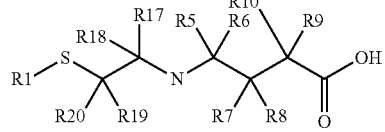

Compound N-16

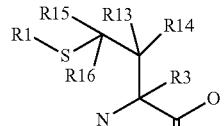

Compound N-17

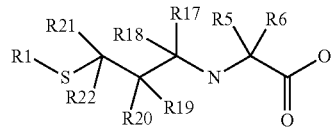

Compound N-18

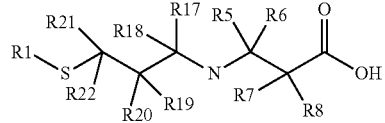

Compound N-19

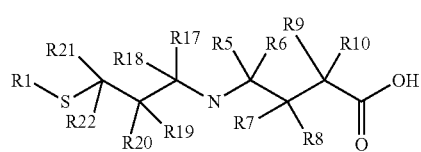

Compound N-20

Although the chemical structures represented by the general formulas of Compounds N-1 and N-2 are described above, the definition of the triangle unit containing the reaction promoting group SH is not limited by them. Specifically, the triangle unit has an amino group and a reaction promoting group as a unit to be reacted with the intersection unit and has any structure selected from among translationally synthesizable structures. The amino group may be derived from the main chain or may be derived from the side chain. The triangle unit is not necessarily required to be located at the N-terminal, and a square unit (linear portion) may be located on the N-terminal side of the triangle unit. A chemical structure is preferred in which the positional relationship between the SH group and the amino group is a relationship having 2 to 6 linking atoms between these two functional groups, such as β (2 linking atoms between these two functional groups) or γ (3 linking atoms therebetween). More preferably, the positional relationship between the SH group and the amino group assumes β or γ. Alternatively, a unit having an active ester functional group may be located in the triangle unit, while a unit containing amine may be located on the intersection unit side.

The amino acid residue having an active ester group at the side chain can be represented by Compound C-1 of the general formula below. Preferably, its substituents except for the active ester site are as defined in the side chain of the drug-like amino acid. The substituents also include substituents wherein even if the derivatives themselves are not translationally synthesized, analogs thereof are translationally synthesized. In the present application, the active ester means a carboxylic acid derivative that can be reacted with the amino group site either directly or through a reaction promoting group. Any active ester or active thioester having such properties can be used without particular limitations. R25 is selected from among a hydrogen atom and an active ester group. The active ester is typified by, for example, a N-hydroxysuccinimide (ONSu) group, OAt group, OBt group, methylthioester, arylthioester and aralkylthioester, as widely used. These activated ester sites also include all derivatives with usual compound substituents widely used (examples of the substituents include: electron-withdrawing groups such as a halogen group, nitro group, trifluoromethyl group and nitrile group often used for the purpose of enhancing reactivity; electron-donating groups such as an alkoxy group (e.g., methoxy group) and alkyl group (e.g., methyl group) often used for the purpose of reducing reactivity and thereby enhancing reaction selectivity; bulky substituents typified by a t-butyl group and isopropyl group; and di-substituted amino groups such as a sulfonic acid group and dimethylamino group in consideration of affinity for water for practice in water or highly lipid-soluble groups such as a long-chain alkyl group in consideration of lipophilicity), as long as the derivatives exhibit similar reactivity.

R2 and R3 are as defined above in the amine site.

R26 is as defined in R4. Hereinafter, a typical structure thereof will be shown. Both the units can be linked by any of C1-C6 units including a methylene group (partial structure N-3), ethylene group (partial structure N-4) and propylene group (partial structure N-5). Preferably, the substituents represented by R13, R14, R15, R16, R17, R18, R19, R20, R21 and R22 are as defined in the side chain of the drug-like amino acid. The substituents also include substituents wherein even if the derivatives themselves are not translationally synthesized, analogs thereof are translationally synthesized. These groups are each selected from, for example, a hydrogen atom and a C1-C4 alkyl group optionally substituted by a C1-C4 alkyl group, halogen atom or the like. A ring structure may be formed between these groups. More preferably, these groups are each selected from a methylene group (C1 unit, partial structure N-3), a C4 unit, a C5 unit and a C-6 unit. Further preferably, a C1 unit (partial structure N-3) is selected. Alternatively, direct linkage may be formed from the aryl carbon of an aromatic compound (partial structure N-6). Alternatively, the linkage may be formed by an aralkyl structure (partial structures N-7 and N-8). In a scheme shown below, the linking position is limited to the ortho-position, but may be, for example, the meta- or para-position without being limited to the ortho-position. Although a phenyl group will be shown as an example of the aryl group, the phenyl group is optionally substituted by a substituent such as a halogen group or alkoxy group. Alternatively, aryl groups other than the phenyl group may be used.

A preferred structure of Compound C-1 is shown in Compound C-2. R27 is selected from among a hydrogen atom, an optionally substituted alkyl group, an optionally substituted alkenyl group, an optionally substituted alkynyl group, an optionally substituted aryl group, an optionally substituted heteroaryl group, an optionally substituted cycloalkyl group and an aralkyl group to which an optionally substituted alkyl group may be added. These substituents are not particularly limited as long as Compound C-2 obtained as a result of selection of the substituents can be translationally synthesized. The substituents are selected from, for example: electron-withdrawing groups such as a halogen group, nitro group, trifluoromethyl group and nitrile group often used for the purpose of enhancing reactivity; electron-donating groups such as an alkoxy group (e.g., methoxy group) and alkyl group (e.g., methyl group) often used for the purpose of reducing reactivity and thereby enhancing reaction selectivity; bulky substituents typified by a t-butyl group and isopropyl group; and di-substituted amino groups such as a sulfonic acid group and dimethylamino group in consideration of affinity for water for practice in water or highly lipid-soluble groups such as a long-chain alkyl group in consideration of lipophilicity. Preferably, the substituents are each selected from an optionally substituted alkyl group, an optionally substituted cycloalkyl group and an optionally substituted aralkyl group. More preferably, the substituents are each selected from an alkyl group and an aralkyl group optionally substituted at the aryl site.

R3 is as defined in the side chain of the drug-like amino acid and is selected from, for example, a C1-C4 alkyl group optionally substituted by a C1-C4 alkyl group, halogen or the like. A hydrogen atom is particularly preferred. Both conformations compatible to L- and D-amino acids are acceptable for the R3 group, provided that the R3 group is a hydrogen atom. Preferably, the R3 group has a conformation compatible to an L-amino acid.

A more preferred structure is shown in Compound C-3. R28 and R29 are each as defined in the side chain of the drug-like amino acid and selected from among, for example, a hydrogen atom, an optionally substituted C1-C6 alkyl group, an optionally substituted C2-C6 alkenyl group, an optionally substituted C2-C6 alkynyl group, an optionally substituted aryl group, an optionally substituted heteroaryl group, an aralkyl group to which an optionally substituted C1-C6 alkyl group may be added and an optionally substituted cycloalkyl group. Examples of these substituents include monomethylation (R28=Me, R29=H), demethylation (R28=R29=Me) and monotrifluoromethylation (R28=CF3, R29=H).

R3 is selected from, for example, a hydrogen atom and a C1-C4 alkyl group optionally substituted by a C1-C4 alkyl group, halogen or the like and is particularly preferably a hydrogen atom. Both conformations compatible to L- and D-amino acids are acceptable for the R3 group, provided that the R3 group is a hydrogen atom. Preferably, the R3 group has a conformation compatible to an L-amino acid.

As in Compounds C-1, C-2 and C-3, Compound COH-1, COH-2 or COH-3 may be selected.

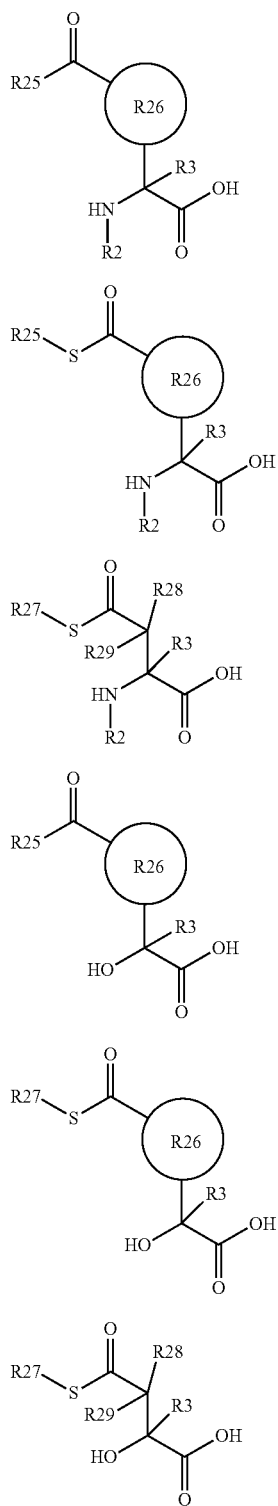

Compound C-1

Compound C-2

Compound C-3

Compound COH-1

Compound COH-2

Compound COH-3

In the case of Compound C-2 or C-3, reaction with Compound N-1 or N-2 can be allowed to proceed mildly and selectively. The reaction can be allowed to proceed smoothly even in a translation solution (e.g., 37° C., pH around 7.3). The removal of the reaction promoting group can also be allowed to proceed easily under reaction conditions where RNA is stable.

When activated ester is located on the N-terminal side (triangle unit), an amine unit having a reaction promoting group may be located on the C-terminal side (intersection unit). In this case, an amino group and a thiol group are located at the side chain of the intersection unit. These groups are optionally protected at the stage of translation, but are deprotected before reaction. The amino group and the thiol group are not particularly limited by their positions as long as these groups are located vicinally each other. Preferably, their positional relationship assumes β or γ.

All drug-like cyclization approaches by amide condensation reaction between the activated ester such as thioester at the side chain of the triangle unit and the amino group (with a reaction promoting group such as thiol vicinally oriented to the amine) at the side chain on the other side (intersection unit) are also included in the present application. Either of the functional groups may be located in the triangle unit or the intersection unit.

Hereinafter, specific examples of structures different from those of Compounds N-1 and N-2 will be shown as the amine site having a reaction promoting group. In any case, the amino group and the thiol group are optionally protected, if necessary. Their protecting groups and deprotection reaction conditions can be selected by using methods described herein. For Compound Na-10, as shown in the drawing, a structure can be selected in which 2 carbon atoms are located between the amino group and the thiol group. For Compound Na-11, as shown in the drawing, a structure can be selected in which 3 carbon atoms are located between the amino group and the thiol group. A Na-7 group, Na-8 group or Na-9 group is located as a substituent in any of Ra20 to Ra25. Ra7 is as already defined. Only in the case of Compound Na-10 or Na-11, Ra7 may be selected from a Na-7 group, Na-8 group and Na-9 group. The Na-7 group, Na-8 group or Na-9 group is restrictedly selected to any one of Ra-7 or Ra20 to Ra25. Ra20 to Ra25 other than the substituent selected as the Na-7 group, Na-8 group or Na-9 group are each selected from a hydrogen atom and drug-like functional groups such as an optionally substituted alkyl group, aryl group, heteroaryl group and aralkyl group. Preferably, they are each selected from a hydrogen atom and an alkyl group.

When a unit having an activated ester group such as a thioester group is selected as the triangle unit (on the N-terminal side), this unit can be selected from, for example, Compounds C-1, C-2, C-3, Ca-1, COH-1, COH-2 and COH-3. The amino group at the main chain of Compound C-1 or the like is remained even after the cyclized compound, whereas Compound Ca-1, COH-1, COH-2 or COH-3 gives a drug-like compound because of the absence of the amino group and is therefore more preferred. In this case, the intersection unit is selected from Compound Na-10 (Na-7 group or Na-8 group), Compound Na-11 (Na-7 group or Na-8 group) and the like. These compounds may be translated in a protected state. Translatable protecting groups and deprotection reaction conditions where RNA is stable can be selected by using methods described herein. The Compound Na-7 group is more preferably used than the Na-8 group, because of its higher metabolic stability.

When Compound C-1, C-2, C-3, COH-1, COH-2, COH-3 or the like having an active ester group is selected as the intersection unit (on the C-terminal side), the triangle unit (on the N-terminal side) can be selected from Compounds N-1 and N-2 already described and also from Compounds Na-10 and Na-11. The N-terminal triangle unit is preferably selected from Compounds N-1 and N-2 and also from Compounds Na-10 (Na-8 group and Na-9 group) and Na-11 (Na-8 group and Na-9 group). This is because use of the Na-7 group allows the amine of main chain to be retained to the resulting compound and thereby reduces druglikeness. On the other hand, Compound Na-10 (Na-7 group and Na-8 group) or Compound Na-11 (Na-7 group and Na-8 group) can be used as the triangle unit located at a site other than the N-terminal. In this case, an amino acid derivative or N-terminal carboxylic acid derivative is more preferably used for the N-terminal. This is not to retain amino group of the main chain as N-terminal amino acid.

The groups added to Compounds Na-10 and Na-11 are not limited to the Na-7 group, Na-8 group or Na-9 group. For example, the Na-7 group is derived from an α-amino acid backbone, but the compound may be derived from a β-amino acid backbone.

The approach of more activating the amine than a common amine is not limited to the approach involving an SH group as a reaction promoting group. Another possible approach of more activating the amine than a common amine involves directly introducing a heteroatom into the amine to improve the reactivity of the amine. Examples of such amines include hydroxyamines (Compounds F-1, F-4, F-5 and F-7) alkoxyamines (Compounds F-2, F-14, F-15 and F-16) and azides (Compounds F-3, F-9, F-10 and F-11). All of such approaches which involve introducing a heteroatom capable of becoming a reaction promoting group either directly into the amino group or via a linker to near the amino group to activate the amino group are included in the present application. Compound F-7, F-8 or the like is selected as an active ester site for reaction with the hydroxyamine. Compound F-17, F-18 or the like is selected for reaction with the alkoxyamine. Compound F-12, F-13 or the like is selected for reaction with the azide.

$R_{101}$, $R_{102}$, $R_{103}$, $R_{104}$, $R_{105}$, $R_{106}$ and $R_{107}$ are substituents that are usually used in the side chains of amino acids not limited to natural amino acids. Specifically, these substituents are each selected from a hydrogen atom, an optionally substituted alkyl group, an optionally substituted alkenyl group, an optionally substituted alkynyl group, an optionally substituted aryl group, an optionally substituted heteroaryl group and an optionally substituted aralkyl group.

More preferably, one of $R_{101}$ and $R_{102}$ is a hydrogen atom, one of $R_{103}$ and $R_{104}$ is a hydrogen atom, and one of $R_{106}$ and $R_{107}$ is a hydrogen atom. The hydrogen atoms are preferably located such that these substituents take the same conformation as that of L-amino acid.

$R_{105}$ is selected from among an optionally substituted alkyl group, an optionally substituted alkenyl group, an optionally substituted alkynyl group, an optionally substituted aryl group and an optionally substituted aralkyl group.

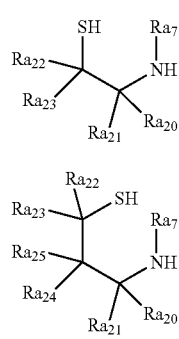

Compound Na-10

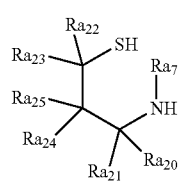

Compound Na-11

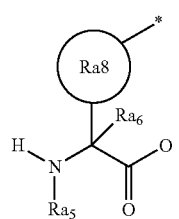

Na-7 group

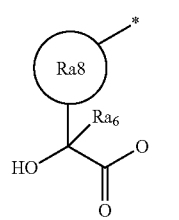

Na-8 group

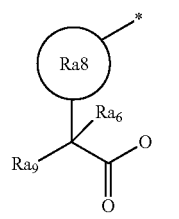

Na-9 group

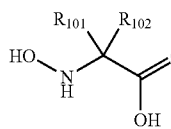

Compound F-1

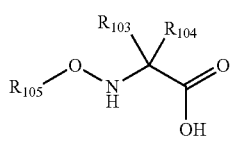

Compound F-2

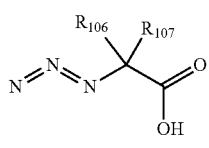

Compound F-3

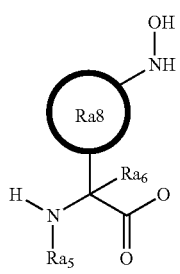

Compound F-4

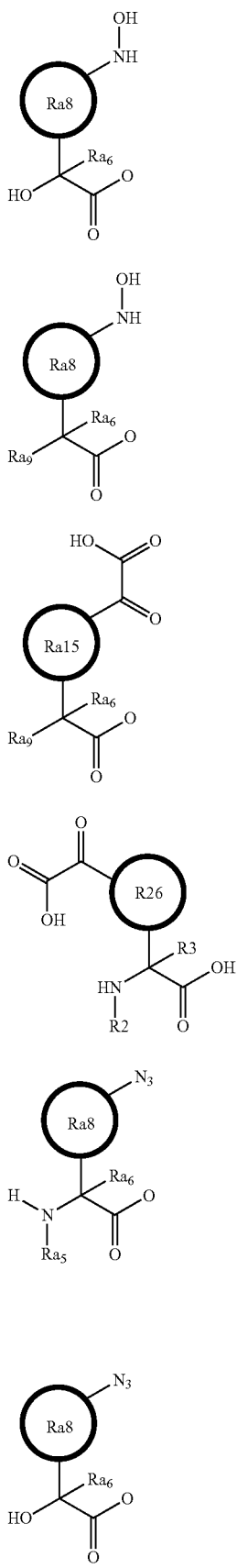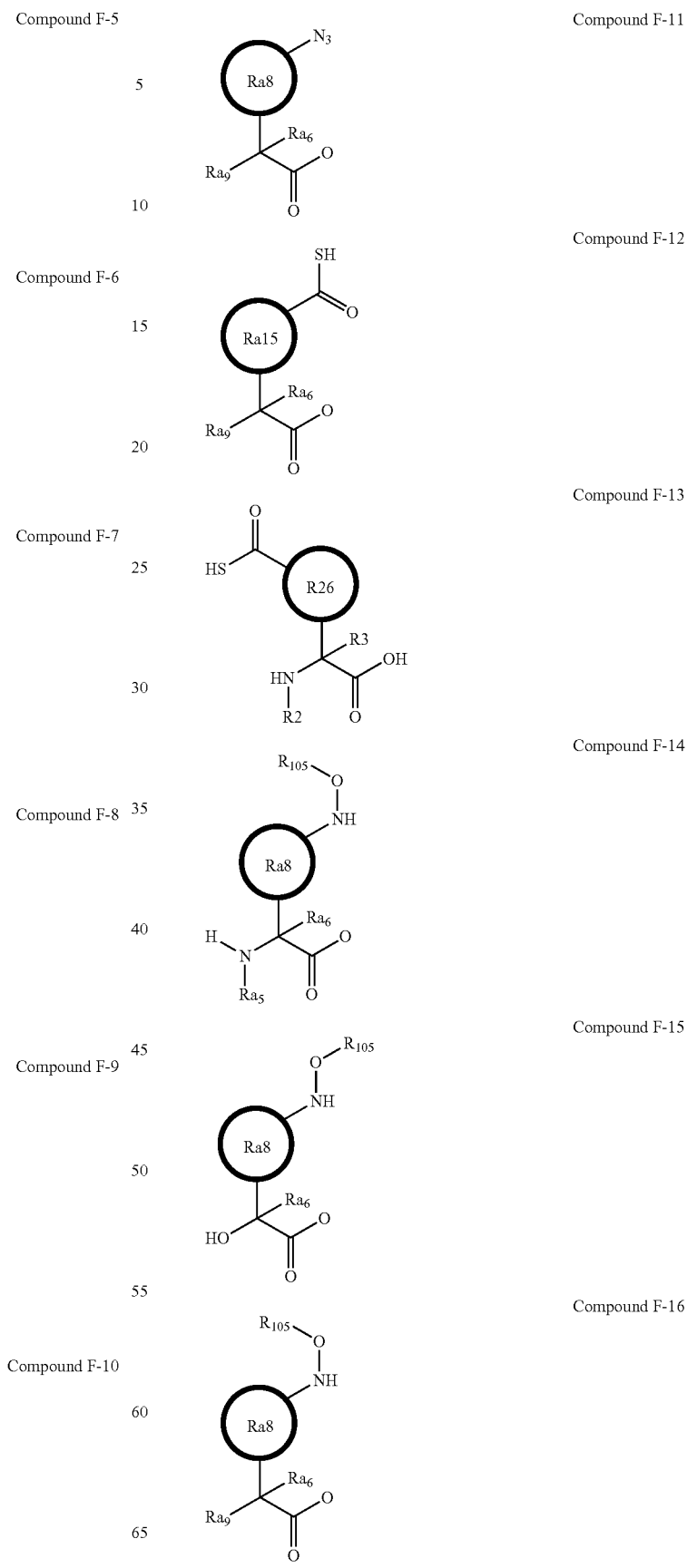

Compound F-17

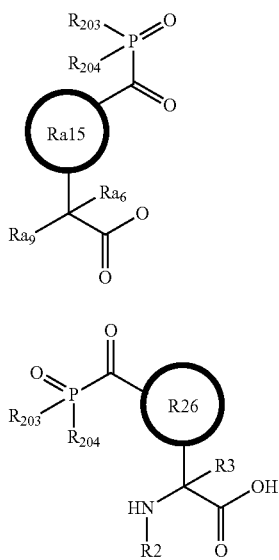

Compound F-18

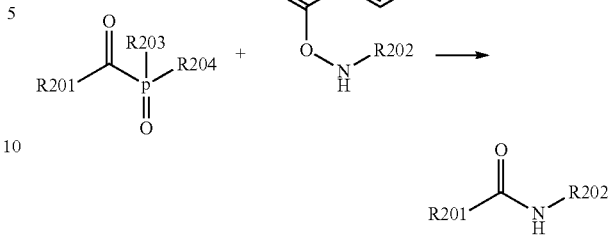

A possible combination of the activated amine selected from above and activated ester as a candidate for the compatible intersection unit is, for example, thioester and amine with a thiol vicinally oriented to the amine or α-ketoester and azide.

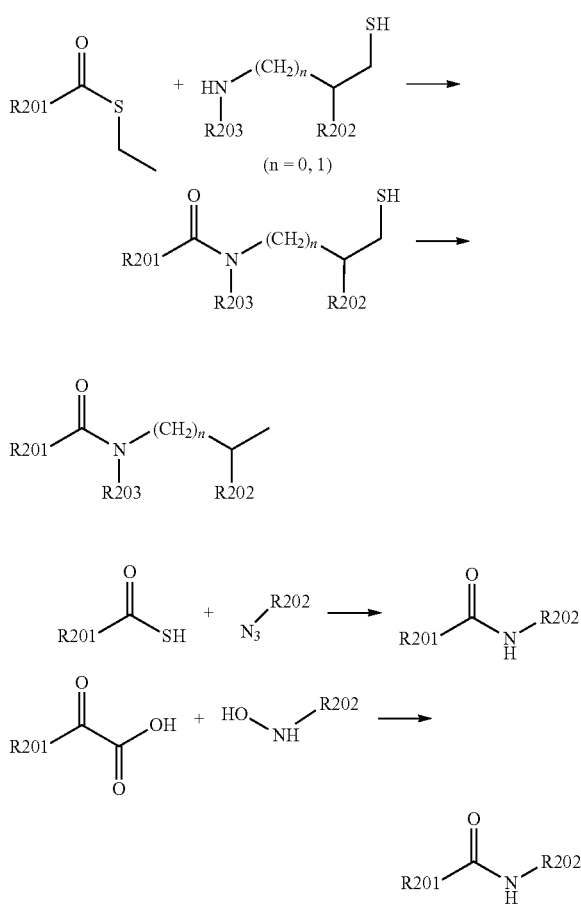

Use of initiation read-through (skipping of an initiation codon) eliminates the need of preparing plural types of aminoacyl translation initiation tRNAs for the method for synthesizing peptide compounds or peptide compound libraries having diverse terminals by the N-terminal introduction of the amino acid, amino acid analog or N-terminal carboxylic acid analog other than methionine. The initiation read-through means a phenomenon in which a translated product is generated from an amino acid encoded by the 2nd or later codon in a cell-free translation system containing no translation initiation methionyl tRNA or at the initiation of translation from a translation initiation tRNA with an unnatural amino acid having low translation efficiency, though general protein or peptide translation is initiated from methionine as the initial amino acid by the translation encoded by an AUC codon.

The method using the initiation read-through can involve allowing the triangle unit to be encoded by the 2nd codon following the initiation codon on a peptide-encoding mRNA sequence, and carrying out translation in a translation system containing neither methionine nor translation initiation methionine-tRNA to obtain a peptide or peptide library having the triangle unit at the N-terminal. According to another report, a method is known, which involves removing the N-terminal methionine of a peptide by the action of enzymes, for example, peptide deformylase and methionine aminopeptidase (Non Patent Literature: Meinnel, T., et al., Biochimie (1993) 75, 1061-1075, Methionine as translation start signal: A review of the enzymes of the pathway in *Escherichia coli*). A library of peptides starting at methionine may be prepared, and methionine aminopeptidase can be allowed to act thereon to remove the N-terminal methionine and thereby prepare a library having random N-terminals. Also, cyclization using the 2nd amino acid following translation initiation methionine or the like, followed by aminopeptidase treatment has been shown to be able to remove the N-terminal amino acid such as methionine. According to these approaches, a methionine residue is not contained in the units of Scheme A (as already defined, the number of units is determined on the basis of a completely posttranslationally modified chemical structure), and an amino acid residue corresponding to the triangle unit becomes an amino acid encoded by the 2nd codon. As a result, the triangle unit can be encoded by a plurality of codons to expand the degree of freedom to 2 or more types, leading to one more variable site. This enables two or more types of amino acids or amino acid analogs to be used as the triangle unit. Hence, the peptide compound or peptide compound library of the present invention can be made as a more diverse peptide compound or peptide compound library. The same number of amino acids or amino acid analogs as that of random regions can be used at the maximum, and the degree of freedom can be expanded to the same number as that of random region. In this context, the random regions mean regions for which amino acids or amino acid analogs can be arbitrarily selected in the peptide compound of the present invention. The random regions, in methods other than this method, refer to regions (i.e., filled circle units and square units) other than the intersection unit and the triangle unit in Scheme A. In this method, the random regions also include the triangle unit. The structure diversity of the filled circle units or the square units can be secured with the reactivity of the triangle unit with the intersection unit maintained. This means that conventional posttranslational cyclization requires fixing two amino acids (corresponding to the triangle unit and the intersection unit) in a display library, whereas use of this method can decrease the number of such fixed amino acids to one (intersection unit). For example, most of amino acids and amino acid analogs selected for random regions have a amino group at main chain. Applying this to the triangle unit, a random amino acid sequence having an amino group is located at the N-terminal. Amide cyclization can be carried out by selective amide bond formation with the common main chain amino group. This approach is particularly useful for constructing, for example, a display library not containing basic amino acids such as lysine or arginine. According to our examination results, the number of residues having druglikeness is 13 or less residues. Thus, the decrease in the number of units to be fixed from 2 to 1 means that the number of units as random regions is increased from 11 to 12. The increase in the number of residues that can be randomized by one is very highly valuable in terms of the maximum use of the degree of freedom under limited chemical space with maintaining druglikeness.

Specifically, carboxylic acid or carboxylic acid activated ester can be translationally incorporated into the side chain of the intersection unit (amino acid at which the linear portion and the triangle unit of the cyclic portion intersect each other). An amide bond can therefore be formed between the fixed intersection unit and the triangle unit selected from random amino acids (Scheme B). For library construction, the intersection unit does not have to be limited to one type, and two or more types of intersection units may be selected. Specifically, a codon encoding each intersection unit and an (amino)acylated tRNA are prepared, and a library can be constructed using template mRNA having the intersection unit codon located at the desired position.

Figure 86:
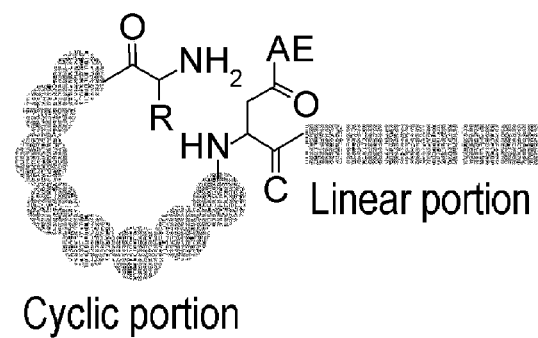
FIG. 86 is a diagram showing scheme B. Scheme B shows an example of an uncyclized translated compound having a random amino acid at the triangle unit and aspartic acid or activated ester at the intersection unit. This is a specific example of A-1. R represents an amino acid side chain, and AE represents OH or active ester.

See FIG. 86.

Examples of the library construction approach by cyclization without fixing the N-terminal (triangle unit) include amide cyclization (however, this approach can also be used for library construction using the fixed N-terminal). An aspartic acid derivative will be taken as an example of the intersection unit in the description below. However, the intersection unit is not limited thereto and can be selected from among, for example, the compound groups represented by Compounds C-1, C-2 and C-3. Any N-alkylated form such as N-methylaspartic acid or any amino acid or amino acid analog having carboxylic acid at the side chain such as glutamic acid derivatives may be used. (i) An amino acid having carboxylic acid at the side chain can be introduced into the intersection unit and posttranslationally converted to active ester. For example, as shown in Compound E-1, aspartic acid itself can be translationally incorporated thereinto. The resulting translated peptide can be amide-cyclized by condensation reaction between the carboxylic acid and the N-terminal amine. For example, as shown in Compound E-2, the amino acid can be converted to N-hydroxysuccinimide active ester or active ester of HOBt, HOAt or the like. The obtained activated ester can be easily reacted with the amine. As a result, amide cyclization reaction can be achieved with the N-terminal randomized. A key to achievement of this approach is to select an approach in which only the carboxylic acid site is converted to activated ester and RNA (or a nucleic acid site such as RNA site) is not reacted. (ii) An amino acid having carboxylic acid activated ester at the side chain is translationally incorporated into the intersection unit, and the active ester can be reacted with the amine. This approach involves translationally synthesizing active ester in advance, as shown in Compound E-2. In addition to Compound E-2, benzylthioester in Compound E-3, arylthioester in Compound E-4, alkylthioester or the like may be translationally incorporated thereinto. Although a phenyl group will be taken as an example in Compound E-4 or E-3, any aryl group or heteroaryl group can be used without limitations. Alternatively, the aryl group or heteroaryl group may have a substituent, for example, an electron-withdrawing group such as a halogen group, nitro group, trifluoromethyl group or nitrile group, or an electron-donating group such as an alkoxy group (e.g., methoxy group) or alkyl group (e.g., methyl group). These substituents are preferably selected in consideration of the rate of thioester exchange reaction, the amine reactivity of thioester after exchange reaction and the selectivity of side reaction with water so that these factors are well balanced. The substituent is also selected from, for example: bulky substituents typified by a t-butyl group and isopropyl group; and di-substituted amino groups such as a sulfonic acid group and dimethylamino group in consideration of affinity for water for practice in water or highly lipid-soluble groups such as a long-chain alkyl group in consideration of lipophilicity. Alternatively, plural types of substituents may be introduced simultaneously, such as a nitro group, trifluoromethyl group and halogen. As shown in Compound E-4, thioaryl active ester more activated than the ester of Compound E-3 may be translationally incorporated into the intersection unit in advance. The thioester can also be selected from alkylthioester, in addition to such aralkyl or arylthioester. A key to achievement of this approach is to have both of two properties: being stable during translational synthesis; and having sufficient reactivity with amine without a reaction promoting group. (iii) Active ester, such as thioester, which can sufficiently secure stability during translational synthesis may be translationally incorporated into the intersection unit in advance, and after translation, more active ester can be generated in the system by the addition of an additive and subjected to cyclization reaction with the amine without a reaction promoting group. Examples of this approach include a method in which, to the translationally incorporated thioester, more electron-poor thiol is externally added to generate, in the system, more active thioester, which is in turn subjected to cyclization reaction with the amine. For example, the thioester of Compound E-3 may be posttranslationally reacted directly with the amino group or may be converted to more active ester E-4 by the addition of more highly reactive thiol such as trifluoromethylphenylthiol into the translation system and then reacted with the amino group. Alternatively, various starting materials known to form active ester, for example, HOBt, HOAt and HONSu, may be added to the system. One type of additive may be selected from among them, or two or more types thereof may be selected. Examples of the advantage brought about by the addition of two or more types of additives include improvement in reactivity. The conversion of translatable activated ester sufficiently stable in a translation solution to activated ester sufficiently highly reactive with every amino group is energetically unfavorable, and such reaction is sometimes difficult to perform in one step. In such a case, the translatable and stable activated ester may be temporarily converted to activated ester of more reactivity, which can then be converted to the active ester sufficiently highly reactive with every amino group. Use of such multi-step activation of activated ester may enable amidation reaction even with a amino group of lower reactivity. A substituent may be introduced into the additive for activated ester or the like. The additive may have a substituent, for example, an electron-withdrawing group such as a halogen group, nitro group, trifluoromethyl group or nitrile group, or an electron-donating group such as an alkoxy group (e.g., methoxy group) or alkyl group (e.g., methyl group). Alternatively, the substituent is selected from, for example: bulky substituents typified by a t-butyl group and isopropyl group; and di-substituted amino groups such as a sulfonic acid group, carboxyl group, hydroxy group and dimethylamino group in consideration of affinity for water for practice in water or highly lipid-soluble groups such as a long-chain alkyl group in consideration of lipophilicity. (iv) Stable active ester may be translationally incorporated into the intersection unit in advance, as in (iii), and after translation, chemical reaction (e.g., deprotection reaction) and activation by intramolecular reaction can be carried out, followed by cyclization reaction with the amine not having a reaction promoting group. For example, as shown in Compound E-5, more stable thioester may be translationally incorporated thereinto and converted to more highly reactive arylthiophenol or the like by intramolecular reaction following the posttranslational deprotection of the S—S bond, and the arylthiophenol or the like can be reacted with the amine. Moreover, two or more of the concepts of (i) to (iv) may be combined to attain this object. Thus, one approach of effectively utilizing the initiation read-through method can involve reacting the common amino group located at the N-terminal with the intersection unit to construct a display library having drug-like cyclization sites and having higher diversity.

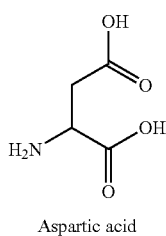

Compound E-1

Aspartic acid

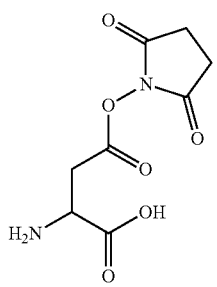

Compound E-2

Aspartic acid
Osu ester

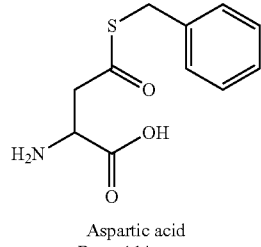

Compound E-3

Aspartic acid
Benzylthioester

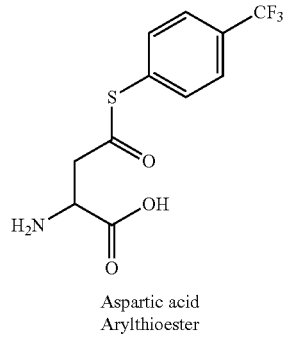

Compound E-4

Aspartic acid
Arylthioester

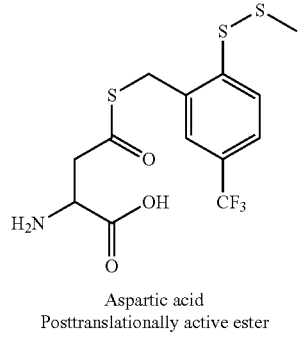

Compound E-5

Aspartic acid
Posttranslationally active ester

Particularly, in the approach (iii) in which active ester, such as alkylthioester or benzylthioester, which can sufficiently secure stability during translational synthesis and can be translationally incorporated, is used and after translation, more active ester can be generated in the system by the addition of an additive and subjected to cyclization reaction with the amine without a reaction promoting group, for example, alkylthioester such as methylthioester (Asp(SMe)) or aralkylthioester such as benzylthioester (Asp(SBn)) of side chain carboxylic acid in aspartic acid can be used as the active ester for the translational synthesis.

Examples of the additive added for the purpose of chemically reacting the translationally synthesized intersection unit with the triangle unit not having a reaction promoting group include arylthiol and heteroarylthiol, such as 4-(trifluoromethyl)benzenethiol. These additives are optionally substituted by an electron-withdrawing group, electron-donating group, lipid-soluble group or water-soluble group, preferably an electron-withdrawing group. Examples of the electron-withdrawing group include a trifluoromethyl group, nitro group and fluoro group. Preferred examples thereof include electron-withdrawing groups such as a trifluoromethyl group.

The amount of the thiol added is not particularly limited and is preferably more than 10 mM for the purpose of sufficiently enhancing reactivity and preferably less than 10

M for the purpose of dissolving the additive. The amount is more preferably in the range of 50 mM to 5 M, further preferably 200 mM to 2 M. The additive may be added directly as thiol (acidic) and is preferably added under neutral conditions by neutralizing the acidic moiety by the addition of the number of equivalents of a base such as triethylamine.

The still more active ester may be reacted with various reagents present in the translation reaction system. For example, an amine component (tris(hydroxymethyl)aminoethane) in a tris buffer usually used may be such a reagent. Preferably, translational synthesis is carried out in a buffer free from the reactive amine component, and an additional buffer is used for chemical reaction. Examples of such buffers include a HEPES buffer and phosphate buffer.

The buffer may be further added to the translation reaction solution for the purpose of preventing the amount of the thiol necessary for progression of the reaction from being decreased due to side reaction (oxidation reaction (S—S formation reaction) in the air) with progression of the reaction, and of avoiding conditions where basicity gets higher to give precedence to the occurrence of hydrolysis. Also, a reducing agent such as tris(2-carboxyethyl)phosphine may be added thereto. It is also effective to keep the cyclization reaction away from oxygen in the air as much as possible.

The solvent for chemical reaction preferably has a pH of 2 to 10 for the purpose of keeping RNA stable. The pH is preferably 7.8 or higher for the purpose of allowing the chemical reaction to proceed smoothly and is preferably kept at 9.2 or lower for the purpose of suppressing the occurrence of hydrolysis. As for the reaction conditions, the chemical reaction may be carried out alone in the translation reaction solution of PureSystem or the like, or an organic solvent such as DMF or NMP may be added to this reaction solution. Alternatively, the translation solution may be purified by column purification or the like, after which the chemical reaction can be carried out using a different solvent. The reaction temperature is not particularly limited as long as the usual chemical reaction can be carried out at this temperature. The reaction temperature is preferably 15° C. to 80° C., more preferably 25° C. to 50° C.

The triangle unit that allows the cyclization reaction to proceed smoothly is not particularly limited. Primary amine and secondary amine (e.g., N-alkyl group such as N-methyl) are both accepted as the amino group. The amino acid side chain site is not limited by substituents. Particularly, when a carbon atom adjacent to the amino group is unsubstituted (CH2), both primary amine and secondary amine are accepted. Secondary amine having a methyl group is more preferred. When the carbon atom adjacent to the amino group has a substituent, primary amine is more preferred. The substituent site more preferably has CH2 at the β-position as found in Ala or Phe rather than Val, Thr or the like. A cyclic secondary amine is also preferred, including an amino acid, such as proline, in which the nitrogen atom and the carbon atom at the α-position form a 5-membered ring, and an amino acid similarly having a 4-membered ring or 6-membered ring.

Although the exemplary library construction approaches by cyclization without fixing the N-terminal (triangle unit) are described above, the utilization of this amide cyclization reaction by condensation reaction between the amino group without the use of a reaction promoting group and the activated ester group is not limited to the reaction with the amino group of N-terminal main chain. The reaction can be carried out by arbitrarily combining the side chain amino group of an amino acid or amino acid analog or the amino group of an N-terminal carboxylic acid derivative and the side chain activated ester of an amino acid or amino acid analog or the active ester of an N-terminal carboxylic acid derivative.

In this approach, as in Scheme C, a unit having activated ester may be located in the triangle unit, while an amine side chain may be located on the intersection unit side. Either of the activated ester and amino groups may be located in the triangle unit or the intersection unit.

Examples of such combinations will be described below.

When a unit having an activated ester group is selected as the intersection unit, this intersection unit may be selected from Compounds C-1, C-2, C-3, COH-1, COH-2 and COH-3. An amino acid on the C-terminal side immediately following the unit selected from these 6 types of compounds is preferably selected from among N-alkylated units. This restriction is intended to avoid side reaction of aspartimide formation. This selection is commonly preferred for these 6 types of compounds thus selected. Compound C-1, C-2 or C-3 is more preferred from the viewpoint of metabolic stability. In such a case, the triangle unit may be selected from among Compounds Na-1, Na-2 and Na-3. When the N-terminal (triangle unit) is not fixed, a plurality of triangle units may be selected simultaneously from these compounds.

The side chain amino group in any of Compounds Na-1, Na-2 and Na-3 is optionally protected. The protected amino group is deprotected simultaneously with or prior to cyclization reaction. A protecting group and deprotection conditions can be selected by using methods described herein.

Ra13 in Compound Na-1 can be selected from a hydrogen atom, a C1-C6 alkyl group, an aralkyl group and the like. These groups are optionally substituted by a functional group defined as being drug-like, such as a hydroxyl group, fluoro group or ether group. Ra13 is preferably a hydrogen atom, a methyl group, an ethyl group, a n-propyl group or a benzyl group.

Ra1 in Compound Na-2 can be selected in the same way as in Ra13. Particularly preferably, Ra1 is selected from a hydrogen atom and a methyl group. Ra2 can be selected in the same way as in Ra13 and is preferably a hydrogen atom or a methyl group, particularly preferably a hydrogen atom. When the hydrogen atom is selected, its conformations corresponding to both L- and D-amino acids are acceptable. L-conformation is more preferred. Ra3 can be selected in the same way as in R13. Ra3 and Ra4 may form a ring. A hydrogen atom is particularly preferred. Ra4 can be selected from a hydrogen atom, an alkyl group, a cycloalkyl group, an aralkyl group, a heteroaryl group and an aryl group. These groups are optionally substituted by a functional group defined as being drug-like. Alternatively, Ra4 may form a ring together with Ra1. For example, proline corresponds to this ring.

Ra11 in Compound Na-3 can be selected in the same way as in Ra13 and is preferably a hydrogen atom, a methyl group, an ethyl group, a n-propyl group or a benzyl group, particularly preferably a hydrogen atom. Ra9 can be selected in the same way as in Ra4. Ra9 is preferably selected from a hydrogen atom, a C1-C6 alkyl group and an aralkyl group. These groups are optionally substituted by a functional group defined as being drug-like. Alternatively, Ra9 and Ra11 may form a ring. The ring is preferably 3 to 8-membered in size. The formed ring is more preferably a 5-membered ring or 6-membered ring. The substituent represented by Ra9 is particularly preferably a hydrogen atom. Ra10 and Ra12 can be selected in the same way as in Ra4. Preferably, Ra10 and Ra12 can be selected in the same way as in Ra13. More preferably, either Ra10 or Ra12 is a hydrogen atom. Particularly preferably, both Ra10 and Ra12 are hydrogen atoms. In this case, the N-terminal is preferably selected from amino acid derivatives and N-terminal carboxylic acid derivatives. This is because an amino group present in the N-terminal main chain is disadvantageous to reaction selectivity and in addition, is carried thereby even after the completion of posttranslational modification to reduce druglikeness.

When the intersection unit is selected from Compounds C-1, C-2 and C-3, the triangle unit may be fixedly located at a site other than the N-terminal. In such a case, the triangle unit can be selected from Compounds Na-4 and Na-5.

Ra5 in Compound Na-4 can be selected in the same way as in Ra1. Ra6 can be selected in the same way as in Ra2. Ra7 can be selected in the same way as in Ra4. A hydrogen atom or a methyl group is more preferred, with a hydrogen atom particularly preferred. Ra8, as with R4, can be selected from alkylene groups of C1-C6 units such as partial structures N-3, N-4 and N-5, N-6, N-7 and N-8 (including ortho-substituted forms as well as meta- and para-substituted forms). In this context, substituents represented by R13 to R22 can be selected from among drug-like functional groups that do not react with an activated ester or amino group. Preferably, these substituents are selected from, for example, C4-C6 alkylene units and partial structures N-6, N-7 and N-8 having an aryl group, which optionally have a substituent.

Ra5 in Compound Na-5 can be selected in the same way as in Ra1. Ra6 can be selected in the same way as in Ra2. Ra7 can be selected in the same way as in Ra4. A hydrogen atom or a methyl group is more preferred, with a hydrogen atom particularly preferred. Ra8, as with R4, can be selected from alkylene groups of C1-C6 units such as partial structures N-3, N-4 and N-5, N-6, N-7 and N-8 (including ortho-substituted forms as well as meta- and para-substituted forms). In this context, substituents represented by R13 to R22 can be selected from among drug-like functional groups that do not react with an activated ester or amino group. Preferably, these substituents are selected from, for example, C4-C6 alkylene units and partial structures N-6, N-7 and N-8 having an aryl group, which optionally have a substituent.

The amino group at side chain in any of Compounds Na-4 and Na-5 is optionally protected. The protected amino group is deprotected simultaneously with or prior to cyclization reaction. A protecting group and deprotection conditions can be selected by using methods described herein.

When the intersection unit is selected from Compounds C-1, C-2 and C-3, the triangle unit may be located at the N-terminal and cyclized with the side chain amino group. In such a case, the triangle unit can be selected from Compounds Na-4 and Na-5 and also from a wide range of compound groups having amino and carboxyl groups. Various units can be translationally synthesized as the N-terminal carboxylic acid analog. Such a unit is not particularly limited as long as the unit has an amino group to be amide-cyclized and a carboxylic acid for peptide translation. Preferably, a functional group having a divalent unit that links the amino group to the carboxylic acid group is selected from among drug-like functional groups. One example of such a compound includes Compound Na-6. Ra9 in Compound Na-6 may be selected from an alkyl group, a cycloalkyl group, an aryl group, a heteroaryl group and an aralkyl group each optionally substituted by a drug-like functional group. In addition, a —NRCOR' group (wherein each of R and R' is a drug-like substituent), —OR (wherein R is a drug-like substituent), NR group (wherein the R moiety includes an amino acid, dipeptide, tripeptide or the like) or the like is acceptable.

On the other hand, a unit on the amino group side may be present in the intersection unit. In the case of selecting, for example, Compound Na-4 or Na-5, the triangle unit may be selected from, for example, Compounds C-1, C-2, C-3, COH-1, COH-2 and COH-3. In this case, preferably, a linear portion is also present on the N-terminal side of the triangle unit, and the N-terminal is selected from N-terminal carboxylic acid derivatives, in terms of druglikeness.

In the case of selecting, for example, Compound Na-4 or Na-5, the triangle unit may be selected from, for example, Compounds COH-1, COH-2 and COH-3. In this case, the triangle unit may be present at the N-terminal. Alternatively, preferably, a linear portion is also present on the N-terminal side of the triangle unit, and the N-terminal is selected from N-terminal carboxylic acid derivatives, in terms of druglikeness.

When the intersection unit is selected from, for example, Compounds Na-4 and Na-5, Compound Ca-1 may be selected as the triangle unit.

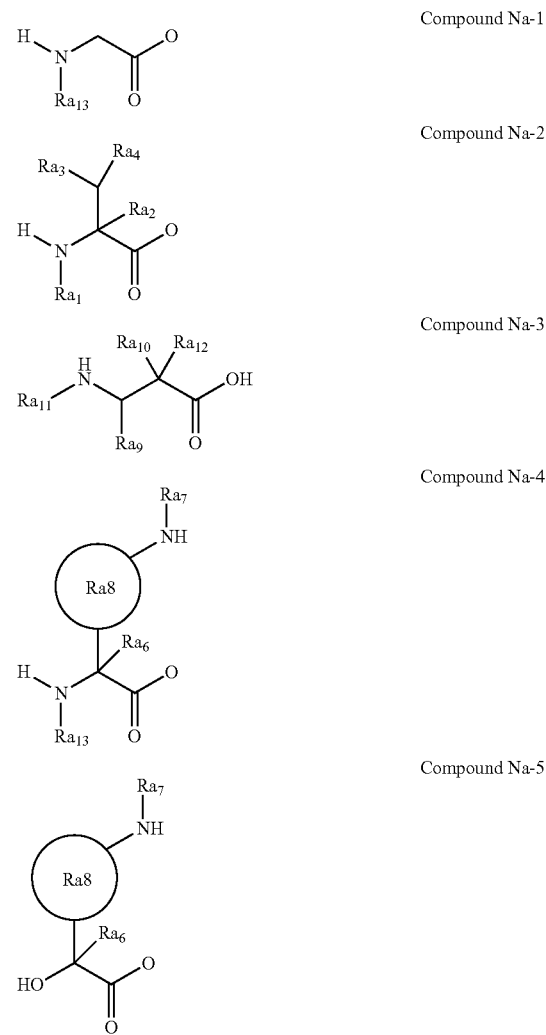

Compound Na-6

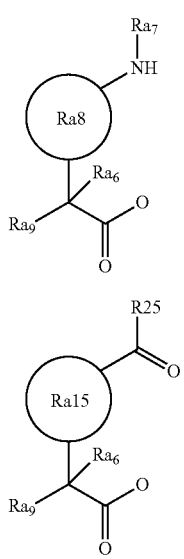

Compound Ca-1

Addition of Linear Portion 2 (Branched Site)

An approach of generating linear portion 2 can involve the translational incorporation of both of an amino acid analog (e.g., α-hydroxycarboxylic acid) that has no amino group in the main chain and can form an ester bond by translational synthesis and an amino acid having an optionally protected amino group side chain (the protecting group is not particularly limited as long as the protecting group acts on the amino group to give a translationally synthesized amino acid), followed by posttranslational modification (Scheme E). For application to a display library, the linear portion is selected from units to be translated. The peptide compound obtained by subsequent optimization, however, includes peptide compounds obtained by posttranslational modification after translational synthesis, even if the peptide compounds themselves are not translationally synthesized. The α-hydroxycarboxylic acid site is not particularly limited by its side chain. In the approach described in Scheme E, Rel preferably has a hydrogen atom (glycolic acid ($^{HO}$Gly) itself) or a thiol group (SH group) or protected thiol group at the side chain, particularly in terms of translational synthesis. The side chain is not particularly limited by its conformation and more preferably assumes a conformation similar to that of an L-amino acid provided that a hydrogen atom is present at the α-position. The thiol group or protected thiol group is not particularly limited by its position and is particularly preferably located at the β- or γ-position of the OH group (i.e., Rel is an optionally protected mercaptomethyl group or mercaptoethyl group). Such a thiol group or protected thiol group is located (added) to an optionally substituted alkyl group, alkenyl group, alkynyl group, cycloalkyl group, aralkyl group, aryl group or heteroaryl group at the α-hydroxycarboxylic acid side chain. These substituents of the α-hydroxycarboxylic acid side chain, except for the added thiol group or protected thiol group, are more preferably substituents defined in the side chain of the drug-like amino acid.

The amino acid having an amino group at side chain is not particularly limited by its type as long as the amino acid has an amino group, which may be any of an optionally substituted alkylamino group, alkenylamino group, alkynylamino group, aralkylamino group, arylamino group, heteroarylamino group and cycloalkylamino group. The amino acid may also have a thiol group (SH group) or protected thiol group at the side chain. These substituents, except for the reaction promoting group (e.g., SH group), are preferably substituents defined in the side chain of the drug-like amino acid. The substituents are more preferably selected from substituents that provide for translational synthesis. One of the hydrogen atoms at a site represented by NH2 in the scheme is determined as a hydrogen atom, and the other hydrogen atom may be replaced with an optionally substituted alkyl group, alkenyl group, alkynyl group, aralkyl group, aryl group, heteroaryl group or cycloalkyl group. A reaction promoting group may be added thereto. A NH2 group is preferred. These substituents, except for the reaction promoting group (e.g., SH group), are also preferably substituents defined in the side chain of the drug-like amino acid. The substituents are more preferably selected from substituents that provide for translational synthesis. A codon (A) encoding the amino acid analog (e.g., α-hydroxycarboxylic acid) that has no amino group and can form an ester bond, an acylated tRNA therefor, a codon (B) encoding the amino acid having an amino group side chain, and an aminoacylated tRNA therefor are prepared, and a peptide obtained by the translation of template mRNA having the desired number (preferably 0 to 7, more preferably 0 to 2) of random codons located between the codon (A) and the codon (B) is first cyclized by the above method or a different method. The codon A is located at a site corresponding to the N-terminal side of codon B. The obtained cyclized peptide (e.g., the approach of Scheme B or Scheme C can be used) is deprotected, if necessary, when having a protecting group in the side chain amino group. The ester bond can be hydrolyzed or activated (converted to activated ester or activated thioester) without hydrolyzing the amide bond, by hydrolysis or by the activation of the ester site by means of an externally added additive. The obtained main chain carboxylic acid or active (thio)ester can be subjected to intramolecular cyclization reaction with the amine of side chain to obtain the desired peptide having linear portion 2 (branched peptide). Examples of the externally added additive include thiol compounds, compound groups forming various activated esters, such as HONSu, HOBt and HOAt, and mixtures of two or more types thereof. In the example shown in Scheme E, Rel-substituted hydroxycarboxylic acid is encoded by the codon A, and lysine is encoded by the codon B.

When Rel is a hydrogen atom, the triangle unit selected for the first cyclization (cyclization at the triangle unit and the intersection unit) reaction may have a reaction promoting group at the amine site or may not have a reaction promoting group. The first cyclization reaction can be allowed to proceed easily by selecting a unit having a reaction promoting group (e.g., Compound N-1 or Compound N-2) as the triangle unit. The reaction with the translationally synthesizable intersection unit having thioester at the side chain may be performed at a pH around 7 (translation conditions) in the presence or absence of a reactive additive. On the other hand, when a unit not having a reaction promoting group is selected as the triangle unit (e.g., Ala or Phe included in Compound Na-2 is selected), an additive such as trifluoromethylthiophenol is more preferably added for allowing the first reaction to proceed. The reaction is more preferably performed at a pH increased to around 7.8 and a reaction temperature of approximately 37° C. to 50° C. for a time of approximately 6 to 10 hours. The amine site for the second branching reaction may not have a reaction promoting group. More preferably, the amine site has a reaction promoting group, and in this case, the NH group is preferably protected. In this case, thiol is preferably added as an ester-activating agent. The thiol is preferably alkylthiol, particularly preferably alkylthiol having a water-soluble substituent, in terms of the solubility of the additive. Specifically, 2-dimethylaminoethanethiol or 2-mercaptoethanesulfonic acid is preferred. The amount of the thiol added is not particularly limited and is preferably more than 10 mM for the purpose of sufficiently enhancing reactivity and preferably less than 10 M for the purpose of dissolving the additive. The amount is more preferably in the range of 100 mM to 5 M, further preferably 500 mM to 4 M. The amine site can be selected without particular limitations. The reaction conditions involving deprotection are the same as those described in Scheme F2.

Figure 87:
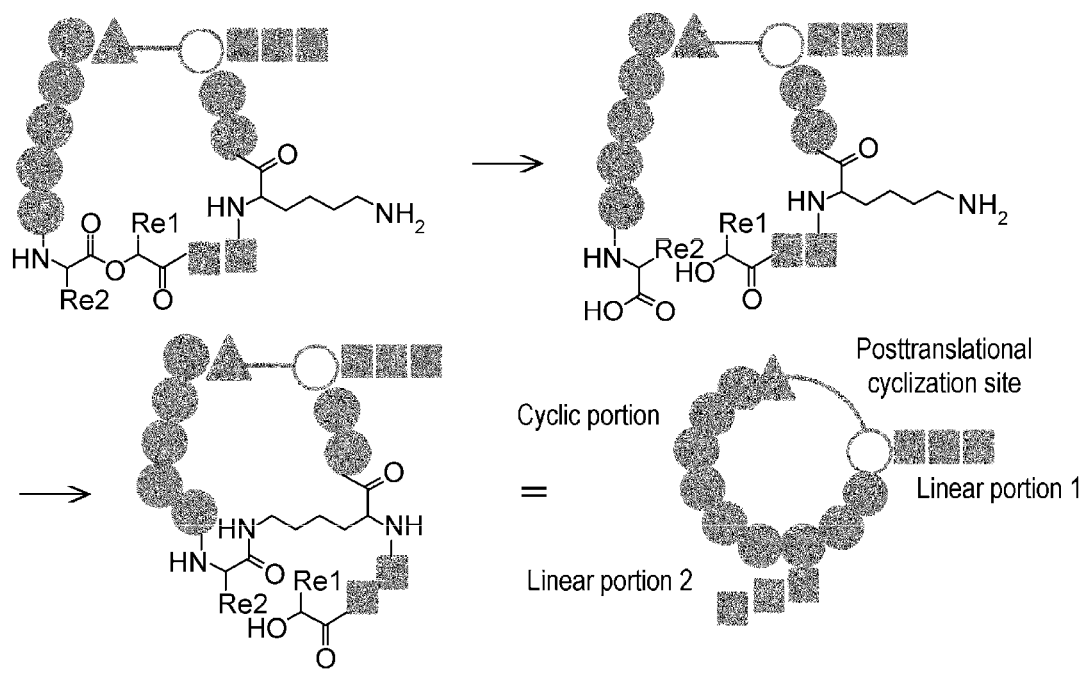
FIG. 87 is a diagram showing scheme E. Scheme E shows an example 1 of approach of forming linear portion 2.

See FIG. 87.

Various approaches are possible as modifications of the method described in Scheme E. For example, hydroxycarboxylic acid having an SH group or protected SH group at the Rel site may be used for the translational incorporation of, for example, an amino acid in which a reaction promoting group such as an SH group or protected SH group is introduced vicinally oriented to the amine at the amine side chain site or protected amine side chain site. In this case, the ester→thioester exchange shown in Scheme F is easily generated by deprotecting the protecting group added to the SH group and the optionally protected amine site in the peptide obtained by translation. Since the obtained thioester easily reacts with the amine having a reaction promoting group, the desired peptide having linear portion 2 (branched peptide) can be obtained. The SH group of the obtained branched peptide containing it can be easily desulfurized under mild reaction conditions where RNA does not participate in the chemical reaction. In this case as well, an additive may be externally added for the purpose of more activating (thio)ester. In the approach of Scheme F, the cyclization reaction at the posttranslational cyclization site may be carried out before or after this linear portion 2 formation reaction.

As described above, the reaction promoting group such as an SH group or protected SH may be carried by either of the hydroxycarboxylic acid or the amine side chain site, or both. Alternatively, the reaction promoting group may be carried by neither of them. In addition, the amine side chain site may or may not have a protecting group.

In any case, an additive may be added to accelerate the reaction. The additive may be, for example, an optionally substituted alkylthiol, an optionally substituted alkenylthiol group, an optionally substituted alkynylthiol group, an optionally substituted aralkylthiol, an optionally substituted arylthiol, an optionally substituted heteroarylthiol group or an optionally substituted cycloalkylthiol group. Alternatively, the additive may be a reagent usually used for conversion to active ester, such as HOBt, HONSu, HOAt or para-nitrophenol, or a derivative thereof. In the case of adding the additive, this linear portion 2 formation reaction is preferably carried out after the cyclization reaction at the posttranslational cyclization site. A substituent can be arbitrarily selected for the additive, as in the definition of the substituent in the side chain of the "amino acid".

Another possible approach of generating linear portion 2 similarly uses the ester functional group of α-hydroxycarboxylic acid or the like as an aid to generate thioester, and can involve respectively locating Cys and Pro to 2 sites on the N-terminal side immediately before the α-hydroxycarboxylic acid, and generating thioester from, for example, the resulting Cys-Pro-$^{HO}$Gly sequence (see Scheme F2). In the example shown in Scheme F2, α-hydroxycarboxylic acid having Rf5 at the side chain, following Cys-Pro is used as an active thioester-generating sequence for branching, while lysine having an amino group at the side chain is used as an amino acid that reacts with the sequence. A codon (A) encoding the amino acid analog (e.g., α-hydroxycarboxylic acid) that has no amino group and can form an ester bond, an acylated tRNA therefor, a codon (B) encoding the amino acid having an amino group side chain, and an aminoacylated tRNA therefor are prepared, and a peptide obtained by the translation of template mRNA having the desired number (preferably 0 to 7, more preferably 0 to 2) of random codons located between the codon (A) and the codon (B) is first cyclized (e.g., Scheme B or Scheme C) by the above method or a different method. The codon A is located at a site corresponding to the N-terminal side of codon B. The branch-generating site such as Cys-Pro-$^{HO}$Gly is stably present under the first cyclization reaction conditions without causing side reaction. Then, a thiol additive such as 4-trifluoromethylphenylthiol is added, if necessary, while the pH is adjusted to a basic region (e.g., 9) to generate new active thioester, which is then allowed via more active trifluoromethylphenylthioester to form an amide bond with, for example, the amino group of lysine side chain to generate a branched peptide (deprotection reaction precedes if the amino group of the side chain has a protecting group). Then, reaction of removing the reaction promoting group, such as dethiolation reaction, may be carried out, if necessary. Cys and Pro in the Cys-Pro-$^{HO}$Gly structure present before the generation of the branched peptide are eliminated in this reaction and therefore, are not contained in the generated branched peptide (completely posttranslationally modified form). Thus, these residues are contained neither in the filled circle units nor in the square units. Accordingly, the number of drug-like units is also calculated on the basis of the number of units in the generated branched peptide.

The α-position (Rf5) in the α-hydroxycarboxylic acid site is selected from among, for example, a hydrogen atom and an optionally substituted alkyl group, aralkyl group, heteroaryl group, cycloalkyl group and aryl group. The substituent is preferably a drug-like functional group. Particularly, this thioester-generating site is preferably stable and kept as a precursor (e.g., Cys-Pro-$^{HO}$Gly) structure under the first cyclization reaction conditions. Rf5 is preferably a hydrogen atom, an alkyl group such as a methyl group, or an aralkyl group such as a benzyl group.

Compounds corresponding to both L- and D-amino acids are acceptable for the substituent of Rf5 at this site, wherein OH group of the main chain is replaced with an amino group. Particularly, the corresponding L-conformation is preferred in terms of translation efficiency. Particularly, a unit translatable by ARS is preferred because this unit can enhance translation efficiency. Such an example includes Lac. The amino acid having amino group side chain to form a branch by the reaction with the thioester is not particularly limited by its side chain as long as the side chain has an amino group or optionally protected amino group. The unprotected amino group used needs to have much lower reactivity than that of the amino group used in the first cyclization. The amino group may be secondary amine or primary amine and is more preferably primary amine for the purpose of allowing the branching reaction to proceed efficiently. A reaction promoting group such as an SH group may be present vicinally oriented to the amino group or optionally protected amino group and is also optionally protected. The amino acid having an amino group side chain is not particularly limited by its type as long as the amino acid has an amino group, which may be any of an optionally substituted alkylamino group, aralkylamino group, arylamino group, heteroarylamino group and cycloalkylamino group. The amino acid may also have a thiol group (SH group) or protected thiol group at the side chain. These substituents, except for the reaction promoting group (e.g., SH group), are preferably substituents defined in the side chain of the drug-like amino acid. The substituents are more preferably selected from substituents that provide for translational synthesis. One of the hydrogen atoms at a site represented by NH2 in the scheme is determined as a hydrogen atom, and the other hydrogen atom may be replaced with an optionally substituted alkyl group, alkenyl group, alkynyl group, aralkyl group, aryl group, heteroaryl group or cycloalkyl group. A reaction promoting group may be added thereto. A NH2 group is preferred. These substituents, except for the reaction promoting group (e.g., SH group), are also preferably substituents defined in the side chain of the drug-like amino acid. The substituents are more preferably selected from substituents that provide for translational synthesis.

Scheme F3 shows an example in which the first cyclization and branching are both carried out by amide bond reaction. In order to obtain this branched peptide, the triangle unit is selected from amino acids, amino acid derivatives or N-terminal carboxylic acid derivatives having a reaction promoting group as typified by Compound N-1 and Compound N-2, and Compounds Na-1, Na-2, Na-3, Na-4, Na-5 and Na-6 not having a reaction promoting group. The intersection unit is selected from among active esters typified by Compound C-1. The site that is converted to activated ester during the second branching reaction is selected from, for example, α-hydroxycarboxylic acid derivatives typified by Compound e1, a 3-component (Cys-Pro-α-hydroxycarboxylic acid) site represented by Compound F5, and active esters typified by Compound C-1 (although Cys, Pro and α-hydroxycarboxylic acid are translated as separate units by tRNAs, Cys and Pro are eliminated after posttranslational modification and therefore belong neither to the filled circle units nor to the square units; the α-hydroxycarboxylic acid becomes the square unit). For this branching reaction, the site having an amino group is selected from compounds typified by Compounds Na-4, Na-10 and Na-11 (wherein a H atom in the moiety represented by NH may be protected during translational synthesis). Such examples include unprotected amine such as lysine as well as Compounds tk100, tk101, tk102, tk103, tk104, tk34, tk7, tk14, tk105, tk106, tk107 and tk108.

According to this concept, more diverse constructs than ever can be displayed by display libraries as a result of branching. This can be expected to produce a more increased potential for obtaining compounds having various functions, such as molecules binding to or inhibiting conventionally difficult-to-address drug targets. This approach, which enables such branching, is valuable not only for the case where the first cyclization reaction is drug-like cyclization but for the case where the first cyclization reaction is any cyclization reaction as long as the second cyclization reaction achieves drug-like cyclization. This method is useful in forming diverse constructs, because the first cyclization reaction is not limited to drug-like cyclization reaction. In such a case, all approaches which involve generating active ester from a translation product are included in the scope of this approach. Examples thereof include Compounds F5, e1, C-1, C-2 and C-3. Examples of the 2nd amine group site include optionally protected Compound Na-4, Compound Na-5, Compound Na-10 (for Na-7 group and Na-8 group) and Compound Na-11 (for Na-7 group and Na-8 group).

The first cyclization reaction can be allowed to proceed easily by selecting a unit having a reaction promoting group (e.g., Compound N-1 or Compound N-2) as the triangle unit. The reaction with the translationally synthesizable intersection unit having thioester at the side chain may be performed at a pH around 7 (translation conditions) in the presence or absence of a reactive additive. In this case, a wider range of sites can be selected for use in the second branching. Specifically, Compound e1 can be stably present, and in Compound F5, a hydrogen atom as Rf5, which is however preferably a group other than a hydrogen atom, can be stably present and is therefore acceptable. A unit having an unprotected amino group, for example, an amino group not having a reaction promoting group as in Lys, is also acceptable as the unit on the amino group side. Alternatively, the amino group may be protected or may be protected with amine having a reaction promoting group. All of these cases can be used in this approach. The protecting group can be removed, if necessary, followed by branching reaction and the subsequent step of removing the reaction promoting group to obtain the desired branched peptide.

The Rf1 group in Compound e1 is selected as mentioned above and is more preferably selected from a hydrogen atom and an optionally protected mercaptoalkyl group (wherein the SH group is protected). Particularly preferably, Rf1 is selected from a hydrogen atom and an optionally protected mercaptomethyl group and 2-mercaptoethyl group.

The Rf2 group in Compound F5 is selected from an optionally protected mercaptoalkyl group. An amino acid containing Rf2 preferably assumes L-conformation. More preferably, Rf2 is selected from an optionally protected mercaptomethyl group and 2-mercaptoethyl group. The Rf3 group can be selected in the same way as in Ra13. Preferably, Rf3 can be selected in the same way as in Ra1. Particularly preferably, Rf3 is a methyl group or forms a ring together with Rf4. The ring is preferably 3- to 8-membered, more preferably 4- to 6-membered, in size. The carbon atoms forming the ring are optionally substituted by the substituents defined in the side chain of the drug-like amino acid. As a typical example, the 5-membered ring is preferably proline. Rf4 can be selected in the same way as in Ra4.

On the other hand, when a unit not having a reaction promoting group is selected as the triangle unit (e.g., Ala or Phe included in Compound Na-2 is selected), an additive such as trifluoromethylthiophenol is more preferably added for allowing the first reaction to proceed. The reaction is more preferably performed at a pH increased to around 7.8 and a reaction temperature of approximately 37° C. to 50° C. for a time of approximately 6 to 10 hours. In this respect, preferably, the branching site is stably present under such reaction conditions without causing chemical reaction. Thus, it is preferred that a unit having an unprotected amino group as in Lys should not be selected for the amino group site that participates in amide bond formation in branching reaction. Specifically, the NH group (and also, the reaction promoting group) in Compound Na-4, Na-10 or Na-11 is preferably protected. This site may have an optionally protected reaction promoting group (e.g., Compound tk100) or may not have an optionally protected reaction promoting group (e.g., tk104) as long as the site has the protected amino group. The protecting group needs to be stably present during translation and during the first cyclization reaction. Examples of such protecting groups include a trifluoroacetyl group, 4-azidobenzyloxycarbonyl group, 3-nitro-2-pyridinesulfenyl group and a protecting group derived from a thiazolidine ring. The trifluoroacetyl group is selectively deprotected only when pH gets larger than 8. The 4-azidobenzyloxycarbonyl group is selectively deprotected only when a reducing agent tris(2-carboxyethyl)phosphine is added thereto. The 3-nitro-2-pyridinesulfenyl group is selectively deprotected only when an additive 2-mercaptopyridine is added thereto at pH 4. The protecting group derived from a thiazolidine ring is selectively deprotected only when an additive dithiodipyridine is added thereto at pH 4 to open the thiazolidine ring, followed by the addition of tris(2-carboxyethyl)phosphine. Thus, the protecting group can be selected from protecting groups for the translationally synthesizable amino group that are stable during translational synthesis and during the first cyclization reaction and are selectively deprotected after the first cyclization under reaction conditions where RNA is stable. When the precursor site for thioester to be generated in the second branching is selected from Compound e1, preferably, the Rf1 site is a hydrogen atom or the Rf1 site has a reaction promoting group (e.g., SH group). The reaction promoting group is preferably protected. When the site is selected from Compound F5, Rf5 is preferably a group other than a hydrogen atom. Such examples include compounds wherein Rf5 is a methyl group, a benzyl group or the like. When the α-position (Rf5) of the hydroxyl site is a hydrogen atom, thioester is inevitably generated so that the first cyclization reaction cannot be performed selectively. When one or more carbon atoms are located at this position, thioester generation can be suppressed under the first cyclization reaction conditions. For the branching site thus selected, the deprotection reaction of the amine site or thioester site is carried out, if necessary, followed by branching at a pH increased to 8.2 or higher. Thus, the branching site is stably present during the first cyclization reaction and subjected to branching reaction after the deprotection step, and finally, the reaction promoting group can be removed, if necessary, to obtain the branched peptide.

The description about a chemical structure having an amino group that forms an amide bond by branching reaction and a protecting group for the amino group will be made below.

Protecting Group for Amino Group for Use in Chemical Modification of Peptide Compound-Nucleic Acid Complex Obtained by Translational Synthesis, and Deprotection Method Thereof The protecting group for the amino group described herein is defined not only as a functional group that inactivates or reduces the reactivity of single primary amine or secondary amine, but as a structure that simultaneously inactivates, by one functional group, a plurality of amino groups or other heteroatoms. The protecting group for the amino group also includes, for example, a thiazolidine ring, thiazinane ring, oxazolidine ring and imidazolidine ring. The carbon atoms forming these protecting groups are optionally substituted.

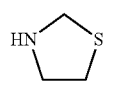
Thiazolidine ring

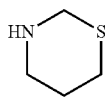
Thiazinane ring

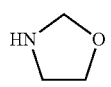
Oxazolidine ring

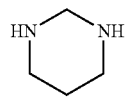
Imidazolidine ring

The protecting group mentioned above refers to any of 1) a protecting group removable under acidic conditions, 2) a protecting group removable under basic conditions, 3) a protecting group removable under oxidative conditions, 4) a protecting group removable under reductive conditions, 5) a protecting group removable by light irradiation and 6) a protecting group removable by the addition of a nucleophile, or a protecting group that can be deprotected by combining two or more of these conditions of 1) to 6).

The protecting group removable under acidic conditions refers to a protecting group that can be removed at a pH ranging from 1 to 7. The protecting group is preferably a protecting group that can be deprotected at a pH ranging from 2 to 6 and is, for example, a trityl group (Tr), N-(4-methoxyphenyl)diphenylmethyl group (MMTr), 3,5-dimethoxyphenylisopropoxycarbonyl group (Ddz) or 2-(4-biphenyl)isopropoxycarbonyl group (Bpoc) shown below (Non Patent Literatures: i) Greene's Protective Groups in Organic Synthesis, Fourth Edition; and ii) Chemical Reviews, 2009, 109 (6), 2455-2504). The carbon atoms forming these protecting groups are optionally substituted.

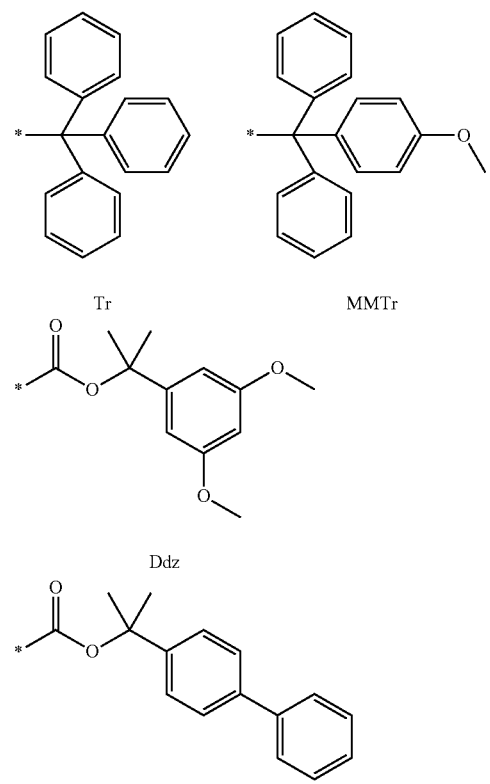

The protecting group removable under basic conditions refers to a protecting group that can be removed at a pH ranging from 7 to 14. The protecting group is preferably a protecting group that can be deprotected at a pH ranging from 7 to 10. Examples thereof include a 2-[phenyl(methyl)sulfonio]ethoxycarbonyl group to which an electron-withdrawing group is excessively added. Alternative examples thereof include a trichloroacetyl group in which one or more groups such as a halogen group, nitro group and trifluoro group are introduced. The protecting group is specifically a trifluoroacetyl group (Tfa) shown below (Non Patent Literatures: i) Greene's Protective Groups in Organic Synthesis, Fourth Edition; and ii) Chemical Reviews, 2009, 109 (6), 2455-2504).

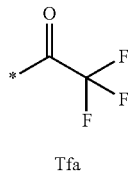

Tfa

The protecting group removable under oxidative conditions is, for example, a pentenoyl group that can be deprotected in the presence of iodine, as shown below (Non Patent Literatures: i) Greene's Protective Groups in Organic Synthesis, Fourth Edition; ii) The Journal of Organic Chemistry, 1997, 62, 778-779; and iii) Method, 2005, 36, 245-251).

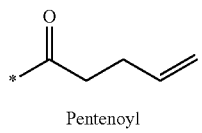 [SMILES: *C(=O)CCC=C]

Pentenoyl

The protecting group removable under reductive conditions refers to a protecting group that can be deprotected in the presence of, for example, tris(2-carboxyethyl)phosphine (TCEP) or dithiothreitol (DTT) and is, for example, an azide group (Non Patent Literature: ChemBioChem, 2009, 10, 1186-1192), 4-azidobenzyloxycarbonyl group (p-Acbz) (Non Patent Literature: Journal of the Chemical Society, Perkin Transactions 1, 1996, 1205-1211), 2-azidobenzyloxycarbonyl group (o-Acbz), azidomethoxycarbonyl (Azoc) (Non Patent Literature: Organic Letters, 2007, 9 (11), 2223-2225), phenyldisulfanylethyloxycarbonyl group (Phdec) or 2-pyridyldisulfanylethyloxycarbonyl group (Pydec) (Non Patent Literature: Chemical Reviews, 2009, 109 (6), 2455-2504). The carbon atoms forming these protecting groups are optionally substituted.

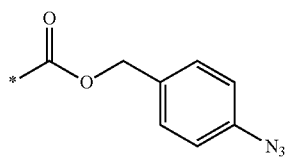

p-Acbz

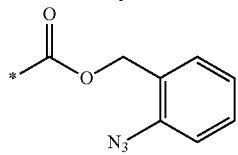

o-Acbz

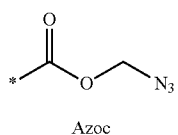

Azoc

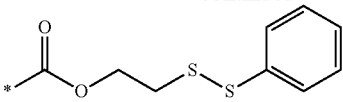

Phdec

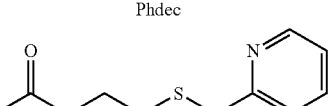

Pydec

The protecting group removable by light irradiation is, for example, an o-nitrobenzyloxycarbonyl group (oNz), 4,5-dimethoxy-2-nitrobenzoxy)carbonyl group (Nvoc) or 2-(2-nitrophenyl) propyloxycarbonyl group (Nppoc) (Non Patent Literatures: i) Chemical Reviews, 2009, 109 (6), 2455-2504; ii) The Journal of Organic Chemistry, 1997, 62, 778-779; and iii) Bioorganic & Medicinal Chemistry, 2012, 20, 2679-2689). The carbon atoms forming these protecting groups are optionally substituted.

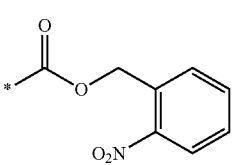

oNz

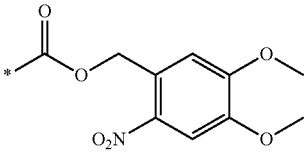

Nvoc

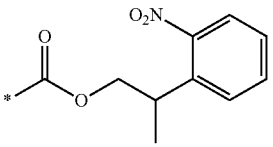

Nppoc

The protecting group removable by the addition of a nucleophile refers to a protecting group that can be deprotected in the presence of, for example, thiol and is, for example, an o-nitrobenzenesulfonyl group (o-NBS), 2,4-dinitrobenzenesulfonyl group (dNBS) or dithiosuccinoyl group (Dts) (Non Patent Literature: Chemical Reviews, 2009, 109 (6), 2455-2504). The carbon atoms forming these protecting groups are optionally substituted.

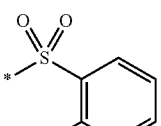   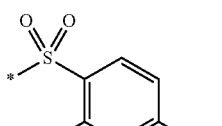

o-NBS             dNBS

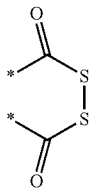

Dts

The protecting group that can be deprotected by combining two or more of these conditions of 1) to 6) is a protecting group that can be deprotected by a deprotection method, for example, under the combined conditions of 1) and 6) which involves adding thiol at a pH ranging from 2 to 6, for example, a 3-nitro-2-pyridinesulfenyl group (Npys) (Non Patent Literatures: i) International Journal of Peptide and Protein Research, 1990, 35, 545-549; and ii) International Journal of Peptide and Protein Research, 1980, 16, 392-401) or 2-nitrophenylsulfenyl group (Nps) (Non Patent Literature: Chemical Reviews, 2009, 109 (6), 2455-2504). The carbon atoms forming these protecting groups are optionally substituted.

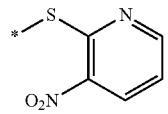 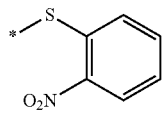

Npys          Nps

Alternatively, the protecting group that is applied to a deprotection method under the combined conditions of 1) and 3) is, for example, a protecting group that can be deprotected by the addition of a disulfide compound at a pH ranging from 2 to 6, for example, a thiazolidine ring or thiazinane ring. The carbon atoms forming these protecting groups are optionally substituted.

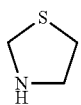 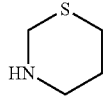

Thiazoline ring     Thiazinane ring

Deprotection Method for Amino Group by Opening of Thiazolidine Ring and Thiazinane Ring Amidation reaction by native chemical ligation (NCL) utilizing the nucleophilicity of thiol is an approach useful in the chemical synthesis of peptides and proteins. The protection of amino and thiol groups in advance is useful means for performing continuous amidation reaction or NCL at an arbitrary timing. For example, a thiazolidine ring has been reported as a structure for the simultaneous protection of amino and thiol groups in cysteine in protein synthesis by the multi-step amidation of peptide chains as described in Non Patent Literature v1 or in the chemical modification of proteins as described in Non Patent Literature v2.

A method which involves adding methoxyamine into a buffer solution of pH 4 to pH 7 is publicly known as a method for deprotecting a thiazolidine ring in a peptide structure into amino and thiol groups (e.g., Non Patent Literature v1 (Angewandte Chemie, International Edition, 2006, 45 (24), 3985-3988) and Non Patent Literature v2 (Journal of the American Chemical Society, 2011, 133, 11418-11421)). For example, the ester- or thioester-containing structure of the peptide compound described herein may have a risk of generating alkoxyamide by side reaction between methoxyamine and the ester moiety during deprotection reaction or subsequent reaction in one pot.

The present inventors have developed a method of adding a disulfide compound as a thiazolidine ring or thiazinane ring deprotection method without the use of methoxyamine.

A feature of this approach is to open the thiazolidine ring or thiazinane ring under acidic conditions to convert the ring to an aminodisulfide structure, which can be converted to aminothiol by the subsequent addition of a reducing agent.

This approach is performed in water, in a buffer solution or in an organic solvent mixed with water. The organic solvent used is selected as from solvents that are miscible with water and are neither reactive with a substrate nor deposited. For example, N,N-dimethylacetamide, N, N-dimethylformamide or acetonitrile is used. The ratio between water and the organic solvent is determined depending on the solubility of the substrate and the disulfide compound. For example, 5% or more N,N-dimethylacetamide is preferably used for reaction using 10 mM dithiodipyridine, from the viewpoint of the solubility of dithiodipyridine.

The pH range for opening the thiazolidine ring is preferably pH 1 to 5 for the purpose of completing the reaction within 12 hours. The pH range is preferably pH 4 to 5 for the treatment of a compound having a thiazolidine ring unstable in the acidic environment.

The reaction temperature for opening the thiazolidine ring is 15° C. or higher for the purpose of completing the reaction within 12 hours. The reaction temperature is preferably in the range of 15 to 50° C. for the treatment of a compound having a thermally unstable thiazolidine ring.

For example, dialkyl disulfide or diaryl disulfide can be added as the disulfide compound. Diaryl disulfide is preferred, with dithiodipyridine more preferred.

The amount of the dithiodipyridine used is determined depending on the amount of the thiazolidine derivative used. For example, 30 mM dithiodipyridine is used with respect to 1.0 mM thiazolidine derivative. In this case, the reaction is performed at pH 4.2 and 36° C. to complete the opening of the thiazolidine ring within 12 hours.

Alkylphosphine, arylphosphine, or a thiol compound having reducing power can be used as the reducing agent for converting the aminodisulfide structure to aminothiol. For example, TCEP or DTT is used. TCEP is preferred for rapid conversion to aminothiol.

The amount of TCEP used is determined depending on the amounts of the thiazolidine derivative and dithiodipyridine used. For example, 1 mM thiazolidine derivative is converted to 2-(2-pyridyldithio)ethylamine by 30 mM dithiodipyridine. In this case, the reaction is performed at pH 4.5 and 24° C. using 40 mM TCEP to complete conversion to aminoethanethiol within 1 hour.

Such a technology of forming a branch structure from a linear peptide sequence translated based on primary sequence information of mRNA enables construction of an mRNA display library of highly structurally diverse peptides having branch structures, which cannot be achieved by conventional technology.

This methodology of peptide synthesis using hydroxycarboxylic acid as an aid to expand chemical space is described above, is not limited by the approaches of Schemes E, F, F2 and F3. The first cyclization reaction is not limited to the cyclization reaction mentioned above and can be applied to all cyclization reactions applicable under reaction conditions that achieve branching reaction (where the branching site is stably present during the first cyclization reaction and activation for branching can be carried out under reaction conditions where RNA is stable). This concept can be utilized in any method using Compound F5 or E1 as the second active ester-generating site and using Compound Na-4, Compound Na-5, Compound Na-10 (Na-7 group or Na-8 group) or Compound Na-11 (Na-7 group or Na-8 group) as the 2nd amino group site. Hydroxycarboxylic acid and an amino acid having an amine site can be located at the desired positions and subjected to appropriate chemical reaction to obtain the desired branched peptide (peptide having linear portion 2). The hydroxycarboxylic acid, the amine and each amino acid or amino acid analog can be arbitrarily selected as long as they have necessary functional groups. The hydroxycarboxylic acid site is preferably located on the N-terminal side. The hydroxycarboxylic acid is not limited to α-hydroxycarboxylic acid, and various hydroxycarboxylic acids typified by β- and γ-hydroxycarboxylic acids may be used. Alternatively, branched peptide formation reaction using thioester as an aid instead of ester may be carried out by the translational incorporation of thiocarboxylic acid instead of the hydroxycarboxylic acid. This approach achieves the expansion of chemical space indispensable for creating Hit compounds from middle molecules having the limited number of amino acids.

Figure 88:
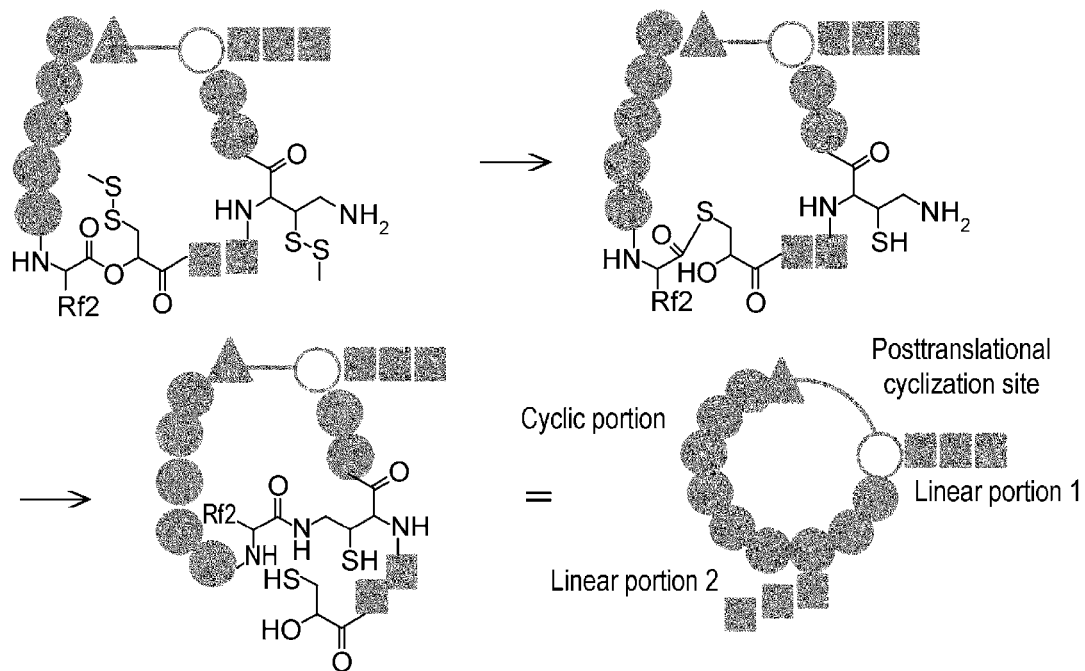
FIG. 88 is a diagram showing scheme F. Scheme F shows an example 2 of approach of forming linear portion 2.
Figure 89:
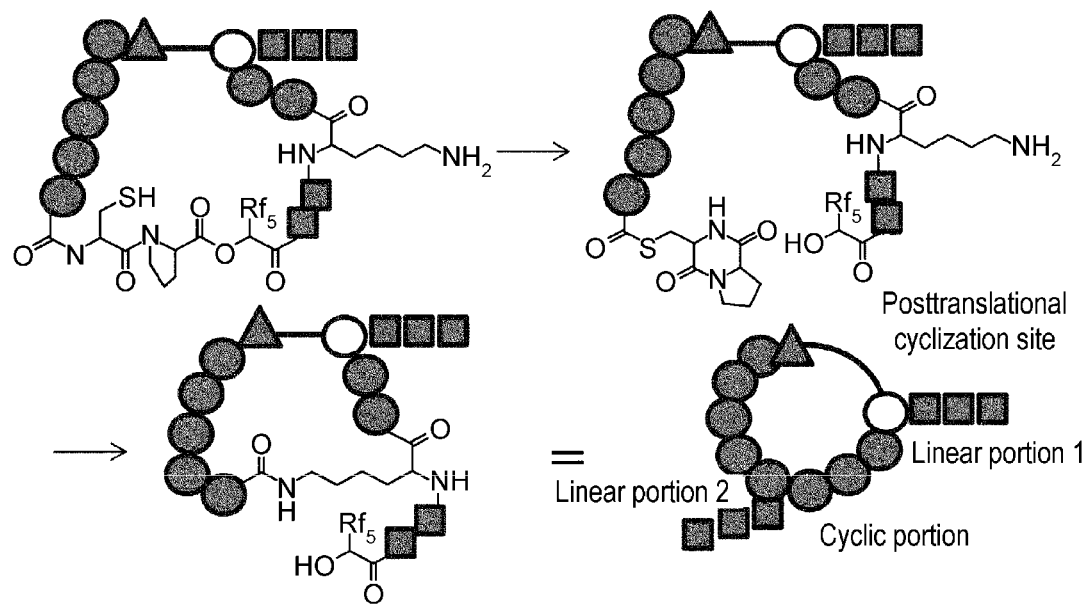
FIG. 89 is a diagram showing scheme F2. Scheme F2 shows an example 3 of approach of forming linear portion 2.
Figure 90:
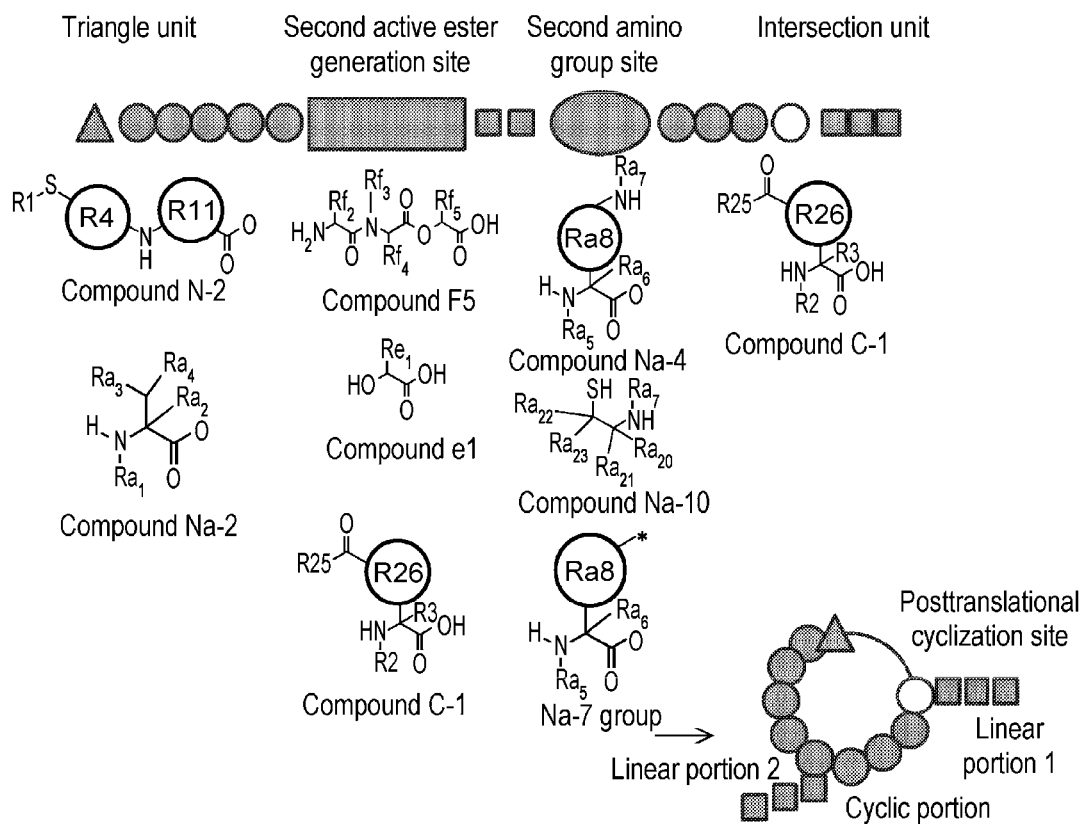
FIG. 90 is a diagram showing scheme F3. Scheme F3 shows an example 4 of approach of forming linear portion 2.

See FIGS. 88, 89 and 90.

Next, a reaction design will be described by taking use of C—C bond cyclization as an example. For example, a carboxylic acid having a double bond can be translationally incorporated as an N-terminal carboxylic acid analog into the triangle unit, while an amino acid having an iodophenyl group at the side chain can be translationally incorporated into the intersection unit (O unit) (Scheme C-2). When functional groups for condensation reaction by Heck reaction using Pd are thus introduced into the triangle unit and the intersection unit, respectively, a C—C bond cyclization product is obtained by the reaction using Pd. Various ligands for Pd can be selected. A phosphine ligand, a phosphine oxide ligand, a ligand composed of a nitrogen atom, a ligand composed of an arsenic atom, a carbene ligand or the like can be used as a ligand for usual Pd-catalyzed reaction. These ligands may be monodentate ligands intramolecularly having one functional group capable of being coordinated to Pd or may be bidentate ligands having in combination two of functional groups capable of being coordinated to Pd. Since the reaction needs to be performed in water, a ligand having a water-soluble functional group may be used. In this context, Pd is subject to inactivation by complex formation due to RNA components and nucleic acid components such as GTP and ATP contained in a translation solution. Thus, a ligand that forms a strong coordinate bond with Pd is preferred. Examples of such ligands include bidentate phosphine ligands such as 1,1'-bis(diphenylphosphino)ferrocene, 2,2'-bis(diphenylphosphino)-1,1'-biphenyl, 2,2'-bis(diphenylphosphino)-1,1'-binaphthyl, 4,5-bis(diphenylphosphino)-9,9-dimethyl xanthene and 1,3-bis(diphenylphosphino)propane. 2,2'-Bis(diphenylphosphino)-1,1'-biphenyl is more preferred in terms of solubility in an aqueous solvent. Use of Pd in a catalytic amount (1 mol % or lower in many cases) suffices for usual organic synthetic chemical reaction. For application to a display library after translational synthesis, however, Pd should be used in an excessive amount for allowing the desired chemical reaction to proceed at a sufficient rate, because Pd is complexed with RNA portions necessary for translational synthesis. On the other hand, the excessive use of Pd reduces the solubility of the complex with RNA and thereby hinders the desired chemical reaction from proceeding at a sufficient rate. Thus, the amount of Pd used is preferably 1 nmol or higher, more preferably 60 nmol, with respect to a translationally synthesized product containing 1 pmol of mRNA. Use of micelle, as described later in Examples, accelerates the reaction and is therefore preferred.

The micelle that may be used can be any of anionic, cationic, amphoteric and nonionic forms. Particularly, nonionic micelle polyoxyethanyl-α-tocopheryl sebacate (PTS) is preferably used. The concentration at which the polyoxyethanyl-α-tocopheryl sebacate is used can be an arbitrary concentration and is preferably 1% or higher (final concentration), more preferably 7.5% or higher (final concentration). Progression of the reaction requires using a base. A buffer composed of components that are not coordinated to Pd is preferably used. A phosphate buffer, carbonate buffer or the like may be used. The pH of the reaction solvent is preferably adjusted to a range where mRNA can be stably present and the cyclization reaction proceeds. The pH is more preferably 7 or higher and 10 or lower, further preferably 7.5 or higher and 8.5 or lower. The reaction temperature is not particularly limited as long as the temperature falls within a range where mRNA can be stably present and usual chemical reaction can be carried out. The reaction temperature is preferably 15° C. to 80° C., more preferably 40° C. to 60° C.

Figure 91:
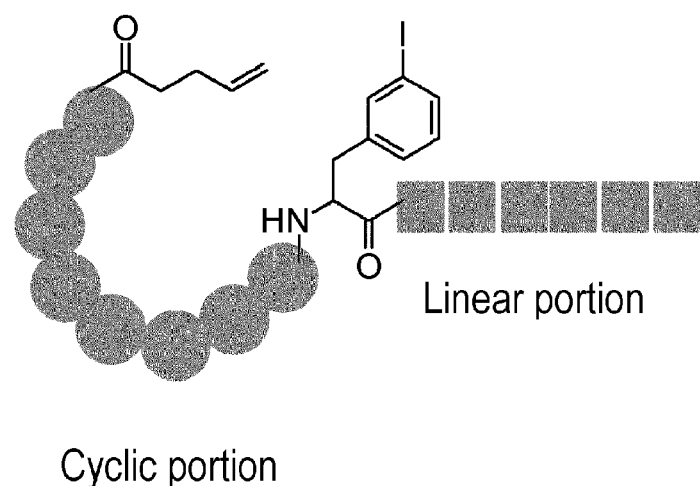
FIG. 91 is a diagram showing scheme C-2. Scheme C-2 shows an example of an uncyclized translated compound having a group forming a carbon-carbon double bond at the triangle unit and an iodophenyl group at the intersection unit. This is a specific example of scheme A-1.

See FIG. 91.

Although the Heck reaction using Pd is described above as an example of the C—C bond formation reaction, the C—C bond cyclization reaction of the present invention is not limited to the Heck reaction using Pd. Various reactions using Pd, such as Suzuki reaction and Sonogashira reaction, can be similarly carried out. In this case, the selection of a ligand or a base may be important. The transition metal is not limited to Pd, and the C—C bond formation reaction may be carried out by using various metals such as Ni, Ru and Co (Non Patent Literatures: Matthew S. Sigman et al., Advances in Transition Metal (Pd,Ni,Fe)-Catalyzed Cross-Coupling Reactions Using Alkyl-organometallics as Reaction Partners. Chem. Rev., 2011, 111, 1417-1492; Lutz Ackermann et al., Ruthenium-Catalyzed Direct Arylations Through C—H Bond Cleavages. Top Curr Chem. 2010, 292, 21; Paul Knochel et al., Pd—, Ni—, Fe—, and Co-Catalyzed Cross-Couplings Using Functionalized Zn—, Mg—, Fe—, and In-Organometallics. Isr. J. Chem. 2010, 50, 547; and Gwilherm Evano et al., Copper-Mediated Coupling Reactions and Their Applications in Natural Products and Designed Biomolecules Synthesis. Chem. Rev. 2008, 108, 3054).

The amino acid, amino acid analog or N-terminal carboxylic acid analog used as the triangle unit for Scheme C-2 is not particularly limited as long as this unit has a reactive functional group. The selection of the amino acid, which leaves amine at the N-terminal, is disadvantageous to membrane permeation, compared with the absence of N-terminal amine. For this reason, a fewer number of heteroatoms is more preferred for the triangle unit. Examples of such N-terminal carboxylic acid analogs can include compounds represented by Compounds CC-1 to CC-4. In Compound CC-1, a carbon-carbon double bond serves as a reactive site. In Compound CC-2, a carbon-carbon triple bond serves as a reactive site. In Compound CC-3, X serves as a reactive site. X is preferably halogen and is selected from among Cl, Br, I and F. Br and I are preferred in terms of reactivity, with I most preferred. In Compound CC-4, a boric acid ester moiety serves as a reactive site. R301, R302 and R303 are each selected from among a hydrogen atom and an optionally substituted alkyl group, alkenyl group, alkynyl group, cycloalkyl group, aryl group, heteroaryl group and aralkyl group. These substituents are not particularly limited as long as Compounds CC-1 to CC-4 obtained as a result of substitution thereby can be translationally synthesized. Examples of such substituents include a halogen group and alkoxy group.

R304 represents a unit that links the reactive site to a translation site (carboxylic acid site). Hereinafter, a typical structure thereof will be shown. Both the units can be linked by any of C1-C6 units including a methylene group (partial structure N-3), ethylene group (partial structure N-4) and propylene group (partial structure N-5). Alternatively, direct linkage may be formed from the aryl carbon of an aromatic compound (partial structure N-6). Alternatively, the linkage may be formed by an aralkyl structure (partial structures N-7 and N-8). In this context, the linking position is not limited to the ortho-position and may be the meta- or para-position. A substituted aryl group other than a phenyl group or a substituted aralkyl group may be used. Examples of the substituent include a halogen group and alkoxy group.

The amino acid used as the triangle unit for Scheme C-2 is not particularly limited as long as the amino acid is, for example, an amino acid having a double bond, triple bond, halogen or boric acid ester at the side chain. The amino acid may be an L-amino acid, D-amino acid or α,α-dialkylamino acid and is particularly preferably an L-amino acid. The N-terminal amino group is preferably substituted for obtaining a drug-like peptide. Although alkylation such as N-methylation is possible, the introduction of a substituent that cancels the basicity of a nitrogen atom, such as amidation (e.g., acylation), is rather preferred.

The amino acid analog or N-terminal carboxylic acid analog used as the triangle unit for Scheme C-2 may be a hydroxycarboxylic acid having a double bond, triple bond, halogen or boric acid ester at the side chain. As in the amino acid, the side chain can be selected without particular limitations. In addition to α-hydroxycarboxylic acid, β- or γ-hydroxycarboxylic acid may be used. Alternatively, dipeptide or tripeptide having a double bond, triple bond, halogen or boric acid ester at the side chain may be used.

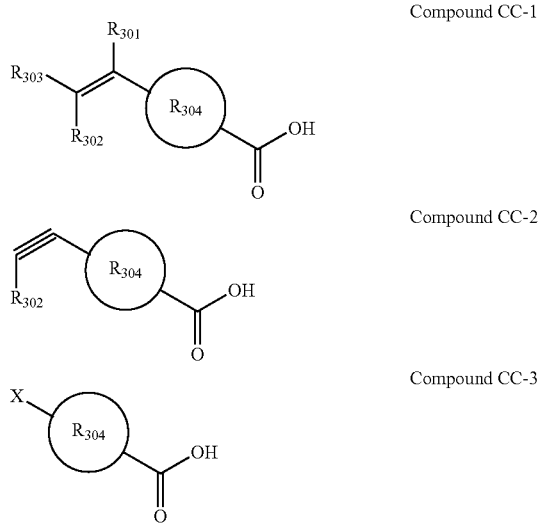

Compound CC-1

Compound CC-2

Compound CC-3

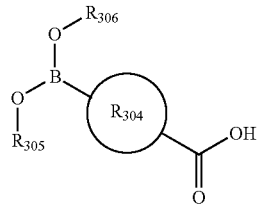

Compound CC-4

Examples of the intersection unit (O unit) for Scheme C-2 include amino acids and α-hydroxycarboxylic acids each having a double bond, triple bond, halogen or boric acid ester at the side chain. The amino acid or α-hydroxycarboxylic acid is not particularly limited as long as its side chain has any of these reactive functional groups. Each reactive functional group is optionally substituted by substituted by a substituent selected from among an optionally substituted alkyl group, alkenyl group, alkynyl group, cycloalkyl group, aryl group, heteroaryl group and aralkyl group. Examples of substituents for these groups include a halogen group and alkoxy group.

Any of L-, D- and α,α-dialkyl forms are acceptable. An L-amino acid or amino acid analog is preferred provided that a hydrogen atom is present at the α-position.

The combination of the triangle unit and the intersection unit (O) unit is not particularly limited as long as the combined units can be condensed by reaction using a transition metal such as Pd.

Chemical Synthesis of Peptide Compound

The peptide compound of the present invention may be prepared by chemical synthesis.

Examples thereof include a method called Fmoc synthesis and a method called Boc synthesis. The Fmoc synthesis employs, as a basic unit, an amino acid containing: a main chain amino group protected with an Fmoc group; a side chain functional group optionally protected with a protecting group that is not cleaved by a base such as piperidine; and an unprotected main chain carboxylic acid. In addition, any basic unit having an Fmoc-protected amino group and a carboxylic acid group in combination may be used without particular limitations. For example, dipeptide may be used as a basic unit. A basic unit other than the Fmoc-amino acid may be located at the N-terminal. The N-terminal unit may be, for example, a Boc-amino acid or a carboxylic acid analog not having an amino group. The carboxylic acid group of main chain is chemically reacted with a functional group on a solid-phase carrier to immobilize the first basic unit onto the carrier. Subsequently, its Fmoc group is deprotected by a base such as piperidine or DBU to generate a fresh amino group, which is then subjected to condensation reaction with a carboxylic acid-containing protected amino acid added as the second basic unit to form a peptide bond. Various combinations including the combination of DIC and HOBt, the combination of DIC and HOAt and the combination of HATU and DIPEA can be used in the condensation reaction. The deprotection of the Fmoc group and the subsequent peptide bond formation reaction can be repetitively performed to produce the desired peptide sequence. The desired sequence thus obtained is excised from the solid phase, and the optionally introduced protecting groups for the side chain functional groups are deprotected. Alternatively, the peptide may be structurally converted or cyclized before the excision from the solid phase. The excision from the solid phase and the deprotection may be carried out under the same conditions, for example, using TFA/H$_2$O at a ratio of 90:10, or the protecting groups may be deprotected, if necessary, under different conditions. The excision from the solid phase may be achieved in some cases by using a weak acid such as 1% TFA and may be achieved in other cases by using a protecting group such as Pd and the orthogonality of chemical reaction between the protecting groups. A step such as cyclization can also be carried out between these steps or as a final step. For example, a side chain carboxylic acid can be condensed with an N-terminal main chain amino group, or a side chain amino group can be condensed with a C-terminal main chain carboxylic acid. In this case, the orthogonality of reaction is required between a carboxylic acid on the C-terminal side and the side chain carboxylic acid to be cyclized or between a main chain amino group or hydroxyl group on the N-terminal side and the side chain amino group to be cyclized. Protecting groups are selected in consideration of the orthogonal protecting groups as mentioned above. The reaction product thus obtained can be purified on a reverse-phase column, molecular sieve column or the like. Details on these procedures are described in, for example, the solid-phase synthesis handbook issued by Merck Japan Co., Ltd. on May 1, 2002.

Production of Drug-Like Peptide Compound or Peptide Compound-Nucleic Acid Complex The present invention provides a method for preparing a drug-like peptide compound or peptide compound-nucleic acid complex having desired activity.

Examples of the method for preparing a drug-like peptide compound-nucleic acid complex having desired activity can include a preparation method comprising the steps of:
(i) translationally synthesizing a noncyclic peptide compound having 9 to 13 amino acids and amino acid analogs in total to form a noncyclic peptide compound-nucleic acid complex in which the noncyclic peptide compound links to a nucleic acid sequence encoding the noncyclic peptide compound through a linker;
(ii) cyclizing the noncyclic peptide compound of the complex translationally synthesized in Step (i) by an amide bond or a carbon-carbon bond to form a cyclic compound having a cyclic portion with 5 to 12 amino acid and amino acid analog residues in total; and
(iii) bringing a library of the peptide compound-nucleic acid complexes having cyclic portions as provided in Step (ii) into contact with a biomolecule to select a complex having binding activity to the biomolecule.

The drug-like peptide compound having desired activity can be further prepared from the complex selected by the above steps.

Examples of such preparation methods can include a preparation method comprising the steps of:
(iv) obtaining sequence information of the peptide compound from the nucleic acid sequence of the complex selected in Step (iii) above, and
(v) chemically synthesizing the peptide compound based on the sequence information obtained in Step (iv) above.

The noncyclic peptide compound contains an α-hydroxycarboxylic acid, and an amino acid or amino acid analog having an optionally protected amino group at the side chain, and wherein the above preparation method may further comprise the step of forming a branched site by chemically reacting the α-hydroxycarboxylic acid site with the amino acid or amino acid analog site having an amino group at the side chain before or following Step (ii) of forming the cyclic compound. This step enables preparation of the peptide compound having linear portion 2 at any of various positions of the cyclic portion as mentioned above.

In this context, the total number of amino acid and amino acid analog residues described in Step (i) above and the total number of amino acid and amino acid analog residues in the cyclic portion described in Step (ii) exclude the number of amino acids or amino acid analogs removed by posttranslational modification. For example, in the preparation of the peptide compound having linear portion 2 according to Scheme F3, the Cys-Pro sequence eliminated from the peptide during posttranslational modification is excluded from the numbers of amino acids and amino acid analogs in Steps (i) and (ii). When, for example, a site containing a Gly-Ser repeat structure is used as the linker site between the peptide compound and RNA, this Gly-Ser repeat structure, the fixed amino acid region, and the site intended to link the peptide compound having a cyclic portion according to the present invention, particularly, the drug-like peptide compound, to the nucleic acid are contained in the linker and therefore excluded from the numbers of amino acids and amino acid analogs in Steps (i) and (ii). In this case, it is only required that the number of residues in the cyclic portion should be 5 to 11 after the reaction of generating linear portion 2, though more than 5 to 11 residues are contained in the cyclic portion after the cyclization of Step (ii).

In the present preparation method, chemical modification may be carried out in Step (ii) or Step (v) for the drug-like peptide compound or for optimization. In the present invention, the target substance is preferably a biomolecule. The "biomolecule" according to the present invention is not particularly limited as long as the biomolecule is a molecule found in vivo. The biomolecule is preferably a molecule serving as a target in the treatment of a disease. Particularly preferably, the biomolecule is, for example, a molecule not having a cavity to which conventional small-molecule compounds having a molecular weight less than 500 can bind, or an intracellular protein, nucleic acid, intracellular region of membrane protein or transmembrane domain of membrane protein inaccessible by high-molecular compounds such as antibodies.

Specific examples thereof include: transcription factors such as STAT, AP1, CREB and SREBP; G-protein-coupled receptors (GPCRs) such as muscarinic acetylcholine receptors, cannabinoid receptors, GLP-1 receptors and PTH receptors; cytokines and their receptors, such as TNF, TNFR, IL-6 and IL-6R; ion channel receptors, ion channels and transporters, such as P2X receptors and nicotinic acetylcholine receptors; and microRNAs such as miR-21 and miR206.

The cyclic portion may be formed by using, for example, the cyclization reaction mentioned above. An amide bond or carbon-carbon bond can be formed by the cyclization reaction.

Also, a technology known in the art, for example, a cell-free translation system, can be used in the step of synthesizing the peptide compound-nucleic acid complex. Specifically, the complex can be made by a method as described below.

A transfer RNA (tRNA) refers to an RNA molecule of 73 to 93 bases in length that has a molecular weight of 25000 to 30000 and contains a 3'-terminal CCA sequence. This tRNA forms an ester bond through its 3'-end with the carboxy terminus of an amino acid. The resulting aminoacylated tRNA forms a ternary complex with polypeptide elongation factor (EF-Tu) and GTP, which is in turn transferred to the ribosome where this RNA is involved in codon recognition by the base pairing between anticodons of the tRNA sequence and mRNA codons in the ribosomal translation of the nucleotide sequence information of mRNA into an amino acid sequence. tRNAs biosynthesized in cells contain bases modified by covalent bonds, which may influence the conformations of the tRNAs or the base pairing of anticodons and help the tRNAs recognize codons. tRNAs synthesized by general in vivo transcription are composed of so-called nucleobases adenine, uracil, guanine and cytosine, whereas tRNAs prepared from cells or synthesized chemically may contain modified bases such as other methylated forms, sulfur-containing derivatives, deaminated derivatives and adenosine derivatives containing isopentenyl groups or threonine. tRNAs obtained by using the pdCpA method or the like may contain deoxy bases.

A template DNA sequence is prepared so as to encode a desired tRNA sequence and to have a T7, T3 or SP6 promoter located upstream thereof. RNA can be synthesized therefrom by transcription using RNA polymerase compatible with the promoter, such as T7, T3 or SP6 RNA polymerase. tRNAs can also be extracted from cells and purified, and the purified tRNA of interest can be extracted by using a probe having a sequence complementary to the tRNA sequence. In this case, cells transformed with expression vectors for the tRNA of interest may be used as a source. The RNA sequence of interest may be synthesized chemically. For example, a tRNA lacking CA at the 3'-terminal CCA sequence thus obtained can be ligated to aminoacylated pdCpA prepared separately by RNA ligase to obtain an aminoacyl-tRNA (pdCpA method). A full-length tRNA may be prepared and aminoacylated by a ribozyme, called flexizyme, which is able to charge active esters of various unnatural amino acids onto tRNAs. In addition, acylated tRNAs can be obtained by using methods described later.

The peptide can be translated by the addition of mRNA to PUREsystem mixed with protein factors necessary for translation in *E. coli* (methionyl tRNA transformylase, EF-G, RF1, RF2, RF3, RRF, IF1, IF2, IF3, EF-Tu, EF-Ts and ARS (necessary one is selected from AlaRS, ArgRS, AsnRS, AspRS, CysRS, GlnRS, GluRS, GlyRS, HisRS, IleRS, LeuRS, LysRS, MetRS, PheRS, ProRS, SerRS, ThrRS, TrpRS, TyrRS and ValRS)), ribosome, amino acids, creatine kinase, myokinase, inorganic pyrophosphatase, nucleoside diphosphate kinase, *E. coli*-derived tRNA, creatine phosphate, potassium glutamate, HEPES-KOH (pH 7.6), magnesium acetate, spermidine, dithiothreitol, GTP, ATP, CTP, UTP and the like. Also, transcription/translation-coupled PUREsystem technology may be performed from template DNA containing a T7 promoter by adding T7 RNA polymerase in advance to the system. In this case, a desired acylated tRNA group and an unnatural amino acid group (e.g., F-Tyr) acceptable by ARS can be added to the system to translationally synthesize peptides containing the unnatural amino acid group (Kawakami T, et al., Ribosomal synthesis of polypeptoids and peptoid-peptide hybrids. J Am Chem Soc. 2008, 130, 16861-3; and Kawakami T, et al., Diverse backbone-cyclized peptides via codon reprogramming. Nat Chem Biol. 2009, 5, 888-90). Alternatively, the translational incorporation efficiency of unnatural amino acids may be enhanced by using variants of ribosome, EF-Tu and the like (Dedkova L M, et al., Construction of modified ribosomes for incorporation of D-amino acids into proteins. Biochemistry. 2006, 45, 15541-51; Doi Y, et al., Elongation factor Tu mutants expand amino acid tolerance of protein biosynthesis system. J Am Chem Soc. 2007, 129, 14458-62; and Park H S, et al. Expanding the genetic code of *Escherichia coli* with phosphoserine. Science. 2011, 333, 1151-4).

For an mRNA display library, first, a library of DNAs in which a desired sequence is located downstream of a promoter such as T7 promoter is chemically synthesized, and this library is used as templates to prepare double-stranded DNAs by primer extension reaction. The double-stranded DNAs are used as templates and transcribed into mRNAs by using RNA polymerase such as T7 RNA polymerase. Linkers (spacers) with an antibiotic puromycin (aminoacyl-tRNA analog) are conjugated to the 3'-ends of the RNAs. The resulting conjugates are added to a cell-free translation system known in the art, such as PUREsystem above, and incubated so that the mRNAs are translated to link each mRNA to the peptide encoded thereby through puromycin. In this way, a display library composed of mRNA-product complexes can be constructed in which the mRNAs are associated with their products.

In addition, the library is brought into contact with desired immobilized targets, and molecules unbound with the targets can be washed off to enrich target-binding molecules (panning). cDNA is synthesized from the mRNA serving as a tag involving gene information in the molecule thus selected, and amplified by PCR. The amplification products can be sequenced to determine the sequence of the peptide linked to the mRNA.

In the present invention, the construction of a display library composed by the conjugate of cyclized peptide compound and nucleic acid and the resulting cyclic peptides that bind to drug targets (peptide compound having a cyclic portion) or cyclized and branched peptide (peptide compound having a cyclic portion and further having linear portion 2) from the constructed display library can be performed specifically by, for example, methods[I] to [XVII] shown in the following aspects.

Initiation Read-Through

[I] The method for preparing a peptide compound having a cyclic portion according to the present invention can comprise one or more of the following steps:

A) Step of providing an aminoacylated pdCpA of Compound C-1
B) Step of providing a tRNA deficient in 3'-terminal CA
C) Step of linking the pdCpA of Step A) to the tRNA of Step B) above to provide an aminoacylated initiation tRNA of Compound C-1
D) Step of providing a cell-free translation system containing the tRNA of Step C) and not containing methionine, methionyl tRNA synthetase (MetRS), translation initiation tRNA for methionine, formyl donor or methionyl tRNA transferase
E) Step of providing a peptide sequence-encoding template DNA library comprising, downstream of a promoter, translation initiation ATG followed by a cysteine codon UGU or UGC and a further downstream codon corresponding to the anticodon of the tRNA of Step C)
F) Step of providing an mRNA library from the template DNA library of Step E)
G) Step of conjugating spacers to the 3'-ends of the mRNA library of Step F)
H) Step of adding the spacer-conjugated mRNA library of Step G) to the cell-free translation system of Step D), followed by translation to provide an uncyclized peptide compound-mRNA complex display library
I) Step of forming cyclic structures In the formation of cyclic structures, desulfurization reaction can be performed, if necessary. The method of the present invention can also comprise a step of synthesizing cDNAs by primers annealing to the 3'-regions of the mRNA library following Step G).

The method of the present invention can further comprise the following steps:
- J) Step of enriching the compounds in mRNA library that bind to a drug by panning
- K) Step of synthesizing cDNA by reverse transcriptase
- L) Step of analyzing the nucleotide sequence

[II] Moreover, the method for preparing a peptide compound having a cyclic portion according to the present invention can comprise one or more of the following steps:
- A) Step of providing an aminoacylated pdCpA of Compound C-1
- B) Step of providing a tRNA deficient in 3'-terminal CA
- C) Step of linking the pdCpA of Step A) to the tRNA of Step B) above to provide an aminoacylated initiation tRNA of Compound C-1
- D) Step of providing a cell-free translation system containing the tRNA of Step C)
- E) Step of providing a peptide sequence-encoding template DNA library comprising, downstream of a promoter, translation initiation ATG followed by a cysteine codon UGU or UGC and a further downstream codon corresponding to the anticodon of the tRNA of Step C)
- F) Step of providing an mRNA library from the template DNA library of Step E)
- G) Step of conjugating spacers to the 3'-ends of the mRNA library of Step F)
- H) Step of adding the spacer-conjugated mRNA library of Step G) to the cell-free translation system of Step D), followed by translation to provide an uncyclized peptide compound-mRNA complex display library
- I) Step of allowing peptide deformylase and methionine aminopeptidase to act on the library of Step H)

Steps H and I can be carried out simultaneously by adding peptide deformylase and methionine aminopeptidase to the system at the time of translation.
- J) Step of forming cyclic structures In the formation of cyclic structures, desulfurization reaction can be performed, if necessary. The method of the present invention can also comprise a step of synthesizing cDNAs by primers annealing to the 3'-regions of the mRNA library following Step H) or Step The method of the present invention can further comprise the following steps:
- J) Step of enriching the sequences in mRNA library that bind to a drug target by panning
- K) Step of synthesizing cDNA by reverse transcriptase
- L) Step of analyzing the nucleotide sequence

[III] Alternatively, the method for preparing a peptide compound having a cyclic portion according to the present invention can comprise one or more of the following steps:
- A) Step of providing an aminoacylated pdCpA of Compound C-3 (R2=R3=R28=R29=H, L-aspartic acid derivative)
- B) Step of providing a tRNA deficient in 3'-terminal CA
- C) Step of linking the pdCpA of Step A) to the tRNA of Step B) to provide an aminoacylated initiation tRNA of Compound C-3
- D) Step of providing a cell-free translation system containing the tRNA of Step C) and not containing methionine, methionyl tRNA synthetase (MetRS), translation initiation tRNA for methionine, formyl donor or methionyl tRNA transferase
- E) Step of providing a peptide sequence-encoding template DNA library having, downstream of a promoter, a translation initiation codon ATG followed by a cysteine codon and a further downstream codon corresponding to the anticodon of the tRNA of Step C)
- F) Step of providing an mRNA library from the template DNA library of Step E)
- G) Step of conjugating spacers to the 3'-ends of the mRNA library of Step F)
- H) Step of adding the spacer-conjugated mRNA library of Step G) to the cell-free translation system of Step D), followed by translation to provide an uncyclized peptide compound-mRNA complex display library
- I) Step of forming cyclic structures, followed by desulfurization reaction The method of the present invention can comprise a step of carrying out a step of synthesizing cDNAs by primers annealing to the 3'-regions of the mRNA library following Step G). The method of the present invention can further comprise the following steps:
- J) Step of enriching sequences in mRNA that bind to a drug target by panning
- K) Step of synthesizing cDNA by reverse transcriptase
- L) Step of analyzing the nucleotide sequence

[IV] Alternatively, the method for preparing a peptide compound having a cyclic portion according to the present invention can comprise one or more of the following steps:
- A) Step of providing an aminoacylated pdCpA of Compound C-3 (R2=R3=R28=R29=H, L-aspartic acid derivative)
- B) Step of providing a tRNA deficient in 3'-terminal CA
- C) Step of linking the pdCpA of Step A) to the tRNA of Step B) to provide an aminoacylated initiation tRNA of Compound C-3
- D) Step of providing a cell-free translation system containing the tRNA of Step C)
- E) Step of providing a peptide sequence-encoding template DNA library having, downstream of a promoter, a translation initiation codon ATG followed by a cysteine codon and a further downstream codon corresponding to the anticodon of the tRNA of Step C)
- F) Step of providing an mRNA library from the template DNA library of Step E)
- G) Step of conjugating spacers to the 3'-ends of the mRNA library of Step F)
- H) Step of adding the spacer-conjugated mRNA library of Step G) to the cell-free translation system of Step D), followed by translation to provide an uncyclized peptide compound-mRNA complex display library
- I) Step of allowing peptide deformylase and methionine aminopeptidase to act on the library of Step H)

Steps H and I can be carried out simultaneously by adding peptide deformylase and methionine aminopeptidase to the system at the time of translation.
- I) Step of forming cyclic structures, followed by desulfurization reaction The method of the present invention can comprise a step of carrying out a step of synthesizing cDNAs by primers annealing to the 3'-regions of the mRNA library following Step G). The method of the present invention can further comprise the following steps:
- J) Step of enriching sequences in mRNA library that bind to a drug target by panning
- K) Step of synthesizing cDNA by reverse transcriptase
- L) Step of analyzing the nucleotide sequence

[V-1] Introduction of an amino acid, amino acid analog or N-terminal carboxylic acid analog other than methionine into the N-terminal Alternatively, the method for preparing a peptide compound having a cyclic portion according to the present invention relates to a method for constructing an amide-cyclized peptide compound library that can be carried out by placing, at the N-terminal, tBSSEtGABA or tBSSEtβAla less acceptable to translation elongation reaction, the method comprising one or more of the following steps:
  A) Step of providing an aminoacylated pdCpA of tBSSEtGABA or tBSSEtβAla
  B) Step of providing an initiation tRNA deficient in 3'-terminal CA
  C) Step of linking the pdCpA of Step A) to the initiation tRNA of Step B) to provide an aminoacylated initiation tRNA of tBSSEtGABA or tBSSEtβAla
  D) Step of providing an aminoacylated pdCpA of Compound C-1
  E) Step of providing a tRNA deficient in 3'-terminal CA
  F) Step of linking the pdCpA of Step D) to the 3'-terminal tRNA of Step E) to provide an aminoacylated tRNA of Compound C-1
  G) Step of providing a cell-free translation system containing the initiation tRNA of Step C) and the tRNA of Step F) and not containing methionine, methionyl tRNA synthetase (MetRS), translation initiation tRNA for methionine, formyl donor or methionyl tRNA transferase
  H) Step of providing a peptide sequence-encoding template DNA library having ATG as the first codon downstream of a promoter and further comprising, downstream thereof, a codon corresponding to the anticodon of the tRNA of Step F), and on the 3' side thereof, a codon for proline or N-methylamino acid serving as another ARS substrate
  I) Step of providing an mRNA library from the template DNA library of Step H)
  J) Step of conjugating spacers to the 3'-ends of the mRNA library of Step I)
  K) Step of adding the spacer-conjugated mRNA library of Step J) to the cell-free translation system of Step G), followed by translation to provide an uncyclized peptide compound-mRNA complex display library
  L) Step of forming cyclic sites and linear sites 2

The method of the present invention can comprise a step of synthesizing cDNAs by primers annealing to the 3'-regions of the mRNA library following Step J). The method of the present invention can further comprise the following steps:
  M) Step of enriching sequences in mRNA library that bind to a drug target by panning
  N) Step of synthesizing cDNA by reverse transcriptase
  O) Step of analyzing the nucleotide sequence

[V-2] Introduction of an amino acid, amino acid analog or N-terminal carboxylic acid analog other than methionine into the N-terminal Alternatively, the method for preparing a peptide compound having a cyclic portion according to the present invention relates to a method for constructing an amide-cyclized peptide compound library that can be carried out by placing, at the N-terminal, tBSSEtGABA or tBSSEtβAla less acceptable to translation elongation reaction, the method comprising one or more of the following steps:
  A) Step of providing an aminoacylated pdCpA of tBSSEtGABA or tBSSEtβAla
  B) Step of providing an initiation tRNA deficient in 3'-terminal CA
  C) Step of linking the pdCpA of Step A) to the initiation tRNA of Step B) to provide an aminoacylated initiation tRNA of tBSSEtGABA or tBSSEtβAla
  D) Step of providing an aminoacylated pdCpA of Compound C-1
  E) Step of providing a tRNA deficient in 3'-terminal CA
  F) Step of linking the pdCpA of Step D) to the 3'-terminal tRNA of Step E) to provide an aminoacylated tRNA of Compound C-1, providing an aminoacylated pdCpA of an arbitrary N-methylamino acid, then providing a tRNA deficient in 3'-terminal CA, and linking the pdCpA to the tRNA to provide an aminoacylated tRNA of the N-methylamino acid
  G) Step of providing a cell-free translation system containing the initiation tRNA of Step C) and the tRNAs of Step F) and not containing methionine, methionyl tRNA synthetase (MetRS), translation initiation tRNA for methionine, formyl donor or methionyl tRNA transferase
  H) Step of providing a peptide sequence-encoding template DNA library having ATG as the first codon downstream of a promoter and further comprising, downstream thereof, a codon corresponding to the anticodon of the tRNA of Step F), and on the 3' side thereof, a codon for the N-methylaminoacylated tRNA of Step F)
  I) Step of providing an mRNA library from the template DNA library of Step H)
  J) Step of conjugating spacers to the 3'-ends of the mRNA library of Step I)
  K) Step of adding the spacer-conjugated mRNA library of Step J) to the cell-free translation system of Step G), followed by translation to provide an uncyclized peptide compound-mRNA complex display library
  L) Step of forming cyclic sites and linear sites 2

The method of the present invention can comprise a step of synthesizing cDNAs by primers annealing to the 3'-regions of the mRNA library following Step J). The method of the present invention can further comprise the following steps:
  M) Step of enriching sequences in mRNA library that bind to a drug target by panning
  N) Step of synthesizing cDNA by reverse transcriptase
  O) Step of analyzing the nucleotide sequence

[VI-1] Introduction of an amino acid, amino acid analog or N-terminal carboxylic acid analog other than methionine into the N-terminal Alternatively, the method for preparing a peptide compound having a cyclic portion according to the present invention relates to a method for constructing an amide-cyclized peptide compound library that can be carried out by placing, at the N-terminal, tBSSEtGABA or tBSSEtβAla less acceptable to translation elongation reaction, the method comprising one or more of the following steps:
  A) Step of providing an aminoacylated pdCpA of tBSSEtGABA or tBSSEtβAla
  B) Step of providing an initiation tRNA deficient in 3'-terminal CA
  C) Step of linking the pdCpA of Step A) to the initiation tRNA of Step B) to provide an aminoacylated initiation tRNA of tBSSEtGABA or tBSSEtβAla
  D) Step of providing an aminoacylated pdCpA of Asp (SBn)
  E) Step of providing a tRNA deficient in 3'-terminal CA
  F) Step of linking the pdCpA of Step D) to the 3'-terminal tRNA of Step E) to provide an aminoacylated tRNA of Asp (SBn)
  G) Step of providing a cell-free translation system containing the initiation tRNA of Step C) and the tRNA of Step F) and not containing methionine, methionyl tRNA synthetase (MetRS), translation initiation tRNA for methionine, formyl donor or methionyl tRNA transferase H) Step of providing a peptide sequence-encoding template DNA library having ATG as the first codon downstream of a promoter and further comprising, downstream thereof, a codon corresponding to the anticodon of the tRNA of Step F), and on the 3' side thereof, a codon for proline or N-methylamino acid serving as another ARS substrate I) Step of providing an mRNA library from the template DNA library of Step H)

J) Step of conjugating spacers to the 3'-ends of the mRNA library of Step I)

K) Step of adding the spacer-conjugated mRNA library of Step J) to the cell-free translation system of Step G), followed by translation to provide an uncyclized peptide compound-mRNA complex display library L) Step of forming cyclic sites and linear sites 2

The method of the present invention can comprise a step of synthesizing cDNAs by primers annealing to the 3'-regions of the mRNA library following Step J). The method of the present invention can further comprise the following steps:

M) Step of enriching sequences in mRNA library that bind to a drug target by panning N) Step of synthesizing cDNA by reverse transcriptase O) Step of analyzing the nucleotide sequence

[VI-2] Introduction of an amino acid, amino acid analog or N-terminal carboxylic acid analog other than methionine into the N-terminal Alternatively, the method for preparing a peptide compound having a cyclic portion according to the present invention relates to a method for constructing an amide-cyclized peptide compound library that can be carried out by placing, at the N-terminal, tBSSEtGABA or tBSSEtβAla less acceptable to translation elongation reaction, the method comprising one or more of the following steps:

A) Step of providing an aminoacylated pdCpA of tBSSEtGABA or tBSSEtβAla

B) Step of providing an initiation tRNA deficient in 3'-terminal CA

C) Step of linking the pdCpA of Step A) to the initiation tRNA of Step B) to provide an aminoacylated initiation tRNA of tBSSEtGABA or tBSSEtβAla D) Step of providing an aminoacylated pdCpA of Asp (SBn)

E) Step of providing a tRNA deficient in 3'-terminal CA

F) Step of linking the pdCpA of Step D) to the 3'-terminal tRNA of Step E) to provide an aminoacylated tRNA of Asp(SBn), providing an aminoacylated pdCpA of an arbitrary N-methylamino acid, then providing a tRNA deficient in 3'-terminal CA, and linking the pdCpA to the tRNA to provide an aminoacylated tRNA of the N-methylamino acid G) Step of providing a cell-free translation system containing the initiation tRNA of Step C) and the tRNAs of Step F) and not containing methionine, methionyl tRNA synthetase (MetRS), translation initiation tRNA for methionine, formyl donor or methionyl tRNA transferase H) Step of providing a peptide sequence-encoding template DNA library having ATG as the first codon downstream of a promoter and further comprising, downstream thereof, a codon corresponding to the anticodon of the tRNA of Step F) and on the 3' side thereof, a codon for the N-methylaminoacylated tRNA of Step F)

I) Step of providing an mRNA library from the template DNA library of Step H)

J) Step of conjugating spacers to the 3'-ends of the mRNA library of Step I)

K) Step of adding the spacer-conjugated mRNA library of Step J) to the cell-free translation system of Step G), followed by translation to provide an uncyclized peptide compound-mRNA complex display library L) Step of forming cyclic sites and linear sites 2

The method of the present invention can comprise a step of synthesizing cDNAs by primers annealing to the 3'-regions of the mRNA library following Step J). The method of the present invention can further comprise the following steps:

M) Step of enriching sequences in mRNA library that bind to a drug target by panning N) Step of synthesizing cDNA by reverse transcriptase O) Step of analyzing the nucleotide sequence

[VII-1] Introduction of an amino acid, amino acid analog or N-terminal carboxylic acid analog other than methionine into the N-terminal Alternatively, the method for preparing a peptide compound having a cyclic portion according to the present invention relates to a method for constructing an amide-cyclized peptide library that can be carried out by placing, at the N-terminal, an amino acid less acceptable to translation elongation reaction, the method comprising one or more of the following steps:

A) Step of providing an aminoacylated pdCpA of Compound N-1

B) Step of providing an initiation tRNA deficient in 3'-terminal CA

C) Step of linking the pdCpA of Step A) to the initiation tRNA of Step B) to provide an aminoacylated initiation tRNA of Compound N-1 or N-2

D) Step of providing an aminoacylated pdCpA of Compound C-1

E) Step of providing a tRNA deficient in 3'-terminal CA

F) Step of linking the pdCpA of Step D) to the tRNA of Step E) to provide an aminoacylated tRNA of Compound C-1

G) Step of providing a cell-free translation system containing the initiation tRNA of Step C) and the tRNA of Step F) and not containing methionine, methionyl tRNA synthetase (MetRS), translation initiation tRNA for methionine, formyl donor or methionyl tRNA transferase H) Step of providing a peptide sequence-encoding template DNA library having a codon corresponding to the anticodon of the translation initiation tRNA of Step C) as the first codon downstream of a promoter and further comprising, downstream thereof, a codon corresponding to the anticodon of the tRNA of Step F)

I) Step of providing an mRNA library from the template DNA library of Step H)

J) Step of conjugating spacers to the 3'-ends of the mRNA library of Step I)

K) Step of adding the spacer-conjugated mRNA library of Step J) to the cell-free translation system of Step G), followed by translation to provide an uncyclized peptide compound-mRNA complex display library L) Step of forming cyclic sites The method of the present invention can comprise a step of carrying out a step of synthesizing cDNAs by primers annealing to the 3'-regions of the mRNA library following Step J). The method of the present invention can further comprise the following steps:

M) Step of enriching a target substance-bound mRNA library by panning

N) Step of synthesizing cDNA by reverse transcriptase

O) Step of analyzing the nucleotide sequence

[VII-2] Introduction of an amino acid, amino acid analog or N-terminal carboxylic acid analog other than methionine into the N-terminal Alternatively, the method for preparing a peptide compound having a cyclic portion according to the present invention relates to a method for constructing an amide-cyclized peptide library that can be carried out by placing, at the N-terminal, an amino acid less acceptable to translation elongation reaction, the method comprising one or more of the following steps:

A) Step of providing an aminoacylated pdCpA of Compound N-2

B) Step of providing an initiation tRNA deficient in 3'-terminal CA

C) Step of linking the pdCpA of Step A) to the initiation tRNA of Step B) to provide an aminoacylated initiation tRNA of Compound N-1 or N-2

D) Step of providing an aminoacylated pdCpA of Compound C-1

E) Step of providing a tRNA deficient in 3'-terminal CA

F) Step of linking the pdCpA of Step D) to the tRNA of Step E) to provide an aminoacylated tRNA of Compound C-1

G) Step of providing a cell-free translation system containing the initiation tRNA of Step C) and the tRNA of Step F) and not containing methionine, methionyl tRNA synthetase (MetRS), translation initiation tRNA for methionine, formyl donor or methionyl tRNA transferase H) Step of providing a peptide sequence-encoding template DNA library having a codon corresponding to the anticodon of the translation initiation tRNA of Step C) as the first codon downstream of a promoter and further comprising, downstream thereof, a codon corresponding to the anticodon of the tRNA of Step F), and on the 3' side thereof, a codon for proline or N-methylamino acid serving as another ARS substrate I) Step of providing an mRNA library from the template DNA library of Step H)

J) Step of conjugating spacers to the 3'-ends of the mRNA library of Step I)

K) Step of adding the spacer-conjugated mRNA library of Step J) to the cell-free translation system of Step G), followed by translation to provide an uncyclized peptide compound-mRNA complex display library L) Step of forming cyclic sites The method of the present invention can comprise a step of carrying out a step of synthesizing cDNAs by primers annealing to the 3'-regions of the mRNA library following Step J). The method of the present invention can further comprise the following steps:

M) Step of enriching sequences in mRNA library that bind to a drug target by panning N) Step of synthesizing cDNA by reverse transcriptase O) Step of analyzing the nucleotide sequence

[VII-3] Introduction of an amino acid, amino acid analog or N-terminal carboxylic acid analog other than methionine into the N-terminal Alternatively, the method for preparing a peptide compound having a cyclic portion according to the present invention relates to a method for constructing an amide-cyclized peptide library that can be carried out by placing, at the N-terminal, an amino acid less acceptable to translation elongation reaction, the method comprising one or more of the following steps:

A) Step of providing an aminoacylated pdCpA of Compound N-2

B) Step of providing an initiation tRNA deficient in 3'-terminal CA

C) Step of linking the pdCpA of Step A) to the initiation tRNA of Step B) to provide an aminoacylated initiation tRNA of Compound N-1 or N-2

D) Step of providing an aminoacylated pdCpA of Compound C-1

E) Step of providing a tRNA deficient in 3'-terminal CA

F) Step of linking the pdCpA of Step D) to the tRNA of Step E) to provide an aminoacylated tRNA of Compound C-1, Step of further providing an aminoacylated pdCpA of an arbitrary N-methylamino acid, Step of further providing a tRNA deficient in 3'-terminal CA, and Step of linking the pdCpA to the tRNA to provide an aminoacylated tRNA of the N-methylamino acid G) Step of providing a cell-free translation system containing the initiation tRNA of Step C) and the tRNAs of Step F) and not containing methionine, methionyl tRNA synthetase (MetRS), translation initiation tRNA for methionine, formyl donor or methionyl tRNA transferase H) Step of providing a peptide sequence-encoding template DNA library having a codon corresponding to the anticodon of the translation initiation tRNA of Step C) as the first codon downstream of a promoter and further comprising, downstream thereof, a codon corresponding to the anticodon of the tRNA of Step F), and on the 3' side thereof, a codon for the N-methylaminoacylated tRNA of Step F)

I) Step of providing an mRNA library from the template DNA library of Step H)

J) Step of conjugating spacers to the 3'-ends of the mRNA library of Step I)

K) Step of adding the spacer-conjugated mRNA library of Step J) to the cell-free translation system of Step G), followed by translation to provide an uncyclized peptide compound-mRNA complex display library L) Step of forming cyclic sites The method of the present invention can comprise a step of carrying out a step of synthesizing cDNAs by primers annealing to the 3'-regions of the mRNA library following Step J). The method of the present invention can further comprise the following steps:

M) Step of enriching sequences in mRNA library that bind to a drug target by panning N) Step of synthesizing cDNA by reverse transcriptase O) Step of analyzing the nucleotide sequence

[VIII-1] Cyclization of a peptide having an N-terminal amino acid other than methionine Alternatively, the method for preparing a peptide compound having a cyclic portion according to the present invention relates to a method for constructing an amide-cyclized peptide library with different structures of cyclization sites that can be carried out by simultaneously translating plural types of peptides differing in N-terminal amino acid, the method comprising one or more of the following steps:

A) Step of providing an aminoacylated pdCpA of Compound C-X (in the present specification, "Compound C-X" refers to any compound selected from Compounds C-1, C-2 and C-3; the same holds true for the description below herein)

B) Step of providing a tRNA deficient in 3'-terminal CA

C) Step of linking the pdCpA of Step A) to the tRNA of Step B) above to provide an aminoacylated initiation tRNA of Compound C-X
D) Step of providing a cell-free translation system containing the tRNA of Step C)
E) Step of providing a peptide sequence-encoding template DNA library comprising, downstream of a promoter, a codon corresponding to the anticodon of the tRNA of Step C), and midstream on the 3' side thereof, a codon for proline or N-methyl amino acid serving as another ARS substrate
F) Step of providing an mRNA library from the template DNA library of Step E)
G) Step of conjugating spacers to the 3'-ends of the mRNA library of Step F)
H) Step of adding the spacer-conjugated mRNA library of Step G) to the cell-free translation system of Step D), followed by translation to provide an uncyclized peptide compound-mRNA complex display library
I) Step of allowing peptide deformylase and methionine aminopeptidase to act on the library of Step H)

Steps H and I can be carried out simultaneously by adding peptide deformylase and methionine aminopeptidase to the system at the time of translation.

J) Step of forming cyclic structures

In the formation of cyclic structures, desulfurization reaction can be performed, if necessary. The method of the present invention can also comprise a step of synthesizing cDNAs by primers annealing to the 3'-regions of the mRNA library following Step H) or Step I.

The method of the present invention can further comprise the following steps:
J) Step of enriching sequences in mRNA library that bind to a drug target by panning
K) Step of synthesizing cDNA by reverse transcriptase
L) Step of analyzing the nucleotide sequence

[IX] Cyclization of a peptide having glycine, alanine or phenylalanine at the N-terminal Alternatively, the method for preparing a peptide compound having a cyclic portion according to the present invention relates to a method for constructing an amide-cyclized peptide library with different structures of cyclization sites that can be carried out by simultaneously translating plural types of peptides differing in N-terminal amino acid, the method comprising one or more of the following steps:
A) Step of providing an aminoacylated pdCpA of Compound C-X
B) Step of providing a tRNA deficient in 3'-terminal CA
C) Step of linking the pdCpA of Step A) to the tRNA of Step B) above to provide an aminoacylated initiation tRNA of Compound C-X
D) Step of providing a cell-free translation system containing the tRNA of Step C)
E) Step of providing a peptide sequence-encoding template DNA library comprising, downstream of a promoter, translation initiation ATG immediately followed by a codon for any of glycine, alanine and phenylalanine, and a codon corresponding to the anticodon of the tRNA of Step C), and midstream on the 3' side thereof, a codon for proline or N-methylamino acid serving as another ARS substrate
F) Step of providing an mRNA library from the template DNA library of Step E)
G) Step of conjugating spacers to the 3'-ends of the mRNA library of Step F)
H) Step of adding the spacer-conjugated mRNA library of Step G) to the cell-free translation system of Step D), followed by translation to provide an uncyclized peptide compound-mRNA complex display library
I) Step of allowing peptide deformylase and methionine aminopeptidase to act on the library of Step H)

Steps H and I can be carried out simultaneously by adding peptide deformylase and methionine aminopeptidase to the system at the time of translation.

J) Step of forming cyclic structures

In the formation of cyclic structures, desulfurization reaction can be performed, if necessary. The method of the present invention can also comprise a step of synthesizing cDNAs by primers annealing to the 3'-regions of the mRNA library following Step H) or Step I)

The method of the present invention can further comprise the following steps:
J) Step of enriching sequences in mRNA library that bind to a drug target by panning
K) Step of synthesizing cDNA by reverse transcriptase
L) Step of analyzing the nucleotide sequence

[X] Cyclization of a peptide having an N-terminal amino acid other than methionine Alternatively, the method for preparing a peptide compound having a cyclic portion according to the present invention relates to a method for constructing an amide-cyclized peptide library with different structures of cyclization sites that can be carried out by simultaneously translating plural types of peptides differing in N-terminal amino acid, the method comprising one or more of the following steps:
A) Step of providing an aminoacylated pdCpA of Asp (SBn)
B) Step of providing a tRNA deficient in 3'-terminal CA
C) Step of linking the pdCpA of Step A) to the tRNA of Step B) above to provide an aminoacylated initiation tRNA of Asp (SBn)
D) Step of providing a cell-free translation system containing the tRNA of Step C)
E) Step of providing a peptide sequence-encoding template DNA library comprising, downstream of a promoter, a codon corresponding to the anticodon of the tRNA of Step C), and midstream on the 3' side thereof, a codon for proline or N-methylamino acid serving as another ARS substrate
F) Step of providing an mRNA library from the template DNA library of Step E)
G) Step of conjugating spacers to the 3'-ends of the mRNA library of Step F)
H) Step of adding the spacer-conjugated mRNA library of Step G) to the cell-free translation system of Step D), followed by translation to provide an uncyclized peptide compound-mRNA complex display library
I) Step of allowing peptide deformylase and methionine aminopeptidase to act on the library of Step H)

Steps H and I can be carried out simultaneously by adding peptide deformylase and methionine aminopeptidase to the system at the time of translation.

J) Step of forming cyclic structures

In the formation of cyclic structures, desulfurization reaction can be performed, if necessary. The method of the present invention can also comprise a step of synthesizing cDNAs by primers annealing to the 3'-regions of the mRNA library following Step H) or Step The method of the present invention can further comprise the following steps:

J) Step of enriching sequences in mRNA library that bind to a drug target by panning K) Step of synthesizing cDNA by reverse transcriptase L) Step of analyzing the nucleotide sequence

[XI] Alternatively, the method for preparing a peptide compound having a cyclic portion according to the present invention relates to a method for constructing a cyclic and branched peptide library, the method comprising one or more of the following steps:

A) Step of providing an aminoacylated pdCpA of Compound N-1 or N-2

B) Step of providing an initiation tRNA deficient in 3'-terminal CA

C) Step of linking the pdCpA of Step A) to the initiation tRNA of Step B) to provide an aminoacylated initiation tRNA of Compound N-1 or N-2

D) Step of providing an aminoacylated pdCpA of Compound C-1

E) Step of providing a tRNA deficient in 3'-terminal CA

F) Step of linking the pdCpA of Step D) to the tRNA of Step E) to provide an aminoacylated tRNA of Compound C-1

G) Step of providing a cell-free translation system containing the initiation tRNA of Step C) and the tRNA of Step F) and not containing methionine, methionyl tRNA synthetase (MetRS), translation initiation tRNA for methionine, formyl donor or methionyl tRNA transferase H) Step of providing a peptide sequence-encoding template DNA library having a codon corresponding to the anticodon of the translation initiation tRNA of Step C) as the first codon downstream of a promoter and further comprising, downstream thereof, 0 to 2 arbitrary codons flanked by a HOGly codon and a lysine codon (alanine is on the side closer to the N-terminal), and a further downstream codon corresponding to the anticodon of the tRNA of Step F), and (provided that an SH group in Compound N-1 or N-2 is protected) on the 3' side thereof, a codon for proline or N-methylamino acid serving as another ARS substrate I) Step of providing an mRNA library from the template DNA library of Step H)

J) Step of conjugating spacers to the 3'-ends of the mRNA library of Step I)

K) Step of adding the spacer-conjugated mRNA library of Step J) to the cell-free translation system of Step J), followed by translation to provide an uncyclized peptide compound-mRNA complex peptide display library L) Step of forming cyclic portions M) Step of activating an ester formed by HOGly and the immediately preceding amino acid on the N-terminal side thereof to generate a thioester N) Step of forming an amide bond between the thioester and the lysine side chain amino group to generate linear site 2

The method of the present invention can comprise a step of carrying out a step of synthesizing cDNAs by primers annealing to the 3'-regions of the mRNA library following Step J). The method of the present invention can further comprise the following steps:

O) Step of enriching sequences in mRNA library that bind to a drug target by panning P) Step of synthesizing cDNA by reverse transcriptase Q) Step of analyzing the nucleotide sequence

[XII] Alternatively, the method for preparing a peptide compound having a cyclic portion according to the present invention relates to a method for constructing a cyclic and branched peptide library, the method comprising one or more of the following steps:

A) Step of providing an aminoacylated pdCpA of Compound N-1 or N-2

B) Step of providing a tRNA deficient in 3'-terminal CA

C) Step of linking the pdCpA of Step A) to the tRNA of Step B) to provide an aminoacylated tRNA of Compound N-1 or N-2

D) Step of providing an aminoacylated pdCpA of Compound C-1

E) Step of providing a tRNA deficient in 3'-terminal CA

F) Step of linking the pdCpA of Step D) to the tRNA of Step E) to provide an aminoacylated tRNA of Compound C-1

G) Step of providing a cell-free translation system containing the tRNA of Step C), the tRNA of Step F) and lactic acid H) Step of providing a peptide sequence-encoding template DNA library having a codon corresponding to the anticodon of the tRNA of Step C) as the 2nd codon downstream of a promoter and further comprising, downstream thereof, codons for a sequence cysteine-proline-lactic acid, a further downstream lysine codon and a further downstream codon corresponding to the anticodon of the tRNA of Step F), and (provided that an SH group in Compound N-1 or N-2 is protected) on the 3' side thereof, a codon for proline or N-methylamino acid serving as another ARS substrate I) Step of providing an mRNA library from the template DNA library of Step H)

J) Step of conjugating spacers to the 3'-ends of the mRNA library of Step I)

K) Step of adding the spacer-conjugated mRNA library of Step J) to the cell-free translation system of Step J), followed by translation to provide an uncyclized peptide compound-mRNA complex peptide display library L) Step of forming cyclic portions M) Step of generating an active thioester from the cysteine, proline and lactic acid sites N) Step of forming an amide bond between the generated active thioester and the lysine side chain amino group to generate linear site 2, followed by desulfurization reaction The method of the present invention can comprise a step of carrying out a step of synthesizing cDNAs by primers annealing to the 3'-regions of the mRNA library following Step J). The method of the present invention can further comprise the following steps:

O) Step of enriching sequences in mRNA library that bind to a drug target by panning P) Step of synthesizing cDNA by reverse transcriptase Q) Step of analyzing the nucleotide sequence

[XIII] Alternatively, the method for preparing a peptide compound having a cyclic portion according to the present invention relates to a method for constructing a cyclic and branched peptide library, the method comprising one or more of the following steps:

A) Step of providing an aminoacylated pdCpA of Compound N-1 or N-2

B) Step of providing a tRNA deficient in 3'-terminal CA

C) Step of linking the pdCpA of Step A) to the tRNA of Step B) to provide an aminoacylated tRNA of Compound N-1 or N-2

D) Step of providing an aminoacylated pdCpA of Compound C-1

E) Step of providing a tRNA deficient in 3'-terminal CA

F) Step of linking the pdCpA of Step D) to the tRNA of Step E) to provide an aminoacylated tRNA of Compound C-1

G) Step of providing a cell-free translation system containing the tRNA of Step C), the tRNA of Step F) and lactic acid H) Step of providing a peptide sequence-encoding template DNA library having a codon corresponding to the anticodon of the tRNA of Step C) as the 2nd codon downstream of a promoter and further comprising, downstream thereof, codons for a sequence cysteine-proline-lactic acid, a further downstream lysine codon and a further downstream codon corresponding to the anticodon of the tRNA of Step F), and on the 3' side thereof, a codon for proline or N-methylamino acid serving as another ARS substrate I) Step of providing an mRNA library from the template DNA library of Step H)

J) Step of conjugating spacers to the 3'-ends of the mRNA library of Step I)

K) Step of adding the spacer-conjugated mRNA library of Step J) to the cell-free translation system of Step J), followed by translation to provide an uncyclized peptide compound-mRNA complex peptide display library L) Step of allowing peptide deformylase and methionine aminopeptidase to act on the library of Step K)

Steps K and L can be carried out simultaneously by adding peptide deformylase and methionine aminopeptidase to the system at the time of translation.

M) Step of forming cyclic structures

In the formation of cyclic structures, desulfurization reaction can be performed, if necessary.

N) Step of generating an active thioester from the cysteine, proline and lactic acid units O) Step of converting the generated carboxylic acid to active ester and forming an amide bond between the active ester and the lysine side chain amino group to generate linear site 2, followed by optional desulfurization reaction The method of the present invention can comprise a step of carrying out a step of synthesizing cDNAs by primers annealing to the 3'-regions of the mRNA library following Step J). The method of the present invention can further comprise the following steps:

P) Step of enriching sequences in mRNA library that bind to a drug target by panning P) Step of synthesizing cDNA by reverse transcriptase Q) Step of analyzing the nucleotide sequence

[XIV] Alternatively, the method for preparing a peptide compound having a cyclic portion according to the present invention relates to a method for constructing a cyclic and branched peptide library, the method comprising one or more of the following steps:

A) Step of providing an aminoacylated pdCpA of Compound C-1

E) Step of providing a tRNA deficient in 3'-terminal CA

F) Step of linking the pdCpA of Step D) to the tRNA of Step E) to provide an aminoacylated tRNA of Compound C-1

G) Step of providing a cell-free translation system containing the tRNA of Step C), the tRNA of Step F) and lactic acid H) Step of providing a peptide sequence-encoding template DNA library having a cysteine codon as the 2nd codon downstream of a promoter and further comprising, downstream thereof, codons for a sequence cysteine-proline-lactic acid, a codon for protected amine Compound Na-4, and a further downstream codon corresponding to the anticodon of the tRNA of Step F), and on the 3' side thereof, a codon for proline or N-methylamino acid serving as another ARS substrate I) Step of providing an mRNA library from the template DNA library of Step H)

J) Step of conjugating spacers to the 3'-ends of the mRNA library of Step I)

K) Step of adding the spacer-conjugated mRNA library of Step J) to the cell-free translation system of Step J), followed by translation to provide an uncyclized peptide compound-mRNA complex peptide display library L) Step of forming cyclic portions M) Step of deprotecting the side chain amino group of Compound Na-4, and Step of generating an active thioester from the cysteine, proline and lactic acid units N) Step of forming an amide bond between the generated active thioester and the side chain amino group of Compound Na-4 to form linear site 2

The method of the present invention can comprise a step of carrying out a step of synthesizing cDNAs by primers annealing to the 3'-regions of the mRNA library following Step J). The method of the present invention can further comprise the following steps:

O) Step of enriching sequences in mRNA library that bind to a drug target by panning P) Step of synthesizing cDNA by reverse transcriptase Q) Step of analyzing the nucleotide sequence

[XV] Alternatively, the method for preparing a peptide compound having a cyclic portion according to the present invention relates to a method for constructing a cyclic and branched peptide library, the method comprising one or more of the following steps:

A) Step of providing an aminoacylated pdCpA of Compound N-1 or N-2

B) Step of providing a tRNA deficient in 3'-terminal CA

C) Step of linking the pdCpA of Step A) to the tRNA of Step B) to provide an aminoacylated tRNA of Compound N-1 or N-2

D) Step of providing an aminoacylated pdCpA of Compound C-1

E) Step of providing a tRNA deficient in 3'-terminal CA

F) Step of linking the pdCpA of Step D) to the tRNA of Step E) to provide an aminoacylated tRNA of Compound C-1

G) Step of providing an aminoacylated pdCpA of Compound Na-4 or Compound Na-10 (Na-7 group) or Compound Na-11 (Na-7 group) having a protected amino group and optionally protected thiol group H) Step of providing a tRNA deficient in 3'-terminal CA I) Step of linking the pdCpA of Step G) to the tRNA of Step H) to provide an aminoacylated tRNA of Compound Na-4 or Compound Na-10 (Na-7 group) or Compound Na-11 (Na-7 group) having a protected amino group and optionally protected thiol group J) Step of providing a cell-free translation system containing the tRNA of Step C), the tRNA of Step F) and the tRNA of Step I)

K) Step of providing a peptide sequence-encoding template DNA library having a codon corresponding to the anticodon of the tRNA of Step C) as the 2nd codon downstream of a promoter and further comprising, downstream thereof, codons corresponding to the anticodons of tRNAs of Cys, Pro and lactic acid, a further downstream codon corresponding to the anticodon of the tRNA of Step G), a further downstream codon corresponding to the anticodon of the tRNA of Step D), and on the 3' side thereof, a codon for proline or N-methylamino acid serving as another ARS substrate L) Step of providing an mRNA library from the template DNA library of Step K)

M) Step of conjugating spacers to the 3'-ends of the mRNA library of Step L)

N) Step of adding the spacer-conjugated mRNA library of Step J) to the cell-free translation system of Step M), followed by translation to provide an uncyclized peptide compound-mRNA complex peptide display library O) Step of allowing peptide deformylase and methionine aminopeptidase to act on the library of Step K)

Steps K and L can be carried out simultaneously by adding peptide deformylase and methionine aminopeptidase to the system at the time of translation.

P) Step of forming cyclic structures

Q) Step of deprotecting Compound Na-4 or Compound Na-10 (Na-7 group) or Compound Na-11 (Na-7 group) having a protected amino group and optionally protected thiol group R) Step of generating linear site 2

In the formation of cyclic structures, desulfurization reaction can be performed, if necessary.

The method of the present invention can comprise a step of carrying out a step of synthesizing cDNAs by primers annealing to the 3'-regions of the mRNA library following Step J). The method of the present invention can further comprise the following steps:

S) Step of enriching sequences in mRNA library that bind to a drug target by panning T) Step of synthesizing cDNA by reverse transcriptase U) Step of analyzing the nucleotide sequence The peptide having Compound N-1 or N-2 at the N-terminal in the above methods[XIII] and [XV] may be prepared in the same way as the above method[XII].

[XVI] The present invention also relates to a method for constructing a cyclic and branched peptide library by the cyclization of a peptide having an N-terminal amino acid other than methionine, the method comprising one or more of the steps described below. The method for preparing a peptide compound having a cyclic portion according to the present invention relates to a method for constructing an amide-cyclized peptide library with different structures of cyclization sites that can be carried out by simultaneously translating plural types of peptides differing in N-terminal amino acid, the method comprising one or more of the following steps:

A) Step of providing an aminoacylated pdCpA of Compound C-1

B) Step of providing a tRNA deficient in 3'-terminal CA

C) Step of linking the pdCpA of Step A) to the tRNA of Step B) to provide an aminoacylated tRNA of Compound C-1

D) Step of providing an aminoacylated pdCpA of Compound Na-4 or Compound Na-10 (Na-7 group) or Compound Na-11 (Na-7 group) having a protected amino group and optionally protected thiol group E) Step of providing a tRNA deficient in 3'-terminal CA F) Step of linking the pdCpA of Step D) to the tRNA of Step E) to provide an aminoacylated tRNA of Compound Na-4 or Compound Na-10 (Na-7 group) or Compound Na-11 (Na-7 group) having a protected amino group and optionally protected thiol group G) Step of providing a cell-free translation system containing the tRNA of Step C), the tRNA of Step F) and the tRNA of Step I)

H) Step of providing a peptide sequence-encoding template DNA library comprising, downstream of a promoter, a codon corresponding to the anticodon of the tRNA of Step F), further downstream codons corresponding to the anticodons of tRANs of Cys, Pro and lactic acid, a further downstream codon corresponding to the anticodon of the tRNA of Step C), and on the 3' side thereof, a codon for proline or N-methylamino acid serving as another ARS substrate I) Step of providing an mRNA library from the template DNA library of Step H)

J) Step of conjugating spacers to the 3'-ends of the mRNA library of Step I)

K) Step of adding the spacer-conjugated mRNA library of Step J) to the cell-free translation system of Step J), followed by translation to provide an uncyclized peptide compound-mRNA complex peptide display library L) Step of allowing peptide deformylase and methionine aminopeptidase to act on the library of Step K)

Steps K and L can be carried out simultaneously by adding peptide deformylase and methionine aminopeptidase to the system at the time of translation.

L) Step of forming cyclic structures

M) Step of deprotecting Compound Na-4 or Compound Na-10 (Na-7 group) or Compound Na-11 (Na-7 group) having a protected amino group and optionally protected thiol group N) Step of generating linear site 2

In the formation of cyclic structures, desulfurization reaction can be performed, if necessary.

The method of the present invention can comprise a step of carrying out a step of synthesizing cDNAs by primers annealing to the 3'-regions of the mRNA library following Step J). The method of the present invention can further comprise the following steps:

O) Step of enriching sequences in mRNA library that bind to a drug target by panning P) Step of synthesizing cDNA by reverse transcriptase Q) Step of analyzing the nucleotide sequence In Step G), normal leucine may be added in place of methionine.

[XVII] The present invention also relates to a method for constructing a cyclic and branched peptide library by the cyclization of a peptide having an N-terminal amino acid other than methionine, the method comprising one or more of the steps described below. The method for preparing a peptide compound having a cyclic portion according to the present invention relates to a method for constructing an amide-cyclized peptide library with different structures of cyclization sites that can be carried out by simultaneously translating plural types of peptides differing in N-terminal amino acid, the method comprising one or more of the following steps:

A) Step of providing an aminoacylated pdCpA of Compound C-1

B) Step of providing a tRNA deficient in 3'-terminal CA

C) Step of linking the pdCpA of Step A) to the tRNA of Step B) to provide an aminoacylated tRNA of Compound C-1

D) Step of providing an aminoacylated pdCpA of Compound Na-4 or Compound Na-10 (Na-7 group) or Compound Na-11 (Na-7 group) having a protected amino group and optionally protected thiol group E) Step of providing a tRNA deficient in 3'-terminal CA F) Step of linking the pdCpA of Step D) to the tRNA of Step E) to provide an aminoacylated tRNA of Compound Na-4 or Compound Na-10 (Na-7 group) or Compound Na-11 (Na-7 group) having a protected amino group and optionally protected thiol group G) Step of providing a cell-free translation system containing the tRNA of Step C), the tRNA of Step F) and lactic acid H) Step of providing a peptide sequence-encoding template DNA library having a codon corresponding to the anticodon of the tRNA of Step C) as the 2nd codon downstream of a promoter and further comprising, downstream thereof, codons for a sequence cysteine-proline-lactic acid, a further downstream codon corresponding to the anticodon of the tRNA of Step F), and on the 3' side thereof, a codon for proline or N-methylamino acid serving as another ARS substrate I) Step of providing an mRNA library from the template DNA library of Step H)

J) Step of conjugating spacers to the 3'-ends of the mRNA library of Step I)

K) Step of adding the spacer-conjugated mRNA library of Step J) to the cell-free translation system of Step J), followed by translation to provide an uncyclized peptide compound-mRNA complex peptide display library L) Step of allowing peptide deformylase and methionine aminopeptidase to act on the library of Step K)

Steps K and L can be carried out simultaneously by adding peptide deformylase and methionine aminopeptidase to the system at the time of translation.

M) Step of forming cyclic structures

In the formation of cyclic structures, desulfurization reaction can be performed, if necessary.

N) Step of deprotecting the side chain protecting group of Compound Na-4 or Compound Na-10 (Na-7 group) or Compound Na-11 (Na-7 group), and Step of generating an active thioester from the Cys, Pro and lactic acid units O) Step of forming an amide bond between the generated active thioester and the side chain amino group to form linear site 2

The method of the present invention can comprise a step of carrying out a step of synthesizing cDNAs by primers annealing to the 3'-regions of the mRNA library following Step J). The method of the present invention can further comprise the following steps:

P) Step of enriching sequences in mRNA library that bind to a drug target by panning Q) Step of synthesizing cDNA by reverse transcriptase R) Step of analyzing the nucleotide sequence In Step G), normal leucine may be added in place of methionine.

The preparation of aminoacyl-tRNAs is not limited to use of pdCpAs and also includes use of aminoacyl-tRNA synthetase, flexizyme, ultrasonic agitation method in cationic micelle, PNA-amino acid active ester method, etc.

Method for Suppressing Aspartimide Formation

In the translational incorporation of aspartic acid-type thioester, the thioester reacts with a hydrogen atom in an amide bond on the C-terminal side immediately following the thioester to form aspartimide. According to the method, however, the desired full-length peptide containing thioester can be translationally synthesized by introducing an amino acid having a N-alkyl group (e.g., proline) as an amino acid residue next to such a aspartic acid-type thioester to be translationally incorporated.

In the present specification, the "alkyl group" refers to a monovalent group derived from aliphatic hydrocarbon by removal of one arbitrary hydrogen atom and has a subset of a hydrocarbyl or hydrocarbon group structure containing neither heteroatoms nor unsaturated carbon-carbon bonds in the backbone and containing hydrogen and carbon atoms. Its carbon chain length n is in the range of 1 to 20. Examples of the alkyl group include "C1-C6 alkyl groups" and specifically include a methyl group, ethyl group, propyl group, butyl group, pentyl group, hexyl group, isopropyl group, t-butyl group, sec-butyl group, 1-methylpropyl group, 1,1-dimethylpropyl group, 2,2-dimethylpropyl group, 1,2-dimethylpropyl group, 1,1,2-trimethylpropyl group, 1,2,2-trimethylpropyl group, 1,1,2,2-tetramethylpropyl group, 1-methylbutyl group, 2-methylbutyl group, 3-methylbutyl group, 1,1-dimethylbutyl group, 1,2-dimethylbutyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethylbutyl group, 2-ethylbutyl group, isopentyl group and neopentyl group.

In the present specification, the "alkyl group" may include an "alkenyl group" and "alkynyl group" described include.

In the present specification, the "alkenyl group" refers to a monovalent group having at least one double bond (two adjacent SP2 carbon atoms). The double bond can assume entgegen (E) or zusammen (Z) and cis or trans geometric forms depending on the arrangement of the double bond and a substituent, if any. Examples of the alkenyl group include linear or branched alkenyl groups including straight chains containing internal olefins. Preferred examples thereof include C2-C10 alkenyl groups, more preferably C2-C6 alkenyl groups. Specific examples of such alkenyl include a vinyl group, allyl group, 1-propenyl group, 2-propenyl group, 1-butenyl group, 2-butenyl group (including cis and trans forms), 3-butenyl group, pentenyl group and hexenyl group.

In the present specification, the "alkynyl" refers to a monovalent group having at least one triple bond (two adjacent SP carbon atoms). Examples thereof include linear or branched alkynyl groups including internal alkylenes. Preferred examples thereof include C2-C10 alkynyl groups, more preferably C2-C6 alkynyl groups. Specific examples of such alkynyl include an ethynyl group, 1-propynyl group, propargyl group, 3-butynyl group, pentynyl group, hexynyl group, 3-phenyl-2-propynyl group, 3-(2'-fluorophenyl)-2-propynyl group, 2-hydroxy-2-propynyl group, 3-(3-fluorophenyl)-2-propynyl group and 3-methyl-(5-phenyl)-4-pentynyl group.

The "cycloalkyl group" means a saturated or partially saturated cyclic monovalent aliphatic hydrocarbon group containing a single ring, bicyclo ring or spiro ring. Preferred examples thereof include C3-C10 cycloalkyl groups. Specific examples of such cycloalkyl groups include a cyclopropyl group, cyclobutyl group, cyclopentyl group, cyclohexyl group, cycloheptyl group, cyclooctyl group and bicyclo[2.2.1]heptyl group.

The "C1-C6 alkyl group which optionally has halogen as a substituent" means a "C1-C6 alkyl group" substituted by one or more halogen atoms. Examples thereof include a trifluoromethyl group, difluoromethyl group, fluoromethyl group, pentafluoroethyl group, tetrafluoroethyl group, trifluoroethyl group, difluoroethyl group, fluoroethyl group, trichloromethyl group, dichloromethyl group, chloromethyl group, pentachloroethyl group, tetrachloroethyl group, trichloroethyl group, dichloroethyl group and chloroethyl group.

The "halogen" means fluorine (F), chlorine (Cl), bromine (Br) or iodine (I).

In the present specification, the "aryl group" means a monovalent aromatic hydrocarbon ring. Preferred examples thereof include C5-C10 aryl. Specific examples of such aryl include a phenyl group and naphthyl (e.g., 1-naphthyl group and 2-naphthyl group).

In the present specification, the "aryl group" may include "heteroaryl" described below.

In the present specification, the "heteroaryl" means an aromatic cyclic monovalent group containing preferably 1 to 5 heteroatoms among ring-constituting atoms and may be partially saturated. The ring may be a single ring or a bicyclic condensed ring (e.g., bicyclic heteroaryl condensed with a benzene ring or monocyclic heteroaryl ring). The number of ring-constituting atoms is preferably 5 to 10 (C5-C10 heteroaryl).

Specific examples of such heteroaryl include a furyl group, thienyl group, pyrrolyl group, imidazolyl group, pyrazolyl group, thiazolyl group, isothiazolyl group, oxazolyl group, isooxazolyl group, oxadiazolyl group, thiadiazolyl group, triazolyl group, tetrazolyl group, pyridyl group, pyrimidyl group, pyridazinyl group, pyrazinyl group, triazinyl group, benzofuranyl group, benzothienyl group, benzothiadiazolyl group, benzothiazolyl group, benzoxazolyl group, benzoxadiazolyl group, benzimidazolyl group, indolyl group, isoindolyl group, indazolyl group, quinolyl group, isoquinolyl group, cinnolinyl group, quinazolinyl group, quinoxalinyl group, benzodioxolyl group, indolizinyl group and imidazopyridyl group.

The "C5-C10 aryl-C1-C6 alkyl group (aralkyl group)" refers to a group derived from the C1-C6 alkyl group by replacement of one hydrogen atom with the C5-C10 aryl group.

The arylalkyl group (aralkyl group) means a group containing both an aryl group and an alkyl group, for example, a group derived from the alkyl group by replacement of at least one hydrogen atom with the aryl group. Preferred examples thereof include "C5-C10 aryl-C1-C6 alkyl groups". Specific examples of such arylalkyl (aralkyl) groups include a benzyl group. The "C5-C10 aryl-C1-C6 alkyl group which optionally has a substituent" refers to a group derived from the "C5-C10 aryl-C1-C6 alkyl group" by replacement of at least one hydrogen atom in the aryl group and/or the alkyl group with a substituent. Examples of the substituent include various substituents defined as the substituent for the side chain of the "amino acid".

The "alkoxy group" means a group in which a hydrogen atom in a hydroxy group is replaced with the alkyl group. Preferred examples thereof include "C1-C6 alkoxy groups".

In the present specification, the "active ester group (activated ester group)" refers to a group containing a carbonyl group that forms an amide bond by reaction with an amino group. The "active ester group" is a group containing the carbonyl group bonded to, for example, OBt, OAt, OSu, OPfp or SR1 and is a group capable of promoting the reaction with an amino group.

The "reaction promoting group" refers to a group that is introduced near a functional group to be bonded for the purpose of selectively causing reaction at a desired position and activates the functional group for bond formation reaction. The reaction promoting group can be introduced, for example, either on a carbonyl group side or on an amino group side, or both, for reacting the carbonyl group with the amino group. Examples of such reaction promoting groups include SH. These reaction promoting groups may be eliminated concurrently with or after bond formation reaction.

The "normal amine" means amine that is not activated by the reaction promoting group.

mRNA Display

In the present invention, the "nucleic acid" can also include deoxyribonucleic acid (DNA), ribonucleic acid (RNA) or nucleotide derivatives having artificial bases. The nucleic acid can also include peptide nucleic acid (PNA). The nucleic acid of the present invention may be any of these nucleic acids or a hybrid of these nucleic acids as long as the resulting nucleic acid retains genetic information of interest. Specifically, the nucleic acid according to the present invention also includes DNA-RNA hybrid nucleotides, and chimeric nucleic acids in which different nucleic acids, such as DNA and RNA, are linked together to make a single strand.

In the present invention, a nucleic acid library (e.g., display library) containing these nucleic acids as templates can be used preferably.

The display library refers to a library in which peptides as phenotypes are associated with their peptide-encoding RNAs or DNAs as genotypes. The library is brought into contact with desired immobilized targets, and molecules unbound with the targets can be washed off to enrich target-binding peptides (panning). The gene information associated with the peptide selected through such a process can be analyzed to determine the sequence of the protein bound with the target. For example, a method using the nonspecific conjugation of an antibiotic puromycin (aminoacyl-tRNA analog) to a protein during its ribosomal mRNA translation elongation has been reported as mRNA display (Proc Natl Acad Sci USA. 1997; 94: 12297-302. RNA-peptide fusions for the in vitro selection of peptides and proteins. Roberts R W, Szostak J W.) or in vitro virus (FEBS Lett. 1997; 414: 405-8. In vitro virus: bonding of mRNA bearing puromycin at the 3'-terminal end to the C-terminal end of its encoded protein on the ribosome in vitro. Nemoto N, Miyamoto-Sato E, Husimi Y, Yanagawa H.).

Spacers such as puromycin are conjugated to the 3'-ends of an mRNA library obtained by transcription from a DNA library containing a promoter such as T7 promoter. The mRNAs are translated into proteins in a cell-free translation system so that the puromycin is mistakenly incorporated in place of an amino acid into each protein by the ribosome to link the mRNA to the protein encoded thereby, resulting in a library in which mRNAs are associated with their products. This process, which does not involve the transformation of $E.$ $coli$ or the like, attains high efficiency and can construct a large-scale display library ($10^{12}$ to $10^{14}$ types of members). cDNA is synthesized from the mRNA serving as a tag involving gene information in the molecule enriched and selected by panning, and then amplified by PCR. The amplification products can be sequenced to determine the sequence of the protein linked to the mRNA. Sites encoding variable amino acid residues in the DNA library used as a template for the library can be obtained by synthesis using a mixture of bases. A string of mixes (N) of 4 bases A, T, G and C is synthesized as a multiple of 3, or N for the first and second letters in each codon and a 2-base mix (W, M, K, S, etc.) for the third letter are synthesized. In another method, the third base may be set to one type if 16 or less types of amino acids are introduced. Also, codon units corresponding to 3 letters for each codon are prepared, as shown in Examples, and a mixture of these codon units at an arbitrary ratio can be used in the synthesis to arbitrarily adjust the frequency of appearance of each amino acid residue.

In addition to the mRNA display, cDNA display which is a library composed of peptide-encoding cDNAs linked to peptide-puromycin complexes (Nucleic Acids Res. 2009; 37 (16): e108. cDNA display: a novel screening method for functional disulfide-rich peptides by solid-phase synthesis and stabilization of mRNA-protein fusions. Yamaguchi J, Naimuddin M, Biyani M, Sasaki T, Machida M, Kubo T, Funatsu T, Husimi Y, Nemoto N.), ribosome display which uses the relative stability of ribosome-translation product complexes during mRNA translation (Proc Natl Acad Sci USA. 1994; 91: 9022-6. An in vitro polysome display system for identifying ligands from very large peptide libraries. Mattheakis L C, Bhatt R R, Dower W J.), covalent display which uses the formation of a covalent bond between bacteriophage endonuclease P2A and DNA (Nucleic Acids Res. 2005; 33: e10. Covalent antibody display—an in vitro antibody-DNA library selection system. Reiersen H, Lobersli I, Loset G A, Hvattum E, Simonsen B, Stacy J E, McGregor D, Fitzgerald K, Welschof M, Brekke O H, Marvik O J.), and CIS display which uses the binding of a microbial plasmid replication initiator protein RepA to a replication origin ori (Proc Natl Acad Sci USA. 2004; 101: 2806-10. CIS display: In vitro selection of peptides from libraries of protein-DNA complexes. Odegrip R, Coomber D, Eldridge B, Hederer R, Kuhlman P A, Ullman C, FitzGerald K, McGregor D.) are known as display libraries using the cell-free translation system. Also, in vitro compartmentalization (Nat Biotechnol. 1998; 16:652-6. Man-made cell-like compartments for molecular evolution. Tawfik D S, Griffiths A D.) is known in which a transcription-translation system is enclosed in a water-in-oil emulsion or liposome per DNA molecule constituting a DNA library and subjected to translation reaction. The method described above can be performed by appropriately using any of these methods known in the art.

In the present invention, these nucleic acid libraries can be translated by using a cell-free translation system described below. In the case of using the cell-free translation system, a spacer-encoding sequence is preferably located downstream of the nucleic acid of interest. Examples of the spacer sequence include, but not limited to, sequences containing glycine or serine. Preferably, a linker formed by RNA, DNA, hexaethylene glycol (spc18) polymers (e.g., 5 polymers) or the like is contained between a compound, such as puromycin or derivative thereof, which is incorporated into a peptide during ribosomal translation, and the nucleic acid library.

Cell-Free Translation System

A protein preparation system such as a cell-free translation system is preferably used in the method for preparing a peptide compound according to the present invention. The cell-free translation system refers to a combination of ribosome extracted from cells as well as a protein factor group involved in translation, tRNAs, amino acids, energy sources (e.g., ATPs) and a regenerating system thereof and can translate mRNAs into proteins. The cell-free translation system of the present invention can additionally contain an initiation factor, an elongation factor, a dissociation factor, aminoacyl-tRNA synthetase, methionyl tRNA transformylase, etc. These factors can be obtained by purification from various cell extracts. Examples of the cells for use in the purification of the factors can include prokaryotic cells and eukaryotic cells. Examples of the prokaryotic cells can include *E. coli* cells, extreme thermophile cells and *Bacillus subtilis* cells. Eukaryotic cells made of yeast cells, wheat germs, rabbit reticulocytes, plant cells, insect cells or animal cells as materials are known.

The cell-free translation system can be obtained by homogenizing material cells and adding tRNAs, amino acids, ATPs and the like to extracts prepared by centrifugation, dialysis or the like. The material used can be, for example, *E. coli* (Methods Enzymol. 1983; 101: 674-90. Prokaryotic coupled transcription-translation. Chen H Z, Zubay G.), yeast (J. Biol. Chem. 1979 254: 3965-3969. The preparation and characterization of a cell-free system from *Saccharomyces cerevisiae* that translates natural messenger ribonucleic acid. E Gasior, F Herrera, I Sadnik, C S McLaughlin, and K Moldave), wheat germs (Methods Enzymol. 1983; 96: 38-50. Cell-free translation of messenger RNA in a wheat germ system. Erickson A H, Blobel G.), rabbit reticulocytes (Methods Enzymol. 1983; 96: 50-74. Preparation and use of nuclease-treated rabbit reticulocyte lysates for the translation of eukaryotic messenger RNA. Jackson R J, Hunt T.), Hela cells (Methods Enzymol. 1996; 275: 35-57. Assays for poliovirus polymerase, 3D(Pol), and authentic RNA replication in HeLa S10 extracts. Barton D J, Morasco B J, Flanegan J B.) or insect cells (Comp Biochem Physiol B. 1989; 93: 803-6. Cell-free translation in lysates from *Spodoptera frugiperda* (Lepidoptera: Noctuidae) cells. Swerdel M R, Fallon A M.). The translation can be coupled to transcription from DNA by the addition of RNA polymerase such as T7 RNA polymerase. Meanwhile, PUREsystem is a reconstituted cell-free translation system containing extracted and purified protein factors necessary for translation in *E. coli*, energy-regenerating enzymes and ribosome mixed with tRNAs, amino acids, ATPs, GTPs, etc. Since PUREsystem has a low content of impurities and, furthermore, is a reconstituted system, a system free from protein factors and amino acids to be excluded can be created easily ((i) Nat Biotechnol. 2001; 19: 751-5. Cell-free translation reconstituted with purified components. Shimizu Y, Inoue A, Tomari Y, Suzuki T, Yokogawa T, Nishikawa K, Ueda T.; and (ii) Methods Mol Biol. 2010; 607: 11-21. PURE technology. Shimizu Y, Ueda T.). The method described above can be performed by appropriately using these methods known in the art.

Various factors, such as ribosome and tRNAs, contained in the cell-free translation system can be purified from *E. coli* cells or yeast cells by a method well known to those skilled in the art. Naturally occurring tRNAs or aminoacyl-tRNA synthetase may be used, or artificial tRNAs or artificial aminoacyl-tRNA synthetase recognizing unnatural amino acids may be used. Use of the artificial tRNA or artificial aminoacyl-tRNA synthetase achieves synthesis of a peptide in which unnatural amino acids are introduced in a site-specific manner.

The translational incorporation of unnatural amino acids into peptides requires aminoacylating tRNAs that have orthogonality and are efficiently incorporated into ribosome ((i) Biochemistry. 2003; 42: 9598-608. Adaptation of an orthogonal archaeal leucyl-tRNA and synthetase pair for four-base, amber, and opal suppression. Anderson J C, Schultz P G.; and (ii) Chem Biol. 2003; 10:1077-84. Using a solid-phase ribozyme aminoacylation system to reprogram the genetic code. Murakami H, Kourouklis D, Suga H.). Five methods described below can be used for aminoacylating tRNAs.

Intracellular tRNA aminoacylation is provided with aminoacyl-tRNA synthetase on an amino acid basis. One method is based on the fact that a certain aminoacyl-tRNA synthetase accepts an unnatural amino acid such as N-Me His. In another method, a variant aminoacyl-tRNA synthetase that accepts an unnatural amino acid is prepared and used ((i) Proc Natl Acad Sci USA. 2002; 99: 9715-20. An engineered *Escherichia coli* tyrosyl-tRNA synthetase for site-specific incorporation of an unnatural amino acid into proteins in eukaryotic translation and its application in a wheat germ cell-free system. Kiga D, Sakamoto K, Kodama K, Kigawa T, Matsuda T, Yabuki T, Shirouzu M, Harada Y, Nakayama H, Takio K, Hasegawa Y, Endo Y, Hirao I, Yokoyama S.; (ii) Science. 2003; 301: 964-7. An expanded eukaryotic genetic code. Chin J W, Cropp T A, Anderson C, Mukherji M, Zhang Z, Schultz P G. Chin, J W.; and (iii) Proc Natl Acad Sci USA. 2006; 103: 4356-61. Enzymatic aminoacylation of tRNA with unnatural amino acids. Hartman M C, Josephson K, Szostak J W.). A method that may be used involves aminoacylating tRNAs in vitro and then chemically modifying amino acids (J Am Chem Soc. 2008; 130: 6131-6. Ribosomal synthesis of N-methyl peptides. Subtelny A O, Hartman M C, Szostak J W.). A tRNA lacking CA at the 3'-terminal CCA sequence can be ligated to aminoacylated pdCpA prepared separately by RNA ligase to obtain an aminoacyl-tRNA (Biochemistry. 1984; 23: 1468-73. T4 RNA ligase mediated preparation of novel "chemically misacylated" tRNAPheS. Heckler T G, Chang L H, Zama Y, Naka T, Chorghade M S, Hecht S M.). The aminoacylation may be carried out by a ribozyme, called flexizyme, which is able to charge active esters of various unnatural amino acids onto tRNAs (J Am Chem Soc. 2002; 124: 6834-5. Aminoacyl-tRNA synthesis by a resin-immobilized ribozyme. Murakami H, Bonzagni N J, Suga H.). Also, a method of ultrasonic agitating tRNAs and amino acid active esters in cationic micelle may be used (Chem Commun (Camb). 2005; (34): 4321-3. Simple and quick chemical aminoacylation of tRNA in cationic micellar solution under ultrasonic agitation. Hashimoto N, Ninomiya K, Endo T, Sisido M.). The aminoacylation may be achieved by adding, to a tRNA, an amino acid active ester linked to a PNA complementary to a 3'-terminal region of the tRNA (J Am Chem Soc. 2004; 126: 15984-9. In situ chemical aminoacylation with amino acid thioesters linked to a peptide nucleic acid. Ninomiya K, Minohata T, Nishimura M, Sisido M.).

Many methods using a stop codon as a codon for unnatural amino acid introduction have been reported. A synthesis system from which natural amino acids and ARS are excluded can be constructed by using the PUREsystem mentioned above. Unnatural amino acids can be introduced in place of the excluded natural amino acids for codons encoding the amino acids (J Am Chem Soc. 2005; 127: 11727-35. Ribosomal synthesis of unnatural peptides. Josephson K, Hartman M C, Szostak J W.). Furthermore, unnatural amino acids can be added without the exclusion of natural amino acids by breaking codon degeneracy (Kwon I, et al., Breaking the degeneracy of the genetic code. J Am Chem Soc. 2003, 125, 7512-3.). Peptides containing N-methylamino acids can be synthesized in the ribosome by utilizing the cell-free translation system such as PureSystem.

Adjustment of Frequency of Appearance of N-Methylamino Acid

The number of N-methylamino acids contained in peptides constituting a library can be adjusted by the frequency of appearance of a codon assigned to each N-methylamino acid in the synthesis of a DNA library. For example, in a library of peptides containing 10 variable sites of amino acid residues, 10 types of N-Me-amino acids (provided that the types of amino acids are selected from 20 types) are selected, and the peptides are synthesized such that codon units for the N-Me-amino acids account for 10/20 (50%) per variable site. The resulting peptides in the library contain five N-methylamino acids on average.

Each peptide compound in a library composed of the peptide compounds having a cyclic portion according to the present invention is composed of 9 to 13 amino acid and/or amino acid analog residues. These 9 to 13 residues are counted from an amino acid on the N-terminal side (first residue) immediately before each random region of the display library to the 13th amino acid residue (based on the number of units in a completely posttranslationally modified form). The amino acids contained in the random regions need to be determined in consideration of the ratios of N-alkylamino acids and NH2-containing amino acids such that 3 to 10, preferably 4 to 9, more preferably 5 to 8 N-methylamino acids on average are included among the 9 to 13 residues forming the peptide compound having a cyclic portion. Likewise, the types of amino acids contained in the random regions need to be selected such that the ClogP values of these 13-residue peptides are set to 4 or more, preferably 5 or more, more preferably 6 or more on average.

For the selected amino acids, it is preferred that all selected amino acids should have functional groups that are neutral (e.g., pH=7.0) and are not excessively ionized. For example, pKa as an acid is preferably 3.5 or more, more preferably 4.5 or more, further preferably 5 or more. For example, aspartic acid has a side chain carboxyl group pKa of 3.9, while tyrosine has a side chain phenolic hydroxy group pKa of 10. Tetrazole has a pKa of 5.6. Also, pKa as a base is preferably 9 or less, more preferably 7.5 or less, further preferably 6.5 or less. For example, arginine has a side chain guanidino group pKa of 12.5; lysine has a side chain amino group pKa of 10.5; and histidine has an imidazolyl group pKa of 6.1. Pyridine has a pKa of 5.2. The N-terminal α-amino acid in the peptide has a main chain amino group pKa of around 8.

In adherence to this rule, the types of amino acids in variable regions, as described in our actual examination of Example 24, were 21 types, 10 types of which were selected as N-alkylamino acids such as N-methylamino acid. Since both of two fixed amino acids had NH2 in the initiation read-through method, the average number of N-alkylamino acids was calculated to be 4.4. One of two fixed amino acids was N-alkylated in the initiation suppression method, and the amino acid on the C-terminal side of the intersection unit was also selected from among N-alkylamino acids. Thus, the average number of N-alkylamino acids was calculated to be 6.0.

Likewise, CLogP values in both methods were 5.97 and 6.12, respectively.

Unnatural Amino Acid that can be Used in Translational Synthesis

Exemplary unnatural amino acids (translation amino acids) that can be used in the present invention will be shown below, though the unnatural amino acids of the present invention are not limited thereto. Most of these unnatural amino acids are purchased with their side chains protected or unprotected and their amine sites protected or unprotected. Unpurchased ones are synthesized by known methods.

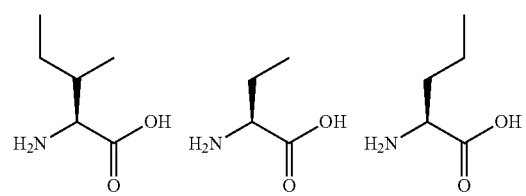

-continued
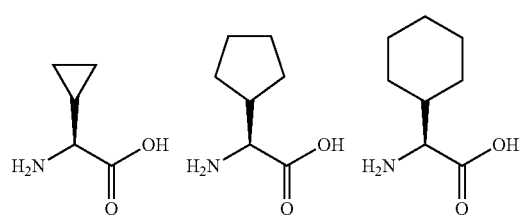
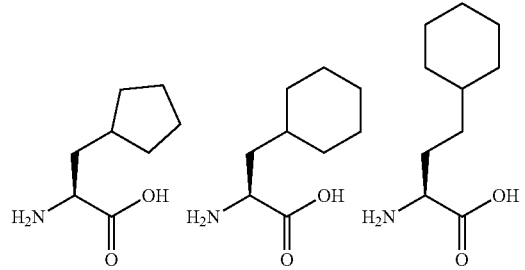
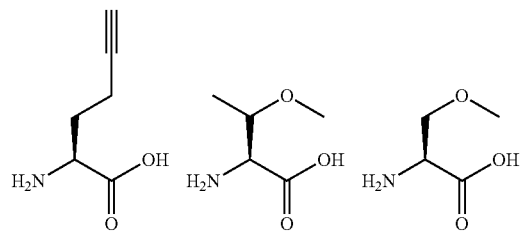
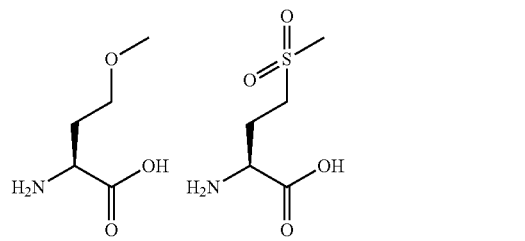
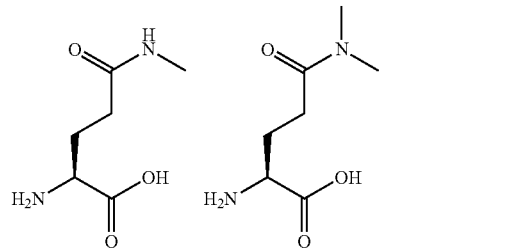
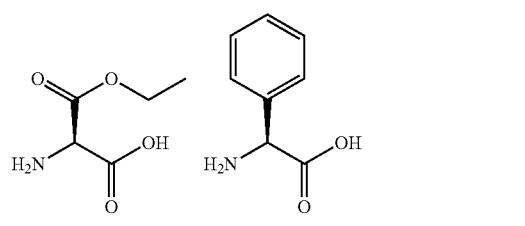
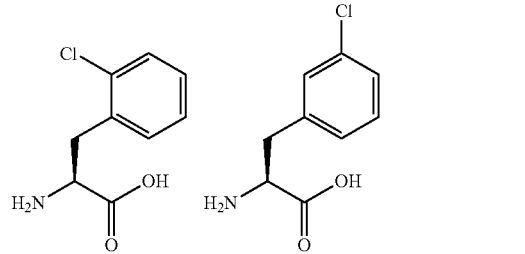
-continued
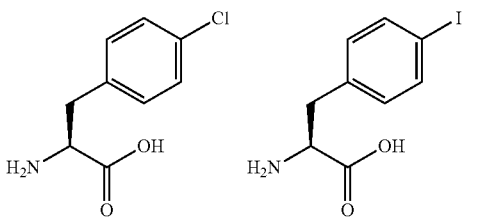
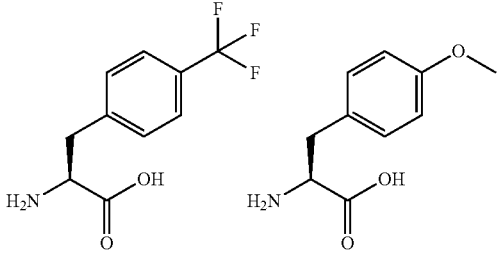
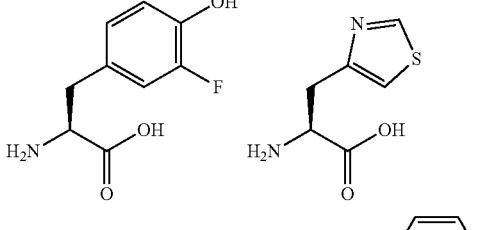
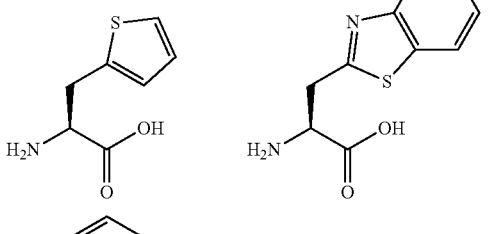
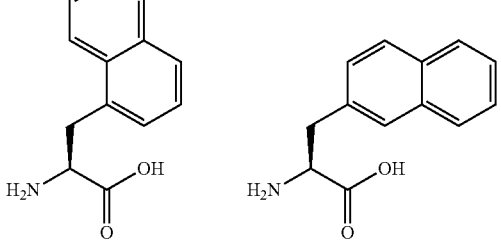
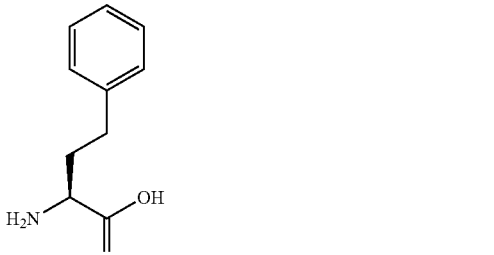
The following N-Me-amino acids can be used as the unnatural amino acids:
N-methylalanine, N-methylglycine, N-methylphenylalanine, N-methyltyrosine, N-methyl-3-chlorophenylalanine, N-methyl-4-chlorophenylalanine, N-methyl-4-methoxyphenylalanine, N-methyl-4-thiazolealanine, N-methylhistidine, N-methylserine, N-methylaspartic acid.

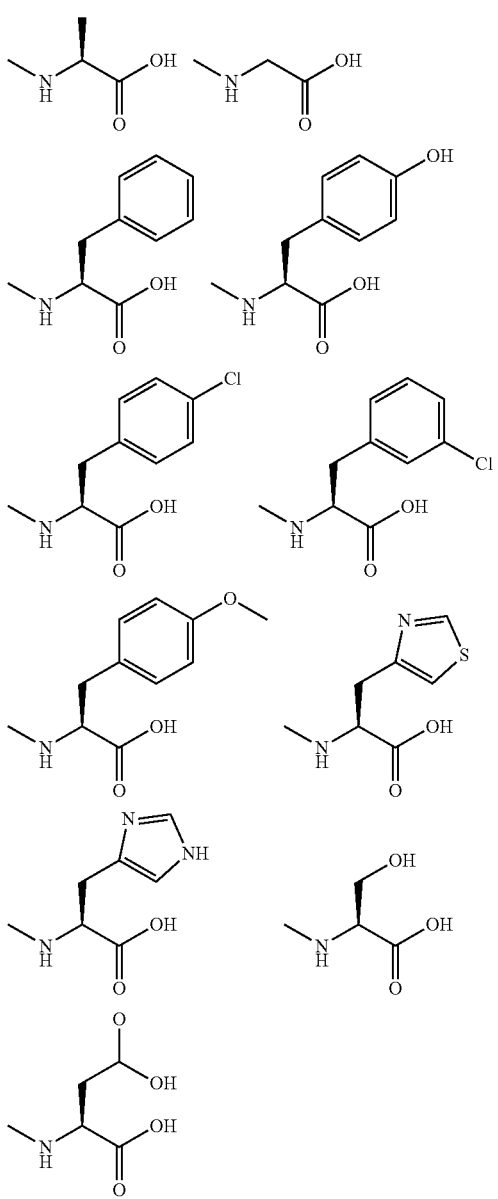

The following N-alkylamino acids can also be used as the unnatural amino acids:

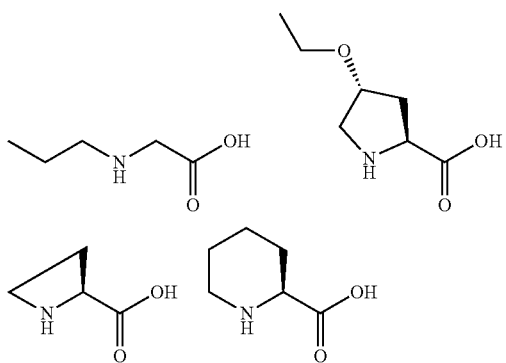

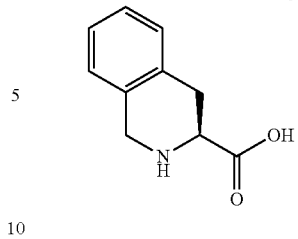

The following D-amino acid can also be used as the unnatural amino acid:

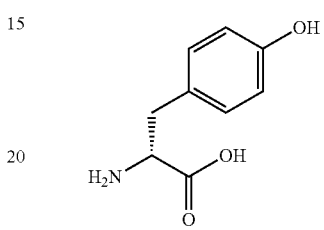

The following α,α-dialkylamino acid can also be used as the unnatural amino acid:

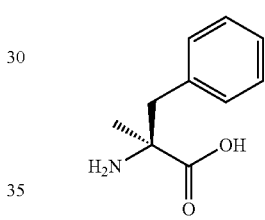

The following amino acid can also be used as the unnatural amino acid:

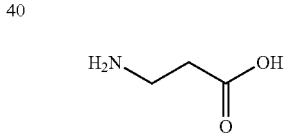

Production of Aminoacyl-tRNA

Each amino acid and amino acid analog can be converted to, for example, an active ester for reaction with pdCpA. Most of these active esters can be isolated as cyanomethyl esters.

Each isolated cyanomethyl ester can be conjugated to pdCpA by reaction and then linked to a tRNA by, for example, ligation, to prepare a conjugate of the tRNA and the amino acid or amino acid analog.

The approach for preparing tRNA-amino acid conjugates is not limited to such a pdCpA method. These conjugates may be synthesized by an approach using flexizyme or by an approach using ARS.

Amide Bond Formation Reaction that can be Utilized for Cyclization after Translational Synthesis The amide bond formation reaction between carboxylic acids and primary and secondary amines are widely used in general organic synthetic chemistry. Exemplary methods that can be used involve activating carboxylic acids in advance to form active esters, which are then isolated and mixed with amines, or involve directly mixing carboxylic acids with amines and then activating the carboxylic acids to form amide bonds. An acid halide group including acid chloride and acid iodide or an active ester group including HOBt, HOAt, HOSu, HOPfp and thioester are widely known as active forms of carboxylic acids.

Examples of the thioester preferably include moieties represented by —C(=O)SR1.

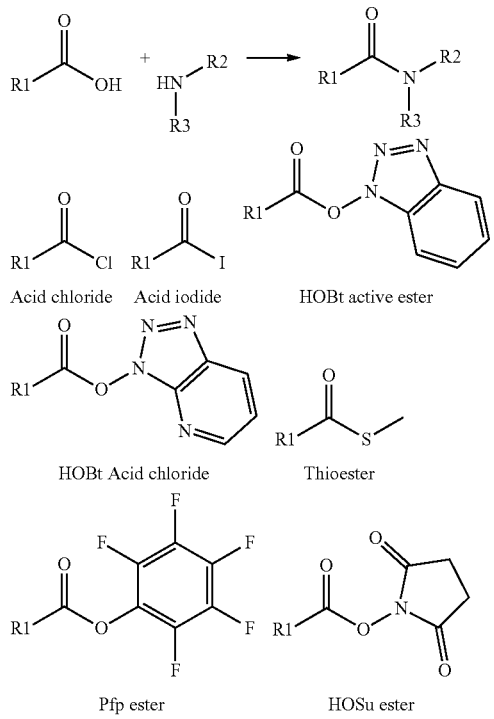

Acid chloride   Acid iodide   HOBt active ester

HOBt Acid chloride   Thioester

Pfp ester   HOSu ester

The acid halides can be isolated by purification operation from mixtures of carboxylic acids and a halogenating agent such as $SOCl_2$. The obtained acid halides have high reactivity. For use in a translation system such as PureSystem, an approach can be used which involves activating carboxylic acids translated by PureSystem into acid iodides using $PPh_3$ and $I_2$ as mild reaction conditions that permit conversion to acid halides (Lakshman et al., Eur. J. Org. Chem. 2010, 2709).

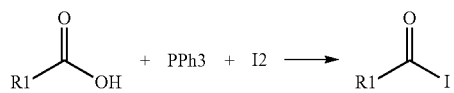

In the active ester method, for example, an approach can be used which involves translating carboxylic acids in PureSystem and then converting the carboxylic acids to active esters by reaction in the reaction system to generate activated esters or which involves translating, in PureSystem, active ester compounds isolated in advance. Among active esters, thioester or the like having lower reactivity is generally suitable for translation following preliminary isolation as active esters, whereas more highly reactive HOAt active ester or the like is desirably generated posttranslationally as activated esters.

For selective reaction between a carboxylic acid and an amino group at a desired position, a reaction promoting group may be introduced either on the carboxylic acid side or on the amino group side, or both.

Examples of the approach for introducing the reaction promoting group near the amino group include an approach of introducing a thiol group near the amino group. The number of atoms (the number of carbon chains) linking the amino group and the thiol group is particularly preferably 2 or 3. The carboxylic acid or activated carboxylic acid and a unit having the amino group with the thiol group introduced near the amino group are introduced by PureSystem, and then, these two sites can be selectively reacted with each other to give a compound having an amide bond. Because of the high nucleophilicity of the SH group, first, the SH group quickly reacts with the active ester and is converted to a thermodynamically stable amide bond by intramolecular transfer reaction. As a result, the amino group having the promoting group can be amidated selectively. Such a reaction example is widely used particularly as reaction between thioester and cysteine (chemical ligation method).

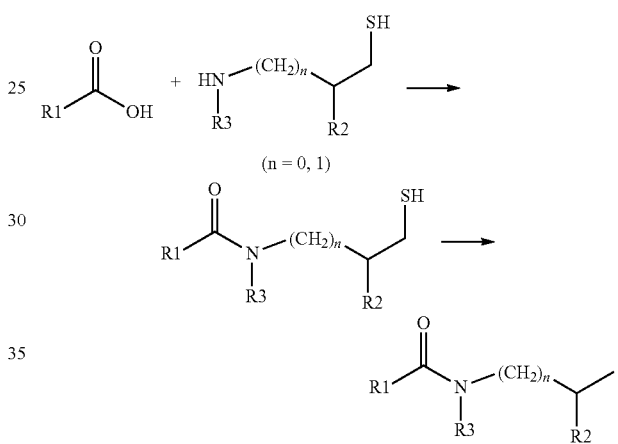

Desirably, the obtained SH group-containing amide compound is desulfurized under mild reaction conditions. This is because the SH group contained therein forms covalent bonds with various targets, making it difficult to efficiently identify Hit compounds.

Examples of the introduction of reaction promoting groups both on the carboxylic acid side and on the amino group side include a scheme shown below (Li et al., Org. Lett. 2010, 12, 1724).

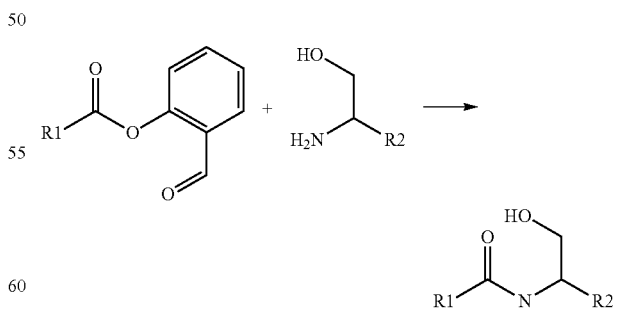

The active ester group on the carboxylic acid side has an aldehyde site and therefore, can quickly form N,O-benzylidene acetal selectively with a substrate having an alcohol moiety near the amino group. This product is subjected to transfer reaction under acidic conditions to form an amide bond. This active ester can be reacted selectively with serine in the presence of phenylthioester. Alternatively, this active ester can be reacted selectively with serine containing an OH group in the presence of lysine.

Carboxylic acids may be reacted directly with amines by bypassing active esters. In this approach by passing active esters, water generated by, for example, condensation, is removed (azeotropy with toluene or combined use with dehydrating agent such as molecular sieves) for dehydration reaction. More mild reaction conditions than proton acid have been reported. For example, an iron catalyst can be used in reaction using a catalyst such as a transition metal (Das et al., J. Org. Chem. 2003, 68, 1165.).

Instead of the reaction between the carboxylic acid and the amine, either or both of them may be reacted as a different functional group. In such an approach, for example, azide can be used instead of the amine and reacted with an active ester.

Thiocarboxylic acid may be used as an activated form of carboxylic acid, while azide may be used as an amine equivalent (Williams et al., J. Am. Chem. Soc. 2003, 125, 7754).

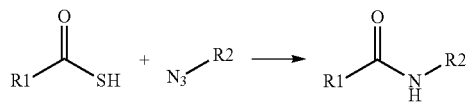

This reaction can be applied in water under relatively mild reaction conditions (60° C., 36 hr).

Azide may be used as an amine equivalent (Vilarrasa et al., J. Org. Chem. 2009, 74, 2203). The carboxylic acid is activated into thioester or selenoester by a dithio catalyst or diseleno catalyst in the presence of tertiary phosphine in a reaction system. Also, the azide site is activated by reaction with tertiary phosphine and then reacted with the active ester. Such an active ester intramolecularly having both thioester and phosphine sites has been reported to form an amide bond more effectively and is widely used as Staudinger reaction (Raines et al., Org. Lett. 2001, 3, 9). This approach is also applicable to peptide synthesis (Hackenberger et al., Angew. Chem. Int. Ed. 2008, 47, 5984).

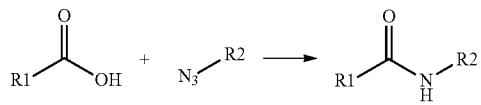

Amidation reaction can be carried out by condensation reaction using keto acid in place of the carboxylic acid and using hydroxyamine in place of the amine (Bode et al., Angew. Chem. Int. Ed. 2006, 45, 1248). This reaction can be performed selectively in the presence of a functional group such as carboxylic acid or amine in an aqueous solvent system under mild conditions (40° C.).

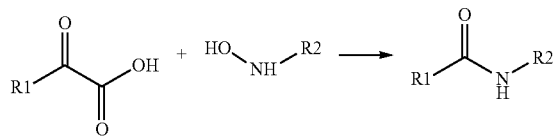

A method as described below may be used as a modification of the above reaction (Bode et al., Angew. Chem. Int. Ed. 2006, 45, 1248).

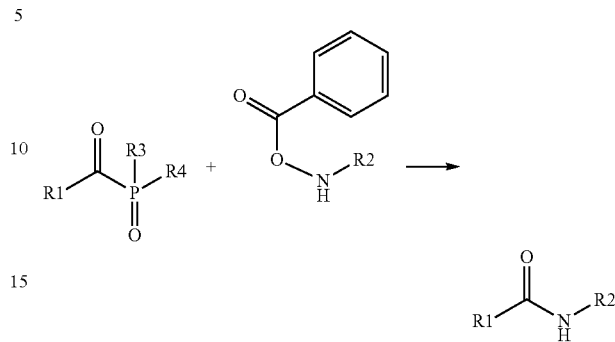

In addition, an approach using alcohol, nitrile and acetylene sites as starting materials can also be used for the conversion of the carboxylic acid site to another functional group. A transition metal catalyst such as ruthenium (Murahashi et al., J. Am. Chem. Soc. 1986, 108, 7846), platinum (Vries et al., Tet. Lett. 2000, 41, 2467) or iron (Williams et al., Tet. Lett. 2009, 50, 4262) can be used in amidation reaction (reaction example shown below) by the condensation of nitrile and amine.

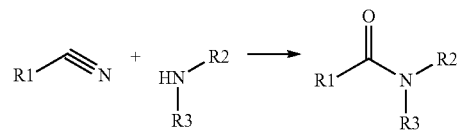

An alkyne and an amine can be amidated by catalyst reaction using a manganese porphyrin catalyst in water at room temperature for 1 hour under mild oxidation conditions (oxon) (Che et al., J. Am. Chem. Soc. 2006, 128, 14796). This method is also applicable to the synthesis of a peptide having an unprotected side chain.

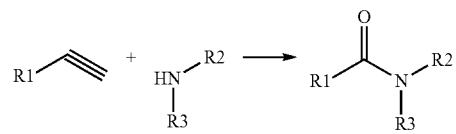

An alcohol and an amine can also be condensed by using a ruthenium complex catalyst (Milstein et al., Science 2007, 317, 790).

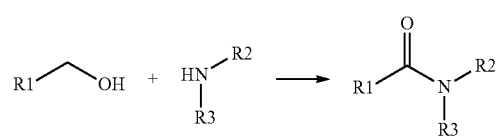

The condensation reaction of an aldehyde and an amine catalyzed by a palladium complex (Yoshida et al., Synthesis, 1983, 474) or by a rhodium complex (Beller et al., Eur. J. Org. Chem. 2001, 423) may be used.

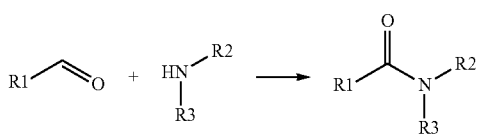

<Pharmaceutical Composition>

The present invention provides a pharmaceutical composition containing a peptide compound prepared by the method of the present invention.

The pharmaceutical composition of the present invention can be formulated according to a method known in the art by supplementing the peptide compound prepared by the method of the present invention with pharmaceutically acceptable carriers. This formulation can be carried out according to a routine method by using an excipient, a binder, a lubricant, a colorant and a corrigent usually used, and optional additives such as a stabilizer, an emulsifier, an absorption promoter, a surfactant, a pH adjuster, an antiseptic and an antioxidant and mixing therewith ingredients generally used as starting materials for pharmaceutical preparations.

For example, oral preparations are prepared by supplementing the compound according to the present invention or a pharmacologically acceptable salt thereof with an excipient and optionally with a binder, a disintegrant, a lubricant, a colorant, a corrigent and the like and then preparing the mixture into, for example, powders, fine granules, granules, tablets, coated tablets or capsules according to a routine method.

Examples of these ingredients include: animal or plant oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; silicon resins; silicon oil; surfactants such as polyoxyethylene fatty acid ester, sorbitan fatty acid ester, glycerin fatty acid ester, polyoxyethylene sorbitan fatty acid ester, polyoxyethylene hydrogenated castor oil and polyoxyethylene-polyoxypropylene block copolymers; water-soluble polymers such as hydroxyethylcellulose, polyacrylic acid, carboxyvinyl polymers, polyethylene glycol, polyvinylpyrrolidone and methylcellulose; lower alcohols such as ethanol and isopropanol; polyhydric alcohols such as glycerin, propylene glycol, dipropylene glycol and sorbitol; sugars such as glucose and sucrose; inorganic powders such as silicic anhydride, magnesium aluminum silicate and aluminum silicate; and purified water.

Examples of the excipient include lactose, corn starch, saccharose, glucose, mannitol, sorbitol, crystalline cellulose and silicon dioxide.

Examples of the binder include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, polypropylene glycol-polyoxyethylene block polymers and meglumine.

Examples of the disintegrant include starch, agar, gelatin powders, crystalline cellulose, calcium carbonate, sodium bicarbonate, calcium citrate, dextrin, pectin and carboxymethylcellulose-calcium.

Examples of the lubricant include magnesium stearate, talc, polyethylene glycol, silica and hydrogenated plant oils.

A colorant permitted to be added to pharmaceutical agents is used. Cocoa powders, menthol, aromatic powders, peppermint oil, borneol, powdered cinnamon bark, or the like is used as the corrigent.

These tablets or granules may be sugar-coated or appropriately coated in any other manner, if necessary. Alternatively, liquid formulations such as syrups or preparations for injection are prepared by supplementing the compound according to the present invention or a pharmacologically acceptable salt thereof with a pH adjuster, a solubilizer, a tonicity agent and the like and optionally with a dissolution adjuvant, a stabilizer and the like and formulating the mixture by a routine method.

For example, the pharmaceutical composition of the present invention can be parenterally used in the form of an aseptic solution or suspension of an injection with water or any other pharmaceutically acceptable liquid. For example, the compound according to the present invention or a pharmacologically acceptable salt thereof may be appropriately combined with pharmacologically acceptable carriers or media, specifically, sterile water or saline, a plant oil, an emulsifier, a suspending agent, a surfactant, a stabilizer, a flavoring agent, an excipient, a vehicle, an antiseptic, a binder and the like and mixed in a unit dosage form required for generally accepted pharmaceutical practice to make preparations. Specific examples of the carriers can include light anhydrous silicic acid, lactose, crystalline cellulose, mannitol, starch, carmellose calcium, carmellose sodium, hydroxypropylcellulose, hydroxypropylmethylcellulose, polyvinyl acetal diethyl aminoacetate, polyvinylpyrrolidone, gelatin, medium-chain fatty acid triglyceride, polyoxyethylene hydrogenated castor oil 60, saccharose, carboxymethylcellulose, corn starch and inorganic salts. The amount of the active ingredient in these preparations is determined such that an appropriate dose is obtained in a prescribed range.

Sterile compositions for injection can be formulated according to general pharmaceutical practice by using a vehicle such as injectable distilled water.

Examples of aqueous solutions for injection include saline and isotonic solutions containing glucose or other adjuvants, for example, D-sorbitol, D-mannose, D-mannitol and sodium chloride. These aqueous solutions may be used in combination with appropriate dissolution adjuvants including alcohols, specifically, ethanol, polyalcohols such as propylene glycol and polyethylene glycol, and nonionic surfactants such as Polysorbate 80® and HCO-50.

Examples of oil solutions include sesame oil and soybean oil. Benzyl benzoate and/or benzyl alcohol may be used as a dissolution adjuvant in combination therewith. These injectable solutions may be mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The prepared injections are usually charged into appropriate ampules.

Preferably, the pharmaceutical composition of the present invention is orally administered, though the administration method is not limited to oral administration. Specific examples of parenteral administration include injection, transnasal, transpulmonary and transdermal dosage forms. The pharmaceutical composition can be administered systemically or locally by injection dosage forms including intravenous injection, intramuscular injection, intraperitoneal injection and hypodermic injection.

The administration method can be appropriately selected according to the age and symptoms of a patient. The single dose of the pharmaceutical composition containing the peptide compound prepared by the method of the present invention can be selected within the range of, for example, 0.0001 mg to 1000 mg per kg body weight. Alternatively, the dose may be selected within the range of, for example, 0.001 to 100000 mg/body per patient, though the dose of the present invention is not necessarily limited to these numeric values. The dose and the administration method vary depending on the body weight, age, symptoms, etc. of the patient. Those skilled in the art can select an appropriate dose and administration method.

EXAMPLES

The present invention will be further illustrated with reference to the following Examples but is not limited thereto.

[Example 1] Synthesis of Compounds (1g) Having Side Chain Carboxylic Acid Converted to Active Ester A series of active esters having thioester (Compounds 1g) were synthesized, and the compounds having Rex1=Me, Et, iPr, tBu, Bn, Ph or phenethyl were synthesized according to the method of FIG. 1.

The following abbreviations are used in Examples.
DCM Dichloromethane
DIC N,N-Diisopropylcarbodiimide
DIPEA N,N-Diisopropylethylamine
DMAP 4-Dimethylaminopyridine
DMF Dimethylformamide
DMSO Dimethyl sulfoxide
DTT Dithiothreitol
FA Formic acid
TFA Trifluoroacetic acid
THF Tetrahydrofuran
HFIP 1,1,1,3,3,3-Hexafluoro-2-propanol
HOBT 1H-Benzo[d][1,2,3]triazol-1-ol
WSCI-HCl 1-Ethyl-3-(3-dimethylaminopropyl)carbodiimide hydrochloride
TCEP Tris(2-carboxyethyl)phosphine
NMP N-Methyl-2-pyrrolidone
DBU 1,8-Diazabicyclo[5.4.0]-7-undecene Reaction solvents for peptide synthesis (purchased from Kanto Chemical, Wako Pure Chemical Industries or Watanabe Chemical Industries) were used for peptide synthesis and solid-phase synthesis. Examples thereof include DCM, DMF, DMSO, 2% DBU in DMF, and 20% piperidine in DMF. Dehydrated solvents or anhydrous solvents (purchased from Kanto Chemical, Wako Pure Chemical Industries, etc.) were used for reactions where water was not added as a solvent.

LCMS analysis conditions are as follows.

TABLE 1

| Analysis condition | Instrument | Column (I.D. × length)(mm) | Mobile phase | Gradient (A/B) | Flow rate (mL/min) | Column temperature (° C.) | Wavelength |
|---|---|---|---|---|---|---|---|
| SQD AA05 | Acquity UPLC/SQD | Ascentis Express C18 (2.1 × 50) | A) 10 mM AcONH$_4$, H$_2$O B) MeOH | 95/5 => 0/100(1.0 min) 0/100(0.4 min) | 1.0 | 35 | 210-400 nm PDA total |
| SQD AA50 | Acquity UPLC/SQD | Ascentis Express C18 (2.1 × 50) | A) 10 mM AcONH$_4$, H$_2$O B) MeOH | 50/50 => 0/100(0.7 min) 0/100(0.7 min) | 1.0 | 35 | 210-400 nm PDA total |
| SQD FA05 | Acquity UPLC/SQD | Ascentis Express C18 (2.1 × 50) | A) 0.1% FA, H$_2$O B) 0.1% FA, MeCN | 95/5 => 0/100(1.0 min) 0/100(0.4 min) | 1.0 | 35 | 210-400 nm PDA total |
| SQD FA50 | Acquity UPLC/SQD | Ascentis Express C18 (2.1 × 50) | A) 0.1% FA, H$_2$O B) 0.1% FA, MeCN | 50/50 => 0/100(0.7 min) 0/100(0.7 min) | 1.0 | 35 | 210-400 nm PDA total |
| ZQ AA05 | 2525BGM/ 2996PDA/ ZQ2000 | Chromolith Flash RP-18e (4.6 × 25) | A) 10 mM AcONH$_4$, H$_2$O B) MeOH | 95/5 => 0/100(3.0 min) 0/100(2.0 min) | 2.0 | Room temperature | 210-400 nm PDA total |
| ZQ AA50 | 2525BGM/ 2996PDA/ ZQ2000 | Chromolith Flash RP-18e (4.6 × 25) | A) 10 mM AcONH$_4$, H$_2$O B) MeOH | 50/50 => 0/100(3.0 min) 0/100(2.0 min) | 2.0 | Room temperature | 210-400 nm PDA total |
| ZQ FA05 | 2525BGM/ 2996PDA/ ZQ2000 | Chromolith Flash RP-18e (4.6 × 25) | A) 0.1% FA, H$_2$O B) 0.1% FA, MeCN | 95/5 => 0/100(3.0 min) 0/100(2.0 min) | 2.0 | Room temperature | 210-400 nm PDA total |
| SMD method 1 | Nexera/2020 | Kinetex 1.7 u C18 (2.1 × 50) | A) 0.05% TFA, H$_2$O B) 0.05% TFA, MeCN | 95/5 => 0/100(1.5 min) 0/100(0.5 min) | 1.0 | 35 | 210-400 nm PDA total |
| SMD method 4 | Shimadzu LCMS-2020 LC-20AD | Shim-Pack XR-ODS (3.0 × 50) | A) 0.05% TFA, H2O B) MeCN | 95/5 => 0/100(1.2 min) 0/100(1.0 min) => 95/5(0.1 min) 95/5(0.2 min) | 1.0 | 40 | 190-800 nm PDA total |
| SMD method 5 | Shimadzu LCMS-2020 LC-20AD | Waters Atlantis T3 (4.6 × 100) | A) 0.05% TFA, H2O B) MeCN | 95/5 => 0/100(1.2 min) 0/100(1.0 min) => 95/5(0.1 min) 95/5(0.2 min) | 1.0 | 40 | 190-800 nm PDA total |
| ZQ HFIP-Et3N | 2525BGM/ 2996PDA/ ZQ2000 | XBridge TM OST C18 (4.6 × 50) | A) 400 mM HFIP- 15 mM Et3N, H$_2$O B) 400 mM HFIP- 15 mM Et3N, MeOH | 95/5 => 5/95(8.0 min) 5/95(2.0 min) | 1.0 | Room temperature | 260 nm PDA |
| ZQ HFIP-Me2NEt | 2525BGM/ 2996PDA/ ZQ2000 | XBridge TM OST C18 (4.6 × 50) | A) 400 mM HFIP- 15 mM Me2NEt, H$_2$O B) 400 mM HFIP- 15 mM Et3N, MeOH | 95/5 => 5/95(8.0 min) 5/95(2.0 min) | 1.0 | Room temperature | 260 nm PDA |
| Orbitrap HFIP-Et3N | Acquity UPLC/LTQ Orbitrap XL | Acquity UPLC BEH C-18 (2.1 × 50) | A) 400 mM HFIP- 15 mM Et3N, H$_2$O B) 400 mM HFIP- 15 mM Et3N, MeOH | 95/5 => 2/98(12.0 min) 2/98(1.0 min) | 0.2 | 60 | 200-500 nm PDA total |

TABLE 1-continued

| Analysis condition | Instrument | Column (I.D. × length)(mm) | Mobile phase | Gradient (A/B) | Flow rate (mL/min) | Column temperature (° C.) | Wavelength |
|---|---|---|---|---|---|---|---|
| SMD Method 6 | Shimadzu LCMS-2020 LC-20AD | Shim-Pack XR-ODS (3.0 × 50) | A) 0.1% FA, H2O B) 0.1% FA, MeCN | 90/10 => 0/100(2.0 min) 0/100(1.0 min) => 90/10(0.3 min) 90/10(0.2 min) | 1.0 | 40 | 190-800 nm PDA total |
| SMD Method 7 | Shimadzu LCMS-2020 LC-20AD | Shim-Pack XR-ODS (3.0 × 50) | A) 0.05% TFA, H2O B) 0.05% TFA, MeCN | 95/5 => 0/100(1.2 min) 0/100(1.0 min) => 95/5(0.13 mi) 95/5(0.17 min) | 1.0 | 40 | 190-800 nm PDA total |
| SMD Method 8 | Shimadzu LCMS-2020 LC-20AD | Shim-Pack XR-ODS (3.0 × 50) | A) 0.05% TFA, H2O B) 0.05% TFA, MeCN | 95/5 => 0/100(2.0 min) 0/100(1.2 min) => 95/5(0.13 min) 95/5(0.27 min) | 1.0 | 40 | 190-800 nm PDA total |
| SMD Method 9 | Shimadzu LCMS-2020 LC-20AD | Shim-Pack XR-ODS (3.0 × 50) | A) 0.05% TFA, H2O B) 0.05% TFA, MeCN | 95/5 => 0/100(1.2 min) 0/100(0.9 min) => 95/5(0.1 min) 95/5(0.5 min) | 1.0 | 40 | 190-800 nm PDA total |
| SMD Method 10 | Shimadzu LCMS-2020 LC-20AD | Waters Xselect (3.0 × 50) | A) 0.1% FA, H2O B) 0.05% FA, MeCN | 95/5 => 45/55(5.0 min) 45/55(2.0 min) => 95/5(0.2 min) 95/5(0.2 min) | 0.9 | 35 | 190-800 nm PDA total |
| SMD Method 11 | Shimadzu LCMS-2020 LC-20AD | Shim-Pack XR-ODS (3.0 × 50) (3.0 × 50) | A) 0.05% TFA, H2O B) 0.05% TFA, MeCN | 90/10 => 0/100(1.7 min) 0/100(1.5 min) => 90/10(0.13 min) 90/10(0.27 min) | 0.9 | 40 | 190-800 nm PDA total |
| Orbitrap HFIP-Et3N-2 | UltiMate3000/ LTQ Orbitrap XL | Acclaim PepMap RSLC C18 (0.075 × 150) | A) 400 mM HFIP-15 mM Et3N, H2O B) 400 mM HFIP-15 mM Et3N, MeOH | 96/4 => 30/70(45.0 min) 2/98(1.0 min) 2/98(2.0 min) | 0.0003 | 40 | — |

1. Synthesis of 1g-ID

1-1. Synthesis of (S)-4-(tert-butoxy)-4-oxo-3-(pent-4-enamido)butanoic Acid (Compound 1b-I)

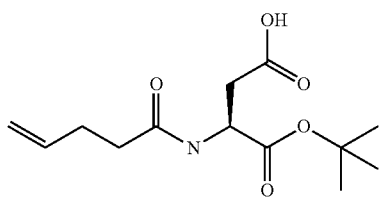 [SMILES: C=CCCC(=O)N[C@@H](CC(=O)O)C(=O)OC(C)(C)C]

Pent-4-enoyl chloride (42.2 mmol, 4.66 ml) was added to a solution of (S)-3-amino-4-(tert-butoxy)-4-oxobutanoic acid (Compound 1a-I) (21.1 mmol, 4.00 g) and $Na_2CO_3$ (63.3 mmol, 6.71 g) in THF (70 mL) and water (140 mL) at 0° C., and the mixture was stirred at room temperature for 20 minutes. The reaction mixture was then adjusted to pH 2 by adding concentrated hydrochloric acid thereto at 0° C. After dilution with ethyl acetate, salting-out extraction was carried out by adding an appropriate amount of NaCl. The resulting organic extract was washed with brine and dried over magnesium sulfate. Concentration under reduced pressure afforded a mixed crude product A (7.69 g, 100%) of (S)-4-(tert-butoxy)-4-oxo-3-(pent-4-enamido)butanoic acid (Compound 1b-I) and pent-4-enoic acid (1:0.8).

1-2. Synthesis of (S)-4-(benzylthio)-4-oxo-2-(pent-4-enamido)butanoic Acid (Compound 1f-ID)

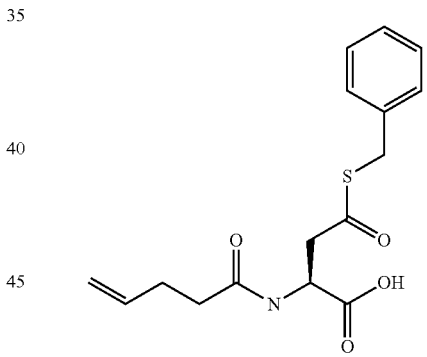

DIC (N,N'-diisopropylcarbodiimide) (2.41 ml, 15.5 mmol), DMAP (N,N-dimethylaminopyridine) (315 mg, 2.58 mmol) and phenylmethanethiol (1.82 ml, 15.5 mmol) were added to a solution of the mixed crude product A (2.51 g, 12.9 mmol) of (S)-4-(tert-butoxy)-4-oxo-3-(pent-4-enamido)butanoic acid (Compound 1b-I) and pent-4-enoic acid (1:0.8) in $CH_2Cl_2$ (35 ml), and the mixture was stirred at room temperature for 4 hours. TFA (21 ml) was then added to the reaction mixture, which was stirred at room temperature for 9.5 hours. The reaction mixture was then concentrated under reduced pressure, and the resulting residue was reverse-phase silica gel column chromatography (10 mM aqueous ammonium acetate solution/methanol=80/20→40/60) to afford (S)-4-(benzylthio)-4-oxo-2-(pent-4-enamido) butanoic acid (Compound 1f-ID) (1.65 g, 74%).

LCMS (ESI) m/z=322 (M+H)+

Retention time: 0.78 min (analysis condition SQDAA05)

1-3. Synthesis of (S)-cyanomethyl 4-(benzylthio)-4-oxo-2-(pent-4-enamido)butanoate (Compound 1g-ID)

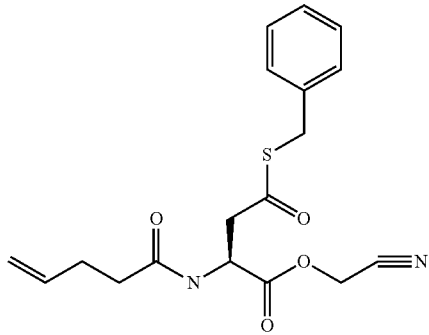 [SMILES: C=CCCC(=O)N[C@@H](CC(=O)SCc1ccccc1)C(=O)OCC#N]

2-Bromoacetonitrile (4.35 ml, 62.4 mmol) and N-ethyl-N-isopropylpropan-2-amine (0.651 ml, 3.74 mmol) were added to a solution of (S)-4-(benzylthio)-4-oxo-2-(pent-4-enamido)butanoic acid (Compound 1f-ID) (1.00 g, 3.12 mmol) in DMSO (4.35 ml), and the mixture was stirred at room temperature for 40 minutes. A saturated aqueous ammonium chloride solution (5 ml) was added to the reaction mixture, after which the mixture was extracted with ethyl acetate and the organic layer was washed with water. The organic extract was then dried over magnesium sulfate. Following concentration under reduced pressure, the resulting residue was purified by silica gel column chromatography (hexane/ethyl acetate=100/0→40/60) to afford (S)-cyanomethyl 4-(benzylthio)-4-oxo-2-(pent-4-enamido)butanoate (Compound 1g-ID) (885.2 mg, 79%).

LCMS (ESI) m/z=361 (M+H)+
Retention time: 0.91 min (analysis condition SQDAA05)

2. Synthesis of 1g-IE 2-1. Synthesis of (S)-4-oxo-2-(pent-4-enamido)-4-(phenethylthio)butanoic Acid (Compound 1f-IE)

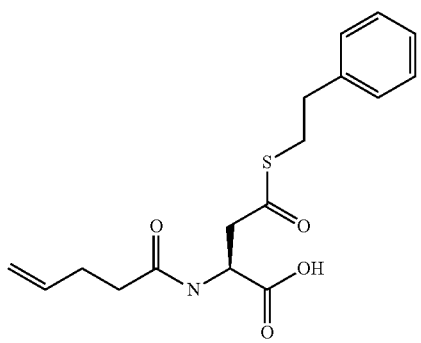 [SMILES: C=CCCC(=O)N[C@@H](CC(=O)SCCc1ccccc1)C(=O)O]

(S)-4-Oxo-2-(pent-4-enamido)-4-(phenethylthio)butanoic acid (Compound 1f-IE) (607 mg, 49%) was obtained using the mixed crude product A (1.3 g, 6.65 mmol) of (S)-4-(tert-butoxy)-4-oxo-3-(pent-4-enamido)butanoic acid (Compound 1b-I) and pent-4-enoic acid (1:0.8) and further using 2-phenylethanethiol (0.889 ml, 6.63 mmol) in place of phenylmethanethiol under the same conditions as in the preparation example for Compound 1f-ID.

LCMS (ESI) m/z=336 (M+H)+
Retention time: 0.83 min (analysis condition SQDAA05)

2-2. Synthesis of (S)-cyanomethyl 4-oxo-2-(pent-4-enamido)-4-(phenethylthio)butanoate (Compound 1g-IE)

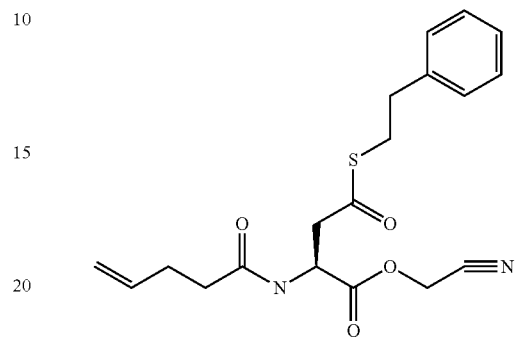

N-Ethyl-N-isopropylpropan-2-amine (0.187 ml, 1.07 mmol) was added to a solution of ((S)-4-oxo-2-(pent-4-enamido)-4-(phenethylthio)butanoic acid (Compound 1f-IE) (300 mg, 0.894 mmol) in 2-bromoacetonitrile (1.87 ml), and the mixture was stirred at room temperature for 30 minutes. A saturated aqueous ammonium chloride solution (5 ml) was added to the reaction mixture, after which the mixture was extracted with ethyl acetate and the organic layer was washed with water. The organic extract was then dried over magnesium sulfate. Following concentration under reduced pressure, the resulting residue was purified by silica gel column chromatography (hexane/ethyl acetate=100/0→60/40) to afford (S)-cyanomethyl 4-oxo-2-(pent-4-enamido)-4-(phenethylthio)butanoate (Compound 1g-IE) (295 mg, 88%).

LCMS (ESI) m/z=375 (M+H)+
Retention time: 0.95 min (analysis condition SQDAA05)

3. Synthesis of 1g-IG 3-1. Synthesis of (S)-4-(ethylthio)-4-oxo-2-(pent-4-enamido)butanoic Acid (Compound 1f-IG)

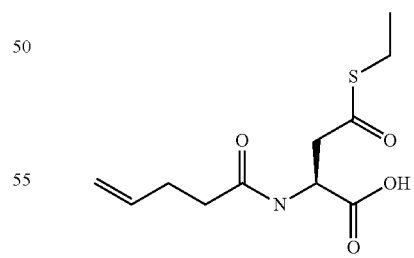

(S)-4-(Ethylthio)-4-oxo-2-(pent-4-enamido)butanoic acid (Compound 1f-IG) (233 mg, 36%) was obtained using the mixed crude product A (889 mg, 4.55 mmol) of (S)-4-(tert-butoxy)-4-oxo-3-(pent-4-enamido)butanoic acid (Compound 1b-I) and pent-4-enoic acid (1:0.8) and further using ethanethiol (0.338 ml, 4.56 mmol) in place of phenylmethanethiol under the same conditions as in the preparation example for Compound 1f-ID.

3-2. Synthesis of (S)-cyanomethyl 4-(ethylthio)-4-oxo-2-(pent-4-enamido)butanoate (Compound 1g-IG)

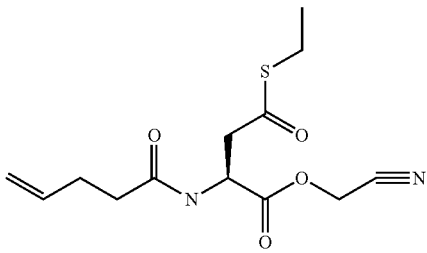 [SMILES: C=CCCC(=O)N[C@@H](CC(=O)SCC)C(=O)OCC#N]

(S)-Cyanomethyl 4-(ethylthio)-4-oxo-2-(pent-4-enamido)butanoate (Compound 1g-IG) (59.8 mg, 52%) was obtained using (S)-4-(ethylthio)-4-oxo-2-(pent-4-enamido)butanoic acid (Compound 1f-IG) (100 mg, 0.386 mmol) in place of (S)-4-(benzylthio)-4-oxo-2-(pent-4-enamido)butanoic acid (Compound 1f-ID) under the same conditions as in the preparation example for Compound 1g-ID.

LCMS (ESI) m/z=299 (M+H)+

Retention time: 0.69 min (analysis condition SQDFA05)

4. Synthesis of 1g-IB

4-1. Synthesis of (S)-4-(isopropylthio)-4-oxo-2-(pent-4-enamido)butanoic Acid (Compound 1f-IB)

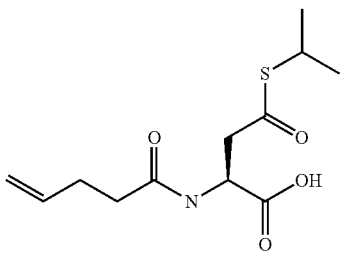 [SMILES: C=CCCC(=O)N[C@@H](CC(=O)SC(C)C)C(=O)O]

(S)-4-(Isopropylthio)-4-oxo-2-(pent-4-enamido)butanoic acid (Compound 1f-IB) (485 mg, 76%) was obtained using the mixed crude product A (788 mg, 4.23 mmol) of (S)-4-(tert-butoxy)-4-oxo-3-(pent-4-enamido)butanoic acid (Compound 1b-I) and pent-4-enoic acid (1:0.8) and further using propane-2-thiol (0.393 ml, 4.23 mmol) in place of phenylmethanethiol under the same conditions as in the preparation example for Compound 1f-ID.

LCMS (ESI) m/z=274 (M+H)+

Retention time: 0.70 min (analysis condition SQDAA05)

4-2. Synthesis of (S)-cyanomethyl 4-(isopropylthio)-4-oxo-2-(pent-4-enamido)butanoate (Compound 1g-IB)

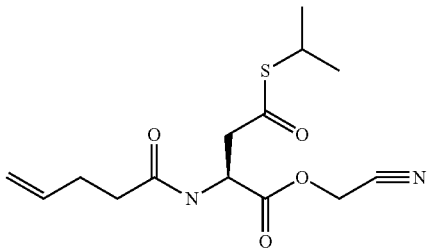 [SMILES: C=CCCC(=O)N[C@@H](CC(=O)SC(C)C)C(=O)OCC#N]

2-Bromoacetonitrile (0.510 ml, 7.32 mmol) and N-ethyl-N-isopropylpropan-2-amine (0.153 ml, 0.878 mmol) were added to a solution of (S)-4-(isopropylthio)-4-oxo-2-(pent-4-enamido)butanoic acid (Compound 1f-IB) (200 mg, 0.732 mmol) in DMF (1 ml), and the mixture was stirred at room temperature for 30 minutes. A saturated aqueous ammonium chloride solution (1 ml) was added to the reaction mixture, after which the mixture was extracted with ethyl acetate and the organic layer was washed with water. The organic extract was then dried over magnesium sulfate. Following concentration under reduced pressure, the resulting residue was purified by silica gel column chromatography (hexane/ethyl acetate=100/0→60/40) to afford (S)-cyanomethyl 4-(isopropylthio)-4-oxo-2-(pent-4-enamido)butanoate (Compound 1g-IB) (161 mg, 70%).

LCMS (ESI) m/z=313 (M+H)+

Retention time: 0.75 min (analysis condition SQDFA05)

5. Synthesis of 1g-IC

5-1. Synthesis of (S)-4-(tert-butylthio)-4-oxo-2-(pent-4-enamido)butanoic Acid (Compound 1f-IC)

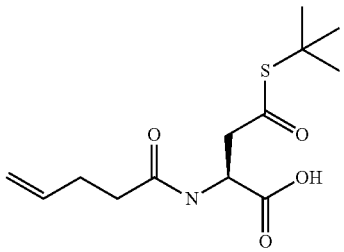 [SMILES: C=CCCC(=O)N[C@@H](CC(=O)SC(C)(C)C)C(=O)O]

(S)-4-(tert-Butylthio)-4-oxo-2-(pent-4-enamido)butanoic acid (Compound 1f-IC) (653 mg, 62%) was obtained using the mixed crude product A (1.23 g, 6.64 mmol) of (S)-4-(tert-butoxy)-4-oxo-3-(pent-4-enamido)butanoic acid (Compound 1b-I) and pent-4-enoic acid (1:0.8) and further using 2-methylpropane-2-thiol (0.748 ml, 6.63 mmol) in place of phenylmethanethiol under the same conditions as in the preparation example for Compound 1f-ID.

LCMS (ESI) m/z=288 (M+H)+

Retention time: 0.79 min (analysis condition SQDAA05)

5-2. Synthesis of (S)-cyanomethyl 4-(tert-butyl-thio)-4-oxo-2-(pent-4-enamido)butanoate (Compound 1g-IC)

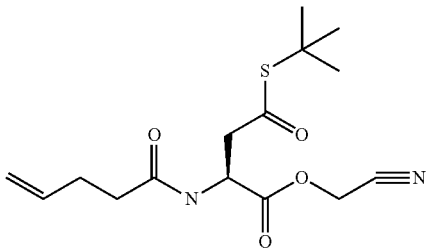 [SMILES: C=CCCC(=O)N[C@@H](CC(=O)SC(C)(C)C)C(=O)OCC#N]

(S)-Cyanomethyl 4-(tert-butylthio)-4-oxo-2-(pent-4-enamido)butanoate (Compound 1g-IC) (293 mg, 86%) was obtained using (S)-4-(tert-butylthio)-4-oxo-2-(pent-4-enamido)butanoic acid (Compound 1f-IC) (300 mg, 1.04 mmol) in place of ((S)-4-oxo-2-(pent-4-enamido)-4-(phenethyl-thio)butanoic acid (Compound 1f-IE) under the same conditions as in the preparation example for Compound 1g-IE.

LCMS (ESI) m/z=327 (M+H)+
Retention time: 0.90 min (analysis condition SQDAA05)

6. Synthesis of 1e-IF

6-1. Synthesis of (S)-tert-butyl 4-oxo-2-(pent-4-enamido)-4-(phenylthio)butanoate (Compound 1e-IF)

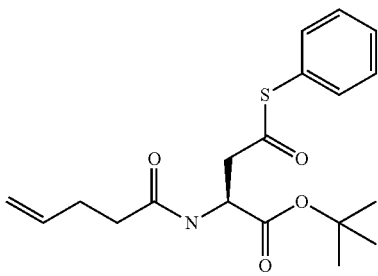 [SMILES: C=CCCC(=O)N[C@@H](CC(=O)Sc1ccccc1)C(=O)OC(C)(C)C]

DIC (2.43 ml, 15.6 mmol), DMAP (318 mg, 2.60 mmol) and benzenethiol (1.59 ml, 15.6 mmol) were added to a solution of the mixed crude product A (2.53 g, 13.0 mmol) of (S)-4-(tert-butoxy)-4-oxo-3-(pent-4-enamido)butanoic acid (Compound 1b-I) and pent-4-enoic acid (1:0.8) in $CH_2Cl_2$ (35 ml), and the mixture was stirred at room temperature for 4 hours. The reaction mixture was filtered, and the resulting filtrate was concentrated, diluted with ethyl acetate and then washed with a saturated aqueous ammonium chloride solution, saturated aqueous sodium bicarbonate and brine. The organic extract was then dried over magnesium sulfate and concentrated under reduced pressure. The resulting residue was purified by reverse-phase silica gel column chromatography (10 mM aqueous ammonium acetate solution/methanol=70/30→0/100, and the resulting crude product was further purified by silica gel column chromatography (hexane/ethyl acetate=100/0→65/35) to afford (S)-tert-butyl 4-oxo-2-(pent-4-enamido)-4-(phenylthio)butanoate (Compound 1e-IF) (1.99 g, 79%).

LCMS (ESI) m/z=364 (M+H)+
Retention time: 1.01 min (analysis condition SQDAA05)

7. Synthesis of 1g-IA

7-1. Synthesis of (S)-tert-butyl 4-(methylthio)-4-oxo-2-(pent-4-enamido)butanoate (Compound 1e-IA)

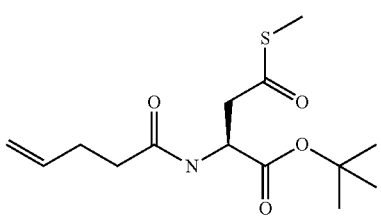 [SMILES: C=CCCC(=O)N[C@@H](CC(=O)SC)C(=O)OC(C)(C)C]

$Et_3N$ (1.54 ml, 11.0 mmol) and ethyl carbonochloridate (1.05 ml, 11.0 mmol) were added to a solution of the mixed crude product A (1.96 g, 9.68 mmol) of (S)-4-(tert-butoxy)-4-oxo-3-(pent-4-enamido)butanoic acid (Compound 1b-I) and pent-4-enoic acid (1:0.8) in THF (44 ml), and the mixture was stirred at room temperature for 25 minutes. A solution of sodium methanethiolate (1.06 g, 15.1 mmol) in DMF (18 ml) was then added to the reaction mixture, which was stirred at room temperature for 1 hour. Water was then added to the reaction mixture, followed by dilution with dichloromethane. The organic layer was washed with water, and then dried over magnesium sulfate and concentrated under reduced pressure. The resulting residue was purified by reverse-phase silica gel column chromatography (10 mM aqueous ammonium acetate solution/methanol=70/30→40/60) to afford (S)-tert-butyl 4-(methylthio)-4-oxo-2-(pent-4-enamido)butanoate (Compound 1e-IA) (1.38 g, 85%).

LCMS (ESI) m/z=302 (M+H)+
Retention time: 0.90 min (analysis condition SQDAA05)

7-2. Synthesis of (S)-4-(methylthio)-4-oxo-2-(pent-4-enamido)butanoic Acid (Compound 1f-IA)

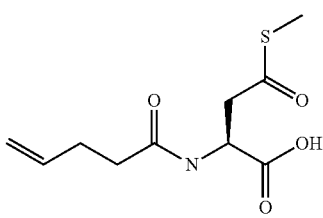 [SMILES: C=CCCC(=O)N[C@@H](CC(=O)SC)C(=O)O]

Trifluoroacetic acid (0.684 ml, 9.20 mmol) was added to a solution of (S)-tert-butyl 4-(methylthio)-4-oxo-2-(pent-4-enamido)butanoate (Compound 1e-IA, 69.3 mg, 0.23 mmol) in dichloromethane (1.2 ml), and the mixture was stirred at room temperature for 6.5 hours. The reaction mixture was then concentrated under reduced pressure, and the residue was purified by reverse-phase silica gel column chromatography (10 mM aqueous ammonium acetate solution/methanol=100/0→60/40) to afford (S)-4-(methylthio)-4-oxo-2-(pent-4-enamido)butanoic acid (Compound 1f-IA) (46.9 mg, 83%).

7-3. Synthesis of (S)-cyanomethyl 4-(methylthio)-4-oxo-2-(pent-4-enamido)butanoate (Compound 1g-IA)

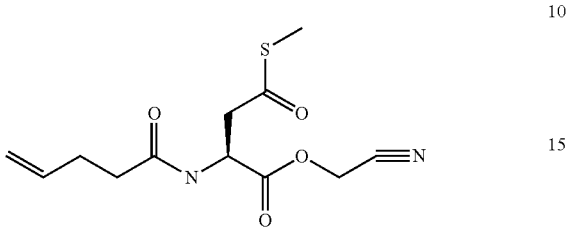

2-Bromoacetonitrile (2.64 ml, 37.8 mmol) and N-ethyl-N-isopropylpropan-2-amine (3.29 ml, 18.9 mmol) were added to a solution of (S)-4-(methylthio)-4-oxo-2-(pent-4-enamido)butanoic acid (Compound 1f-IA) (1.17 g, 3.78 mmol) in DMF (5 ml), and the mixture was stirred at room temperature for 30 minutes. A saturated aqueous ammonium chloride solution (3 ml) was added to the reaction mixture, after which the mixture was extracted with ethyl acetate and the organic layer was washed with water. The organic extract was then dried over magnesium sulfate. Following concentration under reduced pressure, the resulting residue was purified by silica gel column chromatography (hexane/ethyl acetate=100/0→30/70) to afford (S)-cyanomethyl 4-(methylthio)-4-oxo-2-(pent-4-enamido)butanoate (Compound 1g-IA) (368 mg, 34%).

LCMS (ESI) m/z=285 (M+H)+

Retention time: 0.69 min (analysis condition SQDAA05)

8. Synthesis of 1g-IID

8-1. Synthesis of (S)-5-(tert-butoxy)-5-oxo-4-(pent-4-enamido)pentanoic Acid (Compound 1b-II)

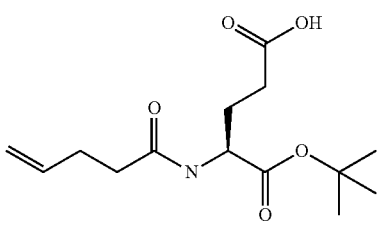 [SMILES: C=CCCC(=O)N[C@@H](CCC(=O)O)C(=O)OC(C)(C)C]

A mixed crude product B (9.28 g, 100%) of (S)-5-(tert-butoxy)-5-oxo-4-(pent-4-enamido)pentanoic acid (Compound 1b-II) and pent-4-enoic acid (1:0.8) was obtained using (S)-4-amino-5-(tert-butoxy)-5-oxopentanoic acid (Compound 1a-II, 5.00 g, 24.2 mmol) in place of (S)-3-amino-4-(tert-butoxy)-4-oxobutanoic acid (Compound 1a-I) under the same conditions as in the preparation example for Compound 1b-I.

8-2. Synthesis of (S)-5-(benzylthio)-5-oxo-2-(pent-4-enamido)pentanoic acid (Compound 1f-IID)

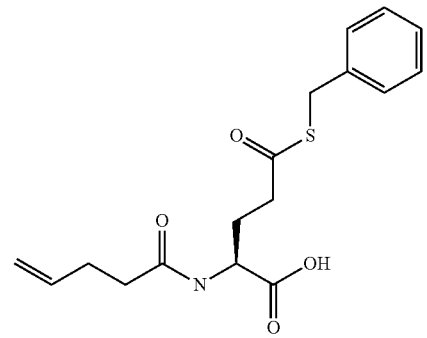 [SMILES: C=CCCC(=O)N[C@@H](CCC(=O)SCc1ccccc1)C(=O)O]

(S)-5-(Benzylthio)-5-oxo-2-(pent-4-enamido)pentanoic acid (Compound 1f-IID) (1.45 g, 72%) was obtained using the mixed crude product B (2.30 g, 10.80 mmol) in place of the mixed crude product A under the same conditions as in the preparation example for Compound 1f-ID.

LCMS (ESI) m/z=336 (M+H)+

Retention time: 0.82 min (analysis condition SQDAA05)

8-3. Synthesis of (S)-cyanomethyl 5-(benzylthio)-5-oxo-2-(pent-4-enamido)pentanoate (Compound 1g-IID)

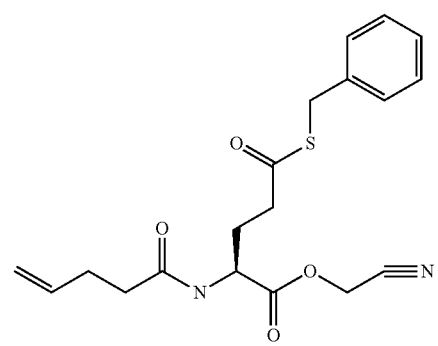 [SMILES: C=CCCC(=O)N[C@@H](CCC(=O)SCc1ccccc1)C(=O)OCC#N]

(S)-Cyanomethyl 5-(benzylthio)-5-oxo-2-(pent-4-enamido)pentanoate (Compound 1g-IID) (951 mg, 89%) was obtained using (S)-5-(benzylthio)-5-oxo-2-(pent-4-enamido)pentanoic acid (Compound 1f-IID) (964 mg, 2.87 mmol) in place of (S)-4-(benzylthio)-4-oxo-2-(pent-4-enamido)butanoic acid (Compound 1f-ID) under the same conditions as in the preparation example for Compound 1g-ID.

LCMS (ESI) m/z=375 (M+H)+

Retention time: 0.93 min (analysis condition SQDAA05)

9. Synthesis of 1g-IIA

9-1. Synthesis of (S)-tert-butyl 5-(methylthio)-5-oxo-2-(pent-4-enamido)pentanoate (Compound 1e-IIA)

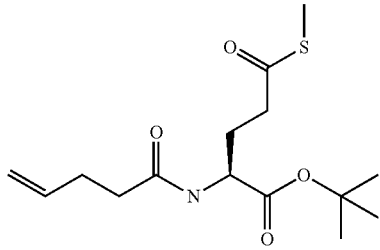 [SMILES: C=CCCC(=O)N[C@@H](CCC(=O)SC)C(=O)OC(C)(C)C]

(S)-tert-Butyl 5-(methylthio)-5-oxo-2-(pent-4-enamido)pentanoate (Compound 1e-IIA) (1.22 g, 76%) was obtained using the mixed crude product B (1.94 g, 9.11 mmol) in place of the mixed crude product A under the same conditions as in the preparation example for Compound 1e-IA.

LCMS (ESI) m/z=316 (M+H)+

Retention time: 0.92 min (analysis condition SQDAA05)

9-2. Synthesis of (S)-5-(methylthio)-5-oxo-2-(pent-4-enamido)pentanoic Acid (Compound 1f-IIA)

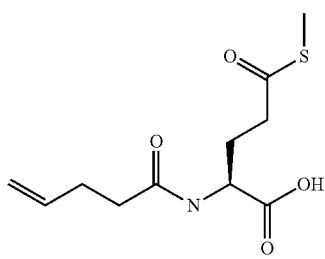 [SMILES: C=CCCC(=O)N[C@@H](CCC(=O)SC)C(=O)O]

(S)-5-(Methylthio)-5-oxo-2-(pent-4-enamido)pentanoic acid (Compound 1f-IIA) (790 mg, 94%) was obtained using (S)-tert-butyl 5-(methylthio)-5-oxo-2-(pent-4-enamido)pentanoate (Compound 1e-IIA) (1.02 g, 3.24 mmol) in place of (S)-tert-butyl 4-(methylthio)-4-oxo-2-(pent-4-enamido)butanoate (Compound 1e-IA) under the same conditions as in the preparation example for Compound 1f-IA.

LCMS (ESI) m/z=260 (M+H)+

Retention time: 0.54 min (analysis condition SQDAA05)

9-3. Synthesis of (S)-cyanomethyl 5-(methylthio)-5-oxo-2-(pent-4-enamido)pentanoate (Compound 1g-IIA)

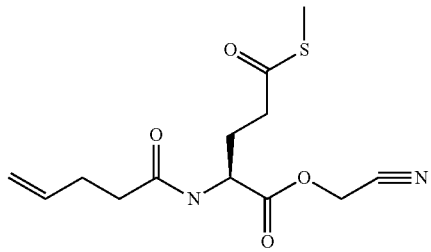 [SMILES: C=CCCC(=O)N[C@@H](CCC(=O)SC)C(=O)OCC#N]

2-Bromoacetonitrile (3.60 ml, 52.0 mmol) and N-ethyl-N-isopropylpropan-2-amine (0.297 ml, 2.86 mmol) were added to a solution of (S)-5-(methylthio)-5-oxo-2-(pent-4-enamido)pentanoic acid (Compound 1f-IIA) (673 mg, 2.60 mmol) in DMSO (5.5 ml), and the mixture was stirred at room temperature for 30 minutes. A saturated aqueous ammonium chloride solution (3 ml) was added to the reaction mixture, after which the mixture was extracted with ethyl acetate and the organic layer was washed with water. The organic extract was then dried over magnesium sulfate. Following concentration under reduced pressure, the resulting residue was purified by silica gel column chromatography (hexane/ethyl acetate=100/0→30/70) to afford (S)-cyanomethyl 5-(methylthio)-5-oxo-2-(pent-4-enamido)pentanoate (Compound 1g-IIA) (772 mg, 100%).

LCMS (ESI) m/z=299 (M+H)+

Retention time: 0.75 min (analysis condition SQDAA05)

10. Synthesis of 1g-IIF

10-1. Synthesis of (S)-tert-butyl 5-oxo-2-(pent-4-enamido)-5-(phenylthio)pentanoate (Compound 1e-IIF)

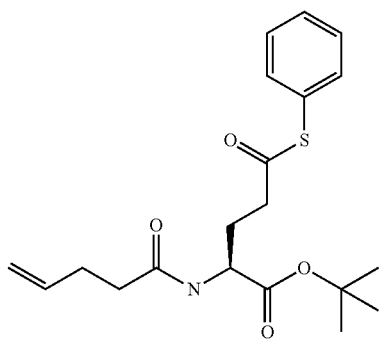 [SMILES: C=CCCC(=O)N[C@@H](CCC(=O)Sc1ccccc1)C(=O)OC(C)(C)C]

(S)-tert-Butyl 5-oxo-2-(pent-4-enamido)-5-(phenylthio)pentanoate (Compound 1e-IIF) (1.52 g, 73%) was obtained using the mixed product B (2.11 g, 9.90 mmol) in place of the mixed crude product A under the same conditions as in the preparation example for Compound 1e-IF.

LCMS (ESI) m/z=378 (M+H)+

Retention time: 1.03 min (analysis condition SQDAA05)

10-2. Synthesis of (S)-cyanomethyl 5-oxo-2-(pent-4-enamido)-5-(phenylthio)pentanoate (Compound 1g-IIF)

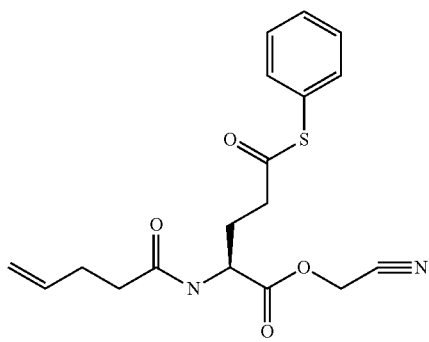 [SMILES: C=CCCC(=O)N[C@@H](CCC(=O)Sc1ccccc1)C(=O)OCC#N]

Trifluoroacetic acid (3.85 ml, 51.8 mmol) was added to a solution of (S)-tert-butyl 5-oxo-2-(pent-4-enamido)-5-(phenylthio)pentanoate (Compound 1e-IIF) (978 mg, 2.59 mmol) in dichloromethane (6.74 ml), and the mixture was stirred at room temperature for 3 hours. The reaction mixture was then concentrated under reduced pressure. N-Ethyl-N-isopropylpropan-2-amine (1.30 ml, 7.47 mmol) was added to a solution of the resulting residue in 2-bromoacetonitrile (8 ml), and the mixture was stirred at room temperature for 30 minutes. After adding water to the reaction mixture, purification by reverse phase silica gel column chromatography (10 mM aqueous ammonium acetate solution/methanol=60/40→20/80) afforded (S)-cyanomethyl 5-oxo-2-(pent-4-enamido)-5-(phenylthio)pentanoate (Compound 1g-IIF) (722 mg, 64%).

LCMS (ESI) m/z=361 (M+H)+

Retention time: 0.89 min (analysis condition SQDAA05)

[Example 2] Synthesis of Aminoacylated pdCpAs Having Side Chain Carboxylic Acid Converted to Active Ester Aminoacylated pdCpAs (Compounds 1i) were synthesized using the compounds synthesized in Example 1 having side chain carboxylic acid converted to active ester (Compounds 1g).

1. Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-(benzylthio)-4-oxo-2-(pent-4-enamido)butanoate (Compound 1i-ID)

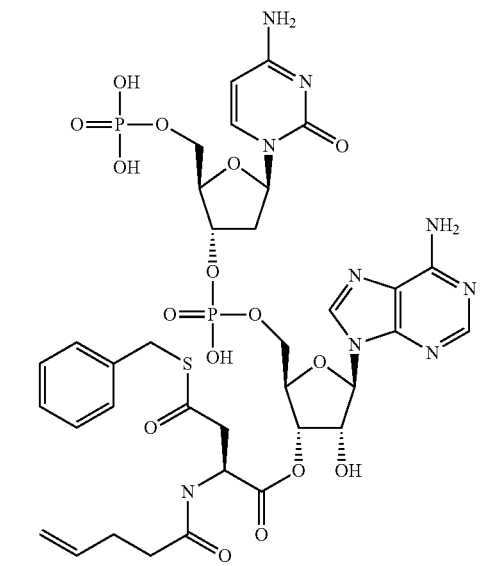 [SMILES: C=CCCC(=O)N[C@@H](CC(=O)SCc1ccccc1)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

pdCpA (((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate; Compound 1h) was synthesized according to the literature, Nucleosides, Nucleotides & Nucleic Acids, 20(3), 197-211; 2001, Xue-Feng Zhu and A. Ian Scott.

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (200 mg, 0.314 mmol) in water (6.25 ml) and a solution of (S)-cyanomethyl 4-(benzylthio)-4-oxo-2-(pent-4-enamido)butanoate (Compound 1g-ID) (454 mg, 1.26 mmol) in tetrahydrofuran (3.15 ml) were added to buffer A (113 ml), and the mixture was stirred at room temperature for 1 hour. Trifluoroacetic acid (2.52 ml, 33.9 mmol) was then added, followed by lyophilization. The resulting residue was purified by reverse-phase silica gel column chromatography (0.05% aqueous trifluoroacetic acid solution/0.05% trifluoroacetic acid-acetonitrile solution=100/0→60/40) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-(benzylthio)-4-oxo-2-(pent-4-enamido)butanoate (Compound 1i-ID) (70.9 mg, 24%).

LCMS (ESI) m/z=940 (M+H)+

Retention time: 0.53 min (analysis condition SQDFA05)

Buffer A was prepared as follows.

Acetic acid was added to an aqueous solution of N,N,N-trimethylhexadecan-1-aminium chloride (6.40 g, 20 mmol)

and imidazole (6.81 g, 100 mmol) to afford buffer A of 20 mM N,N,N-trimethylhexadecan-1-aminium and 100 mM imidazole, pH 8 (1 L).

2. Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-oxo-2-(pent-4-enamido)-4-(phenethylthio)butanoate (Compound 1i-IE)

3. Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-(ethylthio)-4-oxo-2-(pent-4-enamido)butanoate (Compound 1i-IG)

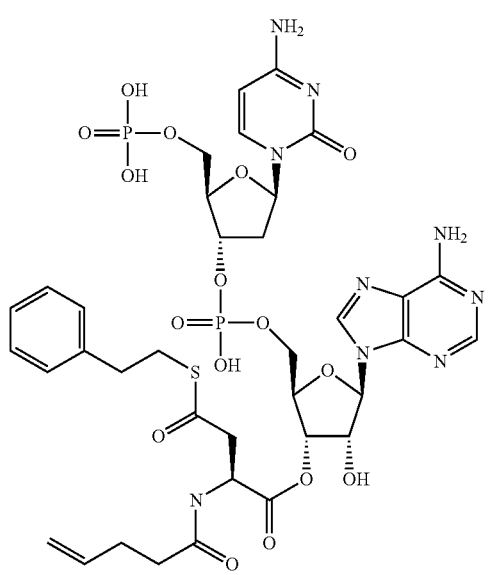 [SMILES: C=CCCC(=O)N[C@@H](CC(=O)SCCc1ccccc1)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

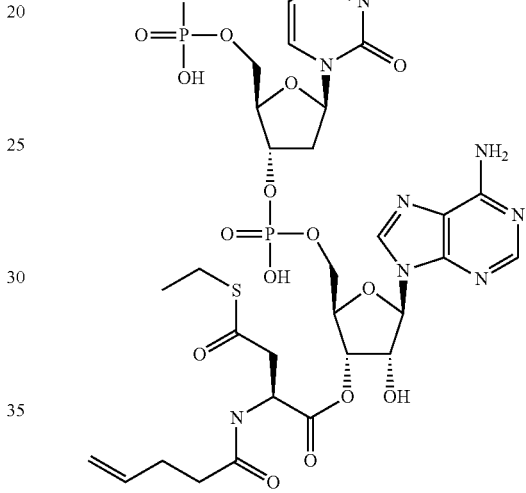

(2S)-(2R,3S,4R,5R)-2-((((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-oxo-2-(pent-4-enamido)-4-(phenethylthio)butanoate (Compound 1i-IE) (22.8 mg, 30%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (50 mg, 0.079 mol) and further using (S)-cyanomethyl 4-oxo-2-(pent-4-enamido)-4-(phenethylthio)butanoate (Compound 1g-IE) (118 mg, 0.314 mmol) in place of (S)-cyanomethyl 4-(benzylthio)-4-oxo-2-(pent-4-enamido)butanoate (Compound 1g-ID) under the same conditions as in the preparation example for Compound 1i-ID.

LCMS (ESI) m/z=954 (M+H)+

Retention time: 0.80 min (analysis condition SMD method 1)

(2S)-(2R,3S,4R,5R)-2-((((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-(ethylthio)-4-oxo-2-(pent-4-enamido)butanoate (Compound 1i-IG) (23.9 mg, 35%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (50 mg, 0.079 mmol) and further using (S)-cyanomethyl 4-(ethylthio)-4-oxo-2-(pent-4-enamido)butanoate (Compound 1g-IG) (94 mg, 0.314 mmol) in place of (S)-cyanomethyl 4-(benzylthio)-4-oxo-2-(pent-4-enamido)butanoate (Compound 1g-ID) under the same conditions as in the preparation example for Compound 1i-ID.

LCMS (ESI) m/z=878 (M+H)+

Retention time: 0.66 min (analysis condition SMD method 1)

4. Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-(isopropylthio)-4-oxo-2-(pent-4-enamido)butanoate (Compound 1i-IB)

5. Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-(tert-butylthio)-4-oxo-2-(pent-4-enamido)butanoate (Compound 1i-IC)

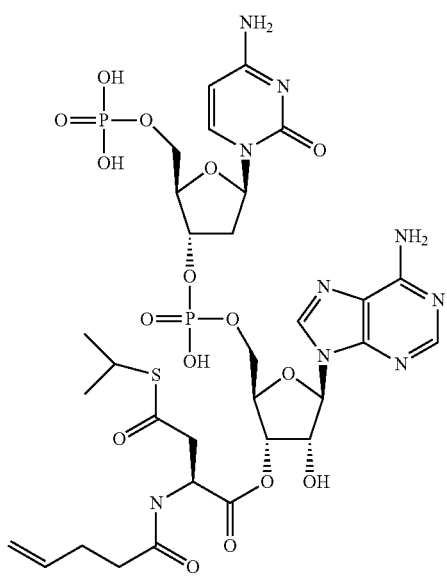 [SMILES: C=CCCC(=O)N[C@@H](CC(=O)SC(C)C)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

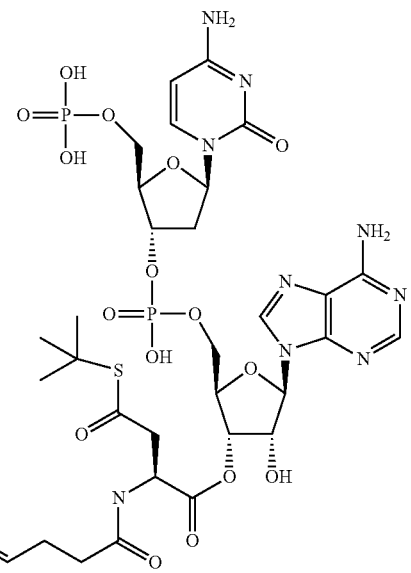

(2S)-(2R,3S,4R,5R)-2-(((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-(isopropylthio)-4-oxo-2-(pent-4-enamido)butanoate (Compound 1i-IB) (27.3 mg, 39%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (50 mg, 0.079 mmol) and further using (S)-cyanomethyl 4-(isopropylthio)-4-oxo-2-(pent-4-enamido)butanoate (Compound 1g-IB) (98 mg, 0.314 mmol) in place of (S)-cyanomethyl 4-(benzylthio)-4-oxo-2-(pent-4-enamido)butanoate (Compound 1g-ID) under the same conditions as in the preparation example for Compound 1i-ID.

LCMS (ESI) m/z=892 (M+H)+

Retention time: 0.70 min (analysis condition SMD method 1)

(2S)-(2R,3S,4R,5R)-2-(((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-(tert-butylthio)-4-oxo-2-(pent-4-enamido)butanoate (Compound 1i-IC) (26.2 mg, 37%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (50 mg, 0.079 mmol) and further using (S)-cyanomethyl 4-(tert-butylthio)-4-oxo-2-(pent-4-enamido)butanoate (Compound 1g-IC) (103 mg, 0.314 mmol) in place of (S)-cyanomethyl 4-(benzylthio)-4-oxo-2-(pent-4-enamido)butanoate (Compound 1g-ID) under the same conditions as in the preparation example for Compound 1i-ID.

LCMS (ESI) m/z=906 (M+H)+

Retention time: 0.74 min (analysis condition SMD method 1)

6. Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-(methylthio)-4-oxo-2-(pent-4-enamido)butanoate (Compound 1i-IA)

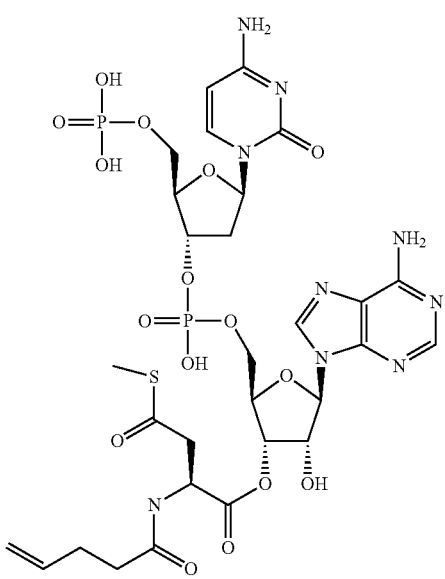 [SMILES: C=CCCC(=O)N[C@@H](CC(=O)SC)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

(2S)-(2R,3S,4R,5R)-2-((((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-(methylthio)-4-oxo-2-(pent-4-enamido)butanoate (Compound 1i-IA) (83.6 mg, 41%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (150 mg, 0.236 mmol) and further using (S)-cyanomethyl 4-(methylthio)-4-oxo-2-(pent-4-enamido)butanoate (Compound 1g-IA) (268 mg, 0.943 mmol) in place of (S)-cyanomethyl 4-(benzylthio)-4-oxo-2-(pent-4-enamido)butanoate (Compound 1g-ID) under the same conditions as in the preparation example for Compound 1i-ID.

LCMS (ESI) m/z=864 (M+H)+

Retention time: 0.40 min (analysis condition SQDFA05)

7. Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-(benzylthio)-5-oxo-2-(pent-4-enamido)pentanoate (Compound 1i-IID)

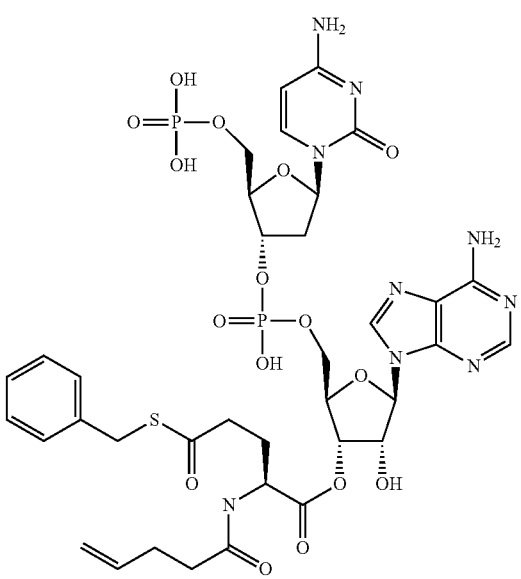 [SMILES: C=CCCC(=O)N[C@@H](CCC(=O)SCc1ccccc1)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

(2S)-(2R,3S,4R,5R)-2-((((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-(benzylthio)-5-oxo-2-(pent-4-enamido)pentanoate (Compound 1i-IID) (31.3 mg, 10%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (200 mg, 0.314 mol) and further using (S)-cyanomethyl 5-(benzylthio)-5-oxo-2-(pent-4-enamido)pentanoate (Compound 1g-IID) (472 mg, 1.26 mmol) in place of (S)-cyanomethyl 4-(benzylthio)-4-oxo-2-(pent-4-enamido)butanoate (Compound 1g-ID) under the same conditions as in the preparation example for Compound 1i-ID.

LCMS (ESI) m/z=954 (M+H)+

Retention time: 0.55 min (analysis condition SQDFA05)

8. Synthesis of (2S)-(2R,3S,4R,5R)-2-((((((2R,3S, 5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-(methylthio)-5-oxo-2-(pent-4-enamido)pentanoate (Compound 1i-IIA)

9. Synthesis of (2S)-(2R,3S,4R,5R)-2-((((((2R,3S, 5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-oxo-2-(pent-4-enamido)-5-(phenylthio)pentanoate (Compound 1i-IIF)

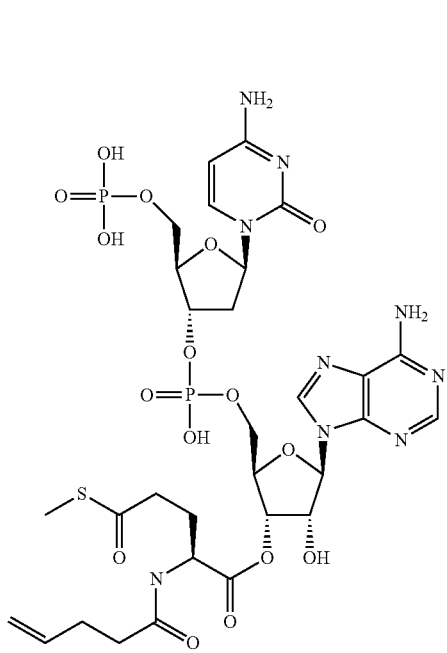 [SMILES: C=CCCC(=O)N[C@@H](CCC(=O)SC)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

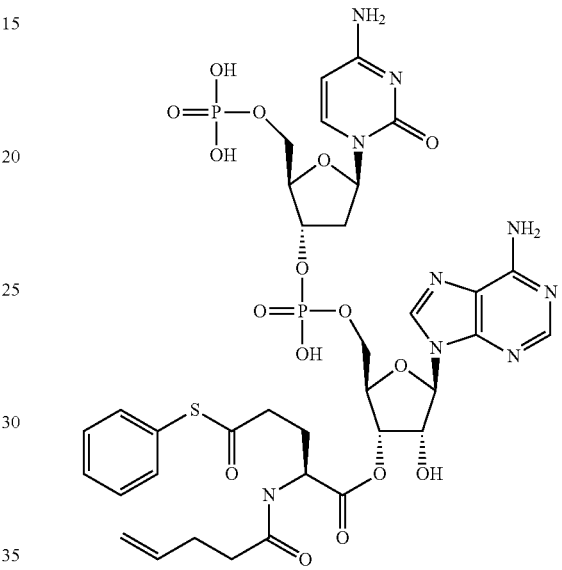

(2S)-(2R,3S,4R,5R)-2-((((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-(methylthio)-5-oxo-2-(pent-4-enamido)pentanoate (Compound 1i-IIA) (68.0 mg, 25%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (200 mg, 0.314 mmol) and further using (S)-cyanomethyl 5-(methylthio)-5-oxo-2-(pent-4-enamido)pentanoate (Compound 1g-IIA) (376 mg, 1.26 mmol) in place of (S)-cyanomethyl 4-(benzylthio)-4-oxo-2-(pent-4-enamido)butanoate (Compound 1g-ID) under the same conditions as in the preparation example for Compound 1i-ID.

LCMS (ESI) m/z=878 (M+H)+

Retention time: 0.43 min (analysis condition SQDFA05)

(2S)-(2R,3S,4R,5R)-2-((((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-oxo-2-(pent-4-enamido)-5-(phenylthio)pentanoate (Compound 1i-IIF) and two estimated compounds in which the thioester site is intramolecularly condensed with the alcohol site or amino group site of the pdCpA site in Compound 1i-IIF (Compound 1i-IIF-B1 and Compound 1i-IIF-B2) were observed by LCMS analysis using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (150 mg, 0.236 mmol) and further using (S)-cyanomethyl 5-oxo-2-(pent-4-enamido)-5-(phenylthio)pentanoate (Compound 1g-IIF) (534 mg, 0.944 mmol) in place of (S)-cyanomethyl 4-(benzylthio)-4-oxo-2-(pent-4-enamido)butanoate (Compound 1g-ID) under the same conditions as in the preparation example for Compound 1i-ID. The ratio of Compound 1i-IIF:(Compound 1i-IIF-B1)+(Compound 1i-IIF-B2) was 20:9 based on UV area % by LCMS.

(Compound 1i-IIF)

LCMS (ESI) m/z=940 (M+H)+

Retention time: 0.70 min (analysis condition SQDFA05)

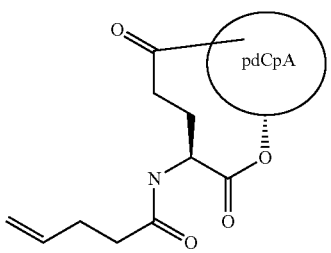

(1i-IIF-B1)
LCMS (ESI) m/z=828 (M–H)–
Retention time: 0.65 min (analysis condition SQDFA05)
(1i-IIF-B2)
LCMS (ESI) m/z=828 (M–H)–
Retention time: 0.66 min (analysis condition SQDFA05)
Aminoacylated pdCpAs having side chains whose carboxylic acids converted to active esters—(For example: Rex1=Me, Et, iPr, Ph, Bz or phenethyl (Compounds 1i)) were synthesized as described in the foregoing.

[Example 3] Synthesis of Aminoacylated tRNAs Having Side Chain Carboxylic Acid Converted to Active Ester Aminoacylated tRNAs having side chain carboxylic acid converted to active ester were synthesized according to the following method.

1. Synthesis of tRNA (Lacking CA) by Transcription tRNAEnAsnGAG (-CA) (SEQ ID NO: R-1) lacking 3'-end CA was synthesized from template DNA (SEQ ID NO: D-1) by in vitro transcription using RiboMAX Large Scale RNA production System T7 (Promega, P1300) and purified with RNeasy Mini kit (Qiagen).

```
SEQ ID NO: D-1
tRNAEnAsnGAG (-CA) DNA sequence:
                                  (SEQ ID NO: 1)
GGCGTAATACGACTCACTATAGGCTCTGTAGTTCAGTCGGTAGAACGGC GGACTgagAATCCGTATGTCACTGGTTCGAGTCCAGTCAGAGCCGC SEQ ID NO: R-1
tRNAEnAsnGAG (-CA) RNA sequence:
                                  (SEQ ID NO: 30)
GGCUCUGUAGUUCAGUCGGUAGAACGGCGGACUgagAAUCCGUAUGUCA

CUGGUUCGAGUCCAGUCAGAGCCGC
```

2. Synthesis of Aminoacylated tRNAs (Compounds AT-1) by Ligation of Aminoacylated pdCpAs Having Side Chain and tRNA (Lacking CA) (SEQ ID NO: R-1)

2 μL of 10× ligation buffer (500 mM HEPES-KOH pH 7.5, 200 mM MgCl$_2$, 10 mM ATP) and 4 μL of nuclease free water were added to 10 μL of 50 μM transcribed tRNAEnAsnGAG (-CA) (SEQ ID NO: R-1). The mixture was heated at 95° C. for 2 minutes and then left to stand at room temperature for 5 minutes, and the tRNA was refolded. 2 μL of 20 units/μL T4 RNA ligase (New England Biolabs) and 2 μL of a 5 mM solution of aminoacylated pdCpA having side chain carboxylic acid converted to active ester (Compound 1i) in DMSO were added, and ligation reaction was carried out at 15° C. for 45 minutes. 4 μL of 3 M sodium acetate and 24 μL of 125 mM iodine (solution in water:THF=1:1) were added to 20 μL of the ligation reaction solution, and deprotection was carried out at room temperature for 1 hour. Aminoacylated tRNA (Compound AT-1) was collected by phenol extraction and ethanol precipitation. Aminoacylated tRNA (Compound AT-1) was dissolved in 1 mM sodium acetate immediately prior to addition to the translation mixture.

(SEQ ID NO: 31)

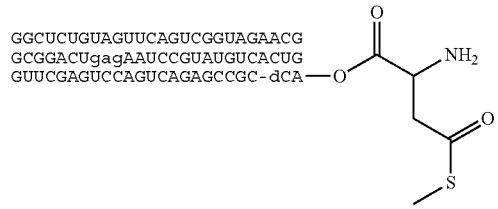

Compound AT-1-IA Asp(SMe)-tRNAEnAsnGAG (SEQ ID NO: 31)

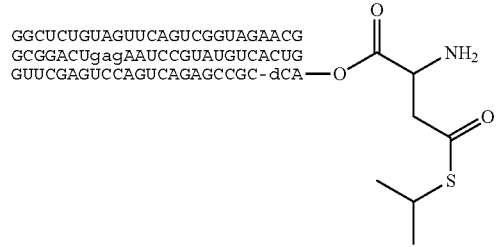

Compound AT-1-IB Asp(SiPr)-tRNAEnAsnGAG (SEQ ID NO: 31)

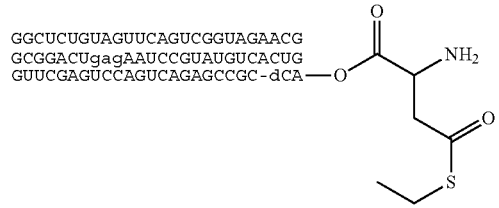

Compound AT-1-IG Asp(SEt)-tRNAEnAsnGAG (SEQ ID NO: 31)

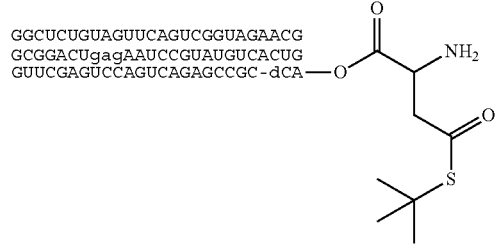

Compound AT-1-IC Asp(StBu)-tRNAEnAsnGAG

-continued (SEQ ID NO: 31)

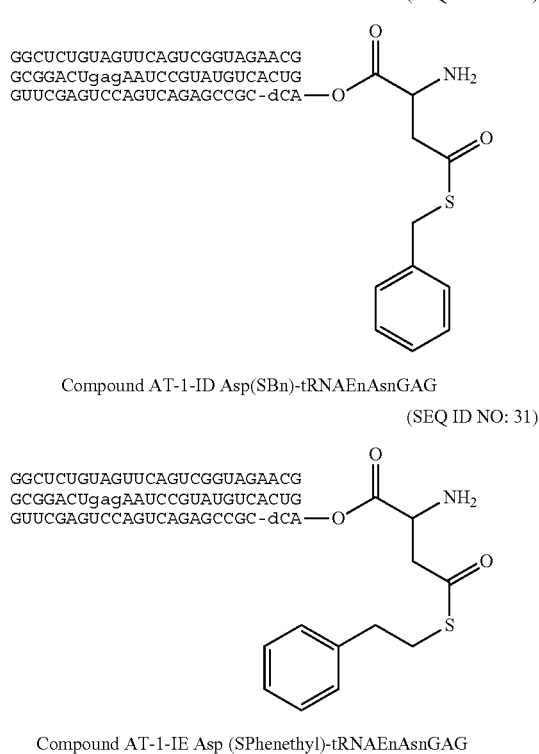

```
GGCUCUGUAGUUCAGUCGGUAGAACG
GCGGACUgagAAUCCGUAUGUCACUG
GUUCGAGUCCAGUCAGAGCCGC-dCA
```

Compound AT-1-ID Asp(SBn)-tRNAEnAsnGAG (SEQ ID NO: 31)

```
GGCUCUGUAGUUCAGUCGGUAGAACG
GCGGACUgagAAUCCGUAUGUCACUG
GUUCGAGUCCAGUCAGAGCCGC-dCA
```

Compound AT-1-IE Asp (SPhenethyl)-tRNAEnAsnGAG

Compound AT-1-IIA
Glu(Sme)-tRNAEnAsnGAG
Compound AT-1-IID
Glu(SBn)-tRNAEnAsnGAG

[Example 4] Translation Synthesis Using Amino Acids Having Side Chain Carboxylic Acid Converted to Active Ester Translation synthesis of desired non-proteinogenic amino acid-containing polypeptides was carried out by adding tRNA aminoacylated by various amino acids to a cell-free translation system and initiating translation. The translation system used was PURE system, a prokaryote-derived reconstituted cell-free protein synthesis system including a transcription system from template DNA. Specifically, the synthesis was carried out by adding 0.02 µM template DNA, 300 µM each of proteinogenic amino acids encoded by the template DNA, respectively, and 50 µM aminoacylated tRNA having side chain carboxylic acid converted to active ester (Compound AT-1) to a transcription and translation solution (5% (v/v) T7 RNA polymerase RiboMAX Enzyme Mix (Promega, P1300), 2 mM GTP, 2 mM ATP, 1 mM CTP, 1 mM UTP, 20 mM creatine phosphate, 50 mM HEPES-KOH pH 7.6, 100 mM potassium glutamate, 12 mM magnesium acetate, 2 mM spermidine, 1 mM dithiothreitol, 1.5 mg/ml E. coli MRE600 (RNase-negative)-derived tRNA (Roche), 4 µg/ml creatine kinase, 3 µg/ml myokinase, 2 units/ml inorganic pyrophosphatase, 1.1 µg/ml nucleoside diphosphate kinase, 0.6 µM methionyl tRNA transformylase, 0.26 µM EF-G, 0.25 µM RF1, 0.24 µM RF2, 0.17 µM RF3, 0.5 µM RRF, 2.7 µM IF1, 0.4 µM IF2, 1.5 µM IF3, 40 µM EF-Tu, 84 µM EF-Ts, 1.2 µM ribosome, 0.73 µM AlaRS, 0.03 µM ArgRS, 0.38 µM AsnRS, 0.13 µM AspRS, 0.02 µM CysRS, 0.06 µM GlnRS, 0.23 µM GluRS, 0.09 µM GlyRS, 0.02 µM HisRS, 0.4 µM IleRS, 0.04 µM LeuRS, 0.11 µM LysRS, 0.03 µM MetRS, 0.68 µM PheRS, 0.16 µM ProRS, 0.04 µM SerRS, 0.09 µM ThrRS, 0.03 µM TrpRS, 0.02 µM TyrRS, 0.02 µM ValRS (self-prepared proteins were basically prepared as His-tagged proteins)) and allowing the translation reaction mixture to stand at 37° C. for 30 minutes to 1 hour.

Translational products were identified by measuring MALDI-MS spectra using α-cyano-4-hydroxycinnamic acid as the matrix.

1. Translation Synthesis of a Peptide Containing a Thioesterified Glutamic Acid Derivative (Compound P-1)

Figure 2:
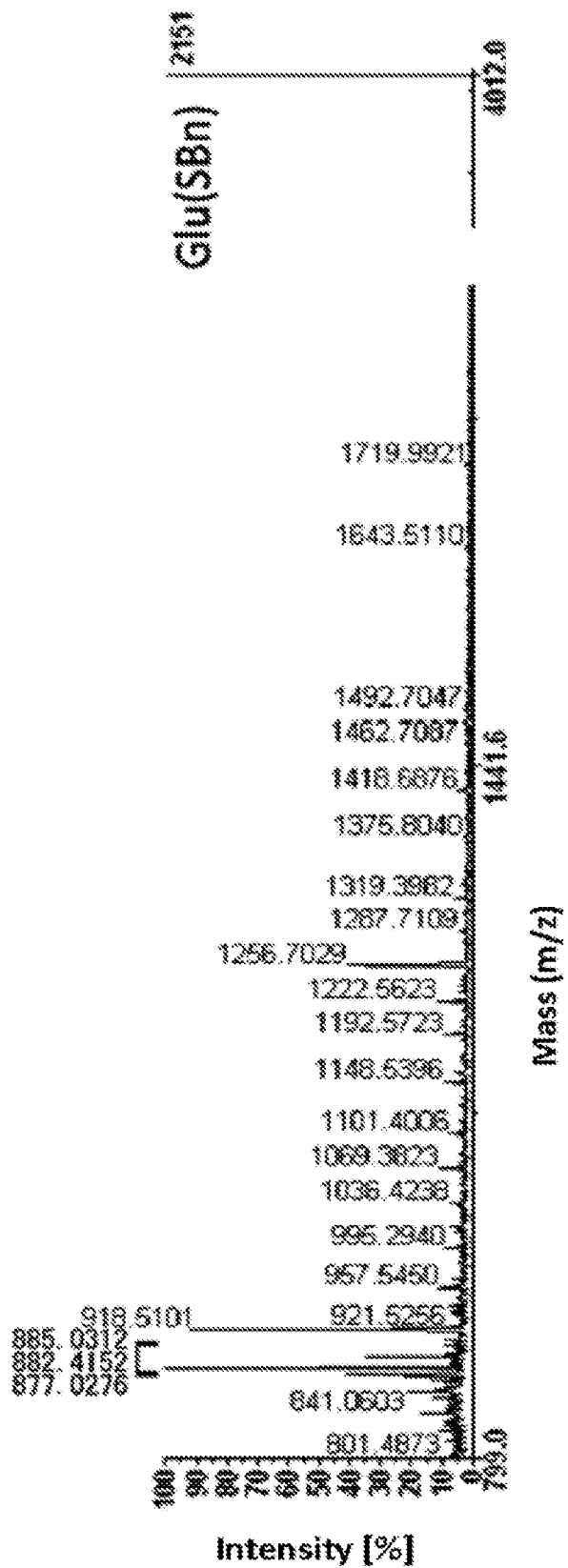
FIG. 2 is a diagram showing mass spectrometry results of a translation product of mRNA encoding peptide sequence P-1 containing Glu(SBn).

The aforementioned transcription and translation solution containing 20 nM template DNA Mtyg_R (SEQ ID NO: D-2) as well as 0.3 mM Gly, 0.3 mM Met, 0.3 mM Arg, 0.3 mM Thr, 0.3 mM Tyr and 50 µM Glu(SBn)-tRNAEnAsn-GAG (Compound AT-1-IID) was incubated at 37° C. for 60 minutes. The resulting translation reaction product was purified with SPE C-TIP (Nikkyo Technos) and analyzed by MALDI-MS. However, as shown in FIG. 2, mass spectral peaks derived from the translated peptide could not be confirmed by MALDI-MS in the molecular weight range of 799 to 2000. For example, the peaks detected near the molecular weight of 882, 918 or 1256 are not peaks derived from the translated peptide, because they are peaks also observed when analyzing PURESystem not containing template DNA as a negative control.

```
SEQ ID NO: D-2
Mtyg_R DNA sequence
                                            (SEQ ID NO: 2)
GTAATACGACTCACTATAGGGTTAACTTTAAGAAGGAGATATACATatg ACTACAACGCGActtactaccgtcgtggcggcTAATAAATAGATAG Peptide sequence P-1
                                          (SEQ ID NO: 186)
MetThrThrThrArg[Glu(SBn)]TyrTyrArgArgGlyGly
```

MALDI-MS:
Not detected (calc. 1595.7)

2. Translation Synthesis of Peptides Containing Thioesterified Aspartic Acid Derivatives 2-1. Translation Synthesis of a Model Peptide Containing Asp(SMe)

Figure 3:
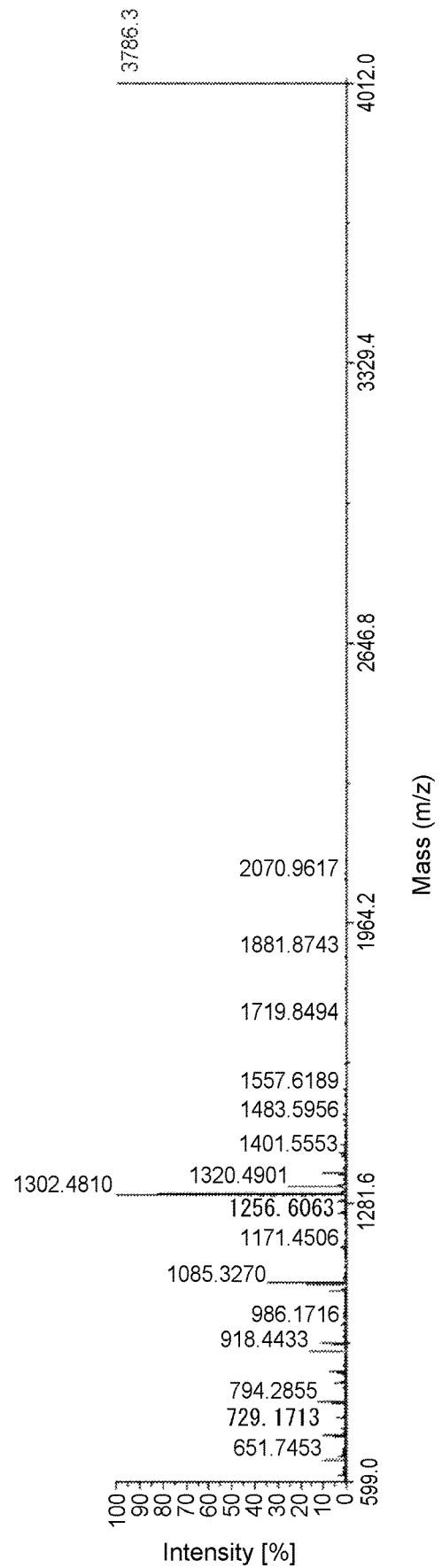
FIG. 3 is a diagram showing mass spectrometry results of a translation product of mRNA encoding peptide sequence P-2 containing Asp(SMe). The translated full-length peptide resulting from demethylthiolation during the translation of Asp(SMe) was detected as the main product (translated peptide P-3).

20 nM template DNA Mtryg3 (SEQ ID NO: D-3), 0.3 mM each of 19 proteinogenic amino acids excluding Leu, and 50 µM Asp(SMe)-tRNAEnAsnGAG (Compound AT-1-IA) were added to the transcription and translation solution, and the mixture was incubated at 37° C. for 60 minutes. The translation reaction product was purified with SPE C-TIP (Nikkyo Technos) and analyzed by MALDI-MS. As a result, a mass spectrum (MS) indicating a molecular weight of full-length peptides resulting from demethylthiolation was observed as the main product (FIG. 3).

SEQ ID NO: D-3
Mtryg3 DNA sequence (SEQ ID NO: 3)
GTAATACGACTCACTATAGGGTTAACTTTAAGAAGGAGATATACATatg ACTACAACGCGActtt actaccgtggcggcTAGTAGATAGATAG Peptide sequence P-2

(SEQ ID NO: 187)
MetThrThrThrArg[Asp(SMe)]TyrTyrArgGlyGly

MALDI-MS:

m/z: [H+M]+=1302.5 (full-length peptide containing thioester Calc. 1349.6, demethylthiolated peptide Calc. 1301.6) (The compound observed having a molecular weight of 1302 is peptide P-3).

2-2. Translation of a Peptide not Containing Most Reactive Tyr and Containing Thioester (Compound P-5)

Figure 5:
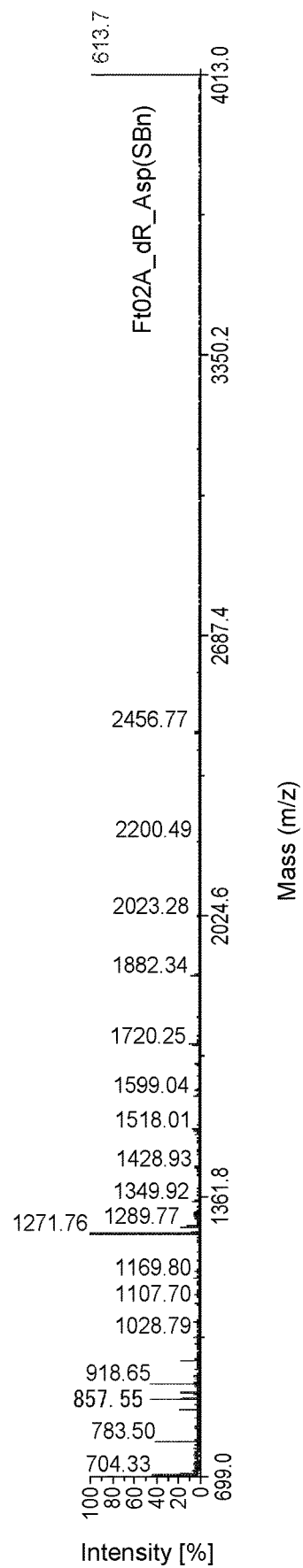
FIG. 5 is a diagram showing the translation of a peptide sequence not containing Tyr and containing thioester.

The aforementioned transcription and translation solution, 0.3 mM each of 19 proteinogenic amino acids excluding Leu, and 50 µM of the compound prepared in the above-described method, AT-1-ID(Asp(SBn)-tRNAEnAsn-GAG), were added to 20 nM template DNA Ft02A_dR (SEQ ID NO: D-4), followed by translation at 37° C. for 60 minutes. The translation reaction product was purified with SPE C-TIP (Nikkyo Technos) and analyzed by MALDI-MS. As a result, the MS spectrum resulting from debenzylthiolation (peptide P-6) was similarly confirmed as the main product after production of full-length peptide P-5 containing thioester amino acid. This confirmed that the debenzylthiolation reaction point is not a phenolic hydroxyl group (FIG. 5).

Ft02A_dR DNA sequence (SEQ ID NO: D-4)

(SEQ ID NO: 4)
GTAATACGACTCACTATAGGGTTAACTTTAAgaaggagatatacatATG

ACTACAACGgcgggcggcCTTtttttttggcggcAAATAATAA

Peptide sequence P-5

(SEQ ID NO: 188)
MetThrThrThrAlaGlyGly[Asp(SBn)]PhePheGlyGlyLys

MALDI-MS: m/z: [H+M]+=1271.8 (peptide P-6 resulting from debenzylthiolation of peptide P-5 Calc. 1270.6)

2-3. Hydrolysis Experiment to Estimate the Structure of Translated Peptide P-6

Figure 4:
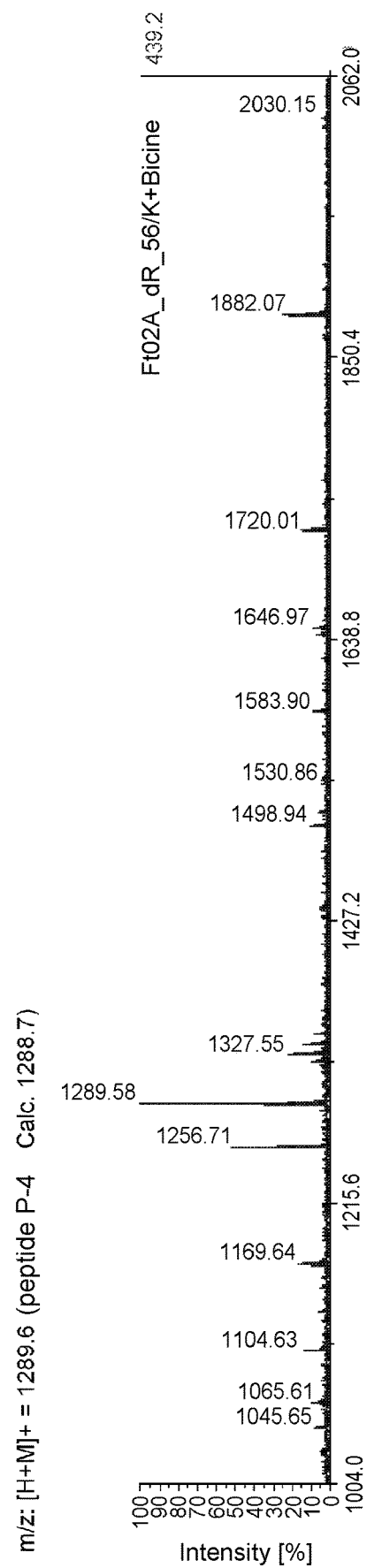
FIG. 4 is a diagram showing the production of peptide P-4 by the hydrolysis reaction of translated peptide P-6.

The aforementioned translation reaction product P-6 was hydrolyzed in 333 mM bicine KOH, pH 9.0, at 95° C. for 15 minutes, purified with SPE C-TIP (Nikkyo Technos) and analyzed by MALDI-MS. As a result, the debenzylthiolated peptide P-6 was hydrolyzed, and the molecular weight was confirmed to be increased by 18 (Peptide compound P-4). It was suggested that the assumed condensation reaction at the thioester site is not amide-forming reaction with an amino group but esterification reaction, thioesterification reaction or the like with a relatively hydrolyzable OH or SH group (FIG. 4).

Peptide Compound P-4
MALDI-MS:

m/z: [H+M]+=1289.6 (hydrolysate of P-6 Calc. 1288.7)

2-4. Translation Synthesis of a Thioester-Containing Peptide, which was Initiated from MOFlac not Having an N-Terminal Amino Group (Compound 7a)

A peptide not having an N-terminal amino group was translationally synthesized and analyzed as follows.

2-4-1. Synthesis of MeOFlac-pdCpA 2-4-1-1. Synthesis of (S)-2-methoxy-3-phenylpropanoic Acid (Compound 7a, MeOFlac)

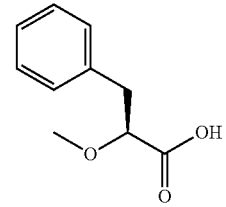

(S)-2-Hydroxy-3-phenylpropanoic acid (1.0 g, 6.02 mmol) was dissolved in THF (100 ml), sodium hydride (0.48 g, 12.00 mmol) and methyl iodide (1.71 g, 12.04 mmol) were added, and the mixture was stirred at 65° C. for one hour. After leaving to cool, the reaction solution was concentrated under reduced pressure and adjusted to pH 4 by adding a 6 M aqueous hydrochloric acid solution thereto. The aqueous layer was extracted with ethyl acetate, the organic layer was concentrated, and the resulting residue was purified by column chromatography (dichloromethane: methanol=10:1) to afford the title compound (0.71 g, 59%).

2-4-1-2. Synthesis of (S)-cyanomethyl 2-methoxy-3-phenylpropanoate (Compound 7b)

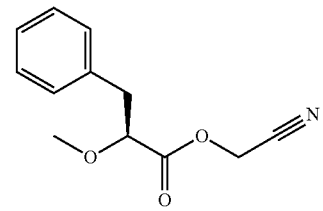 [SMILES: CO[C@@H](Cc1ccccc1)C(=O)OCC#N]

(S)-2-Methoxy-3-phenylpropanoic acid (Compounds 7a, 0.50 g, 2.50 mmol) and 2-bromoacetonitrile (1.20 g, 10.00 mmol) were dissolved in acetonitrile (60 ml). Then triethylamine (0.50 g, 4.99 mmol) was added dropwise under ice-cooling. After stirring at room temperature for 40 minutes, the reaction solution was concentrated under reduced pressure, and the residue was purified by column chromatography (petroleum ether:ethyl acetate=20:1) to afford the title compound (0.39 g, 65%).

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-methoxy-3-phenylpropanoate (Compound 7c)

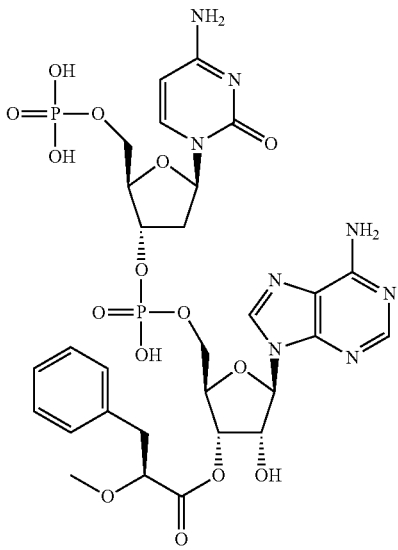 [SMILES: CO[C@@H](Cc1ccccc1)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

((2R,3S,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h, 0.32 g, 0.50 mmol) and (S)-cyanomethyl 2-methoxy-3-phenylpropanoate (Compound 7b, 0.44 g, 2.01 mmol) were added to a solution of imidazole (3.40 g, 50.00 mmol) and N,N,N-trimethylhexadecan-1-aminium chloride (3.20 g, 10.00 mmol) dissolved in water (30 ml), and the mixture was stirred at room temperature for 30 minutes. TFA (1.0 ml) was added to the reaction solution, followed by concentration. The resulting residue was purified by preparative HPLC (0.05% aqueous TFA solution:acetonitrile=84:16→60:40) to afford the title compound (66 mg, 16%).

LCMS: m/z 799 (M+H)+

Retention time: 0.609 min (analysis condition SMD method 1)

2-4-2. Synthesis of tRNA (Lacking CA) by Transcription tRNAfMetCAU (-CA) (SEQ ID NO: R-5) lacking 3'-end CA was synthesized from template DNA (SEQ ID NO: D-5) by in vitro transcription using RiboMAX Large Scale RNA production System T7 (Promega, P1300) and purified with RNeasy Mini kit (Qiagen).

SEQ ID NO: D-5 (SEQ ID NO: 5):
GGCGTAATACGACTCACTATAGGCGGGGTGGAGCAGCCTGGTAGCTCGT
CGGGCTCATAACCCGAAGATCGTCGGTTCAAATCCGGCCCCCGCAAC

SEQ ID NO: R-5 (SEQ ID NO: 32):
GGCGGGGUGGAGCAGCCUGGUAGCUCGUCGGGCUCAUAACCCGAAGAUC
GUCGGUUCAAAUCCGGCCCCCGCAAC 2-4-3. Synthesis of Acylated tRNA (Compound AT-2) by Ligation of Acylated pdCpA not Containing an N-Terminal Amino Group (Compound 7c) and tRNA (Lacking CA) (SEQ ID NO: R-5)

2 µL of 10× ligation buffer (500 mM HEPES-KOH pH 7.5, 200 mM MgCl$_2$, 10 mM ATP) and 4 µL of nuclease free water were added to 10 µL of 50 µM transcribed tRNAfMet-CAU (-CA) (SEQ ID NO: R-5). The mixture was heated at 95° C. for 2 minutes and then left to stand at room temperature for 5 minutes, and the tRNA was refolded. 2 µL of 10 units/µL T4 RNA ligase (New England Biolabs) and 2 µL of a 5 mM solution of acylated pdCpA not containing an N-terminal amino group (Compound 7c) in DMSO were added, and ligation reaction was carried out at 15° C. for 45 minutes. Acylated tRNA (Compound AT-2) was collected by phenol extraction and ethanol precipitation. Acylated tRNA (Compound AT-2) was dissolved in 1 mM sodium acetate immediately prior to addition to the translation mixture.

(SEQ ID NO: 33)
GGCGGGGUGGAGCAGCCUGGUAGCUCGUCGGGCUCAUAA
CCCGAAGAUCGUCGGUUCAAAUCCGGCCCCCGCAAC-dCA

Compound AT-2 MeOFlac-tRNAfMetCAU

Figure 6:
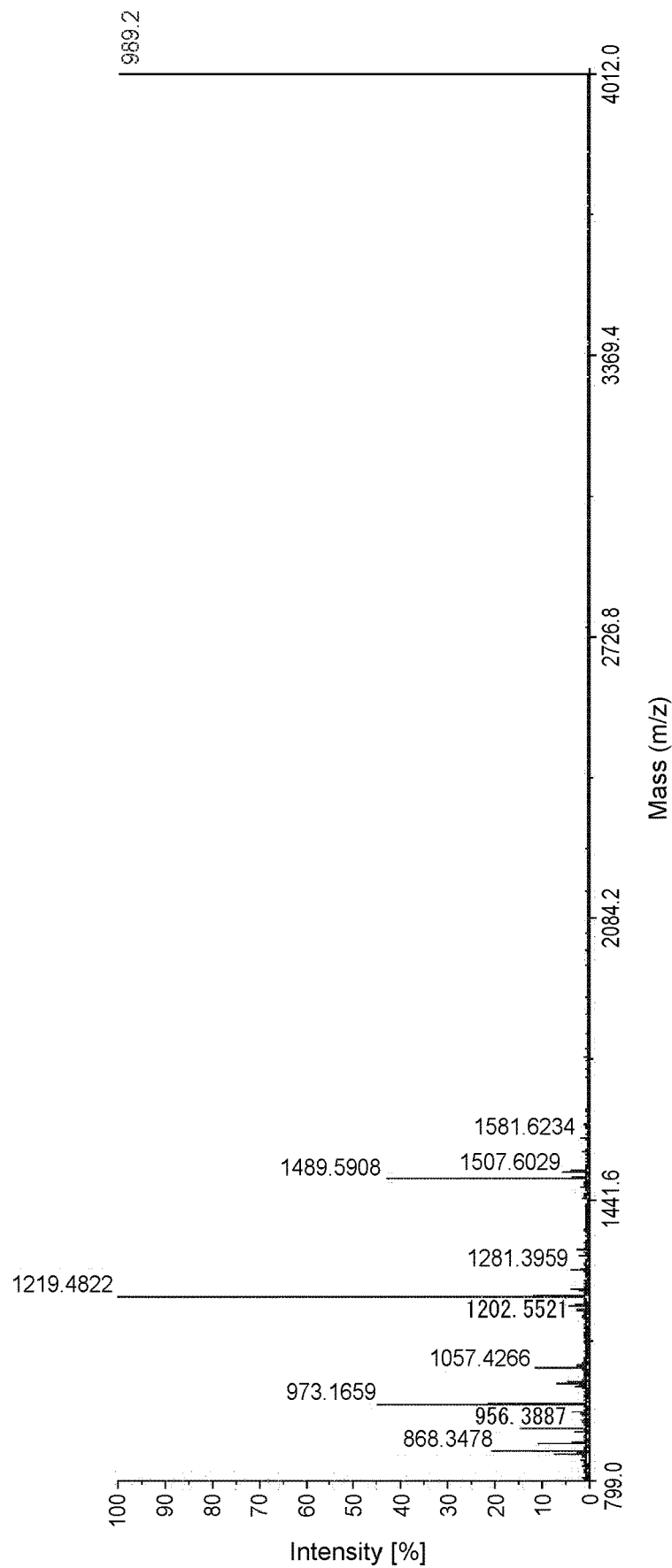
FIG. 6 is a diagram showing the translational synthesis of a peptide not having an N-terminal amino group and containing thioester.

The aforementioned transcription and translation solution, amino acids 0.3 mM Gly, 0.3 mM Arg, 0.3 mM Thr and 0.3 mM Tyr, and 50 µM Asp(SBn)-tRNAEnAsnGAG (Compound AT-1-1D) and 50 µM MeOFlac-tRNAfMetCAU (Compound AT-2) prepared by the above-described methods were added to 20 nM template DNA Mtyg_R (SEQ ID NO: D-2), followed by translation at 37° C. for 60 minutes. The translation reaction product was purified with SPE C-TIP (Nikkyo Technos) and analyzed by MALDI-MS. As a result, the MS corresponding to the debenzylthiolate d peptide (translated peptide P-8) was observed as the main product. Although the peptide not having amine at the N-terminal was translated using MeOFlac for initiation of the translation, the molecular weight was reduced. Therefore, we concluded that reaction with N-terminal amine did not occur (FIG. 6).

Peptide sequence P-7
(SEQ ID NO: 189)
[MeOFlac]ThrThrThrArg[Asp(SBn)]TyrTyrArgArgGlyGly MALDI-MS:
m/z: [H+M]+=1489.6 (peptide P-8 benzylthiolated from peptide sequence P-7 Calc. 1488.6)

2-5. Translation synthesis of a model peptide having N-alkylated amino acid on the C-terminal side immediately following the side chain thioesterified amino acid The aforementioned transcription and translation solution, 0.1 mM 10-HCO—H4 folate (10-formyl-5,6,7,8,-tetrahydrophilic acid, see Japanese Patent Laid-Open No. 2003-102495), 0.3 mM each of 19 proteinogenic amino acids excluding Leu, and 50 µM Asp(SMe)-tRNAEnAsnGAG (Compound AT-1-IA) prepared by the above-described method were added to 20 nM template DNA KA03 (SEQ ID NO: D-6), followed by translation at 37° C. for 60 minutes. The translation reaction product was purified with SPE C-TIP (Nikkyo Technos) and analyzed by MALDI-MS. As a result, the MS of full-length peptide containing thioester was observed as the main product, and peaks resulting from demethylthiolation were not observed.

Figure 7:
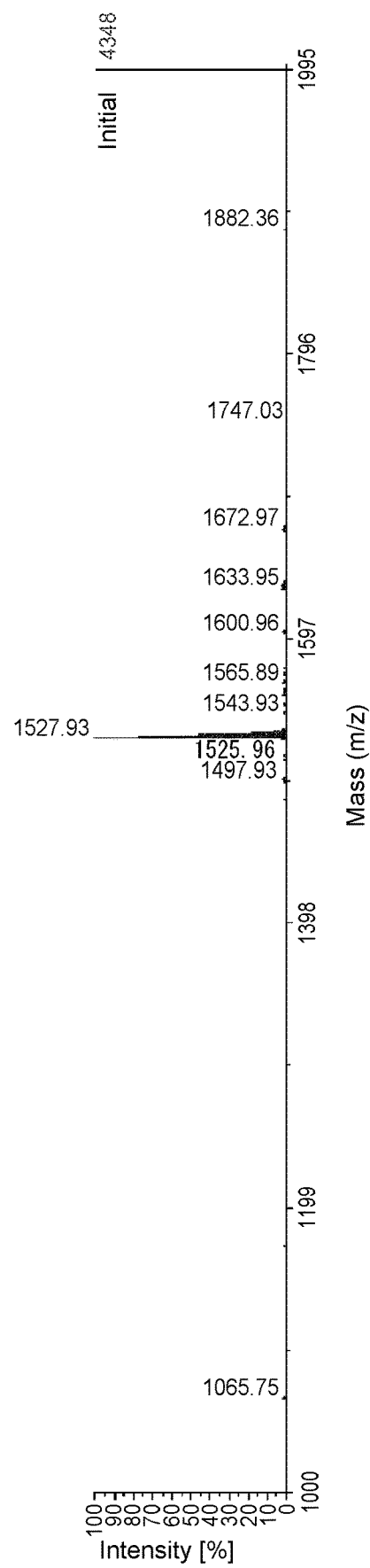
FIG. 7 is a diagram showing the translational synthesis of a model peptide having N-alkylated amino acid on the C-terminal side immediately following the side chain thioesterified amino acid.

The result above revealed that when hydrogen atoms are present in amide bonds immediately following aspartic acid-type thioester residues, the residues are reacted with the hydrogen atoms to form aspartimides (in all of translated peptides P-3, P-6 and P-8, such residues were reacted with hydrogen atoms of amide bonds adjacent to thioesters on the C-terminal side to form aspartimides). Meanwhile, the desired full-length peptide containing thioester was successfully translated by introducing N-alkylated amino acid as the amino acid residue immediately following such a residue (FIG. 7).

```
SEQ ID NO: D-6
KA03 DNA sequence
                                            (SEQ ID NO: 6)
GTAATACGACTCACTATAGGGTTAACTTTAAGAAGGAGATATACATatg ACTAGAACTaaggcgTACTGGAGCcttCCGggcggctaa Peptide sequence P-9
                                          (SEQ ID NO: 190)
MetThrArgThrLysAlaTyrTrpSer[Asp(SMe)]ProGlyGly
```

MALDI-MS: m/z: [H+M]+=1527.7 (translated peptide P-9 Calc. 1526.7)

Chemical structure of translated peptide P-3 (SEQ ID NO: 34)

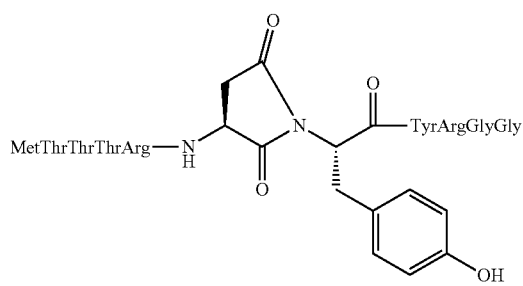

MALDI-MS:

m/z: [H+M]+=1302.5 (full-length peptide containing thioester Calc. 1348.6, demethylthiolated peptide Calc. 1301.6) (The compound observed having a molecular weight of 1302 is peptide P-3).

Chemical structure of translated peptide P-6 (SEQ ID NO: 35)

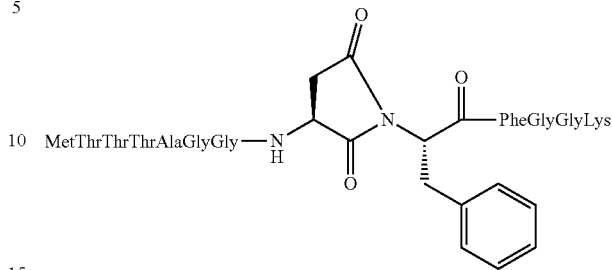

Peptide obtained by producing full-length peptide P-5 containing thioester amino acid and then debenzylthiolating the peptide MALDI-MS: m/z: [H+M]+=1271.8 (peptide debenzylthiolated from peptide P-5 Calc. 1270.6)

Chemical structure of translated peptide P-8 (SEQ ID NO: 191)

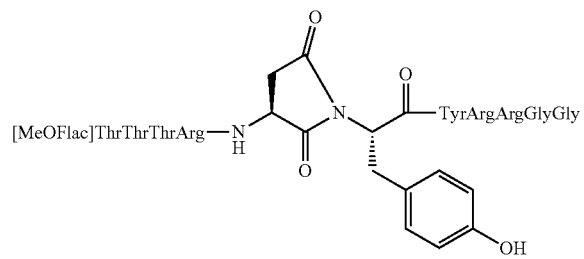

MALDI-MS:m/z: [H+M]+=1489.6 (peptide debenzylthiolated from peptide sequence P-7 Calc. 1488.6)

A full-length peptide (Met-Thr-Arg-Thr-Lys-Ala-Tyr-Trp-Ser-Asp(SBn)-MePhe-Gly-Gly) (SEQ ID NO: 192) containing thioester amino acid was similarly confirmed by an MS spectrum when NMe-phenylalanine was introduced as template DNA adjacent to KA01 thioester amino acid on the C-terminal side.

MALDI-MS: m/z: [H+M]+=1639.7 (Calc. 1638.7)

[Example 5] Experiment to Select Amino Group Units to be Reacted with Thioesters Peptides including thioesters could be translationally synthesized as described in the foregoing, therefore, an experiment to specify requirements for good amino group units to be condensed with such thioesters by amide bonds was carried out according to the following procedure.

1. Synthesis of Model Compounds Having Thioester Sites

Figures 1, 8:
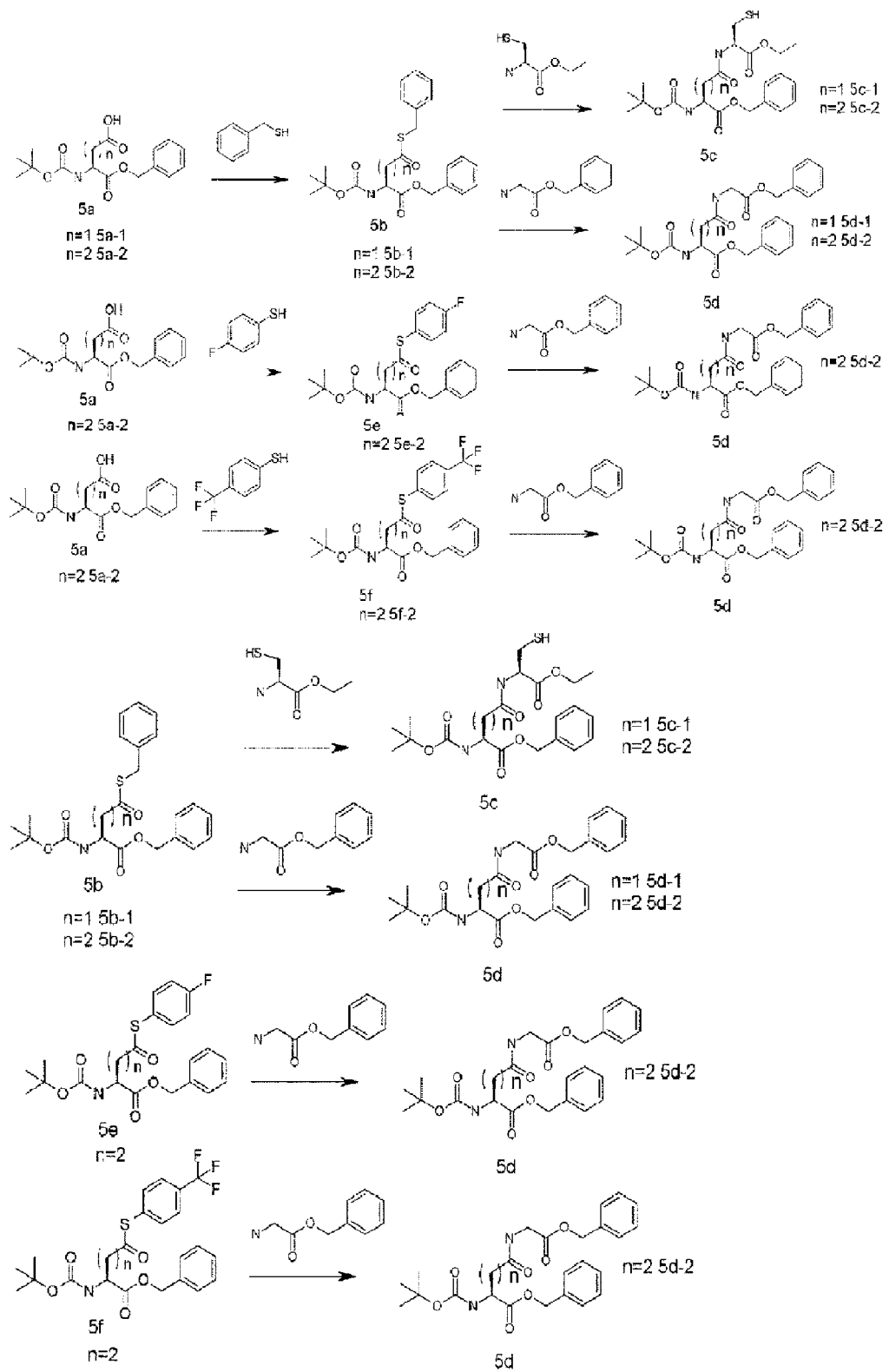

Compounds 5b-1 and 5b-2 were synthesized as peptide models having aspartic or glutamic acid thioesters according to the method described in FIG. 8.

1-1. Synthesis of (S)-benzyl 4-((benzylthio)-2-(tert-butoxycarbonyl)amino)-4-oxobutanoate (Compound 5b-1)

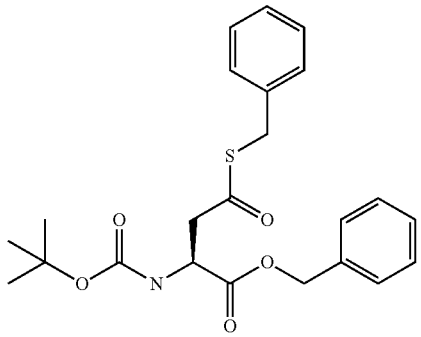 [SMILES: CC(C)(C)OC(=O)N[C@@H](CC(=O)SCc1ccccc1)C(=O)OCc1ccccc1]

N,N'-Diisopropylcarbodiimide (1.06 ml, 6.80 mmol), N,N-dimethylaminopyridine (94.4 mg, 0.773 mmol) and benzylmercaptane (0.380 ml, 3.24 mmol) were added to a solution of (S)-4-(benzyloxy)-3-((tert-butoxycarbonyl)amino)-4-oxobutanoic acid (Compound 5a-1) (1.00 g, 3.09 mmol) in dichloromethane (15 ml), and the mixture was stirred at room temperature overnight. Water was then added to the reaction solution. After dilution with ethyl acetate, the organic layer was washed with a saturated aqueous ammonium chloride solution, saturated aqueous sodium bicarbonate and brine. The organic extract was then dried over magnesium sulfate. Following concentration under reduced pressure, the resulting residue was purified by silica gel column chromatography (hexane/ethyl acetate=100/0→65/35) to afford (S)-benzyl 4-(benzylthio)-2-((tert-butoxycarbonyl)amino)-4-oxobutanoate (Compound 5b-1) (478 mg, 36%). Compound 5a-1 is commercially available.

LCMS (ESI) m/z=430 (M+H)+

Retention time: 1.10 min (analysis condition SQDAA05)

1-2. Synthesis of (S)-benzyl 5-(benzylthio)-2-((tert-butoxycarbonyl)amino)-5-oxopentanoate (Compound 5b-2)

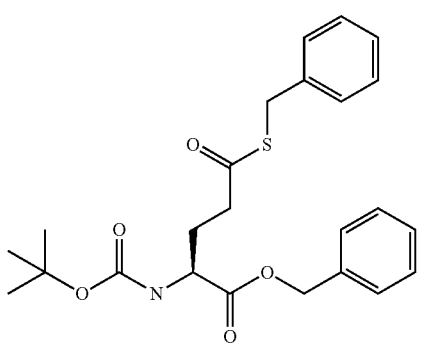 [SMILES: CC(C)(C)OC(=O)N[C@@H](CCC(=O)SCc1ccccc1)C(=O)OCc1ccccc1]

N,N'-Diisopropylcarbodiimide (1.02 ml, 6.51 mmol), N,N-dimethylaminopyridine (90.4 mg, 0.740 mmol) and benzylmercaptane (0.365 ml, 3.11 mmol) were added to a solution of (S)-5-(benzyloxy)-4-((tert-butoxycarbonyl)amino)-5-oxopentanoic acid (Compound 5a-2) (1.00 g, 2.96 mmol) in dichloromethane (14.8 ml), and the mixture was stirred at room temperature overnight. Water was then added to the reaction solution. After dilution with ethyl acetate, the organic layer was washed with a saturated aqueous ammonium chloride solution, saturated aqueous sodium bicarbonate and brine. The organic extract was then dried over magnesium sulfate. Following concentration under reduced pressure, the resulting residue was purified by silica gel column chromatography (hexane/ethyl acetate=100/0→65/35) to afford (S)-benzyl 5-(benzylthio)-2-((tert-butoxycarbonyl)amino)-5-oxopentanoate (Compound 5b-2) (1.18 g, 90%).

LCMS (ESI) m/z=444 (M+H)+

Retention time: 1.11 min (analysis condition SQDAA05)

1-3. Synthesis of (S)-benzyl 2-((tert-butoxycarbonyl)amino)-5-((4-fluorophenyl)thio)-5-oxopentanoate (Compound 5e-2)

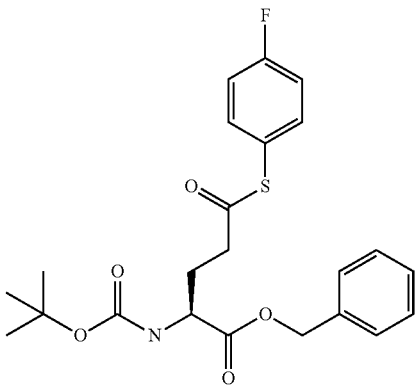 [SMILES: CC(C)(C)OC(=O)N[C@@H](CCC(=O)Sc1ccc(F)cc1)C(=O)OCc1ccccc1]

N,N'-Diisopropylcarbodiimide (0.510 ml, 3.26 mmol), N,N-dimethylaminopyridine (45.2 mg, 0.370 mmol), 4-fluorobenzenethiol (0.164 ml, 1.55 mmol) were added to a solution of (S)-5-(benzyloxy)-4-((tert-butoxycarbonyl)amino)-5-oxopentanoic acid (Compound 5a-2) (500 mg, 1.48 mmol) in dichloromethane (5 ml), and the mixture was stirred at room temperature overnight. The reaction mixture was then purified by reverse-phase silica gel column chromatography (10 mM aqueous ammonium acetate solution/methanol=70/30→20/80) to afford (S)-benzyl 2-((tert-butoxycarbonyl)amino)-5-((4-fluorophenyl)thio)-5-oxopentanoate (Compound 5e-2) (540 mg, 82%).

LCMS (ESI) m/z=448 (M+H)+

Retention time: 1.09 min (analysis condition SQDAA05)

1-4. Synthesis of (S)-benzyl 2-((tert-butoxycarbonyl)amino)-5-oxo-5-((4-(trifluoromethyl)phenyl)thio)pentanoate (Compound 5f-2)

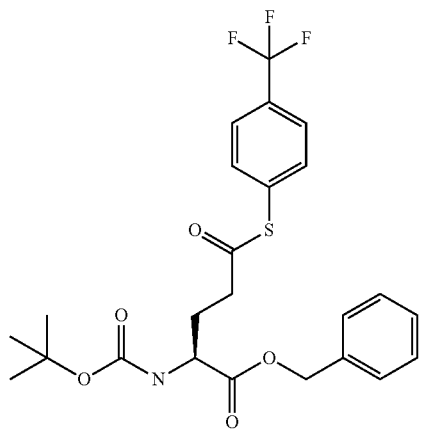 [SMILES: CC(C)(C)OC(=O)N[C@@H](CCC(=O)Sc1ccc(C(F)(F)F)cc1)C(=O)OCc1ccccc1]

N,N'-Diisopropylcarbodiimide (0.510 ml, 3.26 mmol), N,N-dimethylaminopyridine (45.2 mg, 0.370 mmol), 4-(trifluoromethyl)benzenethiol (0.211 ml, 1.55 mmol) were added to a solution of (S)-5-(benzyloxy)-4-((tert-butoxycarbonyl)amino)-5-oxopentanoic acid (Compound 5a-2) (500 mg, 1.48 mmol) in dichloromethane (5 ml), and the mixture was stirred at room temperature overnight. The reaction mixture was then purified by reverse-phase silica gel column chromatography (10 mM aqueous ammonium acetate solution/methanol=70/30→20/80) to afford (S)-benzyl 2-((tert-butoxycarbonyl)amino)-5-oxo-5-((4-(trifluoromethyl)phenyl)thio)pentanoate (Compound 5f-2) (373 mg, 51%).

LCMS (ESI) m/z=498 (M+H)+
Retention time: 1.12 min (analysis condition SQDAA05)

2. Selection of Amino Group Units Having High Reactivity by Examination of Reactions Between Model Compounds Containing Thioesters and Amino Group Units As shown in FIG. 8, thioester model compounds 5b, 5e or 5f were reacted with cysteine or glycine derivative model compounds to select substrates readily producing amide bonds with thioesters.

2-1. Synthesis of (S)-benzyl 2-((tert-butoxycarbonyl)amino)-4-(((R)-1-ethoxy-3-mercapto-1-oxopropan-2-yl)amino)-4-oxobutanoate (Compound 5c-1)

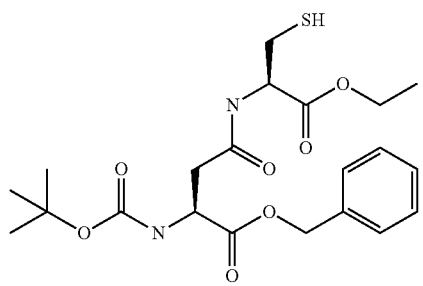 [SMILES: CCOC(=O)[C@H](CS)NC(=O)C[C@H](NC(=O)OC(C)(C)C)C(=O)OCc1ccccc1]

DIPEA (0.098 ml, 0.563 mmol) was added to a solution of (S)-benzyl 4-(benzylthio)-2-((tert-butoxycarbonyl)amino)-4-oxobutanoate (Compound 5b-1) (201.5 mg, 0.469 mmol) and (R)-ethyl 2-amino-3-mercaptopropanoate hydrochloride (104.5 mg, 0.563 mmol) in DMF (1.2 ml) and water (0.3 ml), and the mixture was stirred at 50° C. for three hours. Water was then added to the reaction solution, and the mixture was purified by reverse phase silica gel column chromatography (10 mM aqueous ammonium acetate solution/methanol=80/20→0/100) to afford (S)-benzyl 2-((tert-butoxycarbonyl)amino)-4-(((R)-1-ethoxy-3-mercapto-1-oxopropan-2-yl)amino)-4-oxobutanoate (Compound 5c-1) (133 mg, 67%).

LCMS (ESI) m/z=455 (M+H)+
Retention time: 0.98 min (analysis condition SQDAA05)

2-2. Synthesis of (S)-benzyl 2-((tert-butoxycarbonyl)amino)-5-(((R)-1-ethoxy-3-mercapto-1-oxopropan-2-yl)amino)-5-oxopentanoate (Compound 5c-2)

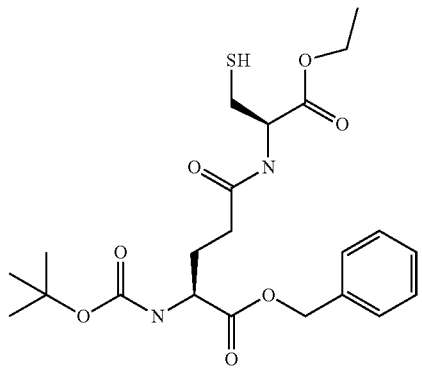 [SMILES: CCOC(=O)[C@H](CS)NC(=O)CC[C@H](NC(=O)OC(C)(C)C)C(=O)OCc1ccccc1]

DIPEA (0.098 ml, 0.563 mmol) was added to a solution of (S)-benzyl 5-(benzylthio)-2-((tert-butoxycarbonyl)amino)-5-oxopentanoate (Compound 5b-2) (208.2 mg, 0.469 mmol) and (R)-ethyl 2-amino-3-mercaptopropanoate hydrochloride (104.5 mg, 0.563 mmol) in DMF (1.2 ml) and water (0.3 ml), and the mixture was stirred at 50° C. for three hours. A 0.4 M aqueous tris(2-carboxyethyl)phosphine (TCEP) solution (3.27 ml) and DMF (3.27 ml) were then added to the reaction solution, after which the mixture was stirred at room temperature for one hour. The reaction mixture was then purified by reverse-phase silica gel column chromatography (10 mM aqueous ammonium acetate solution/methanol=70/30→20/80) to afford (S)-benzyl 2-((tert-butoxycarbonyl)amino)-4-(((R)-1-ethoxy-3-mercapto-1-oxopropan-2-yl)amino)-4-oxobutanoate (Compound 5c-2) (192.4 mg, 88%).

LCMS (ESI) m/z=469 (M+H)+
Retention time: 0.99 min (analysis condition SQDAA05)

The 0.4 M aqueous tris(2-carboxyethyl)phosphine (TCEP) solution was prepared as follows.

A solution of tris(2-carboxyethyl)phosphine (TCEP) hydrochloride (1.0 g, 3.49 mmol) in water (6.8 ml) was adjusted to pH 7 by adding triethylamine (1.64 ml) thereto to give a 0.4 M aqueous tris(2-carboxyethyl)phosphine (TCEP) solution.

2-3. Synthesis of (S)-benzyl 4-((2-(benzyloxy)-2-oxoethyl)amino)-2-((tert-butoxycarbonyl)amino)-4-oxobutanoate (Compound 5d-1)

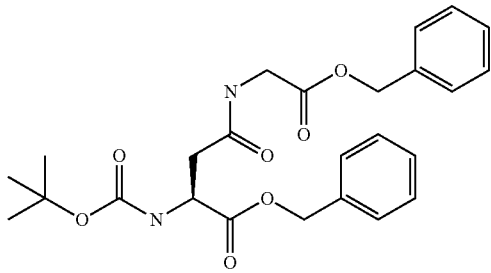 [SMILES: CC(C)(C)OC(=O)N[C@@H](CC(=O)NCC(=O)OCc1ccccc1)C(=O)OCc1ccccc1]

DIPEA (0.0145 ml, 0.0834 mmol) was added to a solution of (S)-benzyl 4-(benzylthio)-2-((tert-butoxycarbonyl)amino)-4-oxobutanoate (Compound 5b-1) (30.0 mg, 0.0698 mmol) and benzyl 2-aminoacetate hydrochloride (16.8 mg, 0.0834 mmol) in DMF (0.18 ml) and water (0.045 ml), and the mixture was stirred at 50° C. The time course of reaction was observed by LCMS. After stirring for three days, the intended Compound 5d-1 was observed, but Compound 5d-1b which is hydrolysate of one benzyl ester of Compound 5d-1 was also observed, and a large amount of the starting material Compound 5b-1 remained. The ratio of Compound 5b-1:Compound 5d-1:Compound 5d-1b which is hydrolysate of one benzyl ester of Compound 5d-1 was 22:1:8 (based on the UV area ratio by LCMS).

Compound 5d-1
LCMS (ESI) m/z=472 (M+H)+
Retention time: 0.99 min (analysis condition SQDAA05)
Compound 5d-1b
LCMS (ESI) m/z=380 (M+H)+
Retention time: 0.90 min (analysis condition SQDAA05)

2-4. Synthesis of (S)-benzyl 5-((2-(benzyloxy)-2-oxoethyl)amino)-2-((tert-butoxycarbonyl)amino)-5-oxopentanoate (Compound 5d-2)

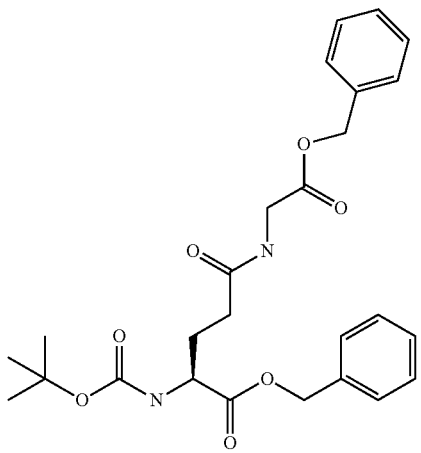 [SMILES: CC(C)(C)OC(=O)N[C@@H](CCC(=O)NCC(=O)OCc1ccccc1)C(=O)OCc1ccccc1]

DIPEA (0.0150 ml, 0.0860 mmol) was added to a solution of (S)-benzyl 5-(benzylthio)-2-((tert-butoxycarbonyl)amino)-5-oxopentanoate (Compound 5b-2) (31.8 mg, 0.0717 mmol) and benzyl 2-aminoacetate hydrochloride (17.3 mg, 0.0860 mmol) in DMF (0.19 ml) and water (0.048 ml), and the mixture was stirred at 50° C. The time course of reaction was observed by LCMS. After stirring for three days, the intended Compound 5d-2 was observed, but a large amount of the starting material Compound 5b-2 remained. The ratio of Compound 5b-2:Compound 5d-2 was 22:10 (based on the UV area ratio by LCMS).

Compound 5d-2
LCMS (ESI) m/z=485 (M+H)+
Retention time: 1.01 min (analysis condition SQDAA05)

2-5. Synthesis of (S)-benzyl 5-((2-(benzyloxy)-2-oxoethyl)amino)-2-((tert-butoxycarbonyl)amino)-5-oxopentanoate (Compound 5d-2)

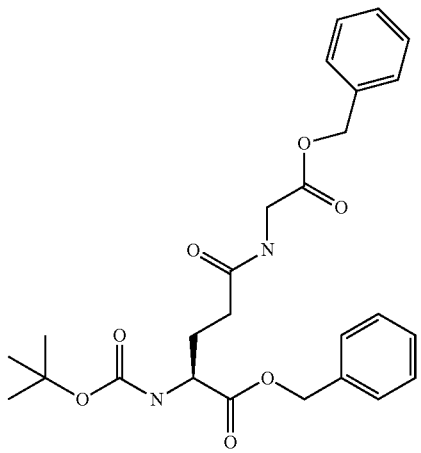 [SMILES: CC(C)(C)OC(=O)N[C@@H](CCC(=O)NCC(=O)OCc1ccccc1)C(=O)OCc1ccccc1]

A solution of benzyl 2-aminoacetate hydrochloride (17.6 mg, 0.0871 mmol) and DIPEA (0.0152 ml, 0.0871 mmol) in DMF (0.0871 ml) was added to a solution of (S)-benzyl 2-((tert-butoxycarbonyl)amino)-5-((4-fluorophenyl)thio)-5-oxopentanoate (Compound 5e-2) (30.0 mg, 0.0670 mmol) in DMF (0.463 ml) and water (0.220 ml), and the mixture was stirred at 50° C. for six hours. The reaction mixture was then purified by reverse-phase silica gel column chromatography (10 mM aqueous ammonium acetate solution/methanol=70/30→20/80) to afford (S)-benzyl 5-((2-(benzyloxy)-2-oxoethyl)amino)-2-((tert-butoxycarbonyl)amino)-5-oxopentanoate (Compound 5d-2) (29.4 mg, 91%).

LCMS (ESI) m/z=485 (M+H)+
Retention time: 2.80 min (analysis condition ZQAA05)

2-6. Synthesis of (S)-benzyl 5-((2-(benzyloxy)-2-oxoethyl)amino)-2-((tert-butoxycarbonyl)amino)-5-oxopentanoate (Compound 5d-2)

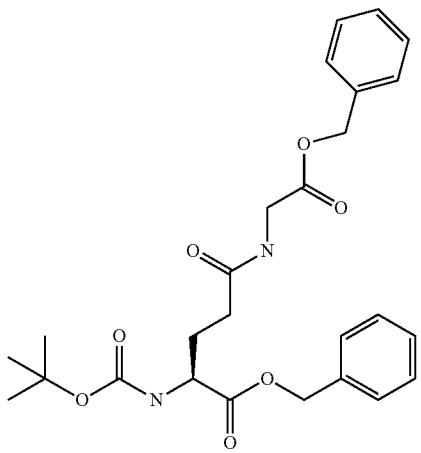 [SMILES: CC(C)(C)OC(=O)N[C@@H](CCC(=O)NCC(=O)OCc1ccccc1)C(=O)OCc1ccccc1]

A solution of benzyl 2-aminoacetate hydrochloride (15.8 mg, 0.0784 mmol) and DIPEA (0.0136 ml, 0.0784 mmol) in DMF (0.0784 ml) was added to a solution of (S)-benzyl 2-((tert-butoxycarbonyl)amino)-5-((4-trifluorophenyl)thio)-5-oxopentanoate (Compound 5f-2) (30.0 mg, 0.0603 mmol) in DMF (0.541 ml) and water (0.200 ml), and the mixture was stirred at 50° C. for 45 minutes. The reaction mixture was then purified by reverse-phase silica gel column chromatography (10 mM aqueous ammonium acetate solution/methanol=70/30→20/80) to afford (S)-benzyl 5-((2-(benzyloxy)-2-oxoethyl)amino)-2-((tert-butoxycarbonyl)amino)-5-oxopentanoate (Compound 5d-2) (26.4 mg, 90%).

LCMS (ESI) m/z=485 (M+H)+

Retention time: 2.80 min (analysis condition ZQAA05)

As described above, there was a huge difference in reactivity with thioesters between Cys derivatives that are model compounds for amines with reaction auxiliary groups and Gly derivatives that are models for amines without reaction auxiliary groups. It was made clear that Cys derivatives with reaction auxiliary groups have sufficiently high reactivity under conditions where RNA is stable. Because amines with reaction auxiliary groups have sufficiently high selectivity as compared with amines without reaction auxiliary groups, it can be determined that selective reaction with an amine having a reaction auxiliary group among multiple reaction points is possible in posttranslational cyclization. It was also made clear that the reactivity of thioaryl esters is higher than that of thioalkyl or thioaralkyl esters, and that the thioaryl esters also have high reactivity with amino groups without reaction auxiliary groups.

Figure 9:
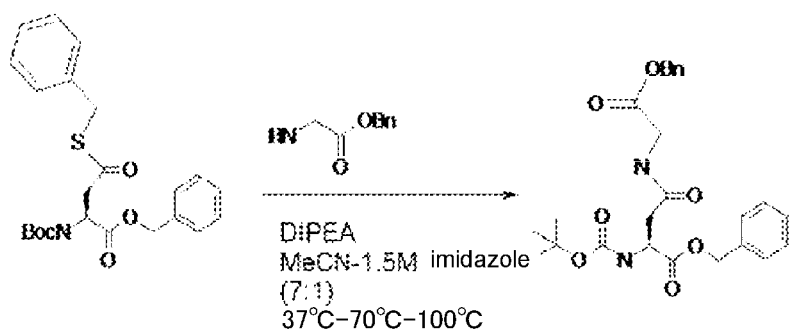
FIG. 9 is a diagram showing the synthesis of amide 5d-1 by the reaction of thioester 5b-1 with a glycine derivative under conditions involving addition of imidazole.

3. Chemical Reactions Under Conditions Involving Addition of Imidazole Known as Conditions Giving High Reactivity in Reactions Between Thioesters and Amines without Reaction Auxiliary Groups The reactions were carried out under the condition of an aqueous acetonitrile-1.5 M imidazole solution (7:1) according to the literature of Yangmei et al. (Journal of combinatorial chemistry 2009, 11, 1066-1072) (FIG. 9).

The reactions were carried out under two acidity or alkalinity conditions of pH 6.4 and pH 7.4 and under three reaction temperature conditions of 37° C., 70° C. and 100° C. The progress of the desired amidation reaction at about 46 UV area % (by LCMS) was confirmed under the reaction conditions showing the highest reaction conversion rate (pH 7.4, 100° C.)

Figure 10:
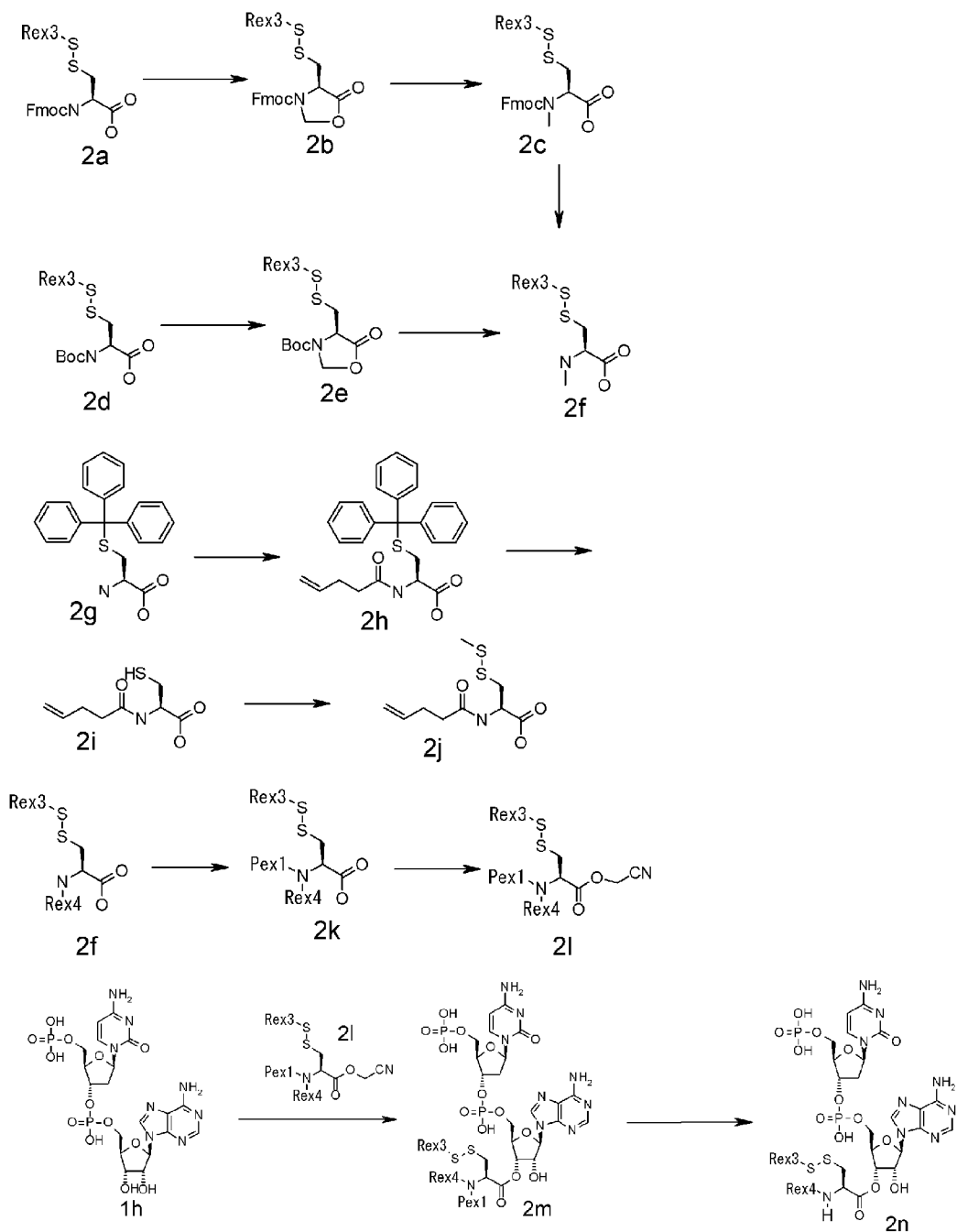
FIG. 10 is a diagram showing a general method for synthesizing aminoacylated pdCpAs of cysteine derivatives.

[Example 6] Synthesis of Amino Acids Activated at a SH Group, and Aminoacylated pdCpAs Thereof Amino acids activated at a SH group such as Cys and MeCys were synthesized as amino acids used for the N-terminals to be posttranslationally cyclized with thioester sites, and aminoacylated pdCpAs having them were synthesized, in the following manner according to the method shown in FIG. 10.

1. Synthesis of 2n-A 1-1. Synthesis of (R)-cyanomethyl 2-((tert-butoxycarbonyl)amino)-3-(tert-butyldisulfanyl)propanoate (Compound 21-A)

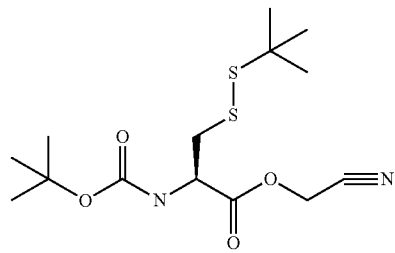 [SMILES: CC(C)(C)OC(=O)N[C@@H](CSSC(C)(C)C)C(=O)OCC#N]

2-Bromoacetonitrile (0.473 ml, 6.78 mmol) and N-ethyl-N-isopropylpropan-2-amine (0.444 ml, 2.49 mmol) were added to a solution of (R)-2-((tert-butoxycarbonyl)amino)-3-(tert-butyldisulfanyl)propanoic acid (Compound 2k-A) (700 mg, 2.26 mmol) in DMF (5 ml), and the mixture was stirred at room temperature for 10 minutes. A saturated aqueous ammonium chloride solution (1 ml) was added to the reaction mixture, after which the mixture was extracted with ethyl acetate and the organic layer was washed with water. The organic extract was then dried over magnesium sulfate. Following concentration under reduced pressure, the resulting residue was purified by silica gel column chromatography (hexane/ethyl acetate=100/0→70/30) to afford (R)-cyanomethyl 2-((tert-butoxycarbonyl)amino)-3-(tert-butyldisulfanyl)propanoate (Compound 21-A) (748 mg, 95%).

LCMS (ESI) m/z=347 (M−H)−

Retention time: 1.00 min (analysis condition SQDAA05)

1-2. Synthesis of (2R)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-3-(tert-butyldisulfanyl)propanoate (2m-A)

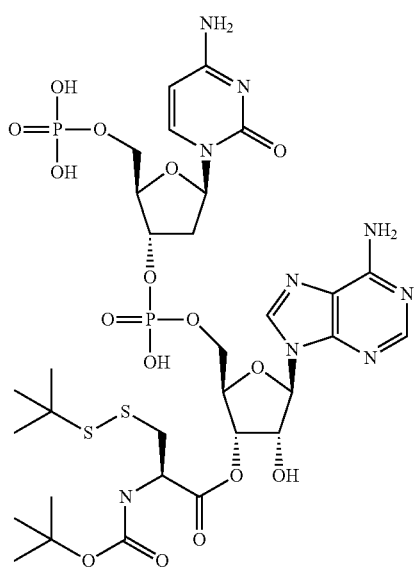 [SMILES: CC(C)(C)OC(=O)N[C@@H](CSSC(C)(C)C)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (200 mg, 0.314 mmol) in water (6.25 ml) and a solution of (R)-cyanomethyl 2-((tert-butoxycarbonyl)amino)-3-(tert-butyldisulfanyl)propanoate (Compound 21-A) (454 mg, 1.26 mmol) in THF (3.15 ml) were added to buffer A (113 ml), and the mixture was stirred at room temperature for 1 hour. The reaction mixture was then lyophilized. The resulting residue was purified by reverse-phase silica gel column chromatography (0.05% aqueous trifluoroacetic acid solution/0.05% trifluoroacetic acid-acetonitrile solution=100/0→60/40) to afford (2R)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-3-(tert-butyldisulfanyl)propanoate (Compound 2m-A) (129 mg, 46%).

LCMS (ESI) m/z=928 (M+H)+

Retention time: 0.58 min (analysis condition SQDFA05)

1-3. Synthesis of (2R)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-3-(tert-butyldisulfanyl)propanoate (2n-A)

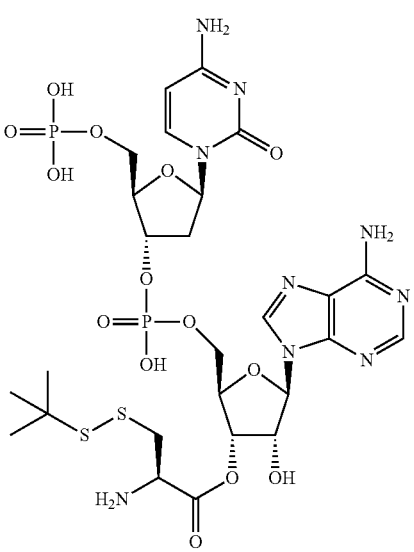 [SMILES: CC(C)(C)SSC[C@H](N)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

Trifluoroacetic acid (0.5 ml) was added to (2R)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-3-(tert-butyldisulfanyl)propanoate (Compound 2m-A) (40 mg, 0.045 mmol), and the mixture was stirred at room temperature for 10 minutes. The reaction mixture was concentrated under reduced pressure to afford (2R)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-3-(tert-butyldisulfanyl)propanoate (Compound 2n-A) (45.1 mg, 100%).

LCMS (ESI) m/z=828 (M+H)+

Retention time: 0.35 min (analysis condition SQDFA05)

2. Synthesis of 2n-B

2-1. Synthesis of (R)-(9H-fluoren-9-yl)methyl 4-((tert-butyldisulfanyl)methyl)-5-oxooxazolidine-3-carboxylate (Compound 2b-B)

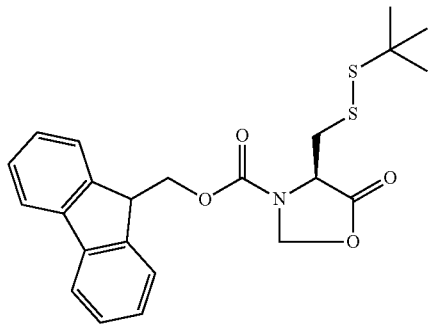 [SMILES: CC(C)(C)SSC[C@H]1C(=O)OCN1C(=O)OCC1c2ccccc2-c2ccccc21]

Paraformaldehyde (843 mg, 9.26 mmol) and 10-camphorsulfonic acid (75 mg, 0.324 mmol) were added to a solution of (R)-2-((((9H-fluoren-9-yl)methoxy)carbonyl)amino)-3-(tert-butyldisulfanyl)propanoic acid (Compound 2a-B) (2.00 g, 4.63 mmol) in toluene (10 ml), and the mixture was stirred at 100° C. for 4 hours. The reaction mixture was returned to room temperature and then concentrated under reduced pressure. The resulting residue was purified by silica gel column chromatography (hexane/ethyl acetate=100/0→70/30) to afford (R)-(9H-fluoren-9-yl)methyl 4-((tert-butyldisulfanyl)methyl)-5-oxooxazolidine-3-carboxylate (Compound 2b-B) (1.936 g, 94%).

LCMS (ESI) m/z=444 (M+H)+
Retention time: 1.16 min (analysis condition SQDAA05)

2-2. Synthesis of (R)-2-((((9H-fluoren-9-yl)methoxy)carbonyl)(methyl)amino)-3-(tert-butyldisulfanyl)propanoic Acid (Compound 2c-B)

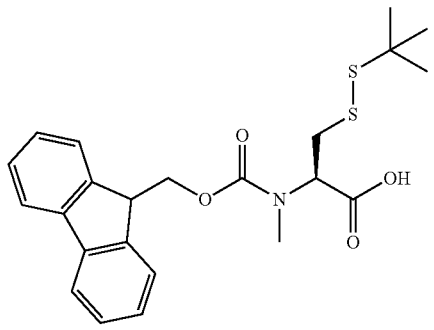 [SMILES: CN(C(=O)OCC1c2ccccc2-c2ccccc21)[C@@H](CSSC(C)(C)C)C(=O)O]

Triethylsilane (6.04 ml, 37.8 mmol) and trifluoroacetic acid (9 ml) were added to a solution of (R)-(9H-fluoren-9-yl)methyl 4-((tert-butyldisulfanyl)methyl)-5-oxooxazolidine-3-carboxylate (Compound 2b-B) (1.68 g, 3.78 mmol) in dichloromethane (18 ml), and the mixture was stirred at room temperature for one day. The reaction mixture was then concentrated under reduced pressure, and the residue was purified by reverse-phase silica gel column chromatography (10 mM aqueous ammonium acetate solution/methanol=70/30→20/80→0/100) to afford (R)-2-((((9H-fluoren-9-yl)methoxy)carbonyl)(methyl)amino)-3-(tert-butyldisulfanyl)propanoic acid (Compound 2c-B) (1.22 g, 72%).

LCMS (ESI) m/z=446 (M+H)+
Retention time: 1.02 min (analysis condition SQDAA05)

2-3. Synthesis of (R)-2-((tert-butoxycarbonyl)(methyl)amino)-3-(tert-butyldisulfanyl)propanoic Acid (Compound 2k-B)

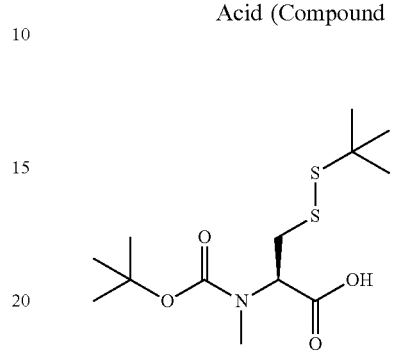

Piperidine (0.586 ml, 5.93 mmol) was added to a solution of (R)-2-((((9H-fluoren-9-yl)methoxy)carbonyl)(methyl)amino)-3-(tert-butyldisulfanyl)propanoic acid (Compound 2c-B) (1.06 g, 2.37 mmol) in tetrahydrofuran (11 ml), and the mixture was stirred at room temperature for 70 minutes. Di-tert-butyl dicarbonate (4.15 g, 19.0 mmol) and triethylamine (3.30 ml, 23.7 mmol) were then added to the reaction mixture, which was stirred at room temperature for 30 minutes. The reaction mixture was then concentrated under reduced pressure, and the resulting residue was purified by reverse-phase silica gel column chromatography (10 mM aqueous ammonium acetate solution/methanol=70/30→20/80→0/100) to afford (R)-2-((tert-butoxycarbonyl)(methyl)amino)-3-(tert-butyldisulfanyl)propanoic acid (Compound 2k-B) (586 mg, 76%).

LCMS (ESI) m/z=322 (M−H)−
Retention time: 0.88 min (analysis condition SQDAA05)

2-4. Synthesis of (R)-cyanomethyl 2-((tert-butoxycarbonyl)(methyl)amino)-3-(tert-butyldisulfanyl)propanoate (Compound 2l-B)

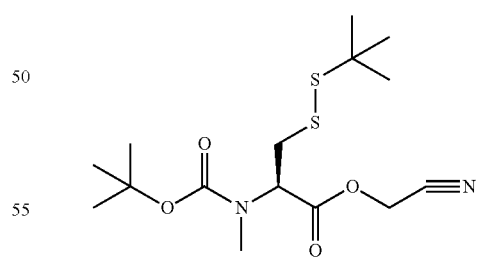

2-Bromoacetonitrile (0.200 ml, 2.87 mmol) and N-ethyl-N-isopropylpropan-2-amine (0.183 ml, 1.05 mmol) were added to a solution of (R)-2-((tert-butoxycarbonyl)(methyl)amino)-3-(tert-butyldisulfanyl)propanoic acid (Compound 2K-B) (309 mg, 0.955 mmol) in N,N-dimethylformamide (2.5 ml), and the mixture was stirred at room temperature for 30 minutes. A saturated aqueous ammonium chloride solution (3 ml) was added to the reaction mixture, after which the mixture was extracted with ethyl acetate and the organic layer was washed with water. The organic extract was then dried over magnesium sulfate. Following concentration under reduced pressure, the resulting residue was purified by silica gel column chromatography (hexane/ethyl acetate=100/0→70/30) to afford (R)-cyanomethyl 2-((tert-butoxycarbonyl)(methyl)amino)-3-(tert-butyldisulfanyl) propanoate (Compound 21-B) (272 mg, 78%).

LCMS (ESI) m/z=363 (M+H)+

Retention time: 1.05 min (analysis condition SQDAA05)

2-5. Synthesis of (2R)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)(methyl)amino)-3-(tert-butyldisulfanyl)propanoate (Compound 2m-B)

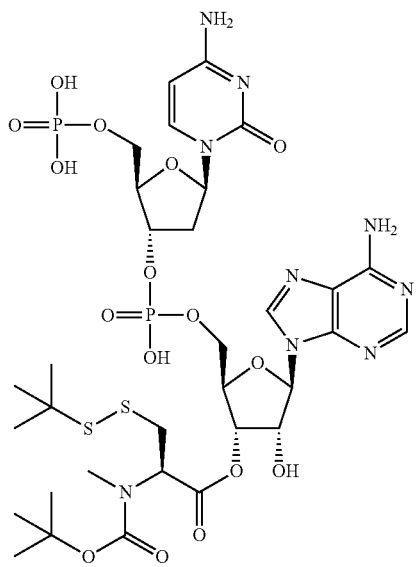 [SMILES: CN(C(=O)OC(C)(C)C)[C@@H](CSSC(C)(C)C)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

(2R)-(2R,3S,4R,5R)-2-((((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)(methyl)amino)-3-(tert-butyldisulfanyl)propanoate (Compound 2m-B) (38.6 mg, 23%) was obtained using ((2R,3S,5R)-5-(4-amino-2-oxopyrimidin-1(2H)-yl)-3-((((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (112 mg, 0.176 mmol) and further using (R)-cyanomethyl 2-((tert-butoxycarbonyl)(methyl)amino)-3-(tert-butyldisulfanyl)propanoate (Compound 21-B) (255 mg, 0.704 mmol) in place of (R)-cyanomethyl 2-((tert-butoxycarbonyl)amino)-3-(tert-butyldisulfanyl)propanoate (Compound 21-A) under the same conditions as in the preparation example for Compound 2m-A.

LCMS (ESI) m/z=942 (M+H)+

Retention time: 0.62 min (analysis condition SQDFA05)

2-6. Synthesis of (2R)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(tert-butyldisulfanyl)-2-(methylamino)propanoate (Compound 2n-B)

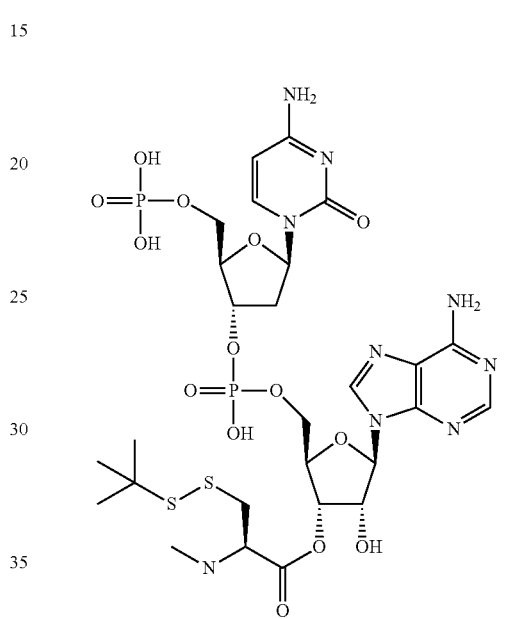

(2R)-(2R,3S,4R,5R)-2-((((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(tert-butyldisulfanyl)-2-(methylamino)propanoate (Compound 2n-B) (26.3 mg, 100%) was obtained using (2R)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)(methyl)amino)-3-(tert-butyldisulfanyl)propanoate (Compound 2m-B) (23.2 mg, 0.025 mmol) in place of (2R)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-3-(tert-butyldisulfanyl)propanoate (2m-A) under the same conditions as in the preparation example for Compound 2n-A.

LCMS (ESI) m/z=842 (M+H)+

Retention time: 0.36 min (analysis condition SQDFA05)

3. Synthesis of 2m-c

3-1. Synthesis of (R)-3-(tert-butyldisulfanyl)-2-(pent-4-enamido)propanoic Acid (Compound 2k-C)

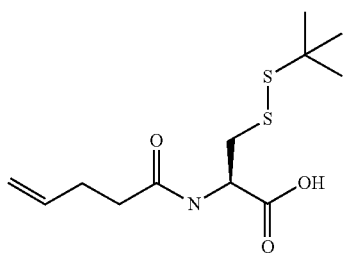

Pent-4-enoyl chloride (1.015 ml, 9.16 mmol) was added to a solution of (R)-2-amino-3-(tert-butyldisulfanyl)propanoic acid (1 g, 4.58 mmol) and sodium carbonate (1.46 g, 13.7 mmol) in tetrahydrofuran (7 ml) and water (14 ml) at 0° C., and the mixture was stirred at room temperature for 20 minutes. The reaction mixture was then adjusted to pH 2 by adding concentrated hydrochloric acid thereto at 0° C. After dilution with ethyl acetate, salting-out extraction was carried out by adding an appropriate amount of NaCl. The resulting organic extract was washed with brine and dried over magnesium sulfate. Concentration under reduced pressure afforded a mixed crude product C (1.71 g, 100%) of (R)-3-(tert-butyldisulfanyl)-2-(pent-4-enamido)propanoic acid (2k-C) and pent-4-enoic acid (1:0.9).

3-2. Synthesis of (R)-cyanomethyl 3-(tert-butyldisulfanyl)-2-(pent-4-enamido)propanoate (Compound 21-C)

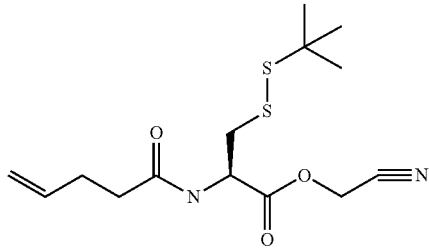

2-Bromoacetonitrile (0.957 ml, 13.74 mmol) and N-ethyl-N-isopropylpropan-2-amine (1.76 ml, 10.1 mmol) were added to a solution of the mixed crude product C (1.75 g, 8.70 mmol) of (R)-3-(tert-butyldisulfanyl)-2-(pent-4-enamido)propanoic acid (Compound 2k-C) and pent-4-enoic acid (1:0.9) in N,N-dimethylformamide (11 ml), and the mixture was stirred at room temperature for 50 minutes. A saturated aqueous ammonium chloride solution (6 ml) was added to the reaction mixture, after which the mixture was extracted with ethyl acetate and the organic layer was washed with water. The organic extract was then dried over magnesium sulfate. Following concentration under reduced pressure, the resulting residue was purified by silica gel column chromatography (hexane/ethyl acetate=100/0→50/50) to afford (R)-cyanomethyl 3-(tert-butyldisulfanyl)-2-(pent-4-enamido)propanoate (Compound 21-C) (940 mg, 62%).

LCMS (ESI) m/z=331 (M+H)+

Retention time: 0.94 min (analysis condition SQDAA05)

3-3. Synthesis of (2R)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(tert-butyldisulfanyl)-2-(pent-4-enamido)propanoate (Compound 2m-C)

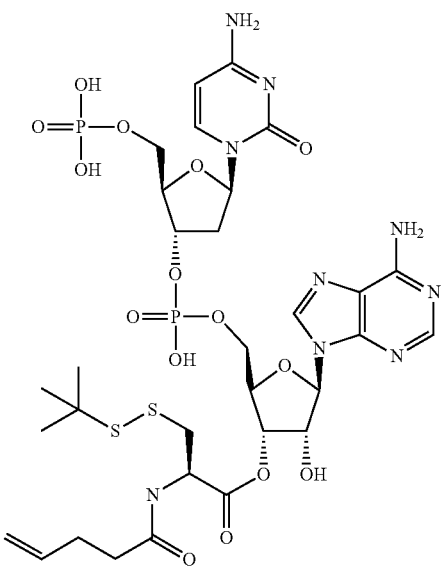

(2R)-(2R,3S,4R,5R)-2-((((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(tert-butyldisulfanyl)-2-(pent-4-enamido)propanoate (Compound 2m-C) (42.0 mg, 15%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (200 mg, 0.314 mmol) and further using (R)-cyanomethyl 3-(tert-butyldisulfanyl)-2-(pent-4-enamido)propanoate (21-C) (415 mg, 1.23 mmol) in place of (R)-cyanomethyl 2-((tert-butoxycarbonyl)amino)-3-(tert-butyldisulfanyl)propanoate (Compound 21-A) under the same conditions as in the preparation example for Compound 2m-A.

LCMS (ESI) m/z=910 (M+H)+

Retention time: 0.53 min (analysis condition SQDFA05)

4. Synthesis of 2m-D

4-1. Synthesis of (R)-2-(pent-4-enamido)-3-(tritylthio)propanoic Acid (Compound 2h)

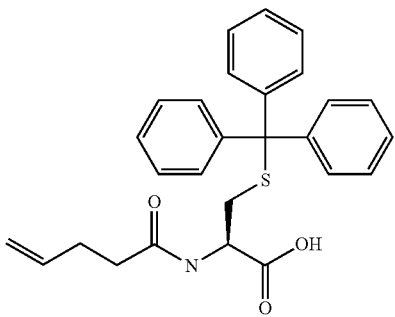

Pent-4-enoyl chloride (0.915 ml, 8.25 mmol) was added to a solution of (R)-2-amino-3-(tritylthio)propanoic acid (1.50 g, 4.13 mmol) and sodium carbonate (1.31 g, 12.4 mmol) in tetrahydrofuran (3.5 ml) and water (7 ml), and the mixture was stirred at room temperature for one hour. The reaction mixture was then adjusted to pH 2 by adding concentrated hydrochloric acid thereto at 0° C. After dilution with ethyl acetate, salting-out extraction was carried out by adding an appropriate amount of NaCl. The resulting organic extract was washed with brine, dried over magnesium sulfate and then concentrated under reduced pressure. The resulting residue was purified by reverse-phase silica gel column chromatography (10 mM aqueous ammonium acetate solution/methanol=70/30→0/100) to afford (R)-2-(pent-4-enamido)-3-(tritylthio)propanoic acid (Compound 2h) (1.14 g, 62%).

LCMS (ESI) m/z=444 (M−H)−
Retention time: 0.95 min (analysis condition SQDAA05)

4-2. Synthesis of (R)-cyanomethyl 3-(methyldisulfanyl)-2-(pent-4-enamido)propanoate (Compound 21-D)

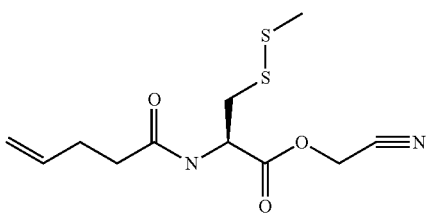

Trifluoroacetic acid (1.76 ml, 22.8 mmol) and triisopropylsilane (0.934 ml, 4.56 mmol) were added to a solution of (R)-2-(pent-4-enamido)-3-(tritylthio)propanoic acid (Compound 2h) (1.01 g, 2.28 mmol) in dichloromethane (10 ml), and the mixture was stirred at room temperature for 10 minutes. The reaction mixture was then concentrated under reduced pressure. A solution of S-methyl methanesulfonothioate (1.44 g, 11.4 mmol) in ethanol (5 ml) was added dropwise to a solution of the resulting residue and sodium carbonate (1.21 g, 11.4 mmol) in water (5 ml) at 0° C., and the mixture was then stirred at room temperature for 30 minutes. The reaction mixture was then adjusted to pH 2 by adding concentrated hydrochloric acid thereto at 0° C. The mixture was extracted by dilution with ethyl acetate. The resulting organic extract was washed with brine, dried over magnesium sulfate and then concentrated under reduced pressure. 2-Bromoacetonitrile (0.438 ml, 6.29 mmol) and N-ethyl-N-isopropylpropan-2-amine (0.440 ml, 2.52 mmol) were added to a solution of the resulting residue in DMF (1 ml), and the mixture was stirred at room temperature for 10 minutes. A saturated aqueous ammonium chloride solution (3 ml) was added to the reaction mixture, after which the mixture was extracted with ethyl acetate and the organic layer was washed with water. The organic extract was then dried over magnesium sulfate. Following concentration under reduced pressure, the resulting residue was purified by reverse-phase silica gel column chromatography (10 mM aqueous ammonium acetate solution/methanol=70/30→0/100) to afford (R)-cyanomethyl 3-(methyldisulfanyl)-2-(pent-4-enamido)propanoate (Compound 21-D) (291 mg, 48%).

LCMS (ESI) m/z=289 (M+H)+
Retention time: 0.79 min (analysis condition SQDAA05)

4-3. Synthesis of (2R)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(methyldisulfanyl)-2-(pent-4-enamido)propanoate (Compound 2m-D)

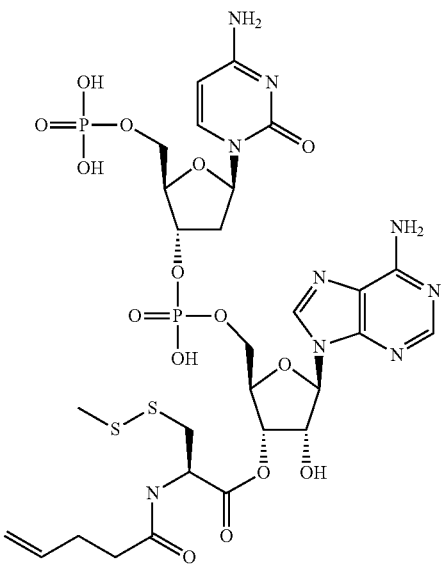

(2R)-(2R,3S,4R,5R)-2-(((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(methyldisulfanyl)-2-(pent-4-enamido)propanoate (Compound 2m-D) (21.2 mg, 10%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (150 mg, 0.236 mmol) and further using (R)-cyanomethyl 3-(methyldisulfanyl)-2-(pent-4-enamido)propanoate (Compound 21-D) (272 mg, 0.943 mmol) in place of (R)-cyanomethyl 2-((tert-butoxycarbonyl)amino)-3-(tert-butyldisulfanyl)propanoate (Compound 21-A) under the same conditions as in the preparation example for Compound 2m-A.

LCMS (ESI) m/z=868 (M+H)+

Retention time: 0.45 min (analysis condition SQDFA05)

5. Synthesis of 2m-E 5-1. Synthesis of (R)-cyanomethyl 3-(tert-butyldisulfanyl)-2-((((4,5-dimethoxy-2-nitrobenzyl)oxy)carbonyl)amino)propanoate (Compound 21-E)

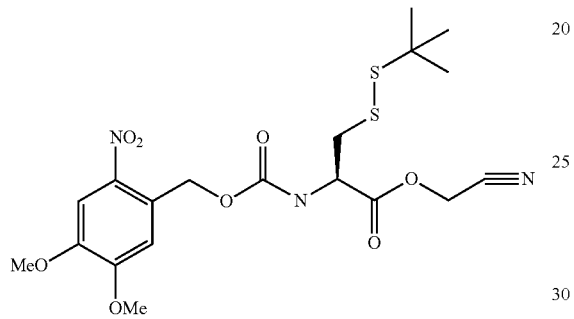

4,5-Dimethoxy-2-nitrobenzyl carbonochloridate (694 mg, 2.52 mmol) was added to a solution of (R)-2-amino-3-(tert-butyldisulfanyl)propanoic acid (Compound 2f-E, 500 mg, 2.29 mmol) and sodium carbonate (534 mg, 5.04 mmol) in dioxane (5 ml) and water (5 ml), and the mixture was stirred at room temperature for 30 minutes. The reaction solution was then adjusted to pH 2 by adding 1 N hydrochloric acid, and was extracted by adding ethyl acetate. The organic extract was dried over magnesium sulfate and concentrated under reduced pressure. 2-Bromoacetonitrile (0.284 ml, 4.08 mmol) and N-ethyl-N-isopropylpropan-2-amine (0.285 ml, 1.63 mmol) were added to a solution of the resulting residue in DMF (6 ml), and the mixture was stirred at room temperature for 20 minutes. A saturated aqueous ammonium chloride solution (3 ml) was added to the reaction mixture, after which the mixture was extracted with ethyl acetate and the organic layer was washed with water. The organic extract was then dried over magnesium sulfate. Following concentration under reduced pressure, the resulting residue was purified by silica gel column chromatography (hexane/ethyl acetate=100/0→60/40) to afford (R)-cyanomethyl 3-(tert-butyldisulfanyl)-2-((((4,5-dimethoxy-2-nitro benzyl)oxy)carbonyl)amino)propanoate (Compound 21-E) (653 mg, 98%).

LCMS (ESI) m/z=486 (M−H)−

Retention time: 0.99 min (analysis condition SQDAA05)

5-2. Synthesis of (2R)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(tert-butyldisulfanyl)-2-((((4,5-dimethoxy-2-nitrobenzyl)oxy)carbonyl)amino)propanoate (Compound 2m-E)

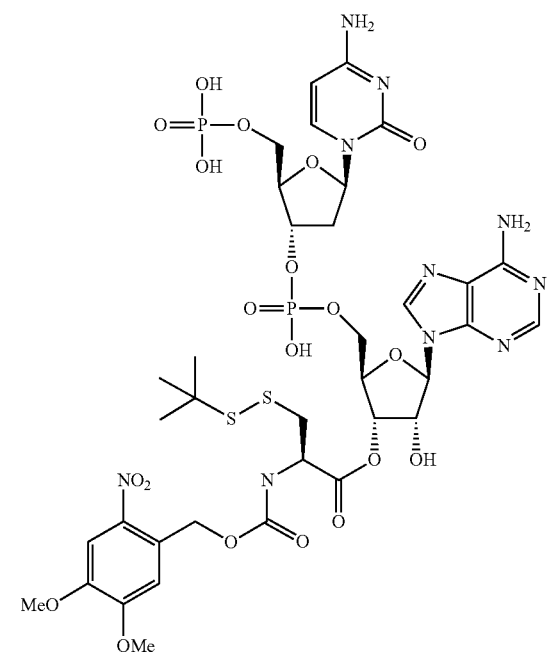

(2R)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(tert-butyldisulfanyl)-2-((((4,5-dimethoxy-2-nitrobenzyl)oxy)carbonyl)amino)propanoate (Compound 2m-E) (10.6 mg, 4%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (150 mg, 0.236 mmol) and further using (R)-cyanomethyl 3-(tert-butyldisulfanyl)-2-((((4,5-dimethoxy-2-nitrobenzyl)oxy)carbonyl)amino)propanoate (Compound 21-E) (460 mg, 0.943 mmol) in place of (R)-cyanomethyl 2-((tert-butoxycarbonyl)amino)-3-(tert-butyldisulfanyl)propanoate (Compound 21-A) under the same conditions as in the preparation example for Compound 2m-A.

LCMS (ESI) m/z=1067 (M+H)+

Retention time: 0.62 min (analysis condition SQDFA05)

6. Synthesis of 2m-F

6-1. Synthesis of (R)-tert-butyl 4-((ethyldisulfanyl)methyl)-5-oxooxazolidine-3-carboxylate (2e-F)

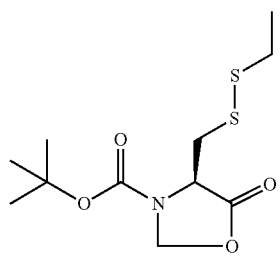 [SMILES: CCSSC[C@H]1C(=O)OCN1C(=O)OC(C)(C)C]

((1S,4R)-7,7-Dimethyl-2-oxobicyclo[2.2.1]heptan-1-yl) methanesulfonic acid (1.07 g, 4.62 mmol) and paraformaldehyde (847 mg, 2.89 mmol) were added to a solution of dicyclohexylamine (R)-2-((tert-butoxycarbonyl)amino)-3-(ethyldisulfanyl)propanoate (Compound 2d-f) (2.00 g, 4.32 mmol) in toluene (8 ml), and the mixture was stirred at 100° C. overnight. The reaction solution was then returned to room temperature and concentrated under reduced pressure. The resulting residue was purified by silica gel column chromatography (hexane/ethyl acetate=100/0→87/13) to afford (R)-tert-butyl 4-((ethyldisulfanyl)methyl)-5-oxooxazolidine-3-carboxylate (2e-F) (847 mg, 67%).

LCMS (ESI) m/z=294 (M+H)+

Retention time: 0.98 min (analysis condition SQDAA05)

6-2. Synthesis of (R)-3-(ethyldisulfanyl)-2-(methylamino)propanoic Acid (2f-F)

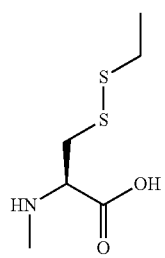

Triethylsilane (4.46 ml, 27.9 mmol) and trifluoroacetic acid (6.88 ml, 89.0 mmol) were added to a solution of (R)-tert-butyl 4-((ethyldisulfanyl)methyl)-5-oxooxazolidine-3-carboxylate (Compound 2e-F) (819 mg, 2.79 mmol) in dichloromethane (14 ml) at 0° C., and the mixture was stirred at room temperature for 1 hour. The reaction mixture was then concentrated under reduced pressure, and the resulting residue was purified by reverse-phase silica gel column chromatography (10 mM aqueous ammonium acetate solution/methanol=100/0→60/40) to afford (R)-3-(ethyldisulfanyl)-2-(methylamino)propanoic acid (Compound 2f-F) (232 mg, 43%).

LCMS (ESI) m/z=196 (M+H)+

Retention time: 0.39 min (analysis condition SQDAA05)

6-3. Synthesis of (R)-2-((((4,5-dimethoxy-2-nitrobenzyl)oxy)carbonyl)(methyl)amino)-3-(ethyldisulfanyl)propanoic Acid (2k-F)

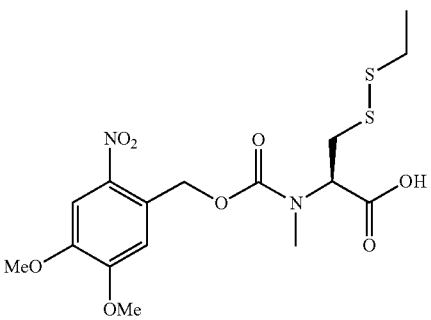 [SMILES: CCSSC[C@@H](C(=O)O)N(C)C(=O)OCc1cc(OC)c(OC)cc1[N+](=O)[O-]]

4,5-Dimethoxy-2-nitrobenzyl carbonochloridate (394 mg, 1.43 mmol) was added to a solution of (R)-3-(ethyldisulfanyl)-2-(methylamino)propanoic acid (Compound 2f-F) (232 mg, 1.19 mmol) and sodium carbonate (252 mg, 2.38 mmol) in dioxane (3 ml) and water (3 ml), and the mixture was stirred at room temperature for 30 minutes. A saturated aqueous ammonium chloride solution (3 ml) was added to the reaction mixture, after which the mixture was extracted with ethyl acetate and the organic layer was washed with water. The organic extract was then dried over magnesium sulfate. Following concentration under reduced pressure, the resulting residue was purified by reverse-phase silica gel column chromatography (10 mM aqueous ammonium acetate solution/methanol=70/30→0/100) to afford (R)-2-((((4,5-dimethoxy-2-nitrobenzyl)oxy)carbonyl)(methyl)amino)-3-(ethyldisulfanyl)propanoic acid (Compound 2k-F) (483 mg, 93%).

LCMS (ESI) m/z=435 (M+H)+

Retention time: 0.82 min (analysis condition SQDAA05)

6-4. Synthesis of (R)-cyanomethyl 2-((((4,5-dimethoxy-2-nitrobenzyl)oxy)carbonyl)(methyl)amino)-3-(ethyldisulfanyl)propanoate (21-F)

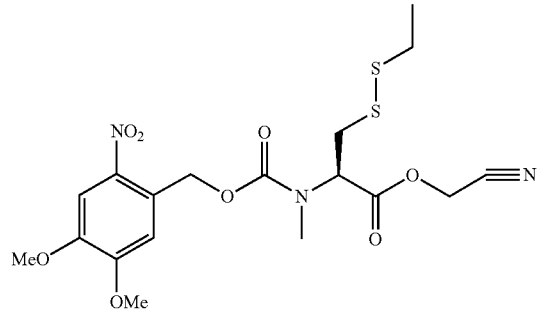 [SMILES: CCSSC[C@@H](C(=O)OCC#N)N(C)C(=O)OCc1cc(OC)c(OC)cc1[N+](=O)[O-]]

2-Bromoacetonitrile (0.115 ml, 1.65 mmol) and N-ethyl-N-isopropylpropan-2-amine (0.105 ml, 0.604 mmol) were added to a solution of (R)-2-((((4,5-dimethoxy-2-nitrobenzyl)oxy)carbonyl)(methyl)amino)-3-(ethyldisulfanyl)propanoic acid (Compound 2k-F) (238 mg, 0.549 mmol) in DMF (2.5 ml), and the mixture was stirred at room temperature for 10 minutes. A saturated aqueous ammonium chloride solution (3 ml) was added to the reaction mixture, after which the mixture was extracted with ethyl acetate and the organic layer was washed with water. The organic extract was then dried over magnesium sulfate. Following concentration under reduced pressure, the resulting residue was purified by reverse-phase silica gel column chromatography (10 mM aqueous ammonium acetate solution/methanol=70/30→0/100) to afford (R)-cyanomethyl 2-((((4,5-dimethoxy-2-nitrobenzyl)oxy)carbonyl)(methyl)amino)-3-(ethyldisulfanyl)propanoate (Compound 21-F) (221 mg, 85%).

LCMS (ESI) m/z=474 (M+H)+

Retention time: 0.97 min (analysis condition SQDAA05)

6-5. Synthesis of (2R)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((((4,5-dimethoxy-2-nitrobenzyl)oxy)carbonyl)(methyl)amino)-3-(ethyldisulfanyl)propanoate (2m-F)

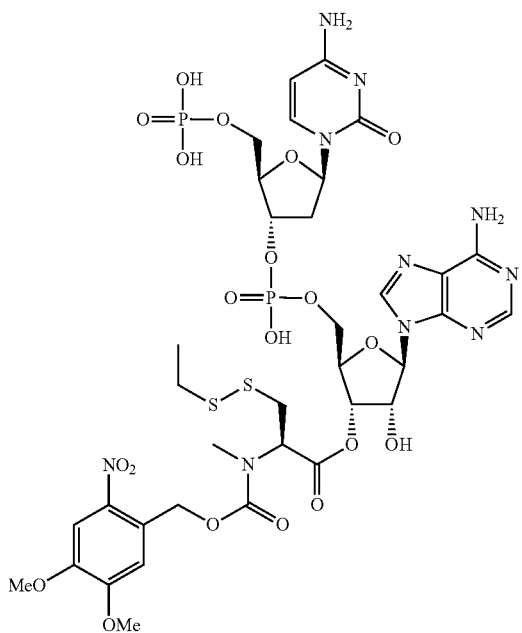 [SMILES: CCSSC[C@@H](C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O)N(C)C(=O)OCc1cc(OC)c(OC)cc1[N+](=O)[O-]]

(2R)-(2R,3S,4R,5R)-2-(((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((((4,5-dimethoxy-2-nitrobenzyl)oxy)carbonyl)(methyl)amino)-3-(ethyldisulfanyl)propanoate (Compound 2m-F) (18.6 mg, 17%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (66.0 mg, 0.104 mmol) and further using (R)-cyanomethyl 2-((((4,5-dimethoxy-2-nitrobenzyl)oxy)carbonyl)(methyl)amino)-3-(ethyldisulfanyl)propanoate (Compound 21-F) (196 mg, 0.415 mmol) in place of (R)-cyanomethyl 2-((tert-butoxycarbonyl)amino)-3-(tert-butyldisulfanyl)propanoate (Compound 21-A) under the same conditions as in the preparation example for Compound 2m-A.

LCMS (ESI) m/z=1053 (M+H)+

Retention time: 0.59 min (analysis condition SQDFA05)

7. Synthesis of 2m-G 7-1. Synthesis of (R)-3-(tert-butyldisulfanyl)-2-(methylamino)propanoic Acid (Compound 2f-G)

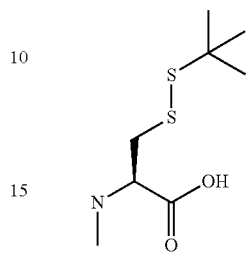

Piperidine (1.8 ml, 18.2 mmol) was added to a solution of (R)-2-((((9H-fluoren-9-yl)methoxy)carbonyl)(methyl)amino)-3-(tert-butyldisulfanyl)propanoic acid (Compound 2c-B) (2.70 g, 6.06 mmol) in tetrahydrofuran (20 ml), and the mixture was stirred at room temperature for 30 minutes. The reaction mixture was then concentrated under reduced pressure, and the residue was purified by reverse-phase silica gel column chromatography (10 mM aqueous ammonium acetate solution/methanol=100/0→60/40) to afford (R)-3-(tert-butyldisulfanyl)-2-(methylamino)propanoic acid (Compound 2f-G) (610 mg, 45%).

LCMS (ESI) m/z=224 (M+H)+

Retention time: 0.63 min (analysis condition SQDAA05)

7-2. Synthesis of (R)-cyanomethyl 2-((tert-butyldisulfanecarbonyl)(methyl)amino)-3-(tert-butyldisulfanyl)propanoate (Compound 21-G)

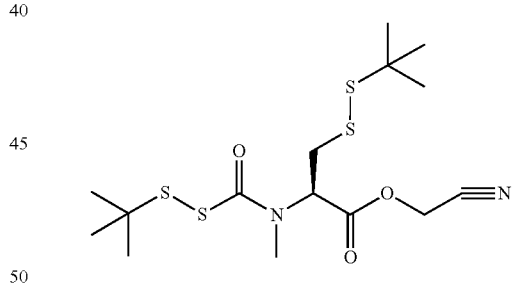

2-Methylpropane-2-thiol (0.663 ml, 5.88 mmol) was added dropwise to a solution of chlorocarbonylsulfenyl chloride (0.497 ml, 6.00 mmol) in tetrahydrofuran (6 ml) at 0° C., and the mixture was stirred at 0° C. for 30 minutes to prepare a 0.8 M SS-tert-butyl carbonochlorido(dithioperoxoate)-tetrahydrofuran solution. Sodium bicarbonate (752 mg, 8.95 mmol) and the 0.8 M SS-tert-butyl carbonochlorido(dithioperoxoate)-tetrahydrofuran solution (4.2 ml, 3.36 mmol) were added to a solution of (R)-3-(tert-butyldisulfanyl)-2-(methylamino)propanoic acid (Compound 2f-G, 500 mg, 2.24 mmol) in tetrahydrofuran (3.4 ml) and water (14.4 ml), and the mixture was stirred at room temperature for 5 minutes. The reaction mixture was then adjusted to pH 2 by adding concentrated hydrochloric acid thereto at 0° C. After dilution with ethyl acetate, salting-out extraction was carried out by adding an appropriate amount of NaCl. The resulting organic extract was washed with brine, and then dried over magnesium sulfate and concentrated under reduced pressure. N-Ethyl-N-isopropylpropan-2-amine (0.282 ml, 1.62 mmol) was added to a solution of the resulting residue in 2-bromoacetonitrile (1.02 ml), and the mixture was stirred at room temperature for 30 minutes. A saturated aqueous ammonium chloride solution (3 ml) was added to the reaction mixture, after which the mixture was extracted with ethyl acetate and the organic layer was washed with water. The organic extract was then dried over magnesium sulfate. Following concentration under reduced pressure, the resulting residue was purified by silica gel column chromatography (hexane/ethyl acetate=100/0→80/20) to afford (R)-cyanomethyl 2-((tert-butyldisulfanecarbonyl)(methyl)amino)-3-(tert-butyldisulfanyl)propanoate (Compound 21-G) (205 mg, 68%).

LCMS (ESI) m/z=411 (M+H)+
Retention time: 1.11 min (analysis condition SQDAA05)

7-5. Synthesis of (2R)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butyldisulfanecarbonyl)(methyl)amino)-3-(tert-butyldisulfanyl)propanoate (Compound 2m-G)

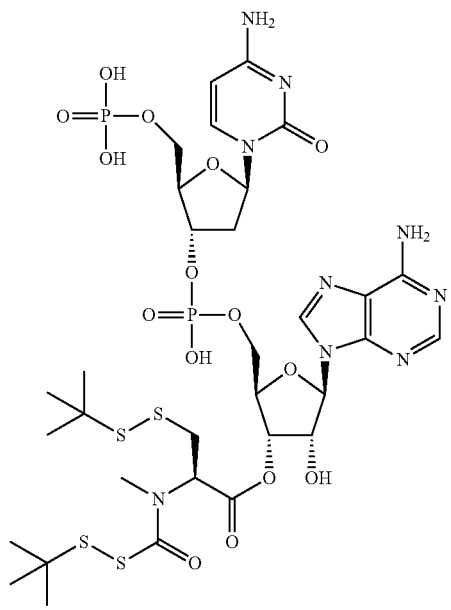 [SMILES: CN(C(=O)SSC(C)(C)C)[C@@H](CSSC(C)(C)C)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (77 mg, 0.121 mmol) in water (2.40 ml) and a solution of (R)-cyanomethyl 2-((tert-butyldisulfanecarbonyl)(methyl)amino)-3-(tert-butyldisulfanyl)propanoate (Compound 21-G) (198 mg, 0.483 mmol) in tetrahydrofuran (1.21 ml) were added to buffer A (46 ml), and the mixture was stirred at room temperature for 2 hours. Trifluoroacetic acid (0.967 ml) was then added, after which the mixture was purified by reverse-phase silica gel column chromatography (0.05% aqueous trifluoroacetic acid solution/0.05% trifluoroacetic acid-acetonitrile solution=100/0→60/40) to afford (2R)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butyldisulfanecarbonyl)(methyl)amino)-3-(tert-butyldisulfanyl)propanoate (Compound 2m-G) (3.8 mg, 3%).

LCMS (ESI) m/z=990 (M+H)+
Retention time: 0.65 min (analysis condition SQDFA05)

[Example 7] Synthesis of Aminoacylated tRNA Having a Cys Derivative

2 µl of 10× ligation buffer (500 mM HEPES-KOH pH 7.5, 200 mM $MgCl_2$, 10 mM ATP) and 4 µl of nuclease free water were added to 10 µl of 50 µM transcribed tRNAfMet-CAU (-CA) (SEQ ID NO: R-5). The mixture was heated at 95° C. for 2 minutes and then left to stand at room temperature for 5 minutes, and the tRNA was refolded. 2 µL of 10 units/µl T4 RNA ligase (New England Biolabs) and 2 µL of a 5 mM solution of aminoacylated pdCpA of Cys(StBu) (Compound 2n-A) in DMSO were added, and ligation reaction was carried out at 15° C. for 45 minutes. Aminoacylated tRNA (Compound AT-2-A) was collected by phenol extraction and ethanol precipitation. Aminoacylated tRNA (Compound AT-2-A) was dissolved in 1 mM sodium acetate immediately prior to addition to the translation mixture.

(SEQ ID NO: 33)

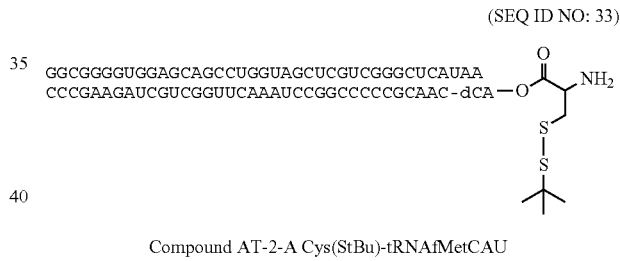

Compound AT-2-A Cys(StBu)-tRNAfMetCAU

[Example 8] Translation Synthesis of Cys(StBu) Using the pdCpA Method

1. Translation Synthesis of Peptide Sequence P-10

Figure 12:
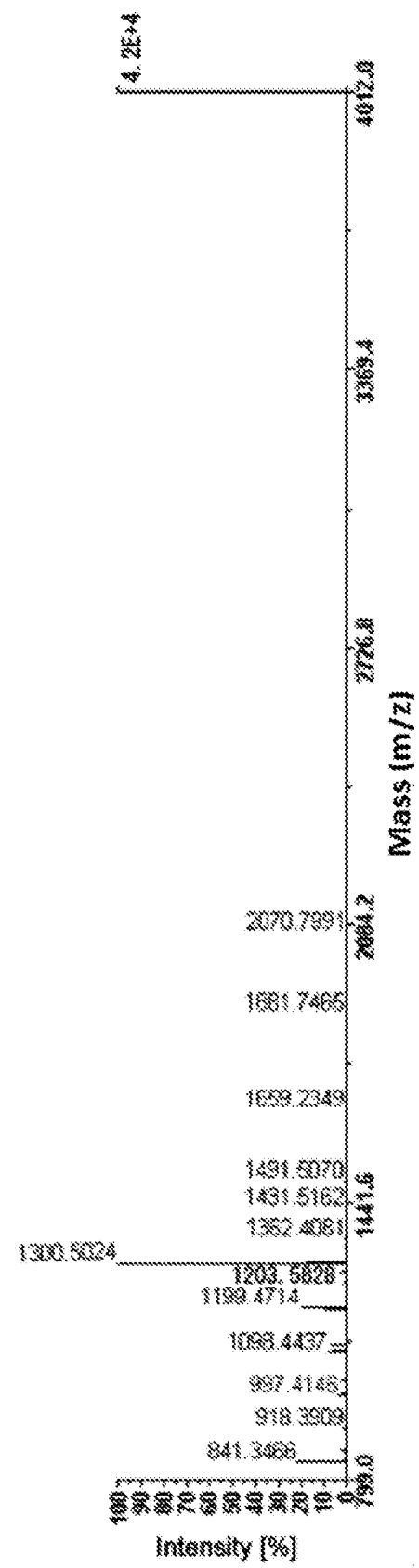
FIG. 12 is a diagram showing the translational synthesis of a peptide having Cys(StBu) at the N-terminal.

The aforementioned transcription and translation solution, 0.1 mM 10-HCO—H4 folate, 0.3 mM Gly, 0.3 mM Arg, 0.3 mM Thr, 0.3 mM Tyr, 0.3 mM Leu, and 50 µM Cys(StBu)-tRNAfMetCAU prepared by the above-described method (Compound AT-2-A) were added to 20 nM template DNA Mtryg3 (SEQ ID NO: D-3), followed by translation at 37° C. for 60 minutes. The resulting translation reaction product was purified with SPE C-TIP (Nikkyo Technos) and analyzed by MALDI-MS. As a result, the target molecule, peptide sequence P-10, could not be observed (FIG. 12). In other words, the translated peptide from initiation AUG was not detected. Efforts are needed to translationally incorporate the Cys derivative to be located at the N-terminal. Meanwhile, an interesting phenomenon was confirmed, where the MS of the peptide (peptide P-11) translated over the full length from Thr, the amino acid encoded by the second codon, was specifically observed.

```
Peptide sequence P-10
                                      (SEQ ID NO: 193)
[Cys(StBu)]ThrThrThrArgLeuTyrTyrArgGlyGly
```

MALDI-MS: m/z: Not detected (Calc. 1345.7)

```
        Peptide sequence (P-11)
                                       (SEQ ID NO: 36)
        ThrThrThrArgLeuTyrTyrArgGlyGly
```

MALDI-MS: m/z: [M+H]+=1300.7 (Calc. 1299.7)

2. Translation Synthesis of Peptide Sequence P-12

The aforementioned transcription and translation solution, 0.1 mM 10-HCO—H4 folate, 0.3 mM each of 18 proteinogenic amino acids excluding Met and Lys, and 50 μM Cys(StBu)-tRNAfMetCAU prepared by the above-described method (Compound AT-2-A) were added to 20 nM template DNA (SEQ ID NO: D-7), followed by translation at 37° C. for 60 minutes. The resulting translation reaction product was purified with SPE C-TIP (Nikkyo Technos) and analyzed by MALDI-MS. As a result, the target molecule, peptide sequence P-12, could be observed. Meanwhile, the MS of peptide P-13 translated over the full length from Thr, the amino acid encoded by the second codon, was specifically observed as the main product. It was shown that a peptide with Cys(StBu) located at the N-terminal can be translationally synthesized, but efficiency of the translation synthesis was low. Examination to improve the synthesis was performed as follows.

```
DNA sequence (D-7)
AKC17 DNA sequence (the same as SEQ ID NO: D-31)
                                       (SEQ ID NO: 7)
GTAATACGACTCACTATAGGGTTAACTTTAAGAAGGAGATATACATATGA CTAGAACTGCCTACTGGAGCcttTGCGGCAGCGGCAGCGGCAGC
Peptide sequence (P-12)
```

```
                    -continued
                                       (SEQ ID NO: 194)
[Cys(StBu)]ThrArgThrAlaTyrTrpSerLeuCysGlySerGlySer GlySer
```

MALDI-MS: m/z: [M+H]+=1723.7 (Calc. 1722.7)

```
        Peptide sequence (P-13)
                                       (SEQ ID NO: 37)
        ThrArgThrAlaTyrTrpSerLeuCysGlySerGlySerGlySer
```

MALDI-MS: m/z: [M+H]+=1532.7 (Calc. 1531.7)

[Example 9] Identification of the Cause of the Low Efficiency in Introduction of N-Terminal Cys by the pdCpA Method The following experiments were carried out to specify the cause of the low efficiency in introduction of N-terminal Cys(StBu) by the pdCpA method.

1. Deprotection of Side Chain StBu of Compound 2n-A

Figure 13:
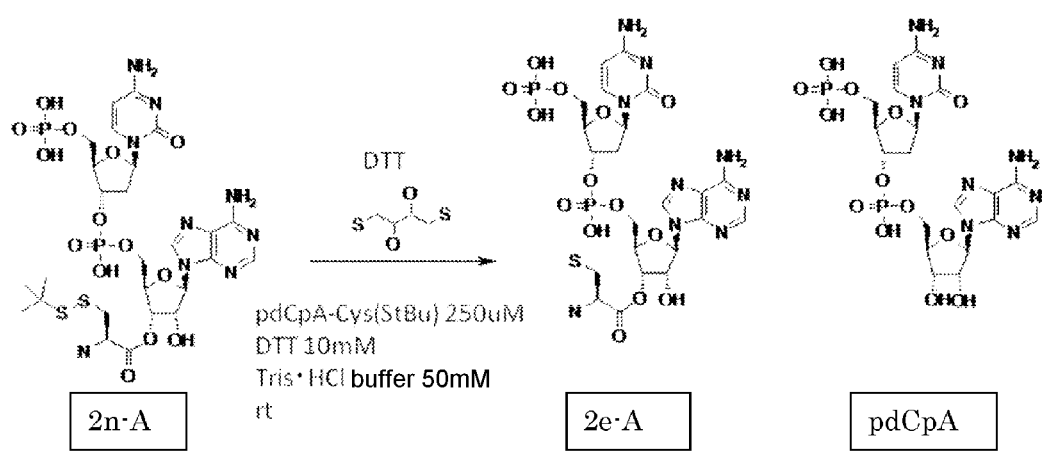
FIG. 13 is a diagram showing the stability of compound 2n-A and compound 2e-A in translation-simulated solutions.

The side chain StBu of pdCpA-Cys was deprotected using the precursor Compound 2n-A, and the following experiment was carried out to examine stability of the deprotected Compound 2e-A. The side chain was deprotected at room temperature under the conditions of 250 μM of Compound 2n-A, 50 mM Tris-HCl buffer, pH 7, and 10 mM DTT, and the time course of the deprotection was observed by LC-MS (SQD). The intended Compound 2e-A was not observed, and pdCpA resulting from hydrolysis of pdCpA-Cys was observed. After 5 minutes, Compound 2n-A was 51%, Compound 2e-A was 0%, and pdCpA was 49%. After 2 hours, deprotection was completed and Compound 2n-A was 0%, but Compound 2e-A was 0% and all hydrolyzed so that pdCpA was 100% (FIG. 13).

The above results revealed that pdCpA-Cys (Compound 2e-A) is disadvantageous for translation, because it is unstable under common translation conditions and is hydrolyzed almost simultaneously with its production.

2. Evaluation of Stability of Compound 2n-A

Stability of Compound 2n-A with the SH group of Cys protected was evaluated. Storage samples were prepared under five conditions as shown in the following Table 2 were prepared, respectively, and analyzed by LC-MS.

TABLE 2

| Storage condition | concentration of pdCpA-Cys(StBu) | pH | Temperature | Time | % remaining pdCpA-Cys(StBu) | by LC-MS pdCpA % |
|---|---|---|---|---|---|---|
| In HEPES buffer | 1 mM | 7 | Room temperature | 1 hour | 30 | 70 |
| In AcONa buffer | 1 mM | 5 | Room temperature | 1 hour | 70 | 30 |
| In AcONa buffer | 2.5 mM | 5 | 0° C. | 2.5 days | 35 | 65 |
| In DMSO | 5 mM | 4 | 0° C. | 2.5 days | 58 | 42 |
| Stored as solid | — | — | Room temperature | 16 days | 64 | 36 |

The percentage of the remaining Compound 2n-A was 30% after one hour in HEPES buffer, pH 7. As described above, Compound 2e-A having the side chain deprotected is rapidly hydrolyzed upon deprotection. Protection of the side chain results in increased stability.

3. Evaluation of Stability of Compound 2n-B

Stability of Compound 2n-B with the SH group of MeCys protected was also evaluated. Storage samples were prepared under four conditions as shown in the following Table 3 were prepared and analyzed by LC-MS.

Compound 2n-B

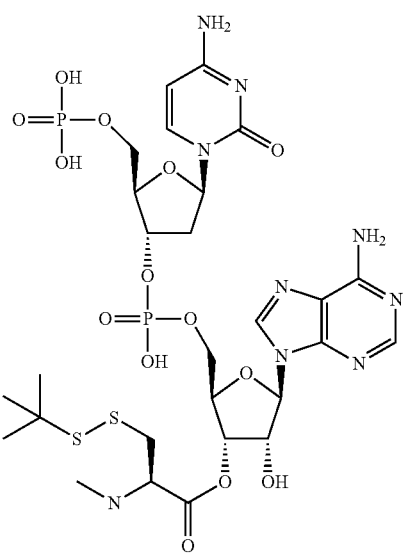

Figure 14:
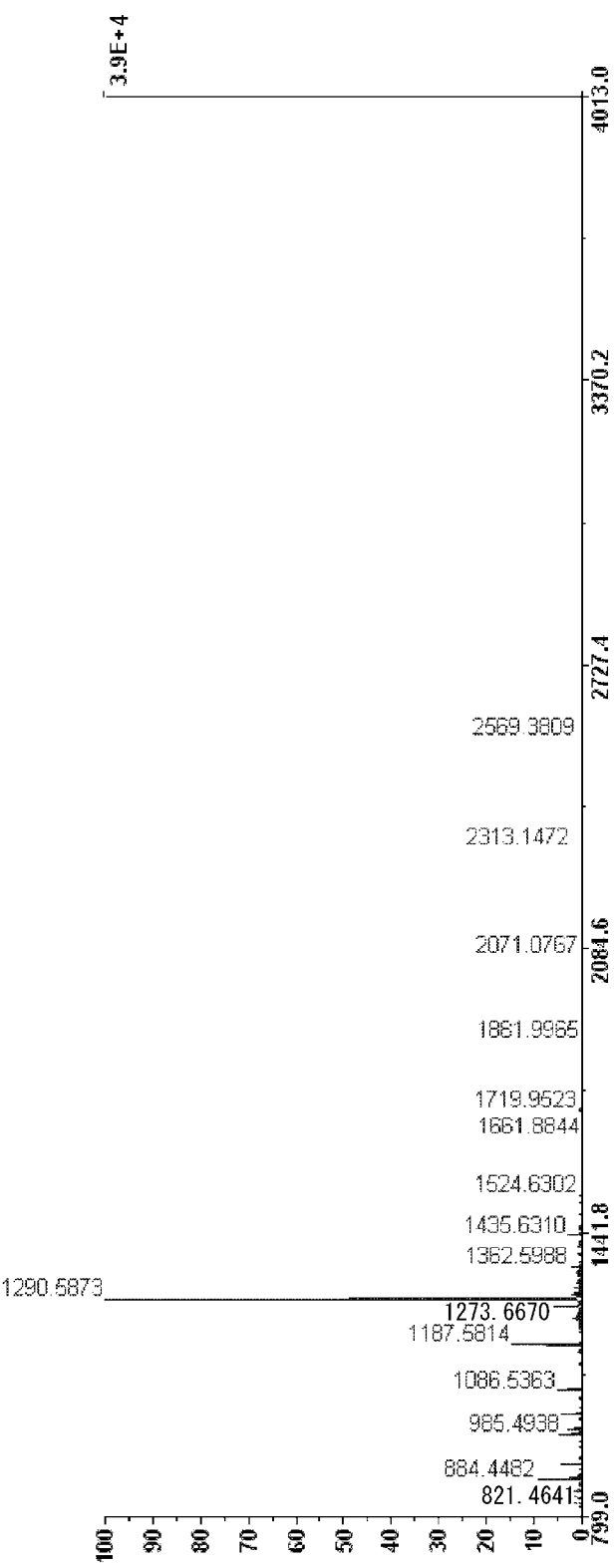
Figures 1, 15:
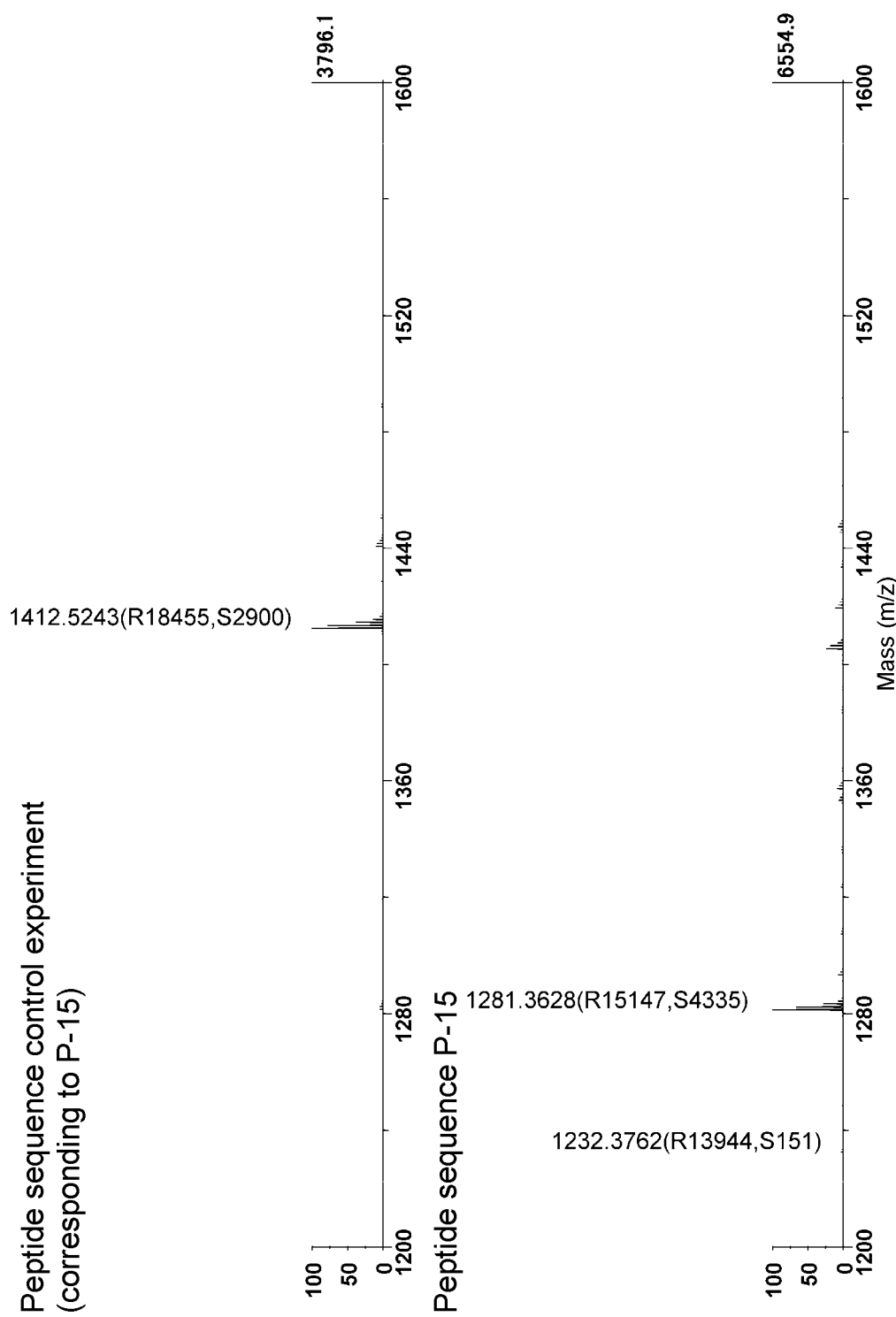
Figure 15:
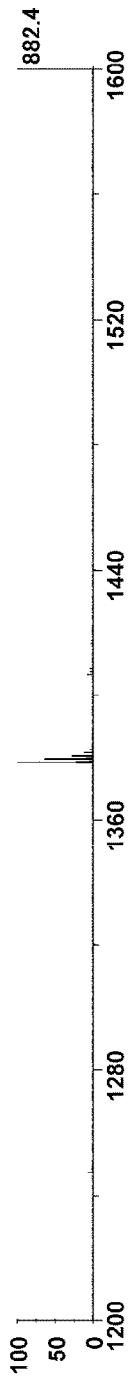
Figure 2:
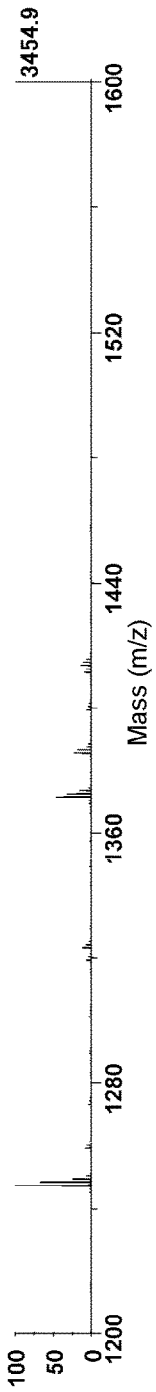
Figures 1, 16:
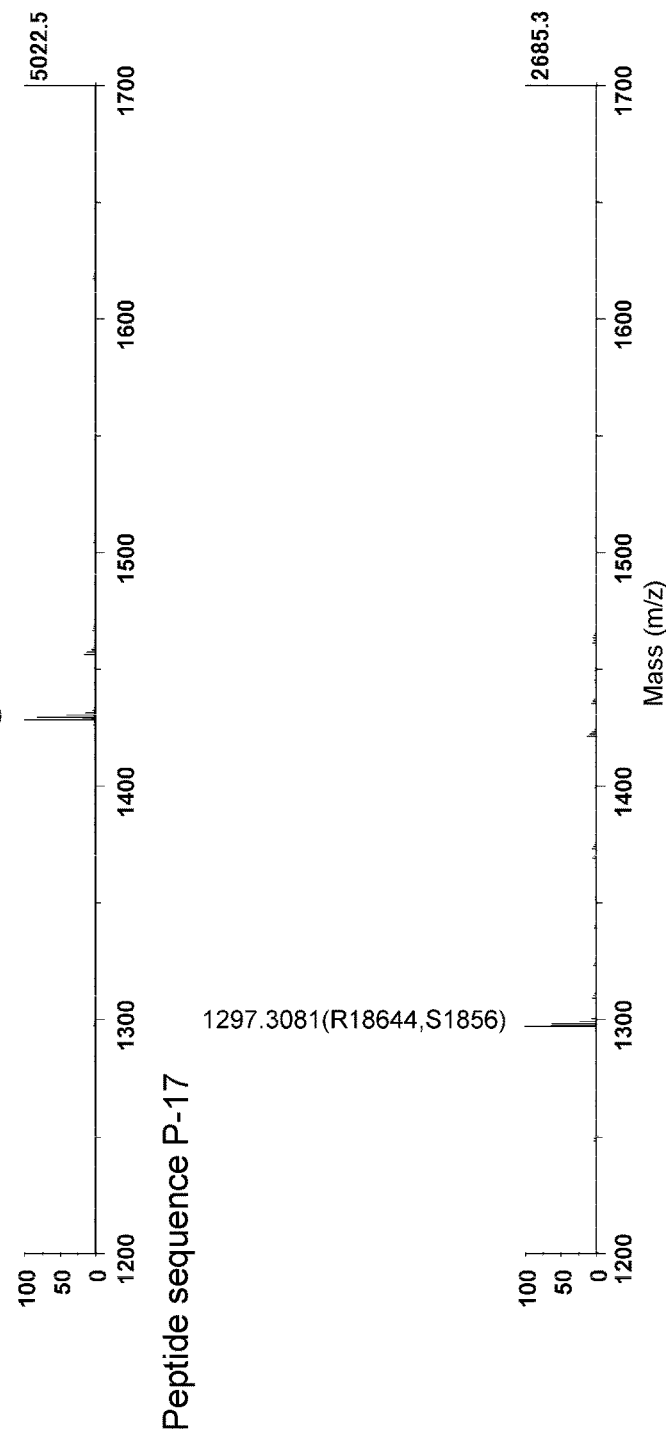
Figure 16:
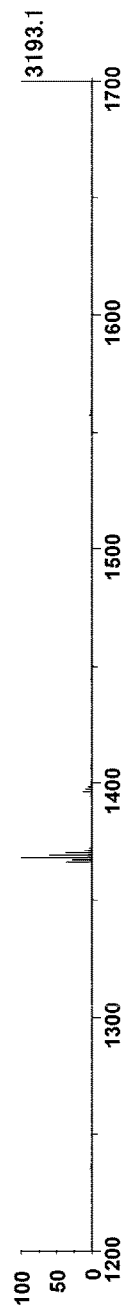
Figure 2:
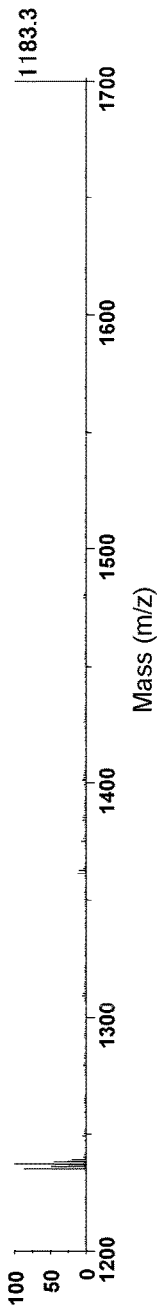
Figures 1, 17:
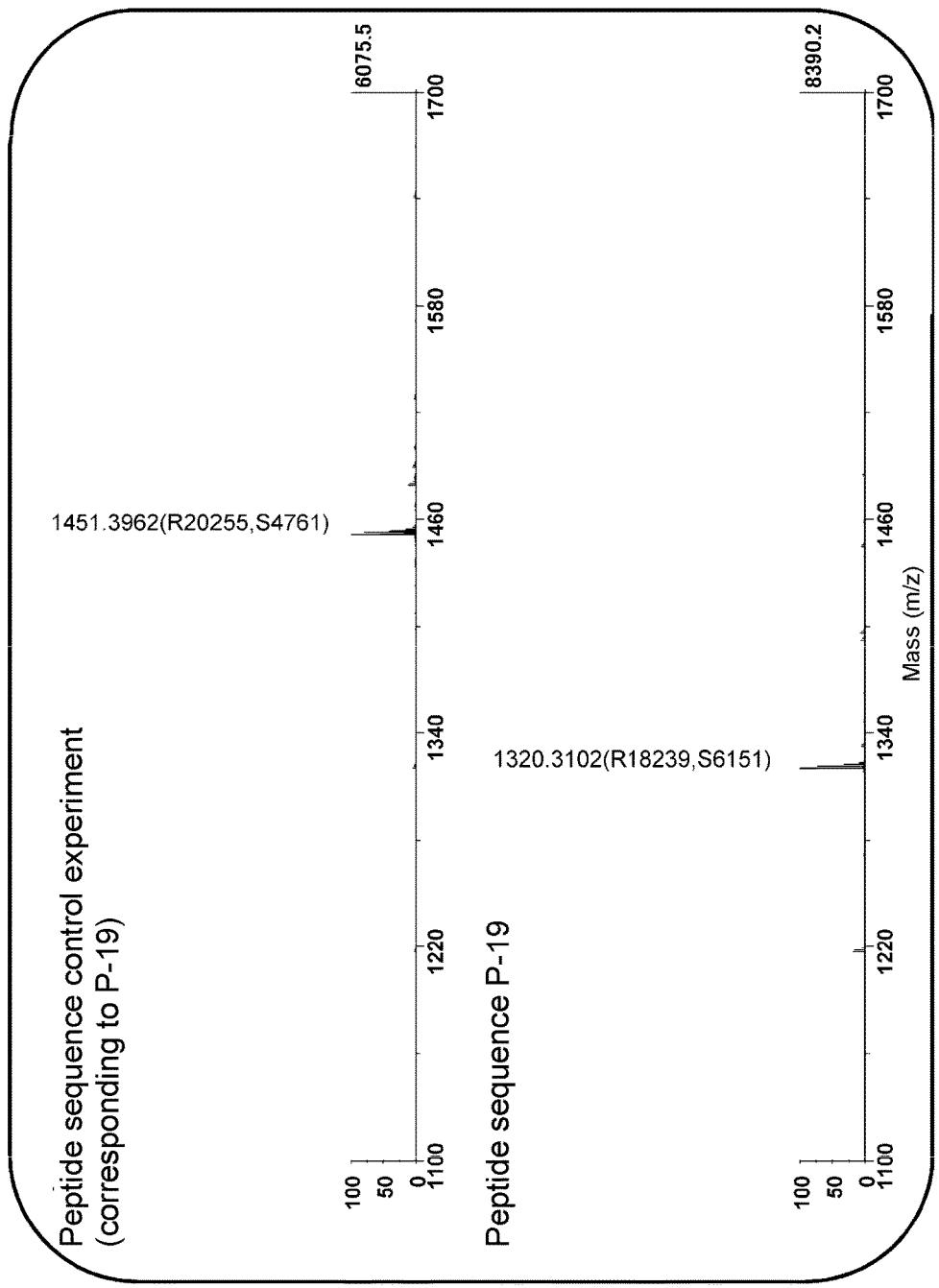
Figure 17:
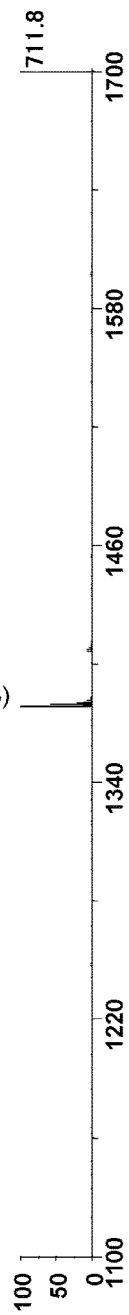
Figure 2:
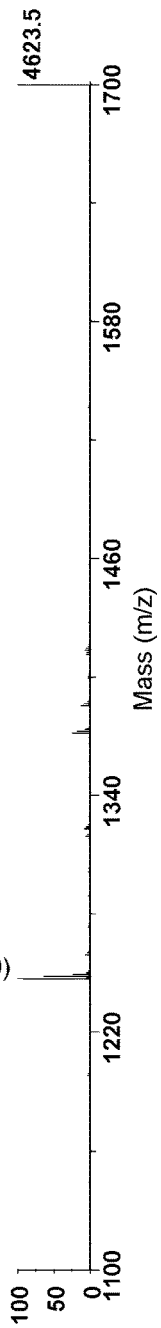
Figures 1, 18:
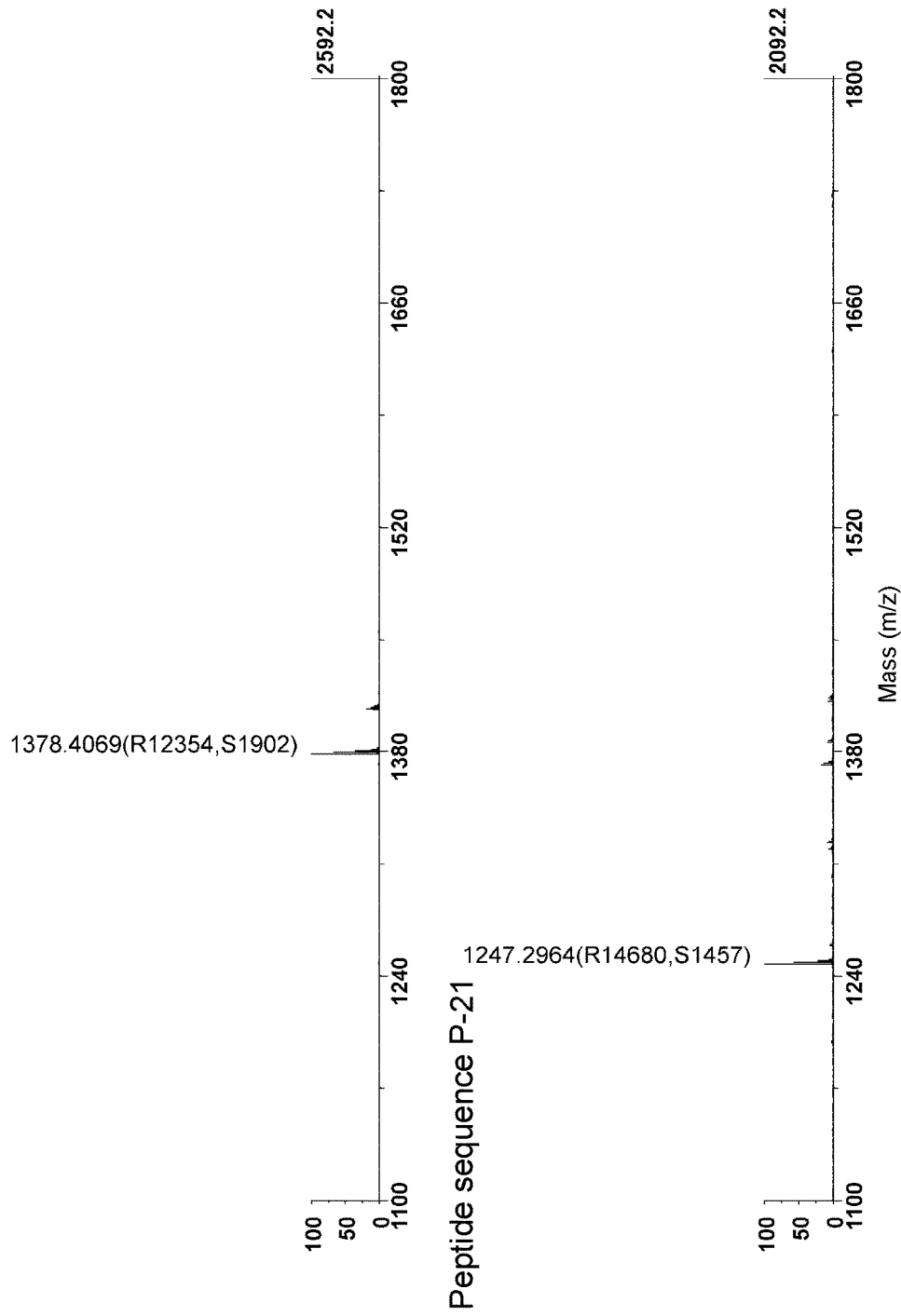
Figures 2, 18:
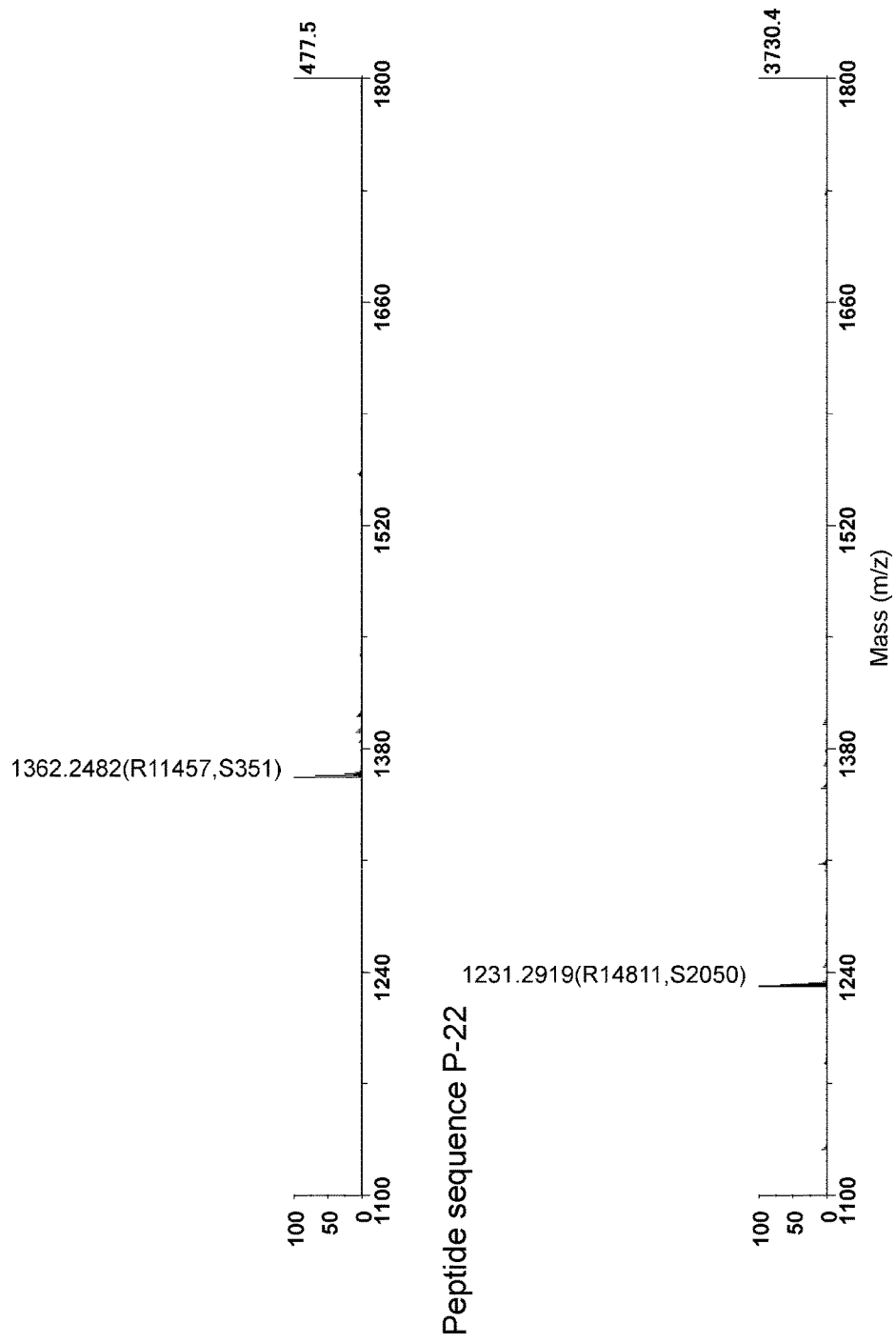
Figures 1, 19:
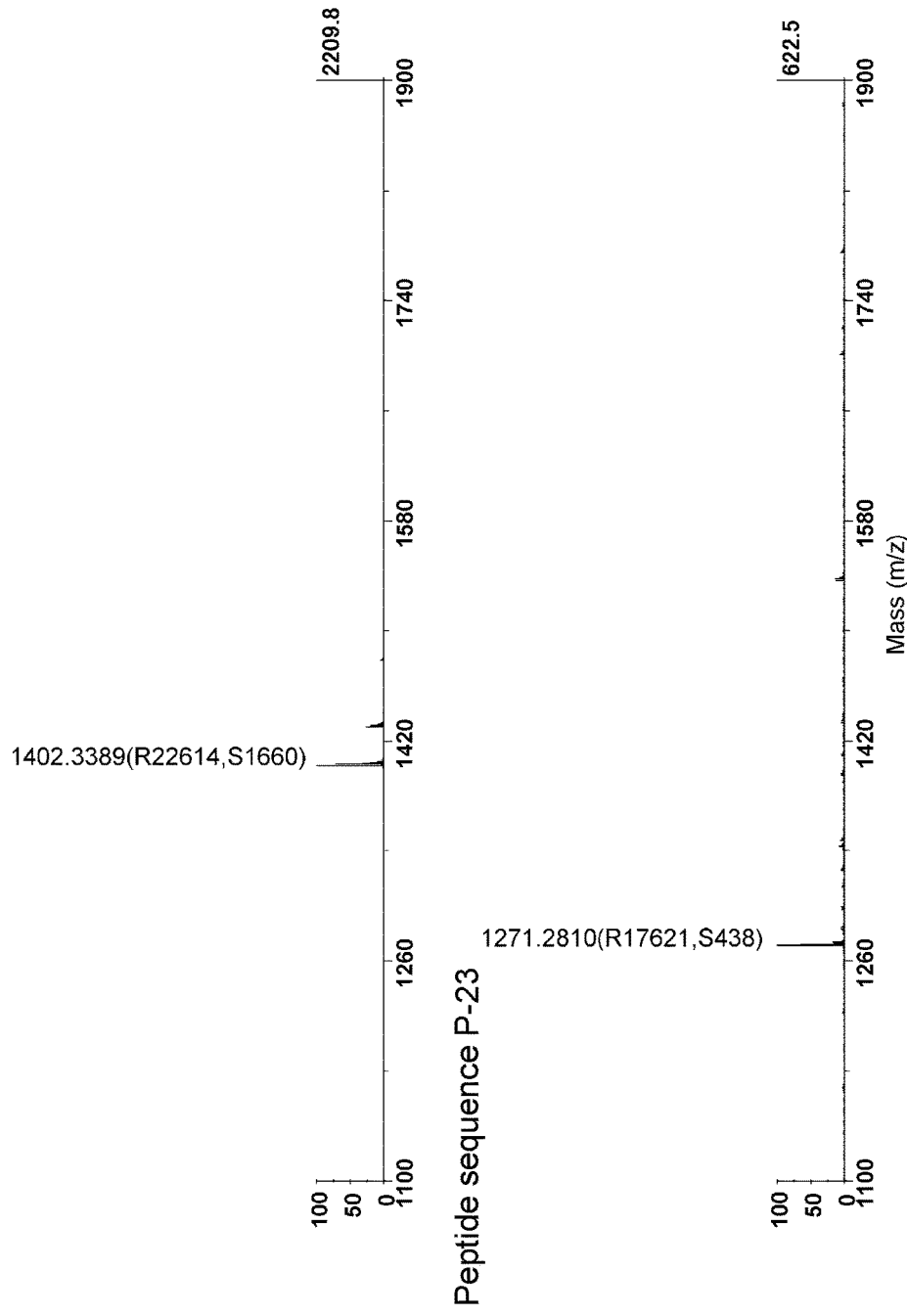
Figures 2, 19:
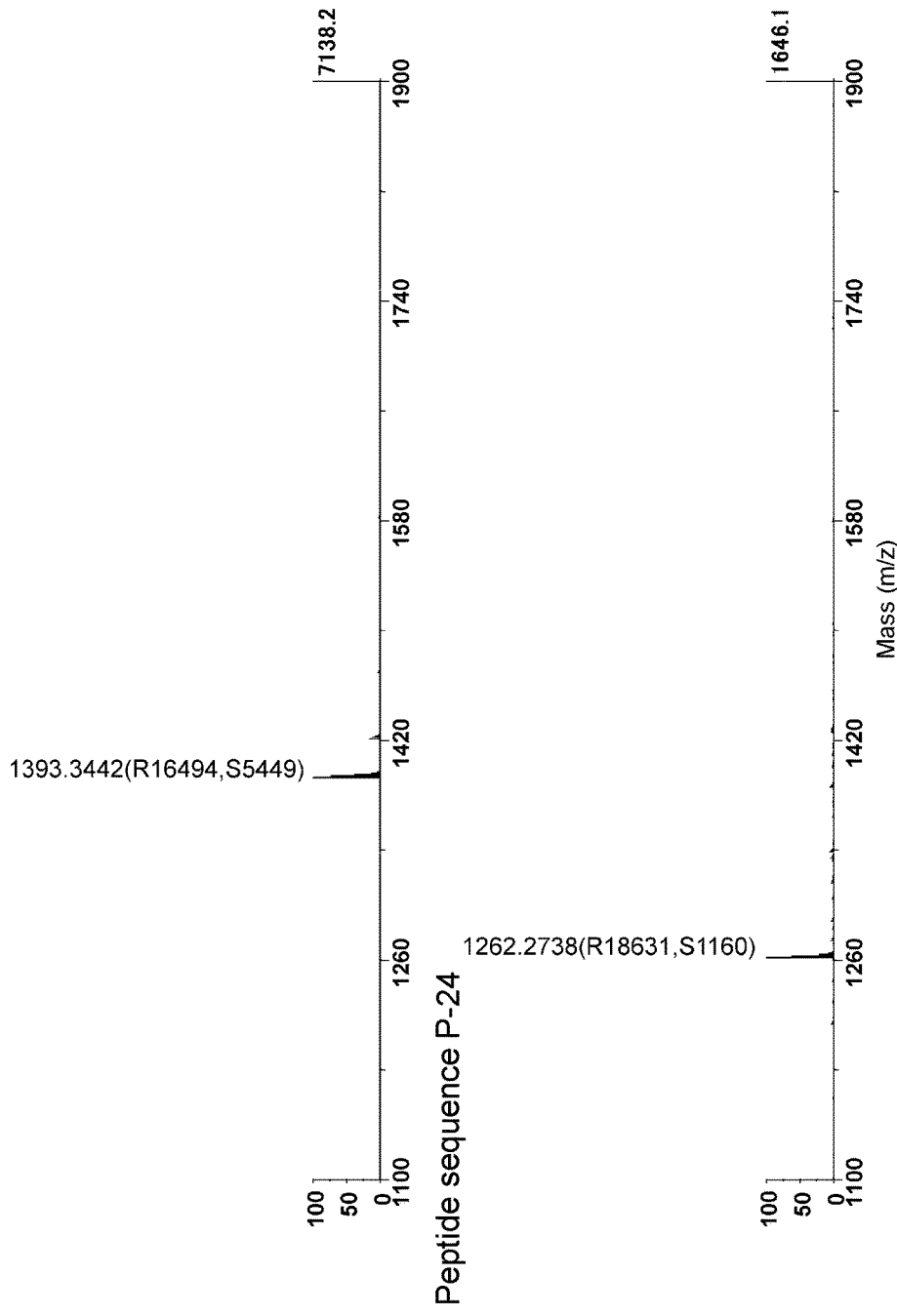
Figure 20:
Figure 1:
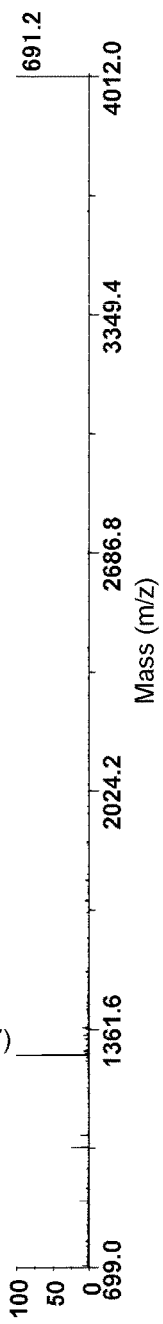
Figure 21:
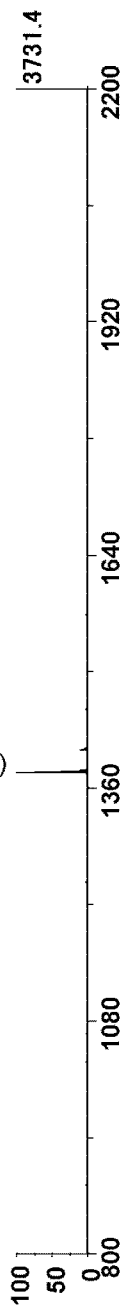
Figure 1:
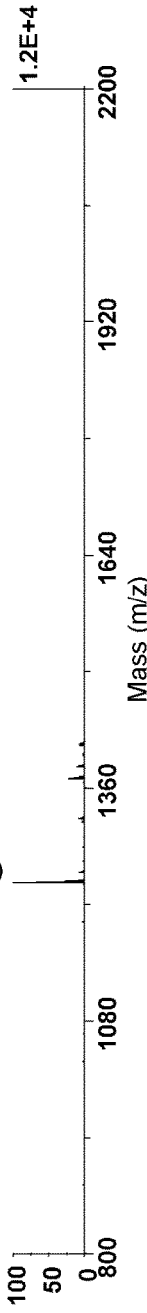
Figures 2, 21:
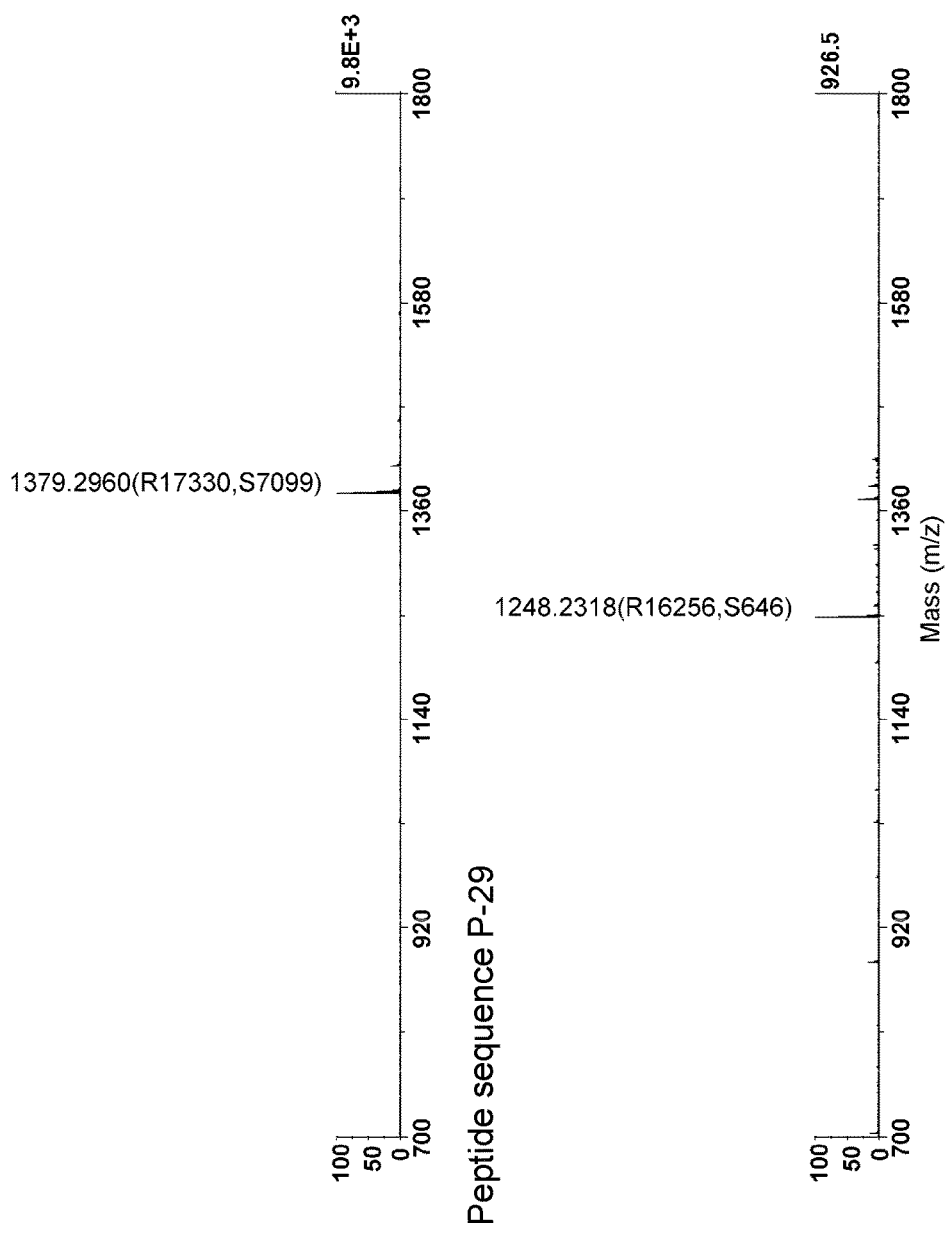
Figure 22:
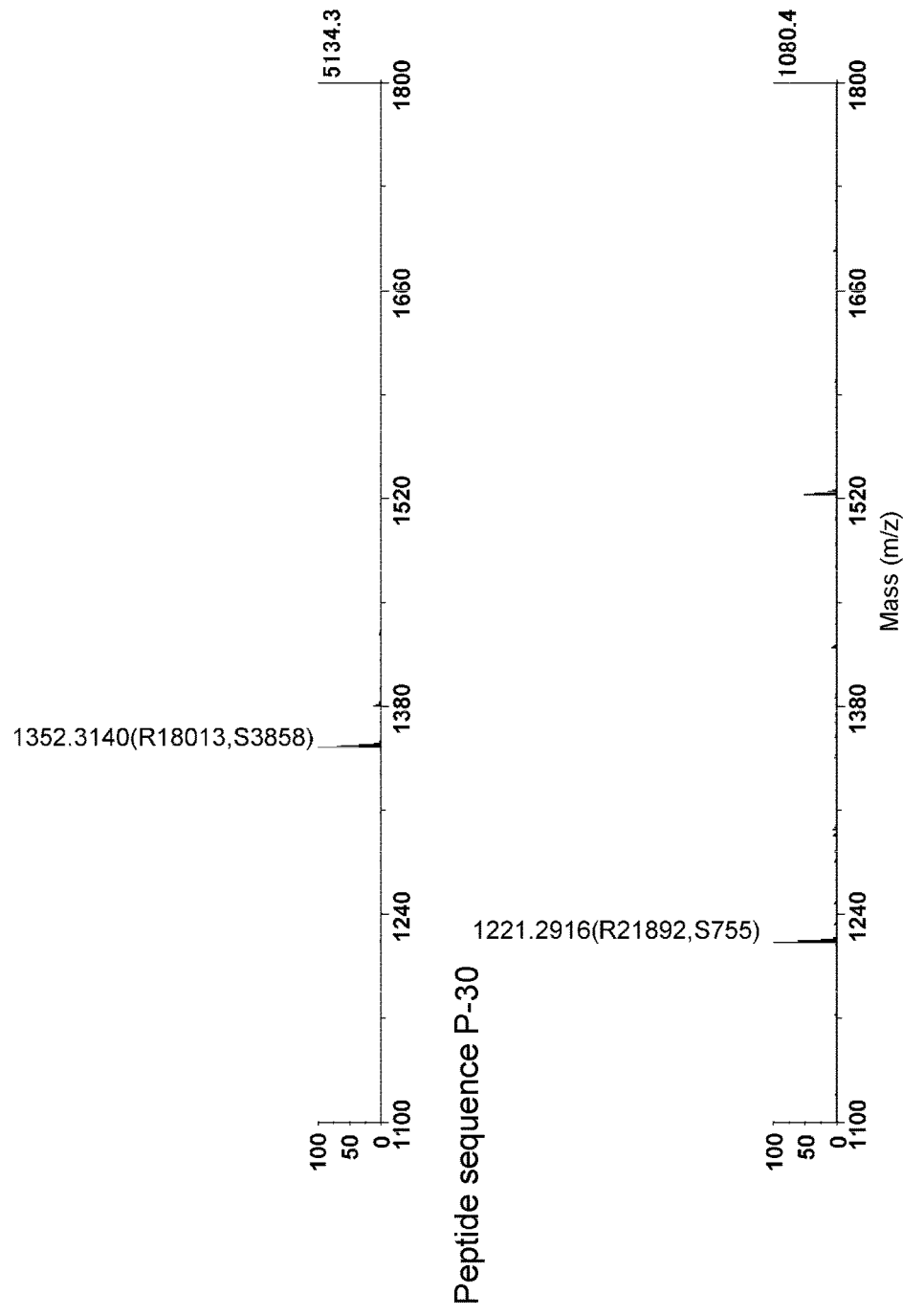
FIG. 22 is a diagram showing the mass spectrum of a translation product containing a distinct amino acid encoded at the third codon immediately following Cys (P-30: Ser).
Figures 1, 23:
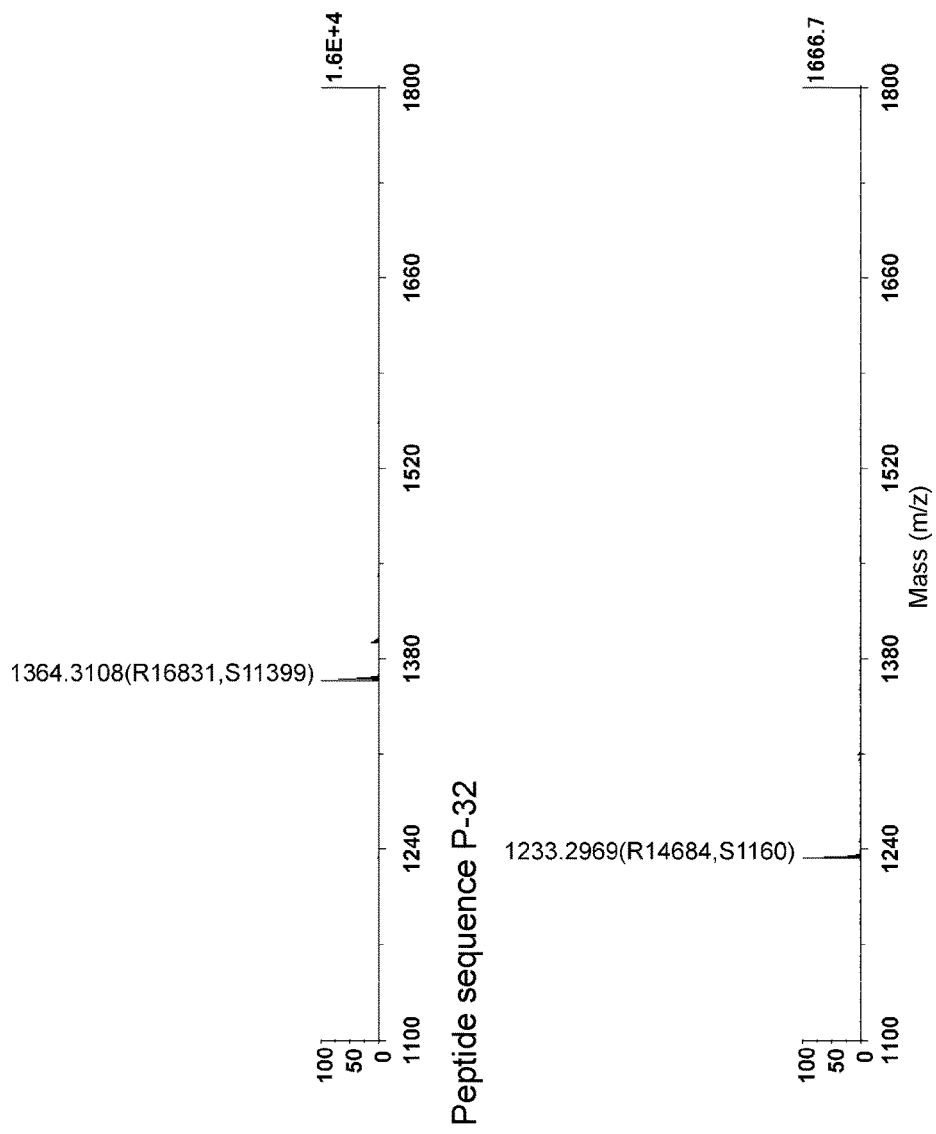
Figures 2, 23:
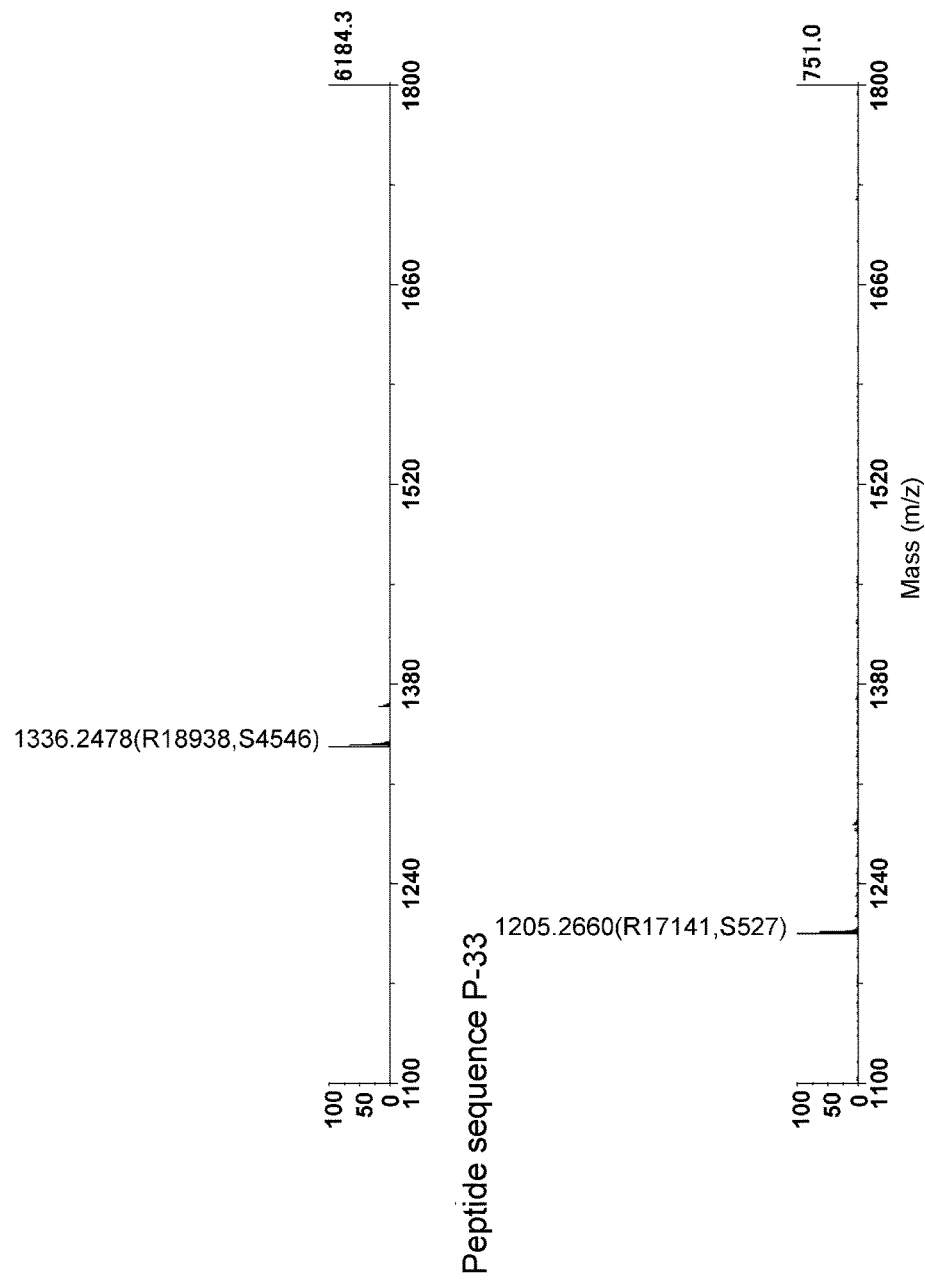

MALDI-MS. As a result, the main peak corresponding to the P-14 was observed in which translation was not initiated from the initiation codon AUG but from the codon encoded next to AUG (corresponding to TGC or Cys) (see FIG. 14).

```
SEQ ID NO: D-8
Mctryg3 DNA sequence
                                          (SEQ ID NO: 8)
GTAATACGACTCACTATAGGGTTAACTTTAAGAAGGAGATATACATatgt gcACTACAACGCGTctttactaccgtggcggcTAGTAGATAGATAG Translated peptide P-14
                                         (SEQ ID NO: 38)
CysThrThrThrArgLeuTyrTyrArgGlyGly
```

2. Examination of the Difference in Initiation Read Through Efficiency Due to the Difference of the Third Codon Immediately Following Cys The influence of the third codon on initiation read through was evaluated. The aforementioned *E. coli*-derived reconstituted cell-free transcription and translation solution and 0.3 mM each of 19 proteinogenic amino acids excluding Met were added to 20 nM template DNA IniRt_XXX_am (SEQ

TABLE 3

| Storage condition | concentration of pdCpA-MeCys(StBu) | pH | Temperature | Time | % remaining pdCpA-MeCys(StBu) | by LC-MS pdCpA % |
|---|---|---|---|---|---|---|
| In HEPES buffer | 1 mM | 7 | Room temperature | 1 hour | 49 | 51 |
| In Tris buffer | 1 mM | 7 | Room temperature | 1 hour | 35 | 65 |
| In AcONa buffer | 1 mM | 5 | Room temperature | 5 hours | 100 | 0 |
| In DMSO | 5 mM | 4 | 0° C. | 1 day | 100 | 0 |

Stability in pH 7 buffer of Compound 2n-B was comparable with that of Compound 2n-A. Stability in pH 5 buffer or DMSO solution of Compound 2n-B was higher than that of Compound 2n-A. It is assumed that stability of pdCpA-amino acid is increased by the electronic effect of a methyl group, because Compound 2n-B is N-methylated.

From the above results, instability of aminoacylated tRNA due to the presence of the side chain SH group was specified as a cause of the low efficiency in incorporation of N-terminal Cys(StBu) by the pdCpA method.

[Example 10] Efficient Translational Incorporation of N-Terminal Cys Using the Initiation Read Through Method Incorporation of Cys at the peptide N-terminal was attempted as follows by allowing a phenomenon observed in Example 9 in which translation was efficiently initiated from the second codon (initiation read through).

1. Initiation Read Through Method

Translation was performed by the following method. The aforementioned transcription and translation solution, 0.3 mM Gly, 0.3 mM Arg, 0.3 mM Thr, 0.3 mM Tyr, 0.3 mM Leu and 0.3 mM Cys were added to 20 nM template DNA Mctryg3 (SEQ ID NO: D-8), followed by translation at 37° C. for 60 minutes. The translation reaction product was purified with SPE C-TIP (Nikkyo Technos) and analyzed by MALDI-MS. As a result, the MS of the peptide translated from Cys encoded next to initiation AUG was observed.

It was found that when mRNA encoding Cys immediately following the translation initiation codon ATG is translated, peptides with Cys as the N-terminal residue are translationally synthesized as main products with high reproducibility for all 19 peptides translated (translated peptides P-15 to P-33) as long as methionine, the original amino acid assigned to the initiation codon, is excluded from the translation system. This made it possible to incorporate Cys at the N-terminal without preparing unstable Cysacyl tRNA outside the system and adding it to the translation system (see FIGS. 15 to 23). A control experiment was also carried out at the same time, where a full-length peptide was translated with methionine added to the above translation system.

```
IniRt_XXX_am template DNA sequence
                                       (SEQ ID NOs: 9-27)
GTAATACGACTCACTATAGGGTTAACTTTAAGAAGGAGATATACATATG tgcXXXACTACAACGctttactaccgtggcggcTAGTAGATAGATAG
(XXX: TTT (SEQ ID NO: D-9 (SEQ ID NO: 9)),
TTG (SEQ ID NO: D-10 (SEQ ID NO: 10)),
TAC (SEQ ID NO: D-11 (SEQ ID NO: 11)),
```

-continued

TGC (SEQ ID NO: D-12 (SEQ ID NO: 12)),
TGG (SEQ ID NO: D-13 (SEQ ID NO: 13)),
CTT (SEQ ID NO: D-14 (SEQ ID NO: 14)),
CTA (SEQ ID NO: D-15 (SEQ ID NO: 15)),
CCG (SEQ ID NO: D-16 (SEQ ID NO: 16)),
CAT (SEQ ID NO: D-17 (SEQ ID NO: 17)),
CAG (SEQ ID NO: D-18 (SEQ ID NO: 18)),
CGT (SEQ ID NO: D-19 (SEQ ID NO: 19)),
CGG (SEQ ID NO: D-20 (SEQ ID NO: 20)),
ATT (SEQ ID NO: D-21 (SEQ ID NO: 21)),
ACT (SEQ ID NO: D-23 (SEQ ID NO: 22)),
AAC (SEQ ID NO: D-24 (SEQ ID NO: 23)),
AGT (SEQ ID NO: D-25 (SEQ ID NO: 24)),
AGG (SEQ ID NO: D-26 (SEQ ID NO: 25)),
GTT (SEQ ID NO: D-27 (SEQ ID NO: 26)),
GCT (SEQ ID NO: D-28 (SEQ ID NO: 27))

IniRt_XXX_am peptide sequence (translated peptide
IDs P-15 to P-33)

(SEQ ID NO: 39-57)
CysXaaThrThrThrLeuTyrTyrArgGlyGly

Table of MALDI-MS Calculated and Found Values

TABLE 4

| Translated peptide ID | 3rd codon XXX | Amino acid Xaa | Calc. | Found [M + H]+ |
|---|---|---|---|---|
| P-15 (SEQ ID NO: 39) | TTT | Phe | 1280.6 | 1281.4 |
| P-16 (SEQ ID NO: 40) | TTG | Leu | 1246.6 | 1247.4 |
| P-17 (SEQ ID NO: 41) | TAC | Tyr | 1296.6 | 1297.3 |
| P-18 (SEQ ID NO: 42) | TGC | Cys | 1236.5 | 1237.2 |
| P-19 (SEQ ID NO: 43) | TGG | Trp | 1319.6 | 1320.3 |
| P-20 (SEQ ID NO: 44) | CTT | Leu | 1246.6 | 1247.3 |
| P-21 (SEQ ID NO: 45) | CTA | Leu | 1246.6 | 1247.3 |
| P-22 (SEQ ID NO: 46) | CCG | Pro | 1230.6 | 1231.3 |
| P-23 (SEQ ID NO: 47) | CAT | His | 1270.6 | 1271.3 |
| P-24 (SEQ ID NO: 48) | CAG | Gln | 1261.6 | 1262.3 |
| P-25 (SEQ ID NO: 49) | CGT | Arg | 1289.6 | 1290.3 |
| P-26 (SEQ ID NO: 50) | CGG | Arg | 1289.6 | 1290.3 |
| P-27 (SEQ ID NO: 51) | ATT | Ile | 1246.6 | 1247.3 |
| P-28 (SEQ ID NO: 52) | ACT | Thr | 1234.6 | 1235.2 |
| P-29 (SEQ ID NO: 53) | AAC | Asn | 1247.6 | 1248.2 |
| P-30 (SEQ ID NO: 54) | AGT | Ser | 1220.5 | 1221.3 |
| P-31 (SEQ ID NO: 55) | AGG | Arg | 1289.6 | 1290.3 |
| P-32 (SEQ ID NO: 56) | GTT | Val | 1232.6 | 1233.3 |
| P-33 (SEQ ID NO: 57) | GCT | Ala | 1204.6 | 1205.3 |

[Example 11] Synthesis of Unnatural Amino Acids with a SH Group Other than Cys, and Aminoacylated pdCpAs Thereof Although Cys, a natural amino acid, was translationally incorporated efficiently by the initiation read through method utilizing ARS, incorporating of unnatural amino acids by ARS has limitations. For this reason, aminoacylated pdCpA compounds modified to have active ester moieties slowly hydrolyzed were synthesized and evaluated. Specifically, a series of compounds having a SH group apart from a carboxylic acid active ester site were synthesized and evaluated.

Figure 24:
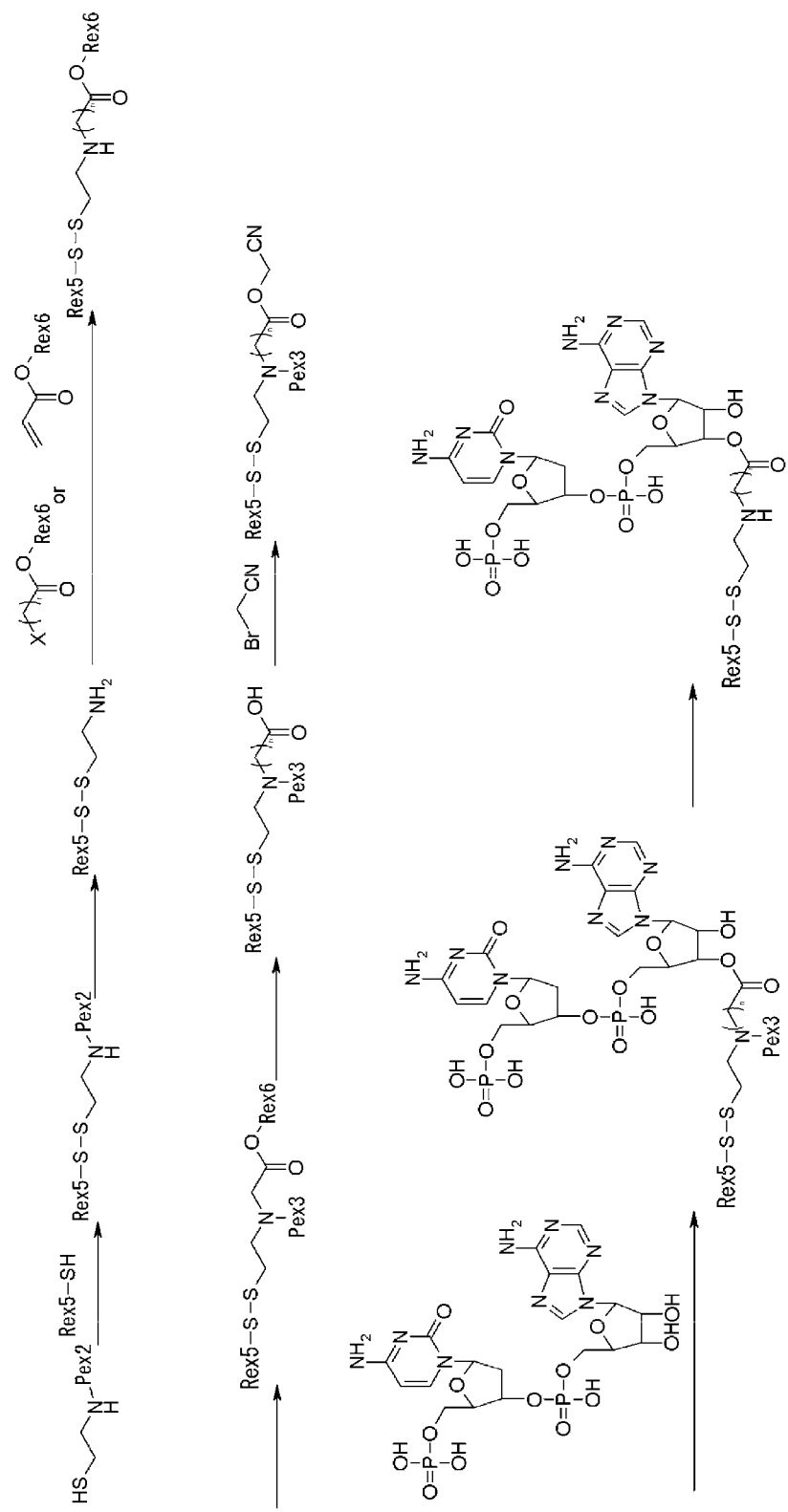
FIG. 24 is a diagram showing general methods for synthesizing unnatural amino acids with an SH group other than Cys, and aminoacylated pdCpAs thereof.

First, aminoacylated pdCpA were synthesized having unnatural amino acid (for N-terminal) having a SH group and an active ester site stable to hydrolysis (FIG. 24).

1. Synthesis of Compound 6i-A 1-1. Synthesis of Tert-Butyl (2-(tert-butyldisulfanyl)ethyl)carbamate (Compound 6b-A)

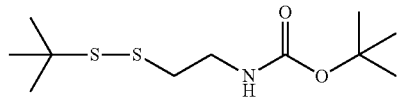 [SMILES: CC(C)(C)OC(=O)NCCSSC(C)(C)C]

1-Chloro-1H-benzo[d][1,2,3]triazole (1.73 g, 11.28 mmol) and 1H-benzo[d][1,2,3]triazole (0.67 g, 5.64 mmol) were dissolved in DCM (24.0 ml) under a nitrogen atmosphere, the mixture was cooled to −78° C., and a solution of tert-butyl (2-mercaptoethyl)carbamate (Compound 6a) (1.00 g, 5.64 mmol) in DCM (3.0 ml) was added dropwise. Following stirring at 78° C. for 10 minutes, a suspension of thiourea (1.29 g, 16.92 mmol) in THF (6.0 ml) was added and the mixture was further stirred for 10 minutes. A solution of 2-methylpropane-2-thiol (0.76 g, 8.46 mmol) in DCM (3.0 ml) was then added dropwise, and the mixture was stirred with warming to room temperature for 20 hours. The solid in the reaction solution was removed by filtration, and the filtrate was concentrated under reduced pressure. The residue was purified by column chromatography (hexane:ethyl acetate=4:1) to afford the title compound (1.15 g, 77%).

LCMS: m/z 266 (M+H)+
Retention time: 1.05 min (analysis condition SQDAA05)

1-2. Synthesis of 2-(tert-butyldisulfanyl)ethanamine (Compound 6c-A)

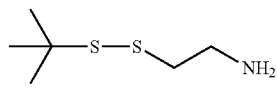

A solution of TFA (1.0 ml) in DCM (1.0 ml) was added to tert-butyl (2-(tert-butyldisulfanyl)ethyl)carbamate (Compound 6b-A, 100 mg, 0.377 mmol), and the mixture was stirred at room temperature for 15 minutes. The reaction solution was concentrated under reduced pressure to afford the title compound (209 mg, quant.).

LCMS: m/z 166 (M+H)+
Retention time: 0.63 min (analysis condition SQDAA05)

1-1. Synthesis of Ethyl 2-((tert-butoxycarbonyl)(2-(tert-butyldisulfanyl)ethyl)amino)acetate (Compound 6e-A)

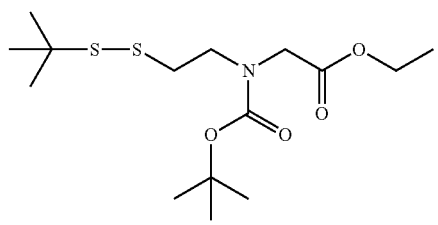 [SMILES: CCOC(=O)CN(CCSSC(C)(C)C)C(=O)OC(C)(C)C]

2-(tert-Butyldisulfanyl)ethanamine (Compound 6c-A, 0.21 g, 1.26 mmol) and ethyl 2-bromoacetate (0.23 g, 1.39 mmol) were dissolved in DCM (6.0 ml), DIPEA (1.10 ml, 6.31 mmol) was added, and the mixture was stirred at room temperature for 17 hours. tert-Butyl dicarbonate (358 mg, 1.64 mmol) was added to the reaction solution, and the mixture was stirred at room temperature for 15 minutes. The reaction solution was then directly purified by column chromatography (hexane:ethyl acetate=4:1) to afford the title compound (334.8 mg, 75%).

LCMS: m/z 352 (M+H)+

Retention time: 1.11 min (analysis condition SQDAA05)

1-4. Synthesis of 2-((tert-butoxycarbonyl)(2-(tert-butyldisulfanyl)ethyl)amino)acetic Acid (Compound 6f-A)

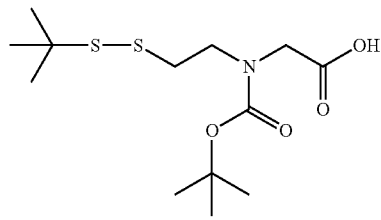 [SMILES: CC(C)(C)OC(=O)N(CCSSC(C)(C)C)CC(=O)O]

Ethyl 2-((tert-butoxycarbonyl)(2-(tert-butyldisulfanyl)ethyl)amino)acetate (Compound 6e-A, 320 mg, 0.91 mmol) was dissolved in methanol (80 ml), an aqueous potassium hydroxide solution (0.18 mol/l, 30.3 ml) was added and the mixture was stirred at room temperature for 2 hours. Methanol in the reaction solution was removed by concentration under reduced pressure, and the aqueous layer was washed with diethyl ether and then adjusted to pH 3 with a 1 mol/l aqueous hydrochloric acid solution. The aqueous layer was extracted with ethyl acetate, and the organic layer was dried over anhydrous magnesium sulfate, filtered and concentrated under reduced pressure to afford the title compound (268.1 mg, 91%).

LCMS: m/z 322 (M−H)−

Retention time: 0.89 min (analysis condition SQDAA05)

1-5. Synthesis of Cyanomethyl 2-((tert-butoxycarbonyl)(2-(tert-butyldisulfanyl)ethyl)amino)acetate (Compound 6g-A)

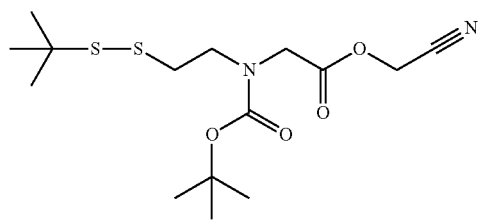 [SMILES: CC(C)(C)OC(=O)N(CCSSC(C)(C)C)CC(=O)OCC#N]

2-((tert-Butoxycarbonyl)(2-(tert-butyldisulfanyl)ethyl)amino)acetic acid (Compound 6f-A, 268.1 mg, 0.83 mmol) and 2-bromoacetonitrile (199 mg, 1.66 mmol) were dissolved in DMF (1.0 ml), DIPEA (0.43 ml, 2.49 mmol) was added and the mixture was stirred at room temperature for 15 minutes. A saturated aqueous ammonium chloride solution was added to the reaction solution, followed by extraction with diethyl ether. The resulting organic layer was dried over anhydrous magnesium sulfate, filtered and concentrated under reduced pressure. The resulting residue was purified by column chromatography (hexane:ethyl acetate=3:1) to afford the title compound (287.7 mg, 96%).

LCMS: m/z 363 (M+H)+

Retention time: 1.04 min (analysis condition SQDAA05)

1-6. Synthesis of (2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)(2-(tert-butyldisulfanyl)ethyl)amino)acetate (Compound 6h-A)

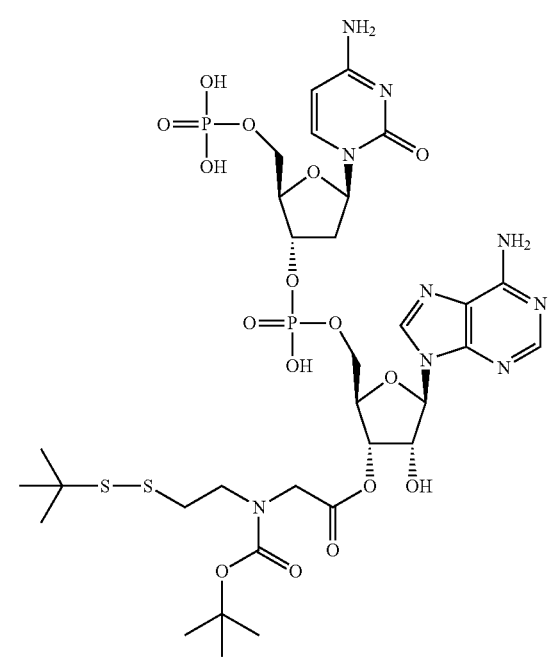 [SMILES: CC(C)(C)OC(=O)N(CCSSC(C)(C)C)CC(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

A solution of ((2R,3S,5R)-5-(4-amino-2-oxopyrimidin-1 (2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h, 100 mg, 0.157 mmol) in water (1.0 ml) was added to a buffer (40 ml) in which imidazole (272.3 mg, 4.00 mmol) and N,N,N-trimethylhexadecan-1-aminium chloride (256.0 mg, 0.80 mmol) were dissolved and which was adjusted to pH 8 with acetic acid. A solution of cyanomethyl 2-((tert-butoxycarbonyl)(2-(tert-butyldisulfanyl)ethyl)amino)acetate (Compound 6g-A, 198 mg, 0.546 mmol) in THF (1.2 ml) was then added and the mixture was stirred at room temperature for 4 hours. The reaction solution was directly lyophilized, and the resulting residue was purified by column chromatography (0.05% aqueous TFA solution:0.05% TFA-acetonitrile solution=85:15).

LCMS: m/z 942 (M+H)+

Retention time: 0.89 min (analysis condition SMD method 1)

1-7. Synthesis of (2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((2-(tert-butyldisulfanyl)ethyl)amino)acetate (Compound 6i-A)

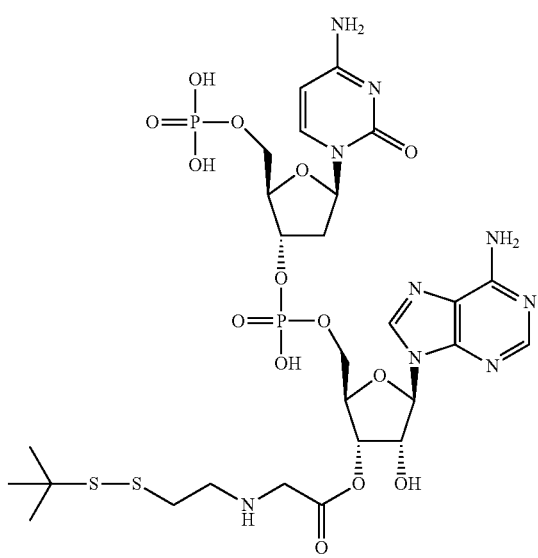 [SMILES: CC(C)(C)SSCCNCC(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)(2-(tert-butyldisulfanyl)ethyl)amino)acetate (Compound 6h-A, 56.2 mg, 0.060 mmol) was dissolved in TFA (1.0 ml), and the mixture was stirred at room temperature for 5 minutes. The reaction solution was concentrated under reduced pressure, and the residue was then purified by Column chromatography (0.05% aqueous TFA solution:0.05% TFA-acetonitrile solution=85:15=85:15) to afford the title compound (40.6 mg, 81%).

LCMS: m/z 842 (M+H)+
Retention time: 0.39 min (analysis condition SQDAA05)

2. Synthesis of Compound 6i-B 2-1. Synthesis of Methyl 3-((tert-butoxycarbonyl)(2-(tert-butyldisulfanyl)ethyl)amino)propanoate (Compound 6e-B)

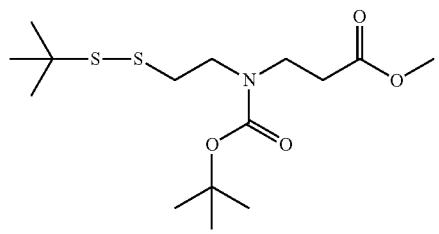 [SMILES: COC(=O)CCN(CCSSC(C)(C)C)C(=O)OC(C)(C)C]

2-(tert-Butyldisulfanyl)ethanamine (Compound 6c-A, 0.80 g, 0.84 mmol) and methyl acrylate (1.74 ml, 19.36 mmol) were dissolved in dichloroethane (14.0 ml), DIPEA (4.23 ml, 24.20 mmol) was added and the mixture was stirred at 85° C. for 2 hours. The reaction mixture was left to cool and tert-butyl dicarbonate (1.37 g, 6.29 mmol) was added. After stirring at room temperature for 45 minutes, a saturated aqueous ammonium chloride solution was added, followed by extraction with DCM. The resulting organic layer was washed with a saturated aqueous sodium chloride solution, and then dried over anhydrous magnesium sulfate, filtered and concentrated under reduced pressure. The resulting residue was purified by column chromatography (hexane:ethyl acetate=3:1) to afford the title compound (1.14 g, 67%).

LCMS: m/z 352 (M+H)+
Retention time: 1.11 min (analysis condition SQDAA05)

2-2. Synthesis of 3-((tert-butoxycarbonyl)(2-(tert-butyldisulfanyl)ethyl)amino)propanoic Acid (Compound 6f-B

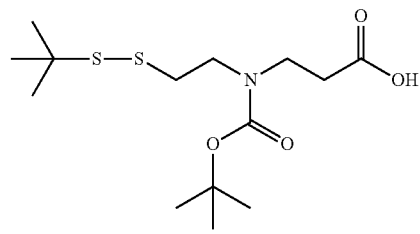 [SMILES: CC(C)(C)OC(=O)N(CCSSC(C)(C)C)CCC(=O)O]

The title compound (1.04 g, 95%) was obtained by the same method as in the synthesis of Compound 6f-A using methyl 3-((tert-butoxycarbonyl)(2-(tert-butyldisulfanyl)ethyl)amino)propanoate (Compound 6e-B, 1.14 g, 3.24 mmol) as a starting material.

LCMS: m/z 336 (M−H)−
Retention time: 0.96 min (analysis condition SQDAA05)

2-3. Synthesis of cyanomethyl 3-((tert-butoxycarbonyl)(2-(tert-butyldisulfanyl)ethyl)amino)propanoate (Compound 6g-B)

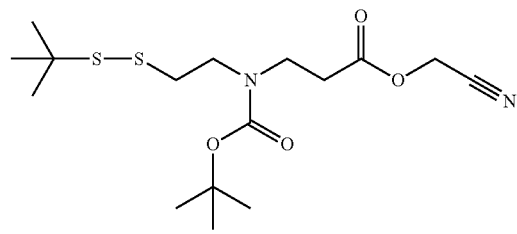 [SMILES: CC(C)(C)OC(=O)N(CCSSC(C)(C)C)CCC(=O)OCC#N]

The title compound (1.05 g, 91%) was obtained by the same method as in the synthesis of Compound 6g-A using 3-((tert-butoxycarbonyl)(2-(tert-butyldisulfanyl)ethyl)amino)propanoic acid (Compound 6f-B, 1.03 g, 3.05 mmol) as a starting material.

LCMS: m/z 377 (M+H)+
Retention time: 1.09 min (analysis condition SQDAA05)

2-4. Synthesis of (2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-((2-(tert-butyldisulfanyl)ethyl)amino)propanoate (Compound 6i-B)

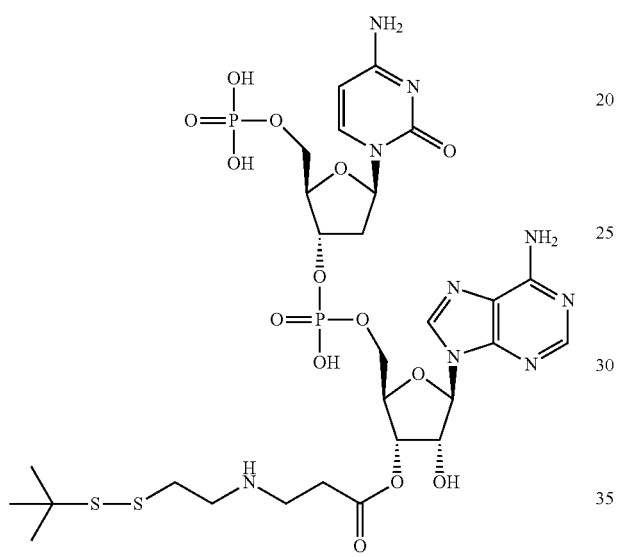

((2R,3S,5R)-5-(4-Amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate tetrabutylammonium salt (Compound 1h, 44.6 mg, 0.314 mmol) and cyanomethyl 3-((tert-butoxycarbonyl)(2-(tert-butyldisulfanyl)ethyl)amino)propanoate (Compound 6g-B, 236 mg, 0.628 mmol) were dissolved in DMF under ice-cooling, followed by addition of triethylamine (0.088 ml, 0.628 mmol). After stirring at room temperature for 1 hour, the reaction solution was purified by column chromatography (0.05% aqueous TFA solution:0.05% TFA-acetonitrile solution=70:30). TFA (1.5 ml) was added to the resulting residue, and the mixture was stirred at room temperature for 5 minutes. The reaction solution was concentrated under reduced pressure, and the resulting residue was purified by column chromatography (0.05% aqueous TFA solution: 0.05% TFA-acetonitrile solution=80:20) to afford the title compound (66.9 mg, 25%).
LCMS: m/z 856 (M+H)+
Retention time: 0.629 min (analysis condition SMD method 1)

3. Synthesis of Compound 6i-C 3-1. Synthesis of Ethyl 4-((tert-butoxycarbonyl)(2-(tert-butyldisulfanyl)ethyl)amino)butanoate (Compound 6e-C)

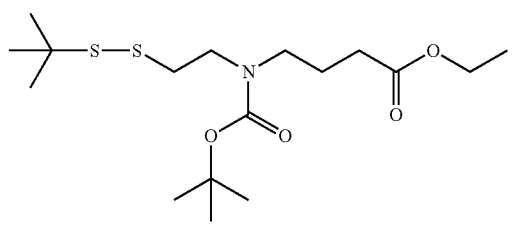 [SMILES: CCOC(=O)CCCN(CCSSC(C)(C)C)C(=O)OC(C)(C)C]

The title compound (556.2 mg, 24.2%) was obtained by the same method as in the synthesis of Compound 6e-A using ethyl 4-bromobutanoate (2.68 ml, 18.15 mmol) in place of ethyl 2-bromoacetate.
LCMS: m/z 380 (M+H)+
Retention time: 1.15 min (analysis condition SQDAA05)

3-2. Synthesis of 4-((tert-butoxycarbonyl)(2-(tert-butyldisulfanyl)ethyl)amino)butanoic Acid (Compound 6f-C)

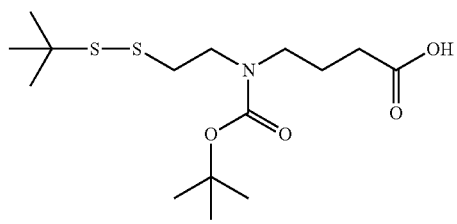 [SMILES: CC(C)(C)OC(=O)N(CCCC(=O)O)CCSSC(C)(C)C]

The title compound (0.86 g, 97%) was obtained by the same method as in the synthesis of Compound 6f-A using ethyl 4-((tert-butoxycarbonyl)(2-(tert-butyldisulfanyl)ethyl)amino)butanoate (Compound 6e-C, 0.96 g, 2.53 mmol) as a starting material in place of ethyl 2-((tert-butoxycarbonyl)(2-(tert-butyldisulfanyl)ethyl)amino)acetate (Compound 6e-A).
LCMS: m/z 352 (M+H)+
Retention time: 0.99 min (analysis condition SQDAA05)

3-3. Synthesis of Cyanomethyl 4-((tert-butoxycarbonyl)(2-(tert-butyldisulfanyl)ethyl)amino)butanoate (Compound 6g-C)

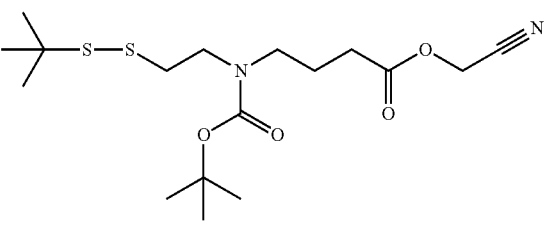 [SMILES: CC(C)(C)OC(=O)N(CCCC(=O)OCC#N)CCSSC(C)(C)C]

The title compound (0.71 g, 74%) was obtained by the same method as in the synthesis of Compound 6g-A using 4-((tert-butoxycarbonyl)(2-(tert-butyldisulfanyl)ethyl) amino)butanoic acid (Compound 6f-C, 0.86 g, 2.45 mmol) as a starting material in place of 2-((tert-butoxycarbonyl)(2-(tert-butyldisulfanyl)ethyl)amino)acetic acid (Compound 6f-A).

LCMS: m/z 391 (M+H)+
Retention time: 1.05 min (analysis condition SQDAA05)

3-4. Synthesis of (2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-((2-(tert-butyldisulfanyl)ethyl)amino)butanoate (Compound 6i-C)

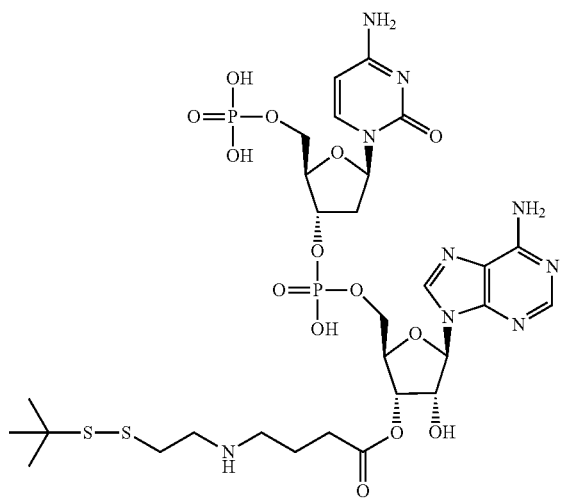 [SMILES: CC(C)(C)SSCCNCCCC(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

The title compound (103 mg, 37.6%) was obtained by the same method as in the synthesis of Compound 6i-B using cyanomethyl 4-((tert-butoxycarbonyl)(2-(tert-butyldisulfanyl)ethyl)amino)butanoate (Compound 6g-C, 245 mg, 0.628 mmol) in place of cyanomethyl 3-((tert-butoxycarbonyl)(2-(tert-butyldisulfanyl)ethyl)amino)propanoate (Compound 6g-B).

LCMS: m/z 870 (M+H)+
Retention time: 0.641 min (analysis condition SMD method 1)

[Example 12] Synthesis of Aminoacylated tRNAs Using Stable Aminoacylated pdCpAs Having a SH Group 2 µl of 10× ligation buffer (500 mM HEPES-KOH pH 7.5, 200 mM MgCl$_2$, 10 mM ATP) and 4 µl of nuclease free water were added to 10 µl of 50 µM transcribed tRNAfMet-CAU (-CA) (SEQ ID NO: R-5). The mixture was heated at 95° C. for 2 minutes and then left to stand at room temperature for 5 minutes, and the tRNA was refolded. 2 µL of 10 units/µl T4 RNA ligase (New England Biolabs) and 2 µL of a 5 mM solution of aminoacylated pdCpA (Compound 6i-A, 6i-B, 6i-C, 2n-A, 2m-c or 2m-E) in DMSO were added, and ligation reaction was carried out at 15° C. for 45 minutes. Aminoacylated tRNA (Compound AT-2-A, AT-2-C, AT-2-E, AT-6-A, AT-6-B or AT-6-C) was collected by phenol extraction and ethanol precipitation. Aminoacylated tRNA (Compound AT-2-A, AT-2-C, AT-2-E, AT-6-A, AT-6-B or AT-6-C) was dissolved in 1 mM sodium acetate immediately prior to addition to the translation mixture.

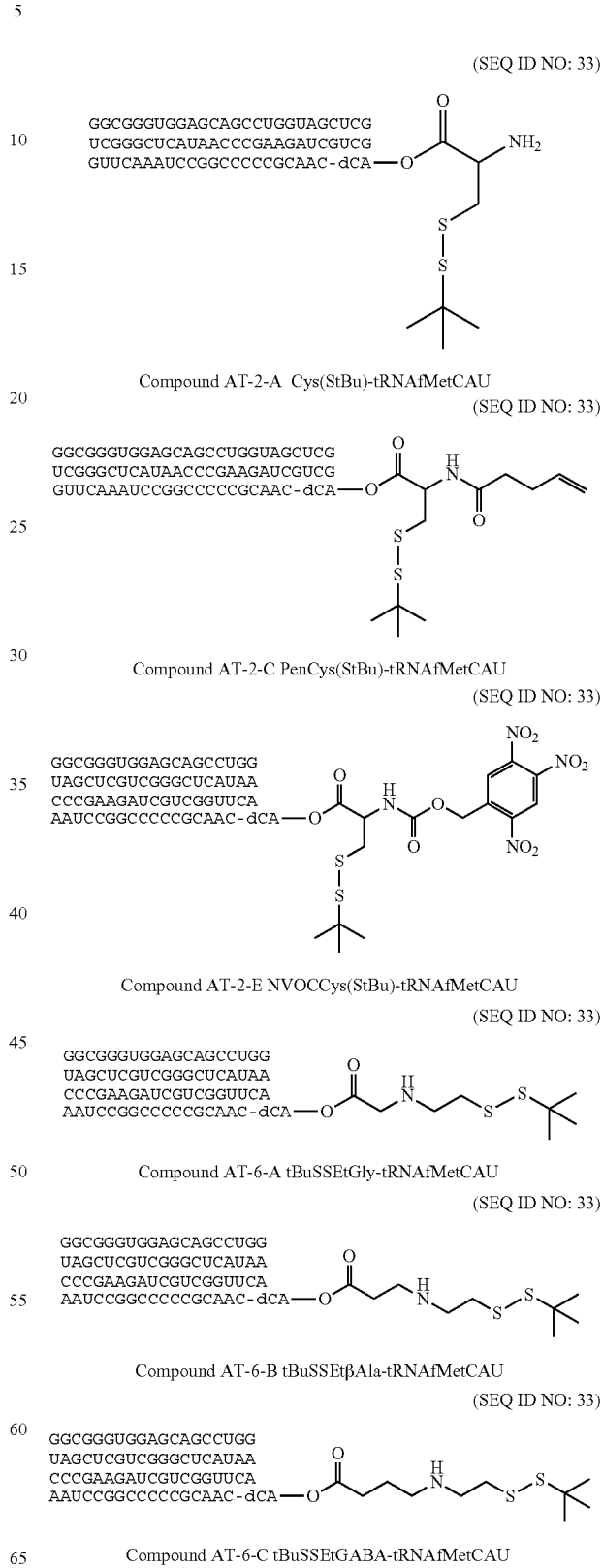

[Example 13] Translation Synthesis Using SH Group-Containing Stable Aminoacylated tRNAs The following experiment showed that protection of the SH group or the main chain amino group of Cys improves stability of aminoacylated pdCpAs in a translation solution model system (HEPES buffer) and also improves translation synthesis efficiency, as compared with the case where Cys is not protected. Various novel SH group-containing unnatural amino acids having a SH group located remotely from a-carboxylic acid site also improved translation efficiency.

The aforementioned transcription and translation solution, 0.1 mM 10-HCO—H4 folate, 0.3 mM each of 19 proteinogenic amino acids excluding Met, and 25 to 50 μM Xaa-tRNAfMetCAU (Xaa: Cys(StBu), PenCys(StBu), NVOC-Cys(StBu), tBuSSEtGly, tBuSSEtβAla or tBuSSEt-GABA) prepared by the above-described method were added to 20 nM template DNA AKC17 (SEQ ID NO: D-31) or KA03 (SEQ ID NO: D-6), followed by translation at 37° C. for 30 minutes. The resulting translation reaction product was purified with SPE C-TIP (Nikkyo Technos) and analyzed by MALDI-MS. As a result, the MS of the peptide having Xaa introduced at the N-terminal was observed (MALDI-MS).

Figure 25:
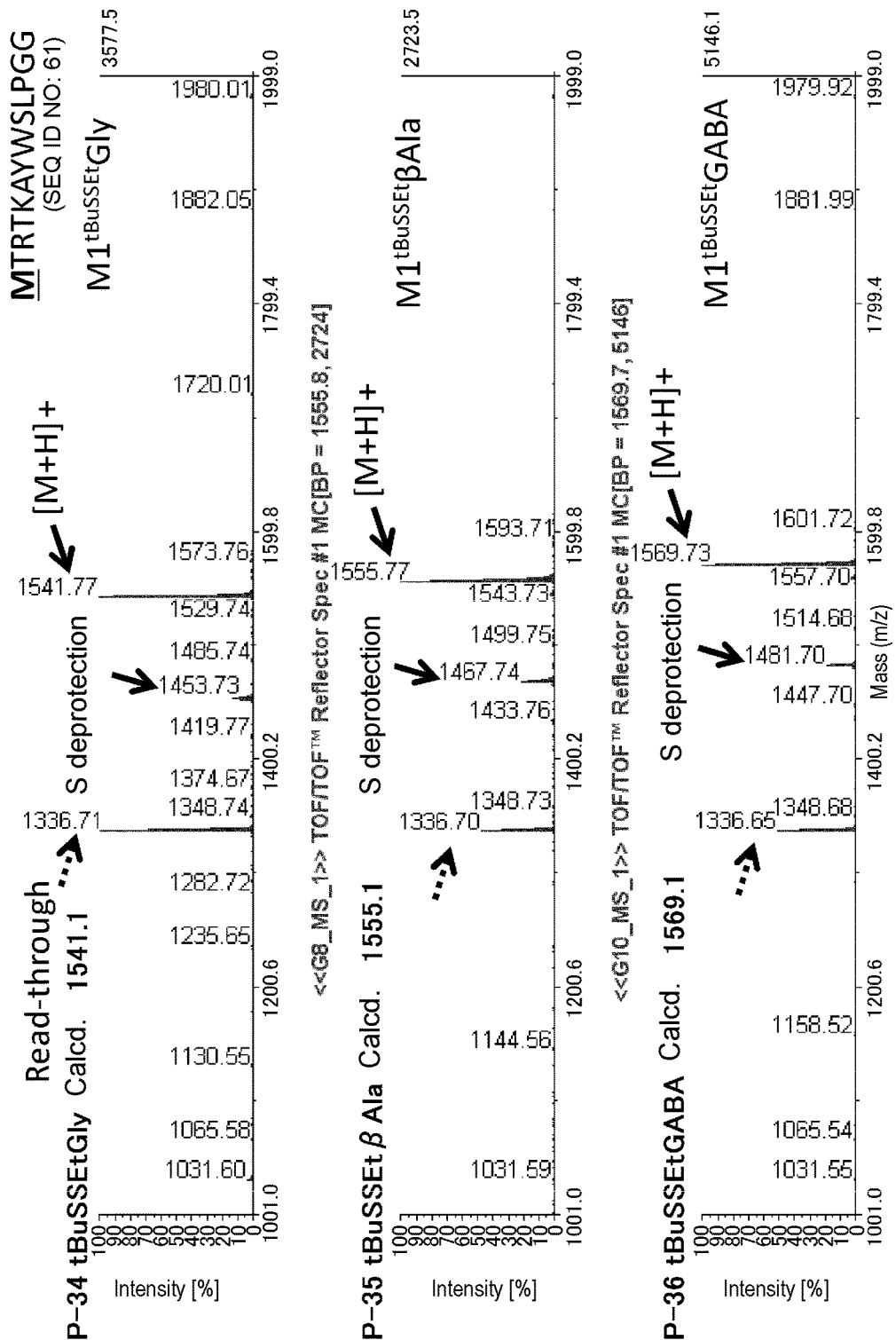
FIG. 25 is a diagram showing the mass spectra of translated peptides using SH group-containing stable aminoacylated tRNAs (P-34: tBuSSEtGly, P-35: tBuSSEtβAla, P-36: tBuSSEtGABA; [M+H] represents a target compound, S deprotection represents a compound derived from the target compound by the elimination of a protecting group added to its SH group and means that the target compound was translated, and Read-through represents a translation product initiated from the 2nd codon encoding Thr, which is a by-product).
Figure 26:
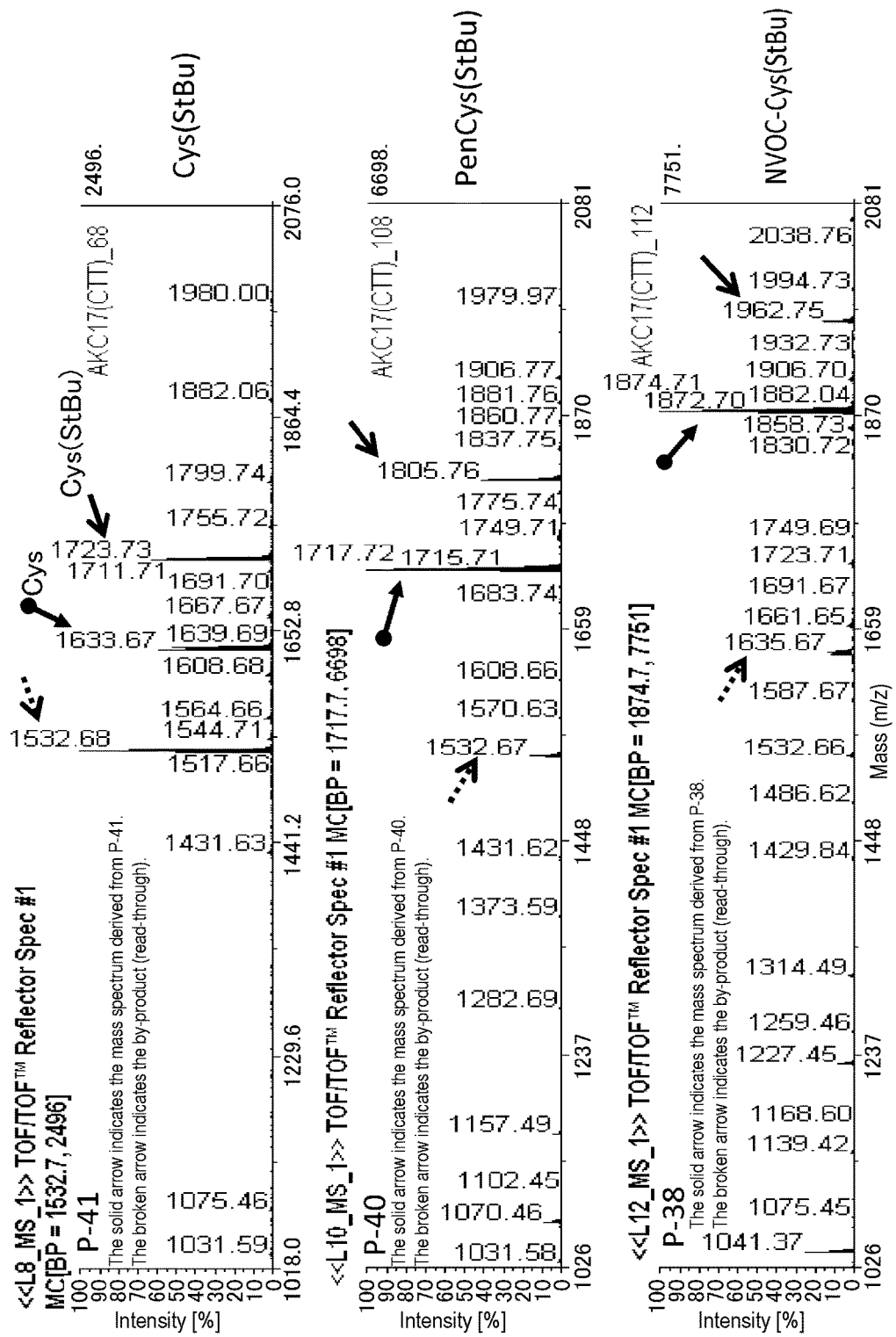
FIG. 26 is a diagram showing the mass spectra of translated peptides using SH group-containing stable aminoacylated tRNAs (P-41: Cys(StBu), P-40: PenCys(StBu), P-38: NVOC-Cys(StBu)).

Consequently, protection of the SH or amino group was shown to improve stability of pdCpA-amino acids and also improve translation synthesis efficiency as compared with the case where Cys is not protected. Such protection also improved translation introduction efficiency for various SH-containing unnatural amino acids having Cys more stabilized (see FIGS. 25 and 26).

TABLE 5

| Peptide SEQ ID NO: | Scaffold | Xaa | Calc. | Found |
|---|---|---|---|---|
| P-34 | KA03 | tBuSSEtGly | 1541.1 | 1541.8 |
| P-35 | KA03 | tBuSSEt β Ala | 1555.1 | 1555.8 |
| P-36 | KA03 | tBuSSEtGABA | 1569.1 | 1569.7 |
| P-38 | AKC17 | NVOC-Cys(StBu) | 1961.8 | 1962.8 |
| P-40 | AKC17 | PenCys(StBu) | 1804.8 | 1805.8 |
| P-41 | AKC17 | Cys(StBu) | 1722.7 | 1723.7 |

```
SEQ ID NO: D-31
AKC17 DNA sequence
                                       (SEQ ID NO: 7)
GTAATACGACTCACTATAGGGTTAACTTTAAGAAGGAGATATACATATGA CTAGAACTGCCTACTGGAGCcttTGCGGCAGCGGCAGCGGCAGC
```

Scaffold sequences of peptide SEQ ID NO:s P-34 to P-41

```
KA03 Peptide sequence
                                     (SEQ ID NO: 195)
[Xaa]ThrArgThrLysAlaTyrTrpSerLeuProGlyGly AKC17 Peptide sequence
                                     (SEQ ID NO: 196)
[Xaa]ThrArgThrAlaTyrTrpSerLeuCysGlySerGlySerGlySer
```

[Example 14] Translation and Cyclization Reaction Using the Initiation Suppression Method

1. Synthesis of Aminoacylated tRNAs Having Side Chain Carboxylic Acid Converted to Active Ester Aminoacylated tRNAs having side chain carboxylic acid converted to active ester were synthesized according to the following method.

1-1. Synthesis of tRNA (Lacking CA) by Transcription tRNAEnAsnGAG (-CA) (SEQ ID NO: R-33) was synthesized from template DNA (SEQ ID NO: D-33) by in vitro transcription using RiboMAX Large Scale RNA production System T7 (Promega, P1300) and purified with RNeasy Mini kit (Qiagen).

SEQ ID NO: D-33 (the same as SEQ ID NO: D-1) (SEQ ID NO: 1)

```
tRNAEnAsnGAG(-CA) DNA sequence:
GGCGTAATACGACTCACTATAGGCTCTGTAGTTCAGTCGGTAGAACGGCG GACTgagAATCCGTATGTCACTGGTTCGAGTCCAGTCAGAGCCGC SEQ ID NO: R-33 (the same as SEQ ID NO: R-1)
tRNAEnAsnGAG(-CA) RNA sequence:
                                      (SEQ ID NO: 30)
GGCUCUGUAGUUCAGUCGGUAGAACGGCGGACUgagAAUCCGUAUGUCAC

UGGUUCGAGUCCAGUCAGAGCCGC
```

1-2. Synthesis of Aminoacylated tRNAs (Compounds AT-1) by Ligation of Aminoacylated pdCpAs Having Side Chain Carboxylic Acid Converted to Active Ester (Compound 1i) and tRNA (lacking CA) (SEQ ID NO: R-33)

2 μL of 10× ligation buffer (500 mM HEPES-KOH pH 7.5, 200 mM MgCl$_2$, 10 mM ATP) and 4 μL of nuclease free water were added to 10 μL of 50 μM transcribed tRNAE-nAsnGAG (-CA) (SEQ ID NO: R-33). The mixture was heated at 95° C. for 2 minutes and then left to stand at room temperature for 5 minutes, and the tRNA was refolded. 2 μL of 10 units/μL T4 RNA ligase (New England Biolabs) and 2 μL of a 5 mM solution of aminoacylated pdCpA having side chain carboxylic acid converted to active ester (Compound 1i) in DMSO were added, and ligation reaction was carried out at 15° C. for 45 minutes. 4 μL of 125 mM iodine (solution in water:THF=1:1) were added to 20 μL of the ligation reaction solution, and deprotection was carried out at room temperature for 1 hour. Aminoacylated tRNA (Compound AT-1) was collected by phenol extraction and ethanol precipitation. Aminoacylated tRNA (Compound AT-1) was dissolved in 1 mM sodium acetate immediately prior to addition to the translation mixture.

Compound AT-1-IA2 (the same as Compound AT-1-IA) Asp(SMe)-tRNAEnAsnGAG

Compound No. AT-1-IB2 (the same as Compound AT-1-IB) Asp(SiPr)-tRNAEnAsnGAG

Compound No. AT-1-IC2 (the same as Compound AT-1-IC) Asp(StBu)-tRNAEnAsnGAG

Compound No. AT-1-ID2 (the same as Compound AT-1-ID) Asp(SBn)-tRNAEnAsnGAG

Compound No. AT-1-IE2 (the same as Compound AT-1-IE) Asp(SPhenetyl)-tRNAEnAsnGAG Compound No. AT-1-IG2 (the same as Compound AT-1-IG) Asp(SEt)-tRNAEnAsnGAG 2. Translation Synthesis and Amide Cyclization Reaction Using the Method of Introducing an Amino Acid Other than Methionine, Amino Acid Analog or N-Terminal Carboxylic Acid Analog Thereof at the N-Terminal Translation reaction was carried out using KA03 DNA sequence (SEQ ID NO: D-6) as template DNA.

The aforementioned transcription and translation solution, 0.3 mM each of 18 proteinogenic amino acids excluding Met and Leu, and 25 µM tBuSSEtGABA-tRNAfMet-CAU (Compound No. AT-6-C) and 50 µM Asp(SMe)-tRNAEnAsnGAG (Compound No. AT-1-IA2) prepared by the above-described methods were added to the template DNA, followed by translation at 37° C. for 3 hours. 200 mM TCEP (pH 6.6) was added to the translational product in a volume ratio of 1/20 (v/v), and the mixture was reacted at 37° C. for 15 minutes to carry out intramolecular cyclization reaction with the Asp(SMe) site. As a result, the intended cyclic peptide (peptide sequence P-43) was confirmed by the MS spectrum (FIG. 27). Translation and cyclization were efficiently achieved with N-alkylamino acid as the amino acid following thioester.

```
Peptide sequence P-42
                                    (SEQ ID NO: 197)
[tBuSSEtGABA]ThrArgThrLysAlaTyrTrpSer[Asp(SMe)]
ProGlyGly
```

MALDI-MS: m/z: [M+H]+=1601.7 (Calc. 1601.0)

Peptide sequence P-43 (SEQ ID NO: 198)

Compound in which the main chain nitrogen atom of GABA of [HSEtGABA]ThrArgThrLysAlaTyrTrpSer[Asp (SMe0]ProGlyGly_ and the side chain carboxylic acid of Asp are amide-cyclized (SEQ ID NO: 313)

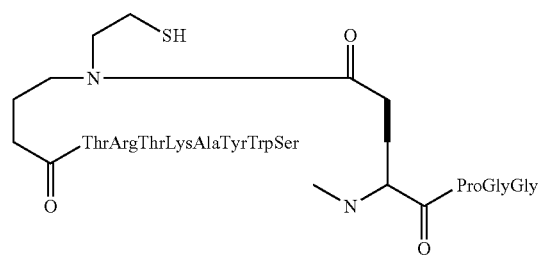

MALDI-MS: m/z: [M+H]+=1465.6 (Calc. 1465.0)

[Example 15] Translation and Cyclization Using the Initiation Read Through Method 1. Synthesis of Amide-Type Cyclized Peptide Through NCL (Native Chemical Ligation)

Translation reaction was carried out using KA02.5U DNA sequence (SEQ ID NO: D-32) as template DNA.

Figure 28:
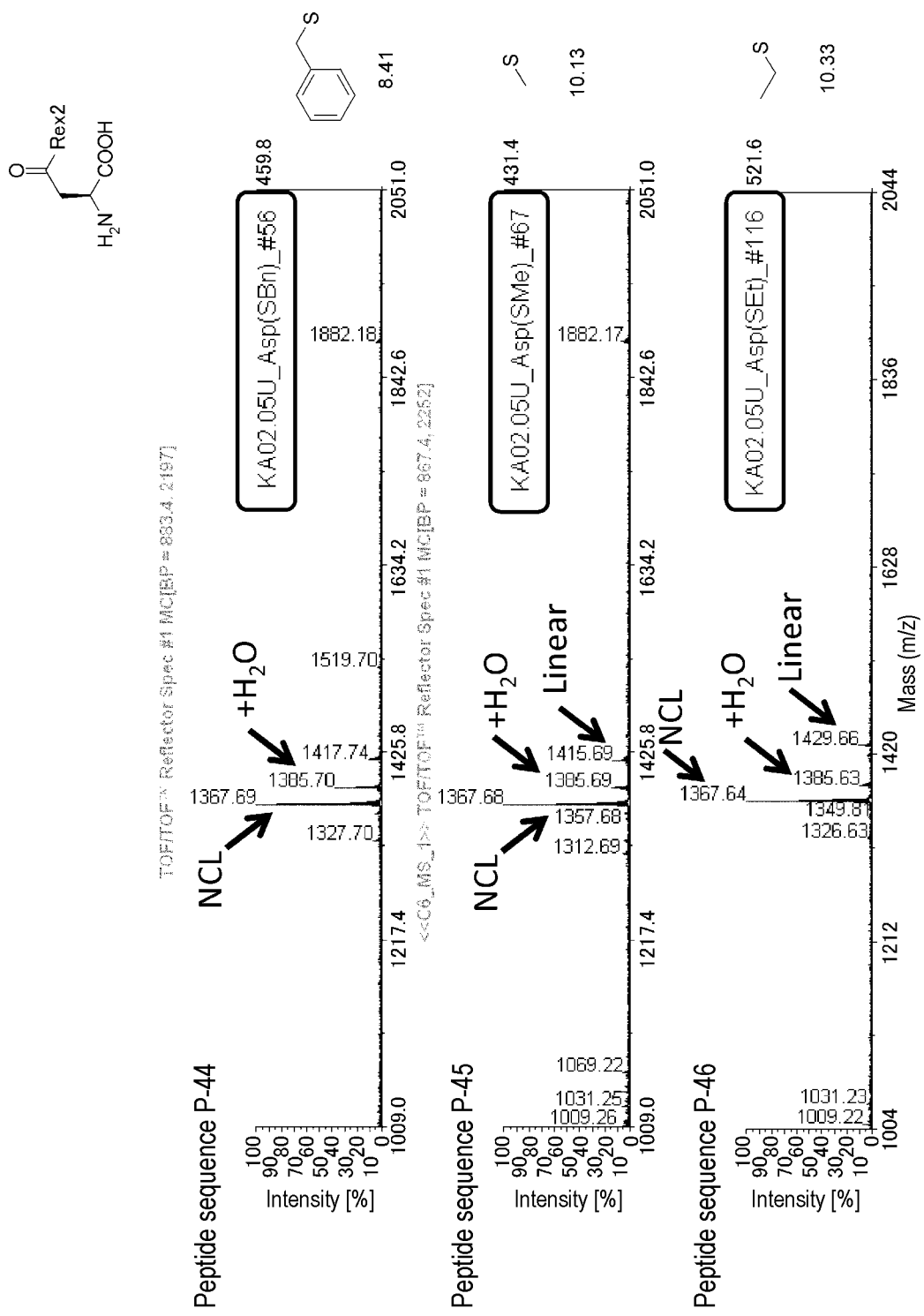
FIG. 28 is a diagram showing translation using initiation read-through and the mass spectrum of an amide-cyclized peptide (NCL: target compound).
Figure 29:
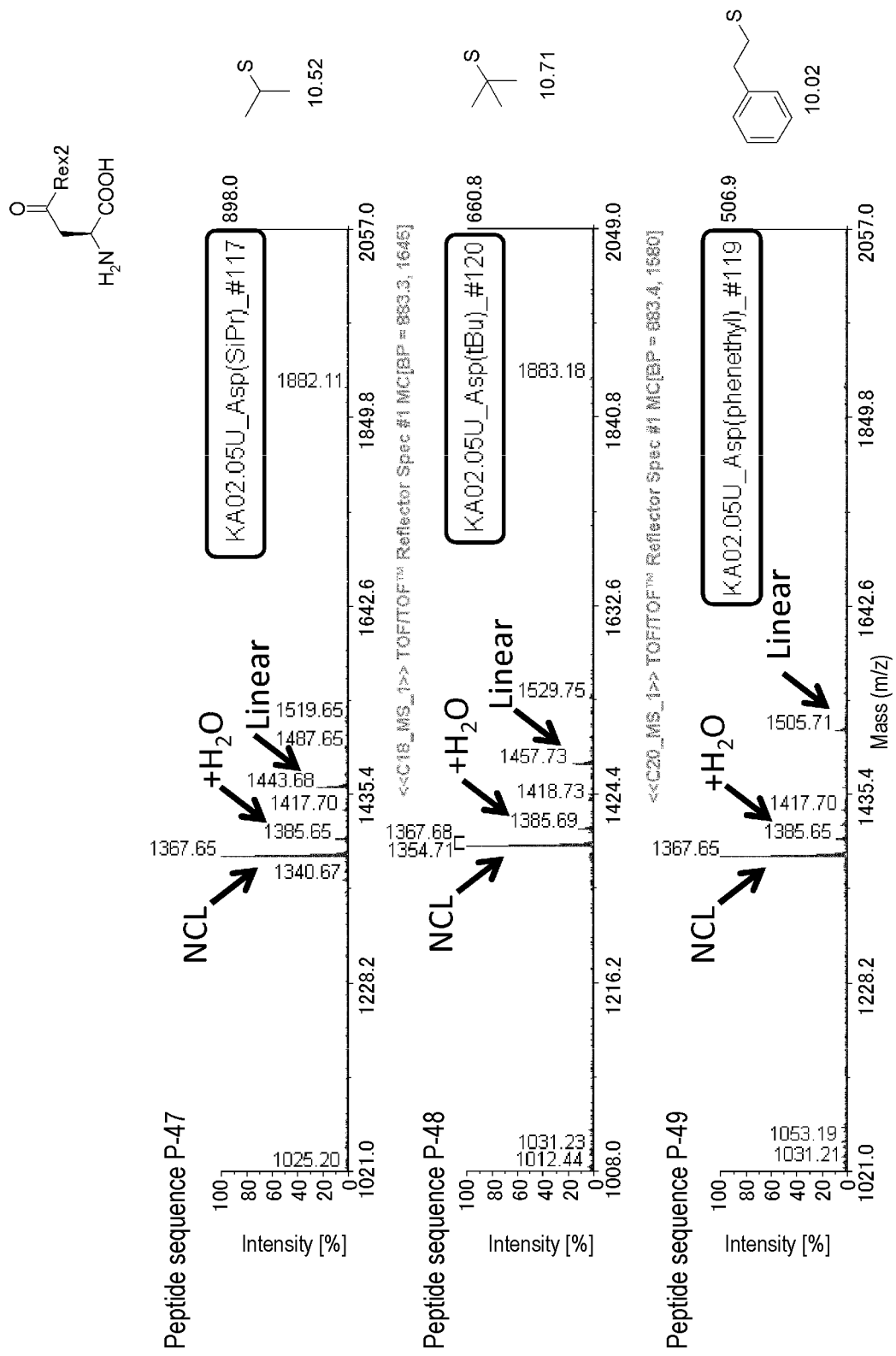
FIG. 29 is a diagram showing translation using initiation read-through and the mass spectrum of an amide-cyclized peptide (NCL: target compound).

The aforementioned transcription and translation solution, 0.3 mM each of 17 proteinogenic amino acids excluding Met, Ala and Leu, 3 mM lactic acid, and 50 µM Asp(SRex2)-tRNAEnAsnGAG (Rex2: benzyl, methyl, ethyl, isopropyl, tert-butyl or phenethyl) (Compound No. AT-1-IA2, IB2, IC2, ID2, 1E2 or IG2) prepared by the above-described method were added to the template DNA, followed by translation at 37° C. for 3 hours. As a result, cyclized full-length peptides were confirmed by the MS spectra (FIGS. 28 to 29).

```
SEQ ID NO: D-32
KA02.5U DNA sequence:
                                    (SEQ ID NO: 28)
GTAATACGACTCACTATAGGGTTAACTTTAAGAAGGAGATATACATATGt gcACTAGAACTaaggcgTACTGGAGCcttCCGggctaa Translated peptide
                                    (SEQ ID NO: 199)
CysThrArgThrLys[Lac]TyrTrpSer[Asp(SRex2)]ProGly
(Rex2: benzyl, methyl, ethyl, isopropyl, tert-
butyl or phenethyl, Lac: lactic acid)
```

Chemical structures of posttranslationally cyclized peptides (peptide SEQ ID NO:s P-44 to P-49) Compound in which the main chain amino group of Cys of CysThrArgThrLys[Lac]TyrTrpSer[Asp(SRex2)]ProGly (SEQ ID NO: 199) and the side chain carboxylic acid of Asp are intramolecularly amidated (SEQ ID NO: 314)

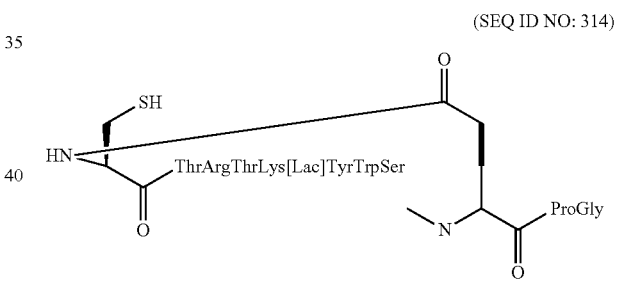

TABLE 6

| Peptide SEQ ID NO: | Thioester Rex2 | Calc. (cyclization) | [M + H]+ |
|---|---|---|---|
| P-44 | Bn | 1366.6 | 1367.7 |
| P-45 | Me | 1366.6 | 1367.7 |
| P-46 | Et | 1366.6 | 1367.7 |
| P-47 | iPr | 1366.6 | 1367.7 |
| P-48 | tBu | 1366.6 | 1367.7 |
| P-49 | phenethyl | 1366.6 | 1367.7 |

The above results revealed that the Initiation read through method translationally incorporate Cys, allows translation and cyclization to proceed smoothly, and provides amide cyclic peptide as main products from various thioesters. Further, it was found for the first time that lactic acid can be selectively and efficiently introduced by AlaRS, because this sequence including lactic acid was effectively translated.

As described for the initiation read through method, when a SH group functioning to assist amide bond formation is not protected, unnatural amino acids (including proteinogenic amino acids) following thioesters may not necessarily be amino acids having N-alkyl groups. This is because amides are produced through reactions with a SH group immediately after translation. When amino acids having a SH group protected are translated, aspartimides are formed within the time between the completion of the translation step and the deprotection step.

2. Determination of Structures of Amide-Cyclized Peptides by Translation

2-1. Preparation of Translated Peptides for LC-MS Analysis

The aforementioned transcription and translation solution, 0.1 mM 10-HCO—H4 folate (10-formyl-5,6,7,8,-tetrahydrophilic acid), 0.3 mM each of 18 proteinogenic amino acids excluding Met and Leu, and 50 μM Asp(SMe)-tR-NAEnAsnGAG (Compound AT-1-IA) prepared by the above-described method were added to 20 nM template DNA Mctryg3 (SEQ ID NO: D-8), followed by translation at 37° C. for 3 hours. 1 mM dithiothreitol was added to the translation reaction product. After reducing at 37° C. for 30 minutes, 10 mM iodoacetamide was added, and the thiol was carboxyamidomethylated under shading at room temperature for 40 minutes.

```
Peptide sequence P-52
                            (SEQ ID NO: 200)
CysThrThrThrArg[Asp(SMe)]TyrTyrArgGlyGly
```

Peptide sequence P-53 (SEQ ID NO: 59) Compound in which the main chain amino group of Cys of CysThrThrThrArg[Asp(SMe)]TyrTyrArgGlyGly (SEQ ID NO: 200) and the side chain carboxylic acid of Asp are intramolecularly amide-cyclized mass spectrum calc. 1273.6

(SEQ ID NO: 59)

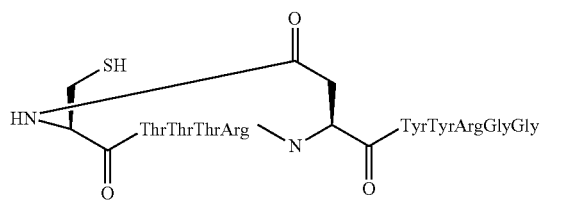

Peptide sequence P-54 after acetamidation Exact Mass Calc. 1330.6

Compound resulting from acetamidation of the SH group of Cys of peptide sequence P-53 in which the main chain amino group of Cys of CysThrThrThrArg[Asp(SMe)]TyrTyrArgGlyGly (peptide sequence P-52) (SEQ ID NO: 200) and the side chain carboxylic acid of Asp are intramolecularly amide-cyclized (SEQ ID NO: 201)

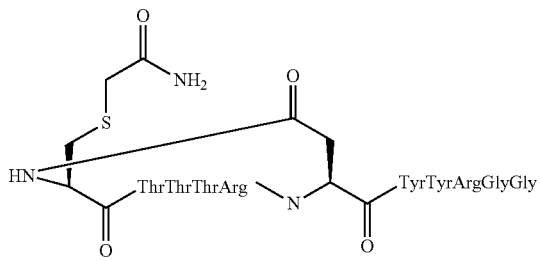

2-2. Chemical Synthesis of Peptides Having the Same Sequences as Those of Translationally Synthesized Products

2-2-1. General Method for Peptide Solid-Phase Synthesis by an Automatic Synthesizer Peptide synthesis was carried out by the Fmoc method using a peptide synthesizer (Multipep RS; manufactured by Intavis). Fmoc-Cys(Mmt)-OH was purchased from Novabiochem, and Fmoc amino acids other than Fmoc-Cys(Mmt)-OH were purchased from Watanabe Chemical Industries. The detailed operational procedure was in accordance with the manual attached to the synthesizer.

2-Chlorotrityl resin to which the C-terminal Fmoc amino acid binds (250 to 300 mg per column), a solution of various Fmoc amino acids (0.6 mol/L) and 1-hydroxy-7-azabenzotriazole (HOAt) (0.375 mol/L) in N,N-dimethylformamide, and a solution of diisopropylcarbodiimide (DIC) in N,N-dimethylformamide (DMF) (10% v/v) were placed in the synthesizer, and synthesis was carried out using, as an Fmoc deprotection solution, a solution of piperidine in N,N-dimethylformamide (20% v/v) containing 5% (wt/v) urea or a solution of diazabicycloundecene (DBU) in N,N-dimethylformamide (2% v/v). Washing of the resin with a DMF solution, subsequent Fmoc deprotection and subsequent Fmoc amino acid condensation reaction form one cycle. The peptide was elongated on the surface of the resin by repeating this cycle. The synthesis was carried out with reference to the Non patent literature of Ramon Subiros-funosas et al. (Org. Biomol. Chem. 2010, 8, 3665-3673) for such an experiment, for example.

2-2-2. Synthesis of H-Cys(CH₂CONH₂)-Thr(tBu)-Thr(tBu)-Thr(tBu)-Arg(Pbf)-Asp-OBn (Peptide P-55) (SEQ ID NO: 315)

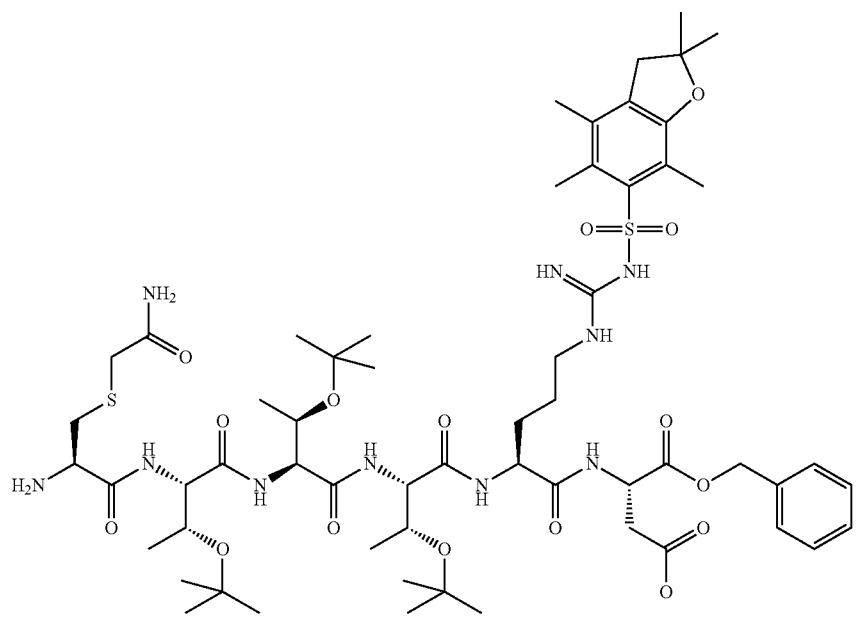 [SMILES: Cc1c(C)c(S(=O)(=O)NC(=N)NCCC[C@H](NC(=O)[C@@H](NC(=O)[C@@H](NC(=O)[C@@H](NC(=O)[C@@H](N)CSCC(N)=O)[C@@H](C)OC(C)(C)C)[C@@H](C)OC(C)(C)C)[C@@H](C)OC(C)(C)C)C(=O)N[C@@H](CC(=O)O)C(=O)OCc2ccccc2)c(C)c2c1CC(C)(C)O2]

Fmoc-Cys(Mmt)-OH, Fmoc-Thr(tBu)-OH and Fmoc-Arg(Pbf)-OH (all purchased from Watanabe Chemical Industries) were used as Fmoc amino acids. 2-Chlorotrityl resin to which Fmoc-Asp-OBn binds (250 mg, 13 columns, 1.36 mmol) was placed in the synthesizer, and the peptide was solid-phase synthesized.

Following completion of the elongation, the resin was washed with dichloromethane, and the peptide was cleaved from the resin and the S-methoxytrityl group was deprotected by adding trifluoroacetic acid/triisopropylsilane/dichloromethane (=2/5/93, 100 mL). The peptide was cleaved from the resin and the S-methoxytrityl group was deprotected. After 1.5 hours, the resin was removed by filtering the solution in the tube through a synthesis column. 2-Iodoacetamide (252 mg, 1.36 mmol), DIPEA (15 mL) and DMF (15 mL) were added to the reaction solution, and S was alkylated. After 1.5 hours, the residue obtained by concentration under reduced pressure was purified by reverse-phase silica gel chromatography (0.1% aqueous formic acid solution/0.1% formic acid-acetonitrile solution=95/5→0/100) to afford a linear peptide H-Cys(CH₂CONH₂)-Thr(tBu)-Thr(tBu)-Thr(tBu)-Asp-Arg(Pbf)-Asp-OBn (peptide P-55) (SEQ ID NO: 316) (180 mg, 10%).

LCMS (ESI) m/z=1262 (M−H)−

Retention time: 0.71 min (analysis condition SQDFA05)

2-2-3. Synthesis of c(Cys(CH$_2$CONH$_2$)-Thr(tBu)-Thr(tBu)-Thr(tBu)-Arg(Pbf)-Asp)-OBn (Peptide P-56) (SEQ ID NO: 317)

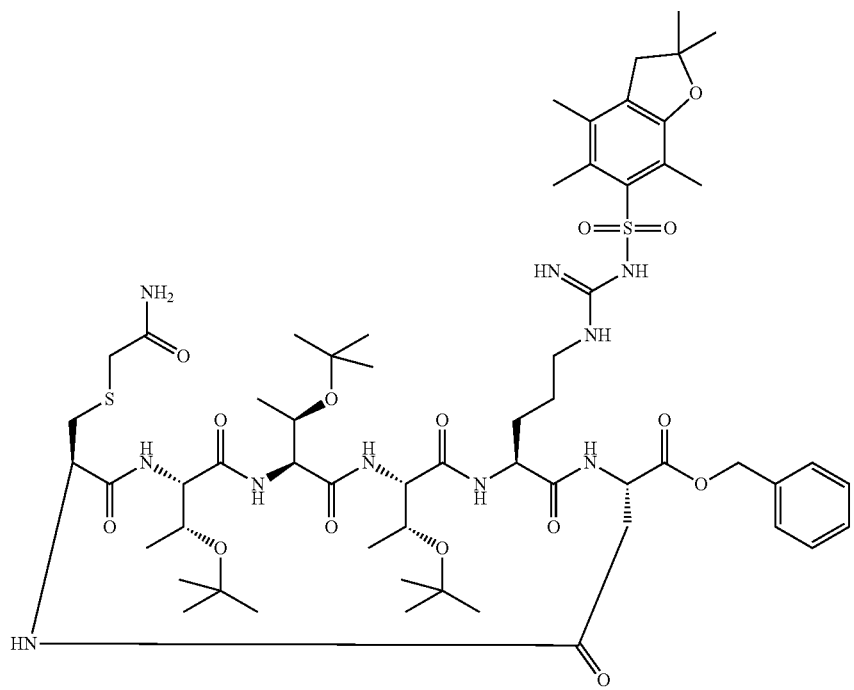 [SMILES: Cc1c(C)c(S(=O)(=O)NC(=N)NCCC[C@@H]2NC(=O)[C@H]([C@@H](C)OC(C)(C)C)NC(=O)[C@H]([C@@H](C)OC(C)(C)C)NC(=O)[C@H]([C@@H](C)OC(C)(C)C)NC(=O)[C@H](CSCC(N)=O)NC(=O)C[C@@H](C(=O)OCc3ccccc3)NC2=O)c(C)c2c1CC(C)(C)O2]

H-Cys(CH$_2$CONH$_2$)-Thr(tBu)-Thr(tBu)-Thr(tBu)-Arg(Pbf)-Asp-OBn (peptide P-55 (SEQ ID NO: 315), 180 mg) was dissolved in dichloromethane/dimethylsulfoxide (9/1) (141 mL), and O-(7-aza-1H-benzotriazol-1-yl)-N,N,N,N-tetramethyluronium hexafluorophosphate (HATU) (81 mg, 0.214 mmol) and diisopropylethylamine (0.149 mL, 0.855 mmol) were added, followed by stirring. After 1.5 hours, the reaction solution was concentrated under reduced pressure, and the resulting residue was purified by reverse-phase silica gel chromatography (0.1% aqueous formic acid solution/0.1% formic acid acetonitrile solution=50/50→0/100) to afford a cyclic peptide c(Cys(CH$_2$CONH$_2$)-Thr(tBu)-Thr(tBu)-Thr(tBu)-Arg(Pbf)-Asp)-OBn (peptide P-56) (SEQ ID NO: 317) (92 mg, 52%).

LCMS (ESI) m/z=1246 (M+H)+
Retention time: 1.02 min (analysis condition SQDFA05)

2-2-4. Synthesis of c(Cys(CH₂CONH₂)-Thr(tBu)-Thr(tBu)-Thr(tBu)-Arg(Pbf)-Asp)-OH (Peptide P-57) (SEQ ID NO: 318)

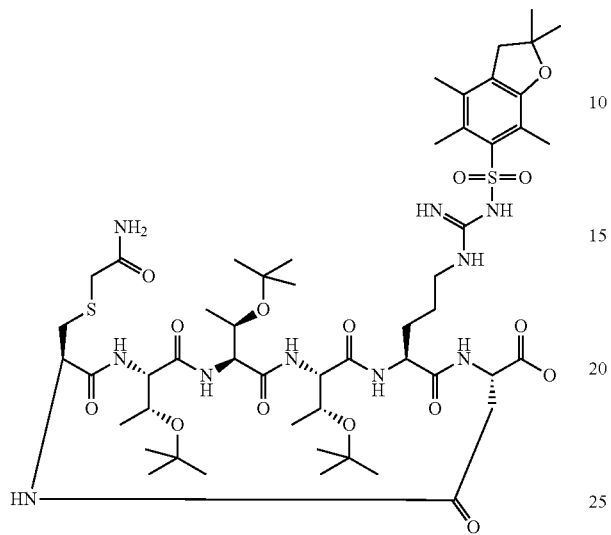

c(Cys(CH₂CONH₂)-Thr(tBu)-Thr(tBu)-Thr(tBu)-Arg(Pbf)-Asp)-OBn (peptide P-56 (SEQ ID NO: 317), 90 mg) was dissolved in an ethanol (2 mL), 10% palladium on carbon (100 mg) was added and the mixture was stirred under a hydrogen atmosphere. After 18 hours, the reaction solution was concentrated under reduced pressure to afford a cyclic peptide c(Cys(CH₂CONH₂)-Thr(tBu)-Thr(tBu)-Thr(tBu)-Arg(Pbf)-Asp)-OH (peptide P-57) (SEQ ID NO: 318) (72 mg, 86%).

LCMS (ESI) m/z=1156 (M+H)+
Retention time: 0.93 min (analysis condition SQDFA05)

2-2-5. Synthesis of C(Cys(CH₂CONH₂)-Thr(tBu)-Thr(tBu)-Thr(tBu)-Arg(Pbf)-Asp)-Tyr(tBu)-Tyr(tBu)-Arg(Pbf)-Gly-Gly-OH (Peptide P-58) (SEQ ID NO: 202)

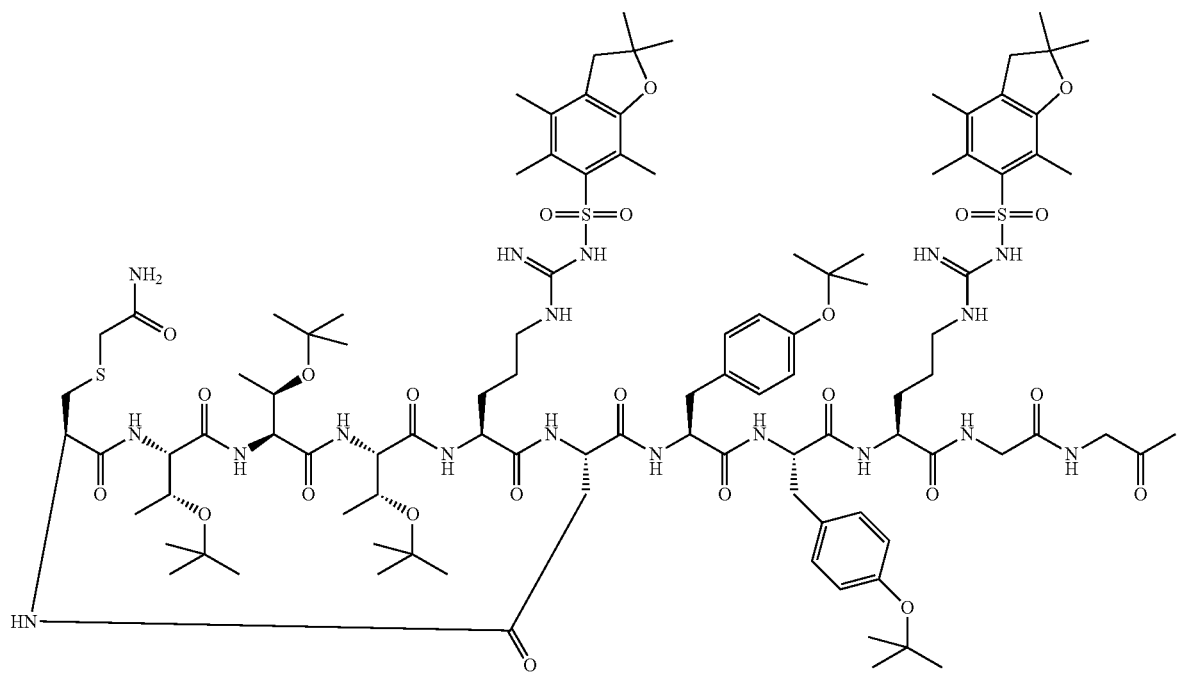 [SMILES: CC(=O)CNC(=O)CNC(=O)[C@H](CCCNC(=N)NS(=O)(=O)c1c(C)c(C)c2c(c1C)OC(C)(C)C2)NC(=O)[C@H](Cc1ccc(OC(C)(C)C)cc1)NC(=O)[C@H](Cc1ccc(OC(C)(C)C)cc1)NC(=O)[C@@H]1CC(=O)N[C@@H](CSCC(N)=O)C(=O)N[C@@H]([C@@H](C)OC(C)(C)C)C(=O)N[C@@H]([C@@H](C)OC(C)(C)C)C(=O)N[C@@H]([C@@H](C)OC(C)(C)C)C(=O)N[C@@H](CCCNC(=N)NS(=O)(=O)c2c(C)c(C)c3c(c2C)OC(C)(C)C3)C(=O)N1]

Fmoc-Gly-OH, Fmoc-Tyr(tBu)-OH, Fmoc-Arg(Pbf)-OH (all purchased from Watanabe Chemical Industries) were used as Fmoc amino acids. 2-Chlorotrityl resin to which Fmoc-Gly-OH binds (250 mg) was placed in the synthesizer, and a peptide having a sequence of H-Tyr(tBu)-Tyr(tBu)-Arg(Pbf)-Gly-Gly-OH (peptide P-59) (SEQ ID NO: 319) was solid-phase synthesized.

A solution of c(Cys(CH₂CONH₂)-Thr(tBu)-Thr(tBu)-Thr(tBu)-Arg(Pbf)-Asp)-OH (peptide P-57 (SEQ ID NO: 318), 46 mg, 0.04 mmol), 1-hydroxy-7-azabenzotriazole (HOAt) (5.4 mg, 0.04 mmol) and diisopropylcarbodiimide (DIC) (0.075 mL, 0.048 mmol) in N,N-dimethylformamide (DMF) was added to the above resin. After 17 hours, the resin was washed with dichloromethane, and the peptide was cleaved from the resin by adding trifluoroacetic acid/dichloromethane (=1/99, 4 mL). The peptide was cleaved from the resin. After 1.5 hours, the resin was removed by filtering the solution in the tube through a synthesis column. The residue obtained by concentration under reduced pressure was purified by reverse-phase silica gel chromatography (10 mM aqueous ammonium acetate solution/methanol=50/50→0/100) to afford C(Cys(CH₂CONH₂)-Thr(tBu)-Thr(tBu)-Thr(tBu)-Arg(Pbf)-Asp)-Tyr(tBu)-Tyr(tBu)-Arg(Pbf)-Gly-Gly-OH (peptide P-58) (SEQ ID NO: 202) (6.2 mg, 7.3%).

LCMS: 1059 m/z (M+2H)2+
Retention time: 0.83 min (analysis condition SQDAA50)

2-2-6. Synthesis of C(Cys(CH₂CONH₂)-Thr-Thr-Thr-Arg-Asp)-Tyr-Tyr-Arg-Gly-Gly-OH (Peptide P-54) (SEQ ID NO: 201)

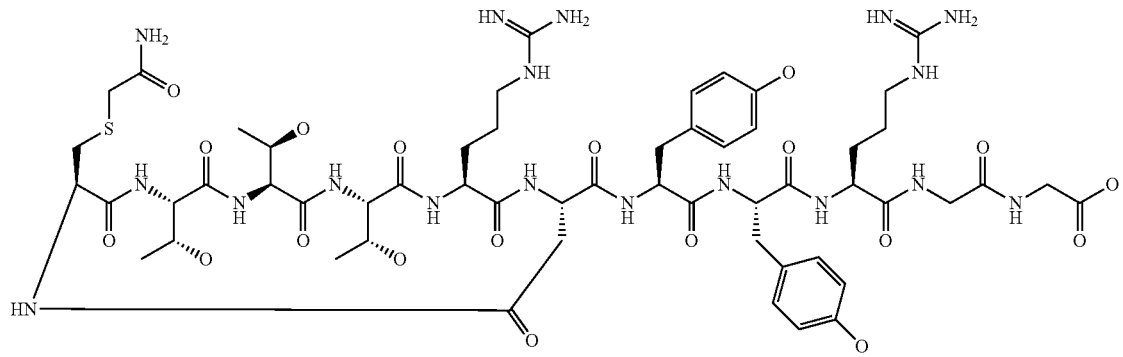 [SMILES: C[C@@H](O)[C@@H]1NC(=O)[C@H](CSCC(N)=O)NC(=O)C[C@@H](C(=O)N[C@@H](Cc2ccc(O)cc2)C(=O)N[C@@H](Cc2ccc(O)cc2)C(=O)N[C@@H](CCCNC(=N)N)C(=O)NCC(=O)NCC(=O)O)NC(=O)[C@H](CCCNC(=N)N)NC(=O)[C@H]([C@@H](C)O)NC(=O)[C@H]([C@@H](C)O)NC1=O]

Trifluoroacetic acid/triisopropylsilane/water (=9/1/1, v/v/v, 1 mL) were added to C(Cys(CH₂CONH₂)-Thr(tBu)-Thr(tBu)-Thr(tBu)-Arg(Pbf)-Asp)-Tyr(tBu)-Tyr(tBu)-Arg(Pbf)-Gly-Gly-OH (peptide P-58 (SEQ ID NO: 202), 6.2 mg), followed by stirring. After 4 hours, the residue obtained by concentration under reduced pressure was purified by reverse-phase silica gel chromatography (10 mM aqueous ammonium acetate solution/methanol=95/5−>0/100) to afford C(Cys(CH₂CONH₂)-Thr-Thr-Thr-Arg-Asp)-Tyr-Tyr-Arg-Gly-Gly-OH (peptide P-54) (SEQ ID NO: 201) (0.8 mg, 20%).

LCMS: 664 m/z (M−2H)2−, 1329.4 (M−H)−
LCMS: 1331.4 m/z (M+H)+
Retention time: 0.49 min (analysis condition SQDAA05)

Figures 1, 30:
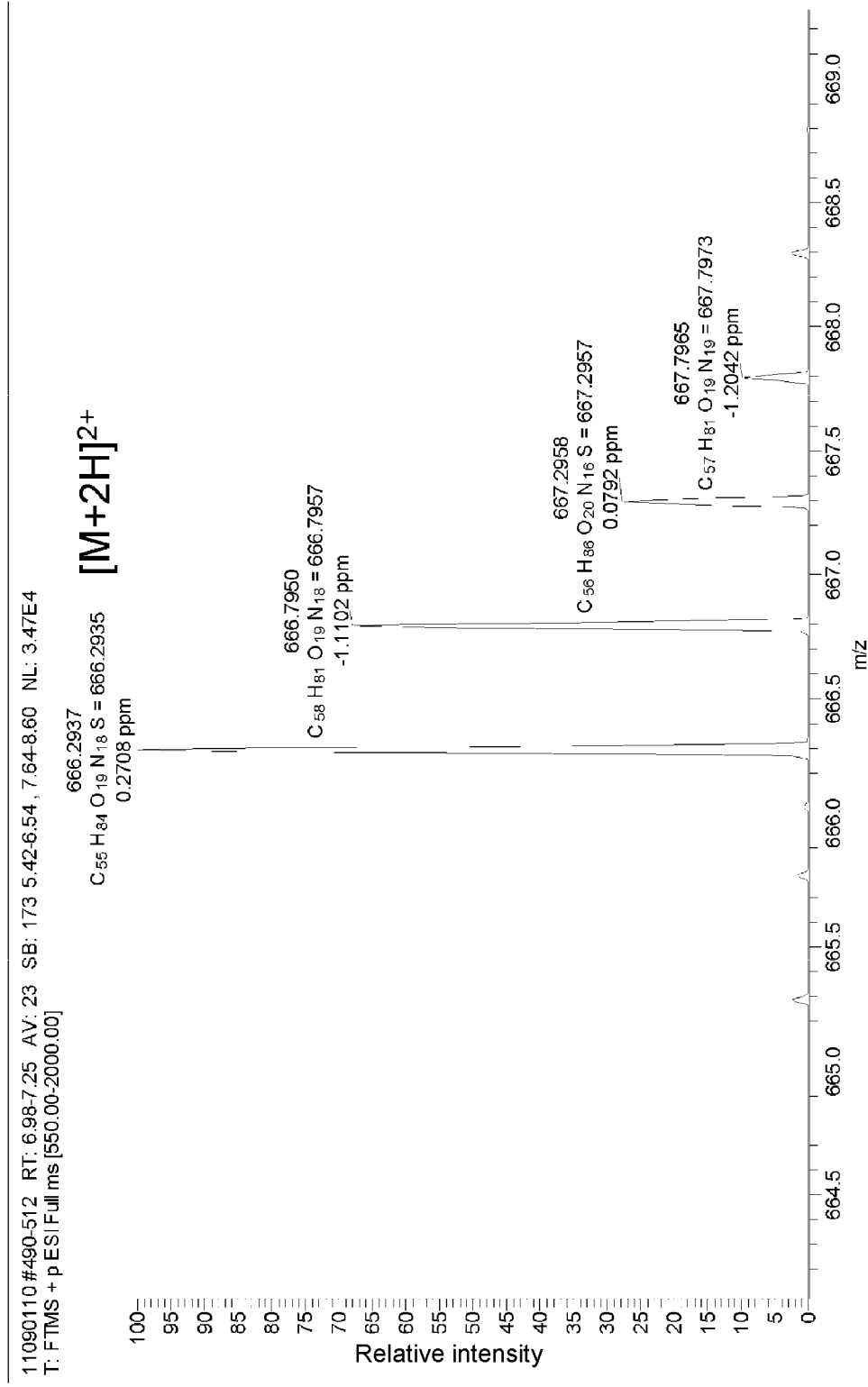
Figures 2, 30:
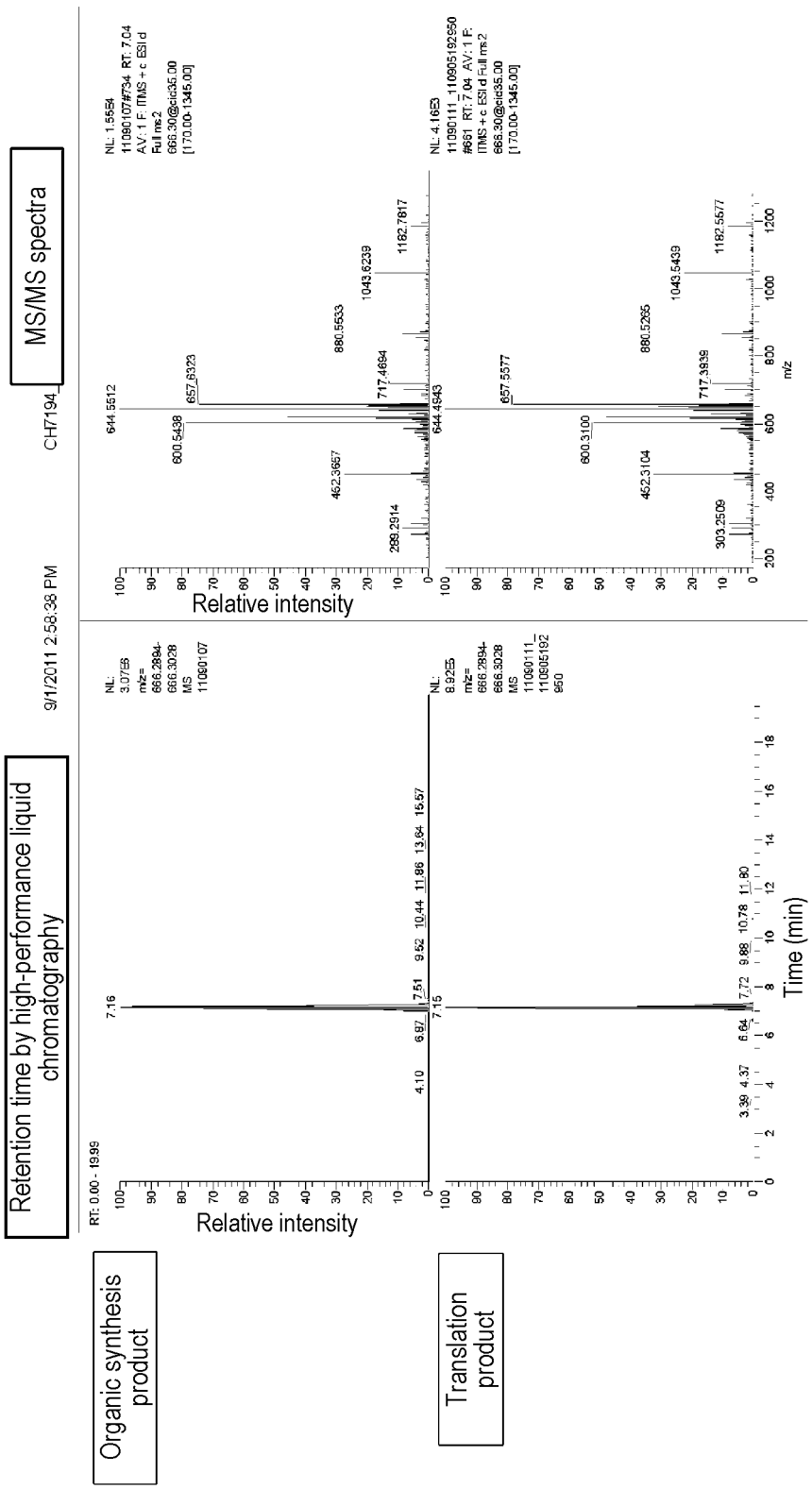

2-3. Cyclization Site Identification and Structure Determination for the Translated Peptide by LC/MS Analysis An organic synthesis product was made having the same sequence as in the translation synthesis product (peptide P-54). The products were comparatively analyzed using a high-resolution LC/MS instrument (Orbitrap Velos, Thermo Fisher Scientific, USA). For the translational product, 60 uL of 0.5% trifluoroacetic acid was added to about 30 uL of a translation solution, the mixture was stirred and then centrifuged, and the supernatant was applied to Oasis HLB cartridge (30 mg, 1 cc, Waters Corporation, USA). After washing with 1 mL of a 0.5% trifluoroacetic acid-containing 5% acetonitrile solution, elution was performed with 1 mL of a 0.5% trifluoroacetic acid-containing 60% acetonitrile solution. The eluate was nitrogen-dried, redissolved in 60 uL of a 0.5% trifluoroacetic acid-containing 20% acetonitrile solution and subjected to LC/MS analysis. As a result of measuring the exact mass of the translational product in the positive ion mode, the divalent protonated molecule [M+2H]²⁺ was assigned to m/z 666.2937, which highly corresponded to the theoretical value m/z 666.2935. The retention time in a high performance liquid chromatograph and the MS/MS spectrum pattern of the translational product were found to highly correspond to those of the organic synthesis product as a result of comparison between them. The above results confirmed that the translation synthesis product is identical to the cyclic peptide by organic synthesis (FIG. 30).

[Example 16] Desulfurization Reaction after Translation Synthesis and Cyclization Although amide cyclization reaction proceeded after translation synthesis, it is necessary to remove the SH group as the reaction auxiliary group in order to achieve the object of the present invention. Since the SH group is known to form covalent bonds with various proteins, it is likely to provide compounds with SH group-dependent bonds, but it is difficult to form pharmaceutical agents from such compounds due to their high reactivity.

Intermolecular reaction is needed to remove the SH group. As described previously, it is highly difficult to accomplish intermolecular reaction at a concentration of 1 uM and under the conditions where various reactive functional groups exist together. The following two methods to achieve such a reaction are possible. (i) Reagents used in excess only cause reversible reactions (such as coordinate bonds) except at the desired reaction points and are removed by posttreatment after completion of the reaction. (ii) Reagents used in excess do not affect RNAs at all.

Various reaction substrates and reaction conditions that can meet such various conditions were examined. The results are shown below.

1. Radical Desulfurization Reaction Using a Model Substrate

Figure 31:
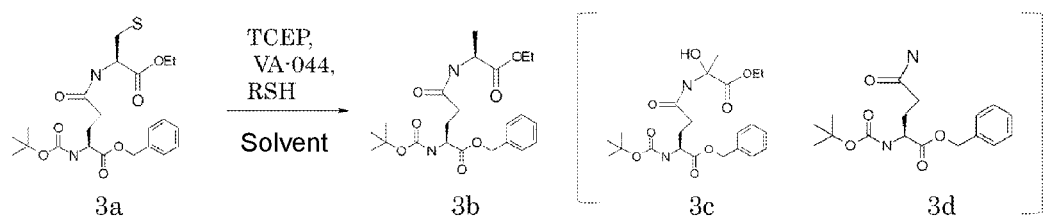
FIG. 31 is a diagram showing radical desulfurization reaction using a model substrate.

Radical desulfurization reaction was confirmed to proceed by the same method as that of Wan et al. (Angew. Chem. Int. Ed. 2007, 46, 9248) using a model substrate (S)-benzyl 2-((tert-butoxycarbonyl)amino)-5-(((R)-1-ethoxy-3-mercapto-1-oxopropan-2-yl)amino)-5-oxopentanoate (Compound 3a) (FIGS. 31 and 32). Method A and Method B were carried out as radical desulfurization reactions.

1-1. Experimental Example of Method a

The experiment described in FIG. 32 was carried out as follows.

1-1-1. Experiment of FIG. 32, Entry 1

Synthesis of (S)-benzyl 2-((tert-butoxycarbonyl)amino)-5-(((S)-1-ethoxy-1-oxopropan-2-yl)amino)-5-oxopentanoate (Compound 3b)

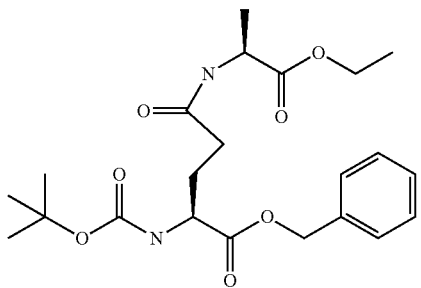 [SMILES: CCOC(=O)[C@H](C)NC(=O)CC[C@H](NC(=O)OC(C)(C)C)C(=O)OCc1ccccc1]

A 0.4 M aqueous tris(2-carboxyethyl)phosphine (TCEP) solution (0.428 ml, 0.171 mmol) was added to a solution of (S)-benzyl 2-((tert-butoxycarbonyl)amino)-5-(((R)-1-ethoxy-3-mercapto-1-oxopropan-2-yl)amino)-5-oxopentanoate (Compound 3a) (20.0 mg, 0.0427 mmol) in DMF (0.8 ml), and the mixture was stirred at room temperature for 15 minutes. tBuSH (0.0144 ml, 0.128 mmol) and a 1 M aqueous 2,2'-azobis-2-(2-imidazolin-2-yl)propane (VA-044) solution (0.0427 ml, 0.0427 mmol) were then added and the mixture was stirred at 50° C. for 2.5 hours. The reaction solution was then diluted by adding water, and subsequent purification by reverse-phase silica gel column chromatography (10 mM aqueous ammonium acetate solution/methanol=70/30→20/80) afforded (S)-benzyl 2-((tert-butoxycarbonyl)amino)-5-(((S)-1-ethoxy-1-oxopropan-2-yl)amino)-5-oxopentanoate (Compound 3b) (18.1 mg, 97%).

LCMS (ESI) m/z=437 (M+H)+
Retention time: 0.96 min (analysis condition SQDAA05)
Reagents and the like used for the reaction were prepared as follows.

Preparation of the 0.4 M Aqueous tris(2-carboxyethyl)phosphine (TCEP) Solution

A solution of tris(2-carboxyethyl)phosphine (TCEP) hydrochloride (1.0 g, 3.49 mmol) in water (6.8 ml) was adjusted to pH 7 by adding triethylamine (1.64 ml) thereto to give a 0.4 M aqueous tris(2-carboxyethyl)phosphine (TCEP) solution.

Preparation of the 1 M Aqueous 2,2'-azobis-2-(2-imidazolin-2-yl)propane (VA-044) Solution Water (0.309 ml) was added to 2,2'-azobis-2-(2-imidazolin-2-yl)propane (VA-044) hydrochloride (100 mg, 0.309 mmol) to prepare a 1 M aqueous 2,2'-azobis-2-(2-imidazolin-2-yl)propane (VA-044) solution.

Preparation of the 0.1 M Aqueous 2,2'-azobis-2-(2-imidazolin-2-yl)propane (VA-044) Solution Water (3.09 ml) was added to 2,2'-azobis-2-(2-imidazolin-2-yl)propane (VA-044) hydrochloride (100 mg, 0.309 mmol) to prepare a 0.1 M aqueous 2,2'-azobis-2-(2-imidazolin-2-yl)propane (VA-044) solution.

1-1-2. Experiments of FIG. 32, Entry 2 and Entry 3

(S)-Benzyl 2-((tert-butoxycarbonyl)amino)-5-(((S)-1-ethoxy-1-oxopropan-2-yl)amino)-5-oxopentanoate (Compound 3b)

Glutathione (19.7 mg, 0.064 mmol) and a 0.4 M aqueous tris(2-carboxyethyl)phosphine (TCEP) solution (0.214 ml, 0.0852 mmol) were added to a solution of (S)-benzyl 2-((tert-butoxycarbonyl)amino)-5-(((R)-1-ethoxy-3-mercapto-1-oxopropan-2-yl)amino)-5-oxopentanoate (Compound 3a) (10.0 mg, 0.0213 mmol) in DMF (0.5 ml) or methanol (0.5 ml), and the mixture was stirred at room temperature for 10 minutes. A 1 M aqueous 2,2'-azobis-2-(2-imidazolin-2-yl)propane (VA-044) solution (0.0213 ml, 0.0213 mmol) was then added at room temperature, and the mixture was stirred at 50° C. for 2 hours. The time course of reaction was observed by LCMS. As a result, in entry 2, the starting material Compound 3a entirely disappeared in two hours, and the intended Compound 3b was observed.

LCMS (ESI) m/z=437 (M+H)+
Retention time: 0.96 min (analysis condition SQDAA05)

1-1-3. Experiment of FIG. 32, Entry 4 (S)-benzyl-2-((tert-butoxycarbonyl)amino)-5-((S)-1-ethoxy-1-oxypropane-2-yl)amino)-5-oxopentanoate (Compound 3b)

A 0.4 M aqueous tris(2-carboxyethyl)phosphine (TCEP) solution (0.268 ml, 0.107 mmol) was added to a solution of (S)-benzyl 2-((tert-butoxycarbonyl)amino)-5-(((R)-1-ethoxy-3-mercapto-1-oxopropan-2-yl)amino)-5-oxopentanoate (Compound 3a) (10.0 mg, 0.0213 mmol) in methanol (4.66 ml) and water (2.06 ml), and the mixture was stirred at room temperature for 10 minutes. A 1 M aqueous 2,2'-azobis-2-(2-imidazolin-2-yl)propane (VA-044) solution (0.0213 ml, 0.0213 mmol) was then added at room temperature, and the mixture was stirred at 50° C. for 1 hour. The time course of reaction was observed by LCMS. As a result, the starting material 3a did not completely disappear, but the intended Compound 3b was observed. Further, estimated compounds 3c and 3d were also observed as by-products. The ratio of the starting material Compound 3a:the intended Compound 3b:3c:3d was 7:20:16:11 based on the UV area intensity ratio by LCMS.

Compound 3b
LCMS (ESI) m/z=437 (M+H)+
Retention time: 0.96 min (analysis condition SQDAA05)
Structurally Estimated Compound 3c
LCMS (ESI) m/z=453 (M+H)+
Retention time: 0.91 min (analysis condition SQDAA05)
Structurally Estimated Compound 3d
LCMS (ESI) m/z=337 (M+H)+
Retention time: 0.87 min (analysis condition SQDAA05)

1-1-4. Experiment of FIG. 32, Entry 5

(S)-Benzyl 2-((tert-butoxycarbonyl)amino)-5-(((S)-1-ethoxy-1-oxopropan-2-yl)amino)-5-oxopentanoate (Compound 3b)

Glutathione (196 mg, 0.639 mmol) and a 0.4 M aqueous tris(2-carboxyethyl)phosphine (TCEP) solution (0.268 ml, 0.107 mmol) were added to a solution of (S)-benzyl 2-((tert-butoxycarbonyl)amino)-5-(((R)-1-ethoxy-3-mercapto-1-oxopropan-2-yl)amino)-5-oxopentanoate (Compound 3a) (10.0 mg, 0.0213 mmol) in methanol (4.66 ml) and water (0.20 ml), and the mixture was stirred at room temperature for 10 minutes. A 1 M aqueous 2,2'-azobis-2-(2-imidazolin-2-yl)propane (VA-044) solution (0.0213 ml, 0.0213 mmol) was then added at room temperature, and the mixture was stirred at 50° C. for 1 hour. The time course of reaction was observed by LCMS. As a result, the starting material 3a completely disappeared, and the intended Compound 3b was observed.
LCMS (ESI) m/z=437 (M+H)+
Retention time: 0.96 min (analysis condition SQDAA05)

1-1-5. Experiment of FIG. 32, Entry 6

(S)-Benzyl 2-((tert-butoxycarbonyl)amino)-5-(((S)-1-ethoxy-1-oxopropan-2-yl)amino)-5-oxopentanoate (Compound 3b)

Glutathione (19.6 mg, 0.0639 mmol) and a 0.4 M aqueous tris(2-carboxyethyl)phosphine (TCEP) solution (0.268 ml, 0.107 mmol) were added to a solution of (S)-benzyl 2-((tert-butoxycarbonyl)amino)-5-(((R)-1-ethoxy-3-mercapto-1-oxopropan-2-yl)amino)-5-oxopentanoate (Compound 3a) (10.0 mg, 0.0213 mmol) in methanol (4.66 ml) and water (2.06 ml), and the mixture was stirred at room temperature for 10 minutes. A 1 M aqueous 2,2'-azobis-2-(2-imidazolin-2-yl)propane (VA-044) solution (0.0213 ml, 0.0213 mmol) was then added at room temperature, and the mixture was stirred at 50° C. for 1 hour. The time course of reaction was observed by LCMS. As a result, the starting material 3a completely disappeared, and the intended Compound 3b was observed. Further, estimated compounds 3c and 3d were also observed as by-products. The ratio of the starting material Compound 3a:the intended Compound 3b:3c:3d was 0:79:14:6 based on the UV area intensity ratio by LCMS.
Compound 3b
LCMS (ESI) m/z=437 (M+H)+
Retention time: 0.96 min (analysis condition SQDAA05)
Structurally Estimated Compound 3c
LCMS (ESI) m/z=453 (M+H)+
Retention time: 0.91 min (analysis condition SQDAA05)
Structurally estimated Compound 3d
LCMS (ESI) m/z=337 (M+H)+
Retention time: 0.87 min (analysis condition SQDAA05)

1-1-6. Experiment of FIG. 32, Entry 7

(S)-Benzyl 2-((tert-butoxycarbonyl)amino)-5-(((S)-1-ethoxy-1-oxopropan-2-yl)amino)-5-oxopentanoate (Compound 3b)

A 0.4 M aqueous tris(2-carboxyethyl)phosphine (TCEP) solution (0.268 ml, 0.107 mmol) was added to a solution of (S)-benzyl 2-((tert-butoxycarbonyl)amino)-5-(((R)-1-ethoxy-3-mercapto-1-oxopropan-2-yl)amino)-5-oxopentanoate (Compound 3a) (10.0 mg, 0.0213 mmol) in methanol (0.5 ml), and the mixture was stirred at room temperature for 10 minutes. A 1 M aqueous 2,2'-azobis-2-(2-imidazolin-2-yl)propane (VA-044) solution (0.0213 ml, 0.0213 mmol) was then added at room temperature, and the mixture was stirred at 50° C. for 1 hour. The time course of reaction was observed by LCMS. As a result, the starting material 3a completely disappeared, and the intended Compound 3b was observed. Further, estimated compounds 3c and 3d were also observed as by-products. The ratio of the starting material Compound 3a:the intended Compound 3b:3c:3d was 0:24:32:19 based on the UV area intensity ratio by LCMS.
Compound 3b
LCMS (ESI) m/z=437 (M+H)+
Retention time: 0.96 min (analysis condition SQDAA05)
Structurally Estimated Compound 3c
LCMS (ESI) m/z=453 (M+H)+
Retention time: 0.91 min (analysis condition SQDAA05)
Structurally Estimated Compound 3d
LCMS (ESI) m/z=337 (M+H)+
Retention time: 0.87 min (analysis condition SQDAA05)

1-2. Experimental Example of Method B

Method B is almost the same preparation method as Method A, except for the temperature of VA-044 addition. A 0.4 M aqueous tris(2-carboxyethyl)phosphine (TCEP) solution and glutathione were added to a solution of (5)-benzyl 2-((tert-butoxycarbonyl)amino)-5-(((R)-1-ethoxy-3-mercapto-1-oxopropan-2-yl)amino)-5-oxopentanoate (Compound 3a) in MeOH—H$_2$O and the mixture was heated to an intended reaction temperature of 30° C., 40° C. or 50° C., after which a 1 M aqueous 2,2'-azobis-2-(2-imidazolin-2-yl)propane (VA-044) solution was added and the mixture was directly stirred at a reaction temperature of 30° C., 40° C. or 50° C. The time course of reaction was observed by LC-MS.

The 0.4 M aqueous tris(2-carboxyethyl)phosphine (TCEP) solution was prepared as follows.

A solution of tris(2-carboxyethyl)phosphine (TCEP) hydrochloride (1.0 g, 3.49 mmol) in water (6.8 ml) was adjusted to pH 7 by adding triethylamine (1.64 ml) thereto to give a 0.4 M aqueous tris(2-carboxyethyl)phosphine (TCEP) solution.

The 1 M aqueous 2,2'-azobis-2-(2-imidazolin-2-yl)propane (VA-044) solution was prepared as follows.

Water (0.309 ml) was added to 2,2'-azobis-2-(2-imidazolin-2-yl)propane (VA-044) hydrochloride (100 mg, 0.309 mmol) to prepare a 1 M aqueous 2,2'-azobis-2-(2-imidazolin-2-yl)propane (VA-044) solution.

1-2-1. Experiment of FIG. 32, Entry 8

(S)-Benzyl 2-((tert-butoxycarbonyl)amino)-5-(((S)-1-ethoxy-1-oxopropan-2-yl)amino)-5-oxopentanoate (Compound 3b)

A 0.4 M aqueous tris(2-carboxyethyl)phosphine (TCEP) solution (0.192 ml, 0.092 mmol) was added to a solution of (S)-benzyl 2-((tert-butoxycarbonyl)amino)-5-(((R)-1-ethoxy-3-mercapto-1-oxopropan-2-yl)amino)-5-oxopentanoate (Compound 3a) (1.1 mg, 0.0023 mmol) in methanol (0.5 ml) and water (0.06 ml), and the mixture was stirred at 50° C. for 10 minutes. A 0.1 M aqueous 2,2'-azobis-2-(2-imidazolin-2-yl)propane (VA-044) solution (0.023 ml, 0.0023 mmol) was then added at 50° C., after which the mixture was stirred at 50° C. for 30 minutes. The time course of reaction was observed by LCMS. As a result, the starting material 3a completely disappeared, and the intended Compound 3b was observed.

LCMS (ESI) m/z=437 (M+H)+
Retention time: 0.95 min (analysis condition SQDAA05)

1-2-2. Experiment of FIG. 32, Entry 9

(S)-Benzyl 2-((tert-butoxycarbonyl)amino)-5-(((S)-1-ethoxy-1-oxopropan-2-yl)amino)-5-oxopentanoate (Compound 3b)

Glutathione (21.2 mg, 0.069 mmol) and a 0.4 M aqueous tris(2-carboxyethyl)phosphine (TCEP) solution (0.192 ml, 0.092 mmol) were added to a solution of (S)-benzyl 2-((tert-butoxycarbonyl)amino)-5-(((R)-1-ethoxy-3-mercapto-1-oxopropan-2-yl)amino)-5-oxopentanoate (Compound 3a) (1.1 mg, 0.0023 mmol) in methanol (0.5 ml) and water (0.06 ml), and the mixture was stirred at 50° C. for 10 minutes. A 0.1 M aqueous 2,2'-azobis-2-(2-imidazolin-2-yl)propane (VA-044) solution (0.023 ml, 0.0023 mmol) was then added at 50° C., after which the mixture was stirred at 50° C. for 30 minutes. The time course of reaction was observed by LCMS. As a result, the starting material 3a completely disappeared, and the intended Compound 3b was observed.

LCMS (ESI) m/z=437 (M+H)+
Retention time: 0.95 min (analysis condition SQDAA05)

1-2-3. Experiment of FIG. 32, Entry 10

(S)-Benzyl 2-((tert-butoxycarbonyl)amino)-5-(((S)-1-ethoxy-1-oxopropan-2-yl)amino)-5-oxopentanoate (Compound 3b)

A 0.4 M aqueous tris(2-carboxyethyl)phosphine (TCEP) solution (0.192 ml, 0.092 mmol) was added to a solution of (S)-benzyl 2-((tert-butoxycarbonyl)amino)-5-(((R)-1-ethoxy-3-mercapto-1-oxopropan-2-yl)amino)-5-oxopentanoate (Compound 3a) (1.1 mg, 0.0023 mmol) in methanol (0.5 ml) and water (0.06 ml), and the mixture was stirred at 40° C. for 15 minutes. A 0.1 M aqueous 2,2'-azobis-2-(2-imidazolin-2-yl)propane (VA-044) solution (0.023 ml, 0.0023 mmol) was then added at 40° C., and the mixture was stirred at 40° C. for 30 minutes. The time course of reaction was observed by LCMS. As a result, the starting material 3a completely disappeared, and the intended Compound 3b was observed.

LCMS (ESI) m/z=437 (M+H)+
Retention time: 0.96 min (analysis condition SQDAA05)

1-2-4. Experiment of FIG. 32, Entry 11

(S)-Benzyl 2-((tert-butoxycarbonyl)amino)-5-(((S)-1-ethoxy-1-oxopropan-2-yl)amino)-5-oxopentanoate (Compound 3b)

Glutathione (21.2 mg, 0.069 mmol) and a 0.4 M aqueous tris(2-carboxyethyl)phosphine (TCEP) solution (0.192 ml, 0.092 mmol) were added to a solution of (S)-benzyl 2-((tert-butoxycarbonyl)amino)-5-(((R)-1-ethoxy-3-mercapto-1-oxopropan-2-yl)amino)-5-oxopentanoate (Compound 3a) (1.1 mg, 0.0023 mmol) in methanol (0.5 ml) and water (0.06 ml), and the mixture was stirred at 40° C. for 15 minutes. A 0.1 M aqueous 2,2'-azobis-2-(2-imidazolin-2-yl)propane (VA-044) solution (0.023 ml, 0.0023 mmol) was then added at 40° C., after which the mixture was stirred at 40° C. for 30 minutes. The time course of reaction was observed by LCMS. As a result, the starting material 3a completely disappeared, and the intended Compound 3b was observed.

LCMS (ESI) m/z=437 (M+H)+
Retention time: 0.95 min (analysis condition SQDAA05)

1-2-5. Experiment of FIG. 32, Entry 12

(S)-Benzyl 2-((tert-butoxycarbonyl)amino)-5-(((S)-1-ethoxy-1-oxopropan-2-yl)amino)-5-oxopentanoate (Compound 3b)

A 0.4 M aqueous tris(2-carboxyethyl)phosphine (TCEP) solution (0.192 ml, 0.092 mmol) was added to a solution of (S)-benzyl 2-((tert-butoxycarbonyl)amino)-5-(((R)-1-ethoxy-3-mercapto-1-oxopropan-2-yl)amino)-5-oxopentanoate (Compound 3a) (1.1 mg, 0.0023 mmol) in methanol (0.5 ml) and water (0.06 ml), and the mixture was stirred at 30° C. for 15 minutes. A 0.1 M aqueous 2,2'-azobis-2-(2-imidazolin-2-yl)propane (VA-044) solution (0.023 ml, 0.0023 mmol) was then added at 30° C., after which the mixture was stirred at 30° C. for 1 hour and 30 minutes. The time course of reaction was observed by LCMS. As a result, the starting material 3a completely disappeared, and the intended Compound 3b was observed.

LCMS (ESI) m/z=437 (M+H)+
Retention time: 0.95 min (analysis condition SQDAA05)

1-2-6. Experiment of FIG. 32, Entry 13

(S)-Benzyl 2-((tert-butoxycarbonyl)amino)-5-(((S)-1-ethoxy-1-oxopropan-2-yl)amino)-5-oxopentanoate (Compound 3b)

Glutathione (21.2 mg, 0.069 mmol) and a 0.4 M aqueous tris(2-carboxyethyl)phosphine (TCEP) solution (0.192 ml, 0.092 mmol) were added to a solution of (S)-benzyl 2-((tert-butoxycarbonyl)amino)-5-(((R)-1-ethoxy-3-mercapto-1-oxopropan-2-yl)amino)-5-oxopentanoate (Compound 3a) (1.1 mg, 0.0023 mmol) in methanol (0.5 ml) and water (0.06 ml), and the mixture was stirred at 30° C. for 15 minutes. A 0.1 M aqueous 2,2'-azobis-2-(2-imidazolin-2-yl)propane (VA-044) solution (0.023 ml, 0.0023 mmol) was then added at 30° C., after which the mixture was stirred at 30° C. for 1 hour and 30 minutes. The time course of reaction was observed by LCMS. As a result, the starting material 3a completely disappeared, and the intended Compound 3b was observed.

LCMS (ESI) m/z=437 (M+H)+
Retention time: 0.95 min (analysis condition SQDAA05)

As shown in FIG. 32, radical desulfurization reactions were examined under various conditions. In Entries 4, 6 and 7 where the total thiol concentrations were low, Compounds 3c and 3d were observed as by-products for Method A. As a result of examination for conditions where by-products 3c and 3d are not produced even at low thiol concentrations in order to allow adaptation to Display Library (low peptide concentrations), production of the by-products could be suppressed by adding a radical initiator (VA-044) while heating the reaction solution (Method B) (Entries 8, 10 and 12).

Consequently, the present inventors discovered a method of translationally introducing an aspartic acid derivative having thioester in the side chain as a carboxylic acid derivative, translationally incorporating Cys or its derivative as an amino acid at the N-terminal, and then cyclizing them. The intended cyclic peptides were obtained by translationally introducing Asp(SBn) into peptides when Cys was incorporated at the N-terminal by the initiation read-through method.

2. RNA Stability Evaluation in Desulfurization Reaction

An RNA compound was subjected to desulfurization reaction conditions and its stability was confirmed.

2-1. Synthesis of 5'-AGCUUAGUCA-Puromycin-3' (Compound RP-1, (SEQ ID NO: 178))

RNA binding elongation was carried out with a DNA synthesizer using puromycin CPG manufactured by Glen Research (22.7 mg, 0.999 μmol). Elongation reaction of A, G, C and U was carried out using A-TOM-CE phosphoramidite, G-TOM-CE phosphoramidite, C-TOM-CE phosphoramidite and U-TOM-CE phosphoramidite manufactured by Glen Research as amidite reagents and using 5-benzylthio-1H-tetrazole as a condensation activator. Following condensation, the solid support was dried, after which ethanol (0.25 mL) and a 40% aqueous methylamine solution (0.25 mL) were added and the mixture was stirred at 65° C. for 1 hour. The solid support was separated by filtration and washed with methanol (0.5 mL). The resulting solution was concentrated and dissolved in methanol (1.0 mL). 0.8 mL of the solution was concentrated and dissolved in tetramethylammonium fluoride hydrate (50 μL), followed by stirring at 65° C. for 15 minutes. A 0.1 M aqueous ammonium acetate solution was added to the reaction solution, and the mixture was purified in a reverse-phase column. Following concentration, the resulting compound was purified again in the reverse-phase column. Water was added to the resulting solution, and the mixture was loaded on the reverse-phase column and then washed with water (30 mL), after which the intended product was eluted with methanol (50 mL). The resulting solution was concentrated and dissolved in water (1.0 mL) to afford an aqueous solution of 5'-AGCUUAGUCA-puromycin-3' (Compound RP-1).

LCMS (ESI) m/z=1224.6 (M−3H)3−
Retention time: 0.38 min (analysis condition SQDAA05)

2-2. Synthesis of (S)-benzyl 2-((tert-butoxycarbonyl)amino)-5-(((S)-1-ethoxy-1-oxopropan-2-yl)amino)-5-oxopentanoate (Compound 5e-2) by Desulfurization Reaction and Evaluation of Stability of 5'-AGCUUAGUCA-puromycin-3' (Compound RP-1) Under its Reaction Condition

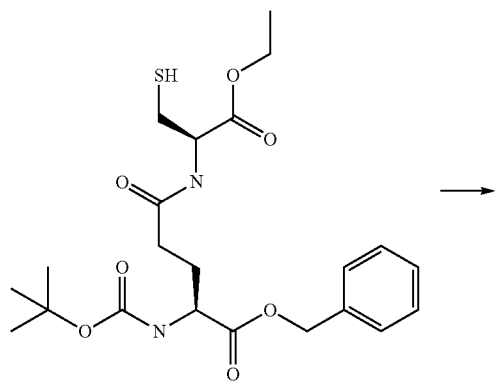

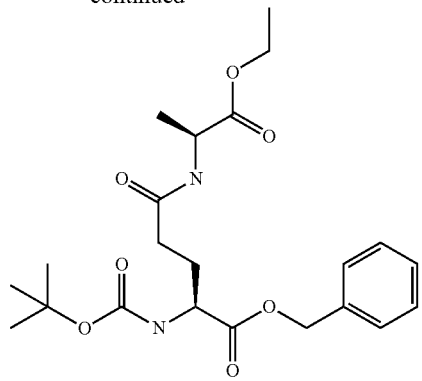

An aqueous solution of 5'-AGCUUAGUCA (SEQ ID NO: 69)-puromycin-3' (Compound RP-1) (10 μL), a 5 mM solution of 3-phenylbenzoic acid in methanol (10 μL) as standard, a 5 mM solution of (S)-benzyl 2-((tert-butoxycarbonyl)amino)-4-(((R)-1-ethoxy-3-mercapto-1-oxopropan-2-yl)amino)-4-oxobutanoate (Compound 5c-2) in methanol (5 μL), a aqueous 100 mM glutathione solution (15 μL) and triethylamine were mixed with a 0.4 M aqueous tris(2-carboxyethyl)phosphine (TCEP) solution previously adjusted to pH 7.1 (5 μL) and a 10 mM aqueous 2,2'-azobis-2-(2-imidazolin-2-yl)propane solution (5 μL), and the mixture was reacted at 50° C. for 2 hours. The reaction solution was analyzed by LC/MS to confirm that the amount of remaining 5'-AGCUUAGUCA (SEQ ID NO: 69)-puromycin-3' (Compound RP-1) was not changed. Under this condition, (S)-benzyl 2-((tert-butoxycarbonyl)amino)-5-(((R)-1-ethoxy-3-mercapto-1-oxopropan-2-yl)amino)-5-oxopentanoate (Compound 5c-2) disappeared, and the desulfurization reaction product, (S)-benzyl 2-((tert-butoxycarbonyl)amino)-5-(((S)-1-ethoxy-1-oxopropan-2-yl)amino)-5-oxopentanoate (Compound 5e-2), was confirmed.

LCMS (ESI) m/z=437.3 (M+H)+
Retention time: 0.96 min (analysis condition SQDAA05)

In this manner, it was confirmed that RNA was not reacted and stably existed under reaction conditions where desulfurization reaction proceeded.

2. Desulfurization Reaction Using a Translational Product

Translation was performed by the following method.
Translation reaction was carried out using the following sequence of DNA (SEQ ID NO: D-34) as template.

```
SEQ ID NO: D-34
Mctryg3_08U05U:
                                    (SEQ ID NO: 29)
GTAATACGACTCACTATAGGGTTAACTTTAAGAAGGAGATATACATATGt gcACTACAACGCGTctttactaccgtggcggcTAGTAGATAGATA
```

19 proteinogenic amino acids excluding methionine were added as amino acids to the reaction system. This resulted in synthesis of a peptide lacking methionine encoded by the initiation codon and having cysteine encoded by the second codon at the N-terminus. VA-044 (250 mM), TCEP (200 mM) and L-cysteine (20 mM) were added to this reaction solution, and the mixture was reacted at 40° C. for 1 hour. Consequently, an MS spectrum was confirmed where the SH group of the cystein side chain in the peptide chain was desulfurized and the molecular weight was reduced by 32 (FIG. 33).

Peptide ID P-50 before desulfurization
(SEQ ID NO: 38)
CysThrThrThrArgLeuTyrTyrArgGlyGly (Calc. 1289.6)

Peptide ID P-51 after desulfurization
(SEQ ID NO: 58)
AlaThrThrThrArgLeuTyrTyrArgGlyGly m/z: [M+H]+=1258.7 (Calc. 1257.7)

[Example 17] Evaluation of Protein Denaturation Under Cyclization Desulfurization Reaction Protein denaturation by a desulfurization reaction solution was evaluated (FIG. 34). As a model system, the effect of the desulfurization reaction condition on IL-6R was evaluated by detecting interaction between IL-6 and IL-6R using electrochemiluminescence immunoassay. First, 750 ng of anti-IL-6R antibody clone No. 17506 (R&D biosystems) was applied to a MSD Multi-array 384-well plate (MSD) and incubated at 4° C. overnight so that the antibody was immobilized on to the plate. The plate was washed with 80 μl of PBST three times to remove the unbound antibody, and blocking was then carried out with 2% skimmed milk for 1 hour. The blocking agent was washed away from the plate with 80 μl of PBST three times, after which 10 μl of 25 nM soluble human IL-6R (IL-6R) was added and the plate was shaken at room temperature for 50 minutes. The plate was washed with 80 μl of PBST three times, a desulfurization reaction solution (25 mM HEPES-K (pH 7.6), 200 mM TCEP, 250 mM VA-044 and 10 mM Cys) was added and the plate was shaken at room temperature for 50 minutes. The plate was washed with 80 μl of PBST three times, 10 μl of human IL-6-BAP (500 nM) was added and the plate was shaken at room temperature for 50 minutes. The plate was washed with 80 μl of PBST three times, 10 μL SULFO-TAG StAv (MSD, cat No. R32AD-5, 1 μg/mL) was added and the plate was then shaken at room temperature for 50 minutes. The plate was washed with 80 μl of PBST three times, and 35 μl of 2× read buffer (MSD, R92SC-3) was added, followed by measurement with SECTOR Imager 2400 (MSD) (FIG. 34).

The results indicated that addition of the desulfurization reaction solution affects IL6-R and weakens the interaction between IL-6R and IL-6. It was also indicated that addition of oxidized DTT (DTTox) reduces the influence on IL-6R and restores the interaction between IL-6R and IL-6.

[Example 18] Comparison with the Thioetherification Method

The cyclization method of the present invention was compared with the thioether cyclization method. Highly lipophilic thioether-cyclized peptides were synthesized which are assumed to penetrate lipid membranes rapidly.

1. Synthesis of Thioether-Cyclized Peptides

A peptide was elongated using an Fmoc amino acid such as Fmoc-MePhe-OH, Fmoc-MeAla-OH, Fmoc-MeLeu-OH, Fmoc-MeGly-OH, Fmoc-MeIle-OH, Fmoc-Ser(tBu)-OH, Fmoc-Thr(Trt)-OH, Fmoc-Ser(Trt)-OH, Fmoc-Phe-OH, Fmoc-Bip-OH, Fmoc-Leu-OH, Fmoc-Cha-OH, Fmoc-Ala-OH and Fmoc-Cys(Mmt)-OH (abbreviations are those in a catalog of Watanabe Chemical Industries). Following the peptide elongation, the Fmoc group at the N-terminal was deprotected, chloroacetic acid was condensed using HOAt and DIC as condensing agents, and the resin was then washed with dichloromethane. The peptide was cleaved from the resin, and at the same time, the O-trityl group and the S-dimethoxytrityl group were deprotected, by adding trifluoroacetic acid/dichloromethane/2,2,2-trifluoroethanol/triisopropylsilane (=1/62/31/6, v/v/v/v, 4 mL) to the resin and reacting for two hours. After completion of the reaction, the solution in the tube was filtered through a synthesis column to remove the resin. The reaction solution was added to a tube containing a diisopropylethylamine solution (1 mL), and cyclization reaction between the chloroacetyl group and cysteine was carried out. After completion of the reaction, the solvent was evaporated. The C-terminal carboxylic acid of the resulting crude product was amidated using piperidine (1.9 eq.) and O-(7-aza-1H-benzotriazol-1-yl)-N,N,N,N-tetramethyluronium hexafluorophosphate (HATU) (1.7 eq.) in DMF. After completion of the reaction, the solvent was evaporated using Genevac. The resulting crude product was dissolved in dimethyl sulfoxide, and the resulting peptide solution was purified by high-performance reverse-phase chromatography (HPLC).

(SEQ ID NO: 203)

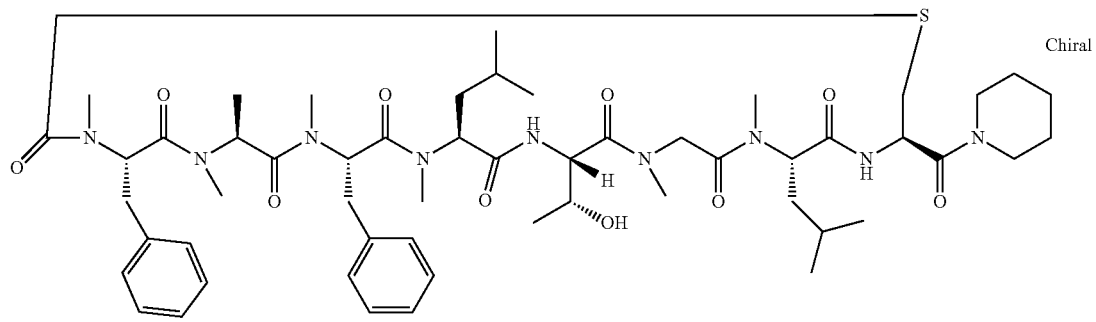

Compound P-101 Ac*-MePhe-MeAla-MePhe-MeLeu-Thr-MeGly-MeLeu-Cys*-piperidine
(cyclized at two * sites)

LCMS: 1063 m/z (M+H)+

Retention time: 0.77 min (analysis condition SQDAA50)

(SEQ ID NO: 204)
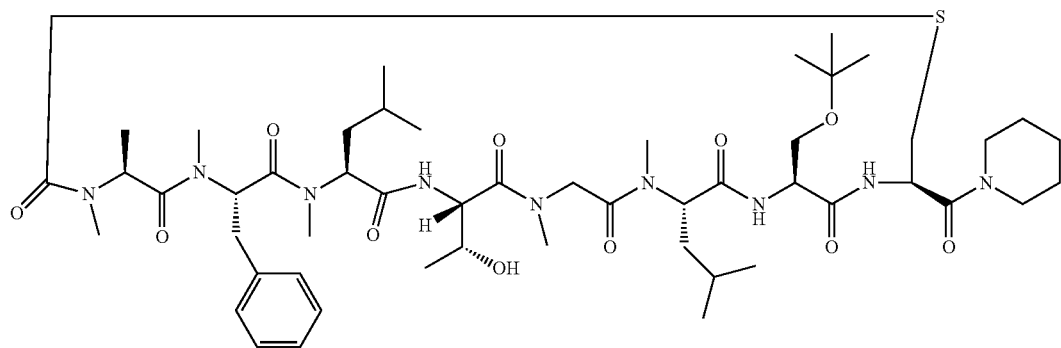
Compound P-102
Ac*–MeAla–MePhe–MeLeu–Thr–MeGly–MeLeu–Ser(tBu)–Cys*–piperidine
(cyclized at two * sites)
LCMS: 1045 m/z (M+H)+
Retention time: 0.76 min (analysis condition SQDAA50)
(SEQ ID NO: 205)
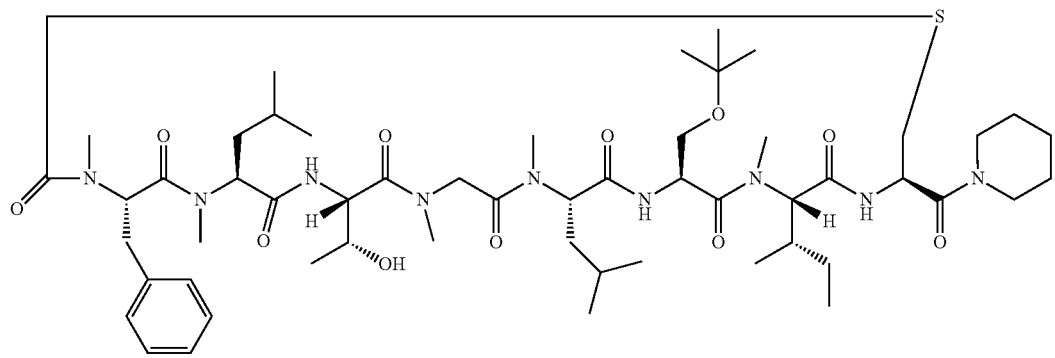
Compound P-103 Ac*-MePhe-MeLeu-Thr-MeGly-MeLeu-Ser(tBu)-MeIle-Cys*-piperidine
(cyclized at two * sites)
LCMS: 1087 m/z (M+H)+
Retention time: 2.72 min (analysis condition ZQAA50)

(SEQ ID NO: 206)
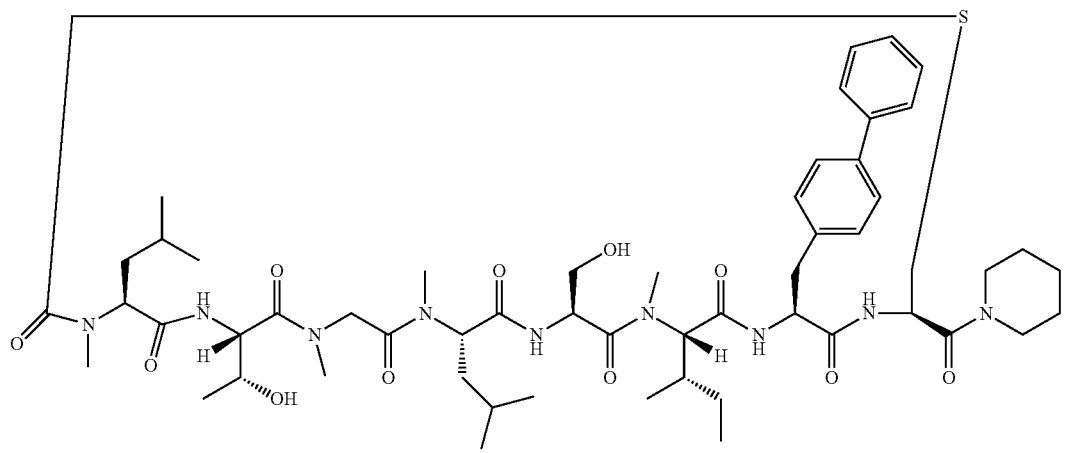
Compound P-104
Ac*-MeLeu-Thr-MeGly-MeLeu-Ser-MeIle-Bip-Cys*-piperidine
(cyclized at two * sites)
LCMS: 1093 m/z (M+H)+
Retention time: 2.52 min (analysis condition ZQAA50)
(SEQ ID NO: 207)
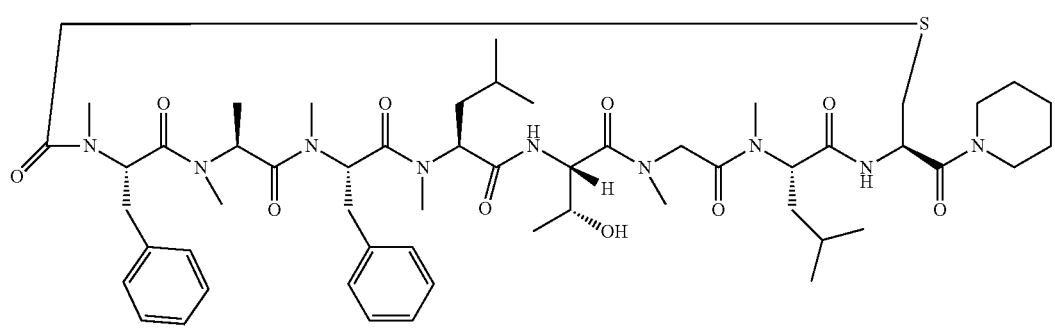
Compound P-105 Ac*-MePhe-MeAla-Phe-MeLeu-Thr-MeGly-MeLeu-Cys*-piperidine
(cyclized at two * sites)
LCMS: 1049 m/z (M+H)+
Retention time: 0.77 min (analysis condition SQDAA50)

(SEQ ID NO: 208)

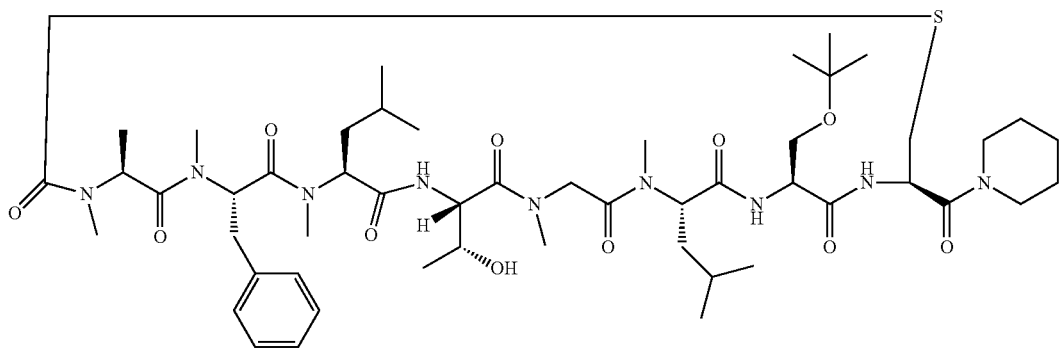

Compound P-106
Ac*–MeAla–Phe–MeLeu–Thr–MeGly–MeLeu–Ser (tBu)–Cys*–piperidine
(cyclized at two * sites)

LCMS: 1031 m/z (M+H)+
Retention time: 0.74 min (analysis condition SQDAA50)

(SEQ ID NO: 209)

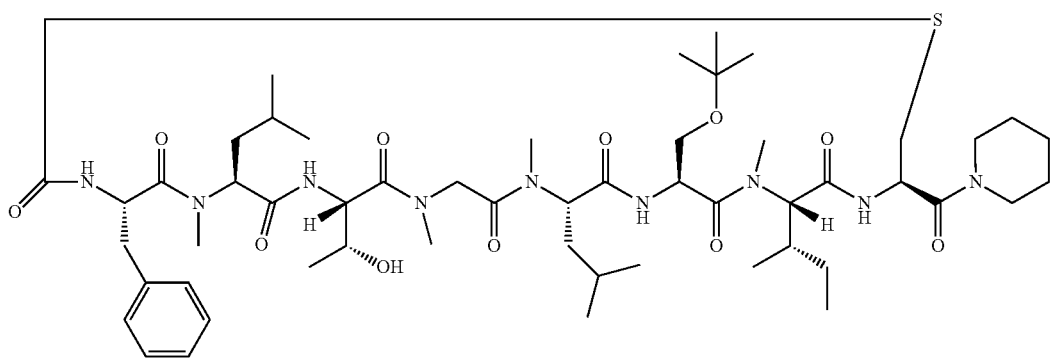

Compound P-107 Ac*-Phe-MeLeu-Thr-MeGly-MeLeu-Ser(tBu)-MeIle-Cys*-piperidine
(cyclized at two * sites)

LCMS: 1073 m/z (M+H)+
Retention time: 0.82 min (analysis condition SQDAA50)

(SEQ ID NO: 210)

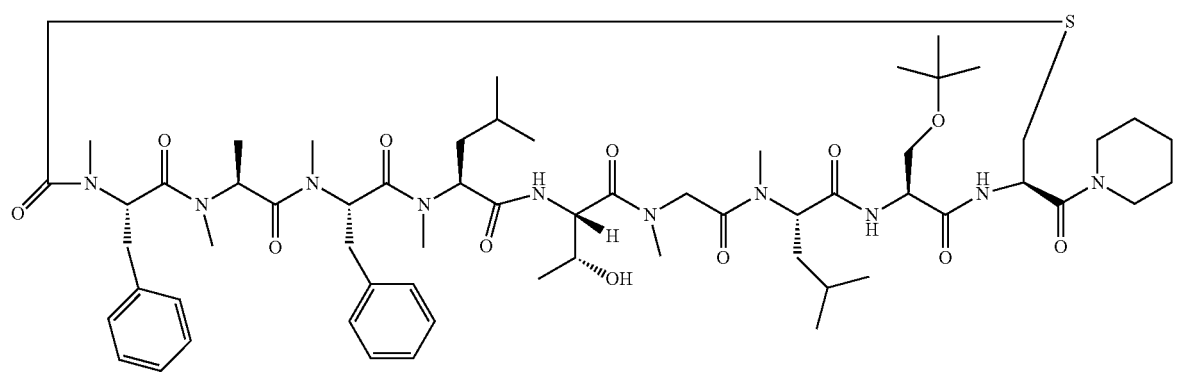

Compound P-108
Ac*-MePhe-MeAla-MePhe-MeLeu-Thr-MeGly-MeLeu-Ser(tBu)-Cys*-piperidine
(cyclized at two * sites)

LCMS: 1206 m/z (M+H)+
Retention time: 2.60 min (analysis condition ZQAA50)

(SEQ ID NO: 211)

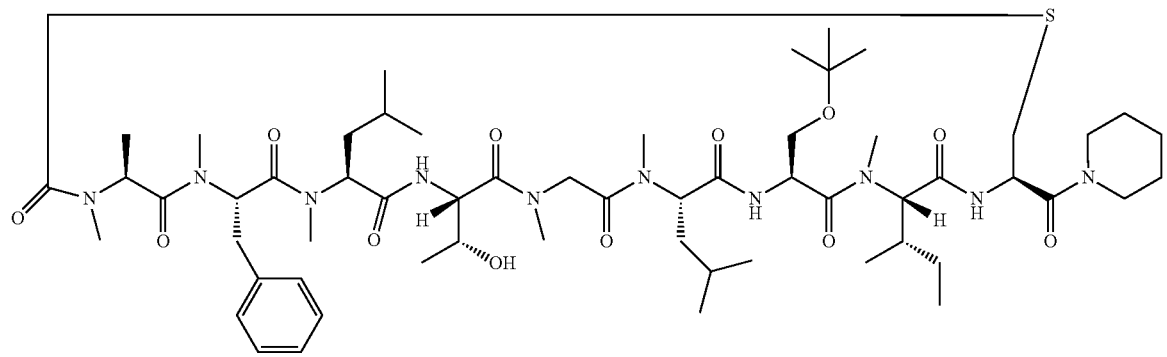

Compound P-109 Ac*-MeAla-MePhe-MeLeu-Thr-MeGly-MeLeu-Ser(tBu)-MeIle-Cys*-piperidine
(cyclized at two * sites)

LCMS: 1172 m/z (M+H)+
Retention time: 2.75 min (analysis condition ZQAA50)

(SEQ ID NO: 212)

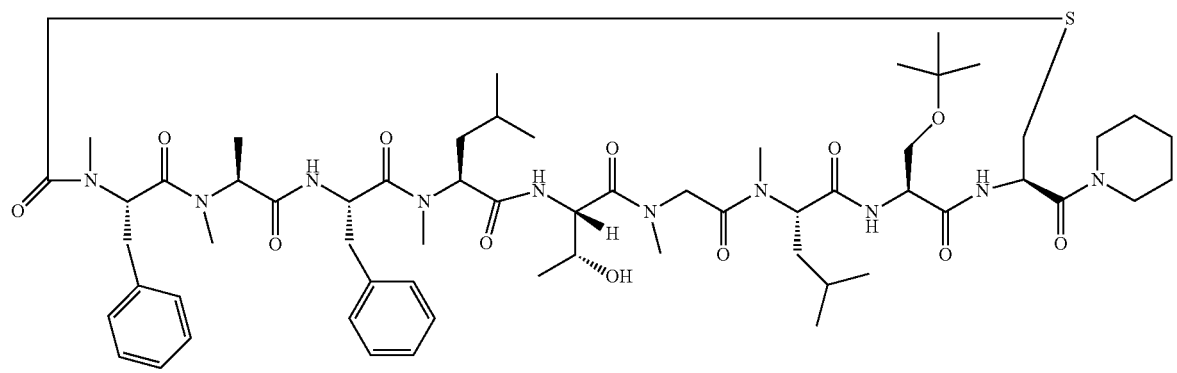

Compound P-110
Ac*-MePhe-MeAla-Phe-MeLeu-Thr-MeGly-MeLeu-Ser(tBu)-Cys*-piperidine
(cyclized at two * sites)

LCMS: 1192 m/z (M+H)+
Retention time: 0.81 min (analysis condition SQDAA50)

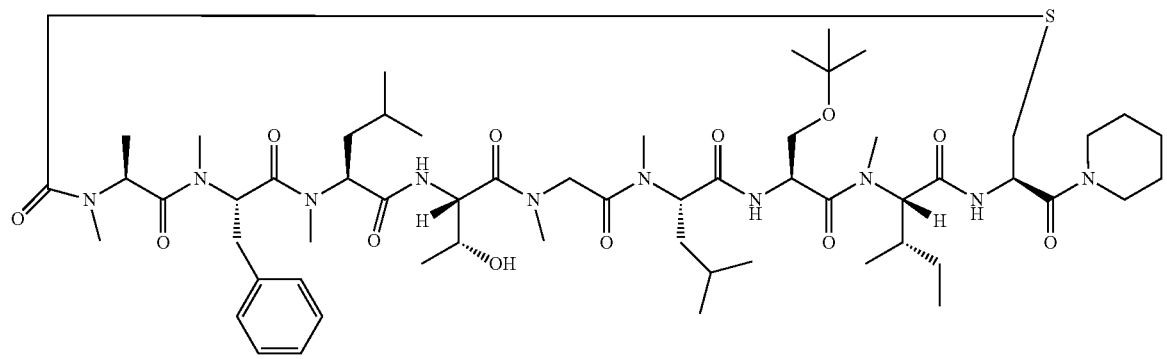

Compound P-111 Ac*-MeAla-Phe-MeLeu-Thr-MeGly-MeLeu-Ser(tBu)-MeIle-Cys*-piperidine
(cyclized at two * sites)

LCMS: 1158 m/z (M+H)+
Retention time: 2.75 min (analysis condition ZQAA50)

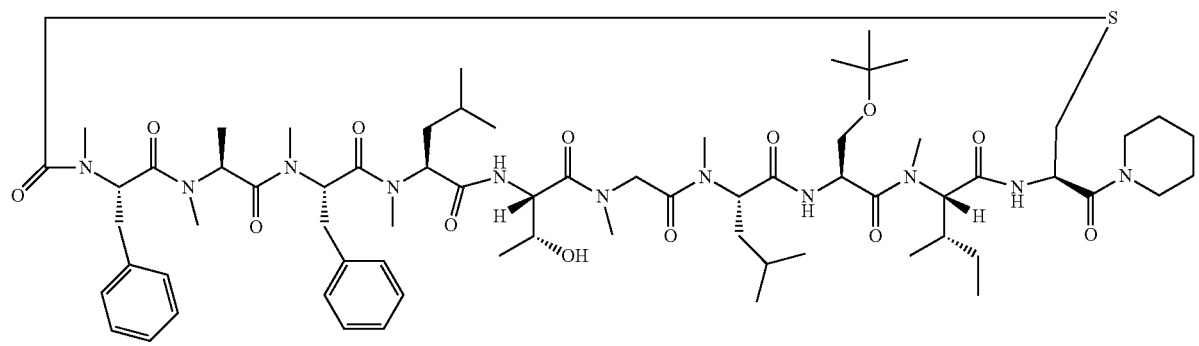

Compound P-112
Ac*-MePhe-MeAla-MePhe-MeLeu-Thr-MeGly-MeLeu-Ser(tBu)-MeIle-Cys*-piperidine
(cyclized at two * sites)

LCMS: 1333 m/z (M+H)+
Retention time: 2.87 min (analysis condition ZQAA05)

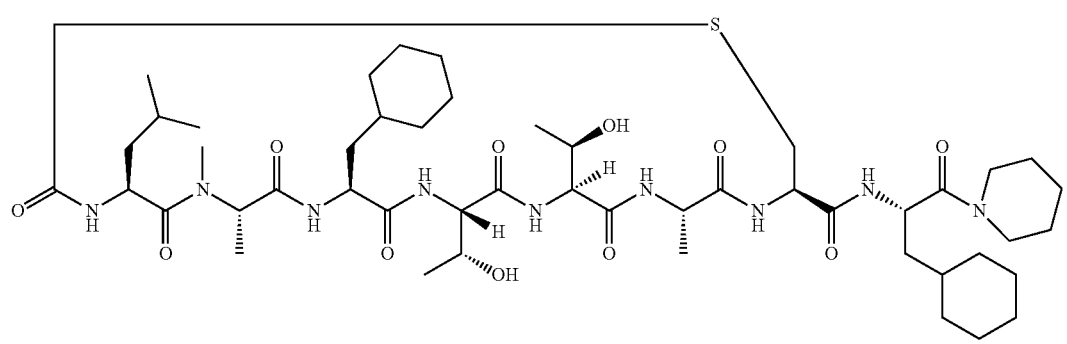

Compound P-113
Ac*-Leu-MeAla-Cha-Thr-Thr-Ala-Cys*-Cha-piperidine
(cyclized at two * sites)

LCMS: 1007 m/z (M+H)+
Retention time: 2.46 min (analysis condition ZQAA50)

2. Evaluation of Stability

2-1. Tests of Serum Stability and Hepatic Microsomal Stability of Thioether-Cyclized Peptides The obtained compound was metabolically reacted at a concentration of 2 uM with mouse serum (male/female mixed, Valley Biomedical, USA) (adjusted to pH 7.4 with 33.5 mM HEPES buffer) for two hours. Deproteinization treatment with acetonitrile was provided over time, the amount of the remaining unchanged compound was analyzed using LC/MS, and the metabolic half-life (t½) was calculated. A microsome solution prepared at 0.5 mg protein/mL from mouse hepatic microsome and small intestinal microsome (male, XENOTECH, USA) using 100 mM phosphate buffer (pH 7.4) was metabolically reacted with the compound at a concentration of 1 uM for 30 minutes in the presence or absence of NADPH. Deproteinization treatment with acetonitrile was provided over time, the amount of the remaining unchanged compound was analyzed using LC/MS, and the hepatic-intrinsic clearance (CLh, int) and the small intestinal-intrinsic clearance (CLg, int) were calculated (Table 7). Such peptides were sufficiently slowly metabolized by hydrolysis with peptidases or the like in mouse sera and microsomes, contrary to peptides composed of natural amino acids having low lipophilicity. When comparing these results, the metabolic rates in microsomes in the presence of NADPH were higher. This revealed that the main metabolic pathway is oxidative metabolism.

Each peptide in Table 7 is cyclized at Ac and C sites.

2-2. Tests of Metabolic Stability in Human Hepatic Microsomes and Metabolic Stability in Mouse Small Intestinal Microsomes of Thioether-Cyclized Peptides Having Relatively High Metabolic Stability and Thioether Site-Oxidized Compounds (Sulfoxide and Sulfone)

Metabolic stability tests were carried out in the same manner as shown in 2-1.

Tests of metabolic stability in mouse small intestinal microsomes and metabolic stability in human hepatic microsomes were carried out for the thioether compounds having relatively high metabolic stability in mice (Compounds P-112, 103, 102 and 109). Metabolic stability in human hepatic microsomes was about three times inferior to that in mouse hepatic microsomes.

Next, the hepatic and small intestinal oxidative metabolic rates of a sulfoxide obtained by oxidizing the S atom of Compound P-112 (sequence Ac\*-MeA-MeF-MeL-Thr-MeG-MeL-SertBu-MeI-Cys\*-piperidine) (Compound P-114) (SEQ ID NO: 216) were measured. As a result, the oxidative metabolic rates were 0.6 times for mouse hepatic microsomes, about 0.3 times for human hepatic microsomes and 0.2 times for small intestinal microsomes as compared with those of Compound P-112. Improvement in human hepatic and small intestinal metabolism was observed (Table 8). The small intestinal oxidative metabolic rate of the sulfone P-115 was about 0.5 times.

Metabolic stabilization by conversion of thioethers to sulfoxides was also observed for mouse hepatic microsomes in some other synthetic samples (Table 9).

TABLE 7

| | | | | | | | | | | | | | Serum stability | Hepatic Microsome CLh, int (Mouse) (ul/min/mg Protein) | |
|---|---|---|---|---|---|---|---|---|---|---|---|---|---|---|---|
| | | | | | | | | | | | | | t½ (Mouse) (h) | In the presence of NADPH | In the absence of NADPH |
| P-101 | | Ac | MeF | MeA | MeF | MeL | T | | MeG | MeL | C | piperidine | >60 | 358 | 1.1 |
| P-102 | | Ac | MeA | MeF | MeL | T | | MeG | MeL | StBu | C | piperidine | >60 | 55.1 | 0 |
| P-103 | | Ac | MeF | MeL | T | | MeG | MeL | StBu | MeI | C | piperidine | >60 | 63 | 11.1 |
| P-104 | | Ac | MeL | T | | MeG | MeL | S | | MeI | Bip | C | piperidine | >60 | 105.7 | 6.9 |
| P-105 | | Ac | MeF | MeA | F | | MeL | T | | MeG | MeL | C | piperidine | >60 | 278.1 | 5.1 |
| P-106 | | Ac | MeA | F | | MeL | T | | MeG | MeL | StBu | C | piperidine | >60 | 150.9 | 1.9 |
| P-107 | | Ac | F | | MeL | T | | MeG | MeL | StBu | MeI | C | piperidine | >60 | 111.1 | 10.1 |
| P-108 | Ac | MeF | MeA | MeF | MeL | T | | MeG | MeL | StBu | C | piperidine | >60 | 72.3 | 5.2 |
| P-109 | Ac | MeA | MeF | MeL | T | | MeG | MeL | StBu | MeI | C | piperidine | >60 | 57.4 | 10.3 |
| P-110 | Ac | MeF | MeA | F | | MeL | T | | MeG | MeL | StBu | C | piperidine | >60 | 162.6 | 6.1 |
| P-111 | Ac | MeA | F | | MeL | T | | MeG | MeL | StBu | MeI | C | piperidine | >60 | 76.4 | 0 |
| P-112 | Ac | MeF | MeA | MeF | MeL | T | | MeG | MeL | StBu | MeI | C | piperidine | >60 | 30.4 | 17.9 |

TABLE 8

| | | | | | | | | | | | | | Hepatic Microsome CLh, int (ul/min/mg Protein) | | Intestinal Microsome CLg, int (ul/min/mg Protein) |
|---|---|---|---|---|---|---|---|---|---|---|---|---|---|---|---|
| | | | | | | | | | | | | | Mouse | Human | Mouse |
| P-112 | Ac | $^{Me}$F | $^{Me}$A | $^{Me}$F | $^{Me}$L | T | $^{Me}$G | $^{Me}$L | Ser$^{tBu}$ | $^{Me}$I | C | thioether | 30.4 | 117.6 | 25.9 |
| P-103 | | Ac | $^{Me}$F | $^{Me}$L | T | $^{Me}$G | $^{Me}$L | Ser$^{tBu}$ | $^{Me}$I | | C | thioether | 63.0 | 220.9 | 66.3 |
| P-102 | | Ac | $^{Me}$A | $^{Me}$F | $^{Me}$L | Thr | $^{Me}$G | $^{Me}$L | Ser$^{tBu}$ | | C | thioether | 55.1 | 124.3 | 79.0 |
| P-109 | | Ac | $^{Me}$A | $^{Me}$F | $^{Me}$L | T | $^{Me}$G | $^{Me}$L | Ser$^{tBu}$ | $^{Me}$I | C | thioether | 57.4 | 157.5 | 45.8 |
| P-114 | | Ac | $^{Me}$A | $^{Me}$F | $^{Me}$L | T | $^{Me}$G | $^{Me}$L | Ser$^{tBu}$ | $^{Me}$I | C | sulfoxide | 33.7 | 35.3 | 9.1 |
| P-115 | | Ac | $^{Me}$A | $^{Me}$F | $^{Me}$L | T | $^{Me}$G | $^{Me}$L | Ser$^{tBu}$ | $^{Me}$I | C | sulfone | 42.1 | 61.6 | 21.8 |

Peptides in Table 8 are cyclized at Ac and C sites.

TABLE 9

| | | | | | | | | | | | | Mouse Hepatic Microsome CLh, int (ul/min/mg Protein) |
|---|---|---|---|---|---|---|---|---|---|---|---|---|
| P-112 | Ac | $^{Me}$F | $^{Me}$A | $^{Me}$F | $^{Me}$L | Thr | $^{Me}$G | $^{Me}$L | Ser$^{tBu}$ | $^{Me}$I | C | thioether | 30.4 |
| P-115 | Ac | $^{Me}$F | $^{Me}$A | $^{Me}$F | $^{Me}$L | Thr | $^{Me}$G | $^{Me}$L | Ser$^{tBu}$ | $^{Me}$I | C | sulfoxide | 12.1 |
| P-111 | Ac | $^{Me}$A | F | $^{Me}$L | Thr | $^{Me}$G | $^{Me}$L | Ser$^{tBu}$ | $^{Me}$I | C | thioether | 76.4 |
| P-116 | Ac | $^{Me}$A | F | $^{Me}$L | Thr | $^{Me}$G | $^{Me}$L | Ser$^{tBu}$ | $^{Me}$I | C | sulfoxide | 56.5 |
| P-103 | Ac | $^{Me}$F | $^{Me}$L | Thr | $^{Me}$G | $^{Me}$L | Ser$^{tBu}$ | $^{Me}$I | C | thioether | 63 |
| P-117 | Ac | $^{Me}$F | $^{Me}$L | Thr | $^{Me}$G | $^{Me}$L | Ser$^{tBu}$ | $^{Me}$I | C | sulfoxide | 36 |

Peptides in Table 9 are cyclized at Ac and C sites.

3. Identification of the Metabolic Site

Figures 1, 35:
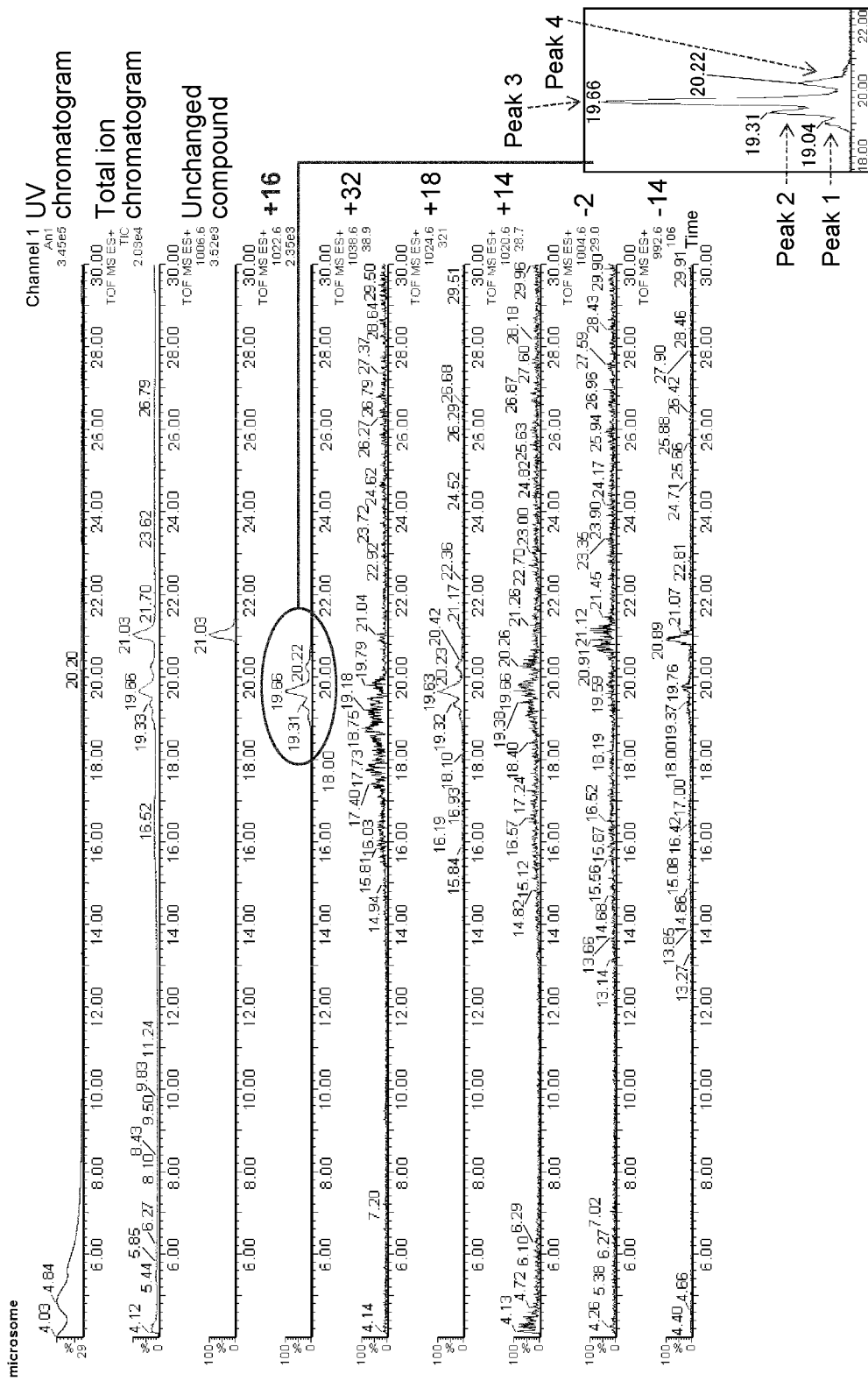
Figures 2, 35:
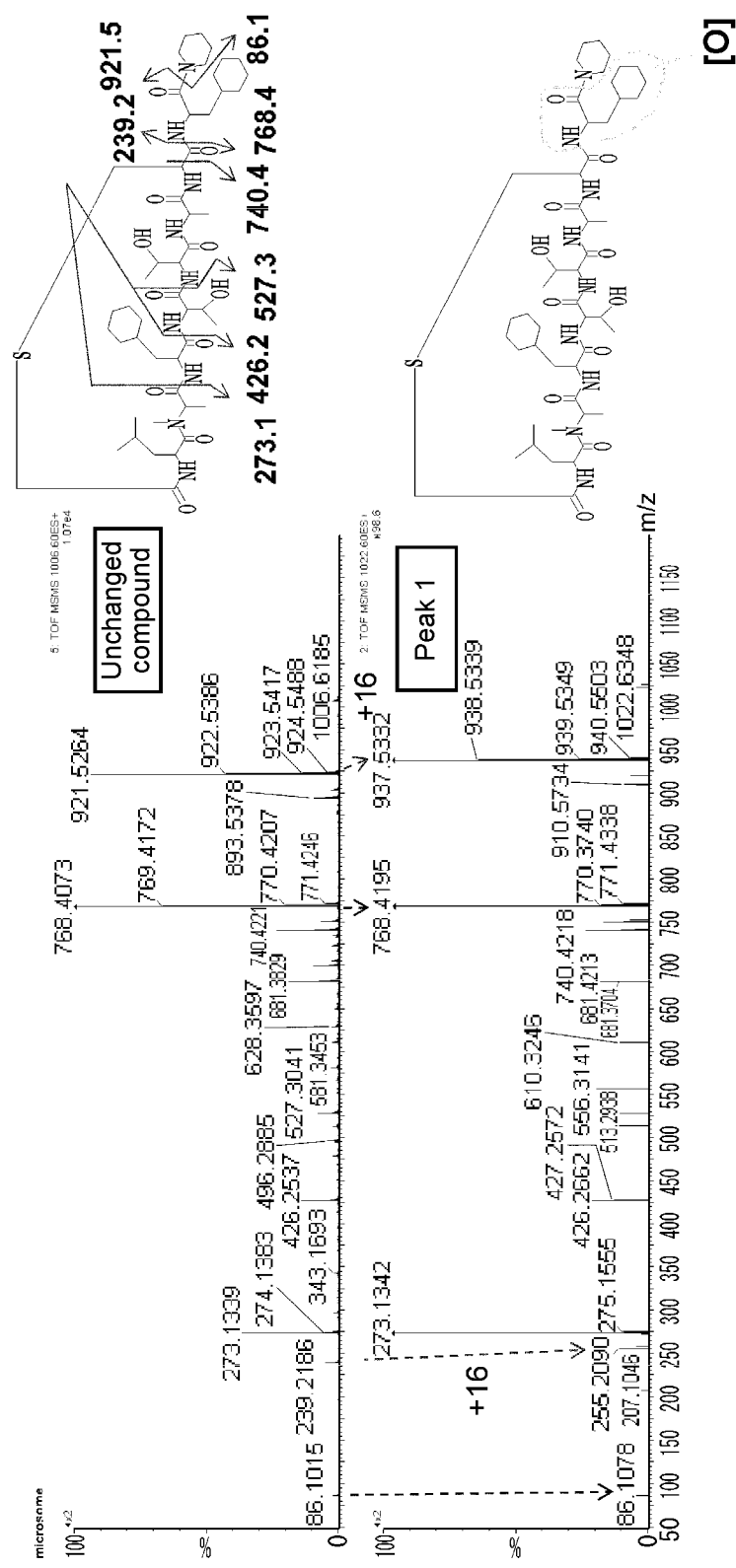
Figures 3, 35:
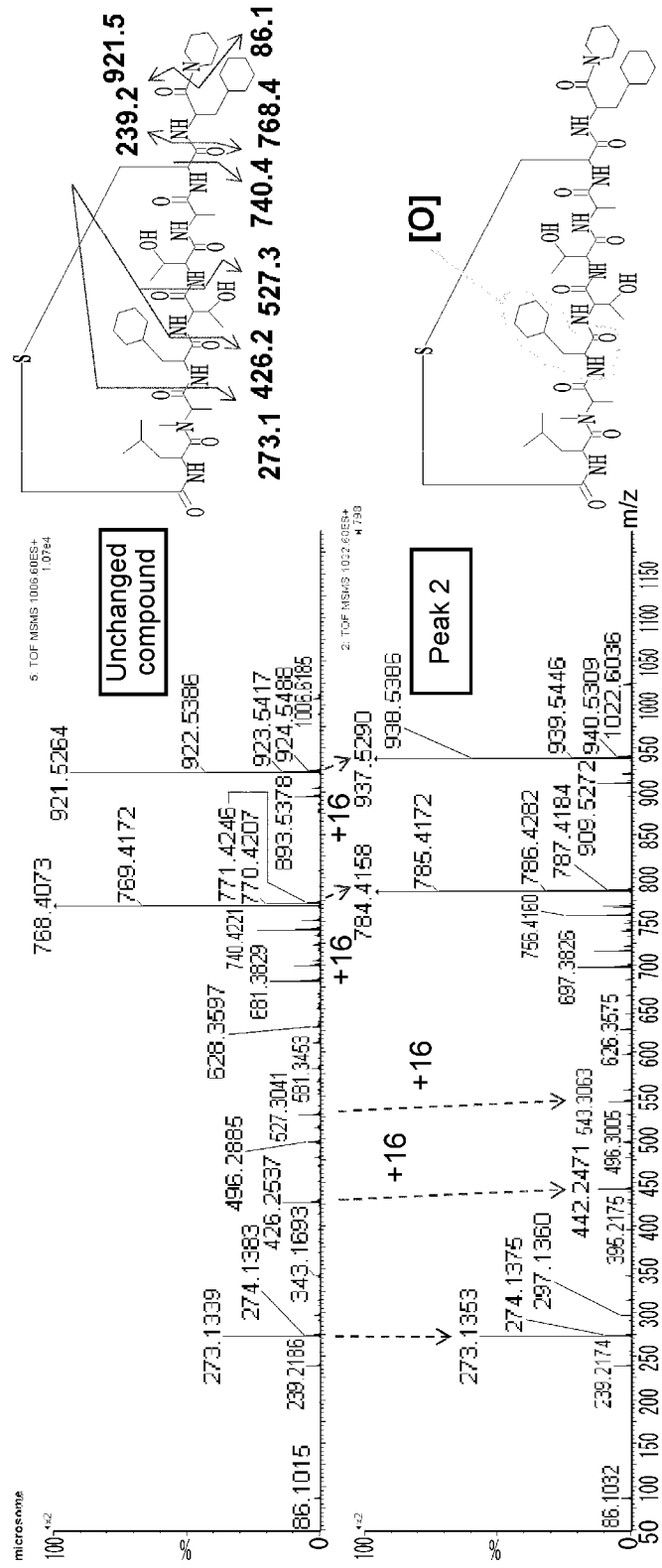
Figures 4, 35:
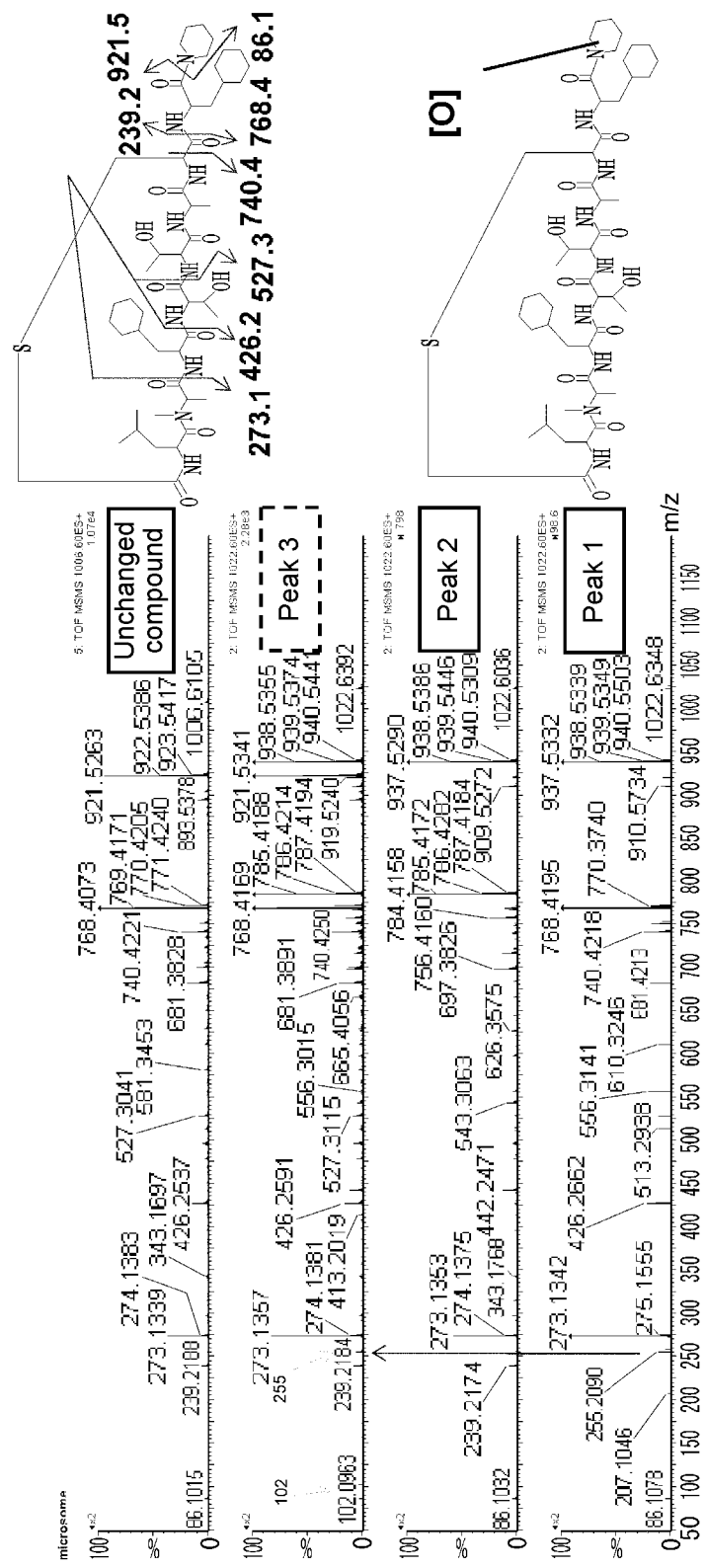
Figures 5, 35:
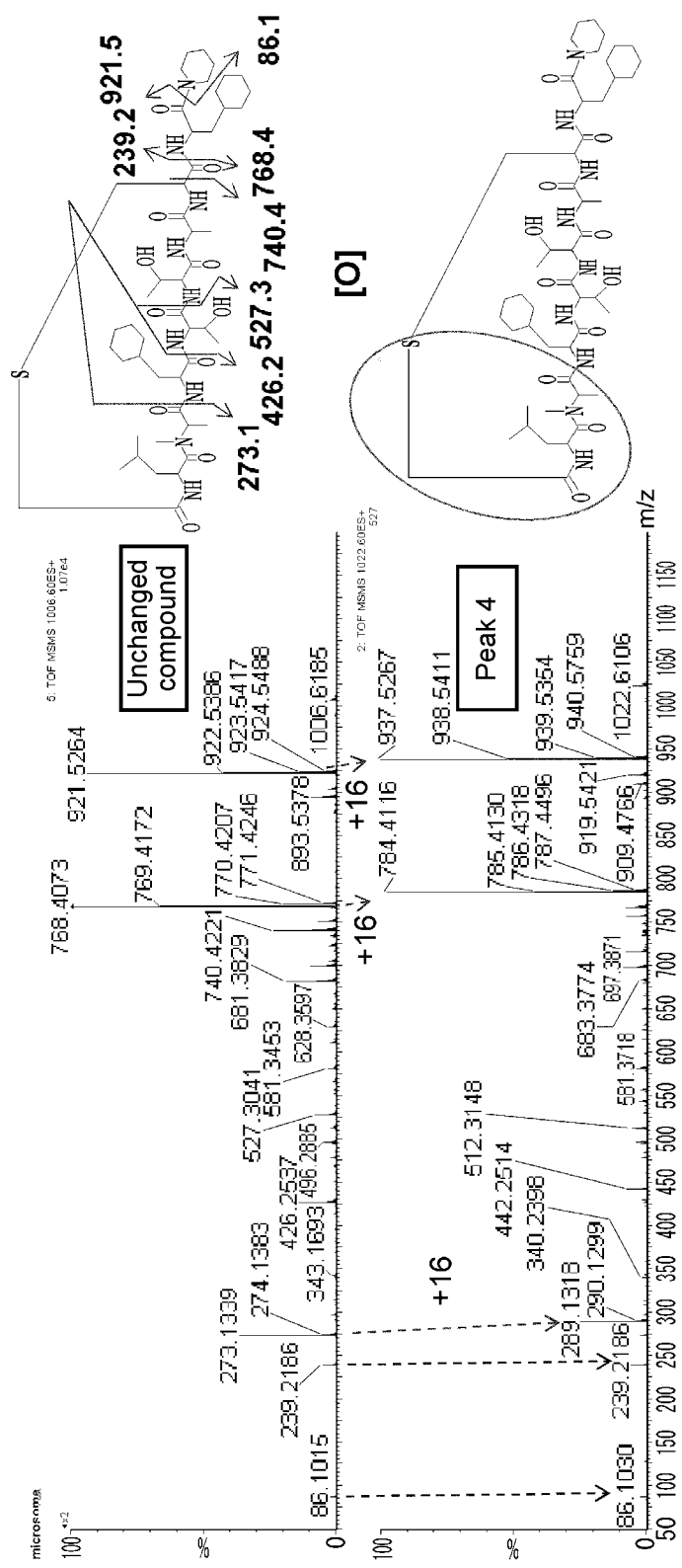

Compound P-113 cyclized peptide was metabolically reacted at a concentration of 10 uM with a microsome solution prepared at 0.5 mg protein/mL from mouse liver (male, manufactured by XENOTECH, USA) using 100 mM phosphate buffer (pH 7.4) for 1 hour in the presence of NADPH (FIG. 35). After the reaction, deproteinization treatment with acetonitrile was provided, and the resulting metabolites were analyzed with a high resolution LC/MS instrument (Q-TOF Ultima API, manufactured by Waters Corporation, USA). Mass chromatograms of the metabolites are shown below. Four peaks corresponding to hydroxides were detected as metabolites having relatively high intensity. MS/MS spectra of the peaks are shown below, respectively. The metabolites of Peak 1 and Peak 2 were assumed to be hydroxylated in the partial structures containing highly lipophilic side chain cyclohexyl groups. The metabolite of Peak 3 provided an ion characteristic to the case where a piperidine ring is hydroxylated at m/z 102, but also provided fragment ions similar to those in Peak 1 and Peak 2. Therefore, it was suggested that analogs of Peak 1 and Peak 2 may be present in Peak 3 or that Peak 1 and Peak 2 are mixed in Peak 3 due to insufficient separation. The metabolite of Peak 4 was assumed to have a thiol-containing site oxidizied. Taking the ease of oxidation of this site into consideration, it was believed that the sulfur atom is likely to be the metabolic site.

4. Direct Oxidation Reaction of Thioether-Cyclized Peptides

To specify the metabolic site more strictly, the obtained thioether-cyclized peptides were subjected to direct oxidation reaction. It was confirmed that direct oxidation of the thioether derivatives using oxone selectively oxidized a methionine derivative (peptide P-130), while oxidation reaction of a tryptophan derivative (peptide P-132) under the same condition did not proceed. Peptides P-114, P-115, P-116, P-117 and P-118 were obtained by selectively oxidizing the thioether moieties of several thioethers (peptides P-109, P-112, P-111 and P-103) using this condition.

18-4-1. Synthesis of (5S,8S,11S,14S,20S,23S,26S, 29R)-8-benzyl-23-(tert-butoxymethyl)-26-((S)-sec-butyl)-14-((R)-1-hydroxyethyl)-11,20-diisobutyl-4,5, 7,10,16,19,25-heptamethyl-29-(piperidine-1-carbonyl)-1-thia-4,7,10,13,16,19,22,25,28-nonaazacyclotriacontane-3,6,9,12,15,18,21,24,27-nonone 1-oxide (Compound P-114)

(SEQ ID NO: 217)

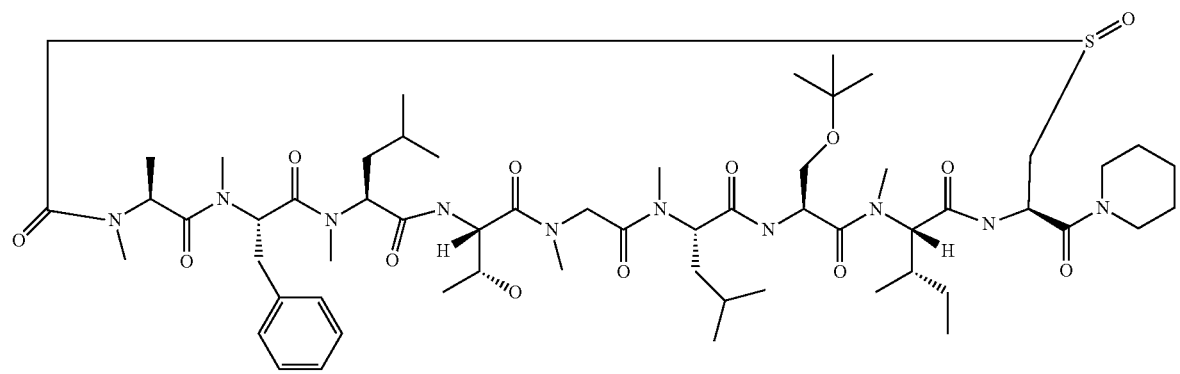

Sulfoxide of Ac*-MeAla-MePhe-MeLeu-Thr-MeGly-MeLeu-Ser(tBu)-MeIle-Cys*-piperidine compounds
(cyclized at two * sites, Compound P-109)

(5S,8S,11S,14S,20S,23S,26S,29R)-8-Benzyl-23-(tert-butoxymethyl)-26-((S)-sec-butyl)-14-((R)-1-hydroxyethyl)-11,20-diisobutyl-4,5,7,10,16,19,25-heptamethyl-29-(piperidine-1-carbonyl)-1-thia-4,7,10,13,16,19,22,25,28-nonaazacyclotriacontane-3,6,9,12,15,18,21,24,27-nonone (Compound P-109) (9.5 mg, 8.11×10$^{-3}$ mmol) was dissolved in methanol (0.5 ml), and water (0.25 ml) was added. The solution was cooled in an ice bath with stirring, and oxone (5.5 mg, 8.92×10$^{-3}$ mmol) was added. The reaction mixture was stirred under ice-cooling for 25 minutes, and DMSO (80 µl) was then added. The mixture was purified by reverse-phase silica gel column chromatography (10 mM aqueous ammonium acetate solution/methanol=60/40→0/100) to afford (5S,8S,11S,14S,20S,23S,26S,29R)-8-benzyl-23-(tert-butoxymethyl)-26-((S)-sec-butyl)-14-((R)-1-hydroxyethyl)-11,20-diisobutyl-4,5,7,10,16,19,25-heptamethyl-29-(piperidine-1-carbonyl)-1-thia-4,7,10,13,16,19,22,25,28-nonaazacyclotriacontane-3,6,9,12,15,18,21,24,27-nonone 1-oxide (Compound P-114) (8.6 mg, 90%).
LCMS (ESI) m/z=1187 (M+H)+
Retention times: 2.48 min, 2.62 min (analysis condition ZQAA50)

18-4-2. Synthesis of (5S,8S,11S,14S,20S,23S,26S, 29R)-8-benzyl-23-(tert-butoxymethyl)-26-((S)-sec-butyl)-14-((R)-1-hydroxyethyl)-11,20-diisobutyl-4,5, 7,10,16,19,25-heptamethyl-29-(piperidine-1-carbonyl)-1-thia-4,7,10,13,16,19,22,25,28-nonaazacyclotriacontane-3,6,9,12,15,18,21,24,27-nonone 1,1-dioxide (Compound P-115)

(SEQ ID NO: 217)

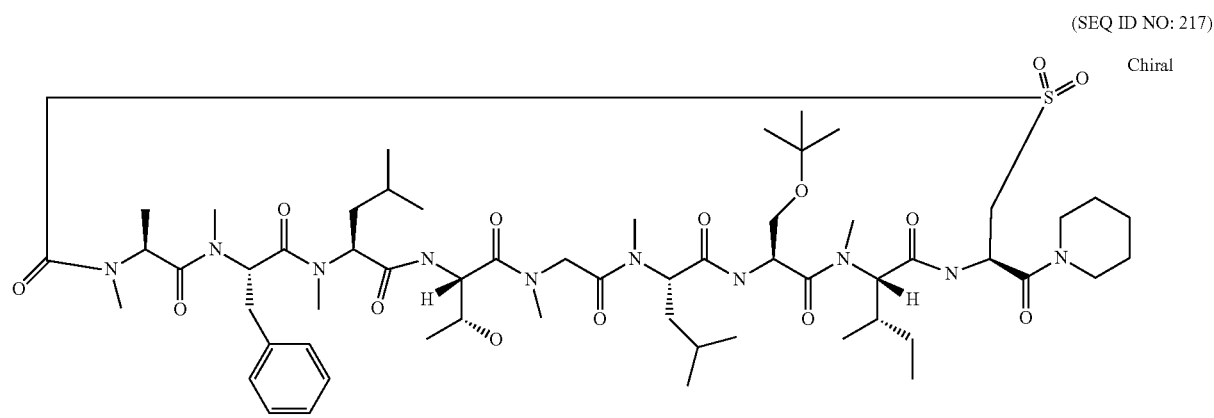

Sulfone of Ac*-MeAla-MePhe-MeLeu-Thr-MeGly-MeLeu-Ser(tBu)-MeIle-Cys*-piperidine compounds
(cyclized at two * sites, Compound P-109)

(5S,8S,11S,14S,20S,23S,26S,29R)-8-Benzyl-23-(tert-butoxymethyl)-26-((S)-sec-butyl)-14-((R)-1-hydroxyethyl)-

11,20-diisobutyl-4,5,7,10,16,19,25-heptamethyl-29-(piperidine-1-carbonyl)-1-thia-4,7,10,13,16,19,22,25,28-nonaazacyclotriacontane-3,6,9,12,15,18,21,24,27-nonone (9.6 mg, 8.19×10⁻³ mmol) was dissolved in methanol (0.6 ml), and water (0.3 ml) was added. While stirring the solution, oxone (15.1 mg, 2.46×10⁻² mmol) was added. The reaction mixture was stirred at room temperature for 14 hours, and DMSO (80 μl) was then added. The mixture was purified by reverse-phase silica gel column chromatography (10 mM aqueous ammonium acetate solution/methanol=60/40→0/100) to afford 5S,8S,11S,14S,20S,23S,26S,29R)-8-benzyl-23-(tert-butoxymethyl)-26-((S)-sec-butyl)-14-((R)-1-hydroxyethyl)-11,20-diisobutyl-4,5,7,10,16,19,25-heptamethyl-29-(piperidine-1-carbonyl)-1-thia-4,7,10,13,16,19,22,25,28-nonaazacyclotriacontane-3,6,9,12,15,18,21,24,27-nonaone 1,1-dioxide (8.3 mg, 84%).

LCMS (ESI) m/z=1203 (M+H)+

Retention time: 0.82 min (analysis condition SQDAA50)

18-4-3. Synthesis of (5S,8S,11S,14S,17S,23S,26S, 29S,32R)-5,11-dibenzyl-26-(tert-butoxymethyl)-29-((S)-sec-butyl)-17-((R)-1-hydroxyethyl)-14,23-diisobutyl-4,7,8,10,13,19,22,28-octamethyl-32-(piperidine-1-carbonyl)-1-thia-4,7,10,13,16,19,22,25,28,31-decaazacyclotritriacontane-3,6,9,12,15,18,21,24,27,30-decone 1-oxide (Compound P-116)

(SEQ ID NO: 218)

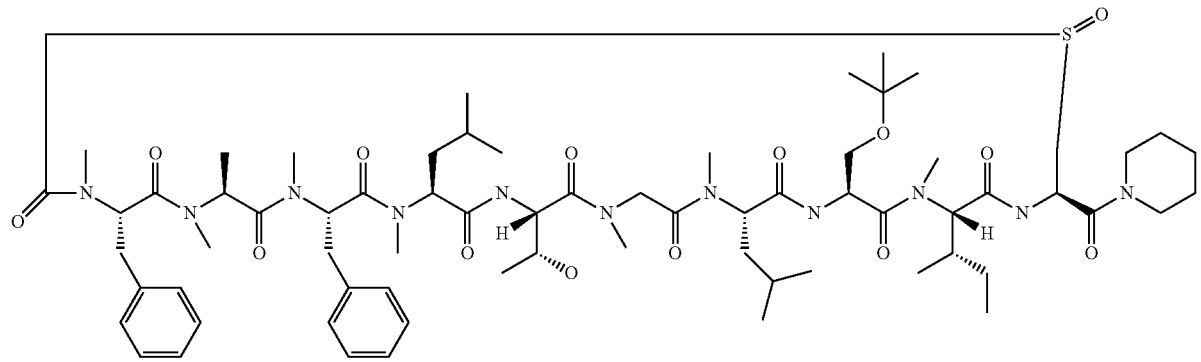

Sulfoxide by direct oxidation of Ac*-MePhe-MeAla-MePhe-MeLeu-Thr-MeGly-MeLeu-Ser(tBu)-MeIle-Cys*-piperidine
(Compound P-112)

5S,8S,11S,14S,17S,23S,26S,29S,32R)-5,11-Dibenzyl-26-(tert-butoxymethyl)-29-((S)-sec-butyl)-17-((R)-1-hydroxyethyl)-14,23-diisobutyl-4,7,8,10,13,19,22,28-octamethyl-32-(piperidine-1-carbonyl)-1-thia-4,7,10,13,16,19,22,25,28,31-decaazacyclotritriacontane-3,6,9,12,15,18,21,24,27,30-decaone 1-oxide (11.6 mg, 68%) was obtained from (5S,8S,11S,14S,17S,23S,26S,29S,32R)-5,11-dibenzyl-26-(tert-butoxymethyl)-29-((S)-sec-butyl)-17-((R)-1-hydroxyethyl)-14,23-diisobutyl-4,7,8,10,13,19,22,28-octamethyl-32-(piperidine-1-carbonyl)-1-thia-4,7,10,13,16,19,22,25,28,31-decaazacyclotritriacontane-3,6,9,12,15,18,21,24,27,30-decaone (16.9 mg, 1.27×10⁻² mmol) by the same method as in 18-4-1.

LCMS (ESI) m/z=1348 (M+H)+

Retention time: 0.84 min (analysis condition SQDAA50)

18-4-4. Synthesis of (5S,8S,11S,14S,20S,23S,26S,29R)-8-benzyl-23-(tert-butoxymethyl)-26-((S)-sec-butyl)-14-((R)-1-hydroxyethyl)-11,20-diisobutyl-4,5,10,16,19,25-hexamethyl-29-(piperidine-1-carbonyl)-1-thia-4,7,10,13,16,19,22,25,28-nonaazacyclotriacontane-3,6,9,12,15,18,21,24,27-nonone 1-oxide (Compound P-117)

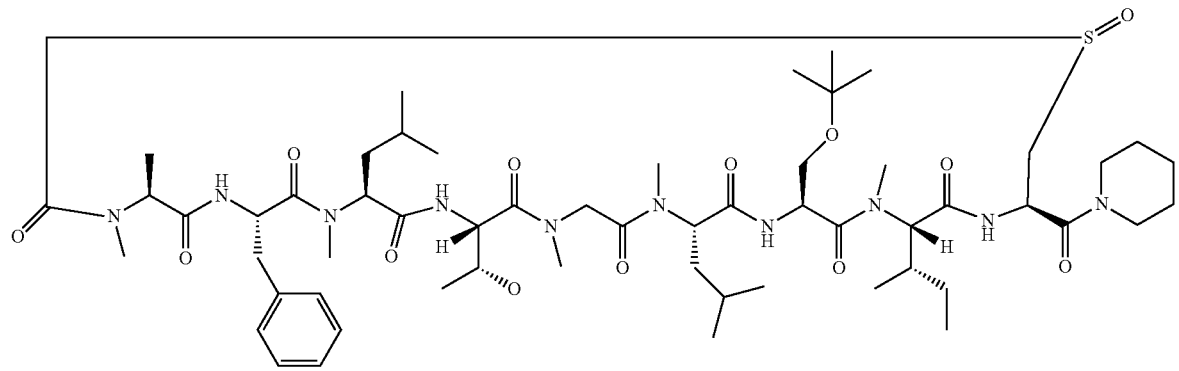

(SEQ ID NO: 219)

Sulfoxide (Compound P-117) by direct oxidation of Ac*-MeAla-Phe-MeLeu-Thr-MeGly-MeLeu-Ser(tBu)-MeIle-Cys*-piperidine (Compound P-111)

(5S,8S,11S,14S,20S,23S,26S,29R)-8-Benzyl-23-(tert-butoxymethyl)-26-((S)-sec-butyl)-14-((R)-1-hydroxyethyl)-11,20-diisobutyl-4,5,10,16,19,25-hexamethyl-29-(piperidine-1-carbonyl)-1-thia-4,7,10,13,16,19,22,25,28-nonaazacyclotriacontane-3,6,9,12,15,18,21,24,27-nonaone 1-oxide (10.5 mg, 83%) was obtained from (5S,8S,11S,14S,20S,23S,26S,29R)-8-Benzyl-23-(tert-butoxymethyl)-26-((S)-sec-butyl)-14-((R)-1-hydroxyethyl)-11,20-diisobutyl-4,5,10,16,19,25-hexamethyl-29-(piperidine-1-carbonyl)-1-thia-4,7,10,13,16,19,22,25,28-nonaazacyclotriacontane-3,6,9,12,15,18,21,24,27-nonaone (12.5 mg, 1.08×10−2 mmol) by the same method as in 18-4-1.

LCMS (ESI) m/z=1173 (M+H)+
Retention time: 2.57 min (analysis condition ZQAA50)

18-4-5. Synthesis of (5S,8S,11S,17S,20S,23S,26R)-5-benzyl-20-(tert-butoxymethyl)-23-((S)-sec-butyl)-11-((R)-1-hydroxyethyl)-8,17-diisobutyl-4,7,13,16,22-pentamethyl-26-(piperidine-1-carbonyl)-1-thia-4,7,10,13,16,19,22,25-octaazacycloheptacosane-3,6,9,12,15,18,21,24-octone 1-oxide (Compound P-118)

Synthesis by Direct Oxidation Reaction of Compound P-103

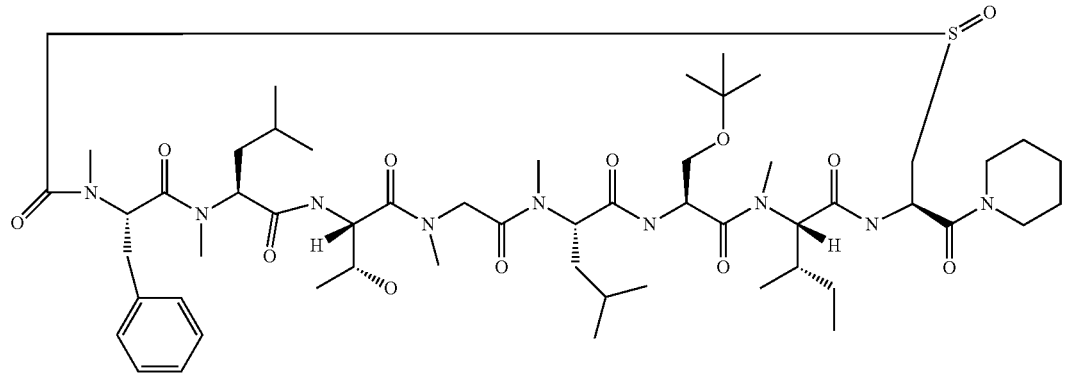 [SMILES: CC[C@H](C)[C@H]1C(=O)N[C@H](C(=O)N2CCCCC2)CS(=O)CC(=O)N(C)[C@@H](Cc2ccccc2)C(=O)N(C)[C@@H](CC(C)C)C(=O)N[C@@H]([C@@H](C)O)C(=O)N(C)CC(=O)N(C)[C@@H](CC(C)C)C(=O)N[C@@H](COC(C)(C)C)C(=O)N1C]

18-4-5. (5S,8S,11S,17S,20S,23S,26R)-5-benzyl-20-(tert-butoxymethyl)-23-((S)-sec-butyl)-11-((R)-1-hydroxyethyl)-8,17-diisobutyl-4,7,13,16,22-pentamethyl-26-(piperidine-1-carbonyl)-1-thia-4,7,10,13,16,19,22,25-octaazacycloheptacosane-3,6,9,12,15,18,21,24-octone 1-oxide (16.8 mg, 77%) was obtained from ((5S,8S,11S,17S,20S,23S,26R)-5-venzyl-20-(tert-butoxymethyl)-23-((S)-sec-butyl)-11-((R)-1-hydroxyethyl)-8,17-diisobutyl-4,7,13,16,22-pentamethyl-26-(piperidine-1-carbonyl)-1-thia-4,7,10,13,16,19,22,25-octaazacycloheptacosane-3,6,9,12,15,18,21,24-octone (21.4 mg, $1.97 \times 10^{-2}$ mmol) by the same method as in 18-4-1.

LCMS (ESI) m/z=1102 (M+H)+

Retention time: 0.80 min (analysis condition SQDAA50)

18-4-6. Oxidation of (S)-2-(9H-fluoren-9-yl-methoxycarbonylamino)-4-methylsulfanyl-butyric Acid

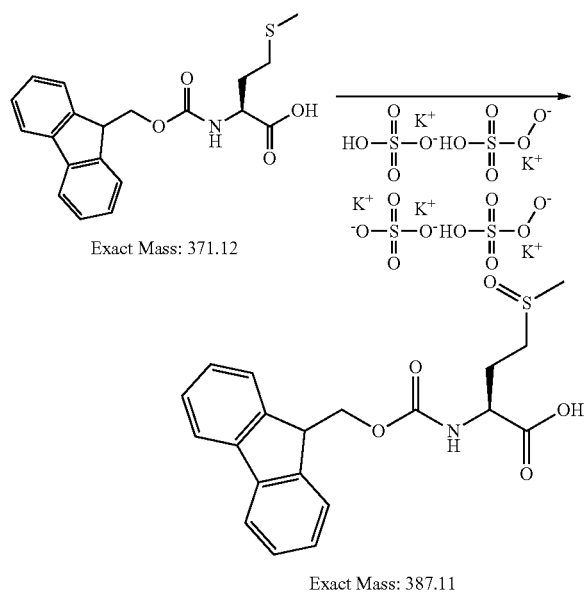

Exact Mass: 371.12

Exact Mass: 387.11

(S)-2-(9H-Fluoren-9-ylmethoxycarbonylamino)-4-methylsulfanyl-butyric acid (peptide P-130, 38 mg, 0.102 mmol) was dissolved in methanol (2 mL) at room temperature, water (0.2 mL) was added and then the mixture was cooled in an ice bath. Oxone (69 mg, 0.113 mmol) was added to the mixture, and the reaction mixture was stirred for 20 minutes, followed by addition of DMSO (100 μL). The progress of the reaction was confirmed by LCMS to find that a single peak was provided for a retention time different from that of the starting material (peptide P-131). (S)-2-(9H-Fluoren-9-ylmethoxycarbonylamino)-4-methylsulfanyl-butyric acid (peptide P-130)

LCMS (ESI) m/z=372 (M+H)+

Retention time: 0.94 min (analysis condition SQDAA05) Product P-131

LCMS (ESI) m/z=388 (M+H)+

Retention time: 0.86 min (analysis condition SQDAA05)

18-4-7. Oxidation of (S)-2-(9H-fluoren-9-yl-methoxycarbonylamino)-3-(1H-indol-3-yl)-propionic Acid: 2-isopropoxy-propane (1:2/3)

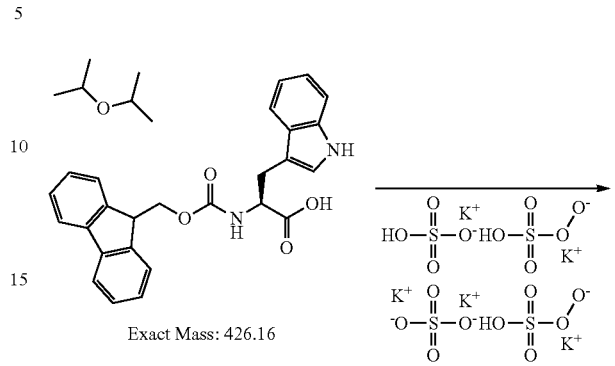

Exact Mass: 426.16

(S)-2-(9H-fluoren-9-ylmethoxycarbonylamino)-3-(1H-indol-3-yl)-propionic acid: 2-isopropoxy-propane (peptide P-132, 1:2/3) (50 mg, 0.101 mmol) was dissolved in methanol (2 mL) at room temperature, water (0.2 mL) was added and then the mixture was cooled in an ice bath. Oxone (68 mg, 0.113 mmol) was added to the mixture, and the reaction mixture was stirred for 20 minutes, followed by addition of DMSO (100 μL). The progress of the reaction was confirmed by LCMS to find that the same peak as that of the starting material was provided.

(S)-2-(9H-Fluoren-9-ylmethoxycarbonylamino)-3-(1H-indol-3-yl)-propionic acid (peptide P-132)

LCMS (ESI) m/z=427 (M+H)+

Retention time: 0.95 min (analysis condition SQDAA05)

The fact that thiols are easily oxidized by oxidation reaction of peptides in this manner is associated with the fact that thioethers are oxidatively metabolized readily as commonly recognized.

These experiments revealed the following facts. Among the peptides defined by the present inventors as membrane-permeable, thioether-cyclized peptides are rapidly metabolized. It was shown that although peptides are to be metabolized, the main metabolism is not amide bond hydrolysis but oxidative metabolism. Comparison with corresponding sulfoxides revealed that metabolic stability is achieved in compounds where thioether sites are previously oxidized so that the oxidative metabolism sites are blocked. Such a thioether site was estimated to be a metabolic site. Thioether sites were shown to be oxidized more easily than other sites, because thioether sites are selectively oxidized even by oxidation reaction by chemical reaction. As commonly known, thioethers are oxidatively metabolized readily. Thioethers are reported to be decomposed to RSCH2R'→RSH+R'CHO by cytochrome P450 and to be metabolized to sulfoxides by flavin-containing monooxygenase (Non patent literature, Drug metabology: As fundamentals of clinical pharmacy and toxicology, 2nd ed., Ryuichi Kato and Tetsuya Kamataki (eds.)). The former is produced as reactive metabolites and therefore may lead to development of toxicity.

Based on the above findings, it was concluded that although amide bonds are stable to metabolism, there is room for improvement in cyclization methods involving thioethers readily oxidized. It can be discussed that cyclic peptides by the method of the present invention in which all units are amide bonds are superior to cyclic peptides by conventional cyclization methods.

5. Comparison Between Metabolic Stability of Thioether-Cyclized Compounds and that of Amide-Cyclized Compounds Three thioethers having relatively high metabolic stability were selected among the highly lipophilic thioether-cyclized peptides. Amide-cyclized peptides having the same sequences as in the three thioethers except for the cyclization sites (MeAla-MePhe-MeLeu-Thr-MeGly-MeLeu-Ser (tBu) (SEQ ID NO: 220), MePhe-MeLeu-Thr-MeGly-MeLeu-Ser(tBu)-MeIle (SEQ ID NO: 221) and MeAla-MePhe-MeLeu-Thr-MeGly-MeLeu-Ser(tBu)-MeIle) (SEQ ID NO: 222) were synthesized. Metabolic stability of the three thioethers was compared with that of the amide-cyclized peptides. As shown in the following table, mouse microsomal metabolic stability of the amide-cyclized peptides was about two times higher than that of the thioesters, and human microsomal metabolic stability of the amide-cyclized peptides was about three times higher than that of the thioesters. Because metabolic stabilization was stably achieved in such a series of compounds, it was believed that an amide cyclization method in which thioether moiety structures contained in all displayed compounds are removed is a more drug-like display method in which many displayed compounds are more metabolically stabilized.

TABLE 10

| | | | | | | | | | | | | Hepatic microsome CLh, int (Human) (ul/min/mg Protein) | |
|---|---|---|---|---|---|---|---|---|---|---|---|---|---|
| | | | | | | | | | | | | in the presence of NADPH | in the absence of NADPH |
| P-102 | | Ac | $^{Me}$Ala | $^{Me}$Phe | $^{Me}$Leu | Thr | $^{Me}$Gly | $^{Me}$Leu | Ser(tBu) | Cys | thioether | 124 | 3 |
| P-119 | | Ala | $^{Me}$Ala | $^{Me}$Phe | $^{Me}$Leu | Thr | $^{Me}$Gly | $^{Me}$Leu | Ser(tBu) | Asp | amide | 56 | 5 |
| P-120 | | $^{Me}$Ala | $^{Me}$Ala | $^{Me}$Phe | $^{Me}$Leu | Thr | $^{Me}$Gly | $^{Me}$Leu | Ser(tBu) | Asp | amide | 67 | 5 |
| P-121 | | Ala | $^{Me}$Ala | $^{Me}$Phe | $^{Me}$Leu | Thr | $^{Me}$Gly | $^{Me}$Leu | Ser(tBu) | Glu | amide | 29 | 8 |
| P-122 | | $^{Me}$Ala | $^{Me}$Ala | $^{Me}$Phe | $^{Me}$Leu | Thr | $^{Me}$Gly | $^{Me}$Leu | Ser(tBu) | Glu | amide | 46 | 1 |
| P-103 | | Ac | $^{Me}$Phe | $^{Me}$Leu | Thr | $^{Me}$Gly | $^{Me}$Leu | Ser(tBu) | $^{Me}$Ile | Cys | thioether | 221 | 3 |
| P-123 | | Ala | $^{Me}$Phe | $^{Me}$Leu | Thr | $^{Me}$Gly | $^{Me}$Leu | Ser(tBu) | $^{Me}$Ile | Asp | amide | 156 | 0 |
| P-124 | | $^{Me}$Ala | $^{Me}$Phe | $^{Me}$Leu | Thr | $^{Me}$Gly | $^{Me}$Leu | Ser(tBu) | $^{Me}$Ile | Glu | amide | 69 | 8 |
| P-109 | Ac | $^{Me}$Ala | $^{Me}$phe | $^{Me}$Leu | Thr | $^{Me}$Gly | $^{Me}$Leu | Ser(tBu) | $^{Me}$Ile | Cys | thioether | 158 | 11 |
| P-125 | Ala | $^{Me}$Ala | $^{Me}$phe | $^{Me}$Leu | Thr | $^{Me}$Gly | $^{Me}$Leu | Ser(tBu) | $^{Me}$Ile | Asp | amide | 35 | 1 |

The peptides of Table 10 are either amide-cyclized at the N-terminal amino acid and Asp or Glu or thioether-cyclized at the Ac site and Cys.

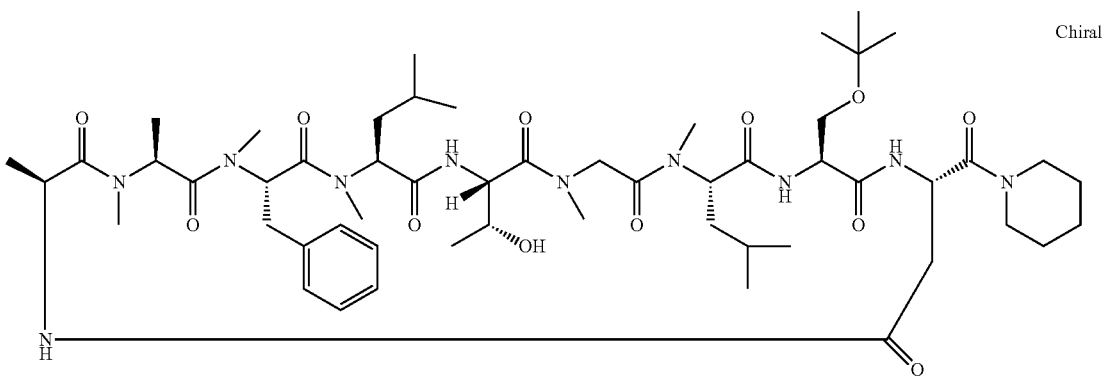

(SEQ ID NO: 223)

Compound P-119
Ala-MeAla-MePhe-MeLeu-Thr-MeGly-MeLeu-Ser(tBu)-Asp-piperidine
amide-cyclized at the N-terminal amine and the Asp side chain LCMS: 1067.8 m/z (M−H)−
Retention time: 0.72 min (analysis condition SQDAA50)

(SEQ ID NO: 224)

Chiral


Compound P-120
MeAla-MeAla-MePhe-MeLeu-Thr-MeGly-MeLeu-Ser(tBu)-Asp-piperidine
amide-cyclized at the N-terminal amine and the Asp side chain LCMS: 1081.9 m/z (M−H)−
Retention time: 0.73 min (analysis condition SQDAA50)

(SEQ ID NO: 225)

Chiral

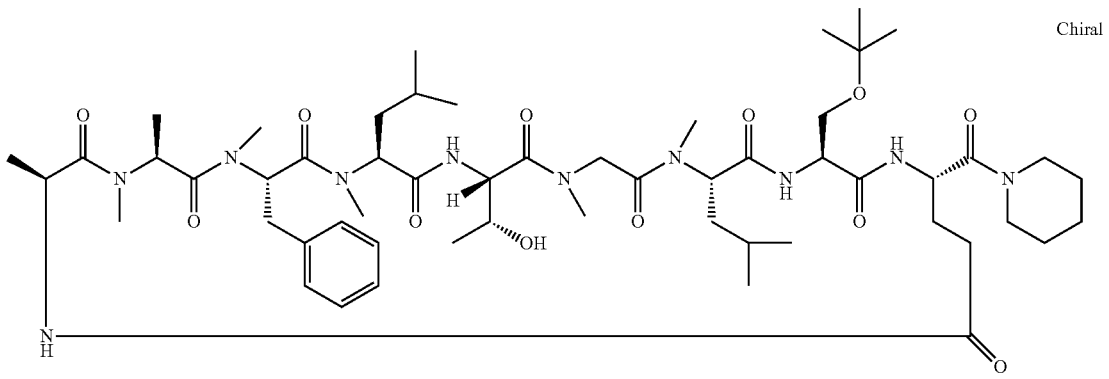

Compound P-121
Ala-MeAla-MePhe-MeLeu-Thr-MeGly-MeLeu-Ser(tBu)-Glu-piperidine
amide-cyclized at the N-terminal amine and the Glu side chain LCMS: 1082.0 m/z (M−H)−
Retention time: 0.73 min (analysis condition SQDAA50)

(SEQ ID NO: 226)

Chiral

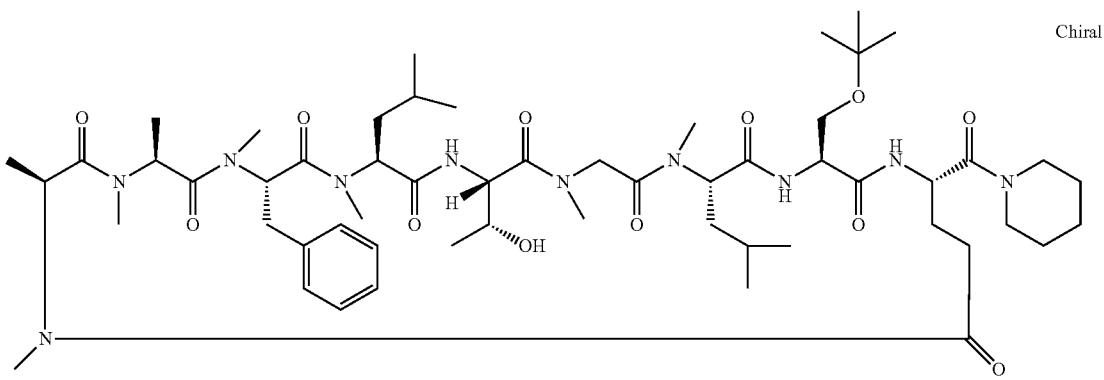

Compound P-122
MeAla-MeAla-MePhe-MeLeu-Thr-MeGly-MeLeu-Ser(tBu)-Glu-piperidine
amide-cyclized at the N-terminal amine and the Glu side chain LCMS: 1096.0 m/z (M−H)−
Retention time: 0.73 min (analysis condition SQDAA50)

(SEQ ID NO: 227)

Chiral

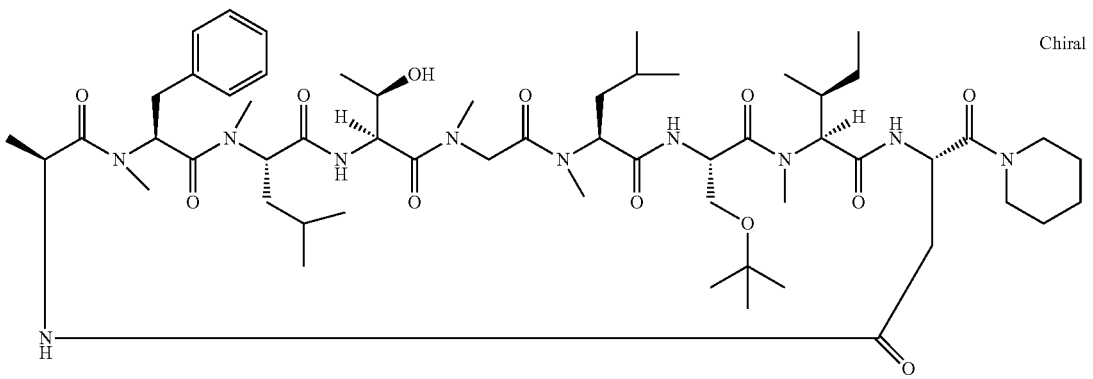

Compound P-123
Ala-MePhe-MeLeu-Thr-MeGly-MeLeu-Ser(tBu)-MeIle-Asp-piperidine
amide-cyclized at the N-terminal amine and the Asp side chain LCMS: 1110.0 m/z (M−H)−
Retention time: 0.82 min (analysis condition SQDAA50)

(SEQ ID NO: 228)

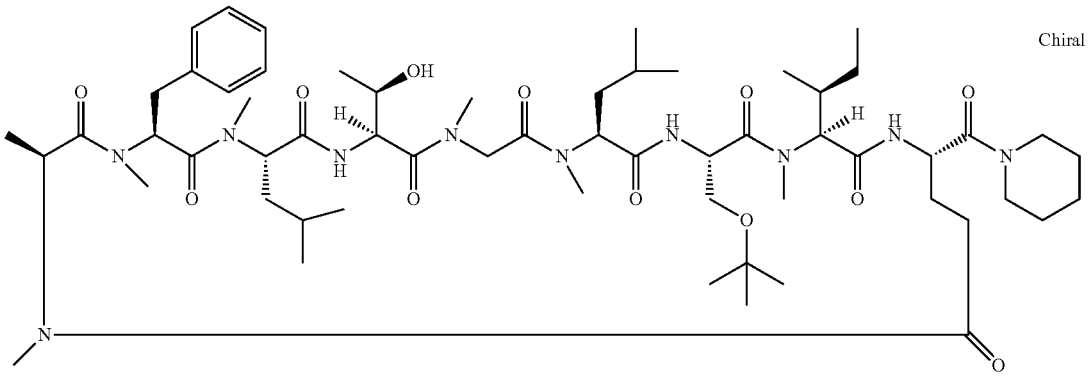

Compound P-124
MeAla-MePhe-MeLeu-Thr-MeGly-MeLeu-Ser(tBu)-MeIle-Glu-piperidine
amide-cyclized at the N-terminal amine and the Glu side chain LCMS: 1137.8 m/z (M−H)−
Retention time: 0.81 min (analysis condition SQDAA50)

(SEQ ID NO: 229)

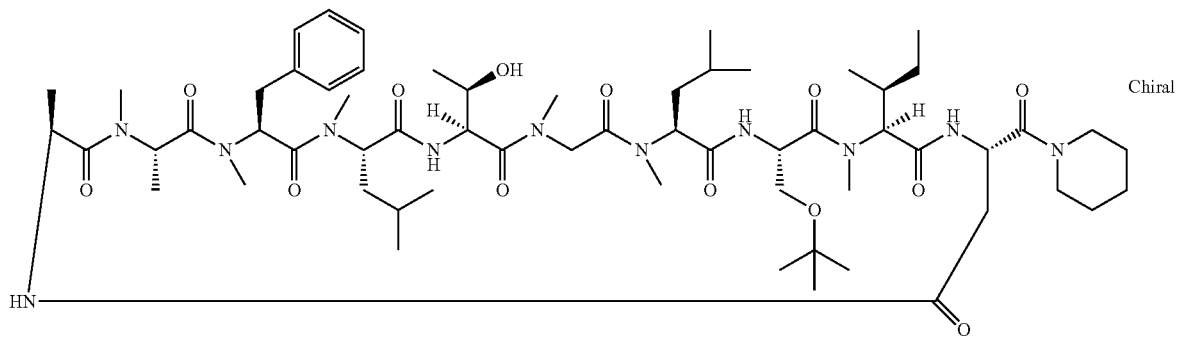

Ala-MeAla-MePhe-MeLeu-Thr-MeGly-MeLeu-Ser(tBu)-MeIle-Asp-piperidine amide-cyclized at the N-terminal amine and the Asp side chain
Compound P-125

LCMS: 1194.7 m/z (M−H)−
Retention time: 0.81 min (analysis condition SQDAA50)

[Example 18-2] Application of a Thioester-Cyclized Peptide to N-Terminal Amino Acid Removal by Enzymes and Amide Cyclization A peptide containing cysteine not located at the N-terminal and an amino acid having activated side chain carboxylic acid was translated to prepare a thioester-cyclized peptide having both functional groups reacted with each other. Next, the amino acid located on the N-terminal side of the cysteine was enzymatically removed to expose the α-amino group of the cysteine residue, and amide cyclization of the peptide using the α-amino group was attempted as follows.

1. Synthesis of tRNA (Lacking CA) by Transcription tRNAGluAAG (-CA) (SEQ ID NO: RT-E1) lacking 3′-end CA was synthesized from template DNA (SEQ ID NO: DT-E1) by in vitro transcription using RiboMAX Large Scale RNA production System T7 (Promega, P1300) and purified with RNeasy Mini kit (Qiagen).

```
SEQ ID NO: DT-E1
tRNAGluAAG (-CA) DNA sequence:
                                      (SEQ ID NO: 179)
GGCGTAATACGACTCACTATAGTCCCCTTCGTCTAGAGGCCCAGGACACC

GCCCTAAGACGGCGGTAACAGGGGTTCGAATCCCCTAGGGGACGC

SEQ ID NO: RT-E1
tRNAGluAAG (-CA) RNA sequence:
                                      (SEQ ID NO: 180)
GUCCCCUUCGUCUAGAGGCCCAGGACACCGCCCUAAGACGGCGGUAACAG

GGGUUCGAAUCCCCUAGGGGACGC
```

2. Synthesis of Aminoacylated tRNA (Compound AT-E1) by Ligation of Aminoacylated pdCpA Having Side Chain Carboxylic Acid Converted to Active Ester (Compound 1i-IA) and tRNA (Lacking CA) (SEQ ID NO: RT-E1)

2 μL of 10× ligation buffer (500 mM HEPES-KOH pH 7.5, 200 mM MgCl₂), 2 μL of 10 mM ATP and 2.8 μL of nuclease free water were added to 10 μL of 50 μM transcribed tRNAGluAAG (-CA) (SEQ ID NO: RT-E1). The mixture was heated at 95° C. for 2 minutes and then incubated at room temperature for 5 minutes to refold the tRNA. 1.2 µL of 20 units/µL T4 RNA ligase (New England Biolabs) and 2 µL of a 5 mM solution of aminoacylated pdCpA (Compound 1i-IA) in DMSO were added, and ligation reaction was carried out at 15° C. for 45 minutes. 4 µL of 3 M sodium acetate and 24 µL of 125 mM iodine (solution in water:THF=1:1) were added to 20 µL of the ligation reaction solution, and deprotection was carried out at room temperature for 1 hour. Aminoacylated tRNA (Compound AT-E1) was collected by phenol extraction and ethanol precipitation. Aminoacylated tRNA (Compound AT-E1) was dissolved in 1 mM sodium acetate immediately prior to addition to the translation mixture.

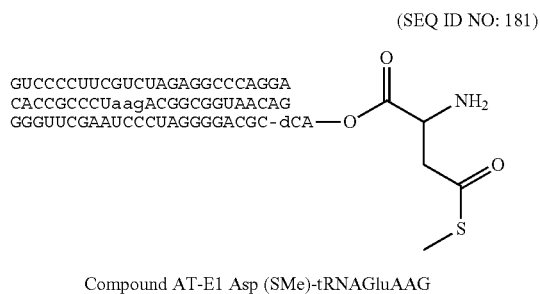

Compound AT-E1 Asp (SMe)-tRNAGluAAG

3. Translation Synthesis of a Peptide Containing a Cysteine Residue not Located at the N-Terminal and an Amino Acid Having Side Chain Carboxylic Acid Converted to Active Ester Translation synthesis of a desired unnatural amino acid-containing polypeptide was carried out by adding tRNA aminoacylated by an aspartic acid derivative having side chain carboxylic acid converted to active thioester to a cell-free translation system. The translation system used was PURE system, a prokaryote-derived reconstituted cell-free protein synthesis system. Specifically, the synthesis was carried out by adding 1 µM template RNA, 250 µM each of proteinogenic amino acids encoded by the respective template DNAs, and 50 µM aminoacylated tRNA having side chain carboxylic acid converted to active ester (Compound AT-E1) to a transcription and translation solution (1% (v/v) RNasein Ribonuclease inhibitor (Promega, N2111), 1 mM GTP, 1 mM ATP, 20 mM creatine phosphate, 50 mM HEPES-KOH pH 7.6, 100 mM potassium acetate, 6 mM magnesium acetate, 2 mM spermidine, 2 mM dithiothreitol, 0.1 mM 10-HCO—H4 folate, 1.5 mg/ml E. coli MRE600 (RNase-negative)-derived tRNA (Roche), 4 µg/ml creatine kinase, 3 µg/ml myokinase, 2 units/ml inorganic pyrophosphatase, 1.1 µg/ml nucleoside diphosphate kinase, 0.6 µM methionyl tRNA transformylase, 0.26 µM EF-G, 0.24 µM RF2, 0.17 µM RF3, 0.5 µM RRF, 2.7 µM IF1, 0.4 µM IF2, 1.5 µM IF3, 40 µM EF-Tu, 93 µM EF-Ts, 1.2 µM ribosome, 0.73 µM AlaRS, 0.03 µM ArgRS, 0.38 µM AsnRS, 0.13 µM AspRS, 0.02 µM CysRS, 0.06 µM GlnRS, 0.23 µM GluRS, 0.09 µM GlyRS, 0.4 µM IleRS, 0.04 µM LeuRS, 0.11 µM LysRS, 0.03 µM MetRS, 0.68 µM PheRS, 0.16 µM ProRS, 0.04 µM SerRS, 0.09 µM ThrRS, 0.03 µM TrpRS, 0.02 µM TyrRS, 0.02 µM ValRS (self-prepared proteins were basically prepared as His-tagged proteins)) and allowing the translation reaction mixture to stand at 37° C. for 1 hour.

The translational product was identified by measuring MALDI-MS spectra using α-cyano-4-hydroxycinnamic acid as the matrix.

Figure 62:
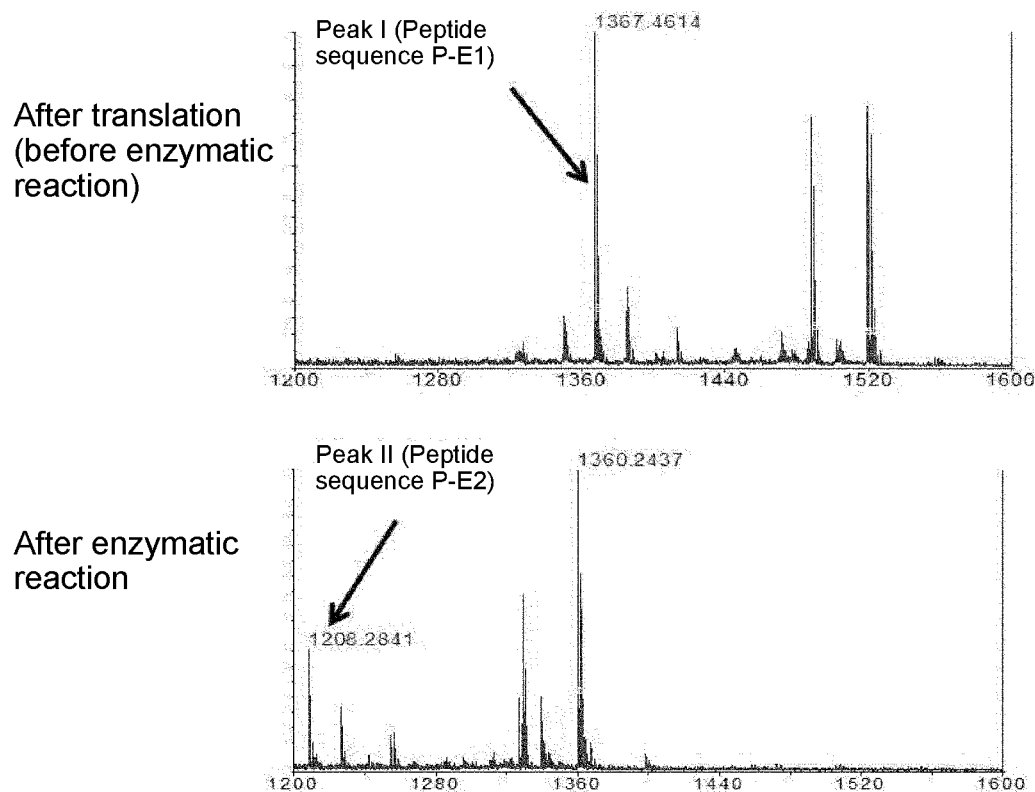
FIG. 62 is a diagram showing MALDI-MS analysis results of peptide P-E1 containing N-terminal formylmethionine and thioester-cyclized at the side chain thiol group and carboxylic acid (Peak I) and compound P-E2 amide-cyclized at the nitrogen atom of the N-terminal amino group exposed as a result of removing N-terminal formylmethionine and the side chain carboxylic acid of Asp (Peak II).

4. Translation Synthesis of a Thioester-Cyclized Peptide and its Conversion to an Amide-Cyclized Peptide Utilizing N-Terminal Amino Acid Removal Using Enzymes The aforementioned translation solution containing 1 µM template RNA OT43 RNA (SEQ ID NO: RM-E1) as well as 0.25 mM Met, 0.25 mM Cys, 0.25 mM Thr, 0.25 mM Arg, 0.25 mM Tyr, 0.25 mM Pro, 0.25 mM Gly and 50 µM Asp(SMe)-tRNAGluAAG (Compound AT-E1) was incubated at 37° C. for 60 minutes. 9 µL of 0.2% trifluoroacetic acid was added to 1 µL of the resulting translation solution. 1 µL of the resulting mixture was loaded on a MALDI target plate, and then blended with 1 µL of a CHCA solution (10 mg/ml α-cyano-4-hydroxycinnamic acid, 50% acetonitrile, 0.1% trifluoroacetic acid), dried on the plate and analyzed by MALDI-MS. As a result, a peak was observed corresponding to peptide P-E1 containing N-terminal formylmethionine and thioester-cyclized at the side chain thiol group and carboxylic acid (FIG. 62, peak I). Subsequently, enzymes peptide deformylase and methionine aminopeptidase were added to the above translation reaction product at 2 µM and 14 µM, respectively, as final concentrations, and incubated at 37° C. for 5 minutes. The resulting reaction product was analyzed by MALDI-MS as described above. As a result, the peak of the starting material thioester cyclic peptide was smaller, and a peak corresponding to Compound P-E2 was observed instead. It showed that the N-terminal formylmethionine of original cyclic peptide was removed and amide-cyclized at the nitrogen atom of the exposed N-terminal amino group and the side chain carboxylic acid of Asp (FIG. 62, peak II). This indicated that the intended amide-cyclized peptide is obtained by removing the N-terminal portion from Cys even after thioester cyclization has progressed.

```
SEQ ID NO: RM-E1
OT43 RNA
                                     (SEQ ID NO: 182)
GGGUUAACUUUAAGAAGGAGAUAUACAUaugUGCACUACAACGCGUCUUC CGUACCGUGGCGGCuaagcuucg Peptide sequence P-E1
                                     (SEQ ID NO: 183)
Compound thioester-cyclized at the side chain
sulfur atom of fMetCysThrThrThrArgAspProTyrArgGly
Gly and the side chain carboxylic acid of Asp
```

MALDI-MS:m/z: [M+H]+=1367.5 (Calc. 1367.6)
Peptide sequence P-E2 (SEQ ID NO: 184)
Compound amide-cyclized at the nitrogen atom of the N-terminal amino group of CysThrThrThrArgAspProTyrArgGlyGly and the side chain carboxylic acid of Asp
MALDI-MS:m/z: [M+H]+=1208.3 (Calc. 1208.6)

[Example 19] Peptide Compounds

1. Synthesis of Amide-Cyclized Peptides

The cyclized peptides shown below were synthesized (Table 11-1: examples of synthesized peptide compounds (965 compounds in total)). Unless otherwise clearly dictated, the amino acid located at 1 in a table corresponds to an intersection unit corresponding to the white circle "○" shown in the above Scheme A or the like, and the amino acid described on the left end in an amino acid sequence similarly corresponds to a ▲ unit. These two sites form a bond and constitutes a cyclic peptide. Amino acids indicated by H-1 to H-6 in a table correspond to a linear portion illustrated in the above Scheme A or the like. Here, the site present on the left end in a table forms the C-terminal. The pip as described here means that the C-terminal carboxylic acid forms an amide bond with piperidine to form piperidine amide. Cyclized peptides without any description in H-1 are intended to be compounds having the C-terminal carboxylic acid eliminated. In this case, one carboxylic acid possessed by the amino acid located at 1 and the N-terminal amine are cyclized by amidation reaction, and a derivative having the C-terminal carboxylic acid site eliminated, for example, replaced with a methyl group or a trifluoromethyl group, is located at the C-terminal. The abbreviations illustrated in Table 11-1 refer to amino acids described in Table 11-2 (a table showing relations between the amino acid abbreviations and the intended structures).

Cyclized peptides described in Table 11-1 were synthesized and the respective compounds were identified using the same methods as described above (Tables 11-3-1 and 11-3-2: Identification of synthesized peptide compounds (965 compounds in total)).

1-1. Synthetic Examples of C-Terminal Site Amino Acids or Peptides to be Bound to Resins and Methods for Supporting the Amino Acids or Peptides on the Resins The following amino acid- or peptide-supported resins were synthesized in order to synthesize various compounds that have main chain sites at the C-terminal sites chemically modified with amides (piperidine amides in many Examples) and that have side chain carboxylic acid sites of aspartic acids (intersection units) forming amide bonds with amino groups on the N-terminal sides (triangle units). The more detailed content of the synthetic examples will be described below. The synthesis methods are not limited to the following methods, and such peptides can also be synthesized by peptide synthesis methods described in other parts of the present specification or generally known.

1-1-1. Synthesis of a Compound Having Side Chain Carboxylic Acid of Fmoc-Asp-pip (Compound SP401) Bound to a Resin (Compound SP402)

Synthesis of tert-butyl (S)-3-((((9H-fluoren-9-yl)methoxy)carbonyl)amino)-4-oxo-4-(piperidin-1-yl)butanoate (Compound SP403, Fmoc-Asp(OtBu)-pip)

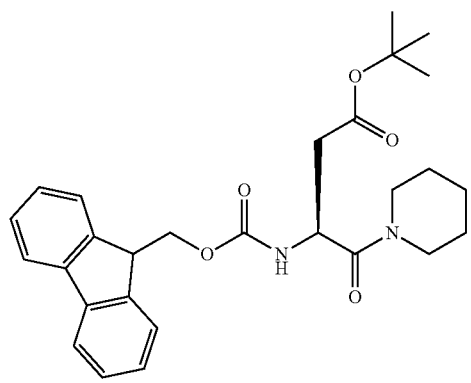 [SMILES: CC(C)(C)OC(=O)C[C@H](NC(=O)OCC1c2ccccc2-c2ccccc21)C(=O)N1CCCCC1]

(S)-2-((((9H-Fluoren-9-yl)methoxy)carbonyl)amino)-4-(tert-butoxy)-4-oxobutanoic acid (Compound SP404, Fmoc-Asp(OtBu)-OH) (30 g, 72.9 mmol) was dissolved in DMF (243 mL). N-methylmorpholine (9.6 ml, 87 mmol) and then O-(7-aza-1H-benzotriazol-1-yl)-N,N,N,N-tetramethyluronium hexafluorophosphate (HATU) (33.3 g, 87 mmol) were added at 0° C., and the mixture was stirred for 10 minutes. Piperidine (7.1 ml, 71.5 mmol) was further added dropwise, and the mixture was stirred for 30 minutes. The reaction mixture was diluted with hexane/ethyl acetate=1/1 (1500 ml), and the organic layer was sequentially washed with a saturated aqueous ammonium chloride solution, a saturated aqueous sodium bicarbonate solution, water and brine. The organic extract was dried over sodium sulfate and then concentrated under reduced pressure, and the resulting residue was purified by silica gel column chromatography (hexane/ethyl acetate=2/1) to afford tert-butyl (S)-3-((((9H-fluoren-9-yl)methoxy)carbonyl)amino)-4-oxo-4-(piperidin-1-yl)butanoate (Compound SP403) (35.2 g, 99%).

LCMS (ESI) m/z=479.5 (M+H)+

Retention time: 1.10 min (analysis condition SQDAA05)

Synthesis of (S)-3-((((9H-fluoren-9-yl)methoxy)carbonyl)amino)-4-oxo-4-(piperidin-1-yl)butanoic Acid (Fmoc-Asp-pip, Compound SP401)

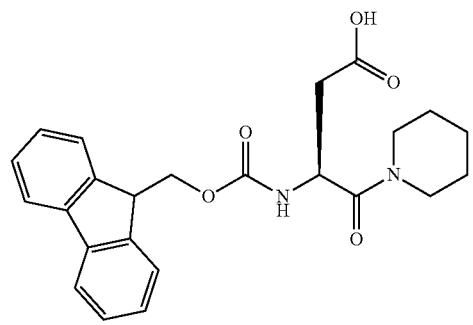 [SMILES: O=C(O)C[C@H](NC(=O)OCC1c2ccccc2-c2ccccc21)C(=O)N1CCCCC1]

Tert-butyl (S)-3-((((9H-fluoren-9-yl)methoxy)carbonyl)amino)-4-oxo-4-(piperidin-1-yl)butanoate (Compound SP403) (9.3 g, 19.4 mmol) was dissolved in toluene (300 mL), and the mixture was concentrated under reduced pressure. This operation was further repeated twice, and the residue was dried under reduced pressure overnight. Dehydrated dichloromethane (8.6 ml) was placed in the reaction vessel, and the mixture was stirred at 0° C. for 5 minutes under a nitrogen atmosphere, followed by dropwise addition of trifluoroacetic acid (8.6 ml, 116 mmol). After stirring at room temperature for 4 hours, triethylamine (16.2 ml, 116 mmol) was added dropwise at 0° C. The reaction mixture was diluted with dichloromethane (100 ml), and the organic layer was washed with a 5% aqueous sodium dihydrogenphosphate solution six times. The organic extract was dried over sodium sulfate and then concentrated under reduced pressure. The resulting residue was diluted again with dichloromethane (100 ml), and the organic layer was washed with a 5% aqueous sodium dihydrogenphosphate solution twice. The organic extract was dried over sodium sulfate and then concentrated under reduced pressure to afford (S)-3-((((9H-fluoren-9-yl)methoxy)carbonyl)amino)-4-oxo-4-(piperidin-1-yl)butanoic acid (Fmoc-Asp-pip, Compound SP401) (7.8 g, 96%). This compound was used in the next step without further purification.

LCMS (ESI) m/z=423 (M+H)+

Retention time: 0.88 min (analysis condition SQDAA05)

Synthesis of (S)-3-((((9H-fluoren-9-yl)methoxy) carbonyl)amino)-4-oxo-4-(piperidin-1-yl)butanoic acid-2-chlorotrityl Resin (Compound SP402, Fmoc-Asp(O-Trt(2-Cl)-Resin)-pip)

In the present specification, when a polymer or resin is bound to a compound, the polymer or resin site may be described as "○". The chemical structure of the reaction site may be described as connected to "○" in order to clarify the reaction point of the resin site. The following structure illustrates a state where the 2-chlorotrityl group of the resin is bound to the side chain carboxylic acid of Asp through an ester bond.

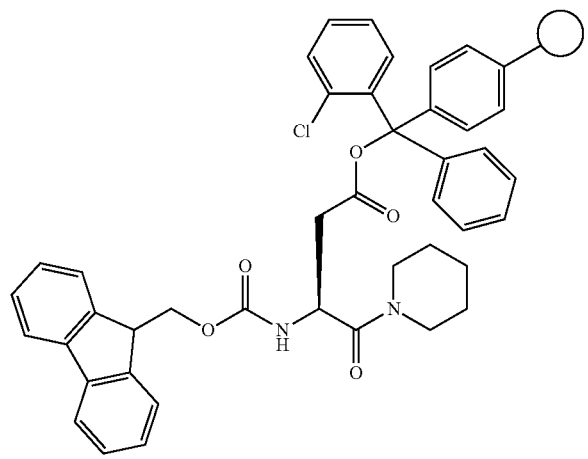 [SMILES: Cc1ccc(C(OC(=O)C[C@H](NC(=O)OCC2c3ccccc3-c3ccccc32)C(=O)N2CCCCC2)(c2ccccc2)c2ccccc2Cl)cc1]

2-Chlorotrityl chloride resin (100-200 mesh, 1% DVB, purchased from Chem-Impex, 29.6 g, 33.4 mmol) and dehydrated dichloromethane (300 ml) were placed in a reaction vessel equipped with a filter, and the vessel was shaken at room temperature for 10 minutes. Dichloromethane was removed by applying nitrogen pressure, after which dehydrated methanol (5.4 ml) and diisopropylethylamine (14 ml) were added to a solution of (S)-3-((((9H-fluoren-9-yl)methoxy)carbonyl)amino)-4-oxo-4-(piperidin-1-yl)butanoic acid (Compound SP401) (7.8 g) in dehydrated dichloromethane (334 ml), the mixture was added to the reaction vessel, and the vessel was shaken for 10 minutes. The reaction solution was removed by applying nitrogen pressure, after which dehydrated methanol (41.6 ml) and diisopropylethylamine (14 ml) were added to dehydrated dichloromethane (334 ml), the mixture was added to the reaction vessel, and the vessel was shaken for 90 minutes. The reaction solution was removed by applying nitrogen pressure, after which dichloromethane (300 ml) was placed and the vessel was shaken for 5 minutes. The reaction solution was removed by applying nitrogen pressure, after which dichloromethane (300 ml) was placed again and the vessel was shaken for 5 minutes. The reaction solution was removed by applying nitrogen pressure, after which the resin was dried under reduced pressure overnight to afford (S)-3-((((9H-fluoren-9-yl)methoxy)carbonyl)amino)-4-oxo-4-(piperidin-1-yl)butanoic acid-2-chlorotrityl resin (Compound SP402) (34.8 g).

The resulting (S)-3-((((9H-fluoren-9-yl)methoxy)carbonyl)amino)-4-oxo-4-(piperidin-1-yl)butanoic acid-2-chlorotrityl resin (Compound SP402) (13.42 mg) was placed in a reaction vessel, DMF (0.2 ml) and piperidine (0.2 ml) were added, and the vessel was shaken at room temperature for 1 hour. After adding DMF (1.6 ml) to the reaction vessel, the reaction mixture (0.4 ml) was diluted with DMF (9.6 ml), and its absorbance (301.2 nm) was measured. The loading rate of (S)-3-((((9H-fluoren-9-yl)methoxy)carbonyl)amino)-4-oxo-4-(piperidin-1-yl)butanoic acid-2-chlorotrityl resin (Compound SP402) was calculated to be 27.8%, 0.267 mmol/g from the following calculation formula.

(Absorbance (301.2 nm)×1000×50)/(13.42×7800)
=0.267 mmol/g 0.267 mmol/g×100/(33.4/34.8)=27.8%

1-1-2. Synthesis of a Compound Having Side Chain Carboxylic Acid of Asp of Fmoc-Asp-MePhe-Ala-pip (Compound SP454) Bound to a Resin (Compound SP455) and Synthesis of a Compound Having Side Chain Carboxylic Acid of Asp of Fmoc-Asp-MePhe-MePhe-Ala-pip (Compound SP458) (SEQ ID NO: 320) Bound to a Resin (Compound SP459)

(3S)-3-(9H-fluoren-9-ylmethoxycarbonylamino)-4-[methyl-[(2S)-1-oxo-1-[[(2S)-1-oxo-1-piperidin-1-ylpropan-2-yl]amino]-3-phenylpropan-2-yl]amino]-4-oxobutanoic acid-2-chlorotrityl resin (Compound SP455, Fmoc-Asp(O-Trt(2-Cl)-Resin)-MePhe-Ala-pip) was synthesized according to the following scheme.

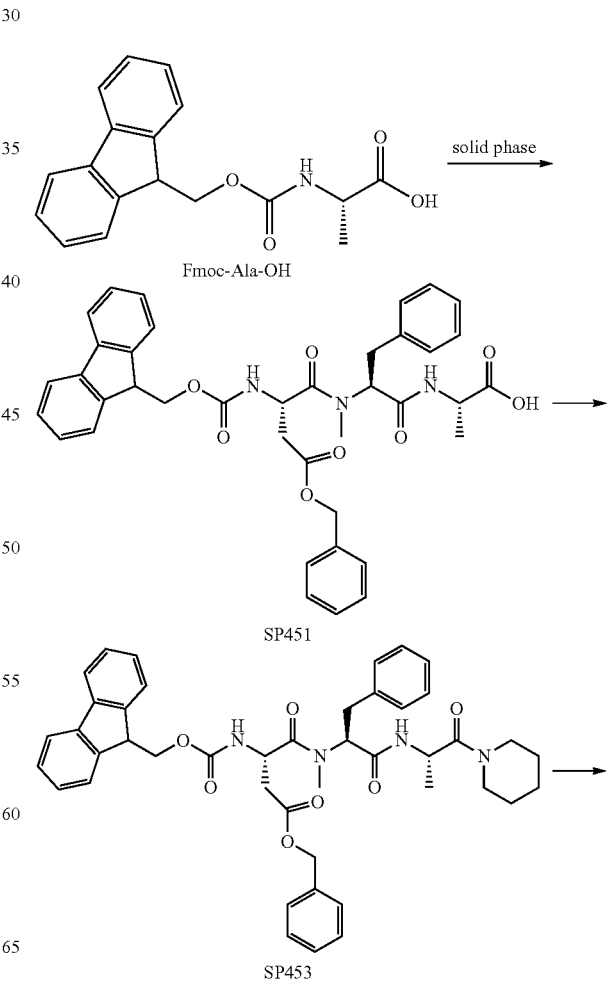

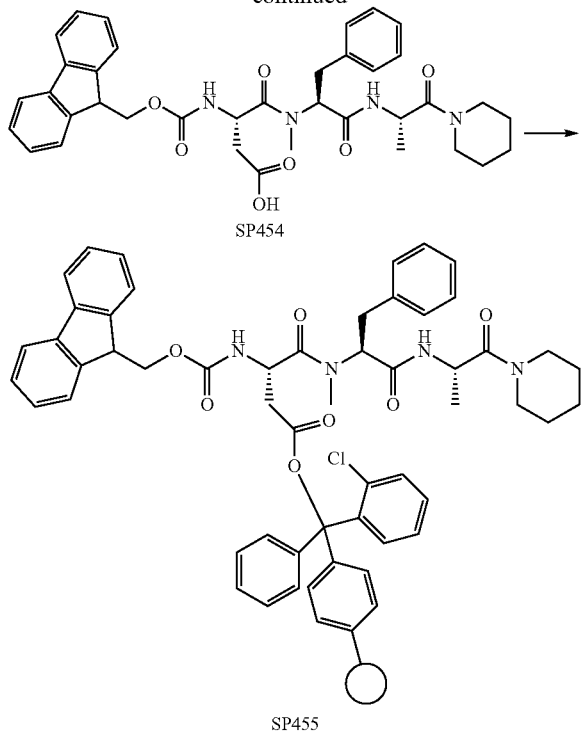

Synthesis of (2S)-2-[[(2S)-2-[[(2S)-2-(9H-fluoren-9-ylmethoxycarbonylamino)-4-oxo-4-phenylmethoxybutanoyl]-methylamino]-3-phenylpropanoyl]amino]propanoic Acid (Compound SP451, Fmoc-Asp(OBn)-MePhe-Ala-OH)

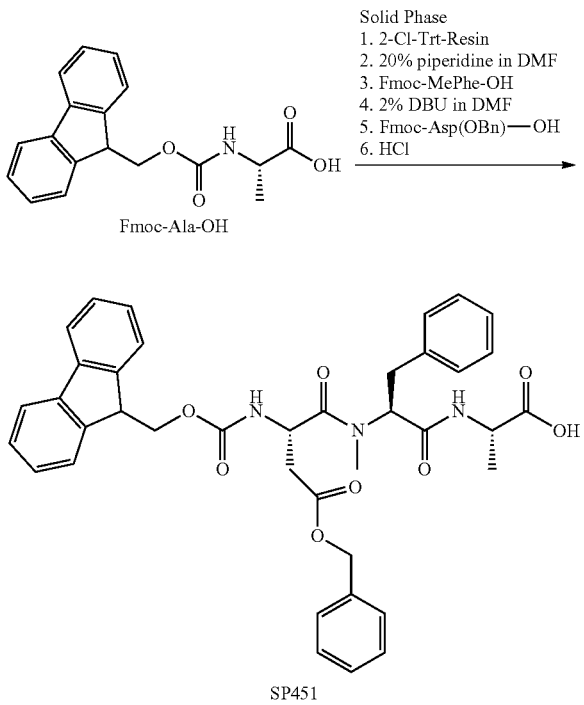

(2S)-2-(9H-fluoren-9-ylmethoxycarbonylamino)propanoic acid (Fmoc-Ala-OH) (4.86 g, 15.8 mmol) and diisopropylethylamine (EtN(iPr)$_2$) (14.5 mL, 83 mmol) were dissolved in dehydrated dichloromethane (60 ml), 2-chlorotrityl chloride resin (100-200 mesh, 1% DVB, purchased from Watanabe Chemical Industries, 6.5 g, 10.5 mmol) was added, and the amino acid was supported on the resin by shaking at room temperature for 90 minutes. The reaction solution was removed, and the resin was washed with dehydrated dichloromethane (100 ml) four times. A 20% solution of piperidine in N,N-dimethylformamide (52 ml) was added to the resin, and the Fmoc group was deprotected by shaking for 60 minutes. The reaction solution was removed, and the resin was washed with N,N-dimethylformamide (45 ml) three times. Subsequently, (2S)-2-[9H-fluoren-9-ylmethoxycarbonyl(methyl)amino]-3-phenylpropanoic acid (Fmoc-MePhe-OH) (3.74 g, 9.3 mmol), 3H-(1,2,3)triazolo(4,5-b)pyridin-3-ol (HOAt) (1.27 g, 9.3 mmol) and N,N'-methanediylidenebis(propan-2-amine) (DIC) (1.44 ml, 9.3 mmol) were dissolved in N,N-dimethylformamide (13.5 ml), the solution was added to the resin, and peptidation was carried out by shaking at room temperature for 90 minutes. The reaction solution was removed, and the resin was washed with N,N-dimethylformamide (23 ml) three times and then further washed with dichloromethane (23 ml) three times. Subsequently, a 2% solution of 2,3,4,6,7,8,9,10-octahydropyrimido[1,2-a]azepine in N,N-dimethylformamide (2% DBU in DMF) (40 ml) was added to the aforementioned resin, and the Fmoc group was deprotected by shaking for 180 minutes. The reaction solution was removed, and the resin was washed with N,N-dimethylformamide (45 ml) three times. Subsequently, (2S)-2-(9H-fluoren-9-ylmethoxycarbonylamino)-4-oxo-4-phenylmethoxybutanoic acid (Fmoc-Asp(OBn)-OH) (5.14 g, 11.5 mmol), 3H-(1,2,3)triazolo(4,5-b)pyridin-3-ol (HOAt) (1.58 g, 11.6 mmol) and N,N'-methanediylidenebis(propan-2-amine) (DIC) (1.78 ml, 211.6 mmol) were dissolved in N,N-dimethylformamide (30 ml), the solution was added to the resin, and peptidation was carried out by shaking at room temperature for 16 hours. The reaction solution was removed, and the resin was washed with N,N-dimethylformamide (45 ml) three times and then further washed with dichloromethane (45 ml) three times. Subsequently, a 4 N solution of hydrochloric acid in ethyl acetate (1.92 ml, 7.69 mmol) was mixed with dichloromethane (100 ml), the resulting solution was added to the aforementioned resin, and the amino acid was cleaved from the resin by performing one-hour shaking twice. The resin was washed with dichloromethane/2,2,2-trifluoroethanol (=1/1, v/v, 25 mL) twice, after which all extracts were combined and concentrated under reduced pressure to afford Fmoc-Asp(OBn)-MePhe-Ala-OH (Compound SP451) (7.11 g).

LCMS (ESI) m/z=678.6 (M+H)+
Retention time: 0.65 min (analysis condition SQDAA50)

251

Synthesis of Benzyl (3S)-3-(9H-fluoren-9-yl-methoxycarbonylamino)-4-[methyl-[(2S)-1-oxo-1-[[(2S)-1-oxo-1-piperidin-1-ylpropan-2-yl]amino]-3-phenylpropan-2-yl]amino]-4-oxobutanoate (Compound SP453, Fmoc-Asp(OBn)-MePhe-Ala-pip)

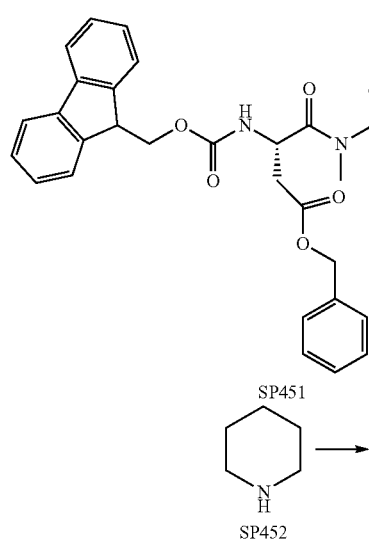

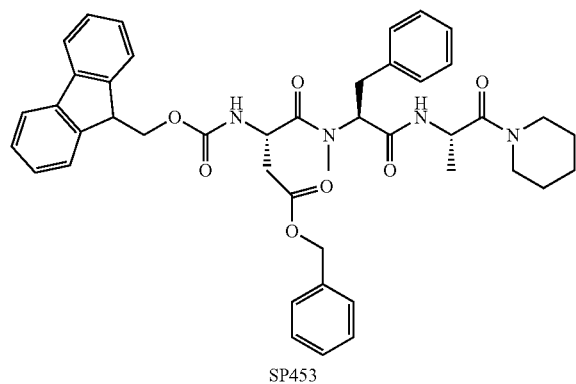

Fmoc-Asp(OBn)-MePhe-Ala-OH (Compound SP451) (7.11 g, 10.5 mmol), diisopropylethylamine (EtN(iPr) 2) (3.29 ml, 18.9 mmol) and O-(7-aza-1H-benzotriazol-1-yl)-N,N,N',N'-tetramethyluronium hexafluorophosphate (HATU) (5.19 g, 13.6 mmol) were dissolved in N,N-dimethylformamide (40 ml) under a nitrogen atmosphere, piperidine (Compound SP452) (0.99 ml, 10.0 mmol) was added and the mixture was stirred at room temperature for 10 minutes. 150 ml of ethyl acetate was added to the reaction solution, and the organic layer was washed with 150 ml of a saturated aqueous ammonium chloride solution, 150 ml of pure water and 150 ml of brine. The organic layer was collected and concentrated under reduced pressure to afford Fmoc-Asp(OBn)-MePhe-Ala-pip (Compound SP453) (7.44 g, 95%).

LCMS (ESI) m/z=745.7 (M+H)+

Retention time: 0.82 min (analysis condition SQDAA50)

252

Synthesis of (3S)-3-(9H-fluoren-9-ylmethoxycarbonylamino)-4-[methyl-[(2S)-1-oxo-1-[[(2S)-1-oxo-1-piperidin-1-ylpropan-2-yl]amino]-3-phenylpropan-2-yl]amino]-4-oxobutanoic Acid (Compound SP454, Fmoc-Asp-MePhe-Ala-pip)

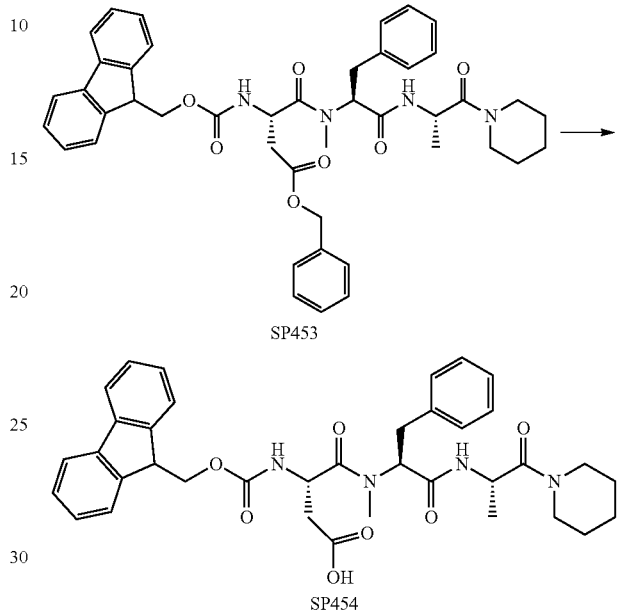

Fmoc-Asp(OBn)-MePhe-Ala-pip (Compound SP453) (7.44 g, 10.0 mmol) and 20% palladium on active carbon (1.49 g, 2.8 mmol) were added to methanol (50 ml) under a nitrogen atmosphere, the atmosphere in the reaction vessel was replaced with hydrogen gas, and the mixture was stirred at room temperature for 5 hours. The reaction solution was filtered through celite, and the organic layer was concentrated under reduced pressure to afford Fmoc-Asp-MePhe-Ala-pip (Compound SP454) (5.69 g, 86%).

LCMS (ESI) m/z=655.6 (M+H)+

Retention time: 0.61 min (analysis condition SQDAA50)

Synthesis of (3S)-3-(9H-fluoren-9-ylmethoxycarbonylamino)-4-[methyl-[(2S)-1-oxo-1-[[(2S)-1-oxo-1-piperidin-1-ylpropan-2-yl]amino]-3-phenylpropan-2-yl]amino]-4-oxobutanoic acid-2-chlorotrityl Resin (Compound SP455, Fmoc-Asp(O-Trt(2-Cl)-Resin)-MePhe-Ala-pip)

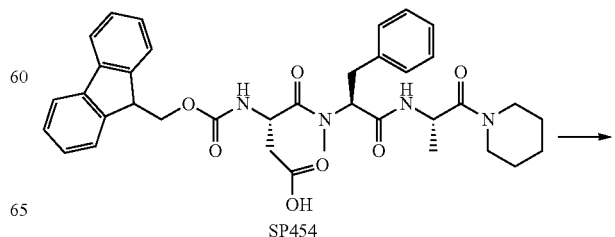

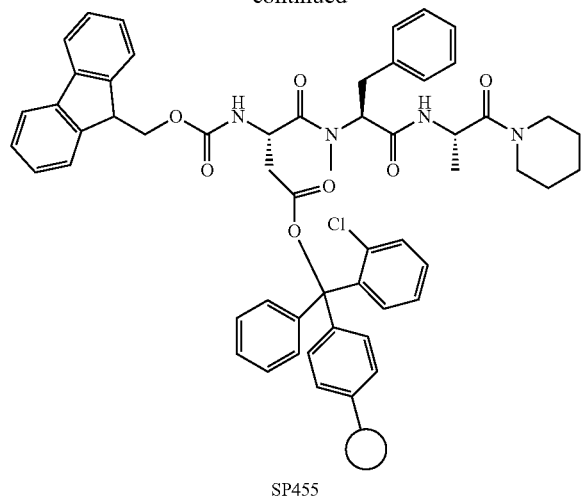

SP455

2-Chlorotrityl chloride resin (100-200 mesh, 1% DVB, purchased from Watanabe Chemical Industries, 10.8 g, 17.2 mmol) and dehydrated dichloromethane (100 ml) were placed in a reaction vessel equipped with a filter, and the vessel was shaken at room temperature for 10 minutes. Dichloromethane was removed by applying nitrogen pressure, after which dehydrated methanol (1.4 ml) and diisopropylethylamine (EtN(iPr) 2) (7.2 ml, 41.3 mmol) were added to a solution of Fmoc-Asp-MePhe-Ala-pip (Compound SP454) (5.64 g, 8.61 mmol) in dehydrated dichloromethane (100 ml), the mixture was added to the reaction vessel, and the vessel was shaken for 40 minutes. The reaction solution was removed by applying nitrogen pressure, after which dehydrated methanol (22.4 ml) and diisopropylethylamine (EtN(iPr) 2) (7.2 ml, 41.3 mmol) were added to dichloromethane (100 ml), the mixture was added to the reaction vessel, and the vessel was shaken for 2 hours. The reaction solution was removed by applying nitrogen pressure, after which dichloromethane (100 ml) was placed and the vessel was shaken for 5 minutes. The reaction solution was removed by applying nitrogen pressure, after which dichloromethane (100 ml) was placed again and the vessel was shaken for 5 minutes. The reaction solution was removed by applying nitrogen pressure, after which the resin was dried under reduced pressure overnight to afford Fmoc-Asp(O-Trt(2-Cl)-Resin)-MePhe-Ala-pip (Compound SP455) (14.0 g).

Loading rate: 0.317 mmol/g, 25.7%

(3S)-3-(9H-fluoren-9-ylmethoxycarbonylamino)-4-[methyl-[(2S)-1-[methyl-[(2S)-1-oxo-1-[[(2S)-1-oxo-1-piperidin-1-ylpropan-2-yl]amino]-3-phenylpropan-2-yl]amino]-1-oxo-3-phenylpropan-2-yl]amino]-4-oxobutanoic acid-2-chlorotrityl resin (Compound SP459, Fmoc-Asp(O-Trt(2-Cl)-Resin)-MePhe-MePhe-Ala-pip) (SEQ ID NO: 321) was synthesized according to the following scheme.

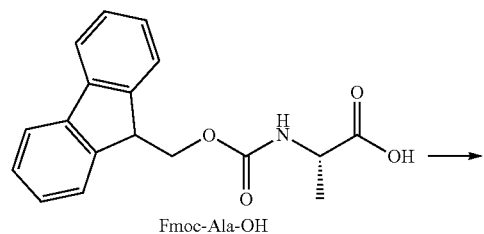

Fmoc-Ala-OH

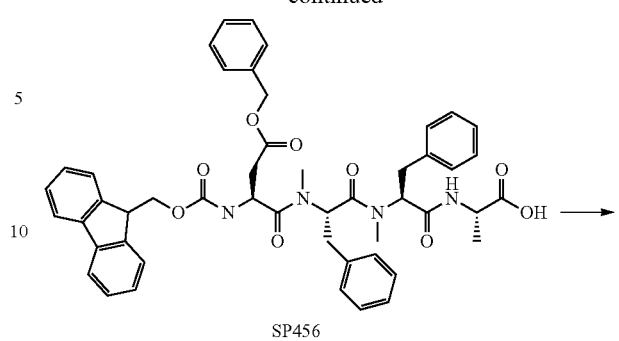

SP456

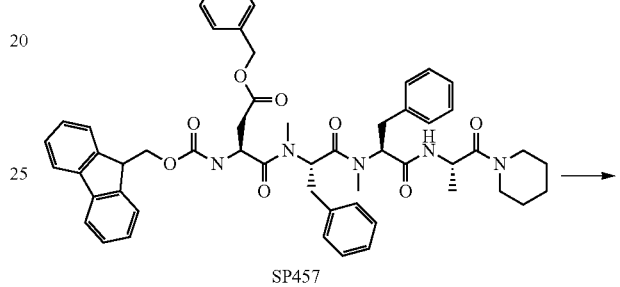

SP457

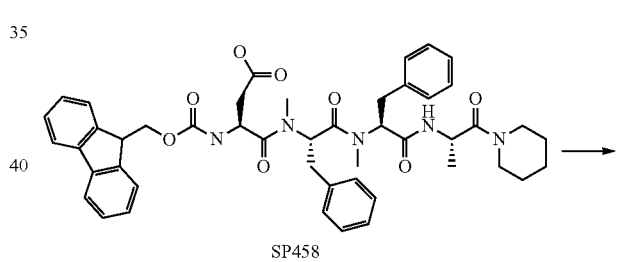

SP458

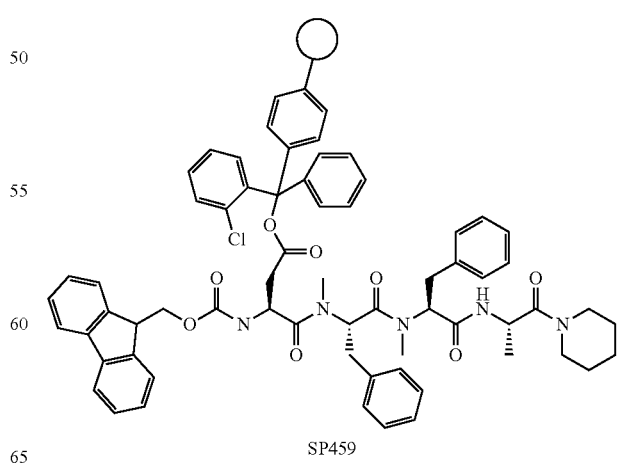

SP459

Synthesis of (2S)-2-[[(2S)-2-[[(2S)-2-[[(2S)-2-(9H-fluoren-9-ylmethoxycarbonylamino)-4-oxo-4-phenylmethoxybutanoyl]-methylamino]-3-phenylpropanoyl]-methylamino]-3-phenylpropanoyl]amino] propanoic Acid (Compound SP456, Fmoc-Asp(OBn)-MePhe-MePhe-Ala-OH) (SEQ ID NO: 230)

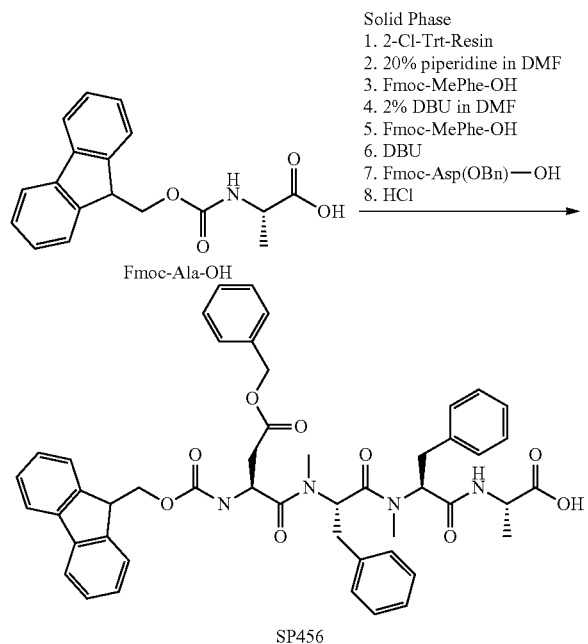

Solid Phase
1. 2-Cl-Trt-Resin
2. 20% piperidine in DMF
3. Fmoc-MePhe-OH
4. 2% DBU in DMF
5. Fmoc-MePhe-OH
6. DBU
7. Fmoc-Asp(OBn)—OH
8. HCl (2S)-2-(9H-fluoren-9-ylmethoxycarbonylamino)propanoic acid (Fmoc-Ala-OH) (4.86 g, 15.8 mmol) and diisopropylethylamine (EtN(iPr)$_2$) (14.5 mL, 83 mmol) were dissolved in dehydrated dichloromethane (60 ml), 2-chlorotrityl chloride resin (100-200 mesh, 1% DVB, purchased from Watanabe Chemical Industries, 6.5 g, 10.5 mmol) was added, and the amino acid was supported on the resin by shaking at room temperature for 90 minutes. The reaction solution was removed, and the resin was washed with dichloromethane (100 ml) four times. A 20% solution of piperidine in N,N-dimethylformamide (52 ml) was added to the resin, and the Fmoc group was deprotected by shaking for 60 minutes. The reaction solution was removed, and the resin was washed with N,N-dimethylformamide (45 ml) three times. Subsequently, (2S)-2-[9H-fluoren-9-ylmethoxycarbonyl(methyl)amino]-3-phenylpropanoic acid (Fmoc-MePhe-OH) (3.74 g, 9.3 mmol), 3H-(1,2,3)triazolo(4,5-b)pyridin-3-ol (HOAt) (1.27 g, 9.3 mmol) and N,N'-methanediylidenebis(propan-2-amine) (DIC) (1.44 ml, 9.3 mmol) were dissolved in N,N-dimethylformamide (13.5 ml), the solution was added to the resin, and peptidation was carried out by shaking at room temperature for 90 minutes. The reaction solution was removed, and the resin was washed with N,N-dimethylformamide (23 ml) three times and then further washed with dichloromethane (23 ml) three times. Subsequently, a 2% solution of 2,3,4,6,7,8,9,10-octahydropyrimido[1,2-a]azepine in N,N-dimethylformamide (2% DBU in DMF) (40 ml) was added to the resin, and the Fmoc group was deprotected by shaking for 60 minutes. The reaction solution was removed, and the resin was washed with N,N-dimethylformamide (45 ml) three times. Subsequently, (2S)-2-[9H-fluoren-9-ylmethoxycarbonyl(methyl)amino]-3-phenylpropanoic acid (Fmoc-MePhe-OH) (4.61 g, 11.5 mmol), 3H-(1,2,3)triazolo(4,5-b)pyridin-3-ol (HOAt) (1.58 g, 11.6 mmol) and N,N'-methanediylidenebis(propan-2-amine) (DIC) (1.78 ml, 11.6 mmol) were dissolved in N,N-dimethylformamide (30 ml), the solution was added to the resin, and peptidation was carried out by shaking at room temperature for 16 hours. The reaction solution was removed, and the resin was washed with N,N-dimethylformamide (45 ml) three times and then further washed with dichloromethane (45 ml) three times. Subsequently, a 2% solution of 2,3,4,6,7,8,9,10-octahydropyrimido[1,2-a]azepine in N,N-dimethylformamide (2% DBU in DMF) (40 ml) was added to the resin, and the Fmoc group was deprotected by shaking for 60 minutes. The reaction solution was removed, and the resin was washed with N,N-dimethylformamide (45 ml) three times. Subsequently, (2S)-2-(9H-fluoren-9-ylmethoxycarbonylamino)-4-oxo-4-phenylmethoxybutanoic acid (Fmoc-Asp(OBn)-OH) (5.14 g, 11.5 mmol), 3H-(1,2,3)triazolo(4,5-b)pyridin-3-ol (HOAt) (1.58 g, 11.6 mmol) and N,N'-methanediylidenebis(propan-2-amine) (DIC) (1.78 ml, 11.6 mmol) were dissolved in N,N-dimethylformamide (30 ml), the solution was added to the resin, and peptidation was carried out by shaking at room temperature for 16 hours. The reaction solution was removed, and the resin was washed with N,N-dimethylformamide (45 ml) three times and then further washed with dichloromethane (45 ml) three times. Subsequently, a 4 N solution of hydrochloric acid in ethyl acetate (1.92 ml, 7.69 mmol) was mixed with dichloromethane (100 ml), the resulting solution was added to the aforementioned resin, and the amino acid was cleaved from the resin by performing one-hour shaking twice. The resin was washed with dichloromethane/2,2,2-trifluoroethanol (=1/1, v/v, 25 mL) twice, after which all extracts were combined and concentrated under reduced pressure to afford Fmoc-Asp(OBn)-MePhe-MePhe-Ala-OH (Compound SP456) (SEQ ID NO: 230) (7.81 g).

LCMS (ESI) m/z=839.6 (M+H)+

Retention time: 0.71 min (analysis condition SQDAA50)

Synthesis of Benzyl (3S)-3-(9H-fluoren-9-ylmethoxycarbonylamino)-4-[methyl-[(2S)-1-[methyl-[(2S)-1-oxo-1-[[(2S)-1-oxo-1-piperidin-1-ylpropan-2-yl]amino]-3-phenylpropan-2-yl]amino]-1-oxo-3-phenylpropan-2-yl]amino]-4-oxobutanoate (Compound SP457, Fmoc-Asp(OBn)-MePhe-MePhe-Ala-pip) (SEQ ID NO: 322)

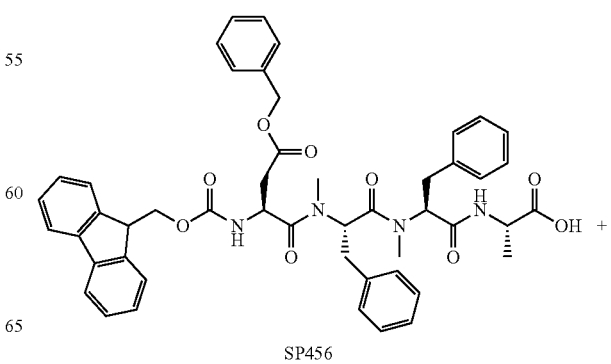

-continued

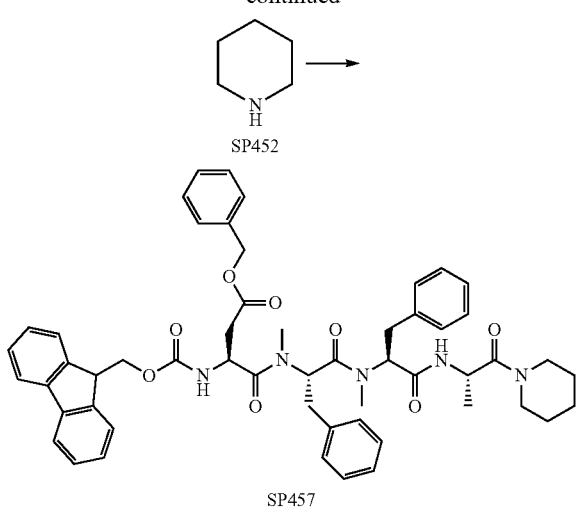

SP452

SP457

Fmoc-Asp(OBn)-MePhe-MePhe-Ala-OH (Compound SP456) (SEQ ID NO: 230) (7.81 g, 9.70 mmol), diisopropylethylamine (EtN(iPr) 2) (3.04 ml, 17.5 mmol) and O-(7-aza-1H-benzotriazol-1-yl)-N,N,N',N'-tetramethyluronium hexafluorophosphate (HATU) (4.80 g, 12.6 mmol) were dissolved in N,N-dimethylformamide (40 ml) under a nitrogen atmosphere, piperidine (Compound SP452) (0.94 ml, 9.51 mmol) was added and the mixture was stirred at room temperature for 15 minutes. 150 ml of ethyl acetate was added to the reaction solution, and the organic layer was washed with 150 ml of a saturated aqueous ammonium chloride solution, 150 ml of pure water and 150 ml of brine. The organic layer was collected and concentrated under reduced pressure to afford Fmoc-Asp(OBn)-MePhe-MePhe-Ala-pip (Compound SP457) (SEQ ID NO: 322) (8.06 g, 92%).

LCMS (ESI) m/z=906.7 (M+H)+

Retention time: 0.87 min (analysis condition SQDAA50)

Synthesis of (3S)-3-(9H-fluoren-9-ylmethoxycarbonylamino)-4-[methyl-[(2S)-1-[methyl-[(2S)-1-oxo-1-[[(2S)-1-oxo-1-piperidin-1-ylpropan-2-yl]amino]-3-phenylpropan-2-yl]amino]-1-oxo-3-phenylpropan-2-yl]amino]-4-oxobutanoic Acid (Compound SP458, Fmoc-Asp-MePhe-MePhe-Ala-pip) (SEQ ID NO: 320)

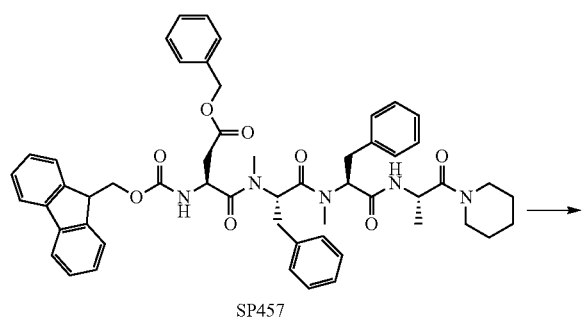

SP457

-continued

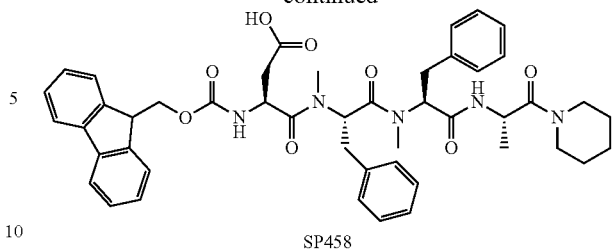

SP458

Fmoc-Asp(OBn)-MePhe-MePhe-Ala-pip (Compound SP457) (SEQ ID NO: 322) (8.06 g, 8.90 mmol) and 20% palladium on active carbon (1.61 g, 3.0 mmol) were added to methanol (50 ml) under a nitrogen atmosphere, the atmosphere in the reaction vessel was replaced with hydrogen gas, and the mixture was stirred at room temperature for 5 hours. The reaction solution was filtered through celite, and the organic layer was concentrated under reduced pressure to afford Fmoc-Asp-MePhe-MePhe-Ala-pip (Compound SP458) (SEQ ID NO: 320) (4.79 g, 66%).

LCMS (ESI) m/z=816.7 (M+H)+

Retention time: 0.69 min (analysis condition SQDAA50)

Synthesis of (3S)-3-(9H-fluoren-9-ylmethoxycarbonylamino)-4-[methyl-[(2S)-1-[methyl-[(2S)-1-oxo-1-[[(2S)-1-oxo-1-piperidin-1-ylpropan-2-yl]amino]-3-phenylpropan-2-yl]amino]-1-oxo-3-phenylpropan-2-yl]amino]-4-oxobutanoic acid-2-chlorotrityl Resin (Compound SP459, Fmoc-Asp(O-Trt(2-Cl)-Resin)-MePhe-MePhe-Ala-pip) (SEQ ID NO: 321)

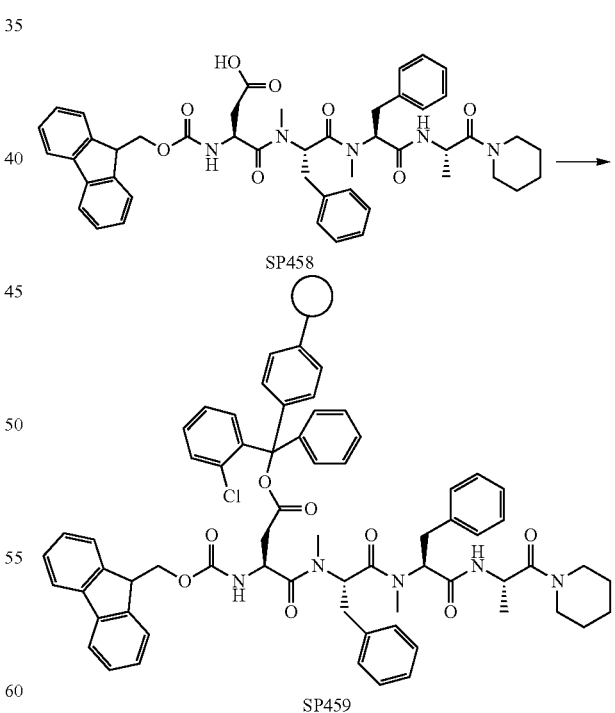

2-Chlorotrityl chloride resin (100-200 mesh, 1% DVB, purchased from Watanabe Chemical Industries, 6.69 g, 11.7 mmol) and dehydrated dichloromethane (50 ml) were placed in a reaction vessel equipped with a filter, and the vessel was shaken at room temperature for 10 minutes. Dichloromethane was removed by applying nitrogen pressure, after which dehydrated methanol (0.95 ml) and diisopropylethylamine (EtN(iPr)$_2$) (4.91 ml, 28.2 mmol) were added to a solution of Fmoc-Asp-MePhe-MePhe-Ala-pip (Compound SP458) (SEQ ID NO: 320) (4.79 g, 5.87 mmol) in dehydrated dichloromethane (100 ml), the mixture was added to the reaction vessel, and the vessel was shaken for 40 minutes. The reaction solution was removed by applying nitrogen pressure, after which dehydrated methanol (15.2 ml) and diisopropylethylamine (EtN(iPr)$_2$) (4.9 ml, 28.2 mmol) were added to dehydrated dichloromethane (100 ml), the mixture was added to the reaction vessel, and the vessel was shaken for 2 hours. The reaction solution was removed by applying nitrogen pressure, after which dichloromethane (100 ml) was placed and the vessel was shaken for 5 minutes. The reaction solution was removed by applying nitrogen pressure, after which dichloromethane (100 ml) was placed again and the vessel was shaken for 5 minutes. The reaction solution was removed by applying nitrogen pressure, after which the resin was dried under reduced pressure overnight to afford Fmoc-Asp(O-Trt(2-Cl)-Resin)-MePhe-MePhe-Ala-pip (Compound SP459) (SEQ ID NO: 321) (8.66 g). Loading rate: 0.285 mmol/g, 21.0%

1-1-3. Synthesis of a Compound Having the Main Chain Carboxylic Acid Site Removed as a Derivative of a Compound Having Side Chain Carboxylic Acid of Fmoc-Asp Bound to a Resin (Compound SP405, a Compound Having the Carboxylic Acid Site of L-3-ABU Bound to a Resin)

Synthesis of (S)-3-((((9H-fluoren-9-yl)methoxy) carbonyl)amino)butanoic acid-2-chlorotrityl Resin (Fmoc-L-3-ABU-(O-Trt-(2-Cl)-Resin, Compound SP405)

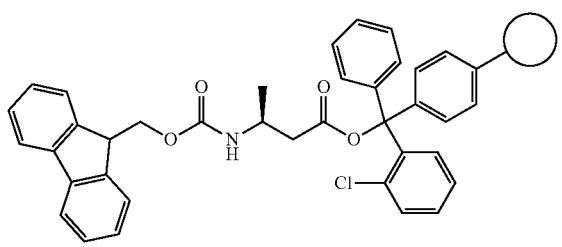 [SMILES: Cc1ccc(C(OC(=O)C[C@H](C)NC(=O)OCC2c3ccccc3-c3ccccc32)(c2ccccc2)c2ccccc2Cl)cc1]

2-Chlorotrityl chloride resin (100-200 mesh, 1% DVB, purchased from Watanabe Chemical Industries, 3.84 g, 6.15 mmol) and dehydrated dichloromethane (61 ml) were placed in a reaction vessel equipped with a filter, and the vessel was shaken at room temperature for 10 minutes. Dichloromethane was removed by applying nitrogen pressure, after which dehydrated methanol (980 µl) and diisopropylethylamine (2.52 ml) were added to a solution of (S)-3-((((9H-fluoren-9-yl)methoxy)carbonyl)amino)butanoic acid (Compound SP406, Fmoc-L-3-ABU-OH) (1.00 g) in dehydrated dichloromethane (61 ml), the mixture was added to the reaction vessel, and the vessel was shaken for 5 minutes. The reaction solution was removed by applying nitrogen pressure, after which dehydrated methanol (8.0 ml) and diisopropylethylamine (2.5 ml) were added to dehydrated dichloromethane (64 ml), the mixture was added to the reaction vessel, and the vessel was shaken for 2 hours. The reaction solution was removed by applying nitrogen pressure, after which dichloromethane (61 ml) was placed and the vessel was shaken for 5 minutes. The reaction solution was removed by applying nitrogen pressure, after which dichloromethane (61 ml) was placed again and the vessel was shaken for 5 minutes. The reaction solution was removed by applying nitrogen pressure, after which the resin was dried under reduced pressure overnight to afford (S)-3-((((9H-fluoren-9-yl)methoxy)carbonyl)amino)butanoic acid-2-chlorotrityl resin (Compound SP405) (4.16 g). Loading rate: 0.470 mmol/g, 31.8%

1-1-4. Synthesis of a Compound Having the Main Chain Carboxylic Acid Site Removed as a Derivative of a Compound Having Side Chain Carboxylic Acid of Fmoc-Asp Bound to a Resin (a Compound Having the Carboxylic Acid Site of 3-CF3-bAla Bound to a Resin, Compound SP407)

Synthesis of (S)-3-((((9H-fluoren-9-yl)methoxy) carbonyl)amino)-4,4,4-trifluorobutanoic Acid-2-Chlorotrityl Resin (Fmoc-3-CF3-bAla-(O-Trt-(2-Cl)-Resin, Compound SP407)

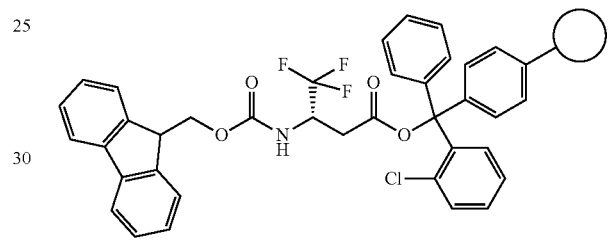

2-Chlorotrityl chloride resin (100-200 mesh, 1% DVB, purchased from Watanabe Chemical Industries, 1.65 g, 2.64 mmol) and dehydrated dichloromethane (26 ml) were placed in a reaction vessel equipped with a filter, and the vessel was shaken at room temperature for 10 minutes. Dichloromethane was removed by applying nitrogen pressure, after which dehydrated methanol (428 µl) and diisopropylethylamine (1.03 ml) were added to a solution of (S)-3-((((9H-fluoren-9-yl)methoxy)carbonyl)amino)-4,4,4-trifluorobutanoic acid (Compound SP408, Fmoc-CF3-bAla-OH) (500 mg) in dehydrated dichloromethane (26 ml), the mixture was added to the reaction vessel, and the vessel was shaken for 5 minutes. The reaction solution was removed by applying nitrogen pressure, after which dehydrated methanol (3.0 ml) and diisopropylethylamine (1.0 ml) were added to dehydrated dichloromethane (25 ml), the mixture was added to the reaction vessel, and the vessel was shaken for 2 hours. The reaction solution was removed by applying nitrogen pressure, after which dichloromethane (25 ml) was placed and the vessel was shaken for 5 minutes. The reaction solution was removed by applying nitrogen pressure, after which dichloromethane (25 ml) was placed again and the vessel was shaken for 5 minutes. The reaction solution was removed by applying nitrogen pressure, after which the resin was dried under reduced pressure overnight to afford (S)-3-((((9H-fluoren-9-yl)methoxy)carbonyl)amino)-4,4,4-trifluorobutanoic acid-2-chloro trityl resin (Compound SP407) (1.76 g). Loading rate: 0.234 mmol/g, 15.6%

1-2. Synthesis of Amino Acid Derivatives

Many amino acid derivatives for evaluating drug-likeness can be purchased or are known in the literature, and can be synthesized by conventional methods. Methods for synthesizing amino acid derivatives not known in the literature will be described below.

Synthesis of (2S)-2-(9H-fluoren-9-ylmethoxycarbonylamino)-3-(1-trityltetrazol-5-yl)propanoic acid and (2S)-2-(9H-fluoren-9-ylmethoxycarbonylamino)-3-(2-trityltetrazol-5-yl)propanoic Acid (Compound SP409, Fmoc-Ala(5-Tet(Trt))-OH)

The synthesis was carried out according to the following scheme.

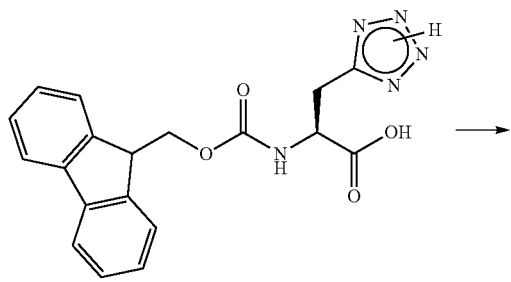

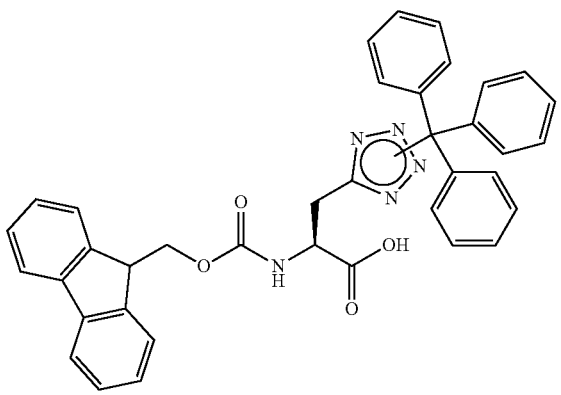

In the scheme, the trityl group is meant to be bonded to any of the four nitrogen atoms of the tetrazole ring.

(2S)-2-(9H-Fluoren-9-ylmethoxycarbonylamino)-3-(1H-tetrazol-5-yl)propanoic acid and (2S)-2-(9H-fluoren-9-ylmethoxycarbonylamino)-3-(2H-tetrazol-5-yl)propanoic acid (Compound SP410, Fmoc-Ala(5-Tet)-OH) (900 mg, 2.37 mmol) were dissolved in tetrahydrofuran (2.7 ml), N,N-diisopropylethylamine (0.36 mL, 2.61 mmol) was added and the mixture was stirred for 5 minutes. A solution of trityl chloride (628 mg, 2.25 mmol) dissolved in tetrahydrofuran (0.6 ml) was added to the aforementioned reaction solution, and the mixture was stirred for 90 minutes. The reaction solution was filtered, and the collected reaction solution was concentrated under reduced pressure, and the residue was purified by reverse-phase silica gel column chromatography (10 mM aqueous ammonium acetate solution/methanol) to afford (2S)-2-(9H-fluoren-9-ylmethoxycarbonylamino)-3-(1-trityltetrazol-5-yl)propanoic acid and (2S)-2-(9H-fluoren-9-ylmethoxycarbonylamino)-3-(2-trityltetrazol-5-yl)propanoic acid (Compound SP409, Fmoc-Ala(5-Tet(Trt))-OH) (644 mg, 44%).

LCMS (ESI) m/z=620.3 (M−H)−

Retention time: 1.06 min (analysis condition SQDAA05)

Synthesis of (S)-2-((((9H-fluoren-9-yl)methoxy)carbonyl)(ethyl)amino)-3-phenylpropanoic Acid (Compound SP443, Fmoc-EtPhe-OH)

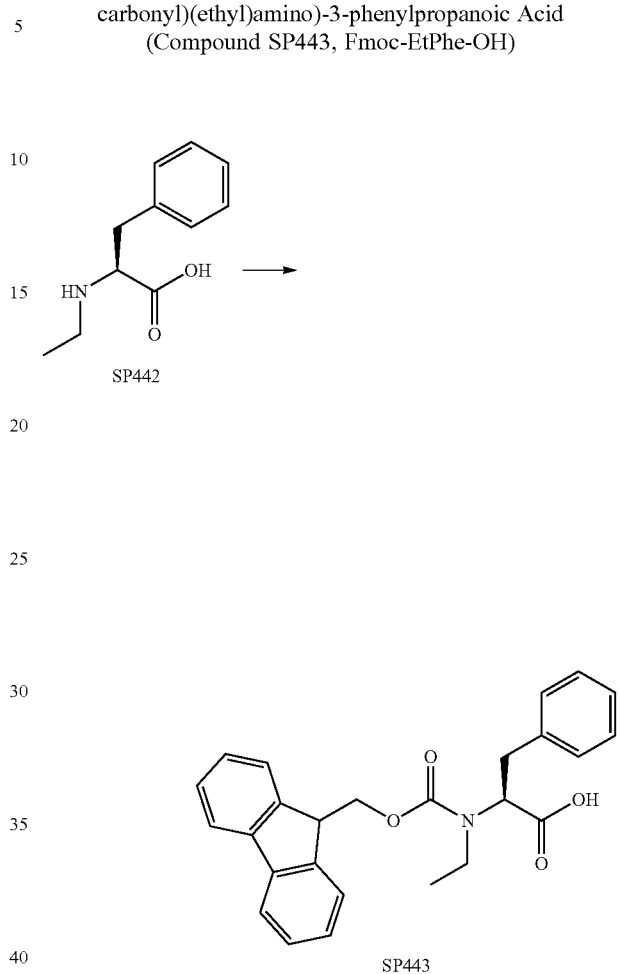

(S)-2-(Ethylamino)-3-phenylpropanoic acid (Compound SP442) was synthesized according to the literature, Tetrahedron Asymmetry, 19(8), 970-975; 2008, Stodulski, Maciej and Mlynarski, Jacek.

(S)-2-(Ethylamino)-3-phenylpropanoic acid (Compound SP442) (4.00 g, 20.7 mmol) was dissolved in a mixture of 1,4-dioxane (100 ml) and water (100 ml), potassium carbonate (8.69 g, 62.9 mmol) and (9H-fluoren-9-yl)methyl (2,5-dioxopyrrolidin-1-yl) carbonate (6.98 g, 20.7 mol) were added, and the mixture was stirred at room temperature for 8 hours. The aqueous layer was adjusted to pH 4 with a aqueous potassium bisulfate solution, and 1,4-dioxane was evaporated under reduced pressure. The resulting aqueous solution was extracted with ethyl acetate, and the resulting organic extract was washed with brine, dried over sodium sulfate and then concentrated under reduced pressure. The resulting residue was purified by column chromatography (ethyl acetate:petroleum ether=1:1) to afford (2S,4R)-1-(((9H-fluoren-9-yl)methoxy)carbonyl)-4-ethoxypyrrolidine-2-carboxylic acid (Compound SP443) (3.2 g, 37%).

LCMS (ESI) m/z=416 (M+H)+

Retention time: 1.97 min (analysis condition SMD method 11)

Synthesis of (S)-2-((((9H-fluoren-9-yl)methoxy)carbonyl)amino)-5-(methylamino)-5-oxopentanoic acid (Fmoc-Gln(Me)-OH, Compound SP446) and (S)-2-((((9H-fluoren-9-yl)methoxy)carbonyl)amino)-5-(dimethylamino)-5-oxopentanoic Acid (Fmoc-Gln(Me2)-OH, Compound SP448)

The synthesis was carried by the following scheme.

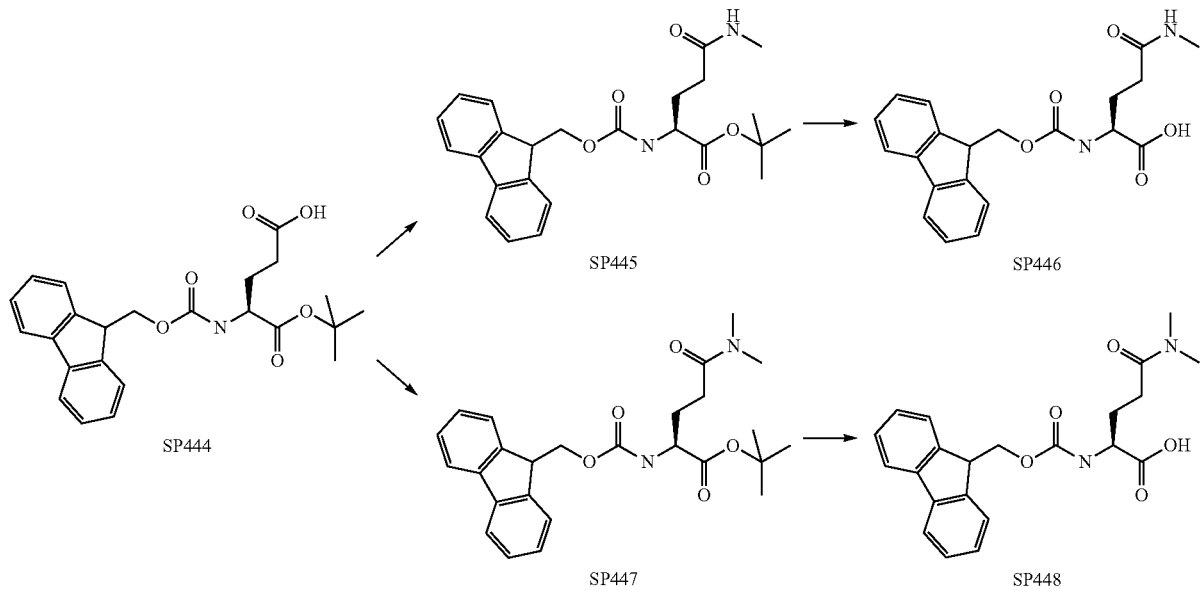

Synthesis of tert-butyl (S)-2-((((9H-fluoren-9-yl)methoxy)carbonyl)amino)-5-(methylamino)-5-oxopentanoate (Compound SP445)

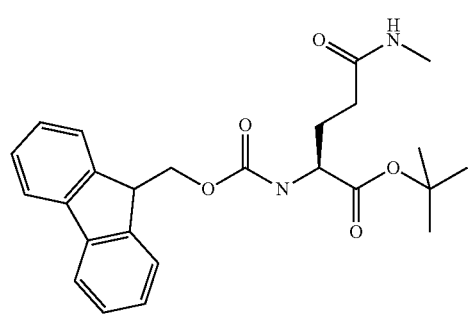 [SMILES: CNC(=O)CC[C@H](NC(=O)OCC1c2ccccc2-c2ccccc21)C(=O)OC(C)(C)C]

(S)-3-((((9H-Fluoren-9-yl)methoxy)carbonyl)amino)-4-(tert-butoxy)-4-oxobutanoic acid (Compound SP444) (7.00 g, 17.0 mmol) was dissolved in dimethylformamide (50 ml), (benzotriazol-1-yloxy)tripyrrolidinophosphonium hexafluorophosphate (PyBOP) (10.3 g, 19.8 mmol) and methylamine (42 mmol) were added as a 2 mol/l solution in tetrahydrofuran, and the mixture was stirred at room temperature for 1 hour. Water was added to the reaction solution, followed by extraction with dichloromethane. The organic extract was sequentially washed with aqueous sodium bicarbonate and water and then dried over magnesium sulfate, and the solvent was evaporated under reduced pressure to afford tert-butyl (S)-2-((((9H-fluoren-9-yl)methoxy)carbonyl)amino)-5-(methylamino)-5-oxopentanoate (Compound SP445) (13.3 g) as a crude product.

LCMS (ESI) m/z=439 (M+H)+
Retention time: 1.05 min (analysis condition SQDAA05)

Synthesis of (S)-2-((((9H-fluoren-9-yl)methoxy)carbonyl)amino)-5-(methylamino)-5-oxopentanoic Acid (Compound SP446)

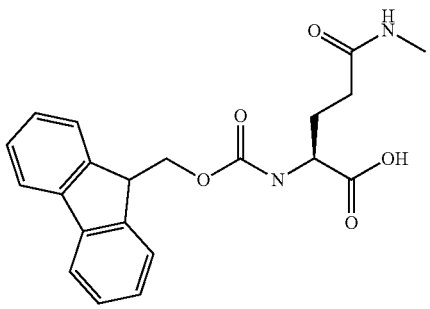

tert-Butyl (S)-2-((((9H-fluoren-9-yl)methoxy)carbonyl)amino)-5-(methylamino)-5-oxopentanoate (Compound SP445) (13.3 g, crude product) was dissolved in a mixture of dichloromethane (140 ml) and trifluoroacetic acid (140 ml), followed by stirring at room temperature for 2 hours. The solvent was evaporated under reduced pressure, and the resulting solid was washed with hexane and then dried in vacuo to afford (S)-2-((((9H-fluoren-9-yl)methoxy)carbonyl)amino)-5-(methylamino)-5-oxopentanoic acid (Compound SP446) (5.84 g, 93%, two steps).

LCMS (ESI) m/z=383 (M+H)+
Retention time: 2.07 min (analysis condition ZQAA05)

Synthesis of tert-butyl (S)-2-((((9H-fluoren-9-yl)methoxy)carbonyl)amino)-5-(dimethylamino)-5-oxopentanoate (Compound SP447)

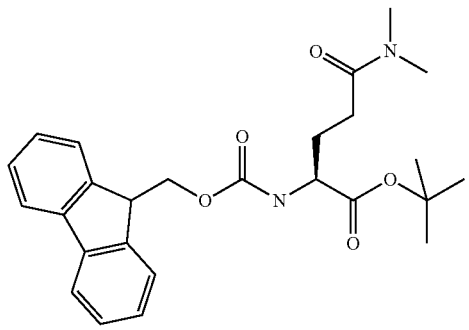

(S)-3-((((9H-Fluoren-9-yl)methoxy)carbonyl)amino)-4-(tert-butoxy)-4-oxobutanoic acid (Compound SP444) (10.0 g, 23.5 mmol) was dissolved in dimethylformamide (70 ml), ((benzotriazol-1-yloxy)-tris(dimethylamino)phosphonium hexafluorophosphate (BOP) (12.5 g, 28.3 mmol) and dimethylamine (58 mmol) were added as a 2 mol/l solution in tetrahydrofuran, and the mixture was stirred at room temperature for 30 minutes. Water was added to the reaction solution, followed by extraction with dichloromethane. The organic extract was dried over magnesium sulfate, and the solvent was evaporated under reduced pressure to afford tert-butyl (S)-2-((((9H-fluoren-9-yl)methoxy)carbonyl)amino)-5-(dimethylamino)-5-oxopentanoate (Compound SP447) (15.2 g) as a crude product.

LCMS (ESI) m/z=453 (M+H)+

Retention time: 3.00 min (analysis condition SQDAA05)

Synthesis of (S)-2-((((9H-fluoren-9-yl)methoxy)carbonyl)amino)-5-(dimethylamino)-5-oxopentanoic Acid (Compound SP448)

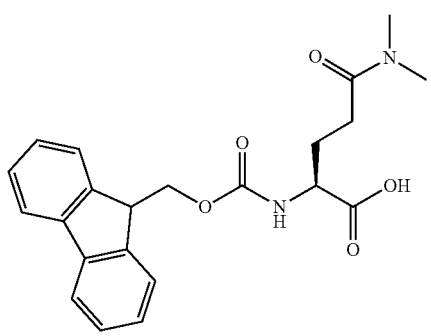 [SMILES: CN(C)C(=O)CC[C@H](NC(=O)OCC1c2ccccc2-c2ccccc21)C(=O)O]

tert-Butyl (S)-2-((((9H-fluoren-9-yl)methoxy)carbonyl)amino)-5-(dimethylamino)-5-oxopentanoate (Compound SP447) (15.2 g, crude product) was dissolved in a mixture of dichloromethane (200 ml) and trifluoroacetic acid (200 ml), followed by stirring at room temperature for 2.5 hours. The solvent was evaporated under reduced pressure, and the resulting solid was washed with a mixed solution of hexane and tert-butyl methyl ether and then dried in vacuo to afford (S)-2-((((9H-fluoren-9-yl)methoxy)carbonyl)amino)-5-(dimethylamino)-5-oxopentanoic acid (Compound SP448) (9.12 g, 85%, two steps).

LCMS (ESI) m/z=397 (M+H)+

Retention time: 2.18 min (analysis condition ZQAA05)

Synthesis of (S)-2-((((9H-fluoren-9-yl)methoxy)carbonyl)amino)-3-(3-fluoro-4-hydroxyphenyl)propanoic Acid (Fmoc-Tyr(3-F)—OH, Compound SP450)

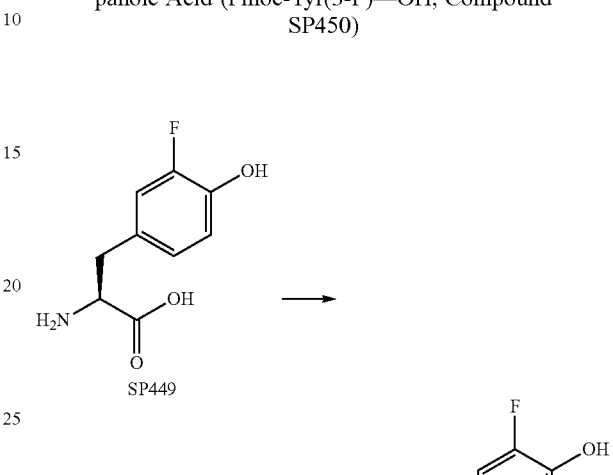

(S)-2-Amino-3-(3-fluoro-4-hydroxyphenyl)propanoic acid (H-Tyr(3-F)—OH, SP449) (7.2 g, 36.2 mmol) was dissolved in a 10% aqueous sodium carbonate solution (250 ml), N-(9-fluorenylmethoxycarbonyloxy)-succinimide (12.2 g, 36.2 mmol) was added and the mixture was stirred at room temperature for 1.5 hours. Water (120 ml) was added to the reaction solution, and the mixture was then washed with 200 ml of diethyl ether twice and with 100 ml of diethyl ether once. The aqueous layer was made acidic (pH=2) by adding a 6 N aqueous HCl solution thereto, and then extracted with 250 ml of ethyl acetate twice and with 200 ml of ethyl acetate once. The resulting ethyl acetate layer was dried over anhydrous magnesium sulfate, filtered and concentrated under reduced pressure to afford the title compound (SP450, 15.3 g, 100%).

LCMS (ESI) m/z=420.3 (M–H)–

Retention time: 0.39 min (analysis condition SQDAA50)

1-3. Synthesis of Amide-Cyclized Drug-Like Peptides 1-3-1. Synthetic examples of peptides cyclized with carboxylic acid in side chain of the C-terminal aspartic acid functioning as intersection unit, that is carboxylic acid in main chain is amidated with amine, piperidine and others, and N-terminal amino group (Δ unit).

Synthetic examples of peptides will be described in which the side chain carboxylic group of the C-terminal aspartic acid having amidated main chain carboxylic group (piperidinated in this example) is cyclized with the main chain amino group at the N-terminal by an amide bond. This example will be described as a representative example, but any method described in different places of the present specification may also be used for peptide chemical synthesis. The following scheme G1 illustrates an example of such synthesis.

A peptide was elongated using Compound SP402 (2-chlorotrityl resin on which Compound SP401 (Fmoc-Asp-pip) is supported) (200 mg) and Fmoc amino acids such as Fmoc-MePhe-OH, Fmoc-EtPhe-OH (Compound SP443), Fmoc-MeAla-OH, Fmoc-MeLeu-OH, Fmoc-D-MeAla-OH, Fmoc-MeGly-OH, Fmoc-MeVal-OH, Fmoc-MeIle-OH, Fmoc-g-MeAbu-OH, Fmoc-b-MeAla-OH, Fmoc-nPrGly-OH (Compound SP815), Fmoc-MeAla(4-Thz)-OH (Compound SP811), Fmoc-Pro-OH, Fmoc-Aze(2)-OH, Fmoc-Pic(2)-OH, Fmoc-Phe-OH, Fmoc-Phg-OH, Fmoc-Val-OH, Fmoc-D-Val-OH, Fmoc-Ser(tBu)-OH, Fmoc-Thr(Trt)-OH, Fmoc-Leu-OH, Fmoc-D-Leu-OH, Fmoc-Ile-OH, Fmoc-Ala-OH, Fmoc-D-Ala-OH, Fmoc-Gly-OH, Fmoc-Lys(Me2)-OH, Fmoc-Arg(Me2)-OH, Fmoc-Gln(Me2)-OH (Compound SP448), Fmoc-Gln(Me)-OH (Compound SP446), Fmoc-Gln-OH, Fmoc-Algly-OH, Fmoc-Ala(4-Thz)-OH, Fmoc-Ala(CN)-OH, Fmoc-Hph-OH, Fmoc-Phe3-OH, Fmoc-Ala(3Pyr)-OH and Fmoc-Tyr(3-F)—OH (Compound SP450) (abbreviations for amino acids are described in Table 11-2). Peptide elongation was carried out according to a peptide synthesis method by the Fmoc method previously described in Examples. Following the peptide elongation, the Fmoc group at the N-terminal was removed on a peptide synthesizer, and the resin was then washed with DMF. The peptide was cleaved from the resin by adding a 4 N solution of HCl in 1,4-dioxane/dichloromethane/2,2,2-trifluoroethanol/triisopropylsilane (=1/60/30/5.7, v/v, 4 mL) to the resin and reacting for two hours. After completion of the reaction, the solution in the tube was filtered through a synthesis column to remove the resin, and the resin was washed with dichloromethane/2,2,2-trifluoroethanol (=1/1, v/v, 1 mL) twice. All extracts were combined, neutralized with DIPEA (43.2 μL, 0.248 mmol) and then concentrated under reduced pressure. The resulting residue was dissolved in dichloromethane (8 mL). A solution of O-(7-aza-1H-benzotriazol-1-yl)-N,N,N,N-tetramethyluronium hexafluorophosphate (HATU) (0.24 mmol) in DMSO (0.24 mL) and DIPEA (50.2 μL, 0.29 mmol) were added, followed by shaking at room temperature for 2 hours. The solvent was evaporated under reduced pressure, after which the residue was dissolved in DMSO and the solution was purified by preparative HPLC to obtain the title amide-cyclized drug-like peptide. DP-1 to 39, DP-47 to 122, DP-125 to 176, DP-215 to 277, DP-317 to 343, DP-408 to 442, DP-465 to 482, DP-485 to 489, DP-494, DP-511 to 564, DP-587 to 588, DP-590 to 591, DP-593 to 594, DP-597 to 630, DP-632 to 638, DP-673 to 675 and DP-677 to 751 can be synthesized by methods in accordance with this synthesis method. The mass spectral value and the retention time of LC/MS of each compound are described in Table 11-3-2.

Figure 92:
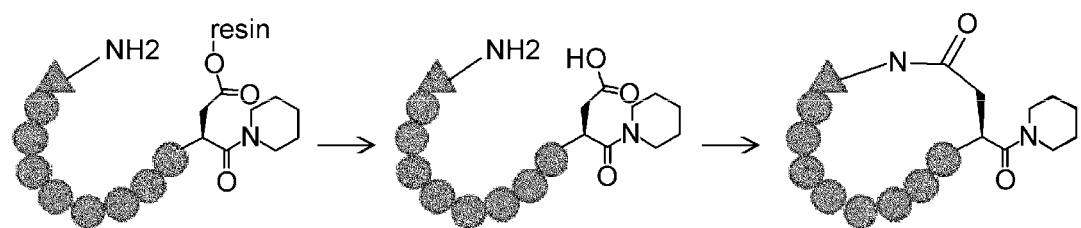
FIG. 92 is a diagram showing scheme G1. Scheme G1 shows an example of the methods for synthesizing the amide-cyclized drug-like peptides.

See FIG. 92.

TABLE 11-1

| | mw | cLogP | 13 | 12 | 11 | 10 | 9 | 8 | 7 | 6 | 5 |
|---|---|---|---|---|---|---|---|---|---|---|---|
| DP-1 | 1481.9 | 12.5 | Ala | Val | MeGly | Leu | MeLeu | Ala | MeIle | Phe | MePhe |
| DP-2 | 1524.0 | 14.4 | Ala | Val | MeLeu | MeGly | MeLeu | MeIle | Ala | MePhe | MePhe |
| DP-3 | 1326.6 | 9.0 | | Ala | Ala | Leu | MeVal | Leu | Phe | Phe | Pro |
| DP-4 | 1348.7 | 11.0 | | Ala | Val | MeAla | Leu | Leu | Ile | Phe | Leu |
| DP-5 | 1306.7 | 9.6 | | Ala | Ile | Pro | MeLeu | Thr | Gly | Phe | MeAla |
| DP-6 | 1354.7 | 10.3 | | Ala | Thr | MeLeu | Leu | Phe | Pro | Phe | Val |
| DP-7 | 1382.8 | 11.4 | | Ala | Leu | MeGly | Leu | Gly | MeAla | Phe | Thr |
| DP-8 | 1398.8 | 12.6 | | Ala | Leu | MeIle | MeLeu | MeIle | MeAla | Phe | Thr |
| DP-9 | 1382.8 | 11.6 | | Ala | Ile | Pro | MeLeu | Val | Thr | MePhe | MeAla |
| DP-10 | 1438.9 | 13.6 | | Ala | Ile | Pro | MeLeu | Thr | MePhe | MePhe | Ala |
| DP-11 | 1396.8 | 12.3 | | Ala | Thr | MePhe | MeLeu | Leu | Pro | MePhe | Leu |
| DP-12 | 1452.9 | 14.3 | | Ala | Thr | MeAla | MeLeu | Leu | MeLeu | MePhe | MePhe |
| DP-13 | 1299.7 | 11.1 | | | Ala | Ile | MeLeu | MeVa | Thr | MePhe | Ala |
| DP-14 | 1283.6 | 10.2 | | | Ala | Leu | MeLeu | MeLeu | Phe | MePhe | Ile |
| DP-15 | 1311.7 | 11.5 | | | Ala | Val | MeLeu | MeLeu | MePhe | MePhe | MeIle |
| DP-16 | 1297.6 | 11.3 | | | Ala | Gly | MeLeu | MeIle | MeAla | MePhe | Thr |
| DP-17 | 1226.6 | 10.5 | | | | Ala | MeLeu | MeIle | Phe | MePhe | Ile |
| DP-18 | 1214.6 | 10.8 | | | | Ala | Leu | MeIle | MeAla | Phe | Thr |
| DP-19 | 1439.8 | 10.5 | Ala | Phe | Ile | Pro | Leu | Thr | Gly | Phe | MeAla |
| DP-20 | 1453.8 | 11.2 | Ala | Gly | Thr | MePhe | Leu | Pro | Val | Phe | Leu |
| DP-21 | 1467.9 | 11.8 | Ala | Val | MeAla | Thr | Leu | Phe | MeLeu | Pro | Phe |
| DP-22 | 1481.9 | 12.5 | Ala | Gly | MeAla | Ala | Leu | MeLeu | MePhe | Ile | Phe |
| DP-23 | 1340.7 | 9.6 | | Ala | Phe | Pro | Leu | Thr | Gly | Phe | Val |
| DP-24 | 1354.7 | 10.3 | | Ala | Thr | MePhe | Leu | Pro | Val | MePhe | MeGly |
| DP-25 | 1424.8 | 13.0 | | Ala | Gly | MeAla | Leu | MeVal | Phe | Phe | Ile |
| DP-26 | 1368.7 | 11.0 | | Ala | Val | MeVal | MeLeu | MeVal | MeIle | MePhe | MePhe |
| DP-27 | 1382.8 | 11.6 | | Ala | Gly | MePhe | Leu | Ala | MeVal | Phe | MeGly |
| DP-28 | 1243.6 | 9.1 | | | Thr | Ile | MeLeu | Pro | Ala | MePhe | Thr |
| DP-29 | 1311.7 | 11.3 | | | Ala | Ala | MeLeu | MeGly | MeAla | MePhe | Phe |
| DP-30 | 1255.6 | 9.3 | | | Ala | Gly | MeLeu | Leu | Ala | MePhe | Thr |
| DP-31 | 1285.6 | 11.1 | | | Ala | Gly | MeLeu | Ile | MeLeu | MePhe | Thr |
| DP-32 | 1221.5 | 9.5 | | | Ala | Leu | Pro | Met | MeGly | Phe | MeVal |
| DP-33 | 1113.4 | 9.0 | | | | | Ala | Thr | MeLeu | Phe | MePhe |
| DP-34 | 1085.4 | 8.3 | | | | | Ala | Leu | MeAla | MePhe | Thr |
| DP-35 | 1370.7 | 11.2 | | | Leu | MeIle | Leu | Ile | Thr | Phe | Ala |
| DP-36 | 1196.5 | 10.2 | | | Ala | Ala | MeAla | MeGly | MeLeu | Thr | MeGly |
| DP-37 | 1111.4 | 9.5 | | | | | Ala | MePhe | MeLeu | Thr | MeGly |
| DP-38 | 1069.4 | 8.0 | | | | | Ala | MePhe | MePhe | Thr | Thr |
| DP-39 | 1083.4 | 8.5 | | | | | MeAla | MeAla | MeAla | MeLeu | Thr |
| DP-40 | 1453.8 | 10.7 | | Ala | Leu | Pro | Ala | Leu | Thr | Thr | Ala |
| DP-41 | 1453.8 | 10.5 | | | Ala | Leu | Phe | Leu | Thr | Pro | MeGly |
| DP-42 | 1453.8 | 10.3 | | | | Ala | Leu | Thr | MeLeu | Phe | Pro |
| DP-43 | 1396.8 | 10.8 | | | | Ala | Phe | Pro | Leu | Thr | Leu |
| DP-44 | 1297.6 | 10.3 | | | | Ala | Thr | Leu | Pro | Phe | MePhe |
| DP-45 | 1200.5 | 10.0 | | | | | | Ala | Ala | MeLeu | Ala |
| DP-46 | 1385.8 | 9.1 | | | MeAla | MePhe | | | | | |
| DP-47 | 1385.8 | 13.2 | | | MeAla | MePhe | Leu | MeLeu | Thr | MeGly | MeIle |
| DP-48 | 1327.7 | 11.9 | | | b-MeAla | Leu | MeLeu | MeIle | Ala | MePhe | Thr |
| DP-49 | 1413.8 | 14.2 | | | D-MeAla | MeLeu | Leu | MePhe | Ser(tBu) | MePhe | Thr |

TABLE 11-1-continued

| ID | Mass | # | | | | | | | | | |
|---|---|---|---|---|---|---|---|---|---|---|---|
| DP-50 | 1244.6 | 9.4 | | | | | b-MeAla | MeLeu | MeLeu | Thr | MePhe |
| DP-51 | 1228.6 | 11.8 | | | | | D-MeAla | MeAla | Ile | MePhe | Thr |
| DP-52 | 1089.3 | 7.4 | | | | | | MeAla | Thr | MePhe | Ser(tBu) |
| DP-53 | 1384.8 | 12.0 | | | | D-Ala | MePhe | Leu | MeAla | Val | MeLeu |
| DP-54 | 1382.8 | 11.4 | | | | D-Ala | MeAla | Leu | MeAla | Phe | Thr |
| DP-55 | 1426.8 | 11.2 | | | | D-Val | MeGly | Leu | MeIle | Gly | Ser(tBu) |
| DP-56 | 1410.8 | 12.6 | | | | D-Val | MeGly | Leu | Phe | Thr | MePhe |
| DP-57 | 1412.8 | 10.8 | | | | MeAla | MeGly | Ser(tBu) | Pro | Phe | Pro |
| DP-58 | 1396.8 | 12.2 | | | | MeAla | MeLeu | Leu | MeVal | Leu | MeGly |
| DP-59 | 1370.7 | 10.7 | | | | b-MeAla | MePhe | Val | MeIle | Phe | MePhe |
| DP-60 | 1111.4 | 9.6 | | | | | Phe | Val | MeIle | Gly | MeLeu |
| DP-61 | 1398.8 | 12.1 | | | | b-MeAla | MePhe | MeGly | Thr | MePhe | Thr |
| DP-62 | 1412.8 | 10.7 | | | | D-MeAla | MeLeu | MeLeu | Ala | MeAla | Leu |
| DP-63 | 1484.9 | 14.2 | | | | D-MeAla | Ala | Ser(tBu) | Pro | MeIle | MeAla |
| DP-64 | 1384.8 | 12.5 | | | | MeGly | MePhe | MeLeu | Phe | MeAla | Thr |
| DP-65 | 1283.6 | 10.6 | | | | | Leu | MeAla | MeVal | Ala | MeVal |
| DP-66 | 1311.7 | 11.7 | | | | D-Ala | Thr | MeGly | Pro | Ala | Pro |
| DP-67 | 1297.6 | 11.3 | | | | D-Val | Thr | MeGly | MePhe | Ala | Pro |
| DP-68 | 1313.7 | 11.2 | | | | MeAla | MeVal | MeLeu | MePhe | MeLeu | Phe |
| DP-69 | 1399.8 | 13.7 | | | | b-MeAla | MeLeu | MePhe | Thr | MeAla | MeIle |
| DP-70 | 1341.7 | 13.5 | | | | MeGly | MeLeu | Leu | Ser(tBu) | MePhe | MePhe |
| DP-71 | 1096.4 | 8.1 | | | | MeGly | Ala | MeAla | MePhe | MeLeu | MePhe |
| DP-72 | 1228.6 | 11.7 | | | | | Thr | Thr | MeVal | MeLeu | MeGly |
| DP-73 | 1110.4 | 8.7 | | | | | Thr | Thr | MeIle | MeVal | Gly |
| DP-74 | 1214.6 | 11.3 | | | | MeAla | Thr | MeAla | MeIle | Phe | MeGly |
| DP-75 | 1096.4 | 8.2 | | | | D-MeAla | Thr | MeAla | MeAla | Gly | MePhe |
| DP-76 | 1196.5 | 10.3 | | | | MeGly | Ser(tBu) | MeGly | MeAla | Phe | MeGly |
| DP-77 | 1111.4 | 9.5 | | | | MeGly | D-Ala | MePhe | MeLeu | Thr | MePhe |
| DP-78 | 1101.4 | 9.4 | | | | | D-Val | Leu | Thr | Thr | MeGly |
| DP-79 | 1103.4 | 7.9 | | | | | MeAla | Ala | MeAla | MeAla | Phe |
| DP-80 | 1103.4 | 7.0 | | | | | Thr | b-MeAla | Thr | MePhe | Ser(tBu) |
| DP-81 | 1125.5 | 10.1 | | | | | MePhe | D-MeAla | MePhe | Thr | MeGly |
| DP-82 | 1427.8 | 10.6 | | | Ala | Leu | Phe | Leu | MeAla | Gly | Val |
| DP-83 | 1455.8 | 11.9 | | | Ala | Gly | MeAla | Val | MeLeu | MePhe | Ile |
| DP-84 | 1314.6 | 9.1 | | | | Ala | Ala | MeVal | Leu | MePhe | MeAla |
| DP-85 | 1271.6 | 10.4 | | | | Ala | Ala | MeLeu | MeVal | MePhe | Ile |
| DP-86 | 1101.4 | 9.2 | | | | | | Ala | Leu | Phe | MePhe |
| DP-87 | 1427.8 | 11.4 | | | Ala | Gly | Thr | Leu | MeAla | Val | Leu |
| DP-88 | 1398.7 | 10.2 | | | | D-Ala | Phe | Leu | Phe | Pro | Ser(tBu) |
| DP-89 | 1398.8 | 12.5 | | | | MeAla | Phe | MeLeu | MeVal | Leu | MeLeu |
| DP-90 | 1484.9 | 14.2 | | | | MeAla | MePhe | Val | Metle | Gly | MeLeu |
| DP-91 | 1396.8 | 11.0 | | | | b-MeAla | MeAla | Ala | Thr | MePhe | MeAla |
| DP-92 | 1484.9 | 13.4 | | | | b-MeAla | Phe | Leu | Pro | MePhe | Metle |
| DP-93 | 1370.7 | 11.7 | | | | D-MeAla | MePhe | MePhe | Thr | MeIle | Ala |
| DP-94 | 1398.8 | 13.0 | | | | D-MeAla | Phe | MeLeu | Val | MeIle | Gly |
| DP-95 | 1209.5 | 9.7 | | | | | Leu | MeLeu | Gly | MeVal | MePhe |
| DP-96 | 1399.8 | 13.7 | | | | D-Ala | MeLeu | MeLeu | Thr | MeGly | Leu |
| DP-97 | 1313.7 | 12.3 | | | | D-Ala | Leu | MeLeu | MePhe | Ser(tBu) | Ser(tBu) |
| DP-98 | 1299.7 | 11.7 | | | | D-Ala | MeLeu | MeLeu | MePhe | Ala | MeLeu |
| DP-99 | 1341.7 | 13.4 | | | | D-Ala | Leu | MeLeu | MeLeu | MePhe | MeAla |
| DP-100 | 1413.8 | 14.2 | | | | MeAla | MeAla | Leu | Metle | Phe | Metle |
| DP-101 | 1327.7 | 12.8 | | | | MeAla | Leu | MeLeu | Ala | MePhe | Thr |
| DP-102 | 1223.6 | 9.2 | | | | b-MeAla | Phe | MeLeu | MeLeu | MeAla | Ala |

TABLE 11-1-continued

| ID | Mass | | | | | | | | | | |
|---|---|---|---|---|---|---|---|---|---|---|---|
| DP-103 | 1413.8 | | | | b-MeAla | MeLeu | Leu | MePhe | Ser(tBu) | MePhe | MeIle |
| DP-104 | 1383.8 | | | | b-MeAla | MeLeu | Thr | MePhe | MeLeu | Ala | MeLeu |
| DP-105 | 1327.7 | | | | D-MeAla | Leu | MeLeu | MePhe | Ala | MePhe | MeIle |
| DP-106 | 1297.6 | | | | MeGly | MeLeu | MeLeu | Leu | Gly | MeIle | MeLeu |
| DP-107 | 1426.8 | | | g-MeAbu | Phe | MeLeu | Phe | Ser(tBu) | Gly | Thr | Leu |
| DP-108 | 1384.8 | | | g-MeAbu | MeAla | MeLeu | MeLeu | MeLeu | Ile | MePhe | MePhe |
| DP-109 | 1410.8 | | | g-MeAbu | MeAla | MeLeu | Leu | Thr | MeGly | MePhe | MeLeu |
| DP-110 | 1371.8 | | | | D-Ala | MePhe | Ile | Thr | MeGly | MeLeu | Thr |
| DP-111 | 1223.6 | | | | MeAla | Leu | Ala | Leu | MeAla | Gly | Ala |
| DP-112 | 1279.7 | | | | MeAla | MeLeu | Thr | Phe | MePhe | Gly | Phe |
| DP-113 | 1325.7 | | | | g-MeAbu | MeLeu | Leu | MePhe | Ser(tBu) | MeLeu | MePhe |
| DP-114 | 1427.9 | | | | g-MeAbu | MeLeu | Ile | MePhe | Leu | Leu | MePhe |
| DP-115 | 1262.6 | | | | D-Ala | Leu | Phe | Leu | MeLeu | Thr | Thr |
| DP-116 | 1234.5 | | | | MeAla | Phe | Phe | MeLeu | MeLeu | Phe | Thr |
| DP-117 | 1234.5 | | | | b-MeAla | Leu | Phe | MeVal | Thr | Leu | MePhe |
| DP-118 | 1152.5 | | | | b-MeAla | MeLeu | Ile | Leu | Thr | Gly | MePhe |
| DP-119 | 1276.6 | | | | D-MeAla | Phe | MeLeu | Thr | MeLeu | MePhe | MeLeu |
| DP-120 | 1244.6 | | | | D-MeAla | Phe | MeLeu | Ile | MeLeu | MeAla | MeAla |
| DP-121 | 1242.6 | | | | g-MeAbu | Ala | MeLeu | MeGly | MePhe | MeAla | MeLeu |
| DP-122 | 1224.6 | | | | g-MeAbul | Ser(tBu) | MePhe | MePhe | Thr | MeLeu | Thr |
| DP-123 | 1412.8 | | | | D-Val | MeAla | MePhe | MeLeu | Thr | MePhe | MePhe |
| DP-124 | 1356.7 | | | | D-MeAla | Ile | MeAla | MeVa | MeAla | MeLeu | MeAla |
| DP-125 | 1129.5 | | | | | MeAla | Thr | Leu | Thr | MePhe | Thr |
| DP-126 | 1219.6 | | | | | b-MeAla | Leu | MeAla | MeLeu | Leu | MePhe |
| DP-127 | 1129.5 | | | | | D-MeAla | Ala | MePhe | Phe | MeLeu | MePhe |
| DP-128 | 1101.4 | | | | | g-MeAbu | Thr | MeAla | MeLeu | Ala | MePhe |
| DP-129 | 1117.4 | | | | | g-MeAbu | Thr | MeLeu | MeVal | MePhe | Ser(tBu) |
| DP-130 | 1111.4 | | | | | g-MeAbu | MeAla | MeLeu | Thr | Thr | MeLeu |
| DP-131 | 1384.8 | D-Ala | | MePhe | MeLeu | Ile | MeVal | MePhe | Thr | MePhe | Thr |
| DP-132 | 1412.8 | D-Val | | MePhe | MeVal | Ala | MeVa | MePhe | MeLeu | MePhe | Thr |
| DP-133 | 1398.8 | MeAla | | MePhe | MeLeu | Ala | MeVa | MePhe | MeAla | MeAla | Thr |
| DP-134 | 1396.8 | b-MeAla | | MePhe | Phe | Ile | Pro | MeVa | MePhe | Thr | MeGly |
| DP-135 | 1066.4 | | | | D-Ala | MeAla | Ile | Ile | Thr | MeGly | MeGly |
| DP-136 | 1214.6 | | | | D-Ala | Phe | MeAla | Ile | Gly | MePhe | MePhe |
| DP-137 | 1384.8 | MeGly | | MeVal | Phe | MeAla | MePhe | Leu | Thr | MePhe | MeAla |
| DP-138 | 1210.6 | | | | MeAla | Ile | MeGly | MeLeu | MePhe | Thr | MeLeu |
| DP-139 | 1327.7 | | | | Leu | Thr | MePhe | Ala | MePhe | MeLeu | Thr |
| DP-140 | 1228.6 | | | | b-MeAla | MeAla | MeGly | MeAla | MeGly | MePhe | MeLeu |
| DP-141 | 1283.6 | | | D-Ala | Thr | MeGly | Phe | MeAla | MeGly | MePhe | MeAla |
| DP-142 | 1110.4 | | | D-Ala | D-MeAla | Thr | MeAla | MePhe | Ala | Ala | Pro |
| DP-143 | 1237.6 | | | | MeLeu | MeLeu | MeLeu | Thr | MePhe | Thr | MeGly |
| DP-144 | 1210.6 | | | D-Val | D-MeAla | MeGly | MeAla | MeAla | MePhe | MeVal |
| DP-145 | 1214.6 | | | | MeGly | MeIle | Ala | MeLeu | MeGly | MePhe | MePhe |
| DP-146 | 1311.7 | | | D-Val | Thr | MeAla | MeIle | MeAla | MeLeu | Leu | MeLeu |
| DP-147 | 1256.6 | | | | MeGly | Pro | MePhe | MeAla | MeLeu | Leu | MeVal |
| DP-148 | 1083.4 | | | | MeGly | D-Ala | MeAla | MeLeu | Ala | MePhe | Thr |
| DP-149 | 1399.8 | | | D-Val | MePhe | Leu | MeAla | MeLeu | MeGly | MeLeu | Thr |
| DP-150 | 1087.4 | | | | MePhe | Ala | Ala | MePhe | Thr | MeGly | Phe |
| DP-151 | 1313.7 | | | D-Val | MeAla | MeLeu | MeLeu | Ala | MeLeu | MePhe | Ala |
| DP-152 | 1125.5 | | | | MeAla | MeLeu | b-MeAla | MeLeu | MePhe | Thr | MeGly |
| DP-153 | 1087.4 | | | | | | MeLeu | Ala | MePhe | MeLeu | MeLeu |
| DP-154 | 1383.8 | MeAla | | | MeLeu | MeLeu | b-MeAla | MePhe | Thr | MeLeu | Ile |
| DP-155 | 1125.5 | | | | | | b-MeAla | MeLeu | Thr | MeLeu | MeGly |

TABLE 11-1-continued

| | | | | | | | | |
|---|---|---|---|---|---|---|---|---|
| DP-156 | 1341.7 | 13.3 | | | MeAla | MeLeu | Thr | MeAla | Ala | MePhe | Leu |
| DP-157 | 1087.4 | 9.0 | | | | MeLeu | D-MeAla | Ala | MePhe | Phe |
| DP-158 | 1355.8 | 14.0 | | MeAla | Ile | MeLeu | MeAla | MeLeu | MePhe |
| DP-159 | 1355.8 | 13.1 | | b-MeAla | | D-MeAla | MeAla | Thr | MePhe |
| DP-160 | 1097.4 | 9.1 | | | | MeGly | Ala | MeLeu | Thr |
| DP-161 | 1073.3 | 8.5 | | | | MeLeu | Ile | MeLeu | MeLeu |
| DP-162 | 1311.7 | 11.3 | | | Phe | MeGly | MePhe | Gly | Thr |
| DP-163 | 1083.4 | 8.5 | | | | MeAla | MePhe | MeLeu | Thr |
| DP-164 | 1297.6 | 11.2 | | | Thr | MeAla | Ile | Pro | MeVal |
| DP-165 | 1313.7 | 12.2 | | D-MeAla | MeAla | MeLeu | Leu | MeVal | MeLeu |
| DP-166 | 1355.8 | 14.0 | | D-MeAla | MeLeu | MeLeu | Ala | MePhe | MePhe |
| DP-167 | 1209.5 | 9.7 | | D-MeAla | Phe | MeLeu | MeVal | Thr | MeAla |
| DP-168 | 1371.8 | 12.7 | | MeGly | MePhe | Ile | MeLeu | MeGly | MePhe |
| DP-169 | 1214.6 | 11.2 | | MeGly | D-Ala | MeLeu | MeAla | MePhe | MeLeu |
| DP-170 | 1196.5 | 10.2 | | | D-Ala | MeAla | MePhe | Thr | MeGly |
| DP-171 | 1258.6 | 10.7 | | | D-Val | Ser(tBu) | MeLeu | Thr | Gly |
| DP-172 | 1242.6 | 12.1 | | | D-Val | MeLeu | MeAla | MePhe | MeLeu |
| DP-173 | 1228.6 | 11.4 | | | MeAla | Ala | MeAla | MePhe | MeLeu |
| DP-174 | 1214.6 | 10.4 | | | b-MeAla | Thr | MeAla | Phe | Gly |
| DP-175 | 1200.5 | 10.8 | | | MeGly | Thr | MeAla | MePhe | MePhe |
| DP-176 | 1117.4 | 8.3 | | | | D-Val | Thr | MeAla | MePhe |
| DP-177 | 1441.8 | 11.1 | | Ala | MeLeu | MeAla | Thr | MeGly | Ala |
| DP-178 | 1574.0 | 14.9 | | Ala | Ile | MeLeu | MeAla | MeVal | Thr |
| DP-179 | 1441.8 | 11.1 | | D-Ala | MeLeu | MeAla | Thr | MePhe | MeVal |
| DP-180 | 1546.0 | 13.7 | | D-Ala | MePhe | Leu | MePhe | Phe | MeAla |
| DP-181 | 1455.8 | 11.6 | | MeAla | MeLeu | MeAla | Thr | MeAla | MeAla |
| DP-182 | 1544.0 | 11.8 | | b-MeAla | Phe | MeAla | Gly | MeVal | Phe |
| DP-183 | 1546.0 | 13.7 | | D-MeAla | Ile | MeLeu | Thr | MeVal | Pro |
| DP-184 | 1588.1 | 15.4 | | D-MeAla | MeLeu | Ala | MeLeu | MeVal | MeAla |
| DP-185 | 1529.9 | 12.2 | | MeGly | Phe | MeLeu | Phe | MePhe | Thr |
| DP-186 | 1546.0 | 13.7 | | MeGly | MePhe | MeLeu | MeAla | MeLeu | Gly |
| DP-187 | 1418.8 | 11.3 | | | Ala | Thr | Thr | Leu | MePhe |
| DP-188 | 1384.8 | 11.7 | | | Ala | MeAla | MeLeu | MePhe | Gly |
| DP-189 | 1488.9 | 14.1 | | | D-Ala | Thr | MePhe | Thr | MeGly |
| DP-190 | 1517.0 | 15.0 | | | D-Val | MeLeu | MePhe | MeAla | MeLeu |
| DP-191 | 1432.8 | 11.8 | | | MeAla | Val | MeLeu | MePhe | MeLeu |
| DP-192 | 1502.9 | 14.7 | | | b-MeAla | Thr | MePhe | Gly | MeLeu |
| DP-193 | 1432.8 | 10.9 | | | b-MeAla | Val | MeLeu | MeLeu | Ala |
| DP-194 | 1398.8 | 11.2 | | | D-MeAla | MeAla | MeLeu | MePhe | MeLeu |
| DP-195 | 1342.7 | 10.1 | | | MeGly | Phe | MeVal | MePhe | Val |
| DP-196 | 1257.6 | 9.5 | | | | Ala | MePhe | Thr | MeAla |
| DP-197 | 1313.7 | 11.5 | | | | D-Ala | MePhe | MeLeu | Thr |
| DP-198 | 1285.6 | 10.4 | | | | D-Val | MePhe | Thr | MeAla |
| DP-199 | 1327.7 | 12.1 | | | | MeAla | MePhe | MeLeu | Thr |
| DP-200 | 1291.6 | 8.4 | | | | b-MeAla | Thr | MeLeu | Val |
| DP-201 | 1327.7 | 11.0 | | | | b-MeAla | MeLeu | MePhe | MeAla |
| DP-202 | 1313.7 | 11.5 | | | Ala | MeGly | MeLeu | MePhe | MeLeu |
| DP-203 | 1560.0 | 13.9 | | | D-Ala | MePhe | MeAla | MePhe | MeAla |
| DP-204 | 1560.0 | 13.9 | | | D-Val | MeAla | MeLeu | Thr | MeAla |
| DP-205 | 1608.0 | 13.9 | | | MeAla | Val | MePhe | Thr | MeLeu |
| DP-206 | 1574.0 | 14.5 | | | MeAla | MeAla | MeLeu | Thr | MeLeu |
| DP-207 | 1664.1 | 16.5 | | | MePhe | MePhe | MeLeu | MeAla | MeLeu |
| DP-208 | 1474.9 | 13.2 | | | D-MeAla | Ala | MePhe | Thr | MeAla |

TABLE 11-1-continued

| ID | MW | RT | | | | | | | | |
|---|---|---|---|---|---|---|---|---|---|---|
| DP-209 | 1438.8 | 10.6 | | | | D-Ala | Thr | MeAla | MePhe | MeLeu |
| DP-210 | 1502.9 | 14.2 | | | | D-Va | MePhe | MeLeu | Thr | MeAla |
| DP-211 | 1488.9 | 13.8 | | | | MeAla | MePhe | Thr | MeAla | MeLeu |
| DP-212 | 1432.8 | 10.8 | | | | b-MeAla | MeAla | MePhe | Thr | MeGly |
| DP-213 | 1452.8 | 11.1 | | | | D-MeAla | Val | MeLeu | Thr | Gly |
| DP-214 | 1432.8 | 11.8 | | | Thr | MePhe | Leu | MePhe | Phe | Thr |
| DP-215 | 1382.8 | 11.6 | | | Leu | MePhe | Thr | MeGly | Phe | MeGly |
| DP-216 | 1412.8 | 12.9 | | | MeVal | Gly | MeLeu | MeVal | Phe | MeLeu |
| DP-217 | 1384.8 | 12.1 | | | Leu | MeIle | Thr | Val | Phe | MePhe |
| DP-218 | 1410.8 | 12.4 | | | MeIle | Leu | MeLeu | Ala | Gly | Thr |
| DP-219 | 1499.0 | 14.6 | | | Leu | Ala | MeAla | MePhe | MePhe | MeLeu |
| DP-220 | 1396.8 | 12.1 | | | MeAla | MeAla | Thr | Phe | Phe | MeIle |
| DP-221 | 1398.8 | 11.4 | | | Phe | Phe | MeAla | Thr | Leu | MeLeu |
| DP-222 | 1412.8 | 9.8 | | | MeVal | Phe | Ser(tBu) | Gly | Thr | Leu |
| DP-223 | 1398.8 | 12.4 | | | Phe | MeVal | Leu | MeAla | Phe | MeLeu |
| DP-224 | 1396.8 | 12.1 | | | Leu | MeAla | Pro | MeAla | Gly | MeIle |
| DP-225 | 1410.8 | 10.8 | | | MePhe | g-MeAbu | MePhe | MeVal | Thr | MeGly |
| DP-226 | 1285.6 | 10.9 | | | Phe | D-Ala | Pro | Phe | MePhe | Ile |
| DP-227 | 1297.6 | 10.7 | | | Leu | D-Ala | MeLeu | MeIle | Thr | Phe |
| DP-228 | 1369.8 | 14.2 | | | MeLeu | D-Ala | MeLeu | MeLeu | MePhe | Ala |
| DP-229 | 1313.7 | 12.2 | | | Ala | D-Ala | MeLeu | MePhe | Thr | MeAla |
| DP-230 | 1313.7 | 11.8 | | | Leu | D-Val | MeLeu | MePhe | MePhe | Ile |
| DP-231 | 1325.7 | 11.7 | | | Phe | D-Val | MeLeu | MeVal | Gly | Thr |
| DP-232 | 1341.7 | 13.2 | | | Leu | D-Val | MeLeu | MeLeu | MePhe | MeLeu |
| DP-233 | 1327.7 | 12.6 | | | MeAla | D-Val | MeLeu | Ala | Phe | MeIle |
| DP-234 | 1369.8 | 14.3 | | | MeAla | D-Val | MeLeu | MePhe | MeLeu | MePhe |
| DP-235 | 1369.8 | 14.4 | | | MeIle | D-Va | MeLeu | Ala | MeLeu | Thr |
| DP-236 | 1311.7 | 11.4 | | | Phe | MeAla | MeLeu | Leu | MeIle | MeVal |
| DP-237 | 1223.6 | 10.2 | | | MeLeu | MeAla | Phe | Thr | MeGly | Ile |
| DP-238 | 1299.7 | 10.5 | | | MeLeu | b-MeAla | Leu | MeVal | MePhe | Ile |
| DP-239 | 1311.7 | 10.3 | | | MeLeu | b-MeAla | MeLeu | Gly | MeIle | Phe |
| DP-240 | 1341.7 | 12.3 | | | MeLeu | b-MeAla | Thr | MePhe | Ala | MePhe |
| DP-241 | 1327.7 | 11.9 | | | Phe | b-MeAla | MeIle | MePhe | Thr | MeAla |
| DP-242 | 1299.7 | 11.5 | | | MeLeu | D-MeAla | Leu | MeVal | MeAla | Ile |
| DP-243 | 1223.6 | 10.2 | | | MeLeu | D-MeAla | Phe | Thr | MeAla | MeVal |
| DP-244 | 1341.7 | 13.3 | | | MeLeu | D-MeAla | Thr | MeGly | MePhe | Ile |
| DP-245 | 1285.6 | 11.0 | | | MeLeu | D-MeAla | Leu | MeAla | MePhe | Ile |
| DP-246 | 1313.7 | 12.3 | | | Leu | MeGly | MeGly | MePhe | Ala | MePhe |
| DP-247 | 1327.7 | 12.8 | | | MeLeu | MeGly | Thr | MeAla | MePhe | MePhe |
| DP-248 | 1397.8 | 13.4 | | | MeLeu | MeGly | Thr | MePhe | MeLeu | Ala |
| DP-249 | 1355.8 | 11.9 | | | MeLeu | g-MeAbu | Thr | MeAla | MePhe | MePhe |
| DP-250 | 1341.7 | 11.5 | | | Phe | g-MeAbu | MeAla | MeAla | Ala | MePhe |
| DP-251 | 1223.6 | 11.5 | | | MeLeu | g-MeAbu | Leu | MeLeu | MePhe | MeIle |
| DP-252 | 1369.8 | 12.5 | | | MeLeu | g-MeAbu | MeVal | MeVal | MeLeu | Thr |
| DP-253 | 1214.6 | 10.8 | | | MePhe | MeAla | MeGly | MeAla | Phe | Thr |
| DP-254 | 1124.4 | 9.1 | | | MeAla | b-MeAla | Ala | Ala | Phe | MeLeu |
| DP-255 | 1124.4 | 9.1 | | | MeAla | D-Val | Thr | MeLeu | Thr | MeGly |
| DP-256 | 1242.6 | 12.2 | | | D-Val | Phe | Ile | MeAla | MeAla | MePhe |
| DP-257 | 1284.7 | 13.6 | | | D-Val | MePhe | MePhe | MeIle | MeAla | Thr |
| DP-258 | 1224.6 | 11.1 | | | D-Val | Ala | MeAla | MeLeu | MePhe | MeGly |
| DP-259 | 1228.6 | 11.8 | | | D-Val | MeLeu | MeAla | MeLeu | Thr | Leu |
| DP-260 | 1244.6 | 10.4 | | | MeAla | MeAla | Ala | MeLeu | Thr | MeLeu |
| DP-261 | 1242.6 | 10.4 | | | b-MeAla | Ala | MeIle | MeLeu | MePhe | MePhe |

TABLE 11-1-continued

| ID | Mass | RT | R1 | R2 | R3 | R4 | R5 | R6 | R7 |
|---|---|---|---|---|---|---|---|---|---|
| DP-262 | 1228.6 | 10.1 | | | | | Thr | MeAla | MePhe | MeLeu |
| DP-263 | 1073.3 | 8.4 | | | | D-Ala | Ala | Thr | MeAla | Phe |
| DP-264 | 1157.5 | 11.5 | | | | D-Val | MeLeu | Leu | MePhe | Thr |
| DP-265 | 1139.5 | 10.4 | | | | D-Val | MePhe | MeAla | Thr | MeGly |
| DP-266 | 1111.4 | 9.4 | | | | D-Val | MeAla | MeAla | MeLeu | Thr |
| DP-267 | 1097.4 | 9.1 | | | | MeAla | MePhe | MePhe | MeLeu | Thr |
| DP-268 | 1143.5 | 10.1 | | | | b-MeAla | MePhe | Leu | MeLeu | MeLeu |
| DP-269 | 1097.4 | 8.0 | | | | b-MeAla | MeAla | MePhe | MeLeu | Thr |
| DP-270 | 1103.4 | 7.9 | | | | D-MeAla | Thr | MeAla | MePhe | Ser(tBu) |
| DP-271 | 1089.3 | 7.4 | | | | MeGly | Thr | Ser(tBu) | MeGly | MePhe |
| DP-272 | 1139.5 | 8.6 | | | | g-MeAbu | MePhe | MeAla | MeAla | Ser(tBu) |
| DP-273 | 1412.8 | 11.1 | | g-MeAbu | | Ile | Leu | Thr | MeAla | MeLeu |
| DP-274 | 1313.7 | 10.0 | MeVal | g-MeAbu | Phe | MeLeu | MeVal | Phe | MePhe | MePhe |
| DP-275 | 1341.7 | 11.6 | g-MeAbu | | Ala | MeLeu | MeAla | Ile | Ala | Thr |
| DP-276 | 1311.7 | 10.1 | g-MeAbu | | Thr | MeGly | MeLeu | MePhe | Thr | MePhe |
| DP-277 | 1258.6 | 9.1 | g-MeAbu | | g-MeAbu | Ser(tBu) | MePhe | MeLeu | Thr | Gly |
| DP-278 | 1558.0 | 13.1 | D-Val | | Phe | MeLeu | Melle | Thr | Thr | Phe |
| DP-279 | 1546.0 | 13.7 | MeAla | | Ile | MeLeu | MePhe | MeVal | MeVal | MeAla |
| DP-280 | 1544.0 | 12.7 | MeAla | | Ile | Thr | MeLeu | Thr | MeAla | Gly |
| DP-281 | 1588.1 | 14.4 | b-MeAla | | MeLeu | MeAla | MeLeu | Gly | Thr | MeAla |
| DP-282 | 1501.9 | 12.7 | MeAla | | MeAla | Phe | Phe | Gly | MeLeu | MeLeu |
| DP-283 | 1544.0 | 12.7 | D-MeAla | | Ile | Leu | MePhe | MeLeu | MePhe | Gly |
| DP-284 | 1574.0 | 14.9 | MeGly | | MeLeu | Melle | MeVal | MePhe | MePhe | Thr |
| DP-285 | 1441.8 | 11.1 | MeGly | | MeLeu | Thr | Phe | MeVal | MePhe | MeAla |
| DP-286 | 1650.1 | 15.9 | | | Ala | MePhe | Ile | MeAla | MePhe | MeLeu |
| DP-287 | 1580.0 | 13.0 | | | Ala | MeLeu | Thr | MeLeu | Gly | Gly |
| DP-288 | 1342.7 | 10.1 | | | Ala | MeLeu | MeVal | MeAla | Thr | MeAla |
| DP-289 | 1650.1 | 15.9 | | | Phe | MeLeu | Ile | MeAla | MePhe | Gly |
| DP-290 | 1384.8 | 11.7 | | | Thr | MePhe | MeLeu | Melle | Thr | MeAla |
| DP-291 | 1418.8 | 11.3 | | | D-Ala | MeLeu | MePhe | MeLeu | MePhe | Gly |
| DP-292 | 1678.2 | 16.8 | | | D-Ala | Val | MeLeu | Thr | MeAla | MeLeu |
| DP-293 | 1517.9 | 12.2 | | | D-Val | Thr | MePhe | Ile | MePhe | Phe |
| DP-294 | 1370.7 | 11.0 | | | D-Val | MeGly | MeAla | MeVal | Thr | MeLeu |
| DP-295 | 1664.1 | 16.5 | | | D-Val | Ile | MeVal | MeAla | MeLeu | MeLeu |
| DP-296 | 1356.7 | 10.7 | | | MeAla | MePhe | MeVal | MeAla | MeLeu | MeLeu |
| DP-297 | 1574.0 | 13.5 | | | MeAla | Phe | Thr | MeLeu | MeLeu | MeVal |
| DP-298 | 1594.0 | 12.6 | | | b-MeAla | MePhe | MePhe | MeLeu | MeLeu | MeLeu |
| DP-299 | 1502.9 | 13.8 | | | b-MeAla | Val | MeLeu | Gly | Gly | Ile |
| DP-300 | 1574.0 | 14.5 | | | b-MeAla | Thr | MePhe | MePhe | MePhe | MeLeu |
| DP-301 | 1432.8 | 11.8 | | | D-MeAla | MeAla | MeLeu | Thr | MeLeu | MeLeu |
| DP-302 | 1560.0 | 14.0 | | | D-MeAla | Val | MePhe | Thr | MeLeu | MePhe |
| DP-303 | 1580.0 | 13.0 | | | MeGly | MeAla | Phe | MeAla | Phe | Gly |
| DP-304 | 1418.8 | 11.3 | | | MeGly | Val | Thr | Thr | MeLeu | MeLeu |
| DP-305 | 1313.7 | 11.5 | | | MeGly | Val | MeLeu | MePhe | MeLeu | MeAla |
| DP-306 | 1446.8 | 12.2 | | | | Ala | MePhe | MeLeu | Thr | Thr |
| DP-307 | 1277.6 | 8.8 | | | | D-Val | MeAla | Thr | MeLeu | Val |
| DP-308 | 1341.7 | 12.4 | | | | D-Val | MePhe | MePhe | MePhe | MeAla |
| DP-309 | 1452.8 | 11.1 | | | | MeAla | Val | MeLeu | MeAla | MePhe |
| DP-310 | 1271.6 | 10.1 | | | | MeAla | Val | MePhe | MeGly | Thr |
| DP-311 | 1291.6 | 9.4 | | | | MeAla | Thr | MeAla | Val | MeGly |
| DP-312 | 1452.8 | 10.1 | | | | b-MeAla | Val | MeLeu | MePhe | Gly |
| DP-313 | 1327.7 | 12.1 | | | | D-MeAla | MePhe | MeLeu | Thr | MeAla |
| DP-314 | 1438.8 | 10.5 | | | | MeGly | Val | MeLeu | MePhe | Gly |

TABLE 11-1-continued

| ID | Mass | RT | | | | | | | | |
|---|---|---|---|---|---|---|---|---|---|---|
| DP-315 | 1418.8 | 11.3 | | | MePhe | Ala | D-Ala | MeAla | MePhe | MeAla | Thr |
| DP-316 | 1277.6 | 8.9 | | | MePhe | Leu | MeGly | Thr | MeGly | Val | MeLeu |
| DP-317 | 1386.7 | 10.9 | | | MeAla | Ala | MeAla | Phe | Thr | MeAla | MeLeu |
| DP-318 | 1384.8 | 11.4 | MeAla | b-MeAla | Ala | MeLeu | MePhe | MeVal | Thr | MeVal | MeGly |
| DP-319 | 1266.6 | 9.6 | b-MeAla | D-MeAla | Ile | MePhe | Ala | MeVal | Thr | Phe | MeGly |
| DP-320 | 1333.7 | 10.9 | | | Ala | Leu | Phe | Phe | MeLeu | Leu | Phe |
| DP-321 | 1285.6 | 10.4 | | | D-Ala | Phe | Thr | Ile | Phe | Phe | Gly |
| DP-322 | 1243.6 | 9.9 | | | MeAla | Thr | MeAla | MePhe | MeLeu | MeLeu | MeVal |
| DP-323 | 1355.8 | 12.0 | | | b-MeAla | Leu | Phe | Phe | Leu | Leu | Leu |
| DP-324 | 1237.6 | 9.3 | | | b-MeAla | Leu | MeAla | Leu | Leu | Thr | Ala |
| DP-325 | 1341.7 | 11.8 | | | b-MeAla | Leu | MeAla | Phe | MeAla | Leu | MeLeu |
| DP-326 | 1243.6 | 8.9 | | | b-MeAla | MePhe | MeAla | MeAla | Thr | Phe | MeVal |
| DP-327 | 1223.6 | 9.5 | | | D-MeAla | Ile | Leu | Ala | MeGly | MeGly | Leu |
| DP-328 | 1237.6 | 10.3 | | | D-MeAla | Thr | Ala | MeGly | Phe | Phe | Leu |
| DP-329 | 1262.6 | 10.8 | | | | Ala | Leu | Phe | Thr | Thr | Ile |
| DP-330 | 1206.5 | 8.8 | | | | Ala | Phe | MeGly | Thr | Thr | Leu |
| DP-331 | 1276.6 | 11.4 | | | MeAla | Leu | Ile | Phe | Thr | Thr | Leu |
| DP-332 | 1290.7 | 12.0 | | | MeAla | Phe | Ile | MeLeu | MeLeu | Phe | Leu |
| DP-333 | 1242.6 | 12.1 | | | MeAla | Thr | MeAla | MeLeu | MePhe | Phe | MePhe |
| DP-334 | 1290.7 | 11.1 | | | b-MeAla | Phe | MeLeu | Ile | Thr | Thr | Leu |
| DP-335 | 1244.6 | 9.1 | | | b-MeAla | MeLeu | Thr | Phe | Gly | MePhe | MePhe |
| DP-336 | 1284.7 | 12.4 | | | b-MeAla | Leu | MeLeu | Thr | Phe | Phe | MeLeu |
| DP-337 | 1172.5 | 8.8 | | | b-MeAla | MeVal | Ala | MeLeu | MePhe | MePhe | Thr |
| DP-338 | 1290.7 | 12.0 | | | D-MeAla | Phe | Ile | MeLeu | Leu | Leu | Thr |
| DP-339 | 1256.6 | 12.2 | | | D-MeAla | Thr | Gly | Leu | MeLeu | Ser(tBu) | Phe |
| DP-340 | 1202.5 | 8.8 | | | D-MeAla | MeAla | MeLeu | Ala | MeLeu | MePhe | MePhe |
| DP-341 | 1144.4 | 8.9 | | | D-MeAla | MeAla | MeLeu | MePhe | MeAla | MeAla | MeAla |
| DP-342 | 1095.4 | 10.6 | | | D-MeAla | D-MeAla | Leu | Leu | MeGly | Thr | MeGly |
| DP-343 | 1171.5 | 11.8 | | | | MeLeu | Ala | Leu | MeLeu | MeLeu | Phe |
| DP-344 | 1503.9 | 12.5 | MeAla | MeAla | MeLeu | Ala | Phe | MeAla | MeAla | MePhe |
| DP-345 | 1433.8 | 9.9 | MeAla | MeAla | Ala | MeLeu | MeLeu | MeLeu | MePhe | Thr |
| DP-346 | 1461.8 | 10.0 | b-MeAla | MeAla | Ala | Thr | MeAla | MeAla | MePhe | Thr |
| DP-347 | 1503.9 | 12.5 | D-MeAla | MeLeu | MeLeu | MeAla | MeAla | MeLeu | MeLeu | Thr |
| DP-348 | 1475.8 | 11.3 | D-MeAla | MeAla | MePhe | MePhe | MeAla | Ala | Ala | Ala |
| DP-349 | 1314.6 | 9.3 | | | MeAla | Thr | Val | MeAla | MePhe | MePhe |
| DP-350 | 1474.9 | 13.3 | | | MeAla | MeLeu | Leu | MeLeu | Thr | Thr |
| DP-351 | 1488.9 | 12.9 | | | MeAla | Phe | MePhe | MePhe | MeAla | Ala |
| DP-352 | 1390.7 | 9.4 | | | Val | MePhe | MeLeu | MeVal | MeAla | MeLeu |
| DP-353 | 1376.7 | 10.3 | | | MePhe | MeAla | Phe | MeVal | MeAla | Thr |
| DP-354 | 1314.6 | 9.2 | | | MeVal | Ala | Phe | Thr | Thr | MePhe |
| DP-355 | 1362.7 | 9.5 | | | Ala | MeLeu | MeLeu | MeLeu | MeAla | Ala |
| DP-356 | 1390.7 | 10.3 | | | MeVal | Phe | MePhe | Thr | MeLeu | MePhe |
| DP-357 | 1243.6 | 9.1 | | | MeAla | MePhe | MePhe | MePhe | MeAla | Thr |
| DP-358 | 1313.7 | 10.5 | | | b-MeAla | MePhe | Leu | MePhe | MeAla | MeAla |
| DP-359 | 1403.8 | 13.3 | | | D-MeAla | MeVal | MeAla | Leu | MeLeu | MeLeu |
| DP-360 | 1475.8 | 10.2 | MePhe | b-MeAla | MeAla | MeAla | Ala | MeLeu | MeAla | Thr |
| DP-361 | 1433.8 | 8.8 | | | b-MeAla | MeAla | MeGly | MeLeu | MeAla | MePhe |
| DP-362 | 1503.9 | 11.5 | | | b-MeAla | MeAla | Ala | Ile | MeAla | Thr |
| DP-363 | 1433.8 | 9.9 | | | D-MeAla | Ala | MeLeu | Phe | MeLeu | MePhe |
| DP-364 | 1558.0 | 11.5 | | | g-MeAbu | Phe | MeLeu | Pro | Ile | MeLeu | Gly |
| DP-365 | 1469.9 | 10.2 | | | g-MeAbu | MeLeu | Thr | MeAla | MeVal | Gly | MeLeu |
| DP-366 | 1602.1 | 14.0 | | | g-MeAbu | MeLeu | MeAla | Ile | MeLeu | MePhe | MePhe |
| DP-367 | 1475.8 | 11.3 | | | MeAla | MePhe | Thr | MeLeu | MeLeu | Ala | MePhe |

TABLE 11-1-continued

| ID | Mass | RT | | | | | | | | |
|---|---|---|---|---|---|---|---|---|---|---|
| DP-368 | 1385.7 | 9.6 | | | MeAla | MeLeu | Ala | MeAla | MePhe | MeAla |
| DP-369 | 1474.9 | 12.3 | | | b-MeAla | MeLeu | Leu | MeLeu | Thr | Ala |
| DP-370 | 1404.8 | 10.2 | | | b-MeAla | MeVal | MePhe | MePhe | Ala | MeGly |
| DP-371 | 1398.8 | 12.2 | | | D-MeAla | MeLeu | Thr | MeAla | MePhe | MeGly |
| DP-372 | 1446.8 | 10.6 | | | g-MeAbu | Val | MeLeu | Thr | MePhe | Gly |
| DP-373 | 1517.0 | 13.3 | | | g-MeAbu | MeAla | MeLeu | MePhe | MePhe | Ile |
| DP-374 | 1412.8 | 10.8 | | | g-MeAbu | MeAla | MeLeu | Thr | MePhe | MeGly |
| DP-375 | 1362.7 | 9.4 | | | MeAla | Ala | MeLeu | Phe | MeVal | MeAla |
| DP-376 | 1440.9 | 13.6 | | | MeAla | MeAla | MeVal | Phe | MeLeu | MeAla |
| DP-377 | 1376.7 | 10.3 | | | MeAla | MePhe | MePhe | Thr | MeAla | Thr |
| DP-378 | 1277.6 | 8.8 | | | | Ala | Thr | MeAla | MePhe | MePhe |
| DP-379 | 1347.7 | 10.4 | | | | b-MeAla | Thr | MeAla | MeLeu | Val |
| DP-380 | 1257.6 | 9.5 | | | | D-MeAla | MeAla | MePhe | MeLeu | Val |
| DP-381 | 1347.7 | 11.3 | | | | D-Val | MeLeu | Thr | Thr | Phe |
| DP-382 | 1305.6 | 9.7 | | | | g-MeAbu | Thr | MePhe | MePhe | Val |
| DP-383 | 1305.6 | 8.1 | | | | g-MeAbu | MeLeu | MeAla | MeAla | Val |
| DP-384 | 1341.7 | 10.6 | | | | g-MeAbu | Thr | MePhe | Thr | MeAla |
| DP-385 | 1285.6 | 8.8 | | | | MeAla | Val | MePhe | MeLeu | Thr |
| DP-386 | 1347.7 | 11.4 | | | | MeAla | Thr | MeAla | MeLeu | Val |
| DP-387 | 1403.8 | 13.3 | | | | MeGly | MeLeu | Leu | MeLeu | MePhe |
| DP-388 | 1257.6 | 9.6 | | | | Ile | Val | MePhe | MeLeu | Thr |
| DP-389 | 1489.9 | 11.3 | | | Ala | MeVal | MePhe | MeVal | Thr | MeGly |
| DP-390 | 1580.0 | 11.9 | | | b-MeAla | Val | MePhe | MePhe | MeLeu | Gly |
| DP-391 | 1475.8 | 9.8 | | | b-MeAla | Ala | MePhe | MeVal | Gly | Thr |
| DP-392 | 1517.9 | 10.6 | | | g-MeAbu | Ile | MeAla | MePhe | Thr | MeGly |
| DP-393 | 1509.9 | 10.7 | | | MeAla | Ile | MeAla | Gly | Thr | MeAla |
| DP-394 | 1503.8 | 11.9 | | | MeAla | Phe | MeAla | Ile | MeGly | Thr |
| DP-395 | 1503.9 | 12.1 | | | MeAla | Phe | MeLeu | Ile | MeAla | Thr |
| DP-396 | 1438.8 | 10.6 | | | | MePhe | MePhe | MeAla | MePhe | Val |
| DP-397 | 1488.9 | 12.9 | | | | Ala | Thr | MeAla | MeLeu | Val |
| DP-398 | 1404.8 | 9.8 | | | | b-MeAla | MeGly | MeAla | Ala | MeLeu |
| DP-399 | 1488.9 | 13.8 | | | | D-MeAla | MePhe | MePhe | MeLeu | MeLeu |
| DP-400 | 1404.8 | 10.9 | | | | D-MeAla | MePhe | Thr | Val | MeAla |
| DP-401 | 1466.8 | 11.5 | | | | D-Val | Thr | MeLeu | MePhe | Val |
| DP-402 | 1466.8 | 9.9 | | | | g-MeAbu | Val | MeAla | Gly | MePhe |
| DP-403 | 1502.9 | 12.6 | | | | g-MeAbu | Thr | MePhe | MeLeu | Val |
| DP-404 | 1446.8 | 10.3 | | | | g-MeAbu | MeAla | MePhe | Ala | MeLeu |
| DP-405 | 1432.8 | 11.8 | | | | MeAla | MePhe | MeGly | MePhe | MeLeu |
| DP-406 | 1362.7 | 9.4 | | | | MePhe | MeGly | MePhe | MeAla | Thr |
| DP-407 | 1418.8 | 11.3 | b-MeAla | | | MeGly | MeLeu | MeVal | Thr | MeAla |
| DP-408 | 1328.7 | 9.4 | D-MeAla | MePhe | | Thr | MeAla | Phe | MeAla | MeGly |
| DP-409 | 1386.7 | 10.8 | MeAla | Ala | | MeAla | Phe | MeAla | MeAla | Thr |
| DP-410 | 1266.6 | 9.6 | | MePhe | | Ala | MeLeu | Val | Val | MeGly |
| DP-411 | 1251.6 | 9.5 | | Leu | | Ile | MeGly | Val | Val | Leu |
| DP-412 | 1307.7 | 11.5 | | MeVal | | Leu | Phe | Leu | Val | Leu |
| DP-413 | 1279.7 | 11.1 | | MeLeu | | Thr | Phe | Ala | Leu | MeLeu |
| DP-414 | 1223.6 | 9.5 | | MeAla | | Ala | MeVal | MeLeu | Ala | Thr |
| DP-415 | 1333.7 | 10.9 | | Ile | | Leu | Phe | MeLeu | MePhe | Phe |
| DP-416 | 1341.7 | 12.4 | | Phe | | Leu | Thr | Leu | Leu | MeLeu |
| DP-417 | 1279.7 | 12.2 | | MeLeu | | Phe | MeLeu | MeAla | MeAla | MeVal |
| DP-418 | 1265.6 | 11.6 | | MeLeu | | Thr | Phe | MeVal | MeVal | Ala |
| DP-419 | 1257.6 | 10.6 | | MeAla | | MeLeu | Thr | MeAla | MePhe | MeGly |
| DP-420 | 1223.6 | 9.5 | | Leu | | Ala | Leu | MeGly | Leu | Leu |

TABLE 11-1-continued

| ID | Mass | RT | P1 | P2 | P3 | P4 | P5 | P6 | P7 |
|---|---|---|---|---|---|---|---|---|---|
| DP-421 | 1237.6 | 10.3 | | MeAla | Thr | Ala | Leu | MeGly | Phe | Leu |
| DP-422 | 1215.5 | 9.0 | | MeAla | MePhe | Thr | MeAla | Ile | Phe | MeAla |
| DP-423 | 1220.5 | 8.5 | | | b-MeAla | Thr | Phe | Ile | Leu | MeLeu |
| DP-424 | 1276.6 | 10.4 | | | b-MeAla | Leu | Thr | Phe | Ile | Leu |
| DP-425 | 1256.6 | 11.2 | | | b-MeAla | Ile | MeVal | Phe | Thr | Leu |
| DP-426 | 1258.6 | 9.8 | | | b-MeAla | MePhe | Gly | MeLeu | Phe | Ser(tBu) |
| DP-427 | 1242.6 | 11.2 | | | b-MeAla | Thr | MeAla | Phe | MeLeu | MePhe |
| DP-428 | 1180.5 | 10.3 | | | b-MeAla | MePhe | Thr | Thr | MeAla | Gly |
| DP-429 | 1312.7 | 13.7 | | | b-MeAla | MeLeu | MeLeu | Ile | MePhe | Thr |
| DP-430 | 1206.5 | 8.8 | | | D-Ala | Phe | Leu | MeGly | Phe | Leu |
| DP-431 | 1220.5 | 9.4 | | | D-MeAla | Phe | Thr | Phe | Leu | MeLeu |
| DP-432 | 1270.7 | 12.8 | | | D-MeAla | MeVal | MeLeu | Thr | Phe | MeLeu |
| DP-433 | 1152.5 | 10.2 | | | D-MeAla | MeVal | Thr | MeGly | Ile | MeAla |
| DP-434 | 1242.6 | 12.1 | | | D-MeAla | Thr | MeAla | Phe | MeLeu | MePhe |
| DP-435 | 1138.5 | 9.9 | | | D-MeAla | MePhe | Thr | MeAla | MeLeu | Gly |
| DP-436 | 1220.5 | 9.4 | | | MeAla | Phe | Gly | Thr | Leu | Phe |
| DP-437 | 1244.6 | 10.2 | | | MeAla | Ser(tBu) | MeLeu | Thr | Gly | MePhe |
| DP-438 | 1202.5 | 8.8 | | | MeAla | Ser(tBu) | Gly | MeVal | MePhe | Phe |
| DP-439 | 1152.5 | 10.2 | | | MeAla | MeGly | Phe | MeLeu | Thr | MeAla |
| DP-440 | 1095.4 | 9.6 | | | | b-MeAla | MePhe | MeLeu | Thr | MeGly |
| DP-441 | 1219.6 | 12.5 | | | | D-MeAla | MeLeu | MePhe | Leu | MePhe |
| DP-442 | 1219.6 | 12.5 | | D-MeAla | MeAla | Ala | MePhe | Thr | MePhe | Thr |
| DP-443 | 1461.8 | 11.1 | | D-MeAla | MeLeu | MeAla | Thr | MeAla | MePhe | MeAla |
| DP-444 | 1385.7 | 9.6 | | MeAla | Ala | MeAla | MeLeu | MePhe | MePhe | Thr |
| DP-445 | 1461.8 | 11.1 | | | | b-MeAla | MeLeu | Leu | MeAla | MeLeu |
| DP-446 | 1418.8 | 10.4 | | | | b-MeAla | MeVal | MeLeu | Ile | MeLeu |
| DP-447 | 1426.8 | 11.9 | | | | b-MeAla | MeVal | MeVal | Gly | Leu |
| DP-448 | 1342.7 | 9.1 | | | | b-MeAla | MeVal | MeVal | Ile | MeAla |
| DP-449 | 1342.7 | 9.2 | | | | b-MeAla | MeVal | Val | Phe | MeGly |
| DP-450 | 1475.8 | 10.0 | | | | b-MeAla | MeVal | Val | MePhe | MeAla |
| DP-451 | 1474.9 | 13.3 | | | | b-MeAla | MeLeu | Leu | Thr | Ala |
| DP-452 | 1551.9 | 12.1 | | | | D-MeAla | MeLeu | MePhe | MeLeu | Gly |
| DP-453 | 1398.8 | 12.1 | | | | D-MeAla | MeVal | Va | Phe | MeGly |
| DP-454 | 1546.0 | 13.3 | | | | D-MeAla | Phe | MeLeu | Thr | MeLeu |
| DP-455 | 1503.9 | 12.1 | | | | D-MeAla | MePhe | MeAla | Ile | MeLeu |
| DP-456 | 1551.9 | 12.1 | | | | D-MeAla | MeAla | Val | Gly | MeLeu |
| DP-457 | 1433.8 | 9.2 | | | | MeAla | Ala | Val | Gly | MePhe |
| DP-458 | 1314.6 | 9.2 | | | | MeAla | MeVal | MeAla | MeAla | Phe |
| DP-459 | 1546.0 | 13.3 | | | | MeAla | MeVal | MeAla | Thr | MeGly |
| DP-460 | 1447.8 | 10.1 | | | | MeAla | MeLeu | MeAla | MePhe | MeAla |
| DP-461 | 1403.8 | 12.2 | | | | b-MeAla | Leu | MeAla | MeLeu | MePhe |
| DP-462 | 1243.6 | 9.1 | | | | D-MeAla | MePhe | MeAla | MeLeu | MeLeu |
| DP-463 | 1362.7 | 9.4 | | | | D-MeAla | MePhe | MeGly | Val | Ala |
| DP-464 | 1404.8 | 10.9 | | | | MeAla | MeAla | MeLeu | Thr | MeAla |
| DP-465 | 1386.7 | 9.8 | | MePhe | Ala | Phe | MeVal | Thr | MeAla | Thr |
| DP-466 | 1356.7 | 11.6 | | MePhe | MeLeu | Leu | MeVal | Thr | MeAla | MeGly |
| DP-467 | 1300.6 | 9.4 | | Phe | MePhe | MeAla | MeVal | Leu | MeGly | Ala |
| DP-468 | 1412.8 | 11.8 | | Ile | MePhe | MeLeu | Ala | Leu | MeVal | Thr |
| DP-469 | 1356.7 | 11.6 | | MePhe | Leu | Leu | MeVal | Ala | MeAla | MeGly |
| DP-470 | 1300.6 | 9.4 | | Ala | MePhe | MeLeu | MeAla | MeVal | MeGly | Phe |
| DP-471 | 1299.7 | 11.0 | | b-MeAla | b-MeAla | Leu | Thr | MeGly | MePhe | MeLeu |
| DP-472 | 1265.6 | 10.3 | | b-MeAla | MeAla | Phe | Val | MeGly | Thr | Leu |
| DP-473 | 1285.6 | 10.3 | | b-MeAla | Thr | MeLeu | MeAla | MePhe | MeLeu | Phe |

TABLE 11-1-continued

| | | | | | | | | |
|---|---|---|---|---|---|---|---|---|
| DP-474 | 1243.6 | 9.9 | | | D-MeAla | Thr | MeAla | Ala | MePhe | MeVal |
| DP-475 | 1223.6 | 9.7 | | | D-MeAla | Leu | Ile | MeGly | Leu | Thr |
| DP-476 | 1195.5 | 9.7 | | | D-MeAla | MeAla | Ala | MeLeu | MeAla | Thr |
| DP-477 | 1327.7 | 10.9 | | | g-MeAbu | MeAla | MeLeu | Thr | MeGly | MePhe |
| DP-478 | 1279.7 | 11.6 | | | MeAla | Leu | MeAla | Phe | Leu | MeLeu |
| DP-479 | 1265.6 | 11.6 | | | MeAla | MeAla | Thr | MeGly | Ala | MeVal |
| DP-480 | 1195.5 | 9.7 | | | MeAla | MeAla | Ala | MeLeu | MePhe | Thr |
| DP-481 | 1327.7 | 12.8 | | | MeAla | Ile | MeLeu | MePhe | Thr | MeAla |
| DP-482 | 1257.6 | 10.6 | | | MeAla | MeAla | MeLeu | MePhe | Thr | MeGly |
| DP-483 | 1531.9 | 13.2 | | | Ile | MeLeu | MePhe | Thr | MeGly |
| DP-484 | 1560.0 | 14.1 | | | Ala | Ile | MeLeu | MeVal | Thr | MeGly |
| DP-485 | 1110.4 | 8.7 | | | D-Val | Ala | MeAla | Phe | Ile | MeLeu |
| DP-486 | 1234.5 | 10.0 | | | D-MeAla | Thr | MeLeu | Ile | Leu | MePhe |
| DP-487 | 1242.6 | 10.4 | | | D-MeAla | Phe | MeLeu | Phe | MeLeu | Thr |
| DP-488 | 1256.6 | 12.2 | | | g-MeAbu | MeLeu | MeVal | Ile | Thr | Leu |
| DP-489 | 1138.5 | 9.9 | | | MeAla | MeAla | MePhe | Phe | MeLeu | Gly |
| DP-490 | 1356.7 | 9.7 | | | b-MeAla | Phe | MeVal | Thr | Thr | MeAla |
| DP-491 | 1342.7 | 10.1 | | | D-Ala | Ile | MeAla | MeAla | MeAla | MeAla |
| DP-492 | 1398.8 | 12.2 | | | MeAla | MeLeu | Thr | MeVal | Thr | Ile |
| DP-493 | 1488.9 | 14.2 | | | MeGly | Thr | MePhe | MeLeu | MePhe | MeLeu |
| DP-494 | 1171.5 | 11.8 | | | | Ile | MeAla | Leu | Ala | MeLeu |
| DP-495 | 1503.9 | 10.9 | | | b-MeAla | Ile | MePhe | MeAla | MeLeu | MeGly |
| DP-496 | 1574.0 | 13.2 | | | b-MeAla | MeLeu | MePhe | MeVal | Thr | MeAla |
| DP-497 | 1489.9 | 10.2 | | | b-MeAla | MeGly | Thr | MeAla | Phe | Ala |
| DP-498 | 1461.8 | 9.5 | | | b-MeAla | Ala | MeVal | MeAla | Thr | MeGly |
| DP-499 | 1664.1 | 15.3 | | | b-MeAla | MePhe | MeLeu | MeAla | Phe | Ile |
| DP-500 | 1531.9 | 12.0 | | | b-MeAla | MePhe | MeLeu | MeAla | MePhe | MeLeu |
| DP-501 | 1580.0 | 13.0 | | | D-Ala | Val | MeLeu | Thr | Val | Gly |
| DP-502 | 1489.9 | 11.3 | | | D-Ala | Phe | MeAla | MeVal | MePhe | MeGly |
| DP-503 | 1594.0 | 13.6 | | | D-MeAla | Val | MeLeu | Thr | MePhe | MeLeu |
| DP-504 | 1509.9 | 10.7 | | | D-MeAla | Phe | Gly | MeAla | MeLeu | MeAla |
| DP-505 | 1433.8 | 9.2 | | | D-MeAla | Ala | MeVal | Thr | MeAla | MeAla |
| DP-506 | 1503.9 | 11.9 | | | D-MeAla | Phe | MeLeu | MeVal | Gly | Thr |
| DP-507 | 1461.8 | 10.4 | | | D-MeAla | MeGly | Thr | MeAla | MeGly | MeLeu |
| DP-508 | 1433.8 | 9.5 | | | D-MeAla | MeAla | Ala | MeAla | Phe | Thr |
| DP-509 | 1447.8 | 10.1 | | | D-MeAla | MeAla | Val | MeAla | MePhe | MeAla |
| DP-510 | 1588.1 | 14.9 | | | D-Val | MeAla | MePhe | Thr | Thr | MeAla |
| DP-511 | 1280.6 | 9.1 | b-MeAla | MeAla | MePhe | Ala | MeLeu | MeLeu | Val |
| DP-512 | 1095.4 | 10.6 | | | | D-MeAla | Thr | MeGly | MeLeu | Ile |
| DP-513 | 1285.6 | 10.4 | | Ala | Leu | Phe | Ile | Thr | Gly |
| DP-514 | 1251.6 | 9.4 | | b-MeAla | Val | Leu | Thr | Ala | Leu |
| DP-515 | 1248.6 | 10.2 | | | MeVal | D-Ala | Leu | Ile | Leu | Phe |
| DP-516 | 1285.6 | 10.4 | | b-MeAla | MeVal | Thr | Phe | MeAla | MeGly |
| DP-517 | 1398.7 | 10.2 | MeGly | Phe | MeLeu | Ser(tBu) | MeAla | Ile | MeAla |
| DP-518 | 1369.8 | 14.3 | | | MeGly | MeLeu | Gly | MePhe | Ala | MeLeu |
| DP-519 | 1214.6 | 11.3 | | | | MeLeu | Thr | MeLeu | MePhe | Thr |
| DP-520 | 1143.5 | 11.1 | | | | MeGly | Ile | Leu | MePhe | MeAla |
| DP-521 | 1032.3 | 7.9 | | | | MeGly | MeGly | Thr | MeAla | Sert(tBu) |
| DP-522 | 942.2 | 4.9 | | | | b-MeAla | b-MeAla | Thr | MeLeu | Sert(tBu) |
| DP-523 | 998.3 | 7.8 | | | | MeAla | MeAla | MePhe | MeAla | Thr |
| DP-524 | 968.2 | 6.7 | | | | g-MeAbu | g-MeAbu | MeAla | MeLeu | Thr |
| DP-525 | 1012.3 | 6.5 | | | | g-MeAbu | MePhe | MeLeu | Thr | MeGly |
| DP-526 | 974.2 | 7.2 | | | | D-Val | Ala | Thr | Thr | MeAla |

TABLE 11-1-continued

| ID | MW | RT | | | | | | |
|---|---|---|---|---|---|---|---|---|
| DP-527 | 998.3 | 7.9 | | | | D-MeAla | MeLeu | Thr |
| DP-528 | 984.2 | 7.3 | | | | D-Ala | MeLeu | Thr |
| DP-529 | 998.3 | 7.8 | | | | D-Ala | MeLeu | Thr |
| DP-530 | 972.2 | 6.7 | | | | Ala | MePhe | Thr |
| DP-531 | 871.1 | 5.7 | | | | MeGly | Thr | MeAla |
| DP-532 | 885.1 | 5.3 | | | | b-MeAla | Thr | MeAla |
| DP-533 | 855.1 | 6.9 | | | | MeAla | MePhe | MeLeu |
| DP-534 | 885.1 | 4.4 | | | | g-MeAbu | Thr | MeLeu |
| DP-535 | 885.1 | 4.3 | | | | g-MeAbu | MePhe | Thr |
| DP-536 | 837.1 | 5.8 | | | | D-MeAla | MePhe | Thr |
| DP-537 | 841.1 | 6.4 | | | | D-Ala | MePhe | MeLeu |
| DP-538 | 813.0 | 5.4 | | | | D-Ala | MeAla | MePhe |
| DP-539 | 875.1 | 6.2 | | | | Ala | MeAla | MePhe |
| DP-540 | 1238.6 | 11.9 | | MePhe | | MeAla | Thr | MeAla |
| DP-541 | 1325.7 | 12.5 | MeAla | Thr | | MePhe | MeLeu | Pro |
| DP-542 | 1311.7 | 12.0 | MeAla | Thr | | EtPhe | MeLeu | Pro |
| DP-543 | 1224.6 | 11.4 | | MeGly | | nPrGly | MeLeu | MePhe |
| DP-544 | 1341.7 | 13.5 | nPrGly | Leu | | MeGly | Thr | MePhe |
| DP-545 | 1341.7 | 13.4 | MeGly | Leu | | nPrGly | Ala | MePhe |
| DP-546 | 1327.7 | 12.8 | MeGly | Leu | | MeGly | Ala | MePhe |
| DP-547 | 1224.6 | 11.4 | | D-Ala | | MePhe | Thr | nPrGly |
| DP-548 | 1235.6 | 9.5 | MeAla | Leu | | Ala | Aze(2) | Thr |
| DP-549 | 1263.6 | 10.6 | MeAla | Leu | | Ala | Pic(2) | Thr |
| DP-550 | 1309.7 | 10.6 | Aze(2) | MeLeu | | Leu | Gly | MeLeu |
| DP-551 | 1337.7 | 11.8 | Pic(2) | Aze(2) | | Leu | Gly | MeLeu |
| DP-552 | 1267.6 | 9.2 | MeAla | Pic(2) | | Leu | Gly | MeLeu |
| DP-553 | 1295.6 | 10.3 | MeAla | MeLeu | | Leu | Gly | MeLeu |
| DP-554 | 1267.6 | 9.2 | MeAla | MeLeu | | Leu | Gly | Aze(2) |
| DP-555 | 1295.6 | 10.3 | MeAla | MeLeu | | Leu | Gly | Pic(2) |
| DP-556 | 1267.6 | 9.2 | MeAla | MeLeu | | Leu | Gly | MeLeu |
| DP-557 | 1295.6 | 10.3 | MeAla | MeLeu | | Leu | Gly | MeLeu |
| DP-558 | 1297.6 | 10.8 | MeAla | MeLeu | | Aib | MeGly | Thr |
| DP-559 | 1325.7 | 11.9 | MeAla | Leu | | Phg | MeGly | Thr |
| DP-560 | 1237.6 | 10.2 | MeAla | Leu | | Thr | MePhe | MePhe |
| DP-561 | 1285.6 | 10.7 | MeAla | | | Thr | MePhe | MePhe |
| DP-562 | 1103.4 | 7.9 | | | | Aib | MeIle | MeLeu |
| DP-563 | 1151.4 | 8.4 | | MeLeu | | Phg | MeIle | MeLeu |
| DP-564 | 1249.6 | 10.5 | MeAla | | | MeLeu | Gly | MeLeu |
| DP-565 | 1402.7 | 9.6 | | Phe | | Ala | MeLeu | Thr |
| DP-566 | 1209.5 | 8.2 | | | | Ala | MeLeu | Thr |
| DP-567 | 1101.4 | 8.6 | | | | Ala | MePhe | Ile |
| DP-568 | 1181.5 | 7.2 | | | | D-Ala | MePhe | Ile |
| DP-569 | 1192.5 | 7.7 | | | | D-Ala | MePhe | MeLeu |
| DP-570 | 1560.0 | 12.8 | | | D-Ala | Val | MePhe | MeLeu |
| DP-571 | 1158.4 | 8.3 | | | D-Ala | Val | MePhe | Val |
| DP-572 | 1508.9 | 12.5 | | | Ala | Leu | MeIle | Val |
| DP-573 | 1302.7 | 13.6 | | | Ala | Leu | MeIle | MePhe |
| DP-574 | 1560.0 | 13.3 | | D-Val | Ala | Leu | MeLeu | MePhe |
| DP-575 | 1315.7 | 9.8 | | D-Val | Thr | MeAla | MePhe | Phe |
| DP-576 | 1412.8 | 12.3 | | D-Val | Ala | Thr | MeAla | Phe |
| DP-577 | 1409.8 | 12.2 | | D-MeAla | MeAla | Thr | MeAla | Thr |
| DP-578 | 1506.9 | 9.5 | | MeAla | MePhe | MePhe | MeLeu | MeGly |
| DP-579 | 1505.9 | 12.5 | D-Ala | MeAla | MePhe | MeLeu | Thr | MeGly |

TABLE 11-1-continued

| ID | Mass | Value | aa1 | aa2 | aa3 | aa4 | aa5 | aa6 | aa7 |
|---|---|---|---|---|---|---|---|---|---|
| DP-580 | 1645.1 | 13.2 | | D-Ala | Leu | Phe | Leu | Leu | MePhe |
| DP-581 | 1522.9 | 10.6 | | MeAla | Thr | MeAla | MeVal | Phe | MeGly |
| DP-582 | 1597.1 | 14.1 | D-Val | MeAla | MeLeu | MeLeu | MeGly | MePhe | Ala |
| DP-583 | 1497.9 | 13.1 | D-MeAla | MeLeu | Phe | Thr | MeGly | MeAla | MeVal |
| DP-584 | 1512.0 | 13.8 | D-Val | MeAla | MeLeu | MeLeu | MeGly | MePhe | Ala |
| DP-585 | 1448.9 | 12.3 | | D-Val | MeLeu | MePhe | MeLeu | His | MeGly |
| DP-586 | 1547.0 | 15.7 | | D-Val | MeLeu | MePhe | MeLeu | His | MeLeu |
| DP-587 | 1482.0 | 14.2 | | D-Val | MeAla | MePhe | MeLeu | Lys(Me2) | MeGly |
| DP-588 | 1580.2 | 17.6 | | D-Val | MeLeu | MePhe | MeLeu | Lys(Me2) | MeLeu |
| DP-589 | 1454.9 | 12.9 | | D-Val | MeAla | MePhe | MeLeu | Glu | MeGly |
| DP-590 | 1496.0 | 12.8 | | D-Val | MeAla | MePhe | MeLeu | Arg(Me2) | MeGly |
| DP-591 | 1431.8 | 12.2 | | D-Val | MeAla | MePhe | MeLeu | Ala(3Pyr) | MeGly |
| DP-592 | 1686.2 | 15.5 | MeGly | Phe | MeLeu | MeLeu | Phe | MeLeu | Leu |
| DP-593 | 1599.1 | 13.8 | MeGly | Phe | MeLeu | MeLeu | Phe | MeLeu | Ala |
| DP-594 | 1705.2 | 16.9 | MeGly | Phe | MeLeu | MeLeu | Phe | MeLeu | Leu |
| DP-595 | 1572.0 | 12.5 | MeGly | Phe | MeLeu | MeLeu | Phe | MeLeu | Leu |
| DP-596 | 1678.1 | 15.6 | MeGly | Phe | MeLeu | MeLeu | Phe | MeLeu | Leu |
| DP-597 | 1613.1 | 12.5 | MeGly | Phe | MeLeu | MeGly | Phe | MeLeu | Leu |
| DP-598 | 1733.3 | 16.0 | MeAla | Phe | MeLeu | MeLeu | Phe | MeLeu | Ala |
| DP-599 | 1563.0 | 12.4 | MeGly | Phe | MeLeu | MeAla | Phe | MeLeu | Leu |
| DP-600 | 1697.2 | 16.4 | | Phe | MeLeu | MeLeu | Gln | MePhe | Phe |
| DP-601 | 1564.0 | 13.1 | | Ala | Phe | MeLeu | Thr | MePhe | Gln |
| DP-602 | 1517.9 | 11.0 | | Ala | Phe | MeLeu | Gln(Me2) | MePhe | Ala |
| DP-603 | 1515.9 | 12.0 | | Ala | Phe | MeLeu | Thr | MePhe | Leu |
| DP-604 | 1546.0 | 11.4 | | Ala | Phe | MeLeu | Thr | MePhe | Gly |
| DP-605 | 1480.8 | 11.9 | | Ala | Tyr(3-F) | MeLeu | Thr | MePhe | Tyr(3-F) |
| DP-606 | 1528.9 | 12.4 | | Ala | Phe | MeLeu | Met(O2) | MePhe | Leu |
| DP-607 | 1565.0 | 12.8 | | Ala | Phe | MeLeu | Thr | MePhe | Gly |
| DP-608 | 1519.9 | 12.3 | | Ala | Phe | MeLeu | Ala(4-Thz) | MePhe | Gly |
| DP-609 | 1499.9 | 12.7 | | Ala | Phe | MeLeu | Gln(Me) | MePhe | Ala |
| DP-610 | 1501.9 | 11.7 | | Ala | Phe | MeLeu | Thr | MePhe | Gly |
| DP-611 | 1430.8 | 11.4 | | Ala | Phe | MeLeu | Thr | MePhe | Algly |
| DP-612 | 1444.8 | 12.0 | | Ala | Phe | MeLeu | Ala(CN) | MePhe | Ala |
| DP-613 | 1413.8 | 11.4 | MeGly | MeAla | MeLeu | Leu | MePhe | Phe | MeLeu |
| DP-614 | 1327.7 | 12.5 | Leu | MeAla | MeLeu | D-Val | MePhe | Phe | MeLeu |
| DP-615 | 1327.7 | 12.6 | Phe | MeAla | MeLeu | Leu | MePhe | D-Val | MeLeu |
| DP-616 | 1368.8 | 12.6 | D-Val | MeAla | MeLeu | Leu | MePhe | Phe | MeLeu |
| DP-617 | 1410.8 | 12.0 | D-Val | MeAla | MeLeu | Leu | MePhe | Phe | MeLeu |
| DP-618 | 1347.0 | 12.8 | D-Val | MeAla | MeLeu | Leu | MePhe | Tyr(3-F) | MeLeu |
| DP-619 | 1417.9 | 11.7 | D-Val | MeAla | MeLeu | Met(O2) | MePhe | Phe | MeLeu |
| DP-620 | 1481.9 | 12.1 | D-Val | MeAla | MeLeu | Leu | MePhe | Phe | MeLeu |
| DP-621 | 1338.7 | 11.4 | D-Val | MeAla | MeLeu | Trp | MePhe | Trp | MeLeu |
| DP-622 | 1338.7 | 11.6 | D-Val | MeAla | MeLeu | Leu | MePhe | Phe | MeLeu |
| DP-623 | 1372.7 | 11.6 | D-Val | MeAla | MeLeu | Trp | MePhe | Phe | MeLeu |
| DP-624 | 1324.7 | 11.2 | D-Val | MeAla | MeLeu | Leu | MePhe | Phe | MeAla |
| DP-625 | 1396.8 | 11.9 | D-Val | MeAla | MeLeu | Leu | MePhe | Ala(4-Thz) | MeLeu |
| DP-626 | 1396.8 | 12.6 | D-Val | MeAla | MeLeu | Gln(Me) | MePhe | Phe | MeLeu |
| DP-627 | 1328.7 | 8.4 | D-Val | MeAla | MeLeu | Algly | MePhe | Phe | MeLeu |
| DP-628 | 1339.7 | 12.7 | D-Val | MeAla | MeLeu | Ala(CN) | MePhe | Phe | MeLeu |
| DP-629 | 1282.6 | 9.5 | D-Val | MeAla | MeLeu | Leu | MeAla | Phe | MeLeu |
| DP-630 | 1338.7 | 11.5 | D-Val | MeAla | MeLeu | MeLeu | MePhe | Lys(Me2) | MeLeu |
| DP-631 | 1425.9 | 12.2 | | D-Val | MeAla | MePhe | EtPhe | Lys(Me2) | MeGly |
| DP-632 | 1311.7 | 12.0 | MeAla | Thr | MeGly | MePhe | MePhe | MeLeu | Pro |

TABLE 11-1-continued

| | | | | | | | | |
|---|---|---|---|---|---|---|---|---|
| DP-633 | 1341.7 | 13.4 | | D-MeAla | Leu | MeLeu | EtPhe | Ala | MePhe | MeIle |
| DP-634 | 1224.6 | 11.5 | | | nPrGly | Ser(tBu) | MeGly | MeLeu | Thr | MePhe |
| DP-635 | 1355.8 | 14.0 | | D-MeAla | Leu | MeLeu | MePhe | Ala | MePhe | MeIle |
| DP-636 | 1341.7 | 13.5 | | D-MeAla | Leu | MeLeu | EtPhe | Ala | MePhe | MeLeu |
| DP-637 | 1341.7 | 13.5 | | D-MeAla | Leu | MeLeu | MePhe | Ala | EtPhe | MeLeu |
| DP-638 | 1313.7 | 12.2 | | MeGly | Leu | Thr | MeGly | MePhe | Ala | EtPhe |
| DP-639 | 1190.6 | 13.7 | | D-Ala | MeLeu | MeLeu | MeLeu | MeSer | Leu | MeGly |
| DP-640 | 1204.6 | 14.0 | | Val | MeLeu | Leu | D-Leu | MeSer | MeLeu | MeLeu |
| DP-641 | 1204.6 | 14.1 | | MeGly | MeLeu | Leu | MeLeu | Abu | D-Leu | MeLeu |
| DP-642 | 1204.6 | 13.9 | | MeLeu | MeSer | MeSer | Leu | MeGly | MeLeu | Val |
| DP-643 | 1204.6 | 14.0 | | Leu | D-Leu | MeLeu | MeLeu | MeSer | MeSer | Leu |
| DP-644 | 1190.6 | 13.6 | | MeLeu | MeLeu | MeSer | MeSer | MeGly | MeLeu | MeSer |
| DP-645 | 1190.6 | 13.8 | | Abu | D-Ala | D-Ala | MeLeu | MeLeu | MeLeu | MeSer |
| DP-646 | 1190.6 | 13.7 | | MeLeu | AOC(2) | MeLeu | Ala | D-Ala | MeLeu | D-Ala |
| DP-647 | 1204.6 | 14.2 | | Leu | MeGly | MeLeu | AOC(2) | MeLeu | Ser | Abu |
| DP-648 | 1204.6 | 14.1 | | MeSer | AOC(2) | MeGly | MeLeu | Val | MeLeu | MeSer |
| DP-649 | 1148.5 | 12.1 | | MeLeu | Ala | D-Ala | D-Ala | MeLeu | MeLeu | MeLeu |
| DP-650 | 1162.6 | 12.5 | | MeLeu | Ala | MeLeu | MeLeu | D-Leu | MeLeu | D-Ala |
| DP-651 | 1148.5 | 12.0 | | Abu | MeGly | MeLeu | Leu | MeLeu | Ser | Val |
| DP-652 | 1148.5 | 11.9 | | MeSer | Leu | MeGly | MeLeu | MeLeu | MeLeu | MeLeu |
| DP-653 | 1148.5 | 11.9 | | MeLeu | MeSer | Val | MeGly | MeLeu | Val | MeLeu |
| DP-654 | 1188.5 | 12.1 | | MeGly | MeLeu | Val | MeLeu | Ala | D-Ala | MeLeu |
| DP-655 | 1188.5 | 12.1 | | MeLeu | Abu | MeLeu | Ala | D-Ala | MeLeu | MeLeu |
| DP-656 | 1188.5 | 12.1 | | Leu | D-Ala | MeLeu | MeLeu | MeLeu | MeSer | Abu |
| DP-657 | 1188.5 | 12.0 | | MeSer | Leu | MeGly | D-Ala | Leu | MeLeu | Ala |
| DP-658 | 1319.7 | 9.7 | | | | | Thr | MeAla | MeLeu | MeLeu |
| DP-659 | 1549.0 | 12.8 | | | | MeAla | Thr | MeGly | MeLeu | Ile |
| DP-660 | 1512.0 | 13.1 | | | | MeAla | Thr | MeGly | MeLeu | Ile |
| DP-661 | 1348.7 | 11.0 | | | | MeAla | Thr | MeGly | MeLeu | Ile |
| DP-662 | 1334.7 | 10.4 | | | | MeAla | Thr | MeGly | MeLeu | Ile |
| DP-663 | 1293.7 | 12.1 | | | | MeAla | Thr | MeGly | MeLeu | Ile |
| DP-664 | 1166.5 | 10.3 | | | | MeAla | Ile | MeAla | MePhe | Ile |
| DP-665 | 1550.9 | 10.6 | | | | Ala | Ile | MeAla | MeLeu | Thr |
| DP-666 | 1529.9 | 11.5 | | | | Ala | Ile | MeAla | MeLeu | Thr |
| DP-667 | 1529.9 | 11.8 | | | | Ala | Ile | MeAla | MeLeu | Thr |
| DP-668 | 1283.6 | 9.7 | | | | Ala | Ile | MeAla | MeLeu | Thr |
| DP-669 | 1198.5 | 9.4 | | | | Ala | Ile | MeAla | MeLeu | Thr |
| DP-670 | 1569.0 | 12.6 | | | D-Ala | Ala | MeIle | MeLeu | Phe | Thr |
| DP-671 | 1481.9 | 11.6 | | | D-Ala | Ala | MeIle | MeLeu | Phe | Thr |
| DP-672 | 1356.7 | 10.5 | | | D-Ala | Ala | MeIle | MeLeu | Phe | Thr |
| DP-673 | 1014.3 | 10.5 | | | | | Ala | Leu | MeLeu | MePhe |
| DP-674 | 799.0 | 4.5 | | | | | | D-Ala | MePhe | Ile |
| DP-675 | 1096.4 | 8.1 | | Ala(5-Tet) | MeAla | Thr | MeAla | MeVa | Phe | MeGly |
| DP-676 | 1551.9 | 11.3 | | | MeLeu | Val | MePhe | MeAla | MeLeu | Thr |
| DP-677 | 899.1 | 4.9 | | | | | | g-MeAbu | Thr | MeLeu |
| DP-678 | 869.1 | 7.5 | | | | | | MeAla | MePhe | MeLeu |
| DP-679 | 911.2 | 8.9 | | | | | | MeAla | MePhe | MeLeu |
| DP-680 | 899.1 | 4.9 | | | | | | g-MeAbu | MePhe | Thr |
| DP-681 | 941.2 | 6.3 | | | | | | g-MeAbu | MePhe | Thr |
| DP-682 | 1012.3 | 8.4 | | | | | D-MeAla | MePhe | MePhe | Thr |
| DP-683 | 1054.4 | 9.8 | | | | | D-MeAla | MePhe | MeLeu | Thr |
| DP-684 | 1040.4 | 9.2 | | | | | D-Ala | MePhe | MeLeu | Thr |
| DP-685 | 1026.3 | 7.0 | | | | | g-MeAbu | MePhe | Thr | MeAla |

TABLE 11-1-continued

| ID | Mass | | | | | | |
|---|---|---|---|---|---|---|---|
| DP-686 | 1068.4 | 8.5 | | | g-MeAbu | MePhe | Thr | MeLeu |
| DP-687 | 986.2 | 7.3 | | | MeAla | MeAla | MePhe | Thr |
| DP-688 | 1028.3 | 8.8 | | | MeLeu | MePhe | MePhe | Thr |
| DP-689 | 1040.4 | 9.3 | | | MeLeu | MePhe | MeLeu | Thr |
| DP-690 | 982.3 | 8.7 | | | Val | MePhe | MeGly | MeLeu |
| DP-691 | 982.3 | 8.7 | | | Val | MePhe | MeLeu | Thr |
| DP-692 | 1026.3 | 8.6 | | | Let | MePhe | MeLeu | Thr |
| DP-693 | 1012.3 | 8.1 | | | Val | MePhe | Thr | MeGly |
| DP-694 | 1012.3 | 8.1 | | | Val | MePhe | MeGly | Thr |
| DP-695 | 1012.3 | 6.5 | | | g-MeAbu | MePhe | Thr | MeGly |
| DP-696 | 1040.4 | 9.2 | | | MeAla | MePhe | MeLeu | Thr |
| DP-697 | 998.3 | 7.8 | | | MeAla | MePhe | MeLeu | Thr |
| DP-698 | 1040.4 | 9.2 | | | MeAla | MePhe | Ser(tBu) | MeLeu |
| DP-699 | 1002.3 | 8.3 | | | MeAla | Ala | Thr | MeLeu |
| DP-700 | 1002.3 | 8.3 | | | MeAla | MeLeu | Phe | MeLeu |
| DP-701 | 1016.3 | 8.6 | | | D-Val | Leu | Thr | MeAla |
| DP-702 | 1016.3 | 8.6 | | | D-Val | Leu | Thr | MeAla |
| DP-703 | 1058.4 | 10.0 | | | D-Val | MePhe | Leu | MeAla |
| DP-704 | 1012.3 | 7.4 | | | b-MeAla | Thr | MeAla | Ser(tBu) |
| DP-705 | 1054.4 | 8.8 | | | b-MeAla | MeLeu | MeLeu | Thr |
| DP-706 | 1070.4 | 10.2 | | | MeLeu | MeLeu | Leu | MePhe |
| DP-707 | 1012.3 | 8.4 | | | MeAla | MePhe | MeLeu | Thr |
| DP-708 | 998.3 | 7.7 | | | D-Ala | MePhe | MePhe | Thr |
| DP-709 | 1032.3 | 7.8 | | | MeGly | Thr | Thr | MePhe |
| DP-710 | 1032.3 | 7.8 | | | MeAla | The | MeGly | Ser(tBu) |
| DP-711 | 1018.3 | 7.1 | | | Ala | MePhe | MeGly | MePhe |
| DP-712 | 954.2 | 6.3 | | | g-MeAbu | MeAla | MeLeu | Thr |
| DP-713 | 982.3 | 7.1 | | | g-MeAbu | MeGly | MeLeu | Thr |
| DP-714 | 982.3 | 8.7 | | | D-Val | MeLeu | MeGly | MePhe |
| DP-715 | 927.2 | 5.7 | | | | g-MeAbu | Thr | MeLeu |
| DP-716 | 927.2 | 5.7 | | | | g-MeAbu | Leu | Ser(tBu) |
| DP-717 | 913.2 | 7.1 | | | | MeLeu | Thr | MeLeu |
| DP-718 | 899.1 | 6.5 | | | | Let | MeGly | MeLeu |
| DP-719 | 869.1 | 7.2 | | | | Va | MeGly | Thr |
| DP-720 | 855.1 | 6.6 | | | | Val | MePhe | MeGly |
| DP-721 | 897.2 | 8.3 | | | | D-Ala | MePhe | MeLeu |
| DP-722 | 939.2 | 9.7 | | | | MeLeu | MePhe | MeLeu |
| DP-723 | 869.1 | 7.1 | | | | Leu | MePhe | MeGly |
| DP-724 | 885.1 | 5.9 | | | | Val | MePhe | MeLeu |
| DP-725 | 893.2 | 7.7 | | | | D-MeAla | MePhe | Thr |
| DP-726 | 835.1 | 7.1 | | | | | Leu | MeGly |
| DP-727 | 821.1 | 6.6 | | | | | Val | Leu |
| DP-728 | 1293.7 | 12.2 | MeAla | Leu | MeAla | Thr | Hph | Leu |
| DP-729 | 1307.7 | 12.7 | MeAla | Leu | MeAla | Thr | Phe3 | Leu |
| DP-730 | 1299.7 | 11.4 | D-Ala | Leu | MeLeu | MeVal | MeVal | Leu |
| DP-731 | 1313.7 | 11.9 | D-Ala | Thr | MeLeu | MeVal | Hph | MePhe |
| DP-732 | 1325.7 | 12.1 | D-Va | Thr | MeAla | MePhe | Phe3 | MePhe |
| DP-733 | 1339.7 | 12.6 | D-Val | Thr | MeAla | MePhe | Pro | Leu |
| DP-734 | 1257.6 | 10.4 | MeAla | Thr | MeAla | Ala | MePhe | MeLeu |
| DP-735 | 1271.6 | 11.0 | MeAla | Thr | MeAla | Ala | MePhe | MeLeu |
| DP-736 | 1251.6 | 11.1 | D-Val | MeLeu | MeAla | Thr | MeGly | Hph |
| DP-737 | 1265.6 | 11.6 | D-Val | MeLeu | MeAla | Thr | MeGly | Phe3 |
| DP-738 | 897.2 | 8.3 | | | | MeLeu | MeLeu | Leu |

TABLE 11-1-continued

| | | | | | | | |
|---|---|---|---|---|---|---|---|
| DP-739 | 855.1 | 6.8 | | | | D-Ala | MeAla |
| DP-740 | 897.2 | 8.3 | | | | D-Ala | MeLeu |
| DP-741 | 841.1 | 6.2 | | | | D-Ala | MePhe |
| DP-742 | 827.0 | 5.6 | | | | D-Ala | MeGly |
| DP-743 | 913.2 | 7.1 | | | | MeGly | Thr |
| DP-744 | 841.1 | 6.3 | | | | MeAla | Thr |
| DP-745 | 841.1 | 6.3 | | | | Leu | MeAla |
| DP-746 | 927.2 | 6.6 | | | | b-MeAla | Thr |
| DP-747 | 927.2 | 6.6 | | | | b-MeAla | MePhe |
| DP-748 | 941.2 | 7.9 | | | | Val | MeLeu |
| DP-749 | 885.1 | 5.9 | | | | Val | MeGly |
| DP-750 | 871.1 | 4.7 | | | | b-MeAla | Thr |
| DP-751 | 861.0 | 5.6 | | | | Ala | MeGly |
| DP-752 | 1273.6 | 9.4 | D-MeAla | Phe | Ser(tBu) | Phe | Thr |
| DP-753 | 1217.5 | 9.7 | D-MeAla | MeAla | MeLeu | Val | Gly |
| DP-754 | 1315.7 | 10.8 | D-MeAla | Phe | Ser(tBu) | Phe | Thr |
| DP-755 | 1273.6 | 11.7 | D-MeAla | MeAla | MeLeu | Val | Gly |
| DP-756 | 1387.8 | 13.3 | D-MeAla | Phe | MeLeu | Thr | MeIle |
| DP-757 | 1357.8 | 14.6 | b-MeAla | MeLeu | MeLeu | Va | Gly |
| DP-758 | 1429.9 | 14.7 | b-MeAla | Phe | MeLeu | Thr | MeIle |
| DP-759 | 1387.8 | 14.3 | MeAla | MePhe | MeLeu | Thr | MeIle |
| DP-760 | 1401.8 | 14.5 | D-Val | MeIle | MeLeu | Thr | MePhe |
| DP-761 | 1429.9 | 15.7 | MeAla | Leu | MeLeu | Thr | MeIle |
| DP-762 | 1392.2 | 15.3 | D-MeAla | MePhe | MeLeu | Va | MePhe |
| DP-763 | 1146.4 | 8.9 | | b-MeAla | MeAla | Thr | Gly |
| DP-764 | 1112.4 | 9.6 | | D-Ala | MeLeu | Thr | Phe |
| DP-765 | 1130.4 | 8.9 | | MeAla | MeGly | MePhe | MeAla |
| DP-766 | 1158.4 | 9.8 | | Ala | MeLeu | MeAla | MePhe |
| DP-767 | 1200.5 | 11.2 | | Ala | MeLeu | MeIle | MePhe |
| DP-768 | 1200.5 | 11.3 | | MeAla | MeGly | MePhe | MeLeu |
| DP-769 | 1202.5 | 11.5 | | D-MeAla | Thr | MeVal | MeAla |
| DP-770 | 1182.6 | 12.2 | | MeAla | Leu | Thr | MeAla |
| DP-771 | 1288.7 | 13.1 | | MeAla | MePhe | Phe | MeGly |
| DP-772 | 1238.7 | 14.2 | | MeAla | Leu | Thr | MeLeu |
| DP-773 | 1222.7 | 14.3 | | MeAla | MeLeu | Phe | MePhe |
| DP-774 | 1228.6 | 12.5 | | D-Val | MeIle | Ala | MeAla |
| DP-775 | 1274.7 | 12.9 | | MeAla | Thr | MePhe | MePhe |
| DP-776 | 1306.7 | 15.1 | | MeAla | MePhe | MeLeu | MeGly |
| DP-777 | 1147.5 | 9.3 | | MeAla | MeLeu | Thr | MeLeu |
| DP-778 | 1103.4 | 8.7 | | b-MeAla | Ser(tBu) | MeLeu | Thr |
| DP-779 | 1113.4 | 10.7 | | g-MeAbu | Ala | Ile | MePhe |
| DP-780 | 1145.5 | 12.1 | | MeAla | MePhe | MeLeu | MeAla |
| DP-781 | 1187.6 | 13.6 | | D-Val | MePhe | MeGly | MeLeu |
| DP-782 | 1222.0 | 14.3 | | D-Val | MePhe | MeLeu | MeLeu |
| DP-783 | 1131.5 | 11.8 | | D-Val | MePhe | MeLeu | MeLeu |
| DP-784 | 1337.4 | 10.1 | | D-MeAla | MeAla | Ile | MePhe |
| DP-785 | 1020.3 | 6.5 | | D-MeAla | Phe | MeLeu | Let |
| DP-786 | 944.2 | 7.0 | | | g-MeAbu | Phe | MePhe |
| DP-787 | 986.3 | 8.4 | | | D-Ala | MeAla | MeAla |
| DP-788 | 1004.3 | 9.3 | | | D-Ala | MeAla | MeLeu |
| DP-789 | 1028.3 | 10.0 | | | D-Val | MePhe | Thr |
| DP-790 | 1114.4 | 11.6 | | | D-MeAla | Leu | MeAla |
| DP-791 | 1074.4 | 11.9 | | | MeAla | MePhe | MeLeu |

TABLE 11-1-continued

| ID | Mass | Time | R1 | R2 | R3 | R4 | R5 | R6 | R7 | R8 |
|---|---|---|---|---|---|---|---|---|---|---|
| DP-792 | 1148.8 | 12.3 | | | | | | D-Val | Leu | Thr | 
| DP-792 | | | | | | | | | | MeAla |
| DP-793 | 1122.5 | 12.5 | | | | | | D-MeAla | MeLeu | MePhe |
| DP-794 | 845.0 | 4.7 | | | | | | | b-MeAla | Thr |
| DP-795 | 915.2 | 6.5 | | | | | | | g-MeAbu | MePhe |
| DP-796 | 877.1 | 7.1 | | | | | | | D-Val | Ala |
| DP-797 | 901.2 | 7.8 | | | | | | | D-MeAla | MePhe |
| DP-798 | 917.2 | 10.5 | | | | | | | Ala | Leu |
| DP-799 | 1062.8 | 10.7 | | | | | | D-MeAla | MePhe(3-Cl) | MeLeu |
| DP-800 | 994.3 | 10.0 | | | | | | D-MeAla | MeLeu | MeLeu |
| DP-801 | 1048.8 | 10.0 | | | | | | D-Val | MePhe(3-Cl) | MeAla |
| DP-802 | 980.3 | 9.4 | | | | | | D-Val | MeLeu | MeAla |
| DP-803 | 1147.9 | 11.4 | | | | | MeAla | MePhe(3-Cl) | MeGly | MeLeu |
| DP-804 | 1079.4 | 10.8 | | | | | MeAla | MeLeu | MeGly | MeLeu |
| DP-805 | 1250.6 | 12.1 | | | | b-MeAla | MeLeu | Thr | Phe(4-CF3) | MeLeu |
| DP-806 | 1148.5 | 11.3 | | | | b-MeAla | MeLeu | Thr | Leu | MeGly |
| DP-807 | 1277.5 | 10.5 | | | Ala | Pro | Pro | MeLeu | Thr | Gly |
| DP-808 | 1175.5 | 9.7 | | | Ala | Ile | Pro | MeLeu | Thr | Gly |
| DP-809 | 1249.9 | 11.0 | | | | Ile | b-MeAla | Ser(tBu) | MeLeu | MePhe(3-Cl) |
| DP-810 | 1360.0 | 12.1 | | | MeAla | Leu | MeAla | Pro | MeLeu | MePhe(3-Cl) |
| DP-811 | 1200.4 | 13.1 | | | | | D-MeAla | Thr | MeAla | MeLeu |
| DP-812 | 1214.4 | 13.5 | | | | | MeAla | MePhe(3-Cl) | Ile | MeLeu |
| DP-813 | 1077.5 | 12.2 | | | | | MeAla | MeLeu | Ile | MeLeu |
| DP-814 | 1395.6 | 12.9 | | | | Ala | D-Val | Gly | MeAla | MePhe(3-Cl) |
| DP-815 | 1230.6 | 10.1 | | | Ala | D-MeAla | MeAla | Ser(tBu) | Phe | Pro |
| DP-816 | 1240.6 | 12.8 | | | | MeAla | Phe | MeLeu | Thr | MeIle |
| DP-817 | 1282.7 | 14.2 | | | | MeAla | MePhe | Leu | Thr | MeIle |
| DP-818 | 965.2 | 8.1 | | | | MeAla | MePhe | MeAla | Thr | MeGly |
| DP-819 | 962.2 | 7.8 | | | | | D-Ala | MeVal | Thr | MeAla |
| DP-820 | 1127.5 | 11.0 | | | | | MeAla | Leu | MeLeu | Thr |
| DP-821 | 1169.6 | 12.5 | | | | | MeLeu | Leu | MeLeu | Thr |
| DP-822 | 1113.4 | 10.7 | | | | | MeAla | AOC(2) | MeLeu | Thr |
| DP-823 | 984.3 | 8.0 | | | | | | g-MeAbu | Ala | MeLeu |
| DP-824 | 1018.3 | 8.0 | | | | | | g-MeAbu | Ala | MeLeu |
| DP-825 | 953.2 | 9.5 | | | | | | D-Val | D-MeAla | Leu |
| DP-826 | 867.1 | 7.9 | | | | | | D-MeAla | MeAla | MeLeu |
| DP-827 | 949.2 | 7.0 | | | MeAla | Leu | | MeLeu | Thr | Pro |
| DP-828 | 1018.7 | 10.7 | | | | | | Let | MeLeu | MeAla |
| DP-829 | 1180.4 | 10.5 | | | | Leu | D-Val | MeAla | Thr | MeAla |
| DP-830 | 1255.6 | 12.2 | | | | | MePhe | MeGly | Gly | Thr |
| DP-831 | 1255.6 | 12.2 | | | | | MePhe | MeGly | MeLeu | Thr |
| DP-832 | 1271.7 | 13.1 | | | | | MePhe | MeGly | MeLeu | Thr |
| DP-833 | 1273.7 | 13.3 | | | | | MePhe | MeLeu | Ile | MeAla |
| DP-834 | 1273.7 | 13.3 | | | | | MePhe | MeLeu | Ile | MeAla |
| DP-835 | 1289.7 | 14.2 | | | | | MePhe | MeLeu | Ile | MeAla |
| DP-836 | 1275.7 | 13.6 | | | | | MeAla | MeLeu | Ile | MeAla |
| DP-837 | 1271.7 | 13.1 | | | | | MePhe | MePhe | MeLeu | Thr |
| DP-838 | 1257.7 | 12.6 | | | | | MePhe | nPrGly | MeLeu | Thr |
| DP-839 | 1283.7 | 13.6 | | | | | MeAla | Ser(tBu) | MeLeu | Thr |
| DP-840 | 1261.7 | 13.3 | | | | | MeAla | Thr | MePhe | Thr |
| DP-841 | 1289.7 | 14.2 | | | | | MeAla | Ile | MePhe | MePhe |
| DP-842 | 1295.7 | 12.6 | | | | | Phe | MeLeu | Phe | Leu |
| DP-843 | 1261.7 | 13.3 | | | | | MeLeu | MeAla | MePhe | Gly |
| DP-844 | 1075.4 | 12.9 | | | | | Thr | MeAla | MePhe | Gly |

TABLE 11-1-continued

| | | | | | | | |
|---|---|---|---|---|---|---|---|
| DP-845 | 1225.6 | 12.8 | | | | MePhe | Thr | MeAla |
| DP-846 | 1273.7 | 13.0 | | | | Ala | Ile | MePhe |
| DP-847 | 1289.7 | 13.9 | | | | Ala | MeLeu | MePhe |
| DP-848 | 1263.6 | 11.4 | | | | Thr | MeLeu | Ser(tBu) |
| DP-849 | 1275.7 | 13.6 | | | | MeAla | MeLeu | MePhe |
| DP-850 | 1430.9 | 14.6 | | | MePhe | Leu | Thr | MeGly |
| DP-851 | 1446.9 | 14.6 | | | MePhe | Leu | Thr | MeGly |
| DP-852 | 1432.9 | 15.5 | | | MePhe | Leu | Thr | MeGly |
| DP-853 | 1372.8 | 15.0 | | | MePhe | Let | Thr | MeGly |
| DP-854 | 1372.8 | 14.5 | | | | Leu | Ala | MePhe |
| DP-855 | 1388.8 | 14.5 | | | | Leu | Ala | MePhe |
| DP-856 | 1374.8 | 15.2 | | | | MeLeu | Ala | MePhe |
| DP-857 | 1416.9 | 14.8 | | | | MeLeu | Ala | MePhe |
| DP-858 | 1402.9 | 16.3 | | | | MeLeu | MeLeu | MePhe |
| DP-859 | 1358.8 | 15.8 | | | | MeLeu | MeLeu | MePhe |
| DP-860 | 1446.9 | 13.8 | | | | Gly | MeAla | MePhe |
| DP-861 | 1460.9 | 15.5 | | | | MePhe | Thr | MeGly |
| DP-862 | 1148.5 | 16.0 | | | | Ile | MePhe | Ser(tBu) |
| DP-863 | 1372.8 | 11.7 | | | | MeLeu | EtPhe | MePhe |
| DP-864 | 1360.8 | 14.5 | | | | MeLeu | Ala | MePhe |
| DP-865 | 1280.7 | 14.2 | | | Leu | MeLeu | Ala | Phe |
| DP-866 | 1402.9 | 11.7 | | | Gly | Pro | MeGly | Ala |
| DP-867 | 1416.9 | 15.9 | | | Leu | Thr | MePhe | Thr |
| DP-868 | 1459.9 | 16.5 | | | Ile | nPrGly | MeLeu | Phe |
| DP-869 | 1269.7 | 14.2 | | | MePhe | MeAla | MeVa | Phe |
| DP-870 | 1269.7 | 14.2 | | | MePhe | Pro | MeVa | Phe |
| DP-871 | 1285.7 | 15.1 | | | MePhe | Pro | MeVa | Phe |
| DP-872 | 1271.7 | 14.6 | | | MePhe | Pro | MeVa | Phe |
| DP-873 | 1546.1 | 16.9 | | Phe | MePhe | MeLeu | MeAla | MeIle |
| DP-874 | 1532.0 | 16.3 | | Phe | MePhe | MeLeu | MeAla | MeIle |
| DP-875 | 1459.9 | 15.6 | | Leu | MePhe | MeLeu | MeVal | MePhe |
| DP-876 | 1445.9 | 15.0 | | Ile | MePhe | MeVa | MeLeu | MePhe |
| DP-877 | 1443.9 | 14.0 | | Leu | MeIle | MeAla | MePhe | Gly |
| DP-878 | 1429.9 | 13.4 | | Thr | MePhe | Pro | Va | Phe |
| DP-879 | 1167.5 | 11.9 | | | | Leu | Va | Phe |
| DP-880 | 1179.6 | 12.3 | | | | Leu | MeVa | Phe |
| DP-881 | 1459.9 | 15.6 | | Leu | MePhe | Ala | MeVal | MeAla |
| DP-882 | 1457.9 | 14.8 | | Leu | MeIle | Gly | MeAla | Phe |
| DP-883 | 1471.9 | 15.4 | | Thr | MePhe | Va | Pro | MePhe |
| DP-884 | 1483.9 | 15.2 | | Va | MeAla | Leu | Phe | MePhe |
| DP-885 | 1429.9 | 13.5 | | Gly | MeVa | Ala | MeIle | Phe |
| DP-886 | 1445.9 | 15.0 | | Ile | MePhe | Ala | MeVa | MeAla |
| DP-887 | 1515.0 | 14.2 | Gly | MeAla | Leu | MeLeu | MeVa | MePhe |
| DP-888 | 1372.8 | 13.9 | | | Leu | Va | Phe | Phe |
| DP-889 | 1515.0 | 14.2 | Gly | MeAla | Leu | Va | Phe | MePhe |
| DP-890 | 1372.8 | 13.9 | | | Leu | MeLeu | Phe | MePhe |
| DP-891 | 1531.0 | 15.1 | Gly | MeAla | Leu | MeLeu | Phe | MePhe |
| DP-892 | 1388.8 | 14.8 | | | Leu | MeLeu | Phe | MePhe |
| DP-893 | 1517.0 | 14.5 | Gly | MeAla | Leu | MeLeu | Phe | MePhe |
| DP-894 | 1374.8 | 14.2 | | | Leu | MeLeu | Phe | MePhe |
| DP-895 | 1557.0 | 15.6 | Val | MeGly | Leu | Va | MeIle | MePhe |
| DP-896 | 1543.0 | 15.1 | Val | MeGly | Leu | MeLeu | MeIle | Phe |
| DP-897 | 1372.8 | 13.9 | | | Leu | MeLeu | MeIle | Phe |

TABLE 11-1-continued

| ID | Mass | RT | R1 | R2 | R3 | R4 | R5 | R6 | R7 |
|---|---|---|---|---|---|---|---|---|---|
| DP-898 | 1486.9 | 12.9 | Leu | Phe | Thr | Leu | MeAla | Phe | Gly |
| DP-899 | 1583.1 | 16.7 | Va | MeLeu | MeGly | MeLeu | MeIle | Ala | MePhe |
| DP-900 | 1529.0 | 14.3 | Va | MeAla | Thr | Leu | Phe | MeLeu | Pro |
| DP-901 | 1344.7 | 12.6 | | MeVal | Thr | Leu | Phe | MeLeu | Ile |
| DP-902 | 1557.0 | 15.6 | Gly | Ile | Ala | Leu | MeLeu | MePhe | Phe |
| DP-903 | 1500.9 | 13.0 | Phe | | Pro | Leu | Thr | Gly | Ile |
| DP-904 | 1207.6 | 11.6 | | | | D-Let | MePhe | His | Leu |
| DP-905 | 1271.6 | 10.9 | | | | MePhe | Thr | MeLeu | MePhe |
| DP-906 | 1449.9 | 13.8 | | MeLeu | Leu | MeLeu | MePhe | Leu | Val |
| DP-907 | 1237.6 | 12.2 | | | | MeLeu | Ala(5-Tet) | Ala | MeLeu |
| DP-908 | 1506.0 | 17.0 | | MeLeu | Leu | MeLeu | MePhe | Phe | MePhe |
| DP-909 | 1336.7 | 13.4 | | | Ala(5-Tet) | MePhe | MeLeu | MeAla | MeLeu |
| DP-910 | 1515.0 | 13.4 | | | | | | Leu | MePhe |
| DP-911 | 1483.4 | 14.8 | | | | | | Phe | MeAla |
| DP-912 | 1461.3 | 12.7 | | | | | | D-Va | Leu |
| DP-913 | 1483.0 | 13.8 | | | | | | MeAla | MeLeu |
| DP-914 | 1545.5 | 15.3 | | | | | | Ala | Thr |
| DP-915 | 1569.4 | 13.8 | | | | | | Phe | MeLeu |
| DP-916 | 1446.3 | 15.0 | | | | | | D-Val | MePhe(3-Cl) |
| DP-917 | 1369.8 | 12.5 | | | | | | D-Ala | MeLeu |
| DP-918 | 1361.7 | 11.3 | | | | | | Ala | MePhe |
| DP-919 | 1259.7 | 11.2 | | | | | | D-Ala | Thr |
| DP-920 | 1418.3 | 13.5 | | | | | | MeAla | Ile |
| DP-921 | 1403.8 | 12.2 | | | | | | MeAla | Val |
| DP-922 | 1572.0 | 12.7 | | | | | Ala | MeAla | MePhe |
| DP-923 | 1745.0 | 16.5 | | | | | Phe | MePhe | Pro |
| DP-924 | 1622.5 | 14.6 | | | | D-Va | D-Val | Va | Thr |
| DP-925 | 1642.6 | 16.3 | | | | Ala | Phe | Leu | MeLeu |
| DP-926 | 1662.6 | 14.7 | | | | b-MeAla | b-MeAla | MePhe | Val |
| DP-927 | 1563.4 | 14.8 | | | | MeAla | MeAla | Val | MePhe |
| DP-928 | 1523.4 | 13.7 | | | | D-Val | Ala | Thr | MeLeu |
| DP-929 | 1472.9 | 12.2 | | | | MeAla | D-Va | Ala | MePhe |
| DP-930 | 1502.9 | 12.7 | | | | b-MeAla | b-MeAla | MeAla | Leu |
| DP-931 | 1579.5 | 15.7 | | | | D-MeAla | Phe | Ile | MeLeu |
| DP-932 | 1327.7 | 11.1 | | | | MeAla | MeAla | Va | Ala |
| DP-933 | 1363.8 | 13.7 | | | | MeLeu | D-Val | Leu | MeLeu |
| DP-934 | 1369.8 | 12.6 | | | | MeLeu | Ala | MePhe | MeLeu |
| DP-935 | 1701.2 | 15.3 | | | D-Va | Ala | Val | Thr | MeAla |
| DP-936 | 1699.6 | 15.8 | | | Ala | Val | MeLeu | MePhe(3-Cl) | Va |
| DP-937 | 1625.2 | 15.4 | | | MeAla | Leu | Leu | MeLeu | Thr |
| DP-938 | 1723.3 | 17.7 | | | D-Val | MeLeu | MeLeu | MePhe | Thr |
| DP-939 | 1512.0 | 12.9 | | | b-MeAla | MeAla | Ala | Thr | Thr |
| DP-940 | 1534.0 | 14.9 | | | MeAla | D-Val | Leu | MePhe | MeAla |
| DP-941 | 1672.6 | 16.8 | | | | MeAla | MePhe(3-Cl) | Leu | Leu |
| DP-942 | 1648.5 | 15.6 | | | | D-MeAla | MeLeu | MePhe | Thr |
| DP-943 | 1586.0 | 13.6 | | | | MeLeu | MeLeu | MePhe | Leu |
| DP-944 | 1695.2 | 16.7 | | | | MeLeu | Thr | Ala | Val |
| DP-945 | 1667.2 | 16.0 | | | | MeLeu | MeLeu | Ala | Phe |
| DP-946 | 1777.7 | 18.0 | | | | Thr | Val | MeLeu | MeLeu |
| DP-947 | 1681.2 | 16.2 | | | | MeLeu | MeAla | Phe | Phe |
| DP-948 | 1665.2 | 14.4 | D-Val | D-Val | b-MeAla | Phe | MeAla | Thr | MePhe |
| DP-949 | 1707.6 | 16.0 | MeAla | MeAla | MeAla | MeLeu | Thr | MeGly | Val |
| DP-950 | 1701.6 | 16.9 | | | Val | MeAla | Thr | MePhe(3-Cl) | Leu |

TABLE 11-1-continued

| ID | Mass | RT | 7 | 6 | 5 | 4 | 3 | 2 | 1 | H-1 | H-2 | H-3 | H-4 | H-5 | H-6 |
|---|---|---|---|---|---|---|---|---|---|---|---|---|---|---|---|
| DP-951 | 1695.2 | 17.6 | | | Ala | Thr | Pro | Leu | Asp | | MeAla | MeLeu | MeLeu | Leu | MePhe |
| DP-952 | 1657.1 | 14.4 | | | Phe | Thr | MeLeu | Pro | Asp | | Thr | MeGly | Leu | Pro | Phe |
| DP-953 | 1773.3 | 17.4 | | | b-MeAla | Ile | Thr | Gly | Asp | | MeLeu | Ala | MeLeu | Ser(tBu) | MeLeu |
| DP-954 | 1725.3 | 16.1 | | b-MeAla | Thr | Pro | Thr | Leu | Asp | | MePhe | MePhe | MeLeu | Thr | MeLeu |
| DP-955 | 1595.0 | 14.0 | | Ala | MePhe | Val | Leu | Leu | Asp | | MeGly | Leu | Pro | Phe | MePhe |
| DP-956 | 1669.2 | 15.7 | | D-MeAla | Leu | MeGly | MeIle | Ala | Asp | | MeAla | MeLeu | MeLeu | Phe | MeAla |
| DP-957 | 1554.9 | 14.9 | | b-MeAla | Ile | Phe | MeLeu | Pro | Asp | | MeLeu | Thr | MeGly | MeLeu | Ile |
| DP-958 | 1596.1 | 16.7 | | b-MeAla | MeAla | MeLeu | MeVal | MeVal | Asp | | MeLeu | MeAla | MePhe | Thr | MeAla |
| DP-959 | 1669.2 | 16.1 | MePhe | | | Val | MeLeu | MeAla | Asp | | MeLeu | Ile | b-MeAla | Phe | MeAla |
| DP-960 | 1545.0 | 14.7 | D-MeAla | | | MeGly | MeIle | MeVal | Asp | | | | Ile | MeLeu | Leu |
| DP-961 | 1630.1 | 15.3 | | | | Ile | Pro | Phe | Asp | | MeAla | b-MeAla | MeLeu | MePhe | Thr |
| DP-962 | 1642.1 | 16.2 | | | | Leu | Val | Thr | Asp | | MeAla | Phe | MeLeu | MeLeu | MeLeu |
| DP-963 | 1725.3 | 17.5 | | D-MeAla | MePhe | Pro | Gly | Phe | Asp | | | MeLeu | HOGly | Phe | MeAla |
| DP-964 | 1481.4 | 14.8 | | | | MePhe | MeLeu | Pro | Asp | | | | | Pro | Lys |
| DP-965 | 1238.6 | 12.3 | | | | MeLeu | Phe | Val | Asp | | | | | Ala | MeIle |

| ID | 4 | 3 | 2 | 1 | H-1 | H-2 | H-3 | H-4 | H-5 | H-6 |
|---|---|---|---|---|---|---|---|---|---|---|
| DP-1 | Thr | Pro | Leu | Asp | pip | MeAla | MeLeu | MeLeu | Leu | MePhe |
| DP-2 | Thr | MeLeu | Pro | Asp | pip | Thr | MeGly | Leu | Pro | Phe |
| DP-3 | Ile | Thr | Gly | Asp | pip | MeLeu | Ala | MeLeu | Ser(tBu) | MeLeu |
| DP-4 | Pro | Thr | Leu | Asp | pip | Phe | MePhe | MeLeu | Thr | MeLeu |
| DP-5 | Val | Leu | Leu | Asp | pip | MeGly | Leu | Pro | MePhe | MePhe |
| DP-6 | MeGly | MeIle | Ala | Asp | pip | MeAla | MeLeu | MeLeu | Phe | MeAla |
| DP-7 | Phe | MeLeu | Pro | Asp | pip | MeLeu | Thr | MeGly | MeLeu | Ile |
| DP-8 | MeLeu | Phe | MeVal | Asp | pip | MeLeu | MeAla | MePhe | Thr | MeAla |
| DP-9 | Leu | MeVal | Phe | Asp | pip | MeLeu | Ile | b-MeAla | Phe | MeAla |
| DP-10 | Val | MeLeu | MeLeu | Asp | pip | MeLeu | Ile | MeLeu | MeLeu | Leu |
| DP-11 | MeGly | MeIle | MeAla | Asp | pip | MeAla | b-MeAla | MeLeu | MePhe | Thr |
| DP-12 | Ile | Pro | MeVal | Asp | pip | MeAla | Phe | MeLeu | MeLeu | MeLeu |
| DP-13 | Leu | Val | Phe | Asp | pip | MePhe | Leu | HOGly | Phe | MeAla |
| DP-14 | Pro | Gly | Thr | Asp | pip | MePhe | MeLeu | MeLeu | Pro | Leu |
| DP-15 | Pro | MeGly | Thr | Asp | pip | MeLeu | Leu | MeLeu | Ala | MeIle |
| DP-16 | MePhe | MeLeu | Pro | Asp | pip | MeLeu | Phe | MeLeu | MeLeu | MeLeu |
| DP-17 | Pro | Thr | Leu | Asp | pip | MeLeu | MeLeu | MePhe | MeLeu | MeLeu |
| DP-18 | Leu | MePhe | MeLeu | Asp | pip | MeLeu | MeLeu | MeLeu | MeLeu | MeLeu |
| DP-19 | Val | Leu | MeIle | Asp | pip | MeLeu | MeLeu | MeLeu | MeLeu | MeLeu |
| DP-20 | MeLeu | Leu | Ile | Asp | pip | MeLeu | MeLeu | MeLeu | MeLeu | MeLeu |
| DP-21 | Ile | Ala | MeIle | Asp | pip | MeLeu | MeLeu | MeLeu | MeLeu | MeLeu |
| DP-22 | Pro | MeGly | MeLeu | Asp | pip | MeLeu | MeLeu | MeLeu | MeLeu | MeLeu |
| DP-23 | MeAla | Thr | Leu | Asp | pip | MeLeu | MeLeu | b-MeAla | MeLeu | MeLeu |
| DP-24 | Leu | MeLeu | MeIle | Asp | pip | MeLeu | MeLeu | Ile | Phe | MeAla |
| DP-25 | Pro | Ala | MeLeu | Asp | pip | MeLeu | MeLeu | MeLeu | MeLeu | MeLeu |
| DP-26 | Thr | Thr | Leu | Asp | pip | MeLeu | MeLeu | MePhe | MeLeu | MeLeu |
| DP-27 | MeLeu | Pro | MeIle | Asp | pip | MeLeu | MeLeu | MeLeu | MeLeu | MePhe |
| DP-28 | Leu | MePhe | Val | Asp | pip | MeLeu | MePhe | MeLeu | MeLeu | MeLeu |
| DP-29 | Pro | Thr | MeLeu | Asp | pip | MeLeu | MeLeu | MeLeu | MeLeu | MeLeu |
| DP-30 | Phe | Leu | Pro | Asp | pip | MeAla | MeLeu | MeLeu | Phe | MeLeu |
| DP-31 | MeLeu | Phe | MeVal | Asp | pip | MeAla | MeLeu | MeLeu | MeLeu | MeAla |
| DP-32 | MeAla | Leu | MeLeu | Asp | pip | MeAla | MeLeu | MeLeu | MeLeu | MeAla |
| DP-33 | Ile | Pro | Thr | Asp | pip | MeLeu | MeLeu | MeLeu | MeLeu | Lys |
| DP-34 | MePhe | Leu | Pro | Asp | pip | MeAla | MeLeu | MeLeu | Leu | MeIle |
| DP-35 | MeLeu | Phe | Val | Asp | pip | MeAla | MeLeu | MeLeu | MeLeu | MeIle |

TABLE 11-1-continued

| | | | | | | | | | |
|---|---|---|---|---|---|---|---|---|---|
| DP-36 | MeLeu | MeLeu | Ser(tBu) | MeIle | Asp | pip | | | |
| DP-37 | MeLeu | MeLeu | Ser(tBu) | MeIle | Asp | pip | | | |
| DP-38 | MeGly | MeLeu | MeLeu | Ser(tBu) | Asp | pip | | | |
| DP-39 | MeGly | MeLeu | MeLeu | Ser(tBu) | Asp | pip | | | |
| DP-40 | Leu | MePhe | MePhe | Val | Asp | Ile | | | |
| DP-41 | Phe | Val | Val | MeAla | Asp | Leu | | | |
| DP-42 | Val | Phe | Phe | MeLeu | Asp | Gly | | | |
| DP-43 | Phe | MeVal | MeVal | Ala | Asp | MeLeu | | | |
| DP-44 | MeVal | Ala | Ala | MeLeu | Asp | Ile | | | |
| DP-45 | Leu | MePhe | MePhe | MeLeu | Asp | Thr | | | |
| DP-46 | MePhe | Phe | Phe | MeAla | Asp | Val | | | |
| DP-47 | Ser(tBu) | MePhe | MePhe | MeVal | Asp | pip | | | |
| DP-48 | MeGly | MePhe | MePhe | MeLeu | Asp | pip | | | |
| DP-49 | MeAla | MeIle | MeIle | MeLeu | Asp | pip | | | |
| DP-50 | Gly | MeVal | MeVal | Phe | Asp | pip | | | |
| DP-51 | MePhe | MeAla | MeAla | MeLeu | Asp | pip | | | |
| DP-52 | MePhe | MeLeu | MeLeu | Gly | Asp | pip | | | |
| DP-53 | Leu | Gly | Gly | MeIle | Asp | pip | | | |
| DP-54 | Phe | MeLeu | MeLeu | Pro | Asp | pip | | | |
| DP-55 | MeLeu | MeIle | MeIle | Ala | Asp | pip | | | |
| DP-56 | MeLeu | Ala | Ala | MeIle | Asp | pip | pip | | |
| DP-57 | Thr | MeIle | MeIle | Phe | Asp | pip | Ile | | |
| DP-58 | MeLeu | MeAla | MeAla | Ala | Asp | pip | Ala | | |
| DP-59 | Thr | MeAla | MeAla | Leu | Asp | pip | Ile | pip | |
| DP-60 | Ser(tBu) | MeLeu | MeLeu | MeIle | Asp | pip | pip | Ile | |
| DP-61 | MeGly | MeIle | MeIle | MeIle | Asp | pip | Ile | pip | pip |
| DP-62 | MeAla | MeIle | MeIle | MePhe | Asp | pip | pip | Ile | |
| DP-63 | Ser(tBu) | MeIle | MeIle | MeLeu | Asp | pip | Pro | Ile | pip |
| DP-64 | MeGly | MeIle | MeIle | MePhe | Asp | pip | MeLeu | | pip |
| DP-65 | Phe | MeIle | MeIle | MeLeu | Asp | pip | | | |
| DP-66 | MeLeu | MePhe | MePhe | MeVal | Asp | pip | | | |
| DP-67 | MeLeu | Ala | Ala | MeVal | Asp | pip | | | |
| DP-68 | MeIle | MeGly | MeGly | MePhe | Asp | pip | | | |
| DP-69 | Thr | MeAla | MeAla | MeLeu | Asp | pip | | | |
| DP-70 | Thr | MeAla | MeAla | MeIle | Asp | pip | | | |
| DP-71 | MeLeu | Ala | Ala | MeIle | Asp | pip | | | |
| DP-72 | MePhe | MeLeu | MeLeu | MeIle | Asp | pip | | | |
| DP-73 | MeLeu | MeIle | MeIle | Ala | Asp | pip | | | |
| DP-74 | MePhe | MeIle | MeIle | MeLeu | Asp | pip | | | |
| DP-75 | Ala | MeIle | MeIle | MeIle | Asp | pip | | | |
| DP-76 | MeIle | MeIle | MeIle | MeAla | Asp | pip | | | |
| DP-77 | MeLeu | Ser(tBu) | Ser(tBu) | MeIle | Asp | pip | | | |
| DP-78 | MeLeu | MePhe | MePhe | MeLeu | Asp | pip | | | |
| DP-79 | MePhe | MeLeu | MeLeu | MeLeu | Asp | pip | | | |
| DP-80 | MeLeu | MeLeu | MeLeu | Gly | Asp | pip | | | |
| DP-81 | Ser(tBu) | Ala | Ala | MeIle | Asp | pip | | | |
| DP-82 | Leu | Leu | Leu | MeLeu | Asp | pip | | | |
| DP-83 | MeAla | Thr | Thr | Thr | Asp | pip | | | |
| DP-84 | Ile | Thr | Thr | Gly | Asp | pip | | | |
| DP-85 | MeAla | Gly | Gly | Thr | Asp | pip | | | |
| DP-86 | Ile | MeAla | MeAla | Thr | Asp | pip | | | |
| DP-87 | MeLeu | Ala | Ala | Ile | Asp | pip | | | |
| DP-88 | MeGly | MeIle | MeIle | Ala | Asp | pip | | | |

TABLE 11-1-continued

| | | | | | | | |
|---|---|---|---|---|---|---|---|
| DP-89 | Phe | Thr | MeAla | Asp | pip | | |
| DP-90 | MeLeu | Ser(tBu) | MeLeu | Asp | pip | | |
| DP-91 | Gly | MeLeu | Leu | Asp | pip | | |
| DP-92 | MeLeu | Ser(tBu) | MeLeu | Asp | pip | | |
| DP-93 | Thr | MeAla | MeAla | Asp | pip | | |
| DP-94 | Thr | MeAla | Leu | Asp | pip | | |
| DP-95 | Ala | MeLeu | Leu | Asp | pip | | |
| DP-96 | MeAla | MeIle | MeLeu | Asp | pip | | |
| DP-97 | MeIle | Thr | MeGly | Asp | pip | | |
| DP-98 | MeVal | MeGly | Thr | Asp | pip | | |
| DP-99 | MePhe | MeLeu | MeAla | Asp | pip | | |
| DP-100 | MeAla | MeIle | MeLeu | Asp | pip | | |
| DP-101 | Thr | MeGly | MeLeu | Asp | pip | | |
| DP-102 | MeVal | MeGly | Leu | Asp | pip | | |
| DP-103 | Thr | MeAla | MeLeu | Asp | pip | | |
| DP-104 | MeIle | MePhe | Leu | Asp | pip | | |
| DP-105 | Thr | MeGly | MeLeu | Asp | pip | | |
| DP-106 | Thr | Pro | Phe | Asp | pip | | |
| DP-107 | MeAla | Ile | MePhe | Asp | pip | | |
| DP-108 | Thr | MeAla | Ile | Asp | pip | | |
| DP-109 | Gly | MeLeu | Leu | Asp | pip | | |
| DP-110 | Ser(tBu) | MePhe | MeVal | Asp | pip | | |
| DP-111 | Phe | Leu | MeVal | Asp | pip | | |
| DP-112 | MeVal | MeLeu | Ile | Asp | pip | | |
| DP-113 | Thr | Pro | Ile | Asp | pip | | |
| DP-114 | Thr | MeAla | MeLeu | Asp | pip | | |
| DP-115 | Ile | Thr | Phe | Asp | pip | | |
| DP-116 | Leu | Gly | MePhe | Asp | pip | | |
| DP-117 | Thr | Gly | MePhe | Asp | pip | | |
| DP-118 | MeGly | Leu | MePhe | Asp | pip | | |
| DP-119 | Phe | MePhe | Leu | Asp | pip | | |
| DP-120 | MeLeu | Leu | Ser(tBu) | Asp | pip | | |
| DP-121 | MeVal | Phe | Thr | Asp | pip | | |
| DP-122 | MeAla | MeLeu | MeLeu | Asp | MePhe | Ala | |
| DP-123 | Val | MeLeu | MeLeu | Asp | MePhe | Ala | |
| DP-124 | MeLeu | Ala | MePhe | Asp | pip | | |
| DP-125 | MePhe | Leu | MeLeu | Asp | pip | | |
| DP-126 | Thr | MePhe | MeLeu | Asp | pip | | |
| DP-127 | Leu | MePhe | MeLeu | Asp | pip | | |
| DP-128 | Thr | MeAla | MeLeu | Asp | pip | | |
| DP-129 | MeLeu | MePhe | Gly | Asp | pip | | |
| DP-130 | MeLeu | MePhe | Ser(tBu) | Asp | pip | | |
| DP-131 | MeGly | MeAla | MeAla | Asp | pip | | |
| DP-132 | MeGly | MeAla | MeAla | Asp | pip | | |
| DP-133 | MeGly | MeLeu | MePhe | Asp | pip | | |
| DP-134 | MeLeu | MeLeu | Ala | Asp | pip | | |
| DP-135 | MeLeu | Ala | MeIle | Asp | pip | | |
| DP-136 | Thr | MeAla | MeLeu | Asp | pip | | |
| DP-137 | Phe | MeLeu | Thr | Asp | pip | | |
| DP-138 | MeLeu | MeIle | Ser(tBu) | Asp | pip | | pip |
| DP-139 | MeLeu | MeAla | MeLeu | Asp | pip | | pip |
| DP-140 | MeAla | MeLeu | MeLeu | Asp | pip | | |
| DP-141 | MeLeu | MePhe | MeVal | Asp | pip | | |

TABLE 11-1-continued

| | | | | | | | |
|---|---|---|---|---|---|---|---|
| DP-142 | MeVal | Ala | MeIle | Asp | pip | | | |
| DP-143 | Leu | MeLeu | Ala | Asp | pip | | | |
| DP-144 | MeLeu | Ser(tBu) | MeIle | Asp | pip | | | |
| DP-145 | Thr | Phe | MeVal | Asp | pip | | | |
| DP-146 | Phe | MeLeu | MeLeu | Asp | pip | | | |
| DP-147 | MePhe | MeLeu | MeLeu | Asp | pip | | | |
| DP-148 | MeAla | MeLeu | Ser(tBu) | Asp | pip | | | |
| DP-149 | Ser(tBu) | MePhe | MeVal | Asp | pip | | | |
| DP-150 | MeLeu | Thr | MeAla | Asp | pip | | | |
| DP-151 | MePhe | MeLeu | Thr | Asp | pip | | | |
| DP-152 | MeLeu | Ser(tBu) | MeIle | Asp | pip | | | |
| DP-153 | Phe | Thr | MeAla | Asp | pip | | | |
| DP-154 | MeAla | MePhe | Leu | Asp | pip | | | |
| DP-155 | MeLeu | Ser(tBu) | MeIle | Asp | pip | | | |
| DP-156 | MeLeu | MePhe | MeLeu | Asp | pip | | | |
| DP-157 | MeLeu | Thr | MeAla | Asp | pip | | | |
| DP-158 | Thr | MeAla | MeLeu | Asp | pip | | | |
| DP-159 | MeAla | MeLeu | MePhe | Asp | pip | | | |
| DP-160 | MeAla | MeLeu | Ser(tBu) | Asp | pip | | | |
| DP-161 | Phe | Thr | MeAla | Asp | pip | | | |
| DP-162 | Pro | Thr | Phe | Asp | pip | | | |
| DP-163 | MeAla | MeLeu | Ser(tBu) | Asp | pip | | | |
| DP-164 | Phe | MeAla | MeLeu | Asp | pip | | | |
| DP-165 | Phe | MeGly | Thr | Asp | pip | | | |
| DP-166 | Thr | MeAla | MeLeu | Asp | pip | | | |
| DP-167 | Ala | MeLeu | Leu | Asp | pip | | | |
| DP-168 | MeLeu | Ser(tBu) | MeVal | Asp | pip | | | |
| DP-169 | MePhe | Thr | Leu | Asp | pip | | | |
| DP-170 | MeLeu | Ser(tBu) | MeLeu | Asp | pip | | | |
| DP-171 | MeLeu | MeVal | Phe | Asp | pip | | | |
| DP-172 | MeAla | Thr | Ile | Asp | pip | | | |
| DP-173 | Thr | MePhe | MeVal | Asp | pip | | | |
| DP-174 | MeLeu | MeLeu | MeLeu | Asp | pip | | | |
| DP-175 | MeLeu | MeLeu | MeLeu | Asp | pip | | | |
| DP-176 | Ser(tBu) | MeLeu | Gly | Asp | pip | | | |
| DP-177 | Phe | MeLeu | Leu | Asp | pip | MePhe | Ala | pip |
| DP-178 | MeAla | MeLeu | MePhe | Asp | pip | MePhe | Ala | pip |
| DP-179 | Ala | MeLeu | Leu | Asp | pip | MePhe | Ala | pip |
| DP-180 | Ile | MePhe | MeVal | Asp | pip | MePhe | Ala | pip |
| DP-181 | MeAla | MeLeu | Leu | Asp | pip | MePhe | Ala | pip |
| DP-182 | MeLeu | Leu | Thr | Asp | pip | MePhe | Ala | pip |
| DP-183 | Thr | MeGly | MePhe | Asp | pip | MePhe | Ala | pip |
| DP-184 | MeAla | MeLeu | MePhe | Asp | pip | MePhe | Ala | pip |
| DP-185 | Pro | Thr | Leu | Asp | pip | MePhe | Ala | pip |
| DP-186 | MeVal | MeLeu | Ile | Asp | pip | MePhe | Ala | pip |
| DP-187 | MeLeu | MeVal | Val | Asp | pip | MePhe | Ala | pip |
| DP-188 | Val | MeLeu | MeLeu | Asp | pip | MePhe | Ala | pip |
| DP-189 | MePhe | MeLeu | Thr | Asp | pip | MePhe | Ala | pip |
| DP-190 | MePhe | MeLeu | Phe | Asp | pip | MePhe | Ala | pip |
| DP-191 | MePhe | MeVal | MeLeu | Asp | pip | MePhe | Ala | pip |
| DP-192 | MePhe | MeVal | Phe | Asp | pip | MePhe | Ala | pip |
| DP-193 | Gly | MeVal | MeLeu | Asp | pip | MePhe | Ala | pip |
| DP-194 | MeGly | MeLeu | MeLeu | Asp | pip | MePhe | Ala | pip |

TABLE 11-1-continued

| ID | | | | | | | | | |
|---|---|---|---|---|---|---|---|---|---|
| DP-195 | Ile | MeLeu | MeLeu | MeAla | Asp | MePhe | Ala | | |
| DP-196 | MeGly | MeLeu | MeLeu | Val | Asp | MePhe | Ala | | |
| DP-197 | MeLeu | Val | Val | MeLeu | Asp | MePhe | Ala | | |
| DP-198 | MeGly | MeLeu | MeLeu | Val | Asp | MePhe | Ala | | |
| DP-199 | Val | MeAla | MeAla | MeLeu | Asp | MePhe | Ala | | |
| DP-200 | MePhe | MeLeu | Phe | MeLeu | Asp | MePhe | Ala | | |
| DP-201 | Val | MeLeu | MeLeu | MeLeu | Asp | MePhe | Ala | | |
| DP-202 | MeLeu | Val | Val | MeLeu | Asp | MePhe | Ala | | |
| DP-203 | MeLeu | Val | Val | MeLeu | Asp | MePhe | MePhe | | |
| DP-204 | MeLeu | Val | Val | MeLeu | Asp | MePhe | MePhe | | |
| DP-205 | Gly | MeVal | MeVal | Phe | Asp | MePhe | MePhe | | |
| DP-206 | MeLeu | Val | Val | MeLeu | Asp | MePhe | MePhe | | |
| DP-207 | Thr | MePhe | MePhe | Thr | Asp | MePhe | MePhe | | |
| DP-208 | MeLeu | Val | Val | MeLeu | Asp | MePhe | MePhe | | |
| DP-209 | Val | MePhe | MePhe | Gly | Asp | MePhe | MePhe | | |
| DP-210 | MeLeu | Val | Val | MeLeu | Asp | MePhe | MePhe | | |
| DP-211 | MeLeu | Val | Val | MeLeu | Asp | MePhe | MePhe | | |
| DP-212 | MeLeu | MeAla | MeAla | Thr | Asp | MePhe | MePhe | | |
| DP-213 | MePhe | MeLeu | MeLeu | Val | Asp | MePhe | MePhe | | |
| DP-214 | MeAla | MeLeu | MeLeu | MeLeu | Asp | MePhe | MePhe | | |
| DP-215 | MeLeu | Ala | MeIle | MeIle | Asp | pip | MePhe | Ala | |
| DP-216 | Leu | Gly | Gly | MeIle | Asp | pip | MePhe | Ala | |
| DP-217 | Thr | MeAla | MeAla | Leu | Asp | pip | MePhe | Ala | |
| DP-218 | Phe | MeLeu | MeLeu | Pro | Asp | pip | MePhe | Ala | |
| DP-219 | Ser(tBu) | MeLeu | MeLeu | MeAla | Asp | pip | MePhe | Ala | |
| DP-220 | Gly | MeLeu | MeLeu | Leu | Asp | pip | MePhe | Ala | |
| DP-221 | Gly | MeIle | MeIle | Phe | Asp | pip | MePhe | Ala | |
| DP-222 | MeAla | Phe | Phe | MeIle | Asp | pip | MePhe | Ala | |
| DP-223 | Leu | Gly | Gly | MeIle | Asp | pip | MePhe | Ala | |
| DP-224 | Phe | MeLeu | MeLeu | Leu | Asp | pip | MePhe | Ala | |
| DP-225 | Ala | MeIle | MeIle | MeLeu | Asp | pip | MePhe | Ala | |
| DP-226 | MeAla | Ala | Ala | Thr | Asp | pip | MePhe | Ala | |
| DP-227 | Pro | Gly | Gly | MeLeu | Asp | pip | MePhe | Ala | |
| DP-228 | MeIle | Thr | Thr | Leu | Asp | pip | MePhe | Ala | |
| DP-229 | MeVal | MeIle | MeIle | Phe | Asp | pip | MePhe | Ala | |
| DP-230 | MeAla | Ala | Ala | Thr | Asp | pip | MePhe | Ala | |
| DP-231 | Pro | Phe | Phe | MeLeu | Asp | pip | MePhe | Ala | |
| DP-232 | MeIle | Thr | Thr | MeGly | Asp | pip | MePhe | Ala | |
| DP-233 | MeGly | MeVal | MeVal | Thr | Asp | pip | MePhe | Ala | |
| DP-234 | MeIle | MeLeu | MeLeu | Thr | Asp | pip | MePhe | Ala | |
| DP-235 | MePhe | MeLeu | MeLeu | MeAla | Asp | pip | MePhe | Ala | |
| DP-236 | Thr | Pro | Pro | Phe | Asp | pip | MePhe | Ala | pip |
| DP-237 | Ala | MeLeu | MeLeu | Leu | Asp | pip | MePhe | Ala | pip |
| DP-238 | Phe | MeAla | MeAla | Ala | Asp | pip | MePhe | Ala | pip |
| DP-239 | Thr | Pro | Pro | Phe | Asp | pip | MePhe | Ala | pip |
| DP-240 | Leu | MeIle | MeIle | MeLeu | Asp | pip | MePhe | Ala | pip |
| DP-241 | MeVal | MeLeu | MeLeu | Ala | Asp | pip | MePhe | Ala | pip |
| DP-242 | MePhe | Ala | Ala | Phe | Asp | pip | MePhe | Ala | pip |
| DP-243 | Ala | MeLeu | MeLeu | Leu | Asp | pip | MePhe | Ala | pip |
| DP-244 | MeIle | MePhe | MePhe | MeLeu | Asp | pip | MePhe | Ala | pip |
| DP-245 | MePhe | Phe | Phe | Ala | Asp | pip | MePhe | Ala | pip |
| DP-246 | MeLeu | MeLeu | MeLeu | MeLeu | Asp | pip | MePhe | Ala | pip |
| DP-247 | MeIle | Leu | Leu | MeLeu | Asp | pip | MePhe | Ala | pip |

TABLE 11-1-continued

| | | | | | | | |
|---|---|---|---|---|---|---|---|
| DP-248 | MeIle | MePhe | Leu | Asp | | | |
| DP-249 | MeIle | Leu | MeLeu | Asp | pip | | |
| DP-250 | MeVal | MeLeu | Thr | Asp | pip | | |
| DP-251 | MeAla | MePhe | MeIle | Asp | pip | | |
| DP-252 | Leu | MePhe | MeVal | Asp | pip | | |
| DP-253 | Ala | MeGly | MeIle | Asp | pip | | |
| DP-254 | MeLeu | MeIle | Ala | Asp | pip | | |
| DP-255 | Thr | MeAla | MeIle | Asp | pip | | |
| DP-256 | MePhe | MeLeu | MeLeu | Asp | pip | | |
| DP-257 | MeLeu | Ser(tBu) | MeIle | Asp | pip | | |
| DP-258 | MeAla | MePhe | MeLeu | Asp | pip | | |
| DP-259 | MeVal | Phe | Thr | Asp | pip | | |
| DP-260 | Gly | MeVal | Phe | Asp | pip | | |
| DP-261 | Thr | MeAla | MeLeu | Asp | pip | | |
| DP-262 | Gly | MeIle | MeLeu | Asp | pip | | |
| DP-263 | MeLeu | MePhe | MeLeu | Asp | pip | | |
| DP-264 | MeAla | MePhe | MeLeu | Asp | pip | | |
| DP-265 | MeAla | Ser(tBu) | MeIle | Asp | pip | | |
| DP-266 | MeAla | MeLeu | MeLeu | Asp | pip | | |
| DP-267 | MeAla | MeLeu | Ser(tBu) | Asp | pip | | |
| DP-268 | Thr | MeAla | MeLeu | Asp | pip | | |
| DP-269 | MeAla | MeLeu | Ser(tBu) | Asp | pip | | |
| DP-270 | Gly | MeLeu | MePhe | Asp | pip | | |
| DP-271 | MeLeu | MePhe | Gly | Asp | pip | | |
| DP-272 | MeLeu | MeLeu | MeIle | Asp | pip | | |
| DP-273 | Gly | MeAla | Phe | Asp | pip | | |
| DP-274 | Ile | MePhe | Ala | Asp | pip | | |
| DP-275 | MeGly | MeLeu | MeLeu | Asp | pip | | |
| DP-276 | Pro | MeLeu | MeVal | Asp | pip | | |
| DP-277 | MeLeu | MeVal | Phe | Asp | pip | | |
| DP-278 | Pro | Gly | MeLeu | Asp | MePhe | Ala | |
| DP-279 | Thr | MeGly | MePhe | Asp | MePhe | Ala | |
| DP-280 | Pro | Leu | MeLeu | Asp | MePhe | Ala | |
| DP-281 | MePhe | MePhe | MeAla | Asp | MePhe | Ala | |
| DP-282 | Leu | Leu | Phe | Asp | MePhe | Ala | |
| DP-283 | Pro | Thr | MePhe | Asp | MePhe | Ala | |
| DP-284 | MeAla | MeLeu | MeAla | Asp | MePhe | Ala | |
| DP-285 | Leu | MeLeu | MeAla | Asp | MePhe | Ala | |
| DP-286 | MePhe | MeLeu | Phe | Asp | MePhe | MePhe | pip |
| DP-287 | MeLeu | MeVal | MeAla | Asp | MePhe | MePhe | pip |
| DP-288 | Ile | MeLeu | MeLeu | Asp | MePhe | Ala | pip |
| DP-289 | MePhe | Ile | MeVal | Asp | MePhe | MePhe | |
| DP-290 | MeLeu | MeLeu | Phe | Asp | MePhe | Ala | |
| DP-291 | MeVal | MeLeu | MeLeu | Asp | MePhe | MePhe | pip |
| DP-292 | MePhe | MeLeu | Ile | Asp | MePhe | MePhe | pip |
| DP-293 | MeLeu | MeAla | MePhe | Asp | MePhe | Ala | |
| DP-294 | MeLeu | Ala | MeLeu | Asp | MePhe | MePhe | pip |
| DP-295 | Thr | MePhe | MeAla | Asp | MePhe | Ala | |
| DP-296 | MeLeu | Ala | Thr | Asp | MePhe | Ala | pip |
| DP-297 | Ile | MeLeu | MeAla | Asp | MePhe | MePhe | pip |
| DP-298 | Phe | MeVal | Thr | Asp | MePhe | Ala | |
| DP-299 | MeLeu | MeAla | MeLeu | Asp | MePhe | Ala | pip |
| DP-300 | Ile | MeLeu | MeVal | Asp | MePhe | MePhe | pip |

TABLE 11-1-continued

| | | | | | | | |
|---|---|---|---|---|---|---|---|
| DP-301 | Gly | MeVal | Phe | Asp | MePhe | Ala | |
| DP-302 | Val | MeLeu | MeIle | Asp | MePhe | MePhe | pip |
| DP-303 | MePhe | MeVal | Thr | Asp | MePhe | Ala | pip |
| DP-304 | Gly | MeLeu | Phe | Asp | MePhe | Ala | |
| DP-305 | Val | MeLeu | MeIle | Asp | MePhe | Ala | pip |
| DP-306 | MeGly | MeLeu | Val | Asp | MePhe | MePhe | |
| DP-307 | MePhe | MeLeu | Gly | Asp | MePhe | Ala | pip |
| DP-308 | MeLeu | Ile | MeVal | Asp | MePhe | Ala | |
| DP-309 | Gly | MeAla | Thr | Asp | MePhe | MePhe | |
| DP-310 | MeAla | MeLeu | MeLeu | Asp | MePhe | Ala | pip |
| DP-311 | MePhe | MeLeu | Phe | Asp | MePhe | Ala | pip |
| DP-312 | MePhe | MeAla | Thr | Asp | MePhe | MePhe | |
| DP-313 | MeLeu | Val | MeLeu | Asp | MePhe | Ala | pip |
| DP-314 | MePhe | MeAla | Thr | Asp | MePhe | MePhe | pip |
| DP-315 | MeGly | MeLeu | Val | Asp | MePhe | MePhe | pip |
| DP-316 | MePhe | MeAla | Phe | Asp | MePhe | Ala | |
| DP-317 | MeAla | Ser(tBu) | MeVal | Asp | pip | | |
| DP-318 | Thr | MeAla | MePhe | Asp | pip | | |
| DP-319 | MeAla | MeAla | Val | Asp | pip | | |
| DP-320 | Thr | Ala | Phe | Asp | pip | | |
| DP-321 | Leu | MeLeu | Leu | Asp | pip | | |
| DP-322 | MeAla | Phe | MeAla | Asp | pip | | |
| DP-323 | MeLeu | Leu | Ile | Asp | pip | | |
| DP-324 | Phe | Leu | MeLeu | Asp | pip | | |
| DP-325 | Phe | MeLeu | Ile | Asp | pip | | |
| DP-326 | MeLeu | MeAla | Ala | Asp | pip | | |
| DP-327 | MeLeu | Thr | Phe | Asp | pip | | |
| DP-328 | MeVal | Leu | MeLeu | Asp | pip | | |
| DP-329 | MePhe | Leu | Phe | Asp | pip | | |
| DP-330 | Ile | Thr | Leu | Asp | pip | | |
| DP-331 | MePhe | Phe | Leu | Asp | pip | | |
| DP-332 | MePhe | Phe | Leu | Asp | pip | | |
| DP-333 | MeVal | Ile | MeLeu | Asp | pip | | |
| DP-334 | MePhe | Phe | Leu | Asp | pip | | |
| DP-335 | Leu | Ile | Ser(tBu) | Asp | pip | | |
| DP-336 | MePhe | MePhe | MeLeu | Asp | pip | | |
| DP-337 | MeAla | Phe | MeAla | Asp | pip | | |
| DP-338 | Leu | MePhe | MePhe | Asp | pip | | |
| DP-339 | MeLeu | Phe | Leu | Asp | pip | | |
| DP-340 | MeAla | Phe | MeVal | Asp | pip | | |
| DP-341 | MePhe | Thr | MeAla | Asp | pip | | |
| DP-342 | MeLeu | Ile | MeLeu | Asp | pip | | |
| DP-343 | MeLeu | MeLeu | Thr | Asp | pip | | |
| DP-344 | Thr | MeAla | MePhe | Asp | MePhe | Ala | pip |
| DP-345 | MeAla | MePhe | MeGly | Asp | MePhe | Ala | pip |
| DP-346 | MeAla | MePhe | MeAla | Asp | MePhe | Ala | pip |
| DP-347 | MePhe | MeAla | MePhe | Asp | MePhe | Ala | pip |
| DP-348 | Ala | MeVal | MeAla | Asp | MePhe | Ala | pip |
| DP-349 | MeGly | MeAla | MeLeu | Asp | MePhe | Ala | pip |
| DP-350 | MePhe | Phe | MeLeu | Asp | MePhe | Ala | pip |
| DP-351 | Thr | Leu | MeLeu | Asp | MePhe | Ala | pip |
| DP-352 | MeAla | Gly | MePhe | Asp | MePhe | Ala | pip |
| DP-353 | MeLeu | Thr | MeAla | Asp | MePhe | Ala | pip |

TABLE 11-1-continued

| ID | 1 | 2 | 3 | 4 | 5 | 6 | 7 | 8 |
|---|---|---|---|---|---|---|---|---|
| DP-354 | MeLeu | Ala | MeAla | Asp | MePhe | Ala | | |
| DP-355 | MePhe | MeVal | Gly | Asp | MePhe | Ala | | |
| DP-356 | Thr | Gly | Val | Asp | MePhe | Ala | | |
| DP-357 | Val | MeLeu | MeAla | Asp | MePhe | Ala | | |
| DP-358 | Thr | MeLeu | MePhe | Asp | MePhe | Ala | | |
| DP-359 | Phe | MeLeu | MeAla | Asp | MePhe | Ala | | |
| DP-360 | Thr | Ala | MeAla | Asp | MePhe | Ala | | |
| DP-361 | MeAla | MePhe | Phe | Asp | MePhe | Ala | | |
| DP-362 | Thr | MeAla | MePhe | Asp | MePhe | Ala | | |
| DP-363 | Thr | MeGly | MePhe | Asp | MePhe | Ala | | |
| DP-364 | MePhe | Leu | Thr | Asp | MePhe | Ala | | |
| DP-365 | Leu | MeLeu | Phe | Asp | MePhe | Ala | | |
| DP-366 | Thr | MeAla | MeLeu | Asp | MePhe | Ala | | |
| DP-367 | MeVal | Ala | MeAla | Asp | MePhe | Ala | | |
| DP-368 | Thr | MeAla | MeAla | Asp | MePhe | Ala | | |
| DP-369 | MePhe | Phe | MeAla | Asp | MePhe | Ala | | |
| DP-370 | MeLeu | Thr | MeAla | Asp | MePhe | Ala | | |
| DP-371 | Ile | MeLeu | MeVal | Asp | MePhe | Ala | | |
| DP-372 | MeLeu | MeVal | Phe | Asp | MePhe | Ala | | |
| DP-373 | MeLeu | MePhe | MeLeu | Asp | MePhe | Ala | | |
| DP-374 | Ile | MeLeu | MeVal | Asp | MePhe | Ala | | |
| DP-375 | MePhe | Thr | Gly | Asp | MePhe | Ala | | |
| DP-376 | MeAla | Ile | MeLeu | Asp | MePhe | Ala | | |
| DP-377 | Ala | MeLeu | MeAla | Asp | MePhe | Ala | | |
| DP-378 | MePhe | MePhe | Gly | Asp | MePhe | Ala | | |
| DP-379 | MePhe | Phe | MeLeu | Asp | MePhe | Ala | | |
| DP-380 | MeGly | MePhe | Val | Asp | MePhe | Ala | | |
| DP-381 | MePhe | Val | MeLeu | Asp | MePhe | Ala | | |
| DP-382 | MePhe | MeLeu | Gly | Asp | MePhe | Ala | | |
| DP-383 | MePhe | MeLeu | Phe | Asp | MePhe | Ala | | |
| DP-384 | Ile | MeLeu | MeVal | Asp | MePhe | Ala | | |
| DP-385 | MeAla | MeGly | MeLeu | Asp | MePhe | Ala | | |
| DP-386 | MePhe | Phe | MeLeu | Asp | MePhe | Ala | | |
| DP-387 | Phe | MeLeu | Thr | Asp | MePhe | Ala | pip | |
| DP-388 | MeGly | MeLeu | MeAla | Asp | MePhe | Ala | pip | |
| DP-389 | MeLeu | MeAla | Ala | Asp | MePhe | Ala | pip | |
| DP-390 | MeVal | Thr | Phe | Asp | MePhe | Ala | pip | |
| DP-391 | MeAla | Val | MeLeu | Asp | MePhe | Ala | pip | |
| DP-392 | Ala | MeLeu | MeVal | Asp | MePhe | Ala | pip | |
| DP-393 | MePhe | Val | MeVal | Asp | MePhe | Ala | pip | |
| DP-394 | MeAla | MeLeu | MeAla | Asp | MePhe | MePhe | Ala | pip |
| DP-395 | MeAla | MeLeu | Gly | Asp | MePhe | MePhe | Ala | pip |
| DP-396 | MePhe | MeLeu | Phe | Asp | MePhe | MePhe | Ala | pip |
| DP-397 | MePhe | MeLeu | MeVal | Asp | MePhe | MePhe | Ala | pip |
| DP-398 | MeLeu | Thr | MeAla | Asp | MePhe | MePhe | Ala | pip |
| DP-399 | MeLeu | Ile | MeVal | Asp | MePhe | MePhe | Ala | pip |
| DP-400 | MeAla | Thr | MeAla | Asp | MePhe | MePhe | Ala | pip |
| DP-401 | MePhe | MeLeu | Gly | Asp | MePhe | MePhe | Ala | pip |
| DP-402 | MePhe | Thr | MeAla | Asp | MePhe | MePhe | Ala | pip |
| DP-403 | MeLeu | MeAla | MeLeu | Asp | MePhe | MePhe | Ala | pip |
| DP-404 | MeLeu | Thr | Val | Asp | MePhe | MePhe | Ala | pip |
| DP-405 | MeGly | MeLeu | Val | Asp | MePhe | MePhe | Ala | pip |
| DP-406 | MeAla | MeLeu | Thr | Asp | MePhe | MePhe | Ala | pip |

TABLE 11-1-continued

| | | | | | | | |
|---|---|---|---|---|---|---|---|
| DP-407 | MeGly | MeLeu | Val | Asp | MePhe | MePhe | Ala | pip |
| DP-408 | MeVal | MeAla | Leu | Asp | pip | | | |
| DP-409 | MeAla | MeVal | Ser(tBu) | Asp | pip | | | |
| DP-410 | MeAla | Thr | MeAla | Asp | pip | | | |
| DP-411 | Thr | Phe | Leu | Asp | pip | | | |
| DP-412 | Val | MeLeu | Ile | Asp | pip | | | |
| DP-413 | Ile | MeLeu | MeLeu | Asp | pip | | | |
| DP-414 | MeAla | MeLeu | MeAla | Asp | pip | | | |
| DP-415 | Ala | Thr | Phe | Asp | pip | | | |
| DP-416 | Val | Leu | Ile | Asp | pip | | | |
| DP-417 | Ile | MeLeu | Ala | Asp | pip | | | |
| DP-418 | MeLeu | Leu | MeLeu | Asp | pip | | | |
| DP-419 | Ala | MePhe | MeLeu | Asp | pip | | | |
| DP-420 | Leu | Phe | Thr | Asp | pip | | | |
| DP-421 | MeVal | Leu | MeLeu | Asp | pip | | | |
| DP-422 | Ala | MeAla | MeLeu | Asp | pip | | | |
| DP-423 | Gly | Phe | Phe | Asp | pip | | | |
| DP-424 | Phe | MePhe | Leu | Asp | pip | | | |
| DP-425 | MeLeu | Leu | MePhe | Asp | pip | | | |
| DP-426 | MeLeu | MeLeu | Thr | Asp | pip | | | |
| DP-427 | Ile | MeVa | MeLeu | Asp | pip | | | |
| DP-428 | MeLeu | MeLeu | MeLeu | Asp | pip | | | |
| DP-429 | MePhe | MeLeu | MeLeu | Asp | pip | | | |
| DP-430 | Ile | Phe | Thr | Asp | pip | | | |
| DP-431 | Ile | Phe | Gly | Asp | pip | | | |
| DP-432 | Ile | MePhe | Leu | Asp | pip | | | |
| DP-433 | MeLeu | MePhe | Leu | Asp | pip | | | |
| DP-434 | Ile | MeVal | MeLeu | Asp | pip | | | |
| DP-435 | MeLeu | MeAla | MeLeu | Asp | pip | | | |
| DP-436 | Ile | MePhe | Phe | Asp | pip | | | |
| DP-437 | Leu | MeLeu | Phe | Asp | pip | | | |
| DP-438 | MeAla | MeVal | Thr | Asp | pip | | | |
| DP-439 | MeLeu | MeLeu | Ile | Asp | pip | | | |
| DP-440 | Ile | MeLeu | MeLeu | Asp | pip | | | |
| DP-441 | Thr | MePhe | MeLeu | Asp | pip | | | |
| DP-442 | MePhe | MePhe | MeLeu | Asp | pip | | | |
| DP-443 | MeAla | MeLeu | MeAla | Asp | MePhe | Ala | | |
| DP-444 | Ala | MeAla | MeAla | Asp | MePhe | Ala | | |
| DP-445 | MeAla | MePhe | MeAla | Asp | MePhe | Ala | | |
| DP-446 | Phe | Thr | MeAla | Asp | MePhe | Ala | | |
| DP-447 | MeAla | MePhe | Thr | Asp | MePhe | Ala | | |
| DP-448 | MeLeu | MeAla | Val | Asp | MePhe | Ala | | |
| DP-449 | Thr | MeAla | MeLeu | Asp | MePhe | MePhe | Ala | |
| DP-450 | Thr | MeAla | MeAla | Asp | MePhe | Ala | | |
| DP-451 | MePhe | Phe | MeLeu | Asp | MePhe | MePhe | Ala | pip |
| DP-452 | Thr | MeVal | Phe | Asp | MePhe | Ala | | |
| DP-453 | Ile | MeLeu | MeAla | Asp | MePhe | MePhe | pip | pip |
| DP-454 | MeLeu | Thr | MeAla | Asp | MePhe | MePhe | Ala | pip |
| DP-455 | MeAla | Thr | MeAla | Asp | MePhe | MePhe | Ala | pip |
| DP-456 | Phe | MeVal | Thr | Asp | MePhe | MePhe | Ala | pip |
| DP-457 | MeLeu | MeAla | Val | Asp | MePhe | Ala | pip | |
| DP-458 | MeAla | Ala | MeAla | Asp | MePhe | MePhe | Ala | pip |
| DP-459 | MeLeu | Ile | MeVal | Asp | MePhe | MePhe | Ala | |

TABLE 11-1-continued

| ID | | | | | | | | |
|---|---|---|---|---|---|---|---|---|
| DP-460 | Val | MeAla | MeAla | Asp | MePhe | | MePhe | Ala | |
| DP-461 | Phe | MeLeu | Thr | Asp | MePhe | | Ala | pip | |
| DP-462 | MeAla | Thr | MeAla | Asp | MePhe | | Ala | pip | |
| DP-463 | MeAla | MeLeu | MeAla | Asp | MePhe | | MePhe | Ala | pip |
| DP-464 | Val | MeAla | MeAla | Asp | MePhe | | MePhe | Ala | |
| DP-465 | MeAla | MeVal | Ser(tBu) | Asp | pip | | | | |
| DP-466 | Ala | MeAla | MePhe | Asp | pip | | | | |
| DP-467 | MeAla | MeAla | Thr | Asp | pip | | | | |
| DP-468 | MeGly | MeLeu | MePhe | Asp | pip | | | | |
| DP-469 | Thr | MeAla | MePhe | Asp | pip | | | | |
| DP-470 | MeAla | MeAla | Thr | Asp | pip | | | | |
| DP-471 | MePhe | MeLeu | Ala | Asp | pip | | | | |
| DP-472 | MeVal | Leu | MeLeu | Asp | pip | | | | |
| DP-473 | MeLeu | MeVal | MeAla | Asp | pip | | | | |
| DP-474 | Phe | MeAla | MeAla | Asp | pip | | | | |
| DP-475 | Phe | Leu | MeVal | Asp | pip | | | | |
| DP-476 | MeAla | MeLeu | MePhe | Asp | pip | | | | |
| DP-477 | Ile | MeVal | MePhe | Asp | pip | | | | |
| DP-478 | Val | Leu | Ile | Asp | pip | | | | |
| DP-479 | MeLeu | Leu | MeLeu | Asp | pip | | | | |
| DP-480 | MeAla | MeLeu | MeAla | Asp | pip | | | | |
| DP-481 | MeVal | MeLeu | Phe | Asp | pip | | | | |
| DP-482 | MePhe | MeLeu | Ala | Asp | pip | | | | |
| DP-483 | MeVal | MeAla | Phe | Asp | MePhe | | Ala | | |
| DP-484 | MeVal | MePhe | Leu | Asp | MePhe | | Ala | | |
| DP-485 | MeGly | MePhe | Ala | Asp | pip | | | | |
| DP-486 | Thr | Gly | MePhe | Asp | pip | | | | |
| DP-487 | Thr | MePhe | MeAla | Asp | pip | | | | |
| DP-488 | MeLeu | MePhe | Leu | Asp | MePhe | | | | |
| DP-489 | MeLeu | MePhe | MeLeu | Asp | MePhe | | | | |
| DP-490 | MeLeu | Ile | MeAla | Asp | pip | | Ala | | |
| DP-491 | MeLeu | Ala | MePhe | Asp | MePhe | | Ala | | |
| DP-492 | MeGly | MeLeu | MeVal | Asp | MePhe | | Ala | | |
| DP-493 | MeLeu | MePhe | MeLeu | Asp | MePhe | | Ala | | |
| DP-494 | Phe | MeLeu | Thr | Asp | pip | | | | |
| DP-495 | Ala | MeVal | MeVal | Asp | MePhe | | MePhe | Ala | pip |
| DP-496 | MeGly | MeLeu | MeGly | Asp | MePhe | | MePhe | Ala | pip |
| DP-497 | MeLeu | MeVal | MeVal | Asp | MePhe | | MePhe | Ala | pip |
| DP-498 | MeAla | MePhe | Ile | Asp | MePhe | | MePhe | Ala | pip |
| DP-499 | MeLeu | MeLeu | Thr | Asp | MePhe | | MePhe | Ala | pip |
| DP-500 | MeAla | Thr | MeAla | Asp | MePhe | | MePhe | Ala | pip |
| DP-501 | MeLeu | MeVal | Phe | Asp | MePhe | | MePhe | Ala | pip |
| DP-502 | MeLeu | MeAla | Ile | Asp | MePhe | | MePhe | Ala | pip |
| DP-503 | Gly | MeVal | Phe | Asp | MePhe | | MePhe | Ala | pip |
| DP-504 | MePhe | Val | MeVal | Asp | MePhe | | MePhe | Ala | pip |
| DP-505 | Val | MeAla | MePhe | Asp | MePhe | | MePhe | Ala | pip |
| DP-506 | MeAla | MeAla | Ile | Asp | MePhe | | MePhe | Ala | pip |
| DP-507 | MeAla | MeVal | Ala | Asp | MePhe | | MePhe | Ala | pip |
| DP-508 | MeAla | Ile | MePhe | Asp | MePhe | | MePhe | Ala | pip |
| DP-509 | Thr | MeAla | MeAla | Asp | MePhe | | MePhe | Ala | pip |
| DP-510 | Ile | MeLeu | MeVa | Asp | MePhe | | MePhe | Ala | pip |
| DP-511 | MeAla | Thr | MeAla | Asp | pip | | MePhe | Ala | pip |
| DP-512 | MeLeu | MePhe | MeLeu | Asp | pip | | MePhe | Ala | pip |

TABLE 11-1-continued

| | | | | | | | | | | |
|---|---|---|---|---|---|---|---|---|---|---|
| DP-513 | Leu | Phe | MeLeu | Asp | pip | | | | | |
| DP-514 | Leu | Phe | Leu | Asp | pip | | | | | |
| DP-515 | Thr | Leu | Phe | Asp | pip | | | | | |
| DP-516 | MePhe | MeLeu | Ile | Asp | pip | | | | | |
| DP-517 | Thr | Phe | MeLeu | Asp | pip | | | | | |
| DP-518 | MeLeu | MePhe | Ile | Asp | pip | | | | | |
| DP-519 | MePhe | MeAla | MeLeu | Asp | pip | | | | | |
| DP-520 | MeAla | MePhe | MeLeu | Asp | pip | | | | | |
| DP-521 | MePhe | MeLeu | MePhe | Asp | pip | | | | | |
| DP-522 | MePhe | MeLeu | Gly | Asp | pip | | | | | |
| DP-523 | MeGly | MeLeu | Ser(tBu) | Asp | pip | | | | | |
| DP-524 | MeAla | MeLeu | MePhe | Asp | pip | | | | | |
| DP-525 | Ser(tBu) | MeLeu | MeLeu | Asp | pip | | | | | |
| DP-526 | Phe | MeLeu | MePhe | Asp | pip | | | | | |
| DP-527 | MeGly | Ser(tBu) | MeLeu | Asp | pip | | | | | |
| DP-528 | MeGly | MeLeu | Ser(tBu) | Asp | pip | | | | | |
| DP-529 | MeAla | MeLeu | Ser(tBu) | Asp | pip | | | | | |
| DP-530 | MePhe | Leu | Pro | Asp | pip | | | | | |
| DP-531 | Ser(tBu) | MePhe | MeLeu | Asp | pip | | | | | |
| DP-532 | Ser(tBu) | MePhe | MeLeu | Asp | pip | | | | | |
| DP-533 | Thr | MeGly | MeLeu | Asp | pip | | | | | |
| DP-534 | MeGly | MePhe | Ser(tBu) | Asp | pip | | | | | |
| DP-535 | MeGly | Ser(tBu) | MeLeu | Asp | pip | | | | | |
| DP-536 | MeGly | Ser(tBu) | MeLeu | Asp | pip | | | | | |
| DP-537 | Thr | MeGly | MeLeu | Asp | pip | | | | | |
| DP-538 | MeLeu | Thr | MeAla | Asp | pip | | | | | |
| DP-539 | Thr | MePhe | Leu | Asp | pip | | | | | |
| DP-540 | MeLeu | MeIle | Ser(tBu) | Asp | pip | | | | | |
| DP-541 | MeLeu | Ala | MeVa | Asp | pip | | | | | |
| DP-542 | MeLeu | Ala | MeVal | Asp | pip | | | | | |
| DP-543 | MeLeu | MeIle | MeAla | Asp | pip | | | | | |
| DP-544 | MeLeu | MeIle | MeLeu | Asp | pip | | | | | |
| DP-545 | MeLeu | MeIle | MeLeu | Asp | pip | | | | | |
| DP-546 | MeLeu | MeIle | MeLeu | Asp | pip | | | | | |
| DP-547 | MeLeu | Ser(tBu) | MeLeu | Asp | pip | | | | | |
| DP-548 | Phe | Leu | MeVal | Asp | pip | | | | | |
| DP-549 | Phe | Leu | MeVal | Asp | pip | | | | | |
| DP-550 | Thr | Pro | Phe | Asp | pip | | | | | |
| DP-551 | Thr | Pro | Phe | Asp | pip | | | | | |
| DP-552 | Thr | Pro | Phe | Asp | pip | | | | | |
| DP-553 | Thr | Pro | Phe | Asp | pip | | | | | |
| DP-554 | Thr | Pro | Phe | Asp | pip | | | | | |
| DP-555 | Thr | Pro | Phe | Asp | pip | | | | | |
| DP-556 | Thr | Pro | Phe | Asp | pip | | | | | |
| DP-557 | Thr | Pro | Phe | Asp | pip | | | | | |
| DP-558 | Thr | Aze(2) | Phe | Asp | pip | | | | | |
| DP-559 | Thr | Pic(2) | Phe | Asp | pip | | | | | |
| DP-560 | Phe | Leu | MeVal | Asp | pip | | | | | |
| DP-561 | Phe | Leu | MeVal | Asp | pip | | | | | |
| DP-562 | Ser(tBu) | MeLeu | Gly | Asp | pip | | | | | |
| DP-563 | Ser(tBu) | MeLeu | Gly | Asp | pip | | | | | |
| DP-564 | Thr | Pro | Aib | Asp | pip | | | | | |
| DP-565 | MeGly | MePhe | Leu | Asp | MePhe | MeAla | Pro | MePhe | Ala | pip |

TABLE 11-1-continued

| | | | | | | | | | |
|---|---|---|---|---|---|---|---|---|---|
| DP-566 | MeGly | MePhe | Leu | Asp | MeLeu | Val | Ala | | |
| DP-567 | MeGly | MePhe | Leu | Asp | MePhe | Ile | pip | | |
| DP-568 | Thr | MeGly | Val | Asp | MeLeu | Gly | MeLeu | | |
| DP-569 | Thr | MeGly | Val | Asp | MePhe | MePhe | Ala | | |
| DP-570 | MeAla | Thr | Phe | Asp | MePhe | MePhe | Val | Ile | pip |
| DP-571 | MePhe | Thr | Phe | Asp | MeLeu | Leu | pip | | |
| DP-572 | MePhe | Leu | MePhe | Asp | MePhe | Ala | Thr | | |
| DP-573 | MePhe | Leu | MePhe | Asp | MePhe | Ile | pip | | |
| DP-574 | Ala | MeLeu | MePhe | Asp | MeAla | Thr | MePhe | Phe | |
| DP-575 | Ser(tBu) | MePhe | Gly | Asp | MeLeu | Ala | pip | Ala | pip |
| DP-576 | MeLeu | MePhe | MeLeu | Asp | MeGly | MeLeu | MePhe | MeLeu | |
| DP-577 | MePhe | MeLeu | MeLeu | Asp | MePhe | Phe | pip | Ile | |
| DP-578 | MeAla | MeLeu | Ser | Asp | MeAla | Ile | pip | | |
| DP-579 | MeLeu | Ser(tBu) | MeLeu | Asp | Pro | Val | Val | Ala | pip |
| DP-580 | Ile | Phe | Phe | Asp | MeAla | Leu | pip | | |
| DP-581 | MeLeu | Ile | Ala | Asp | MeLeu | Ala | Ile | | |
| DP-582 | MePhe | MeLeu | Thr | Asp | MeAla | Thr | Ala | | |
| DP-583 | Ala | MeLeu | Leu | Asp | MeIle | MeLeu | pip | | |
| DP-584 | MePhe | MeLeu | Thr | Asp | MeAla | Phe | | | |
| DP-585 | Val | MeLeu | MeLeu | Asp | MePhe | Ile | | | |
| DP-586 | Val | MeLeu | MeLeu | Asp | MePhe | Ala | | | |
| DP-587 | Leu | MeLeu | MeLeu | Asp | MePhe | Ala | | | |
| DP-588 | Leu | MeLeu | MeLeu | Asp | MePhe | Ala | | | |
| DP-589 | Val | MeLeu | MeLeu | Asp | MePhe | Ala | | | |
| DP-590 | Ala | MeLeu | Leu | Asp | MePhe | Ala | | | |
| DP-591 | MePhe | His | Leu | Asp | MePhe | Ala | | | |
| DP-592 | Pro | Lys(Me2) | Leu | Asp | MePhe | Ala | | | |
| DP-593 | MePhe | Lys(Me2) | Leu | Asp | MePhe | Ala | | | |
| DP-594 | Pro | Glu | Leu | Asp | MePhe | Ala | | | |
| DP-595 | MePhe | Glu | Leu | Asp | MePhe | Ala | | | |
| DP-596 | Pro | Arg(Me2) | Leu | Asp | MePhe | Ala | | | |
| DP-597 | MePhe | Arg(Me2) | Leu | Asp | MePhe | Ala | | | |
| DP-598 | Pro | Ala(3Pyr) | Leu | Asp | MePhe | Ala | | | |
| DP-599 | MePhe | Ala(3Pyr) | Leu | Asp | MePhe | Ala | | | |
| DP-600 | MeLeu | MeLeu | Leu | Asp | MePhe | Ala | | | |
| DP-601 | MeLeu | MeLeu | Leu | Asp | MePhe | Ala | | | |
| DP-602 | MeLeu | MeLeu | Leu | Asp | MePhe | Ala | | | |
| DP-603 | MeLeu | MeLeu | Gln(Me2) | Asp | MePhe | Ala | | | |
| DP-604 | MeLeu | MeLeu | Leu | Asp | MePhe | Ala | | | |
| DP-605 | MeAla | MeLeu | Leu | Asp | MePhe | Ala | | | |
| DP-606 | MeLeu | MeLeu | Leu | Asp | MePhe | Ala | | | |
| DP-607 | MeLeu | MeLeu | Trp | Asp | MePhe | Ala | | | |
| DP-608 | MeLeu | MeLeu | Leu | Asp | MePhe | Ala | | | |
| DP-609 | MeLeu | MeLeu | Leu | Asp | MePhe | Ala | | | |
| DP-610 | MeLeu | MeLeu | Algly | Asp | MePhe | Ala | | | |
| DP-611 | MeAla | MeLeu | Leu | Asp | MePhe | Ala | | | |
| DP-612 | MeAla | MeLeu | Ala | Asp | MePhe | Ala | | | |
| DP-613 | MeLeu | MeLeu | Thr | Asp | MePhe | Ala | | | |
| DP-614 | D-Val | MeVal | Thr | Asp | pip | | | | |
| DP-615 | MeGly | MeVal | Thr | Asp | pip | | | | |
| DP-616 | MeGly | MeVal | Gln | Asp | pip | | | | |
| DP-617 | MeGly | MeLeu | Gln(Me2) | Asp | pip | | | | |
| DP-618 | MeAla | MeLeu | Gln(Me2) | Asp | pip | | | | |

TABLE 11-1-continued

| | | | | | | | | | | | |
|---|---|---|---|---|---|---|---|---|---|---|---|
| DP-619 | MeAla | MeAla | MeLeu | Thr | Asp | | | | | | |
| DP-620 | MeAla | MeAla | MeLeu | Met(O2) | Asp | pip | | | | | |
| DP-621 | MePhe | MeLeu | MeLeu | Thr | Asp | pip | | | | | |
| DP-622 | MeGly | MeAla | MeAla | Thr | Asp | pip | | | | | |
| DP-623 | MeGly | MeAla | MeAla | Thr | Asp | pip | | | | | |
| DP-624 | MeAla | MeAla | MeAla | Ala(4-Thz) | Asp | pip | | | | | |
| DP-625 | MeAla | MePhe | MePhe | Thr | Asp | pip | | | | | |
| DP-626 | MeAla | MeLeu | MeLeu | Gln(Me) | Asp | pip | | | | | |
| DP-627 | MeGly | MeAla | MeAla | Thr | Asp | pip | | | | | |
| DP-628 | MeAla | MeAla | MeAla | Thr | Asp | pip | | | | | |
| DP-629 | MeGly | MeAla | MeAla | Thr | Asp | pip | | | | | |
| DP-630 | MeAla | MePhe | MePhe | Thr | Asp | MePhe | Ala | | | | |
| DP-631 | Val | MeLeu | MeLeu | Val | Asp | pip | | | | | |
| DP-632 | MeLeu | Ala | MeVal | MeLeu | Asp | pip | | | | | |
| DP-633 | Thr | MeGly | MeLeu | MeLeu | Asp | pip | | | | | |
| DP-634 | MeLeu | MeIle | MeAla | MeAla | Asp | pip | | | | | |
| DP-635 | Thr | nPrGly | MeLeu | MeLeu | Asp | pip | | | | | |
| DP-636 | Thr | MeGly | MeLeu | MeLeu | Asp | pip | | | | | |
| DP-637 | Thr | MeGly | MeLeu | MeLeu | Asp | pip | | | | | |
| DP-638 | Leu | MeIle | MeLeu | MeLeu | Asp | pip | | | | | |
| DP-639 | MeLeu | Leu | MeLeu | MeLeu | L-3-ABU | | | | | | |
| DP-640 | MeSer | Leu | MeGly | MeVal | L-3-ABU | | | | | | |
| DP-641 | MeLeu | Leu | MeSer | MeLeu | L-3-ABU | | | | | | |
| DP-642 | MeLeu | Leu | D-Leu | MeAla | L-3-ABU | | | | | | |
| DP-643 | MeGly | MeLeu | Val | MeLeu | L-3-ABU | | | | | | |
| DP-644 | Leu | MeLeu | Ala | MeLeu | L-3-ABU | | | | | | |
| DP-645 | AOC(2) | MeGly | MeLeu | MeLeu | L-3-ABU | | | | | | |
| DP-646 | MeLeu | MeSer | Abu | MeLeu | L-3-ABU | | | | | | |
| DP-647 | MeLeu | MeLeu | MeLeu | MeLeu | L-3-ABU | | | | | | |
| DP-648 | D-Leu | MeLeu | D-Leu | MeLeu | L-3-ABU | | | | | | |
| DP-649 | Leu | MeGly | Abu | MeLeu | L-3-ABU | | | | | | |
| DP-650 | MeLeu | MeSer | MeLeu | MeLeu | L-3-ABU | | | | | | |
| DP-651 | MeLeu | MeLeu | MeLeu | MeLeu | L-3-ABU | | | | | | |
| DP-652 | D-Ala | D-Ala | MeLeu | MeLeu | L-3-ABU | | | | | | |
| DP-653 | Leu | MeLeu | MeSer | MeLeu | L-3-ABU | | | | | | |
| DP-654 | MeLeu | MeSer | Abu | MeLeu | —CF3-bAla | | | | | | |
| DP-655 | MeLeu | MeLeu | Val | MeLeu | —CF3-bAla | | | | | | |
| DP-656 | MeGly | MeLeu | MeLeu | MeLeu | —CF3-bAla | | | | | | |
| DP-657 | D-Ala | MeLeu | Phe | MeLeu | —CF3-bAla | | | | | | |
| DP-658 | MeAla | Thr | MePhe | Asp | MePhe | Leu | Ala | pip | | | |
| DP-659 | MeLeu | MePhe | MeLeu | Asp | MeAla | Leu | Val | MeAla | Ala | | |
| DP-660 | MeLeu | MePhe | MeLeu | Asp | MePhe | MeAla | Ala | Ala | pip | | |
| DP-661 | MeLeu | MePhe | MeLeu | Asp | MeAla | Pro | Val | pip | | | |
| DP-662 | MeLeu | MePhe | MeLeu | Asp | Ala | Pro | Ala | pip | | | |
| DP-663 | MeLeu | MePhe | MeLeu | Asp | MeLeu | Ala | pip | | | | |
| DP-664 | MePhe | MePhe | MeLeu | Asp | Ala | pip | | | | | |
| DP-665 | MePhe | MePhe | MeLeu | Asp | MeAla | Ile | MeAla | Val | Ala | | |
| DP-666 | MePhe | Leu | Pro | Asp | Phe | Leu | Pro | Ala | Ala | | pip |
| DP-667 | MePhe | Leu | Pro | Asp | MeLeu | MeAla | Ile | MePhe | pip | | pip |
| DP-668 | MePhe | Leu | Pro | Asp | MeAla | Ile | pip | | | | |
| DP-669 | MePhe | Leu | Pro | Asp | Ile | pip | MeAla | Ala | pip | | |
| DP-670 | Leu | MePhe | MeVal | Asp | MeGly | MeLeu | MeLeu | Ala | | | |
| DP-671 | Leu | MePhe | MeVal | Asp | Pro | Ala | pip | | | | |

TABLE 11-1-continued

| | | | | | | | |
|---|---|---|---|---|---|---|---|
| DP-672 | Leu | MePhe | MeVal | Asp | MeGly | Ala | pip |
| DP-673 | Ala | MeLeu | MePhe | Asp | pip | | |
| DP-674 | Thr | MeGly | Val | Asp | pip | | |
| DP-675 | MeLeu | Ile | Ala | Asp | pip | | |
| DP-676 | MeGly | MePhe | Val | Asp | MePhe | Ala | pip |
| DP-677 | MeAla | MePhe | Ser(tBu) | Asp | pip | | |
| DP-678 | Thr | MeLeu | MeAla | Asp | pip | | |
| DP-679 | Thr | MeLeu | MeLeu | Asp | pip | | |
| DP-680 | MeAla | Ser(tBu) | MeLeu | Asp | pip | | |
| DP-681 | MeLeu | Ser(tBu) | MeLeu | Asp | pip | | |
| DP-682 | MeAla | Ser(tBu) | MeLeu | Asp | pip | | |
| DP-683 | MeLeu | Ser(tBu) | MeLeu | Asp | pip | | |
| DP-684 | MeLeu | Ser(tBu) | MeLeu | Asp | pip | | |
| DP-685 | Ser(tBu) | MeLeu | MeLeu | Asp | pip | | |
| DP-686 | Ser(tBu) | MeLeu | MeLeu | Asp | pip | | |
| DP-687 | MePhe | Leu | Pro | Asp | pip | | |
| DP-688 | MePhe | Leu | Pro | Asp | pip | | |
| DP-689 | MeGly | Ser(tBu) | MeLeu | Asp | pip | | |
| DP-690 | Thr | Leu | MeLeu | Asp | pip | | |
| DP-691 | MeLeu | MeGly | Leu | Asp | pip | | |
| DP-692 | MeGly | MeLeu | Ser(tBu) | Asp | pip | | |
| DP-693 | Ser(tBu) | MeLeu | MeLeu | Asp | pip | | |
| DP-694 | MeLeu | MeLeu | Ser(tBu) | Asp | pip | | |
| DP-695 | MeLeu | MeLeu | Ser(tBu) | Asp | pip | | |
| DP-696 | Leu | MeLeu | Ser(tBu) | Asp | pip | | |
| DP-697 | MeGly | Ser(tBu) | MeLeu | Asp | pip | | |
| DP-698 | Leu | Thr | MeLeu | Asp | pip | | |
| DP-699 | Phe | MeLeu | MePhe | Asp | pip | | |
| DP-700 | Thr | Ala | MePhe | Asp | pip | | |
| DP-701 | Phe | MeLeu | MePhe | Asp | pip | | |
| DP-702 | MePhe | MeLeu | Phe | Asp | pip | | |
| DP-703 | Thr | MeLeu | Phe | Asp | pip | | |
| DP-704 | MePhe | MeLeu | MeLeu | Asp | pip | | |
| DP-705 | MePhe | MeLeu | Ser(tBu) | Asp | pip | | |
| DP-706 | Thr | Pro | MeLeu | Asp | pip | | |
| DP-707 | MeAla | MeLeu | Ser(tBu) | Asp | pip | | |
| DP-708 | MeAla | Ser(tBu) | MeLeu | Asp | pip | | |
| DP-709 | MePhe | MeLeu | Ser(tBu) | Asp | pip | | |
| DP-710 | MePhe | MeLeu | MePhe | Asp | pip | | |
| DP-711 | Thr | MeLeu | Ser(tBu) | Asp | pip | | |
| DP-712 | MeGly | MeLeu | MePhe | Asp | pip | | |
| DP-713 | MePhe | MeLeu | Leu | Asp | pip | | |
| DP-714 | Thr | MeLeu | Leu | Asp | pip | | |
| DP-715 | Leu | MePhe | Ser(tBu) | Asp | pip | | |
| DP-716 | MeLeu | Thr | MePhe | Asp | pip | | |
| DP-717 | MeGly | MePhe | Ser(tBu) | Asp | pip | | |
| DP-718 | MePhe | Thr | Ser(tBu) | Asp | pip | | |
| DP-719 | MeLeu | MeLeu | MePhe | Asp | pip | | |
| DP-720 | MeLeu | Thr | MeLeu | Asp | pip | | |
| DP-721 | Thr | MeLeu | Leu | Asp | pip | | |
| DP-722 | Thr | Leu | MeLeu | Asp | pip | | |
| DP-723 | MeLeu | Thr | Leu | Asp | pip | | |
| DP-724 | Ser(tBu) | MeGly | Thr | Asp | pip | | |

TABLE 11-1-continued

| | | | | | |
|---|---|---|---|---|---|
| DP-725 | MeLeu | Ser(tBu) | MeLeu | Asp | pip |
| DP-726 | Thr | MeLeu | Leu | MeLeu | pip |
| DP-727 | MeLeu | MeLeu | MeGly | Thr | pip |
| DP-728 | MeLeu | Va | Leu | Ile | pip |
| DP-729 | MeLeu | Va | Leu | Ile | pip |
| DP-730 | Ile | MeAla | Ala | Thr | pip |
| DP-731 | Ile | MeAla | Ala | Thr | pip |
| DP-732 | MeVal | Hph | MeAla | MeLeu | pip |
| DP-733 | MeVal | Phe3 | MeAla | MeLeu | pip |
| DP-734 | MeVal | MeAla | Hph | MeAla | pip |
| DP-735 | MeVal | MeAla | Phe3 | MeAla | pip |
| DP-736 | MeVa | Leu | MeLeu | Ala | pip |
| DP-737 | MeVal | Leu | MeLeu | Ala | pip |
| DP-738 | MePhe | Thr | MeLeu | MeAla | pip |
| DP-739 | MePhe | MeLeu | Thr | MeLeu | pip |
| DP-740 | MePhe | MeLeu | Thr | MeLeu | pip |
| DP-741 | Thr | MeAla | MeLeu | Leu | pip |
| DP-742 | MePhe | MeLeu | Thr | Leu | pip |
| DP-743 | MeLeu | Ser(tBu) | MePhe | MeLeu | pip |
| DP-744 | MeGly | MeLeu | Leu | MePhe | pip |
| DP-745 | MePhe | MeGly | MeLeu | Thr | pip |
| DP-746 | MeLeu | Ser(tBu) | MePhe | MeLeu | pip |
| DP-747 | MeLeu | MeLeu | Thr | Ser(tBu) | pip |
| DP-748 | Ser(tBu) | Thr | MePhe | MeLeu | pip |
| DP-749 | MeLeu | Thr | MePhe | Ser(tBu) | pip |
| DP-750 | MeGly | Ser(tBu) | MePhe | MeLeu | pip |
| DP-751 | Thr | MePhe | MePhe | LeL | pip |
| DP-752 | Leu | MeAla | MeAla | Gly | Asp |
| DP-753 | MePhe | Thr | MeAla | Leu | Asp |
| DP-754 | Leu | MeAla | MeIle | Gly | Asp |
| DP-755 | MePhe | Thr | MeAla | Leu | Asp |
| DP-756 | Ala | MeLeu | Ser(tBu) | MeLeu | Asp |
| DP-757 | MePhe | Thr | MeLeu | Leu | Asp |
| DP-758 | Leu | MeLeu | Ser(tBu) | MeLeu | Asp |
| DP-759 | MeAla | MeLeu | Ser(tBu) | MeLeu | Asp |
| DP-760 | MeLeu | Ser(tBu) | MeLeu | MeAla | Asp |
| DP-761 | MeAla | MeLeu | Ser(tBu) | MeLeu | Asp |
| DP-762 | AePhe(3-C | Thr | MeLeu | Leu | L-3-ABU |
| DP-763 | MeVal | MeLeu | MeAla | Ala | L-3-ABU |
| DP-764 | MeVal | Ala | MeLeu | Leu | L-3-ABU |
| DP-765 | Pro | MeLeu | Ala | MeAla | L-3-ABU |
| DP-766 | Thr | MePhe | MeLeu | Pro | L-3-ABU |
| DP-767 | Thr | MePhe | MeLeu | Prc | L-3-ABU |
| DP-768 | Pro | MeLeu | Ala | MeVal | L-3-ABU |
| DP-769 | Ile | MePhe | MePhe | Phe | L-3-ABU |
| DP-770 | Ala | MeVal | MeLeu | Ile | L-3-ABU |
| DP-771 | MeIle | Ser(tBu) | MeLeu | MeVal | L-3-ABU |
| DP-772 | Ala | MeLeu | MeLeu | Ile | L-3-ABU |
| DP-773 | Thr | MePhe | MeLeu | MeAla | L-3-ABU |
| DP-774 | Pro | MeLeu | AOC(2) | MeVal | L-3-ABU |
| DP-775 | MeAla | Ser(tBu) | MePhe | MeVal | L-3-ABU |
| DP-776 | Ala | MeLeu | MeLeu | Ile | L-3-ABU |
| DP-777 | MePhe | Gly | MeVal | Phe | L-3-ABU |

TABLE 11-1-continued

| | | | | | |
|---|---|---|---|---|---|
| DP-778 | MeAla | MeVal | Phe | Thr | L-3-ABU | |
| DP-779 | MeAla | MeLeu | MeIle | Ser(tBu) | L-3-ABU | |
| DP-780 | MePhe | Thr | MeAla | MeLeu | L-3-ABU | |
| DP-781 | MePhe | Thr | MeAla | MeLeu | L-3-ABU | |
| DP-782 | MePhe(3-Cl) | Thr | MeAla | MeLeu | L-3-ABU | |
| DP-783 | Thr | MePhe | MeAla | MeLeu | L-3-ABU | |
| DP-784 | Let | Thr | Gly | MePhe | L-3-ABU | |
| DP-785 | Ser(tBu) | MeLeu | MePhe | Gly | L-3-ABU | |
| DP-786 | Thr | MeAla | MeLet | Ser(tBu) | L-3-ABU | |
| DP-787 | Thr | MeLeu | MePhe | Ser(tBu) | L-3-ABU | |
| DP-788 | Phe | MeLeu | MePhe | MeLeu | L-3-ABU | |
| DP-789 | MeGly | Ser(tBu) | MeLeu | MeIle | L-3-ABU | |
| DP-790 | Phe(4-CF3) | MeLeu | MePhe | MeLeu | L-3-ABU | |
| DP-791 | MeLeu | Phe | MeLeu | Thr | L-3-ABU | |
| DP-792 | Phe(4-CF3) | MeLeu | MePhe(3-Cl) | MeLeu | L-3-ABU | |
| DP-793 | MePhe | Thr | MePhe | MeLeu | L-3-ABU | |
| DP-794 | Ser(tBu) | MePhe | MeLeu | Gly | L-3-ABU | |
| DP-795 | MeGly | Ser(tBu) | MeLeu | MeLeu | L-3-ABU | |
| DP-796 | MeAla | Phe | MeLeu | MePhe | L-3-ABU | |
| DP-797 | The | MeGly | Ser(tBu) | MeLeu | L-3-ABU | |
| DP-798 | MePhe | Ala | MeLeu | MePhe | L-3-ABU | |
| DP-799 | MeGly | Ser(tBu) | MeLeu | MeIle | L-3-ABU | |
| DP-800 | MeGly | Ser(tBu) | MeLet | MeIle | L-3-ABU | |
| DP-801 | Thr | MeAla | MeLeu | Ser(tBu) | L-3-ABU | |
| DP-802 | Thr | MeAla | MeLeu | Ser(tBu) | L-3-ABU | |
| DP-803 | MeAla | MeLeu | MeIle | MeLeu | L-3-ABU | |
| DP-804 | MeAla | MeLeu | MeIle | Ser(tBu) | L-3-ABU | |
| DP-805 | MeLet | Ile | Ile | MeLeu | L-3-ABU | |
| DP-806 | MeLet | Ile | MeLeu | MeLeu | L-3-ABU | |
| DP-807 | MeAla | Va | Leu | Leu | L-3-ABU | |
| DP-808 | MeAla | Va | Leu | Leu | L-3-ABU | |
| DP-809 | MePhe(3-Cl) | Gly | MeVal | Phe(4-CF3) | L-3-ABU | |
| DP-810 | MeIle | Gly | MeAla | Leu | L-3-ABU | |
| DP-811 | Thr | MePhe(3-Cl) | MeAla | MeLeu | L-3-ABU | |
| DP-812 | MePhe(3-Cl) | Thr | MeAla | MeLeu | L-3-ABU | |
| DP-813 | MeLeu | Thr | MeAla | MeLeu | L-3-ABU | |
| DP-814 | Thr | MeLeu | Phe(4-CF3) | MeVal | L-3-ABU | |
| DP-815 | Thr | Leu | MeIle | Gly | L-3-ABU | |
| DP-816 | MeAla | MeLeu | Ser(tBu) | MeLeu | L-3-ABU | |
| DP-817 | MeAla | MeLeu | Ser(tBu) | MeLeu | L-3-ABU | |
| DP-818 | MeVal | Ala | MeLet | Leu | L-3-ABU | |
| DP-819 | Ile | MePhe | Ala | Phe | L-3-ABU | |
| DP-820 | MeGly | MeIle | Ser(tBu) | MeVal | L-3-ABU | |
| DP-821 | MeGly | MeIle | Ser(tBu) | MeVal | L-3-ABU | |
| DP-822 | MeGly | MeAla | Ser(tBu) | MeVa | L-3-ABU | |
| DP-823 | MeLeu | MeVal | Phe | Thr | L-3-ABU | |
| DP-824 | MePhe | MeVa | MeIle | Gly | L-3-ABU | |
| DP-825 | MeAla | Phe(4-CF3) | MeLeu | MeLeu | L-3-ABU | |
| DP-826 | MeGly | Ser(tBu) | MeLeu | MeIle | L-3-ABU | |
| DP-827 | MeIle | Gly | MeAla | Leu | L-3-ABU | |
| DP-828 | MePhe(3-Cl) | Thr | MeAla | MeLeu | L-3-ABU | |
| DP-829 | Phe(4-CF3) | Thr | MeAla | MeVa | L-3-ABU | |
| DP-830 | MeAla | MeLeu | MeIle | Ser(tBu) | Phe(4A) | pip |

TABLE 11-1-continued

| | | | | | |
|---|---|---|---|---|---|
| DP-831 | MeAla | MeLeu | MeIle | Ser(tBu) | Phe(3A) | pip |
| DP-832 | MeAla | MeLeu | MeIle | Ser(tBu) | Phe(4B) | pip |
| DP-833 | MePhe | Thr | MeAla | MeLeu | Phe(4A) | pip |
| DP-834 | MePhe | Thr | MeAla | MeLeu | Phe(3A) | pip |
| DP-835 | MePhe | Thr | MeAla | MeLeu | Phe(4B) | pip |
| DP-836 | MePhe | Thr | MeAla | MeLeu | Phe(3C) | pip |
| DP-837 | MePhe | Thr | Ser(tBu) | MeLet | Phe(4B) | pip |
| DP-838 | MeGly | MeLeu | Ser(tBu) | MeLeu | Phe(3C) | pip |
| DP-839 | MePhe | MeLeu | MeIle | MeAla | Phe(4A) | pip |
| DP-840 | MeLeu | Gly | MeIle | MeLeu | Phe(3C) | pip |
| DP-841 | Thr | MeAla | MeLeu | MeLeu | Phe(4B) | pip |
| DP-842 | Leu | Thr | Gly | MePhe | Phe(4B) | pip |
| DP-843 | MePhe | MeLeu | MeLeu | MeLeu | Phe(3C) | pip |
| DP-844 | MePhe | MeLeu | MeLeu | MeLeu | Phe(3C) | pip |
| DP-845 | Gly | MeLeu | MeLeu | MeLeu | Phe(4A) | pip |
| DP-846 | MeLeu | MeVa | Phe | Thr | Phe(3A) | pip |
| DP-847 | Leu | MeVa | Phe | Thr | Phe(4B) | pip |
| DP-848 | MePhe | MeAla | Phe | MeVa | Phe(4B) | pip |
| DP-849 | MePhe | Thr | MeAla | MeLeu | Phe(3C) | pip |
| DP-850 | MeIle | Ser(tBu) | MePhe | MeVa | Phe(4A) | pip |
| DP-851 | MeIle | Ser(tBu) | MePhe | MeVa | Phe(3A) | pip |
| DP-852 | MeIle | Ser(tBu) | MePhe | MeVa | Phe(4B) | pip |
| DP-853 | MeIle | Ser(tBu) | MePhe | MeVa | Phe(3C) | pip |
| DP-854 | MeIle | Thr | MePhe | MeVa | Phe(4A) | pip |
| DP-855 | MeIle | Thr | MeGly | MeLeu | Phe(3A) | pip |
| DP-856 | MeIle | Thr | MeGly | MeLeu | Phe(4B) | pip |
| DP-857 | MeIle | Thr | MeGly | MeLeu | Phe(3C) | pip |
| DP-858 | MePhe | Thr | MeAla | MeLeu | Phe(4B) | pip |
| DP-859 | MePhe | Thr | MeAla | MeLeu | Phe(3C) | pip |
| DP-860 | Thr | MePhe | MeLeu | Pro | Phe(3C) | pip |
| DP-861 | MeLeu | Ser(tBu) | MePhe | MeVa | Phe(4B) | pip |
| DP-862 | MeLeu | Thr | MeAla | MeLeu | Phe(3C) | pip |
| DP-863 | MeLeu | Thr | MeGly | MePhe | Phe(4A) | pip |
| DP-864 | Thr | MeGly | MePhe | MeLeu | Phe(4B) | pip |
| DP-865 | Thr | MeLet | Phe | MeVa | Phe(3A) | pip |
| DP-866 | MeVa | MeAla | Leu | MeLeu | Phe(3C) | pip |
| DP-867 | MePhe | MeLeu | MeIle | MePhe | Phe(4B) | pip |
| DP-868 | MePhe | MeAla | MeLeu | MeIle | Phe(4A) | pip |
| DP-869 | MePhe | MeLeu | Ala | MeIle | Phe(3A) | pip |
| DP-870 | MePhe | MeLeu | Ala | MeIle | Phe(4B) | pip |
| DP-871 | MePhe | MeLeu | Ala | MeIle | Phe(3C) | pip |
| DP-872 | MePhe | MeLeu | MeLeu | MeIle | Phe(4B) | pip |
| DP-873 | Ala | MeLeu | Ser(tBu) | MeLeu | Phe(3C) | pip |
| DP-874 | Ala | MeLeu | Ser(tBu) | MeLeu | Phe(4B) | pip |
| DP-875 | Thr | MeGly | MeAla | MeAla | Phe(3C) | pip |
| DP-876 | Thr | MeGly | MeLeu | MeAla | Phe(4B) | pip |
| DP-877 | Thr | Phe | MeLeu | Pro | Phe(3C) | pip |
| DP-878 | MeGly | Leu | Ala | MeIle | Phe(4B) | pip |
| DP-879 | MeGly | Leu | Ala | MeIle | Phe(4B) | pip |
| DP-880 | MeGly | MeLet | Al | MeIle | Phe(4A) | pip |
| DP-881 | Thr | MeGly | MeLeu | MePhe | Phe(4B) | pip |
| DP-882 | Thr | MeLeu | Phe | MeVa | Phe(3A) | pip |
| DP-883 | Leu | MeGly | MeIle | MeAla | Phe(4B) | pip |

TABLE 11-1-continued

| | | | | | | | | |
|---|---|---|---|---|---|---|---|---|
| DP-884 | Ile | Pro | Thr | MeLeu | Phe(3A) | pip | | | |
| DP-885 | MePhe | Thr | Pro | Leu | Phe(3C) | pip | | | |
| DP-886 | Thr | MeGly | MeLeu | MePhe | Phe(3C) | pip | | | |
| DP-887 | Ile | MeAla | Leu | Thr | Phe(4A) | pip | | | |
| DP-888 | Ile | MeAla | Leu | Thr | Phe(4A) | pip | | | |
| DP-889 | Ile | MeAla | Leu | Thr | Phe(3A) | pip | | | |
| DP-890 | Ile | MeAla | Leu | Thr | Phe(4B) | pip | | | |
| DP-891 | Ile | MeAla | Leu | Thr | Phe(4B) | pip | | | |
| DP-892 | Ile | MeAla | Leu | Thr | Phe(3C) | pip | | | |
| DP-893 | Ile | MeAla | Leu | Thr | Phe(3C) | pip | | | |
| DP-894 | Ile | MeAla | Leu | Thr | Phe(4B) | pip | | | |
| DP-895 | MePhe | Thr | Pro | Leu | Phe(3C) | pip | | | |
| DP-896 | MePhe | Thr | Pro | Leu | Phe(3C) | pip | | | |
| DP-897 | MePhe | Thr | Pro | Leu | Phe(4A) | pip | | | |
| DP-898 | Va | Leu | Ala | MeLeu | Phe(3A) | pip | | | |
| DP-899 | MePhe | Thr | MeLeu | Pro | Phe(3C) | pip | | | |
| DP-900 | Phe | Ile | MeGly | Leu | Phe(3C) | pip | | | |
| DP-901 | Phe | Ile | MeGly | Leu | Phe(4B) | pip | | | |
| DP-902 | Phe | Pro | Thr | MeLeu | Phe(3C) | pip | | | |
| DP-903 | MeAla | Val | Leu | Leu | Asp | pip | | | |
| DP-904 | MeAla | MeLeu | Phe | MeLeu | Asp | pip | | | |
| DP-905 | MePhe | MePhe | His | MeLeu | Asp | pip | | | |
| DP-906 | MeLeu | MePhe | MeAla | MeLeu | Asp | pip | | | |
| DP-907 | MePhe | MePhe | Leu | MeLeu | Asp | pip | | | |
| DP-908 | MeLeu | Ala(5-Tet) | MeLeu | MeLeu | Asp | pip | | | |
| DP-909 | MePhe | D-Leu | MeAla | MeLeu | Asp | pip | | | |
| DP-910 | MeLeu | Thr | MeLeu | MeLeu | Asp | Leu | | | |
| DP-911 | MePhe(3-Cl) | MeLeu | Thr | MeLeu | Asp | MeLeu | Pro | Phe | Ile |
| DP-912 | MeLeu | MeAla | MePhe(3-Cl) | Thr | Asp | Val | Ile | MeAla | Ile |
| DP-913 | Va | MePhe | Va | Ile | Asp | MePhe | MeLeu | MePhe | Ile |
| DP-914 | Leu | MePhe | MePhe | MeAla | Asp | Ile | MePhe(3-Cl) | Thr | Ile |
| DP-915 | MePhe | Thr | MePhe | MePhe | Asp | Pro | MePhe(3-Cl) | MeLeu | Ile |
| DP-916 | MeAla | MeLeu | Thr | MeLeu | Asp | MePhe | MeLeu | MeLeu | Ile |
| DP-917 | Thr | MeLeu | MeLeu | MePhe | Asp | Va | Phe | Ile | pip |
| DP-918 | MeLeu | MePhe | MeGly | MePhe | Asp | MeLeu | MePhe | Ile | pip |
| DP-919 | MeLeu | Ile | MeLeu | Leu | Asp | MeGly | Let | MePhe | pip |
| DP-920 | MeLeu | Thr | Leu | MePhe(3-Cl) | Asp | Va | MePhe | MeLeu | pip |
| DP-921 | Leu | MePhe | Leu | Pro | Asp | MePhe | MeLeu | Phe | pip |
| DP-922 | Thr | MePhe(3-Cl) | Thr | Let | Asp | Ile | MeLeu | Val | pip |
| DP-923 | Let | Phe | MePhe(3-Cl) | MePhe(3-Cl) | Asp | MeLeu | MeAla | MePhe(3-Cl) | pip |
| DP-924 | Leu | MePhe(3-Cl) | MeAla | MeLeu | Asp | MePhe | MeAla | MeLeu | Ile |
| DP-925 | Thr | Thr | MeLeu | MeLeu | Asp | MeLeu | Leu | Leu | Ile |
| DP-926 | MeLeu | Pro | Ile | Leu | Asp | Va | MeGly | Pro | Ile |
| DP-927 | Thr | Pro | MePhe | MePhe | Asp | MePhe(3-Cl) | MePhe(3-Cl) | MePhe(3-Cl) | pip |
| DP-928 | Val | MePhe(3-Cl) | MeLeu | Ile | Asp | MeLeu | MeLeu | MeLeu | pip |
| DP-929 | MeAla | Phe | MeLeu | Phe | Asp | MeAla | MeAla | Ile | pip |
| DP-930 | Thr | MePhe | MeGly | Thr | Asp | Prc | Phe | Ile | pip |
| DP-931 | MeLeu | Phe | MeLeu | MePhe(3-Cl) | Asp | MeLeu | Va | Ile | pip |
| DP-932 | Leu | MePhe | Thr | Thr | Asp | MeLeu | MeAla | pip | pip |
| DP-933 | Thr | Val | Leu | MePhe | Asp | Leu | Ile | pip | pip |
| DP-934 | MeLeu | Phe | MeLeu | Va | Asp | MeLeu | Ile | pip | pip |
| DP-935 | Phe | MeLeu | MePhe | Ile | Asp | MePhe | Va | MeAla | Ile |
| DP-936 | MeLeu | MeLeu | Thr | Phe | Asp | MeAla | Val | Prc | Ile |

TABLE 11-1-continued

| | | | | | | | | | | |
|---|---|---|---|---|---|---|---|---|---|---|
| DP-937 | MeAla | Ile | MeLeu | MeLeu | Asp | Prc | MeLeu | Leu | Ile | pip |
| DP-938 | MeLeu | MeLeu | Ile | MeLeu | Asp | MeLeu | Va | MePhe | Ile | pip |
| DP-939 | Phe | MeLeu | MePhe | MeLeu | Asp | Val | MeLeu | Ile | pip | |
| DP-940 | MeGly | MeLeu | Ile | MeLeu | Asp | Thr | MeLeu | Ile | pip | |
| DP-941 | Let | Ile | MeLeu | Leu | Asp | MePhe | Ile | Ile | pip | |
| DP-942 | MePhe(3-Cl) | Thr | MePhe | MePhe | Asp | Ile | MeAla | Ile | pip | |
| DP-943 | Pro | MePhe | Leu | Leu | Asp | Val | Pro | Ile | pip | |
| DP-944 | Thr | Leu | MePhe | MePhe | Asp | MeAla | MeLeu | Ile | pip | |
| DP-945 | MeLeu | MePhe | Thr | MeLeu | Asp | MeAla | Leu | MeLeu | Ile | pip |
| DP-946 | MePhe(3-Cl) | MeLeu | Ile | MePhe | Asp | Ile | Leu | MePhe | Ile | pip |
| DP-947 | MeLeu | Ile | Thr | Va | Asp | MeLeu | MeLeu | MeAla | Ile | pip |
| DP-948 | Gly | Thr | Leu | Let | Asp | MePhe | Val | MeAla | Ile | pip |
| DP-949 | MeLeu | MePhe(3-Cl) | MeLeu | MeLeu | Asp | Phe | Pro | MeLeu | Ile | |
| DP-950 | MeLeu | MeAla | Leu | Ala | Asp | MePhe | Val | Ile | pip | |
| DP-951 | MePhe | Thr | MeAla | Ile | Asp | MePhe | MeLeu | Ile | pip | |
| DP-952 | MePhe | MeLeu | Ala | MeLeu | Asp | MeAla | Val | Ile | pip | |
| DP-953 | Thr | Phe | MePhe | MeAla | Asp | Phe | Ile | pip | | |
| DP-954 | Va | MeLeu | Ser(tBu) | MeLeu | Asp | Ile | Ile | pip | | |
| DP-955 | MeAla | MeLeu | Ala | MeLeu | Asp | Val | Ile | pip | | |
| DP-956 | Ile | Ser | Thr | MeLeu | Asp | Ile | pip | | | |
| DP-957 | MeLeu | Phe | MePhe | Ala | Asp | pip | pip | | | |
| DP-958 | MeLeu | MeLeu | Phe | MeLeu | Asp | pip | pip | | | |
| DP-959 | Let | Ser | Thr | MeLeu | Asp | pip | | | | |
| DP-960 | MeLeu | Thr | MeAla | MeAla | Asp | MePhe | MePhe | Ile | pip | |
| DP-961 | MeGly | Val | MeLeu | MeLeu | Asp | MePhe | MePhe | Ile | pip | |
| DP-962 | Ile | Pro | Thr | Leu | Asp | Ile | Ile | pip | | |
| DP-963 | Ser(tBu) | Thr | Leu | MeLeu | Asp | pip | pip | | | |
| DP-964 | MeAla | Leu | MeLeu | MeLeu | Asp-pip | MeLeu | MePhe(3-Cl) | Ile | | |
| DP-965 | Va | MePhe | Lev | MePhe | Asp | Pro | Ile | pip | | |

*cLogP values for DP-910 to DP-964 were calculated using Daylight Version ver4.95 by Daylight Chemical Information Systems, Inc.
**For DP-964, MeLeu in H-1 corresponds to a ▲ unit.

TABLE 11-2

| Chem CODE | MOLSTRUCTURE |
|---|---|
| Met(O2) | |
| nPrGly | |
| bAla | |
| Tyr(3-F) | |
| Phg | |
| Leu | |
| Glu | |
| Arg | |
| MeGly | |
| Gln | |
| Gly | |

TABLE 11-2-continued
| | | |
|---|---|---|
| MeAla | 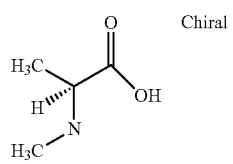 | Chiral |
| MeVal | 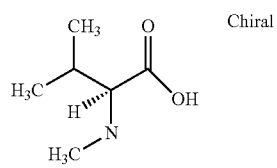 | Chiral |
| MeIle | 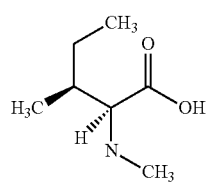 | |
| MeSer | 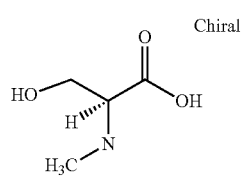 | Chiral |
| MePhe | 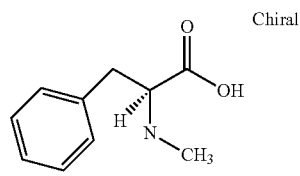 | Chiral |
| Val | 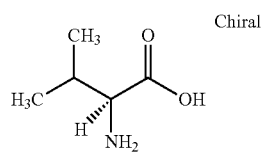 | Chiral |
| Ile | 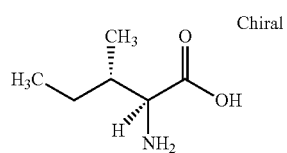 | Chiral |
| Ser | 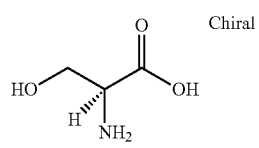 | Chiral |
| Phe | 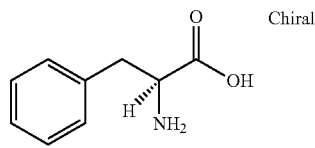 [SMILES: N[C@@H](Cc1ccccc1)C(=O)O] | Chiral |

TABLE 11-2-continued
| | | |
|---|---|---|
| Thr | 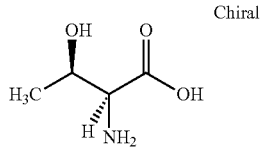 | Chiral |
| His | 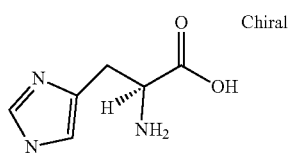 [SMILES: N[C@@H](Cc1c[nH]cn1)C(=O)O] | Chiral |
| Pro | 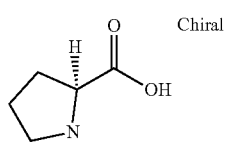 | Chiral |
| Trp | 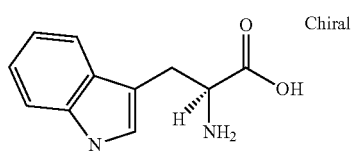 [SMILES: N[C@@H](Cc1c[nH]c2ccccc12)C(=O)O] | Chiral |
| Ala | 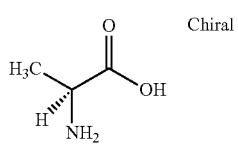 | Chiral |
| Lys | 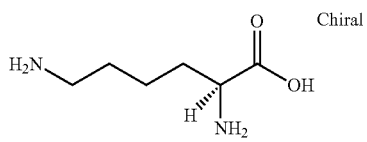 | Chiral |
| MeLeu | 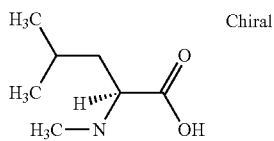 | Chiral |
| Aib | 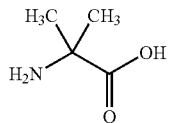 | |
| Abu | 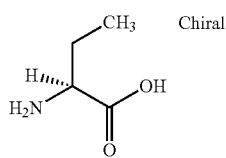 | Chiral |
| Algly | 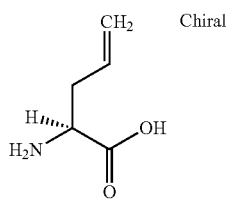 | Chiral |

TABLE 11-2-continued

| | | |
|---|---|---|
| D-Ala | (structure: alanine with NH₂, CH₃, COOH) | Chiral |
| D-Pro | (structure: proline) | Chiral |
| D-Val | (structure: valine) | Chiral |
| Ser(tBu) | (structure: O-tert-butyl serine) | Chiral |
| MeSer(tBu) | (structure: N-methyl O-tert-butyl serine) | Chiral |
| D-MeAla | (structure: N-methyl D-alanine) | Chiral |
| b-MeAla | (structure: β-(methylamino)propionic acid) | |
| g-MeAbu | (structure: 4-(methylamino)butanoic acid) | |
| g-EtAbu | (structure: 4-(ethylamino)butanoic acid) | |
| EtPhe | (structure: N-ethyl phenylalanine) | Chiral |
| Aze(2) | (structure: azetidine-2-carboxylic acid) | Chiral |

TABLE 11-2-continued

| | | |
|---|---|---|
| Pic(2) | *structure* | Chiral |
| D-3-ABU | *structure* | Chiral |
| 3-CF3-bAla | *structure* | Chiral |
| Lys(Me2) | *structure* | Chiral |
| Arg(Me2) | *structure* | Chiral |
| Ala(3Pyr) | *structure* | Chiral |
| Gln(Me2) | *structure* | Chiral |
| Gln(Me) | *structure* | Chiral |
| Ala(4-Thz) | *structure* | Chiral |

TABLE 11-2-continued

| Abbreviation | Structure |
|---|---|
| Ala(CN) | (Chiral) 2-amino-3-cyanopropanoic acid |
| AOC(2) | (Chiral) 2-aminooctanoic acid |
| L-3-ABU | (Chiral) 3-amino-butanoic acid |
| D-MeLeu | (Chiral) N-methyl-D-leucine |
| Ala(5-Tet) | (Chiral) 3-(tetrazol-5-yl)alanine |
| Asp | aspartic acid |
| D-Leu | D-leucine |
| MeHis | (Chiral) N-methyl-histidine |
| Phe(4-CF3) | (Chiral) 4-(trifluoromethyl)phenylalanine |

TABLE 11-2-continued
| | | |
|---|---|---|
| Hph | 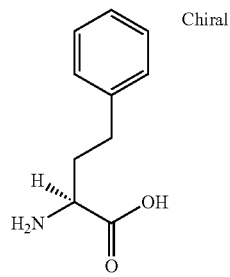 [SMILES: N[C@@H](CCc1ccccc1)C(=O)O] | Chiral |
| Cha | 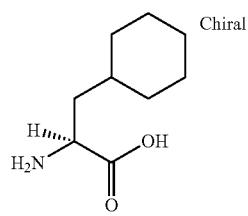 [SMILES: N[C@@H](CC1CCCCC1)C(=O)O] | Chiral |
| Nle | 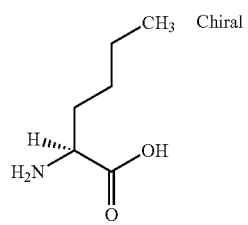 | Chiral |
| Nva | 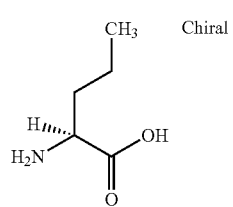 | Chiral |
| D-Phe | 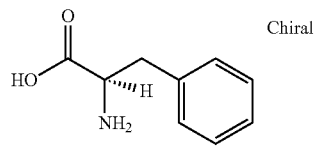 [SMILES: N[C@H](Cc1ccccc1)C(=O)O] | Chiral |
| D-Tyr | 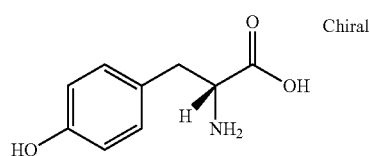 [SMILES: N[C@H](Cc1ccc(O)cc1)C(=O)O] | Chiral |
| Phe3 | 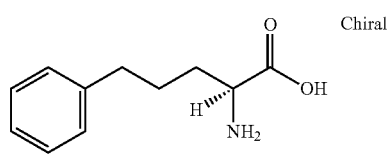 [SMILES: N[C@@H](CCCc1ccccc1)C(=O)O] | Chiral |

TABLE 11-2-continued
| | | |
|---|---|---|
| Phe(4A) | 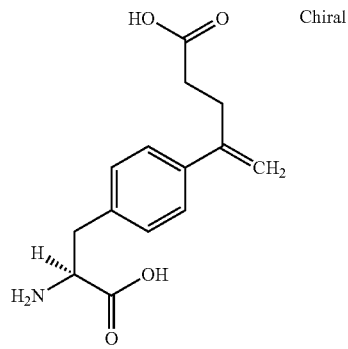 [SMILES: C=C(CCC(=O)O)c1ccc(C[C@H](N)C(=O)O)cc1] | Chiral |
| Phe(4B) | 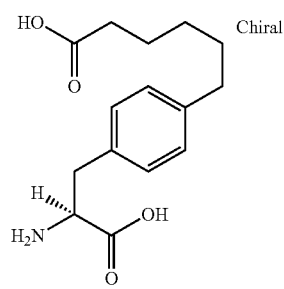 [SMILES: N[C@@H](Cc1ccc(CCCCCC(=O)O)cc1)C(=O)O] | Chiral |
| Phe(3A) | 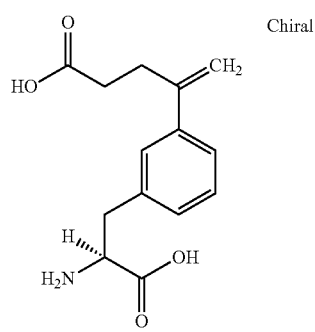 [SMILES: C=C(CCC(=O)O)c1cccc(C[C@H](N)C(=O)O)c1] | Chiral |
| Phe(3C) | 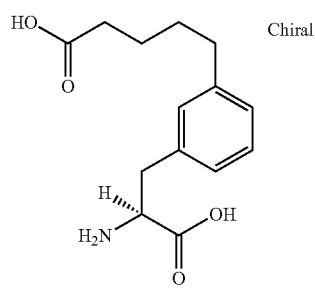 [SMILES: N[C@@H](Cc1cccc(CCCCC(=O)O)c1)C(=O)O] | Chiral |
| $^{HO}$Gly | 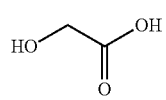 | |
| Asp-pip | 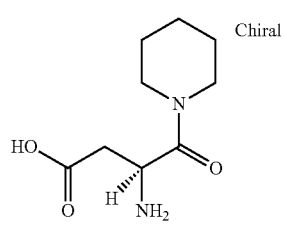 [SMILES: N[C@@H](CC(=O)O)C(=O)N1CCCCC1] | Chiral |

TABLE 11-2-continued
| Ala(4Pyr) | 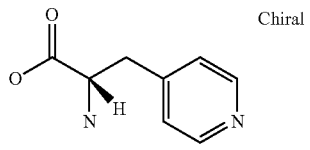 [SMILES: N[C@@H](Cc1ccncc1)C(=O)O] | Chiral |
| Ala(2Pyr) | 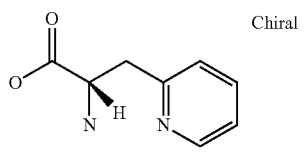 [SMILES: N[C@@H](Cc1ccccn1)C(=O)O] | Chiral |
| D-Leu | 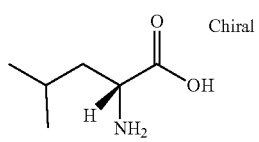 | Chiral |
| MePhe(3-Cl) | 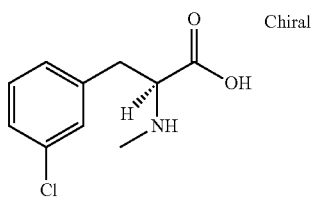 | Chiral |
| Hyp(Et) | 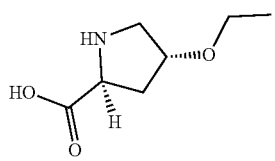 | Chiral |
| MeAla(4-Thz) | 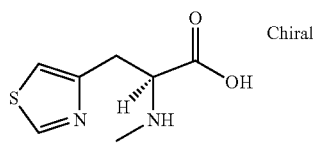 | Chiral |
| Fmoc-MeHis(Trt)-OH | 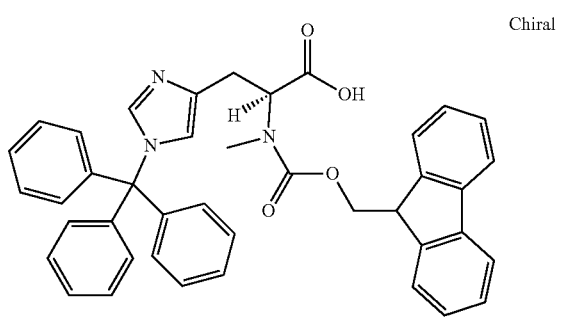 [SMILES: CN(C(=O)OCC1c2ccccc2-c2ccccc21)[C@@H](Cc1cn(C(c2ccccc2)(c2ccccc2)c2ccccc2)cn1)C(=O)O] | Chiral |

TABLE 11-2-continued
Fmoc-Phe(4-CF3)-OH     Chiral
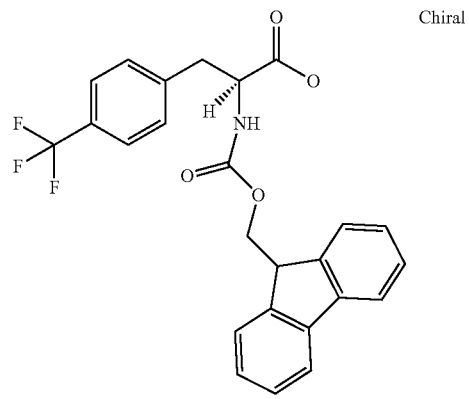 [SMILES: O=C(N[C@@H](Cc1ccc(C(F)(F)F)cc1)C(=O)O)OCC1c2ccccc2-c2ccccc21]
Fmoc-Hph-OH     Chiral
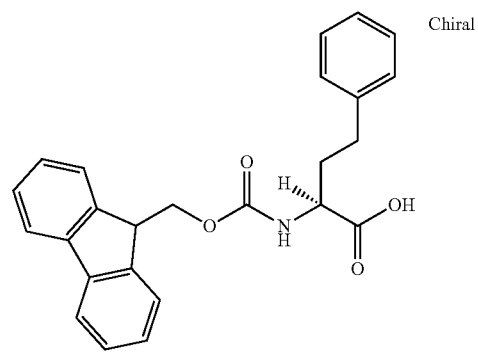 [SMILES: O=C(N[C@@H](CCc1ccccc1)C(=O)O)OCC1c2ccccc2-c2ccccc21]
Fmoc-D-Tyr(tBu)-OH     Chiral
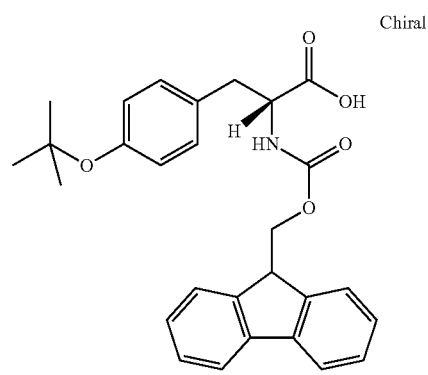 [SMILES: CC(C)(C)Oc1ccc(C[C@@H](NC(=O)OCC2c3ccccc3-c3ccccc32)C(=O)O)cc1]
Fmoc-Phe3-OH     Chiral
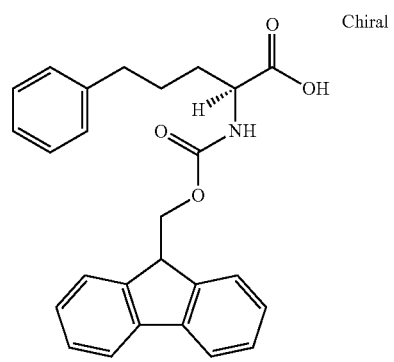 [SMILES: O=C(N[C@@H](CCCc1ccccc1)C(=O)O)OCC1c2ccccc2-c2ccccc21]

TABLE 11-2-continued
| Fmoc-Phe(4A)-pip | 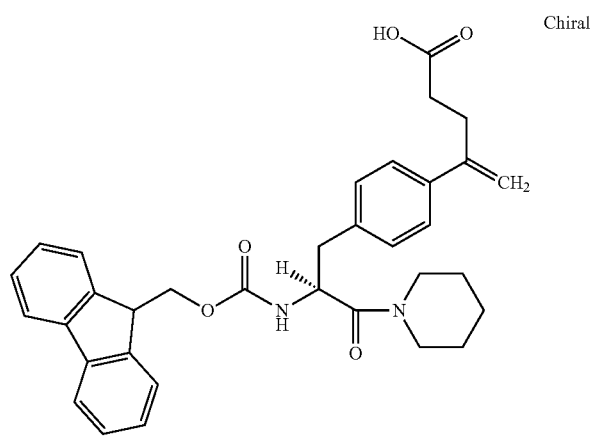 [SMILES: C=C(CCC(=O)O)c1ccc(C[C@H](NC(=O)OCC2c3ccccc3-c3ccccc32)C(=O)N2CCCCC2)cc1] | Chiral |
| Fmoc-Phe(4B)-pip | 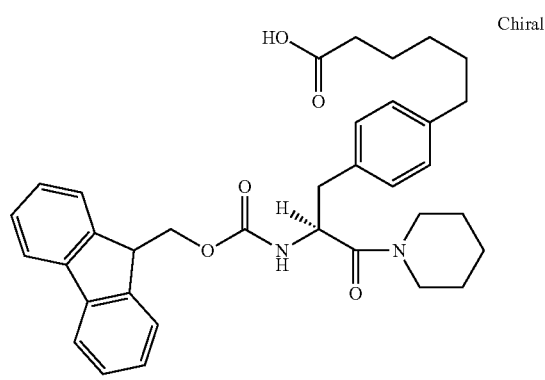 [SMILES: O=C(O)CCCCCc1ccc(C[C@H](NC(=O)OCC2c3ccccc3-c3ccccc32)C(=O)N2CCCCC2)cc1] | Chiral |
| Fmoc-Phe(3A)-pip | 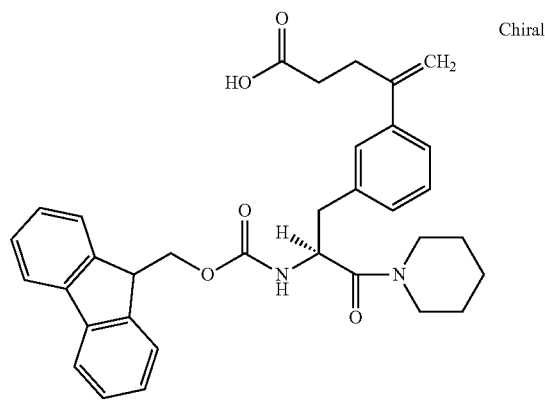 [SMILES: C=C(CCC(=O)O)c1cccc(C[C@H](NC(=O)OCC2c3ccccc3-c3ccccc32)C(=O)N2CCCCC2)c1] | Chiral |
| Fmoc-Phe(3C)-pip | 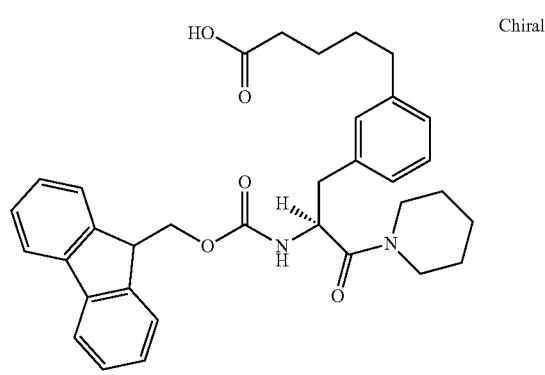 [SMILES: O=C(O)CCCCc1cccc(C[C@H](NC(=O)OCC2c3ccccc3-c3ccccc32)C(=O)N2CCCCC2)c1] | Chiral |

TABLE 11-2-continued
Fmoc-Asp-pip    Chiral
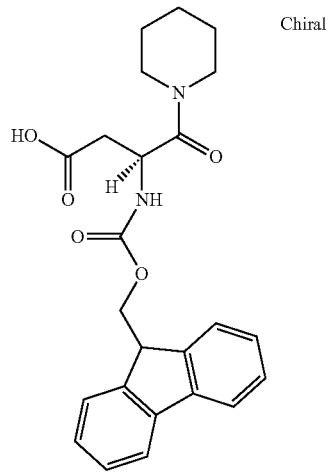 [SMILES: O=C(O)C[C@H](NC(=O)OCC1c2ccccc2-c2ccccc21)C(=O)N1CCCCC1]
Fmoc-D-Leu-OH    Chiral
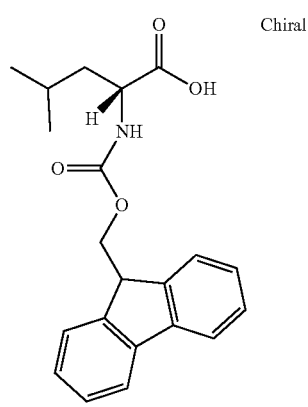 [SMILES: CC(C)C[C@@H](NC(=O)OCC1c2ccccc2-c2ccccc21)C(=O)O]
Fmoc-MePhe(3-Cl)-OH    Chiral
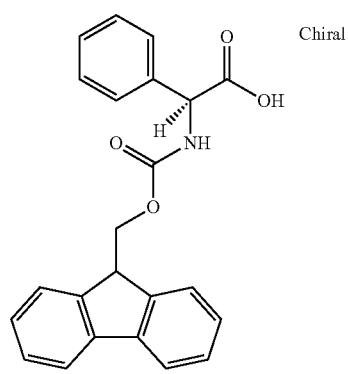 [SMILES: O=C(N[C@H](C(=O)O)c1ccccc1)OCC1c2ccccc2-c2ccccc21]
Fmoc-Met(O2)-OH    Chiral
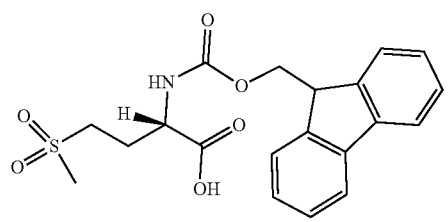

TABLE 11-2-continued
| | |
|---|---|
| Fmoc-nPrGly-OH | 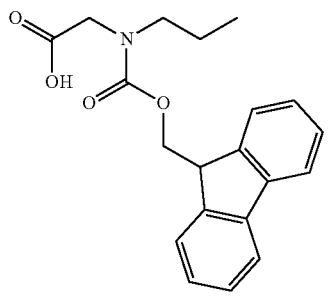 [SMILES: CCCN(CC(=O)O)C(=O)OCC1c2ccccc2-c2ccccc21] |
| Fmoc-bAla-OH | 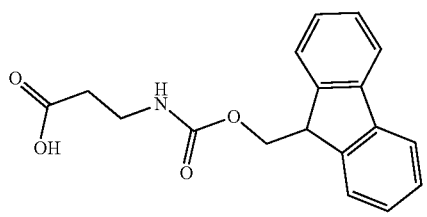 [SMILES: O=C(O)CCNC(=O)OCC1c2ccccc2-c2ccccc21] |
| Fmoc-Tyr(3-F)-OH | 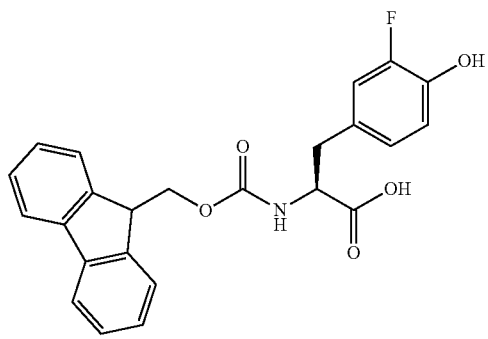 [SMILES: O=C(N[C@@H](Cc1ccc(O)c(F)c1)C(=O)O)OCC1c2ccccc2-c2ccccc21] |
| Fmoc-Phg-OH | 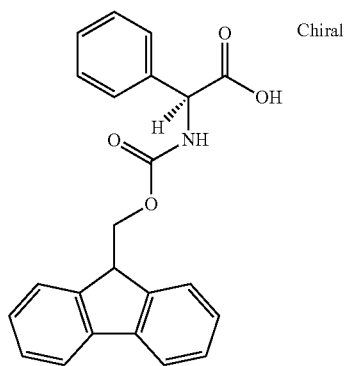 [SMILES: O=C(N[C@H](C(=O)O)c1ccccc1)OCC1c2ccccc2-c2ccccc21] |
| Fmoc-Leu-OH | 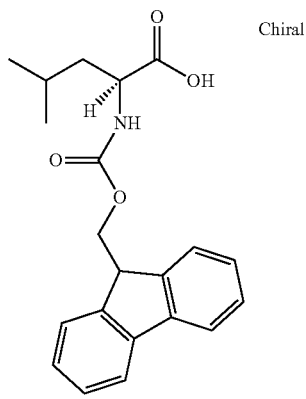 [SMILES: CC(C)C[C@H](NC(=O)OCC1c2ccccc2-c2ccccc21)C(=O)O] |

TABLE 11-2-continued
Fmoc-Glu(OAl)-OH 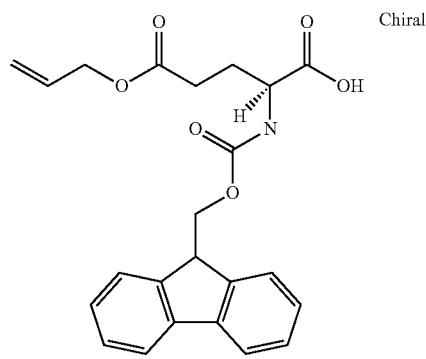 [SMILES: C=CCOC(=O)CC[C@H](NC(=O)OCC1c2ccccc2-c2ccccc21)C(=O)O]
Fmoc-Arg(Me2)-OH 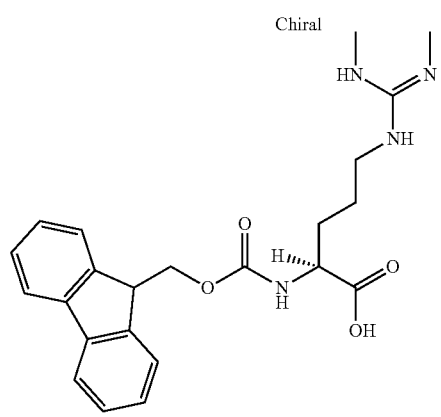 [SMILES: C/N=C(\NC)NCCC[C@H](NC(=O)OCC1c2ccccc2-c2ccccc21)C(=O)O]
Fmoc-MeGly-OH 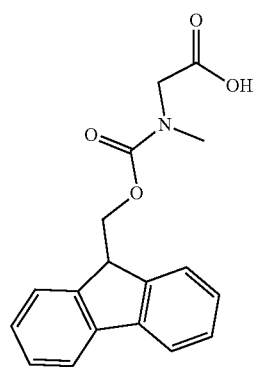 [SMILES: CN(CC(=O)O)C(=O)OCC1c2ccccc2-c2ccccc21]
Fmoc-Gln-OH 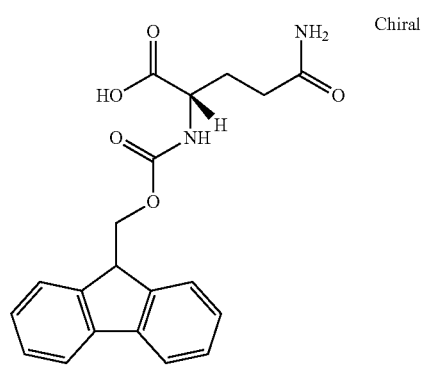 [SMILES: NC(=O)CC[C@H](NC(=O)OCC1c2ccccc2-c2ccccc21)C(=O)O]

TABLE 11-2-continued
Fmoc-Gly-OH 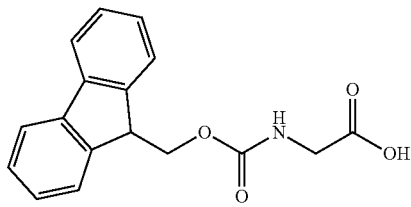 [SMILES: O=C(O)CNC(=O)OCC1c2ccccc2-c2ccccc21]
Fmoc-MeAla-OH 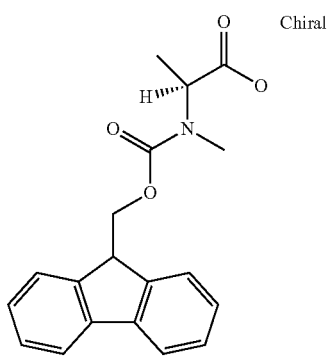 [SMILES: C[C@@H](C(=O)O)N(C)C(=O)OCC1c2ccccc2-c2ccccc21] Chiral
Fmoc-MeVal-OH 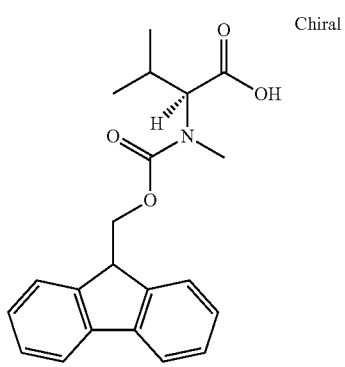 [SMILES: CC(C)[C@@H](C(=O)O)N(C)C(=O)OCC1c2ccccc2-c2ccccc21] Chiral
Fmoc-MeIle-OH 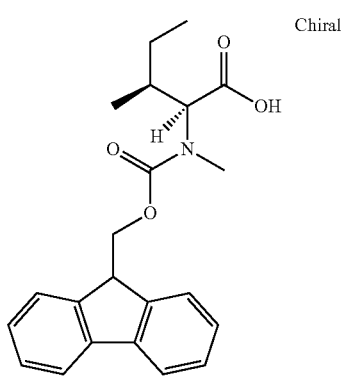 [SMILES: CC[C@H](C)[C@@H](C(=O)O)N(C)C(=O)OCC1c2ccccc2-c2ccccc21] Chiral TABLE 11-2-continued
Fmoc-MeSer(DMT)-OH 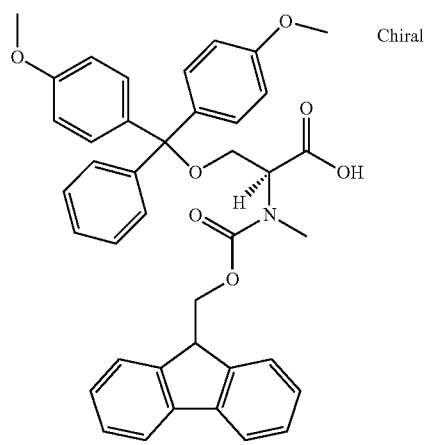 [SMILES: COc1ccc(C(OC[C@@H](C(=O)O)N(C)C(=O)OCC2c3ccccc3-c3ccccc32)(c2ccccc2)c2ccc(OC)cc2)cc1]
Fmoc-MePhe-OH 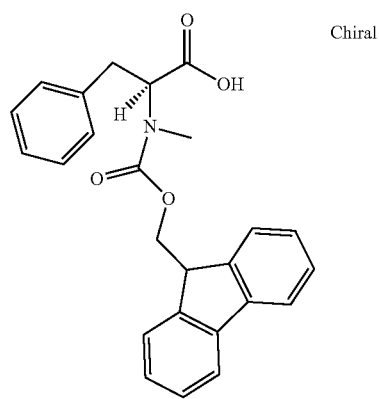 [SMILES: CN(C(=O)OCC1c2ccccc2-c2ccccc21)[C@@H](Cc1ccccc1)C(=O)O]
Fmoc-Val-OH 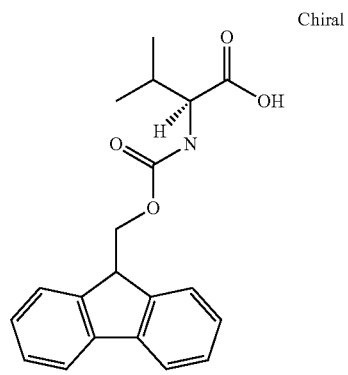 [SMILES: CC(C)[C@H](NC(=O)OCC1c2ccccc2-c2ccccc21)C(=O)O]
Fmoc-Ile-OH 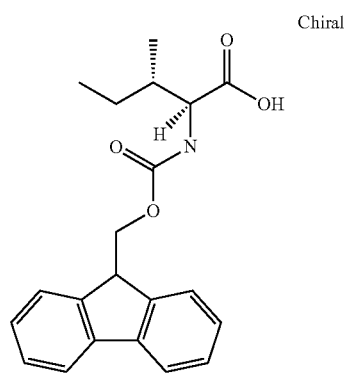 [SMILES: CC[C@H](C)[C@H](NC(=O)OCC1c2ccccc2-c2ccccc21)C(=O)O]

TABLE 11-2-continued
Fmoc-Ser(Trt)-OH 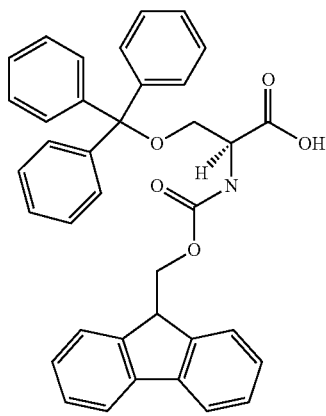 Chiral
Fmoc-Phe-OH 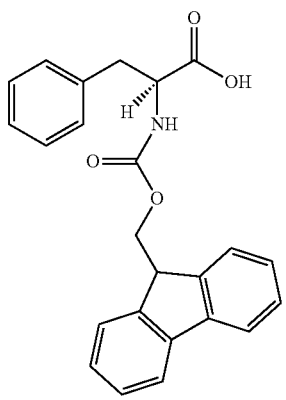 Chiral
Fmoc-Thr(Trt)-OH 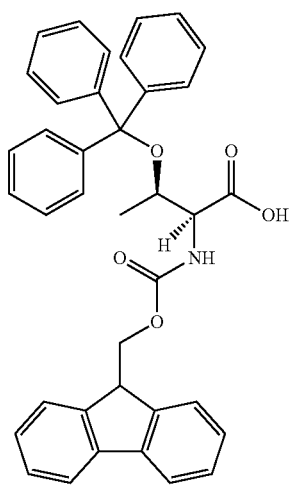 Chiral
Fmoc-His(MMT)-OH 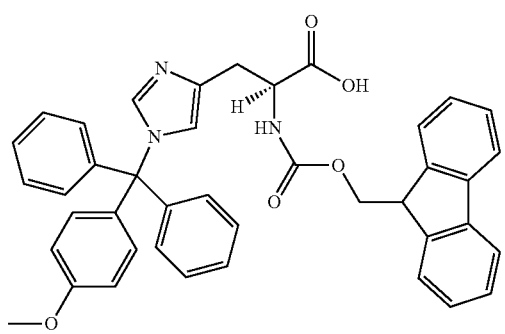 Chiral TABLE 11-2-continued
Fmoc-Pro-OH 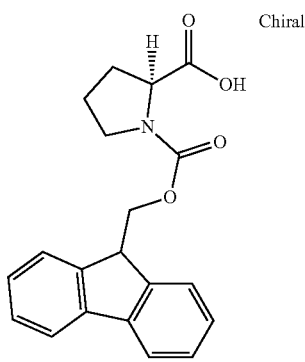 [SMILES: O=C(O)[C@@H]1CCCN1C(=O)OCC1c2ccccc2-c2ccccc21]
Fmoc-Trp-OH 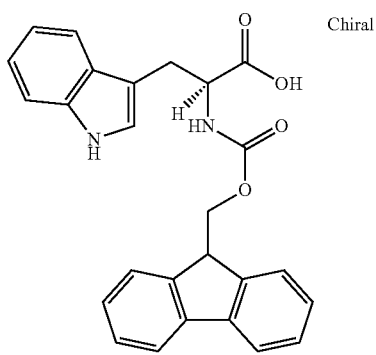 [SMILES: O=C(N[C@@H](Cc1c[nH]c2ccccc12)C(=O)O)OCC1c2ccccc2-c2ccccc21]
Fmoc-Ala-OH 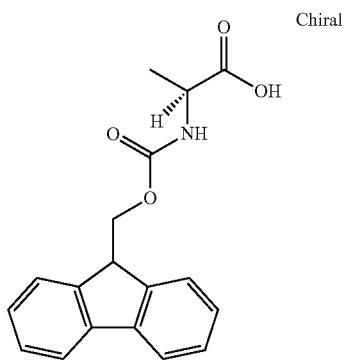 [SMILES: C[C@H](NC(=O)OCC1c2ccccc2-c2ccccc21)C(=O)O]
Fmoc-Lys(Boc)-OH 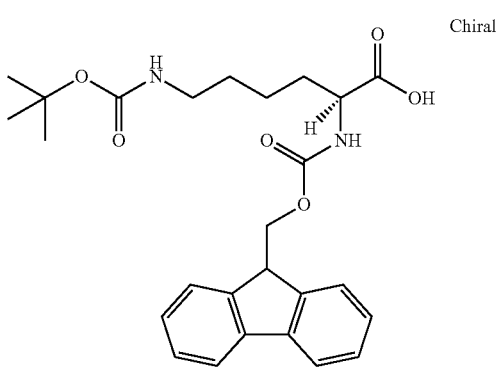 [SMILES: CC(C)(C)OC(=O)NCCCC[C@H](NC(=O)OCC1c2ccccc2-c2ccccc21)C(=O)O]

TABLE 11-2-continued
| Fmoc-MeLeu-OH | 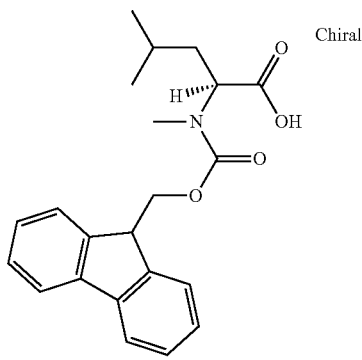 [SMILES: CC(C)C[C@@H](C(=O)O)N(C)C(=O)OCC1c2ccccc2-c2ccccc21] |
| Fmoc-Aib-OH | 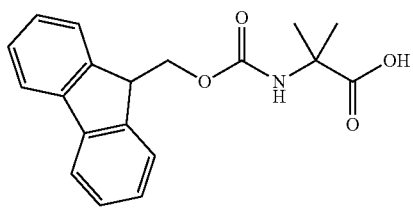 [SMILES: CC(C)(NC(=O)OCC1c2ccccc2-c2ccccc21)C(=O)O] |
| Fmoc-Abu-OH | 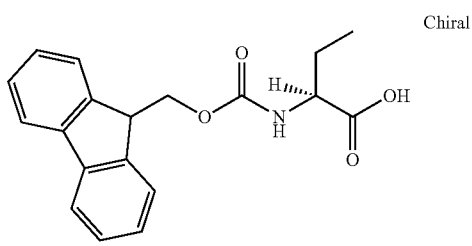 [SMILES: CC[C@H](NC(=O)OCC1c2ccccc2-c2ccccc21)C(=O)O] |
| Fmoc-Algly-OH | 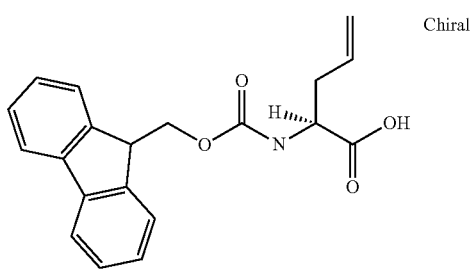 [SMILES: C=CC[C@H](NC(=O)OCC1c2ccccc2-c2ccccc21)C(=O)O] |
| Fmoc-D-Ala-OH | 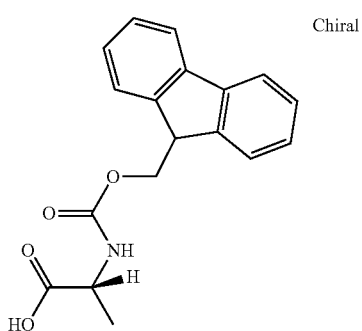 [SMILES: C[C@@H](NC(=O)OCC1c2ccccc2-c2ccccc21)C(=O)O] |

TABLE 11-2-continued
| Fmoc-D-Pro-OH | 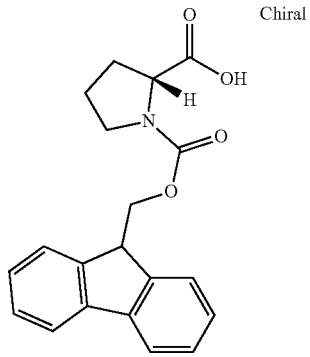 [SMILES: O=C(O)[C@H]1CCCN1C(=O)OCC1c2ccccc2-c2ccccc21] | Chiral |
| Fmoc-D-Val-OH | 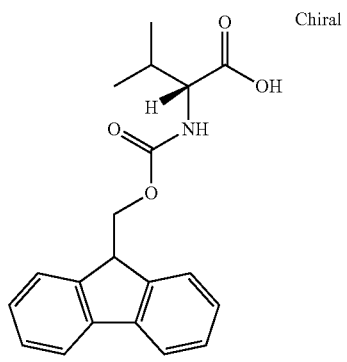 [SMILES: CC(C)[C@@H](NC(=O)OCC1c2ccccc2-c2ccccc21)C(=O)O] | Chiral |
| Fmoc-Ser(tBu)-OH | 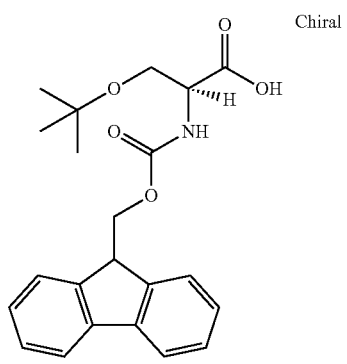 | Chiral |
| Fmoc-MeSer(tBu)-OH | 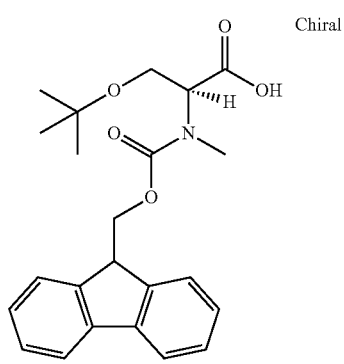 [SMILES: CN(C(=O)OCC1c2ccccc2-c2ccccc21)[C@@H](COC(C)(C)C)C(=O)O] | Chiral |

TABLE 11-2-continued
| Fmoc-D-MeAla-OH | 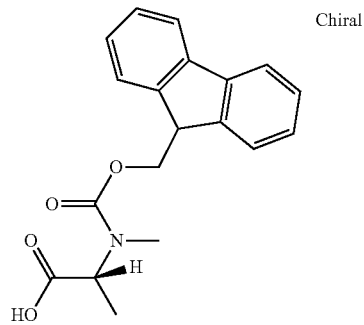 [SMILES: C[C@H](C(=O)O)N(C)C(=O)OCC1c2ccccc2-c2ccccc21] Chiral |
| Fmoc-b-MeAla-OH | 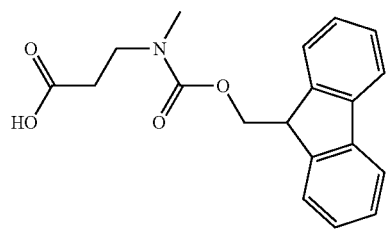 [SMILES: CN(CCC(=O)O)C(=O)OCC1c2ccccc2-c2ccccc21] |
| Fmoc-g-MeAbu-OH | 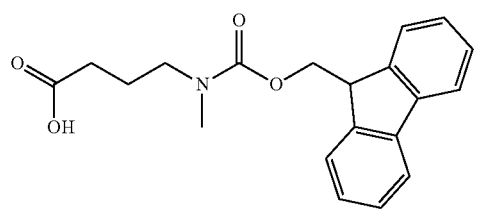 [SMILES: CN(CCCC(=O)O)C(=O)OCC1c2ccccc2-c2ccccc21] |
| Fmoc-g-EtAbu-OH | 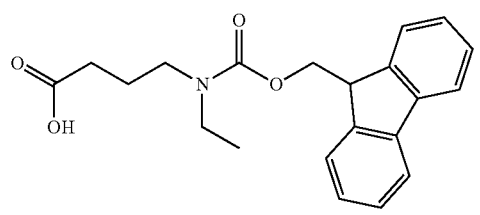 [SMILES: CCN(CCCC(=O)O)C(=O)OCC1c2ccccc2-c2ccccc21] |
| Fmoc-EtPhe-OH | 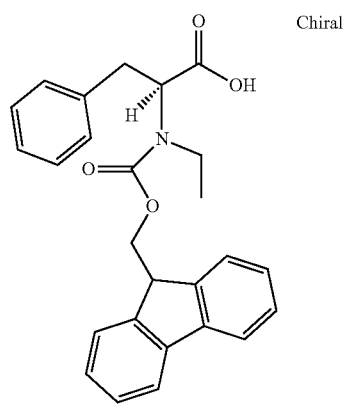 [SMILES: CCN(C(=O)OCC1c2ccccc2-c2ccccc21)[C@@H](Cc1ccccc1)C(=O)O] Chiral |

TABLE 11-2-continued
| Fmoc-Aze(2)-OH | 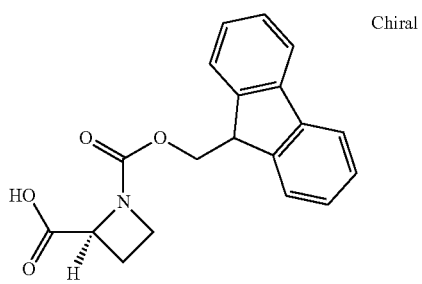 [SMILES: O=C(O)[C@@H]1CCN1C(=O)OCC1c2ccccc2-c2ccccc21] | Chiral |
| Fmoc-Pic(2)-OH | 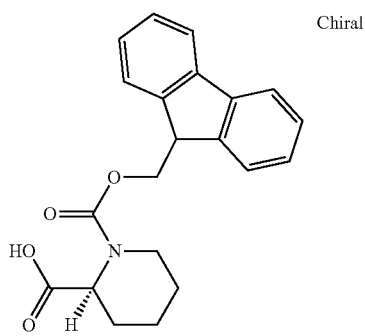 [SMILES: O=C(O)[C@@H]1CCCCN1C(=O)OCC1c2ccccc2-c2ccccc21] | Chiral |
| Fmoc-D-3-ABU-OH | 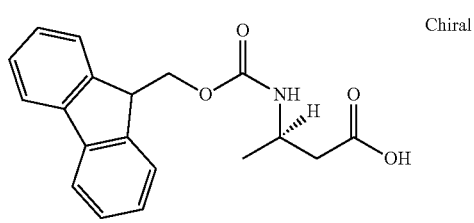 [SMILES: C[C@H](CC(=O)O)NC(=O)OCC1c2ccccc2-c2ccccc21] | Chiral |
| Fmoc-CF3-bAla-OH | 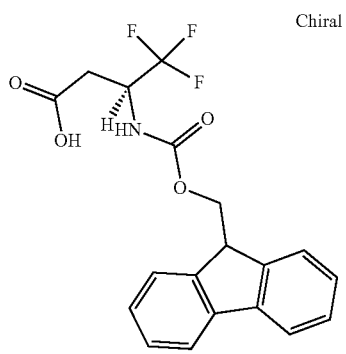 [SMILES: O=C(O)C[C@H](NC(=O)OCC1c2ccccc2-c2ccccc21)C(F)(F)F] | Chiral |
| Fmoc-Lys(Me2)-OH | 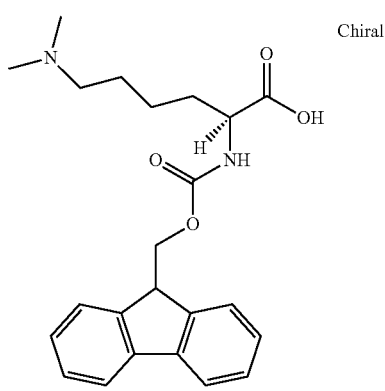 [SMILES: CN(C)CCCC[C@H](NC(=O)OCC1c2ccccc2-c2ccccc21)C(=O)O] | Chiral |

TABLE 11-2-continued
Fmoc-Ala(3Pyr)-OH 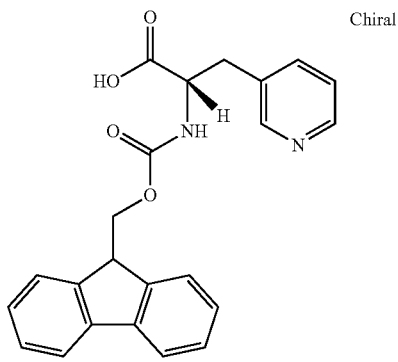 [SMILES: O=C(N[C@@H](Cc1cccnc1)C(=O)O)OCC1c2ccccc2-c2ccccc21] Chiral
Fmoc-Gln(Me2)-OH 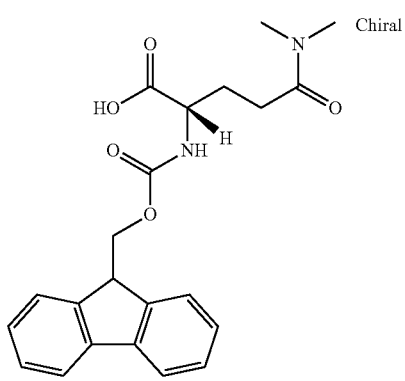 [SMILES: CN(C)C(=O)CC[C@H](NC(=O)OCC1c2ccccc2-c2ccccc21)C(=O)O] Chiral
Fmoc-Gln(Me)-OH 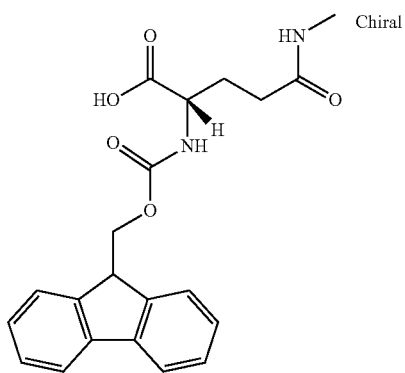 [SMILES: CNC(=O)CC[C@H](NC(=O)OCC1c2ccccc2-c2ccccc21)C(=O)O] Chiral
Fmoc-MeAla(4-Thz)-OH 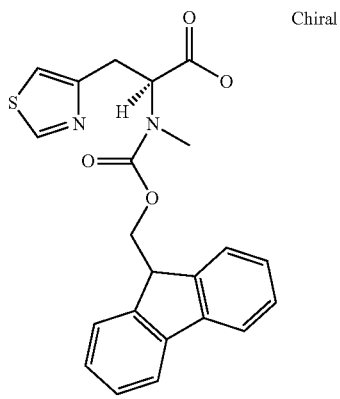 [SMILES: CN(C(=O)OCC1c2ccccc2-c2ccccc21)[C@@H](Cc1cscn1)C(=O)O] Chiral TABLE 11-2-continued
Fmoc-Ala(CN)-OH 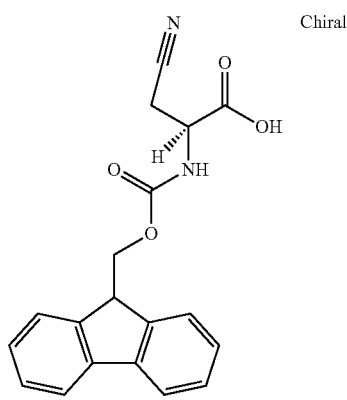 [SMILES: N#CC[C@H](NC(=O)OCC1c2ccccc2-c2ccccc21)C(=O)O] Chiral
Fmoc-AOC(2)-OH 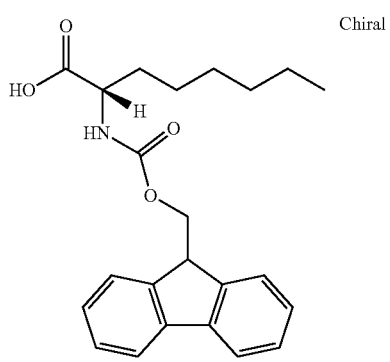 [SMILES: CCCCCC[C@H](NC(=O)OCC1c2ccccc2-c2ccccc21)C(=O)O] Chiral
Fmoc-L-3-ABU-OH 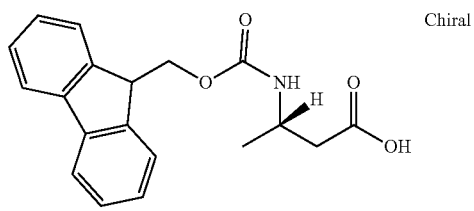 [SMILES: C[C@@H](CC(=O)O)NC(=O)OCC1c2ccccc2-c2ccccc21] Chiral
Fmoc-Ala(5-Tet(Trt))-OH 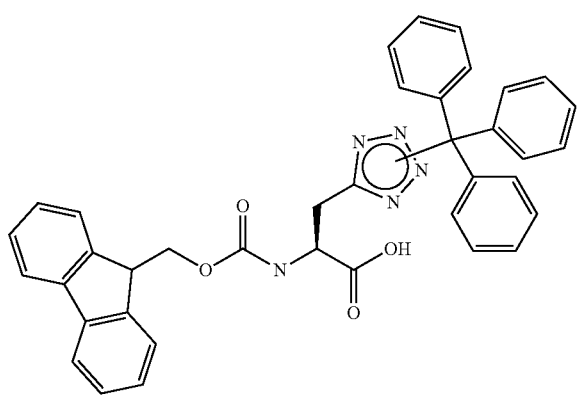
Fmoc-Hyp(Et)-OH 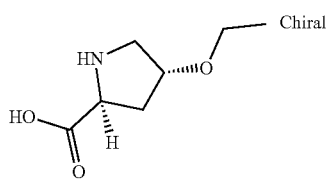 Chiral TABLE 11-2-continued
| Fmoc-Ala(4-Thz)-OH | 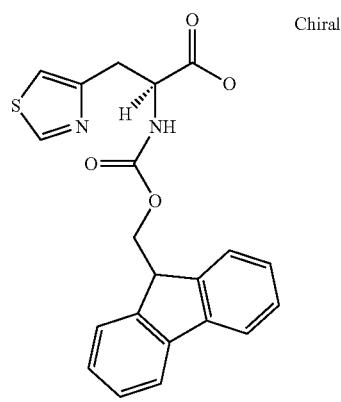 [SMILES: O=C(N[C@@H](Cc1cscn1)C(=O)O)OCC1c2ccccc2-c2ccccc21] |
| Fmoc-Asp(OBn)-OH | 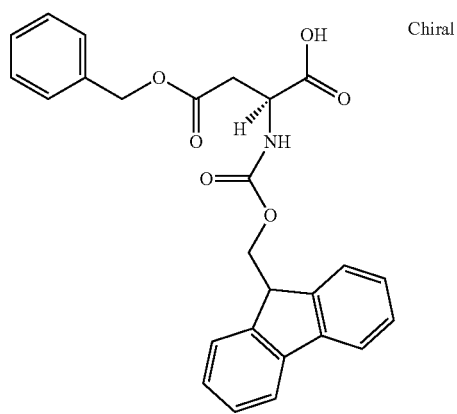 [SMILES: O=C(C[C@H](NC(=O)OCC1c2ccccc2-c2ccccc21)C(=O)O)OCc1ccccc1] |
| Fmoc-Ser-OCF3Pis | 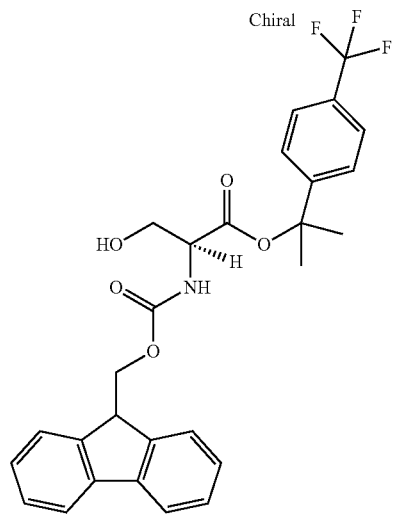 [SMILES: CC(C)(OC(=O)[C@H](CO)NC(=O)OCC1c2ccccc2-c2ccccc21)c1ccc(C(F)(F)F)cc1] |

TABLE 11-2-continued
| Fmoc-Asp(OtBu)-OH | 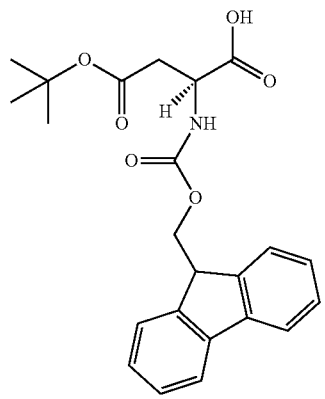 | Chiral |

TABLE 11-3-1
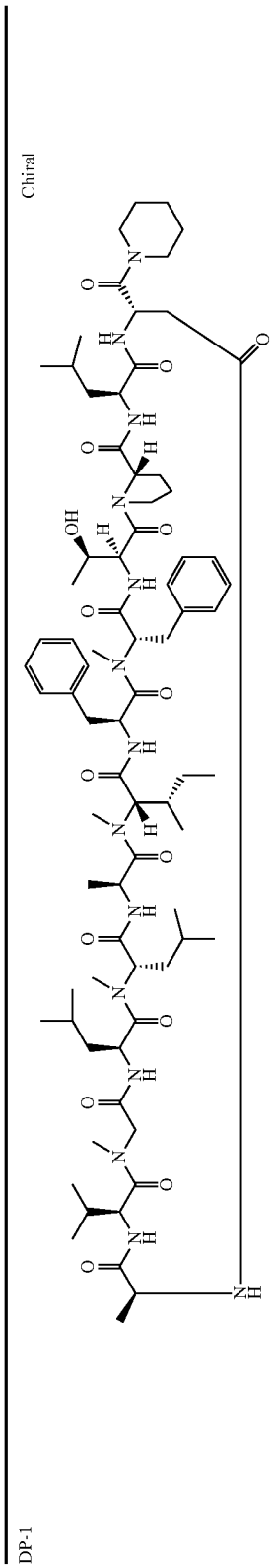
DP-1
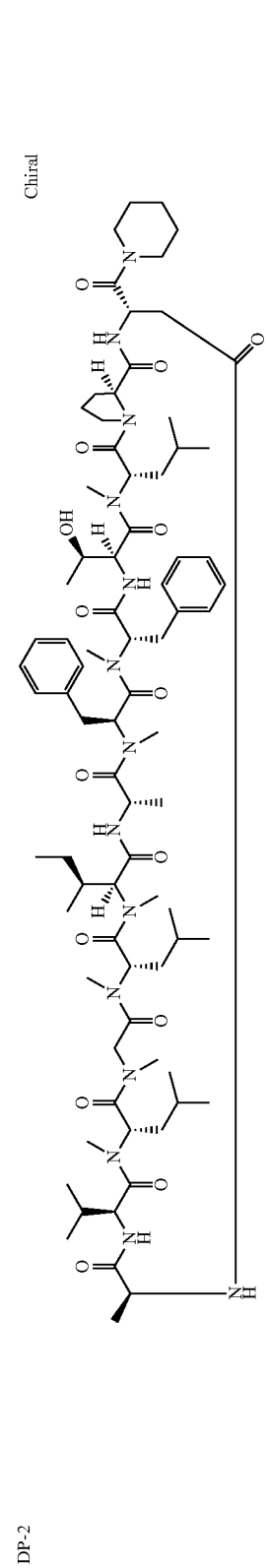
DP-2
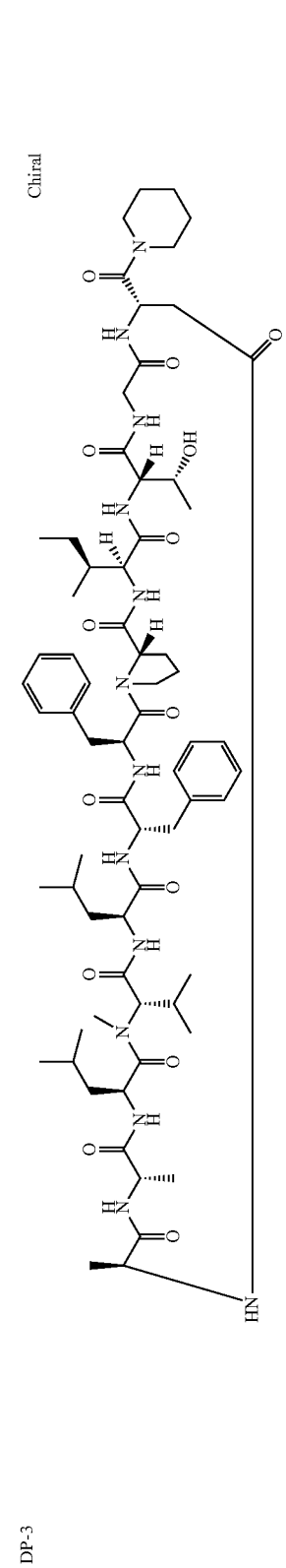
DP-3

TABLE 11-3-1-continued
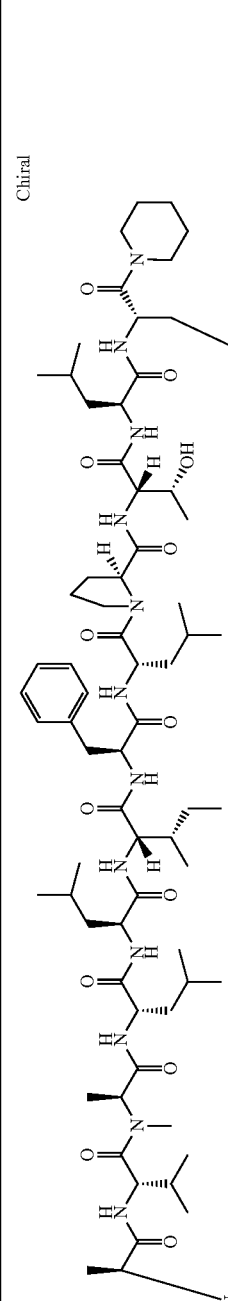
DP-4
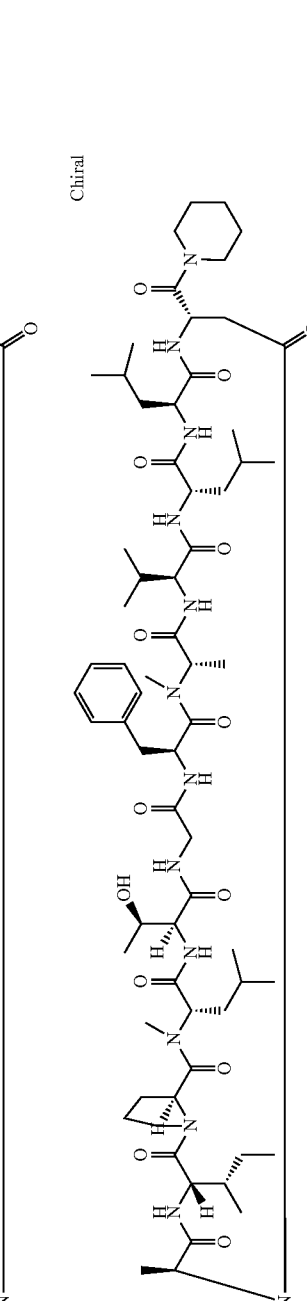
DP-5
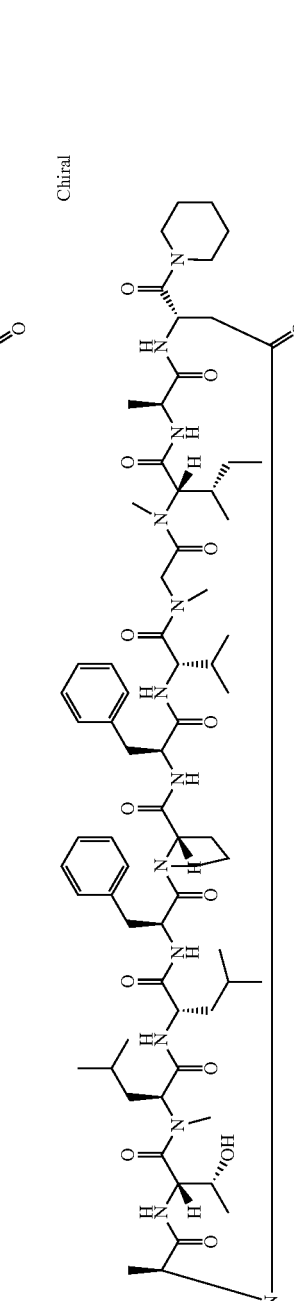
DP-6
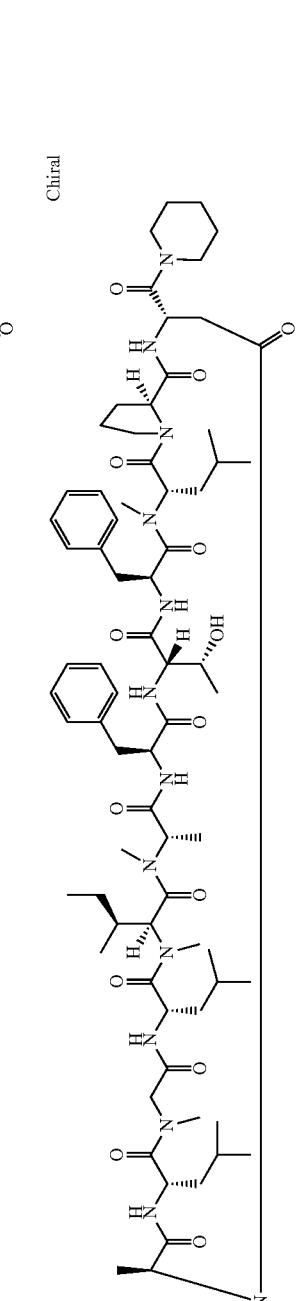
DP-7

TABLE 11-3-1-continued

| DP-8 | DP-9 | DP-10 | DP-11 |

TABLE 11-3-1-continued
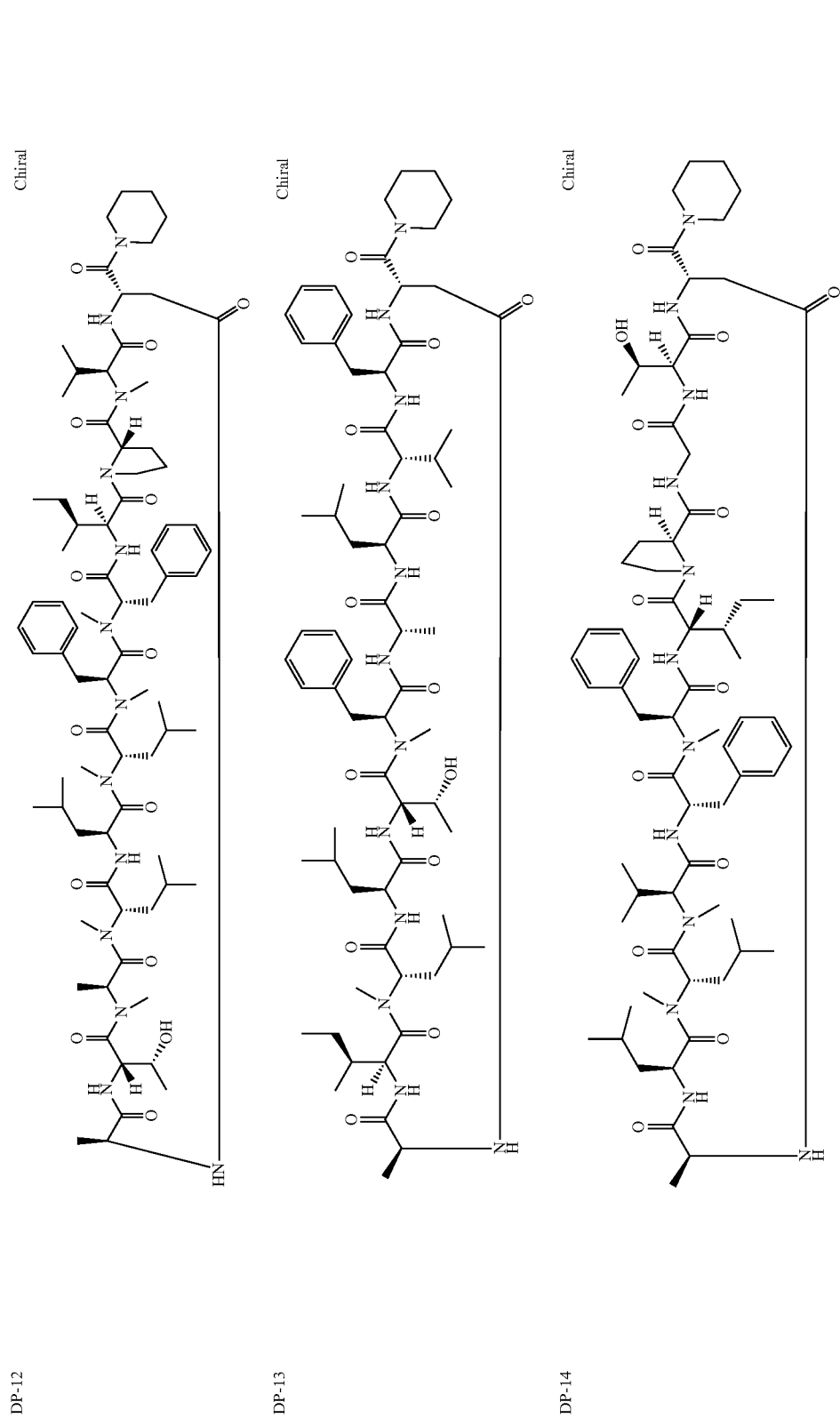
DP-12
DP-13
DP-14

TABLE 11-3-1-continued
| | |
|---|---|
| DP-15 | 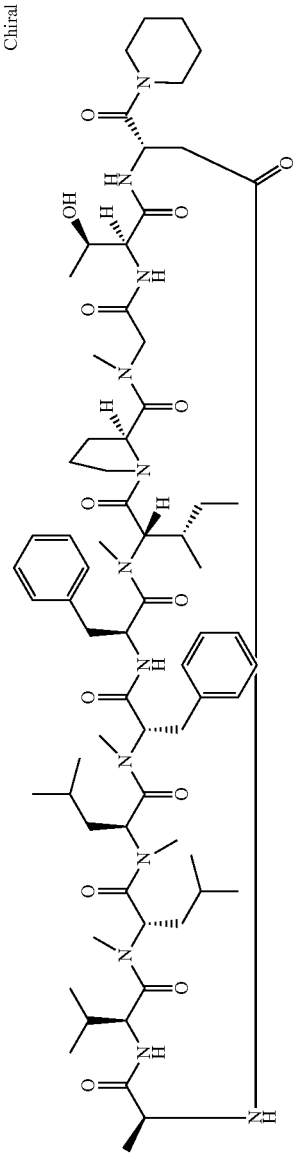 |
| DP-16 | 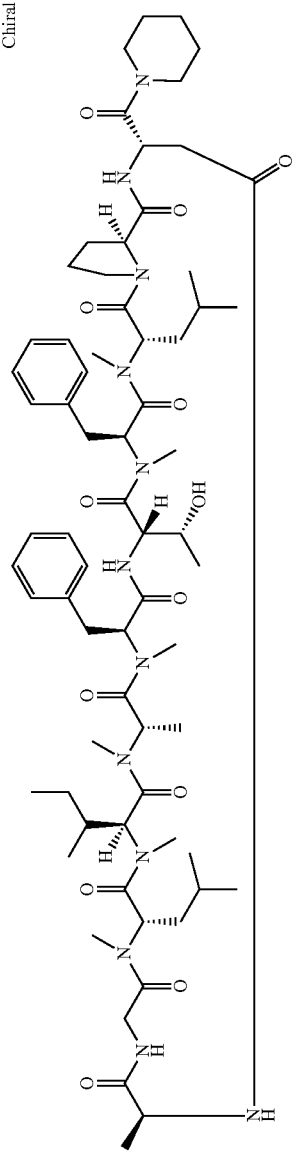 |
| DP-17 | 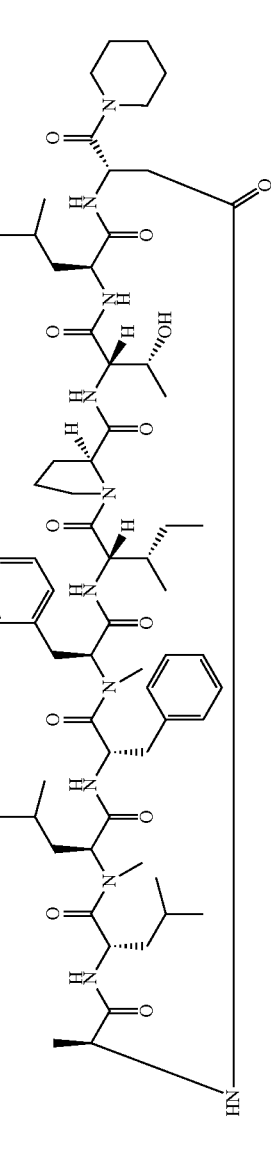 |

TABLE 11-3-1-continued
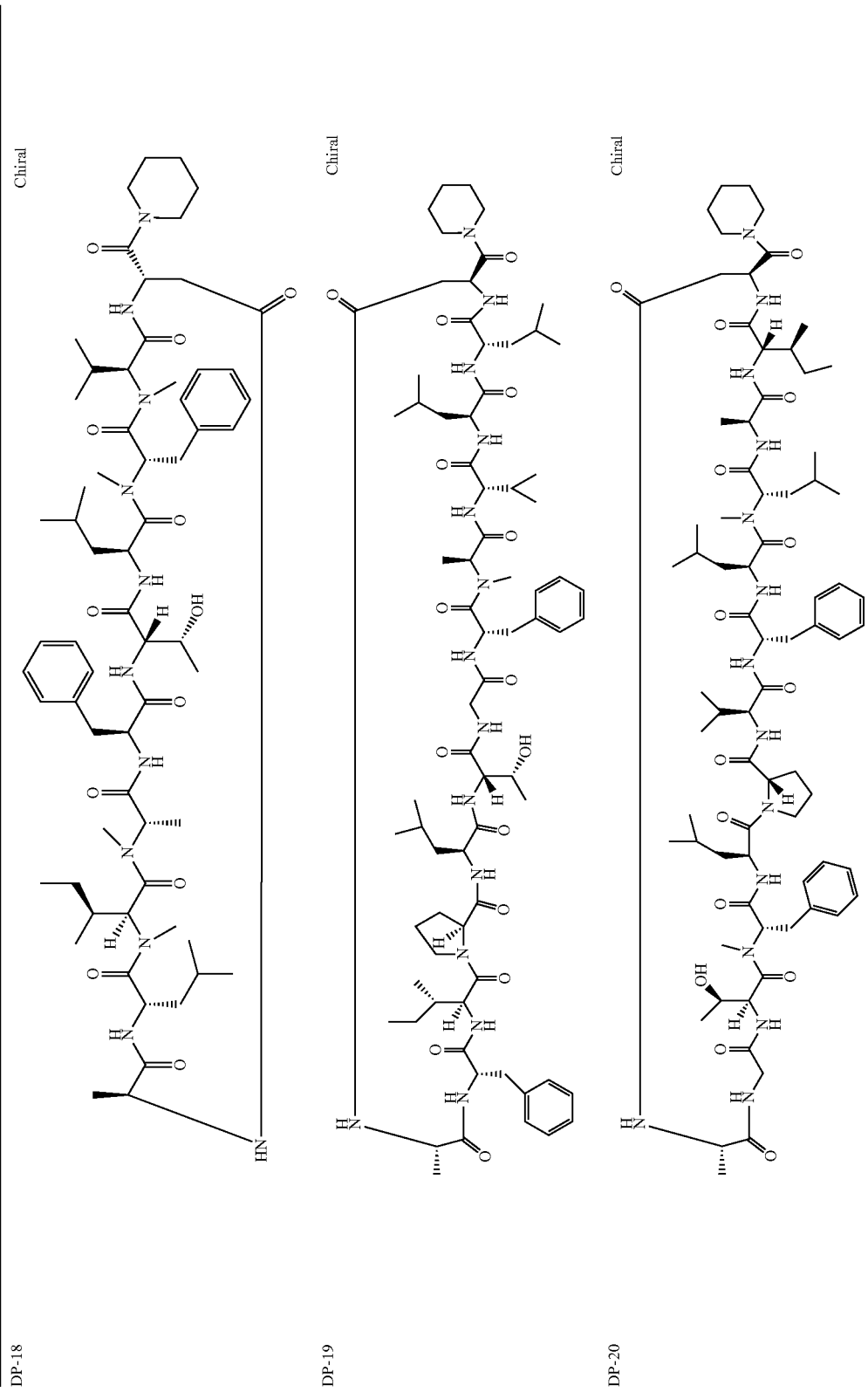
DP-18
DP-19
DP-20

TABLE 11-3-1-continued
| | |
|---|---|
| DP-21 | 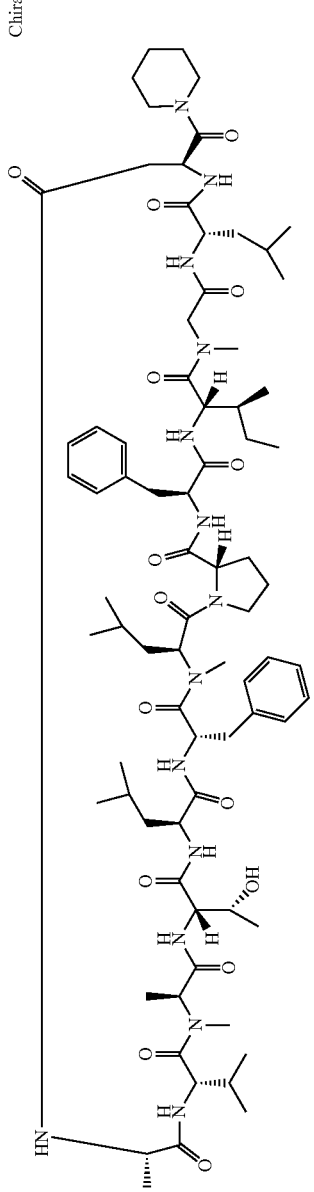 |
| DP-22 | 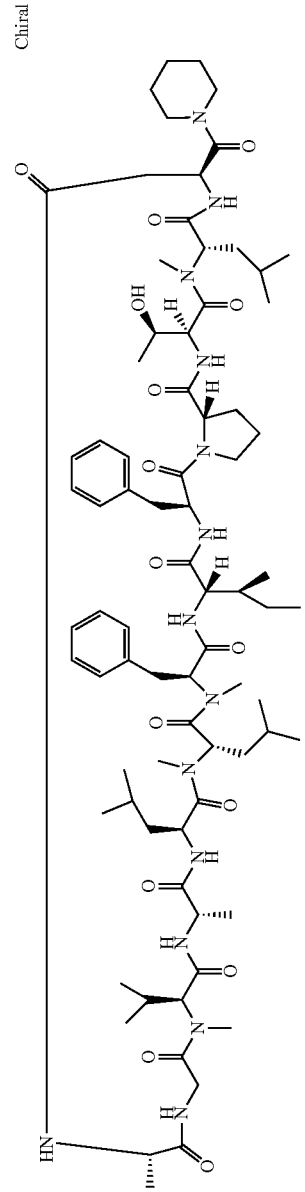 |
| DP-23 | 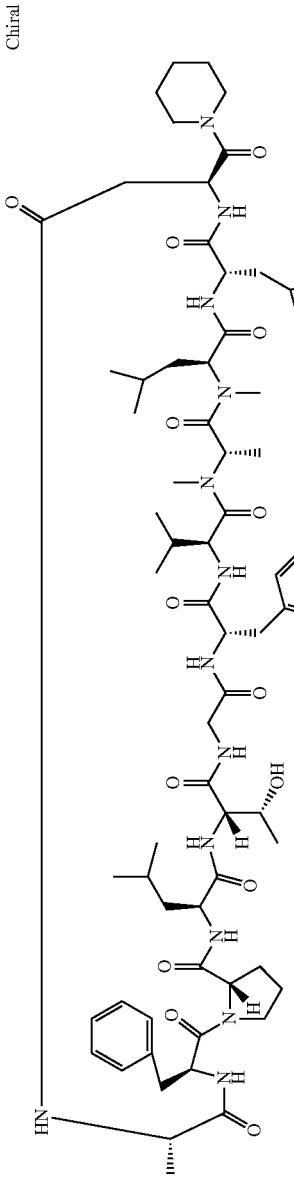 |

TABLE 11-3-1-continued
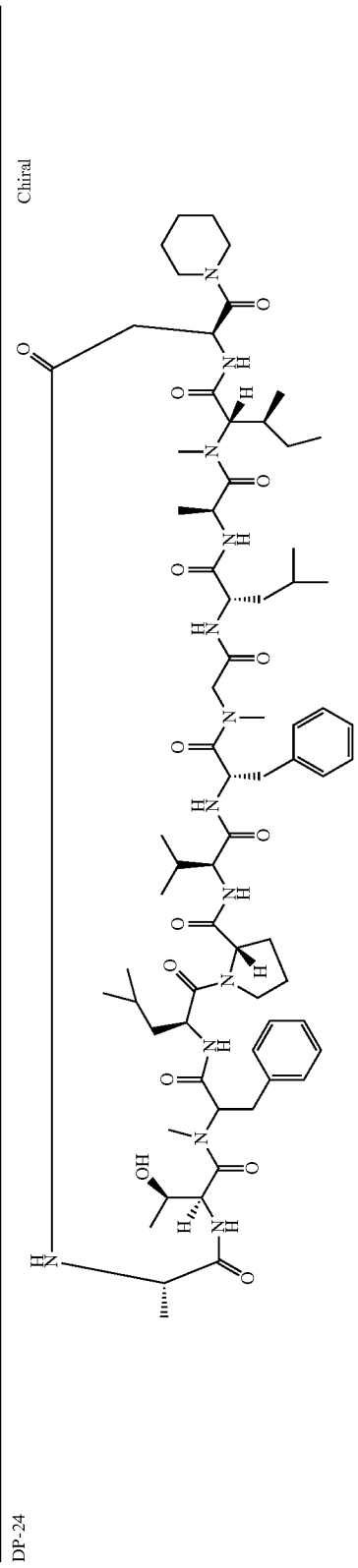
DP-24
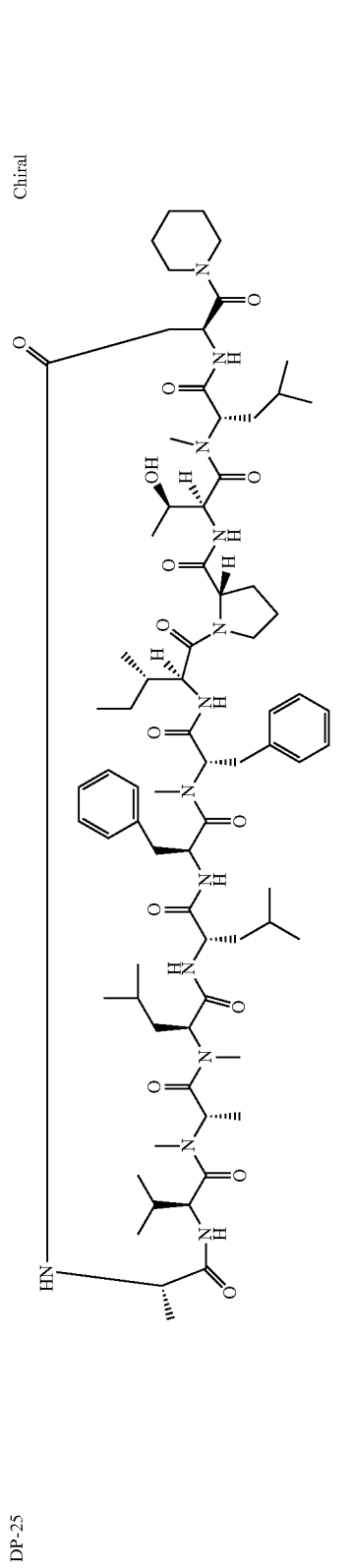
DP-25
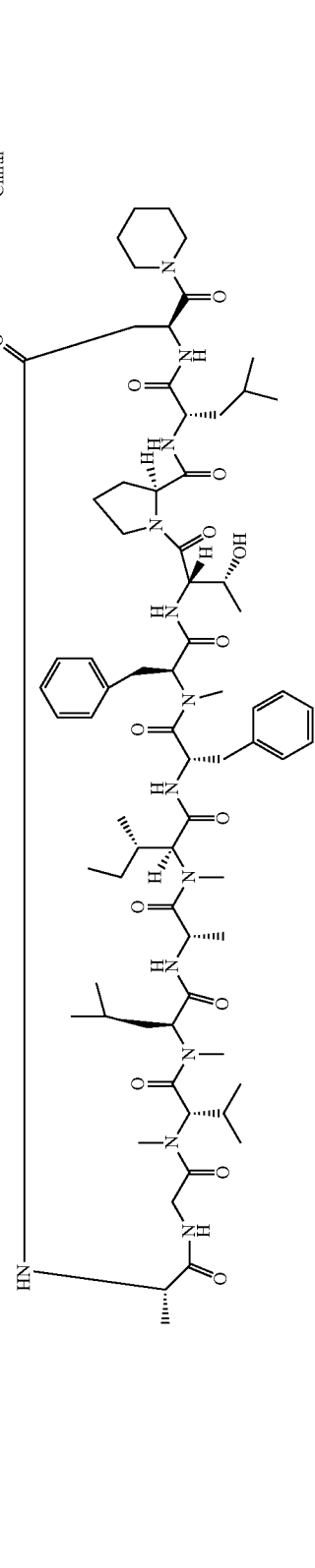
DP-26

TABLE 11-3-1-continued
| DP-27 | 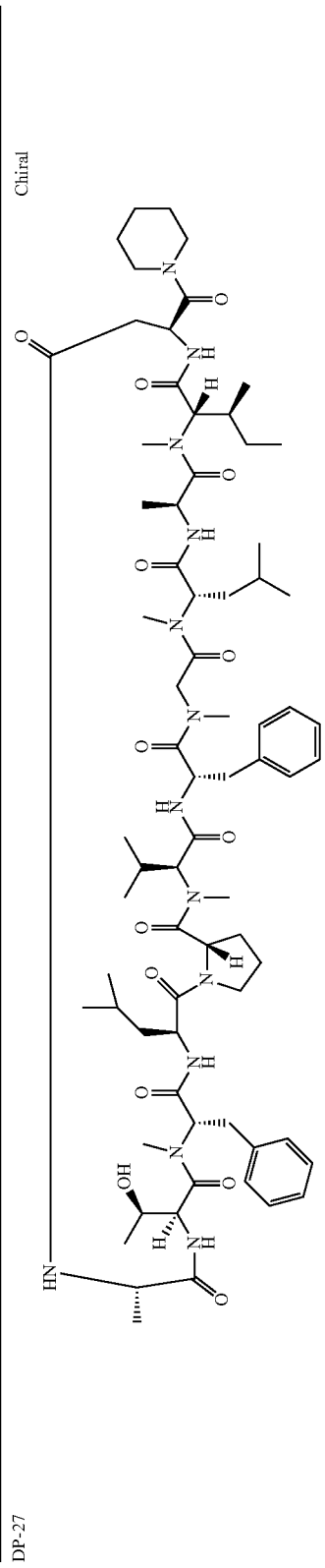 |
| DP-28 | 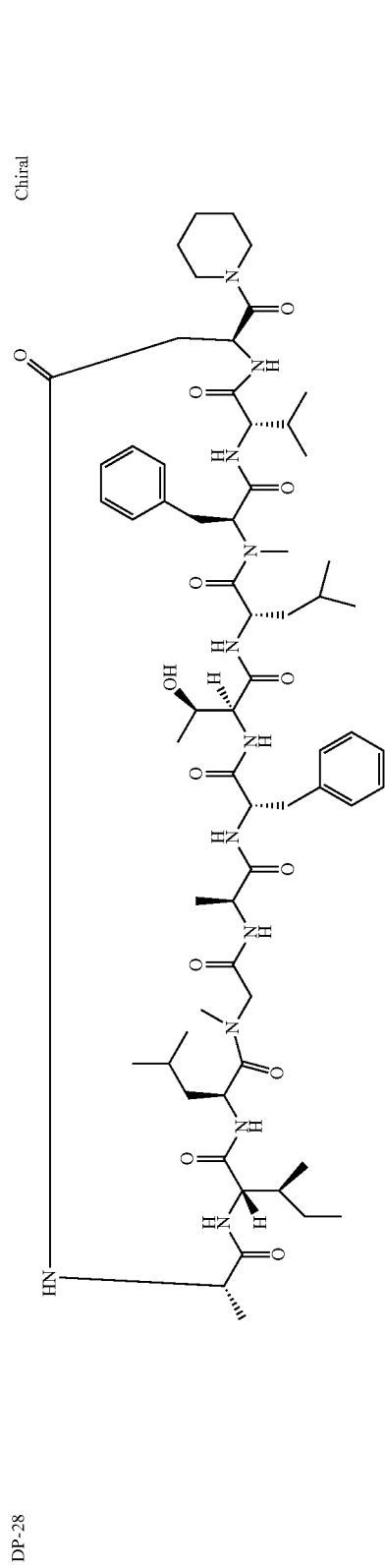 |
| DP-29 | 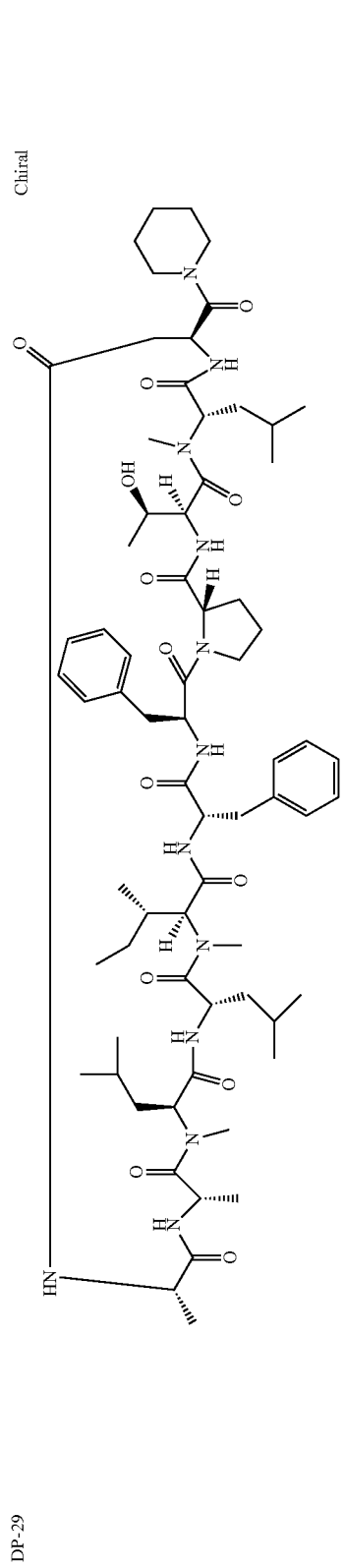 |

TABLE 11-3-1-continued
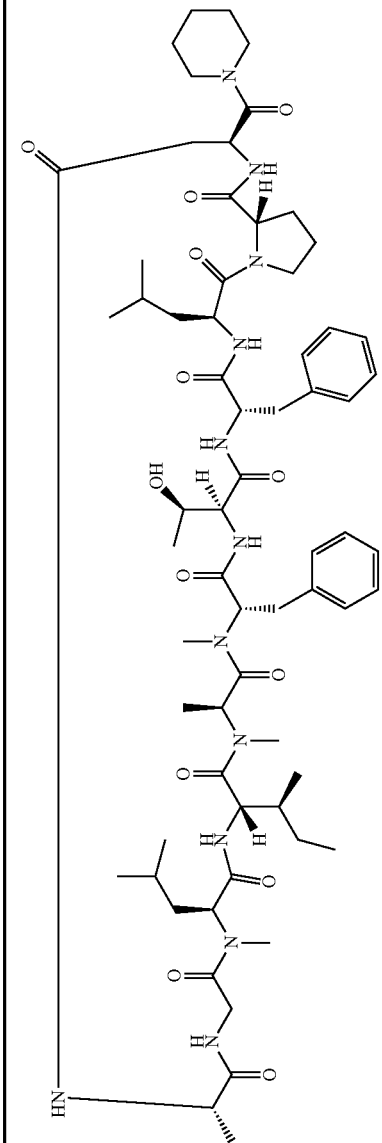
DP-30
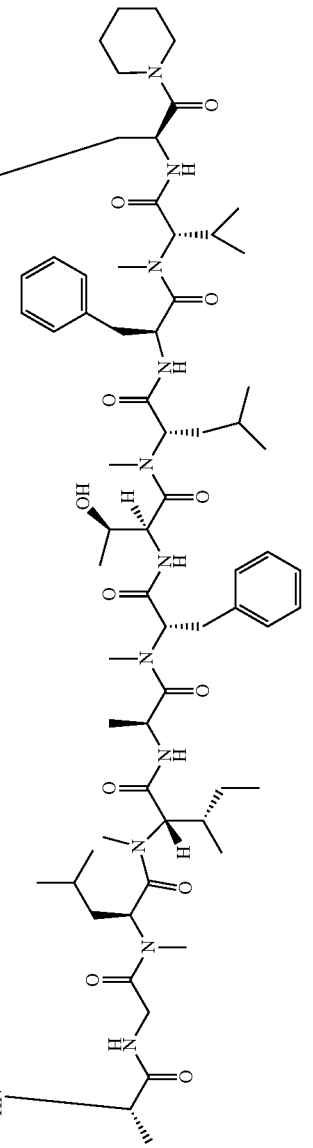
DP-31
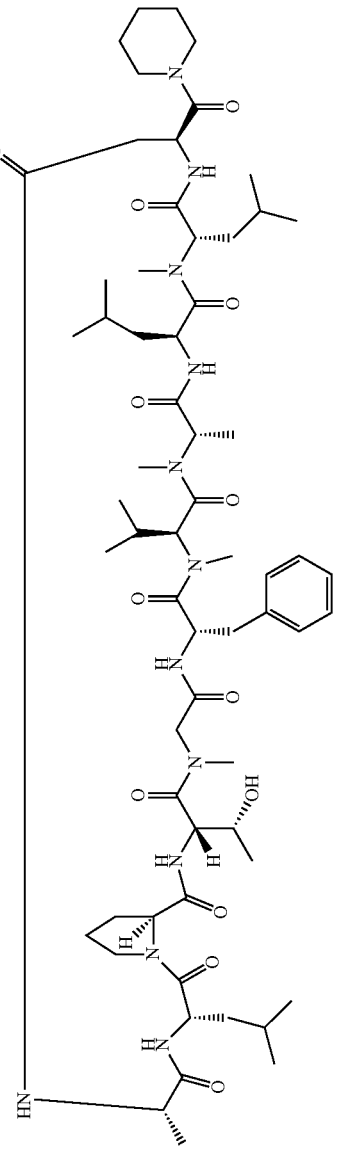
DP-32

TABLE 11-3-1-continued
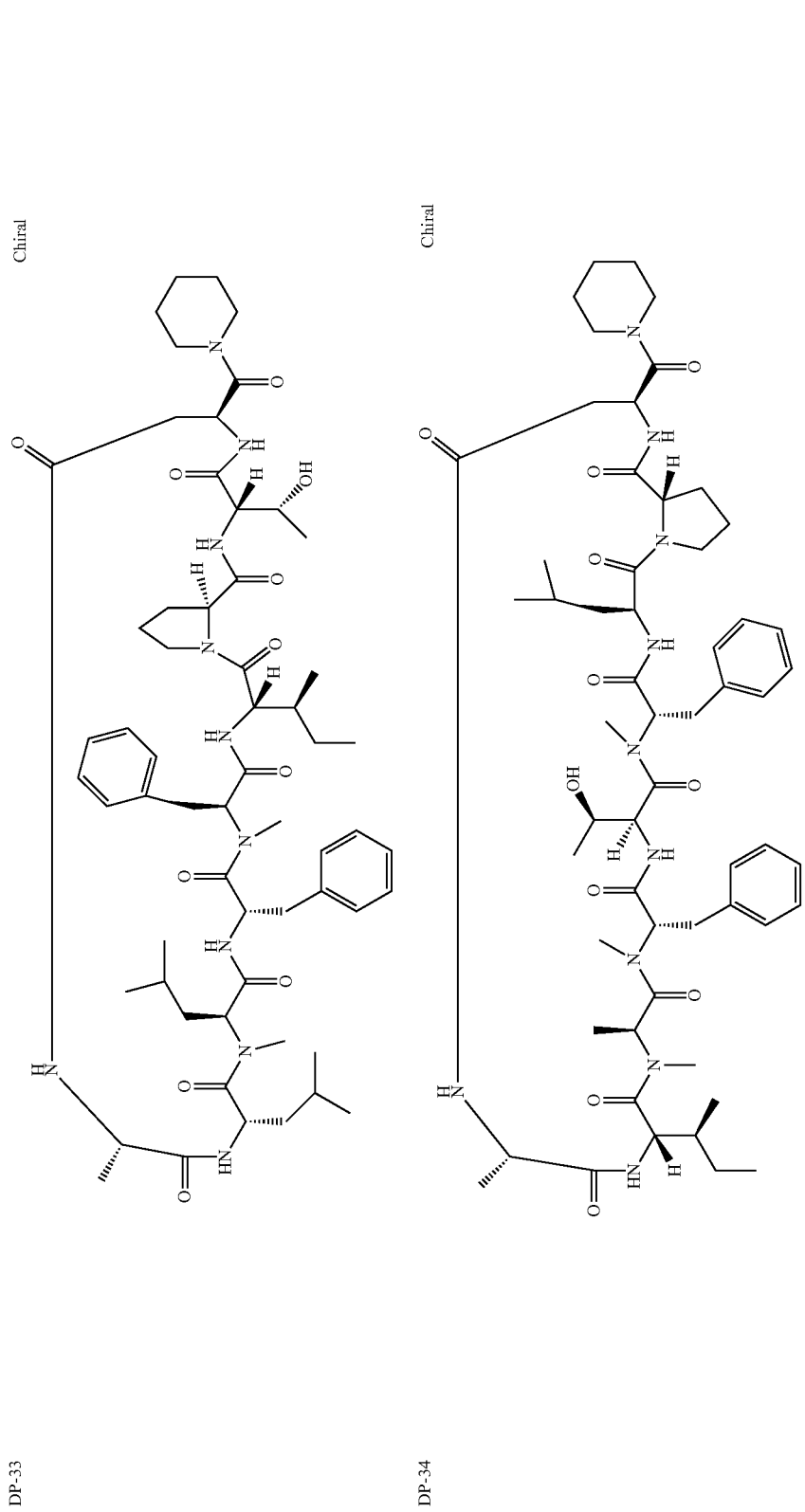
DP-33
DP-34

TABLE 11-3-1-continued
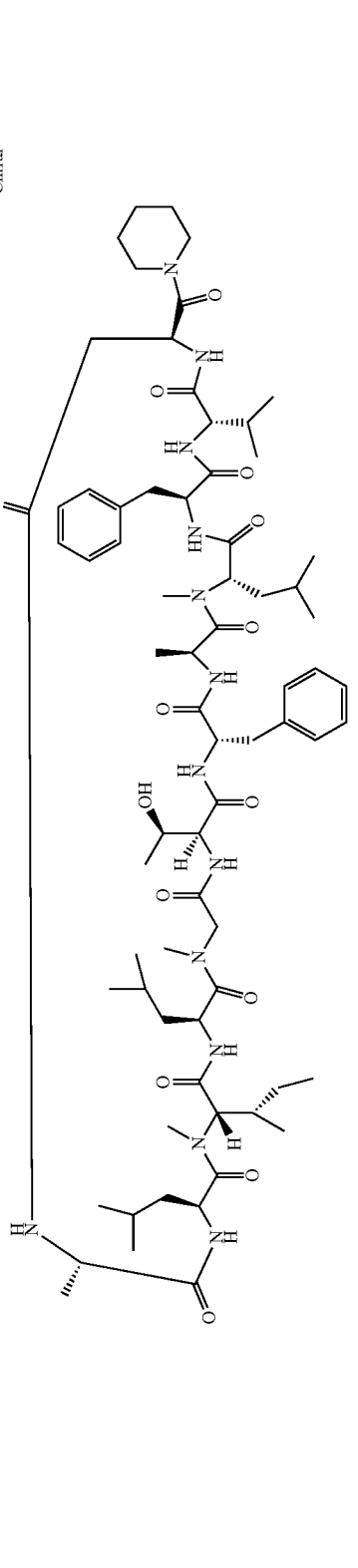
DP-35
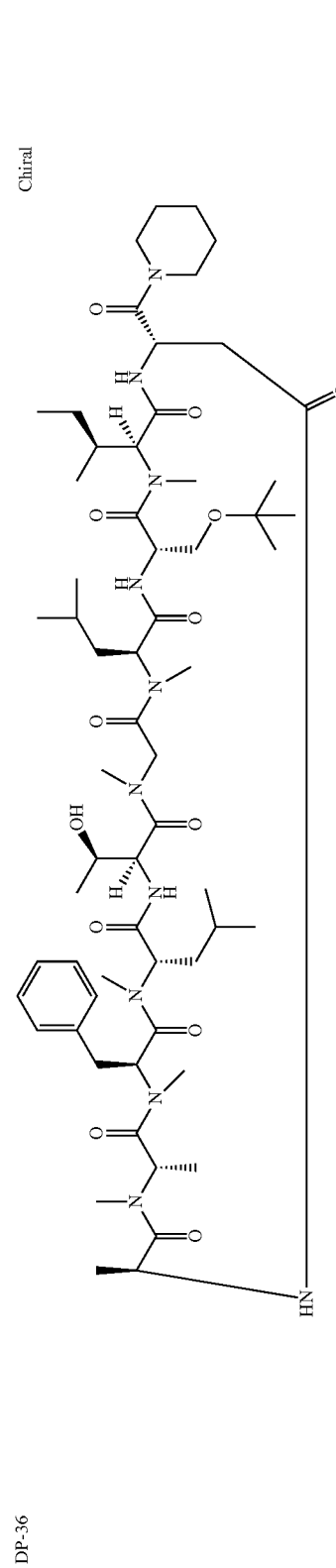
DP-36
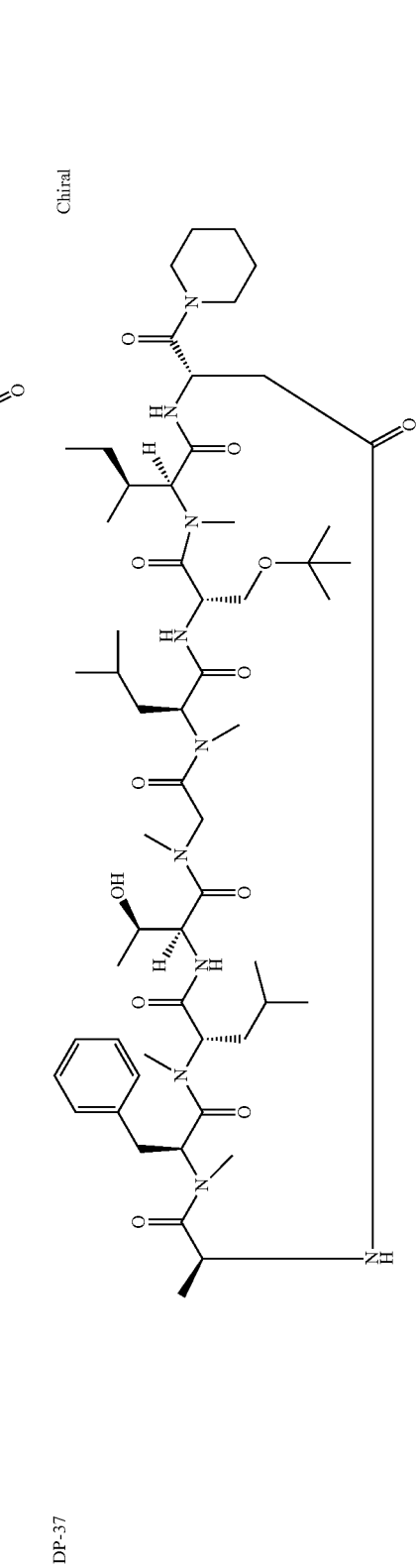
DP-37

TABLE 11-3-1-continued
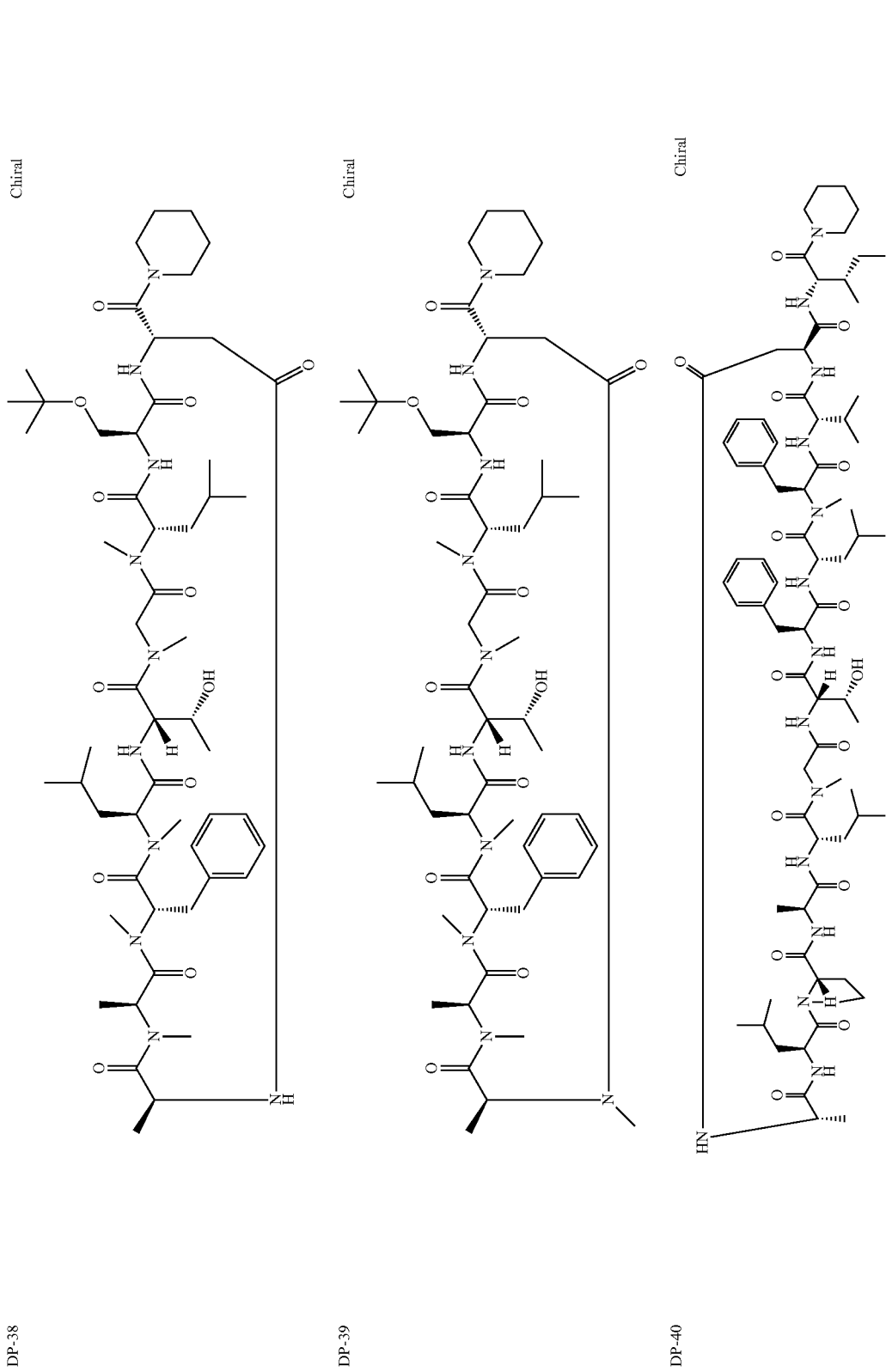
DP-38
DP-39
DP-40

TABLE 11-3-1-continued
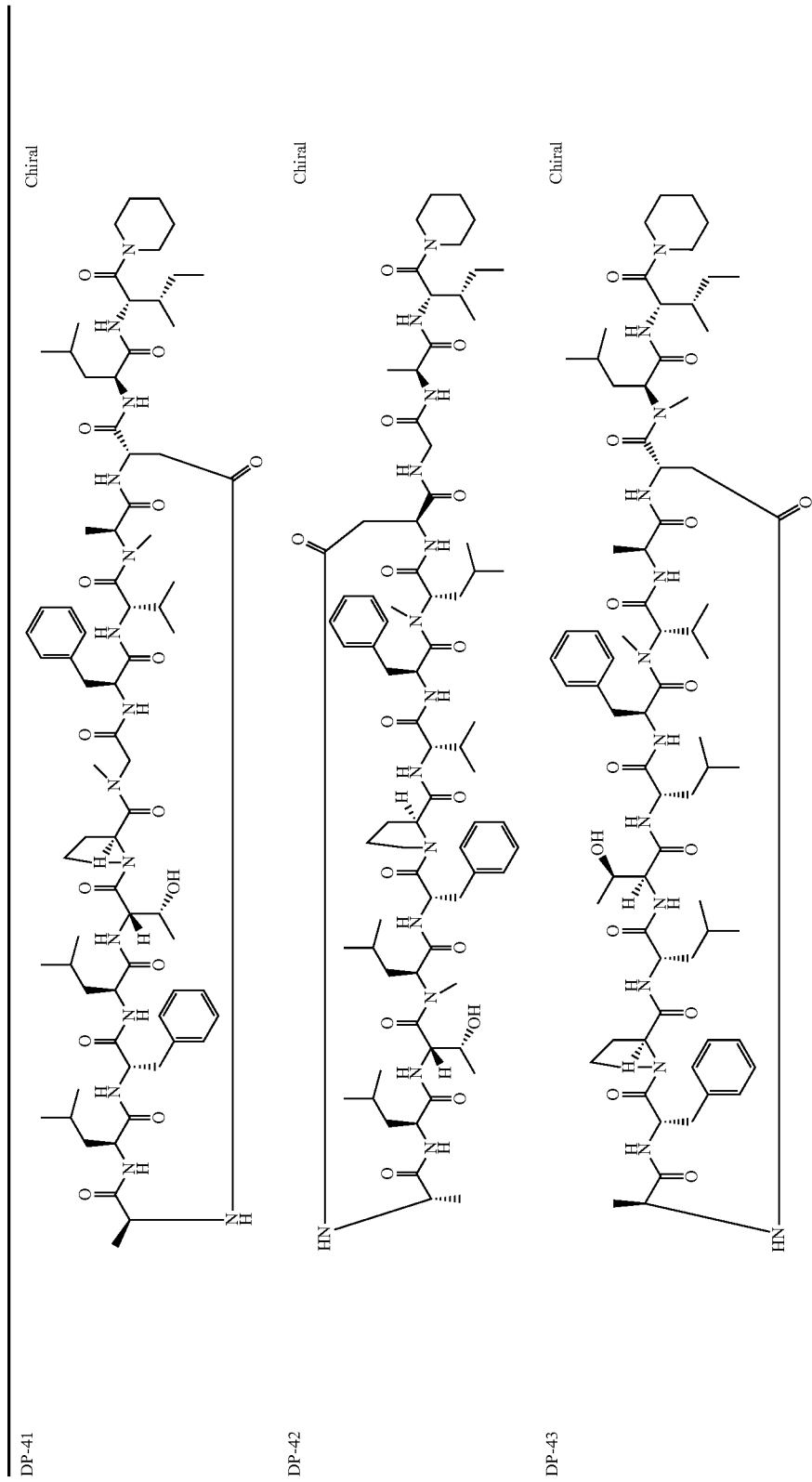

TABLE 11-3-1-continued
| DP-44 | 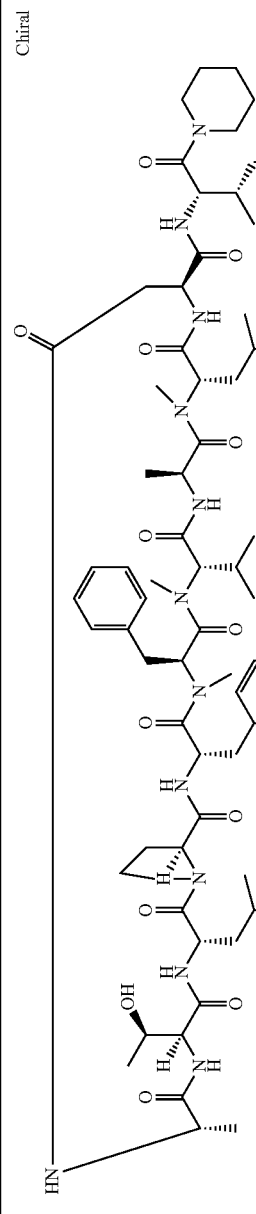 |
| DP-45 | 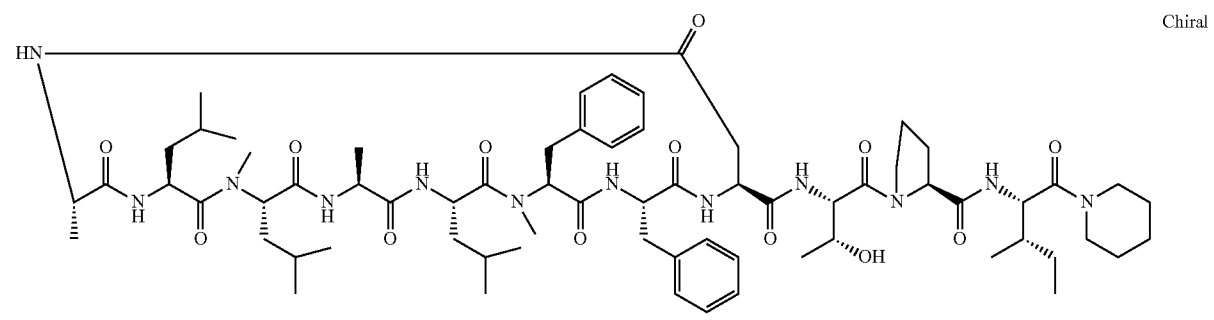 [SMILES: CC[C@H](C)[C@H](NC(=O)[C@@H]1CCCN1C(=O)[C@@H](NC(=O)[C@@H]1CC(=O)N[C@@H](C)C(=O)N[C@@H](CC(C)C)C(=O)N(C)[C@@H](CC(C)C)C(=O)N[C@@H](C)C(=O)N[C@@H](CC(C)C)C(=O)N(C)[C@@H](Cc2ccccc2)C(=O)N[C@@H](Cc2ccccc2)C(=O)N1)[C@@H](C)O)C(=O)N1CCCCC1] |
| DP-46 | 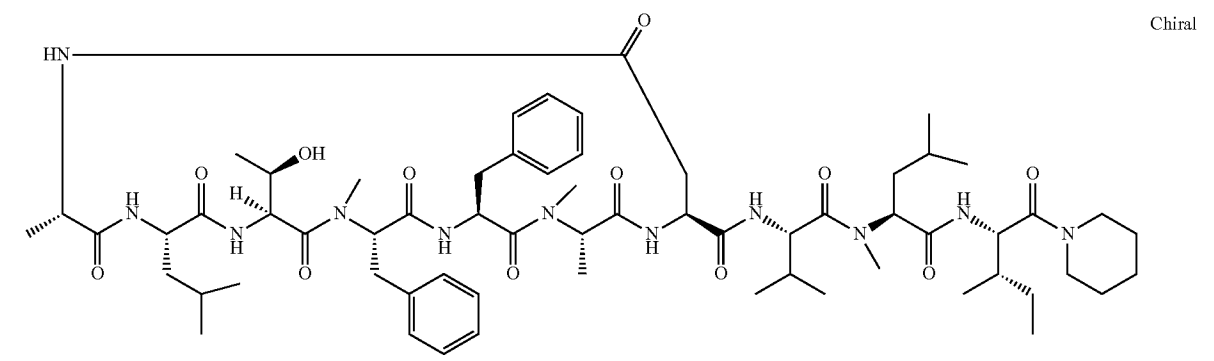 [SMILES: CC[C@H](C)[C@H](NC(=O)[C@H](CC(C)C)N(C)C(=O)[C@@H](NC(=O)[C@@H]1CC(=O)N[C@@H](C)C(=O)N[C@@H](CC(C)C)C(=O)N[C@@H]([C@@H](C)O)C(=O)N(C)[C@@H](Cc2ccccc2)C(=O)N[C@@H](Cc2ccccc2)C(=O)N(C)[C@@H](C)C(=O)N1)C(C)C)C(=O)N1CCCCC1] |

TABLE 11-3-1-continued
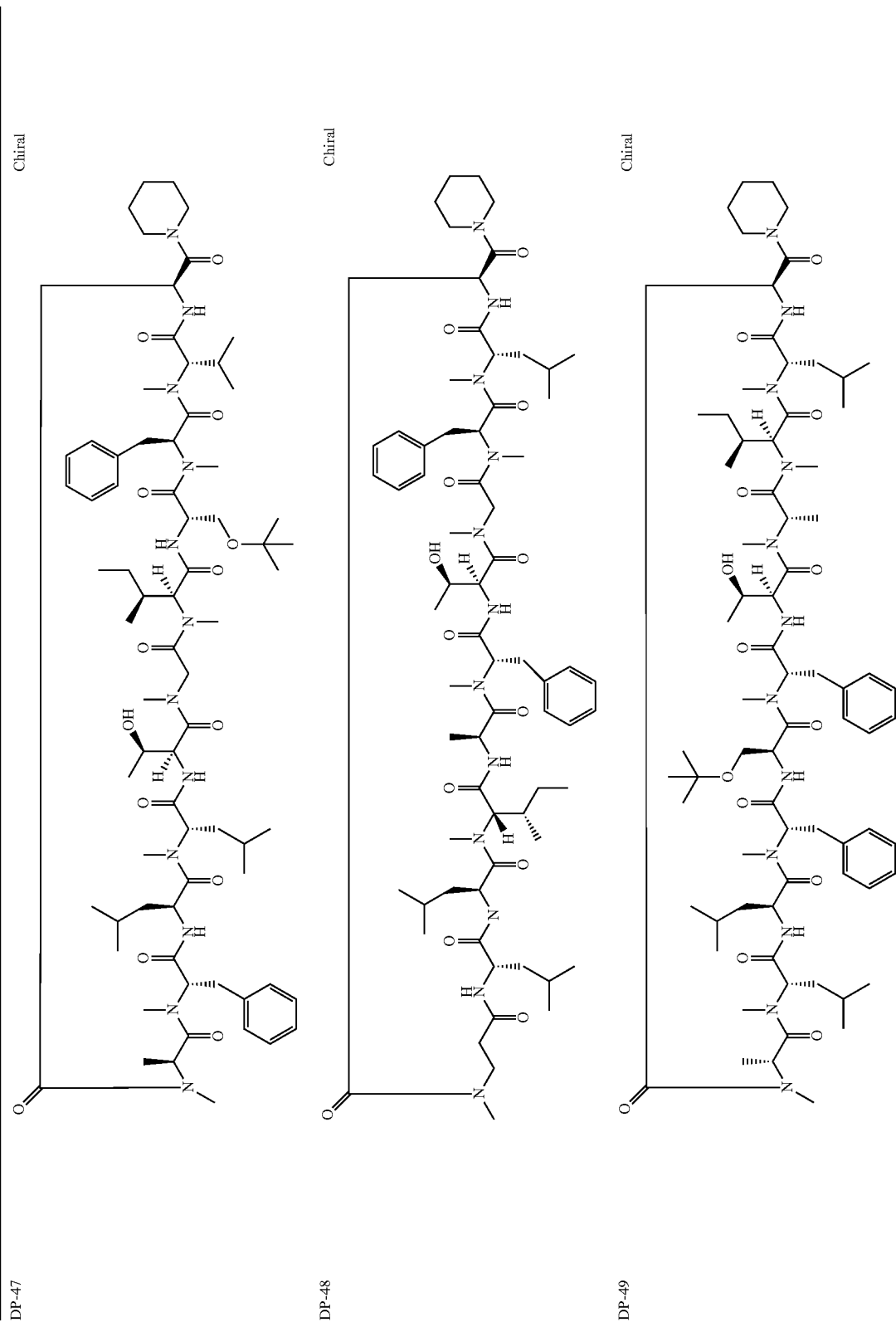
DP-47
DP-48
DP-49

TABLE 11-3-1-continued
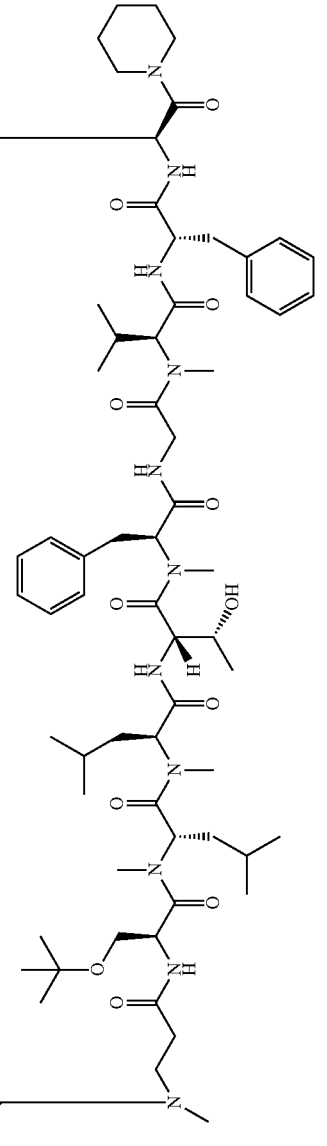
DP-50
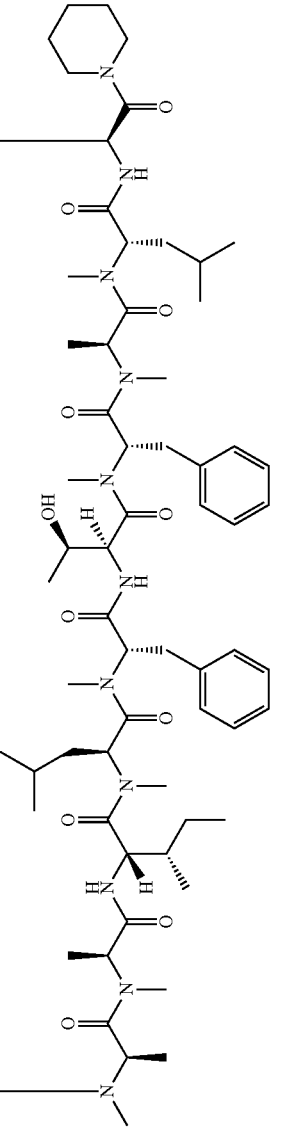
DP-51
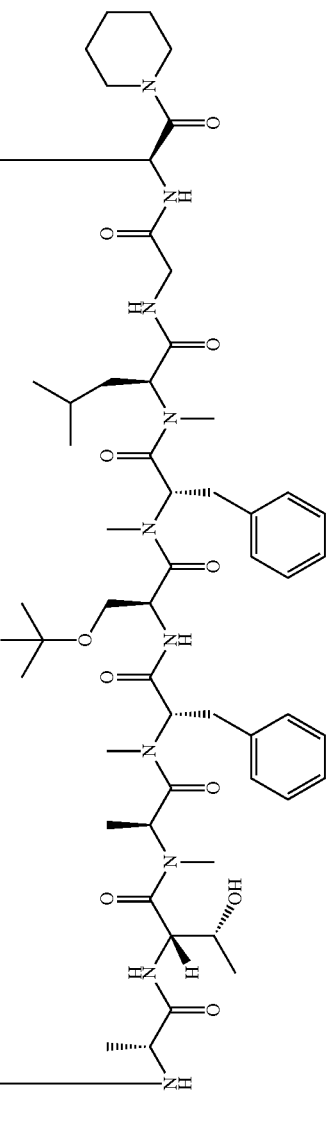
DP-52

TABLE 11-3-1-continued
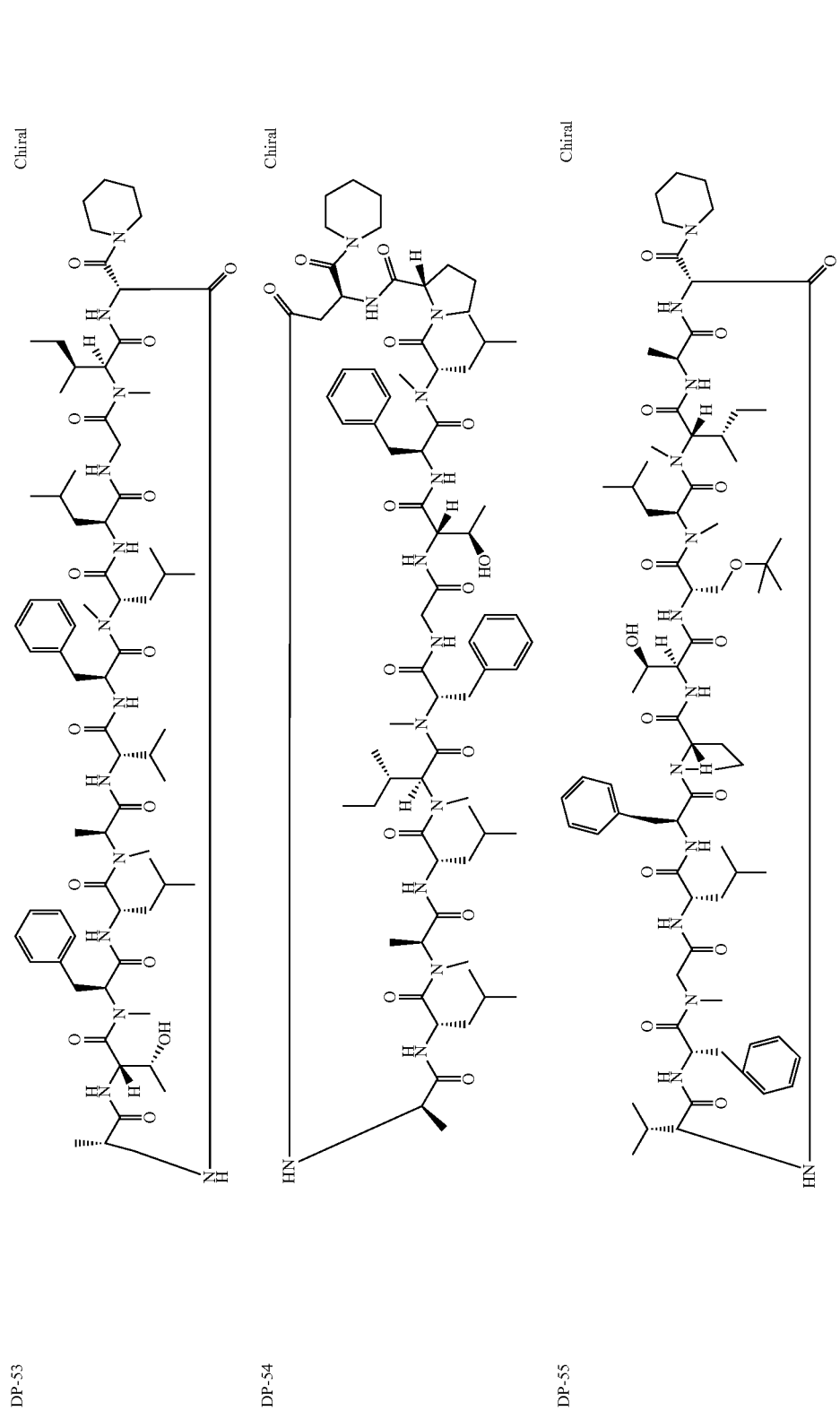

TABLE 11-3-1-continued
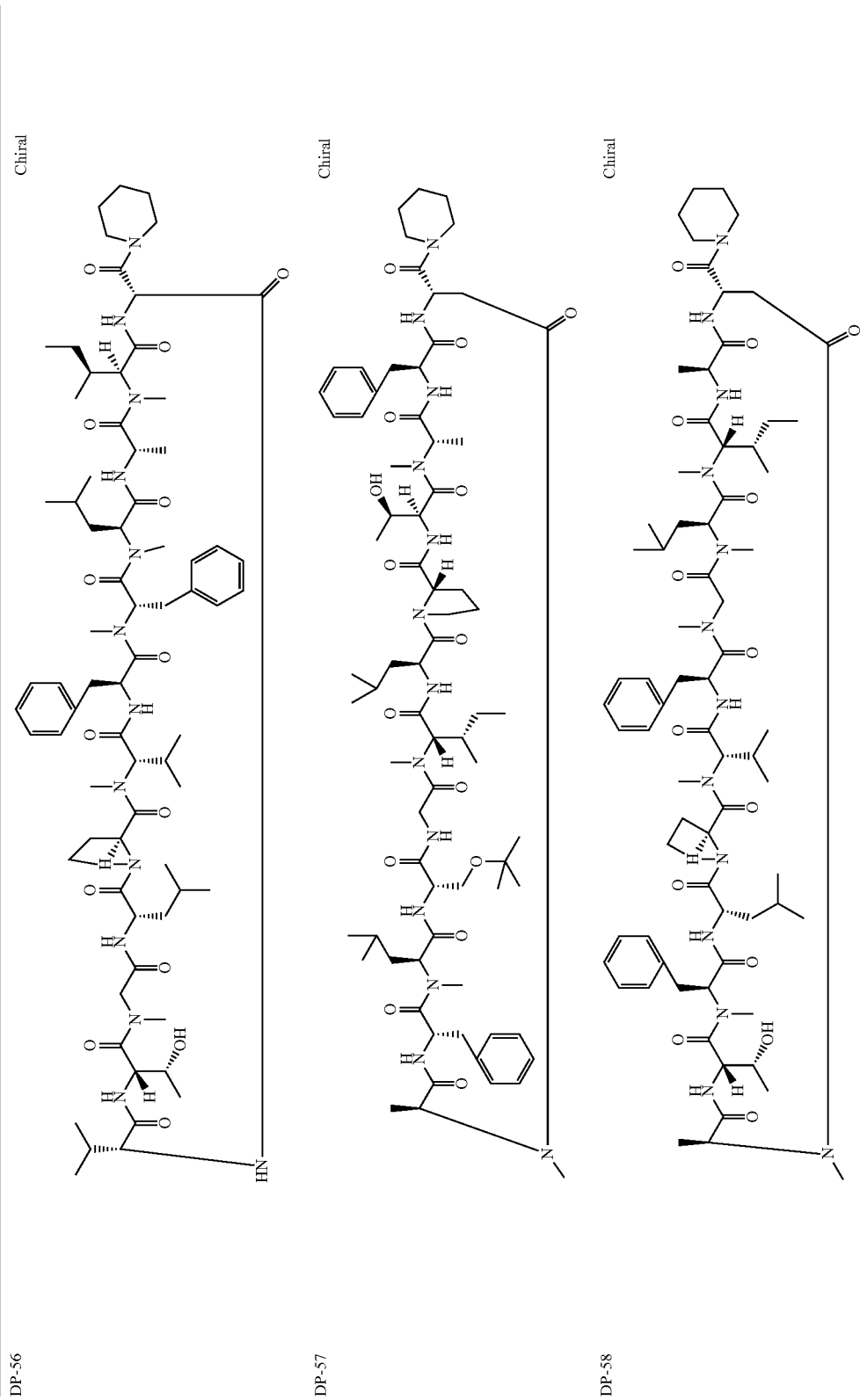
DP-56
DP-57
DP-58

TABLE 11-3-1-continued
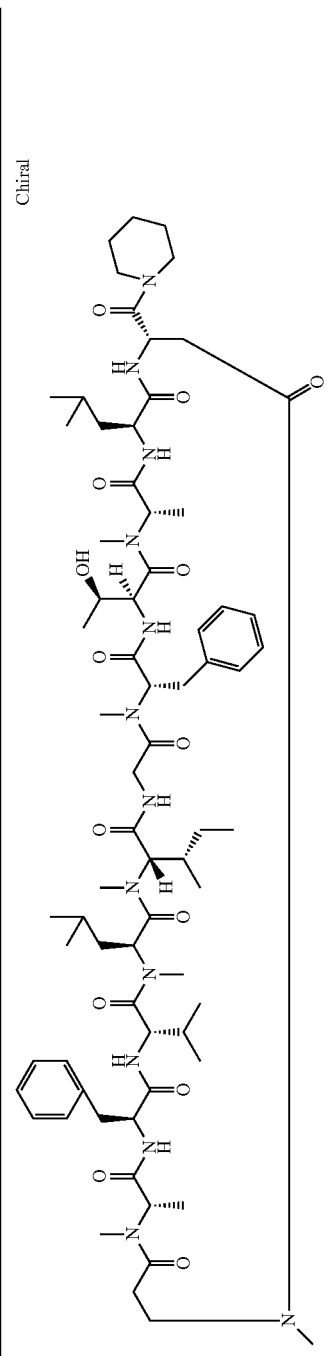
DP-59
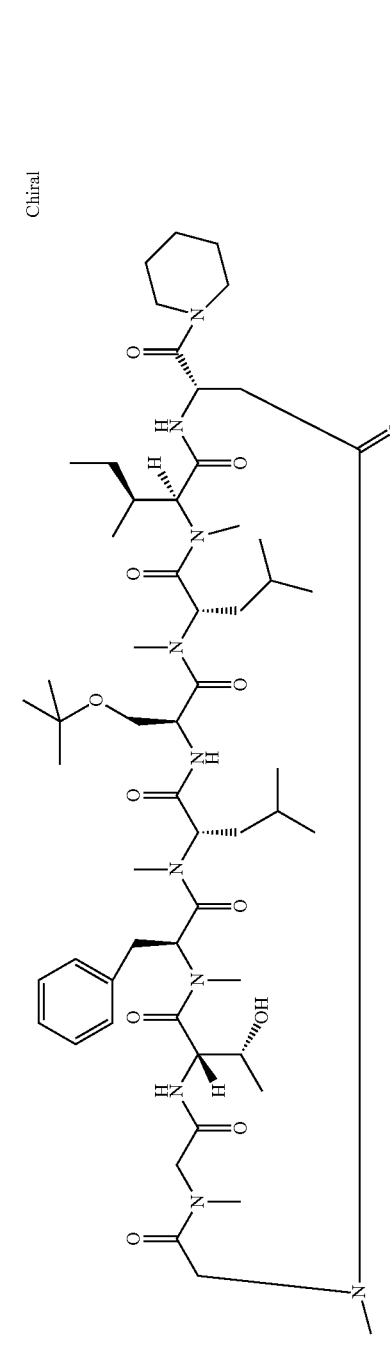
DP-60
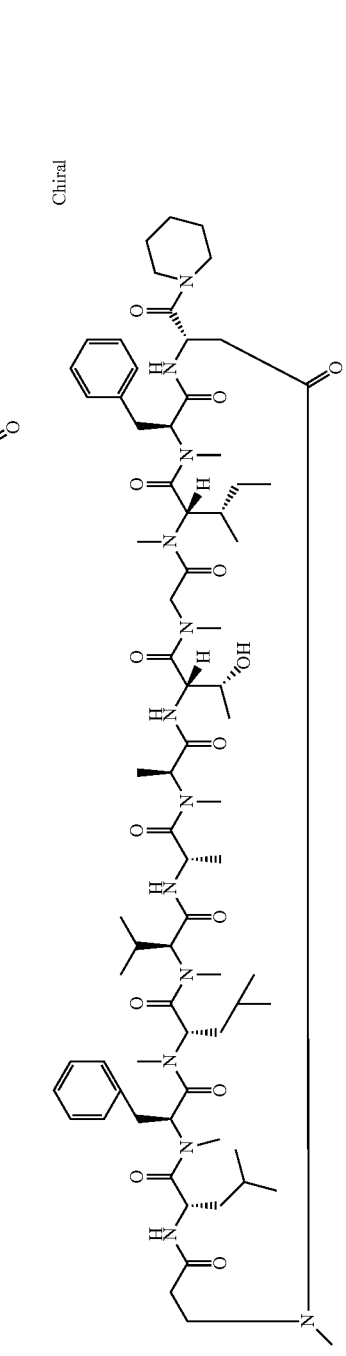
DP-61

TABLE 11-3-1-continued

DP-62

DP-63

DP-64

TABLE 11-3-1-continued
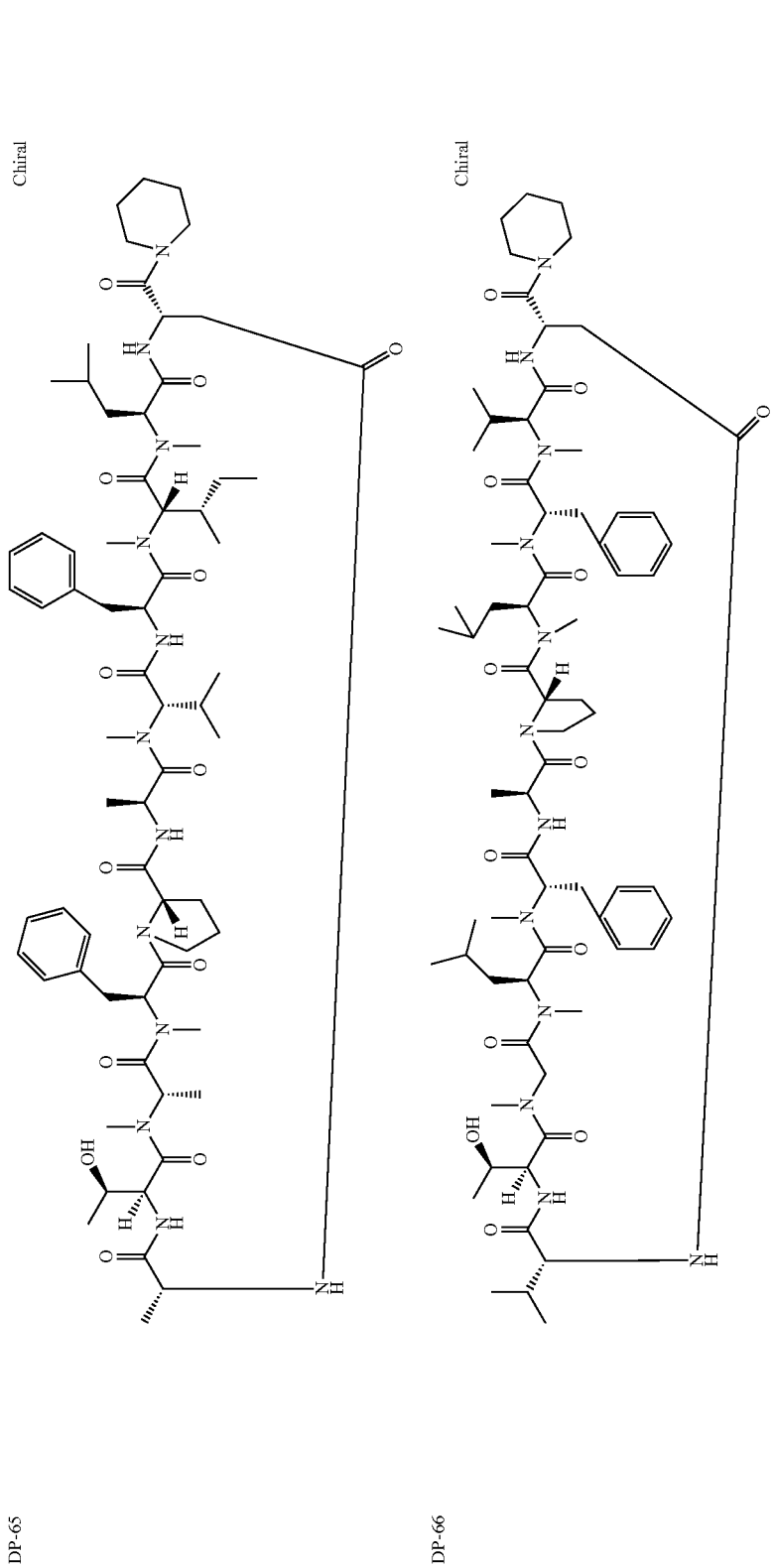
DP-65
DP-66

TABLE 11-3-1-continued
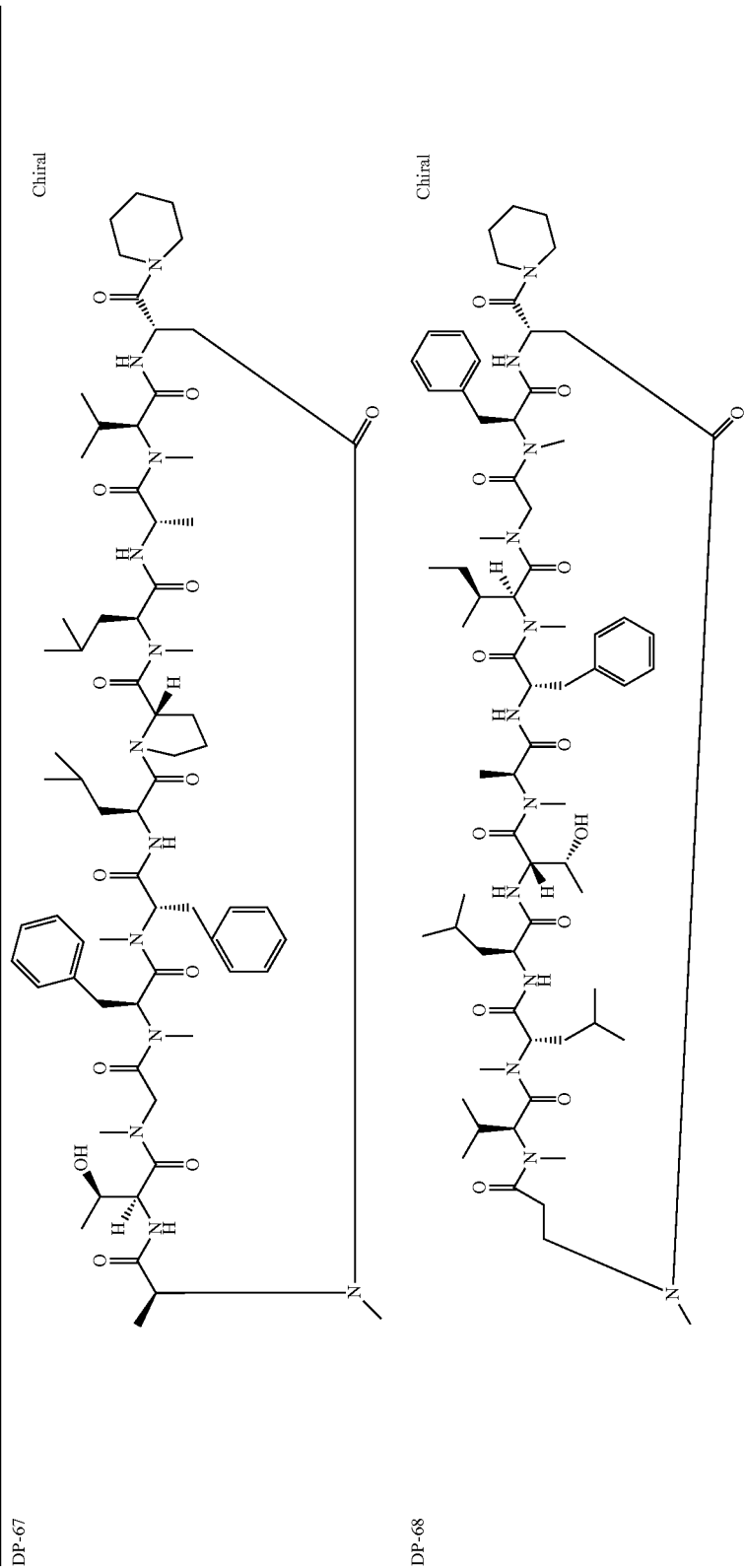
DP-67
DP-68

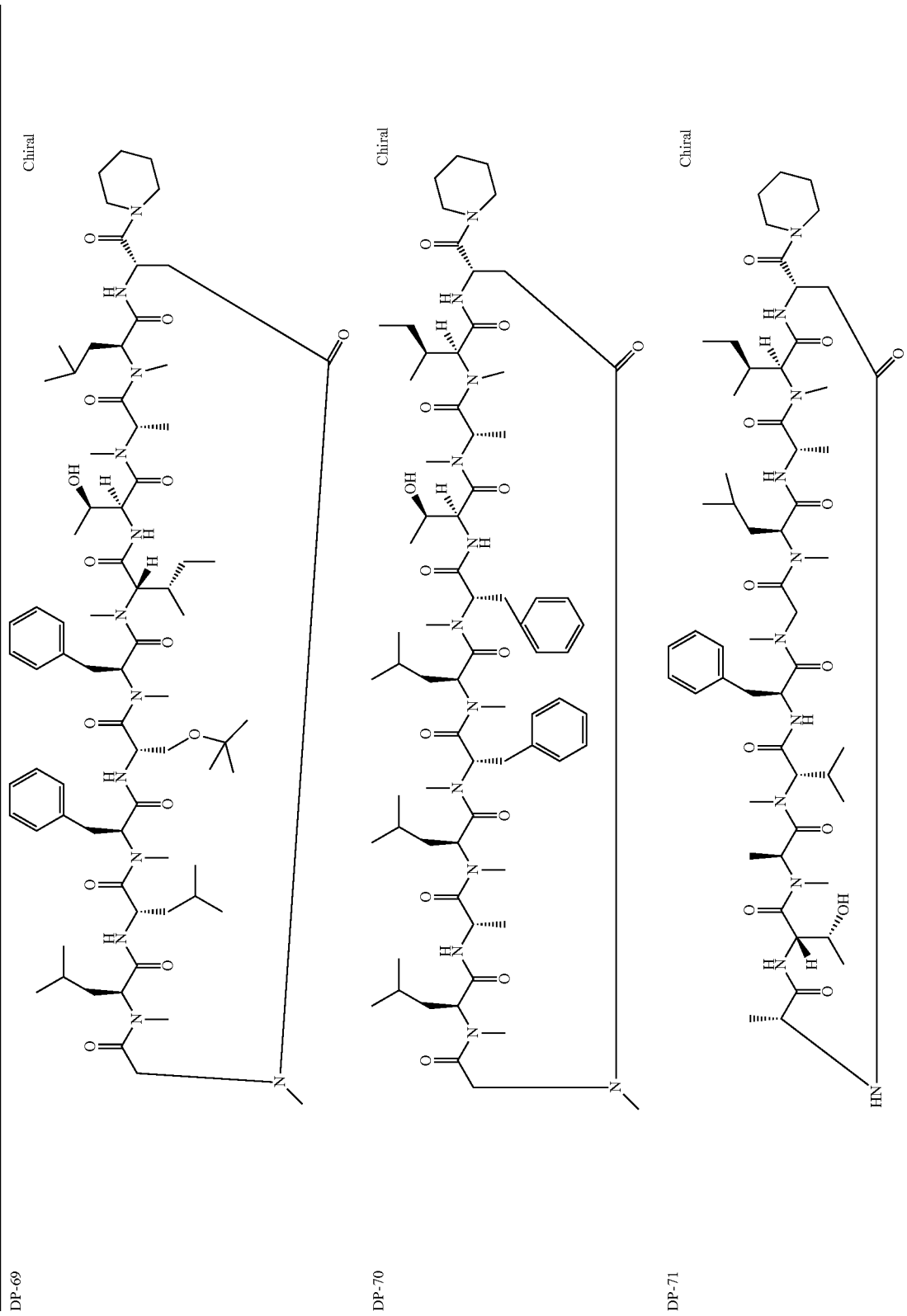

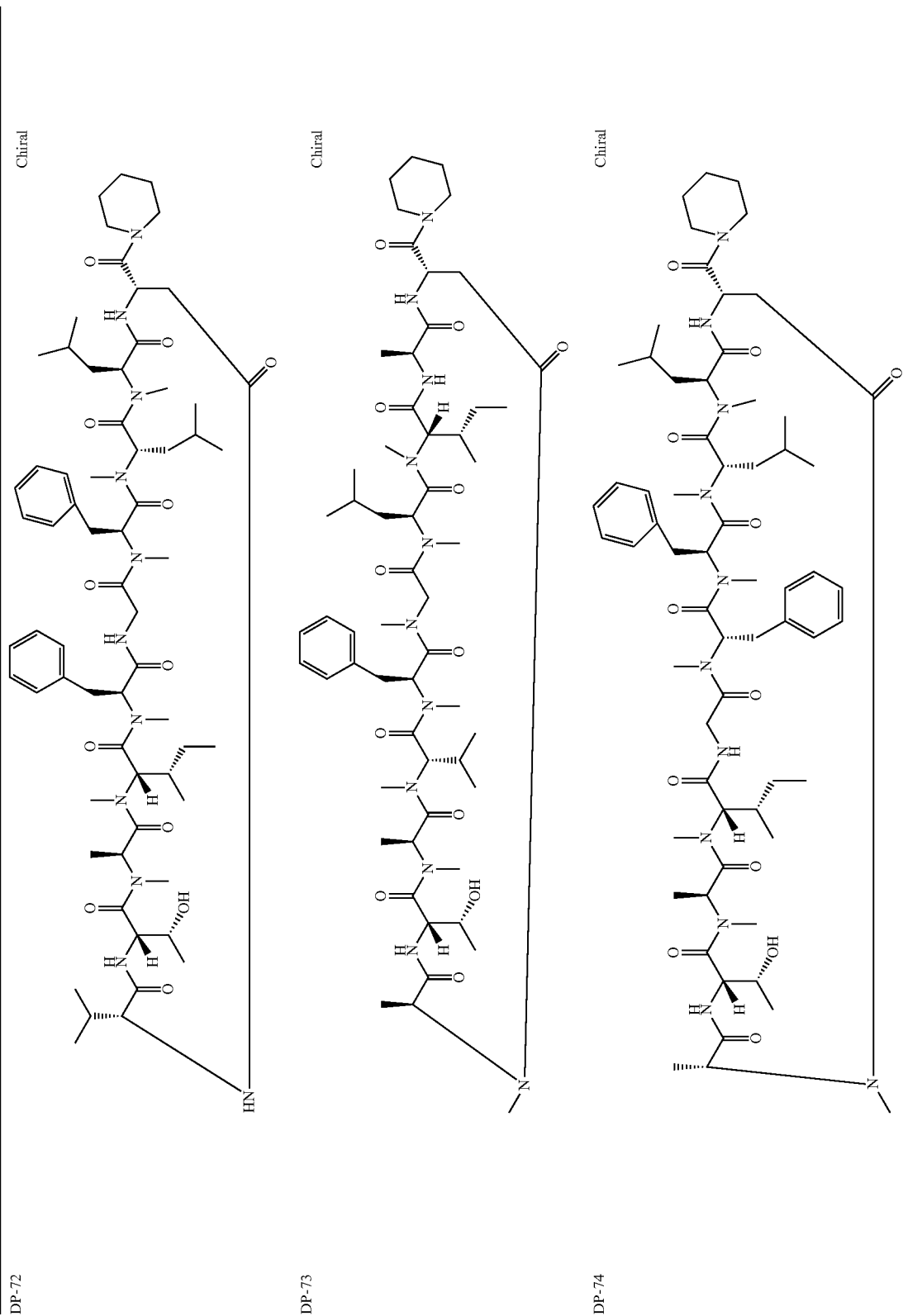

TABLE 11-3-1-continued
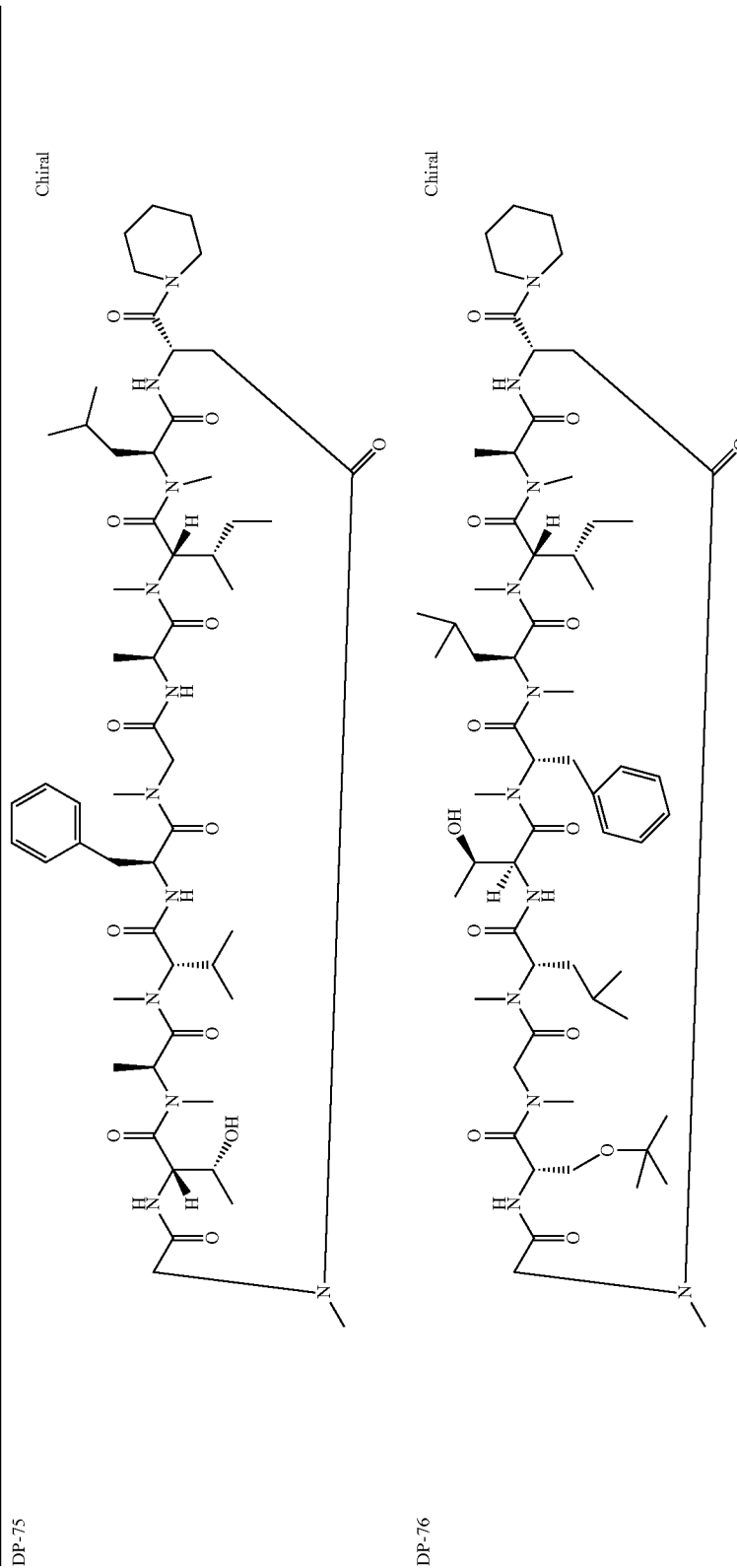
DP-75
DP-76

TABLE 11-3-1-continued
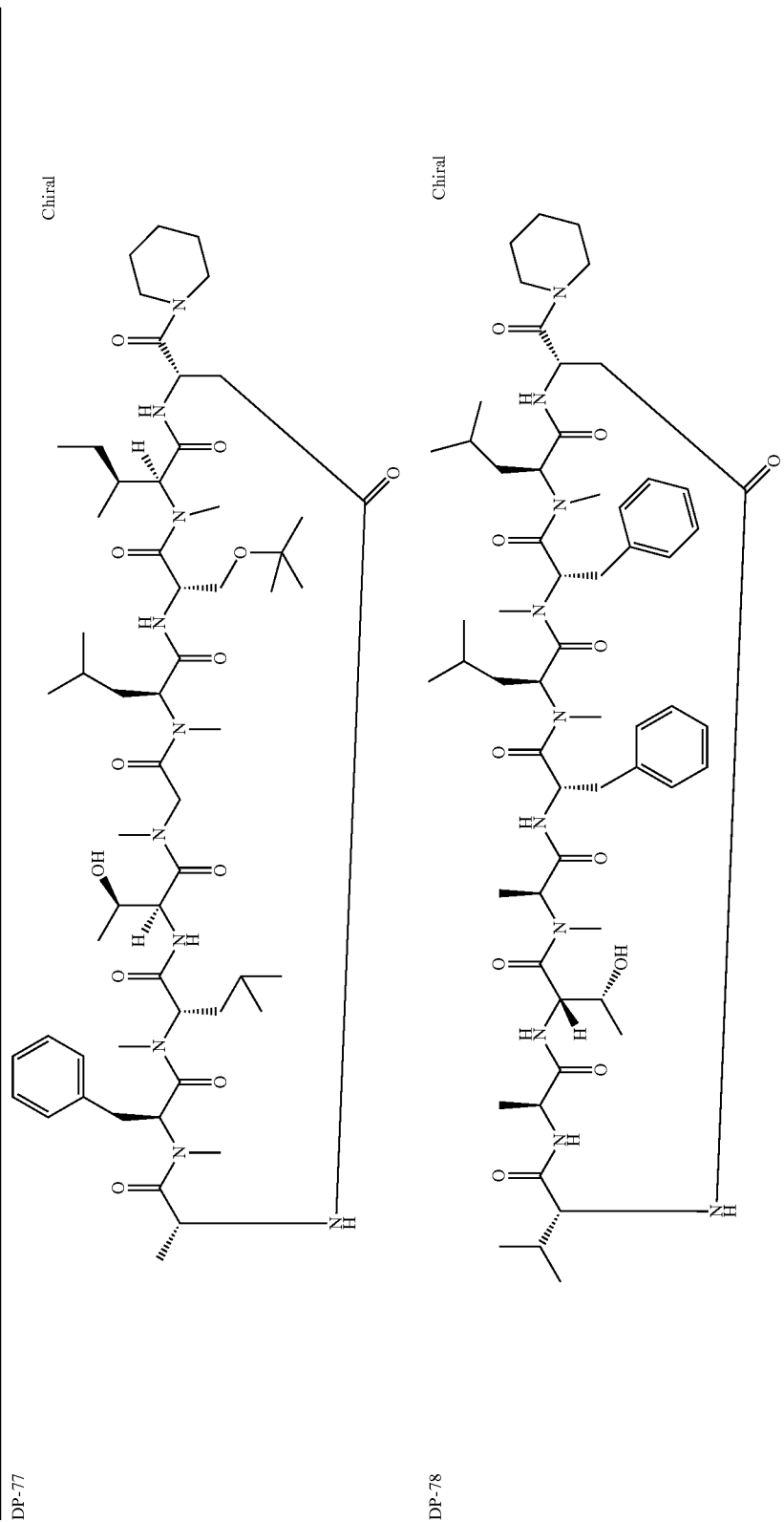
DP-77
DP-78

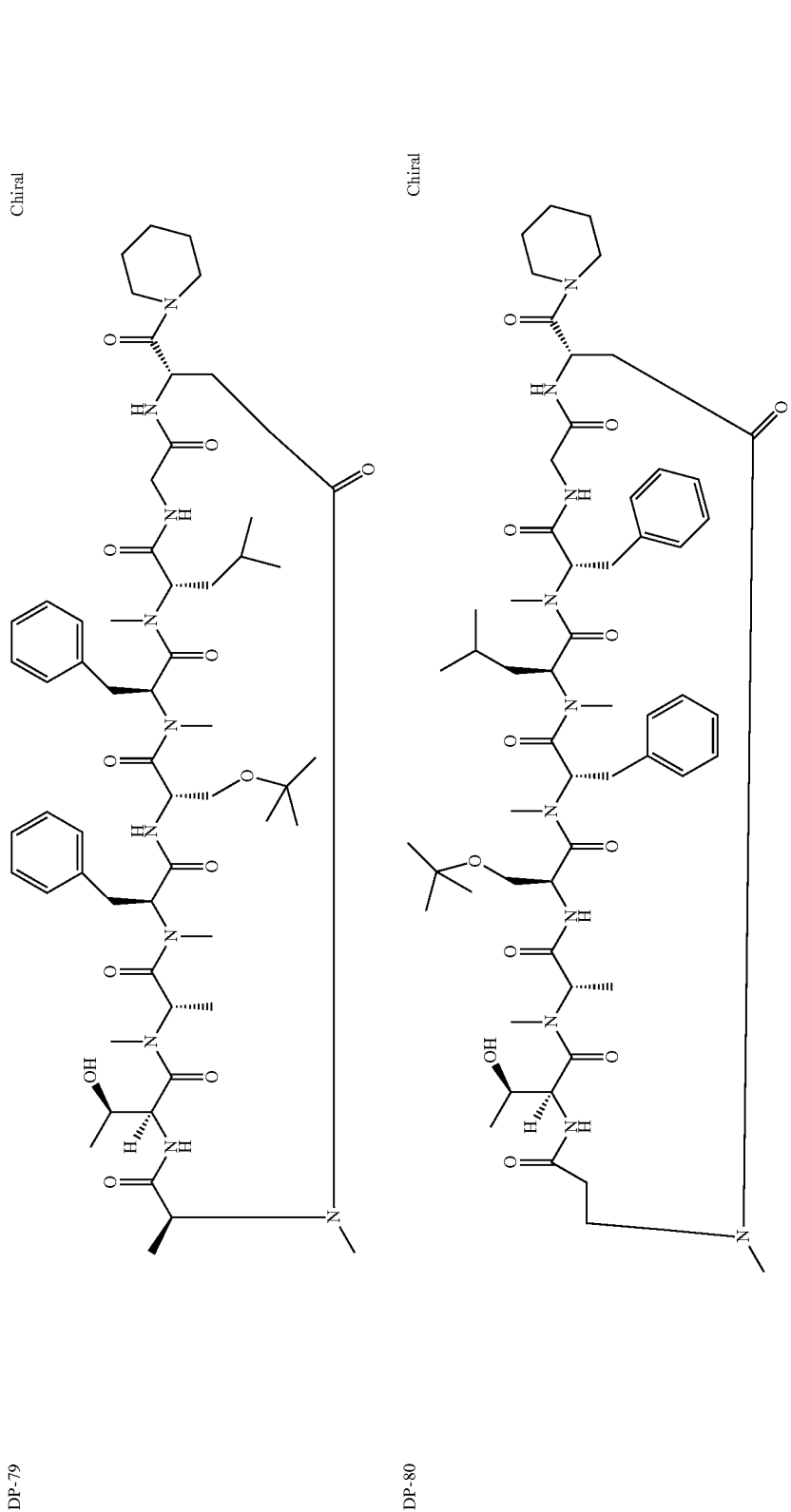

TABLE 11-3-1-continued
| | |
|---|---|
| 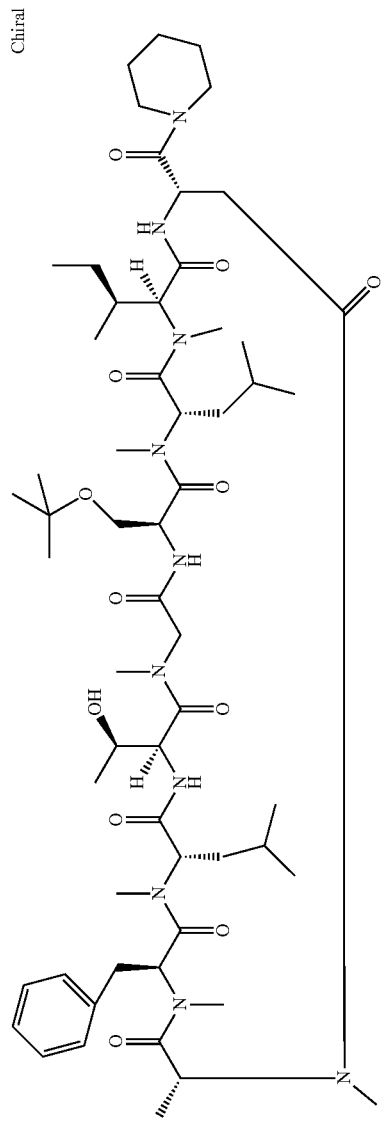 DP-81 | 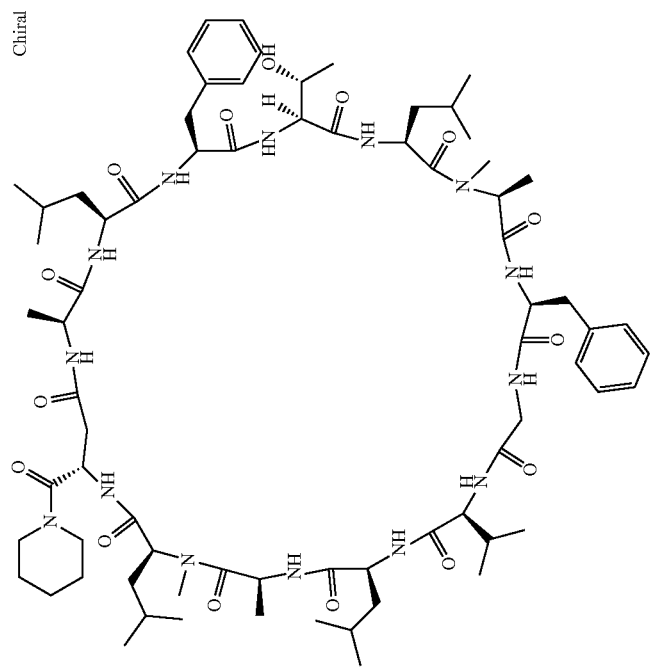 DP-82 |

TABLE 11-3-1-continued
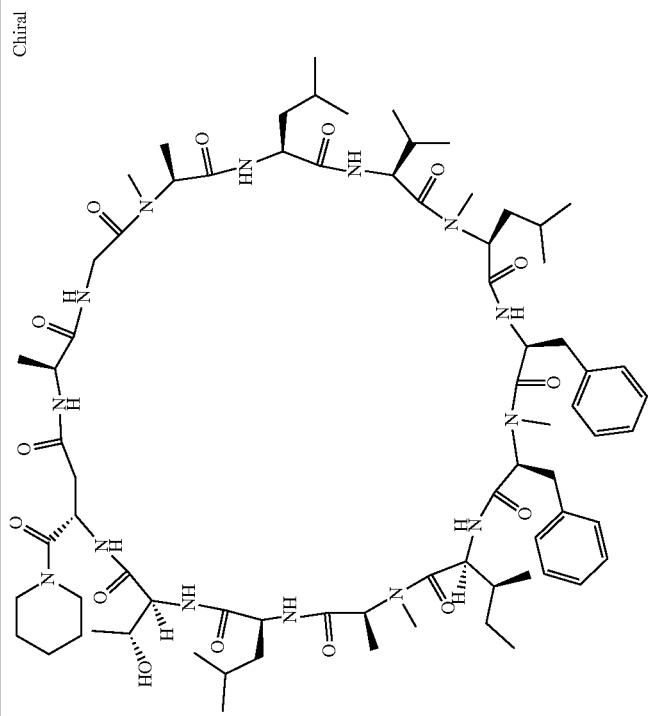
Chiral
DP-83

TABLE 11-3-1-continued
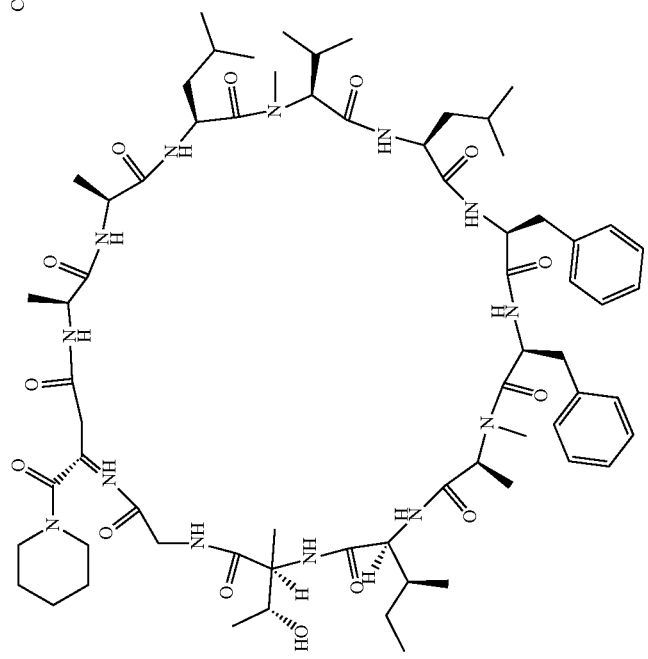
DP-84

TABLE 11-3-1-continued
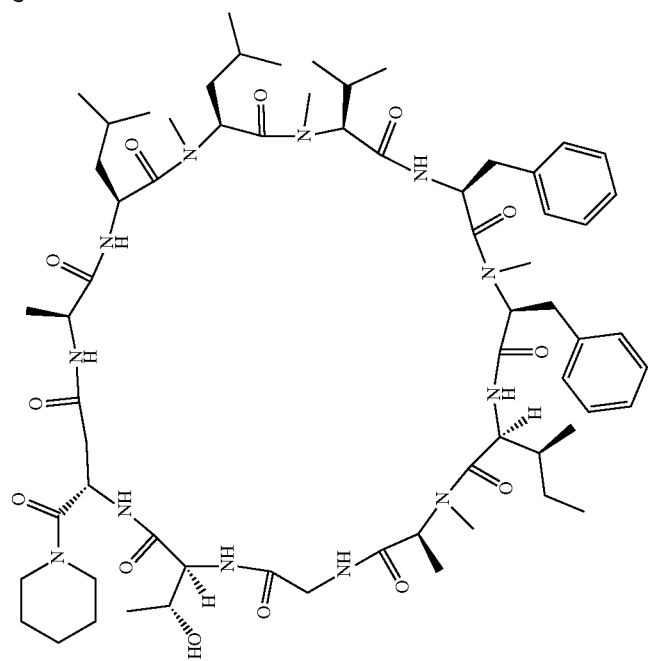
DP-85

TABLE 11-3-1-continued
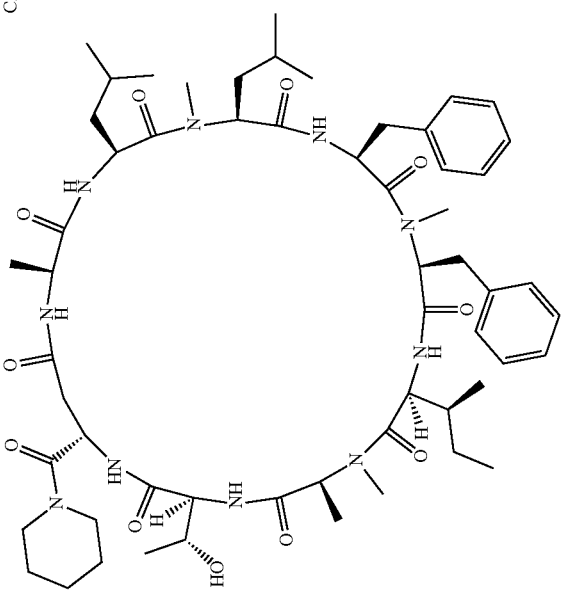
DP-86

TABLE 11-3-1-continued
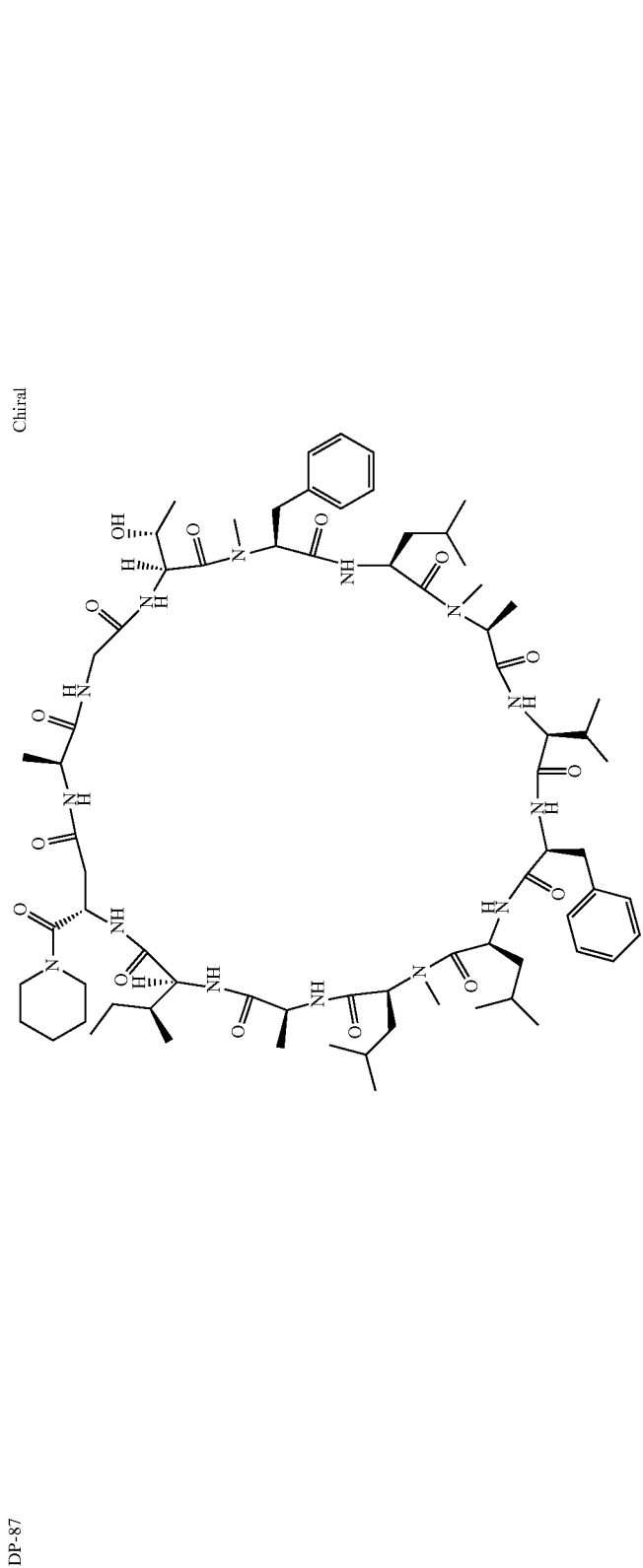
DP-87
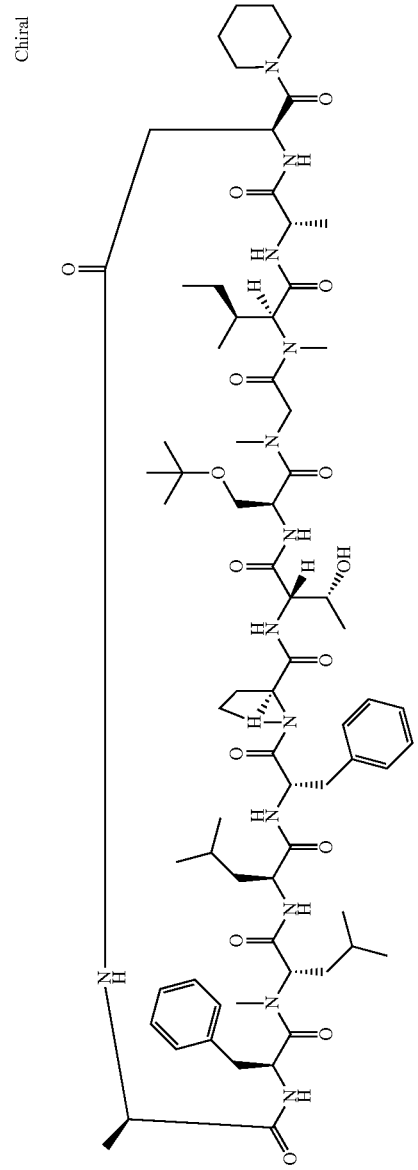
DP-88

TABLE 11-3-1-continued
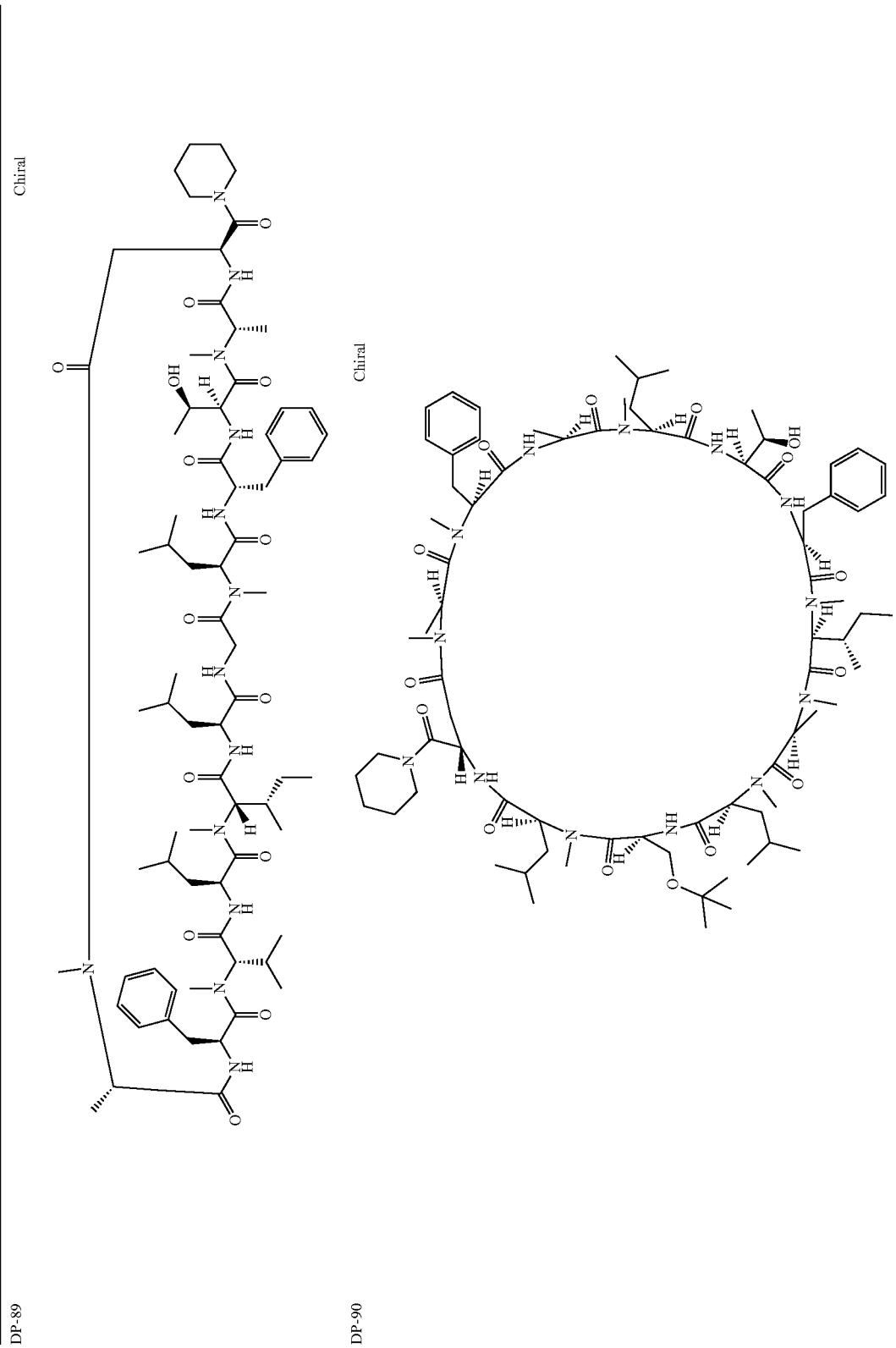
DP-89
DP-90

TABLE 11-3-1-continued
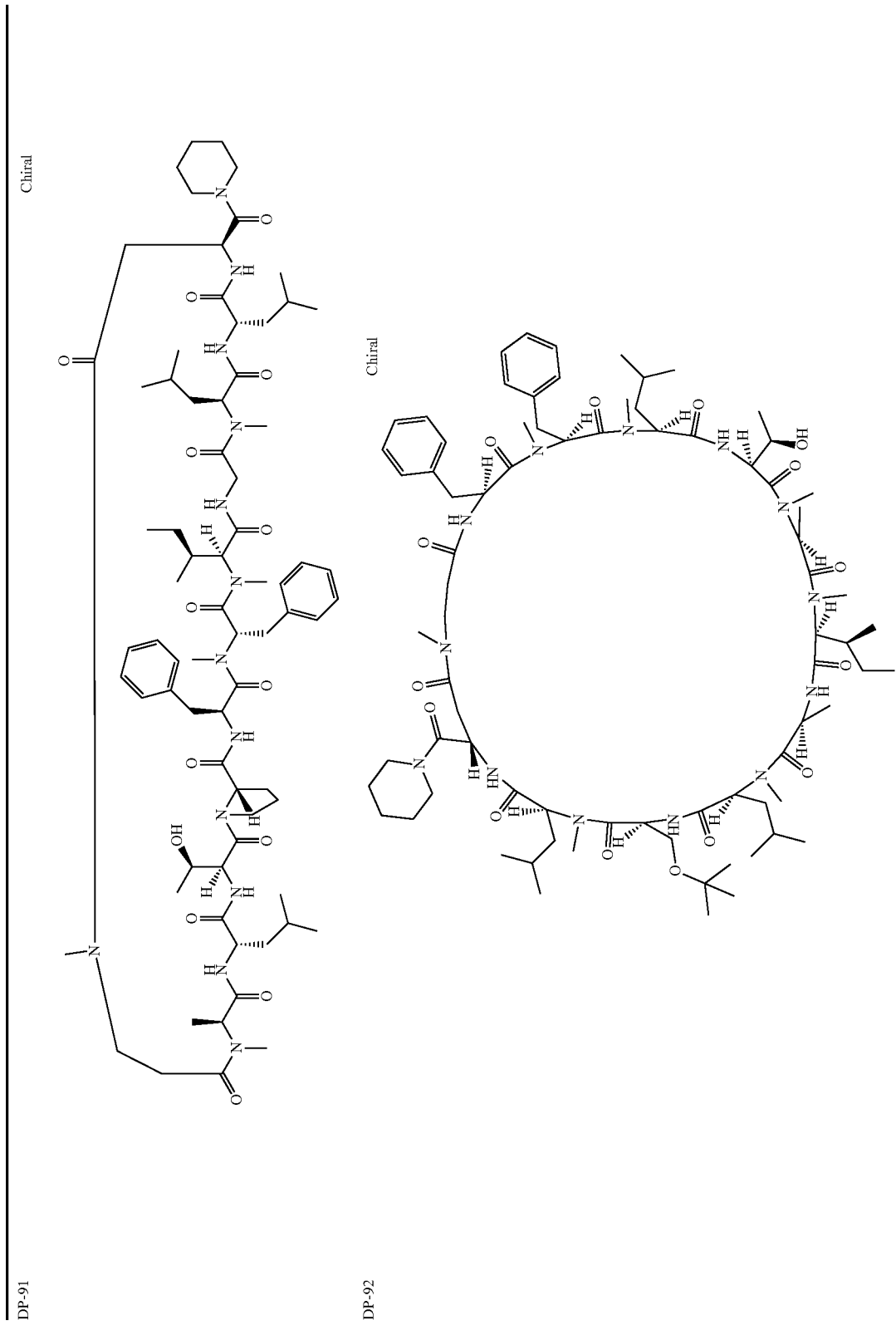
DP-91
DP-92

TABLE 11-3-1-continued
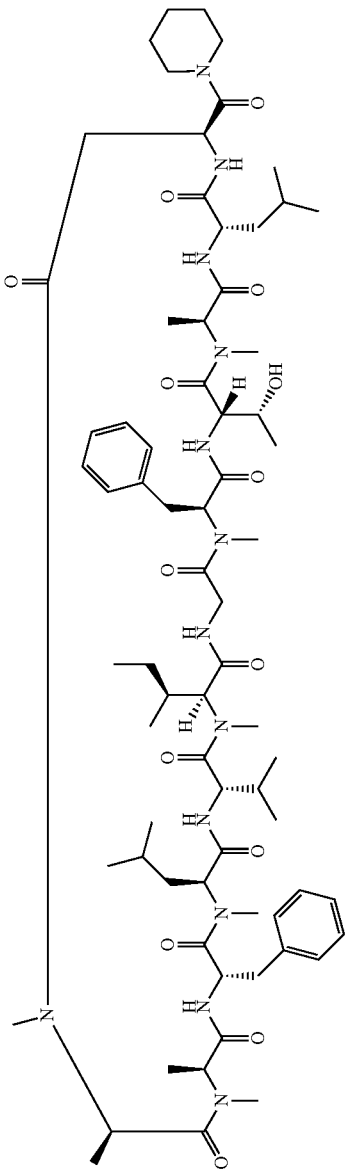
DP-93
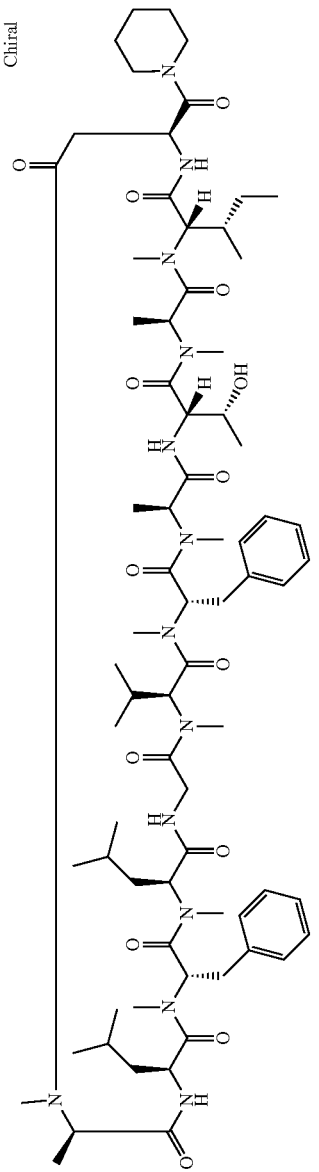
DP-94
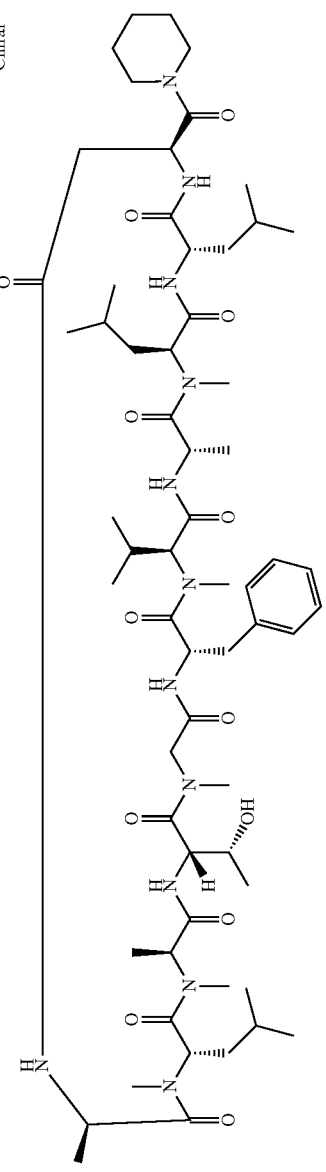
DP-95

TABLE 11-3-1-continued
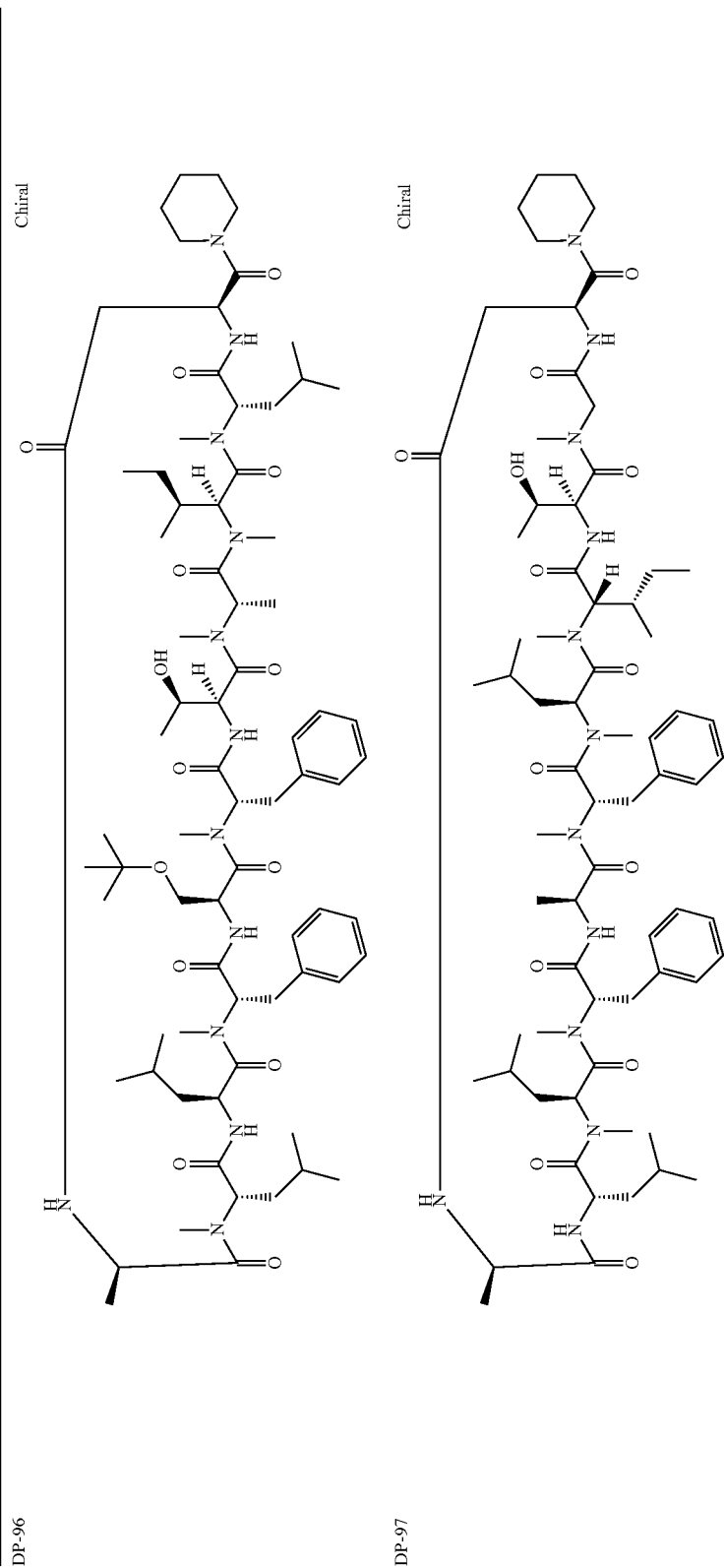
DP-96
DP-97

TABLE 11-3-1-continued
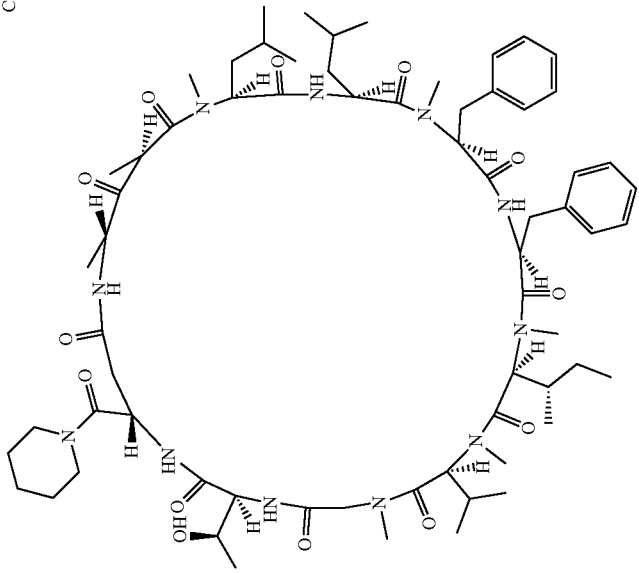
DP-98
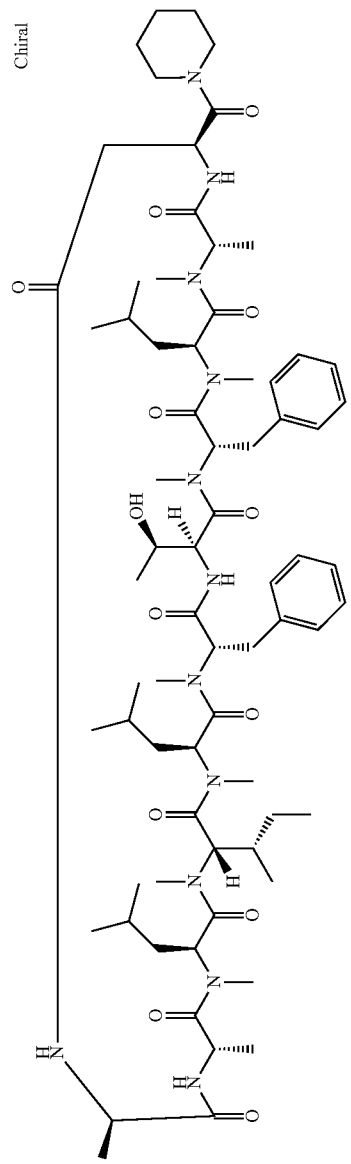
DP-99

TABLE 11-3-1-continued
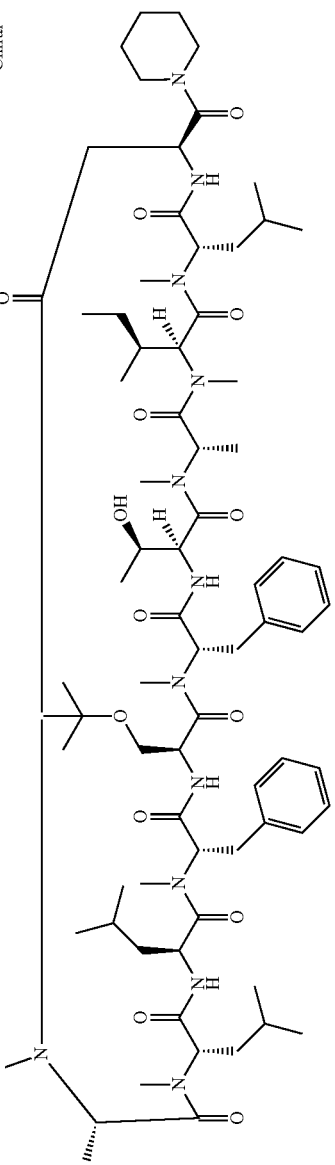
DP-100
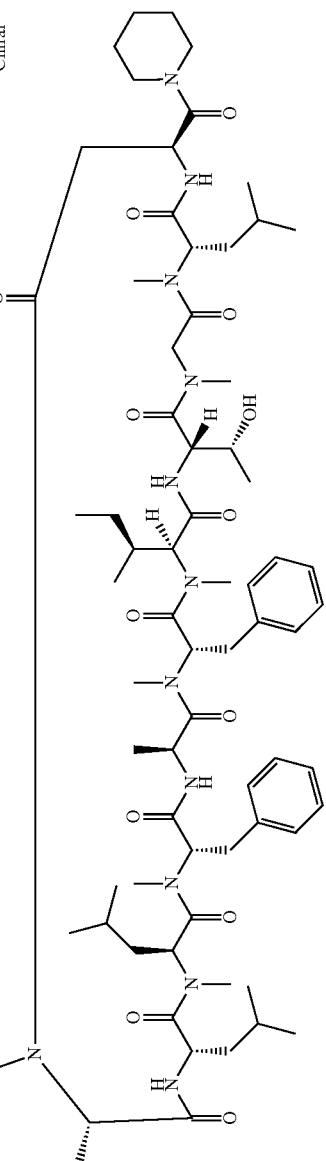
DP-101
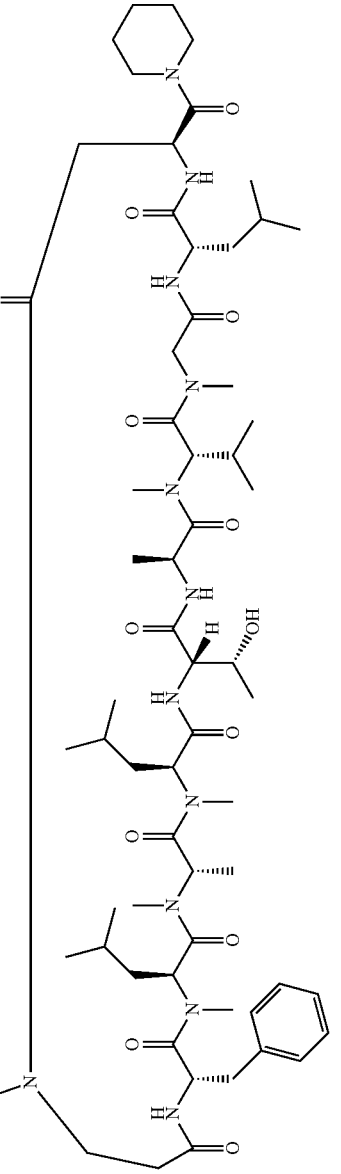
DP-102

TABLE 11-3-1-continued
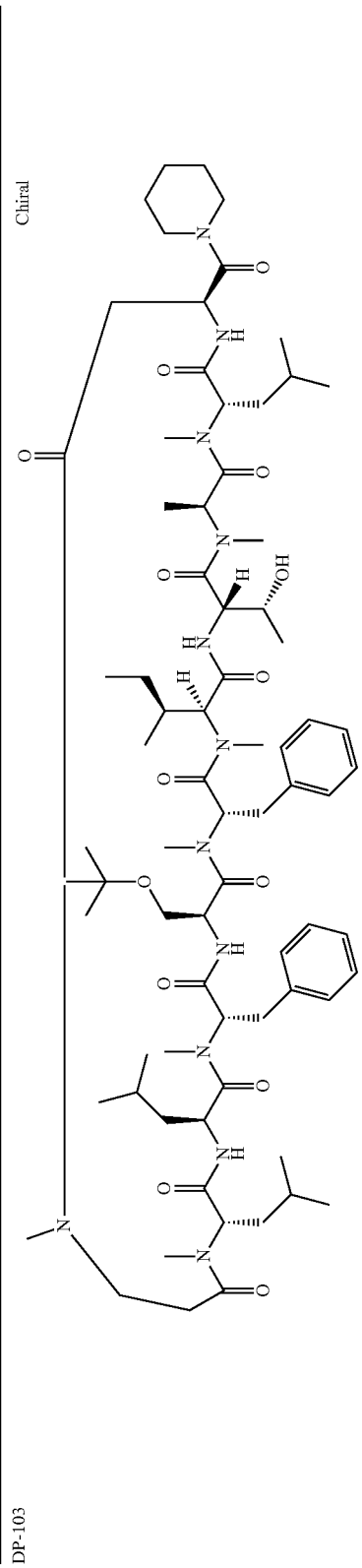
DP-103
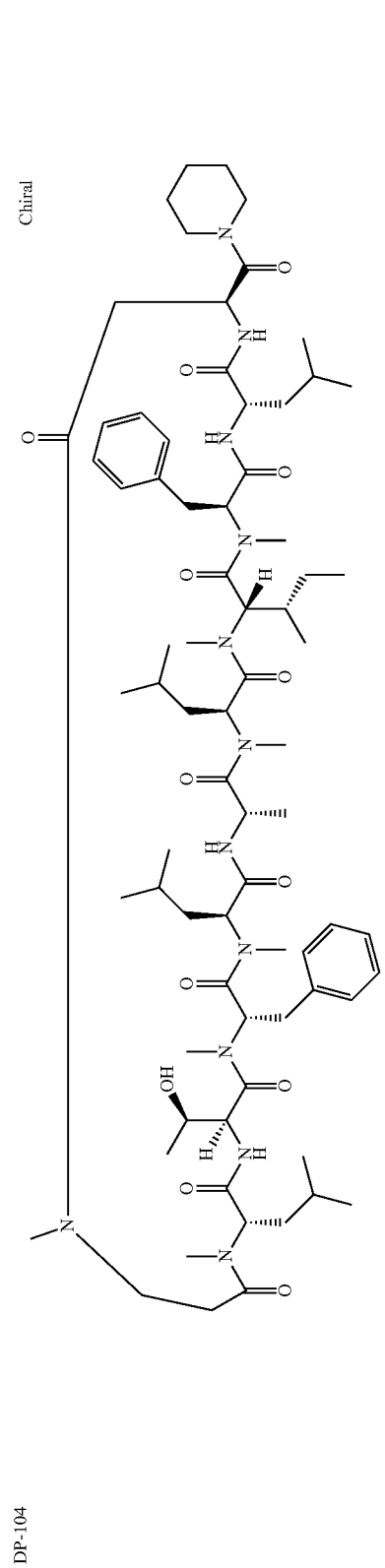
DP-104
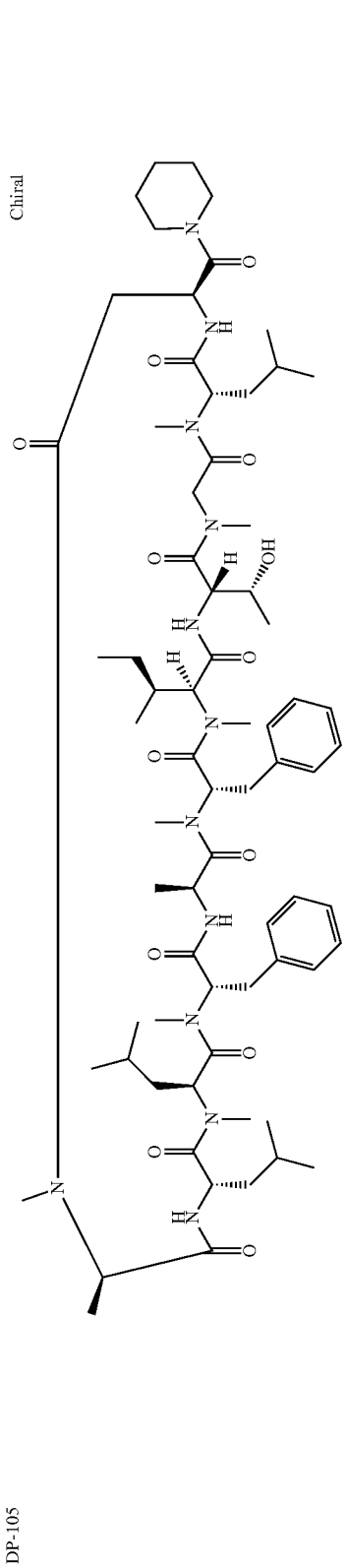
DP-105

TABLE 11-3-1-continued
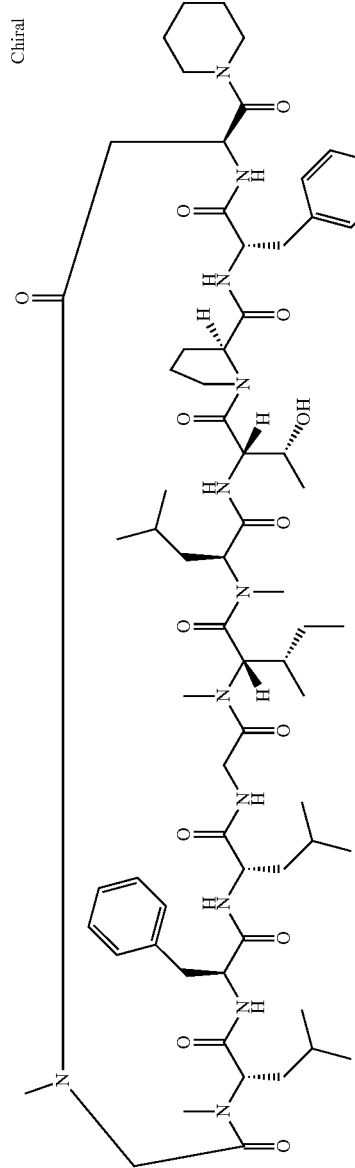
DP-106
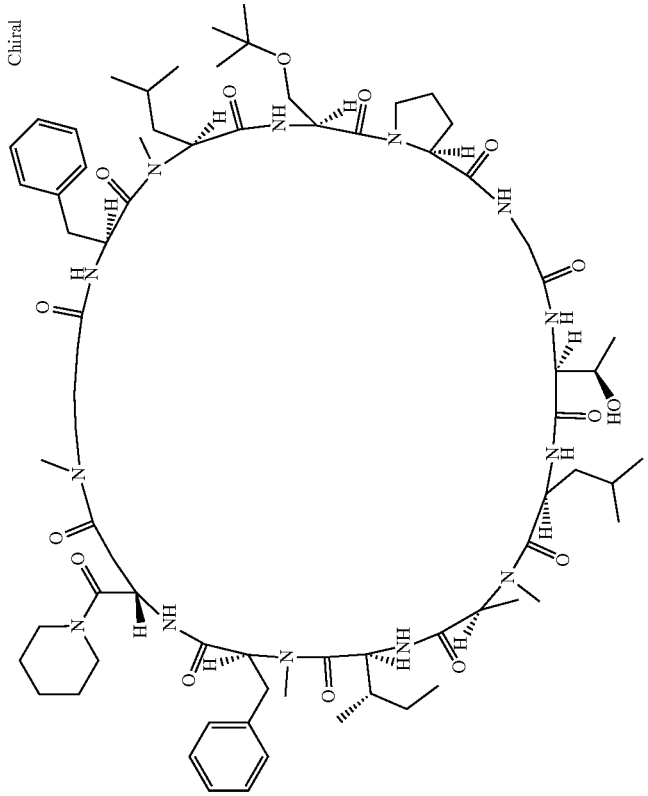
DP-107

TABLE 11-3-1-continued
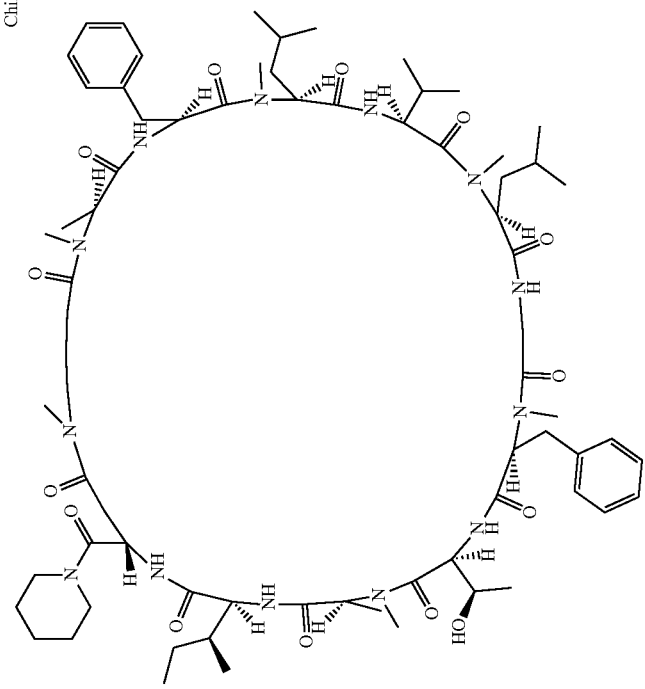
DP-108

TABLE 11-3-1-continued
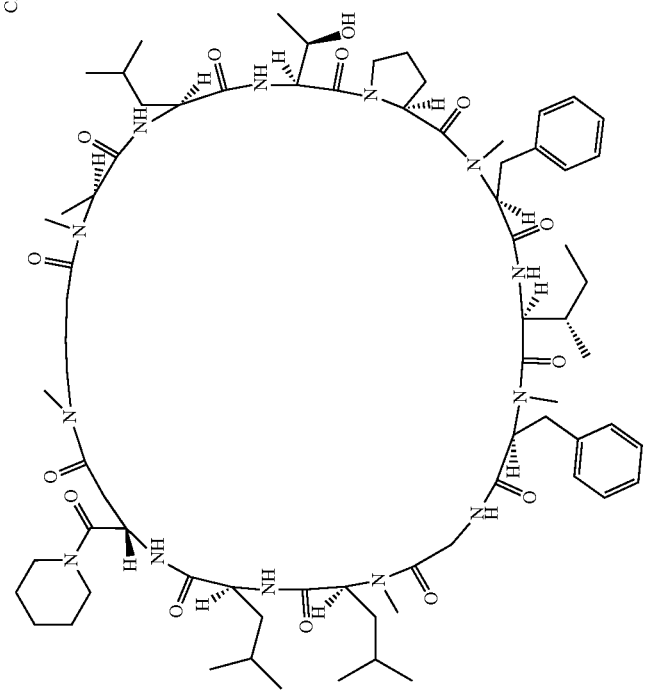
DP-109

TABLE 11-3-1-continued
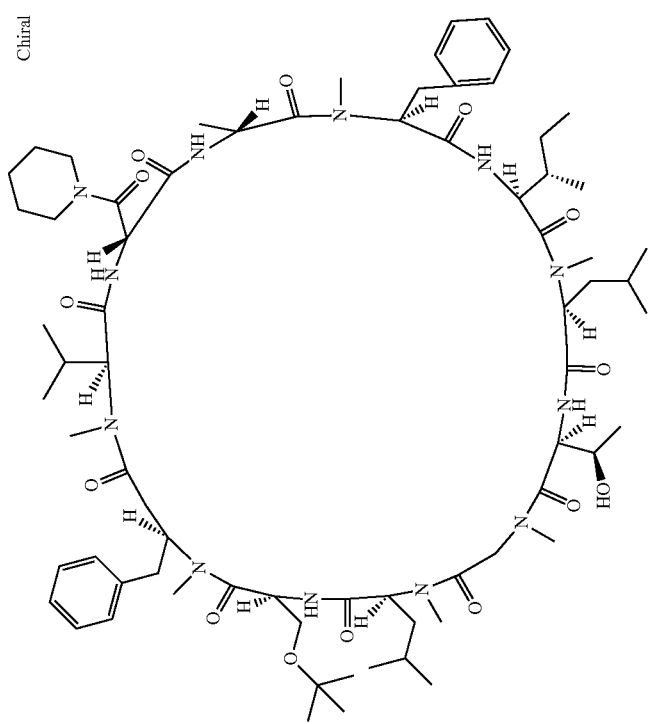
DP-110

TABLE 11-3-1-continued
DP-111
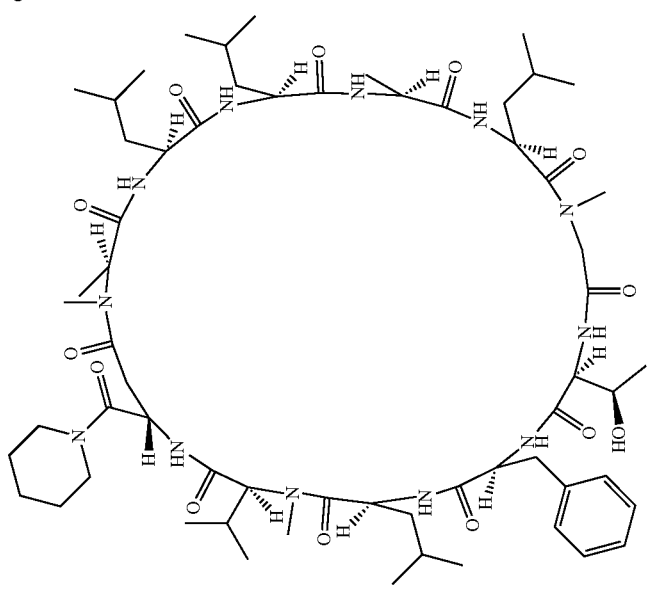

TABLE 11-3-1-continued
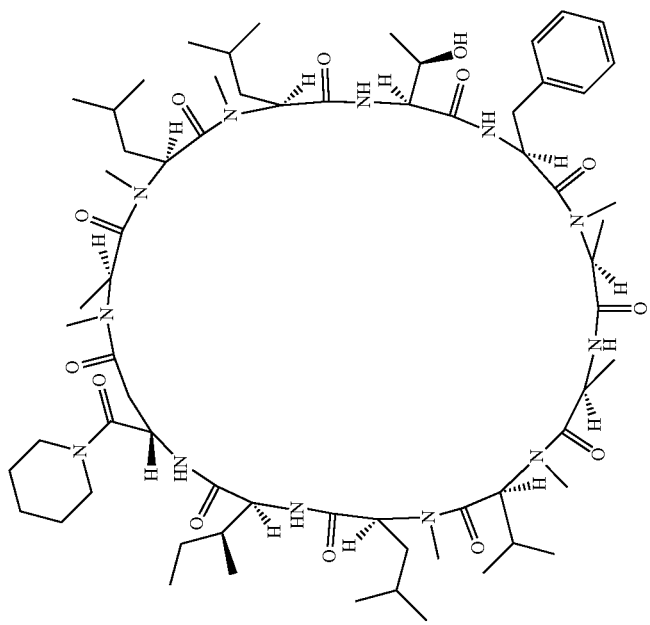
DP-112

TABLE 11-3-1-continued
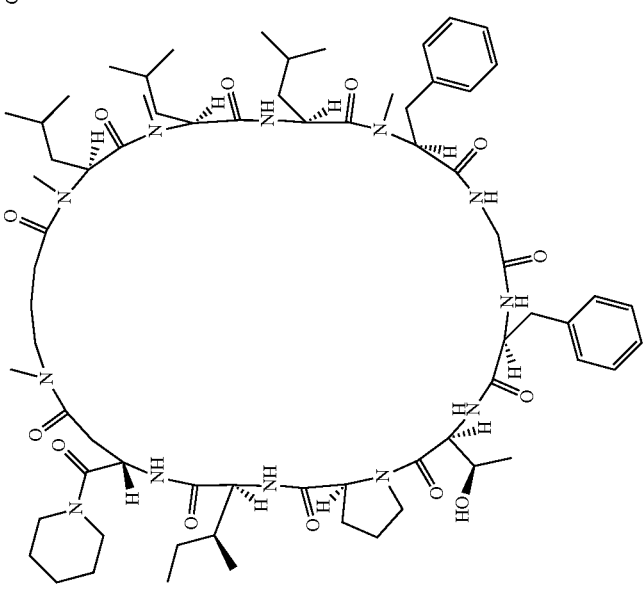
DP-113

TABLE 11-3-1-continued
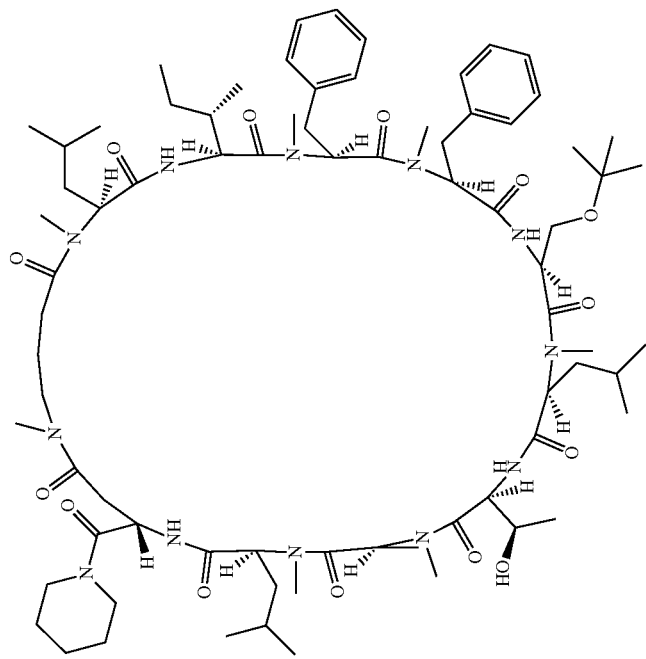
DP-114

TABLE 11-3-1-continued
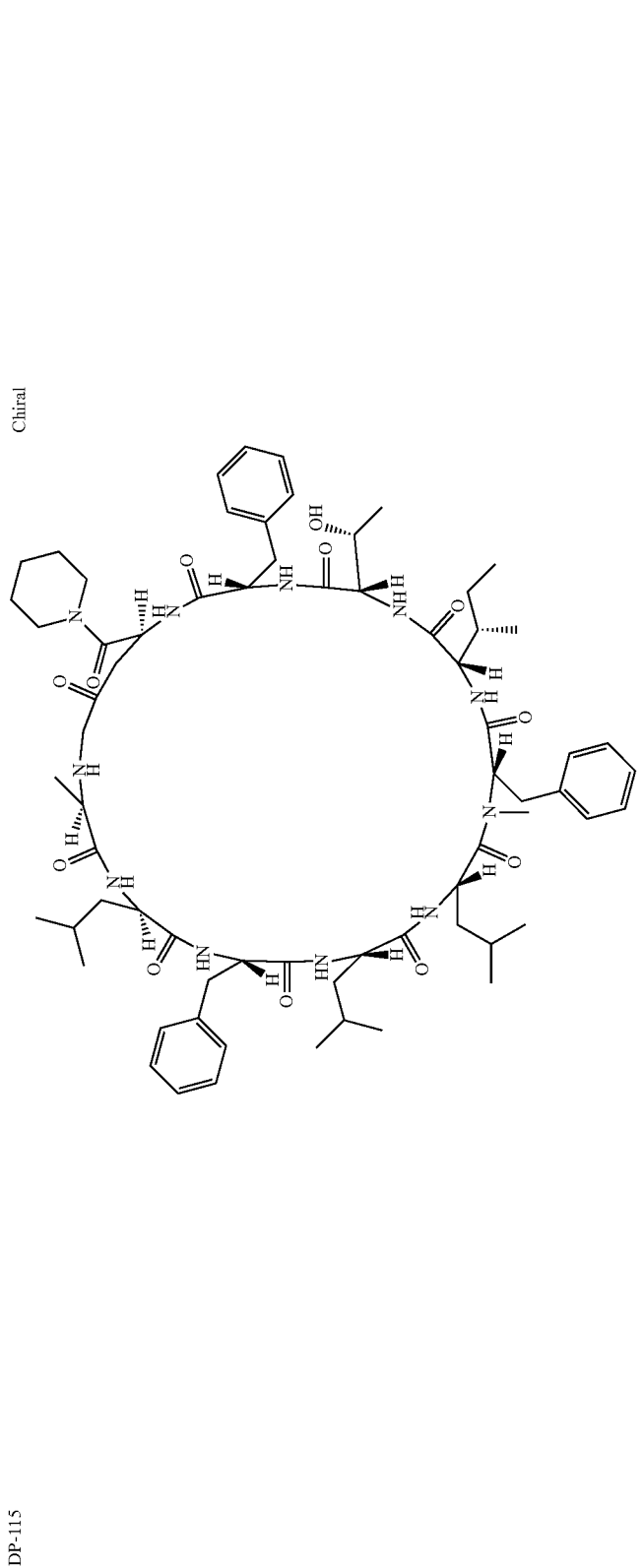
DP-115

TABLE 11-3-1-continued
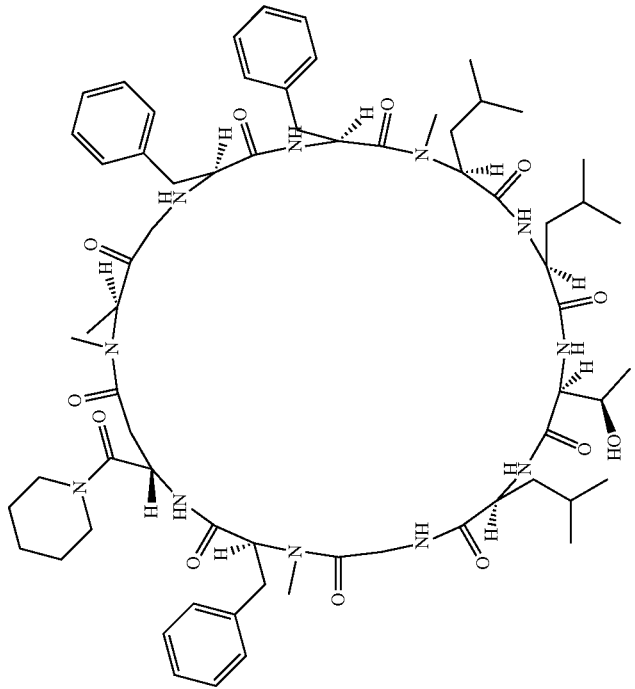
DP-116

TABLE 11-3-1-continued
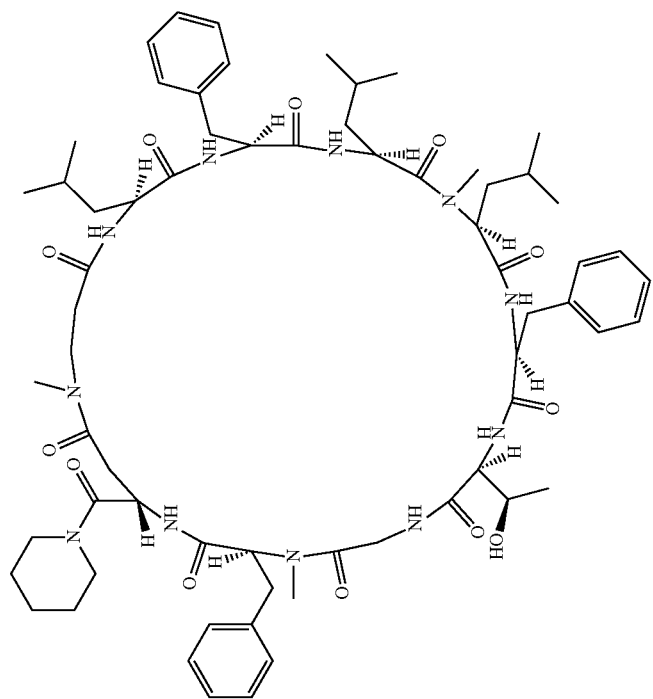
DP-117

TABLE 11-3-1-continued
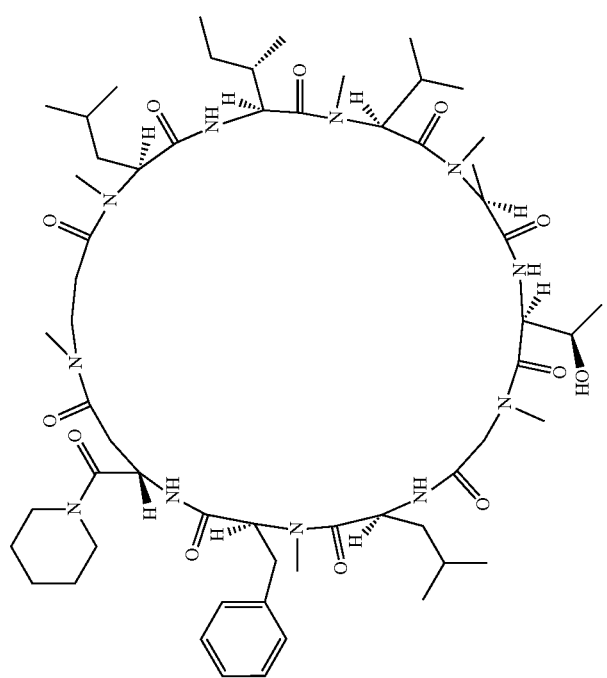
DP-118

TABLE 11-3-1-continued
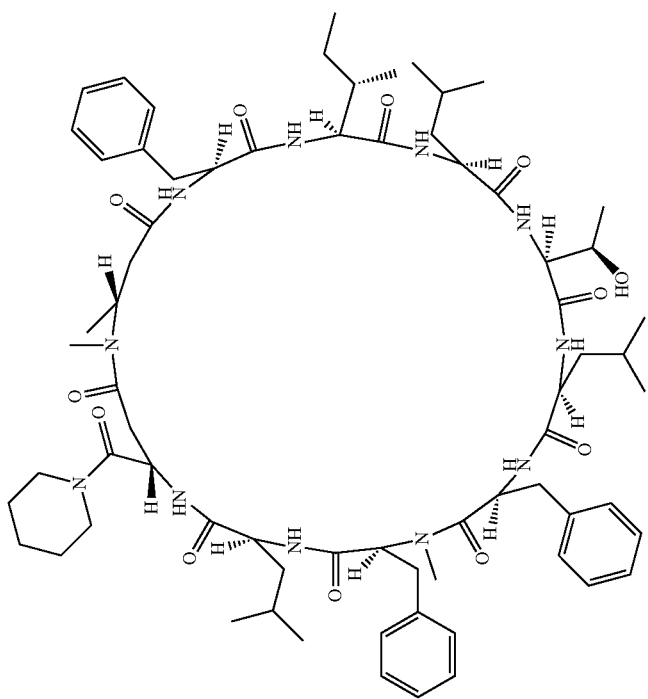
DP-119

TABLE 11-3-1-continued
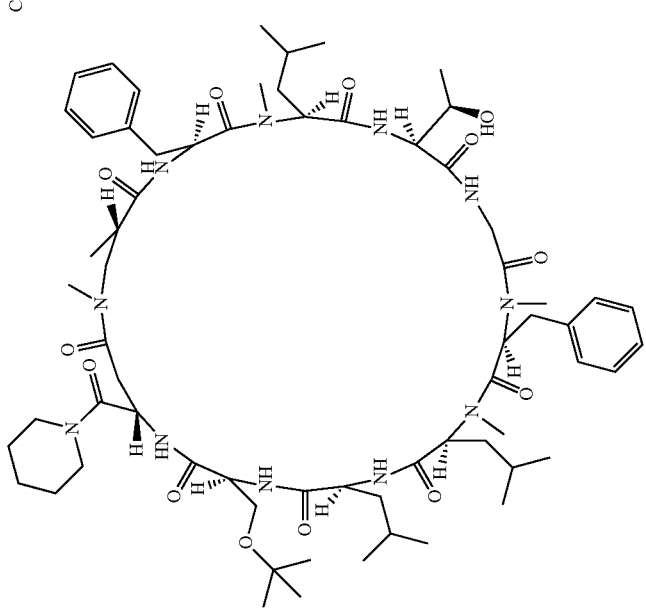
Chiral
DP-120

TABLE 11-3-1-continued
DP-121
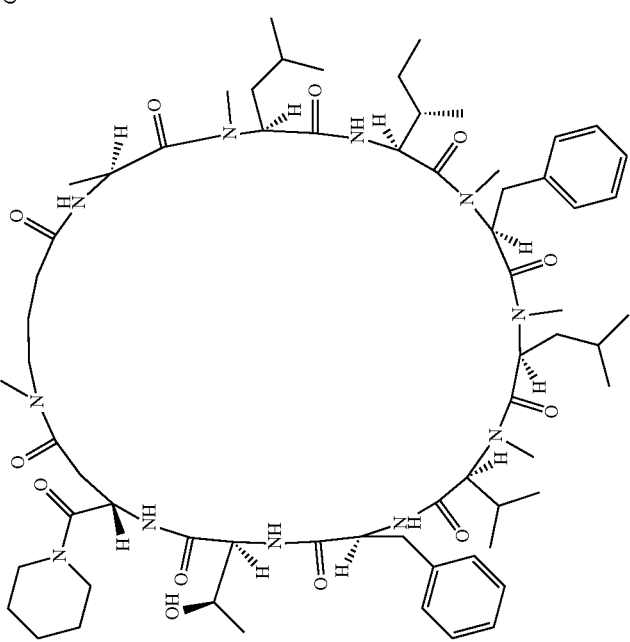

TABLE 11-3-1-continued
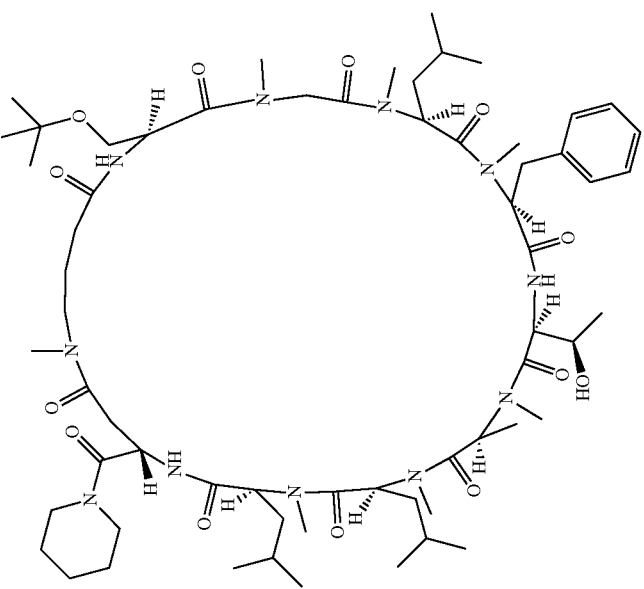
DP-122

TABLE 11-3-1-continued
Chiral
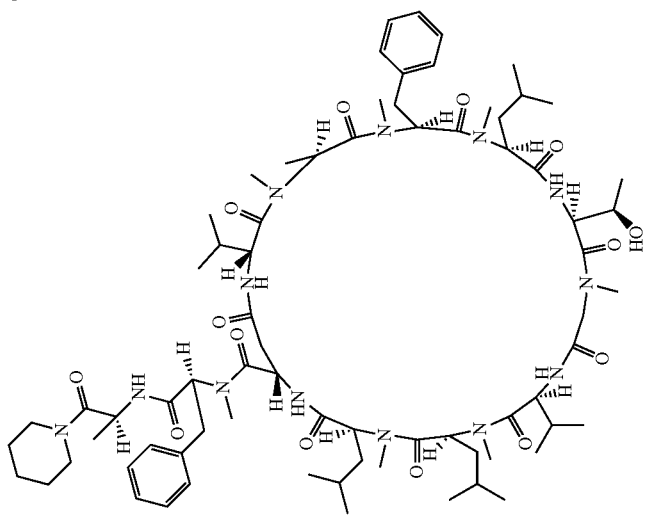
DP-123

TABLE 11-3-1-continued
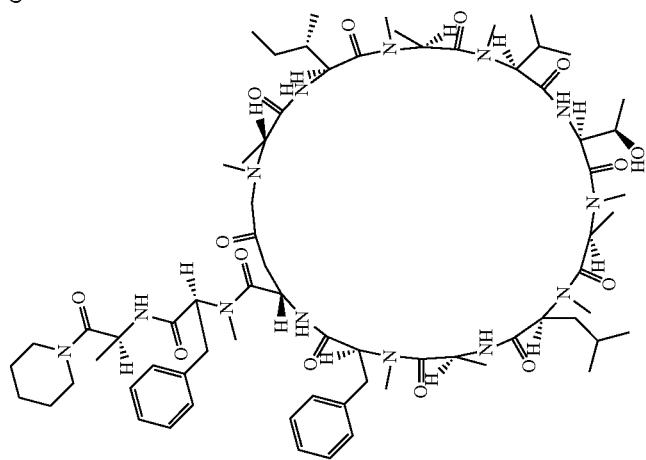
DP-124

TABLE 11-3-1-continued
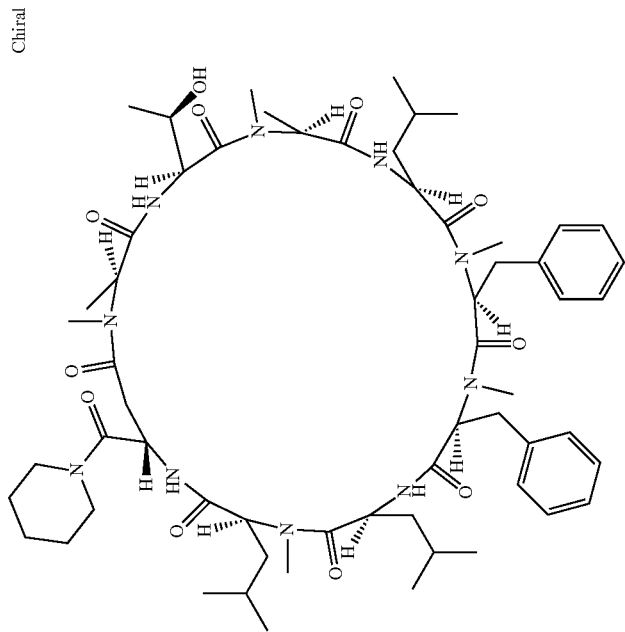
DP-125

TABLE 11-3-1-continued
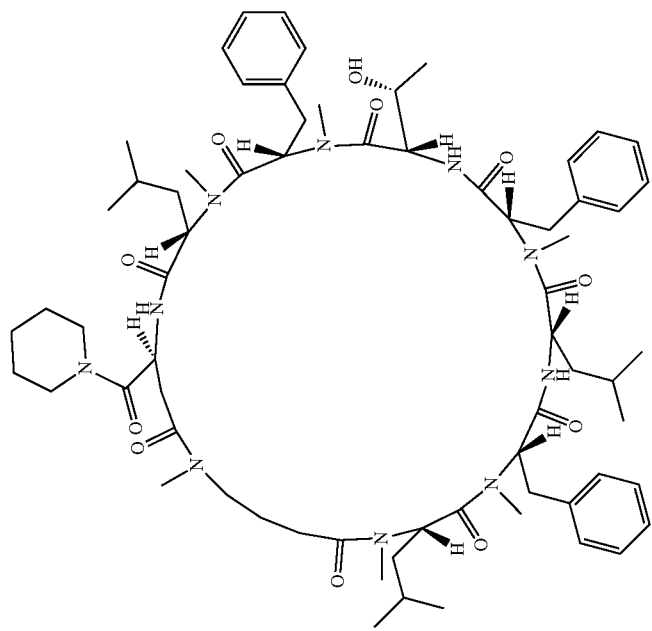
DP-126

TABLE 11-3-1-continued
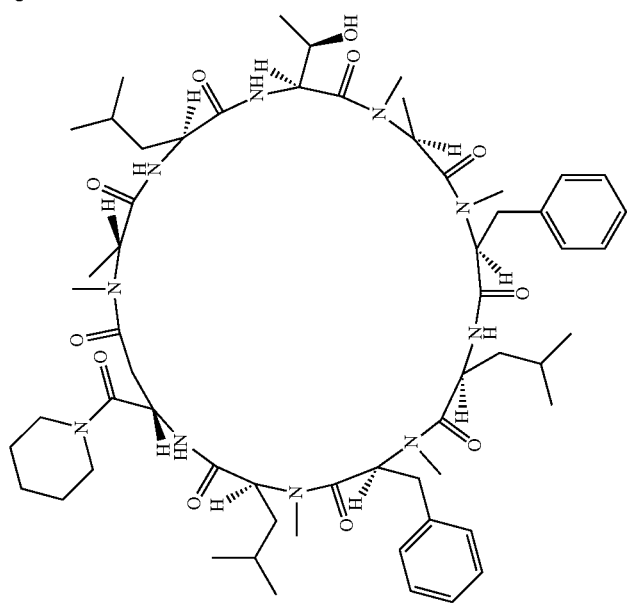
DP-127

TABLE 11-3-1-continued
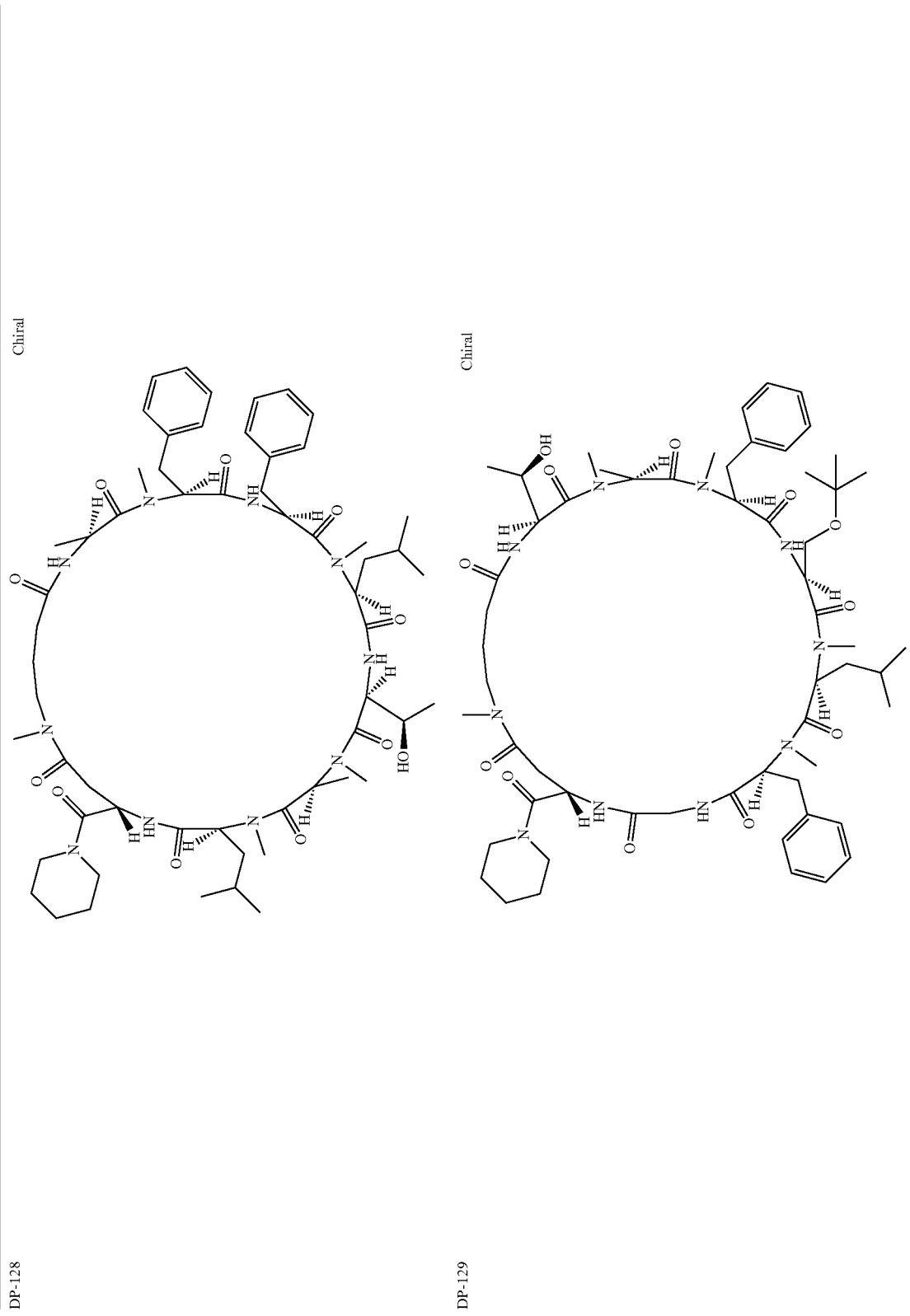
DP-128
DP-129

TABLE 11-3-1-continued
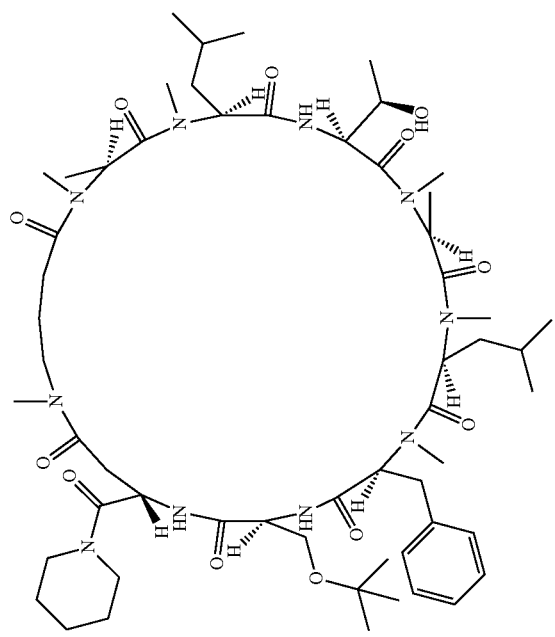
DP-130

TABLE 11-3-1-continued
DP-131
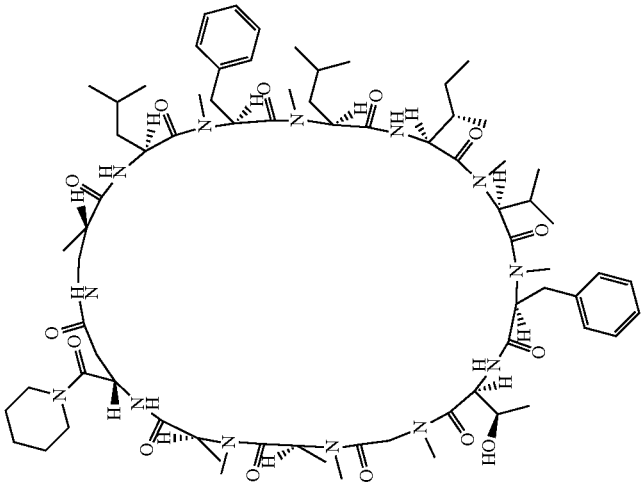
Chiral

TABLE 11-3-1-continued
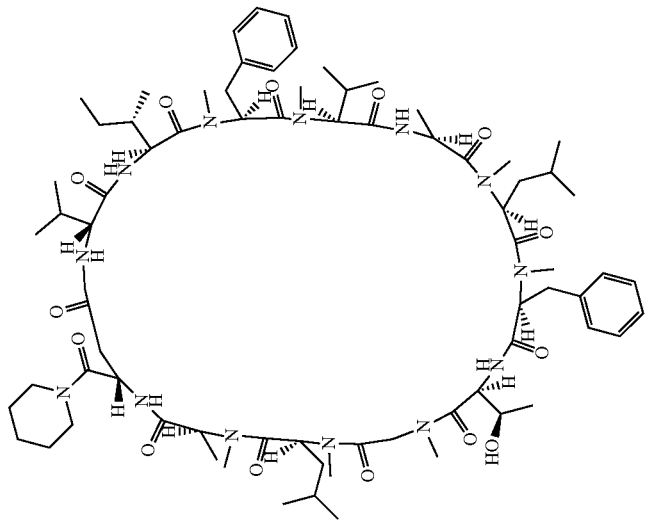
DP-132

TABLE 11-3-1-continued
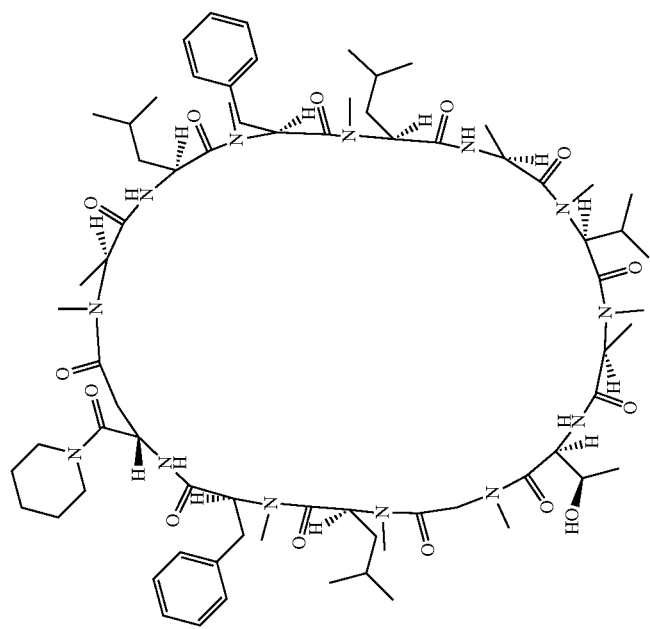
DP-133

TABLE 11-3-1-continued
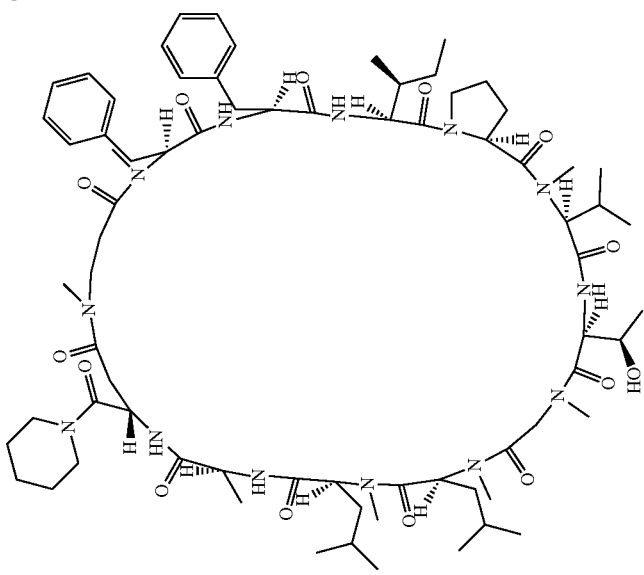
DP-134

TABLE 11-3-1-continued
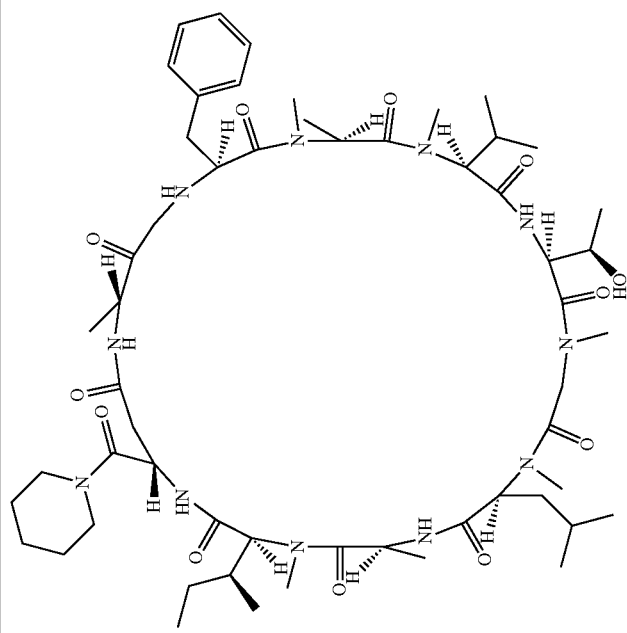
DP-135

TABLE 11-3-1-continued
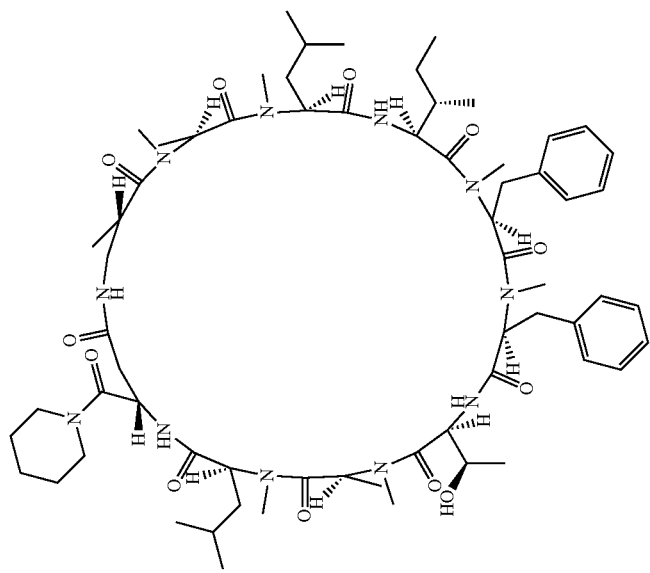
DP-136

TABLE 11-3-1-continued
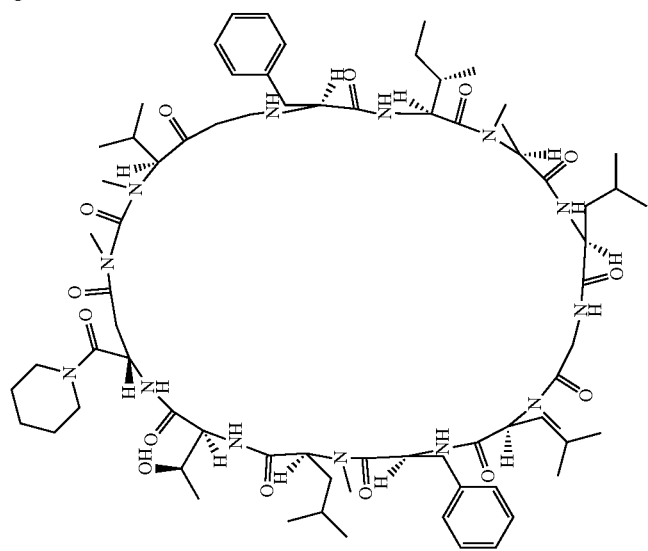
DP-137

TABLE 11-3-1-continued
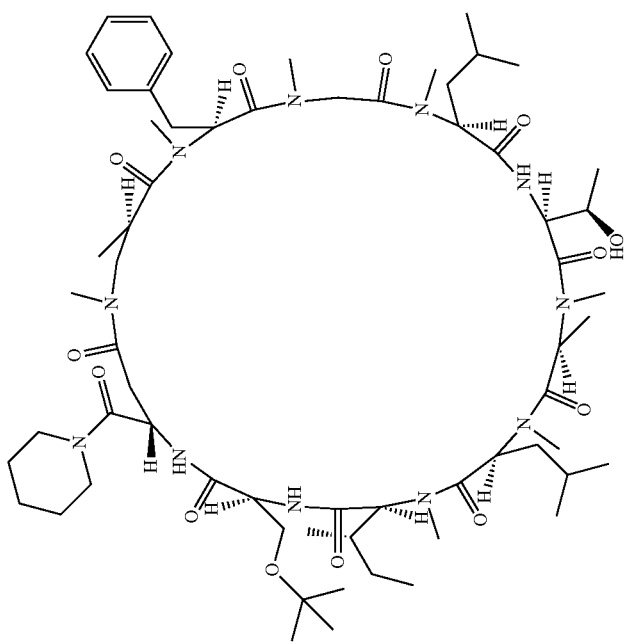
DP-138

TABLE 11-3-1-continued
Chiral
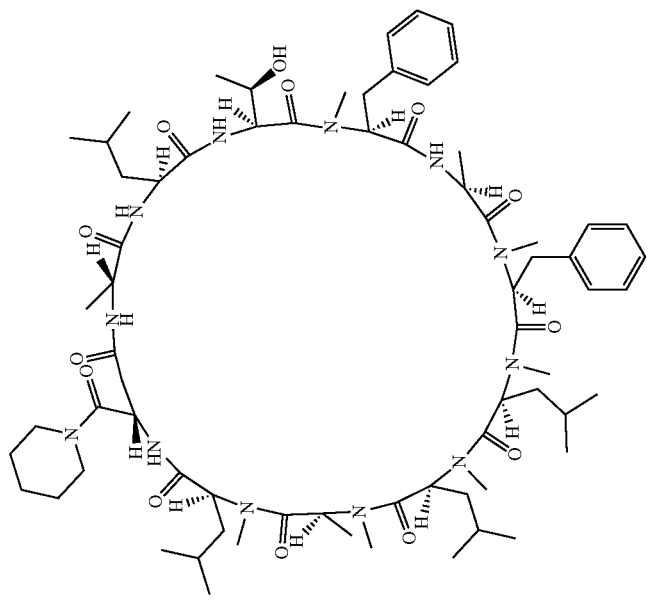
DP-139

TABLE 11-3-1-continued
Chiral
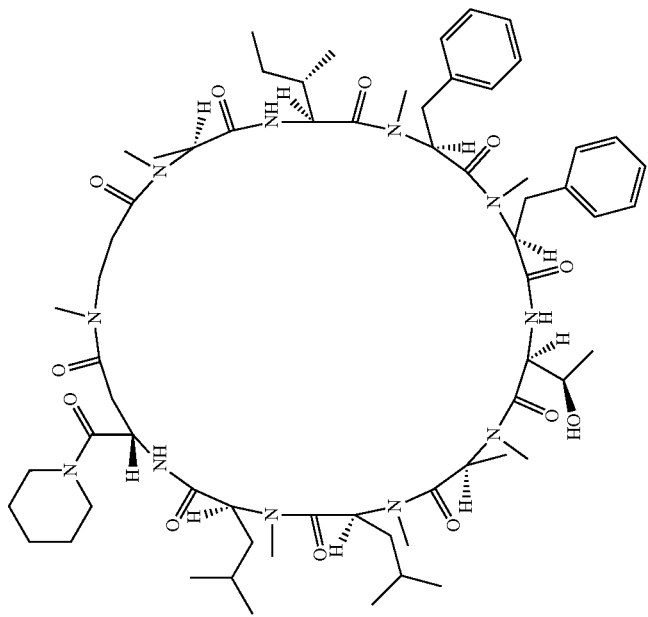
DP-140

TABLE 11-3-1-continued
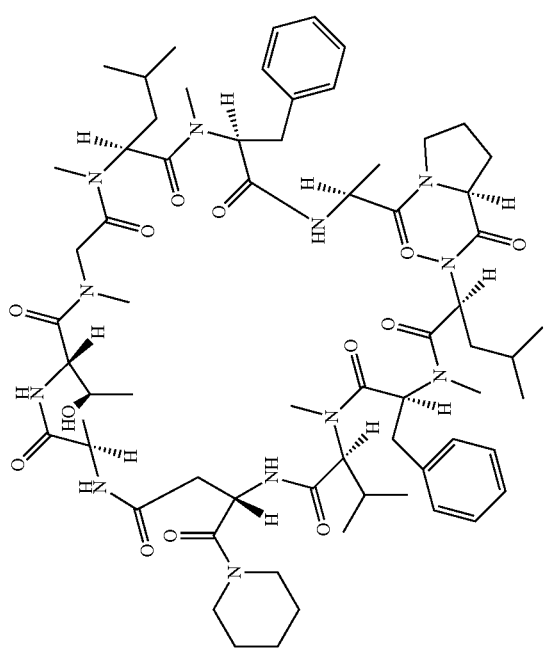
DP-141

TABLE 11-3-1-continued
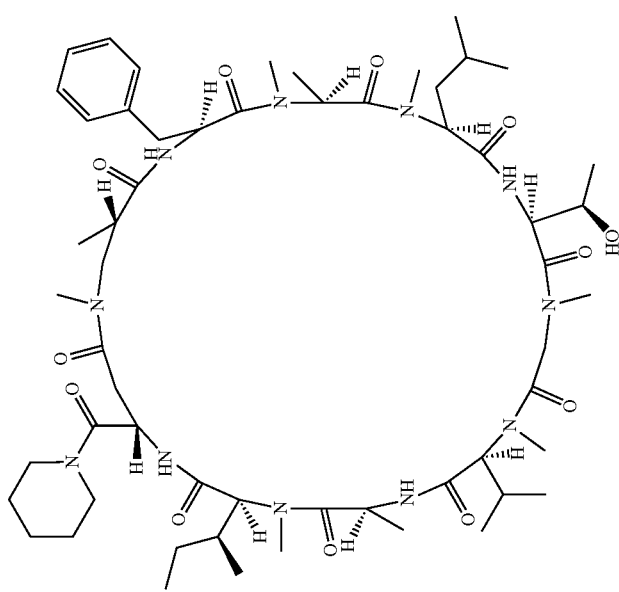
DP-142

TABLE 11-3-1-continued
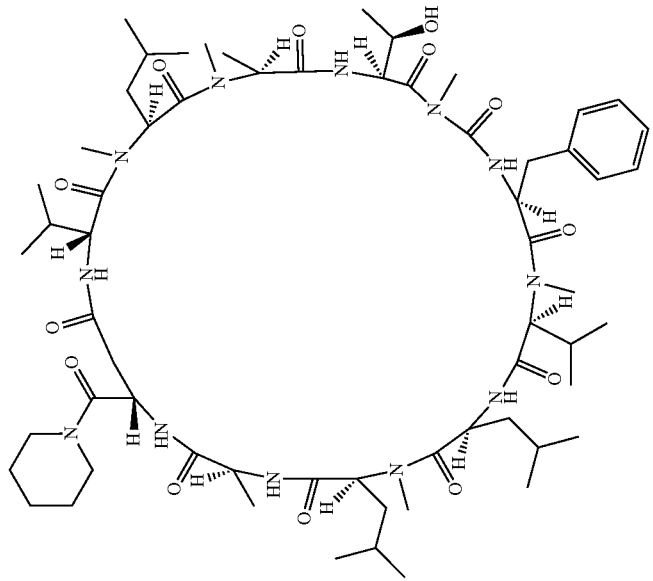
DP-143

TABLE 11-3-1-continued
DP-144
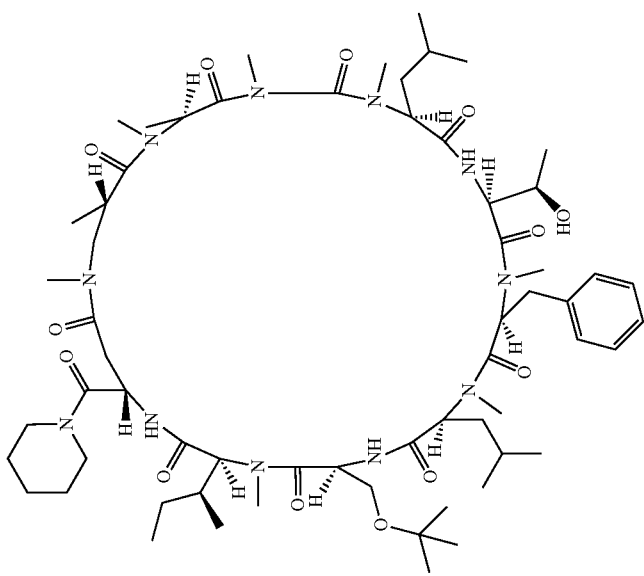
Chiral

TABLE 11-3-1-continued
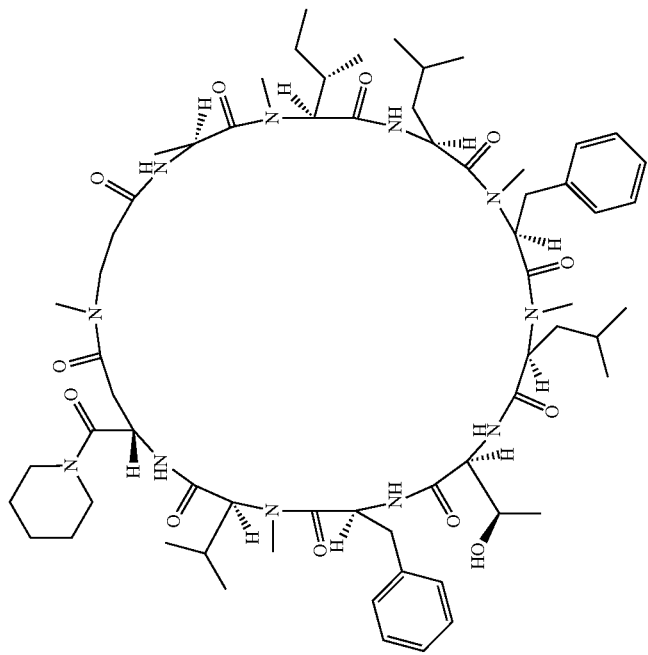
DP-145

TABLE 11-3-1-continued
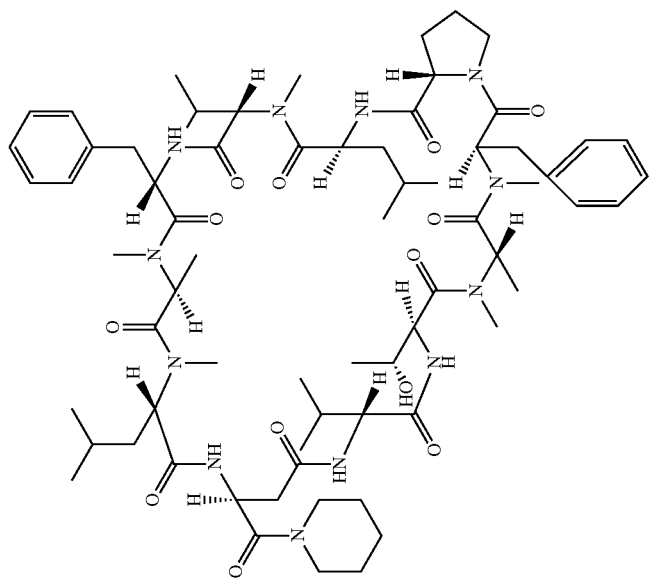
DP-146

TABLE 11-3-1-continued
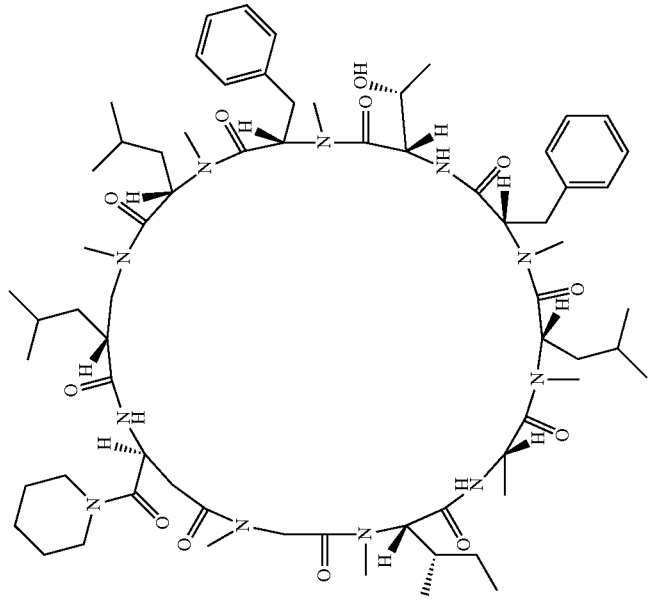
DP-147

TABLE 11-3-1-continued
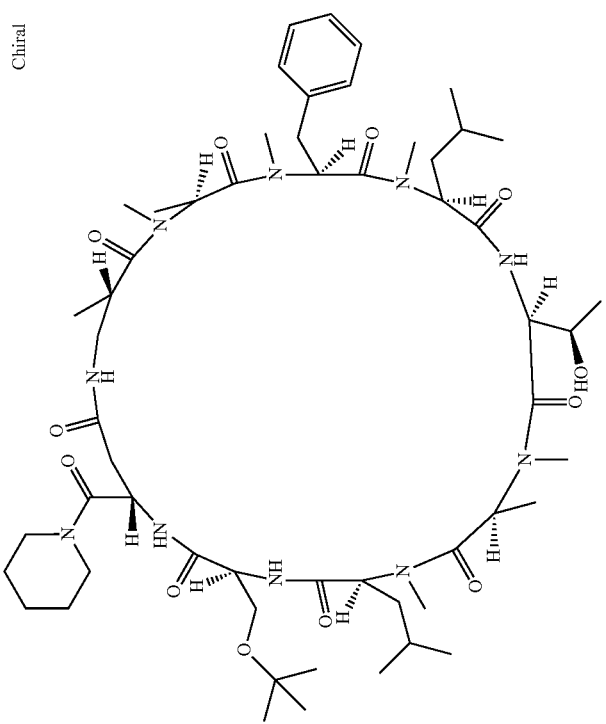
DP-148

TABLE 11-3-1-continued
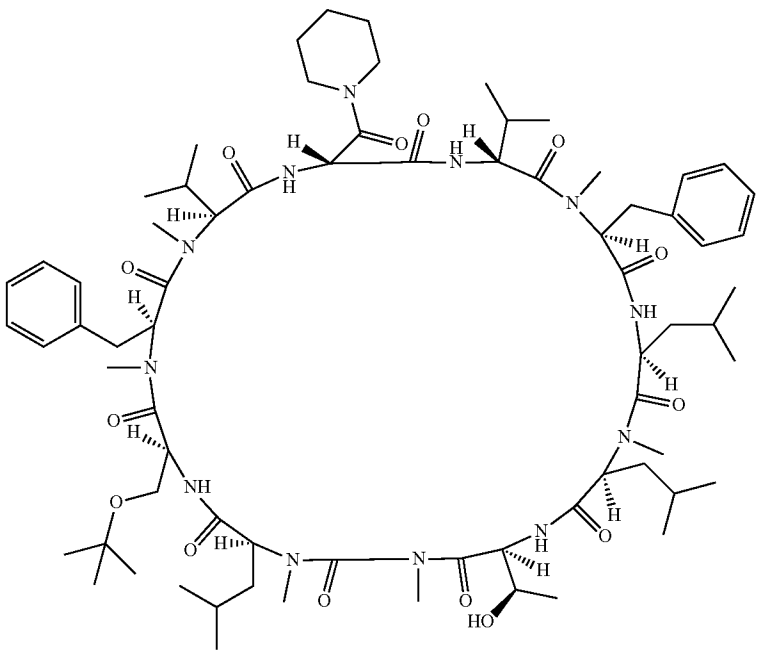
DP-149

TABLE 11-3-1-continued
Chiral
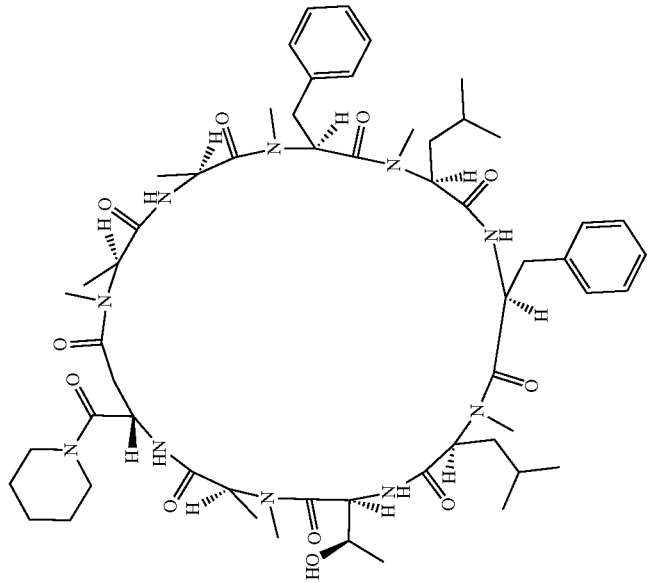
DP-150

TABLE 11-3-1-continued
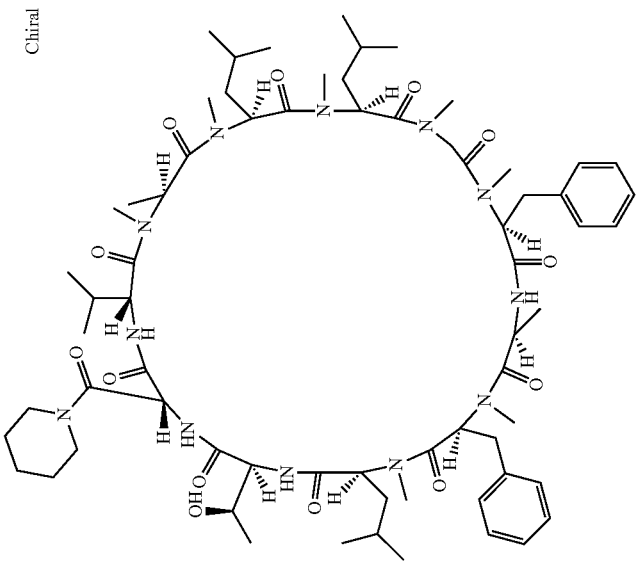
DP-151

TABLE 11-3-1-continued
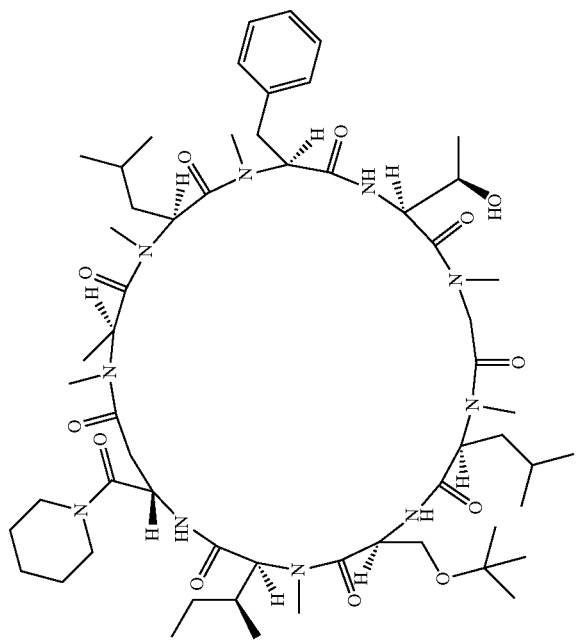
DP-152

TABLE 11-3-1-continued
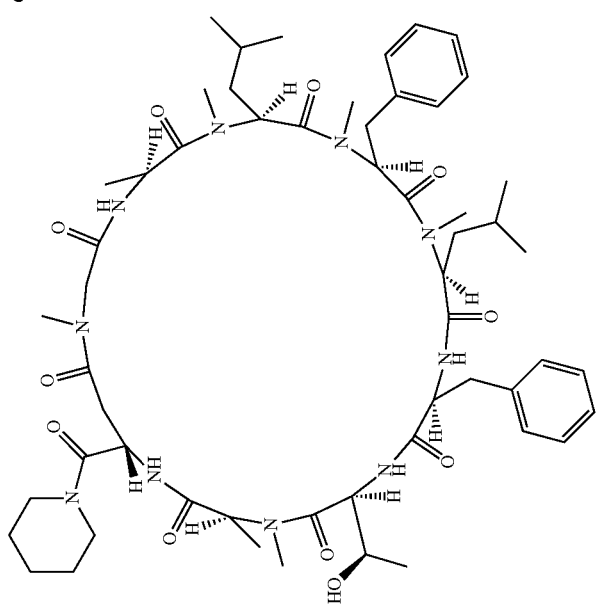
DP-153

TABLE 11-3-1-continued
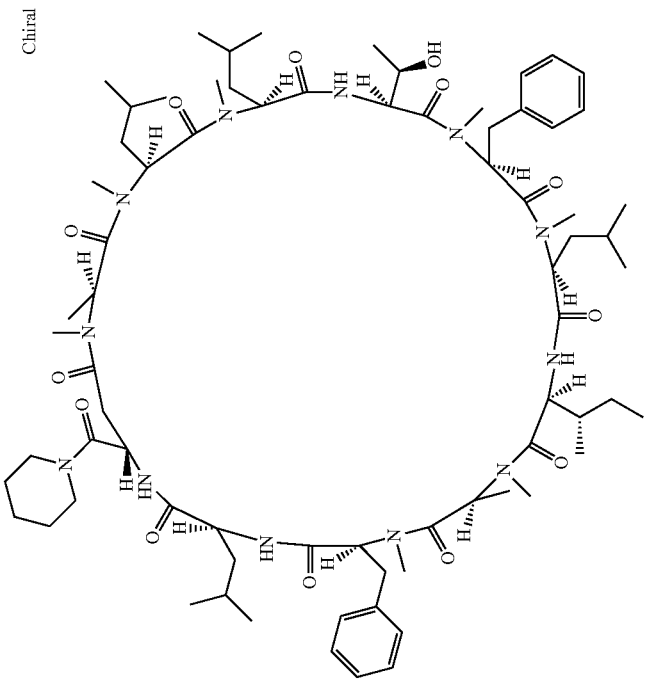
DP-154

TABLE 11-3-1-continued
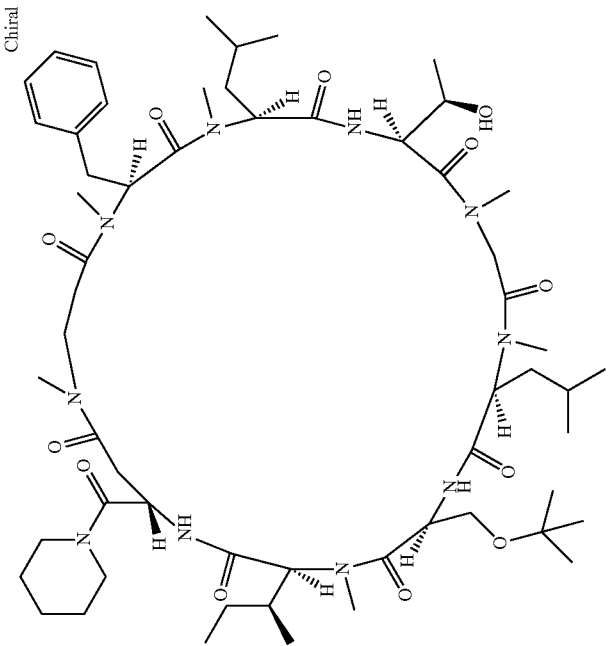
DP-155

TABLE 11-3-1-continued
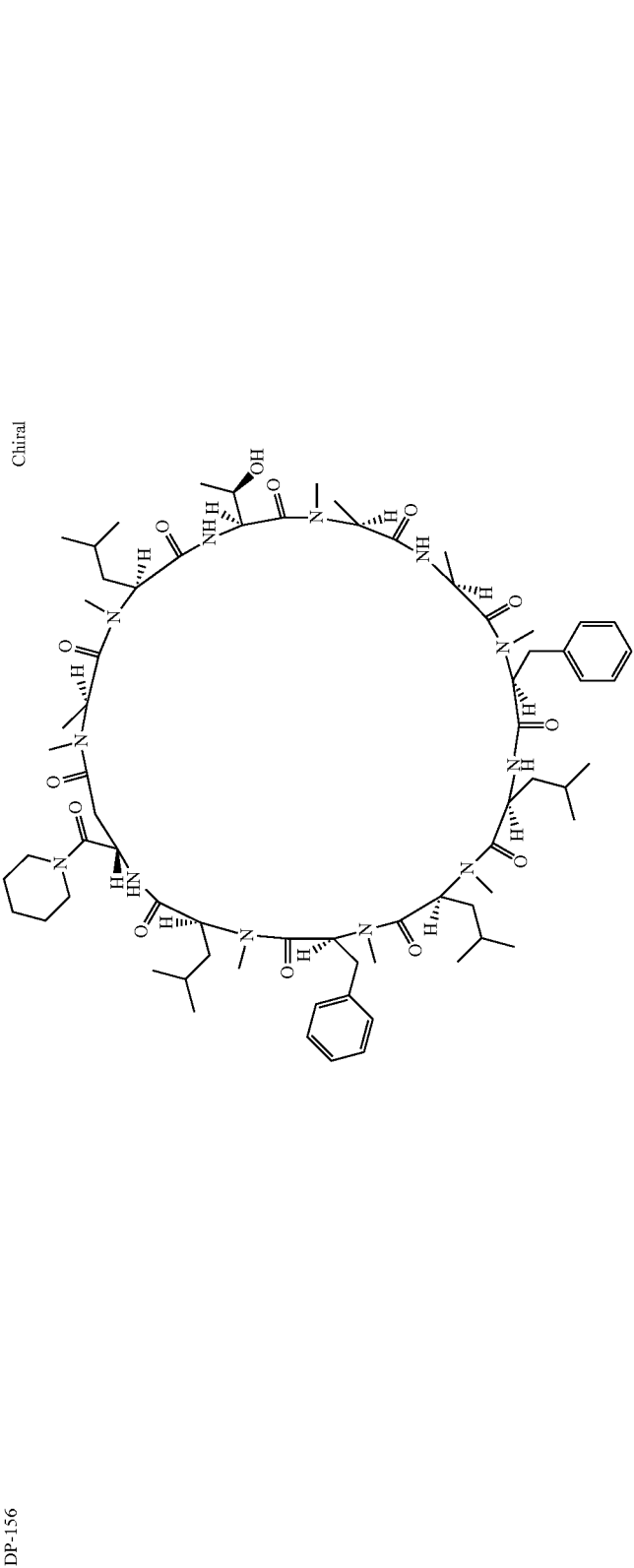
DP-156

TABLE 11-3-1-continued
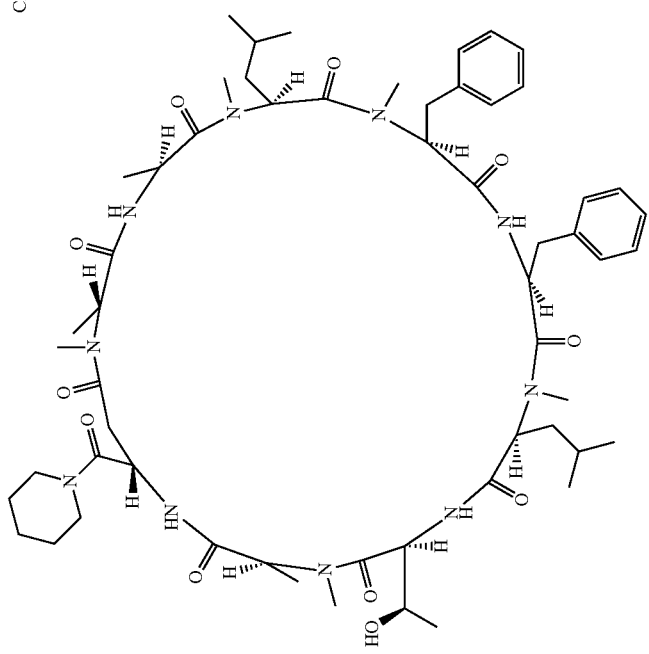
DP-157

TABLE 11-3-1-continued
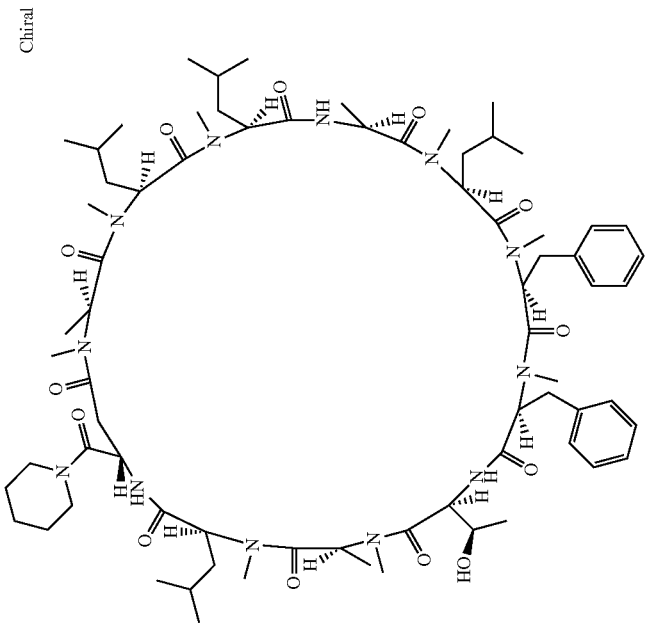
DP-158

TABLE 11-3-1-continued
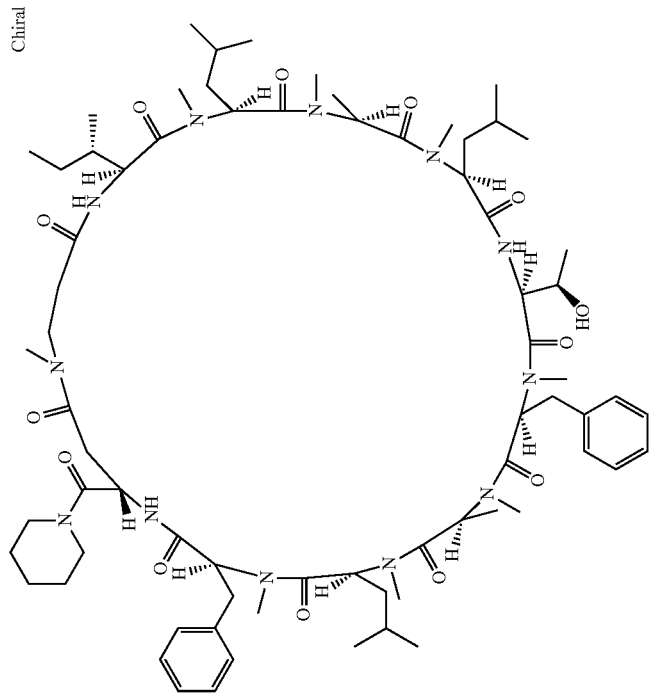
DP-159

TABLE 11-3-1-continued
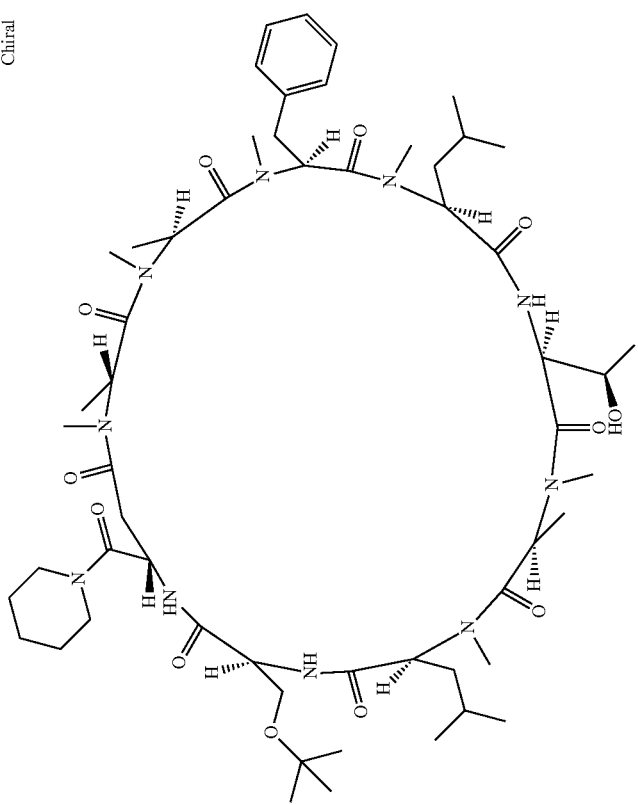
DP-160

TABLE 11-3-1-continued
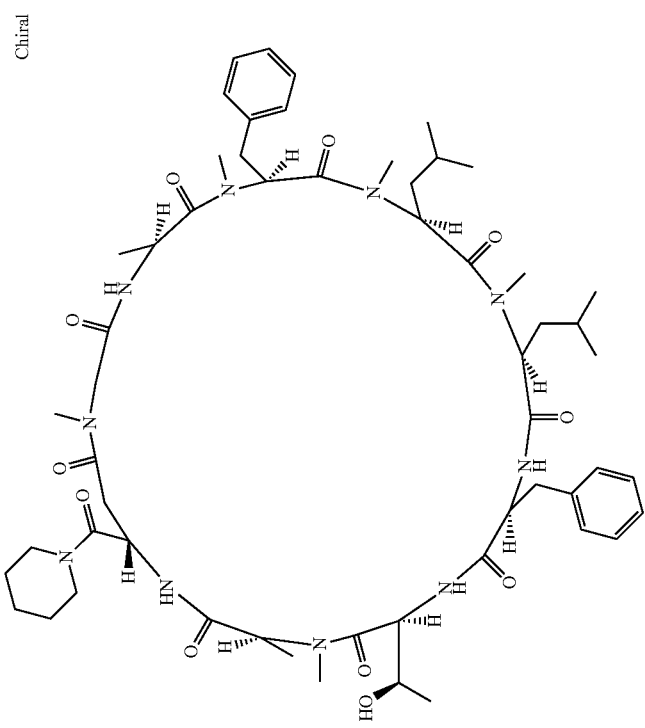
DP-161

TABLE 11-3-1-continued
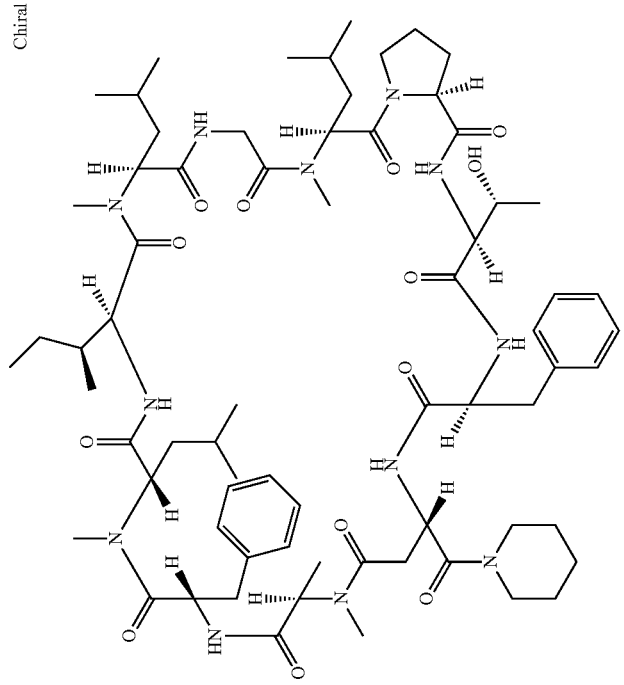
DP-162

TABLE 11-3-1-continued
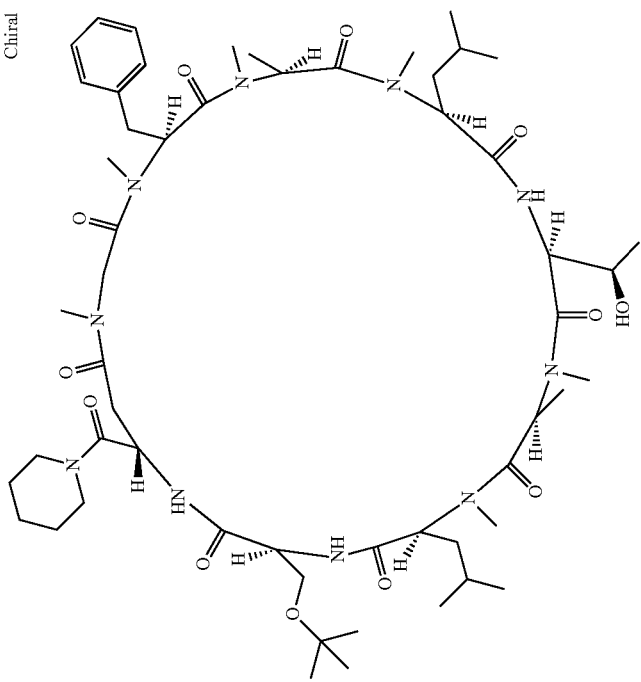
DP-163

TABLE 11-3-1-continued
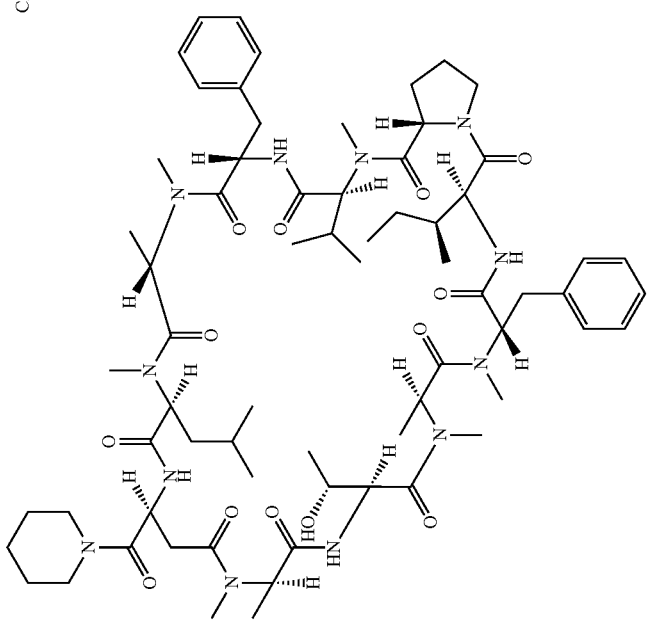
DP-164

TABLE 11-3-1-continued
DP-165
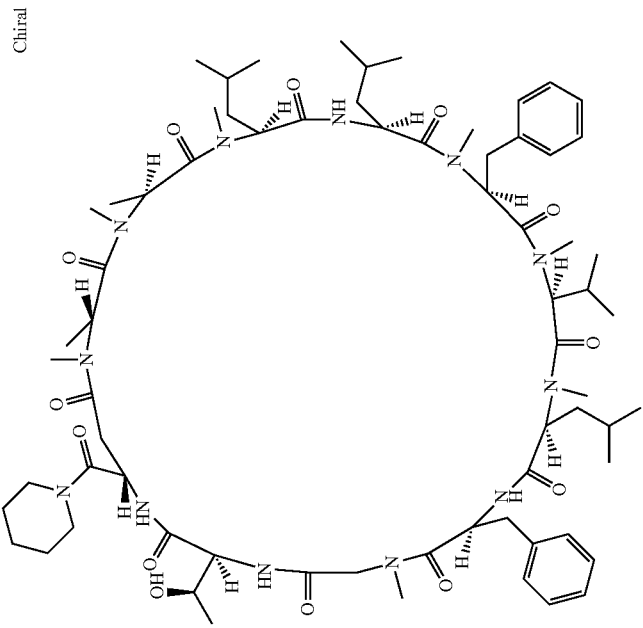

TABLE 11-3-1-continued
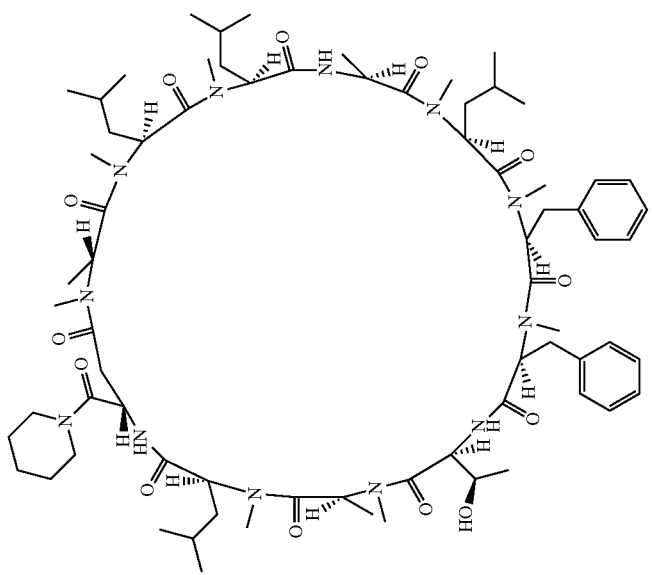
DP-166

TABLE 11-3-1-continued
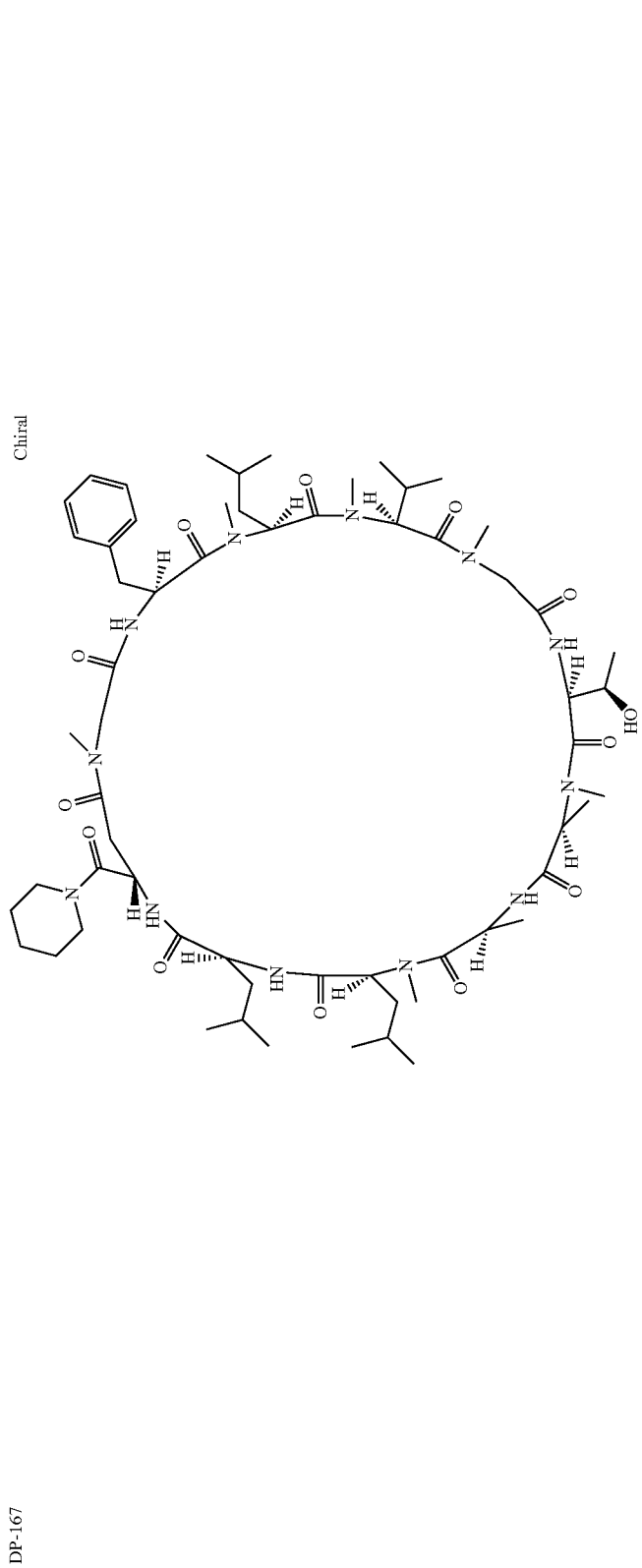
DP-167

TABLE 11-3-1-continued
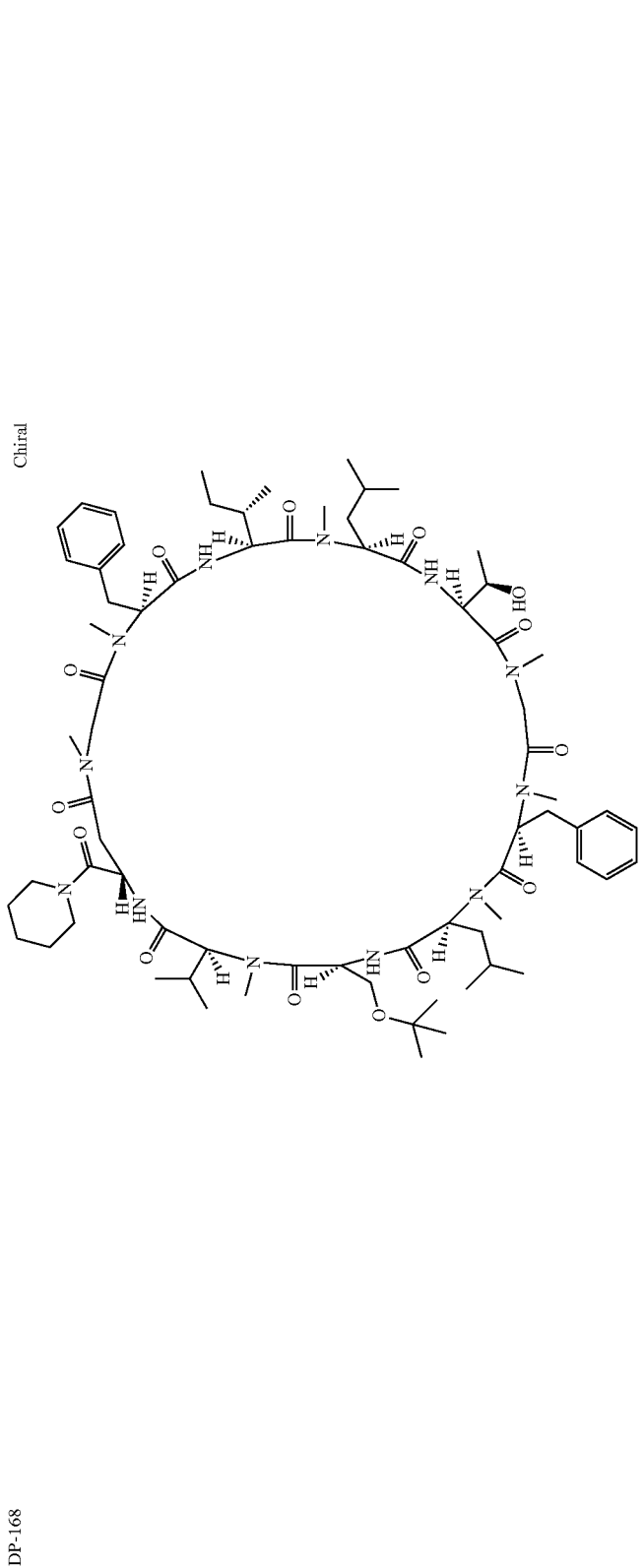
DP-168

TABLE 11-3-1-continued
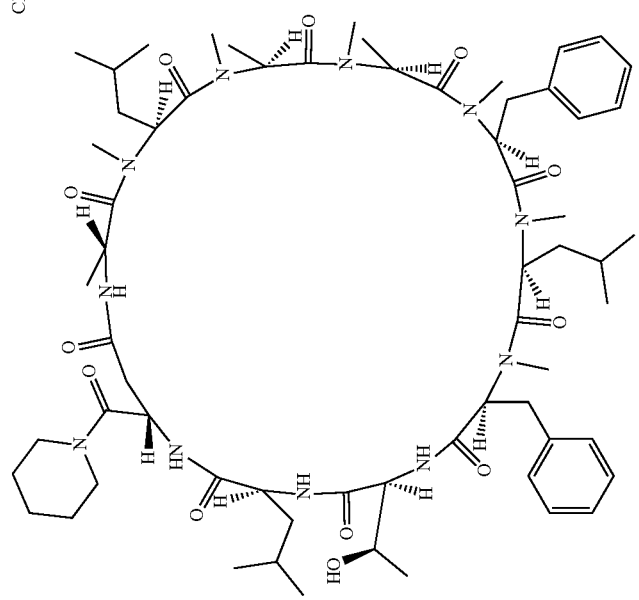
DP-169

TABLE 11-3-1-continued
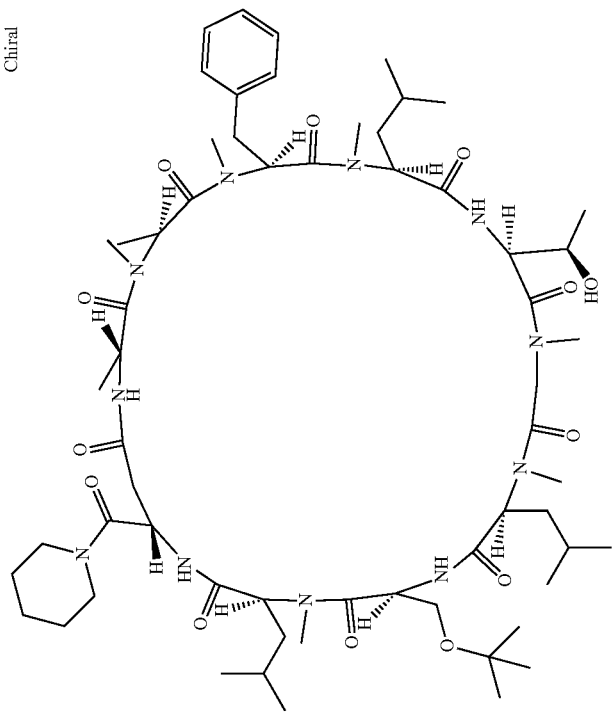
DP-170

TABLE 11-3-1-continued
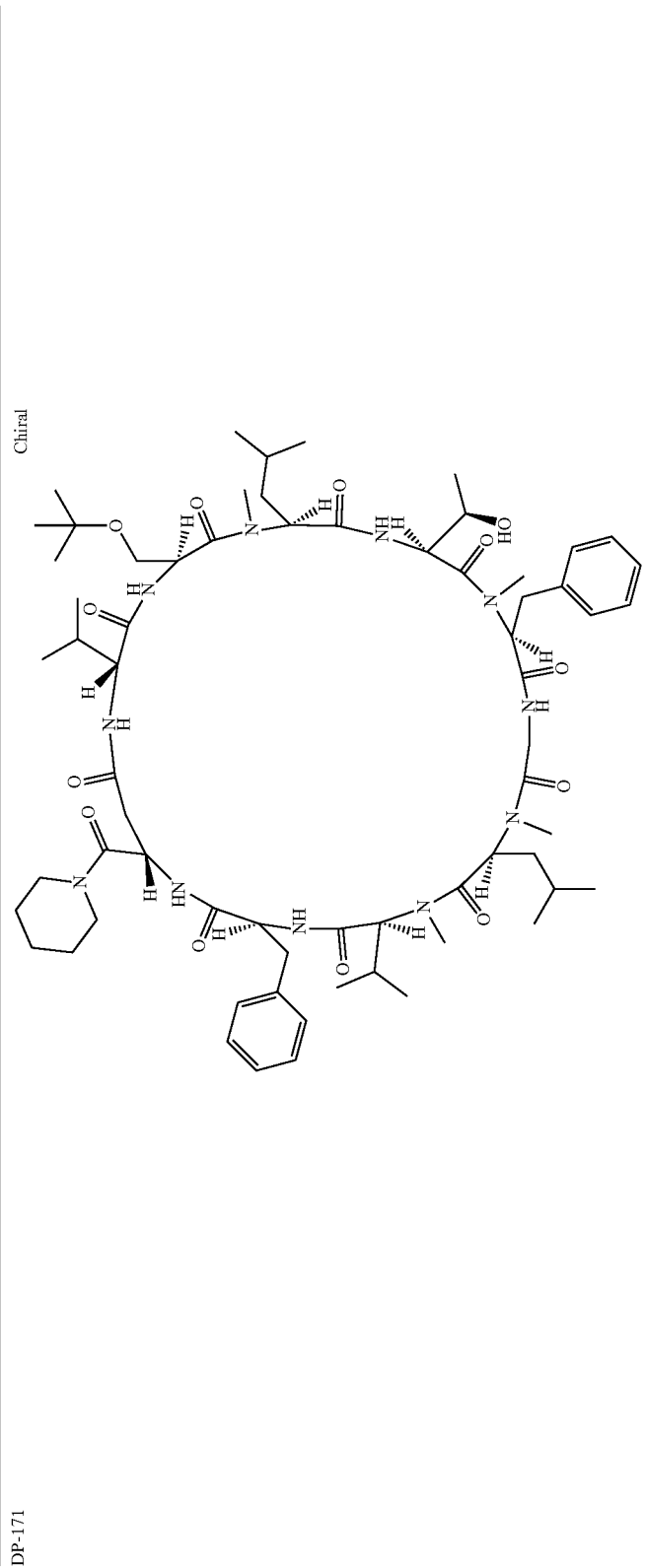
DP-171

TABLE 11-3-1-continued
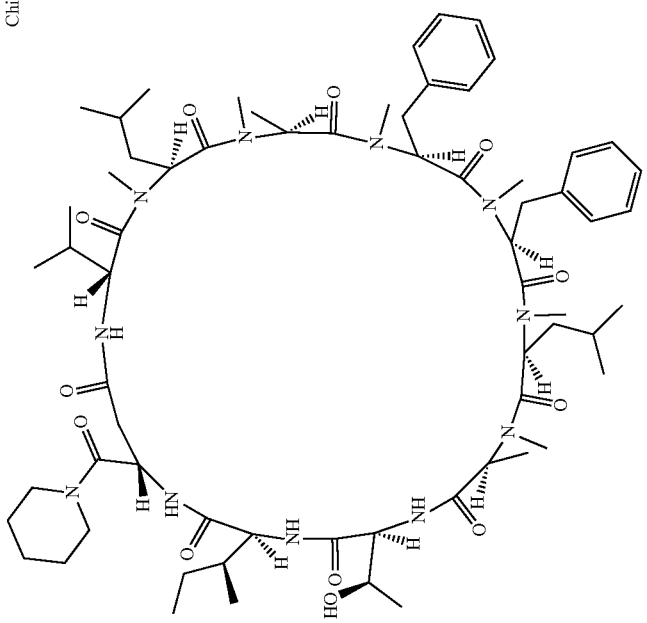
DP-172

TABLE 11-3-1-continued
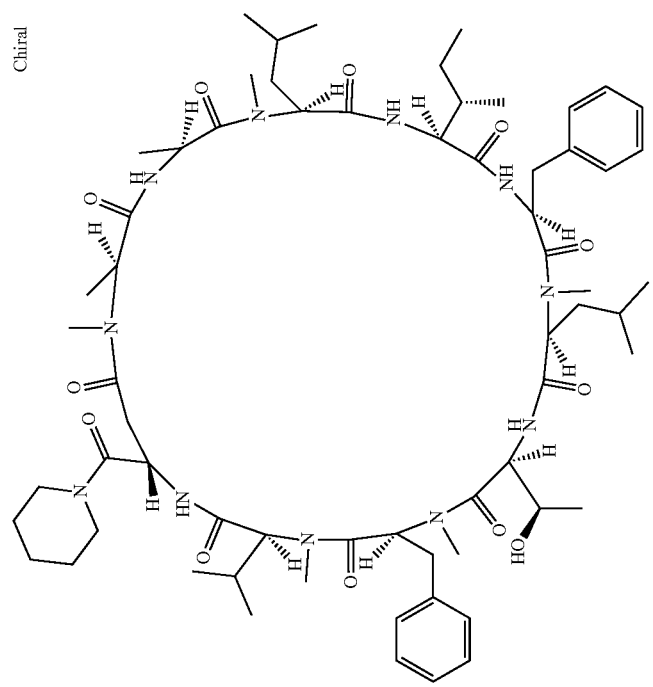
DP-173

TABLE 11-3-1-continued
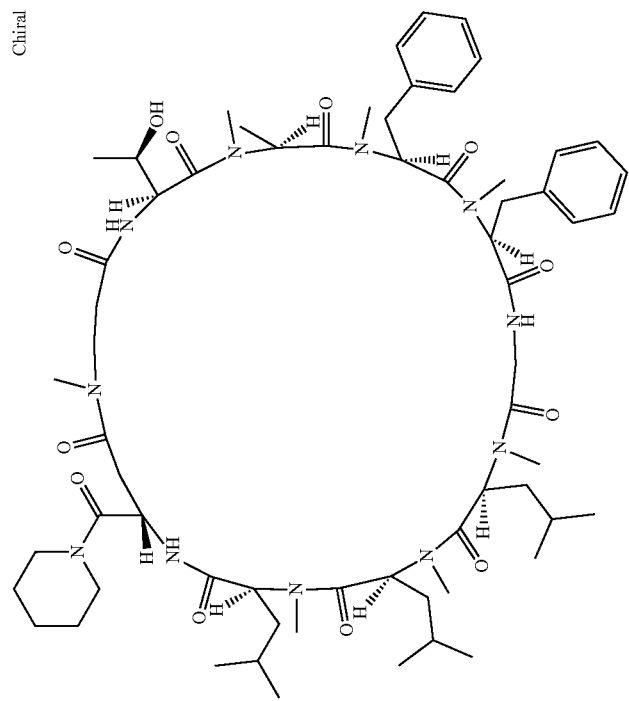
DP-174

TABLE 11-3-1-continued
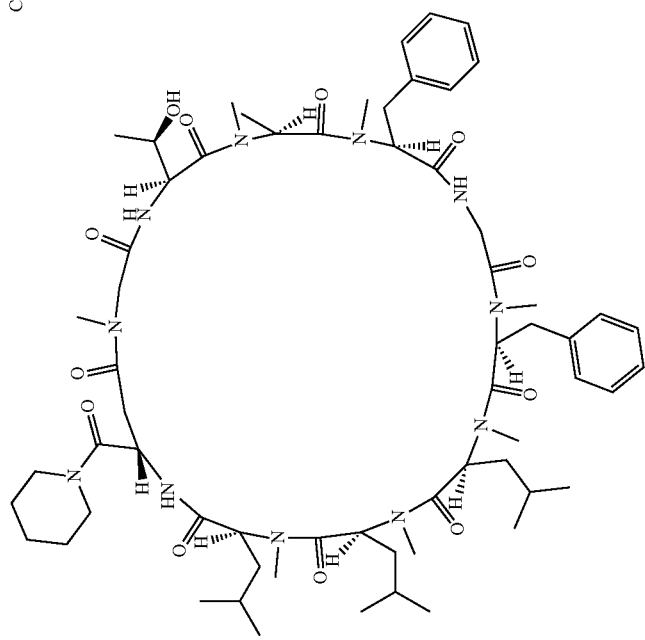
DP-175

TABLE 11-3-1-continued
DP-176
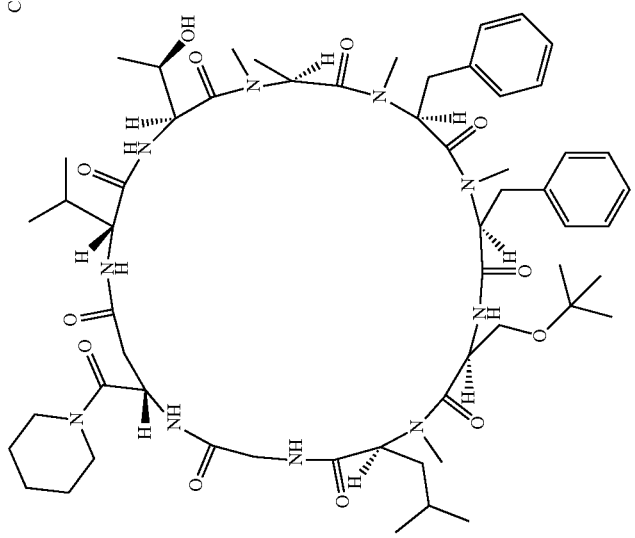

TABLE 11-3-1-continued
DP-177
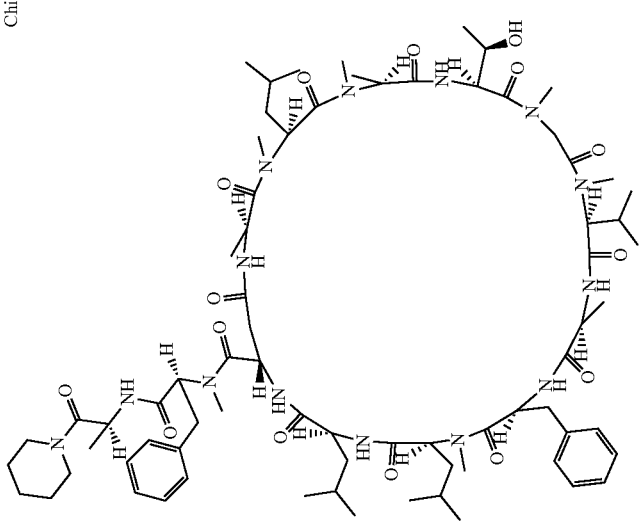

TABLE 11-3-1-continued
DP-178
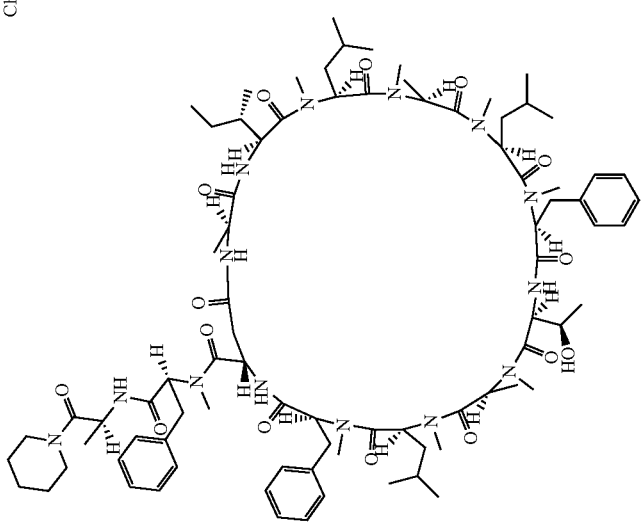

TABLE 11-3-1-continued
DP-179
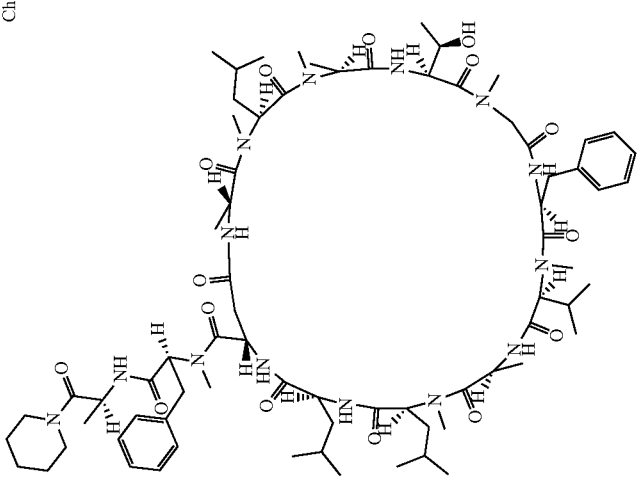

TABLE 11-3-1-continued
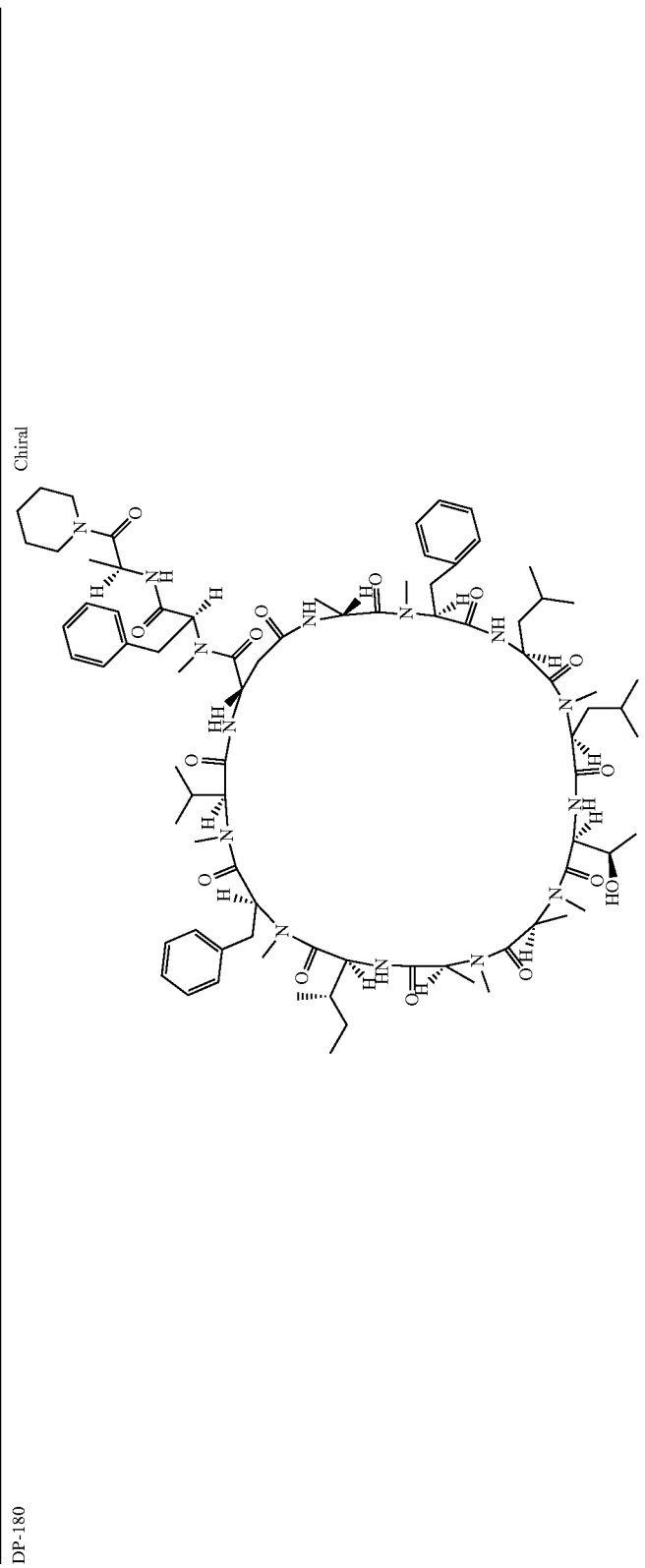
DP-180

TABLE 11-3-1-continued
| | |
|---|---|
| DP-181 | 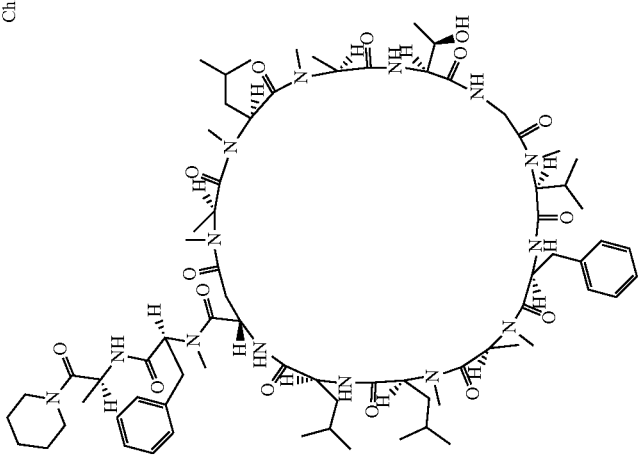 Chiral |

TABLE 11-3-1-continued
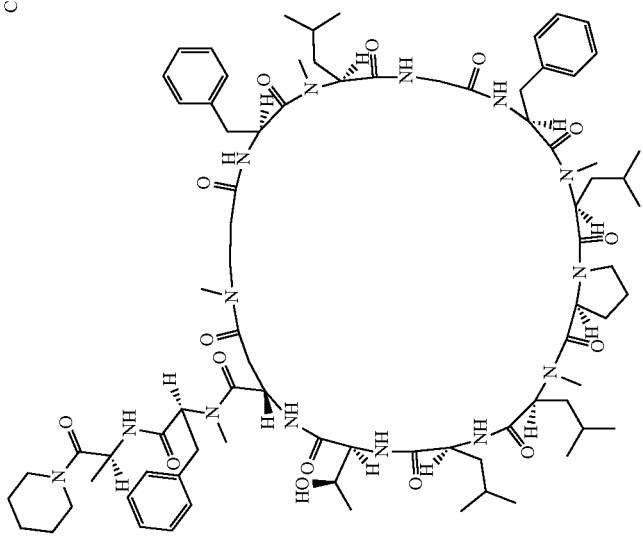
DP-182

TABLE 11-3-1-continued
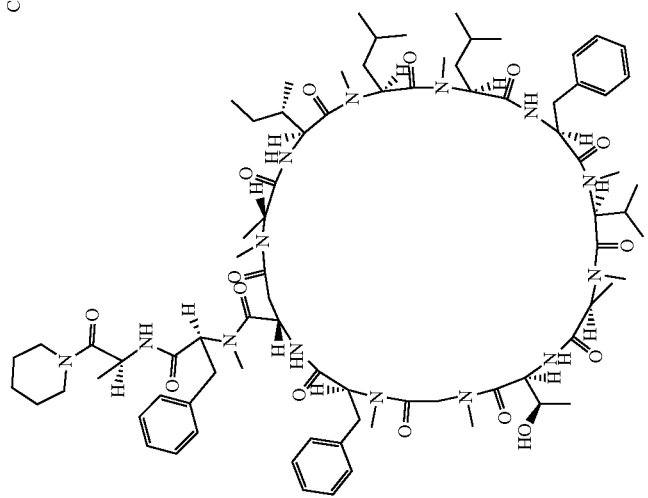
DP-183

TABLE 11-3-1-continued
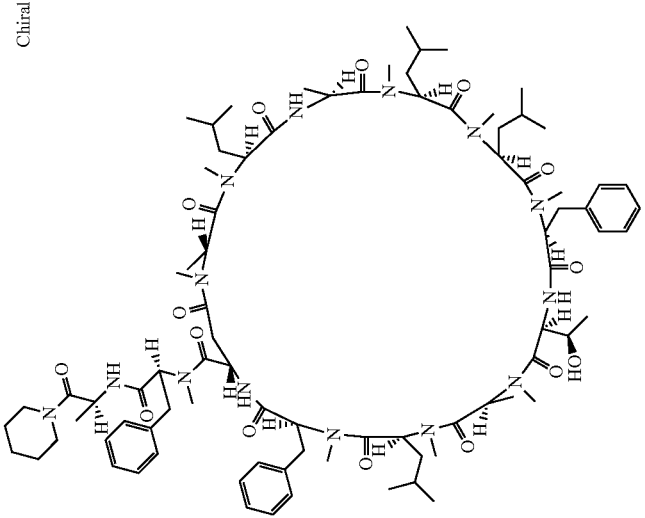
DP-184

TABLE 11-3-1-continued
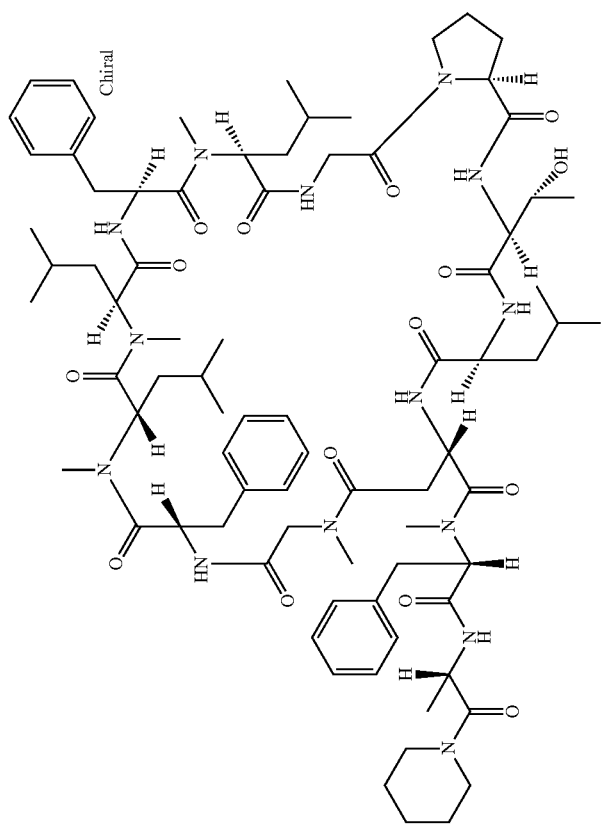
DP-185

TABLE 11-3-1-continued
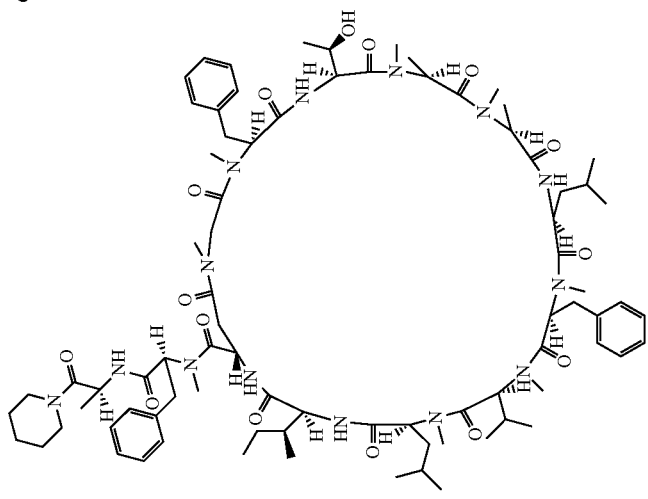
DP-186

TABLE 11-3-1-continued
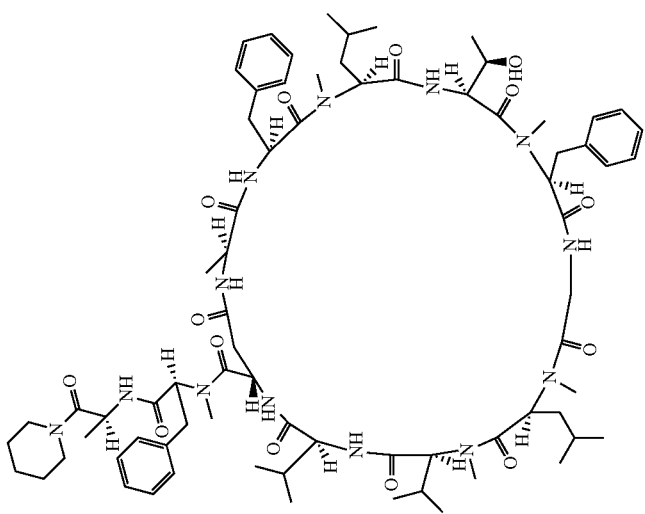
Chiral
DP-187

TABLE 11-3-1-continued
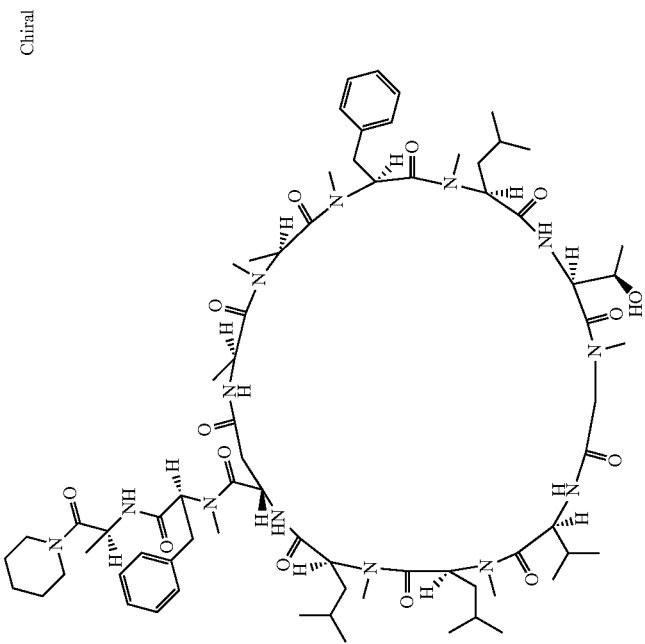
DP-188

TABLE 11-3-1-continued
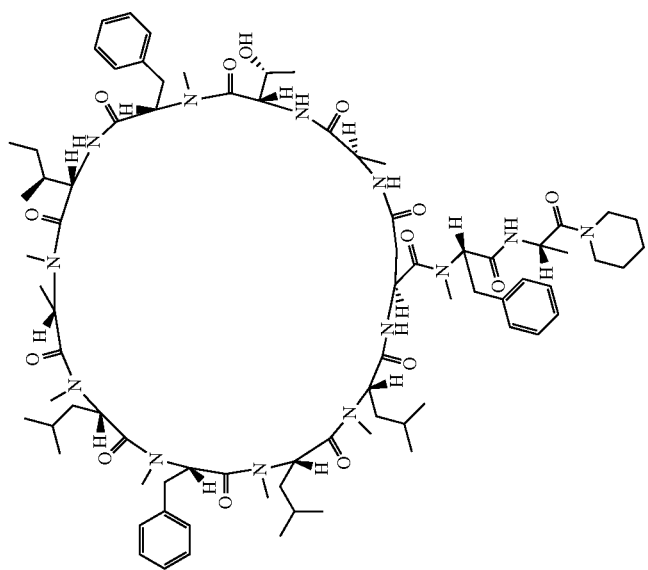
DP-189

TABLE 11-3-1-continued
DP-190
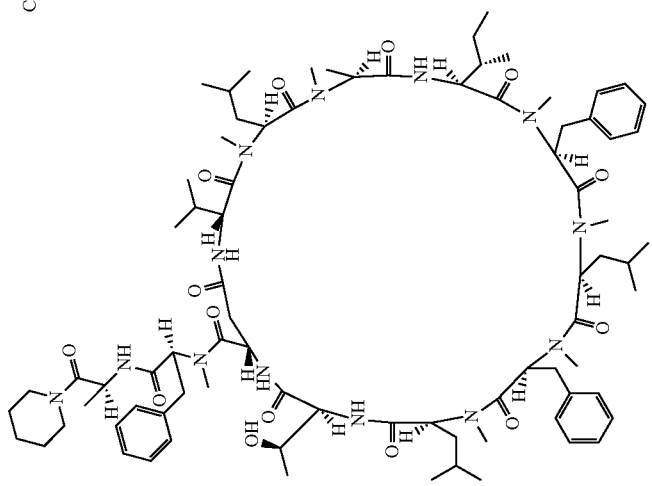
Chiral

TABLE 11-3-1-continued
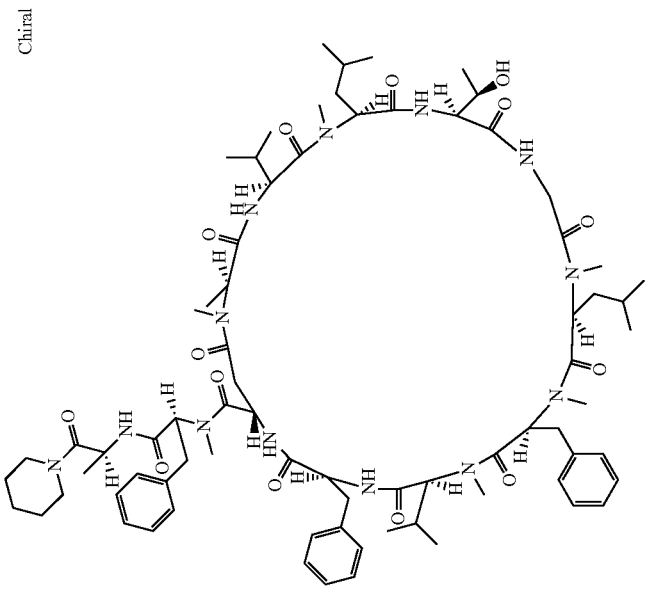
Chiral
DP-191

TABLE 11-3-1-continued
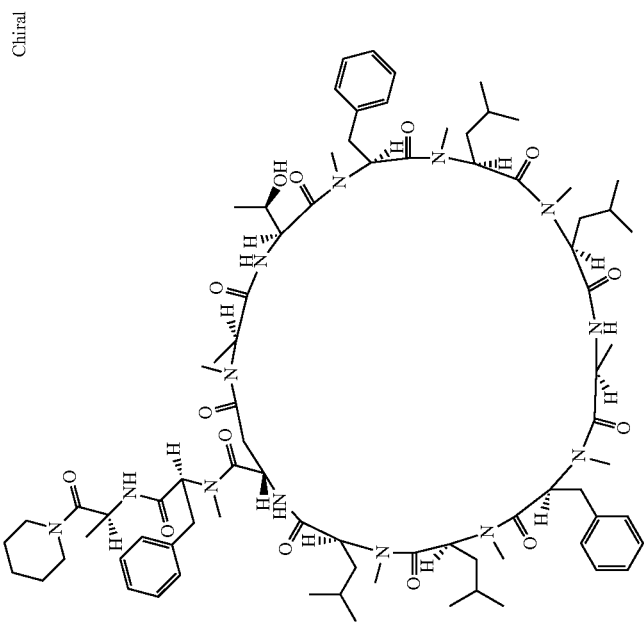
DP-192

TABLE 11-3-1-continued
DP-193
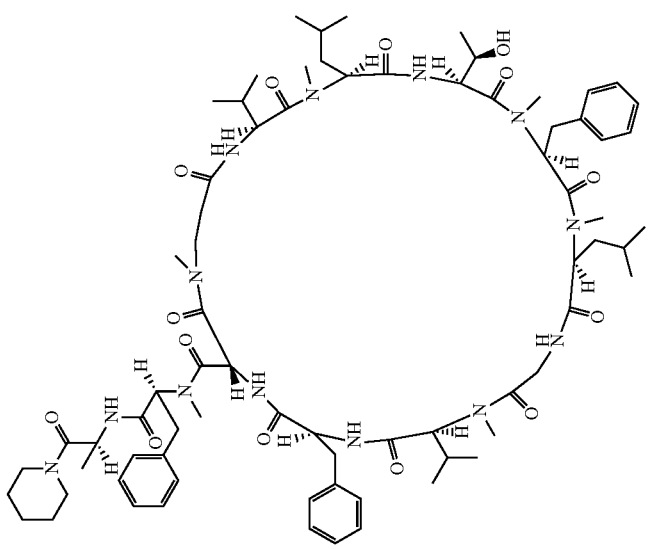

TABLE 11-3-1-continued
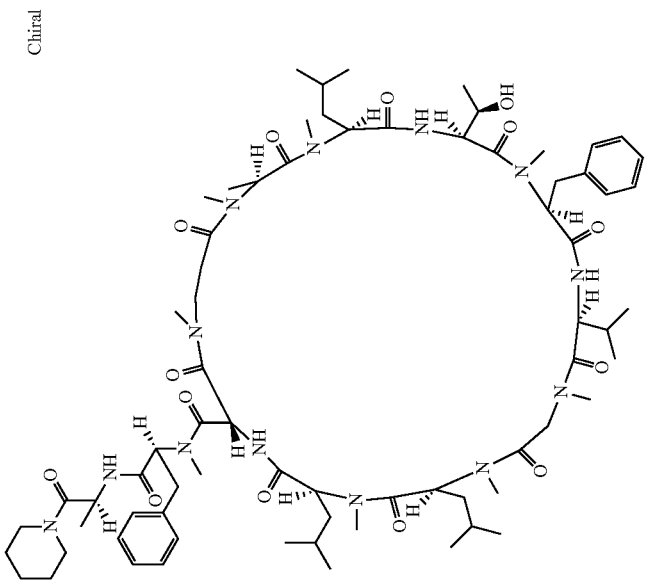
DP-194

TABLE 11-3-1-continued
Chiral
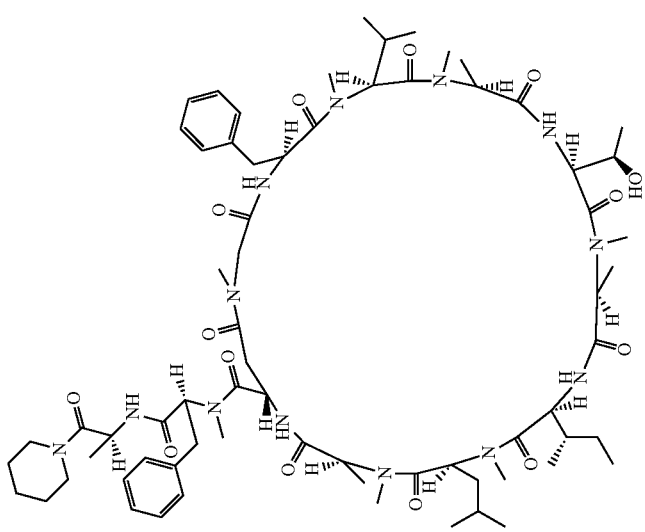
DP-195

TABLE 11-3-1-continued
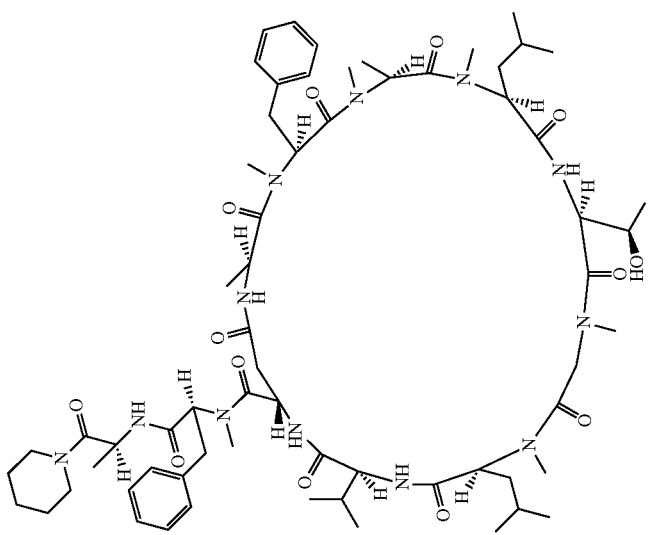
DP-196

TABLE 11-3-1-continued
DP-197
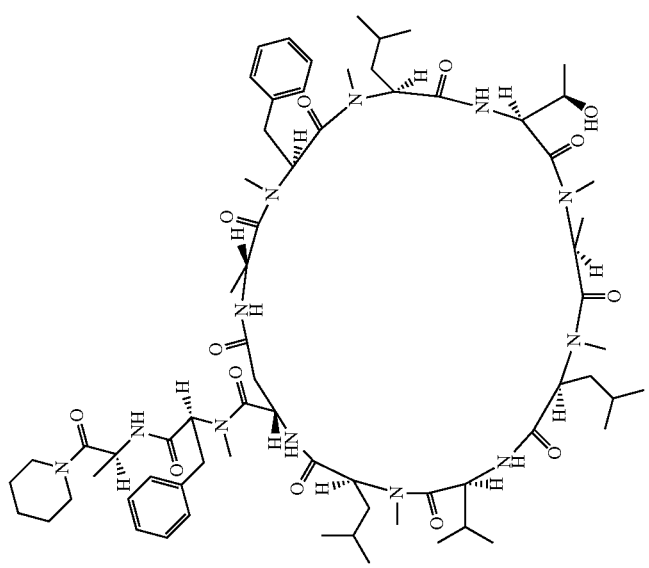
Chiral

TABLE 11-3-1-continued
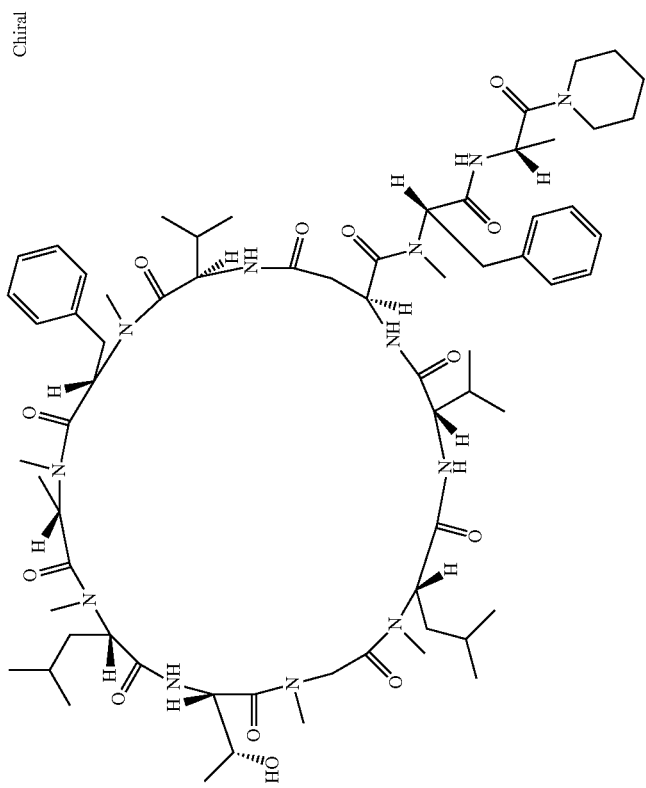
DP-198

TABLE 11-3-1-continued
Chiral
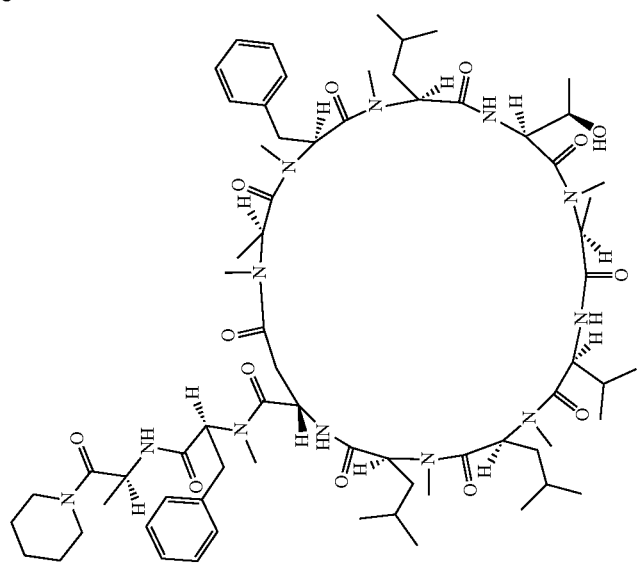
DP-199

TABLE 11-3-1-continued
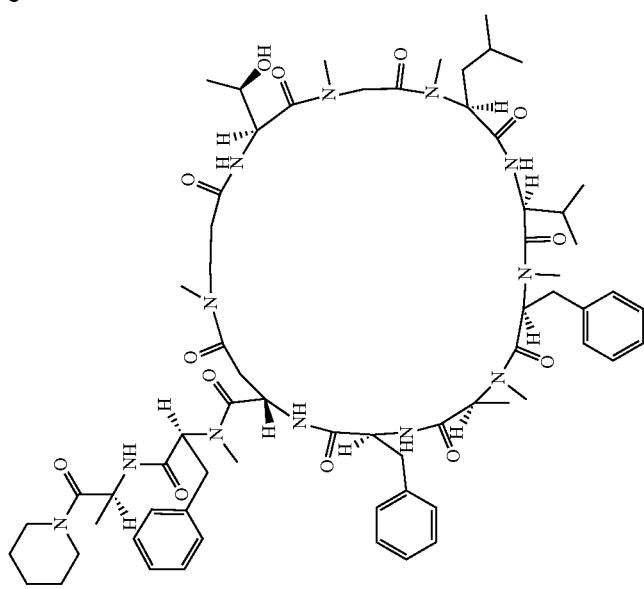
DP-200

TABLE 11-3-1-continued
Chiral
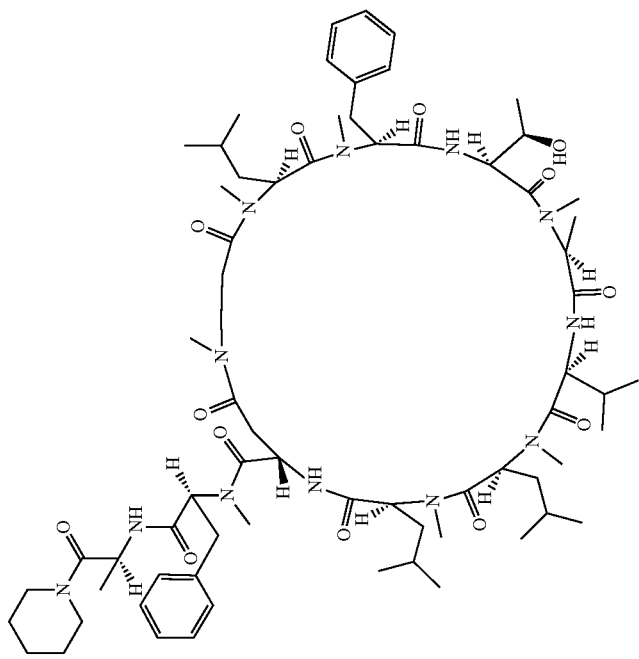
DP-201

TABLE 11-3-1-continued
Chiral
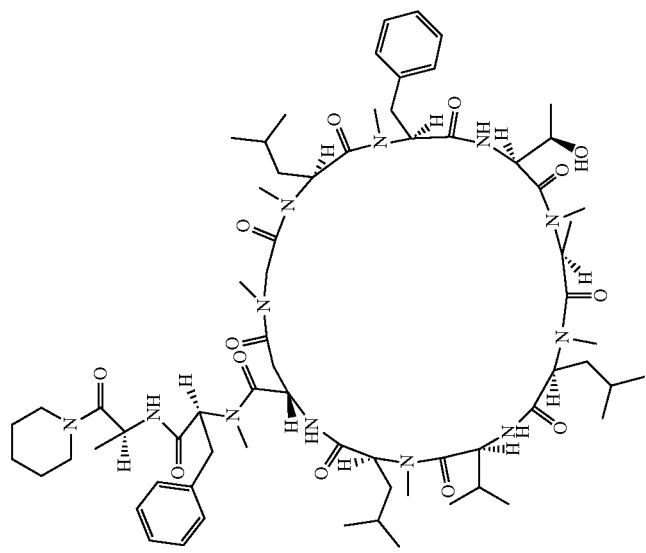
DP-202

TABLE 11-3-1-continued
Chiral
DP-203

TABLE 11-3-1-continued
Chiral
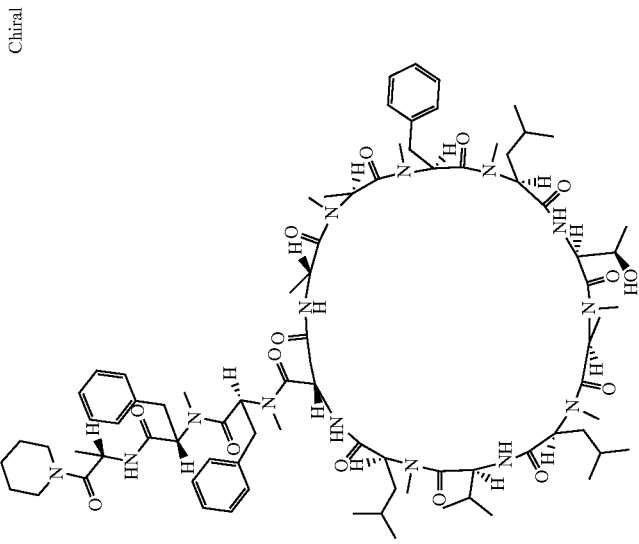
DP-204

TABLE 11-3-1-continued
Chiral
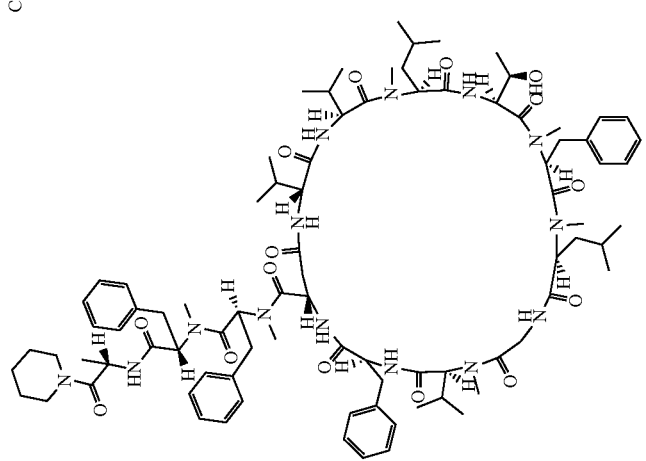
DP-205

TABLE 11-3-1-continued
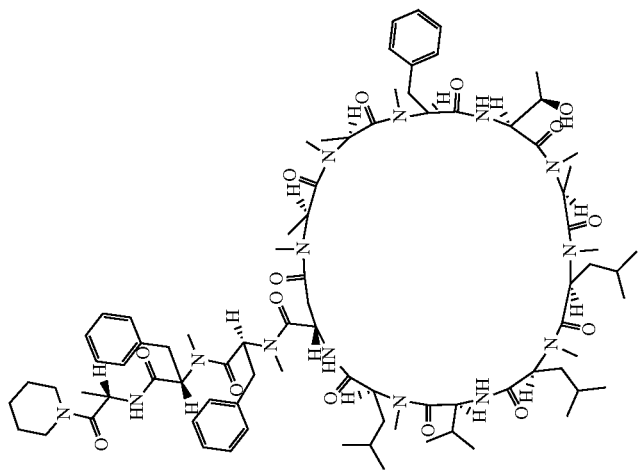
DP-206

TABLE 11-3-1-continued
DP-207
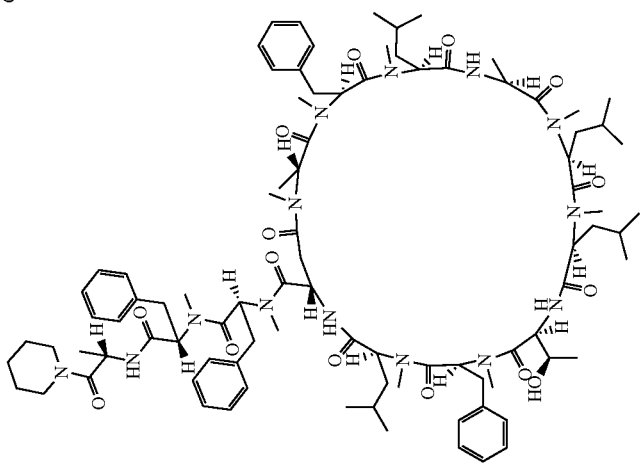
Chiral

TABLE 11-3-1-continued
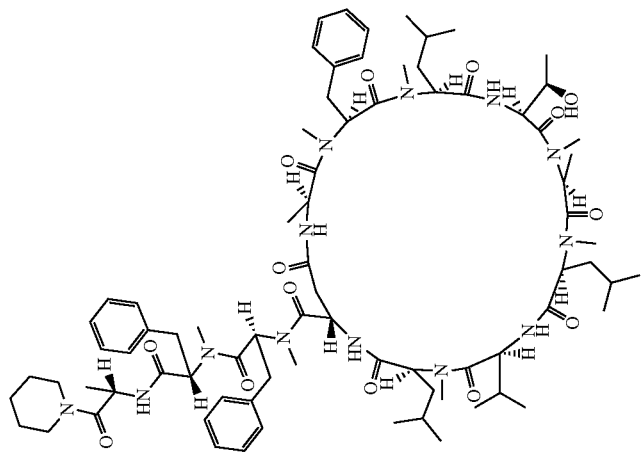
Chiral
DP-208

TABLE 11-3-1-continued
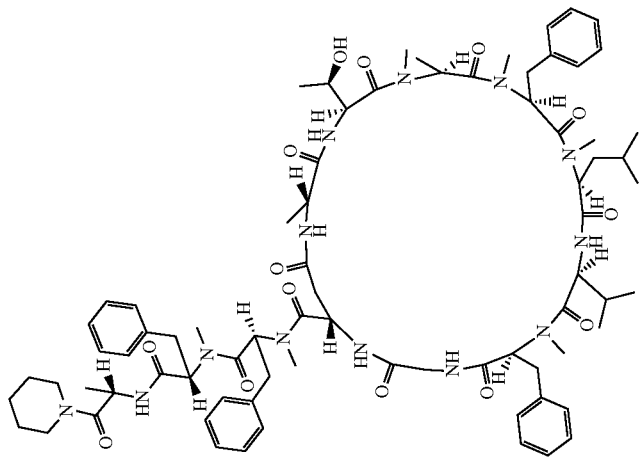
DP-209

TABLE 11-3-1-continued
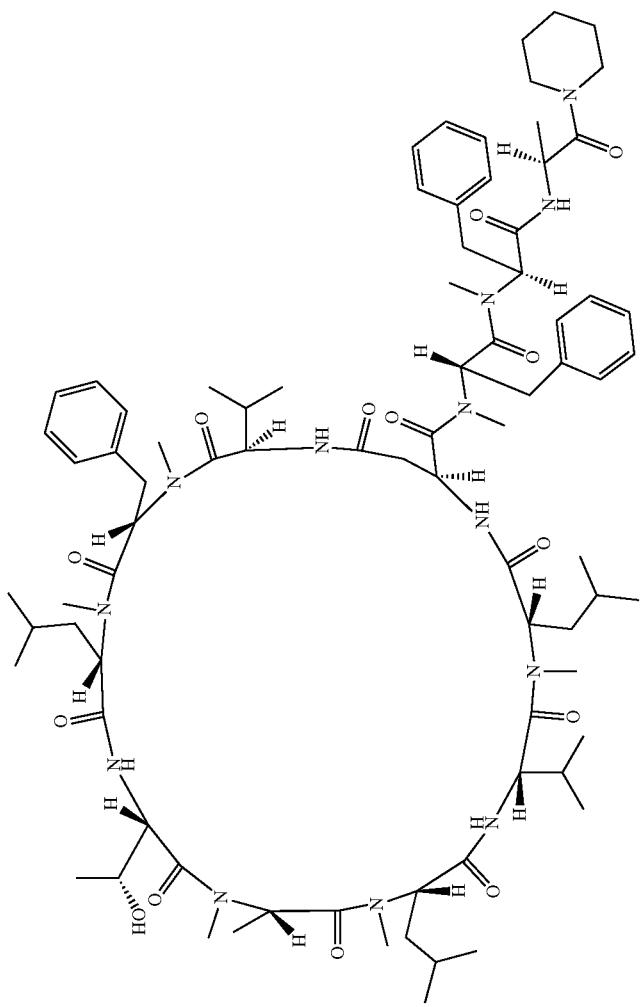
DP-210

TABLE 11-3-1-continued
DP-211
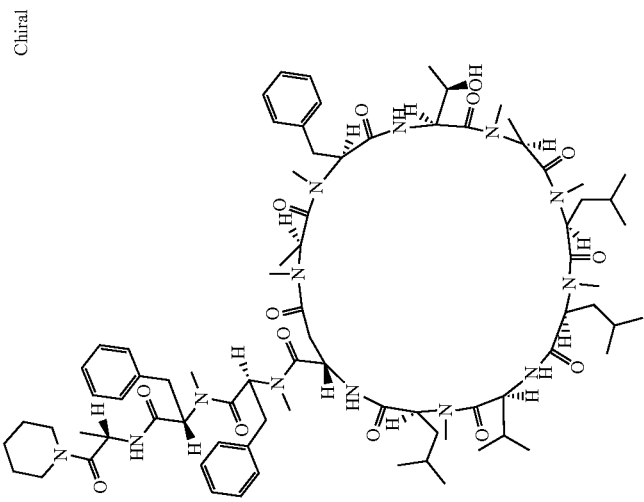

TABLE 11-3-1-continued
Chiral
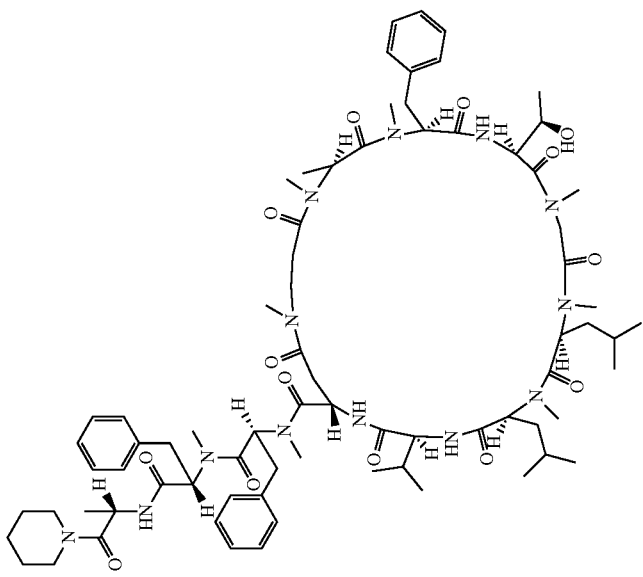
DP-212

TABLE 11-3-1-continued
Chiral
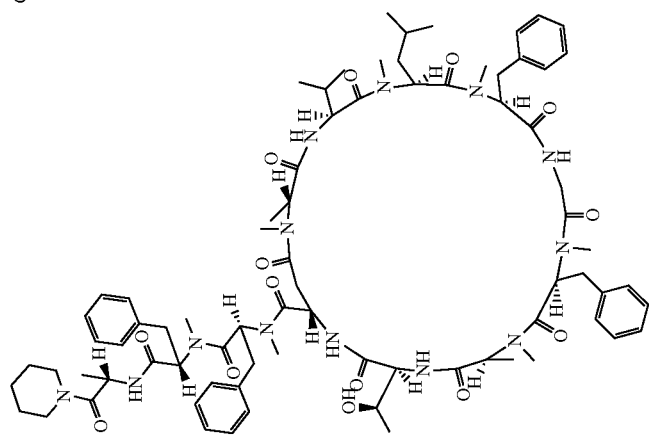
DP-213

TABLE 11-3-1-continued
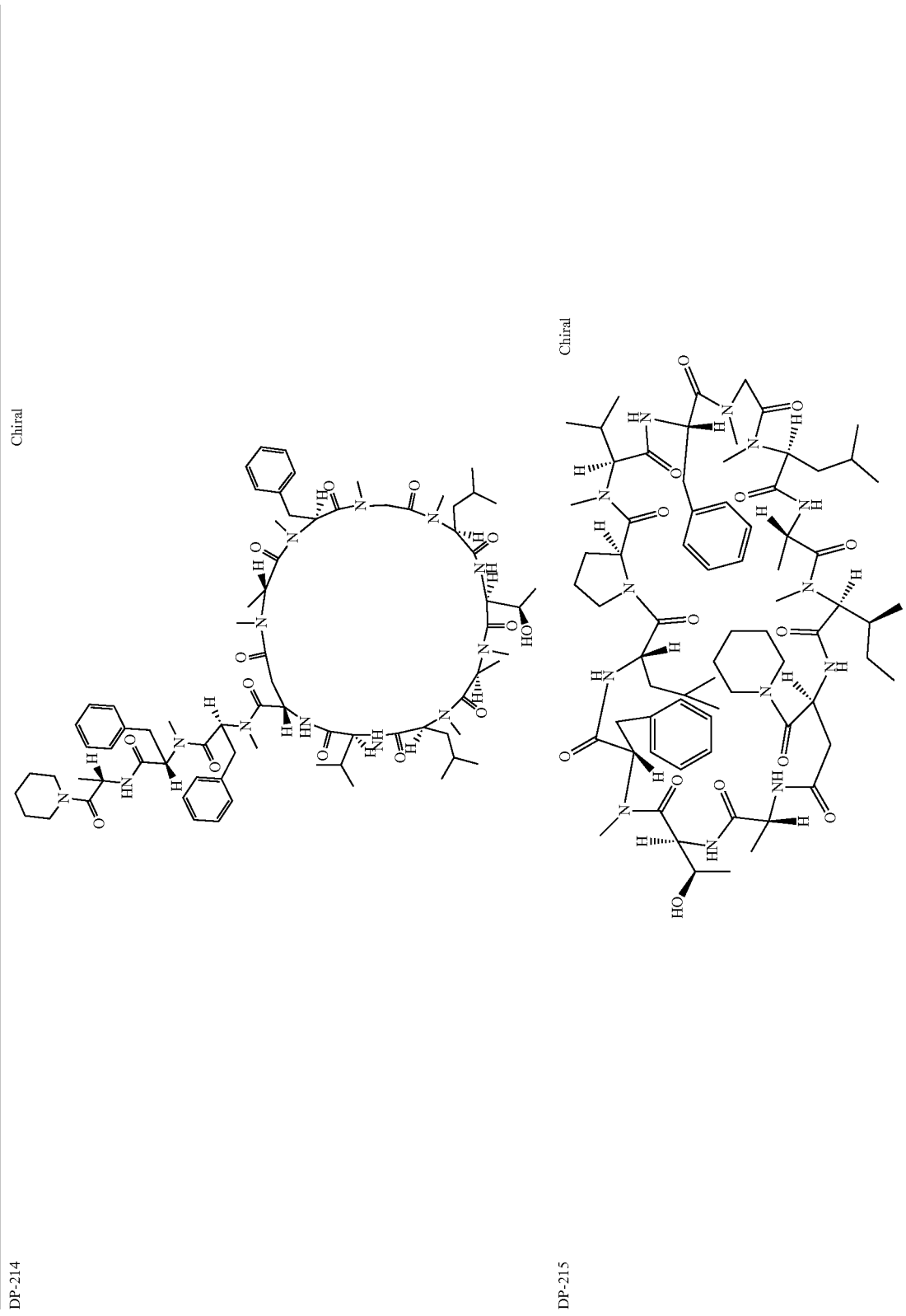
DP-214
DP-215

TABLE 11-3-1-continued
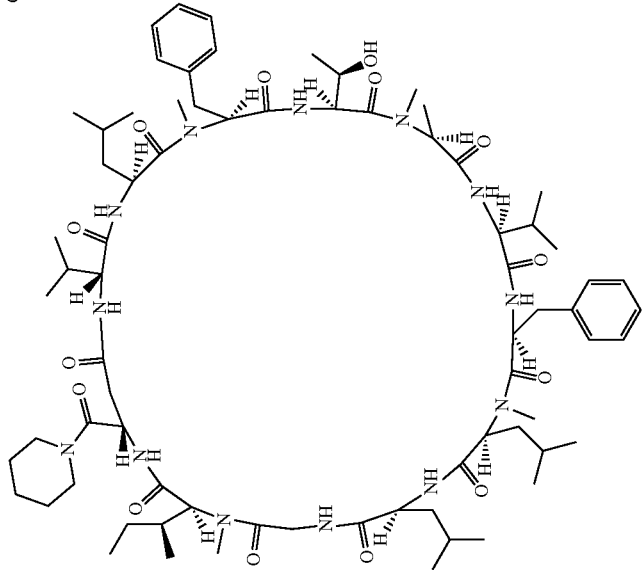
DP-216

TABLE 11-3-1-continued
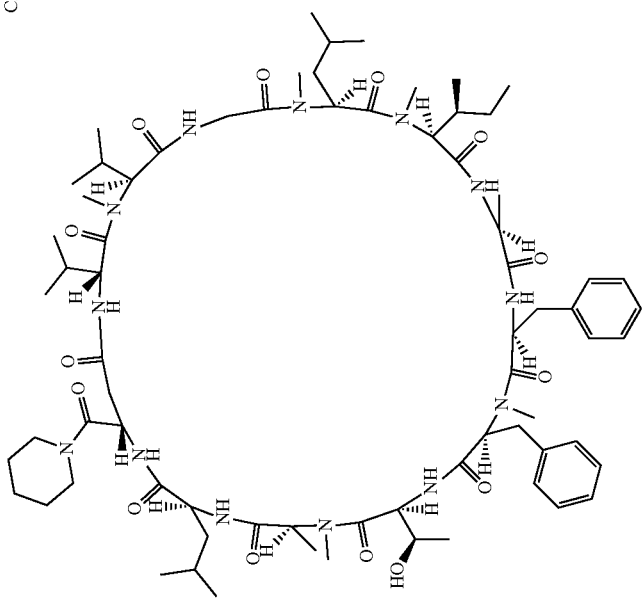
DP-217

TABLE 11-3-1-continued
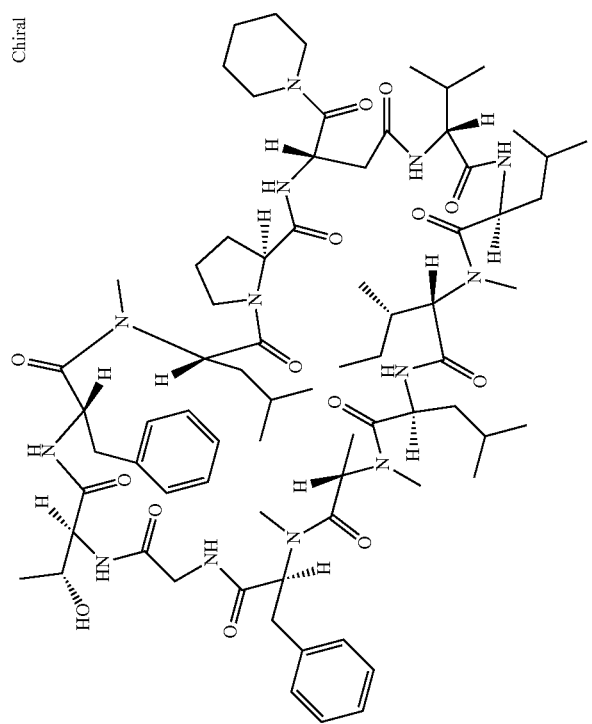
Chiral
DP-218

TABLE 11-3-1-continued
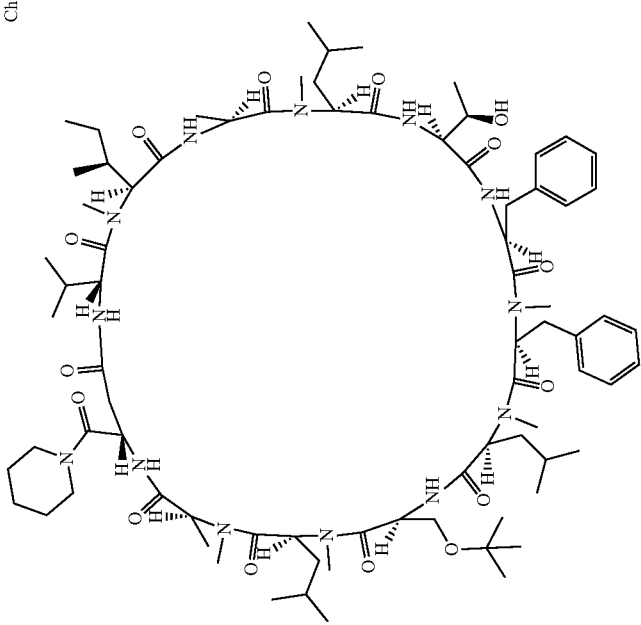
DP-219

TABLE 11-3-1-continued
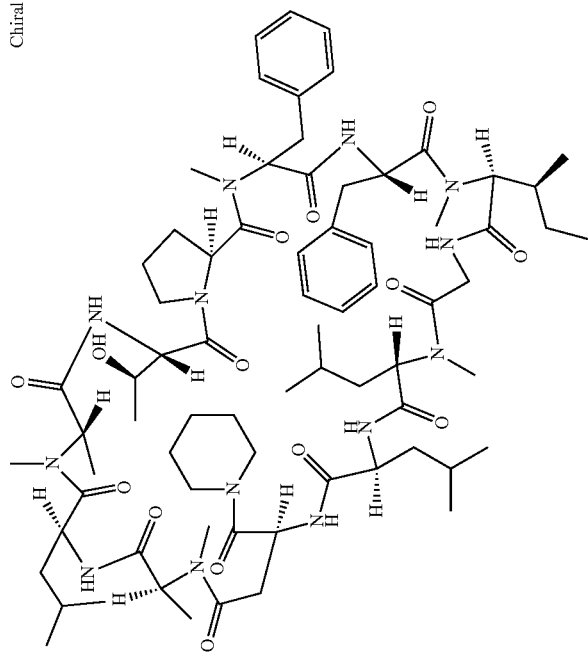
DP-220

TABLE 11-3-1-continued
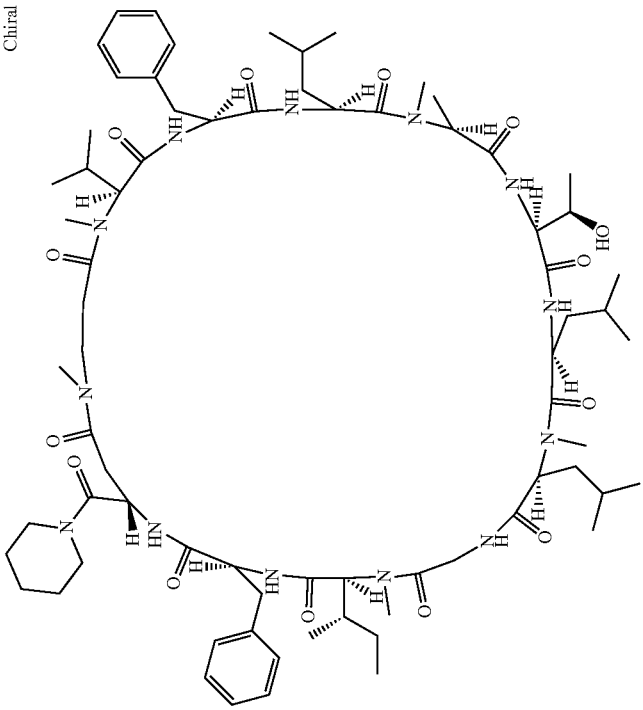
DP-221

TABLE 11-3-1-continued
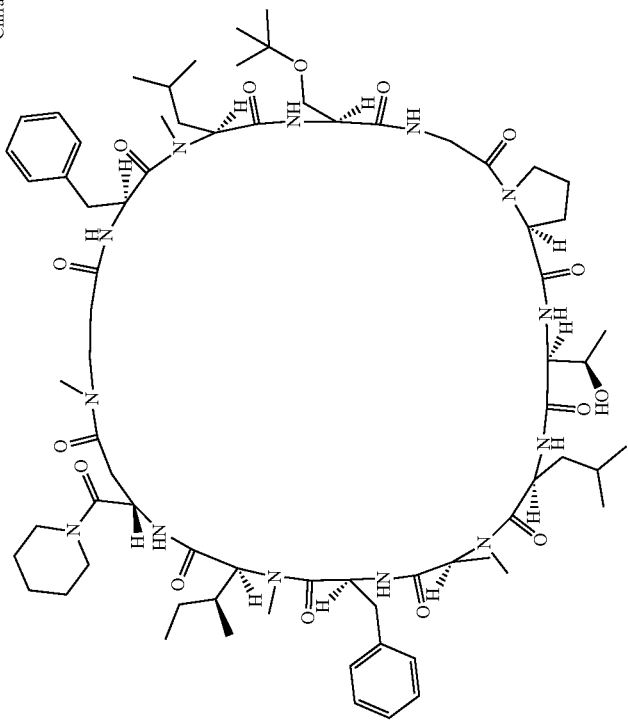
DP-222

TABLE 11-3-1-continued
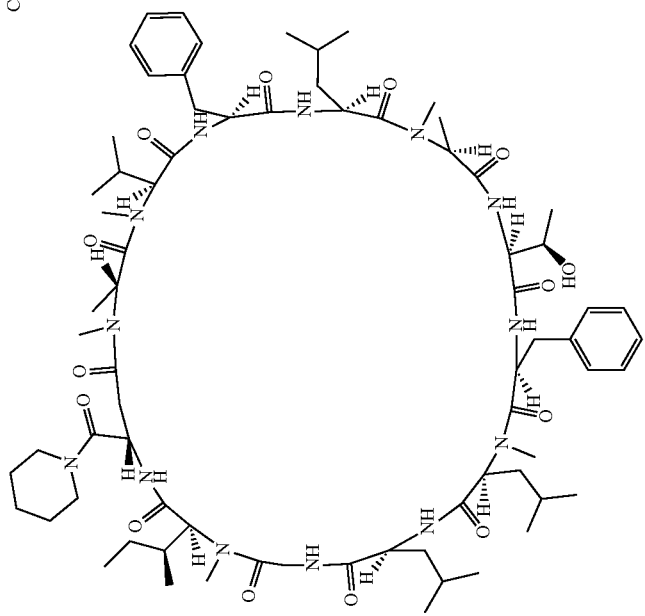
DP-223

TABLE 11-3-1-continued
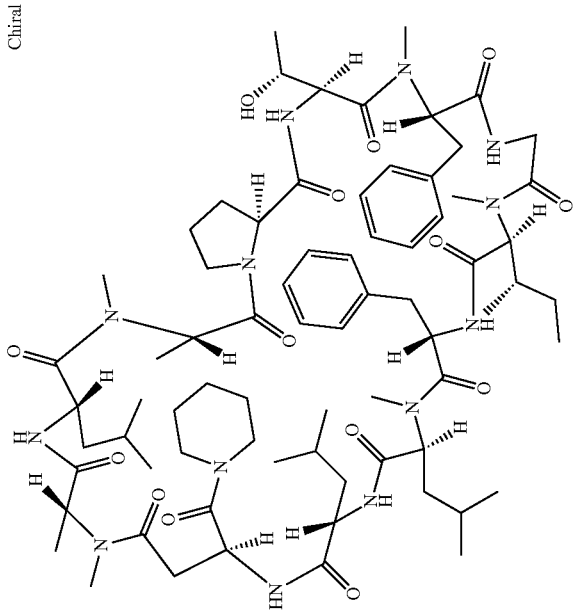
DP-224

TABLE 11-3-1-continued
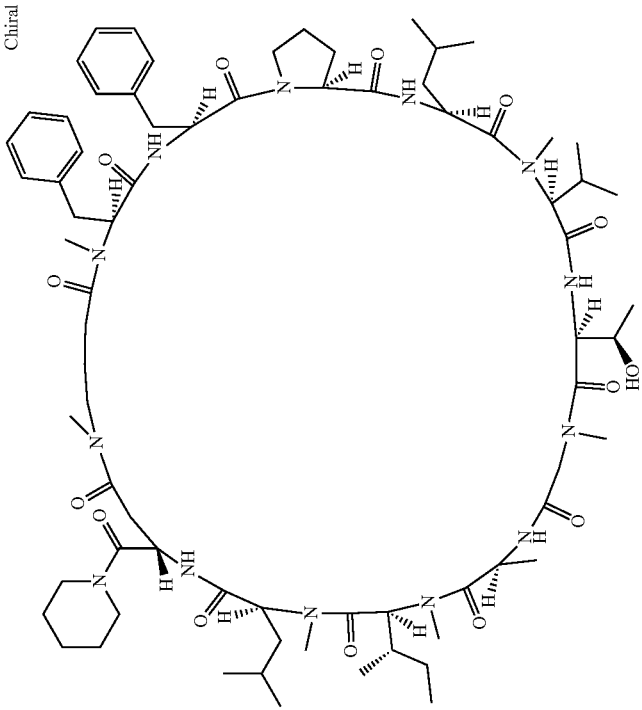
DP-225

TABLE 11-3-1-continued
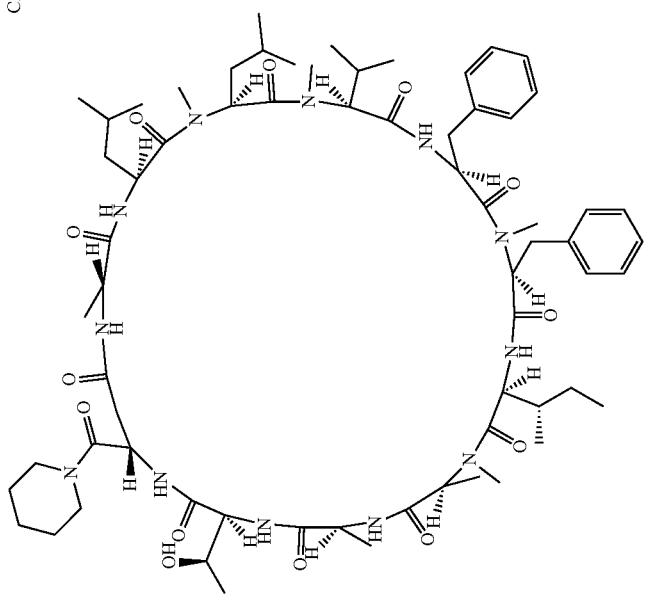
DP-226

TABLE 11-3-1-continued
DP-227
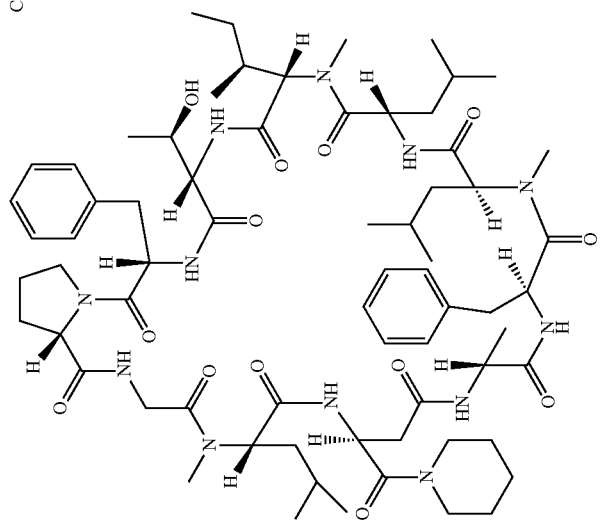

TABLE 11-3-1-continued
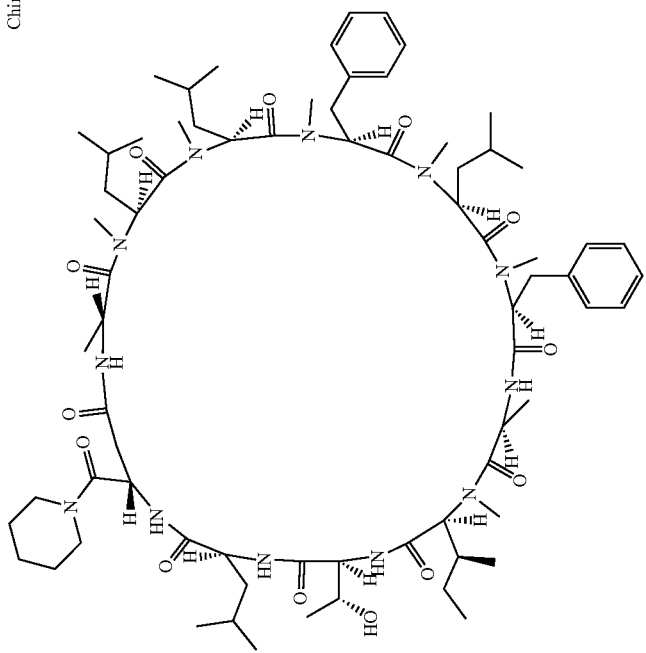
DP-228

TABLE 11-3-1-continued
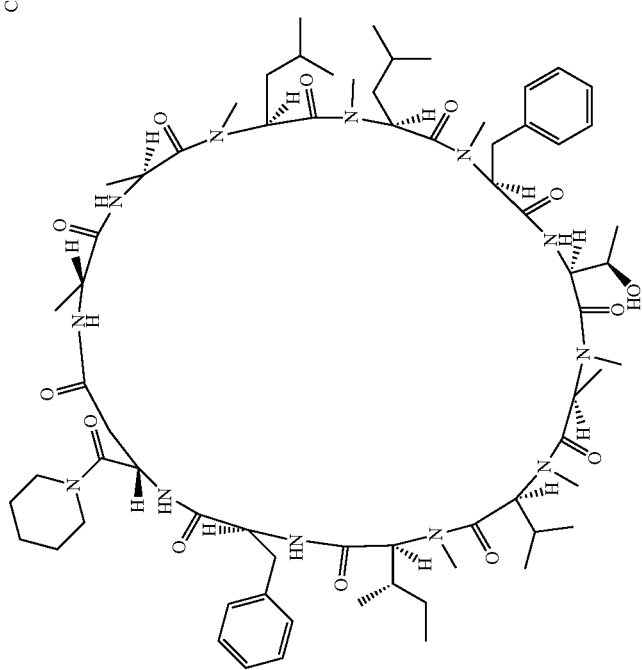
DP-229

TABLE 11-3-1-continued
DP-230
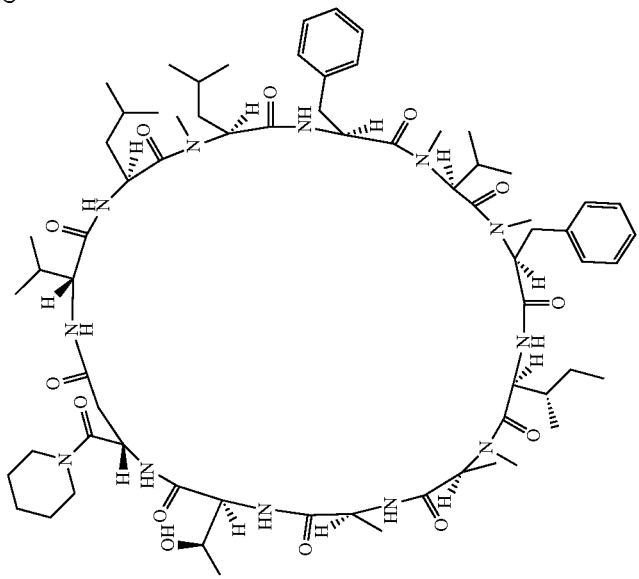

TABLE 11-3-1-continued
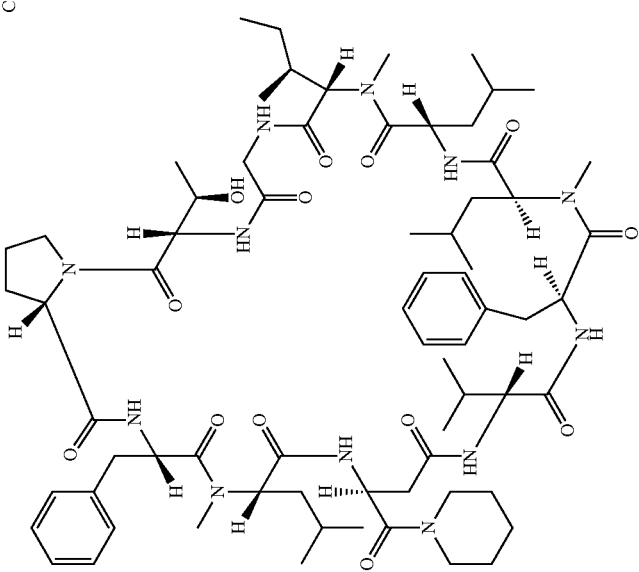
DP-231

TABLE 11-3-1-continued
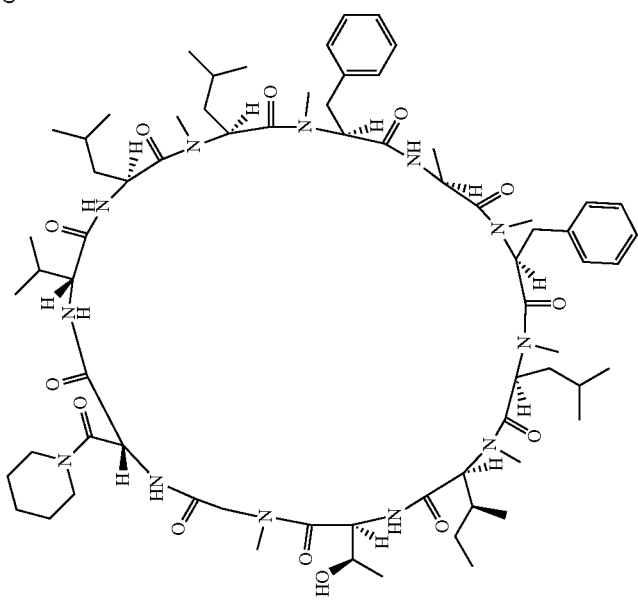
DP-232

TABLE 11-3-1-continued
DP-233
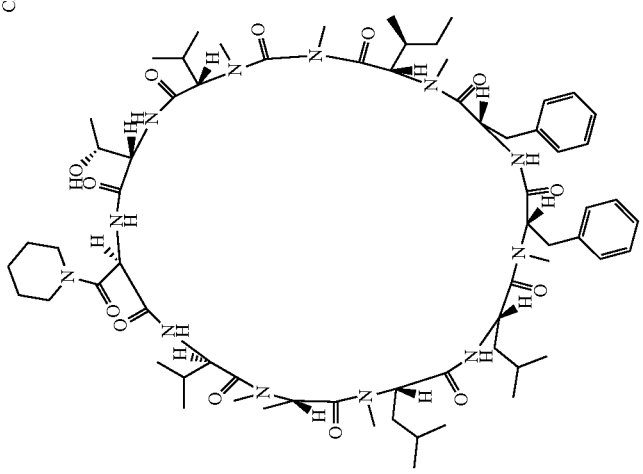

TABLE 11-3-1-continued
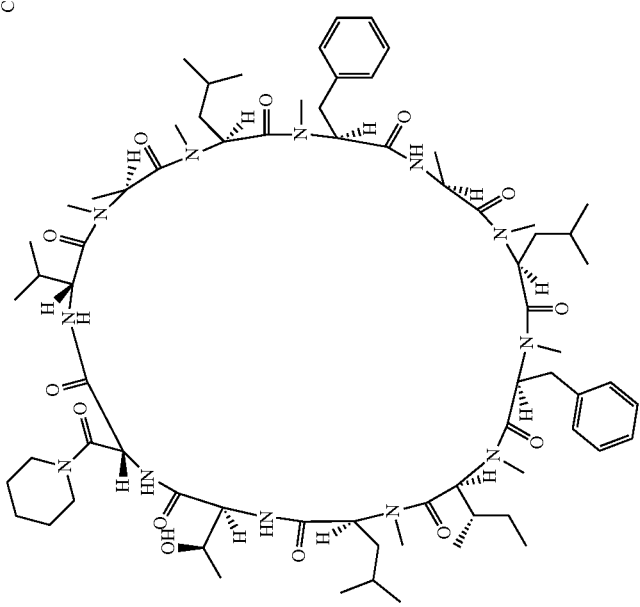
DP-234

TABLE 11-3-1-continued
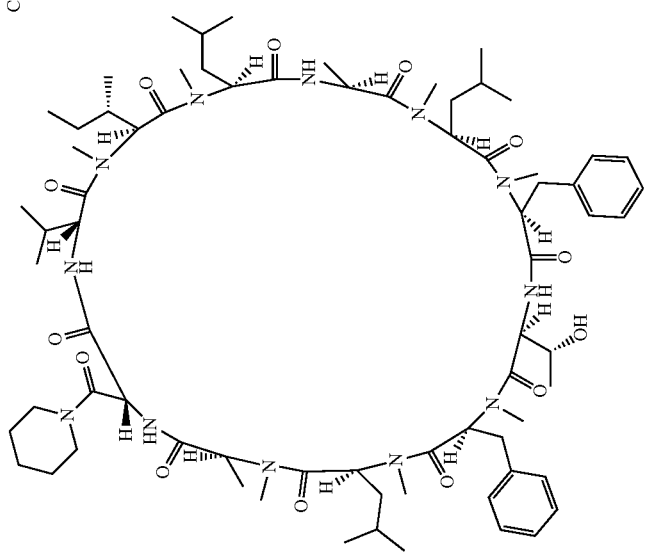
DP-235

TABLE 11-3-1-continued
Chiral
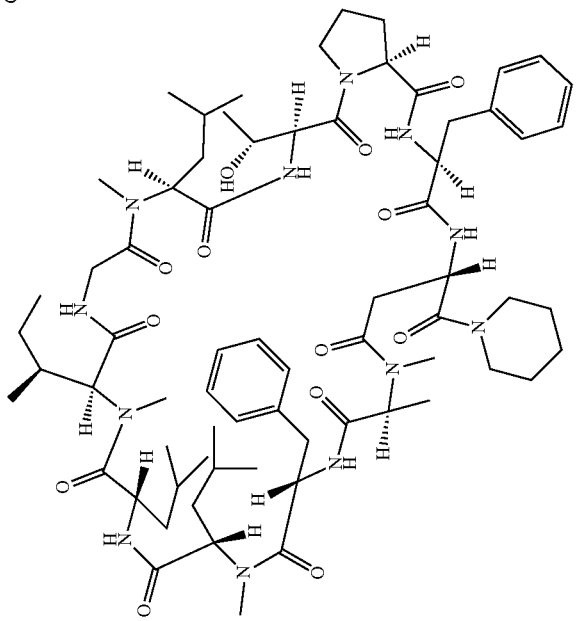
DP-236

TABLE 11-3-1-continued
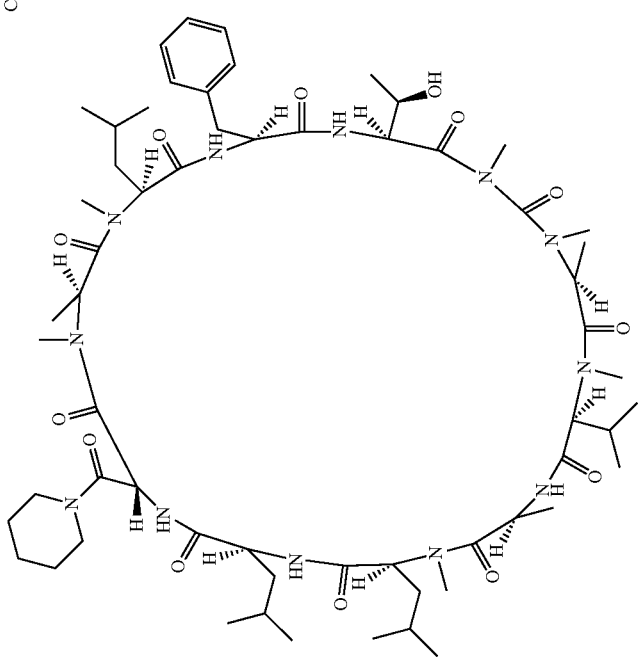
DP-237

TABLE 11-3-1-continued
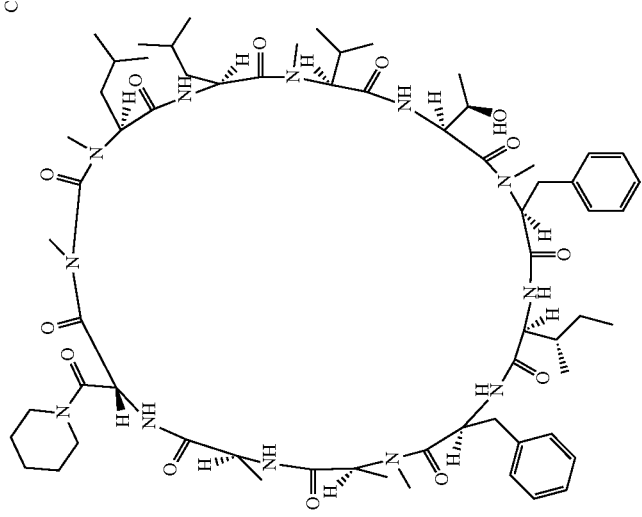
DP-238

TABLE 11-3-1-continued
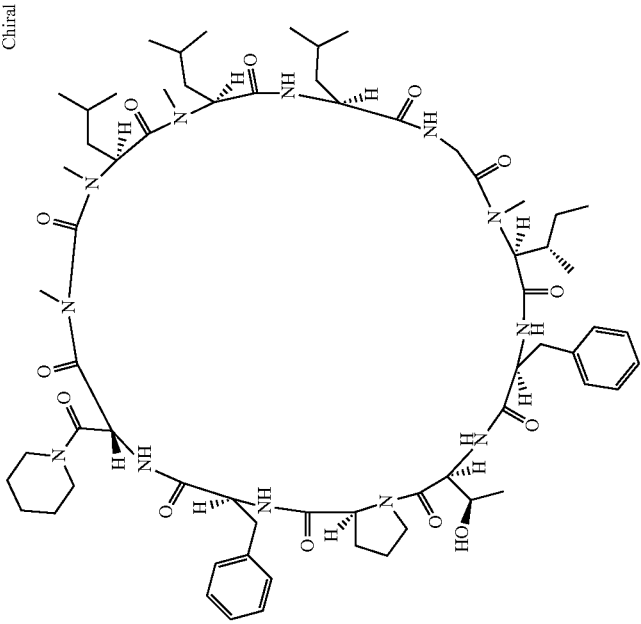
DP-239

TABLE 11-3-1-continued
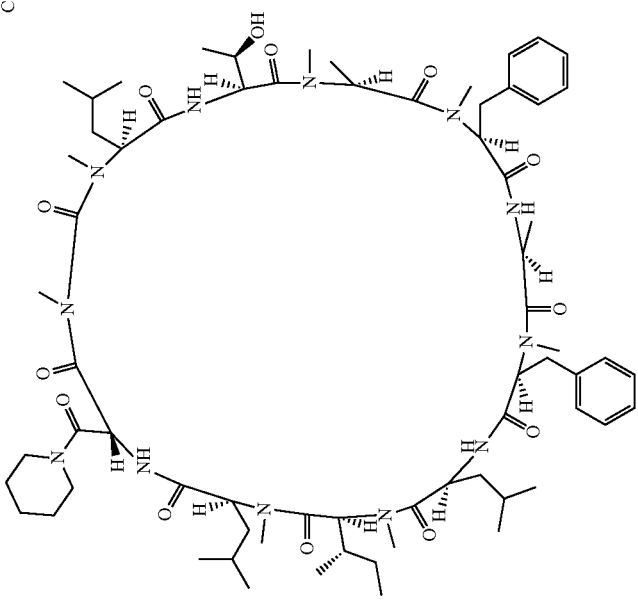
DP-240

TABLE 11-3-1-continued
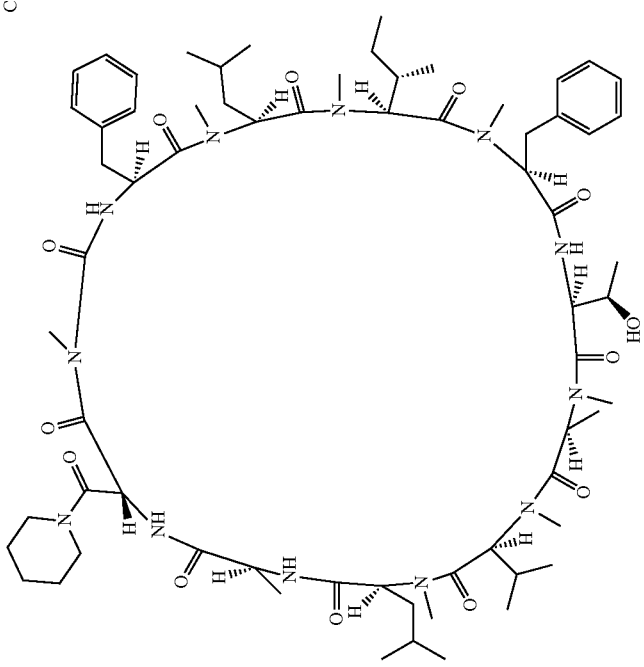
DP-241

TABLE 11-3-1-continued
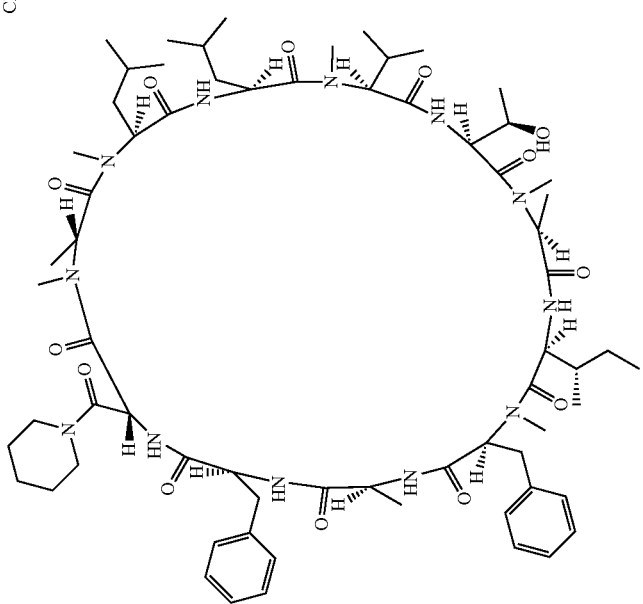
DP-242

TABLE 11-3-1-continued
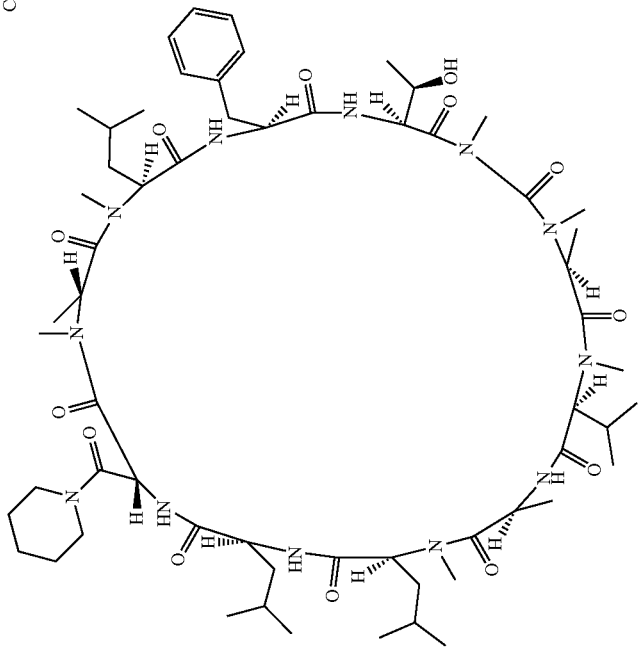
DP-243

TABLE 11-3-1-continued
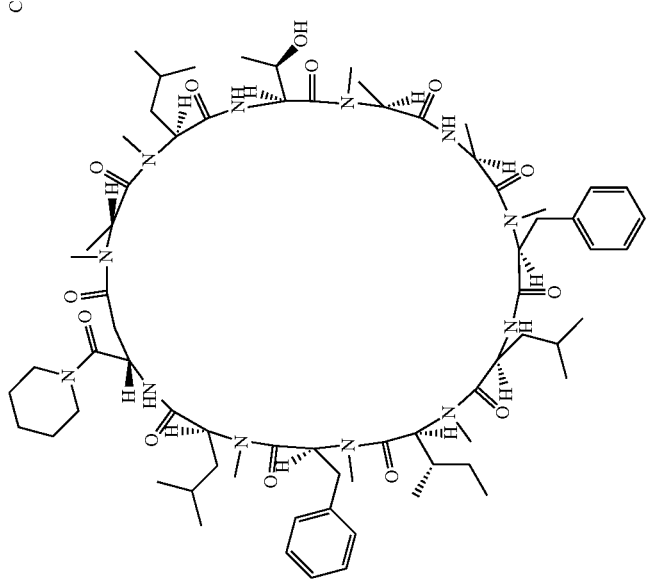
DP-244

TABLE 11-3-1-continued
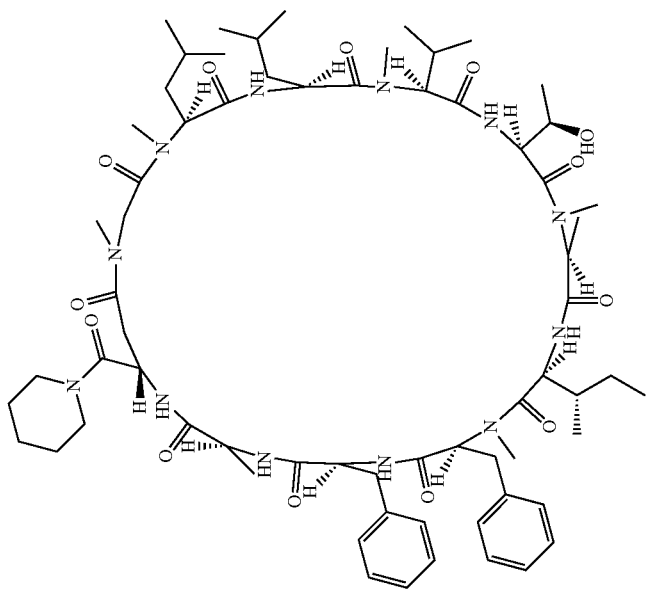
DP-245

TABLE 11-3-1-continued
| | Chiral |
|---|---|
| DP-246 | 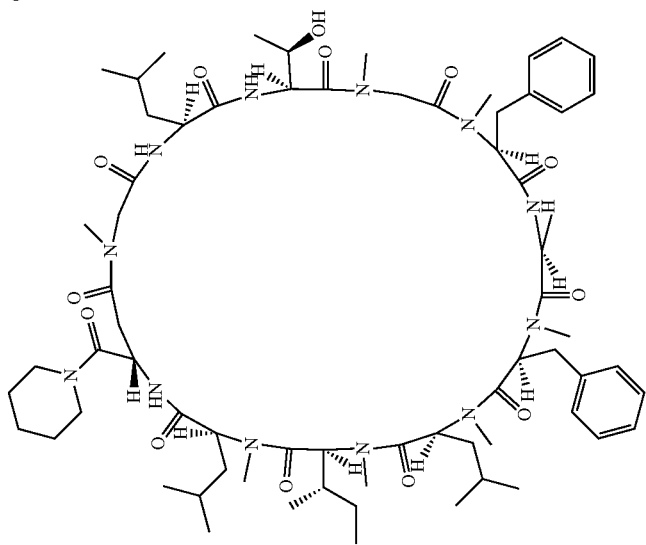 |

TABLE 11-3-1-continued
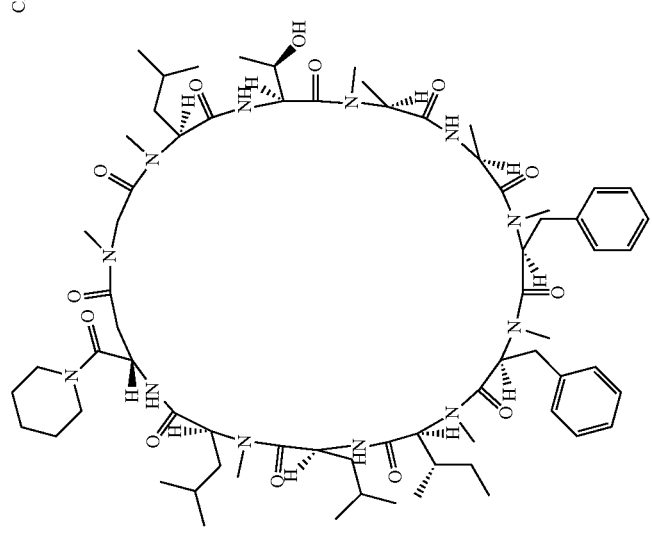
DP-247

TABLE 11-3-1-continued
DP-248
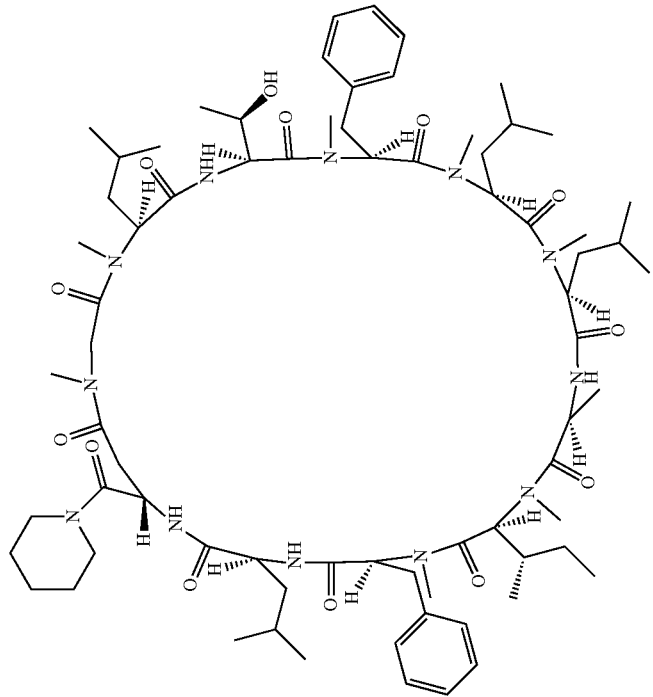
Chiral

TABLE 11-3-1-continued
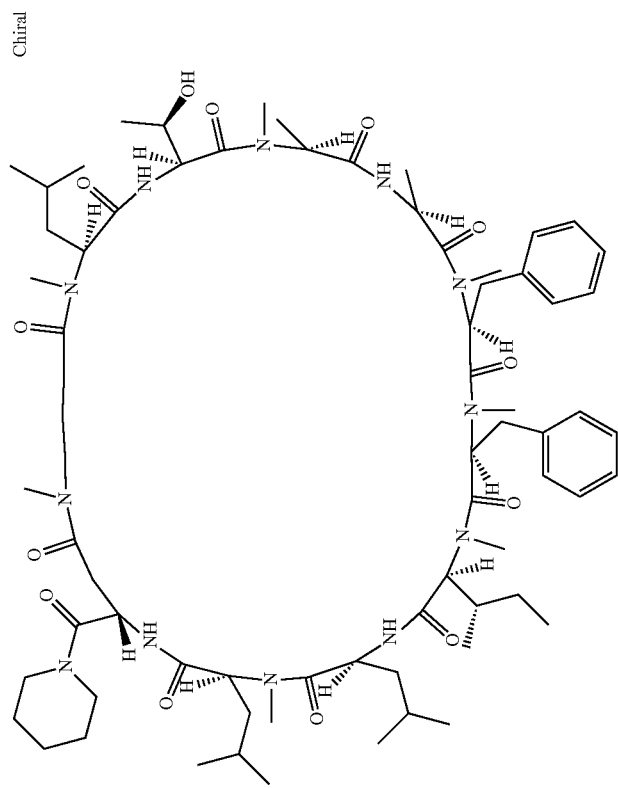
DP-249

TABLE 11-3-1-continued
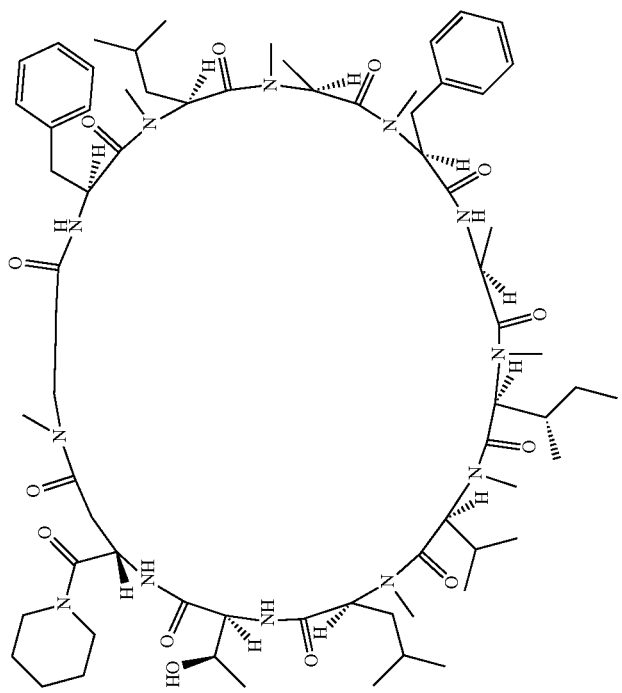
DP-250

TABLE 11-3-1-continued
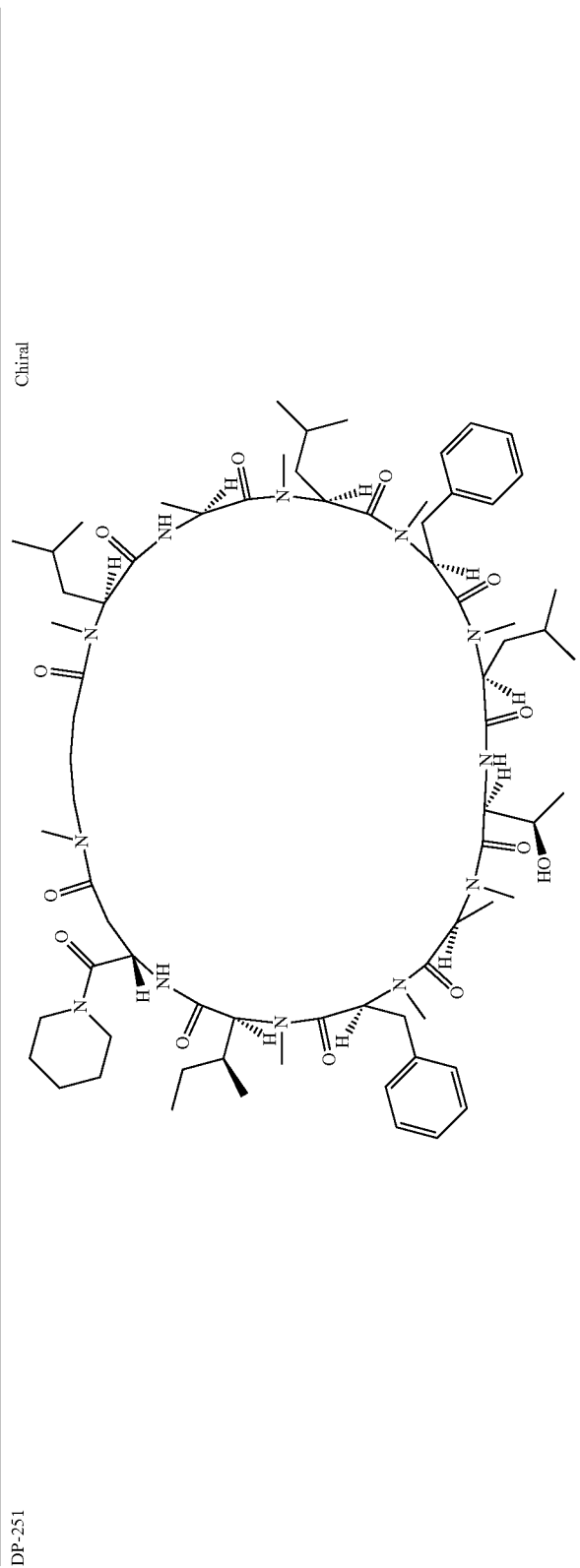
DP-251

TABLE 11-3-1-continued
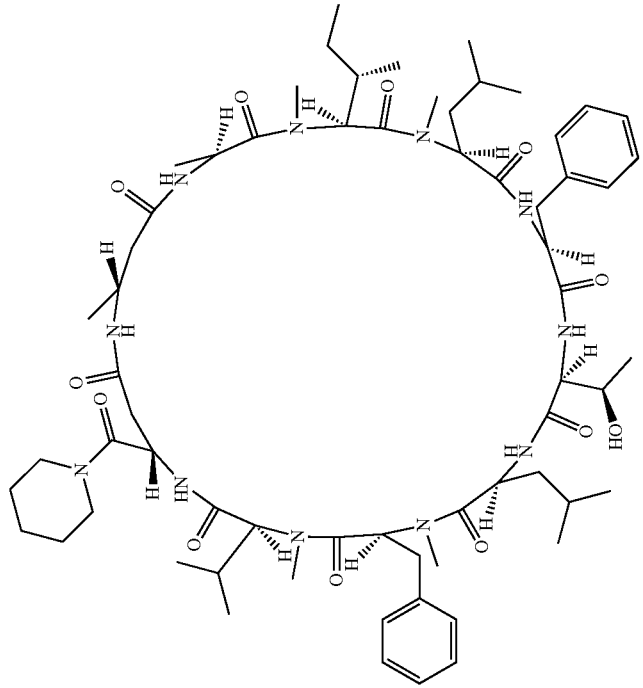
DP-252

TABLE 11-3-1-continued
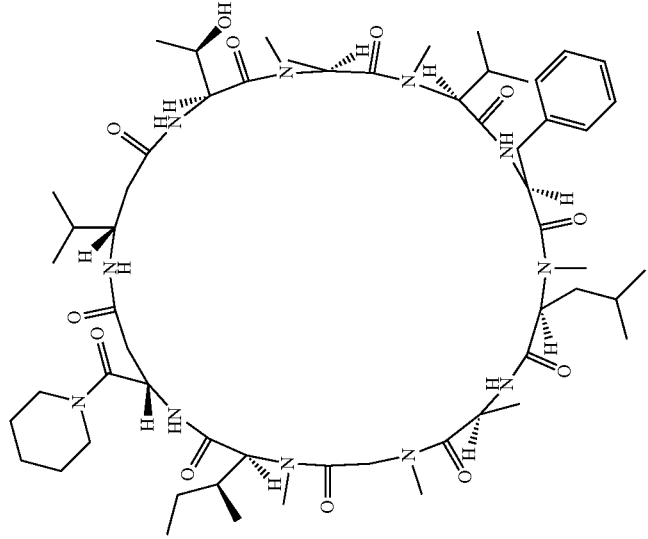
DP-253

TABLE 11-3-1-continued
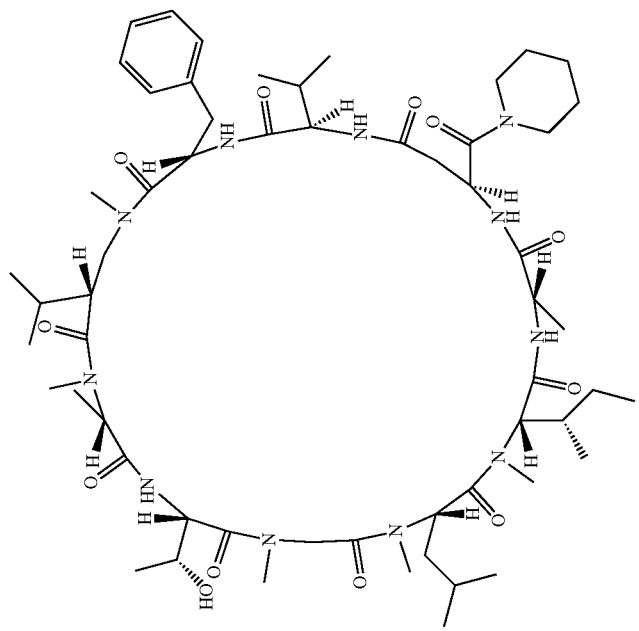
DP-254

TABLE 11-3-1-continued
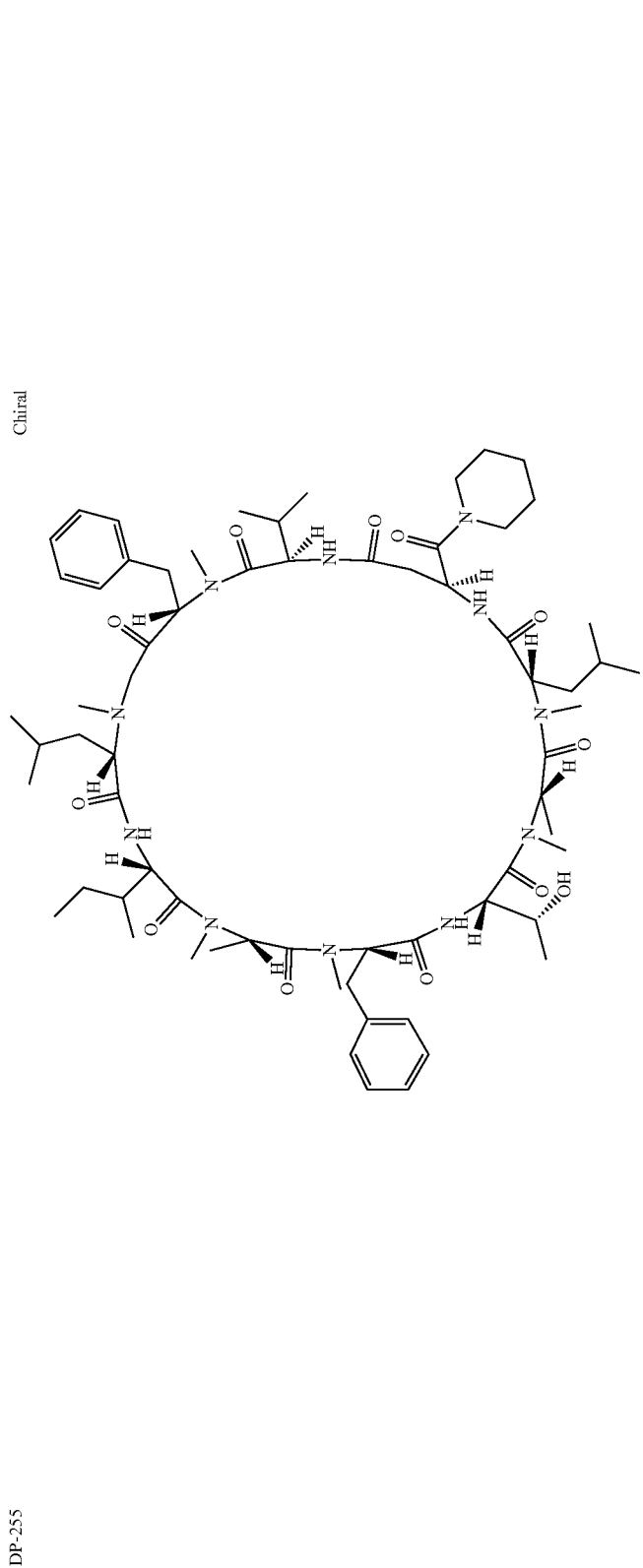
DP-255

TABLE 11-3-1-continued
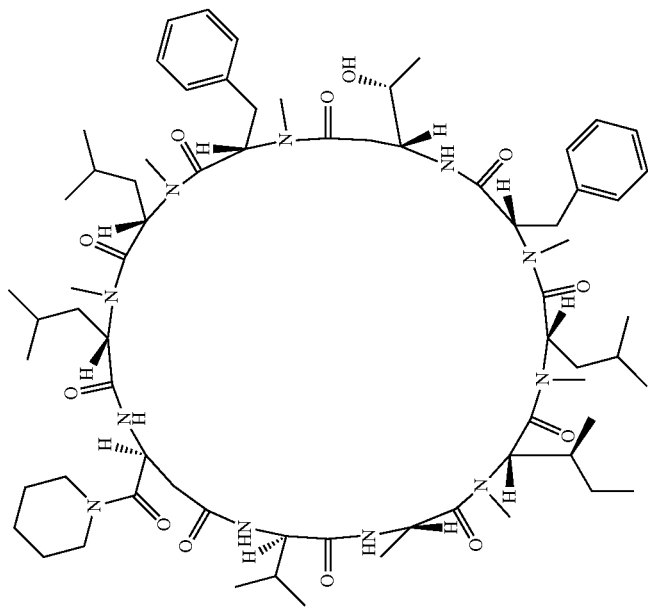
DP-256

TABLE 11-3-1-continued
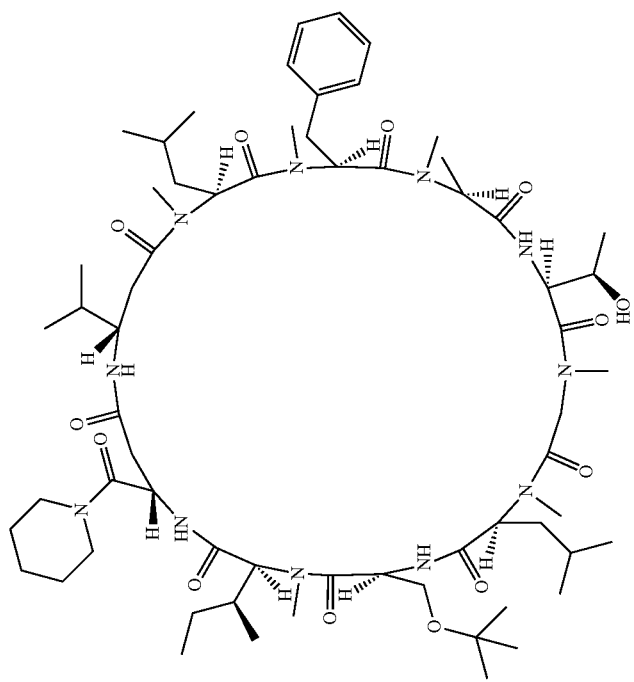
DP-257

TABLE 11-3-1-continued
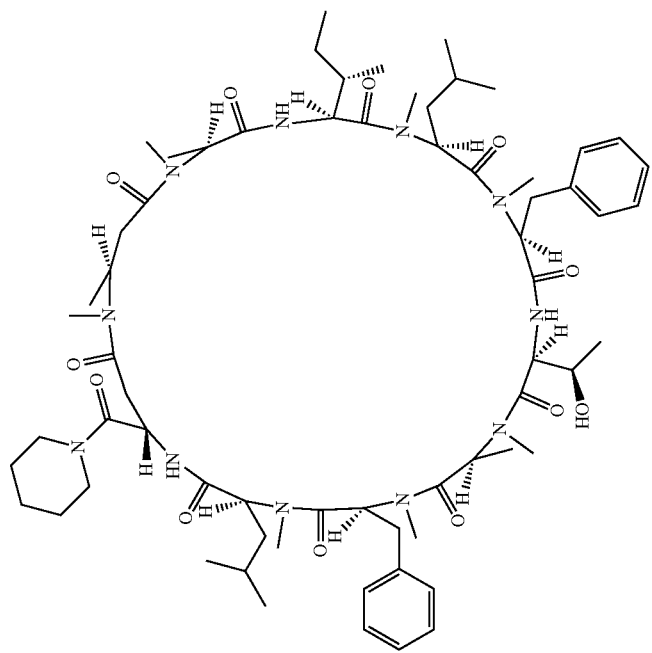
Chiral
DP-258

TABLE 11-3-1-continued
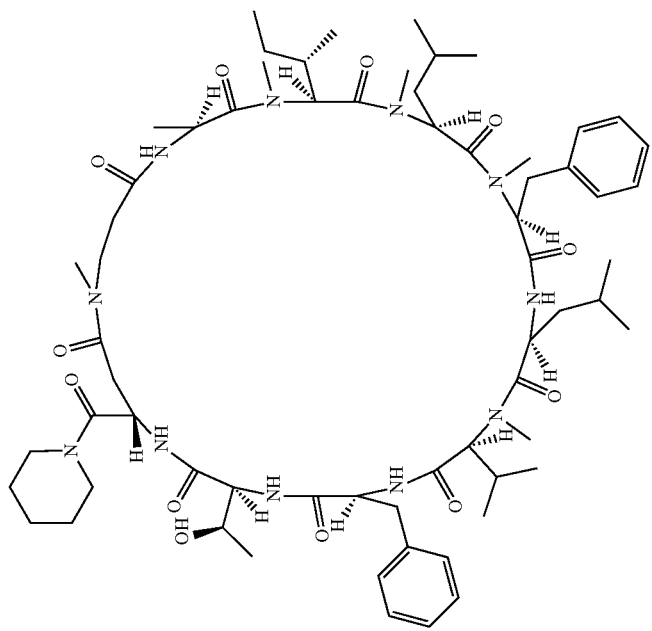
DP-259

TABLE 11-3-1-continued
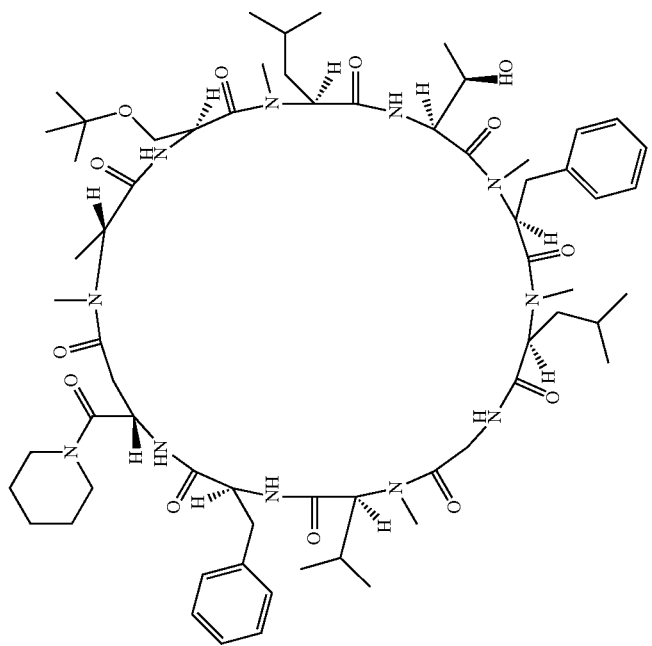
DP-260

TABLE 11-3-1-continued
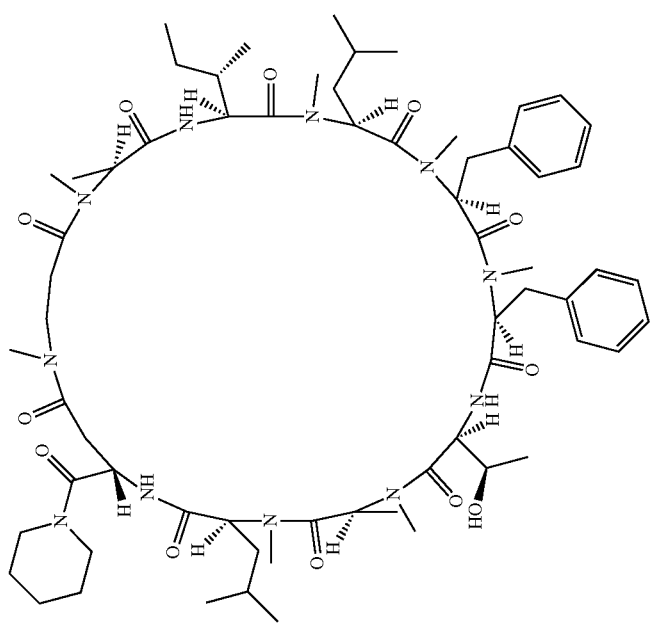
DP-261

TABLE 11-3-1-continued
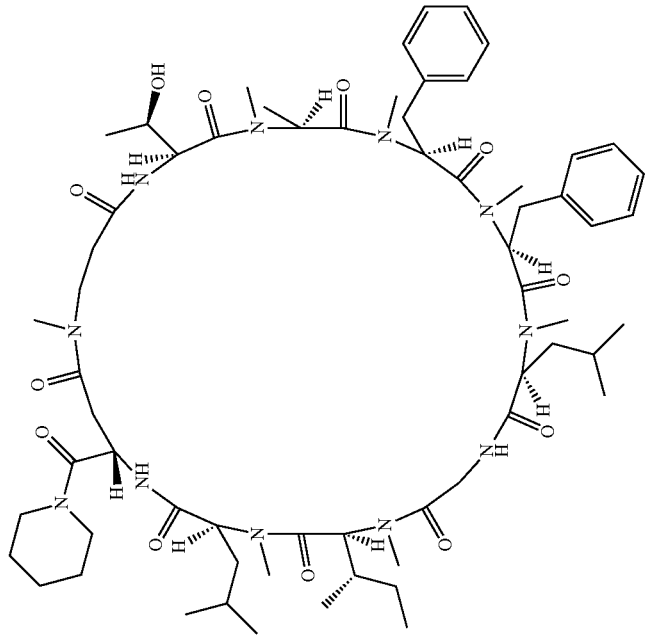
DP-262

TABLE 11-3-1-continued
DP-263
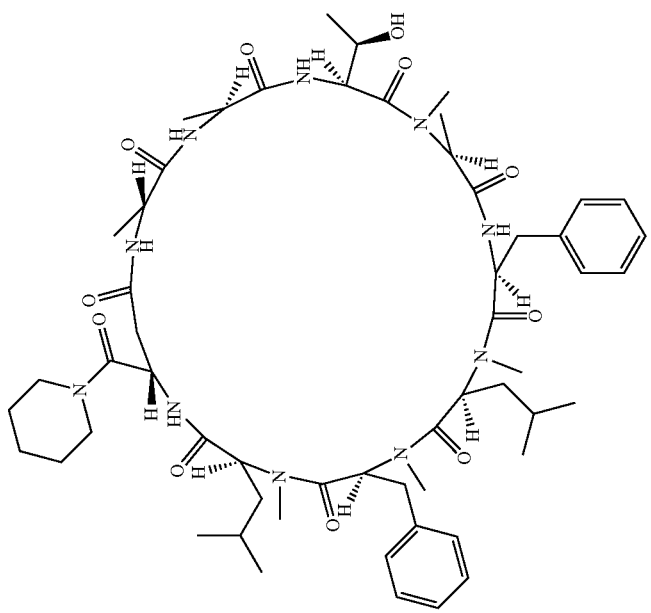

TABLE 11-3-1-continued
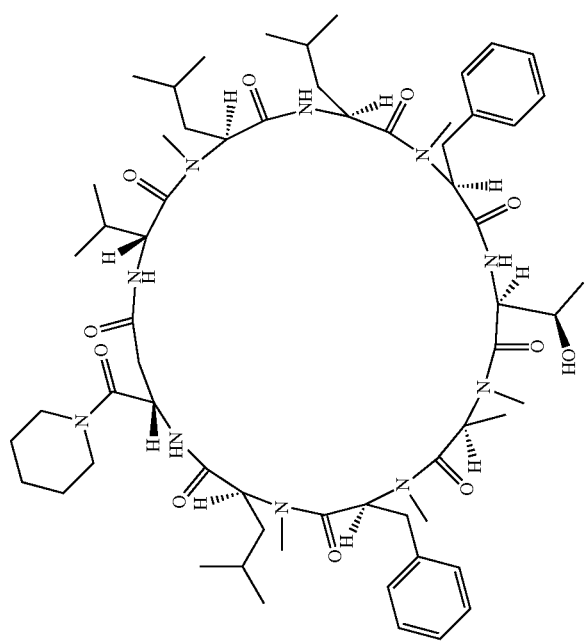
DP-264

TABLE 11-3-1-continued
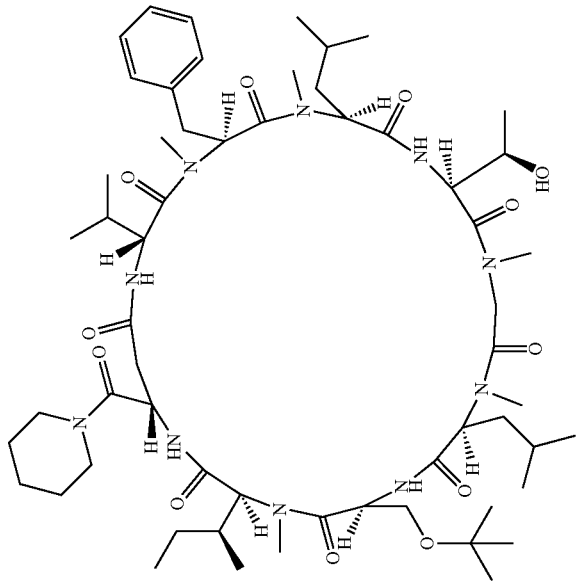
DP-265

TABLE 11-3-1-continued
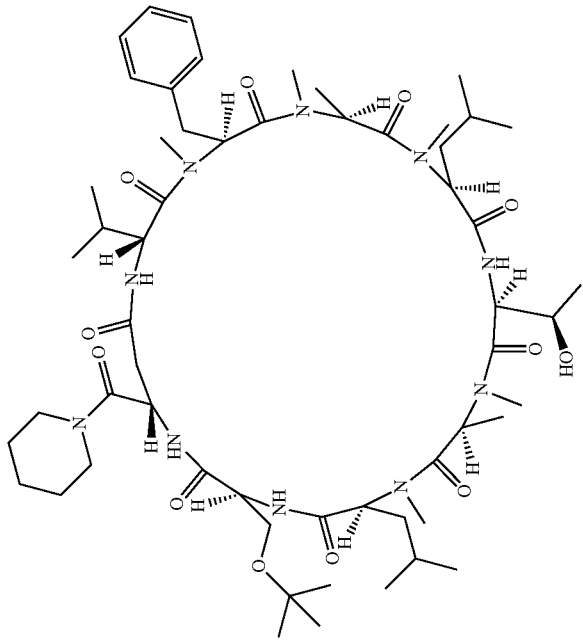
DP-266

TABLE 11-3-1-continued
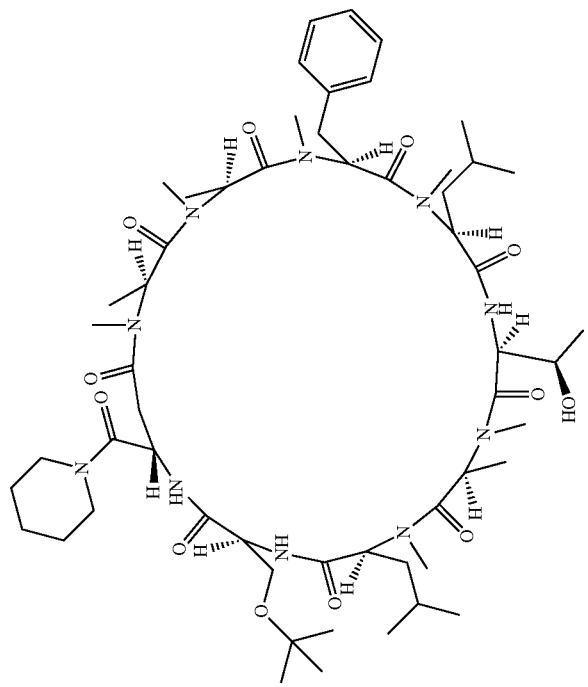
DP-267

TABLE 11-3-1-continued
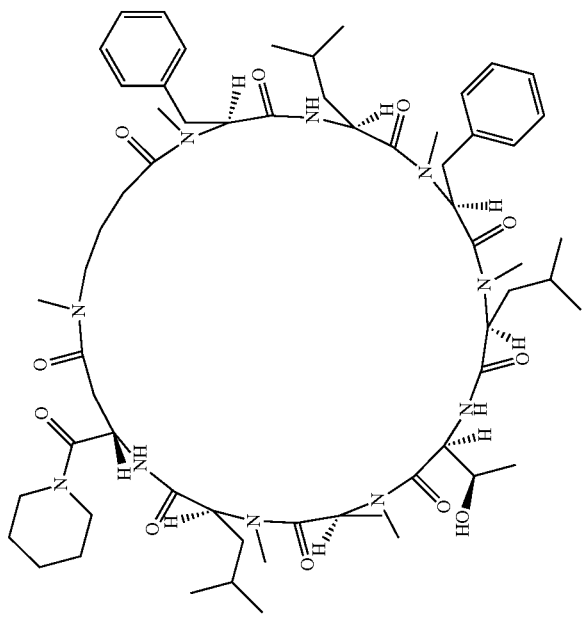
DP-268

TABLE 11-3-1-continued
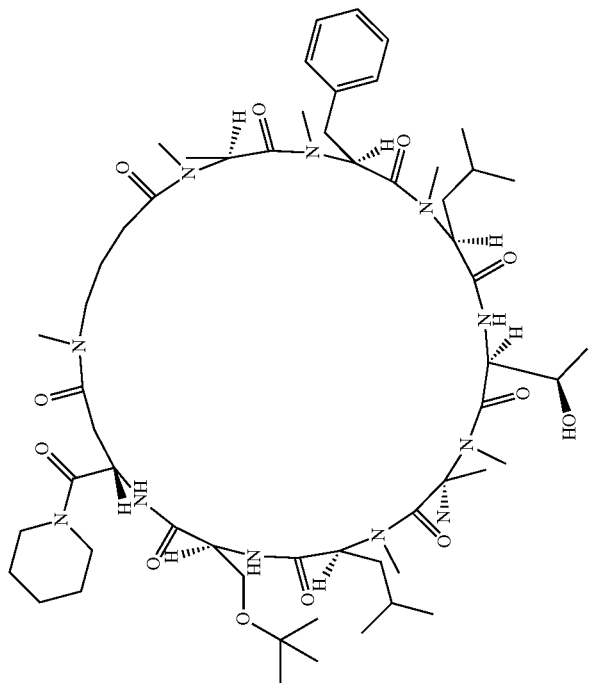
DP-269

TABLE 11-3-1-continued
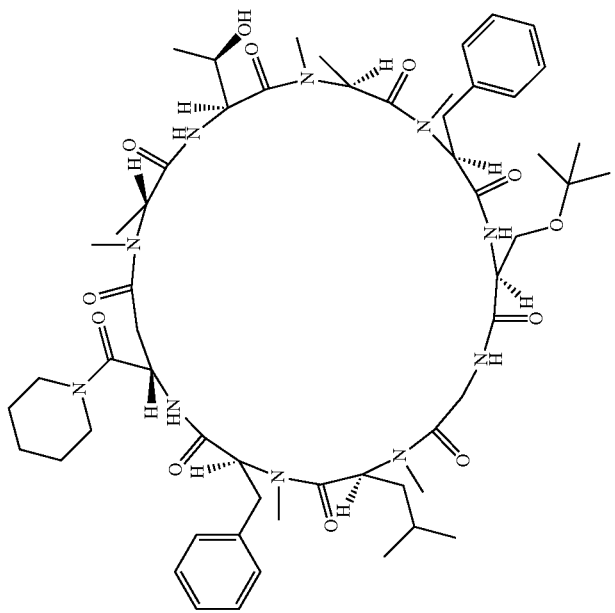
DP-270

TABLE 11-3-1-continued
DP-271
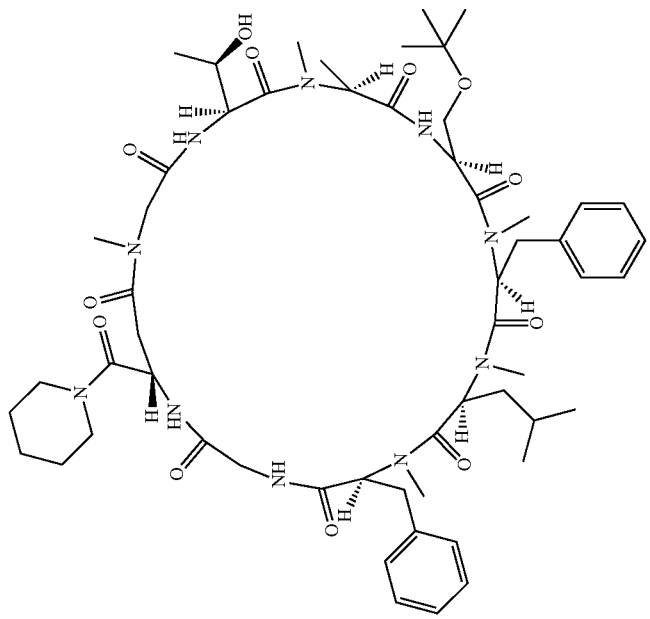

TABLE 11-3-1-continued
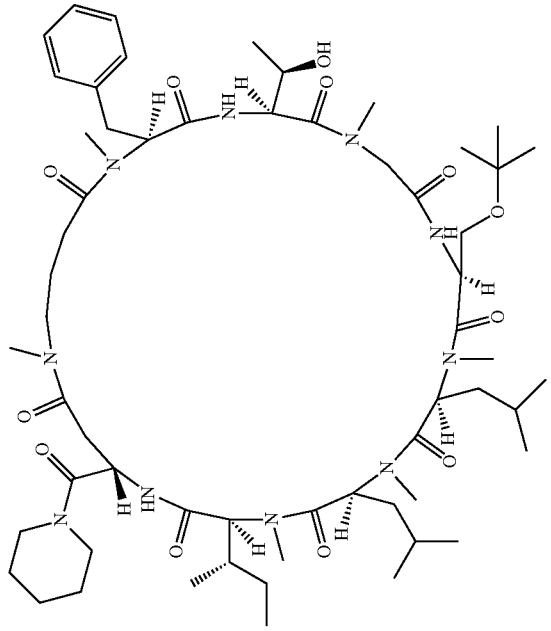
DP-272
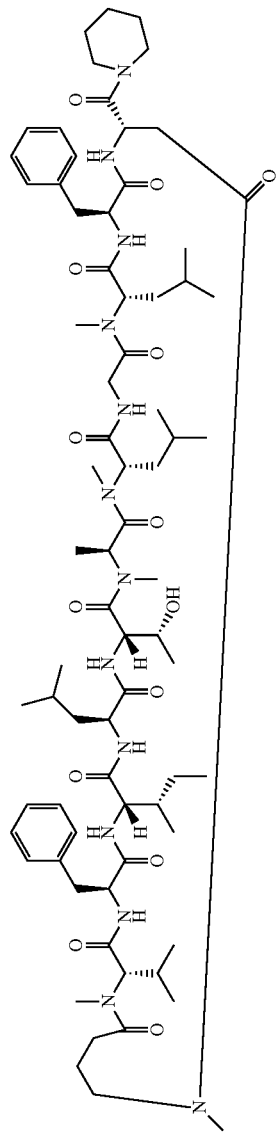
DP-273

TABLE 11-3-1-continued
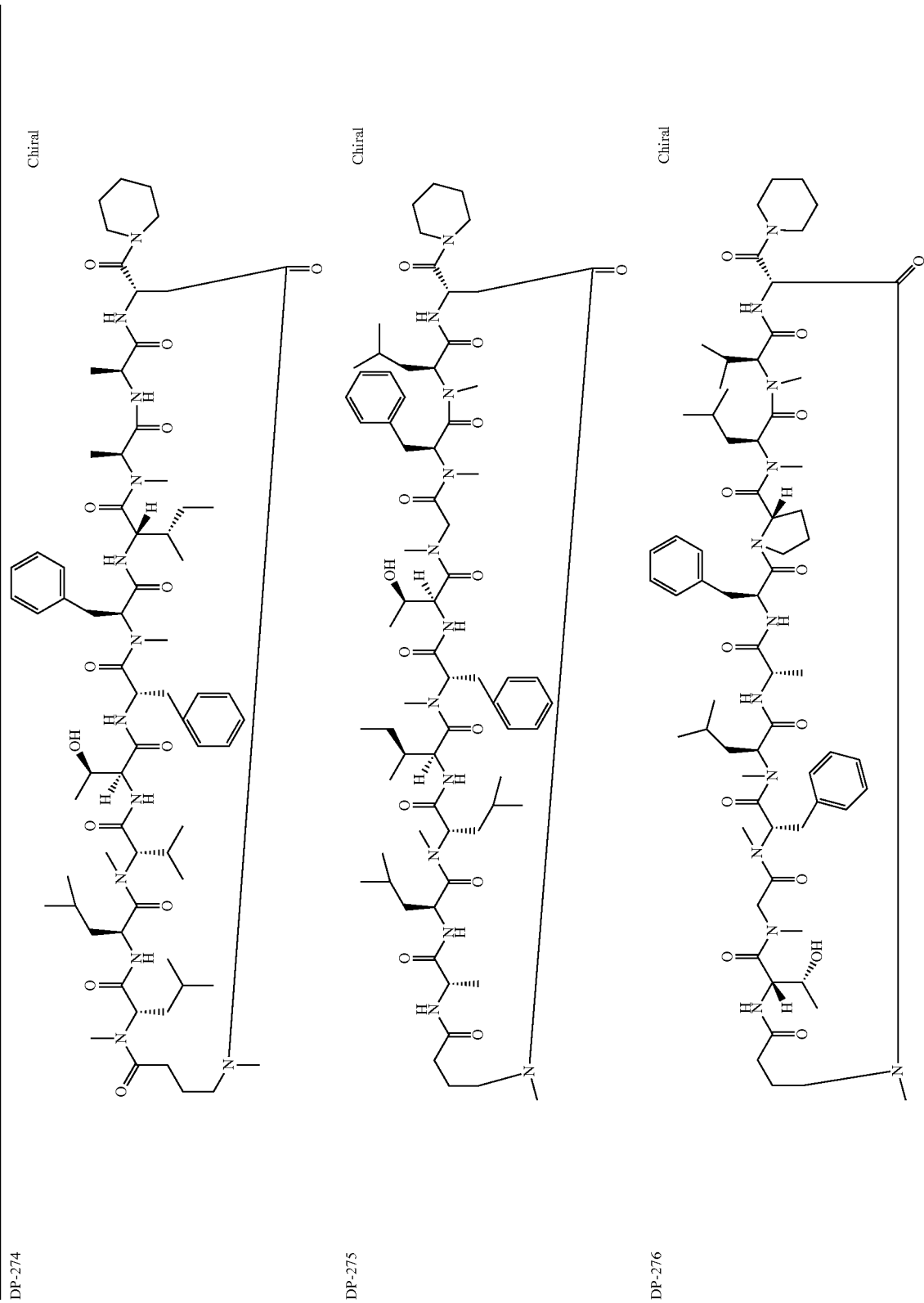
DP-274
DP-275
DP-276

TABLE 11-3-1-continued
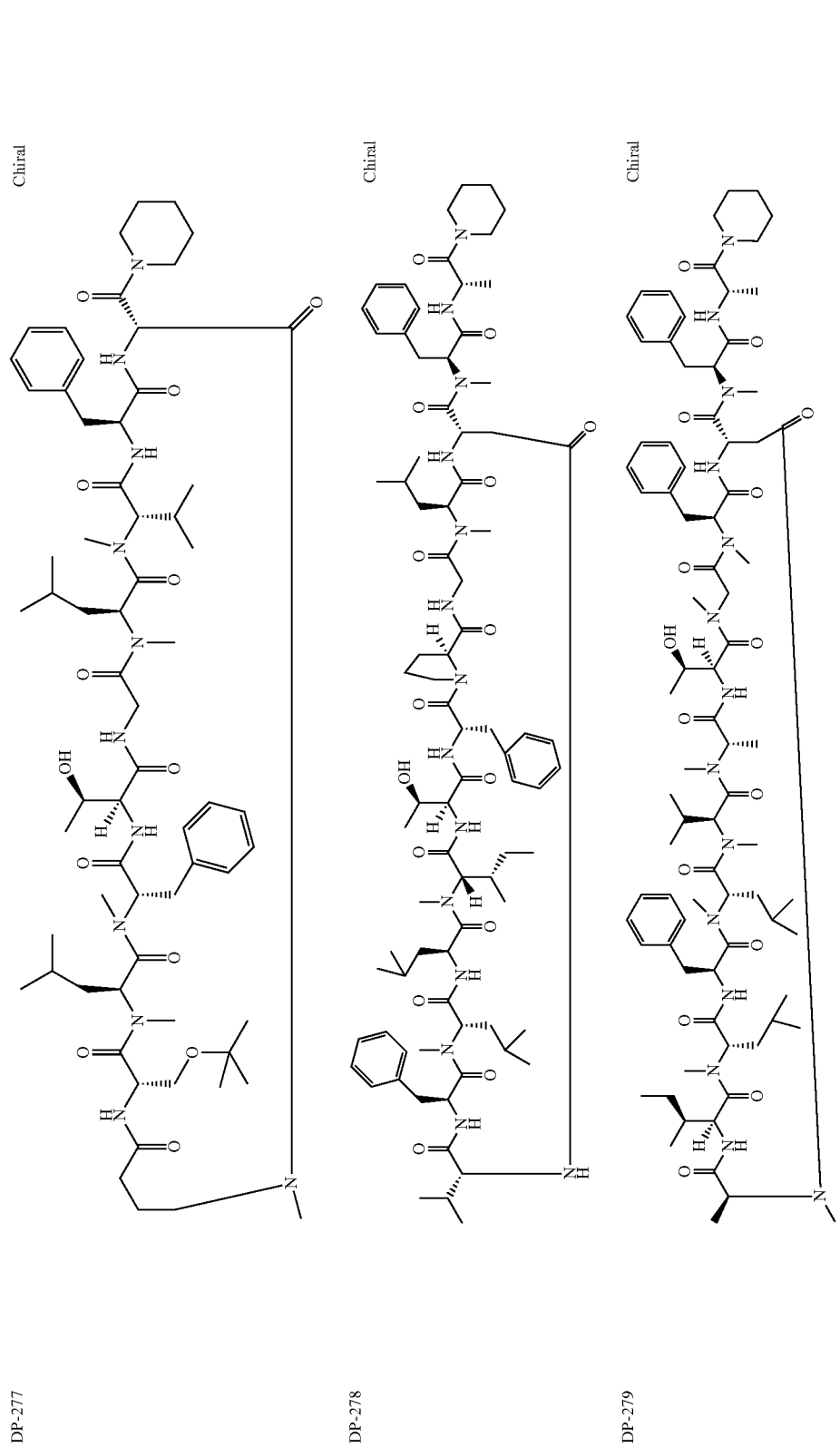
DP-277
DP-278
DP-279

TABLE 11-3-1-continued
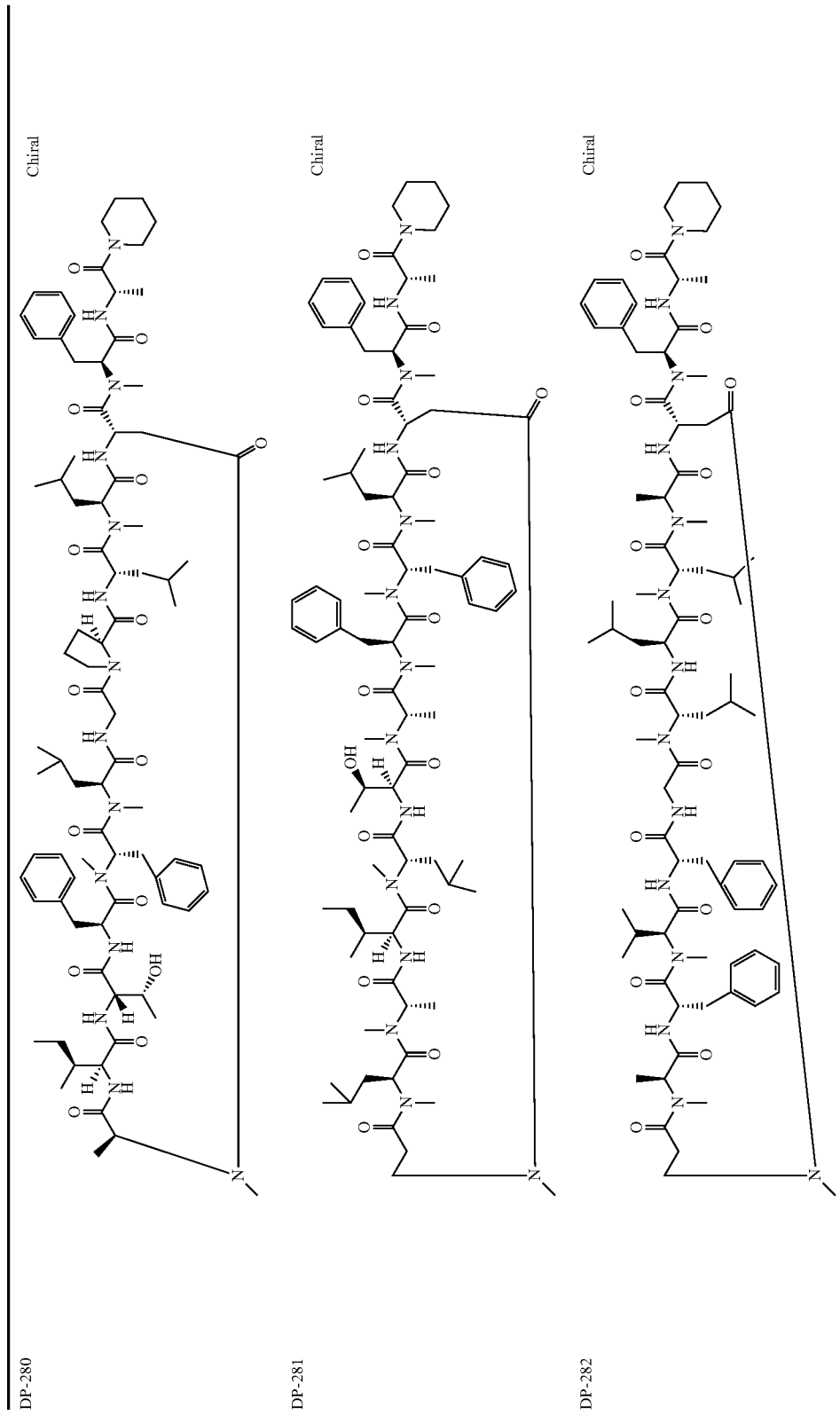
DP-280
DP-281
DP-282

TABLE 11-3-1-continued
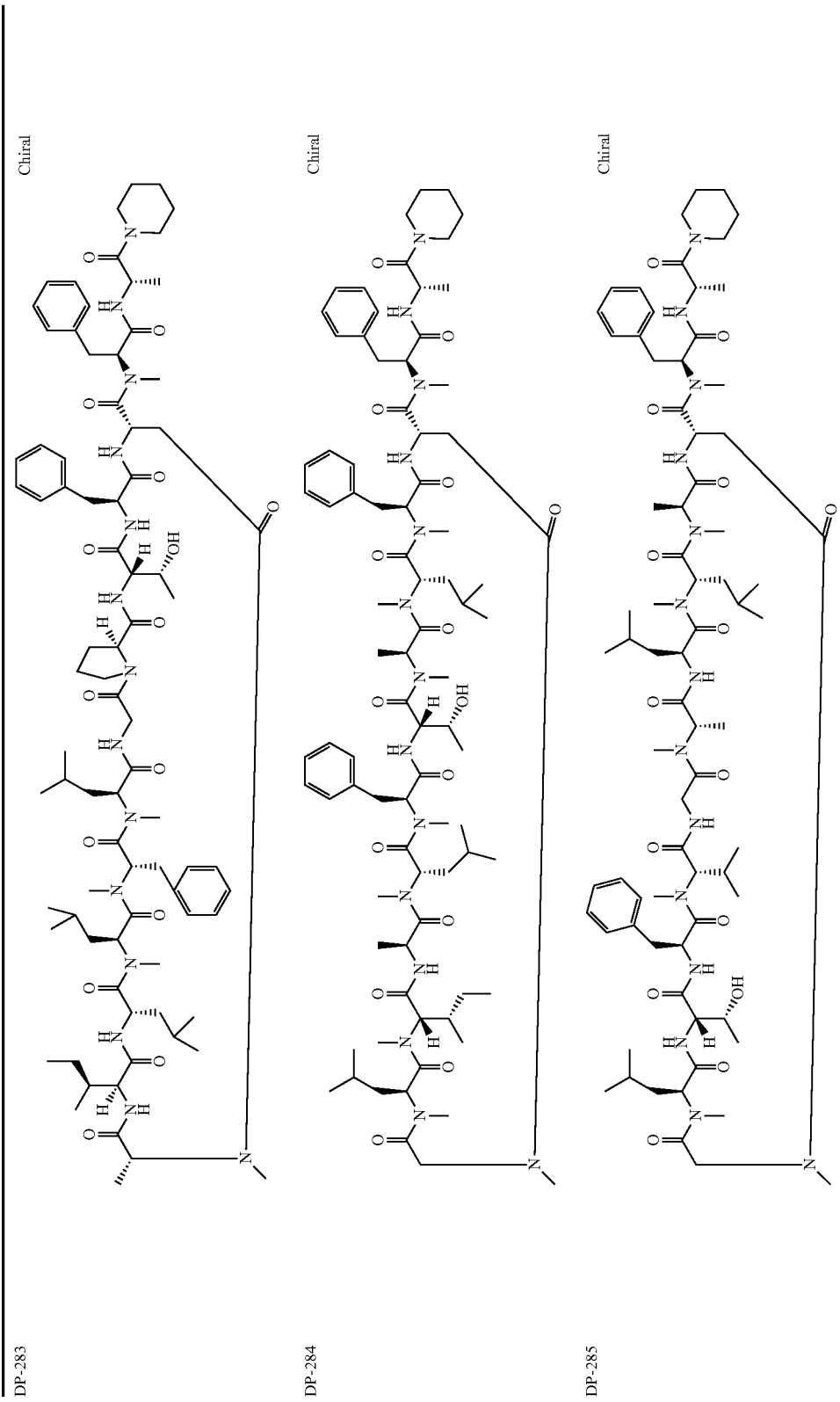
DP-283
DP-284
DP-285

TABLE 11-3-1-continued
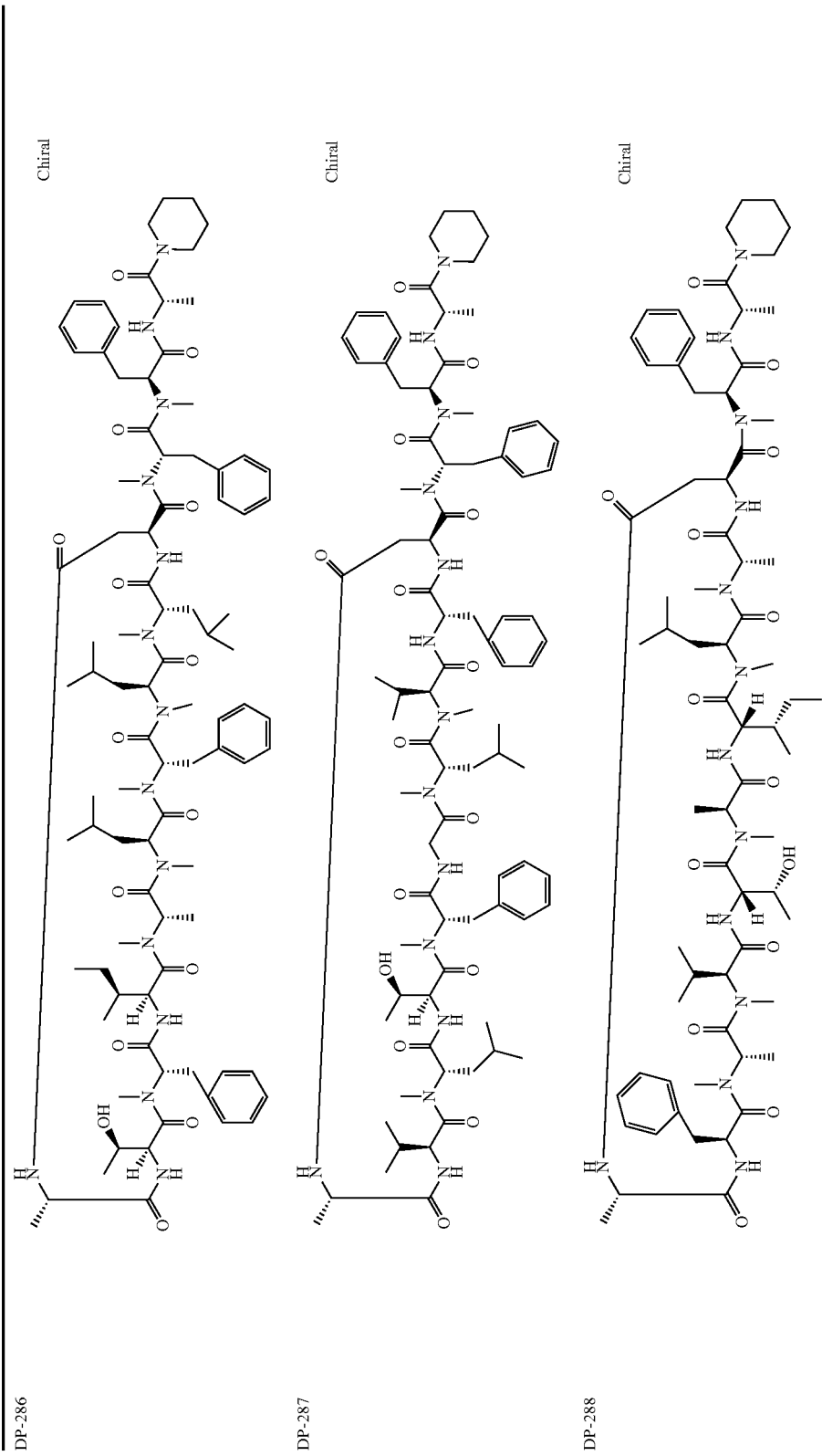
DP-286
DP-287
DP-288

TABLE 11-3-1-continued
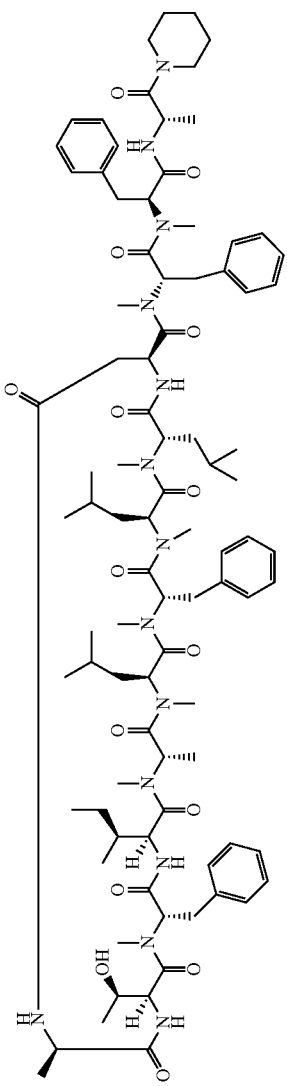
DP-289
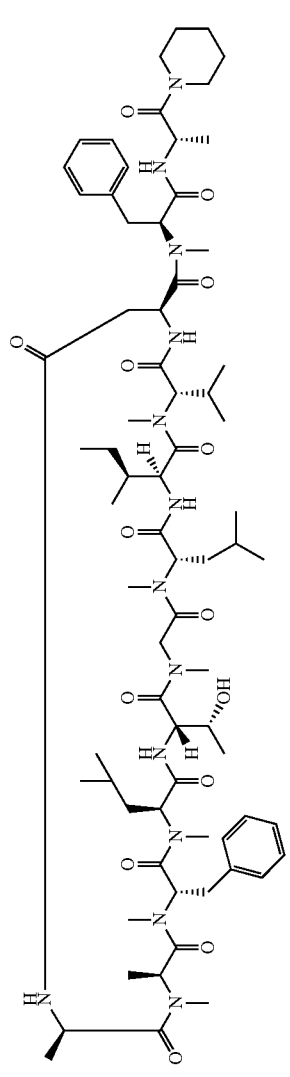
DP-290
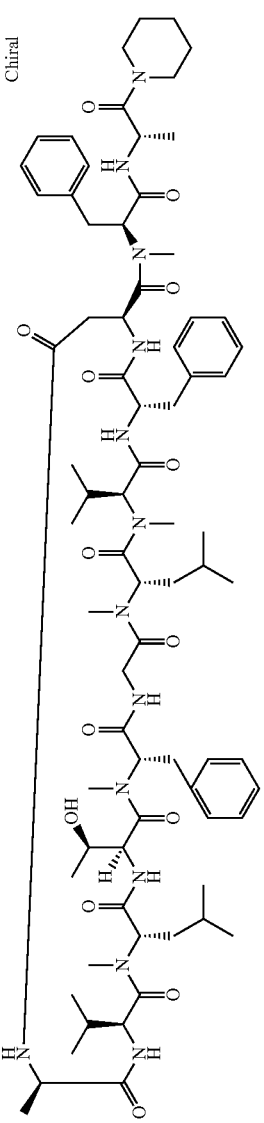
DP-291

TABLE 11-3-1-continued
| DP-292 | 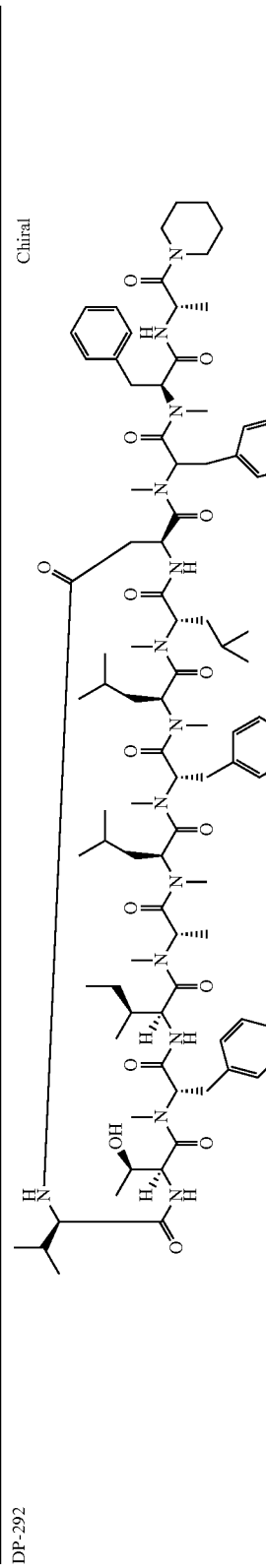 |
| DP-293 | 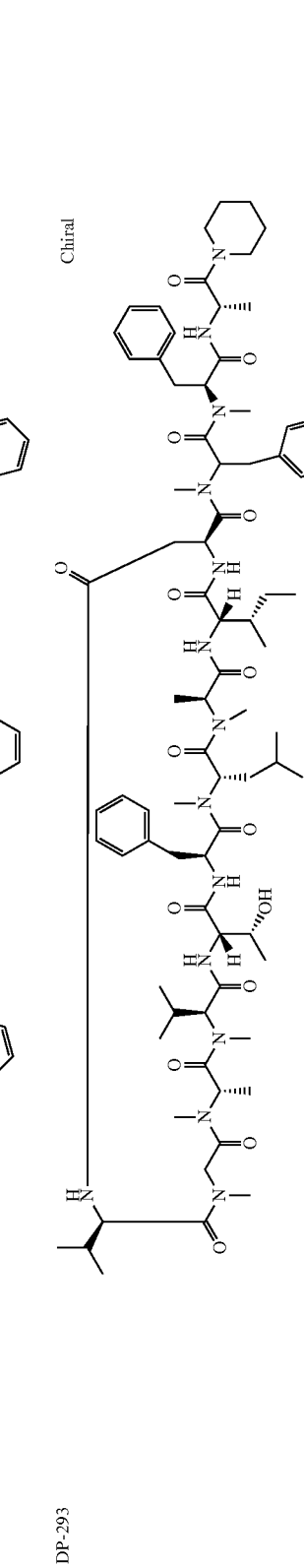 |
| DP-294 | 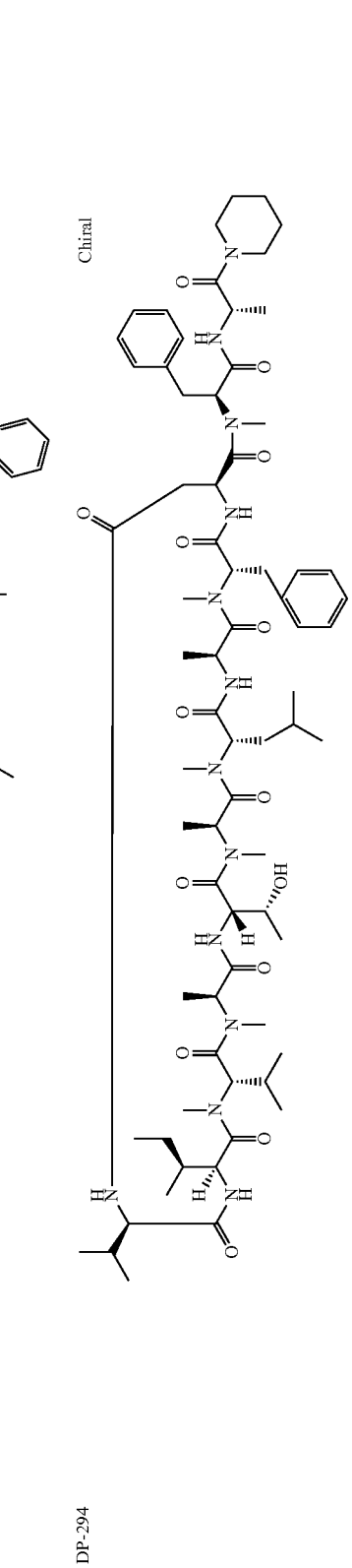 |

TABLE 11-3-1-continued
| | |
|---|---|
| DP-295 | 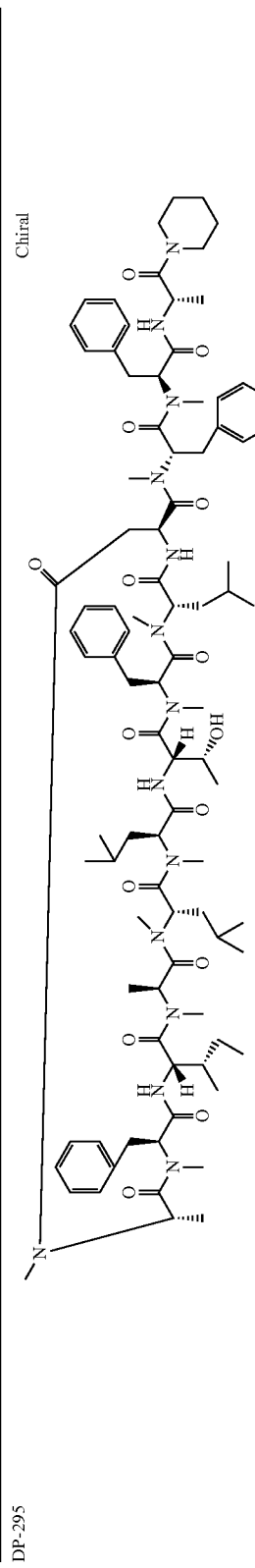 |
| DP-296 | 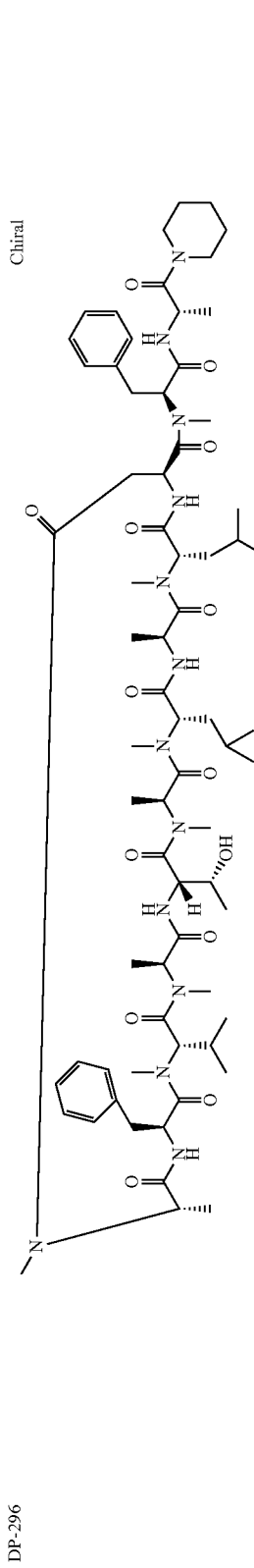 |
| DP-297 | 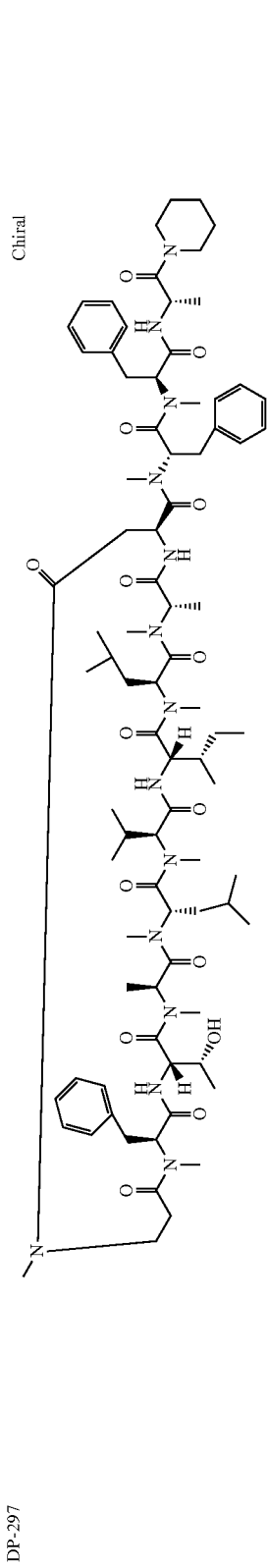 |

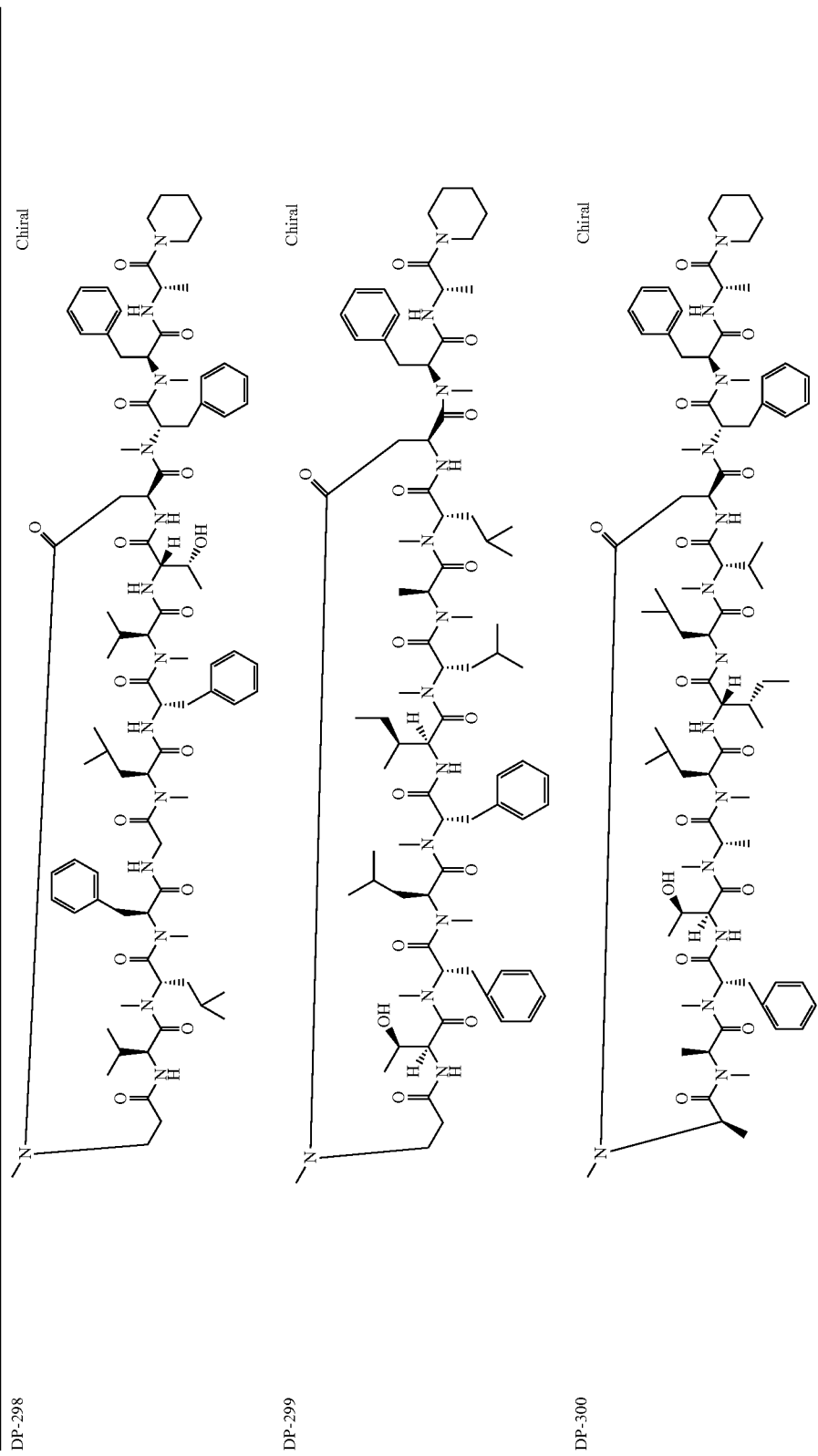

TABLE 11-3-1-continued
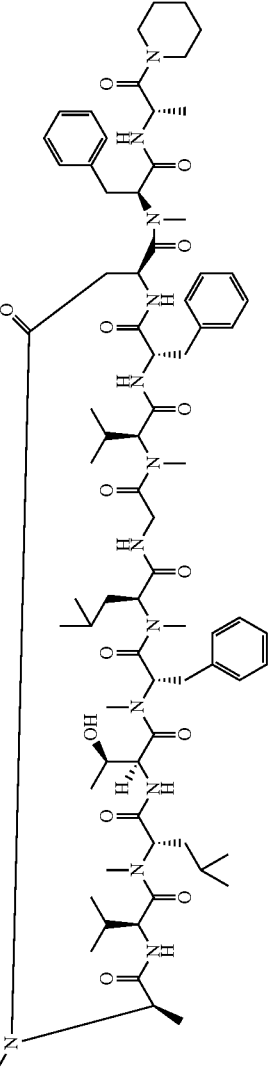
DP-301
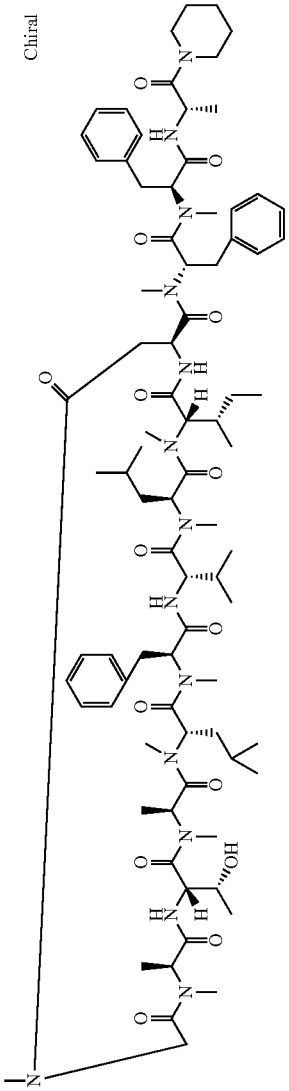
DP-302
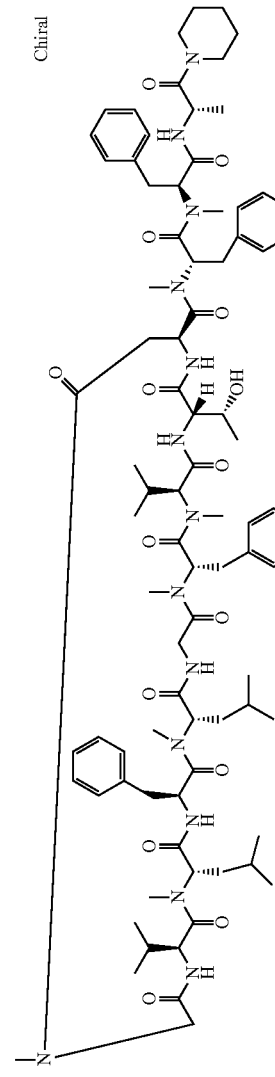
DP-303

TABLE 11-3-1-continued
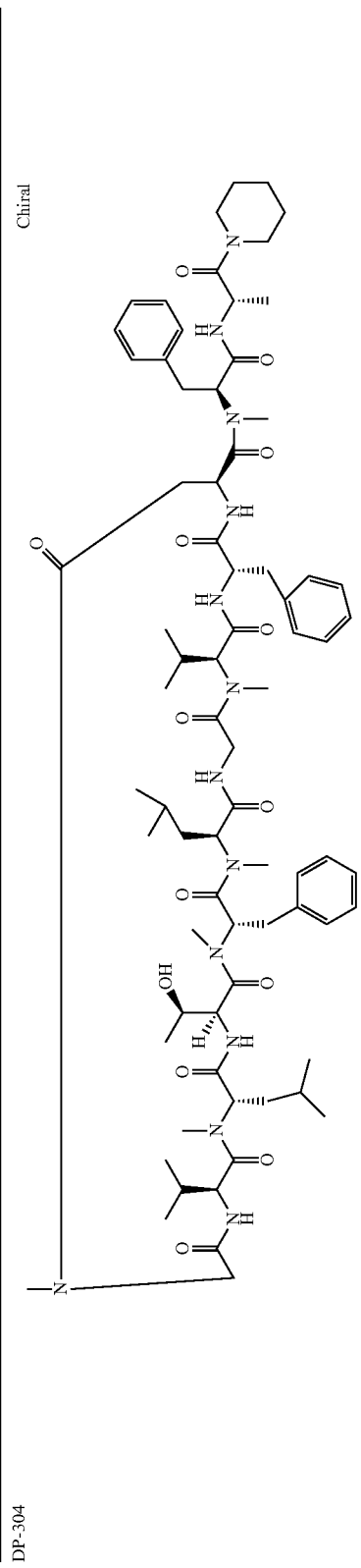
DP-304
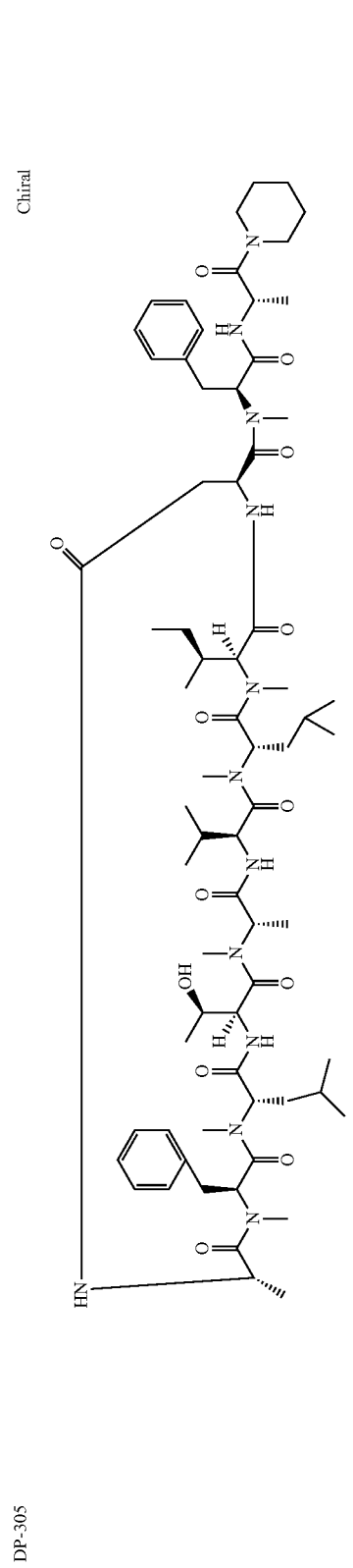
DP-305
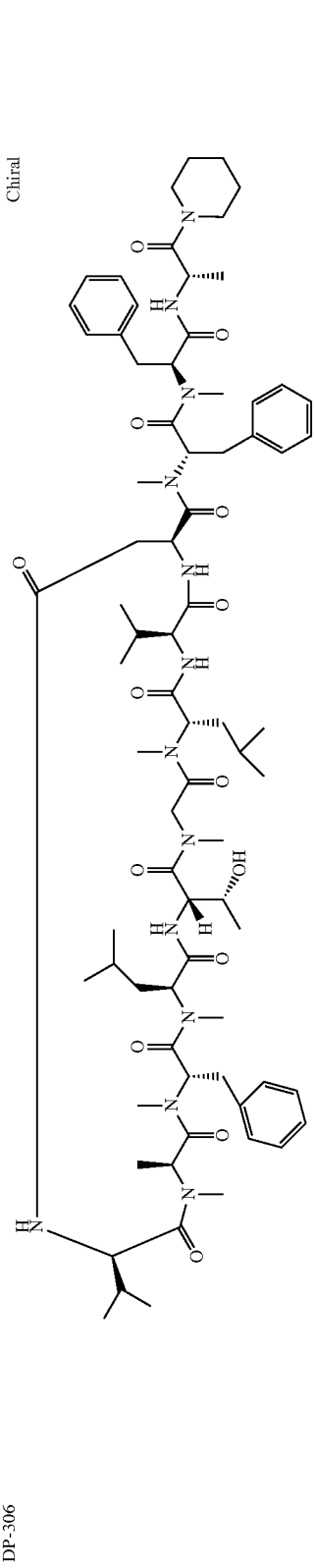
DP-306

TABLE 11-3-1-continued
| DP-307 | 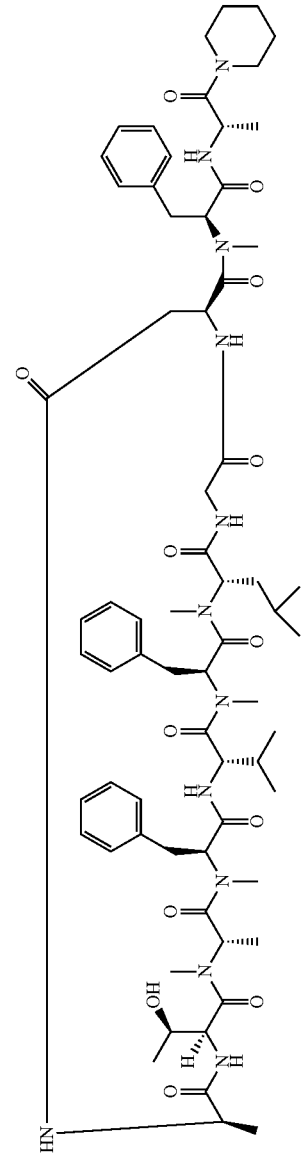 |
| DP-308 | 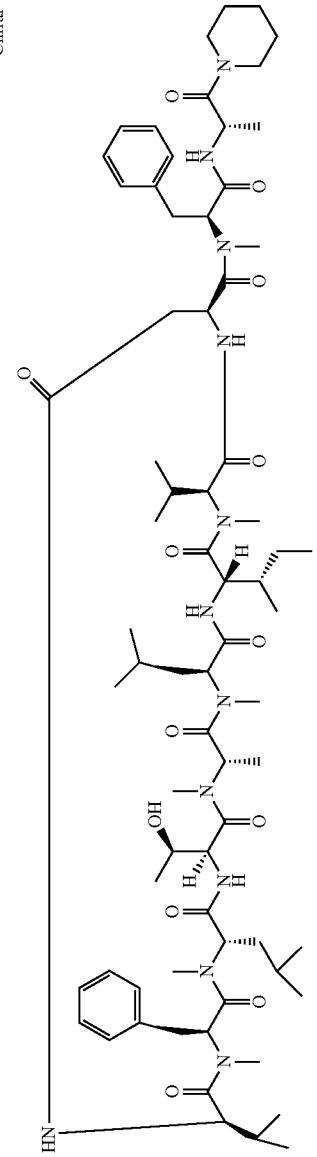 |
| DP-309 | 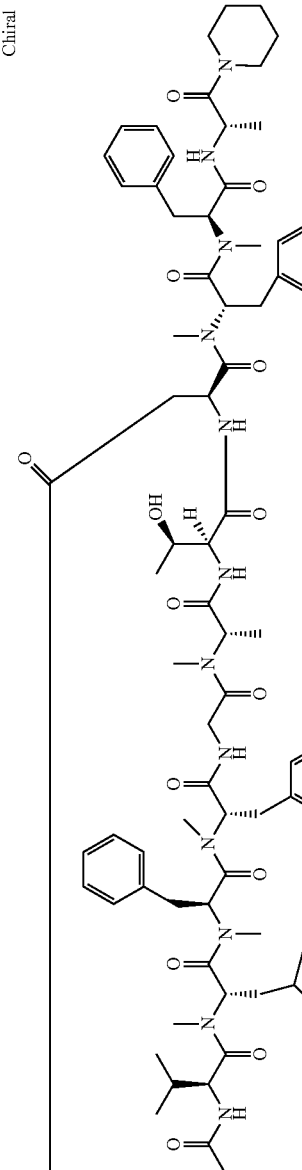 |

TABLE 11-3-1-continued
| DP-310 | 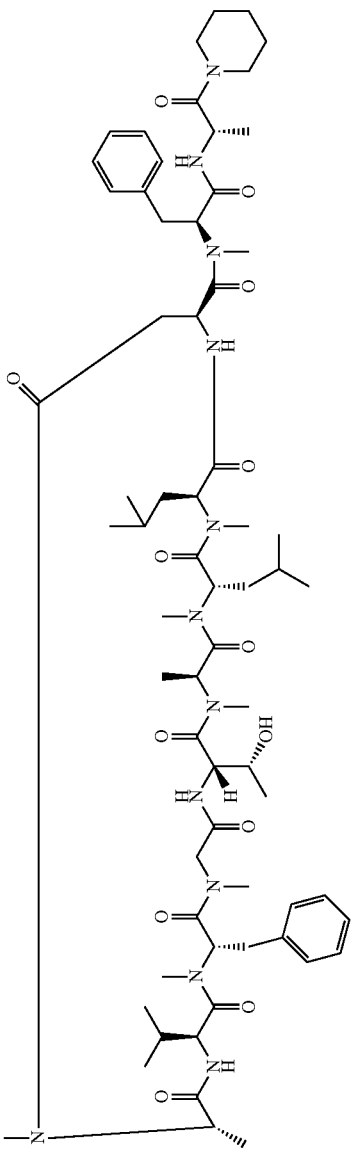 |
| DP-311 | 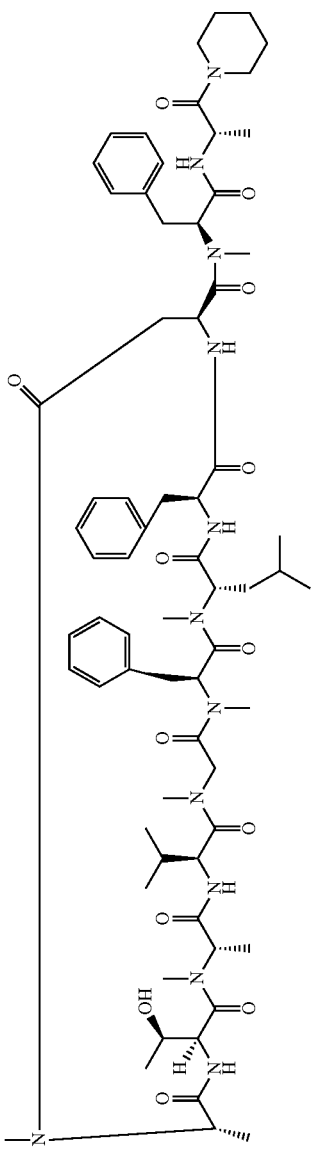 |
| DP-312 | 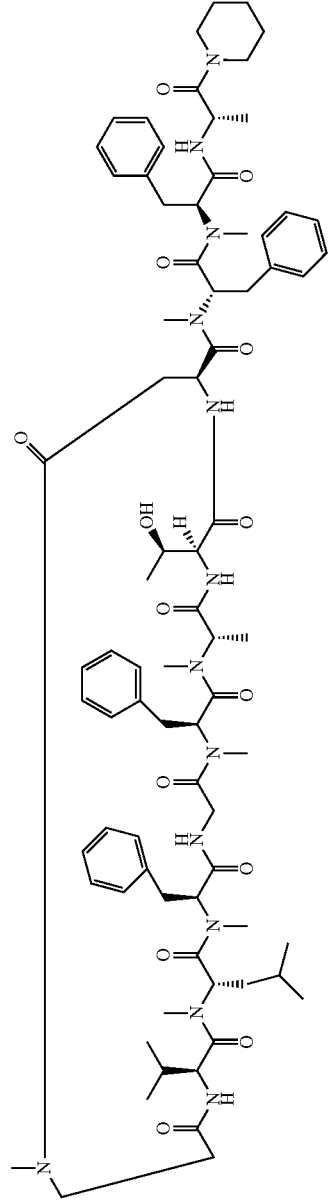 |

TABLE 11-3-1-continued
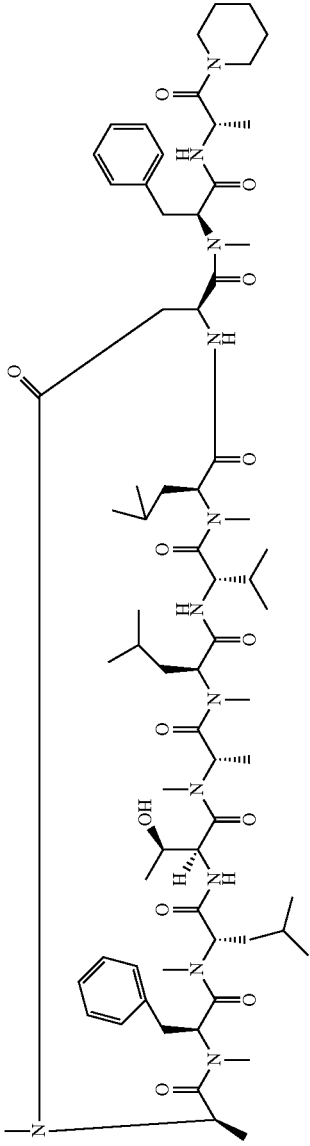
DP-313
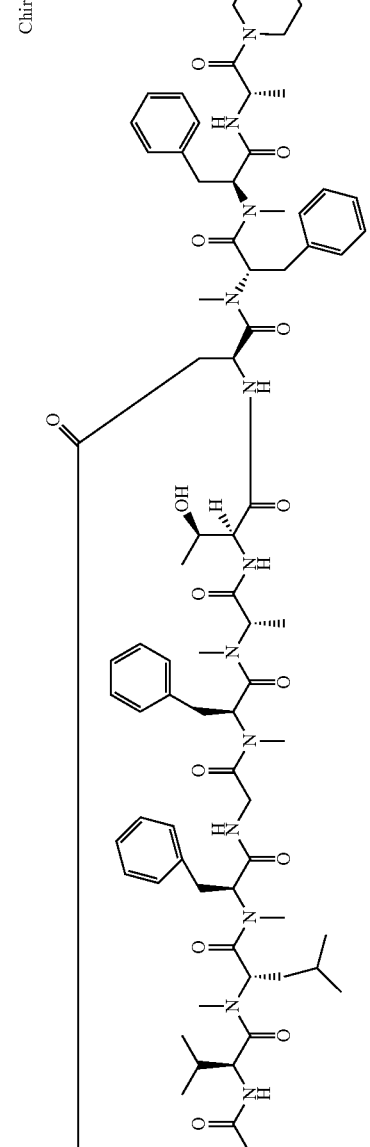
DP-314
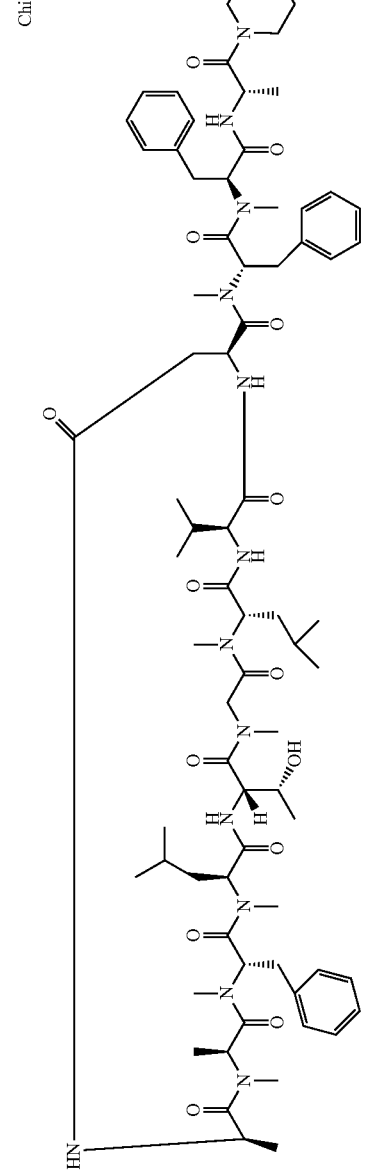
DP-315

TABLE 11-3-1-continued
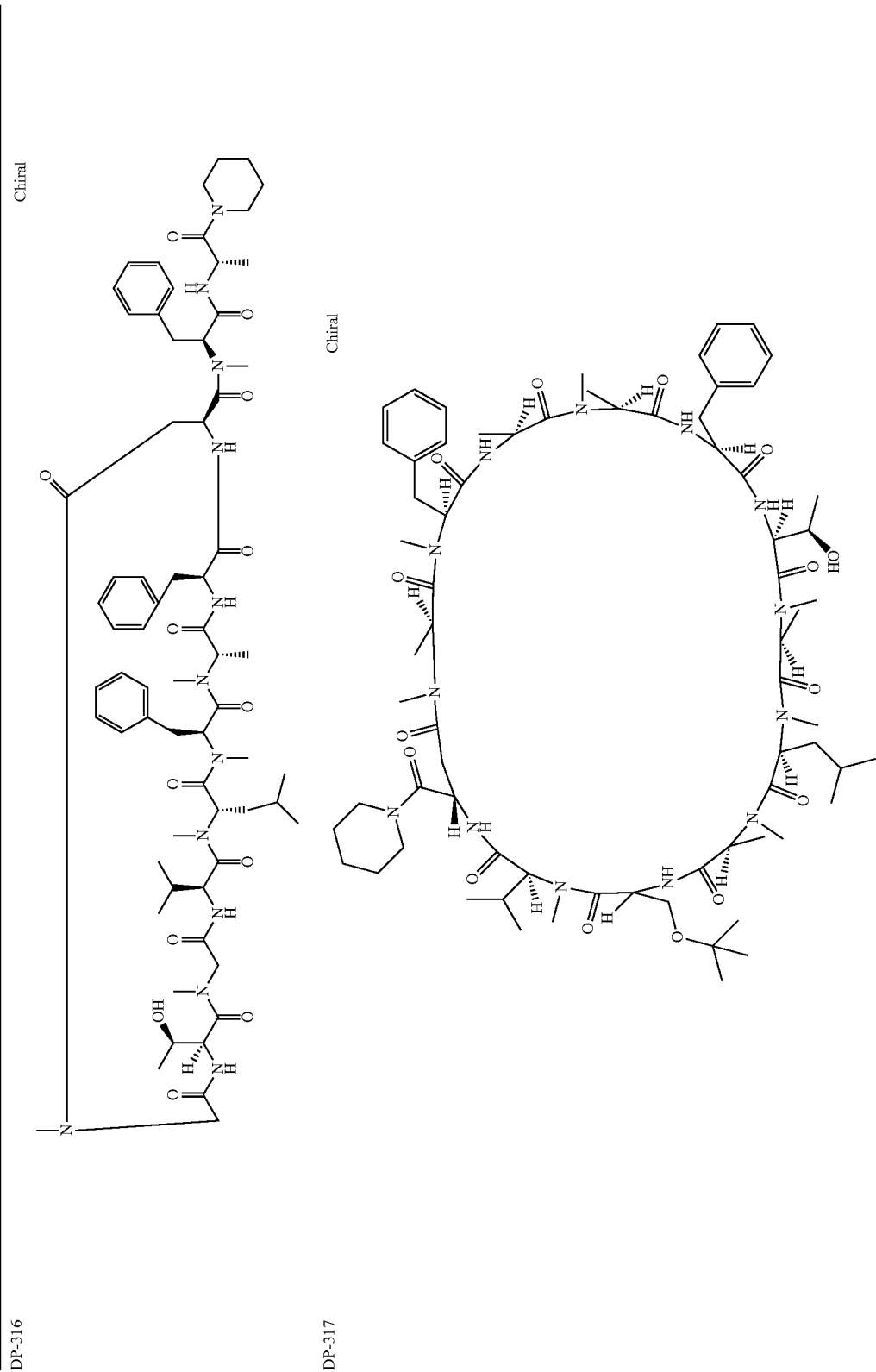
DP-316
DP-317

TABLE 11-3-1-continued
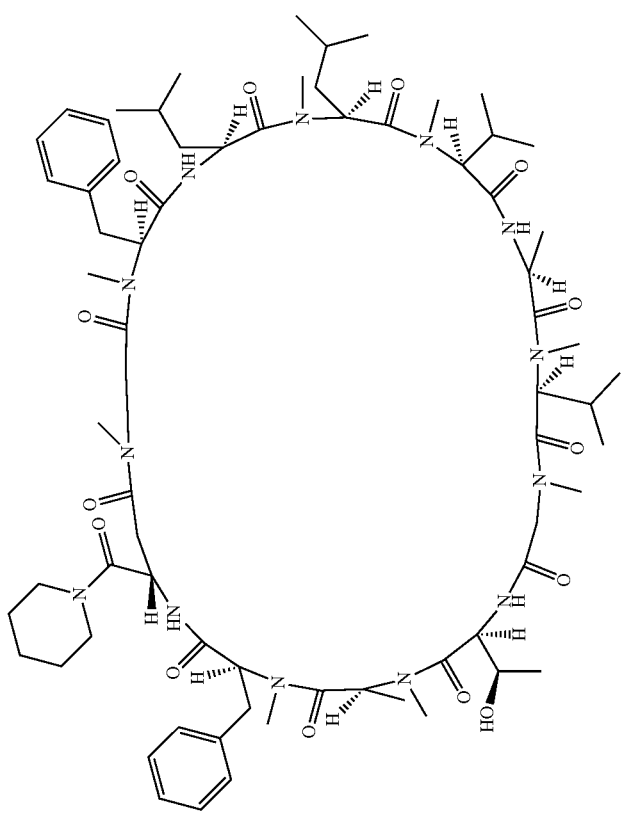
DP-318

TABLE 11-3-1-continued
Chiral
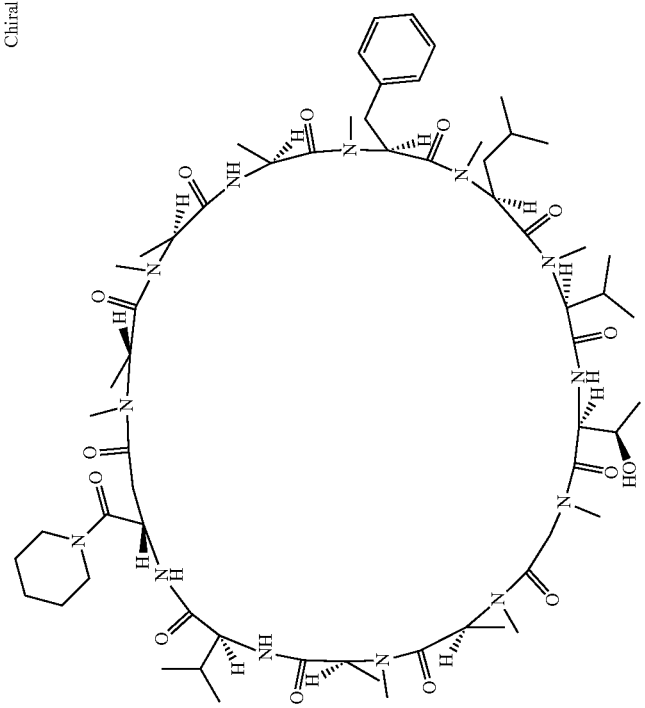
DP-319

TABLE 11-3-1-continued
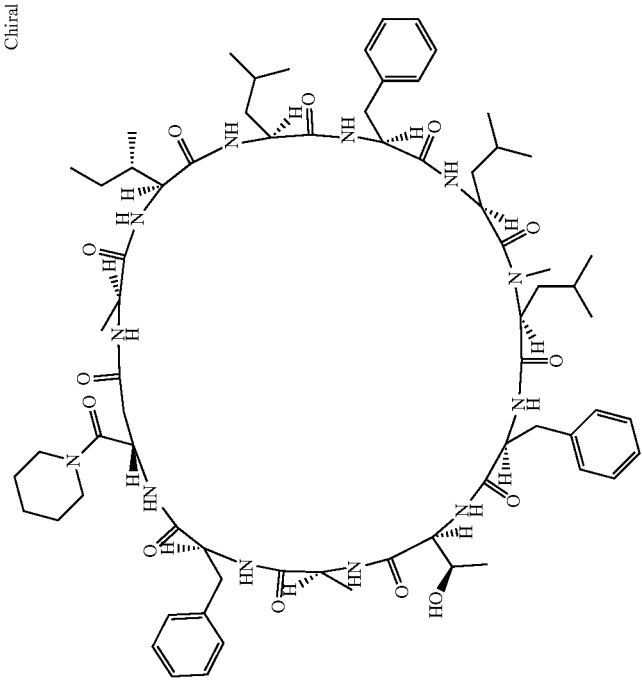
DP-320

TABLE 11-3-1-continued
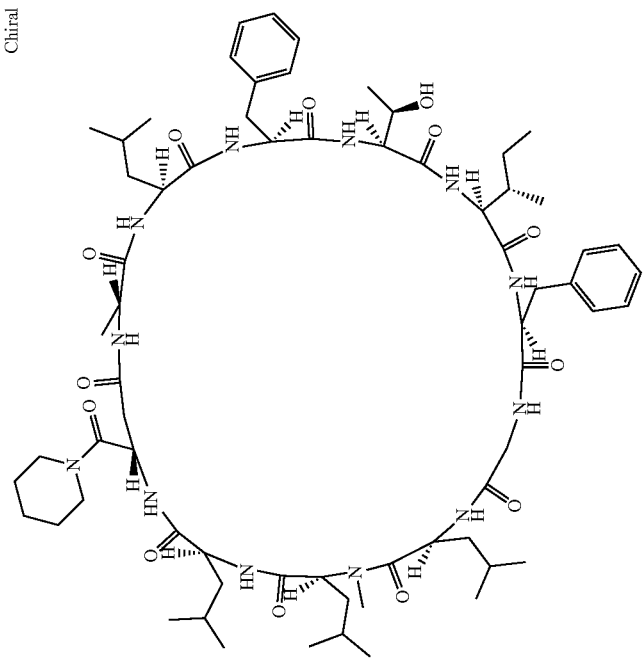
DP-321

TABLE 11-3-1-continued
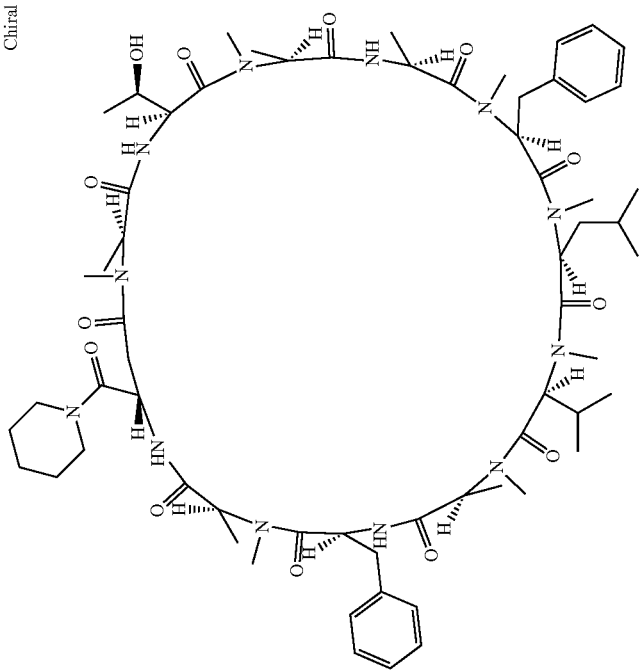
DP-322

TABLE 11-3-1-continued
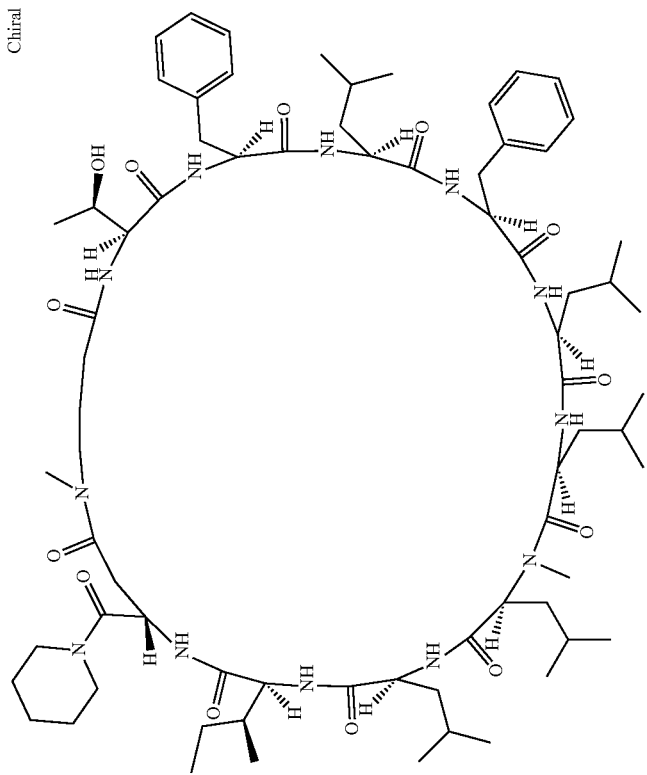
DP-323

TABLE 11-3-1-continued
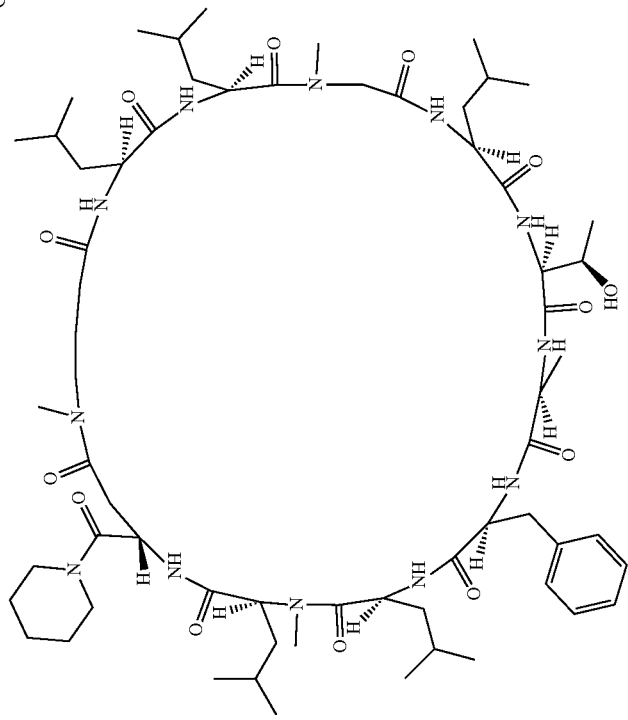
DP-324

TABLE 11-3-1-continued
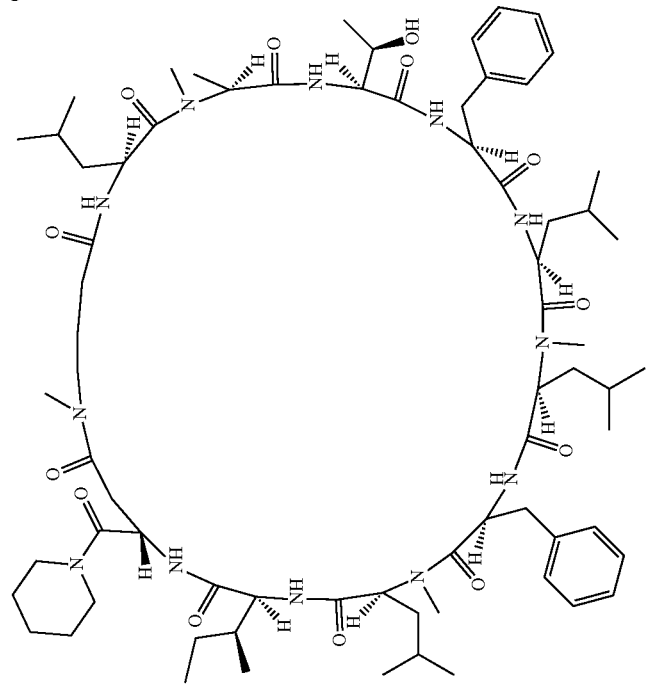
DP-325

TABLE 11-3-1-continued
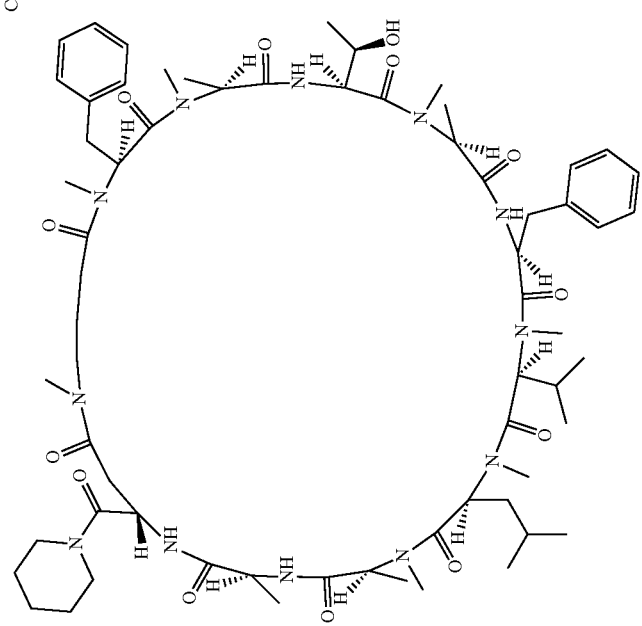
DP-326

TABLE 11-3-1-continued
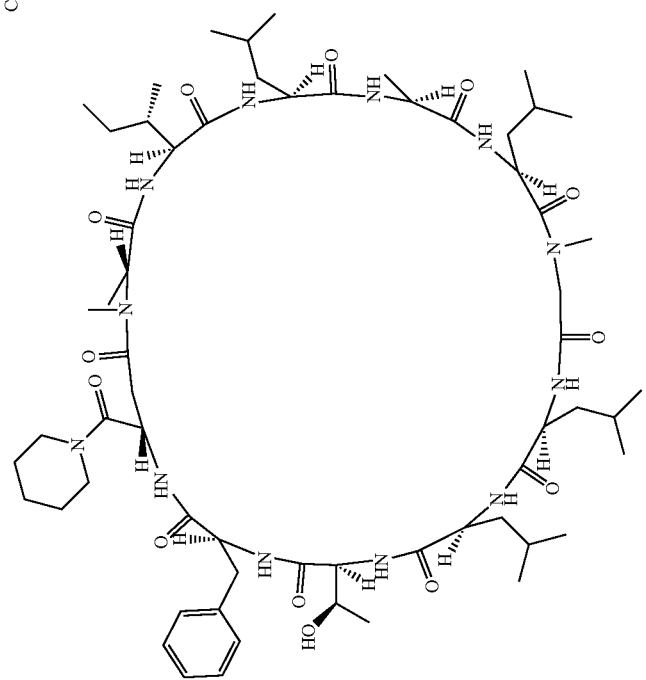
DP-327

TABLE 11-3-1-continued
DP-328
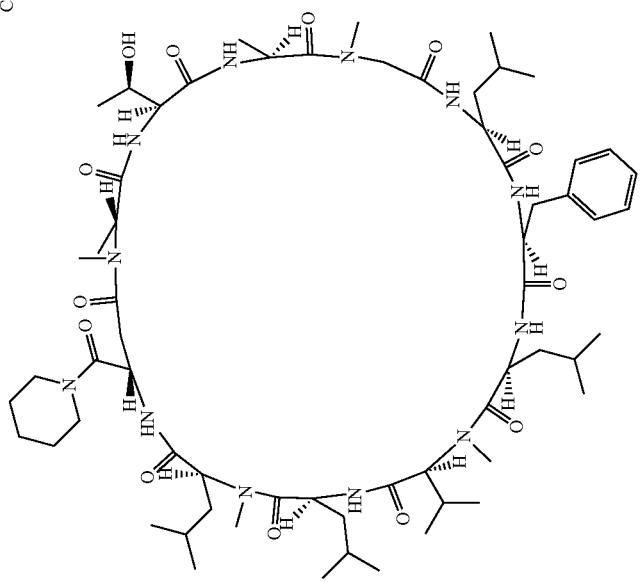

TABLE 11-3-1-continued
DP-329
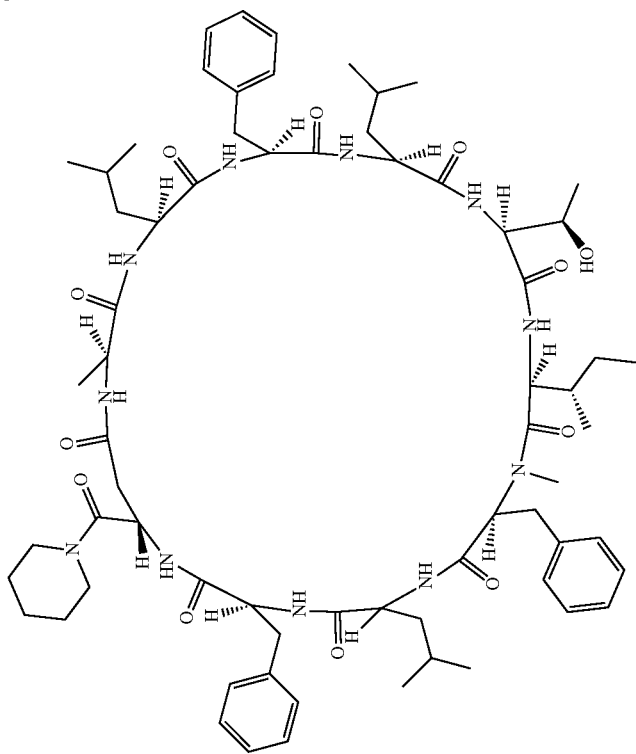
Chiral

TABLE 11-3-1-continued
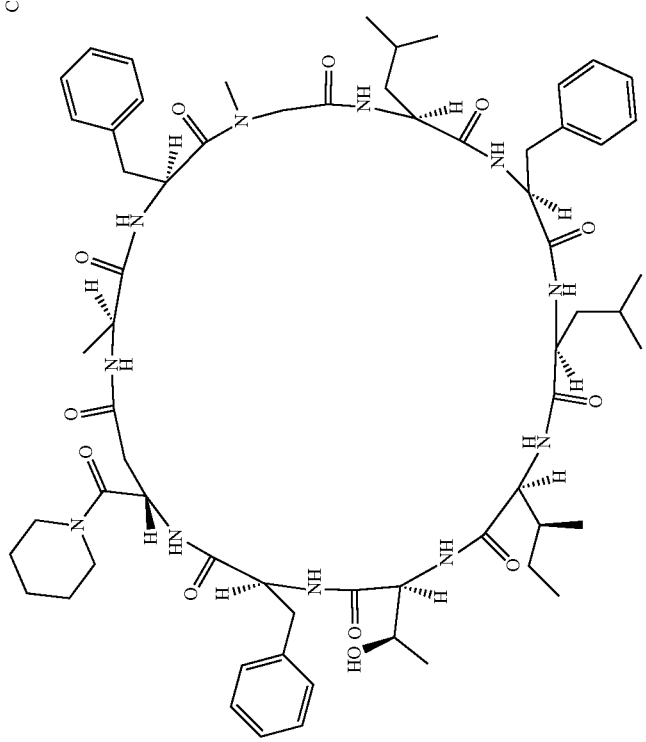
DP-330

TABLE 11-3-1-continued
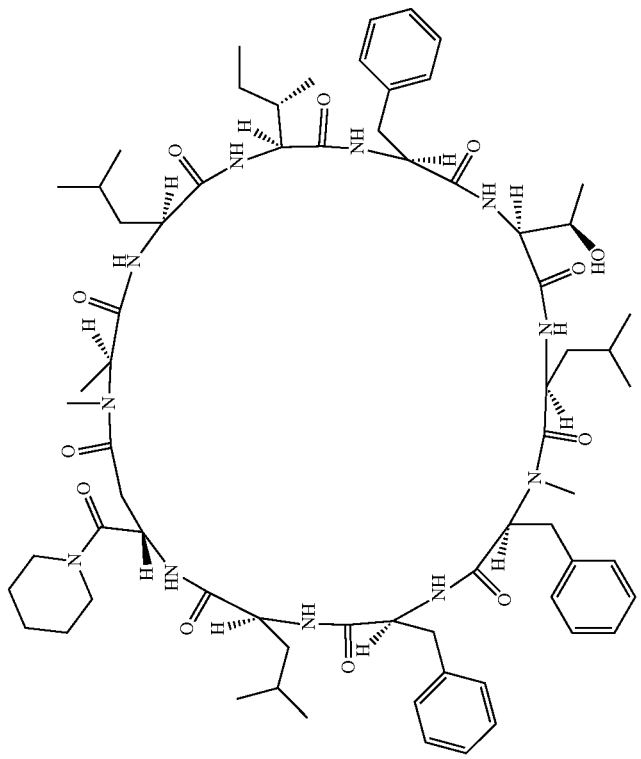
DP-331

TABLE 11-3-1-continued
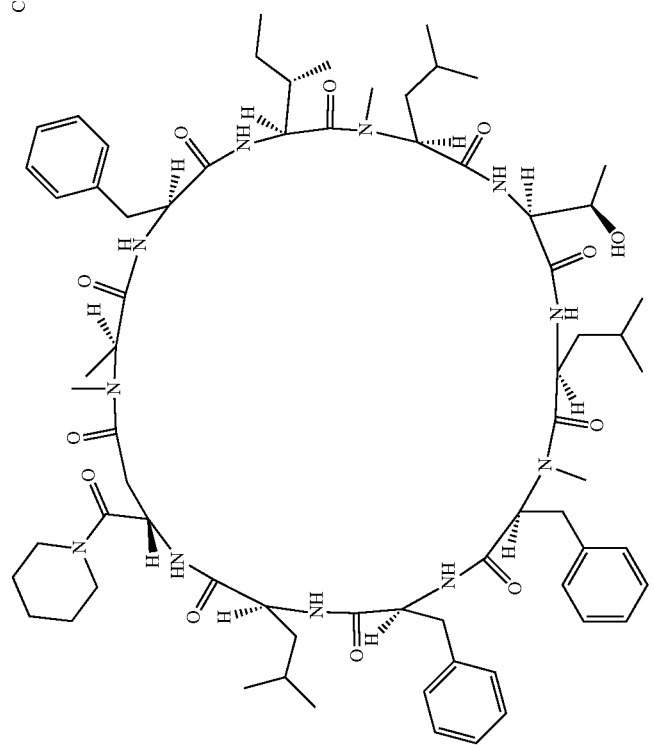
DP-332

TABLE 11-3-1-continued
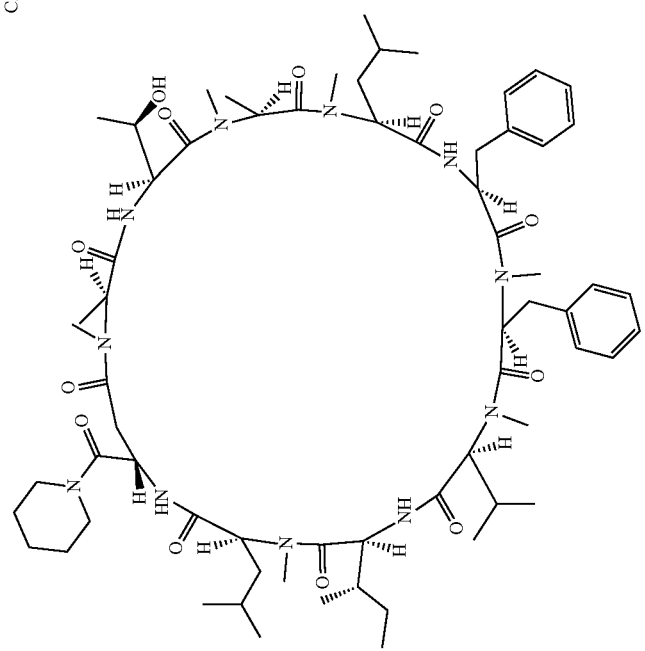
DP-333

TABLE 11-3-1-continued
DP-334

TABLE 11-3-1-continued
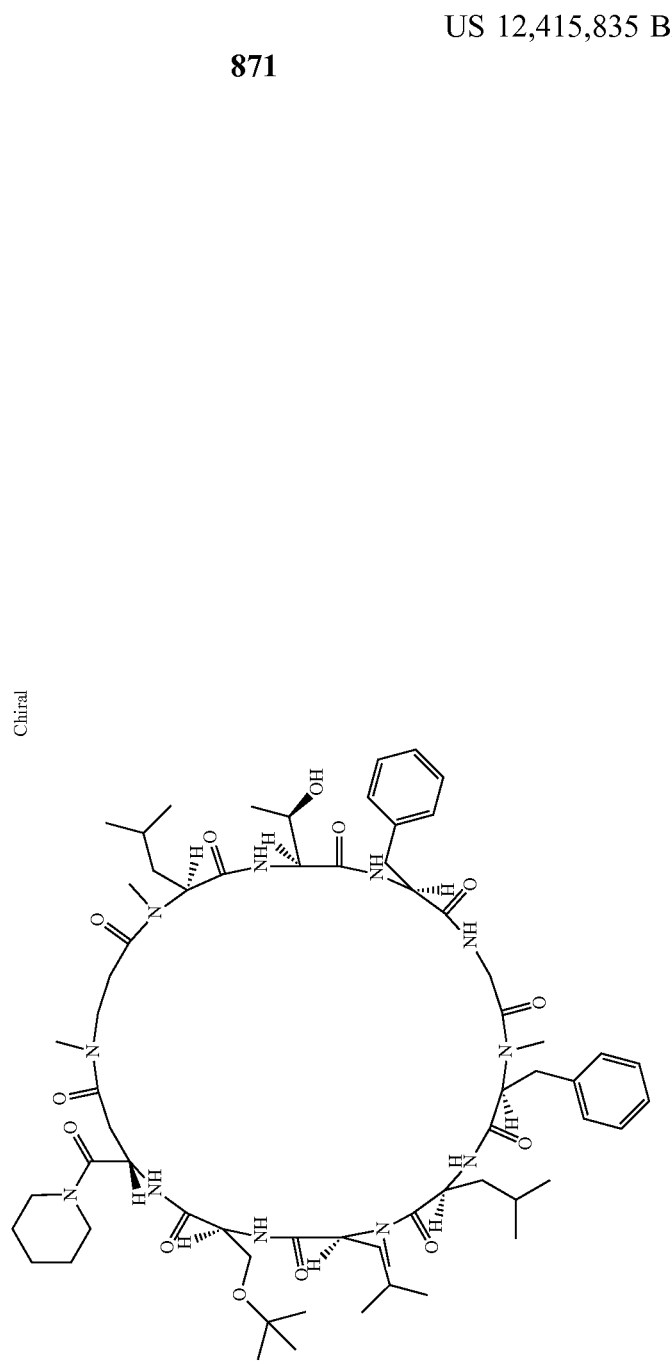
DP-335

TABLE 11-3-1-continued
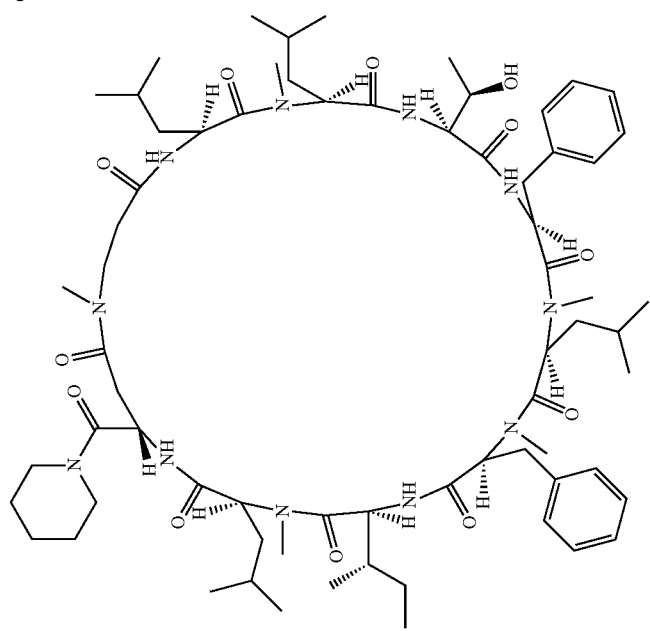
DP-336

TABLE 11-3-1-continued
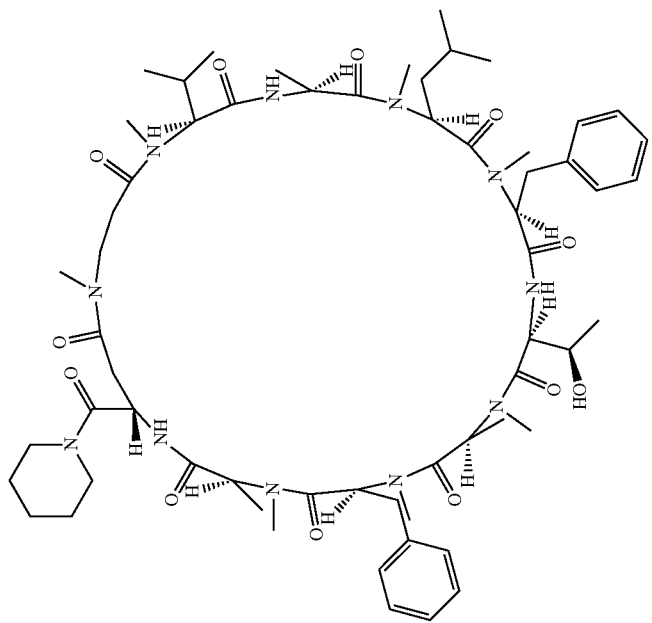
DP-337

TABLE 11-3-1-continued
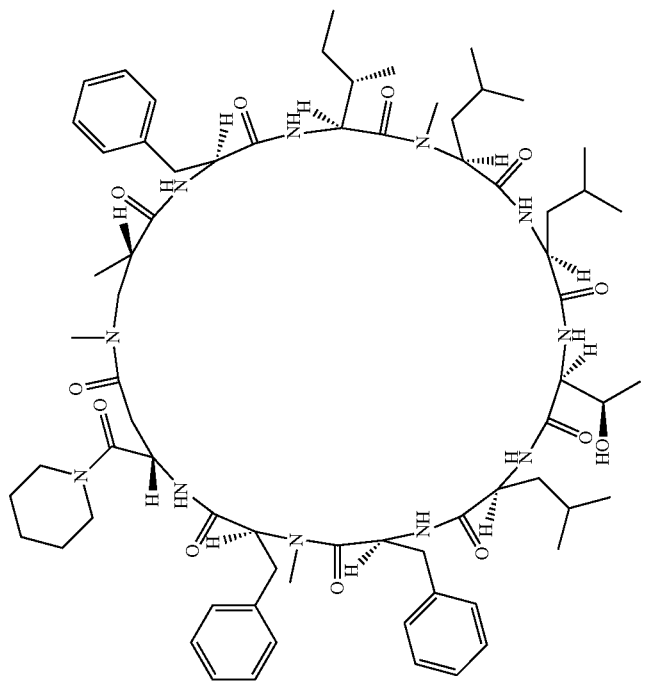
DP-338

TABLE 11-3-1-continued
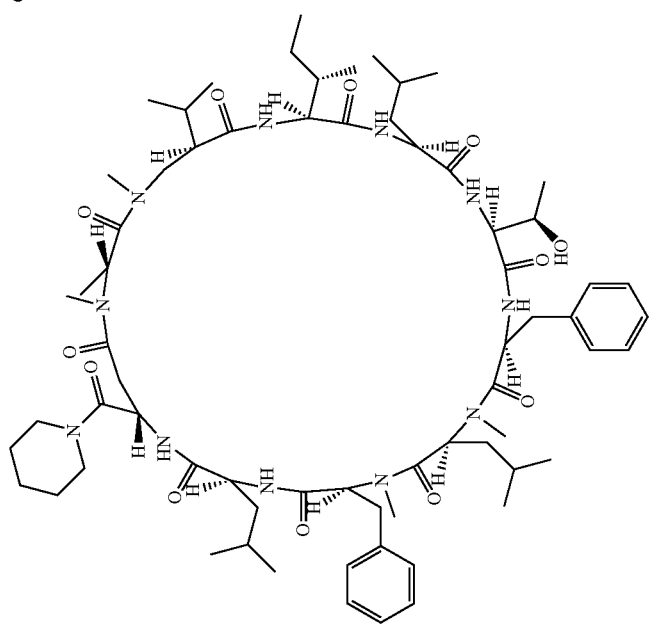
DP-339

TABLE 11-3-1-continued
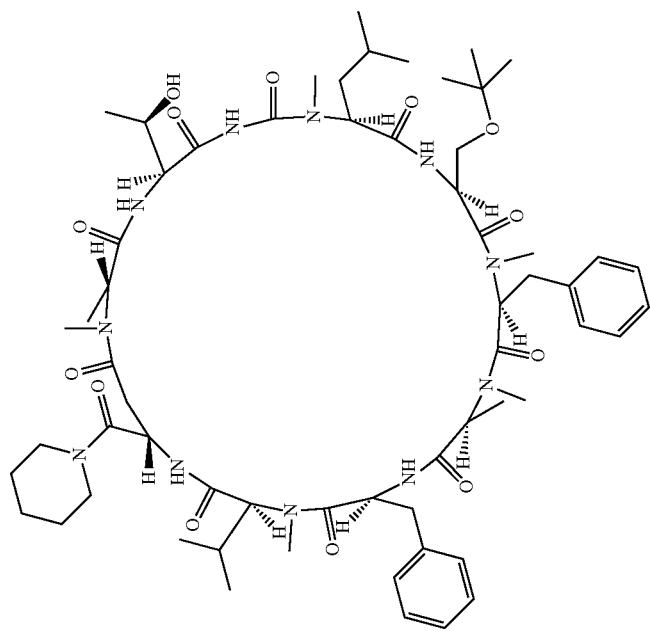
DP-340

TABLE 11-3-1-continued
DP-341
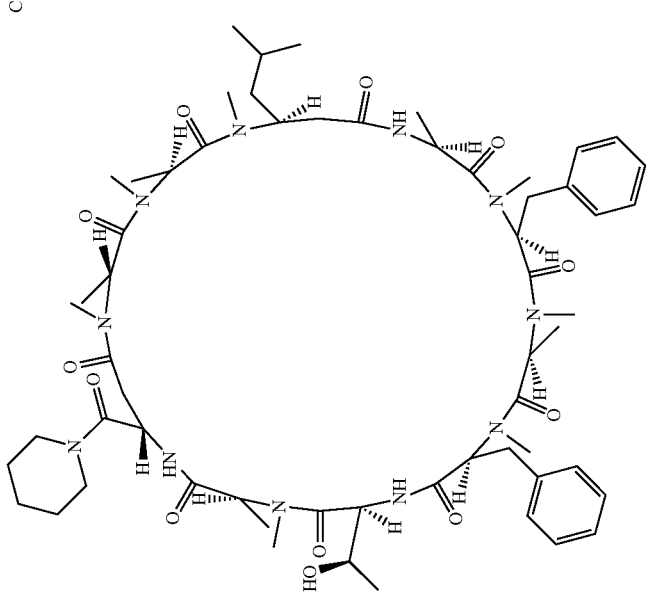

TABLE 11-3-1-continued
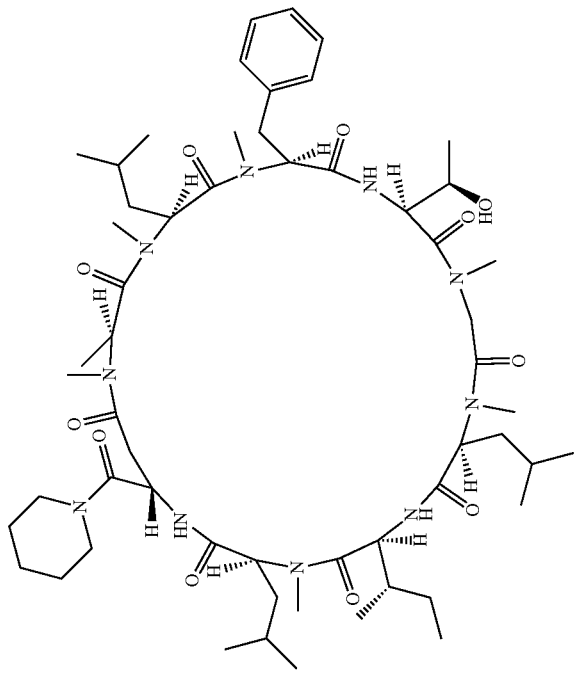
DP-342

TABLE 11-3-1-continued
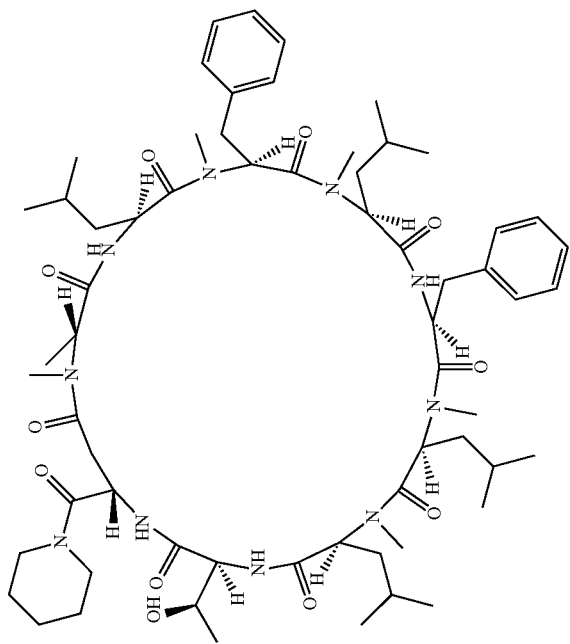
DP-343

TABLE 11-3-1-continued
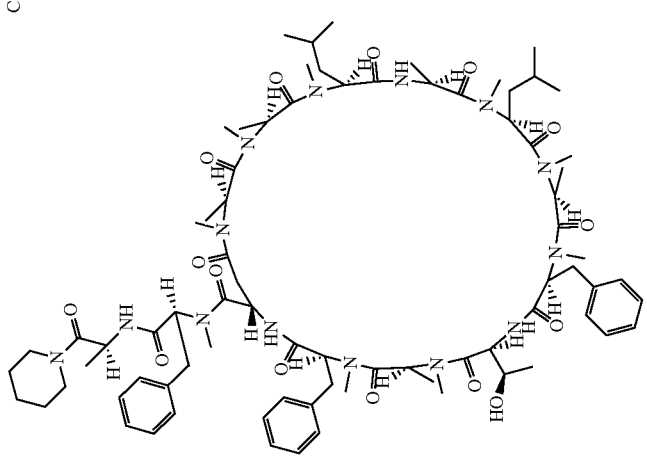
DP-344

TABLE 11-3-1-continued
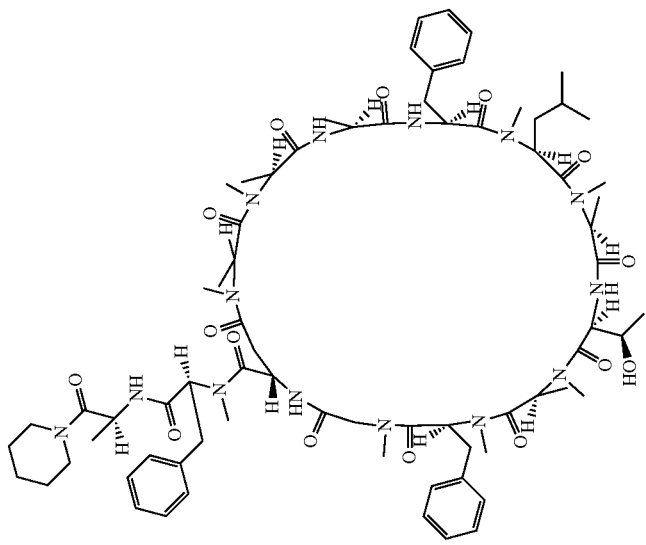
DP-345

TABLE 11-3-1-continued
Chiral
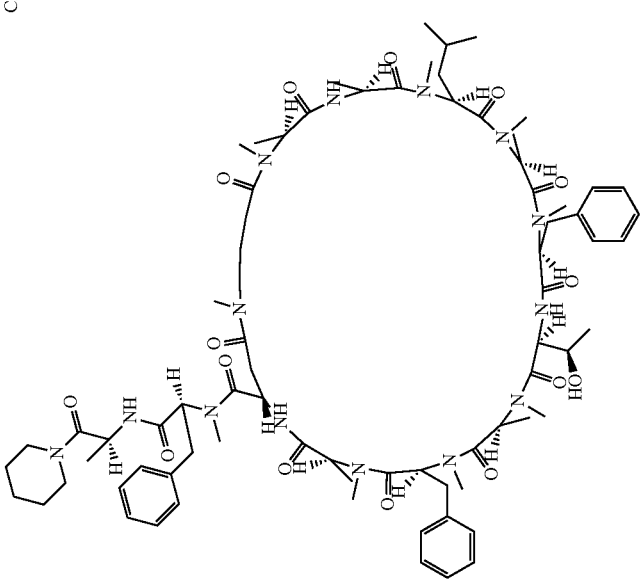
DP-346

TABLE 11-3-1-continued
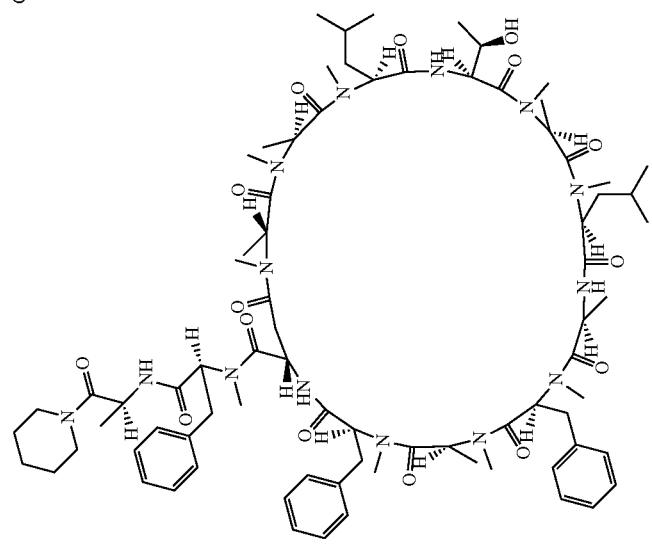
DP-347

TABLE 11-3-1-continued
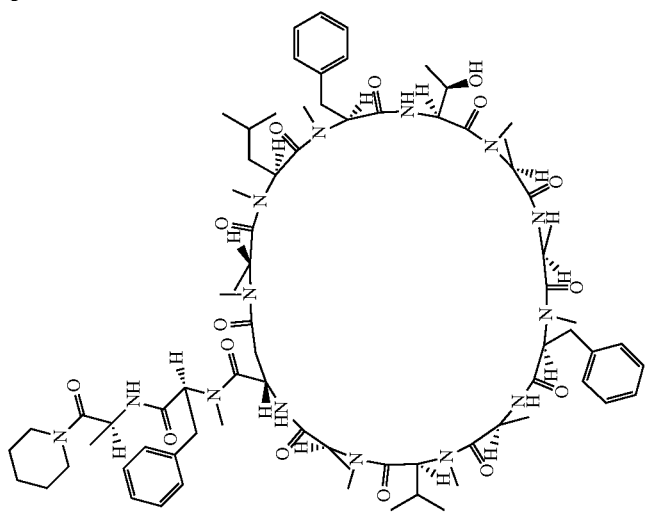
DP-348

TABLE 11-3-1-continued
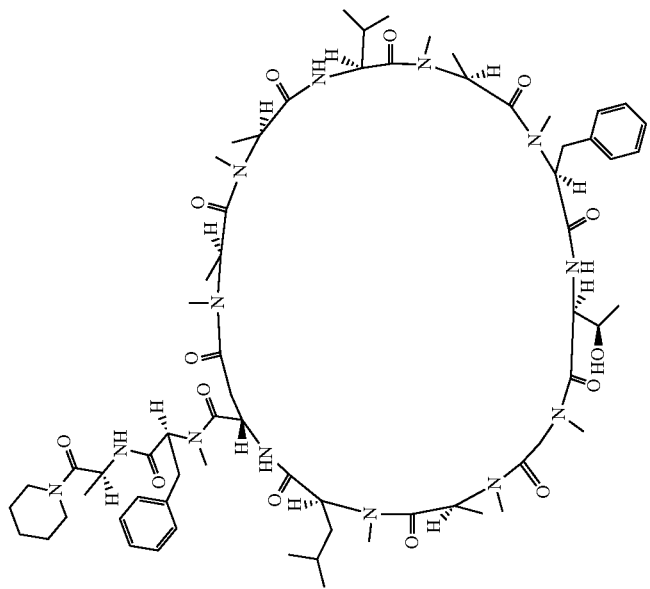
DP-349

TABLE 11-3-1-continued
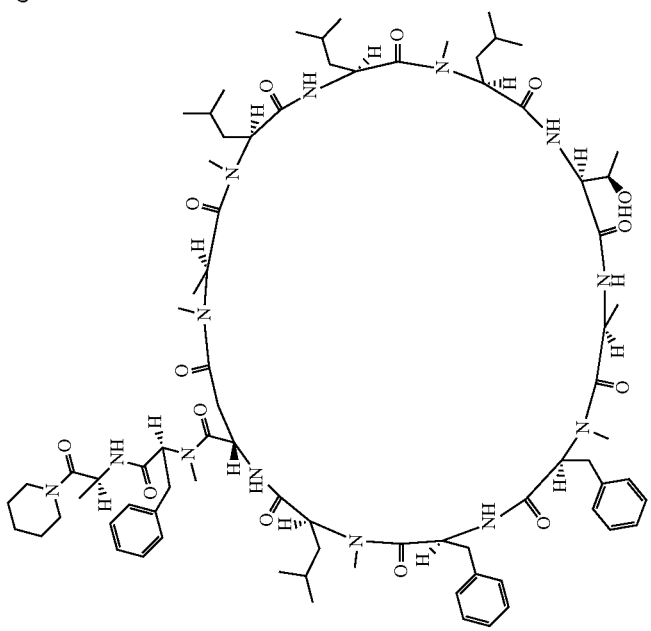
DP-350

TABLE 11-3-1-continued
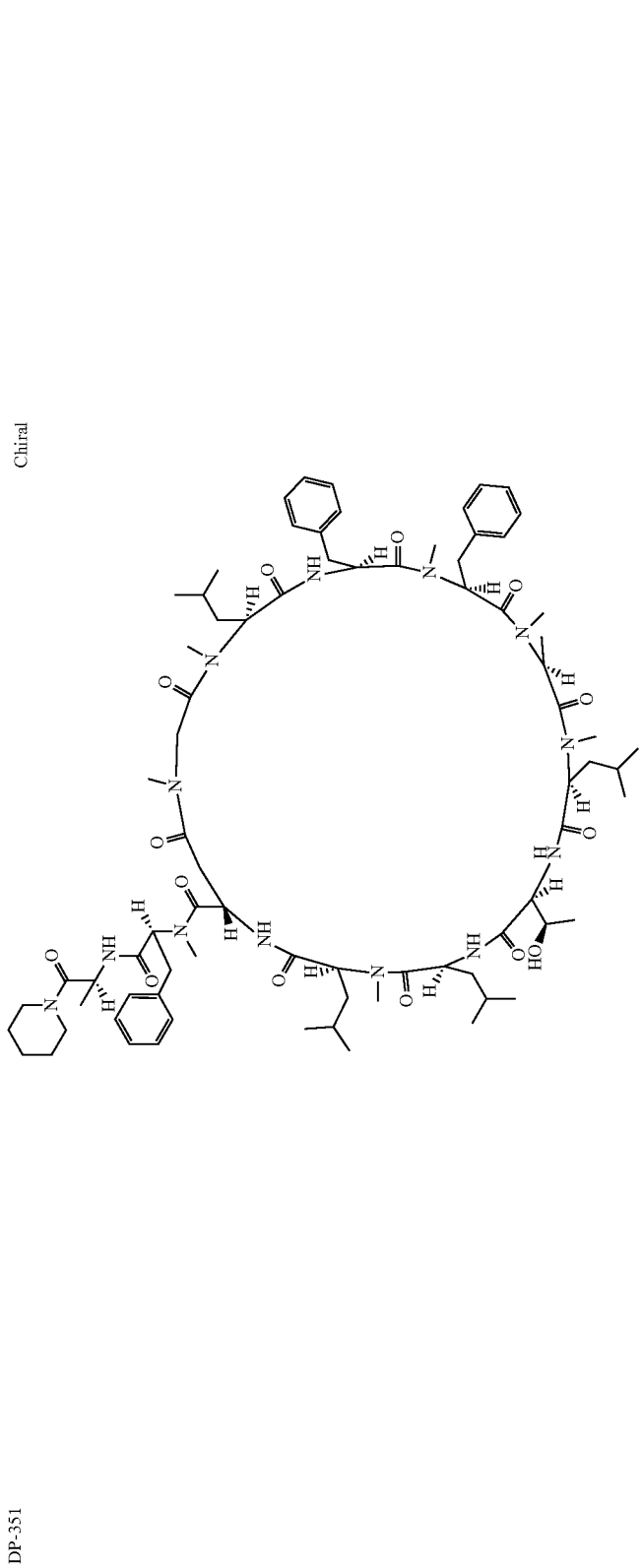
DP-351

TABLE 11-3-1-continued
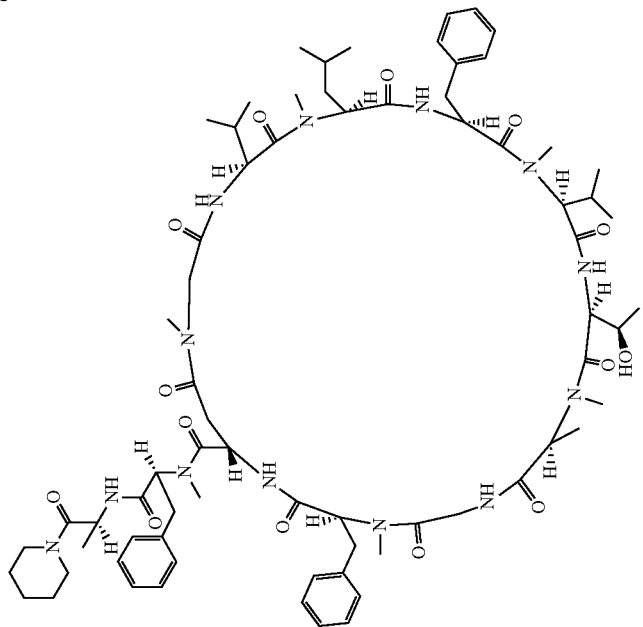
DP-352

TABLE 11-3-1-continued
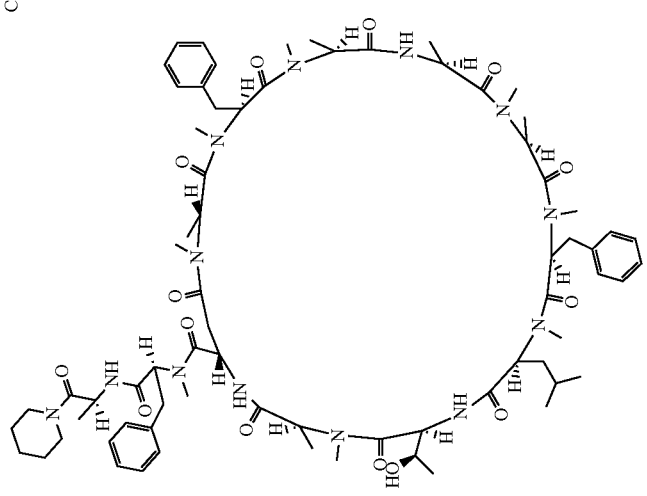
DP-353

TABLE 11-3-1-continued
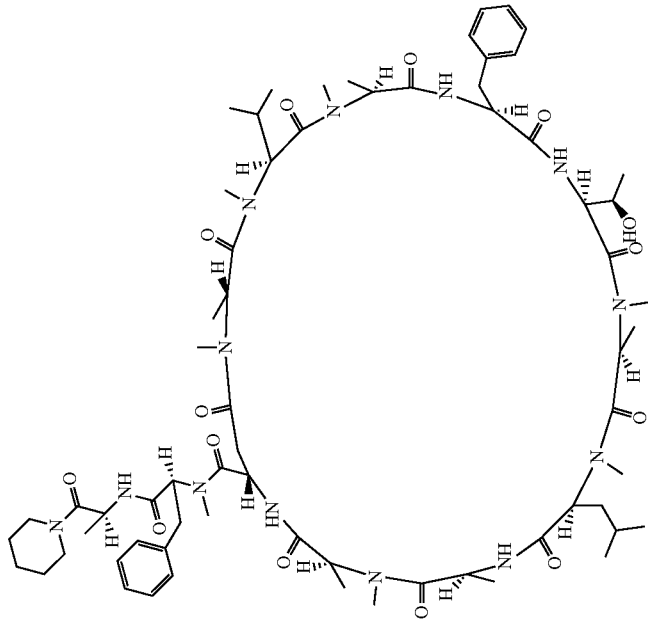
DP-354

TABLE 11-3-1-continued
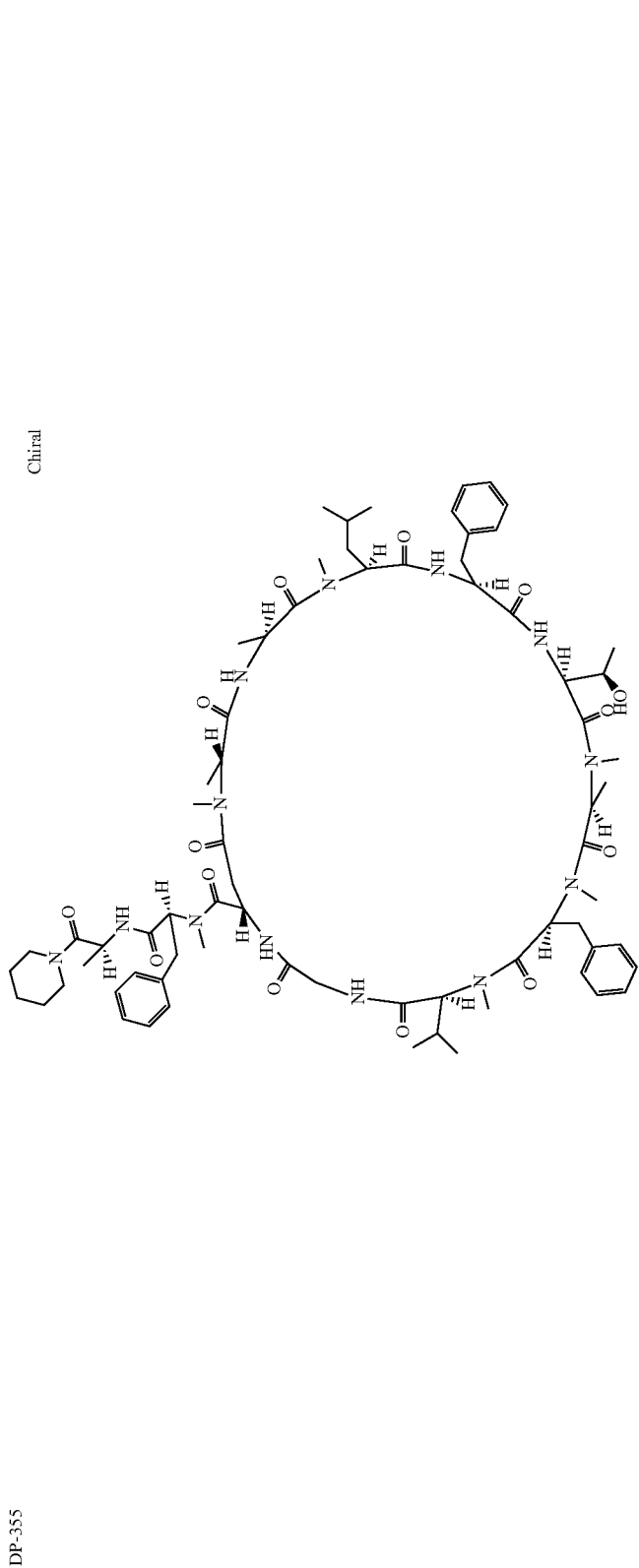
DP-355

TABLE 11-3-1-continued
Chiral
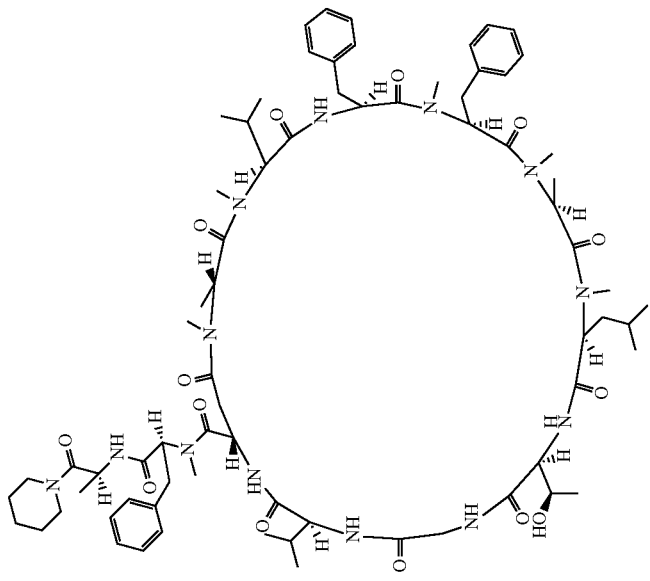
DP-356

TABLE 11-3-1-continued
Chiral
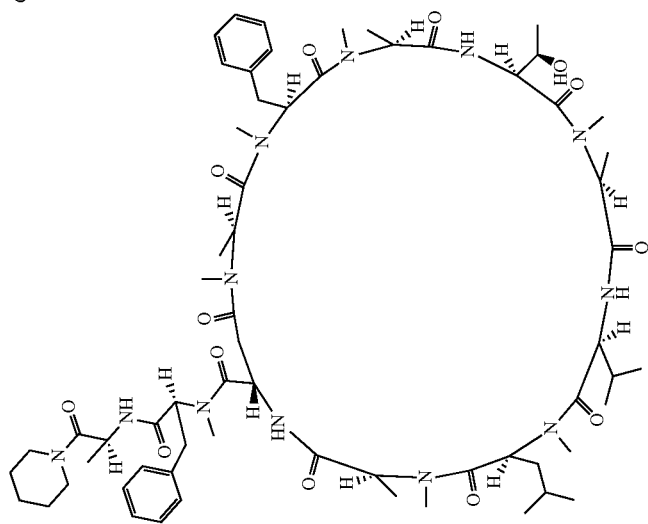
DP-357

TABLE 11-3-1-continued
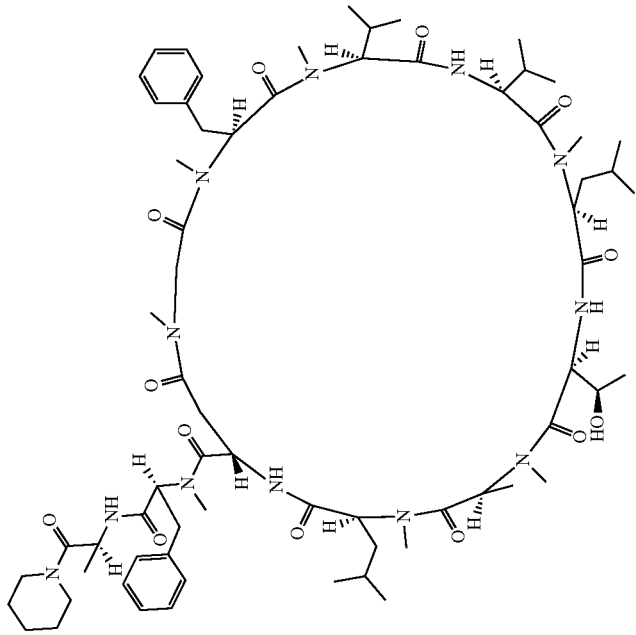
DP-358

TABLE 11-3-1-continued
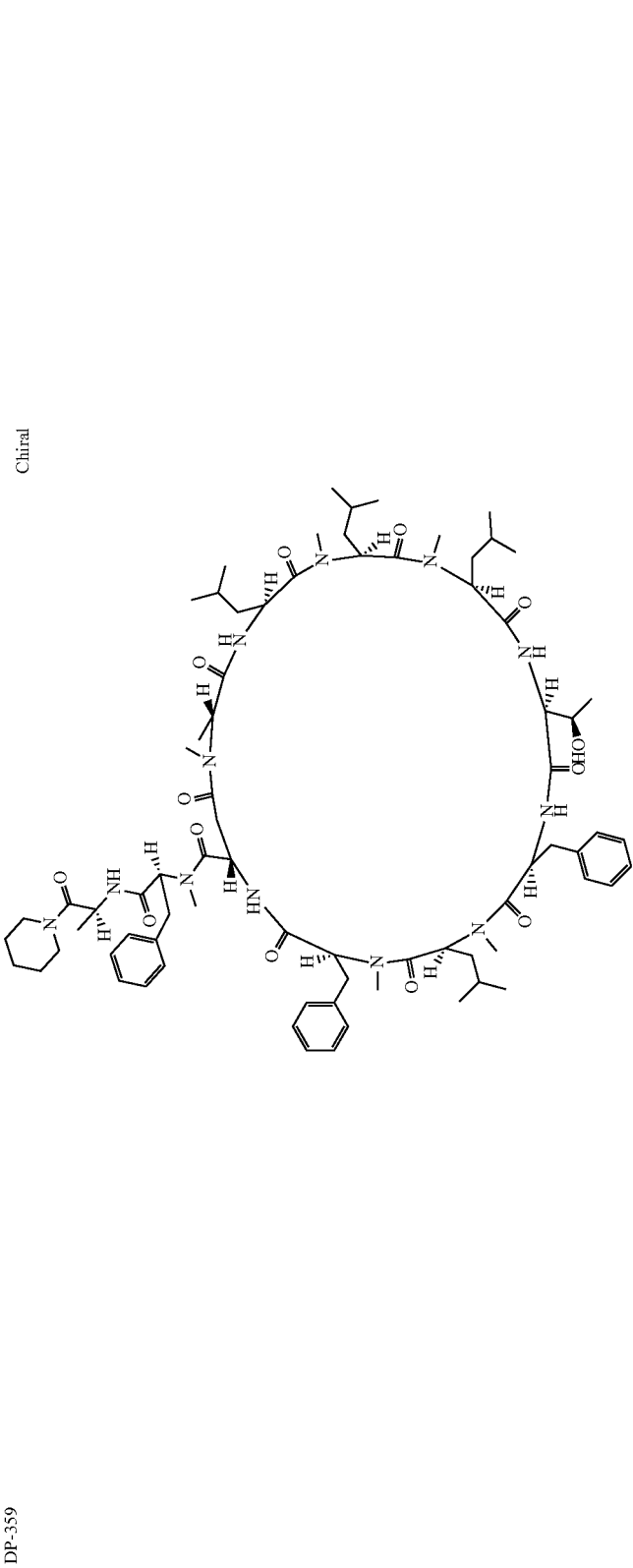
DP-359

TABLE 11-3-1-continued
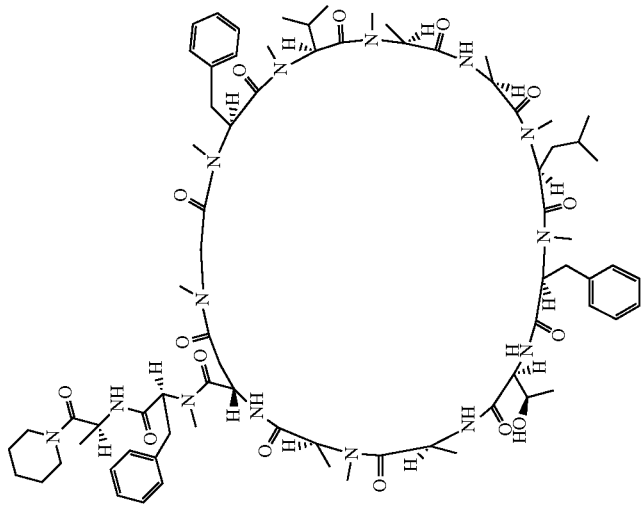
DP-360

TABLE 11-3-1-continued
DP-361
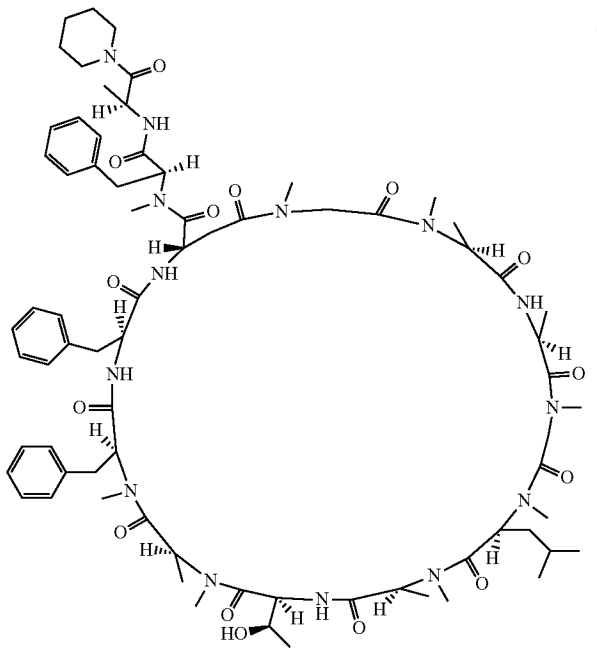

TABLE 11-3-1-continued
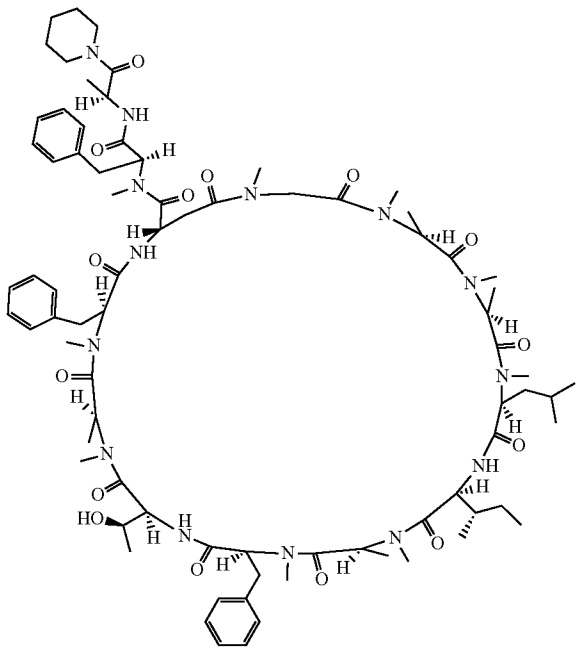
DP-362

TABLE 11-3-1-continued
DP-363
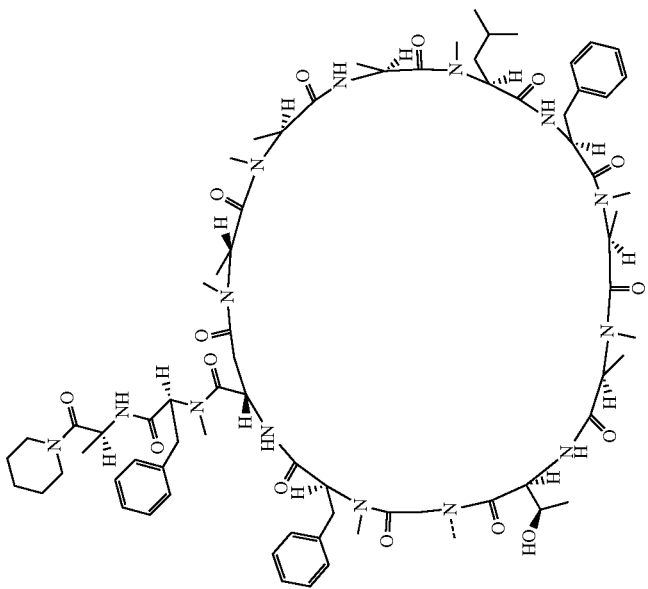

TABLE 11-3-1-continued
Chiral
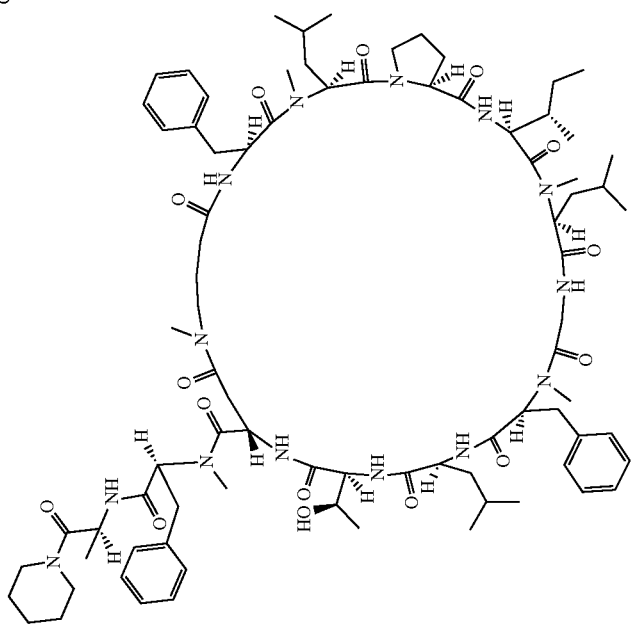
DP-364

TABLE 11-3-1-continued
Chiral
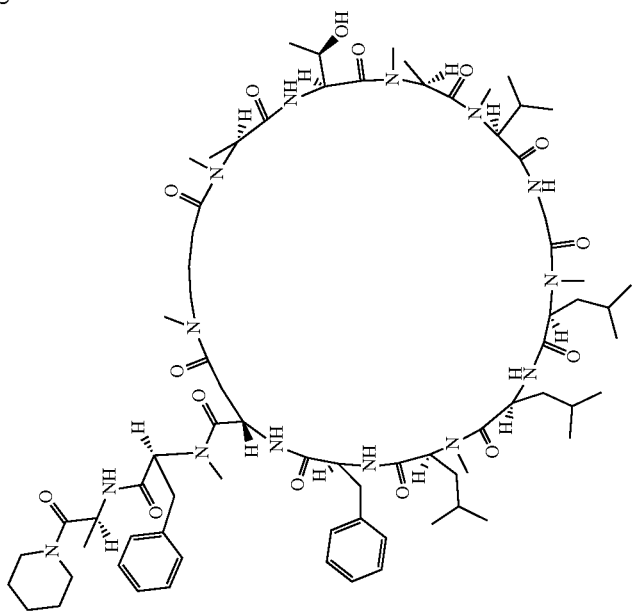
DP-365

TABLE 11-3-1-continued
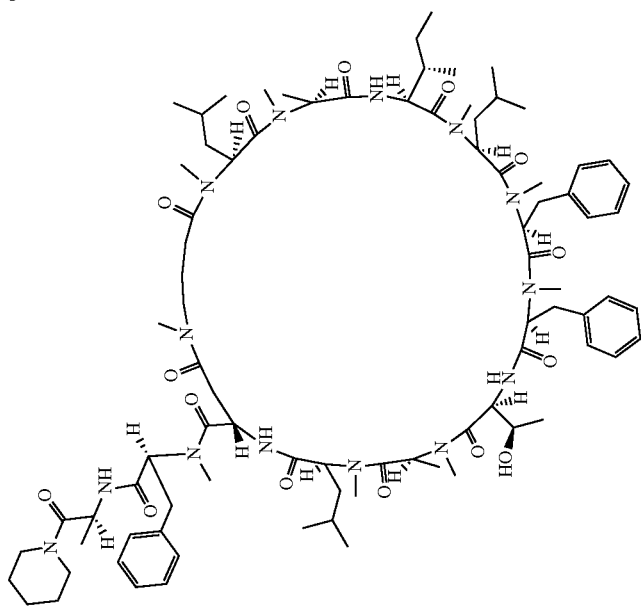
DP-366

TABLE 11-3-1-continued
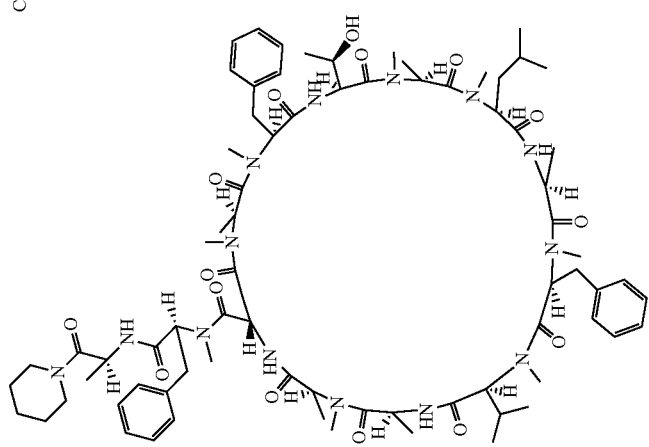
DP-367

TABLE 11-3-1-continued
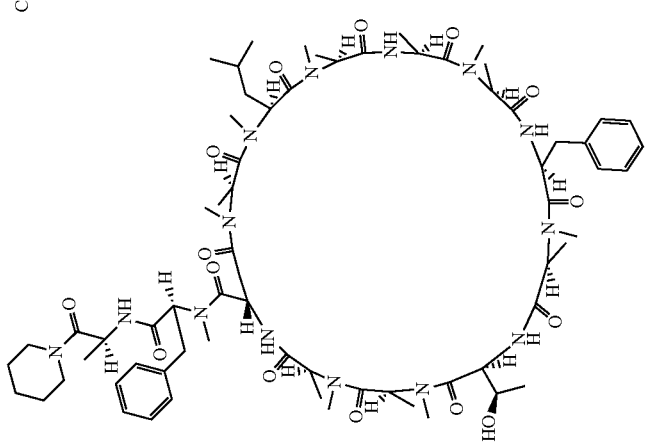
DP-368

TABLE 11-3-1-continued
Chiral
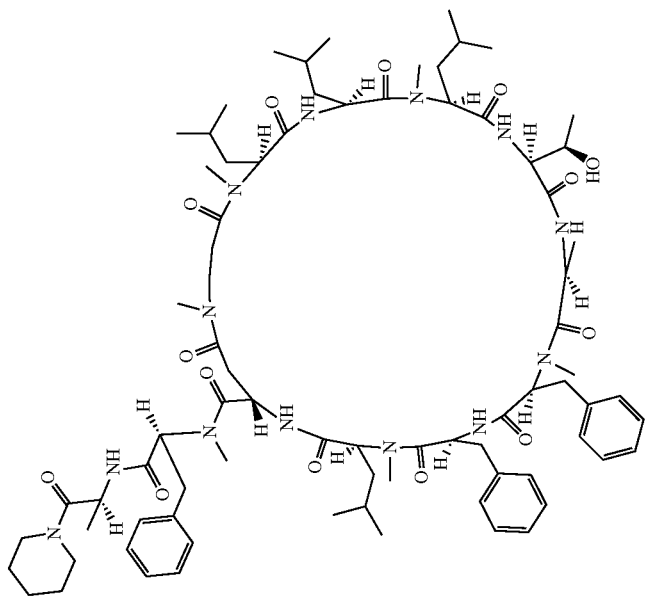
DP-369

TABLE 11-3-1-continued
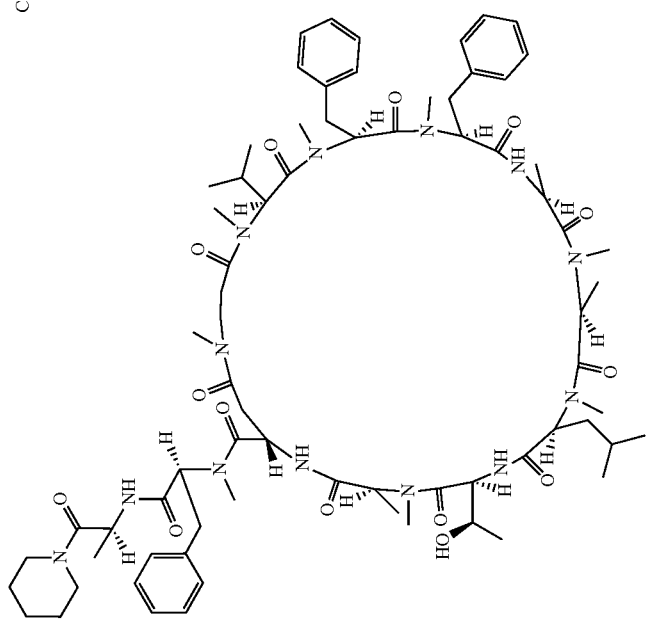
DP-370

TABLE 11-3-1-continued
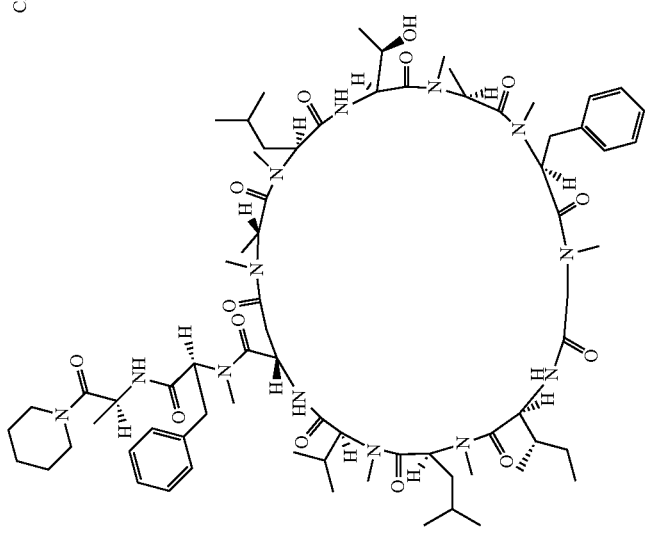
DP-371

TABLE 11-3-1-continued
Chiral
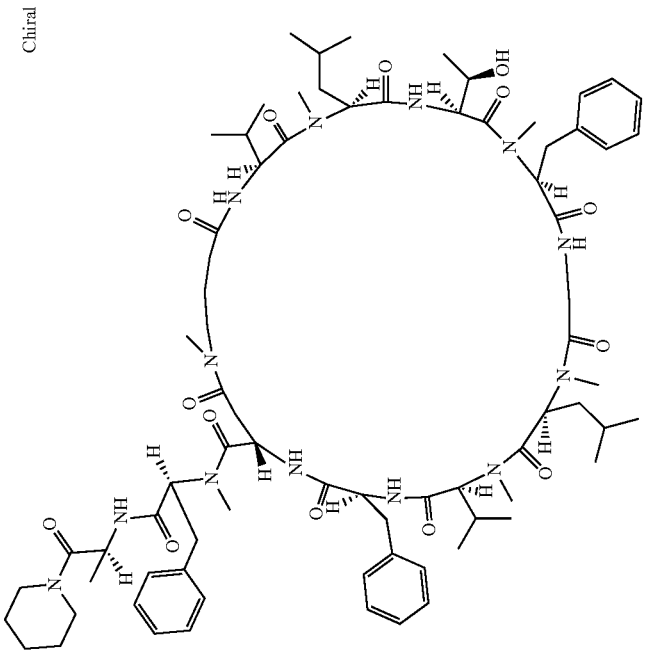
DP-372

TABLE 11-3-1-continued
DP-373
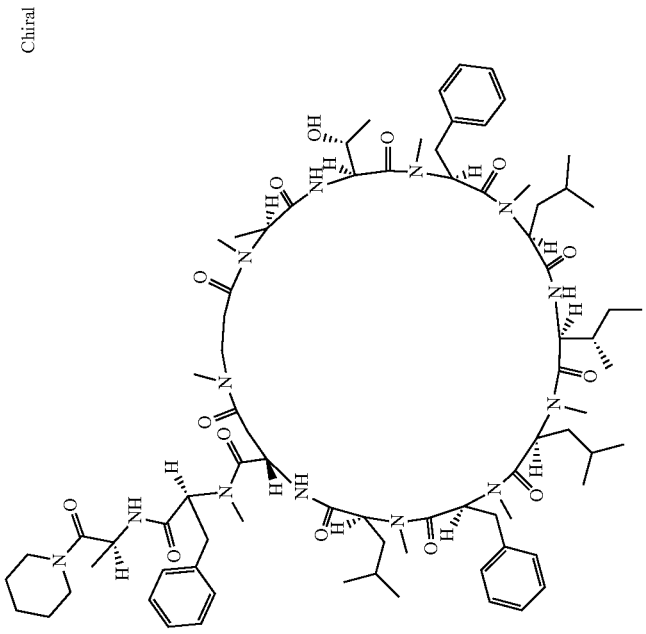

TABLE 11-3-1-continued
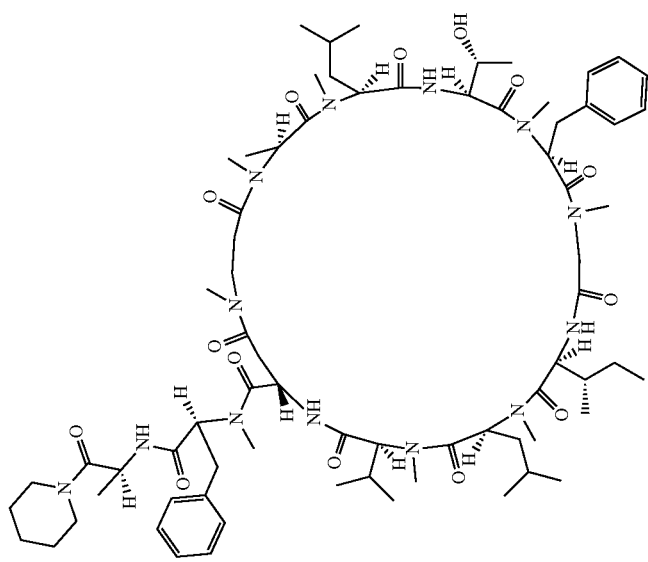
DP-374

TABLE 11-3-1-continued
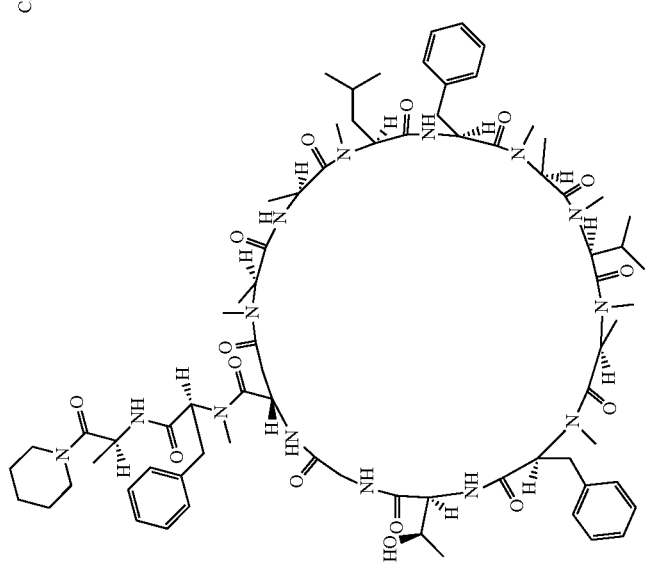
DP-375

TABLE 11-3-1-continued
DP-376
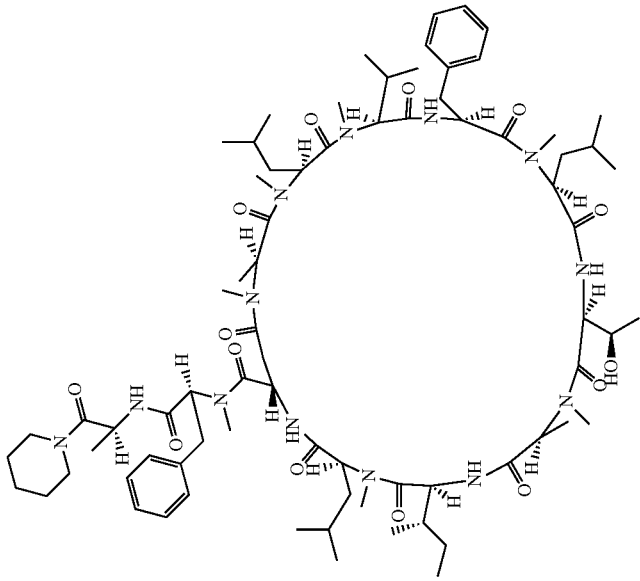

TABLE 11-3-1-continued
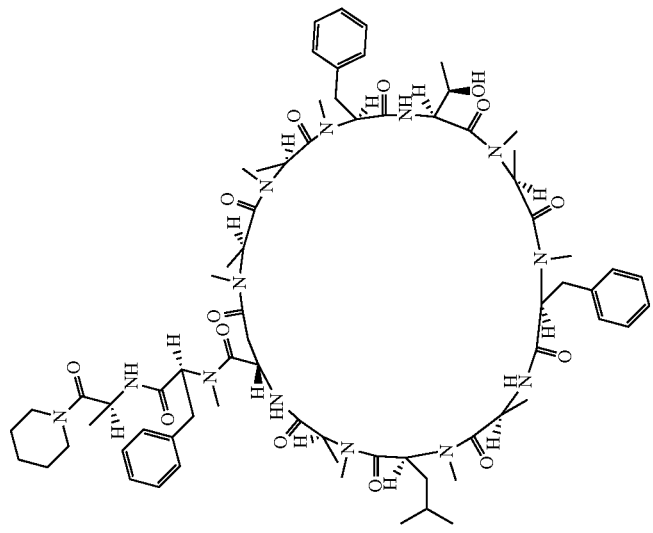
DP-377

TABLE 11-3-1-continued
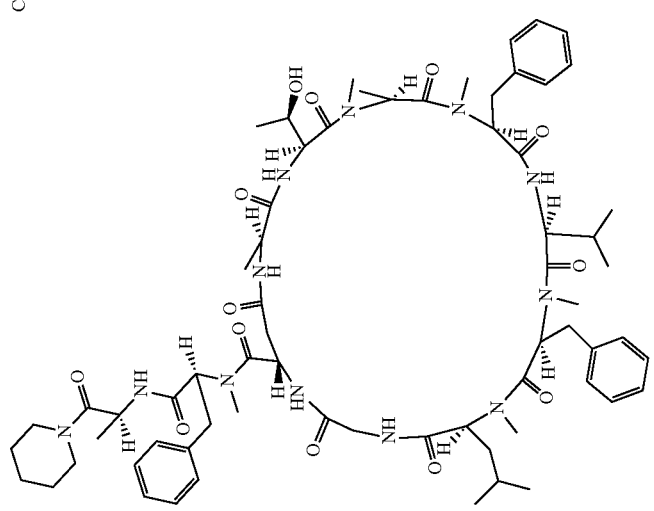
DP-378

TABLE 11-3-1-continued
DP-379
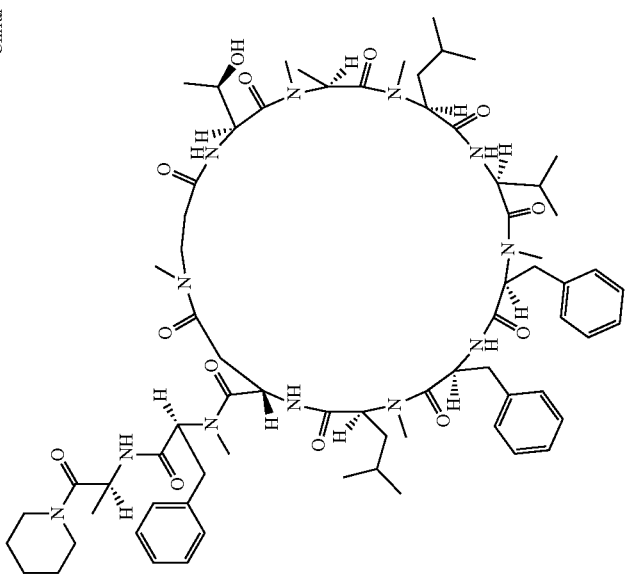

TABLE 11-3-1-continued
DP-380
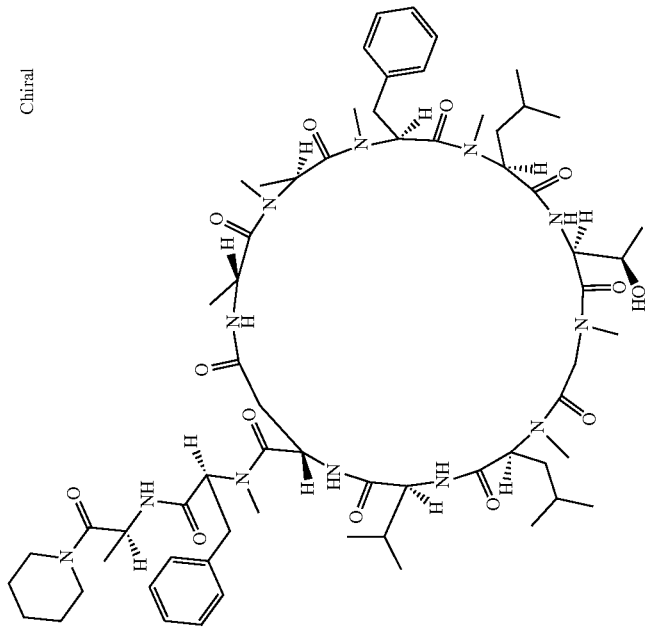

TABLE 11-3-1-continued
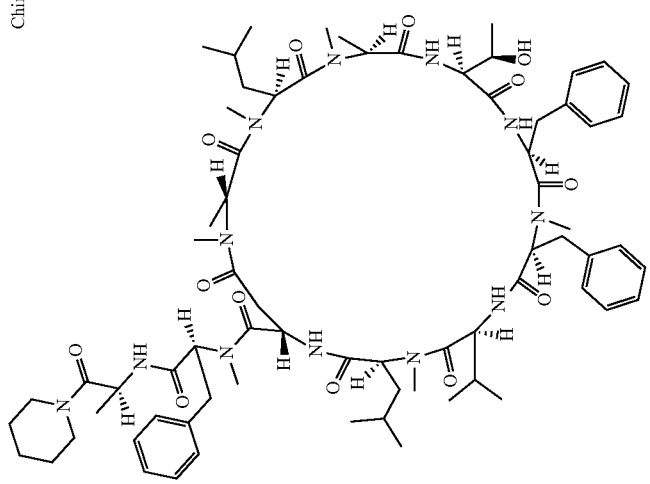
DP-381

TABLE 11-3-1-continued
Chiral
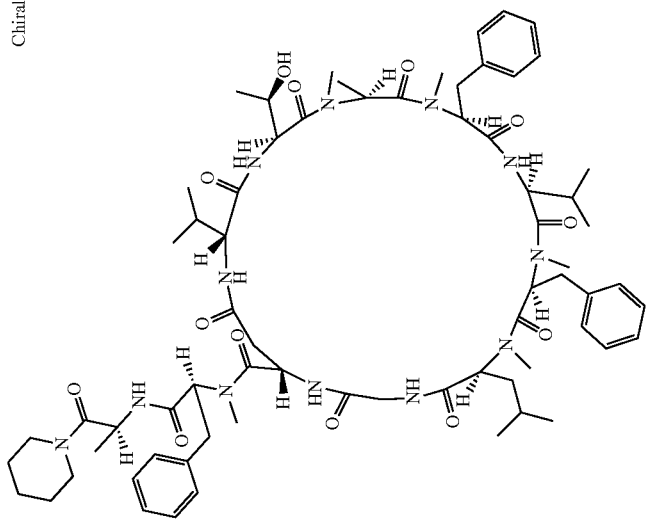
DP-382

TABLE 11-3-1-continued
Chiral
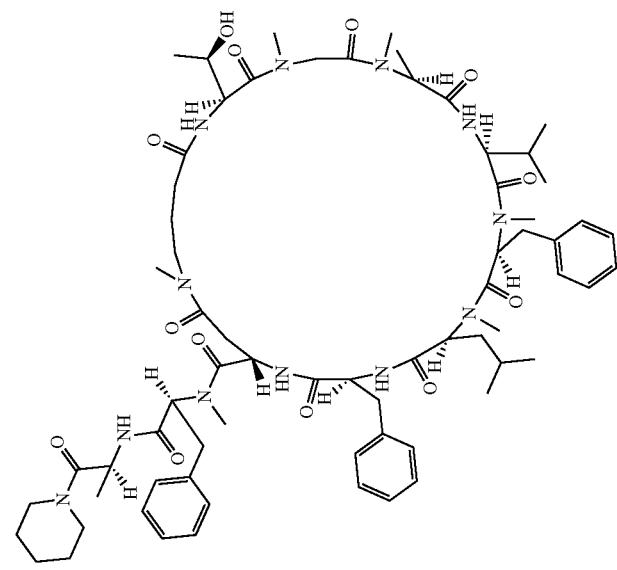
DP-383

TABLE 11-3-1-continued
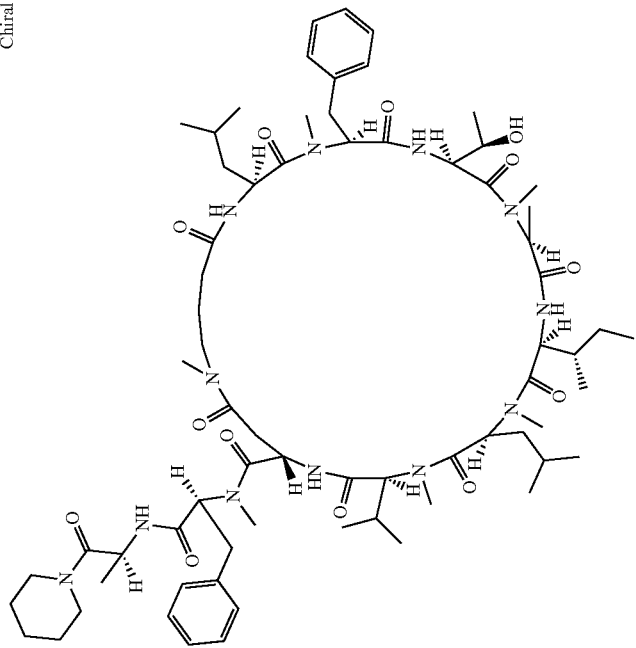
DP-384

TABLE 11-3-1-continued
Chiral
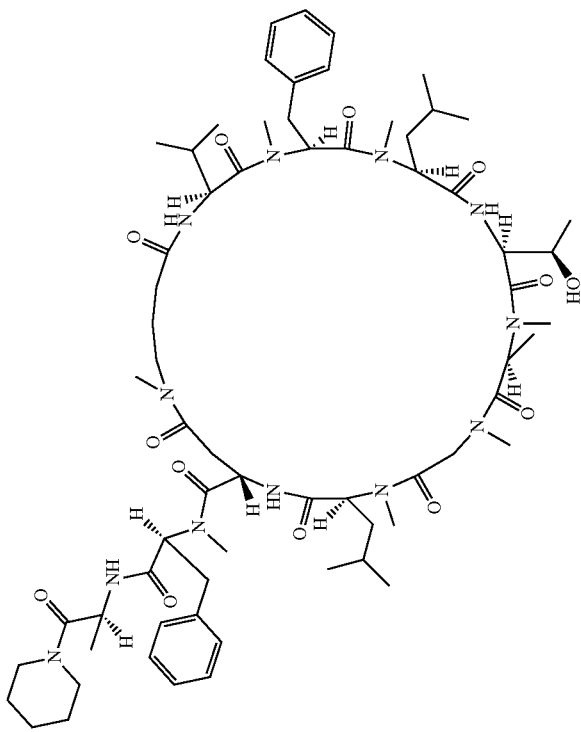
DP-385

TABLE 11-3-1-continued
Chiral
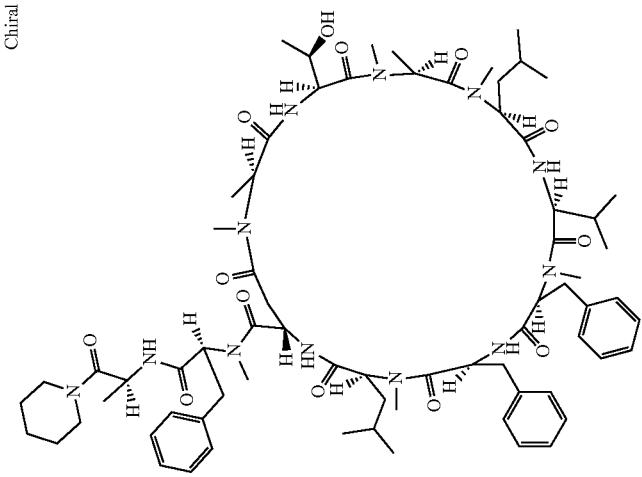
DP-386

TABLE 11-3-1-continued
Chiral
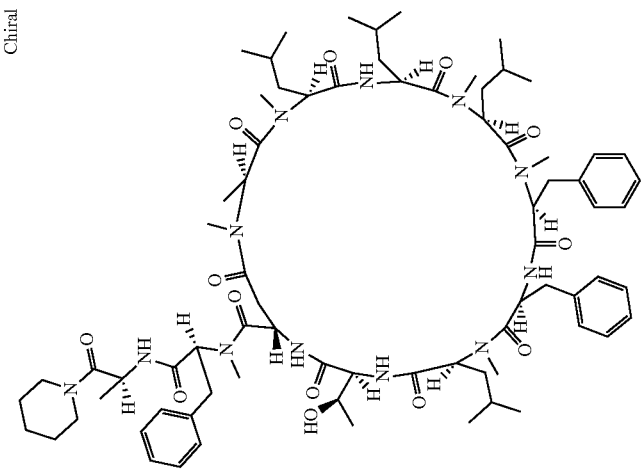
DP-387

TABLE 11-3-1-continued
Chiral
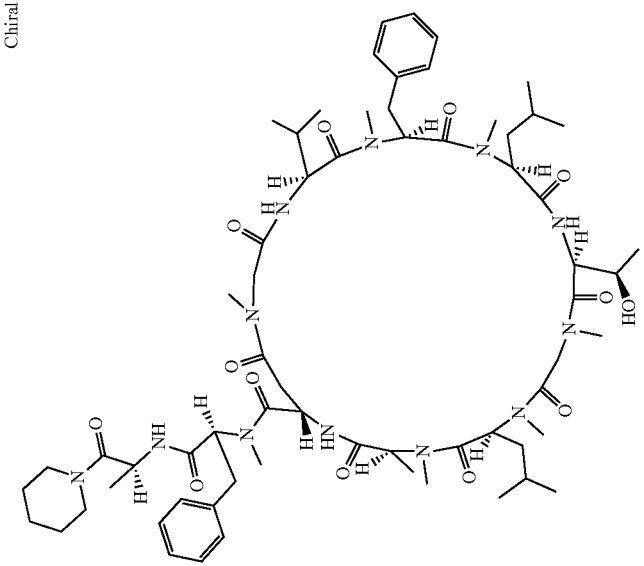
DP-388

TABLE 11-3-1-continued
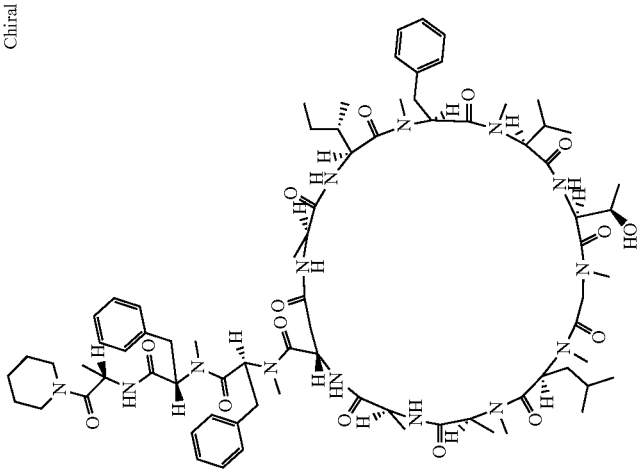
DP-389

TABLE 11-3-1-continued
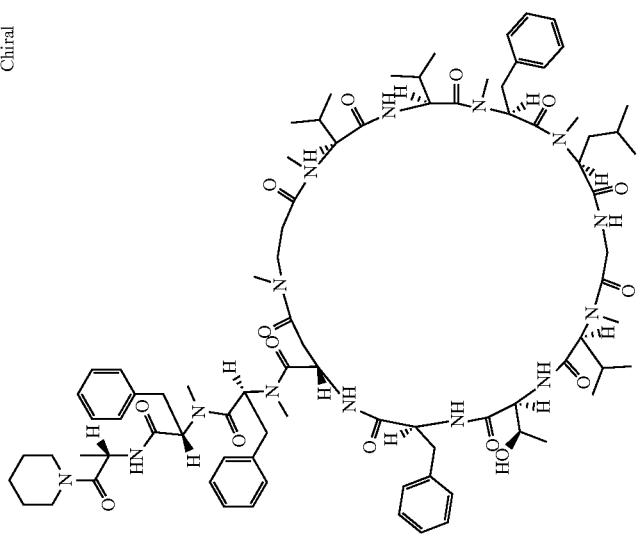
DP-390

TABLE 11-3-1-continued
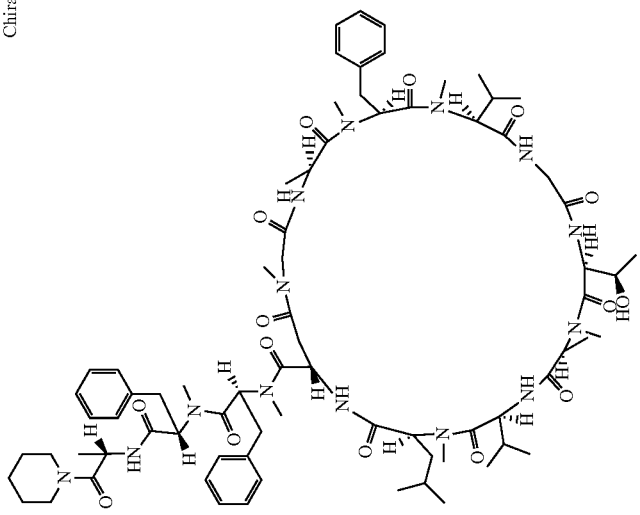
DP-391

TABLE 11-3-1-continued
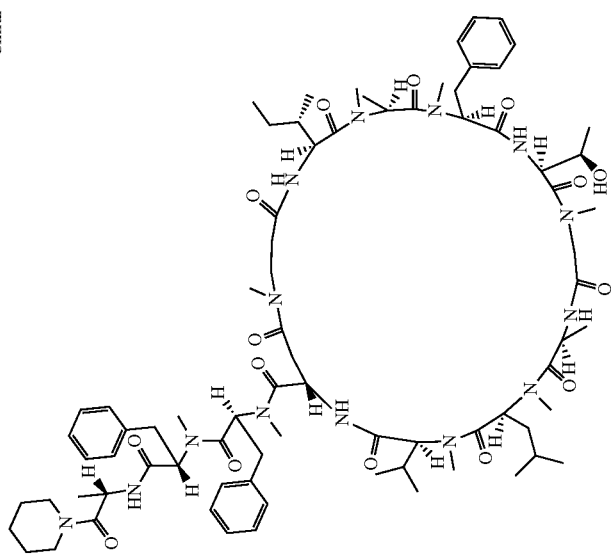
DP-392

TABLE 11-3-1-continued
Chiral
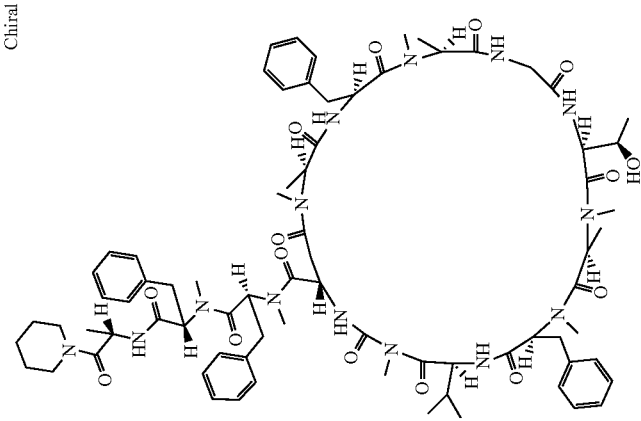
DP-393

TABLE 11-3-1-continued
DP-394
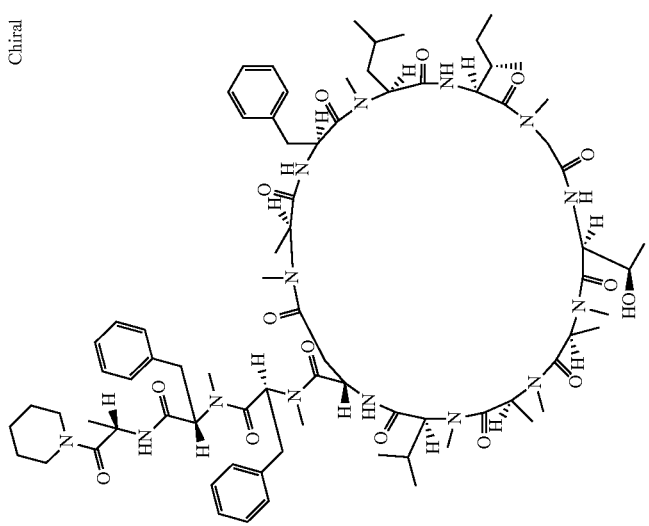

TABLE 11-3-1-continued
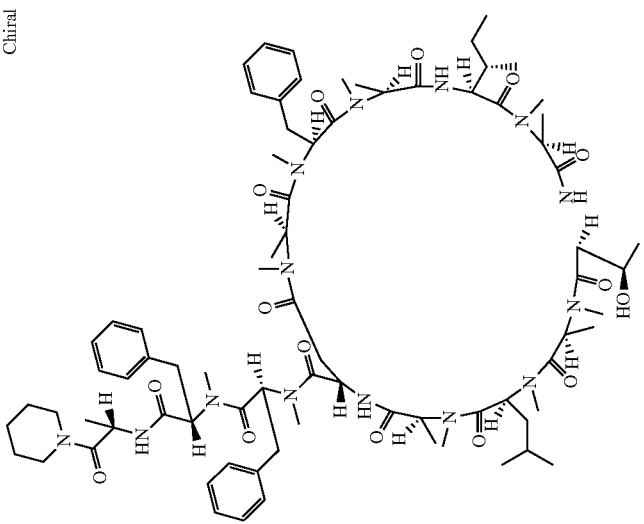
DP-395

TABLE 11-3-1-continued
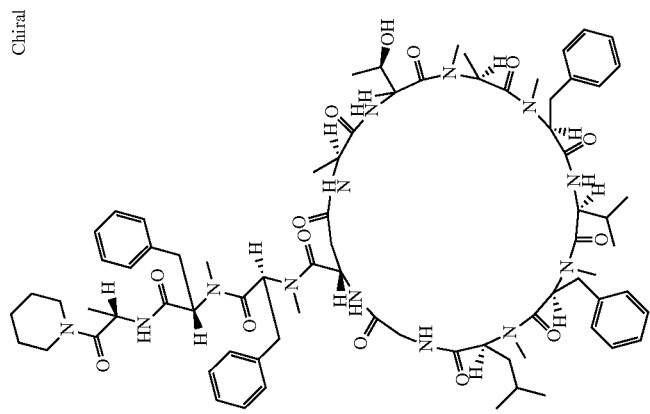
DP-396

TABLE 11-3-1-continued
Chiral
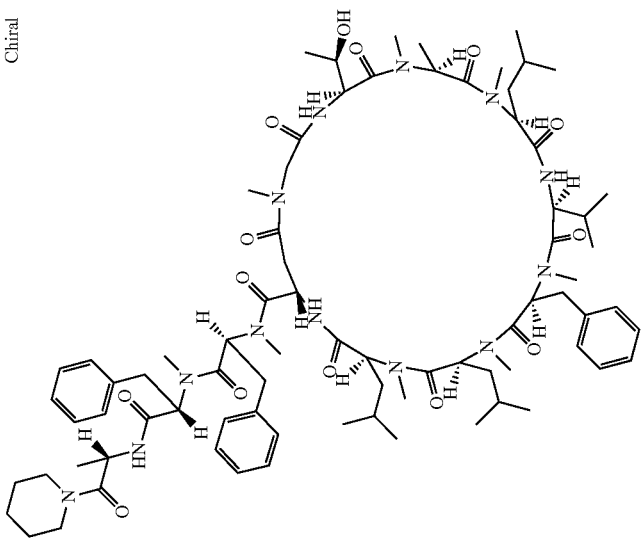
DP-397

TABLE 11-3-1-continued
DP-398
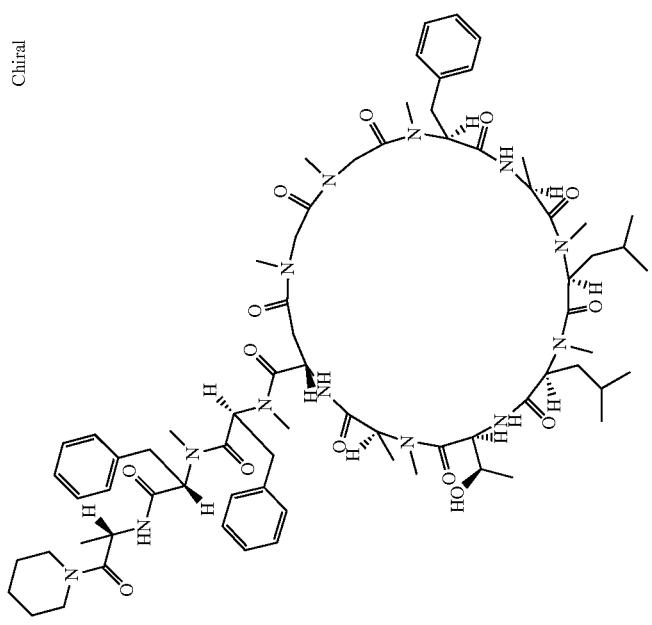

TABLE 11-3-1-continued
DP-399
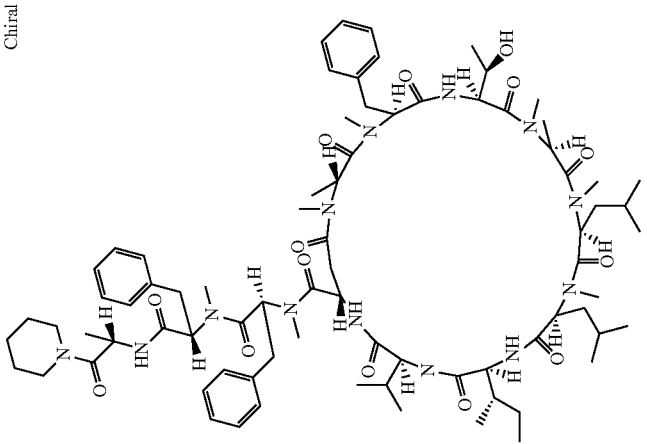
Chiral

TABLE 11-3-1-continued
DP-400
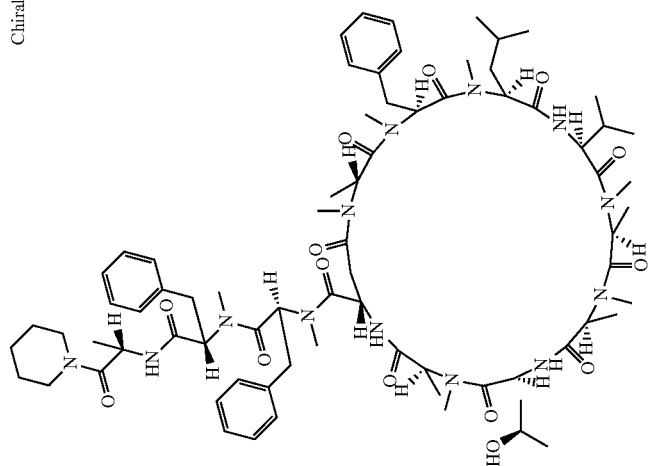

TABLE 11-3-1-continued
DP-401 Chiral
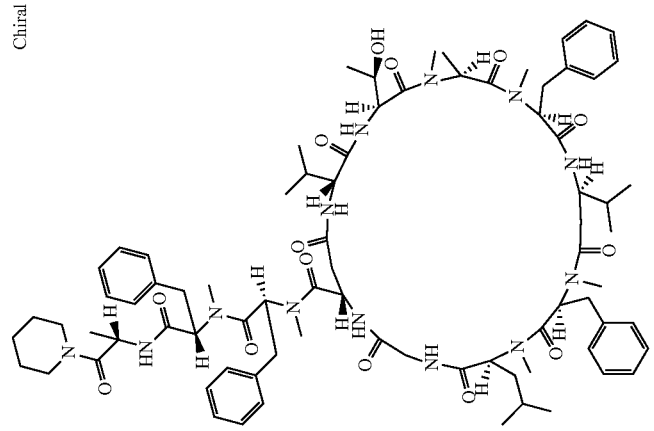

TABLE 11-3-1-continued
DP-402
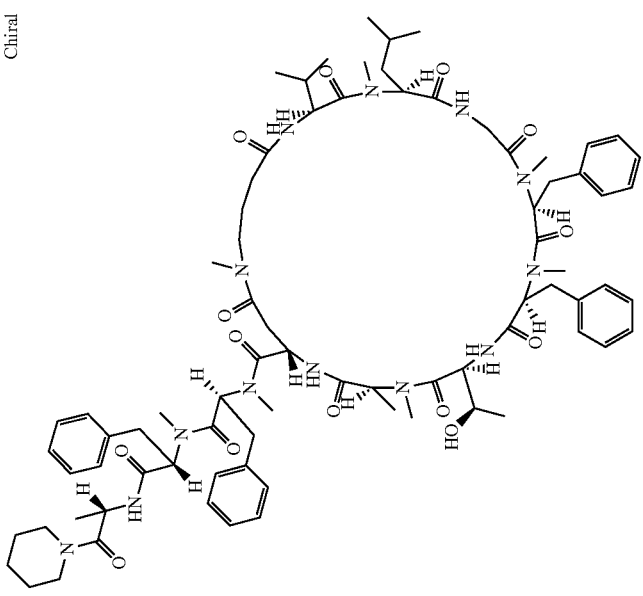

TABLE 11-3-1-continued
DP-403
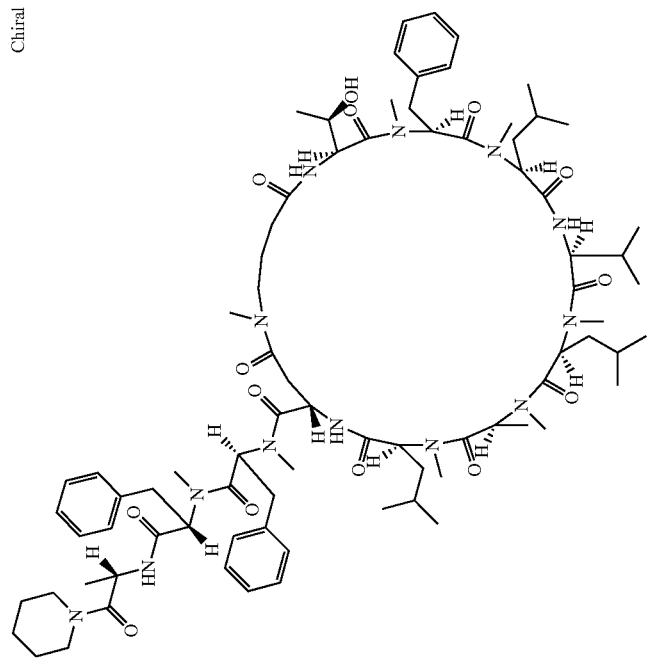

TABLE 11-3-1-continued
DP-404
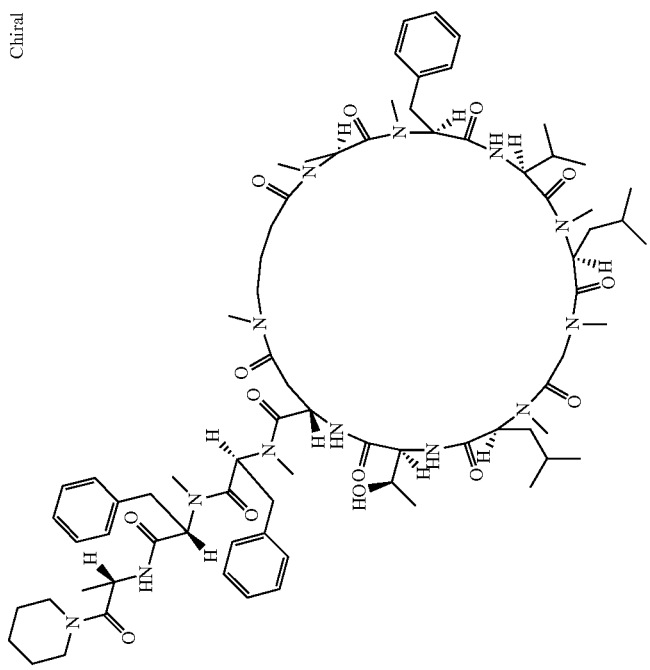

TABLE 11-3-1-continued
DP-405
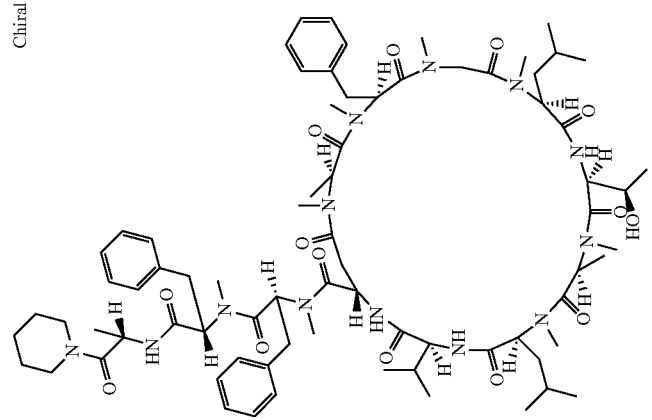
Chiral

TABLE 11-3-1-continued
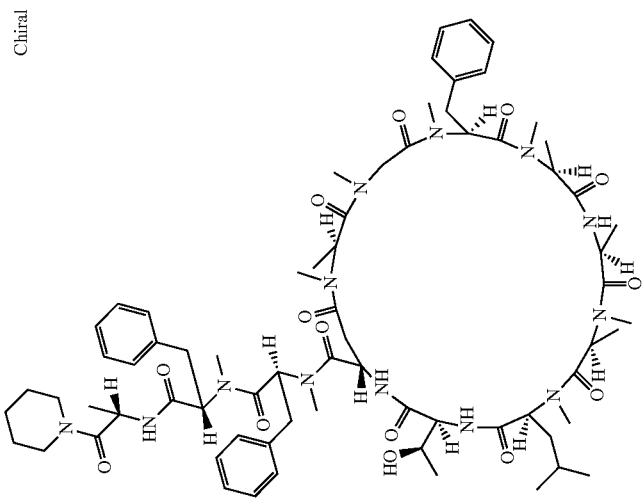
DP-406

TABLE 11-3-1-continued
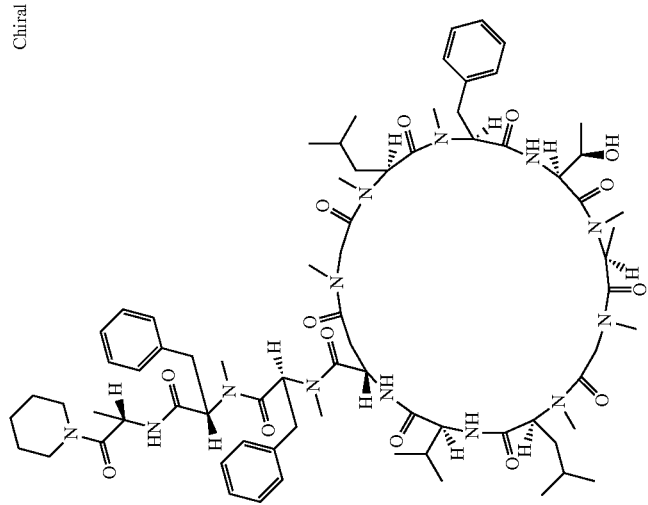
DP-407

TABLE 11-3-1-continued
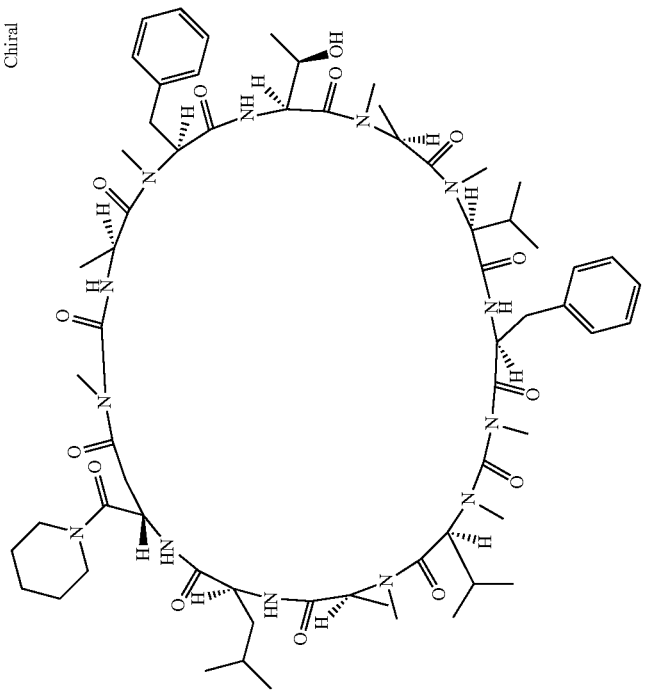
DP-408

TABLE 11-3-1-continued
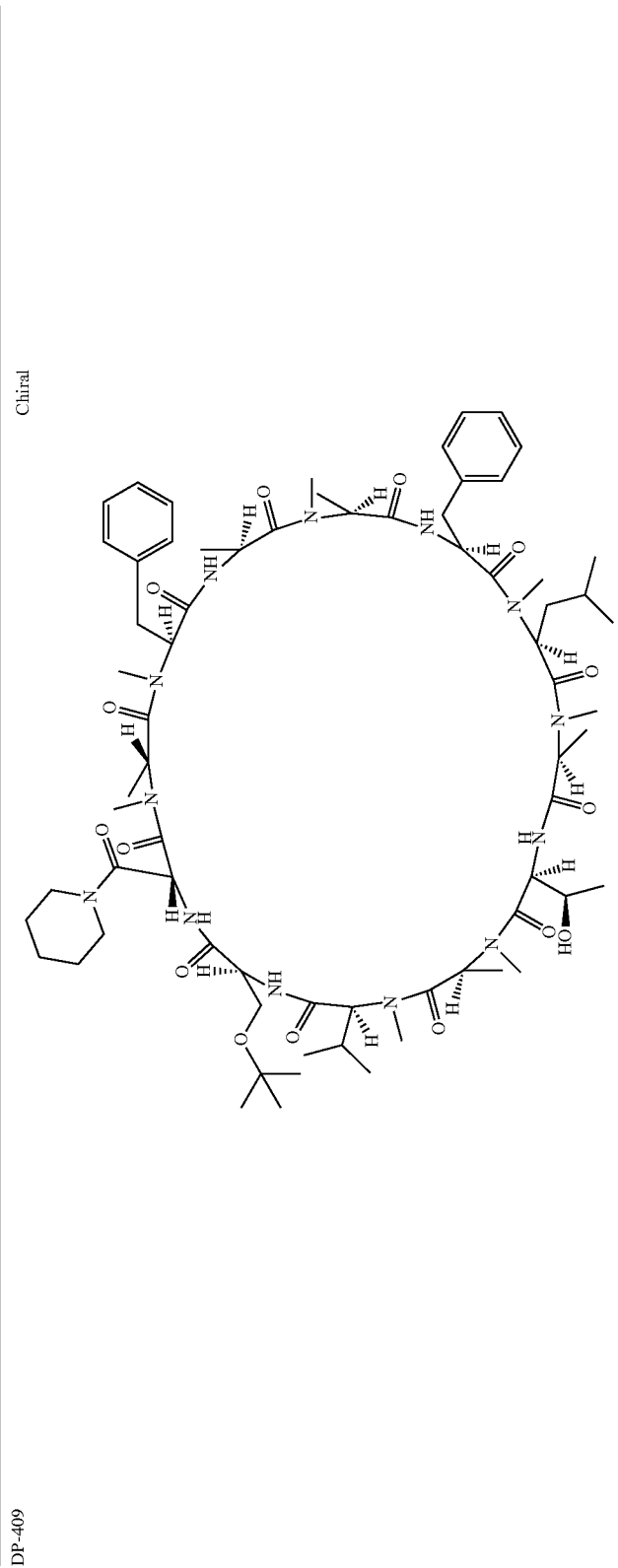
DP-409

TABLE 11-3-1-continued
DP-410
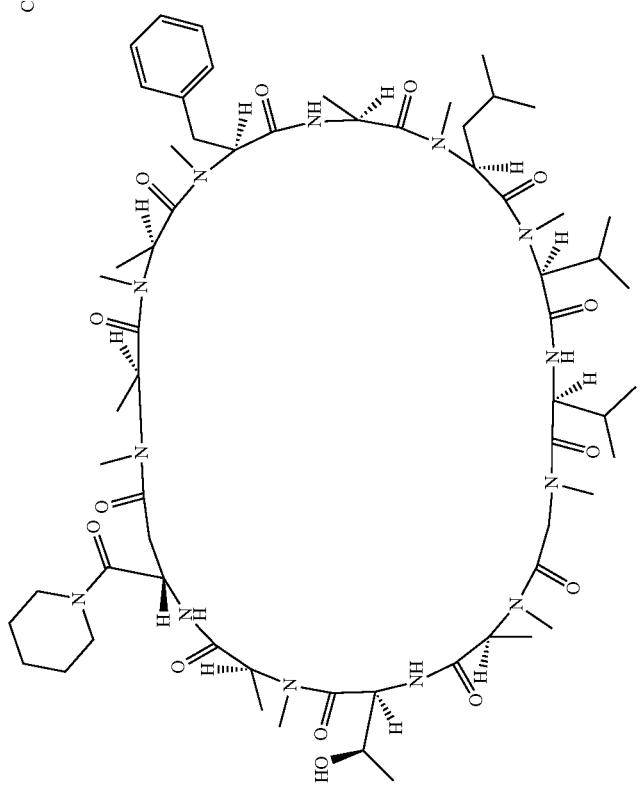

TABLE 11-3-1-continued
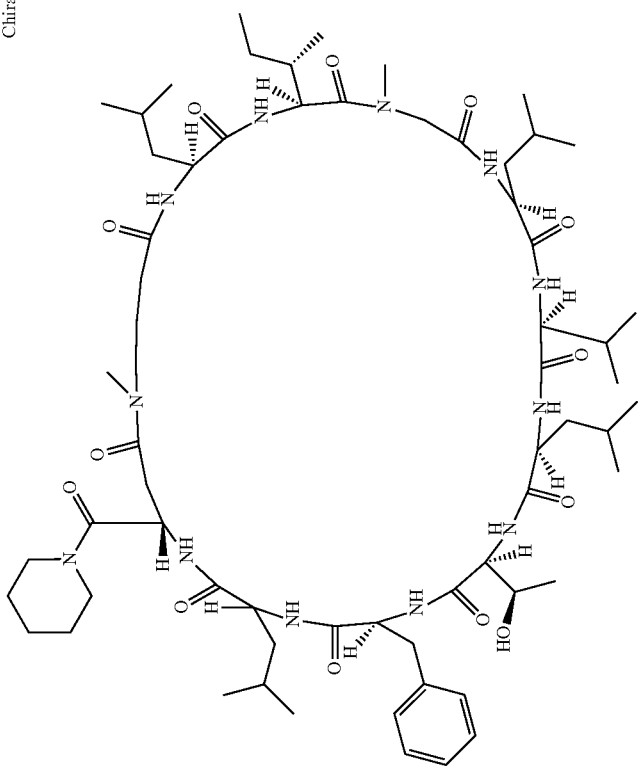
DP-411

TABLE 11-3-1-continued
DP-412
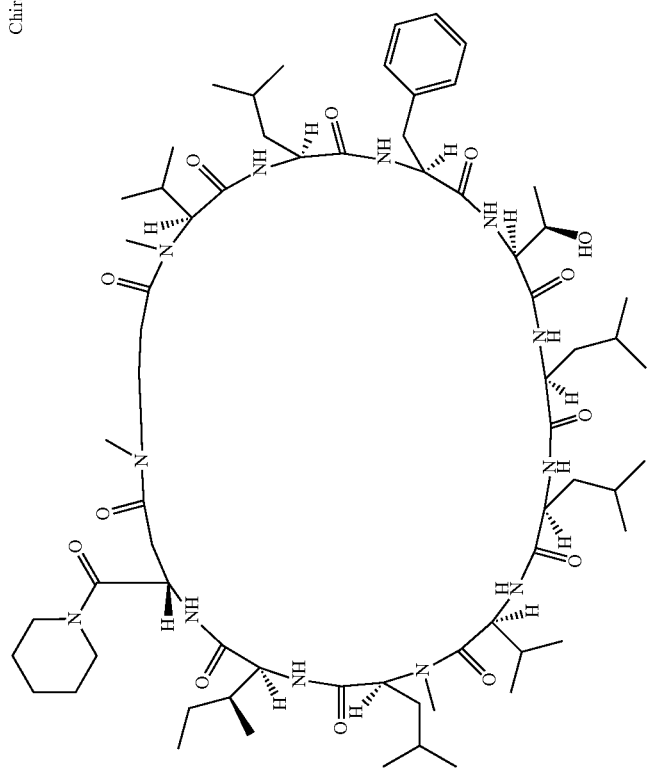
Chiral

TABLE 11-3-1-continued
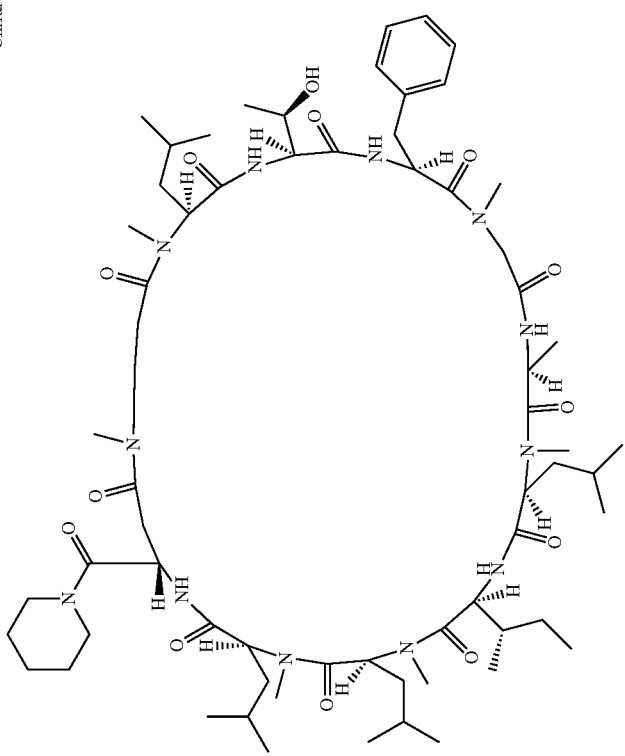
DP-413

TABLE 11-3-1-continued
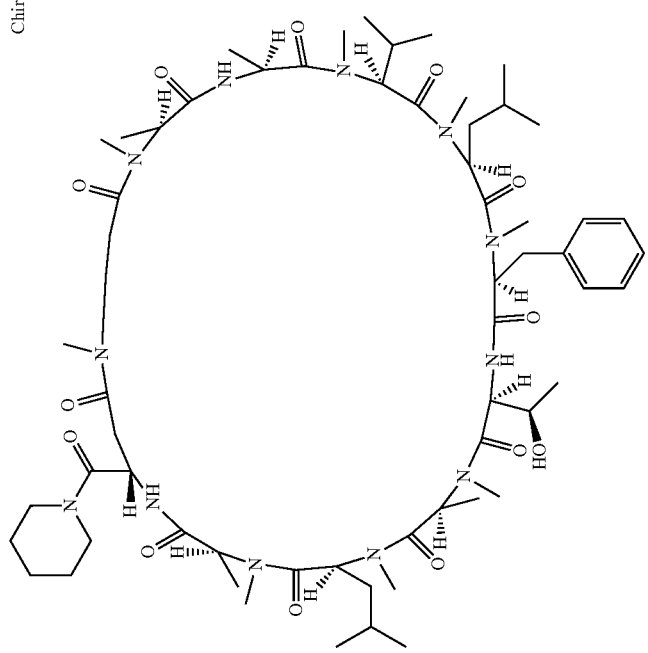
DP-414

TABLE 11-3-1-continued
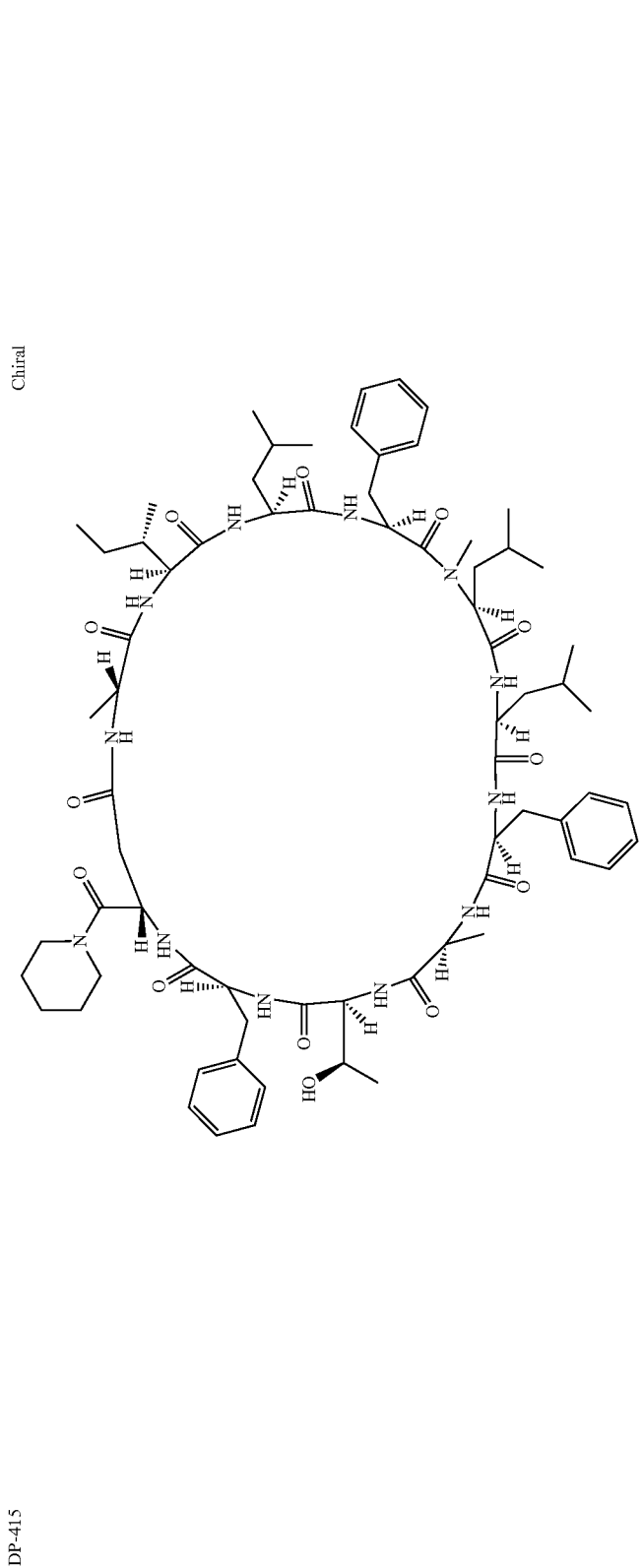
DP-415

TABLE 11-3-1-continued
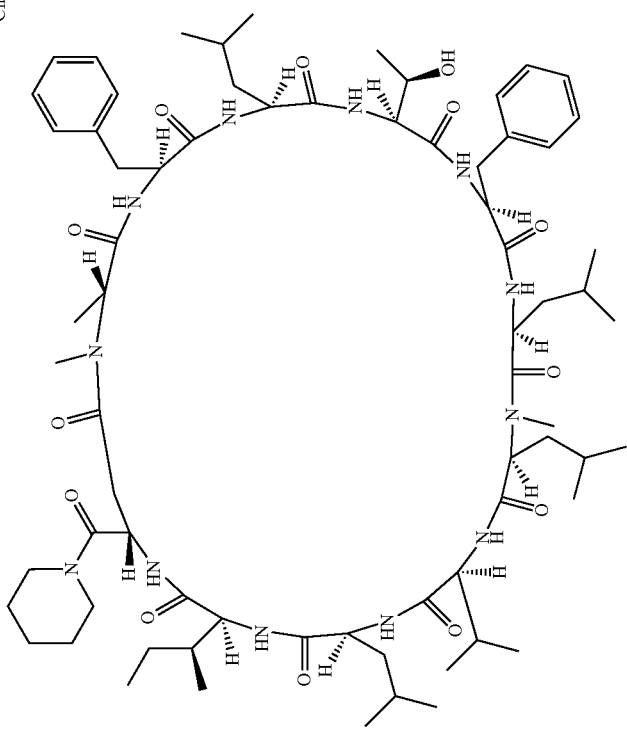
DP-416

TABLE 11-3-1-continued
DP-417
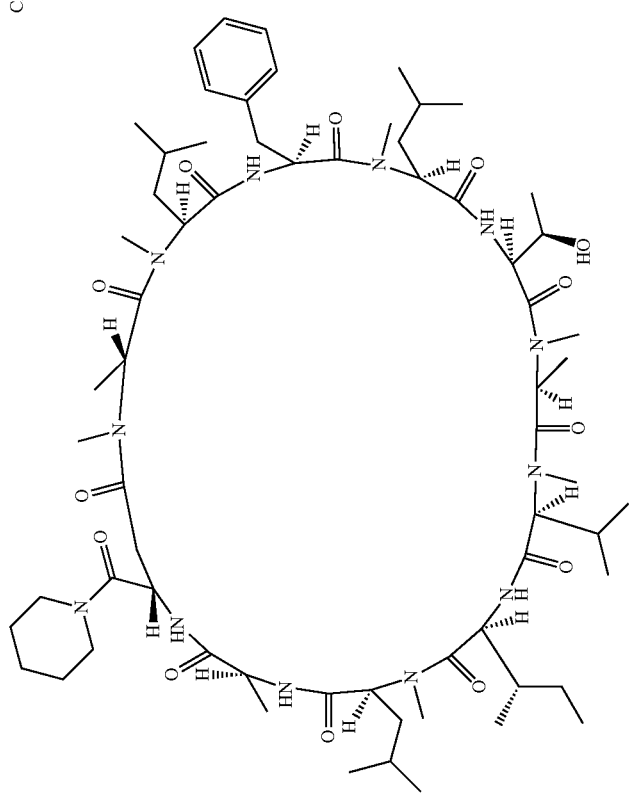

TABLE 11-3-1-continued
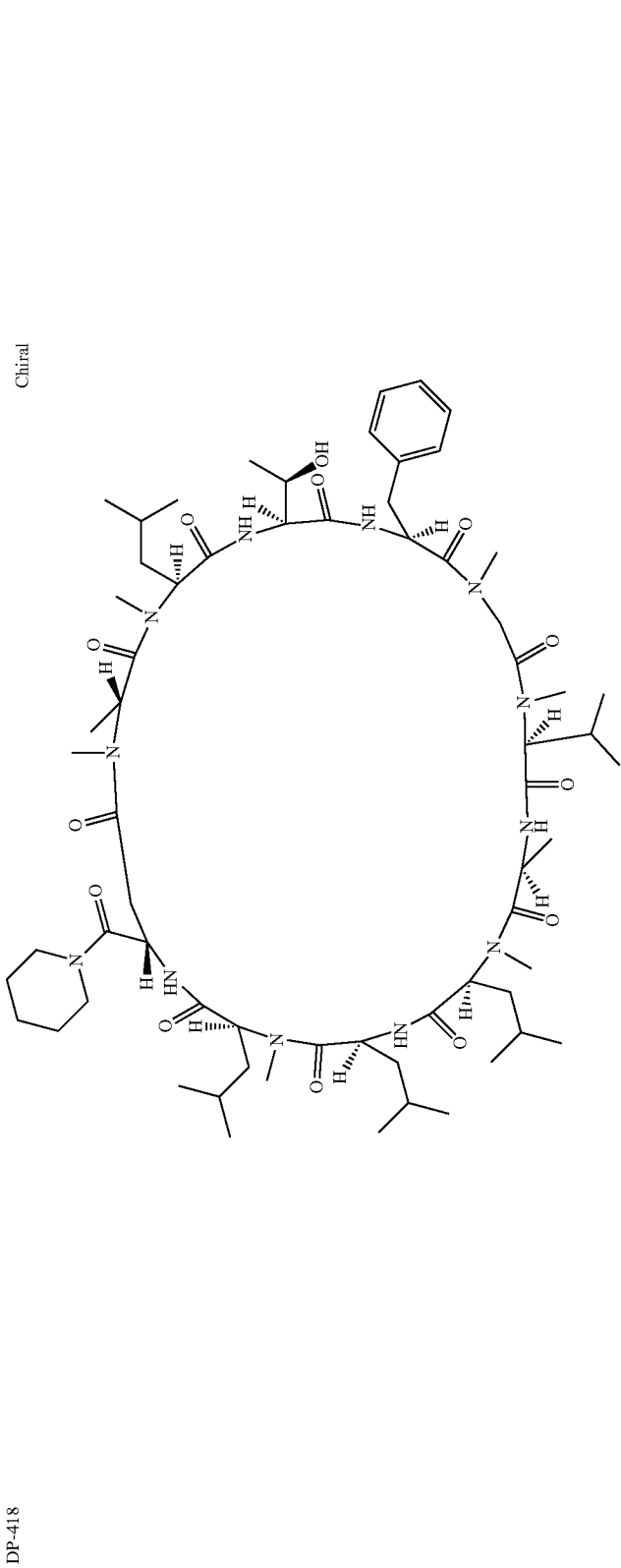
DP-418

TABLE 11-3-1-continued
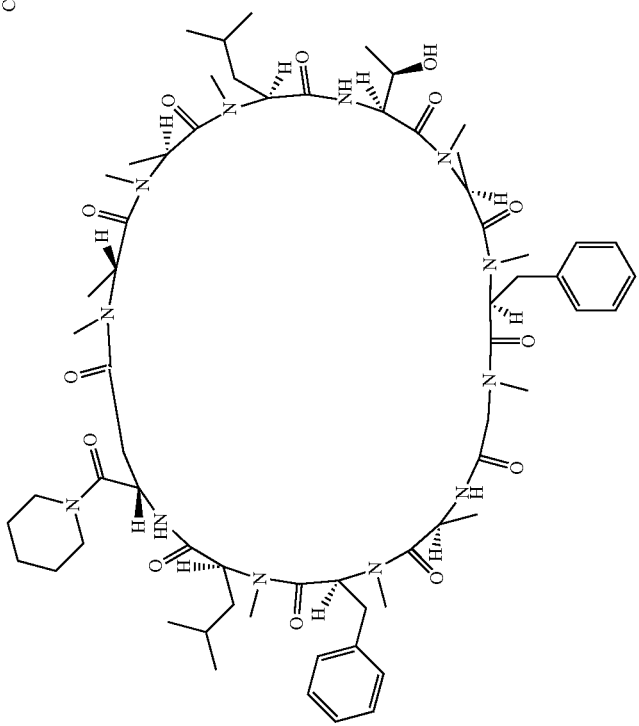
DP-419

TABLE 11-3-1-continued
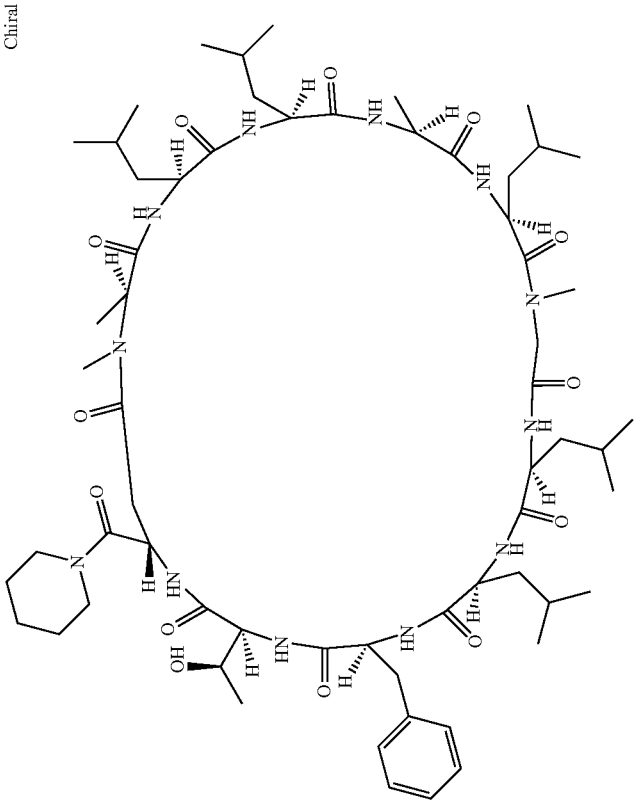
DP-420

TABLE 11-3-1-continued
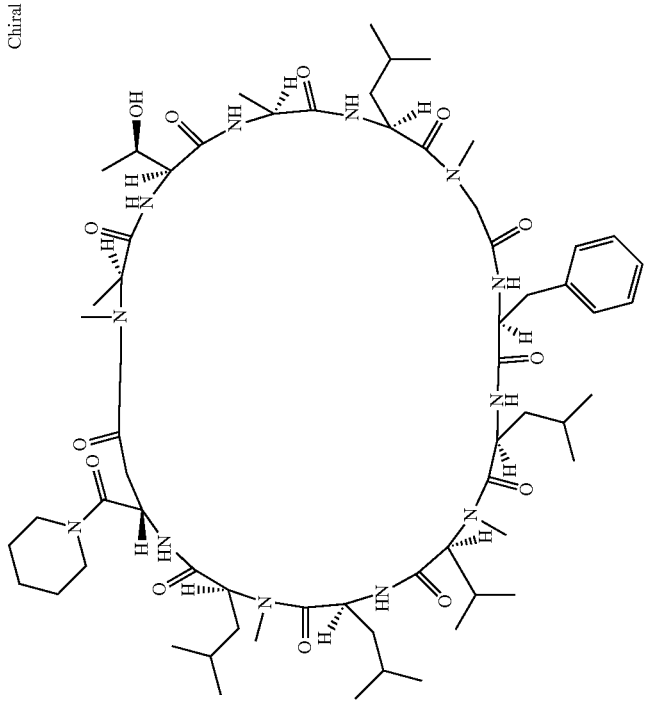
DP-421

TABLE 11-3-1-continued
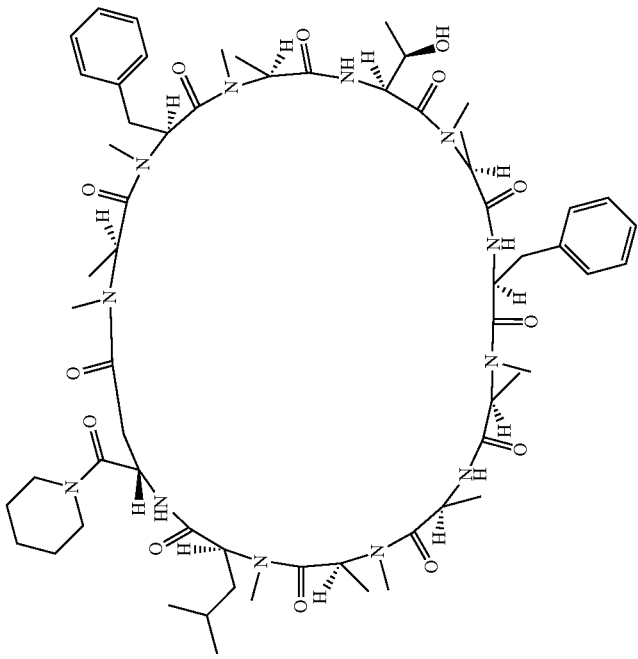
DP-422

TABLE 11-3-1-continued
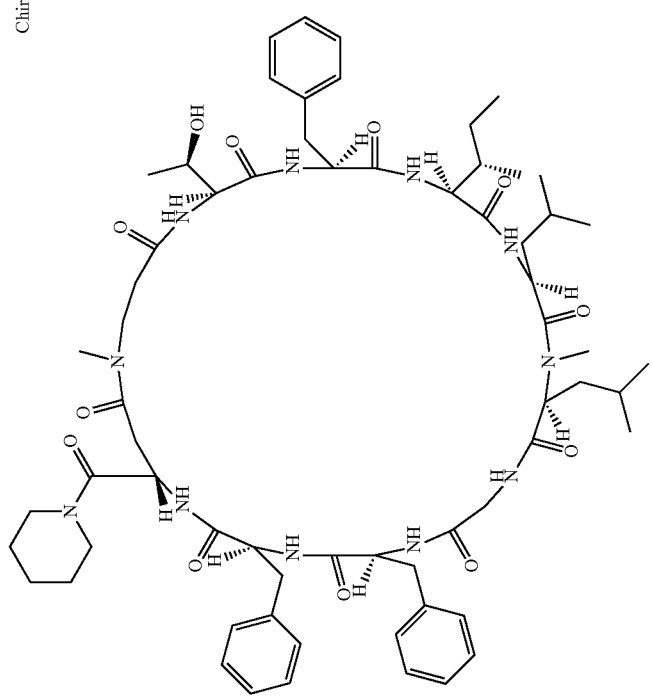
DP-423

TABLE 11-3-1-continued
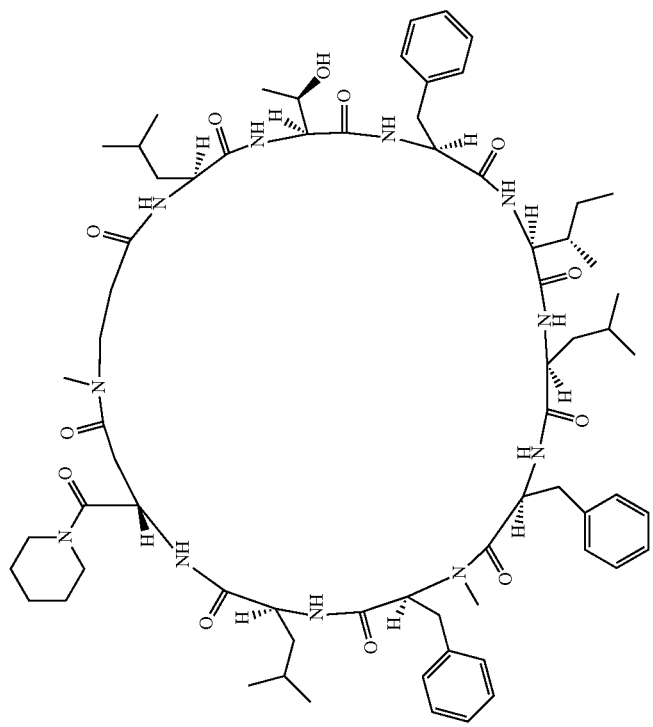
DP-424

TABLE 11-3-1-continued
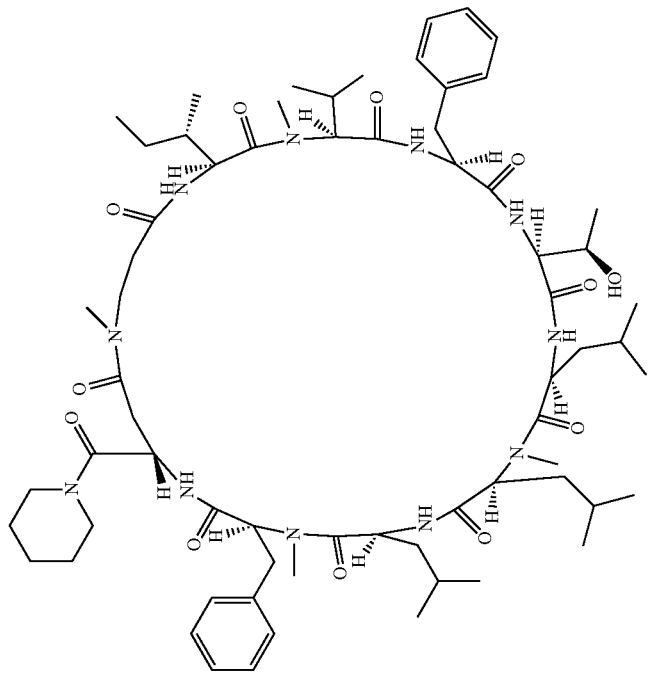
DP-425

TABLE 11-3-1-continued
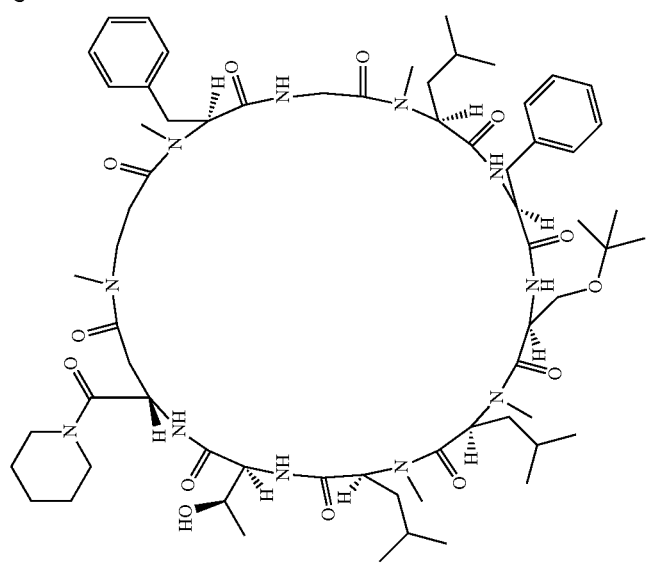
DP-426

TABLE 11-3-1-continued
Chiral
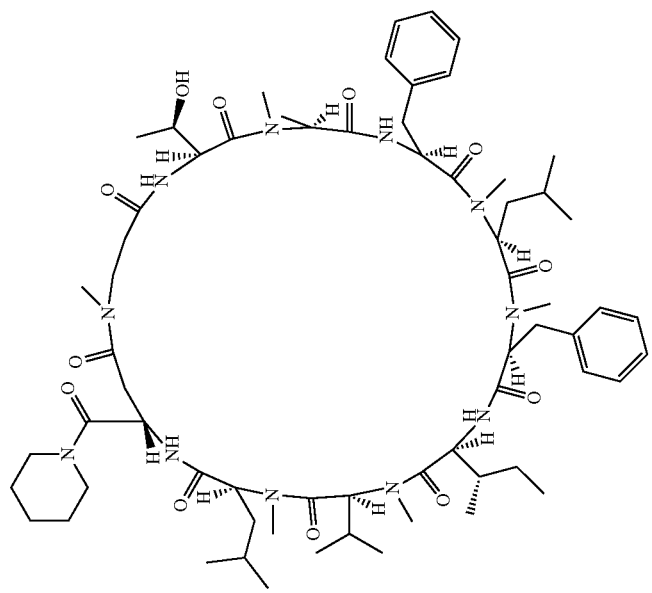
DP-427

TABLE 11-3-1-continued
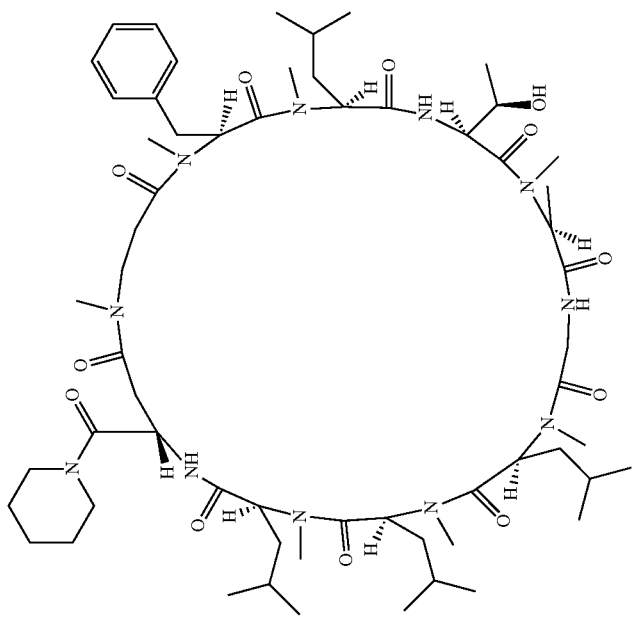
DP-428

TABLE 11-3-1-continued
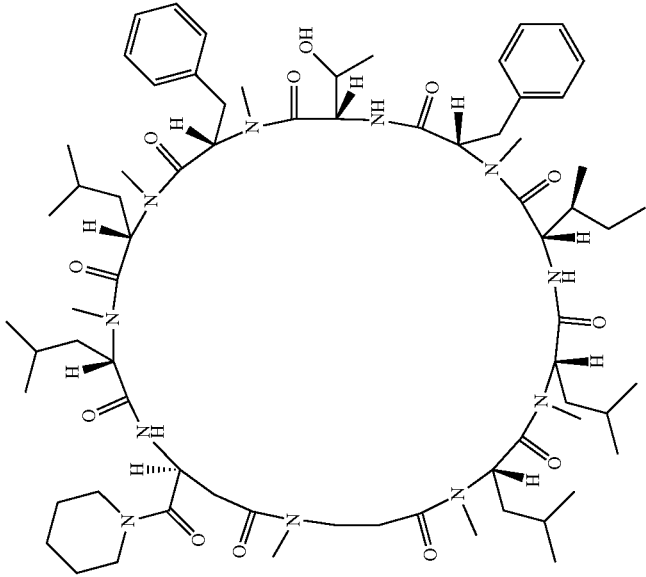
DP-429

TABLE 11-3-1-continued
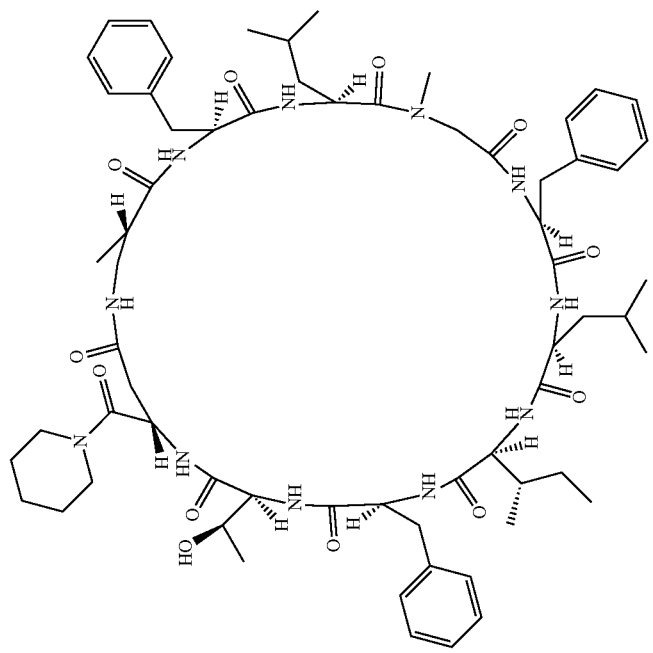
DP-430

TABLE 11-3-1-continued
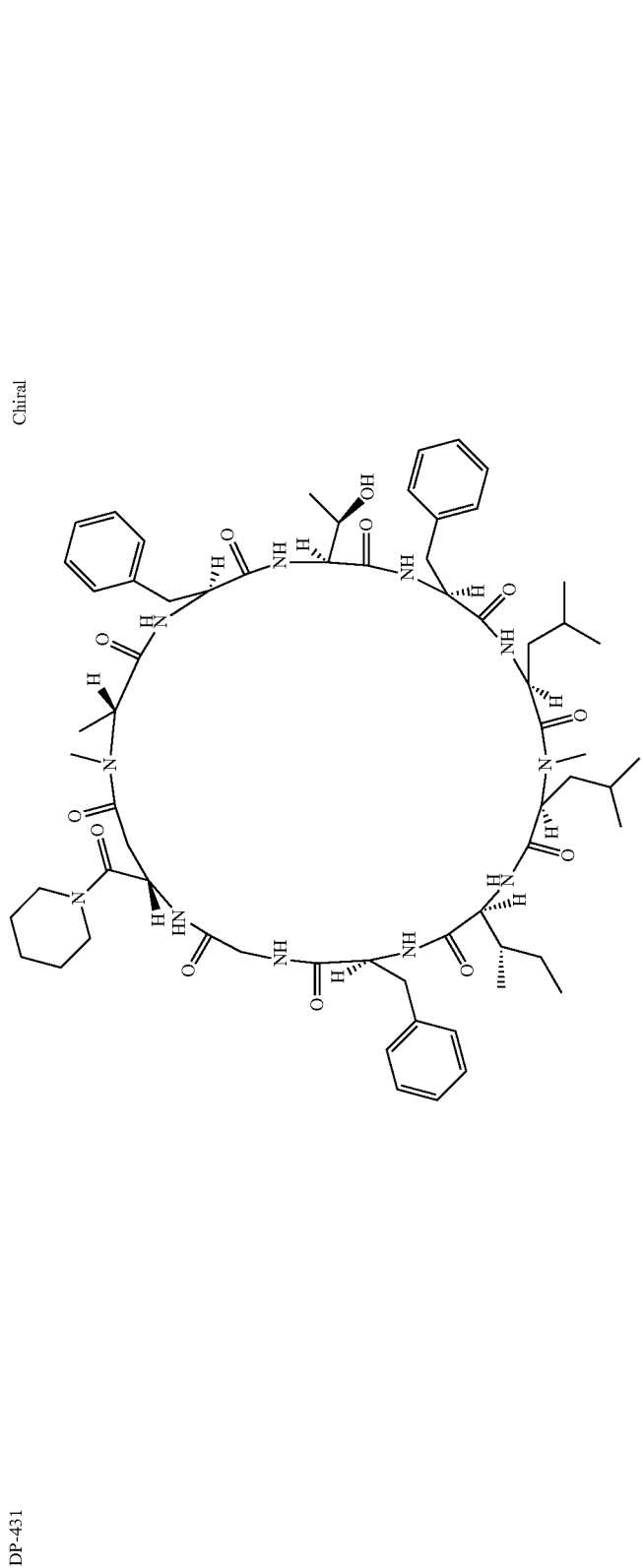
DP-431

TABLE 11-3-1-continued
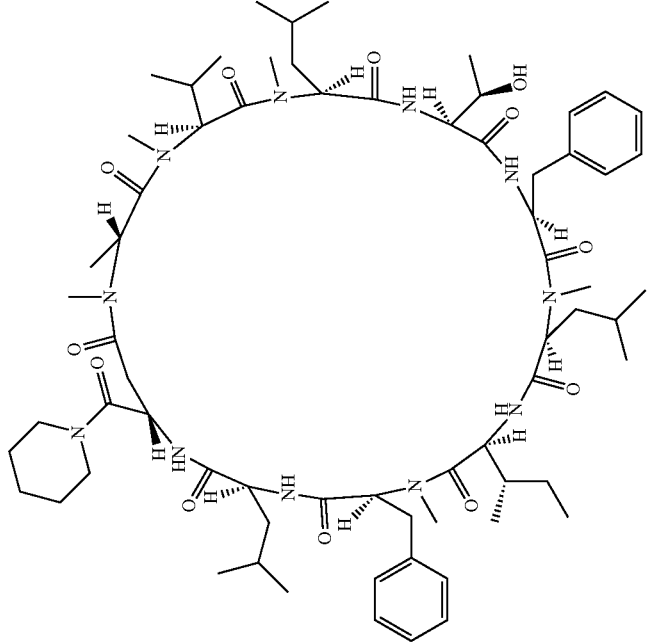
DP-432

TABLE 11-3-1-continued
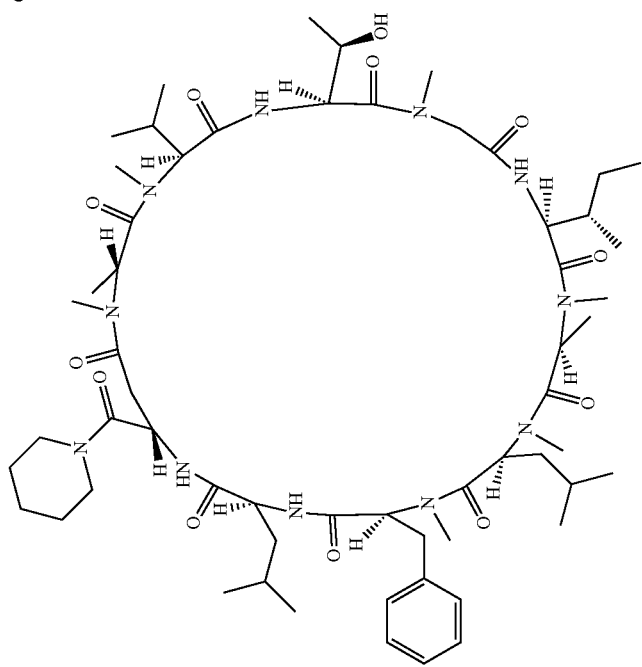
DP-433

TABLE 11-3-1-continued
DP-434

TABLE 11-3-1-continued
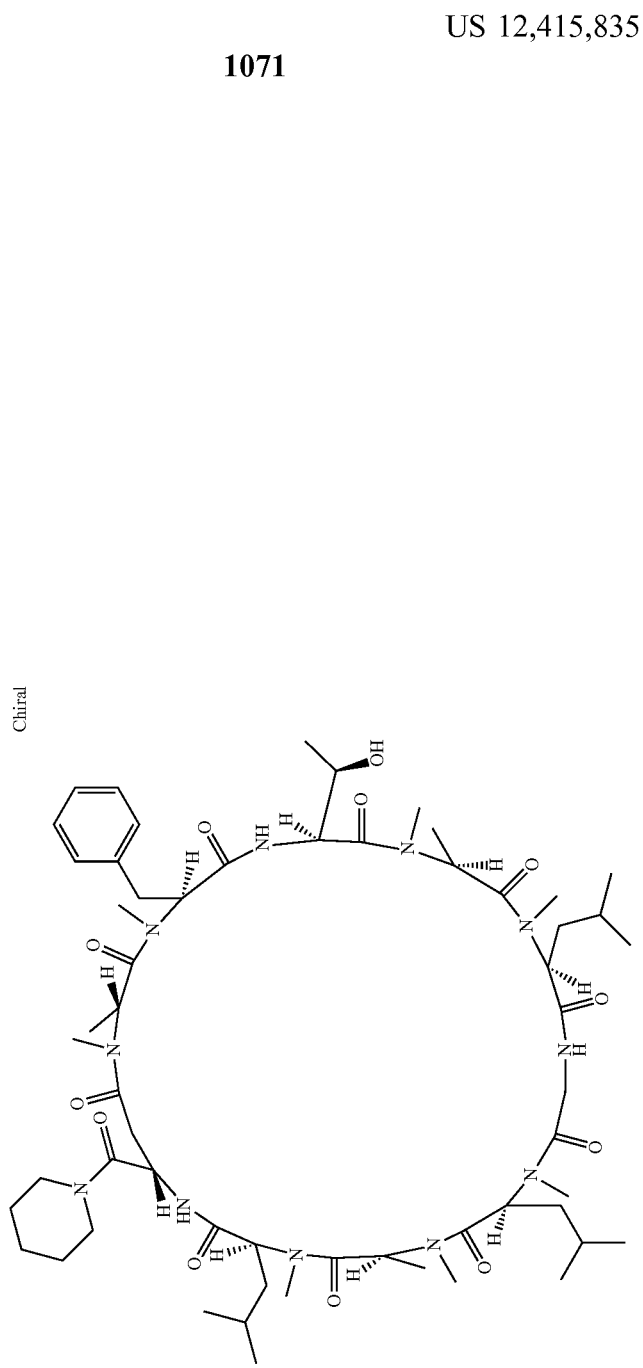
DP-435

TABLE 11-3-1-continued
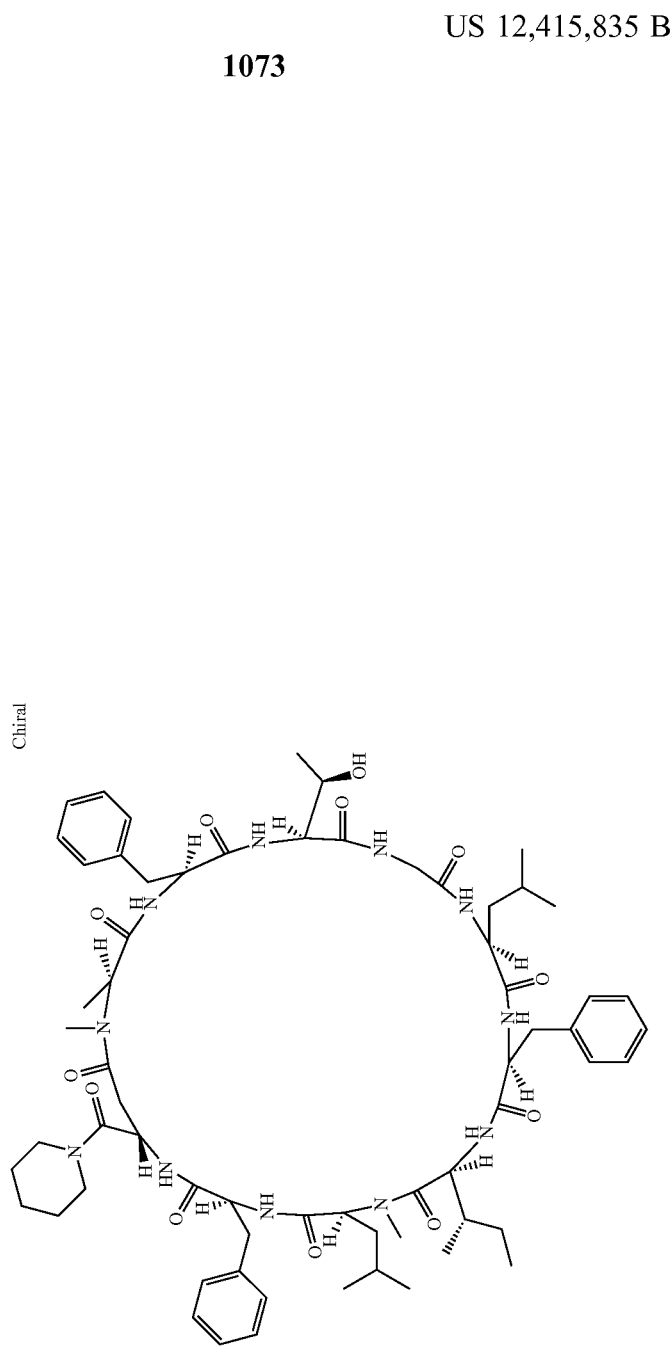
DP-436

TABLE 11-3-1-continued
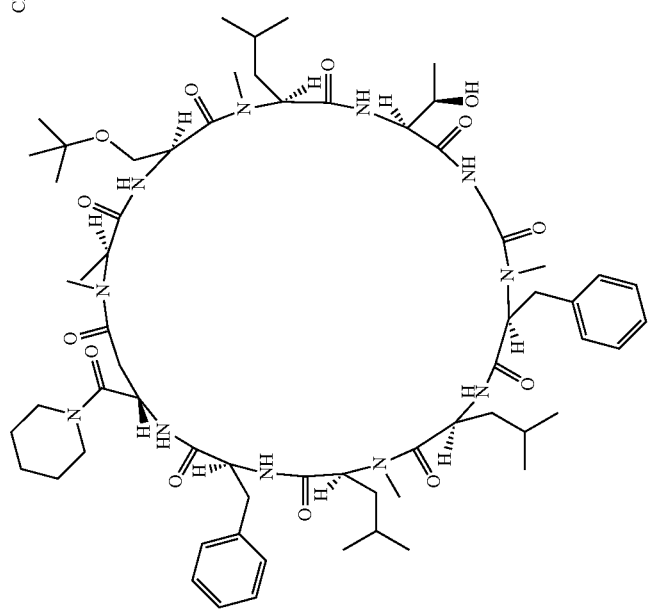
DP-437

TABLE 11-3-1-continued
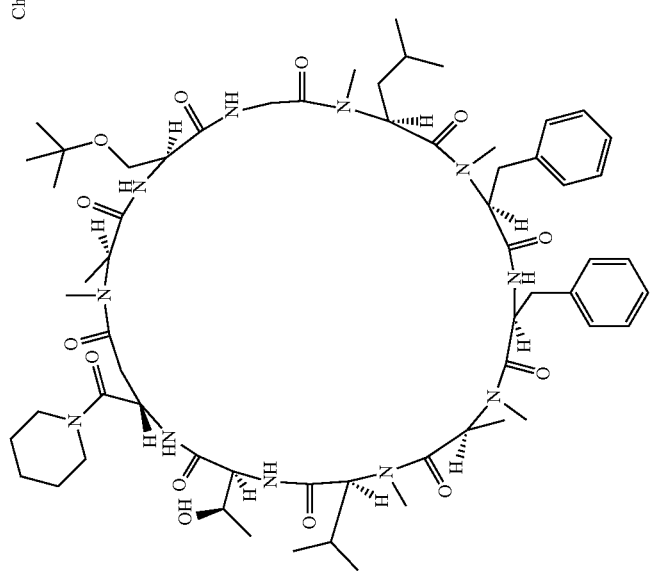
DP-438

TABLE 11-3-1-continued
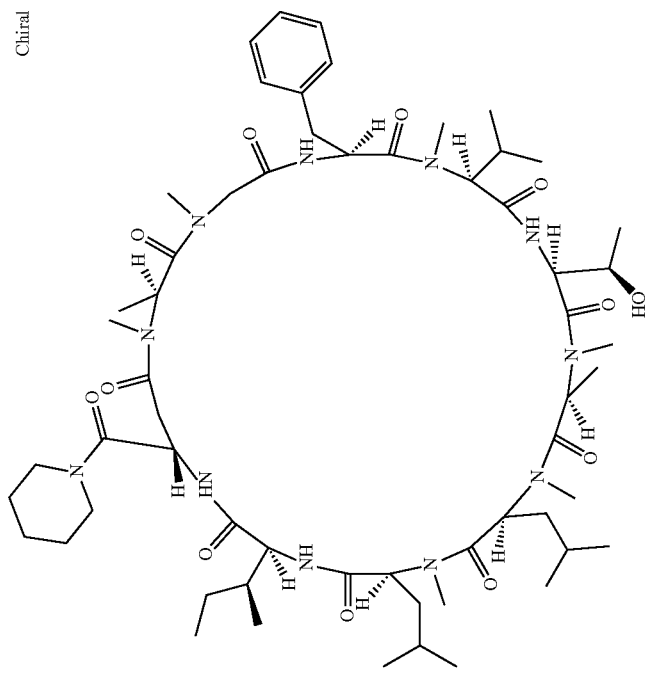
DP-439

TABLE 11-3-1-continued
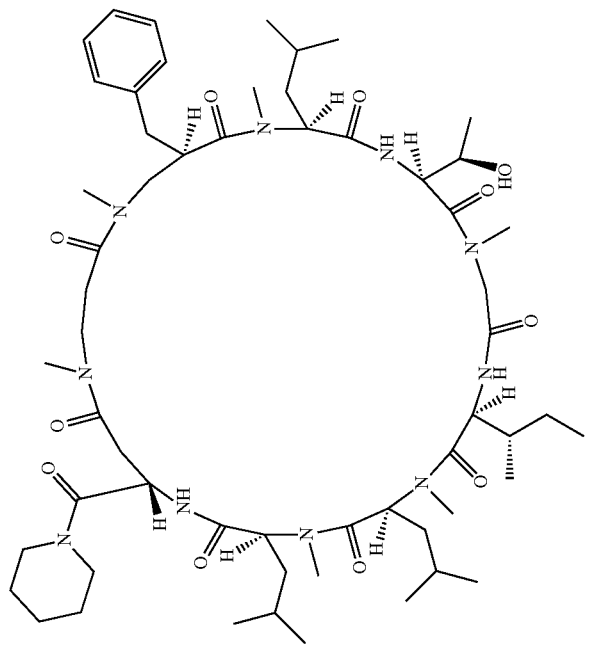
DP-440

TABLE 11-3-1-continued
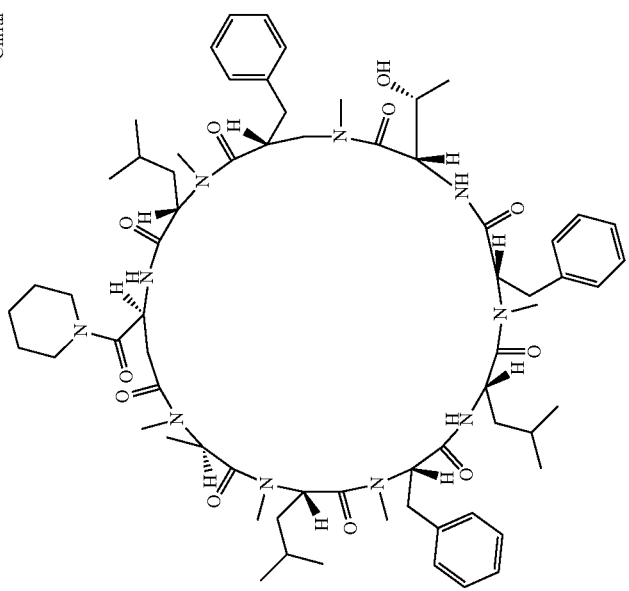
DP-441

TABLE 11-3-1-continued
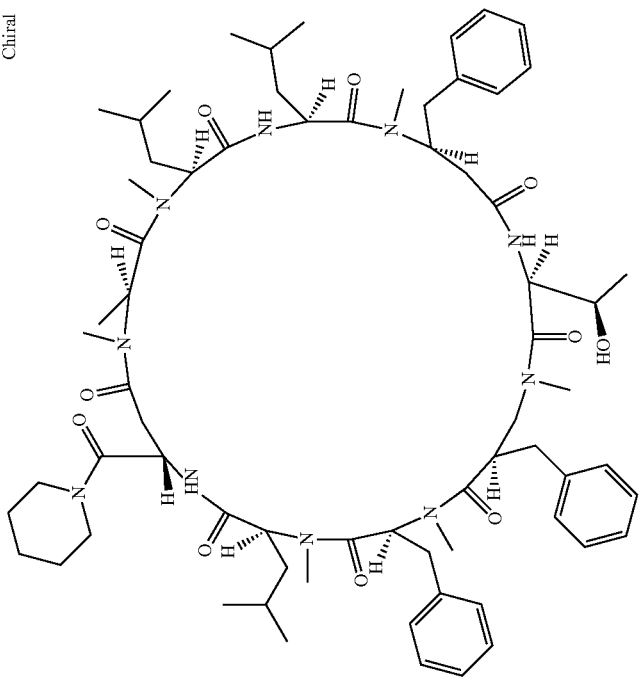
DP-442

TABLE 11-3-1-continued
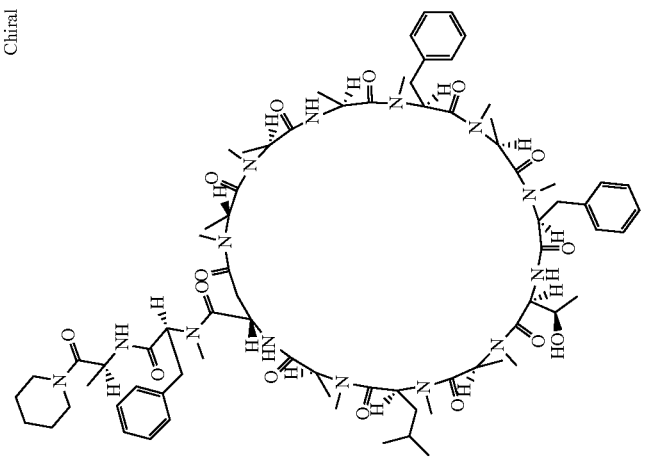
DP-443

TABLE 11-3-1-continued
DP-444
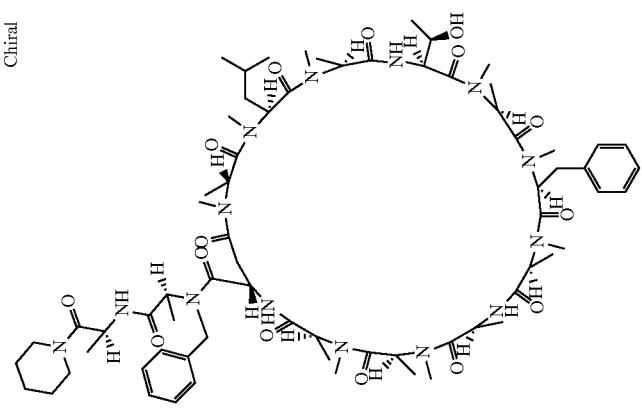

TABLE 11-3-1-continued
Chiral
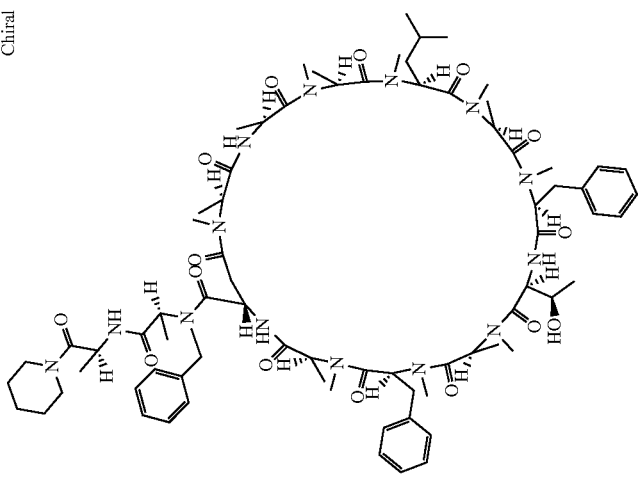
DP-445

TABLE 11-3-1-continued
Chiral
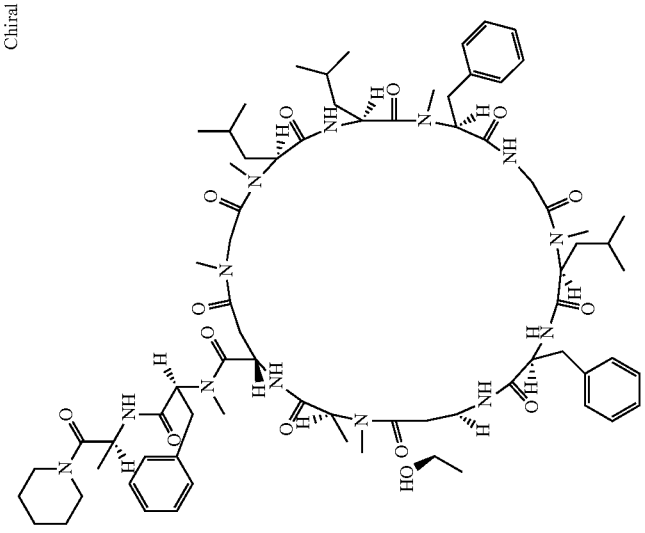
DP-446

TABLE 11-3-1-continued
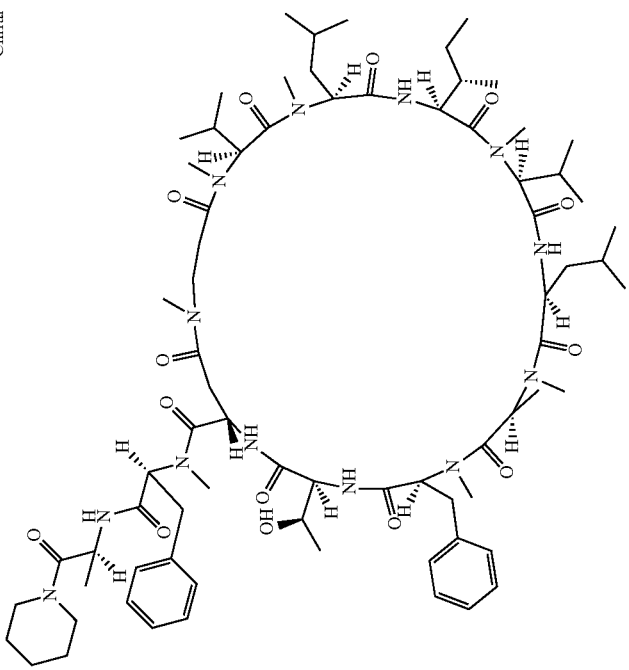
DP-447

TABLE 11-3-1-continued
Chiral
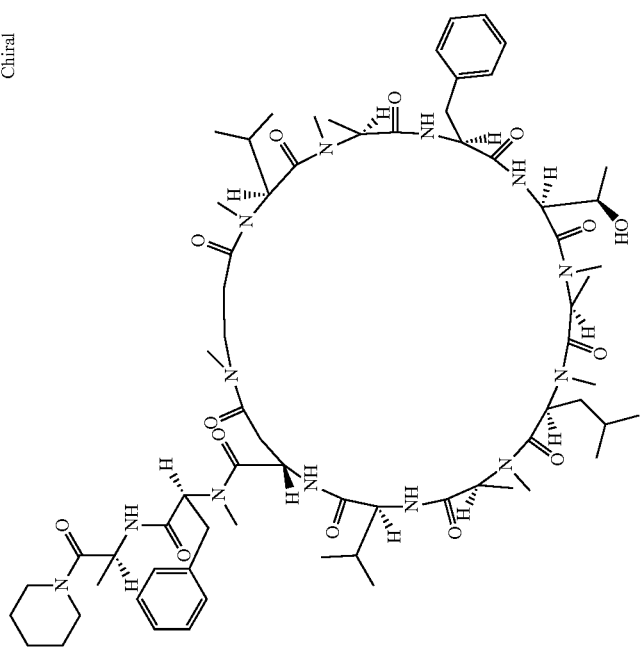
DP-448

TABLE 11-3-1-continued
DP-449
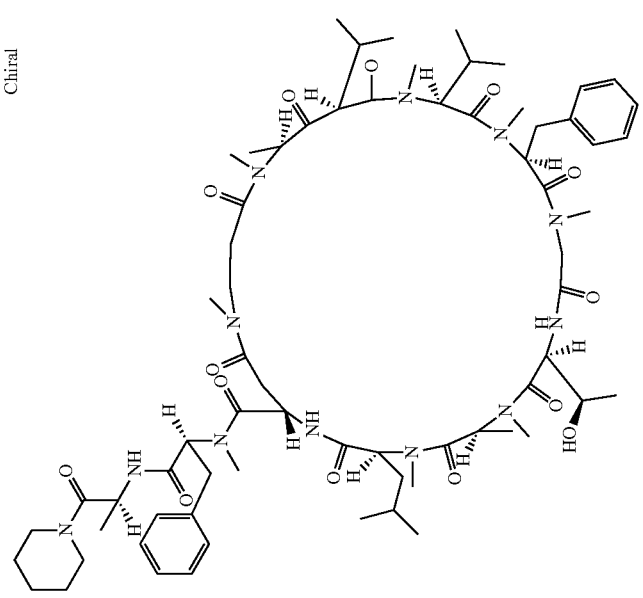

TABLE 11-3-1-continued
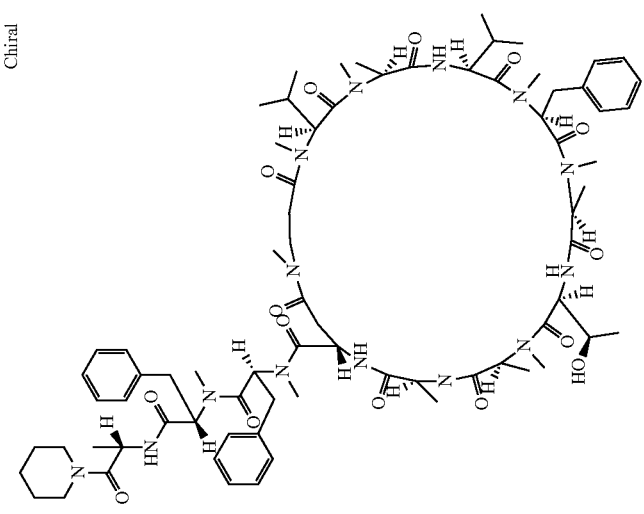
DP-450

TABLE 11-3-1-continued
Chiral
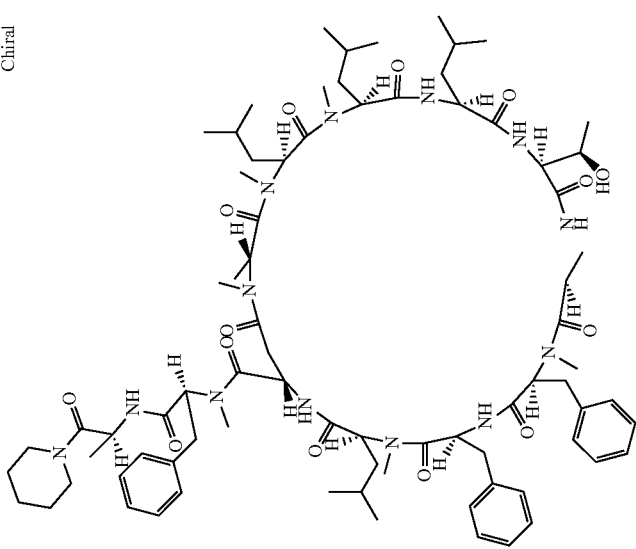
DP-451

TABLE 11-3-1-continued
Chiral
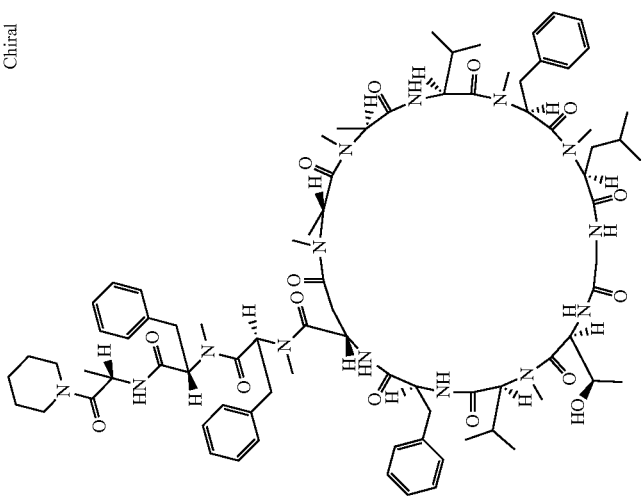
DP-452

TABLE 11-3-1-continued
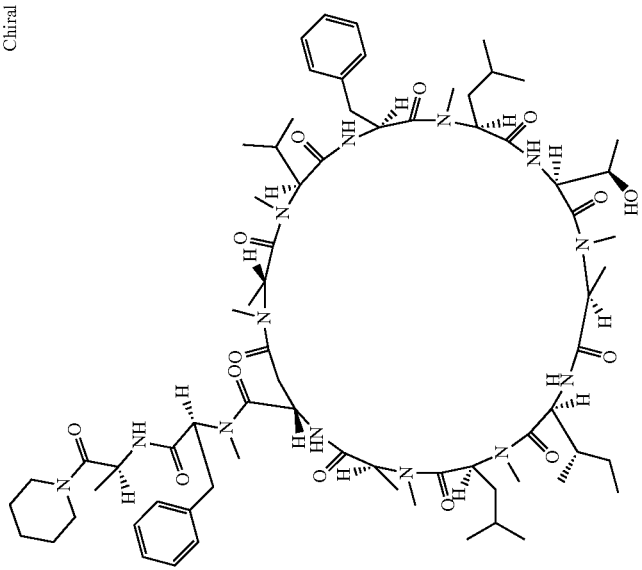
DP-453

TABLE 11-3-1-continued
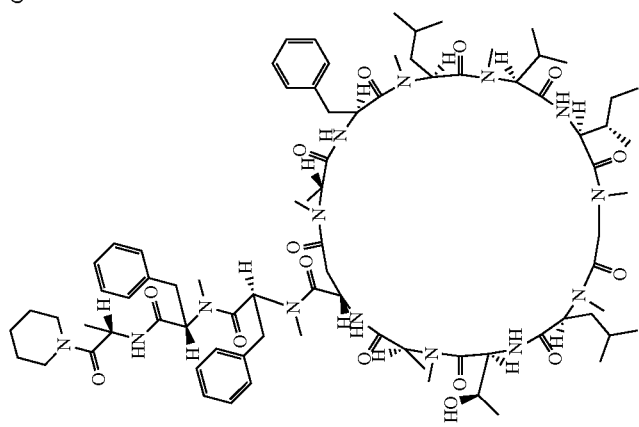
DP-454

TABLE 11-3-1-continued
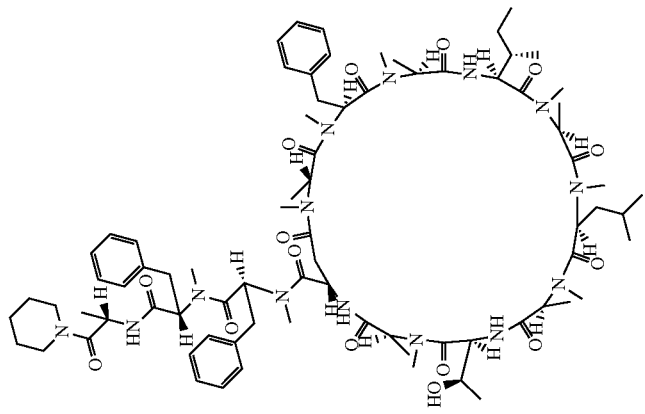
DP-455

TABLE 11-3-1-continued
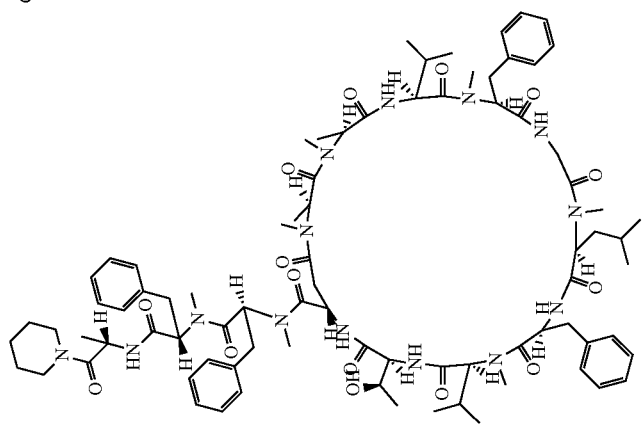
DP-456

TABLE 11-3-1-continued
Chiral
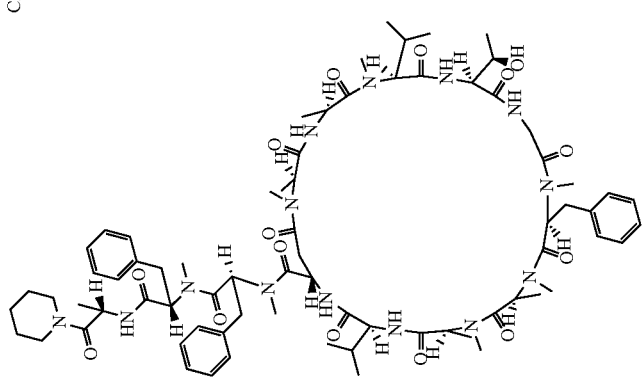
DP-457

TABLE 11-3-1-continued
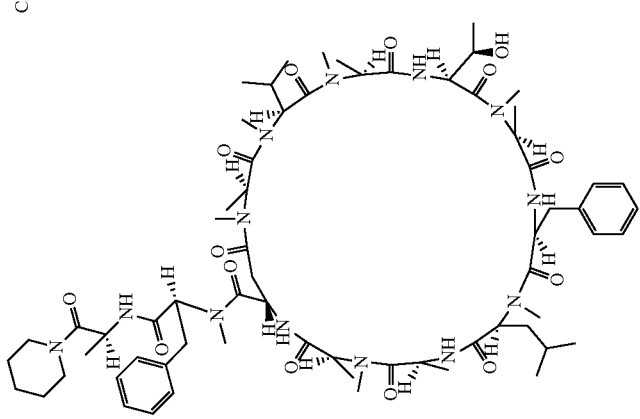
DP-458

TABLE 11-3-1-continued
Chiral
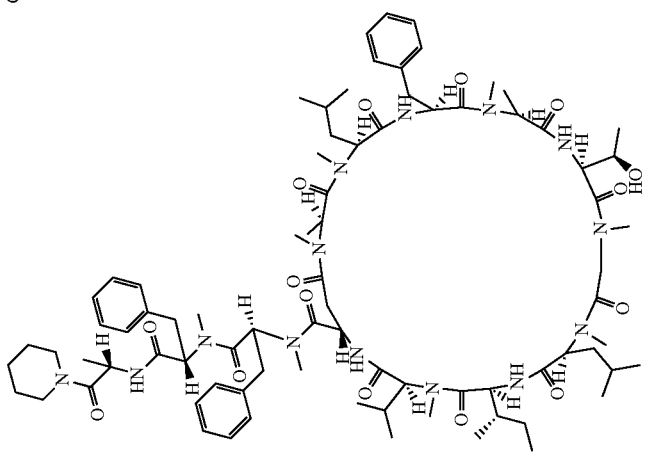
DP-459

TABLE 11-3-1-continued
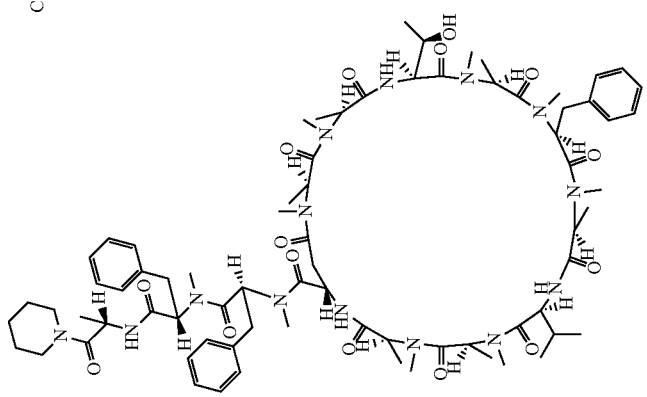
DP-460

TABLE 11-3-1-continued
DP-461
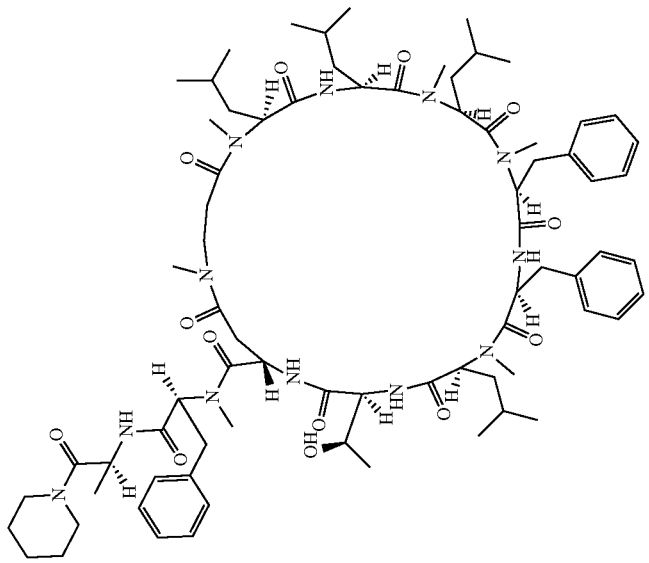

TABLE 11-3-1-continued
DP-462
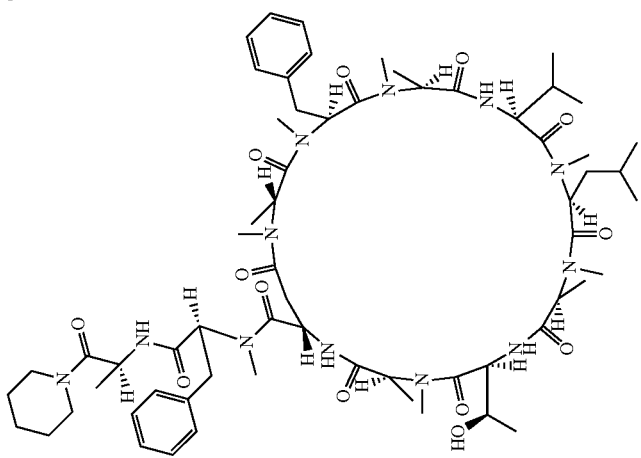

TABLE 11-3-1-continued
Chiral
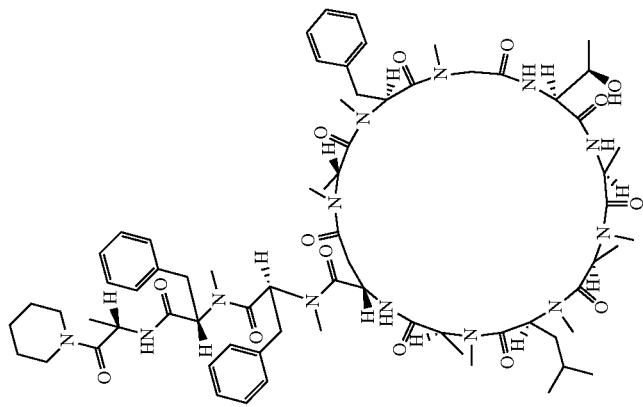
DP-463

TABLE 11-3-1-continued
Chiral
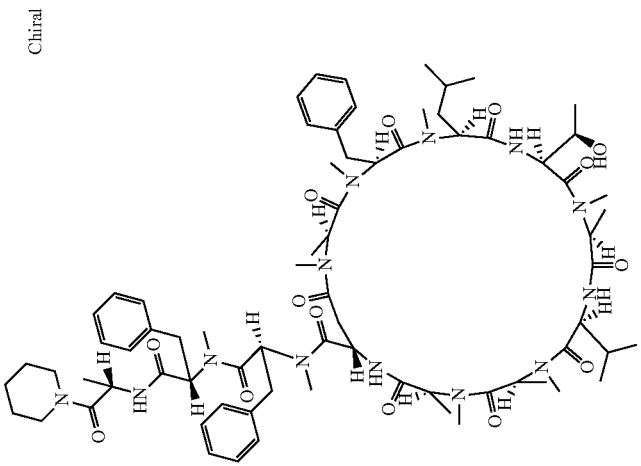
DP-464

TABLE 11-3-1-continued
DP-465
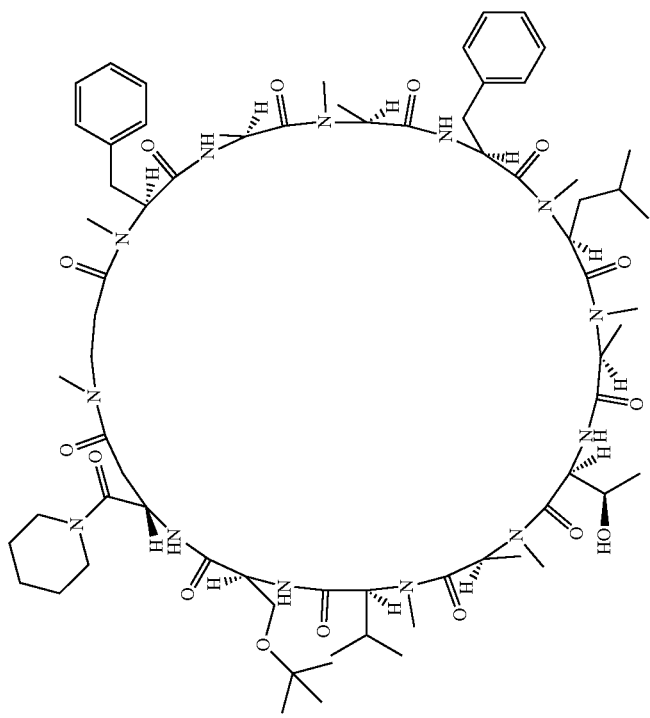

TABLE 11-3-1-continued
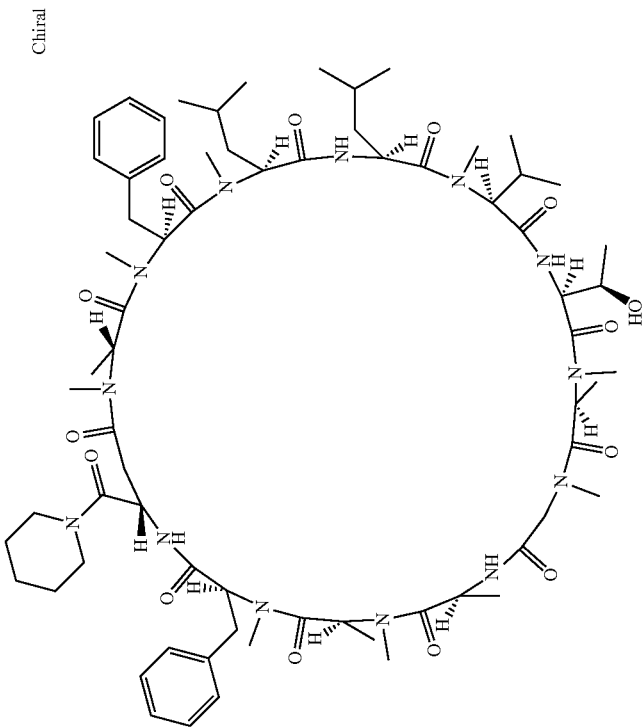
DP-466

TABLE 11-3-1-continued
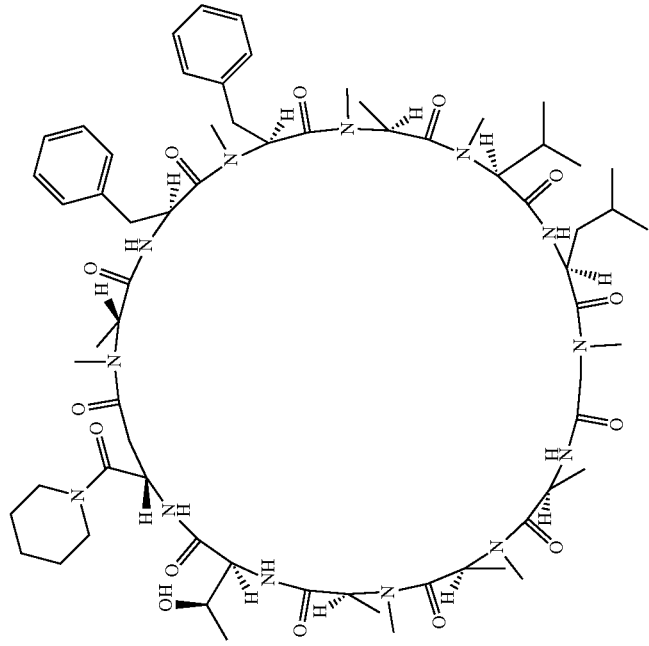
DP-467

TABLE 11-3-1-continued
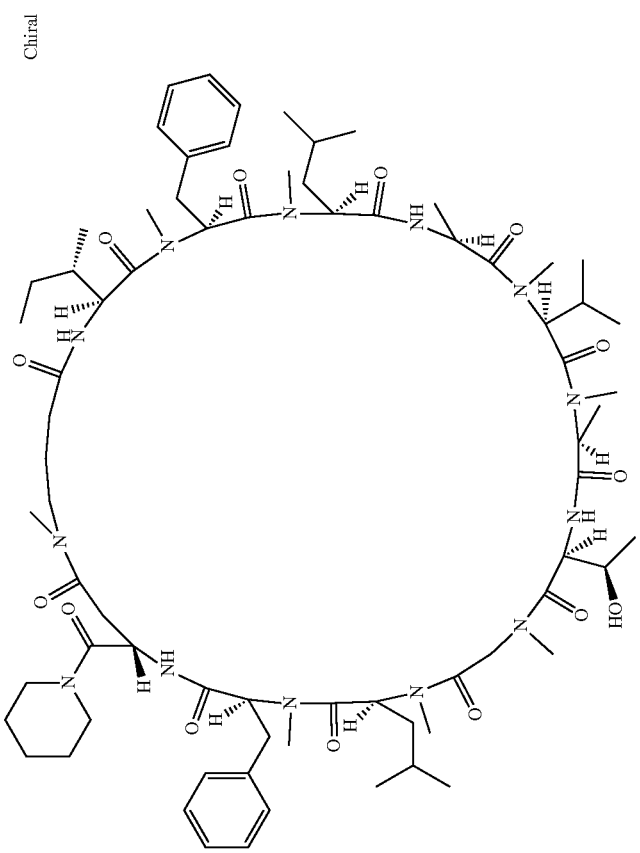
DP-468

TABLE 11-3-1-continued
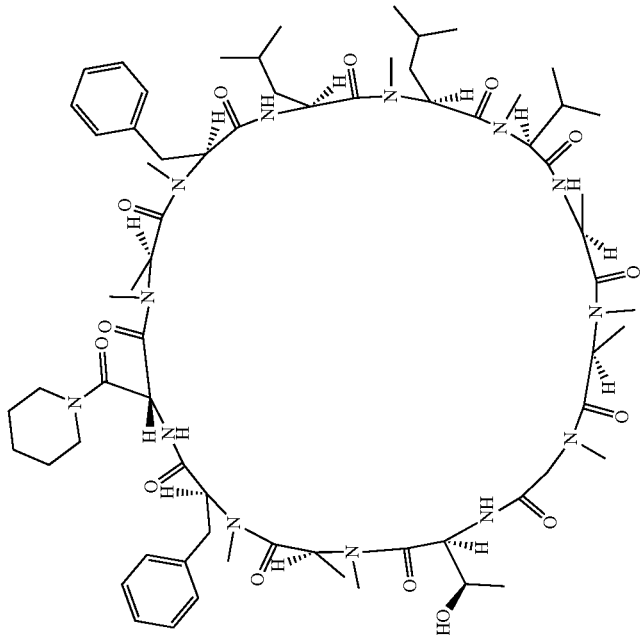
DP-469

TABLE 11-3-1-continued
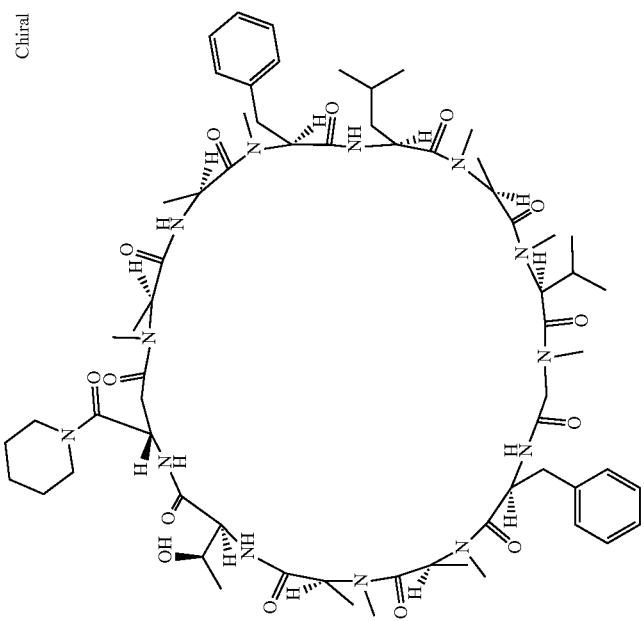
DP-470

TABLE 11-3-1-continued
DP-471
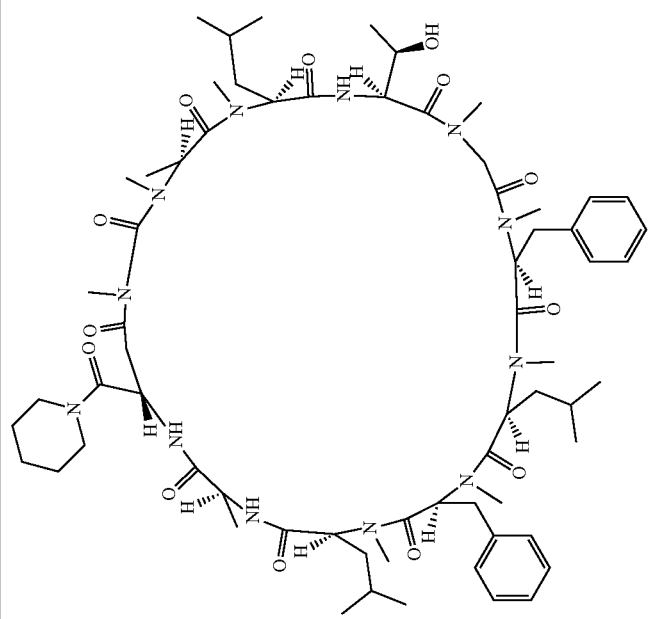

TABLE 11-3-1-continued
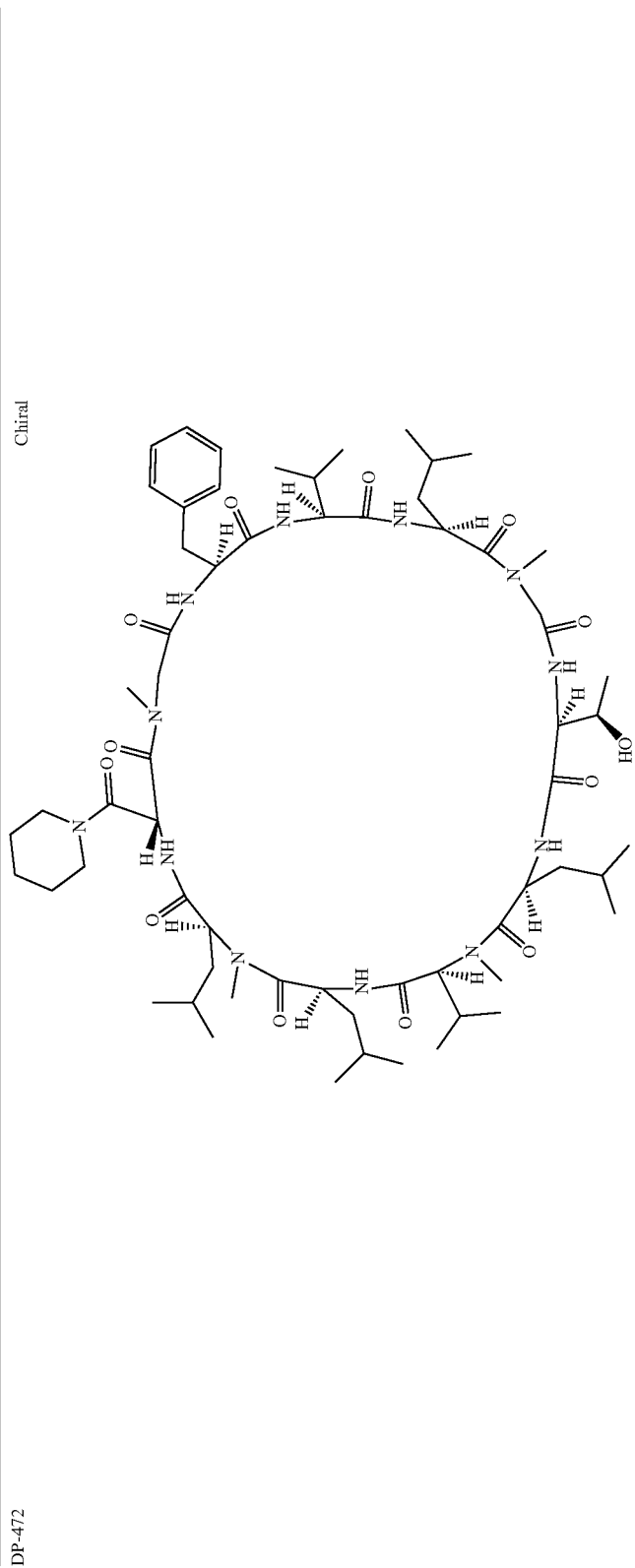
DP-472

TABLE 11-3-1-continued
DP-473
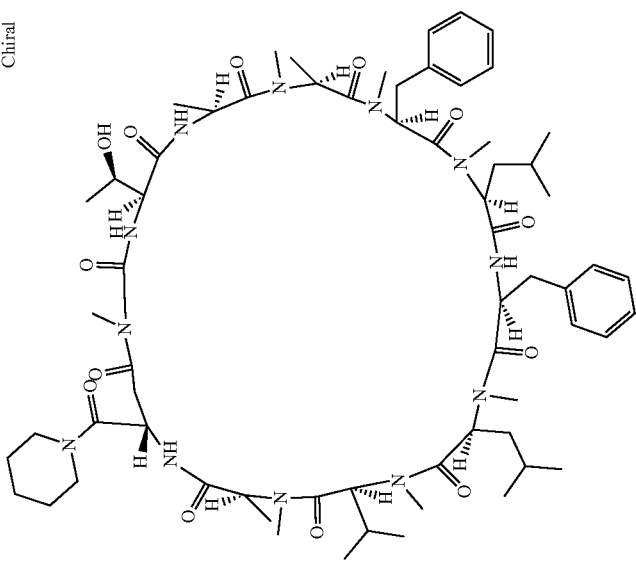

TABLE 11-3-1-continued
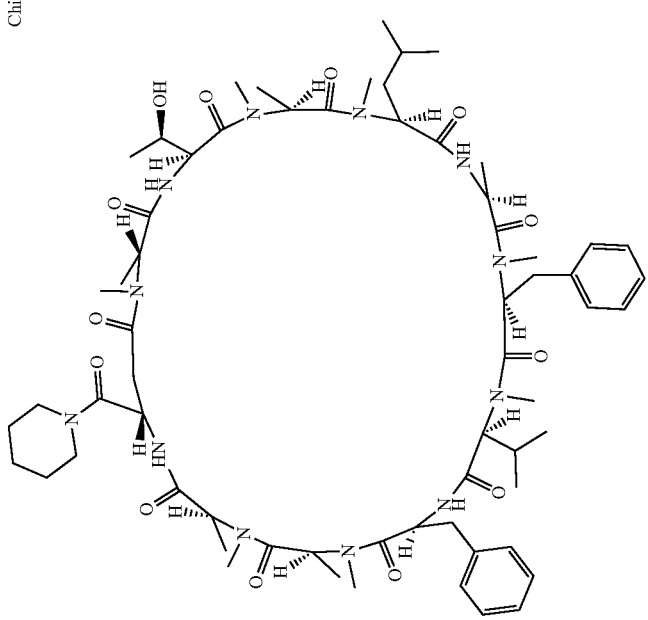
DP-474

TABLE 11-3-1-continued
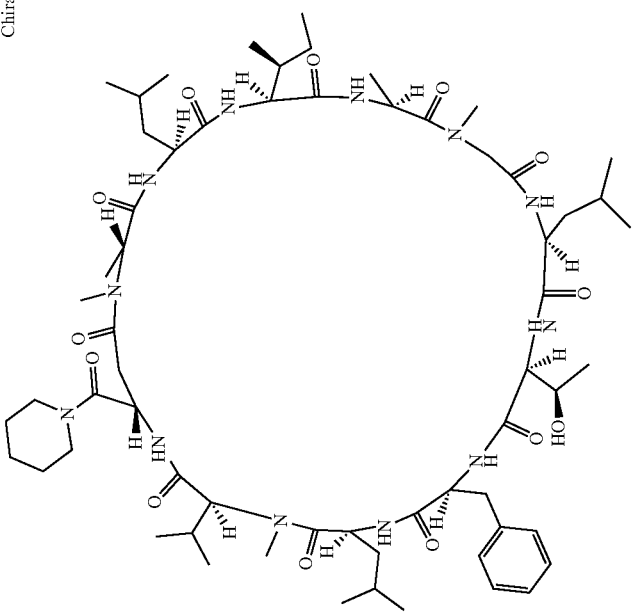
DP-475

TABLE 11-3-1-continued
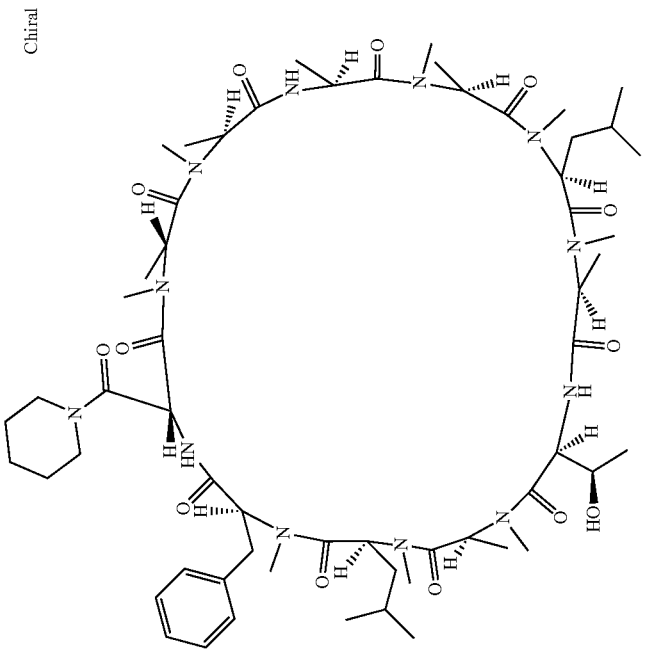
DP-476

TABLE 11-3-1-continued
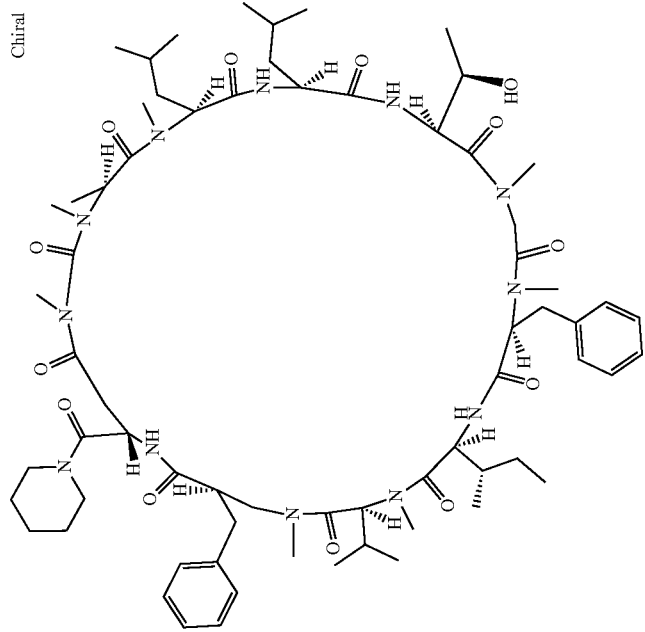
DP-477

TABLE 11-3-1-continued
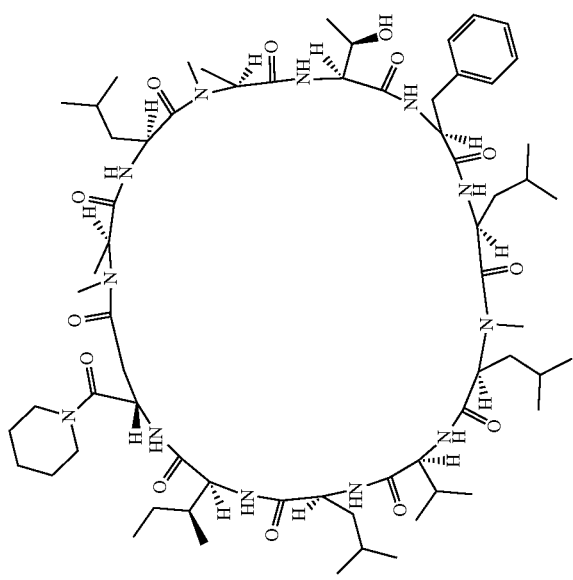
DP-478

TABLE 11-3-1-continued
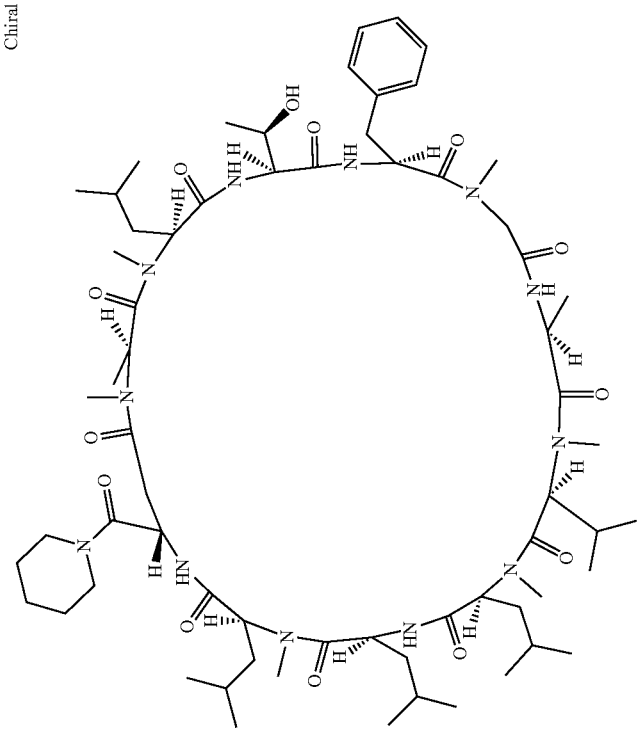
DP-479

TABLE 11-3-1-continued
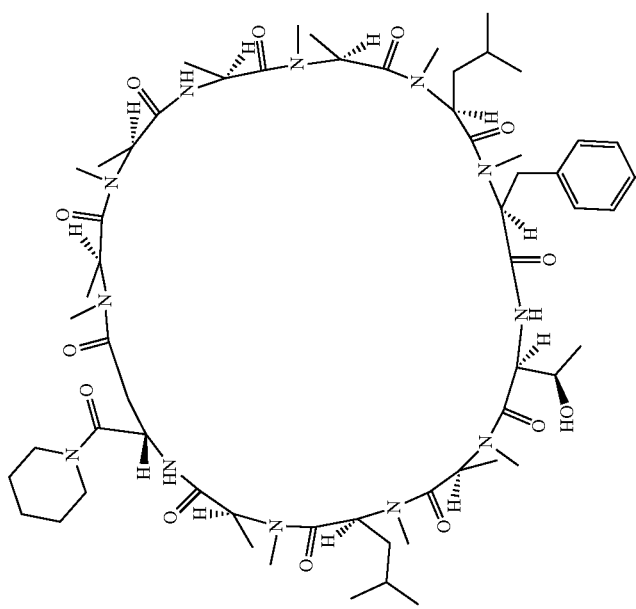
DP-480

TABLE 11-3-1-continued
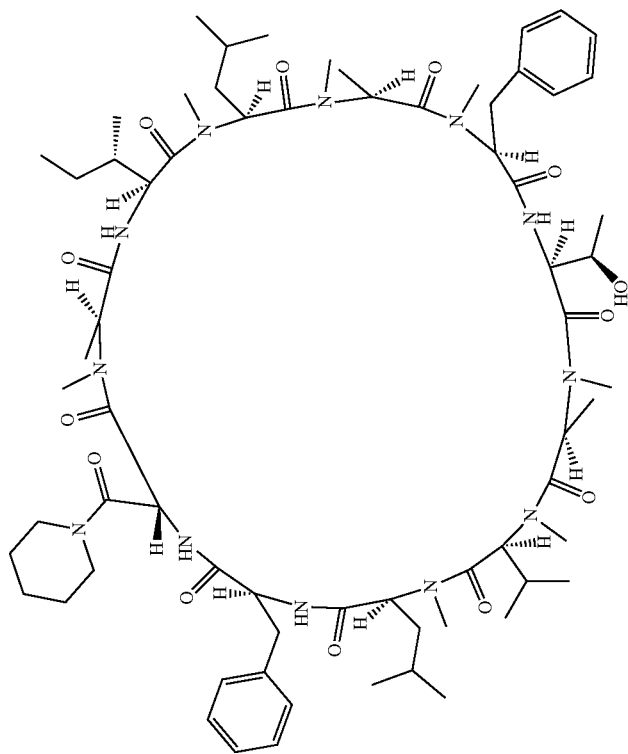
DP-481

TABLE 11-3-1-continued
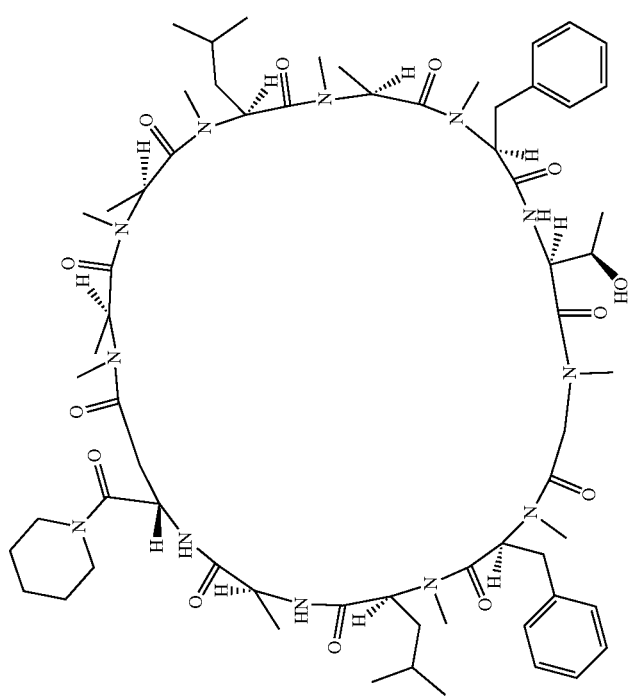
DP-482

TABLE 11-3-1-continued
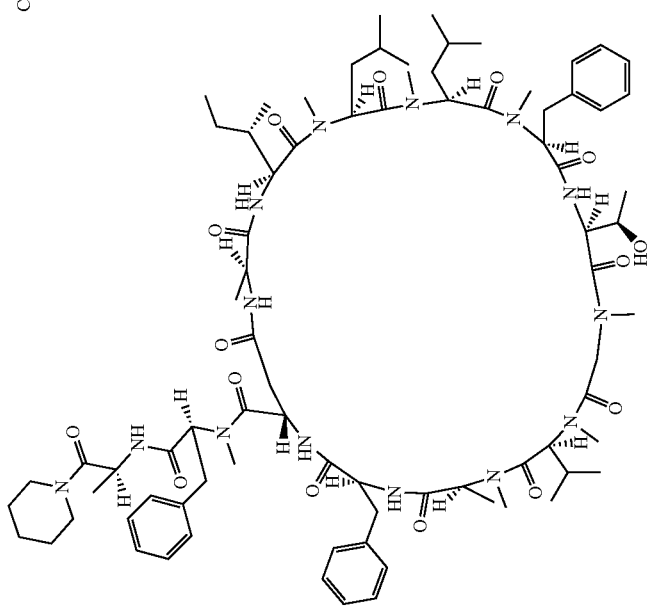
DP-483

TABLE 11-3-1-continued
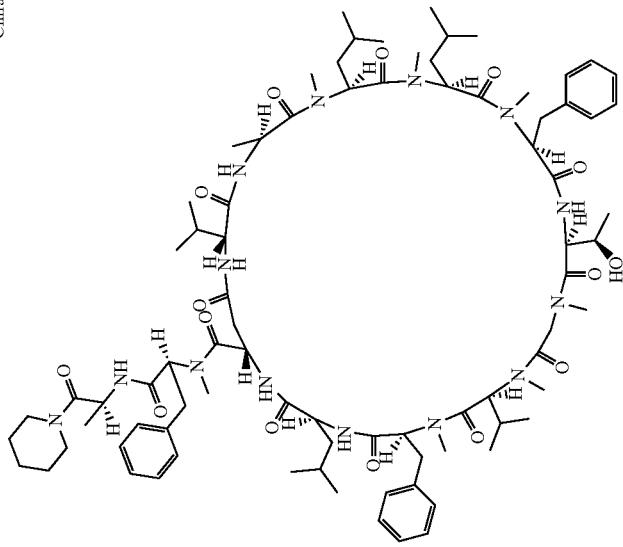
DP-484

TABLE 11-3-1-continued
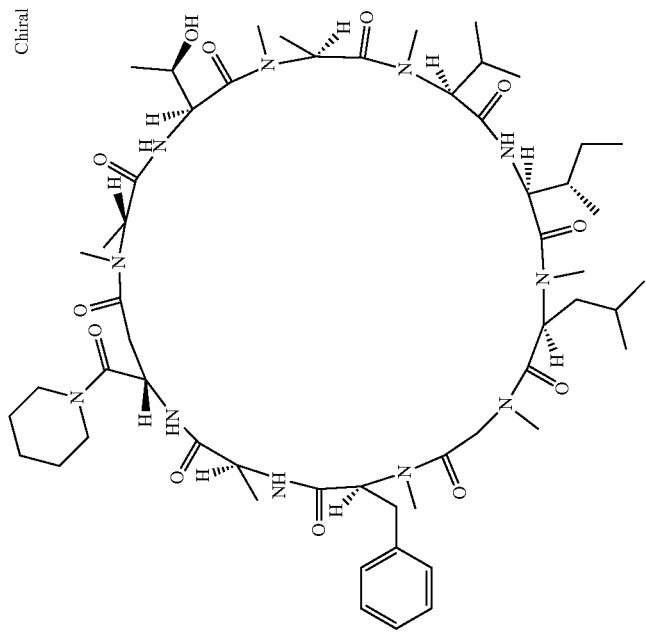
DP-485

TABLE 11-3-1-continued
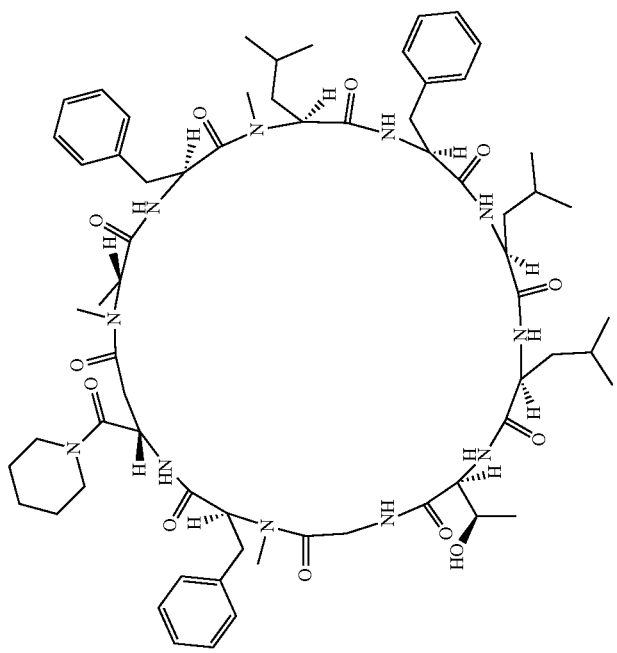

TABLE 11-3-1-continued
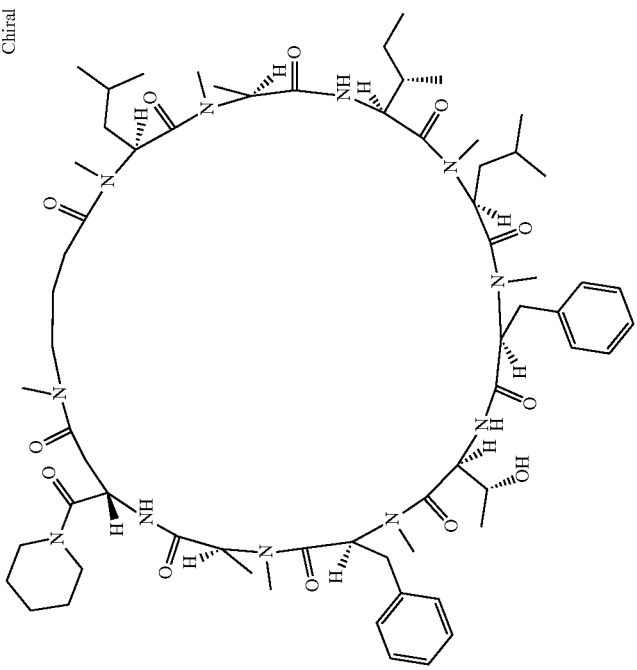
DP-487

TABLE 11-3-1-continued
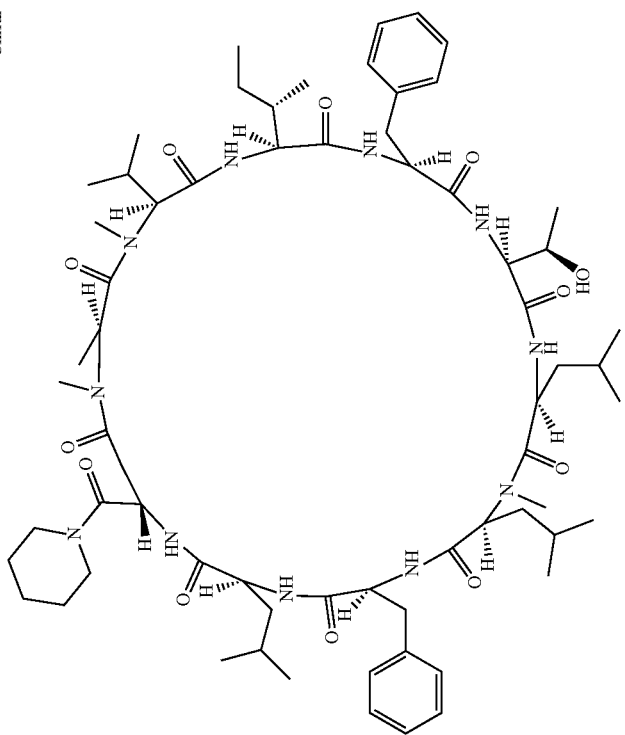
DP-488

TABLE 11-3-1-continued
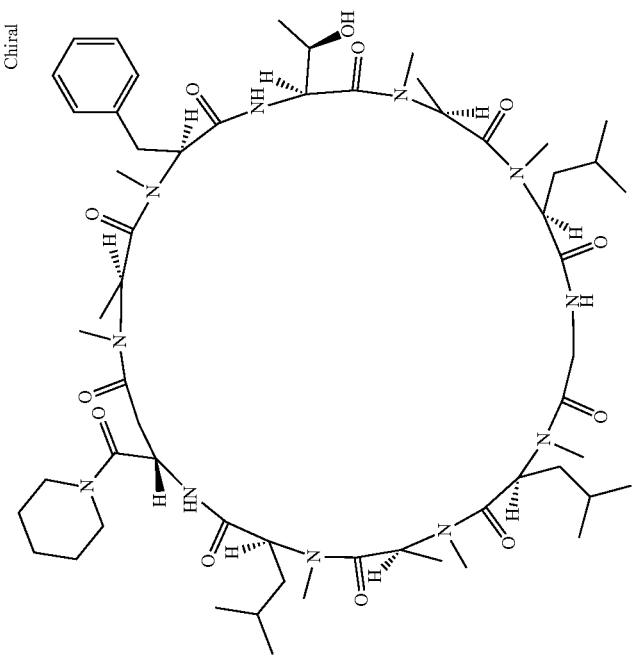
DP-489

TABLE 11-3-1-continued
DP-490
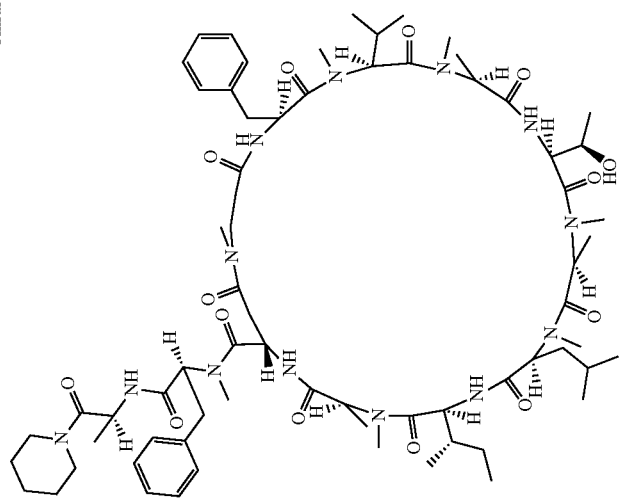

TABLE 11-3-1-continued
| DP-491 | 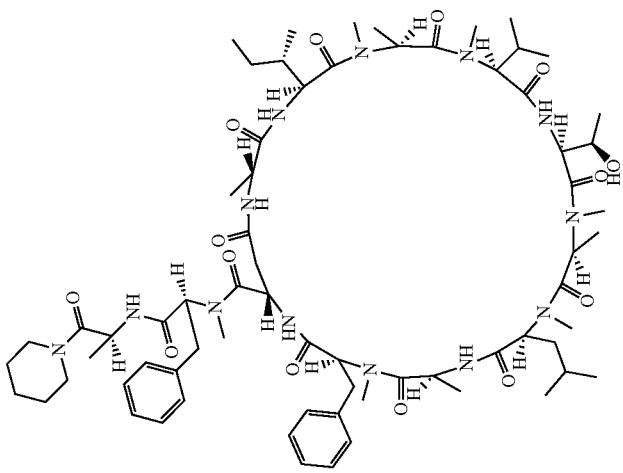 | Chiral |

TABLE 11-3-1-continued
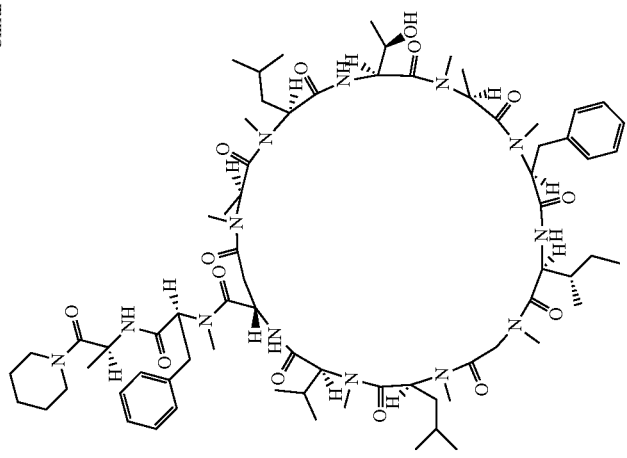
DP-492

TABLE 11-3-1-continued
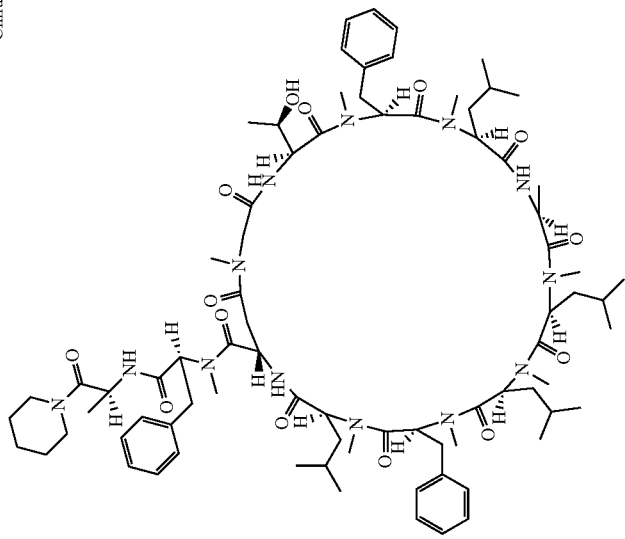
DP-493

TABLE 11-3-1-continued
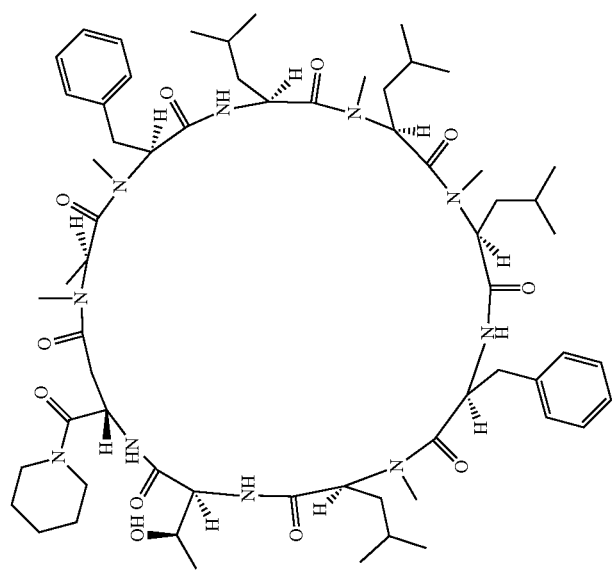
DP-494

TABLE 11-3-1-continued
Chiral
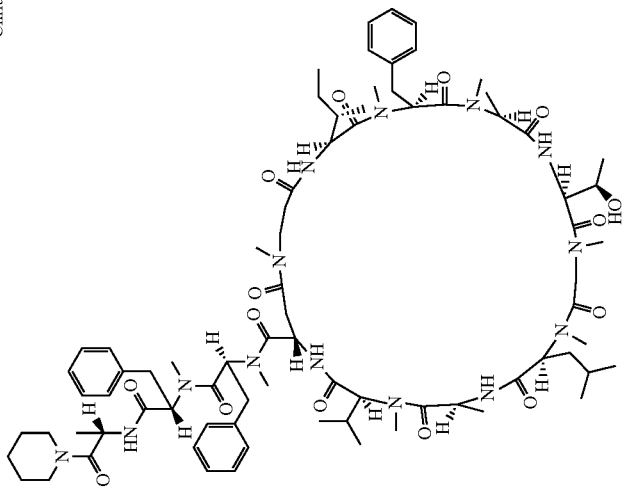
DP-495

TABLE 11-3-1-continued
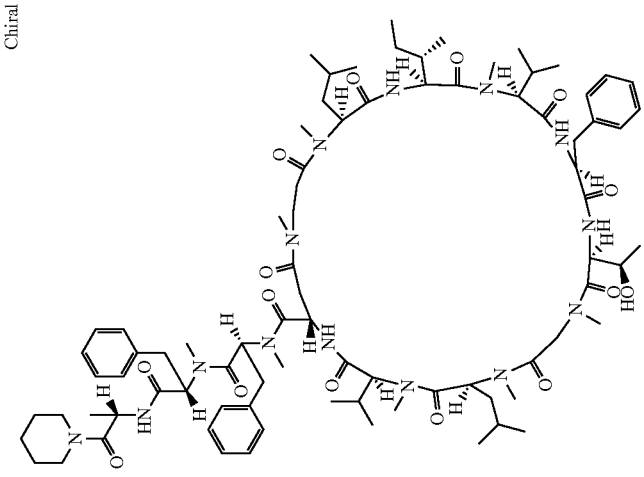
DP-496

TABLE 11-3-1-continued
Chiral
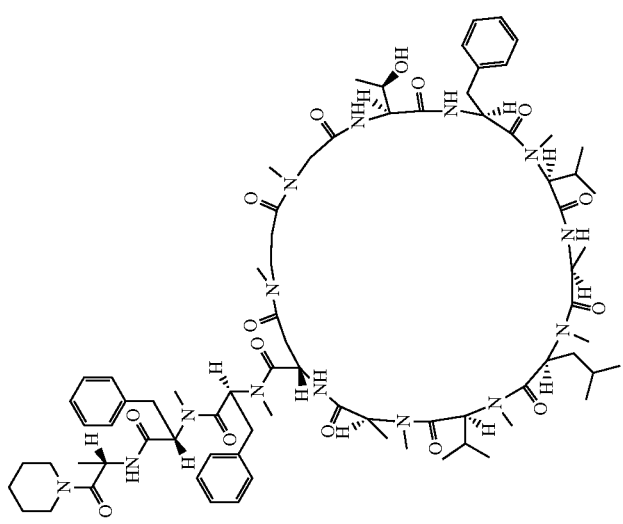
DP-497

TABLE 11-3-1-continued
Chiral
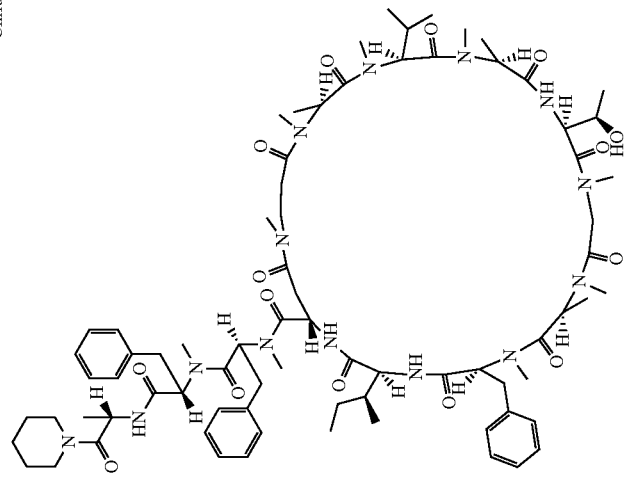
DP-498

TABLE 11-3-1-continued
DP-499
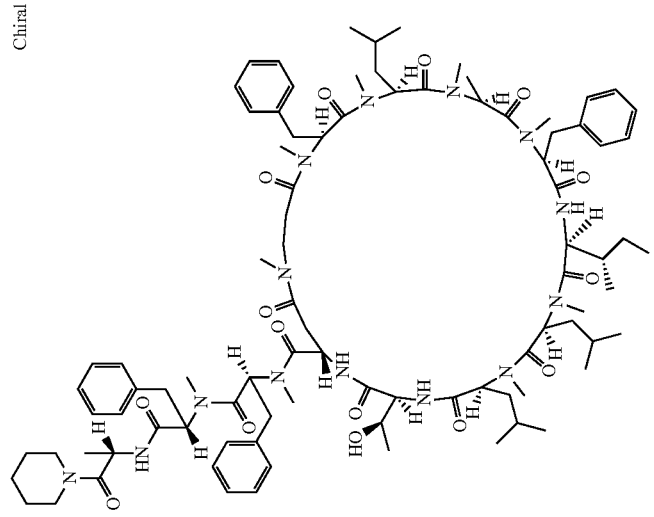
Chiral

TABLE 11-3-1-continued
DP-500
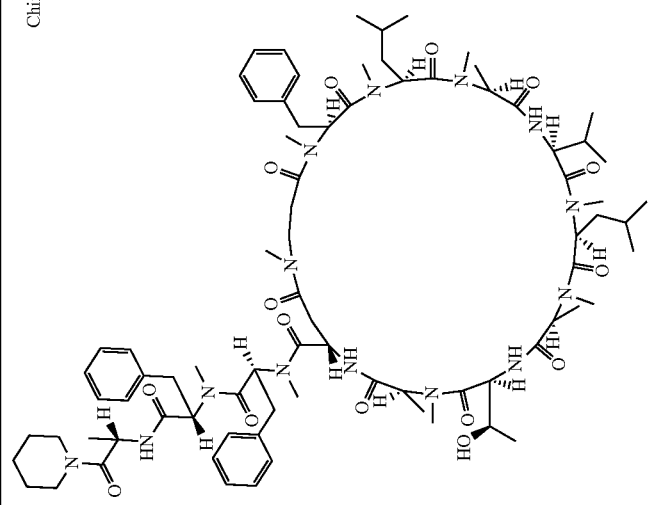

TABLE 11-3-1-continued
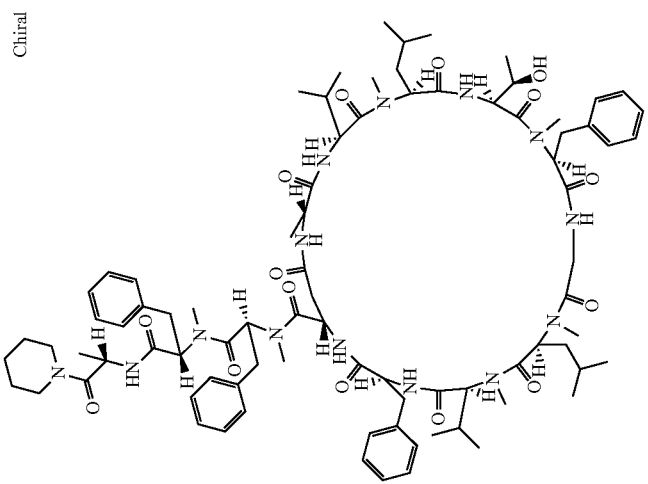
DP-501

TABLE 11-3-1-continued
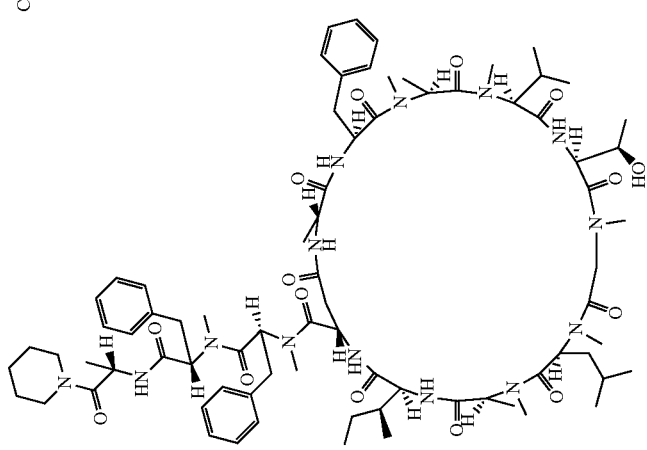
DP-502

TABLE 11-3-1-continued
Chiral
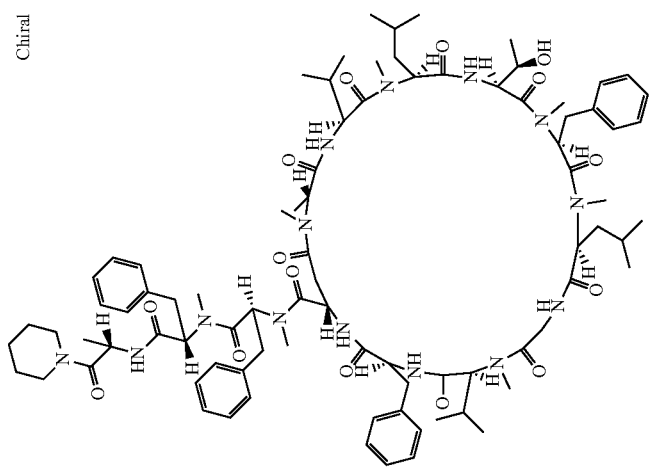
DP-503

TABLE 11-3-1-continued
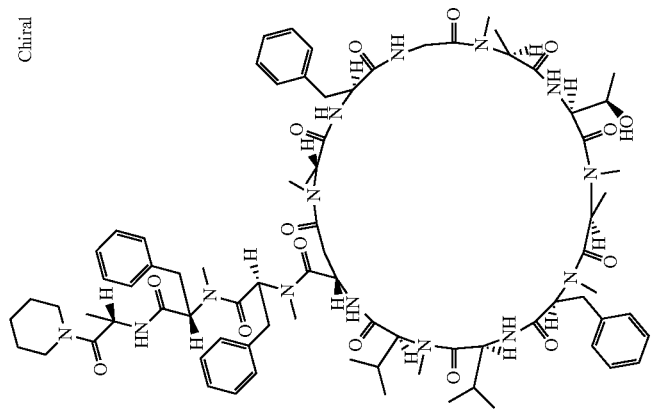
Chiral
DP-504

TABLE 11-3-1-continued
DP-505
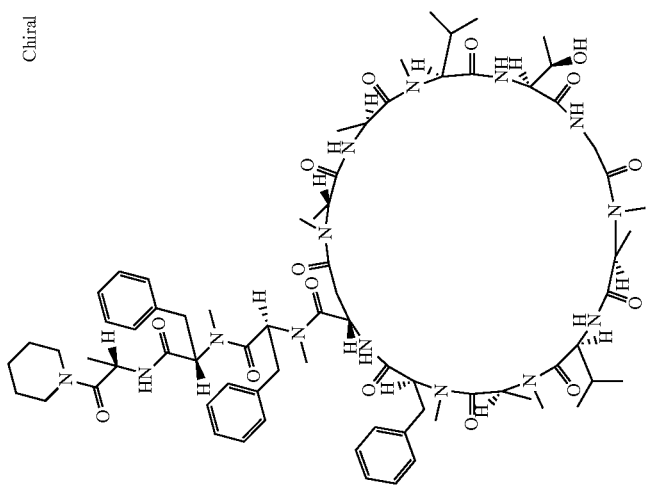

TABLE 11-3-1-continued
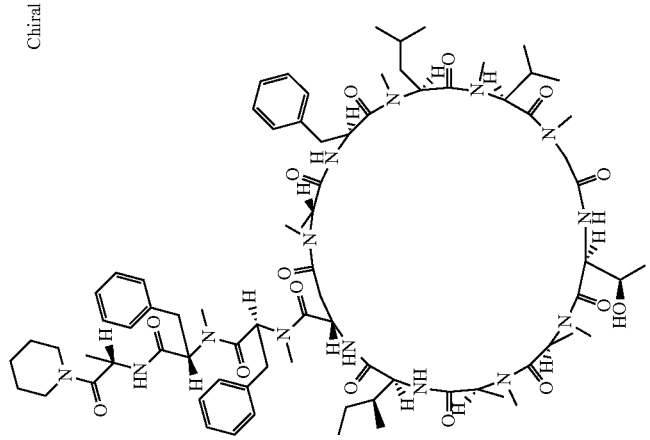
DP-506

TABLE 11-3-1-continued
DP-507
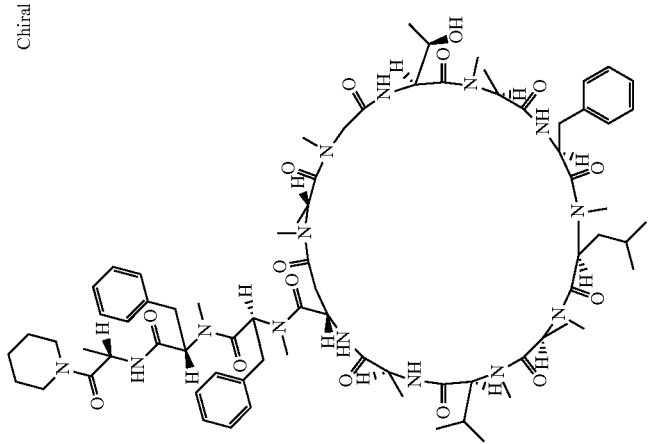

TABLE 11-3-1-continued
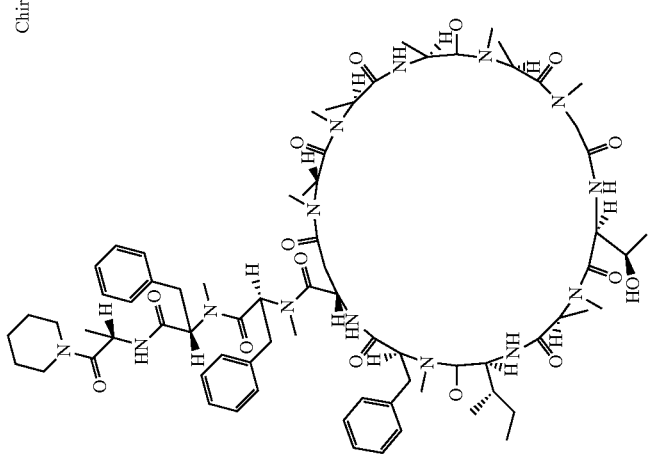
DP-508

TABLE 11-3-1-continued
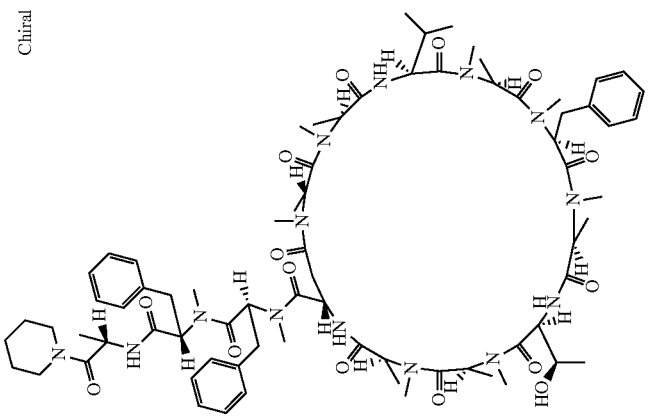
DP-509

TABLE 11-3-1-continued
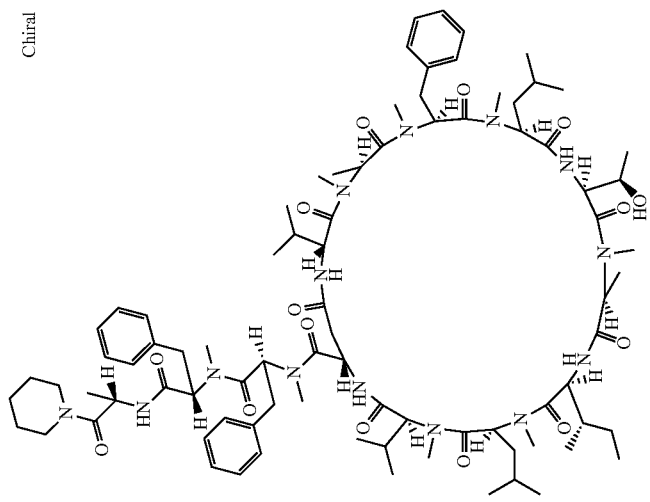
DP-510

TABLE 11-3-1-continued
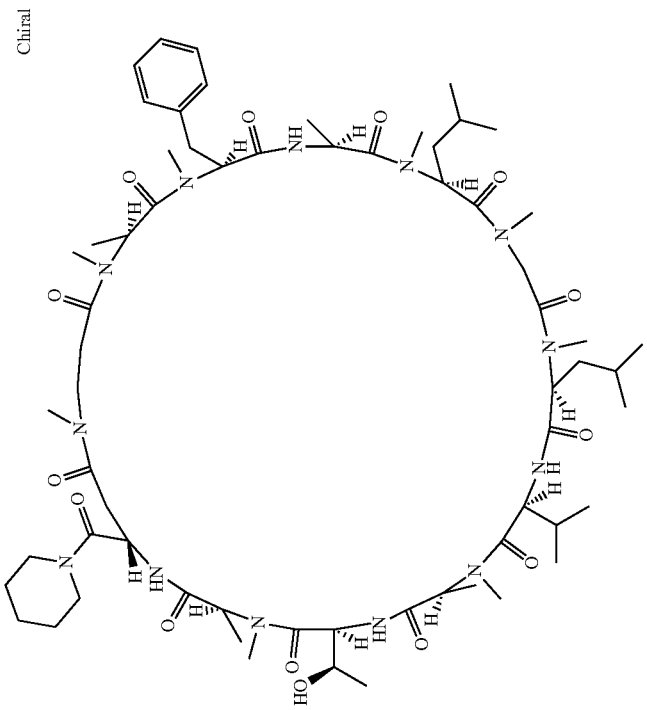
DP-511

TABLE 11-3-1-continued
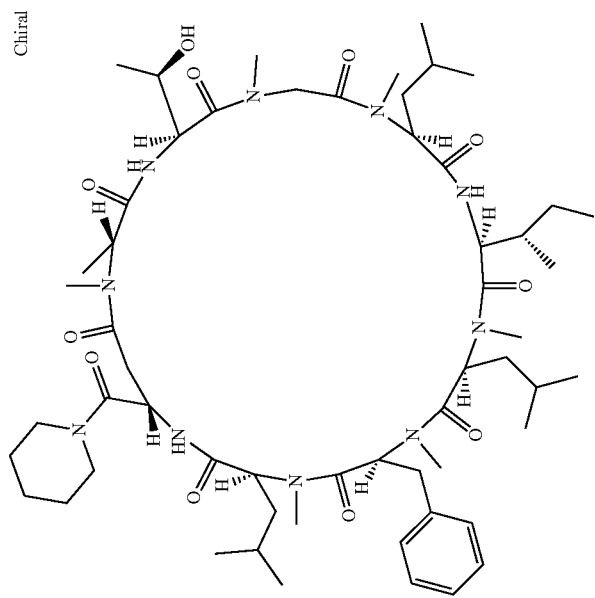
DP-512

TABLE 11-3-1-continued
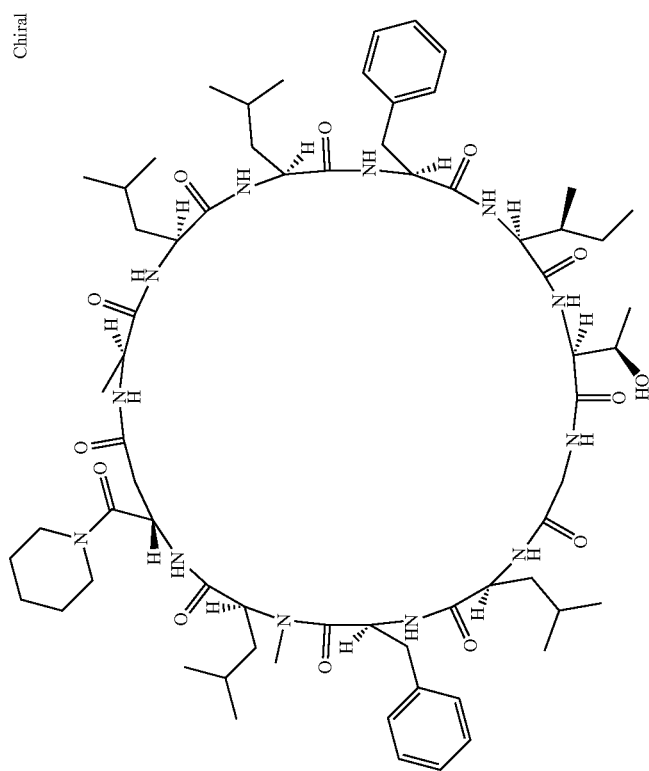
DP-513

TABLE 11-3-1-continued
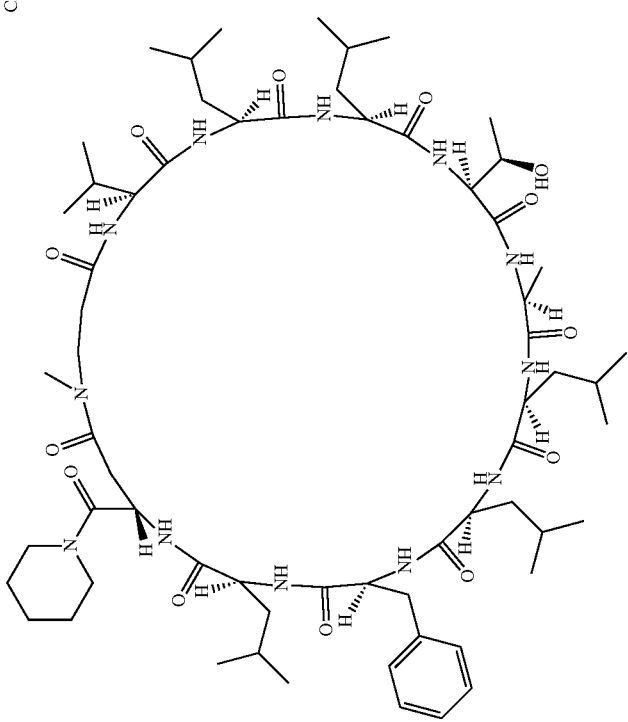
Chiral
DP-514

TABLE 11-3-1-continued
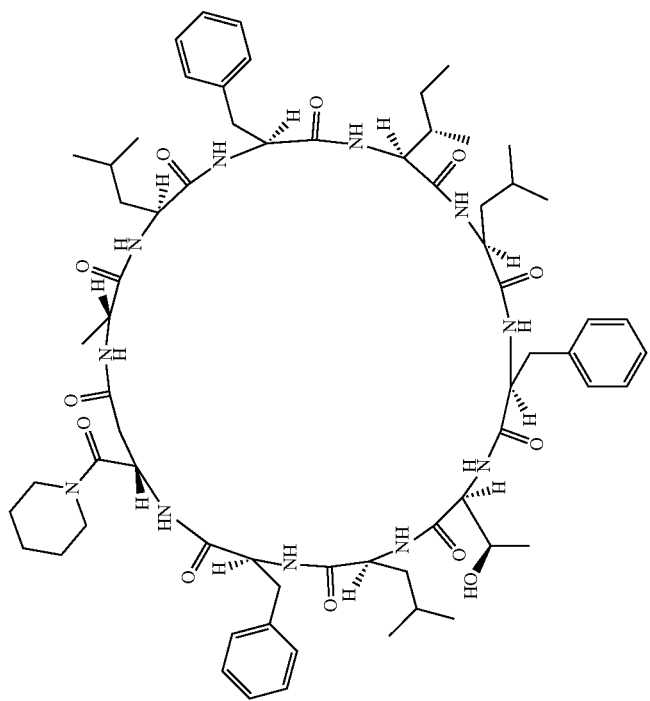
DP-515

TABLE 11-3-1-continued
Chiral
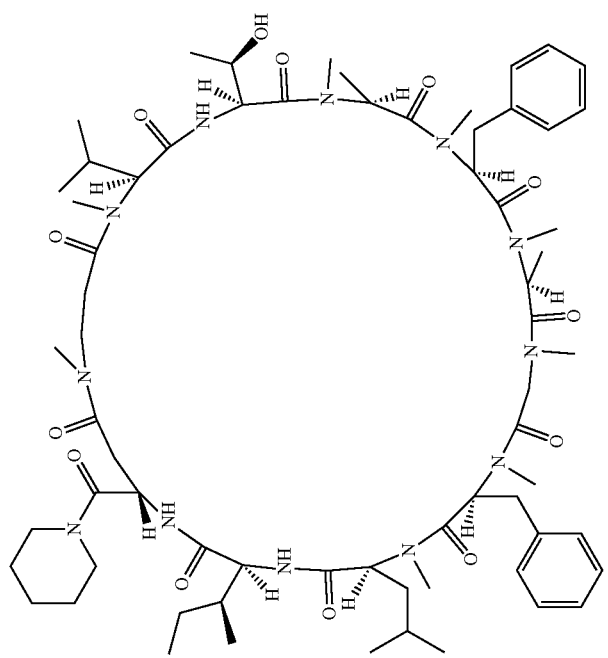
DP-516

TABLE 11-3-1-continued
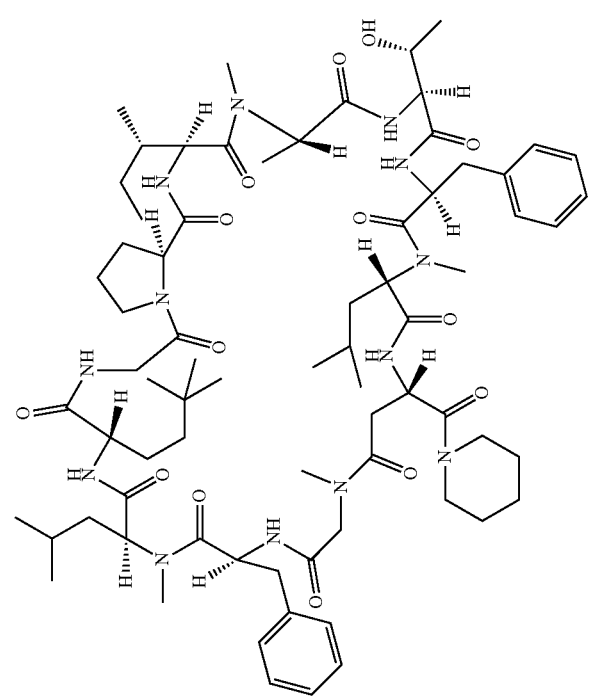
DP-517

TABLE 11-3-1-continued
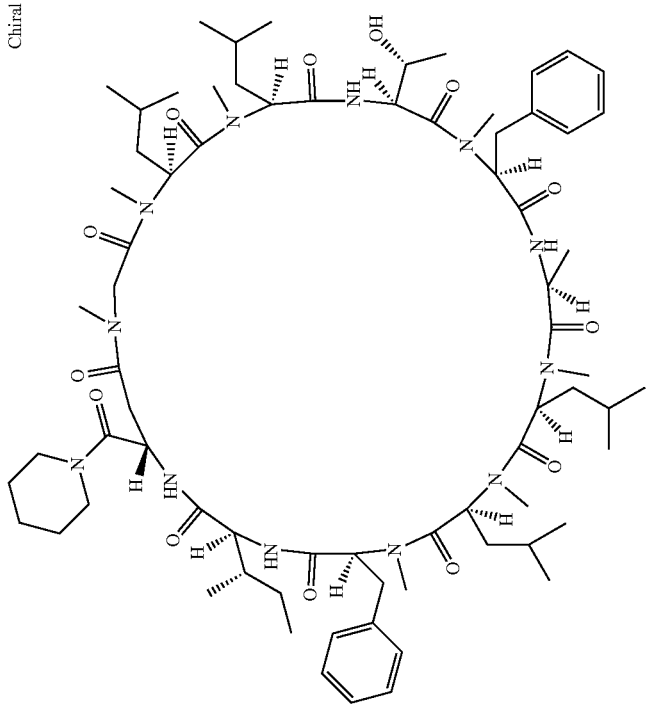
DP-518

TABLE 11-3-1-continued
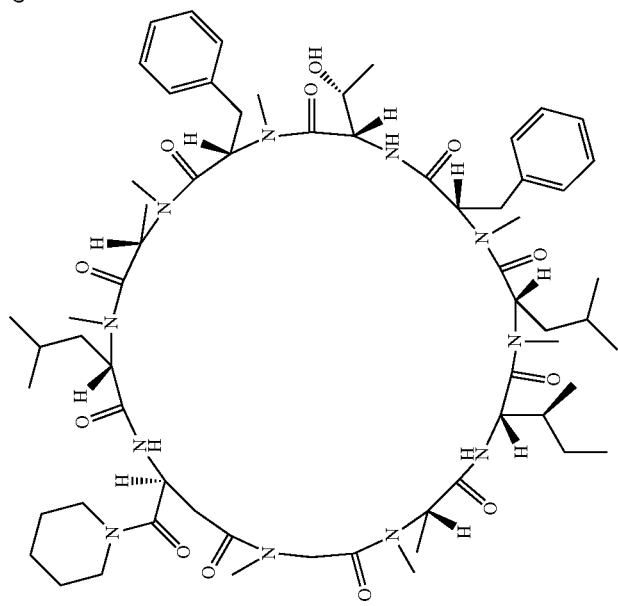
DP-519

TABLE 11-3-1-continued
DP-520
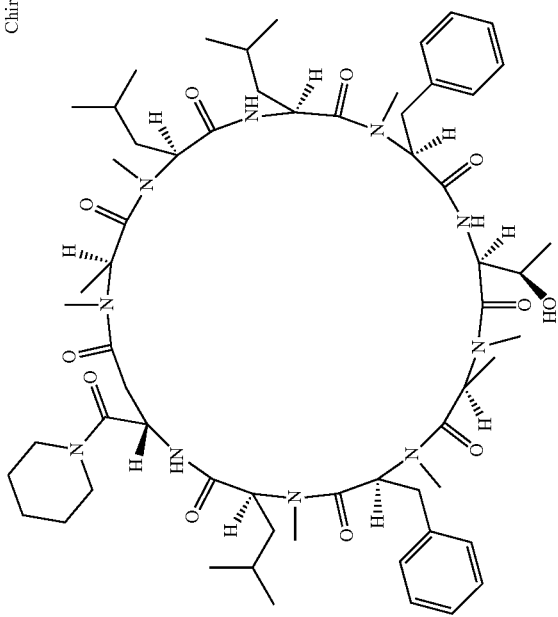

TABLE 11-3-1-continued
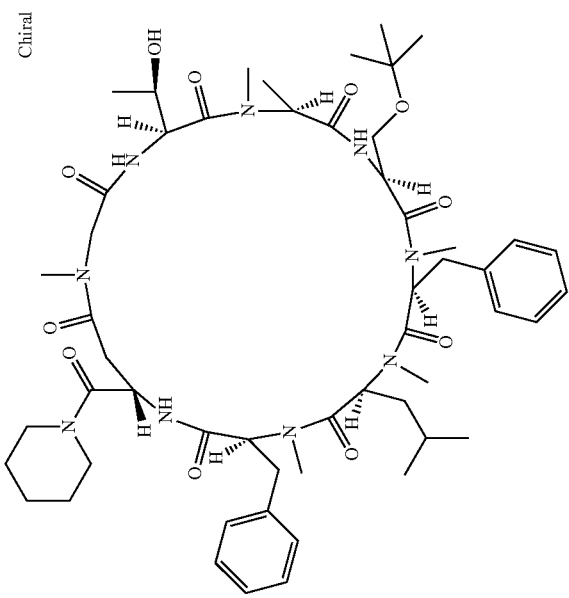
DP-521

TABLE 11-3-1-continued
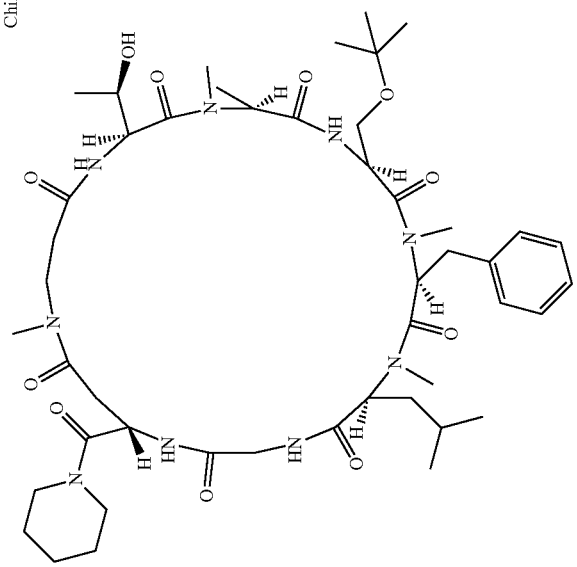
DP-522
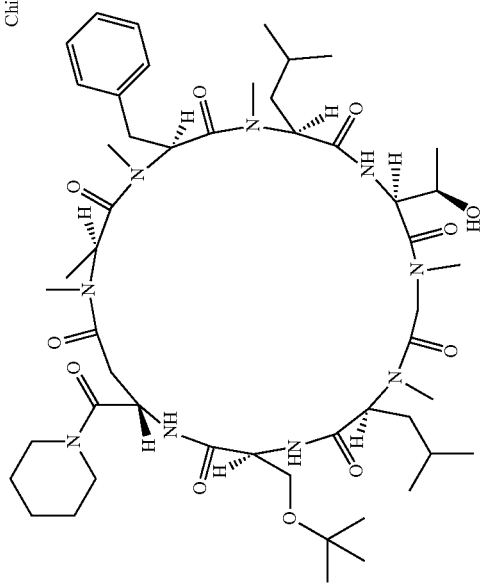
DP-523

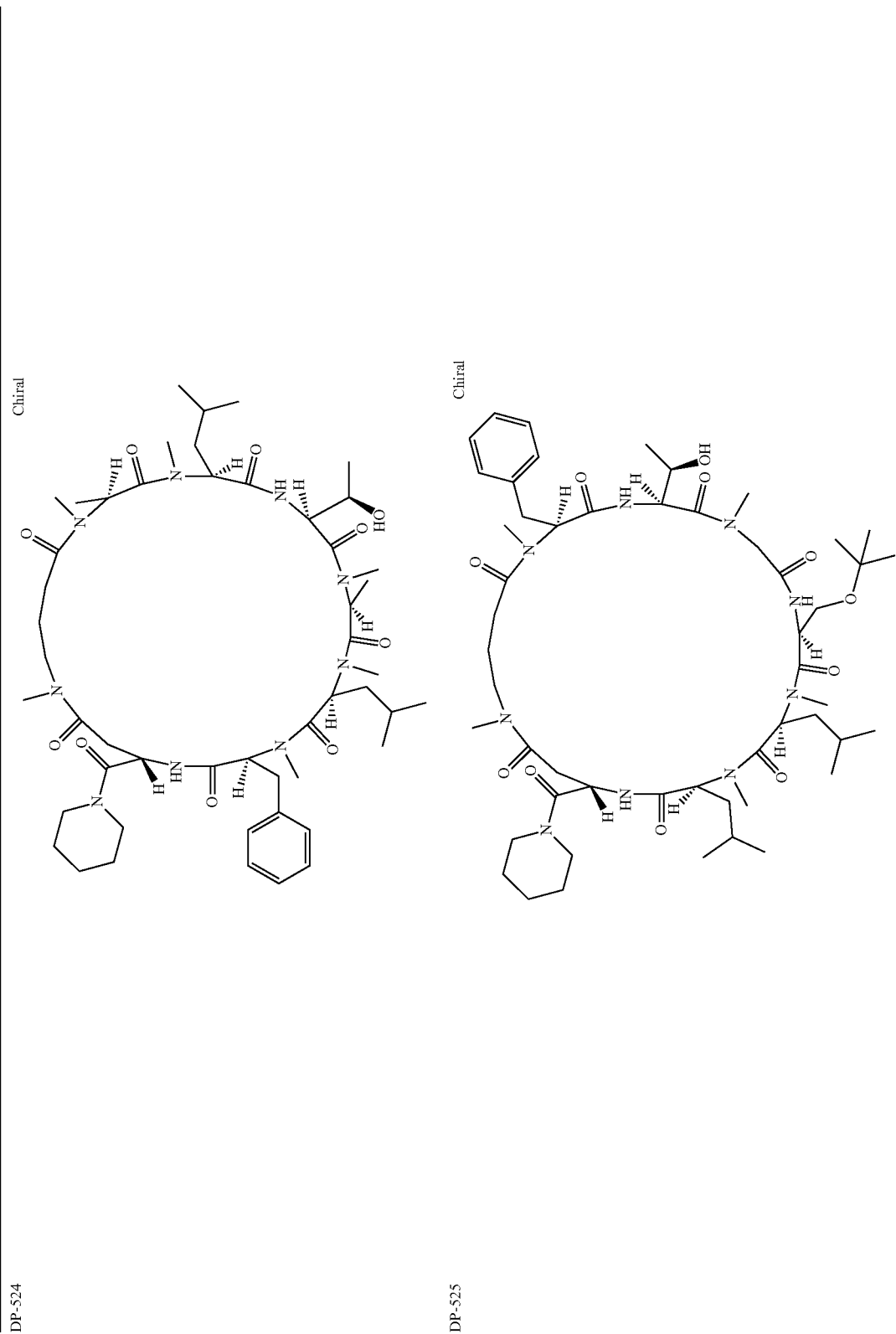

TABLE 11-3-1-continued
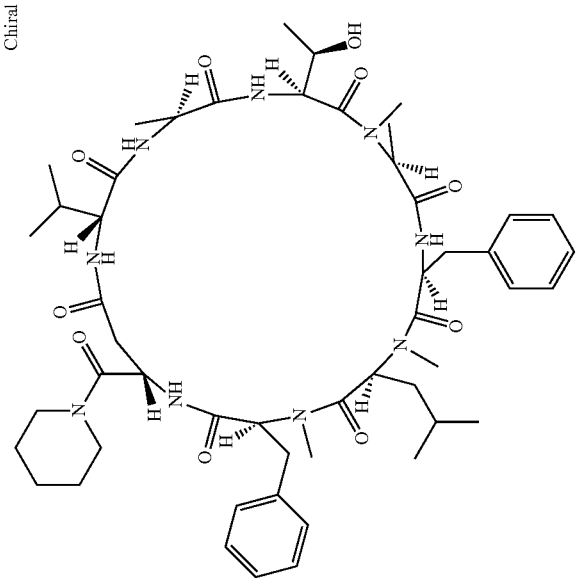
DP-526
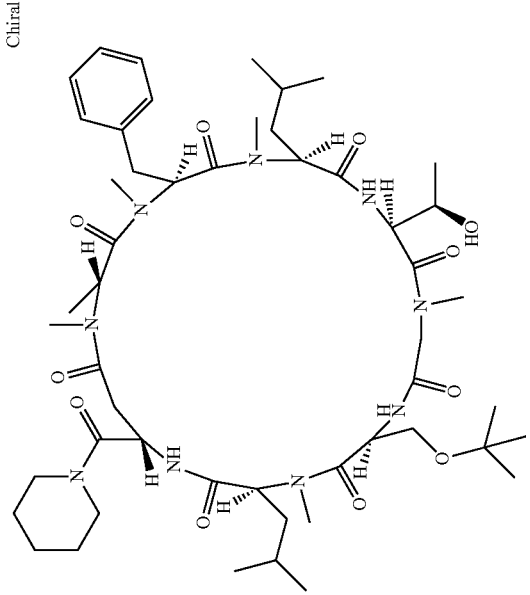
DP-527

TABLE 11-3-1-continued
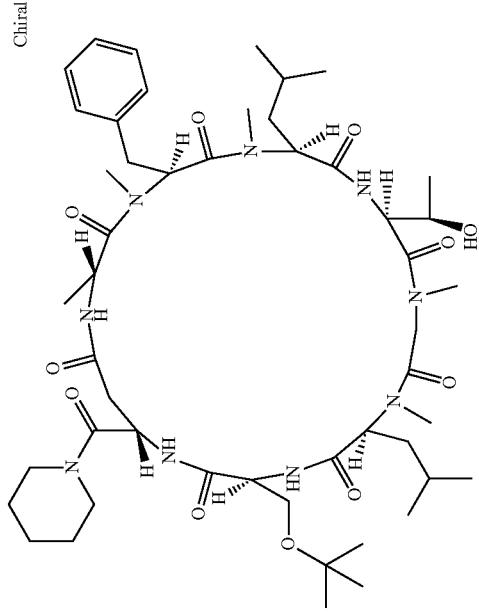
DP-528
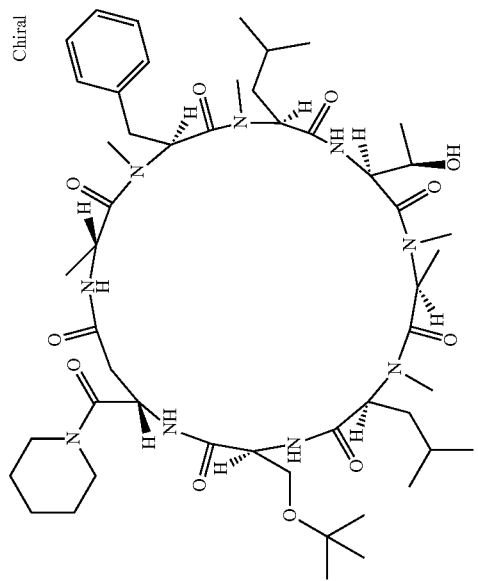
DP-529

TABLE 11-3-1-continued
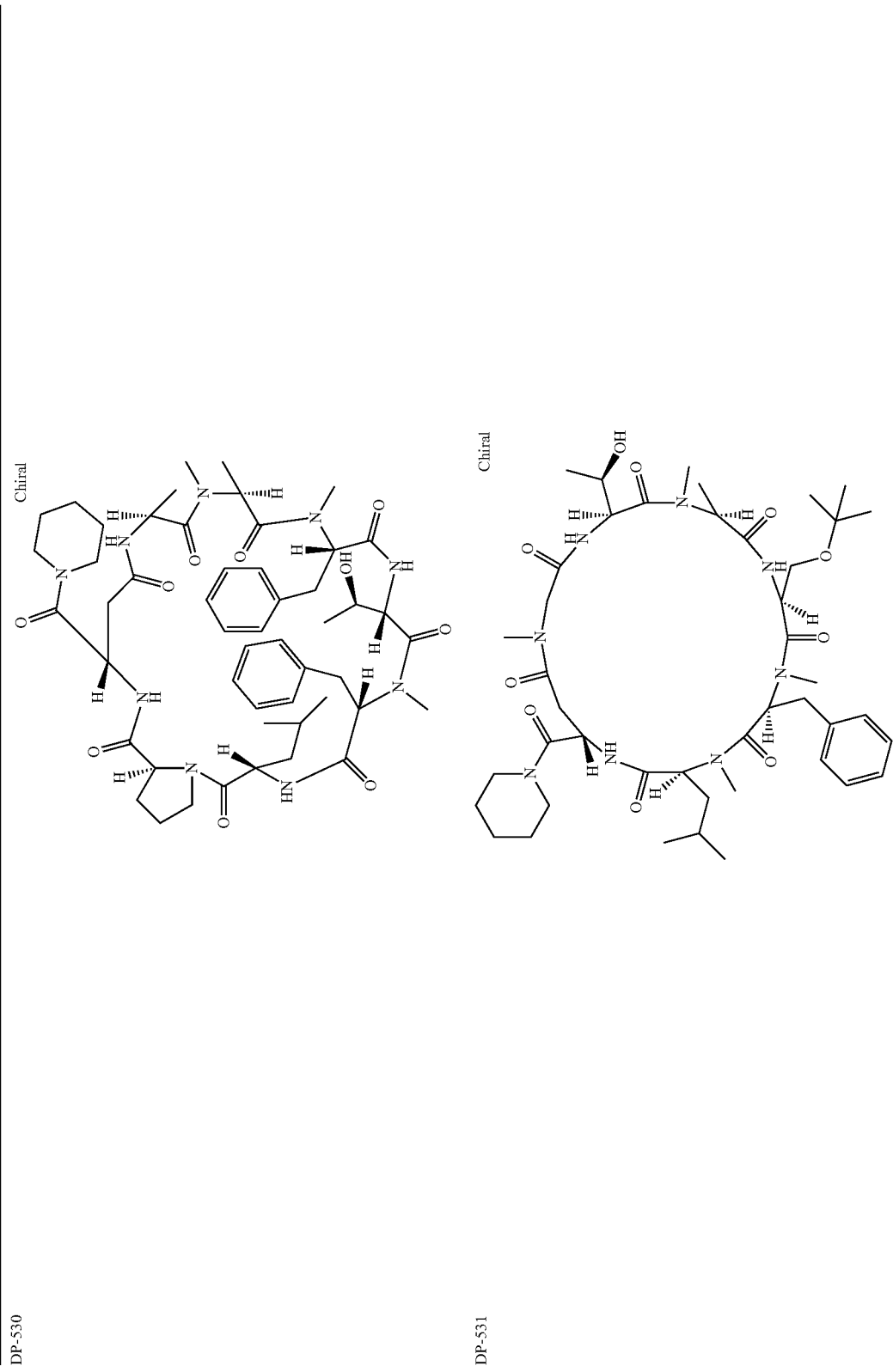
DP-530
DP-531

TABLE 11-3-1-continued
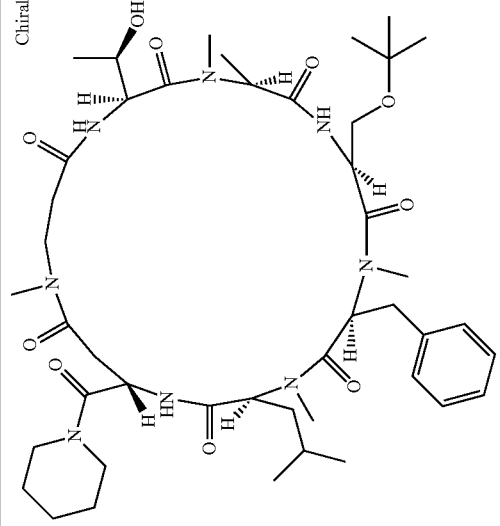
DP-532
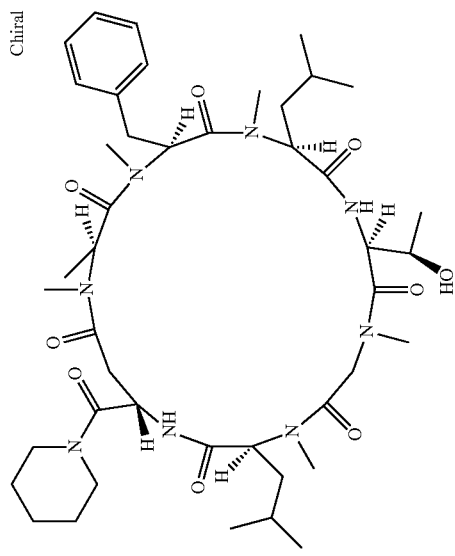
DP-533

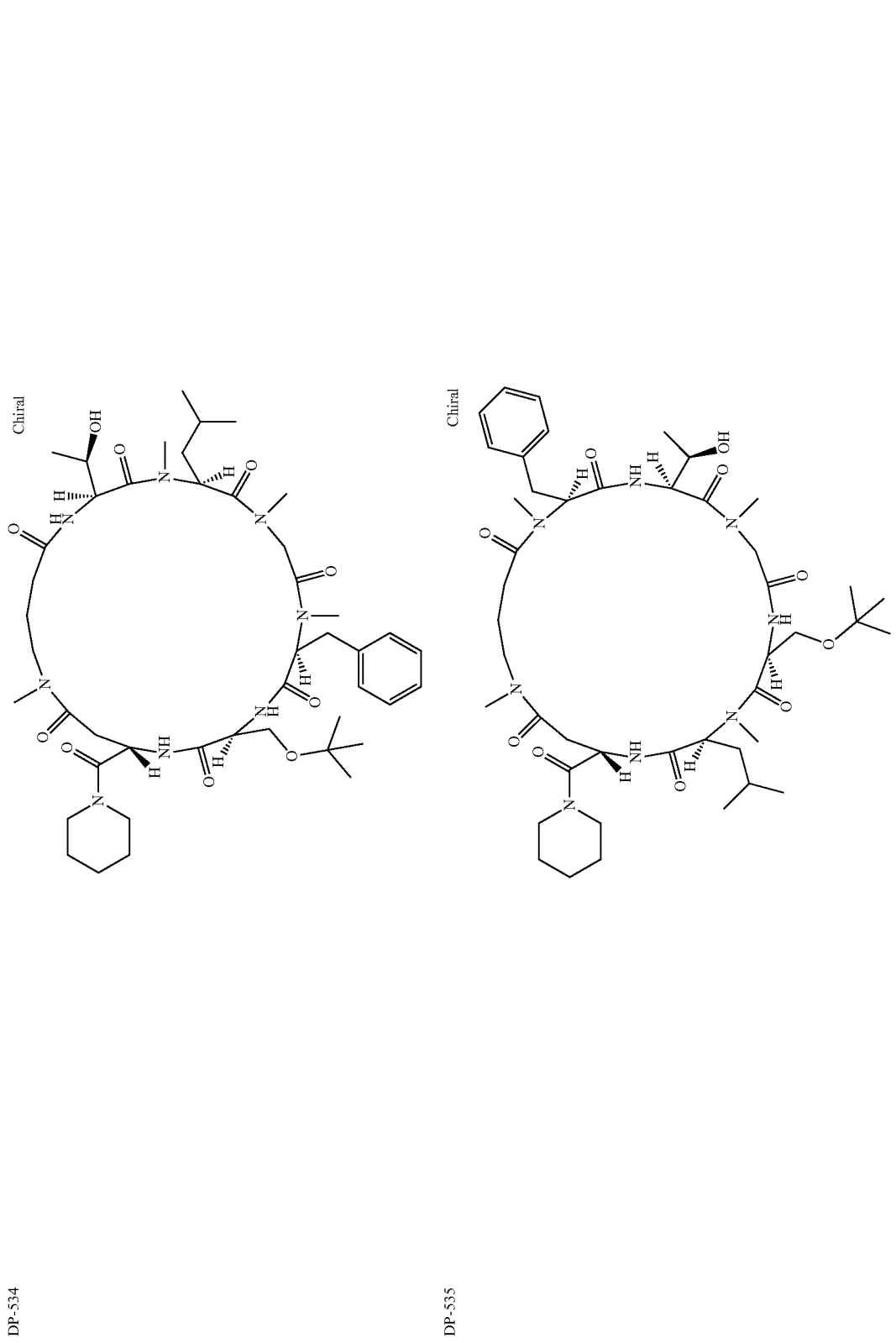

TABLE 11-3-1-continued
| Chiral | Chiral |
|---|---|
| 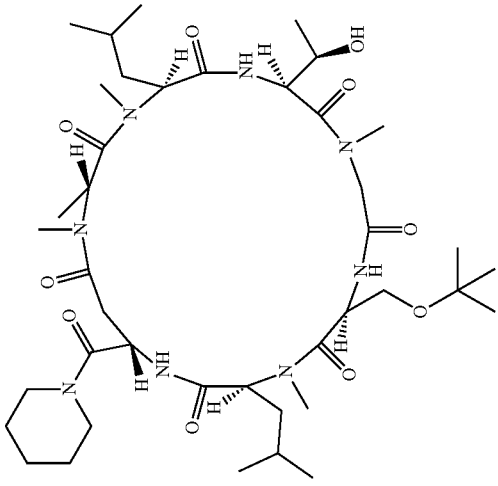 | 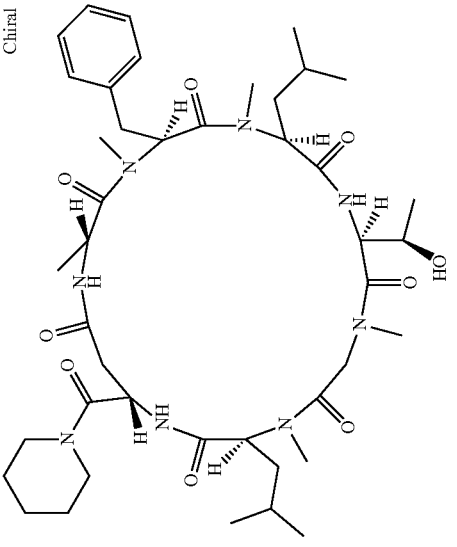 |
| DP-536 | DP-537 |

TABLE 11-3-1-continued
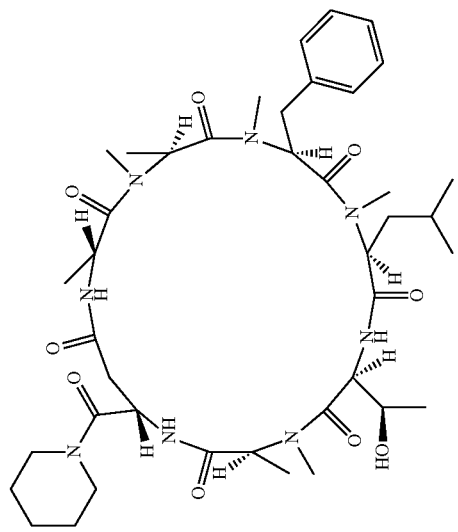
DP-538
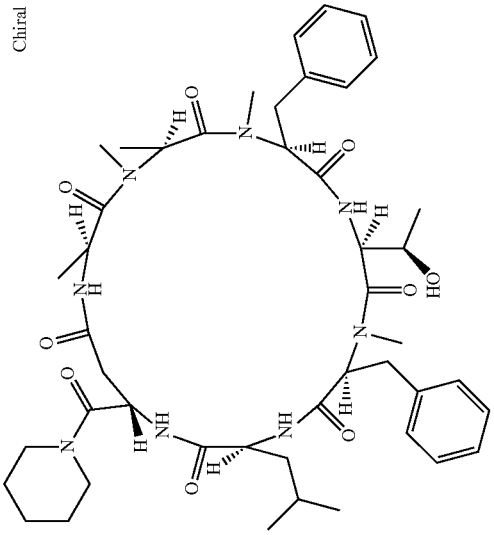
DP-539

TABLE 11-3-1-continued
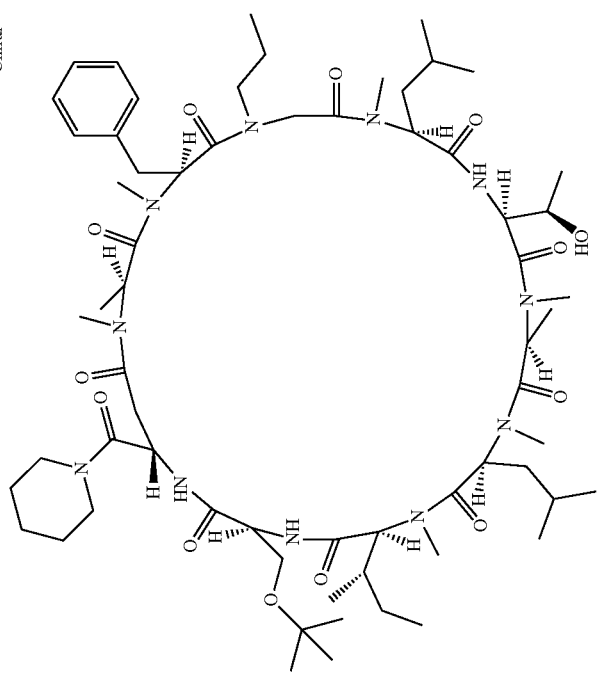
DP-540

TABLE 11-3-1-continued

| | |
|---|---|
| DP-541 | DP-542 |

TABLE 11-3-1-continued
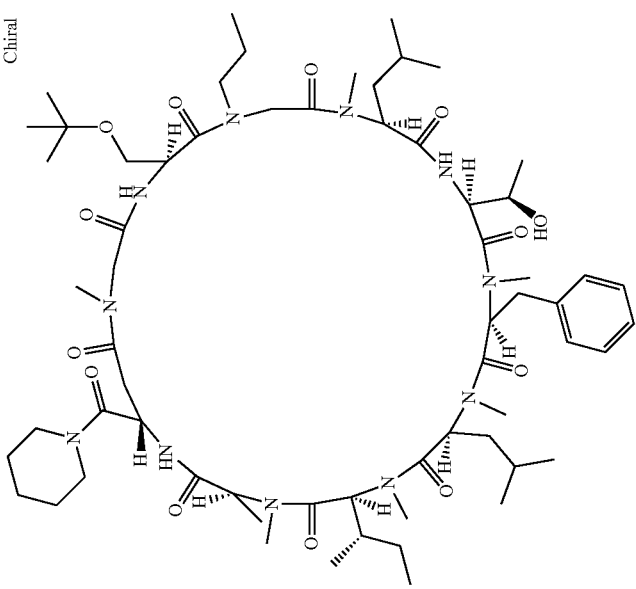
DP-543

TABLE 11-3-1-continued
DP-544

TABLE 11-3-1-continued
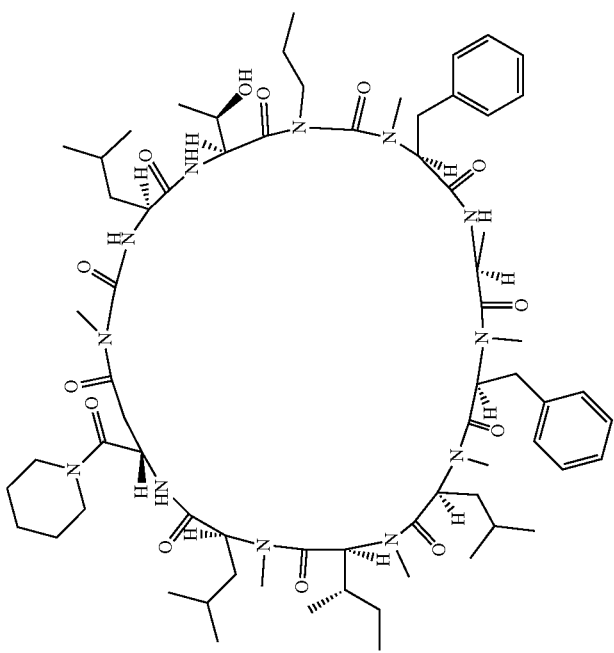
DP-545

TABLE 11-3-1-continued
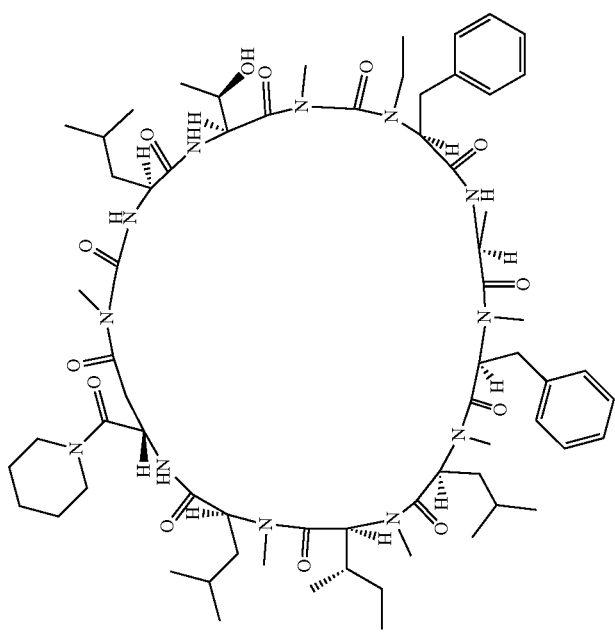
DP-546

TABLE 11-3-1-continued
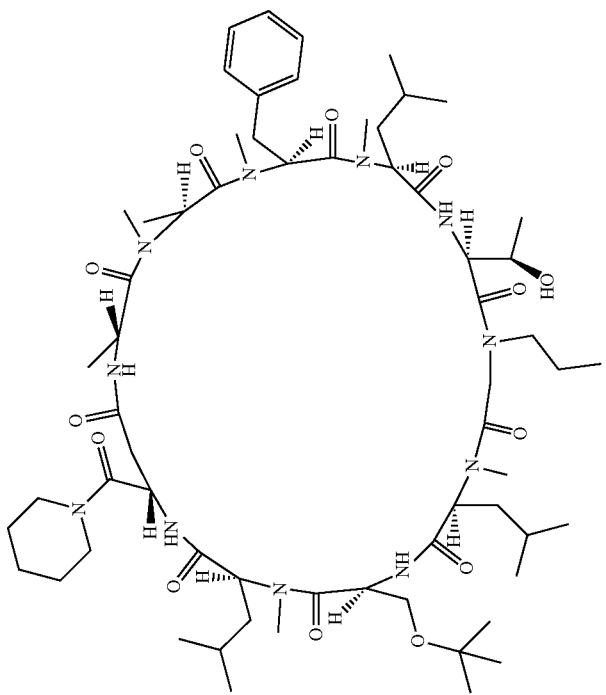
DP-547

TABLE 11-3-1-continued
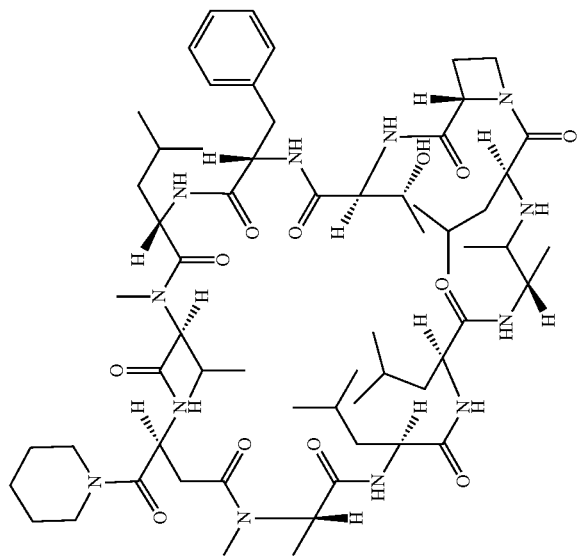
DP-548

TABLE 11-3-1-continued
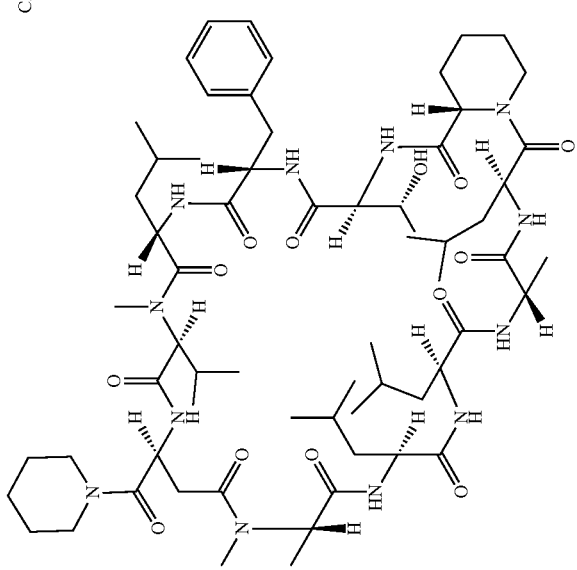
DP-549

TABLE 11-3-1-continued
DP-550
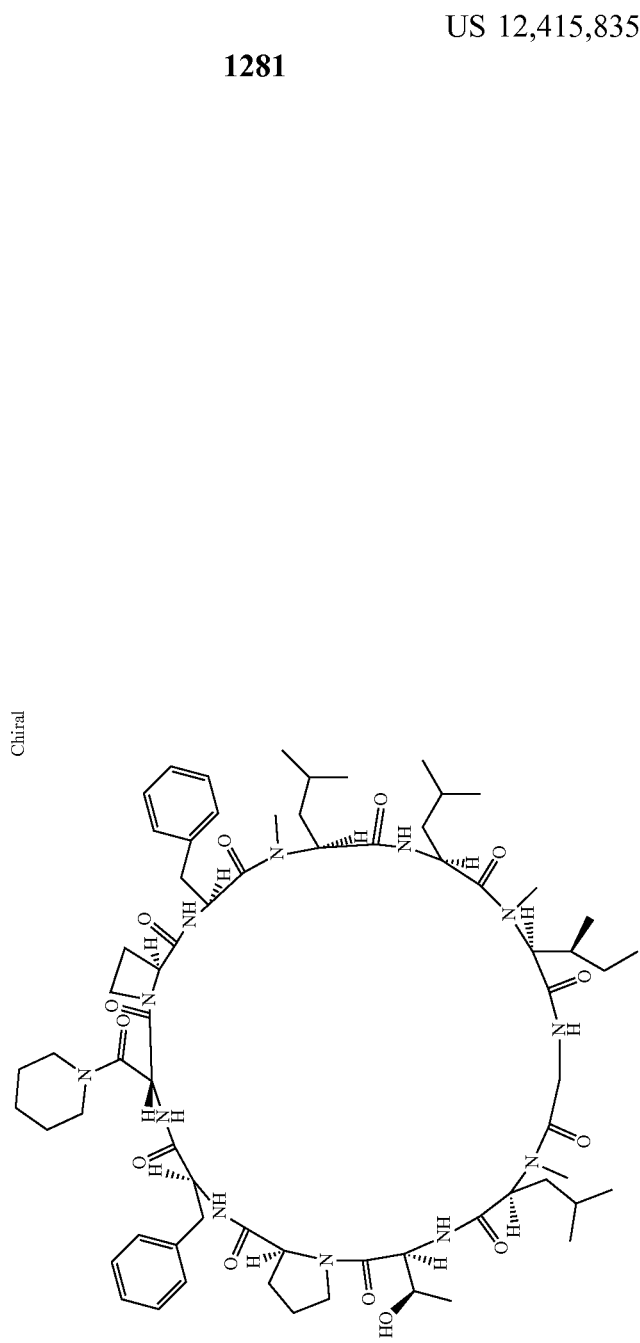

TABLE 11-3-1-continued
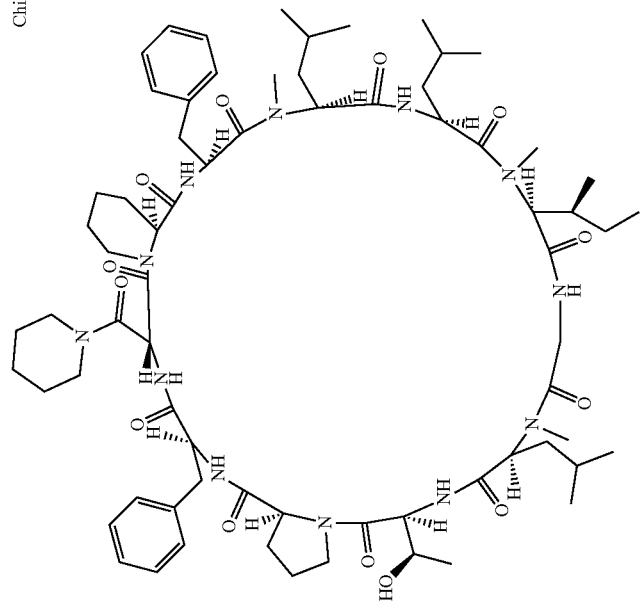
DP-551

TABLE 11-3-1-continued
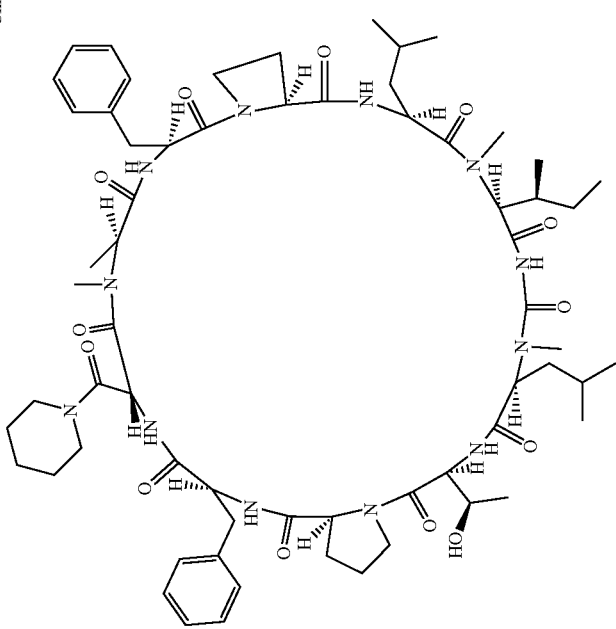
DP-552

TABLE 11-3-1-continued
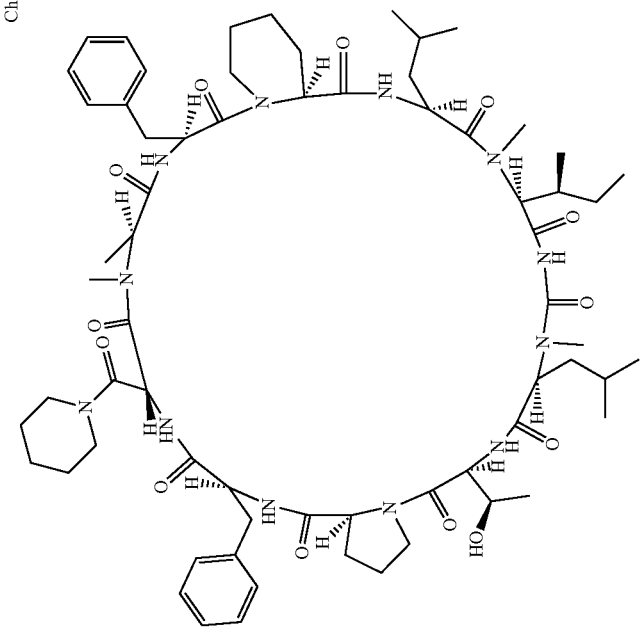
DP-553

TABLE 11-3-1-continued
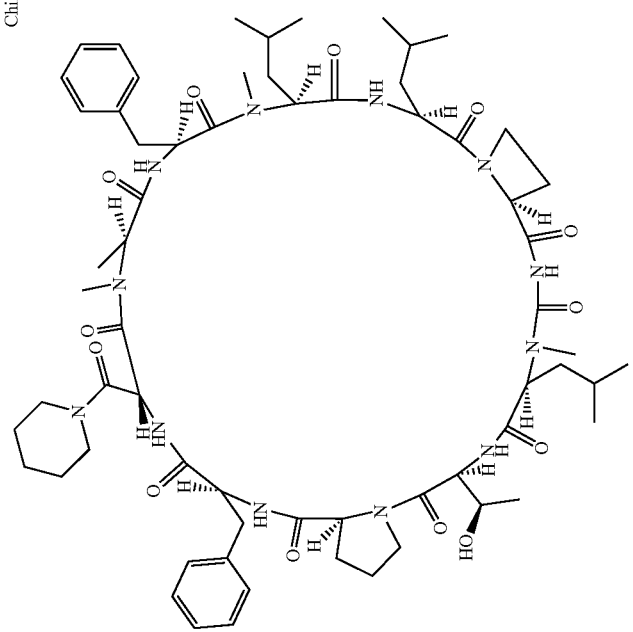
DP-554

TABLE 11-3-1-continued
Chiral
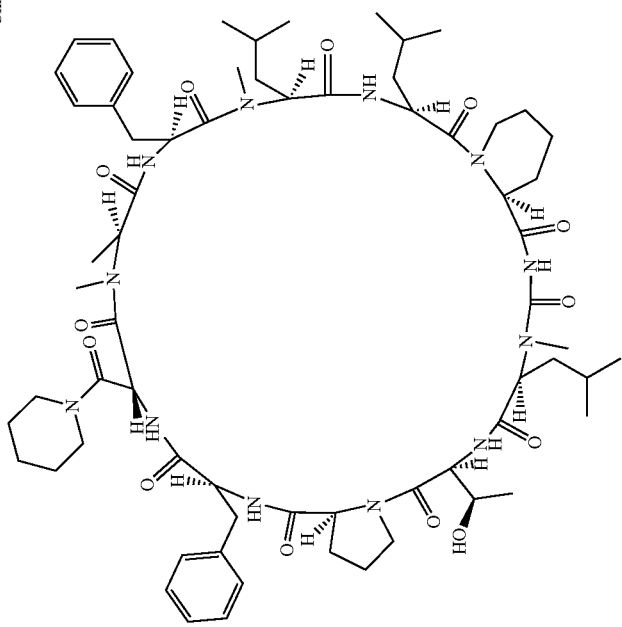
DP-555

TABLE 11-3-1-continued
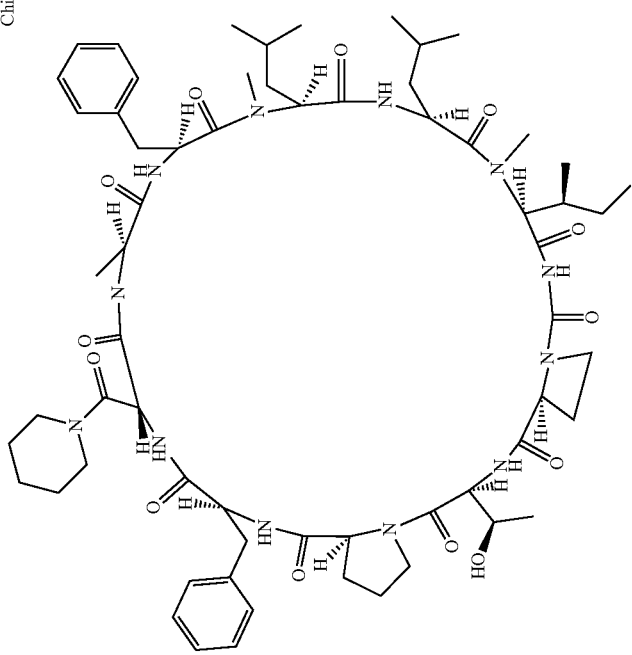
DP-556

TABLE 11-3-1-continued
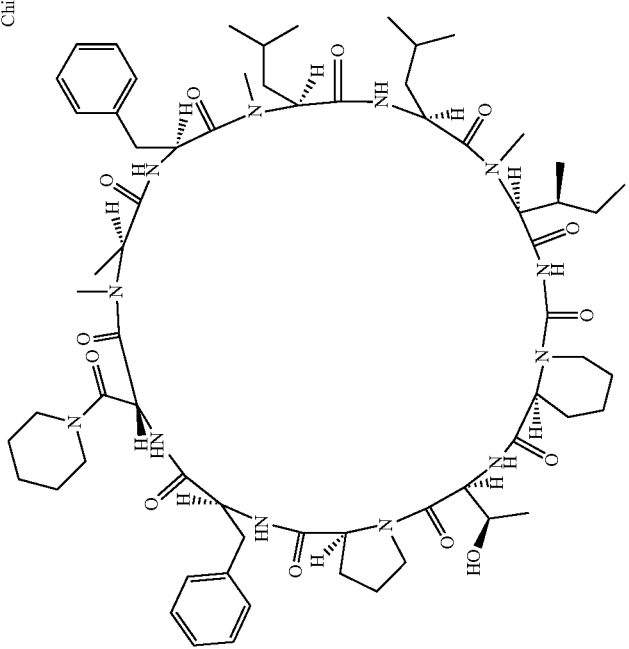
DP-557

TABLE 11-3-1-continued
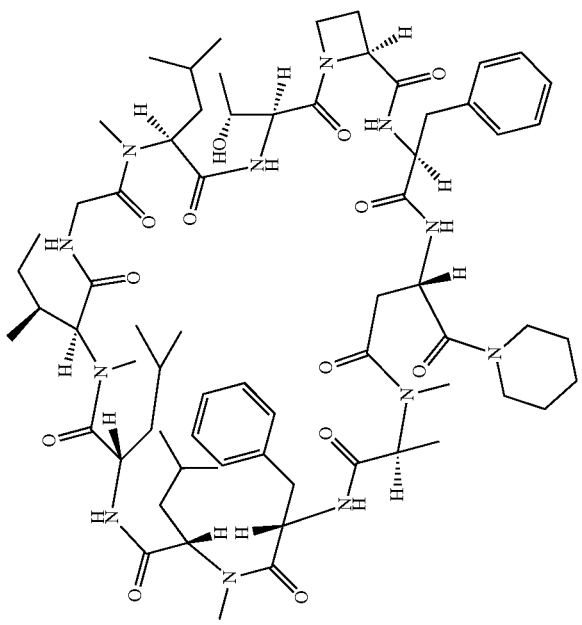
DP-558

TABLE 11-3-1-continued
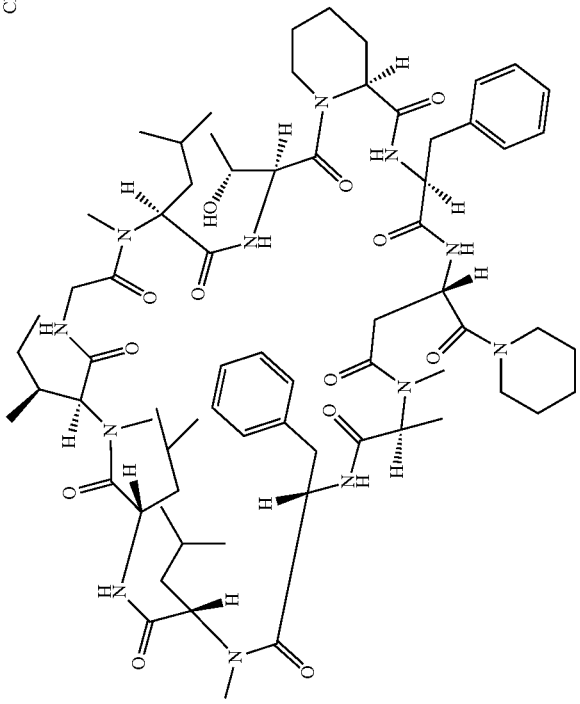
DP-559

TABLE 11-3-1-continued
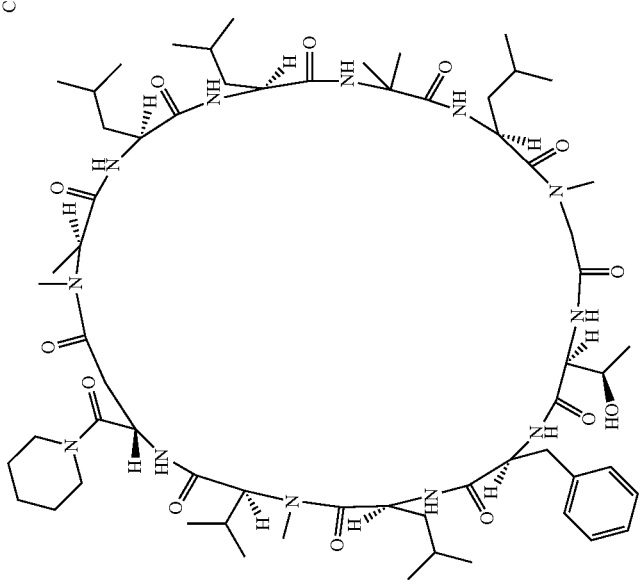
DP-560

TABLE 11-3-1-continued
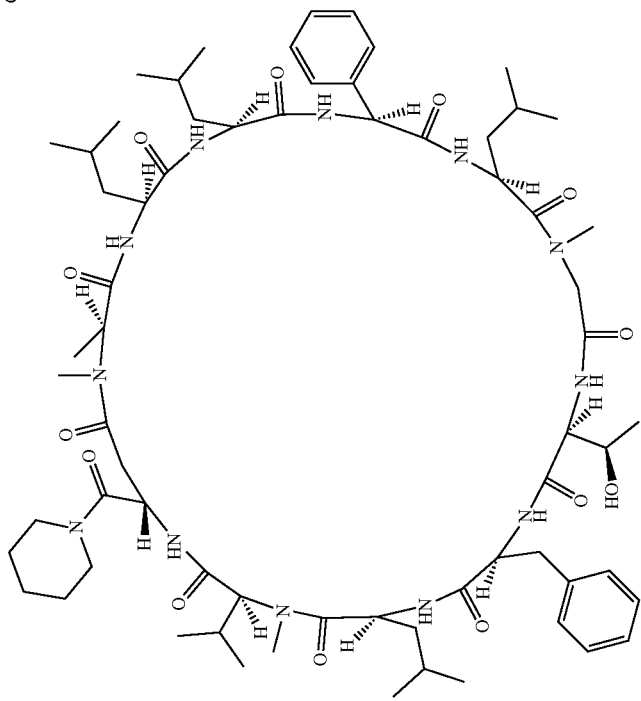
DP-561

TABLE 11-3-1-continued
DP-562
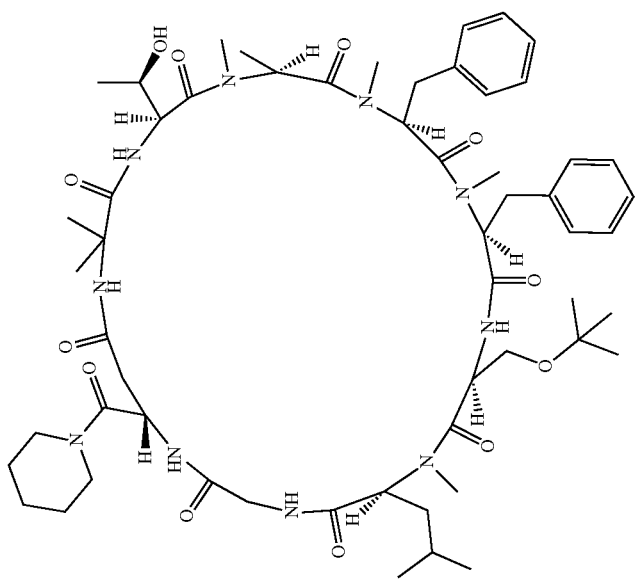

TABLE 11-3-1-continued
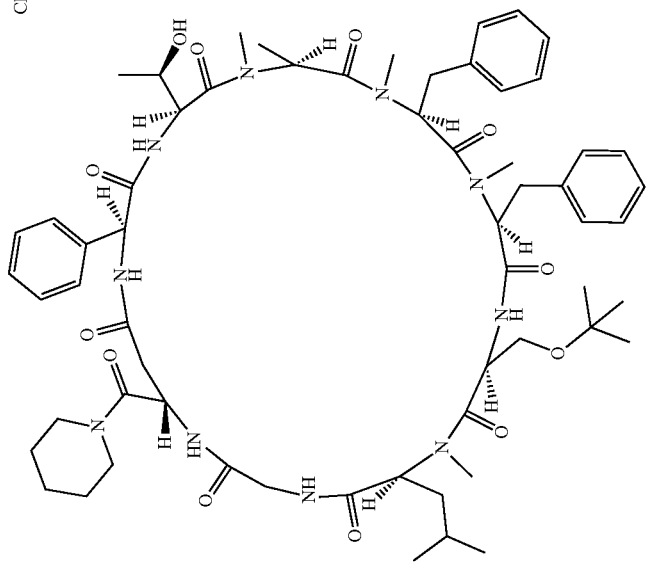
DP-563

TABLE 11-3-1-continued
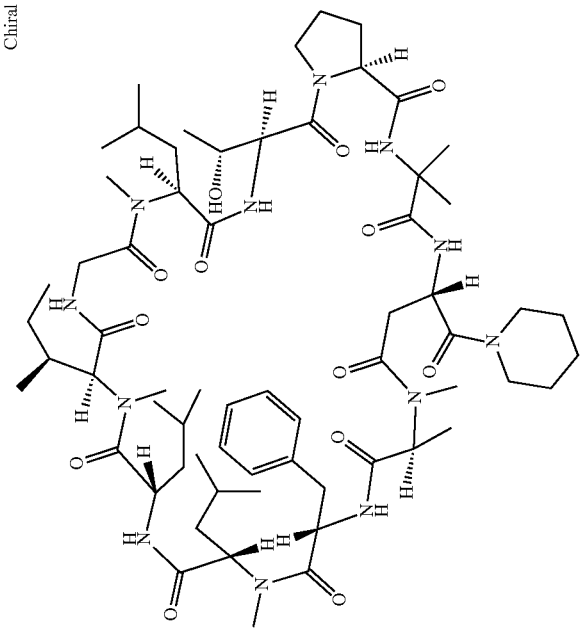
DP-564

TABLE 11-3-1-continued
DP-565
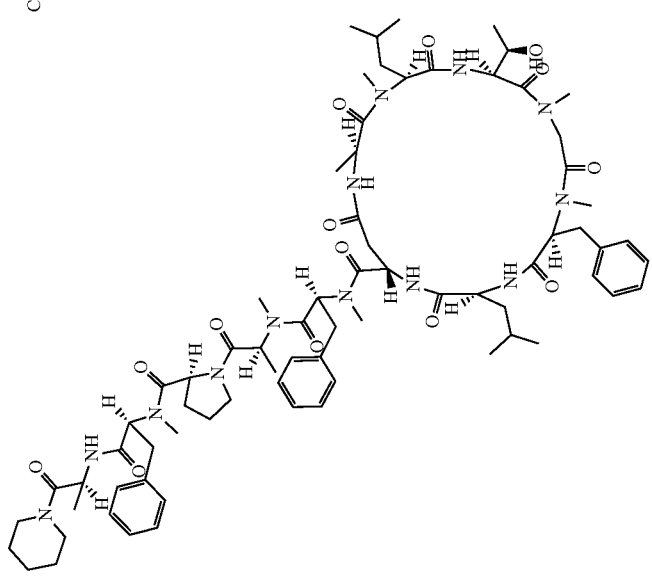

TABLE 11-3-1-continued
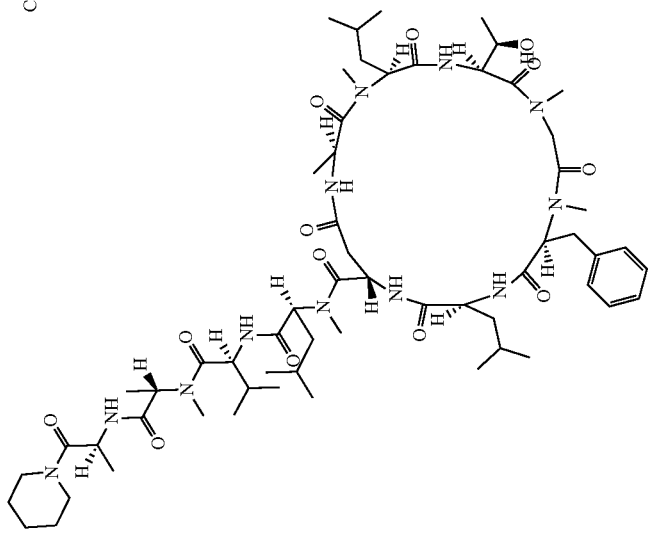
DP-566

TABLE 11-3-1-continued
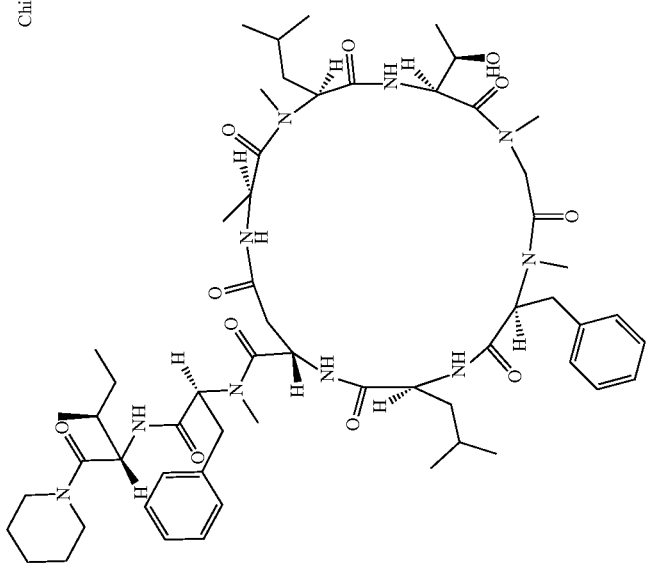
DP-567

TABLE 11-3-1-continued
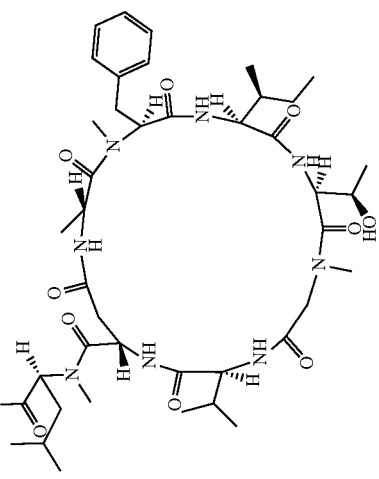
DP-568

TABLE 11-3-1-continued
Chiral
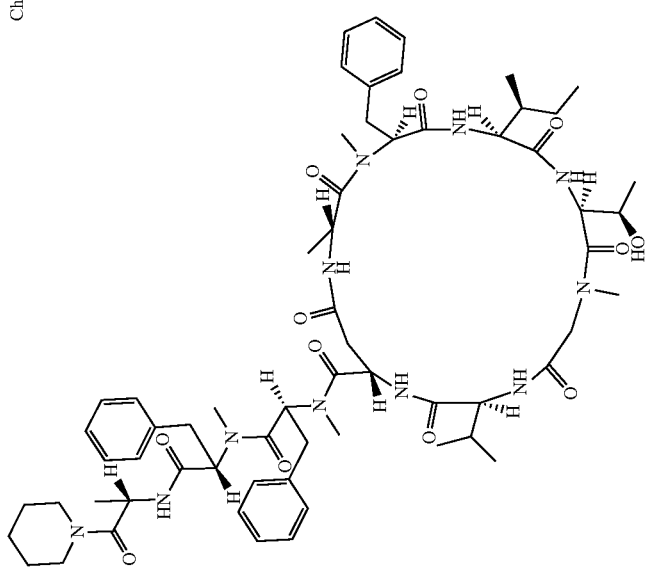
DP-569

TABLE 11-3-1-continued
DP-570
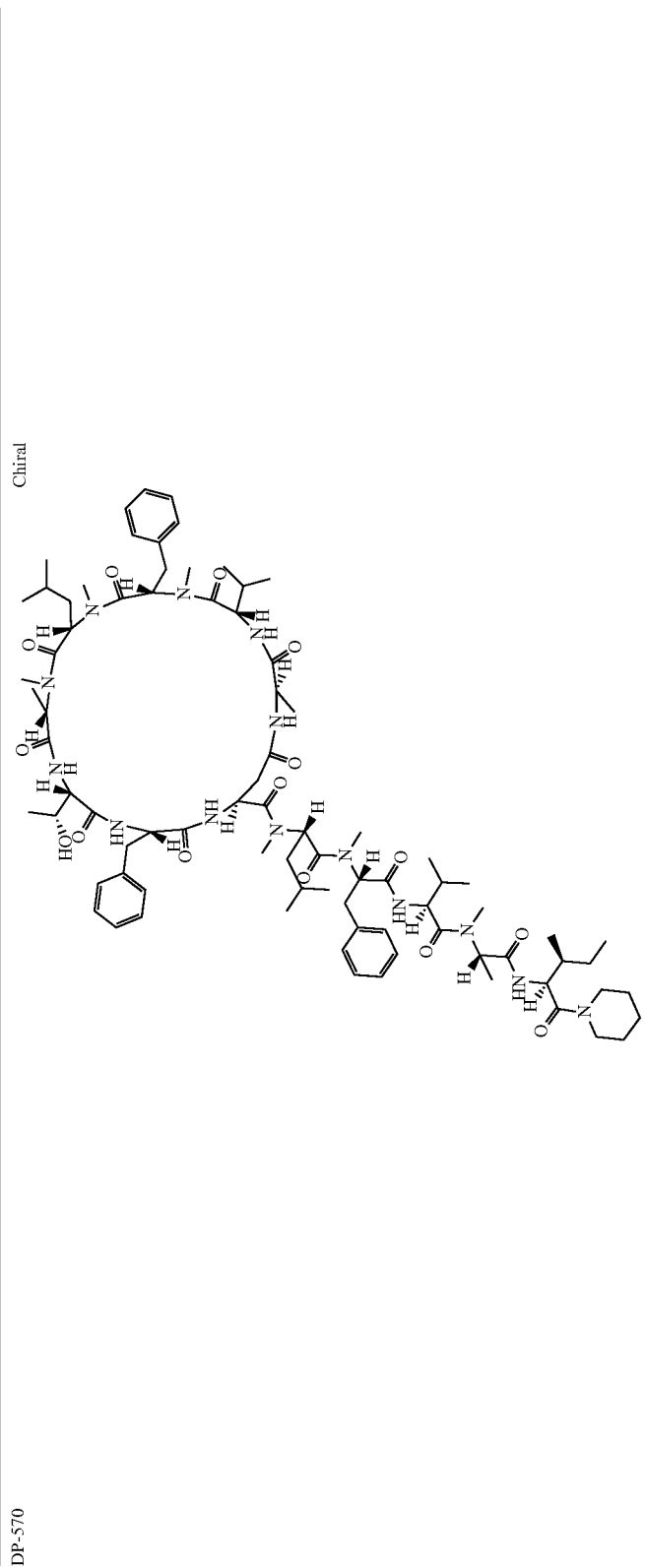

TABLE 11-3-1-continued
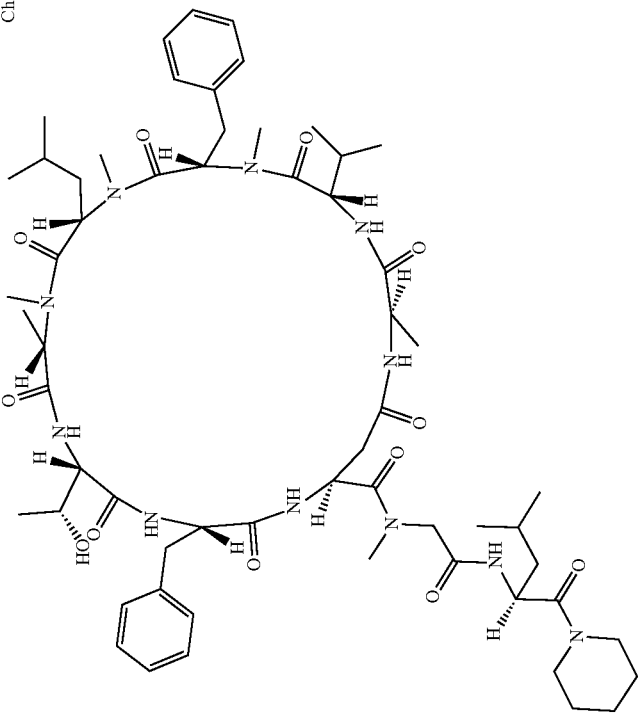
DP-571

TABLE 11-3-1-continued
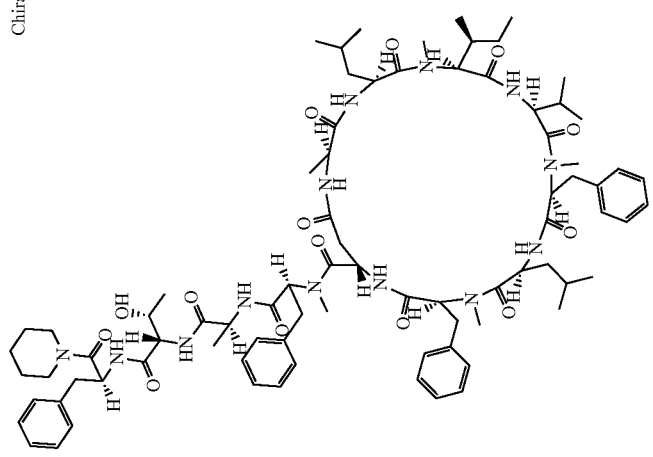
DP-572

TABLE 11-3-1-continued
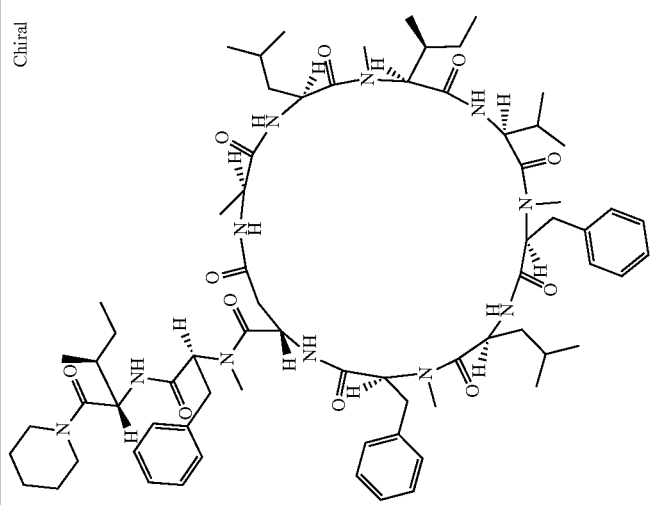
DP-573

TABLE 11-3-1-continued
Chiral
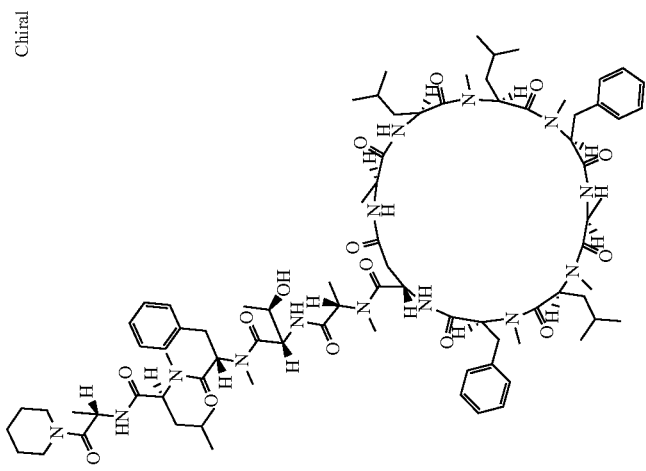
DP-574

TABLE 11-3-1-continued
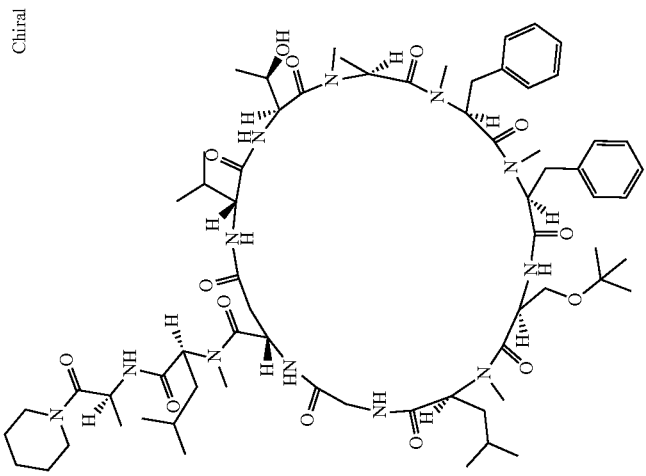
DP-575

TABLE 11-3-1-continued
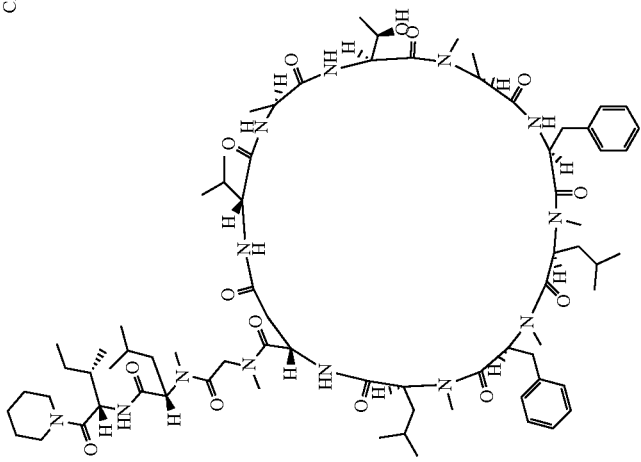
DP-576

TABLE 11-3-1-continued
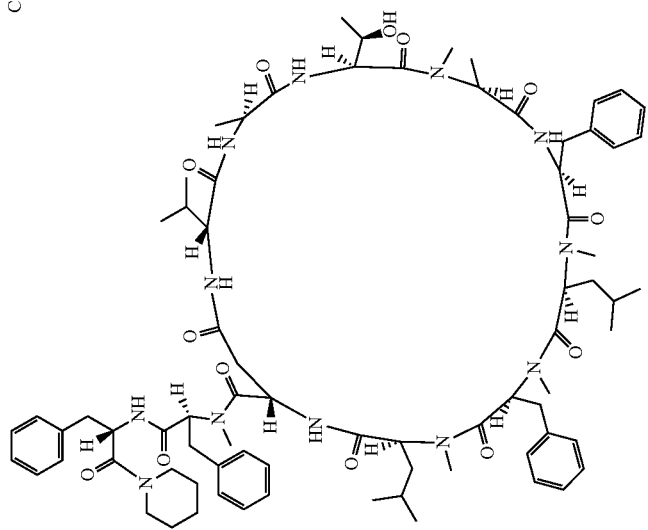
DP-577

TABLE 11-3-1-continued
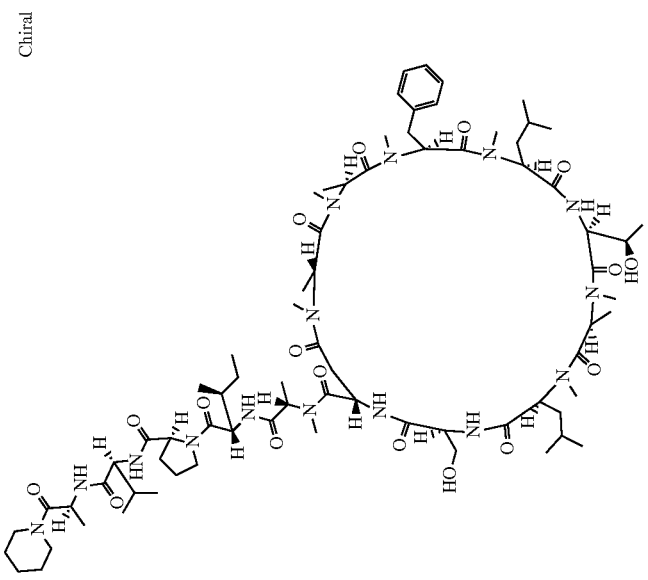
DP-578

TABLE 11-3-1-continued
DP-579
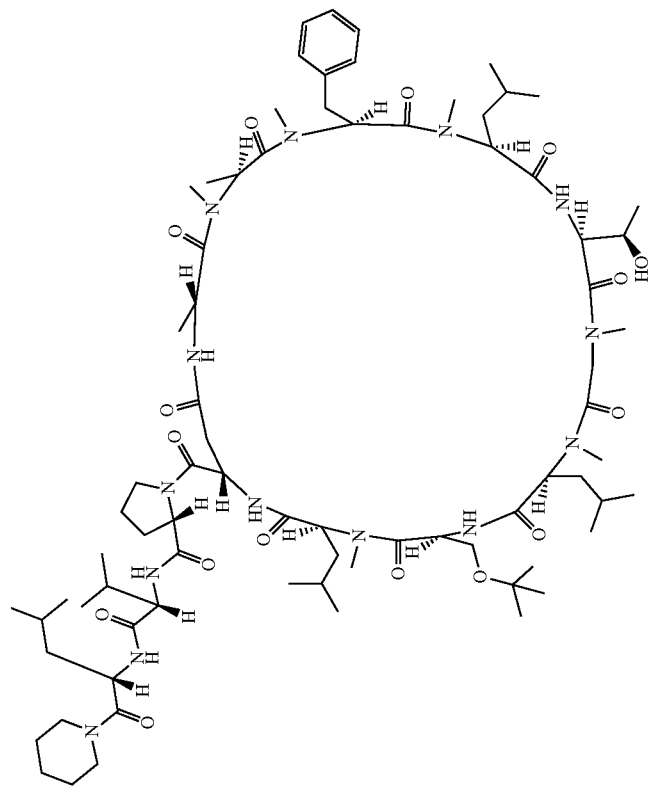

TABLE 11-3-1-continued
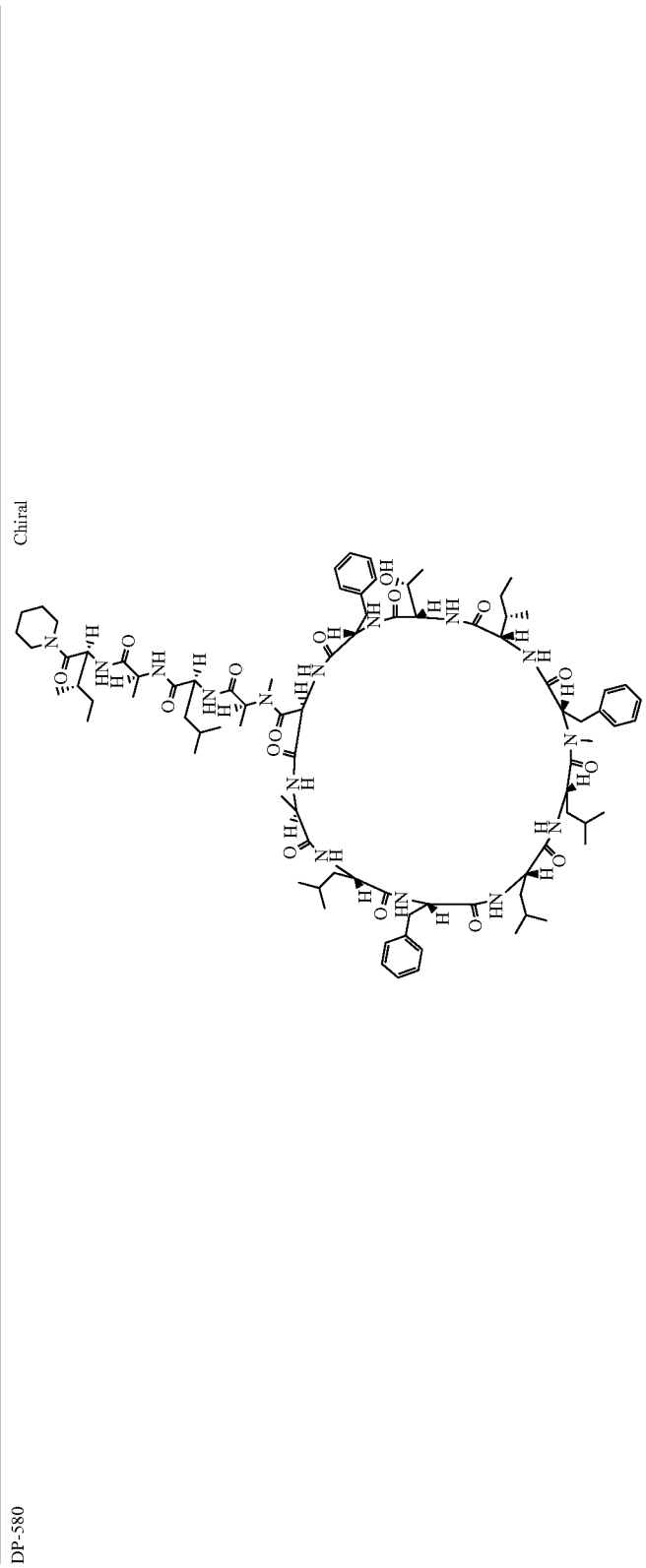
DP-580

TABLE 11-3-1-continued
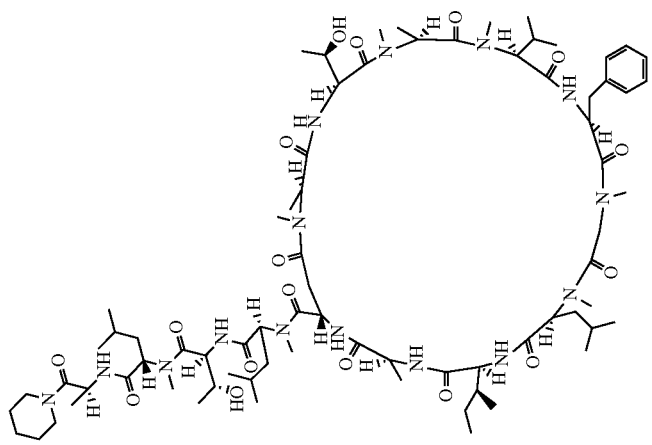
DP-581

TABLE 11-3-1-continued
DP-582
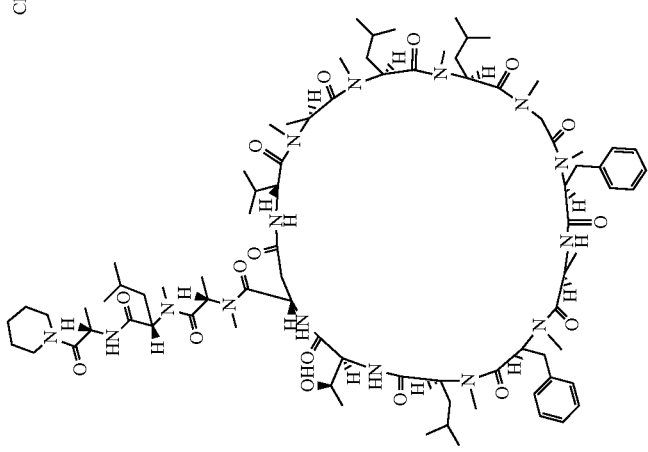

TABLE 11-3-1-continued
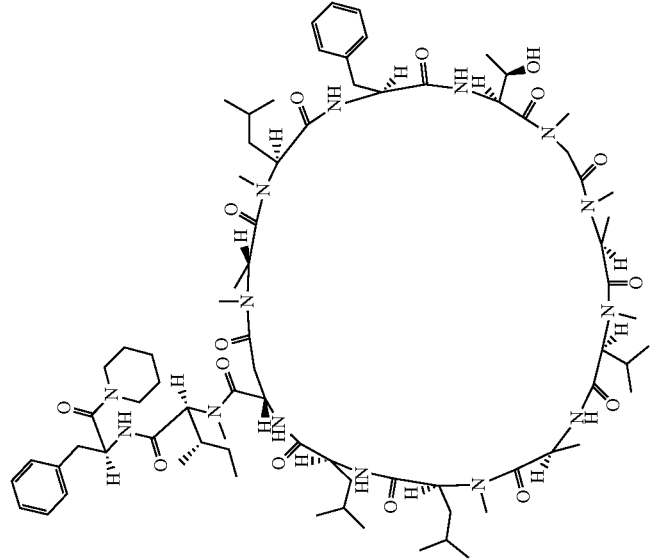
DP-583

TABLE 11-3-1-continued
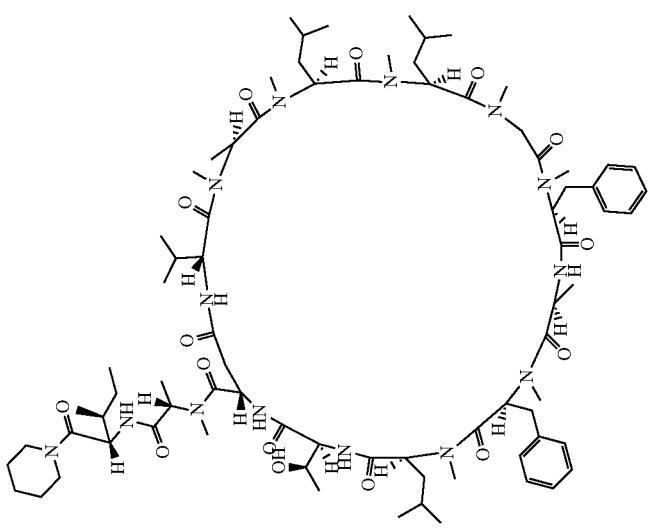
DP-584

TABLE 11-3-1-continued
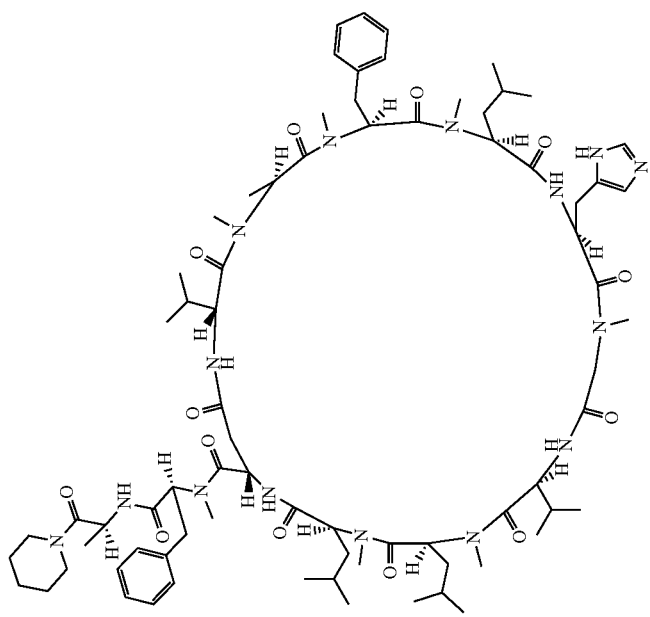
DP-585

TABLE 11-3-1-continued
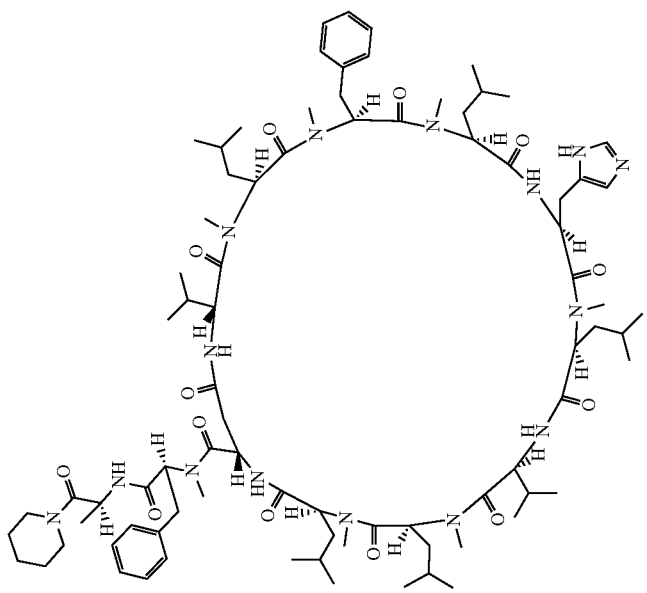
DP-586

TABLE 11-3-1-continued
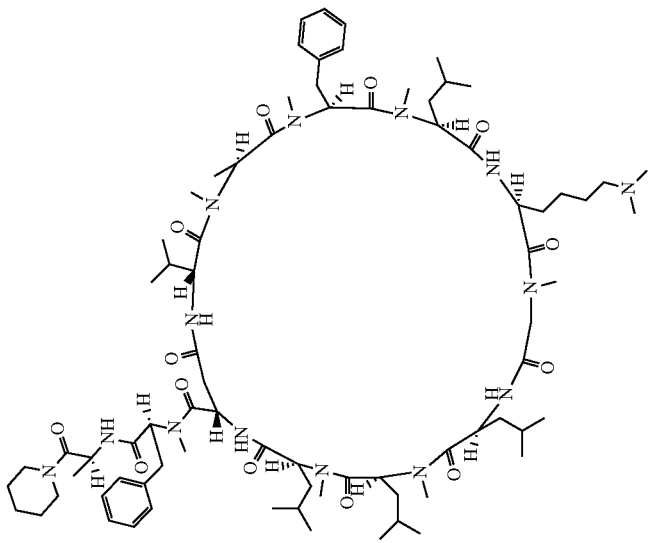
DP-587

TABLE 11-3-1-continued
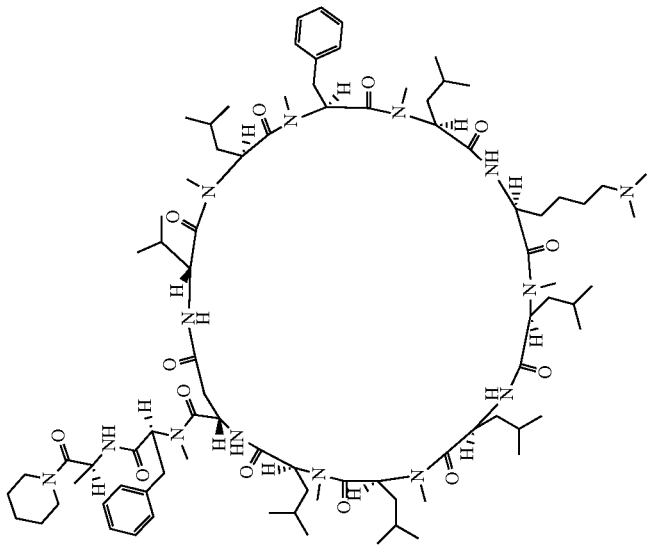
DP-588

TABLE 11-3-1-continued
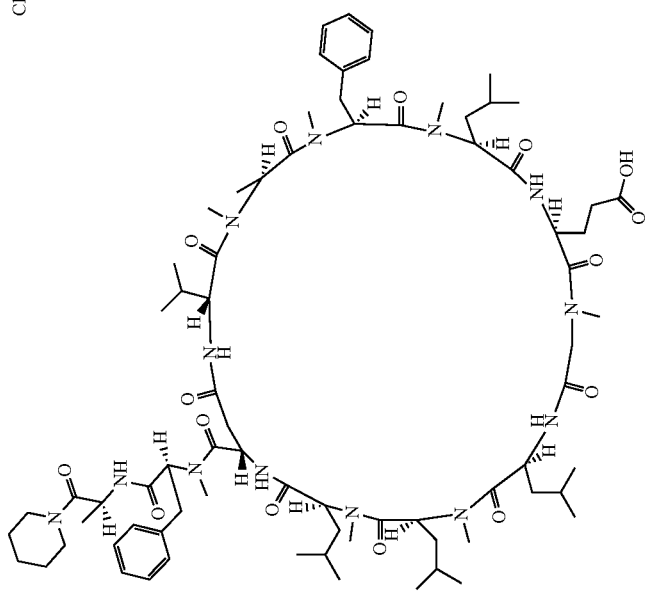
DP-589

TABLE 11-3-1-continued
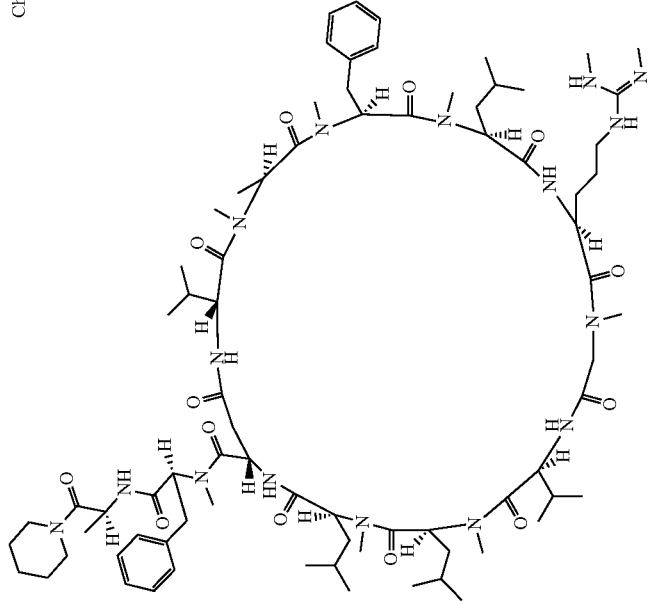
DP-590

TABLE 11-3-1-continued
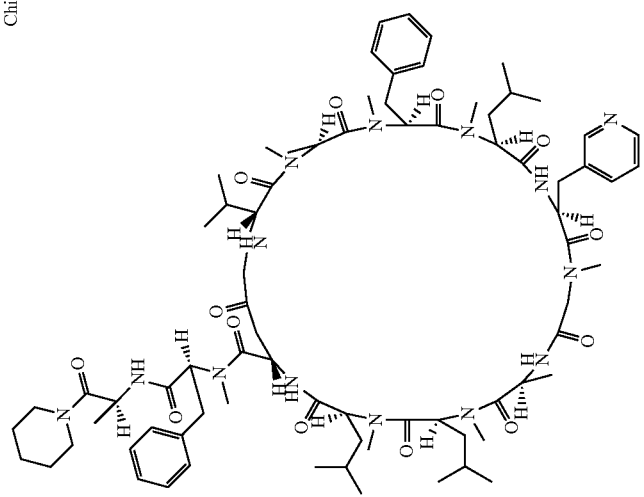
DP-591

TABLE 11-3-1-continued
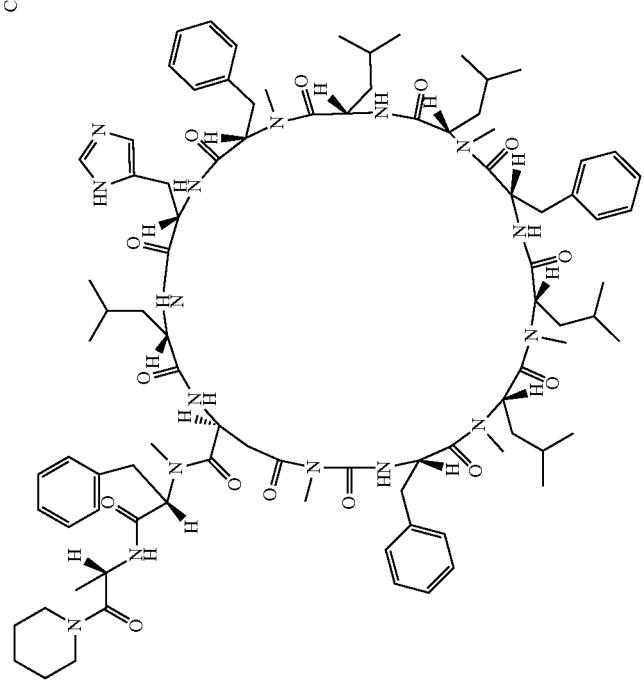
DP-592

TABLE 11-3-1-continued
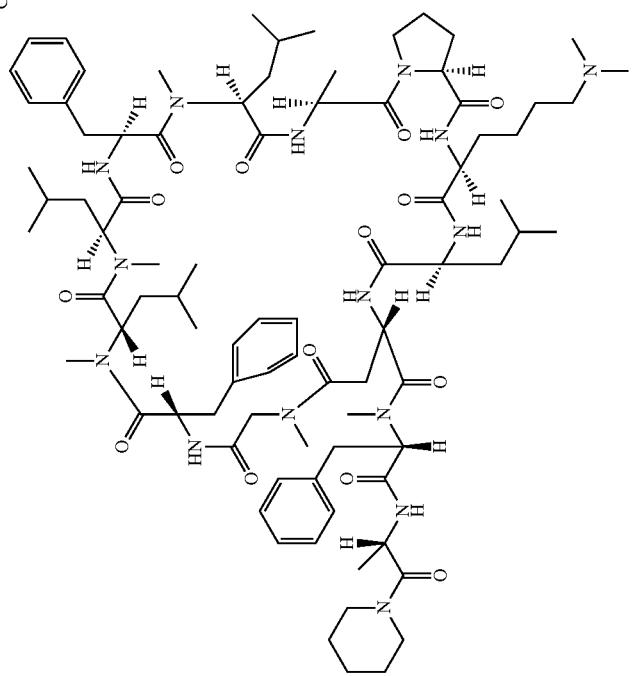
DP-593

TABLE 11-3-1-continued
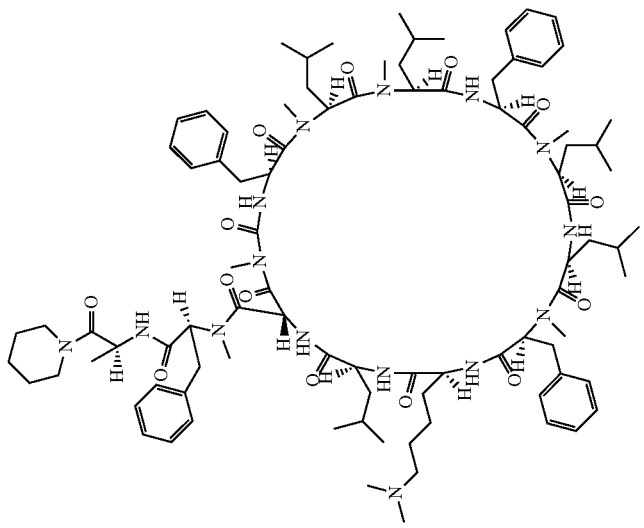
DP-594

TABLE 11-3-1-continued
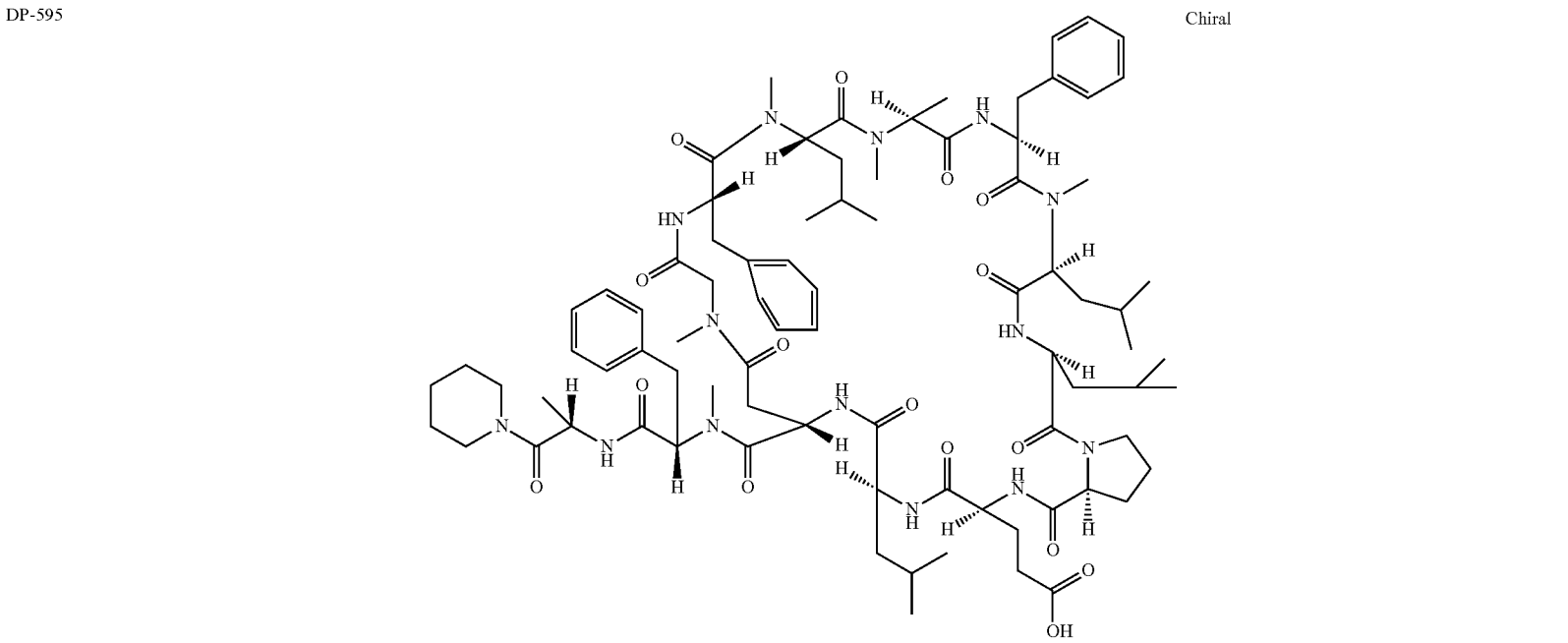
DP-595

TABLE 11-3-1-continued
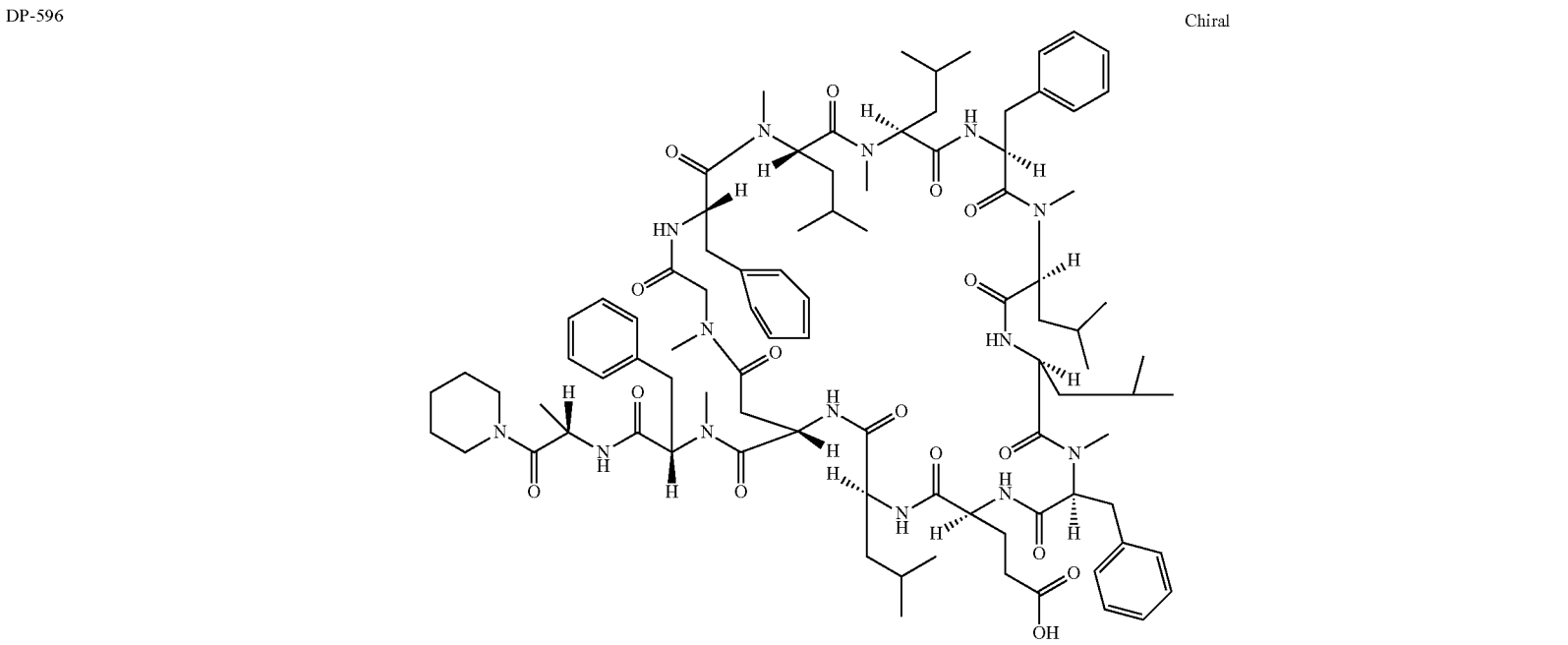
DP-596

TABLE 11-3-1-continued
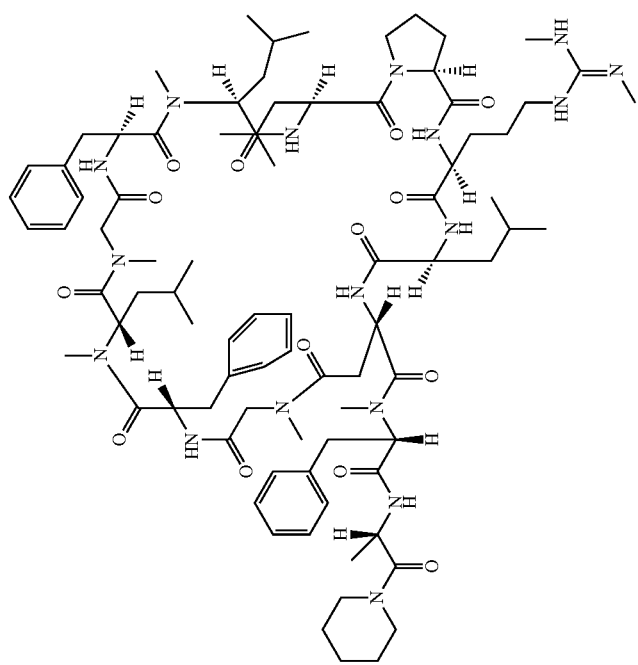
DP-597

TABLE 11-3-1-continued
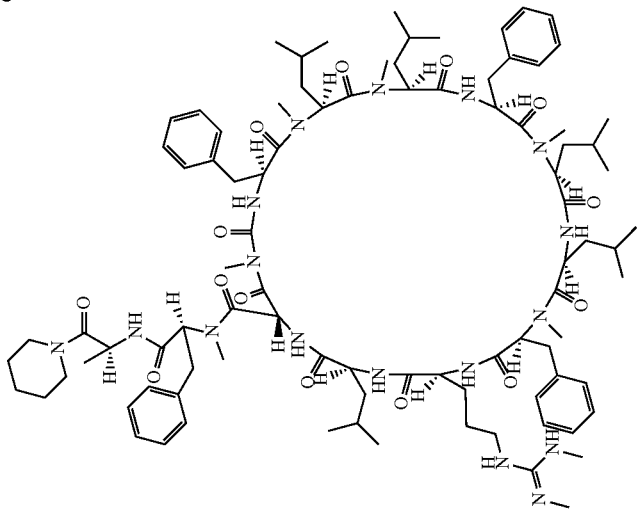
DP-598

TABLE 11-3-1-continued
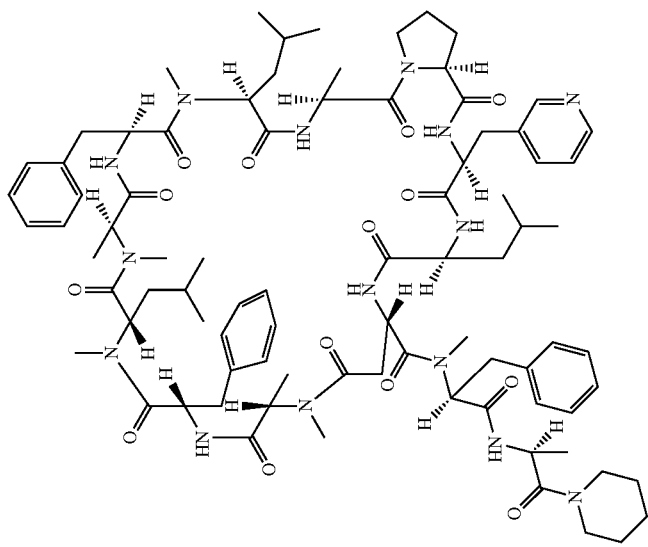
DP-599

TABLE 11-3-1-continued
Chiral
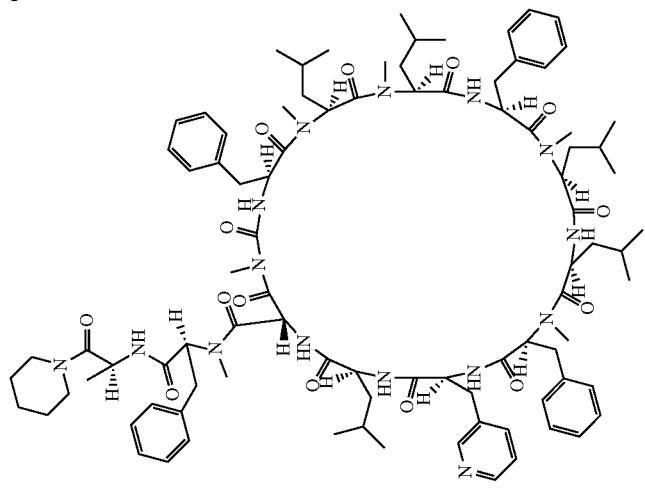
DP-600

TABLE 11-3-1-continued
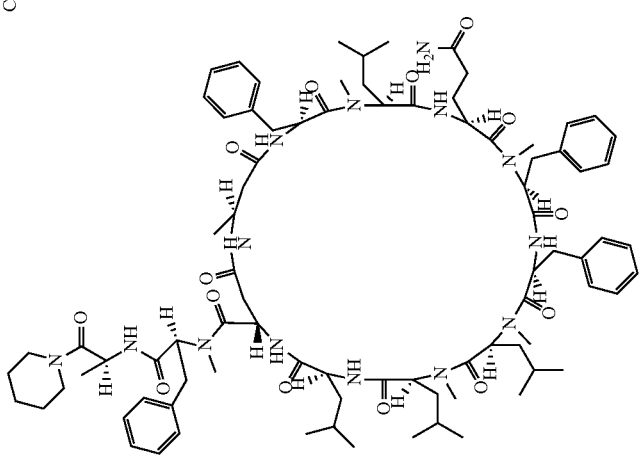
DP-601

TABLE 11-3-1-continued
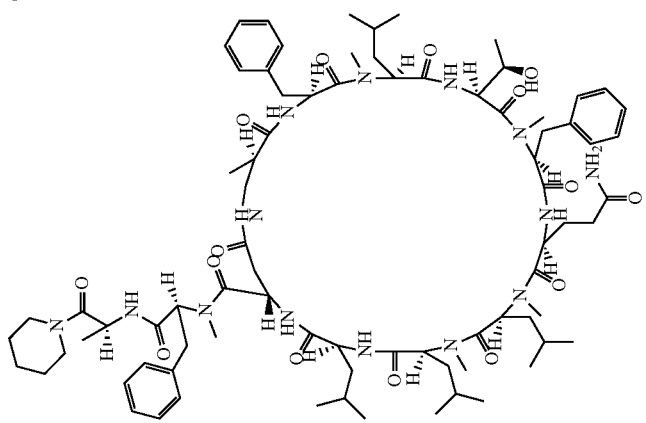
DP-602

TABLE 11-3-1-continued
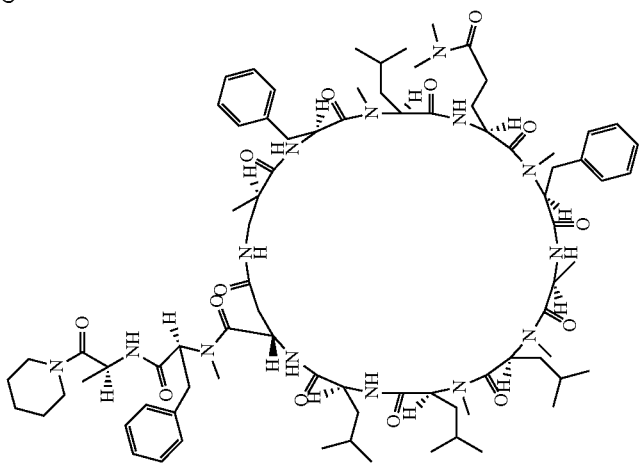
DP-603

TABLE 11-3-1-continued
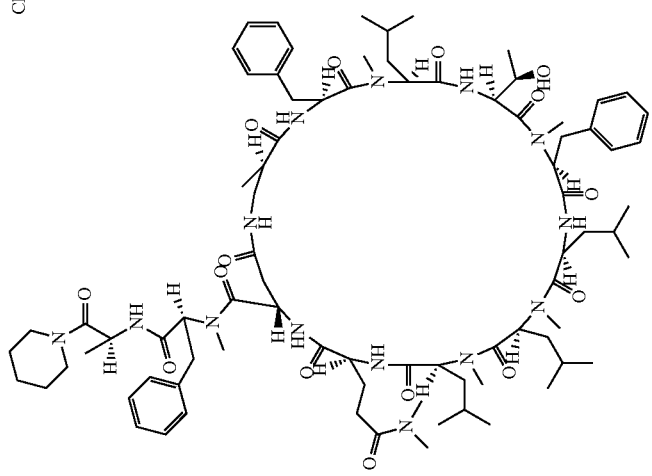
DP-604

TABLE 11-3-1-continued
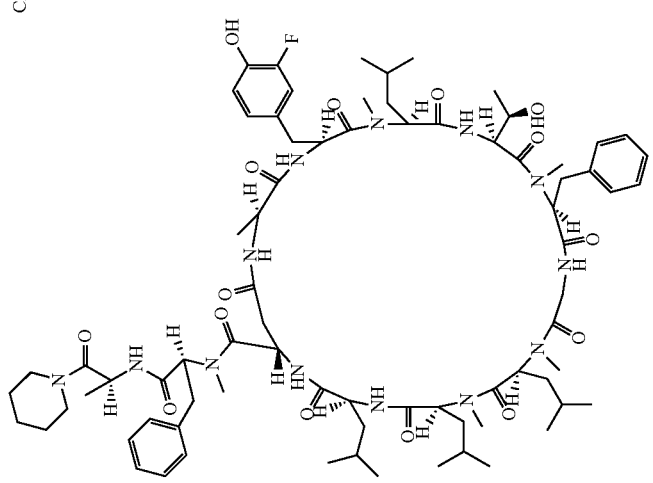
DP-605

TABLE 11-3-1-continued
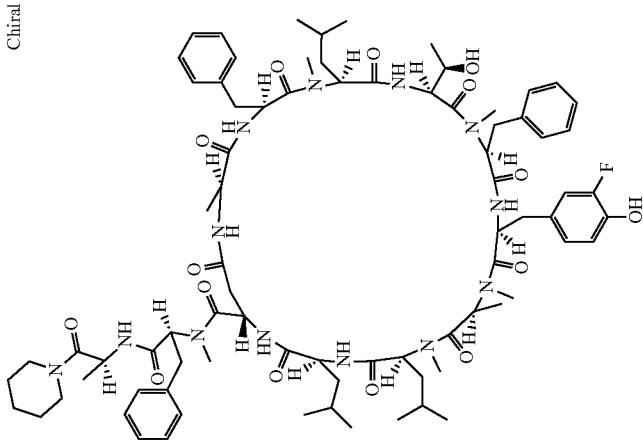
DP-606

TABLE 11-3-1-continued
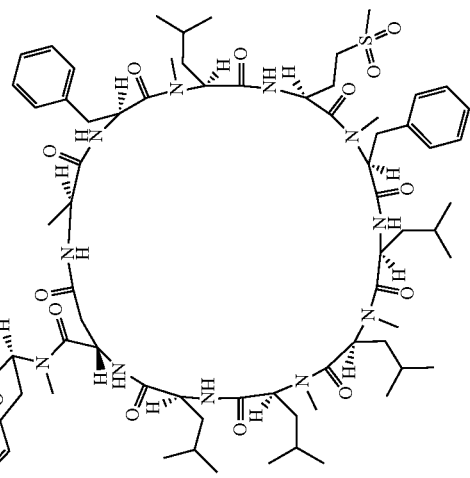
DP-607

TABLE 11-3-1-continued
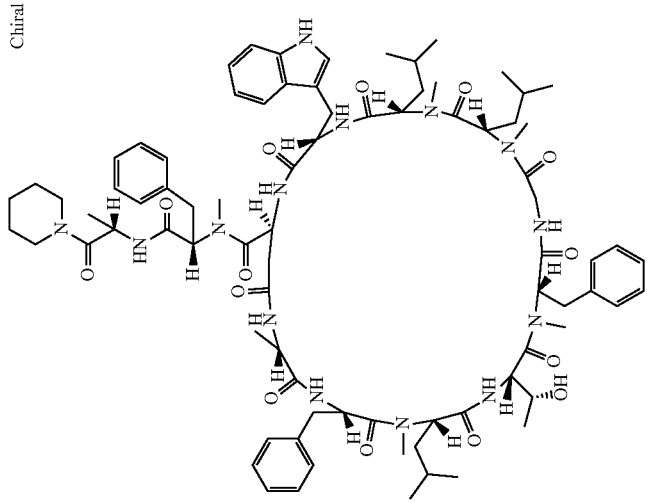
DP-608

TABLE 11-3-1-continued
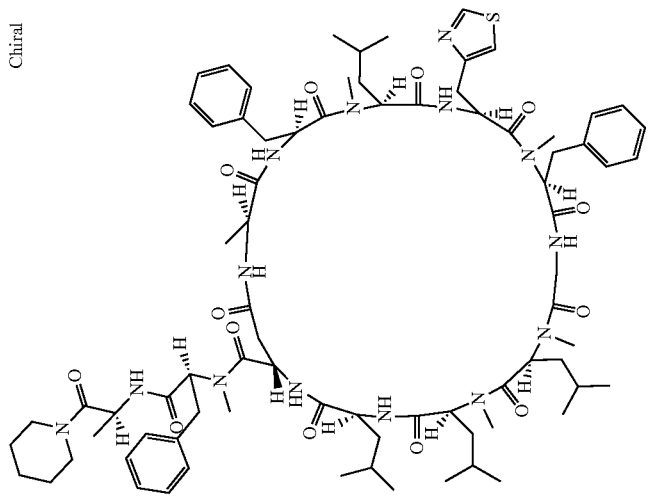
DP-609

TABLE 11-3-1-continued
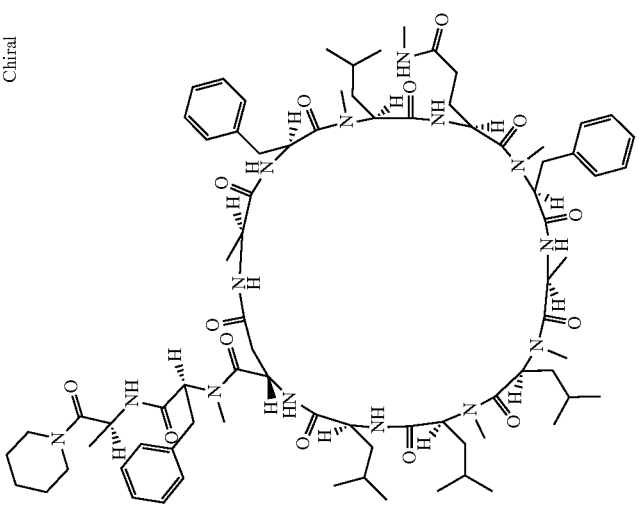
DP-610

TABLE 11-3-1-continued
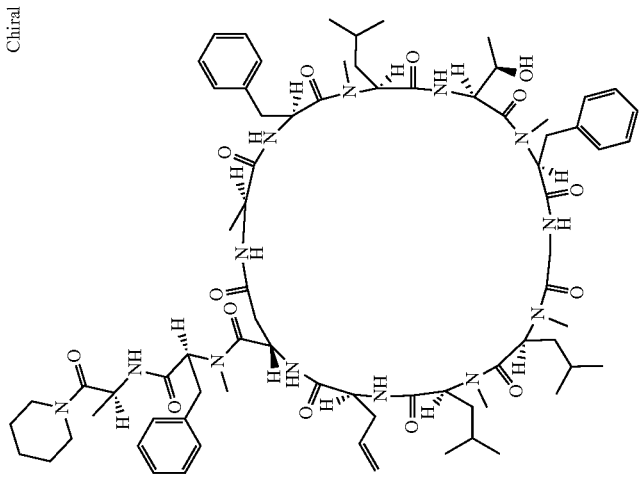
DP-611

TABLE 11-3-1-continued
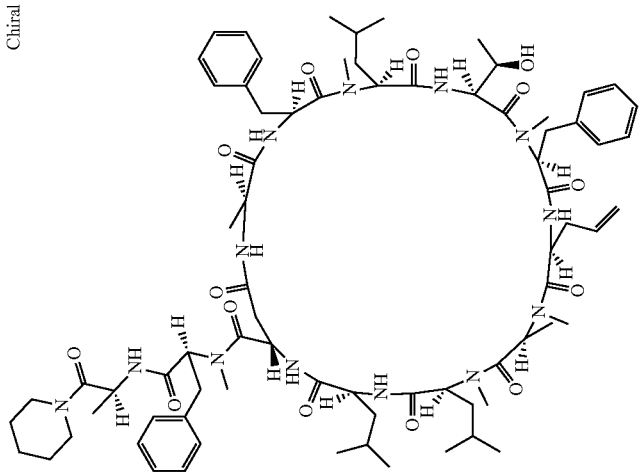
DP-612

TABLE 11-3-1-continued
Chiral
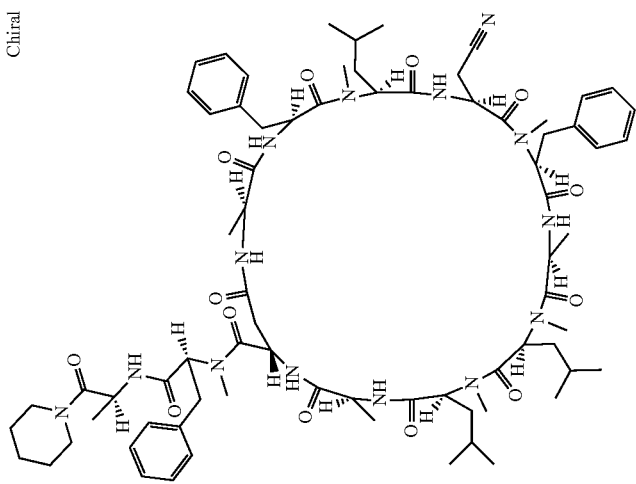
DP-613

TABLE 11-3-1-continued
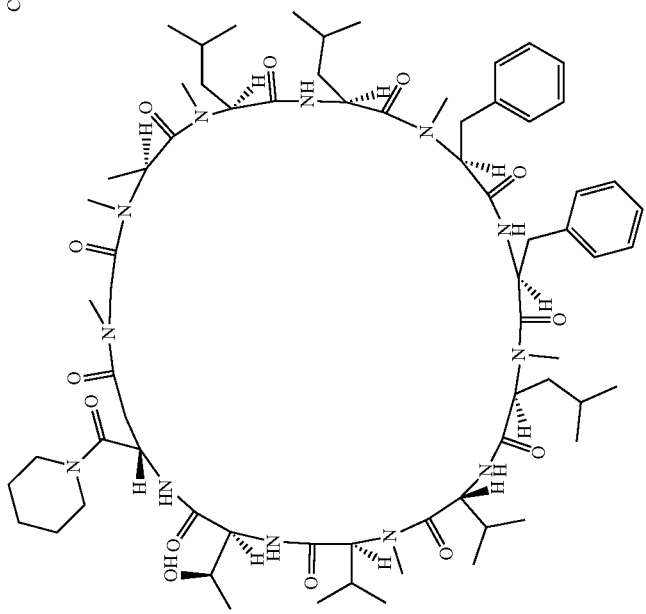
DP-614

TABLE 11-3-1-continued
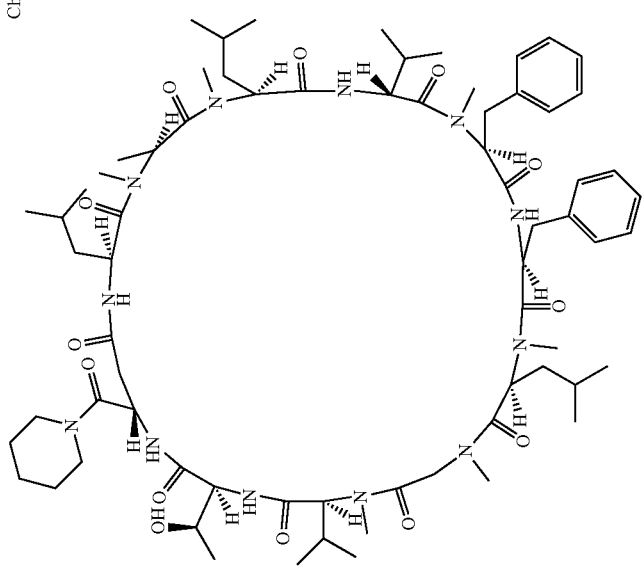
DP-615

TABLE 11-3-1-continued
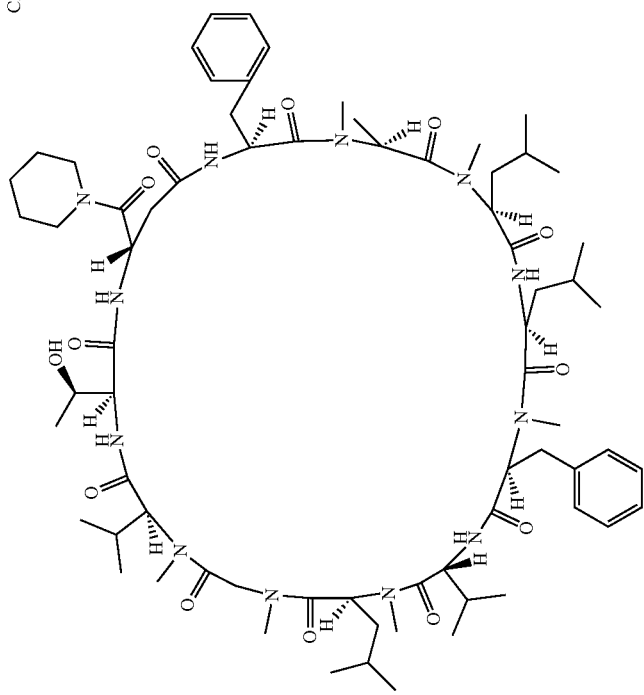
DP-616

TABLE 11-3-1-continued
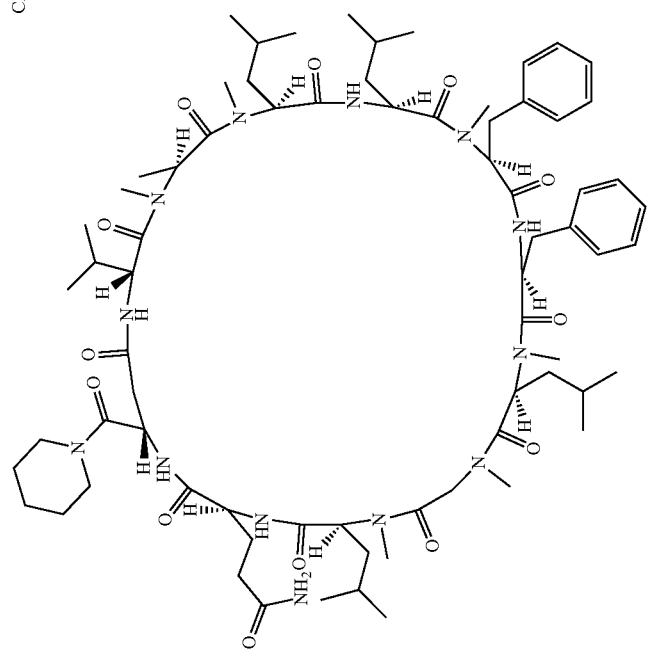
DP-617

TABLE 11-3-1-continued
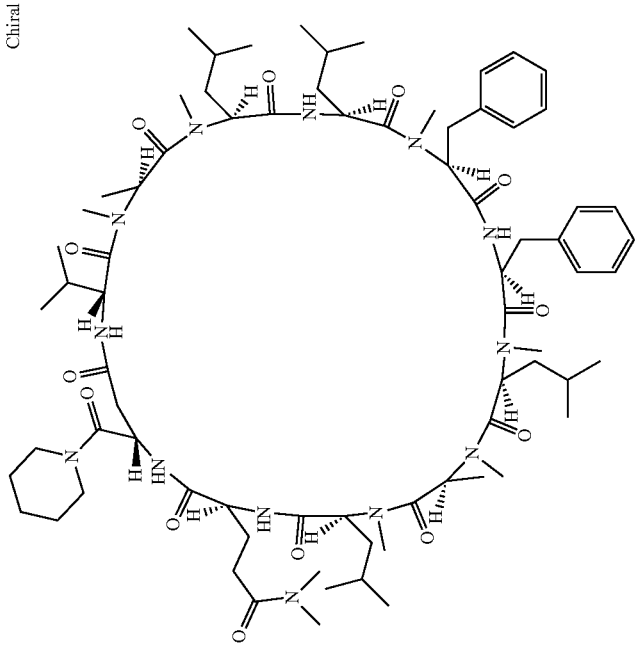
DP-618

TABLE 11-3-1-continued
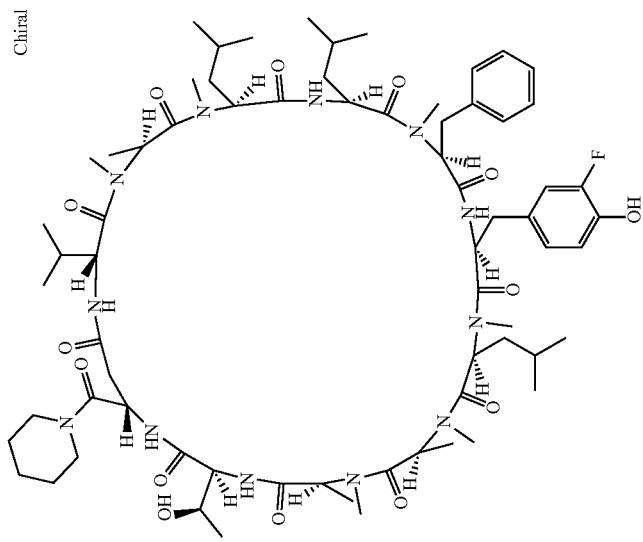
DP-619

TABLE 11-3-1-continued
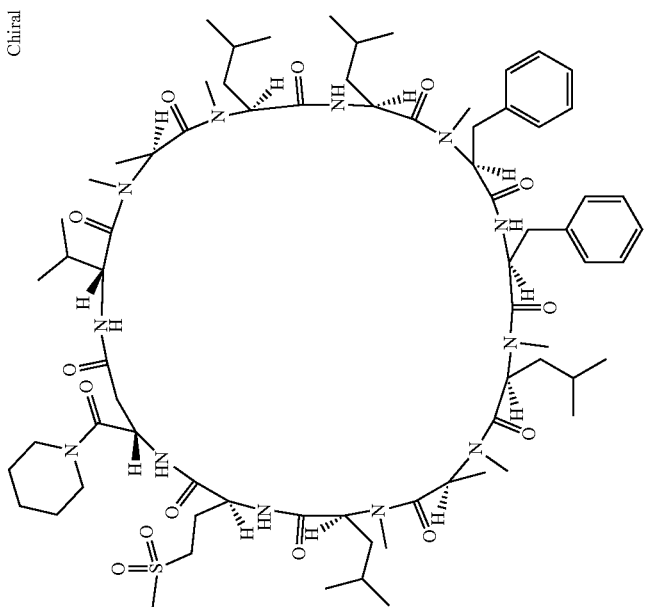
DP-620

TABLE 11-3-1-continued
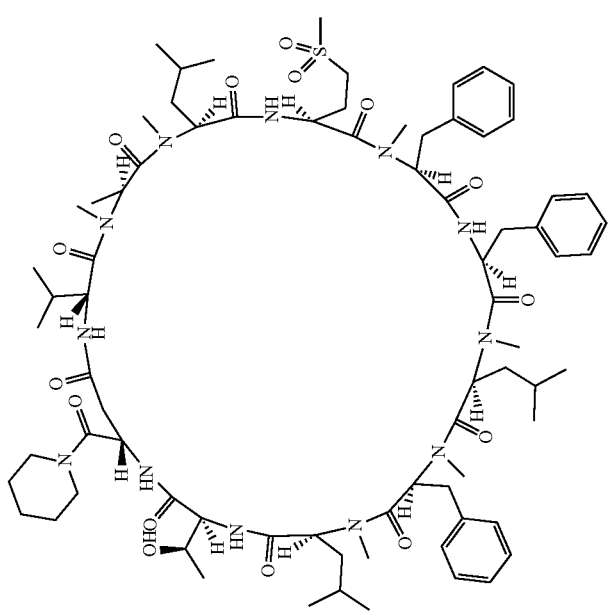
DP-621

TABLE 11-3-1-continued
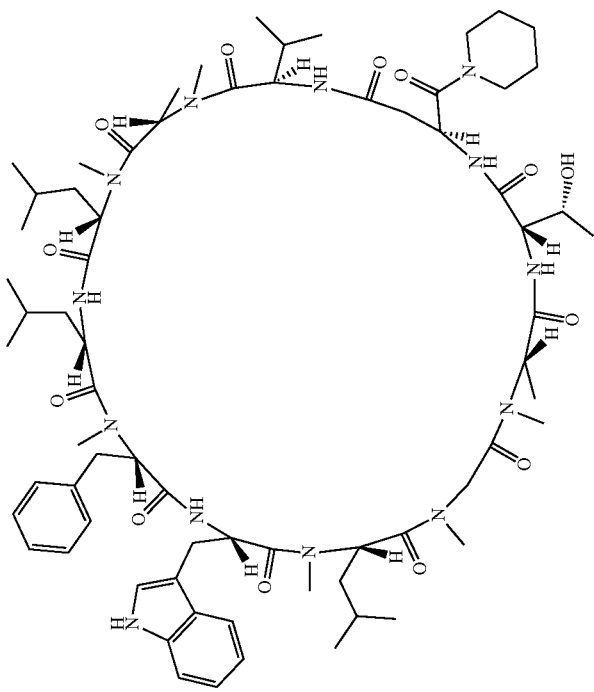
DP-622

TABLE 11-3-1-continued
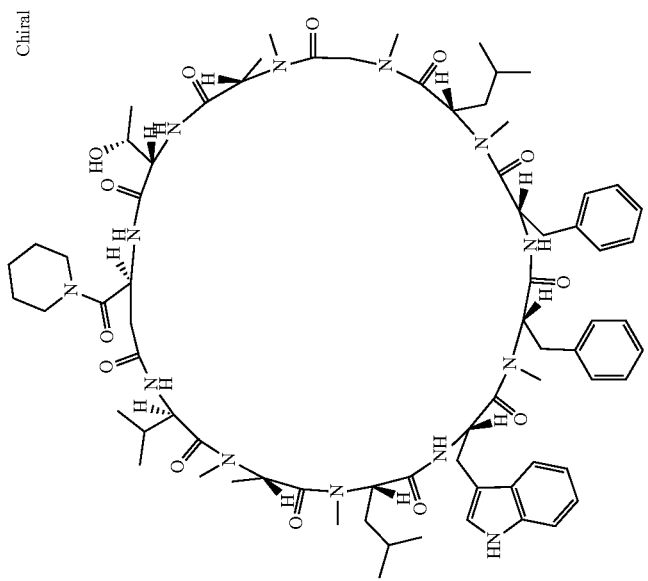
DP-623

TABLE 11-3-1-continued
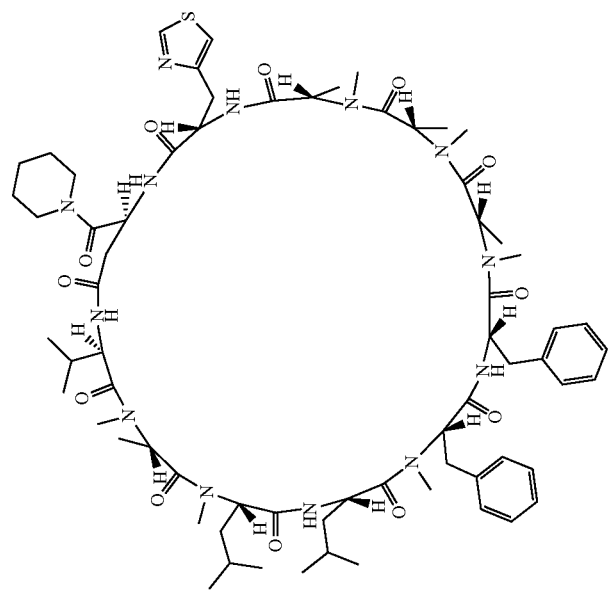
DP-624

TABLE 11-3-1-continued
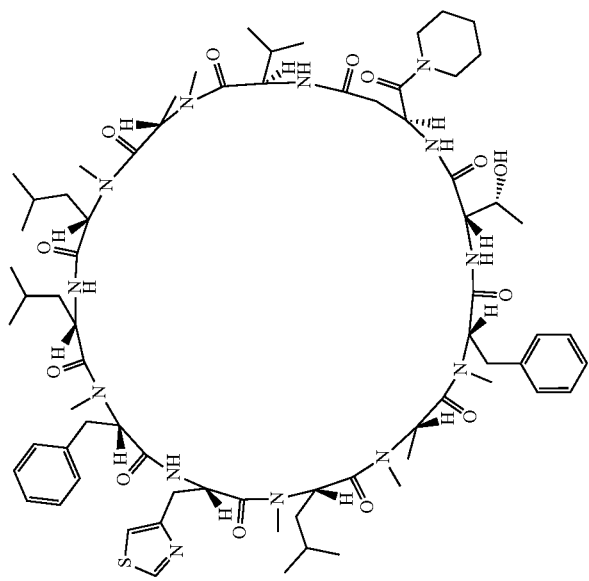
DP-625

TABLE 11-3-1-continued
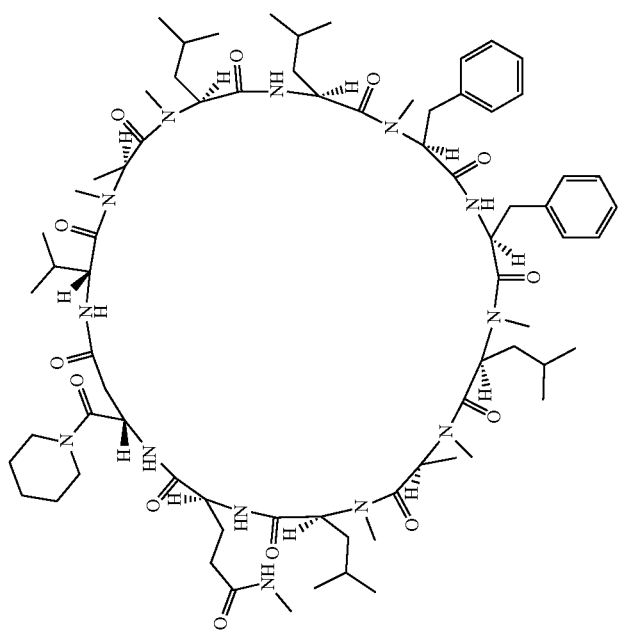
DP-626

TABLE 11-3-1-continued
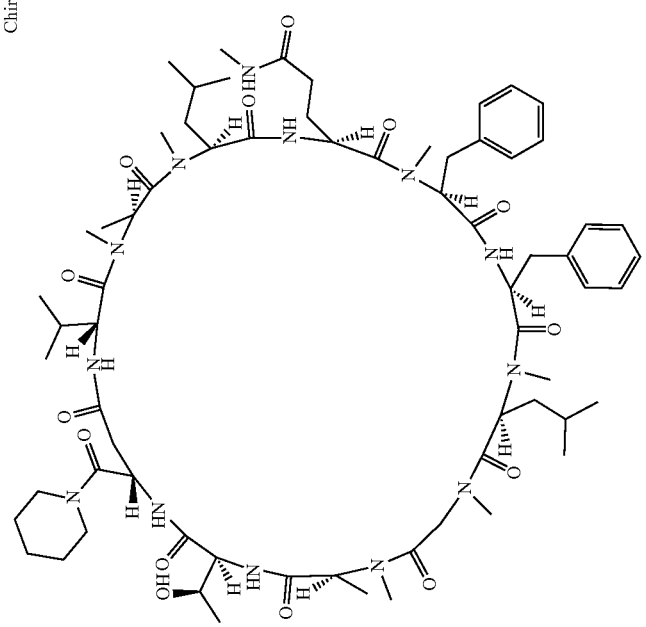
DP-627

TABLE 11-3-1-continued
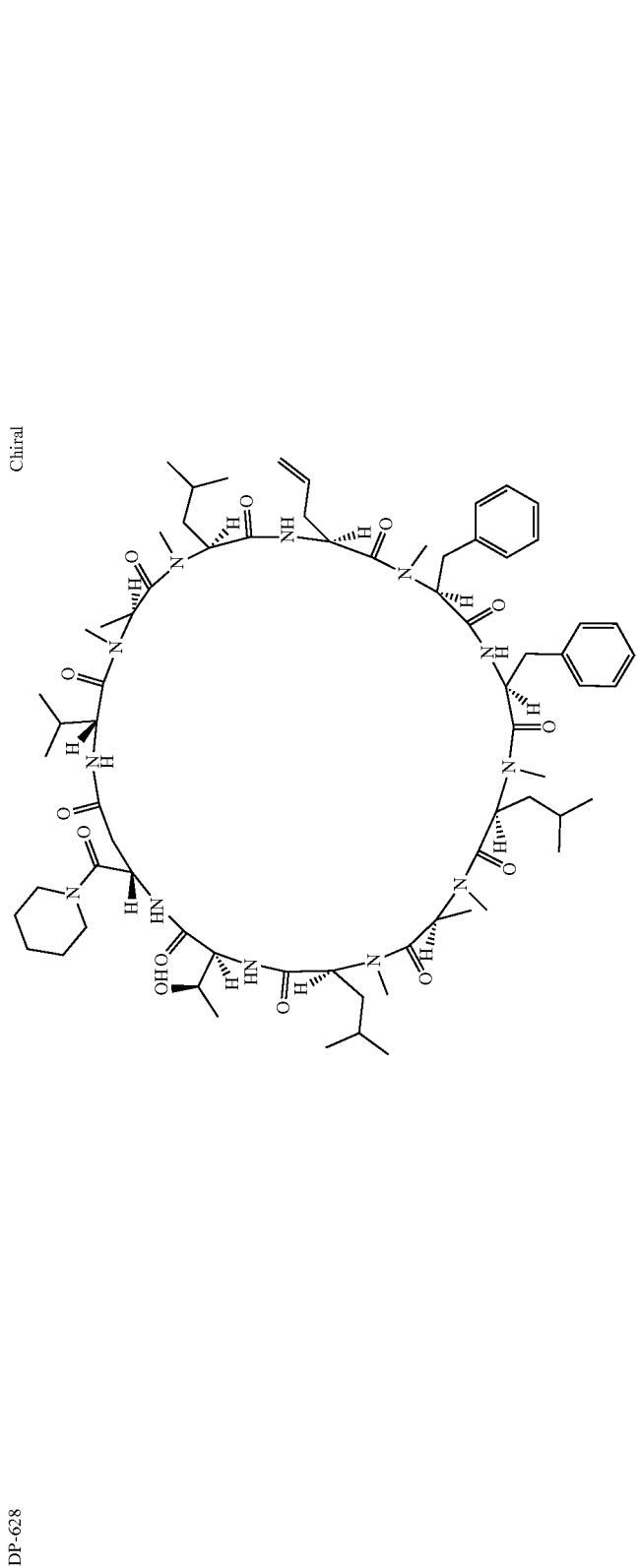
DP-628

TABLE 11-3-1-continued
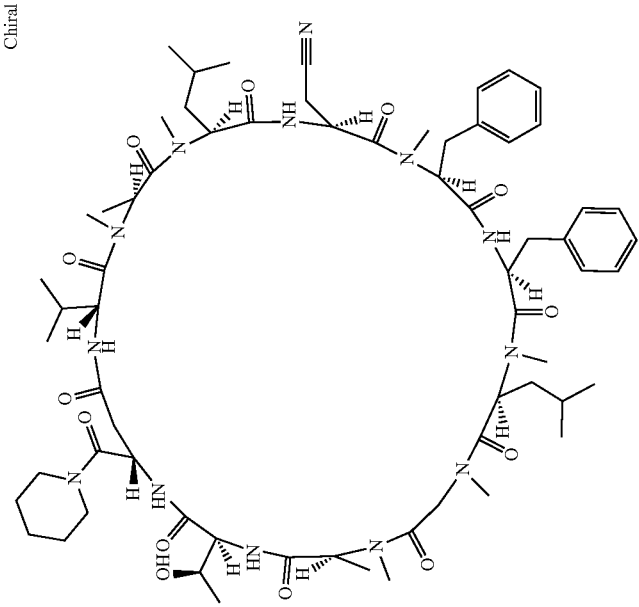
DP-629

TABLE 11-3-1-continued
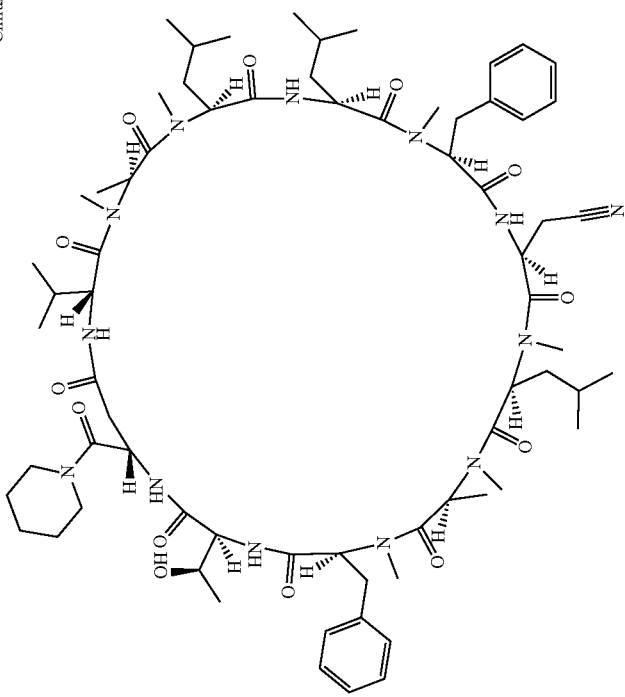
DP-630

TABLE 11-3-1-continued
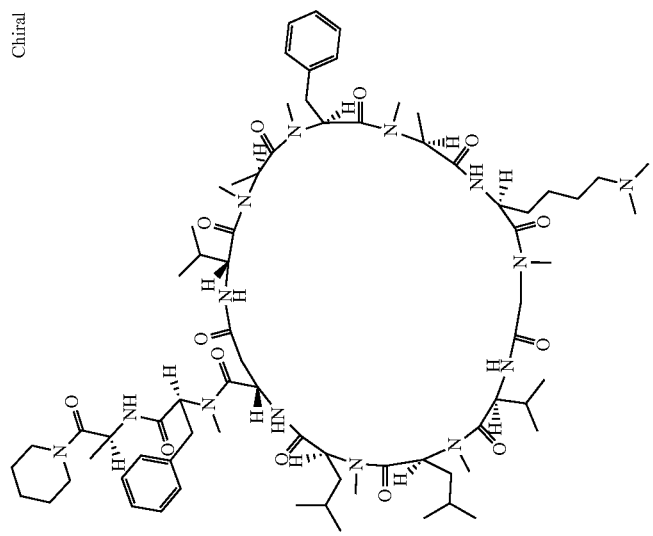
DP-631

TABLE 11-3-1-continued
Chiral
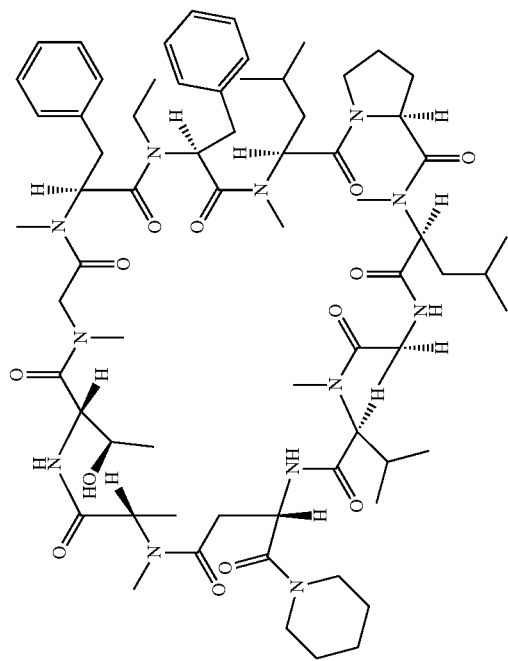
DP-632

TABLE 11-3-1-continued
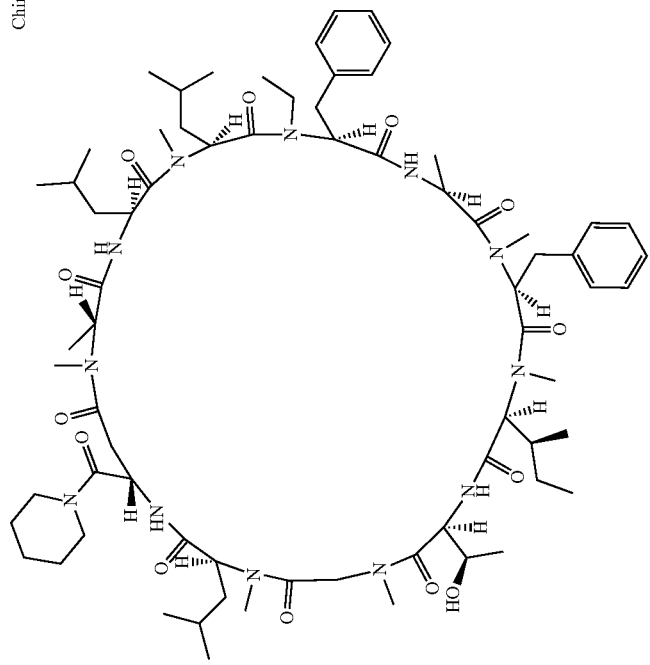
DP-633

TABLE 11-3-1-continued
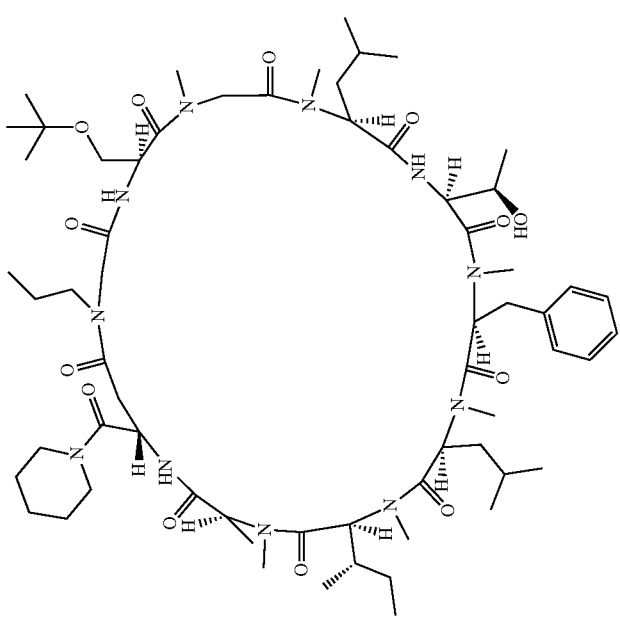
DP-634

TABLE 11-3-1-continued
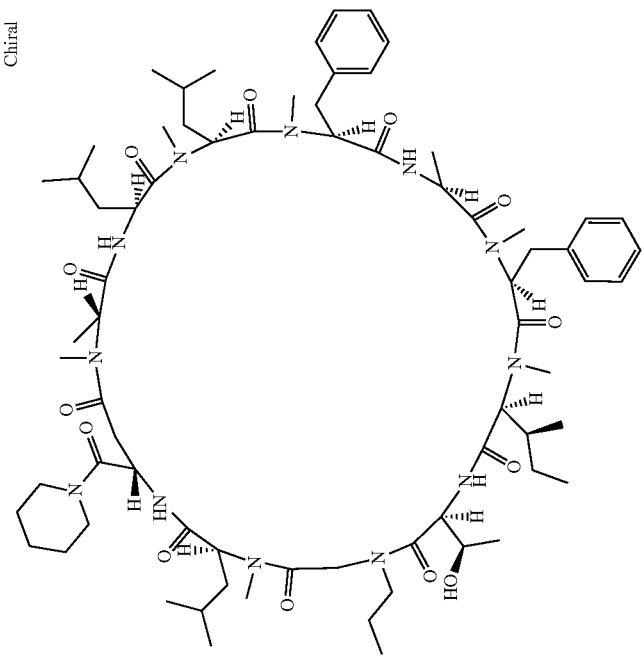
DP-635

TABLE 11-3-1-continued
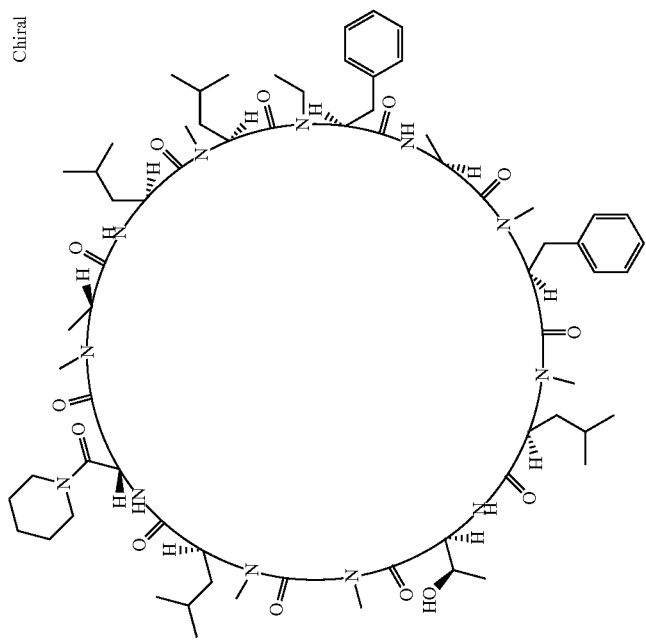
DP-636

TABLE 11-3-1-continued
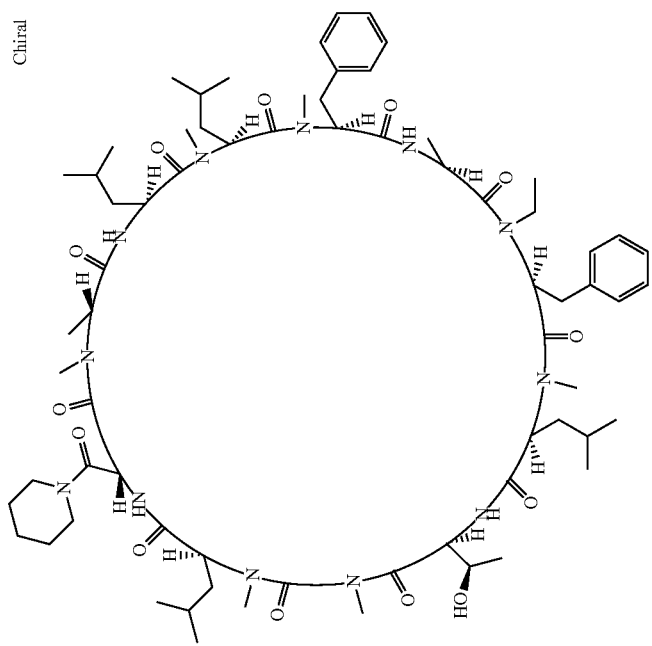
DP-637

TABLE 11-3-1-continued
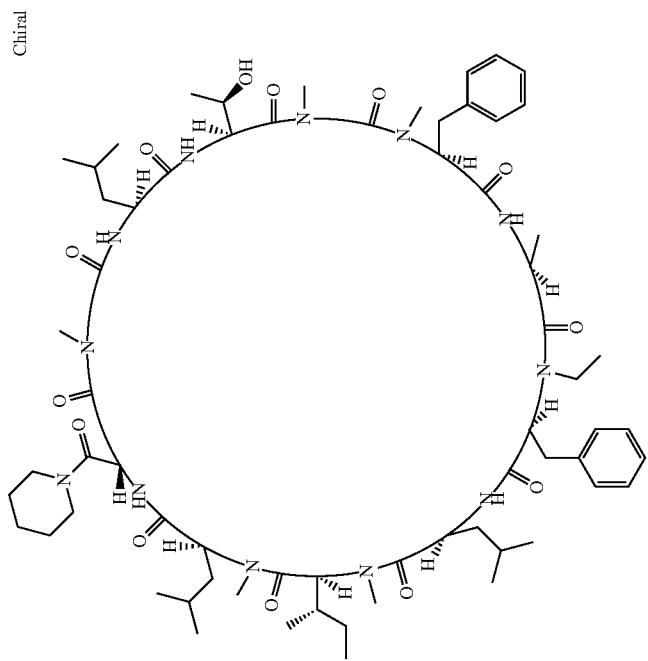
DP-638

TABLE 11-3-1-continued
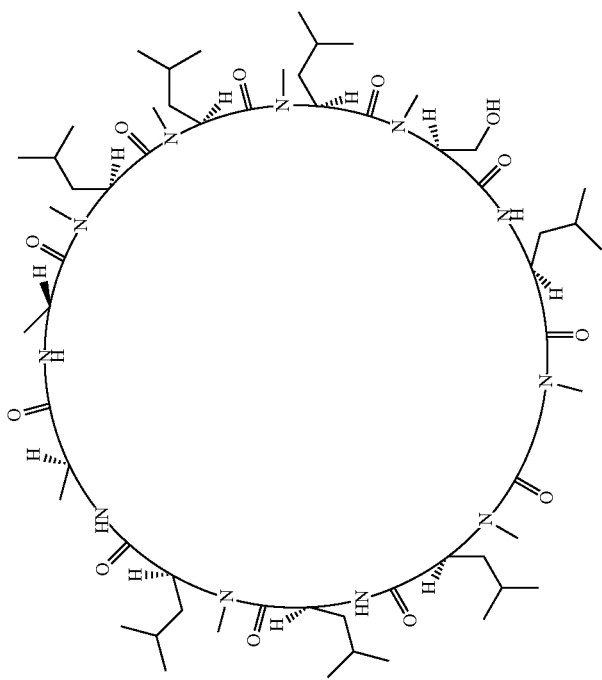
DP-639

TABLE 11-3-1-continued
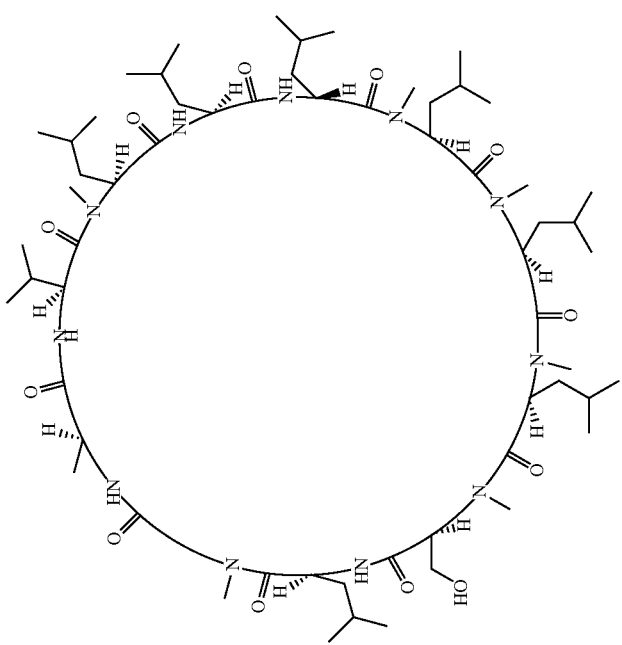
DP-640

TABLE 11-3-1-continued
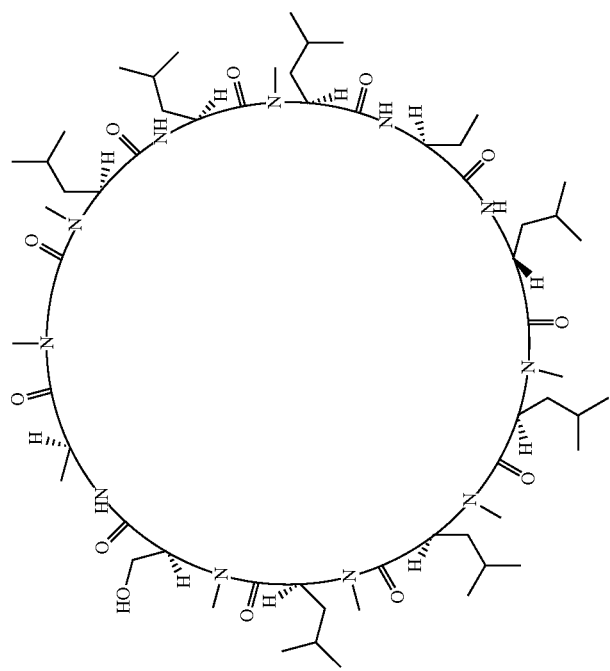
DP-641

TABLE 11-3-1-continued
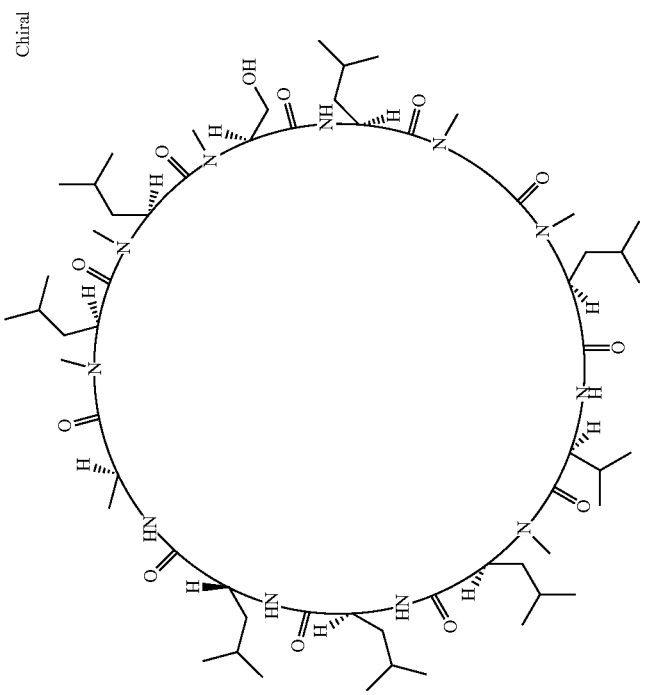
DP-642

TABLE 11-3-1-continued
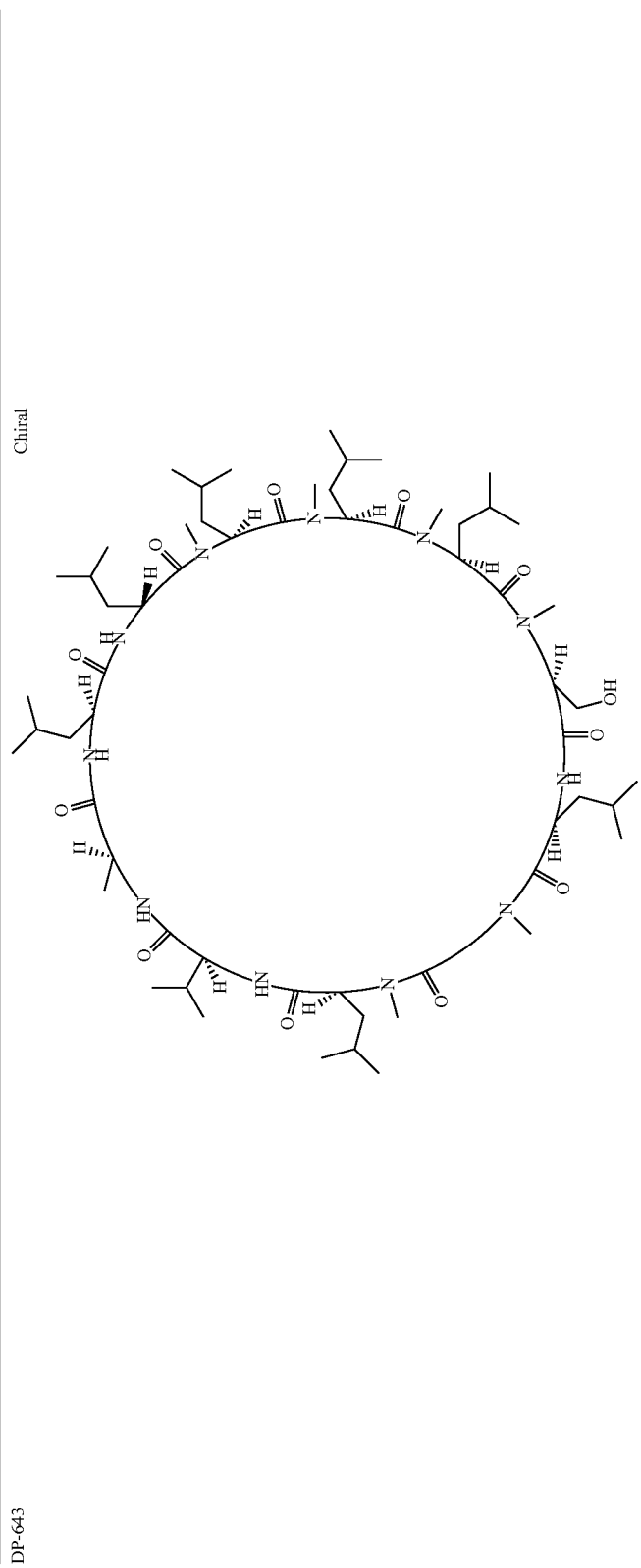
DP-643

TABLE 11-3-1-continued
DP-644

TABLE 11-3-1-continued
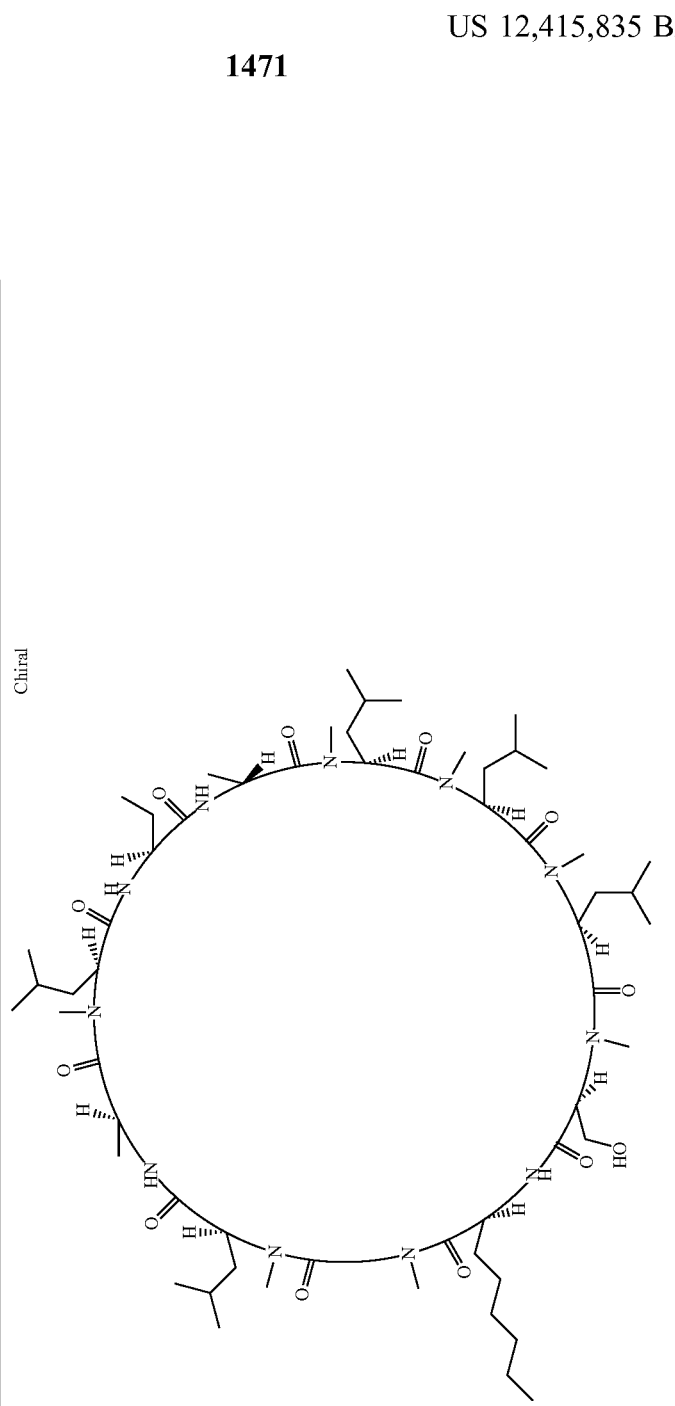
DP-645

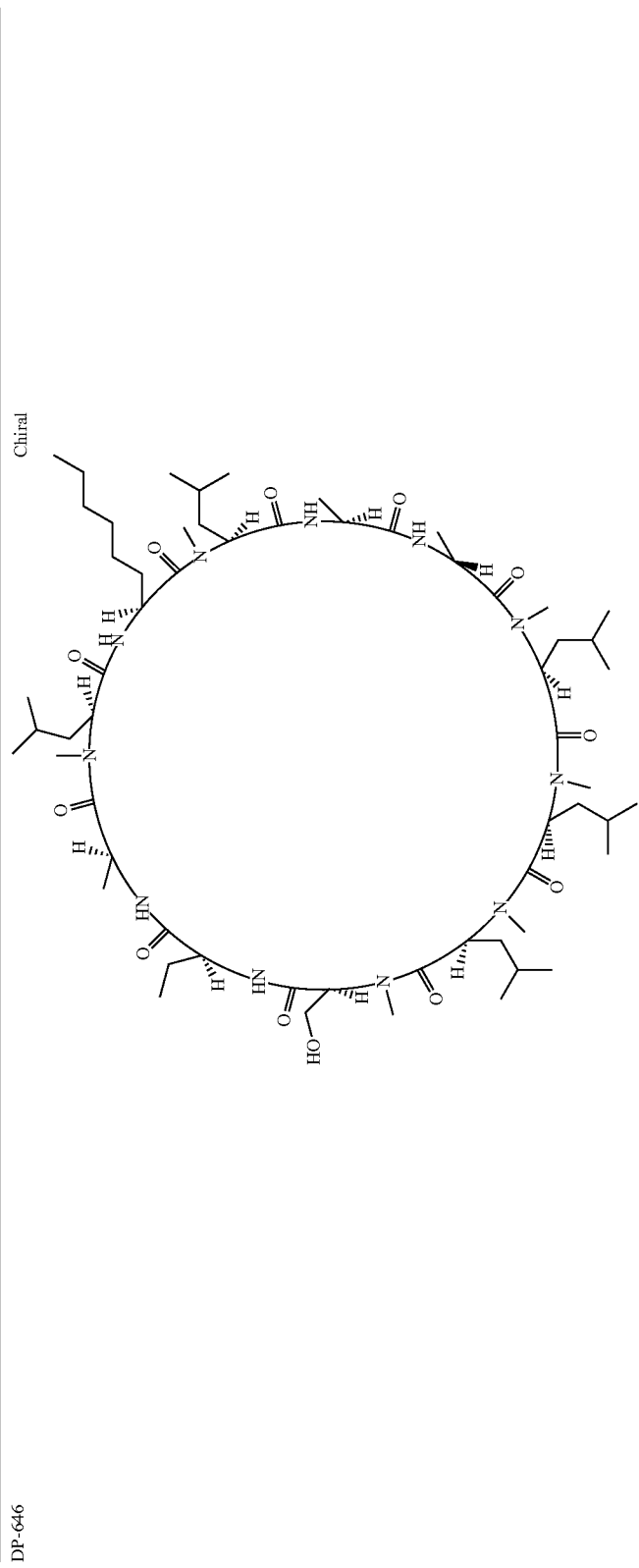
DP-646

TABLE 11-3-1-continued
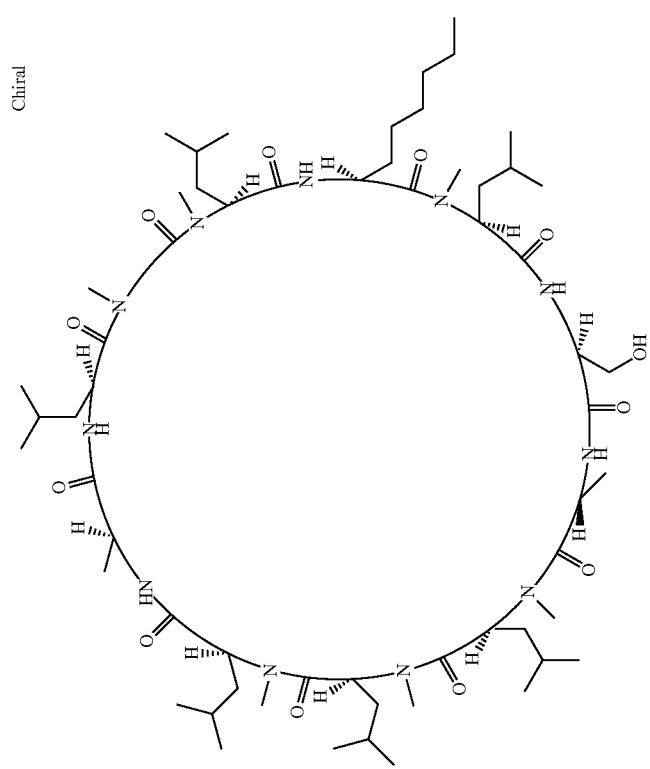
DP-647

TABLE 11-3-1-continued
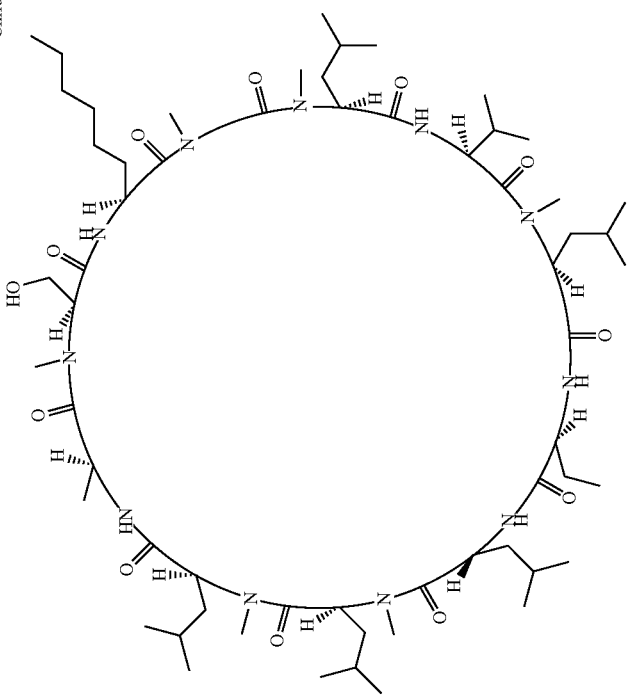
DP-648

TABLE 11-3-1-continued
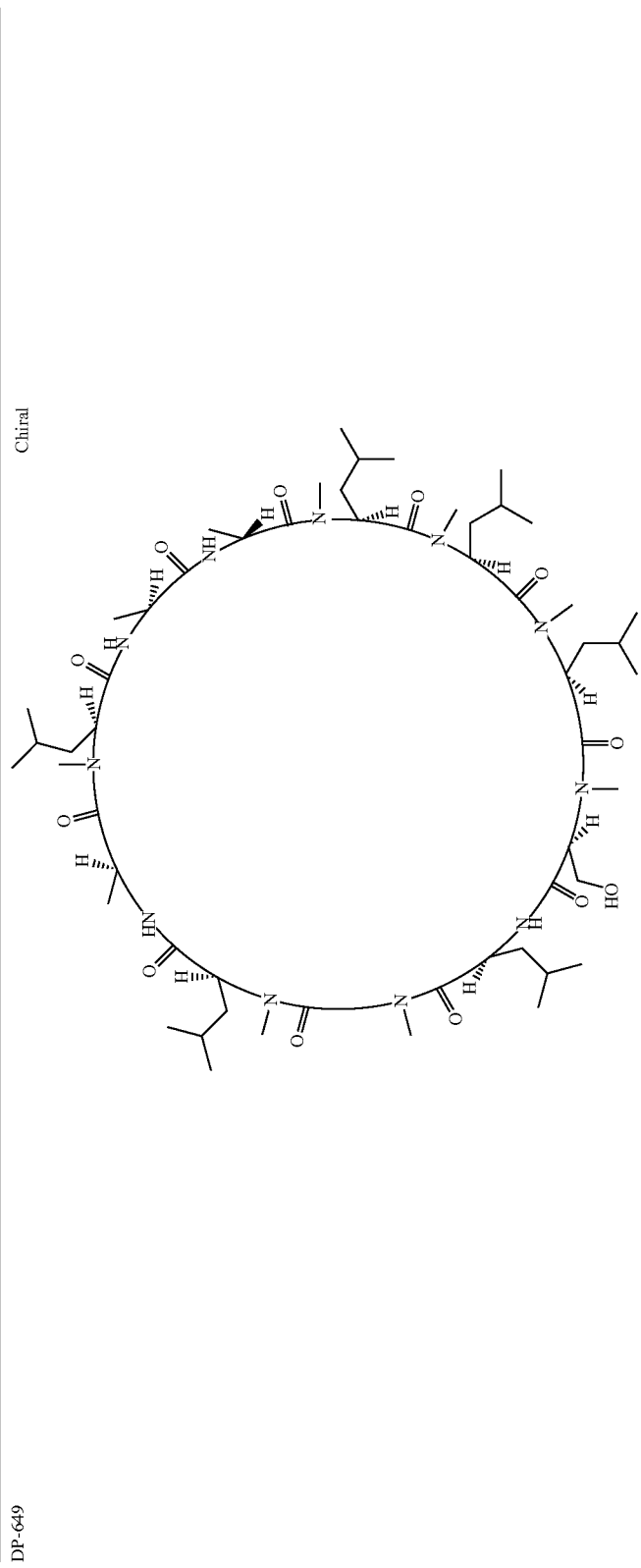
DP-649

TABLE 11-3-1-continued
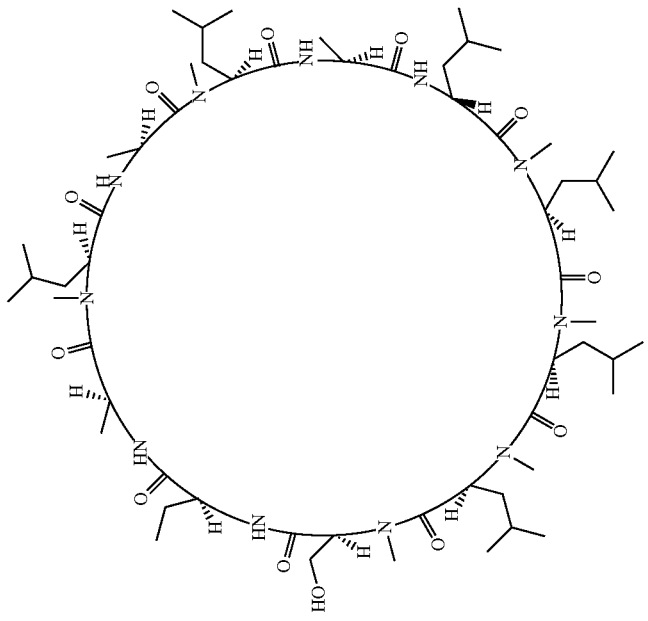
DP-650

TABLE 11-3-1-continued
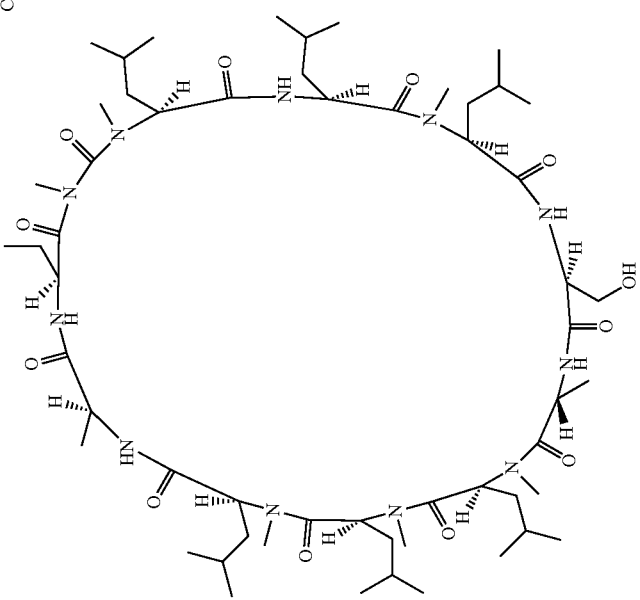
DP-651

TABLE 11-3-1-continued
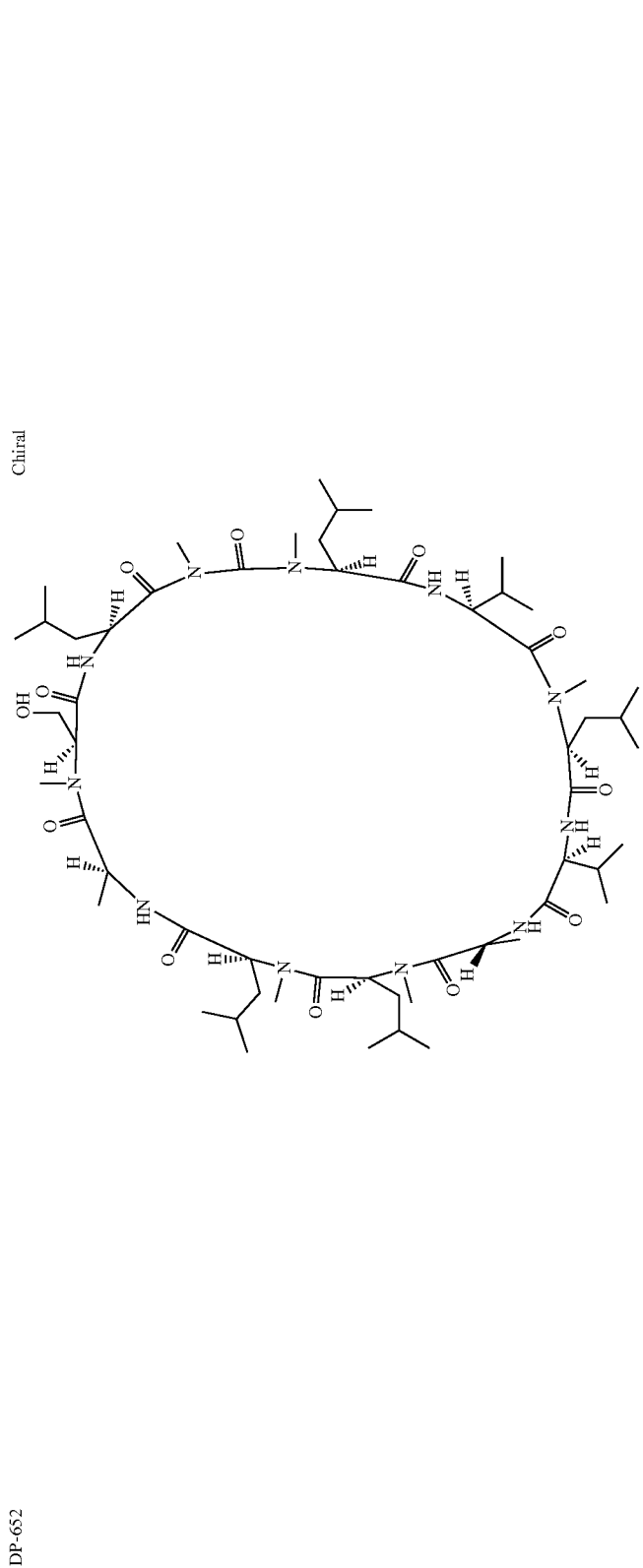
DP-652

TABLE 11-3-1-continued
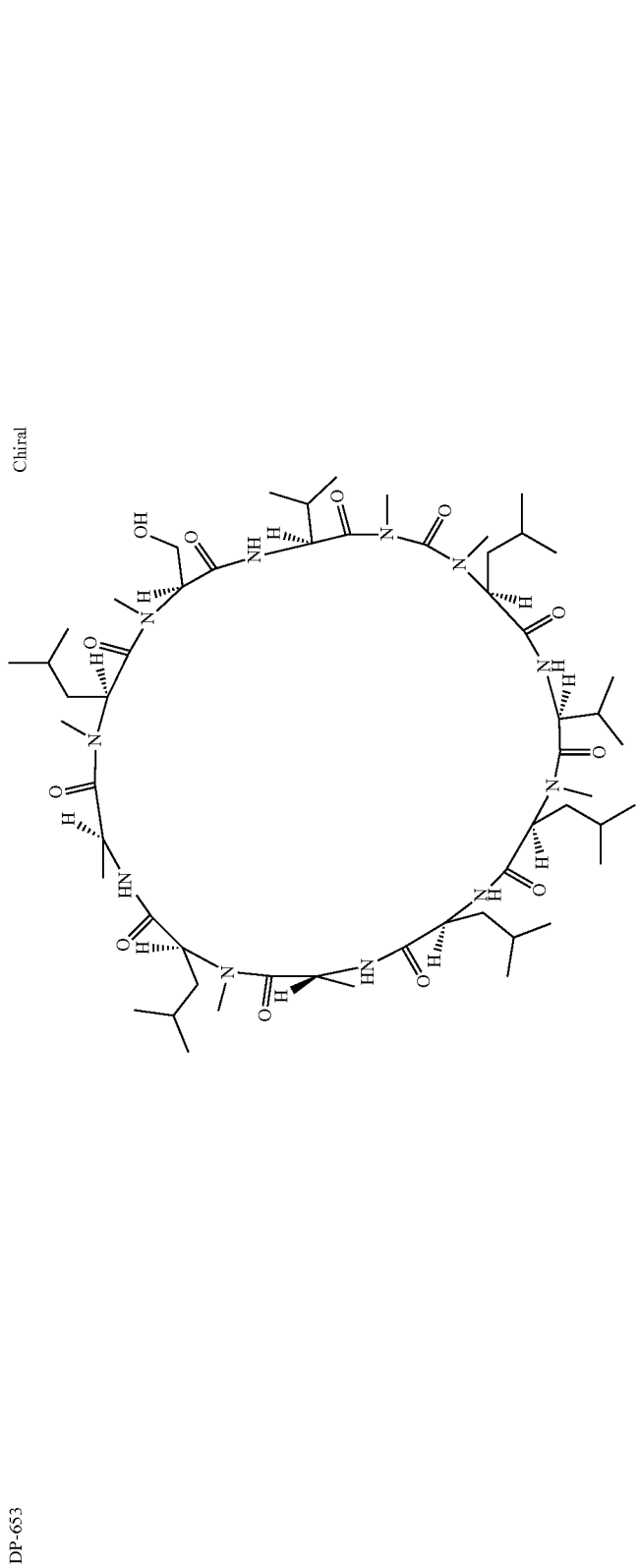
DP-653

TABLE 11-3-1-continued
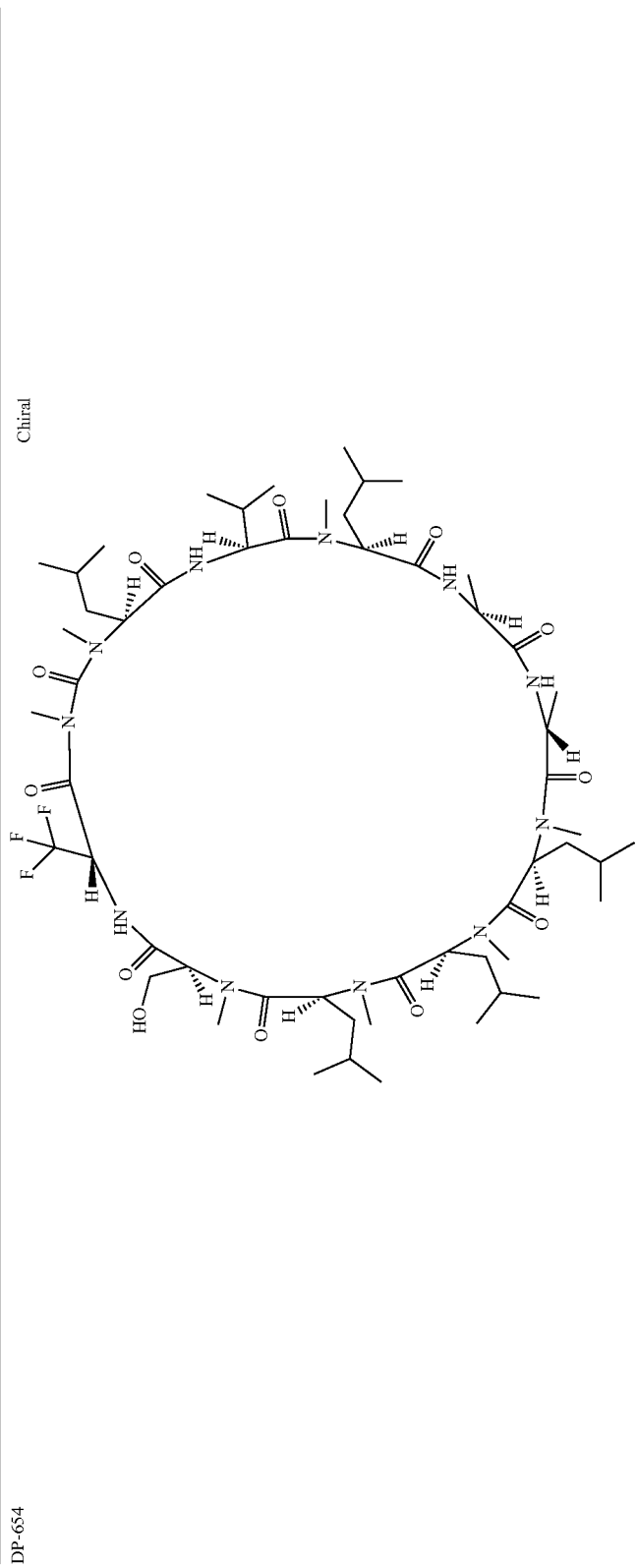
DP-654

TABLE 11-3-1-continued
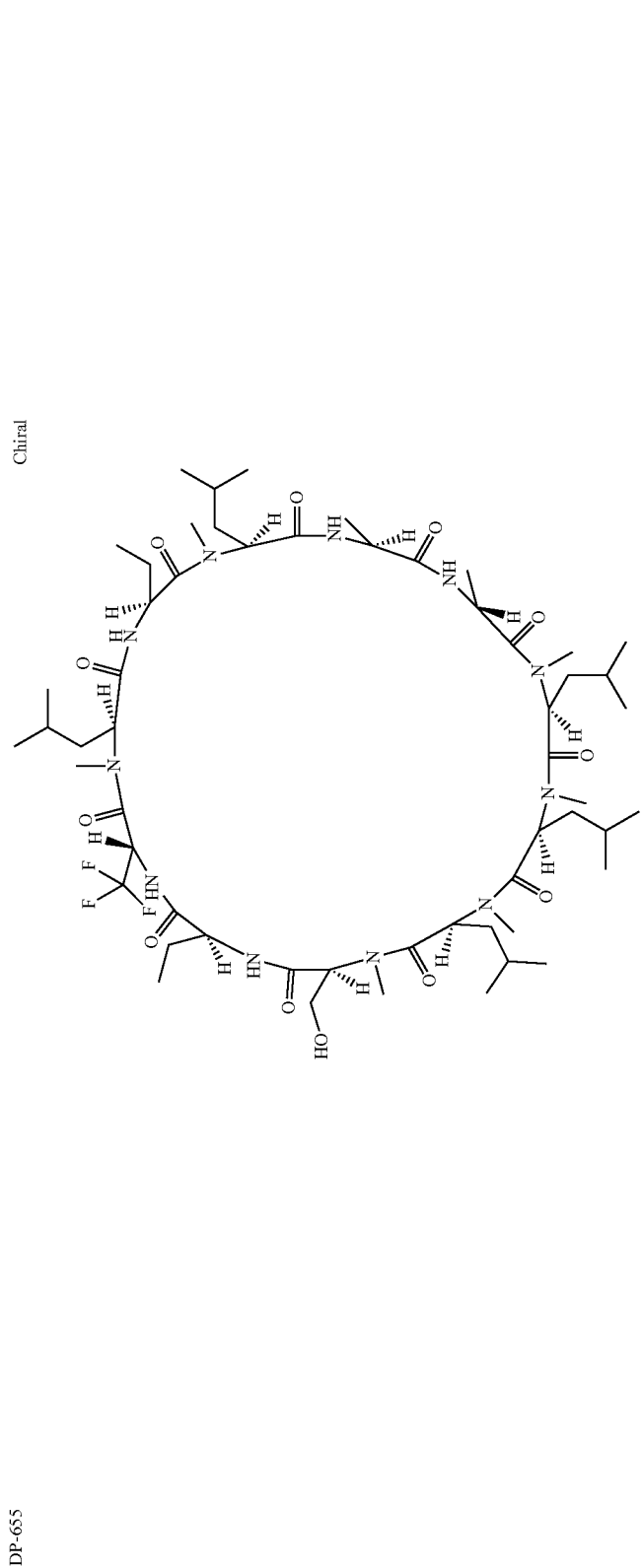
DP-655

TABLE 11-3-1-continued
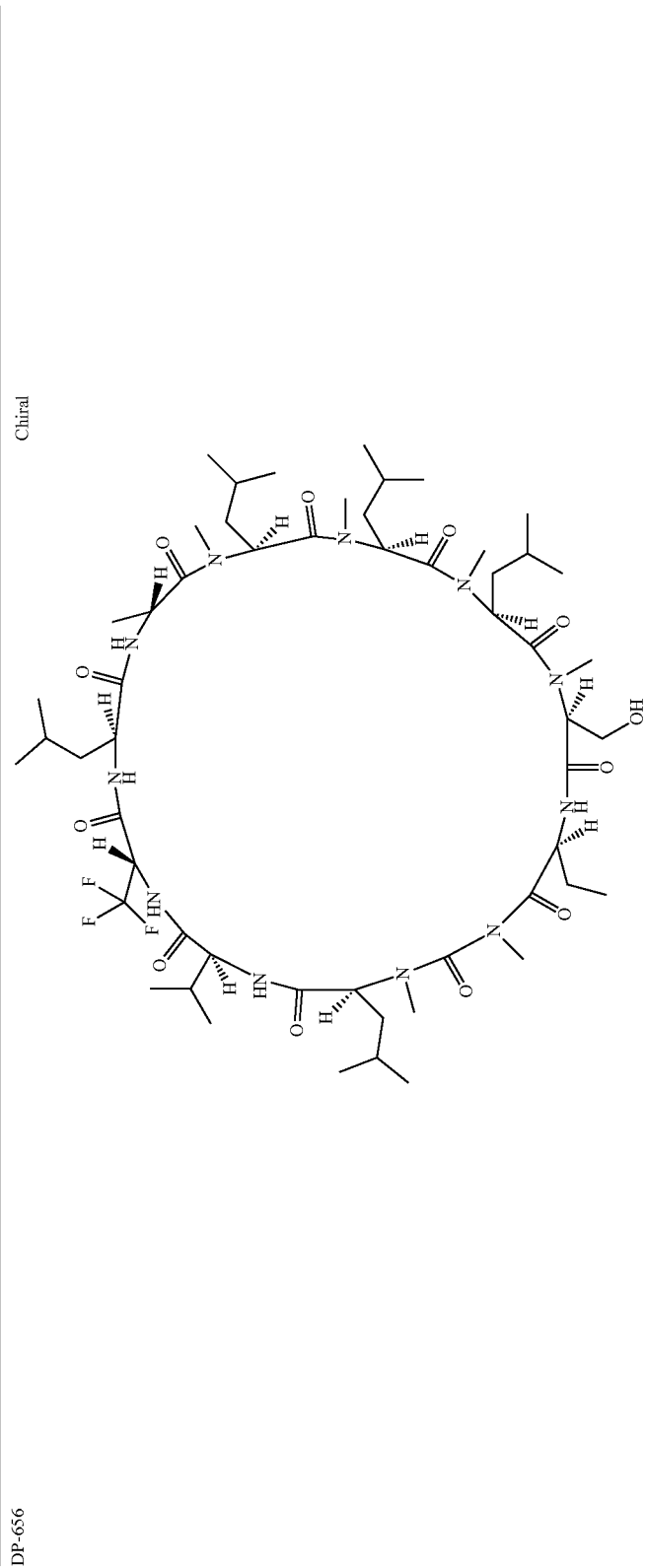
DP-656

TABLE 11-3-1-continued
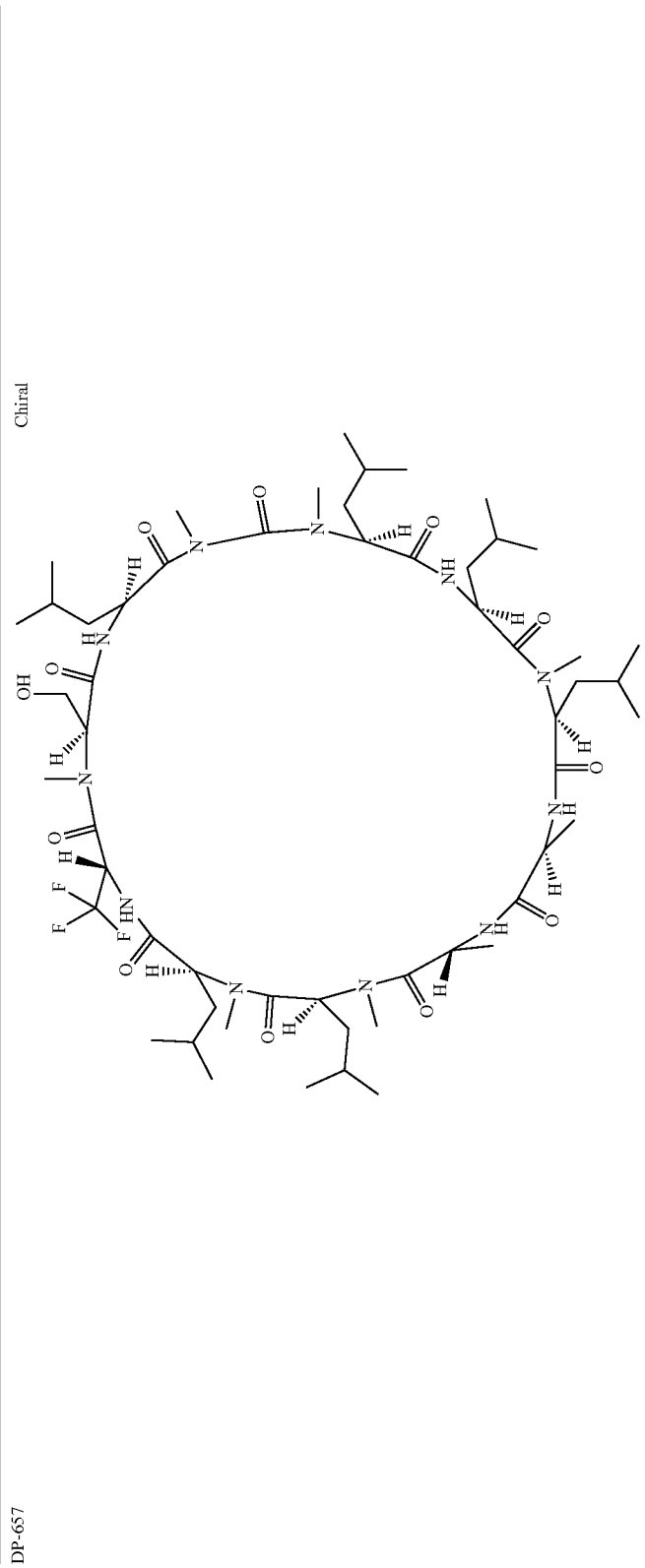
DP-657

TABLE 11-3-1-continued
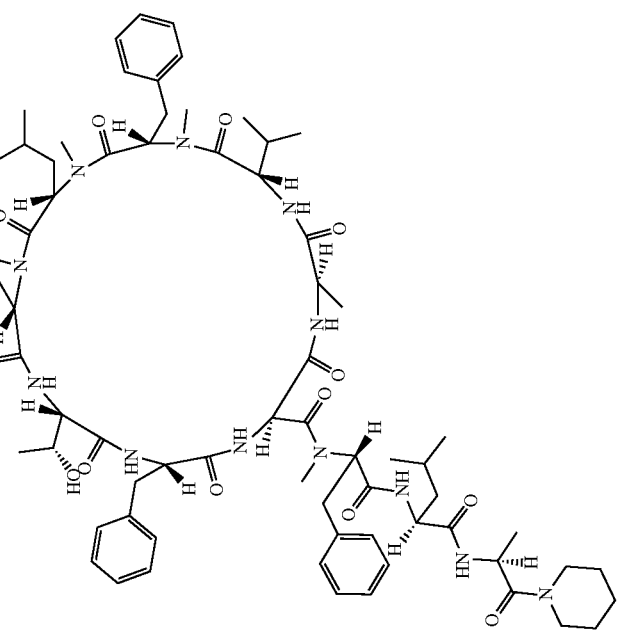
DP-658

TABLE 11-3-1-continued
Chiral
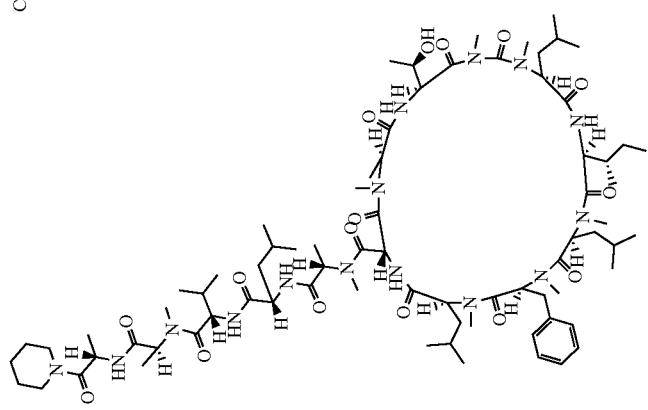
DP-659

TABLE 11-3-1-continued
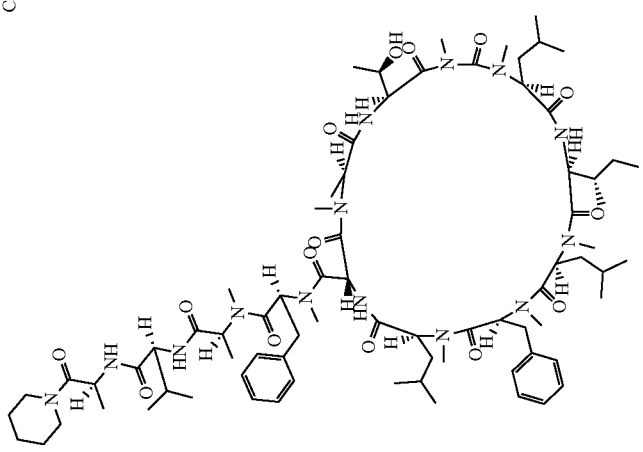
DP-660

TABLE 11-3-1-continued
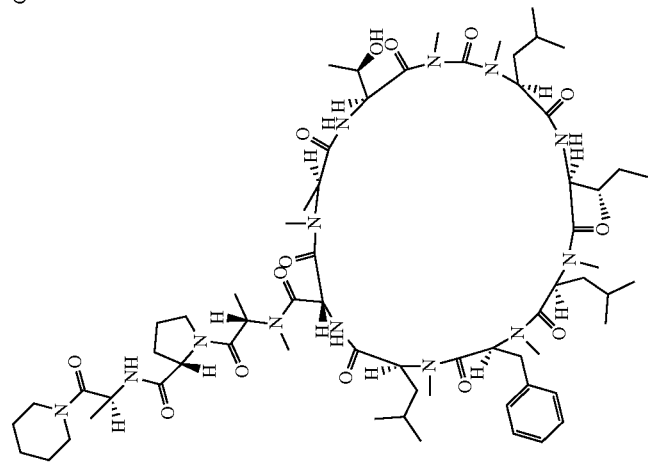
DP-661

TABLE 11-3-1-continued
Chiral
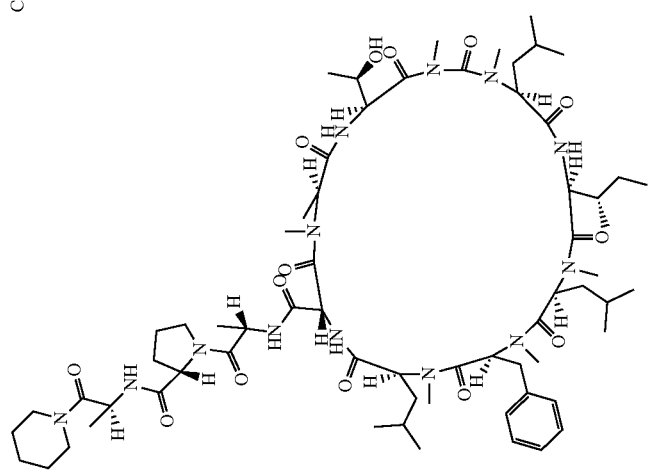
DP-662

TABLE 11-3-1-continued
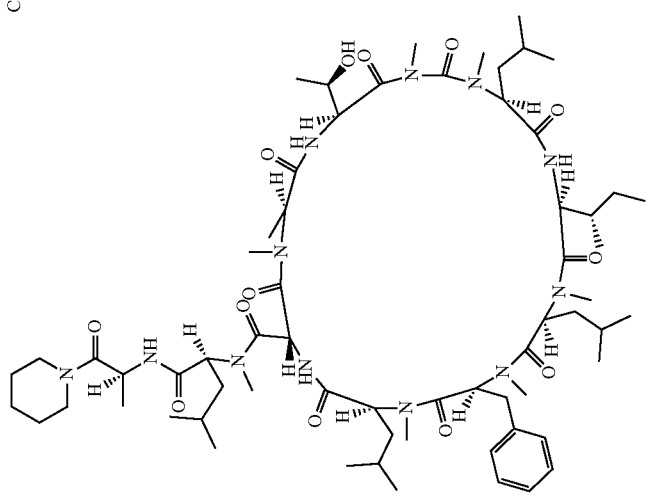
DP-663

TABLE 11-3-1-continued
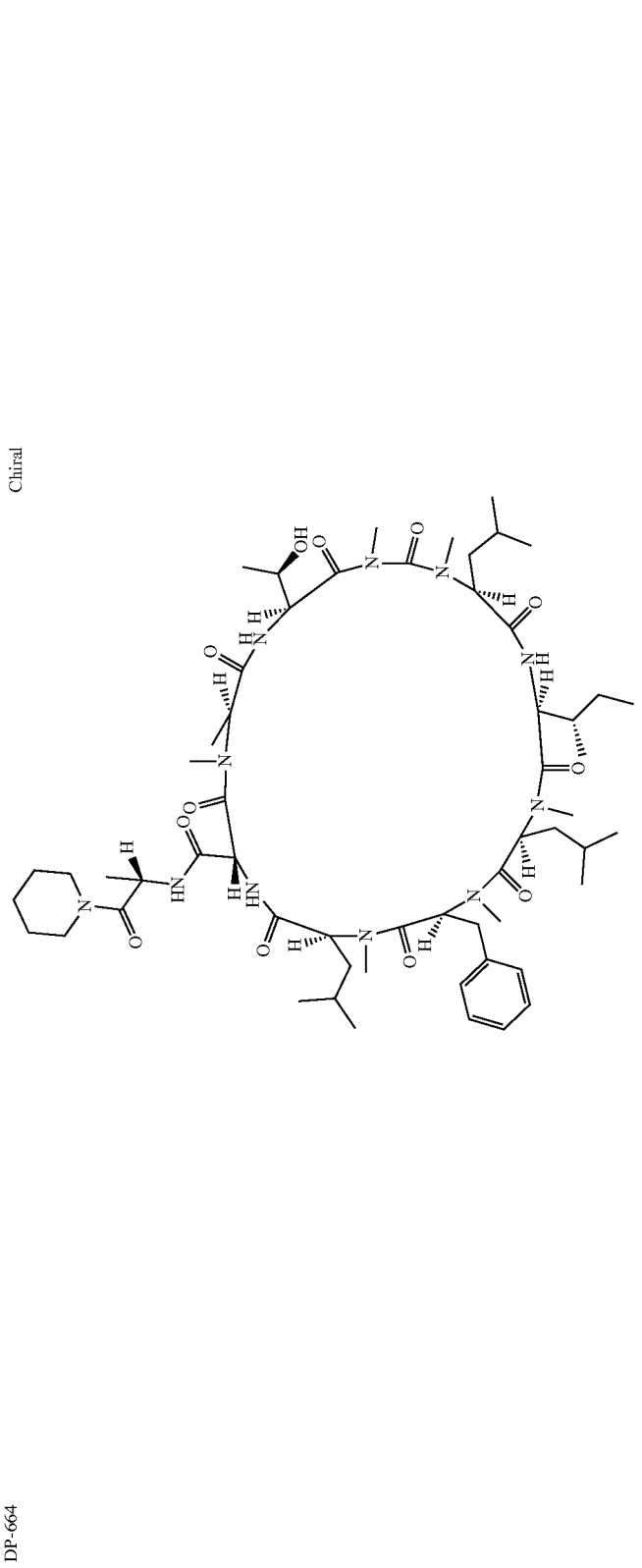
DP-664
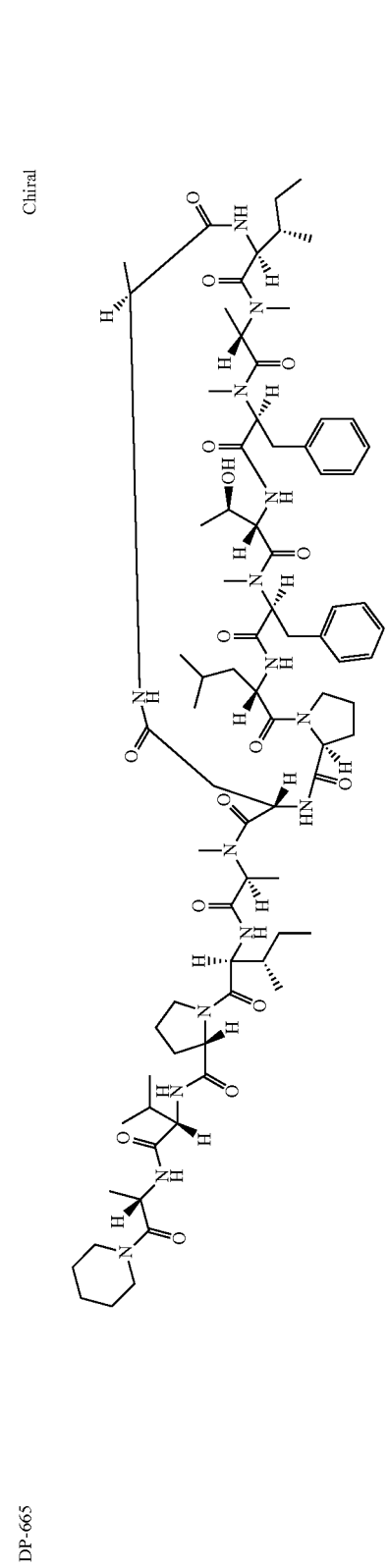
DP-665

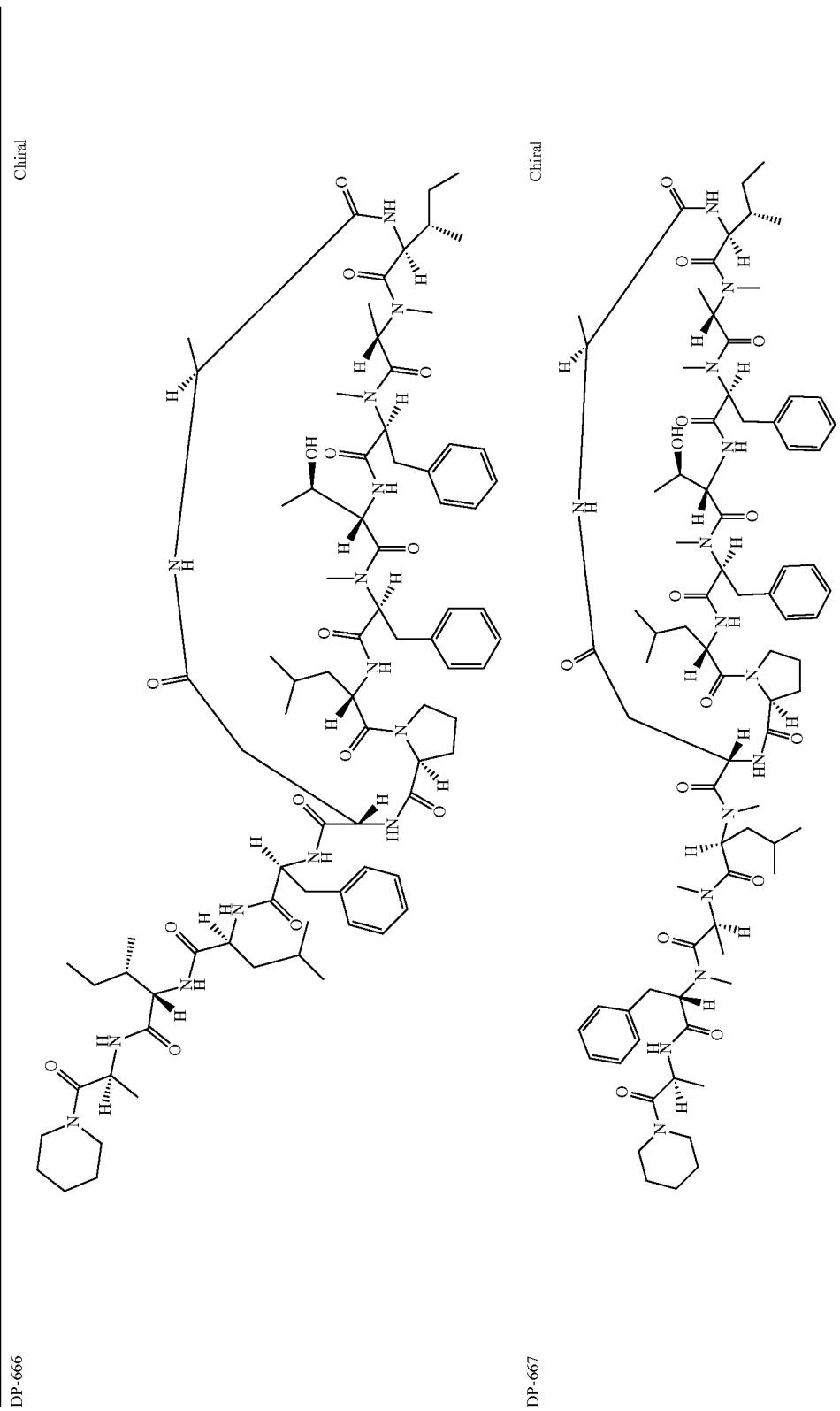

TABLE 11-3-1-continued
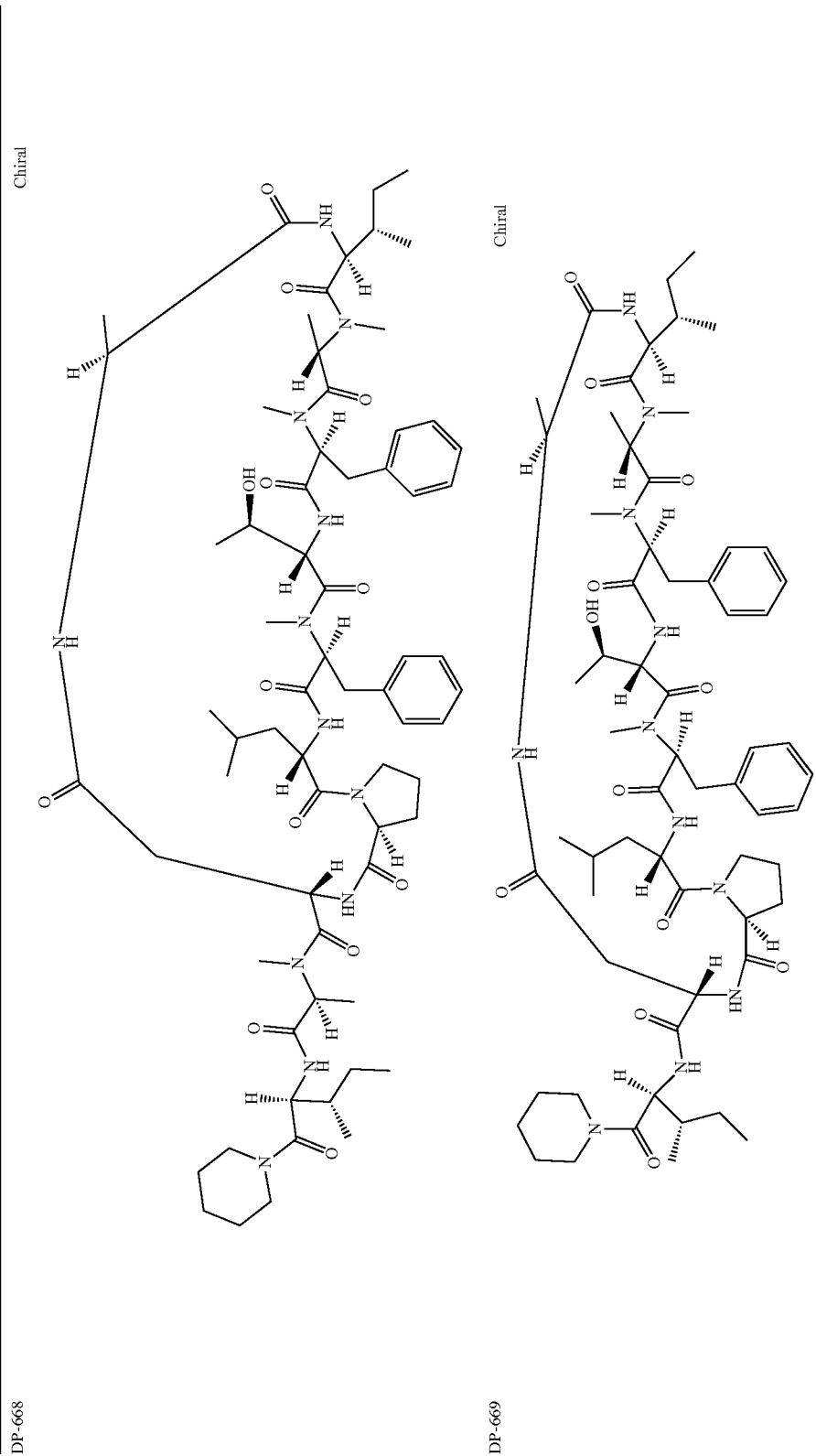
DP-668
DP-669

TABLE 11-3-1-continued
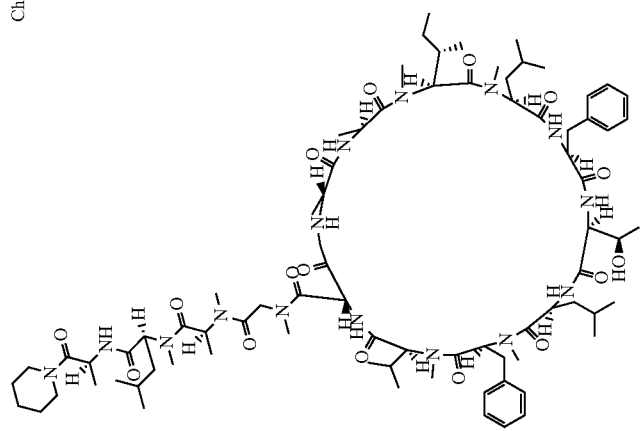
DP-670

TABLE 11-3-1-continued
Chiral
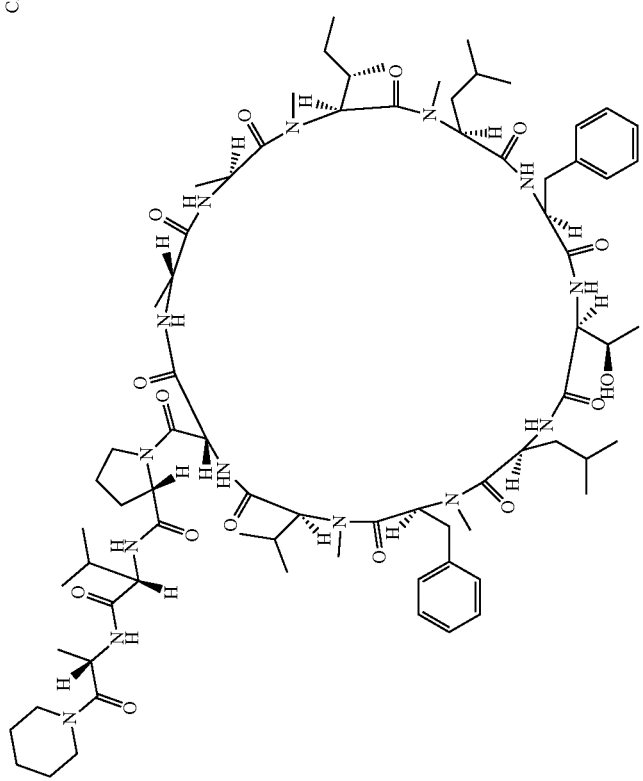
DP-671

TABLE 11-3-1-continued
DP-672
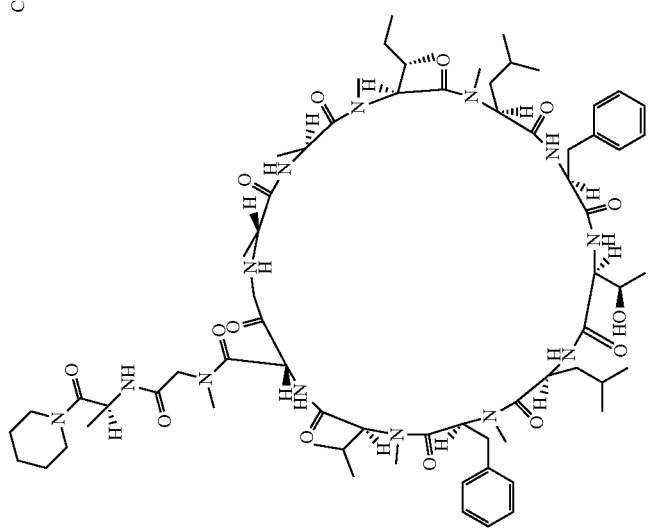

TABLE 11-3-1-continued
| DP-673 | 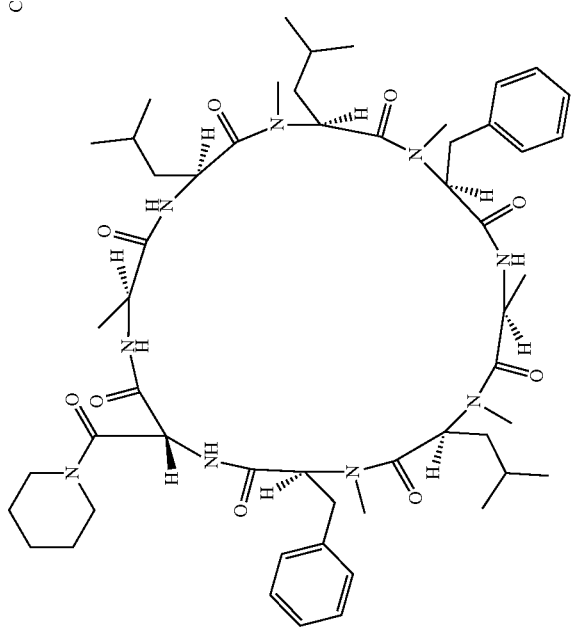 |
| DP-674 | 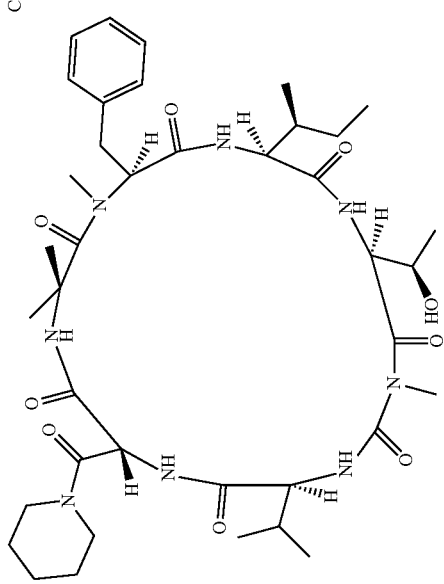 |

TABLE 11-3-1-continued
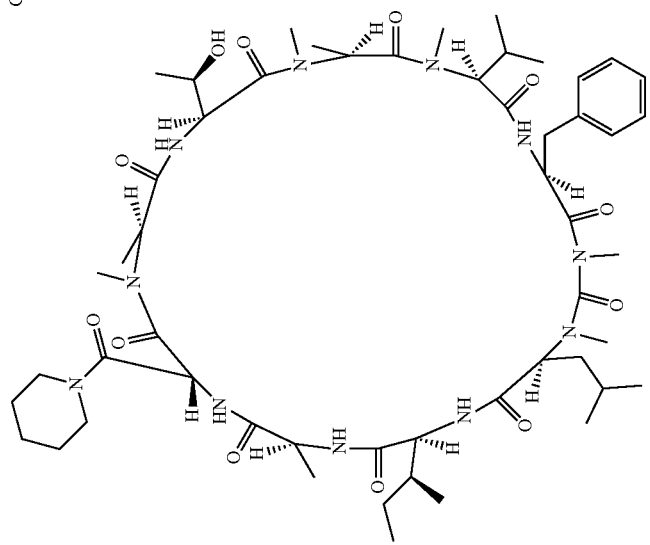
DP-675
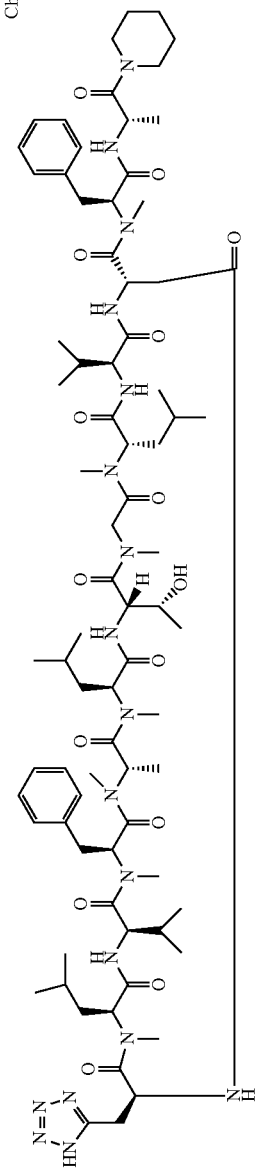
DP-676

TABLE 11-3-1-continued
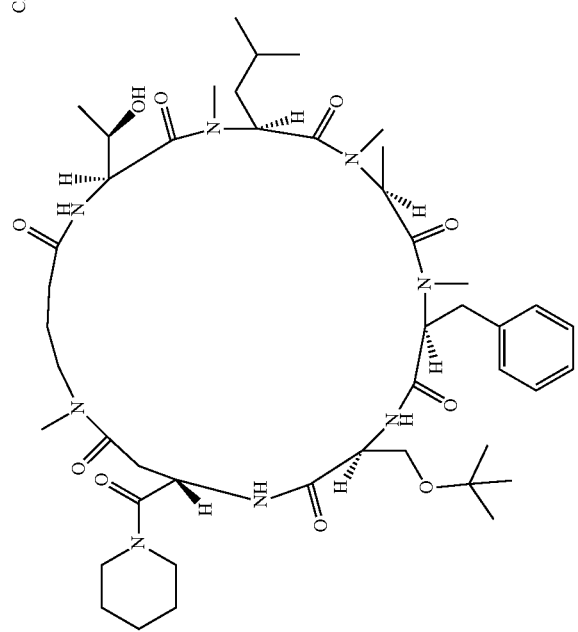
DP-677
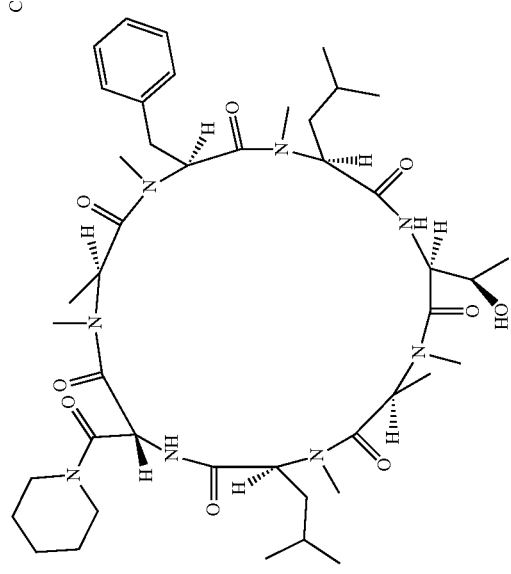
DP-678

TABLE 11-3-1-continued
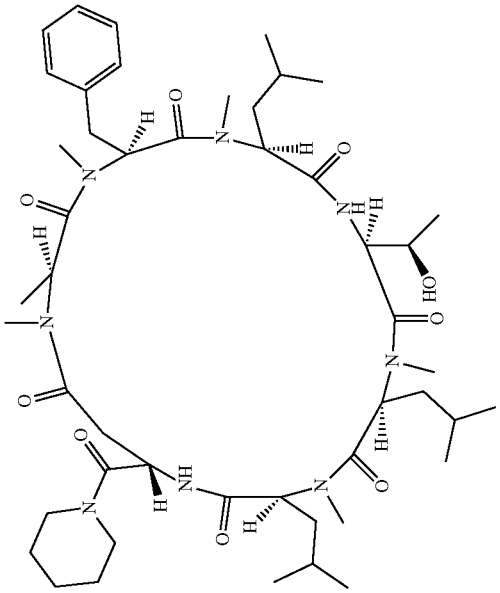
DP-679
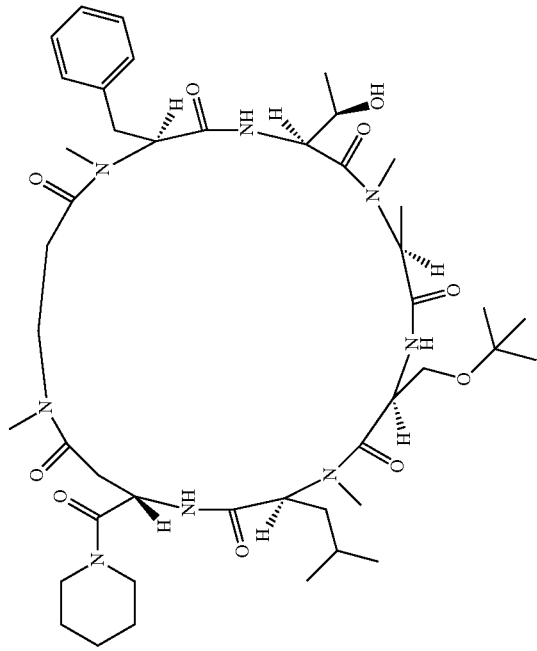
DP-680

TABLE 11-3-1-continued
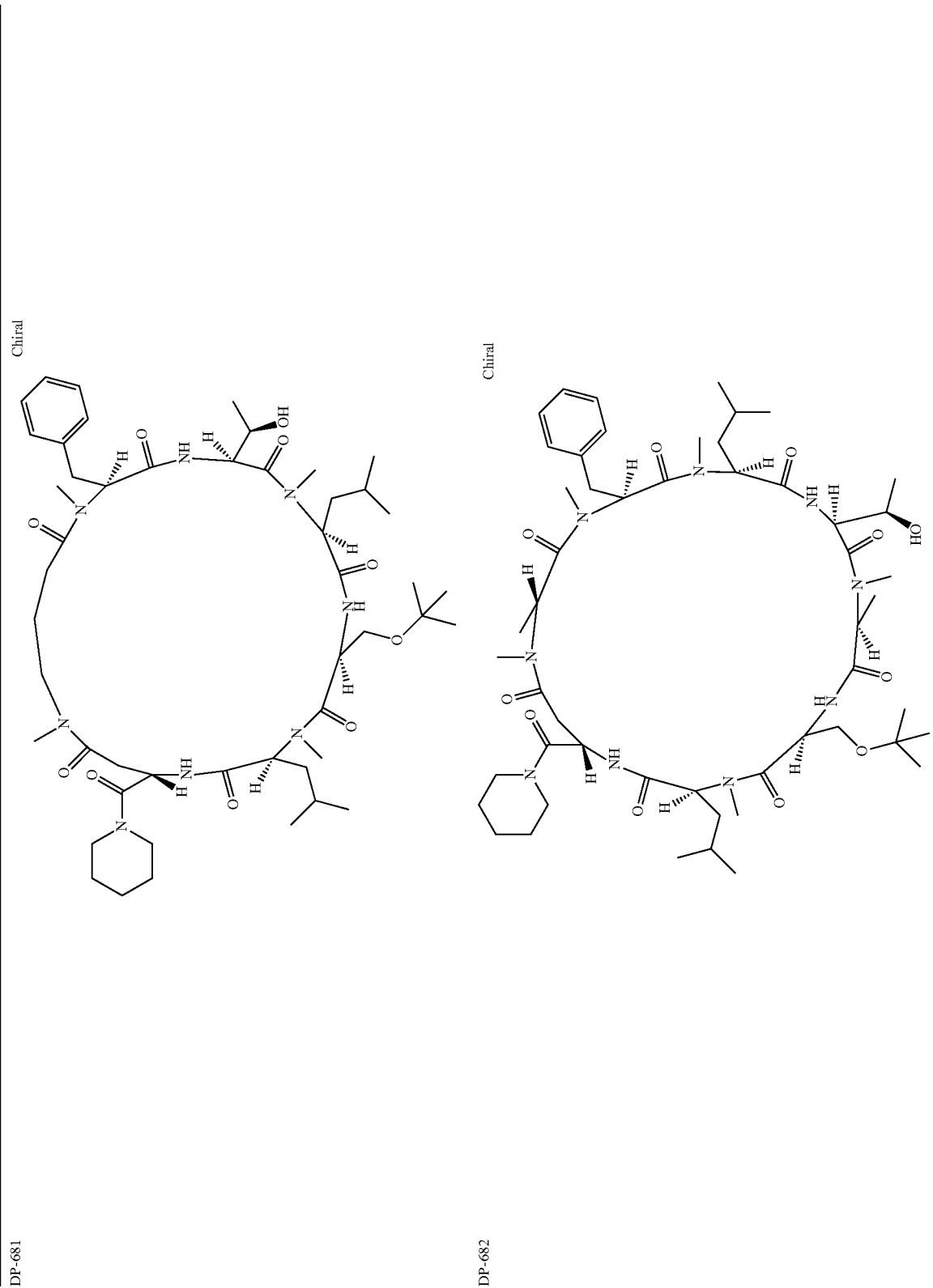
DP-681
DP-682

TABLE 11-3-1-continued
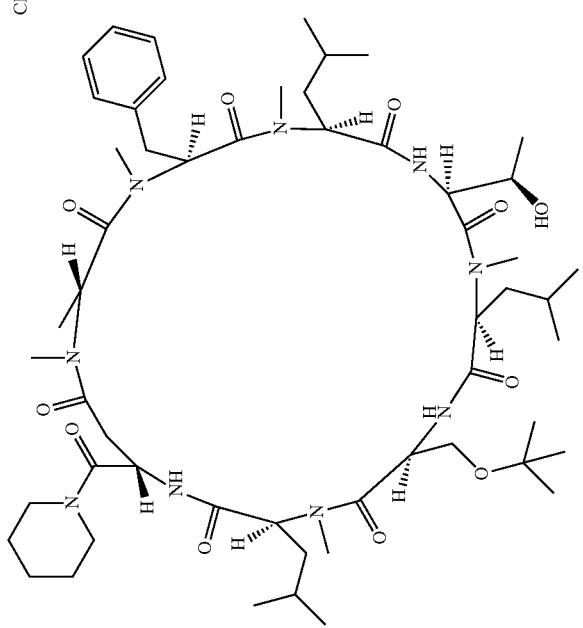
DP-683

TABLE 11-3-1-continued
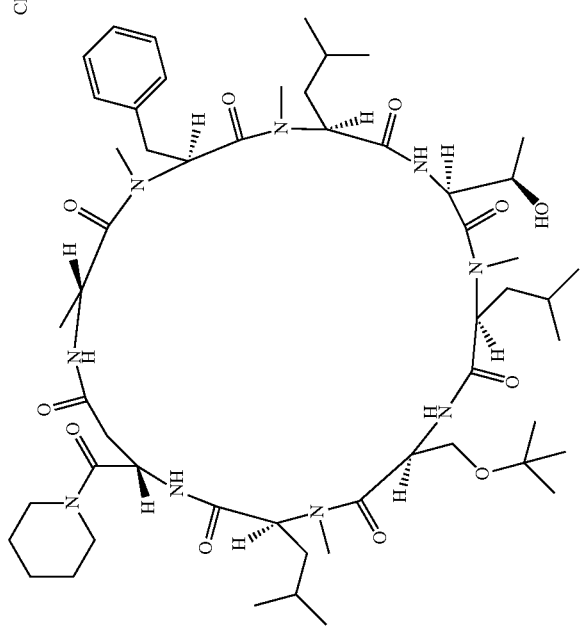
DP-684

TABLE 11-3-1-continued
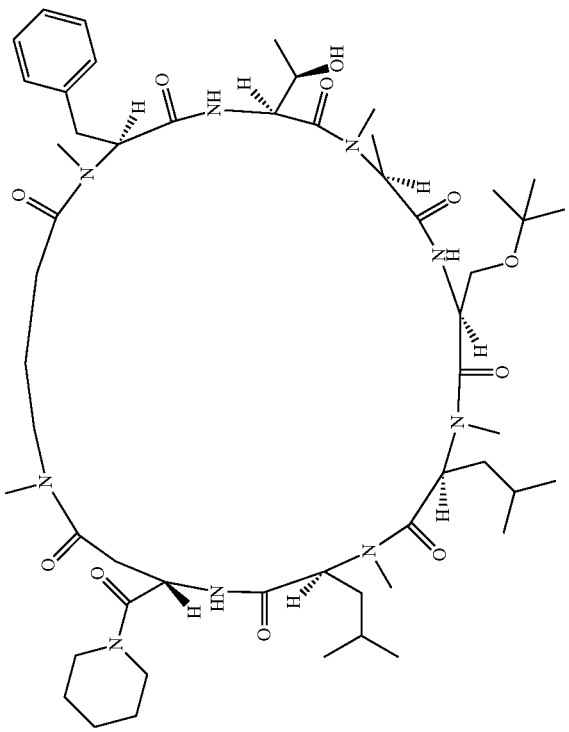
DP-685

TABLE 11-3-1-continued
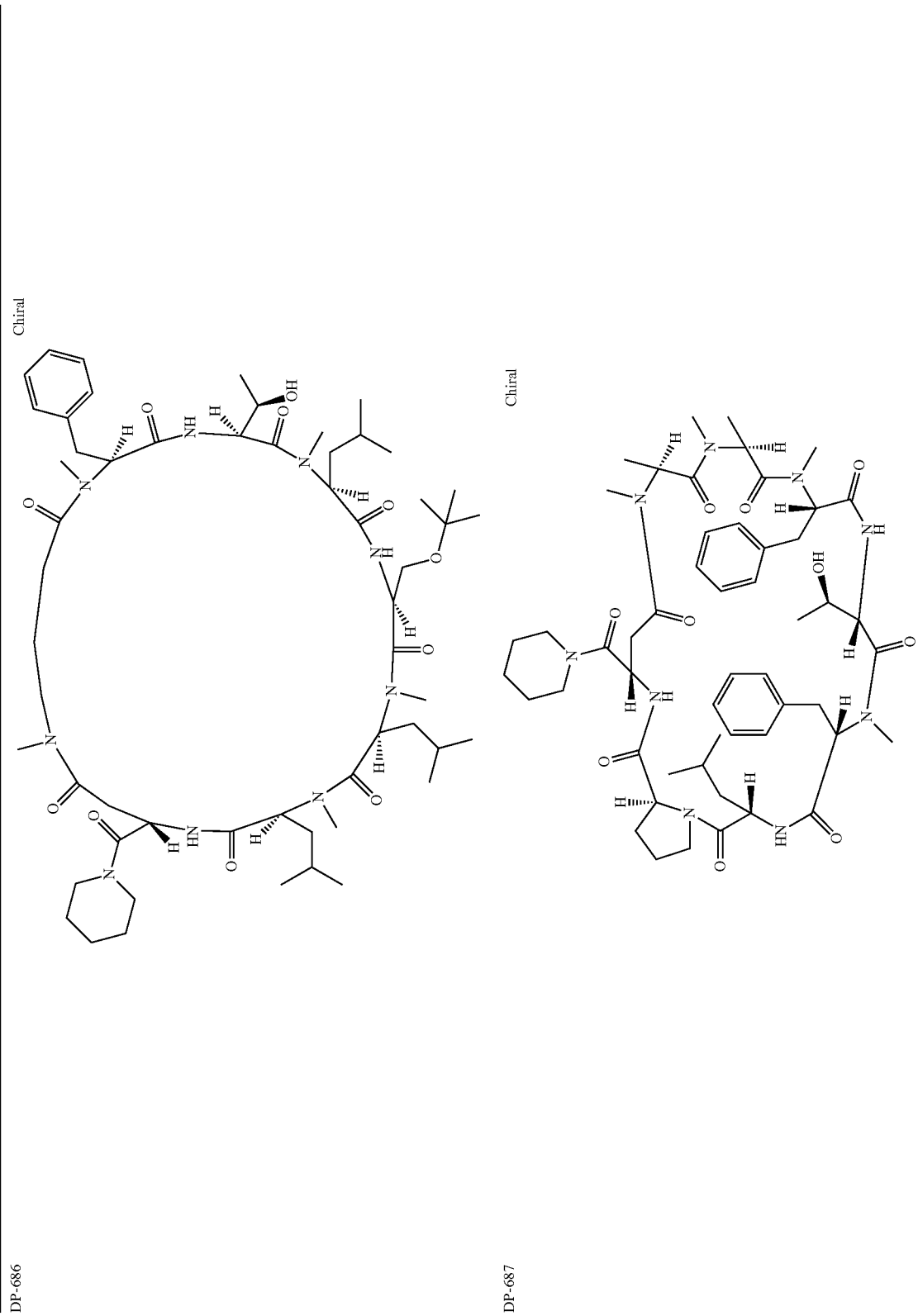
DP-686
DP-687

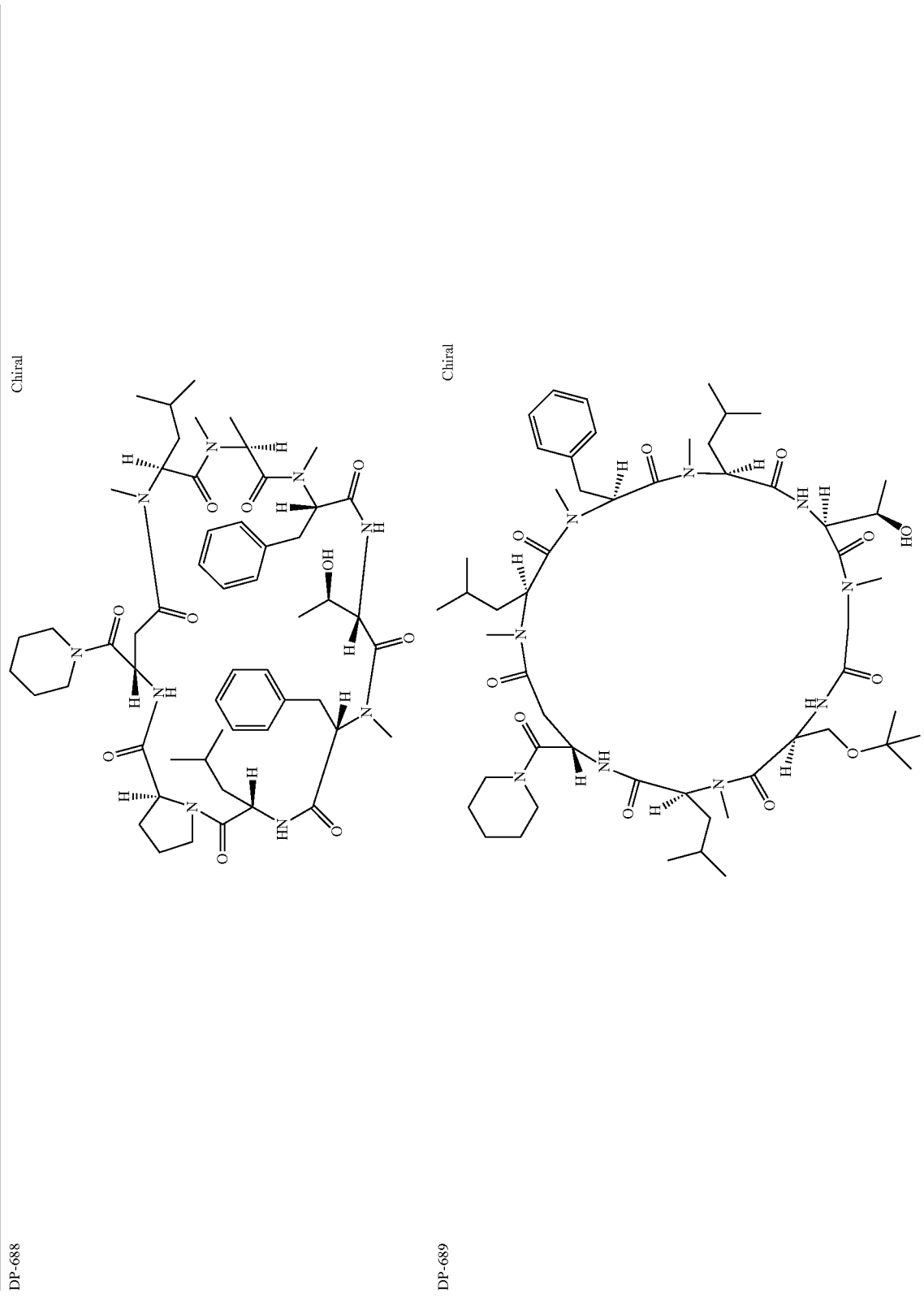

TABLE 11-3-1-continued
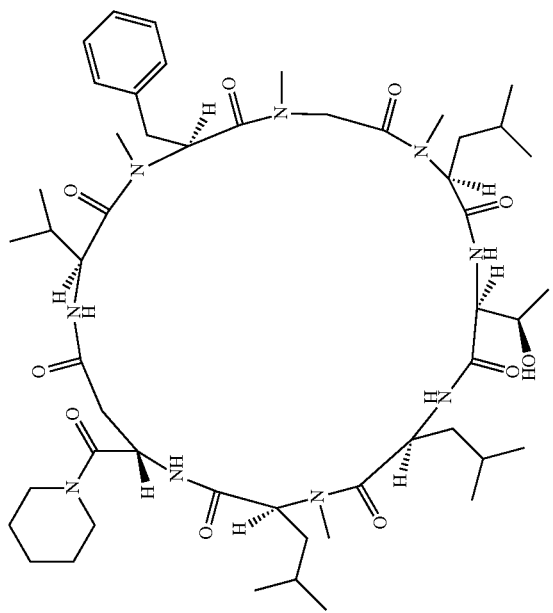
DP-690

TABLE 11-3-1-continued
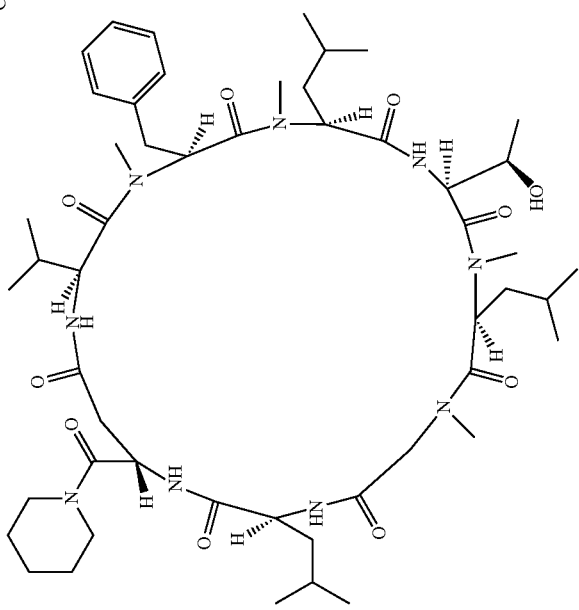
DP-691

TABLE 11-3-1-continued
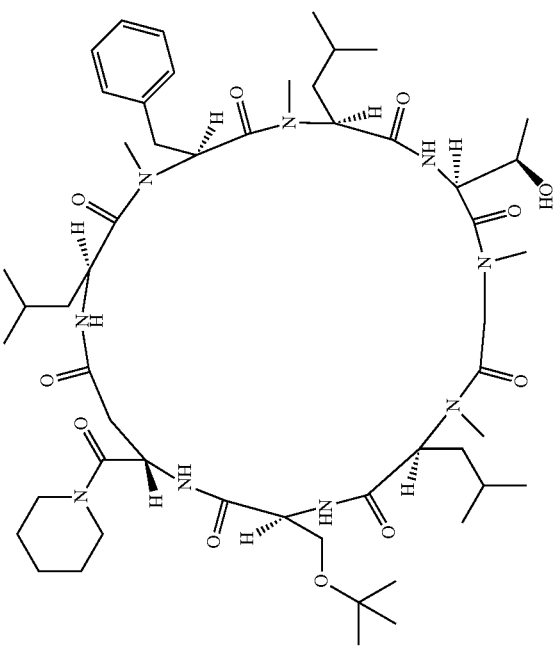
DP-692

TABLE 11-3-1-continued
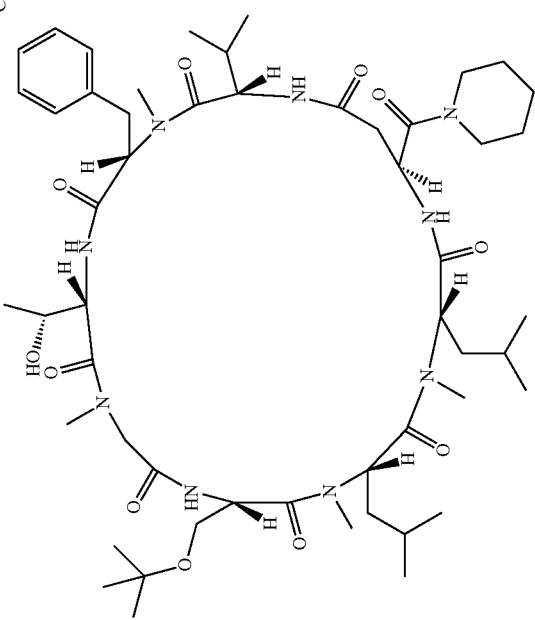
DP-693

TABLE 11-3-1-continued
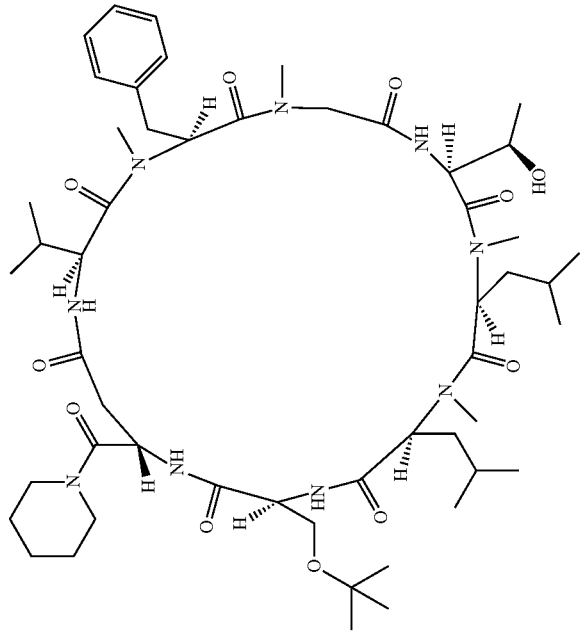
DP-694

TABLE 11-3-1-continued
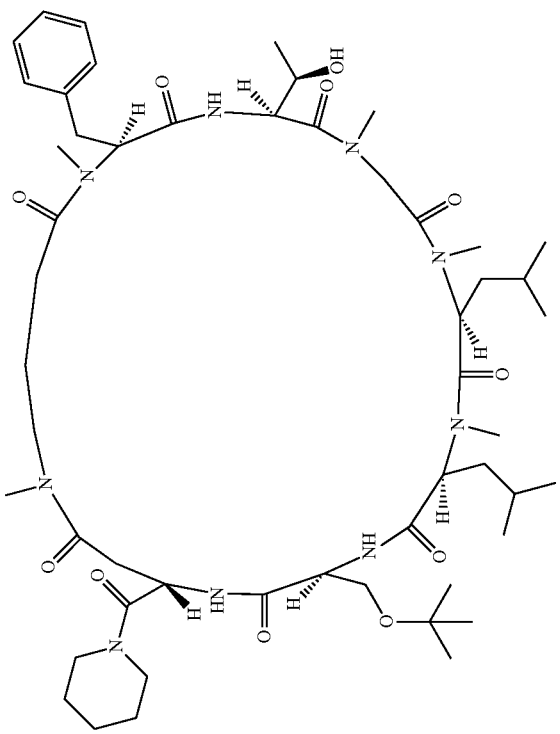
DP-695

TABLE 11-3-1-continued
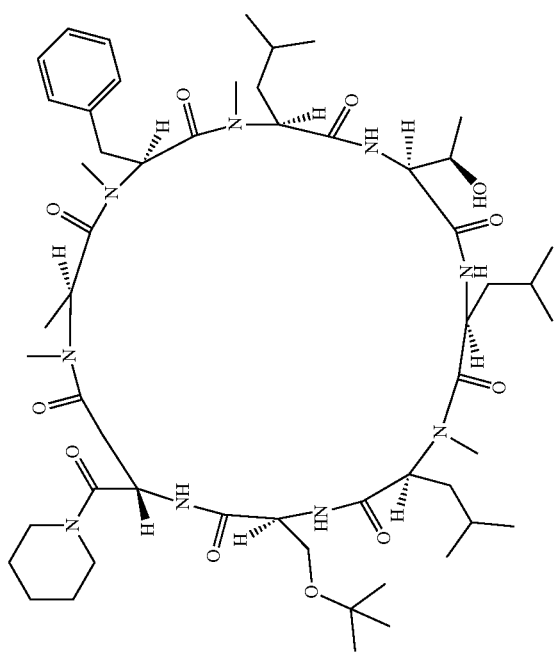
DP-696

TABLE 11-3-1-continued
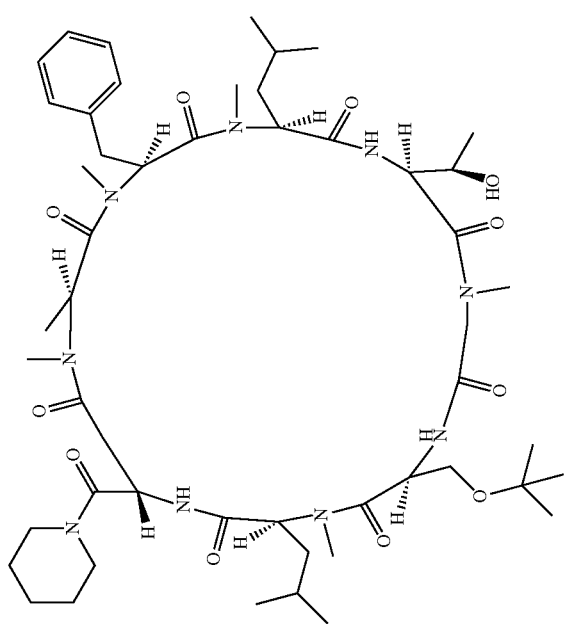
DP-697

TABLE 11-3-1-continued
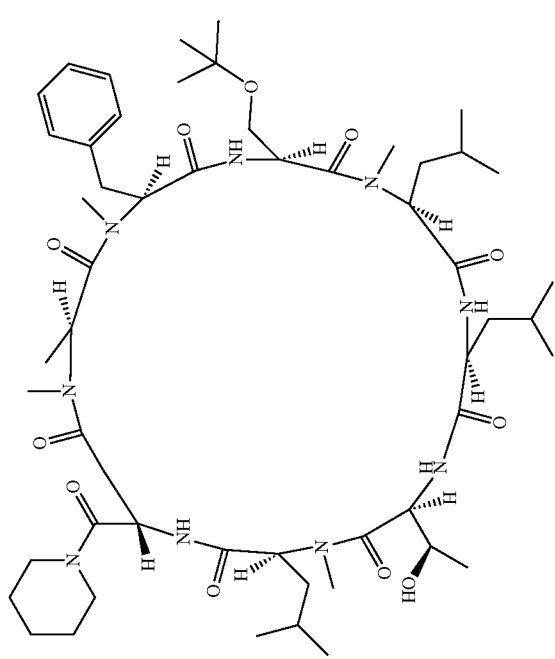
DP-698

TABLE 11-3-1-continued
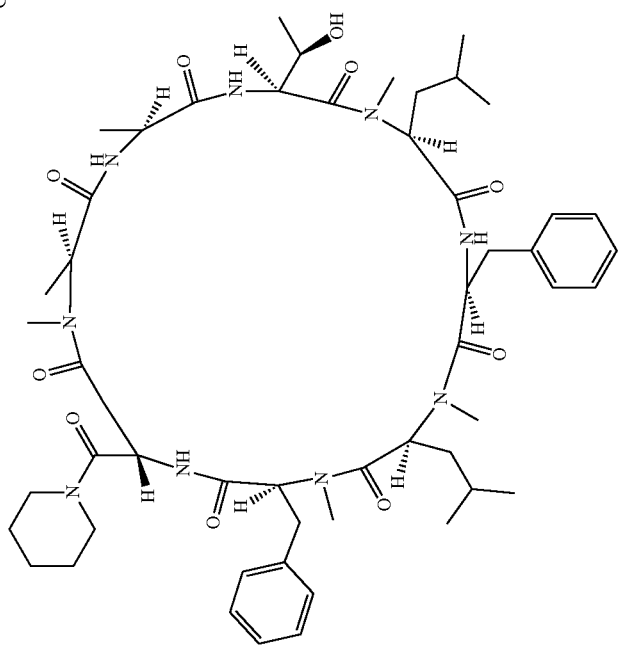
DP-699

TABLE 11-3-1-continued
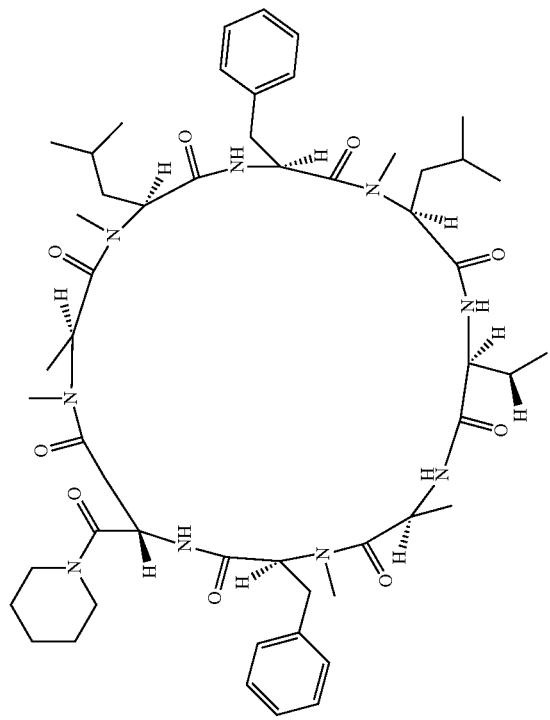
DP-700

TABLE 11-3-1-continued
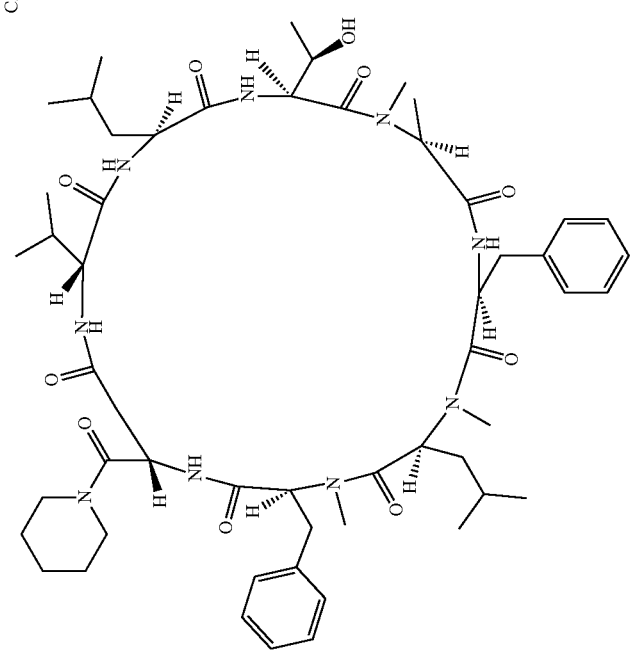
DP-701

TABLE 11-3-1-continued
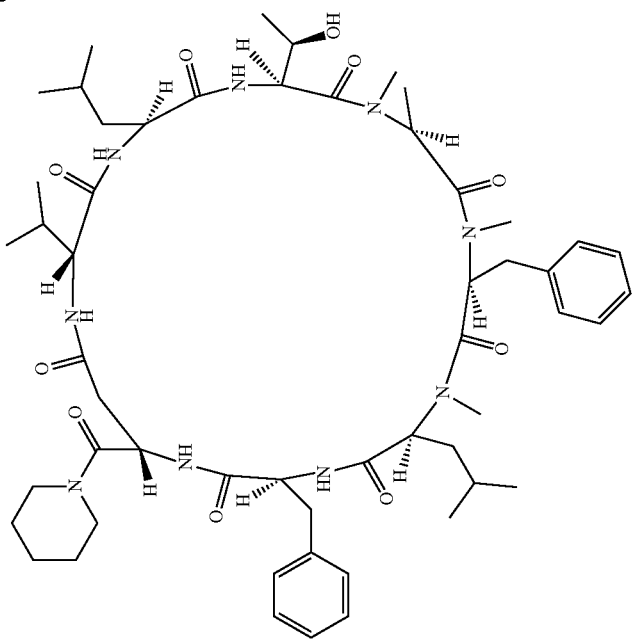
DP-702

TABLE 11-3-1-continued
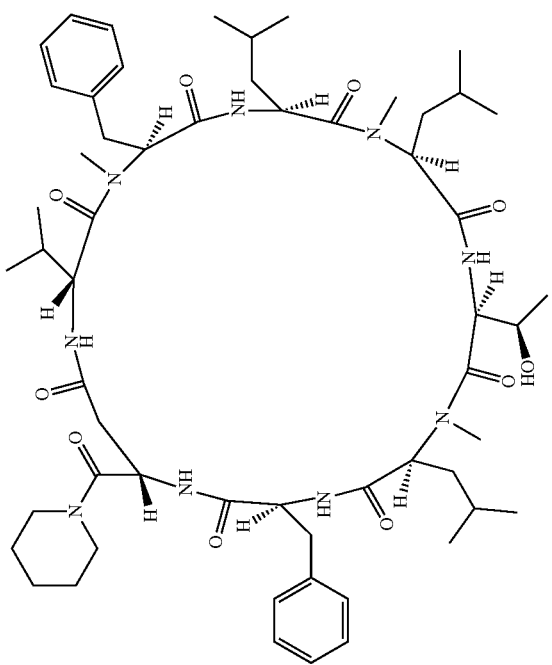
DP-703

TABLE 11-3-1-continued
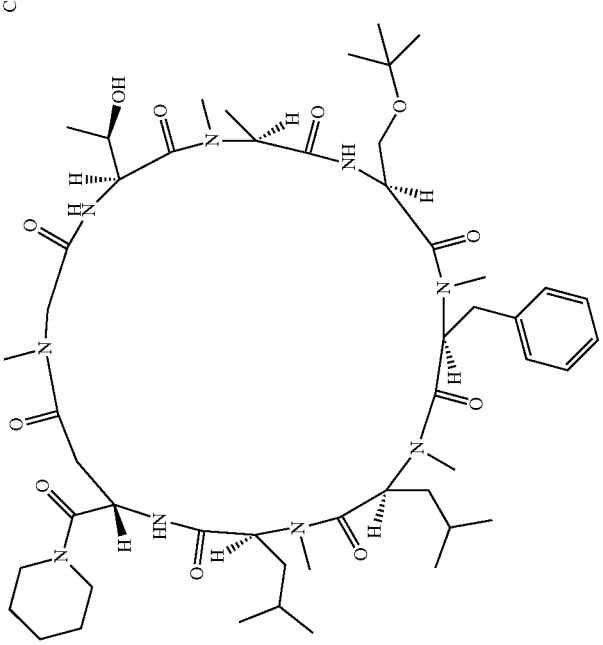
DP-704

TABLE 11-3-1-continued
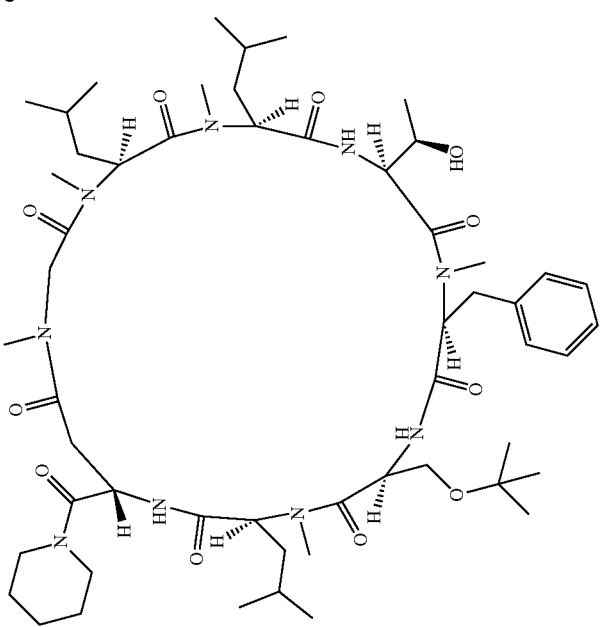
DP-705

TABLE 11-3-1-continued
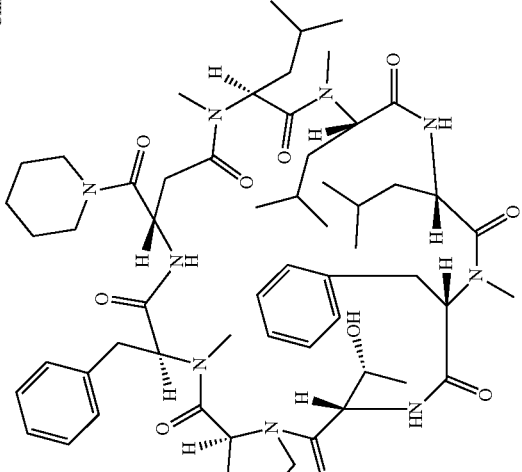
DP-706
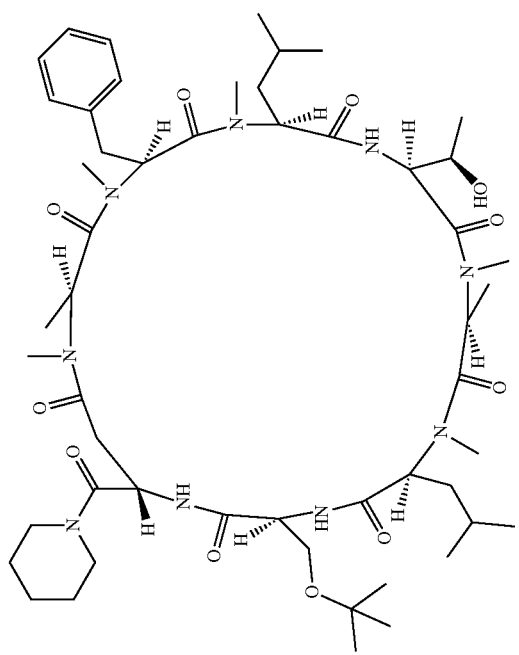
DP-707

TABLE 11-3-1-continued
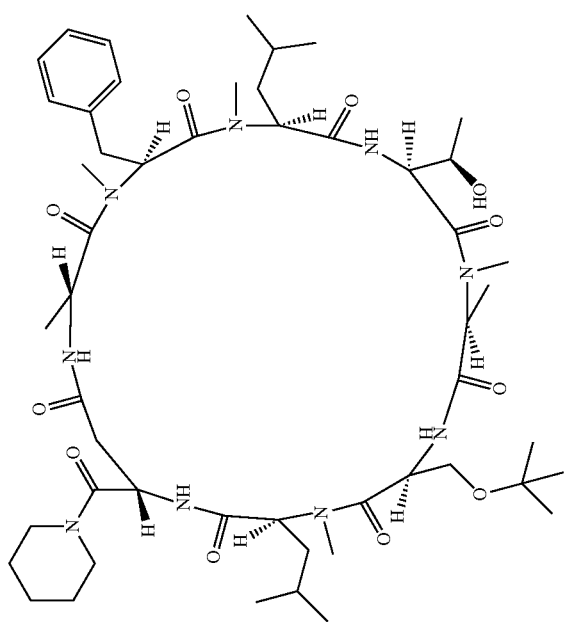
DP-708

TABLE 11-3-1-continued
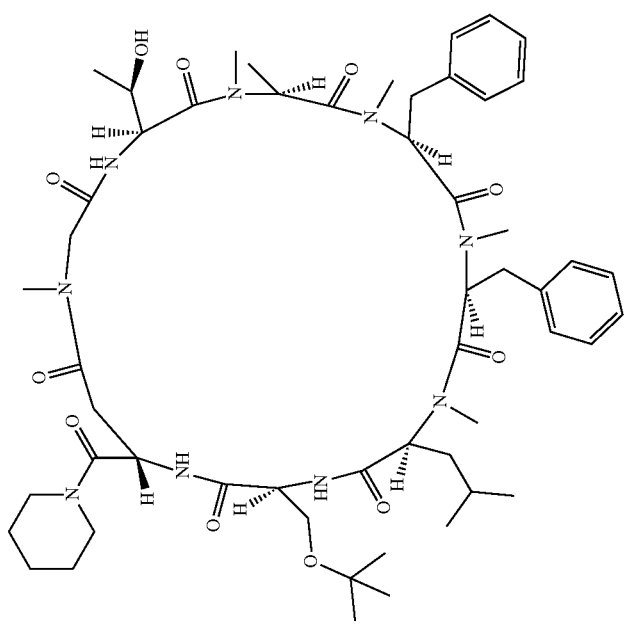
DP-709

TABLE 11-3-1-continued
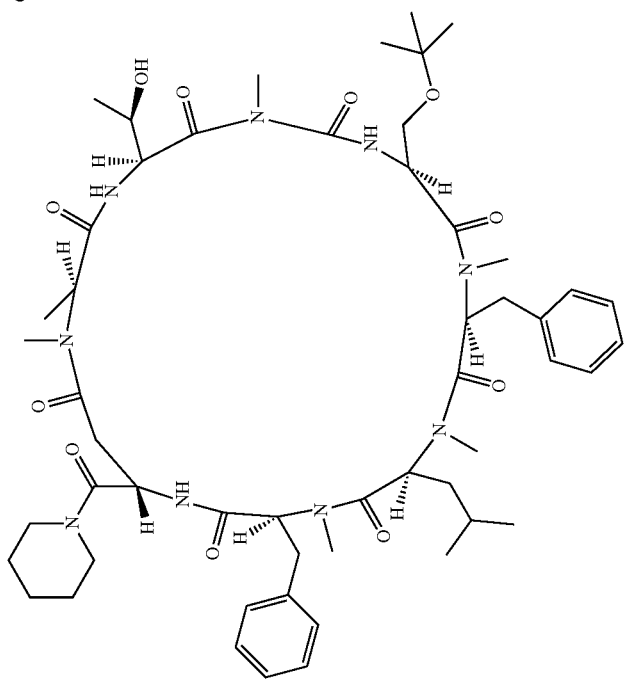
DP-710

TABLE 11-3-1-continued
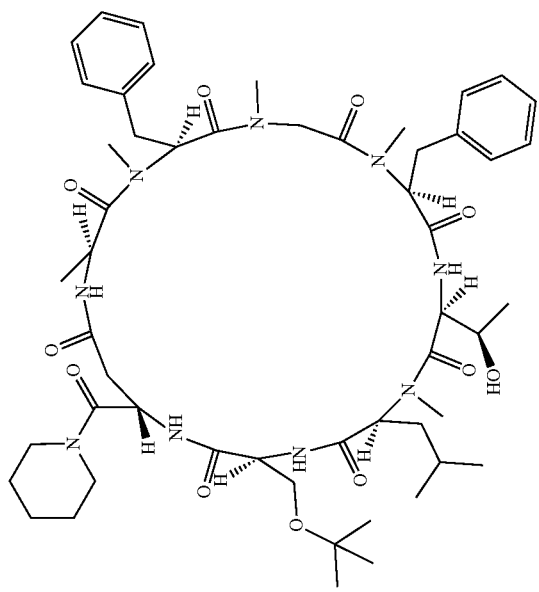
DP-711

TABLE 11-3-1-continued
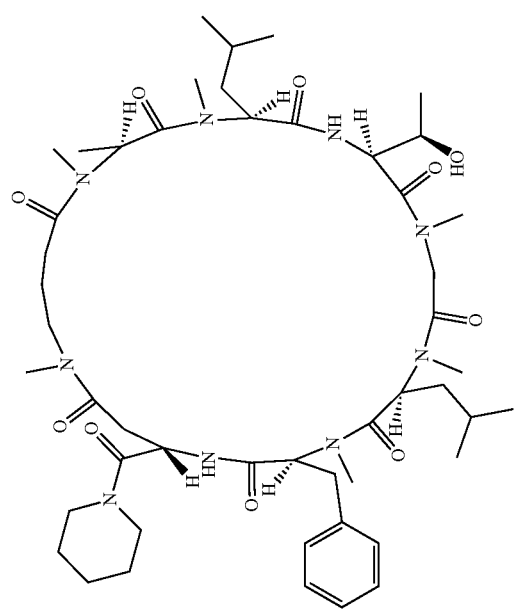
DP-712

TABLE 11-3-1-continued
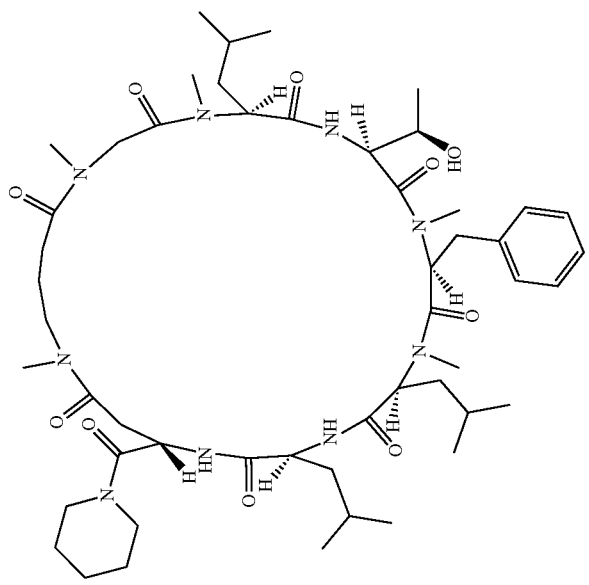
DP-713

TABLE 11-3-1-continued
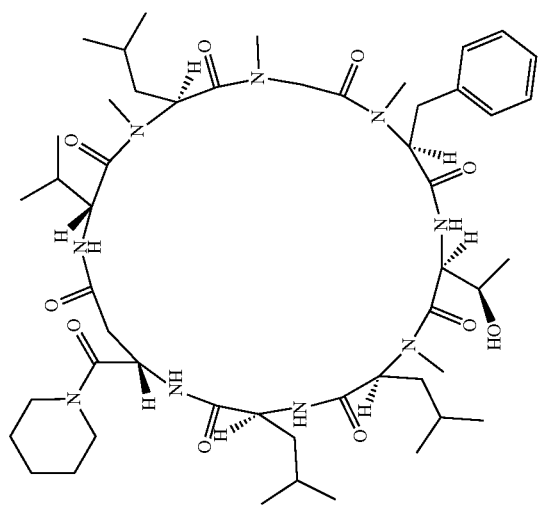
DP-714

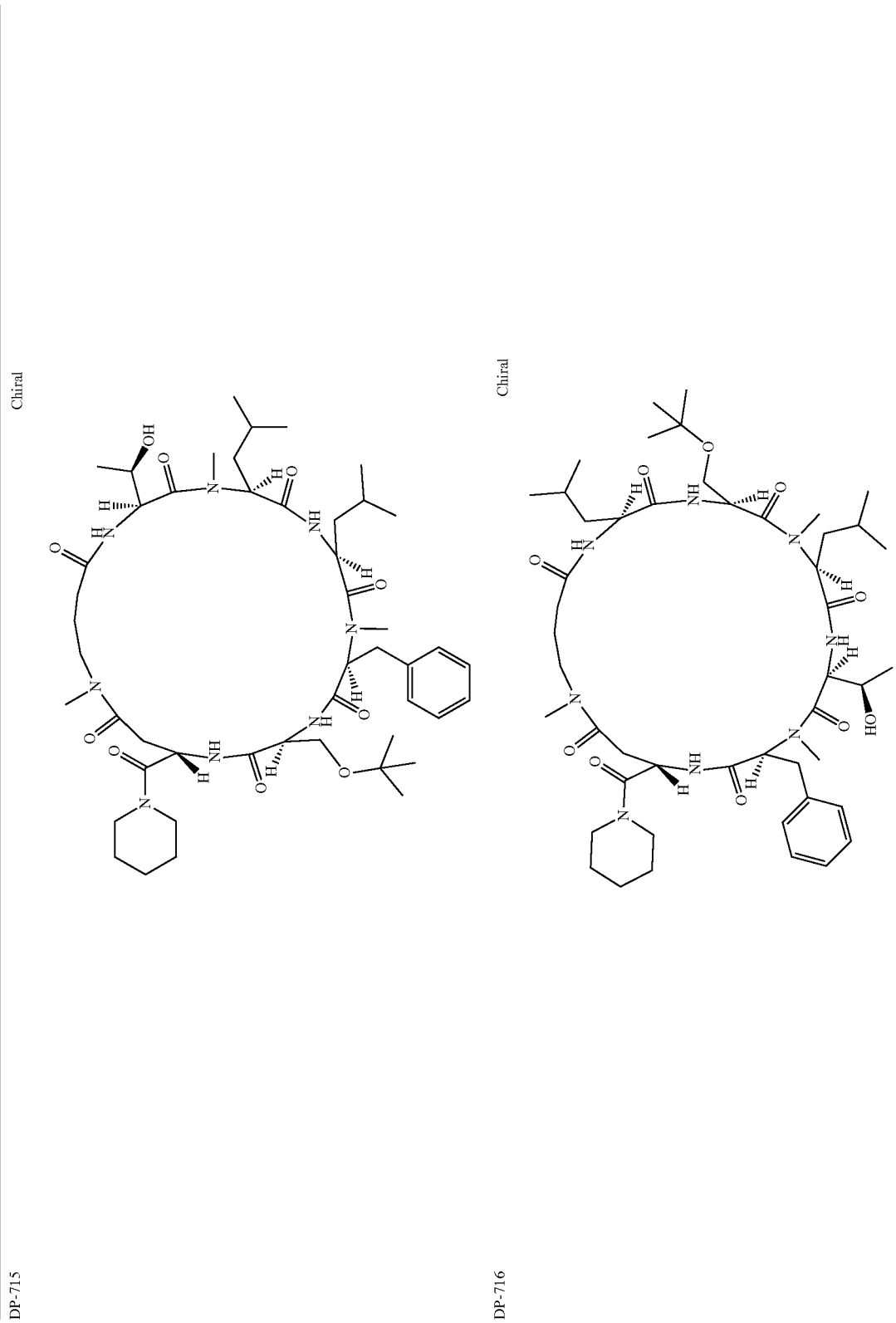

TABLE 11-3-1-continued
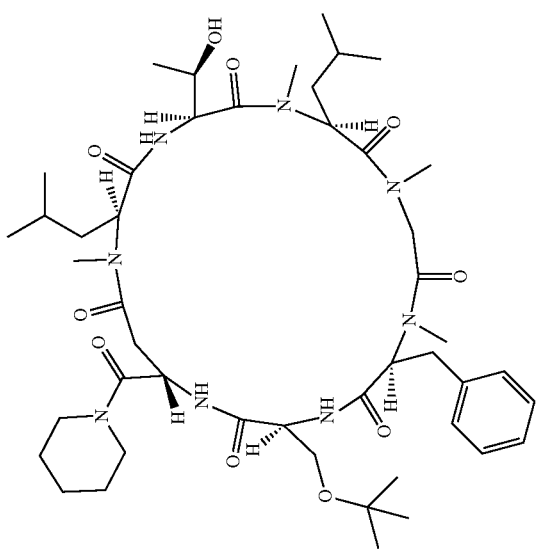
DP-717

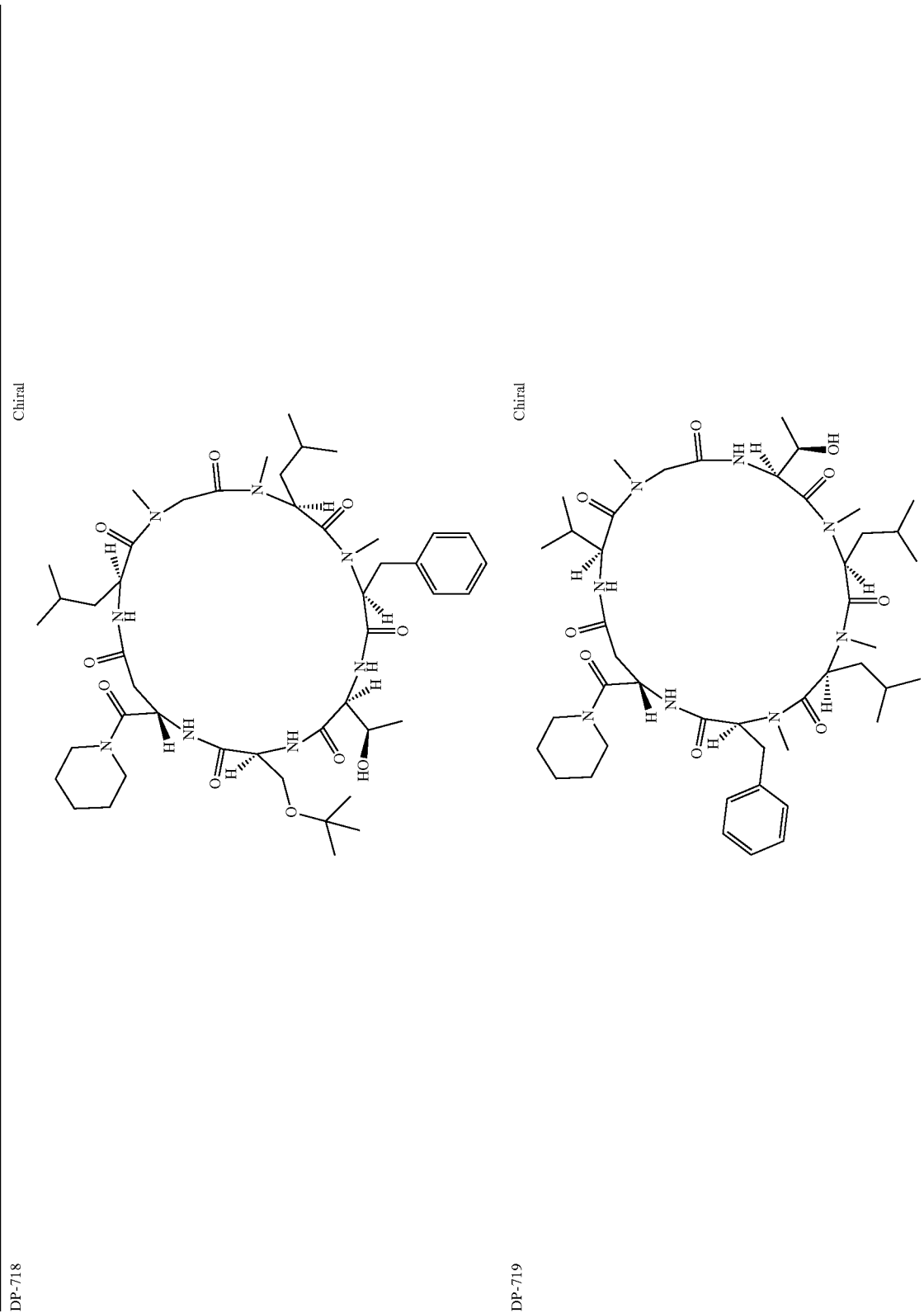

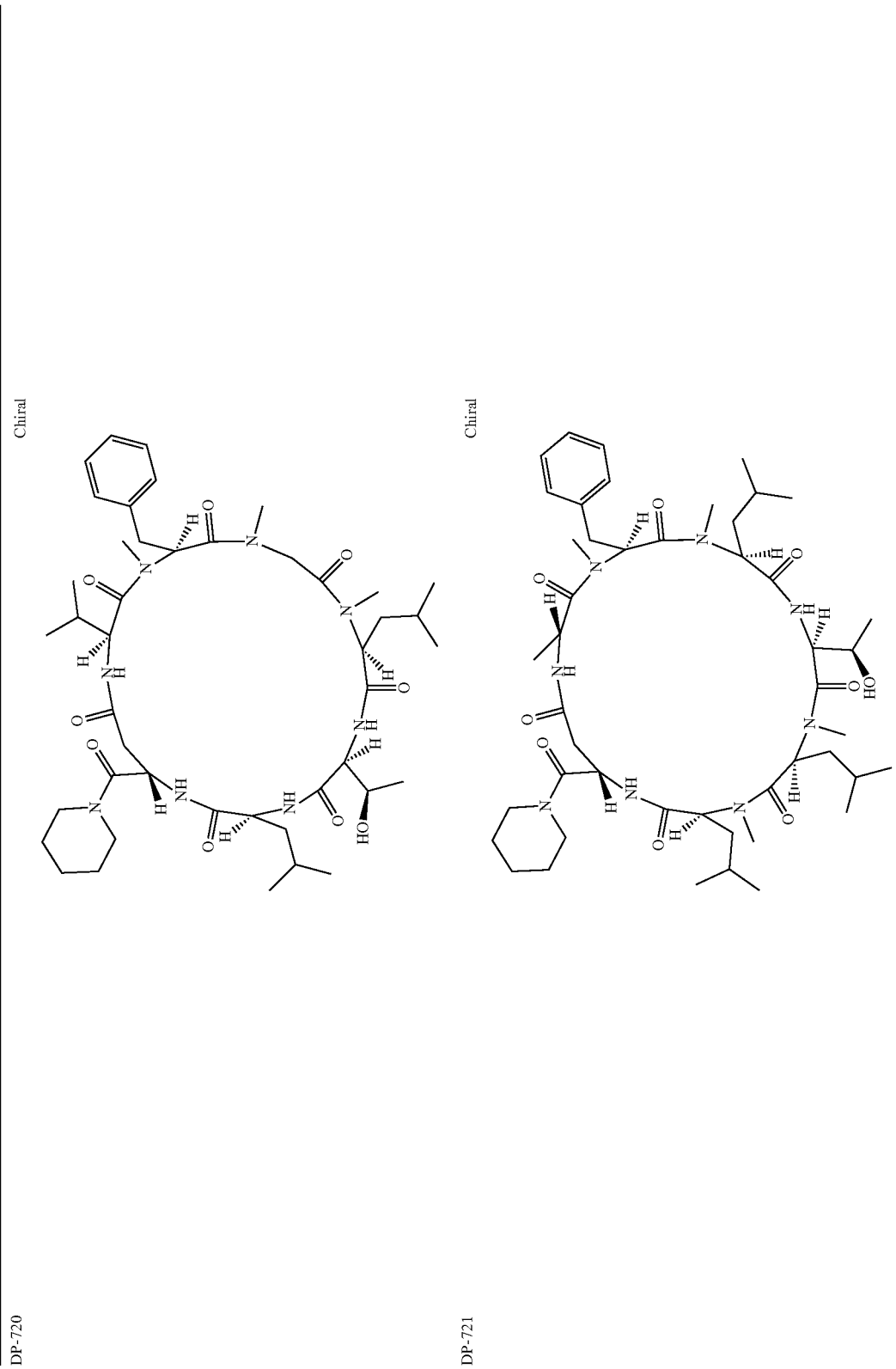

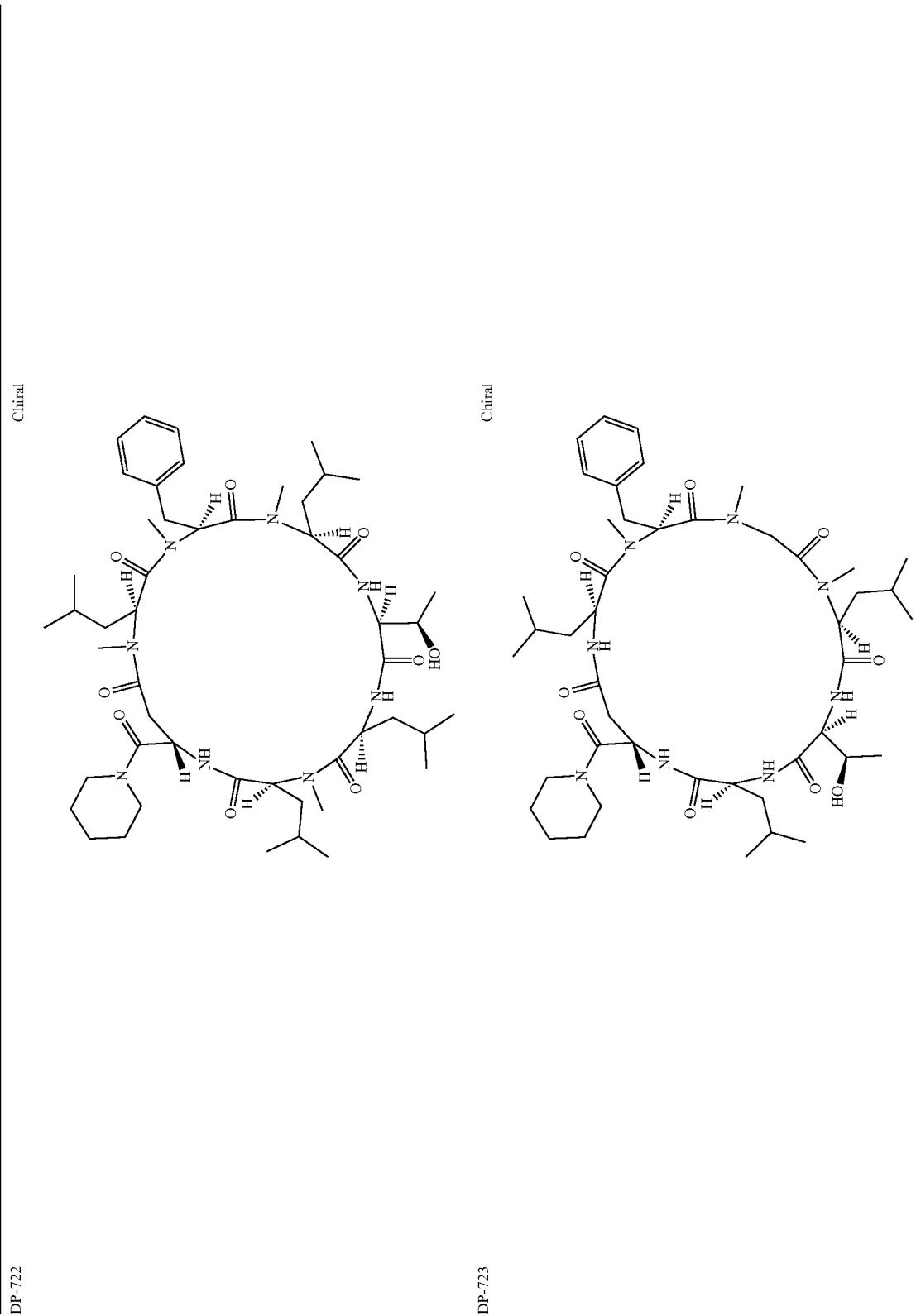

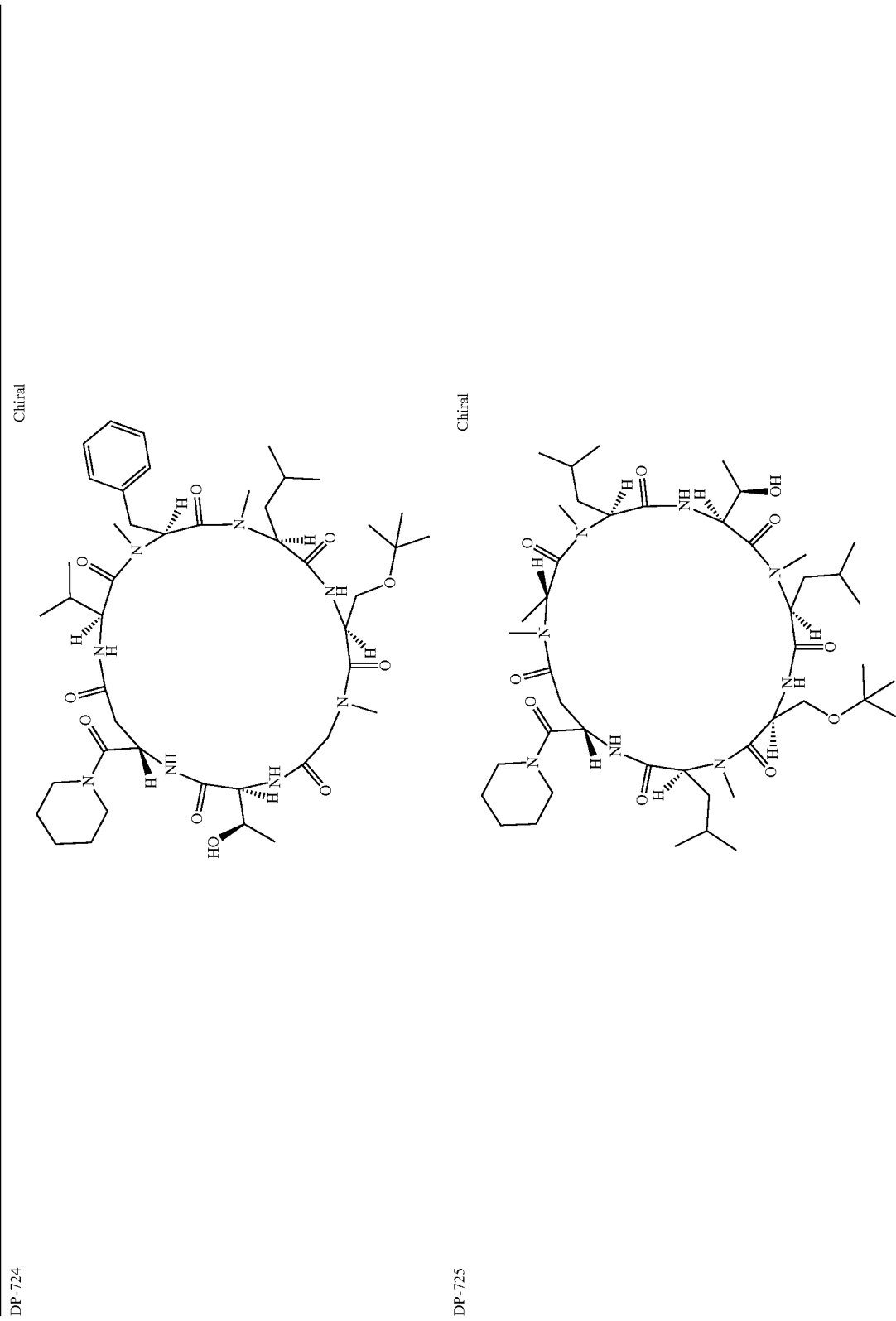

TABLE 11-3-1-continued
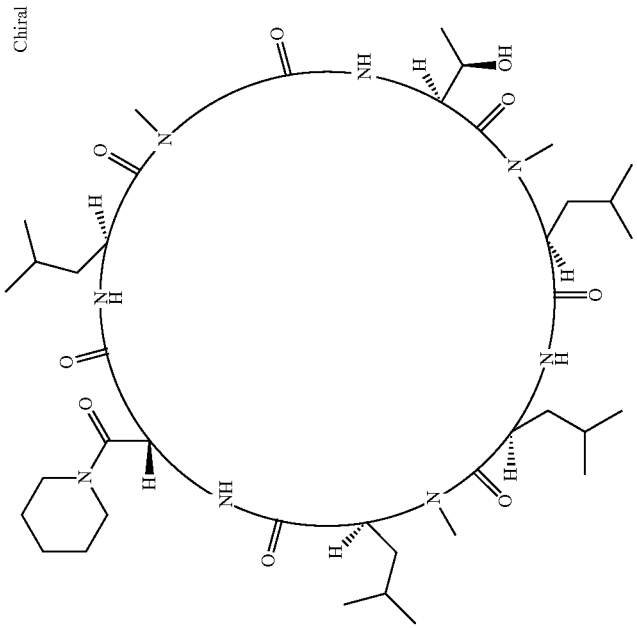
DP-726

TABLE 11-3-1-continued
DP-727
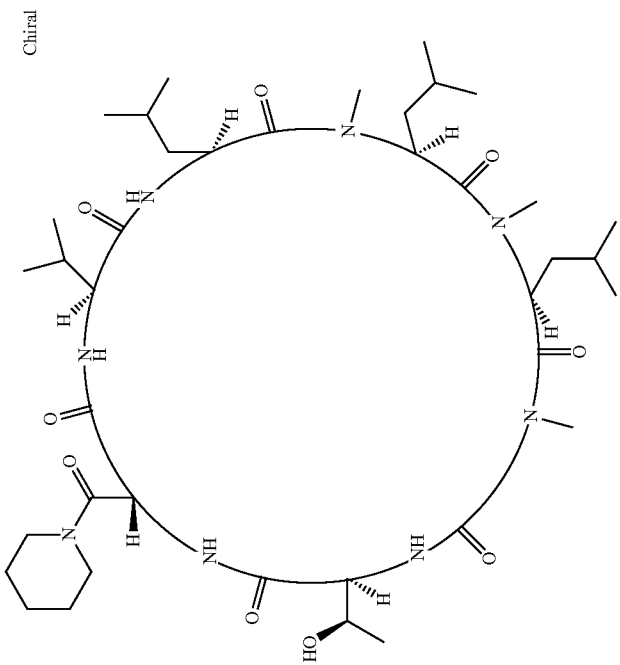

TABLE 11-3-1-continued
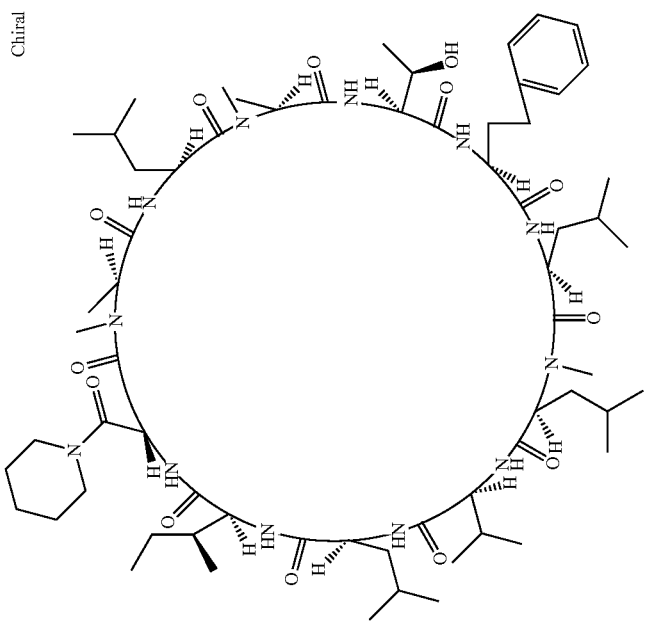
DP-728

TABLE 11-3-1-continued
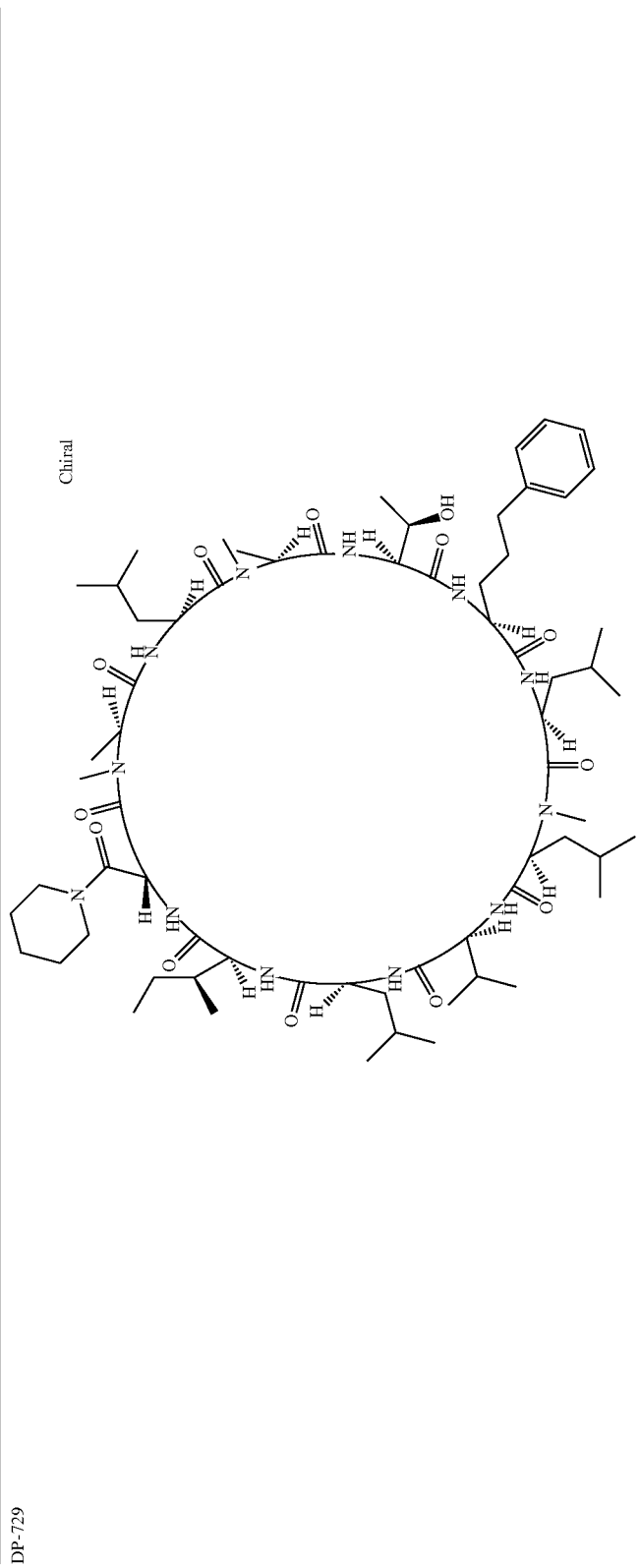
DP-729

TABLE 11-3-1-continued
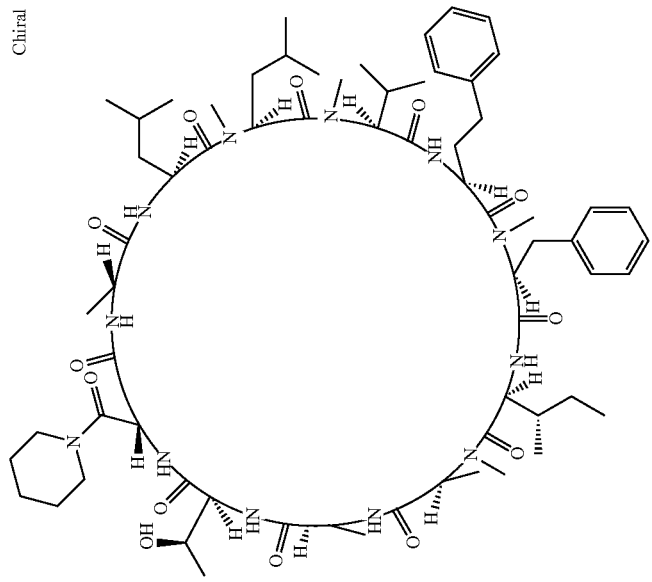
DP-730

TABLE 11-3-1-continued
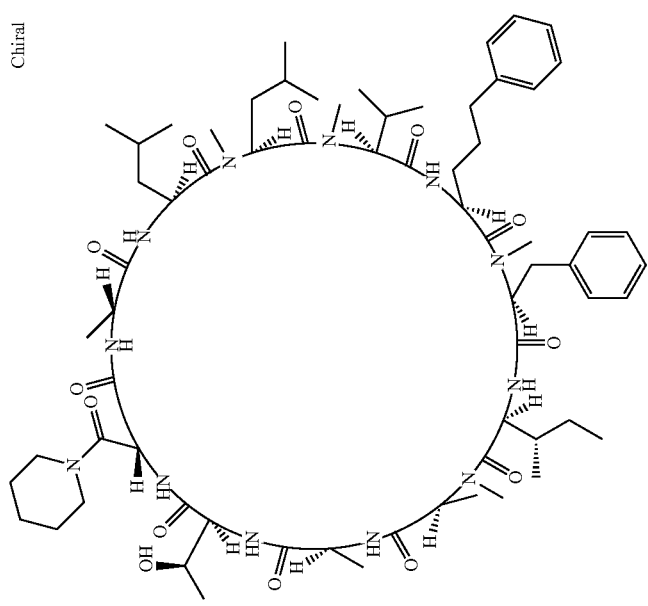
DP-731

TABLE 11-3-1-continued
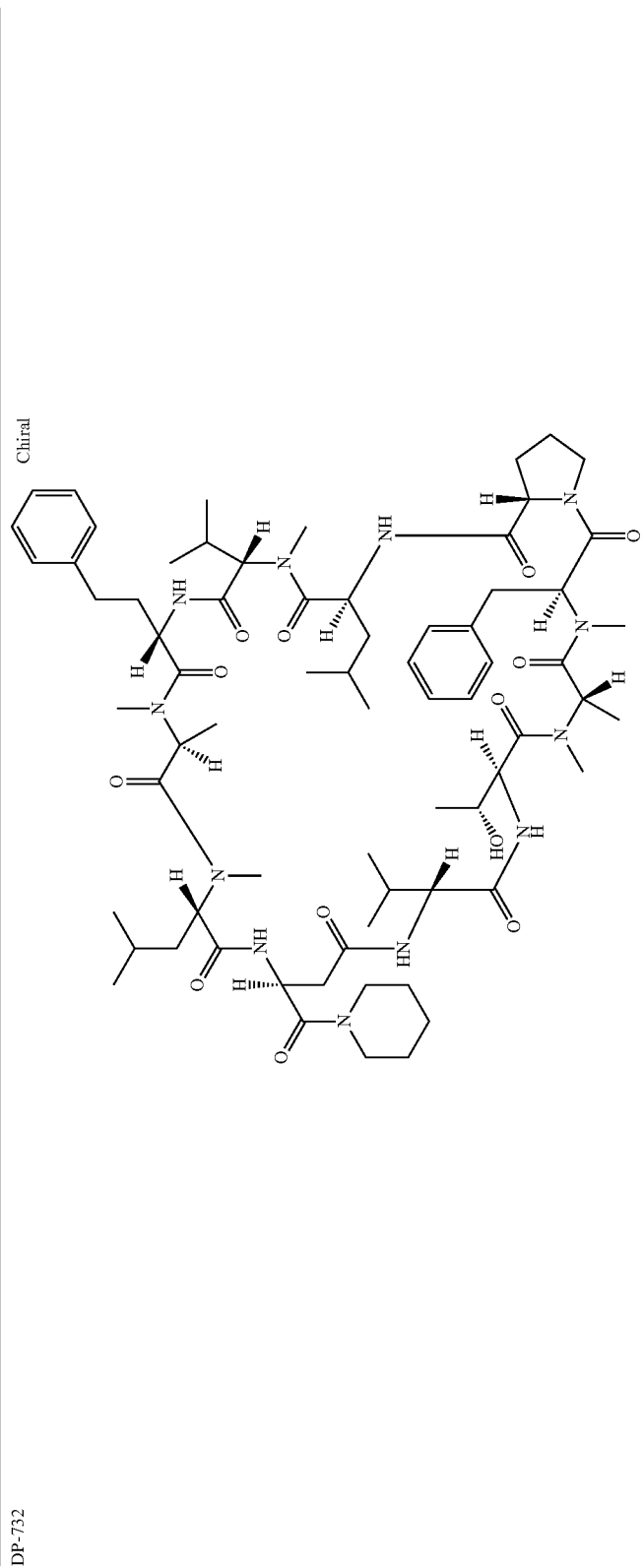
DP-732

TABLE 11-3-1-continued
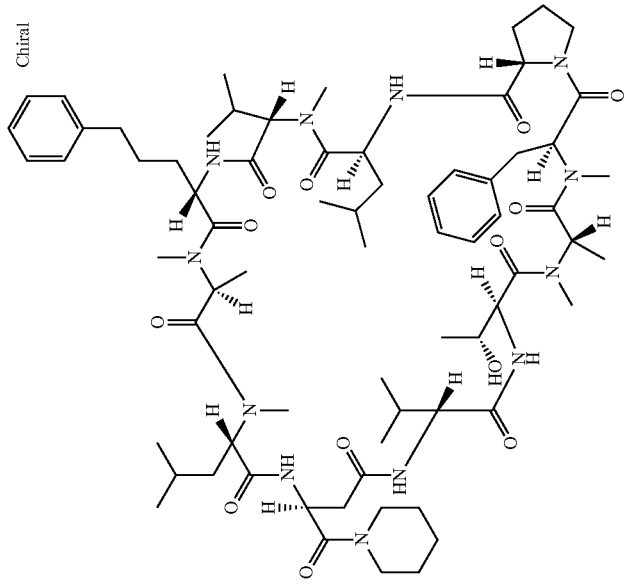
DP-733

TABLE 11-3-1-continued
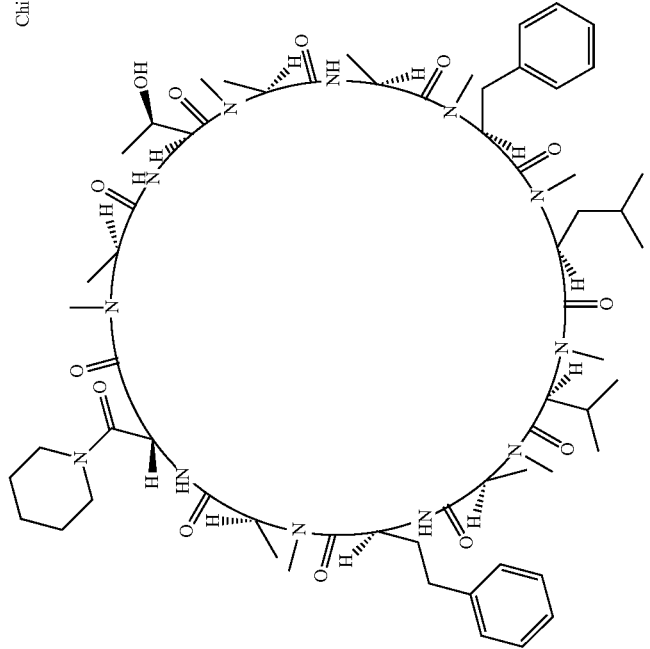
DP-734

TABLE 11-3-1-continued
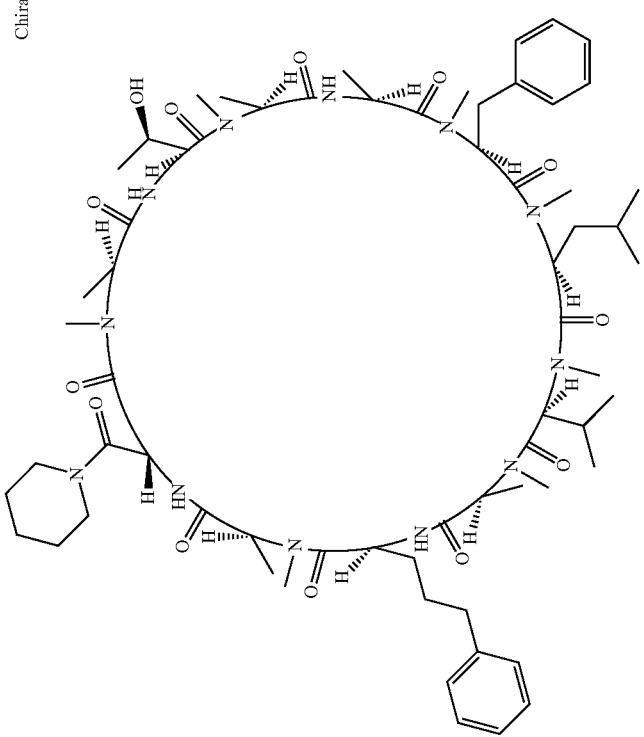
DP-735

TABLE 11-3-1-continued
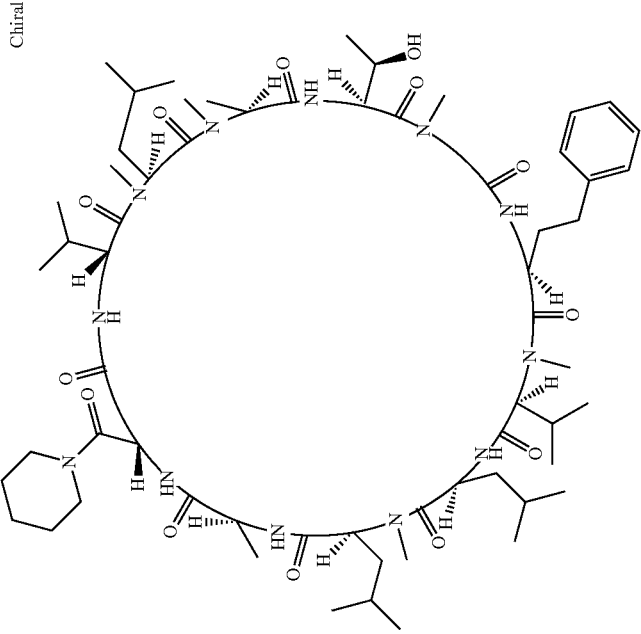
DP-736

TABLE 11-3-1-continued
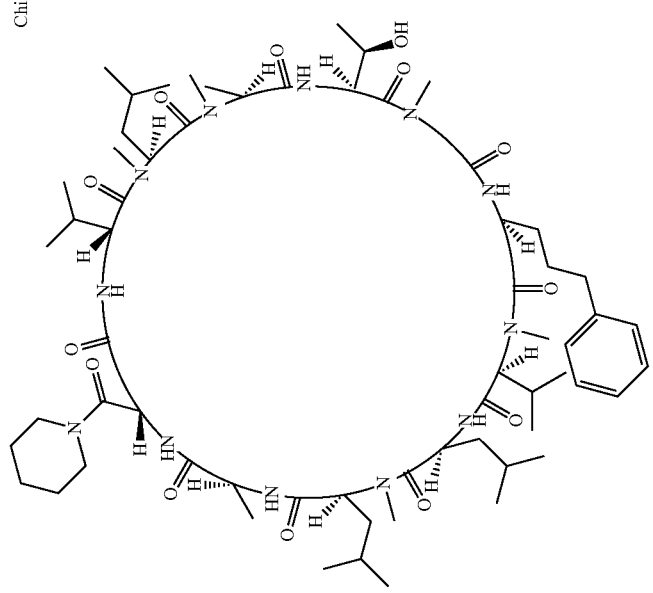
DP-737

TABLE 11-3-1-continued
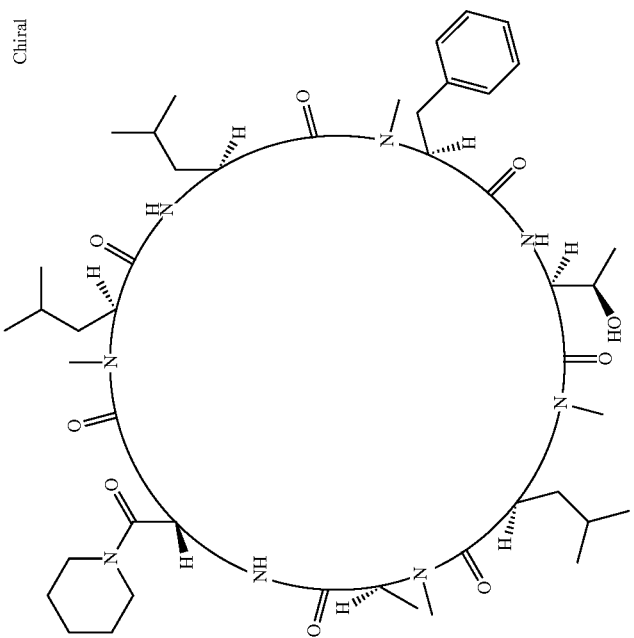
DP-738

TABLE 11-3-1-continued
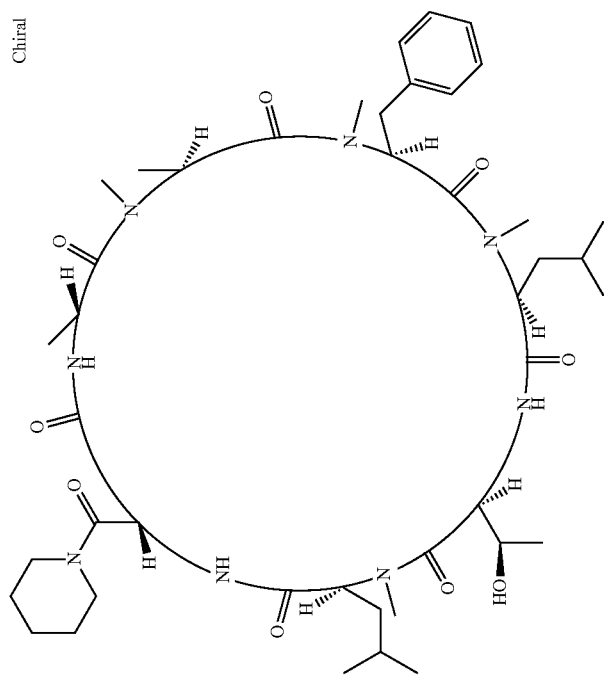
DP-739

TABLE 11-3-1-continued
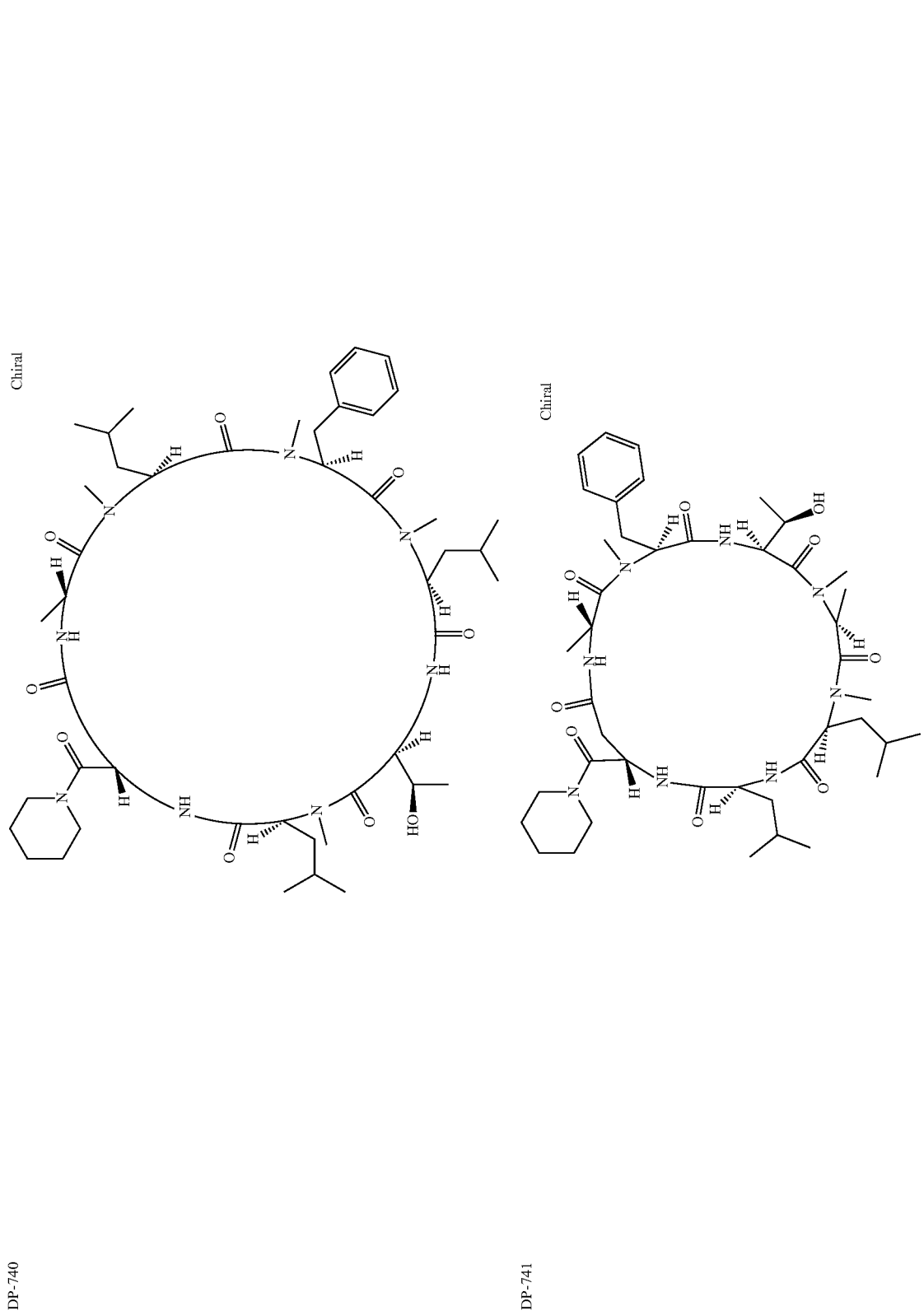
DP-740
DP-741

TABLE 11-3-1-continued
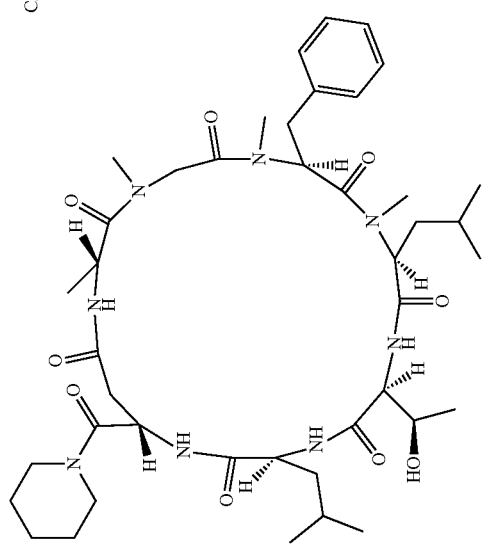
DP-742
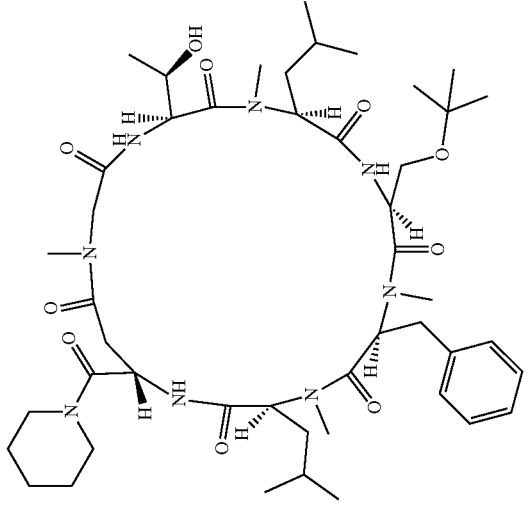
DP-743

TABLE 11-3-1-continued
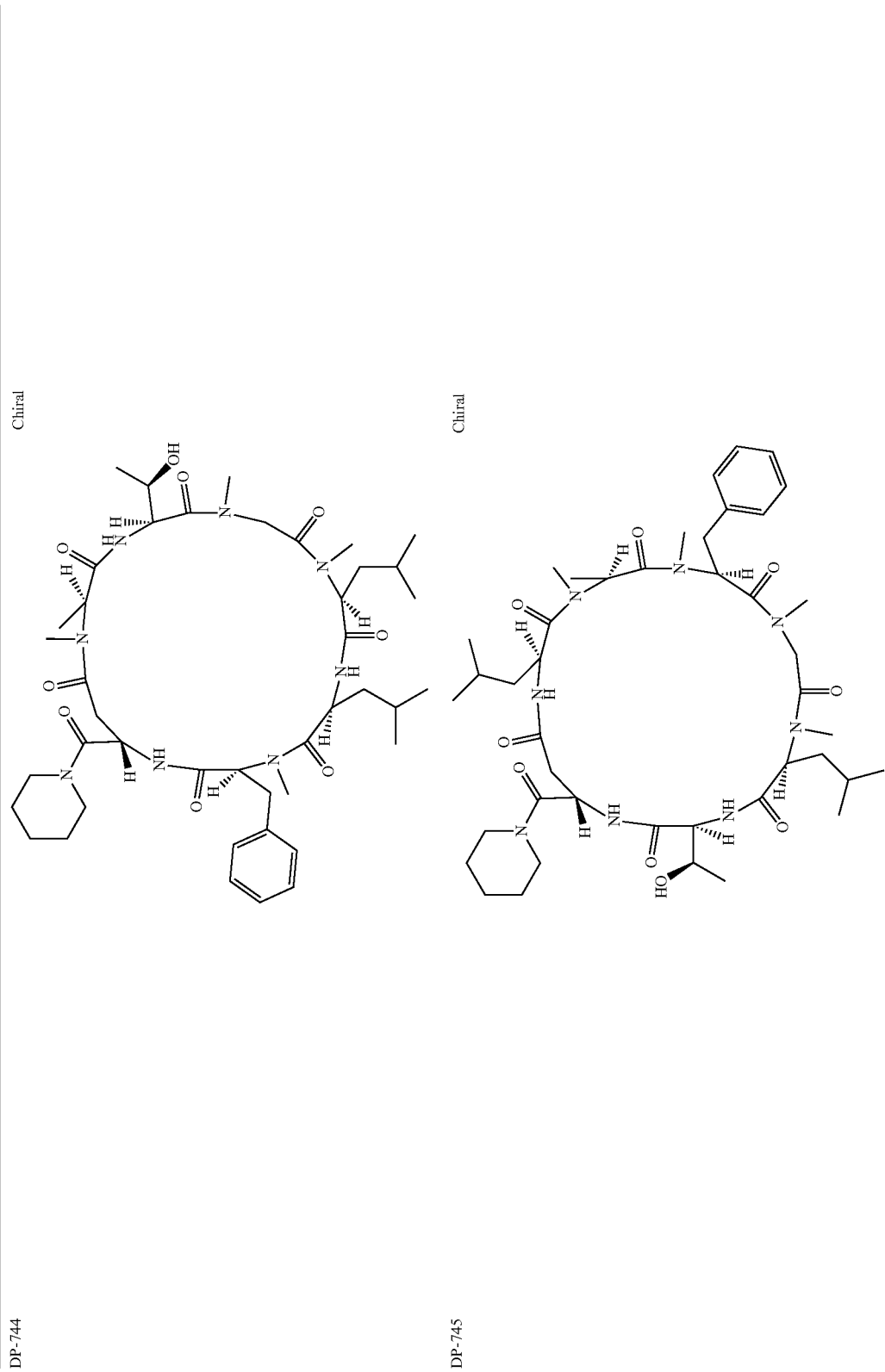
DP-744
DP-745

TABLE 11-3-1-continued
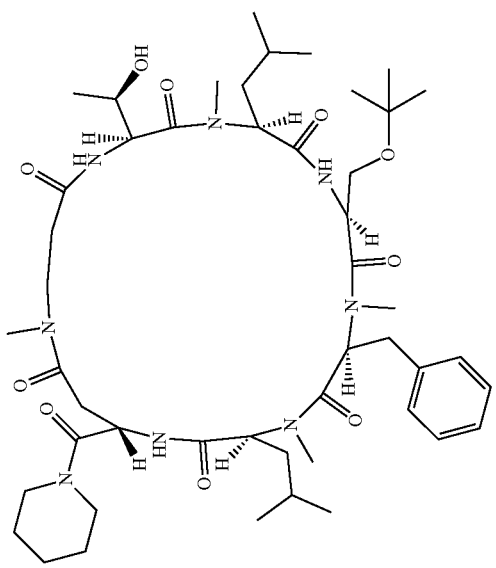
DP-746
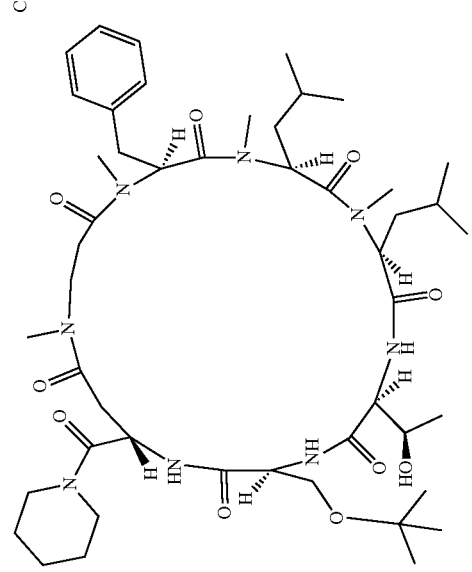
DP-747

TABLE 11-3-1-continued
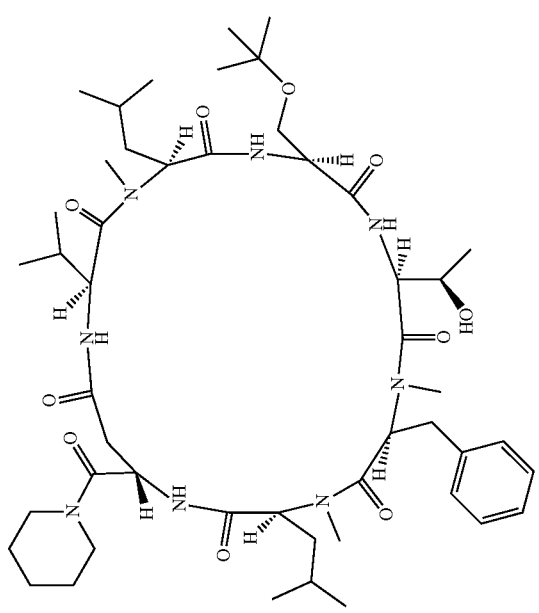
DP-748
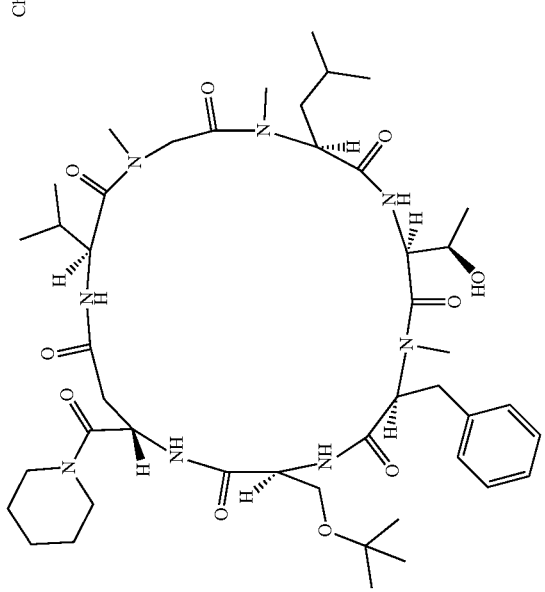
DP-749

TABLE 11-3-1-continued
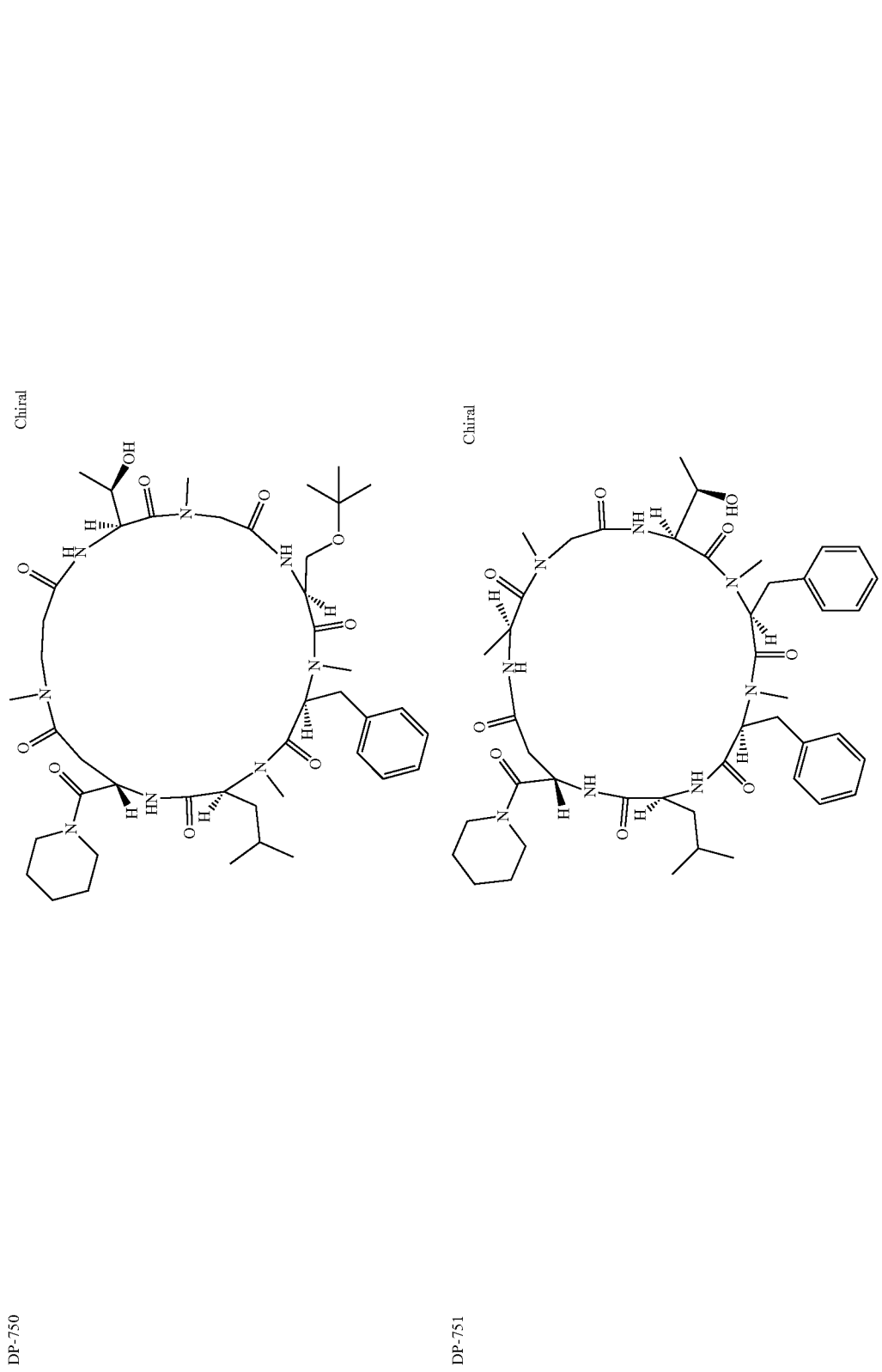
DP-750
DP-751

TABLE 11-3-1-continued
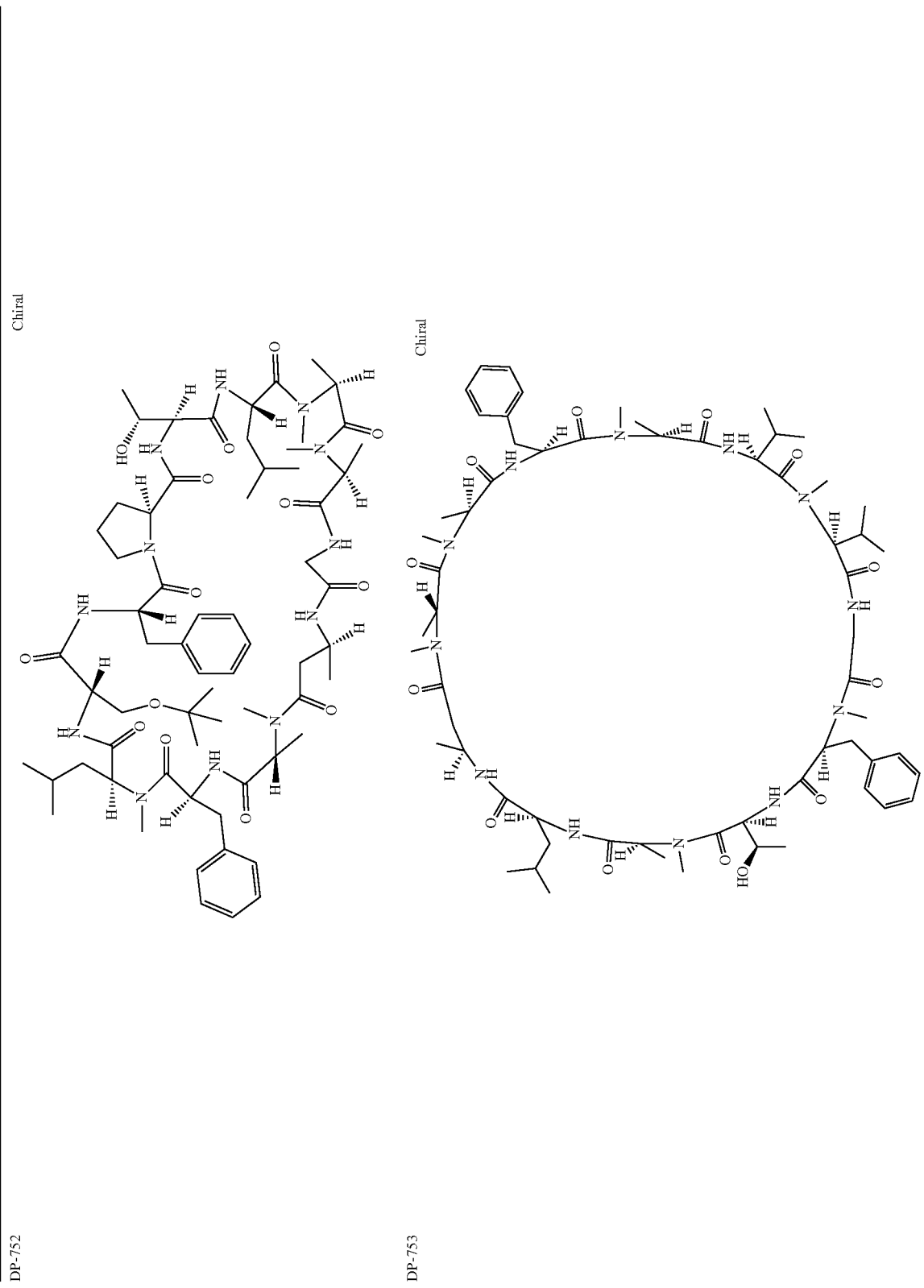
DP-752
DP-753

TABLE 11-3-1-continued
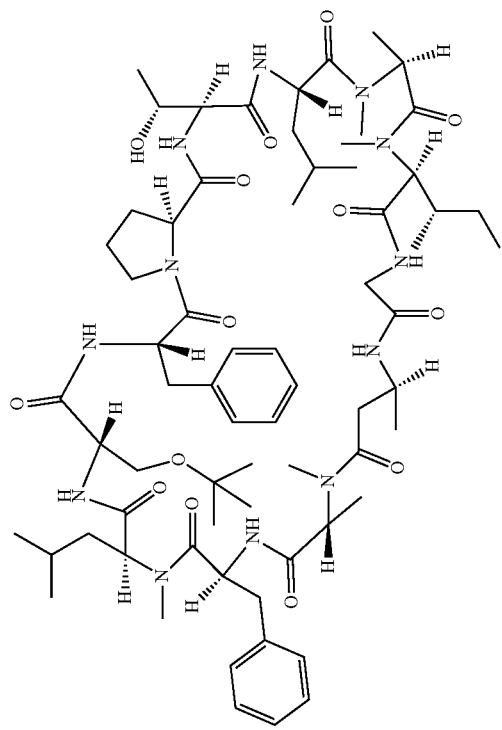
DP-754

TABLE 11-3-1-continued
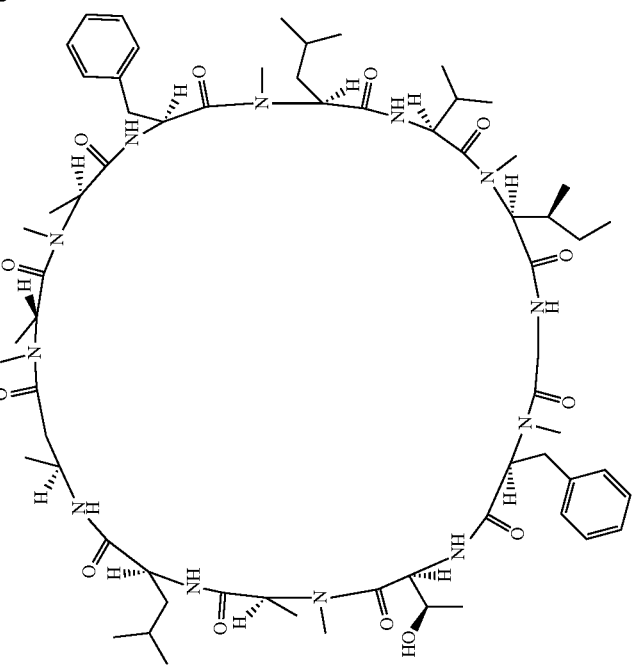
DP-755

TABLE 11-3-1-continued
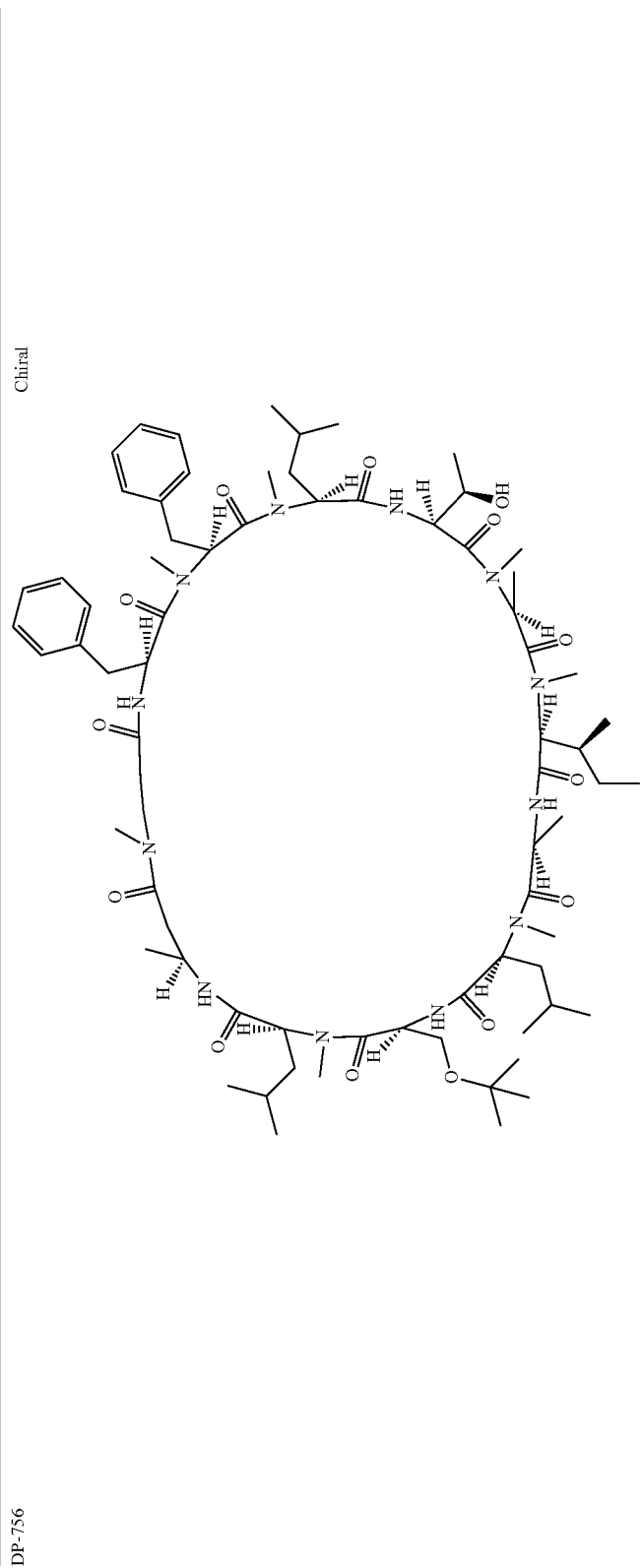
DP-756

TABLE 11-3-1-continued
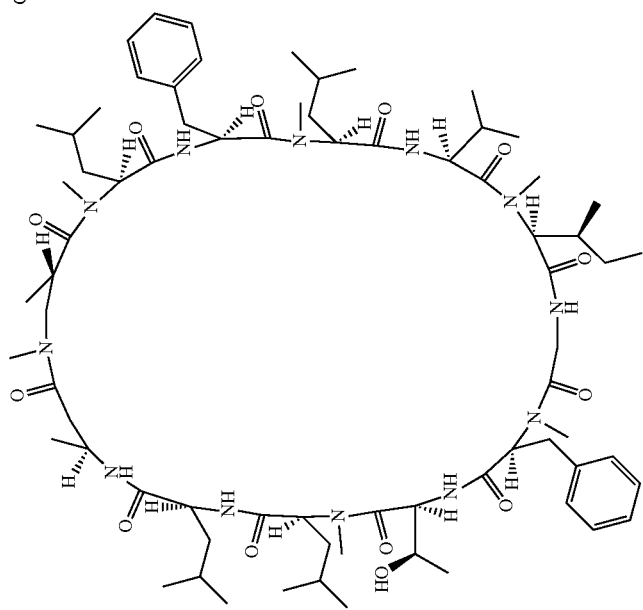
DP-757

TABLE 11-3-1-continued
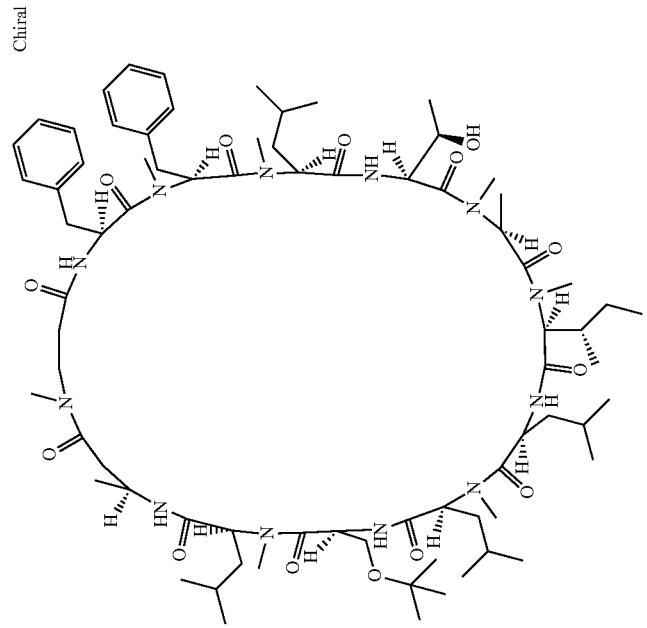
DP-758

TABLE 11-3-1-continued
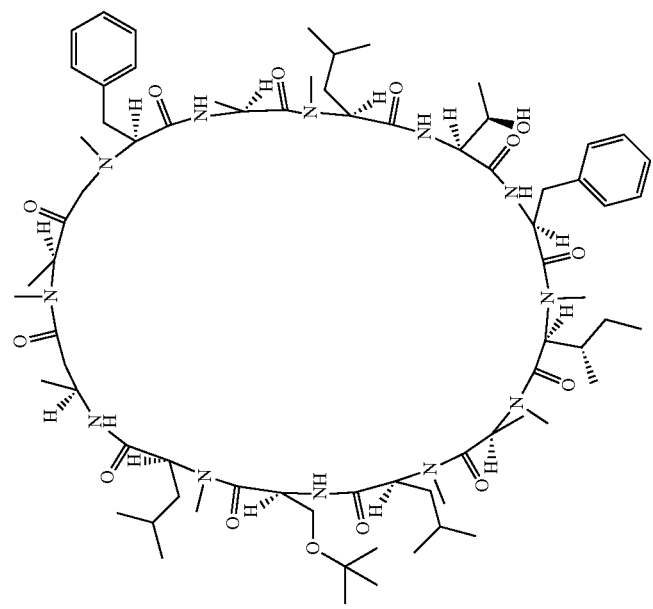
DP-759

TABLE 11-3-1-continued
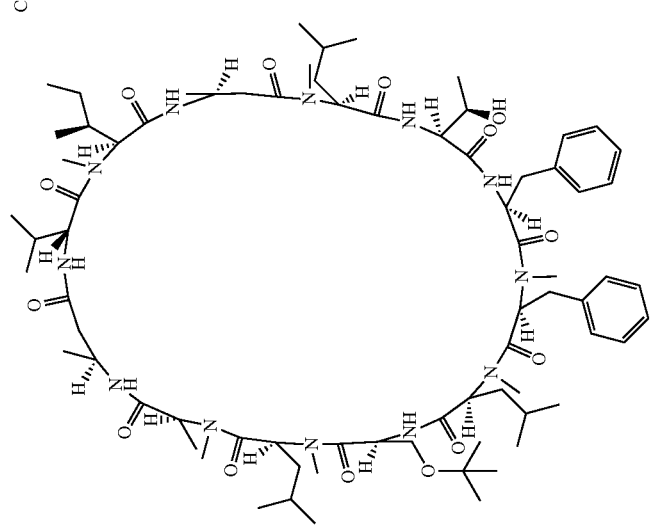
DP-760

TABLE 11-3-1-continued
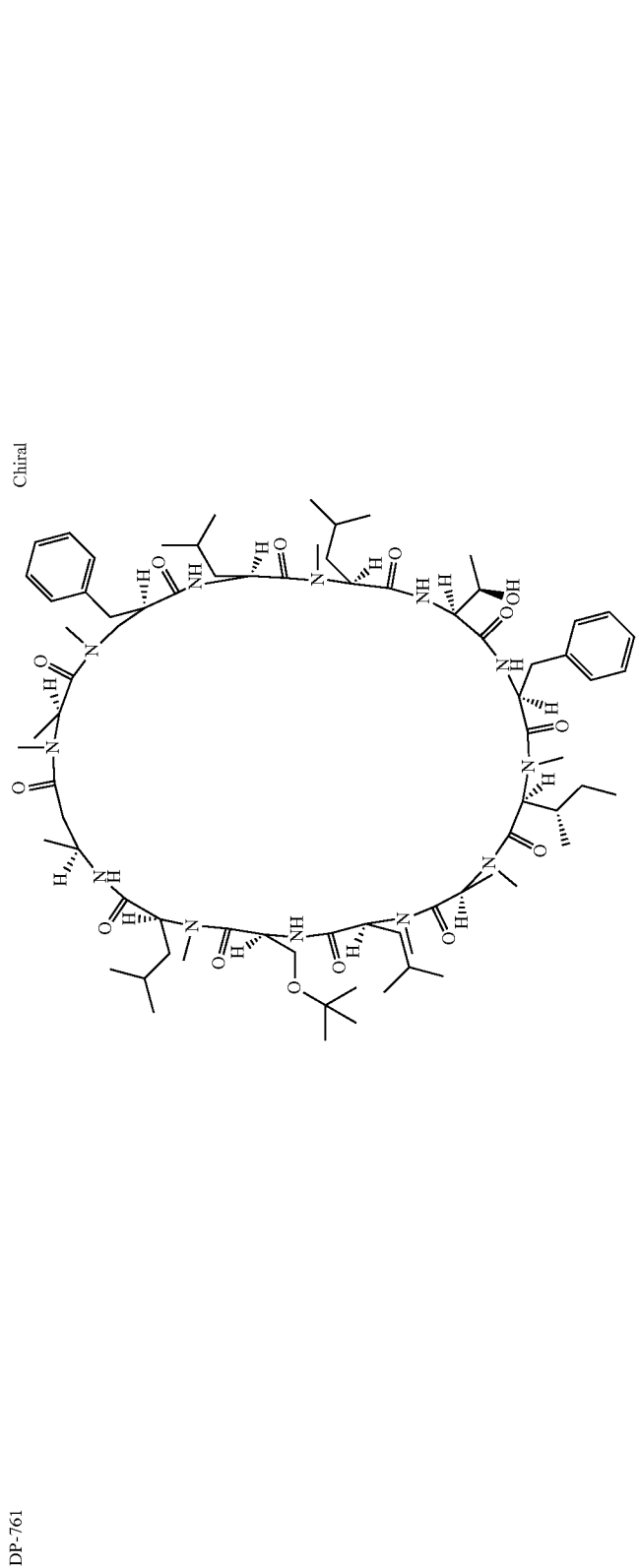
DP-761

TABLE 11-3-1-continued
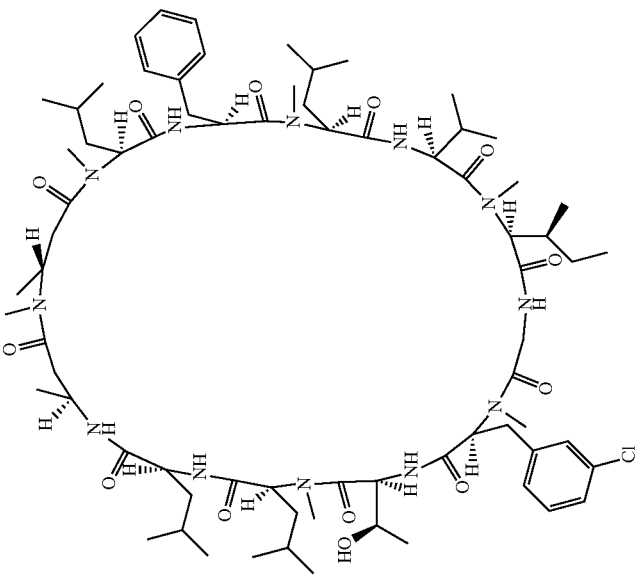
DP-762

TABLE 11-3-1-continued
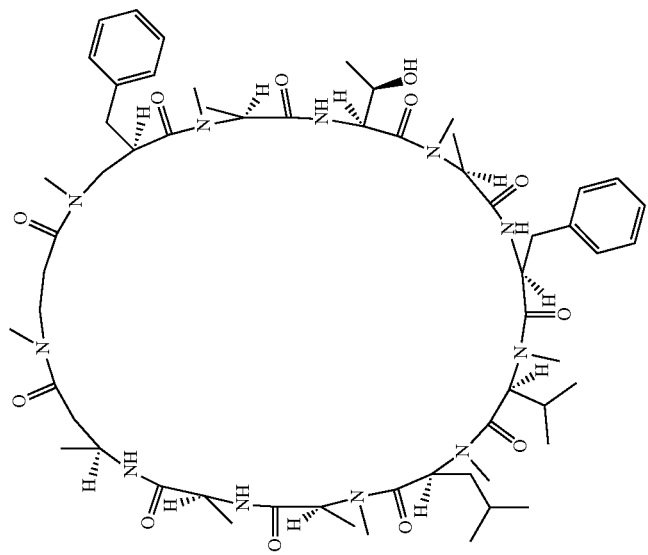
DP-763

TABLE 11-3-1-continued
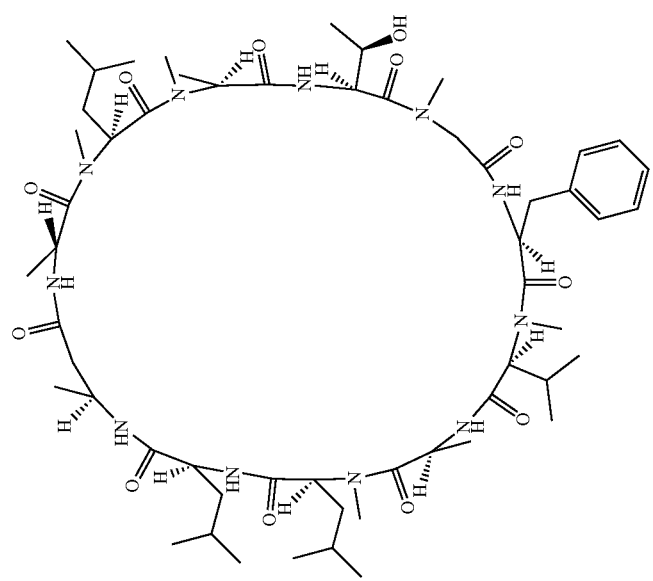
DP-764

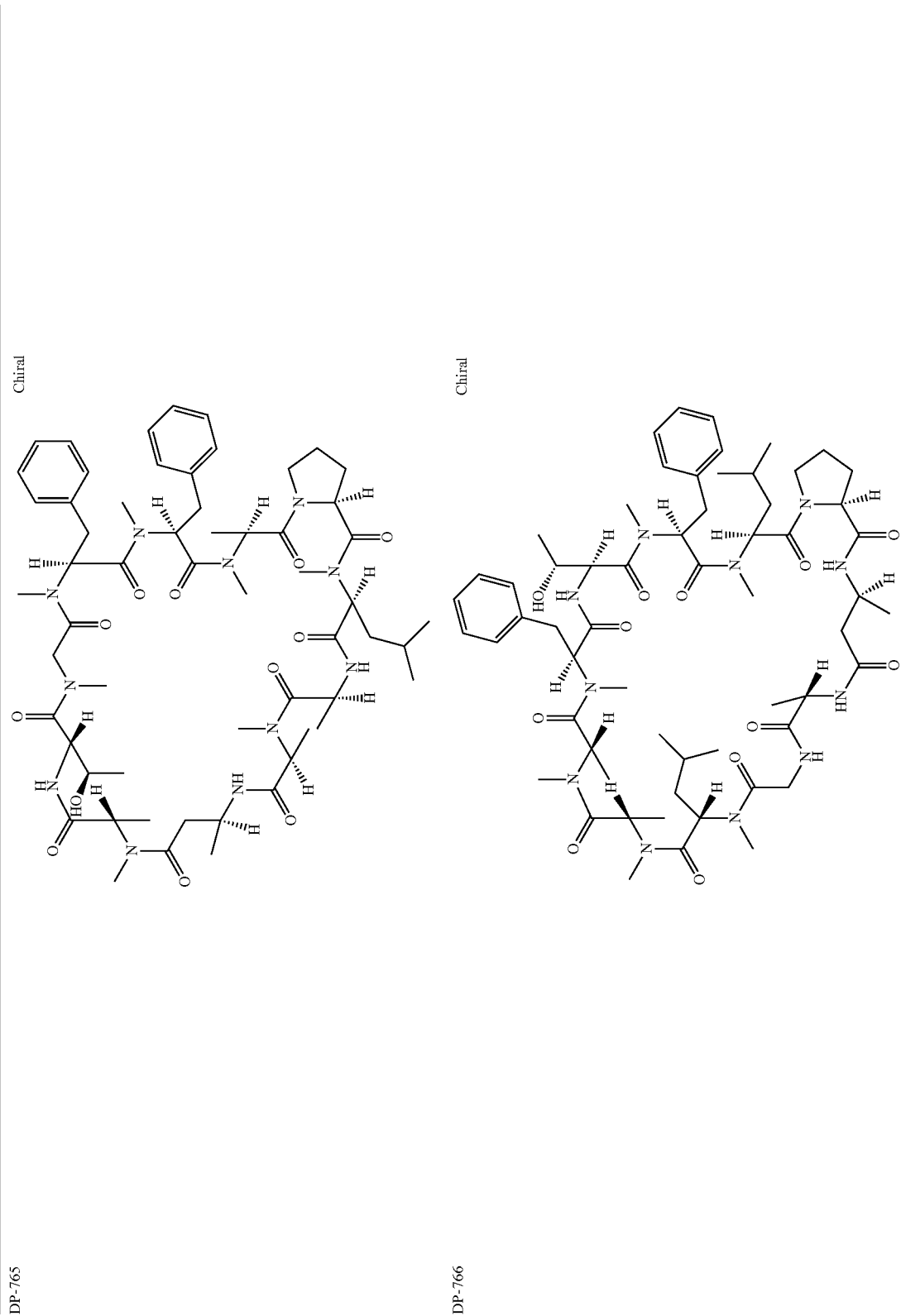

TABLE 11-3-1-continued
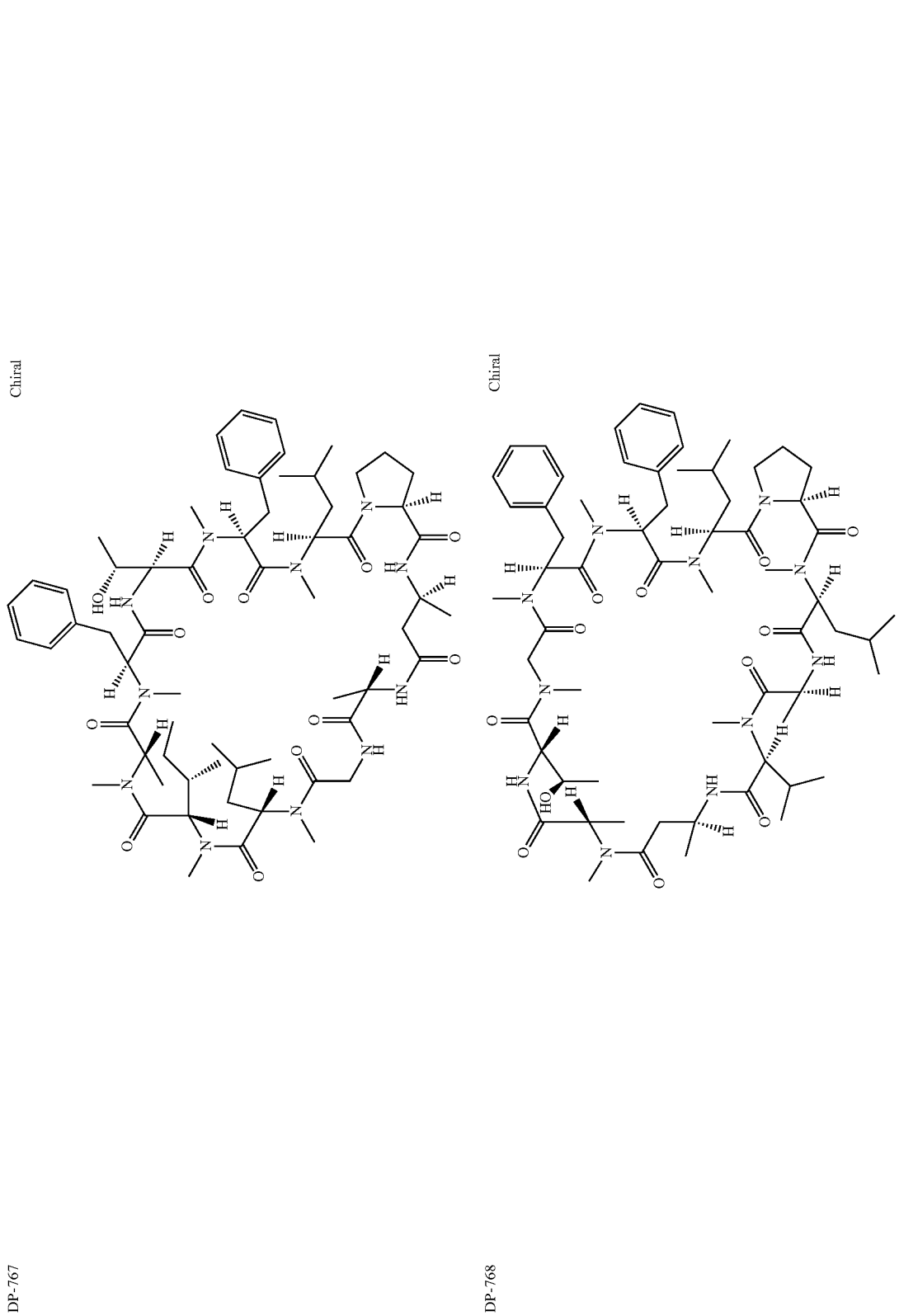
DP-767
DP-768

TABLE 11-3-1-continued
DP-769

TABLE 11-3-1-continued
DP-770
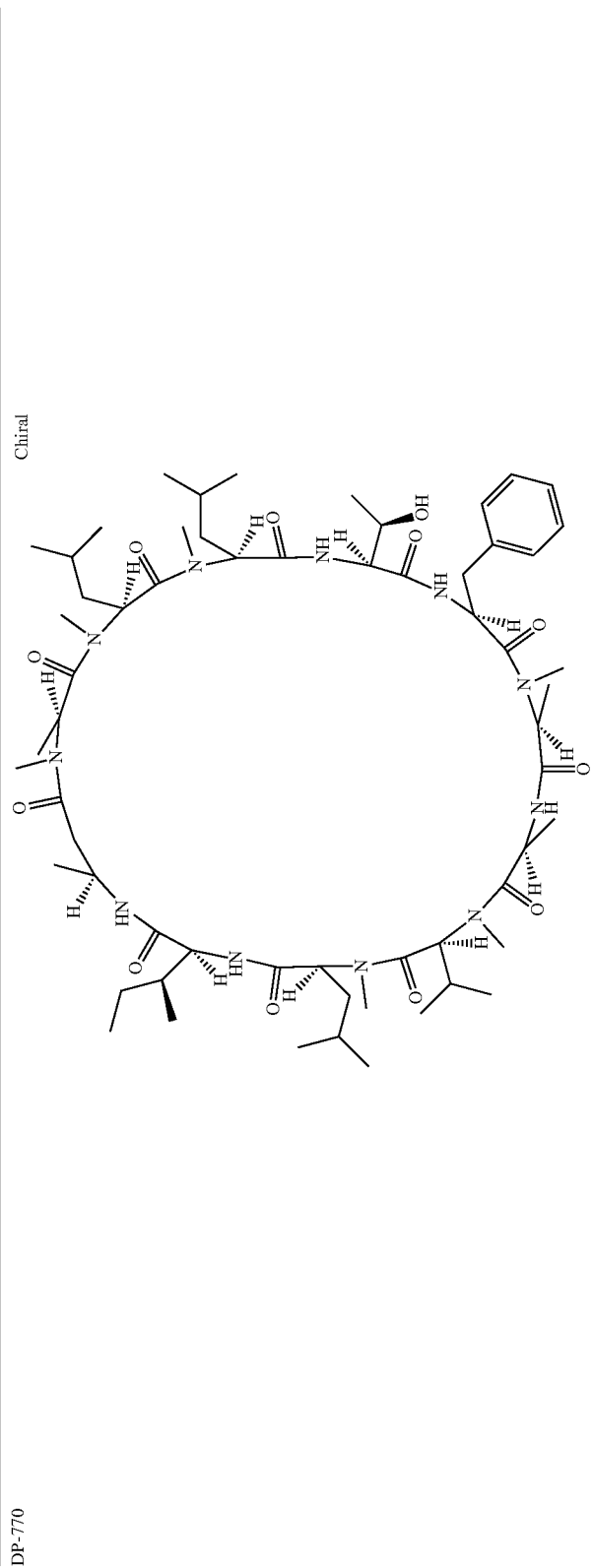

TABLE 11-3-1-continued
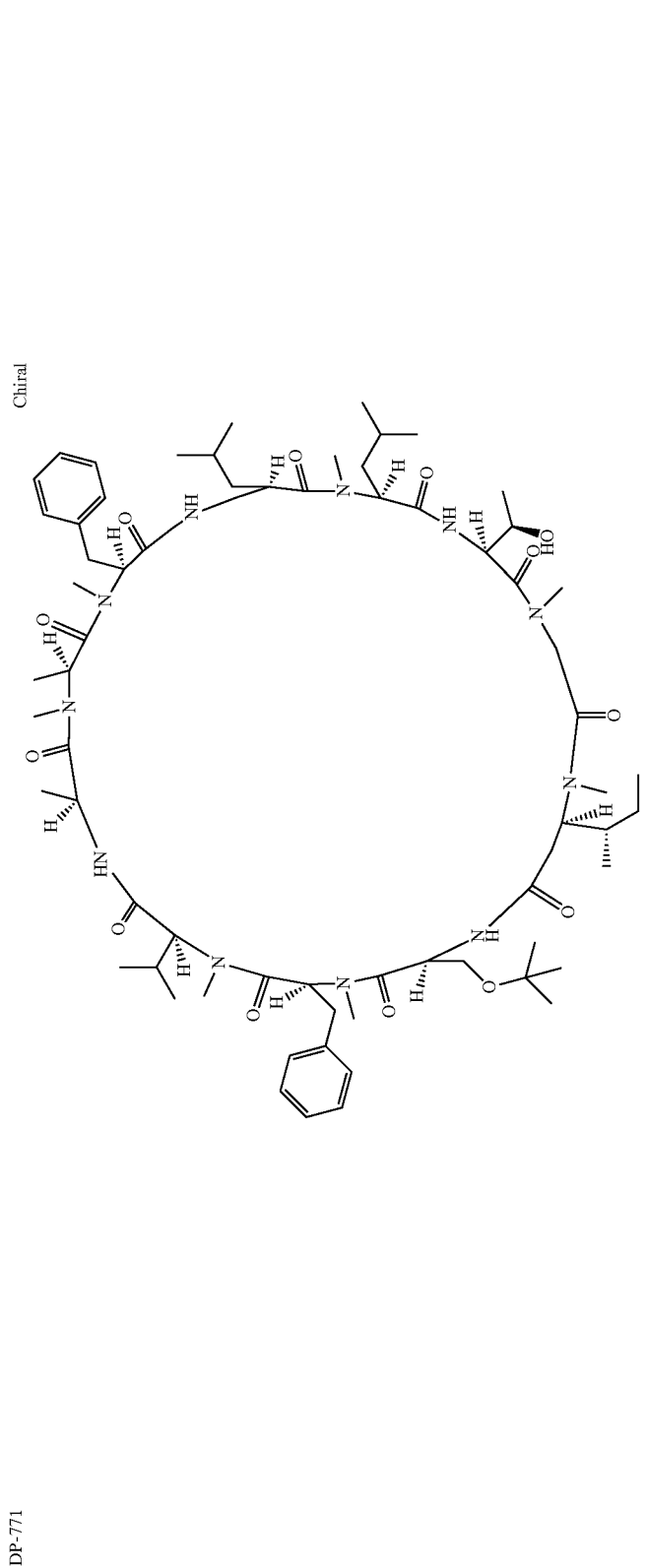
DP-771

TABLE 11-3-1-continued
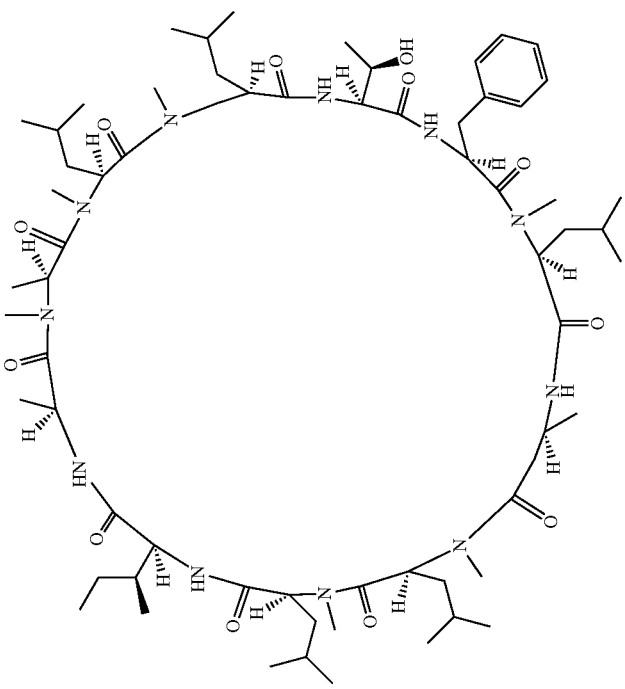
DP-772

TABLE 11-3-1-continued
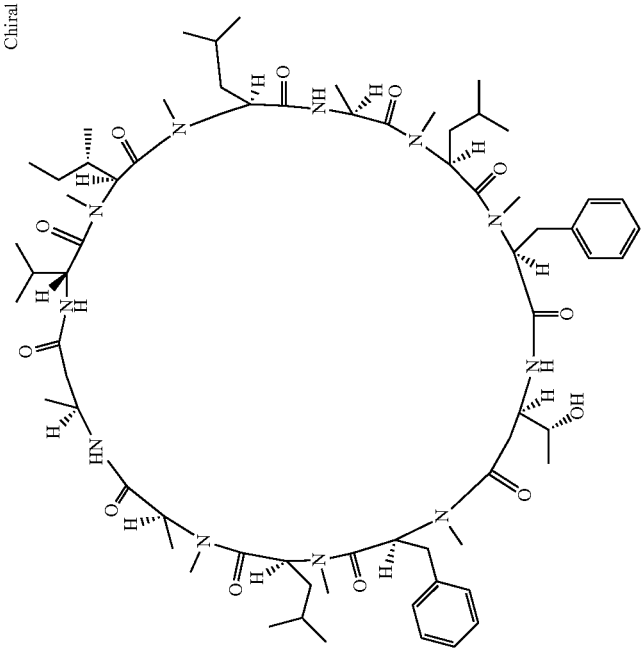
DP-773

TABLE 11-3-1-continued
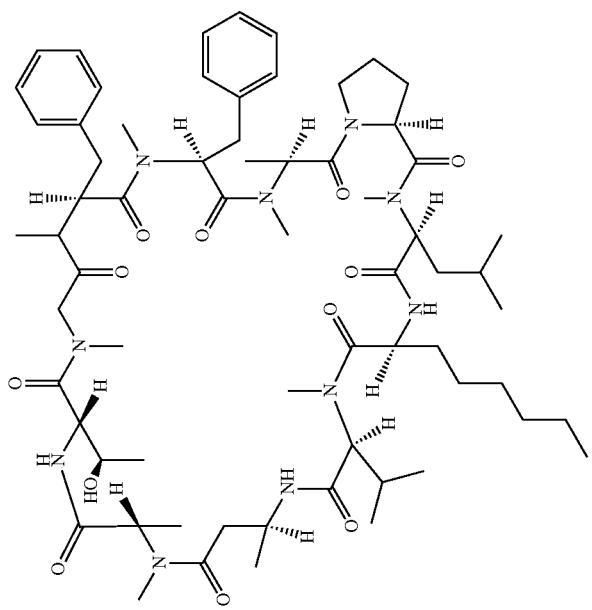
DP-774

TABLE 11-3-1-continued
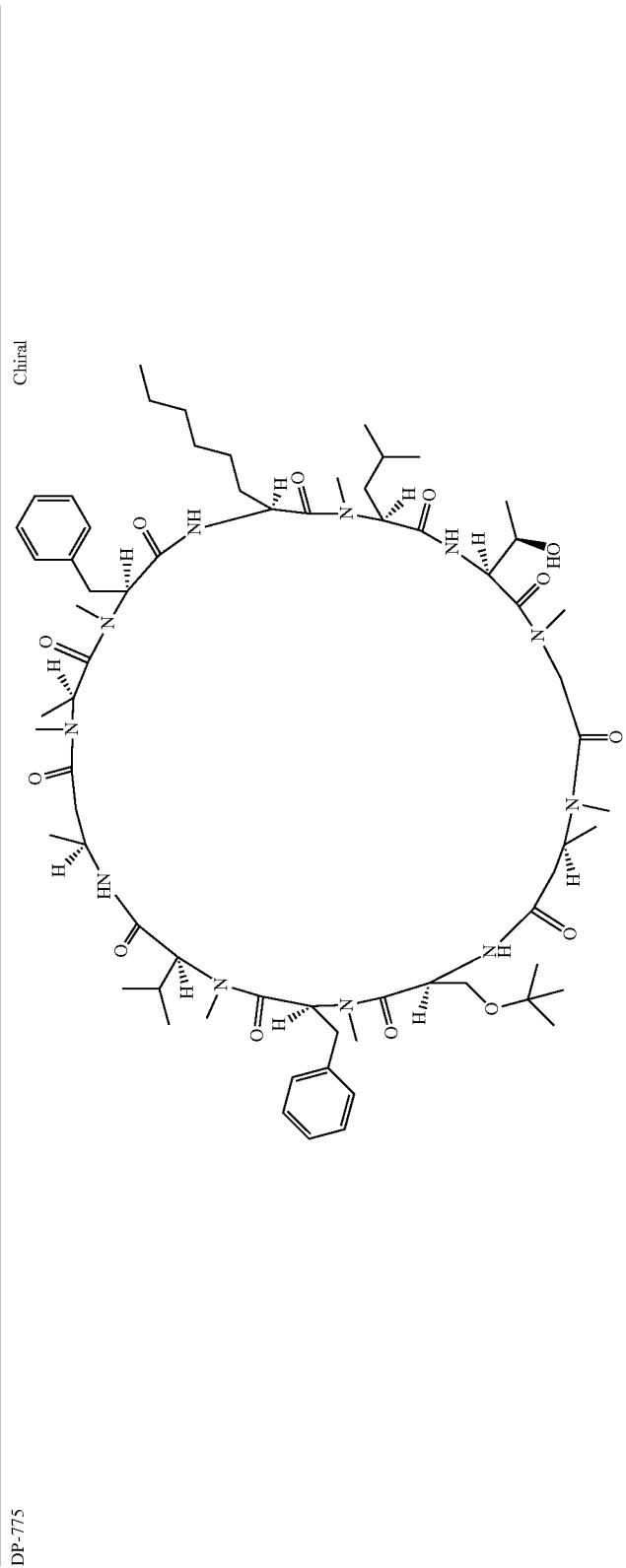
DP-775

TABLE 11-3-1-continued
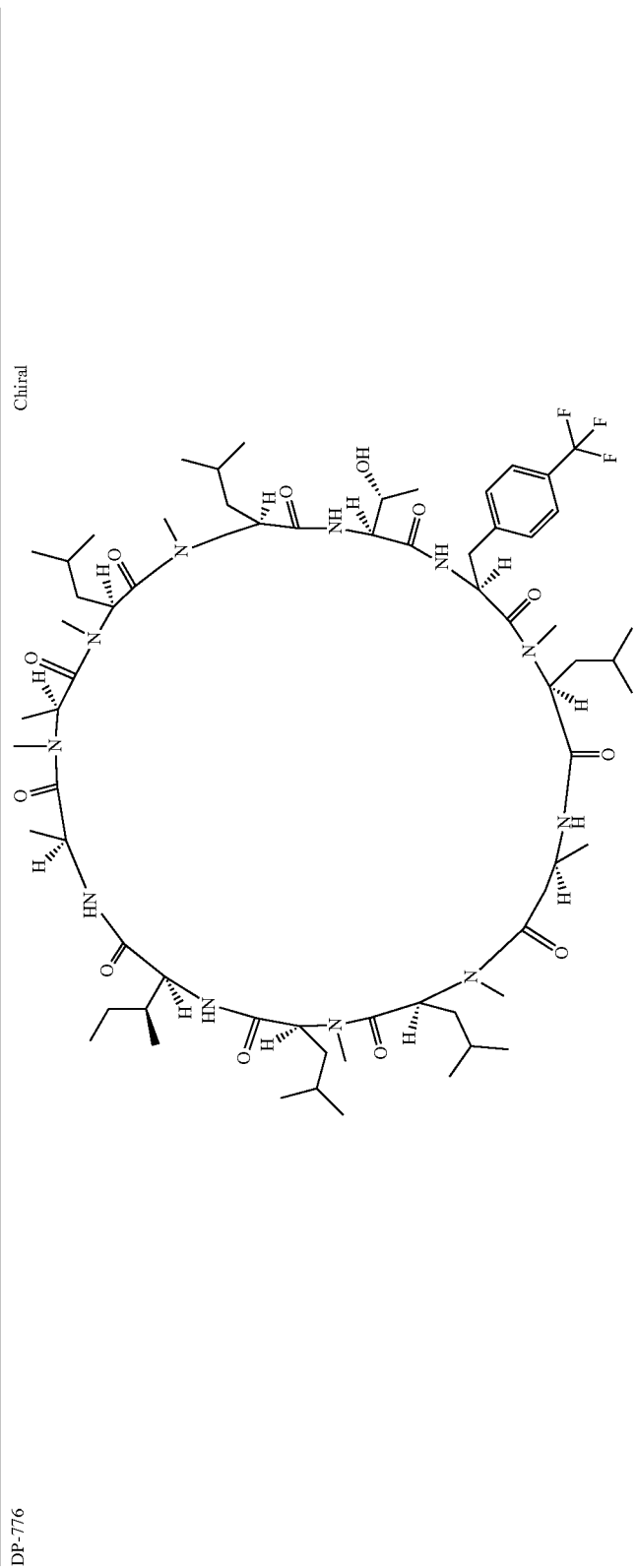
DP-776

TABLE 11-3-1-continued
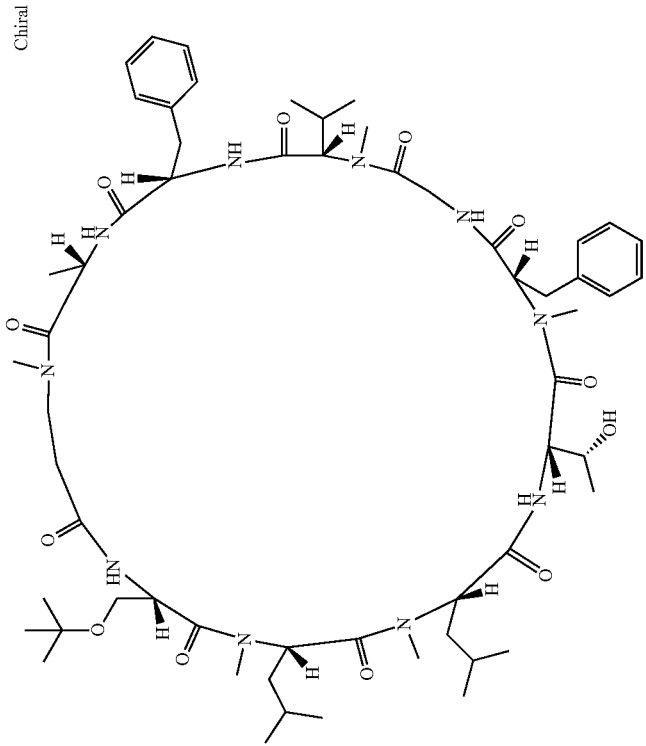
DP-777

TABLE 11-3-1-continued
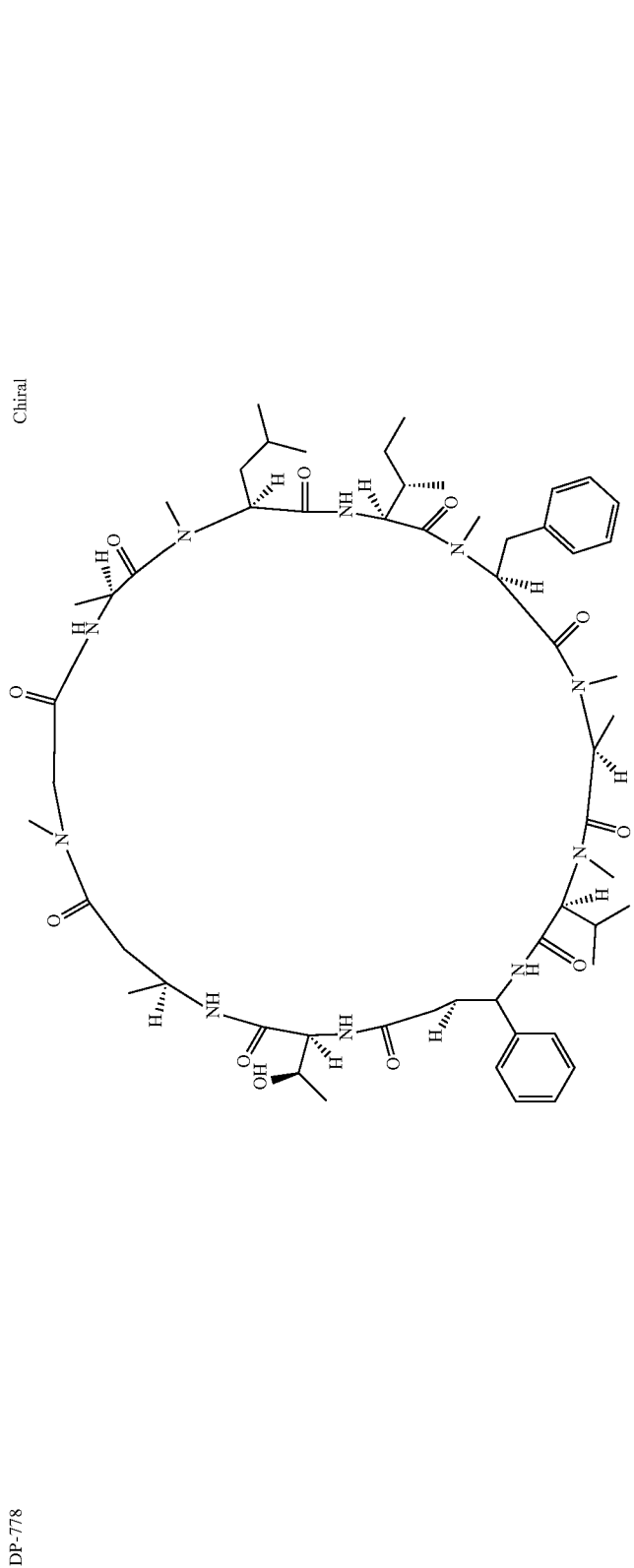
DP-778

TABLE 11-3-1-continued
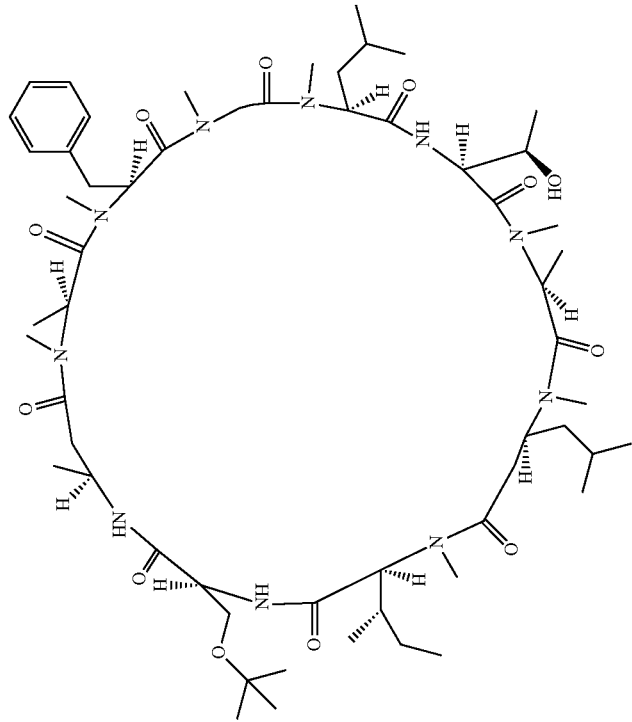
DP-779

TABLE 11-3-1-continued
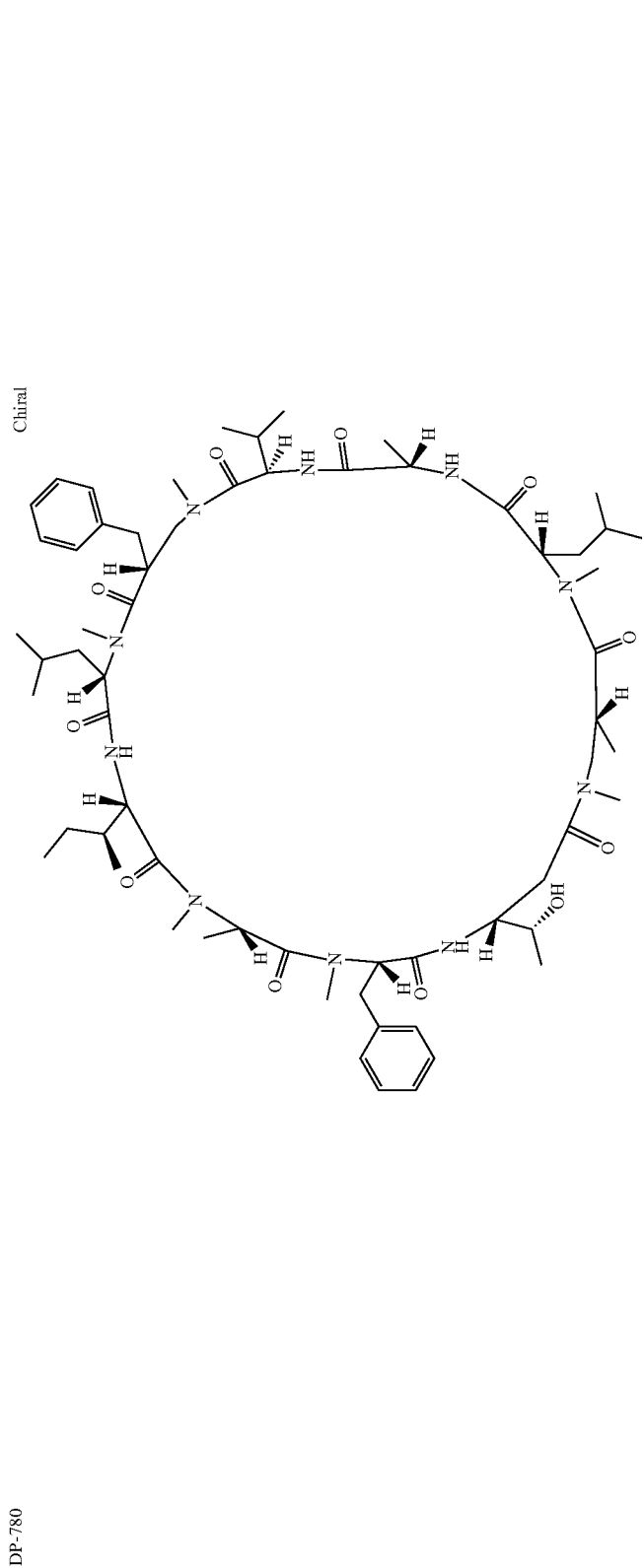
DP-780

TABLE 11-3-1-continued
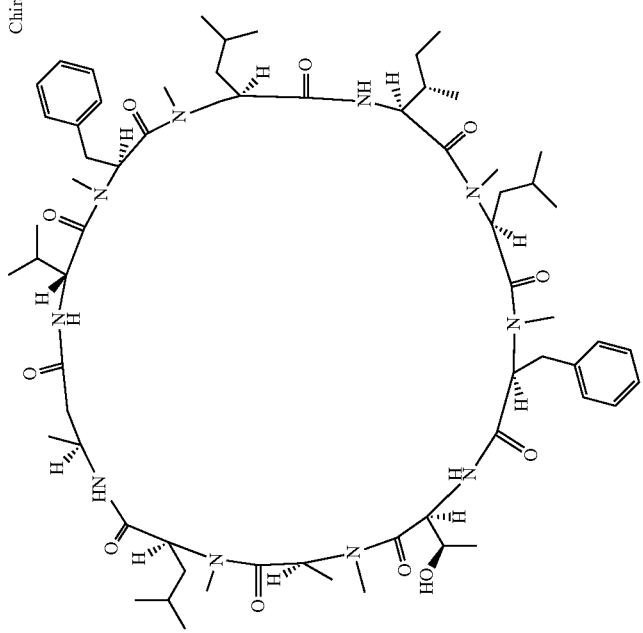
DP-781

TABLE 11-3-1-continued
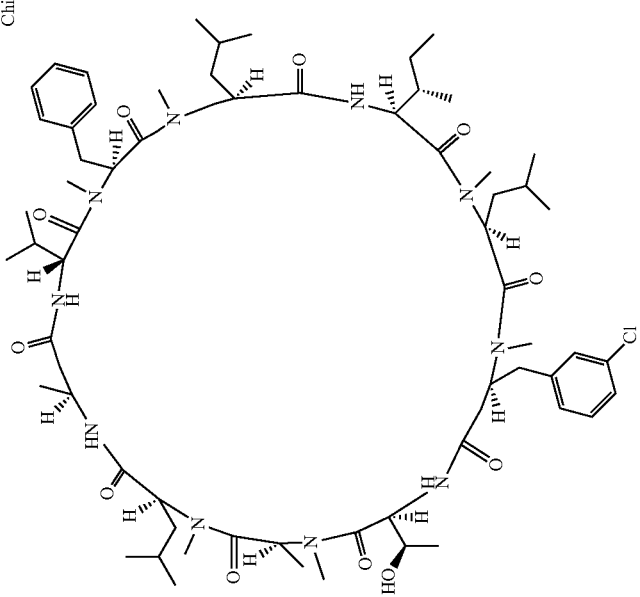
DP-782

TABLE 11-3-1-continued
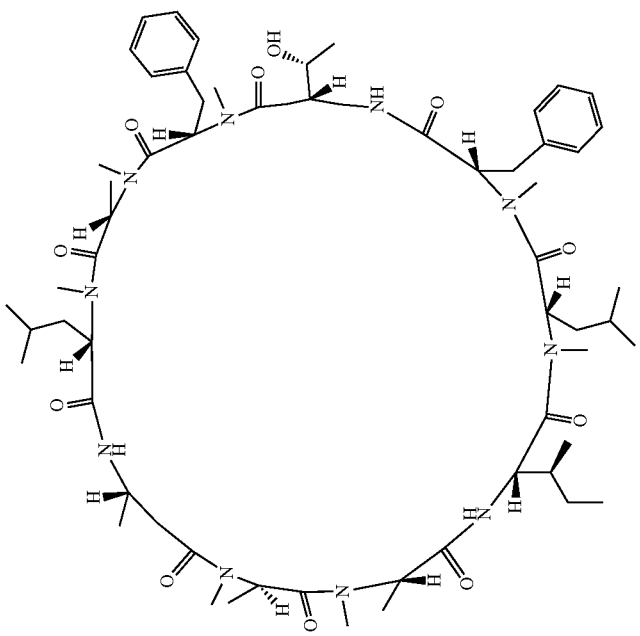
DP-783

TABLE 11-3-1-continued
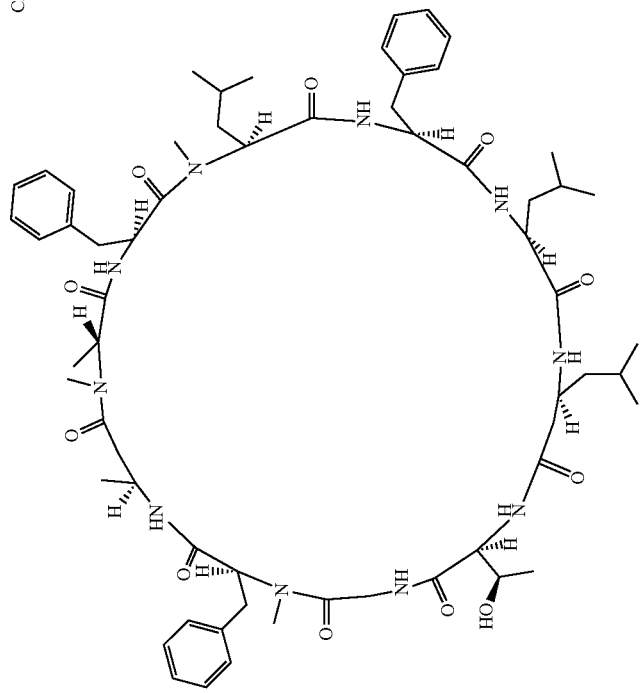
DP-784

TABLE 11-3-1-continued
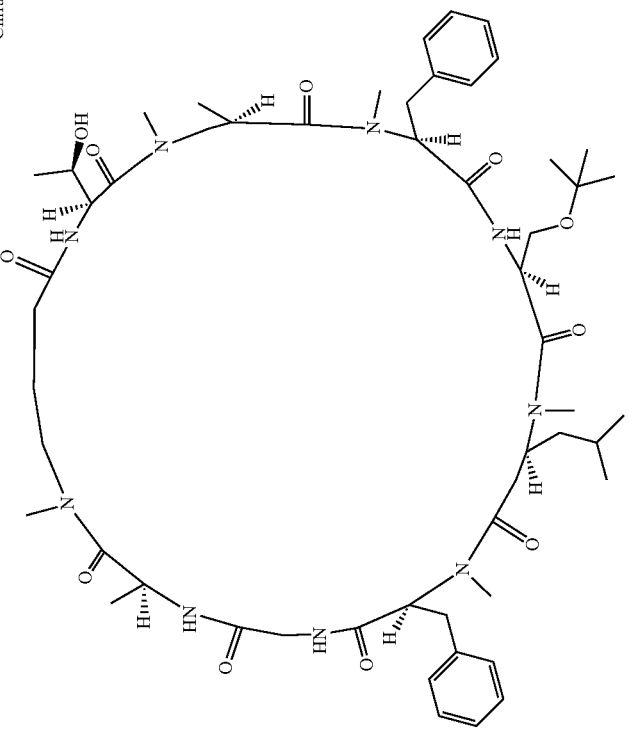
DP-785

TABLE 11-3-1-continued
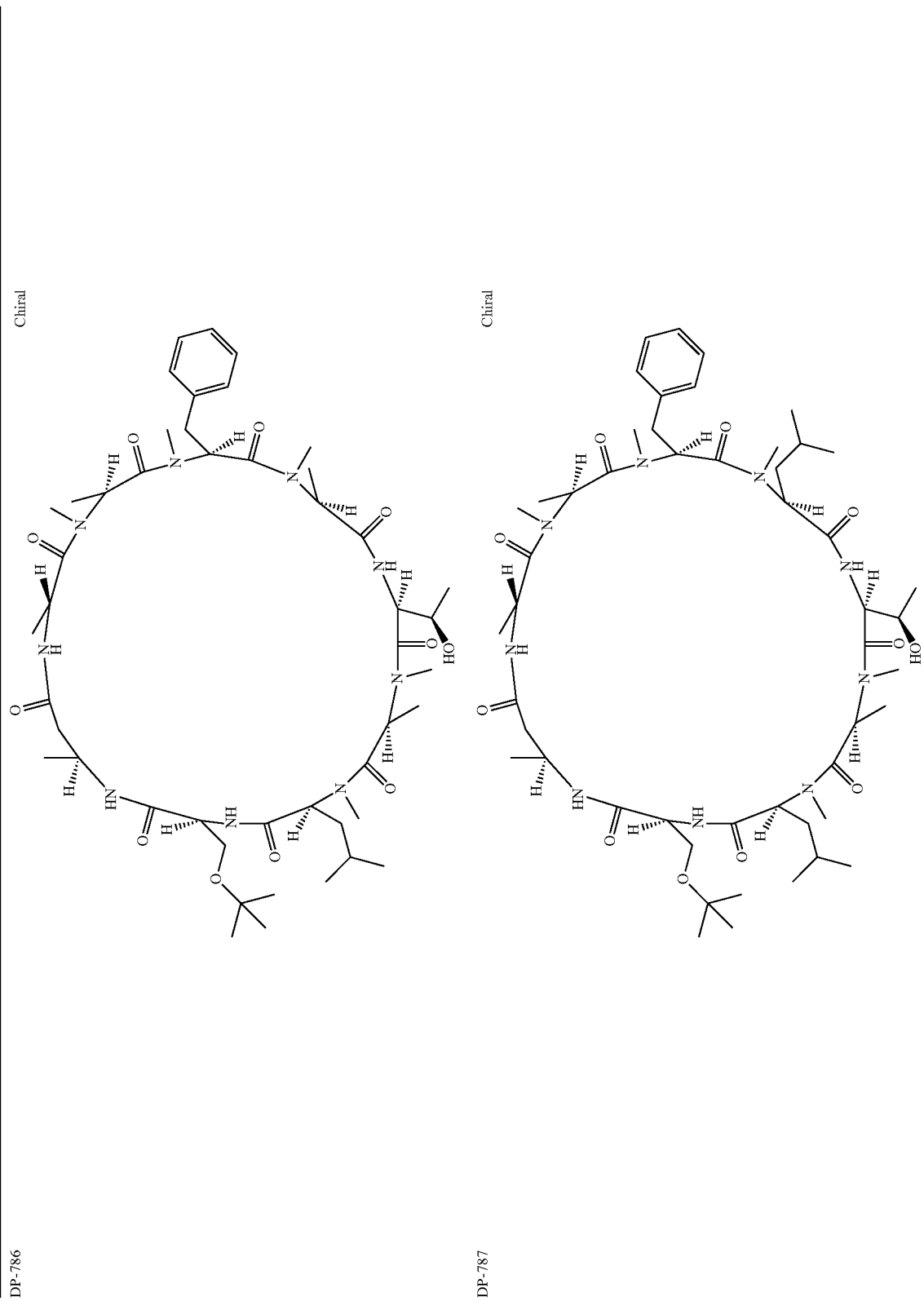
DP-786
DP-787

TABLE 11-3-1-continued
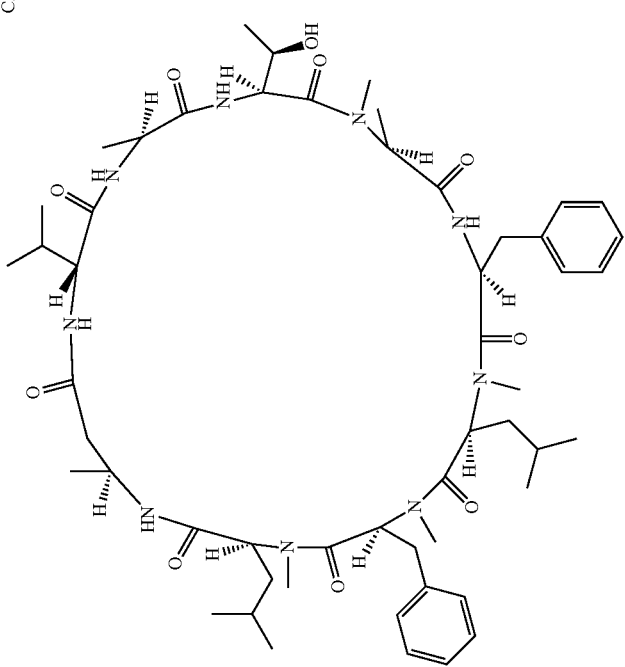
DP-788

TABLE 11-3-1-continued
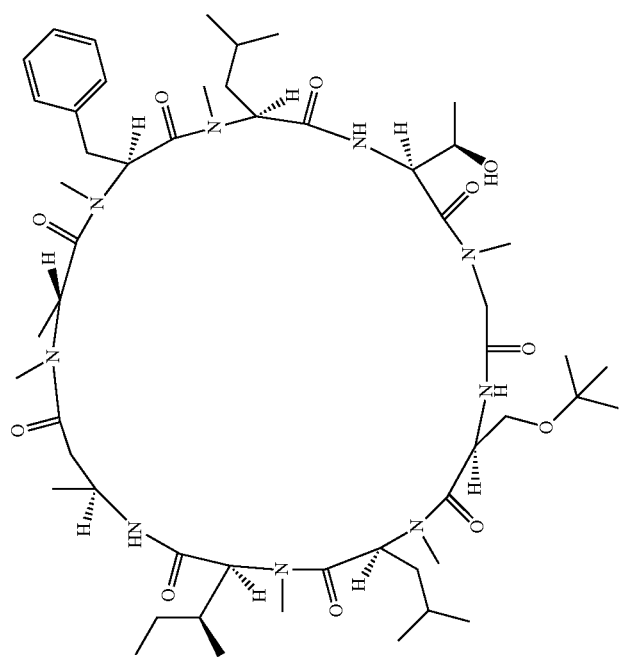
DP-789

TABLE 11-3-1-continued
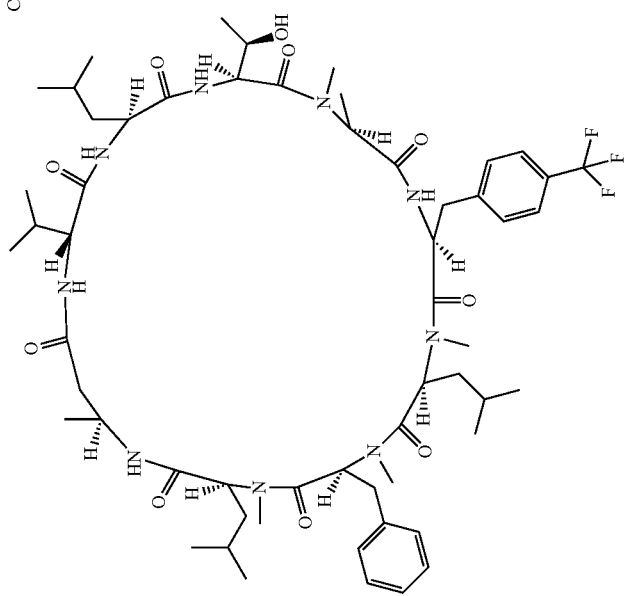
DP-790

TABLE 11-3-1-continued
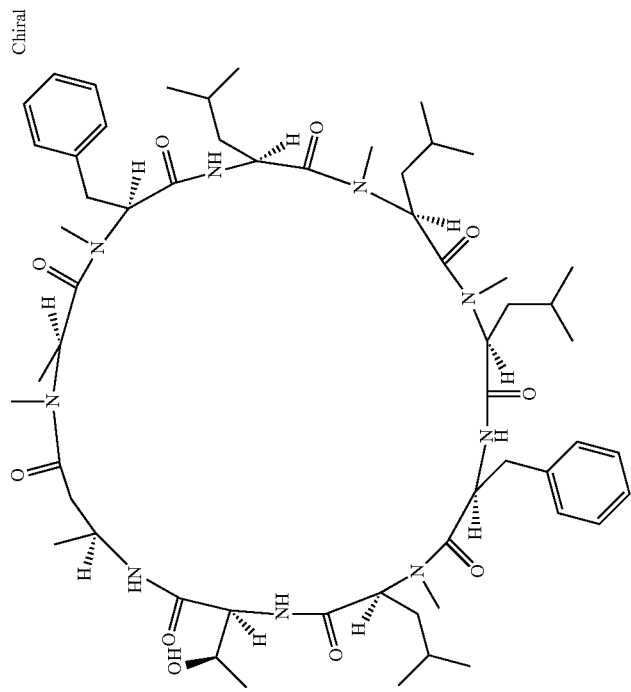
DP-791

TABLE 11-3-1-continued
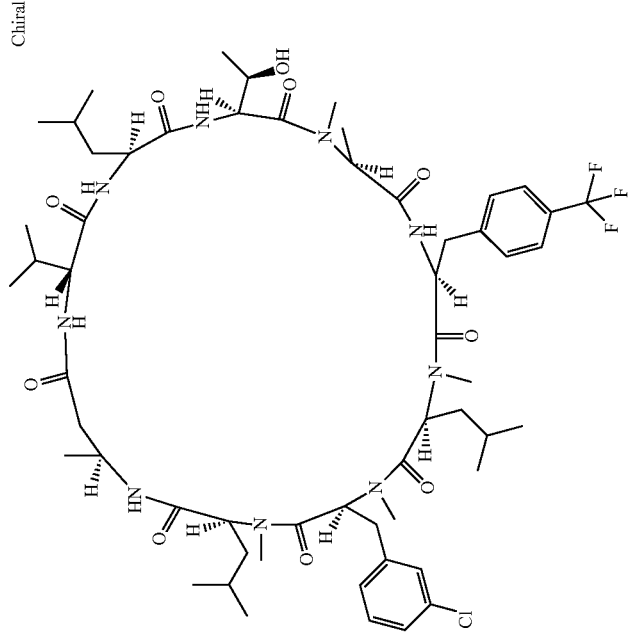
DP-792

TABLE 11-3-1-continued
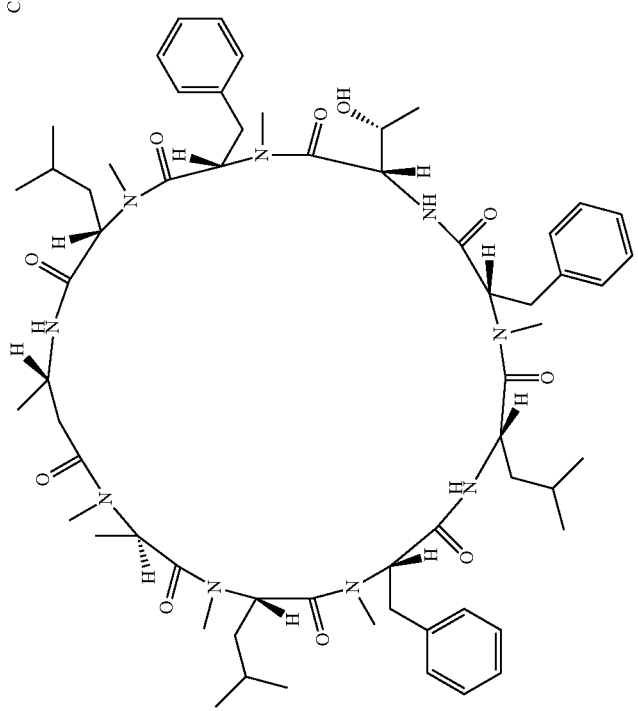
DP-793

TABLE 11-3-1-continued
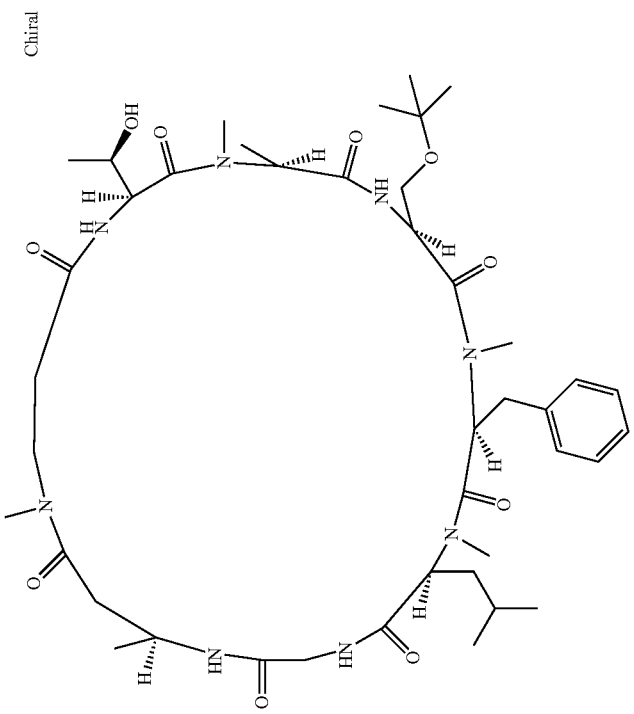
DP-794

TABLE 11-3-1-continued
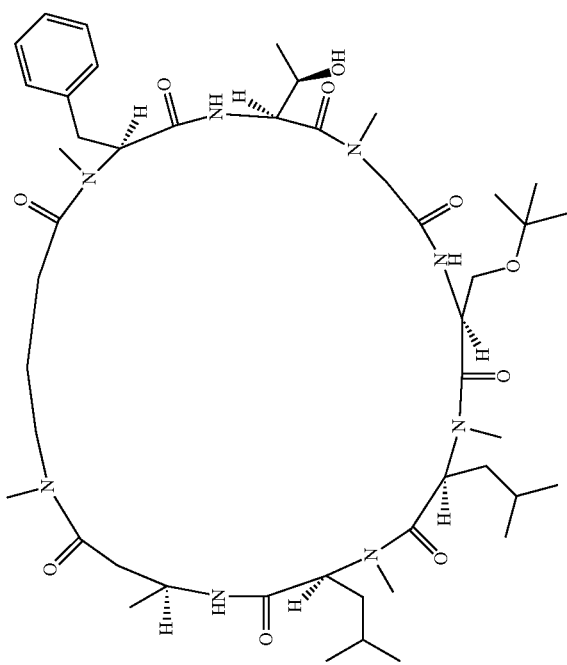
DP-795

TABLE 11-3-1-continued
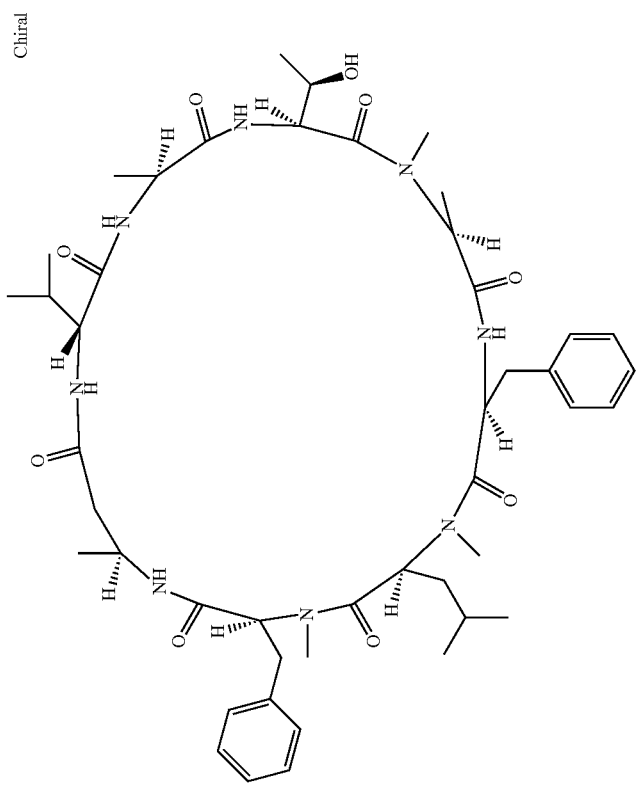
DP-796

TABLE 11-3-1-continued
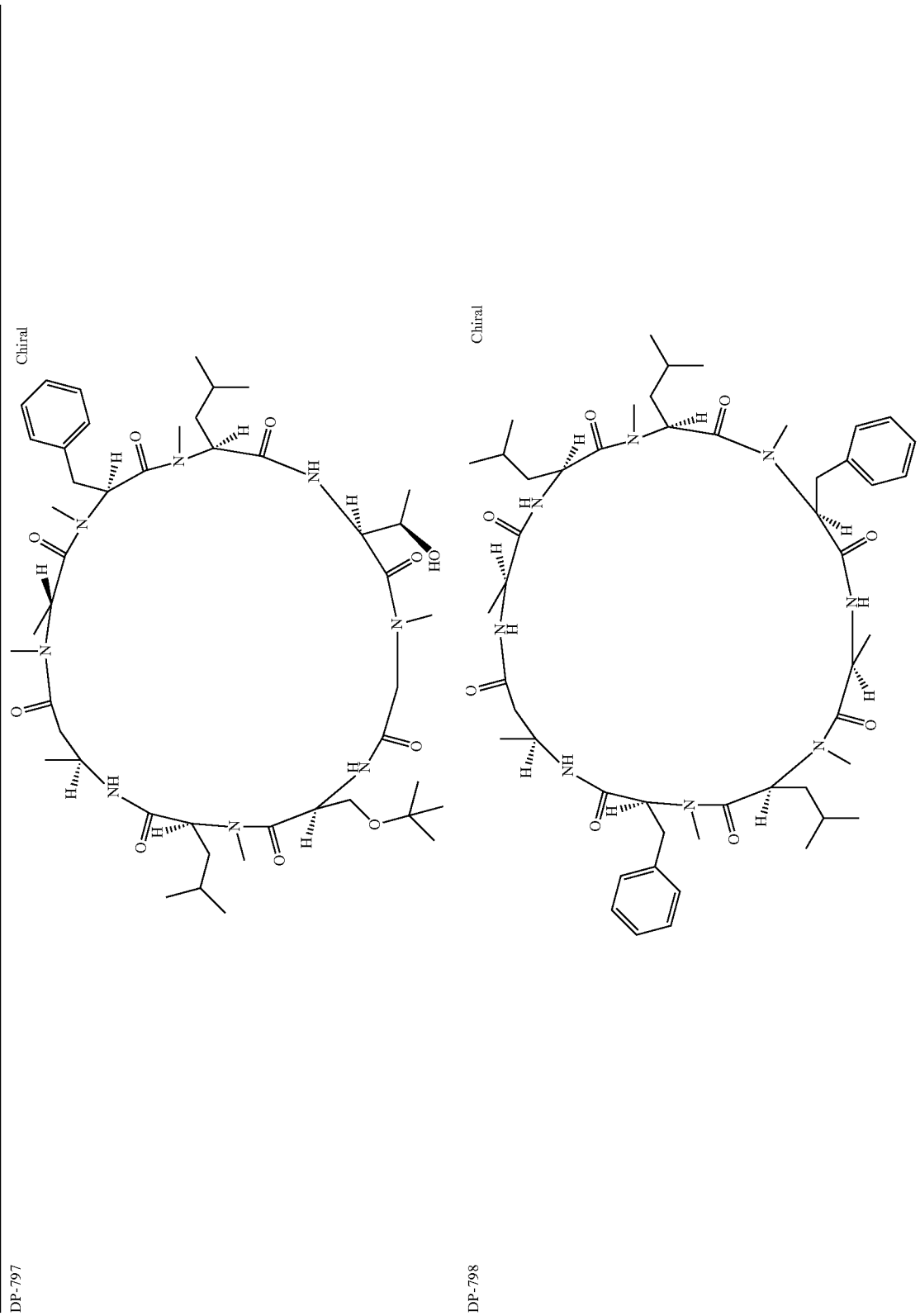
DP-797
DP-798

TABLE 11-3-1-continued
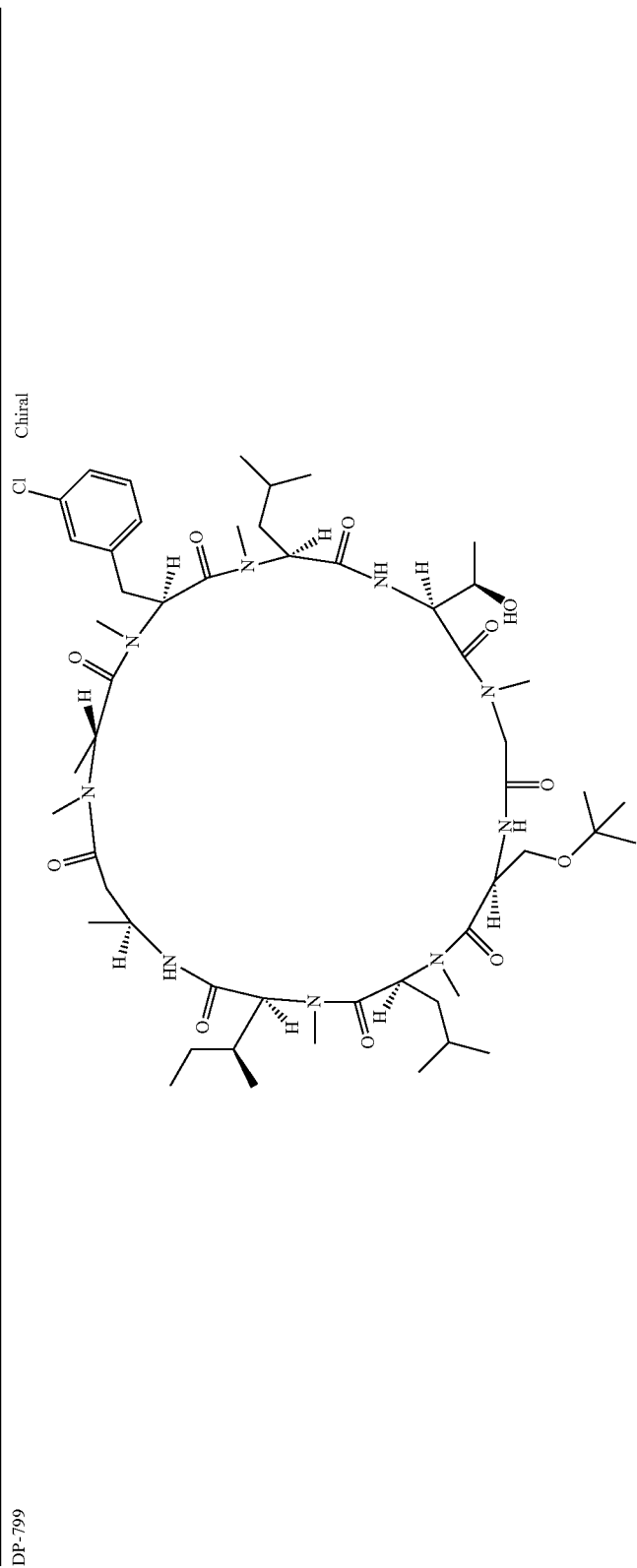
DP-799

TABLE 11-3-1-continued
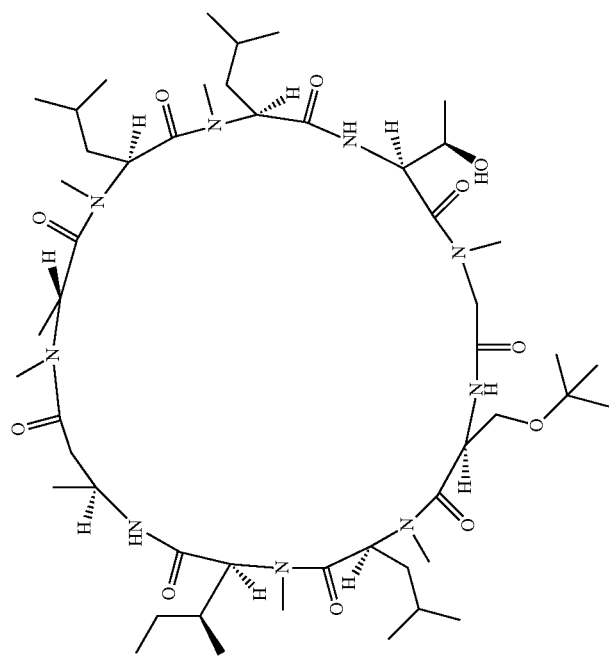
DP-800

TABLE 11-3-1-continued
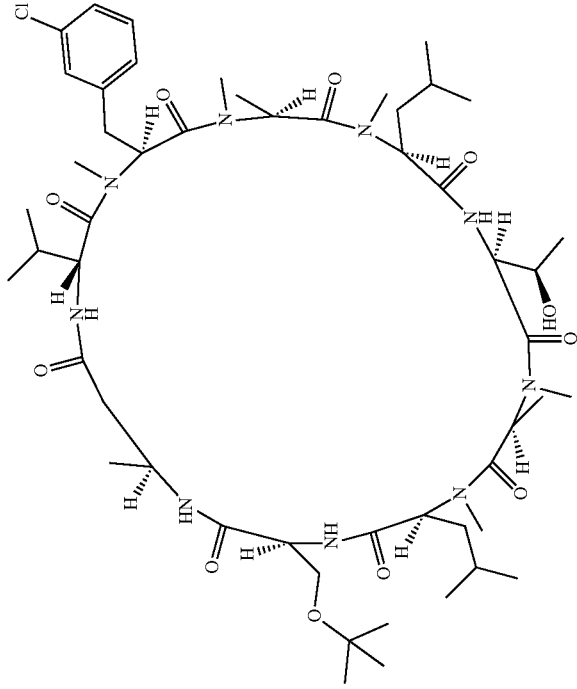
DP-801

TABLE 11-3-1-continued
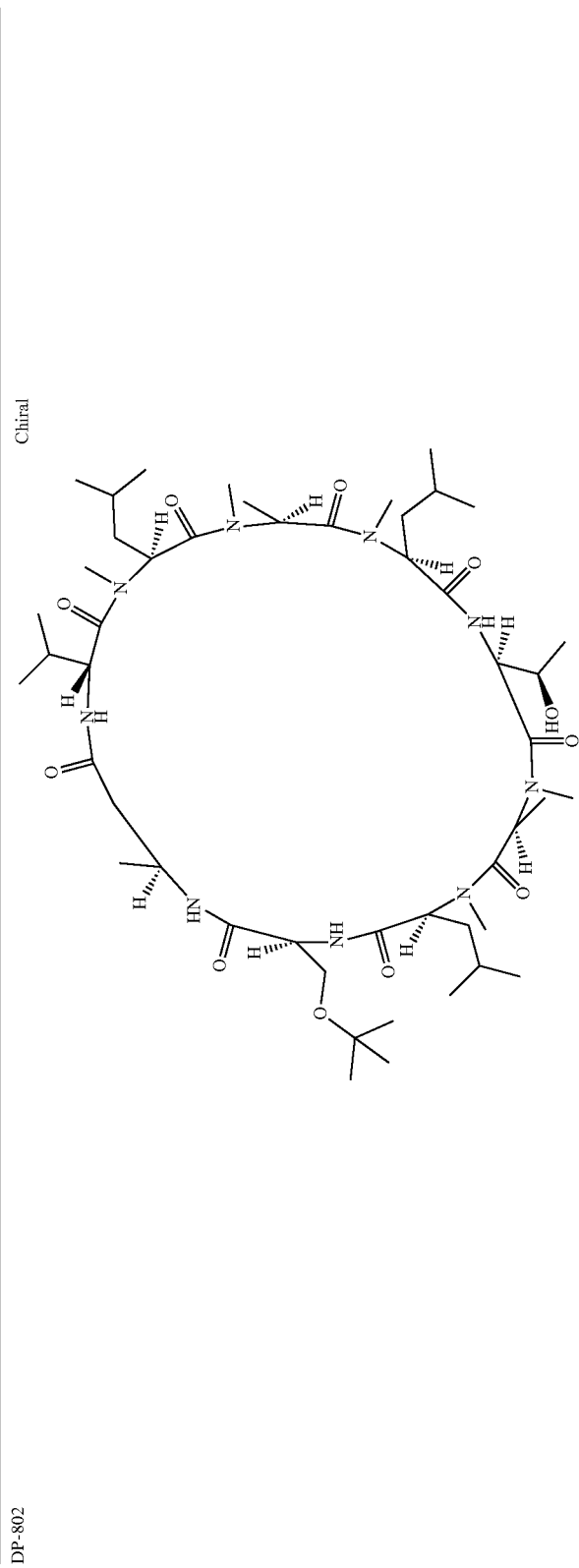
DP-802

TABLE 11-3-1-continued
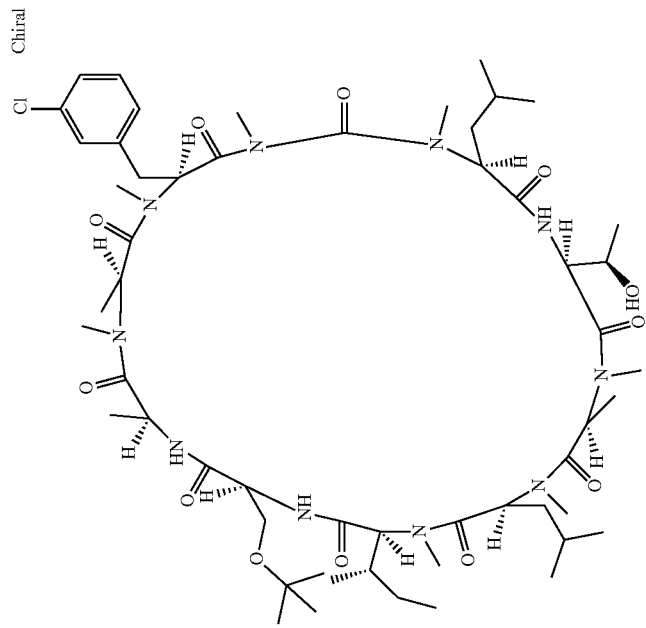
DP-803

TABLE 11-3-1-continued
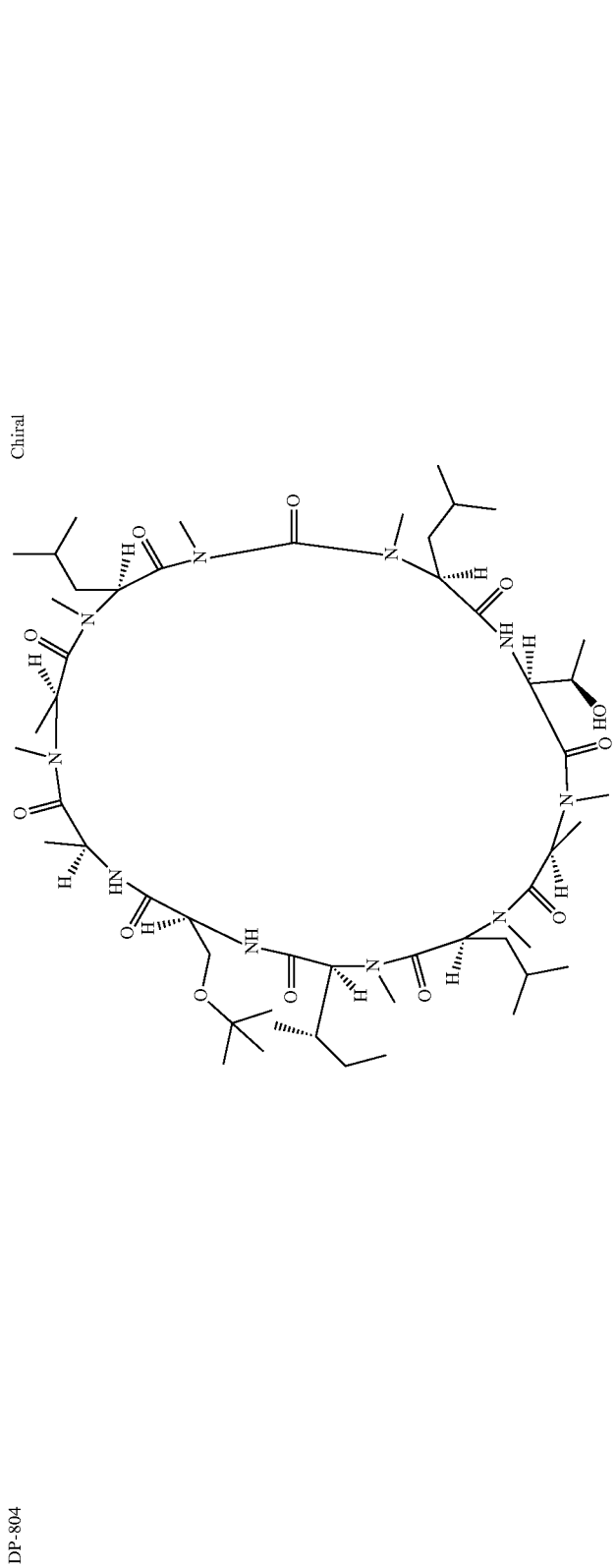
DP-804

TABLE 11-3-1-continued
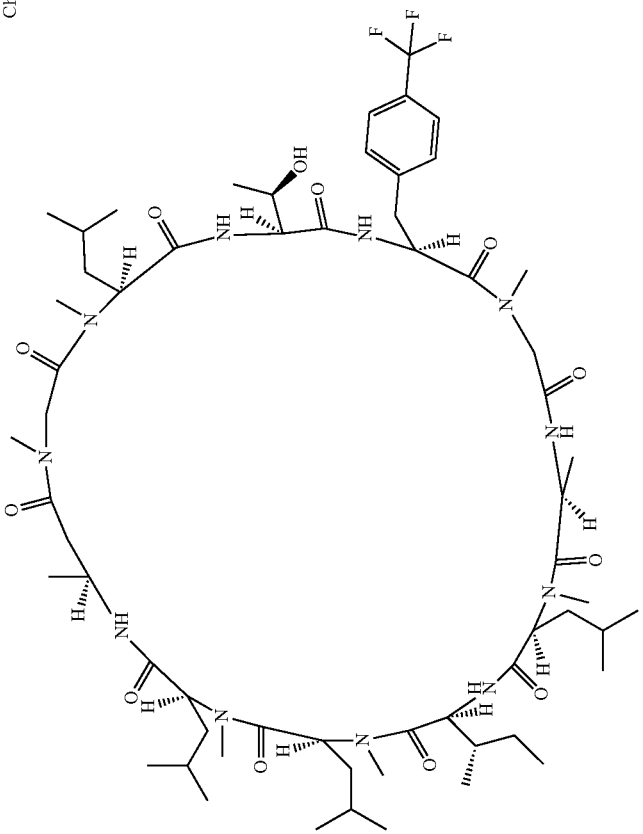
DP-805

TABLE 11-3-1-continued
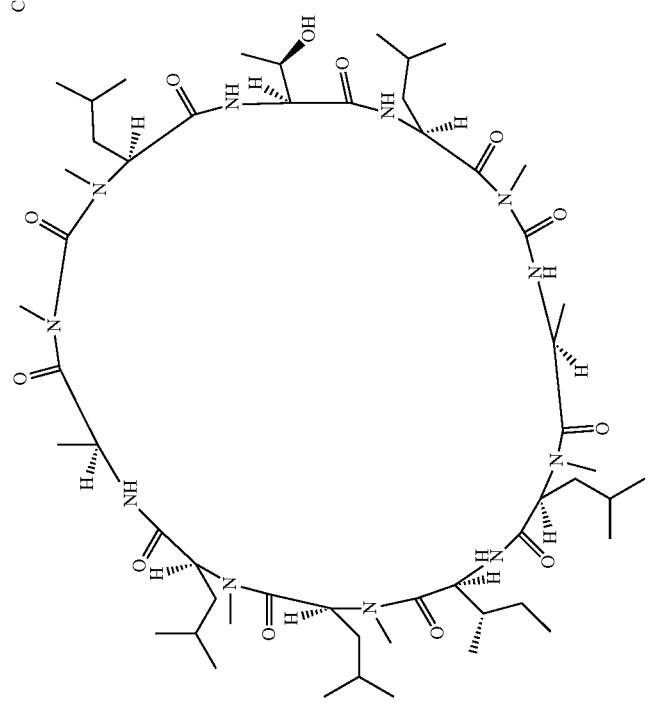
DP-806

TABLE 11-3-1-continued
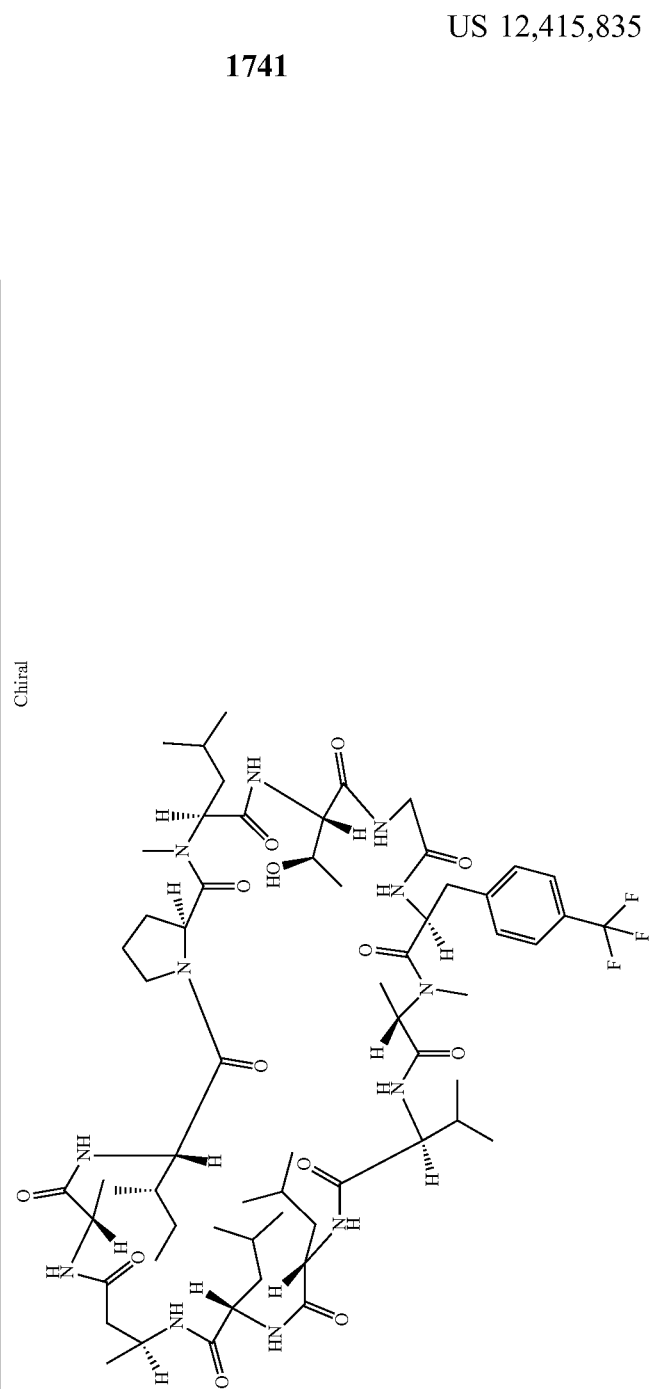
DP-807

TABLE 11-3-1-continued
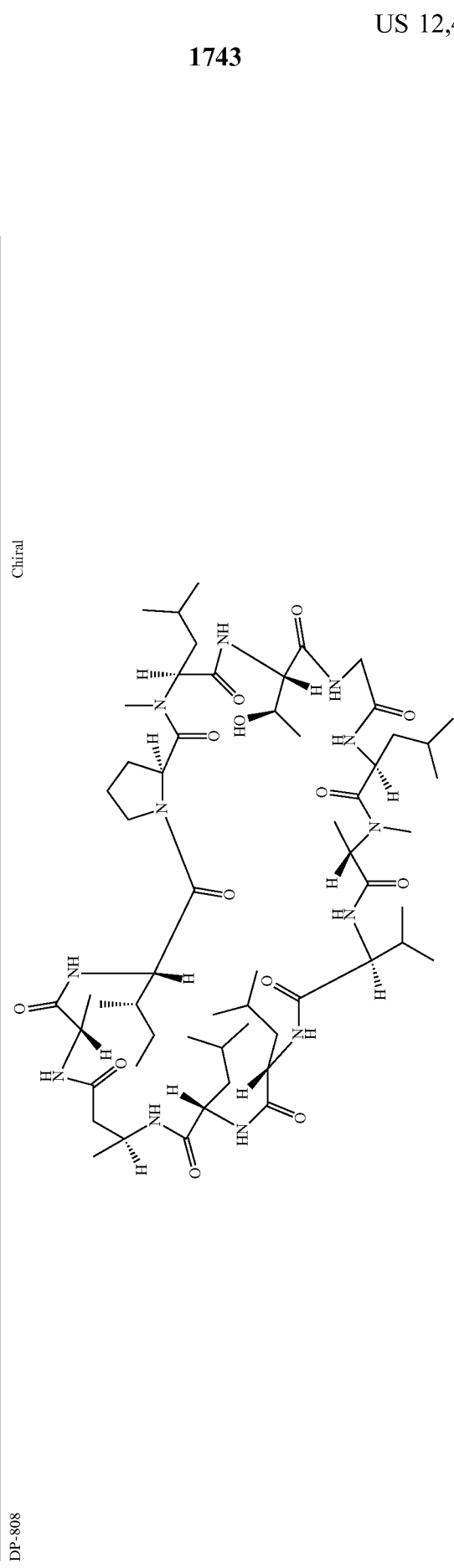
DP-808

TABLE 11-3-1-continued
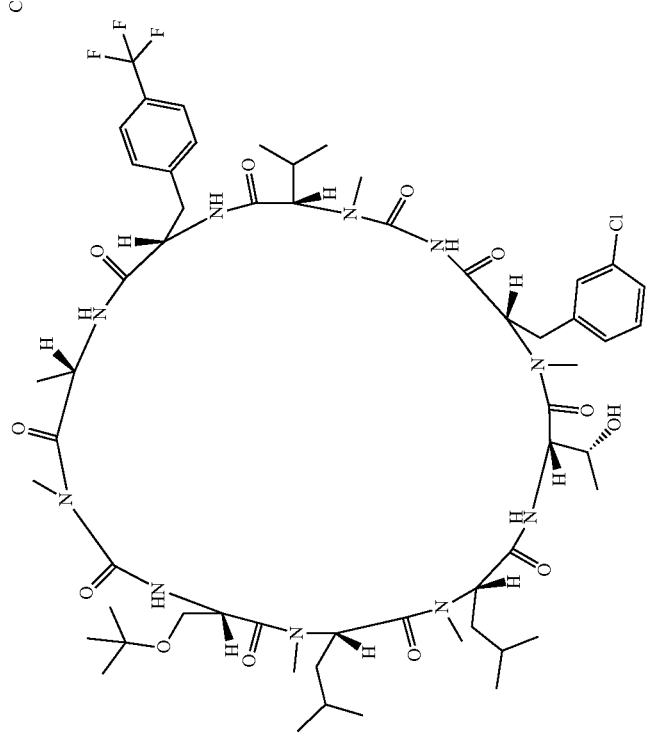
DP-809

TABLE 11-3-1-continued
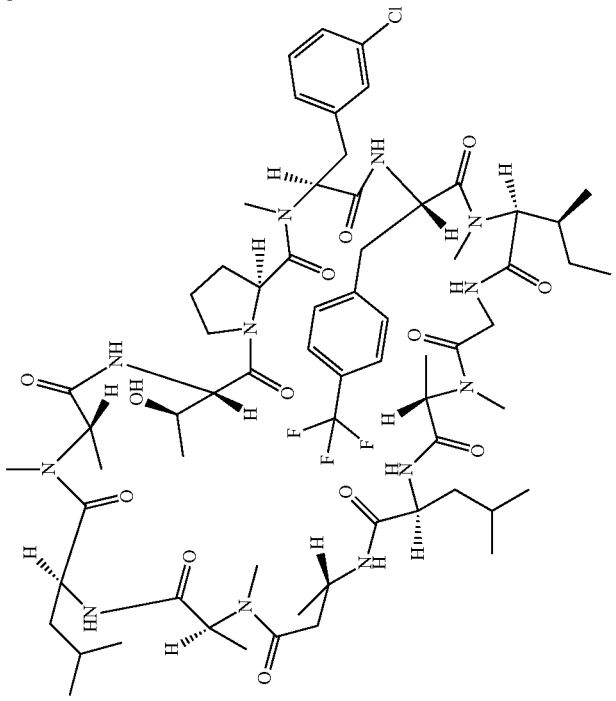
DP-810

TABLE 11-3-1-continued
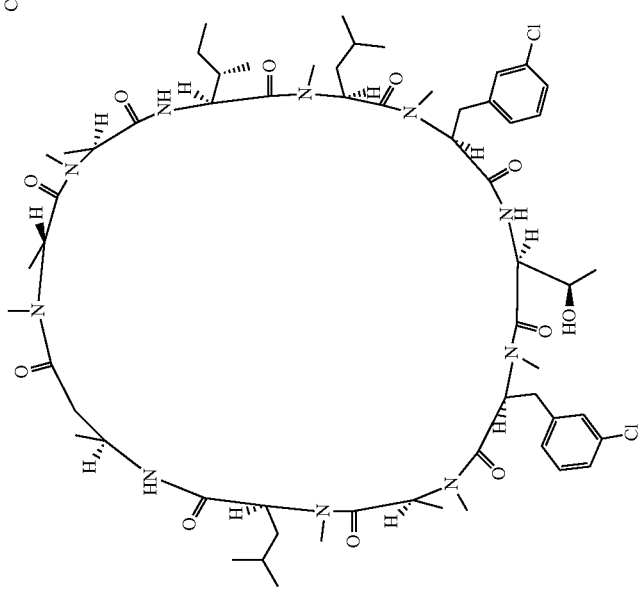
DP-811

TABLE 11-3-1-continued
DP-812
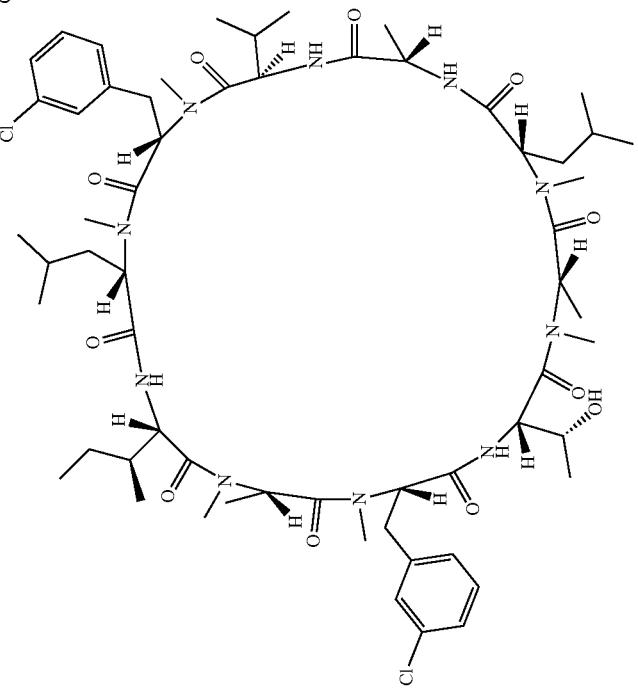

TABLE 11-3-1-continued
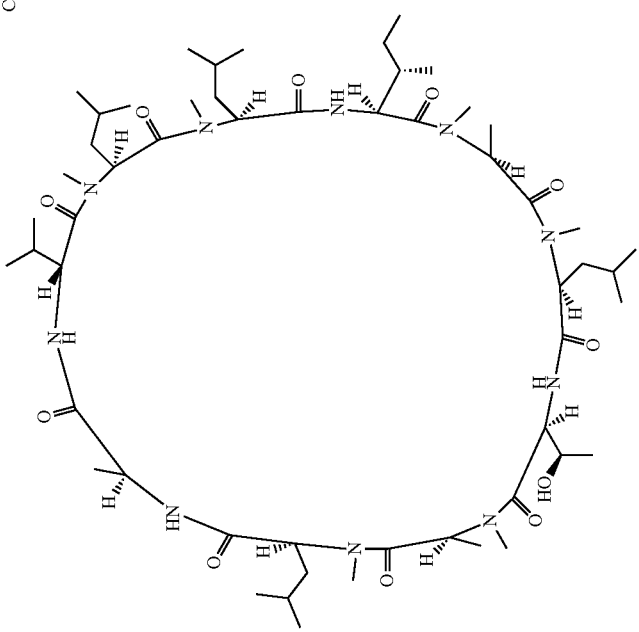
DP-813

TABLE 11-3-1-continued
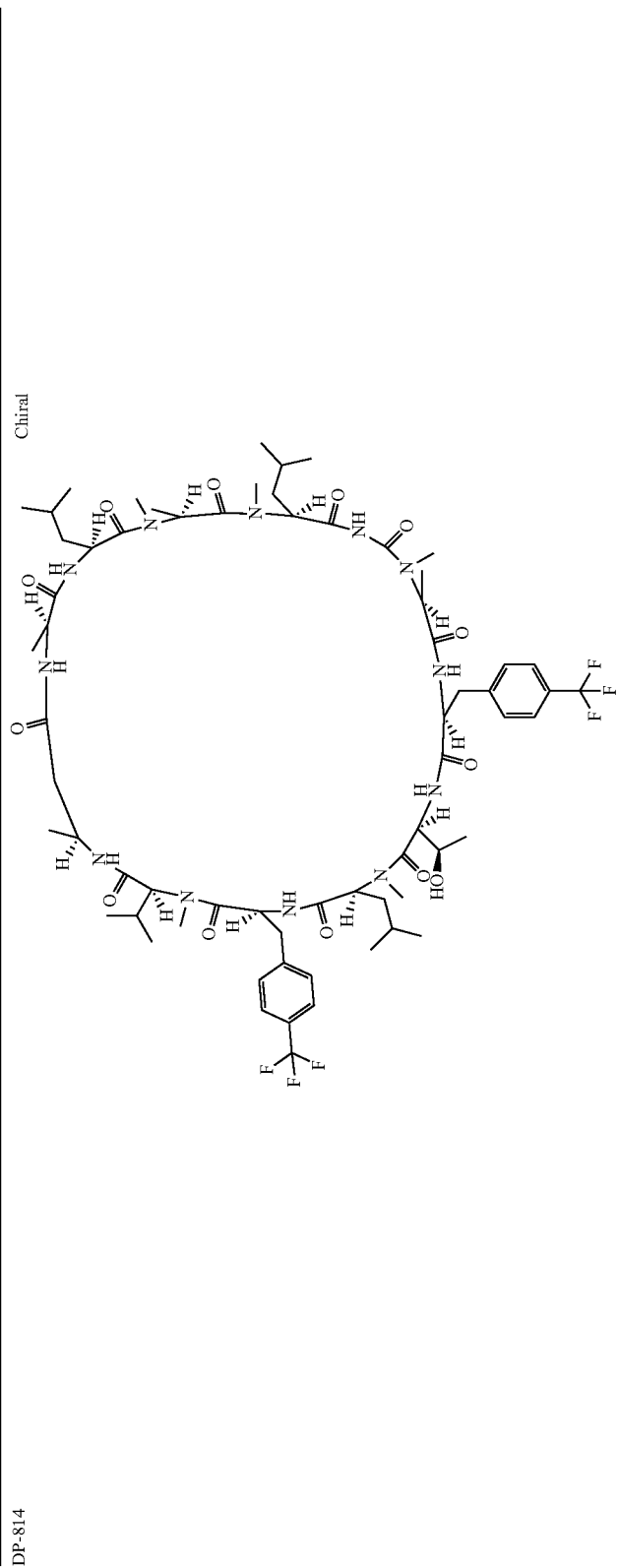
DP-814

TABLE 11-3-1-continued
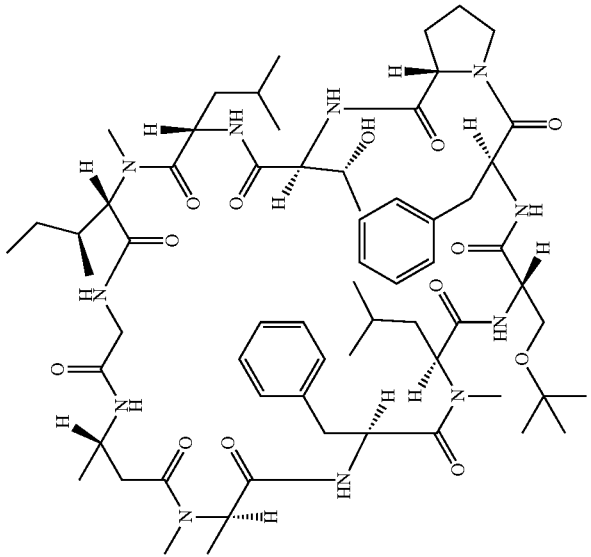

TABLE 11-3-1-continued
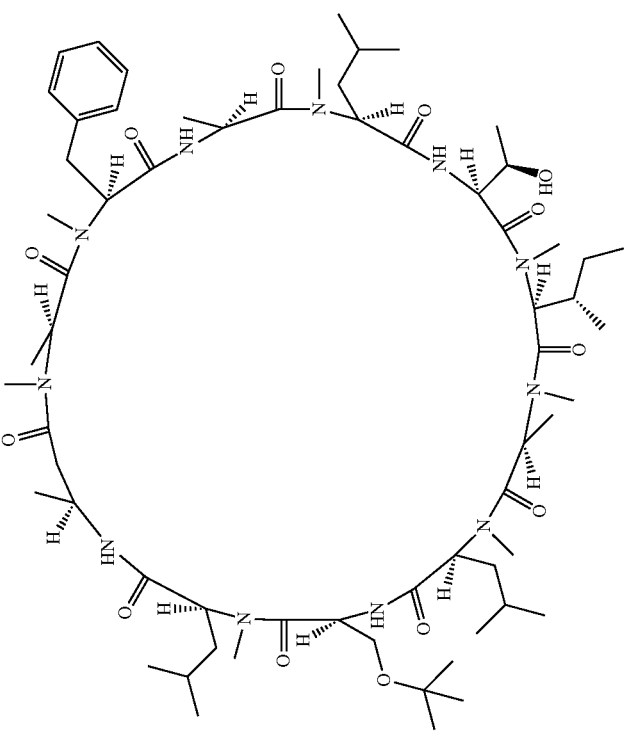
DP-816

TABLE 11-3-1-continued
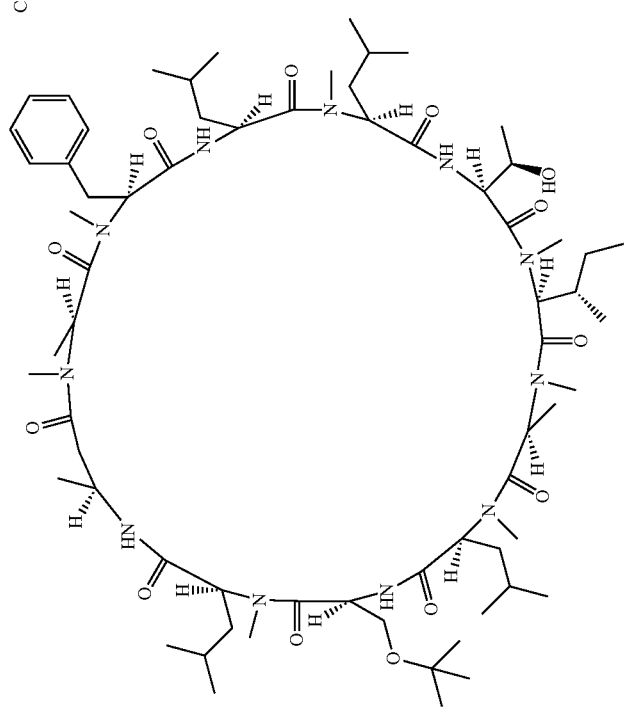
DP-817

TABLE 11-3-1-continued
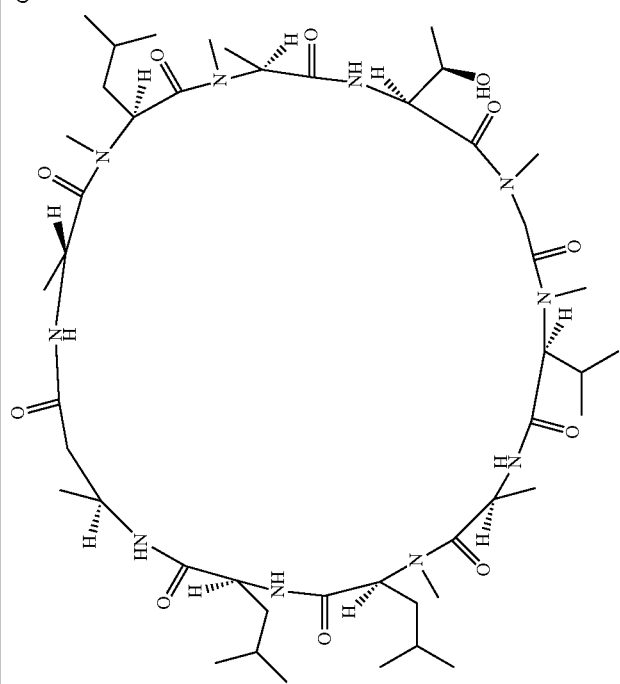
DP-818

TABLE 11-3-1-continued
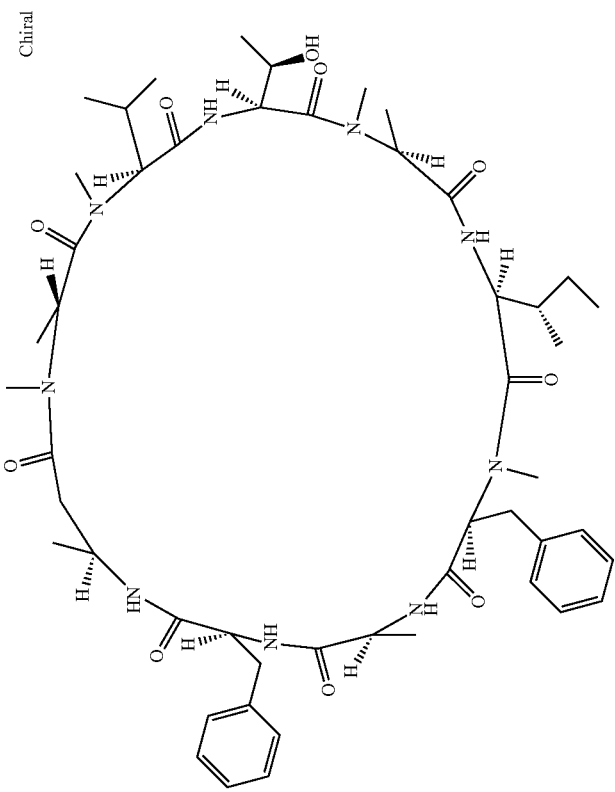
DP-819

TABLE 11-3-1-continued
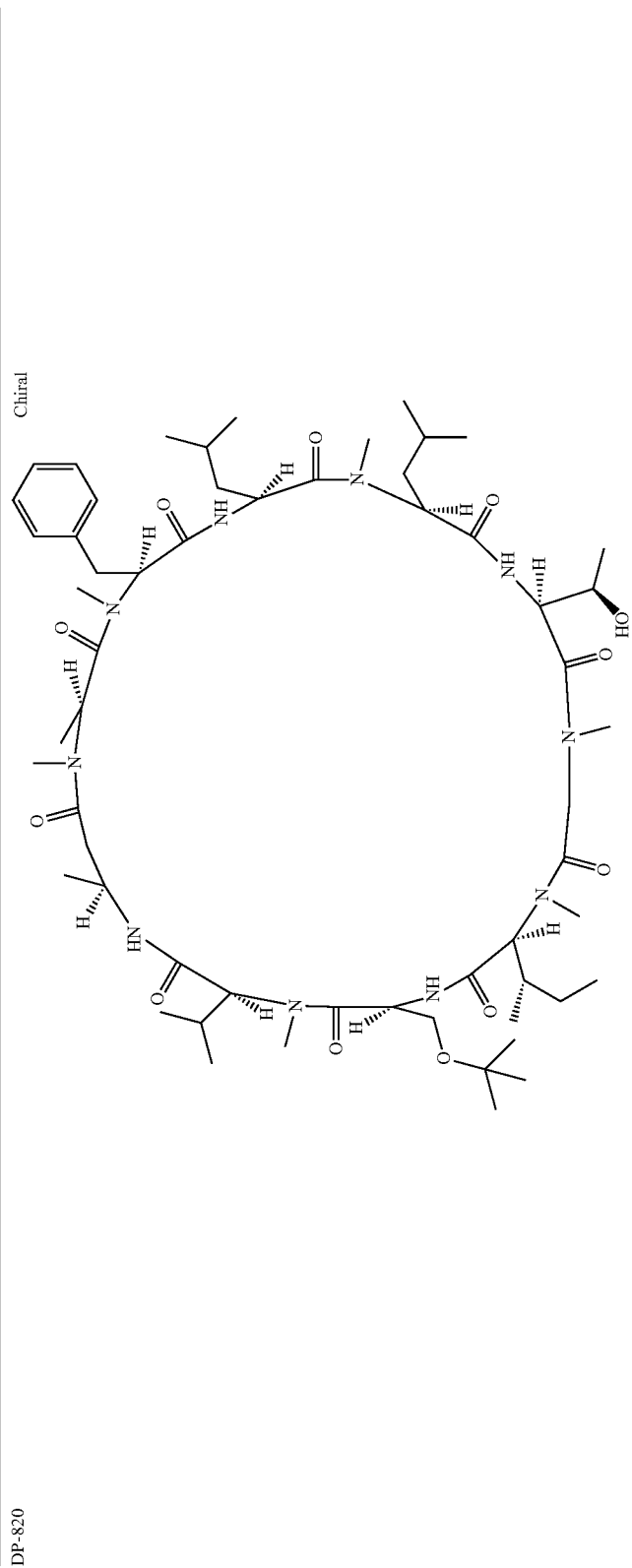
DP-820

TABLE 11-3-1-continued
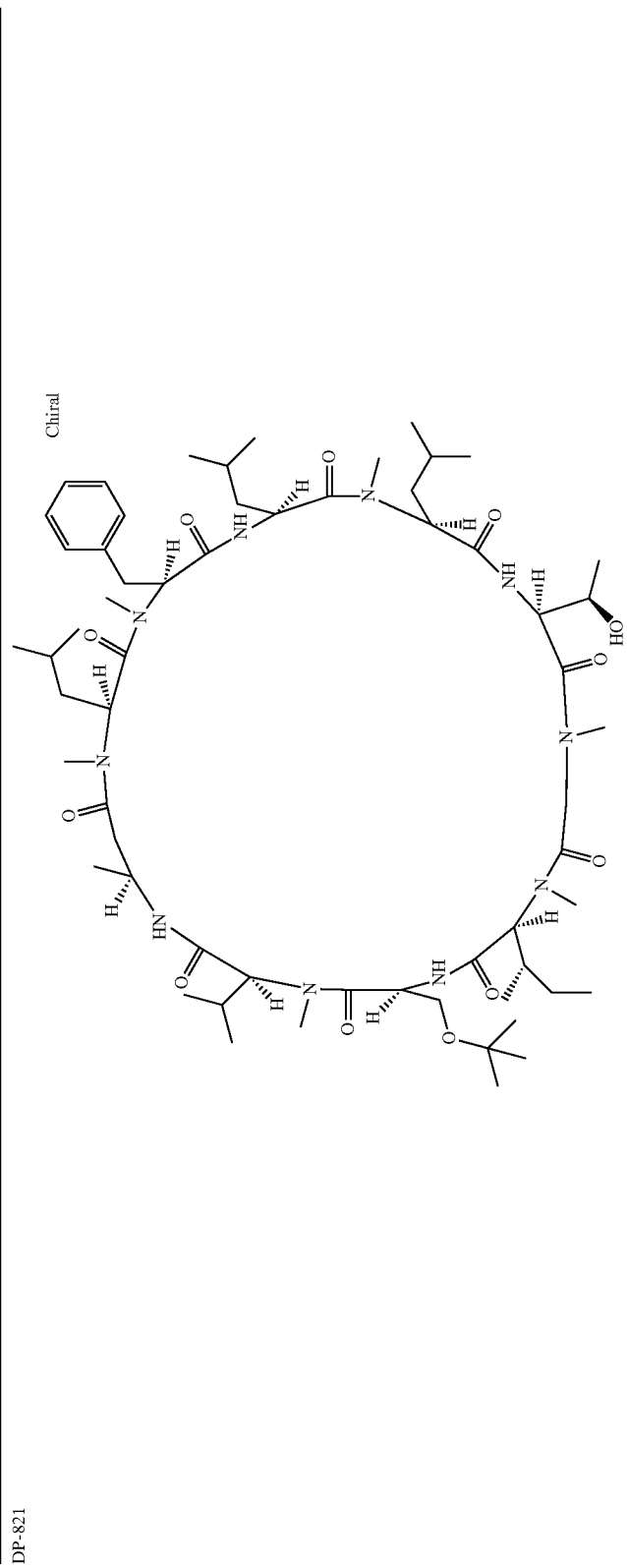
DP-821

TABLE 11-3-1-continued
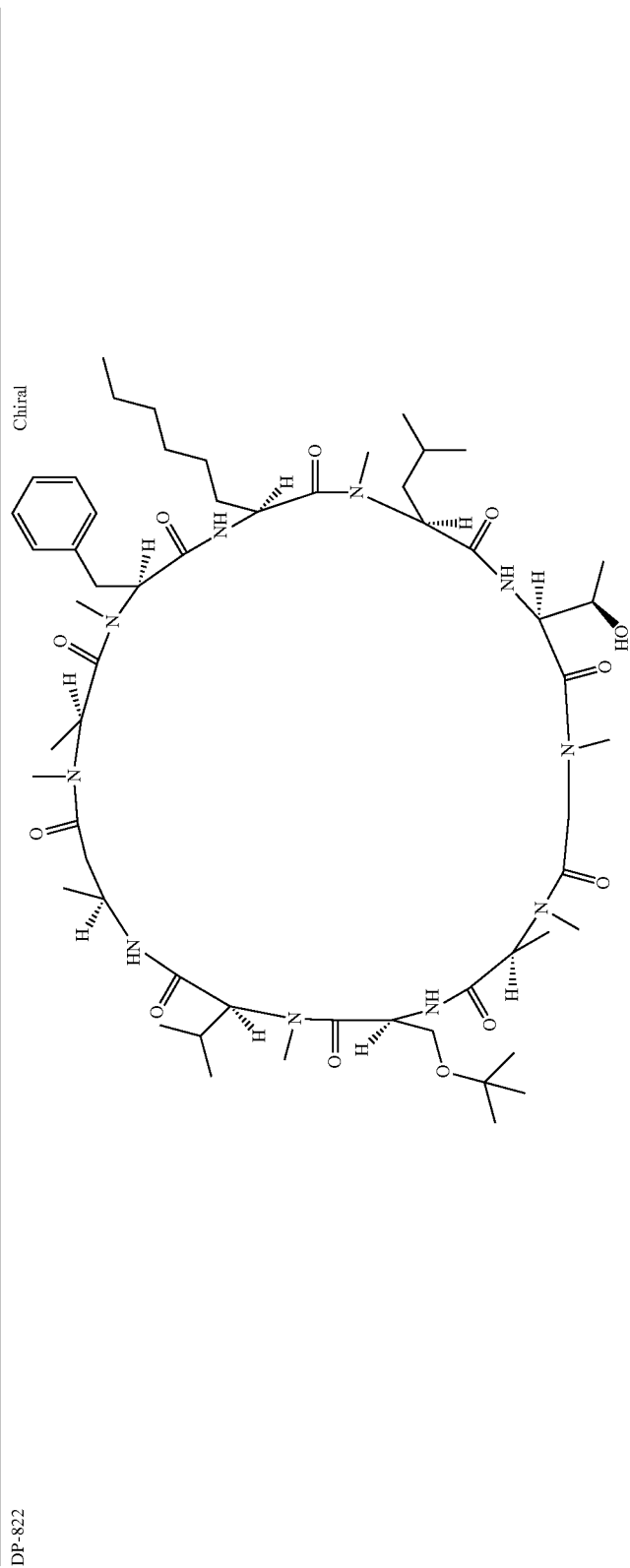
DP-822

TABLE 11-3-1-continued
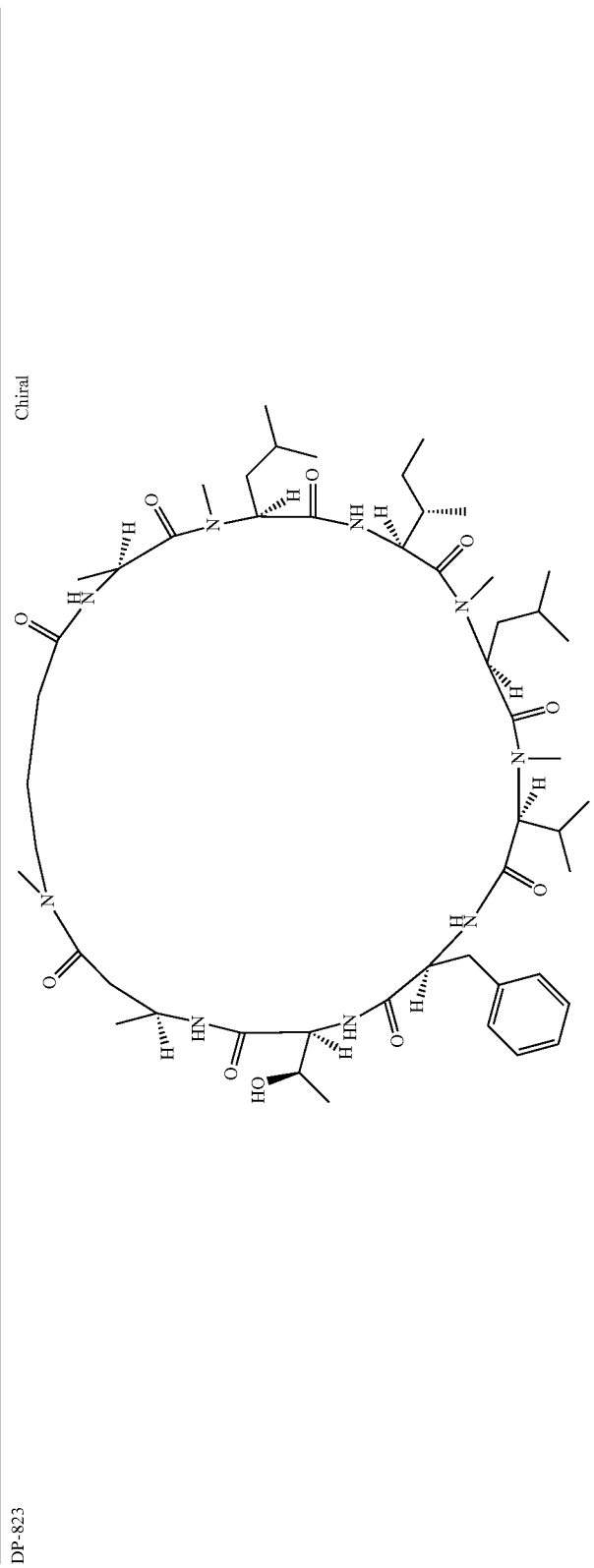
DP-823

TABLE 11-3-1-continued
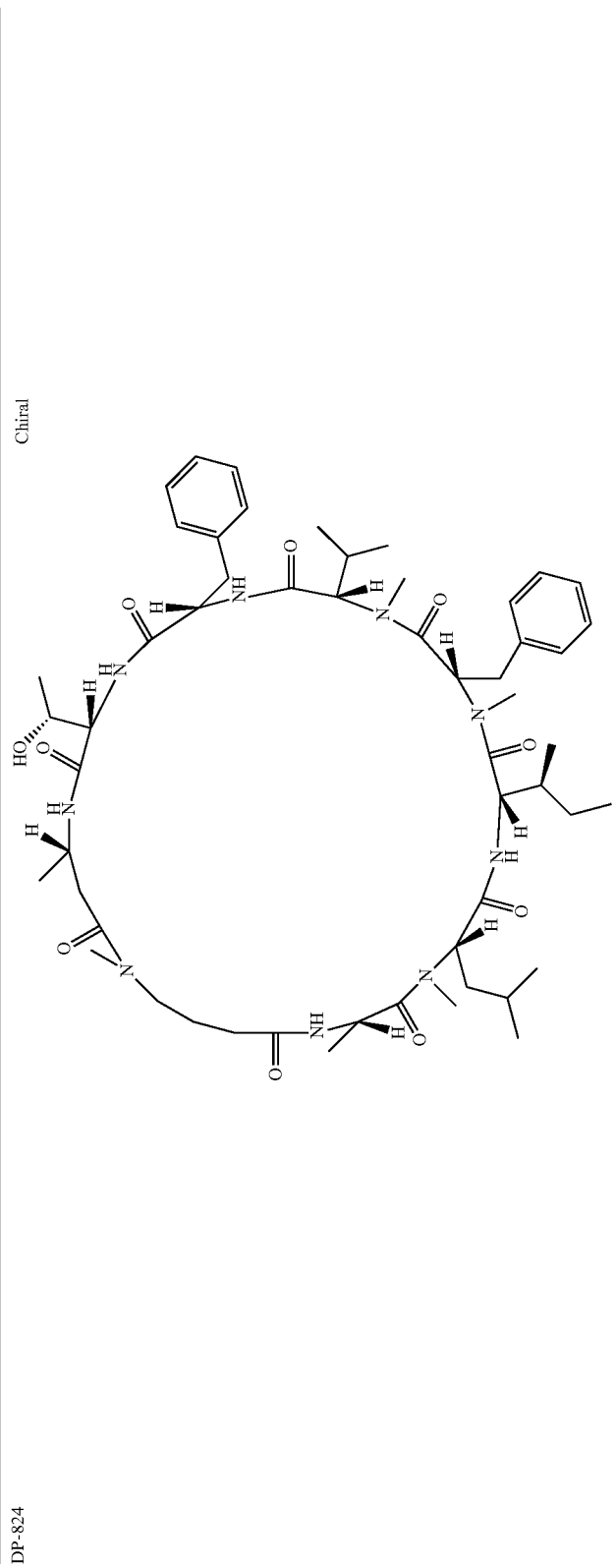
DP-824

TABLE 11-3-1-continued
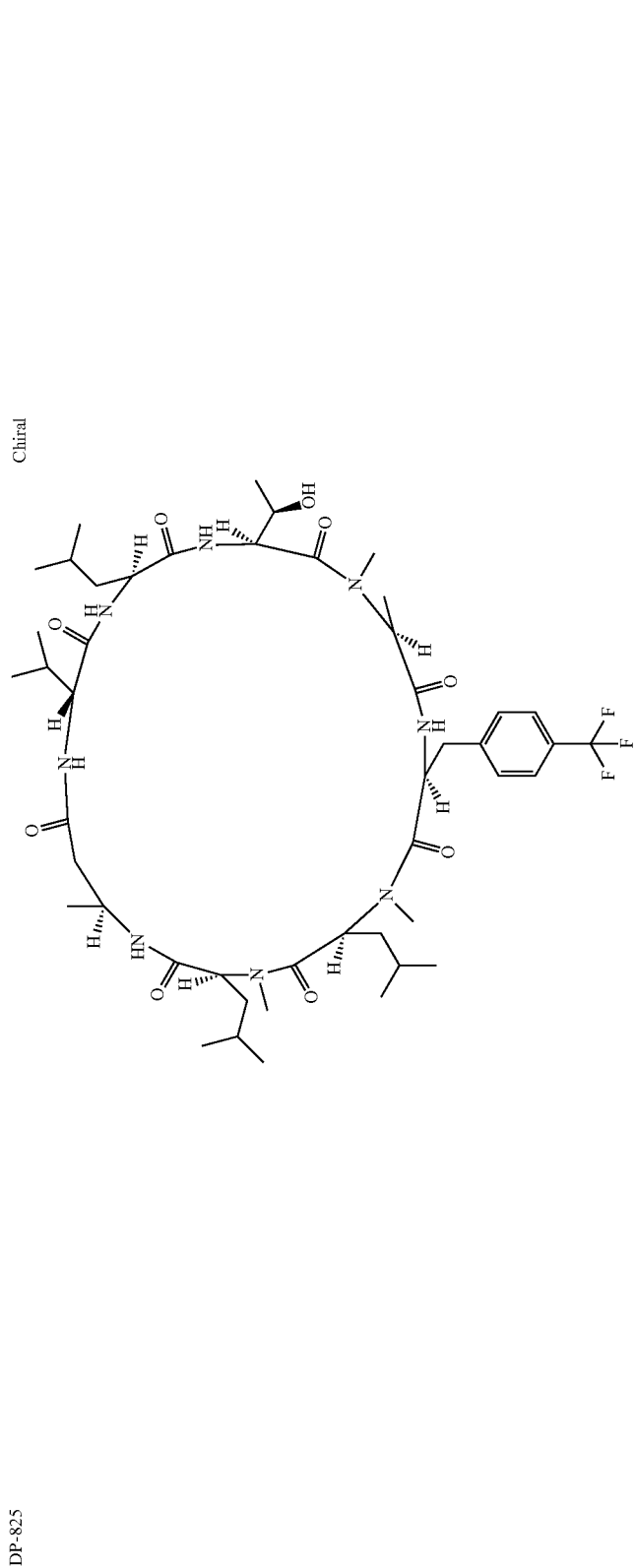
DP-825

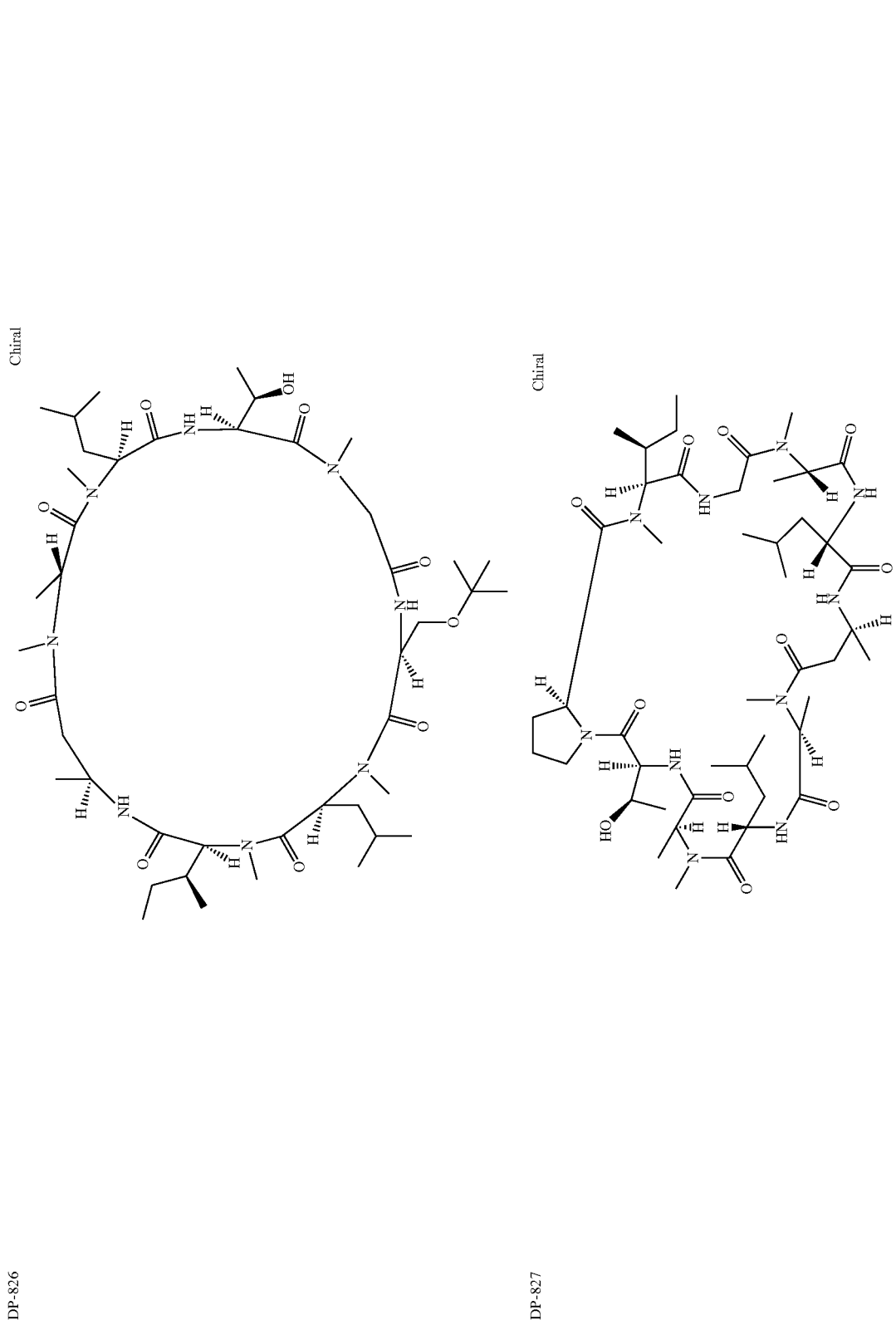

TABLE 11-3-1-continued
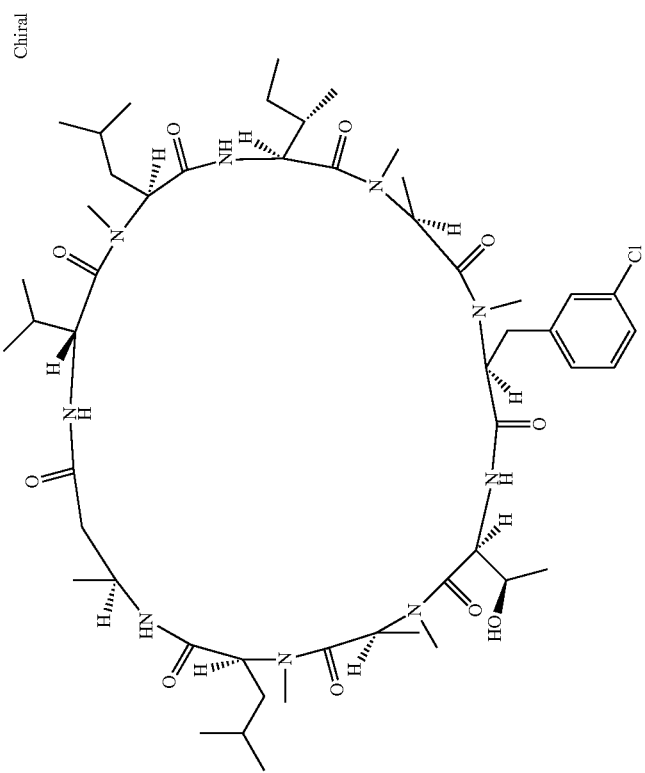
DP-828

TABLE 11-3-1-continued
DP-829
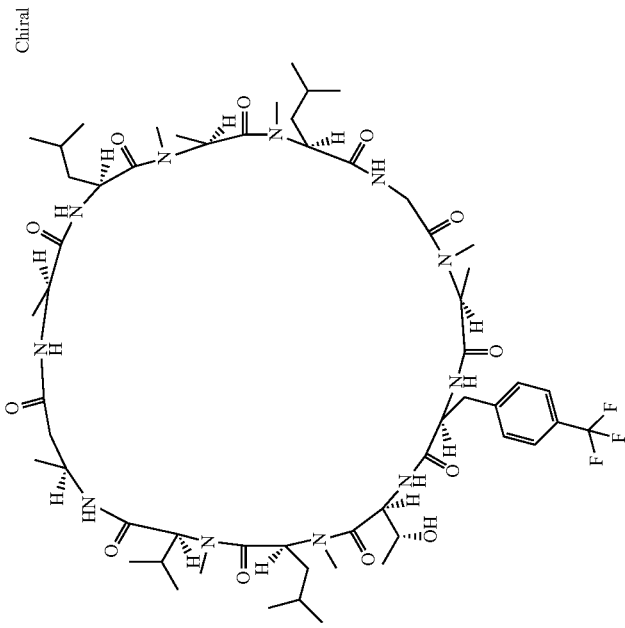

TABLE 11-3-1-continued
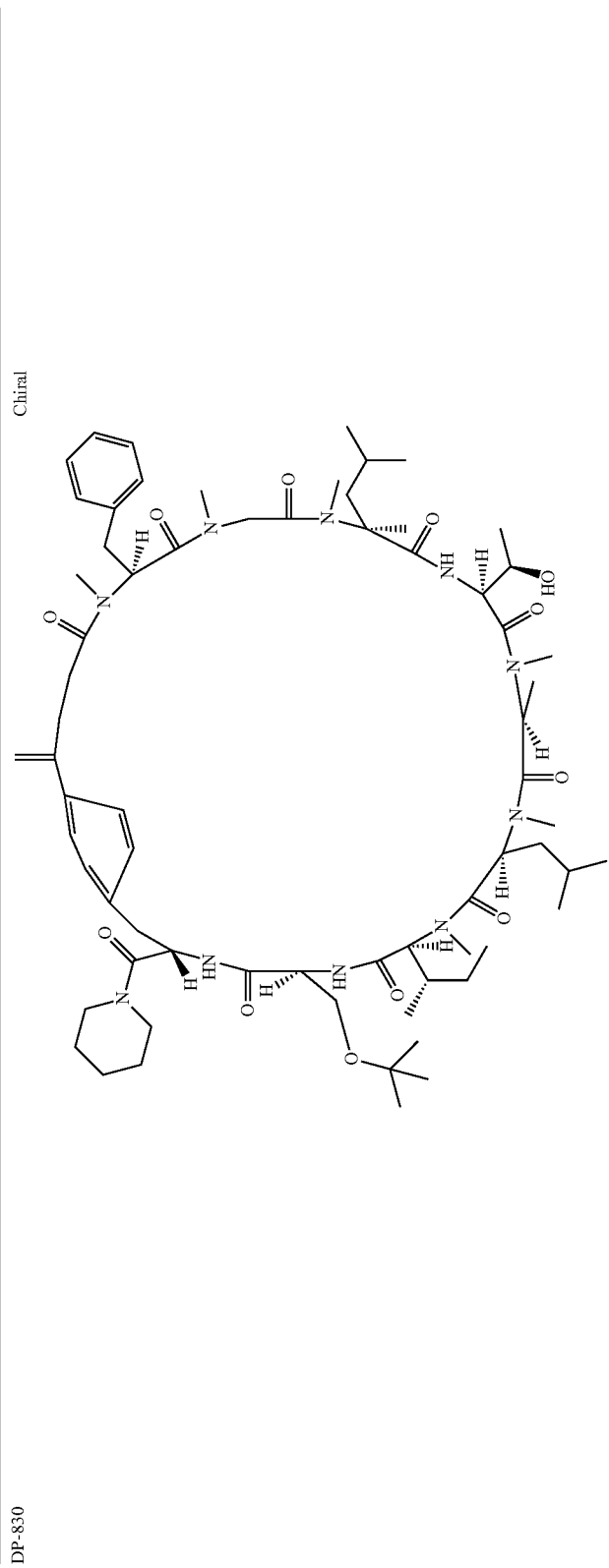
DP-830

TABLE 11-3-1-continued
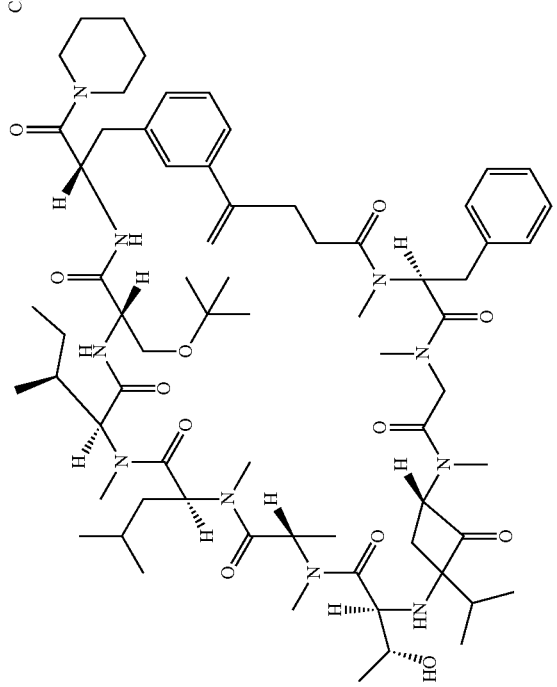
DP-831

TABLE 11-3-1-continued
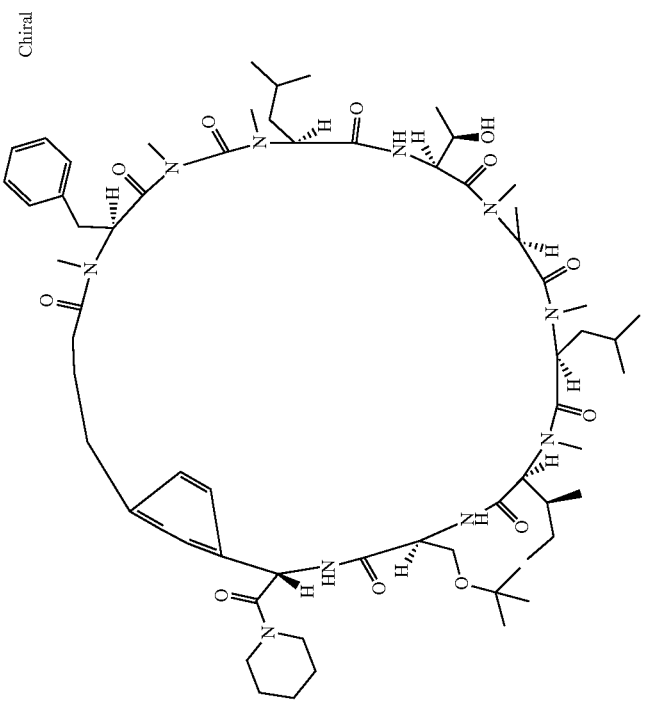
DP-832

TABLE 11-3-1-continued
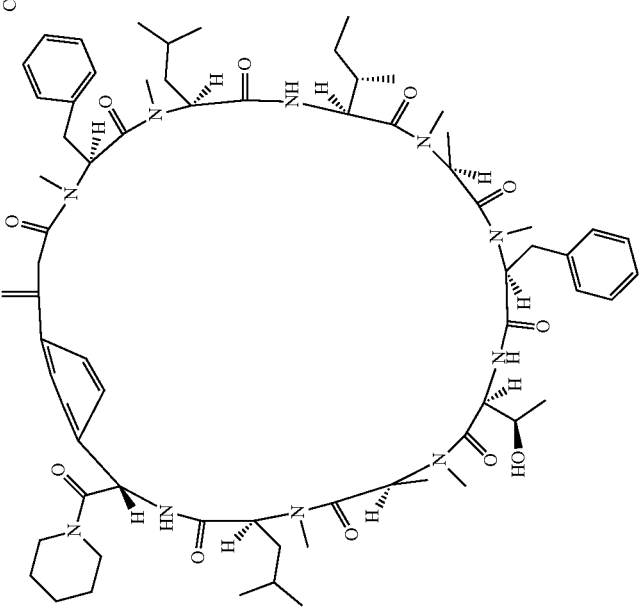
DP-833

TABLE 11-3-1-continued
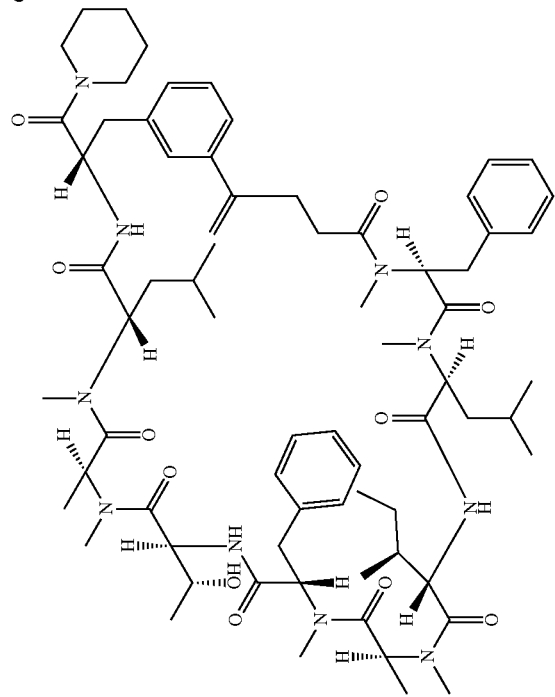
DP-834

TABLE 11-3-1-continued
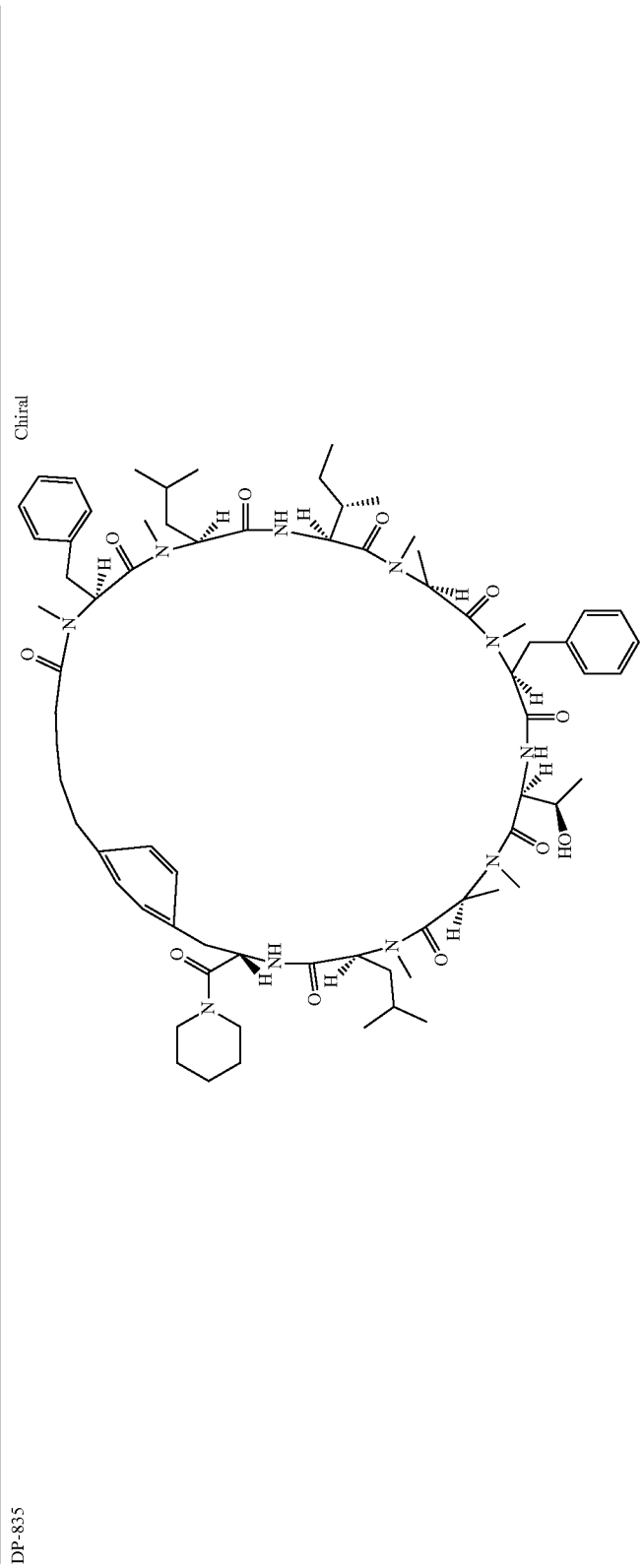
DP-835

TABLE 11-3-1-continued
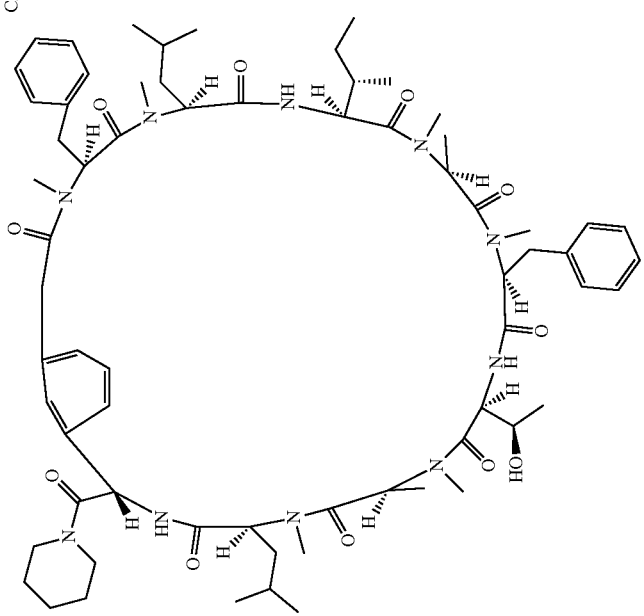
DP-836

TABLE 11-3-1-continued
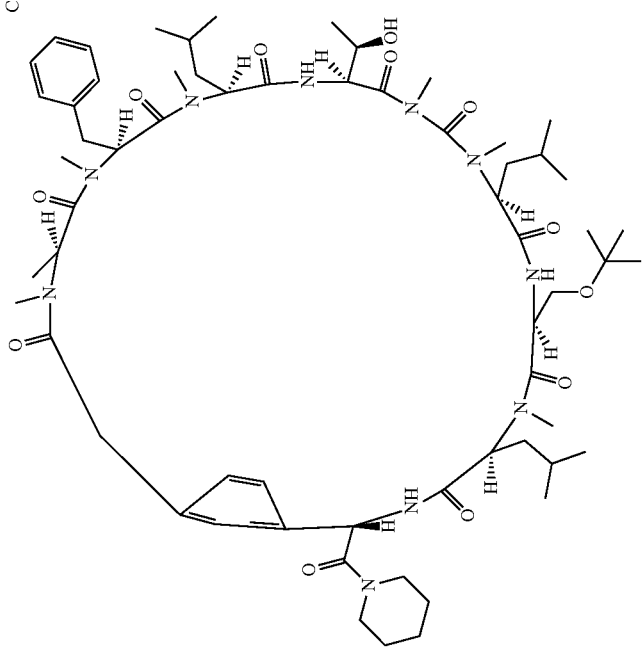
DP-837

TABLE 11-3-1-continued
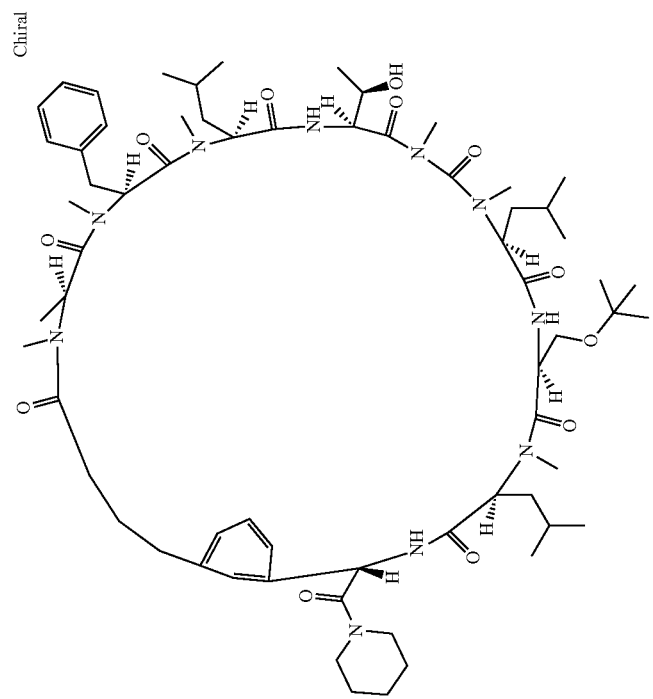
DP-838

TABLE 11-3-1-continued
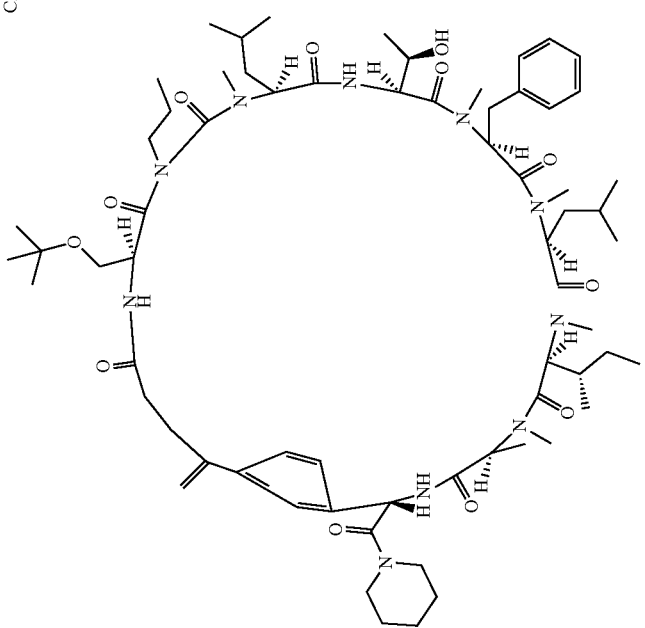
DP-839

TABLE 11-3-1-continued
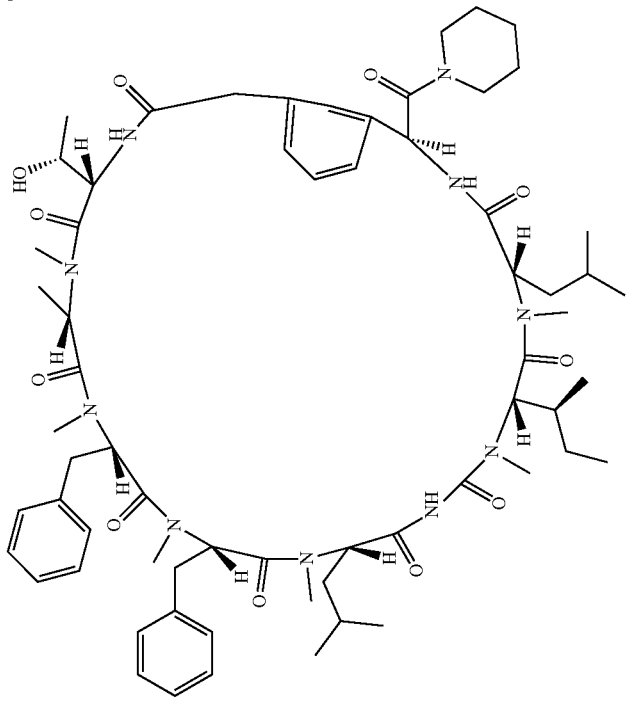
DP-840

TABLE 11-3-1-continued
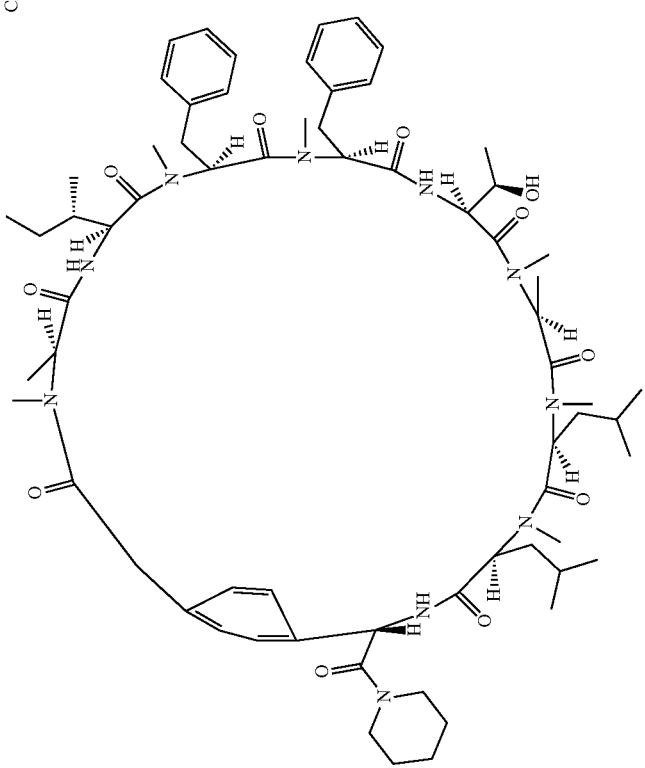
DP-841

TABLE 11-3-1-continued
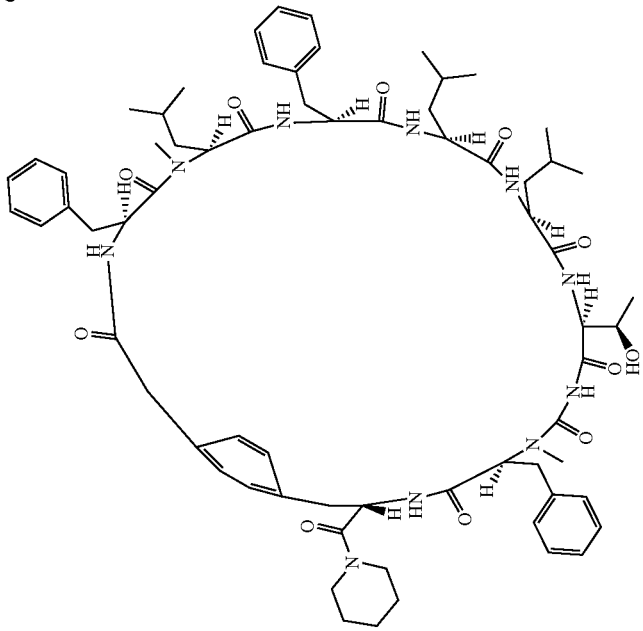
DP-842

TABLE 11-3-1-continued
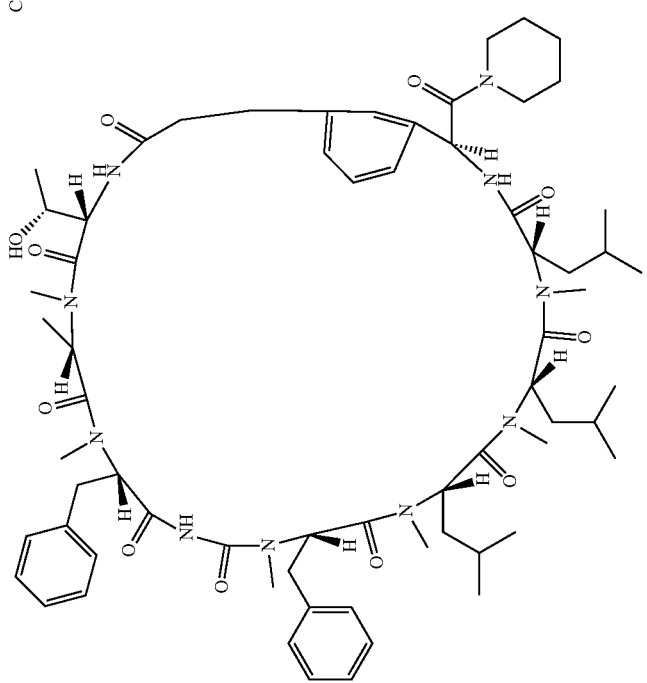
DP-843

TABLE 11-3-1-continued
Chiral
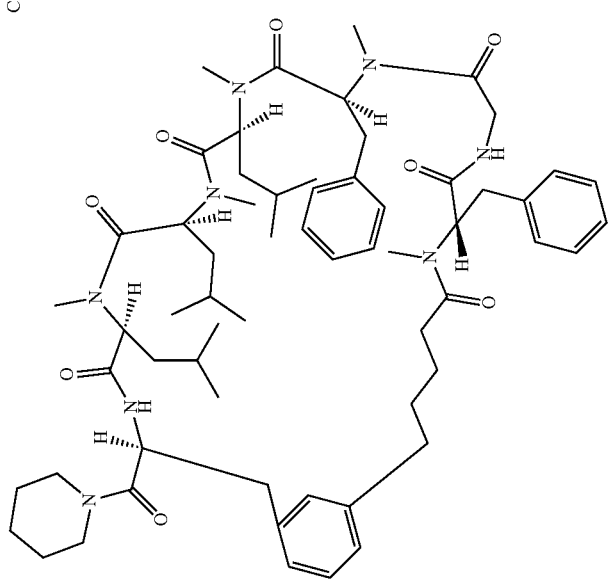
DP-844

TABLE 11-3-1-continued
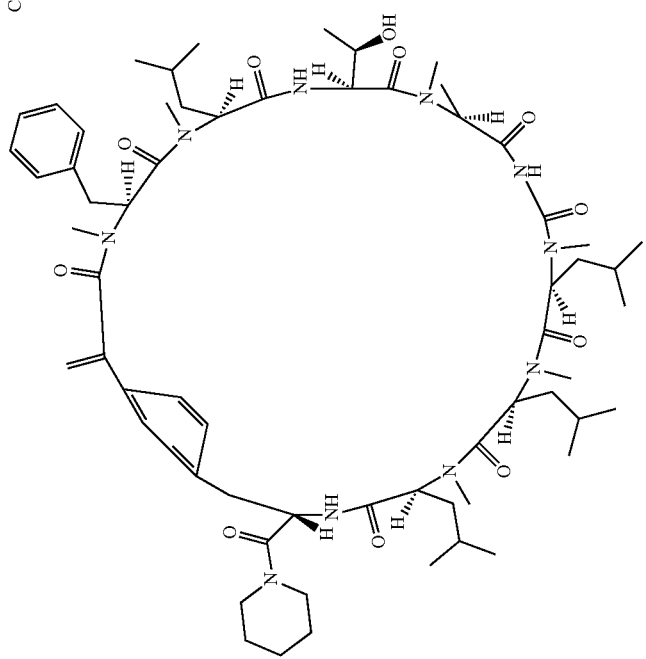
DP-845

TABLE 11-3-1-continued
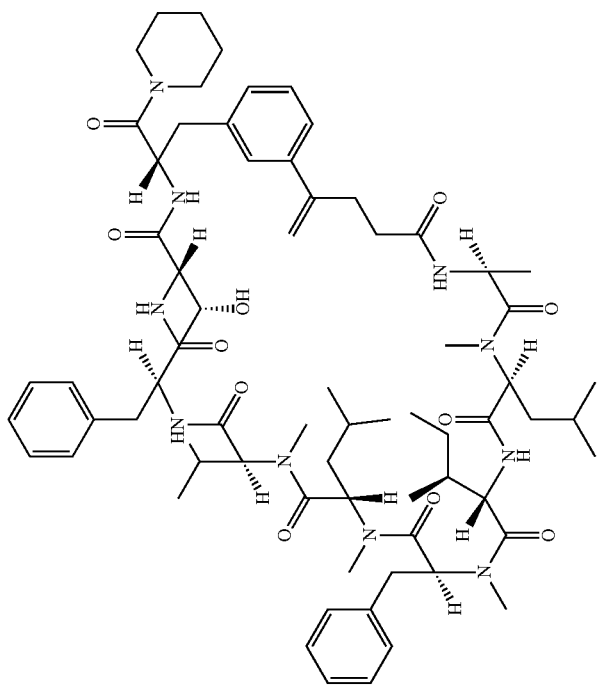
DP-846

TABLE 11-3-1-continued
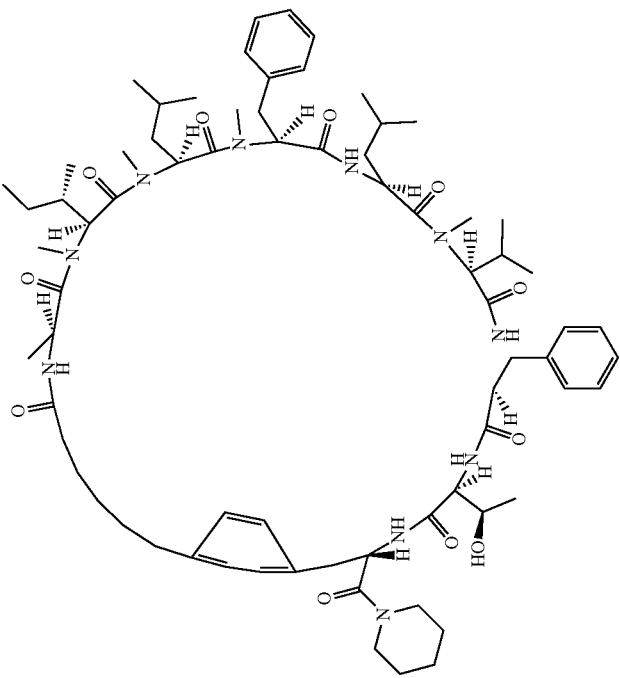
DP-847

TABLE 11-3-1-continued
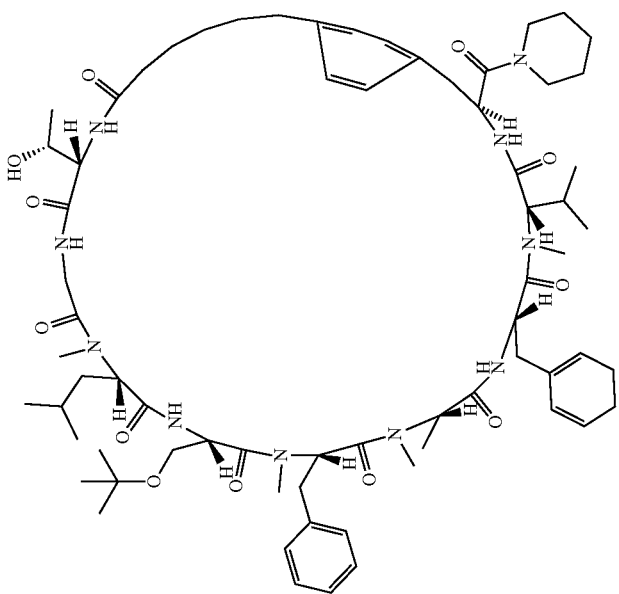
DP-848

TABLE 11-3-1-continued
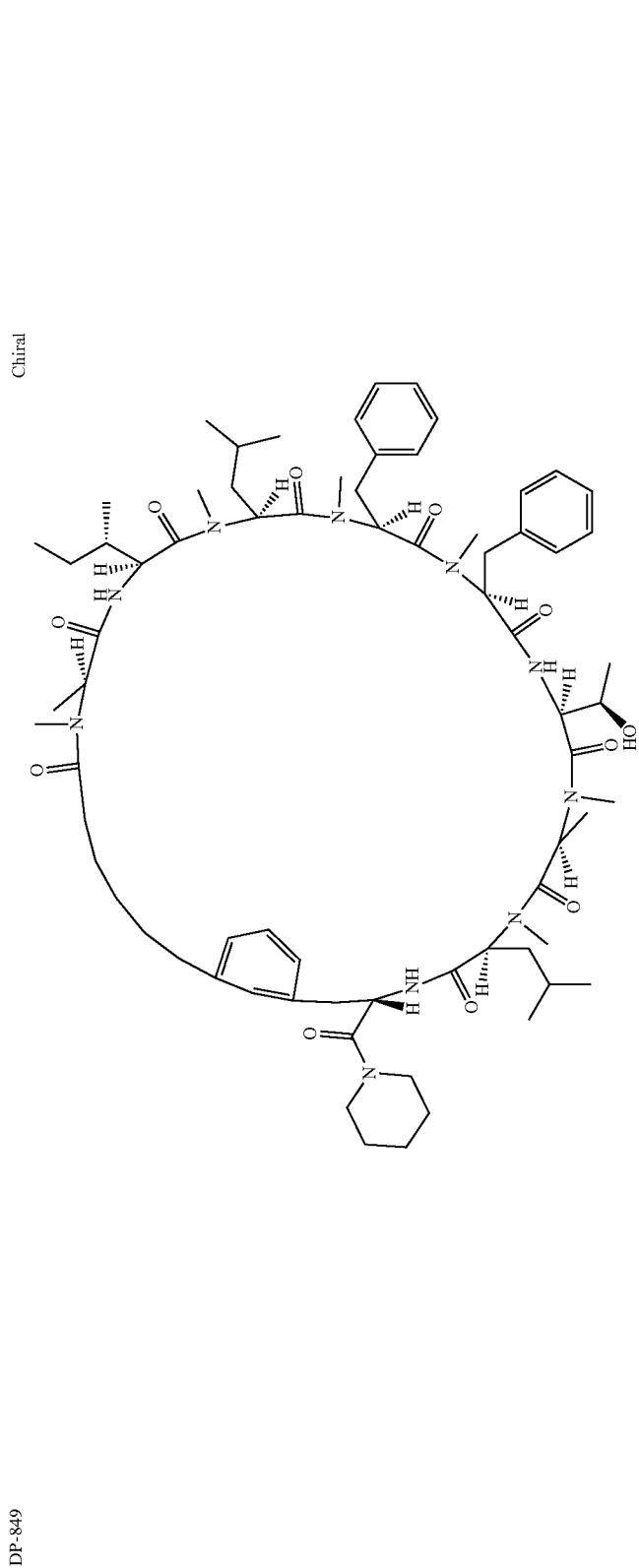
DP-849

TABLE 11-3-1-continued
DP-850
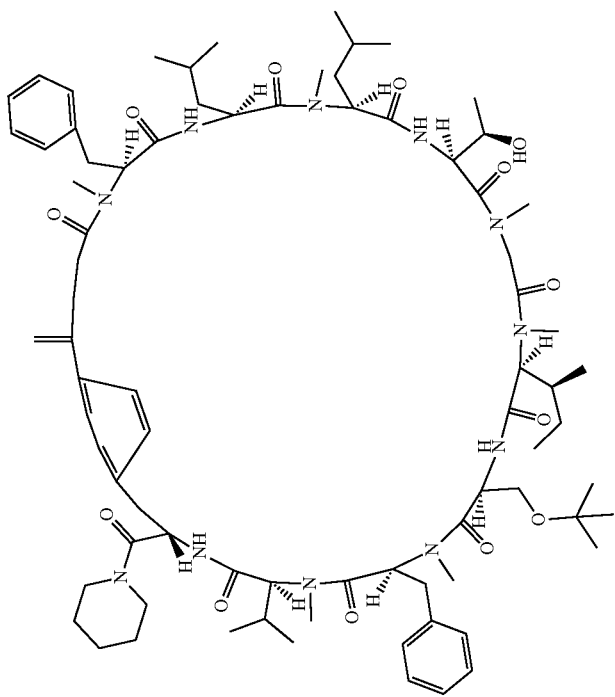

TABLE 11-3-1-continued
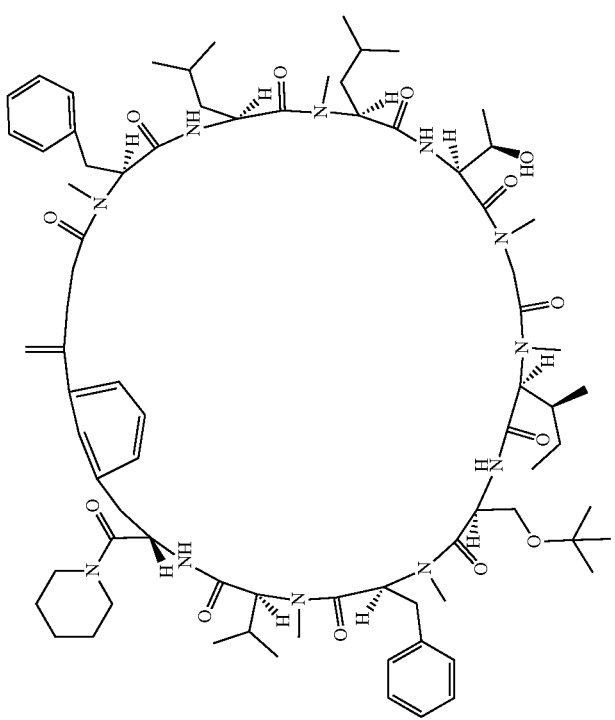
DP-851

TABLE 11-3-1-continued
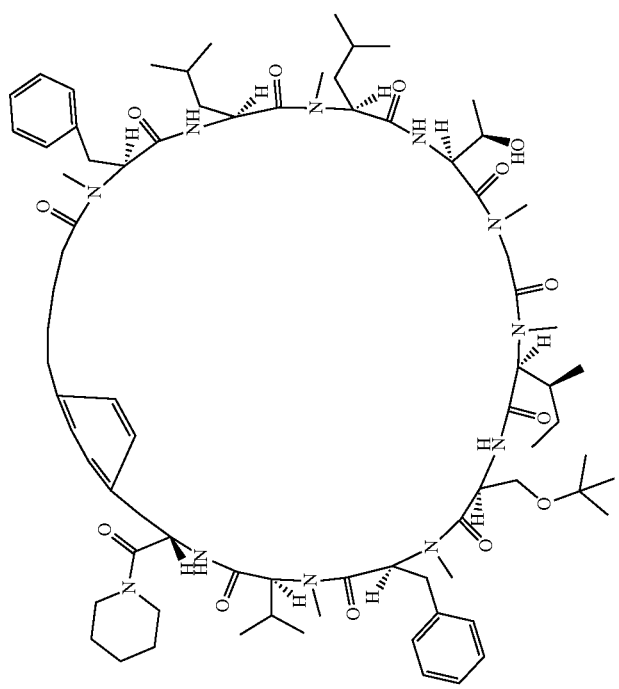
DP-852

TABLE 11-3-1-continued
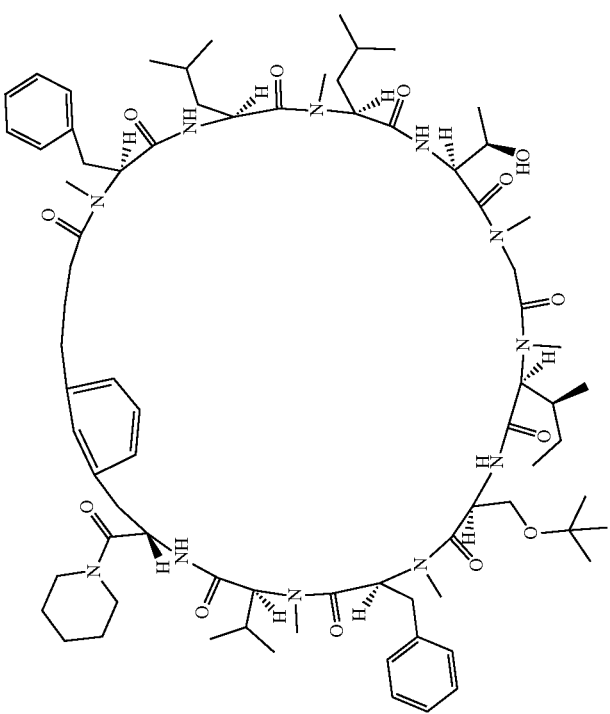
DP-853

TABLE 11-3-1-continued
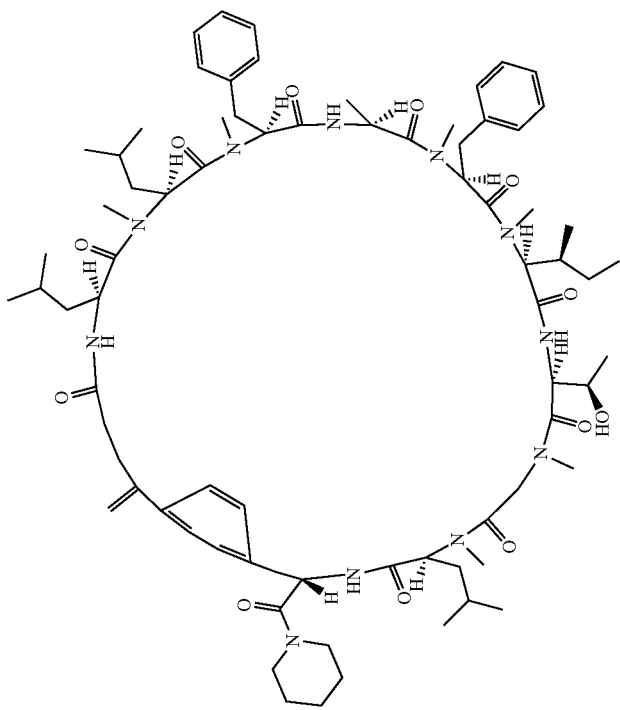
DP-854

TABLE 11-3-1-continued
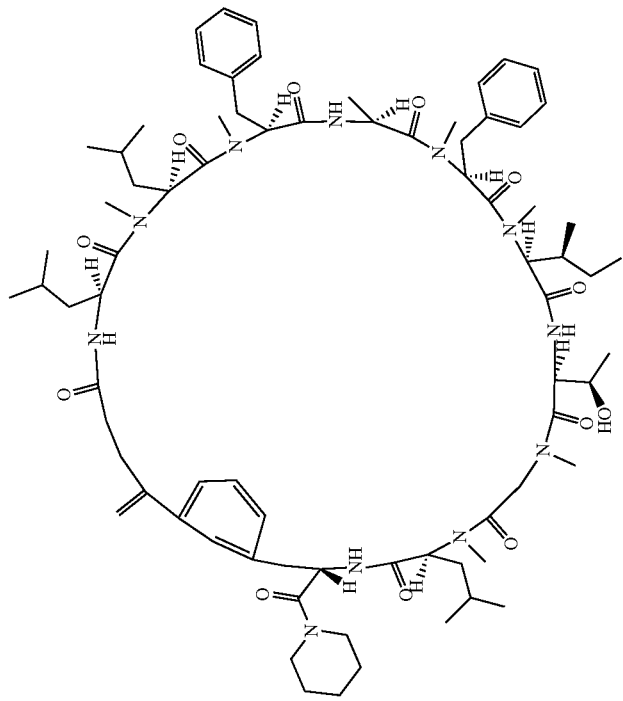
DP-855

TABLE 11-3-1-continued
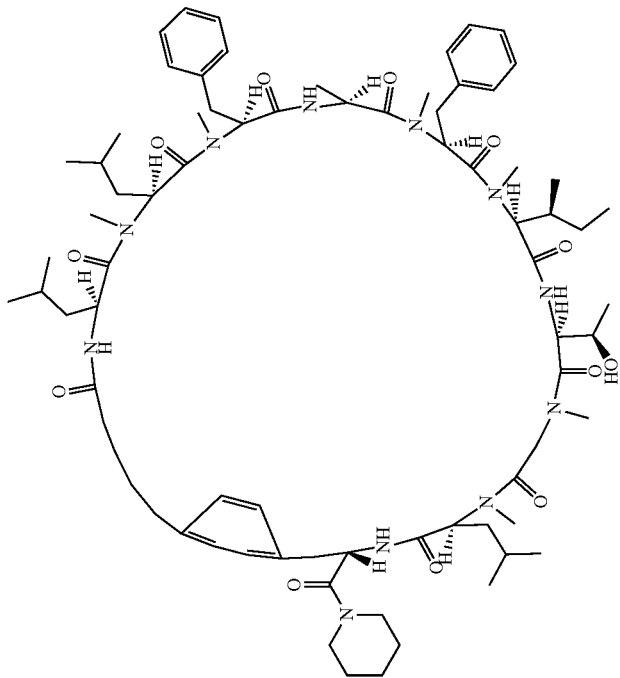
DP-856

TABLE 11-3-1-continued
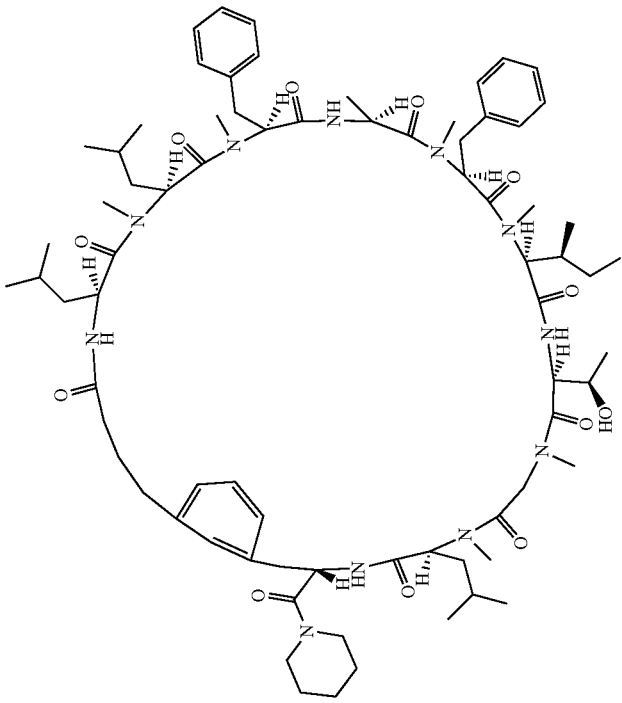
DP-857

TABLE 11-3-1-continued
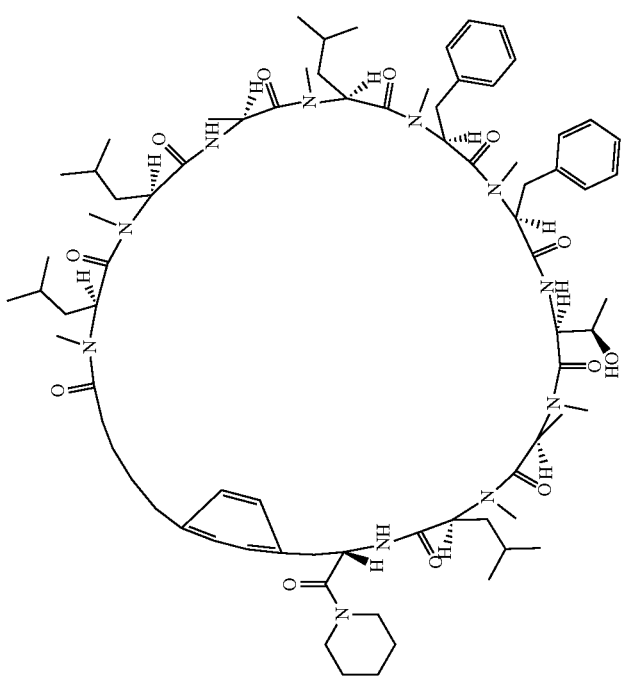
DP-858

TABLE 11-3-1-continued
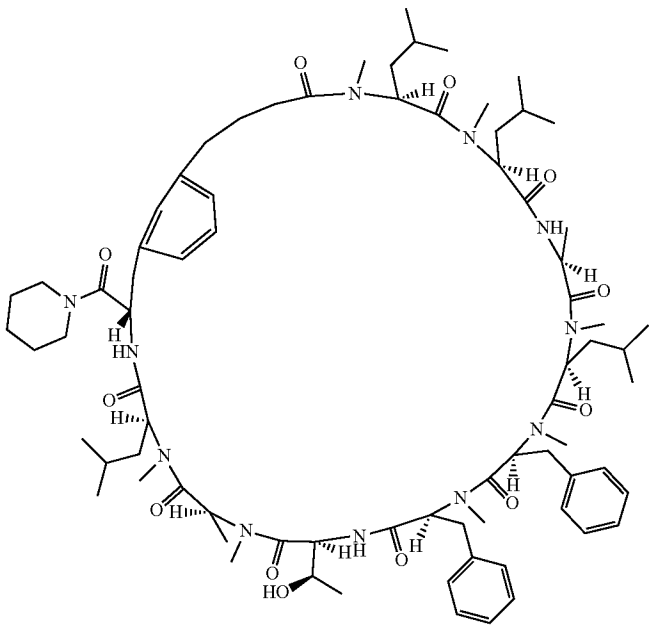
DP-859

TABLE 11-3-1-continued
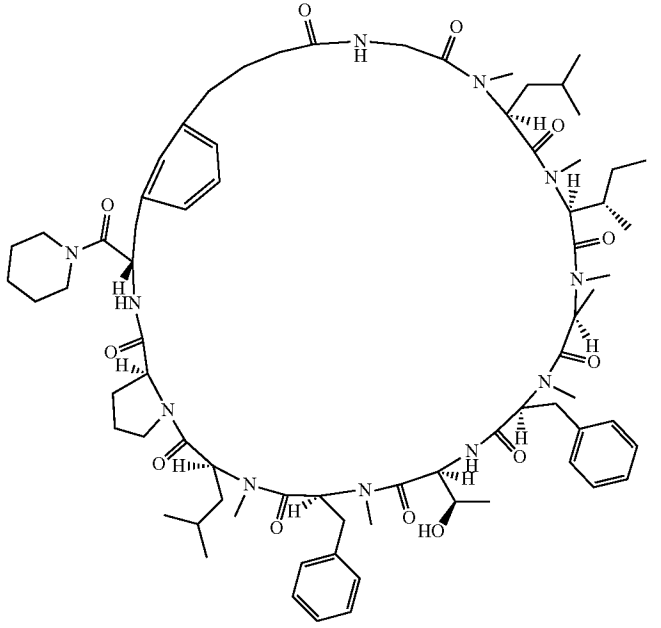
DP-860

TABLE 11-3-1-continued
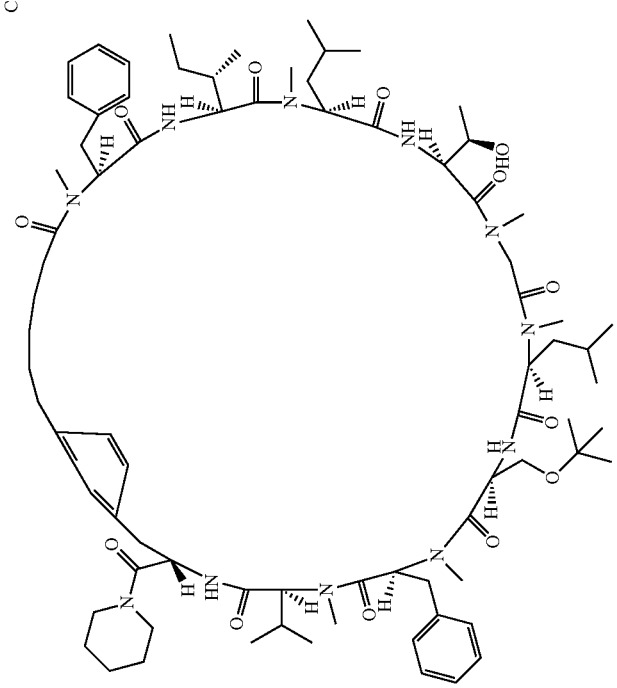
DP-861

TABLE 11-3-1-continued
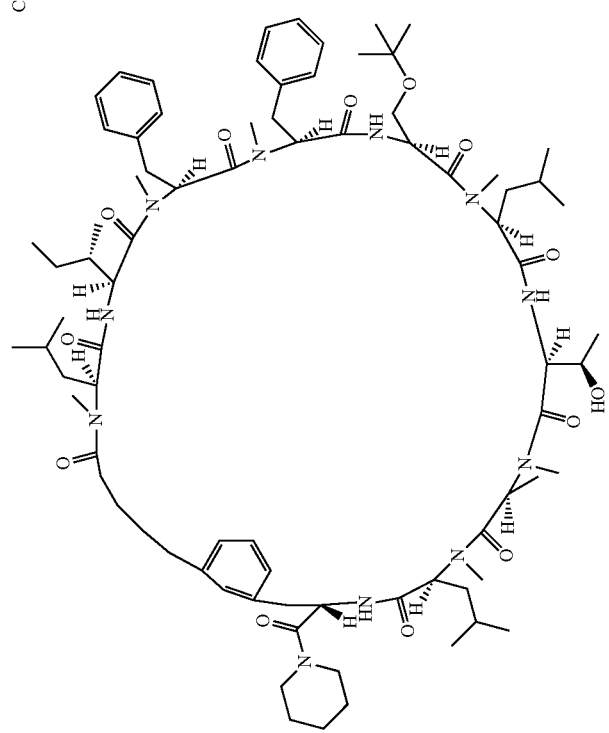
DP-862

TABLE 11-3-1-continued
Chiral
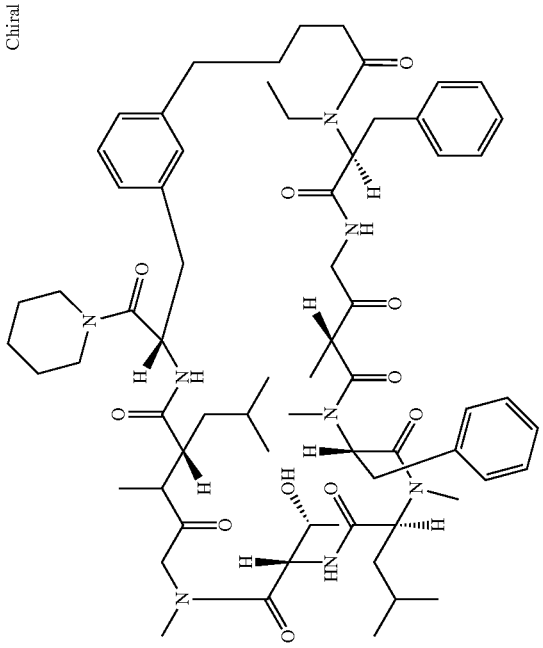
DP-863

TABLE 11-3-1-continued
DP-864
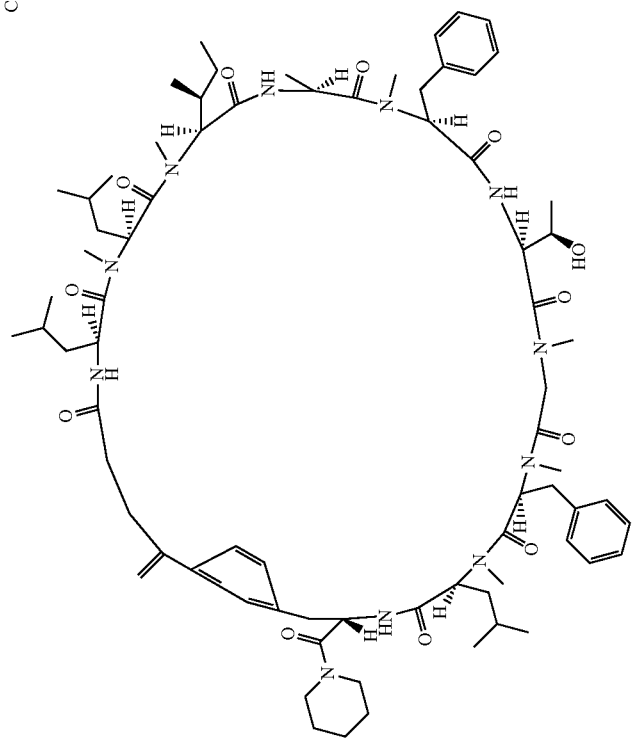

TABLE 11-3-1-continued
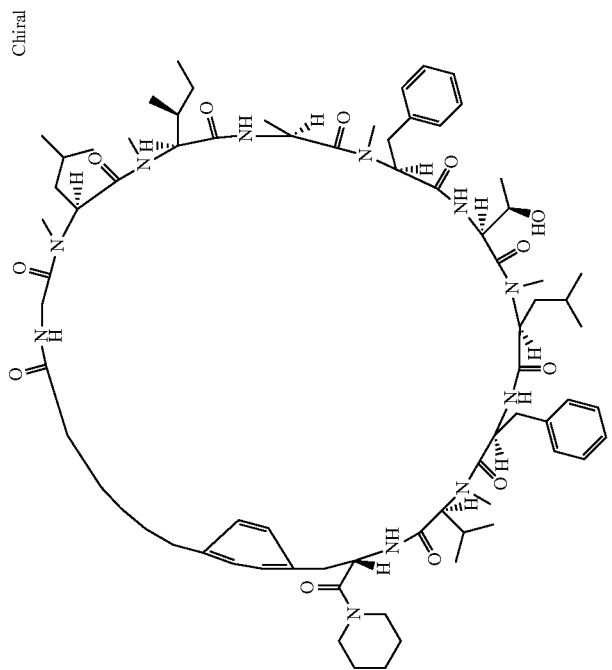
DP-865

TABLE 11-3-1-continued
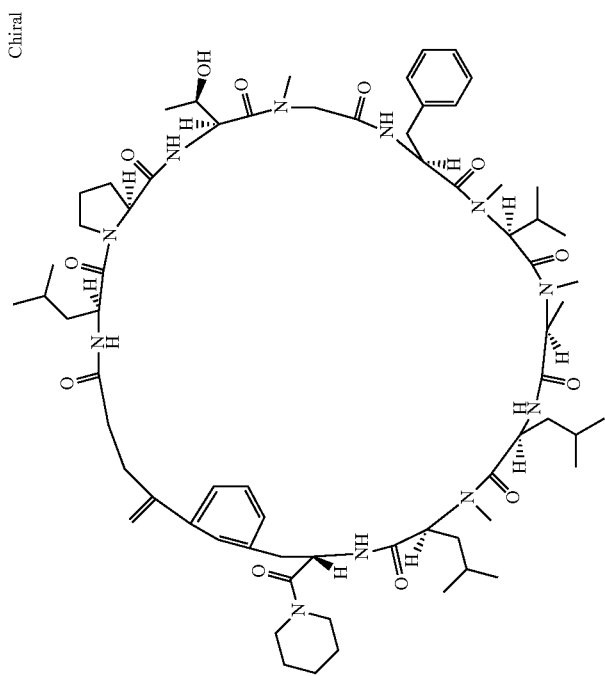
DP-866

TABLE 11-3-1-continued
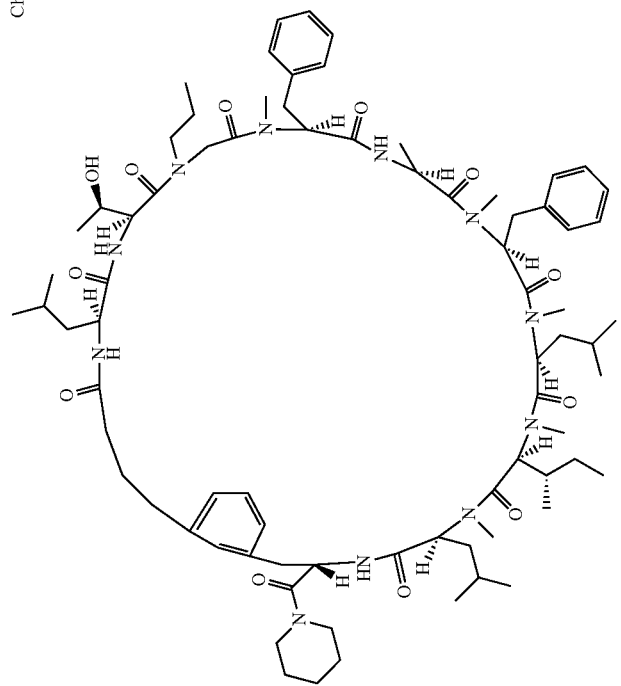
DP-867

TABLE 11-3-1-continued
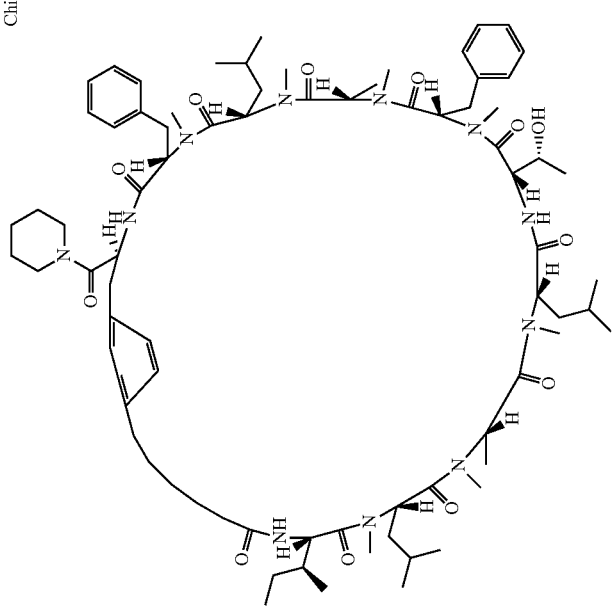
DP-868

TABLE 11-3-1-continued
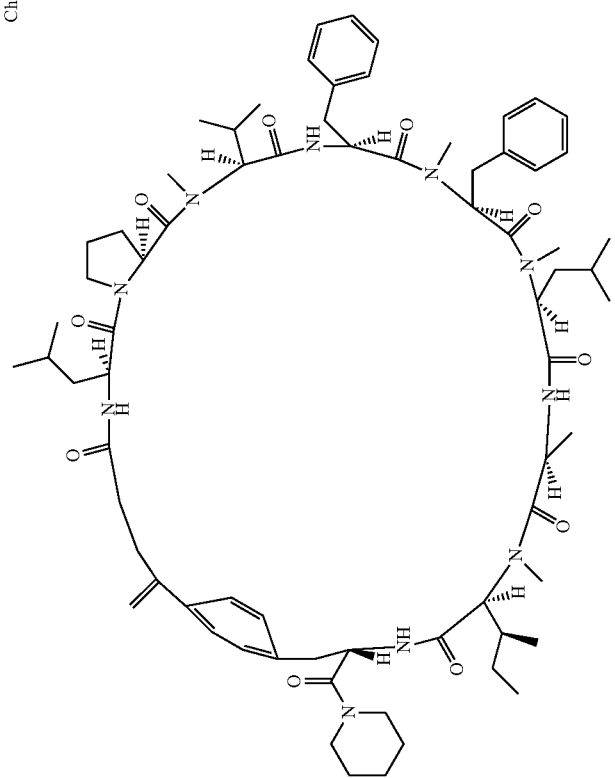
DP-869

TABLE 11-3-1-continued

DP-870

TABLE 11-3-1-continued
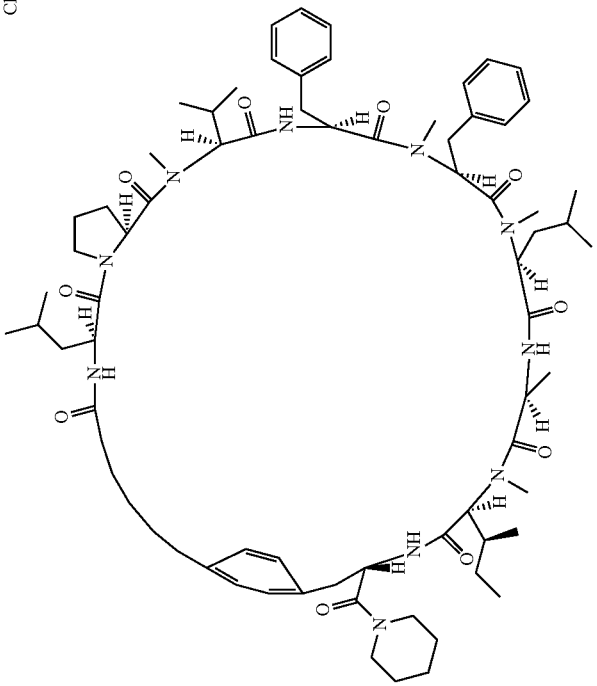
DP-871

TABLE 11-3-1-continued
DP-872

TABLE 11-3-1-continued
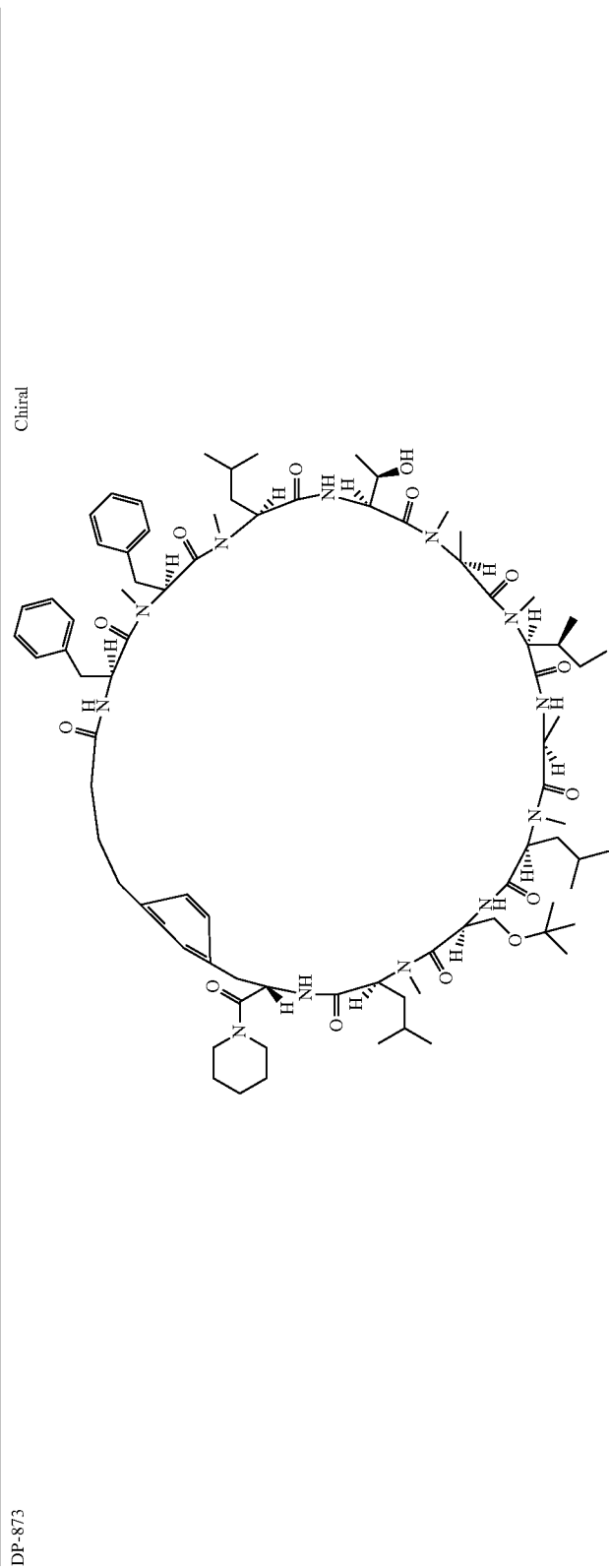
DP-873

TABLE 11-3-1-continued
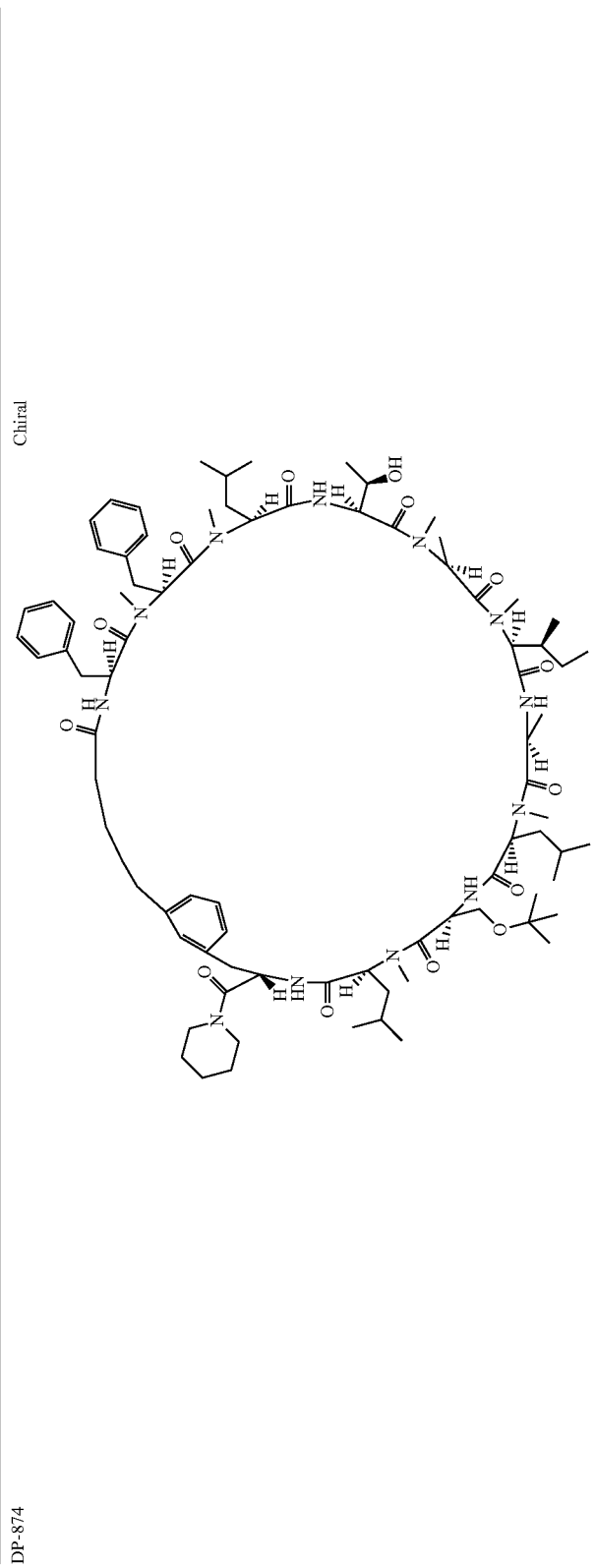

TABLE 11-3-1-continued
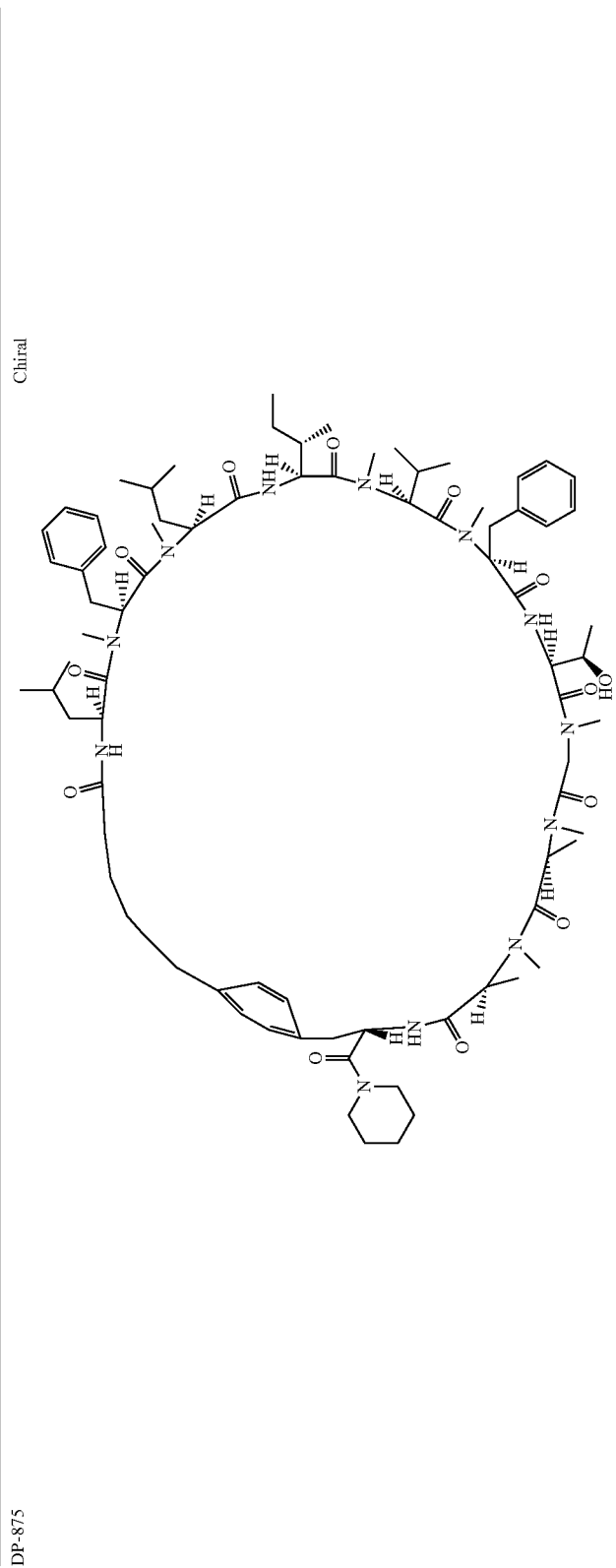
DP-875

TABLE 11-3-1-continued
DP-876
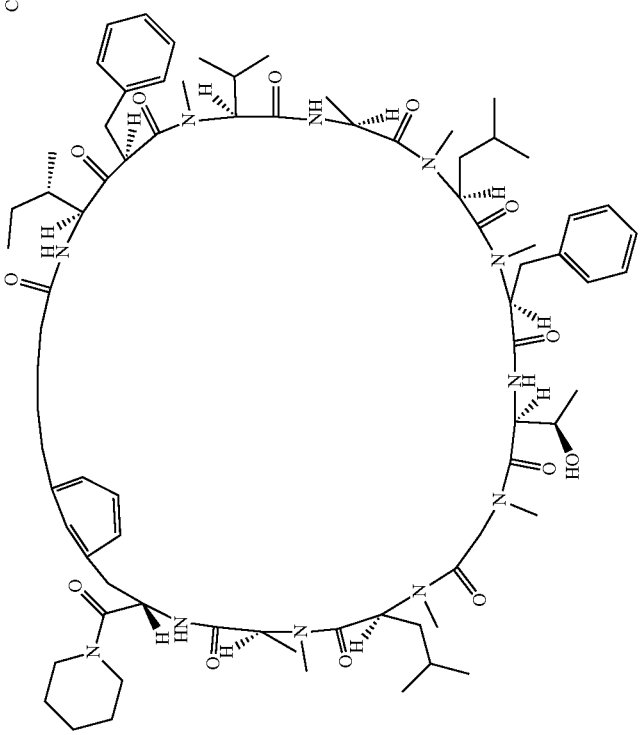

TABLE 11-3-1-continued
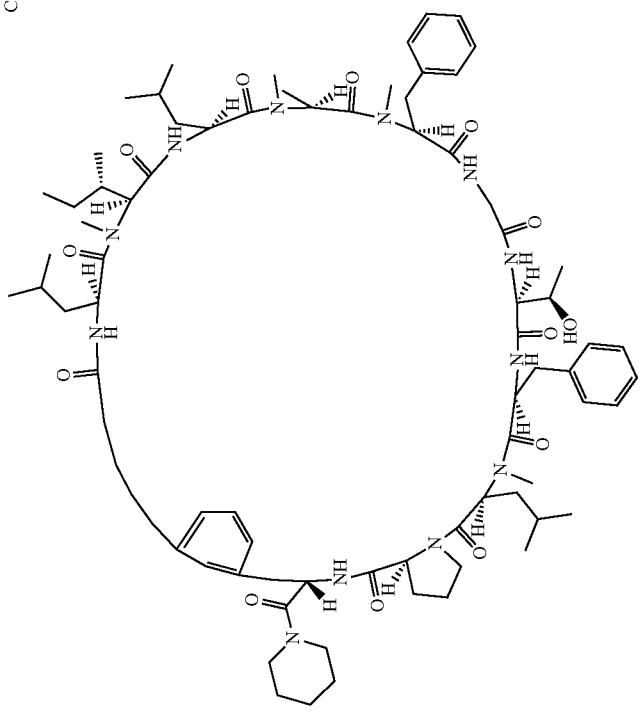
DP-877

TABLE 11-3-1-continued
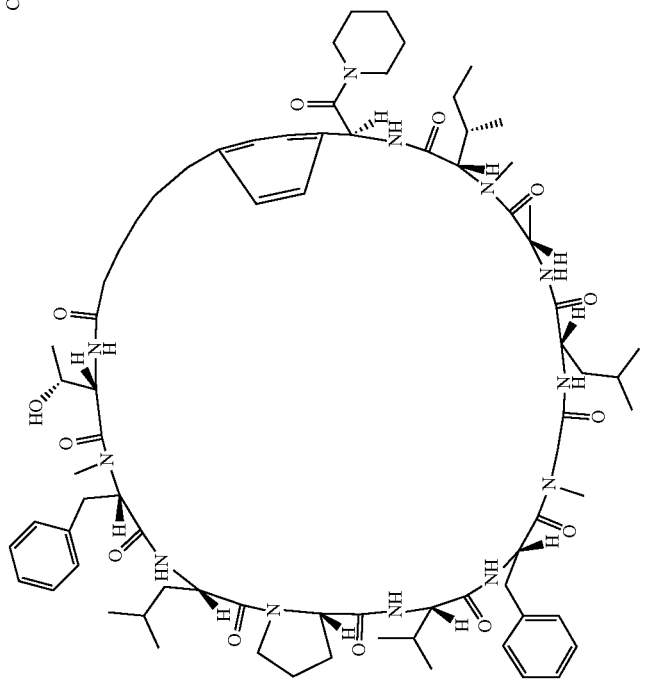
DP-878

TABLE 11-3-1-continued
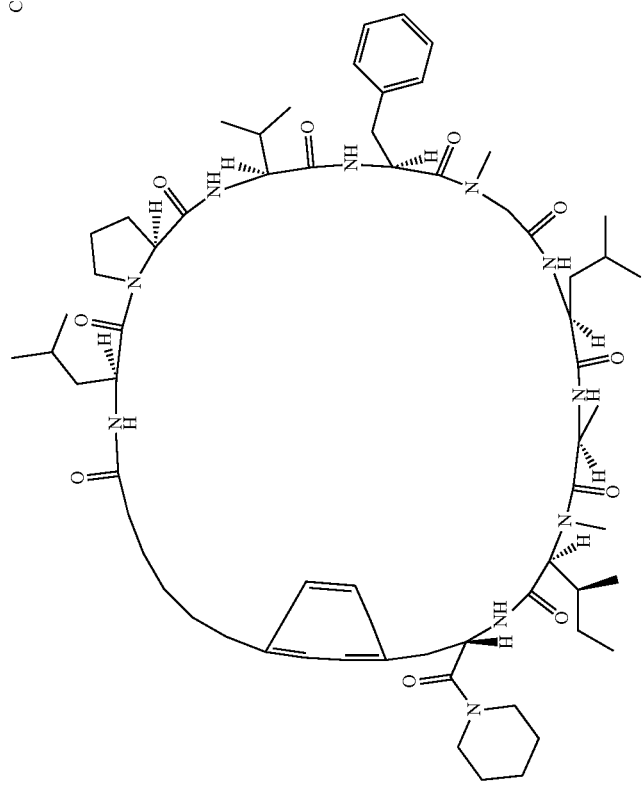
DP-879

TABLE 11-3-1-continued
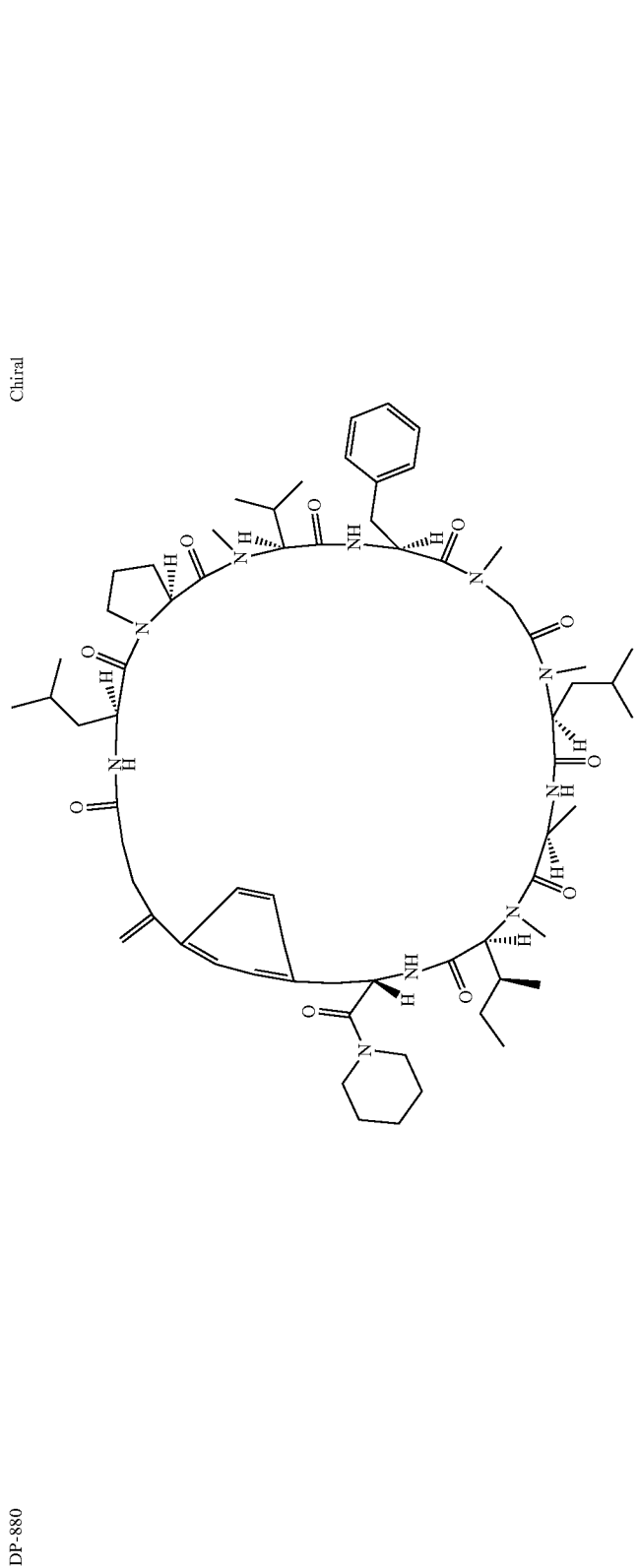
DP-880

TABLE 11-3-1-continued
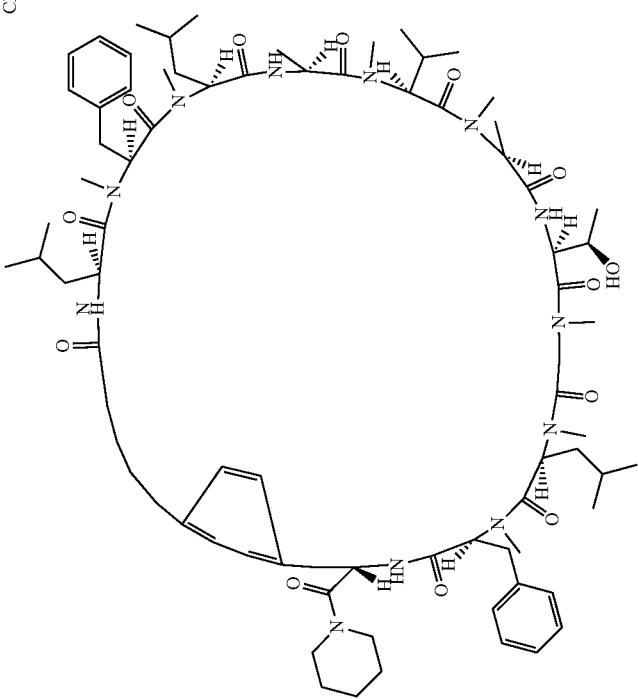
DP-881

TABLE 11-3-1-continued
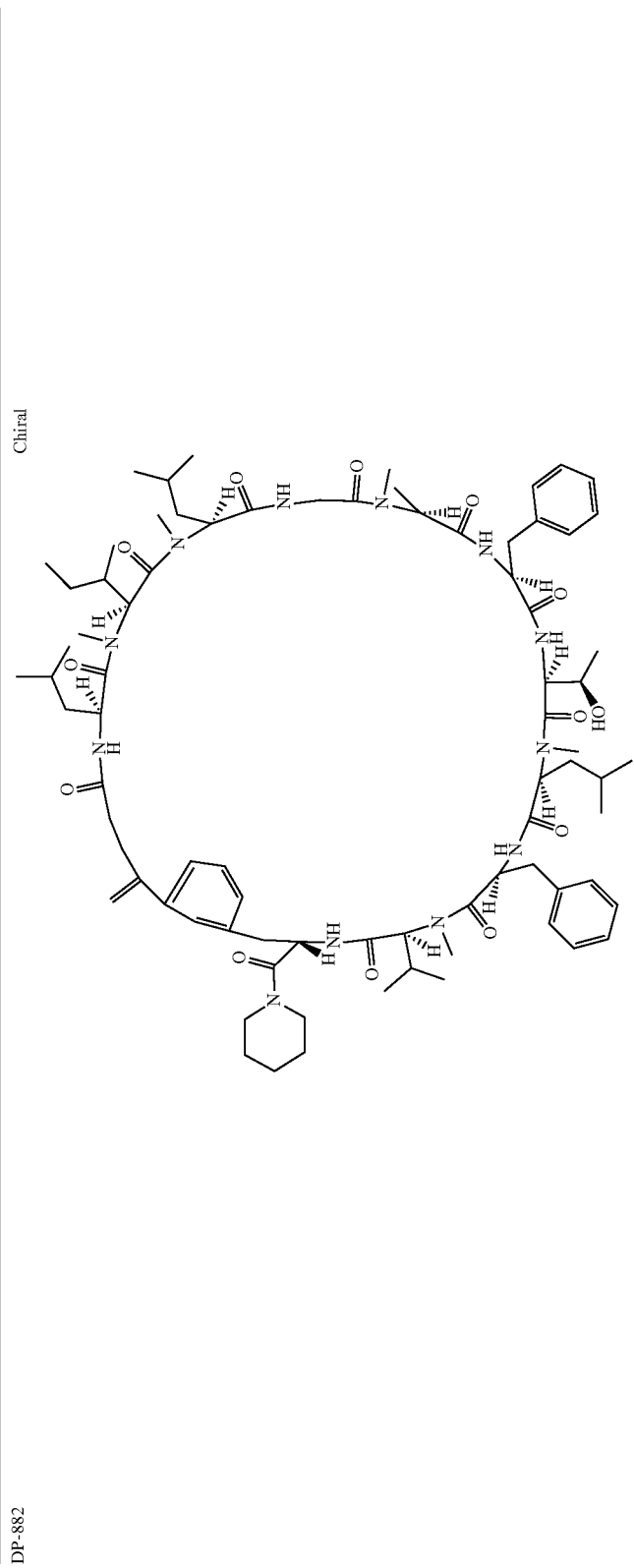
DP-882

TABLE 11-3-1-continued
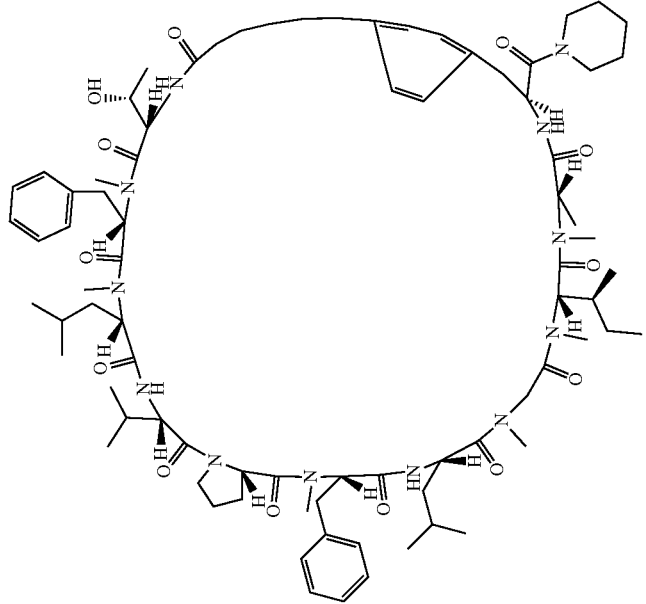
DP-883

TABLE 11-3-1-continued
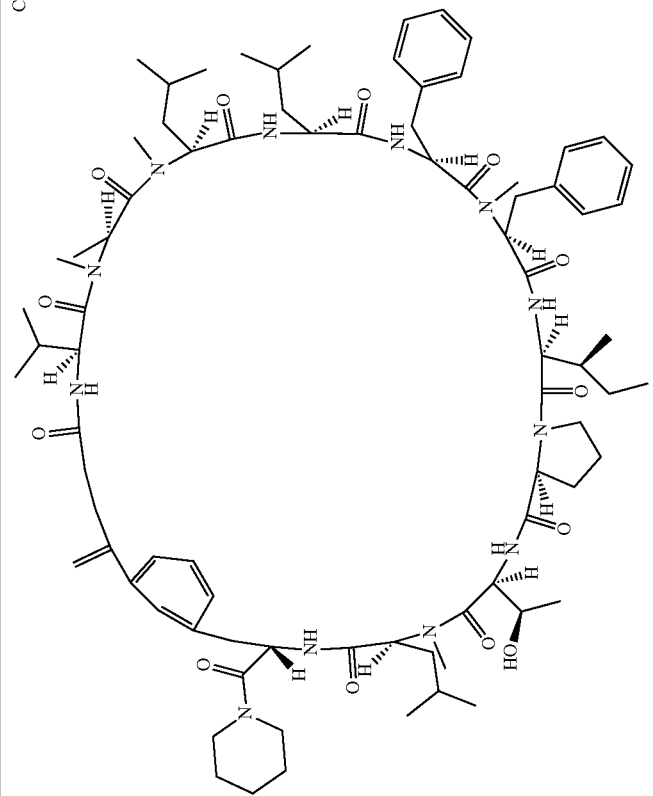
DP-884

TABLE 11-3-1-continued
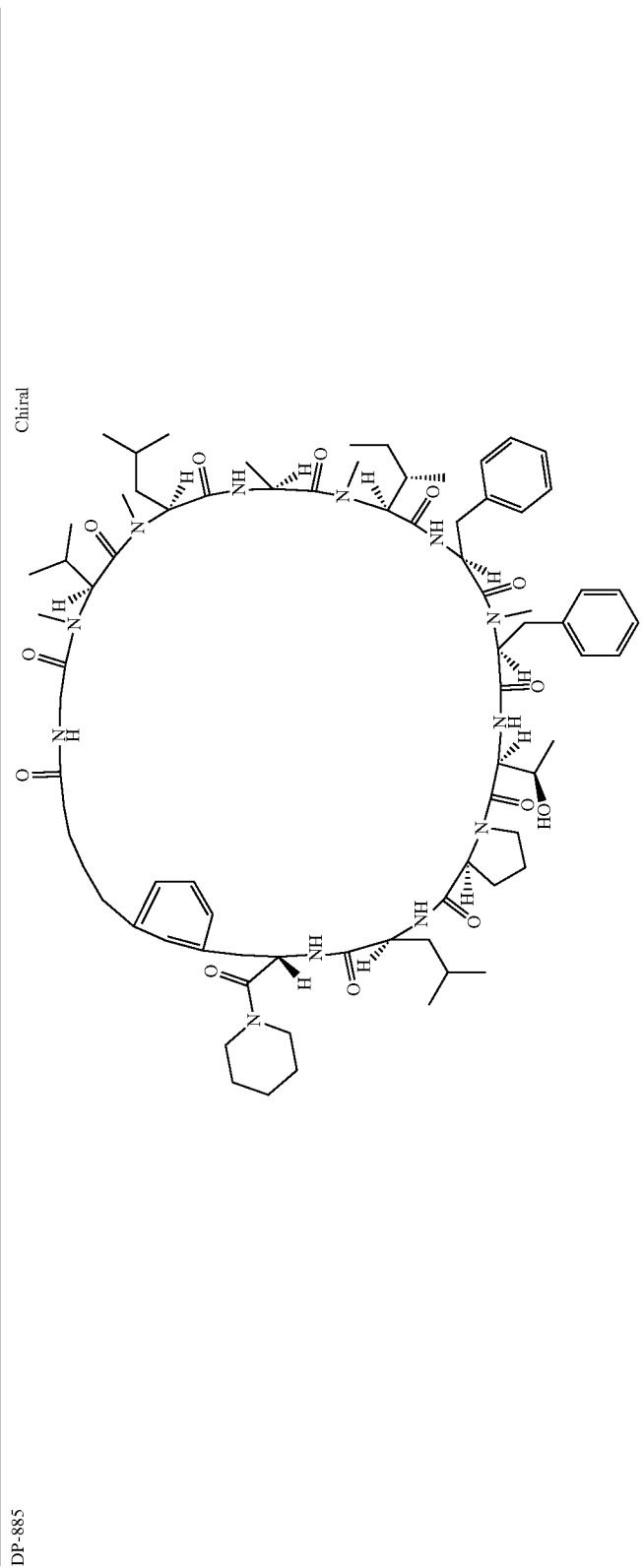
DP-885

TABLE 11-3-1-continued
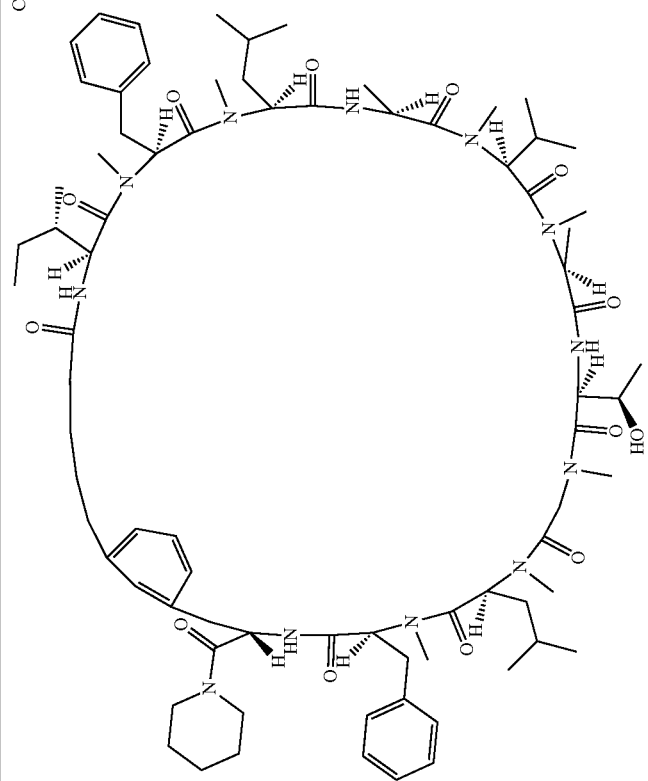
DP-886

TABLE 11-3-1-continued
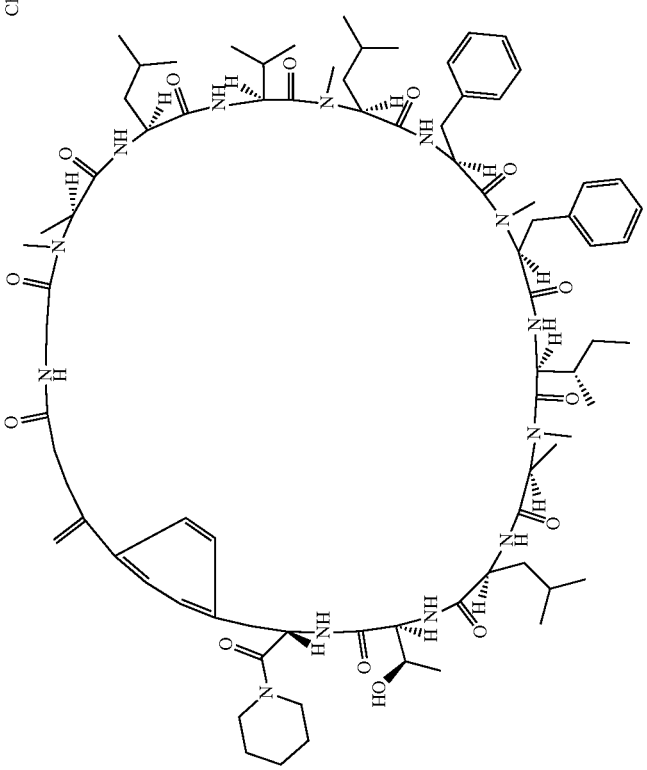
DP-887

TABLE 11-3-1-continued
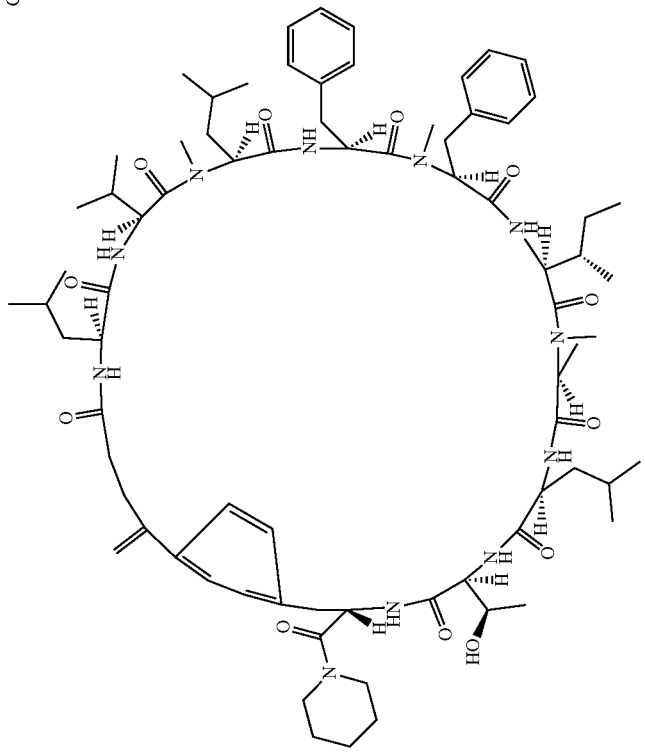
DP-888

TABLE 11-3-1-continued
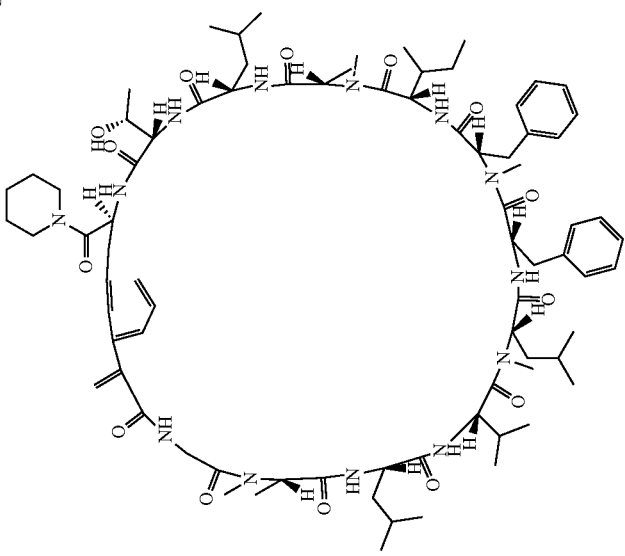
DP-889

TABLE 11-3-1-continued
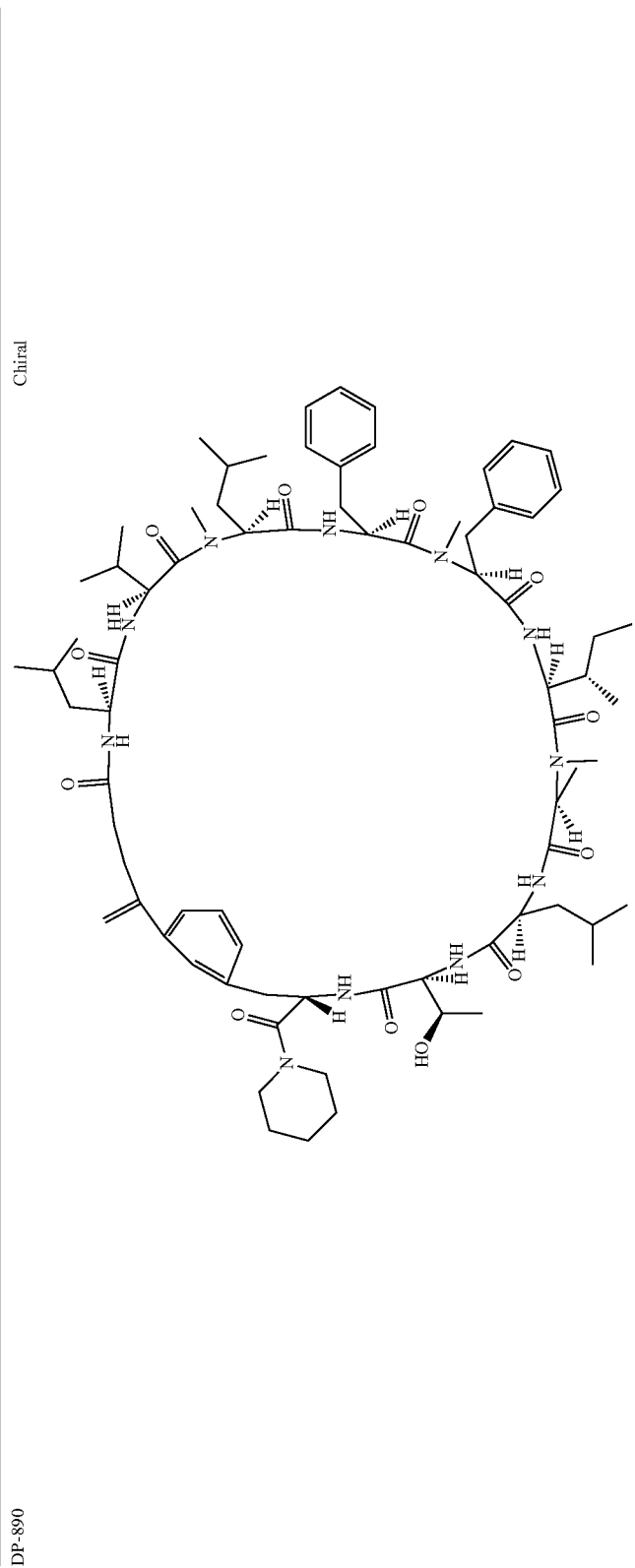
DP-890

TABLE 11-3-1-continued
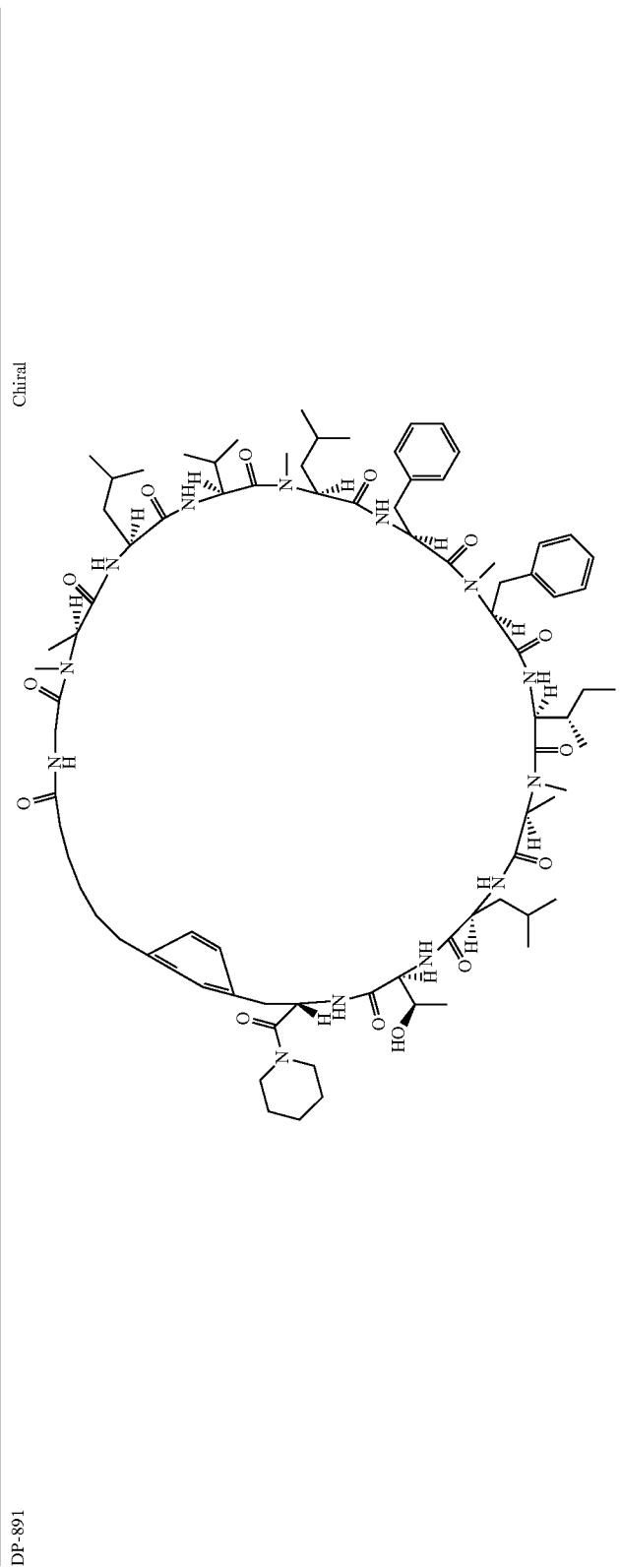
DP-891

TABLE 11-3-1-continued
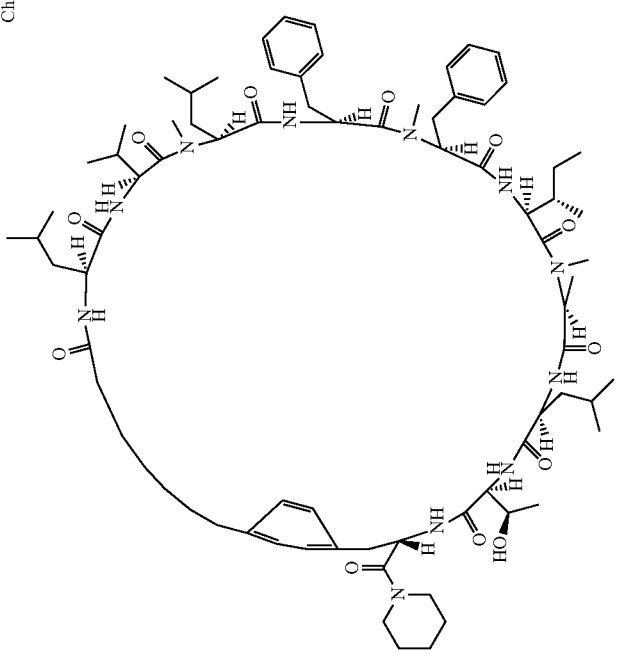
DP-892

TABLE 11-3-1-continued
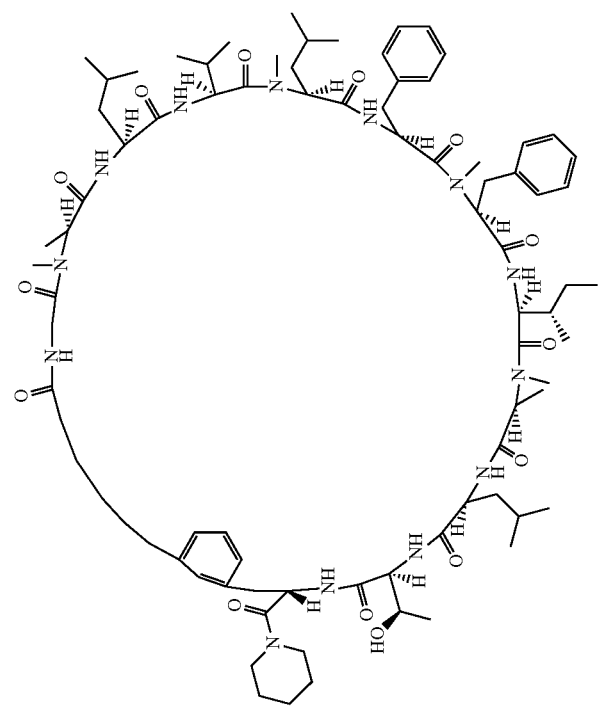
DP-893

TABLE 11-3-1-continued
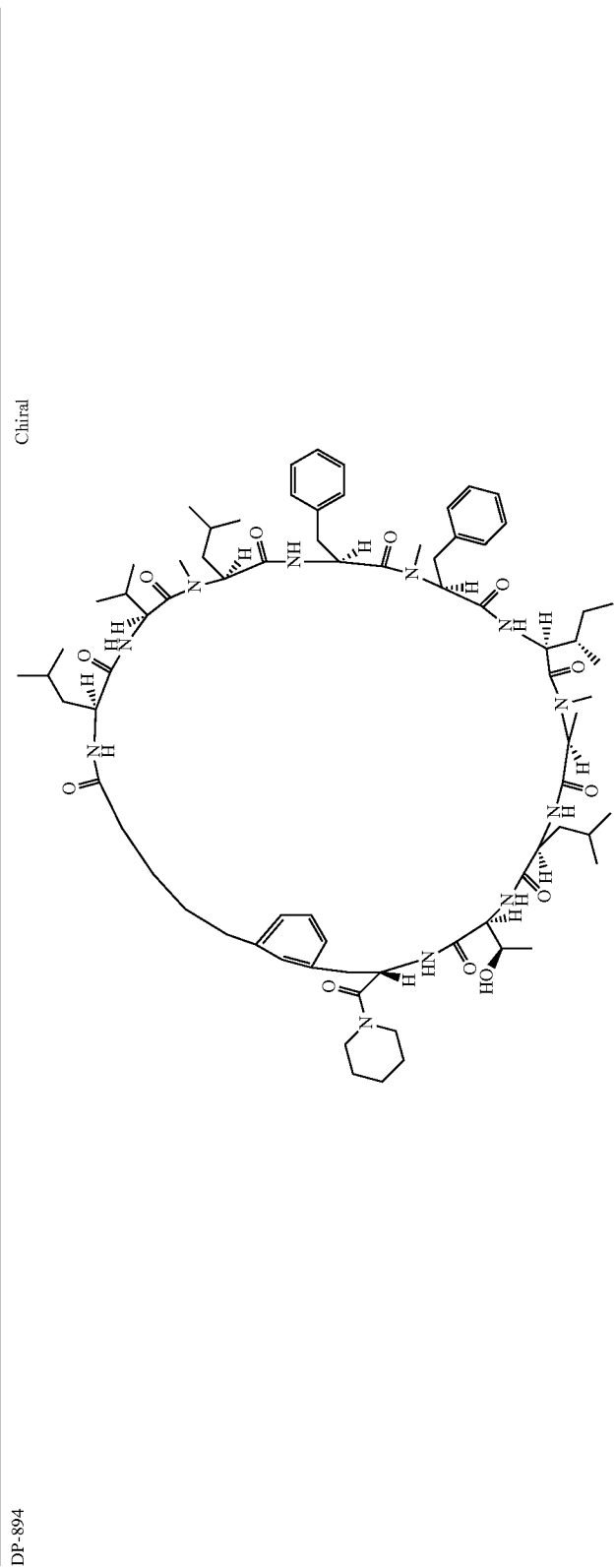
DP-894

TABLE 11-3-1-continued
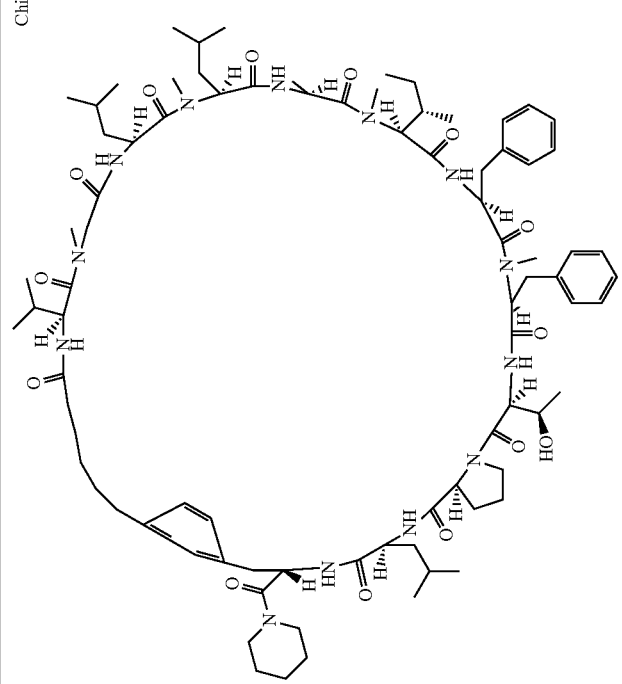
DP-895

TABLE 11-3-1-continued
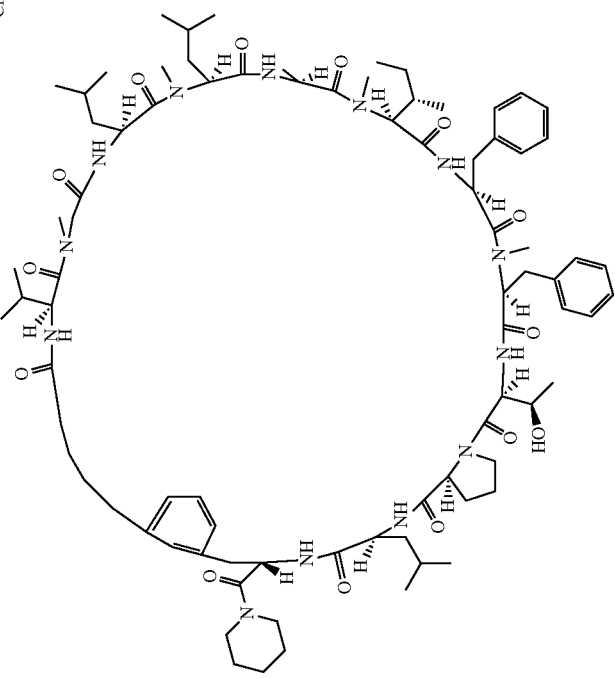
DP-896

TABLE 11-3-1-continued
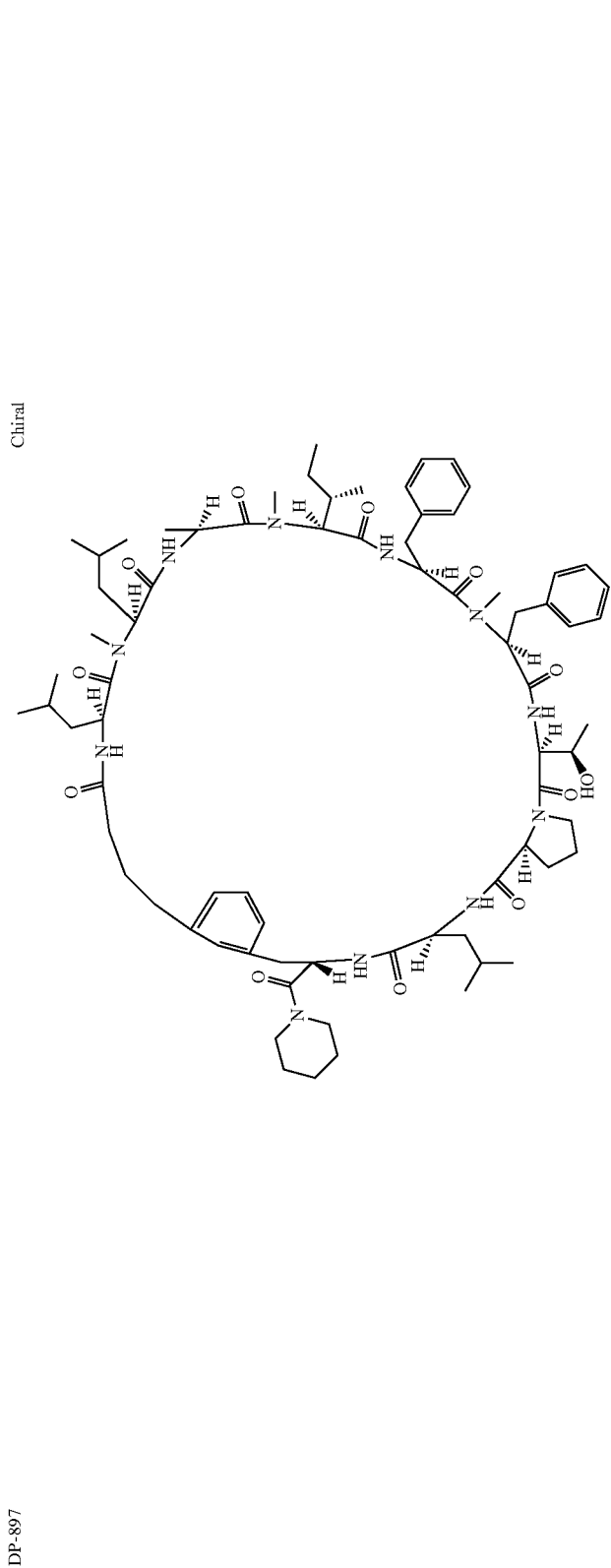
DP-897

TABLE 11-3-1-continued
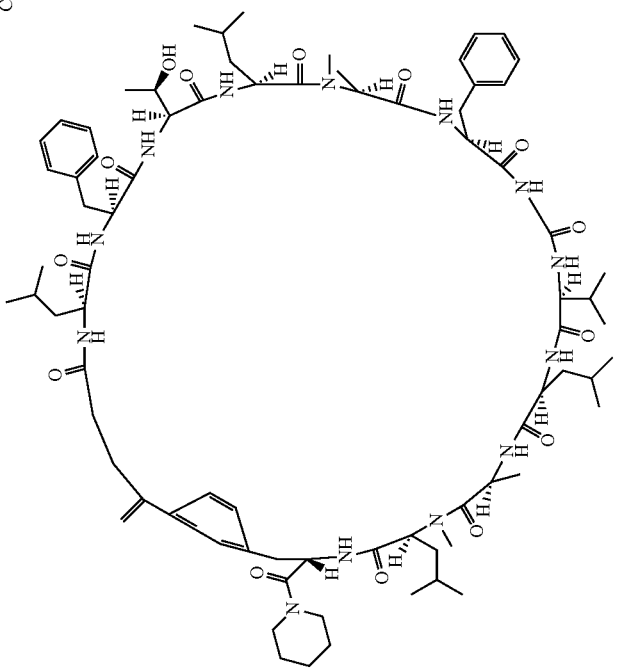

TABLE 11-3-1-continued
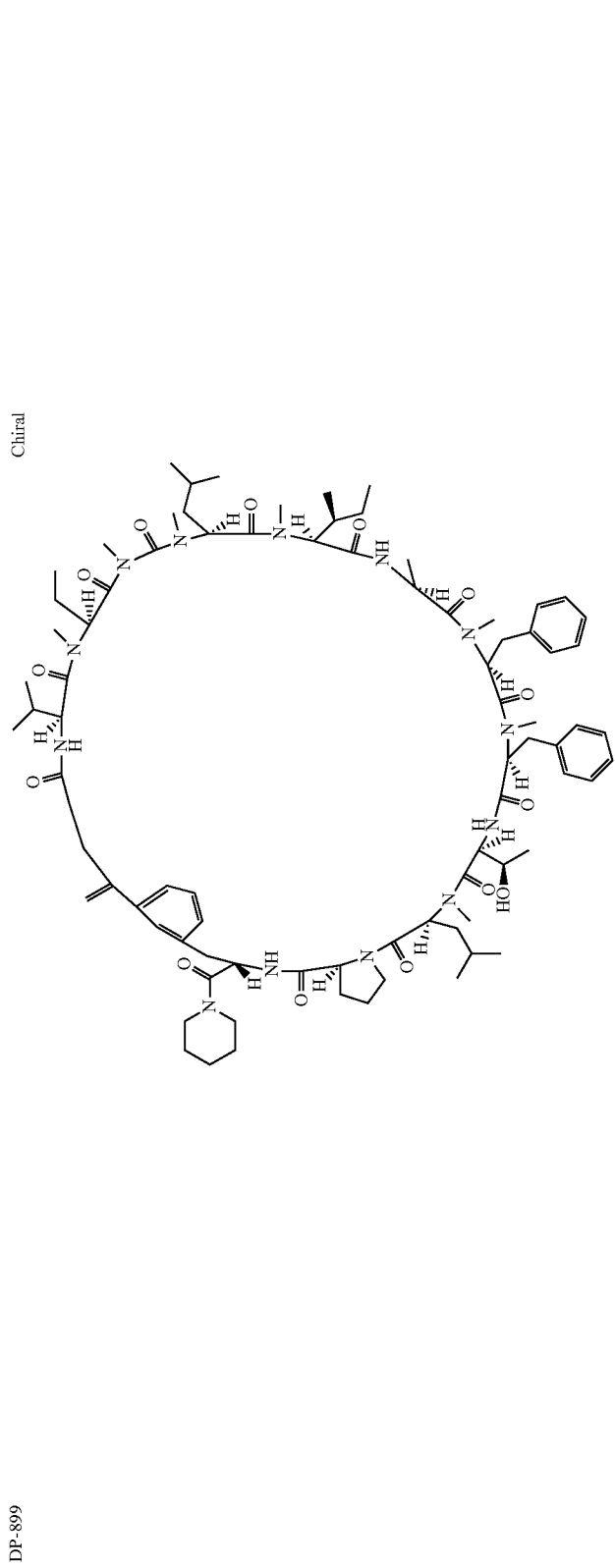
DP-899

TABLE 11-3-1-continued
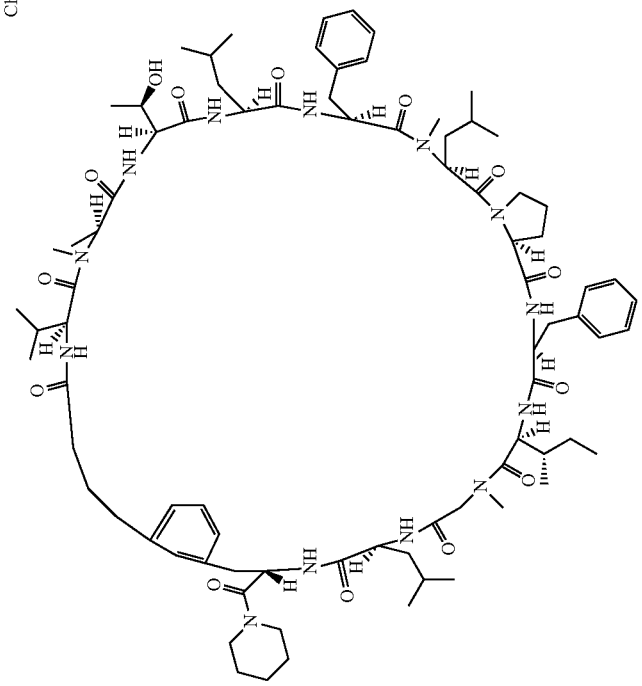
DP-900

TABLE 11-3-1-continued
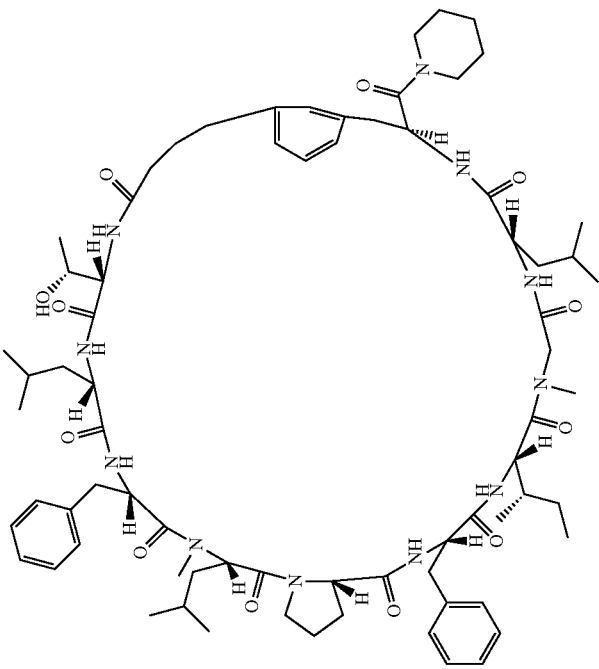
DP-901

TABLE 11-3-1-continued
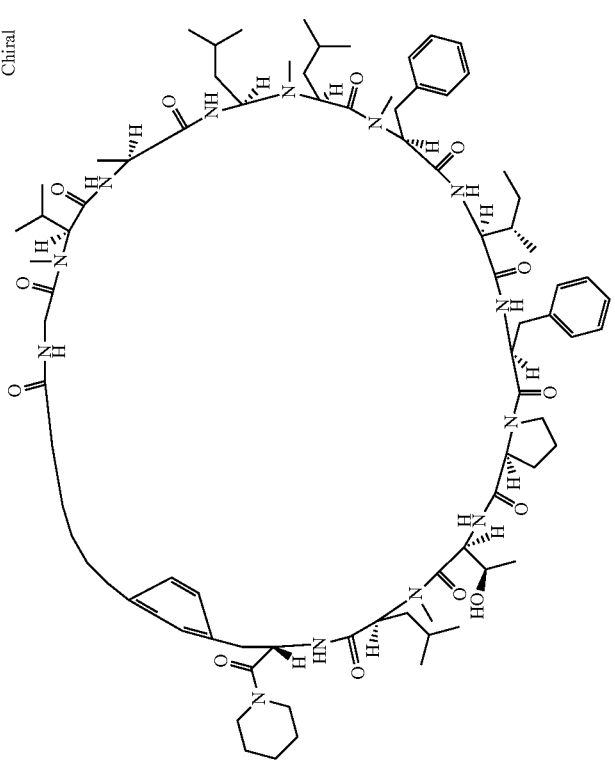
DP-902

TABLE 11-3-1-continued
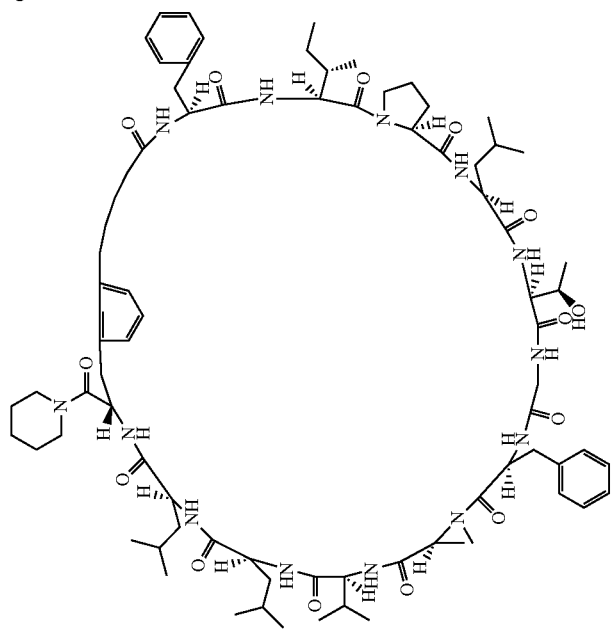
DP-903

TABLE 11-3-1-continued
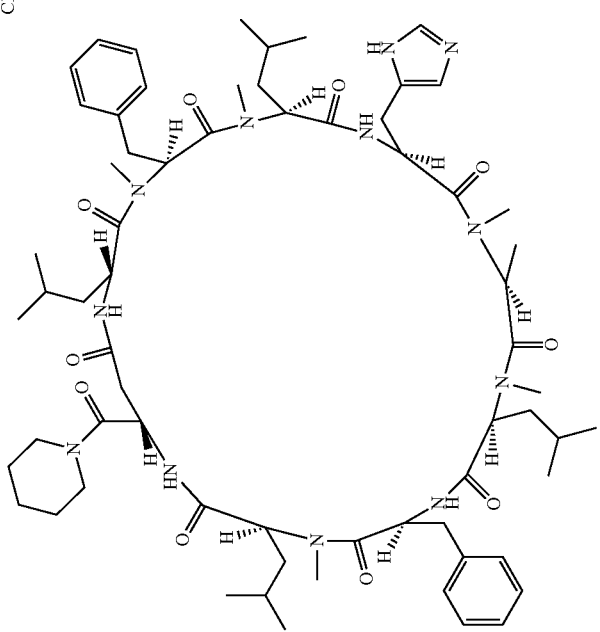
DP-904

TABLE 11-3-1-continued
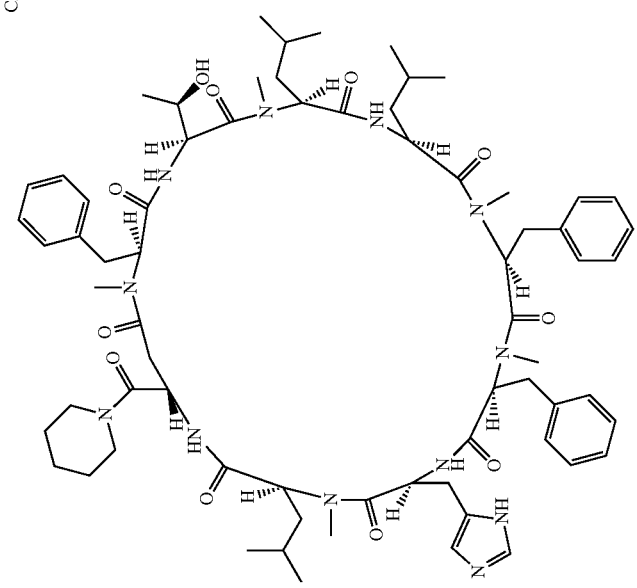
DP-905

TABLE 11-3-1-continued
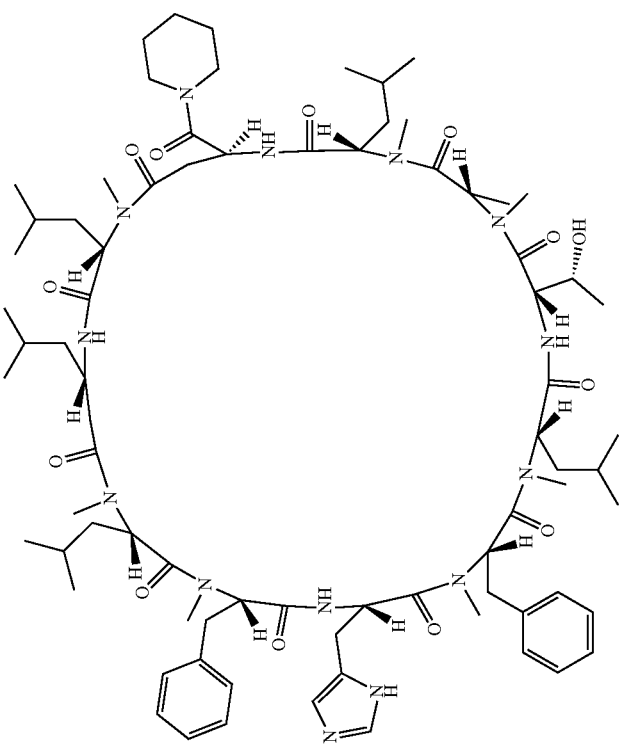
DP-906

TABLE 11-3-1-continued
DP-907
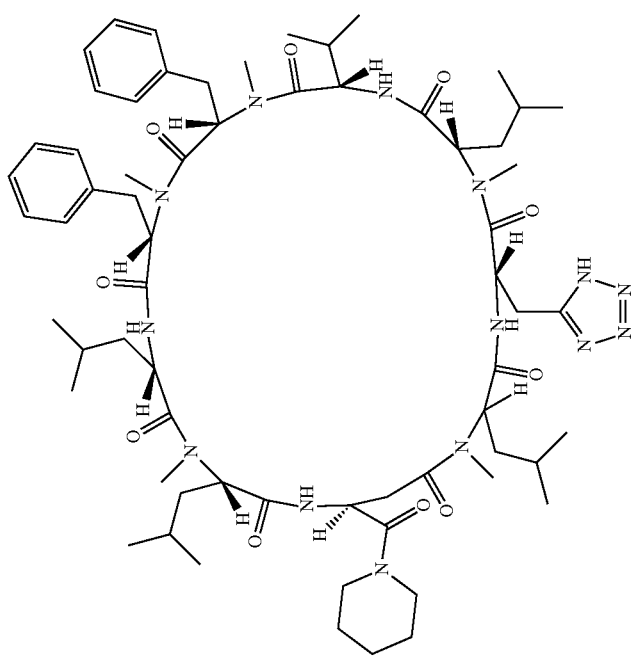

TABLE 11-3-1-continued
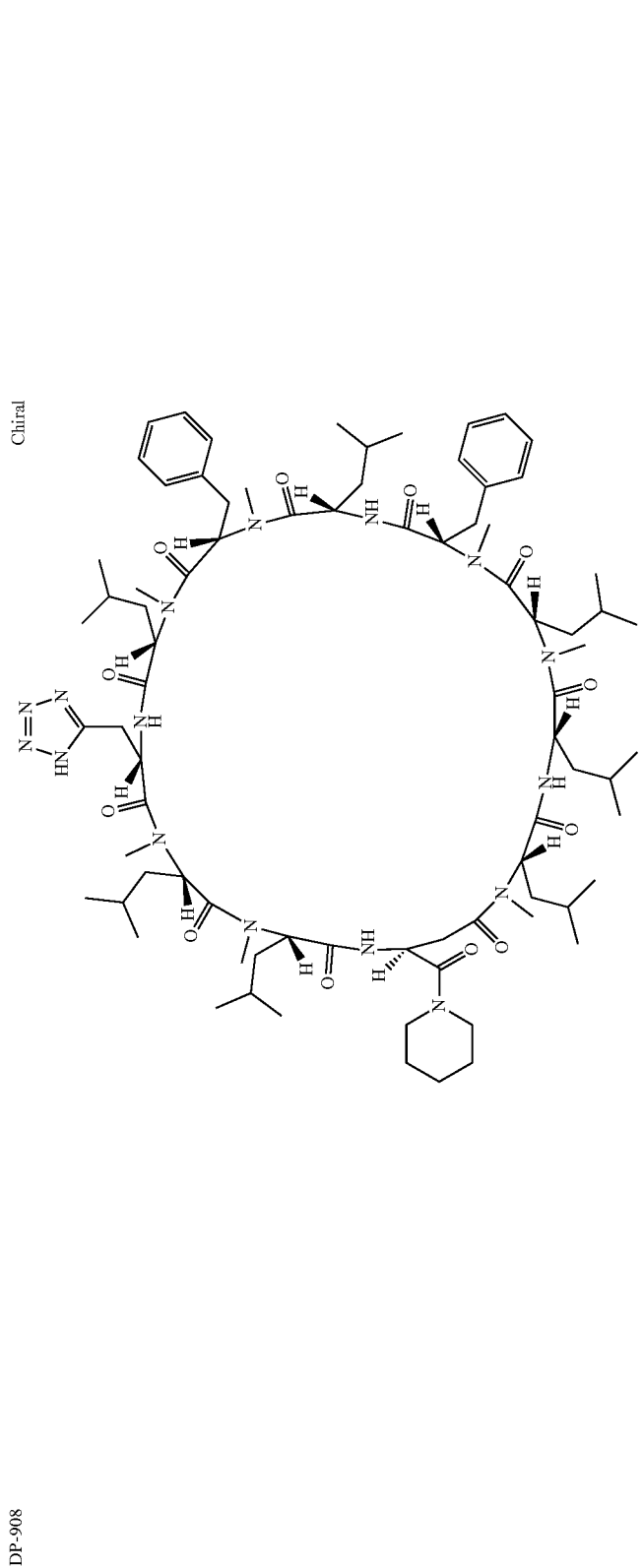
DP-908

TABLE 11-3-1-continued
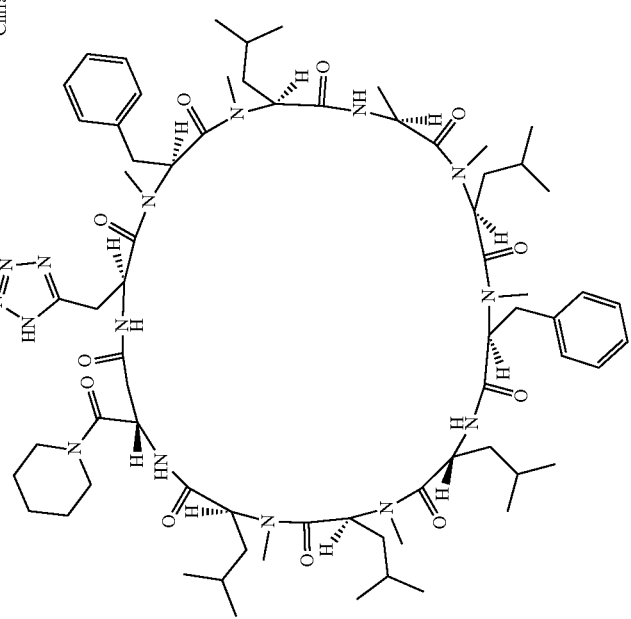
DP-909

TABLE 11-3-1-continued
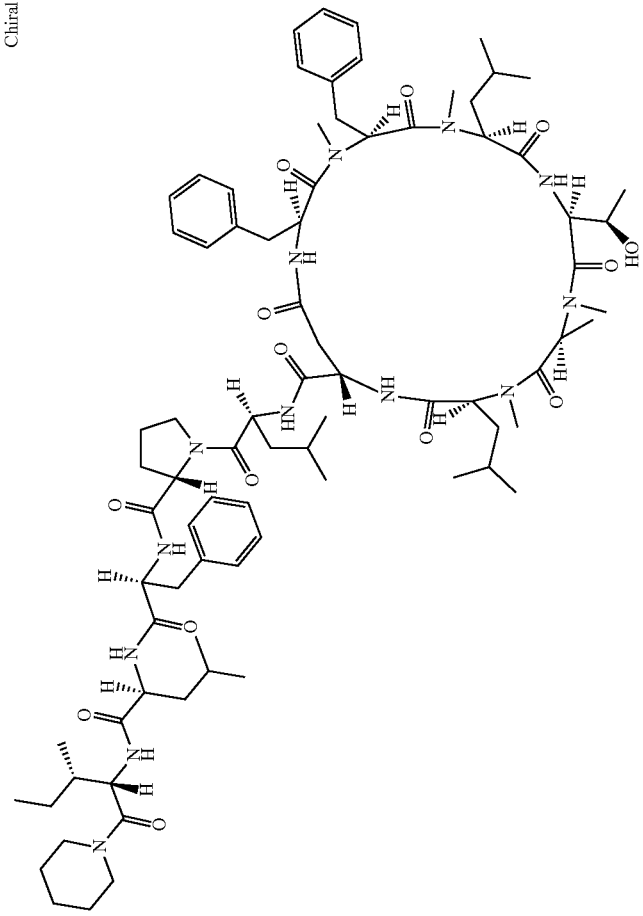
DP-910

TABLE 11-3-1-continued
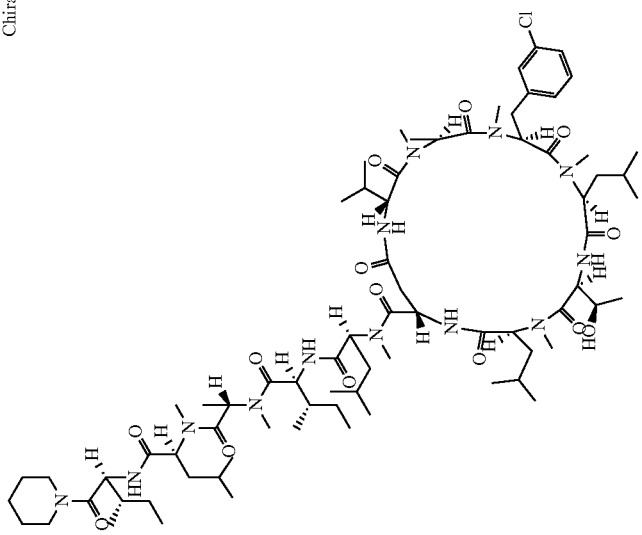
DP-911

TABLE 11-3-1-continued
Chiral
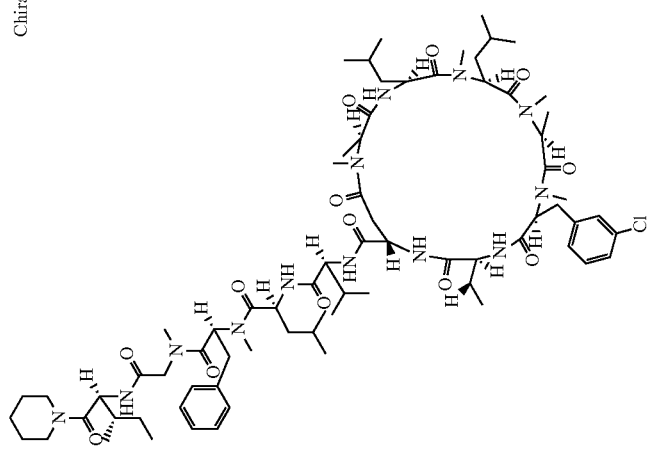
DP-912

TABLE 11-3-1-continued
| DP-913 | 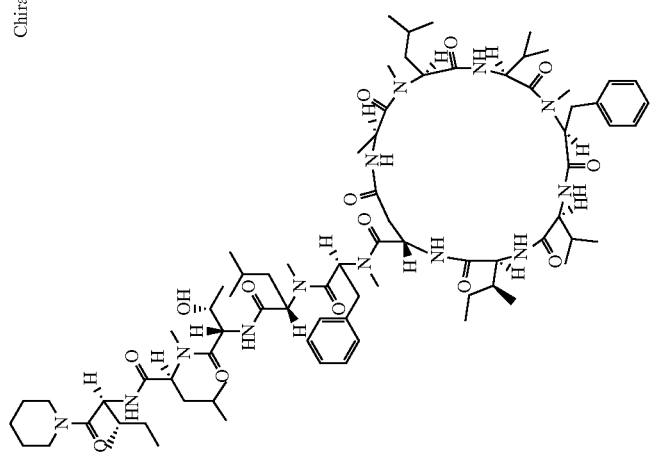 Chiral |

TABLE 11-3-1-continued
DP-914
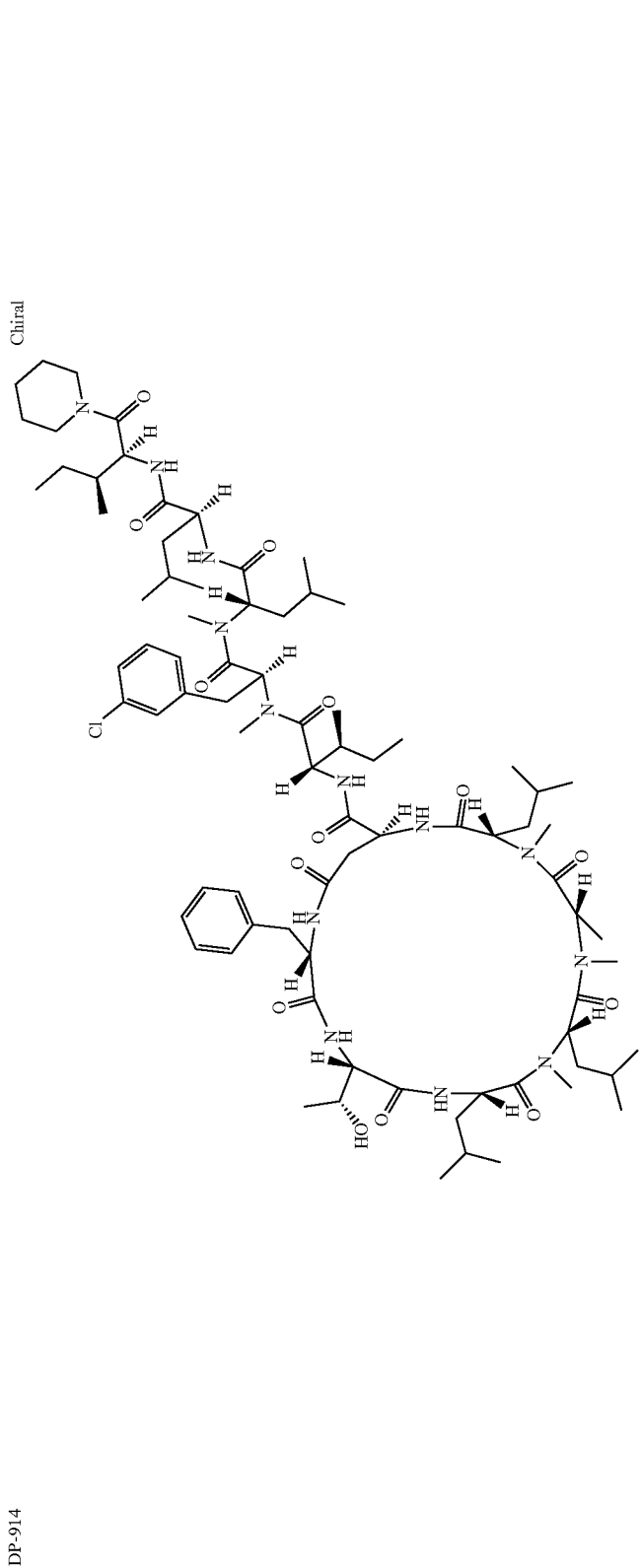

TABLE 11-3-1-continued
DP-915
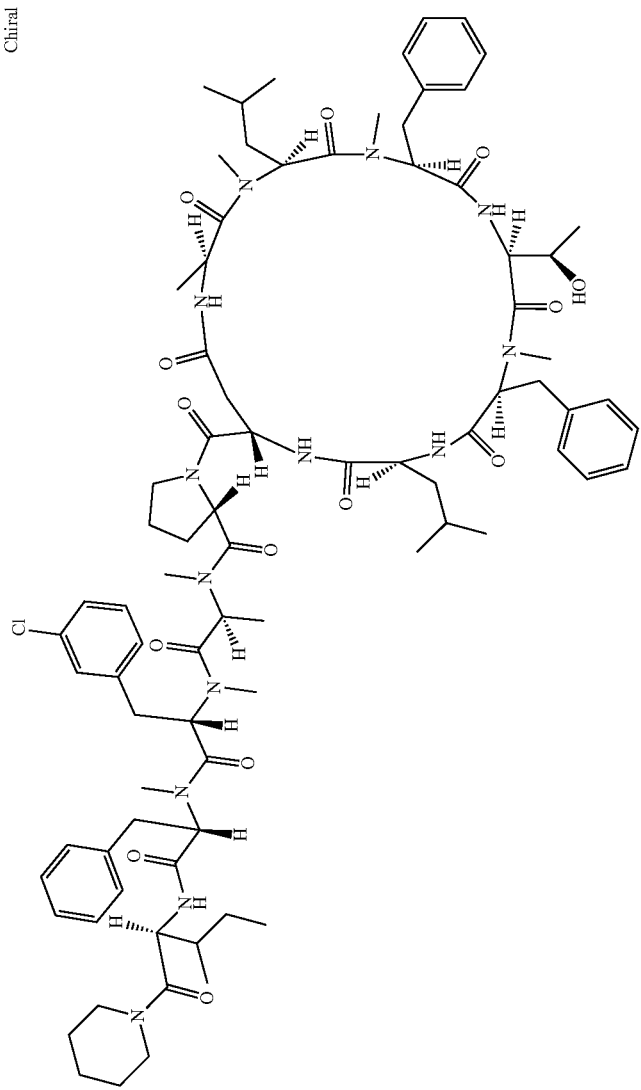

TABLE 11-3-1-continued
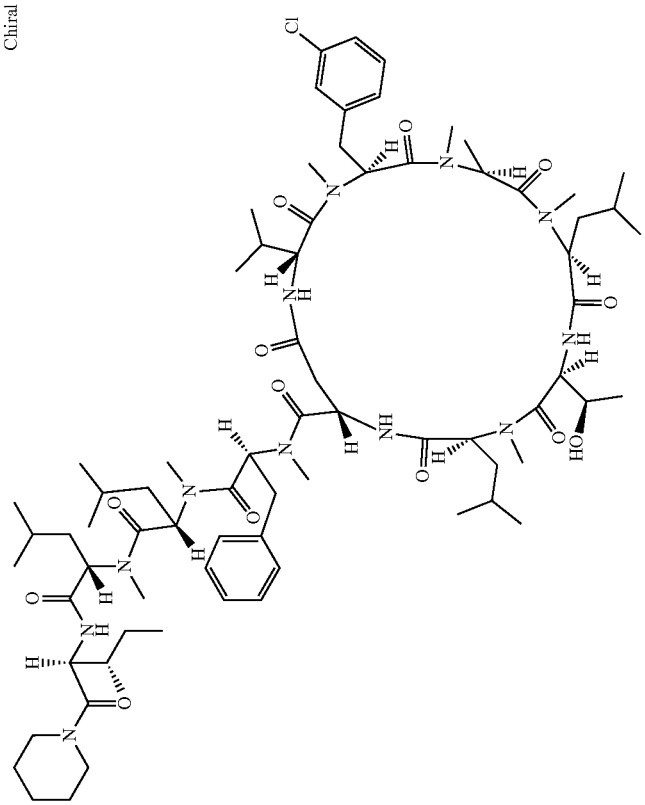
DP-916

TABLE 11-3-1-continued
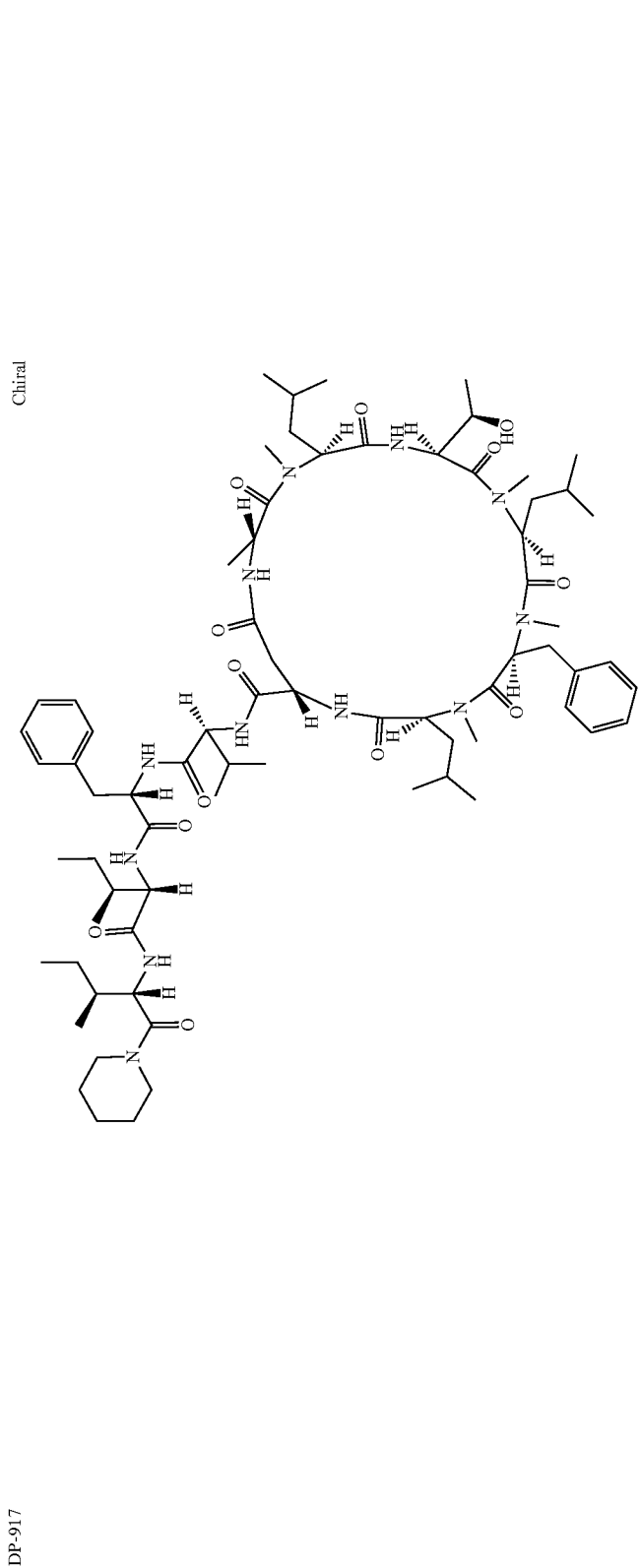
DP-917

TABLE 11-3-1-continued
DP-918
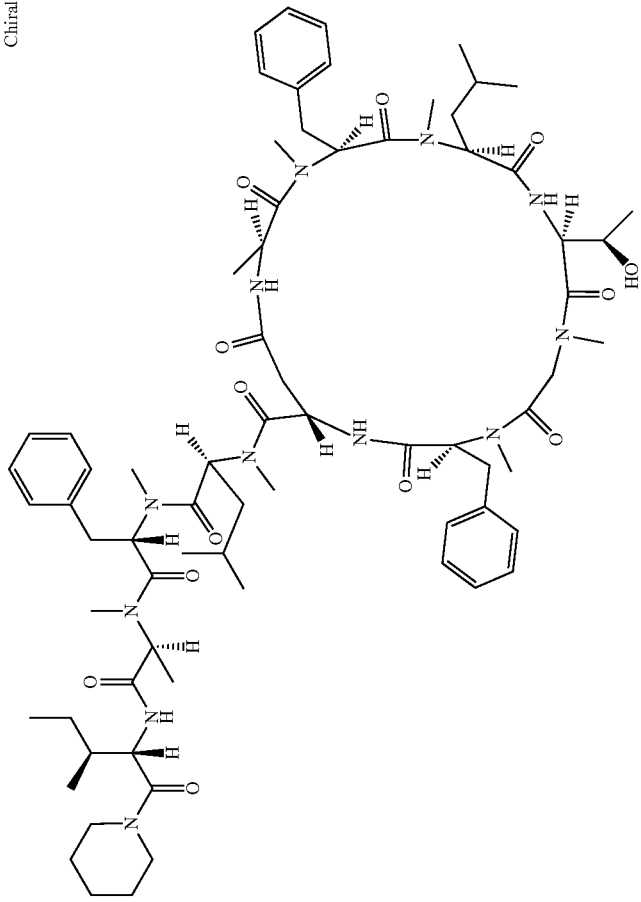

TABLE 11-3-1-continued
Chiral
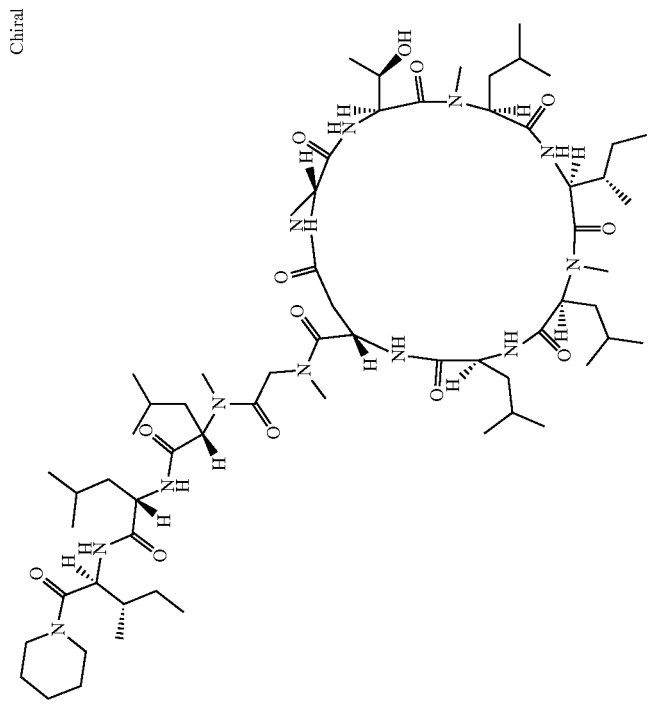
DP-919

TABLE 11-3-1-continued
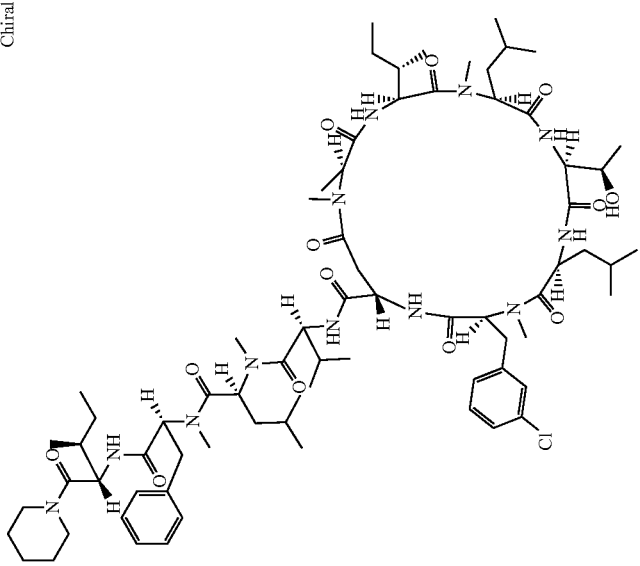

TABLE 11-3-1-continued
DP-921
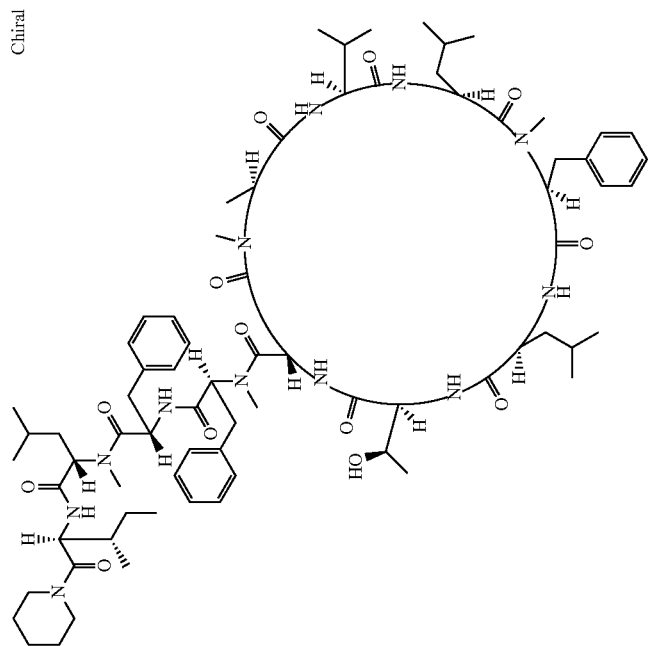

TABLE 11-3-1-continued
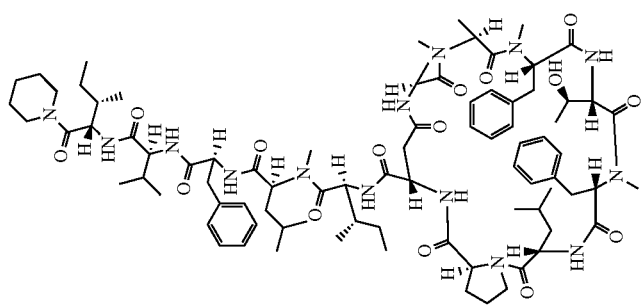
DP-922

TABLE 11-3-1-continued
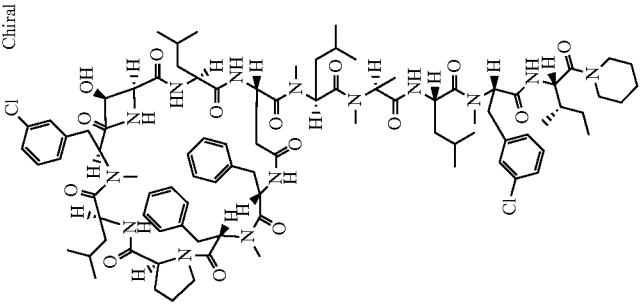
DP-923

TABLE 11-3-1-continued
Chiral
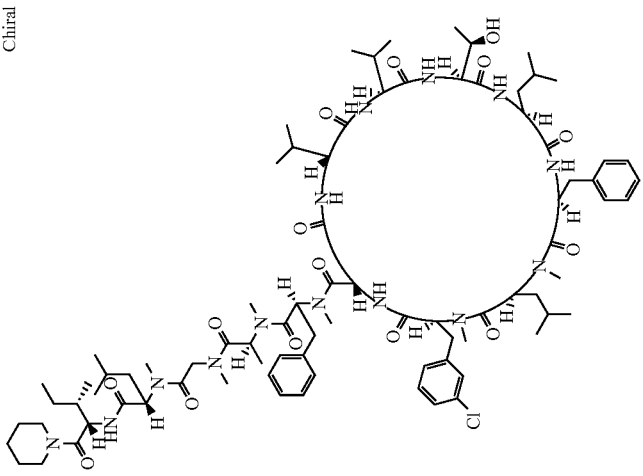
DP-924

TABLE 11-3-1-continued
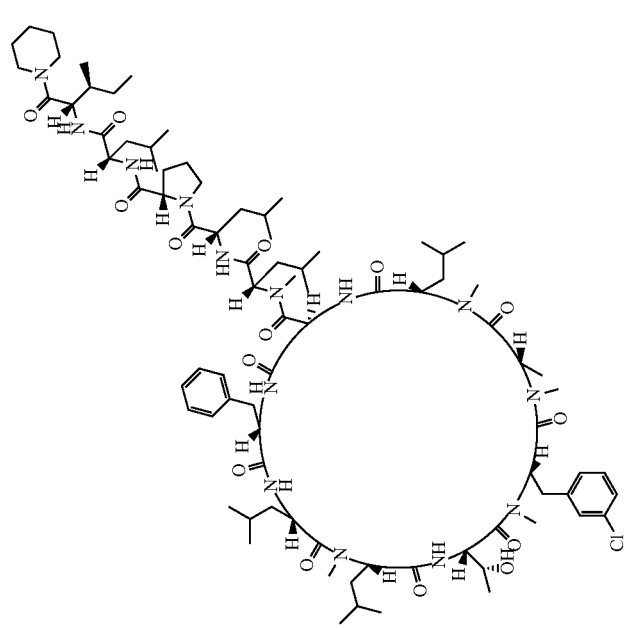
DP-925

TABLE 11-3-1-continued
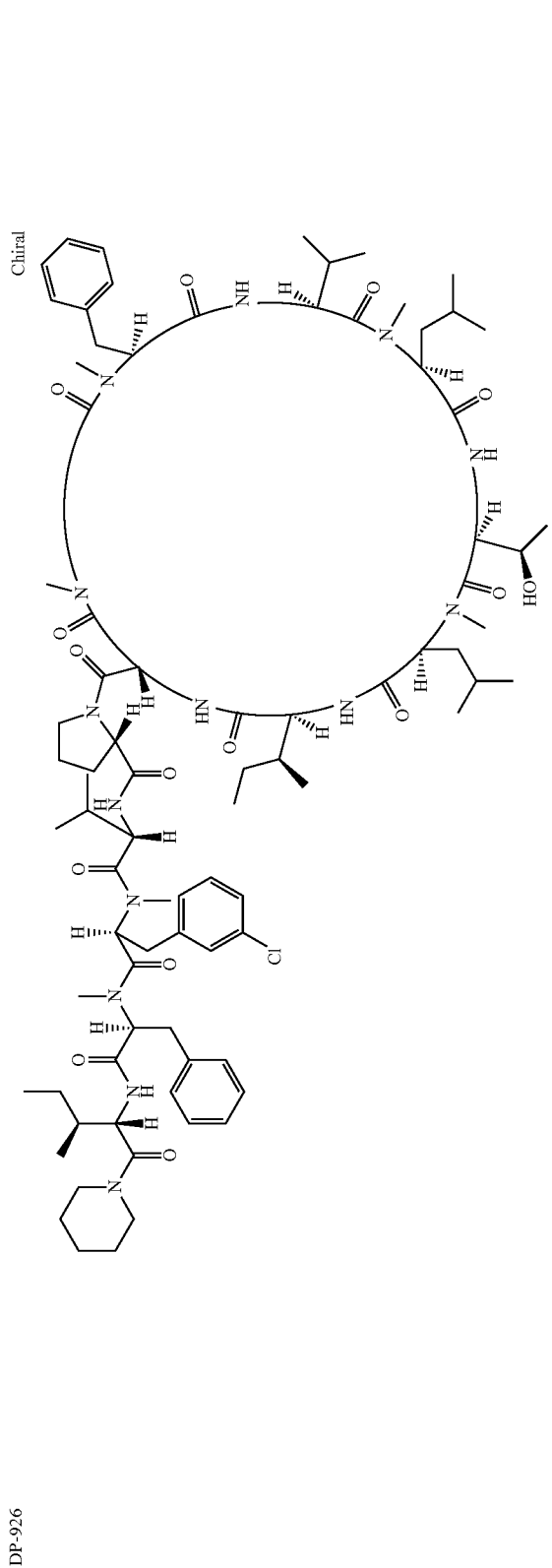
DP-926

TABLE 11-3-1-continued
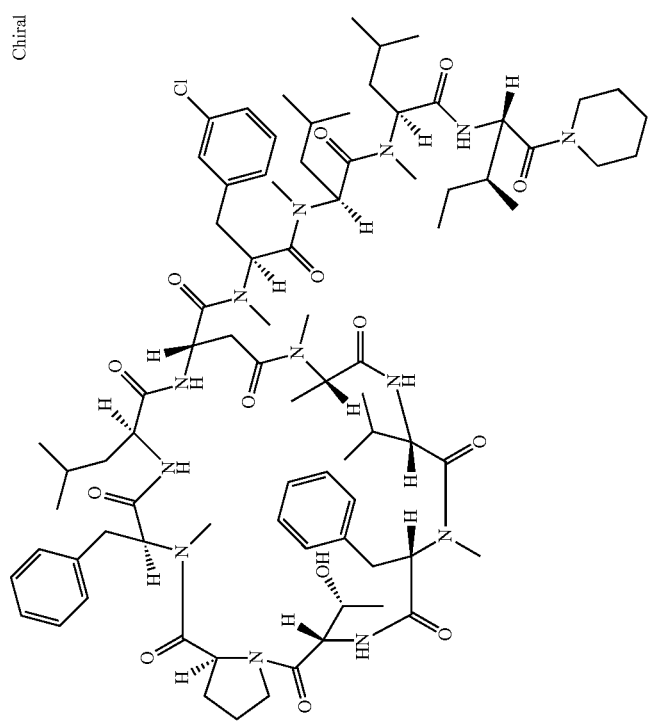
DP-927

TABLE 11-3-1-continued
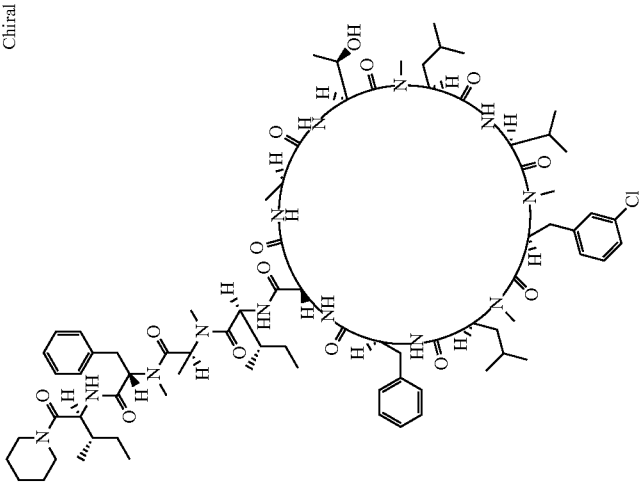
DP-928

TABLE 11-3-1-continued
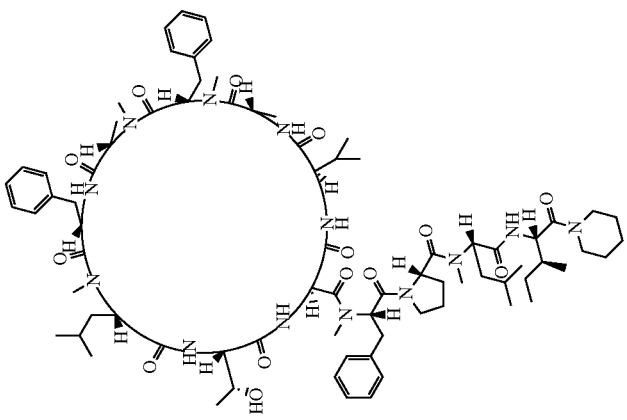
DP-929

TABLE 11-3-1-continued
DP-930
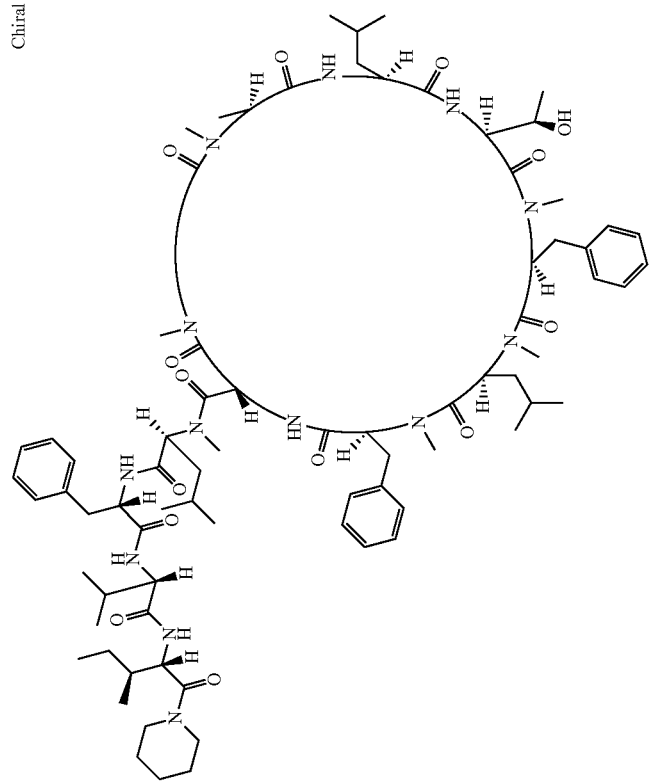

TABLE 11-3-1-continued
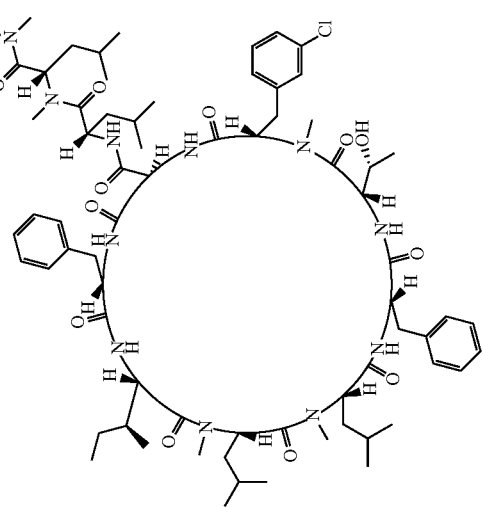
DP-931

TABLE 11-3-1-continued
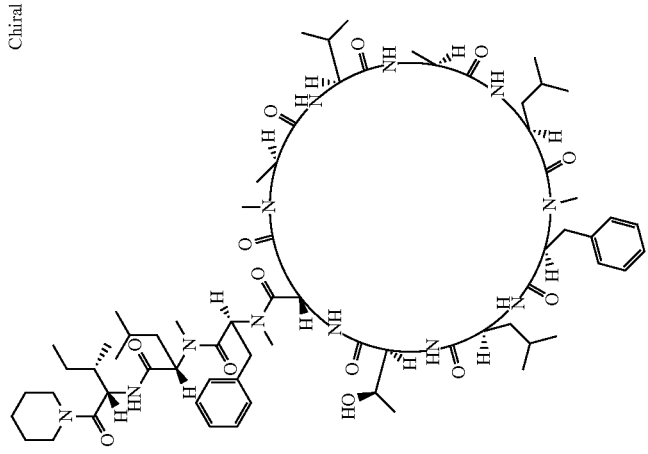
DP-932

TABLE 11-3-1-continued
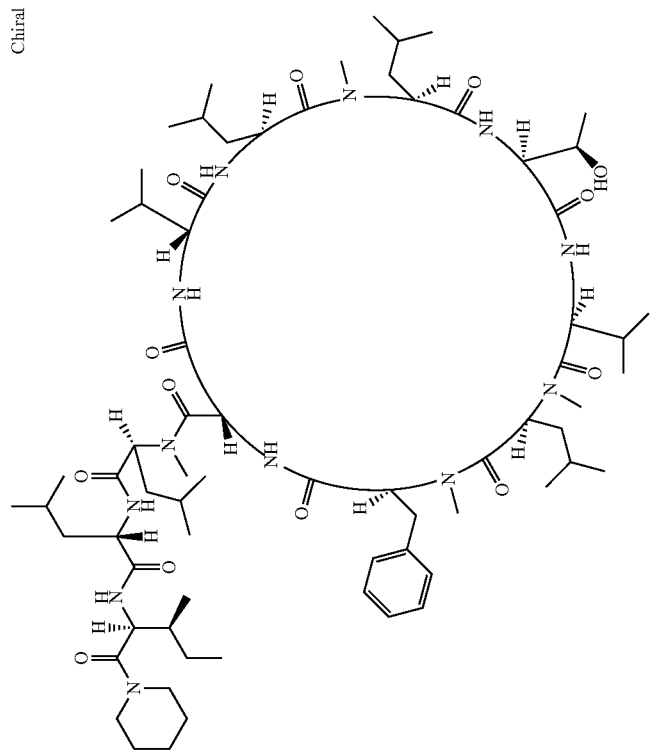
DP-933

TABLE 11-3-1-continued
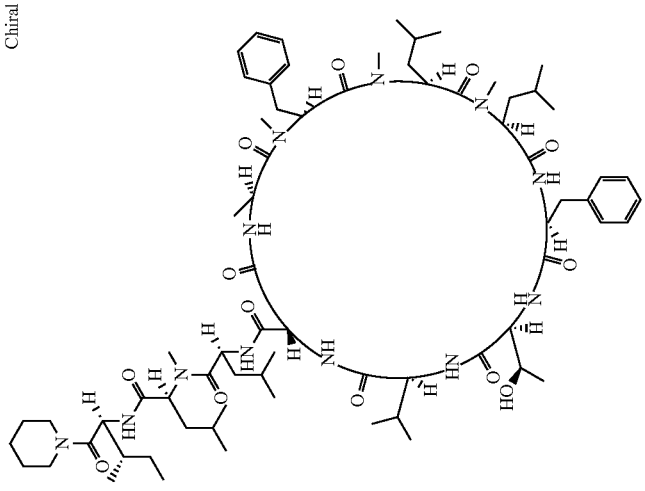
DP-934

TABLE 11-3-1-continued
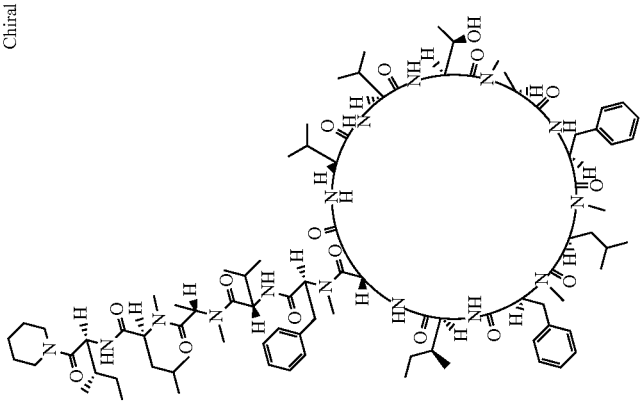
DP-935

TABLE 11-3-1-continued
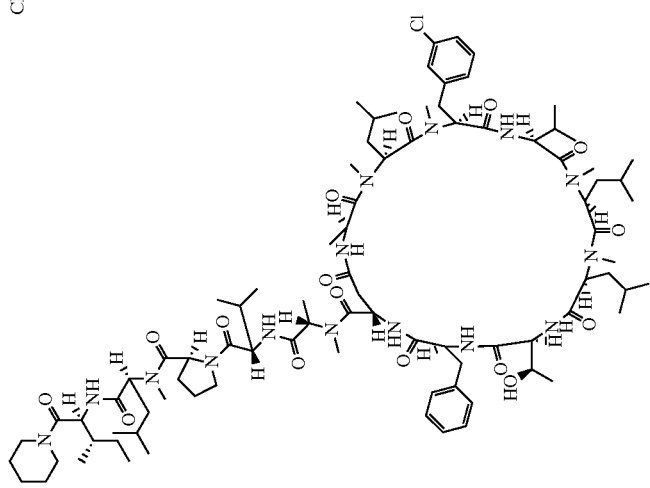
DP-936

TABLE 11-3-1-continued
DP-937
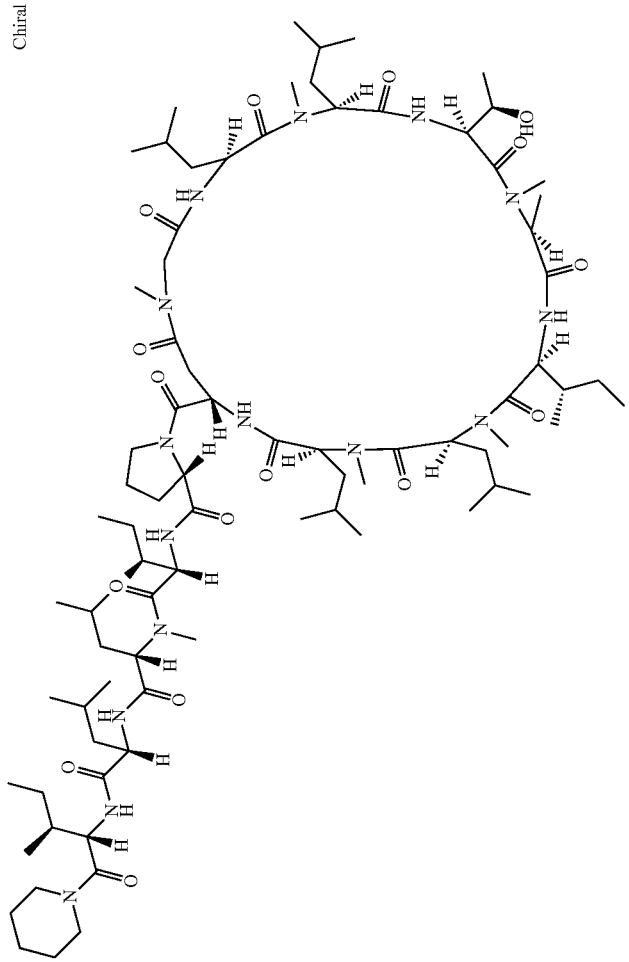

TABLE 11-3-1-continued
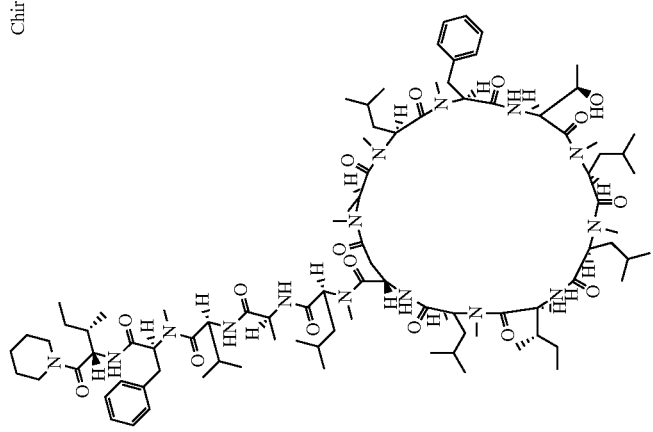
DP-938

TABLE 11-3-1-continued
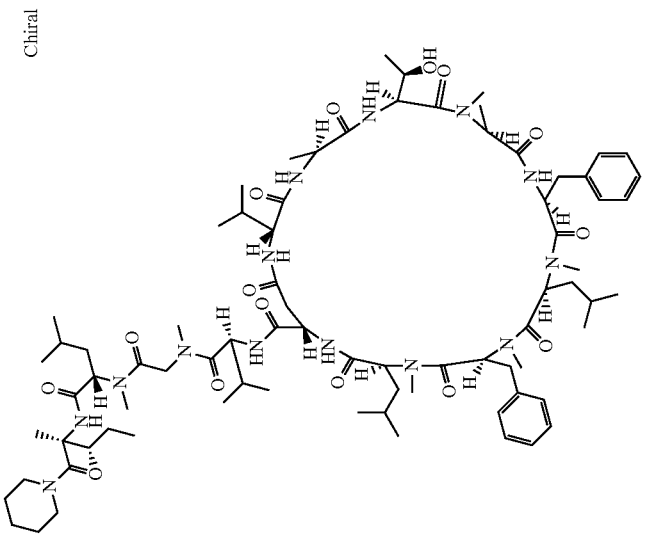
DP-939

TABLE 11-3-1-continued
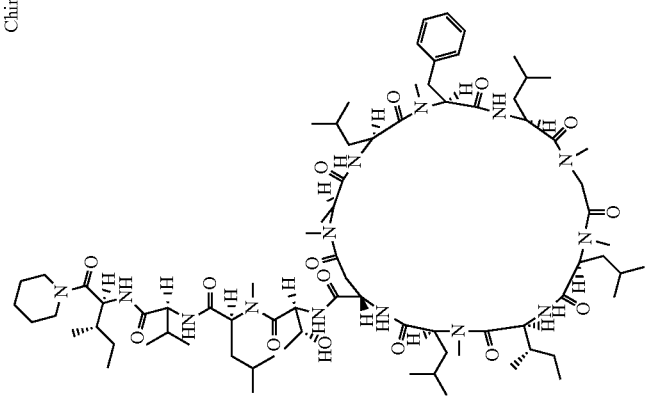
DP-940

TABLE 11-3-1-continued
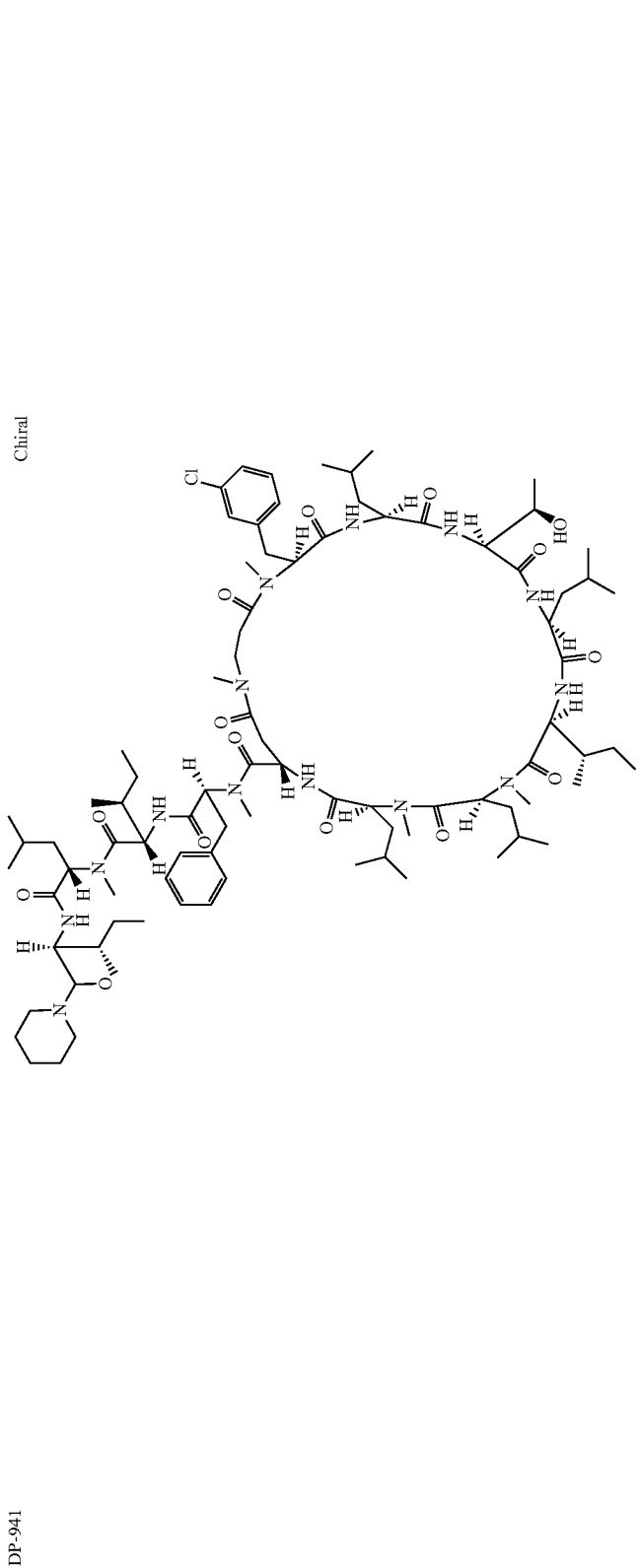
DP-941

TABLE 11-3-1-continued
| 2009 | 2010 |
|---|---|
| 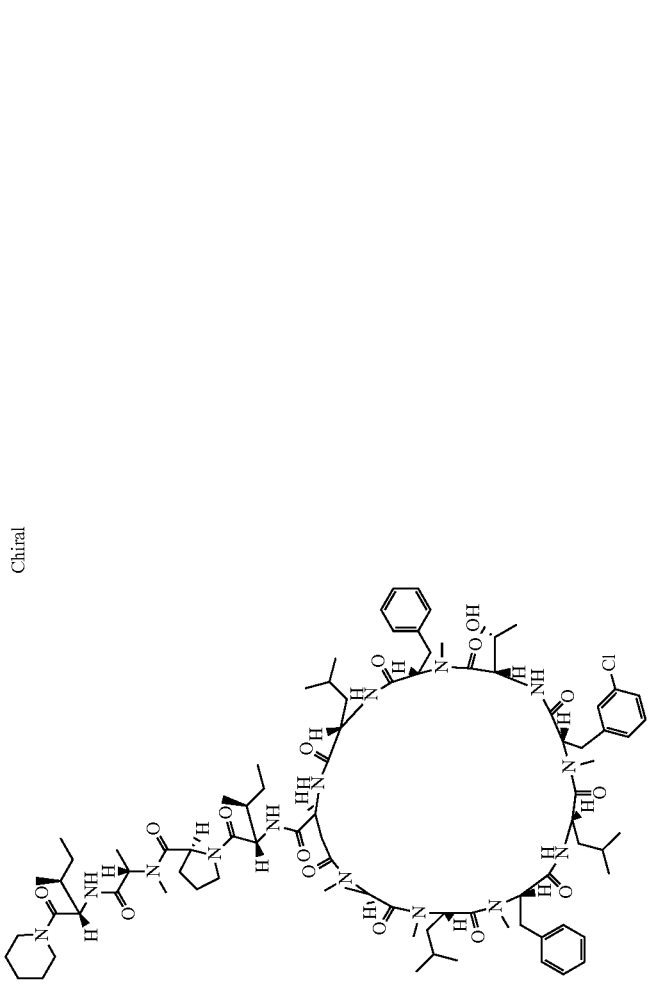 | 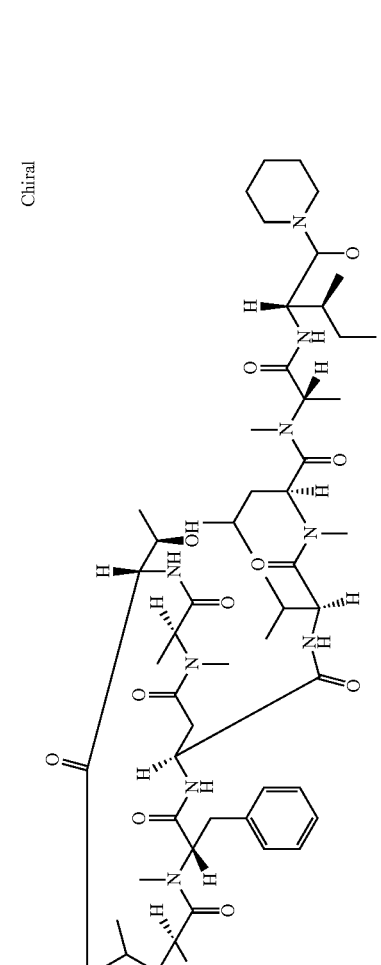 |
| DP-942 | DP-943 |

TABLE 11-3-1-continued
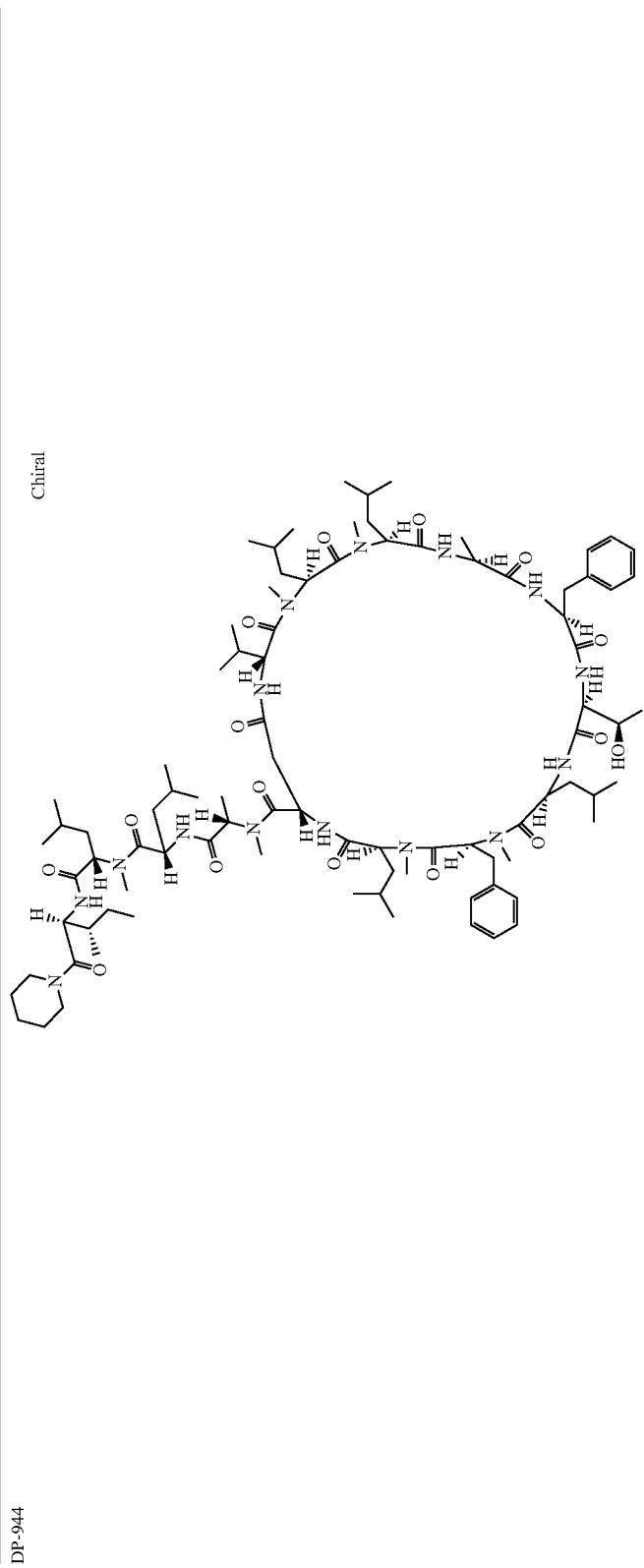
DP-944

TABLE 11-3-1-continued
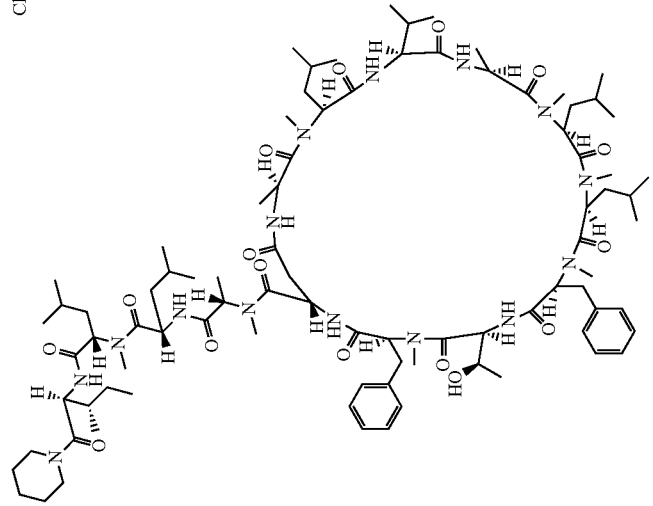
DP-945

TABLE 11-3-1-continued
DP-946
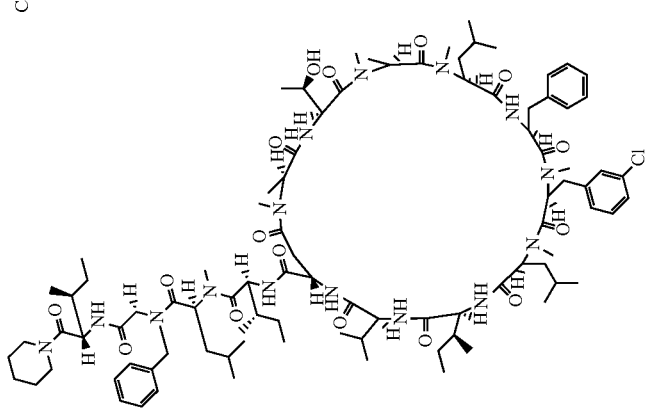

TABLE 11-3-1-continued
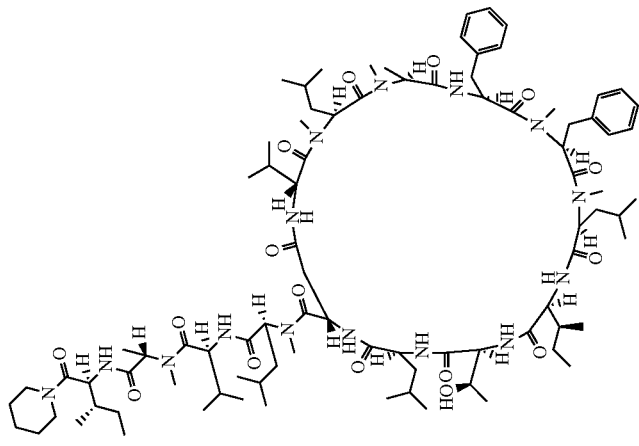
DP-947

TABLE 11-3-1-continued
DP-948
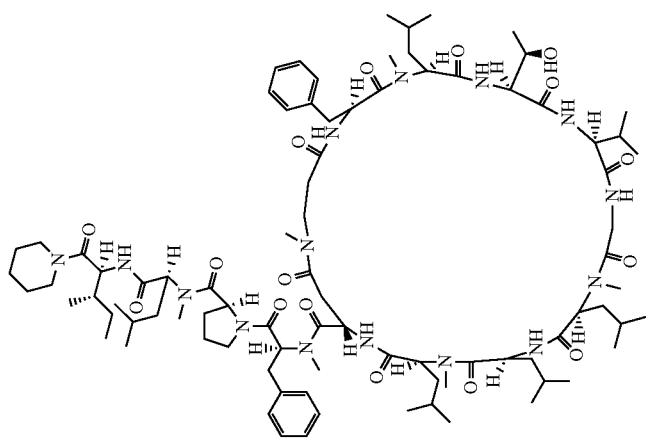

TABLE 11-3-1-continued
DP-949
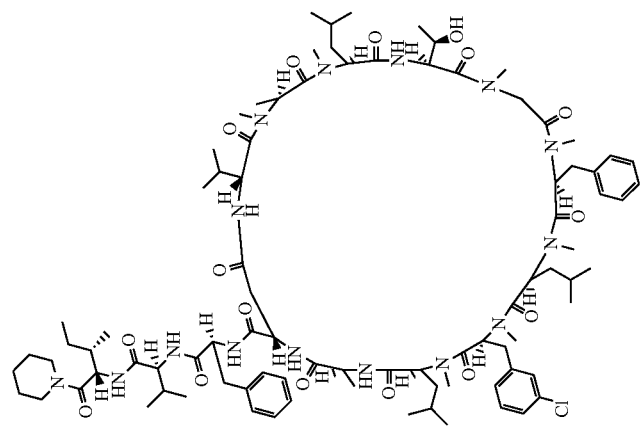

TABLE 11-3-1-continued
DP-950
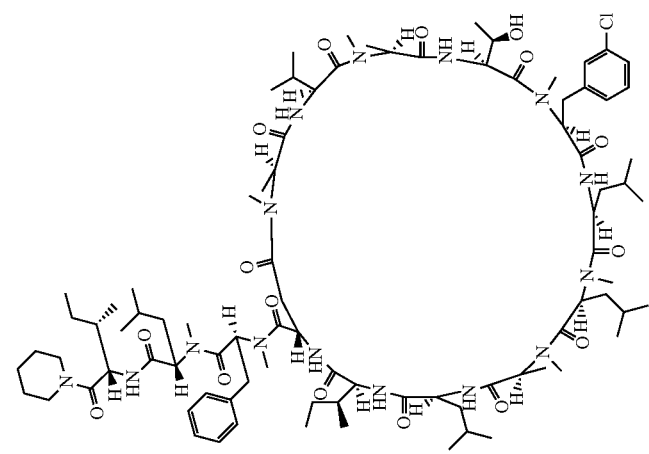

TABLE 11-3-1-continued
DP-951 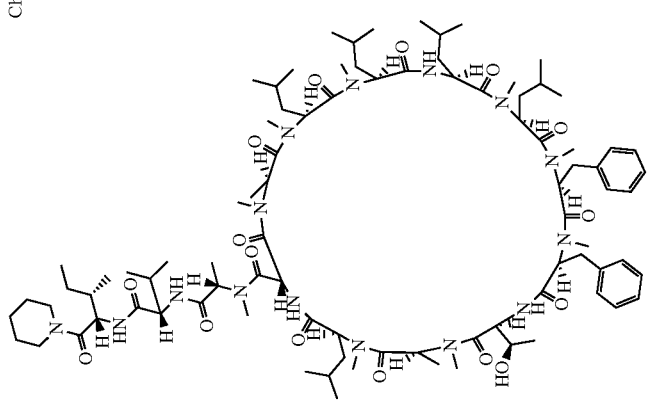

TABLE 11-3-1-continued
DP-952
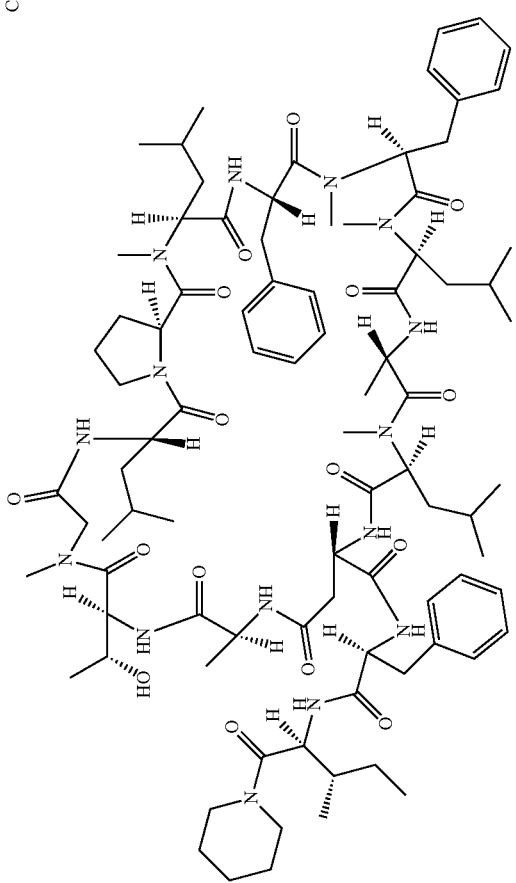

TABLE 11-3-1-continued
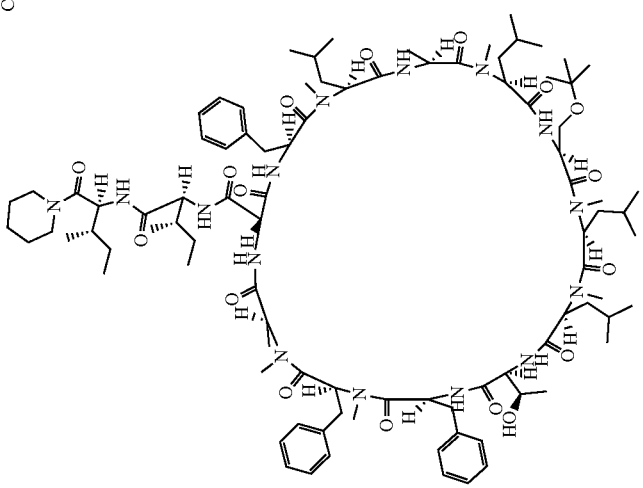
DP-953

TABLE 11-3-1-continued
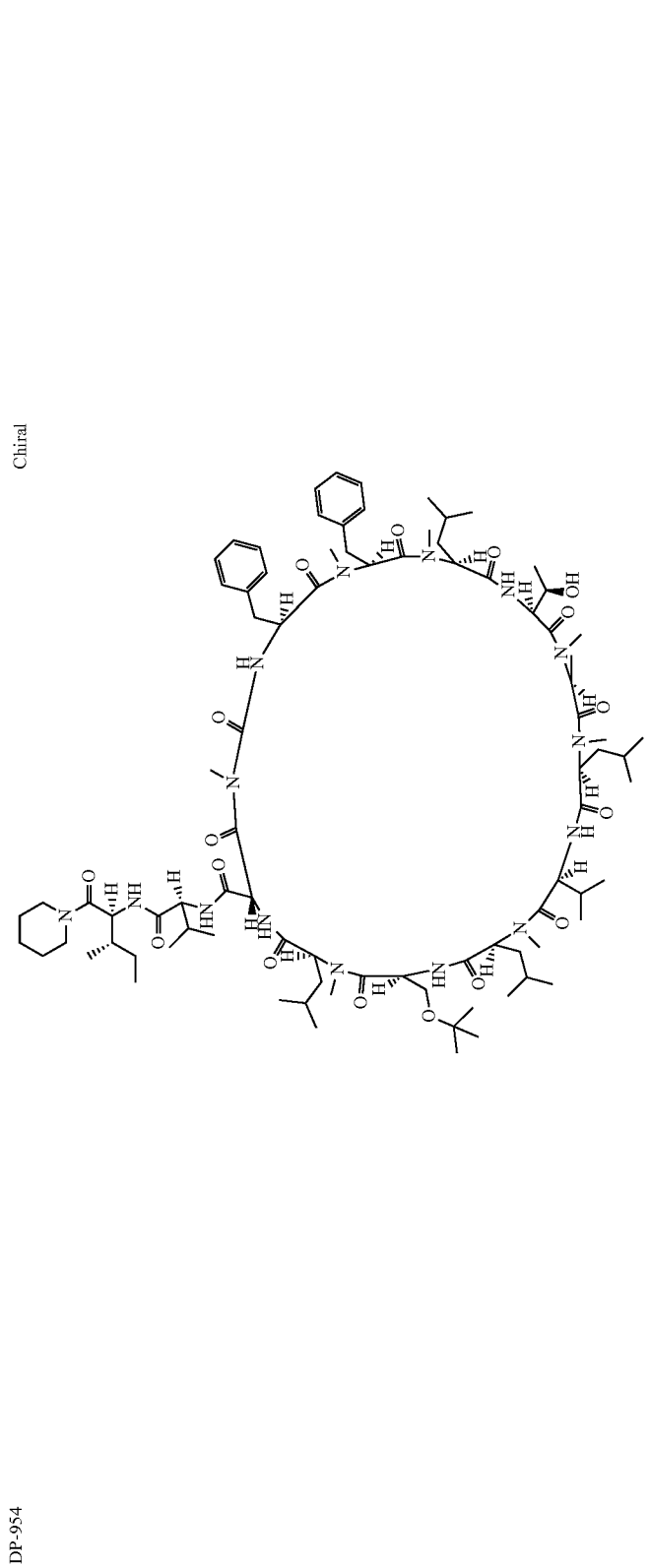
DP-954

TABLE 11-3-1-continued
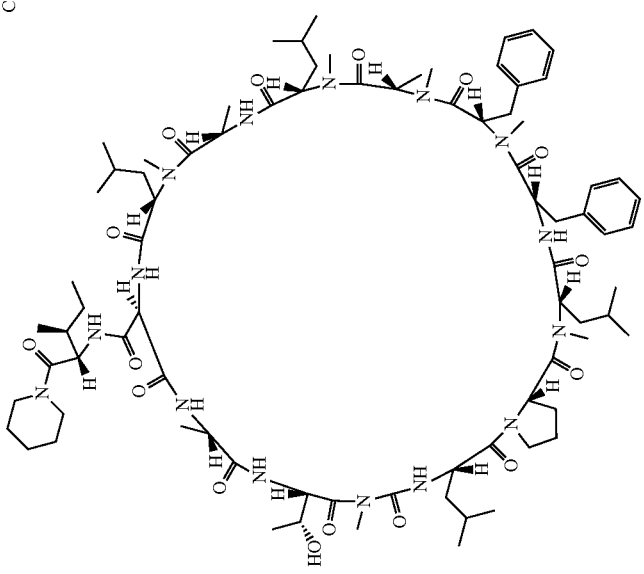
DP-955

TABLE 11-3-1-continued
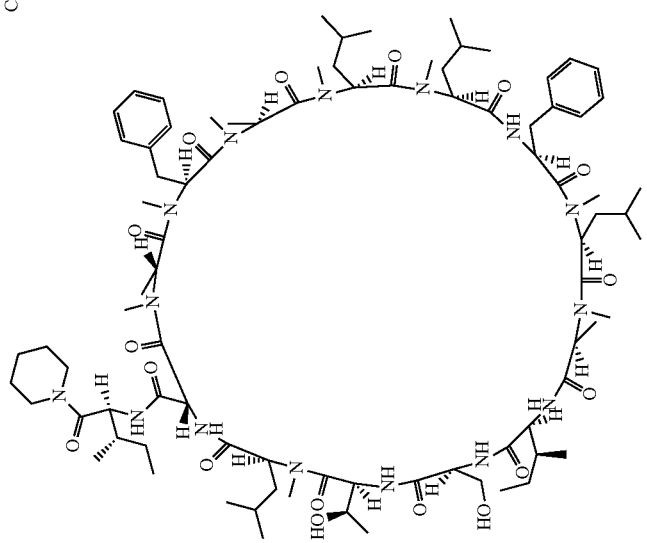
DP-956

TABLE 11-3-1-continued
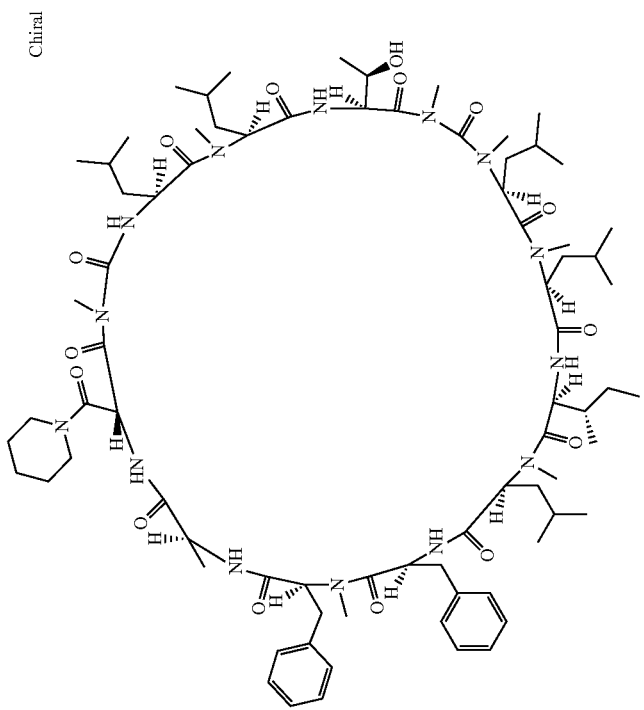
DP-957

TABLE 11-3-1-continued
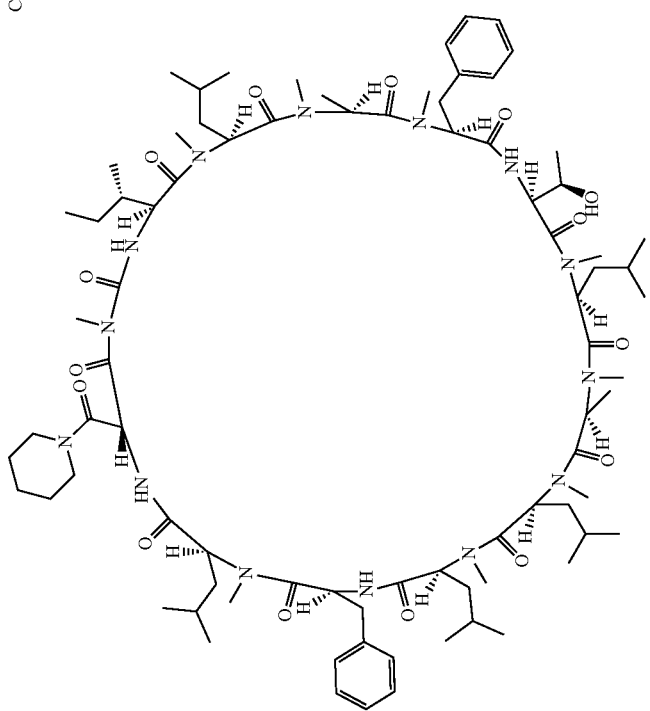
DP-958

TABLE 11-3-1-continued
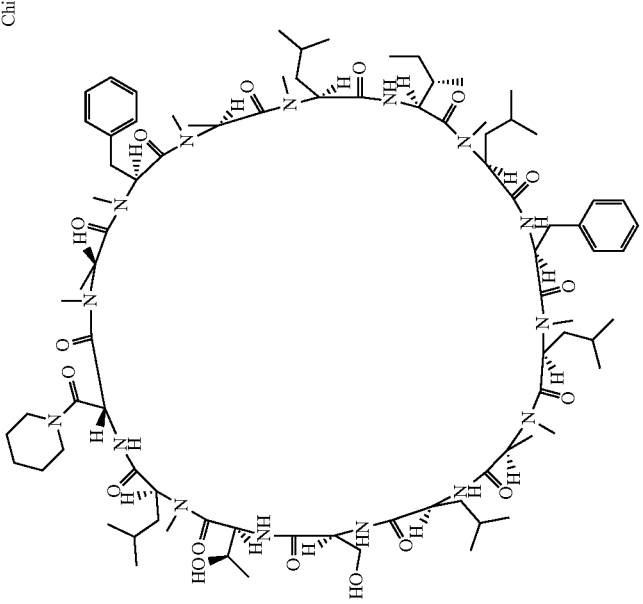
DP-959

TABLE 11-3-1-continued
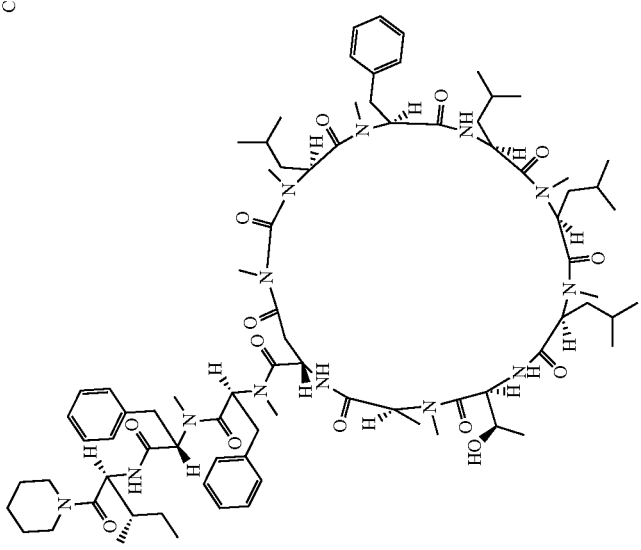
DP-960

TABLE 11-3-1-continued
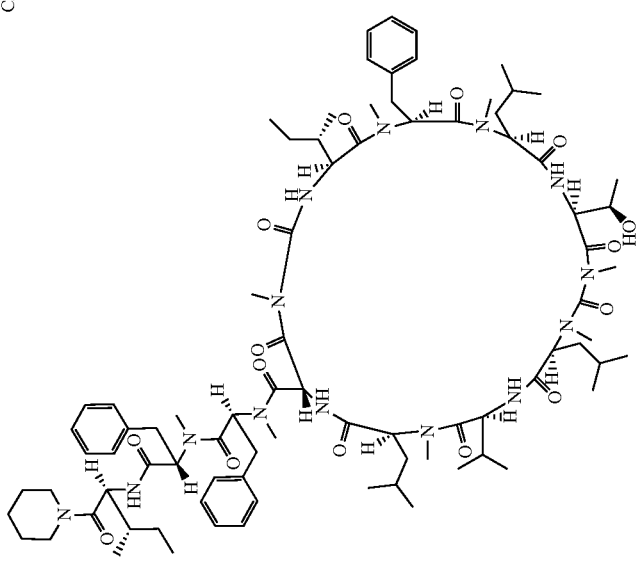
DP-961

TABLE 11-3-1-continued
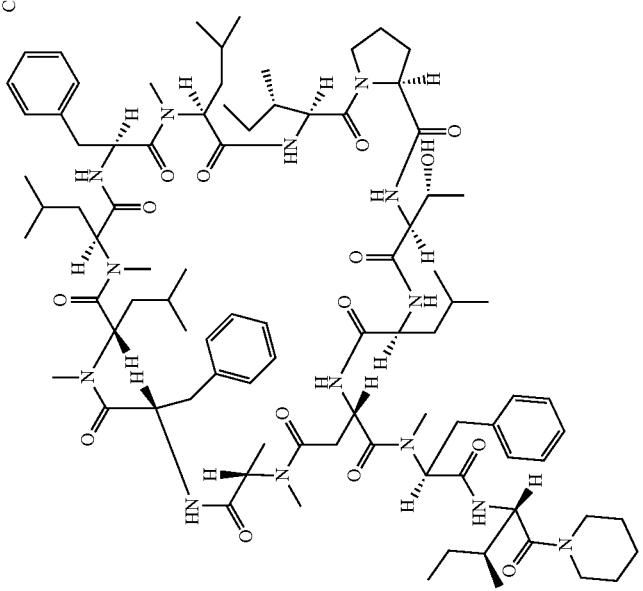
DP-962

TABLE 11-3-1-continued

| DP-963 | DP-964 |

TABLE 11-3-1-continued
DP-965
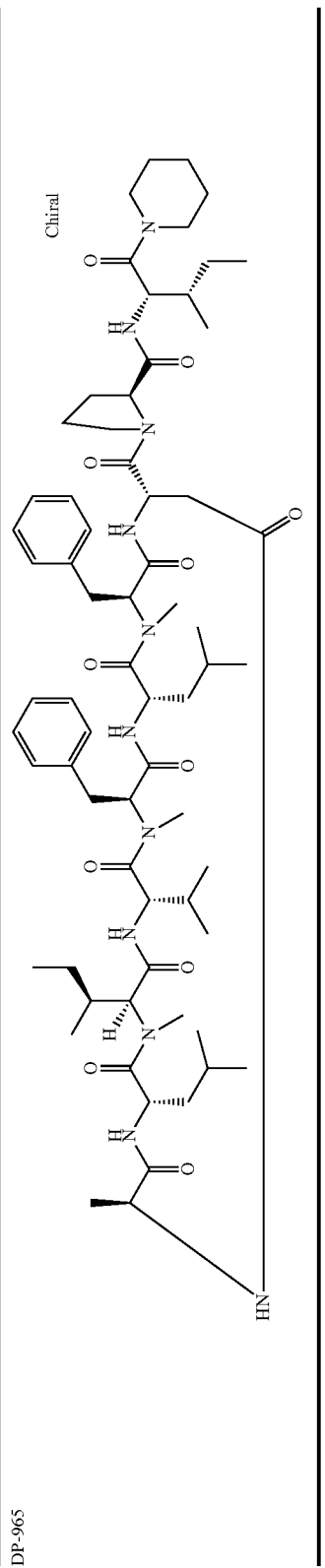

TABLE 11-3-2

| | LCMS condition | Retention time (min) | LCMS (ESI) m/z | |
|---|---|---|---|---|
| DP-1 | SQDAA50 | 0.82 | 1480 | (M − H)− |
| DP-2 | SQDAA50 | 0.83 | 1522 | (M − H)− |
| DP-3 | SQDAA50 | 0.75 | 1325 | (M − H)− |
| DP-4 | SQDAA50 | 0.78 | 1349 | (M + H)+ |
| DP-5 | SQDAA50 | 0.76 | 1307 | (M + H)+ |
| DP-6 | SQDAA50 | 0.74 | 1355 | (M + H)+ |
| DP-7 | SQDAA50 | 0.77 | 1381 | (M − H)− |
| DP-8 | SQDAA50 | 0.80 | 1397 | (M − H)− |
| DP-9 | SQDAA50 | 0.78 | 1381 | (M − H)− |
| DP-10 | SQDAA50 | 0.81 | 1437 | (M − H)− |
| DP-11 | SQDAA50 | 0.79 | 1395 | (M − H)− |
| DP-12 | SQDAA50 | 0.88 | 1451.5 | (M − H)− |
| DP-13 | SQDAA50 | 0.77 | 1298 | (M − H)− |
| DP-14 | SQDAA50 | 0.77 | 1282 | (M − H)− |
| DP-15 | SQDAA50 | 0.78 | 1310 | (M − H)− |
| DP-16 | SQDAA50 | 0.81 | 1296 | (M − H)− |
| DP-17 | SQDAA50 | 0.80 | 1225 | (M − H)− |
| DP-18 | SQDAA50 | 0.77 | 1215 | (M + H)+ |
| DP-19 | SQDFA05 | 0.87 | 1438 | (M − H)− |
| DP-20 | SQDAA50 | 0.85 | 1452.5 | (M − H)− |
| DP-21 | SQDAA50 | 0.84 | 1466.6 | (M − H)− |
| DP-22 | SQDAA50 | 0.85 | 1480.6 | (M − H)− |
| DP-23 | SQDAA50 | 0.79 | 1339 | (M − H)− |
| DP-24 | SQDAA50 | 0.81 | 1353 | (M − H)− |
| DP-25 | SQDFA05 | 1.04 | 1423.5 | (M − H)− |
| DP-26 | SQDAA50 | 0.83 | 1367 | (M − H)− |
| DP-27 | SQDAA50 | 0.83 | 1381.5 | (M − H)− |
| DP-28 | SQDAA50 | 0.79 | 1242 | (M − H)− |
| DP-29 | SQDAA50 | 0.85 | 1310 | (M − H)− |
| DP-30 | SQDAA50 | 0.78 | 1254 | (M − H)− |
| DP-31 | SQDAA50 | 0.83 | 1284 | (M − H)− |
| DP-32 | SQDAA50 | 0.76 | 1220 | (M − H)− |
| DP-33 | SQDAA50 | 0.82 | 1112 | (M − H)− |
| DP-34 | SQDAA50 | 0.74 | 1084 | (M − H)− |
| DP-35 | SQDAA50 | 0.82 | 1369 | (M − H)− |
| DP-36 | SQDAA50 | 0.79 | 1195 | (M − H)− |
| DP-37 | SQDAA50 | 0.80 | 1110 | (M − H)− |
| DP-38 | SQDAA50 | 0.70 | 1068 | (M − H)− |
| DP-39 | SQDAA50 | 0.71 | 1082 | (M − H)− |
| DP-40 | SQDAA50 | 0.77 | 1452 | (M − H)− |
| DP-41 | SQDAA50 | 0.76 | 1452 | (M − H)− |
| DP-42 | SQDAA50 | 0.79 | 1452 | (M − H)− |
| DP-43 | SQDAA50 | 0.84 | 1395 | (M − H)− |
| DP-44 | SQDAA50 | 0.79 | 1296 | (M − H)− |
| DP-45 | SQDAA50 | 0.81 | 1296 | (M − H)− |
| DP-46 | SQDAA50 | 0.78 | 1199 | (M − H)− |
| DP-47 | SQDAA50 | 0.86 | 1386 | (M + H)+ |
| DP-48 | SQDAA50 | 0.77 | 1328 | (M + H)+ |
| DP-49 | SQDAA50 | 0.88 | 1414 | (M + H)+ |
| DP-50 | SQDAA50 | 0.76 | 1245 | (M + H)+ |
| DP-51 | SQDAA50 | 0.79 | 1229 | (M + H)+ |
| DP-52 | SQDAA50 | 0.73 | 1090 | (M + H)+ |
| DP-53 | SQDAA50 | 0.83 | 1383 | (M − H)− |
| DP-54 | SQDAA50 | 0.79 | 1381 | (M − H)− |
| DP-55 | SQDAA50 | 0.82 | 1425 | (M − H)− |
| DP-56 | SQDAA50 | 0.84 | 1409 | (M − H)− |
| DP-57 | SQDAA50 | 0.81 | 1411 | (M − H)− |
| DP-58 | SQDAA50 | 0.80 | 1395 | (M − H)− |
| DP-59 | SQDAA50 | 0.77 | 1369 | (M − H)− |
| DP-60 | SQDAA50 | 0.82 | 1110 | (M − H)− |
| DP-61 | SQDAA50 | 0.82 | 1397 | (M − H)− |
| DP-62 | SQDAA50 | 0.81 | 1411 | (M − H)− |
| DP-63 | SQDAA50 | 0.86 | 1483 | (M − H)− |
| DP-64 | SQDAA50 | 0.77 | 1383 | (M − H)− |
| DP-65 | SQDAA50 | 0.77 | 1282 | (M − H)− |
| DP-66 | SQDAA50 | 0.78 | 1310 | (M − H)− |
| DP-67 | SQDAA50 | 0.80 | 1296 | (M − H)− |
| DP-68 | SQDAA50 | 0.78 | 1312 | (M − H)− |
| DP-69 | SQDAA50 | 0.87 | 1398 | (M − H)− |
| DP-70 | SQDAA50 | 0.85 | 1340 | (M − H)− |
| DP-71 | SQDAA50 | 0.70 | 1095 | (M − H)− |
| DP-72 | SQDAA50 | 0.80 | 1227 | (M − H)− |
| DP-73 | SQDAA50 | 0.70 | 1109 | (M − H)− |
| DP-74 | SQDAA50 | 0.81 | 1213 | (M − H)− |
| DP-75 | SQDAA50 | 0.65 | 1095 | (M − H)− |
| DP-76 | SQDAA50 | 0.77 | 1195 | (M − H)− |
| DP-77 | SQDAA50 | 0.80 | 1110 | (M − H)− |
| DP-78 | SQDAA50 | 0.81 | 1100 | (M − H)− |
| DP-79 | SQDAA50 | 0.77 | 1102 | (M − H)− |
| DP-80 | SQDAA50 | 0.74 | 1102 | (M − H)− |
| DP-81 | SQDAA50 | 0.79 | 1124 | (M − H)− |
| DP-82 | SQDAA50 | 0.78 | 1426 | (M − H)− |
| DP-83 | SQDAA50 | 0.83 | 1454 | (M − H)− |
| DP-84 | SQDAA50 | 0.74 | 1313 | (M − H)− |
| DP-85 | SQDAA50 | 0.77 | 1270 | (M − H)− |
| DP-86 | SQDAA50 | 0.79 | 1100 | (M − H)− |
| DP-87 | SQDAA50 | 0.83 | 1440 | (M − H)− |
| DP-88 | SQDAA50 | 0.79 | 1397 | (M − H)− |
| DP-89 | SQDAA05 | 1.18 | 1397 | (M − H)− |
| DP-90 | SQDAA05 | 1.22 | 1483 | (M − H)− |
| DP-91 | SQDAA05 | 0.79 | 1395 | (M − H)− |
| DP-92 | SQDAA05 | 1.20 | 1483 | (M − H)− |
| DP-93 | SQDAA05 | 1.15 | 1369 | (M − H)− |
| DP-94 | SQDAA05 | 1.15 | 1397 | (M − H)− |
| DP-95 | SQDAA05 | 1.10 | 1208 | (M − H)− |
| DP-96 | SQDAA05 | 1.22 | 1398 | (M − H)− |
| DP-97 | SQDAA05 | 1.18 | 1312 | (M − H)− |
| DP-98 | SQDAA05 | 1.15 | 1298 | (M − H)− |
| DP-99 | SQDAA05 | 1.18 | 1340 | (M − H)− |
| DP-100 | SQDAA05 | 1.22 | 1412 | (M − H)− |
| DP-101 | SQDAA05 | 1.17 | 1326 | (M − H)− |
| DP-102 | SQDAA05 | 1.09 | 1222 | (M − H)− |
| DP-103 | SQDAA05 | 1.22 | 1412 | (M − H)− |
| DP-104 | SQDAA05 | 1.23 | 1382 | (M − H)− |
| DP-105 | SQDAA05 | 1.18 | 1326 | (M − H)− |
| DP-106 | SQDAA05 | 1.17 | 1296 | (M − H)− |
| DP-107 | SQDAA50 | 0.82 | 1427 | (M + H)+ |
| DP-108 | SQDAA50 | 0.79 | 1383 | (M + H)+ |
| DP-109 | SQDAA50 | 0.81 | 1411 | (M + H)+ |
| DP-110 | SQDAA50 | 0.84 | 1372 | (M + H)+ |
| DP-111 | SQDFA05 | 0.88 | 1222 | (M − H)− |
| DP-112 | SQDAA50 | 0.80 | 1280 | (M + H)+ |
| DP-113 | SQDAA50 | 0.81 | 1326 | (M + H)+ |
| DP-114 | SQDAA50 | 0.88 | 1428 | (M + H)+ |
| DP-115 | SQDAA50 | 0.84 | 1263 | (M + H)+ |
| DP-116 | SQDAA50 | 0.80 | 1235 | (M + H)+ |
| DP-117 | SQDAA50 | 0.80 | 1235 | (M + H)+ |
| DP-118 | SQDAA50 | 0.76 | 1153 | (M + H)+ |
| DP-119 | SQDAA50 | 0.83 | 1277 | (M + H)+ |
| DP-120 | SQDAA50 | 0.82 | 1245 | (M + H)+ |
| DP-121 | SQDAA50 | 0.84 | 1243 | (M + H)+ |
| DP-122 | SQDAA50 | 0.80 | 1225 | (M + H)+ |
| DP-123 | SQDAA50 | 0.81 | 1413 | (M + H)+ |
| DP-124 | SQDAA50 | 0.80 | 1355 | (M − H)− |
| DP-125 | SQDAA50 | 0.82 | 1130 | (M + H)+ |
| DP-126 | SQDAA50 | 0.86 | 1220 | (M + H)+ |
| DP-127 | SQDAA50 | 0.81 | 1130 | (M + H)+ |
| DP-128 | SQDAA50 | 0.76 | 1102 | (M + H)+ |
| DP-129 | SQDAA50 | 0.75 | 1118 | (M + H)+ |
| DP-130 | SQDAA50 | 0.77 | 1112 | (M + H)+ |
| DP-131 | SQDAA50 | 0.81 | 1383 | (M − H)− |
| DP-132 | SQDAA50 | 0.84 | 1411 | (M − H)− |
| DP-133 | SQDAA50 | 0.82 | 1397 | (M − H)− |
| DP-134 | SQDAA50 | 0.79 | 1395 | (M − H)− |
| DP-135 | SQDAA50 | 0.71 | 1095 | (M − H)− |
| DP-136 | SQDAA50 | 0.80 | 1213 | (M − H)− |
| DP-137 | SQDAA50 | 0.80 | 1383 | (M − H)− |
| DP-138 | SQDAA50 | 0.81 | 1209 | (M − H)− |
| DP-139 | SQDAA50 | 0.88 | 1326 | (M − H)− |
| DP-140 | SQDAA50 | 0.82 | 1227 | (M − H)− |
| DP-141 | SQDFA05 | 0.88 | 1284 | (M + H)+ |
| DP-142 | SQDAA50 | 0.72 | 1109 | (M − H)− |
| DP-143 | SQDAA50 | 0.80 | 1236 | (M − H)− |
| DP-144 | SQDAA50 | 0.84 | 1209 | (M − H)− |
| DP-145 | SQDAA50 | 0.81 | 1213 | (M − H)− |
| DP-146 | SQDAA50 | 0.81 | 1310 | (M − H)− |
| DP-147 | SQDAA50 | 0.88 | 1255 | (M − H)− |
| DP-148 | SQDAA50 | 0.79 | 1082 | (M − H)− |
| DP-149 | SQDAA50 | 0.88 | 1398 | (M − H)− |
| DP-150 | SQDAA50 | 0.78 | 1086 | (M − H)− |
| DP-151 | SQDAA50 | 0.83 | 1312 | (M − H)− |
| DP-152 | SQDAA50 | 0.88 | 1124 | (M − H)− |
| DP-153 | SQDAA50 | 0.76 | 1086 | (M − H)− |
| DP-154 | SQDAA50 | 0.88 | 1382 | (M − H)− |

TABLE 11-3-2-continued

| | LCMS condition | Retention time (min) | LCMS (ESI) m/z | |
|---|---|---|---|---|
| DP-155 | SQDAA50 | 0.83 | 1124 | (M − H)− |
| DP-156 | SQDAA50 | 0.87 | 1340 | (M − H)− |
| DP-157 | SQDAA50 | 0.76 | 1086 | (M − H)− |
| DP-158 | SQDAA50 | 0.86 | 1354 | (M − H)− |
| DP-159 | SQDAA50 | 0.86 | 1354 | (M − H)− |
| DP-160 | SQDAA50 | 0.79 | 1096 | (M − H)− |
| DP-161 | SQDAA50 | 0.76 | 1072 | (M − H)− |
| DP-162 | SQDAA50 | 0.83 | 1310 | (M − H)− |
| DP-163 | SQDAA50 | 0.78 | 1082 | (M − H)− |
| DP-164 | SQDAA50 | 0.80 | 1296 | (M − H)− |
| DP-165 | SQDAA50 | 0.83 | 1312 | (M − H)− |
| DP-166 | SQDAA50 | 0.84 | 1354 | (M − H)− |
| DP-167 | SQDAA50 | 0.71 | 1208 | (M − H)− |
| DP-168 | SQDAA50 | 0.84 | 1370 | (M − H)− |
| DP-169 | SQDAA50 | 0.81 | 1213 | (M − H)− |
| DP-170 | SQDAA50 | 0.81 | 1195 | (M − H)− |
| DP-171 | SQDAA50 | 0.89 | 1257 | (M − H)− |
| DP-172 | SQDAA50 | 0.82 | 1241 | (M − H)− |
| DP-173 | SQDAA50 | 0.83 | 1227 | (M − H)− |
| DP-174 | SQDAA50 | 0.76 | 1213 | (M − H)− |
| DP-175 | SQDAA50 | 0.79 | 1199 | (M − H)− |
| DP-176 | SQDAA50 | 0.76 | 1116 | (M − H)− |
| DP-177 | SQDAA50 | 0.81 | 1440 | (M − H)− |
| DP-178 | SQDAA50 | 0.90 | 1572 | (M − H)− |
| DP-179 | SQDAA50 | 0.81 | 1440 | (M − H)− |
| DP-180 | SQDAA50 | 0.86 | 1544 | (M − H)− |
| DP-181 | SQDAA50 | 0.80 | 1454 | (M − H)− |
| DP-182 | SQDAA50 | 0.87 | 1542 | (M − H)− |
| DP-183 | SQDAA50 | 0.86 | 1544 | (M − H)− |
| DP-184 | SQDAA50 | 0.90 | 1586 | (M − H)− |
| DP-185 | SQDAA50 | 0.84 | 1528 | (M − H)− |
| DP-186 | SQDAA50 | 0.89 | 1544 | (M − H)− |
| DP-187 | SQDAA50 | 0.86 | 1417 | (M − H)− |
| DP-188 | SQDAA50 | 0.81 | 1383 | (M − H)− |
| DP-189 | SQDAA50 | 0.90 | 1487 | (M − H)− |
| DP-190 | SQDAA50 | 0.93 | 1515 | (M − H)− |
| DP-191 | SQDAA50 | 0.82 | 1431 | (M − H)− |
| DP-192 | SQDAA50 | 0.91 | 1501 | (M − H)− |
| DP-193 | SQDAA50 | 0.84 | 1431 | (M − H)− |
| DP-194 | SQDAA50 | 0.83 | 1397 | (M − H)− |
| DP-195 | SQDAA50 | 0.72 | 1341 | (M − H)− |
| DP-196 | SQDAA50 | 0.77 | 1256 | (M − H)− |
| DP-197 | SQDAA50 | 0.80 | 1312 | (M − H)− |
| DP-198 | SQDAA50 | 0.81 | 1284 | (M − H)− |
| DP-199 | SQDAA50 | 0.84 | 1326 | (M − H)− |
| DP-200 | SQDAA50 | 0.77 | 1290 | (M − H)− |
| DP-201 | SQDAA50 | 0.81 | 1326 | (M − H)− |
| DP-202 | SQDAA50 | 0.81 | 1312 | (M − H)− |
| DP-203 | SQDAA50 | 0.88 | 1558 | (M − H)− |
| DP-204 | SQDAA50 | 0.86 | 1558 | (M − H)− |
| DP-205 | SQDAA50 | 0.89 | 1606 | (M − H)− |
| DP-206 | SQDAA50 | 0.88 | 1572 | (M − H)− |
| DP-207 | SQDAA50 | 0.94 | 1662 | (M − H)− |
| DP-208 | SQDAA50 | 0.87 | 1473 | (M − H)− |
| DP-209 | SQDAA50 | 0.82 | 1437 | (M − H)− |
| DP-210 | SQDAA50 | 0.89 | 1501 | (M − H)− |
| DP-211 | SQDAA50 | 0.88 | 1487 | (M − H)− |
| DP-212 | SQDAA50 | 0.83 | 1431 | (M − H)− |
| DP-213 | SQDAA50 | 0.82 | 1451 | (M − H)− |
| DP-214 | SQDAA50 | 0.81 | 1431 | (M − H)− |
| DP-215 | SQDAA50 | 0.88 | 1380.4 | (M − H)− |
| DP-216 | SQDAA50 | 0.89 | 1413 | (M + H)+ |
| DP-217 | SQDAA50 | 0.86 | 1385 | (M + H)+ |
| DP-218 | SQDAA50 | 0.81 | 1409 | (M − H)− |
| DP-219 | SQDAA50 | 0.93 | 1497 | (M − H)− |
| DP-220 | SQDAA50 | 0.82 | 1395 | (M − H)− |
| DP-221 | SQDAA50 | 0.83 | 1397 | (M − H)− |
| DP-222 | SQDAA50 | 0.82 | 1411 | (M − H)− |
| DP-223 | SQDAA50 | 0.84 | 1397 | (M − H)− |
| DP-224 | SQDAA50 | 0.83 | 1395 | (M − H)− |
| DP-225 | SQDAA50 | 0.78 | 1409 | (M − H)− |
| DP-226 | SQDAA50 | 0.80 | 1284 | (M − H)− |
| DP-227 | SQDAA50 | 0.86 | 1295.4 | (M − H)− |
| DP-228 | SQDAA50 | 0.92 | 1368 | (M − H)− |
| DP-229 | SQDAA50 | 0.84 | 1311.5 | (M − H)− |
| DP-230 | SQDAA50 | 0.86 | 1311.4 | (M − H)− |
| DP-231 | SQDAA50 | 0.84 | 1323.4 | (M − H)− |
| DP-232 | SQDAA50 | 0.87 | 1339.4 | (M − H)− |
| DP-233 | SQDAA50 | 0.84 | 1326 | (M − H)− |
| DP-234 | SQDAA50 | 0.91 | 1368 | (M − H)− |
| DP-235 | SQDAA50 | 0.89 | 1368 | (M − H)− |
| DP-236 | SQDAA50 | 0.85 | 1309.4 | (M − H)− |
| DP-237 | SQDAA50 | 0.76 | 1224 | (M + H)+ |
| DP-238 | SQDAA50 | 0.80 | 1297.4 | (M − H)− |
| DP-239 | SQDAA50 | 0.81 | 1312 | (M + H)+ |
| DP-240 | SQDAA50 | 0.84 | 1339.4 | (M − H)− |
| DP-241 | SQDAA50 | 0.83 | 1326 | (M − H)− |
| DP-242 | SQDAA50 | 0.82 | 1297.4 | (M − H)− |
| DP-243 | SQDAA50 | 0.75 | 1221.4 | (M − H)− |
| DP-244 | SQDAA50 | 0.87 | 1339.4 | (M − H)− |
| DP-245 | SQDAA50 | 0.82 | 1283.4 | (M − H)− |
| DP-246 | SQDAA50 | 0.83 | 1314 | (M + H)+ |
| DP-247 | SQDAA50 | 0.87 | 1326 | (M − H)− |
| DP-248 | SQDAA50 | 0.90 | 1396 | (M − H)− |
| DP-249 | SQDAA50 | 0.87 | 1354 | (M − H)− |
| DP-250 | SQDAA50 | 0.83 | 1340 | (M − H)− |
| DP-251 | SQDAA50 | 0.86 | 1368 | (M − H)− |
| DP-252 | SQDAA50 | 0.80 | 1215 | (M + H)+ |
| DP-253 | SQDAA50 | 0.76 | 1123 | (M − H)− |
| DP-254 | SQDAA50 | 0.76 | 1123 | (M − H)− |
| DP-255 | SQDAA50 | 0.85 | 1241 | (M − H)− |
| DP-256 | SQDAA50 | 0.88 | 1283 | (M − H)− |
| DP-257 | SQDAA50 | 0.85 | 1223 | (M − H)− |
| DP-258 | SQDAA50 | 0.84 | 1227 | (M − H)− |
| DP-259 | SQDAA50 | 0.82 | 1227 | (M − H)− |
| DP-260 | SQDAA50 | 0.86 | 1242.4 | (M − H)− |
| DP-261 | SQDAA50 | 0.81 | 1243 | (M + H)+ |
| DP-262 | SQDAA50 | 0.79 | 1227 | (M − H)− |
| DP-263 | SQDAA50 | 0.80 | 1071.4 | (M − H)− |
| DP-264 | SQDAA50 | 0.85 | 1158 | (M + H)+ |
| DP-265 | SQDAA50 | 0.86 | 1138 | (M − H)− |
| DP-266 | SQDAA50 | 0.85 | 1110 | (M − H)− |
| DP-267 | SQDAA50 | 0.80 | 1096 | (M − H)− |
| DP-268 | SQDAA50 | 0.82 | 1141.4 | (M − H)− |
| DP-269 | SQDAA50 | 0.81 | 1098 | (M + H)+ |
| DP-270 | SQDAA50 | 0.79 | 1101.4 | (M − H)− |
| DP-271 | SQDAA50 | 0.78 | 1087.4 | (M − H)− |
| DP-272 | SQDAA50 | 0.83 | 1138 | (M − H)− |
| DP-273 | SQDAA50 | 0.80 | 1411 | (M − H)− |
| DP-274 | SQDAA50 | 0.80 | 1312 | (M − H)− |
| DP-275 | SQDAA50 | 0.83 | 1340 | (M − H)− |
| DP-276 | SQDAA50 | 0.80 | 1310 | (M − H)− |
| DP-277 | SQDAA50 | 0.82 | 1257 | (M − H)− |
| DP-278 | SQDAA50 | 0.91 | 1556 | (M − H)− |
| DP-279 | SQDAA50 | 0.91 | 1544 | (M − H)− |
| DP-280 | SQDAA50 | 0.87 | 1542 | (M − H)− |
| DP-281 | SQDAA50 | 0.88 | 1586 | (M − H)− |
| DP-282 | SQDAA50 | 0.84 | 1500 | (M − H)− |
| DP-283 | SQDAA50 | 0.91 | 1542 | (M − H)− |
| DP-284 | SQDAA50 | 0.89 | 1572 | (M − H)− |
| DP-285 | SQDAA50 | 0.81 | 1440 | (M − H)− |
| DP-286 | SQDAA50 | 0.95 | 1648 | (M − H)− |
| DP-287 | SQDAA50 | 0.89 | 1578 | (M − H)− |
| DP-288 | SQDAA50 | 0.77 | 1341 | (M − H)− |
| DP-289 | SQDAA50 | 0.93 | 1648 | (M − H)− |
| DP-290 | SQDAA50 | 0.81 | 1383 | (M − H)− |
| DP-291 | SQDAA50 | 0.88 | 1417 | (M − H)− |
| DP-292 | SQDAA50 | 0.95 | 1676 | (M − H)− |
| DP-293 | SQDAA50 | 0.86 | 1516 | (M − H)− |
| DP-294 | SQDAA50 | 0.80 | 1369 | (M − H)− |
| DP-295 | SQDAA50 | 0.95 | 1662 | (M − H)− |
| DP-296 | SQDAA50 | 0.78 | 1355 | (M − H)− |
| DP-297 | SQDAA50 | 0.88 | 1572 | (M − H)− |
| DP-298 | SQDAA50 | 0.85 | 1592 | (M − H)− |
| DP-299 | SQDAA50 | 0.90 | 1501 | (M − H)− |
| DP-300 | SQDAA50 | 0.89 | 1572 | (M − H)− |
| DP-301 | SQDAA50 | 0.86 | 1431 | (M − H)− |
| DP-302 | SQDAA50 | 0.87 | 1558 | (M − H)− |
| DP-303 | SQDAA50 | 0.89 | 1578 | (M − H)− |
| DP-304 | SQDAA50 | 0.84 | 1417 | (M − H)− |
| DP-305 | SQDAA50 | 0.86 | 1312 | (M − H)− |
| DP-306 | SQDAA50 | 0.85 | 1445 | (M − H)− |
| DP-307 | SQDAA50 | 0.79 | 1276 | (M − H)− |
| DP-308 | SQDAA50 | 0.86 | 1340 | (M − H)− |

TABLE 11-3-2-continued

| | LCMS condition | Retention time (min) | LCMS (ESI) m/z | |
|---|---|---|---|---|
| DP-309 | SQDAA50 | 0.82 | 1451 | (M − H)− |
| DP-310 | SQDAA50 | 0.80 | 1270 | (M − H)− |
| DP-311 | SQDAA50 | 0.81 | 1290 | (M − H)− |
| DP-312 | SQDAA50 | 0.80 | 1451 | (M − H)− |
| DP-313 | SQDAA50 | 0.81 | 1326 | (M − H)− |
| DP-314 | SQDAA50 | 0.80 | 1437 | (M − H)− |
| DP-315 | SQDAA50 | 0.81 | 1417 | (M − H)− |
| DP-316 | SQDAA50 | 0.77 | 1276 | (M − H)− |
| DP-317 | SQDAA50 | 0.79 | 1385 | (M − H)− |
| DP-318 | SQDAA50 | 0.80 | 1383 | (M − H)− |
| DP-319 | SQDAA50 | 0.65 | 1265 | (M − H)− |
| DP-320 | SQDAA50 | 0.84 | 1332 | (M − H)− |
| DP-321 | SQDAA50 | 0.83 | 1284 | (M − H)− |
| DP-322 | SQDAA50 | 0.73 | 1242 | (M − H)− |
| DP-323 | SQDAA50 | 0.85 | 1354 | (M − H)− |
| DP-324 | SQDAA50 | 0.76 | 1236 | (M − H)− |
| DP-325 | SQDAA50 | 0.86 | 1340 | (M − H)− |
| DP-326 | SQDAA50 | 0.69 | 1242 | (M − H)− |
| DP-327 | SQDAA50 | 0.82 | 1222 | (M − H)− |
| DP-328 | SQDAA50 | 0.79 | 1236 | (M − H)− |
| DP-329 | SQDAA50 | 0.85 | 1261 | (M − H)− |
| DP-330 | SQDAA50 | 0.77 | 1205 | (M − H)− |
| DP-331 | SQDAA50 | 0.83 | 1275 | (M − H)− |
| DP-332 | SQDAA50 | 0.84 | 1289 | (M − H)− |
| DP-333 | SQDAA50 | 0.87 | 1241 | (M − H)− |
| DP-334 | SQDAA50 | 0.84 | 1289 | (M − H)− |
| DP-335 | SQDAA50 | 0.80 | 1243 | (M − H)− |
| DP-336 | SQDAA50 | 0.88 | 1283 | (M − H)− |
| DP-337 | SQDAA50 | 0.73 | 1171 | (M − H)− |
| DP-338 | SQDAA50 | 0.87 | 1289 | (M − H)− |
| DP-339 | SQDAA50 | 0.82 | 1255 | (M − H)− |
| DP-340 | SQDAA50 | 0.77 | 1201 | (M − H)− |
| DP-341 | SQDAA50 | 0.68 | 1143 | (M − H)− |
| DP-342 | SQDAA50 | 0.85 | 1094 | (M − H)− |
| DP-343 | SQDAA50 | 0.86 | 1170 | (M − H)− |
| DP-344 | SQDAA50 | 0.81 | 1502 | (M − H)− |
| DP-345 | SQDAA50 | 0.71 | 1432 | (M − H)− |
| DP-346 | SQDAA50 | 0.73 | 1460 | (M − H)− |
| DP-347 | SQDAA50 | 0.85 | 1502 | (M − H)− |
| DP-348 | SQDAA50 | 0.79 | 1474 | (M − H)− |
| DP-349 | SQDAA50 | 0.70 | 1313 | (M − H)− |
| DP-350 | SQDAA50 | 0.94 | 1473 | (M − H)− |
| DP-351 | SQDAA50 | 0.85 | 1487 | (M − H)− |
| DP-352 | SQDAA50 | 0.81 | 1389 | (M − H)− |
| DP-353 | SQDAA50 | 0.77 | 1375 | (M − H)− |
| DP-354 | SQDAA50 | 0.72 | 1313 | (M − H)− |
| DP-355 | SQDAA50 | 0.77 | 1361 | (M − H)− |
| DP-356 | SQDAA50 | 0.79 | 1389 | (M − H)− |
| DP-357 | SQDAA50 | 0.72 | 1242 | (M − H)− |
| DP-358 | SQDAA50 | 0.83 | 1312 | (M − H)− |
| DP-359 | SQDAA50 | 0.85 | 1402 | (M − H)− |
| DP-360 | SQDFA05 | 0.88 | 1474 | (M − H)− |
| DP-361 | SQDAA50 | 0.70 | 1432 | (M − H)− |
| DP-362 | SQDAA50 | 0.78 | 1502 | (M − H)− |
| DP-363 | SQDAA50 | 0.72 | 1432 | (M − H)− |
| DP-364 | SQDAA50 | 0.83 | 1556 | (M − H)− |
| DP-365 | SQDAA50 | 0.81 | 1468 | (M − H)− |
| DP-366 | SQDAA50 | 0.86 | 1600 | (M − H)− |
| DP-367 | SQDAA50 | 0.76 | 1474 | (M − H)− |
| DP-368 | SQDAA50 | 0.69 | 1384 | (M − H)− |
| DP-369 | SQDAA50 | 0.85 | 1473 | (M − H)− |
| DP-370 | SQDAA50 | 0.76 | 1403 | (M − H)− |
| DP-371 | SQDAA50 | 0.83 | 1397 | (M − H)− |
| DP-372 | SQDAA50 | 0.85 | 1445 | (M − H)− |
| DP-373 | SQDAA50 | 0.89 | 1515 | (M − H)− |
| DP-374 | SQDAA50 | 0.79 | 1411 | (M − H)− |
| DP-375 | SQDAA50 | 0.77 | 1361 | (M − H)− |
| DP-376 | SQDAA50 | 0.87 | 1439 | (M − H)− |
| DP-377 | SQDAA50 | 0.75 | 1375 | (M − H)− |
| DP-378 | SQDAA50 | 0.77 | 1276 | (M − H)− |
| DP-379 | SQDAA50 | 0.81 | 1346 | (M − H)− |
| DP-380 | SQDAA50 | 0.76 | 1256 | (M − H)− |
| DP-381 | SQDAA50 | 0.81 | 1346 | (M − H)− |
| DP-382 | SQDAA50 | 0.80 | 1304 | (M − H)− |
| DP-383 | SQDAA50 | 0.76 | 1304 | (M − H)− |
| DP-384 | SQDAA50 | 0.82 | 1340 | (M − H)− |
| DP-385 | SQDAA50 | 0.75 | 1284 | (M − H)− |
| DP-386 | SQDAA50 | 0.83 | 1346 | (M − H)− |
| DP-387 | SQDAA50 | 0.88 | 1402 | (M − H)− |
| DP-388 | SQDAA50 | 0.71 | 1256 | (M − H)− |
| DP-389 | SQDAA50 | 0.78 | 1488 | (M − H)− |
| DP-390 | SQDAA50 | 0.86 | 1578 | (M − H)− |
| DP-391 | SQDAA50 | 0.79 | 1474 | (M − H)− |
| DP-392 | SQDAA50 | 0.78 | 1516 | (M − H)− |
| DP-393 | SQDAA50 | 0.84 | 1508 | (M − H)− |
| DP-394 | SQDAA50 | 0.79 | 1502 | (M − H)− |
| DP-395 | SQDAA50 | 0.78 | 1502 | (M − H)− |
| DP-396 | SQDAA50 | 0.81 | 1437 | (M − H)− |
| DP-397 | SQDAA50 | 0.90 | 1487 | (M − H)− |
| DP-398 | SQDAA50 | 0.80 | 1403 | (M − H)− |
| DP-399 | SQDAA50 | 0.87 | 1487 | (M − H)− |
| DP-400 | SQDAA50 | 0.74 | 1403 | (M − H)− |
| DP-401 | SQDAA50 | 0.84 | 1465 | (M − H)− |
| DP-402 | SQDAA50 | 0.80 | 1465 | (M − H)− |
| DP-403 | SQDAA50 | 0.88 | 1501 | (M − H)− |
| DP-404 | SQDAA50 | 0.77 | 1445 | (M − H)− |
| DP-405 | SQDAA50 | 0.79 | 1431 | (M − H)− |
| DP-406 | SQDAA50 | 0.70 | 1361 | (M − H)− |
| DP-407 | SQDAA50 | 0.78 | 1417 | (M − H)− |
| DP-408 | SQDAA50 | 0.78 | 1329 | (M + H)+ |
| DP-409 | SQDAA50 | 0.88 | 1387 | (M + H)+ |
| DP-410 | SQDAA50 | 0.74 | 1267 | (M + H)+ |
| DP-411 | SQDAA50 | 0.85 | 1252 | (M + H)+ |
| DP-412 | SQDAA50 | 0.95 | 1308 | (M + H)+ |
| DP-413 | SQDAA50 | 0.92 | 1280 | (M + H)+ |
| DP-414 | SQDAA50 | 0.78 | 1224 | (M + H)+ |
| DP-415 | SQDAA50 | 0.97 | 1332 | (M − H)− |
| DP-416 | SQDAA50 | 0.99 | 1342 | (M + H)+ |
| DP-417 | SQDAA50 | 0.98 | 1280 | (M + H)+ |
| DP-418 | SQDAA50 | 0.96 | 1266 | (M + H)+ |
| DP-419 | SQDAA50 | 0.78 | 1258 | (M + H)+ |
| DP-420 | SQDAA50 | 0.84 | 1224 | (M + H)+ |
| DP-421 | SQDAA50 | 0.92 | 1238 | (M + H)+ |
| DP-422 | SQDAA50 | 0.75 | 1216 | (M + H)+ |
| DP-423 | SQDAA50 | 0.89 | 1221 | (M + H)+ |
| DP-424 | SQDAA50 | 0.92 | 1277 | (M + H)+ |
| DP-425 | SQDAA50 | 0.99 | 1257 | (M + H)+ |
| DP-426 | SQDAA50 | 0.96 | 1259 | (M + H)+ |
| DP-427 | SQDAA50 | 1.02 | 1243 | (M + H)+ |
| DP-428 | SQDAA50 | 0.91 | 1181 | (M + H)+ |
| DP-429 | SQDAA50 | 1.13 | 1313 | (M + H)+ |
| DP-430 | SQDAA50 | 0.88 | 1207 | (M + H)+ |
| DP-431 | SQDAA50 | 0.93 | 1221 | (M + H)+ |
| DP-432 | SQDAA50 | 1.03 | 1271 | (M + H)+ |
| DP-433 | SQDAA50 | 0.90 | 1153 | (M + H)+ |
| DP-434 | SQDAA50 | 1.04 | 1243 | (M + H)+ |
| DP-435 | SQDAA50 | 0.86 | 1139 | (M + H)+ |
| DP-436 | SQDAA50 | 0.90 | 1221 | (M + H)+ |
| DP-437 | SQDAA50 | 0.95 | 1245 | (M + H)+ |
| DP-438 | SQDAA05 | 0.90 | 1203 | (M + H)+ |
| DP-439 | SQDAA50 | 0.92 | 1153 | (M + H)+ |
| DP-440 | SQDAA50 | 0.83 | 1096 | (M + H)+ |
| DP-441 | SQDAA50 | 1.02 | 1220 | (M + H)+ |
| DP-442 | SQDAA50 | 1.05 | 1220 | (M + H)+ |
| DP-443 | SQDAA50 | 0.85 | 1462 | (M + H)+ |
| DP-444 | SQDAA50 | 0.80 | 1384 | (M − H)− |
| DP-445 | SQDAA50 | 0.86 | 1462 | (M + H)+ |
| DP-446 | SQDAA50 | 0.96 | 1419 | (M + H)+ |
| DP-447 | SQDAA50 | 1.11 | 1427 | (M + H)+ |
| DP-448 | SQDAA50 | 0.81 | 1341 | (M − H)− |
| DP-449 | SQDAA50 | 0.81 | 1341 | (M − H)− |
| DP-450 | SQDAA50 | 0.83 | 1476 | (M + H)+ |
| DP-451 | SQDAA05 | 1.01 | 1475 | (M + H)+ |
| DP-452 | SQDAA50 | 0.93 | 1550 | (M − H)− |
| DP-453 | SQDAA50 | 0.98 | 1399 | (M + H)+ |
| DP-454 | SQDAA50 | 1.04 | 1544 | (M − H)− |
| DP-455 | SQDAA50 | 0.91 | 1504 | (M + H)+ |
| DP-456 | SQDAA50 | 0.99 | 1550 | (M − H)− |
| DP-457 | SQDAA50 | 0.82 | 1434 | (M + H)+ |
| DP-458 | SQDAA50 | 0.81 | 1315 | (M + H)+ |
| DP-459 | SQDAA50 | 1.05 | 1546 | (M + H)+ |
| DP-460 | SQDAA50 | 0.81 | 1448 | (M + H)+ |
| DP-461 | SQDAA50 | 1.11 | 1404 | (M + H)+ |
| DP-462 | SQDAA50 | 0.83 | 1244 | (M + H)+ |

TABLE 11-3-2-continued

| | LCMS condition | Retention time (min) | LCMS (ESI) m/z | |
|---|---|---|---|---|
| DP-463 | SQDAA50 | 0.80 | 1363 | (M + H)+ |
| DP-464 | SQDAA50 | 0.91 | 1405 | (M + H)+ |
| DP-465 | SQDAA50 | 0.75 | 1387 | (M + H)+ |
| DP-466 | SQDAA50 | 0.76 | 1357 | (M + H)+ |
| DP-467 | SQDFA05 | 0.74 | 1301 | (M + H)+ |
| DP-468 | SQDAA50 | 0.81 | 1413 | (M + H)+ |
| DP-469 | SQDAA50 | 0.75 | 1357 | (M + H)+ |
| DP-470 | SQDFA05 | 0.74 | 1301 | (M + H)+ |
| DP-471 | SQDAA50 | 0.78 | 1300 | (M + H)+ |
| DP-472 | SQDAA50 | 0.79 | 1266 | (M + H)+ |
| DP-473 | SQDAA50 | 0.78 | 1286 | (M + H)+ |
| DP-474 | SQDAA50 | 0.74 | 1244 | (M + H)+ |
| DP-475 | SQDAA50 | 0.78 | 1224 | (M + H)+ |
| DP-476 | SQDAA50 | 0.68 | 1196 | (M + H)+ |
| DP-477 | SQDAA50 | 0.80 | 1328 | (M + H)+ |
| DP-478 | SQDAA50 | 0.80 | 1280 | (M + H)+ |
| DP-479 | SQDAA50 | 0.81 | 1266 | (M + H)+ |
| DP-480 | SQDFA05 | 0.78 | 1196 | (M + H)+ |
| DP-481 | SQDAA50 | 0.81 | 1328 | (M + H)+ |
| DP-482 | SQDFA05 | 0.78 | 1256 | (M − H)− |
| DP-483 | SQDAA50 | 0.85 | 1532 | (M + H)+ |
| DP-484 | SQDAA50 | 0.85 | 1560 | (M + H)+ |
| DP-485 | SQDFA05 | 0.75 | 1109 | (M − H)− |
| DP-486 | SQDAA50 | 0.81 | 1235 | (M + H)+ |
| DP-487 | SQDAA50 | 0.81 | 1243 | (M + H)+ |
| DP-488 | SQDAA50 | 0.83 | 1257 | (M + H)+ |
| DP-489 | SQDAA50 | 0.75 | 1139 | (M + H)+ |
| DP-490 | SQDAA50 | 0.76 | 1357 | (M + H)+ |
| DP-491 | SQDAA50 | 0.81 | 1343 | (M + H)+ |
| DP-492 | SQDAA50 | 0.81 | 1399 | (M + H)+ |
| DP-493 | SQDAA50 | 0.89 | 1489 | (M + H)+ |
| DP-494 | SQDAA50 | 0.85 | 1172 | (M + H)+ |
| DP-495 | SQDAA50 | 0.80 | 1502 | (M − H)− |
| DP-496 | SQDAA50 | 0.85 | 1572 | (M − H)− |
| DP-497 | SQDAA50 | 0.80 | 1488 | (M − H)− |
| DP-498 | SQDAA50 | 0.74 | 1460 | (M − H)− |
| DP-499 | SQDAA50 | 0.88 | 1662 | (M − H)− |
| DP-500 | SQDAA50 | 0.81 | 1530 | (M − H)− |
| DP-501 | SQDAA50 | 0.91 | 1578 | (M − H)− |
| DP-502 | SQDAA50 | 0.80 | 1488 | (M − H)− |
| DP-503 | SQDAA50 | 0.89 | 1592 | (M − H)− |
| DP-504 | SQDAA50 | 0.81 | 1508 | (M − H)− |
| DP-505 | SQDAA50 | 0.74 | 1432 | (M − H)− |
| DP-506 | SQDAA50 | 0.80 | 1502 | (M − H)− |
| DP-507 | SQDAA50 | 0.76 | 1460 | (M − H)− |
| DP-508 | SQDAA50 | 0.74 | 1432 | (M − H)− |
| DP-509 | SQDAA50 | 0.72 | 1446 | (M − H)− |
| DP-510 | SQDAA50 | 0.89 | 1586 | (M − H)− |
| DP-511 | SQDAA50 | 0.69 | 1279 | (M − H)− |
| DP-512 | SQDAA50 | 0.83 | 1094 | (M − H)− |
| DP-513 | SQDAA50 | 0.80 | 1284 | (M − H)− |
| DP-514 | SQDAA50 | 0.77 | 1250 | (M − H)− |
| DP-515 | SQDAA50 | 0.84 | 1247 | (M − H)− |
| DP-516 | SQDAA50 | 0.74 | 1286 | (M + H)+ |
| DP-517 | SQDFA05 | 0.97 | 1399 | (M + H)+ |
| DP-518 | SQDFA05 | 1.12 | 1370 | (M + H)+ |
| DP-519 | SQDFA05 | 0.97 | 1215 | (M + H)+ |
| DP-520 | SQDFA05 | 0.99 | 1144 | (M + H)+ |
| DP-521 | SQDFA05 | 0.92 | 1033 | (M + H)+ |
| DP-522 | SQDFA05 | 0.72 | 943 | (M + H)+ |
| DP-523 | SQDFA05 | 0.91 | 999 | (M + H)+ |
| DP-524 | SQDFA05 | 0.84 | 969 | (M + H)+ |
| DP-525 | SQDFA05 | 0.83 | 1013 | (M + H)+ |
| DP-526 | SQDFA05 | 0.81 | 975 | (M + H)+ |
| DP-527 | SQDFA05 | 0.86 | 999 | (M + H)+ |
| DP-528 | SQDFA05 | 0.87 | 985 | (M + H)+ |
| DP-529 | SQDFA05 | 0.93 | 999 | (M + H)+ |
| DP-530 | SQDFA05 | 0.82 | 973 | (M + H)+ |
| DP-531 | SQDFA05 | 0.71 | 872 | (M + H)+ |
| DP-532 | SQDFA05 | 0.82 | 886 | (M + H)+ |
| DP-533 | SQDFA05 | 0.80 | 856 | (M + H)+ |
| DP-534 | SQDFA05 | 0.76 | 886 | (M + H)+ |
| DP-535 | SQDFA05 | 0.80 | 886 | (M + H)+ |
| DP-536 | SQDFA05 | 0.80 | 838 | (M + H)+ |
| DP-537 | SQDFA05 | 0.80 | 842 | (M + H)+ |
| DP-538 | SQDFA05 | 0.71 | 813.8 | (M + H)+ |
| DP-539 | SQDFA05 | 0.84 | 875.8 | (M + H)+ |
| DP-540 | SQDFA05 | 1.07 | 1239 | (M + H)+ |
| DP-541 | SQDFA05 | 1.03 | 1326 | (M + H)+ |
| DP-542 | SQDFA05 | 0.97 | 1312 | (M + H)+ |
| DP-543 | SQDFA05 | 1.02 | 1225 | (M + H)+ |
| DP-544 | SQDFA05 | 1.04 | 1342 | (M + H)+ |
| DP-545 | SQDFA05 | 1.04 | 1342 | (M + H)+ |
| DP-546 | SQDFA05 | 1.02 | 1328 | (M + H)+ |
| DP-547 | SQDFA05 | 1.05 | 1225 | (M + H)+ |
| DP-548 | SQDFA05 | 0.92 | 1236 | (M + H)+ |
| DP-549 | SQDFA05 | 0.97 | 1264 | (M + H)+ |
| DP-550 | SQDFA05 | 0.99 | 1310 | (M + H)+ |
| DP-551 | SQDFA05 | 1.06 | 1338 | (M + H)+ |
| DP-552 | SQDFA05 | 0.89 | 1268 | (M + H)+ |
| DP-553 | SQDFA05 | 0.96 | 1296 | (M + H)+ |
| DP-554 | SQDFA05 | 0.89 | 1268 | (M + H)+ |
| DP-555 | SQDFA05 | 0.97 | 1296 | (M + H)+ |
| DP-556 | SQDFA05 | 0.94 | 1268 | (M + H)+ |
| DP-557 | SQDFA05 | 0.97 | 1296 | (M + H)+ |
| DP-558 | SQDFA05 | 1.00 | 1298 | (M + H)+ |
| DP-559 | SQDFA05 | 1.04 | 1326 | (M + H)+ |
| DP-560 | SQDFA05 | 0.93 | 1238 | (M + H)+ |
| DP-561 | SQDFA05 | 0.97 | 1286 | (M + H)+ |
| DP-562 | SQDFA05 | 0.89 | 1104 | (M + H)+ |
| DP-563 | SQDFA05 | 0.94 | 1152 | (M + H)+ |
| DP-564 | SQDFA05 | 0.93 | 1250 | (M + H)+ |
| DP-565 | SQDAA50 | 0.80 | 1401 | (M − H)− |
| DP-566 | SQDAA50 | 0.76 | 1208 | (M − H)− |
| DP-567 | SQDAA50 | 0.82 | 1100 | (M − H)− |
| DP-568 | SQDAA50 | 0.75 | 1180 | (M − H)− |
| DP-569 | SQDAA50 | 0.77 | 1191 | (M − H)− |
| DP-570 | SQDAA50 | 0.89 | 1558 | (M − H)− |
| DP-571 | SQDAA50 | 0.81 | 1157 | (M − H)− |
| DP-572 | SQDAA50 | 0.94 | 1507 | (M − H)− |
| DP-573 | SQDAA50 | 0.98 | 1301 | (M − H)− |
| DP-574 | SQDAA50 | 0.89 | 1558 | (M − H)− |
| DP-575 | SQDAA50 | 0.83 | 1314 | (M − H)− |
| DP-576 | SQDAA50 | 0.90 | 1411 | (M − H)− |
| DP-577 | SQDAA50 | 0.92 | 1408 | (M − H)− |
| DP-578 | SQDAA50 | 0.79 | 1505 | (M − H)− |
| DP-579 | SQDAA50 | 0.85 | 1504 | (M − H)− |
| DP-580 | SQDAA50 | 0.89 | 1643 | (M − H)− |
| DP-581 | SQDAA50 | 0.80 | 1521 | (M − H)− |
| DP-582 | SQDAA50 | 0.87 | 1595 | (M − H)− |
| DP-583 | SQDAA50 | 0.86 | 1496 | (M − H)− |
| DP-584 | SQDAA50 | 0.90 | 1510 | (M − H)− |
| DP-585 | SQDFA05 | 0.77 | 1447 | (M − H)− |
| DP-586 | SQDFA05 | 1.01 | 1545 | (M − H)− |
| DP-587 | SQDFA05 | 0.75 | 1480.5 | (M − H)− |
| DP-588 | SQDFA05 | 1.00 | 1578.6 | (M − H)− |
| DP-589 | SQDFA05 | 0.98 | 1453.6 | (M − H)− |
| DP-590 | SQDFA05 | 0.82 | 1494.7 | (M − H)− |
| DP-591 | SQDFA05 | 0.82 | 1430.5 | (M − H)− |
| DP-592 | SQDFA05 | 0.88 | 1684 | (M − H)− |
| DP-593 | SQDFA05 | 0.78 | 1597 | (M − H)− |
| DP-594 | SQDFA05 | 0.88 | 1703 | (M − H)− |
| DP-595 | SQDFA05 | 1.00 | 1570 | (M − H)− |
| DP-596 | SQDFA05 | 1.09 | 1676 | (M − H)− |
| DP-597 | SQDFA05 | 0.72 | 1611 | (M − H)− |
| DP-598 | SQDFA05 | 0.88 | 1731 | (M − H)− |
| DP-599 | SQDFA05 | 0.79 | 1561 | (M − H)− |
| DP-600 | SQDFA05 | 1.01 | 1695 | (M − H)− |
| DP-601 | SQDFA05 | 1.15 | 1562 | (M − H)− |
| DP-602 | SQDFA05 | 1.09 | 1516 | (M − H)− |
| DP-603 | SQDFA05 | 1.15 | 1514 | (M − H)− |
| DP-604 | SQDFA05 | 1.17 | 1544 | (M − H)− |
| DP-605 | SQDFA05 | 0.98 | 1479 | (M − H)− |
| DP-606 | SQDFA05 | 1.03 | 1527 | (M − H)− |
| DP-607 | SQDFA05 | 1.19 | 1563 | (M − H)− |
| DP-608 | SQDFA05 | 1.09 | 1518 | (M − H)− |
| DP-609 | SQDFA05 | 1.10 | 1498 | (M − H)− |
| DP-610 | SQDFA05 | 1.14 | 1500 | (M − H)− |
| DP-611 | SQDFA05 | 1.07 | 1429 | (M − H)− |
| DP-612 | SQDFA05 | 1.08 | 1443 | (M − H)− |
| DP-613 | SQDFA05 | 1.11 | 1412 | (M − H)− |
| DP-614 | SQDFA05 | 1.06 | 1326 | (M − H)− |
| DP-615 | SQDFA05 | 1.10 | 1326 | (M − H)− |
| DP-616 | SQDFA05 | 1.12 | 1326 | (M − H)− |

TABLE 11-3-2-continued

| | LCMS condition | Retention time (min) | LCMS (ESI) m/z | |
|---|---|---|---|---|
| DP-617 | SQDFA05 | 0.93 | 1367 | (M − H)− |
| DP-618 | SQDFA05 | 1.01 | 1409 | (M − H)− |
| DP-619 | SQDFA05 | 0.84 | 1346 | (M − H)− |
| DP-620 | SQDFA05 | 1.01 | 1416 | (M − H)− |
| DP-621 | SQDFA05 | 1.03 | 1480 | (M − H)− |
| DP-622 | SQDFA05 | 0.91 | 1337 | (M − H)− |
| DP-623 | SQDFA05 | 0.92 | 1371 | (M − H)− |
| DP-624 | SQDFA05 | 0.88 | 1323 | (M − H)− |
| DP-625 | SQDFA05 | 0.94 | 1395 | (M − H)− |
| DP-626 | SQDFA05 | 0.98 | 1395 | (M − H)− |
| DP-627 | SQDFA05 | 0.82 | 1327 | (M − H)− |
| DP-628 | SQDFA05 | 0.99 | 1338 | (M − H)− |
| DP-629 | SQDFA05 | 0.87 | 1281 | (M − H)− |
| DP-630 | SQDFA05 | 0.91 | 1337 | (M − H)− |
| DP-631 | SQDFA05 | 0.68 | 1424 | (M − H)− |
| DP-632 | SQDFA05 | 1.01 | 1312 | (M + H)+ |
| DP-633 | SQDFA05 | 1.06 | 1342 | (M + H)+ |
| DP-634 | SQDFA05 | 0.98 | 1225 | (M + H)+ |
| DP-635 | SQDFA05 | 1.09 | 1356.5 | (M + H)+ |
| DP-636 | SQDFA05 | 1.05 | 1342 | (M + H)+ |
| DP-637 | SQDFA05 | 1.05 | 1342.5 | (M + H)+ |
| DP-638 | SQDFA05 | 1.03 | 1314 | (M + H)+ |
| DP-639 | SQDAA50 | 0.84 | 1189 | (M − H)− |
| DP-640 | SQDAA50 | 0.88 | 1203.5 | (M − H)− |
| DP-641 | SQDAA50 | 0.87 | 1203 | (M − H)− |
| DP-642 | SQDAA50 | 0.88 | 1203 | (M − H)− |
| DP-643 | SQDAA50 | 0.86 | 1203 | (M − H)− |
| DP-644 | SQDAA50 | 0.82 | 1189 | (M − H)− |
| DP-645 | SQDAA50 | 0.84 | 1189 | (M − H)− |
| DP-646 | SQDAA50 | 0.85 | 1189 | (M − H)− |
| DP-647 | SQDAA50 | 0.87 | 1203 | (M − H)− |
| DP-648 | SQDAA50 | 0.91 | 1203 | (M − H)− |
| DP-649 | SQDAA50 | 0.78 | 1147 | (M − H)− |
| DP-650 | SQDAA50 | 0.83 | 1161 | (M − H)− |
| DP-651 | SQDAA50 | 0.80 | 1147 | (M − H)− |
| DP-652 | SQDAA50 | 0.82 | 1147 | (M − H)− |
| DP-653 | SQDAA50 | 0.83 | 1147 | (M − H)− |
| DP-654 | SQDAA50 | 0.78 | 1187 | (M − H)− |
| DP-655 | SQDAA50 | 0.88 | 1187 | (M − H)− |
| DP-656 | SQDAA50 | 0.87 | 1187 | (M − H)− |
| DP-657 | SQDAA50 | 0.83 | 1187 | (M − H)− |
| DP-658 | SQDAA50 | 0.80 | 1318 | (M − H)− |
| DP-659 | SQDAA50 | 0.88 | 1547.5 | (M − H)− |
| DP-660 | SQDAA50 | 0.89 | 1510.5 | (M − H)− |
| DP-661 | SQDAA50 | 0.83 | 1347 | (M − H)− |
| DP-662 | SQDAA50 | 0.83 | 1333 | (M − H)− |
| DP-663 | SQDAA50 | 0.88 | 1292 | (M − H)− |
| DP-664 | SQDAA50 | 0.84 | 1165 | (M − H)− |
| DP-665 | SQDAA50 | 0.79 | 1549.5 | (M − H)− |
| DP-666 | SQDAA50 | 0.84 | 1528.5 | (M − H)− |
| DP-667 | SQDAA50 | 0.83 | 1528.5 | (M − H)− |
| DP-668 | SQDAA50 | 0.80 | 1282 | (M − H)− |
| DP-669 | SQDAA50 | 0.80 | 1197 | (M − H)− |
| DP-670 | SQDAA50 | 0.82 | 1567.5 | (M − H)− |
| DP-671 | SQDAA50 | 0.81 | 1480 | (M − H)− |
| DP-672 | SQDAA50 | 0.78 | 1355 | (M − H)− |
| DP-673 | SQDAA50 | 0.83 | 1013 | (M − H)− |
| DP-674 | SQDAA50 | 0.53 | 797.5 | (M − H)− |
| DP-675 | SQDAA50 | 0.67 | 1095 | (M − H)− |
| DP-676 | SQDFA05 | 1.02 | 1550.4 | (M − H)− |
| DP-677 | SQDFA05 | 0.74 | 900 | (M + H)+ |
| DP-678 | SQDFA05 | 0.84 | 870 | (M + H)+ |
| DP-679 | SQDFA05 | 0.97 | 912 | (M + H)+ |
| DP-680 | SQDFA05 | 0.82 | 900 | (M + H)+ |
| DP-681 | SQDFA05 | 0.95 | 942 | (M + H)+ |
| DP-682 | SQDFA05 | 0.87 | 1013 | (M + H)+ |
| DP-683 | SQDFA05 | 1.04 | 1055 | (M + H)+ |
| DP-684 | SQDFA05 | 1.08 | 1041 | (M + H)+ |
| DP-685 | SQDFA05 | 0.86 | 1027 | (M + H)+ |
| DP-686 | SQDFA05 | 1.01 | 1069 | (M + H)+ |
| DP-687 | SQDFA05 | 0.77 | 987 | (M + H)+ |
| DP-688 | SQDFA05 | 0.89 | 1029 | (M + H)+ |
| DP-689 | SQDFA05 | 1.05 | 1041 | (M + H)+ |
| DP-690 | SQDFA05 | 0.91 | 983 | (M + H)+ |
| DP-691 | SQDFA05 | 0.90 | 983 | (M + H)+ |
| DP-692 | SQDFA05 | 0.97 | 1027 | (M + H)+ |
| DP-693 | SQDFA05 | 0.93 | 1013 | (M + H)+ |
| DP-694 | SQDFA05 | 0.93 | 1013 | (M + H)+ |
| DP-695 | SQDFA05 | 0.86 | 1013 | (M + H)+ |
| DP-696 | SQDFA05 | 0.98 | 1041 | (M + H)+ |
| DP-697 | SQDFA05 | 0.94 | 999 | (M + H)+ |
| DP-698 | SQDFA05 | 1.01 | 1041 | (M + H)+ |
| DP-699 | SQDFA05 | 0.85 | 1003 | (M + H)+ |
| DP-700 | SQDFA05 | 0.96 | 1003 | (M + H)+ |
| DP-701 | SQDFA05 | 0.87 | 1017 | (M + H)+ |
| DP-702 | SQDFA05 | 0.86 | 1017 | (M + H)+ |
| DP-703 | SQDFA05 | 1.02 | 1059 | (M + H)+ |
| DP-704 | SQDFA05 | 0.88 | 1013 | (M + H)+ |
| DP-705 | SQDFA05 | 1.03 | 1055 | (M + H)+ |
| DP-706 | SQDFA05 | 1.10 | 1071 | (M + H)+ |
| DP-707 | SQDFA05 | 0.94 | 1013 | (M + H)+ |
| DP-708 | SQDFA05 | 0.95 | 999 | (M + H)+ |
| DP-709 | SQDFA05 | 0.89 | 1033 | (M + H)+ |
| DP-710 | SQDFA05 | 0.89 | 1033 | (M + H)+ |
| DP-711 | SQDFA05 | 0.88 | 1019 | (M + H)+ |
| DP-712 | SQDFA05 | 0.76 | 955 | (M + H)+ |
| DP-713 | SQDFA05 | 0.86 | 983 | (M + H)+ |
| DP-714 | SQDFA05 | 0.92 | 983 | (M + H)+ |
| DP-715 | SQDFA05 | 0.82 | 928 | (M + H)+ |
| DP-716 | SQDFA05 | 0.88 | 928 | (M + H)+ |
| DP-717 | SQDFA05 | 0.86 | 914 | (M + H)+ |
| DP-718 | SQDFA05 | 0.80 | 900 | (M + H)+ |
| DP-719 | SQDFA05 | 0.86 | 870 | (M + H)+ |
| DP-720 | SQDFA05 | 0.78 | 856 | (M + H)+ |
| DP-721 | SQDFA05 | 0.95 | 898 | (M + H)+ |
| DP-722 | SQDFA05 | 0.97 | 940 | (M + H)+ |
| DP-723 | SQDFA05 | 0.81 | 870 | (M + H)+ |
| DP-724 | SQDFA05 | 0.78 | 886 | (M + H)+ |
| DP-725 | SQDFA05 | 0.94 | 894 | (M + H)+ |
| DP-726 | SQDFA05 | 0.76 | 836 | (M + H)+ |
| DP-727 | SQDFA05 | 0.79 | 822 | (M + H)+ |
| DP-728 | SQDFA05 | 0.94 | 1294 | (M + H)+ |
| DP-729 | SQDFA05 | 0.95 | 1308 | (M + H)+ |
| DP-730 | SQDFA05 | 0.84 | 1300 | (M + H)+ |
| DP-731 | SQDFA05 | 0.87 | 1314 | (M + H)+ |
| DP-732 | SQDFA05 | 0.93 | 1326 | (M + H)+ |
| DP-733 | SQDFA05 | 0.95 | 1340 | (M + H)+ |
| DP-734 | SQDFA05 | 0.82 | 1258 | (M + H)+ |
| DP-735 | SQDFA05 | 0.86 | 1272 | (M + H)+ |
| DP-736 | SQDFA05 | 0.89 | 1252 | (M + H)+ |
| DP-737 | SQDFA05 | 0.93 | 1266 | (M + H)+ |
| DP-738 | SQDFA05 | 0.85 | 898 | (M + H)+ |
| DP-739 | SQDFA05 | 0.80 | 856 | (M + H)+ |
| DP-740 | SQDFA05 | 0.91 | 898 | (M + H)+ |
| DP-741 | SQDFA05 | 0.74 | 842 | (M + H)+ |
| DP-742 | SQDFA05 | 0.73 | 828 | (M + H)+ |
| DP-743 | SQDFA05 | 0.78 | 914 | (M + H)+ |
| DP-744 | SQDFA05 | 0.76 | 842 | (M + H)+ |
| DP-745 | SQDFA05 | 0.79 | 842 | (M + H)+ |
| DP-746 | SQDFA05 | 0.91 | 928 | (M + H)+ |
| DP-747 | SQDFA05 | 0.90 | 928 | (M + H)+ |
| DP-748 | SQDFA05 | 0.96 | 942 | (M + H)+ |
| DP-749 | SQDFA05 | 0.81 | 886 | (M + H)+ |
| DP-750 | SQDFA05 | 0.73 | 872 | (M + H)+ |
| DP-751 | SQDFA05 | 0.75 | 862 | (M + H)+ |
| DP-752 | SQDFA05 | 0.79 | 1274 | (M + H)+ |
| DP-753 | SQDFA05 | 0.76 | 1218 | (M + H)+ |
| DP-754 | SQDFA05 | 0.92 | 1316 | (M + H)+ |
| DP-755 | SQDFA05 | 0.89 | 1274 | (M + H)+ |
| DP-756 | SQDFA05 | 1.01 | 1388 | (M + H)+ |
| DP-757 | SQDFA05 | 1.05 | 1358 | (M + H)+ |
| DP-758 | SQDFA05 | 1.10 | 1430 | (M + H)+ |
| DP-759 | SQDFA05 | 1.04 | 1388 | (M + H)+ |
| DP-760 | SQDFA05 | 1.08 | 1402 | (M + H)+ |
| DP-761 | SQDFA05 | 1.11 | 1430 | (M + H)+ |
| DP-762 | SQDFA05 | 1.09 | 1392 | (M + H)+ |
| DP-763 | SQDFA05 | 0.73 | 1147 | (M + H)+ |
| DP-764 | SQDFA05 | 0.75 | 1113 | (M + H)+ |
| DP-765 | SQDFA05 | 0.72 | 1131 | (M + H)+ |
| DP-766 | SQDFA05 | 0.78 | 1159 | (M + H)+ |
| DP-767 | SQDFA05 | 0.85 | 1201 | (M + H)+ |
| DP-768 | SQDFA05 | 0.90 | 1201 | (M + H)+ |
| DP-769 | SQDFA05 | 0.96 | 1203 | (M + H)+ |
| DP-770 | SQDFA05 | 0.87 | 1183 | (M + H)+ |

TABLE 11-3-2-continued

| | LCMS condition | Retention time (min) | LCMS (ESI) m/z | |
|---|---|---|---|---|
| DP-771 | SQDFA05 | 1.07 | 1289 | (M + H)+ |
| DP-772 | SQDFA05 | 1.04 | 1239 | (M + H)+ |
| DP-773 | SQDFA05 | 1.05 | 1273 | (M + H)+ |
| DP-774 | SQDFA05 | 0.99 | 1229 | (M + H)+ |
| DP-775 | SQDFA05 | 1.02 | 1275 | (M + H)+ |
| DP-776 | SQDFA05 | 1.09 | 1307 | (M + H)+ |
| DP-777 | SQDFA05 | 0.90 | 1148 | (M + H)+ |
| DP-778 | SQDFA05 | 0.83 | 1104 | (M + H)+ |
| DP-779 | SQDFA05 | 0.95 | 1114 | (M + H)+ |
| DP-780 | SQDFA05 | 0.93 | 1146 | (M + H)+ |
| DP-781 | SQDFA05 | 1.07 | 1188 | (M + H)+ |
| DP-782 | SQDFA05 | 1.11 | 1222 | (M + H)+ |
| DP-783 | SQDFA05 | 0.97 | 1132 | (M + H)+ |
| DP-784 | SQDFA05 | 0.90 | 1138 | (M + H)+ |
| DP-785 | SQDFA05 | 0.80 | 1021 | (M + H)+ |
| DP-786 | SQDFA05 | 0.74 | 945 | (M + H)+ |
| DP-787 | SQDFA05 | 0.87 | 987 | (M + H)+ |
| DP-788 | SQDFA05 | 0.90 | 1005 | (M + H)+ |
| DP-789 | SQDFA05 | 0.89 | 1029 | (M + H)+ |
| DP-790 | SQDFA05 | 1.04 | 1115 | (M + H)+ |
| DP-791 | SQDFA05 | 1.02 | 1075 | (M + H)+ |
| DP-792 | SQDFA05 | 1.09 | 1149 | (M + H)+ |
| DP-793 | SQDFA05 | 1.02 | 1123 | (M + H)+ |
| DP-794 | SQDFA05 | 0.65 | 846 | (M + H)+ |
| DP-795 | SQDFA05 | 0.77 | 916 | (M + H)+ |
| DP-796 | SQDFA05 | 0.78 | 878 | (M + H)+ |
| DP-797 | SQDFA05 | 0.81 | 902 | (M + H)+ |
| DP-798 | SQDFA05 | 1.01 | 918 | (M + H)+ |
| DP-799 | SQDFA05 | 0.94 | 1063 | (M + H)+ |
| DP-800 | SQDFA05 | 0.89 | 995 | (M + H)+ |
| DP-801 | SQDFA05 | 1.02 | 1049 | (M + H)+ |
| DP-802 | SQDFA05 | 0.96 | 981 | (M + H)+ |
| DP-803 | SQDFA05 | 1.00 | 1148 | (M + H)+ |
| DP-804 | SQDFA05 | 0.96 | 1080 | (M + H)+ |
| DP-805 | SQDFA05 | 0.94 | 1251 | (M + H)+ |
| DP-806 | SQDFA05 | 0.89 | 1149 | (M + H)+ |
| DP-807 | SQDFA05 | 0.85 | 1278 | (M + H)+ |
| DP-808 | SQDFA05 | 0.79 | 1176 | (M + H)+ |
| DP-809 | SQDFA05 | 1.00 | 1250 | (M + H)+ |
| DP-810 | SQDFA05 | 0.98 | 1360 | (M + H)+ |
| DP-811 | SQDFA05 | 1.06 | 1200 | (M + H)+ |
| DP-812 | SQDFA05 | 1.01 | 1214 | (M + H)+ |
| DP-813 | SQDFA05 | 0.93 | 1078 | (M + H)+ |
| DP-814 | SQDFA05 | 0.95 | 1396 | (M + H)+ |
| DP-815 | SQDFA05 | 0.87 | 1231 | (M + H)+ |
| DP-816 | SQDFA05 | 1.05 | 1241 | (M + H)+ |
| DP-817 | SQDFA05 | 1.14 | 1283 | (M + H)+ |
| DP-818 | SQDFA05 | 0.70 | 966 | (M + H)+ |
| DP-819 | SQDFA05 | 0.78 | 963 | (M + H)+ |
| DP-820 | SQDFA05 | 1.03 | 1128 | (M + H)+ |
| DP-821 | SQDFA05 | 1.12 | 1170 | (M + H)+ |
| DP-822 | SQDFA05 | 0.97 | 1114 | (M + H)+ |
| DP-823 | SQDFA05 | 0.82 | 985 | (M + H)+ |
| DP-824 | SQDFA05 | 0.82 | 1019 | (M + H)+ |
| DP-825 | SQDFA05 | 0.93 | 954 | (M + H)+ |
| DP-826 | SQDFA05 | 0.91 | 868 | (M + H)+ |
| DP-827 | SQDFA05 | 0.74 | 950 | (M + H)+ |
| DP-828 | SQDFA05 | 0.92 | 1019 | (M + H)+ |
| DP-829 | SQDFA05 | 0.83 | 1181 | (M + H)+ |
| DP-830 | SQDFA05 | 1.08 | 1254 | (M − H)− |
| DP-831 | SQDFA05 | 1.10 | 1254 | (M − H)− |
| DP-832 | SQDFA05 | 1.11 | 1270 | (M − H)− |
| DP-833 | SQDFA05 | 1.08 | 1272 | (M − H)− |
| DP-834 | SQDFA05 | 1.09 | 1272 | (M − H)− |
| DP-835 | SQDFA05 | 1.12 | 1288 | (M − H)− |
| DP-836 | SQDFA05 | 1.10 | 1274 | (M − H)− |
| DP-837 | SQDFA05 | 1.14 | 1270 | (M − H)− |
| DP-838 | SQDFA05 | 1.14 | 1256 | (M − H)− |
| DP-839 | SQDFA05 | 1.07 | 1282 | (M − H)− |
| DP-840 | SQDFA05 | 1.03 | 1260 | (M − H)− |
| DP-841 | SQDFA05 | 1.11 | 1288 | (M − H)− |
| DP-842 | SQDFA05 | 1.05 | 1294 | (M − H)− |
| DP-843 | SQDFA05 | 1.03 | 1260 | (M − H)− |
| DP-844 | SQDFA05 | 1.14 | 1074 | (M − H)− |
| DP-845 | SQDFA05 | 1.04 | 1224 | (M − H)− |
| DP-846 | SQDFA05 | 1.12 | 1272 | (M − H)− |
| DP-847 | SQDFA05 | 1.09 | 1288 | (M − H)− |
| DP-848 | SQDFA05 | 0.92 | 1262 | (M − H)− |
| DP-849 | SQDFA05 | 1.09 | 1274 | (M − H)− |
| DP-850 | SQDFA05 | 1.15 | 1429 | (M − H)− |
| DP-851 | SQDFA05 | 1.16 | 1429 | (M − H)− |
| DP-852 | SQDFA05 | 1.21 | 1445 | (M − H)− |
| DP-853 | SQDFA05 | 1.18 | 1431 | (M − H)− |
| DP-854 | SQDFA05 | 1.10 | 1371 | (M − H)− |
| DP-855 | SQDFA05 | 1.12 | 1371 | (M − H)− |
| DP-856 | SQDFA05 | 1.12 | 1387 | (M − H)− |
| DP-857 | SQDFA05 | 1.12 | 1373 | (M − H)− |
| DP-858 | SQDFA05 | 1.24 | 1415 | (M − H)− |
| DP-859 | SQDFA05 | 1.19 | 1401 | (M − H)− |
| DP-860 | SQDFA05 | 1.00 | 1357 | (M − H)− |
| DP-861 | SQDFA05 | 1.20 | 1445 | (M − H)− |
| DP-862 | SQDFA05 | 1.25 | 1459 | (M − H)− |
| DP-863 | SQDFA05 | 1.05 | 1147 | (M − H)− |
| DP-864 | SQDFA05 | 1.12 | 1371 | (M − H)− |
| DP-865 | SQDFA05 | 1.02 | 1359 | (M − H)− |
| DP-866 | SQDFA05 | 0.97 | 1279 | (M − H)− |
| DP-867 | SQDFA05 | 1.14 | 1401 | (M − H)− |
| DP-868 | SQDFA05 | 1.14 | 1415 | (M − H)− |
| DP-869 | SQDFA05 | 1.12 | 1270 | (M + H)+ |
| DP-870 | SQDFA05 | 1.13 | 1268 | (M − H)− |
| DP-871 | SQDFA05 | 1.14 | 1284 | (M − H)− |
| DP-872 | SQDFA05 | 1.20 | 1270 | (M − H)− |
| DP-873 | SQDFA05 | 1.21 | 1544 | (M − H)− |
| DP-874 | SQDFA05 | 1.20 | 1530 | (M − H)− |
| DP-875 | SQDFA05 | 1.10 | 1458 | (M − H)− |
| DP-876 | SQDFA05 | 1.08 | 1444 | (M − H)− |
| DP-877 | SQDFA05 | 1.07 | 1444 | (M + H)+ |
| DP-878 | SQDFA05 | 0.96 | 1428 | (M − H)− |
| DP-879 | SQDFA05 | 0.95 | 1166 | (M − H)− |
| DP-880 | SQDFA05 | 1.01 | 1178 | (M − H)− |
| DP-881 | SQDFA05 | 1.09 | 1458 | (M − H)− |
| DP-882 | SQDFA05 | 1.13 | 1456 | (M − H)− |
| DP-883 | SQDFA05 | 1.05 | 1470 | (M − H)− |
| DP-884 | SQDFA05 | 1.14 | 1482 | (M − H)− |
| DP-885 | SQDFA05 | 1.03 | 1428 | (M − H)− |
| DP-886 | SQDFA05 | 1.08 | 1444 | (M − H)− |
| DP-887 | SQDFA05 | 0.98 | 1513 | (M − H)− |
| DP-888 | SQDFA05 | 1.04 | 1371 | (M − H)− |
| DP-889 | SQDFA05 | 1.01 | 1513 | (M − H)− |
| DP-890 | SQDFA05 | 1.09 | 1371 | (M − H)− |
| DP-891 | SQDFA05 | 1.00 | 1529 | (M − H)− |
| DP-892 | SQDFA05 | 1.06 | 1387 | (M − H)− |
| DP-893 | SQDFA05 | 1.01 | 1517 | (M + H)+ |
| DP-894 | SQDFA05 | 1.09 | 1373 | (M − H)− |
| DP-895 | SQDFA05 | 1.01 | 1555 | (M − H)− |
| DP-896 | SQDFA05 | 1.02 | 1541 | (M − H)− |
| DP-897 | SQDFA05 | 1.07 | 1371 | (M − H)− |
| DP-898 | SQDFA05 | 0.96 | 1485 | (M − H)− |
| DP-899 | SQDFA05 | 1.13 | 1581 | (M − H)− |
| DP-900 | SQDFA05 | 0.73 | 1527 | (M − H)− |
| DP-901 | SQDFA05 | 0.91 | 1343 | (M − H)− |
| DP-902 | SQDFA05 | 1.04 | 1555 | (M − H)− |
| DP-903 | SQDFA05 | 0.97 | 1499 | (M − H)− |
| DP-904 | SQDFA05 | 0.77 | 1206 | (M − H)− |
| DP-905 | SQDFA05 | 0.80 | 1269.9 | (M − H)− |
| DP-906 | SQDFA05 | 0.83 | 1448.2 | (M − H)− |
| DP-907 | SQDFA05 | 1.08 | 1236 | (M − H)− |
| DP-908 | SQDFA05 | 1.34 | 1504.3 | (M − H)− |
| DP-909 | SQDFA05 | 1.21 | 1335.1 | (M − H)− |
| DP-910 | SQDAA50 | 0.87 | 1513 | (M − H)− |
| DP-911 | SQDAA50 | 0.89 | 1481 | (M − H)− |
| DP-912 | SQDAA50 | 0.88 | 1459 | (M − H)− |
| DP-913 | SQDAA50 | 0.93 | 1481 | (M − H)− |
| DP-914 | SQDAA50 | 0.91 | 1543 | (M − H)− |
| DP-915 | SQDAA50 | 0.86 | 1567 | (M − H)− |
| DP-916 | SQDAA50 | 0.91 | 1444 | (M − H)− |
| DP-917 | SQDAA50 | 0.87 | 1368 | (M − H)− |
| DP-918 | SQDAA50 | 0.85 | 1360 | (M − H)− |
| DP-919 | SQDAA50 | 0.83 | 1258 | (M − H)− |
| DP-920 | SQDAA50 | 0.90 | 1416 | (M − H)− |

TABLE 11-3-2-continued

| | LCMS condition | Retention time (min) | LCMS (ESI) m/z | |
|---|---|---|---|---|
| DP-921 | SQDAA50 | 0.86 | 1402 | (M − H)− |
| DP-922 | SQDAA50 | 0.85 | 1570 | (M − H)− |
| DP-923 | SQDAA50 | 0.96 | 1742 | (M − H)− |
| DP-924 | SQDAA50 | 0.90 | 1620 | (M − H)− |
| DP-925 | SQDAA50 | 0.94 | 1640 | (M − H)− |
| DP-926 | SQDAA50 | 0.90 | 1660 | (M − H)− |
| DP-927 | SQDAA50 | 0.93 | 1561 | (M − H)− |
| DP-928 | SQDAA50 | 0.88 | 1521 | (M − H)− |
| DP-929 | SQDAA50 | 0.85 | 1471 | (M − H)− |
| DP-930 | SQDAA50 | 0.87 | 1501 | (M − H)− |
| DP-931 | SQDAA50 | 0.95 | 1577 | (M − H)− |
| DP-932 | SQDAA50 | 0.80 | 1326 | (M − H)− |
| DP-933 | SQDAA50 | 0.89 | 1362 | (M − H)− |
| DP-934 | SQDAA50 | 0.87 | 1368 | (M − H)− |
| DP-935 | SQDAA50 | 0.93 | 1699 | (M − H)− |
| DP-936 | SQDAA50 | 0.90 | 1697 | (M − H)− |
| DP-937 | SQDAA50 | 0.89 | 1623 | (M − H)− |
| DP-938 | SQDAA50 | 0.98 | 1721 | (M − H)− |
| DP-939 | SQDAA50 | 0.89 | 1510 | (M − H)− |
| DP-940 | SQDAA50 | 0.91 | 1532 | (M − H)− |
| DP-941 | SQDAA50 | 0.93 | 1670 | (M − H)− |
| DP-942 | SQDAA50 | 0.92 | 1646 | (M − H)− |
| DP-943 | SQDAA50 | 0.91 | 1584 | (M − H)− |
| DP-944 | SQDAA50 | 0.92 | 1693 | (M − H)− |
| DP-945 | SQDAA50 | 0.92 | 1665 | (M − H)− |
| DP-946 | SQDAA50 | 0.94 | 1775 | (M − H)− |
| DP-947 | SQDAA50 | 0.92 | 1679 | (M − H)− |
| DP-948 | SQDAA50 | 0.91 | 1663 | (M − H)− |
| DP-949 | SQDAA50 | 0.88 | 1705 | (M − H)− |
| DP-950 | SQDAA50 | 0.92 | 1699 | (M − H)− |
| DP-951 | SQDAA50 | 0.92 | 1693 | (M − H)− |
| DP-952 | SQDAA50 | 0.88 | 1655 | (M − H)− |
| DP-953 | SQDAA50 | 0.94 | 1771 | (M − H)− |
| DP-954 | SQDAA50 | 0.91 | 1723 | (M − H)− |
| DP-955 | SQDAA50 | 0.87 | 1593 | (M − H)− |
| DP-956 | SQDAA50 | 0.89 | 1667 | (M − H)− |
| DP-957 | SQDAA50 | 0.87 | 1552 | (M − H)− |
| DP-958 | SQDAA50 | 0.90 | 1594 | (M − H)− |
| DP-959 | SQDAA50 | 0.87 | 1667 | (M − H)− |
| DP-960 | SQDAA50 | 0.90 | 1543 | (M − H)− |
| DP-961 | SQDAA50 | 0.89 | 1628 | (M − H)− |
| DP-962 | SQDAA50 | 0.93 | 1640 | (M − H)− |
| DP-963 | SQDAA50 | 0.94 | 1723 | (M − H)− |
| DP-964 | SQDAA50 | 0.85 | 1479 | (M − H)− |
| DP-965 | SQDAA50 | 0.90 | 1237 | (M − H)− |

The details of LC/MS conditions are described in Table 11-4.

1-3-2. Synthetic Example of Peptides Having Linear Portions 1

Synthesis of Peptides Having Fixed Linear Portions (MePhe-Ala-pip and MePhe-MePhe-Ala-pip)

Synthetic examples of peptides will be described in which the C-terminal is amidated (piperidinated in this example) and side chain carboxylic acid of aspartic acid located at a site other than the C-terminal is cyclized with the N-terminal amino group to form an amide bond. This example will be described as a representative example, but any method described in different places of the present specification (such as pages 142, 512 (Example 15, 2-2) and 553 (Example 18)) may also be used for peptide chemical synthesis. The following scheme X illustrates an example of such synthesis.

Figure 93:
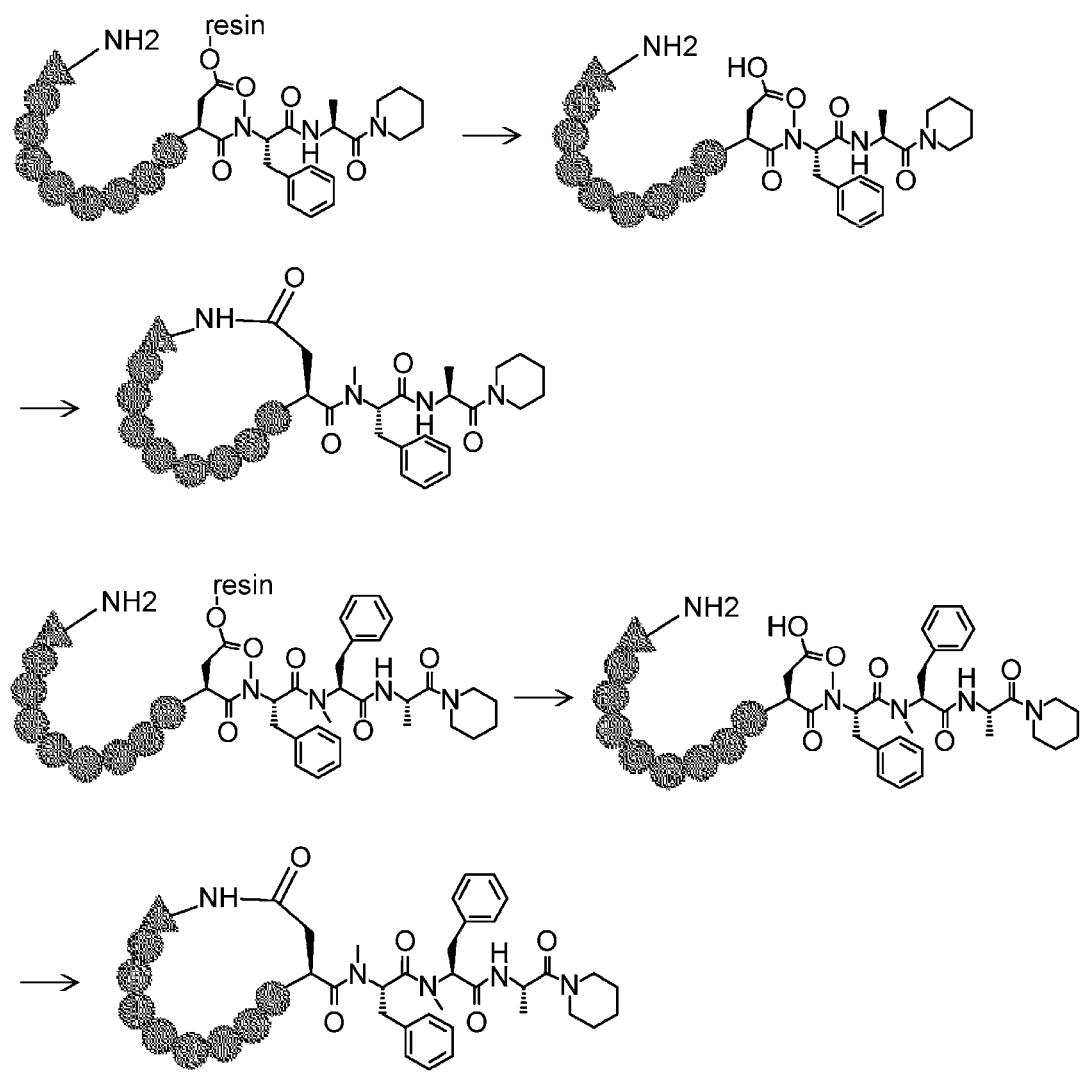
FIG. 93 is a diagram showing scheme x. Scheme x shows an example of the methods for synthesizing the amide-cyclized drug-like peptides having fixed linear portions (MePhe-Ala-pip and MePhe-MePhe-Ala-pip).

See FIG. 93.

Peptides were elongated using Fmoc-Asp(O-Trt(2-Cl)-Resin)-MePhe-Ala-pip, which was synthesized by the same method as for Compound SP455 (200 mg) and Fmoc amino acids such as Fmoc-MePhe-OH, Fmoc-EtPhe-OH (Compound SP443), Fmoc-MeAla-OH, Fmoc-MeLeu-OH, Fmoc-D-MeAla-OH, Fmoc-MeGly-OH, Fmoc-MeVal-OH, Fmoc-MeIle-OH, Fmoc-g-MeAbu-OH, Fmoc-b-MeAla-OH, Fmoc-nPrGly-OH (Compound SP815), Fmoc-MeAla(4-Thz)-OH (Compound SP811), Fmoc-Pro-OH, Fmoc-Aze(2)-OH, Fmoc-Pic(2)-OH, Fmoc-Phe-OH, Fmoc-Phg-OH, Fmoc-Val-OH, Fmoc-D-Val-OH, Fmoc-Ser(tBu)-OH, Fmoc-Thr(Trt)-OH, Fmoc-Leu-OH, Fmoc-D-Leu-OH, Fmoc-Ile-OH, Fmoc-Ala-OH, Fmoc-D-Ala-OH, Fmoc-Gly-OH, Fmoc-Lys(Me2)-OH, Fmoc-Arg(Me2)-OH, Fmoc-Gln(Me2)-OH (Compound SP448), Fmoc-Gln(Me)-OH (Compound SP446), Fmoc-Gln-OH, Fmoc-AlGly-OH, Fmoc-Ala(4-Thz)-OH, Fmoc-Ala(CN)—OH, Fmoc-Hph-OH, Fmoc-Phe3-OH, Fmoc-Ala(3Pyr)-OH, Fmoc-Tyr(3-F)—OH (Compound SP450), Fmoc-Glu(OA1)-OH, Fmoc-His(Mmt)-OH and Fmoc-Ala(5-Tet(Trt))-OH (Compound SP409) (abbreviations for amino acids are described in Table 11-2). Peptide elongation was carried out according to a peptide synthesis method by the Fmoc method previously described in Examples. For example, in the synthesis of Compound DP-177, the Fmoc group at the N-terminal was

TABLE 11-4

| Analysis condition | Instrument | Column(I.D. × length) (mm) | Mobile phase | Gradient (A/B) | Flow rate (mL/min) | Column temperature (° C.) | Wavelength |
|---|---|---|---|---|---|---|---|
| SQDAA05 | Acquity UPLC/SQD | Ascentis Express C18 (2.1 × 50) | A) 10 mM AcONH$_4$, H$_2$O B) MeOH | 95/5 => 0/100(1.0 min) 0/100(0.4 min) | 1 | 35 | 210-400 nm PDA total |
| SQDAA50 | Acquity UPLC/SQD | Ascentis Express C18 (2.1 × 50) | A) 10 mM AcONH$_4$, H$_2$O B) MeOH | 50/50 => 0/100(0.7 min) 0/100(0.7 min) | 1 | 35 | 210-400 nm PDA total |
| SQDFA05 | Acquity UPLC/SQD | Ascentis Express C18 (2.1 × 50) | A) 0.1% FA, H$_2$O B) 0.1% FA, MeCN | 95/5 => 0/100(1.0 min) 0/100(0.4 min) | 1 | 35 | 210-400 nm PDA total |
| SQDFA50 | Acquity UPLC/SQD | Ascentis Express C18 (2.1 × 50) | A) 0.1% FA, H$_2$O B) 0.1% FA, MeCN | 50/50 => 0/100(0.7 min) 0/100(0.7 min) | 1 | 35 | 210-400 nm PDA total |
| ZQAA05 | 2525BGM/ 2996PDA/ ZQ2000 | Chromolith Flash RP-18e (4.6 × 25) | A) 10 mM AcONH$_4$, H$_2$O B) MeOH | 95/5 => 0/100(3.0 min) 0/100(2.0 min) | 2 | Room temperature | 210-400 nm PDA total |
| ZQAA50 | 2525BGM/ 2996PDA/ ZQ2000 | Chromolith Flash RP-18e (4.6 × 25) | A) 10 mM AcONH$_4$, H$_2$O B) MeOH | 50/50 => 0/100(3.0 min) 0/100(2.0 min) | 2 | Room temperature | 210-400 nm PDA total |
| ZQFA05 | 2525BGM/ 2996PDA/ ZQ2000 | Chromolith Flash RP-18e (4.6 × 25) | A) 0.1% FA, H$_2$O B) 0.1% FA, MeCN | 95/5 => 0/100(3.0 min) 0/100(2.0 min) | 2 | Room temperature | 210-400 nm PDA total |
| SMDmethod1 | Nexera/2020 | Kinetex 1.7 u C18 (2.1 × 50) | A) 0.05% TFA, H$_2$O B) 0.05% TFA, MeCN | 95/5 => 0/100(1.5 min) 0/100(0.5 min) | 1 | 35 | 210-400 nm PDA total | removed on a peptide synthesizer after the peptide elongation, and the resin was then washed with DMF. The peptide was cleaved from the resin by adding a 4 N solution of HCl in 1,4-dioxane/dichloromethane/2,2,2-trifluoroethanol/triisopropylsilane (=1/60/30/5.7, v/v, 4 mL) to the resin and reacting for two hours. After completion of the reaction, the solution in the tube was filtered through a synthesis column to remove the resin, and the resin was washed with dichloromethane/2,2,2-trifluoroethanol (=1/1, v/v, 1 mL) twice. All extracts were combined, neutralized with DIPEA (50.0 µL, 0.286 mmol) and then concentrated under reduced pressure. The resulting residue was dissolved in dichloromethane (8 mL). A solution of O-(7-aza-1H-benzotriazol-1-yl)-N,N,N,N-tetramethyluronium hexafluorophosphate (HATU) (68 mg, 0.18 mmol) in DMSO (0.20 mL) and DIPEA (37 µL, 0.21 mmol) were added, followed by shaking at room temperature for 2 hours. The solvent was evaporated under reduced pressure, after which the residue was dissolved in DMSO and the solution was purified by preparative HPLC to afford DP-177 (4.27 mg, 5%). The title amide-cyclized drug-like peptide was synthesized by the same method as described above or using Fmoc-Asp(O-Trt(2-Cl)-Resin)-MePhe-MePhe-Ala-pip (SEQ ID NO: 321) prepared in the same manner as for Compound SP459 in place of Fmoc-Asp(O-Trt(2-Cl)-Resin)-MePhe-Ala-pip. DP-123 to 124, DP-177 to 214, DP-278 to 316, DP-344 to 407, DP-443 to 464, DP-483 to 484, DP-490 to 493, DP-495 to 510, DP-587 to 588, DP-590 to 591, DP-593 to 594, DP-597 to 613 and DP-631 can be synthesized by this synthetic method. The mass spectral value and the liquid chromatography retention time of each compound are described in Table 11-3-2.

1-3-3. Synthetic Examples of Peptides Having Linear Portion 1 (2)

Synthetic examples of peptides will be described in which the C-terminal carboxylic group is amidated (piperidinated in this example) and the side chain carboxylic acid of aspartic acid located at a site other than the C-terminal is cyclized with the N-terminal amino group by an amide bond. This example will be described as a representative example, but any method described in different places of the present specification may also be used for peptide chemical synthesis. The following scheme G2 illustrates an example of such chemical synthesis of peptides.

A peptide was elongated according to a peptide synthesis method by the Fmoc method previously described, using amino acid with Boc on amino group in place of Fmoc amino acid at the N-terminal, using 2-chlorotrityl resin on which Fmoc-Ile-OH, Fmoc-Phe-OH, Fmoc-Val-OH or Fmoc-Ala-OH is supported (100 mg) (the amino acid was supported on the resin according to the aforementioned method) and using Fmoc-Asp(OtBu)-OH as an aspartic acid source. After the peptide elongation, the peptide was cleaved from the resin by treating with dichloromethane/2,2,2-trifluoroethanol/triisopropylsilane (=1/1/0.2, v/v, 2 mL) and shaking for two hours. After completion of the cleaving reaction, the solution in the tube was filtered through a synthesis column to remove the resin, and the resin was washed with dichloromethane/2,2,2-trifluoroethanol (=1/1, v/v, 1 mL) twice. All extracts were then combined and concentrated under reduced pressure. The C-terminal carboxylic acid was piperidinated by treating the resulting residue with O-(7-aza-1H-benzotriazol-1-yl)-N,N,N,N-tetramethyluronium hexafluorophosphate (HATU) (0.12 mmol), DIPEA (0.145 mmol) and piperidine (0.145 mmol), and the solvent was then evaporated under reduced pressure. The Boc group at the N-terminal, the o-trityl group, and the tert-butyl group of aspartic acid side chain carboxylic acid were removed at the same time by treating the resulting residue with TFA/triisopropylsilane/dichloromethane (3/1/6, v/v, 0.5 mL). After completion of the reaction, ice-cooled DMF (3 mL) was added and the solvent was then evaporated under reduced pressure. The resulting residue was dissolved in dichloromethane (3 mL). Further, water (0.5 mL) was added, and the solution was allowed to pass through a diatomaceous earth column (1 mL, Chem Elut, manufactured by Agilent Technologies) wetted with water (0.5 mL) and was extracted with dichloromethane (3 mL) twice. All extracts were combined, and the peptide was cyclized by treating the solution with O-(7-aza-1H-benzotriazol-1-yl)-N,N,N,N-tetramethyluronium hexafluorophosphate (HATU) (0.12 mmol) and DIPEA (0.145 mmol). The solvent was evaporated under reduced pressure. After that, the residue was dissolved in DMSO and the solution was purified by preparative HPLC to synthesize the amide-cyclized drug-like peptide having a linear portion 1. DP-40 to 46, DP-565 to 584, DP-658 to 672, DP-910 to 956, DP-960 to 963 and DP-965 can be synthesized by methods in accordance with this synthesis method. The mass spectral value and the retention time of LC/MS of each compound are described in Table 11-3-2.

Figure 94:
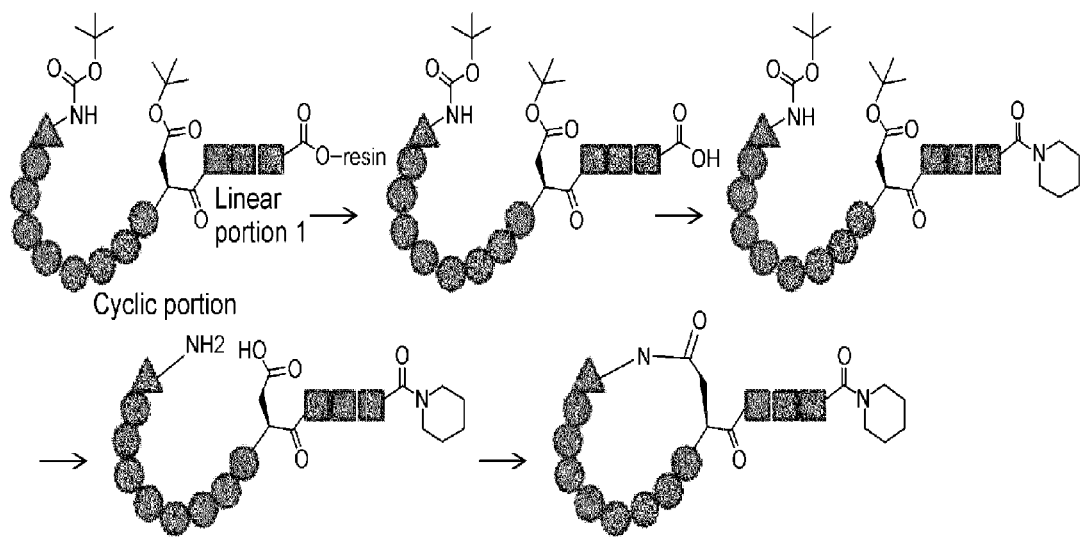
FIG. 94 is a diagram showing scheme G2. Scheme G2 shows an example of the methods for synthesizing the amide-cyclized drug-like peptides having linear portions 1.

See FIG. 94.

1-3-4. Synthesis of Peptides Having Linear Portions 1 and 2

Chemical synthetic examples of peptides will be described in which the carboxylic acid in side chain of aspartic acid located at a site other than the C-terminal is amidated (piperidinated in this example but optionally bound to a peptide of linear portion 1) and the amino group in side chain of an amino acid having an amino group in side chain located at a site other than the N-terminal is cyclized with carboxylic acid of an amino acid located at the C-terminal by amide bond. Here, synthetic example of peptide using Asp-pip as an intersection unit (○ unit), an amino acid having protected amino group in side chain as an amino group source, and a carboxylic acid analog at the N-terminal is illustrated as a representative example of peptides having linear portions 1 and 2. $^{HO}$Gly protected on hydroxyl group can be used instead of $^{HO}$Gly without protecting group. Any method described in different places of the present specification may also be used for peptide chemical synthesis. The following scheme G3 illustrates an example of such synthesis.

Figure 95:
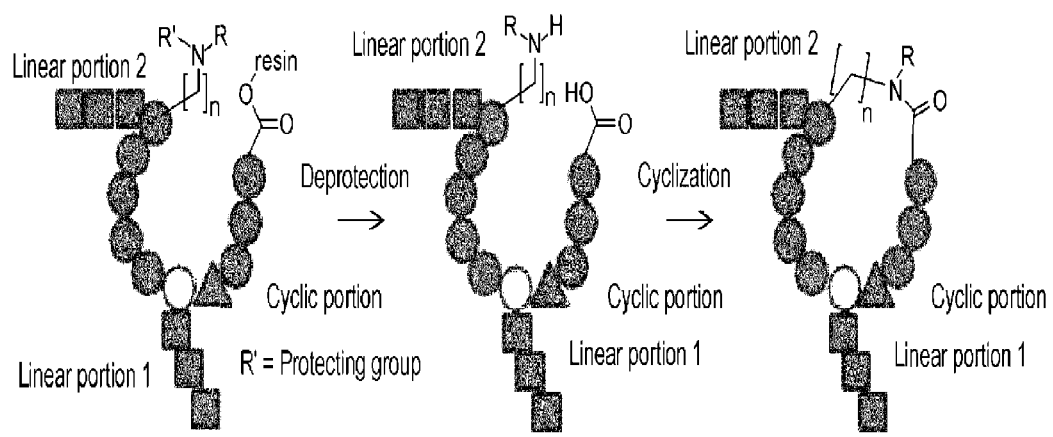
FIG. 95 is a diagram showing scheme G3. Scheme G3 shows an example of the methods for synthesizing the amide-cyclized drug-like peptides having linear portions 1 and 2.

See FIG. 95.

Although this example will be described as a representative example, the synthesis method is not limited to this method, and various methods are possible as applications of this method. For example, such synthesis is also possible by elongating a peptide using an allyl ester as a protecting group for the side chain carboxylic group and a 1-(4,4-dimethyl-2,6-dioxocyclohexylidene)ethyl group (Dde) as a protecting group for the cyclization site amino group and then condensing the oligopeptide with the amino group resulting from deprotection of the Dde group and cyclizing with the carboxylic group resulting from deprotection with the allyl ester on a resin, as in the Non patent literature (Tetrahedron Lett. 1993, 34, 4709-4712).

DP-964

(SEQ ID NO: 323)
$^{HO}$Gly-Pro-MeLeu-*Lys-MeAla-Leu-MeLeu-MeLeu-Asp-piperidine-MeLeu-MePhe(3-Cl)-Ile*
(cyclized at two * sites)

the reaction, the solution in the tube was filtered through a synthesis column to remove the resin. The reaction solution was diluted by DMF (1 mL). The resin was washed with dichloromethane/2,2,2-trifluoroethanol (=1/1, v/v, 1 mL) twice, followed by combining all solution and purification by reverse-phase column chromatography. The resulting Scheme x2. An example of the methods for synthesizing the amide-cyclized drug-like peptides having linear portion 2(DP-964)

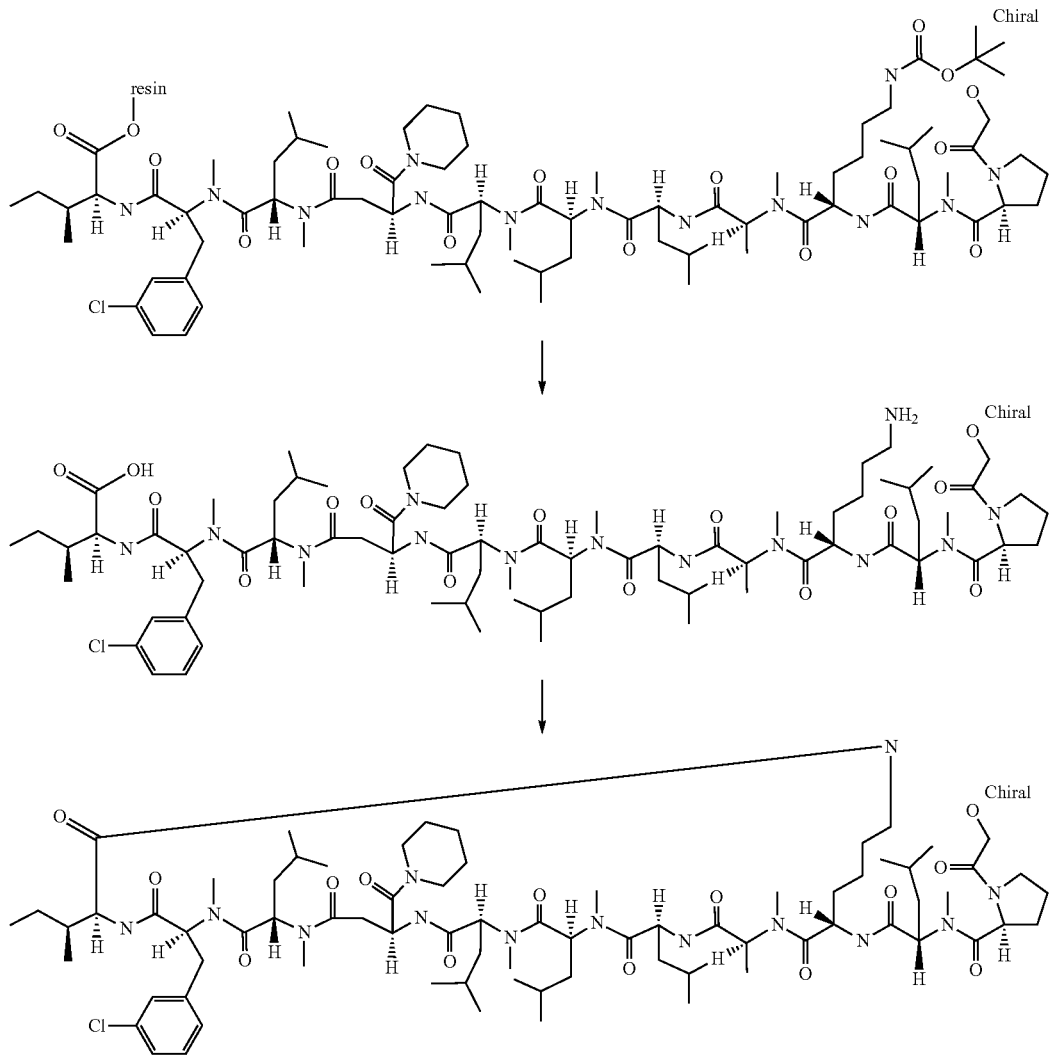

A peptide was elongated using $^{HO}$Gly in place of Fmoc amino acid at the N-terminal, using Fmoc-Asp-Piperidine as an aspartic acid source, using 2-chlorotrityl resin on which Fmoc-Ile-OH is supported (100 mg), and using Fmoc amino acids such as Fmoc-MePhe(3-Cl)—OH (Compound SP812), Fmoc-MeAla-OH, Fmoc-MeLeu-OH, Fmoc-Pro-OH, Fmoc-Leu-OH and Fmoc-Lys(Boc)-OH (abbreviations for amino acids are described in Table 11-2). Peptide elongation was carried out according to a peptide synthesis method by the Fmoc method previously described in Examples. The peptide was cleaved from the resin by treating with a 4 N solution of HCl in 1,4-dioxane/dichloromethane/trifluoroethanol/triisopropylsilane (1/40/20/4, v/v, 2 mL) and shaking for two hours. After completion of product was dissolved in dichloromethane (8 mL), a solution of O-(7-aza-1H-benzotriazol-1-yl)-N,N,N,N-tetramethyluronium hexafluorophosphate (HATU) (0.129 mmol) in DMSO (0.129 mL) and DIPEA (30.0 μL, 0.155 mmol) were then added, followed by shaking at room temperature for 1 hour. The solvent was evaporated under reduced pressure, then the residue was dissolved in DMSO and the solution was purified by reverse-phase column chromatography (Wakosil 25C18, 0.1% aqueous formic acid solution/0.1% formic acid-acetonitrile) to afford the title compound DP-964 (1.6 mg, 1.6%).

LCMS (ESI) m/z=1479 (M–H)–

Retention time: 0.85 min (analysis condition SQDAA50)

1-3-5. Synthesis of Peptides Having Amino Acids (Fmoc-Ala(5-Tet(Trt))-OH and Fmoc-His(Mmt)-OH in this Example) that is Needed to be Deprotected Using a Weak Acid after Peptide Cyclization A peptide was elongated using Fmoc-Asp(O-Trt(2-Cl)-Resin)-pip synthesized by the same method as for Compound SP402 (100 mg) and Fmoc amino acids such as Fmoc-MePhe-OH, Fmoc-MeAla-OH, Fmoc-MeLeu-OH, Fmoc-D-MeAla-OH, Fmoc-MeGly-OH, Fmoc-MeVal-OH, Fmoc-Pro-OH, Fmoc-Phe-OH, Fmoc-Val-OH, Fmoc-D-Val-OH, Fmoc-Ser(tBu)-OH, Fmoc-Thr(Trt)-OH, Fmoc-Leu-OH, Fmoc-D-Leu-OH, Fmoc-Ile-OH, Fmoc-Ala-OH, Fmoc-D-Ala-OH, Fmoc-Gly-OH, Fmoc-His(Mmt)-OH and Fmoc-Ala(5-Tet(Trt))-OH (Compound 409) (abbreviations for amino acids are described in Table 11-2). Peptide elongation was carried out according to a peptide synthesis method by the Fmoc method previously described in Examples. For example, in the synthesis of Compound DP-908, the Fmoc group at the N-terminal was deprotected, and the peptide was cleaved from the resin by adding dichloromethane/trifluoroethanol (=2/1, v/v, 2 ml) to the resin and shaking for 2 hours. After completion of the reaction, the solution in the tube was filtered through a synthesis column to remove the resin. Further, dichloromethane/trifluoroethanol (=2/1, v/v, 1 ml) were added to the resin, followed by shaking for 15 minutes. The solution was combined with the above solution, and the solvent was evaporated under reduced pressure. The resulting residue was dissolved in DCM (8 ml), and then, DIPEA (17 µL, 0.096 mmol) was added. Cyclization reaction between the N-terminal amine and the Asp side chain carboxylic acid was carried out by adding 1 M O-(7-aza-1H-benzotriazol-1-yl)-N,N,N,N-tetramethyluronium hexafluorophosphate (HATU) (30 mg, 0.08 mmol) in DMSO (250 µL). After completion of the reaction, the solvent was evaporated. The resulting residue was dissolved in trifluoroethanol (1.0 ml). The protecting group was deprotected by adding TFA/triisopropylsilane/DCM (1/5/94, v/v/v, 1.0 ml) and stirred for 10 minutes. After completion of the reaction, TFA was neutralized by adding DIPEA (50 µL, 0.286 mmol), and the solvent was evaporated. The resulting crude product was dissolved in dimethyl sulfoxide, the resulting peptide solution was purified by high-performance reverse-phase chromatography (HPLC), and the solvent was evaporated. The resulting residue was dissolved in trifluoroethanol (1.5 ml), followed by addition of water (0.5 ml) and hexane (2 ml). The mixture was stirred and the hexane layer was removed. Hexane (2 ml) was added once again, the mixture was stirred and the hexane layer was removed, after which the solvent was evaporated to afford Compound DP-908 (1.92 mg, 4.8%). The title amide-cyclized drug-like peptide was synthesized by the same method as described above or using Fmoc-Asp(O-Trt(2-Cl)-Resin)-MePhe-Ala-pip prepared in the same manner as for Compound SP455 in place of Fmoc-Asp(O-Trt(2-Cl)-Resin)-pip. DP-585 to 586, DP-592, DP-676, DP-904 to 909 can be synthesized by this synthetic method. The mass spectral value and the liquid chromatography retention time of each compound are described in Table 11-3-2.

1-3-5. Synthesis of Peptides Having an Amino Acid (Fmoc-Glu(OA1)-OH in this Example) that is Needed to be Deprotected Using Reduction Reaction after Peptide Cyclization A peptide was elongated using Fmoc-Asp(O-Trt(2-Cl)-Resin)-MePhe-Ala-pip synthesized by the same method as for Compound SP455 (100 mg) and Fmoc amino acids such as Fmoc-MePhe-OH, Fmoc-MeAla-OH, Fmoc-MeLeu-OH, Fmoc-MeGly-OH, Fmoc-MeVal-OH, Fmoc-Pro-OH, Fmoc-Phe-OH, Fmoc-Val-OH, Fmoc-D-Val-OH, Fmoc-Ser(tBu)-OH, Fmoc-Thr(Trt)-OH, Fmoc-Leu-OH, Fmoc-Ala-OH, Fmoc-D-Ala-OH, Fmoc-Gly-OH, and Fmoc-Glu(OA1)-OH (abbreviations for amino acids are described in Table 11-2). Peptide elongation was carried out according to a peptide synthesis method by the Fmoc method previously described in Examples. For example, in the synthesis of Compound DP-595, the Fmoc group at the N-terminal was deprotected, and the peptide was cleaved from the resin by adding dichloromethane/trifluoroethanol (=2/1, v/v, 2 ml) to the resin and shaking for 2 hours. After completion of the reaction, the solution in the tube was filtered through a synthesis column to remove the resin. Further, dichloromethane/trifluoroethanol (=2/1, v/v, 1 ml) were added to the resin, followed by shaking for 15 minutes. The solution was combined with the above solution, and the solvent was evaporated under reduced pressure. The resulting residue was dissolved in DCM (8 ml), and then, DIPEA (20 µL, 0.115 mmol) was added. Cyclization reaction between the N-terminal amine and the Asp side chain carboxylic acid was carried out by adding 1 M O-(7-aza-1H-benzotriazol-1-yl)-N,N,N,N-tetramethyluronium hexafluorophosphate (HATU) (37 mg, 0.096 mmol) in DMSO (200 µL). After completion of the reaction, the solvent was evaporated. The resulting crude product was dissolved in DMF, followed by addition of a solution of tetrakis(triphenylphosphine)palladium(0) (Pd(PPh3)4) (7 mg, 0.006 mmol) in dichloromethane (1 ml). Subsequently, phenylsilane (7.4 ul, 0.06 mmol) was added and the mixture was stirred at room temperature for 1 hour. The reaction solution was filtrated and then, the organic layer was then concentrated under reduced pressure. The resulting crude product was dissolved in DMSO, and the resulting peptide solution was purified by high performance reverse-phase chromatography (HPLC), after which the solvent was evaporated to afford Compound DP-595 (14.7 mg, 22%). Amide-cyclized drug-like peptides DP-589 and DP-596 were synthesized by the same method as described above. The mass spectral value and the liquid chromatography retention time of each compound are described in Table 11-3-2.

1-3-7. Synthesis of Peptide Derivatives in which the Main Chain Carboxylic Acid Sites Possessed by C-Terminal Amino Acids are Removed and Replaced with Alkyl Groups or the Like Synthetic examples of compounds will be described each having a β-amino acid derivative at the C-terminal, which was cyclized with an N-terminal amino group by an amide bond, and not having a linear portion. Any method described in different places of the present specification may also be used for peptide chemical synthesis.

A peptide was elongated according to a peptide synthesis method by the Fmoc method previously described in Examples using a compound bound to 2-chlorotrityl resin (Compound SP405, 100 mg) and using Fmoc amino acids such as Fmoc-MePhe-OH, Fmoc-MePhe(3-Cl)—H, Fmoc-MeAla-OH, Fmoc-b-MeAla-OH, Fmoc-g-MeAbu-OH, Fmoc-MeLeu-OH, Fmoc-MeIle-OH, Fmoc-MeVal-OH, Fmoc-D-MeAla-OH, Fmoc-MeGly-OH, Fmoc-MeSer(DMT)-OH, Fmoc-Pro-OH, Fmoc-Phe-OH, Fmoc-Phe(4-CF3)-OH, Fmoc-Val-OH, Fmoc-D-Val-OH, Fmoc-Ser(Trt)-OH, Fmoc-Ser(tBu)-OH, Fmoc-Thr(Trt)-OH, Fmoc-Leu-OH, Fmoc-D-Leu-OH, Fmoc-Ile-OH, Fmoc-AOC(2)-OH, Fmoc-Abu-OH, Fmoc-Ala-OH, Fmoc-D-Ala-OH and Fmoc-Gly-OH (abbreviations for amino acids are described in Table 11-2). For example, in the synthesis of Compound DP-639, the Fmoc group at the N-terminal was deprotected after the peptide elongation, and the peptide was cleaved from the resin by adding dichloromethane/trifluoroethanol (=2/1, v/v, 2 ml) to the resin and shaking for 2 hours. After completion of the reaction, the solution in the tube was filtered through a synthesis column to remove the resin. Further, dichloromethane/trifluoroethanol (=2/1, v/v, 1 ml) were added to the resin, followed by shaking for 15 minutes. The solution was combined with the above solution, and the solvent was evaporated under reduced pressure. The resulting residue was dissolved in DCM (4 ml), and DIPEA (31.6 µl, 3.6 eq.) was added. Cyclization reaction between the N-terminal main chain amine and the C-terminal carboxylic acid was carried out by adding 1 M O-(7-aza-1H-benzotriazol-1-yl)-N,N,N,N-tetramethyluronium hexafluorophosphate (HATU) in DMSO (155 µl, 3.0 eq.) thereto. After completion of the reaction, the solvent was evaporated. The resulting residue was dissolved in trifluoroethanol (1.1 ml), and triisopropylsilane (5.0 eq.) was added. The protecting group was deprotected by adding TFA/DCM (1/99, v/v, 1.1 ml) thereto and stirring for 10 minutes. After completion of the reaction, TFA was neutralized by adding DIPEA (43.9 µl, 5.0 eq.), and the solvent was evaporated. The resulting crude product was dissolved in dimethyl sulfoxide, the resulting peptide solution was purified by high-performance reverse-phase chromatography (HPLC), and the solvent was evaporated. The resulting residue was dissolved in trifluoroethanol (1.5 ml), followed by addition of water (0.5 ml) and hexane (2 ml). The mixture was stirred and the hexane layer was removed. Hexane (2 ml) was added once again, the mixture was stirred and the hexane layer was removed, after which the solvent was evaporated to afford DP-639. DP-640 to DP-657 and DP-752 to DP829 were obtained by the same method as for DP-639 or using Fmoc-3-CF3-bAla-(O-Trt-(2-Cl)-Resin ((S)-3-((((9H-fluoren-9-yl)methoxy)carbonyl)amino)-4,4,4-trifluorobutanoic acid-2-chlorotrityl resin, Compound SP407) in place of Fmoc-L-3-ABU-(O-Trt-(2-Cl)-Resin ((S)-3-((((9H-fluoren-9-yl)methoxy)carbonyl)amino)butanoic acid-2-chlorotrityl resin). The mass spectral value and the liquid chromatography retention time of each compound are described in Table 11-3-2.

2. Synthesis of C—C Cyclized Peptides 2-1. Synthesis of an N-Terminal Carboxylic Acid Derivative for Synthesizing C—C Cyclized Peptides 2-1-1. Methyl pent-4-ynoate

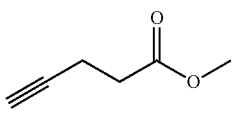

Pent-4-ynoic acid (5.0 g, 51.0 mmol) was dissolved in MeOH (20 ml), and a solution of trimethylsilyldiazomethane in diethyl ether (2.0 M, 50 ml, 100 mmol) was added under ice-cooling. After stirring at room temperature for 30 minutes, the reaction solution was concentrated under reduced pressure to afford the title compound (5.7 g, 100%).

¹H-NMR (Varian 400-MR, 400 MHz, CDCl₃) δ ppm 3.72 (3H, s), 2.50-2.60 (4H, m), 1.99 (1H, m)

2-1-2. Methyl (E)-5-(4,4,5,5-tetramethyl-1,3,2-dioxaborolan-2-yl)pent-4-enoate

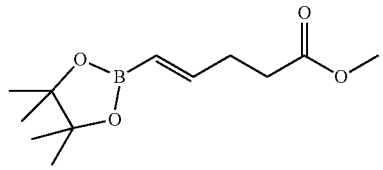

Methyl pent-4-ynoate (5.0 g, 44.6 mmol) and 4,4,5,5-tetramethyl-1,3,2-dioxaborolane (7.42 g, 58.0 mmol) were mixed, zirconocene chloride hydride (1.18 g, 4.46 mmol) and triethylamine (0.622 ml, 4.46 mmol) were added and the mixture was stirred at 65° C. overnight. The reaction solution was left to cool and then diluted with diethyl ether, and the precipitated white solid was removed by filtration through celite. The filtrate was concentrated under reduced pressure, and the resulting residue was purified by column chromatography (hexane:ethyl acetate) to afford the title compound (5.36 g, 50.1%).

¹H-NMR (Varian 400-MR, 400 MHz, CDCl₃) δ ppm 6.02 (1H, dt, 18, 5.6 Hz), 5.48 (1H, d, 18 Hz), 3.68 (3H, s), 2.40-2.53 (4H, m), 1.28 (12H, s)

2-1-3. (E)-5-Boronopent-4-enoic Acid

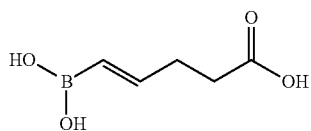

Methyl (E)-5-(4,4,5,5-tetramethyl-1,3,2-dioxaborolan-2-yl)pent-4-enoate (2.0 g, 8.33 mmol) was dissolved in MeOH (100 ml), a 0.8 M aqueous potassium hydroxide solution (52.1 ml, 41.6 mmol) was added and the mixture was stirred at room temperature overnight. MeOH was removed by concentration under reduced pressure, and 3 M hydrochloric acid was then added until the pH was 3. This aqueous solution was washed with tert-butyl methyl ether and then concentrated under reduced pressure. The resulting residue was purified by column chromatography (10 mM aqueous ammonium acetate solution:methanol). Obtained fractions were concentrated under reduced pressure, and the resulting solid was washed with tert-butyl methyl ether again to afford the title compound (674.6 mg, 56.3%).

¹H-NMR (Varian 400-MR, 400 MHz, D₂O) δ ppm 6.59 (1H, m), 5.51 (1H, d, 18 Hz), 2.44-2.51 (4H, m)

2-2. Synthesis of C—C Cyclized Drug-Like Peptides 2-2-1. Synthesis of *Phe-MeLeu-MeVal-MeGly-Thr-MeAla-Ala-MeLeu-Leu-Phe*-piperidine (C—C-Bonded Between Two * Sites) (Compound DCC-1) (SEQ ID NO: 324)

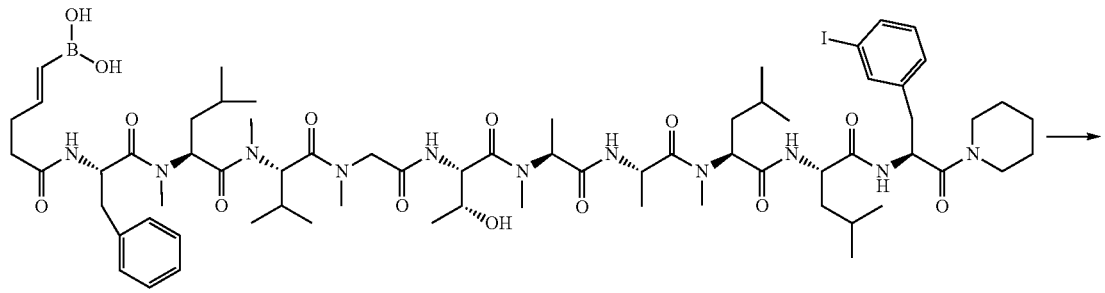

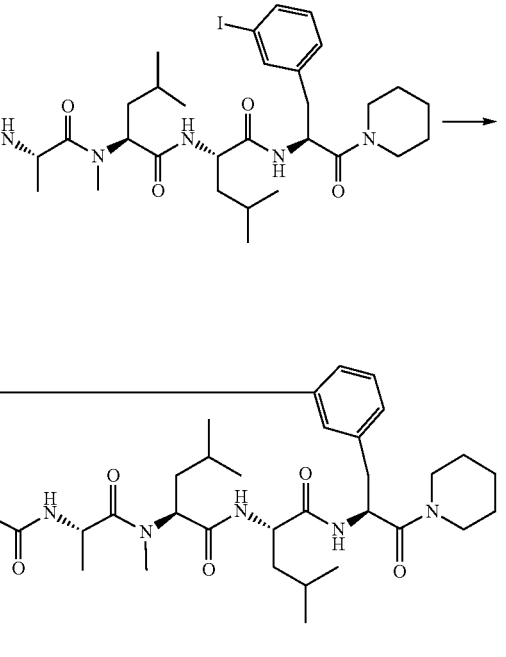

((2S,5S,8S,11S,14S,17S,23S,26S,29S,E)-29-benzyl-17-((R)-1-hydroxyethyl)-2-(3-iodobenzyl)-5,8,26-triisobutyl-23-isopropyl-9,11,14,15,21,24,27-heptamethyl-1,4,7,10,13,16,19,22,25,28,31-undecaoxo-1-(piperidin-1-yl)-3,6,9,12,15,18,21,24,27,30-decaazapentatriacont-34-en-35-yl) boronic acid (Phe-MeLeu-MeVal-MeGly-Thr-MeAla-Ala-MeLeu-Leu-Phe(3-I)-piperidine (SEQ ID NO: 325), the starting material compound of the above reaction scheme, 0.02 g, 0.0405 mmol) synthesized using (E)-5-boronopent-4-enoic acid in place of Fmoc amino acid at the N-terminal according to a peptide synthesis method by the Fmoc method previously described in Example was dissolved in DMF (7.0 ml), Pd(dppf)Cl₂·CH₂Cl₂ (10.0 mg, 0.012 mmol) and triethylamine (0.282 ml, 2.025 mmol) were added and the mixture was stirred at 80° C. for 2.5 hours. The reaction solution was left to cool and concentrated under reduced pressure, after which the residue was dissolved in DMSO and the solution was purified by preparative HPLC to afford the title compound DCC-1 (3.32 mg, 6.5%).

LCMS: m/z 1268.8 (M+H)+

Retention time: 0.75 min (analysis condition SQDAA50)

2-2-1. Synthesis of *Phe-$^{Me}$Leu-$^{Me}$Val-meGly-Thr-$^{Me}$Ala-Ala-$^{Me}$Leu-Leu-Phe*-piperidine (C—C Bonded Between Two * Sites) (Compound DCC-2) (SEQ ID NO: 324)

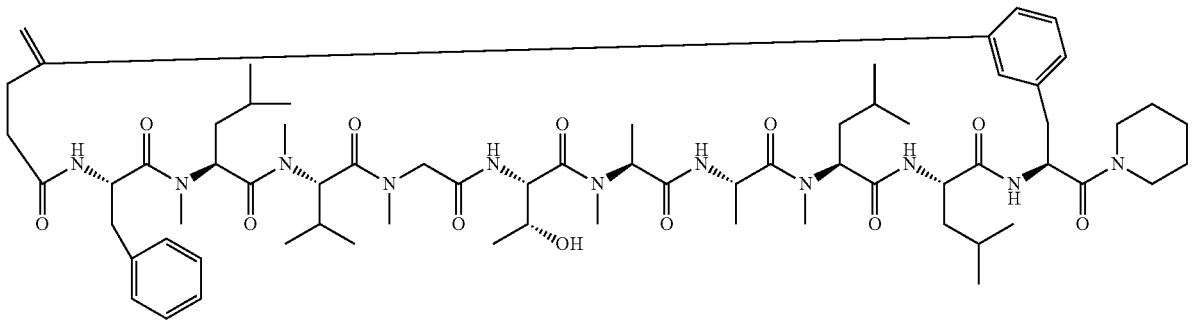 [SMILES: C=C1CCC(=O)N[C@@H](Cc2ccccc2)C(=O)N(C)[C@@H](CC(C)C)C(=O)N(C)[C@@H](C(C)C)C(=O)N(C)CC(=O)N[C@@H]([C@@H](C)O)C(=O)N(C)[C@@H](C)C(=O)N[C@@H](C)C(=O)N(C)[C@@H](CC(C)C)C(=O)N[C@@H](CC(C)C)C(=O)N[C@H](C(=O)N2CCCCC2)Cc2cccc1c2]

The title compound DCC-2 (2.43 mg, 4.8%) was obtained as a by-product in the above reaction for synthesizing DCC-1.
LCMS: m/z 1268.8 (M+H)+
Retention time: 0.78 min (analysis condition SQDAA50)

2-3. Evaluation of Drug-Likeness of C—C Bonded Compounds

Another method for synthesizing C—C bond-cyclized peptides will be described. A display library utilizing C—C bond cyclization can provide a C—C bond cyclized compound by translationally synthesized peptide having a carbon-carbon double bond at a triangle unit on the N-terminal side and an iodophenyl group in the amino acid side chain of an intersection unit on the C-terminal side(Scheme C-2) and then subjecting the peptide to Heck reaction using Pd for example.

Figure 96:
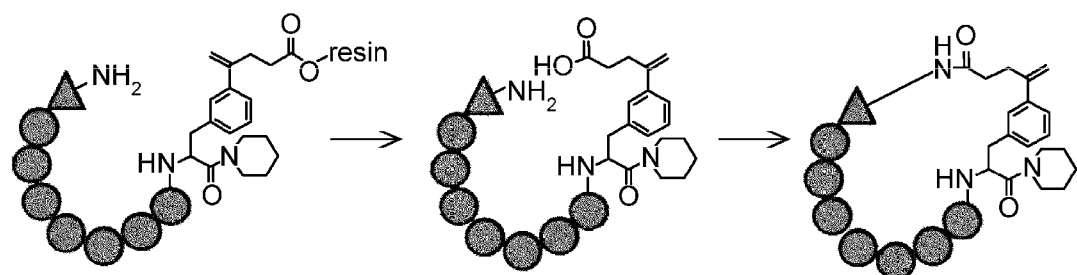
FIG. 96 is a diagram showing scheme H. Scheme H shows an example of the method for synthesizing C—C bond cyclized compounds for drug-likeness evaluation.

C—C bond cyclized peptides were synthesized to evaluate drug-likeness of C—C bond cyclized compounds obtained by the above method. The following scheme H illustrates an example of such synthesis. Cyclized peptides were synthesized not by cyclization reaction using Pd but by amidation reaction. Specifically, a phenylalanine derivative was synthesized in which the main chain carboxylic acid of the C-terminal phenylalanine intersection unit is chemically modified with an amide (piperidine amide) and which is bound to a resin at the carboxylic acid of the side chain, and peptide elongation reaction was carried out according to the Fmoc synthesis method using this resin. After the elongation, a C—C bond cyclized peptide corresponding to a product of the display library by cleaving from the resin and condensing the amino group on the N-terminal side (triangle unit) with the carboxylic acid of the C-terminal phenylalanine derivative (intersection unit) to form a cyclized compound. Although Scheme H describes only a case of providing a C=C double bond, a C—C single or triple bond is also possible, and these compounds were also synthesized.
See FIG. 96.

2-3-1. Synthesis of Amino Acid Units and Resin-Bound Amino Acid Units

Amino acids and their resin-bound compounds were synthesized as phenylalanine derivatives at intersection unit sites used for drug-likeness evaluation.

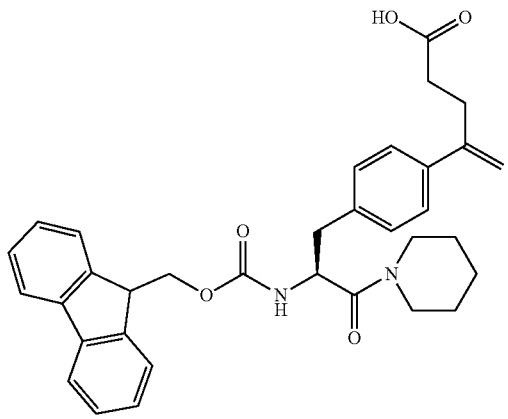

Compound SP416

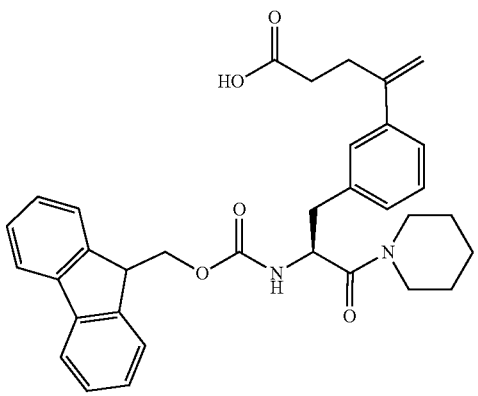

Compound SP421

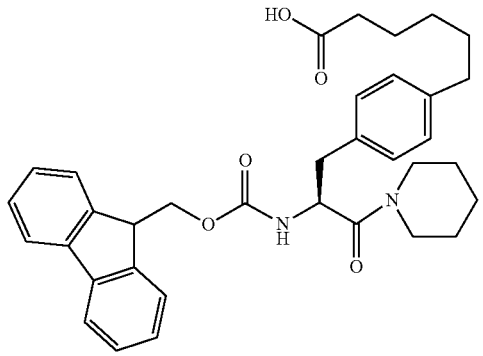

Compound SP427

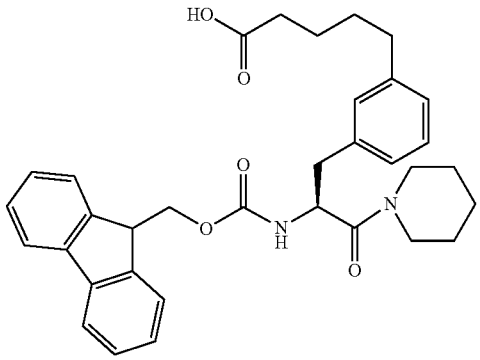

Compound SP432

-continued
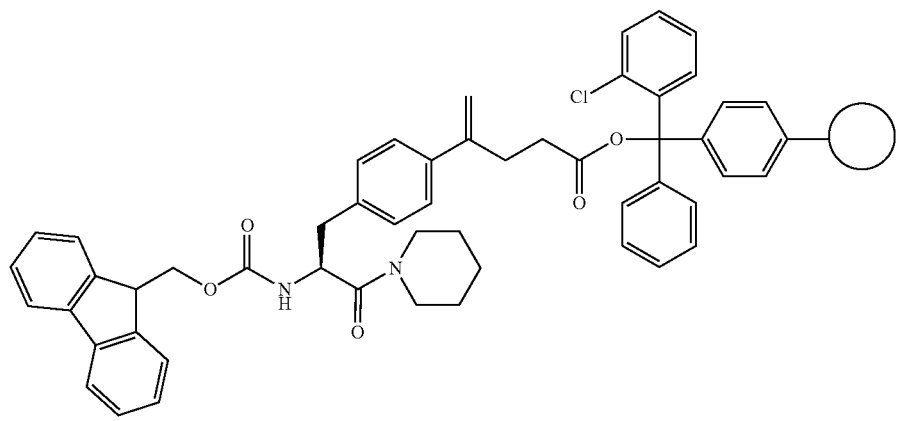
Compound SP417
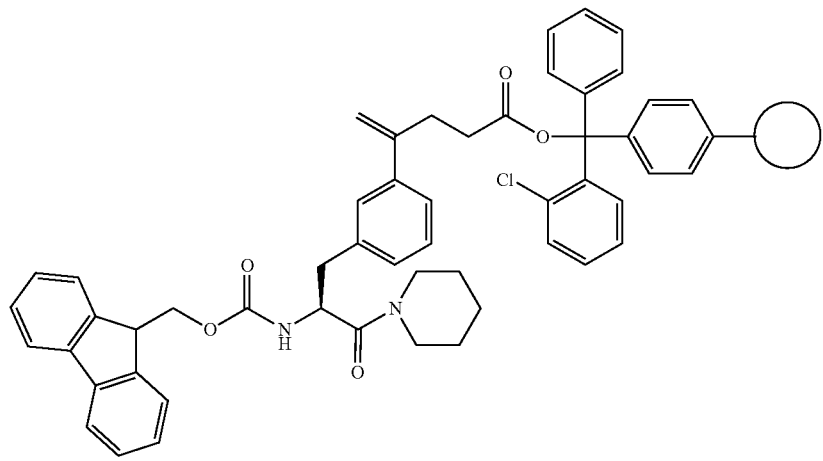
Compound SP422
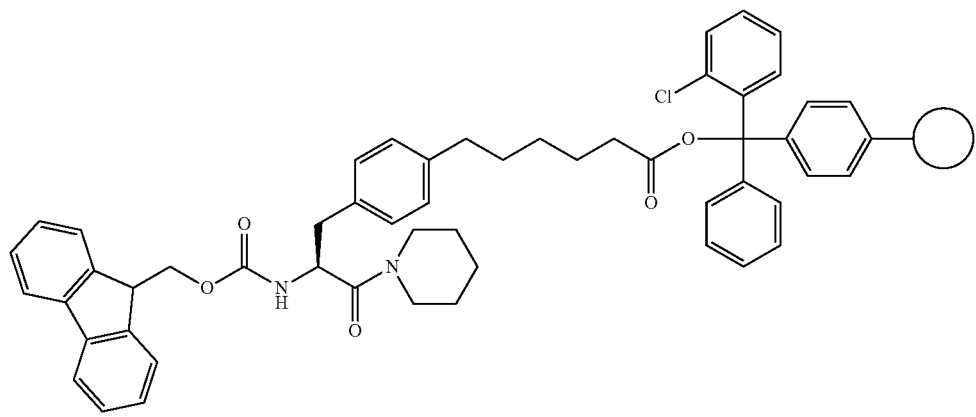
Compound SP428

Compound SP433

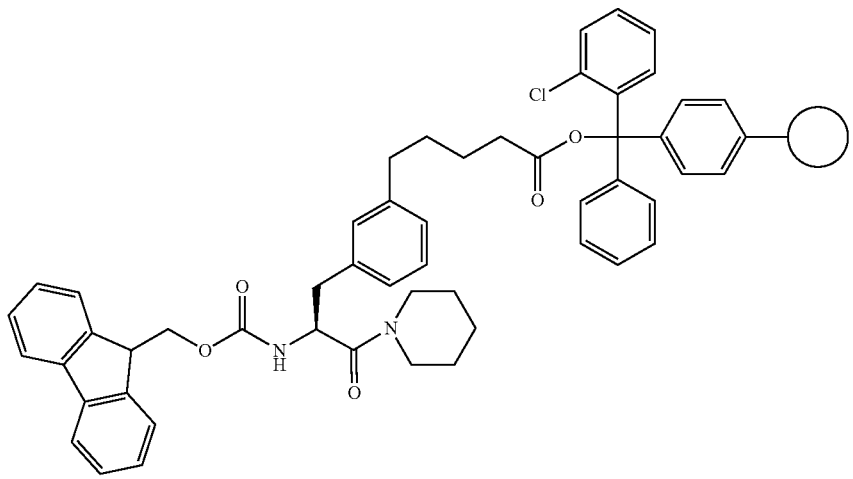

Synthesis of Compound SP416 and Compound SP417

Synthesis of tert-butyl (S)-(3-(4-iodophenyl)-1-oxo-1-(piperidin-1-yl)propan-2-yl)carbamate (Compound SP413, Boc-Phe(4-I)-pip)

Synthesis of tert-butyl (S)-(1-oxo-1-(piperidin-1-yl)-3-(4-(4,4,5,5-tetramethyl-1,3,2-dioxaborolan-2-yl)phenyl)propan-2-yl)carbamate (Compound SP414)

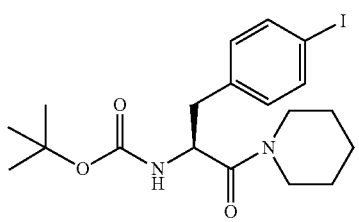 [SMILES: CC(c1ccc(I)cc1)[C@H](NC(=O)OC(C)(C)C)C(=O)N1CCCCC1]

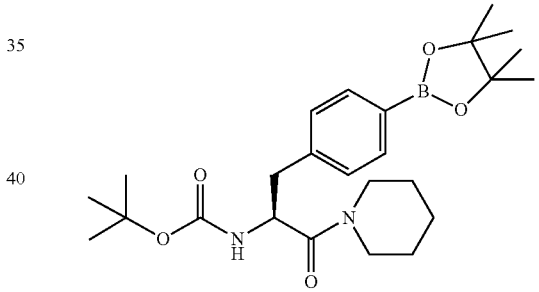

(S)-2-((tert-Butoxycarbonyl)amino)-3-(4-iodophenyl) propanoic acid (Boc-Phe(4-I)—OH) (15.0 g, 38.3 mmol) was dissolved in DMF (180.0 ml), and piperidine (7.95 ml, 80.6 mmol), HATU (17.5 g, 46.0 mmol) and DIPEA (8.01 ml, 46.0 mmol) were added under ice-cooling. After stirring at room temperature for 30 minutes, the reaction solution was diluted with hexane/ethyl acetate (1/1, 400 ml) and washed with a saturated aqueous sodium bicarbonate solution and a saturated aqueous ammonium chloride solution. The organic layer was dried over anhydrous magnesium sulfate and then filtered and concentrated under reduced pressure to afford the title compound SP413 (16.9 g, 96%) as a pale yellow solid.

LCMS (ESI) m/z=459.5 (M+H)+

Retention time: 1.05 min (analysis condition SQDAA05)

tert-Butyl (S)-(3-(4-iodophenyl)-1-oxo-1-(piperidin-1-yl) propan-2-yl)carbamate (Compound SP413) (6.0 g, 13.09 mmol) was dissolved in DMSO (60.0 ml), bis(pinacolato) diboron (4.99 g, 19.64 mmol), Pd(dppf)Cl₂·CH₂Cl₂ (0.538 g, 0.655 mmol) and potassium acetate (5.40 g, 55.02 mmol) were added and the mixture was stirred at room temperature for 5 hours. The reaction solution was diluted with hexane/ethyl acetate (1/1) and washed with a saturated aqueous ammonium chloride solution and a saturated aqueous sodium bicarbonate solution. The organic layer was dried over anhydrous magnesium sulfate, and then filtered and concentrated under reduced pressure, and the resulting residue was purified by column chromatography (hexane:ethyl acetate=100:0-60:40) to afford the title compound SP414 (5.55 g, 92%).

LCMS (ESI) m/z=459.4 (M+H)+

Retention time: 0.99 min (analysis condition SQDFA05)

2083

Synthesis of tert-butyl (S)-4-(4-(2-((tert-butoxycarbonyl)amino)-3-oxo-3-(piperidin-1-yl)propyl)phenyl)pent-4-enoate (Compound SP415)

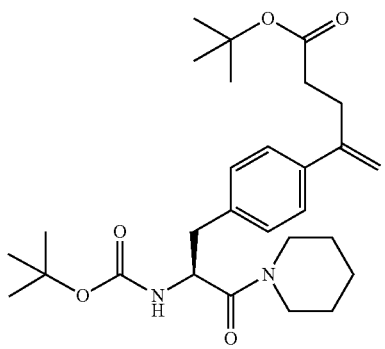 [SMILES: C=C(CCC(=O)OC(C)(C)C)c1ccc(C(C)[C@H](NC(=O)OC(C)(C)C)C(=O)N2CCCCC2)cc1]

tert-Butyl (S)-(1-oxo-1-(piperidin-1-yl)-3-(4-(4,4,5,5-tetramethyl-1,3,2-dioxaborolan-2-yl)phenyl)propan-2-yl)carbamate (Compound SP414) (3.00 g, 6.54 mmol) was dissolved in DMF (24.0 ml) and water (6.0 ml), tert-butyl 4-bromopent-4-enoate synthesized by the method described in the literature (Organic Letters, 2011, 13, 5830-5833) (2.31 g, 9.82 mmol), Pd(PPh3)$_4$ (1.13 g, 0.978 mmol) and potassium carbonate (1.81 g, 13.10 mmol) were added and the mixture was stirred at 80° C. for 2 hours. The reaction solution was left to cool, and then diluted with hexane/ethyl acetate (1/1) and washed with a saturated aqueous sodium bicarbonate solution and a saturated aqueous ammonium chloride solution. The organic layer was dried over anhydrous magnesium sulfate, and then filtered and concentrated under reduced pressure, and the resulting residue was purified by column chromatography (hexane:ethyl acetate=100:0-75:25) to afford the title compound SP415 (2.72 g, 85%).

LCMS (ESI) m/z=487.6 (M+H)+

Retention time: 1.05 min (analysis condition SQDFA05)

2084

Synthesis of (S)-4-(4-(2-((((9H-fluoren-9-yl)methoxy)carbonyl)amino)-3-oxo-3-(piperidin-1-yl)propyl)phenyl)pent-4-enoic Acid (Compound SP416)

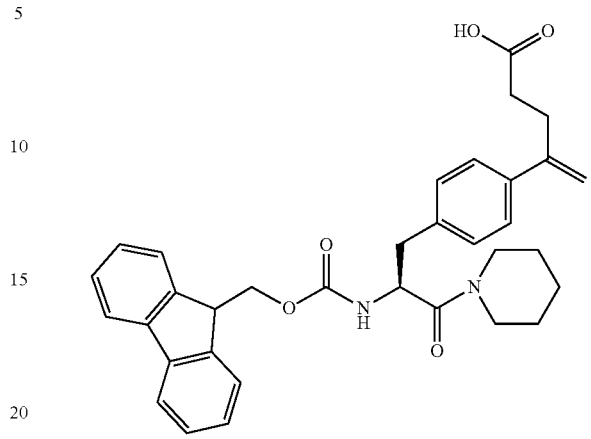

tert-Butyl (S)-4-(4-(2-((tert-butoxycarbonyl)amino)-3-oxo-3-(piperidin-1-yl)propyl)phenyl)pent-4-enoate (Compound SP415) (0.50 g, 1.03 mmol) was suspended in acetic acid (7.0 ml, 122.28 mmol) and water (7.0 ml), and the suspension was stirred with heating at reflux for 8 hours. The same reaction was additionally carried out four times. The reaction solutions were combined and concentrated under reduced pressure, and the resulting residue was suspended in a 10% aqueous sodium carbonate solution (38 ml). A solution of N-(9-fluorenylmethoxycarbonyloxy)-succinimide (1.65 g, 4.89 mmol) in 1,4-dioxane (19.0 ml) was added and the mixture was stirred at room temperature for 1 hour. The reaction solution was washed with diethyl ether, made acidic by adding acetic acid and then extracted with ethyl acetate. The organic layer was dried over anhydrous magnesium sulfate, filtered and concentrated under reduced pressure, and the resulting residue was purified by column chromatography (hexane:ethyl acetate=100:0-40:60) to afford the title compound SP416 (1.60 g, 56.3%).

LCMS (ESI) m/z=553.4 (M+H)+

Retention time: 0.89 min (analysis condition SQDFA05)

Synthesis of (S)-4-(4-(2-((((9H-fluoren-9-yl)methoxy)carbonyl)amino)-3-oxo-3-(piperidin-1-yl)propyl)phenyl)pent-4-enoic acid-2-chlorotrityl Resin (Compound SP417)

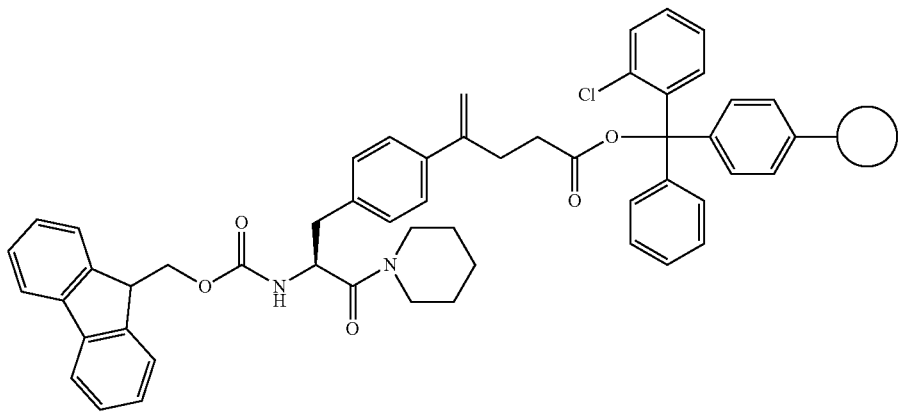 [SMILES: C=C(CCC(=O)OC(c1ccccc1)(c1ccc(C)cc1)c1ccccc1Cl)c1ccc(C[C@H](NC(=O)OCC2c3ccccc3-c3ccccc32)C(=O)N2CCCCC2)cc1]

2-Chlorotrityl chloride resin (1.07 mmol/g, 100-200 mesh, 1% DVB, manufactured by Chem-Impex, 2.50 g, 2.68 mmol) and dichloromethane (18 ml) were mixed, followed by shaking at room temperature for 5 minutes. Dichloromethane was removed, after which methanol (0.43 ml, 10.7 mmol) and diisopropylethylamine (1.1 ml, 6.32 mmol) were added to a solution of (S)-4-(4-(2-((((9H-fluoren-9-yl)methoxy)carbonyl)amino)-3-oxo-3-(piperidin-1-yl)propyl)phenyl)pent-4-enoic acid (Compound SP416) (0.74 g, 1.34 mmol) in dichloromethane (16.5 ml) and the resulting mixture was added to the resin, followed by shaking at room temperature for 10 minutes. The reaction solution was removed, after which methanol (5 ml) and diisopropylethylamine (1.7 ml) were added to dichloromethane (16.5 ml), and the resulting mixture was added, followed by shaking at room temperature for 2 hours. This reaction solution was removed, and dichloromethane (18 ml) was then placed, followed by shaking. Dichloromethane was removed, and dichloromethane (18 ml) was then placed again, followed by shaking. Dichloromethane was removed, and the resin was then dried under reduced pressure to afford the title compound SP417 (2.53 g).

DMF (0.2 ml) and piperidine (0.2 ml) were added to the resulting (S)-4-(4-(2-((((9H-fluoren-9-yl)methoxy)carbonyl)amino)-3-oxo-3-(piperidin-1-yl)propyl)phenyl)pent-4-enoic acid-2-chlorotrityl resin (Compound SP417) (7.94 mg), followed by shaking at room temperature for 30 minutes. After adding DMF (1.6 ml) to the reaction solution, the reaction mixture (0.4 ml) was diluted with DMF (9.6 ml), and its absorbance (301 nm) was measured to be 0.328. The loading rate of (S)-4-(4-(2-((((9H-fluoren-9-yl)methoxy)carbonyl)amino)-3-oxo-3-(piperidin-1-yl)propyl)phenyl)pent-4-enoic acid (Compound SP416) was calculated to be 25.0%, 0.265 mmol/g by the following calculation formulas.

(Absorbance (301 nm)×1000×50)/(amount of resin used×7800)=0.265 mmol/g 0.265 mmol/g×100/(2.68/2.53)=25.0%

Synthesis of tert-butyl (S)-(3-(3-iodophenyl)-1-oxo-1-(piperidin-1-yl)propan-2-yl)carbamate (Compound SP418, Boc-Phe(3-I)-pip)

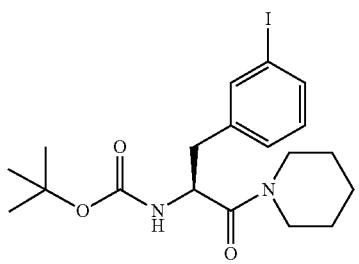 [SMILES: CC(c1cccc(I)c1)[C@H](NC(=O)OC(C)(C)C)C(=O)N1CCCCC1]

(S)-2-((tert-Butoxycarbonyl)amino)-3-(3-iodophenyl)propanoic acid (Boc-Phe(3-I)—OH) (10.0 g, 25.6 mmol) was dissolved in DMF (100.0 ml), and piperidine (5.30 ml, 53.7 mmol), HATU (11.7 g, 30.8 mmol) and DIPEA (5.34 ml, 30.7 mmol) were added under ice-cooling. After stirring at room temperature for 30 minutes, the reaction solution was diluted with hexane/ethyl acetate (1/1) and washed with a saturated aqueous sodium bicarbonate solution and a saturated aqueous ammonium chloride solution. The organic layer was dried over anhydrous magnesium sulfate and then filtered and concentrated under reduced pressure to afford the title compound SP418 (11.6 g, 99%) as a pale yellow amorphous.

LCMS (ESI) m/z=459.2 (M+H)+
Retention time: 0.95 min (analysis condition SQDFA05)

Synthesis of tert-butyl (S)-(1-oxo-1-(piperidin-1-yl)-3-(3-(4,4,5,5-tetramethyl-1,3,2-dioxaborolan-2-yl)phenyl)propan-2-yl)carbamate (Compound SP419)

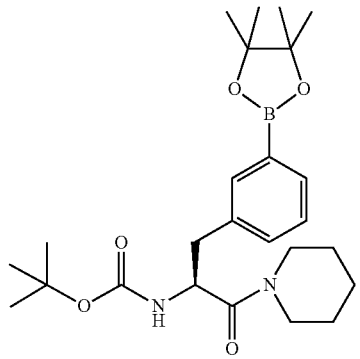 [SMILES: CC(c1cccc(B2OC(C)(C)C(C)(C)O2)c1)[C@H](NC(=O)OC(C)(C)C)C(=O)N1CCCCC1]

tert-Butyl (S)-(3-(3-iodophenyl)-1-oxo-1-(piperidin-1-yl)propan-2-yl)carbamate (Compound SP418) (6.76 g, 14.75 mmol) was dissolved in DMSO (60.0 ml), bis(pinacolato)diboron (5.62 g, 22.12 mmol), Pd(dppf)Cl$_2$·CH$_2$Cl$_2$ (607.0 mg, 0.737 mmol) and potassium acetate (6.08 g, 61.9 mmol) were added and the mixture was stirred at room temperature for 6 hours, after which bis(pinacolato)diboron (5.62 g, 22.12 mmol), Pd(dppf)Cl$_2$·CH$_2$Cl$_2$ (607.0 mg, 0.737 mmol) and potassium acetate (6.08 g, 61.9 mmol) were further added and the mixture was stirred at room temperature overnight. The reaction solution was diluted with hexane/ethyl acetate (1/1) and washed with a saturated aqueous ammonium chloride solution and a saturated aqueous sodium bicarbonate solution. The organic layer was dried over anhydrous magnesium sulfate, and then filtered and concentrated under reduced pressure, and the resulting residue was purified by column chromatography (hexane:ethyl acetate=100:0-60:40) to afford the title compound SP419 (6.50 g, 96%).

LCMS (ESI) m/z=459.6 (M+H)+
Retention time: 0.99 min (analysis condition SQDFA05)

Synthesis of tert-butyl (S)-4-(3-(2-((tert-butoxycarbonyl)amino)-3-oxo-3-(piperidin-1-yl)propyl)phenyl)pent-4-enoate (Compound SP420)

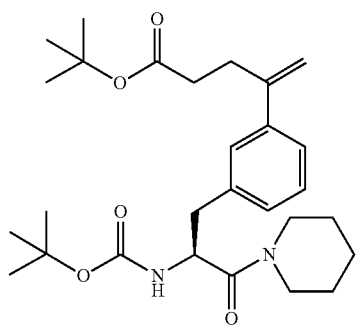 [SMILES: C=C(CCC(=O)OC(C)(C)C)c1cccc(C[C@H](NC(=O)OC(C)(C)C)C(=O)N2CCCCC2)c1]

tert-Butyl (S)-(1-oxo-1-(piperidin-1-yl)-3-(3-(4,4,5,5-tetramethyl-1,3,2-dioxaborolan-2-yl)phenyl)propan-2-yl)carbamate (Compound SP419) (3.00 g, 6.54 mmol) was dissolved in DMF (24.0 ml) and water (6.0 ml), tert-butyl 4-bromopent-4-enoate synthesized by the method described in the literature (Organic Letters, 2011, 13, 5830-5833) (2.31 g, 9.82 mmol), Pd(PPh3)4 (1.134 g, 0.982 mmol) and potassium carbonate (1.81 g, 13.1 mmol) were added and the mixture was stirred at 80° C. for 2 hours. The reaction solution was left to cool, and then diluted with hexane/ethyl acetate (1/1) and washed with a saturated aqueous sodium bicarbonate solution and a saturated aqueous ammonium chloride solution. The organic layer was dried over anhydrous magnesium sulfate, and then filtered and concentrated under reduced pressure, and the resulting residue was purified by column chromatography (hexane:ethyl acetate=100:0-75:25) to afford the title compound SP420 (2.94 g, 92%).

LCMS (ESI) m/z=487.6 (M+H)+

Retention time: 1.05 min (analysis condition SQDFA05)

Synthesis of (S)-4-(3-(2-((((9H-fluoren-9-yl)methoxy)carbonyl)amino)-3-oxo-3-(piperidin-1-yl)propyl)phenyl)pent-4-enoic Acid (Compound SP421)

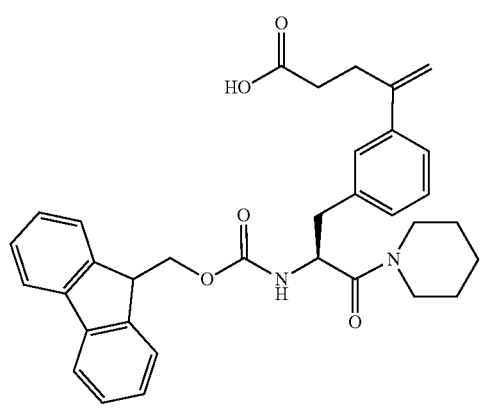 [SMILES: C=C(CCC(=O)O)c1cccc(C[C@H](NC(=O)OCC2c3ccccc3-c3ccccc32)C(=O)N2CCCCC2)c1]

tert-Butyl (S)-4-(3-(2-((tert-butoxycarbonyl)amino)-3-oxo-3-(piperidin-1-yl)propyl)phenyl)pent-4-enoate (Compound SP420) (0.50 g, 1.03 mmol) was suspended in acetic acid (7.0 ml, 122.28 mmol) and water (7.0 ml), and the suspension was stirred with heating at reflux for 8 hours. The same reaction was additionally carried out four times. The reaction solutions were combined and concentrated under reduced pressure, and the resulting residue was suspended in a 10% aqueous sodium carbonate solution (38 ml). A solution of N-(9-fluorenylmethoxycarbonyloxy)-succinimide (1.65 g, 4.89 mmol) in 1,4-dioxane (19.0 ml) was added and the mixture was stirred at room temperature for 1 hour. The reaction solution was washed with diethyl ether, made acidic by adding acetic acid and then extracted with ethyl acetate. The organic layer was dried over anhydrous magnesium sulfate, filtered and concentrated under reduced pressure, and the resulting residue was purified by column chromatography (hexane:ethyl acetate=100:0-50:50) to afford the title compound SP421 (0.78 g, 27.5%).

LCMS (ESI) m/z=553.5 (M+H)+

Retention time: 0.90 min (analysis condition SQDFA05)

Synthesis of (S)-4-(3-(2-((((9H-fluoren-9-yl)methoxy)carbonyl)amino)-3-oxo-3-(piperidin-1-yl)propyl)phenyl)pent-4-enoic acid-2-chlorotrityl Resin (Compound SP422)

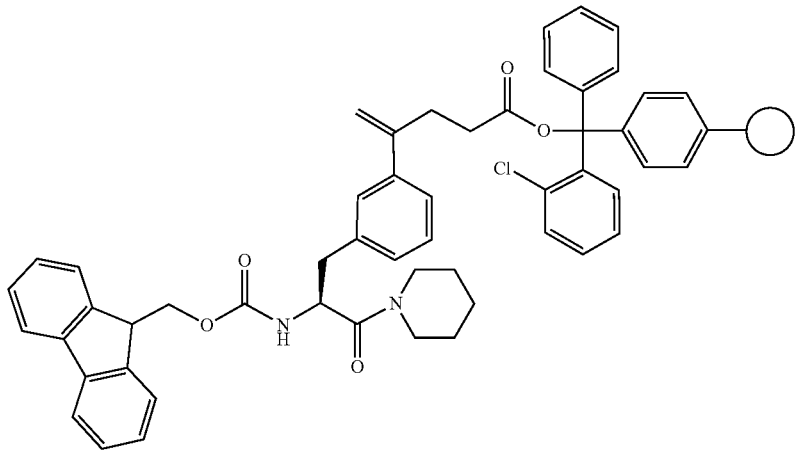 [SMILES: C=C(CCC(=O)OC(c1ccccc1)(c1ccc(C)cc1)c1ccccc1Cl)c1cccc(C[C@H](NC(=O)OCC2c3ccccc3-c3ccccc32)C(=O)N2CCCCC2)c1]

2-Chlorotrityl chloride resin (1.07 mmol/g, 100-200 mesh, 1% DVB, manufactured by Chem-Impex, 2.50 g, 2.68 mmol) and dichloromethane (18 ml) were mixed, followed by shaking at room temperature for 5 minutes. Dichloromethane was removed, after which methanol (0.43 ml, 10.7 mmol) and diisopropylethylamine (1.1 ml, 6.32 mmol) were added to a solution of (S)-4-(3-(2-((((9H-fluoren-9-yl)methoxy)carbonyl)amino)-3-oxo-3-(piperidin-1-yl)propyl)phenyl)pent-4-enoic acid (Compound SP421) (0.74 g, 1.34 mmol) in dichloromethane (16.5 ml) and the resulting mixture was added to the resin, followed by shaking at room temperature for 10 minutes. The reaction solution was removed, after which methanol (5 ml) and diisopropylethylamine (1.7 ml) were added to dichloromethane (16.5 ml), and the resulting mixture was added, followed by shaking at room temperature for 2 hours. This reaction solution was removed, and dichloromethane (18 ml) was then placed, followed by shaking. Dichloromethane was removed, and dichloromethane (18 ml) was then placed again, followed by shaking. Dichloromethane was removed, and the resin was then dried under reduced pressure to afford the title compound SP422 (2.52 g).

Loading rate: 0.278 mmol/g, 26.1%

Synthesis of tert-butyl hex-5-ynoate (Compound SP423)

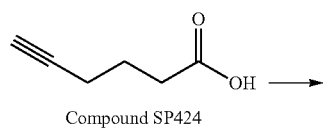

Compound SP424

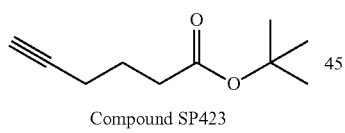

Compound SP423

Hex-5-ynoic acid (Compound SP424) (8.0 g, 71.3 mmol), 2-methylpropan-2-ol (10.6 g, 143.0 mmol) and 4-(dimethylamino)pyridine (0.44 g, 3.60 mmol) were dissolved in DCM (17.5 ml), a solution of dicyclohexylcarbodiimide (16.2 g, 78.5 mmol) in DCM (17.5 ml) was added, and the mixture was stirred at room temperature overnight. The white solid in the reaction solution was removed by filtration, after which the filtrate was washed with a 0.5 M aqueous hydrochloric acid solution and a saturated aqueous sodium bicarbonate solution and dried over anhydrous magnesium sulfate. The residue obtained by filtration and concentration under reduced pressure was purified by column chromatography (hexane:ethyl acetate=100:0-90:10) to afford the title compound SP423 (6.73 g, 56.1%).

$^1$H-NMR (Varian 400-MR, 400 MHz, CDCl$_3$) δ ppm 2.39 (2H, t, 7.2 Hz), 2.28 (2H, m), 2.08 (1H, s), 1.85 (2H, m), 1.49 (9H, s)

Synthesis of tert-butyl (S)-6-(4-(2-((tert-butoxycarbonyl)amino)-3-oxo-3-(piperidin-1-yl)propyl)phenyl)hex-5-ynoate (Compound SP425)

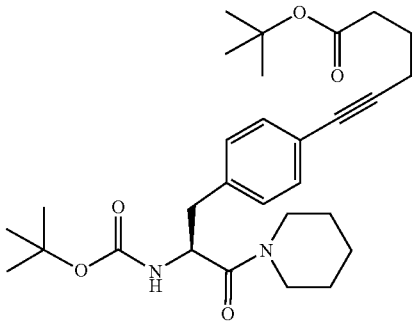 [SMILES: CC(C)(C)OC(=O)CCCC#Cc1ccc(C[C@H](NC(=O)OC(C)(C)C)C(=O)N2CCCCC2)cc1]

tert-Butyl (S)-(3-(4-iodophenyl)-1-oxo-1-(piperidin-1-yl)propan-2-yl)carbamate (Compound SP413, Boc-Phe(4-I)-pip) (6.00 g, 13.09 mmol), tert-butyl hex-5-ynoate (Compound SP423) (4.40 g, 26.2 mmol) and triethylamine (5.47 ml, 39.3 mmol) were dissolved in DMF (60.0 ml), CuI (0.125 g, 0.655 mmol) and Pd(dppf)Cl$_2$·CH$_2$Cl$_2$ (0.538 g, 0.655 mmol) were added and the mixture was stirred at room temperature for 4 hours. The reaction solution was diluted with hexane/ethyl acetate (1/1) and washed with a saturated aqueous ammonium chloride solution and brine. The organic layer was dried over anhydrous magnesium sulfate, and then filtered and concentrated under reduced pressure, and the resulting residue was purified by column chromatography (hexane:ethyl acetate=100:0-60:40) to afford the title compound SP425 (6.19 g, 95%).

LCMS (ESI) m/z=499.4 (M+H)+
Retention time: 1.07 min (analysis condition SQDFA05)

Synthesis of tert-butyl (S)-6-(4-(2-((tert-butoxycarbonyl)amino)-3-oxo-3-(piperidin-1-yl)propyl)phenyl)hexanoate (Compound SP426)

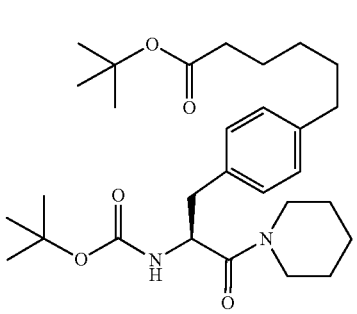 [SMILES: CC(C)(C)OC(=O)CCCCCc1ccc(C[C@H](NC(=O)OC(C)(C)C)C(=O)N2CCCCC2)cc1]

tert-Butyl (S)-6-(4-(2-((tert-butoxycarbonyl)amino)-3-oxo-3-(piperidin-1-yl)propyl)phenyl)hex-5-ynoate (Compound SP425) (5.74 g, 11.51 mmol) was dissolved in ethyl acetate (40 ml), and 10% palladium(II) on carbon (1.72 g) was added under a nitrogen atmosphere. The mixture was then stirred at room temperature for 2 hours under a hydrogen atmosphere. After filtration through celite, the filtrate was concentrated under reduced pressure to afford the title compound SP426 (5.65 g, 98%).

LCMS (ESI) m/z=503.6 (M+H)+
Retention time: 1.14 min (analysis condition SQDAA05)

Synthesis of (S)-6-(4-(2-((((9H-fluoren-9-yl)methoxy)carbonyl)amino)-3-oxo-3-(piperidin-1-yl)propyl)phenyl)hexanoic Acid (Compound SP427)

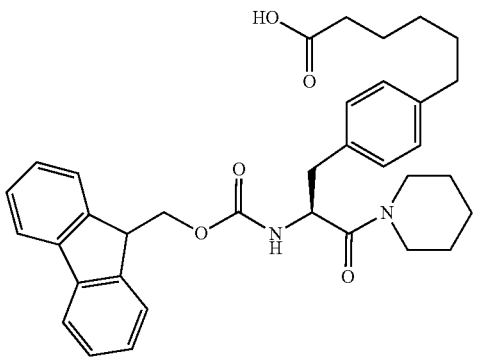 [SMILES: O=C(O)CCCCCc1ccc(C[C@H](NC(=O)OCC2c3ccccc3-c3ccccc32)C(=O)N2CCCCC2)cc1]

tert-Butyl (S)-6-(4-(2-((tert-butoxycarbonyl)amino)-3-oxo-3-(piperidin-1-yl)propyl)phenyl)hexanoate (Compound SP426) (5.65 g, 11.24 mmol) was dissolved in DCM (30.0 ml), trifluoroacetic acid (15.0 ml, 195 mmol) was added and the mixture was stirred for 30 minutes at room temperature, after which the reaction solution was concentrated under reduced pressure. The resulting residue was dissolved in dioxane (40 ml) and a 10% aqueous sodium carbonate solution (80 ml), N-(9-fluorenylmethoxycarbonyloxy)-succinimide (3.68 g, 10.90 mmol) was added and the mixture was stirred at room temperature for 1 hour. The reaction solution was washed with diethyl ether, made acidic by adding a 5 N aqueous HCl solution and then extracted with ethyl acetate. The ethyl acetate layer was dried over anhydrous Na$_2$SO$_4$, filtered and concentrated under reduced pressure to afford the title compound SP427 (6.39 g, 100%).

LCMS (ESI) m/z=569.6 (M+H)+
Retention time: 1.02 min (analysis condition SQDAA05)

Synthesis of (S)-6-(4-(2-((((9H-fluoren-9-yl)methoxy)carbonyl)amino)-3-oxo-3-(piperidin-1-yl)propyl)phenyl)hexanoic acid-2-chlorotrityl Resin (Compound SP428)

2-Chlorotrityl chloride resin (1.07 mmol/g, 100-200 mesh, 1% DVB, manufactured by Chem-Impex, 3.00 g, 3.21 mmol) and dichloromethane (20 ml) were mixed, followed by shaking at room temperature. Dichloromethane was removed, after which methanol (0.52 ml, 12.85 mmol) and diisopropylethylamine (1.35 ml, 7.75 mmol) were added to a solution of (S)-6-(4-(2-((((9H-fluoren-9-yl)methoxy)carbonyl)amino)-3-oxo-3-(piperidin-1-yl)propyl)phenyl)hexanoic acid (Compound SP427) (0.91 g, 1.60 mmol) in dichloromethane (14 ml) and the resulting mixture was added to the resin, followed by shaking at room temperature for 5 minutes. The reaction solution was removed, after which methanol (4.2 ml) and diisopropylethylamine (1.4 ml) were added to dichloromethane (14 ml), and the resulting mixture was added, followed by shaking at room temperature for 2.5 hours. This reaction solution was removed, and dichloromethane (20 ml) was then placed, followed by shaking. Dichloromethane was removed, and dichloromethane (20 ml) was then placed again, followed by shaking. Dichloromethane was removed, and the resin was then dried under reduced pressure to afford the title compound (Compound SP428) (3.15 g).

Loading rate: 0.217 mmol/g, 21.3%

Synthesis of tert-butyl pent-4-ynoate (Compound SP429)

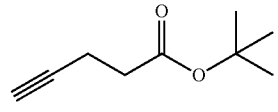

Pent-4-ynoic acid (5.0 g, 51.0 mmol), 2-methylpropan-2-ol (7.56 g, 102.0 mmol) and 4-(dimethylamino)pyridine (0.31 g, 2.54 mmol) were dissolved in DCM (17.5 ml), a solution of dicyclohexylcarbodiimide (11.6 g, 56.2 mmol) in DCM (17.5 ml) was added and the mixture was stirred at room temperature overnight. The white solid in the reaction solution was removed by filtration, after which the filtrate was washed with a 0.5 M aqueous hydrochloric acid solution and a saturated aqueous sodium bicarbonate solution and dried over anhydrous magnesium sulfate. The residue obtained by filtration and concentration under reduced pres-

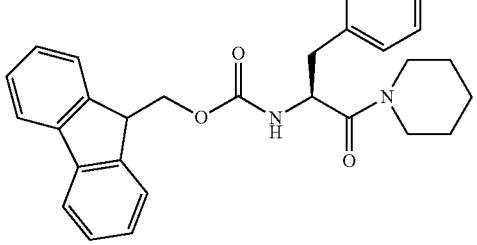

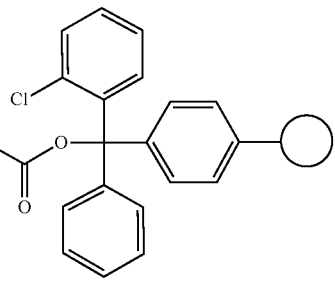

sure was purified by silica gel column chromatography (DCM) to afford the title compound (Compound SP429) (7.15 g, 91.0%).

¹H-NMR (Varian 400-MR, 400 MHz, CDCl₃) δ ppm 2.48-2.50 (4H, m), 2.00 (1H, s), 1.49 (9H, s)

Synthesis of tert-butyl (S)-5-(3-(2-((tert-butoxycarbonyl)amino)-3-oxo-3-(piperidin-1-yl)propyl)phenyl)pent-4-ynoate (Compound SP430)

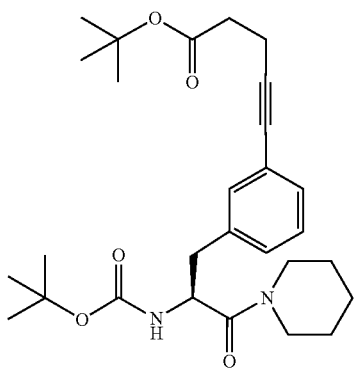 [SMILES: CC(C)(C)OC(=O)CCC#Cc1cccc(C[C@H](NC(=O)OC(C)(C)C)C(=O)N2CCCCC2)c1]

tert-Butyl (S)-(3-(3-iodophenyl)-1-oxo-1-(piperidin-1-yl)propan-2-yl)carbamate (Compound SP418, Boc-Phe(3-I)-pip) (5.00 g, 10.91 mmol), tert-butyl pent-4-ynoate (3.36 g, 21.82 mmol) and triethylamine (4.56 ml, 32.7 mmol) were dissolved in DMF (50.0 ml), CuI (0.104 g, 0.545 mmol) and Pd(dppf)Cl₂·CH₂Cl₂ (0.449 g, 0.545 mmol) were added and the mixture was stirred at room temperature for 5 hours. The reaction solution was diluted with hexane/ethyl acetate (1/1) and washed with a saturated aqueous ammonium chloride solution and brine. The organic layer was dried over anhydrous magnesium sulfate, and then filtered and concentrated under reduced pressure, and the resulting residue was purified by silica gel column chromatography (hexane:ethyl acetate=100:0-60:40) to afford the title compound (Compound SP430) (4.84 g, 92%).

LCMS (ESI) m/z=485.6 (M+H)+

Retention time: 1.03 min (analysis condition SQDFA05)

Synthesis of tert-butyl (S)-5-(3-(2-((tert-butoxycarbonyl)amino)-3-oxo-3-(piperidin-1-yl)propyl)phenyl)pentanoate (Compound SP431)

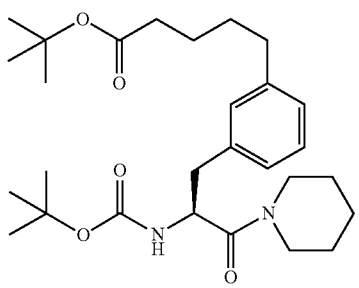 [SMILES: CC(C)(C)OC(=O)CCCCc1cccc(C[C@H](NC(=O)OC(C)(C)C)C(=O)N2CCCCC2)c1]

tert-Butyl (S)-5-(3-(2-((tert-butoxycarbonyl)amino)-3-oxo-3-(piperidin-1-yl)propyl)phenyl)pent-4-ynoate (Compound SP430) (4.84 g, 9.99 mmol) was dissolved in ethyl acetate (40 ml), and 10% palladium(II) on carbon (968 mg) was added under a nitrogen atmosphere. The mixture was then stirred at room temperature for 3.5 hours under a hydrogen atmosphere. After filtration through celite, the filtrate was concentrated under reduced pressure to afford the title compound (Compound SP431) (4.74 g, 97%).

LCMS (ESI) m/z=489.6 (M+H)+

Retention time: 1.08 min (analysis condition SQDFA05)

Synthesis of (S)-5-(3-(2-((((9H-fluoren-9-yl)methoxy)carbonyl)amino)-3-oxo-3-(piperidin-1-yl)propyl)phenyl)pentanoic Acid (Compound SP432)

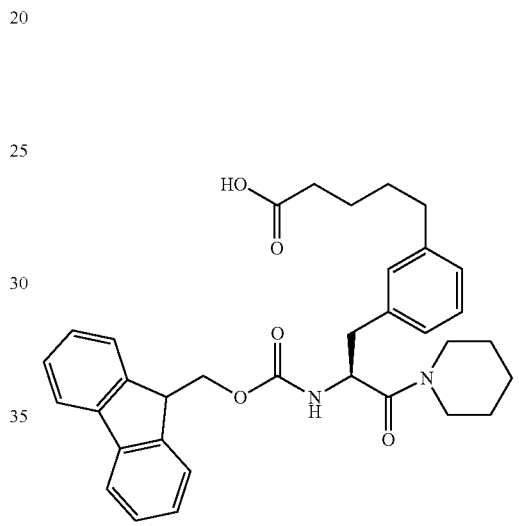

tert-Butyl (S)-5-(3-(2-((tert-butoxycarbonyl)amino)-3-oxo-3-(piperidin-1-yl)propyl)phenyl)pentanoate (Compound SP431) (4.70 g, 9.62 mmol) was dissolved in DCM (30.0 ml), trifluoroacetic acid (15.0 ml, 195 mmol) was added and the mixture was stirred for 50 minutes at room temperature, after which the reaction solution was concentrated under reduced pressure. The resulting residue was dissolved in dioxane (34 ml) and a 10% aqueous sodium carbonate solution (68 ml), N-(9-fluorenylmethoxycarbonyloxy)-succinimide (3.15 g, 9.33 mmol) was added and the mixture was stirred at room temperature for 3 hours. The reaction solution was made acidic by adding a 5 N aqueous HCl solution and then extracted with ethyl acetate. The ethyl acetate layer was dried over anhydrous Na₂SO₄, and then filtered and concentrated under reduced pressure, and the resulting residue was purified by silica gel column chromatography (hexane:ethyl acetate=100:0-30:70) to afford the title compound (Compound SP432) (4.65 g, 87%).

LCMS (ESI) m/z=555.6 (M+H)+

Retention time: 0.92 min (analysis condition SQDFA05)

Synthesis of (S)-5-(3-(2-((((9H-fluoren-9-yl)methoxy)carbonyl)amino)-3-oxo-3-(piperidin-1-yl)propyl)phenyl)pentanoic acid-2-chlorotrityl Resin (Compound SP433)

to a 50 mM MOPSO buffer, pH 6.5, containing 5.0% (w/v) of glycocholic acid, and 330 μL of the mixture was added to a 96-well plate made of Teflon (donor plate). The above artificial phospholipid membrane plate was attached onto the donor plate, and 280 μL of a solution obtained by adding

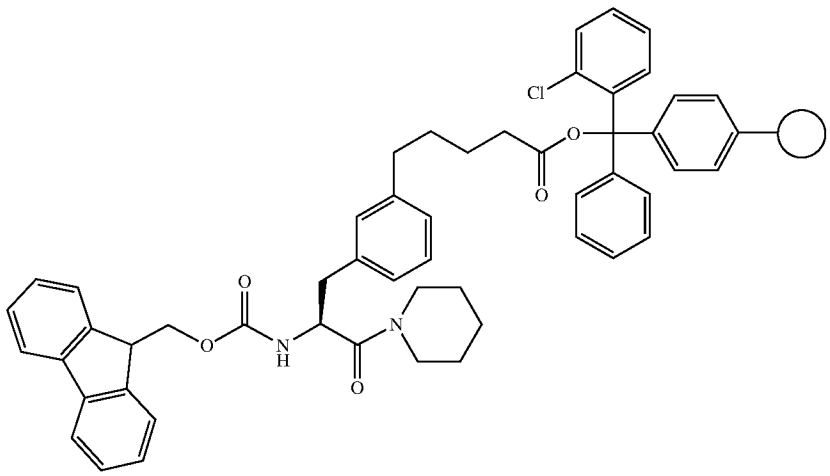 [SMILES: Cc1ccc(C(OC(=O)CCCCc2cccc(C[C@H](NC(=O)OCC3c4ccccc4-c4ccccc43)C(=O)N3CCCCC3)c2)(c2ccccc2)c2ccccc2Cl)cc1]

2-Chlorotrityl chloride resin (1.07 mmol/g, 100-200 mesh, 1% DVB, manufactured by Chem-Impex, 5.00 g, 5.35 mmol) and dichloromethane (35 ml) were placed, followed by shaking at room temperature. Dichloromethane was removed, after which methanol (0.87 ml, 21.50 mmol) and diisopropylethylamine (2.24 ml, 12.86 mmol) were added to a solution of (S)-5-(3-(2-((((9H-fluoren-9-yl)methoxy)carbonyl)amino)-3-oxo-3-(piperidin-1-yl)propyl)phenyl)pentanoic acid (Compound SP432) (1.48 g, 2.67 mmol) in dichloromethane (33 ml), and the resulting mixture was added to the resin, followed by shaking at room temperature for 10 minutes. The reaction solution was removed, after which methanol (10 ml) and diisopropylethylamine (3.3 ml) were added to dichloromethane (33 ml), and the resulting mixture was added, followed by shaking at room temperature for 2 hours. This reaction solution was removed, and dichloromethane (33 ml) was then placed, followed by shaking. Dichloromethane was removed, and dichloromethane (33 ml) was then placed again, followed by shaking. Dichloromethane was removed, and the resin was then dried under reduced pressure to afford the title compound (Compound SP433) (5.80 g).

Loading rate: 0.326 mmol/g, 35.3%

2. Evaluation of Membrane Permeability of the Synthesized Cyclized Peptides by PAMPA A test by PAMPA (parallel artificial membrane permeability assay) was carried out in order to compare and examine membrane permeability of the synthesized cyclized peptides.

4 μL of a phospholipid-organic solvent solution composed of 10% (w/v) of egg lecithin, 0.5% (w/v) of cholesterol and dodecane (all purchased from Fluka) was added to a Millipore 96-well membrane filter (hydrophobic PVDF (polyvinylidene difluoride), pore size 0.45 microm) (purchased from Millipore Japan) to make an artificial phospholipid membrane.

A DMSO solution containing the compound at a concentration of 10 mM was added in a percentage of 0.5% (v/v) DMSO in a percentage of 0.5% (v/v) to a 50 mM MOPSO buffer, pH 6.5, containing 5.0% (w/w) of glycocholic acid was added onto the artificial phospholipid membrane (acceptor plate). These plates were allowed to stand at 37° C. for 18 hours, after which the concentrations of the compound in the solutions in the donor plate and the acceptor plate were measured by LC/MS or LC/UV, and the membrane permeation rate of the compound (P e) was calculated by the following formulas (1) and (2), where t is the testing time, A is the membrane filter area, $V_D$ is the amount of the donor solution, $V_A$ is the amount of the acceptor solution, $C_{D,t}$ is the concentration of the compound in the donor solution at the time t, and $C_{A,t}$ is the concentration of the compound in the acceptor solution at the time t. The results obtained by this method are described in Table 11-5 (results of evaluation of membrane permeation of the cyclized peptides by PAMPA).

(Formula 1)

$$P_e = \frac{2.303 V_D}{A \cdot t} \cdot \left(\frac{1}{1 + V_D/V_A}\right) \log_{10}\left[1 - \left(\frac{1 + V_A/V_D}{1 - R}\right)\left(\frac{C_{A,t}}{C_{D,t=0}}\right)\right] \quad (1)$$

$$R = 1 - \frac{(C_{D,t} + (C_{A,t} V_A / V_D))}{C_{D,t=0}} \quad (2)$$

TABLE 11-5

| | iPAMPA Pe |
|---|---|
| DP-3 | 5.6E–07 |
| DP-4 | 1.1E–05 |
| DP-5 | 1.3E–05 |
| DP-7 | 1.0E–05 |
| DP-9 | 1.3E–05 |
| DP-16 | 3.0E–05 |
| DP-17 | 3.8E–05 |
| DP-18 | 3.0E–05 |
| DP-29 | 3.1E–05 |
| DP-35 | 1.2E–05 |

TABLE 11-5-continued

| | iPAMPA Pe |
|---|---|
| DP-36 | 2.7E−05 |
| DP-37 | 3.1E−05 |
| DP-38 | 1.6E−05 |
| DP-39 | 1.6E−05 |
| DP-40 | 5.8E−06 |
| DP-41 | 1.1E−05 |
| DP-44 | 2.0E−05 |
| DP-47 | 5.0E−05 |
| DP-48 | 3.3E−05 |
| DP-49 | 1.8E−05 |
| DP-50 | 3.5E−05 |
| DP-51 | 3.4E−05 |
| DP-52 | 2.3E−05 |
| DP-53 | 3.0E−05 |
| DP-54 | 1.5E−05 |
| DP-55 | 2.1E−05 |
| DP-56 | 3.0E−05 |
| DP-57 | 2.6E−05 |
| DP-58 | 2.0E−05 |
| DP-59 | 2.1E−05 |
| DP-60 | 4.2E−05 |
| DP-61 | 1.9E−05 |
| DP-62 | 3.3E−05 |
| DP-63 | 1.7E−05 |
| DP-64 | 2.4E−05 |
| DP-65 | 1.4E−05 |
| DP-66 | 1.9E−05 |
| DP-67 | 2.3E−05 |
| DP-68 | 2.6E−05 |
| DP-69 | 2.1E−05 |
| DP-70 | 4.0E−05 |
| DP-71 | 5.4E−06 |
| DP-72 | 2.7E−05 |
| DP-73 | 5.4E−06 |
| DP-74 | 2.9E−05 |
| DP-75 | 3.3E−06 |
| DP-76 | 1.6E−05 |
| DP-77 | 2.1E−05 |
| DP-78 | 3.8E−05 |
| DP-79 | 2.8E−05 |
| DP-80 | 1.2E−05 |
| DP-81 | 2.5E−05 |
| DP-88 | 1.3E−05 |
| DP-89 | 2.3E−05 |
| DP-90 | 9.1E−06 |
| DP-91 | 2.0E−05 |
| DP-92 | 2.6E−05 |
| DP-93 | 2.2E−05 |
| DP-94 | 2.8E−05 |
| DP-95 | 7.3E−06 |
| DP-96 | 1.3E−05 |
| DP-97 | 2.7E−05 |
| DP-98 | 2.6E−05 |
| DP-99 | 5.6E−05 |
| DP-100 | 1.7E−06 |
| DP-101 | 5.6E−05 |
| DP-102 | 1.8E−06 |
| DP-103 | 1.9E−05 |
| DP-104 | 6.7E−06 |
| DP-105 | 4.5E−05 |
| DP-106 | 3.4E−05 |
| DP-107 | 2.3E−05 |
| DP-108 | 2.2E−05 |
| DP-109 | 3.0E−05 |
| DP-110 | 3.0E−05 |
| DP-111 | 1.2E−05 |
| DP-112 | 3.5E−05 |
| DP-113 | 2.8E−05 |
| DP-114 | 4.4E−05 |
| DP-115 | 4.5E−07 |
| DP-116 | 2.3E−05 |
| DP-117 | 2.5E−05 |
| DP-118 | 1.4E−05 |
| DP-119 | 1.6E−05 |
| DP-120 | 5.0E−05 |
| DP-121 | 4.1E−05 |
| DP-122 | 3.2E−05 |
| DP-123 | 5.8E−05 |
| DP-124 | 2.0E−05 |
| DP-125 | 5.5E−05 |
| DP-126 | 5.4E−05 |
| DP-127 | 4.7E−05 |
| DP-128 | 2.3E−05 |
| DP-129 | 1.7E−05 |
| DP-130 | 2.1E−05 |
| DP-131 | 6.1E−05 |
| DP-132 | 3.9E−05 |
| DP-133 | 3.0E−05 |
| DP-134 | 1.3E−05 |
| DP-135 | 5.2E−06 |
| DP-136 | 3.5E−05 |
| DP-137 | 3.2E−05 |
| DP-138 | 3.1E−05 |
| DP-139 | 2.3E−05 |
| DP-140 | 6.1E−05 |
| DP-142 | 4.0E−06 |
| DP-143 | 2.0E−05 |
| DP-144 | 6.5E−05 |
| DP-145 | 2.9E−05 |
| DP-146 | 2.6E−05 |
| DP-147 | 2.9E−05 |
| DP-148 | 3.1E−05 |
| DP-149 | 1.7E−05 |
| DP-150 | 3.3E−05 |
| DP-151 | 2.7E−05 |
| DP-152 | 6.1E−05 |
| DP-153 | 2.6E−05 |
| DP-154 | 9.3E−06 |
| DP-155 | 5.5E−05 |
| DP-156 | 2.4E−05 |
| DP-157 | 2.7E−05 |
| DP-158 | 4.9E−05 |
| DP-159 | 3.9E−05 |
| DP-160 | 3.7E−05 |
| DP-161 | 2.6E−05 |
| DP-162 | 3.5E−05 |
| DP-163 | 2.3E−05 |
| DP-164 | 3.0E−05 |
| DP-165 | 5.6E−05 |
| DP-166 | 5.5E−05 |
| DP-167 | 9.5E−06 |
| DP-168 | 2.3E−05 |
| DP-169 | 3.6E−05 |
| DP-170 | 4.3E−05 |
| DP-171 | 5.0E−05 |
| DP-172 | 7.0E−05 |
| DP-173 | 5.8E−05 |
| DP-174 | 2.2E−05 |
| DP-175 | 4.8E−05 |
| DP-176 | 2.5E−05 |
| DP-177 | 2.3E−05 |
| DP-178 | 1.0E−06 |
| DP-179 | 1.7E−05 |
| DP-180 | 2.3E−05 |
| DP-181 | 1.8E−05 |
| DP-182 | 2.6E−05 |
| DP-183 | 2.9E−05 |
| DP-184 | 1.3E−06 |
| DP-185 | 4.6E−05 |
| DP-186 | 3.7E−05 |
| DP-187 | 4.3E−05 |
| DP-188 | 2.8E−05 |
| DP-189 | 1.4E−06 |
| DP-190 | 6.0E−07 |
| DP-191 | 3.4E−05 |
| DP-192 | 6.4E−07 |
| DP-193 | 5.3E−05 |
| DP-194 | 2.2E−05 |
| DP-195 | 8.0E−06 |
| DP-196 | 2.9E−05 |
| DP-197 | 2.7E−05 |
| DP-198 | 3.6E−05 |
| DP-199 | 5.9E−05 |
| DP-200 | 2.2E−05 |
| DP-201 | 2.7E−05 |
| DP-202 | 5.5E−05 |

TABLE 11-5-continued

| | iPAMPA Pe |
|---|---|
| DP-203 | 1.1E−05 |
| DP-204 | 2.2E−05 |
| DP-205 | 1.2E−07 |
| DP-206 | 9.0E−06 |
| DP-207 | 1.6E−07 |
| DP-208 | 2.7E−05 |
| DP-209 | 4.2E−05 |
| DP-210 | 1.8E−06 |
| DP-211 | 3.2E−06 |
| DP-212 | 2.9E−05 |
| DP-213 | 5.5E−05 |
| DP-214 | 3.4E−05 |
| DP-215 | 2.4E−05 |
| DP-216 | 4.5E−06 |
| DP-217 | 3.8E−05 |
| DP-218 | 3.3E−05 |
| DP-219 | 1.3E−06 |
| DP-220 | 3.3E−05 |
| DP-221 | 3.1E−05 |
| DP-222 | 1.6E−05 |
| DP-223 | 2.3E−05 |
| DP-224 | 1.8E−05 |
| DP-225 | 1.6E−05 |
| DP-226 | 3.2E−05 |
| DP-227 | 3.8E−05 |
| DP-228 | 5.2E−06 |
| DP-229 | 3.3E−05 |
| DP-230 | 4.4E−05 |
| DP-231 | 1.8E−05 |
| DP-232 | 1.8E−05 |
| DP-233 | 3.2E−05 |
| DP-234 | 2.0E−06 |
| DP-235 | 9.0E−06 |
| DP-236 | 7.0E−05 |
| DP-237 | 1.2E−05 |
| DP-238 | 1.9E−05 |
| DP-239 | 2.5E−05 |
| DP-240 | 3.8E−05 |
| DP-241 | 2.6E−05 |
| DP-242 | 2.9E−05 |
| DP-243 | 8.4E−06 |
| DP-244 | 3.1E−05 |
| DP-245 | 3.1E−05 |
| DP-246 | 4.1E−05 |
| DP-247 | 2.8E−05 |
| DP-248 | 2.6E−06 |
| DP-249 | 3.4E−05 |
| DP-250 | 2.9E−05 |
| DP-251 | 2.4E−05 |
| DP-252 | 4.7E−05 |
| DP-253 | 7.5E−06 |
| DP-254 | 3.5E−06 |
| DP-255 | 4.8E−05 |
| DP-256 | 1.9E−05 |
| DP-257 | 3.3E−05 |
| DP-258 | 5.2E−05 |
| DP-259 | 2.8E−05 |
| DP-260 | 4.4E−05 |
| DP-261 | 2.7E−05 |
| DP-262 | 3.8E−05 |
| DP-263 | 3.4E−05 |
| DP-264 | 3.7E−05 |
| DP-265 | 4.2E−05 |
| DP-266 | 4.3E−05 |
| DP-267 | 2.5E−05 |
| DP-268 | 5.0E−05 |
| DP-269 | 1.1E−05 |
| DP-270 | 2.2E−05 |
| DP-271 | 1.0E−05 |
| DP-272 | 4.9E−05 |
| DP-273 | 2.1E−05 |
| DP-274 | 2.5E−05 |
| DP-275 | 3.6E−05 |
| DP-276 | 1.9E−05 |
| DP-277 | 3.8E−05 |
| DP-278 | 1.5E−06 |
| DP-279 | 1.5E−05 |
| DP-280 | 2.1E−05 |

TABLE 11-5-continued

| | iPAMPA Pe |
|---|---|
| DP-281 | 1.7E−05 |
| DP-282 | 2.8E−05 |
| DP-283 | 1.5E−06 |
| DP-284 | 2.1E−07 |
| DP-285 | 1.6E−05 |
| DP-286 | 2.4E−07 |
| DP-287 | 1.4E−06 |
| DP-288 | 1.8E−05 |
| DP-289 | 1.4E−07 |
| DP-290 | 1.9E−05 |
| DP-291 | 1.4E−05 |
| DP-292 | 1.0E−07 |
| DP-293 | 4.5E−05 |
| DP-294 | 1.7E−05 |
| DP-295 | 1.0E−07 |
| DP-296 | 1.5E−05 |
| DP-297 | 1.9E−05 |
| DP-298 | 7.0E−06 |
| DP-299 | 5.3E−06 |
| DP-300 | 8.2E−06 |
| DP-301 | 1.5E−05 |
| DP-302 | 1.8E−05 |
| DP-303 | 1.2E−06 |
| DP-304 | 3.5E−05 |
| DP-305 | 3.5E−05 |
| DP-306 | 5.6E−05 |
| DP-307 | 2.2E−05 |
| DP-308 | 2.7E−05 |
| DP-309 | 2.6E−05 |
| DP-310 | 3.5E−05 |
| DP-311 | 4.8E−05 |
| DP-312 | 4.7E−05 |
| DP-313 | 2.1E−05 |
| DP-314 | 4.9E−05 |
| DP-315 | 3.0E−05 |
| DP-316 | 1.2E−05 |
| DP-317 | 2.0E−05 |
| DP-318 | 2.6E−05 |
| DP-319 | 1.0E−06 |
| DP-320 | 1.5E−06 |
| DP-321 | 6.2E−06 |
| DP-322 | 1.0E−05 |
| DP-323 | 7.8E−06 |
| DP-324 | 7.7E−06 |
| DP-325 | 4.4E−05 |
| DP-326 | 2.5E−06 |
| DP-327 | 3.5E−06 |
| DP-328 | 1.6E−05 |
| DP-329 | 2.4E−06 |
| DP-330 | 9.9E−06 |
| DP-331 | 2.4E−07 |
| DP-332 | 1.4E−05 |
| DP-333 | 4.7E−05 |
| DP-334 | 2.0E−05 |
| DP-335 | 2.2E−05 |
| DP-336 | 3.5E−05 |
| DP-337 | 1.7E−05 |
| DP-338 | 4.9E−06 |
| DP-339 | 1.8E−05 |
| DP-340 | 3.1E−05 |
| DP-341 | 9.5E−06 |
| DP-342 | 3.3E−05 |
| DP-343 | 3.6E−05 |
| DP-344 | 2.2E−05 |
| DP-345 | 2.8E−06 |
| DP-346 | 4.0E−06 |
| DP-347 | 2.5E−05 |
| DP-348 | 1.9E−05 |
| DP-349 | 3.9E−06 |
| DP-350 | 2.0E−06 |
| DP-351 | 6.3E−05 |
| DP-352 | 2.5E−05 |
| DP-353 | 1.6E−05 |
| DP-354 | 3.3E−06 |
| DP-355 | 1.7E−05 |
| DP-356 | 3.4E−05 |
| DP-357 | 1.4E−05 |
| DP-358 | 3.2E−05 |

TABLE 11-5-continued

| | iPAMPA Pe |
|---|---|
| DP-359 | 4.3E−05 |
| DP-360 | 7.3E−06 |
| DP-361 | 1.5E−06 |
| DP-362 | 2.7E−05 |
| DP-363 | 5.0E−06 |
| DP-364 | 2.8E−05 |
| DP-365 | 2.0E−05 |
| DP-366 | 1.4E−05 |
| DP-367 | 1.2E−05 |
| DP-368 | 1.6E−06 |
| DP-369 | 2.6E−05 |
| DP-370 | 2.5E−05 |
| DP-371 | 3.4E−05 |
| DP-372 | 4.2E−05 |
| DP-373 | 9.2E−06 |
| DP-374 | 2.4E−05 |
| DP-375 | 1.9E−05 |
| DP-376 | 2.9E−05 |
| DP-377 | 2.3E−05 |
| DP-378 | 3.1E−05 |
| DP-379 | 4.1E−05 |
| DP-380 | 1.7E−05 |
| DP-381 | 4.5E−05 |
| DP-382 | 4.9E−05 |
| DP-383 | 1.4E−05 |
| DP-384 | 2.6E−05 |
| DP-385 | 1.8E−05 |
| DP-386 | 5.4E−05 |
| DP-387 | 2.8E−06 |
| DP-388 | 1.1E−05 |
| DP-389 | 1.5E−05 |
| DP-390 | 3.5E−06 |
| DP-391 | 4.5E−06 |
| DP-392 | 2.0E−05 |
| DP-393 | 1.8E−05 |
| DP-394 | 2.2E−05 |
| DP-395 | 1.9E−05 |
| DP-396 | 5.5E−05 |
| DP-397 | 1.1E−05 |
| DP-398 | 2.4E−05 |
| DP-399 | 8.9E−07 |
| DP-400 | 1.5E−05 |
| DP-401 | 8.6E−06 |
| DP-402 | 2.4E−05 |
| DP-403 | 1.8E−05 |
| DP-404 | 2.0E−05 |
| DP-405 | 2.6E−05 |
| DP-406 | 4.4E−06 |
| DP-407 | 3.8E−05 |
| DP-408 | 1.9E−06 |
| DP-409 | 1.3E−05 |
| DP-410 | 1.4E−06 |
| DP-411 | 8.4E−06 |
| DP-412 | 2.6E−05 |
| DP-413 | 2.9E−05 |
| DP-414 | 4.4E−06 |
| DP-415 | 2.9E−06 |
| DP-416 | 2.3E−07 |
| DP-417 | 4.3E−05 |
| DP-418 | 2.8E−05 |
| DP-419 | 6.7E−06 |
| DP-420 | 1.0E−05 |
| DP-421 | 2.9E−05 |
| DP-422 | 3.8E−06 |
| DP-423 | 1.5E−05 |
| DP-424 | 4.6E−05 |
| DP-425 | 2.7E−05 |
| DP-426 | 3.6E−05 |
| DP-427 | 3.7E−05 |
| DP-428 | 2.6E−05 |
| DP-429 | 1.5E−05 |
| DP-430 | 3.2E−05 |
| DP-431 | 3.4E−05 |
| DP-432 | 2.6E−05 |
| DP-433 | 4.5E−05 |
| DP-434 | 3.8E−05 |
| DP-435 | 1.6E−05 |
| DP-436 | 4.5E−05 |

TABLE 11-5-continued

| | iPAMPA Pe |
|---|---|
| DP-437 | 3.7E−05 |
| DP-438 | 3.8E−05 |
| DP-439 | 3.4E−05 |
| DP-440 | 2.9E−05 |
| DP-441 | 3.7E−05 |
| DP-442 | 3.8E−05 |
| DP-443 | 9.1E−06 |
| DP-444 | 7.2E−07 |
| DP-445 | 1.1E−05 |
| DP-446 | 4.0E−05 |
| DP-447 | 3.3E−05 |
| DP-448 | 6.2E−06 |
| DP-449 | 6.0E−06 |
| DP-450 | 2.3E−06 |
| DP-451 | 3.5E−05 |
| DP-452 | 2.2E−05 |
| DP-453 | 2.5E−05 |
| DP-454 | 1.4E−05 |
| DP-455 | 1.5E−05 |
| DP-456 | 4.1E−05 |
| DP-457 | 1.0E−05 |
| DP-458 | 7.7E−06 |
| DP-459 | 1.9E−05 |
| DP-460 | 5.1E−06 |
| DP-461 | 3.3E−05 |
| DP-462 | 9.5E−06 |
| DP-463 | 3.1E−06 |
| DP-464 | 2.5E−05 |
| DP-465 | 5.1E−06 |
| DP-466 | 1.5E−05 |
| DP-467 | 1.5E−06 |
| DP-468 | 2.7E−05 |
| DP-469 | 1.4E−05 |
| DP-470 | 1.2E−06 |
| DP-471 | 2.1E−05 |
| DP-472 | 2.4E−05 |
| DP-473 | 1.4E−05 |
| DP-474 | 1.3E−05 |
| DP-475 | 1.6E−05 |
| DP-476 | 2.8E−06 |
| DP-477 | 2.9E−05 |
| DP-478 | 1.8E−05 |
| DP-479 | 4.6E−05 |
| DP-480 | 6.6E−06 |
| DP-481 | 3.1E−05 |
| DP-482 | 3.7E−06 |
| DP-483 | 1.8E−05 |
| DP-484 | 1.3E−05 |
| DP-485 | 5.9E−06 |
| DP-486 | 3.8E−05 |
| DP-487 | 2.4E−05 |
| DP-488 | 6.2E−06 |
| DP-489 | 2.4E−05 |
| DP-490 | 1.1E−05 |
| DP-491 | 1.8E−05 |
| DP-492 | 2.0E−05 |
| DP-493 | 2.4E−06 |
| DP-494 | 5.5E−05 |
| DP-495 | 2.1E−05 |
| DP-496 | 2.3E−05 |
| DP-497 | 9.3E−06 |
| DP-498 | 2.7E−06 |
| DP-499 | 3.1E−07 |
| DP-500 | 2.7E−05 |
| DP-501 | 2.3E−07 |
| DP-502 | 1.7E−05 |
| DP-503 | 2.0E−07 |
| DP-504 | 3.1E−05 |
| DP-505 | 6.8E−06 |
| DP-506 | 2.0E−05 |
| DP-507 | 1.1E−05 |
| DP-508 | 2.5E−06 |
| DP-509 | 5.1E−06 |
| DP-510 | 2.2E−06 |
| DP-511 | 1.1E−06 |
| DP-512 | 1.8E−05 |
| DP-513 | 3.0E−05 |
| DP-514 | 6.8E−06 |

TABLE 11-5-continued

| | iPAMPA Pe |
|---|---|
| DP-515 | 1.0E−07 |
| DP-516 | 9.1E−06 |
| DP-520 | 2.9E−05 |
| DP-521 | 4.4E−05 |
| DP-522 | 5.3E−06 |
| DP-523 | 2.0E−05 |
| DP-524 | 1.6E−05 |
| DP-525 | 2.2E−05 |
| DP-526 | 1.4E−05 |
| DP-527 | 1.1E−05 |
| DP-528 | 1.3E−05 |
| DP-529 | 2.3E−05 |
| DP-530 | 1.1E−05 |
| DP-531 | 5.8E−06 |
| DP-532 | 2.0E−05 |
| DP-533 | 1.0E−05 |
| DP-534 | 6.3E−06 |
| DP-535 | 2.1E−05 |
| DP-536 | 9.9E−06 |
| DP-537 | 1.0E−05 |
| DP-538 | 5.5E−06 |
| DP-539 | 2.0E−05 |
| DP-540 | 3.6E−05 |
| DP-541 | 2.3E−05 |
| DP-542 | 2.2E−05 |
| DP-543 | 2.8E−05 |
| DP-544 | 4.2E−05 |
| DP-545 | 4.0E−05 |
| DP-546 | 4.1E−05 |
| DP-547 | 3.4E−05 |
| DP-560 | 2.6E−05 |
| DP-561 | 2.4E−05 |
| DP-563 | 3.5E−05 |
| DP-564 | 2.7E−05 |
| DP-565 | 1.8E−05 |
| DP-566 | 1.1E−05 |
| DP-567 | 3.0E−05 |
| DP-568 | 4.4E−06 |
| DP-569 | 2.1E−05 |
| DP-570 | 2.1E−06 |
| DP-571 | 2.3E−05 |
| DP-572 | 1.0E−07 |
| DP-573 | 1.0E−07 |
| DP-574 | 1.2E−06 |
| DP-575 | 2.8E−05 |
| DP-576 | 1.5E−05 |
| DP-577 | 9.4E−07 |
| DP-578 | 3.4E−06 |
| DP-579 | 2.4E−05 |
| DP-580 | 1.3E−07 |
| DP-581 | 2.7E−06 |
| DP-582 | 2.1E−05 |
| DP-583 | 2.5E−05 |
| DP-584 | 1.8E−05 |
| DP-585 | 1.5E−05 |
| DP-586 | 4.4E−07 |
| DP-587 | 3.3E−06 |
| DP-588 | 6.0E−07 |
| DP-589 | 1.1E−05 |
| DP-590 | 1.4E−06 |
| DP-591 | 2.6E−05 |
| DP-592 | 1.8E−07 |
| DP-593 | 1.1E−06 |
| DP-594 | 1.3E−06 |
| DP-595 | 4.9E−06 |
| DP-596 | 3.2E−06 |
| DP-597 | 1.7E−06 |
| DP-598 | 1.0E−07 |
| DP-599 | 2.8E−05 |
| DP-600 | 1.0E−07 |
| DP-607 | 1.2E−06 |
| DP-617 | 2.9E−05 |
| DP-618 | 2.8E−05 |
| DP-619 | 1.2E−05 |
| DP-620 | 2.4E−05 |
| DP-621 | 2.1E−05 |
| DP-624 | 2.4E−05 |
| DP-625 | 2.6E−05 |
| DP-626 | 3.6E−05 |
| DP-627 | 2.4E−06 |
| DP-631 | 1.6E−06 |
| DP-639 | 3.3E−05 |
| DP-640 | 5.0E−05 |
| DP-641 | 4.6E−05 |
| DP-642 | 3.2E−05 |
| DP-643 | 2.9E−05 |
| DP-644 | 3.3E−05 |
| DP-645 | 4.9E−05 |
| DP-646 | 2.9E−05 |
| DP-647 | 2.9E−05 |
| DP-648 | 5.3E−05 |
| DP-649 | 2.2E−05 |
| DP-650 | 2.6E−05 |
| DP-651 | 2.4E−05 |
| DP-652 | 3.0E−05 |
| DP-653 | 3.3E−05 |
| DP-654 | 2.3E−05 |
| DP-655 | 3.4E−05 |
| DP-656 | 3.0E−05 |
| DP-657 | 2.4E−05 |
| DP-658 | 3.2E−05 |
| DP-659 | 2.2E−05 |
| DP-660 | 2.7E−05 |
| DP-661 | 2.5E−05 |
| DP-662 | 1.8E−05 |
| DP-663 | 4.3E−05 |
| DP-664 | 7.0E−05 |
| DP-665 | 4.0E−06 |
| DP-666 | 3.0E−06 |
| DP-667 | 1.9E−05 |
| DP-668 | 2.6E−05 |
| DP-669 | 2.9E−05 |
| DP-670 | 1.2E−05 |
| DP-671 | 1.6E−05 |
| DP-672 | 1.3E−05 |
| DP-673 | 3.0E−05 |
| DP-677 | 7.2E−06 |
| DP-678 | 2.6E−05 |
| DP-679 | 2.5E−05 |
| DP-680 | 1.5E−05 |
| DP-681 | 2.8E−05 |
| DP-682 | 1.3E−05 |
| DP-683 | 3.2E−05 |
| DP-684 | 2.3E−05 |
| DP-685 | 2.8E−05 |
| DP-686 | 3.6E−05 |
| DP-687 | 1.0E−05 |
| DP-688 | 1.7E−05 |
| DP-689 | 4.4E−05 |
| DP-690 | 3.3E−05 |
| DP-691 | 3.3E−05 |
| DP-692 | 2.9E−05 |
| DP-693 | 3.5E−05 |
| DP-694 | 3.3E−05 |
| DP-695 | 1.5E−05 |
| DP-696 | 3.7E−05 |
| DP-697 | 3.5E−05 |
| DP-698 | 3.1E−05 |
| DP-699 | 2.9E−05 |
| DP-700 | 4.9E−05 |
| DP-701 | 3.1E−05 |
| DP-702 | 2.5E−05 |
| DP-703 | 3.4E−05 |
| DP-704 | 2.9E−05 |
| DP-705 | 4.9E−05 |
| DP-706 | 4.8E−05 |
| DP-707 | 2.9E−05 |
| DP-708 | 1.6E−05 |
| DP-709 | 3.5E−05 |
| DP-710 | 4.4E−05 |
| DP-711 | 2.9E−05 |
| DP-712 | 1.2E−05 |
| DP-713 | 2.7E−05 |
| DP-714 | 3.1E−05 |
| DP-715 | 2.4E−05 |
| DP-716 | 2.1E−05 |

TABLE 11-5-continued

| | iPAMPA Pe |
|---|---|
| DP-717 | 2.1E−05 |
| DP-718 | 1.7E−05 |
| DP-719 | 2.6E−05 |
| DP-720 | 1.6E−05 |
| DP-721 | 4.9E−05 |
| DP-722 | 4.5E−05 |
| DP-723 | 2.6E−05 |
| DP-724 | 2.0E−05 |
| DP-725 | 3.5E−05 |
| DP-726 | 1.7E−05 |
| DP-727 | 1.6E−05 |
| DP-728 | 6.5E−06 |
| DP-729 | 4.7E−06 |
| DP-730 | 3.7E−05 |
| DP-731 | 4.8E−05 |
| DP-732 | 2.6E−05 |
| DP-733 | 2.6E−05 |
| DP-734 | 1.6E−05 |
| DP-735 | 2.1E−05 |
| DP-736 | 2.7E−05 |
| DP-737 | 3.0E−05 |
| DP-738 | 2.2E−05 |
| DP-739 | 1.8E−05 |
| DP-740 | 3.1E−05 |
| DP-741 | 1.0E−05 |
| DP-742 | 1.5E−05 |
| DP-743 | 1.6E−05 |
| DP-744 | 1.2E−05 |
| DP-745 | 1.7E−05 |
| DP-746 | 4.7E−05 |
| DP-747 | 2.0E−05 |
| DP-748 | 4.5E−05 |
| DP-749 | 1.7E−05 |
| DP-750 | 1.3E−05 |
| DP-751 | 1.8E−05 |
| DP-752 | 6.2E−06 |
| DP-753 | 1.0E−05 |
| DP-754 | 3.2E−05 |
| DP-755 | 3.6E−05 |
| DP-756 | 3.0E−05 |
| DP-757 | 3.3E−05 |
| DP-758 | 2.4E−05 |
| DP-759 | 2.7E−05 |
| DP-760 | 2.8E−05 |
| DP-761 | 9.2E−06 |
| DP-762 | 1.3E−05 |
| DP-763 | 2.5E−06 |
| DP-764 | 5.0E−06 |
| DP-765 | 3.0E−06 |
| DP-766 | 1.3E−05 |
| DP-767 | 3.0E−05 |
| DP-768 | 2.5E−05 |
| DP-769 | 5.3E−05 |
| DP-770 | 3.3E−05 |
| DP-771 | 4.7E−05 |
| DP-772 | 7.0E−05 |
| DP-773 | 4.6E−05 |
| DP-774 | 2.6E−05 |
| DP-775 | 3.7E−05 |
| DP-776 | 1.8E−05 |
| DP-777 | 3.9E−05 |
| DP-778 | 2.6E−05 |
| DP-779 | 3.7E−05 |
| DP-780 | 4.1E−05 |
| DP-781 | 2.9E−05 |
| DP-782 | 1.0E−05 |
| DP-783 | 3.1E−05 |
| DP-784 | 4.6E−05 |
| DP-785 | 2.9E−05 |
| DP-786 | 5.9E−06 |
| DP-787 | 2.9E−05 |
| DP-788 | 4.9E−05 |
| DP-789 | 3.5E−05 |
| DP-790 | 5.6E−05 |
| DP-791 | 4.1E−05 |
| DP-792 | 3.3E−05 |
| DP-793 | 5.3E−05 |
| DP-794 | 3.7E−06 |
| DP-795 | 1.9E−05 |
| DP-796 | 2.0E−05 |
| DP-797 | 2.6E−05 |
| DP-798 | 6.9E−05 |
| DP-799 | 3.2E−05 |
| DP-800 | 2.5E−05 |
| DP-801 | 6.0E−05 |
| DP-802 | 2.9E−05 |
| DP-803 | 2.8E−05 |
| DP-804 | 2.9E−05 |
| DP-805 | 4.1E−05 |
| DP-806 | 2.7E−05 |
| DP-807 | 1.5E−05 |
| DP-808 | 3.3E−06 |
| DP-809 | 7.0E−05 |
| DP-810 | 1.4E−05 |
| DP-811 | 7.0E−05 |
| DP-812 | 3.4E−05 |
| DP-813 | 3.0E−05 |
| DP-814 | 5.7E−05 |
| DP-815 | 4.2E−05 |
| DP-816 | 3.2E−05 |
| DP-817 | 2.5E−05 |
| DP-818 | 2.0E−06 |
| DP-819 | 3.0E−05 |
| DP-820 | 4.8E−05 |
| DP-821 | 6.2E−05 |
| DP-822 | 3.7E−05 |
| DP-823 | 3.1E−05 |
| DP-824 | 2.9E−05 |
| DP-825 | 3.9E−05 |
| DP-826 | 3.0E−05 |
| DP-827 | 5.8E−06 |
| DP-828 | 4.2E−05 |
| DP-829 | 2.1E−05 |
| DP-830 | 4.0E−05 |
| DP-831 | 5.5E−05 |
| DP-832 | 2.1E−05 |
| DP-833 | 1.2E−05 |
| DP-834 | 1.4E−05 |
| DP-835 | 8.0E−06 |
| DP-836 | 1.8E−05 |
| DP-837 | 5.8E−05 |
| DP-838 | 5.4E−05 |
| DP-839 | 2.4E−05 |
| DP-840 | 6.4E−05 |
| DP-841 | 2.0E−05 |
| DP-842 | 2.5E−07 |
| DP-843 | 3.1E−05 |
| DP-844 | 1.1E−05 |
| DP-845 | 2.8E−05 |
| DP-846 | 3.4E−06 |
| DP-847 | 3.3E−06 |
| DP-848 | 3.0E−05 |
| DP-849 | 4.1E−05 |
| DP-850 | 4.3E−06 |
| DP-851 | 2.5E−06 |
| DP-852 | 7.0E−07 |
| DP-853 | 6.3E−06 |
| DP-854 | 7.4E−06 |
| DP-855 | 4.3E−06 |
| DP-856 | 4.4E−07 |
| DP-857 | 3.7E−06 |
| DP-858 | 1.0E−06 |
| DP-859 | 3.7E−06 |
| DP-860 | 5.5E−05 |
| DP-861 | 2.9E−06 |
| DP-862 | 1.0E−07 |
| DP-863 | 3.5E−05 |
| DP-864 | 2.3E−06 |
| DP-865 | 1.5E−05 |
| DP-866 | 5.1E−05 |
| DP-867 | 1.4E−07 |
| DP-868 | 2.4E−07 |
| DP-869 | 8.6E−07 |
| DP-870 | 8.3E−06 |
| DP-871 | 1.2E−06 |
| DP-872 | 3.1E−06 |

TABLE 11-5-continued

| | iPAMPA Pe |
|---|---|
| DP-873 | 1.0E−07 |
| DP-874 | 1.5E−07 |
| DP-875 | 1.9E−05 |
| DP-876 | 5.5E−05 |
| DP-877 | 4.6E−06 |
| DP-878 | 2.3E−05 |
| DP-879 | 3.5E−05 |
| DP-880 | 3.4E−05 |
| DP-881 | 6.8E−06 |
| DP-882 | 1.8E−06 |
| DP-883 | 1.4E−05 |
| DP-884 | 2.0E−07 |
| DP-885 | 3.0E−05 |
| DP-886 | 2.2E−05 |
| DP-887 | 3.9E−06 |
| DP-888 | 8.1E−07 |
| DP-889 | 3.6E−06 |
| DP-890 | 1.5E−07 |
| DP-891 | 2.9E−06 |
| DP-892 | 3.2E−07 |
| DP-893 | 5.3E−06 |
| DP-894 | 4.6E−07 |
| DP-895 | 5.5E−06 |
| DP-896 | 1.3E−05 |
| DP-897 | 2.4E−06 |
| DP-898 | 1.5E−07 |
| DP-899 | 3.8E−06 |
| DP-900 | 1.3E−06 |
| DP-901 | 2.3E−05 |
| DP-902 | 9.3E−07 |
| DP-903 | 3.4E−07 |
| DP-904 | 7.8E−06 |
| DP-905 | 6.0E−07 |
| DP-906 | 6.5E−07 |
| DP-907 | 2.1E−05 |
| DP-908 | 1.6E−06 |
| DP-909 | 1.2E−05 |
| DP-910 | 1.6E−07 |
| DP-911 | 1.0E−07 |
| DP-912 | 1.3E−06 |
| DP-913 | 1.0E−07 |
| DP-914 | 1.0E−07 |
| DP-915 | 1.0E−07 |
| DP-916 | 1.0E−07 |
| DP-917 | 1.0E−07 |
| DP-918 | 5.3E−06 |
| DP-919 | 2.7E−05 |
| DP-920 | 2.2E−07 |
| DP-921 | 3.4E−07 |
| DP-922 | 1.2E−07 |
| DP-923 | 1.0E−07 |
| DP-924 | 1.0E−07 |
| DP-925 | 1.0E−07 |
| DP-926 | 1.0E−07 |
| DP-927 | 1.0E−07 |
| DP-928 | 1.0E−07 |
| DP-929 | 1.2E−05 |
| DP-930 | 4.6E−07 |
| DP-931 | 1.0E−07 |
| DP-932 | |
| DP-933 | |
| DP-934 | |
| DP-935 | 1.0E−07 |
| DP-936 | 1.1E−07 |
| DP-937 | 4.7E−07 |
| DP-938 | 1.0E−07 |
| DP-939 | 3.6E−06 |
| DP-940 | 1.4E−07 |
| DP-941 | 1.0E−07 |
| DP-942 | 1.0E−07 |
| DP-943 | 1.0E−07 |
| DP-944 | 1.0E−07 |
| DP-945 | 1.0E−07 |
| DP-946 | 1.0E−07 |
| DP-947 | 1.0E−07 |
| DP-948 | 7.8E−07 |
| DP-949 | 1.1E−07 |
| DP-950 | 1.0E−07 |
| DP-951 | 1.0E−07 |
| DP-952 | 4.4E−06 |
| DP-953 | 1.0E−07 |
| DP-954 | 1.0E−07 |
| DP-955 | 6.3E−06 |
| DP-956 | 5.8E−07 |
| DP-957 | 4.0E−06 |
| DP-958 | 5.4E−07 |
| DP-959 | 2.9E−06 |
| DP-960 | |
| DP-961 | 5.7E−07 |
| DP-962 | |
| DP-963 | 1.0E−07 |
| DP-964 | 8.9E−06 |
| DP-965 | 1.6E−05 |

3. Test of Metabolic Stability in Human Hepatic Microsome of the Cyclized Peptide Compounds A test of metabolic stability in human hepatic microsome was carried out in order to compare and examine metabolic stability of the synthesized cyclized peptides (the method is previously described, and the results are shown in Table 11-6: Results of the test of metabolic stability in human hepatic microsome).

TABLE 11-6

| | CL NADPH(+) |
|---|---|
| DP-1 | 27 |
| DP-2 | 7 |
| DP-3 | 45 |
| DP-4 | 42 |
| DP-5 | 68 |
| DP-6 | 35 |
| DP-7 | 48 |
| DP-8 | 36 |
| DP-9 | 18 |
| DP-10 | 14 |
| DP-11 | 67 |
| DP-12 | 32 |
| DP-13 | 66 |
| DP-14 | 57 |
| DP-15 | 34 |
| DP-16 | 74 |
| DP-17 | 94 |
| DP-18 | 202 |
| DP-19 | 80 |
| DP-20 | 97 |
| DP-21 | 25 |
| DP-22 | 71 |
| DP-23 | 105 |
| DP-24 | 52 |
| DP-25 | 24 |
| DP-26 | 62 |
| DP-27 | 31 |
| DP-28 | 113 |
| DP-29 | 158 |
| DP-30 | 63 |
| DP-31 | 57 |
| DP-32 | 26 |
| DP-33 | 202 |
| DP-34 | 102 |
| DP-35 | 32 |
| DP-36 | 35 |
| DP-37 | 156 |
| DP-38 | 55 |
| DP-39 | 67 |
| DP-40 | 38 |
| DP-41 | 72 |
| DP-42 | 17 |
| DP-43 | 44 |

TABLE 11-6-continued

| | CL NADPH(+) |
|---|---|
| DP-44 | 59 |
| DP-45 | 129 |
| DP-46 | 249 |
| DP-47 | 37 |
| DP-48 | 32 |
| DP-49 | 51 |
| DP-50 | 80 |
| DP-51 | 96 |
| DP-52 | 136 |
| DP-53 | 60 |
| DP-54 | 13 |
| DP-55 | 79 |
| DP-56 | 43 |
| DP-57 | 23 |
| DP-58 | 27 |
| DP-59 | 65 |
| DP-60 | 145 |
| DP-61 | 47 |
| DP-62 | 22 |
| DP-63 | 58 |
| DP-64 | 25 |
| DP-65 | 97 |
| DP-66 | 69 |
| DP-67 | 15 |
| DP-68 | 35 |
| DP-69 | 68 |
| DP-72 | 58 |
| DP-73 | 30 |
| DP-74 | 118 |
| DP-75 | 27 |
| DP-76 | 27 |
| DP-77 | 33 |
| DP-78 | 57 |
| DP-79 | 145 |
| DP-80 | 43 |
| DP-81 | 38 |
| DP-82 | 16 |
| DP-83 | 39 |
| DP-84 | 21 |
| DP-85 | 58 |
| DP-86 | 237 |
| DP-87 | 120 |
| DP-88 | 32 |
| DP-89 | 58 |
| DP-90 | 30 |
| DP-91 | 58 |
| DP-92 | 29 |
| DP-93 | 17 |
| DP-94 | 17 |
| DP-95 | 19 |
| DP-96 | 51 |
| DP-97 | 72 |
| DP-98 | 27 |
| DP-99 | 52 |
| DP-100 | 80 |
| DP-101 | 101 |
| DP-102 | 5 |
| DP-103 | 73 |
| DP-104 | 29 |
| DP-105 | 60 |
| DP-106 | 155 |
| DP-107 | 14 |
| DP-108 | 48 |
| DP-109 | 36 |
| DP-110 | 36 |
| DP-111 | 17 |
| DP-112 | 49 |
| DP-113 | 84 |
| DP-114 | 56 |
| DP-115 | 28 |
| DP-116 | 333 |
| DP-117 | 194 |
| DP-118 | 79 |
| DP-119 | 67 |
| DP-120 | 84 |
| DP-121 | 46 |
| DP-122 | 169 |
| DP-123 | 21 |
| DP-124 | 27 |
| DP-125 | 189 |
| DP-126 | 239 |
| DP-127 | 194 |
| DP-128 | 276 |
| DP-129 | 120 |
| DP-130 | 76 |
| DP-131 | 48 |
| DP-132 | 37 |
| DP-133 | 51 |
| DP-134 | 18 |
| DP-135 | 15 |
| DP-136 | 147 |
| DP-137 | 86 |
| DP-138 | 48 |
| DP-139 | 22 |
| DP-140 | 96 |
| DP-141 | 77 |
| DP-142 | 22 |
| DP-143 | 25 |
| DP-144 | 125 |
| DP-145 | 232 |
| DP-146 | 52 |
| DP-147 | 147 |
| DP-148 | 69 |
| DP-150 | 701 |
| DP-151 | 30 |
| DP-152 | 93 |
| DP-153 | 179 |
| DP-155 | 101 |
| DP-157 | 368 |
| DP-158 | 41 |
| DP-159 | 54 |
| DP-160 | 68 |
| DP-161 | 194 |
| DP-162 | 90 |
| DP-163 | 68 |
| DP-164 | 253 |
| DP-165 | 42 |
| DP-167 | 75 |
| DP-168 | 85 |
| DP-169 | 43 |
| DP-170 | 22 |
| DP-171 | 191 |
| DP-172 | 25 |
| DP-173 | 251 |
| DP-174 | 66 |
| DP-175 | 94 |
| DP-176 | 47 |
| DP-177 | 27 |
| DP-179 | 13 |
| DP-180 | 35 |
| DP-181 | 13 |
| DP-182 | 9 |
| DP-183 | 25 |
| DP-185 | 19 |
| DP-187 | 22 |
| DP-188 | 84 |
| DP-189 | 3 |
| DP-190 | 3 |
| DP-191 | 46 |
| DP-193 | 124 |
| DP-194 | 72 |
| DP-195 | 52 |
| DP-196 | 65 |
| DP-197 | 48 |
| DP-198 | 34 |
| DP-199 | 170 |
| DP-200 | 57 |
| DP-201 | 209 |
| DP-202 | 134 |
| DP-203 | 18 |
| DP-204 | 48 |
| DP-205 | 29 |
| DP-207 | 12 |
| DP-208 | 34 |
| DP-209 | 98 |
| DP-211 | 178 |

TABLE 11-6-continued

| | CL NADPH(+) |
|---|---|
| DP-212 | 27 |
| DP-213 | 71 |
| DP-214 | 33 |
| DP-215 | 35 |
| DP-216 | 43 |
| DP-217 | 37 |
| DP-218 | 18 |
| DP-219 | 49 |
| DP-220 | 26 |
| DP-221 | 75 |
| DP-222 | 30 |
| DP-223 | 42 |
| DP-224 | 18 |
| DP-225 | 32 |
| DP-226 | 46 |
| DP-227 | 141 |
| DP-228 | 28 |
| DP-229 | 100 |
| DP-230 | 31 |
| DP-231 | 56 |
| DP-232 | 77 |
| DP-233 | 39 |
| DP-234 | 91 |
| DP-235 | 58 |
| DP-236 | 79 |
| DP-237 | 37 |
| DP-238 | 129 |
| DP-239 | 109 |
| DP-240 | 125 |
| DP-241 | 30 |
| DP-242 | 43 |
| DP-243 | 32 |
| DP-244 | 16 |
| DP-245 | 71 |
| DP-246 | 42 |
| DP-247 | 48 |
| DP-248 | 36 |
| DP-249 | 151 |
| DP-250 | 42 |
| DP-251 | 45 |
| DP-252 | 119 |
| DP-253 | 42 |
| DP-254 | 13 |
| DP-255 | 79 |
| DP-256 | 44 |
| DP-257 | 46 |
| DP-258 | 188 |
| DP-259 | 91 |
| DP-260 | 259 |
| DP-261 | 84 |
| DP-262 | 94 |
| DP-263 | 136 |
| DP-264 | 94 |
| DP-265 | 58 |
| DP-266 | 134 |
| DP-267 | 75 |
| DP-268 | 508 |
| DP-269 | 58 |
| DP-270 | 79 |
| DP-271 | 38 |
| DP-272 | 82 |
| DP-273 | 102 |
| DP-274 | 183 |
| DP-275 | 440 |
| DP-276 | 68 |
| DP-277 | 389 |
| DP-280 | 28 |
| DP-281 | 28 |
| DP-282 | 138 |
| DP-284 | 11 |
| DP-285 | 69 |
| DP-288 | 80 |
| DP-290 | 23 |
| DP-291 | 97 |
| DP-293 | 29 |
| DP-294 | 35 |
| DP-296 | 64 |
| DP-297 | 78 |

TABLE 11-6-continued

| | CL NADPH(+) |
|---|---|
| DP-298 | 39 |
| DP-299 | 56 |
| DP-300 | 166 |
| DP-301 | 184 |
| DP-302 | 102 |
| DP-303 | 27 |
| DP-304 | 212 |
| DP-305 | 700 |
| DP-306 | 63 |
| DP-307 | 125 |
| DP-309 | 212 |
| DP-310 | 143 |
| DP-311 | 74 |
| DP-313 | 61 |
| DP-314 | 133 |
| DP-315 | 63 |
| DP-316 | 35 |
| DP-319 | 12 |
| DP-320 | 36 |
| DP-321 | 19 |
| DP-322 | 74 |
| DP-323 | 182 |
| DP-324 | 59 |
| DP-325 | 99 |
| DP-326 | 15 |
| DP-327 | 70 |
| DP-328 | 32 |
| DP-329 | 66 |
| DP-330 | 61 |
| DP-331 | 198 |
| DP-332 | 284 |
| DP-333 | 157 |
| DP-334 | 80 |
| DP-335 | 109 |
| DP-337 | 74 |
| DP-338 | 146 |
| DP-339 | 213 |
| DP-340 | 86 |
| DP-341 | 69 |
| DP-342 | 121 |
| DP-343 | 427 |
| DP-344 | 30 |
| DP-345 | 7 |
| DP-346 | 7 |
| DP-347 | 40 |
| DP-348 | 17 |
| DP-349 | 13 |
| DP-350 | 29 |
| DP-351 | 51 |
| DP-352 | 66 |
| DP-353 | 13 |
| DP-354 | 8 |
| DP-355 | 66 |
| DP-356 | 66 |
| DP-357 | 56 |
| DP-358 | 82 |
| DP-361 | 9 |
| DP-363 | 15 |
| DP-364 | 75 |
| DP-365 | 35 |
| DP-367 | 17 |
| DP-368 | 6 |
| DP-370 | 36 |
| DP-371 | 31 |
| DP-372 | 78 |
| DP-374 | 53 |
| DP-375 | 39 |
| DP-377 | 70 |
| DP-378 | 219 |
| DP-379 | 236 |
| DP-380 | 58 |
| DP-381 | 84 |
| DP-382 | 188 |
| DP-383 | 138 |
| DP-384 | 214 |
| DP-385 | 102 |
| DP-386 | 222 |
| DP-388 | 41 |

TABLE 11-6-continued

| | CL NADPH(+) |
|---|---|
| DP-389 | 14 |
| DP-390 | 52 |
| DP-391 | 14 |
| DP-392 | 18 |
| DP-394 | 10 |
| DP-395 | 23 |
| DP-396 | 141 |
| DP-397 | 92 |
| DP-398 | 123 |
| DP-400 | 24 |
| DP-401 | 145 |
| DP-402 | 185 |
| DP-403 | 57 |
| DP-404 | 107 |
| DP-405 | 83 |
| DP-406 | 11 |
| DP-407 | 29 |
| DP-408 | 14 |
| DP-409 | 28 |
| DP-410 | 19 |
| DP-411 | 114 |
| DP-412 | 122 |
| DP-413 | 68 |
| DP-414 | 20 |
| DP-415 | 118 |
| DP-416 | 20 |
| DP-417 | 113 |
| DP-418 | 71 |
| DP-419 | 17 |
| DP-420 | 69 |
| DP-421 | 171 |
| DP-422 | 26 |
| DP-423 | 110 |
| DP-424 | 135 |
| DP-425 | 150 |
| DP-426 | 546 |
| DP-427 | 141 |
| DP-428 | 77 |
| DP-429 | 115 |
| DP-430 | 96 |
| DP-431 | 239 |
| DP-432 | 396 |
| DP-433 | 35 |
| DP-434 | 166 |
| DP-435 | 41 |
| DP-436 | 142 |
| DP-437 | 265 |
| DP-438 | 155 |
| DP-439 | 139 |
| DP-440 | 124 |
| DP-441 | 123 |
| DP-442 | 159 |
| DP-443 | 17 |
| DP-444 | 3 |
| DP-445 | 14 |
| DP-446 | 104 |
| DP-447 | 159 |
| DP-448 | 27 |
| DP-449 | 6 |
| DP-450 | 17 |
| DP-451 | 14 |
| DP-452 | 21 |
| DP-453 | 64 |
| DP-454 | 50 |
| DP-455 | 17 |
| DP-456 | 29 |
| DP-457 | 14 |
| DP-458 | 10 |
| DP-459 | 143 |
| DP-460 | 17 |
| DP-461 | 78 |
| DP-462 | 17 |
| DP-463 | 10 |
| DP-464 | 30 |
| DP-465 | 23 |
| DP-466 | 17 |
| DP-467 | 12 |
| DP-468 | 53 |

TABLE 11-6-continued

| | CL NADPH(+) |
|---|---|
| DP-469 | 23 |
| DP-470 | 11 |
| DP-471 | 30 |
| DP-472 | 52 |
| DP-473 | 82 |
| DP-474 | 129 |
| DP-475 | 35 |
| DP-476 | 10 |
| DP-477 | 30 |
| DP-478 | 50 |
| DP-479 | 183 |
| DP-480 | 15 |
| DP-481 | 82 |
| DP-482 | 11 |
| DP-483 | 23 |
| DP-484 | 29 |
| DP-485 | 45 |
| DP-486 | 87 |
| DP-487 | 386 |
| DP-488 | 261 |
| DP-489 | 59 |
| DP-490 | 27 |
| DP-491 | 39 |
| DP-492 | 61 |
| DP-493 | 52 |
| DP-494 | 330 |
| DP-495 | 7 |
| DP-496 | 13 |
| DP-497 | 58 |
| DP-498 | 9 |
| DP-500 | 28 |
| DP-501 | 7 |
| DP-502 | 19 |
| DP-503 | 43 |
| DP-504 | 216 |
| DP-505 | 18 |
| DP-506 | 14 |
| DP-507 | 17 |
| DP-508 | 11 |
| DP-509 | 30 |
| DP-511 | 15 |
| DP-512 | 62 |
| DP-513 | 184 |
| DP-514 | 103 |
| DP-515 | 23 |
| DP-516 | 19 |
| DP-517 | 31 |
| DP-519 | 157 |
| DP-520 | 130 |
| DP-521 | 125 |
| DP-522 | 87 |
| DP-523 | 99 |
| DP-524 | 162 |
| DP-525 | 86 |
| DP-526 | 49 |
| DP-527 | 30 |
| DP-528 | 55 |
| DP-529 | 100 |
| DP-530 | 37 |
| DP-531 | 42 |
| DP-532 | 105 |
| DP-533 | 86 |
| DP-534 | 55 |
| DP-535 | 129 |
| DP-536 | 113 |
| DP-537 | 78 |
| DP-538 | 37 |
| DP-539 | 260 |
| DP-540 | 67 |
| DP-541 | 22 |
| DP-542 | 21 |
| DP-543 | 23 |
| DP-544 | 45 |
| DP-545 | 36 |
| DP-546 | 34 |
| DP-547 | 33 |
| DP-548 | 16 |
| DP-550 | 108 |

TABLE 11-6-continued

| | CL NADPH(+) |
|---|---|
| DP-552 | 157 |
| DP-553 | 106 |
| DP-554 | 80 |
| DP-555 | 95 |
| DP-556 | 65 |
| DP-557 | 96 |
| DP-558 | 133 |
| DP-559 | 145 |
| DP-560 | 28 |
| DP-561 | 48 |
| DP-562 | 91 |
| DP-563 | 111 |
| DP-564 | 80 |
| DP-565 | 56 |
| DP-566 | 38 |
| DP-567 | 224 |
| DP-568 | 30 |
| DP-569 | 203 |
| DP-571 | 62 |
| DP-573 | 72 |
| DP-574 | 113 |
| DP-575 | 70 |
| DP-576 | 17 |
| DP-579 | 19 |
| DP-580 | 54 |
| DP-581 | 7 |
| DP-582 | 12 |
| DP-583 | 27 |
| DP-584 | 20 |
| DP-586 | 15 |
| DP-591 | 15 |
| DP-592 | 5 |
| DP-595 | 9 |
| DP-597 | 12 |
| DP-599 | 84 |
| DP-600 | 12 |
| DP-601 | 21 |
| DP-602 | 26 |
| DP-603 | 17 |
| DP-605 | 30 |
| DP-606 | 70 |
| DP-607 | 2 |
| DP-608 | 13 |
| DP-609 | 16 |
| DP-611 | 20 |
| DP-612 | 155 |
| DP-613 | 37 |
| DP-615 | 42 |
| DP-616 | 69 |
| DP-617 | 30 |
| DP-618 | 39 |
| DP-619 | 29 |
| DP-620 | 26 |
| DP-621 | 11 |
| DP-622 | 36 |
| DP-623 | 16 |
| DP-624 | 30 |
| DP-625 | 27 |
| DP-626 | 28 |
| DP-627 | 9 |
| DP-628 | 36 |
| DP-629 | 16 |
| DP-630 | 34 |
| DP-631 | 5 |
| DP-632 | 41 |
| DP-633 | 98 |
| DP-634 | 32 |
| DP-635 | 112 |
| DP-636 | 73 |
| DP-637 | 56 |
| DP-638 | 47 |
| DP-639 | 134 |
| DP-641 | 91 |
| DP-642 | 65 |
| DP-643 | 24 |
| DP-644 | 80 |
| DP-645 | 74 |
| DP-646 | 139 |

TABLE 11-6-continued

| | CL NADPH(+) |
|---|---|
| DP-647 | 132 |
| DP-648 | 109 |
| DP-649 | 27 |
| DP-650 | 33 |
| DP-651 | 68 |
| DP-652 | 51 |
| DP-653 | 235 |
| DP-655 | 62 |
| DP-657 | 157 |
| DP-658 | 86 |
| DP-659 | 13 |
| DP-660 | 222 |
| DP-661 | 17 |
| DP-662 | 101 |
| DP-664 | 304 |
| DP-665 | 77 |
| DP-666 | 74 |
| DP-667 | 39 |
| DP-668 | 142 |
| DP-669 | 54 |
| DP-670 | 22 |
| DP-671 | 39 |
| DP-672 | 72 |
| DP-673 | 631 |
| DP-674 | 10 |
| DP-675 | 22 |
| DP-677 | 45 |
| DP-678 | 284 |
| DP-679 | 342 |
| DP-680 | 96 |
| DP-681 | 275 |
| DP-682 | 20 |
| DP-683 | 53 |
| DP-684 | 126 |
| DP-685 | 90 |
| DP-686 | 227 |
| DP-687 | 10 |
| DP-688 | 23 |
| DP-689 | 103 |
| DP-690 | 217 |
| DP-691 | 326 |
| DP-692 | 212 |
| DP-693 | 246 |
| DP-694 | 170 |
| DP-695 | 47 |
| DP-696 | 194 |
| DP-697 | 87 |
| DP-698 | 142 |
| DP-699 | 81 |
| DP-700 | 398 |
| DP-701 | 69 |
| DP-702 | 123 |
| DP-703 | 222 |
| DP-704 | 83 |
| DP-705 | 265 |
| DP-706 | 264 |
| DP-707 | 84 |
| DP-708 | 35 |
| DP-709 | 90 |
| DP-710 | 121 |
| DP-711 | 217 |
| DP-712 | 57 |
| DP-713 | 169 |
| DP-714 | 145 |
| DP-715 | 134 |
| DP-716 | 133 |
| DP-717 | 101 |
| DP-718 | 99 |
| DP-719 | 218 |
| DP-720 | 62 |
| DP-721 | 915 |
| DP-722 | 311 |
| DP-723 | 154 |
| DP-724 | 160 |
| DP-725 | 138 |
| DP-726 | 75 |
| DP-727 | 59 |
| DP-728 | 42 |

TABLE 11-6-continued

| | CL NADPH(+) |
|---|---|
| DP-729 | 54 |
| DP-730 | 50 |
| DP-731 | 53 |
| DP-732 | 57 |
| DP-733 | 97 |
| DP-734 | 84 |
| DP-735 | 88 |
| DP-736 | 47 |
| DP-737 | 45 |
| DP-738 | 221 |
| DP-739 | 164 |
| DP-740 | 483 |
| DP-741 | 169 |
| DP-742 | 175 |
| DP-743 | 126 |
| DP-744 | 61 |
| DP-745 | 232 |
| DP-746 | 318 |
| DP-747 | 248 |
| DP-748 | 341 |
| DP-749 | 56 |
| DP-750 | 49 |
| DP-751 | 156 |
| DP-752 | 33 |
| DP-753 | 35 |
| DP-754 | 41 |
| DP-755 | 144 |
| DP-756 | 65 |
| DP-757 | 124 |
| DP-758 | 59 |
| DP-759 | 144 |
| DP-760 | 194 |
| DP-761 | 118 |
| DP-762 | 81 |
| DP-763 | 15 |
| DP-764 | 27 |
| DP-765 | 13 |
| DP-766 | 54 |
| DP-767 | 34 |
| DP-768 | 34 |
| DP-769 | 78 |
| DP-770 | 95 |
| DP-771 | 228 |
| DP-772 | 153 |
| DP-773 | 17 |
| DP-774 | 71 |
| DP-775 | 119 |
| DP-776 | 44 |
| DP-777 | 428 |
| DP-778 | 139 |
| DP-779 | 78 |
| DP-780 | 249 |
| DP-781 | 142 |
| DP-782 | 127 |
| DP-783 | 269 |
| DP-784 | 97 |
| DP-785 | 193 |
| DP-786 | 14 |
| DP-787 | 33 |
| DP-788 | 158 |
| DP-789 | 113 |
| DP-790 | 40 |
| DP-791 | 794 |
| DP-792 | 16 |
| DP-793 | 218 |
| DP-794 | 43 |
| DP-795 | 143 |
| DP-796 | 66 |
| DP-797 | 91 |
| DP-798 | 1539 |
| DP-799 | 222 |
| DP-800 | 58 |
| DP-801 | 133 |
| DP-802 | 77 |
| DP-803 | 85 |
| DP-804 | 40 |
| DP-805 | 169 |
| DP-806 | 88 |
| DP-807 | 81 |
| DP-808 | 33 |
| DP-809 | 201 |
| DP-810 | 46 |
| DP-811 | 241 |
| DP-812 | 222 |
| DP-813 | 195 |
| DP-814 | 22 |
| DP-815 | 104 |
| DP-816 | 192 |
| DP-817 | 165 |
| DP-818 | 1 |
| DP-819 | 134 |
| DP-820 | 511 |
| DP-821 | 547 |
| DP-822 | 518 |
| DP-823 | 254 |
| DP-824 | 501 |
| DP-825 | 168 |
| DP-826 | 213 |
| DP-827 | 49 |
| DP-828 | 154 |
| DP-829 | 65 |
| DP-830 | 321 |
| DP-831 | 683 |
| DP-832 | 850 |
| DP-833 | 427 |
| DP-834 | 501 |
| DP-835 | 497 |
| DP-836 | 552 |
| DP-837 | 284 |
| DP-838 | 224 |
| DP-839 | 91 |
| DP-840 | 357 |
| DP-841 | 386 |
| DP-842 | 135 |
| DP-843 | 505 |
| DP-844 | 356 |
| DP-845 | 248 |
| DP-846 | 310 |
| DP-847 | 329 |
| DP-848 | 148 |
| DP-849 | 202 |
| DP-850 | 119 |
| DP-851 | 99 |
| DP-852 | 484 |
| DP-853 | 120 |
| DP-854 | 252 |
| DP-855 | 210 |
| DP-856 | 183 |
| DP-857 | 284 |
| DP-858 | 77 |
| DP-859 | 87 |
| DP-860 | 322 |
| DP-861 | 320 |
| DP-862 | 118 |
| DP-863 | 927 |
| DP-864 | 171 |
| DP-865 | 87 |
| DP-866 | 211 |
| DP-867 | 211 |
| DP-868 | 61 |
| DP-869 | 331 |
| DP-870 | 474 |
| DP-871 | 389 |
| DP-872 | 397 |
| DP-873 | 39 |
| DP-874 | 48 |
| DP-875 | 34 |
| DP-876 | 103 |
| DP-877 | 43 |
| DP-878 | 152 |
| DP-879 | 239 |
| DP-880 | 490 |
| DP-881 | 83 |
| DP-882 | 32 |
| DP-883 | 294 |
| DP-884 | 64 |

TABLE 11-6-continued

| | CL NADPH(+) |
|---|---|
| DP-885 | 75 |
| DP-886 | 162 |
| DP-887 | 103 |
| DP-888 | 69 |
| DP-889 | 89 |
| DP-890 | 47 |
| DP-891 | 100 |
| DP-892 | 57 |
| DP-893 | 86 |
| DP-894 | 71 |
| DP-895 | 54 |
| DP-896 | 57 |
| DP-897 | 56 |
| DP-898 | 21 |
| DP-899 | 32 |
| DP-900 | 244 |
| DP-901 | 131 |
| DP-902 | 121 |
| DP-903 | 26 |
| DP-904 | 89 |
| DP-905 | 73 |
| DP-906 | 49 |
| DP-907 | |
| DP-908 | 3 |
| DP-909 | 15 |
| DP-910 | |
| DP-911 | 152 |
| DP-912 | 8 |
| DP-913 | 30 |
| DP-914 | 29 |
| DP-915 | 89 |
| DP-916 | 55 |
| DP-917 | 177 |
| DP-918 | 55 |
| DP-919 | 128 |
| DP-920 | 27 |
| DP-921 | 88 |
| DP-922 | 70 |
| DP-923 | 8 |
| DP-924 | 19 |
| DP-925 | 2 |
| DP-926 | 53 |
| DP-927 | 5 |
| DP-928 | 60 |
| DP-929 | 49 |
| DP-930 | 168 |
| DP-931 | 12 |
| DP-932 | 108 |
| DP-933 | 43 |
| DP-934 | 143 |
| DP-935 | 29 |
| DP-936 | 29 |
| DP-937 | 164 |
| DP-938 | 8 |
| DP-939 | 8 |
| DP-940 | 37 |
| DP-941 | 49 |
| DP-942 | 23 |
| DP-943 | 7 |
| DP-944 | 20 |
| DP-945 | 28 |
| DP-946 | 15 |
| DP-947 | 14 |

TABLE 11-6-continued

| | CL NADPH(+) |
|---|---|
| DP-948 | 20 |
| DP-949 | 37 |
| DP-950 | 12 |
| DP-951 | 11 |
| DP-952 | 91 |
| DP-953 | 8 |
| DP-954 | 26 |
| DP-955 | 30 |
| DP-956 | 40 |
| DP-957 | 54 |
| DP-958 | 31 |
| DP-959 | |
| DP-960 | 36 |
| DP-961 | 33 |
| DP-962 | 22 |
| DP-963 | 18 |
| DP-964 | 38 |
| DP-965 | 56 |

Mouse PK Test of Peptides

The changes in the plasma concentrations after intravenous administration and oral administration in mice were evaluated for eight peptides satisfying the conditions (chain length, number of N-methylamino acids and ClogP) for peptides to possess drug-likeness as revealed by the present inventors. The compound was intravenously and orally administered at a dose of 20 mg/kg to male mice (C57BL/6J, six-week-old, manufactured by CLEA Japan: three mice per group). Blood until 24 hours after the administration was collected over time from the dorsal foot vein using a hematocrit tube previously treated with heparin as an anticoagulant. Plasma was separated from the blood by centrifugation and subjected to deproteinization treatment with acetonitrile, after which the plasma concentration was measured using an LC/MS/MS instrument (API3200, manufactured by ABSCIEX, USA). Pharmacokinetic parameters were calculated from the resulting change in the plasma concentration by noncompartment analysis using analysis software Phoenix WinNonlin 6.1 (manufactured by Pharsight Corporation, USA).

Each parameter is defined as follows. The concentration at the time 0 after intravenous administration (C0; extrapolated value, ng/mL), the highest plasma concentration after oral administration (Cmax; ng/mL), the time to reach the maximum plasma concentration (Tmax; time), the area under the plasma concentration-time curve (AUC; ng·time/mL), the systemic clearance (CL; mL/min/kg), the steady state distribution volume (Vss; mL/kg), the elimination half-life (t½; time) and the bioavailability (F; 9) were calculated. The systemic clearance after intravenous administration was small in every case (1.7-9.5 mL/min/kg), and this suggested that metabolic stability is high. The highest bioavailability of the compound was 35%, and the eight peptides evaluated had oral absorbability allowing them to be developed as oral administration agents, as expected.

TABLE 11-7

| Compound | | | | | | | | | | | | |
|---|---|---|---|---|---|---|---|---|---|---|---|---|
| DP-125 | | | MeAla | Thr | MeAla | Leu | MePhe | MePhe | Leu | MeLeu | Asp | pip |
| DP-265 | | | D-Val | MePhe | MeLeu | Thr | MeGly | MeLeu | Ser(tBu) | MeIle | Asp | pip |
| DP-540 | | MeAla | MePhe | nPrGly | MeLeu | Thr | MeAla | MeLeu | MeIle | Ser(tBu) | Asp | pip |
| DP-547 | | D-Ala | MeAla | MePhe | MeLeu | Thr | nPrGly | MeLeu | Ser(tBu) | MeLeu | Asp | pip |
| DP-965 | | Ala | Leu | MeI | Val | MePhe | Leu | MePhe | Asp | Pro | Ile | pip |
| DP-47 | MeAla | MePhe | Leu | MeLeu | Thr | MeGly | MeIle | Ser(tBu) | MePhe | MeVal | Asp | pip |

TABLE 11-7-continued

| Compound | | | | | | | | | | | | |
|---|---|---|---|---|---|---|---|---|---|---|---|---|
| DP-67 | MeAla | Thr | MeGly | MePhe | MePhe | MeLeu | Pro | MeLeu | Ala | MeVal | Asp | pip |
| DP-101 | MeAla | Leu | MeLeu | MePhe | Ala | MePhe | MeIle | Thr | MeGly | MeLeu | Asp | pip |

TABLE 11-8

Pharmacokinetic parameters at the time of intravenous administration

| Compound | Number of amino acid residues | C0 (ng/mL) | AUC (ng/time * mL) | CL (mL/min/kg) | Vss (L/kg) | T½ (time) |
|---|---|---|---|---|---|---|
| DP-125 | 9 | 46400 | 35400 | 9.49 | 0.545 | 1.44 |
| DP-265 | 9 | 58300 | 35300 | 9.48 | 0.713 | 1.82 |
| DP-540 | 10 | 48100 | 41400 | 8.16 | 0.803 | 1.63 |
| DP-547 | 10 | 44500 | 37200 | 8.98 | 0.541 | 1.10 |
| DP-965 | 10 | 171000 | 193000 | 1.73 | 0.403 | 2.99 |
| DP-47 | 11 | 107000 | 202000 | 1.66 | 0.381 | 2.68 |
| DP-67 | 11 | 102000 | 70700 | 4.74 | 0.431 | 3.25 |
| DP-101 | 11 | 112000 | 83300 | 4.01 | 0.455 | 1.91 |

TABLE 11-9

Pharmacokinetic parameters at the time of oral administration

| Compound | Number of amino acid residues | Cmax (ng/mL) | Tmax (h) | AUC (ng/time * mL) | CL/F (mL/min/kg) | T½ (time) | F (%) |
|---|---|---|---|---|---|---|---|
| DP-125 | 9 | 3090 | 3.50 | 12100 | 27.5 | Not calculable | 34.6 |
| DP-265 | 9 | 2850 | 0.67 | 5120 | 65.1 | 1.96 | 14.5 |
| DP-540 | 10 | 1870 | 1.83 | 9800 | 35.8 | 3.11 | 23.7 |
| DP-547 | 10 | 1470 | 1.00 | 4510 | 74.6 | 1.84 | 12.1 |
| DP-965 | 10 | 1920 | 2.67 | 13700 | 28.9 | 2.99 | 7.12 |
| DP-47 | 11 | 4490 | 2.67 | 38000 | 8.86 | 3.88 | 18.8 |
| DP-67 | 11 | 2310 | 3.50 | 10900 | 37.9 | 4.36 | 15.5 |
| DP-101 | 11 | 2320 | 1.83 | 12700 | 26.2 | 2.27 | 15.2 |

[Example 20] Amidation Condensation Reaction Between N-Terminal Amino Acids without Reaction Auxiliary Groups and C-Terminal Active Esters 1. Amidation Reaction Between N-Terminal Amino Groups without Reaction Auxiliary Groups and Active Esters in Translation Solutions 1-1. Examples of Methods in which Relatively Stable Active Esters are Translationally Synthesized and then the Esters are Activated and Reacted with Amines without Reaction Auxiliary Groups by Adding Activating Agents 1-1-1. Synthesis of Model Reaction Starting Material Compounds (Compound P-145)

Synthesis of (9S,12S,18S,21S,24S,27S,30S)-30-
(((S)-1-(((S)-1-((2-amino-2-oxoethyl)amino)-3-(tert-butoxy)-1-oxopropan-2-yl)amino)-1-oxopropan-2-yl)(methyl)carbamoyl)-12,27-dibenzyl-18-isobutyl-24-isopropyl-2,2,9,11,17,21-hexamethyl-4,7,10,13,16,19,22,25,28-nonaoxo-3-oxa-5,8,11,14,17,20,23,26,29-nonaazadotriacontan-32-oic Acid (Boc-Gly-Ala-$^{Me}$Phe-Gly-$^{Me}$Leu-Ala-Val-Phe-Asp-$^{Me}$Ala-Ser(tBu)-Gly-NH2) (SEQ ID NO: 231)

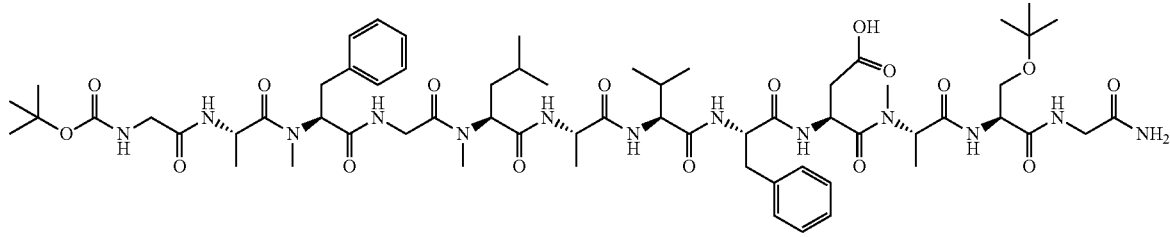 [SMILES: CC(C)C[C@@H](C(=O)N[C@@H](C)C(=O)N[C@H](C(=O)N[C@@H](Cc1ccccc1)C(=O)N[C@@H](CC(=O)O)C(=O)N(C)[C@@H](C)C(=O)N[C@@H](COC(C)(C)C)C(=O)NCC(N)=O)C(C)C)N(C)C(=O)CNC(=O)[C@H](Cc1ccccc1)N(C)C(=O)[C@H](C)NC(=O)CNC(=O)OC(C)(C)C]

Dihydroxypalladium/carbon (312 mg, 50% wet w/w) was added to a solution of benzyl (9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-12,27-dibenzyl-18-isobutyl-24-isopropyl-2,2,9,11,17,21-hexamethyl-4,7,10,13,16,19,22,25,28-nonaoxo-3-oxa-5,8,11,14,17,20,23,26,29-nonaazadotriacontan-32-oate synthesized by peptide synthesis by the Fmoc method previously described using Boc amino acid in place of Fmoc amino acid at the N-terminal (Boc-Gly-Ala-$^{Me}$Phe-Gly-$^{Me}$Leu-Ala-Val-Phe-Asp-(OBn)-$^{Me}$Ala-Ser(tBu)-Gly-NH2 (SEQ ID NO: 232), 919 mg, 0.657 mmol) in methanol (6 ml) under a nitrogen atmosphere, the atmosphere was replaced with hydrogen, and the mixture was then stirred at room temperature for 2 hours. The reaction solution was then filtered through celite, the filtrate was concentrated under reduced pressure, and the resulting residue is purified by column chromatography (10 mM aqueous ammonium acetate solution:methanol=70/30-0/100) to afford the title compound P-145 (Boc-Gly-Ala-$^{Me}$Phe-Gly-$^{Me}$Leu-Ala-Val-Phe-Asp-$^{Me}$Ala-Ser(tBu)-Gly-NH2) (SEQ ID NO: 231) (374 mg, 44%). LCMS: m/z 1307 (M−H)−

Retention time: 1.09 minutes (analysis condition SQD AA05)

(Compound P-146)

Synthesis of S-benzyl (9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-12,27-dibenzyl-18-isobutyl-24-isopropyl-2,2,9,11,17,21-hexamethyl-4,7,10,13,16,19,22,25,28-nonaoxo-3-oxa-5,8,11,14,17,20,23,26,29-nonaazadotriacontane-32-thioate (Boc-Gly-Ala-$^{Me}$Phe-Gly-$^{Me}$Leu-Ala-Val-Phe-Asp(SBn)-$^{Me}$Ala-Ser (tBu)-Gly-NH2) (SEQ ID NO: 233)

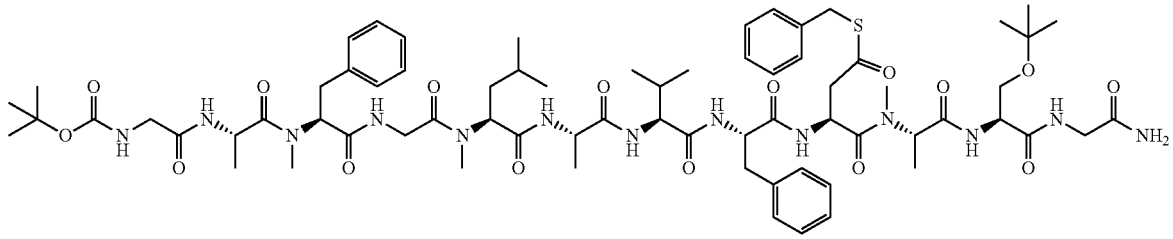 [SMILES: CC(C)C[C@@H](C(=O)N[C@@H](C)C(=O)N[C@H](C(=O)N[C@@H](Cc1ccccc1)C(=O)N[C@@H](CC(=O)SCc1ccccc1)C(=O)N(C)[C@@H](C)C(=O)N[C@@H](COC(C)(C)C)C(=O)NCC(N)=O)C(C)C)N(C)C(=O)CNC(=O)[C@H](Cc1ccccc1)N(C)C(=O)[C@H](C)NC(=O)CNC(=O)OC(C)(C)C]

(9S,12S,18S,21S,24S,27S,30S)-30-(((S)-1-(((S)-1-((2-Amino-2-oxoethyl)amino)-3-(tert-butoxy)-1-oxopropan-2-yl)amino)-1-oxopropan-2-yl)(methyl)carbamoyl)-12,27-dibenzyl-18-isobutyl-24-isopropyl-2,2,9,11,17,21-hexamethyl-4,7,10,13,16,19,22,25,28-nonaoxo-3-oxa-5,8,11,14,17,20,23,26,29-nonaazadotriacontan-32-oic acid (Compound P-145, (Boc-Gly-Ala-$^{Me}$Phe-Gly-$^{Me}$Leu-Ala-Val-Phe-Asp-$^{Me}$Ala-Ser(tBu)-Gly-NH2) (SEQ ID NO: 231)) (50.0 mg, 0.038 mmol) was dissolved in dichloromethane (320 μL) and DMF (80 μL), phenylmethanethiol (9.49 mg, 0.076 mmol), DIC (9.64 mg, 0.076 mmol) and N,N-dimethylpyridin-4-amine (3.54 mg, 0.029 mmol) were added and the mixture was stirred at room temperature overnight. The reaction solution was concentrated under reduced pressure, and the resulting residue was purified by column chromatography (10 mM aqueous ammonium acetate solution:methanol) to afford the title compound (11.8 mg, 21.8%).

LCMS: m/z 1414.8 (M+H)+

Retention time: 1.08 min (analysis condition SQD AA05)

(Compound P-147)

Synthesis of S-benzyl (4S,7S,13S,16S,19S,22S, 25S)-1-amino-25-(((S)-1-(((S)-1-((2-amino-2-oxo-ethyl)amino)-3-hydroxy-1-oxopropan-2-yl)amino)-1-oxopropan-2-yl)(methyl)carbamoyl)-7,22-dibenzyl-13-isobutyl-19-isopropyl-4,6,12,16-tetramethyl-2,5,8,11,14,17,20,23-octaoxo-3,6,9,12, 15,18,21,24-octaazaheptacosane-27-thioate (Gly-Ala-$^{Me}$Phe-Gly-$^{Me}$Leu-Ala-Val-Phe-Asp(SBn)-$^{Me}$Ala-Ser-Gly-NH2) (SEQ ID NO: 326)

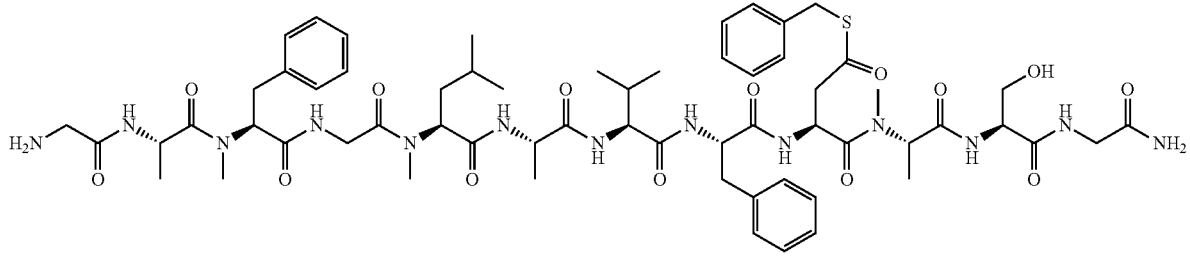 [SMILES: CC(C)C[C@@H](C(=O)N[C@@H](C)C(=O)N[C@H](C(=O)N[C@@H](Cc1ccccc1)C(=O)N[C@@H](CC(=O)SCc1ccccc1)C(=O)N(C)[C@@H](C)C(=O)N[C@@H](CO)C(=O)NCC(N)=O)C(C)C)N(C)C(=O)CNC(=O)[C@H](Cc1ccccc1)N(C)C(=O)[C@H](C)NC(=O)CN]

S-benzyl (9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-12,27-dibenzyl-18-isobutyl-24-isopropyl-2,2,9,11,17, 21-hexamethyl-4,7,10,13,16,19,22,25,28-nonaoxo-3-oxa-5, 8,11,14,17,20,23,26,29-nonaazadotriacontane-32-thioate (Compound P-146) (11.8 mg, 0.0083 mmol) was dissolved in dichloromethane (150 µL), TFA (75.0 µL, 0.973 mmol) was added and the mixture was stirred at room temperature for 1.5 hours. The reaction solution was concentrated under reduced pressure, and the resulting residue was purified by column chromatography (0.1% aqueous FA solution: 0.1% FA-acetonitrile solution) to afford the title compound (7.3 mg, 69.5%).

LCMS: m/z 1258.6 (M+H)+

Retention time: 0.58 min (analysis condition SQD FA05)

(Compound P-133)

Synthesis of (6S,9S,12S,15S,18S,24S,27S,30S,33S)-18,30-dibenzyl-12,24-diisobutyl-9,27-diisopropyl-2, 2,6,11,17,23,26-heptamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22, 25,28,31-decaoxo-15-((R)-1-(trityloxy)ethyl)-3-oxa-5,8,11,14,17,20,23,26,29,32-decaazapentatriacontan-35-oic Acid (Boc-Ala-Val-MeLeu-Thr(Trt)-MePhe-Gly-MeLeu-MeVal-Phe-Asp-MePhe-Ala-piperidine) (SEQ ID NO: 327)

Ala-piperidine or Ala-pip herein refers to a compound having an amide bond formed by the nitrogen atom of piperidine and the main chain carboxylic acid site of Ala. The same description is also used when a peptide site has this partial structure.

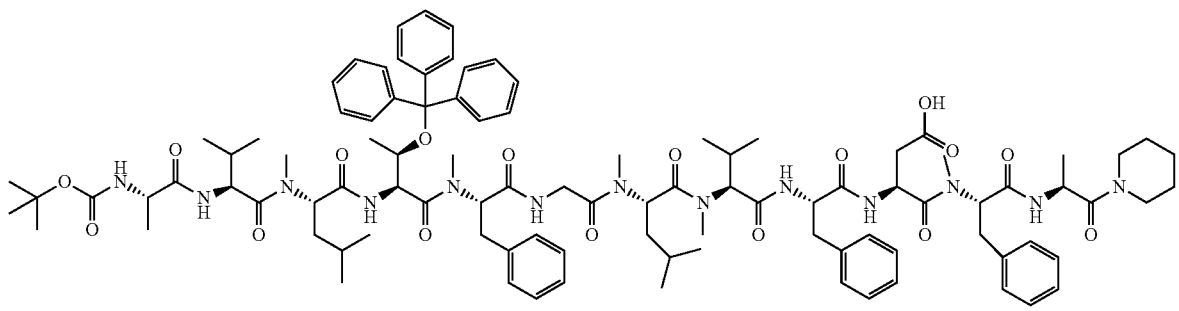 [SMILES: CC(C)C[C@@H](C(=O)N(C)[C@H](C(=O)N[C@@H](Cc1ccccc1)C(=O)N[C@@H](CC(=O)O)C(=O)N(C)[C@@H](Cc1ccccc1)C(=O)N[C@@H](C)C(=O)N1CCCCC1)C(C)C)N(C)C(=O)CNC(=O)[C@H](Cc1ccccc1)N(C)C(=O)[C@@H](NC(=O)[C@H](CC(C)C)N(C)C(=O)[C@@H](NC(=O)[C@H](C)NC(=O)OC(C)(C)C)C(C)C)[C@@H](C)OC(c1ccccc1)(c1ccccc1)c1ccccc1]

Hydroxypalladium/carbon (256 mg, 50% wet w/w) was added to a solution of benzyl (6S,9S,12S,15S,18S,24S,27S, 30S,33S)-18,30-dibenzyl-12,24-diisobutyl-9,27-diisopropyl-2,2,6,11,17,23,26-heptamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28, 31-decaoxo-15-((R)-1-(trityloxy)ethyl)-3-oxa-5,8,11,14,17, 20,23,26,29,32-decaazapentatriacontan-35-oate synthesized according to a conventional method (Boc-Ala-Val-MeLeu-Thr(Trt)-MePhe-Gly-MeLeu-MeVal-Phe-Asp(OBn)-MePhe-Ala-piperidine) (SEQ ID NO: 328) (770 mg, 0.412 mmol) in methanol (4 ml) under a nitrogen atmosphere, the atmosphere was replaced with hydrogen, and the mixture was stirred at room temperature for 2.5 hours. The reaction solution was then filtered through celite, and the filtrate was concentrated under reduced pressure to afford the title compound (726 mg, 99%).

LCMS: m/z 1777.6 (M−H)−

Retention time: 0.86 min (analysis condition SQD AA50) (Compound P-134)

Synthesis of S-benzyl (6S,9S,12S,15S,18S,24S,27S,30S,33S)-18,30-dibenzyl-12,24-diisobutyl-9,27-diisopropyl-2,2,6,11,17,23,26-heptamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-((R)-1-(trityloxy)ethyl)-3-oxa-5,8,11,14,17,20,23,26,29,32-decaazapentatriacontane-35-thioate (Boc-Ala-Val-MeLeu-Thr(Trt)-MePhe-Gly-MeLeu-MeVal-Phe-Asp(SBn)-MePhe-Ala-piperidine) (SEQ ID NO: 329)

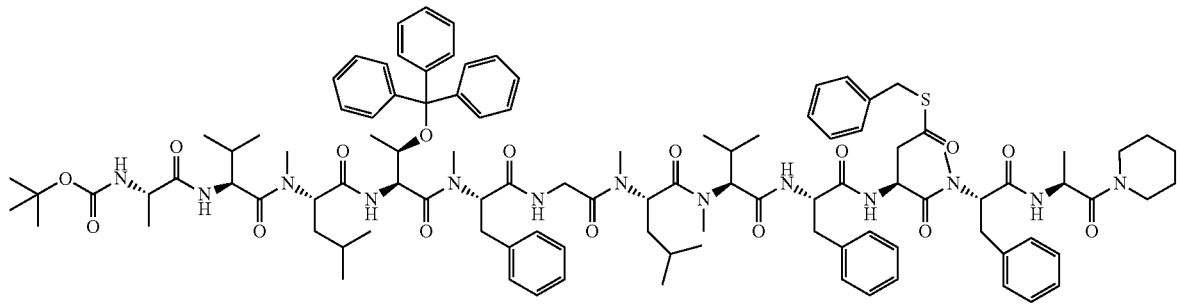 [SMILES: CC(C)C[C@@H](C(=O)N(C)[C@H](C(=O)N[C@@H](Cc1ccccc1)C(=O)N[C@@H](CC(=O)SCc1ccccc1)C(=O)N(C)[C@@H](Cc1ccccc1)C(=O)N[C@@H](C)C(=O)N1CCCCC1)C(C)C)N(C)C(=O)CNC(=O)[C@H](Cc1ccccc1)N(C)C(=O)[C@@H](NC(=O)[C@H](CC(C)C)N(C)C(=O)[C@@H](NC(=O)[C@H](C)NC(=O)OC(C)(C)C)C(C)C)[C@@H](C)OC(c1ccccc1)(c1ccccc1)c1ccccc1]

The title compound (33.0 mg, 62.3%) was obtained in the same manner as in the synthesis of Compound P-146 using (6S,9S,12S,15S,18S,24S,27S,30S,33S)-18,30-dibenzyl-12,24-diisobutyl-9,27-diisopropyl-2,2,6,11,17,23,26-heptamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-NR)-1-(trityloxy)ethyl)-3-oxa-5,8,11,14,17,20,23,26,29,32-decaazapentatriacontan-35-oic acid (Compound P-133) (50.0 mg, 0.028 mmol) as a starting material.

LCMS: m/z 1883.3 (M−H)−

Retention time: 0.93 min (analysis condition SQD AA50)

(Compound P-135)

Synthesis of S-benzyl (3S,6S,9S,12S,18S,21S,24S,27S,30S)-30-amino-6,18-dibenzyl-21-((R)-1-hydroxyethyl)-12,24-diisobutyl-9,27-diisopropyl-10,13,19,25-tetramethyl-3-(methyl((S)-1-oxo-1-(((S)-1-oxo-1-(piperidin-1-yl)propan-2-yl)amino)-3-phenylpropan-2-yl)carbamoyl)-5,8,11,14,17,20,23,26,29-nonaoxo-4,7,10,13,16,19,22,25,28-nonaazahentriacontane-1-thioate (Ala-Val-MeLeu-Thr-MePhe-Gly-MeLeu-MeVal-Phe-Asp(SBn)-MePhe-Ala-piperidine) (SEQ ID NO: 330)

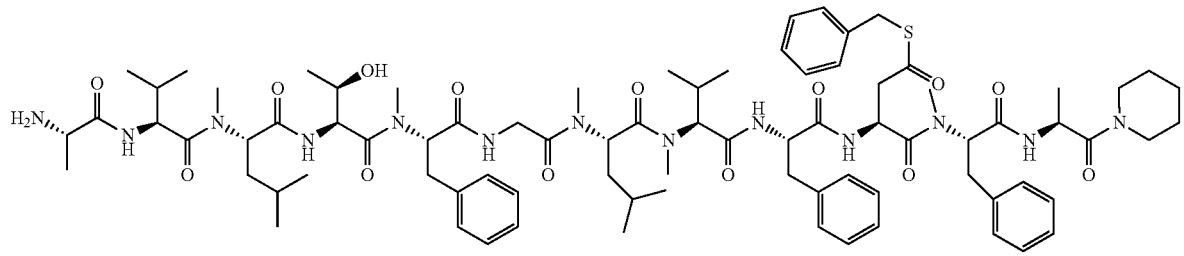 [SMILES: CC(C)C[C@@H](C(=O)N(C)[C@H](C(=O)N[C@@H](Cc1ccccc1)C(=O)N[C@@H](CC(=O)SCc1ccccc1)C(=O)N(C)[C@@H](Cc1ccccc1)C(=O)N[C@@H](C)C(=O)N1CCCCC1)C(C)C)N(C)C(=O)CNC(=O)[C@H](Cc1ccccc1)N(C)C(=O)[C@@H](NC(=O)[C@H](CC(C)C)N(C)C(=O)[C@@H](NC(=O)[C@H](C)N)C(C)C)[C@@H](C)O]

The title compound (6.0 mg, 22.9%) was obtained in the same manner as in the synthesis of Compound P-147 using S-benzyl (6S,9S,12S,15S,18S,24S,27S,30S,33S)-18,30-dibenzyl-12,24-diisobutyl-9,27-diisopropyl-2,2,6,11,17,23,26-heptamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-((R)-1-(trityloxy)ethyl)-3-oxa-5,8,11,14,17,20,23,26,29,32-decaazapentatriacontane-35-thioate (Compound P-134) (33.0 mg, 0.018 mmol) as a starting material.

LCMS: m/z 1541.0 (M−H)−

Retention time: 0.77 min (analysis condition SQD FA05)

Synthesis of 2-(ethyldisulfanyl)-6-methylphenyl (6S,9S,12S,15S,18S,24S,27S,30S,33S)-18,30-dibenzyl-12,24-diisobutyl-9,27-diisopropyl-2,2,6,11,17,23,26-heptamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-((R)-1-(trityloxy)ethyl)-3-oxa-5,8,11,14,17,20,23,26,29,32-decaazapentatriacontan-35-oate (Compound P-138)

20,23,26,29,32-decaazapentatriacontan-35-oic acid (Boc-Ala-Val-$^{Me}$Leu-Thr(Trt)-$^{Me}$Phe-Gly-$^{Me}$Leu-$^{Me}$Val-Phe-Asp-$^{Me}$Phe-Ala-piperidine (SEQ ID NO: 327), 60.9 mg, 0.034 mmol) synthesized by peptide synthesis by the Fmoc method previously described using Boc amino acid in place of Fmoc amino acid at the N-terminal in dichloromethane (300 ul), and the mixture was stirred at room temperature overnight. The reaction solution was then concentrated under reduced pressure and purified by reverse phase silica gel column chromatography (10 mM aqueous ammonium acetate solution/methanol=70/30→0/100) to afford 2-(ethyldisulfanyl)-6-methylphenyl (6S,9S,12S,15S,18S,24S,27S,30S,33S)-18,30-dibenzyl-12,24-diisobutyl-9,27-diisopropyl-2,2,6,11,17,23,26-heptamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-((R)-1-(trityloxy)ethyl)-3-oxa-5,8,11,14,17,20,23,26,29,32-decaazapentatriacontan-35-oate (Compound P-138) (53.8 mg, 80%).

LCMS (ESI) m/z=1959.2 (M−H)−

Retention time: 1.05 min (analysis condition SQDAA50)

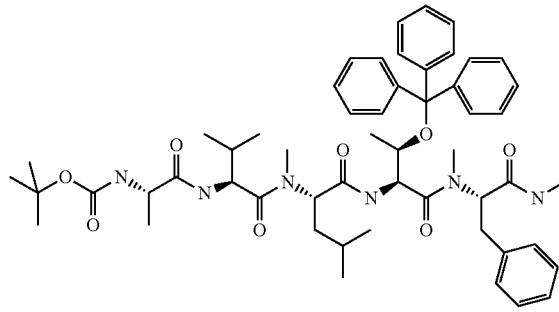

2-(Ethyldisulfanyl)-6-methylphenol separately synthesized according to a conventional method (J. AM. CHEM. SOC. 2009, 131, 5432-5437) (10.3 mg, 0.051 mmol), 1,N'-methanediylidenebis(propan-2-amine) (8.0 ul, 0.051 mmol) and N,N-dimethylpyridin-4-amine (4.2 mg, 0.034 mmol) were added to a solution of (6S,9S,12S,15S,18S,24S,27S,30S,33S)-18,30-dibenzyl-12,24-diisobutyl-9,27-diisopropyl-2,2,6,11,17,23,26-heptamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-((R)-1-(trityloxy)ethyl)-3-oxa-5,8,11,14,17, Synthesis of 2-(ethyldisulfanyl)-6-methylphenyl (3S,6S,9S,12S,18S,21S,24S,27S,30S)-30-amino-6,18-dibenzyl-21-((R)-1-hydroxyethyl)-12,24-diisobutyl-9,27-diisopropyl-10,13,19,25-tetramethyl-3-(methyl((S)-1-oxo-1-(((S)-1-oxo-1-(piperidin-1-yl)propan-2-yl)amino)-3-phenylpropan-2-yl)carbamoyl)-5,8,11,14,17,20,23,26,29-nonaoxo-4,7,10,13,16,19,22,25,28-nonaazahentriacontan-1-oate (Compound P-139)

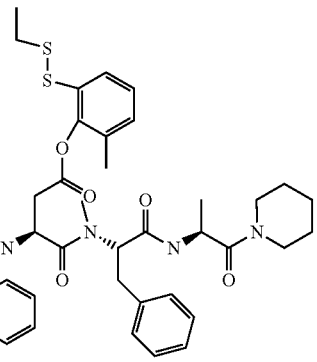

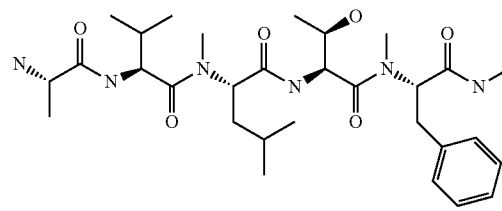

2131

Trifluoroacetic acid (300 ul) and triisopropyisilane (27.7 ul, 0.135 mmol) were added to a solution of 2-(ethyldisulfanyl)-6-methylphenyl (6S,9S,12S,15S,18S,24S,27S,30S,33S)-18,30-dibenzyl-12,24-diisobutyl-9,27-diisopropyl-2,2,6,11,17,23,26-heptamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-((R)-1-(trityloxy)ethyl)-3-oxa-5,8,11,14,17,20,23,26,29,32-decaazapentatriacontan-35-oate (Compound P-138) (53.0 mg, 27 umol) in dichloromethane (200 ul), and the mixture was stirred at room temperature for 1 hour. The reaction solution was then concentrated under reduced pressure and purified by reverse phase silica gel column chromatography (0.1% aqueous formic acid solution/0.1% formic acid-acetonitrile solution=70/30→0/100) to afford 2-(ethyldisulfanyl)-6-methylphenyl (3S,6S,9S,12S,18S,21S,24S,27S,30S)-30-amino-6,18-dibenzyl-21-((R)-1-hydroxyethyl)-12,24-diisobutyl-9,27-diisopropyl-10,13,19,25-tetramethyl-3-

2132

(methyl((S)-1-oxo-1-(((S)-1-oxo-1-(piperidin-1-yl)propan-2-yl)amino)-3-phenylpropan-2-yl)carbamoyl)-5,8,11,14,17,20,23,26,29-nonaoxo-4,7,10,13,16,19,22,25,28-nonaazahentriacontan-1-oate (Compound P-139) (22.4 mg, 51%).

LCMS (ESI) m/z=1620 (M+H)+

Retention time: 0.88 min (analysis condition SQDAA50)

Synthesis of (6S,9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-12,27-dibenzyl-18-isobutyl-24-isopropyl-2,2,6,9,11,21-hexamethyl-4,7,10,13,16,19,22,25,28-nonaoxo-3-oxa-5,8,11,14,17,20,23,26,29-nonaazadotriacontan-32-oic Acid (Boc-Ala-Ala-MePhe-Gly-Leu-Ala-Val-Phe-Asp-MeAla-Ser(tBu)-Gly-NH2) (Compound SP-501) (SEQ ID NO: 331)

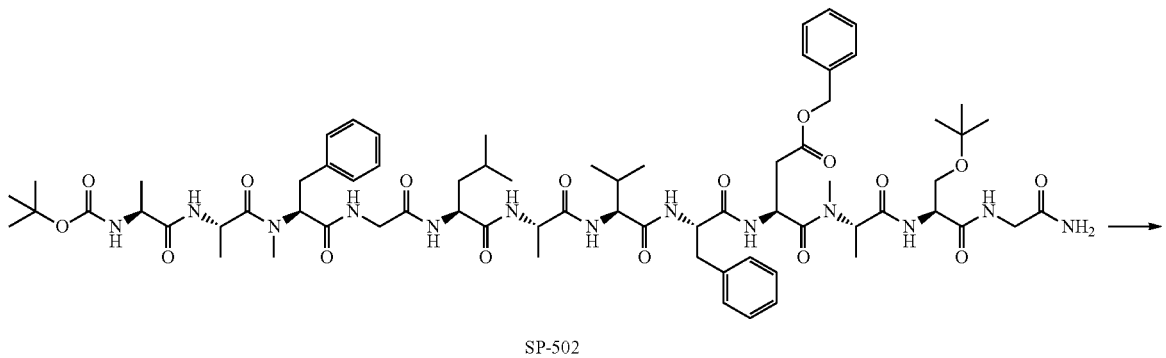

SP-502

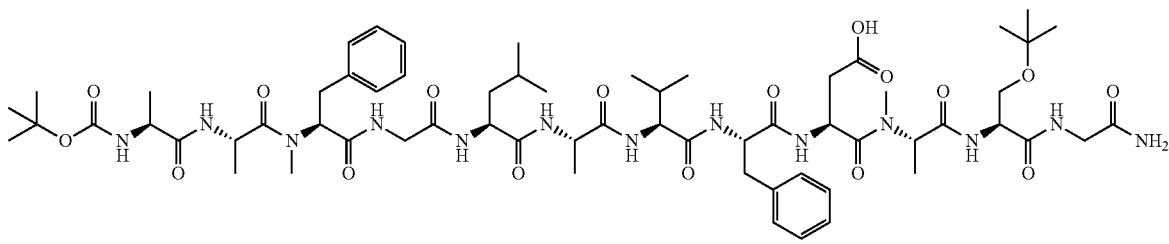

SP-501

Hydroxypalladium/carbon (250 mg, 50% wet w/w) was added to a solution of benzyl (6S,9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-12,27-dibenzyl-18-isobutyl-24-isopropyl-2,2,6,9,11,21-hexamethyl-4,7,10,13,16,19,22,25,28-nonaoxo-3-oxa-5,8,11,14,17,20,23,26,29-nonaazadotriacontan-32-oate synthesized according to a conventional method (Compound SP-502, Boc-Ala-Ala-MePhe-Gly-Leu-Ala-Val-Phe-Asp(OBn)-MeAla-Ser(tBu)-Gly-NH2 (SEQ ID NO: 332)) (749 mg, 0.536 mmol) in methanol (5 ml)-ethyl acetate (5 ml) under a nitrogen atmosphere, the atmosphere was replaced with hydrogen, and the mixture was then stirred at room temperature for 3.5 hours. The reaction solution was then filtered through celite, and the filtrate was concentrated under reduced pressure to afford the title compound (SP-501) (620 mg, 88%).

LCMS (ESI) m/z=1306.4 (M−H)−

Retention time: 0.74 min (analysis condition SQD FA05)

Synthesis of S-benzyl (6S,9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-12,27-dibenzyl-18-isobutyl-24-isopropyl-2,2,6,9,11,21-hexamethyl-4,7,10,13,16,19,22,25,28-nonaoxo-3-oxa-5,8,11,14,17,20,23,26,29-nonaazadotriacontane-32-thioate (Boc-Ala-Ala-MePhe-Gly-Leu-Ala-Val-Phe-Asp(SBn)-MeAia-Ser(tBu)-Gly-NH2) (Compound SP-503) (SEQ ID NO: 333)

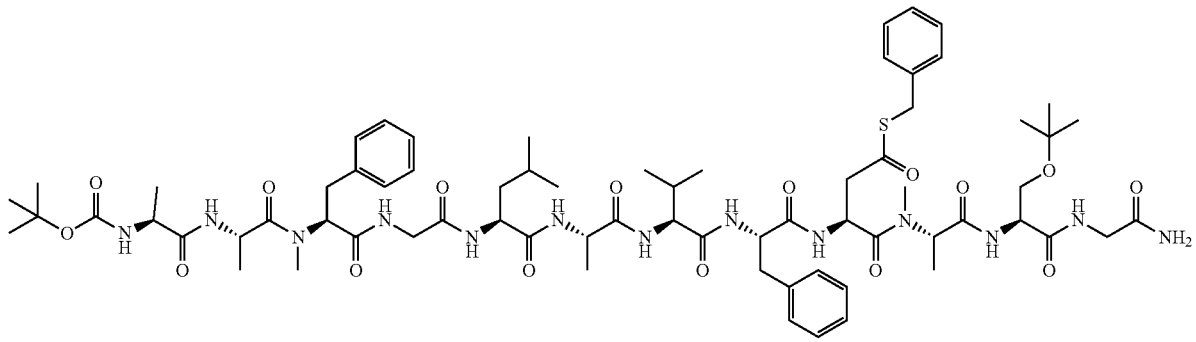 [SMILES: CC(C)C[C@H](NC(=O)CNC(=O)[C@H](Cc1ccccc1)N(C)C(=O)[C@H](C)NC(=O)[C@H](C)NC(=O)OC(C)(C)C)C(=O)N[C@@H](C)C(=O)N[C@H](C(=O)N[C@@H](Cc1ccccc1)C(=O)N[C@@H](CC(=O)SCc1ccccc1)C(=O)N(C)[C@@H](C)C(=O)N[C@@H](COC(C)(C)C)C(=O)NCC(N)=O)C(C)C]

The title compound (SP-503) (178.2 mg, 51%) was obtained in the same manner as in the synthesis of Compound P-146 using (6S,9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-12,27-dibenzyl-18-isobutyl-24-isopropyl-2,2,6,9,11,21-hexamethyl-4,7,10,13,16,19,22,25,28-nonaoxo-3-oxa-5,8,11,14,17,20,23,26,29-nonaazadotriacontan-32-oic acid (Compound SP-501) (325.5 mg, 0.249 mmol) as a starting material.
LCMS (ESI) m/z=1412.6 (M−H)−
Retention time: 0.87 min (analysis condition SQD FA05)

Synthesis of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-4,7,10,13,16,19,22,25-octaazaoctacosane-1-thioate (Ala-Ala-MePhe-Gly-Leu-Ala-Val-Phe-Asp(SBn)-MeAla-Ser-Gly-NH2) (Compound SP-504) (SEQ ID NO: 334)

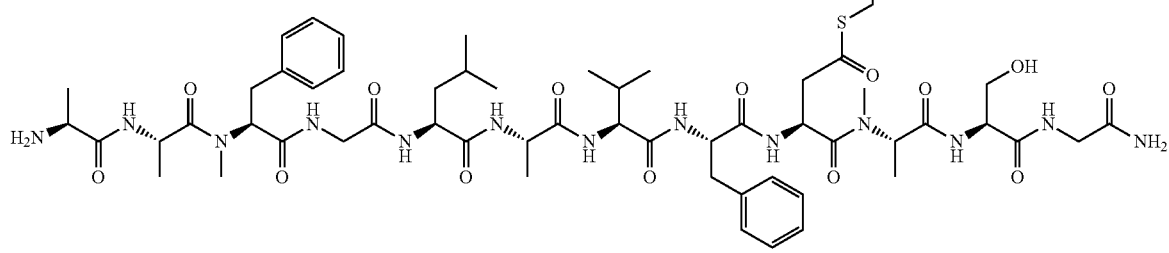

The title compound (SP-504) (47.3 mg, 73%) was obtained in the same manner as in the synthesis of Compound P-147 using S-benzyl (6S,9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-12,27-dibenzyl-18-isobutyl-24-isopropyl-2,2,6,9,11,21-hexamethyl-4,7,10,13,16,19,22,25,28-nonaoxo-3-oxa-5,8,11,14,17,20,23,26,29-nonaazadotriacontane-32-thioate (Compound SP-503) (72.9 mg, 0.052 mmol) as a starting material.
LCMS (ESI) m/z=1256.8 (M−H)−
Retention time: 0.58 min (analysis condition SQD FA05)

Synthesis of (6S,9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-6,12,27-tribenzyl-18-isobutyl-24-isopropyl-2,2,9,11,21-pentamethyl-4,7,10,13,16,19,22,25,28-nonaoxo-3-oxa-5,8,11,14,17,20,23,26,29-nonaazadotriacontan-32-oic Acid (Boc-Phe-Ala-MePhe-Gly-Leu-Ala-Val-Phe-Asp-MeAla-Ser(tBu)-Gly-NH2)) (Compound SP-505) (SEQ ID NO: 335)

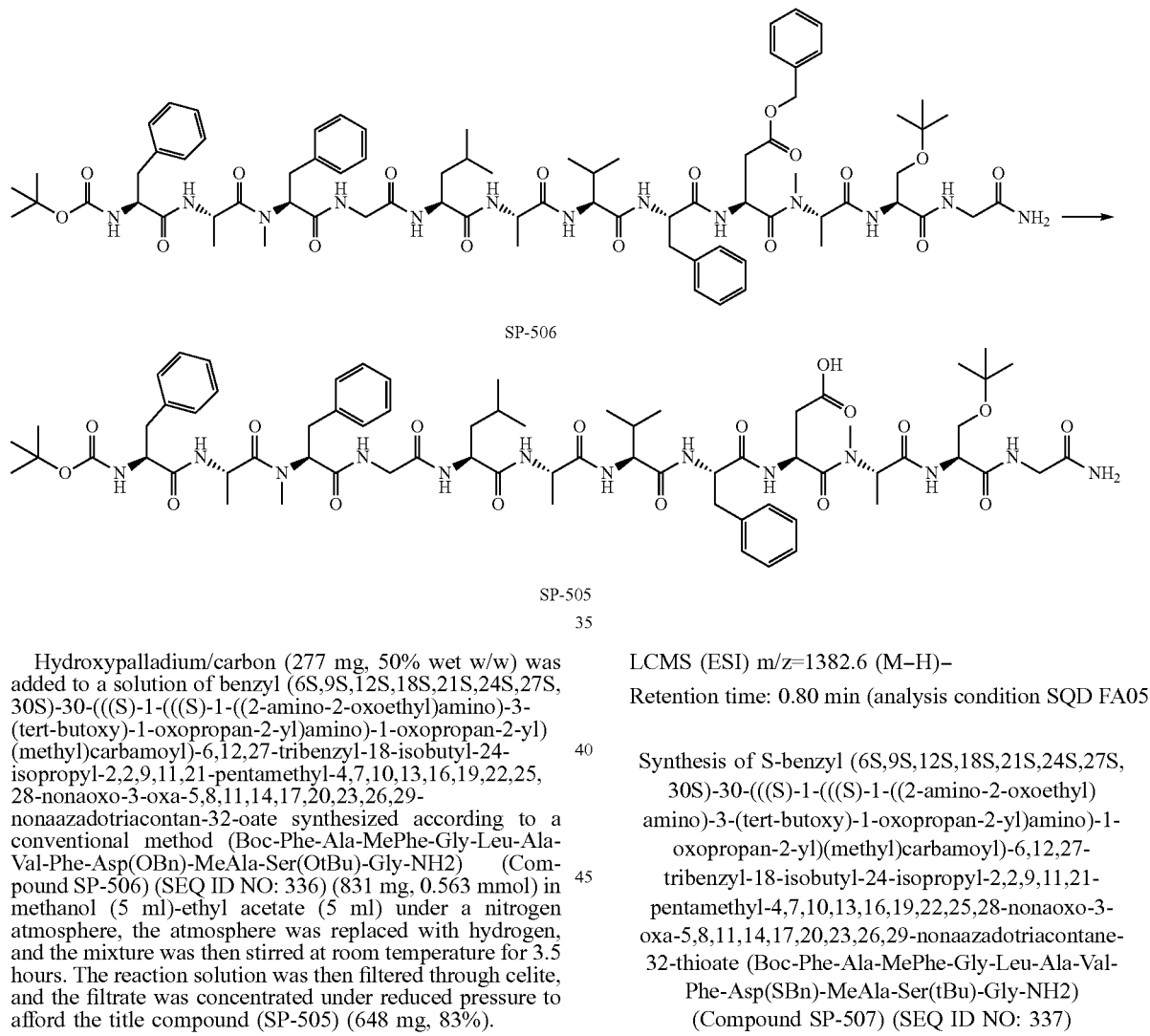

Hydroxypalladium/carbon (277 mg, 50% wet w/w) was added to a solution of benzyl (6S,9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-6,12,27-tribenzyl-18-isobutyl-24-isopropyl-2,2,9,11,21-pentamethyl-4,7,10,13,16,19,22,25,28-nonaoxo-3-oxa-5,8,11,14,17,20,23,26,29-nonaazadotriacontan-32-oate synthesized according to a conventional method (Boc-Phe-Ala-MePhe-Gly-Leu-Ala-Val-Phe-Asp(OBn)-MeAla-Ser(OtBu)-Gly-NH2) (Compound SP-506) (SEQ ID NO: 336) (831 mg, 0.563 mmol) in methanol (5 ml)-ethyl acetate (5 ml) under a nitrogen atmosphere, the atmosphere was replaced with hydrogen, and the mixture was then stirred at room temperature for 3.5 hours. The reaction solution was then filtered through celite, and the filtrate was concentrated under reduced pressure to afford the title compound (SP-505) (648 mg, 83%).

LCMS (ESI) m/z=1382.6 (M−H)−

Retention time: 0.80 min (analysis condition SQD FA05)

Synthesis of S-benzyl (6S,9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-6,12,27-tribenzyl-18-isobutyl-24-isopropyl-2,2,9,11,21-pentamethyl-4,7,10,13,16,19,22,25,28-nonaoxo-3-oxa-5,8,11,14,17,20,23,26,29-nonaazadotriacontane-32-thioate (Boc-Phe-Ala-MePhe-Gly-Leu-Ala-Val-Phe-Asp(SBn)-MeAla-Ser(tBu)-Gly-NH2) (Compound SP-507) (SEQ ID NO: 337)

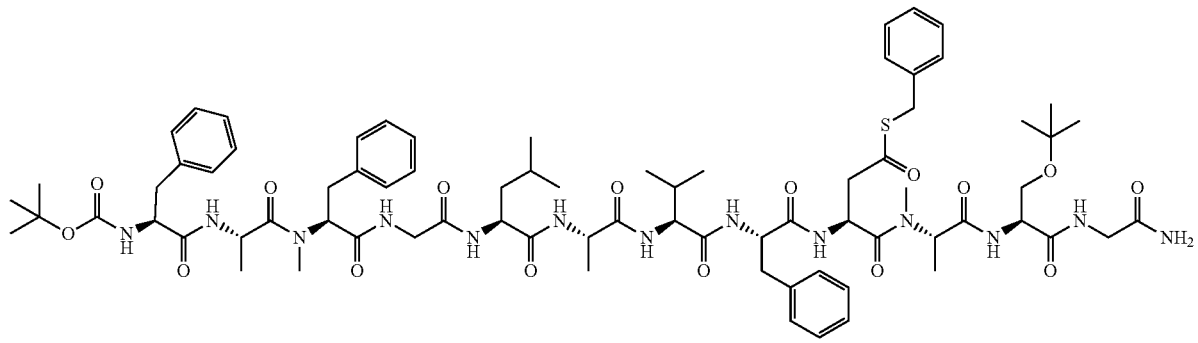 [SMILES: CC(C)C[C@H](NC(=O)CNC(=O)[C@H](Cc1ccccc1)N(C)C(=O)[C@H](C)NC(=O)[C@H](Cc1ccccc1)NC(=O)OC(C)(C)C)C(=O)N[C@@H](C)C(=O)N[C@H](C(=O)N[C@@H](Cc1ccccc1)C(=O)N[C@@H](CC(=O)SCc1ccccc1)C(=O)N(C)[C@@H](C)C(=O)N[C@@H](COC(C)(C)C)C(=O)NCC(N)=O)C(C)C]

The title compound (SP-507) (143.8 mg, 39%) was obtained in the same manner as in the synthesis of Compound P-146 using (6S,9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-6,12,27-tribenzyl-18-isobutyl-24-isopropyl-2,2,9,11,21-pentamethyl-4,7,10,13,16,19,22,25,28-nonaoxo-3-oxa-5,8,11,14,17,20,23,26,29-nonaazadotriacontan-32-oic acid (Compound SP-505) (344.5 mg, 0.249 mmol) as a starting material.

LCMS (ESI) m/z=1490.6 (M+H)+
Retention time: 0.93 min (analysis condition SQD FA05)

Synthesis of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate (Phe-Ala-MePhe-Gly-Leu-Ala-Val-Phe-Asp(SBn)-MeAla-Ser-Gly-NH2) (Compound SP-508) (SEQ ID NO: 338)

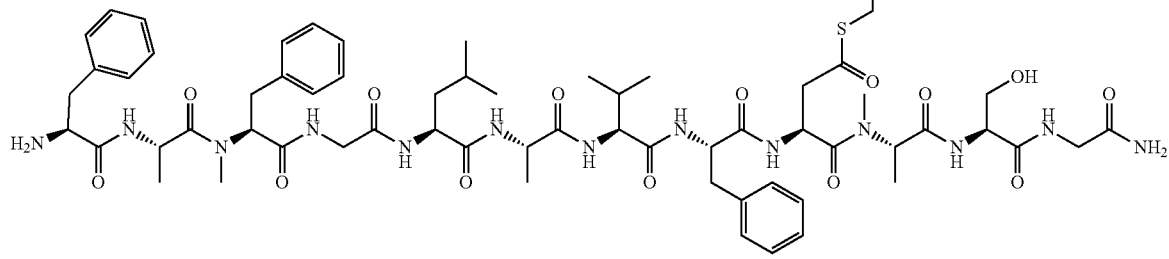

The title compound (SP-508) (56.1 mg, 87%) was obtained in the same manner as in the synthesis of Compound P-147 using S-benzyl (6S,9S,12S,18S,21S,24S,27S,30S)-30-(((S)-1-(((S)-1-((2-amino-2-oxoethyl)amino)-3-(tert-butoxy)-1-oxopropan-2-yl)amino)-1-oxopropan-2-yl)(methyl)carbamoyl)-6,12,27-tribenzyl-18-isobutyl-24-isopropyl-2,2,9,11,21-pentamethyl-4,7,10,13,16,19,22,25,28-nonaoxo-3-oxa-5,8,11,14,17,20,23,26,29-nonaazadotriacontane-32-thioate (Compound SP-507) (72.1 mg, 0.048 mmol) as a starting material.

LCMS (ESI) m/z=1332.7 (M−H)−
Retention time: 0.60 min (analysis condition SQD FA05)

1-1-2. Cyclization Model Reaction Examples

Reaction examples where the N-terminal is Gly will be illustrated below.
(Compound P-136)

Synthesis of (5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-8,23-dibenzyl-14-isobutyl-20-isopropyl-N,5,7,13,17-pentamethyl-3,6,9,12,15,18,21,24,28-nonaoxo-1,4,7,10,13,16,19,22,25-nonaazacyclooctacosane-26-carboxamide

Figure 36:
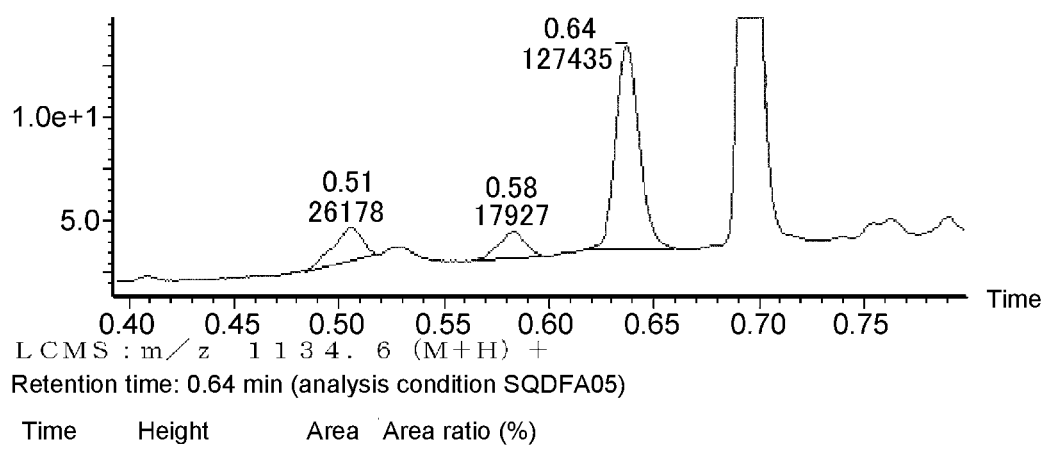
FIG. 36 is a diagram showing LCMS analysis results of a reaction solution containing compound P-136 produced by cyclization reaction.

First Example 4-(Trifluoromethyl)benzenethiol (0.018 g, 0.10 mmol) and triethylamine (10.1 mg, 0.10 mmol) were dissolved in a 100 mM aqueous disodium hydrogenphosphate solution (80 µL) and NMP (10 µL). A solution of S-benzyl (4S,7S,13S, 16S,19S,22S,25S)-1-amino-25-(((S)-1-(((S)-1-((2-amino-2-oxoethyl)amino)-3-hydroxy-1-oxopropan-2-yl)amino)-1-oxopropan-2-yl)(methyl)carbamoyl)-7,22-dibenzyl-13-isobutyl-19-isopropyl-4,6,12,16-tetramethyl-2,5,8,11,14,17, 20,23-octaoxo-3,6,9,12,15,18,21,24-octaazaheptacosane-27-thioate (Compound P-147) in NMP (10 mM, 10 µl, 0.10 µmol) was added to this solution, and the mixture was stirred at room temperature for 5 hours. The reaction solution was analyzed by LCMS to confirm that the title compound was produced. The production ratio of the title compound, the starting material (retention time: 0.58 min, analysis condition SQDFA05) and the hydrolysate obtained by hydrolysis of the thioester of Asp (retention time: 0.51 min, analysis condition SQDFA05) was about 74:11:15 based on the UV area ratio by LCMS. The result is shown in FIG. 36.

LCMS: m/z 1134.6 (M+H)+

Retention time: 0.64 min (analysis condition SQDFA05)

Second Example

Figure 37:
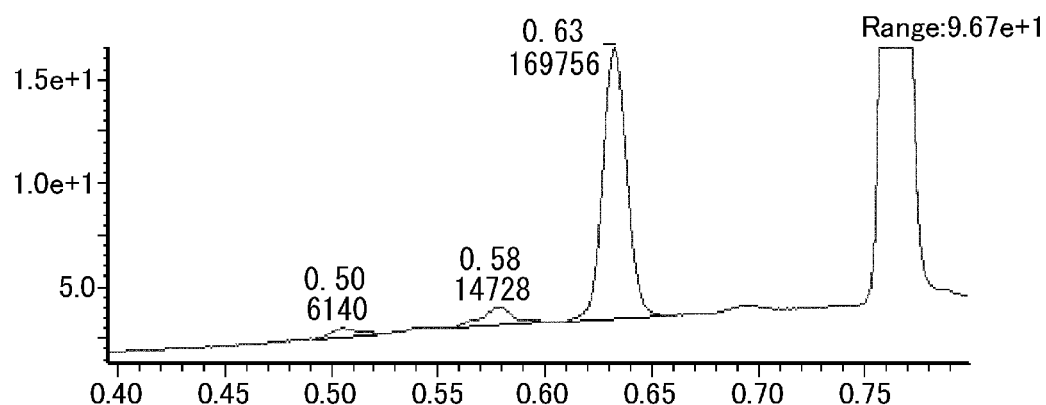
FIG. 37 is a diagram showing LCMS analysis results of a reaction solution containing compound P-136 produced by cyclization reaction.

Benzenethiol (0.110 mg, 0.001 mmol) and triethylamine (0.202 mg, 0.002 mmol) were dissolved in a 100 mM aqueous disodium hydrogenphosphate solution (80 µL) and NMP (10 µL). A solution of S-benzyl (4S,7S,13S,16S,19S, 22S,25S)-1-amino-25-(((S)-1-(((S)-1-((2-amino-2-oxoethyl)amino)-3-hydroxy-1-oxopropan-2-yl)amino)-1-oxopropan-2-yl)(methyl)carbamoyl)-7,22-dibenzyl-13-isobutyl-19-isopropyl-4,6,12,16-tetramethyl-2,5,8,11,14,17, 20,23-octaoxo-3,6,9,12,15,18,21,24-octaazaheptacosane-27-thioate (Compound P-147) in NMP (10 mM, 10 µL, 0.10 µmol) was added to this solution, and the mixture was stirred at room temperature for 8 hours. The reaction solution was analyzed by LCMS to confirm that the title compound was produced. The production ratio of the title compound, the starting material (retention time: 0.58 min, analysis condition SQDFA05) and the hydrolysate obtained by hydrolysis of the thioester of Asp (retention time: 0.50 min, analysis condition SQDFA05) was about 89:8:3 based on the UV area ratio by LCMS. The result is shown in FIG. 37.

LCMS: m/z 1134.6 (M+H)+

Retention time: 0.63 min (analysis condition SQDFA05)

Reaction examples where the N-terminal is Ala will be illustrated below.

(Compound P-137)

Synthesis of (2R,5S,8S,11S,14S,20S,23S,26S,29S)-14,26-dibenzyl-11-((R)-1-hydroxyethyl)-8,20-diisobutyl-5,23-diisopropyl-N,2,7,13,19,22-hexamethyl-3,6,9,12,15,18,21,24,27,31-decaoxo-N—((S)-1-oxo-1-(((S)-1-oxo-1-(piperidin-1-yl)propan-2-yl)amino)-3-phenylpropan-2-yl)-1,4,7,10,13,16,19,22, 25,28-decaazacyclohentriacontane-29-carboxamide

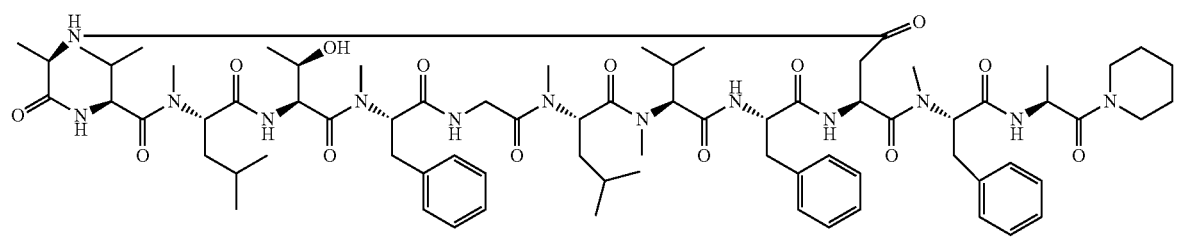 [SMILES: CC(C)C[C@H]1C(=O)N(C)[C@@H](C(C)C)C(=O)N[C@@H](Cc2ccccc2)C(=O)N[C@H](C(=O)N(C)[C@@H](Cc2ccccc2)C(=O)N[C@@H](C)C(=O)N2CCCCC2)CC(=O)N[C@H](C)C(=O)N[C@@H](C(C)C)C(=O)N(C)[C@@H](CC(C)C)C(=O)N[C@@H]([C@@H](C)O)C(=O)N(C)[C@@H](Cc2ccccc2)C(=O)NCC(=O)N1C]

First Example

Figure 38:
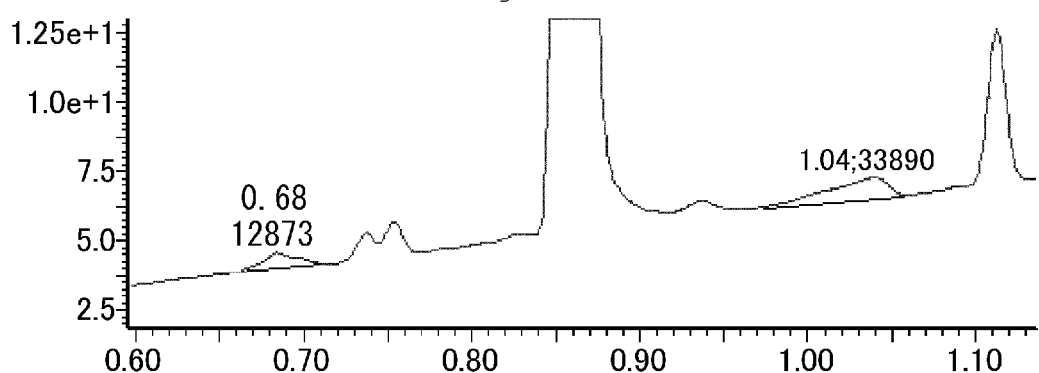
FIG. 38 is a diagram showing LCMS analysis results of a reaction solution containing compound P-137 produced by cyclization reaction.

A solution of 4-(trifluoromethyl)benzenethiol (8.91 mg, 0.05 mmol) and triethylamine (5.06 mg, 0.05 mmol) in water (25 µL) and a solution of S-benzyl (3S,6S,9S,12S, 18S,21S,24S,27S,30S)-30-amino-6,18-dibenzyl-21-((R)-1-hydroxyethyl)-12,24-diisobutyl-9,27-diisopropyl-10,13,19, 25-tetramethyl-3-(methyl((S)-1-oxo-1-(((S)-1-oxo-1-(piperidin-1-yl)propan-2-yl)amino)-3-phenylpropan-2-yl) carbamoyl)-5,8,11,14,17,20,23,26,29-nonaoxo-4,7,10,13, 16,19,22,25,28-nonaazahentriacontane-1-thioate (Compound P-135) in NMP (5 mM, 20 µL, 0.1 µmol) were mixed, water (25 µL) and NMP (30 µL) were further added, and the mixture was stirred at 50° C. overnight. LCMS measurement confirmed that the starting material disappeared and the title compound was produced. The production ratio of the title compound and the hydrolysate obtained by hydrolysis of the thioester of Asp (retention time: 0.68 min, analysis condition SQDFA05) was about 72:28 based on the UV area ratio by LCMS. The result is shown in FIG. 38.

LCMS: m/z 1417 (M–H)–

Retention time: 1.04 min (analysis condition SQDFA05)

Second Example

A 1 M aqueous tris(2-carboxyethyl)phosphine (TCEP) solution (5 ul) was added to a solution of 2-(ethyldisulfanyl)-6-methylphenyl (3S,6S,9S,12S,18S,21S,24S,27S,30S)-30-amino-6,18-dibenzyl-21-((R)-1-hydroxyethyl)-12,24-diisobutyl-9,27-diisopropyl-10,13,19,25-tetramethyl-3-(methyl((S)-1-oxo-1-(((S)-1-oxo-1-(piperidin-1-yl)propan- 2-yl)amino)-3-phenylpropan-2-yl)carbamoyl)-5,8,11,14,17,
20,23,26,29-nonaoxo-4,7,10,13,16,19,22,25,28-
nonaazahentriacontan-1-oate (0.162 mg, 0.1 umol)
(Compound P-139) and 1-hydroxypyrrolidine-2,5-dione
(0.575 mg, 5 umol) in a 1:1 mixed solution of DMF-400 mM
phosphate buffer (pH 8.5) (95 ul), and the mixture was
stirred at room temperature for 30 minutes, after which the
reaction was observed by LCMS. As a result, the precursor
of cyclic peptide completely disappeared, the title compound P-137 and the hydrolysate P-140 were observed at 3:1
(LCMS: UV area ratio).

LCMS (ESI) m/z=1417.2 (M–H)–
Retention time: 1.04 min (analysis condition SQDFA05)

Hydrolysate P-140

(3S,6S,9S,12S,18S,21S,24S,27S,30S)-30-amino-6,
18-dibenzyl-21-((R)-1-hydroxyethyl)-12,24-di-
isobutyl-9,27-diisopropyl-10,13,19,25-tetramethyl-3-
(methyl((S)-1-oxo-1-(((S)-1-oxo-1-(piperidin-1-yl)
propan-2-yl)amino)-3-phenylpropan-2-yl)
carbamoyl)-5,8,11,14,17,20,23,26,29-nonaoxo-4,7,
10,13,16,19,22,25,28-nonaazahentriacontan-1-oic
Acid

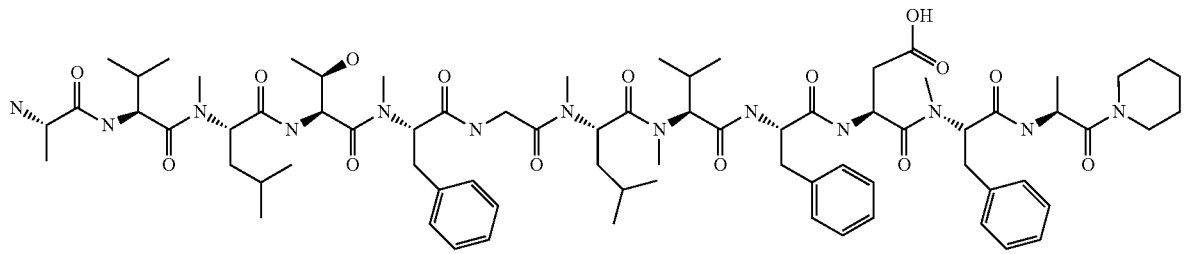

LCMS (ESI) m/z=1435.3 (M–H)–
Retention time: 0.67 min (analysis condition SQDFA05)

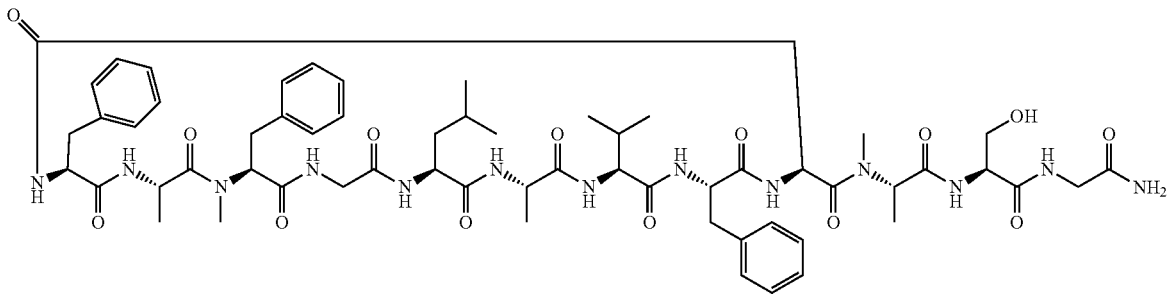 [SMILES: CC(C)C[C@@H]1NC(=O)CNC(=O)[C@H](Cc2ccccc2)N(C)C(=O)[C@H](C)NC(=O)[C@H](Cc2ccccc2)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

Reaction examples where the N-terminal is Phe will be illustrated below.

Synthesis of (2S,5S,8S,14S,17S,20S,23S,26S)—
N—((S)-1-(((S)-1-((2-amino-2-oxoethyl)amino)-3-
hydroxy-1-oxopropan-2-yl)amino)-1-oxopropan-2-
yl)-2,8,23-tribenzyl-14-isobutyl-20-isopropyl-N,5,7,
17-tetramethyl-3,6,9,12,15,18,21,24,28-nonaoxo-1,4,
7,10,13,16,19,22,25-nonaazacyclooctacosane-26-
carboxamide (Compound SP-509)

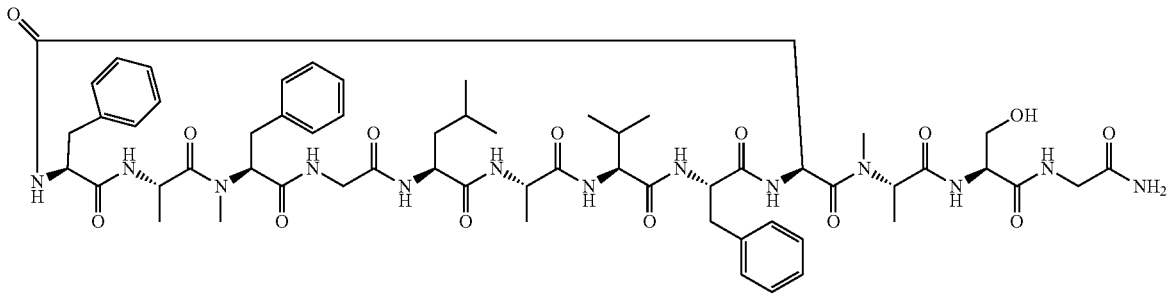 [SMILES: CC(C)C[C@@H]1NC(=O)CNC(=O)[C@H](Cc2ccccc2)N(C)C(=O)[C@H](C)NC(=O)[C@H](Cc2ccccc2)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

4-(Trifluoromethyl)benzenethiol (13.6 ul, 0.10 mmol) and triethylamine (13.9 ul, 0.10 mmol) were dissolved in a 100 mM aqueous disodium hydrogenphosphate solution (80 μL) and NMP (10 μL). A solution of S-benzyl (3S,6S,9S,12S, 15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20, 23,26-octaoxo-28-phenyl-4,7,10,13,16,19,22,25-octaazaoctacosane-1-thioate (Compound SP-508) in NMP (10 mM, 10 μL, 0.10 μmol) and a solution of phthalic acid in acetonitrile as internal standard (50 mM, 1.0 μl) were added to this solution, and the mixture was stirred at 30° C.

LCMS (ESI) m/z=1228.5 (M+H)+
Retention time: 0.89 min (analysis condition SMD method 1)

First Cyclization Reaction Example in PureSystem (Translation Solution) Using a Model Peptide Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-8,23-dibenzyl-14-isobutyl-20-isopropyl-N,2,5,7, 17-pentamethyl-3,6,9,12,15,18,21,24,28-nonaoxo-1, 4,7,10,13,16,19,22,25-nonaazacyclooctacosane-26-carboxamide (Compound SP-511)

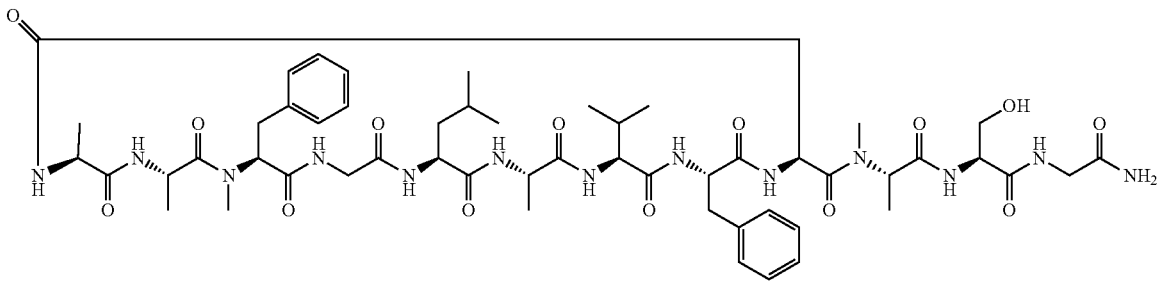

for 3 hours. The pH at the start of the reaction was 9.7. The reaction solution was analyzed by LCMS to confirm that the title compound was produced. After stirring for 3 hours, the conversion rate was 90% based on the area ratio to the internal standard and the starting material, and the production ratio of the title compound (SP-509) and the hydrolysate (Compound SP-510) was about 3:2 based on the UV area ratio by LCMS.
Title Compound
LCMS (ESI) m/z=1210.4 (M+H)+
Retention time: 1.04 min (analysis condition SMD method 1)
Hydrolysate (Compound SP-510)

(3S,6S,9S,12S,15S,21S,24S,27S)-27-amino-3-(((S)-1-(((S)-1-((2-amino-2-oxoethyl)amino)-3-hydroxyl-oxopropan-2-yl)amino)-1-oxopropan-2-yl)(methyl) carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosan-1-oic Acid 4-(Trifluoromethyl)benzenethiol (6.8 μL, 0.050 mmol) and triethylamine (7.0 μl, 0.050 mmol) were dissolved in water (8.2 μl) to prepare a thiol solution.
A solution of 4-propylbenzoic acid as internal standard in NMP (11 mM, 2.25 μl) was added to a solution of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8, 11,14,17,20,23,26-octaoxo-4,7,10,13,16,19,22,25-octaazaoctacosane-1-thioate (Compound SP-504) in NMP (10 mM, 5.0 μl, 0.050 μmol). Next, a translation buffer (6.25 μL), PURESYSTEM® classic II Sol. B (BioComber, product No. PURE2048C) (10 μl) and 20 natural amino acid solutions (each 5 mM, 2.5 μl) were added.
The ingredients of the translation buffer are 8 mM GTP, 8 mM ATP, 160 mM creatine phosphate, 400 mM HEPES-KOH, pH 7.6, 800 mM potassium acetate, 48 mM magnesium acetate, 16 mM spermidine, 8 mM dithiothreitol, 0.8 mM 10-HCO—H4 folate and 12 mg/ml E. coli MRE600 (RNase negative)-derived tRNA (Roche). An aqueous tris (2-carboxyethyl)phosphine solution (pH=7.5, 1.25 M, 2.0

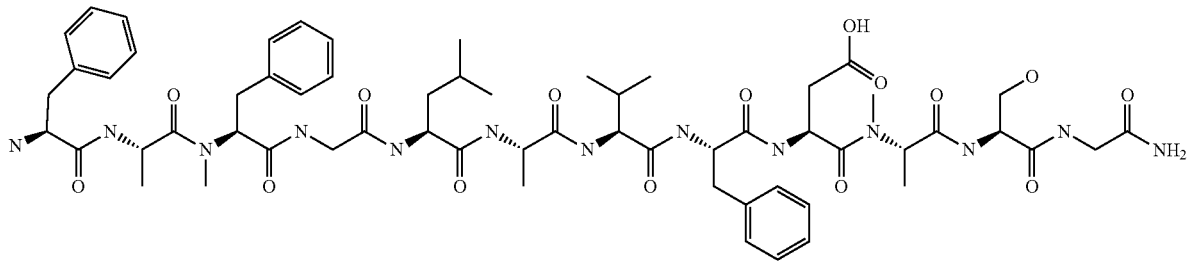 [SMILES: CC(C)C[C@H](NC(=O)CNC(=O)[C@H](Cc1ccccc1)N(C)C(=O)[C@H](C)NC(=O)[C@@H](N)Cc1ccccc1)C(=O)N[C@@H](C)C(=O)N[C@H](C(=O)N[C@@H](Cc1ccccc1)C(=O)N[C@@H](CC(=O)O)C(=O)N(C)[C@@H](C)C(=O)N[C@@H](CO)C(=O)NCC(N)=O)C(C)C]

μl) and the thiol solution prepared above were added thereto. The pH of the reaction solution at this time was 7.8.

The reaction solution was stirred at 30° C. for 20 hours and then analyzed by LC/MS to confirm that the title compound was produced. The pH of the reaction solution after stirring for 20 hours was 9.4. The production ratio of the title compound (SP-511) and the hydrolysate (Compound SP-512) was 1:1.6 based on the UV area ratio.

Title Compound

LCMS (ESI) m/z=1134.4 (M+H)+

Retention time: 0.64 min (analysis condition SQDFA05)

Hydrolysate (Compound SP-512)

(3S,6S,9S,12S,15S,21S,24S,27S)-27-amino-3-(((S)-1-(((S)-1-((2-amino-2-oxoethyl)amino)-3-hydroxyl-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-4,7,10,13,16,19,22,25-octaazaoctacosan-1-oic Acid

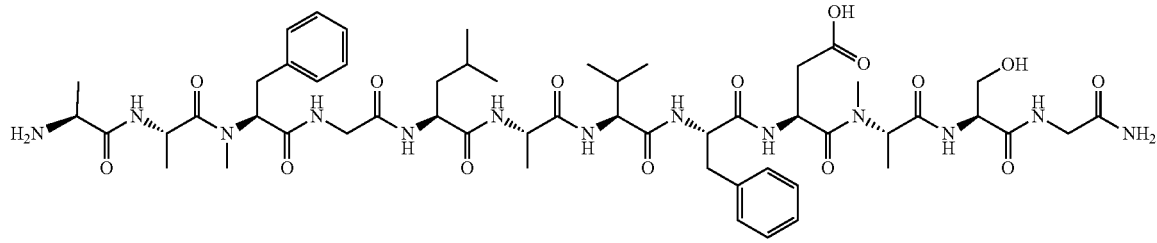 [SMILES: CC(C)C[C@H](NC(=O)CNC(=O)[C@H](Cc1ccccc1)N(C)C(=O)[C@H](C)NC(=O)[C@H](C)N)C(=O)N[C@@H](C)C(=O)N[C@H](C(=O)N[C@@H](Cc1ccccc1)C(=O)N[C@@H](CC(=O)O)C(=O)N(C)[C@@H](C)C(=O)N[C@@H](CO)C(=O)NCC(N)=O)C(C)C]

LCMS (ESI) m/z=1152.5 (M+H)+

Retention time: 0.48 min (analysis condition SQDFA05)

As illustrated above, it was revealed that cyclization reaction proceeds in water using a method of further activating a translatable thioester not only at Cys (having a reaction auxiliary group) and Gly (not having a substituent at the α-position and being most reactive) but also at Ala and Phe. Also, such reaction could be confirmed to proceed in translation solutions.

1-1-3. Synthesis of pdCpA-AA Having an Active Ester to be Cyclized

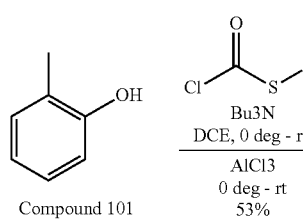

Compound 101

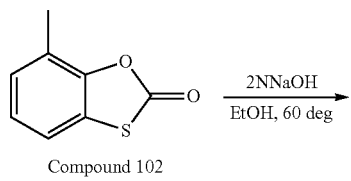

Compound 102

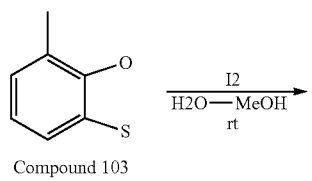

Compound 103

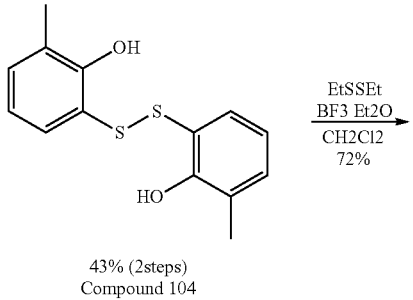

43% (2steps)
Compound 104

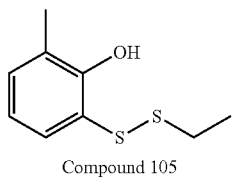

Compound 105

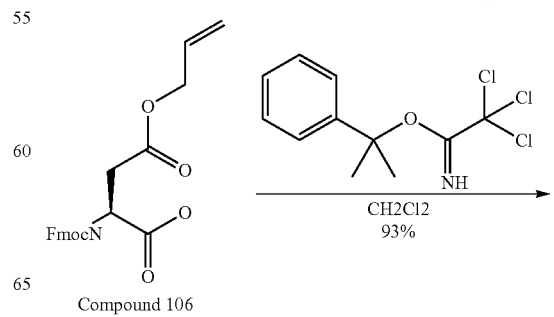

Compound 106

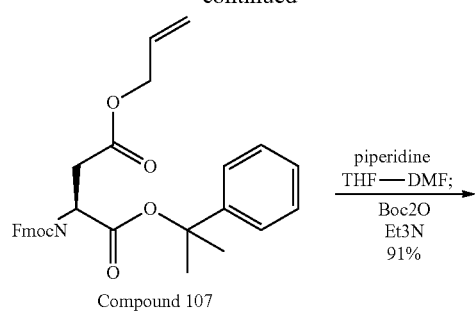
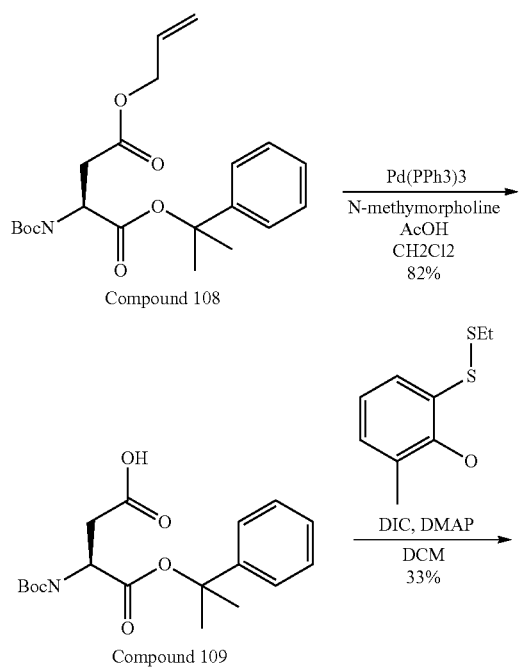
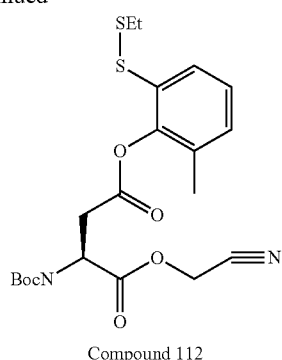
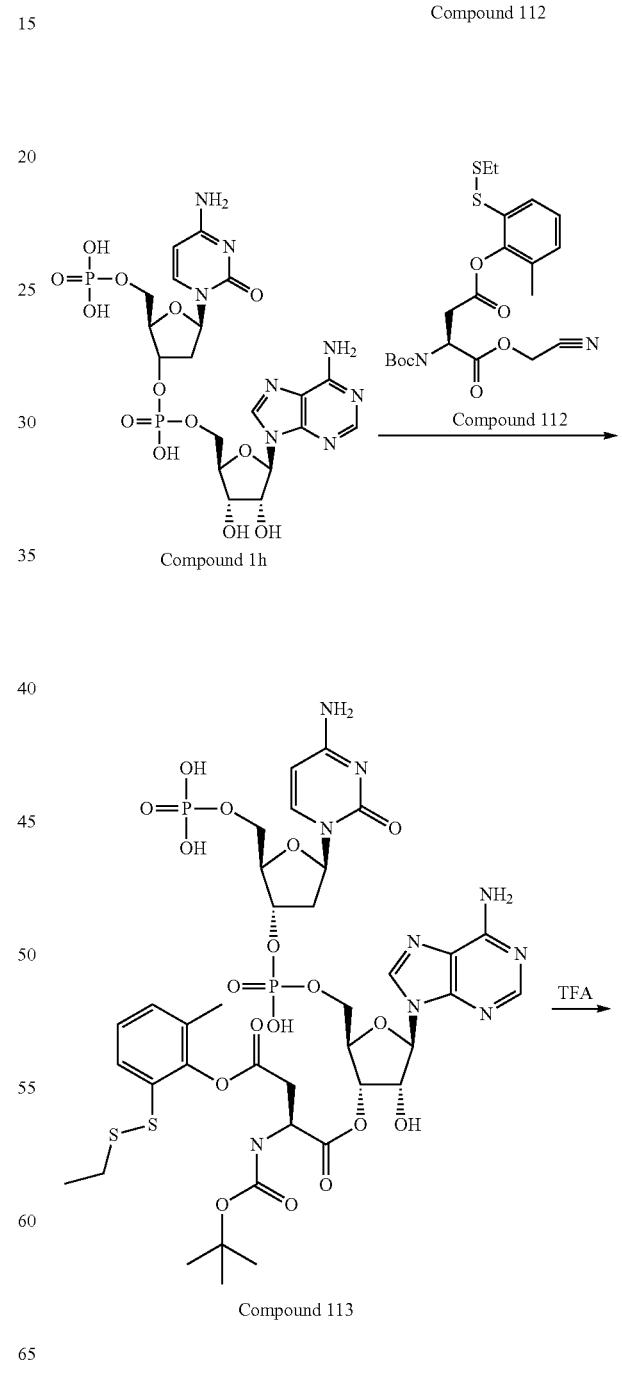

-continued

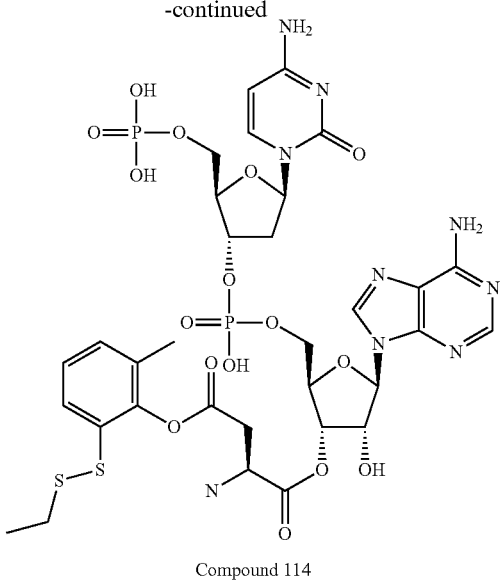

Compound 114

Synthesis of 7-methylbenzo[d][1,3]oxathiol-2-one (Compound 102)

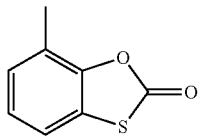

Chlorocarbonylsulfenyl chloride (30.5 mmol, 2.58 ml) was added to a solution of o-cresol (Compound 101) (27.7 mmol, 3.00 g) and tributylamine (30.5 mmol, 7.35 ml) in dichloroethane (48 mL) at 0° C., and the mixture was stirred at room temperature for 2 hours. Aluminum chloride (66.6 mmol, 8.88 g) was then added to the reaction mixture at 0° C., and the mixture was stirred at room temperature overnight. Water (10 ml) was then added to the reaction mixture at 0° C., after which the mixture was extracted with ethyl acetate and the organic layer was washed with water. The organic extract was then dried over sodium sulfate. Following concentration under reduced pressure, the resulting residue was purified by reverse-phase silica gel column chromatography (0.1% aqueous formic acid solution/0.1% formic acid-acetonitrile solution=100/0→30/70) to afford 7-methylbenzo[d][1,3]oxathiol-2-one (Compound 102) (2.46 g, 53%).

LCMS (ESI) m/z=167 (M+H)+
Retention time: 0.81 min (analysis condition SQDFA05)

Synthesis of 2-Mercapto-6-Methylphenol (Compound 103)

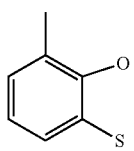

A 2 N aqueous sodium hydroxide solution (15 ml) was added to a solution of 7-methylbenzo[d][1,3]oxathiol-2-one (Compound 102) (2.34 g, 14.44 mmol) in ethanol (15 ml), and the mixture was stirred at 60° C. for 1 hour. The reaction mixture was then quenched by adding concentrated hydrochloric acid thereto at 0° C., after which the mixture was extracted with ethyl acetate and the organic layer was washed with water. The organic extract was then dried over sodium sulfate to afford 2-mercapto-6-methylphenol (Compound 103) (1.90 g). This compound was used in the next step without further purification.

LCMS (ESI) m/z=139 (M−H)−
Retention time: 0.70 min (analysis condition SQDFA05)

Synthesis of 6,6'-Disulfanediylbis(2-Methylphenol) (Compound 104)

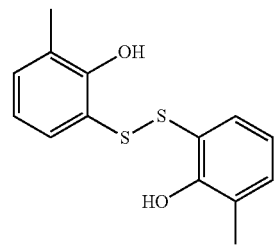 [SMILES: Cc1cccc(SSc2cccc(C)c2O)c1O]

A solution of I2 (1.717 g, 6.76 mmol) in methanol (7 ml) was added to a biphase solution of 2-mercapto-6-methylphenol obtained above (Compound 103) (1.90 g) in water (10 ml), and the mixture was stirred at room temperature for 10 minutes. The reaction mixture was diluted with ethyl acetate, and the organic layer was washed with a saturated aqueous Na2S2O3 solution and water. The organic extract was then dried over sodium sulfate. Following concentration under reduced pressure, the resulting residue was purified by silica gel column chromatography (hexane/ethyl acetate=100/0→92/8) to afford 6,6'-disulfanediylbis(2-methylphenol) (Compound 104) (1.61 g, 43% (two steps)).

LCMS (ESI) m/z=277 (M−H)−
Retention time: 0.95 min (analysis condition SQDFA05)

Synthesis of 2-(ethyldisulfanyl)-6-methyl Phenol (Compound 105)

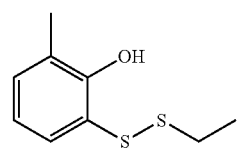

Diethyl disulfide (14.24 ml, 116 mmol) and BF3·OEt2 (14.66 mml, 16.42 mmol) were added to a solution of 6,6'-disulfanediylbis(2-methylphenol) (Compound 104) (1.61 g, 5.78 mmol) in dichloromethane (30 ml), and the mixture was stirred at room temperature for 5 hours. The reaction mixture was then quenched by slowly adding a saturated NaHCO3 solution dropwise thereto at 0° C., after which the mixture was extracted with ethyl acetate and the organic layer was washed with water. The organic extract was then dried over sodium sulfate and concentrated. The resulting residue was purified by silica gel column chromatography (hexane/ethyl acetate=100/0→90/10) to afford 2-(ethyldisulfanyl)-6-methylphenol (Compound 105) (1.67 g, 72%).

LCMS (ESI) m/z=199 (M−H)−
Retention time: 0.92 min (analysis condition SQDFA05)

Synthesis of 4-allyl 1-(2-phenylpropan-2-yl) (S)-2-((((9H-fluoren-9-yl)methoxy)carbonyl)amino)succinate (Compound 107)

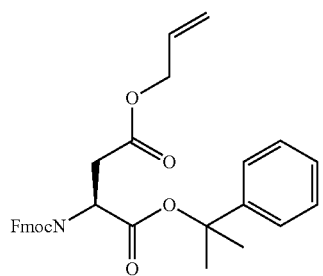

2-Phenylpropan-2-yl 2,2,2-trichloroacetimidate separately synthesized by a conventional method (2.17 g, 7.74 mmol) was added to a solution of (S)-2-((((9H-fluoren-9-yl)methoxy)carbonyl)amino)-4-(allyloxy)-4-oxobutanoic acid (Compound 106) (1.80 g, 4.55 mmol) in dichloromethane (40 ml), and the mixture was stirred at room temperature for 1 hour. The reaction mixture was then concentrated under reduced pressure. The resulting residue was purified by silica gel column chromatography (hexane/ethyl acetate=100/0→65/35) to afford 4-allyl 1-(2-phenylpropan-2-yl) (S)-2-((((9H-fluoren-9-yl)methoxy)carbonyl)amino)succinate (Compound 107) (2.17 g, 93%).

LC retention time: 1.12 min (analysis condition SQDAA05)
$^1$H-NMR (Varian 400-MR, 400 MHz, CDCl$_3$) δ ppm 7.76 (2H, d, 7.6 Hz), 7.49 (2H, d, 7.2 Hz), 7.41-7.24. (9H, m), 5.90 (1H, m) 5.77 (1H, d, 8.4 Hz), 5.29 (2H, m), 4.62 (3H, m), 4.37 (2H, m), 4.21 (1H, t, 6.8 Hz), 3.08 (1H, dd, 17.2, 4.4 Hz), 2.90 (1H, dd, 17.2, 4.8 Hz), 1.80 (3H, s), 1.78 (3H, s)

Synthesis of 4-allyl 1-(2-phenylpropan-2-yl) (S)-2-((tert-butoxycarbonyl)amino)succinate (Compound 108)

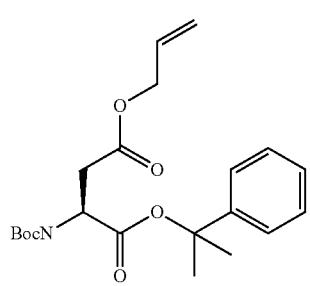

Piperidine (0.297 ml, 3.00 mmol) was added to a solution of 4-allyl 1-(2-phenylpropan-2-yl) (S)-2-((((9H-fluoren-9-yl)methoxy)carbonyl)amino)succinate (Compound 107) (1.03 g, 2.00 mmol) in THF (6 ml)-DMF (1.5 ml), and the mixture was stirred at room temperature for 3.5 hours.

Di-tert-butyl dicarbonate (1.31 g, 6.00 mmol) and triethylamine (0.837 ml, 6 mmol) were then added to the reaction mixture, which was stirred at room temperature for 15 minutes. The reaction mixture was then concentrated under reduced pressure. The resulting residue was purified by reverse-phase silica gel column chromatography (10 mM aqueous ammonium acetate solution/methanol=70/30→0/100) to afford 4-allyl 1-(2-phenylpropan-2-yl) (S)-2-((tert-butoxycarbonyl)amino)succinate (Compound 108) (710 mg, 91%).

LCMS (ESI) m/z=390 (M−H)−
Retention time: 0.63 min (analysis condition SQDAA50)

Synthesis of (S)-3-((tert-butoxycarbonyl)amino)-4-oxo-4-((2-phenylpropan-2-yl)oxy)butanoic Acid (Compound 109)

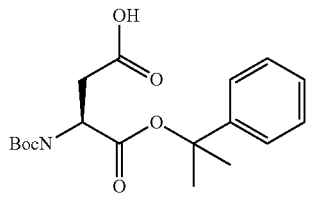

Pd(Ph3p)4 (210 mg, 0.181 mmol) was added to a solution of 4-allyl 1-(2-phenylpropan-2-yl) (S)-2-((tert-butoxycarbonyl)amino)succinate (Compound 108) (710 mg, 1.81 mmol) in dichloromethane (20 ml)-acetic acid (1.08 ml)-N-methylmorpholine (0.541 ml), and the mixture was stirred at room temperature for 3.5 hours. The reaction mixture was then concentrated under reduced pressure. The resulting residue was purified by reverse-phase silica gel column chromatography (10 mM aqueous ammonium acetate solution/methanol=100/0→30/70) to afford (S)-3-((tert-butoxycarbonyl)amino)-4-oxo-4-((2-phenylpropan-2-yl)oxy)butanoic acid (Compound 109) (525 mg, 82%).

LCMS (ESI) m/z=350 (M−H)−
Retention time: 0.80 min (analysis condition SQDAA05)

Synthesis of 4-(2-(ethyldisulfanyl)-6-methylphenyl) 1-(2-phenylpropan-2-yl) (S)-2-((tert-butoxycarbonyl)amino)succinate (Compound 110)

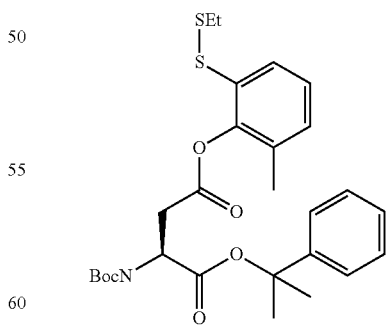

2-(ethyldisulfanyl)-6-methylphenol (Compound 105) (423 mg, 2.11 mmol), N,N'-diisopropylcarbodiimide (0.329 ml, 2.11 mmol) and N,N-dimethylpyridin-4-amine (34.4 mg, 0.282 mmol) were added to a solution of (S)-3-((tert-butoxycarbonyl)amino)-4-oxo-4-((2-phenylpropan-2-yl)

oxy)butanoic acid (Compound 109) (495 mg, 1.41 mmol) in dichloromethane (7 ml), and the mixture was stirred at room temperature for 1 hour. The reaction solution was then purified by reverse-phase silica gel column chromatography (10 mM aqueous ammonium acetate solution/methanol=70/30→0/100) to afford 4-(2-(ethyldisulfanyl)-6-methylphenyl) 1-(2-phenylpropan-2-yl) (S)-2-((tert-butoxycarbonyl)amino)succinate (Compound 110) (249 mg, 33%).

LCMS (ESI) m/z=532 (M–H)–

Retention time: 1.15 min (analysis condition SQDAA05)

Synthesis of 1-(cyanomethyl) 4-(2-(ethyldisulfanyl)-6-methylphenyl) (S)-2-((tert-butoxycarbonyl)amino)succinate (Compound 112)

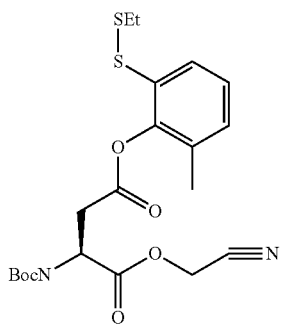

Trifluoroacetic acid (0.040 ml, 0.519 mmol) was added to a solution of 4-(2-(ethyldisulfanyl)-6-methylphenyl) 1-(2-phenylpropan-2-yl) (S)-2-((tert-butoxycarbonyl)amino)succinate (Compound 110) (240 mg, 0.450 mmol) in dichloromethane (4 ml), and the mixture was stirred at room temperature for 1.5 hours. Trifluoroacetic acid (0.040 ml, 0.519 mmol) was further added and the mixture was stirred at room temperature for 1.5 hours. The reaction solution was then concentrated under reduced pressure. DIPEA (0.259 ml, 1.49 mmol) was added to a solution of the resulting residue in bromoacetonitrile (4.70 ml), and the mixture was stirred at room temperature for 10 minutes. The reaction solution was purified by silica gel column chromatography (hexane/ethyl acetate=100/0→50/50) to afford 1-(cyanomethyl) 4-(2-(ethyldisulfanyl)-6-methylphenyl) (S)-2-((tert-butoxycarbonyl)amino)succinate (Compound 112) (151 mg, 74%).

LCMS (ESI) m/z=453 (M–H)–

Retention time: 1.04 min (analysis condition SQDAA05)

Synthesis of 1-((2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl) 4-(2-(ethyldisulfanyl)-6-methylphenyl) (2S)-2-aminosuccinate (Compound 114)

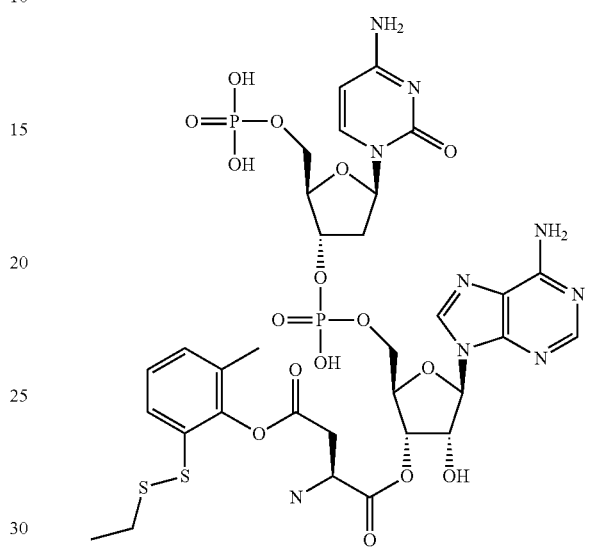

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (pdCpA, Compound 1h) (49.0 mg, 0.077 mmol) in water (1.52 ml) and a solution of 1-(cyanomethyl) 4-(2-(ethyldisulfanyl)-6-methylphenyl) (S)-2-((tert-butoxycarbonyl)amino)succinate (140 mg, 0.308 mmol) in tetrahydrofuran (0.764 ml) were added to buffer A (29.2 ml), and the mixture was stirred at room temperature for 1.5 hours. Trifluoroacetic acid (0.396 ml, 5.37 mmol) was then added, followed by lyophilization. The resulting residue was purified by reverse-phase silica gel column chromatography (0.1% aqueous formic acid solution/0.1% formic acid-acetonitrile solution=100/0→50/50) to afford a mixture of 1-((2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl) 4-(2-(ethyldisulfanyl)-6-methylphenyl) (2S)-2-((tert-butoxycarbonyl)amino)succinate and N,N,N-trimethylhexadecan-1-aminium. The resulting mixture was dissolved in trifluoroacetic acid (0.10 ml), and the mixture was stirred at room temperature for 10 minutes, after which the reaction solution was concentrated under reduced pressure. The resulting residue was purified by reverse-phase silica gel column chromatography (0.1% aqueous formic acid solution/0.1% formic acid-acetonitrile solution=100/0→60/40) to afford 1-((2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl) 4-(2-(ethyldisulfanyl)-6-methylphenyl) (2S)-2-aminosuccinate (Compound 114) (2.9 mg, 40%).

LCMS (ESI) m/z=932 (M–H)–

Retention time: 0.70 min (analysis condition SQDAA05)

2. Amidation Reaction in Translated Peptides

Amidation reaction not utilizing a reaction auxiliary group after translation synthesis was confirmed to occur by TOE-MS.

2-1. Synthesis of tRNA (Lacking CA) by Transcription tRNAGluAAG (-CA) (SEQ ID NO: R-40) lacking 3'-end CA was synthesized from template DNA (SEQ ID NO: D-40) by in vitro transcription using RiboMAX Large Scale RNA production System T7 (Promega, P1300) and purified with RNeasy Mini kit (Qiagen).

SEQ ID NO: D-40
tRNAGluAAG (-CA) DNA sequence:
(SEQ ID NO: 64)
GGCGTAATACGACTCACTATAGTCCCCTTCGTCTAGAGGCCCAGGACACC

GCCCTAAGACGGCGGTAACAGGGGTTCGAATCCCCTAGGGGACGC

SEQ ID NO: R-40
tRNAGluAAG (-CA) RNA sequence:
(SEQ ID NO: 65)
GUCCCCUUCGUCUAGAGGCCCAGGACACCGCCCUAAGACGGCGGUAACAG

GGGUUCGAAUCCCCUAGGGGACGC 2-2. Synthesis of Aminoacylated tRNA (Compound AT-7-a) by Ligation of Aminoacylated pdCpA Having Side Chain Carboxylic Acid Converted to Active Ester (Compound 1i-ID) and tRNA (Lacking CA) (SEQ ID NO: R-40)

2 μL of 10× ligation buffer (500 mM HEPES-KOH pH 7.5, 200 mM MgCl$_2$, 10 mM ATP) and 4 μL of nuclease free water were added to 10 μL of 50 μM transcribed tRNAGlu-AAG (-CA) (SEQ ID NO: R-40). The mixture was heated at 95° C. for 2 minutes and then incubated at room temperature for 5 minutes to refold the tRNA. 2 μL of 20 units/μL T4 RNA ligase (New England Biolabs) and 2 μL of a 5 mM solution of aminoacylated pdCpA having side chain carboxylic acid converted to active ester (Compound 1i-ID) in DMSO were added, and ligation reaction was carried out at 15° C. for 45 minutes. 4 μL of 3 M sodium acetate and 24 μL of 125 mM iodine (solution in water:THF=1:1) were added to 20 μL of the ligation reaction solution, and deprotection was carried out at room temperature for 1 hour. Aminoacylated tRNA (Compound AT-7-A) was collected by phenol extraction and ethanol precipitation. Aminoacylated tRNA (Compound AT-7-A) was dissolved in 1 mM sodium acetate immediately prior to addition to the translation mixture.

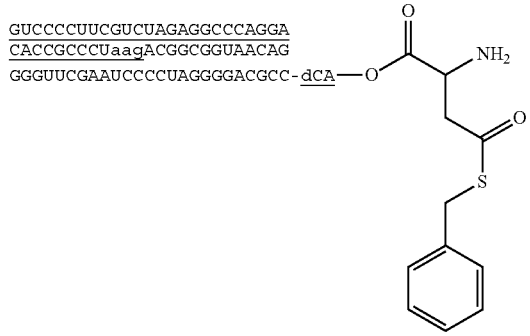

(SEQ ID NO: 66)
GUCCCCUUCGUCUAGAGGCCCAGGA
CACCGCCCUaagACGGCGGUAACAG
GGGUUCGAAUCCCCUAGGGGACGCC-dCA Compound AT-7-A Asp(SBn)-tRNAGluAAG 2-3. Translation Synthesis Using an Amino Acid Having Side Chain Carboxylic Acid Converted to Active Ester Translation synthesis of a desired unnatural amino acid-containing polypeptide was carried out by adding tRNA aminoacylated by an aspartic acid derivative having side chain carboxylic acid converted to active thioester to a cell-free translation system. The translation system used was PURE system, a prokaryote-derived reconstituted cell-free protein synthesis system. Specifically, the synthesis was carried out by adding 1 μM template RNA, 250 μM each of proteinogenic amino acids encoded by the respective template DNAs, and 50 μM aminoacylated tRNA having side chain carboxylic acid converted to active ester (Compound AT-7-A) to a transcription and translation solution (1% (v/v) RNasein Ribonuclease inhibitor (Promega, N2111), 1 mM GTP, 1 mM ATP, 20 mM creatine phosphate, 50 mM HEPES-KOH pH 7.6, 100 mM potassium acetate, 6 mM magnesium acetate, 2 mM spermidine, 1 mM dithiothreitol, 0.1 mM 10-HCO—H4 folate, 1.5 mg/ml E. coli MRE600 (RNase-negative)-derived tRNA (Roche), 4 μg/ml creatine kinase, 3 μg/mi myokinase, 2 units/ml inorganic pyrophosphatase, 1.1 μg/ml nucleoside diphosphate kinase, 0.6 μM methionyl tRNA transformylase, 0.26 μM EF-G, 0.24 μM RF2, 0.17 μM RF3, 0.5 μM RRF, 2.7 μM IF1, 0.4 μM IF2, 1.5 μM IF3, 40 μM EF-Tu, 93 μM EF-Ts, 1.2 μM ribosome, 0.73 μM AlaRS, 0.03 μM ArgRS, 0.38 μM AsnRS, 0.13 μM AspRS, 0.02 μM CysRS, 0.06 μM GlnRS, 0.23 μM GluRS, 0.09 μM GlyRS, 0.02 μM HisRS, 0.4 μM IleRS, 0.04 μM LeuRS, 0.11 μM LysRS, 0.03 μM MetRS, 0.68 μM PheRS, 0.16 μM ProRS, 0.04 μM SerRS, 0.09 μM ThrRS, 0.03 μM TrpRS, 0.02 μM TyrRS, 0.02 μM ValRS (self-prepared proteins were basically prepared as His-tagged proteins)) and allowing the translation reaction mixture to stand at 37° C. for 1 hour.

The translational product was identified by measuring MALDI-MS spectra using α-cyano-4-hydroxycinnamic acid as the matrix.

2-4. Translation Synthesis of a Peptide Containing a Benzylthioesterified Aspartic Acid Derivative (Compound P-141)

Figure 39:
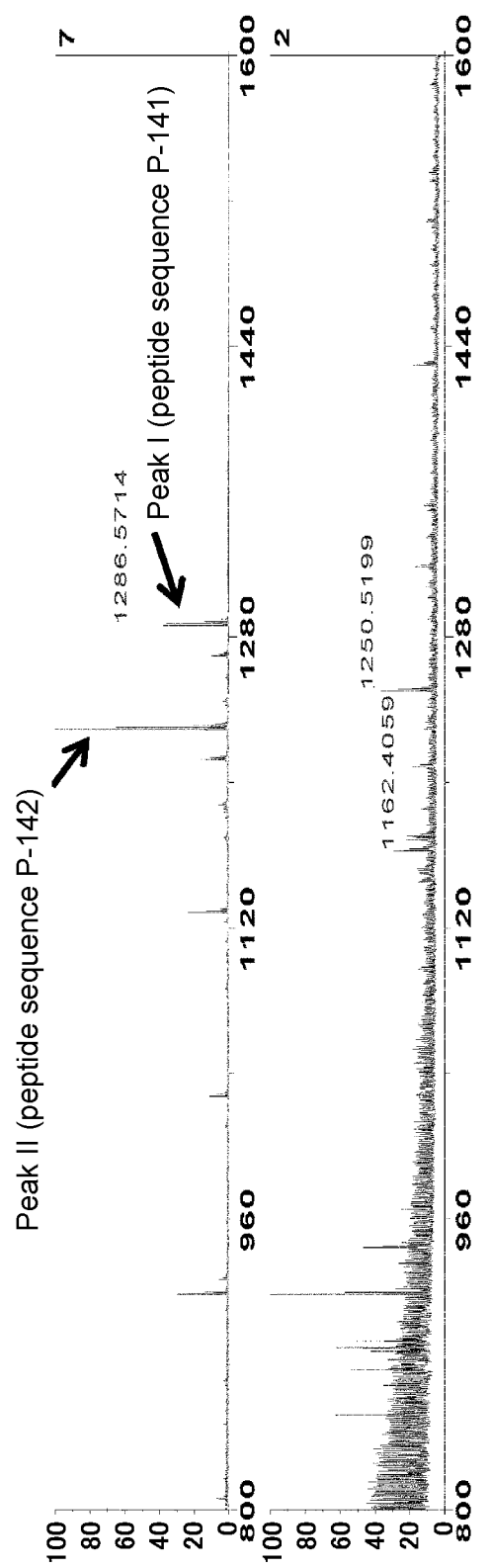
FIG. 39 is a diagram showing mass spectrometry results of translation reaction products obtained by the translational synthesis of peptides containing benzylthioesterified aspartic acid derivatives.

The aforementioned translation solution containing 1 μM template DNA Mgtp_R (SEQ ID NO: R-41 (SEQ ID NO: 67)) as well as 0.25 mM Gly, 0.25 mM Pro, 0.25 mM Arg, 0.25 mM Thr, 0.25 mM Tyr and 50 µM Asp(SBn)-tRNA-GluAAG (Compound AT-7-A) was incubated at 37° C. for 60 minutes. The resulting translation reaction product was purified with SPE C-TIP (Nikkyo Technos) and analyzed by MALDI-MS. As a result, the main products observed (FIG. 39) were peptide P-141 translated from Gly encoded by the second codon immediately following the initiation methionine and containing an N-terminal α-amino group and a thioester (FIG. 39, peak I) and peptide P-142 translated from Thr located immediately following the Gly (FIG. 39, peak II).

```
SEQ ID NO: R-41
Mgtp_R RNA sequence
                                        (SEQ ID NO: 67)
GGGUUAACUUUAAGAAGGAGAUAUACAUaugGGUACUACAACGCGUCUUC CGUACCGUGGCGGCuaagcuucg Peptide sequence P-141
                                       (SEQ ID NO: 339)
GlyThrThrThrArg[Asp(SBn)]ProTyrArgGlyGly Peptide sequence P-142
                                       (SEQ ID NO: 340)
ThrThrThrArg[Asp(SBn)]ProTyrArgGlyGly
```

MALDI-MS:

m/z: [H+M]+=1286.6 (peptide corresponding to the sequence P-141; Calc. 1286.6)

m/z: [H+M]+=1229.6 (peptide corresponding to the sequence P-142; Calc. 1229.6)

2-5. Experiment of Peptide Amide Cyclization Using the Thioester and the N-Terminal α-Amino Group on the Translated Peptide P-141

Figure 40:
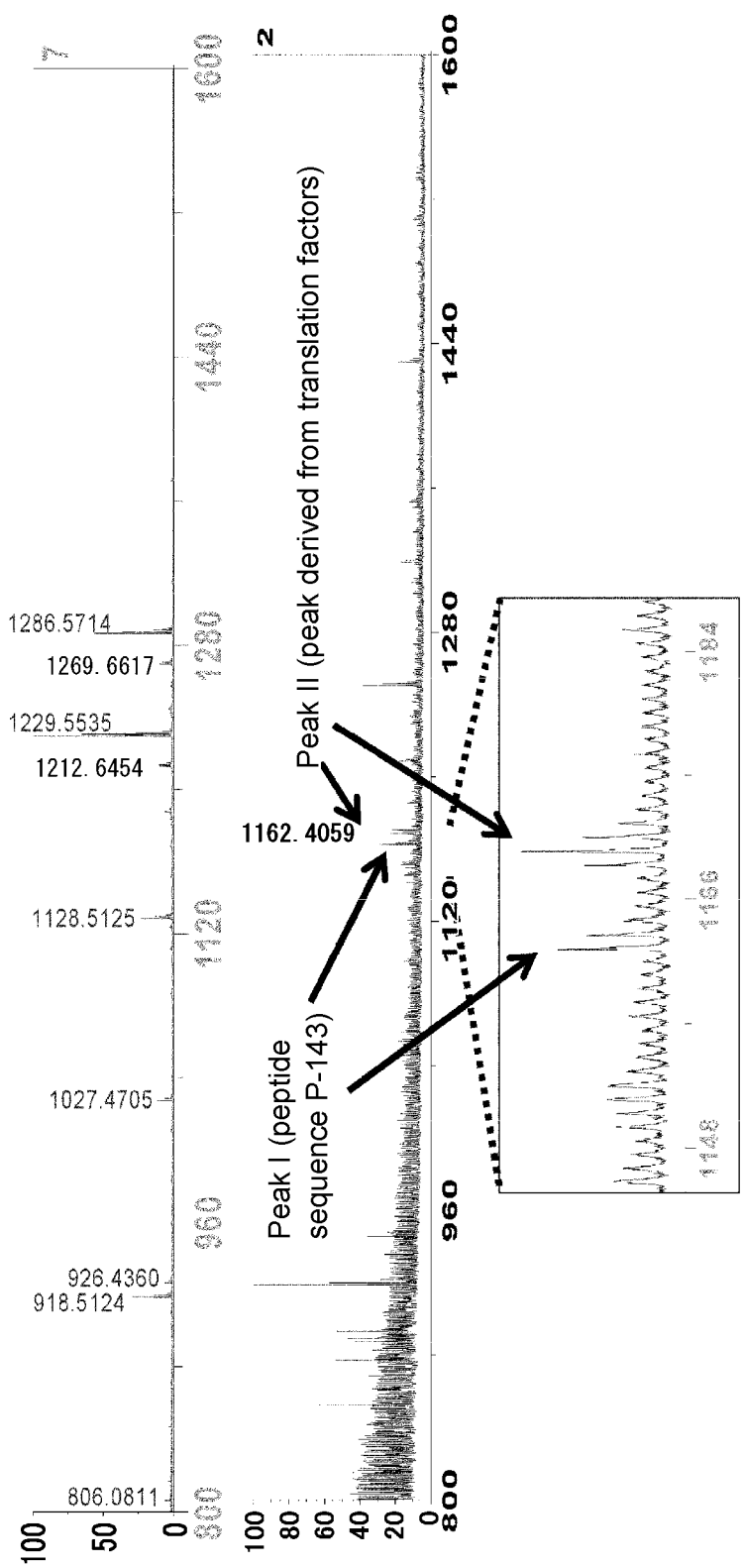
FIG. 40 is a diagram showing mass spectrometry results of products obtained by the experiment of peptide amide cyclization using the thioester and the N-terminal α-amino group on the translated peptide P141.

3.5 µL of the aforementioned translation solution containing the translation reaction product P-141, 1 µL of a thiophenol solution (in which 5 M 4-trifluoromethylthiophenol and 5 M triethylamine are mixed in equal amounts), and 0.5 µL of a 500 mM tricarboxyethylphosphine solution (pH 7.5) were mixed, and the mixture was incubated at 50° C. for 2 hours. As a result, the peak of the starting material P-141 disappeared, and a peak was observed instead corresponding to Compound P-143 amide-cyclized at the nitrogen atom of the N-terminal α-amino group and the side chain carboxylic acid of Asp (FIG. 40, peak I).

```
Peptide sequence P-143
                                       (SEQ ID NO: 68)
Compound amide-cyclized at the nitrogen atom of
the N-terminal amino group of
GlyThrThrThrArg[Asp(SBn)]ProTyrArgGlyGly and the
side chain carboxylic acid of Asp
```

MALDI-MS: m/z: [H+M]+=1162.4 (Calc. 1162.6)

(SEQ ID NO: 68)

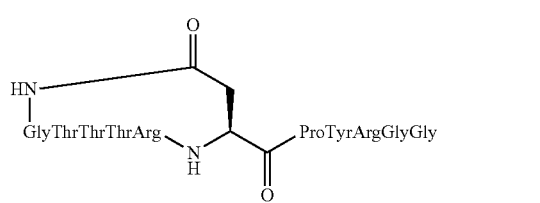

2-6. Synthesis of a Peptide Containing a Plurality of Non-Cys Residue N-Terminal Amino Acids Using the Initiation Read Through Method and Peptide Cyclization without a Reaction Auxiliary Group Translation synthesis of a desired unnatural amino acid-containing polypeptide was carried out by adding tRNA aminoacylated by an aspartic acid derivative having side chain carboxylic acid converted to active thioester and a proteinogenic amino acid mixture excluding initiation methionine to a cell-free translation system. The translation system used was PURE system, a prokaryote-derived reconstituted cell-free protein synthesis system. Specifically, the synthesis was carried out by adding 1 µM template RNA, 250 µM each of proteinogenic amino acids and 50 µM aminoacylated tRNA having side chain carboxylic acid converted to active ester (Compound AT-7-A) to a translation solution (1% (v/v) RNasein Ribonuclease inhibitor (Promega, N2111), 1 mM GTP, 1 mM ATP, 20 mM creatine phosphate, 50 mM HEPES-KOH pH 7.6, 100 mM potassium acetate, 6 mM magnesium acetate, 2 mM spermidine, 0.1 mM 10-HCO—H4 folate, 1.5 mg/ml E. coli MRE600 (RNase-negative)-derived tRNA (Roche), 4 µg/ml creatine kinase, 3 µg/mi myokinase, 2 units/ml inorganic pyrophosphatase, 1.1 µg/ml nucleoside diphosphate kinase, 0.6 µM methionyl tRNA transformylase, 0.26 µM EF-G, 0.24 µM RF2, 0.17 µM RF3, 0.5 µM RRF, 2.7 µM IF1, 0.4 µM IF2, 1.5 µM IF3, 40 µM EF-Tu, 93 µM EF-Ts, 1.2 µM ribosome, 0.73 µM AlaRS, 0.03 µM ArgRS, 0.38 µM AsnRS, 0.13 µM AspRS, 0.02 µM CysRS, 0.06 µM GlnRS, 0.23 µM GluRS, 0.09 µM GlyRS, 0.4 µM IleRS, 0.04 µM LeuRS, 0.11 µM LysRS, 0.03 µM MetRS, 0.68 µM PheRS, 0.16 µM ProRS, 0.04 µM SerRS, 0.09 µM ThrRS, 0.03 µM TrpRS, 0.02 µM TyrRS, 0.02 µM ValRS (self-prepared proteins were basically prepared as His-tagged proteins)) and allowing the translation reaction mixture to stand at 37° C. for 1 hour.

The translational product was identified by measuring MALDI-MS spectra using α-cyano-4-hydroxycinnamic acid as the matrix.

2-7. Translation Synthesis of Peptides Containing N-Terminal Phe or Ala and Benzylthioesterified Aspartic Acid Derivatives (P-D1 and P-D2)

The aforementioned translation solution containing 1 µM template RNA OT89 (SEQ ID NO: RM-D1) as well as 0.25 mM Phe, 0.25 mM Gly, 0.25 mM Pro, 0.25 mM Arg, 0.25 mM Thr, 0.25 mM Tyr and 50 µM Asp(SBn)-tRNAGluAAG (Compound AT-7-A) was incubated at 37° C. for 60 minutes. Similarly, the aforementioned translation solution containing 1 µM template RNA OT90 (SEQ ID NO: RM-D2) as well as 0.25 mM Ala, 0.25 mM Gly, 0.25 mM Pro, 0.25 mM Arg, 0.25 mM Thr, 0.25 mM Tyr and 50 µM Asp(SBn)-tRNAGluAAG (Compound AT-7-A) was incubated at 37° C. for 60 minutes in another tube. 9 µL each of 0.2% trifluoroacetic acid was added to 1 each of the resulting two translational products. 1 µL each of the resulting mixtures was loaded on a MALDI target plate, and then blended with 1 µL of a CHCA solution (10 mg/ml α-cyano-4-hydroxycinnamic acid, 50% acetonitrile, 0.1% trifluoroacetic acid) and dried on the plate. As a result of MALDI-MS analysis, the desired peptides P-D1 (FIG. 44, peak I) and P-D2 (FIG. 45, peak I) translated from Phe or Ala immediately following the initiation methionine were observed as main products from the templates RM-D1 and RM-D2, respectively.

```
SEQ ID NO: RM-D1
OT89 RNA sequence
                                          (SEQ ID NO: 78)
GGGUUAACUUUAAGAAGGAGAUAUACAUaugUUUACUACAACGCGUCUUC CGUACCGUGGCGGCuaagcuucg Peptide sequence P-D1
                                          (SEQ ID NO: 234)
PheThrThrThrArg[Asp(SBn)]ProTyrArgGlyGly SEQ ID NO: RM-D2
OT90 RNA sequence
                                          (SEQ ID NO: 79)
GGGUUAACUUUAAGAAGGAGAUAUACAUaugGCUACUACAACGCGUCUUC CGUACCGUGGCGGCuaagcuucg Peptide sequence P-D2
                                          (SEQ ID NO: 235)
AlaThrThrThrArg[Asp(SBn)]ProTyrArgGlyGly
```

MALDI-MS:

m/z: [H+M]+=1376.4 (peptide corresponding to the sequence P-D1; Calc. 1376.6)

m/z: [H+M]+=1300.4 (peptide corresponding to the sequence P-02; Cabo. 1300.6)

2-8. Experiment of Peptide Amide Cyclization Using the Thioesters and the N-Terminal α-Amino Groups on the Translated Peptides P-D1 and P-D2

Figure 44:
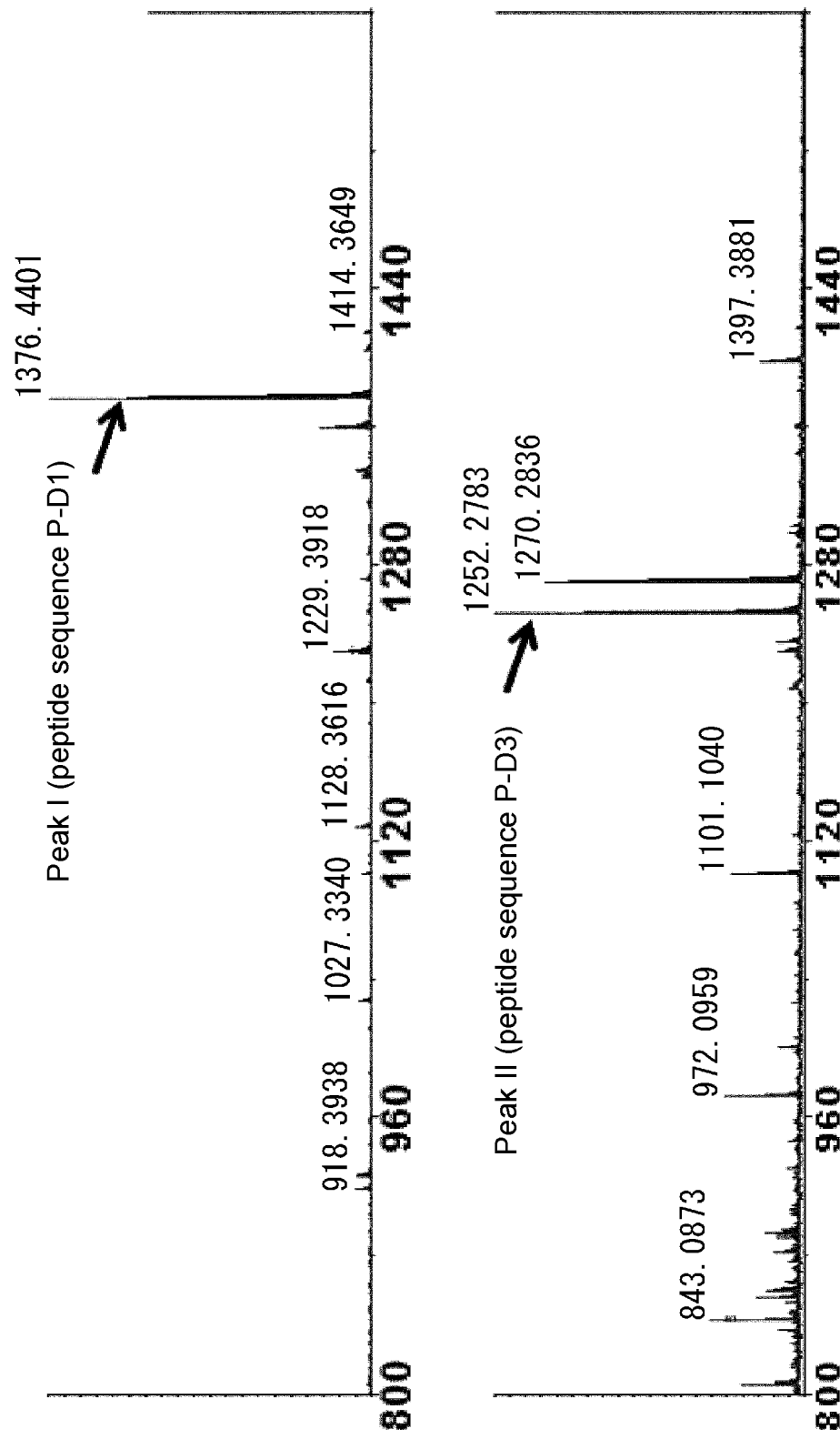
FIG. 44 is a diagram showing MALDI-MS analysis results of peptides containing N-terminal Phe, Ala, and benzylthioesterified aspartic acid derivatives.
Figure 45:
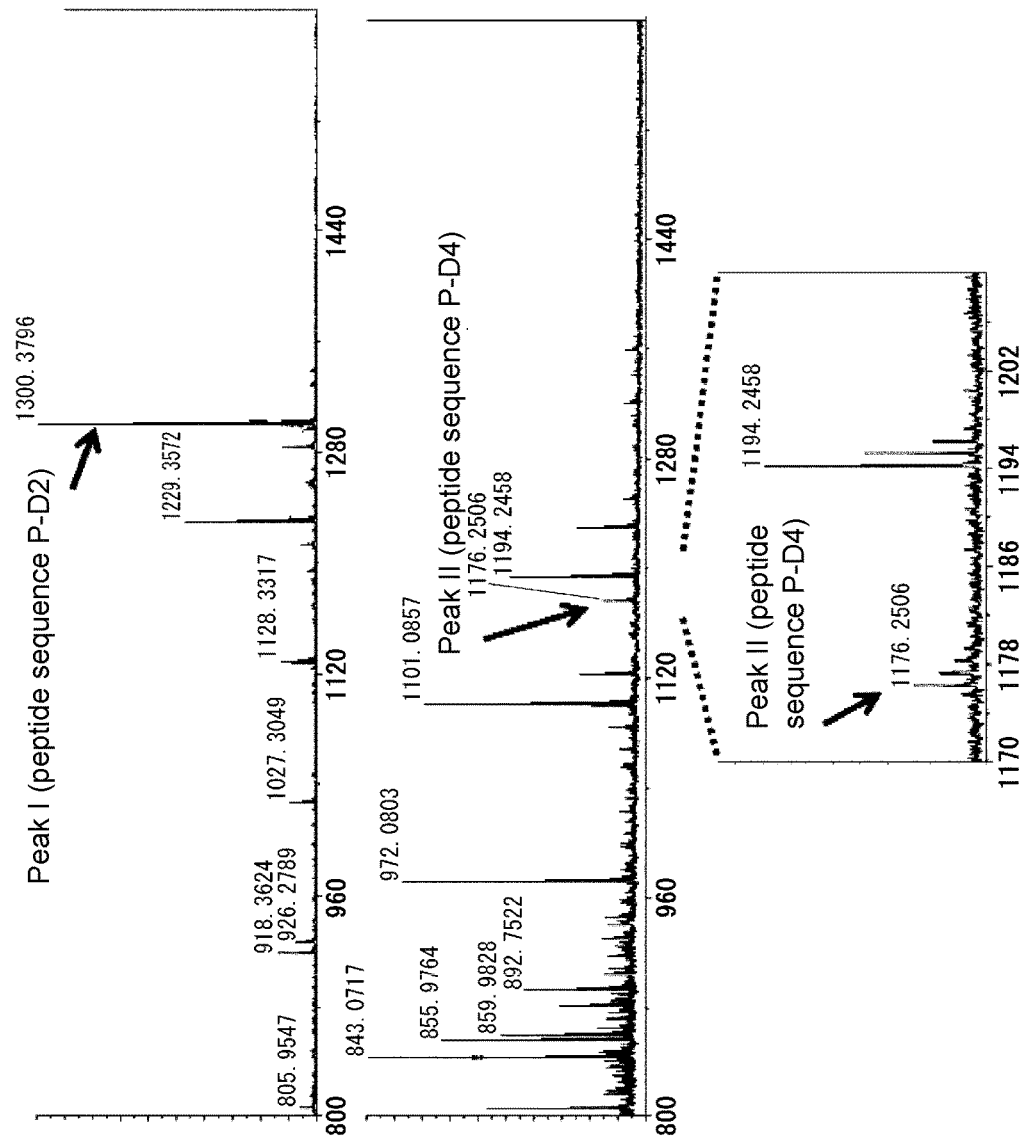
FIG. 45 is a diagram showing MALDI-MS analysis results of peptides containing N-terminal Phe, Ala, and benzylthioesterified aspartic acid derivatives.

3.5 μL of the aforementioned translation solution containing the translation reaction product P-D1, 1 μL of a thiophenol solution (in which 5 M 4-trifluoromethylthiophenol and 5 M triethylamine are mixed in equal amounts), and 0.5 μL of a 500 mM tricarboxyethylphosphine solution (pH 7.5) were mixed, and the mixture was incubated at 50° C. for 2 hours. 12 μL of 2% trifluoroacetic acid was added to 2 μL of the resulting reaction solution. 1 μL of the resulting mixture was loaded on a MALDI target plate, and then blended with 1 μL of a CHCA solution (10 mg/ml α-cyano-4-hydroxycinnamic acid, 50% acetonitrile, 0.1% trifluoroacetic acid), dried on the plate and then analyzed by MALDI-MS. As a result, the peak of the starting material P-D1 disappeared, and a peak was observed instead corresponding to Compound P-D3 amide-cyclized at the nitrogen atom of the N-terminal α-amino group and the side chain carboxylic acid of Asp (FIG. 44, peak II). The aforementioned translation solution containing the translation reaction product D-2 was also subjected to the same operation as described above and analyzed by MALDI-MS. As a result, a peak was observed corresponding to Compound P-D4 amide-cyclized at the nitrogen atom of the N-terminal α-amino group and the side chain carboxylic acid of Asp (FIG. 45, peak II).

```
Peptide sequence P-D3
                                          (SEQ ID NO: 80)
Compound amide-cyclized at the nitrogen atom of
the N-terminal amino group of
PheThrThrThrArg[Asp(SBn)]ProTyrArgGlyGly and the
side chain carboxylic acid of Asp
```

MALDI-MS: m/z: [M+H]+=1252.3 (Calc. 1252.6)

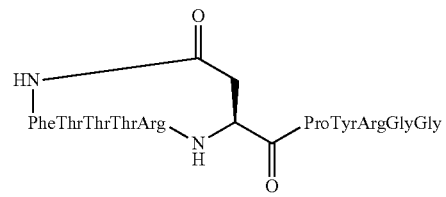
(SEQ ID NO: 80)

```
Peptide sequence P-D4
                                          (SEQ ID NO: 81)
Compound amide-cyclized at the nitrogen atom of
the N-terminal amino group of
AlaThrThrThrArg[Asp(SBn)]ProTyrArgGlyGly and the
side chain carboxylic acid of Asp
```

MALDI-MS: m/z: [M+H]+=1176.3 (Calc. 1176.6)

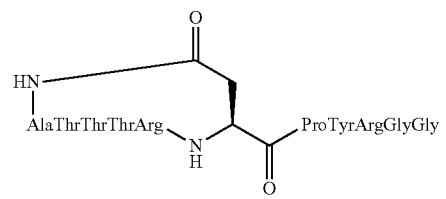
(SEQ ID NO: 81)

2-9. RNA Stability Evaluation Under Cyclization Reaction Conditions

RNA subjected to reaction conditions was analyzed by gel Electrophoresis in order to evaluate whether or not RNA is decomposed under amidation cyclization reaction conditions not utilizing a reaction auxiliary group.

3.5 μL of a solution containing 1 uM Mgtp_R RNA (SEQ ID NO: R-41) (1 mM GTP, 1 mM ATP, 20 mM creatine phosphate, 50 mM HEPES-KOH, pH 7.6, 100 mM potassium acetate, 6 mM magnesium acetate, 2 mM spermidine, 1 mM dithiothreitol, 0.1 mM 10-HCO—H4 folate), 1 μL of a thiophenol solution (in which 5 M 4-trifluoromethylthiophenol and 5 M triethylamine are mixed in equal amounts) and 0.5 μL of a 500 mM tricarboxyethylphosphine solution (pH 7.6) were mixed, and the mixture was incubated at 50° C. for 0.5 to 2 hours. The reaction solution was then purified with RNeasy minelute (Qiagen). As control experiments where RNA was not subjected to cyclization conditions, the above mixture where the incubation time was omitted, where water was added in place of the thiophenol solution, or where purification was omitted in addition to the omission of the incubation time and the addition of water, was also subjected to the same operation. The resulting RNA solutions were subjected to electrophoresis using 10% polyacrylamide gel containing 6 M urea and the gel was stained with SYBR gold nucleic acid stain (Invitrogen).

Figure 46:
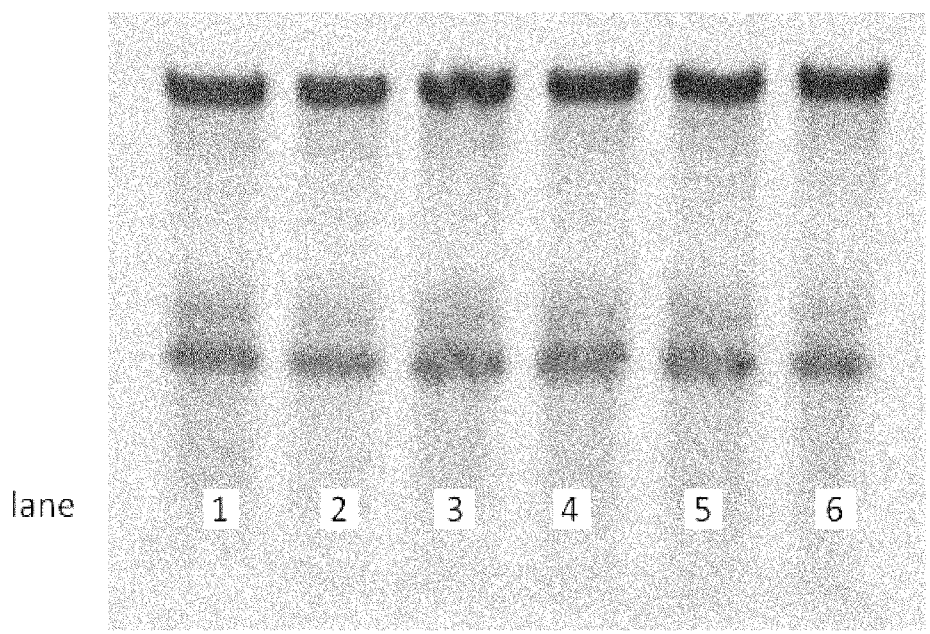
FIG. 46 is a diagram showing electrophoretic evaluation results of RNA stability under cyclization reaction conditions.

The results revealed that the RNA (lane 6) subjected to reaction conditions does not differ in band pattern and band density from RNAs (lanes 1 to 3) not subjected to cyclization conditions as control experiments and thus the RNA is stable under cyclization reaction conditions (FIG. 46).

This experiment disclosed the following facts. (1) The initiation read through method also effectively functions for Ala and Phe as in the case of Cys and Gly and can selectively translate a desired peptide sequence. (2) Desired cyclization reaction could proceed for both Ala and Phe. It could be disclosed for the first time that amino acids other than Cys (having a reaction auxiliary group) and Gly (most reactive due to the absence of the α-position substituent) also allow amidation reaction through thioesters to proceed in translation solutions. In order to allow this reaction to proceed, it is necessary to translationally synthesize active esters stable in translation solutions and select N-alkylated units such as N-methylated units (including proline) for amino acids in the units adjacent to the intersection units including the active esters on the C-terminal side (to avoid formation of aspartimides). (3) Main by-products are hydrolysates at the thioester sites. (4) RNAs can be stably present under the present reaction conditions, and the same reaction can be allowed to proceed for peptide-RNA complexes.

3-1. Optimization of Cyclization Reaction Conditions

Since the cyclization reaction examples for translated peptides and the reaction examples for synthetic peptides in translation solutions provided similar results, it can be understood that the cyclization reaction yields of translated peptides are improved if it can be confirmed that the reaction yields of synthetic peptides in translation solutions are improved. Optimization of reaction of synthetic peptides in translation solutions was examined as described below.

3-1-1. Effects of pH

Reactions had been carried out at around pH 9 to 10. As a result of cyclization reactions at three pHs, pH 7.8, 8.1 and 9.2, it was revealed that the cyclization:hydrolysis ratio is improved at lower pH.

Synthesis of (2S,5S,8S,14S,17S,20S,23S,26S)—
N—((S)-1-(((S)-1-((2-amino-2-oxoethyl)amino)-3-hydroxy-1-oxopropan-2-yl)amino)-1-oxopropan-2-yl)-8,23-dibenzyl-14-isobutyl-20-isopropyl-N,2,5,7,17-pentamethyl-3,6,9,12,15,18,21,24,28-nonaoxo-1,4,7,10,13,16,19,22,25-nonaazacyclooctacosane-26-carboxamide (Compound SP-511)

4-(Trifluoromethyl)benzenethiol (13.6 ul, 0.10 mmol) and triethylamine (13.9 ul, 0.10 mmol) were dissolved in a 100 mM aqueous disodium hydrogenphosphate solution (80 μl) and NMP (10 μl). A solution of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate (Compound SP-504) in NMP (10 mM, 10 μl, 0.10 μmol) and a solution of 4-propylbenzoic acid as internal standard in acetonitrile (50 mM, 1.0 μL) were added to this solution, and the mixture was stirred at 30° C. overnight. The pH at the start of the reaction was 9.0. The reaction solution was analyzed by LCMS to confirm that the title compound was produced. The conversion rate after stirring for 2 hours was 72% based on the LCMS-UV area ratio to the internal standard, and the production ratio of the title compound (SP-511) and the hydrolysate (Compound SP-512) was 12:1 (based on the UV area ratio by LCMS). Moreover, the conversion rate after 4 hours was 81%, and the production ratio of the title compound (SP-511) and the hydrolysate (Compound SP-512) was 8:1 (based on the UV area ratio by LCMS). After stirring overnight, the starting material compound (SP-504) disappeared, but the production ratio of the title compound (SP-511) and the hydrolysate (Compound SP-512) was 3:1 (based on the change in UV area ratio and mass intensity ratio by LCMS (by comparison between data after six hours and data after stirring overnight)). That is, extension of the reaction time resulted in a decrease in selectivity of the title compound against the hydrolysate (Table 12). The pH of the reaction solution after stirring overnight was measured to be 10.0.

Title Compound
   LCMS (ESI) m/z=1132.3 (M–H)–
   Retention time: 0.64 min (analysis condition SQDFA05)
Hydrolysate (Compound SP-512)

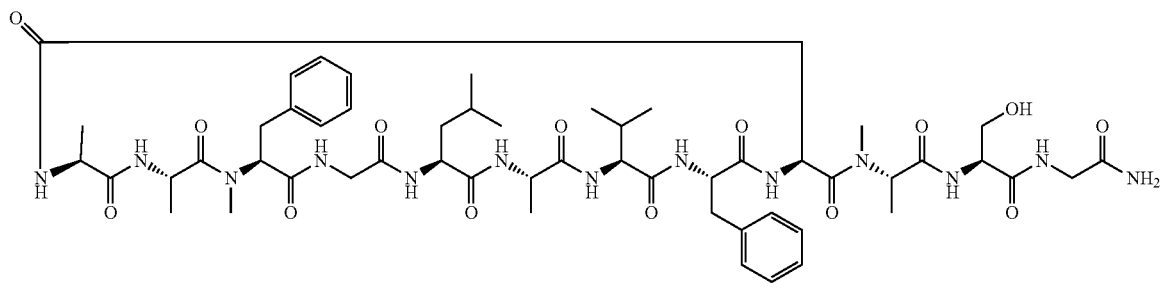

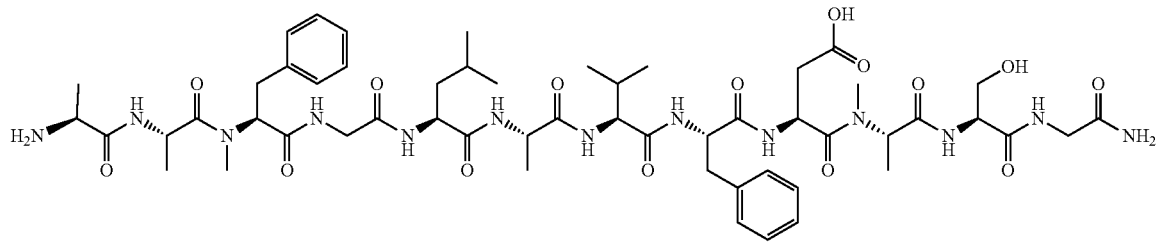 [SMILES: CC(C)C[C@H](NC(=O)CNC(=O)[C@H](Cc1ccccc1)N(C)C(=O)[C@H](C)NC(=O)[C@H](C)N)C(=O)N[C@@H](C)C(=O)N[C@H](C(=O)N[C@@H](Cc1ccccc1)C(=O)N[C@@H](CC(=O)O)C(=O)N(C)[C@@H](C)C(=O)N[C@@H](CO)C(=O)NCC(N)=O)C(C)C]

LCMS (ESI) m/z=1150.4 (M–H)–
Retention time: 0.49 min (analysis condition SQDFA05)

TABLE 12

| Time | 0 hour | 1 hour | 2 hours | 4 hours | 6 hours | overnight |
|---|---|---|---|---|---|---|
| Conversion rate (%) | 0 | 43 | 72 | 81 | 99 | 100 |
| Title compound/hydrolysate | — | 13/1 | 12/1 | 8/1 | 3/1 | 3/1 |
| pH | 9.0 | — | — | — | — | 10.3 |

The results above revealed that the pH is increased and accordingly the selectivity for the cyclized compound (title compound)/hydrolysate was decreased as the reaction time passes. Generation of free triethylamine causes the increase in pH due to the passage of time. In this reaction, 4-(trifluoromethyl)benzenethiol used as an additive is added as a salt with triethylamine in order to enhance water solubility. When the 4-(trifluoromethyl)benzenethiol is oxidized to be a disulfide, then the amine neutralized with an SH group before oxidation becomes excessive, and free triethylamine is produced in the system, resulting in an increase in the pH.

It can be concluded that reaction conditions established to maintain basicity and avoid increasing basicity in the reaction are essential in order to improve selectivity for the cyclized compound (title compound)/hydrolysate. Methods for such reaction conditions include a method of increasing the concentration of the buffer so that the increase in the pH is suppressed by a buffering action even when free triethylamine is generated. It is also possible to use a method of suppressing thiol oxidation so that free triethylamine is not generated in the system. In other words, it is desirable to carry out the reaction under a nitrogen atmosphere or in the presence of a reducing agent such as tris(2-carboxyethyl)phosphine.

Accordingly, in terms of such a perspective, experiments were carried out under conditions where the concentration of the buffer in the reaction solution was increased from 62 mM to 500 mM and 50 mM tris(2-carboxyethyl)phosphine was added as a reducing agent in order to suppress the increase in the pH of the reaction. The reactions below were carried out at three pHs, pH 7.8, 8.1 and 9.2, in order to confirm the influence of pHs on selectivity for the cyclized compound (title compound)/hydrolysate.

Synthesis of (2S,5S,8S,14S,17S,20S,23S,26S)—
N—((S)-1-(((S)-1-((2-amino-2-oxoethyl)amino)-3-hydroxy-1-oxopropan-2-yl)amino)-1-oxopropan-2-yl)-8,23-dibenzyl-14-isobutyl-20-isopropyl-N,2,5,7,17-pentamethyl-3,6,9,12,15,18,21,24,28-nonaoxo-1,4,7,10,13,16,19,22,25-nonaazacyclooctacosane-26-carboxamide (Compound SP-511)

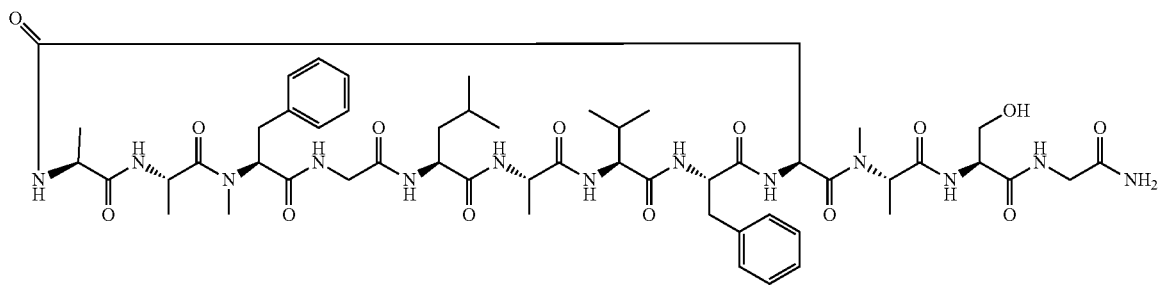 [SMILES: CC(C)C[C@@H]1NC(=O)CNC(=O)[C@H](Cc2ccccc2)N(C)C(=O)[C@H](C)NC(=O)[C@H](C)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

Synthesis of Compound SP-511 at pH 7.8

A mixed solution of water (10.9 ul), 4-(trifluoromethyl)benzenethiol (6.80 ul, 0.050 mmol) and triethylamine (6.97 ul, 0.050 mmol) was prepared. 1.9 M HEPES buffer (pH=7.5, 13.1 ul) and a 0.5 M aqueous tris(2-carboxyethyl)phosphine solution (pH=7.6, 5.0 ul) were added to the mixed solution. Further, 5 ul of a 10 mM solution of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate (Compound SP-504) in N-methylpyrrolidone and a 11 mM solution of internal standard (4-propylbenzoic acid) in N-methylpyrrolidone (2.25 ul) were added, and the mixture was stirred at 30° C. for 6 hours. The pH at the start of the reaction was 7.8. The change in the reaction was observed by LCMS to confirm that the title compound was produced. After 6 hours, the conversion rate was 96% based on the area ratio to the internal standard, and the production ratio of the title compound (SP-511) and the hydrolysate (Compound SP-512) was about 38:1 based on the UV area ratio by LCMS.
Title Compound
    LCMS (ESI) m/z=1132.3 (M–H)–
    Retention time: 0.63 min (analysis condition SQDFA05)
Hydrolysate (Compound SP-512)

Synthesis of Compound SP-511 at pH 9.2

The reaction was carried out by the same method as in the above synthesis of Compound SP-511 at pH 7.8 using 1.9 M bicine buffer (pH=9.5, 13.1 ul) in place of 1.9 M HEPES buffer (pH=7.5, 13.1 ul). The mixture was stirred at 30° C. for 6 hours. The pH at the start of the reaction was 9.2. The change in the reaction was observed by LCMS to confirm that the title compound was produced. After 6 hours, the conversion rate was 87% based on the area ratio to the internal standard, and the production ratio of the title compound (SP-511) and the hydrolysate (Compound SP-512) was about 22:1 based on the UV area ratio by LCMS.

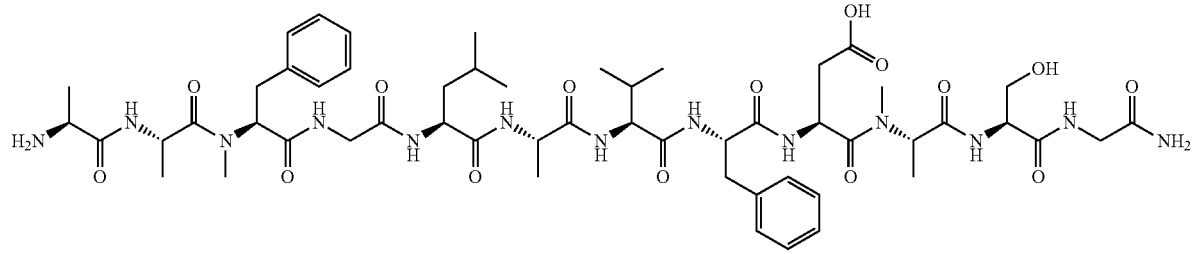 [SMILES: CC(C)C[C@H](NC(=O)CNC(=O)[C@H](Cc1ccccc1)N(C)C(=O)[C@H](C)NC(=O)[C@H](C)N)C(=O)N[C@@H](C)C(=O)N[C@H](C(=O)N[C@@H](Cc1ccccc1)C(=O)N[C@@H](CC(=O)O)C(=O)N(C)[C@@H](C)C(=O)N[C@@H](CO)C(=O)NCC(N)=O)C(C)C]

LCMS (ESI) m/z=1150.5 (M–H)–
Retention time: 0.48 min (analysis condition SQDFA05)

Synthesis of Compound SP-511 at pH 8.1

The reaction was carried out by the same method as in the above synthesis of Compound SP-511 at pH 7.8 using 1.9 M HEPES buffer (pH=8.1, 13.1 ul) in place of 1.9 M HEPES buffer (pH=7.5, 13.1 ul). The mixture was stirred at 30° C. for 6 hours. The pH at the start of the reaction was 8.1. The change in the reaction was observed using LCMS to confirm that the title compound was produced. After 6 hours, the conversion rate was 93% based on the area ratio to the internal standard, and the production ratio of the title compound (SP-511) and the hydrolysate (Compound SP-512) was about 40:1 based on the UV area ratio by LCMS.
Title Compound (SP-511)
    LCMS (ESI) m/z=1132.3 (M–H)–
    Retention time: 0.63 minute (analysis condition SQDFA05)
Hydrolysate (Compound SP-512)
    LCMS (ESI) m/z=1150.4 (M–H)–
    Retention time: 0.48 minute (analysis condition SQDFA05)

Title Compound (SP-511)
    LCMS (ESI) m/z=1132.4 (M–H)–
    Retention time: 0.63 min (analysis condition SQDFA05)
Hydrolysate (Compound SP-512)
    LCMS (ESI) m/z=1150.3 (M–H)–
    Retention time: 0.48 min (analysis condition SQDFA05)

3-1-2. Effect of the Concentration of the Additive (4-(trifluoromethyl)benzenethiol)

It was revealed that the ratio of the hydrolysate is increased when the concentration is 100 mM instead of 1 M.

Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-8,23-dibenzyl-14-isobutyl-20-isopropyl-N,2,5,7,17-pentamethyl-3,6,9,12,15,18,21,24,28-nonaoxo-1,4,7,10,13,16,19,22,25-nonaazacyclooctacosane-26-carboxamide (Compound SP-511)

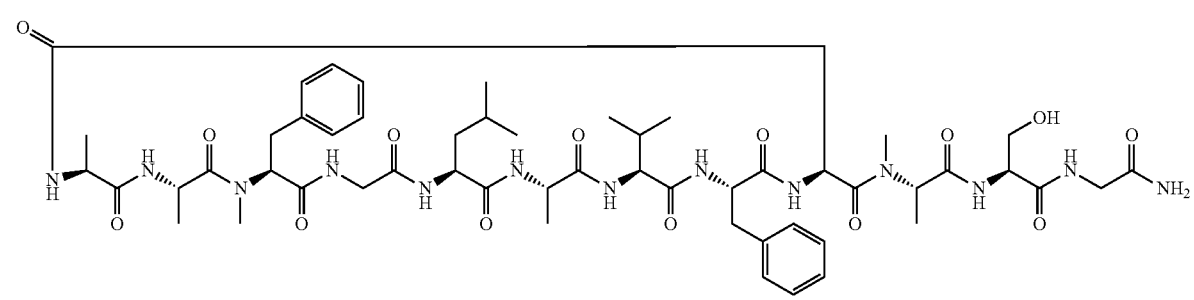 [SMILES: CC(C)C[C@@H]1NC(=O)CNC(=O)[C@H](Cc2ccccc2)N(C)C(=O)[C@H](C)NC(=O)[C@H](C)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

A mixed solution of water (41.6 ul), 4-(trifluoromethyl) benzenethiol (1.36 ul, 0.01 mmol) and triethylamine (1.39 ul, 0.01 mmol) was prepared. 1.9 M HEPES buffer (pH=8.1, 26.2 ul) and a 0.5H aqueous tris(2-carboxyethyl)phosphine solution (pH=7.6, 10 ul) were added to the mixed solution. Further, 10 ul of a 10 mM solution of S-benzyl (3S,6S,9S, 12S,15S,21S,24S,27S)-27-amino-3-(((S)-1-(((S)-1-((2-amino-2-oxoethyl)amino)-3-hydroxy-1-oxopropan-2-yl) amino)-1-oxopropan-2-yl)(methyl)carbamoyl)-6,21-dibenzyl-15-isobutyl-9-isopropyl-12,22,24-trimethyl-5,8, 11,14,17,20,23,26-octaoxo-28-phenyl-4,7,10,13,16,19,22, 25-octaazaoctacosane-1-thioate (Compound SP-504) in N-methylpyrrolidone, a 11 mM solution of internal standard (4-propylbenzoic acid) in N-methylpyrrolidone (4.56 ul) and N-methylpyrrolidone (4.89 ul) were added, and the mixture was stirred at 30° C. for overnight. The pH at the start of the reaction was 7.9. The change in the reaction was observed by LCMS to confirm that the title compound was produced. After stirring overnight, the conversion rate was 98% based on the area ratio to the internal standard, and the production ratio of the title compound (SP-511) and the hydrolysate (Compound SP-512) was about 6:1 based on the UV area ratio by LCMS.
Title Compound (SP-511)
  LCMS (ESI) m/z=1132.3 (M−H)−
  Retention time: 0.63 min (analysis condition SQDFA05)
Hydrolysate (Compound SP-512)
  LCMS (ESI) m/z=1150.2 (M−H)−
  Retention time: 0.48 min (analysis condition SQDFA05)

3-1-3. Change in the Production Ratio of the Cyclized Compound and the Hydrolysate by Changing the Ratio of the Organic Solvent and Water The results indicated that increasing the ratio of the organic solvent is advantageous.

Reaction Example at a Ratio of an Organic Solvent (NMP):Water=50:50 Using an Additive (4-(trifluoromethyl)benzenethiol) at a Concentration of 1 M Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-8,23-dibenzyl-14-isobutyl-20-isopropyl-N,2,5,7, 17-pentamethyl-3,6,9,12,15,18,21,24,28-nonaoxo-1, 4,7,10,13,16,19,22,25-nonaazacyclooctacosane-26-carboxamide (Compound SP-511)

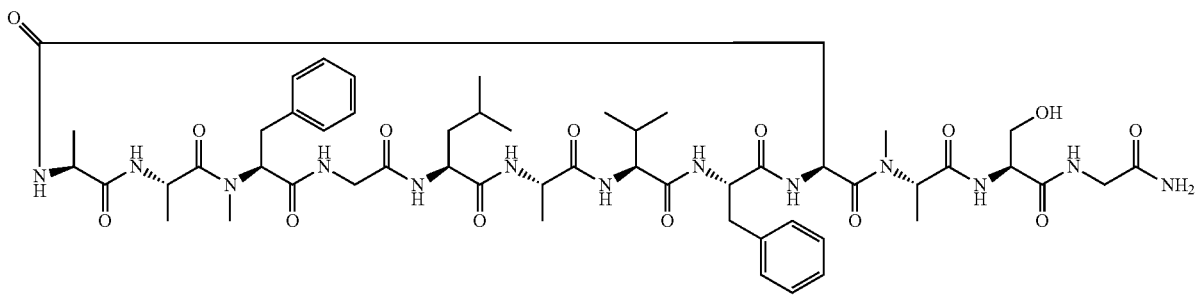 [SMILES: CC(C)C[C@@H]1NC(=O)CNC(=O)[C@H](Cc2ccccc2)N(C)C(=O)[C@H](C)NC(=O)[C@H](C)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

A mixed solution of HEPES buffer (5 M, pH=7.5, 10.0 μl), 4-(trifluoromethyl)benzenethiol (13.6 μl, 0.10 mmol) and triethylamine (13.9 μl, 0.10 mmol) was prepared. Water (21.75 μl), NMP (21.75 μl) and an aqueous tris(2-carboxyethyl)phosphine solution (1.1 M, pH=7.5, 4.5 μl) were added to the mixed solution. Further, a solution of S-benzyl (3S, 6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8, 11,14,17,20,23,26-octaoxo-4,7,10,13,16,19,22,25-octaazaoctacosane-1-thioate (Compound SP-504) in NMP (10 mM, 10 μl, 0.10 μmol) and a solution of 4-propylbenzoic acid as internal standard in NMP (11 mM, 4.5 μl) were added, followed by stirring at 30° C. The pH at the start of the reaction was 7.5. After 6 hours, the reaction was analyzed by LC/MS to confirm that the title compound was produced. The reaction conversion rate was 91% based on the area ratio to the internal standard, and the production ratio of the title compound (SP-511) and the hydrolysate (Compound SP-512) was about 35:1 based on the UV area ratio for LC/MS.
Title Compound (SP-511)
  LCMS (ESI) m/z=1134.5 (M+H)+
  Retention time: 0.64 min (analysis condition SQDFA05)

Reaction Example at a Ratio of an Organic Solvent (NMP):Water=10:90 Using an Additive (4-(trifluoromethyl)benzenethiol) at a Concentration of 1 M Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-8,23-dibenzyl-14-isobutyl-20-isopropyl-N,2,5,7,17-pentamethyl-3,6,9,12,15,18,21,24,28-nonaoxo-1,4,7,10,13,16,19,22,25-nonaazacyclooctacosane-26-carboxamide (Compound SP-511)

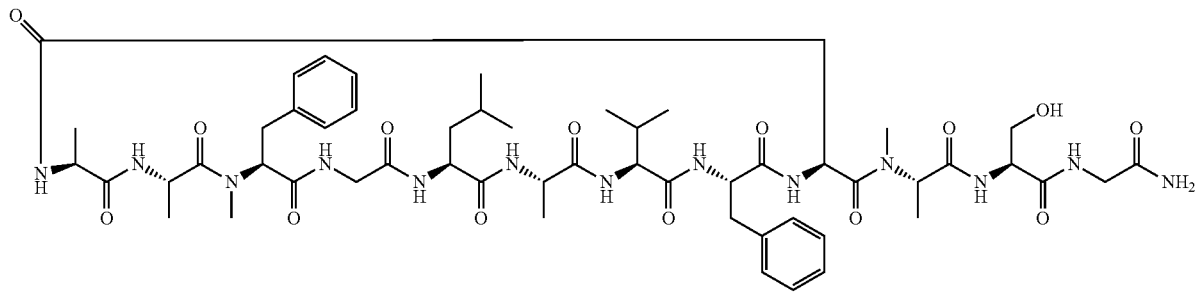 [SMILES: CC(C)C[C@@H]1NC(=O)CNC(=O)[C@H](Cc2ccccc2)N(C)C(=O)[C@H](C)NC(=O)[C@H](C)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

A mixed solution of HEPES buffer (5 M, pH=7.5, 10.0 µl), 4-(trifluoromethyl)benzenethiol (13.6 µl, 0.10 mmol) and triethylamine (13.9 µl, 0.10 mmol) was prepared. Water (50.75 µl) and an aqueous tris(2-carboxyethyl)phosphine solution (1.1 M, pH=7.5, 4.5 µl) were added to the mixed solution. Further, a solution of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-4,7,10,13,16,19,22,25-octaazaoctacosane-1-thioate (Compound SP-504) in NMP (18.2 mM, 5.5 µl, 0.10 µmol) and a solution of 4-propylbenzoic acid as internal standard in NMP (28.5 mM, 1.75 µl) were added, followed by stirring at 30° C. The pH at the start of the reaction was 7.4. After 6 hours, the reaction was analyzed by LC/MS to confirm that the title compound was produced. The reaction conversion rate was 93% based on the area ratio to the internal standard, and the production ratio of the title compound (SP-511) and the hydrolysate (Compound SP-512) was about 12:1 based on the UV area ratio for LC/MS.

Title Compound

LCMS (ESI) m/z=1134.5 (M+H)+

Retention time: 0.64 min (analysis condition SQDFA05)

3-1-4. Optimization of the Additive

Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-2,8,23-tribenzyl-14-isobutyl-20-isopropyl-N,5,7,17-tetramethyl-3,6,9,12,15,18,21,24,28-nonaoxo-1,4,7,10,13,16,19,22,25-nonaazacyclooctacosane-26-carboxamide (Compound SP-509)

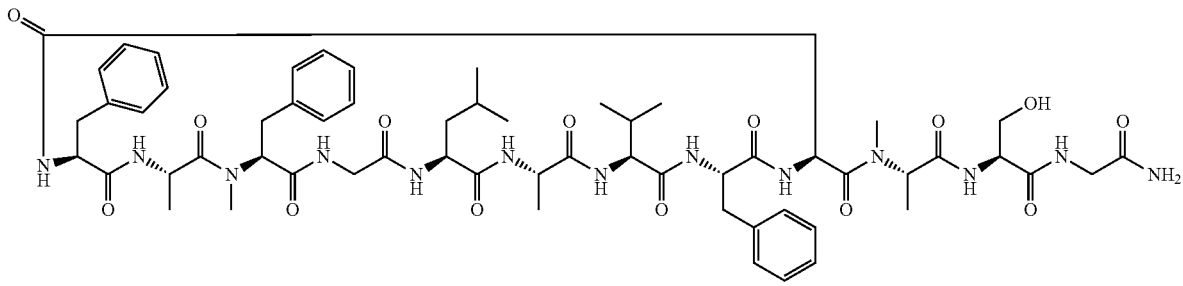 [SMILES: CC(C)C[C@@H]1NC(=O)CNC(=O)[C@H](Cc2ccccc2)N(C)C(=O)[C@H](C)NC(=O)[C@H](Cc2ccccc2)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

A mixed solution of water (21.8 ul), 4-(trifluoromethyl)benzenethiol (13.6 ul, 0.100 mmol) and triethylamine (13.9 ul, 0.100 mmol) was prepared. 1.9 M HEPES buffer (pH=8.1, 26.2 ul) and a 0.5 M aqueous tris(2-carboxyethyl)phosphine solution (pH=7.0, 10.0 ul) were added to the mixed solution. Further, 10 ul of a 10 mM solution of S-benzyl (3S,6S,9S,12S,15S,21S,24S,27S)-27-amino-3-(((S)-1-(((S)-1-((2-amino-2-oxoethyl)amino)-3-hydroxyl-- oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate (Phe-Ala-MePhe-Gly-Leu-Ala-Val-Phe-Asp(SBn)-MeAla-Ser-Gly-NH2) (Compound SP-508) (SEQ ID NO: 236) in N-methylpyrrolidone and a 11 mM solution of internal standard (4-propylbenzoic acid) in N-methylpyrrolidone (4.56 ul) were added, and the mixture was stirred at 30° C. overnight. The pH at the start of the reaction was 8.1. The change in the reaction was observed by LCMS to find that the starting material Compound SP-508 disappeared. The masses of the title compound (SP-509) and the hydrolysate (Compound SP-510) were observed to find that the mass intensity ratio (+) by LCMS is approximately 8:1.

Title Compound (SP-509)

LCMS (ESI) m/z=1210.4 (M+H)+

Hydrolysate (Compound SP-510)

(3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosan-1-oic Acid

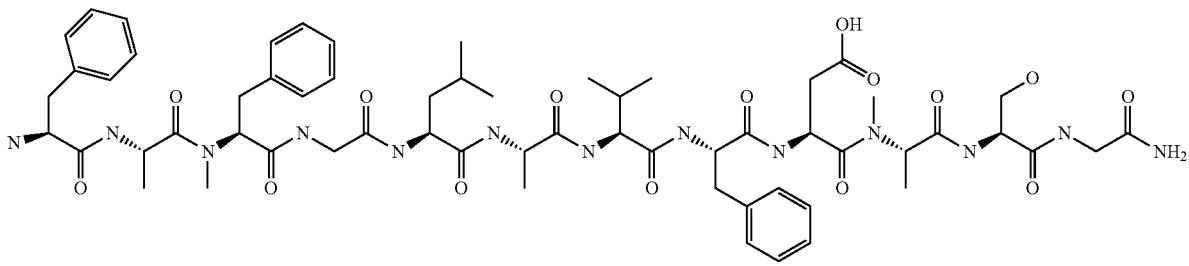 [SMILES: CC(C)C[C@H](NC(=O)CNC(=O)[C@H](Cc1ccccc1)N(C)C(=O)[C@H](C)NC(=O)[C@@H](N)Cc1ccccc1)C(=O)N[C@@H](C)C(=O)N[C@H](C(=O)N[C@@H](Cc1ccccc1)C(=O)N[C@@H](CC(=O)O)C(=O)N(C)[C@@H](C)C(=O)N[C@@H](CO)C(=O)NCC(N)=O)C(C)C]

LCMS (ESI) m/z=1228.4 (M+H)+

3-1-4-1. The Case where 4-nitrobenzenethiol (1 M) was Used in Place of 4-(trifluoromethyl)benzenethiol (1 M) as an Additive Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-2,8,23-tribenzyl-14-isobutyl-20-isopropyl-N,5,7,17-tetramethyl-3,6,9,12,15,18,21,24,28-nonaoxo-1,4,7,10,13,16,19,22,25-nonaazacyclooctacosane-26-carboxamide (Compound SP-509)

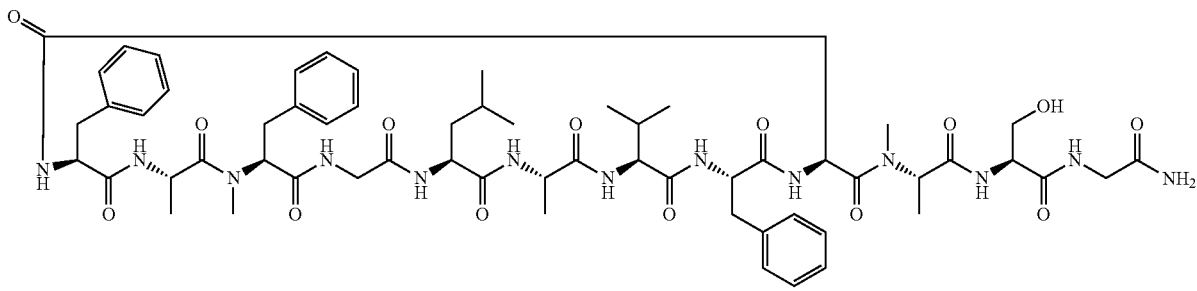 [SMILES: CC(C)C[C@@H]1NC(=O)CNC(=O)[C@H](Cc2ccccc2)N(C)C(=O)[C@H](C)NC(=O)[C@H](Cc2ccccc2)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

A mixed solution of water (32.68 ul), 4-nitrobenzenethiol (16.0 mg, 0.100 mmol), triethylamine (13.94 ul, 0.100 mmol), 1.9 M HEPES buffer (pH=8.1, 26.2 ul), a 0.5 M aqueous tris(2-carboxyethyl)phosphine solution (pH=7.6, 10.0 ul) and N-methylpyrrolidone (2.66 ul) was prepared. 10 ul of a 10 mM solution of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25- octaazaoctacosane-1-thioate (Compound SP-508) in N-methylpyrrolidone and a 11 mM solution of internal standard (4-propylbenzoic acid) in N-methylpyrrolidone (4.56 ul) were added to the mixed solution, and the mixture was stirred at 30° C. overnight. The pH at the start of the reaction was 8.3. The change in the reaction was observed by LCMS to find that the starting material compound disappeared after stirring overnight. The masses of the title compound (SP-509), the hydrolysate (Compound SP-510) and the thioester-exchanged compound (Compound SP-513) were observed to find that the mass intensity ratio (+) by LCMS is approximately 7:7:2.

Title Compound (SP-509)

LCMS (ESI) m/z=1210.4 (M+H)+

Hydrolysate (Compound SP-510)

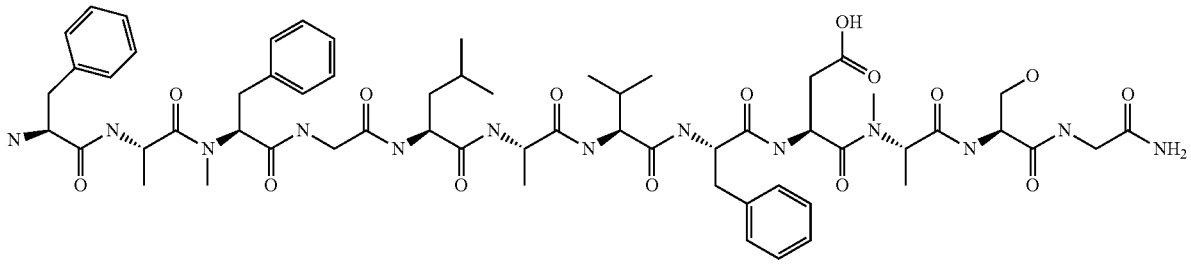 [SMILES: CC(C)C[C@H](NC(=O)CNC(=O)[C@H](Cc1ccccc1)N(C)C(=O)[C@H](C)NC(=O)[C@@H](N)Cc1ccccc1)C(=O)N[C@@H](C)C(=O)N[C@H](C(=O)N[C@@H](Cc1ccccc1)C(=O)N[C@@H](CC(=O)O)C(=O)N(C)[C@@H](C)C(=O)N[C@@H](CO)C(=O)NCC(N)=O)C(C)C]

LCMS (ESI) m/z=1228.4 (M+H)+

Thioester-Exchanged Compound (Compound SP-513)

S-(4-Nitrophenyl) (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate

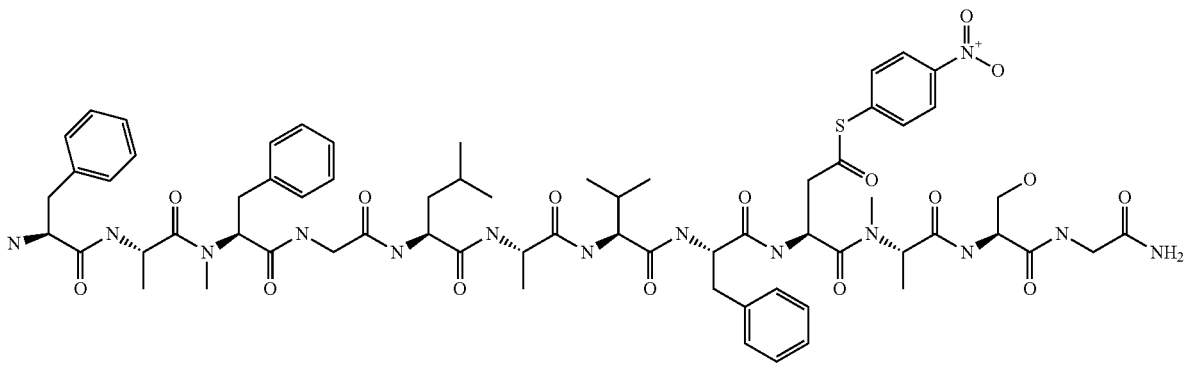

LCMS (ESI) m/z=1365.3 (M+H)+

3-1-4-2. The Case where 2,3,4,5,6-pentafluorobenzenethiol (1 M) was Used in Place of 4-(trifluoromethyl)benzenethiol (1 M) as an Additive Synthesis of (2S,5S,8S,14S,17S,20S,23S,26S)—N—(((S)-1-(((S)-1-((2-amino-2-oxoethyl)amino)-3-hydroxy-1-oxopropan-2-yl)amino)-1-oxopropan-2-yl)-2,8,23-tribenzyl-14-isobutyl-20-isopropyl-N,5,7,17-tetramethyl-3,6,9,12,15,18,21,24,28-nonaoxo-1,4,7,10,13,16,19,22,25-nonaazacyclooctacosane-26-carboxamide (Compound SP-509)

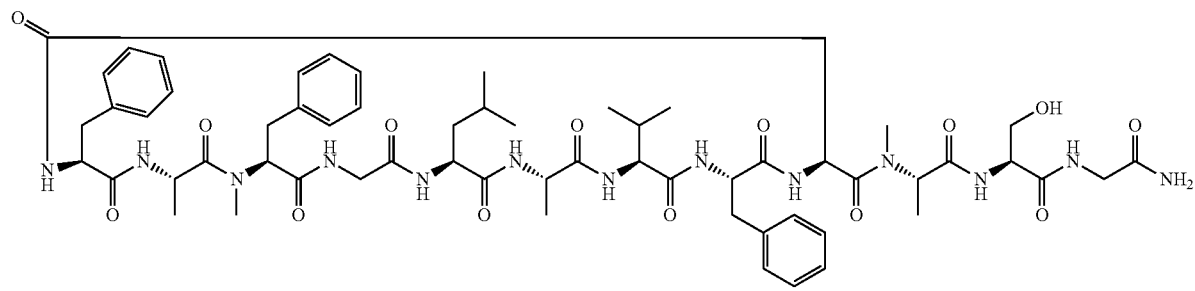 [SMILES: CC(C)C[C@@H]1NC(=O)CNC(=O)[C@H](Cc2ccccc2)N(C)C(=O)[C@H](C)NC(=O)[C@H](Cc2ccccc2)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

A mixed solution of water (22.04 ul), 2,3,4,5,6-pentafluorobenzenethiol (13.3 ul, 0.100 mmol), triethylamine (13.94 ul, 0.100 mmol), 1.9 M HEPES buffer (pH=8.1, 26.2 ul) and a 0.5 M aqueous tris(2-carboxyethyl)phosphine solution (pH=7.6, 10.0 ul) was prepared. 10 ul of a 10 mM solution of S-benzyl (3S,6S,9S,12S,15S,21S,24S,27S)-27-amino-3-(((S)-1-(((S)-1-((2-amino-2-oxoethyl)amino)-3-hydroxyl-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate (Compound SP-508) in N-methylpyrrolidone and a 11 mM solution of internal standard (4-propylbenzoic acid) in N-methylpyrrolidone (4.56 ul) were added to the mixed solution, and the mixture was stirred at 30° C. overnight. The pH at the start of the reaction was 8.0. The change in the reaction was observed by LCMS to find that the starting material compound (Compound SP-508) did not disappear even after stirring overnight. The masses of the title compound (SP-509) and the thioester-exchanged compound (Compound SP-514) were not observed. Meanwhile, the mass of the hydrolysate (Compound SP-510) was observed. The mass intensity ratio (+) by LCMS of the starting material compound (Compound SP-508) and the hydrolysate (Compound SP-510) was approximately 18:1.

Starting Material Compound (Compound SP-508)
  LCMS (ESI) m/z=1334.4 (M+H)+
Hydrolysate (Compound SP-510)
  LCMS (ESI) m/z=1228.4 (M+H)+
Thioester-Exchanged Compound (Compound SP-514)

S-(Perfluorophenyl) (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate

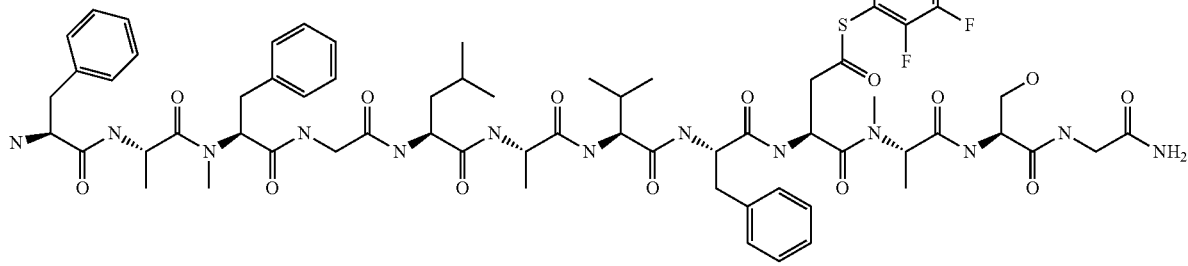

LCMS (ESI) m/z was not observed.

3-1-4-3. The Case where 2-mercaptobenzoic Acid (1 M) was Used in Place of 4-(trifluoromethyl)benzenethiol (1 M) as an Additive Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-2,8,23-tribenzyl-14-isobutyl-20-isopropyl-N,5,7,17-tetramethyl-3,6,9,12,15,18,21,24,28-nonaoxo-1,4,7,10,13,16,19,22,25-nonaazacyclooctacosane-26-carboxamide (Compound SP-509)

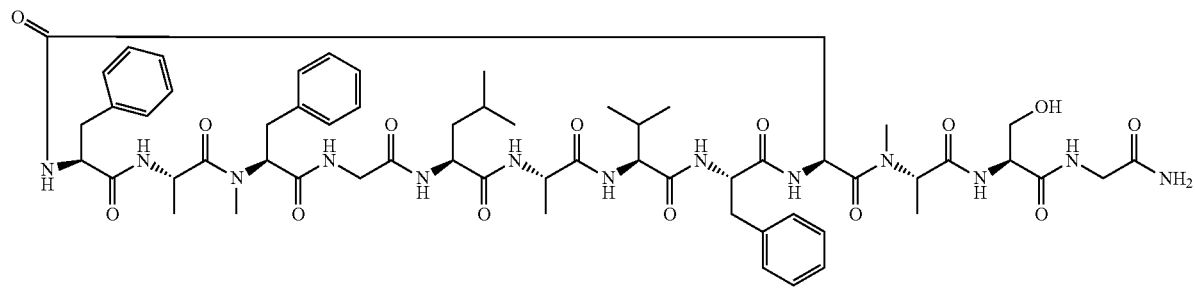 [SMILES: CC(C)C[C@@H]1NC(=O)CNC(=O)[C@H](Cc2ccccc2)N(C)C(=O)[C@H](C)NC(=O)[C@H](Cc2ccccc2)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

A mixed solution of water (32.68 ul), 2-mercaptobenzoic acid (15.0 mg, 0.100 mmol), triethylamine (13.94 ul, 0.100 mmol), 1.9 M HEPES buffer (pH=8.1, 26.2 ul), a 0.5 M aqueous tris(2-carboxyethyl)phosphine solution (pH=7.6, 10.0 ul) and N-methylpyrrolidone (2.66 ul) was prepared. 10 ul of a 10 mM solution of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate (Compound SP-508) in N-methylpyrrolidone and a 11 mM solution of internal standard (4-propylbenzoic acid) in N-methylpyrrolidone (4.56 ul) were added to the mixed solution, and the mixture was stirred at 30° C. overnight. The pH at the start of the reaction was 8.0. The change in the reaction was observed by LCMS to find that the starting material compound disappeared after stirring overnight. The masses of the title compound (SP-509), the hydrolysate (Compound SP-510) and the thioester-exchanged compound (Compound SP-515) were observed to find that the mass intensity ratio (−) by LCMS is approximately 1:10:7.

Title Compound (SP-509)
  LCMS (ESI) m/z=1208.9 (M−H)−
Hydrolysate (Compound SP-510)
  LCMS (ESI) m/z=1226.3 (M−H)−
Thioester-Exchanged Compound (Compound SP-515)

2-(((3S,6S,9S,12S,15S,21S,24S,27S)-27-amino-3-(((S)-1-H(S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosan-1-oyl)thio)benzoic Acid

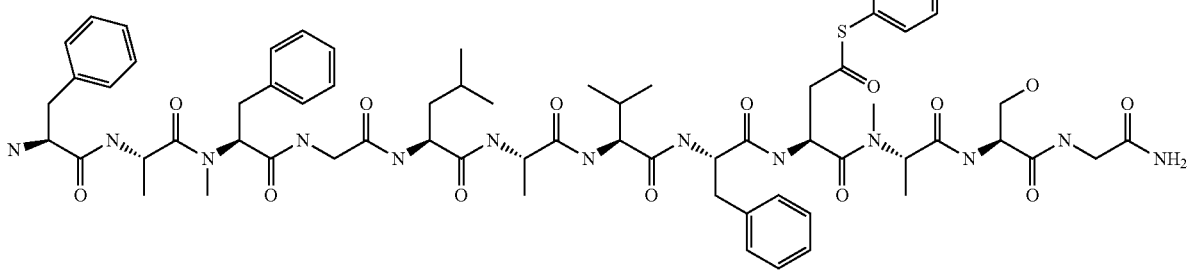

LCMS (ESI) m/z=1362.1 (M−H)−

3-1-4-4. The Case where 2-mercaptophenol (1 M) was Used in Place of 4-(trifluoromethyl)benzenethiol (1 M) as an Additive Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-2,8,23-tribenzyl-14-isobutyl-20-isopropyl-N,5,7,17-tetramethyl-3,6,9,12,15,18,21,24,28-nonaoxo-1,4,7,10,13,16,19,22,25-nonaazacyclooctacosane-26-carboxamide (Compound SP-509)

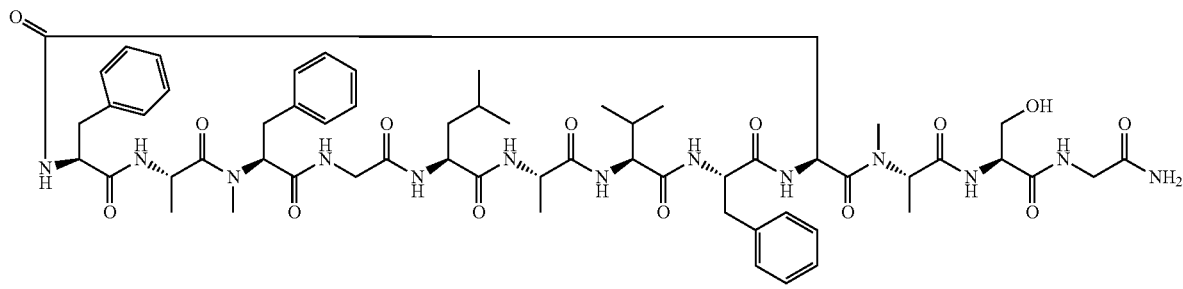 [SMILES: CC(C)C[C@@H]1NC(=O)CNC(=O)[C@H](Cc2ccccc2)N(C)C(=O)[C@H](C)NC(=O)[C@H](Cc2ccccc2)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

A mixed solution of water (24.64 ul), 2-mercaptophenol (10.05 ul, 0.100 mmol), triethylamine (13.94 ul, 0.100 mmol), 1.9 M HEPES buffer (pH=8.1, 26.2 ul), a 0.5 M aqueous tris(2-carboxyethyl)phosphine solution (pH=7.6, 10.0 ul) and N-methylpyrrolidone (0.65 ul) was prepared. 10 ul of a 10 mM solution of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate (Compound SP-508) in N-methylpyrrolidone and a 11 mM solution of internal standard (4-propylbenzoic acid) in N-methylpyrrolidone (4.56 ul) were added to the mixed solution, and the mixture was stirred at 30° C. for 1 hour. The pH at the start of the reaction was 8.0. The change in the reaction was observed by LCMS to find that the starting material compound disappeared after stirring for 1 hour. The masses of the title compound (SP-509) and the hydrolysate (Compound SP-510) were observed to find that the mass intensity ratio (+) by LCMS is approximately 1.1:1.

Title Compound (SP-509)
  LCMS (ESI) m/z=1210.4 (M+H)+
Hydrolysate (Compound SP-510)
  LCMS (ESI) m/z=1228.4 (M+H)+

3-1-4-5. The Case where 2-Mercaptophenol (0.5 M) and (S,Z)-(2,2-dimethyl-1,3-dioxolan-4-yl)methyl 2-cyano-2-(hydroxyimino)acetate (0.5 M) were Used in Place of 4-(trifluoromethyl)benzenethiol (1 M) as Additives Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-2,8,23-tribenzyl-14-isobutyl-20-isopropyl-N,5,7,17-tetramethyl-3,6,9,12,15,18,21,24,28-nonaoxo-1,4,7,10,13,16,19,22,25-nonaazacyclooctacosane-26-carboxamide (Compound SP-509)

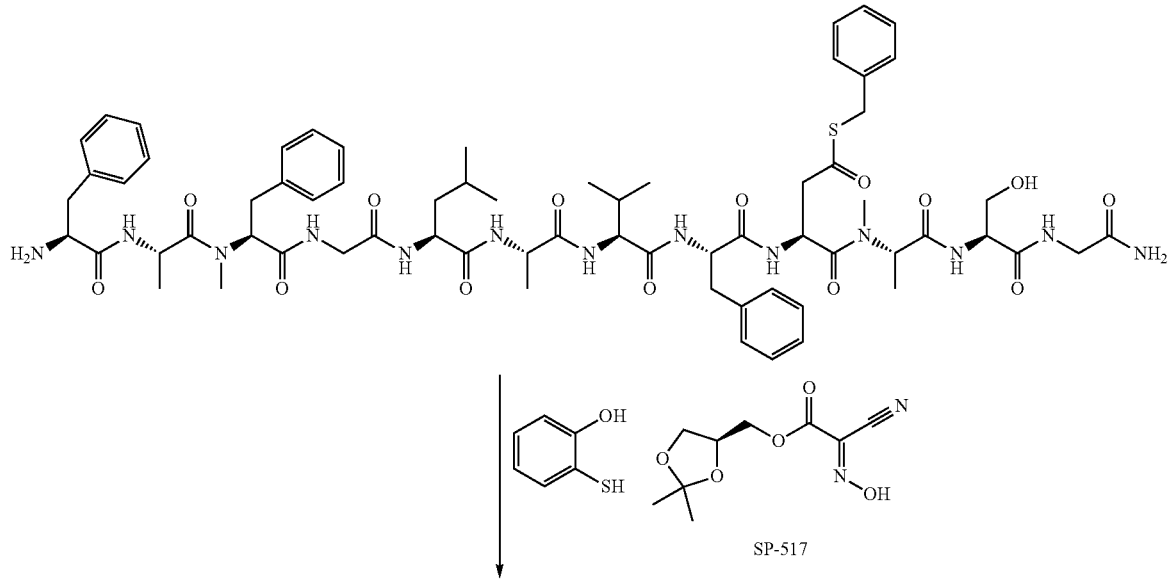

SP-517

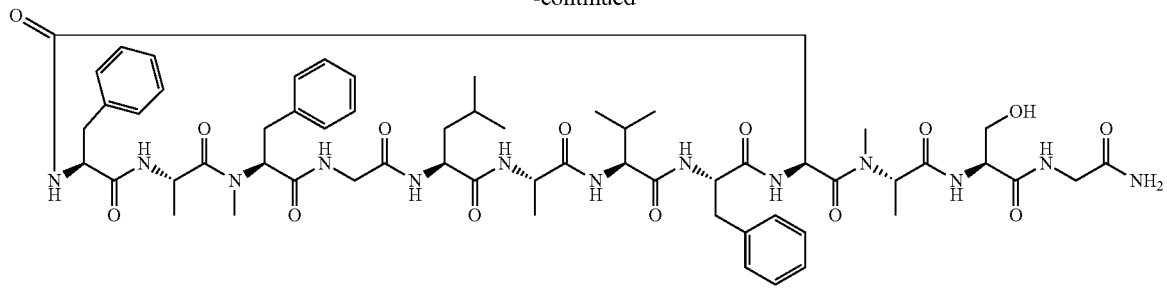

A mixed solution of water (2.46 ul), 2-mercaptophenol (5.03 ul, 0.050 mmol), (S,Z)-(2,2-dimethyl-1,3-dioxolan-4-yl)methyl 2-cyano-2-(hydroxyimino)acetate separately synthesized according to a conventional method (Organic Letter, 2012, 14, 3372-3375) (Compound SP517) (11.0 mg, 0.050 mmol), triethylamine (13.94 ul, 0.100 mmol), 1 M phosphate buffer (pH=7.7, 52.4 ul), a 0.5 M aqueous tris(2-carboxyethyl)phosphine solution (pH=7.6, 10.0 ul) and N-methylpyrrolidone (1.65 ul) was prepared. 10 ul of a 10 mM solution of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate (Compound SP-508) in N-methylpyrrolidone and a 11 mM solution of internal standard (4-propylbenzoic acid) in N-methylpyrrolidone (4.56 ul) were added to the mixed solution, and the mixture was stirred at 30° C. for 1 hour. The pH at the start of the reaction was 7.0. The time course of the reaction was observed by LCMS. After stirring for 1 hour, the masses of the title compound (SP-509), the hydrolysate (Compound SP-510) and the ester-exchanged compound (Compound SP-516) were observed to find that the mass intensity ratio (−) by LCMS is approximately 4:5:2.

Title Compound (SP-509)

LCMS (ESI) m/z=1208.1 (M−H)−

Hydrolysate (Compound SP-510)

LCMS (ESI) m/z=1226.2 (M−H)−

Ester-Exchanged Compound (Compound SP-516)

((S)-2,2-Dimethyl-1,3-dioxolan-4-yl)methyl (7S,10S,13S,16S,19S,25S,28S,31S,E)-31-amino-7-(((S)-1-(((S)-1-((2-amino-2-oxoethyl)amino)-3-hydroxy-1-oxopropan-2-yl)amino)-1-oxopropan-2-yl)(methyl)carbamoyl)-10,25-dibenzyl-2-cyano-19-isobutyl-13-isopropyl-16,26,28-trimethyl-5,9,12,15,18,21,24,27,30-nonaoxo-32-phenyl-4-oxa-3,8,11,14,17,20,23,26,29-nonaazadotriacont-2-en-1-oate

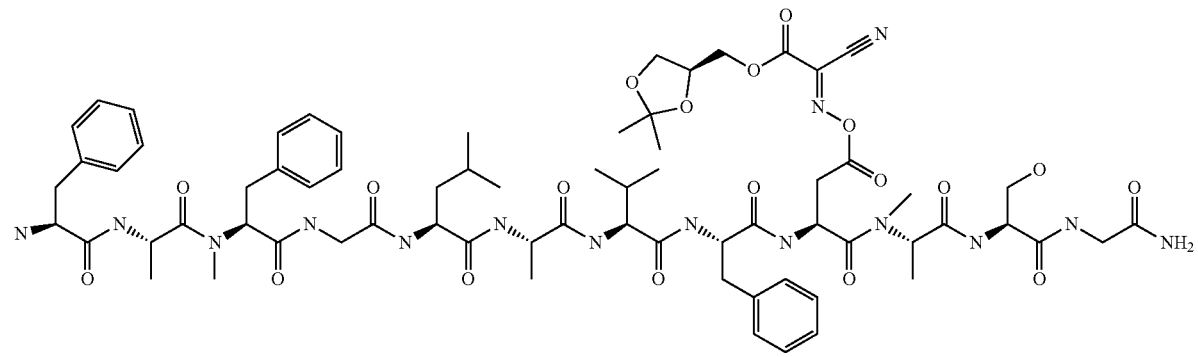 [SMILES: CC(C)C[C@H](NC(=O)CNC(=O)[C@H](Cc1ccccc1)N(C)C(=O)[C@H](C)NC(=O)[C@@H](N)Cc1ccccc1)C(=O)N[C@@H](C)C(=O)N[C@H](C(=O)N[C@@H](Cc1ccccc1)C(=O)N[C@@H](CC(=O)O/N=C(\C#N)C(=O)OC[C@@H]1COC(C)(C)O1)C(=O)N(C)[C@@H](C)C(=O)N[C@@H](CO)C(=O)NCC(N)=O)C(C)C]

LCMS (ESI) m/z=1436.4 (M−H)−

3-1-4-6. The Case where (S,Z)-(2,2-dimethyl-1,3-dioxolan-4-yl)methyl 2-cyano-2-(hydroxyimino)acetate (0.5 M) was Used in Place of 4-(trifluoromethyl)benzenethiol (1 M) as an Additive Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-2,8,23-tribenzyl-14-isobutyl-20-isopropyl-N,5,7,17-tetramethyl-3,6,9,12,15,18,21,24,28-nonaoxo-1,4,7,10,13,16,19,22,25-nonaazacyclooctacosane-26-carboxamide (Compound SP-509)

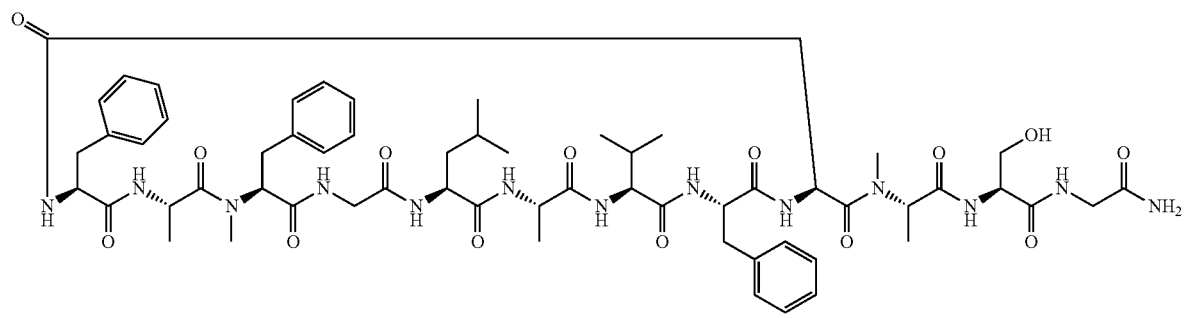 [SMILES: CC(C)C[C@@H]1NC(=O)CNC(=O)[C@H](Cc2ccccc2)N(C)C(=O)[C@H](C)NC(=O)[C@H](Cc2ccccc2)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

A mixed solution of water (6.48 ul), (S,Z)-(2,2-dimethyl-1,3-dioxolan-4-yl)methyl 2-cyano-2-(hydroxyimino)acetate separately synthesized according to a conventional method (Organic Letter, 2012, 14, 3372-3375) (Compound SP517) (11.0 mg, 0.050 mmol), triethylamine (13.94 ul, 0.100 mmol), 1 M phosphate buffer (pH=7.7, 52.4 ul), a 0.5 M aqueous tris(2-carboxyethyl)phosphine solution (pH=7.6, 10.0 ul) and N-methylpyrrolidone (2.7 ul) was prepared. 10 ul of a 10 mM solution of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate (Compound SP-508) in N-methylpyrrolidone and a 11 mM solution of internal standard (4-propylbenzoic acid) in N-methylpyrrolidone (4.56 ul) were added to the mixed solution, and the mixture was stirred at 30° C. for 1 hour. The pH at the start of the reaction was 9.8. The time course of the reaction was observed by LCMS. After stirring for 1 hour, the mass of the hydrolysate (Compound SP-510) was observed. The masses of the title compound (SP-509) and the ester-exchanged compound (SP-516) were not observed.
Hydrolysate (Compound SP-510)
LCMS (ESI) m/z=1226.7 (M−H)−

3-1-4-7. The Case where Benzenethiol (100 mM) was Used in Place of 4-(trifluoromethyl)benzenethiol (100 mM) as an Additive Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-8,23-dibenzyl-14-isobutyl-20-isopropyl-N,2,5,7,17-pentamethyl-3,6,9,12,15,18,21,24,28-nonaoxo-1,4,7,10,13,16,19,22,25-nonaazacyclooctacosane-26-carboxamide (Compound SP-511)

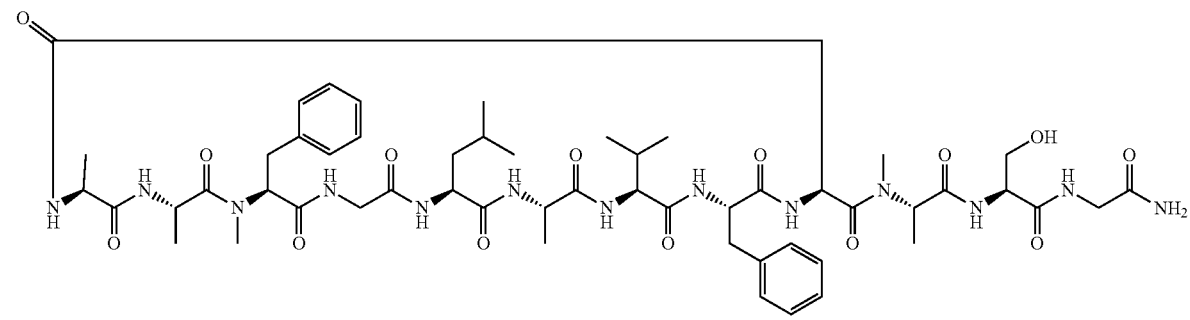 [SMILES: CC(C)C[C@@H]1NC(=O)CNC(=O)[C@H](Cc2ccccc2)N(C)C(=O)[C@H](C)NC(=O)[C@H](C)NC(=O)C[C@@H](C(=O)N(C)[C@@H](C)C(=O)N[C@@H](CO)C(=O)NCC(N)=O)NC(=O)[C@H](Cc2ccccc2)NC(=O)[C@H](C(C)C)NC(=O)[C@H](C)NC1=O]

A mixed solution of water (41.86 ul), benzenethiol (1.03 ul, 0.01 mmol) and triethylamine (1.39 ul, 0.01 mmol) was prepared. 1.9 M HEPES buffer (pH=8.1, 26.2 ul) and a 0.5 M aqueous tris(2-carboxyethyl)phosphine solution (pH=7.6, 10 ul) were added to the mixed solution. Further, 10 ul of a 10 mM solution of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate (Compound SP-504) in N-methylpyrrolidone, a 11 mM solution of internal standard (4-propylbenzoic acid) in N-methylpyrrolidone (4.56 ul) and N-methylpyrrolidone (4.96 ul) were added, and the mixture was stirred at 30° C. overnight. The pH at the start of the reaction was 7.9. The time course of reaction was observed by LCMS to confirm that the title compound was produced. After stirring overnight, the conversion rate was 94% based on the area ratio to the internal standard, and the production ratio of the title compound (SP-511) and the hydrolysate (Compound SP-512) was about 3:1 based on the UV area ratio by LCMS.

Title Compound (SP-511)
LCMS (ESI) m/z=1132.3 (M−H)−
Retention time: 0.63 min (analysis condition SQDFA05)
Hydrolysate (Compound SP-512)
LCMS (ESI) m/z=1150.2 (M−H)−
Retention time: 0.48 min (analysis condition SQDFA05)

3-1-4-8. The Case where Benzenethiol (1 N) was Used in Place of 4-(trifluoromethyl)benzenethiol (1 M) as an Additive Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-8,23-dibenzyl-14-isobutyl-20-isopropyl-N,2,5,7,17-pentamethyl-3,6,9,12,15,18,21,24,28-nonaoxo-1,4,7,10,13,16,19,22,25-nonaazacyclooctacosane-26-carboxamide (Compound SP-511)

A mixed solution of water (24.44 ul), benzenethiol (10.3 ul, 0.10 mmol) and triethylamine (13.9 ul, 0.10 mmol) was prepared. 1.9 M HEPES buffer (pH=8.1, 26.2 ul) and a 0.5 M aqueous tris(2-carboxyethyl)phosphine solution (pH=7.6, 10 ul) were added to the mixed solution. Further, 10 ul of a 10 mM solution of S-benzyl (3S,6S,9S,12S,15S,21S,24S,27S)-27-amino-3-(((S)-1-(((S)-1-((2-amino-2-oxoethyl)amino)-3-hydroxyl-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-28-phenyl-4,7,10,13,16,19,22,25-octaazaoctacosane-1-thioate (Compound SP-504) in N-methylpyrrolidone and a 11 mM solution of internal standard (phthalic acid) in N-methylpyrrolidone (4.56 ul) were added, and the mixture was stirred at 30° C. for 40 hours. The pH at the start of the reaction was 8.1. The time course of reaction was observed by LCMS to confirm that the title compound was produced. After stirring for 40 hours, the starting material (Compound SP-504) disappeared, and the production ratio of the title compound (SP-511) and the hydrolysate (Compound SP-512) was about 7:1 based on the UV area ratio by LCMS.

Title Compound (SP-511)
LCMS (ESI) m/z=1132.3 (M−H)−
Retention time: 0.63 min (analysis condition SQDFA05)
Hydrolysate (Compound SP-512)
LCMS (ESI) m/z=1150.4 (M−H)−
Retention time: 0.48 min (analysis condition SQDFA05)

The above results revealed that various arylthioesters can be used as additives. As revealed above, higher electron-donating properties of thiol groups are more advantageous in order to activate translatable thioesters at high reaction rates, higher electron-withdrawing properties of thiol groups are more advantageous in order to achieve cyclization reaction between activated thioesters and amines at sufficient rates, and it is important to balance both properties.

In the case of highly reactive amines such as glycine, sufficient cyclization reaction selectivity (cyclization reaction:hydrolysis=30:1) can be achieved when benzenethiol is used as an additive at a concentration of 10 mM. However, in the case of less reactive amines such as alanine, the cyclization reaction:hydrolysis is reduced to 3:1 under conditions where the benzenethiol concentration is increased from 10 mM to 100 mM. Further, the ratio is 7:1 even under conditions where the benzenethiol concentration is increased to 1 M, and such selectivity (30:1) as in highly reactive amines cannot be achieved. In this case, the cyclization:hydrolysis ratio is 30:1 and the selectivity can be improved when 4-(trifluoromethyl)benzenethiol having an electron-withdrawing group is used at 1 M in place of benzenethiol as an additive. However, the selectivity is

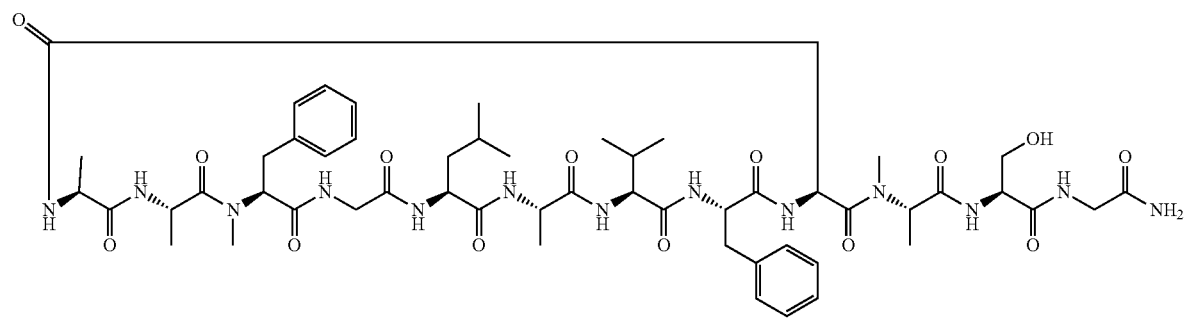

decreased (6:1) when the 4-(trifluoromethyl)benzenethiol concentration is reduced to 100 mM. Accordingly, in the case of less reactive amines, it is desirable to use 4-(trifluoromethyl)benzenethiol as an additive at a high concentration.

Exchange reaction to active esters can also be achieved by adding a plurality of additives instead of a single additive. Although activation with (S,Z)-(2,2-dimethyl-1,3-dioxolan-4-yl)methyl 2-cyano-2-(hydroxyimino)acetate (Compound SP-517) could not achieve direct conversion from translatable thioesters, it was revealed that translatable thioesters can be first activated with 2-mercaptophenol and then further activated with this compound. (S,Z)-(2,2-dimethyl-1,3-dioxolan-4-yl)methyl 2-cyano-2-(hydroxyimino)acetate (Compound SP-517) has been reported to cause Highly efficient amidation reaction to N-methylated amino acids or peptides in water (Organic Letter, 2012, 14, 3372-3375), and the fact that activation to this active species was achieved through two-step activation is worth noting.

3-2-1. Cyclization Reaction in a Reaction Translation Solution Under Reaction Optimization Conditions As a result of carrying out cyclization reaction in a reaction translation solution according to the reaction condition optimization as described above, the ratio of the hydrolysate could be decreased and the ratio of the intended compound could be improved as compared with conditions under which experiments for cyclizing translated peptides were carried out.

Synthesis of (2S,5S,8S,14S,17S,20S,23S,26S)—N—((S)-1-(((S)-1-((2-amino-2-oxoethyl)amino)-3-hydroxy-1-oxopropan-2-yl)amino)-1-oxopropan-2-yl)-8,23-dibenzyl-14-isobutyl-20-isopropyl-N,2,5,7,17-pentamethyl-3,6,9,12,15,18,21,24,28-nonaoxo-1,4,7,10,13,16,19,22,25-nonaazacyclooctacosane-26-carboxamide (Compound SP-511)

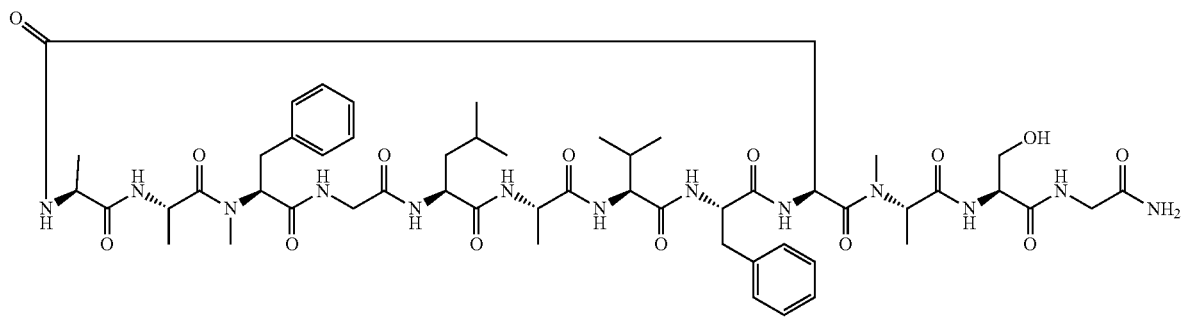

4-(Trifluoromethyl)benzenethiol (6.8 µL, 0.050 mmol) and triethylamine (7.0 µl, 0.050 mmol) were dissolved in HEPES buffer (pH=7.6, 1.9 M, 8.2 µl) to prepare a thiol solution.

A solution of 4-propylbenzoic acid as internal standard in NMP (11 mM, 2.25 µl) was added to a solution of S-benzyl (3S,6S,9S,12S,15S,21S,24S,27S)-27-amino-3-(((S)-1-(((S)-1-((2-amino-2-oxoethyl)amino)-3-hydroxy-1-oxopropan-2-yl)amino)-1-oxopropan-2-yl)(methyl)carbamoyl)-6,21-dibenzyl-15-isobutyl-9-isopropyl-12,22,24-trimethyl-5,8,11,14,17,20,23,26-octaoxo-4,7,10,13,16,19,22,25-octaazaoctacosane-1-thioate (Compound SP-504) in NMP (10 mM, 5.0 µl, 0.050 µmol). Next, a translation buffer (6.25 µl), PURESYSTEM® classic II Sol. B (BioComber, product No. PURE2048C) (10 µl) and 20 natural amino acid solutions (each 5 mM, 2.5 µl) were added.

The ingredients of the translation buffer are 8 mM GTP, 8 mM ATP, 160 mM creatine phosphate, 400 mM HEPES-KOH, pH 7.6, 800 mM potassium acetate, 48 mM magnesium acetate, 16 mM spermidine, 8 mM dithiothreitol, 0.8 mM 10-HCO—H4 folate and 12 mg/ml *E. coli* MRE600 (RNase negative)-derived tRNA (Roche). An aqueous tris (2-carboxyethyl)phosphine solution (pH=7.5, 1.25 M, 2.0 µl) and the thiol solution prepared above were added thereto. The pH of the reaction solution at this time was 7.7.

The reaction solution was stirred at 30° C. for 22 hours and then analyzed by LC/MS to confirm that the title compound was produced. The pH of the reaction solution after stirring for 22 hours was 9.4. The production ratio of the title compound (Compound SP-511) and the hydrolysate (Compound SP-512) was 2.6:1 based on the UV area ratio.
Title Compound (SP-511)
LCMS (ESI) m/z=1134.4 (M+H)+
Retention time: 0.64 min (analysis condition SQDFA05)
Hydrolysate (Compound SP-512)
LCMS (ESI) m/z=1152.5 (M+H)+
Retention time: 0.48 min (analysis condition SQDFA05)

3-3. Cyclization Reaction Using N-Terminal MeAla Model Peptides

Model reaction of a N-alkylamino acid, MeAla, was carried out like those of Ala and Phe, and production of cyclized compounds was confirmed.

3-3-1. Synthesis of N-Terminal MeAla Model Peptides

Synthesis of (6S,9S,12S,15S,18S,24S,27S,30S,33S)-18,30-dibenzyl-12,24-diisobutyl-9,27-diisopropyl-2,2,5,6,11,17,23,26-octamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-((R)-1-(trityloxy)ethyl)-3-oxa-5,8,11,14,17,20,23,26,29,32-decaazapentatriacontan-35-oic Acid (Boc-MeAla-Val-MeLeu-Thr(Trt)-MePhe-Gly-MeLeu-MeVal-Phe-Asp-MePhe-Ala-piperidine) (Compound SP-518) (SEQ ID NO: 341)

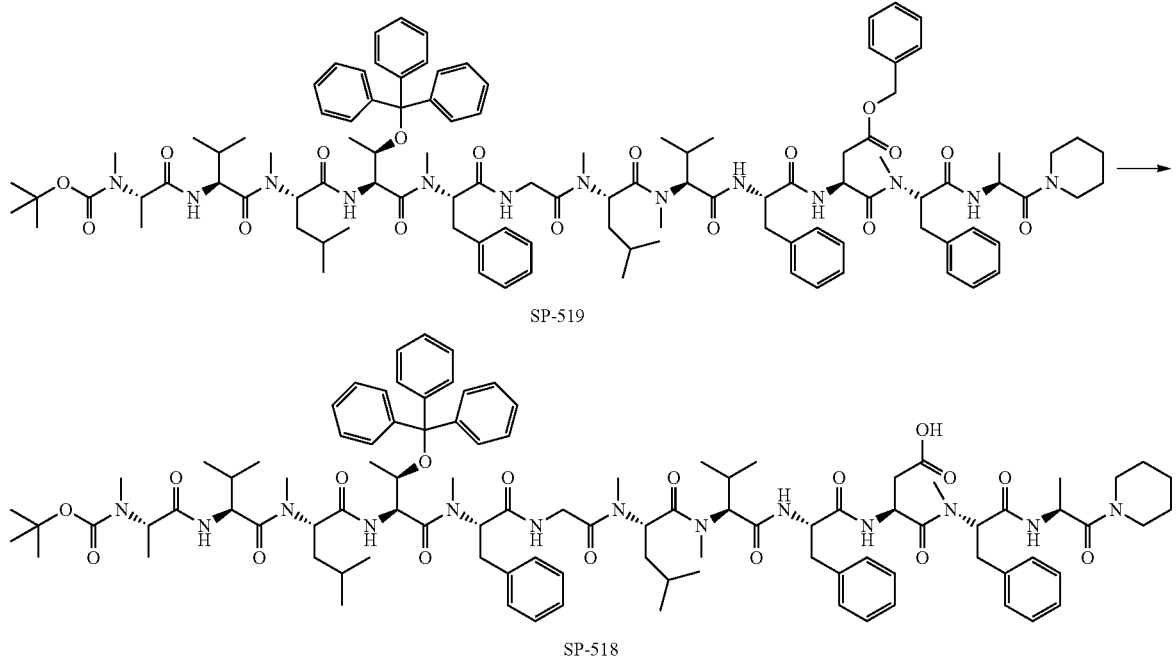

SP-519

SP-518

Hydroxypalladium/carbon (172 mg, 50% wet w/w) was added to a solution of benzyl (6S,9S,12S,15S,18S,24S,27S,30S,33S)-18,30-dibenzyl-12,24-diisobutyl-9,27-diisopropyl-2,2,5,6,11,17,23,26-octamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-((R)-1-(trityloxy)ethyl)-3-oxa-5,8,11,14,17,20,23,26,29,32-decaazapentatriacontan-35-oate (Compound SP-519, Boc-MeAla-Val-MeLeu-Thr(Trt)-MePhe-Gly-MeLeu-MeVal-Phe-Asp(OBn)-MePhe-Ala-piperidine (SEQ ID NO: 342)) synthesized according to a conventional method (516 mg, 0.274 mmol) in methanol (3.5 ml), the atmosphere was replaced with hydrogen, and the mixture was then stirred at room temperature for 2.5 hours. The reaction solution was then filtered through celite, and the filtrate was concentrated under reduced pressure to afford the title compound (SP-518) (468 mg, 95%).

LCMS (ESI) m/z=1790.9 (M−H)−

Retention time: 0.87 min (analysis condition SQDAA50)

Synthesis of S-benzyl (6S,9S,12S,15S,18S,24S,27S, 30S,33S)-18,30-dibenzyl-12,24-diisobutyl-9,27-diisopropyl-2,2,5,6,11,17,23,26-octamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-((R)-1-(trityloxy)ethyl)-3-oxa-5,8,11,14,17,20,23,26,29,32-decaazapentatriacontane-35-thioate (Boc-MeAla-Val-MeLeu-Thr(Trt)-MePhe-Gly-MeLeu-MeVal-Phe-Asp(SBn)-MePhe-Ala-piperidine) (Compound SP-520) (SEQ ID NO: 343)

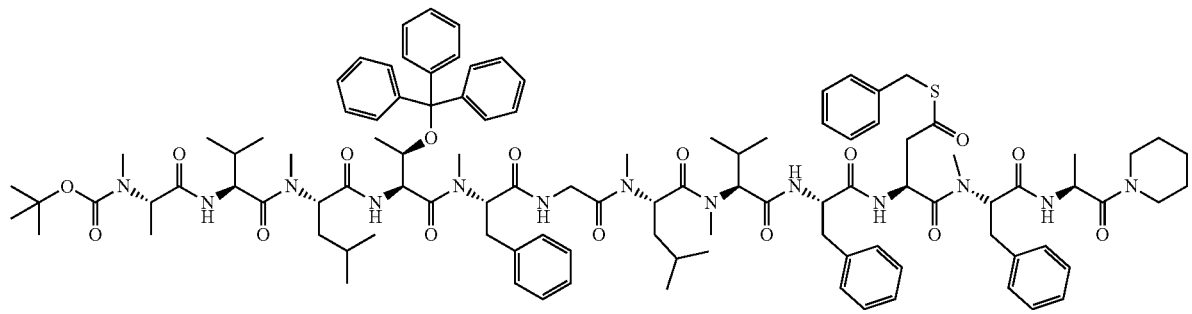

(6S,9S,12S,15S,18S,24S,27S,30S,33S)-18,30-dibenzyl-12,24-diisobutyl-9,27-diisopropyl-2,2,5,6,11,17,23,26-octamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-((R)-1-(trityloxy)ethyl)-3-oxa-5,8,11,14,17,20,23,26,29,32-decaazapentatriacontan-35-oic acid (Compound SP-518) (50.0 mg, 0.028 mmol) was dissolved in dichloromethane (320 µl) and DMF (80 µl), phenylmethanethiol (6.93 mg, 0.056 mmol), DIC (7.04 mg, 0.056 mmol) and N,N-dimethylpyridin-4-amine (2.58 mg, 0.021 mmol) were added and the mixture was stirred at room temperature overnight. The reaction solution was concentrated under reduced pressure, and the resulting residue was purified by column chromatography (10 mM aqueous ammonium acetate solution:methanol) to afford the title compound (SP-520) (37.6 mg, 71.09).

LCMS (ESI) m/z=1897.3 (M−H)−

Retention time: 0.99 min (analysis condition SQDAA50)

Synthesis of S-benzyl (3S,6S,9S,12S,15S,21S,24S, 27S,30S)-15,27-dibenzyl-12-((R)-1-hydroxyethyl)-9, 21-diisobutyl-6,24-diisopropyl-3,8,14,20,23-pentamethyl-30-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28-nonaoxo-2,5,8,11,14,17,20,23,26,29-decaazadotriacontane-32-thioate (MeAla-Val-MeLeu-Thr-MePhe-Gly-MeLeu-MeVal-Phe-Asp(SBn)-MePhe-Ala-piperidine) (Compound SP-521) (SEQ ID NO: 344)

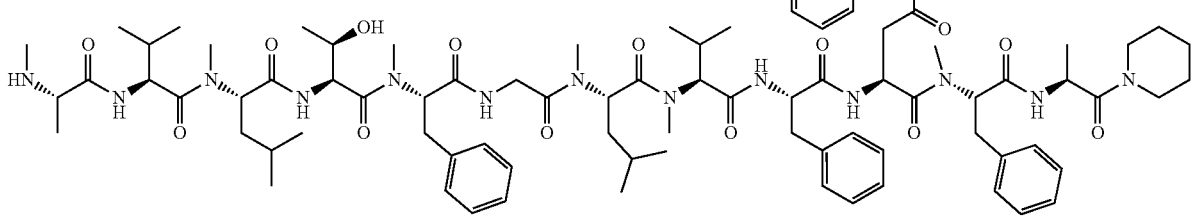

S-benzyl (6S,9S,12S,15S,18S,24S,27S,30S,33S)-18,30-dibenzyl-12,24-diisobutyl-9,27-diisopropyl-2,2,5,6,11,17,23,26-octamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-((R)-1-(trityloxy)ethyl)-3-oxa-5,8,11,14,17,20,23,26,29,32-decaazapentatriacontane-35-thioate (Compound SP-520) (37.6 mg, 0.020 mmol) was dissolved in dichloromethane (300 µl), TFA (150.0 µl, 1.95 mmol) was added and the mixture was stirred at room temperature for 1.5 hours.

Triisopropylsilane (15.7 mg, 0.099 mmol) was added to the reaction solution, after which the reaction solution was concentrated under reduced pressure, and the resulting residue was purified by column chromatography (0.1% aqueous FA solution:0.1% FA-acetonitrile solution) to afford the title compound (SP-521) (18.5 mg, 60.0%).

LCMS (ESI) m/z=1555.1 (M−H)−

Retention time: 0.79 min (analysis condition SQDFA05)

Synthesis of 2-(ethyldisulfanyl)-6-methylphenyl (6S,9S,12S,15S,18S,24S,27S,30S,33S)-18,30-dibenzyl-12,24-diisobutyl-9,27-diisopropyl-2,2,5,6,11,17, 23,26-octamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22, 25,28,31-decaoxo-15-((R)-1-(trityloxy)ethyl)-3-oxa-5,8,11,14,17,20,23,26,29,32-decaazapentatriacontan-35-oate (Boc-MeAla-Val-MeLeu-Thr(Trt)-MePhe-Gly-MeLeu-MeVal-Phe-Asp(O(2-EtSS-6-Me-pH))-MePhe-Ala-piperidine) (Compound SP-522) (SEQ ID NO: 345)

In the present specification, a compound having side chain carboxylic acid of Asp substituted with a 2-(ethyldisulfanyl)-6-methylphenyl ester group is described as Asp(O (2-EtSS-6-Me-Ph)). This site contained in a peptide is also described in the same manner.

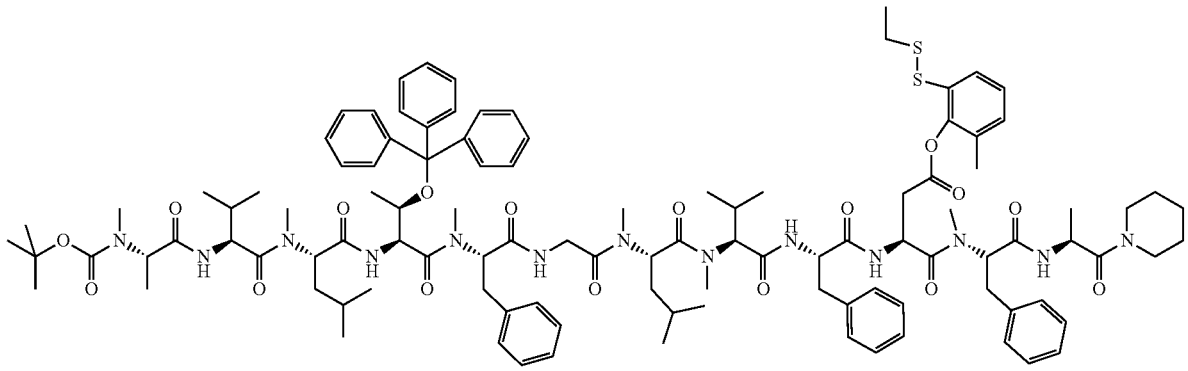

2-(ethyldisulfanyl)-6-methylphenol separately synthesized according to a conventional method (J. AM. CHEM. SOC. 2009, 131, 5432-5437) (8.38 mg, 0.042 mmol), N,N'-methanediylidenebis(propan-2-amine) (6.52 ul, 0.042 mmol) and N,N-dimethylpyridin-4-amine (3.41 mg, 0.028 mmol) were added to a solution of (6S,9S,12S,15S,18S,24S, 27S,30S,33S)-18,30-dibenzyl-12,24-diisobutyl-9,27-diisopropyl-2,2,5,6,11,17,23,26-octamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28, 31-decaoxo-15-NR)-1-(trityloxy)ethyl)-3-oxa-5,8,11,14,17, 20,23,26,29,32-decaazapentatriacontan-35-oic acid (Compound SP-518) (50.0 mg, 0.028 mmol) in dichloromethane (300 ul), and the mixture was stirred at room temperature overnight. The reaction solution was then concentrated under reduced pressure and purified by reverse phase silica gel column chromatography (10 mM aqueous ammonium acetate solution/methanol=70/30→0/100) to afford the title compound (Compound SP-522) (43.8 mg, 80%).

LCMS (ESI) m/z=1973.5 (M−H)−

Retention time: 1.01 min (analysis condition SQDAA50)

Synthesis of 2-(ethyldisulfanyl)-6-methylphenyl (3S,6S,9S,12S,15S,21S,24S,27S,30S)-15,27-dibenzyl-12-((R)-1-hydroxyethyl)-9,21-diisobutyl-6,24-diisopropyl-3,8,14,20,23-pentamethyl-30-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28-nonaoxo-2,5,8,11,14,17,20,23,26,29-decaazadotriacontan-32-oate (MeAla-Val-MeLeu-Thr-MePhe-Gly-MeLeu-MeVal-Phe-Asp(O(2-EtSS-6-Me-Ph))-MePhe-Ala-piperidine) (Compound SP-523) (SEQ ID NO: 237)

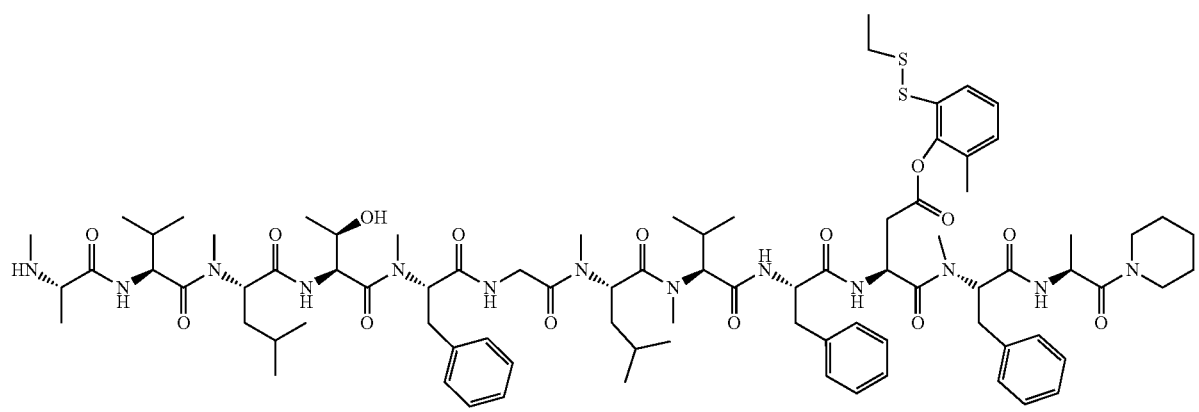

Trifluoroacetic acid (100 ul) and triisopropylsilane (22.3 ul, 0.109 mmol) were added to a solution of 2-(ethyldisulfanyl)-6-methylphenyl (6S,9S,12S,15S,18S,24S,27S,30S,33S)-18,30-dibenzyl-12,24-diisobutyl-9,27-diisopropyl-2,2,5,6,11,17,23,26-octamethyl-33-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28,31-decaoxo-15-NR)-1-(trityloxy)ethyl)-3-oxa-5,8,11,14,17,20,23,26,29,32-decaazapentatriacontan-35-oate (Compound SP-522) (42.9 mg, 22 umol) in dichloromethane (200 ul), and the mixture was stirred at room temperature for 10 minutes. The reaction solution was then concentrated under reduced pressure and purified by reverse phase silica gel column chromatography (0.1% aqueous formic acid solution/0.1% formic acid-acetonitrile solution=70/30→0/100) to afford the title compound (Compound SP-523) (11.7 mg, 33%).

LCMS (ESI) m/z=1632.9 (M+H)+

Retention time: 0.83 min (analysis condition SQDFA05)

3-3-2. Cyclization Reaction Examples in N-Terminal MeAla Model Peptides

Synthesis of (2R,5S,8S,11S,14S,20S,23S,26S,29S)-14,26-dibenzyl-11-((R)-1-hydroxyethyl)-8,20-diisobutyl-5,23-diisopropyl-N,1,2,7,13,19,22-heptamethyl-3,6,9,12,15,18,21,24,27,31-decaoxo-N—((S)-1-oxo-1-(((S)-1-oxo-1-(piperidin-1-yl)propan-2-yl)amino)-3-phenylpropan-2-yl)-1,4,7,10,13,16,19,22,25,28-decaazacyclohentriacontane-29-carboxamide (Compound SP-524)

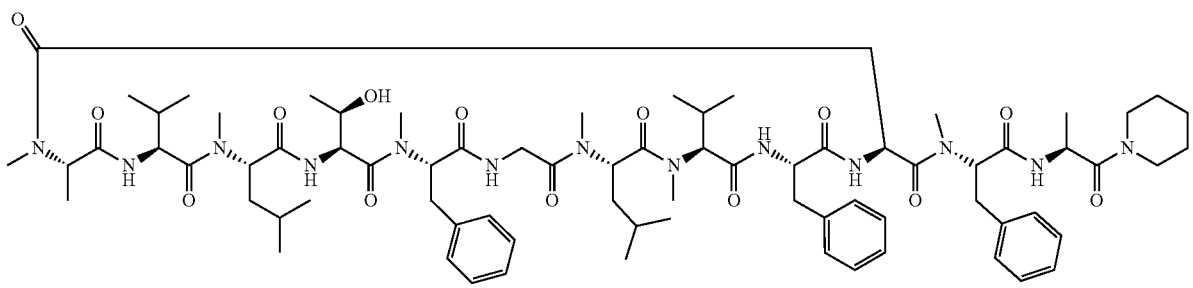

4-(Trifluoromethyl)benzenethiol in 400 mM disodium hydrogenphosphate buffer (0.2 M, 50.0 μl, 10.0 μmol), a solution of triethylamine in NMP (1 M, 10 μl, 10.0 μmol) and NMP (30.0 μl) were added to a solution of S-benzyl (3S,6S,9S,12S,15S,21S,24S,27S,30S)-15,27-dibenzyl-12-((R)-1-hydroxyethyl)-9,21-diisobutyl-6,24-diisopropyl-3,8,14,20,23-pentamethyl-30-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28-nonaoxo-2,5,8,11,14,17,20,23,26,29-decaazadotriacontane-32-thioate (Compound SP-521) in NMP (10 mM, 10 μl, 0.10 μmol), and the mixture was stirred at room temperature for 4 hours. Analysis by LC/MS confirmed that the title compound (SP-524) was produced.

LCMS (ESI) m/z=1432.8 (M+H)+

Retention time: 1.06 min (analysis condition SQDFA05)

Synthesis of (2S,5S,8S,11S,14S,20S,23S,26S,29S)-14,26-dibenzyl-11-((R)-1-hydroxyethyl)-8,20-diisobutyl-5,23-diisopropyl-N,1,2,7,13,19,22-heptamethyl-3,6,9,12,15,18,21,24,27,31-decaoxo-N—((S)-1-oxo-1-(((S)-1-oxo-1-(piperidin-1-yl)propan-2-yl)amino)-3-phenylpropan-2-yl)-1,4,7,10,13,16,19,22,25,28-decaazacyclohentriacontane-29-carboxamide (Compound SP-524)

5-1. Preparation of Puromycin-Containing Template mRNAs and Translation Synthesis of RNA-Peptide Fusions mRNAs (SEQ ID NO: RM-D3, R-D4, R-D5) were prepared by in vitro transcription from three DNAs prepared by PCR (SEQ ID NO: DM-D1, DM-D2, DM-D3) as templates, respectively, and purified using RNeasy mini kit (Qiagen). 50 μM puromycin linker (Sigma) (SEQ ID NO: C-D1), 1×T4 RNA ligase reaction buffer (NEB), 1 mM DTT, 1 mM ATP, 0.02% BSA (Takara), 510 μM PEG2000 (Wako), 10% DMSO, 1% (v/v) RNasein Ribonuclease inhibitor (Promega, N2111) and 0.85 units/μl T4 RNA ligase (NEB) were added to 10 μM of each mRNA, ligation reaction was carried out at 15° C. overnight, and the mixture was then purified with RNeasy MinElute kit (Qiagen). Next, the aforementioned cell-free translation solution as well as 0.25 mM Ser, 0.25 mM Gly, 0.25 mM Pro, 0.25 mM Arg, 0.25 mM Thr, 0.25 mM Tyr and 50 μM Asp(SBn)-tRNAGluAAG (Compound AT-7-A) were added to 1 μM each of the three mRNA-puromycin linker conjugates prepared above as templates, and the mixture was incubated at 37° C. for 60 minutes and then at room temperature for 12 minutes. When the mRNA-puromycins derived from OT98RNA (SEQ ID NO: RM-D4) and OT99RNA (SEQ ID NO: RM-D5) were

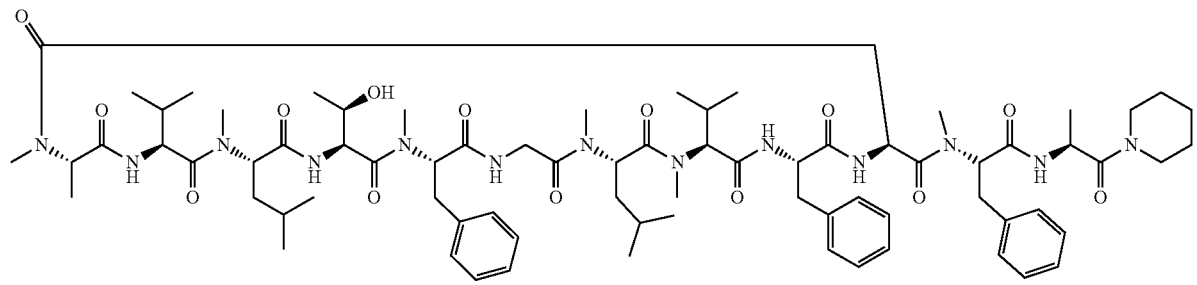

1M phosphate buffer (pH 8.5, 20 ul) and water (25 ul) were added to a solution of 2-(ethyldisulfanyl)-6-methylphenyl (3S,6S,9S,12S,15S,21S,24S,27S,30S)-15,27-dibenzyl-12-((R)-1-hydroxyethyl)-9,21-diisobutyl-6,24-diisopropyl-3,8,14,20,23-pentamethyl-30-(methyl((S)-1-oxo-1-(((S)-1-oxo-1-(piperidin-1-yl)propan-2-yl)amino)-3-phenylpropan-2-yl)carbamoyl)-4,7,10,13,16,19,22,25,28-nonaoxo-2,5,8,11,14,17,20,23,26,29-decaazadotriacontan-32-oate (Compound P-523) (0.163 mg, 0.100 umol) and 1-hydroxypyrrolidine-2,5-dione (0.575 mg, 5.0 umol) in DMF (50 ul). A 1 M aqueous tris(2-carboxyethyl)phosphine (TCEP) solution (5 ul) was further added and the mixture was stirred at room temperature for 2 hours. The reaction was observed by LCMS. As a result, the title compound (Compound SP-524) was observed.

LCMS (ESI) m/z=1432.9 (M+H)+

Retention time: 1.09 min (analysis condition SQDFA05)

5. Peptide Cyclization of RNA-Peptide Fusions not Utilizing a Reaction Auxiliary Group RNA-peptide fusions were subjected to peptide cyclization reaction not utilizing a reaction auxiliary group, and the products were analyzed by electrophoresis.

used as templates, translation was carried out by adding 0.25 mM Phe and 0.25 mM Ala thereto, respectively. The reaction solutions were then purified with RNeasy minelute (Qiagen) to provide RNA-peptide fusions.

```
SEQ ID NO: DM-D1 OT-97
OT-97 DNA sequence
                                          (SEQ ID NO: 82)
GTAATACGACTCACTATAGGGTTAACTTTAAGAAGGAGATATACATATGG

GTACTACAACGCGTCTTCCGTACCGTAGCGGCTCTGGCTCTGGCTCTAAA

AAAA

SEQ ID NO: DM-D2 OT-98
OT-98 DNA sequence
                                          (SEQ ID NO: 83)
GTAATACGACTCACTATAGGGTTAACTTTAAGAAGGAGATATACATATGT

TTACTACAACGCGTCTTCCGTACCGTAGCGGCTCTGGCTCTGGCTCTAAA

AAAA

SEQ ID NO: DM-D3 OT-99
OT-99 DNA sequence
                                          (SEQ ID NO: 84)
GTAATACGACTCACTATAGGGTTAACTTTAAGAAGGAGATATACATATGG

CTACTACAACGCGTCTTCCGTACCGTAGCGGCTCTGGCTCTGGCTCTAAA

AAAA
```

-continued

SEQ ID NO: RM-D3 OT-97
OT-97 RNA sequence
(SEQ ID NO: 85)
GGGUUAACUUUAAGAAGGAGAUAUACAUAUGGGUACUACAACGCGUCUUC

CGUACCGUAGCGGCUCUGGCUCUGGCUCUAAAAAAA

SEQ ID NO: RM-D4 OT-98
OT-98 RNA sequence
(SEQ ID NO: 86)
GGGUUAACUUUAAGAAGGAGAUAUACAUAUGUUUACUACAACGCGUCUUC

CGUACCGUAGCGGCUCUGGCUCUGGCUCUAAAAAAA

SEQ ID NO: RM-D5 OT-99
OT-99 RNA sequence
(SEQ ID NO: 87)
GGGUUAACUUUAAGAAGGAGAUAUACAUAUGGCUACUACAACGCGUCUUC

CGUACCGUAGCGGCUCUGGCUCUGGCUCUAAAAAAA

SEQ ID NO: C-D1 HY_C18_dCdClinker
[P]dCdC [Fluorecein-dT][Spacer18][Spacer18]

[Spacer18][Spacer18]dcdC[puromycin]([P]:

5'-phosphorylated)

5-2. Peptide Cyclization Reaction of Peptide-RNA Complexes not Utilizing a Reaction Auxiliary Group 70 µL of the RNA-peptide complex prepared above and derived from the OT-97 RNA sequence (SEQ ID NO: RM-D3), 20.1 µL of a thiophenol solution (in which 5 M aqueous 4-trifluoromethylthiophenol solution and 5 M aqueous triethylamine solution are mixed in equal amounts) and 10 µL of a 500 mM tricarboxyethylphosphine solution (pH 7.5) were mixed under a nitrogen atmosphere, and the mixture was reacted at 50° C. for 2 hours. 5 M 4-trifluoromethylthiophenol solution and 5M triethylamine solution were prepared using HEPES buffer solution (pH-value 7.6) and mixed in equal amounts to prepare a thiophenol solution, after which 70 µL each of the RNA-peptide fusions derived from the OT-98 RNA sequence (SEQ ID NO: RM-D4) and the OT-99 RNA sequence (SEQ ID NO: RM-D5) were mixed with 20.1 µL of NMP, 20.1 µL of thiophenol solution described above and 10 µL of a 500 mM tricarboxyethylphosphine solution (pH 7.5) under a nitrogen atmosphere, and the mixture was stirred at 30° C. for 22 hours.

Figure 47:
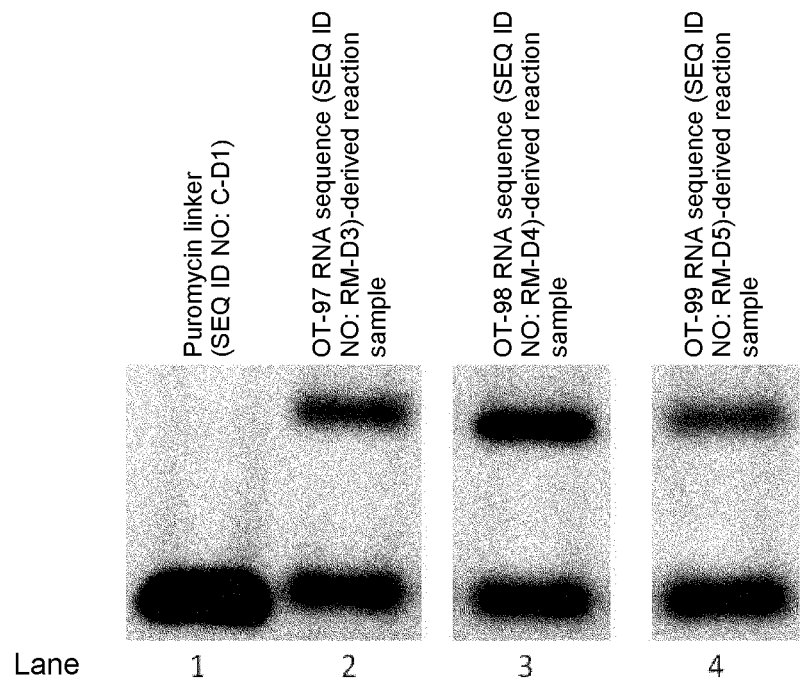
FIG. 47 is a diagram showing electrophoretic analysis results of a reaction product from peptide cyclization reaction.

The peptide-RNA complex was purified from each of the resulting three reaction solutions using RNeasy minelute (Qiagen) and eluted from the column with 70 µL of pure water. Subsequently, 8.4 µL of 10× RNase ONE ribonuclease reaction buffer (Promega), 2.8 µL of RNase ONE ribonuclease (Promega) and 2.8 µL of RNase H (Life Technologies) were added and the mixture was incubated at 37° C. overnight. Subsequently, the resulting reaction solution and unreacted puromycin linker (SEQ ID NO: C-D1) were subjected to electrophoresis using peptide-PAGE mini (TEFCO), and the band was visualized with fluorescein derived from the puromycin linker. As a result, the difference in band mobility due to conjugating of the peptide to the puromycin linker was observed in any of the reaction solutions (FIG. 47). This indicated the presence of the intended cyclized peptide-RNA complexes.

6. Replacement of Methionine with Norleucine and its Application to Peptide Cyclization Utilizing Aminopeptidase After translation, the formylated translation initiation amino acid at the N-terminal was cleaved with methionine aminopeptidase and peptide deformylase, the a-amino group exposed by the cleavage was subjected to peptide cyclization reaction, followed by MALDI-MS analysis. Norleucine (CAS No. 327-57-1), an amino acid free from a sulfur atom susceptible to oxidation, was assigned to the initiation codon in place of methionine.

Figure 48:
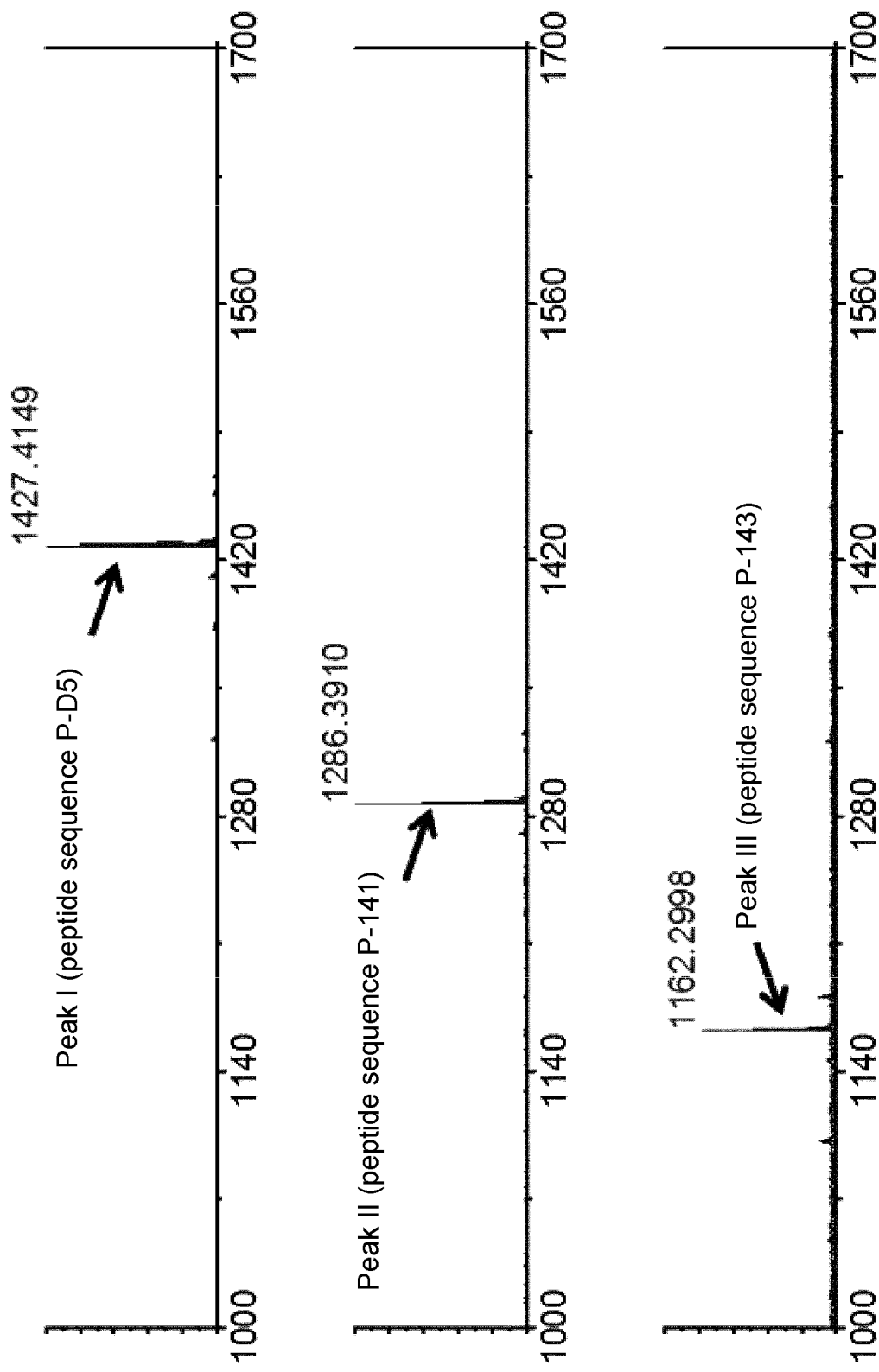
FIG. 48 is a diagram showing MALDI-MS analysis results of a cyclized peptide resulting from posttranslational initiation amino acid removal and peptide cyclization not utilizing a reaction auxiliary group, using a peptide containing norleucine at the N-terminus and a benzylthioesterified aspartic acid derivative in the side chain.

6-1. Posttranslational Initiation Amino Acid Removal and Peptide Cyclization not Utilizing a Reaction Auxiliary Group, Using a Peptide Containing Norleucine at the N-Terminus and a Benzylthioesterified Aspartic Acid Derivative in the Side Chain The aforementioned translation solution containing 1 µM template DNA Mgtp_R (SEQ ID NO: R-41) as well as 0.25 mM Pro, 0.25 mM Gly, 0.25 mM Thr, 0.25 mM Arg, 0.25 mM Tyr, 2.5 mM norleucine (Nle) and 50 µM Asp(SBn)-tRNAGluAAG (Compound AT-7-A) was incubated at 37° C. for 60 minutes. 9 µL of 0.2% trifluoroacetic acid was added to 1 µL of the resulting translation solution. 1 µL of the resulting mixture was loaded on a MALDI target plate, and then blended with 1 µL of a CHCA solution (10 mg/ml α-cyano-4-hydroxycinnamic acid, 50% acetonitrile, 0.1% trifluoroacetic acid), dried on the plate. As a result of MALDI-MS, a peak derived from the intended peptide P-D5 translated from formylnorleucine was observed (FIG. 48, peak I). Next, 0.5 µL each of 150 µM methionine aminopeptidase and 20 µM peptide deformylase prepared as His-tagged proteins were added to 4 µL of the translation solution obtained above, and the mixture was incubated at 37° C. for 30 minutes. 1 µL of the resulting reaction solution was pretreated as described above and analyzed by MALDI-MS. A peak corresponding to the peptide P-141 was observed in which formylnorleucine assigned to the initiation codon was removed and Gly assigned to the second codon was exposed at the N-terminal (FIG. 48, peak II). Finally, 3.5 µL of the translation solution containing P-141, 1 µL of thiophenol solution (in which 5 M 4-trifluoromethylthiophenol and 5 M triethylamine are mixed in equal amounts), and 0.5 µL of a 500 mM tricarboxyethylphosphine solution (pH 7.6) were mixed, and the mixture was incubated at 50° C. for 2 hours. 12 µL of 2% trifluoroacetic acid was added to 2 µL of the resulting reaction solution. 1 µL of the resulting mixture was loaded on a MALDI target plate, and then blended with 1 µL of a CHCA solution (10 mg/ml α-cyano-4-hydroxycinnamic acid, 50% acetonitrile, 0.1% trifluoroacetic acid), dried on the plate and then analyzed by MALDI-MS. As a result, a peak was observed corresponding to the intended Compound P-143 amide-cyclized at the nitrogen atom of the N-terminal α-amino group and the side chain carboxylic acid of Asp (FIG. 48, peak III).

Peptide sequence P-D5
(SEQ ID NO: 238)
fNleGlyThrThrThrArg[Asp(SBn)]ProTyrArgGlyGly

MALDI-MS:

m/z: [H+M]+=1427.4 (peptide corresponding to the sequence P-D5; Cabo. 1427.7)

m/z: [H+M]+=1286.4 (peptide corresponding to the sequence P-141; Cabo. 1286.6)

m/z: [H+M]+=1162.3 (peptide corresponding to the sequence P-143; Calc. 1162.6)

[Example 21] Production of Branched Peptides from Translational Products (Production of Linear Portions 2)

1. Selection of Units which Enable Production of Branched Peptides from Translational Products and Examination of Reaction Conditions 1-1. Amidation Reaction by Intermolecular Reaction As a result of examination of the synthesis of (S)-tert-butyl 1-(2-mercaptoethylamino)-1-oxo-3-phenylpropan-2-ylcarbamate (Compound 10) illustrated below, it was revealed that ester functional groups can be activated to form thioesters by addition of thiols in water and amide bonds can be selectively produced from the activated thioesters by condensation reaction with amines.

Figure 41:
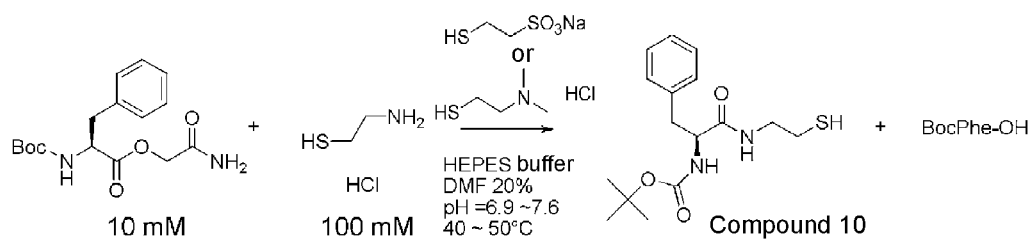
FIG. 41 is a diagram showing the comparison of the synthesis condition of compound 10.

The results of the following reactions are shown in FIG. 41.

Entry 1

Sodium 2-mercaptoethanesulfonate (33 mg, 0.200 mmol) and 2-aminoethanethiol hydrochloride (22.7 mg, 0.200 mmol) were adjusted to pH 7.4 by adding 0.2M HEPES buffer, pH 7.7 (1.60 ml) and DMF (0.400 ml) thereto, and the mixture was stirred at room temperature for 5 minutes. (S)-2-Amino-2-oxoethyl 2-(tert-butoxycarbonylamino)-3-phenylpropanoate (Compound 11) (6.4 mg, 0.02 mmol) was then added, and the mixture was stirred at 50° C. for 24 hours.

The change in the reaction was analyzed by LCMS to confirm that (S)-tert-butyl 1-(2-mercaptoethylamino)-1-oxo-3-phenylpropan-2-ylcarbamate (Compound 10) was produced at 24 hours. The production ratio of the hydrolysate and the intended Compound 10 was 46:43 based on the UV area ratio by LCMS.

Entry 2

0.2 M HEPES buffer, pH 7.0 (0.250 ml), DMF (0.200 ml) and water (0.500 ml) were added to sodium 2-mercaptoethanesulfonate (164 mg, 1.000 mmol) and 2-aminoethanethiol hydrochloride (11.4 mg, 0.100 mmol), and the mixture was stirred at room temperature for 5 minutes. The reaction mixture was adjusted to pH 7.6 by further adding a 1 M aqueous sodium hydroxide solution (0.050 ml) thereto, after which (S)-2-amino-2-oxoethyl 2-(tert-butoxycarbonylamino)-3-phenylpropanoate (Compound 11) (3.2 mg, 0.01 mmol) was added, and the mixture was stirred at 40° C. for 24 hours.

The change in the reaction was observed by LCMS to confirm that (S)-tert-butyl 1-(2-mercaptoethylamino)-1-oxo-3-phenylpropan-2-ylcarbamate (Compound 10) was produced at 24 hours. The production ratio of the hydrolysate and the intended Compound 10 was 24:60 based on the UV area ratio by LCMS.

Entry 3

0.2 M HEPES buffer, pH 7.0 (0.750 ml), DMF (0.200 ml) and water (0.100 ml) were added to 2-dimethylaminoethanethiol hydrochloride (142 mg, 1.000 mmol) and 2-aminoethanethiol hydrochloride (11.4 mg, 0.100 mmol), and the mixture was stirred at room temperature for 5 minutes. The reaction mixture was adjusted to pH 7.3 by further adding a 1 M aqueous sodium hydroxide solution (0.150 ml) thereto, after which (S)-2-amino-2-oxoethyl 2-(tert-butoxycarbonylamino)-3-phenylpropanoate (Compound 11) (3.2 mg, 0.01 mmol) was added, and the mixture was stirred at 40° C. for 24 hours.

The change in the reaction was observed by LCMS to confirm that (S)-tert-butyl 1-(2-mercaptoethylamino)-1-oxo-3-phenylpropan-2-ylcarbamate (Compound 10) was produced at 24 hours. The production ratio of the hydrolysate and the intended Compound 10 was 23:71 based on the UV area ratio by LCMS.

Entry 4

0.5 M HEPES buffer, pH 7.0 (0.300 ml), DMF (0.200 ml) and water (0.200 ml) were added to 2-dimethylaminoethanethiol hydrochloride (425 mg, 3.000 mmol) and 2-aminoethanethiol hydrochloride (11.4 mg, 0.100 mmol), and the mixture was stirred at room temperature for 5 minutes. The reaction mixture was adjusted to pH 6.9 by further adding a 1 N aqueous sodium hydroxide solution (0.300 ml) thereto, after which (S)-2-amino-2-oxoethyl 2-(tert-butoxycarbonylamino)-3-phenylpropanoate (Compound 11) (3.2 mg, 0.01 mmol) was added, and the mixture was stirred at 40° C. for 24 hours.

The change in the reaction was observed by LCMS to confirm that (S)-tert-butyl 1-(2-mercaptoethylamino)-1-oxo-3-phenylpropan-2-ylcarbamate (Compound 10) was produced at 24 hours. The production ratio of the hydrolysate and the intended Compound 10 was 15:84 based on the UV area ratio by LCMS.

LCMS (ESI) m/z=325 (M+H)+

Retention time: 0.71 min (analysis condition SQDFA05)

1-2. Example of Reaction of Producing an Intramolecular Branched Peptide (Linear Portion 2) from a Compound that Mimic a Translated Peptide Branching (production of a linear portion 2) was confirmed in a model reaction of a pre-formed cyclic peptide. A model compound amide-cyclized (main chain cyclization was used in the amide-cyclized portion) having an ester functional group in the main chain and an amino group with a reactive auxiliary group in the side chain of amino acid was synthesized according to the following scheme. Next, a branching experiment was carried out, and branching from the cyclic peptide was observed in water under mild reaction conditions where RNA can stably exist.

1-2-1. Synthesis of a Compound that Mimic a Translated Peptide P-150

Figure 97:
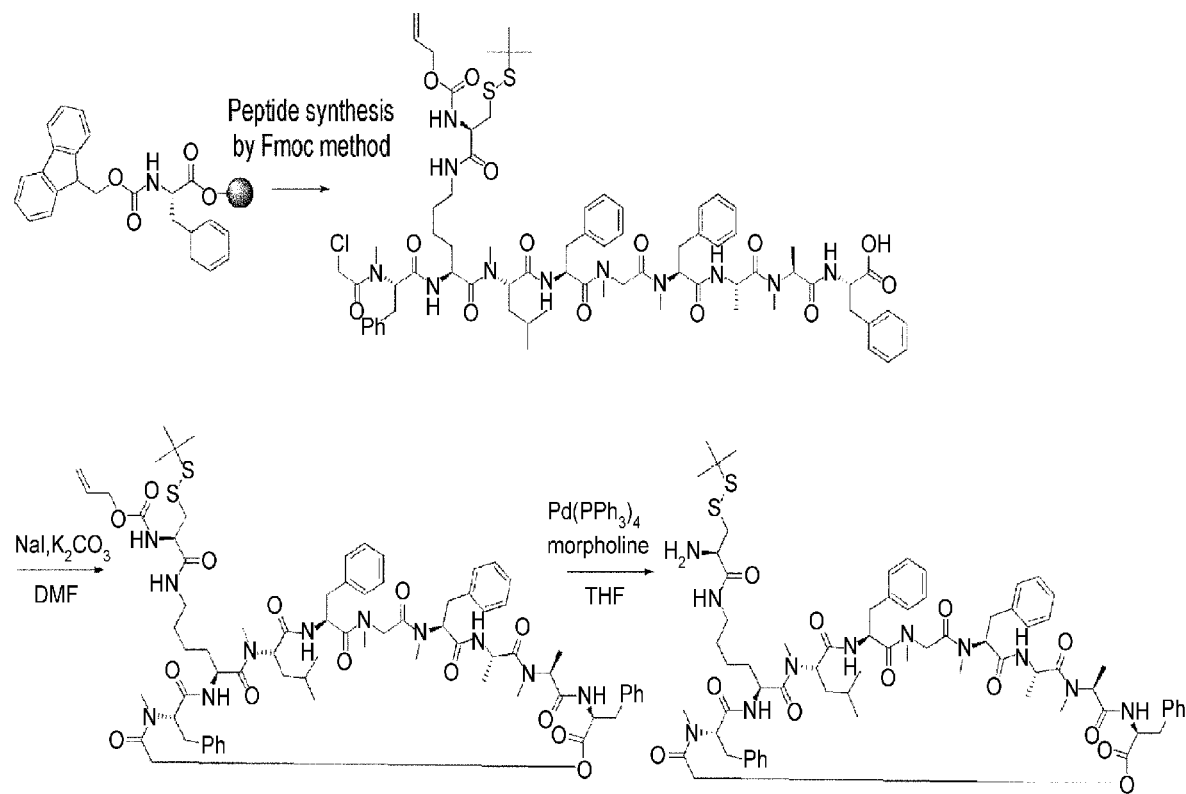
FIG. 97 is a diagram showing the synthesis of a compound that mimic a translated peptide P-150.

See FIG. 97.

Synthesis of (S)-2-(((9H-fluoren-9-yl)methoxy)carbonylamino)-6-((R)-2-(allyloxycarbonylamino)-3-(tert-butyldisulfanyl)propanamido)hexanoic Acid (Fmoc-Lys(Alloc-Cys(StBu))-OH) (Compound 150a)

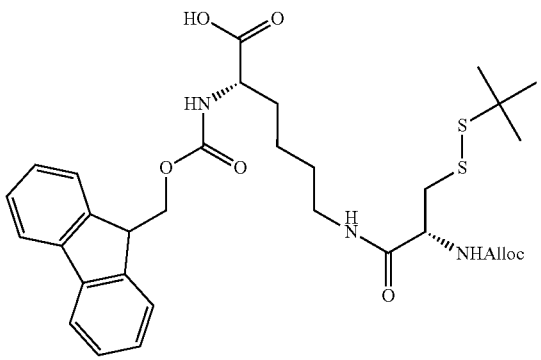

A solution of (R)-2-(allyloxycarbonylamino)-3-(tert-butyldisulfanyl)propanoic acid (Alloc-Cys(StBu)-OH) (1.9 g, 6.48 mmol) and N-hydroxysuccinimide (0.745 g, 6.48 mmol) in dichloromethane (10 ml) was cooled to 0° C., after which 1-(3-dimethylaminopropyl)-3-ethylcarbodiimide hydrochloride (EDC·HCl, 1.24 g, 6.48 mmol) was added and the reaction solution was stirred at room temperature for 20 hours. After 20 hours, the reaction solution was cooled to 0° C., after which N,N-diisopropylethylamine (2.49 ml, 14.25 mmol) and Fmoc-Lys-OH (2.39 g, 6.48 mmol) were added and the reaction solution was stirred at room temperature for 2 hours. Dichloromethane and 1 M hydrochloric acid were added to the reaction mixture, followed by extraction with dichloromethane. The organic layer was washed with 25 wt % brine, the resulting solution was concentrated under reduced pressure, and the concentration residue was purified by reverse-phase silica gel column chromatography (0.1% aqueous formic acid solution/0.1% formic acid-acetonitrile solution) to afford (S)-2-((9H-fluoren-9-yl)methoxy)carbonylamino)-6-((R)-2-(allyloxycarbonylamino)-3-(tert-butyldisulfanyl)propanamido)hexanoic acid (Compound 150a, Fmoc-Lys(Alloc-Cys(StBu))—OH) (2.66 g, 64%).

LCMS (ESI) m/z=644.6 (M+H)+
Retention time: 0.91 min (analysis condition SQD FA05)

Synthesis of Allyl (R)-3-(tert-butyldisulfanyl)-1-oxo-1-(4-((5S,8S,11S,14S,20S,23S,26S,29S)-5,14,20,29-tetrabenzyl-11-isobutyl-4,10,16,19,23,25,26-heptamethyl-3,6,9,12,15,18,21,24,27,30-decaoxo-1-oxa-4,7,10,13,16,19,22,25,28-nonaazacyclotriacontan-8-yl)butylamino)propan-2-ylcarbamate (Compound 150b)

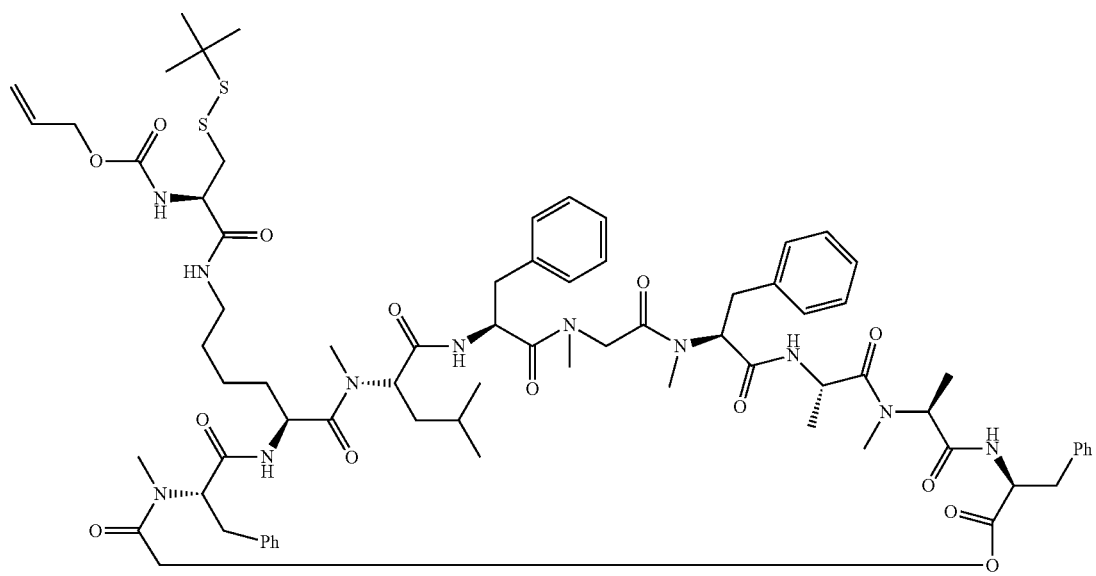

Peptide elongation was carried out using Fmoc-MePhe-OH, Fmoc-MeAla-OH, Fmoc-MeLeu-OH, Fmoc-MeGly-OH, Fmoc-Phe-OH, Fmoc-Ala-OH and Fmoc-Lys(Alloc-Cys(StBu))—OH (Compound 150a) as Fmoc amino acids. Following the peptide elongation, the Fmoc group at the N-terminal was deprotected, chloroacetic acid was condensed using HOAt and DIC as condensing agents, and the resin was then washed with DMF. The peptide was cleaved from the resin by adding dichloromethane/2,2,2-trifluoroethanol (=1/1, v/v, 4 mL) to the resin and reacting for 1 hour. After completion of the reaction, the solution in the tube was filtered through a synthesis column to remove the resin, and the resin was washed with dichloromethane/2,2,2-trifluoroethanol (=1/1, v/v, 1 mL). The resulting solution was concentrated under reduced pressure, the resulting crude product (2S,5S,8S,11S,17S,20S,23S,30R)-2,11,17-tribenzyl-30-((tert-butyldisulfanyl)methyl)-23-((S)-2-(2-chloro-N-methylacetamide)-3-phenylpropanamide)-20-isobutyl-5,6,8,12,15,21-hexamethyl-4,7,10,13,16,19,22,29,32-nonaoxo-33-oxa-3,6,9,12,15,18,21,28,31-nonaazahexatriacont-35-en-1-oic acid (ClAc-MePhe-Lys(Alloc-Cys(StBu))-MeLeu-Phe-MeGly-MePhe-Ala-MeAla-Phe) (SEQ ID NO: 239) (87.2 mg, 0.059 mmol) was obtained. The resulting crude product (ClAc-MePhe-Lys(Ailoc-Cys(StBu)-MeLeu-Phe-MeGly-MePhe-Ala-MeAla-Phe) (SEQ ID NO: 239) (87.2 mg, 0.059 mmol) and sodium iodide (22.2 mg, 0.148 mmol) were dissolved in DMF (7.5 ml), potassium carbonate (12.3 mg, 0.089 mmol) was added to the solution under a nitrogen atmosphere, and the reaction solution was stirred at 35° C. for 2.5 hours. The reaction solution was concentrated under reduced pressure, and the resulting residue was purified by reverse-phase silica gel column chromatography (0.1% aqueous formic acid solution/0.1% formic acid-acetonitrile solution) to afford the title compound 150b (74.2 mg, 87%).

LCMS (ESI) m/z=1433 (M+H)+

Retention time: 0.66 min (analysis condition SQD FA50)

Compound P-150

Synthesis of (R)-2-amino-3-(tert-butyldisulfanyl)-N-(4-((5S,8S,11S,14S,20S,23S,26S,29S)-5,14,20,29-tetrabenzyl-11-isobutyl-4,10,16,19,23,25,26-heptamethyl-3,6,9,12,15,18,21,24,27,30-decaoxo-1-oxa-4,7,10,13,16,19,22,25,28-nonaazacyclotriacontan-8-yl)butyl)propanamide

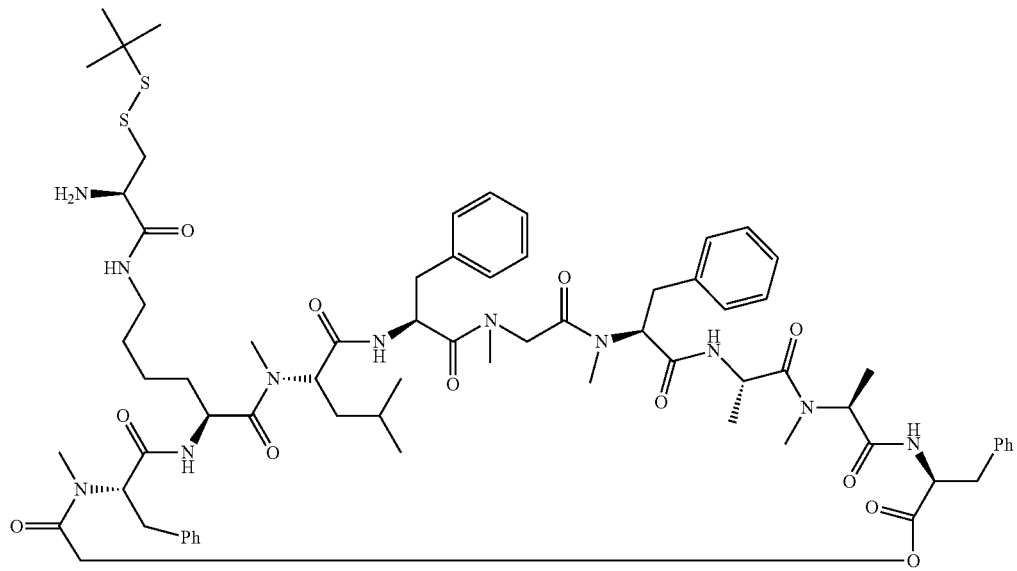

Tetrakis(triphenylphosphine)palladium(0) (2.0 mg, 0.002 mmol) and morpholine (5.62 ml, 0.064 mmol) were added to a solution of allyl (R)-3-(tert-butyldisulfanyl)-1-oxo-1-(4-((5S,8S,11S,14S,20S,23S,26S,29S)-5,14,20,29-tetrabenzyl-11-isobutyl-4,10,16,19,23,25,26-heptamethyl-3,6,9,12,15,18,21,24,27,30-decaoxo-1-oxa-4,7,10,13,16,19,22,25,28-nonaazacyclotriacontan-8-yl)butylamino)propan-2-ylcarbamate (Compound 150b) (23.1 mg, 0.016 mmol) in THF (0.16 ml) under a nitrogen atmosphere, and the reaction solution was stirred at 30° C. for 4 hours. The reaction solution was concentrated under reduced pressure, and the resulting residue was purified by reverse-phase silica gel column chromatography (0.1% aqueous formic acid solution/0.1% formic acid-acetonitrile solution) to afford the title compound P-150 (10.2 mg, 47%).

LCMS (ESI) m/z=1349 (M+H)+

Retention time: 0.74 min (analysis condition SQD FA05)

1-2-2. Reaction of Producing an Intramolecular Branched Peptide from the Translated Model Peptide Compound P-151

Synthesis of (S)-2-(2-hydroxy-N-methylacetamide)-3-phenyl-N-((3R,6S,9S,12S,15S,21S,24S,27S)-6,15,21-tribenzyl-24-isobutyl-3-(mercaptomethyl)-9,10,12,16,19,25-hexamethyl-2,5,8,11,14,17,20,23,26-nonaoxo-1,4,7,10,13,16,19,22,25-nonaazacyclohentriacontan-27-yl)propanamide

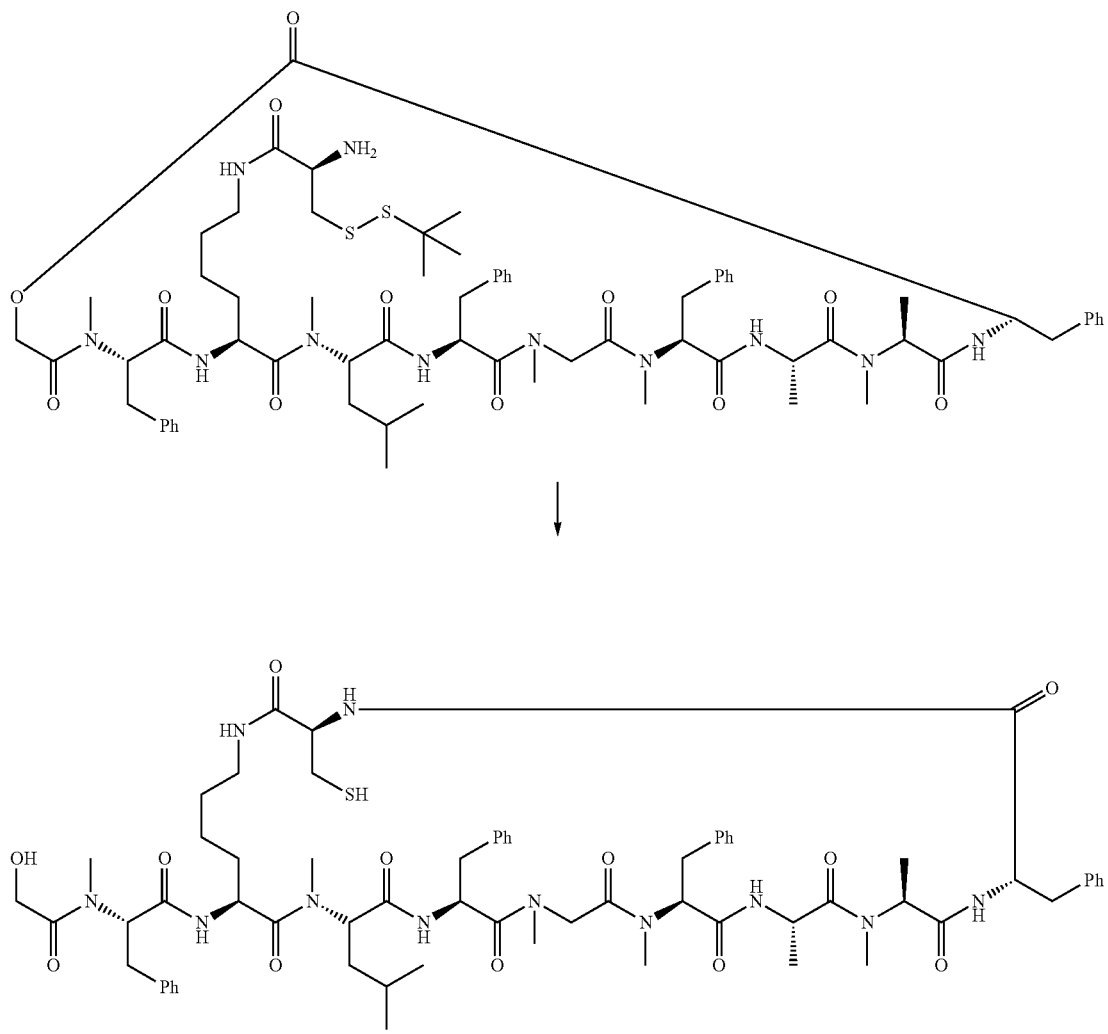

Figure 42:
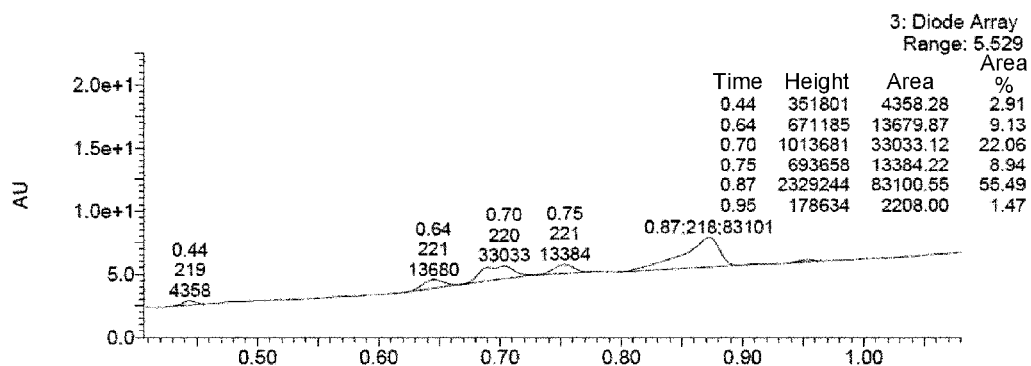
FIG. 42 is a diagram showing LCMS analysis results of the reaction of producing compound P-151.

0.5 M HEPES buffer, pH 7.0 (0.060 ml), 1,3-dimethyl-2-imidazolidinone (DMI) (0.010 ml) and water (0.010 ml) were added to sodium 2-mercaptoethanesulfonate (99 mg, 0.600 mmol) and tris(2-carboxyethyl)phosphine hydrochloride (2.9 mg, 0.010 mmol), and the mixture was stirred at room temperature for 5 minutes. The reaction mixture was adjusted to pH 8.5 by further adding a 2 M aqueous sodium hydroxide solution (0.060 ml) thereto, after which a 0.01 M solution of R)-2-amino-3-(tert-butyldisulfanyl)-N-(4-((5S,8S,11S,14S,20S,23S,26S,29S)-5,14,20,29-tetrabenzyl-11-isobutyl-4,10,16,19,23,25,26-heptamethyl-3,6,9,12,15,18,21,24,27,30-decaoxo-1-oxa-4,7,10,13,16,19,22,25,28-nonaazacyclotriacontan-8-yl)butyl)propanamide (Compound P-150) in 1,3-dimethyl-2-imidazolidinone (DMI) (0.050 ml, 0.5 μmol) was added and the mixture was stirred at 30° C. for 6 hours and 30 minutes. The change in the reaction was observed by LCMS to confirm that the intended compound was produced after 6 hours and 30 minutes. The production ratio of the intended Compound P-151 and the hydrolyzed compound was 55:9 based on the UV area ratio by LCMS (FIG. 42, retention time of the hydrolyzed compound: 0.64 min).

LCMS (ESI) m/z=1261 (M+H)+

Retention time: 0.87 min (analysis condition SQDFA05)

2. Implementation of Examples where the First Cyclization was the Amide Cyclization Between Triangle Unit Having Reaction Auxiliary Group at the N-Terminal and Active Thioester (Intersection Unit) in the Side Chain of the Amino Acid at the C-Terminal, and Following Secondary Branching Reaction was the Reaction Between the Active Ester Generated from Cys-Pro-$^{HO}$Gly and Unprotected Amino Group in the Side Chain of the Amino Acid 2-1. General Method for Solid-Phase Synthesis of Peptides Containing Ester Groups in the Main Chains by Automatic Synthesizers Sieber Amide resin (160 to 200 mg per column, Purchased from Novabiochem), a solution of various Fmoc amino acids (0.6 mol/L) and 1-hydroxy-7-azabenzotriazole (HOAt) (0.375 mol/L) in N-methyl-2-pyrrolidone (NMP), and a solution of diisopropylcarbodiimide (DIC) in N,N-dimethylformamide (DMF) (10% v/v) were placed in a peptide synthesizer, and Fmoc deprotection reaction was carried out using a solution of piperidine in N,N-dimethylformamide (20% v/v) for 5 minutes. Washing with DMF, subsequent Fmoc deprotection and subsequent Fmoc amino acid condensation reaction form one cycle. The peptide was elongated on the surface of the resin by repeating this cycle. The synthesis can be carried out with reference to the Non patent literature of Aimoto et al. (Tetrahedron 2009, 65, 3871-3877) for such an experiment, for example. This method can also be used as a method for synthesizing other peptides in appropriate cases throughout the present specification.

2-2. Establishment of Chemical Reaction Conditions for Examples where the First Cyclization was the Amide Cyclization Between Triangle Unit Having Reaction Auxiliary Group at the N-Terminal and Active Thioester (Intersection Unit) in the Side Chain of the Amino Acid at the C-Terminal, and Following Secondary Branching Reaction was the Reaction Between the Active Ester Generated from Cys-Pro-$^{HO}$Gly and Unprotected Amino Group in the Side Chain of the Amino Acid 2-2-1. Synthesis of a Translated Peptide Model Compound SP605

Figure 98:
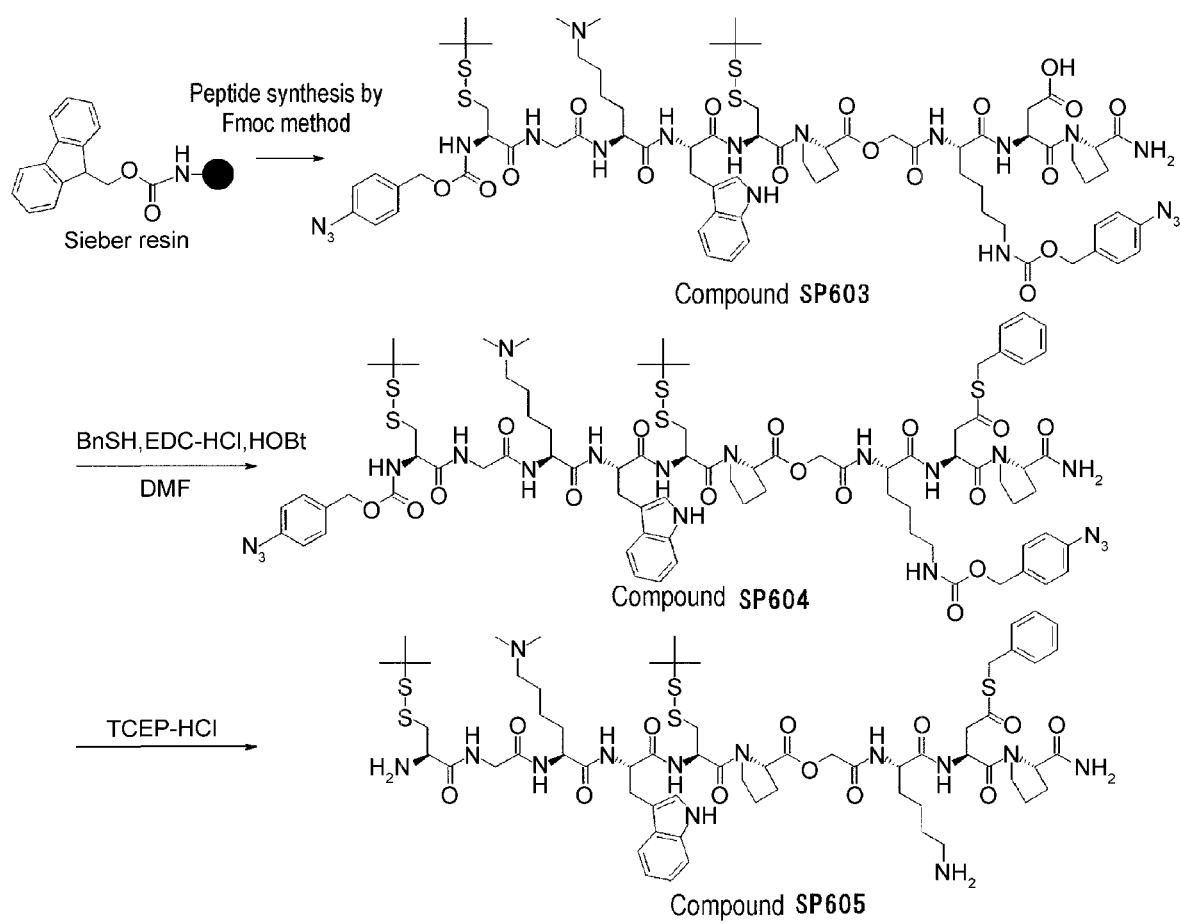
FIG. 98 is a diagram showing the synthesis of a translated peptide model compound SP605.

In accordance with the following scheme, a model peptide was synthesized having Cys at the N-terminal, having Asp (SBn) as a primary cyclization unit on the C-terminal side, and having Cys-Pro-$^{HO}$Gly in the active thioester generation part and the amino group in the side chain of Lys as secondary branching units. See FIG. 98.

Synthesis of (5S,8R)-5-((1H-indol-3-yl)methyl)-1-(9H-fluoren-9-yl)-12,12-dimethyl-3,6-dioxo-2-oxa-10,11-dithia-4,7-diazatridecane-8-carboxylic Acid (Compound SP602, Fmoc-Trp-Cys(StBu)-OH)

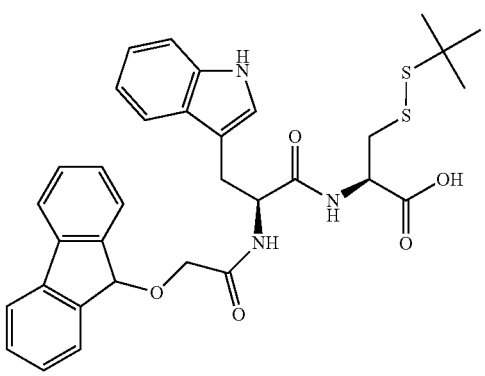 [SMILES: CC(C)(C)SSC[C@H](NC(=O)[C@H](Cc1c[nH]c2ccccc12)NC(=O)COC1c2ccccc2-c2ccccc21)C(=O)O]

A solution of Fmoc-Trp-OH (5 g, 11.72 mmol) and N-hydroxysuccinimide (1.35 g, 11.72 mmol) in dichloromethane (23 ml) was cooled to 0° C., after which 1-(3-dimethylaminopropyl)-3-ethylcarbodiimide hydrochloride (EDC·HCl, 2.25 g, 11.72 mmol) was added and the reaction solution was stirred at room temperature for 5.5 hours. The reaction solution was cooled to 0° C., after which N,N-diisopropylethylamine (2.05 ml, 11.72 mmol) and H-Cys (StBu)-OH (2.45 g, 11.72 mmol) were added and the reaction solution was stirred at room temperature for 14 hours. Dichloromethane and 1 M hydrochloric acid were added to the reaction mixture, followed by extraction with dichloromethane. The organic layer was washed with 25 wt % brine and dried over sodium sulfate. The resulting solution was concentrated under reduced pressure, and the concentration residue was purified by reverse-phase silica gel column chromatography (0.1% aqueous formic acid solution/0.1% formic acid-acetonitrile solution) to afford (5S, 8R)-5-((1H-indol-3-yl)methyl)-1-(9H-fluoren-9-yl)-12,12-dimethyl-3,6-dioxo-2-oxa-10,11-dithia-4,7-diazatridecane-8-carboxylic acid (Compound SP602, Fmoc-Trp-Cys (StBu)-OH) (4.15 g, 57%).

LCMS (ESI) m/z=618 (M+H)+

Retention time: 0.93 min (analysis condition SQD FA05)

Synthesis of (S)-3-((S)-2-(2-((S)-1-((6R,12S,15S,18R)-15-((1H-indol-3-yl)methyl)-6-((4-azidobenzyloxy)carbonylamino)-18-((tert-butyldisulfanyl)methyl)-12-(4-(dimethylamino)butyl)-2,2-dimethyl-7,10,13,16-tetraoxo-3,4-dithia-8,11,14,17-tetraazanonadecane)pyrrolidine-2-carbonyloxy)acetamido)-6-((4-azidobenzyloxy)carbonylamino)hexanamido)-4-((S)-2-carbamoylpyrrolidin-1-yl)-4-oxobutanoic Acid (Compound SP603, Acbz-Cys(StBu)-Gly-Lys(Me$_2$)-Trp-Cys(StBu)-Pro-$^{HO}$Gly-Lys(Acbz)-Asp-Pro-NH2) (SEQ ID NO: 240)

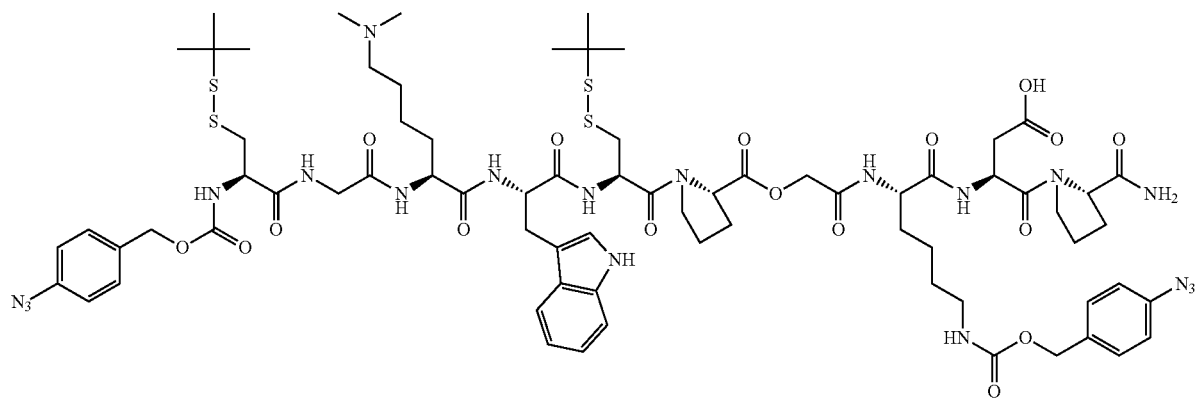 [SMILES: CN(C)CCCC[C@H](NC(=O)CNC(=O)[C@H](CSSC(C)(C)C)NC(=O)OCc1ccc(N=[N+]=[N-])cc1)C(=O)N[C@@H](Cc1c[nH]c2ccccc12)C(=O)N[C@@H](CSSC(C)(C)C)C(=O)N1CCC[C@H]1C(=O)OCC(=O)N[C@@H](CCCCNC(=O)OCc1ccc(N=[N+]=[N-])cc1)C(=O)N[C@@H](CC(=O)O)C(=O)N1CCC[C@H]1C(N)=O]

Definition of Terms

Acbz: 4-Azidobenzyloxycarbonyl group

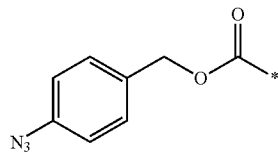 [SMILES: *C(=O)OCc1ccc(N=[N+]=[N-])cc1]

$^{HO}$Gly: Glycolic acid

Fmoc-Lys(Me$_2$)-OH·HCl: N-α-(9-fluorenylmethoxycarbonyl)-N-εε,N-ε-dimethyl-L-lysine hydrochloride

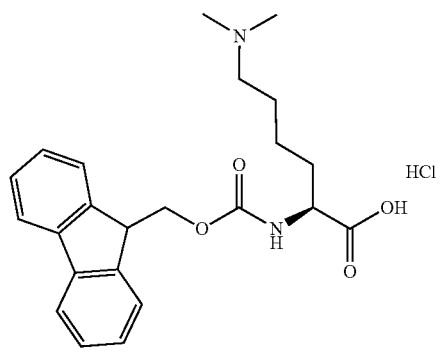 [SMILES: CN(C)CCCC[C@H](NC(=O)OCC1c2ccccc2-c2ccccc21)C(=O)O ; Cl]

Fmoc-Asp(OPis)-OH: N-α-(9-fluorenylmethoxycarbonyl)-L-aspartic acid β-(2-phenyl)isopropyl ester

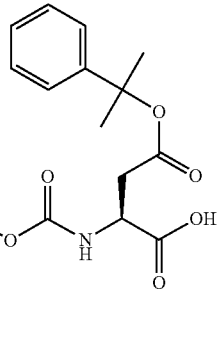

Peptide elongation was carried out based on t method described in Example 2-1 using Acbz-Cys(StBu)-OH as N-terminal amino acid and Fmoc-Gly-OH, Fmoc-Lys(Me$_2$)-OH·HCl, Fmoc-Trp-Cys(StBu)-OH, Fmoc-Pro-$^{HO}$Gly-OH (Compound SP632), Fmoc-Lys(Acbz)-OH (Compound SP661), Fmoc-Asp(OPis)-OH, Fmoc-Pro-OH and Fmoc-Trp-Cys(StBu)-OH (Compound SP602) as Fmoc amino acids.

After the peptide elongation, the resin was washed with DMF and dichloromethane. The peptide was cleaved from the resin by adding dichloromethane/2,2,2-trifluoroethanol (=1/1, v/v, 4 mL) containing 2% TFA (v/v) to the resin and reacting for 3 hours at room temperature. After completion of the reaction, the solution in the tube was filtered through a synthesis column to remove the resin, and the resin was washed with dichloromethane/2,2,2-trifluoroethanol (=1/1, v/v, 2 mL) four times. The resulting solution was concentrated under reduced pressure, and the resulting residue was purified by reverse-phase silica gel column chromatography (0.1% aqueous formic acid solution/0.1% formic acid-acetonitrile solution) to afford the title compound (Acbz-Cys(StBu)-Gly-Lys(Me2)-Trp-Cys(StBu)-Pro-$^{HO}$Gly-Lys(Acbz)-Asp-Pro-NH2) (Compound SP603) (SEQ ID NO: 240) (360 mg, 39%).
LCMS (ESI) m/z=1645 (M+H)+
Retention time: 0.75 min (analysis condition SQD FA05)

Synthesis of (S)-2-((9S,12S)-1-(4-azidophenyl)-12-((s)-2-carbamoylpyrrolidine-1-carbonyl)-3,10,14-trioxo-16-phenyl-2-oxa-15-thia-4,11-diazahexadecan-9-ylamino)-2-oxoethyl 1-((6R,12S,15S,18R)-15-((1H-indol-3-yl)methyl)-6-((4-azidobenzyloxy)carbonylamino)-18-((tert-butyldisulfanyl)methyl)-12-(4-(dimethylamino)butyl)-2,2-dimethyl-7,10,13,16-tetraoxo-3,4-dithia-8,11,14,17-tetraazanonadecane)pyrrolidine-2-carboxylate (Compound SP604, Acbz-Cys(StBu)-Gly-Lys(Me$_2$)-Trp-Cys(StBu)-Pro-$^{HO}$Gly-Lys(Acbz)-Asp(SBn)-Pro-NH2) (SEQ ID NO: 242)

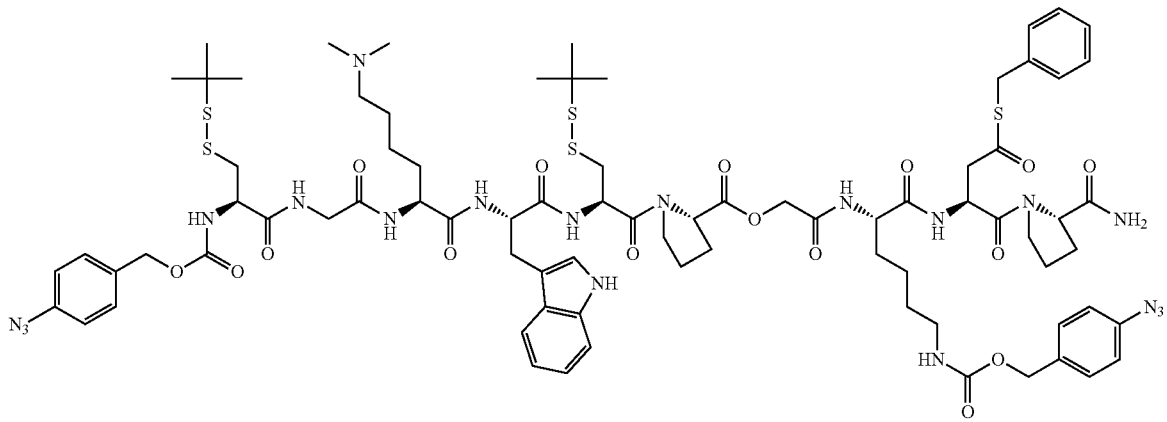 [SMILES: CN(C)CCCC[C@H](NC(=O)CNC(=O)[C@H](CSSC(C)(C)C)NC(=O)OCc1ccc(N=[N+]=[N-])cc1)C(=O)N[C@@H](Cc1c[nH]c2ccccc12)C(=O)N[C@@H](CSSC(C)(C)C)C(=O)N1CCC[C@H]1C(=O)OCC(=O)N[C@@H](CCCCNC(=O)OCc1ccc(N=[N+]=[N-])cc1)C(=O)N[C@@H](CC(=O)SCc1ccccc1)C(=O)N1CCC[C@H]1C(N)=O]

A solution of (S)-3-((S)-2-(2-((S)-1-((6R,12S,15S,18R)-15-((1H-indol-3-yl)methyl)-6-((4-azidobenzyloxy)carbonylamino)-18-((tert-butyldisulfanyl)methyl)-12-(4-(dimethylamino)butyl)-2,2-dimethyl-7,10,13,16-tetraoxo-3,4-dithia-8,11,14,17-tetraazanonadecane)pyrrolidine-2-carbonyloxy)acetamido)-6-((4-azidobenzyloxy)carbonylamino)hexanamido)-4-((S)-2-carbamoylpyrrolidin-1-yl)-4-oxobutanoic acid (Compound SP603, Acbz-Cys(StBu)-Gly-Lys(Me$_2$)-Trp-Cys(StBu)-Pro-$^{HO}$Gly-Lys(Acbz)-Asp-Pro-NH2) (SEQ ID NO: 240) (180 mg, 0.110 mmol) and HOBt (44.4 mg, 0.329 mmol) in DMF (1.096 ml) was cooled to 0° C., after which 1-(3-dimethylaminopropyl)-3-ethylcarbodiimide hydrochloride (EDC·HCl, 63 mg, 0.329 mmol) was added, the mixture was stirred for 3 minutes, and benzylmercaptane (64.3 μl, 0.548 mmol) was then added. The reaction solution was stirred at room temperature for 1 hour and purified by reverse phase silica gel column chromatography (0.1% aqueous formic acid solution/0.1% formic acid-acetonitrile solution) to afford the title compound (Compound SP604, Acbz-Cys(StBu)-Gly-Lys(Me$_2$)-Trp-Cys (StBu)-Pro-$^{HO}$Gly-Lys(Acbz)-Asp(SBn)-Pro-NH2) (SEQ ID NO: 242) (136.3 mg, 71%).
LCMS (ESI) m/z=1751 (M+H)+
Retention time: 0.78 min (analysis condition SQD FA05)

Synthesis of (S)-2-((S)-6-amino-1-((S)-4-(benzyl-thio)-1-((S)-2-carbamoylpyrrolidin-1-yl)-1,4-di-oxobutan-2-ylamino)-1-oxohexan-2-ylamino)-2-oxoethyl 1-((6R,12S,15S,18R)-15-((1H-indol-3-yl)methyl)-6-amino-18-((tert-butyldisulfanyl)methyl)-12-(4-(dimethylamino)butyl)-2,2-dimethyl-7,10,13,16-tetraoxo-3,4-dithia-8,11,14,17-tetraazanonadecane)pyrrolidine-2-carboxylate (Compound SP605, H-Cys(StBu)-Gly-Lys(Me₂)-Trp-Cys(StBu)-Pro-$^{HO}$Gly-Lys-Asp(SBn)-Pro-NH2) (SEQ ID NO: 241)

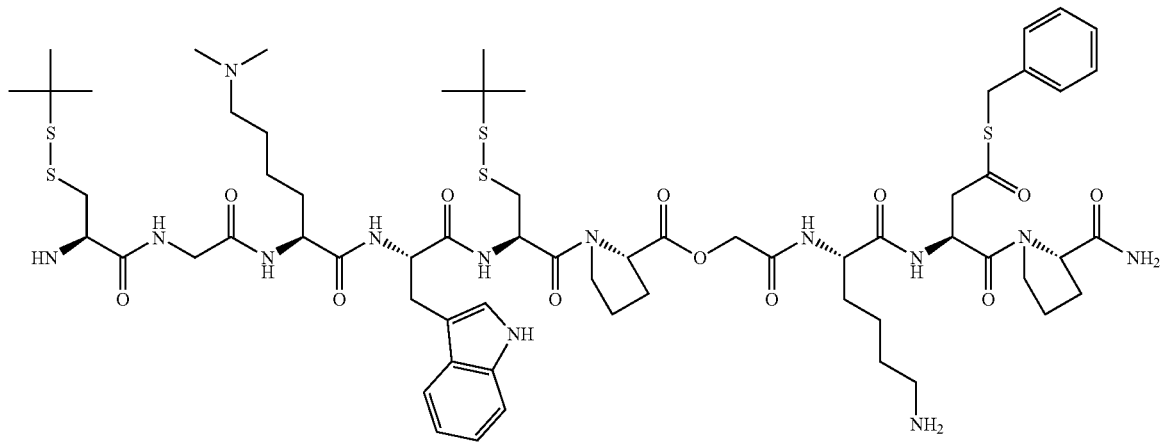 [SMILES: CN(C)CCCC[C@H](NC(=O)CNC(=O)[C@@H](N)CSSC(C)(C)C)C(=O)N[C@@H](Cc1c[nH]c2ccccc12)C(=O)N[C@@H](CSSC(C)(C)C)C(=O)N1CCC[C@H]1C(=O)OCC(=O)N[C@@H](CCCCN)C(=O)N[C@@H](CC(=O)SCc1ccccc1)C(=O)N1CCC[C@H]1C(N)=O]

A solution of (S)-2-((9S,12S)-1-(4-azidophenyl)-12-((S)-2-carbamoylpyrrolidine-1-carbonyl)-3,10,14-trioxo-16-phenyl-2-oxa-15-thia-4,11-diazahexadecan-9-ylamino)-2-oxoethyl 1-((6R,12S,15S,18R)-15-((1H-indol-3-yl)methyl)-6-((4-azidobenzyloxy)carbonylamino)-18-((tert-butyldisulfanyl)methyl)-12-(4-(dimethylamino)butyl)-2,2-dimethyl-7,10,13,16-tetraoxo-3,4-dithia-8,11,14,17-tetraazanonadecane)pyrrolidine-2-carboxylate (Compound SP604, Acbz-Cys(StBu)-Gly-Lys(Me2)-Trp-Cys(StBu)-Pro-$^{HO}$Gly-Lys(Acbz)-Asp(SBn)-Pro-NH2) (SEQ ID NO: 242) (136.3 mg, 0.078 mmol) in 1,3-dimethyl-2-imidazolidinone (DMI) (1.6 ml) was cooled to 0° C., followed by addition of a solution of TCEP (tris(2-carboxylethyl)phosphine) hydrochloride (66.9 mg, 0.234 mmol) in water (1.6 ml). The reaction solution was stirred at room temperature for 90 minutes and purified by reverse phase silica gel column chromatography (0.1% aqueous formic acid solution/0.1% formic acid-acetonitrile solution) to afford the title compound (Compound SP605, H-Cys(StBu)-Gly-Lys(Me₂)-Trp-Cys(StBu)-Pro-$^{HO}$Gly-Lys-Asp(SBn)-Pro-NH2). (SEQ ID NO: 241) (63 mg, 58%).

LCMS (ESI) m/z=1401 (M+H)+

Retention time: 0.46 min (analysis condition SQD FA05)

2-2-2. Example of Reaction for Producing an Branched Peptide Compound SP606 (in a Buffer) by Cyclization Reaction by Native Chemical Ligation Using a Linear Peptide as a Substrate and Subsequent Amidation Reaction of an Amino Group without a Reaction Auxiliary Group Utilizing N—S Transfer
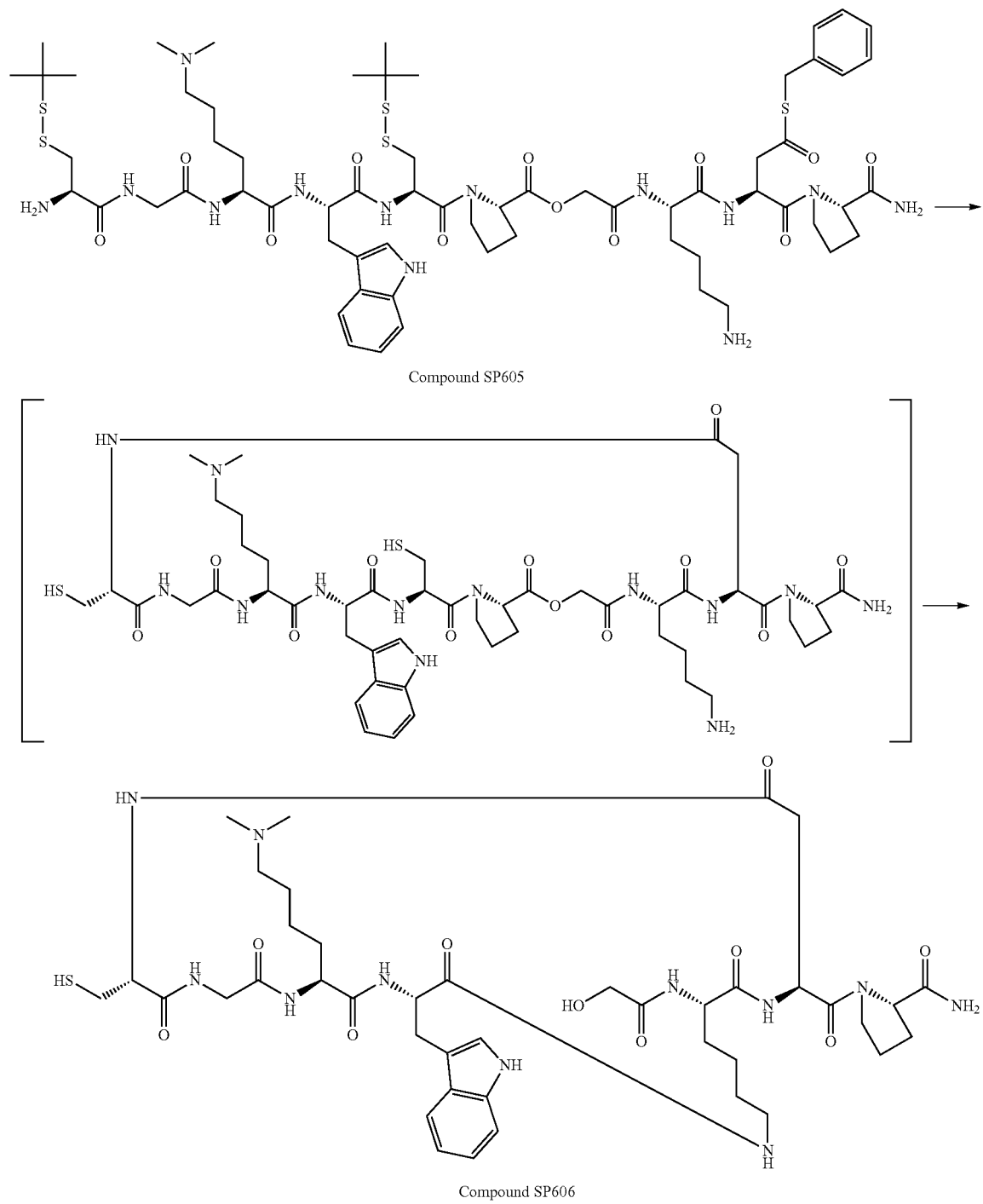

Figure 49:
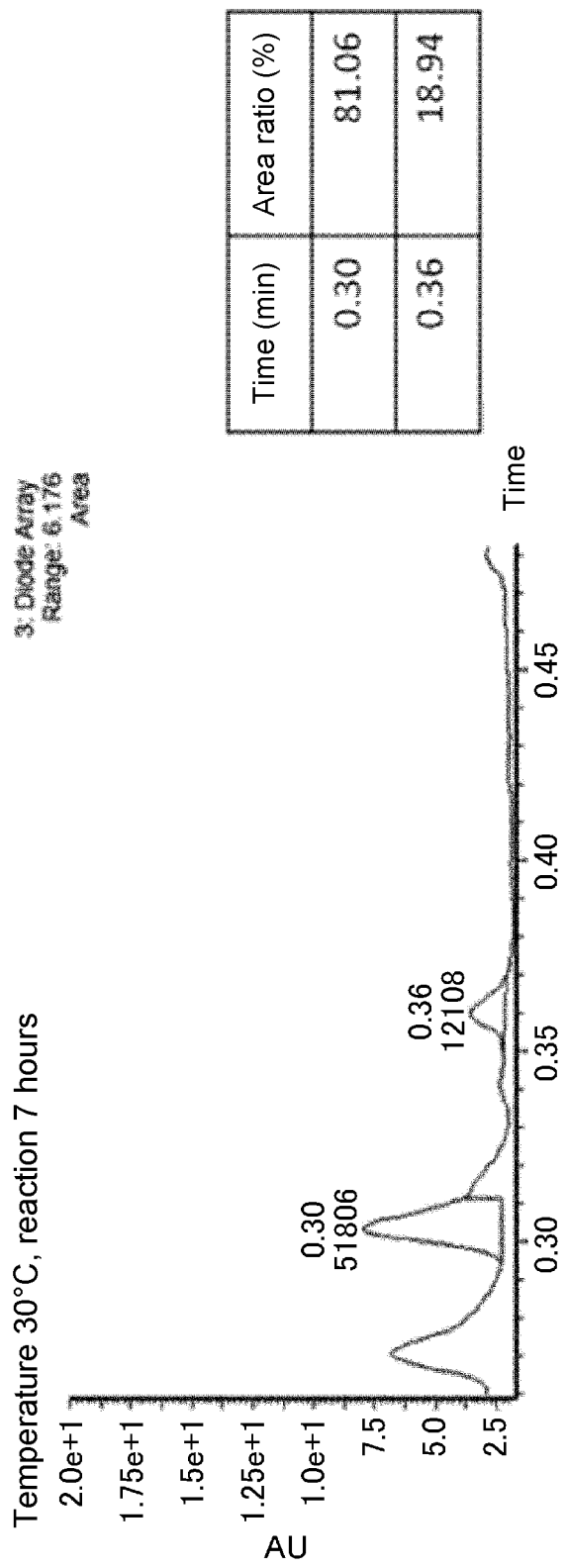
FIG. 49 is a diagram showing LCMS analysis results of a reaction solution containing produced compound SP-606.

A solution was prepared containing 0.5 M HEPES buffer (pH 7.0, 10 μl), water (78 μl), a 1 M aqueous sodium hydroxide solution (5 μl) and a 0.5 M aqueous TCEP hydrochloride solution (2 μl). (S)-2-((S)-6-Amino-1-((S)-4-(benzylthio)-1-((S)-2-carbamoylpyrrolidin-1-yl)-1,4-dioxobutan-2-ylamino)-1-oxohexan-2-ylamino)-2-oxoethyl 1-((6R,12S,15S,18R)-15-((1H-indol-3-yl)methyl)-6-amino-18-((tert-butyldisulfanyl)methyl)-12-(4-(dimethylamino)butyl)-2,2-dimethyl-7,10,13,16-tetraoxo-3,4-dithia-8,11,14,17-tetraazanonadecane)pyrrolidine-2-carboxylate (Compound SP605, H-Cys(StBu)-Gly-Lys(Me$_2$)-Trp-Cys(StBu)-Pro-$^{HO}$Gly-Lys-Asp(SBn)-Pro-NH2) (SEQ ID NO: 241) (20 mM, 0.10 μmol) and a solution of 4-pentylbenzoic acid as internal standard (20 mM, 0.10 μmol) in DMA (5 μl) were added to this solution at room temperature, and the reaction solution was allowed to stand at 37° C. for 60 minutes. The reaction solution (50 μl) was then added to a 2-(4-mercaptophenyl)acetic acid solution (100 mM 2-(4-mercaptophenyl)acetic acid, 250 mM HEPES, 100 mM TCEP) (50 μl) at room temperature (the pH of the mixed solution after addition of the reaction solution was 8.2), the resulting reaction solution was allowed to stand at 30° C. for 7 hours, and the change in the reaction was observed by LCMS. It was confirmed that (S)-1-((3S,6S,12R,16S,19S)-3-((1H-indol-3-yl)methyl)-6-(4-(dimethylamino)butyl)-19-(2-hydroxyacetamide)-12-(mercaptomethyl)-2,5,8,11,14,18-hexaoxo-1,4,7,10,13,17-hexaazacyclotricosane-16-carbonyl)pyrrolidine-2-carboxamide (Compound SP606) was produced at 7 hours. The production ratio of Compound SP606 and the hydrolysate (by-product) was 19:81 based on the UV area ratio by LCMS (FIG. 49, retention time of the hydrolyzed compound: 0.30 min).

LCMS (ESI) m/z=900 (M+H)+

Retention time: 0.36 min (analysis condition SQD FA05)

2-3. Example of Reaction of Producing an Intramolecular Branched Peptide (Linear Portion 2) from a Translated Peptide Since reaction conditions were established under which the peptide synthesized in 2-2 is branched in a buffer (water) under mild reaction conditions where RNA is stable, the fact that an intramolecular branched peptide is similarly produced after translation synthesis was confirmed by MALDI-MS.

2-3-1. Synthesis of tRNAs (Lacking CA) by Transcription tRNAGluAAG (-CA) (SEQ ID NO: RT-H1) and tRNAGluCUG (-CA) (SEQ ID NO: RT-H2) lacking 3'-end CA were synthesized from two template DNAs (SEQ ID NO: DT-H1 and SEQ ID NO: DT-H2) by in vitro transcription using RiboMAX Large Scale RNA production System T7 (Promega, P1300), respectively, and purified with RNeasy Mini kit (Qiagen).

```
SEQ ID NO: DT-H1 (the same as SEQ ID NO: D-40)
tRNAGluAAG (-CA) DNA sequence:
                                    (SEQ ID NO: 64)
GGCGTAATACGACTCACTATAGTCCCCTTCGTCTAGAGGCCCAGGACACC

GCCCTAAGACGGCGGTAACAGGGGTTCGAATCCCCTAGGGGACGC

SEQ ID NO: DT-H2
tRNAGluCTG (-CA) DNA sequence:
                                    (SEQ ID NO: 88)
GGCGTAATACGACTCACTATAGTCCCCTTCGTCTAGAGGCCCAGGACACC

GCCCTCTGACGGCGGTAACAGGGGTTCGAATCCCCTAGGGGACGC

SEQ ID NO: RT-H1
tRNAGluAAG (-CA) RNA sequence:
                                    (SEQ ID NO: 65)
GUCCCCUUCGUCUAGAGGCCCAGGACACCGCCCUAAGACGGCGGUAACAG

GGGUUCGAAUCCCCUAGGGGACGC

SEQ ID NO: RT-H2
tRNAGluCUG (-CA) RNA sequence:
                                    (SEQ ID NO: 89)
GUCCCCUUCGUCUAGAGGCCCAGGACACCGCCCUCUGACGGCGGUAACAG

GGGUUCGAAUCCCCUAGGGGACGC
```

2-3-2. Synthesis of Aminoacylated tRNA (Compound AT-H1) by Ligation of Aminoacylated pdCpA Having Side Chain Carboxylic Acid Converted to Active Ester (Compound 1i-IA) and tRNA (Lacking CA) (SEQ ID NO: RT-H1)

2 μL of 10× ligation buffer (500 mM HEPES-KOH pH 7.5, 200 mM MgCl$_2$), 2 μL of 10 mM ATP and 2.8 μL of nuclease free water were added to 10 μL of 50 μM transcribed tRNAGluAAG (-CA) (SEQ ID NO: RT-H1). The mixture was heated at 95° C. for 2 minutes and then left to stand at room temperature for 5 minutes, and the tRNA was refolded. 1.2 μL of 20 units/μL T4 RNA ligase (New England Biolabs) and 2 μL of a 5 mM solution of aminoacylated pdCpA (Compound 1i-IA) in DMSO were added, and ligation reaction was carried out at 15° C. for 45 minutes. 4 μL of 3 M sodium acetate and 24 μL of 125 mM iodine (solution in water:THF=1:1) were added to 20 μL of the ligation reaction solution, and deprotection was carried out at room temperature for 1 hour. Aminoacylated tRNA (Compound AT-H1) was collected by phenol extraction and ethanol precipitation. Aminoacylated tRNA (Compound AT-H1) was dissolved in 1 mM sodium acetate immediately prior to addition to the translation mixture.

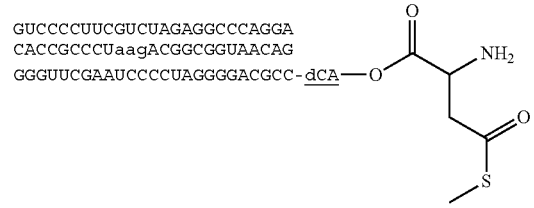

(SEQ ID NO: 66)

Compound AT-H1 Asp(SMe)-tRNAGluAAG

2-3-3. Synthesis of Aminoacylated tRNA (Compound AT-H2) by Ligation of pdCpA Acylated by Glycolic Acid (Compound 20) and tRNA (Lacking CA) (SEQ ID NO: RT-H2)

2 μL of 10× ligation buffer (500 mM HEPES-KOH pH 7.5, 200 mM MgCl$_2$), 2 μL of 10 mM ATP and 2.8 μL of nuclease free water were added to 10 μL of 50 μM transcribed tRNAGluCTG (-CA) (SEQ ID NO: RT-H2). The mixture was heated at 95° C. for 2 minutes and then left to stand at room temperature for 5 minutes, and the tRNA was refolded. 1.2 µL of 20 units/µL T4 RNA ligase (New England Biolabs) and 2 µL of a 5 mM solution of pdCpA acylated by glycolic acid (Compound 20) in DMSO were added, and ligation reaction was carried out at 15° C. for 45 minutes. Aminoacylated tRNA (Compound AT-H2) was collected by phenol extraction and ethanol precipitation. Aminoacylated tRNA (Compound AT-H2) was dissolved in 1 mM sodium acetate immediately prior to addition to the translation mixture.

(SEQ ID NO: 90)
```
GUCCCCUUCGUCUAGAGGCCCAGGA
CACCGCCCUcugACGGCGGUAACAG
GGGUUCGAAUCCCCUAGGGGACGCC-dCA—O
```

Compound AT-H2 $^{HO}$Gly-tRNAGluCUG

2-3-4. Translation Synthesis of a Cyclic Peptide Having a Cysteinyl Prolyl Ester Sequence and a Side Chain Amino Group (Compound P-H1)

Translation synthesis of a desired unnatural amino acid-containing polypeptide was carried out by adding the acylated tRNAs described above (Compound AT-H1 and Compound AT-H2) to a cell-free translation system and initiating translation. The translation system used was PURE system, a prokaryote-derived reconstituted cell-free protein synthesis system.

Figure 50:
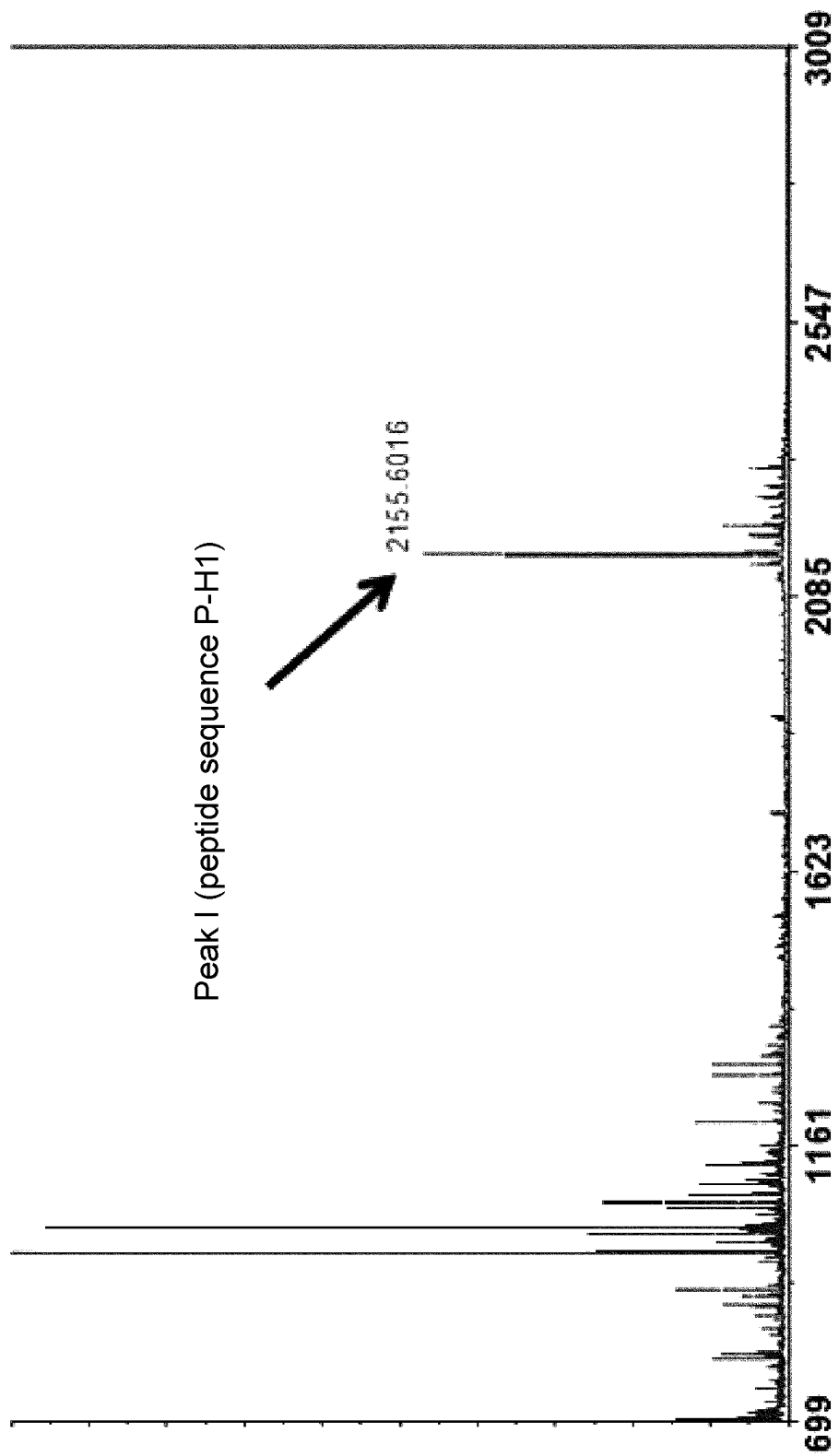
FIG. 50 is a diagram showing MALDI-MS analysis results of a cyclic peptide having a cysteinyl prolyl ester sequence and a side chain amino group (compound P—H1).

Specifically, 1 µM template RNA OT86b (SEQ ID NO: RM-H1), 0.25 mM Cys, 0.25 mM Thr, 0.25 mM Trp, 0.25 mM Phe, 0.25 mM Arg, 0.25 mM Pro, 0.25 mM Lys, 0.25 mM Ser, 20 mM tris(2-carboxyethyl)phosphine (TCEP), 50 µM Asp(SMe)-tRNAGluAAG (Compound AT-H1) and 50 µM 1-1° Gly-tRNAGluCUG (Compound AT-H2) were added to a translation solution (1% (v/v) RNasein Ribonuclease inhibitor (Promega, N2111), 1 mM GTP, 1 mM ATP, 20 mM creatine phosphate, 50 mM HEPES-KOH pH 7.6, 100 mM potassium acetate, 6 mM magnesium acetate, 2 mM spermidine, 1 mM dithiothreitol, 1.5 mg/ml *E. coli* MRE600 (RNase-negative)-derived tRNA (Roche), 4 µg/ml creatine kinase, 3 µg/ml myokinase, 2 units/ml inorganic pyrophosphatase, 1.1 µg/ml nucleoside diphosphate kinase, 0.6 µM methionyl tRNA transformylase, 0.26 µM EF-G, 0.24 µM RF2, 0.17 µM RF3, 0.5 µM RRF, 2.7 µM IF1, 0.4 µM IF2, 1.5 µM IF3, 40 µM EF-Tu, 93 µM EF-Ts, 1.2 µM ribosome, 0.73 µM AlaRS, 0.03 µM ArgRS, 0.38 µM AsnRS, 0.13 µM AspRS, 0.02 µM CysRS, 0.06 µM GlnRS, 0.23 µM GluRS, 0.09 µM GlyRS, 0.4 µM IleRS, 0.04 µM LeuRS, 0.11 µM LysRS, 0.03 µM MetRS, 0.68 µM PheRS, 0.16 µM ProRS, 0.04 µM SerRS, 0.09 µM ThrRS, 0.03 µM TrpRS, 0.02 µM TyrRS, 0.02 µM ValRS (self-prepared proteins were basically prepared as His-tagged proteins)), and the mixture was incubated at 37° C. for 60 minutes. The resulting translation reaction product was purified with SPE C-TIP (Nikkyo Technos) and analyzed by MALDI-MS using α-cyano-4-hydroxycinnamic acid as the matrix. As a result, a peptide P-H1 (FIG. 50, peak I) was observed which is initiated from a second position (Cys) following the initiation methionine and amide-cyclized at the nitrogen atom on the α-amino group and the side chain carboxylic acid of aspartic acid (FIG. 50). As a control experiment, a translation solution obtained by excluding the template RNA OT86b (SEQ ID NO: RM-H1) from the above translation reaction composition was also incubated at 37° C. for 60 minutes.

SEQ ID NO: RM-H1
OT86b RNA sequence
(SEQ ID NO: 91)
GGGUUAACUUUAAGAAGGAGAUAUACAUaugUGCACUACAUGGUUCCGUU

GGUGCCCACAGUUCAAGUGGCUUCCUCGUAGUUAAGG

Peptide sequence P-H1 (SEQ ID NO: 243) Compound amide-cyclized at the nitrogen atom of the N-terminal amino group of CysThrThrTrpPheArgTrpCysPro$^{HO}$GlyPheLysTrp[Asp(SMe)] ProArg Ser and the side chain carboxylic acid of Asp ($^{HO}$Gly refers to glycolic acid)

MALDI-MS:

m/z: [H+M]+=2155.6 (peptide corresponding to the sequence P-H1; Calc. 2156.0)

2-3-5. Reaction of Producing an Intramolecular Branched Peptide (Linear Portion 2) Using the Translated Peptide P-H1

Figure 51:
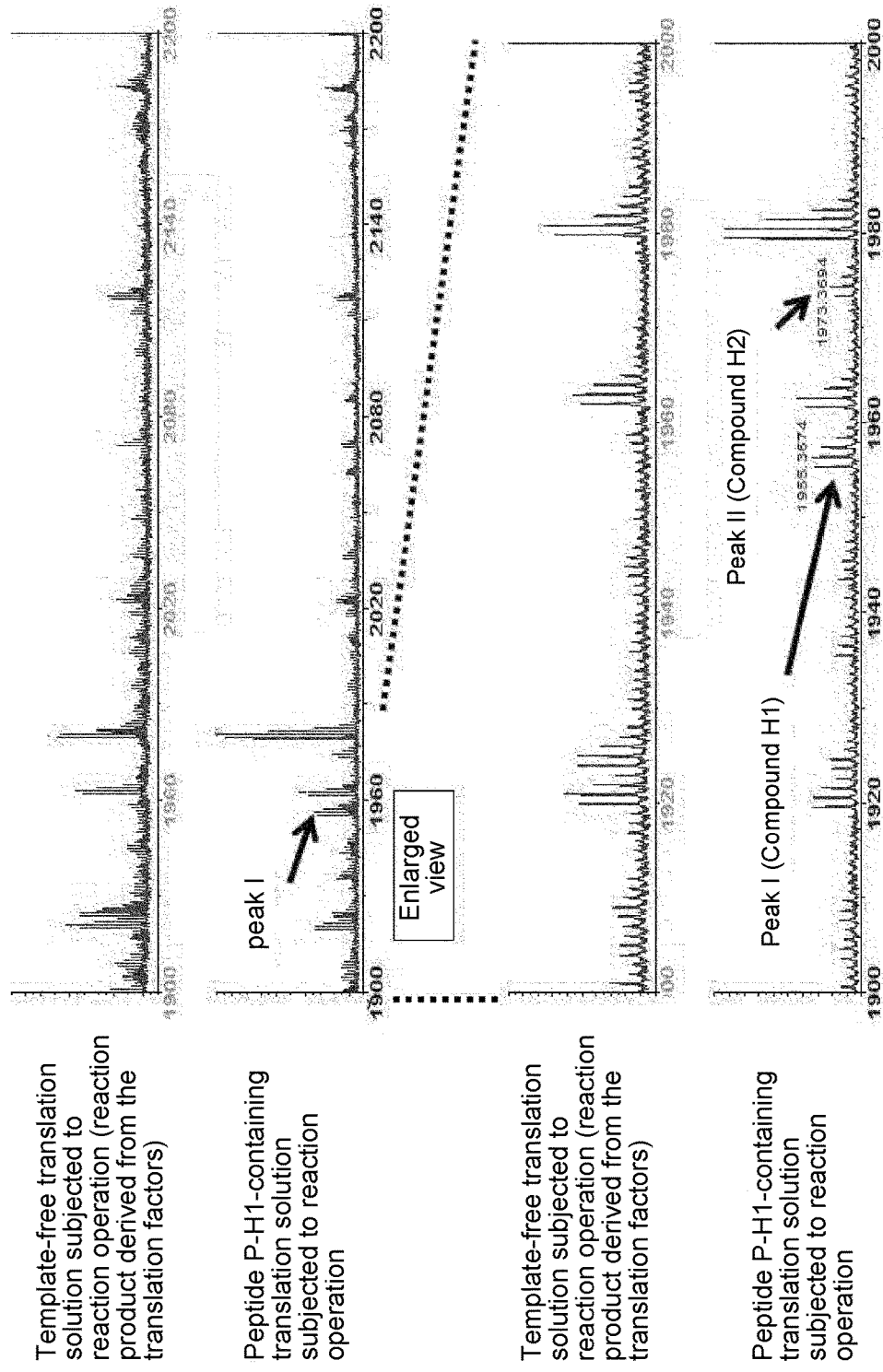
FIG. 51 is a diagram showing MALDI-MS analysis results of a product from reaction of producing an intramolecular branched peptide (linear portion 2) using translated peptide P—H1.

5 µL of the aforementioned translation solution containing the translation reaction product P-H1 and 5 µL of a cyclization reaction reagent solution adjusted to pH 8.5 (0.3 M HEPES-KOH, 0.1 M TCEP, 0.1 M p-mercaptophenylacetic acid) were mixed, and the mixture was incubated at 30° C. for 17 hours. The resulting reaction solution was then purified with SPE C-TIP (Nikkyo Technos) and analyzed by MALDI-MS using α-cyano-4-hydroxycinnamic acid as the matrix. As a control experiment, the aforementioned translation solution not containing the template RNA OT86b (SEQ ID NO:91; RM-H1) was also subjected to the same operation, a peak derived from the template RNA-dependently synthesized translational product was distinguished by comparing the two solutions and was analyzed. Consequently, a peak corresponding to Compound H1 having the intended intramolecular branched backbone was observed and production of an intramolecular branched peptide (linear portion 2) using the translated peptide was confirmed in the translation reaction solution containing the template RNA OT86b (SEQ ID NO: RM-H1) (FIG. 51, peak I).

(SEQ ID NO: 244)

Compound H1

A more detailed structure (in which amino acids each described as three letters are converted to a chemical structure) is illustrated below.

2223 2224

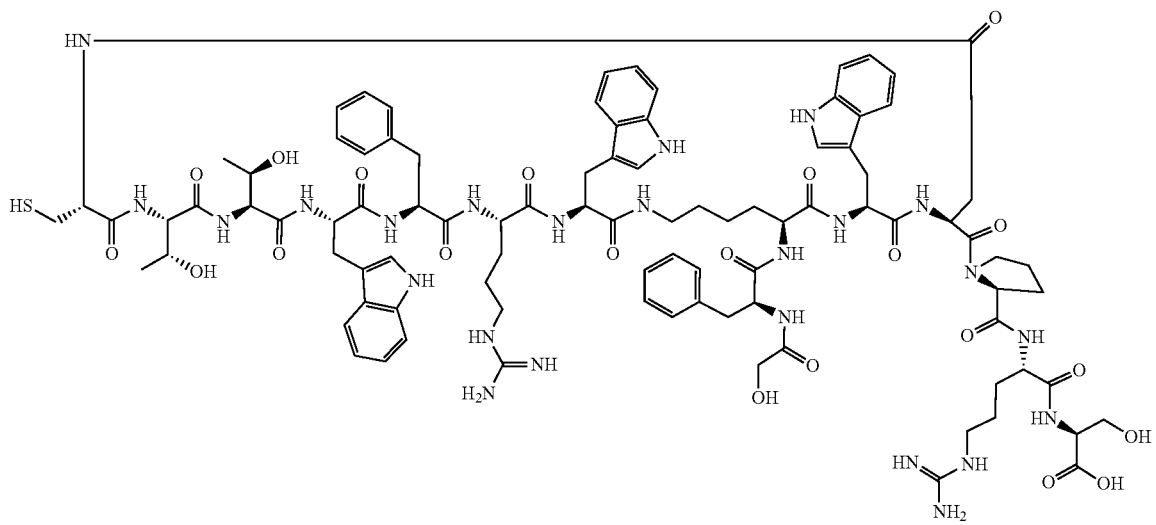 [SMILES: C[C@@H](O)[C@@H]1NC(=O)[C@H](CS)NC(=O)C[C@@H](C(=O)N2CCC[C@H]2C(=O)N[C@@H](CCCNC(=N)N)C(=O)N[C@@H](CO)C(=O)O)NC(=O)[C@H](Cc2c[nH]c3ccccc23)NC(=O)[C@@H](NC(=O)[C@H](Cc2ccccc2)NC(=O)CO)CCCCNC(=O)[C@H](Cc2c[nH]c3ccccc23)NC(=O)[C@H](CCCNC(=N)N)NC(=O)[C@H](Cc2ccccc2)NC(=O)[C@H](Cc2c[nH]c3ccccc23)NC(=O)[C@H]([C@@H](C)O)NC1=O]

MALDI-MS:

m/z: [H+M]+=1955.4 (peptide corresponding to Compound H1; Calc. 1955.9)

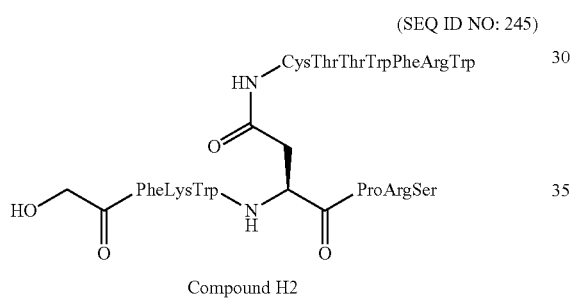

(SEQ ID NO: 245)

Compound H2

A more detailed structure (in which amino acids each described as three letters are converted to a chemical structure) is illustrated below.

MALDI-MS:

m/z: [H+M]+=1973.4 (peptide corresponding to Compound H2; Calc. 1973.9)

3. Improvement of Chemical Reaction Conditions for Examples where the First Cyclization was the Amide Cyclization Between Triangle Unit Having Reaction Auxiliary Group at the N-Terminal and Active Thioester (Intersection Unit) in the Side Chain of the Amino Acid at the C-Terminal, and Following Secondary Branching was the Reaction Between the Active Ester Generated from Cys-Pro-$^{HO}$Gly and Unprotected Amino Group in the Side Chain of the Amino Acid, and Examples of Desulfurization Reaction for Removing Thiol Groups Possessed by Branched Peptides Having Linear Portions 2 Produced Under Improved Conditions As illustrated above, branching reaction was also confirmed to proceed in translated peptides as a result of

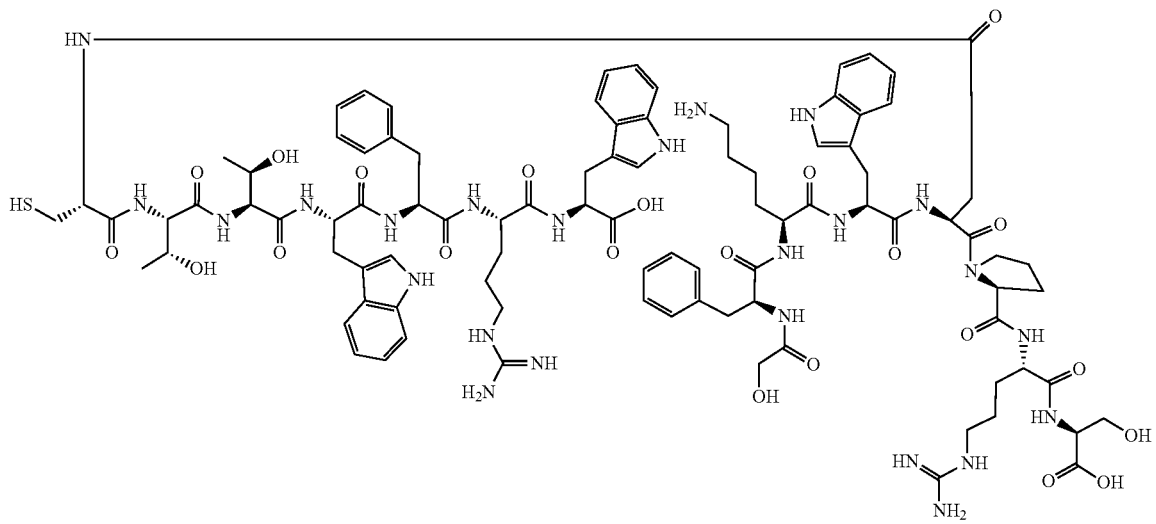 [SMILES: C[C@@H](O)[C@H](NC(=O)[C@H](CS)NC(=O)C[C@H](NC(=O)[C@H](Cc1c[nH]c2ccccc12)NC(=O)[C@H](CCCCN)NC(=O)[C@H](Cc1ccccc1)NC(=O)CO)C(=O)N1CCC[C@H]1C(=O)N[C@@H](CCCNC(=N)N)C(=O)N[C@@H](CO)C(=O)O)C(=O)N[C@H](C(=O)N[C@@H](Cc1c[nH]c2ccccc12)C(=O)N[C@@H](Cc1ccccc1)C(=O)N[C@@H](CCCNC(=N)N)C(=O)N[C@@H](Cc1c[nH]c2ccccc12)C(=O)O)[C@@H](C)O]

adapting branching reaction conditions established for conversion of the synthetic peptide Compound SP605 to Compound SP606 to a translated peptide. The following experiment is optimization of synthetic peptide-modeled reaction from Compound SP605 to Compound SP606. Reactions in water and in a translation solution were carried out, and branching reaction was optimized by a translated peptide. Consequently, reaction conditions with high reaction selectivity were established.

3-1. Intramolecular Branched Peptide Forming Reaction in a Buffer

Experiment for Comparing the Effects of Organic Solvents

The reaction was modified in that the content of the organic solvent (DMA) was increased from 5% to 50% for primary cyclization reaction and from 2.5% to 50% for secondary branching reaction. The results are shown below.

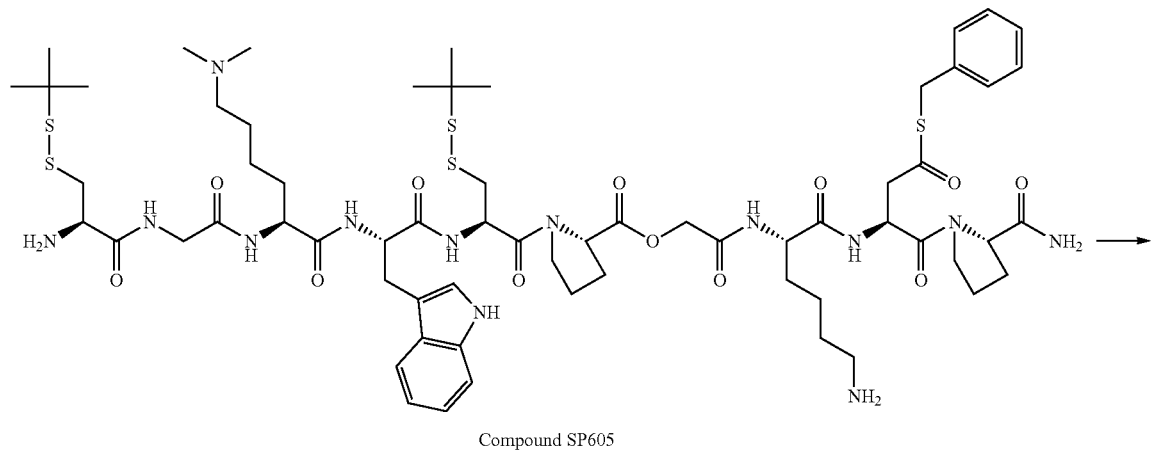

Compound SP605

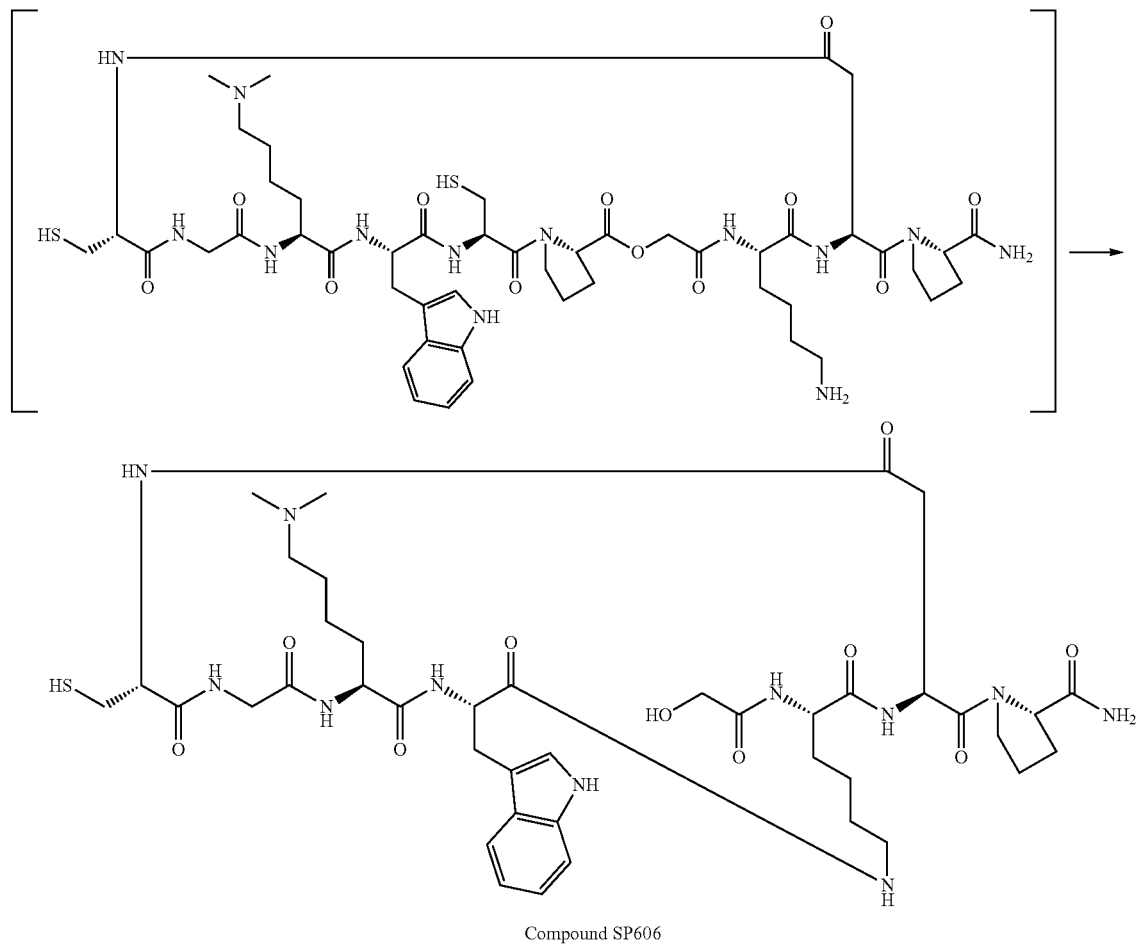

Compound SP606

A solution was prepared containing 0.5 M HEPES buffer (pH 7.0, 10 µl), water (33 µl), a 1 M aqueous sodium hydroxide solution (5 µl), DMA (45 µl) and a 0.5 M aqueous TCEP hydrochloride solution (2 µl). (S)-2-((S)-6-amino-1-((S)-4-(benzylthio)-1-((S)-2-carbamoylpyrrolidin-1-yl)-1,4-dioxobutan-2-ylamino)-1-oxohexan-2-ylamino)-2-oxoethyl 1-((6R,12S,15S,18R)-15-((1H-indol-3-yl)methyl)-6-amino-18-((tert-butyldisulfanyl)methyl)-12-(4-(dimethylamino)butyl)-2,2-dimethyl-7,10,13,16-tetraoxo-3,4-dithia-8,11,14,17-tetraazanonadecane)pyrrolidine-2-carboxylate (Compound SP605, H-Cys(StBu)-Gly-Lys(Me$_2$)-Trp-Cys(StBu)-Pro-$^{HO}$Gly-Lys-Asp(SBn)-Pro-NH2) (SEQ ID NO: 246) (20 mM, 0.10 µmol) and a solution of 4-pentylbenzoic acid as internal standard (20 mM, 0.10 µmol) in DMA (5 WI) were added to this solution at room temperature, and the reaction solution was allowed to stand at 37° C. for 60 minutes. After 60 minutes, the reaction solution (20 µl) was added to a solution containing a 125 mM solution of 2-(4-mercaptophenyl)acetic acid in DMA (40 µl), 0.5 M HEPES buffer (pH 7.0, 18 µl), water (6 µl), a 5 M aqueous sodium hydroxide solution (6 µl) and a 0.5 M aqueous TCEP hydrochloride solution (10 µl) at room temperature (the pH of the mixed solution after adding the reaction solution was 8.2), the resulting reaction solution was allowed to stand at 30° C. for 24 hours, and the change in the reaction was observed by LCMS. It was confirmed that (S)-1-((3S,6S,12R,16S,19S)-3-((1H-indol-3-yl)methyl)-6-(4-(dimethylamino)butyl)-19-(2-hydroxyacetamide)-12-(mercaptomethyl)-2,5,8,11,14,18-hexaoxo-1,4,7,10,13,17-hexaazacyclotricosane-16-carbonyl)pyrrolidine-2-carboxamide (Compound SP606) was produced after 24 hours. The production ratio of Compound SP606, the hydrolyzate (by-product) and the reaction intermediate was 40:4:56 based on the UV area ratio by LCMS.

The above result revealed that an increase in the organic solvent content is advantageous for primary cyclization reaction. This suppressed hydrolysis and improved selectivity to afford the intended compound. On the other hand, such an increase for secondary branching reaction reduced the rate of chemical reaction to afford the intended compound. Hence, examination for improvement was further continued.

Experiment for Comparison with the Effect in the Case where Thiophenol was Used in Place of 2-(4-Mercaptophenyl) Acetic Acid A solution was prepared containing 0.5 M HEPES buffer (pH 7.0, 10 µl), water (33 µl), a 1 M aqueous sodium hydroxide solution (5 µl), DMA (45 µl) and a 0.5 M aqueous TCEP hydrochloride solution (2 µl). (S)-2-((S)-6-amino-1-((S)-4-(benzylthio)-1-((S)-2-carbamoylpyrrolidin-1-yl)-1,4-dioxobutan-2-ylamino)-1-oxohexan-2-ylamino)-2-oxoethyl 1-((6R,12S,15S,18R)-15-((1H-indol-3-yl)methyl)-6-amino-18-((tert-butyldisulfanyl)methyl)-12-(4-(dimethylamino)butyl)-2,2-dimethyl-7,10,13,16-tetraoxo-3,4-dithia-8,11,14,17-tetraazanonadecane)pyrrolidine-2-carboxylate (Compound SP605, H-Cys(StBu)-Gly-Lys(Me$_2$)-Trp-Cys(StBu)-Pro-$^{HO}$Gly-Lys-Asp(SBn)-Pro-NH2) (SEQ ID NO: 246) (20 mM, 0.10 µmol) and a solution of 4-butylbenzoic acid as internal standard (20 mM, 0.10 µmol) in DMA (5 µl) were added to this solution at room, temperature, and the reaction solution was allowed to stand at 37° C. for 30 minutes. A solution was then prepared containing thiophenol (0.52 µl 5 µmol), DMA (40 µl), 2 M bicine (N,N-bis-(2-hydroxyethyl)glycine) buffer (pH 8.7, 18 µl), a 0.5 M aqueous TCEP hydrochloride solution (10 µl) and a 1 M aqueous sodium hydroxide solution (12 µl), after which the above reaction solution (20 µl) was added thereto at room temperature (the pH of the mixed solution after adding the reaction solution was 8.1), the resulting reaction solution was allowed to stand at 30° C. for 24 hours, and the change in the reaction was observed by LCMS. It was confirmed that (S)-1-((3S,6S,12R,16S,19S)-3-((1H-indol-3-yl)methyl)-6-(4-(dimethylamino)butyl)-19-(2-hydroxyacetamide)-12-(mercaptomethyl)-2,5,8,11,14,18-hexaoxo-1,4,7,10,13,17-hexaazacyclotricosane-16-carbonyl)pyrrolidine-2-carboxamide (Compound SP606) was produced at 24 hours. The production ratio of Compound SP606 and the hydrolyzate (by-product) was 84:16 based on the UV area ratio by LCMS.

Figure 52:
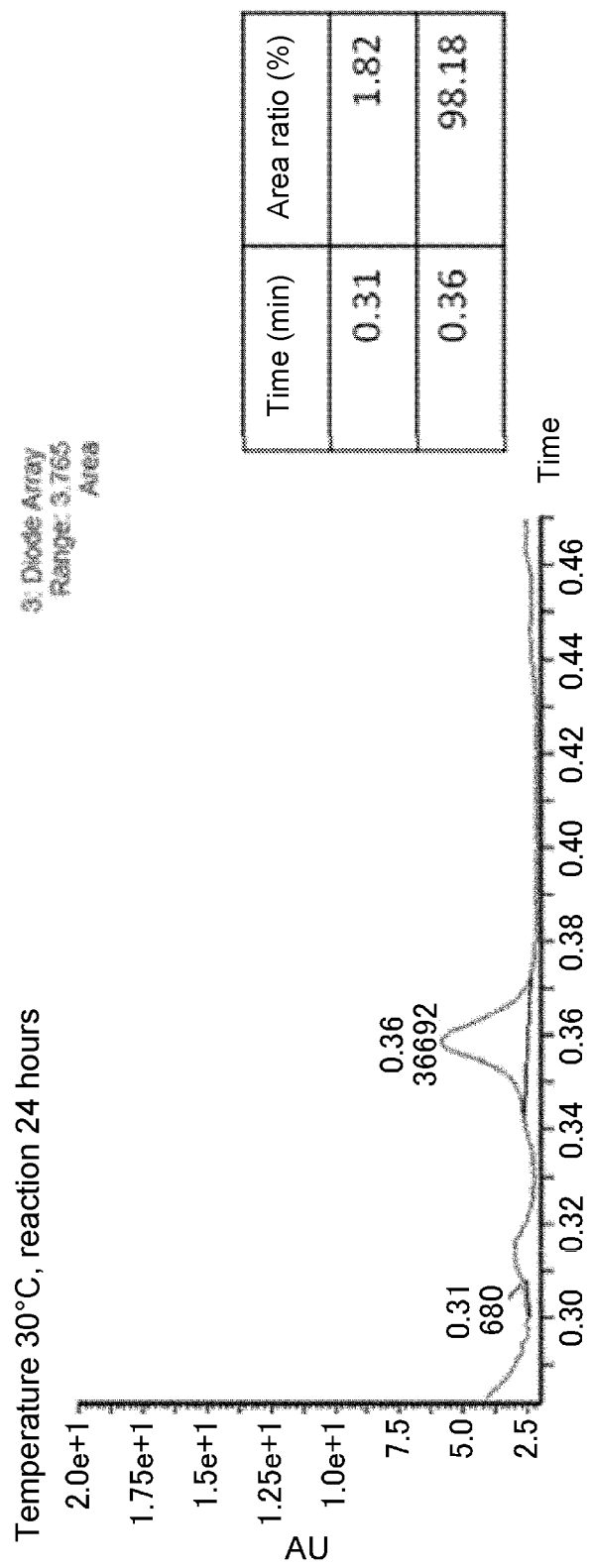
FIG. 52 is a diagram showing LCMS analysis results of a reaction solution containing produced compound SP-606.

Implementation Example Under Reaction Conditions where Branching Reaction Proceeds Well As a result of examination, it was found that the following reaction conditions are superior to the above conditions (2-2-2). The reaction was modified in that the organic solvent content was increased for primary cyclization reaction (50%), the organic solvent content was also increased for secondary branching reaction, the thiol additive was changed (4-(trifluoromethyl)benzenethiol) and the additive concentration was increased (500 mM). Further, the buffer was changed from 150 mM HEPES to 360 mM bicine (N,N-bis-(2-hydroxylethyl)glycine). A solution was prepared containing 0.5 M HEPES buffer (pH 7.0, 10 µL), water (33 µl), a 1 M aqueous sodium hydroxide solution (5 µl), N-methyl-2-pyrrolidone (NMP) (45 µl) and a 0.5 M aqueous TCEP hydrochloride solution (2 µl). (S)-2-((S)-6-Amino-1-((S)-4-(benzylthio)-1-((S)-2-carbamoylpyrrolidin-1-yl)-1,4-dioxobutan-2-ylamino)-1-oxohexan-2-ylamino)-2-oxoethyl 1-((6R,12S,15S,18R)-15-((1H-indol-3-yl)methyl)-6-amino-18-((tert-butyldisulfanyl)methyl)-12-(4-(dimethylamino)butyl)-2,2-dimethyl-7,10,13,16-tetraoxo-3,4-dithia-8,11,14,17-tetraazanonadecane)pyrrolidine-2-carboxylate (Compound SP605, H-Cys(StBu)-Gly-Lys(Me$_2$)-Trp-Cys(StBu)-Pro-$^{HO}$Gly-Lys-Asp(SBn)-Pro-NH2) (SEQ ID NO: 246) (20 mM, 0.10 µmol) and a solution of 4-butylbenzoic acid as internal standard (20 mM, 0.10 µmol) in NMP (5 µl) were added to this solution at room temperature, and the reaction solution was allowed to stand at 37° C. for 30 minutes. A solution was then prepared containing 4-(trifluoromethyl)benzenethiol (6.8 µl, 50 µmol), NMP (40 µl), 2 M bicine (N,N-bis-(2-hydroxyethyl)glycine) buffer (pH 8.7, 18 µl), a 0.5 M aqueous TCEP hydrochloride solution (10 µl) and a 5 M aqueous sodium hydroxide solution (12 µl), after which the above reaction solution (20 µl) was added thereto at room temperature (the pH of the mixed solution after adding the reaction solution was 8.2), the resulting reaction solution was allowed to stand at 30° C. for 24 hours, and the change in the reaction was observed by LCMS. It was confirmed that (S)-1-((3S,6S,12R,16S,19S)-3-((1H-indol-3-yl)methyl)-6-(4-(dimethylamino)butyl)-19-(2-hydroxyacetamide)-12-(mercaptomethyl)-2,5,8,11,14,18-hexaoxo-1,4,7,10,13,17-hexaazacyclotricosane-16-carbonyl)pyrrolidine-2-carboxamide (Compound SP606) was produced at 24 hours. The production ratio of Compound SP606 and the hydrolysate (by-product) was 98:2 based on the UV area ratio by LCMS (FIG. 52, retention time of the hydrolyzed compound: 0.31 min).

3-2. Intramolecular Branched Peptide Forming Reaction in which Conversion Reaction from Compound SP605 to SP606 to which Improved Chemical Reaction Conditions in a Buffer were Applied was Carried Out in PURE System (Translation Solution)

Figure 53:
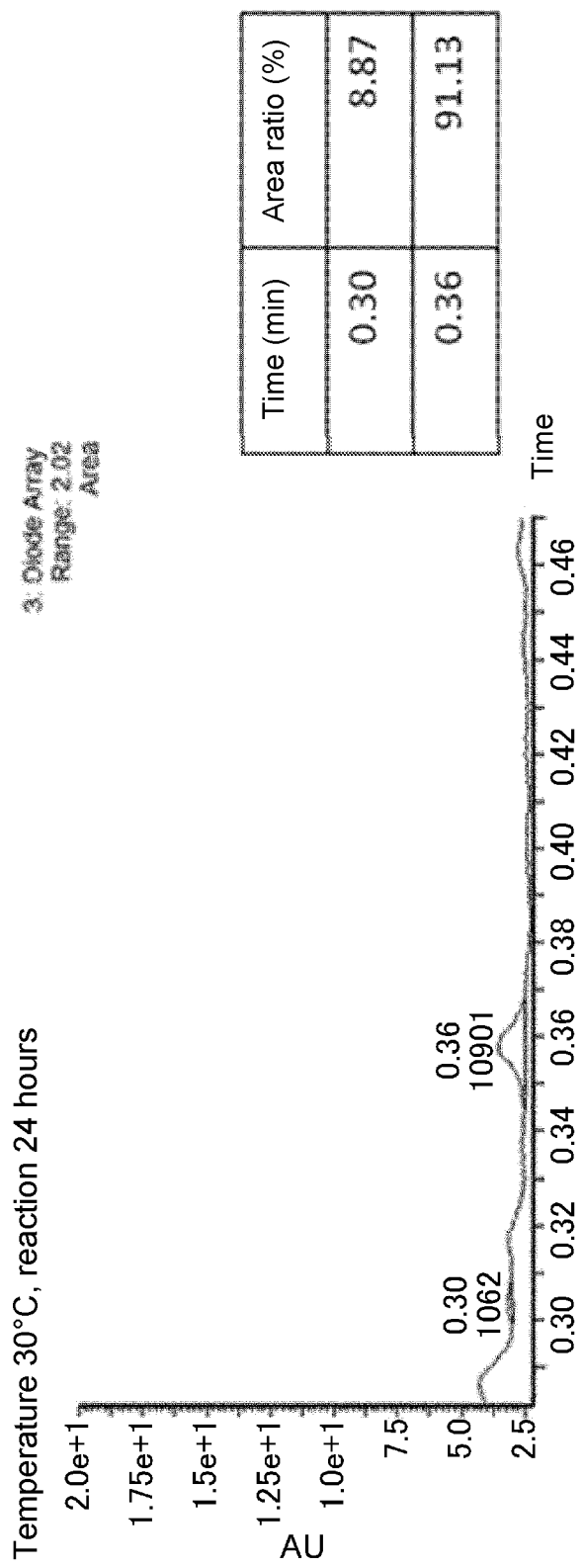
FIG. 53 is a diagram showing LCMS analysis results of a reaction solution containing produced compound SP-606.

A translation buffer (6.25 µL), water (1.25 µl), PURE-SYSTEM® classic II Sol. B (manufactured by BioComber, product No. PURE2048C) (10 µl) and 20 natural amino acid solutions (each 5 mM, 2.5 µl) were mixed and dimethylacetamide (DMA) (22.5 µl) and an aqueous TCEP solution (100 mM, 5 µl) were added thereto to prepare a solution. The ingredients of the translation buffer are 8 mM GTP, 8 mM ATP, 160 mM creatine phosphate, 400 mM HEPES-KOH, pH 7.6, 800 mM potassium acetate, 48 mM magnesium acetate, 16 mM spermidine, 8 mM dithiothreitol, 0.8 mM 10-HCO—H4 folate and 12 mg/ml E. coli MRE600 (RNase negative)-derived tRNA (Roche). (S)-2-((S)-6-Amino-1-((S)-4-(benzylthio)-1-((S)-2-carbamoylpyrrolidin-1-yl)-1,4-dioxobutan-2-ylamino)-1-oxohexan-2-ylamino)-2-oxoethyl 1-((6R,12S,15S,18R)-15-((1H-indol-3-yl)methyl)-6-amino-18-((tert-butyldisulfanyl)methyl)-12-(4-(dimethylamino)butyl)-2,2-dimethyl-7,10,13,16-tetraoxo-3,4-dithia-8,11,14,17-tetraazanonadecane)pyrrolidine-2-carboxylate (Compound SP605, H-Cys(StBu)-Gly-Lys(Me$_2$)-Trp-Cys(StBu)-Pro-$^{HO}$Gly-Lys-Asp(SBn)-Pro-NH2) (SEQ ID NO: 246) (20 mM, 0.05 µmol) and a solution of 4-butylbenzoic acid as internal standard (20 mM, 0.05 µmol) in DMA (2.5 µl) were added to this solution at room temperature, and the reaction solution was allowed to stand at 37° C. for 30 minutes. A solution was prepared containing 4-(trifluoromethyl)benzenethiol (6.8 µl, 50 µmol), DMA (40 µl), 2 M bicine (N,N-bis-(2-hydroxyethyl)glycine) buffer (pH 8.7, 18 µl), a 0.5 M aqueous TCEP hydrochloride solution (10 µl) and a 5 M aqueous sodium hydroxide solution (12 µl), after which the above reaction solution (20 µl) was added thereto at room temperature (the pH of the mixed solution after adding the reaction solution was 8.2), the resulting reaction solution was allowed to stand at 30° C. for 24 hours, and the change in the reaction was observed by LCMS. It was confirmed that (S)-1-((3S,6S,12R,16S,19S)-3-((1H-indol-3-yl)methyl)-6-(4-(dimethylamino)butyl)-19-(2-hydroxyacetamide)-12-(mercaptomethyl)-2,5,8,11,14,18-hexaoxo-1,4,7,10,13,17-hexaazacyclotricosane-16-carbonyl)pyrrolidine-2-carboxamide (Compound SP606) was produced at 24 hours. The production ratio of Compound SP606 and the hydrolysate (by-product) was 91:9 based on the UV area ratio by LCMS (FIG. 53, retention time of the hydrolyzed compound: 0.30 min).

3-3. Branched Peptide Production Reaction in an Eluate Obtained by Purifying the Translation Solvent of PURE SYSTEM Using RNeasy® MinElute™ Cleanup Kit (Qiagen) (Conversion from Compound SP605 to Compound SP606)

When display libraries are used for translated peptides, posttranslational modification can be carried out by adding reagents to translation solutions directly, or partial or entire posttranslational modification can be carried out after purifying peptide-RNA complexes once. Such purification processes include purification using RNeasy® MinElute™ Cleanup Kit (Qiagen). The following experiment was carried out as an example of posttranslational modification after performing such purification.

An eluate obtained by purifying the translation solvent of PURE SYSTEM using RNeasy® MinElute™ Cleanup Kit (Qiagen) (35 µl), dimethylacetamide (DMA) (45 µl) and a 100 mM tris(2-carboxyethyl)phosphine (TCEP) hydrochloride solution (10 µl, 1.0 µmol) were mixed, and a solution of (S)-2-((S)-6-amino-1-((S)-4-(benzylthio)-1-((S)-2-carbamoylpyrrolidin-1-yl)-1,4-dioxobutan-2-ylamino)-1-oxohexan-2-ylamino)-2-oxoethyl 1-((6R,12S,15S,18R)-15-((1H-indol-3-yl)methyl)-6-amino-18-((tert-butyldisulfanyl)methyl)-12-(4-(dimethylamino)butyl)-2,2-dimethyl-7,10,13,16-tetraoxo-3,4-dithia-8,11,14,17-tetraazanonadecane)pyrrolidine-2-carboxylate (Compound SP605) (H-Cys(StBu)-Gly-Lys(Me$_2$)-Trp-Cys(StBu)-Pro-$^{HO}$Gly-Lys-Asp(SBn)-Pro-NH$_2$) (SEQ ID NO: 246) (20 mM, 0.10 µmol) and 4-butylbenzoic acid used as internal standard (20 mM, 0.10 µmol) in DMA (5.0 µl) was added to the mixture at room temperature. 2M HEPES buffer (5 µl, pH=7.5) and a 1 N aqueous sodium hydroxide solution (1.5 µl) were added and the mixture was allowed to stand at 37° C. for 30 minutes in a thermal cycler at pH=7.5.

Figure 54:
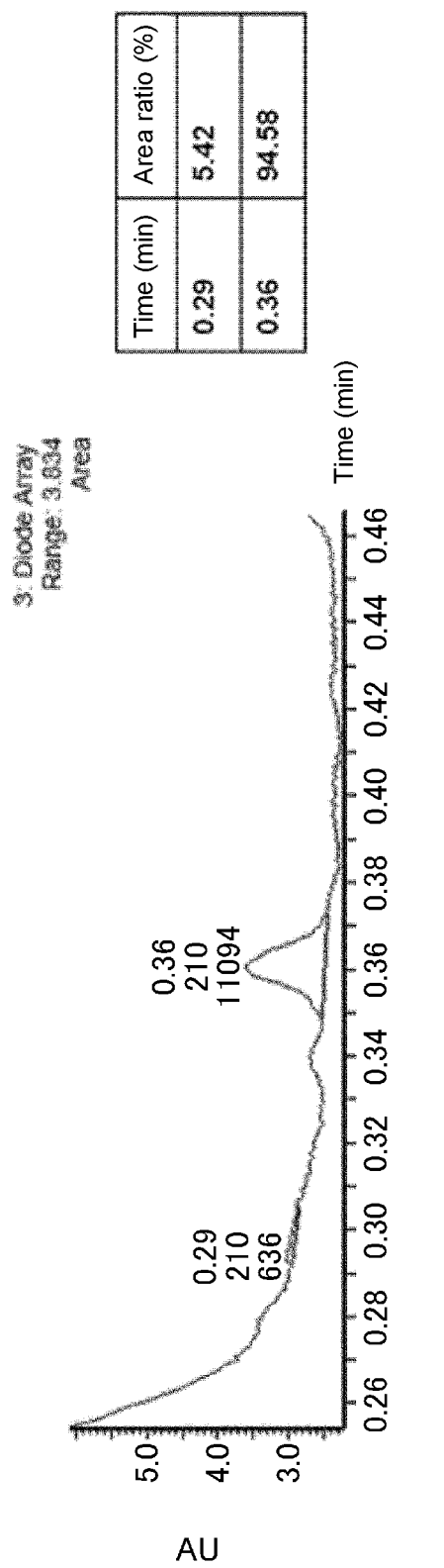
FIG. 54 is a diagram showing LCMS analysis results of a reaction solution containing produced compound SP-606.

The resulting reaction solution (20 µl) was added at room temperature to a solution prepared from 4-(trifluoromethyl)benzenethiol (6.8 µl, 50 µmol), dimethylacetamide (DMA) (40 µl), 2 M bicine (N,N-bis-(2-hydroxyethyl)glycine) buffer (pH 8.7, 16 µl), a 0.5 M aqueous tris(2-carboxyethyl)phosphine (TCEP) hydrochloride solution (10 µl) and a 5 N aqueous sodium hydroxide solution (14 µl), the mixture was allowed to stand at 37° C. for 20 hours in the thermal cycler at pH=8.2, and the change in the reaction was observed by LCMS. It was confirmed that (S)-1-((3S,6S,12R,16S,19S)-3-((1H-indol-3-yl)methyl)-6-(4-(dimethylamino)butyl)-19-(2-hydroxyacetamide)-12-(mercaptomethyl)-2,5,8,11,14,18-hexaoxo-1,4,7,10,13,17-hexaazacyclotricosane-16-carbonyl)pyrrolidine-2-carboxamide (Compound SP606) was produced after 20 hours. The production ratio of the intended compound and the hydrolysate (LCMS retention time 0.29 min) was 95:5 based on the UV area ratio by LCMS (FIG. 54).

LCMS (ESI) m/z=900 (M+H)+

Retention time: 0.36 min (analysis condition SQDFA05)

The eluate obtained by purifying the translation solvent of PURE SYSTEM using RNeasy® MinElute™ Cleanup Kit (Qiagen) was prepared as follows. The translation buffer previously described in Example (12.5 µl), PURESYSTEM® classic II Sol. B (BioComber, product No. PURE2048C) (20 µL), 20 natural amino acid solutions (each 5 mM, 5.0 µl) and water (62.5 µl) were added to prepare a translation solution. Buffer RLT (70 µl) and EtOH (135 µl) were added to the translation solution (20 µl), and the mixture was pipetted and applied to RNeasy MinElute Spin Column. The filtrate was removed by centrifugation at 10000 rpm for 15 seconds. Buffer RPE (500 µl) was added to RNeasy MinElute Spin Column, and the filtrate was removed by centrifugation at 10000 rpm for 15 seconds. A 80% aqueous EtOH solution (500 µl) was added to RNeasy MinElute Spin Column, and the filtrate was removed by centrifugation at 10000 rpm for 2 minutes. The cover of RNeasy MinElute Spin Column was opened, centrifugation was performed at 15000 rpm for 5 minutes to dry the column. After that, water (22 µl) was applied and the eluted solution was used. RNase free water was used in this case.

The 100 mM tris(2-carboxyethyl)phosphine (TCEP) hydrochloride solution was prepared by the following method. The solution was prepared by adding a 2 N aqueous sodium hydroxide solution (18 µl) and water (62 µl) to a 500 mM aqueous tris(2-carboxyethyl)phosphine (TCEP) hydrochloride solution (20 µl, 10 µmol).

As described above, it was confirmed that the intended reaction similarly proceeded in water (buffer) and in PureSystem (reaction translation solution) without significant difference. RNA was sufficiently stable under such reaction conditions, and this made it clear that branching reaction efficiently proceeds from linear peptide compounds after reaction and that branching reaction can be allowed to efficiently proceed in peptide-RNA complexes without RNA decomposition.

These results disclosed the following facts.

When an amino group having a reaction auxiliary group is located in a triangle unit, primary cyclization reaction proceeds highly selectively so that selectivity for activation of Cys-Pro-HOGly for secondary branching can be attained. Reaction selectivity is particularly high when the content of the organic solvent miscible with water is high. Secondary branching is preferably carried out in the presence of a thiol (preferably an arylthiol) as an additive, in the presence of an organic solvent miscible with water, at a pH of the reaction solution of 7.0 and 9.0 and at a reaction temperature of 0° C. to 100° C. (more preferably 15° C. to 50° C.). As is clear from the results previously shown, the present conditions provide similar results both in a buffer (water) and in a translation solution (PureSystem).

3-4. Desulfurization Reaction from Intramolecular Branched Peptides Having Linear Portions 2

Synthesis of (S)-1-((3S,6S,12S,16S,19S)-3-((1H-indol-3-yl)methyl)-6-(4-(dimethylamino)butyl)-19-(2-hydroxyacetamide)-12-methyl-2,5,8,11,14,18-hexaoxo-1,4,7,10,13,17-hexaazacyclotricosane-16-carbonyl)pyrrolidine-2-carboxamide (Compound SP607)

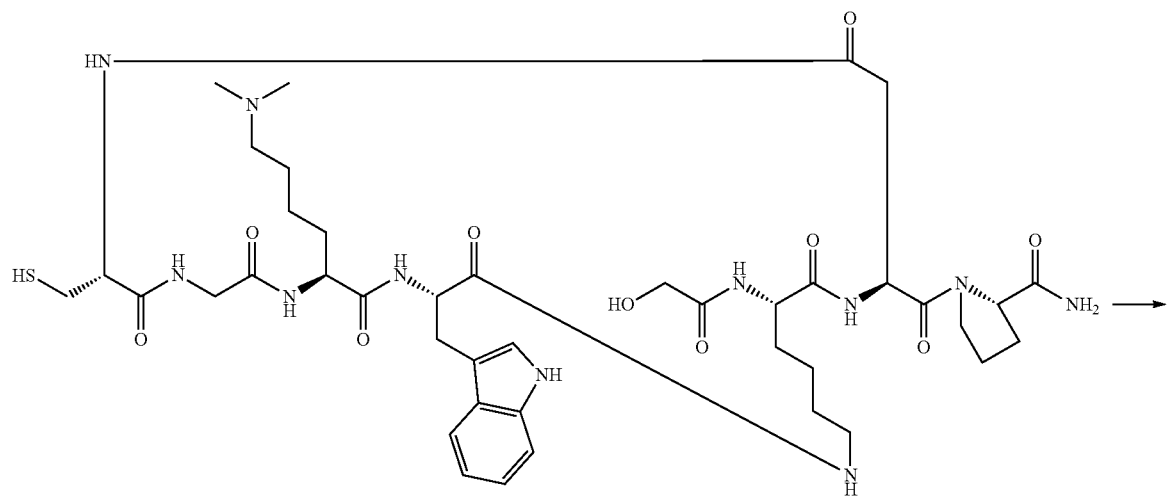

Compound SP606

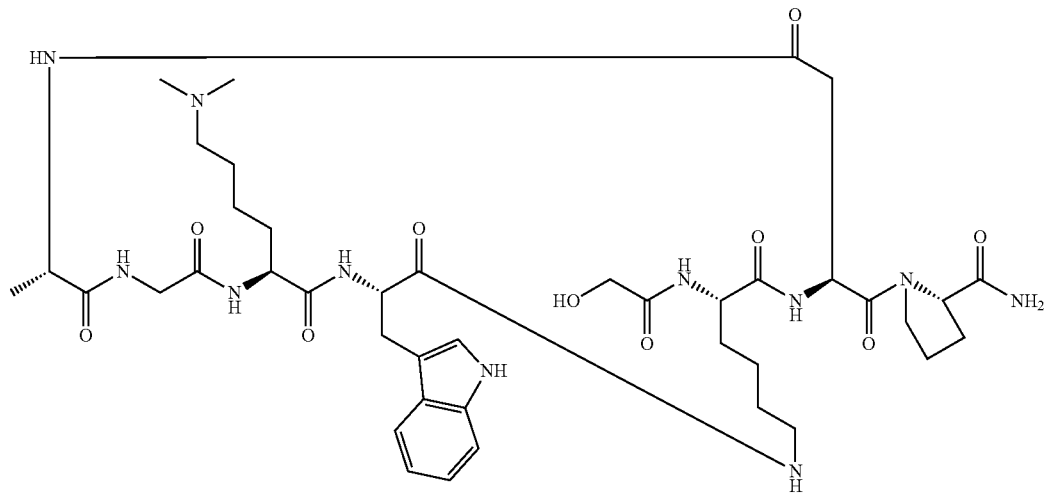

Compound SP607

Desulfurization Reaction from an Intramolecular Branched Peptide in PURE System

Figure 55:
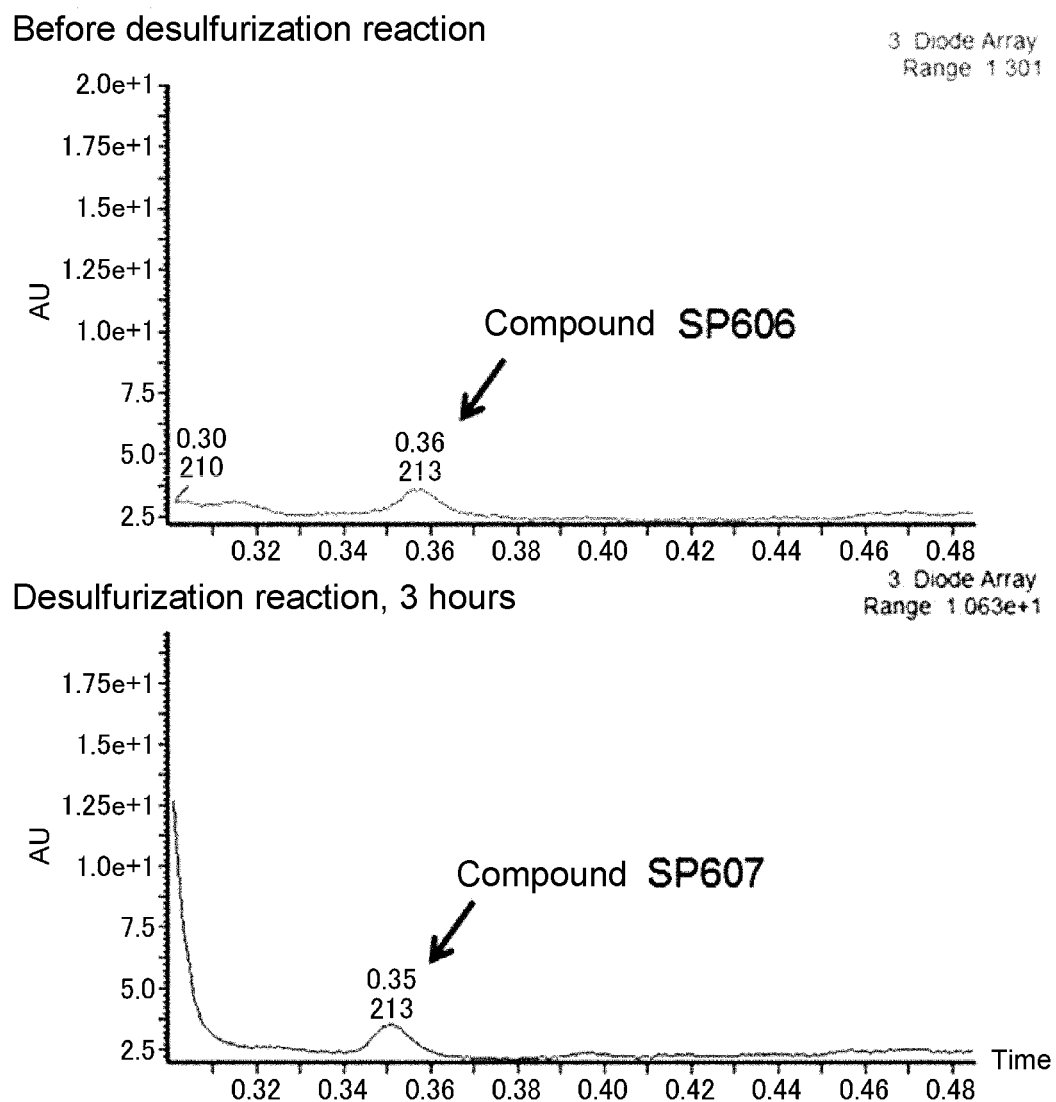
FIG. 55 is a diagram showing LCMS analysis results of a reaction solution containing produced compound SP-607.

A 0.5 M aqueous tris(2-carboxyethyl)phosphine (TCEP) hydrochloride solution (10 μl) was added to the aforementioned reaction solution (10 μl) used for intramolecular branched peptide forming reaction from the compound that mimicked the translated peptide(Compound SP605) as described in 3-2. The mixed solution was washed with hexane (200 μl) (washing with hexane was performed seven times), after which a aqueous 500 mM glutathione solution (4 μl), a 1 M aqueous 2,2-azobis[2-(2-imidazolin-2-yl)propane] dihydrochloride ($V_A$-044) solution (2 μl) and a 5 M aqueous sodium hydroxide solution (2 μl) were added to the resulting aqueous layer at room temperature and the mixture was allowed to stand at 40° C. for 3 hours. The change in the reaction was traced by LCMS to confirm that the starting material Compound SP606 was completely consumed and converted to the intended (S)-1-((3S,6S,12S,16S,19S)-3-((1H-indol-3-yl)methyl)-6-(4-(dimethylamino)butyl)-19-(2-hydroxyacetamide)-12-methyl-2,5,8,11,14,18-hexaoxo-1,4,7,10,13,17-hexaazacyclotricosane-16-carbonyl)pyrrolidine-2-carboxamide (Compound SP607) after 3 hours (FIGS. 55 and 56).

LCMS (ESI) m/z=868 (M+H)+
Retention time: 0.35 min (analysis condition SQDFA05)

Desulfurization Reaction from a Branched Peptide Produced by Reaction Carried Out in an Eluate Obtained by Purifying the Translation Solvent of PURE SYSTEM Using RNeasy® MinElute™ Cleanup Kit (Qiagen)

Figure 57:
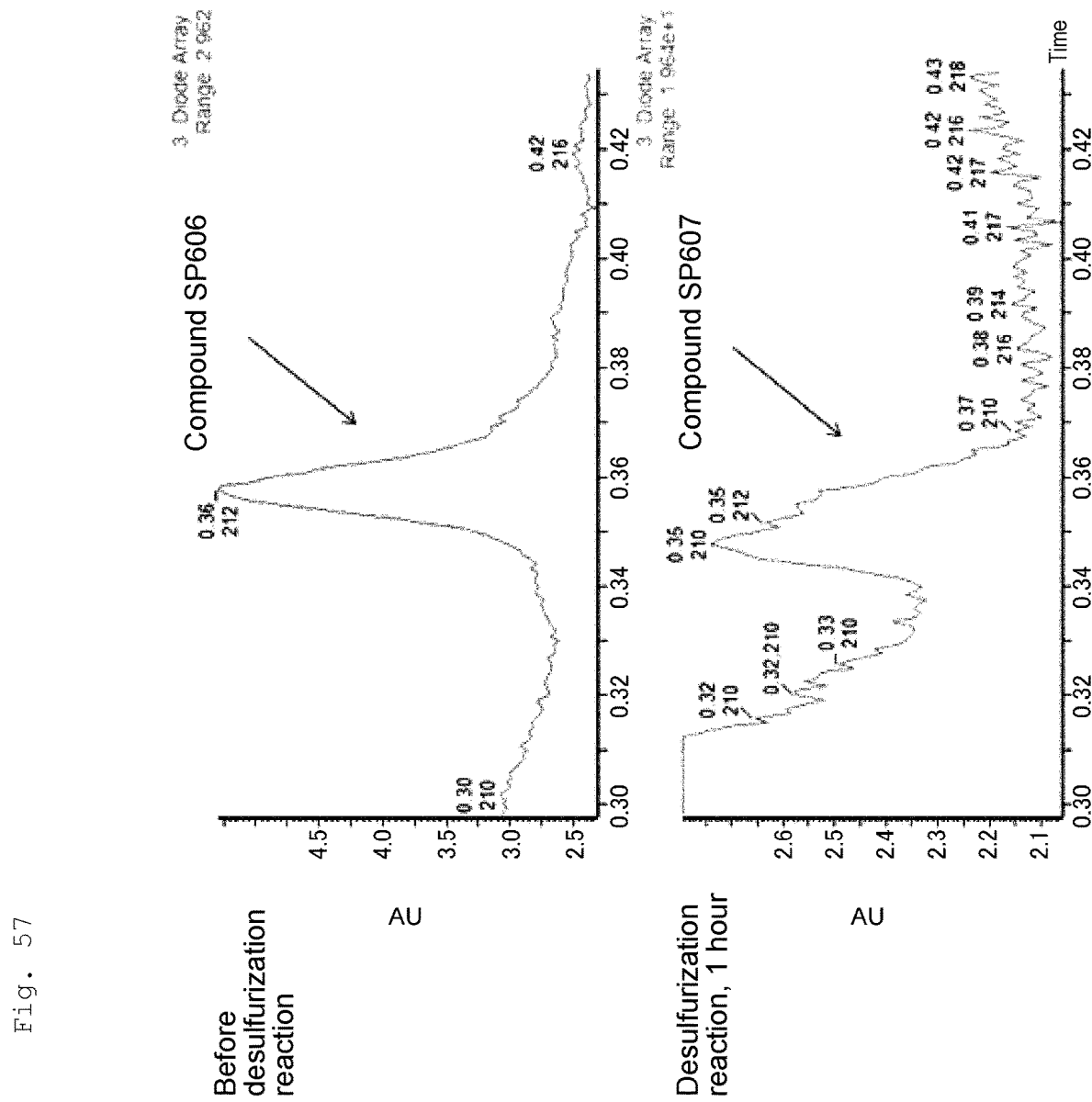
FIG. 57 is a diagram showing LCMS analysis results of a reaction solution containing produced compound SP-607.
Figure 58:
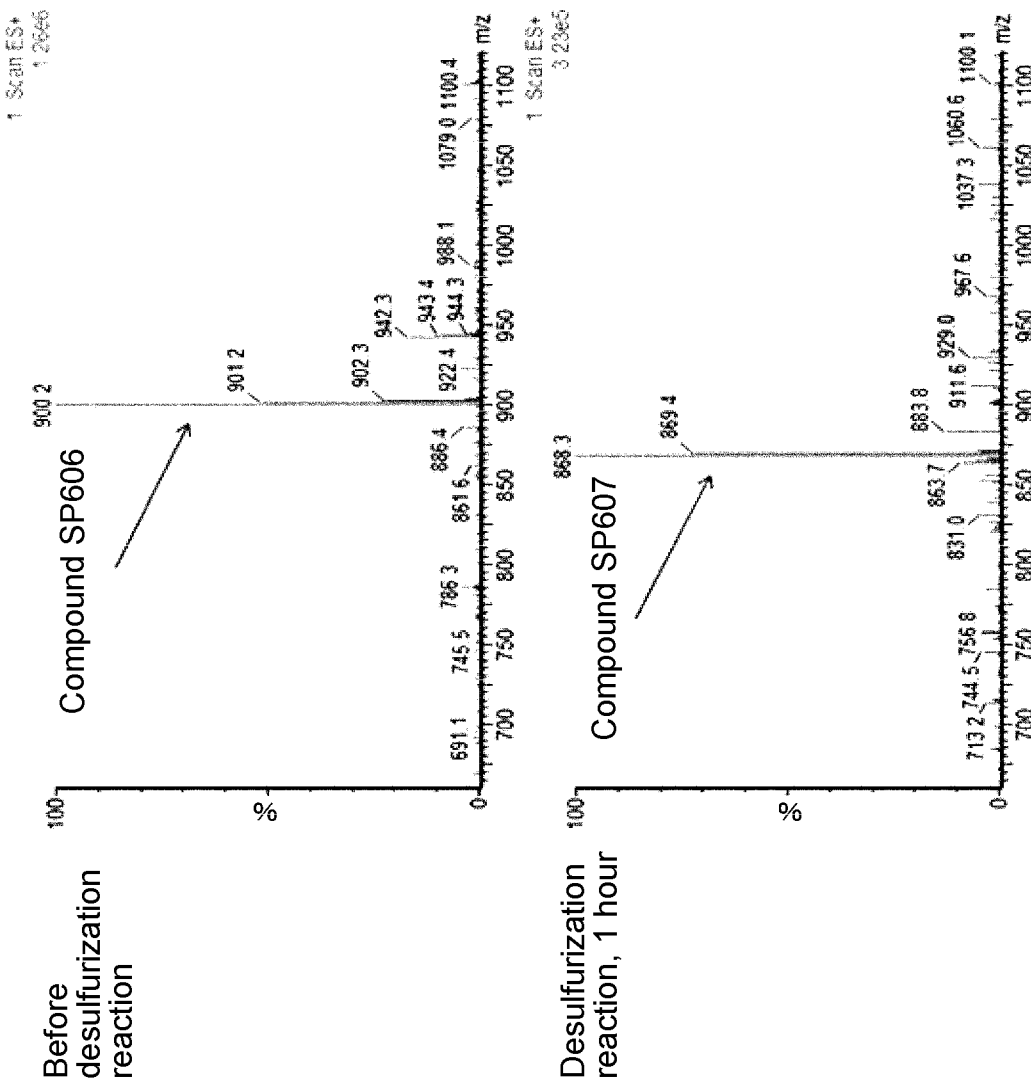
FIG. 58 is a diagram showing a mass chromatogram (upper) before desulfurization reaction (compound SP606) and a mass chromatogram (lower) obtained by integrating and averaging mass chromatograms of retention times from 0.34 minutes to 0.39 minutes after desulfurization reaction for 3 hours (analysis condition SQD FA05).

A 0.5 M aqueous tris(2-carboxyethyl)phosphine (TCEP) hydrochloride solution (50 μl) was added to the aforementioned reaction solution (50 μl) used for branched peptide forming reaction in an eluate obtained by purifying the translation solvent of PURE SYSTEM using RNeasy® MinElute™ Cleanup Kit (Qiagen) (Conversion from Compound SP605 to Compound SP606) (3-3.). After the mixed solution was washed with hexane (1.0 ml) (washing with hexane was performed seven times), a aqueous 500 mM glutathione solution (20 μl), a 1 M aqueous 2,2-azobis[2-(2-imidazolin-2-yl)propane] dihydrochloride ($V_A$-044) solution (10 μl) and a 5 N aqueous sodium hydroxide solution (8 μl) were added to the resulting aqueous layer at room temperature and the mixture was allowed to stand at 45° C. for 30 minutes. The change in the reaction was traced by LCMS to confirm that the intended (S)-1-((3S,6S,12S,16S,19S)-3-((1H-indol-3-yl)methyl)-6-(4-(dimethylamino)butyl)-19-(2-hydroxyacetamide)-12-methyl-2,5,8,11,14,18-hexaoxo-1,4,7,10,13,17-hexaazacyclotricosane-16-carbonyl)pyrrolidine-2-carboxamide (Compound SP607) was produced after 1 hour (FIGS. 57 and 58).

LCMS (ESI) m/z=868 (M+H)+
Retention time: 0.35 min (analysis condition SQD FA05)

4. Implementation of Examples where the First Cyclization Reaction is the Amidation Reaction Between N-Terminals Having Reaction Auxiliary Groups and Active Thioesters on the C-Terminal Side Occurs, and then Active Esters are Directly Generated from the Esters and the Protecting Group of Amines is Removed. The Cyclic Peptide is Branched by Reaction Between Active Esters and Amines Having Reaction Auxiliary Groups in Secondary Reaction Effectiveness was confirmed by the same concept as described in 3.

4-1. Synthesis of a Translated Peptide Model Compound (Compound SP616)

The model compound SP616 was synthesized according to the following scheme in order to implement an example where amidation cyclization reaction (native chemical ligation) is carried out using Cys at the N-terminal and Asp (SBn) on the C-terminal side in primary cyclization, and active ester is generated from activating glycolic acid ester and amidation reaction is carried out by deprotecting N, S-acetal of Cys which is located at the side chain amino group of Lys in secondary branching reaction.

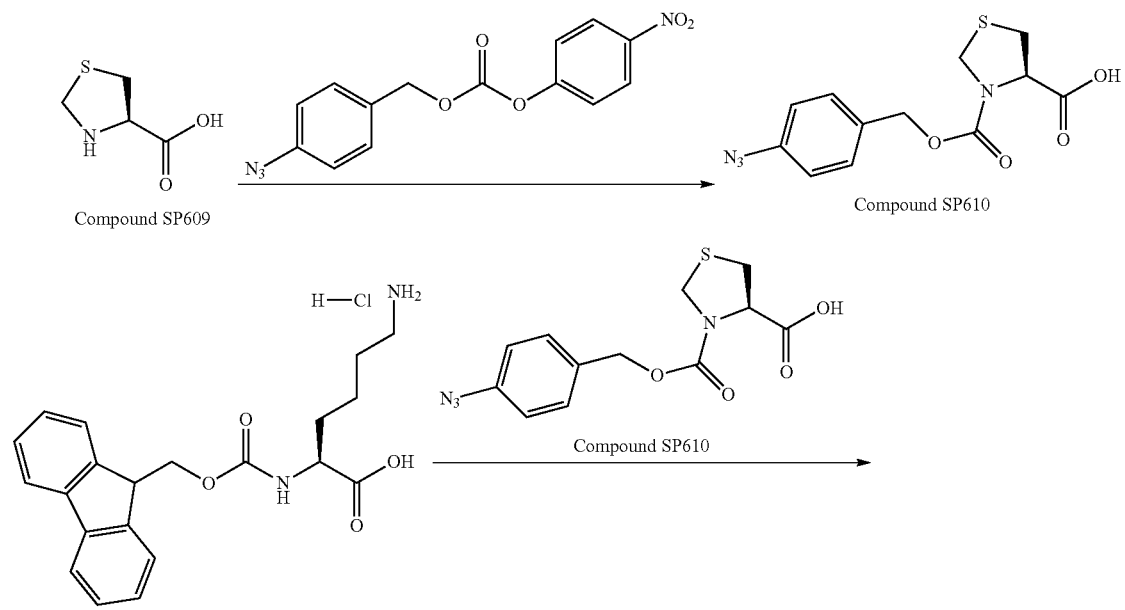

Figure 99:
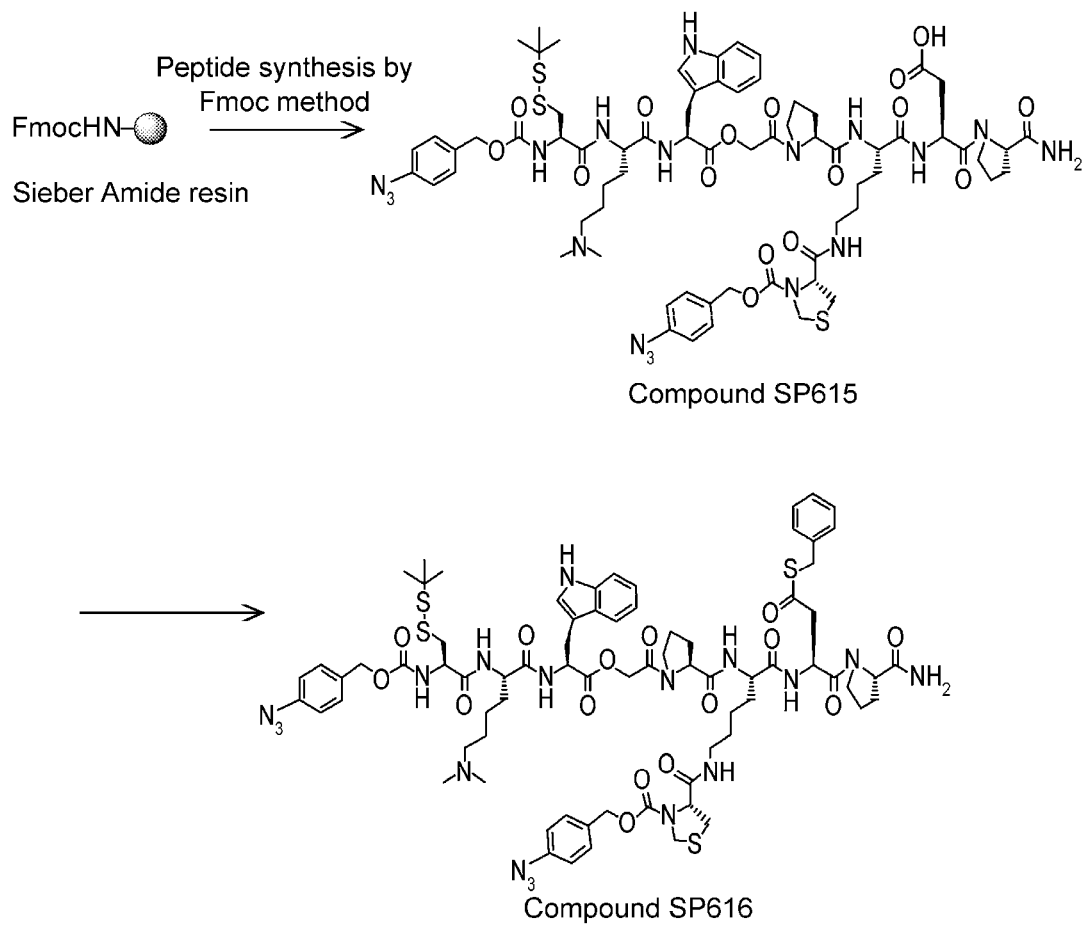
FIG. 99 is a diagram showing the synthesis of a translated peptide model compound SP616.

-continued
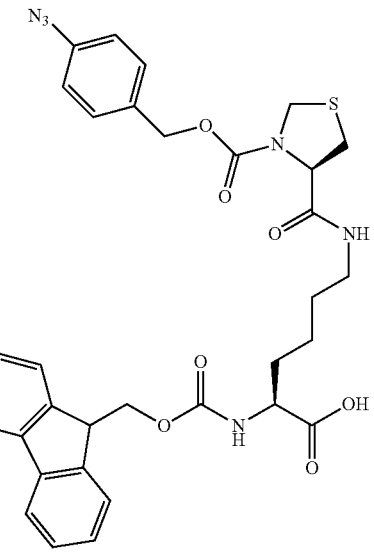
Compound SP611
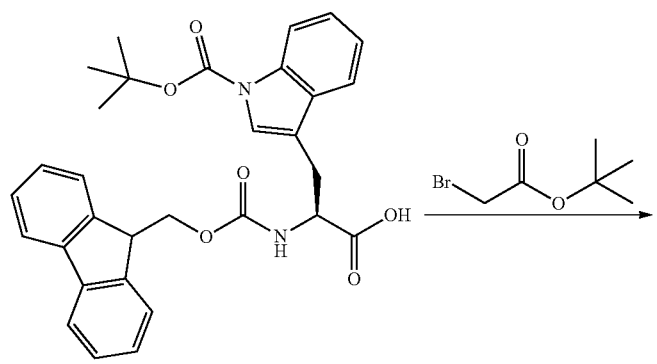
Compound SP613
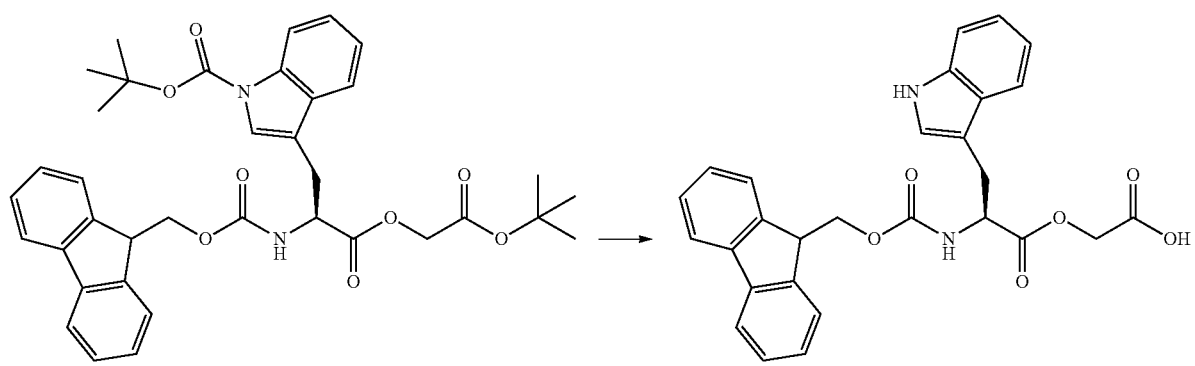
Compound SP614                    Compound SP612
See FIG. 99.

Synthesis of (R)-3-(((4-azidobenzyl)oxy)carbonyl)thiazolidine-4-carboxylic Acid (Acbz-Thz-OH) (Compound SP610)

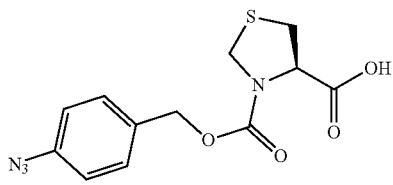 [SMILES: [N-]=[N+]=Nc1ccc(COC(=O)N2CSC[C@H]2C(=O)O)cc1]

4-Azidobenzyl (4-nitrophenyl) carbonate prepared by a method known in the literature (Bioconjugate Chem. 2008, 19, 714) (3.50 g, 11.1 mmol) was added to a solution of (R)-thiazolidine-4-carboxylic acid (H-Thz-OH) (Compound SP609) (1.48 g, 11.1 mmol) and triethylamine (Et₃N) (4.66 ml, 33.4 mmol) in Dimethylformamide (DNF) (11.0 ml) at 0° C. under a nitrogen atmosphere, and the mixture was stirred at room temperature for 19 hours. Formic acid (2.1 ml) was added to the reaction solution, and the mixture was purified by reverse-phase silica gel chromatography (0.1% aqueous formic acid solution/0.1% formic acid-acetonitrile solution) to afford (R)-3-(((4-azidobenzyl)oxy)carbonyl)thiazolidine-4-carboxylic acid (Acbz-Thz-OH) (Compound SP610) (3.17 g, 92%).

LCMS (ESI) m/z=307 (M–H)–
Retention time: 0.68 min (analysis condition SQDFA05)

Synthesis of (S)-2-((((9H-fluoren-9-yl)methoxy)carbonyl)amino)-6-((R)-3-(((4-azidobenzyl)oxy)carbonyl)thiazolidine-4-carboxamido)hexanoic Acid (Fmoc-Lys(Acbz-Thz)-OH) (Compound SP611)

In the present specification, a compound amidated between the amino group at side chain of Fmoc-Lys-OH and the carboxylic group of Acbz-Thz-OH is defined as Fmoc-Lys(Acbz-Thz)-OH like in other examples.

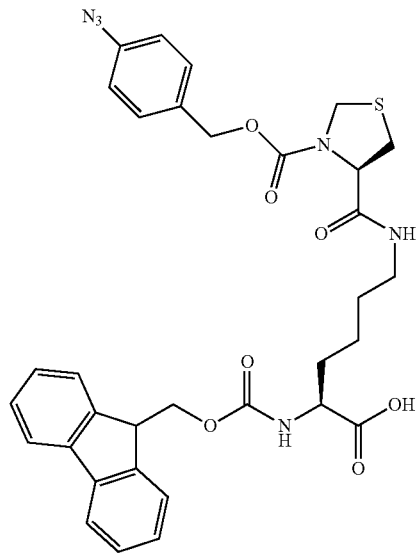 [SMILES: [N-]=[N+]=Nc1ccc(COC(=O)N2CSC[C@H]2C(=O)NCCCC[C@H](NC(=O)OCC2c3ccccc3-c3ccccc32)C(=O)O)cc1]

4-(4,6-Dimethoxy[1.3.5]triazin-2-yl)-4-methylmorpholinium chloride (DMT-MM) (2.85 g, 10.3 mmol) was added to a solution of (R)-3-(((4-azidobenzyl)oxy)carbonyl)thiazolidine-4-carboxylic acid (Acbz-Thz-OH) (Compound SP610) (3.17 g, 10.3 mmol) in dimethylformamide (DMF) (17.0 ml) at room temperature under a nitrogen atmosphere, and the mixture was stirred at the same temperature for 1 hour and 30 minutes. A solution of (S)-2-((((9H-fluoren-9-yl)methoxy)carbonyl)amino)-6-aminohexanoic acid (Fmoc-Lys-OH) hydrochloride (4.16 g, 10.3 mmol) and diisopropylethylamine (DIPEA) (2.69 ml, 15.4 mmol) in dimethylformamide (DMF) (17 ml) was added to the reaction solution at room temperature, and the mixture was stirred at the same temperature for 4 hours. Formic acid (1.9 ml) was added to the reaction solution, and the mixture was purified by reverse-phase silica gel chromatography (0.1% aqueous formic acid solution/0.1% formic acid-acetonitrile solution) to afford (S)-2-((((9H-fluoren-9-yl)methoxy) carbonyl)amino)-6-((R)-3-(((4-azidobenzyl)oxy)carbonyl)thiazolidine-4-carboxamido)hexanoic acid (Fmoc-Lys(Acbz-Thz)-OH) (Compound SP611) (3.48 g, 51%).

LCMS (ESI) m/z=659 (M+H)+
Retention time: 0.87 min (analysis condition SQDFA05)

Synthesis of (S)-2-((2-((((9H-fluoren-9-yl)methoxy)carbonyl)amino)-3-(1H-indol-3-yl)propanoyl)oxy)acetic Acid (Fmoc-Trp-$^{HO}$Gly-OH) (Compound SP612)

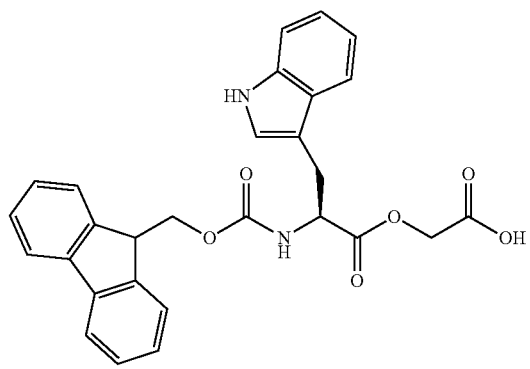 [SMILES: O=C(O)COC(=O)[C@H](Cc1c[nH]c2ccccc12)NC(=O)OCC1c2ccccc2-c2ccccc21]

tert-Butyl 2-bromoacetate (2.09 ml, 14.2 mmol) was added to a solution of (S)-2-((((9H-fluoren-9-yl)methoxy)carbonyl)amino)-3-(1-(tert-butoxycarbonyl)-1H-indol-3-yl)propanoic acid (Fmoc-Trp(Boc)-OI-1) (Compound SP613) (5.0 g, 9.50 mmol) and diisopropylethylamine (DIPEA) (4.98 ml, 28.5 mmol) in dichloromethane (DCM) (9.5 ml) at room temperature under a nitrogen atmosphere, and the mixture was stirred at the same temperature for 48 hours. An aqueous ammonium chloride solution was added to the reaction solution, the mixture was extracted with dichloromethane (DCM) twice, and the organic layer was washed with brine twice. The organic layer was dried over sodium sulfate, and then filtered and concentrated under reduced pressure. The resulting residue was purified by normal-phase silica gel chromatography (hexane/ethyl acetate) to afford (S)-tert-butyl 3-(2-((((9H-fluoren-9-yl)methoxy)carbonyl)amino)-3-(2-(tert-butoxy)-2-oxoethoxy)-3-oxopropyl)-1H-indole-1-carboxylate (Fmoc-Trp(Boc)-Gly-OtBu) (Compound SP614) as a mixture (5.25 g).

Triisopropylsilane (TIPS) (4.20 ml, 20.5 mmol) and trifluoroacetic acid (TFA) (8.21 ml, 107 mmol) were added to a solution of the resulting mixture (5.25 g) in dichloromethane (DCM) (8.19 ml) at room temperature, and the mixture was stirred at the same temperature for 5 hours and 30 minutes. The reaction solution was concentrated under reduced pressure, and the resulting residue was purified by reverse-phase silica gel chromatography (0.1% aqueous formic acid solution/0.1% formic acid-acetonitrile solution) to afford (S)-2-((2-((((9H-fluoren-9-yl)methoxy)carbonyl)amino)-3-(1H-indol-3-yl)propanoyl)oxy)acetic acid (Fmoc-Trp-$^{HO}$Gly-OH) (Compound SP612) (3.40 g, yield in two steps: 74%).

LCMS (ESI) m/z=485 (M+H)+
Retention time: 0.83 min (analysis condition SQDFA05)

Synthesis of (S)-3-((S)-2-((S)-1-((6R,9S,12S)-12-((1H-indol-3-yl)methyl)-6-((((4-azidobenzyl)oxy)carbonyl)amino)-9-(4-(dimethylamino)butyl)-2,2-dimethyl-7,10,13-trioxo-14-oxa-3,4-dithia-8,11-diazahexadecane-16-oyl)pyrrolidine-2-carboxamido)-6-((R)-3-(((4-azidobenzyl)oxy)carbonyl)thiazolidine-4-carboxamido) hexanamido)-4-((S)-2-carbamoylpyrrolidin-1-yl)-4-oxobutanoic Acid (Acbz-Cys(StBu)-Lys(Me$_2$)-Trp-Fic)Gly-Pro-Lys (Acbz-Thz)-Asp-Pro-NH$_2$) (Compound 5P615) (SEQ ID NO: 247)

OH, Fmoc-Asp(OPis)-OH, (S)-2-((((9H-fluoren-9-yl)methoxy)carbonyl)amino)-6-((R)-3-(((4-azidobenzyl)oxy)carbonyl)thiazolidine-4-carboxamido)hexanoic acid (Fmoc-Lys(Acbz-Thz)-OH) (Compound SP611), (S)-2-((2-((((9H-fluoren-9-yl)methoxy)carbonyl)amino)-3-(1H-indol-3-yl)propanoyl)oxy)acetic acid (Fmoc-Trp-$^{HO}$Gly-OH) (Compound SP612) and Fmoc-Lys(Me$_2$)-OH hydrochloride were used as Fmoc amino acids.

After the peptide elongation, the resin was washed with dimethylformamide (DMF) and dichloromethane (DCM). The peptide was cleaved from the resin by adding a 2% solution of trifluoroacetic acid (TFA) in dichloromethane (DCM)/2,2,2-trifluoroethanol (TFE) (=1/1, v/v, 4.0 ml) to the resin and reacting for 3 hours at room temperature. After completion of the reaction, the solution in the tube was filtered through a synthesis column to remove the resin, and the resin was washed with dichloromethane (DCM)/2,2,2-trifluoroethanol (TFE) (=1/1, v/v, 4.0 mL) four times. The resulting solution was concentrated under reduced pressure, and the residue was purified by reverse-phase silica gel chromatography (0.1% aqueous formic acid solution/0.1% formic acid-acetonitrile solution) to afford (S)-3-((S)-2-((S)-1-((6R,9S,12S)-12-((1H-indol-3-yl)methyl)-6-((((4-azido-

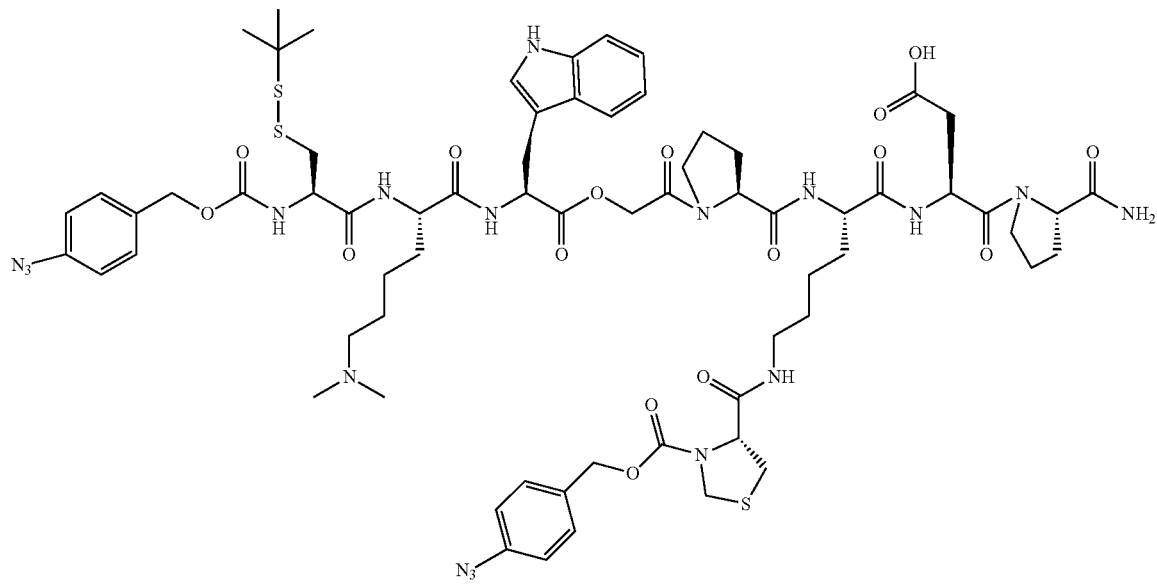 [SMILES: CN(C)CCCC[C@H](NC(=O)[C@H](CSSC(C)(C)C)NC(=O)OCc1ccc(N=[N+]=[N-])cc1)C(=O)N[C@@H](Cc1c[nH]c2ccccc12)C(=O)OCC(=O)N1CCC[C@H]1C(=O)N[C@@H](CCCCNC(=O)[C@@H]1CSCN1C(=O)OCc1ccc(N=[N+]=[N-])cc1)C(=O)N[C@@H](CC(=O)O)C(=O)N1CCC[C@H]1C(N)=O]

Peptide chain elongation was carried out according to the general method for solid-phase synthesis of peptides containing ester groups in the main chains by automatic synthesizers as previously described in Examples (2-1). Sieber Amide Resin (160 mg per column, 8 columns used, purchased from Novabiochem) was used as the resin. (R)-2-((((4-azidobenzyl)oxy)carbonyl)amino)-3-(tert-butyldisulfanyl)propanoic acid (Acbz-Cys(StBu)-OH) (Compound tk20) was used as N-terminal amino acid, and Fmoc-Probenzyl)oxy)carbonyl)amino)-9-(4-(dimethylamino)butyl)-2,2-dimethyl-7,10,13-trioxo-14-oxa-3,4-dithia-8,11-diazahexadecane-16-oyl)pyrrolidine-2-carboxamido)-6-((R)-3-(((4-azidobenzyl)oxy)carbonyl)thiazolidine-4-carboxamido)hexanamido)-4-((S)-2-carbamoylpyrrolidin-1-yl)-4-oxobutanoic acid (Acbz-Cys(StBu)-Lys(Me$_2$)-Trp-$^{HO}$Gly-Pro-Lys(Acbz-Thz)-Asp-Pro-NH$_2$) (Compound SP615) (SEQ ID NO: 247) (179 mg, 13%).

LCMS (ESI) m/z=1511.4 (M+H)+
Retention time: 0.69 min (analysis condition SQDFA05)

Synthesis of (R)-4-Azidobenzyl 4-(((S)-5-((S)-1-((6R,9S,12S)-12-((1H-indol-3-yl)methyl)-6-((((4-azidobenzyl)oxy)carbonyl)aminooxy)carbonyl)amino)-9-(4-(dimethylamino)butyl)-2,2-dimethyl-7,10,13-trioxo-14-oxa-3,4-dithia-8,11-diazahexadecan-16-oyl)pyrrolidine-2-carboxamido)-6-(((s)-4-(benzyithio)-1-((S)-2-carbamoylpyrrolidin-1-yl)-1,4-dioxobutan-2-yl)amino)-6-oxohexyl)carbamoyl)thiazolidine-3-carboxylate (Acbz-Cys(StBu)-Lys(Me₂)-Trp-$^{HO}$Gly-Pro-Lys(Acbz-Thz)-Asp(SBn)-Pro-NH₂) (Compound SP616) (SEQ ID NO: 248)

pyrrolidine-2-carboxamido)-6-(((S)-4-(benzyithio)-1-((S)-2-carbamoylpyrrolidin-1-yl)-1,4-dioxobutan-2-yl)amino)-6-oxohexyl)carbamoyl)thiazolidine-3-carboxylate (Acbz-Cys (StBu)-Lys(Me₂)-Tr-$^{HO}$Gly-Pro-Lys(Acbz-Thz)-Asp(SBn)-Pro-NH₂) (Compound SP616) (SEQ ID NO: 248) (45.7 mg, 85%).

LCMS (ESI) m/z=1617.4 (M+H)+

Retention time: 0.74 minute (analysis condition SQDFA05)

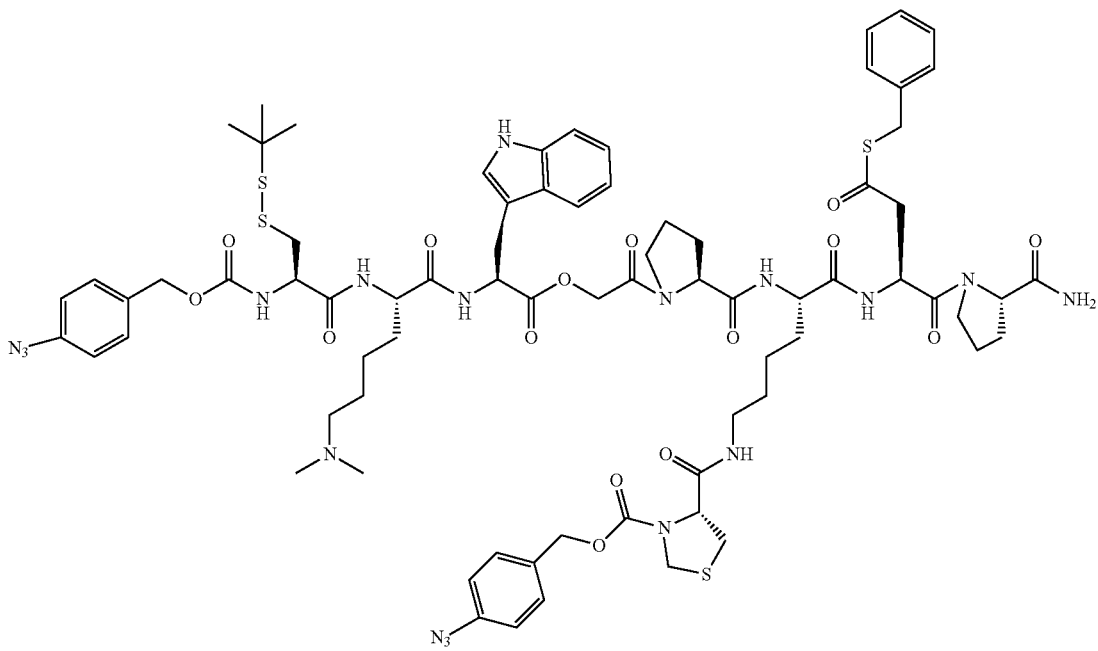 [SMILES: CN(C)CCCC[C@H](NC(=O)[C@H](CSSC(C)(C)C)NC(=O)OCc1ccc(N=[N+]=[N-])cc1)C(=O)N[C@@H](Cc1c[nH]c2ccccc12)C(=O)OCC(=O)N1CCC[C@H]1C(=O)N[C@@H](CCCCNC(=O)[C@@H]1CSCN1C(=O)OCc1ccc(N=[N+]=[N-])cc1)C(=O)N[C@@H](CC(=O)SCc1ccccc1)C(=O)N1CCC[C@H]1C(N)=O]

1-Hydroxybenzotriazole (HOBt) (13.4 mg, 0.099 mmol), 1-ethyl-3-(3-dimethylaminopropyl)carbodiimide hydrochloride (EDCI·HCl) (19.2 mg, 0.099 mmol) and benzylmercaptane (BnSH) (19.4 μl, 0.165 mmol) were added to a solution of (S)-3-((S)-2-((S)-1-((6R,9S,12S)-12-((1H-indol-3-yl)methyl)-6-((((4-azidobenzyl)oxy)carbonyl)amino)-9-(4-(dimethylamino)butyl)-2,2-dimethyl-7,10,13-trioxo-14-oxa-3,4-dithia-8,11-diazahexadecane-16-oyl)pyrrolidine-2-carboxamido)-6-((R)-3-(((4-azidobenzyl)oxy)carbonyl)thiazolidine-4-carboxamido)hexanamido)-4-((S)-2-carbamoylpyrrolidin-1-yl)-4-oxobutanoic acid (Acbz-Cys (StBu)-Lys(Me₂)-Trp-$^{HO}$Gly-Pro-Lys(Acbz-Thz)-Asp-Pro-NH₂) (Compound SP615) (SEQ ID NO: 247) (50 mg, 0.033 mmol) in Dimethylformamide (DMF) (331 μl) at room temperature under a nitrogen atmosphere, and the mixture was stirred at the same temperature for 1 hour. A 1 N aqueous hydrochloric acid solution (43 μl) was added to the reaction solution, and the mixture was purified by reverse-phase silica gel chromatography (0.1% aqueous formic acid solution/0.1% formic acid-acetonitrile solution) to afford (R)-4-azidobenzyl 4-(((S)-5-((S)-1-((6R,9S,12S)-12-((1H-indol-3-yl)methyl)-6-((((4-azidobenzyl)oxy)carbonyl)amino)-9-(4-(dimethylamino)butyl)-2,2-dimethyl-7,10,13-trioxo-14-oxa-3,4-dithia-8,11-diazahexadecan-16-oyl)

4-2. Reaction of Producing a Branched Peptide (Linear Portion 2) from a Translated Peptide Model Compound (Compound SP616) in Water or a Translation Reaction Solution Synthesis of (S)—N-((3R,6S,9S,12R,16S,19S)-6-((1H-indol-3-yl)methyl)-16-((S)-2-carbamoylpyrrolidine-1-carbonyl)-9-(4-(dimethylamino)butyl)-3,12-bis(mercaptomethyl)-2,5,8,11,14,18-hexaoxo-1,4,7,10,13,17-hexaazacyclotricosan-19-yl)-1-(2-hydroxyacetyl)pyrrolidine-2-carboxamide ($^{HO}$Gly-Pro-Lys(*Cys-Lys(Me₂)-Trp-Cys)-Asp*-Pro-NH₂, Cyclized at Two * Sites) (Compound SP617) (SEQ ID NO: 249)

In the present specification, a compound amidated between the amino group at side chain of Lys and the C-terminal carboxylic group of H-Cys-Lys(Me₂)-Trp-Cys-OH (SEQ ID NO: 346) is described as H-Lys(H-Cys-Lys(Me₂)-Trp-Cys)-OH like in other examples.

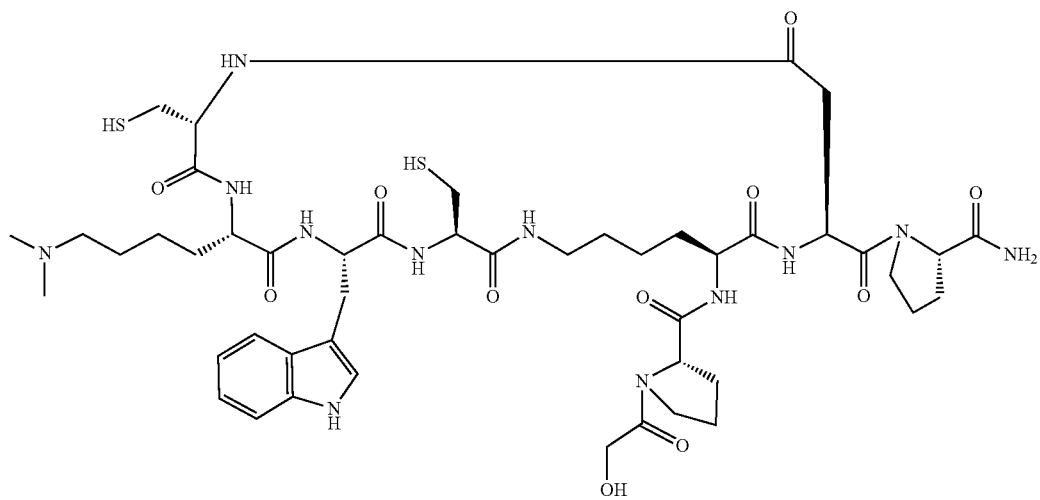 [SMILES: CN(C)CCCC[C@@H]1NC(=O)[C@H](CS)NC(=O)C[C@@H](C(=O)N2CCC[C@H]2C(N)=O)NC(=O)[C@@H](NC(=O)[C@@H]2CCCN2C(=O)CO)CCCCNC(=O)[C@H](CS)NC(=O)[C@H](Cc2c[nH]c3ccccc23)NC1=O]

(SEQ ID NO: 249)

4-2-1. Reaction of Producing a Branched Peptide in HEPES Buffer

The reaction was carried out according to the following scheme. Specifically, in Step 1, the intended Compound SP618 could be selectively obtained by deprotecting the protecting groups for two amino groups from Compound SP616 (each unit for forming the reaction at this time is structurally the same as in the translated peptide, except that the C-terminal is not carboxylic acid but carboxylic acid amide) and then directly carrying out primary cyclization reaction. Subsequently, Compound SP620 in which deprotection was attained for amino groups with reaction auxiliary groups was obtained from Compound 618 in Steps 2 and 3. Amine-protecting groups could be deprotected under chemical reaction conditions where RNA is stable. A branched peptide compound SP617 was obtained by a method of directly generating a thioester from an ester functional group.

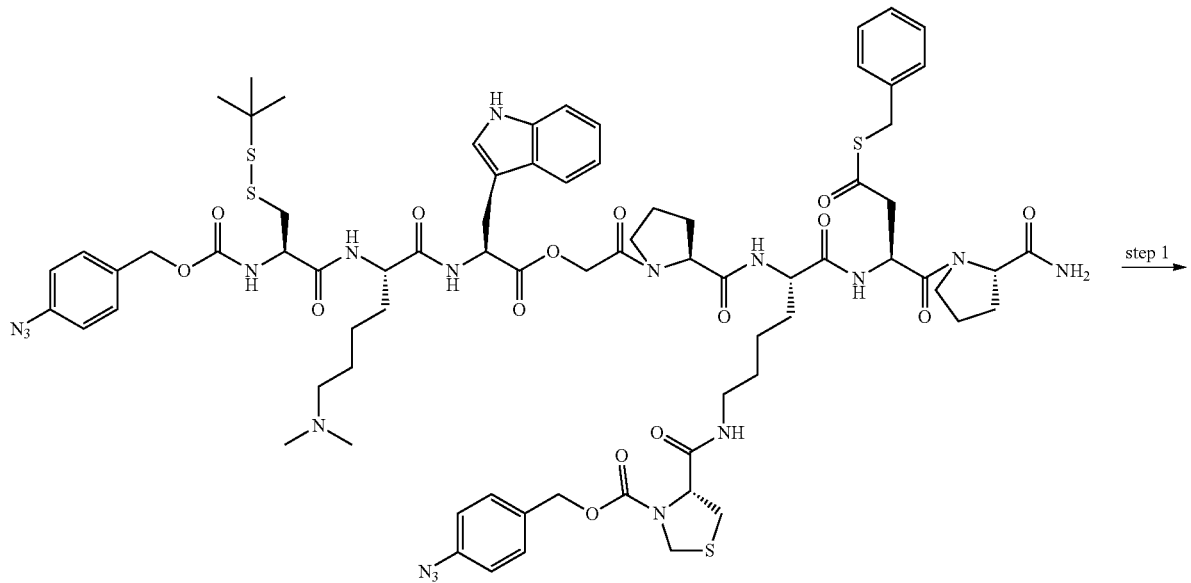

Compound SP616

-continued
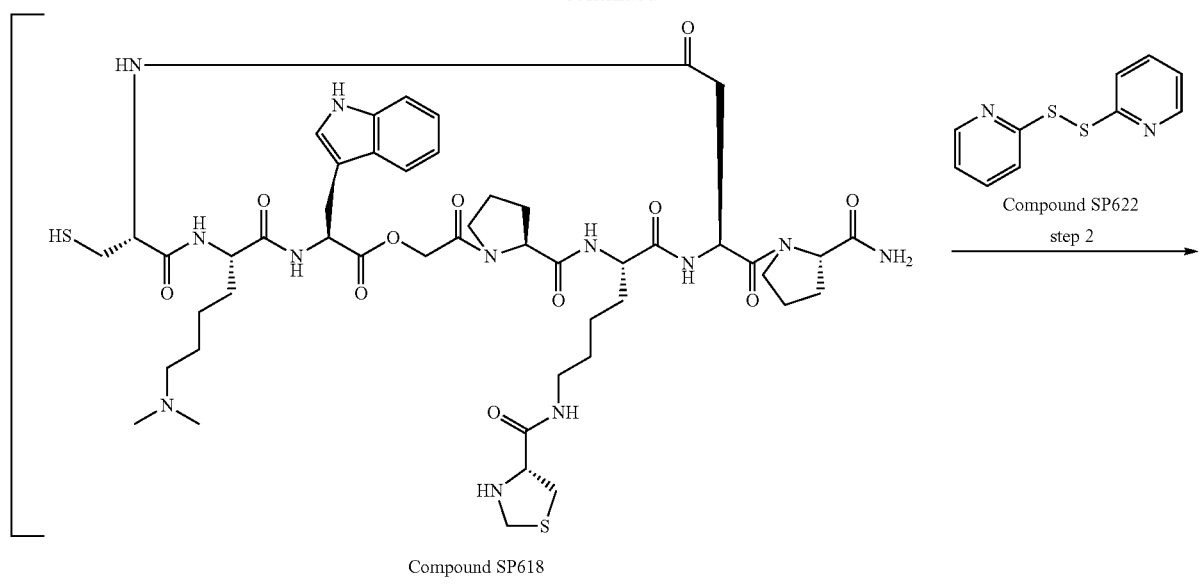
Compound SP618
Compound SP622
step 2
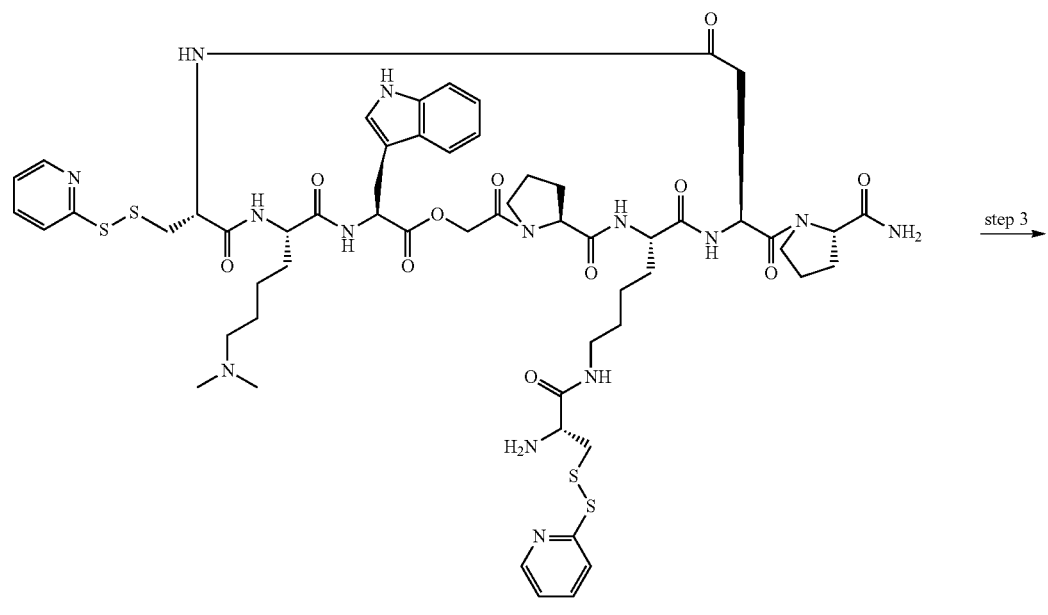
Compound SP619
step 3

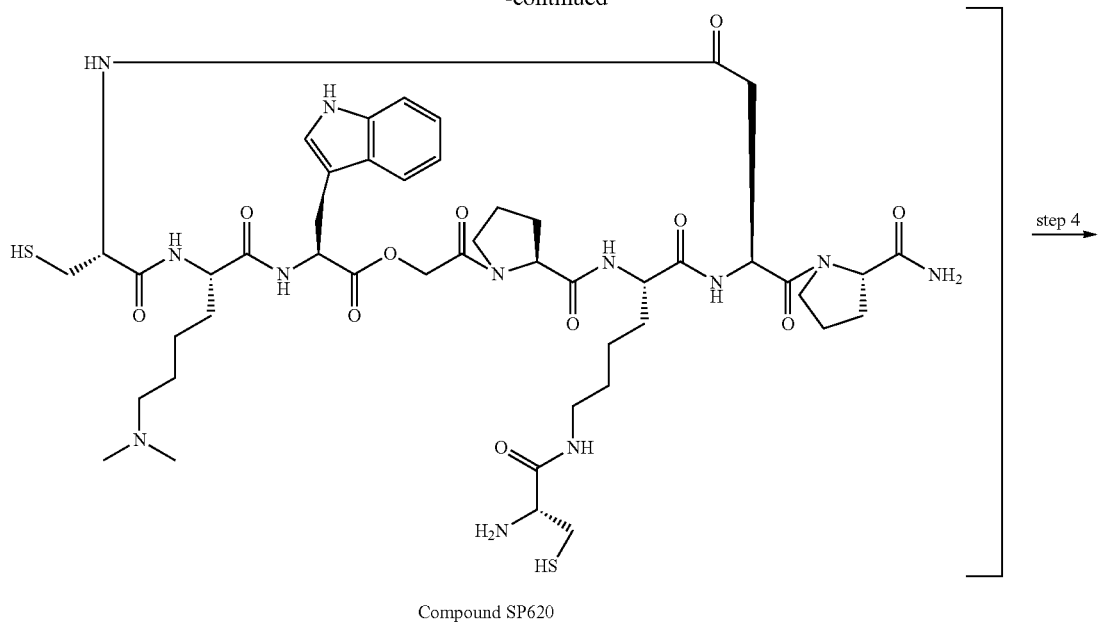

Compound SP620

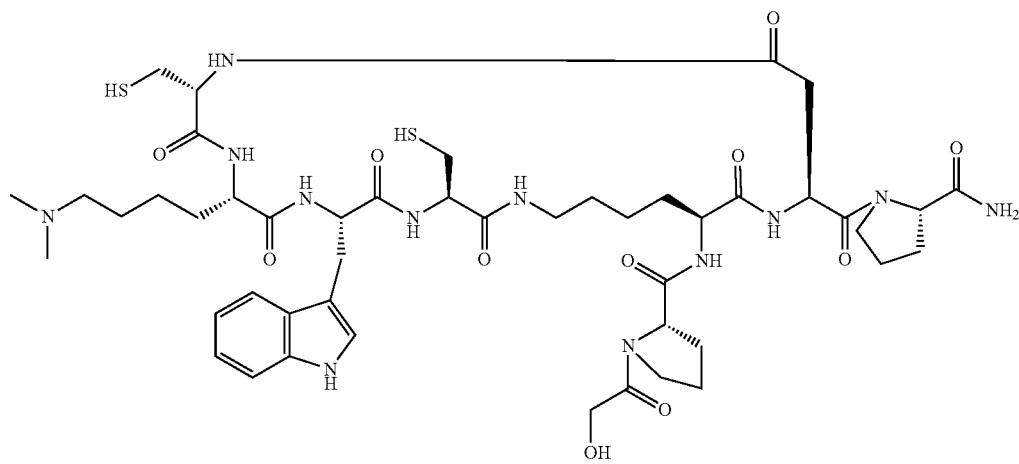

Compound SP617

Step 1 (Reaction of Conversion from Compound SP616 to Compound SP618)

Figure 59:
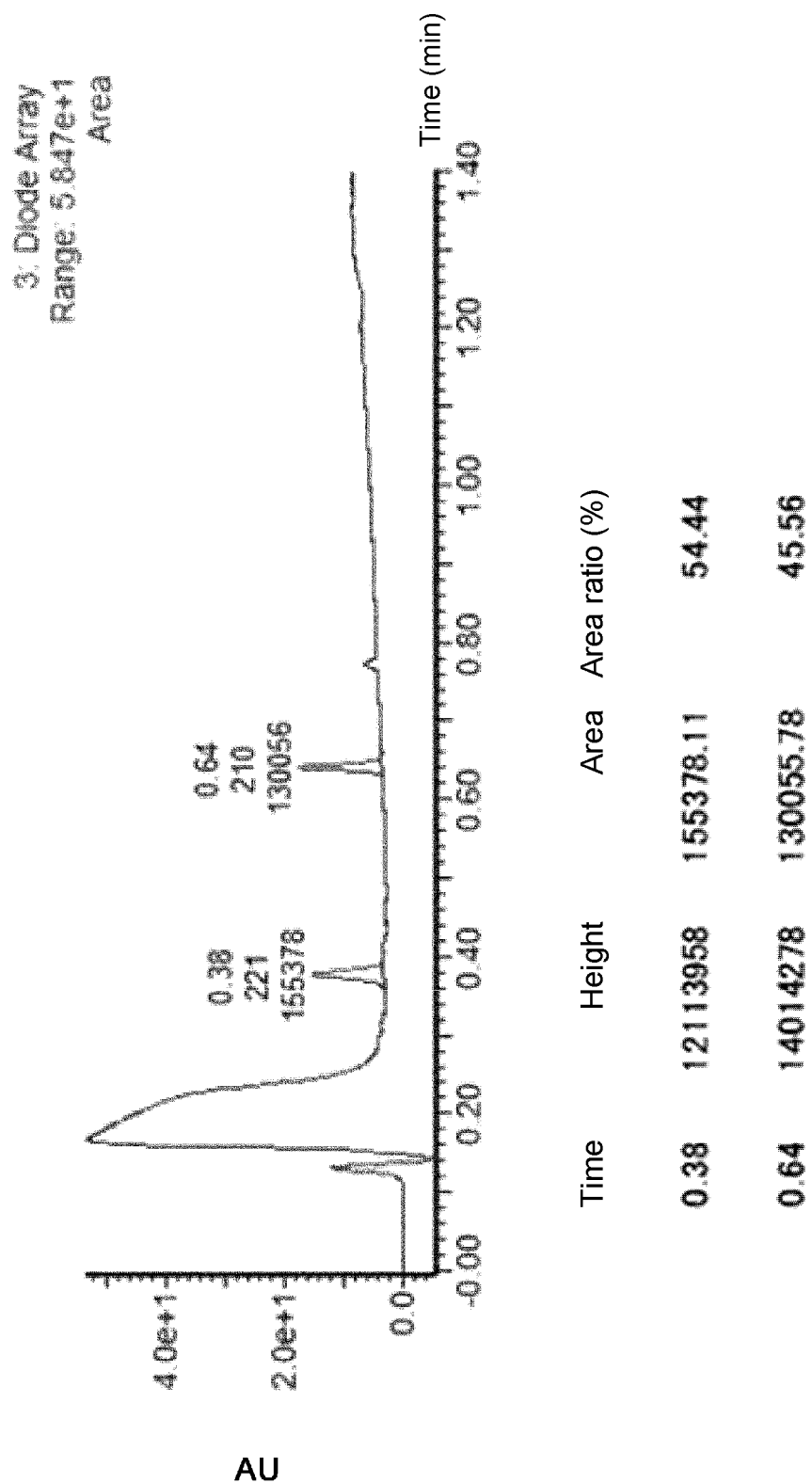
FIG. 59 is a diagram showing LCMS analysis results of a reaction solution containing produced compound SP618.

A 4 mM solution of (R)-4-azidobenzyl 4-(((S)-5-((S)-1-((6R,9S,12S)-12-((1H-indol-3-yl)methyl)-6-((((4-azidobenzyl)oxy)carbonyl)amino)-9-(4-(dimethylamino)butyl)-2,2-dimethyl-7,10,13-trioxo-14-oxa-3,4-dithia-8,11-diazahexadecan-16-oyl)pyrrolidine-2-carboxamido)-6-(((S)-4-(benzylthio)-1-((S)-2-carbamoylpyrrolidin-1-yl)-1,4-dioxobutan-2-yl)amino)-6-oxohexyl)carbamoyl)thiazolidine-3-carboxylate (Compound SP616, Acbz-Cys(StBu)-Lys(Me$_2$)-Trp-$^{HO}$Gly-Pro-Lys(Acbz-Thz)-Asp(SBn)-Pro-NH$_2$ (SEQ ID NO: 248)) in dimethylacetamide (DMA) (25 µl, 0.1 µmol), a 20 mM solution of 2,4-dimethylbenzoic acid used as internal standard in dimethylacetamide (DMA) (5.0 µl, 0.1 µmol) and a separately prepared 200 mM tris(2-carboxyethyl)phosphine (TCEP) hydrochloride solution (10 µl, 2.0 µmol, pH=7.4) were added to 50 mM HEPES buffer (70 µl, pH=7.5) at room temperature under a nitrogen atmosphere, and the mixture was stirred at the same temperature for 1 hour and 30 minutes at pH=7.4. The change in the reaction was traced by LCMS. After 1 hour and 30 minutes, the intended SP618 was observed as a main product and side reaction was not observed (the ratio of the intended Compound SP618 (LCMS retention time 0.38 min) and the internal standard (LCMS retention time 0.64 min) was 54:46 based on the UV area ratio by LCMS) (FIG. 59).

The 200 mM tris(2-carboxyethyl)phosphine (TCEP) hydrochloride solution was prepared by the following method. Tris(2-carboxyethyl)phosphine (TCEP) hydrochloride (5.0 mg, 17 µmol) was adjusted to pH=7.4 by dissolving it in 50 mM HEPES buffer (57.0 µl, pH=7.5) and a 2 N aqueous sodium hydroxide solution (30 µl).

LCMS (ESI) m/z=1053 (M–H)–

Retention time: 0.38 min (analysis condition SQDFA05)

Step 2 (Conversion from Compound SP618 to Compound SP619)

Figure 60:
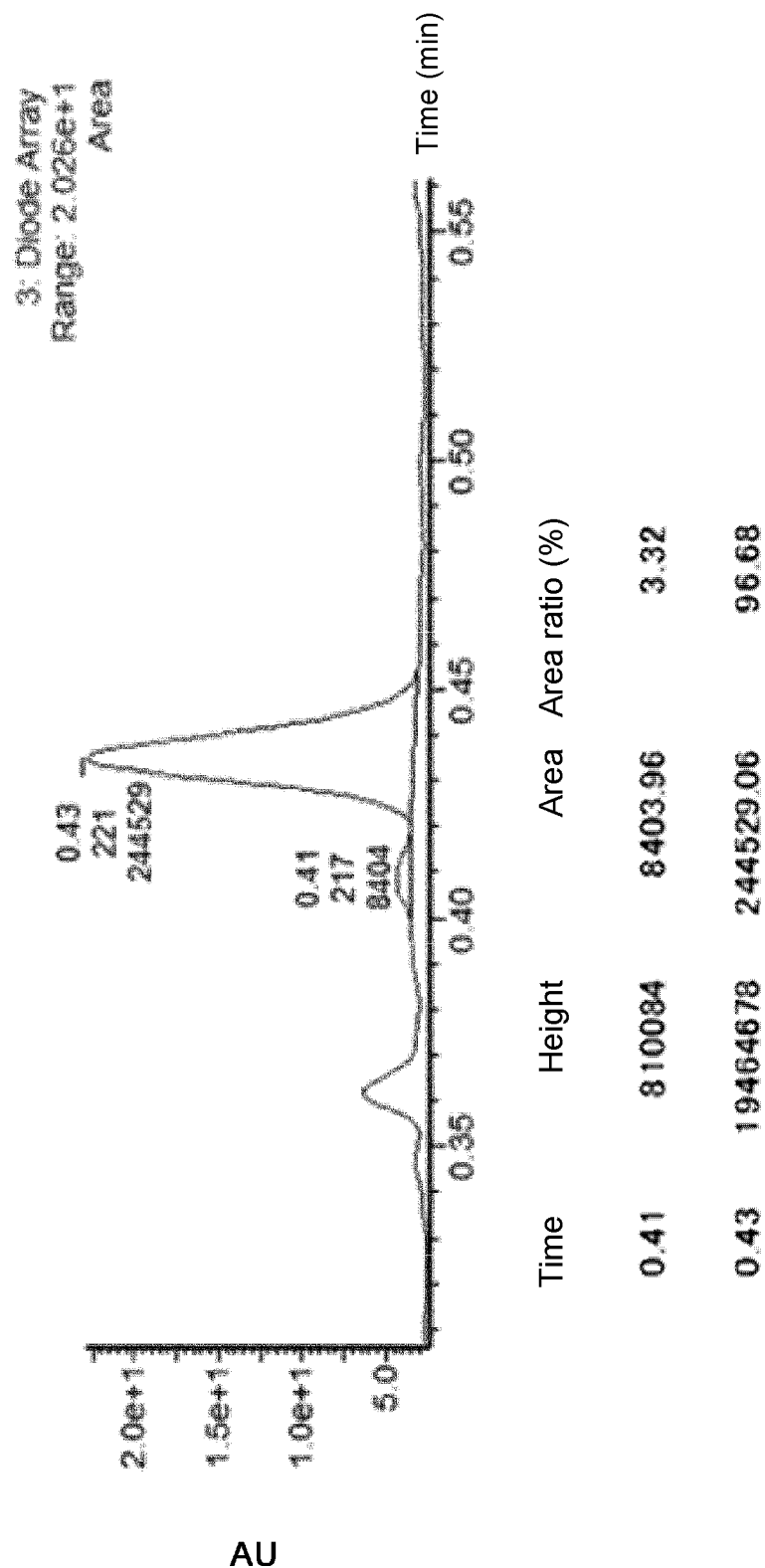
FIG. 60 is a diagram showing LCMS analysis results of a reaction solution containing produced compound SP619.

A 80 mM 2,2'-dithiodipyridine (Compound SP622, 2,2'-PySSPy) solution (90 µl) was added to the reaction solution prepared in Step 1 (90 µl) at room temperature under a nitrogen atmosphere, and the mixture was allowed to stand at 37° C. for 12 hours in a thermal cycler at pH=3.0. The change in the reaction was traced by LCMS to confirm that the intended compound was produced after 12 hours. The production ratio of the intended compound (Compound SP619, LCMS retention time 0.43 min) and the hydrolysate (by-product, LCMS retention time 0.41 min) was 97:3 based on the UV area ratio by LCMS (FIG. 60).

The 80 mM 2,2'-dithiodipyridine (2,2'-PySSPy) solution was prepared by the following method. Dimethylacetamide (DMA) (10 µl) and a 100 mM aqueous hydrochloric acid solution (70 µl) were added to a 400 mM solution of 2,2'-dithiodipyridine (2,2'-PySSPy) in dimethylacetamide (DMA) (20 µl, 8.0 µmol).

LCMS (ESI) m/z=1261.3 (M+H)+

Retention time: 0.43 min (analysis condition SQDFA05)

Step 3 (Conversion from Compound SP619 to Compound SP620)

A separately prepared 600 mM tris(2-carboxyethyl)phosphine (TCEP) hydrochloride solution (10 µl, 6.0 µmol, pH=7.2) was added to the reaction solution prepared in Step 2 (90 µL) at room temperature under a nitrogen atmosphere, and the mixture was allowed to stand at the same temperature for 1 hour at pH=4.6. The change in the reaction was traced by LCMS to confirm that the intended compound (Compound SP620) was produced after 1 hour.

The 600 mM tris(2-carboxyethyl)phosphine (TCEP) hydrochloride solution was prepared by the following method. Tris(2-carboxyethyl)phosphine (TCEP) hydrochloride (13.8 mg, 48 µmol) was adjusted to pH=7.2 by adding a 2 N aqueous sodium hydroxide solution (80 µl) thereto.

Figure 61:
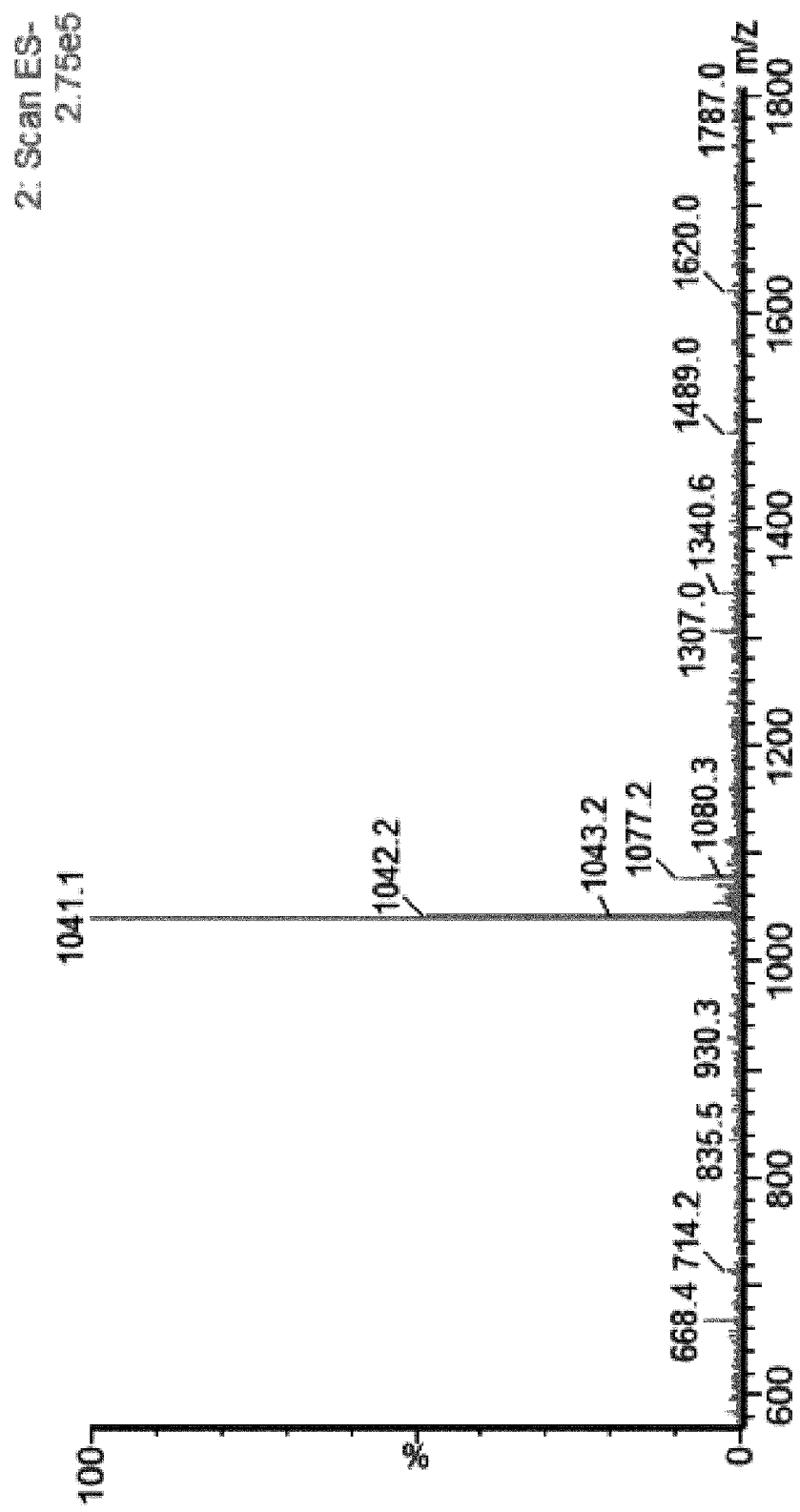
FIG. 61 is a diagram showing a mass chromatogram at retention times of 0.3 minutes to 0.6 minutes in LCMS. All peptide components are eluted at the retention times from 0.3 minutes to 0.6 minutes under this analysis condition. Thus, as a result of integrating and averaging mass chromatograms from 0.3 minutes to 0.6 minutes for the purpose of evaluating reaction selectivity, this reaction was found to proceed selectively.

LCMS (ESI) m/z=1041 (M–H)– (FIG. 61)

Retention time: 0.36 min (analysis condition SQDFA05)

Step 4 (Conversion from Compound SP620 to Compound SP617)

A separately prepared 5.0 M sodium 2-mercaptoethanesulfonate solution (30 µl, pH=8.5) was added to the reaction solution prepared in Step 3 (30 µl) at room temperature under a nitrogen atmosphere, and the mixture was allowed to stand at 30° C. for 15 hours in a thermal cycler at pH=8.5. The change in the reaction was traced by LCMS to confirm that the intended (S)—N-((3R,6S,9S,12R,16S,19S)-6-((1H-indol-3-yl)methyl)-16-((S)-2-carbamoylpyrrolidine-1-carbonyl)-9-(4-(dimethylamino)butyl)-3,12-bis(mercaptomethyl)-2,5,8,11,14,18-hexaoxo-1,4,7,10,13,17-hexaazacyclotricosan-19-yl)-1-(2-hydroxyacetyl) pyrrolidine-2-carboxamide 0° Gly-Pro-Lys(*Cys-Lys(Me$_2$)-Trp-Cys)-Asp*-Pro-NH$_2$ (SEQ ID NO: 249). cyclized at two * sites) (Compound SP617) was produced after 15 hours.

The 5.0 M sodium 2-mercaptoethanesulfonate solution was prepared by the following method. Sodium 2-mercaptoethanesulfonate (74.0 mg, 0.45 mmol) was adjusted to pH=8.5 by adding a 1 N aqueous sodium hydroxide solution (45 µl) and water (45 µl) thereto.

LCMS (ESI) m/z=1043 (M+H)+

Retention time: 0.40 min (analysis condition SQDFA05)

4-2-2. Reaction of Producing a Branched Peptide in a Translation Condition Solution Reaction was carried out under the following conditions simulating translation actually performed. Reaction was carried out until deprotection (Compound SP620) in the translation system of PURE SYSTEM. In the following reaction of producing a branched peptide, purification with RNeasy® MinElute™ Cleanup Kit (Qiagen) can also be performed in a display library experiment. In this purification process, an RNA-peptide complex can be purified, and protein and low-molecular-weight components are particularly removed. In this experiment, Compound SP620 was isolated and subjected to branching reaction, assuming that purification should be performed when Compound SP620 is obtained. For this reason, an eluate obtained by purifying the translation system solvent of PURE SYSTEM using RNeasy® MinElute™ Cleanup Kit (Qiagen) was used as a reaction solvent taking purification in a display library into consideration. During purification, Compound SP620 was converted to Compound SP623 in which two SH groups in the peptide form an S—S bond in the molecule. Accordingly, Compound SP617 was obtained by generating Compound SP620 again from Compound SP623 in the simulated display library and then performing branching reaction.

The reaction was carried out in the translation system of PURE SYSTEM according to the following scheme.

2251  2252
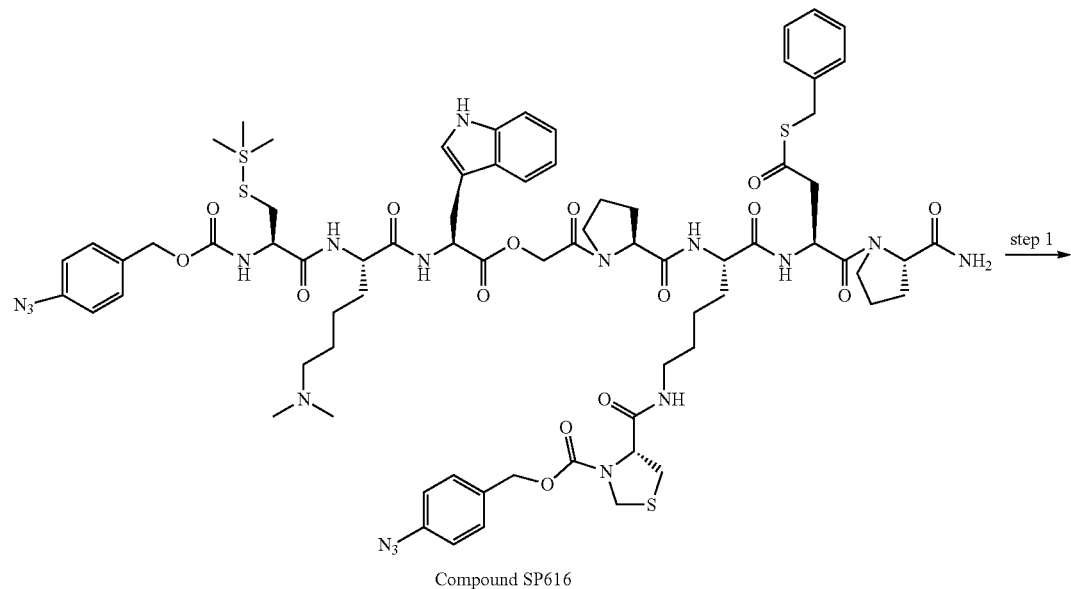
Compound SP616 → step 1
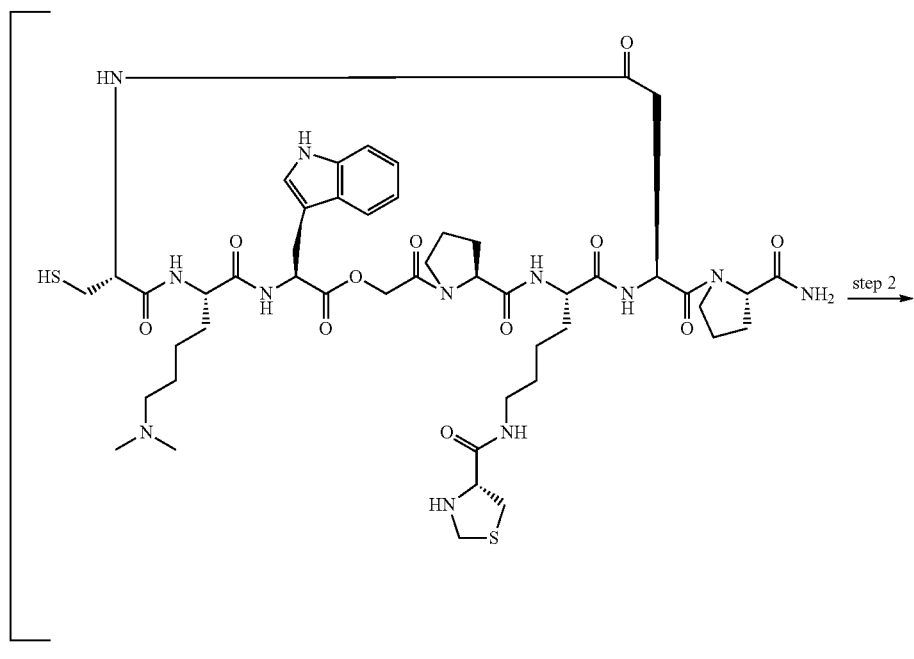
Compound SP618 → step 2

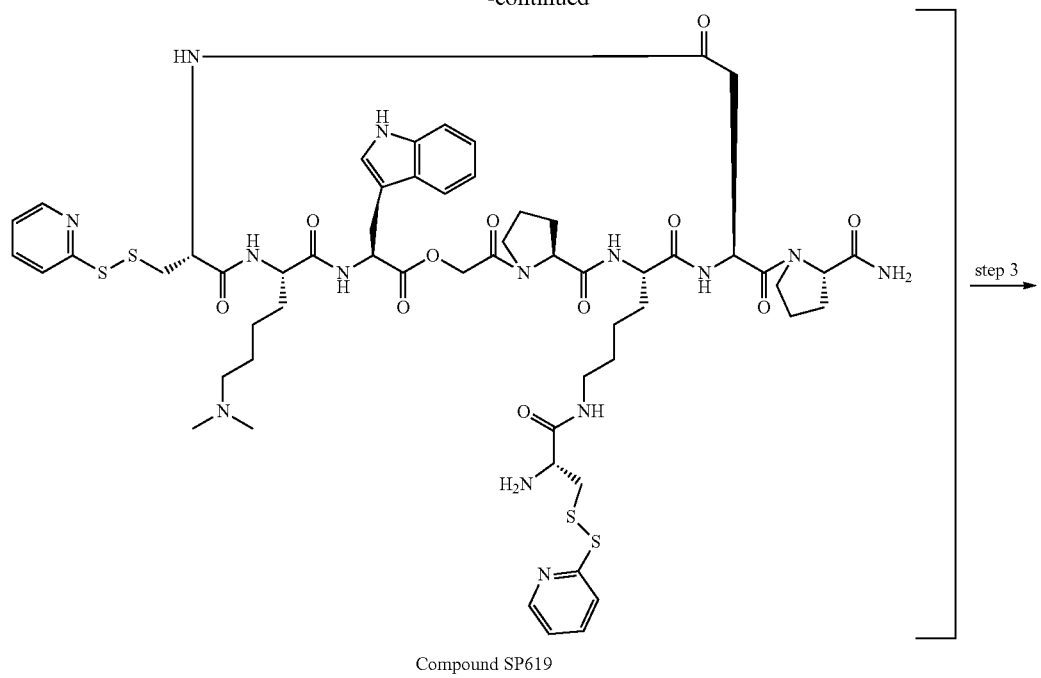

Compound SP619 step 3

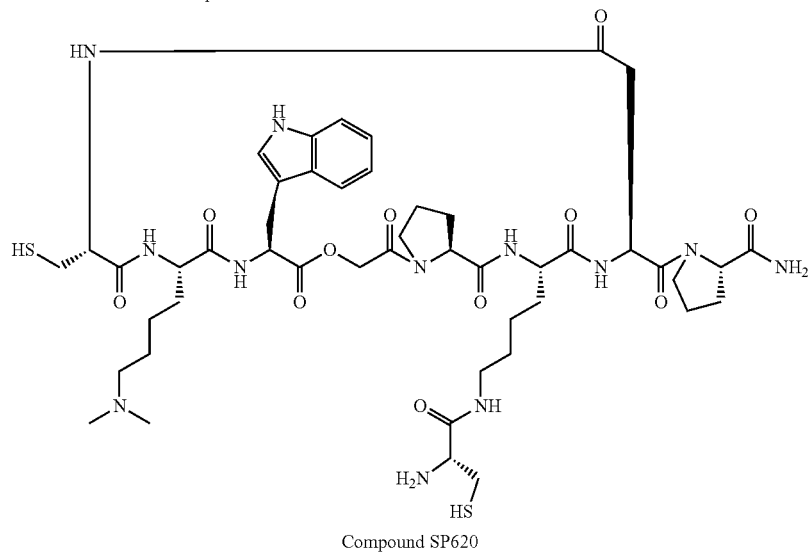

Compound SP620

Step 1 (Conversion from Compound SP616 to Compound SP618)

Figure 63:
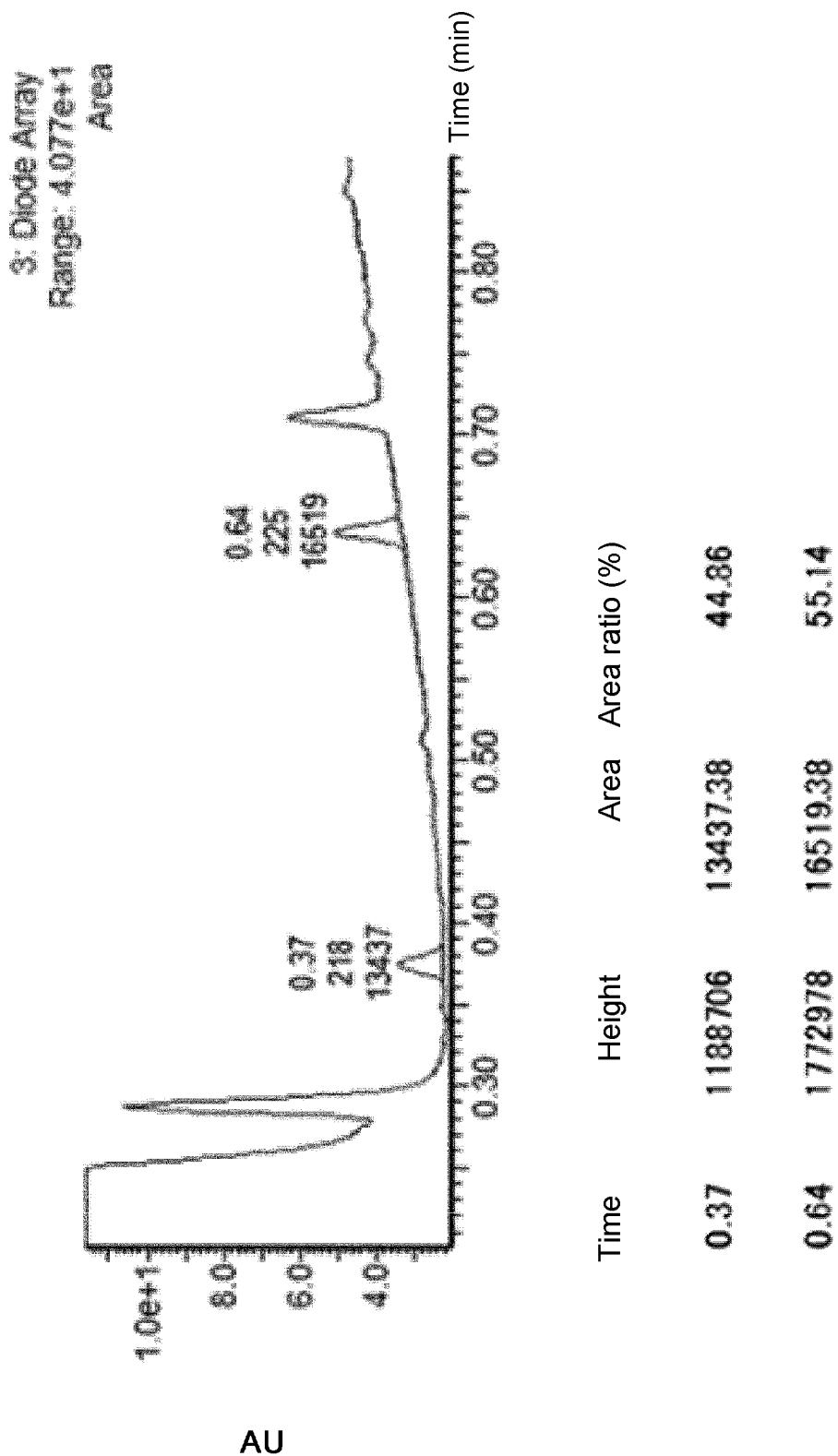
FIG. 63 is a diagram showing LCMS analysis results of a reaction solution containing produced compound SP618.

A translation buffer (12.5 μl), PURESYSTEM® classic II Sol. B (BioComber, product No. PURE2048C) (20 μl), 20 natural amino acid solutions (each 5 mM, 5.0 μl) and water (32.5 μl) were mixed under a nitrogen atmosphere, and dimethylacetamide (DMA) (26.25 μl) was added to prepare a solution. A 4 mM solution of (R)-4-azidobenzyl 4-(((S)-5-((S)-1-((6R,9S,12S)-12-((1H-indol-3-yl)methyl)-6-((((4-azidobenzyl)oxy)carbonyl)amino)-9-(4-(dimethylamino)butyl)-2,2-dimethyl-7,10,13-trioxo-14-oxa-3,4-dithia-8,11-diazahexadecan-16-oyl)pyrrolidine-2-carboxamido)-6-(((S)-4-(benzylthio)-1-((S)-2-carbamoylpyrrolidin-1-yl)-1,4-dioxobutan-2-yl)amino)-6-oxohexyl)carbamoyl)thiazolidine-3-carboxylate (Acbz-Cys (StBu)-Lys(Me$_2$)-Trp-$^{HO}$Gly-Pro-Lys(Acbz-Thz)-Asp(SBn)-Pro-NH$_2$) (Compound SP616) (SEQ ID NO: 248) in dimethylacetamide (DMA) (2.5 μl, 0.01 μmol), a 8 mM solution of 2,4-dimethylbenzoic acid used as internal standard in dimethylacetamide (DMA) (1.25 μl, 0.01 μmol) and a separately prepared 100 mM tris(2-carboxyethyl)phosphine (ICES) hydrochloride solution (10 μl, 1.0 μmol, pH=7.6) were added at room temperature, and the mixture was allowed to stand at the same temperature for 1 hour at pH=7.5. The change in the reaction was traced by LCMS to confirm that the intended compound (Compound SP618) was produced after 1 hour. The ratio of the intended compound (LCMS retention time 0.37 min) and the internal standard (LCMS retention time 0.64 min) was 45:55 based on the UV area ratio by LCMS, and this made it clear that the same reaction selectivity and reaction rate as in the buffer were achieved in the translation solution (FIG. 63).

The ingredients of the translation buffer are as follows. 8 mM GTP, 8 mM ATP, 160 mM creatine phosphate, 400 mM HEPES-KOH, pH 7.6, 800 mM potassium acetate, 48 mM magnesium acetate, 16 mM spermidine, 8 mM dithiothreitol, 0.8 mM 10-HCO—H4 folate and 12 mg/ml *E. coli* MRE600 (RNase negative)-derived tRNA (Roche).

The 100 mM tris(2-carboxyethyl)phosphine (TCEP) hydrochloride solution was prepared by the following method. Tris(2-carboxyethyl)phosphine (TCEP) hydrochloride (5.0 mg, 17 μmol) was adjusted to pH=7.6 by dissolving it in 50 mM HEPES buffer (122 μl, pH=7.5) and a 1 N aqueous sodium hydroxide solution (52 μl).

LCMS (ESI) m/z=1053 (M−H)−
Retention time: 0.37 min (analysis condition SQDFA05)

Step 2 (Conversion from Compound SP618 to Compound SP619)

Figure 64:
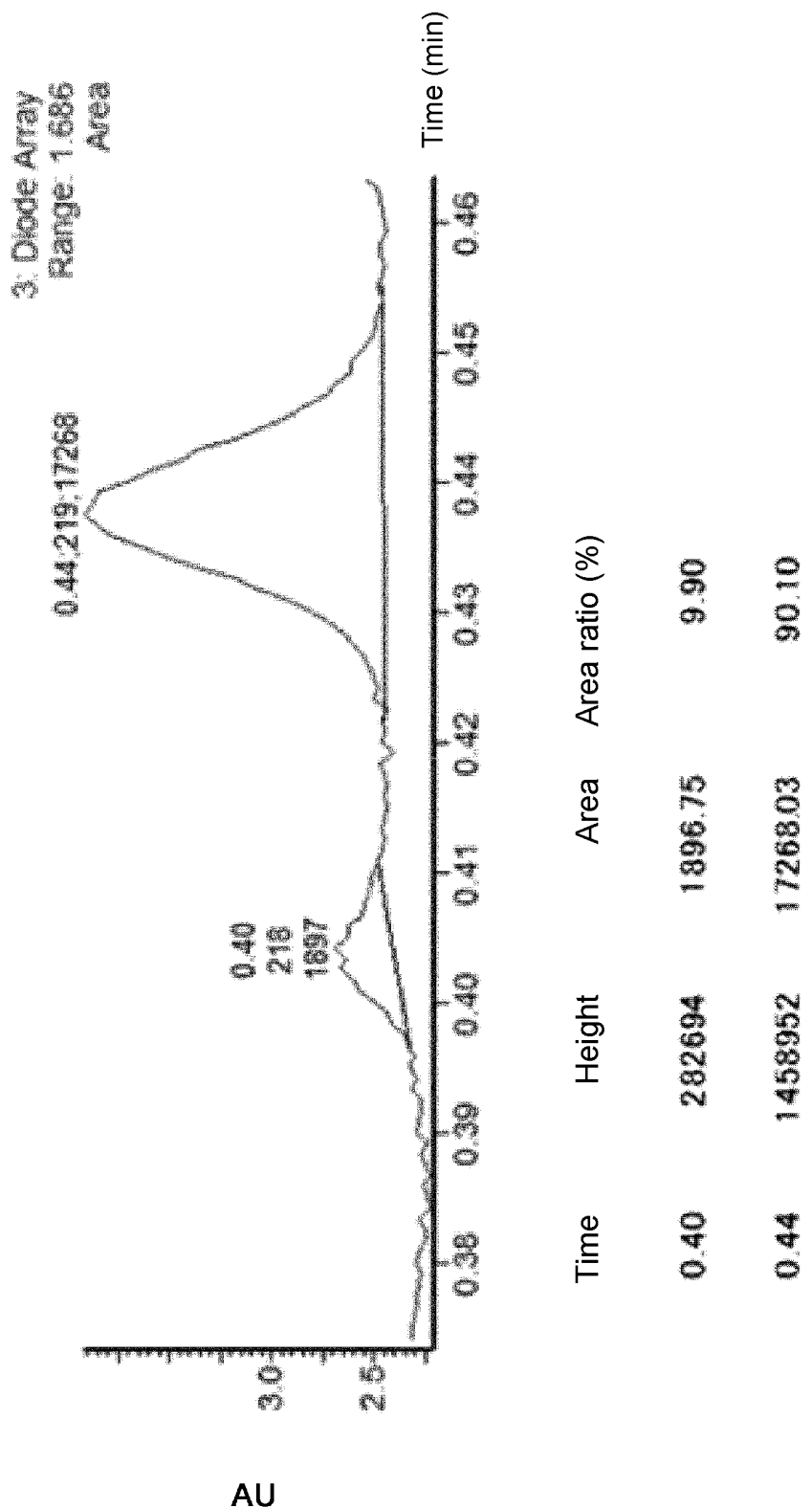
FIG. 64 is a diagram showing LCMS analysis results of a reaction solution containing produced compound SP619.

A 80 mM 2,2'-dithiodipyridine (Compound SP622, 2,2'-PySSPy) solution (80 μl) was added to the reaction solution prepared in Step 1 (80 μl) at room temperature under a nitrogen atmosphere, a 500 mM aqueous sodium hydroxide solution (2.0 μl) was added at room temperature, and the mixture was allowed to stand at 37° C. for 13 hours in a thermal cycler at pH=4.0. The change in the reaction was traced by LCMS to confirm that the intended compound (Compound SP619) was produced after 13 hours. The production ratio of the intended compound (LCMS retention time 0.44 min) and the hydrolysate (LCMS retention time 0.40 min) was 90:10 based on the UV area ratio by LCMS (FIG. 64).

The 80 mM 2,2'-dithiodipyridine (Compound SP622, 2,2'-PySSPy) solution was prepared by the following method. Dimethylacetamide (DMA) (10 μl) and a 230 mM aqueous hydrochloric acid solution (70 μl) were added to a 400 mM solution of 2,2'-dithiodipyridine (Compound SP622, 2,2'-PySSPy) in dimethylacetamide (DMA) (20 μl, 8.0 μmol).

LCMS (ESI) m/z=1261.3 (M+H)+
Retention time: 0.44 min (analysis condition SQDFA05)

Step 3 (Conversion from Compound SP619 to Compound SP620)

Figure 65:
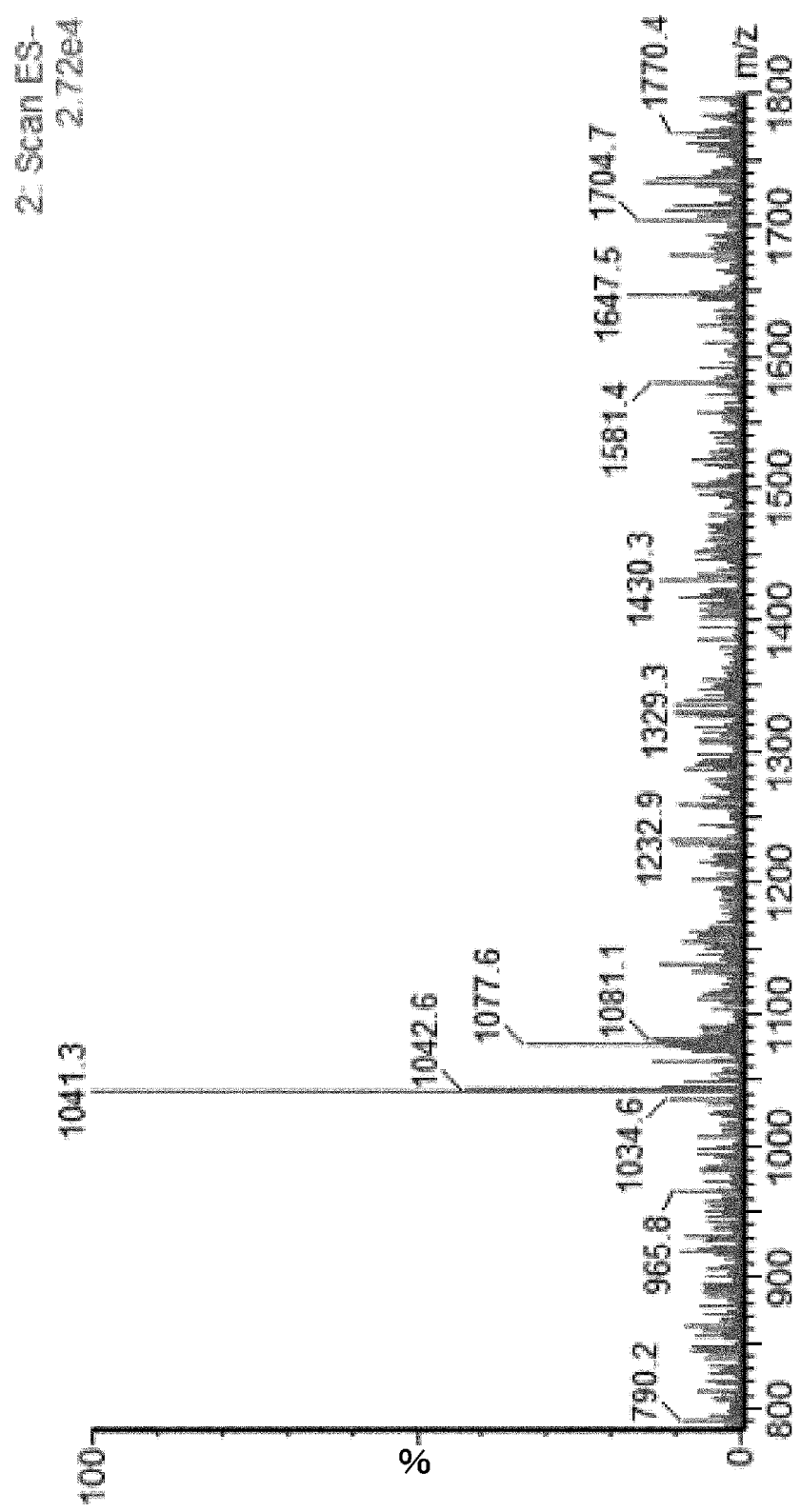
FIG. 65 is a diagram showing a mass chromatogram at retention times of 0.3 minutes to 0.6 minutes in LCMS. All peptide components are eluted at the retention times from 0.3 minutes to 0.6 minutes under this analysis condition. Thus, mass chromatograms from 0.3 minutes to 0.6 minutes were integrated and averaged for the purpose of evaluating reaction selectivity.

A separately prepared 600 mM tris(2-carboxyethyl)phosphine (TCEP) hydrochloride solution (9.0 μl, pH=7.2) was added to the reaction solution prepared in Step 2 (81 μl) at room temperature under a nitrogen atmosphere, and the mixture was allowed to stand at the same temperature for 1 hour at pH=5.1. The change in the reaction was traced by LCMS to confirm that the intended compound (Compound SP620) was produced after 1 hour. A new by-product due to the use of PURE SYSTEM was not observed as compared with the reaction in HEPES buffer (FIG. 65).

The 600 mM tris(2-carboxyethyl)phosphine (TCEP) hydrochloride solution was prepared by the following method. Tris(2-carboxyethyl)phosphine (TCEP) hydrochloride (17.6 mg, 61 μmol) was adjusted to pH=7.2 by adding a 2 N aqueous sodium hydroxide solution (102 μl) thereto.

LCMS (ESI) m/z=1041 (M−H)−
Retention time: 0.36 min (analysis condition: SQDFA05)

Compound SP620 was reproduced using a branched peptide precursor having an S—S bond newly formed as a result of purification (Compound SP623) (the preparation method is described in the following (4-2-4)), (S)-1-((3S,10R,15R,18S,21S,29aS,33S)-21-((1H-indol-3-yl)methyl)-10-amino-18-(4-(dimethylamino)butyl)-1,9,16,19,22,25,31,35-octaoxohexacosahydro-15,3-(epiminopropanoiminomethano)pyrrolo[2,1-x][1,11,12,4,7,16,22,25]oxadithiapentaazacycloheptacosyne-33-carbonyl)pyrrolidine-2-carboxamide (*Cys #-Lys(Me$_2$)-Trp-$^{HO}$Gly-Pro-Lys(H-Cys #)-Asp*-Pro-NH$_2$ (SEQ ID NO: 252), cyclized at two * sites and two # sites and having two SH groups forming a disulfide bond at # sites), in an eluate obtained by purifying the translation solvent of PURE SYSTEM using RNeasy® MinElute™ Cleanup Kit (Qiagen). After that, reaction of producing a branched peptide to afford Compound SP617 was carried out according to the

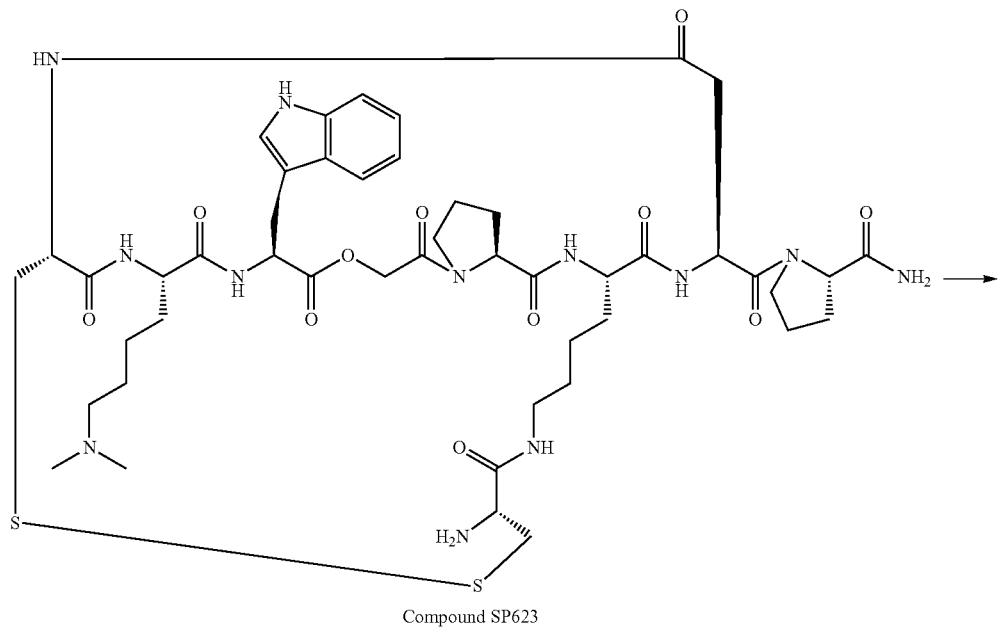

Compound SP623

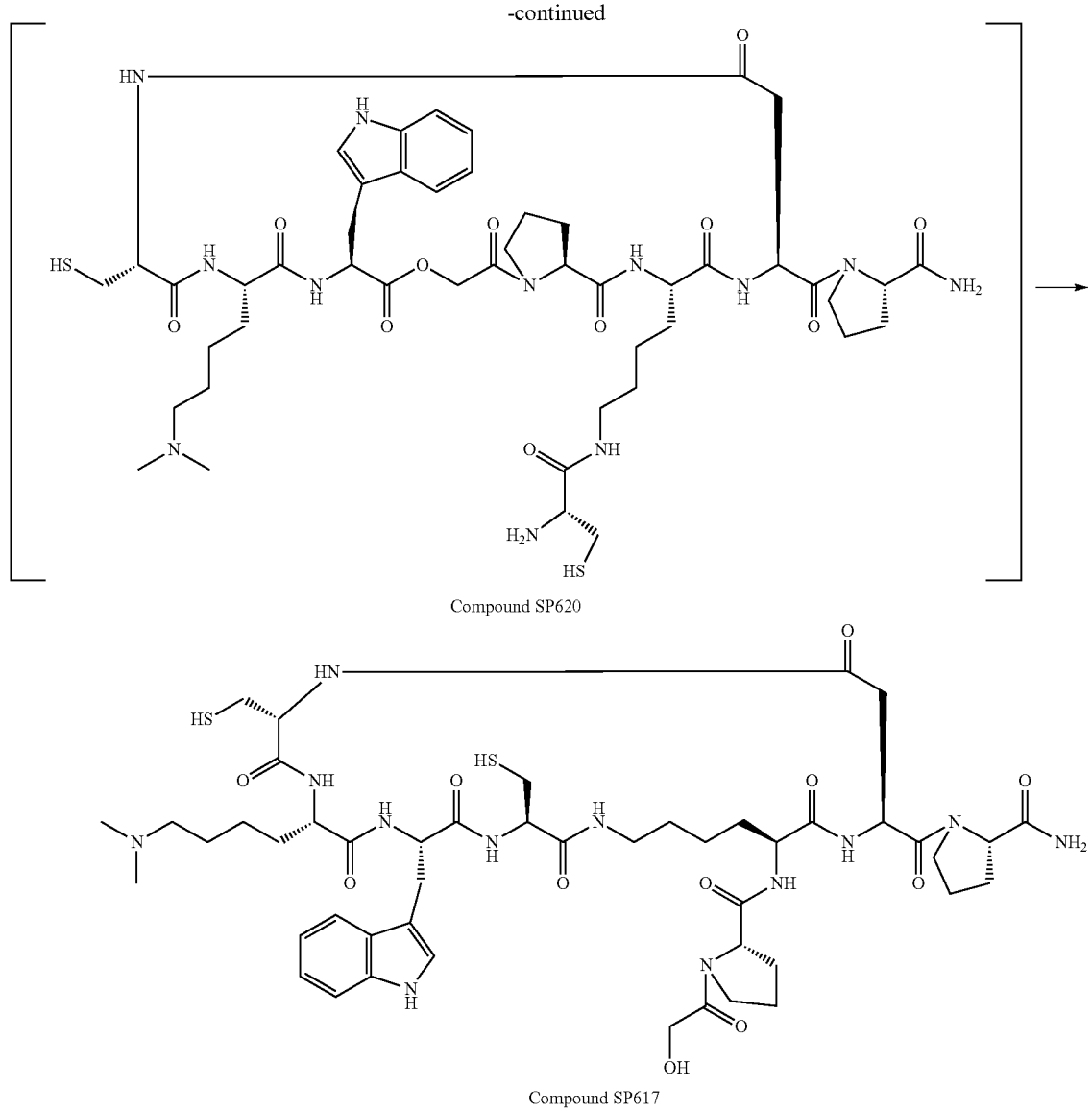

Compound SP620

Compound SP617

Under a nitrogen atmosphere, A 10 mM solution of (S)-1-((3S,10R,15R,18S,21S,29aS,33S)-21-((1H-indol-3-yl)methyl)-10-amino-18-(4-(dimethylamino)butyl)-1,9,16,19,22,25,31,35-octaoxohexacosahydro-15,3-(epiminopropanoiminomethano)pyrrolo[2,1-x][1,11,12,4,7,16,22,25]oxadithiapentaazacycloheptacosyne-33-carbonyl)pyrrolidine-2-carboxamide (*Cys #-Lys(Me')-Trp-$^{HO}$Gly-Pro-Lys(H-Cys #)-Asp*-Pro-NH$_2$ (SEQ ID NO: 252), cyclized at two * sites and two # sites and having two SH groups forming a disulfide bond at # sites) (Compound SP623) in dimethylimidazolidinone (DMI) (12.5 µl, 0.125 µmol) and a 50 mM solution of 2,4-dimethylbenzoic acid used as internal standard in dimethylimidazolidinone (DMI) (2.5 µl, 0.125 µmol) were added to a solution in which an eluate obtained by purifying the translation system solvent of PURE SYSTEM using RNeasy® MinElute™ Cleanup Kit (Qiagen) (25 µl) was mixed with a 500 mM tris(2-carboxyethyl) phosphine (TCEP) hydrochloride solution (5.0 µl, 2.5 µmol), 2 N sodium hydroxide (8 µl) and sodium 2-mercaptoethanesulfonate (24.8 mg, 0.15 mmol), and the mixture was allowed to stand at 30° C. for 30 hours in a thermal cycler at pH=8.4. The change in the reaction was traced by LCMS to confirm that the intended (S)—N-((3R,6S,9S,12R,16S,19S)-6-((1H-indol-3-yl)methyl)-16-((S)-2-carbamoylpyrrolidine-1-carbonyl)-9-(4-(dimethylamino)butyl)-3,12-bis(mercaptomethyl)-2,5,8,11,14,18-hexaoxo-1,4,7,10,13,17-hexaazacyclotricosan-19-yl)-1-(2-hydroxyacetyl)pyrrolidine-2-carboxamide ($^{HO}$Gly-Pro-Lys(*Cys-Lys(Me$_2$)-Trp-Cys)-Asp*-Pro-NH$_2$ (SEQ ID NO: 249), cyclized at two * sites) (Compound SP617) was produced after 30 hours. A new by-product due to the use of the eluate obtained by purifying the translation solvent of PURE SYSTEM was not observed as compared with the reaction in HEPES buffer.

The eluate obtained by purifying the translation solvent of PURE SYSTEM using RNeasy® MinElute™ Cleanup Kit (Qiagen) was prepared as follows. The translation buffer previously described in Example (12.5 µl), PURE SYSTEM® classic II Sol. B (BioComber, product No. PURE2048C) (20 µL), 20 natural amino acid solutions (each 5 mM, 5.0 µl) and water (62.5 µl) were added to prepare a translation solution. Buffer RLT (70 µl) and EtOH (135 µl) were added to the translation solution (20 µl), and the mixture was pipetted and applied to RNeasy MinElute Spin Column. The filtrate was removed by centrifugation at 10000 rpm for 15 seconds. Buffer RPE (500 µl) was added to the column, and the filtrate was removed by centrifugation at 10000 rpm for 15 seconds. A 80% aqueous EtOH solution (500 µl) was added to the column, and the filtrate was removed by centrifugation at 10000 rpm for 2 minutes. The cover of the column was opened, centrifugation was performed at 15000 rpm for 5 minutes, and the column was dried, followed by elution by adding water (22 µl). RNase free water was used in this case.

LCMS (ESI) m/z=1043 (M+H)+

Retention time: 0.40 min (analysis condition SQDFA05)

As described above, it was confirmed that the intended reaction similarly proceeded in water and in PureSystem (translation reaction solution) without significant difference. RNA was sufficiently stable under such reaction conditions, and this made it clear that branching reaction efficiently proceeds from linear peptide compounds after translation reaction and that branching reaction can be allowed to efficiently proceed in peptide-RNA complexes without RNA decomposition.

These facts revealed that the progress of a reaction similar to such reactions in a translation reaction solution can be estimated by measuring reactivity in water (buffer).

4-2-3. Desulfurization Reaction from a Branched Peptide (Linear Portion 2) Under Conditions Simulating Translation Conditions Desulfurization reaction was carried out for the reaction solution containing the branched peptide (Compound 617) in an eluate obtained by purifying the translation system solvent of Pure SYSTEM using RNeasy® MinElute® Cleanup Kit (Qiagen) as used in 4-2-2.

Synthesis of (S)—N-((3S,6S,9S,12S,16S,19S)-6-((1H-indol-3-yl)methyl)-16-((S)-2-carbamoylpyrrolidine-1-carbonyl)-9-(4-(dimethylamino)butyl)-3,12-dimethyl-2,5,8,11,14,18-hexaoxo-1,4,7,10,13,17-hexaazacyclotricosan-19-yl)-1-(2-hydroxyacetyl)pyrrolidine-2-carboxamide (Compound SP624, $^{HO}$Gly-Pro-Lys(*Ala-Lys(Me$_2$)-Trp-Ala)-Asp*-Pro-NH$_2$ (SEQ ID NO: 250), Cyclized at Two * Sites)

In the present specification, a compound amidated between the amino group at side chain of Lys and the C-terminal carboxylic group of H-Ala-Lys(Me$_2$)-Trp-Ala-OH (SEQ ID NO: 251) is described as H-Lys(H-Ala-Lys(Me$_2$)-Trp-Ala)-OH like in other examples.

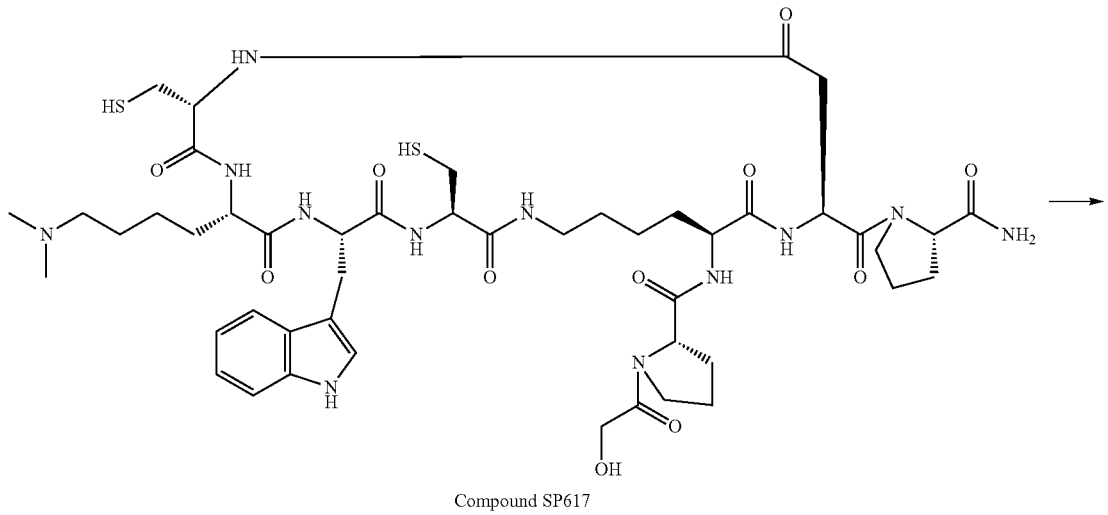
Compound SP617

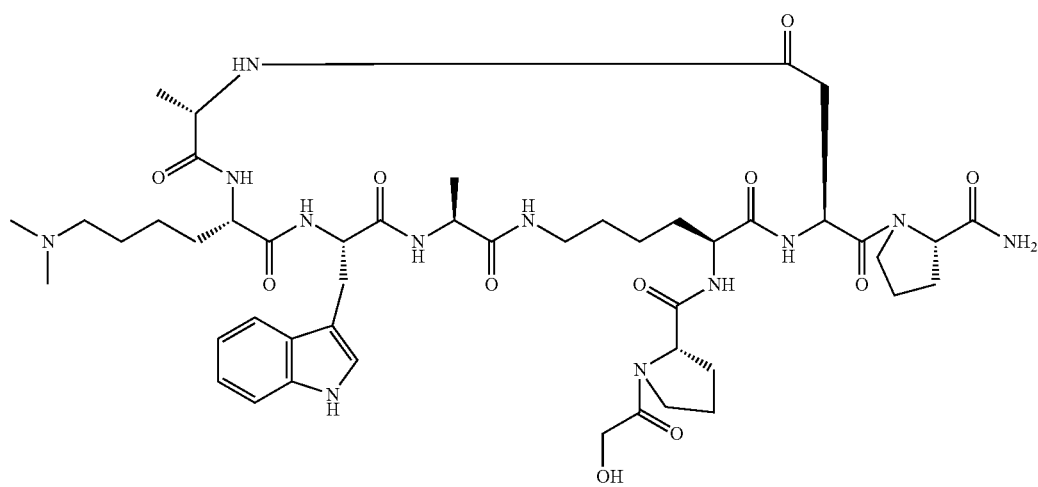
Compound SP624

A 1.5 M tris(2-carboxyethyl)phosphine (TCEP) hydrochloride solution (20 pH=7.4) was added to the reaction solution containing the branched peptide (Compound SP617) in an eluate obtained by purifying the translation system solvent of Pure SYSTEM using RNeasy® MinElute® Cleanup Kit (Qiagen) as used in 4-2-2 (9.0 μl) under a nitrogen atmosphere, and the mixture was stirred at 50° C. for 5 minutes. A 250 mM aqueous 2,2-azobis[2-(2-imidazolin-2-yl)propane] dihydrochloride (VA-044) solution (1.2 μl) was added at room temperature, and the mixture was stirred at 50° C. for 1 hour. The change in the reaction was traced by LCMS to confirm that the intended (S)—N-((3S, 6S,9S,12S,16S,19S)-6-((1H-indol-3-yl)methyl)-16-((S)-2-carbamoylpyrrolidine-1-carbonyl)-9-(4-(dimethylamino)butyl)-3,12-dimethyl-2,5,8,11,14,18-hexaoxo-1,4,7,10,13,17-hexaazacyclotricosan-19-yl)-1-(2-hydroxyacetyl)pyrrolidine-2-carboxamide (Compound SP624, $^{HO}$Gly-Pro-Lys(*Ala-Lys(Me$_2$)-Trp-Ala)-Asp*-Pro-NH$_2$ (SEQ ID NO: 250), cyclized at two * sites) was produced after 1 hour.

The 1.5 M tris(2-carboxyethyl)phosphine (TCEP) hydrochloride solution was prepared by the following method. Tris(2-carboxyethyl)phosphine (TCEP) hydrochloride (24.5 mg, 85.5 μmol) was adjusted to pH=7.4 by adding a 5 N aqueous sodium hydroxide solution (57 μl) thereto.

LCMS (ESI) m/z=979 (M+H)+
Retention time: 0.36 min (analysis condition SQDFA05)

4-2-4. Purification Step after Carrying Out Primary Cyclization and Subsequent Deprotection of the Amino Group Site Synthesis of (S)-1-((3S,10R,15R,18S,21S,29aS, 33S)-21-((1H-indol-3-yl)methyl)-10-amino-18-(4-(dimethylamino)butyl)-1,9,16,19,22,25,31,35-octaoxohexacosahydro-15,3-(epiminopropanoiminomethano)pyrrolo[2,1-x][1,11, 12,4,7,16,22,25]oxadithiapentaazacycloheptacosyne-33-carbonyl)pyrrolidine-2-carboxamide (*Cys #-Lys(Me2)-Trp-$^{HO}$Gly-Pro-Lys(H-Cys #)-Asp*-Pro-NH$_2$ (SEQ ID NO: 252), Cyclized at Two * Sites and Two # Sites and Having Two SH Groups Forming a Disulfide Bond at # Sites) (Compound SP623) Used for Reaction of Producing a Branched Peptide As a result of purification, SP620 itself could not be purified and Compound SP623 was formed. Because Compound SP623 can be readily converted to SP620 again under reduction conditions, Compound SP623 was purified and isolated. Resynthesis was performed in addition to the above experiment, because a large amount of the compound is needed for purification.

The reaction was carried out according to the

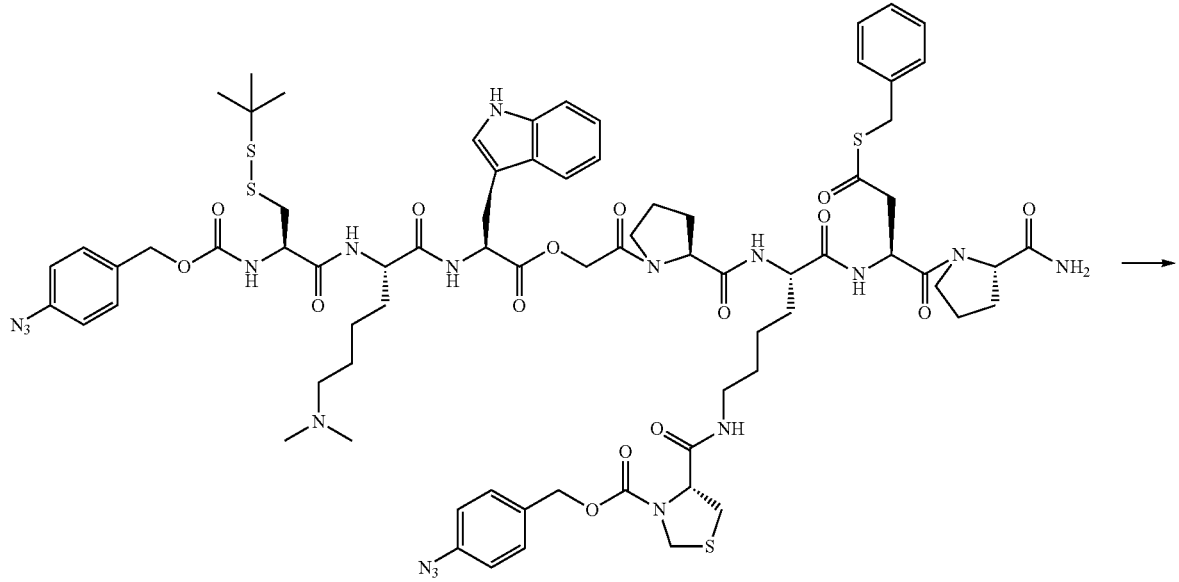

Compound SP616

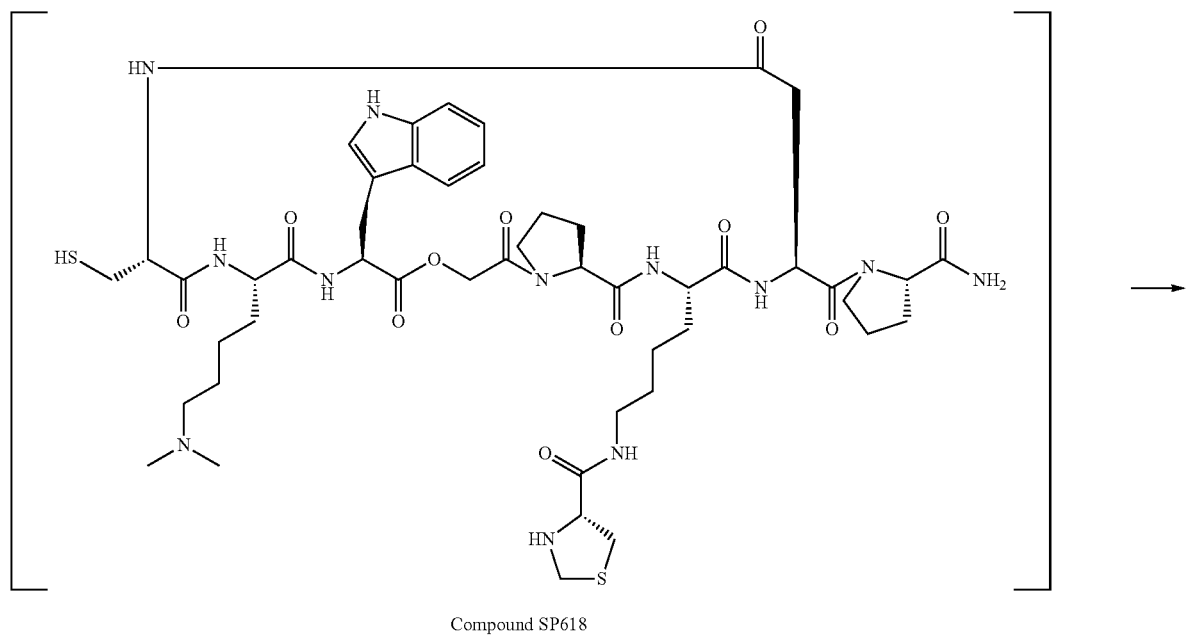
Compound SP618
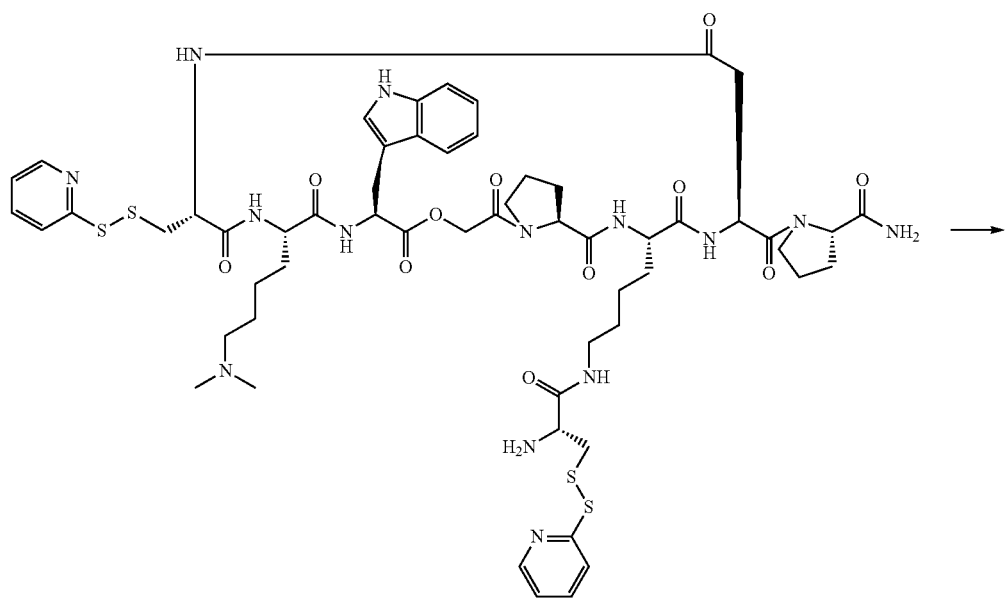
Compound SP619

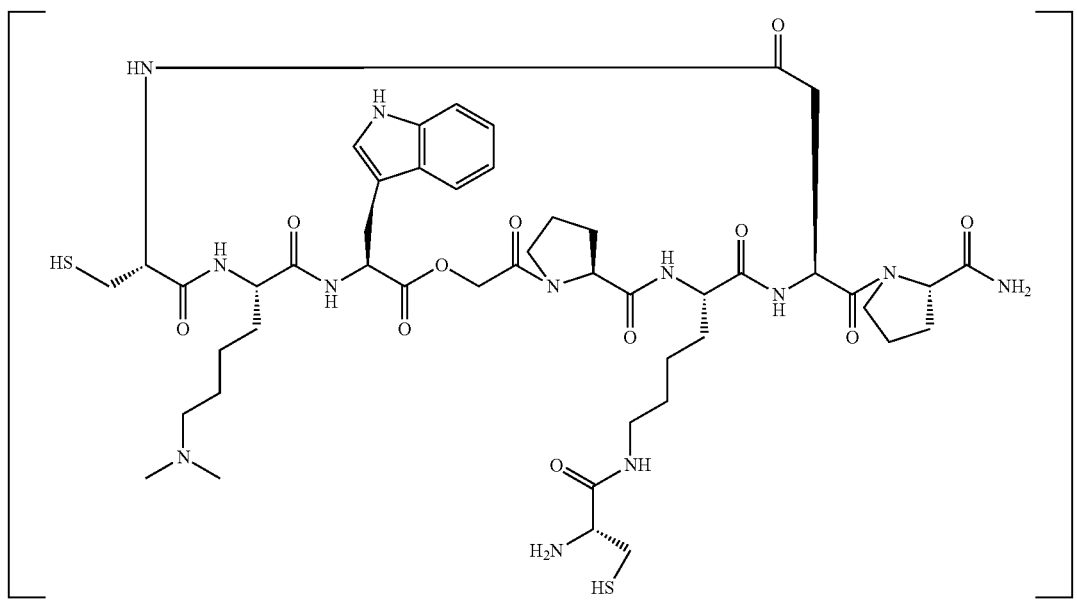
Compound SP620
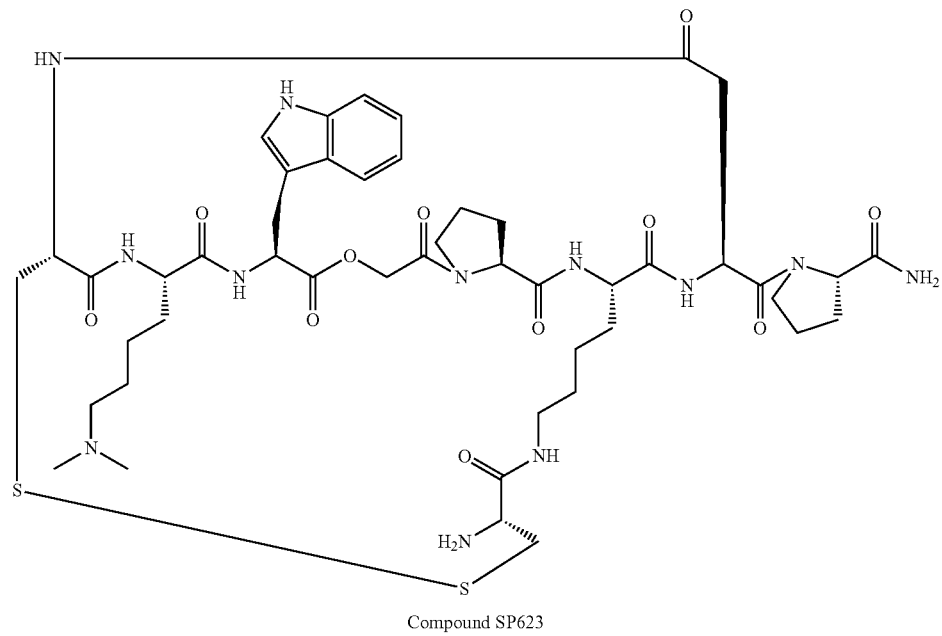
Compound SP623

Synthesis of (S)-1-((3S,6S,10R,13S,16S,24aS)-16-((1H-indol-3-yl)methyl)-3-(4-((R)-2-amino-3-(pyridin-2-yldisulfanyl)propanamide)butyl)-13-(4-(dimethylamino)butyl)-1,4,8,11,14,17,20-heptaoxo-10-((pyridin-2-yldisulfanyl)methyl)docosahydro-1H-pyrrolo[1,2-d][1,4,7,10,14,17,20]oxahexaazacyclodocosyne-6-carbonyl)pyrrolidine-2-carboxamide (*Cys(SPy)-Lys(Me2)-Trp-$^{HO}$Gly-Pro-Lys(H-Cys(SPy))-Asp*-Pro-NH$_2$ (SEQ ID NO: 253), Cyclized at Two Sites) (Compound SP619)

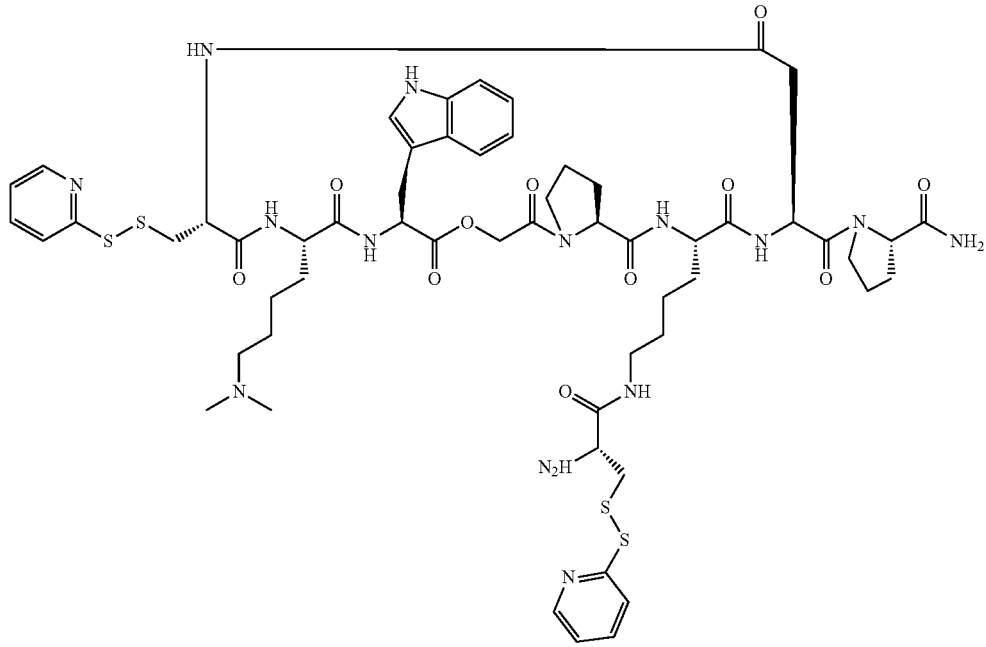

(R)-4-Azidobenzyl 4-(((S)-5-((S)-1-((6R,9S,12S)-12-((1H-indol-3-yl)methyl)-6-((((4-azidobenzyl)oxy)carbonyl)amino)-9-(4-(dimethylamino)butyl)-2,2-dimethyl-7,10,13-trioxo-14-oxa-3,4-dithia-8,11-diazahexadecan-16-oyl)pyrrolidine-2-carboxamido)-6-(((S)-4-(benzylthio)-1-((S)-2-carbamoylpyrrolidin-1-yl)-1,4-dioxobutan-2-yl)amino)-6-oxohexyl)carbamoyl)thiazolidine-3-carboxylate (Acbz-Cys (StBu)-Lys(Me$_2$)-Trp-$^{HO}$Gly-Pro-Lys(Acbz-Thz)-Asp (SBn)-Pro-NH$_2$) (Compound SP616) (SEQ ID NO: 254) (8.0 mg, 4.94 µmol) was added to a mixed solution of 200 mM phosphate buffer (691 µl, pH=7.6) and dimethylacetamide (DMA) (797 µl) at room temperature under a nitrogen atmosphere. A separately prepared 1 M tris(2-carboxyethyl)phosphine (TCEP) hydrochloride solution (100 µl, 100 µmol, pH=7.4) was added at room temperature, and the reaction solution was allowed to stand at the same temperature for 2 hours at pH=7.4. The change in the reaction was traced by LCMS to confirm that cyclization reaction proceeded and Compound SP618 was produced after 2 hours.

The 1 M tris(2-carboxyethyl)phosphine (TCEP) hydrochloride solution was prepared by the following method. Tris(2-carboxyethyl)phosphine (TCEP) hydrochloride (39 mg, 0.136 mmol) was adjusted to pH=7.4 by dissolving it in a 5 N aqueous sodium hydroxide solution (91 µl) and water (45 µl).

A 330 mM 2,2'-dithiodipyridine (Compound SP622, 2,2'-PySSPy) solution (1.5 ml) was added to the resulting reaction solution containing Compound SP618 (1.5 ml) at room temperature under a nitrogen atmosphere, and the mixture was allowed to stand at 37° C. for 13 hours at pH=2.1. The resulting reaction solution was purified by reverse-phase silica gel chromatography (0.1% aqueous formic acid/0.1% formic acid-acetonitrile solution) to afford (S)-1-((3S,6S, 10R,13S,16S,24aS)-16-((1H-indol-3-yl)methyl)-3-(4-((R)-2-amino-3-(pyridin-2-yldisulfanyl)propanamide)butyl)-13-(4-(dimethylamino)butyl)-1,4,8,11,14,17,20-heptaoxo-10-((pyridin-2-yldisulfanyl)methyl)docosahydro-1H-pyrrolo[1,2-d][1,4,7,10,14,17,20]oxahexaazacyclodocosyne-6-carbonyl)pyrrolidine-2-carboxamide (*Cys(SPy)-Lys(Me$_2$)-Trp-$^{HO}$Gly-Pro-Lys(H-Cys(SPy))-Asp*-Pro-NH$_2$ (SEQ ID NO: 253), cyclized at two * sites) (Compound SP619) (3.7 mg, 60%).

The 330 mM 2,2'-dithiodipyridine (Compound SP622, 2,2'-PySSPy) solution was prepared by the following method. A 2 N aqueous hydrochloric acid solution (238 µl) and water (80 µl) were added to a 400 mM solution of 2,2-dithiodipyridine (Compound SP622, 2,2'-PySSPy) in dimethylacetamide (DMA) (1.5 ml, 0.6 mmol).

LCMS (ESI) m/z=1261.4 (M+H)+

Retention time: 0.43 min (analysis condition SQDFA05)

Synthesis of a Branched Peptide Precursor, (S)-1-((3S,10R,15R,18S,21S,29aS,33S)-21-((1H-indol-3-yl)methyl)-10-amino-18-(4-(dimethylamino)butyl)-1,9,16,19,22,25,31,35-octaoxohexacosahydro-15,3-(epiminopropanoiminomethano)pyrrolo[2,1-x][1,11,12,4,7,16,22,25]oxadithiapentaazacycloheptacosyne-33-carbonyl)pyrrolidine-2-carboxamide (*Cys #-Lys(Me2)-Trp-$^{HO}$Gly-Pro-Lys(H-Cys #)-Asp*-Pro-NH$_2$ (SEQ ID NO: 255), Cyclized at Two * Sites and Two # Sites and Having Two SR Groups Forming a Disulfide Bond at # Sites) (Compound SP623)

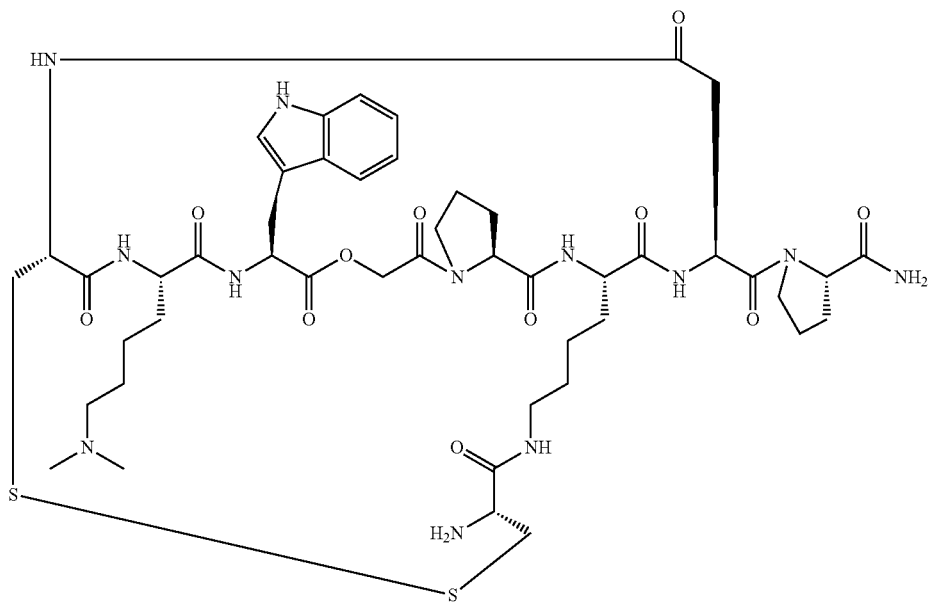 [SMILES: CN(C)CCCC[C@@H]1NC(=O)[C@@H]2CSSC[C@H](N)C(=O)NCCCC[C@H](NC(=O)[C@@H]3CCCN3C(=O)COC(=O)[C@H](Cc3c[nH]c4ccccc34)NC1=O)C(=O)N[C@H](C(=O)N1CCC[C@H]1C(N)=O)CC(=O)N2]

(S)-1-((3S,6S,10R,13S,16S,24aS)-16-((1H-indol-3,-yl)methyl)-3-(4-((R)-2-amino-3-(pyridin-2-yldisulfanyl)propanamide)butyl)-13-(4-(dimethylamino)butyl)-1,4,8,11,14,17,20-heptaoxo-10-((pyridin-2-yldisulfanyl)methyl)docosahydro-11-1-pyrrolo[1,2-d][1,4,7,10,14,17,20]oxahexaazacyclodocosyne-6-carbonyl)pyrrolidine-2-carboxamide (*Cys(SPy)-Lys(Me$_2$)-Trp-$^{HO}$Gly-Pro-Lys(H-Cys(SPy))-Asp*-Pro-NH$_2$ (SEQ ID NO: 256), cyclized at two * sites) (Compound SP619) (9.1 mg, 7.2 µmol) was added to a solution of 200 mM phosphate buffer (720 µl, pH=7.6) and dimethylacetamide (DMA) (720 µl) at room temperature under a nitrogen atmosphere. A separately prepared 600 mM tris(2-carboxyethyl)phosphine (TCEP) hydrochloride solution (100 µl, 60 µmol, pH=3.7) was added at room temperature, and the reaction solution was allowed to stand at the same temperature for 30 minutes at pH=5.6. The resulting reaction solution was purified by reverse-phase silica gel chromatography (0.1% aqueous formic-acid solution/0.1% formic acid-acetonitrile solution). The resulting fraction was lyophilized, so that disulfide formation occurred, and (S)-1-((3S,10R,15R,18S,21S,29aS,33S)-21-((1H-indol-3-yl)methyl)-10-amino-18-(4-(dimethylamino)butyl)-1,9,16,19,22,25,31,35-octaoxohexacosahydro-15,3-(epiminopropanoiminomethano)pyrrolo[2,1-x][1,11,12,4,7,16,22,25]oxadithiapentaazacycloheptacosyne-33-carbonyl)pyrrolidine-2-carboxamide (*Cys#-Lys(Me$_2$)-Trp-$^{HO}$Gly-Pro-Lys (H-Cys#)-Asp*-Pro-NH$_2$ (SEQ ID NO: 255), cyclized at two * sites and two # sites and having two SH groups forming a disulfide bond at # sites) (Compound SP623) (3.7 mg, 49%) was obtained as a branched peptide precursor.

The 600 mM tris(2-carboxyethyl)phosphine (TCEP) hydrochloride solution was prepared by the following method. Tris(2-carboxyethyl)phosphine (TCEP) hydrochloride (22.5 mg, 78.5 mmol) was adjusted to pH=3.7 by dissolving it in a 1 N aqueous sodium hydroxide solution (131 µl).

LCMS (ESI) m/z=1039 (M−H)−

Retention time: 0.34 min (analysis condition SQDFA05)

5. Examination for Optimization of an Active Thioester-Creating Unit Generated in Secondary Branching Reaction As described later, it was found that reaction conditions under which a thioester is generated from Cys-Pro-$^{HO}$Gly are mild, therefore allow reaction to proceed slowly even at pH=7.3. In order to maximize selectivity for primary cyclization and to allow less mild reaction conditions to be used in primary cyclization reaction, modified units which are more stable than Cys-Pro-HOGly and can switch the reaction on and off are investigated. And as a result of it, more preferred units were found. It was confirmed that cyclization reaction and branching reaction in translation solutions proceeded using the preferred Cys-Pro-Lac units.

5-1. Synthesis of Materials for Model Reaction

Five-residue peptides containing Cys-$^{HO}$Gly and alternative units thereof were used as model peptides to find conditions for generating their thioesters. The model compounds were synthesized.

Synthesis of (S)-1-((9H-fluoren-9-yl)methyl) 2-(2-(tert-butoxy)-2-oxoethyl) pyrrolidine-1,2-dicarboxylate (Fmoc-Pro-$^{HO}$Gly-OtBu) (Compound SP631)

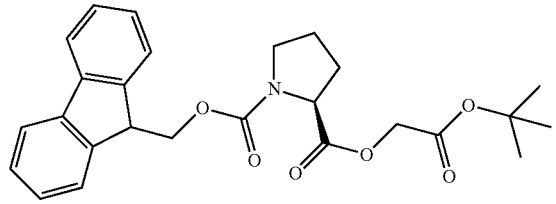 [SMILES: CC(C)(C)OC(=O)COC(=O)[C@@H]1CCCN1C(=O)OCC1c2ccccc2-c2ccccc21]

A solution of (S)-1-(((9H-fluoren-9-yl)methoxy)carbonyl)pyrrolidine-2-carboxylic acid (Fmoc-Pro-OH) (5.00 g, 14.8 mmol) in methylene chloride (59 mL) was mixed with N-ethyldiisopropylamine (DIPEA) (7.77 mL, 44.5 mmol) and tert-butyl 2-bromoacetate (4.34 g, 22.2 mmol) with stirring at room temperature, and the reaction mixture was stirred at room temperature for 48 hours. The reaction mixture was washed with a saturated aqueous ammonium chloride solution, and the organic layer was extracted with methylene chloride. The resulting organic layer was washed with a saturated aqueous sodium chloride solution and dried over sodium sulfate. The organic layer was concentrated under reduced pressure, and the resulting residue was purified by silica gel column chromatography (hexane/ethyl acetate) to afford (S)-1-((9H-fluoren-9-yl)methyl) 2-(2-(tert-butoxy)-2-oxoethyl) pyrrolidine-1,2-dicarboxylate (Fmoc-Pro-$^{HO}$Gly-OtBu) (Compound SP631) (6.40 g, 14.2 mmol, 96%).

LCMS (ESI) m/z=396 (M-tBu+H)+
Retention time: 1.02 min (analysis condition SQDFA05)

Synthesis of (S)-2-((1-(((9H-fluoren-9-yl)methoxy)carbonyl)pyrrolidin-2-carbonyl)oxy)acetic Acid (Fmoc-Pro-$^{HO}$Gly-OH) (Compound SP632)

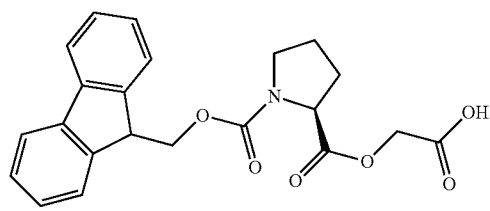 [SMILES: O=C(O)COC(=O)[C@@H]1CCCN1C(=O)OCC1c2ccccc2-c2ccccc21]

A solution of (S)-1-((9H-fluoren-9-yl)methyl) 2-(2-(tert-butoxy)-2-oxoethyl) pyrrolidine-1,2-dicarboxylate (Fmoc-Pro-$^{HO}$Gly-OtBu) (Compound SP631) (6.40 g, 14.2 mmol) in methylene chloride (29 mL) was mixed with triisopropylsilane (7.29 mL, 35.4 mmol) and trifluoroacetic acid (14.2 mL, 184 mmol) with stirring at room temperature, and the reaction mixture was stirred at room temperature for 16 hours. The reaction solution was concentrated under reduced pressure, and the resulting residue was purified by reverse-phase silica gel column chromatography (0.1% aqueous formic acid solution/0.1% formic acid-acetonitrile solution) to afford (S)-2-((1-(((9H-fluoren-9-yl)methoxy)carbonyl)pyrrolidin-2-carbonyl)oxy)acetic acid (Fmoc-Pro-$^{HO}$Gly-OH) (Compound SP632) (5.6 g, 14.2 mmol, 100%).

LCMS (ESI) m/z=396 (M+H)+
Retention time: 0.77 min (analysis condition SQDFA05)

Synthesis of (S)-2-(((S)-1-(((9H-fluoren-9-yl)methoxy)carbonyl)pyrrolidine-2-carbonyl)oxy)propanoic Acid (Fmoc-Pro-Lac-OH) (Compound SP633)

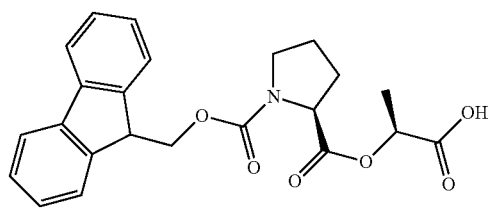 [SMILES: C[C@H](OC(=O)[C@@H]1CCCN1C(=O)OCC1c2ccccc2-c2ccccc21)C(=O)O]

Oxalyl chloride (2.34 mL, 26.7 mmol) was added dropwise to a solution of (S)-1-(((9H-fluoren-9-yl)methoxy)carbonyl)pyrrolidine-2-carboxylic acid (Fmoc-Pro-OH) (6.00 g, 17.8 mmol) and N,N-dimethylformamide (69 µL, 0.889 mmol) in methylene chloride (71 mL) with stirring at 0° C. under a nitrogen atmosphere, and the reaction mixture was then stirred at room temperature for 1 hour. The reaction solution was concentrated under reduced pressure, the resulting residue was mixed with methylene chloride (71 mL), N-ethyldiisopropylamine (DIPEA) (46.6 mL, 267 mmol) and L-(+)-lactic acid (24.0 g, 267 mmol) at 0° C., and the reaction mixture was stirred at room temperature for 2 hours. The reaction solution was washed with 1 N hydrochloric acid twice and a saturated aqueous sodium chloride solution twice, dried over sodium sulfate and then concentrated under reduced pressure. The resulting residue was purified by reverse-phase silica gel column chromatography (0.1% aqueous formic acid solution/0.1% formic acid-acetonitrile solution) to afford (S)-2-(((S)-1-(((9H-fluoren-9-yl)methoxy)carbonyl)pyrrolidine-2-carbonyl)oxy)propanoic acid (Fmoc-Pro-Lac-OH) (Compound SP633) (5.2 g, 12.7 mmol, 71%).

LCMS (ESI) m/z=410 (M+H)+
Retention time: 0.81 min (analysis condition SQDFA05)

Synthesis of (S)-2-(((S)-1-(((9H-fluoren-9-yl)methoxy)carbonyl)pyrrolidine-2-carbonyl)oxy)-3-phenylpropanoic Acid (Fmoc-Pro-PhLac-OH) (Compound SP634)

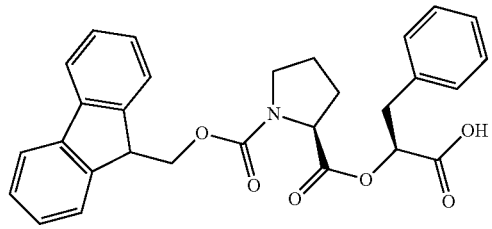 [SMILES: O=C(O)[C@H](Cc1ccccc1)OC(=O)[C@@H]1CCCN1C(=O)OCC1c2ccccc2-c2ccccc21]

Oxalyl chloride (1.17 mL, 13.3 mmol) was added dropwise to a solution of (S)-1-(((9H-fluoren-9-yl)methoxy)carbonyl)pyrrolidine-2-carboxylic acid (Fmoc-Pro-OH) (3.00 g, 8.89 mmol) and N,N-dimethylformamide (34 µL, 0.445 mmol) in methylene chloride (40 mL) with stirring at 0° C. under a nitrogen atmosphere, and the reaction mixture was then stirred at room temperature for 1 hour. The reaction solution was concentrated under reduced pressure, the resulting residue was mixed with methylene chloride (36 mL), N-ethyldiisopropylamine (DIPEA) (2.33 mL, 13.3 mmol) and (S)-2-hydroxy-3-phenylpropanoic acid (HO-PhLac-OH, 2.22 g, 13.3 mmol) at 0° C., and the reaction mixture was stirred at room temperature for 2 hours. The reaction solution was washed with 1 N hydrochloric acid twice and a saturated aqueous sodium chloride solution twice, dried over sodium sulfate and then concentrated under reduced pressure. The resulting residue was purified by reverse-phase silica gel column chromatography (0.1% aqueous formic acid solution/0.1% formic acid-acetonitrile solution) to afford (S)-2-(((S)-1-(((9H-fluoren-9-yl)methoxy)carbonyl)pyrrolidine-2-carbonyl)oxy)-3-phenylpropanoic acid (Fmoc-Pro-PhLac-OH) (Compound SP634) (3.00 g, 6.18 mmol, 70%).

LCMS (ESI) m/z=486 (M+H)+

Retention time: 0.92 min (analysis condition SQDFA05)

PhLac herein refers to a partial structure obtained by removing the hydroxyl group itself and the hydroxyl group forming the carboxylic acid group from (S)-hydroxy-3-phenylpropanoic acid.

Synthesis of (R)-2-(((S)-1-(((9H-fluoren-9-yl)methoxy)carbonyl)pyrrolidine-2-carbonyl)oxy)-3-phenylpropanoic Acid (Fmoc-Pro-D-PhLac-OH) (Compound SP635)

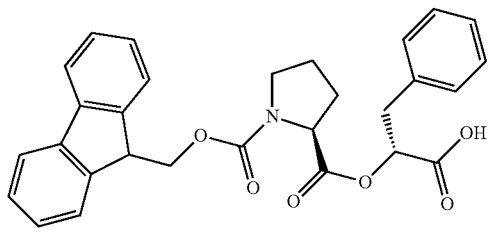 [SMILES: O=C(O)[C@@H](Cc1ccccc1)OC(=O)[C@@H]1CCCN1C(=O)OCC1c2ccccc2-c2ccccc21]

Oxalyl chloride (1.17 mL, 13.3 mmol) was added dropwise to a solution of (S)-1-(((9H-fluoren-9-yl)methoxy)carbonyl)pyrrolidine-2-carboxylic acid (Fmoc-Pro-OH) (3.00 g, 8.89 mmol) and N,N-dimethylformamide (34 µL, 0.445 mmol) in methylene chloride (36 mL) with stirring at 0° C. under a nitrogen atmosphere, and the reaction mixture was then stirred at room temperature for 1 hour. The reaction solution was concentrated under reduced pressure, the resulting residue was mixed with methylene chloride (36 mL), N-ethyldiisopropylamine (DIPEA) (2.33 mL, 13.3 mmol) and (R)-2-hydroxy-3-phenylpropanoic acid (2.22 g, 13.3 mmol) at 0° C., and the reaction mixture was stirred at room temperature for 2 hours. The reaction solution was washed with 1 N hydrochloric acid twice and a saturated aqueous sodium chloride solution twice, dried over sodium sulfate and then concentrated under reduced pressure. The resulting residue was purified by reverse-phase silica gel column chromatography (0.1% aqueous formic acid solution/0.1% formic acid-acetonitrile solution) to afford (R)-2-(((S)-1-(((9H-fluoren-9-yl)methoxy)carbonyl)pyrrolidine-2-carbonyl)oxy)-3-phenylpropanoic acid (Fmoc-Pro-D-PhLac-OH) (Compound SP635) (3.20 g, 6.59 mmol, 74%).

LCMS (EST) m/z=486 (M+H)+

Retention time: 0.91 min (analysis condition SQDFA05)

Synthesis of (S)-2-((1-(((9H-fluoren-9-yl)methoxy)carbonyl)pyrrolidin-2-carbonyl)oxy)-2-methylpropanoic Acid (Fmoc-Pro-$^{HO}$Gly(Me)$_2$-OH) (Compound SP636)

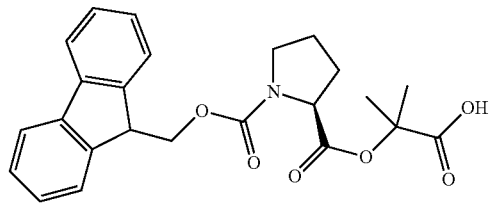 [SMILES: CC(C)(OC(=O)[C@@H]1CCCN1C(=O)OCC1c2ccccc2-c2ccccc21)C(=O)O]

Oxalyl chloride (1.17 mL, 13.3 mmol) was added dropwise to a solution of (S)-1-(((9H-fluoren-9-yl)methoxy)carbonyl)pyrrolidine-2-carboxylic acid (Fmoc-Pro-OH) (3.00 g, 8.89 mmol) and N,N-dimethylformamide (34 µL, 0.445 mmol) in methylene chloride (36 mL) with stirring at 0° C. under a nitrogen atmosphere, and the reaction mixture was then stirred at room temperature for 1 hour. The reaction solution was concentrated under reduced pressure, the resulting residue was mixed with methylene chloride (36 mL), N-ethyldiisopropylamine (DIPEA) (4.66 mL, 26.7 mmol) and 2-hydroxy-2-methylpropanoic acid (2.78 g, 26.7 mmol) at 0° C., and the reaction mixture was stirred at room temperature for 2 hours. The reaction solution was washed with 1 N hydrochloric acid twice and a saturated aqueous sodium chloride solution twice, dried over sodium sulfate and then concentrated under reduced pressure. The resulting residue was purified by reverse-phase silica gel column chromatography (0.1% aqueous formic acid solution/0.1% formic acid-acetonitrile solution) to afford (S)-2-((1-(((9H-fluoren-9-yl)methoxy)carbonyl)pyrrolidine-2-carbonyl)oxy)-2-methylpropanoic acid (Fmoc-Pro-$^{HO}$Gly(Me)$_2$-OH) (Compound SP636) (3.70 g, 8.74 mmol, 98%).

LCMS (ESI) m/z=424 (M+H)+

Retention time: 0.85 min (analysis condition SQDFA05)

$^{HO}$Gly(Me)$_2$ herein refers to a partial structure obtained by removing the hydroxyl group itself and the hydroxyl group forming the carboxylic acid from 2-hydroxy-2-methylpropanoic acid.

Synthesis of 2-(tert-butoxy)-2-oxoethyl 2-((((9H-fluoren-9-yl)methoxy)carbonyl)(methyl)amino)acetate (Fmoc-MeGly-$^{HO}$Gly-OtBu) (Compound SP637)

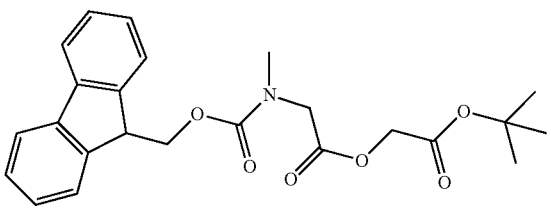 [SMILES: CN(CC(=O)OCC(=O)OC(C)(C)C)C(=O)OCC1c2ccccc2-c2ccccc21]

A solution of 2-((((9H-fluoren-9-yl)methoxy)carbonyl)(methyl)amino)acetic acid (Fmoc-MeGly-OH) (1.94 g, 6.23 mmol) in methylene chloride (25 mL) was mixed with N-ethyldiisopropylamine (DIPEA) (3.26 mL, 18.7 mmol) and tert-butyl 2-bromoacetate (1.82 g, 9.34 mmol) with stirring at room temperature, and the reaction mixture was stirred at room temperature for 48 hours. The reaction mixture was washed with 1 N hydrochloric acid, and the organic layer was extracted with methylene chloride. The resulting organic layer was washed with a saturated aqueous sodium chloride solution and then dried over sodium sulfate. The organic layer was concentrated under reduced pressure, and the resulting residue was purified by silica gel column chromatography (hexane/ethyl acetate) to afford 2-(tert-butoxy)-2-oxoethyl 2-((((9H-fluoren-9-yl)methoxy)carbonyl)(methyl)amino)acetate (Fmoc-MeGly-Gly-OtBu) (Compound SP637) (2.30 g, 5.41 mmol, 87%).

LCMS (PSI) m/z=370 (M-tBu+H)+

Retention time: 0.99 min (analysis condition SQDFA05)

Synthesis of 2-(2-((((9H-fluoren-9-yl)methoxy)carbonyl)(methyl)amino)acetoxy)acetic Acid (Fmoc-MeGly-$^{HO}$Gly-OH) (Compound SP638)

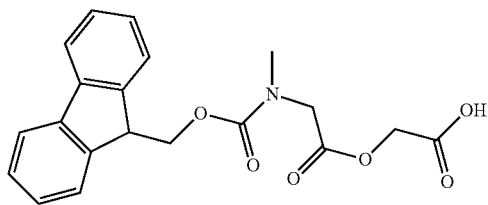 [SMILES: CN(CC(=O)OCC(=O)O)C(=O)OCC1c2ccccc2-c2ccccc21]

A solution of 2-(tert-butoxy)-2-oxoethyl 2-((((9H-fluoren-9-yl)methoxy)carbonyl)(methyl)amino)acetate (Fmoc-MeGly-$^{HO}$Gly-OtBu) (Compound SP637) (2.30 g, 5.41 mmol) in methylene chloride (18 mL) was mixed with triisopropylsilane (2.78 mL, 13.5 mmol) and trifluoroacetic acid (5.41 mL, 70.3 mmol) with stirring at room temperature, and the reaction mixture was stirred at room temperature for 2 hours. The reaction solution was concentrated under reduced pressure, and the resulting residue was purified by reverse-phase silica gel column chromatography (0.1% aqueous formic acid solution/0.1% formic acid-acetonitrile solution) to afford 2-(2-((((9H-fluoren-9-yl)methoxy)carbonyl)(methyl)amino)acetoxy)acetic acid (Fmoc-MeGly-$^{HO}$Gly-OH) (Compound SP638) (2.00 g, 5.41 mmol, 100%).

LCMS (ESI) m/z=370 (M+H)+

Retention time: 0.75 min (analysis condition SQDFA05)

Synthesis of (R)-2-((S)-2-amino-3-(1H-indol-3-yl)propanamido)-3-(tert-butyldisulfanyl)propanoic Acid (H-Trp-Cys(StBu)-OH) (Compound SP639)

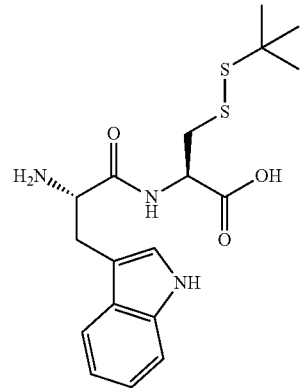 [SMILES: CC(C)(C)SSC[C@H](NC(=O)[C@@H](N)Cc1c[nH]c2ccccc12)C(=O)O]

A solution of the prepared (R)-2-((S)-2-((((9H-fluoren-9-yl)methoxy)carbonyl)amino)-3-(1H-indol-3-yl)propanamido)-3-(tert-butyldisulfanyl)propanoic acid (Fmoc-Trp-Cys(StBu)-OH) (Compound SP602) (500 mg, 0.809 mmol) in N,N-dimethylformamide (1.6 mL) was mixed with 1,8-diazabicyclo[5.4.0]-7-undecene (DBU) (134 μL, 0.890 mmol) with stirring at room temperature, and the reaction solution was stirred at room temperature for 30 minutes. The reaction solution was purified by reverse-phase silica gel column chromatography (0.1% aqueous formic acid solution/0.1% formic acid-acetonitrile solution) to afford (R)-2-((S)-2-amino-3-(1H-indol-3-yl)propanamido)-3-(tert-butyldisulfanyl)propanoic acid (H-Trp-Cys(StBu)-OH) (Compound SP639) (290 mg, 0.733 mmol, 91%).

LCMS (ESI) m/z=396 (M+H)+

Retention time: 0.49 min (analysis condition SQDFA05)

Synthesis of (R)-2-((S)-2-acetamido-3-(1H-indol-3-yl)propanamido)-3-(tert-butyldisulfanyl)propanoic Acid (Ac-Trp-Cys(StBu)-OH) (Compound SP640)

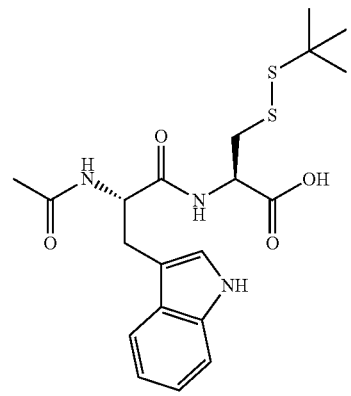 [SMILES: CC(=O)N[C@@H](Cc1c[nH]c2ccccc12)C(=O)N[C@@H](CSSC(C)(C)C)C(=O)O]

A solution of (R)-2-((S)-2-amino-3-(1H-indol-3-yl)propanamido)-3-(tert-butyldisulfanyl)propanoic acid (H-Trp-Cys(StBu)-OH) (Compound SP639) (280 mg, 0.708 mmol) in methylene chloride (1.4 mL) was mixed with N-ethyldiisopropylamine (DIPEA) (371 μL, 2.12 mmol) and acetic anhydride (66.8 μL, 0.708 mmol) with stirring at room temperature, and the reaction solution was stirred at room temperature for 1 hour. The reaction solution was purified by reverse-phase silica gel column chromatography (0.1% aqueous formic acid solution/0.1% formic acid-acetonitrile solution) to afford (R)-2-((S)-2-acetamido-3-(1H-indol-3-yl)propanamido)-3-(tert-butyldisulfanyl)propanoic acid (Ac-Trp-Cys(StBu)-OH) (Compound SP640) (270 mg, 0.617 mmol, 87%).

LCMS (ESI) m/z=438 (M+H)+

Retention time: 0.66 min (analysis condition SQDFA05)

Synthesis of S-tert-butyl Methanesulfonothioate (Compound SP684)

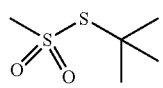

Tetrahydrofuran (100 ml) was added to sodium 2-methyl-2-propanethiolate (7.83 g, 69.8 mmol), and the mixture was cooled to −60° C. or lower. A solution of methanesulfonyl chloride (6.77 ml, 87.0 mmol) in tetrahydrofuran (50 ml) was added dropwise to this suspension over 25 minutes. The reaction solution was gradually warmed to room temperature over 2 hours and stirred at room temperature for additional 1 hour. The reaction solution was diluted with dichloromethane (300 ml) and washed with saturated aqueous sodium bicarbonate and brine. The organic layer was dried over anhydrous sodium sulfate, filtered and then concentrated under reduced pressure to afford S-tert-butyl methanesulfonothioate (Compound SP684) (11.17 g, 76%). The obtained compound was confirmed based on the compound data described in Non patent literature (Inorganic Chemistry, 2010, 49, 8637-8644).

Synthesis of (S)-2-amino-3-(tert-butyldisulfanyl) propanoic Acid (H-D-Cys(StBu)-OH) (Compound SP641)

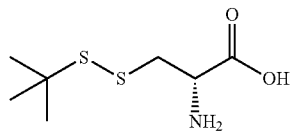

A solution of (S)-2-amino-3-mercaptopropanoic acid hydrochloride hydrate (1.00 g, 5.69 mmol) in methanol (5.1 mL) was mixed with a solution of the prepared S-tert-butyl methanesulfonothioate (Compound SP684, 1.05 g, 6.26 mmol) in tetrahydrofuran (2.0 mL) and triethylamine (2.38 mL, 17.1 mmol) with stirring at 0° C., and the reaction mixture was stirred at room temperature for 3 hours. The reaction mixture was purified by reverse-phase silica gel column chromatography (0.1% aqueous formic acid solution/0.1% formic acid-acetonitrile solution) to afford (S)-2-amino-3-(tert-butyldisulfanyl)propanoic acid (H-D-Cys(StBu)-OH) (Compound SP641) (620 mg, 2.96 mmol, 52%).

LCMS (ESI) m/z=210 (N+H)+

Retention time: 0.56 min (analysis condition SQDAA05)

Synthesis of (S)-2-((S)-2-((((9H-fluoren-9-yl) methoxy)carbonyl)amino)-3-(1H-indol-3-yl)propanamido)-3-(tert-butyldisulfanyl)propanoic Acid (Fmoc-Trp-D-Cys(StBu)-OH) (Compound SP642)

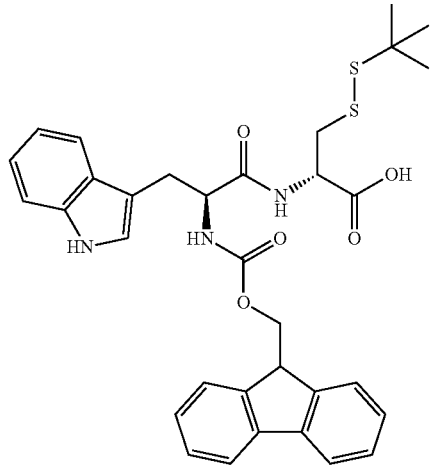 [SMILES: CC(C)(C)SSC[C@@H](NC(=O)[C@H](Cc1c[nH]c2ccccc12)NC(=O)OCC1c2ccccc2-c2ccccc21)C(=O)O]

(S)-2-((((9H-fluoren-9-yl)methoxy)carbonyl)amino)-3-(1H-indol-3-yl)propanoic acid (Fmoc-Trp-OH) (1.26 g, 2.96 mmol) and N-hydroxysuccinimide (341 mg, 2.96 mmol) in methylene chloride (5.9 mL) were mixed with 1-ethyl-3-(3-dimethylaminopropyl)carbodiimide hydrochloride (WSCI·HCl) (568 mg, 2.96 mmol) at 0° C., and the reaction solution was stirred at room temperature for 16 hours. N-Ethyl-N-isopropyl propane 2-amine (DIPEA, 517 μL, 2.96 mmol) and (S)-2-amino-3-(tert-butyldisulfanyl)propanoic acid (H-D-Cys(StBu)-OH) (Compound SP641) (620 mg, 2.96 mmol) were then mixed at 0° C., and the reaction solution was stirred at room temperature for 5 hours. After washing with 1 N hydrochloric acid, the organic layer was extracted with ethyl acetate, and the resulting organic layer was washed with a saturated aqueous sodium chloride solution and then dried over sodium sulfate. Following concentration under reduced pressure, the resulting residue was crude purified by reverse-phase silica gel column chromatography (0.1% aqueous formic acid solution/0.1% formic acid-acetonitrile solution) to afford (S)-2-((S)-2-((((9H-fluoren-9-yl)methoxy)carbonyl)amino)-3-(1H-indol-3-yl)propanamido)-3-(tert-butyldisulfanyl)propanoic acid (Fmoc-Trp-D-Cys(StBu)-OH) (Compound SP642).

LCMS (ESI) m/z=618 (M+H)+

Retention time: 0.94 min (analysis condition SQDFA05)

Synthesis of (S)-2-((S)-2-amino-3-(1H-indol-3-yl)propanamido)-3-(tert-butyldisulfanyl)propanoic Acid (H-Trp-D-Cys(StBu)-OH) (Compound SP643)

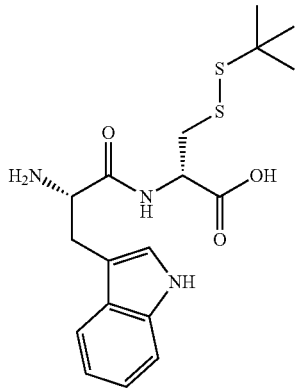 [SMILES: CC(C)(C)SSC[C@@H](NC(=O)[C@@H](N)Cc1c[nH]c2ccccc12)C(=O)O]

A solution of ((S)-2-((S)-2-((((9H-fluoren-9-yl)methoxy)carbonyl)amino)-3-(1H-indol-3-yl)propanamido)-3-(tert-butyldisulfanyl)propanoic acid (Fmoc-Trp-D-Cys(StBu)-OH) (Compound SP642) (1.93 g, 3.12 mmol) in N,N-dimethylformamide (6.3 mL) was mixed with 1,8-diazabicyclo[5.4.0]-7-undecene (DBU) (706 μL, 4.69 mmol) with stirring at room temperature, and the reaction solution was stirred at room temperature for 1 hour. 1 N hydrochloric acid was added to the reaction solution, and the organic layer was extracted with ethyl acetate, washed with brine and then dried over sodium sulfate. Following concentration under reduced pressure, the resulting residue was purified by reverse-phase silica gel column chromatography (0.1% aqueous formic acid solution/0.1% formic acid-acetonitrile solution) to afford (S)-2-((S)-2-amino-3-(1H-indol-3-yl)propanamido)-3-(tert-butyldisulfanyl)propanoic acid (H-Trp-D-Cys(StBu)-OH) (Compound SP643) (870 mg, 2.20 mmol, 70%)

LCMS (ESI) m/z=396 (M+H)+
Retention time: 0.83 min (analysis condition SQDAA05)

Synthesis of (S)-2-((S)-2-acetamido-3-(1H-indol-3-yl)propanamido)-3-(tert-butyldisulfanyl)propanoic Acid (Ac-Trp-D-Cys(StBu)-OH) (Compound SP644)

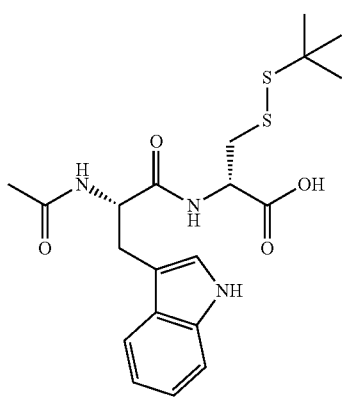 [SMILES: CC(=O)N[C@@H](Cc1c[nH]c2ccccc12)C(=O)N[C@H](CSSC(C)(C)C)C(=O)O]

A solution of (S)-2-((S)-2-amino-3-(1H-indol-3-yl)propanamido)-3-(tert-butyldisulfanyl)propanoic acid (H-Trp-D-Cys(StBu)-OH) (Compound SP643) (870 mg, 2.20 mmol) in methylene chloride (4.4 mL) was mixed with N-ethyldiisopropylamine (DIPEA) (1.15 mL, 6.60 mmol) and acetic anhydride (208 μL, 2.20 mmol) with stirring at room temperature, and the reaction solution was stirred at room temperature for 1 hour. The reaction solution was purified by reverse-phase silica gel column chromatography (0.1% aqueous formic acid solution/0.1% formic acid-acetonitrile solution) to afford (S)-2-((S)-2-acetamido-3-(1H-indol-3-yl)propanamido)-3-(tert-butyldisulfanyl)propanoic acid (Ac-Trp-D-Cys(StBu)-OH) (Compound SP644) (960 mg, 2.20 mmol, 100%).

LCMS (ESI) m/z=438 (M+H)+
Retention time: 0.67 min (analysis condition SQDFA05)

Preparation of Fmoc-Ala-O-Trt(2-Cl) Resin (Compound SP645)

Figure 100:
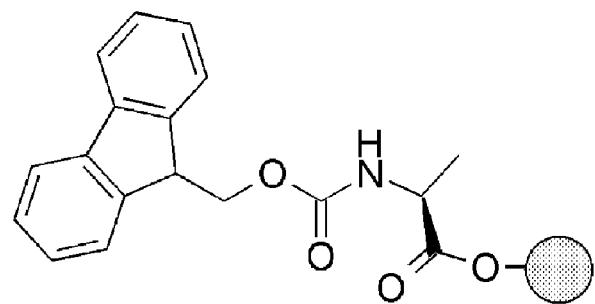
FIG. 100 is a diagram showing the structure of Fmoc-Ala-O-Trt(2-Cl) resin (Compound SP645).

See FIG. 100.

Methylene chloride (100 mL) was added to chloro-trityl (2-chloro) resin (Cl-Trt-(2-Cl)-Resin (100-200 mesh, 1% DVB), purchased from Watanabe Chemical Industries, 14.4 g, 22.96 mmol), and the mixture was allowed to stand at room temperature for 45 minutes. The liquid phase was removed, and the solid phase was washed with methylene chloride (100 mL). The solid phase was mixed with methylene chloride (100 mL), methanol (3.5 mL), N-ethyldiisopropylamine (DIPEA) (10 mL) and (S)-2-((((9H-fluoren-9-yl)methoxy)carbonyl)amino)propanoic acid (3.57 g, 11.5 mmol), and the reaction mixture was shaken at room temperature for 5 minutes. The solid phase and the liquid phase were separated, the resulting resin was mixed with methylene chloride (100 mL), methanol (30 mL) and N-ethyldiisopropylamine (DIPEA) (10 mL), and the reaction mixture was shaken at room temperature for 2 hours. The solid phase and the liquid phase were separated, and the resulting resin was washed with methylene chloride (100 mL) three times and dried under reduced pressure to afford 15.96 g of the title compound (Compound SP645). The loading rate was calculated to be 25.4% according to the method described herein.

Synthesis of (S)-2-(2-(((S)-1-((R)-2-((S)-2-acetamido-3-(1H-indol-3-yl)propanamido)-3-(tert-butyldisulfanyl)propanoyl)pyrrolidine-2-carbonyl)oxy)acetamido)propanoic Acid (Ac-Trp-Cys(StBu)-Pro-$^{HO}$Gly-Ala-OH) (Compound SP646) (SEQ ID NO: 347)

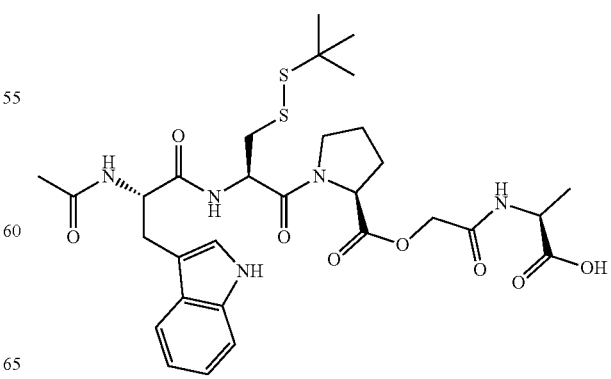

DMF (0.8 mL) was added to the prepared Fmoc-Ala-O-resin (Compound SP645) (200 mg, 0.405 mmol/g, 80.9 µmol), the mixture was shaken at room temperature for 15 minutes, and the solid phase and the liquid phase were separated. A 2% DBU/N,N-dimethylformamide solution (0.8 mL) was added to the resulting resin, the mixture was stirred at room temperature for 30 minutes, and the liquid phase was removed; this series of operations was repeated twice. The resulting resin was washed with N,N-dimethylformamide (0.8 mL) four times and then mixed with a solution of (S)-2-((1-(((9H-fluoren-9-yl)methoxy)carbonyl)pyrrolidin-2-carbonyl)oxy)acetic acid (Fmoc-Pro-$^{HO}$Gly-OH) (Compound SP632) (154 mg, 0.388 mmol) and 1-hydroxy-7-azabenzotriazole (HOAt) (33.0 mg, 0.243 mmol) in NMP (0.64 mL) and a solution of diisopropylcarbodiimide (DIC) (65 µL, 0.417 mmol) in N,N-dimethylformamide (0.52 mL), after which the mixture was shaken at room temperature for 3 hours.

The solid phase and the liquid phase were separated, and the resulting resin was washed with N,N-dimethylformamide (0.8 mL) four times and then mixed with a 5% piperidine/N,N-dimethylformamide solution (0.8 mL), after which the mixture was shaken at room temperature for 1 hour. The solid phase and the liquid phase were separated, and the resulting resin was washed with a N,N-dimethylformamide solution (0.8 mL) four times and then mixed with a solution of (R)-2-((S)-2-acetamido-3-(1H-indol-3-yl)propanamido)-3-(tert-butyldisulfanyl)propanoic acid (Ac-Trp-Cys(StBu)-OH) (Compound SP640) (170 mg, 0.388 mmol) and 3,4-dihydro-3-hydroxy-4-oxo-1,2,3-benzotriazine (HOObt) (39.6 mg, 0.243 mmol) in NMP (0.64 mL) and a solution of diisopropylcarbodiimide (DIC) (65 µL, 0.417 mmol) in N,N-dimethylformamide (0.52 mL), after which the mixture was shaken at room temperature for 15 hours.

The solid phase and the liquid phase were separated, and the resulting resin was washed with N,N-dimethylformamide (0.8 mL) four times and then with methylene chloride (0.8 mL) four times and then mixed with a 50% 2,2,2-trifluoroethanol/methylene chloride solution (1.0 mL), after which the mixture was shaken at room temperature for 2 hours.

The solid phase and the liquid phase were separated, the solid phase was washed with methylene chloride (1.0 mL), and the resulting liquid phase was concentrated under reduced pressure. The resulting residue was purified by reverse-phase silica gel column chromatography (0.1% aqueous formic acid solution/0.1% formic acid-acetonitrile solution) to afford (S)-2-(2-(((S)-1-((R)-2-((S)-2-acetamido-3-(1H-indol-3-yl)propanamido)-3-(tert-butyldisulfanyl)propanoyl)pyrrolidine-2-carbonyl)oxy)acetamido)propanoic acid (Ac-Trp-Cys(StBu)-Pro-$^{HO}$Gly-Ala-OH) (Compound SP646) (SEQ ID NO: 347) (37.8 mg, 57 µmol, 70%).

LCMS (ESI) m/z=664 (M+H)+
Retention time: 0.80 min (analysis condition SQDAA05)

Synthesis of (S)-2-((S)-2-(((S)-1-((R)-2-((S)-2-acetamido-3-(1H-indol-3-yl)propanamido)-3-(tert-butyldisulfanyl)propanoyl)pyrrolidine-2-carbonyl)oxy)propanamido)propanoic Acid (Ac-Trp-Cys(StBu)-Pro-Lac-Ala-OH) (Compound SP647) (SEQ ID NO: 348)

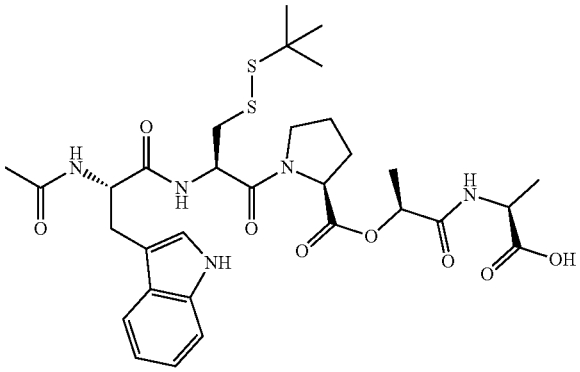 [SMILES: CC(=O)N[C@@H](Cc1c[nH]c2ccccc12)C(=O)N[C@@H](CSSC(C)(C)C)C(=O)N1CCC[C@H]1C(=O)O[C@@H](C)C(=O)N[C@@H](C)C(=O)O]

DMF (0.8 mL) was added to the prepared Fmoc-Ala-O-resin (Compound SP645) (200 mg, 0.405 mmol/g, 80.9 µmol), the mixture was shaken at room temperature for 15 minutes, and the solid phase and the liquid phase were separated. A 2% DBU/N,N-dimethylformamide solution (0.8 mL) was added to the resulting resin, the mixture was stirred at room temperature for 30 minutes, and the liquid phase was removed; this series of operations was repeated twice. The resulting resin was washed with N,N-dimethylformamide (0.8 mL) four times and then mixed with a solution of (S)-2-(((S)-1-(((9H-fluoren-9-yl)methoxy)carbonyl)pyrrolidine-2-carbonyl)oxy)propanoic acid (Fmoc-Pro-Lac-OH) (Compound SP633) (159 mg, 0.388 mmol) and 1-hydroxy-7-azabenzotriazole (HOAt) (33.0 mg, 0.243 mmol) in NMP (0.64 mL) and a solution of diisopropylcarbodiimide (DIC) (65 µL, 0.417 mmol) in N,N-dimethylformamide (0.52 mL), after which the mixture was shaken at room temperature for 3 hours. The solid phase and the liquid phase were separated, and the resulting resin was washed with N,N-dimethylformamide (0.8 mL) four times and then mixed with a 5% piperidine/N,N-dimethylformamide solution (0.8 mL), after which the mixture was shaken at room temperature for 1 hour.

The solid phase and the liquid phase were separated, and the resulting resin was washed with a N,N-dimethylformamide solution (0.8 mL) four times and then mixed with a solution of (R)-2-((S)-2-acetamido-3-(1H-indol-3-yl)propanamido)-3-(tert-butyldisulfanyl)propanoic acid (Ac-Trp-Cys(StBu)-OH) (Compound SP640) (170 mg, 0.388 mmol) and 3,4-dihydro-3-hydroxy-4-oxo-1,2,3-benzotriazine (HOObt) (39.6 mg, 0.243 mmol) in NMP (0.64 mL) and a solution of diisopropylcarbodiimide (DIC) (65 µL, 0.417 mmol) in N,N-dimethylformamide (0.52 mL), after which the mixture was shaken at room temperature for 15 hours.

The solid phase and the liquid phase were separated, and the resulting resin was washed with N,N-dimethylformamide (0.8 mL) four times and then with methylene chloride (0.8 mL) four times and then mixed with a 50% 2,2,2-trifluoroethanol/methylene chloride solution (1.0 mL), after which the mixture was shaken at room temperature for 2 hours.

The solid phase and the liquid phase were separated, the solid phase was washed with methylene chloride (1.0 mL), and the resulting liquid phase was concentrated under reduced pressure. The resulting residue was purified by reverse-phase silica gel column chromatography (0.1% aqueous formic acid solution/0.1% formic acid-acetonitrile solution) to afford (S)-2-((S)-2-(((S)-1-((R)-2-((S)-2-acetamido-3-(1H-indol-3-yl)propanamido)-3-(tert-butyldisulfanyl)propanoyl)pyrrolidine-2-carbonyl)oxy)propanamido)propanoic acid (Ac-Trp-Cys(StBu)-Pro-Lac-Ala-OH) (Compound SP647) (SEQ ID NO: 348) (51.4 mg, 76 μmol, 94%).

LCMS (ESI) m/z=678 (M+H)+
Retention time: 0.82 min (analysis condition SQDAA05)

Synthesis of (S)-2-((S)-2-(((S)-1-((R)-2-((S)-2-acetamido-3-(1H-indol-3-yl)propanamido)-3-(tert-butyldisulfanyl)propanoyl)pyrrolidine-2-carbonyl)oxy)-3-phenylpropanamido)propanoic Acid (Ac-Trp-Cys(StBu)-Pro-PhLac-Ala-OH) (Compound SP648) (SEQ ID NO: 349)

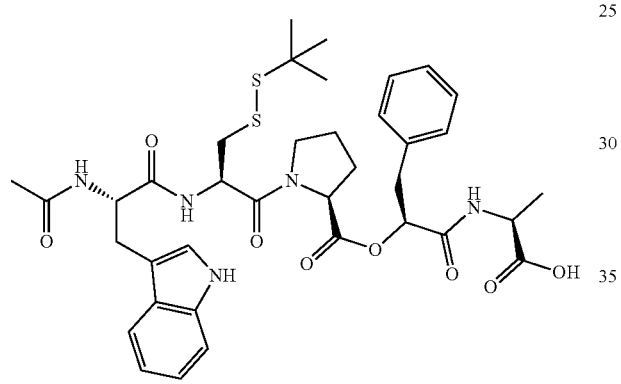

DMF (0.8 mL) was added to the prepared Fmoc-Ala-O-resin (Compound SP645) (200 mg, 0.405 mmol/g, 80.9 μmol), the mixture was shaken at room temperature for 15 minutes, and the solid phase and the liquid phase were separated. A 2% DBU/N,N-dimethylformamide solution (0.8 mL) was added to the resulting resin, the mixture was stirred at room temperature for 30 minutes, and the liquid phase was removed; this series of operations was repeated twice. The resulting resin was washed with N,N-dimethylformamide (0.8 mL) four times and then mixed with a solution of (S)-2-(((S)-1-(((9H-fluoren-9-yl)methoxy)carbonyl)pyrrolidine-2-carbonyl)oxy)-3-phenylpropanoic acid (Fmoc-Pro-PhLac-OH) (Compound SP634) (189 mg, 0.388 mmol) and 1-hydroxy-7-azabenzotriazole (HOAt) (33.0 mg, 0.243 mmol) in NMP (0.64 mL) and a solution of diisopropylcarbodiimide (DIC) (65 μL, 0.417 mmol) in N,N-dimethylformamide (0.52 mL), after which the mixture was shaken at room temperature for 3 hours.

The solid phase and the liquid phase were separated, and the resulting resin was washed with N,N-dimethylformamide (0.8 mL) four times and then mixed with a 5% piperidine/N,N-dimethylformamide solution (0.8 mL), after which the mixture was shaken at room temperature for 1 hour. The solid phase and the liquid phase were separated, and the resulting resin was washed with a N,N-dimethylformamide solution (0.8 mL) four times and then mixed with a solution of (R)-2-((S)-2-acetamido-3-(1H-indol-3-yl)propanamido)-3-(tert-butyldisulfanyl)propanoic acid (Ac-Trp-Cys(StBu)-OH) (Compound SP640) (170 mg, 0.388 mmol) and 3,4-dihydro-3-hydroxy-4-oxo-1,2,3-benzotriazine (HOObt) (39.6 mg, 0.243 mmol) in NMP (0.64 mL) and a solution of diisopropylcarbodiimide (DIC) (65 μL, 0.417 mmol) in N,N-dimethylformamide (0.52 mL), after which the mixture was shaken at room temperature for 15 hours. The solid phase and the liquid phase were separated, and the resulting resin was washed with N,N-dimethylformamide (0.8 mL) four times and then with methylene chloride (0.8 mL) four times and then mixed with a 50% 2,2,2-trifluoroethanol/methylene chloride solution (1.0 mL), after which the mixture was shaken at room temperature for 2 hours.

The solid phase and the liquid phase were separated, the solid phase was washed with methylene chloride (1.0 mL), and the resulting liquid phase was concentrated under reduced pressure. The resulting residue was purified by reverse-phase silica gel column chromatography (0.1% aqueous formic acid solution/0.1% formic acid-acetonitrile solution) to afford (S)-2-((S)-2-(((S)-1-((R)-2-((S)-2-acetamido-3-(1H-indol-3-yl)propanamido)-3-(tert-butyldisulfanyl)propanoyl)pyrrolidine-2-carbonyl)oxy)-3-phenylpropanamido)propanoic acid (Ac-Trp-Cys(StBu)-Pro-PhLac-Ala-OH) (Compound SP648) (SEQ ID NO: 349) (51.2 mg, 68 μmol, 84%).

LCMS (ESI) m/z=754 (M+H)+
Retention time: 0.92 min (analysis condition SQDAA05)

Synthesis of (S)-2-((R)-2-(((S)-1-((R)-2-((S)-2-acetamido-3-(1H-indol-3-yl)propanamido)-3-(tert-butyldisulfanyl)propanoyl)pyrrolidine-2-carbonyl)oxy)-3-phenylpropanamido)propanoic Acid (Ac-Trp-Cys(StBu)-Pro-D-PhLac-Ala-OH) (Compound SP649) (SEQ ID NO: 350)

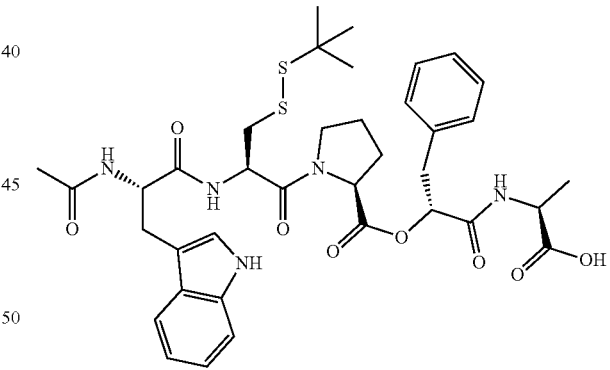

DMF (0.8 mL) was added to the prepared Fmoc-Ala-O-resin (Compound SP645) (200 mg, 0.405 mmol/g, 80.9 μmol), the mixture was shaken at room temperature for 15 minutes, and the solid phase and the liquid phase were separated. A 2% DBU/N,N-dimethylformamide solution (0.8 mL) was added to the resulting resin, the mixture was stirred at room temperature for 30 minutes, and the liquid phase was removed; this series of operations was repeated twice. The resulting resin was washed with N,N-dimethylformamide (0.8 mL) four times and then mixed with a solution of (R)-2-(((S)-1-(((9H-fluoren-9-yl)methoxy)carbonyl)pyrrolidine-2-carbonyl)oxy)-3-phenylpropanoic acid (Fmoc-Pro-D-PhLac-OH) (Compound SP635) (189 mg, 0.388 mmol) and 1-hydroxy-7-azabenzotriazole (HOAt)

(33.0 mg, 0.243 mmol) in NMP (0.64 mL) and a solution of diisopropylcarbodiimide (DIC) (65 µL, 0.417 mmol) in N,N-dimethylformamide (0.52 mL), after which the mixture was shaken at room temperature for 3 hours.

The solid phase and the liquid phase were separated, and the resulting resin was washed with N,N-dimethylformamide (0.8 mL) four times and then mixed with a 5% piperidine/N,N-dimethylformamide solution (0.8 mL), after which the mixture was shaken at room temperature for 1 hour. The solid phase and the liquid phase were separated, and the resulting resin was washed with a N,N-dimethylformamide solution (0.8 mL) four times and then mixed with a solution of (R)-2-((S)-2-acetamido-3-(1H-indol-3-yl)propanamido)-3-(tert-butyldisulfanyl)propanoic acid (Ac-Trp-Cys(StBu)-OH) (Compound SP640) (170 mg, 0.388 mmol) and 3,4-dihydro-3-hydroxy-4-oxo-1,2,3-benzotriazine (HOObt) (39.6 mg, 0.243 mmol) in NMP (0.64 mL) and a solution of diisopropylcarbodiimide (DIC) (65 µL, 0.417 mmol) in N,N-dimethylformamide (0.52 mL), after which the mixture was shaken at room temperature for 15 hours. The solid phase and the liquid phase were separated, and the resulting resin was washed with N,N-dimethylformamide (0.8 mL) four times and then with methylene chloride (0.8 mL) four times and then mixed with a 50% 2,2,2-trifluoroethanol/methylene chloride solution (1.0 mL), after which the mixture was shaken at room temperature for 2 hours.

The solid phase and the liquid phase were separated, the solid phase was washed with methylene chloride (1.0 mL), and the resulting liquid phase was concentrated under reduced pressure. The resulting residue was purified by reverse-phase silica gel column chromatography (0.1% aqueous formic acid solution/0.1% formic acid-acetonitrile solution) to afford (S)-2-((R)-2-(((S)-1-((R)-2-((S)-2-acetamido-3-(1H-indol-3-yl)propanamido)-3-(tert-butyldisulfanyl)propanoyl)pyrrolidine-2-carbonyl)oxy)-3-phenylpropanamido)propanoic acid (Ac-Trp-Cys(StBu)-Pro-D-PhLac-Ala-OH) (Compound SP649) (SEQ ID NO: 350) (50.0 mg, 66.0 µmol, 82%).

LCMS (ESI) m/z=754 (M+H)+
Retention time: 0.93 min (analysis condition SQDAA05)

Synthesis of (S)-2-(2-(((S)-1-((R)-2-((S)-2-acetamido-3-(1H-indol-3-yl)propanamido)-3-(tert-butyldisulfanyl)propanoyl)pyrrolidine-2-carbonyl)oxy)-2-methylpropanamido)propanoic Acid (Ac-Trp-Cys(StBu)-Pro-$^{HO}$Gly(Me)$_2$-Ala-OH) (Compound SP650) (SEQ ID NO: 351)

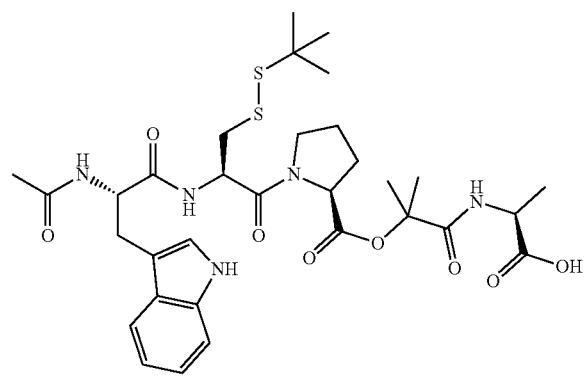 [SMILES: CC(=O)N[C@@H](Cc1c[nH]c2ccccc12)C(=O)N[C@@H](CSSC(C)(C)C)C(=O)N1CCC[C@H]1C(=O)OC(C)(C)C(=O)N[C@@H](C)C(=O)O]

DMF (0.8 mL) was added to the prepared Fmoc-Ala-O-resin (Compound SP645) (200 mg, 0.405 mmol/g, 80.9 µmol), the mixture was shaken at room temperature for 15 minutes, and the solid phase and the liquid phase were separated. A 2% DBU/N,N-dimethylformamide solution (0.8 mL) was added to the resulting resin, the mixture was stirred at room temperature for 30 minutes, and the liquid phase was removed; this series of operations was repeated twice. The resulting resin was washed with N,N-dimethylformamide (0.8 mL) four times and then mixed with a solution of (S)-2-((1-(((9H-fluoren-9-yl)methoxy)carbonyl)pyrrolidin-2-carbonyl)oxy)-2-methylpropanoic acid (Fmoc-Pro-$^{HO}$Gly(Me)$_2$-OH) (Compound SP636) (164 mg, 0.388 mmol) and 1-hydroxy-7-azabenzotriazole (HOAt) (33.0 mg, 0.243 mmol) in NMP (0.64 mL) and a solution of diisopropylcarbodiimide (DIC) (65 µl, 0.417 mmol) in N,N-dimethylformamide (0.52 mL), after which the mixture was shaken at room temperature for 3 hours. The solid phase and the liquid phase were separated, and the resulting resin was washed with N,N-dimethylformamide (0.8 mL) four times and then mixed with a 5% piperidine/N,N-dimethylformamide solution (0.8 mL), after which the mixture was shaken at room temperature for 1 hour.

The solid phase and the liquid phase were separated, and the resulting resin was washed with a N,N-dimethylformamide solution (0.8 mL) four times and then mixed with a solution of (R)-2-((S)-2-acetamido-3-(1H-indol-3-yl)propanamido)-3-(tert-butyldisulfanyl)propanoic acid (Ac-Trp-Cys(StBu)-OH) (Compound SP640) (170 mg, 0.388 mmol) and 3,4-dihydro-3-hydroxy-4-oxo-1,2,3-benzotriazine (HOObt) (39.6 mg, 0.243 mmol) in NMP (0.64 mL) and a solution of diisopropylcarbodiimide (DIC) (65 µL, 0.417 mmol) in N,N-dimethylformamide (0.52 mL), after which the mixture was shaken at room temperature for 15 hours.

The solid phase and the liquid phase were separated, and the resulting resin was washed with N,N-dimethylformamide (0.8 mL) four times and then with methylene chloride (0.8 mL) four times and then mixed with a 50% 2,2,2-trifluoroethanol/methylene chloride solution (1.0 mL), after which the mixture was shaken at room temperature for 2 hours. The solid phase and the liquid phase were separated, the solid phase was washed with methylene chloride (1.0 mL), and the resulting liquid phase was concentrated under reduced pressure. The resulting residue was purified by reverse-phase silica gel column chromatography (0.1% aqueous formic acid solution/0.1% formic acid-acetonitrile solution) to afford (S)-2-(2-(((S)-1-((R)-2-((S)-2-acetamido-3-(1H-indol-3-yl)propanamido)-3-(tert-butyldisulfanyl)propanoyl)pyrrolidine-2-carbonyl)oxy)-2-methylpropanamido)propanoic acid (Ac-Trp-Cys(StBu)-Pro-$^{HO}$Gly(Me)$_2$-Ala-OH) (Compound SP650) (SEQ ID NO: 351) (46.4 mg, 67 µmol, 83%).

LCMS (ESI) m/z=692 (M+H)+
Retention time: 0.84 min (analysis condition SQDAA05)

Synthesis of (4S,7R,16S)-4-((1H-indol-3-yl)methyl)-7-((tert-butyldisulfanyl)methyl)-9,16-dimethyl-2,5,8,11,14-pentaoxo-12-oxa-3,6,9,15-tetraazaheptadecan-17-oic Acid (Ac-Trp-Cys(StBu)-MeGly-$^{HO}$Gly-Ala-OH) (Compound SP651) (SEQ ID NO: 257)

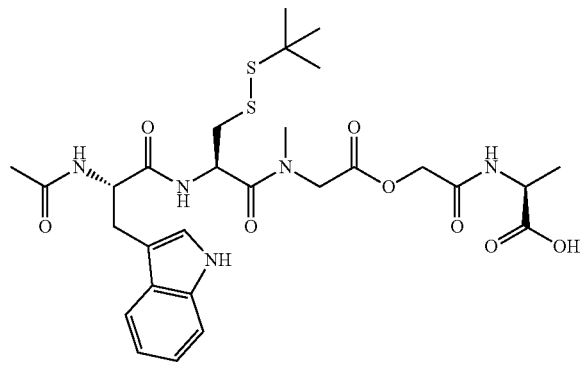 [SMILES: CC(=O)N[C@@H](Cc1c[nH]c2ccccc12)C(=O)N[C@@H](CSSC(C)(C)C)C(=O)N(C)CC(=O)OCC(=O)N[C@@H](C)C(=O)O]

DMF (0.8 mL) was added to the prepared Fmoc-Ala-O-resin (Compound SP645) (200 mg, 0.405 mmol/g, 80.9 µmol), the mixture was shaken at room temperature for 15 minutes, and the solid phase and the liquid phase were separated. A 2% DBU/N,N-dimethylformamide solution (0.8 mL) was added to the resulting resin, the mixture was stirred at room temperature for 30 minutes, and the liquid phase was removed; this series of operations was repeated twice. The resulting resin was washed with N,N-dimethylformamide (0.8 mL) four times and then mixed with a solution of 2-(2-((((9H-fluoren-9-yl)methoxy)carbonyl)(methyl)amino)acetoxy)acetic acid (Fmoc-MeGly-$^{HO}$Gly-OH) (Compound SP638) (143 mg, 0.388 mmol) and 1-hydroxy-7-azabenzotriazole (HOAt) (33.0 mg, 0.243 mmol) in NMP (0.64 mL) and a solution of diisopropylcarbodiimide (DIC) (65 µL, 0.417 mmol) in N,N-dimethylformamide (0.52 mL), after which the mixture was shaken at room temperature for 3 hours.

The solid phase and the liquid phase were separated, and the resulting resin was washed with N,N-dimethylformamide (0.8 mL) four times and then mixed with a 5% piperidine/N,N-dimethylformamide solution (0.8 mL), after which the mixture was shaken at room temperature for 1 hour. The solid phase and the liquid phase were separated, and the resulting resin was washed with a N,N-dimethylformamide solution (0.8 mL) four times and then mixed with a solution of (R)-2-((S)-2-acetamido-3-(1H-indol-3-yl)propanamido)-3-(tert-butyldisulfanyl)propanoic acid (Ac-Trp-Cys(StBu)-OH) (Compound SP640) (170 mg, 0.388 mmol) and 3,4-dihydro-3-hydroxy-4-oxo-1,2,3-benzotriazine (HOObt) (39.6 mg, 0.243 mmol) in NMP (0.64 mL) and a solution of diisopropylcarbodiimide (DIC) (65 µL, 0.417 mmol) in N,N-dimethylformamide (0.52 mL), after which the mixture was shaken at room temperature for 15 hours. The solid phase and the liquid phase were separated, and the resulting resin was washed with N,N-dimethylformamide (0.8 mL) four times and then with methylene chloride (0.8 mL) four times and then mixed with a 50% 2,2,2-trifluoroethanol/methylene chloride solution (1.0 mL), after which the mixture was shaken at room temperature for 2 hours. The solid phase and the liquid phase were separated, the solid phase was washed with methylene chloride (1.0 mL), and the resulting liquid phase was concentrated under reduced pressure. The resulting residue was purified by reverse-phase silica gel column chromatography (0.1% aqueous formic-acid solution/0.1% formic acid-acetonitrile solution) to afford (4S,7R,16S)-4-((1H-indol-3-yl)methyl)-7-((tert-butyldisulfanyl)methyl)-9,16-dimethyl-2,5,8,11,14-pentaoxo-12-oxa-3,6,9,15-tetraazaheptadecan-17-oic acid (Ac-Trp-Cys(StBu)-MeGly-$^{HO}$Gly-Ala-OH) (Compound SP651) (SEQ ID NO: 257) (26.7 mg, 42 µmol, 52%).

LCMS (ESI) m/z=638 (M+H)+

Retention time: 0.79 min (analysis condition SQDAA05)

Synthesis of (4S,7S,16S)-4-((1H-indol-3-yl)methyl)-7-((tert-butyldisulfanyl)methyl)-9,16-dimethyl-2,5,8,11,14-pentaoxo-12-oxa-3,6,9,15-tetraazaheptadecan-17-oic Acid (Ac-Trp-D-Cys(StBu)-MeGly-Gly-Ala-OH) (Compound SP652) (SEQ ID NO: 258)

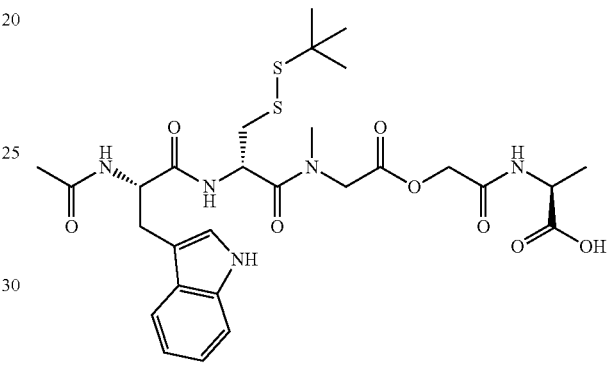

DMF (0.8 mL) was added to the prepared Fmoc-Ala-O-resin (Compound SP645) (200 mg, 0.405 mmol/g, 80.9 µmol), the mixture was shaken at room temperature for 15 minutes, and the solid phase and the liquid phase were separated. A 2% DBU/N,N-dimethylformamide solution (0.8 mL) was added to the resulting resin, the mixture was stirred at room temperature for 30 minutes, and the liquid phase was removed; this series of operations was repeated twice. The resulting resin was washed with N,N-dimethylformamide (0.8 mL) four times and then mixed with a solution of 2-(2-((((9H-fluoren-9-yl)methoxy)carbonyl)(methyl)amino)acetoxy)acetic acid (Fmoc-MeGly-$^{HO}$Gly-OH) (Compound SP638) (143 mg, 0.388 mmol) and 1-hydroxy-7-azabenzotriazole (HOAt) (33.0 mg, 0.243 mmol) in NMP (0.64 mL) and a solution of diisopropylcarbodiimide (DIC) (65 µL, 0.417 mmol) in N,N-dimethylformamide (0.52 mL), after which the mixture was shaken at room temperature for 3 hours.

The solid phase and the liquid phase were separated, and the resulting resin was washed with N,N-dimethylformamide (0.8 mL) four times and then mixed with a 5% piperidine/N,N-dimethylformamide solution (0.8 mL), after which the mixture was shaken at room temperature for 1 hour. The solid phase and the liquid phase were separated, and the resulting resin was washed with a N,N-dimethylformamide solution (0.8 mL) four times and then mixed with a solution of (S)-2-((S)-2-acetamido-3-(1H-indol-3-yl)propanamido)-3-(tert-butyldisulfanyl)propanoic acid (Ac-Trp-D-Cys(StBu)-OH) (Compound SP644) (170 mg, 0.388 mmol) and 3,4-dihydro-3-hydroxy-4-oxo-1,2,3-benzotriazine (HOObt) (39.6 mg, 0.243 mmol) in NMP (0.64 mL) and a solution of diisopropylcarbodiimide (DIC) (65 µL, 0.417 mmol) in N,N-dimethylformamide (0.52 mL), after which the mixture was shaken at room temperature for 15 hours. The solid phase and the liquid phase were separated, and the resulting resin was washed with N,N-dimethylformamide (0.8 mL) four times and then with methylene chloride (0.8 mL) four times and then mixed with a 50% 2,2,2-trifluoroethanol/methylene chloride solution (1.0 mL), after which the mixture was shaken at room temperature for 2 hours. The solid phase and the liquid phase were separated, the solid phase was washed with methylene chloride (1.0 mL), and the resulting liquid phase was concentrated under reduced pressure. The resulting residue was purified by reverse-phase silica gel column chromatography (0.1% aqueous formic acid solution/0.1% formic acid-acetonitrile solution) to afford (4S,7S,16S)-4-((1H-indol-3-yl)methyl)-7-((tert-butyldisulfanyl)methyl)-9,16-dimethyl-2,5,8,11,14-pentaoxo-12-oxa-3,6,9,15-tetraazaheptadecan-17-oic acid (Ac-Trp-D-Cys(StBu)-MeGly-$^{HO}$Gly-Ala-OH) (Compound SP652) (SEQ ID NO: 258) (36.5 mg, 57 µmol, 71%).

LCMS (ESI) m/z=638 (M+H)+
Retention time: 0.81 min (analysis condition SQDAA05)

Synthesis of (S)-2-(2-(((S)-1-((S)-2-((S)-2-acetamido-3-(1H-indol-3-yl)propanamido)-3-(tert-butyldisulfanyl)propanoyl)pyrrolidine-2-carbonyl)oxy)acetamido)propanoic Acid (Ac-Trp-D-Cys(StBu)-Pro-$^{HO}$Gly-Ala-OH) (Compound SP653) (SEQ ID NO: 259)

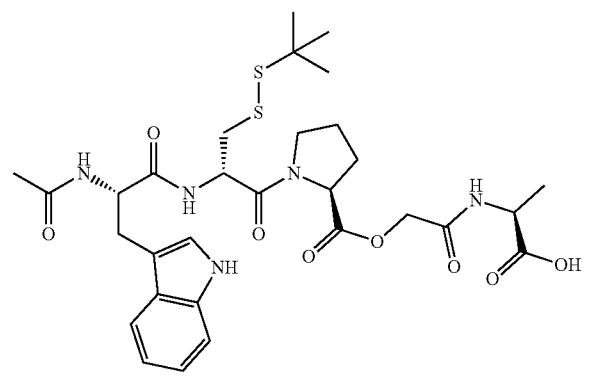 [SMILES: CC(=O)N[C@@H](Cc1c[nH]c2ccccc12)C(=O)N[C@H](CSSC(C)(C)C)C(=O)N1CCC[C@H]1C(=O)OCC(=O)N[C@@H](C)C(=O)O]

DMF (0.2 mL) was added to the prepared Fmoc-Ala-O-resin (Compound SP645) (50 mg, 0.405 mmol/g, 20.2 µmol), the mixture was shaken at room temperature for 15 minutes, and the solid phase and the liquid phase were separated. A 2% DBU/N,N-dimethylformamide solution (0.2 mL) was added to the resulting resin, the mixture was stirred at room temperature for 30 minutes, and the liquid phase was removed; this series of operations was repeated twice. The resulting resin was washed with N,N-dimethylformamide (0.2 mL) four times and then mixed with a solution of (S)-2-((1-(((9H-fluoren-9-yl)methoxy)carbonyl)pyrrolidin-2-carbonyl)oxy)acetic acid (Fmoc-Pro-$^{HO}$Gly-OH) (Compound SP632) (38.4 mg, 0.097 mmol) and 1-hydroxy-7-azabenzotriazole (HOAt) (8.26 mg, 60.7 µmol) in NMP (0.16 mL) and a solution of diisopropylcarbodiimide (DIC) (16 µL, 0.104 mmol) in N,N-dimethylformamide (0.13 mL), after which the mixture was shaken at room temperature for 6 hours. The solid phase and the liquid phase were separated, and the resulting resin was washed with N,N-dimethylformamide (0.2 mL) four times and then mixed with a 5% piperidine/N,N-dimethylformamide solution (0.2 mL), after which the mixture was shaken at room temperature for 1 hour.

The solid phase and the liquid phase were separated, and the resulting resin was washed with a N,N-dimethylformamide solution (0.2 mL) four times and then mixed with a solution of (S)-2-((S)-2-acetamido-3-(1H-indol-3-yl)propanamido)-3-(tert-butyldisulfanyl)propanoic acid (Ac-Trp-D-Cys(StBu)-OH) (Compound SP644) (42.5 mg, 0.097 mmol) and 3,4-dihydro-3-hydroxy-4-oxo-1,2,3-benzotriazine (HOObt) (9.9 mg, 60.8 mol) in NMP (0.160 mL) and a solution of diisopropylcarbodiimide (DIC) (16 µL, 0.104 mmol) in N,N-dimethylformamide (0.13 mL), after which the mixture was shaken at room temperature for 15 hours. The solid phase and the liquid phase were separated, and the resulting resin was washed with N,N-dimethylformamide (0.2 mL) four times and then with methylene chloride (0.2 mL) four times and then mixed with a 50% 2,2,2-trifluoroethanol/methylene chloride solution (0.25 mL), after which the mixture was shaken at room temperature for 2 hours. The solid phase and the liquid phase were separated, and the resulting liquid phase was concentrated under reduced pressure. The resulting residue was purified by reverse-phase silica gel column chromatography (10 mM aqueous ammonium acetate solution/methanol) to afford (S)-2-(2-(((S)-1-((S)-2-((S)-2-acetamido-3-(1H-indol-3-yl)propanamido)-3-(tert-butyldisulfanyl)propanoyl)pyrrolidine-2-carbonyl)oxy)acetamido)propanoic acid (Ac-Trp-D-Cys(StBu)-Pro-$^{HO}$Gly-Ala-OH) (Compound SP653) (SEQ ID NO: 259) (3.0 mg, 4.5 µmol, 22%).

LCMS (ESI) m/z=664 (M+H)+
Retention time: 0.85 min (analysis condition SQDAA05)

Synthesis of (S)-2-((S)-2-(((S)-1-((S)-2-((S)-2-acetamido-3-(1H-indol-3-yl)propanamido)-3-(tert-butyldisulfanyl)propanoyl)pyrrolidine-2-carbonyl)oxy)propanamido)propanoic Acid (Ac-Trp-D-Cys(StBu)-Pro-Lac-Ala-OH) (Compound SP654) (SEQ ID NO: 352)

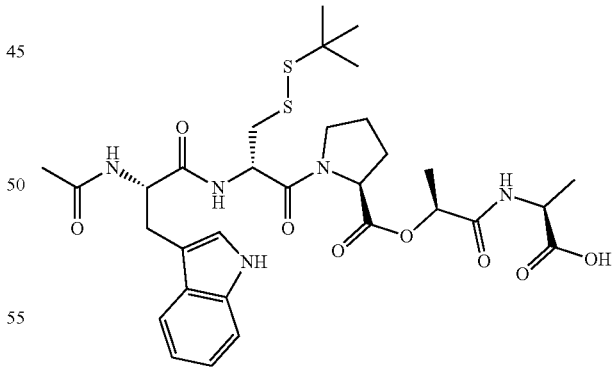

DMF (0.2 mL) was added to the prepared Fmoc-Ala-O-resin (Compound SP645) (50 mg, 0.405 mmol/g, 20.2 µmol), the mixture was shaken at room temperature for 15 minutes, and the solid phase and the liquid phase were separated. A 2% DBU/N,N-dimethylformamide solution (0.2 mL) was added to the resulting resin, the mixture was stirred at room temperature for 30 minutes, and the liquid phase was removed; this series of operations was repeated twice. The resulting resin was washed with N,N-dimethylformamide (0.2 mL) four times and then mixed with a solution of (S)-2-(((S)-1-(((9H-fluoren-9-yl)methoxy)carbonyl)pyrrolidine-2-carbonyl)oxy)propanoic acid (Fmoc-Pro-Lac-OH) (Compound SP633) (39.8 mg, 0.097 mmol) and 1-hydroxy-7-azabenzotriazole (HOAt) (8.2633.0 mg, 60.7 µl, 0.243 mmol) in NMP (0.16 mL) and a solution of diisopropylcarbodiimide (DIC) (16 µL, 0.104 mmol) in N,N-dimethylformamide (0.13 mL), after which the mixture was shaken at room temperature for 63 hours.

The solid phase and the liquid phase were separated, and the resulting resin was washed with N,N-dimethylformamide (0.2 mL) four times and then mixed with a 5% piperidine/N,N-dimethylformamide solution (0.2 mL), after which the mixture was shaken at room temperature for 1 hour. The solid phase and the liquid phase were separated, and the resulting resin was washed with a N,N-dimethylformamide solution (0.2 mL) four times and then mixed with a solution of (S)-2-((S)-2-acetamido-3-(1H-indol-3-yl)propanamido)-3-(tert-butyldisulfanyl)propanoic acid (Ac-Trp-D-Cys(StBu)-OH) (Compound SP644) (42.5 mg, 0.097 mmol) and 3,4-dihydro-3-hydroxy-4-oxo-1,2,3-benzotriazine (HOObt) (9.9 mg, 60.8 mol) in NMP (0.160 mL) and a solution of diisopropylcarbodiimide (DIC) (16 µL, 0.104 mmol) in N,N-dimethylformamide (0.13 mL), after which the mixture was shaken at room temperature for 15 hours. The solid phase and the liquid phase were separated, and the resulting resin was washed with N,N-dimethylformamide (0.2 mL) four times and then with methylene chloride (0.2 mL) four times and then mixed with a 50% 2,2,2-trifluoroethanol/methylene chloride solution (0.5 mL), after which the mixture was shaken at room temperature for 2 hours. The solid phase and the liquid phase were separated, and the resulting liquid phase was concentrated under reduced pressure. The resulting residue was purified by reverse-phase silica gel column chromatography (10 mM aqueous ammonium acetate solution/methanol) to afford (S)-2-((S)-2-(((S)-1-((S)-2-((S)-2-acetamido-3-(1H-indol-3-yl)propanamido)-3-(tert-butyldisulfanyl)propanoyl)pyrrolidine-2-carbonyl)oxy)propanamido)propanoic acid (Ac-Trp-D-Cys(StBu)-Pro-Lac-Ala-OH) (Compound SP654) (SEQ ID NO: 352) (3.0 mg, 4.4 µmol, 22%).

LCMS (ESI) m/z=678 (M+H)+
Retention time: 0.86 min (analysis condition SQDAA05)

5-2. Evaluation of Reactivity of Five-Residue Model Compounds in the Translation PURESYSTEM Stability of five-residue model compounds at each pH (the compounds are desirably unreacted and stably present during primary cyclization reaction) and reaction selectivity of them at increased pHs (confirmed in reaction with mercaptoethylamine) were evaluated.
Confirmation of Reactivity of Five-Residue Model Compounds with 2-Aminoethanethiol in the Translation PURESYSTEM at pH 7.3
Stability and reaction selectivity of five-residue model compounds at pH 7.3 were evaluated.

10 mM Ac-Trp-Cys(StBu)-Pro-RRR-Ala-OH (SEQ ID NO: 353)/25% aqueous DMA (2.0 µL), 10 mM 2,4-dimethylbenzoic acid/25% aqueous DMA (2.0 µL, used as internal standard) and a 100 mM TCEP/50 mM HEPES buffer solution (pH 7.6, 2.0 µL) were mixed, and the mixture was allowed to stand at room temperature for 1 hour under a nitrogen atmosphere. Subsequently, a translation buffer (3.8 µL), PURESYSTEM® classic II Sol. B (BioComber, product No. PURE2048C) (4.0 µL), a 50 mM aqueous 1,2-dithiane-4,5-diol solution (4.2 µL) and a 500 mM 2-aminoethanethiol/50 mM HEPES buffer solution (pH 7.6, 2.0 µL) were mixed, and the mixture was allowed to stand at 37° C. under a nitrogen atmosphere. The concentrations of the respective ingredients of the translation buffer in the reaction solution are as follows. 2 mM GTP, 2 mM ATP, 1 mM CTP, 1 mM UTP, 20 mM creatine phosphate, 50 mM HEPES-KOH pH 7.6, 100 mM potassium acetate, 14 mM magnesium acetate, 2 mM spermidine, 1 mM dithiothreitol, 0.5 mg/ml E. coli MRE600 (RNase-negative)-derived tRNA (Roche), amino acids (each 0.3 mM of Ala, Cys, Phe, Gly, His, Ile, Leu, Met, Pro, Ser, Thr, Val, Trp). The progress of the reaction was confirmed by LCMS measurement. RRR represents any of $^{HO}$Gly, Lac, PhLac, D-PhLac and $^{HO}$Gly(Me)$_2$.

TABLE 13

| Entry | Substrate | | Substrate recovery | Aimoto reaction | Direct amidation | Hydrolysis |
|---|---|---|---|---|---|---|
| 1 | Cys-Pro-$^{HO}$Gly | SP646 | 45%/32% | 55%/68% | 0%/0% | 0%/0% |
| 2 | Cys-Pro-Lac | SP647 | >99%/95% | <1%/5% | 0%/0% | 0%/0% |
| 3 | Cys-Pro-PhLac | SP648 | 96%/90% | 4%/10% | 0%/0% | 0%/0% |
| 4 | Cys-Pro-D-PhLac | SP649 | 92%/87% | 8%/13% | 0%/0% | 0%/0% |
| 5 | Cys-Pro-$^{HO}$Gly(Me)$_2$ | SP650 | 100%/100% | 0%/0% | 0%/0% | 0%/0% |
| 6 | Cys-MeGly-$^{HO}$Gly | SP651 | Separately described | Separately described | Separately described | Separately described |
| 7 | D-Cys-MeGly-$^{HO}$Gly | SP652 | Separately described | Separately described | Separately described | Separately described |
| 8 | D-Cys-Pro-$^{HO}$Gly | SP653 | 0%/0% | 0%/0% | 100%/100% | 0%/0% |
| 9 | D-Cys-Pro-Lac | SP654 | 89%/81% | 0%/0% | 11%/19% | 0%/0% |

(Yield at 8 h/yield at 24 h), the yield is determined by the UV area ratio for LC In the above table, "substrate" indicates a Cys-Pro-RRR site in the center of the five-residual model Ac-Trp-Cys-Pro-RRR-Ala-OH (SEQ ID NO: 260) (part of the table also describes examples where D-cys is used in place of Cys or MeGly is used in place of Pro). "Substrate recovery" indicates a total of the percentages of Ac-Trp-Cys-Pro-RRR-Ala-OH (SEQ ID NO: 260), Ac-Trp-Cys(SCH$_2$CH$_2$NH$_2$)-Pro-RRR-Ala-OH (SEQ ID NO: 261), which is disulfide-bond formed substrate with 2-mercaptoethylamine at Cys site, and Ac-Trp-Cys(SCH$_2$COCH$_2$CH$_2$SH)-Pro-RRR-Ala-OH (SEQ ID NO: 262) or Ac-Trp-Cys(SCH$_2$CH$_2$COCH$_2$SH)-Pro-RRR-Ala-OH (SEQ ID NO: 263), which is disulfide-bond formed substrate at Cys site with 1,4-di-mercaptobutane-2-one assumed to be a dehydrate of dithiothreitol (DTT) contained in the reaction system. Specifically, this is a total of the compounds in which the basic backbones of the main chains are still maintained. "Aimoto reaction" indicates a total of percentages of Ac-Trp-NHCH$_2$CH$_2$SH obtained by reacting a thioester resulting from a five-residue model with 2-mercaptoethylamine, and its disulfide-bond formed compound with 2-mercaptoethylamine, Ac-Trp-NHCH$_2$CH$_2$SSCH$_2$CH$_2$NH$_2$. "Direct amidation" indicates a total of percentages of Ac-Trp-Cys-Pro-NHCH$_2$CH$_2$SH resulting from side reaction, a product obtained by disulfide-bonding and cyclizing at * in Ac-Trp-Cys*-Pro-NHCH$_2$CH$_2$S*, and Ac-Trp-Cys(SCH$_2$CH$_2$NH$_2$)-Pro-NHCH$_2$CH$_2$SSCH$_2$CH$_2$NH$_2$. "Hydrolysis" indicates a percentage of Ac-Trp-OH, which was formed by the reaction of a generated thioester from, a five-residue model with water in place of 2-mercaptoethylamine.

Accordingly, when primary cyclization reaction is assumed to be carried out at a designated pH, higher percentage of the substrate recovery is desired. When secondary cyclization reaction is assumed to be carried out at a designated pH, higher percentage of the Aimoto reaction is desired.

For Entry 6 and Entry 7 of Table 13, the UV area ratio is not calculated due to the overlapping of retention times between peaks, and the mass intensity ratios (negative mode) of the respective compounds are as follows.

Entry 6
 (8 hours) Substrate recovery: 27%, Aimoto reaction: 39%, direct amidation: 33%, hydrolysis: 0%
 (24 hours) Substrate recovery: 13%, Aimoto reaction: 31%, direct amidation: 56%, hydrolysis: 0%

Entry 7
 (8 hours) Substrate recovery: 12%, Aimoto reaction: 50%, direct amidation: 38%, hydrolysis: 0%
 (24 hours) Substrate recovery: 0%, Aimoto reaction: 50%, direct amidation: 50%, hydrolysis: 0%

Confirmation of Reactivity of Five-Residue Model Compounds with 2-Aminoethanethiol in the Translation PURESYSTEM at pH 7.8

10 mM Ac-Trp-Cys(StBu)-Pro-RRR-Ala-OH (SEQ ID NO: 353)/25% aqueous DMA (5.0 μL), 10 mM 4-pentylbenzoic acid/25% aqueous DMA (5.0 μL, used as internal standard) and a 100 mM TCEP/50 mM HEPES buffer solution (pH 7.6, 5.0 μL) were mixed, the cysteine residue side chain protecting group was quickly deprotected, and the mixture was allowed to stand at room temperature for 1 hour under a nitrogen atmosphere. Subsequently, a translation buffer (9.5 μL), PURESYSTEM® classic II Sol. B (BioComber, product No. PURE2048C) (10 μL), a 50 mM aqueous 1,2-dithiane-4,5-diol solution (10.5 μL) and a 500 mM 2-aminoethanethiol/50 mM HEPES buffer solution (pH 7.6, 5.0 μL) were mixed, the reaction solution was adjusted to pH 7.8 by further mixing with a 1 N aqueous sodium hydroxide solution (1.0 μL), and the mixture was allowed to stand at 37° C. under a nitrogen atmosphere. The concentrations of the respective ingredients of the translation buffer in the reaction solution are as follows. 2 mM GTP, 2 mM ATP, 1 mM CTP, 1 mM UTP, 20 mM creatine phosphate, 50 mM HEPES-KOH pH 7.6, 100 mM potassium acetate, 14 mM magnesium acetate, 2 mM spermidine, 1 mM dithiothreitol, 0.5 mg/ml E. coli MRE600 (RNase-negative)-derived tRNA (Roche), amino acids (each 0.3 mM of Ala, Cys, Phe, Gly, His, Ile, Leu, Met, Pro, Ser, Thr, Val, Trp). The progress of the reaction was confirmed by LCMS measurement.

TABLE 14

| Entry | Substrate | | Substrate recovery | Aimoto reaction | Direct amidation | Hydrolysis |
|---|---|---|---|---|---|---|
| 1 | Cys-Pro-$^{HO}$Gly | SP646 | 10%/2% | 85%/92% | 5%/7% | 0%/0% |
| 2 | Cys-Pro-Lac | SP647 | 93%/84% | 7%/16% | 0%/0% | 0%/0% |

(Yield at 8 h/yield at 24 h), the yield is determined by the UV area ratio for LC As already shown in Example, when Cys-Pro-$^{HO}$Gly was used, primary cyclization using Cys and Asp(SBn) was highly selective. However, the above results revealed that Cys-Pro-$^{HO}$Gly at around pH=7.8, which was used for primary cyclization (it can be understood as follows: Cys-Pro-$^{HO}$Gly had reaction selectivity as a result of sufficiently rapid primary cyclization reaction when an amino group with a reaction auxiliary group was used). To enhance selectivity, that is, to generate a thioester not in primary reaction but in secondary reaction, it was found that increasing steric hindrance of a site close to the ester as Cys-Pro-Lac is preferred.

Confirmation of Reactivity of Five-Residue Model Compounds with 2-Aminoethanethiol in a Buffer at pH 8.5

10 mM Ac-Trp-Cys(StBu)-Pro-RRR-Ala-OH (SEQ ID NO: 353)/25% aqueous DMA (5.0 μL), 10 mM 4-pentylbenzoic acid/25% aqueous DMA (5.0 μL, used as internal standard) and a 100 mM TCEP/50 mM HEPES buffer solution (pH 7.8, 5.0 μL) were mixed, the cysteine residue side chain protecting group was quickly deprotected, and the mixture was allowed to stand at room temperature for 1 hour under a nitrogen atmosphere. Subsequently, 100 mM bicine buffer (pH 8.9, 19.5 μL), a 50 mM 1,2-dithiane-4,5-diol/100 mM bicine buffer (pH 8.9, 10.5 μL) and a 500 mM 2-aminoethanethiol/100 mM bicine buffer solution (pH 8.5, 5.0 μL) were mixed, the reaction solution was adjusted to pH 8.5 by further mixing with a 0.5 N aqueous sodium hydroxide solution (1.0 μL), and the mixture was allowed to stand at 37° C. or 57° C. under a nitrogen atmosphere. The progress of the reaction was confirmed by LCMS measurement.

TABLE 15

At 37° C. for 24 h

| Entry | Substrate | | Substrate recovery | Aimoto reaction | Hydrolysis | Others |
|---|---|---|---|---|---|---|
| 1 | Cys-Pro-Lac | SP647 | 31% | 55% | 6% | 8% |
| 2 | Cys-Pro-PhLac | SP648 | 17% | 75% | 2% | 5% |
| 3 | Cys-Pro-D-PhLac | SP649 | 6% | 89% | 0% | 5% |

The yield is determined by the UV area ratio for LC.

TABLE 16

At 57° C. for 24 h

| Entry | Substrate | | Substrate recovery | Aimoto reaction | Hydrolysis | Others |
|---|---|---|---|---|---|---|
| 1 | Cys-Pro-Lac | SP647 | 0% | 84% | 7% | 8% |
| 2 | Cys-Pro-PhLac | SP648 | 0% | 90% | 5% | 5% |
| 3 | Cys-Pro-D-PhLac | SP649 | 0% | 94% | 0% | 5% |

The yield is determined by the UV area ratio for LC.

It was found that in the case of Cys-Pro-Lac and Cys-Pro-PhLac, increasing pH to 8.5 generates a thioester selectively and allows a desired reaction to proceed selectively against hydrolysis in a translation solution. Reaction could be avoided at pH 7.8 and a desired reaction could be allowed to proceed at pH 8.5.

Confirmation of Reactivity of Five-Residue Model Compounds with 2-Aminoethanethiol in a Buffer at pH 9.0

10 mM Ac-Trp-Cys(StBu)-Pro-RRR-Ala-OH (SEQ ID NO: 353)/25% aqueous DMA (5.0 µL), 10 mM 4-pentylbenzoic acid/25% aqueous DMA (5.0 µL, used as internal standard) and a 100 mM TCEP/50 mM HEPES buffer solution (pH 7.8, 5.0 µL) were mixed, the cysteine residue side chain protecting group was quickly deprotected, and the mixture was allowed to stand at room temperature for 1 hour under a nitrogen atmosphere. Subsequently, 100 mM bicine buffer (pH 8.9, 19.5 µL), a 50 mM 1,2-dithiane-4,5-diol/100 mM bicine buffer (pH 8.9, 10.5 µL) and a 500 mM 2-aminoethanethiol/100 mM bicine buffer solution (pH 8.5, 5.0 µL) were mixed, the reaction solution was adjusted to pH 9.0 by further mixing with a 0.5 N aqueous sodium hydroxide solution (2.0 µL), and the mixture was allowed to stand at 37° C. or 57° C. under a nitrogen atmosphere. The progress of the reaction was confirmed by LCMS measurement.

TABLE 17

At 37° C. for 24 h

| Entry | Substrate | | Substrate recovery | Aimoto reaction | Hydrolysis | Others |
|---|---|---|---|---|---|---|
| 1 | Cys-Pro-Lac | SP647 | 5% | 82% | 8% | 5% |
| 2 | Cys-Pro-PhLac | SP648 | 5% | 87% | 3% | 5% |
| 3 | Cys-Pro-D-PhLac | SP649 | 0% | 95% | 0% | 5% |

The yield is determined by the UV area ratio for LC.

TABLE 18

At 57° C. for 24 h

| Entry | Substrate | | Substrate recovery | Aimoto reaction | Hydrolysis | Others |
|---|---|---|---|---|---|---|
| 1 | Cys-Pro-Lac | SP647 | 0% | 91% | 6% | 3% |
| 2 | Cys-Pro-PhLac | SP648 | 0% | 90% | 5% | 5% |
| 3 | Cys-Pro-D-PhLac | SP649 | 0% | 95% | 0% | 5% |

The yield is determined by the UV area ratio for LC.

It was shown that desired branching is also possible for peptide-RNA complexes using the present conditions because RNA stably exists and does not decomposed even at pH 9.0 as previously described in Examples.

5-3. Establishment of Chemical Reaction Conditions for Examples where the First Cyclization was the Amide Cyclization Between Triangle Unit Having Reaction Auxiliary Group at the N-Terminal and Active Thioester (Intersection Unit) in the Side Chain of the Amino Acid at the C-Terminal, and Protected Amino Groups Having Reaction Auxiliary Groups are Subjected to Deprotection Reaction and Active Esters are then Generated from Cys-Pro-Lac and Branched by Reaction with Side Chain Amino Groups in Secondary Branching 5-3-1. Synthesis of a Translated Peptide Model Compound SP655

Figure 101:
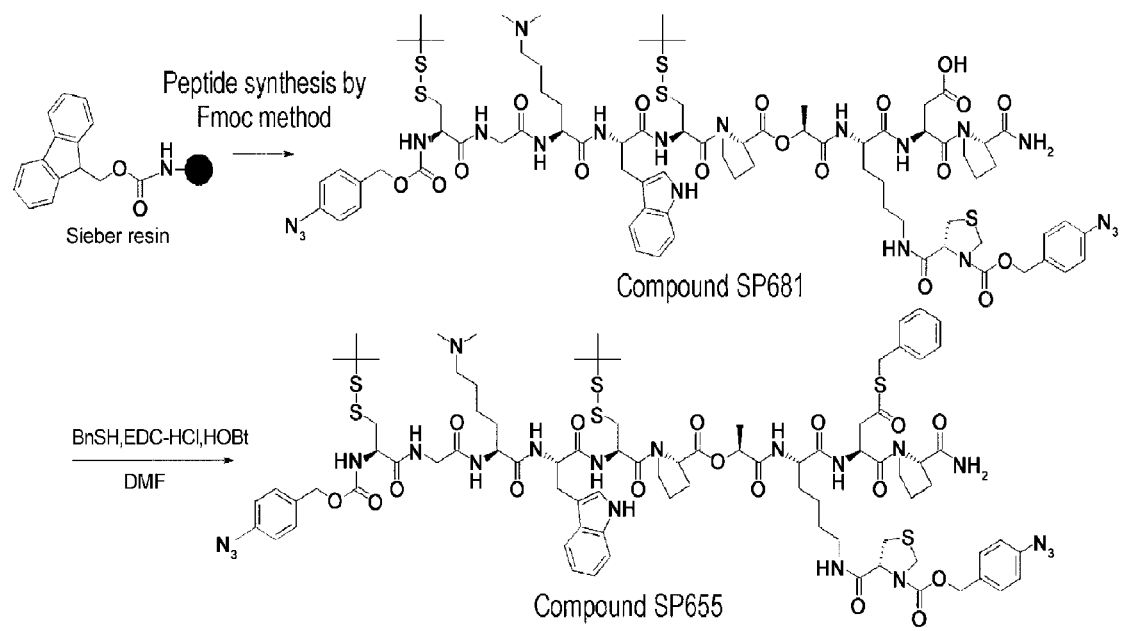
FIG. 101 is a diagram showing the synthesis of a translated peptide model compound SP655.

The following model compound SP655 was synthesized according to the following scheme in order to implement an example where amidation cyclization reaction is carried out using Cys at the N-terminal and Asp(SBn) on the C-terminal side in primary cyclization, and amidation reaction is carried out by deprotecting the S and N atoms of a compound which has Cys-Pro-Lac as an active thioester generation part and in which Cys having N and S atoms protected is located at the side chain amino group of Lys in secondary branching. See FIG. 101.

Synthesis of (S)-3-((S)-2-((S)-2-((S)-1-((6R,12S,15S,18R)-15-((1H-indol-3-yl)methyl)-6-((4-azidobenzyloxy)carbonylamino)-18-((tert-butyldisulfanyl)methyl)-12-(4-(dimethylamino)butyl)-2,2-dimethyl-7,10,13,16-tetraoxo-3,4-dithia-8,11,14,17-tetraazanonadecanepyrrolidine-2-carbonyloxy)propanamido)-6-((R)-3-((4-azidobenzyloxy)carbonyl)thiazolidine-4-carboxamido)hexanamido)-4-((S)-2-carbamoylpyrrolidin-1-yl)-4-oxobutanoic Acid (Compound SP681, Acbz-Cys(StBu)-Gly-Lys(Me$_2$)-Trp-Cys(StBu)-Pro-Lac-Lys(Acbz-Thz)-Asp-Pro-NH2) (SEQ ID NO: 264)

In the present specification, a compound amidated between amino group at side chain of Lys and the carboxylic group having Acbz-Thz moiety is described as Lys(Acbz-Thz).

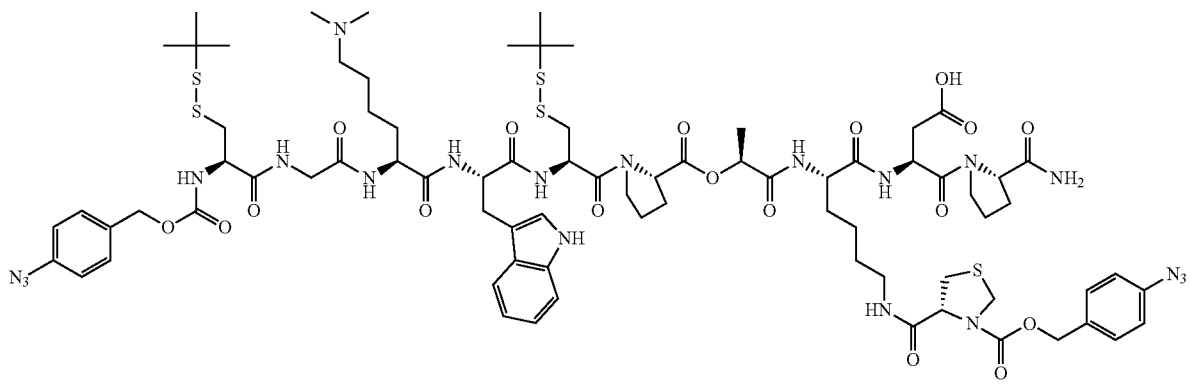 [SMILES: C[C@H](OC(=O)[C@@H]1CCCN1C(=O)[C@H](CSSC(C)(C)C)NC(=O)[C@H](Cc1c[nH]c2ccccc12)NC(=O)[C@H](CCCCN(C)C)NC(=O)CNC(=O)[C@H](CSSC(C)(C)C)NC(=O)OCc1ccc(N=[N+]=[N-])cc1)C(=O)N[C@@H](CCCCNC(=O)[C@@H]1CSCN1C(=O)OCc1ccc(N=[N+]=[N-])cc1)C(=O)N[C@@H](CC(=O)O)C(=O)N1CCC[C@H]1C(N)=O]

Peptide chain elongation was carried out according to the general method for solid-phase synthesis of peptides containing ester groups in the main chains by automatic synthesizers as previously described in Examples. Sieber Amide Resin (160 mg per column, purchased from Novabiochem) was used as the resin. Peptide elongation was carried out using Acbz-Cys(StBu)-OH as N-terminal amino acid and Fmoc-Gly-OH, Fmoc-Lys(Me₂)—OH·HCl, Fmoc-Trp-Cys(StBu)-OH (Compound SP602), Fmoc-Pro-Lac-OH (Compound SP633), Fmoc-Lys(Acbz-Thz)-OH (Compound SP611), Fmoc-Asp(OPis)-OH and Fmoc-Pro-OH as Fmoc amino acids.

After the peptide elongation, the resin was washed with dimethylformamide (DMF) and dichloromethane (DCM). The peptide was cleaved from the resin by adding a 2% solution of trifluoroacetic acid (TEA) in dichloromethane (DCM)/2,2,2-trifluoroethanol (TFE) (=1/1, v/v, 4.0 ml) to the resin and reacting for 3 hours at room temperature. After completion of the reaction, the solution in the tube was filtered through a synthesis column to remove the resin, and the resin was washed with dichloromethane (DCM)/2,2,2-trifluoroethanol (TFE) (=1/1, v/v, 4.0 mL) four times. The resulting solution was concentrated under reduced pressure, and the residue was purified by reverse-phase silica gel chromatography (0.1% aqueous formic acid solution/0.1% formic acid-acetonitrile solution) to afford (S)-3-((S)-2-((S)-2-((S)-1-((6R,12S,15S,18R)-15-((1H-indol-3-yl)methyl)-6-((4-azidobenzyloxy)carbonylamino)-18-((tert-butyldisulfanyl)methyl)-12-(4-(dimethylamino)butyl)-2,2-dimethyl-7,10,13,16-tetraoxo-3,4-dithia-8,11,14,17-tetraazanonadecanepyrrolidine-2-carbonyloxy)propanamido)-6-((R)-3-((4-azidobenzyloxy)carbonyl)thiazolidine-4-carboxamido)hexanamido)-4-((S)-2-carbamoylpyrrolidin-1-yl)-4-oxobutanoic acid (Acbz-Cys(StBu)-Gly-Lys(Me₂)-Trp-Cys(StBu)-Pro-Lac-Lys(Acbz-Thz)-Asp-Pro-NH2) (Compound SP681) (SEQ ID NO: 264) (184.6 mg, 24%).

LCMS (ESI) m/z=1773.9 (M+H)+
Retention time: 0.76 min (analysis condition SQDFA05)

Synthesis of (R)-4-Azidobenzyl 4-(((S)-5-((S)-2-(((S)-1-((6R,12S,15S,18R)-15-((1H-indol-3-yl)methyl)-6-((((4-azidobenzyl)oxy)carbonyl)amino)-18-((tert-butyldisulfanyl)methyl)-12-(4-(dimethylamino)butyl)-2,2-dimethyl-7,10,13,16-tetraoxo-3,4-dithia-8,11,14,17-tetraazanonadecan-19-oyl)pyrrolidine-2-carbonyl)oxy)propanamido)-6-(((S)-4-(benzylthio)-1-((S)-2-carbamoylpyrrolidin-1-yl)-1,4-dioxobutan-2-yl)amino)-6-oxohexyl)carbamoyl)thiazolidine-3-carboxylate (Compound SP655, Acbz-Cys(StBu)-Gly-Lys(Me₂)-Trp-Cys(StBu)-Pro-Lac-Lys(Acbz-Thz)-Asp(SBn)-Pro-NH2)
(SEQ ID NO: 265)

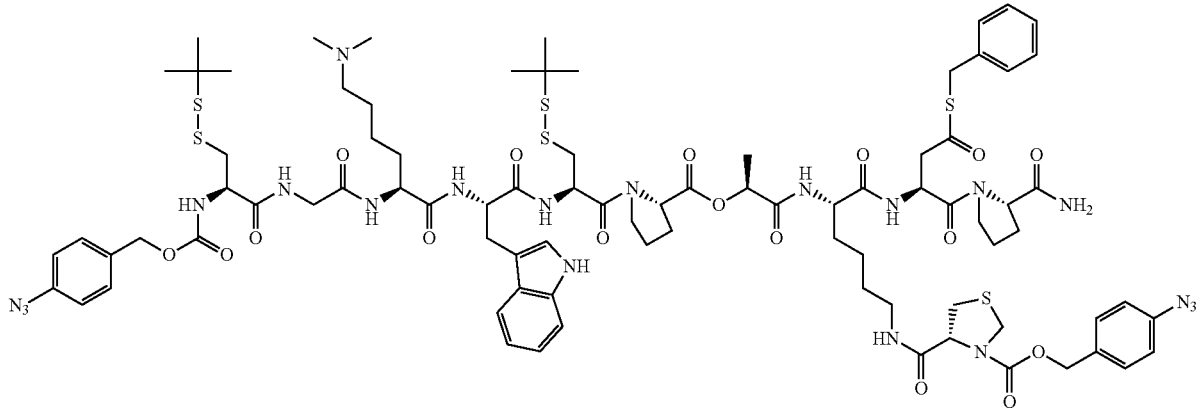 [SMILES: C[C@H](OC(=O)[C@@H]1CCCN1C(=O)[C@H](CSSC(C)(C)C)NC(=O)[C@H](Cc1c[nH]c2ccccc12)NC(=O)[C@H](CCCCN(C)C)NC(=O)CNC(=O)[C@H](CSSC(C)(C)C)NC(=O)OCc1ccc(N=[N+]=[N-])cc1)C(=O)N[C@@H](CCCCNC(=O)[C@@H]1CSCN1C(=O)OCc1ccc(N=[N+]=[N-])cc1)C(=O)N[C@@H](CC(=O)SCc1ccccc1)C(=O)N1CCC[C@H]1C(N)=O]

A solution of (S)-3-((S)-2-((S)-2-((S)-1-((6R,12S,15S,18R)-15-((1H-indol-3-yl)methyl)-6-((4-azidobenzyloxy)carbonylamino)-18-((tert-butyldisulfanyl)methyl)-12-(4-(dimethylamino)butyl)-2,2-dimethyl-7,10,13,16-tetraoxo-3,4-dithia-8,11,14,17-tetraazanonadecanepyrrolidine-2-carbonyloxy)propanamido)-6-((R)-3-((4-azidobenzyloxy)carbonyl)thiazolidine-4-carboxamido)hexanamido)-4-((S)-2-carbamoylpyrrolidin-1-yl)-4-oxobutanoic acid (Compound SP681, Acbz-Cys(StBu)-Gly-Lys(Me₂)-Trp-Cys(StBu)-Pro-Lac-Lys(Acbz-Thz)-Asp-Pro-NH2) (SEQ ID NO: 264) (102 mg, 0.057 mmol) and HOBt (23.2 mg, 0.172 mmol) in DMF (0.6 ml) was cooled to 0° C., after which 1-(3-dimethylaminopropyl)-3-ethylcarbodiimide hydrochloride (EDC·HCl, 32.9 mg, 0.172 mmol) was added, the mixture was stirred for 5 minutes, and benzylmercaptane (34 μl, 0.286 mmol) was then added. The reaction solution was stirred at room temperature for 70 minutes and purified by reverse phase silica gel column chromatography (0.1% aqueous formic acid solution/0.1% formic acid-acetonitrile solution) to afford the title compound (Compound SP655, Acbz-Cys(StBu)-Gly-Lys(Me₂)-Trp-Cys(StBu)-Pro-Lac-Lys(Acbz-Thz)-Asp(SBn)-Pro-NH2) (SEQ ID NO: 265) (75.7 mg, 70%).

LCMS (ESI) m/z=1880.0 (M+H)+
Retention time: 0.80 min (analysis condition SQDFA05)

5-4. Cyclization by NCL Reaction and Subsequent Branch-Forming Reaction Using a Linear Model Peptide Having Cys-Pro-Lac in the Sequence in the Translation PURESYSTEM It was found that a Cys-Pro-Lac unit can stably exist irrespective of the presence or absence of a reaction auxiliary group during primary cyclization reaction, and can achieve with high selectivity during secondary branching reaction. Therefore, branching reaction in a translation solution was confirmed using a model peptide.

Figure 68:
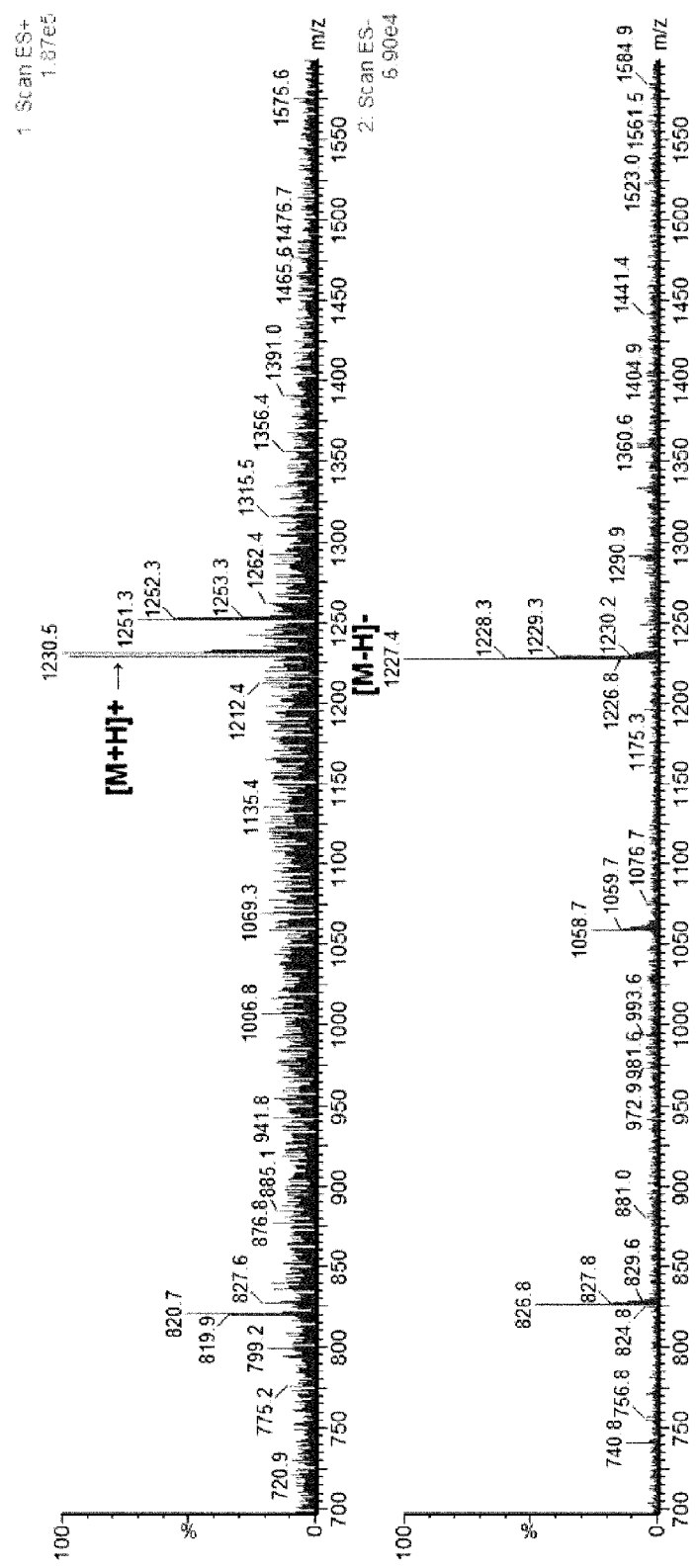
FIG. 68 is a mass chromatogram obtained by integrating and averaging mass chromatograms in the entire range of LCMS.

First Step: Reaction of Producing Compound SP656 by Cyclization of a Linear Model Peptide (Compound SP655, Acbz-Cys(StBu)-Gly-Lys(Me₂)-Trp-Cys(StBu)-Pro-Lac-Lys (Acbz-Thz)-Asp(SBn)-Pro-NH₂) (SEQ ID NO: 265) by NCL Reaction A 54 mM (R)-4-azidobenzyl 4-(((S)-5-((S)-2-(((S)-1-((6R,12S,15S,18R)-15-((1H-indol-3-yl)methyl)-6-((((4-azidobenzyl)oxy)carbonyl)amino)-18-((tert-butyldisulfanyl)methyl)-12-(4-(dimethylamino)butyl)-2,2-dimethyl-7,10,13,16-tetraoxo-3,4-dithia-8,11,14,17-tetraazanonadecan-19-oyl)pyrrolidine-2-carbonyl)oxy)propanamido)-6-(((S)-4-(benzylthio)-1-((S)-2-carbamoylpyrrolidin-1-yl)-1,4-dioxobutan-2-yl)amino)-6-oxohexyl)carbamoyl) thiazolidine-3-carboxylate (Compound SP655, Acbz-Cys(StBu)-Gly-Lys(Me₂)-Trp-Cys(StBu)-Pro-Lac-Lys(Acbz-Thz)-Asp(SBn)-Pro-NH₂ (SEQ ID NO: 265))/DMA solution (9.4 μL), a 54 mM 2,4-dimethylbenzoic acid/DMA solution (9.4 μL, used as internal standard), a translation buffer (6.3 μL), PURE SYSTEM® classic II Sol. B (BioComber, product No. PURE2048C) (10 μL), 20 natural amino acid solutions (2.5 μL) and 1.0 M TCEP (12.5 μL, pH 7.5) were mixed, and the mixture was allowed to stand at 25° C. for 2 hours. The ingredients of the translation buffer are 8 mM GTP, 8 mM ATP, 160 mM creatine phosphate, 400 mM HEPES-KOH, pH 7.6, 800 mM potassium acetate, 48 mM magnesium acetate, 16 mM spermidine, 8 mM dithiothreitol, 0.8 mM 10-HCO—H4 folate and 12 mg/mi E. coli MRE600 (RNase negative)-derived tRNA (Roche). The reaction solution was measured by LCMS to confirm that the intended cyclized compound, (R)—N-(4-((3S,6S,9S,13R,19S,22S,25R,30aS)-22-((1H-indol-3-yl)methyl)-9-((S)-2-carbamoylpyrrolidine-1-carbonyl)-19-(4-(dimethylamino)butyl)-13,25-bis(mercaptomethyl)-3-methyl-1,4,7,11,14,17,20,23,26-nonaoxooctacosahydro-1H-pyrrolo[2,1-c][1,4,7,10,13,16,19,23,26]oxaoctaazacyclooctacosyn-6-yl)butyl) thiazolidine-4-carboxamide (Compound SP656, a compound cyclized at * in *Cys-Gly-Lys(Me2)-Trp-Cys-Pro-Lac-Lys(Thz)-Asp*-Pro-NH₂ (SEQ ID NO: 266)), was produced (FIG. 68).

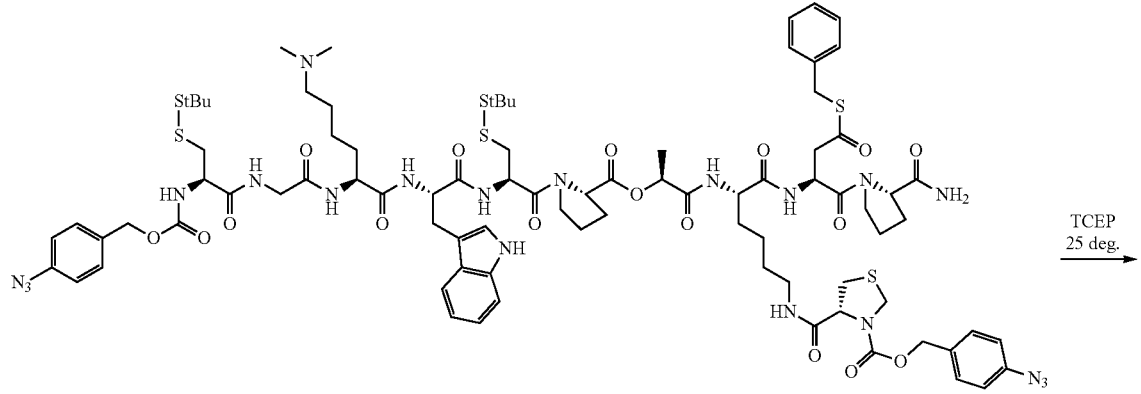

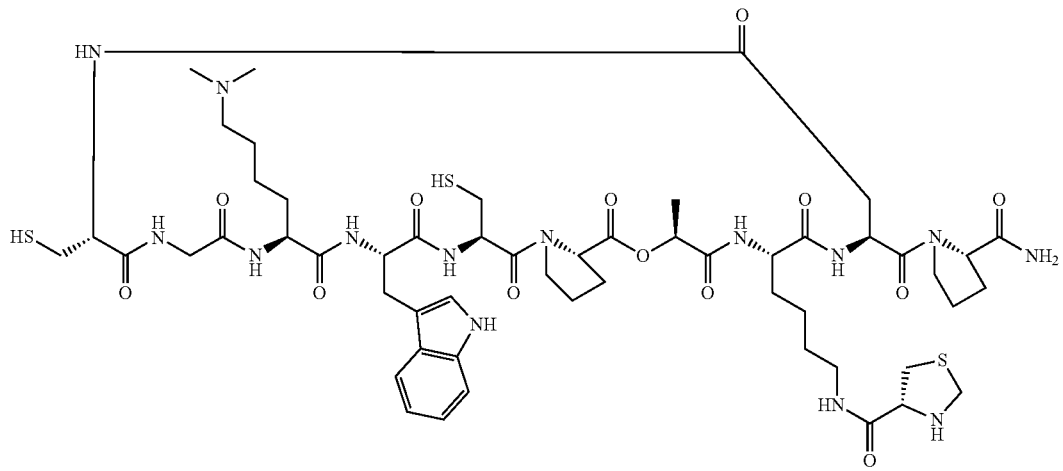

LCMS (ESI) m/z=1227 (M−H)−

Retention time: 0.76 min (analysis condition SQDAA05)

Second Step: Reaction of Producing Compound SP657 by Deprotection Reaction of Thz of Compound SP656

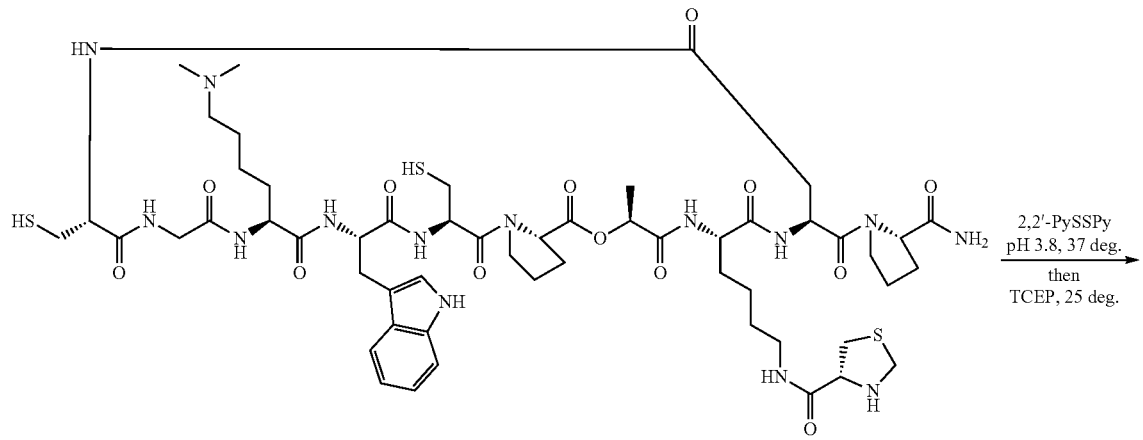

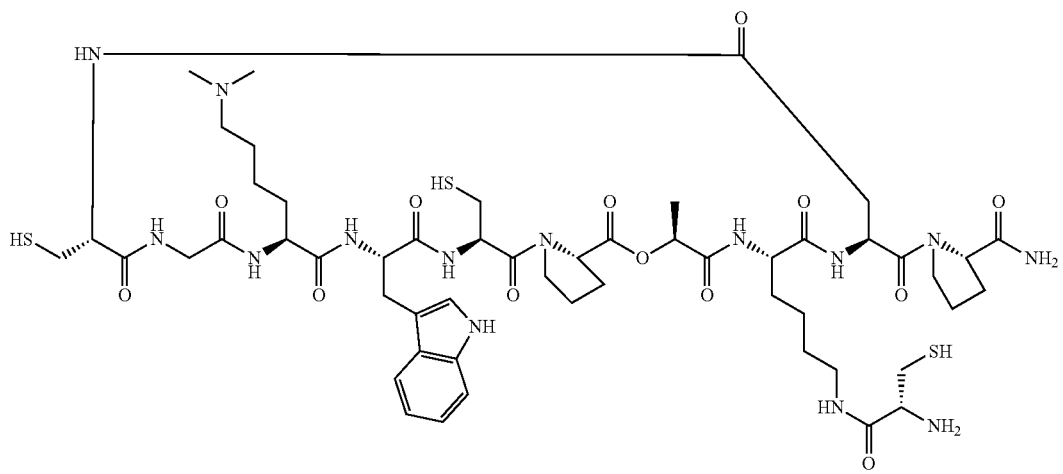

The resulting reaction mixture of cyclized Compound SP656 by NCL (the above reaction mixture, 25 μL), DMA (25 μL), and a 6.7 M 1,2-di(pyridin-2-yl)disulfane/DMA solution (15 μL) were mixed, and the mixture was adjusted to pH 3.8 with 5 N hydrochloric acid and allowed to stand at 37° C. for 15 hours. Subsequently, 25 μL of the reaction mixture was withdrawn, mixed with a 1.25 M aqueous TCEP solution (50 μL, pH 7.5) and allowed to stand at 25° C. for 3 hours. The reaction solution was measured by LCMS to confirm that a compound having a Thz site deprotected, (S)-1-((3S,6S,9S,13R,19S,22S,25R,30aS)-22-((1H-indol-3-yl)methyl)-6-(4-NR)-2-amino-3-mercaptopropanamide)butyl)-19-(4-(dimethylamino)butyl)-13,25-bis (mercaptomethyl)-3-methyl-1,4,7,11,14,17,20,23,26-nonaoxooctacosahydro-1H-pyrrolo[2,1-c][1,4,7,10,13,16,19,23,26]oxaoctaazacyclooctacosyne-9-carbonyl) pyrrolidine-2-carboxamide (Compound SP657, a compound cyclized at * in *Cys-Gly-Lys(Me')-Trp-Cys-Pro-Lac-Lys (H-Cys)-Asp*-Pro-NH$_2$ (SEQ ID NO: 267)), was produced.

Figure 69:
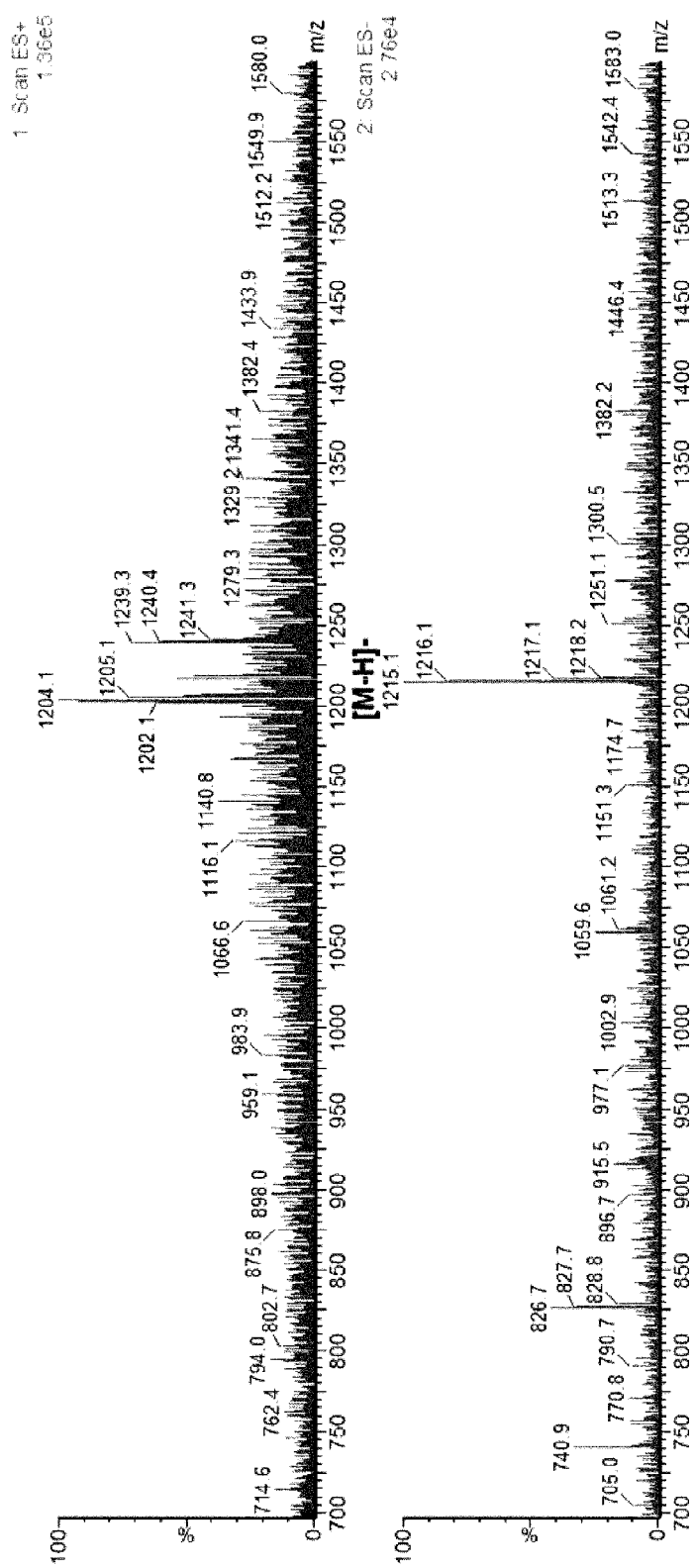
FIG. 69 is a mass chromatogram obtained by integrating and averaging mass chromatograms in the entire range of LCMS.

LCMS (ESI) m/z=1215 (M−H)−(FIG. 69)

Retention time: 0.73 min (analysis condition SQDAA05)

Third Step: Reaction of Producing Compound SP658 by Branch-Forming Reaction of the Cyclic Peptide of Compound SP657

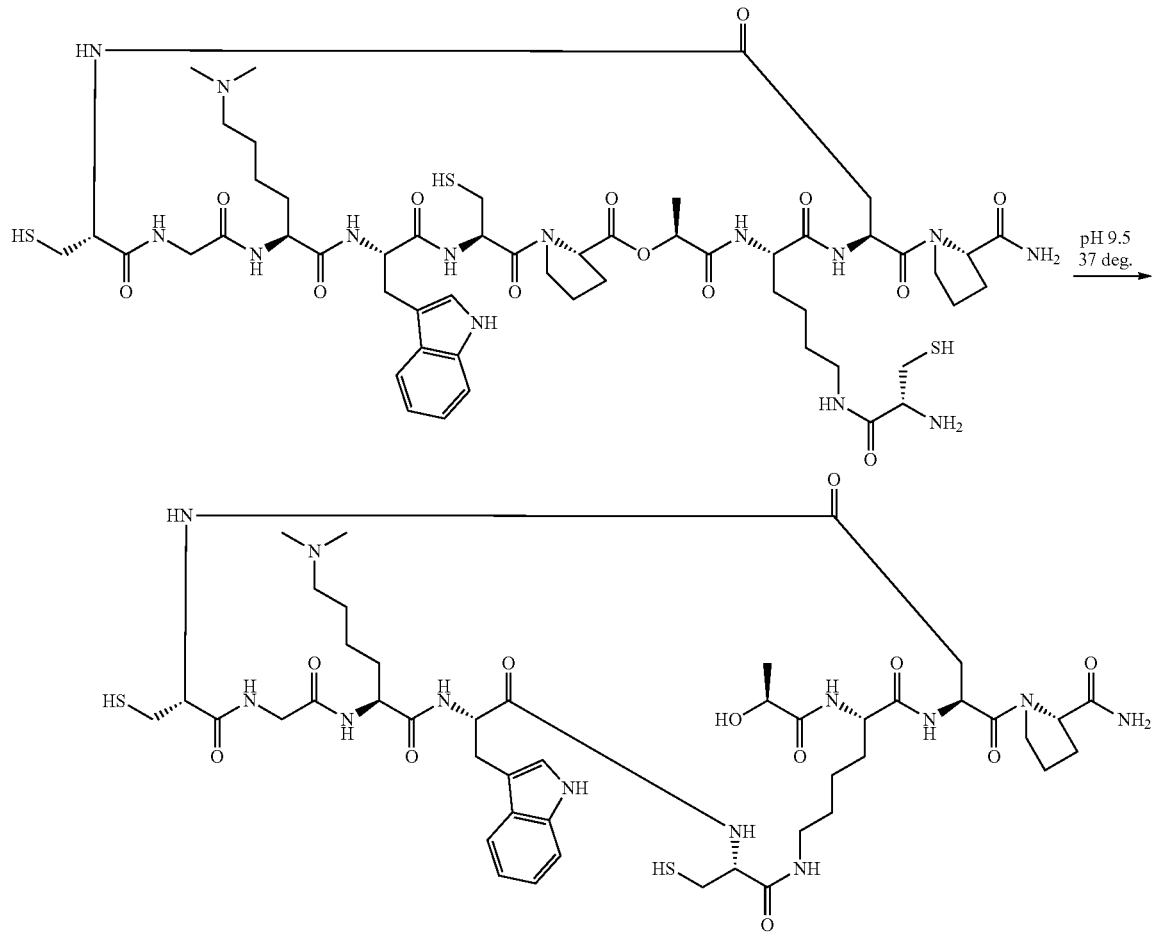

The resulting reaction mixture of Compound SP657, which was obtained by Thz deprotection of SP656 and subsequent disulfide reduction, (the above reaction mixture, 25 µL) and 2.0 M bicine buffer (pH 8.7, 30 µL) were mixed, and the reaction mixture was adjusted to pH 9.5 with a 5 N aqueous sodium hydroxide solution and allowed to stand at 37° C. for 4 hours. The reaction solution was measured by LCMS to confirm that a branch-formed cyclic peptide, (S)-1-((3R,6S,9S,15R,19S,22S)-6-((1H-indol-3-yl)methyl)-9-(4-(dimethylamino)butyl)-22-((S)-2-hydroxypropanamide)-3,15-bis(mercaptomethyl)-2,5,8,11,14,17,21-heptaoxo-1,4,7,10,13,16,20-heptaazacyclohexacosane-19-carbonyl)pyrrolidine-2-carboxamide (Compound SP658, a compound cyclized at * in H-Lac-Lys(*Cys-Gly-Lys(Me₂)-Trp-Cys)-Asp*-Pro-NH₂ (SEQ ID NO: 268)), was produced.

LCMS (ESI) m/z=1017 (M+H)+

Figure 70:
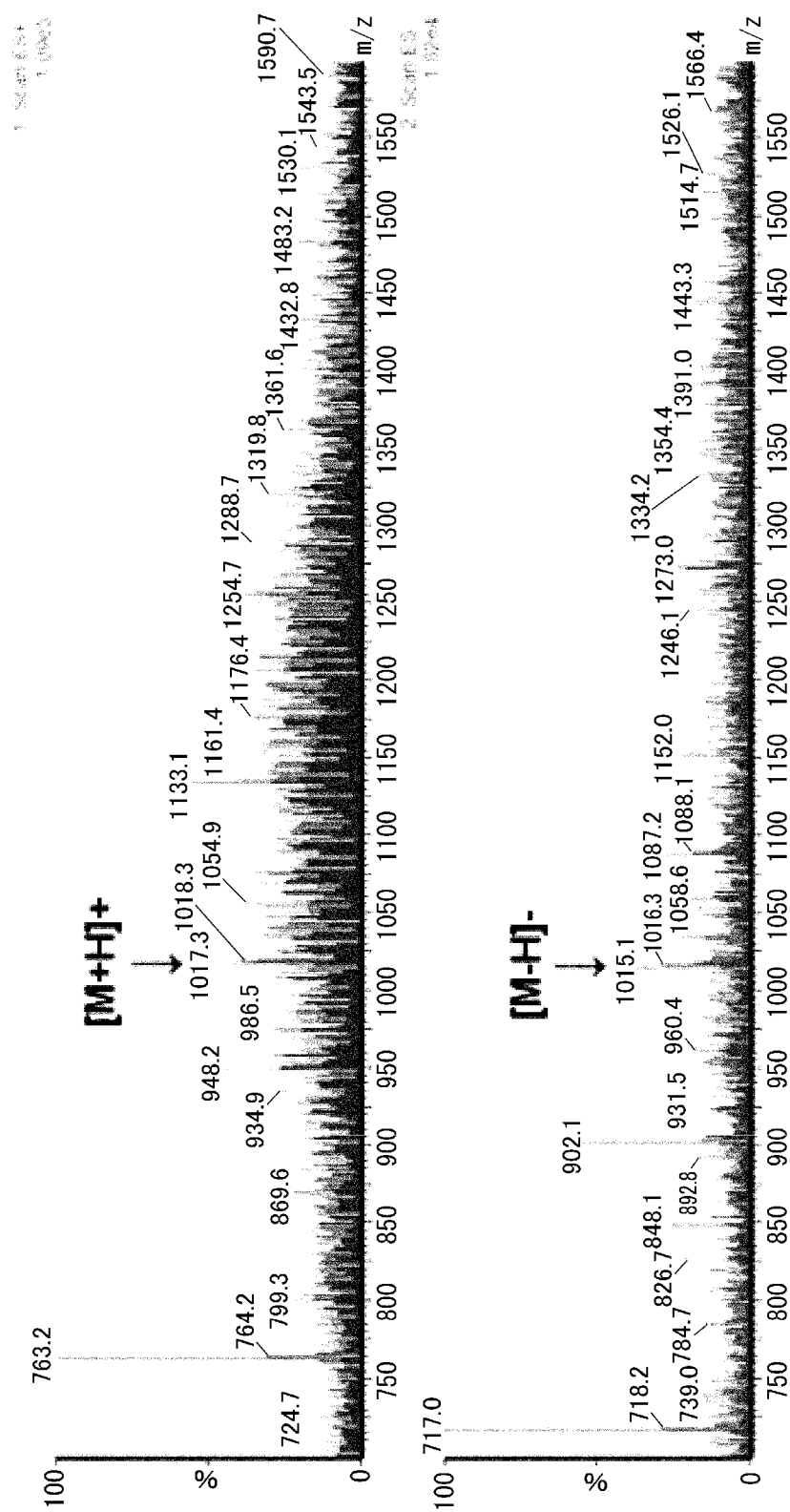
FIG. 70 is a mass chromatogram obtained by integrating and averaging mass chromatograms in the entire range of LCMS.

Retention time: 0.65 minute (analysis condition SQDAA05) (FIG. 70)

6. Implementation of an Example where an Active Ester Generated from Cys-Pro-$^{HO}$Gly is Reacted with a Deprotected Amino Group to Form a Branched Peptide in Secondary Branching, Assuming that Primary Cyclization has been Completed This is another experiment for demonstrating the concept of secondary branching. This experiment is performed assuming that primary cyclization has been completed. Accordingly, a main chain-cyclized model compound was prepared without amide cyclization between the carboxylic acid in the side chain of Asp and the amino group at the N-terminal. The following model reaction was carried out in which an active ester was generated from Cys-Pro-$^{HO}$Gly and the protected amine was deprotected and branched before or after the generation in secondary branching.

6-1. Synthesis of a Translated Peptide Model Compound SP662

The synthesis was carried out according to the following scheme.

Figure 102:
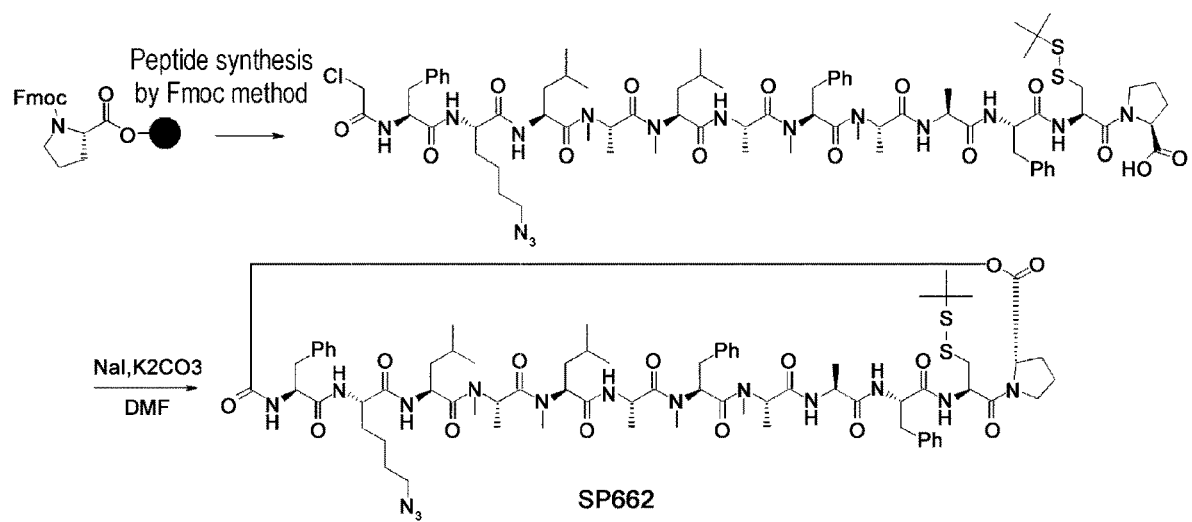
FIG. 102 is a diagram showing the synthesis of a translated peptide model compound SP662.

See FIG. 102.

Synthesis of (5S,8R)-5-benzyl-1-(9H-fluoren-9-yl)-12,12-dimethyl-3,6-dioxo-2-oxa-10,11-dithia-4,7-diazatridecane-8-carboxylic Acid (Compound SP663, Fmoc-Phe-Cys(StBu)-OH)

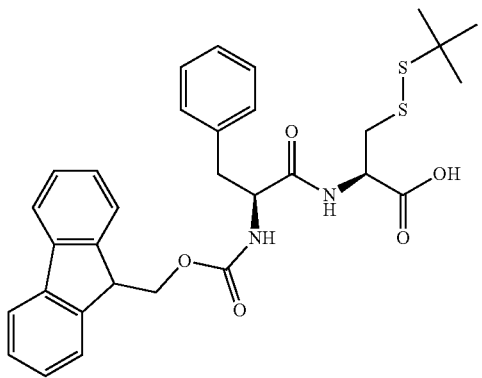 [SMILES: CC(C)(C)SSC[C@H](NC(=O)[C@H](Cc1ccccc1)NC(=O)OCC1c2ccccc2-c2ccccc21)C(=O)O]

A solution of Fmoc-Phe-OH (4 g, 10.32 mmol) and N-hydroxysuccinimide (1.19 g, 10.32 mmol) in dichloromethane (20 ml) was cooled to 0° C., after which 1-(3-dimethylaminopropyl)-3-ethylcarbodiimide hydrochloride (EDC·HCl, 1.98 g, 10.32 mmol) was added and the reaction solution was stirred at room temperature for 6 hours. The reaction solution was cooled to 0° C., after which N,N-diisopropylethylamine (1.80 ml, 10.23 mmol) and S-(t-butylthio)-L-cysteine (H-Cys(StBu)-OH) (2.16 g, 10.32 mmol) were added and the reaction solution was stirred at room temperature for 12 hours. Ethyl acetate and 2 M hydrochloric acid were added to the reaction mixture, followed by extraction with ethyl acetate. The organic layer was washed with 25 wt % brine and dried over sodium sulfate. The resulting solution was concentrated under reduced pressure, and the concentration residue was purified by reverse-phase silica gel column chromatography (0.1% aqueous formic acid solution/0.1% formic acid-acetonitrile solution) to afford (5S,8R)-5-benzyl-1-(9H-fluoren-9-yl)-12,12-dimethyl-3,6-dioxo-2-oxa-10,11-dithia-4,7-diazatridecane-8-carboxylic acid (Compound SP663, Fmoc-Phe-Cys(StBu)-OH) (4.22 g, 71%).

LCMS (ESI) m/z=579 (M+H)+
Retention time: 0.97 min (analysis condition SQD FA05)

Synthesis of (6S,9S,12S,15S,18S,21S,24S,27S,30S,33S,36R,41aS)-9-(4-azidobutyl)-6,24,33-tribenzyl-36-((tert-butyldisulfanyl)methyl)-12,18-diisobutyl-14,15,17,21,23,26,27,30-octamethyl hexacosahydropyrrolo[2,1-c][1,4,7,10,13,16,19,22,25,28,31,34,37]oxadodecaazacyclon onatriacontyne-1,4,7,10,13,16,19,22,25,28,31,34,37(3H)-tridecone (Compound SP662, c($^{HO}$Gly-Phe-Lys(N3)-Leu-MeAla-MeLeu-Ala-MePhe-MeAla-Ala-Phe-Cys(StBu)-Pro)) (SEQ ID NO: 269)

($^{HO}$Gly represents glycolic acid.)

Definition of Terms

Fmoc-Lys(N3)-OH: (S)-2-(((9H-Fluoren-9-yl)methoxy)carbonylamino)-6-azidohexanoic acid

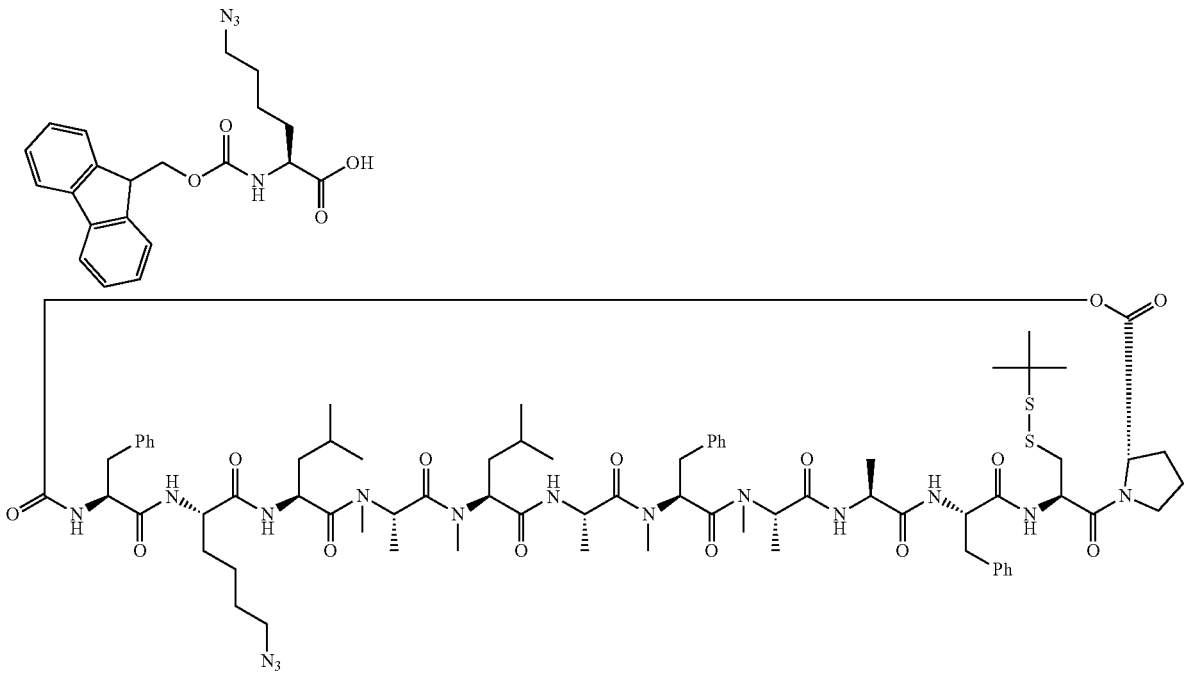 [SMILES: [N-]=[N+]=NCCCC[C@H](NC(=O)OCC1c2ccccc2-c2ccccc21)C(=O)O ; CC(C)C[C@@H]1NC(=O)[C@H](CCCCN=[N+]=[N-])NC(=O)[C@H](Cc2ccccc2)NC(=O)COC(=O)[C@@H]2CCCN2C(=O)[C@H](CSSC(C)(C)C)NC(=O)[C@H](Cc2ccccc2)NC(=O)[C@H](C)NC(=O)[C@H](C)N(C)C(=O)[C@H](Cc2ccccc2)N(C)C(=O)[C@H](C)NC(=O)[C@H](CC(C)C)N(C)C(=O)[C@H](C)N(C)C1=O]

Peptide elongation was carried out using Fmoc-MePhe-OH, Fmoc-MeAla-OH, Fmoc-MeLeu-OH, Fmoc-Lys(N3)-OH, Fmoc-Phe-OH, Fmoc-Ala-OH, Fmoc-Leu-OH, Fmoc-Phe-Cys(StBu)-OH (Compound SP663) as Fmoc amino acids. Following the peptide elongation, the Fmoc group at the N-terminal was deprotected, chloroacetic acid was condensed using HOAt and DIC as condensing agents, and the resin was then washed with DMF and dichloromethane. The peptide was cleaved from the resin by adding dichloromethane/2,2,2-trifluoroethanol (=1/1, v/v, 4 mL) to the resin and reacting for 1 hour. After completion of the reaction, the solution in the tube was filtered through a synthesis column to remove the resin, and the resin was washed with dichloromethane/2,2,2-trifluoroethanol (=1/1, v/v, 1 mL). The resulting solution was concentrated under reduced pressure to afford a crude product, ((S)-1-((2R,5S,8S,11S,14S,17S,20S,23S,26S,29S,32S)-29-(4-azidobutyl)-5,14,32-tribenzyl-2-((tert-butyldisulfanyl)methyl)-35-chloro-20,26-diisobutyl-8,11,12,15,17,21,23,24-octamethyl-4,7,10,13,16,19,22,25,28,31,34-undecaoxo-3,6,9,12,15,18,21,24,27,30,33-undecaazapentatriacontane)pyrrolidine-2-carboxylic acid (ClAc-Phe-Lys(N3)-Leu-MeAla-MeLeu-Ala-MePhe-MeAla-Ala-Phe-Cys(StBu)-Pro) (SEQ ID NO: 270) (419 mg). Potassium carbonate (56.2 mg, 0.407 mmol) was added to a solution of the resulting crude product (ClAc-Phe-Lys(N3)-Leu-MeAla-MeLeu-Ala-MePhe-MeAla-Ala-Phe-Cys(StBu)-Pro) (SEQ ID NO: 270) (419 mg, 0.271 mmol) and sodium iodide (102 mg, 0.678 mmol) in DMF (20 ml) and THF (20 ml) under a nitrogen atmosphere, and the reaction solution was stirred at 40° C. for 5.5 hours. The reaction solution was concentrated under reduced pressure, and the resulting residue was purified by reverse-phase silica gel column chromatography (0.1% aqueous formic acid solution/0.1% formic acid-acetonitrile solution) to afford the title compound (Compound SP662, 158 mg, 39%).

LCMS (ESI) m/z=1509 (M+H)+

Retention time: 0.63 min (analysis condition SQD FA50)

6-2. Reaction of Producing an Intramolecular Branched Peptide from the Translated Model Peptide Synthesis of (S)—N-((3S,6S,9S,12S,15S,18S,21S,24S,27S)-3,12-dibenzyl-18,24-diisobutyl-6,9,10,13,15,19,21,22-octamethyl-2,5,8,11,14,17,20,23,26-nonaoxo-1,4,7,10,13,16,19,22,25-nonaazacyclohentriacontan-27-yl)-2-(2-hydroxyacetamide)-3-phenylpropanamide (Compound SP664)

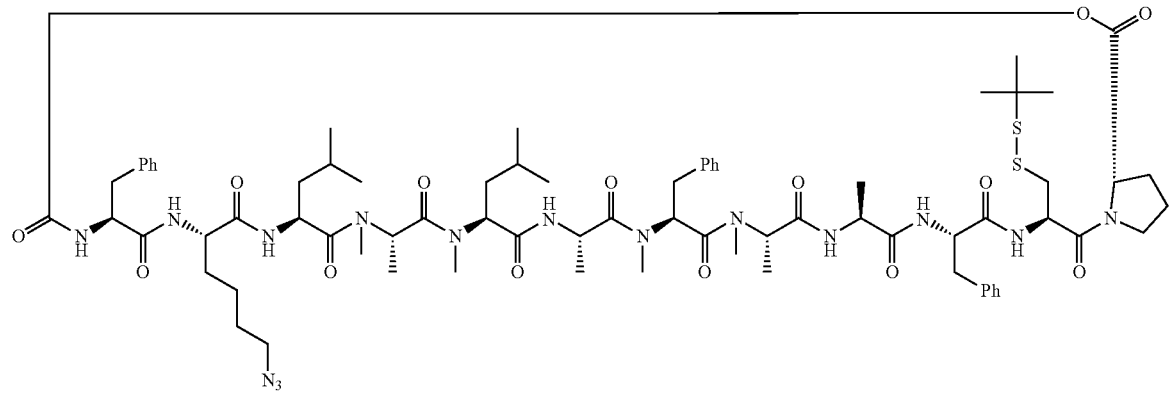

Compound SP662

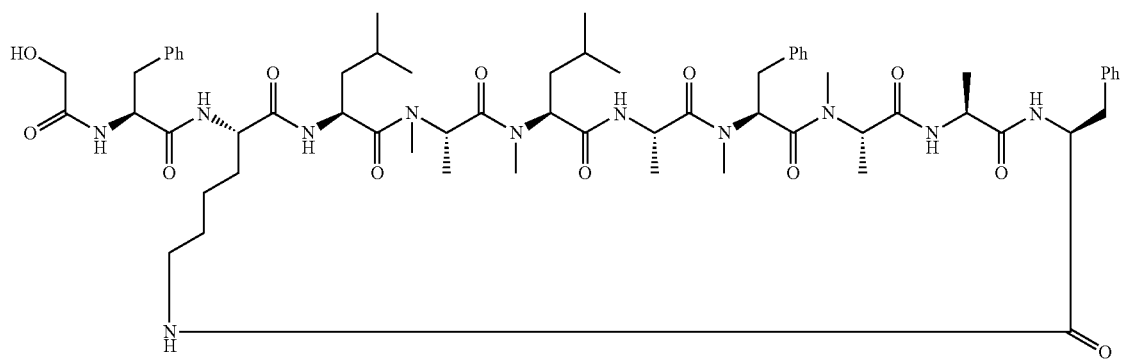

Compound SP664

2309

Intramolecular Branched Peptide Forming Reaction in a Buffer

Figure 71:
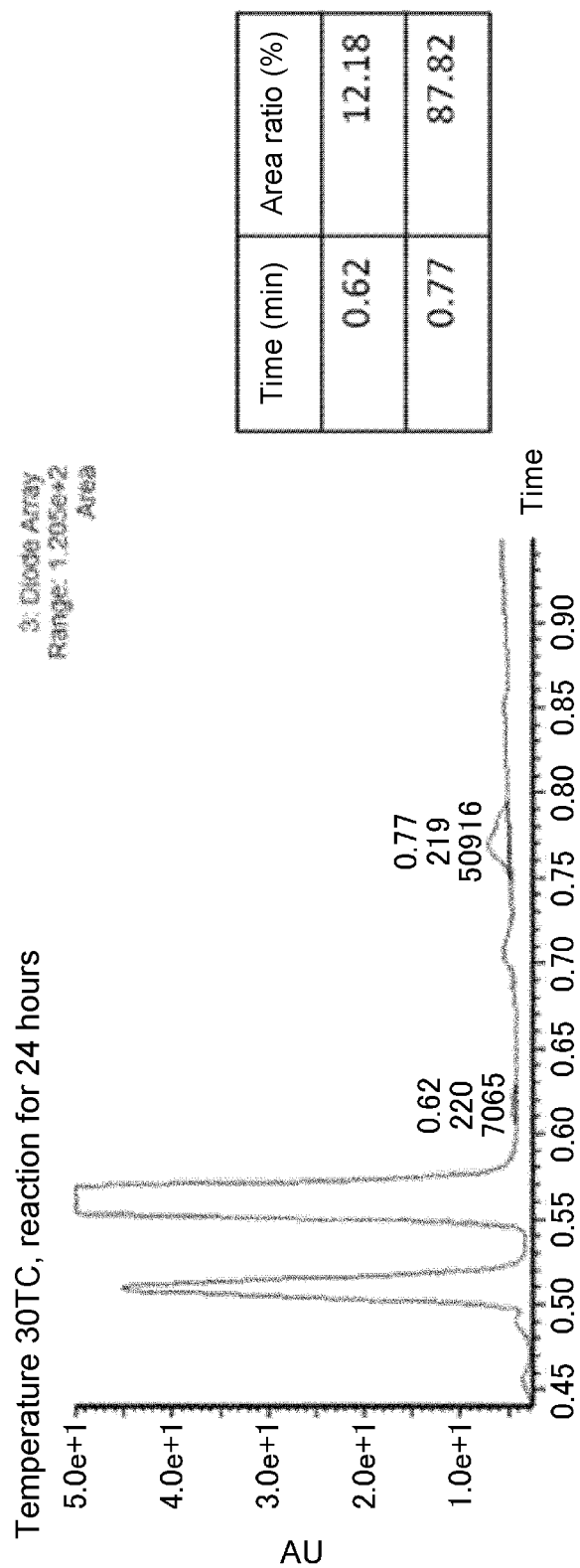
FIG. 71 is a diagram showing LCMS analysis results of a reaction solution containing produced compound SP664.

TCEP hydrochloride (tris(2-carboxyethyl)phosphine hydrochloride) (2.9 mg, 0.010 mmol) and 2-(4-mercaptophenyl)acetic acid (1.7 mg, 0.010 mmol) were added to a mixed solution of 0.5 M HEPES buffer (pH 7.0, 60 µl) and 1,3-dimethyl-2-imidazolidinone (DMI) (40 µl). Further, this solution was adjusted to pH 8.5 by adding a 2 N aqueous sodium hydroxide solution (35 µl) and water (45 µl) thereto, and the mixture was stirred at room temperature for 5 minutes. A 0.01 M solution of (6S,9S,12S,15S,18S,21S,24S, 27S,30S,33S,36R,41aS)-9-(4-azidobutyl)-6,24,33-tribenzyl-36-((tert-butyldisulfanyl)methyl)-12,18-diisobutyl-14, 15,17,21,23,26,27,30-octamethylhexacosahydropyrrolo[2, 1-c][1,4,7,10,13,16,19,22,25,28,31,34,37] oxadodecaazacyclon onatriacontyne-1,4,7,10,13,16,19,22, 25,28,31,34,37(3H)-tridecone (c($^{HO}$Gly-Phe-Lys(N3)-Leu-MeAla-MeLeu-Ala-MePhe-MeAla-Ala-Phe-Cys(StBu)-Pro)) (Compound SP662) (SEQ ID NO: 269) in 1,3-dimethyl-2-imidazolidinone (DMI) (20 µl, 0.2 µmol) was then added, and the reaction solution was stirred at 30° C. for 24 hours. The change in the reaction was observed by LCMS to confirm that (S)—N-((3S,6S,9S,12S,15S,18S,21S,24S, 27S)-3,12-dibenzyl-1,24-diisobutyl-6,9,10,13,15,19,21,22-octamethyl-2,5,8,11,14,17,20,23,26-nonaoxo-1,4,7,10,13, 16,19,22,25-nonaazacyclohentriacontan-27-yl)-2-(2-hydroxyacetamide)-3-phenylpropanamide (Compound SP664) was produced at 24 hours. The production ratio of the hydrolysate and Compound SP664 was 12:88 based on the UV area ratio by LCMS (FIG. 71, retention time of the hydrolyzed compound: 0.62 min).

LCMS (ESI) m/z=1195 (M+H)+

Retention time: 0.77 min (analysis condition SQD FA05)

7. Implementation of an Example where an Active Ester is Directly Generated from an Ester Having a Reaction Auxiliary Group and Branched by Amidation Reaction of the (Protected) Amino Group in Secondary Branching Reaction, Assuming that Primary Cyclization Reaction has been Completed This is another experiment for concept demonstration. The experiment was assumed to be performed after completion of primary cyclization reaction. Accordingly, the side chain carboxylic acid of Asp and the N-terminal amine were not cyclized, but the carboxylic acid of the C-terminal Ala and the N-terminal amine were amide-cyclized. The protecting group for the amino group for secondary branching reaction is not assumed for use in a display library. The experiment is a model experiment for concept demonstration to confirm that branching reaction from an ester having a reaction auxiliary group can proceed.

7-1. Synthesis of a Translated Peptide Model Compound (Compound 665)

The synthesis was carried out according to the following scheme.

See FIGS. 103-1 and 103-2.

2310

Synthesis of 3-(tert-butyldisulfanyl)-2-hydroxypropanoic Acid (Compound SP666, H-tBuSSlac-OH)

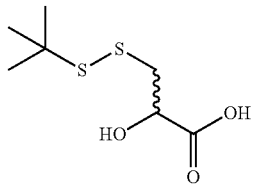

A 1 N aqueous hydrochloric acid solution (300 µL) was added to a solution of 2-(tert-butyldimethylsilyloxy)-3-(tert-butyldisulfanyl)propionic acid prepared by the method known in the literature (J. Am. Chem. Soc. 2008, 130, 4919) (Compound 24) (30.0 mg, 0.092 mol) in tetrahydrofuran (THF) (300 µl) at room temperature, and the mixture was stirred at 60° C. for 16 hours. The reaction solution was purified by Reverse-phase silica-gel chromatography (0.1% aqueous formic acid solution/0.1% formic acid-acetonitrile solution) to afford 3-(tert-butyldisulfanyl)-2-hydroxypropanoic acid (H-tBuSSlac-OH) (Compound SP666) (7.4 mg, 54%).

In the present specification, a divalent structure from Compound SP666 in which the hydrogen atom on the hydroxyl group and the hydroxyl group on the carboxylic acid are removed is called tBuSSlac.

LCMS (ESI) m/z=209 (M−H)−

Retention time: 0.60 min (analysis condition SQDFA05)

Synthesis of 2-(((S)-2-((((9H-fluoren-9-yl)methoxy) carbonyl)amino)-3-phenylpropanoyl)oxy)-3-(tert-butyldisulfanyl)propanoic Acid (Fmoc-Phe-tBuS-Slac-OH) (Compound SP667)

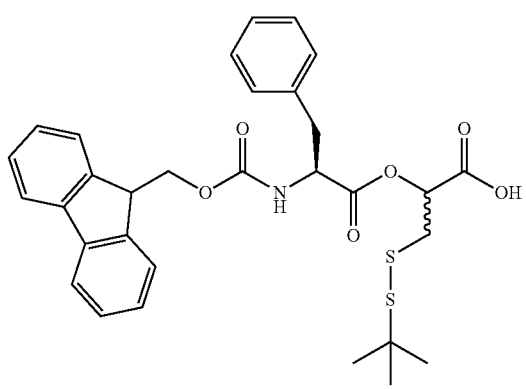 [SMILES: CC(C)(C)SSCC(OC(=O)[C@H](Cc1ccccc1)NC(=O)OCC1c2ccccc2-c2ccccc21)C(=O)O]

1-Ethyl-3-(3-dimethylaminopropyl)carbodiimide hydrochloride (EDCI·HCl) (247 mg, 1.29 mmol) was added to a solution of (S)-2-((((9H-fluoren-9-yl)methoxy)carbonyl) amino)-3-phenylpropanoic acid (Fmoc-Phe-OH) (500 mg, 1.29 mmol) and N-hydroxysuccinimide (HOSu) (149 mg, 1.29 mmol) in dimethylformamide (DMF) (4.5 ml) at room temperature under a nitrogen atmosphere, and the mixture was stirred at the same temperature for 18 hours. 3-(tert-Butyldisulfanyl)-2-hydroxypropanoic acid (Compound SP666) (100 mg, 0.475 mmol) and 4-dimethylaminopyridine (DMAP) (58.1 mg, 0.475 mmol) were added to the reaction solution (1.7 ml) at room temperature, and the mixture was stirred at the same temperature for 5 hours. Formic acid (18 μl) was added to the reaction solution, and the mixture was purified by reverse-phase silica gel chromatography (0.1% aqueous formic acid solution/0.1% formic acid-acetonitrile solution) to afford 2-(((S)-2-((((9H-fluoren-9-yl)methoxy)carbonyl)amino)-3-phenylpropanoyl)oxy)-3-(tert-butyldisulfanyl)propanoic acid (Fmoc-Phe-tBuSSlac-OH) (Compound SP667) (110 mg, 40%).

LCMS (ESI) m/z=580.5 (M+H)+
Retention time: 1.05 min (analysis condition SQDFA05)

Synthesis of (5S,11S,14S,17S,20S,23S,26S,29S, 32S,35S)-14-(4-((R)-2-(((allyloxy)carbonyl)amino)-3-(tert-butyldisulfanyl)propanamide)butyl)-5,11,29-tribenzyl-8-((tert-butyldisulfanyl)methyl)-1-(9H-fluoren-9-yl)-17,23-diisobutyl-19,20,22,26,28,31,32, 35-octamethyl-3,6,9,12,15,18,21,24,27,30,33-undecaoxo-2,7-dioxa-4,10,13,16,19,22,25,28,31,34-decaazahexatriacontan-36-oic Acid (Fmoc-Phe-tBuSSlac-Phe-Lys(Alloc-Cys(StBu))-Leu-MeAla-MeLeu-Ala-MePhe-MeAla-Ala-OH) (Compound SP668) (SEQ ID NO: 354)

In the present specification, a compound amidated between the amino group at side chain of H-Lys-OH and the carboxyl group of Alloc-Cys(StBu)-OH is described as H-Lys(Alloc-Cys(StBu))-OH like in other examples.

romethane (DCM)/2,2,2-trifluoroethanol (TFE) (=1/1, v/v, 1 mL) four times. The resulting solution was concentrated under reduced pressure to afford (2S,5S,8S,11S,14S,17S, 20S,23S,30R)-23-((S)-2-amino-3-phenylpropanamide)-8-benzyl-30-((tert-butyldisulfanyl)methyl)-14,20-diisobutyl-2,5,6,9,11,15,17,18-octamethyl-4,7,10,13,16,19,22,29,32-nonaoxo-33-oxa-3,6,9,12,15,18,21,28,31-nonaazahexatriacont-35-en-1-oic acid (H-Phe-Lys(Alloc-Cys(StBu))-Leu-MeAla-MeLeu-Ala-MePhe-MeAla-Ala-OH) (Compound SP669) (SEQ ID NO: 271) (71.0 mg) as a crude product.

1-Ethyl-3-(3-dimethylaminopropyl)carbodiimide hydrochloride (EDCI·HCl) (3.31 mg, 17 μmol) was added to a solution of 2-(((S)-2-((((9H-fluoren-9-yl)methoxy)carbonyl)amino)-3-phenylpropanoyl)oxy)-3-(tert-butyldisulfanyl)propanoic acid (Fmoc-Phe-tBuSSlac-OH) (Compound SP667) (10.0 mg, 17 μmol) and N-hydroxysuccinimide (HOSu) (1.99 mg, 17 μmol) in dimethylformamide (DMF) (100 μl) at room temperature under a nitrogen atmosphere, and the mixture was stirred at the same temperature for 15 hours. A solution of (2S,5S,8S,11S,14S,17S,20S,23S,30R)-23-((S)-2-amino-3-phenylpropanamide)-8-benzyl-30-((tert-butyldisulfanyl)methyl)-14,20-diisobutyl-2,5,6,9,11,15,17, 18-octamethyl-4,7,10,13,16,19,22,29,32-nonaoxo-33-oxa-3,6,9,12,15,18,21,28,31-nonaazahexatriacont-35-en-1-oic acid (H-Phe-Lys(Alloc-Cys(StBu))-Leu-MeAla-MeLeu-Ala-MePhe-MeAla-Ala-OH) (Compound SP669) (SEQ ID

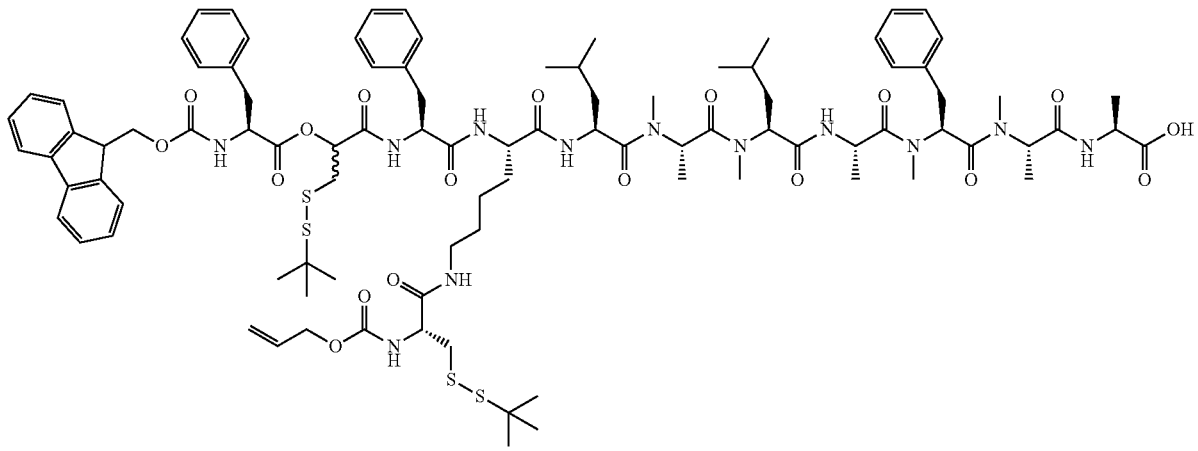 [SMILES: C=CCOC(=O)N[C@@H](CSSC(C)(C)C)C(=O)NCCCC[C@H](NC(=O)[C@H](Cc1ccccc1)NC(=O)C(CSSC(C)(C)C)OC(=O)[C@H](Cc1ccccc1)NC(=O)OCC1c2ccccc2-c2ccccc21)C(=O)N[C@@H](CC(C)C)C(=O)N(C)[C@@H](C)C(=O)N(C)[C@@H](CC(C)C)C(=O)N[C@@H](C)C(=O)N(C)[C@@H](Cc1ccccc1)C(=O)N(C)[C@@H](C)C(=O)N[C@@H](C)C(=O)O]

H-Phe-Lys(Alloc-Cys(StBu))-Leu-MeAla-MeLeu-Ala-MePhe-MeAla-Ala-OH (Compound SP669) (SEQ ID NO: 271) was synthesized by the Fmoc method as previously described in Example. Cl-Trt(2-Cl)-Resin (100-200 mesh, 1% DVB, purchased from Watanabe Chemical Industries) was used as the resin. Fmoc-Ala-OH, Fmoc-MeAla-OH, Fmoc-MePhe-OH, Fmoc-MeLeu-OH, Fmoc-Leu-OH, Fmoc-Lys(Alloc-Cys(StBu))—OH (Compound 150a) and Fmoc-Phe-OH were used as Fmoc amino acids. Following the peptide elongation, the Fmoc group at the N-terminal was deprotected with a 20% solution of piperidine in dimethylformamide (DMF) (4.0 ml), and the resin was washed with dimethylformamide (DMF). The peptide was cleaved from the resin by adding dichloromethane (DCM)/2,2,2-trifluoroethanol (TFE) (=1/1, v/v, 4.0 ml) to the resin and reacting for 1 hour. After completion of the reaction, the solution in the tube was filtered through a synthesis column to remove the resin, and the resin was washed with dichlo- NO: 271) (22.1 mg) in dimethylformamide (DMF) (220 μl) and diisopropylethylamine (DIPEA) (3.01 μl, 17 μmol) were added to the reaction solution at room temperature, and the mixture was stirred at 30° C. for 3 hours and 30 minutes.

The reaction solution was purified by reverse-phase silica gel chromatography (10 mM aqueous ammonium acetate solution/methanol) to afford (5S,11S,14S,17S,20S,23S,26S, 29S,32S,35S)-14-(4-((R)-2-(((allyloxy)carbonyl)amino)-3-(tert-butyldisulfanyl)propanamide)butyl)-5,11,29-tribenzyl-8-((tert-butyldisulfanyl)methyl)-1-(9H-fluoren-9-yl)-17,23-diisobutyl-19,20,22,26,28,31,32,35-octamethyl-3,6,9,12,15, 18,21,24,27,30,33-undecaoxo-2,7-dioxa-4,10,13,16,19,22, 25,28,31,34-decaazahexatriacontan-36-oic acid (Fmoc-Phe-tBuSSlac-Phe-Lys(Alloc-Cys(StBu))-Leu-MeAla-MeLeu-Ala-MePhe-MeAla-Ala-OH) (Compound SP668) (SEQ ID NO: 272) (17.0 mg, 54%).

LCMS (ESI) m/z=1844.6 (M+H)+
Retention time: 0.84 min (analysis condition SQDAA50)

Synthesis of (9S,12S,15S,18S,21S,24S,27S,30S,33S)-12-(4-((R)-2-(((allyloxy)carbonyl)amino)-3-(tert-butyldisulfanyl)propanamide)butyl)-6-(((S)-2-amino-3-phenylpropanoyl)oxy)-9,27-dibenzyl-15,21-diisobutyl-2,2,17,18,20,24,26,29,30,33-decamethyl-7,10,13,16,19,22,25,28,31-nonaoxo-3,4-dithia-8,11,14,17,20,23,26,29,32-nonaazatetratriacontan-34-oic Acid (H-Phe-tBuSSlac-Phe-Lys(Alloc-Cys(StBu))-Leu-MeAla-MeLeu-Ala-MePhe-MeAla-Ala-OH) (Compound SP670) (SEQ ID NO: 273)

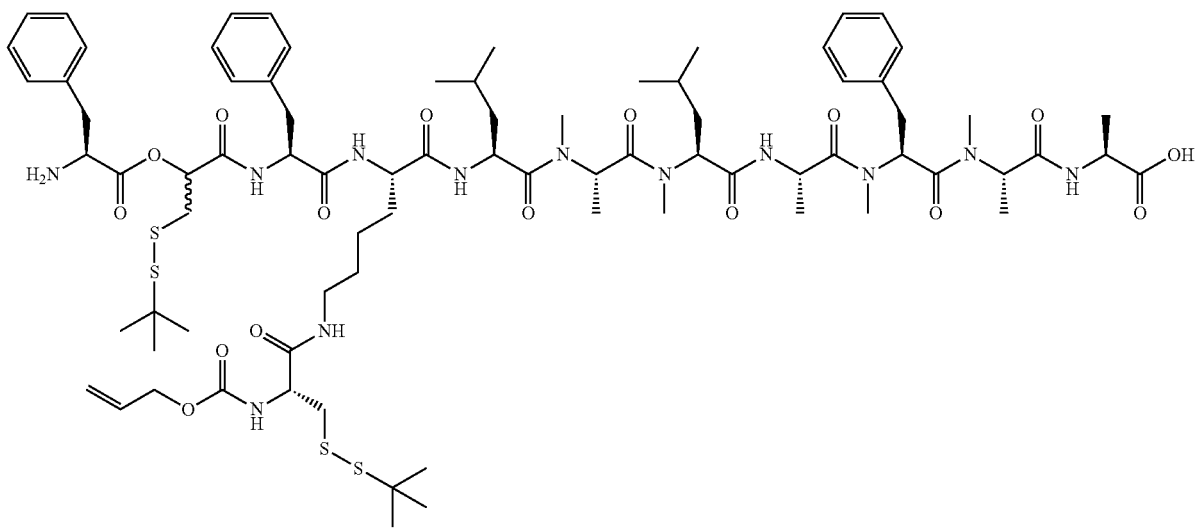 [SMILES: C=CCOC(=O)N[C@@H](CSSC(C)(C)C)C(=O)NCCCC[C@H](NC(=O)[C@H](Cc1ccccc1)NC(=O)C(CSSC(C)(C)C)OC(=O)[C@@H](N)Cc1ccccc1)C(=O)N[C@@H](CC(C)C)C(=O)N(C)[C@@H](C)C(=O)N(C)[C@@H](CC(C)C)C(=O)N[C@@H](C)C(=O)N(C)[C@@H](Cc1ccccc1)C(=O)N(C)[C@@H](C)C(=O)N[C@@H](C)C(=O)O]

A 5% solution of piperidine in dimethylformamide (DMF) (250 μl) was added to (5S,11S,14S,17S,20S,23S,26S,29S,32S,35S)-14-(4-((R)-2-(((allyloxy)carbonyl)amino)-3-(tert-butyldisulfanyl)propanamide)butyl)-5,11,29-tribenzyl-8-((tert-butyldisulfanyl)methyl)-1-(9H-fluoren-9-yl)-17,23-diisobutyl-19,20,22,26,28,31,32,35-octamethyl-3,6,9,12,15,18,21,24,27,30,33-undecaoxo-2,7-dioxa-4,10,13,16,19,22,25,28,31,34-decaazahexatriacontan-36-oic acid (Fmoc-Phe-tBuSSlac-Phe-Lys(Alloc-Cys(StBu))-Leu-MeAla-MeLeu-Ala-MePhe-NeAla-Ala-OH) (Compound SP668) (SEQ ID NO: 272) (23.0 mg, 0.012 mmol) at room temperature, and the mixture was stirred at the same temperature for 10 minutes. Formic acid (5.0 μL) was added to the reaction solution, and the mixture was purified by reverse-phase silica gel chromatography (0.1% aqueous formic acid solution/0.1% formic acid-acetonitrile solution) to afford (9S,12S,15S,18S,21S,24S,27S,30S,33S)-12-(4-((R)-2-(((allyloxy)carbonyl)amino)-3-(tert-butyldisulfanyl)propanamide)butyl)-6-(((S)-2-amino-3-phenylpropanoyl)oxy)-9,27-dibenzyl-15,21-diisobutyl-2,2,17,18,20,24,26,29,30,33-decamethyl-7,10,13,16,19,22,25,28,31-nonaoxo-3,4-dithia-8,11,14,17,20,23,26,29,32-nonaazatetratriacontan-34-oic acid (H-Phe-tBuSSlac-Phe-Lys(Alloc-Cys(StBu))-Leu-MeAla-MeLeu-Ala-MePhe-MeAla-Ala-OH) (Compound SP670) (SEQ ID NO: 273) (21.0 mg) quantitatively.

LCMS (ESI) m/z=1622 (M+H)+

Retention time: 0.30 min, 0.34 min (analysis condition SQDFA50)

Since the tBuSSlac site is an optical isomer mixture, diastereomers existed as compounds, and two peaks were observed.

Synthesis of Allyl ((2R)-3-(tert-butyldisulfanyl)-1-oxo-1-((4-((5S,8S,11S,14S,17S,20S,23S,26S,29S,32S)-5,23,32-tribenzyl-2-((tert-butyldisulfanyl)methyl)-11,17-diisobutyl-13,14,16,20,22,25,26,29-octamethyl-3,6,9,12,15,18,21,24,27,30,33-undecaoxo-1-oxa-4,7,10,13,16,19,22,25,28,31-decaazacyclotritriacontan-8-yl)butyl)amino)propan-2-yl)carbamate (*Phe-tBuSSiac-Phe-Lys(Alloc-Cys(StBu))-Leu-MeAla-MeLeu-Ala-MePhe-MeAla-Ala*, Cyclized at Two Sites) (Compound SP671) (SEQ ID NO: 274)

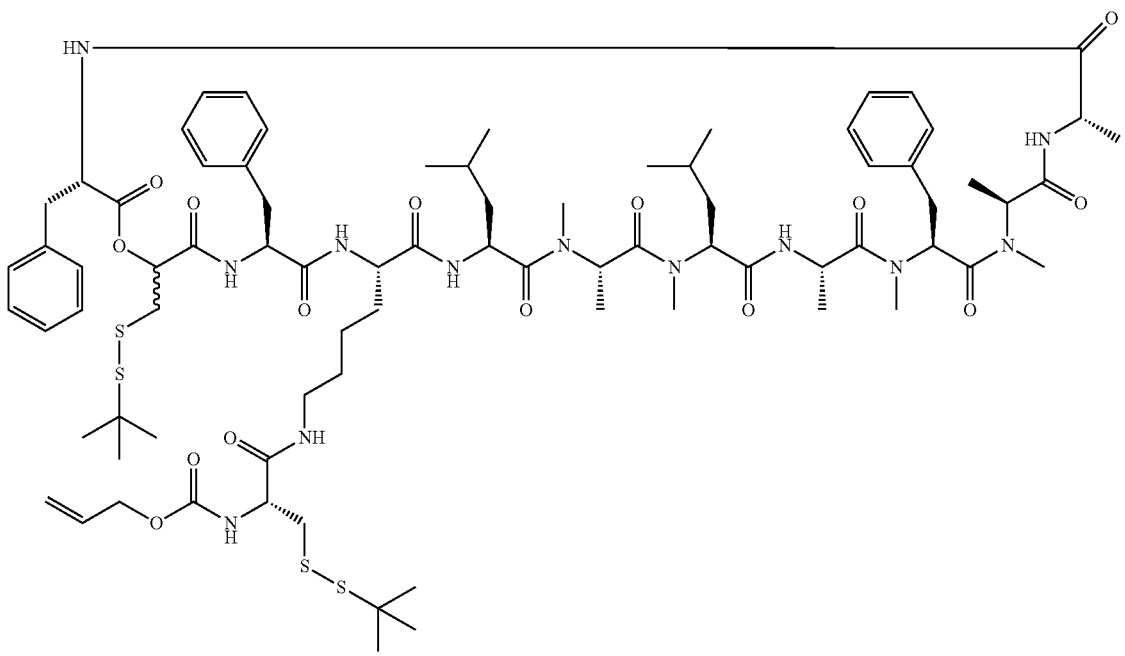 [SMILES: C=CCOC(=O)N[C@@H](CSSC(C)(C)C)C(=O)NCCCC[C@@H]1NC(=O)[C@H](Cc2ccccc2)NC(=O)C(CSSC(C)(C)C)OC(=O)[C@H](Cc2ccccc2)NC(=O)[C@H](C)NC(=O)[C@H](C)N(C)C(=O)[C@H](Cc2ccccc2)N(C)C(=O)[C@H](C)NC(=O)[C@H](CC(C)C)N(C)C(=O)[C@H](C)N(C)C(=O)[C@H](CC(C)C)NC1=O]

A solution of O-(7-aza-1H-benzotriazol-1-yl)-N,N,N',N'-tetramethyluronium hexafluorophosphate (HATU) (0.42 mg, 1.11 μmol) in Dimethyl formamide (DMF) (4.2 μl) and a solution of diisopropylethylamine (DIPEA) (0.194 μl, 1.11 μmol) in dimethylformamide (DMF) (2.0 μl) were added to a solution of (9S,12S,15S,18S,21S,24S,27S,30S,33S)-12-(4-((R)-2-(((allyloxy)carbonyl)amino)-3-(tert-butyldisulfanyl)propanamide)butyl)-6-(((S)-2-amino-3-phenylpropanoyl)oxy)-9,27-dibenzyl-15,21-diisobutyl-2,2,17,18,20,24,26,29,30,33-decamethyl-7,10,13,16,19,22,25,28,31-nonaoxo-3,4-dithia-8,11,14,17,20,23,26,29,32-nonaazatetratriacontan-34-oic acid (H-Phe-tBuSSlac-Phe-Lys(Alloc-Cys(StBu))-Leu-MeAla-MeLeu-Ala-MePhe-MeAla-Ala-OH) (Compound SP670) (SEQ ID NO: 273) (1.2 mg, 0.74 μmmol) in dimethylformamide (DMF)/dichloromethane (DCM) (=4/1, v/v, 800 μl) at room temperature, and the mixture was stirred at the same temperature for 3 hours. Formic acid (0.28 μL) was added to the reaction solution, and the mixture was purified by reverse-phase silica gel chromatography (0.1% aqueous formic acid solution/0.1% formic acid-acetonitrile solution) to afford allyl ((2R)-3-(tert-butyldisulfanyl)-1-oxo-1-((4-((5S,3S,11S,14S,17S,20S,23S,26S,29S,32S)-5,23,32-tribenzyl-2-((tert-butyldisulfanyl)methyl)-11,17-diisobutyl-13,14,16,20,22,25,26,29-octamethyl-3,6,9,12,15,18,21,24,27,30,33-undecaoxo-1-oxa-4,7,10,13,16,19,22,25,28,31-decaazacyclotritriacontan-8-yl)butyl)amino)propan-2-yl) carbamate (*Phe-tBuSSiac-Phe-Lys(Alloc-Cys(StBu))-Leu-MeAla-MeLeu-Ala-MePhe-MeAla-Ala*, cyclized at two * sites) (Compound SP671) (SEQ ID NO: 274) (0.90 mg, 76%).

LCMS (ESI) m/z=1604.5 (M+H)+

Retention time: 0.79 min (analysis condition SQDFA50)

Synthesis of (2R)-2-amino-3-(tert-butyldisulfanyl)-N-(4-((5S,8S,11S,14S,17S,20S,23S,26S,29S,32S)-5,23,32-tribenzyl-2-((tert-butyldisulfanyl)methyl)-11,17-diisobutyl-13,14,16,20,22,25,26,29-octamethyl-3,6,9,12,15,18,21,24,27,30,33-undecaoxo-1-oxa-4,7,10,13,16,19,22,25,28,31-decaazacyclotritriacontan-8-yl)butyl)propanamide (*Phe-tBuSSiac-Phe-Lys(H-Cys(StBu))-Leu-MeAla-MeLeu-Ala-MePhe-MeAla-Ala*, Cyclized at Two Sites) (Compound SP665) (SEQ ID NO: 275)

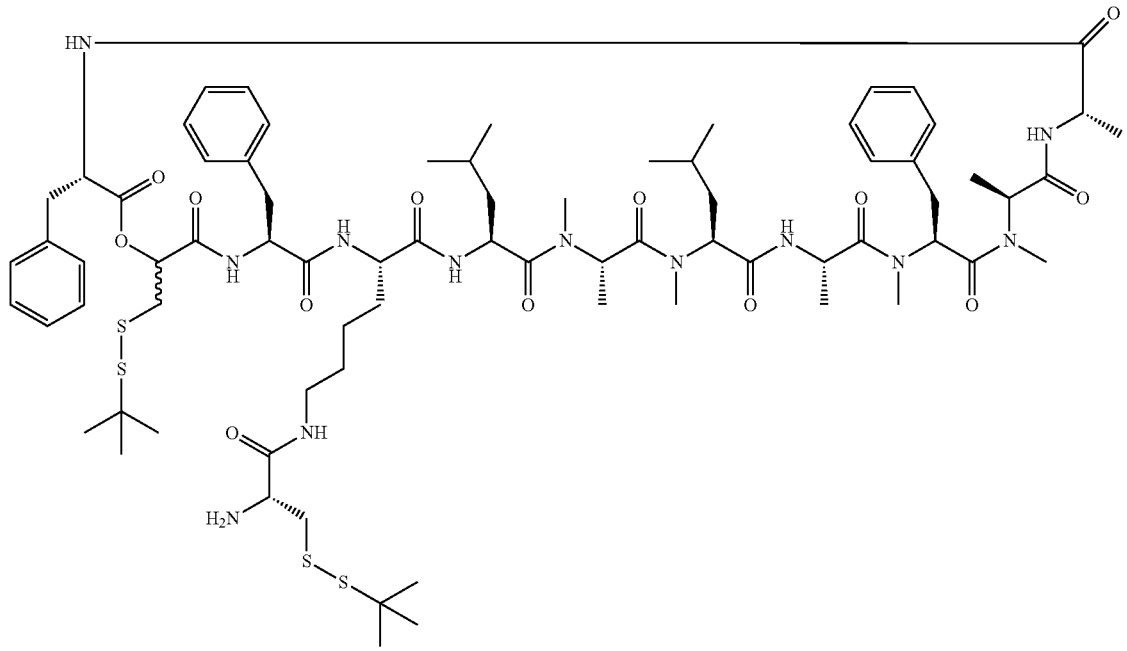 [SMILES: CC(C)C[C@@H]1NC(=O)[C@H](CCCCNC(=O)[C@@H](N)CSSC(C)(C)C)NC(=O)[C@H](Cc2ccccc2)NC(=O)C(CSSC(C)(C)C)OC(=O)[C@H](Cc2ccccc2)NC(=O)[C@H](C)NC(=O)[C@H](C)N(C)C(=O)[C@H](Cc2ccccc2)N(C)C(=O)[C@H](C)NC(=O)[C@H](CC(C)C)N(C)C(=O)[C@H](C)N(C)C1=O]

A solution of phenylsilane (PhSiH$_3$) (0.385 µl, 3.12 µmol) in 1,3-dimethyl-2-imidazolidinone (DMI) (140 µl), and tetrakis(triphenylphosphine)palladium (0) (Pd(Ph$_3$P) 4) (1.80 mg, 1.56 µmol) were added to allyl ((2R)-3-(tert-butyldisulfanyl)-1-oxo-1-((4-((5S,8S,11S,14S,17S,20S,23S,26S,29S,32S)-5,23,32-tribenzyl-2-((tert-butyldisulfanyl)methyl)-11,17-diisobutyl-13,14,16,20,22,25,26,29-octamethyl-3,6,9,12,15,18,21,24,27,30,33-undecaoxo-1-oxa-4,7,10,13,16,19,22,25,28,31-decaazacyclotritriacontan-8-yl)butyl)amino)propan-2-yl)carbamate (*Phe-tBuSSiac-Phe-Lys(Alloc-Cys(StBu))-Leu-MeAla-MeLeu-Ala-MePhe-MeAla-Ala*, cyclized at two * sites) (Compound SP671) (SEQ ID NO: 274) (2.5 mg, 1.56 µmol) at room temperature, and the reaction solution was stirred at 30° C. for 1 hour and 30 minutes. The reaction solution was purified by reverse-phase silica gel chromatography (0.1% aqueous formic acid/0.1% formic acid-acetonitrile solution) to afford (2R)-2-amino-3-(tert-butyldisulfanyl)-N-(4-((5S,8S,11S,14S,17S,20S,23S,26S,29S,32S)-5,23,32-tribenzyl-2-((tert-butyldisulfanyl)methyl)-11,17-diisobutyl-13,14,16,20,22,25,26,29-octamethyl-3,6,9,12,15,18,21,24,27,30,33-undecaoxo-1-oxa-4,7,10,13,16,19,22,25,28,31-decaazacyclotritriacontan-8-yl)butyl)propanamide (*Phe-tBuSSiac-Phe-Lys(H-Cys(StBu))-Leu-MeAla-MeLeu-Ala-MePhe-MeAla-Ala*, cyclized at two sites) (Compound SP665) (SEQ ID NO: 275) (2.60 mg, 88%).

LCMS (ESI) m/z=1520 (M+H)+

Retention time: 0.83 min (analysis condition SQDFA05)

7-2. Reaction of Producing a Branched Peptide from the Translated Peptide Model Compound (Compound SP665)

Synthesis of (2S)—N-((3R,6S,9S,12S,15S,18S,21S,24S,27S,30S)-6,15-dibenzyl-21,27-diisobutyl-3-(mercaptomethyl)-9,12,13,16,18,22,24,25-octamethyl-2,5,8,11,14,17,20,23,26,29-decaoxo-1,4,7,10,13,16,19,22,25,28-decaazacyclotetratriacontan-30-yl)-2-(2-hydroxy-3-mercaptopropanamide)-3-phenylpropanamide(H-HSlac-Phe-Lys(*Cys)-Leu-MeAla-MeLeu-Ala-MePhe-MeAla-Ala-Phe*, Cyclized at Two * Sites) (Compound SP672) (SEQ ID NO: 276)

HSlac herein refers to a divalent structure from Compound SP666 in which the side chain tBuS group is deprotected and the hydrogen atom on the hydroxyl group and the hydroxyl group on the carboxylic acid are removed.

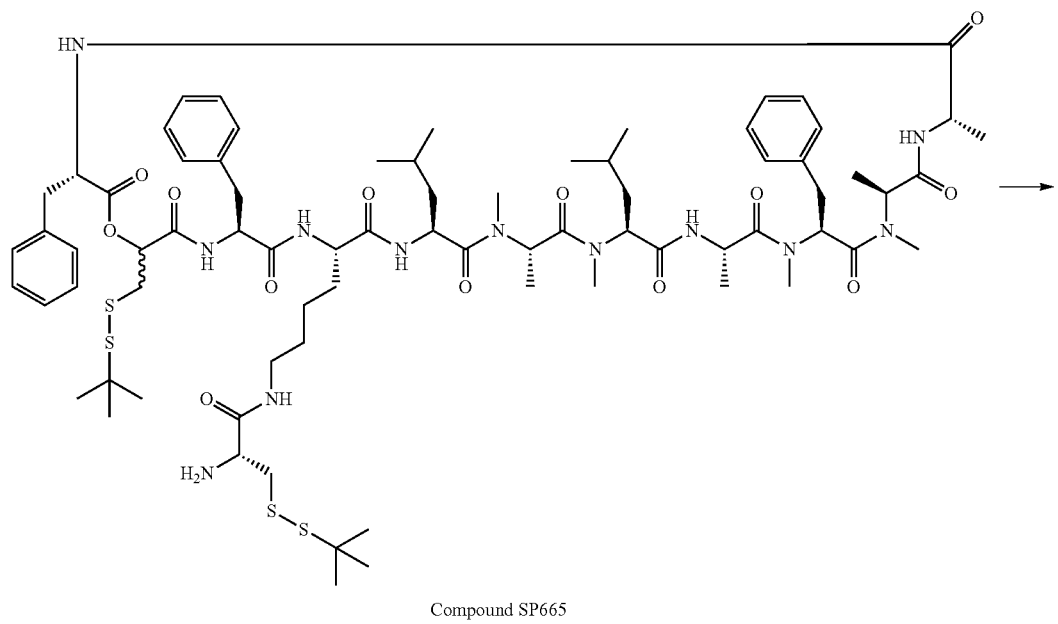

Compound SP665

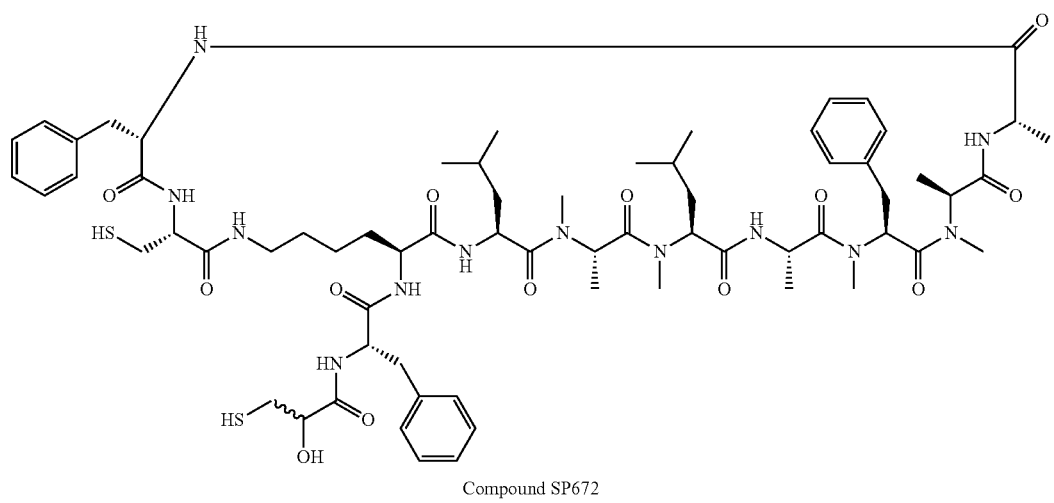

Compound SP672

Figure 72:
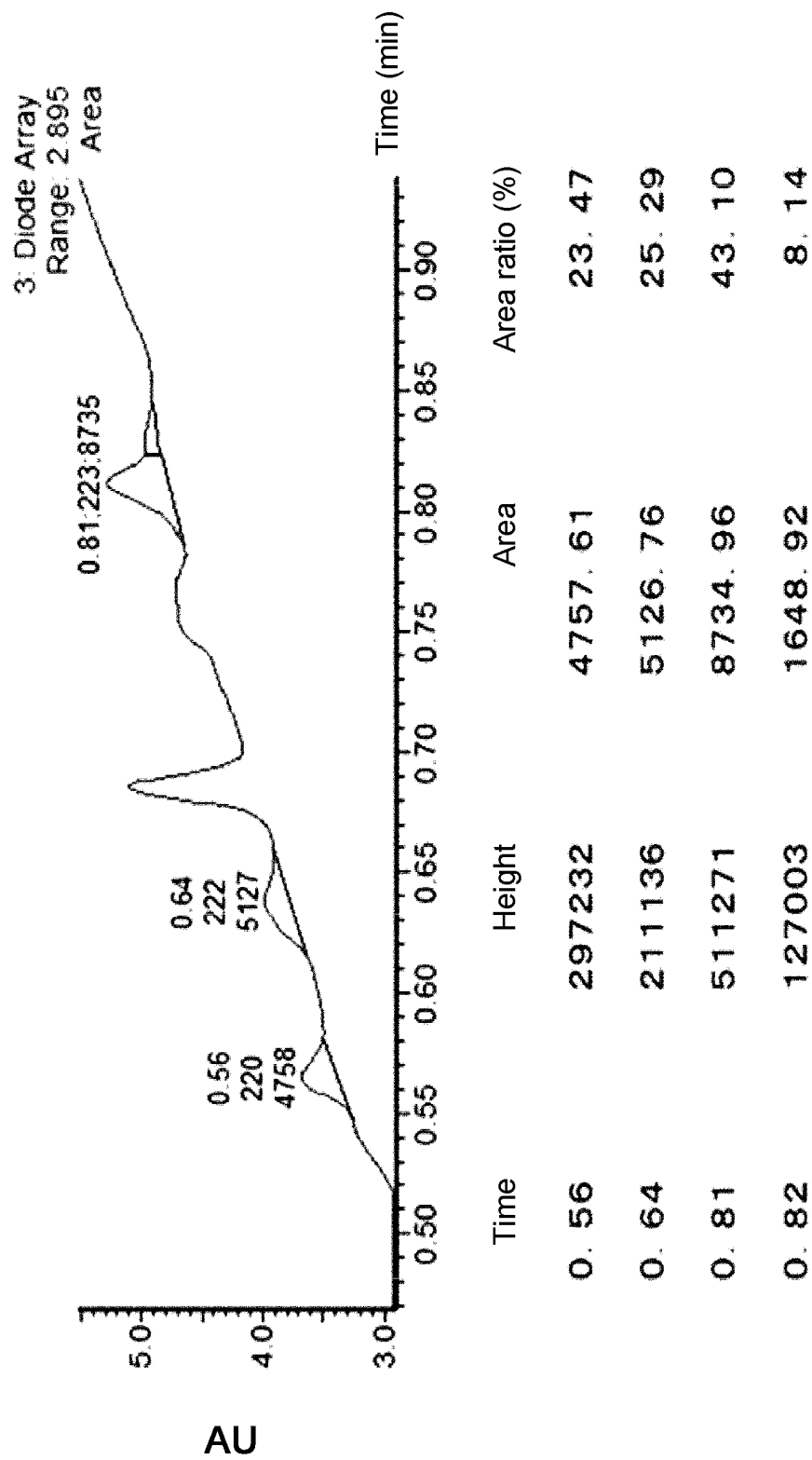
FIG. 72 is a diagram showing LCMS analysis results of a reaction solution containing produced compound SP672.

A solution of (2R)-2-amino-3-(tert-butyldisulfanyl)-N-(4-((5S,8S,11S,14S,17S,20S,23S,26S,29S,32S)-5,23,32-tribenzyl-2-((tert-butyldisulfanyl)methyl)-11,17-diisobutyl-13,14,16,20,22,25,26,29-octamethyl-3,6,9,12,15,18,21,24,27,30,33-undecaoxo-1-oxa-4,7,10,13,16,19,22,25,28,31-decaazacyclotritriacontan-8-yl)butyl)propanamide (*Phe-tBuSSiac-Phe-Lys(H-Cys(StBu))-Leu-MeAla-MeLeu-Ala-MePhe-MeAla-Ala*, cyclized at two sites) (Compound SP665) (SEQ ID NO: 277) (76 μg, 0.05 plod) in 1,3-dimethyl-2-imidazolidinone (DMI) (7.5 μl) was added to a mixed solution of a 1 M aqueous tris(2-carboxyethyl)phosphine (TCEP) hydrochloride solution (1 μl), 2 M HEPES. buffer (1.5 μl, pH=7.6), a 1 N aqueous sodium hydroxide solution (1.8 μl) and water (38.2 μl) at room temperature under a nitrogen atmosphere, and the mixture was stirred at 30 degrees for 13 hours at pH=6.6. The change in the reaction was traced by LCMS to confirm that the intended Compound SP672 was produced after 13 hours. In addition to the intended compound, a hydrolysate (m/z=1359.8 (M–H)–), m/z=1309.6 (M–H)–(LCMS retention time 0.64 min for both compounds), m/z=1377.8 (M–H)– (LCMS retention time 0.82 min) and m/z=1559.9 (M–H)– (LCMS retention time 0.56 min) were observed as by-products. The intended compound was 43% based on the UV area ratio by LCMS (FIG. 72).

LCMS (ESI) m/z=1342 (M–H)–

Retention time: 0.81 min (analysis condition SQDFA05)

7-3. Desulfurization Reaction from the Branched Peptide

Synthesis of (2S)—N-((3S,6S,9S,12S,15S,18S,21S,24S,27S,30S)-6,15-dibenzyl-21,27-diisobutyl-3,9,12,13,16,18,22,24,25-nonamethyl-2,5,8,11,14,17,20,23,26,29-decaoxo-1,4,7,10,13,16,19,22,25,28-decaazacyclotetratriacontan-30-yl)-2-(2-hydroxypropanamide)-3-phenylpropanamide (H-Lac-Phe-Lys(Ala)-Leu-MeAla-MeLeu-Ala-MePhe-MeAla-Ala-Phe*, Cyclized at Two Sites) (Compound SP673) (SEQ ID NO: 278)

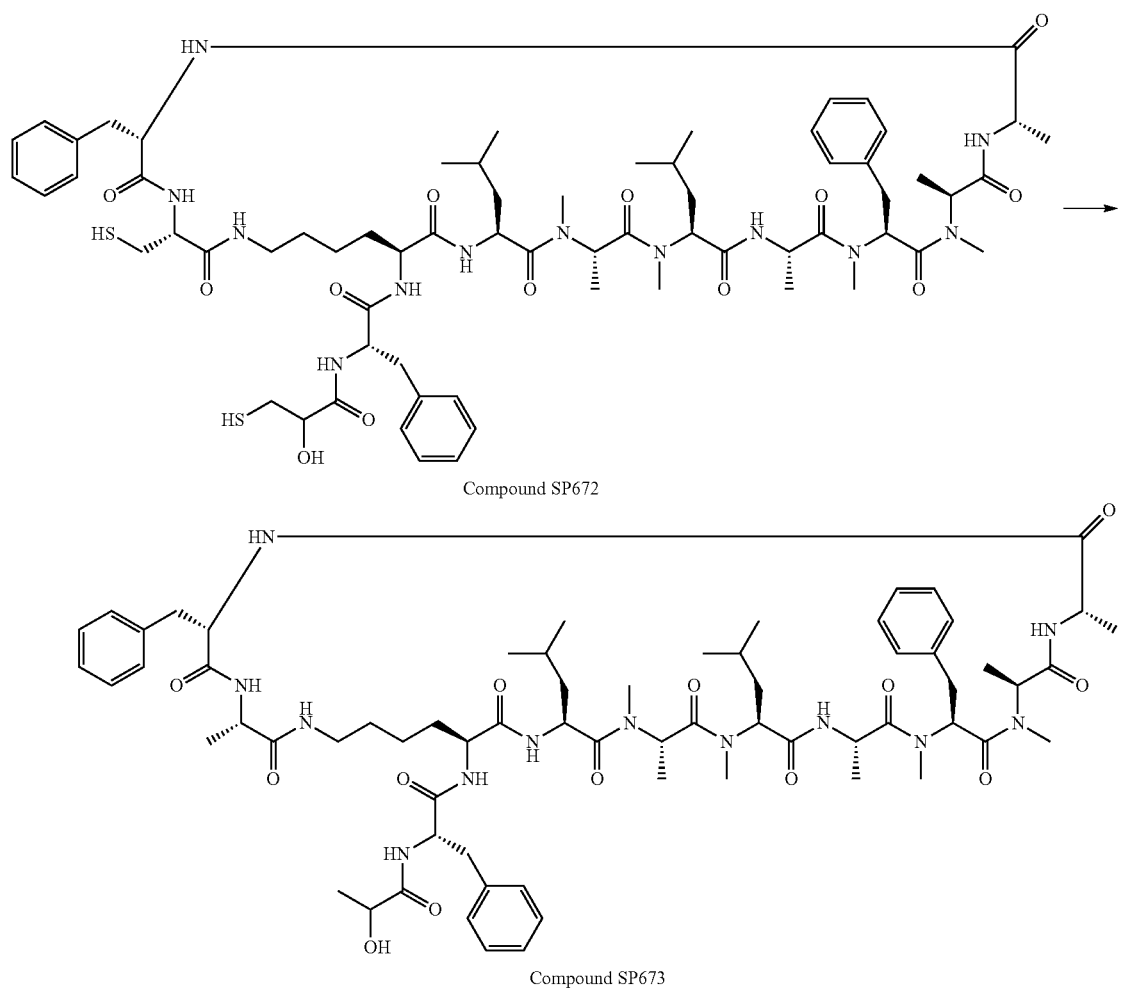

Compound SP672

Compound SP673

A 330 mM aqueous glutathione solution (10.8 μl) and a 670 mM tris(2-carboxyethyl)phosphine (TCEP) hydrochloride solution (7.2 μl, pH=7.1) were added to the aforementioned reaction solution (20 μl) as used in 7-2. under a nitrogen atmosphere, and the mixture was stirred at 50° C. for 5 minutes. A 250 mM aqueous 2,2-azobis[2-(2-imidazolin-2-yl)propane] dihydrochloride (VA-044) solution (1.6 μl) was added at room temperature, and the mixture was stirred at 50° C. for 20 minutes. The change in the reaction was traced by LCMS to confirm that the intended (2S)—N-((3S,6S,9S,12S,15S,18S,21S,24S,27S,30S)-6,15-dibenzyl-21,27-diisobutyl-3,9,12,13,16,18,22,24,25-nonamethyl-2,5,8,11,14,17,20,23,26,29-decaoxo-1,4,7,10,13,16,19,22, 25,28-decaazacyclotetratriacontan-30-yl)-2-(2-hydroxypropanamide)-3-phenylpropanamide (H-lac-Phe-Lys(*Ala)-Leu-MeAla-MeLeu-Ala-MePhe-MeAla-Ala-Phe*, cyclized at two * sites) (Compound SP673) (SEQ ID NO: 278) was produced after 20 minutes.

The 670 mM tris(2-carboxyethyl)phosphine (TCEP) hydrochloride solution was prepared by the following method. Tris(2-carboxyethyl)phosphine (TCEP) hydrochloride (29 mg, 101 μmol) was adjusted to pH=7.1 by adding water (100 μl) and triethylamine (Et₃N) (50 μl) thereto.

LCMS (ESI) m/z=1280 (M+H)+

Retention time: 0.77 min (analysis condition SQDFA05)

8. Reaction of Producing an Intramolecular Branched Peptide (Linear Portions 2) Using a Peptide-RNA Complex A RNA-peptide complex was subjected to intramolecular branched peptide reaction, and the product was analyzed by electrophoresis.

8-1. Preparation of a Puromycin-Containing Template mRNA and Translation Synthesis of a RNA-Peptide Complex mRNA (SEQ ID NO: RM-H2) was prepared by in vitro transcription using DNA (SEQ ID NO: DM-H1) prepared by PCR as a template, and was purified using RNeasy mini kit (Qiagen). 15 µM puromycin linker (Sigma) (SEQ ID NO: C-H1), 1×T4 RNA ligase reaction buffer (NEB), 1 mM ATP, 10% DMSO and 0.63 unit/µl T4 RNA ligase (NEB) were added to 10 µM mRNA, ligation reaction was carried out at room temperature for 30 minutes, and the mixture was then purified by RNeasy MiniElutekit (Qiagen). Next, a translation reaction solution was prepared by using the above-prepared 1 µM mRNA-puromycin linker conjugate in place of the template RNA OT86b (SEQ ID NO: RM-H1) of the above-described translation system as a template and further adding 0.25 mM Gly to the mixture, and was incubated at 37° C. for 60 minutes and subsequently at room temperature for 12 minutes. The reaction solution was then purified with RNeasy minelute (Qiagen) to provide a peptide-RNA complex molecule.

```
SEQ ID NO: DM-H1 OT-104
OT-104 DNA sequence
                                    (SEQ ID NO: 92)
GGCGTAATACGACTCACTATAGGGTTAACTTTAAGAAGGAGATATACATa tgTGCACTACATGGTTCCGTTGGTGCCCACAGTTCAAGTGGCTTCCTCGT

AGTGGCTCTGGCTCTGGCTCTTAGGGCGGCGGGGACAAA

SEQ ID NO: RM-H2 OT-104
OT-104 RNA sequence
                                    (SEQ ID NO: 93)
GGGUUAACUUUAAGAAGGAGAUAUACAUaugUGCACUACAUGGUUCCGUU

GGUGCCCACAGUUCAAGUGGCUUCCUCGUAGUGGCUCUGGCUCUGGCUCU

UAGGGCGGGGGACAAA

SEQ ID C-H1 S2PuFLin sequence
                                    (SEQ ID NO: 76)
[P]CCCGTCCCCGCCGCCC [Fluorecein-dT][Spacer18]

[Spacer18][Spacer18][Spacer18][Spacer18]CC

[Puromycin]([P]: 5'-phosphorylated)
```

8-2. Production of a Peptide-RNA Complex Having an Intramolecular Branched Peptide (Linear Portion 2)

Figure 74:
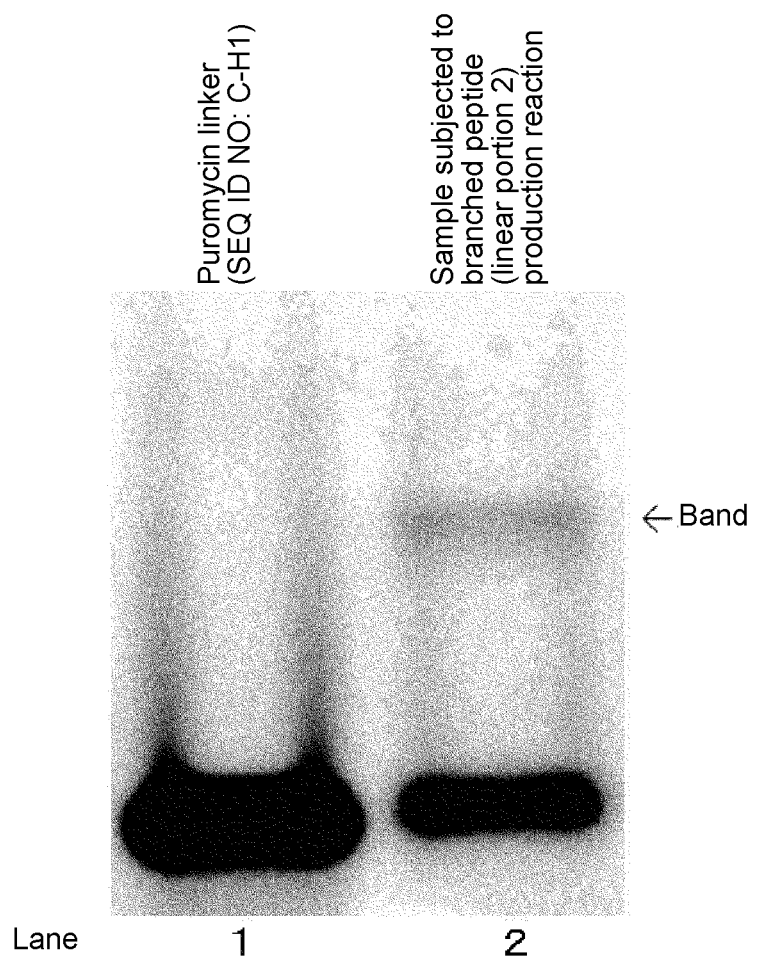
FIG. 74 is a diagram showing electrophoretic analysis results of reaction products containing a peptide-RNA complex having an intramolecular branched peptide (linear portion 2).

100 µL of N,N-dimethylacetamide (DMA), 5.5 µL of 2 M HEPES-KOH (pH 7.6) and 2.1 µL of 1 M tris(2-carboxyethyl)phosphine (TCEP) (pH 7.6) were added to 100 µL of the peptide-RNA complex solution prepared above, and the mixture was incubated at 37° C. for 2 hours. Subsequently, 848 µL of a reagent solution (59 mM tris(2-carboxyethyl) phosphine hydrochloride, 425 mM N,N-bis-(2-hydroxyethyl)glycine (bicine) (pH 8.7), 590 mM Sodium hydroxide, 47% (v/v) N,N-dimethylacetamide (DMA) and 593 mM 4-(trifluoromethyl)benzenethiol) was added to the reaction solution, and the mixture was incubated at 37° C. for a further 20 hours. The peptide-RNA complex was purified from the resulting reaction solution using RNeasy minelute (Qiagen) and eluted from the column with 100 µL of pure water. Subsequently, 12 µL of 10×RNase ONE ribonuclease reaction buffer (Promega), 6 µL of RNase ONE ribonuclease (Promega) and 6 µL of RNase H (Life Technologies) were added and the mixture was incubated at room temperature for 3 days. The resulting reaction solution and unreacted puromycin linker (SEQ ID NO: C-H1) were subjected to electrophoresis using peptide-PAGE mini (TEFCO), and the band was visualized with fluorescein derived from the puromycin linker (FIG. 74). As a result, the difference in band mobility due to conjugating of the peptide to the puromycin linker was observed in the sample subjected to reaction of producing a branched peptide (linear portion 2) (FIG. 74, lane 2, band I). This indicated the presence of the intended intramolecular branched peptide-RNA complex.

9. Synthesis of Aminoacylated pdCpAs of Units which Enable Production of Branched Peptides from Translational Products In the present specification, a compounds in which the main chain carboxylic acid of an amino acids, amino acid derivative or amino acid analog and the hydroxyl group (at the 2- or 3-position) of pdCpA form an ester bond is described as amino acid-pdCpA. Amino acid, amino acid derivative or amino acid analog sites are indicated by abbreviations, and each abbreviation is defined as follows.

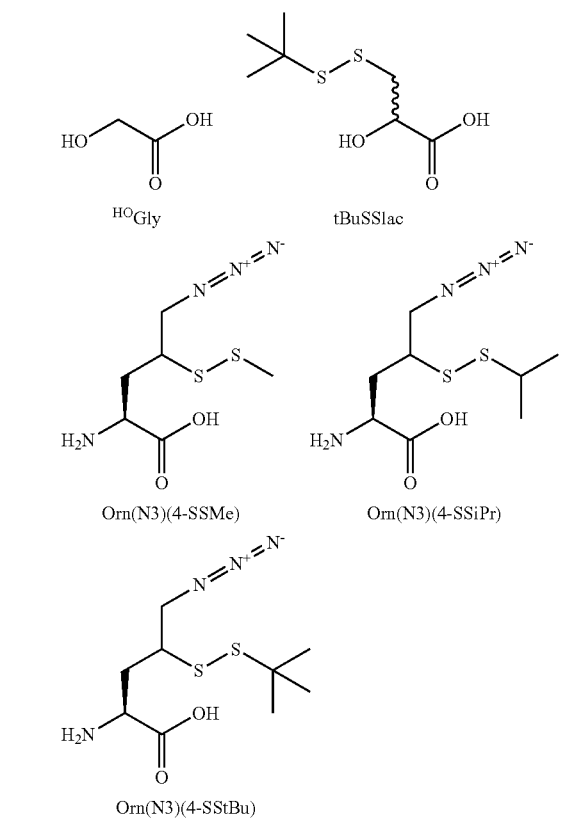

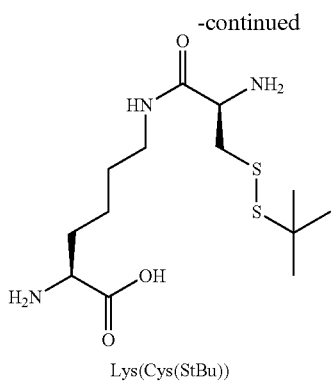

Lys(Cys(StBu))

9-1. Synthesis of Aminoacylated pdCpA Compound 20

Compound 21

Synthesis of Cyanomethyl 2-(tert-butyldimethylsilyloxy)acetate

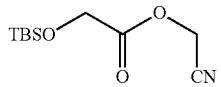

A solution of glycolic acid (1.0 g, 13.15 mmol) and imidazole (4.48 g, 65.7 mmol) in DMF (13.15 ml) was cooled to 0° C., after which tert-butyldimethylchlorosilane (4.76 g, 31.6 mmol) was added and the reaction solution was stirred at room temperature for 12 hours. The reaction mixture was extracted with diethyl ether/water, and the organic layer was washed with 25 wt % brine. The organic layer was dried over anhydrous sodium sulfate, filtered and concentrated under reduced pressure. THF (30 mL) was added to the resulting residue. After cooling to 0° C., methanol (90 mL) and a 9.1 wt % aqueous potassium carbonate solution (30 mL) were added and the reaction solution was stirred at room temperature for 1 hour. The reaction mixture was concentrated under reduced pressure to afford a crude product (4.25 g).

Acetonitrile (6.7 ml) and DMF (6.7 ml) were added to the crude product (1.53 g), and the mixture was cooled to 0° C., after which diisopropylethylamine (3.51 mL, 20.1 mmol) and 2-bromoacetonitrile (0.93 ml, 13.4 mmol) were added and the reaction solution was stirred at room temperature for 6 hours. The reaction mixture was extracted with diethyl ether/water, and the organic layer was washed with 25 wt % brine. The organic layer was dried over anhydrous sodium sulfate, filtered and concentrated under reduced pressure. The resulting residue was purified by normal-phase silica gel column chromatography (hexane/ethyl acetate) to afford cyanomethyl 2-(tert-butyldimethylsilyloxy)acetate (Compound 21) (556 mg, 52%).

LCMS (ESI) m/z=230 (M+H)+

Retention time: 0.54 min (analysis condition SQDAA50)

Compound 22

Synthesis of (2R,3S,4R,5R)-2-(((((2R,3S,5R)-5-(4-amino-2-oxopyrimidin-1(2H)-yl)-2-(phosphonooxymethyl)tetrahydrofuran-3-yloxy)(hydroxy)phosphoryloxy)methyl)-5-(6-amino-9H-purin-9-yl)-4-hydroxytetrahydrofuran-3-yl 2-(tert-butyldimethylsilyloxy)acetate

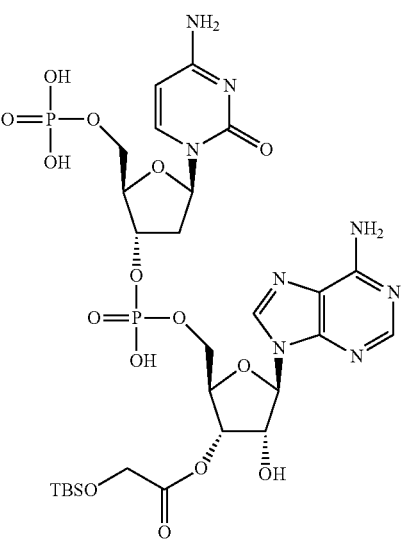 [SMILES: CC(C)(C)[Si](C)(C)OCC(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

A solution of ((2R,3S,5R)-5-(4-amino-2-oxopyrimidin-1 (2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (144 mg, 0.227 mmol) in water (1 ml) and a solution of cyanomethyl 2-(tert-butyldimethylsilyloxy)acetate (Compound 21) (104 mg, 0.453 mmol) in tetrahydrofuran (1 ml) were added to buffer A (30 mL), and the mixture was stirred at room temperature for 2 hours. Following lyophilization, the resulting residue was purified by reverse-phase silica gel column chromatography (0.1% aqueous formic acid solution/0.1% formic acid-acetonitrile solution) to afford (2R,3S,4R,5R)-2-(((((2R,3S,5R)-5-(4-amino-2-oxopyrimidin-1(2H)-yl)-2-(phosphonooxymethyl)tetrahydrofuran-3-yloxy)(hydroxy)phosphoryloxy)methyl)-5-(6-amino-9H-purin-9-yl)-4-hydroxytetrahydrofuran-3-yl 2-(tert-butyldimethylsilyloxy)acetate (Compound 22) (104.5 mg, 57%).

LCMS (ESI) m/z=809.5 (M+H)+

Retention time: 0.52 min (analysis condition SQDFA05)

Compound 20

Synthesis of (2R,3S,4R,5R)-2-((((2R,3S,5R)-5-(4-amino-2-oxopyrimidin-1(2H)-yl)-2-(phosphonooxymethyl)tetrahydrofuran-3-yloxy)(hydroxy)phosphoryloxy)methyl)-5-(6-amino-9H-purin-9-yl)-4-hydroxytetrahydrofuran-3-yl 2-hydroxyacetate ($^{HO}$Gly-pdCpA)

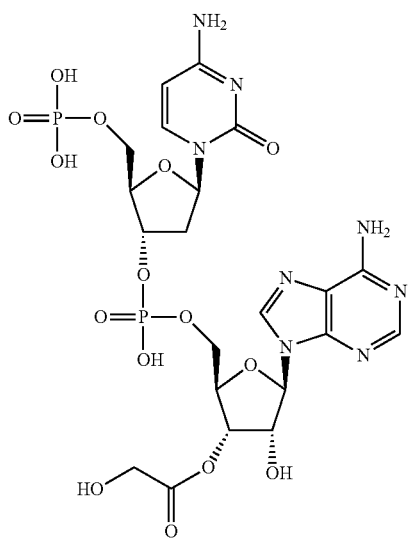 [SMILES: Nc1ccn([C@H]2C[C@H](OP(=O)(O)OC[C@H]3O[C@@H](n4cnc5c(N)ncnc54)[C@H](O)[C@@H]3OC(=O)CO)[C@@H](COP(=O)(O)O)O2)c(=O)n1]

Trifluoroacetic acid (2 ml) was added to a solution of (2R,3S,4R,5R)-2-((((2R,3S,5R)-5-(4-amino-2-oxopyrimidin-1(2H)-yl)-2-(phosphonooxymethyl)tetrahydrofuran-3-yloxy)(hydroxy)phosphoryloxy)methyl)-5-(6-amino-9H-purin-9-yl)-4-hydroxytetrahydrofuran-3-yl 2-(tert-butyldimethylsilyloxy)acetate (Compound 22) (70.0 mg, 87 μmol) in dichloromethane (2 ml) at room temperature, and the mixture was stirred at the same temperature for 30 minutes. Following concentration under reduced pressure, the resulting residue was purified by reverse-phase silica gel column chromatography (0.1% aqueous formic acid solution/0.1% formic acid-acetonitrile solution) to afford (2R,3S,4R,5R)-2-((((2R,3S,5R)-5-(4-amino-2-oxopyrimidin-1(2H)-yl)-2-(phosphonooxymethyl)tetrahydrofuran-3-yloxy)(hydroxy)phosphoryloxy)methyl)-5-(6-amino-9H-purin-9-yl)-4-hydroxytetrahydrofuran-3-yl 2-hydroxyacetate ($^{HO}$Gly-pdCpA) (Compound 20) (14.0 mg, 23%).

LCMS (ESI) m/z=695 (M+H)+

Retention time: 0.28 min (analysis condition SQDAA05)

2-2. Synthesis of Aminoacylated pdCpA Compound 23

The synthesis was carried out according to the following scheme.

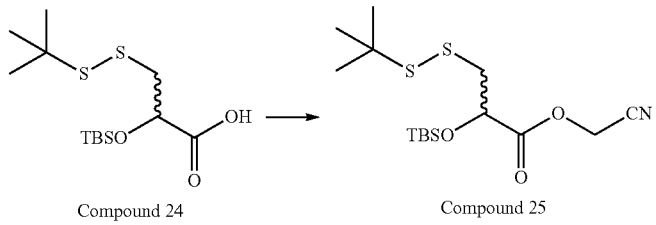

Compound 24　　　　　　Compound 25

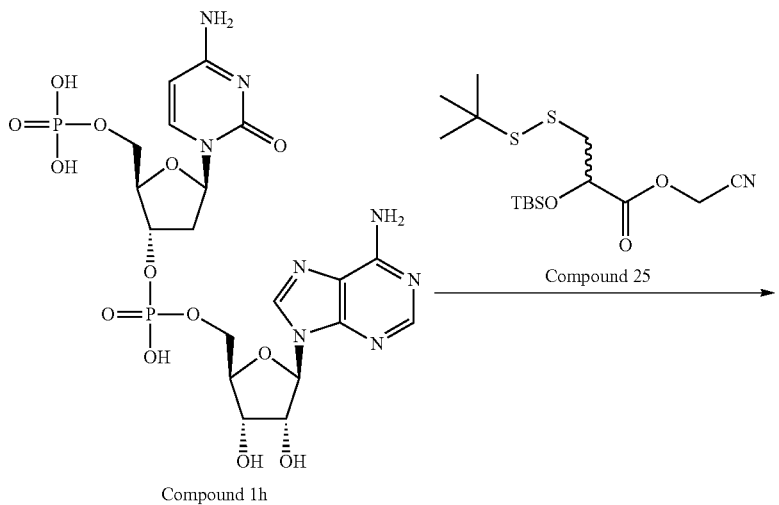

Compound 1h

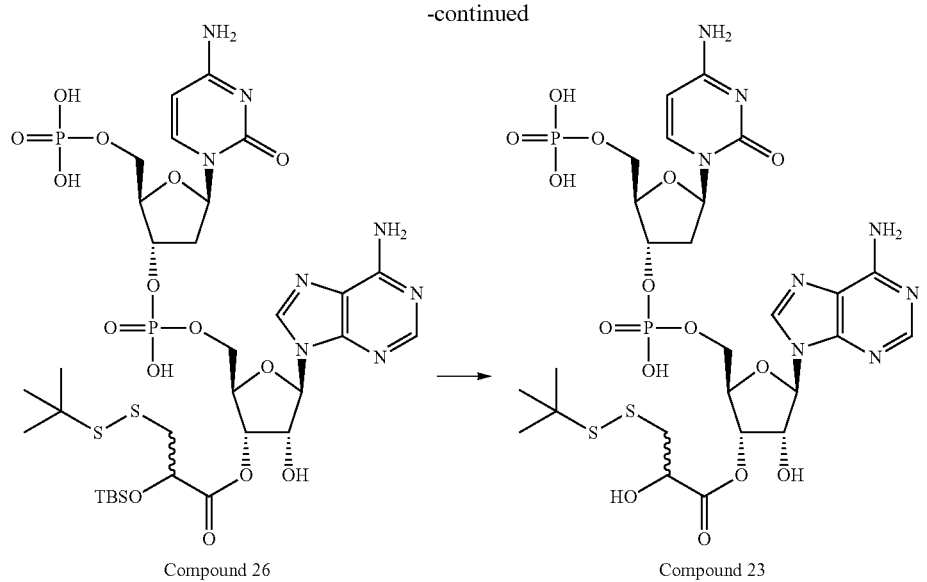

Compound 26 → Compound 23

Synthesis of Cyanomethyl 2-(tert-butyldimethylsilyloxy)-3-(tert-butyldisulfanyl)propionate (Compound 25)

Synthesis of (2R,3S,4R,5R)-2-(((((2R,3S,5R)-5-(4-amino-2-oxopyrimidin-1(2H)-yl)-2-(phosphonooxymethyl)tetrahydrofuran-3-yloxy)(hydroxy)phosphoryloxy)methyl)-5-(6-amino-9H-purin-9-yl)-4-hydroxytetrahydrofuran-3-yl 3-(tert-butyldisulfanyl)-2-hydroxypropionate (Compound 23) (tBuSSlac-pdCpA)

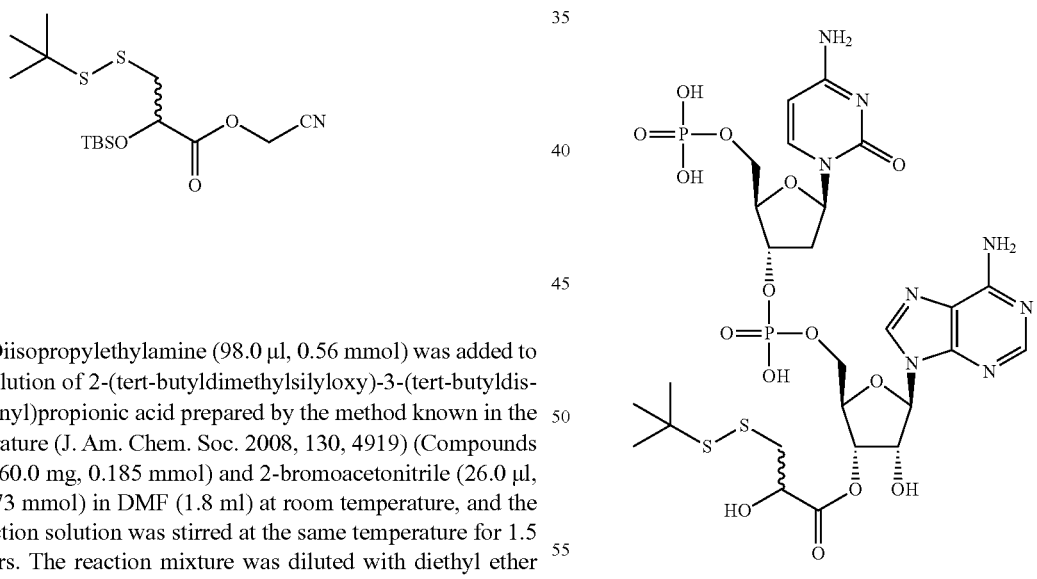

Diisopropylethylamine (98.0 μl, 0.56 mmol) was added to a solution of 2-(tert-butyldimethylsilyloxy)-3-(tert-butyldisulfanyl)propionic acid prepared by the method known in the literature (J. Am. Chem. Soc. 2008, 130, 4919) (Compounds 24, 60.0 mg, 0.185 mmol) and 2-bromoacetonitrile (26.0 μl, 0.373 mmol) in DMF (1.8 ml) at room temperature, and the reaction solution was stirred at the same temperature for 1.5 hours. The reaction mixture was diluted with diethyl ether and washed with a saturated aqueous ammonium chloride solution and brine. The organic layer was dried over anhydrous sodium sulfate, filtered and concentrated under reduced pressure. The resulting residue was purified by normal-phase silica gel column chromatography (hexane/ethyl acetate) to afford cyanomethyl 2-(tert-butyldimethylsilyloxy)-3-(tert-butyldisulfanyl)propionate (Compound 25) (48 mg, 71%).

LCMS (ESI) m/z=364 (M+H)+

Retention time: 0.84 min (analysis condition SQDAA50)

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) tetrabutylammonium salt (48 mg, 0.032 mmol) in DMF (640 μl), and triethylamine (44.8 μl, 0.321 mmol) were added to cyanomethyl 2-(tert-butyldimethylsilyloxy)-3-(tert-butyldisulfanyl)propionate (Compound 25) (23.4 mg, 0.064 mmol) at room temperature, and the reaction solution was stirred at 35° C.

for 1 hour. Formic acid (30 μl) was added to the reaction mixture, and purification by reverse-phase silica gel chromatography (0.1% aqueous formic acid solution/0.1% formic acid-acetonitrile solution) afforded (2R,3S,4R,5R)-2-((((2R,3S,5R)-5-(4-amino-2-oxopyrimidin-1(2H)-yl)-2-(phosphonooxymethyl)tetrahydrofuran-3-yloxy)(hydroxy)phosphoryloxy)methyl)-5-(6-amino-9H-purin-9-yl)-4-hydroxytetrahydrofuran-3-yl 2-(tert-butyldimethylsilyloxy)-3-(tert-butyldimethylsulfanyl)propionate (Compound 26) as a mixture (29.4 mg).

Trifluoroacetic acid (1 ml, 13.0 mmol) was added to the resulting mixture (29.4 mg), and the reaction solution was stirred at room temperature for 5 hours. Following concentration under reduced pressure, the resulting residue was purified by reverse-phase silica gel column chromatography (0.1% aqueous formic acid solution/0.1% formic acid-acetonitrile solution) to afford (2R,3S,4R,5R)-2-((((2R,3S,5R)-5-(4-amino-2-oxopyrimidin-1(2H)-yl)-2-(phosphonooxymethyl)tetrahydrofuran-3-yloxy)(hydroxy)phosphoryloxy)methyl)-5-(6-amino-9H-purin-9-yl)-4-hydroxytetrahydrofuran-3-yl 3-(tert-butyldisulfanyl)-2-hydroxypropionate (18.0 mg, yield in two steps: 68%) (Compound 23) (tBuSSlac-pdCpA).

LCMS (ESI) m/z=829 (M+H)+

Retention time: 0.41 min (analysis condition SQDFA05)

2-4. Synthesis of Aminoacylated pdCpA Compound 27

The synthesis was carried out according to the following scheme.

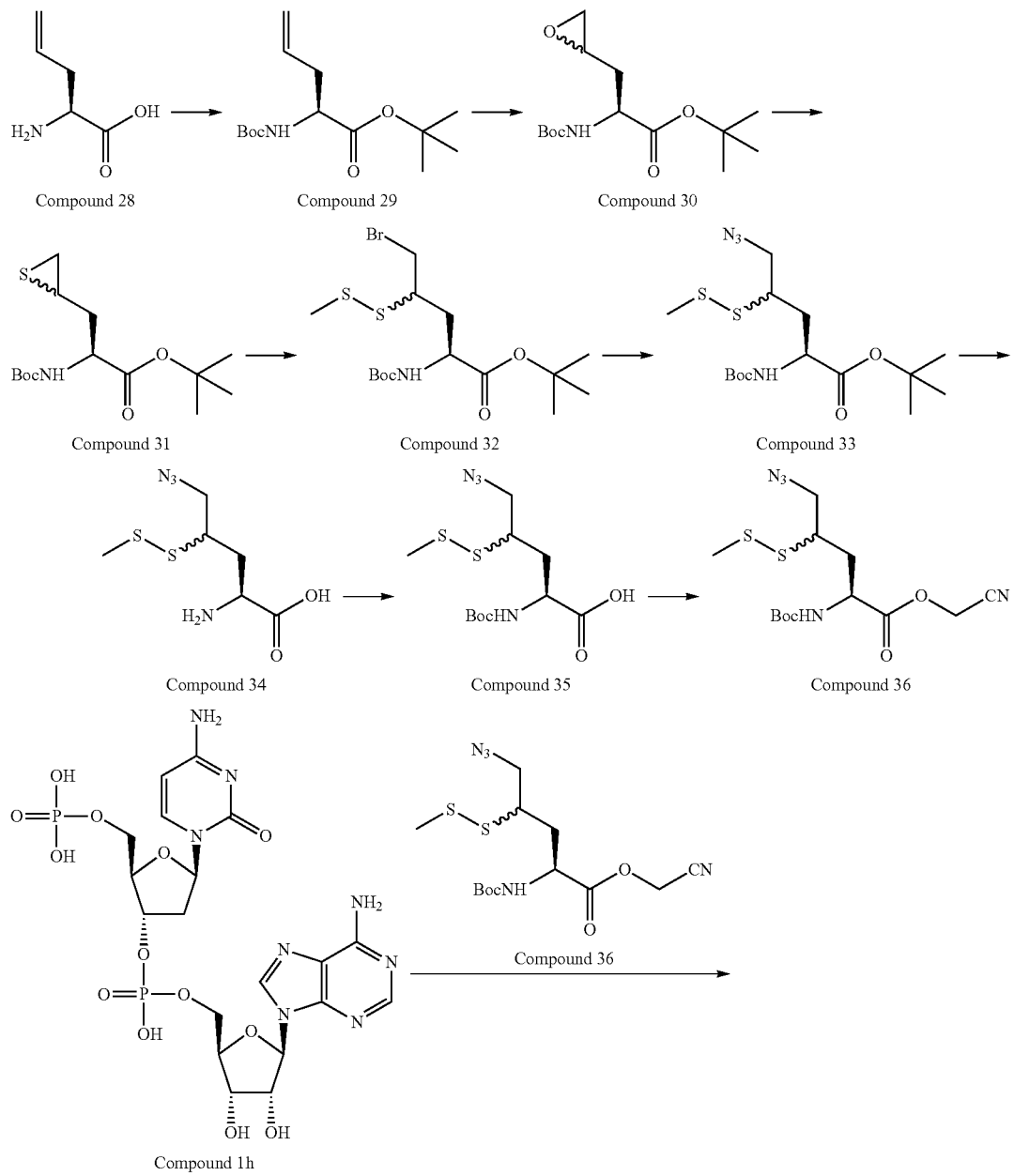

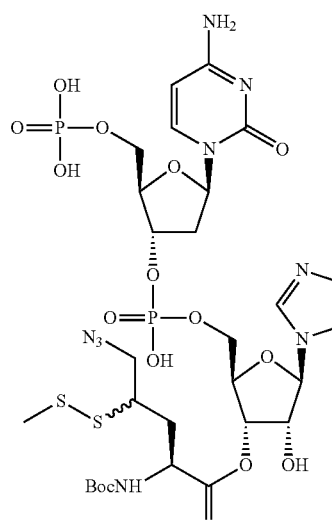

Compound 37

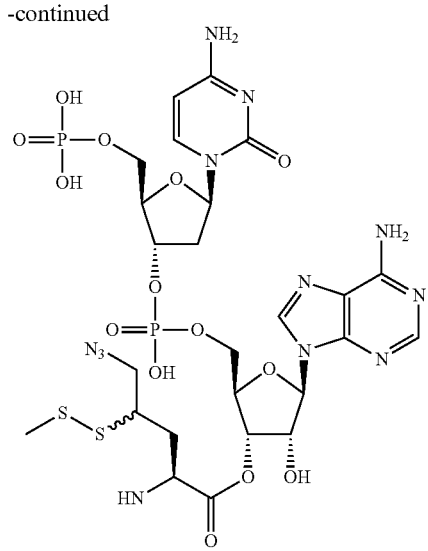

Compound 27

Synthesis of (S)-2-tert-butoxycarbonylamino-pent-4-enoic Acid Tert-Butyl Ester (Compound 29)

Synthesis of (S)-2-tert-butoxycarbonylamino-3-oxiranyl-propionic Acid Tert-Butyl Ester (Compound 30)

A suspension of L-allylglycine (Compound 28) (25.0 g, 217 mmol) in 1,4-dioxane (250 ml)/water (125 ml) was cooled to 0° C., after which di-tert-butyl dicarbonate (52.1 g, 239 mol) and sodium bicarbonate (36.5 g, 434 mol) were added and the reaction solution was stirred at room temperature for 12 hours. After completion of the reaction, the reaction solution was cooled to 0° C., and 1 M hydrochloric acid was added until the pH was 4. The mixture was extracted with ethyl acetate, and the organic layer was washed with brine. The organic layer was dried over anhydrous sodium sulfate, filtered and then concentrated under reduced pressure to afford (S)-2-tert-butoxycarbonylamino-pent-4-enoic acid. The resulting (S)-2-tert-butoxycarbonylamino-pent-4-enoic acid was dissolved in toluene (200 ml), N,N-dimethylformamide di-tert-butylacetal (130 ml) was added and the mixture was stirred at 90° C. for 4 hours. N,N-Dimethylformamide di-tert-butylacetal (25 ml) was further added and the mixture was stirred at 90° C. for 2 hours. The reaction solution was concentrated under reduced pressure, and the resulting residue was purified by normal-phase silica gel column chromatography (hexane/ethyl acetate) to afford (S)-2-tert-butoxycarbonylamino-pent-4-enoic-acid tert-butyl ester (Compound 29) (33.16 g, 56%).

LCMS (ESI) m/z=294 (M+Na)+

Retention time: 1.05 min (analysis condition SQDAA05)

m-Chloroperoxybenzoic acid (40.7 g, 236 mmol) was added to a solution of (S)-2-tert-butoxycarbonylaminopent-4-enoic acid tert-butyl ester (Compound 29) (32.0 g, 118 mmol) in dichloromethane (384 ml), and the mixture was stirred at room temperature for 15 hours. The reaction mixture was cooled to 0° C., and the reaction was terminated by adding a solution of sodium bicarbonate (20 g) in water (300 ml) and a saturated aqueous sodium thiosulfate solution (100 ml). The mixture was extracted with ethyl acetate, and the organic layer was washed with brine. The organic layer was dried over anhydrous sodium sulfate, filtered and concentrated under reduced pressure. The resulting residue was purified by reverse-phase silica gel column chromatography (10 mM aqueous ammonium acetate solution/methanol) to afford (S)-2-tert-butoxycarbonylamino-3-oxiranyl-propionic acid tert-butyl ester (Compound 30) (18.53 g, 55%).

LCMS (ESI) m/z=310 (M+Na)+

Retention time: 1.03 min (analysis condition SQDAA05)

2335

Synthesis of (S)-2-tert-butoxycarbonylamino-3-thiiranyl-propionic Acid Tert-Butyl Ester (Compound 31)

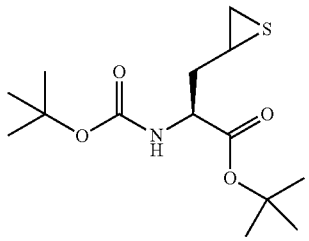 [SMILES: CC(C)(C)OC(=O)N[C@@H](CC1CS1)C(=O)OC(C)(C)C]

Methanol (4 ml) and thiourea (83 mg, 1.096 mmol) were added to (S)-2-tert-butoxycarbonylamino-3-oxiranyl-propionic acid tert-butyl ester (Compound 30) (315 mg, 1.096 mmol), and the reaction solution was heated at reflux for 1.5 hours. The reaction solution was concentrated under reduced pressure, and the resulting residue was purified by normal-phase silica gel column chromatography (hexane/ethyl acetate) to afford (S)-2-tert-butoxycarbonylamino-3-thiiranyl-propionic acid tert-butyl ester (Compound 31) (278 mg, 84%).

LCMS (ESI) m/z=326 (M+Na)+

Retention time: 0.59 min (analysis condition SQDAA50)

Synthesis of (3)-5-bromo-2-tert-butoxycarbonylamino-4-methyldisulfanyl-pentanoic Acid Tert-Butyl Ester (Compound 32)

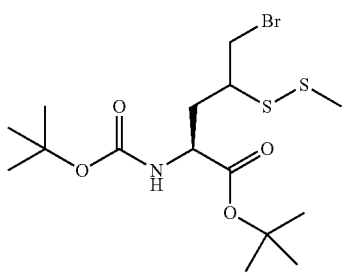 [SMILES: CSSC(CBr)C[C@H](NC(=O)OC(C)(C)C)C(=O)OC(C)(C)C]

Tetramethylurea (1.06 ml, 9.02 mmol) was added to a solution of (S)-2-tert-butoxycarbonylamino-3-thiiranyl-propionic acid tert-butyl ester (Compound 31) (2.28 g, 7.51 mmol) in dichloromethane (35 ml), and the mixture was cooled to −78° C. A separately prepared 1.60 M solution of methanesulfenyl bromide in 1,2-dichloroethane (5.17 ml) was added according to the method described in the Non patent literature (J. Org. Chem. 2001, 66, 910-914). The reaction solution was warmed from −78° C. to 0° C. with stirring over 2 hours. The reaction solution was concentrated under reduced pressure to afford (S)-5-bromo-2-tert-butoxycarbonylamino-4-methyldisulfanyl-pentanoic acid tert-butyl ester (Compound 32) as a crude product.

LCMS (ESI) m/z=430 (M+H)+

Retention time: 0.74 min (analysis condition SQDAA50)

2336

Synthesis of (S)-5-azido-2-tert-butoxycarbonylamino-4-methyldisulfanyl-pentanoic Acid Tert-Butyl Ester (Compound 33)

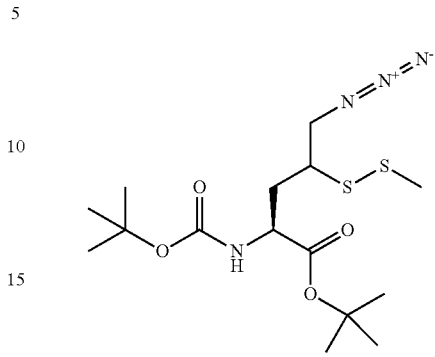

Sodium azide (2.44 g, 37.6 mmol) was added to a solution of the crude (S)-5-bromo-2-tert-butoxycarbonylamino-4-methyldisulfanyl-pentanoic acid tert-butyl ester (Compound 32) obtained in the foregoing in N,N-dimethylformamide (100 ml), and the reaction mixture was stirred at room temperature for 6 hours. After completion of the reaction, the insoluble matter was separated by filtration, and the filtrate was concentrated under reduced pressure. The resulting residue was purified by normal-phase silica gel column chromatography (hexane/ethyl acetate) to afford (S)-5-azido-2-tert-butoxycarbonylamino-4-methyldisulfanyl-pentanoic acid tert-butyl ester (Compound 33) (1.87 g, 64%).

LCMS (ESI) m/z=415 (M+Na)+

Retention time: 0.80 min (analysis condition SQDAA50)

Synthesis of (S)-2-amino-5-azido-4-methyldisulfanyl-pentanoic Acid Hydrochloride (Compound 34)

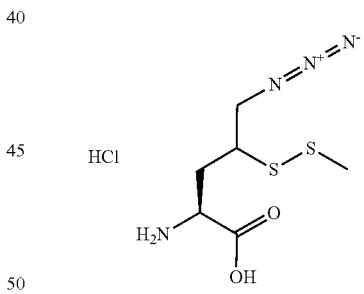

Chlorotrimethylsilane (297 µl, 2.344 mmol) was added to a solution of (S)-5-azido-2-tert-butoxycarbonylamino-4-methyldisulfanyl-pentanoic acid tert-butyl ester (Compound 33) (92 mg, 0.234 mmol) in 2,2,2-trifluoroethanol (0.9 ml), and the mixture was stirred at room temperature for 2 hours. Chlorotrimethylsilane (150 µL, 1.184 mmol) was further added, and the reaction solution was stirred at room temperature for 12 hours. After completion of the reaction, the reaction solution was concentrated under reduced pressure, and the resulting residue was washed with a mixed solvent of hexane/ethyl acetate/dichloromethane (3:1:0.1) to afford (S)-2-amino-5-azido-4-methyldisulfanyl-pentanoic acid hydrochloride (Compound 34) (58 mg, 91%).

LCMS (ESI) m/z=237 (M+H)+

Retention time: 0.36 min (analysis condition SQDFA05)

2337

Synthesis of (S)-5-azido-2-tert-butoxycarbonylamino-4-methyldisulfanyl-pentanoic Acid (Compound 35)

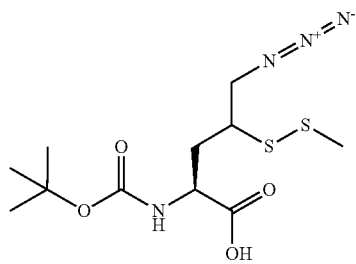 [SMILES: CSSC(CN=[N+]=[N-])C[C@H](NC(=O)OC(C)(C)C)C(=O)O]

Di-tert-butyl dicarbonate (112 mg, 0.513 mmol) and sodium bicarbonate (54 mg, 0.642 mmol) were added to a suspension of (S)-2-amino-5-azido-4-methyldisulfanyl-pentanoic acid hydrochloride (Compound 34) (70 mg, 0.257 mmol) in 1,4-dioxane (0.7 ml)/water (0.35 ml), and the reaction solution was stirred at room temperature for 3 hours. After completion of the reaction, the reaction solution was purified by reverse-phase silica gel column chromatography (10 mM aqueous ammonium acetate solution/methanol) to afford (S)-5-azido-2-tert-butoxycarbonylamino-4-methyldisulfanyl-pentanoic acid (Compound 35) (79 mg, 92%).

LCMS (ESI) m/z=335 (M−H)−
Retention time: 0.78 min (analysis condition SQDFA05)

Synthesis of (S)-5-azido-2-tert-butoxycarbonylamino-4-methyldisulfanyl-pentanoic Acid Cyanomethyl Ester (Compound 36)

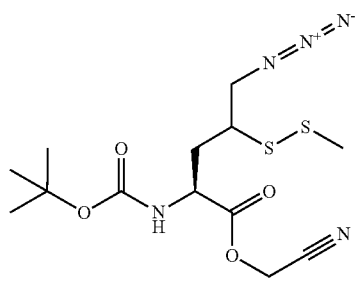 [SMILES: CSSC(CN=[N+]=[N-])C[C@H](NC(=O)OC(C)(C)C)C(=O)OCC#N]

Bromoacetonitrile (45 µl, 0.669 mmol) and N,N-diisopropylethylamine (58 µl, 0.334 mmol) were added to a solution of (S)-5-azido-2-tert-butoxycarbonylamino-4-methyldisulfanyl-pentanoic acid (Compound 35) (75 mg, 0.223 mmol) in acetonitrile (2 ml), and the reaction solution was stirred at room temperature for 5 hours. The reaction mixture was extracted with ethyl acetate/saturated ammonium chloride, and the organic layer was washed with brine. The organic layer was dried over anhydrous sodium sulfate, filtered and concentrated under reduced pressure. The resulting residue was purified by normal-phase silica gel column chromatography (hexane/ethyl acetate) to afford (S)-5-azido-2-tert-butoxycarbonylamino-4-methyldisulfanyl-pentanoic acid cyanomethyl ester (Compound 36) (81 mg, 97%).

LCMS (ESI) m/z=374 (M−H)−
Retention time: 0.87 min (analysis condition SQDFA05)

2338

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-azide-2-((tert-butoxycarbonyl)amino)-4-(methyldisulfanyl)pentanoate (Compound 37)

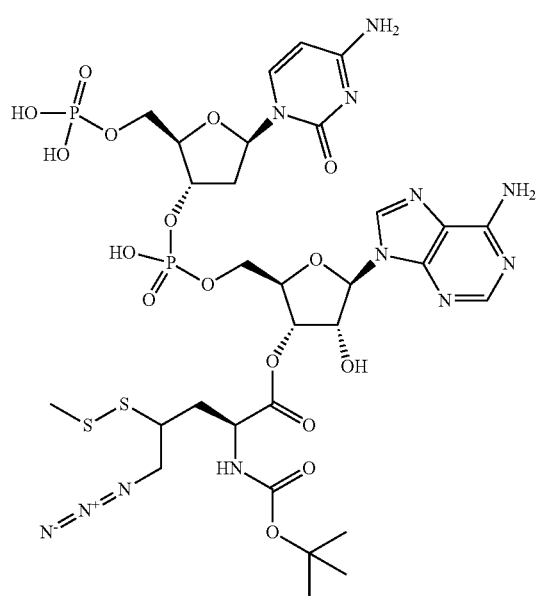 [SMILES: CSSC(CN=[N+]=[N-])C[C@H](NC(=O)OC(C)(C)C)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

A solution of H2R,3S,5R)-5-(4-amino-2-oxopyrimidin-1 (2H)-yl)-3-(((((2R,3S,4R,5R)-5-(6-amino-9H-purin-9-yl)-3, 4-dihydroxytetrahydrofuran-2-yl)methoxy)(hydroxy)phosphoryl)oxy)tetrahydrofuran-2-yl)methyl dihydrogenphosphate (Compound 1h) (45 mg, 0.071 mmol) in water (1 ml) and a solution of (S)-5-azido-2-tert-butoxycarbonylamino-4-methyldisulfanyl-pentanoic acid cyanomethyl ester (Compound 36) (80 mg, 0.213 mmol) in tetrahydrofuran (1 ml) were added to buffer A (29 mL), and the mixture was stirred at room temperature for 3 hours. Following lyophilization, the resulting residue was purified by reverse-phase silica gel column chromatography (0.1% aqueous formic-acid solution/0.1% formic acid-acetonitrile solution) to afford (2S)-(2R,3S,4R,5R)-2-(((((2R,3S,5R)-5-(4-amino-2-oxopyrimidin-1(2H)-yl)-2-((phosphonooxy) methyl)tetrahydrofuran-3-yl)oxy)(hydroxy)phosphoryl) oxy)methyl)-5-(6-amino-9H-purin-9-yl)-4-hydroxytetrahydrofuran-3-yl 5-azide-2-((tert-butoxycarbonyl)amino)-4-(methyldisulfanyl)pentanoate (Compound 37) (15 mg, 22%).

LCMS (ESI) m/z=955 (N+H)+
Retention time: 0.55 min (analysis condition SQDFA05)

2-4. Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-azido-4-(methyldisulfanyl)pentanoate (Orn(N3)(4-SSMe)-pdCpA) (Compound 27)

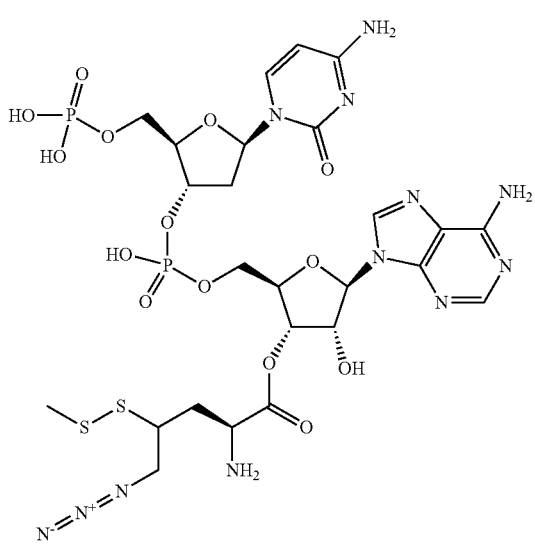 [SMILES: CSSC(CN=[N+]=[N-])C[C@H](N)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

Trifluoroacetic acid (0.2 mL) was added to (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-azide-2-((tert-butoxycarbonyl)amino)-4-(methyldisulfanyl)pentanoate (Compound 37) (10 mg, 10.47 μmol) at room temperature, and the mixture was stirred at the same temperature for 20 minutes. Following concentration under reduced pressure, the resulting residue was purified by reverse-phase silica gel column chromatography (0.1% aqueous formic acid solution/0.1% formic acid-acetonitrile solution) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-azido-4-(methyldisulfanyl)pentanoate (Orn(N3)(4-SSMe)-pdCpA) (Compound 27) (2 mg, 26%).

LCMS (ESI) m/z=855 (M+H)+

Retention time: 0.32 minute (analysis condition SQDFA05)

2-5. Synthesis of Aminoacylated pdCpA Compound 43

Synthesis of (2S,2'S)-di-tert-butyl 4,4'-disulfanediylbis(5-azide-2-((tert-butoxycarbonyl)amino)pentanoate) (Compound 38)

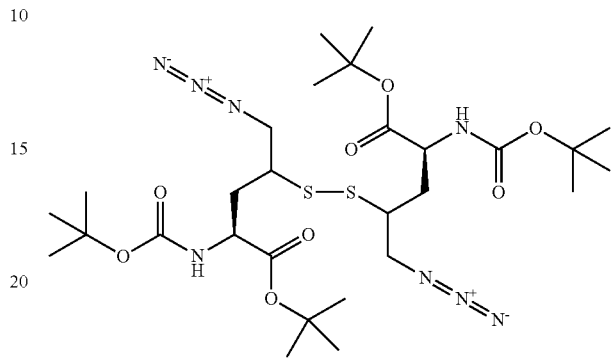

(2S,2'S)-Di-tert-butyl 4,4'-disulfanediylbis(5-azido-2-((tert-butoxycarbonyl)amino)pentanoate) (Compound 38) (414 mg) was obtained as a by-product in the above-described synthesis of (S)-5-azido-2-tert-butoxycarbonylamino-4-methyldisulfanyl-pentanoic acid tert-butyl ester (Compound 33).

LCMS (ESI) m/z=691.7 (M+H)+

Retention time: 0.80 min (analysis condition SQDAA50)

Synthesis of (S)-5-azido-2-tert-butoxycarbonylamino-4-tert-butyldisulfanyl-pentanoic Acid Tert-Butyl Ester (Compound 39)

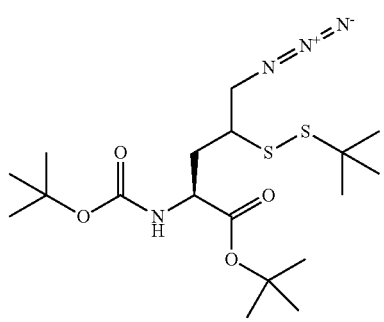 [SMILES: CC(C)(C)OC(=O)N[C@@H](CC(CN=[N+]=[N-])SSC(C)(C)C)C(=O)OC(C)(C)C]

Di-tert-butyl disulfide (5.67 ml, 29.4 mmol) and iodine (57 mg, 0.226 mmol) were added to (2S,2'S)-di-tert-butyl 4,4'-disulfanediylbis(5-azido-2-((tert-butoxycarbonyl)amino)pentanoate) (Compound 38) (312 mg, 0.452 mmol), and the mixture was stirred at 60° C. for 18 hours. The reaction solution was purified by normal-phase silica gel column chromatography (hexane/ethyl acetate) to afford (S)-5-azido-2-tert-butoxycarbonylamino-4-tert-butyldisulfanyl-pentanoic acid tert-butyl ester (Compound 39) (161 mg, 81%).

LCMS (ESI) m/z=435.5 (M+H)+

Retention time: 0.77 min (analysis condition SQDAA50)

2341

Synthesis of (S)-2-amino-5-azido-4-tert-butyldisulfanyl-pentanoic Acid Hydrochloride (Compound 40)

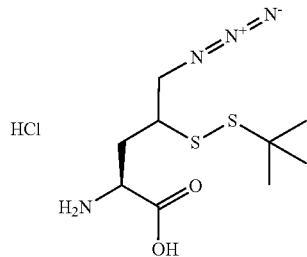 [SMILES: Cl ; CC(C)(C)SSC(CN=[N+]=[N-])C[C@H](N)C(=O)O]

Chlorotrimethylsilane (467 μl, 2.344 mmol) was added to a solution of (S)-5-azido-2-tert-butoxycarbonylamino-4-tert-butyldisulfanyl-pentanoic acid tert-butyl ester (Compound 39) (160 mg, 0.368 mmol) in 2,2,2-trifluoroethanol (3.2 ml), and the mixture was stirred at room temperature for 2 hours. Chlorotrimethylsilane (467 μl, 2.344 mmol) was further added, and the reaction solution was stirred at room temperature for 3 hours. After completion of the reaction, the reaction solution was concentrated under reduced pressure, and the resulting residue was washed with a mixed solvent of hexane/ethyl acetate/dichloromethane (3:1:0.1) to afford (S)-2-amino-5-azido-4-tert-butyldisulfanyl-pentanoic acid hydrochloride (Compound 40) (113 mg, 97%).

LCMS (ESI) m/z=279 (M+H)+
Retention time: 0.78 min (analysis condition SQDAA05)

Synthesis of (S)-5-azido-2-tert-butoxycarbonylamino-4-tert-butyldisulfanyl-pentanoic Acid (Compound 40a)

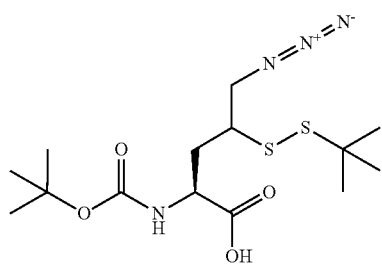 [SMILES: CC(C)(C)OC(=O)N[C@@H](CC(CN=[N+]=[N-])SSC(C)(C)C)C(=O)O]

Di-tert-butyl dicarbonate (152 mg, 0.699 mmol) and sodium bicarbonate (73 mg, 0.873 mmol) were added to a solution of (S)-2-amino-5-azido-4-tert-butyldisulfanyl-pentanoic acid hydrochloride (Compound 40) (110 mg, 0.349 mmol) in 1,4-dioxane (1 ml)/water (0.5 ml), and the reaction solution was stirred at room temperature for 1.5 hours. Di-tert-butyl dicarbonate (152 mg, 0.699 mmol) and sodium bicarbonate (73 mg, 0.873 mmol) were further added, and the reaction solution was stirred at room temperature for 2 hours. After completion of the reaction, The reaction solution was purified by normal-phase silica gel column chromatography (dichloromethane/methanol) to afford (S)-5-azido-2-tert-butoxycarbonylamino-4-tert-butyldisulfanyl-pentanoic acid (Compound 40a) (120 mg, 91%).

LCMS (ESI) m/z=377 (M–H)–
Retention time: 0.89 min (analysis condition SQDFA05)

2342

Synthesis of (S)-5-azido-2-tert-butoxycarbonylamino-4-tert-butyldisulfanyl-pentanoic Acid Cyanomethyl Ester (Compound 41)

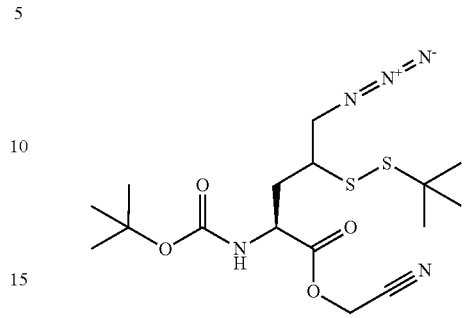

Bromoacetonitrile (62 μl, 0.911 mmol) and N,N-diisopropylethylamine (79 μl, 0.456 mmol) were added to a solution of (S)-5-azido-2-tert-butoxycarbonylamino-4-tert-butyldisulfanyl-pentanoic acid (Compound 40a) (115 mg, 0.304 mmol) in acetonitrile (1 ml), and the reaction solution was stirred at room temperature for 2 hours. The reaction mixture was extracted with ethyl acetate/saturated ammonium chloride, and the organic layer was washed with brine. The organic layer was dried over anhydrous sodium sulfate, filtered and concentrated under reduced pressure. The resulting residue was purified by normal-phase silica gel column chromatography (hexane/ethyl acetate) to afford (S)-5-azido-2-tert-butoxycarbonylamino-4-tert-butyldisulfanyl-pentanoic acid cyanomethyl ester (Compound 41) (120 mg, 95%).

LCMS (ESI) m/z=416 (M–H)–
Retention time: 0.97 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-azide-2-((tert-butoxycarbonyl)amino)-4-(tert-butyldisulfanyl)pentanoate (Compound 42)

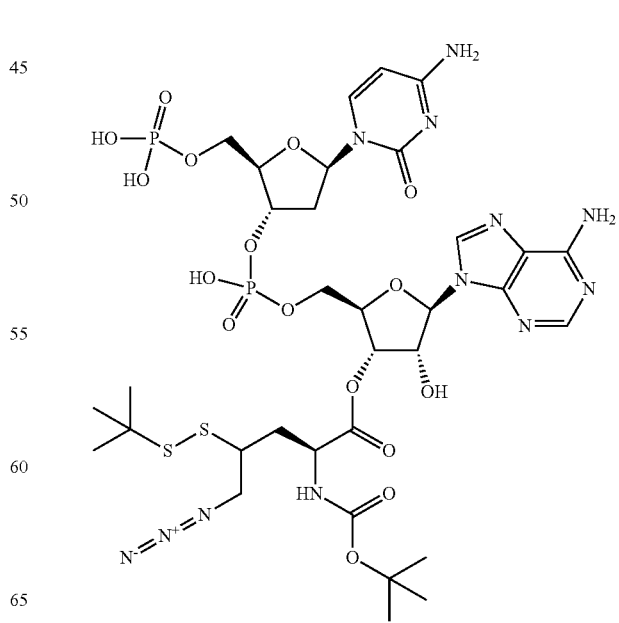

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (56 mg, 0.088 mmol) in water (1 ml) and a solution of (S)-5-azido-2-tert-butoxycarbonylamino-4-tert-butyldisulfanyl-pentanoic acid cyanomethyl ester (Compound 41) (110 mg, 0.263 mmol) in tetrahydrofuran (1 ml) were added to buffer A (29 mL), and the mixture was stirred at room temperature for 3 hours. Following lyophilization, the resulting residue was purified by reverse-phase silica gel column chromatography (0.05% aqueous trifluoroacetic acid solution/0.05% trifluoroacetic acid-acetonitrile solution) to afford a crude product of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-azido-2-((tert-butoxycarbonyl)amino)-4-(tert-butyldisulfanyl)pentanoate (Compound 42) (55 mg).

LCMS (ESI) m/z=997 (M+H)+

Retention time: 0.64 minute (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-azido-4-(tert-butyldisulfanyl)pentanoate (Orn(N3)(4-SStBu)-pdCpA) (Compound 43)

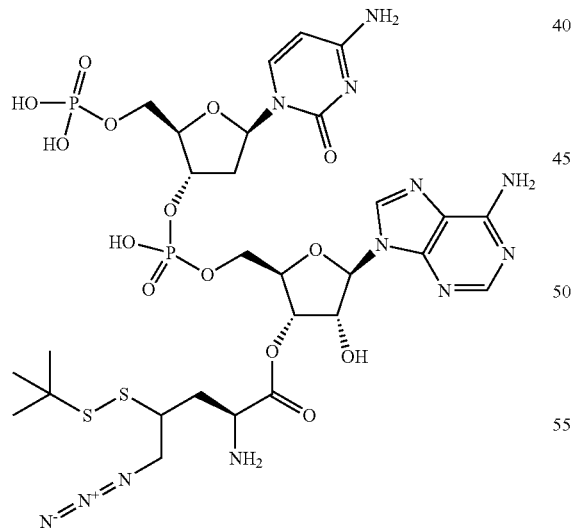

The aforementioned crude product of (2,9)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-azide-2-((tert-butoxycarbonyl)amino)-4-(tert-butyldisulfanyl)pentanoate (Compound 42) (53 mg) was suspended by adding dichloromethane (2 ml) thereto, after which trifluoroacetic acid (0.5 mL) was added at room temperature, and the mixture was stirred at the same temperature for 30 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-azido-4-(tert-butyldisulfanyl)pentanoate (Orn(N3)(4-SStBu)-pdCpA) (Compound 43) (24 mg, 31% in two steps).

LCMS (ESI) m/z=897 (M+H)+

Retention time: 0.41 min (analysis condition SQDFA05)

2-6. Synthesis of Aminoacylated pdCpA Compound 47

The method described below that can modify the protecting group for SH in Compound 36 in one step established a method of easily synthesizing a pdCpA derivative.

Synthesis of (2S)-cyanomethyl 5-azido-2-(tert-butoxycarbonylamino)-4-(isopropyldisulfanyl)pentanoate (Compound 45)

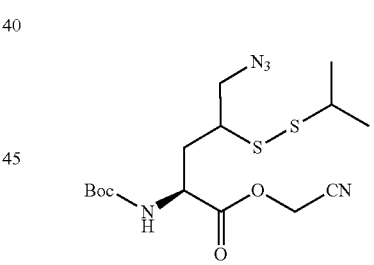

Diisopropyl disulfide (4.67 ml, 29.3 mmol) and iodine (30 mg, 0.117 mmol) were added to (2S)-cyanomethyl 5-azido-2-(tert-butoxycarbonylamino)-4-(methyldisulfanyl)pentanoate (Compound 36) (110 mg, 0.293 mmol), and the mixture was stirred at 60° C. for 24 hours.

The reaction solution was purified by normal-phase silica gel column chromatography (hexane/ethyl acetate) to afford (2S)-cyanomethyl 5-azido-2-(tert-butoxycarbonylamino)-4-(isopropyldisulfanyl)pentanoate (Compound 45) (89 mg, 75%).

LCMS (ESI) m/z=402 (M−H)−

Retention time: 0.61 min (analysis condition SQDAA50)

Compound 46

Synthesis of (2S)-(2R,3S,4R,5R)-2-((((((2R,3S,5R)-5-(4-amino-2-oxopyrimidine-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-azido-2-((tert-butoxycarbonyl)amino)-4-(isopropyldisulfanyl)pentanoate

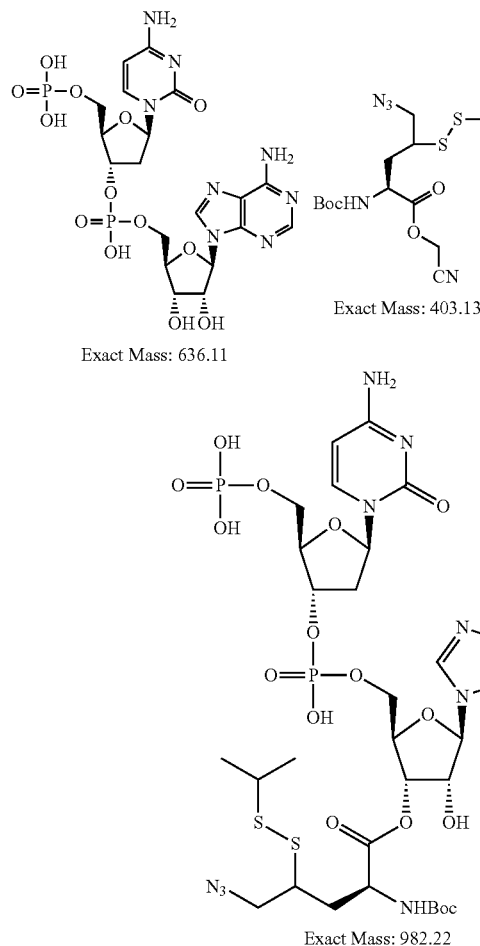

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h, 43.6 mg, 0.069 mmol) in water (0.3 mL) and a solution of (2S)-cyanomethyl 5-azido-2-((tert-butoxycarbonyl)amino)-4-(isopropyldisulfanyl)pentanoate (Compound 45) (83 mg, 0.206 mmol) in tetrahydrofuran (0.2 mL) were added to buffer A (12 mL), and the mixture was stirred at room temperature for 55 minutes. Following lyophilization, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidine-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-azido-2-((tert-butoxycarbonyl)amino)-4-(isopropyldisulfanyl)pentanoate (Compound 46) (27.7 mg, 41%).

LCMS (ESI) m/z=981.6 (M−H)−
Retention time: 0.58 min (analysis condition SQDFA05)

Compound 47

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-azido-4-(isopropyldisulfanyl)pentanoate (Orn(N3)(4-SSiPr)-pdCpA)

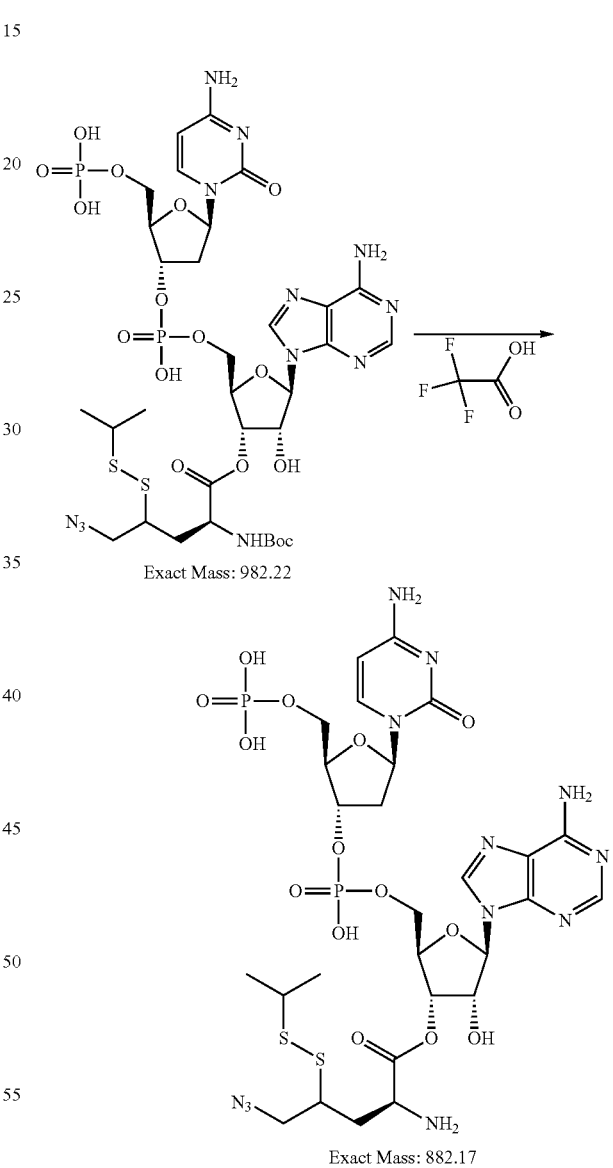

Trifluoroacetic acid (0.1 mL) was added to a solution of (2S)-(2R,3S,4R,5R)-2-((((((2R,3S,5R)-5-(4-amino-2-oxopyrimidine-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-azido-2-((tert-butoxycarbonyl)amino)-4-(isopropyldisulfanyl)pentanoate (Compound 46) (27.7 mg, 28 μmol) in dichloromethane (0.4 mL), and the mixture was stirred for 35 minutes at room temperature. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-azido-4-(isopropyldisulfanyl)pentanoate (Orn(N3) (4-SSiPr)-pdCpA) (Compound 47) (21.5 mg, 86%).

LCMS (ESI) m/z=881.4 (M–H)–
Retention time: 0.39 min (analysis condition SQDFA05)

2-5. Synthesis of Aminoacylated pdCpA Compound 48 (Lys(Cys(StBu))-pdCpA)

The synthesis was carried out according to the following scheme.

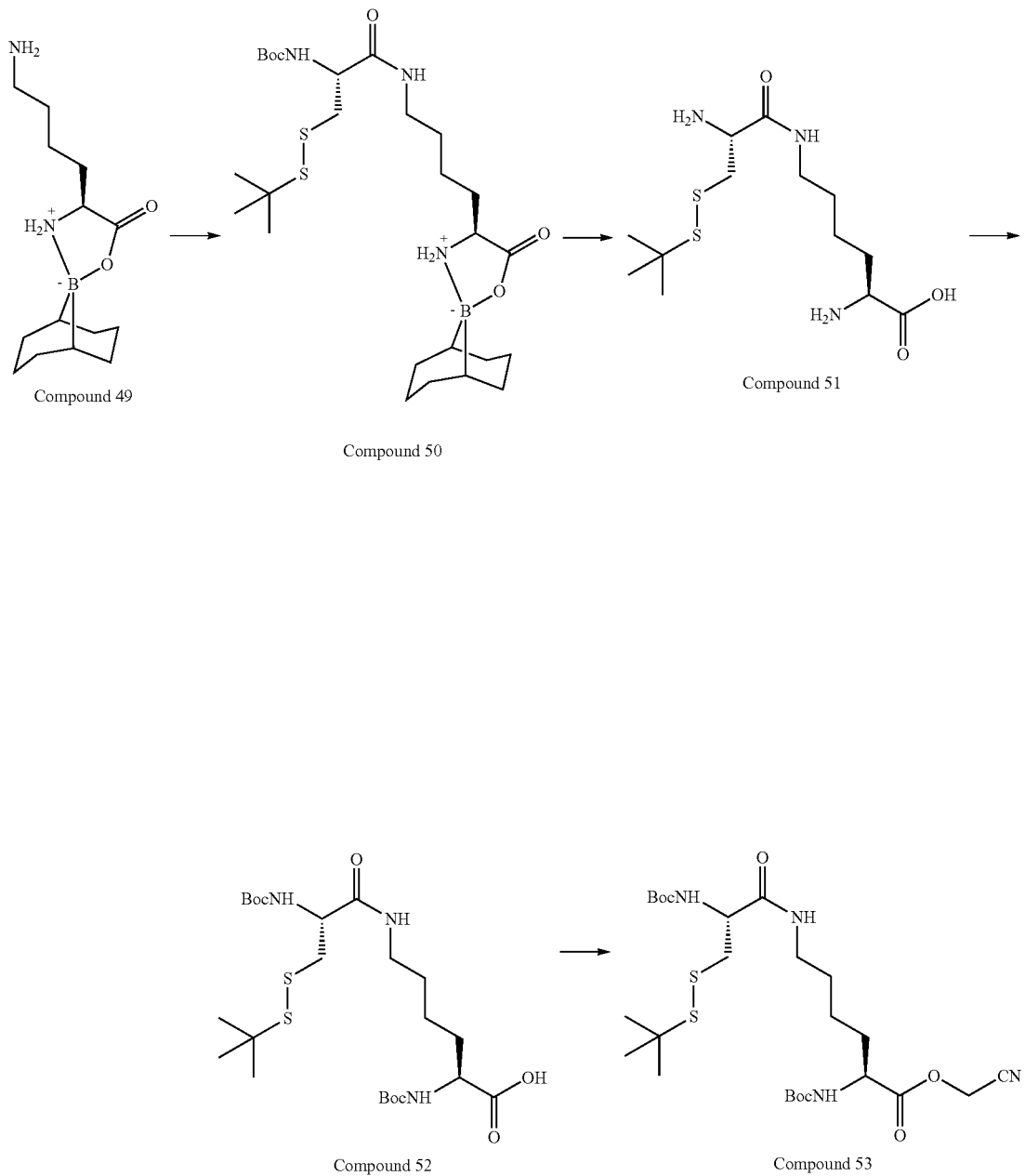

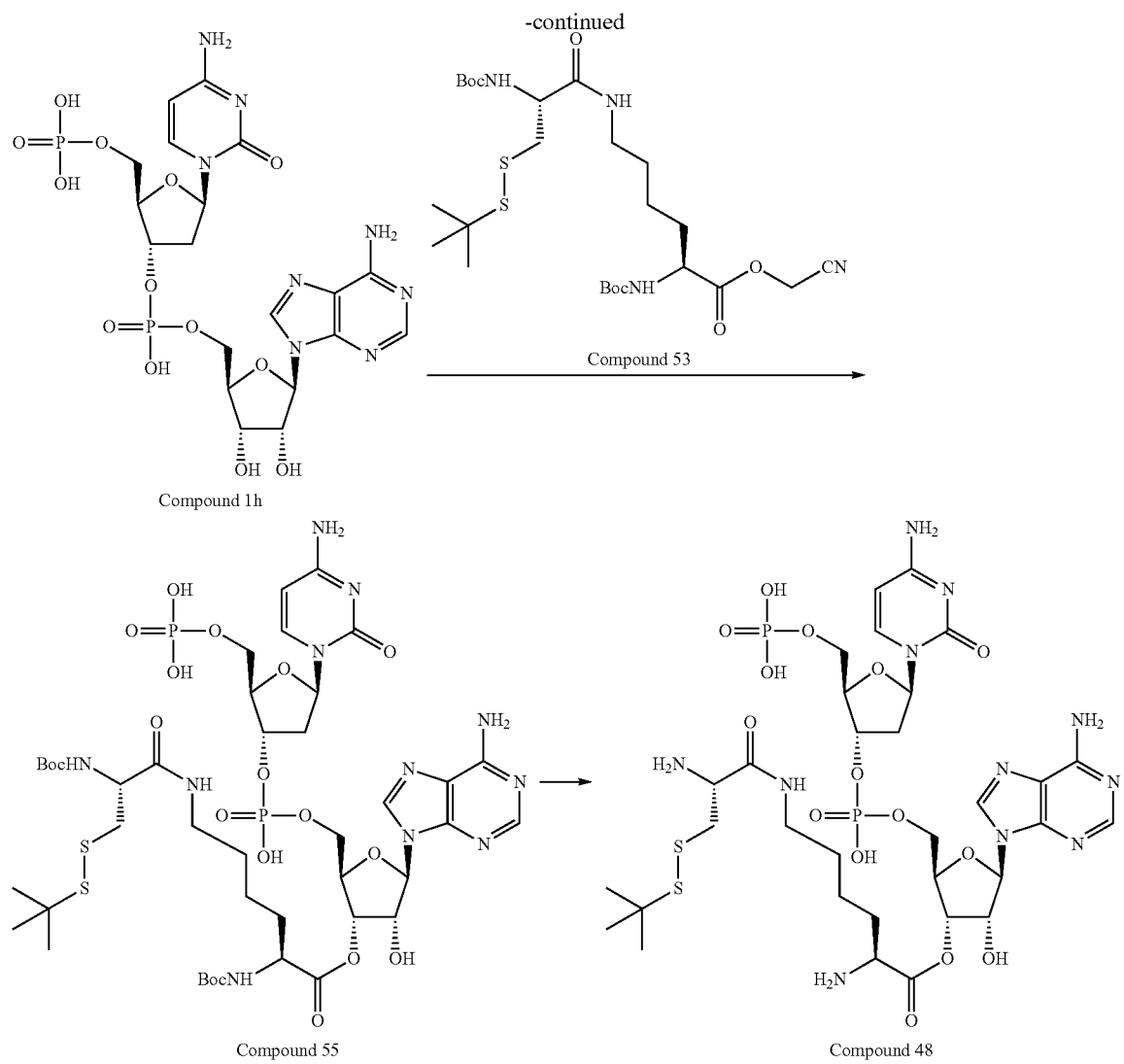

Synthesis of (S)-2,6-diaminohexanoic Acid, Diammonium Salt Hydrochloride (Compound 56)

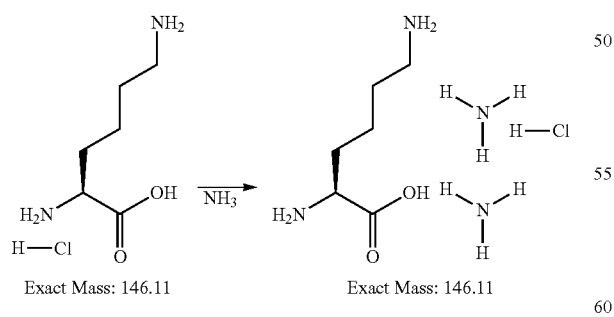

L(+)-lysine monohydrochloride (3.08 g, 16.86 mmol) was cooled in an ice bath, followed by addition of aqueous ammonia (15 mL). The reaction solution was stirred at the same temperature for 25 minutes and then concentrated under reduced pressure, and the resulting crude product (3.20 g) was directly used for the next step.

Synthesis of (1R,4'S,5S)-4'-(4-aminobutyl)-5'-oxospiro[bicyclo[3.3.1]nonane-9,2'-[1,3,2]oxazaboroliin]-3'-ium-11-uide (Compound 49)

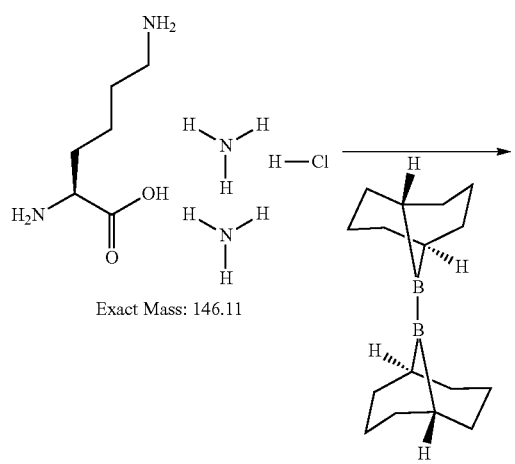

Exact Mass: 146.11

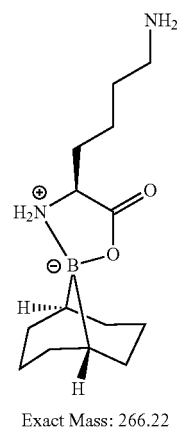

Exact Mass: 266.22

A suspension of (S)-2,6-diaminohexanoic acid, diammonium salt hydrochloride (Compound 56) (3.20 g, 14.77 mmol) and 9-BBN dimer (4.11 g, 16.98 mmol) in methanol (40 mL) was heated at reflux for 1 hour under a nitrogen atmosphere. After cooling to room temperature, the solvent was evaporated under reduced pressure, and the resulting crude product was directly used for the next step.

LCMS (ESI) m/z=265 (M–H)–
Retention time: 0.43 min (analysis condition SQDFA05)

Synthesis of (1R,4'S,5S)-4'-(4-((R)-2-((tert-butoxycarbonyl)amino)-3-(tert-butyldisulfanyl)propanamide)butyl)-5'-oxospiro[bicyclo[3.3.1]nonane-9,2'-[1,3,2]oxazaboroliin]-3'-ium-11-uide (Compound 50)

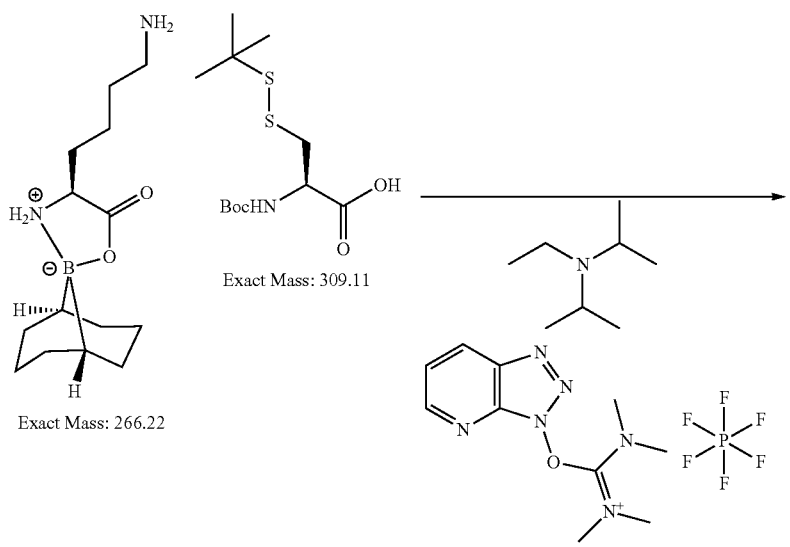

Exact Mass: 266.22

Exact Mass: 309.11

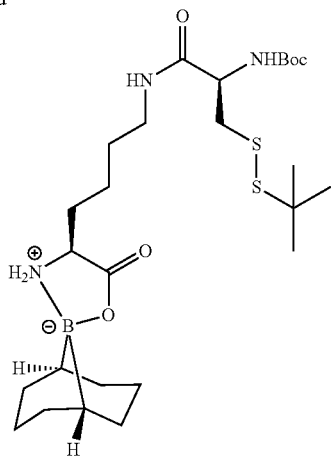

Exact Mass: 557.3

N,N-Diisopropylethylamine (3.66 mL, 21 mmol) was added to a suspension of (1R,4'S,5S)-4'-(4-aminobutyl)-5'-oxospiro[bicyclo[3.3.1]nonane-9,2'-[1,3,2]oxazaboroliin]-3'-ium-11-uide (Compound 49) (3.73 g, 14 mmol) and Boc-Cys(StBu)-OH (4.33 g, 14 mmol) in DMF (10 mL) with stirring at room temperature under a nitrogen atmosphere. HATU (5.86 g, 15.4 mmol) was added to the resulting mixture, followed by stirring at room temperature for one day. Brine was added to the reaction mixture, followed by extraction with ethyl acetate. The organic phase was dried over anhydrous sodium sulfate and then concentrated under reduced pressure, and the resulting crude product was purified by normal-phase silica gel column chromatography (dichloromethane/ethyl acetate) to afford (1R, 4'S,5S)-4'-(4-((R)-2-((tert-butoxycarbonyl)amino)-3-(tert-butyldisulfanyl)propanamide)butyl)-5,-oxospiro[bicyclo[3.3.1]nonane-9,2'-[1,3,2]oxazaborolidin]-3'-ium-11-uide (Compound 50) (7.34 g, 94%).

LCMS (ESI) m/z=558.5 (M+H)+
Retention time: 0.98 min (analysis condition SQDFA05)

Synthesis of (S)-2-amino-6-((R)-2-amino-3-(tert-butyldisulfanyl)propanamido)hexanoic Acid (Lys(Cys(StBu))) (Compound 51)

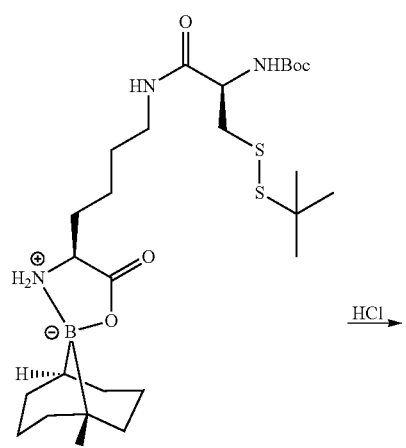

Exact Mass: 557.3

-continued

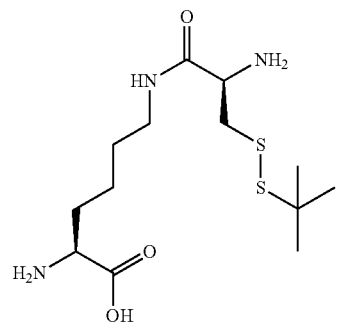

Exact Mass: 337.15

Concentrated hydrochloric acid (1.1 mL) was added to a solution of (1R,4'S,5S)-4'-(4-((R)-2-((tert-butoxycarbonyl)amino)-3-(tert-butyldisulfanyl)propanamide)butyl)-5'-oxospiro[bicyclo[3.3.1]nonane-9,2'-[1,3,2]oxazaborolidin]-3'-ium-11-uide (Compound 50) (715.8 mg, 1.28 mmol) in 1,4-dioxane (3 mL) at room temperature, and the resulting reaction mixture was stirred at 40° C. for 13 hours and 15 minutes. After cooling to room temperature, the reaction mixture was concentrated under reduced pressure, and the resulting crude product was purified by Reverse-phase silica gel column chromatography (10 mM aqueous ammonium acetate solution/methanol) to afford (S)-2-amino-6-((R)-2-amino-3-(tert-butyldisulfanyl)propanamido)hexanoic acid (Lys(Cys(StBu))) (Compound 51) (394.1 mg, 91%).

LCMS (ESI) m/z=336 (M−H)−
Retention time: 0.67 min (analysis condition SQDAA05)

2355

Synthesis of (S)-2-((tert-butoxycarbonyl)amino)-6-((R)-2-((tert-butoxycarbonyl)amino)-3-(tert-butyldisulfanyl)propanamido)hexanoic Acid (Compound 52)

2356

Synthesis of (S)-cyanomethyl 2-((tert-butoxycarbonyl)amino)-6-((R)-2-((tert-butoxycarbonyl)amino)-3-(tert-butyldisulfanyl)propanamido)hexanoate (Compound 53)

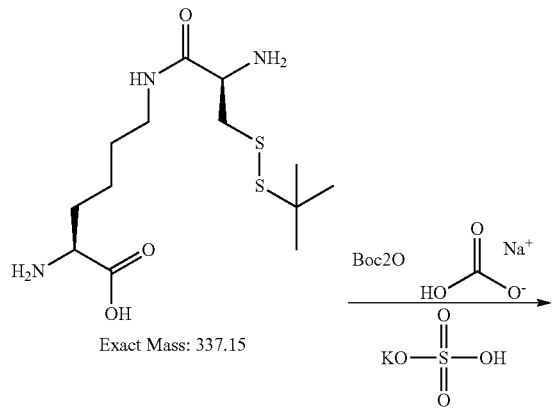

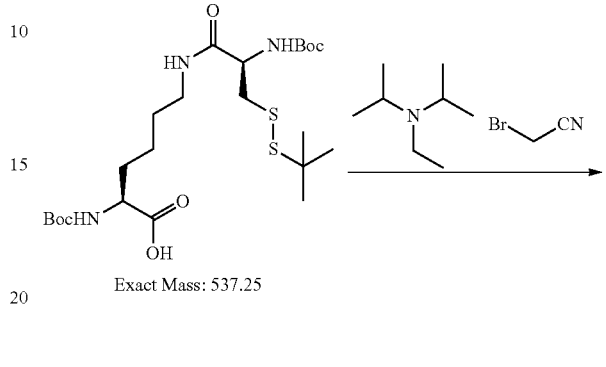

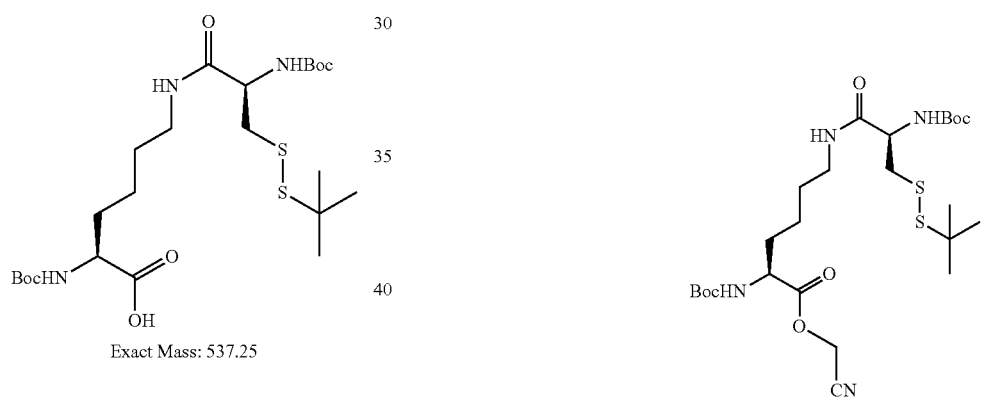

A mixture of (S)-2-amino-6-((R)-2-amino-3-(tert-butyldisulfanyl)propanamido)hexanoic acid (Lys(Cys(StBu))) (Compound 51) (390 mg, 1.16 mmol) in 1,4-dioxane (5 mL) and water (6 mL) was cooled in an ice bath, and sodium bicarbonate (388 mg, 4.62 mmol) and subsequently Boc$_2$O (807 mg, 3.70 mmol) were added. The reaction mixture was stirred at room temperature for 3 hours. The reaction mixture was cooled in an ice bath and then adjusted to pH 2 by adding potassium bisulfate (157 mg, 1.16 mmol) and a saturated aqueous potassium bisulfate solution (1 mL) thereto. The resulting mixture was extracted with ethyl acetate. The organic phase was dried over anhydrous sodium sulfate and then concentrated under reduced pressure, and the resulting crude product was purified by normal-phase silica gel column chromatography (ethyl acetate) to afford (S)-2-((tert-butoxycarbonyl)amino)-6-((R)-2-((tert-butoxycarbonyl)amino)-3-(tert-butyldisulfanyl)propanamido)hexanoic acid (Compound 52) (579.5 mg, 93%).

LCMS (ESI) m/z=536 (M-H)-

Retention time: 0.86 min (analysis condition SQDFA05)

N,N-diisopropylethylamine (0.073 mL, 0.421 mmol) and subsequently bromoacetonitrile (0.080 mL, 1.15 mmol) were added to a solution of (S)-2-((tert-butoxycarbonyl)amino)-6-((R)-2-((tert-butoxycarbonyl)amino)-3-(tert-butyldisulfanyl)propanamido)hexanoic acid (Compound 52) (206 mg, 0.383 mmol) in acetonitrile (0.3 mL) at room temperature under a nitrogen atmosphere. The reaction mixture was stirred at the same temperature for 5 hours and then concentrated under reduced pressure, and the resulting crude product was purified by normal-phase silica gel column chromatography (hexane/ethyl acetate) to afford (S)-cyanomethyl 2-((tert-butoxycarbonyl)amino)-6-((R)-2-((tert-butoxycarbonyl)amino)-3-(tert-butyldisulfanyl) propanamido)hexanoate (Compound 53) (172.2 mg, 78%).

LCMS (ESI) m/z=577.6 (M+H)+

Retention time: 0.92 min (analysis condition SQDFA05)

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-6-((R)-2-((tert-butoxycarbonyl)amino)-3-(tert-butyldisulfanyl)propanamido)hexanoate (Compound 55)

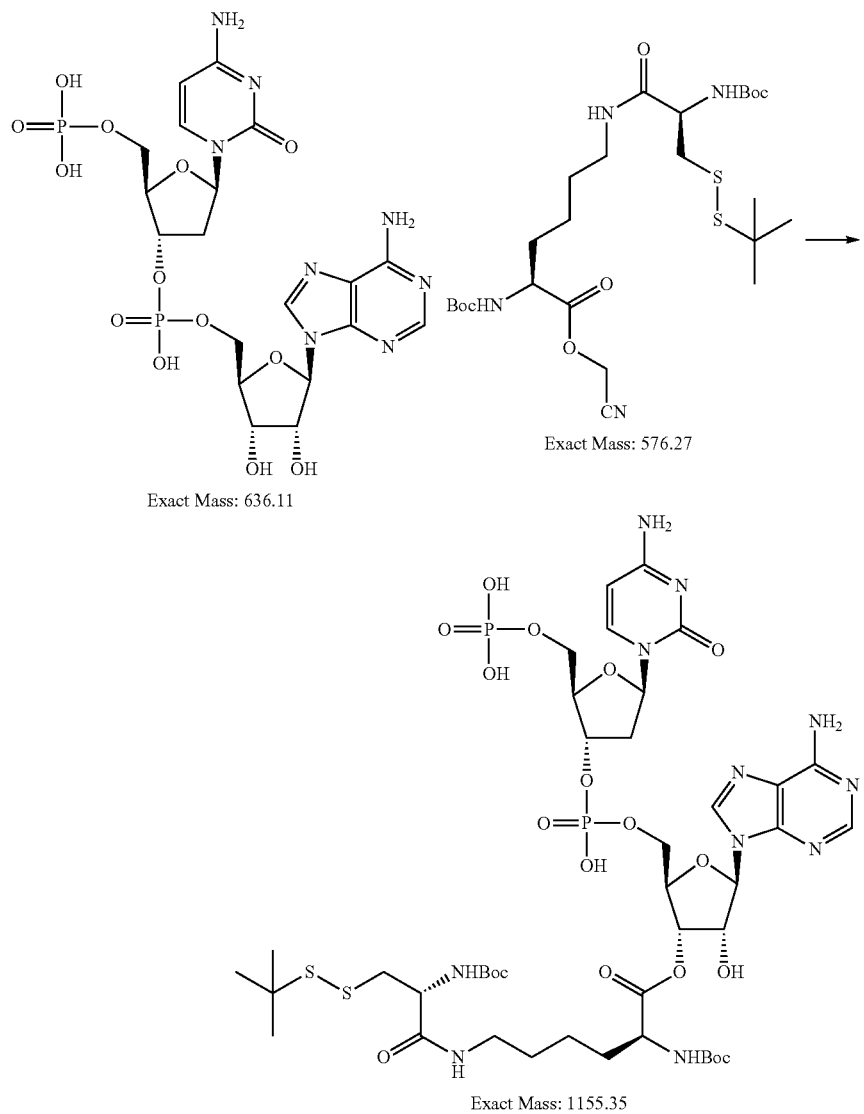

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (37.9 mg, 0.060 mmol) in water (0.3 mL) and a solution of (S)-cyanomethyl 2-((tert-butoxycarbonyl)amino)-6-((R)-2-((tert-butoxycarbonyl)amino)-3-(tert-butyldisulfanyl)propanamido)hexanoate (Compound 53) (103 mg, 0.179 mmol) in tetrahydrofuran (0.3 mL) were added to buffer A (11 mL), and the mixture was stirred at room temperature for 2 hours. Following lyophilization, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-6-((R)-2-((tert-butoxycarbonyl)amino)-3-(tert-butyldisulfanyl)propanamido)hexanoate (Compound 55) (12 mg, 17%).

LCMS (ESI) m/z=1156.7 (M+H)+

Retention time: 0.63 min (analysis condition SQDFA05)

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-((R)-2-amino-3-(tert-butyldisulfanyl)propanamido)hexanoate (Lys(Cys(StBu))-pdCpA) (Compound 48)

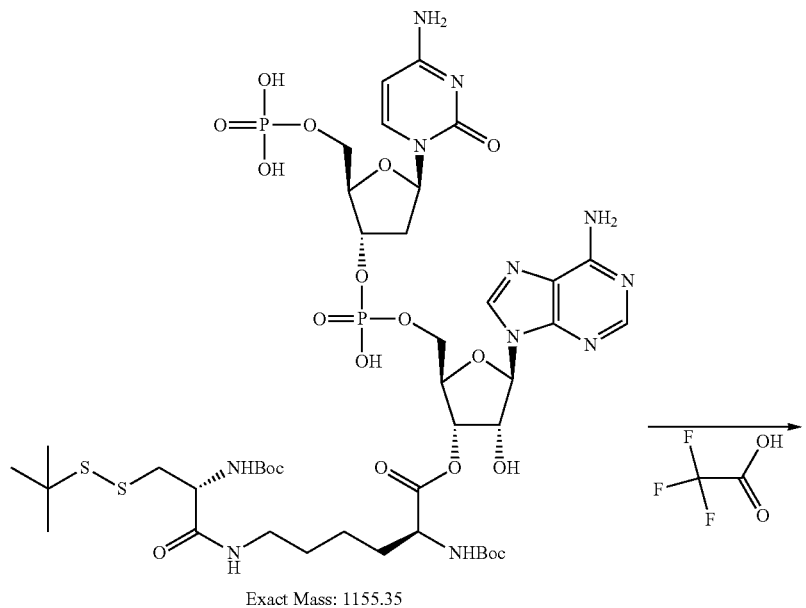

Exact Mass: 1155.35

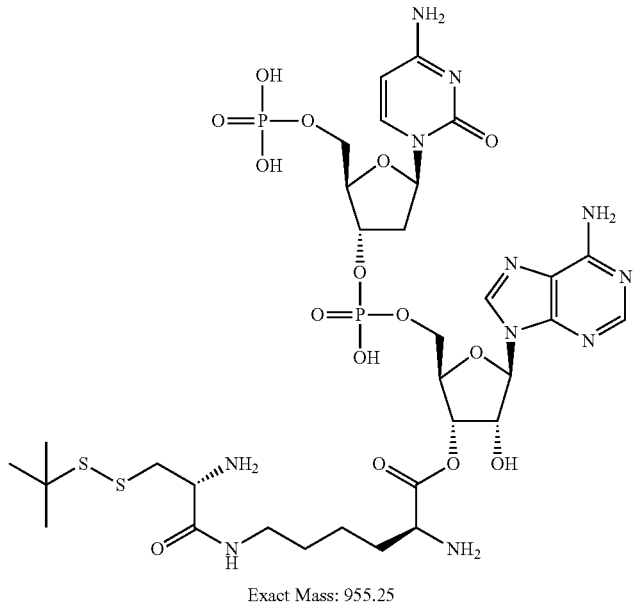

Exact Mass: 955.25

Trifluoroacetic acid (0.1 mL) was added to a solution of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-6-((R)-2-((tert-butoxycarbonyl)amino)-3-(tert-butyldisulfanyl)propanamido)hexanoate (Compound 55) (12 mg, 10.38 μmol) in dichloromethane (0.4 mL) at room temperature, and the mixture was stirred at the same temperature for 15 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-((R)-2- amino-3-(tert-butyldisulfanyl)propanamido)hexanoate (Lys (Cys(StBu))-pdCpA) (Compound 48) (9.3 mg, 94%).

LCMS (ESI) m/z=956 (M+H)+

Retention time: 0.29 min (analysis condition SQDFA05)

10. Synthesis of Amine Sites Having Protecting Groups (Part 2)

Searching for protecting groups that can be translationally synthesized and protected under reaction conditions where RNA is stable, and examples of combinations of them with amino acid units will be illustrated below. Abbreviations of the respective amino acids used herein are shown below together with Compound Nos. Such abbreviations indicate the same units contained either in peptides or in RNAs or DNAs such as pdCpAs. In addition, H-Gly-OH may be simply described as Gly by omitting the description of H and OH groups when the N- or C-terminal is not chemically modified.

Compound tk100

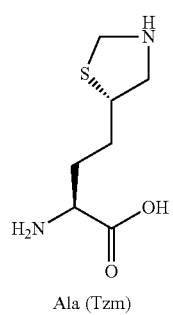

Ala (Tzm)

Compound tk101

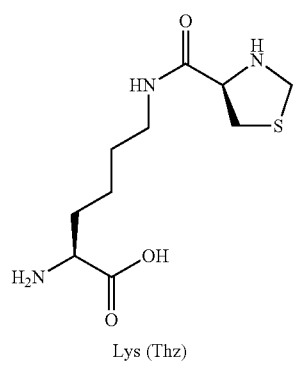

Lys (Thz)

Compound tk102

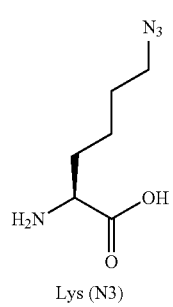

Lys (N3)

Compound tk103

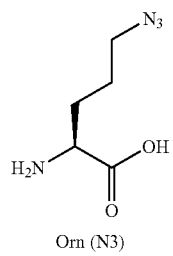

Orn (N3)

Compound tk104

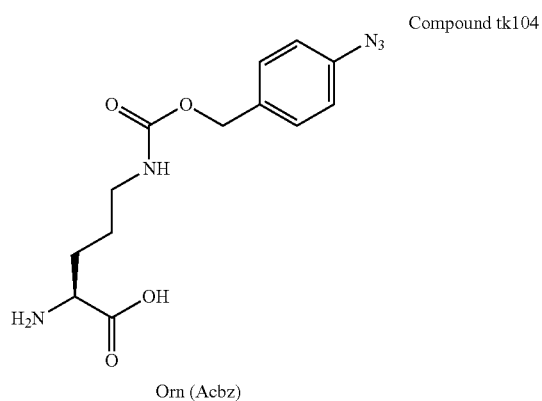

Orn (Acbz)

Compound tk34

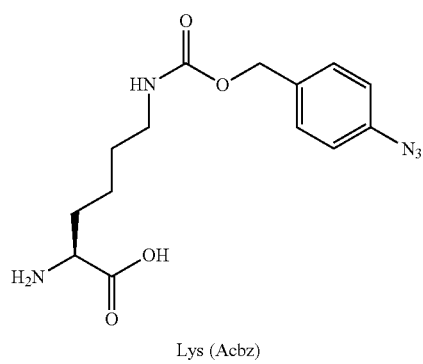

Lys (Acbz)

Compound tk7

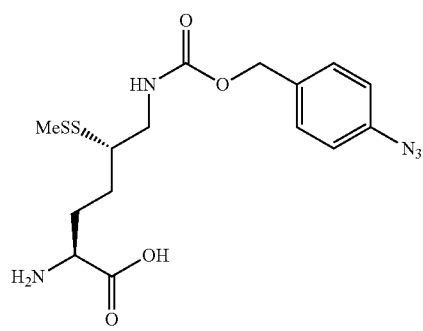

Lys (5S-SSMe) (Acbz)

Compound tk14

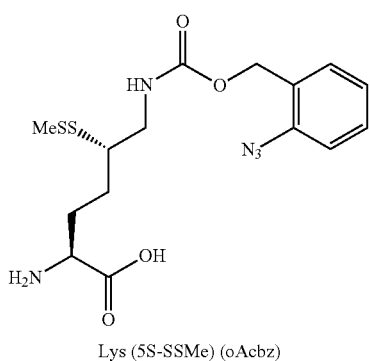

Lys (5S-SSMe) (oAcbz)

Compound tk105

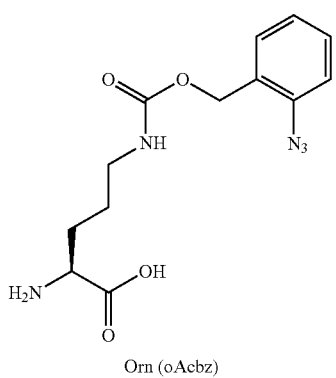

Orn (oAcbz)

Compound tk106

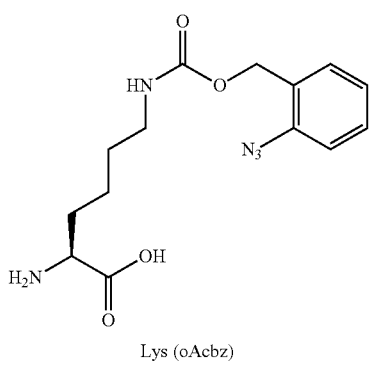

Lys (oAcbz)

Compound tk107

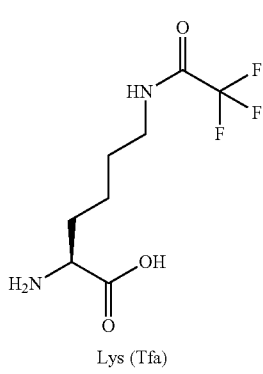

Lys (Tfa)

Compound tk108

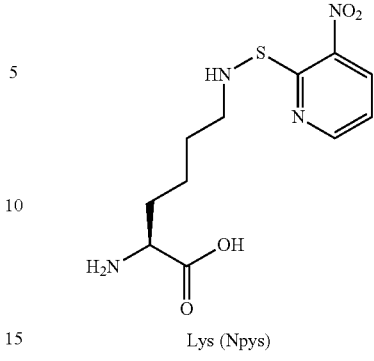

Lys (Npys)

Abbreviations of the respective amino acids used herein are defined below as amino acids that can be translationally synthesized.

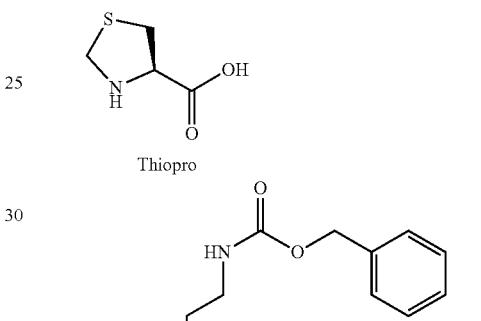

Thiopro

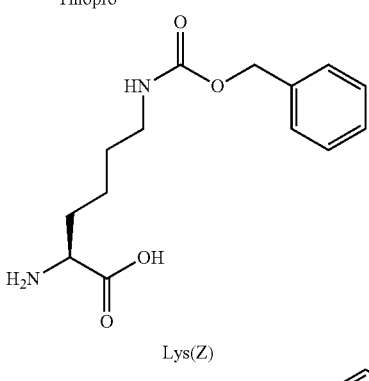

Lys(Z)

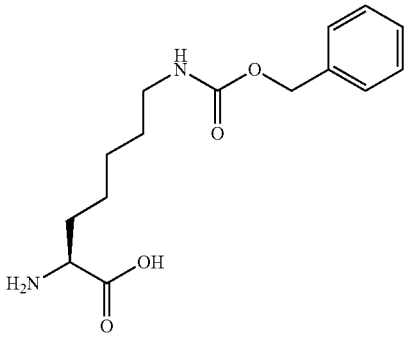

Orn(Z)

10-1. Synthesis of pdCpA Linked Amino Acids Having Side Chain Amino Group Protected 10-1-1. Searching for Amine Sites Having Protecting Groups: Synthesis of Aminoacylated pdCpA Compound tk5

The synthesis was carried out according to the following scheme.

TK scheme 1
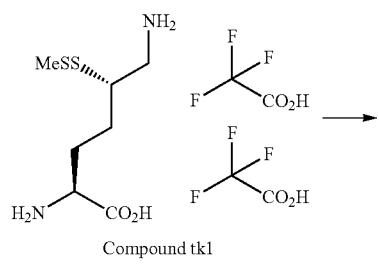
Compound tk1
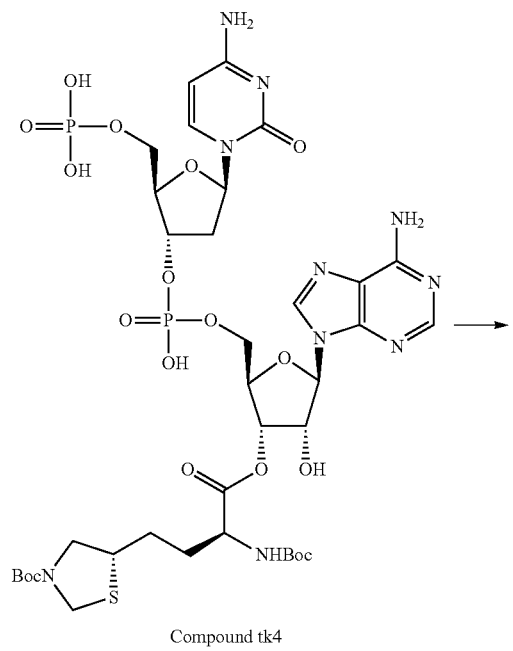
Compound tk4
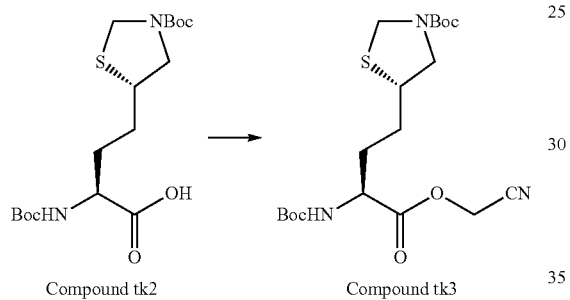
Compound tk2 → Compound tk3
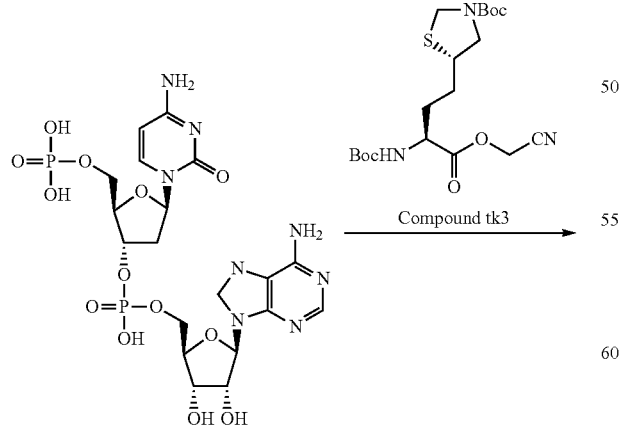
Compound 1h + Compound tk3 →
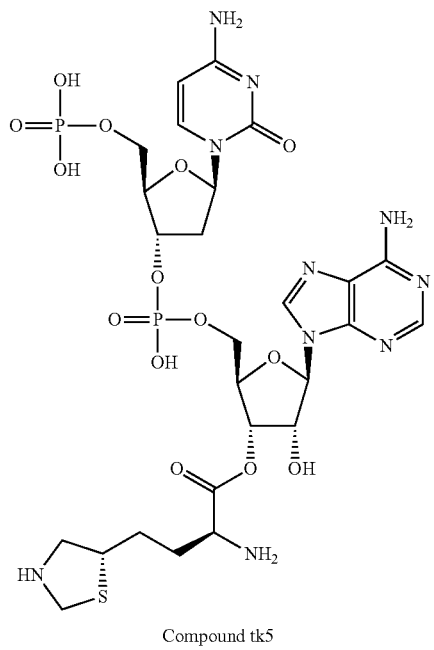
Compound tk5

Synthesis of (S)-2-((tert-butoxycarbonyl)amino)-4-((S)-3-(tert-butoxycarbonyl)thiazolidin-5-yl)butanoic Acid (Compound tk2)

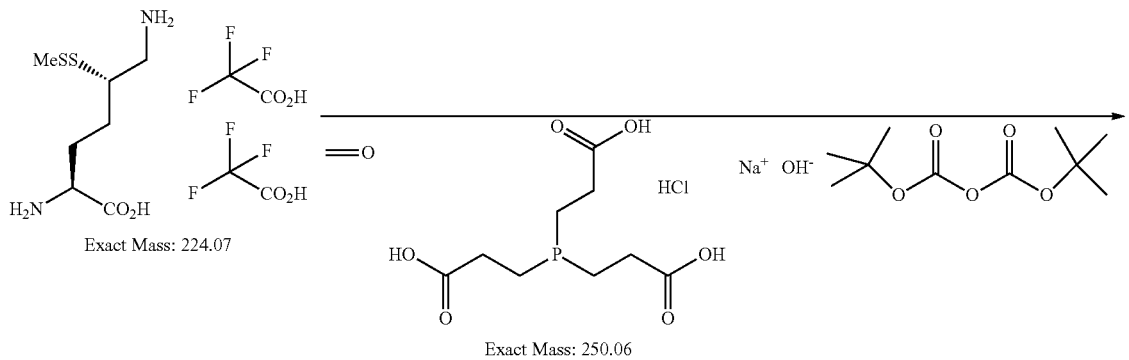

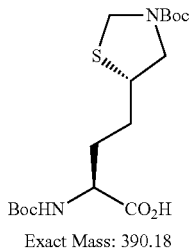

(1S,4S)-1-carboxy-4-(methylsulfinothioyl)pentane-1,5-diaminium 2,2,2-trifluoroacetate synthesized by the method described in the literature (J. Am. Chem. Soc. 2011, 133, 10708) (Compound tk1) (273.4 mg, 0.604 mmol) was dissolved in a 2 M aqueous sodium hydroxide solution (2.1 mL) at room temperature, followed by addition of tris(2-carboxyethyl)phosphine hydrochloride (182 mg, 0.635 mmol). The mixture was stirred at the same temperature for 15 minutes, followed by addition of a 37% aqueous formalin solution (0.9 mL). The mixture was stirred at the same temperature for 1.5 hours, followed by addition of a solution of a 2 M aqueous sodium hydroxide solution (0.15 mL) and Boc$_2$O (528 mg, 2.417 mmol) in 1,4-dioxane (2 mL). The reaction mixture was stirred at the same temperature for 17.5 hours, followed by addition of Boc$_2$O (250 mg). The mixture was stirred for 6.5 hours, followed by dilution with ethyl acetate. The resulting mixture was cooled in an ice bath, and a saturated aqueous potassium bisulfate solution (0.8 mL) was added. The mixture was extracted with ethyl acetate (twice), and the organic phase was washed with brine (4 mL). The organic phase was dried over sodium sulfate and then concentrated under reduced pressure, and the resulting crude product was purified by normal-phase silica gel column chromatography (hexane/ethyl acetate) to afford (S)-2-((tert-butoxycarbonyl)amino)-4-((S)-3-(tert-butoxycarbonyl)thiazolidin-5-yl)butanoic acid (Compound tk2) (131.7 mg, 56%).

LCMS (ESI) m/z=389 (M–H)–

Retention time: 0.83 min (analysis condition SQDAA05)

Synthesis of (S)-tert-butyl 5-((S)-3-((tert-butoxycarbonyl)amino)-4-(cyanomethoxy)-4-oxobutyl)thiazolidine-3-carboxylate (Compound tk3)

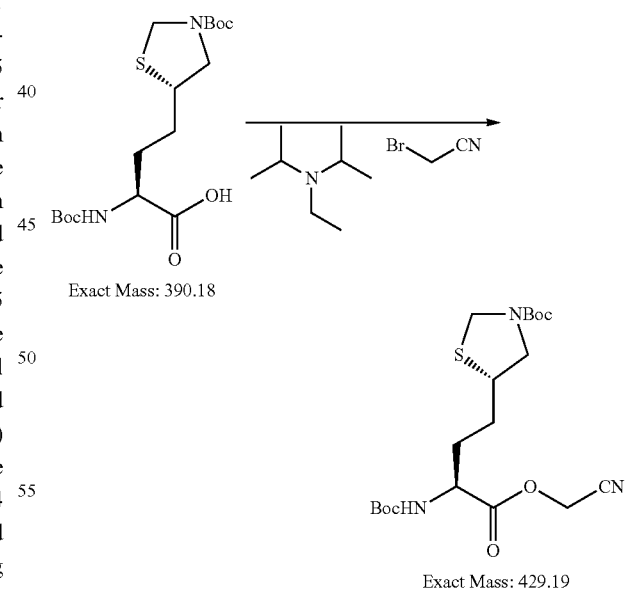

N,N-Diisopropylethylamine (48 μL, 0.276 mmol) and subsequently bromoacetonitrile (88 μL, 1.255 mmol) were added to a solution of (S)-2-((tert-butoxycarbonyl)amino)-4-((S)-3-(tert-butoxycarbonyl)thiazolidin-5-yl)butanoic acid (Compound tk2) (98 mg, 0.251 mmol) in acetonitrile (0.5 mL) at room temperature under a nitrogen atmosphere. The reaction mixture was stirred at the same temperature for 3 hours and then concentrated under reduced pressure, and the resulting crude product was purified by normal-phase silica gel column chromatography (hexane/ethyl acetate) to afford (S)-tert-butyl 5-((S)-3-((tert-butoxycarbonyl)amino)-4-(cyanomethoxy)-4-oxobutyl)thiazolidine-3-carboxylate (Compound tk3) (94.0 mg, 87%).—

LCMS (ESI) m/z=428.1 (M–H)–
Retention time: 0.85 min (analysis condition SQDFA05)

Synthesis of (5S)-tert-butyl 5-((3S)-4-(((2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl)oxy)-3-((tert-butoxycarbonyl)amino)-4-oxobutyl)thiazolidine-3-carboxylate (Compound tk4)

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (44.0 mg, 0.069 mmol) and (S)-tert-butyl 5-((S)-3-((tert-butoxycarbonyl)amino)-4-(cyanomethoxy)-4-oxobutyl)thiazolidine-3-carboxylate (Compound tk3) (89 mg, 0.207 mmol) in acetonitrile (0.3 mL) was added to buffer A (12.5 mL), and the mixture was stirred at room temperature for 1.25 hours. Following lyophilization, the resulting residue was purified by reverse-phase silica gel column chromatography (0.05% aqueous trifluoroacetic acid solution/0.05% trifluoroacetic acid-acetonitrile solution) to afford (5S)-tert-butyl 5-((3S)-4-(((2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl)oxy)-3-((tert-butoxycarbonyl)amino)-4-oxobutyl)thiazolidine-3-carboxylate (Compound tk4) (17.4 mg, 25%).

LCMS (ESI) m/z=1007.7 (M–H)–
Retention time: 0.54 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-4-((S)-thiazolidin-5-yl)butanoate (Ala(Tzm)-pdCpA) (Compound tk5)

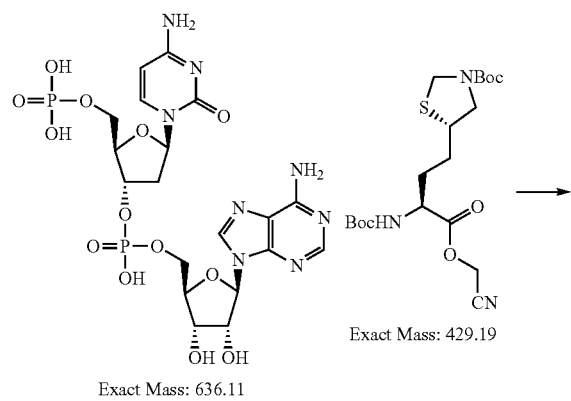

Exact Mass: 636.11
Exact Mass: 429.19

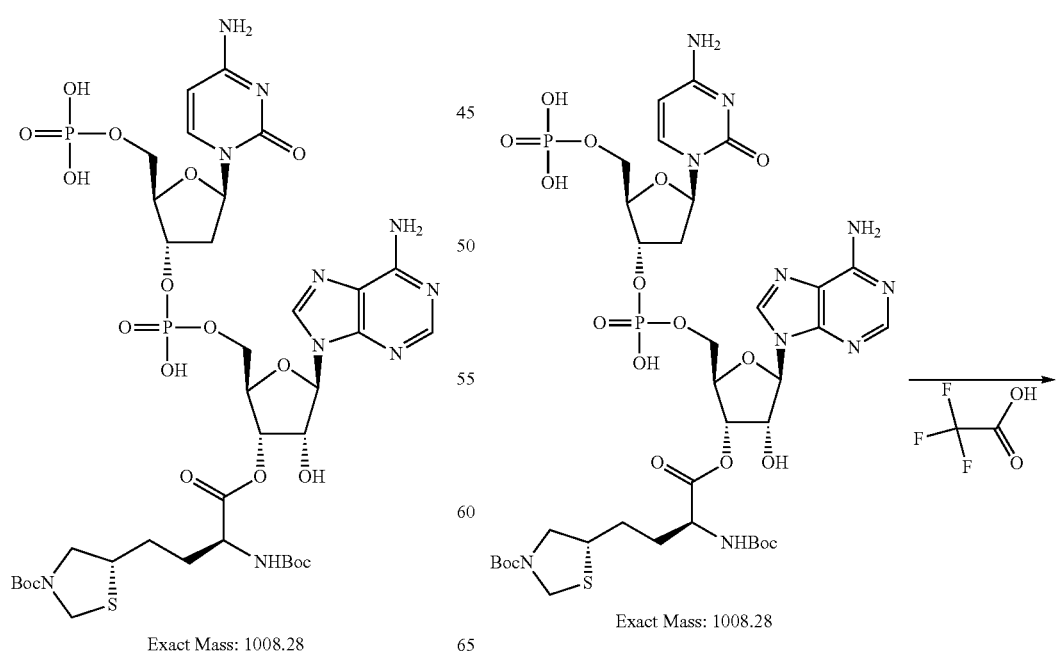

Exact Mass: 1008.28
Exact Mass: 1008.28

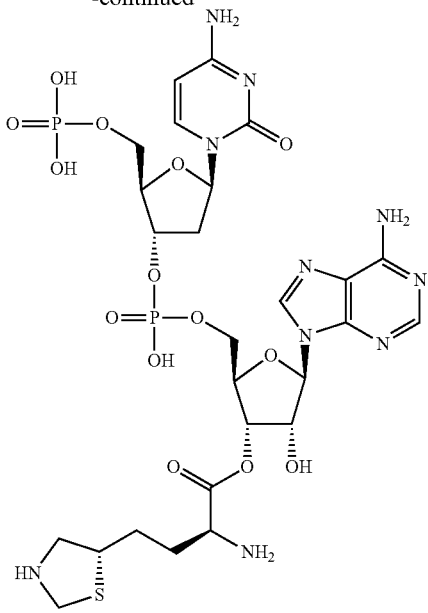

Exact Mass: 808.18

A 10% solution of trifluoroacetic acid in dichloromethane (0.16 mL) was added to a solution of (5S)-tert-butyl 5-((3S)-4-(((2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl)oxy)-3-((tert-butoxycarbonyl)amino)-4-oxobutyl)thiazolidine-3-carboxylate (Compound tk4) (8.5 mg, 8.43 μmol) in dichloromethane (0.2 mL), and the mixture was stirred at room temperature for 1.25 hours. Following concentration under reduced pressure, (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-4-((S)-thiazolidin-5-yl)butanoate (Ala(Tzm)-pdCpA) (Compound tk5) (10.6 mg, quant.) was obtained.

LCMS (ESI) m/z=807.5 (M–H)–

Retention time: 0.14 min (analysis condition SQDFA05)

10-1-2. Synthesis of Aminoacylated pdCpA Compound tk12

The synthesis was carried out according to the following scheme.

TK scheme 2

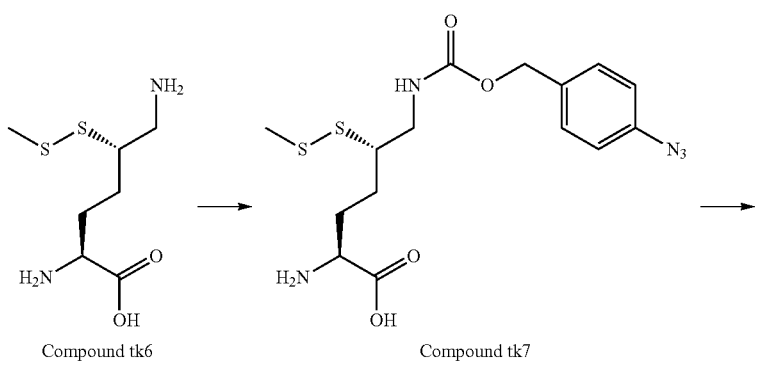

Compound tk6      Compound tk7

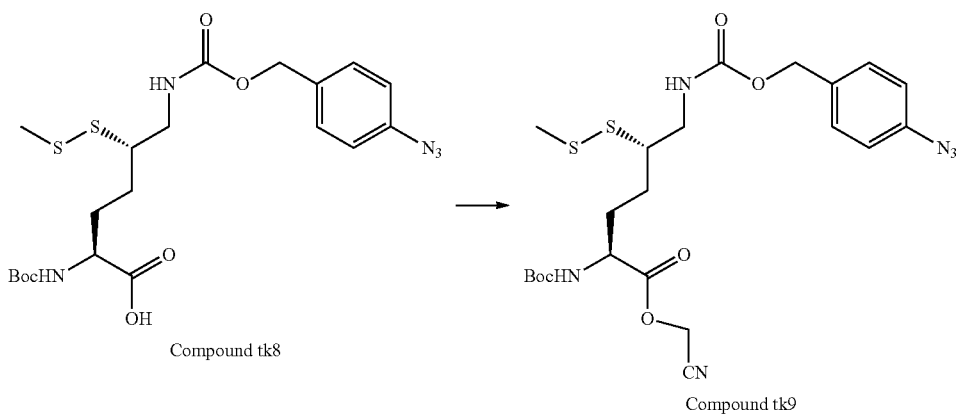

Compound tk8      Compound tk9

-continued
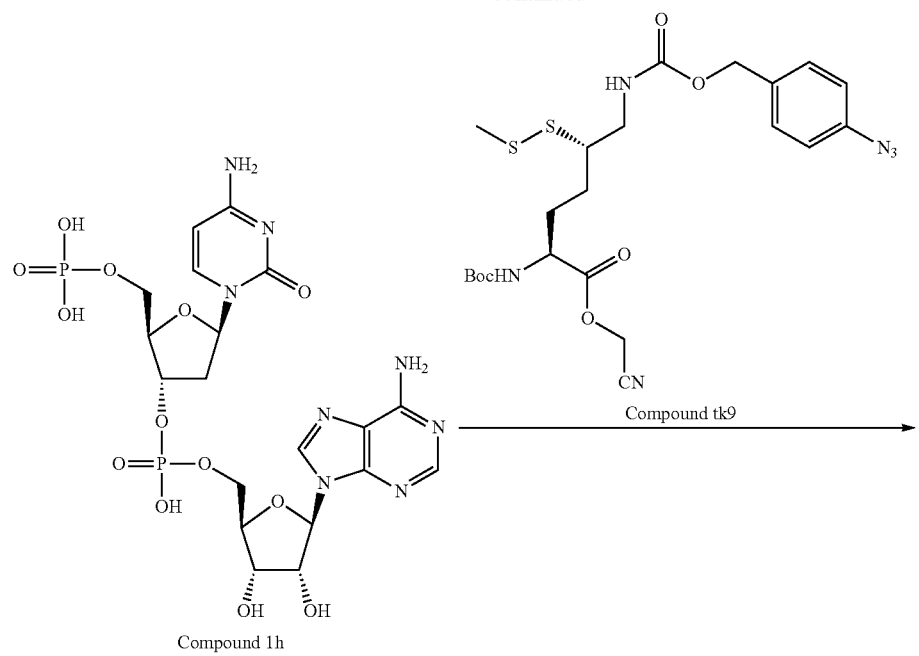
Compound 1h
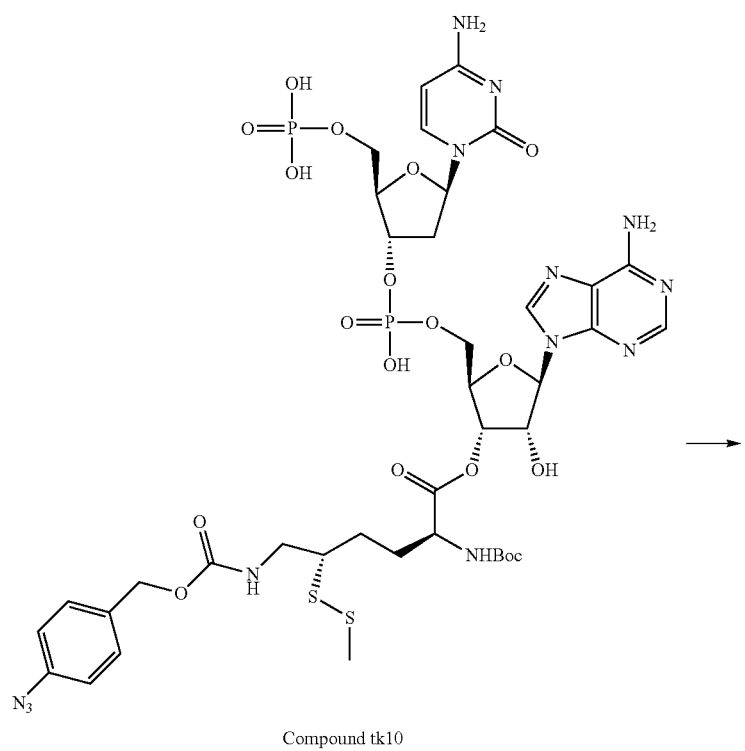
Compound tk10

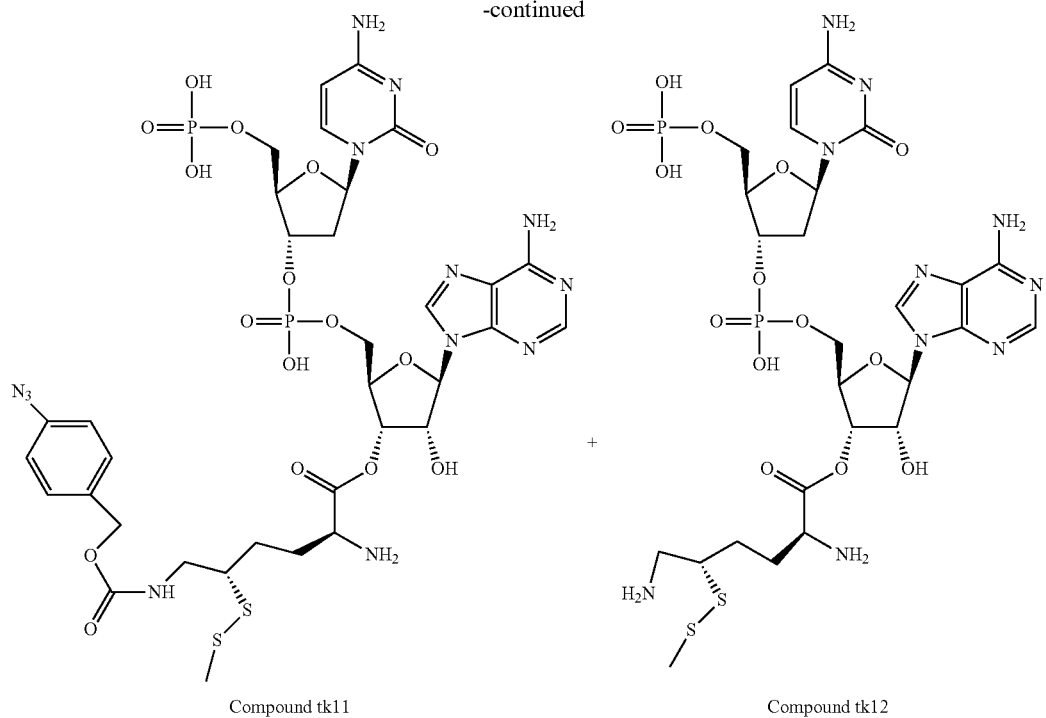
Compound tk11      Compound tk12
Synthesis of (2S,5S)-2-amino-6-((((4-azidobenzyl)oxy)carbonyl)amino)-5-(methyldisulfanyl)hexanoic Acid (Lys(5S-SSMe)(Acbz)) (Compound tk7)
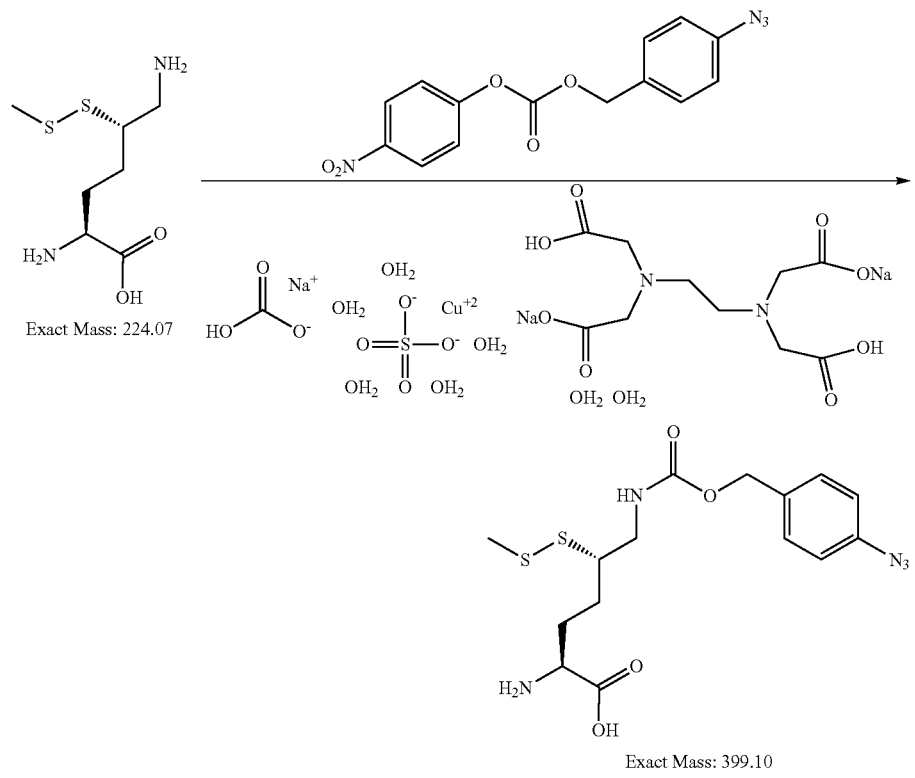

A solution of copper sulfate pentahydrate (100 mg, 0.4 mmol) in water (0.3 mL) was added to a solution of (2S,5S)-2,6-diamino-5-(methyldisulfanyl)hexanoic acid (Compound tk6) (176 mg, 0.785 mol) and sodium bicarbonate (659 mg, 7.85 mmol) in water (1.2 mL) at room temperature, followed by addition of a solution of 4-azidobenzyl (4-nitrophenyl) carbonate synthesized by the method described in the literature (Bioconjugate Chem. 2008, 19, 714) (296 mg, 0.941 mmol) in acetone (2.7 mL). The reaction mixture was stirred at the same temperature for 25.75 hours and then filtered, and the solid on the filter paper was washed with water. The solid collected by filtration was suspended in water (10 mL)-methanol (1 mL), followed by addition of disodium dihydrogen ethylenediaminetetraacetate (350 mg, 0.941 mmol) at room temperature. The reaction mixture was stirred at the same temperature for 7.75 hours and then filtered, and the white solid on the filter paper was purified by reverse-phase silica gel column chromatography (10 mM ammonium acetate aqueous solution/methanol) to afford (2S,5S)-2-amino-6-((((4-azidobenzyl)oxy)carbonyl)amino)-5-(methyldisulfanyl)hexanoic acid (Lys(5S-SSMe)(Acbz)) (Compound tk7) (50.2 mg, 16%).

LCMS (ESI) m/z=398 (M−H)−

Retention time: 0.85 min (analysis condition SQDAA05)

Synthesis of (2S,5S)-6-((((4-azidobenzyl)oxy)carbonyl)amino)-2-((tert-butoxycarbonyl)amino)-5-(methyldisulfanyl)hexanoic Acid (Compound tk8)

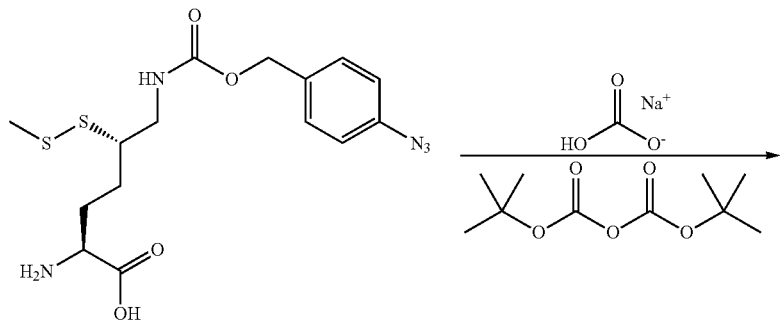

Exact Mass: 399.10

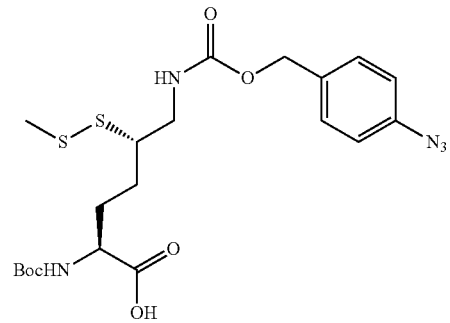

Exact Mass: 499.16

Sodium bicarbonate (44.2 mg, 0.526 mmol), water (1 mL) and Boc$_2$O (115 mg, 0.526 mmol) were added to a solution of (2S,5S)-2-amino-6-((((4-azidobenzyl)oxy)carbonyl)amino)-5-(methyldisulfanyl)hexanoic acid (Lys(5S-SSMe)(Acbz)) (Compound tk7) (70 mg, 0.175 mmol) in 1,4-dioxane (2 mL)-acetonitrile (1 mL) at room temperature. The reaction mixture was stirred at the same temperature for 22.5 hours and then concentrated under reduced pressure. The resulting crude product was purified by reverse-phase silica gel column chromatography (10 mM aqueous ammonium acetate solution/methanol) to afford (2S,5S)-6-((((4-azidobenzyl)oxy)carbonyl)amino)-2-((tert-butoxycarbonyl)amino)-5-(methyldisulfanyl)hexanoic acid (Compound tk8) (71.6 mg, 82%).

LCMS (ESI) m/z=498.4 (M−H)−

Retention time: 0.91 min (analysis condition SQDAA05)

2379

Synthesis of (2S,5S)-cyanomethyl 6-((((4-azidobenzyl)oxy)carbonyl)amino)-2-((tert-butoxycarbonyl)amino)-5-(methyldisulfanyl)hexanoate (Compound tk9)

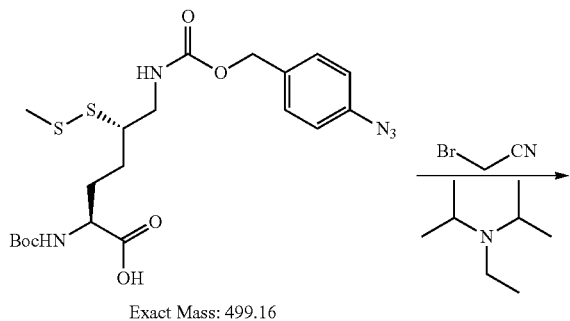

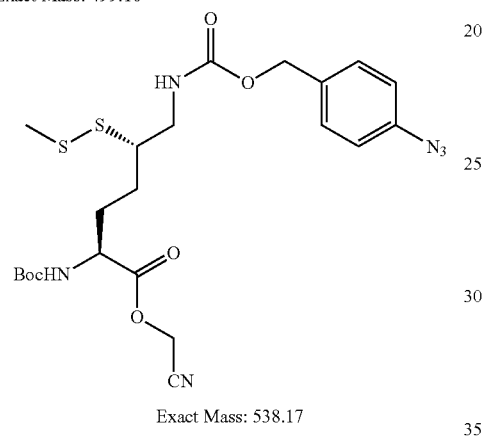

2380

N,N-Diisopropylethylamine (51 µL, 0.291 mmol) and subsequently bromoacetonitrile (92 µL, 1.321 mmol) were added to a solution of (2S,5S)-6-((((4-azidobenzyl)oxy) carbonyl)amino)-2-((tert-butoxycarbonyl)amino)-5-(methyldisulfanyl)hexanoic acid (Compound tk8) (132 mg, 0.264 mmol) in acetonitrile (0.4 mL) at room temperature under a nitrogen atmosphere. The reaction mixture was stirred at the same temperature for 4.5 hours and then concentrated under reduced pressure, and the resulting crude product was purified by normal-phase silica gel column chromatography (hexane/ethyl acetate) to afford (2S,5S)-cyanomethyl 6-((((4-azidobenzyl)oxy)carbonyl)amino)-2-((tert-butoxycarbonyl)amino)-5-(methyldisulfanyl)hexanoate (Compound tk9) (127.3 mg, 89%).

LCMS (ESI) m/z=537.6 (M–H)–
Retention time: 0.91 min (analysis condition SQDFA05)

Synthesis of (2S,5S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-((((4-azidobenzyl)oxy)carbonyl)amino)-2-((tert-butoxycarbonyl)amino)-5-(methyldisulfanyl) hexanoate (Compound tk10)

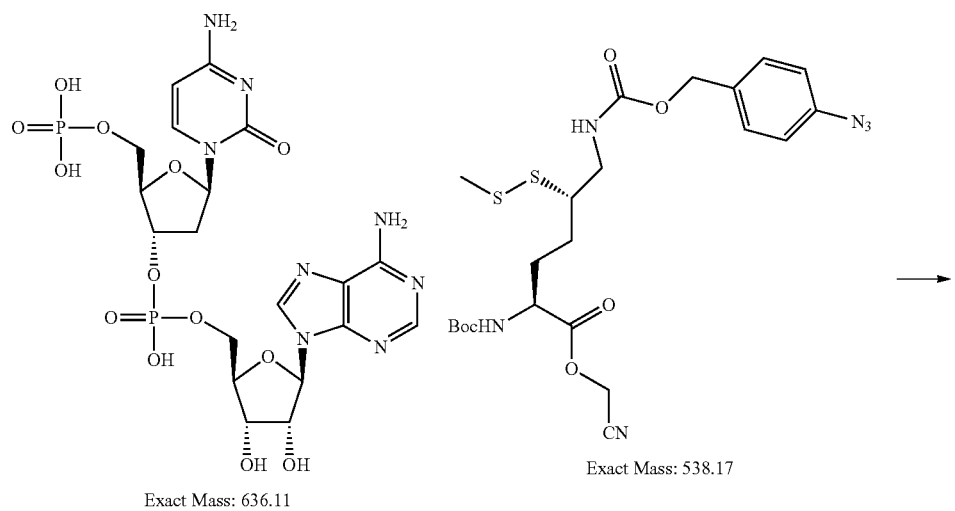

-continued

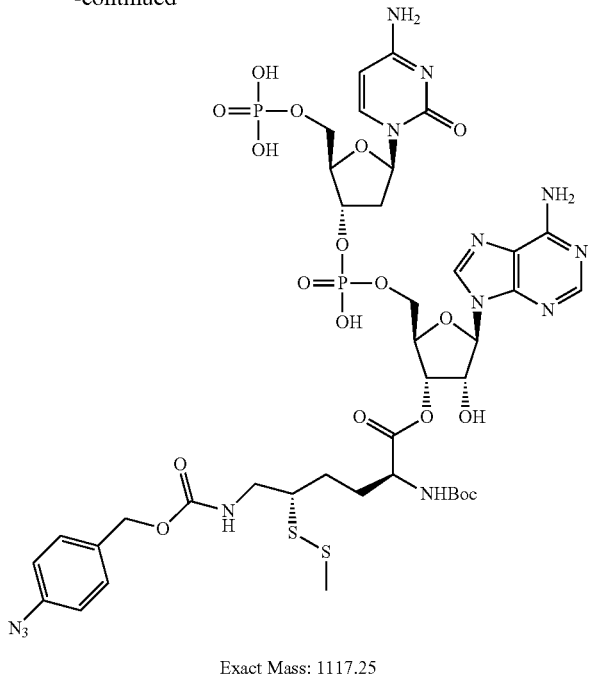

Exact Mass: 1117.25

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (49.2 mg, 0.077 mmol) and (2S,5S)-cyanomethyl 6-((((4-azidobenzyl)oxy)carbonyl)amino)-2-((tert-butoxycarbonyl)amino)-5-(methyldisulfanyl)hexanoate (Compound tk9) (125 mg, 0.232 mmol) in acetonitrile (0.5 mL) was added to buffer A (13 mL), and the mixture was stirred at room temperature for 2 hours. Acetonitrile (0.5 mL) was added and the mixture was stirred for 1.25 hours, followed by addition of acetonitrile (0.5 mL). After stirring for a further 1.25 hours, acetonitrile (0.5 mL) was added and the mixture was stirred for 1.5 hours. Following lyophilization, the resulting residue was purified by reverse-phase silica gel column chromatography (0.05% aqueous trifluoroacetic acid solution/0.05% trifluoroacetic acid-acetonitrile solution) to afford (2S,5S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-((((4-azidobenzyl)oxy)carbonyl)amino)-2-((tert-butoxycarbonyl)amino)-5-(methyldisulfanyl)hexanoate (Compound tk10) (14.0 mg, 16%).

LCMS (ESI) m/z=1116.7 (M−H)−
Retention time: 0.62 min (analysis condition SQDFA05)

Synthesis of (2S,5S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-((((4-azidobenzyl)oxy)carbonyl)amino)-5-(methyldisulfanyl)hexanoate (Lys(5S-SSMe)(Acbz)-pdCpA) (Compound tk11) and (2S,5S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2,6-diamino-5-(methyldisulfanyl)hexanoate (Lys(5S-SSMe)-pdCpA, Compound tk12)

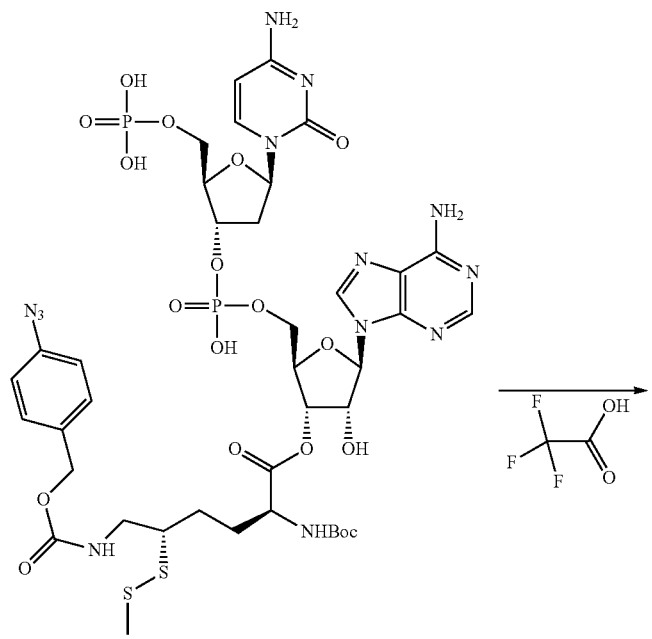

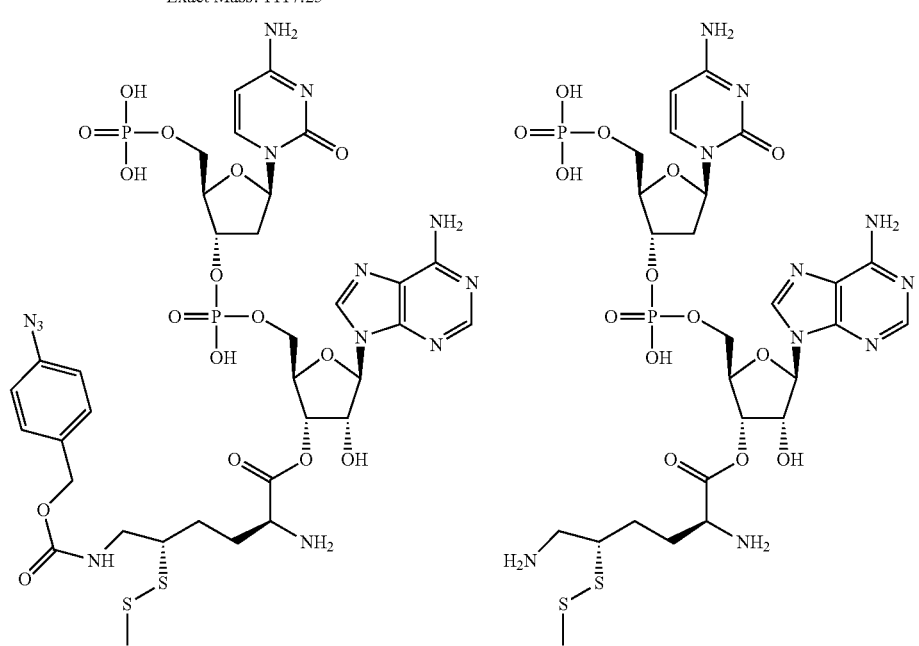

A 10% solution of trifluoroacetic acid in dichloromethane (0.24 mL) was added to a solution of (2S,5S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-((((4-azidobenzyl)oxy)carbonyl)amino)-2-((tert-butoxycarbonyl)amino)-5-(methyldisulfanyl)hexanoate (Compound tk10) (14.0 mg, 0.013 mmol) in dichloromethane (0.2 mL), and the mixture was stirred at room temperature for 30 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S,5S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-((((4-azidobenzyl)oxy)carbonyl)amino)-5-(methyldisulfanyl) hexanoate (Lys(5S-SSMe)(Acbz)-pdCpA) (Compound tk11) (3.2 mg, 25%) and (2S,5S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2,6-diamino-5-(methyldisulfanyl)hexanoate (Lys(5S-SSMe)-pdCpA) (Compound tk12) (1.5 mg, 14%).

(2S,5S)-(2R,3S,4R,5R)-2-(((((2R,3S,5R)-5-(4-Amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-((((4-azidobenzyl)oxy)carbonyl)amino)-5-(methyldisulfanyl)hexanoate (Lys(5S-SSMe)(Acbz)-pdCpA) (Compound tk11)

LCMS (ESI) m/z=1016.5 (M−H)−
Retention time: 0.45 min (analysis condition SQDFA05)

(2S,5S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2,6-diamino-5-(methyldisulfanyl) hexanoate (Lys(5S-SSMe)-pdCpA) (Compound tk12)

LCMS (ESI) m/z=841.4 (M−H)−
Retention time: 0.20 min (analysis condition SQDFA05)

10-1-3. Synthesis of Aminoacylated pdCpA Compound tk18

The synthesis was carried out according to the following scheme.

TK scheme 3

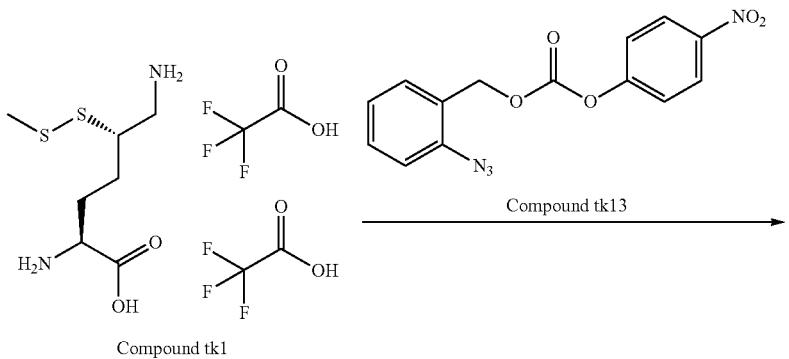

Compound tk1

Compound tk13

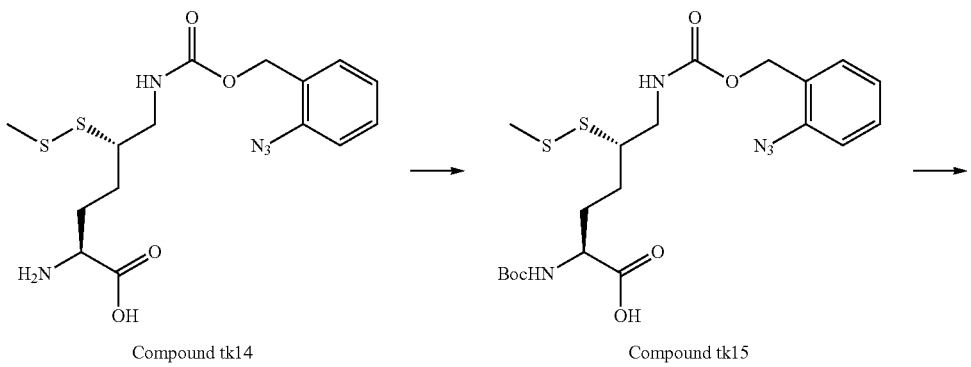

Compound tk14

Compound tk15

-continued
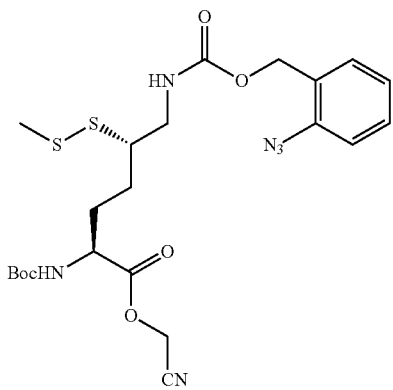
Compound tk16
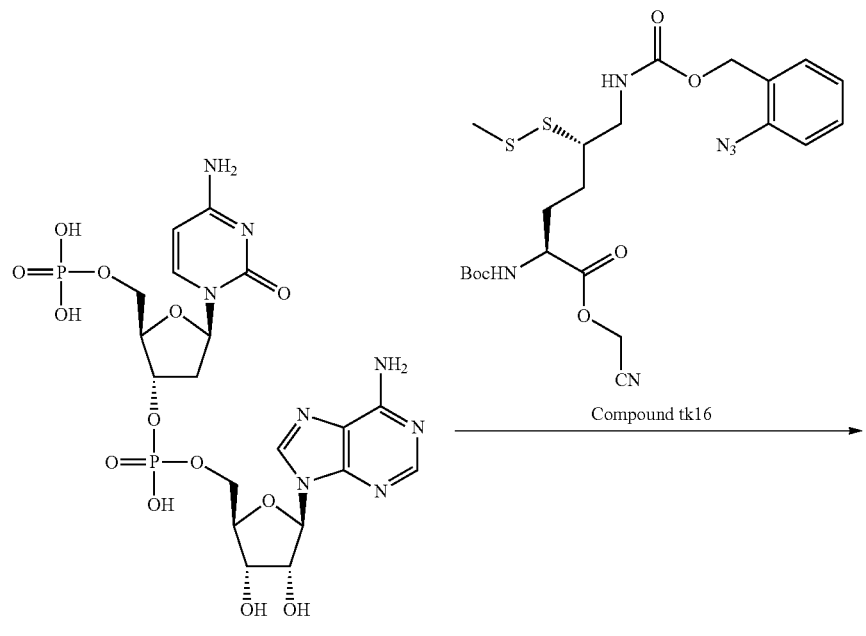
Compound tk16

-continued

2389

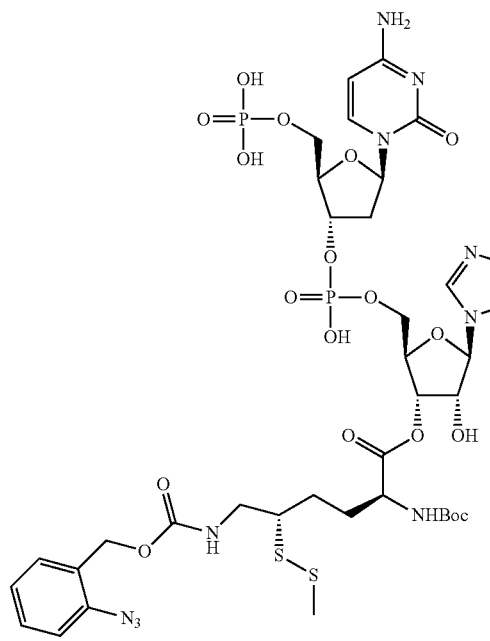

Compound tk17

2390

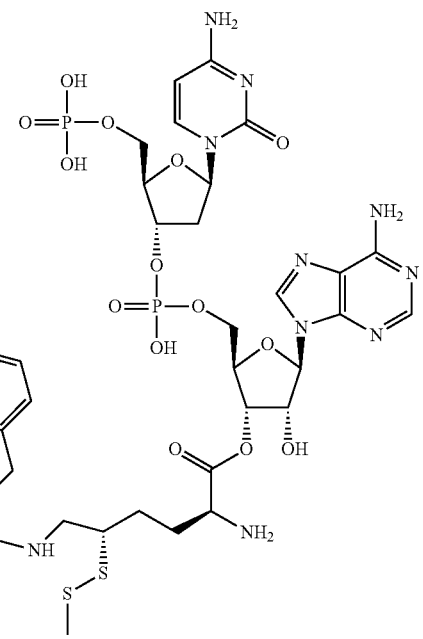

Compound tk18

Synthesis of 2-azidobenzyl (4-nitrophenyl) Carbonate (Compound tk13)

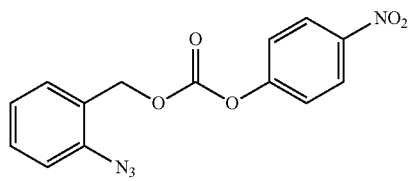

Exact Mass: 314.07

The compound was synthesized from (2-azidophenyl) methanol and 4-nitrophenyl chloroformate in the same manner as in the method described in the literature (Bioconjugate Chem. 2008, 19, 714).

LCMS (ESI) m/z=138 (HOC$_6$H$_4$NO$_2$—H)—

Retention time: 1.03 min (analysis condition SQDAA05)

Synthesis of (2S,5S)-2-amino-6-((((2-azidobenzyl)oxy)carbonyl)amino)-5-(methyldisulfanyl)hexanoic Acid (Lys(5S-SSMe)(oAcbz)) (Compound tk14)

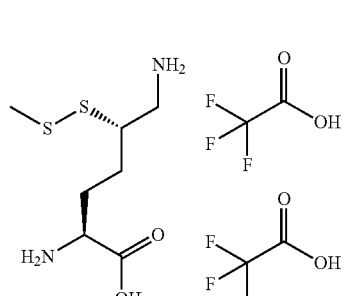

Exact Mass: 224.07

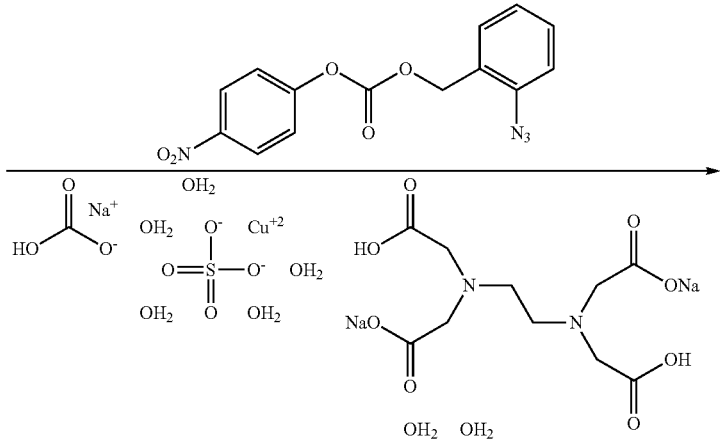

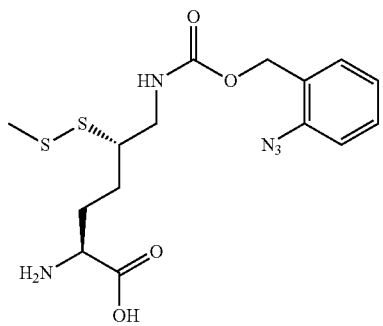

Exact Mass: 399.10

A solution of copper sulfate pentahydrate (63.6 mg, 0.255 mmol) in water (0.3 mL) was added to a solution of (1S,4S)-1-carboxy-4-(methylsulfinothioyl)pentane-1,5-diaminium 2,2,2-trifluoroacetate synthesized by the method described in the literature (J. Am. Chem. Soc. 2011, 133, 10708) (Compound tk1) (226 mg, 0.50 mmol) and sodium bicarbonate (420 mg, 5.00 mmol) in water (1.2 mL) at room temperature, followed by addition of a solution of 2-azidobenzyl (4-nitrophenyl) carbonate (Compound tk13) (188 mg, 0.599 mmol) in acetonitrile (6 mL). The reaction mixture was stirred at the same temperature for 49 hours and then filtered, and the solid on the filter paper was washed with water. The solid collected by filtration was suspended in water (10 mL)-methanol (1 mL), followed by addition of disodium dihydrogen ethylenediaminetetraacetate (223 mg, 0.599 mmol) at room temperature. The reaction mixture was stirred at the same temperature for 17.25 hours and then filtered, and the white solid on the filter paper was purified by reverse-phase silica gel column chromatography (10 mM ammonium acetate aqueous solution/methanol) to afford ((2S,5S)-2-amino-6-((((2-azidobenzyl)oxy)carbonyl)amino)-5-(methyldisulfanyl)hexanoic acid (Lys(5S-SSMe)(oAcbz)) (Compound tk14) (30.2 mg, 15%).

LCMS (ESI) m/z=398 (M−H)−

Retention time: 0.85 min (analysis condition SQDAA05)

Synthesis of (2S,5S)-6-((((2-azidobenzyl)oxy)carbonyl)amino)-2-((tert-butoxycarbonyl)amino)-5-(methyldisulfanyl)hexanoic Acid (Compound tk15)

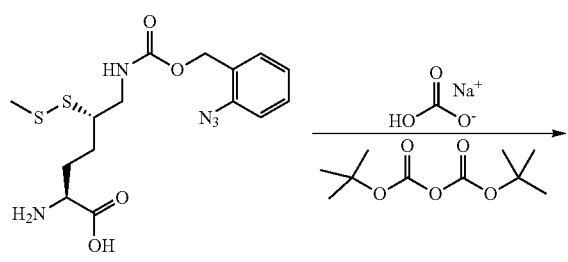

Exact Mass: 399.10

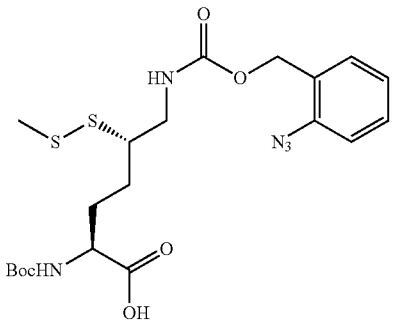

Exact Mass: 499.16

A solution of water (1 mL) and Boc$_2$O (170 mg, 0.781 mmol) in 1,4-dioxane (1 mL) was added to a mixture of ((2S,5S)-2-amino-6-((((2-azidobenzyl)oxy)carbonyl)amino)-5-(methyldisulfanyl)hexanoic acid (Lys(5S-SSMe)(oAcbz)) (Compound tk14) (78 mg, 0.195 mmol) and sodium bicarbonate (65.6 mg, 0.781 mmol) at room temperature. After stirring at the same temperature for 12.5 hours, the mixture was cooled in an ice bath and diluted with ethyl acetate and water, and an aqueous solution of potassium bisulfate (115 mg) was added thereto. The mixture was extracted with ethyl acetate (×2), and the organic phase was washed with brine (1 mL×2) and dried over sodium sulfate. Following concentration under reduced pressure, the resulting crude product was purified by normal-phase silica gel column chromatography (hexane/ethyl acetate) to afford (2S,5S)-6-((((2-azidobenzyl)oxy)carbonyl)amino)-2-((tert-butoxycarbonyl)amino)-5-(methyldisulfanyl)hexanoic acid (Compound tk15) (90.3 mg, 93%).

LCMS (ESI) m/z=498 (M−H)−

Retention time: 0.90 minute (analysis condition SQDAA05)

2393

Synthesis of (2S,5S)-cyanomethyl 6-((((2-azidobenzyl)oxy)carbonyl)amino)-2-((tert-butoxycarbonyl)amino)-5-(methyldisulfanyl)hexanoate (Compound tk16)

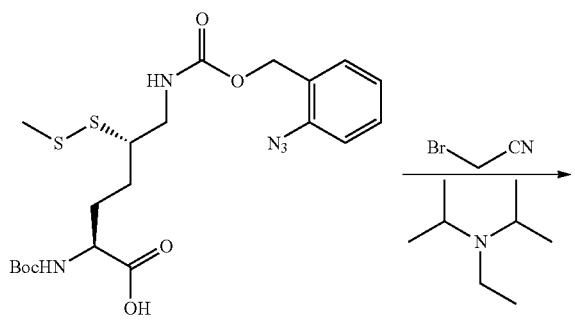

Exact Mass: 499.16

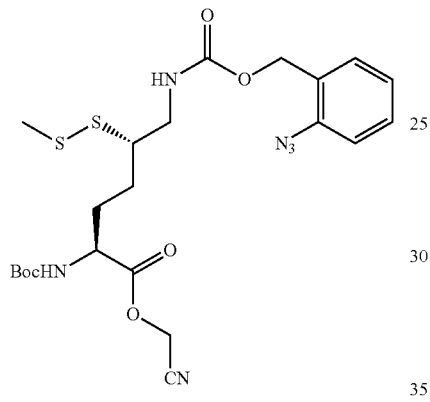

Exact Mass: 538.17

2394

N,N-Diisopropylethylamine (34 µL, 0.197 mmol) and subsequently bromoacetonitrile (62 µL, 0.896 mmol) were added to a solution of (2S,5S)-6-((((2-azidobenzyl)oxy)carbonyl)amino)-2-((tert-butoxycarbonyl)amino)-5-(methyldisulfanyl)hexanoic acid (Compound tk15) (89.5 mg, 0.179 mmol) in acetonitrile (0.3 mL) at room temperature under a nitrogen atmosphere. The reaction mixture was stirred at the same temperature for 1.25 hours and then concentrated under reduced pressure, and the resulting crude product was purified by normal-phase silica gel column chromatography (hexane/ethyl acetate) to afford (2S,5S)-cyanomethyl 6-((((2-azidobenzyl)oxy)carbonyl)amino)-2-((tert-butoxycarbonyl)amino)-5-(methyldisulfanyl)hexanoate (Compound tk16) (77.5 mg, 80%).

LCMS (ESI) m/z=539.5 (M+H)+
Retention time: 0.92 min (analysis condition SQDFA05)

Synthesis of (2S,5S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-((((2-azidobenzyl)oxy)carbonyl)amino)-2-((tert-butoxycarbonyl)amino)-5-(methyldisulfanyl) hexanoate (Compound tk17)

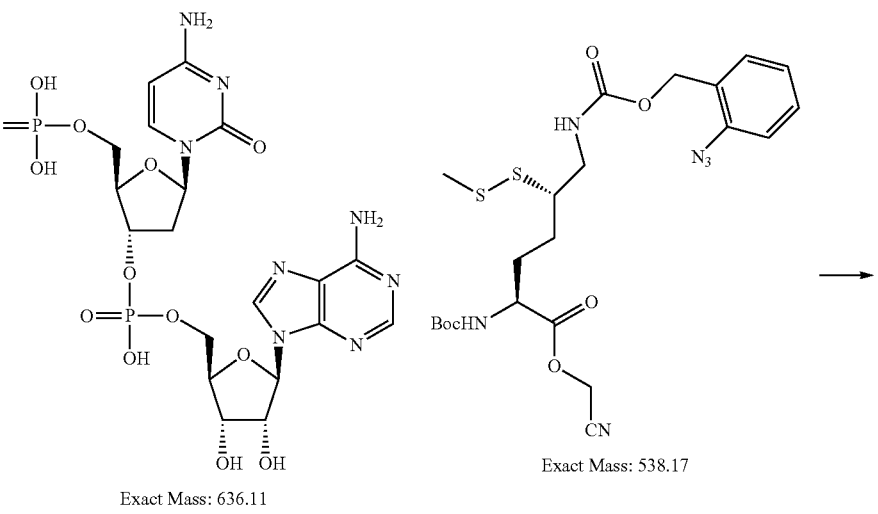

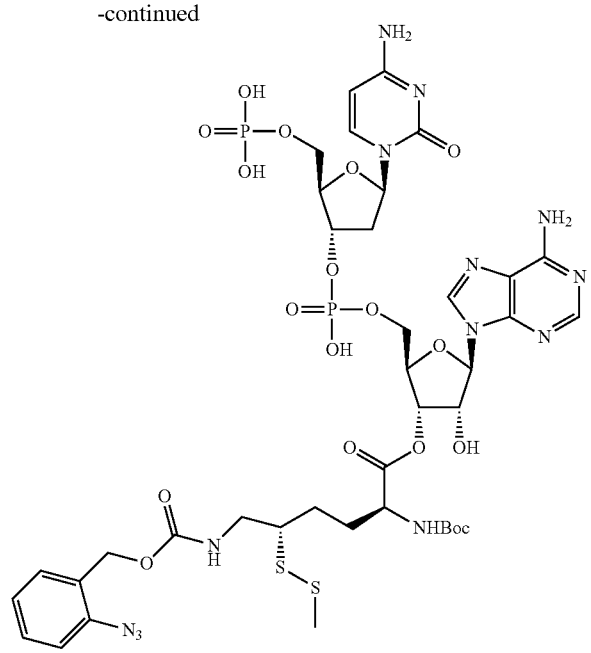

Exact Mass: 1117.25

A solution of ((2R,3S,5R)-5-(4-amino-2-oxopyrimidin-1 (2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (30.3 mg, 0.048 mmol) and (2S,5S)-cyanomethyl 6-((((2-azidobenzyl)oxy)carbonyl)amino)-2-((tert-butoxycarbonyl)amino)-5-(methyldisulfanyl)hexanoate (Compound tk16) (77 mg, 0.143 mmol) in acetonitrile (0.7 mL) was added to buffer A (8 mL), and the mixture was stirred at room temperature for 40 minutes. Acetonitrile (3 mL) was added, followed by stirring for 55 minutes. Acetonitrile (2 mL) was further added, followed by stirring for 5 hours. Following lyophilization, the resulting residue was purified by reverse-phase silica gel column chromatography (0.05% aqueous trifluoroacetic acid solution/0.05% trifluoroacetic acid-acetonitrile solution) to afford (2S,5S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-((((2-azidobenzyl)oxy)carbonyl)amino)-2-((tert-butoxycarbonyl)amino)-5-(methyldisulfanyl)hexanoate (Compound tk17) (2.8 mg, 5%).

LCMS (ESI) m/z=1116.2 (M–H)–
Retention time: 0.65 min (analysis condition SQDFA05)

Synthesis of (2S,5S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-((((2-azidobenzyl)oxy)carbonyl)amino)-5-(methyldisulfanyl)hexanoate (Lys(5S-SSMe)(oAcbz)-pdCpA) (Compound tk18)

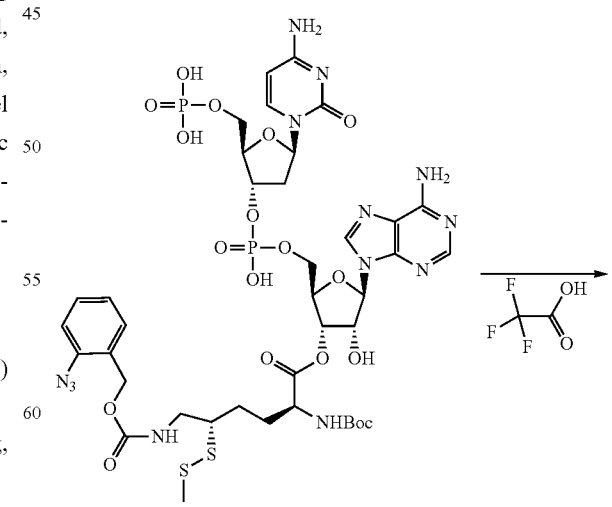

Exact Mass: 1117.25

2397
-continued

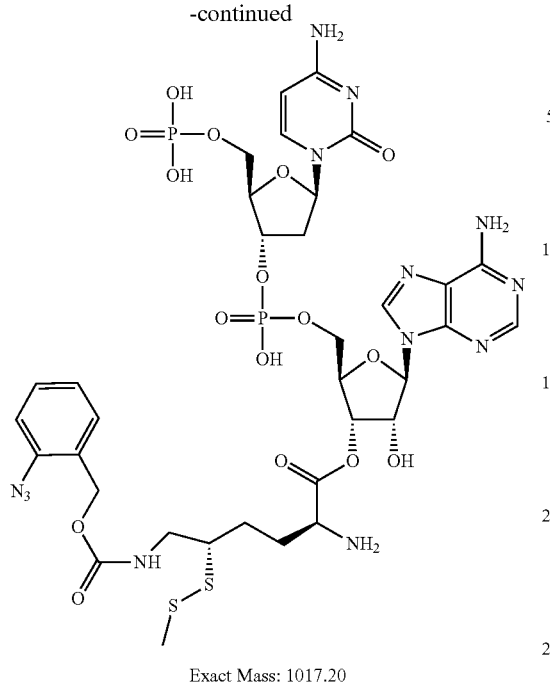

Exact Mass: 1017.20

A 10% solution of trifluoroacetic acid in dichloromethane (0.1 mL) was added to a solution of (2S,5S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-((((2-azidobenzyl)oxy)carbonyl)amino)-2-((tert-butoxycarbonyl)amino)-5-(methyldisulfanyl)hexanoate (Compound tk17) (2.8 mg, 2.504 μmol) in dichloromethane (0.1 mL), and the mixture was stirred at room temperature for 60 minutes. Following concentrated under reduced pressure, the resulting residue was purified by reverse-phase silica gel column chromatography (0.05% aqueous trifluoroacetic acid solution/0.05% trifluoroacetic acid-acetonitrile solution) to afford (2S,5S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-((((2-azidobenzyl)oxy)carbonyl)amino)-5-(methyldisulfanyl)hexanoate (Lys(5S-SSMe)(oAcbz)-pdCpA) (Compound tk18) (1.4 mg, 55%).

LCMS (ESI) m/z=1016.0 (M−H)−

Retention time: 0.44 min (analysis condition SQDFA05)

10-1-4. Synthesis of Aminoacylated pdCpA Compound tk26

The synthesis was carried out according to the following scheme.

2398

TK scheme 4-1

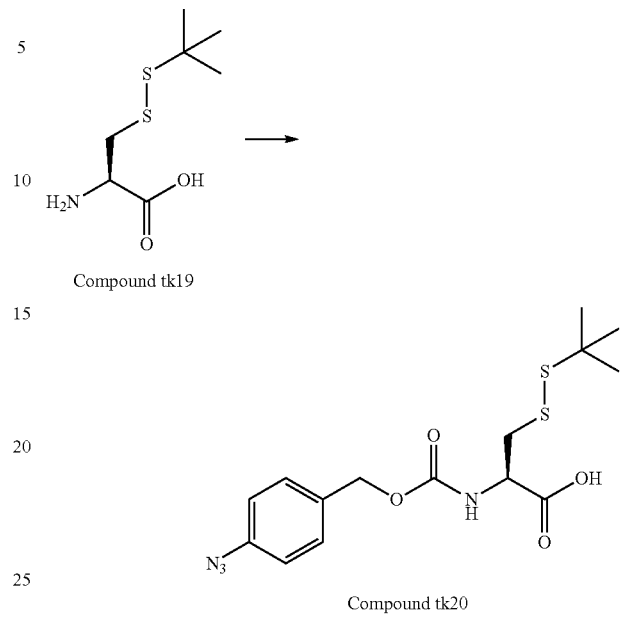

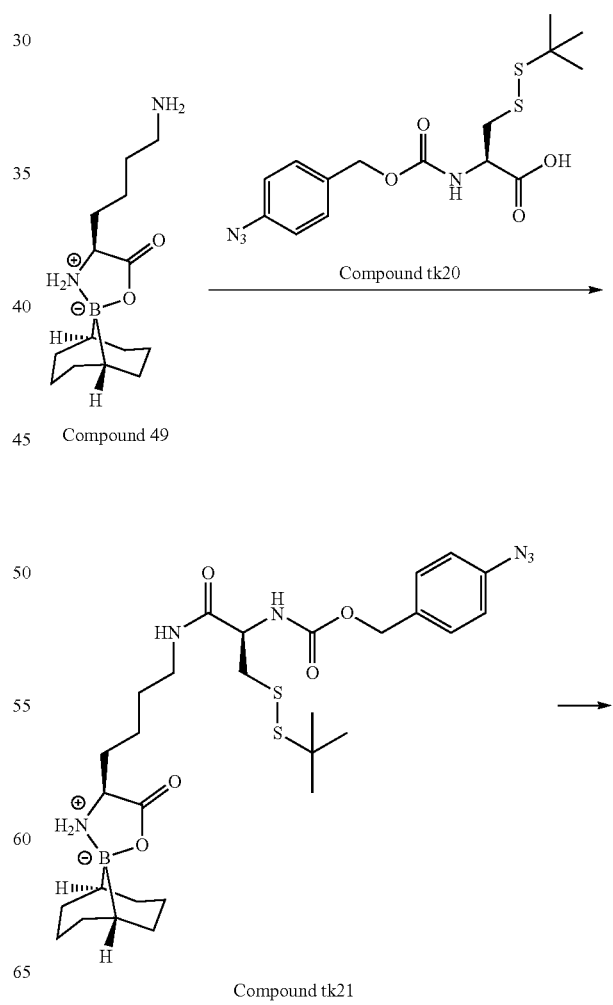

2399
-continued
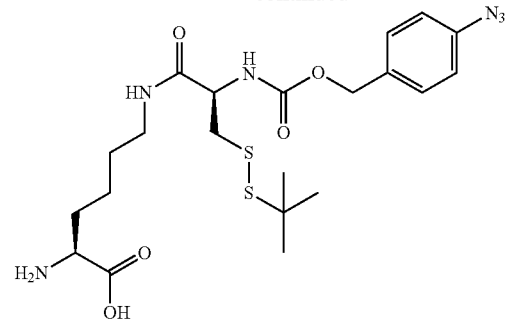
Compound tk22
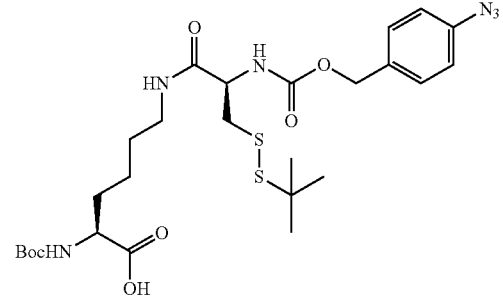
Compound tk23
2400
-continued
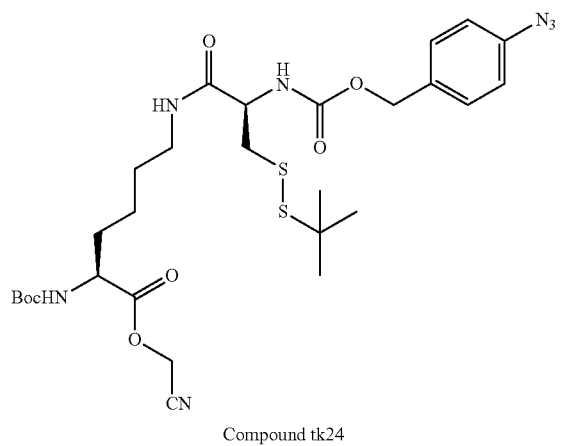
Compound tk24
TK scheme 4-2
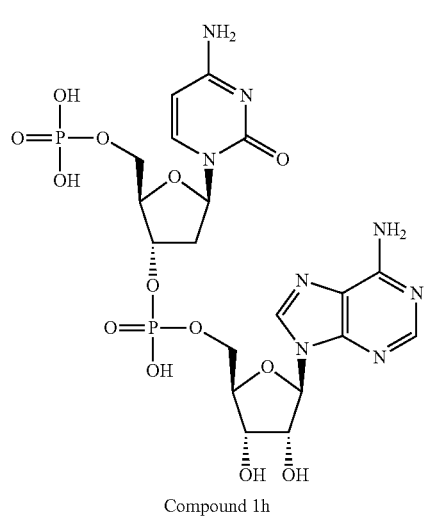
Compound 1h
→ Compound tk24 →

-continued
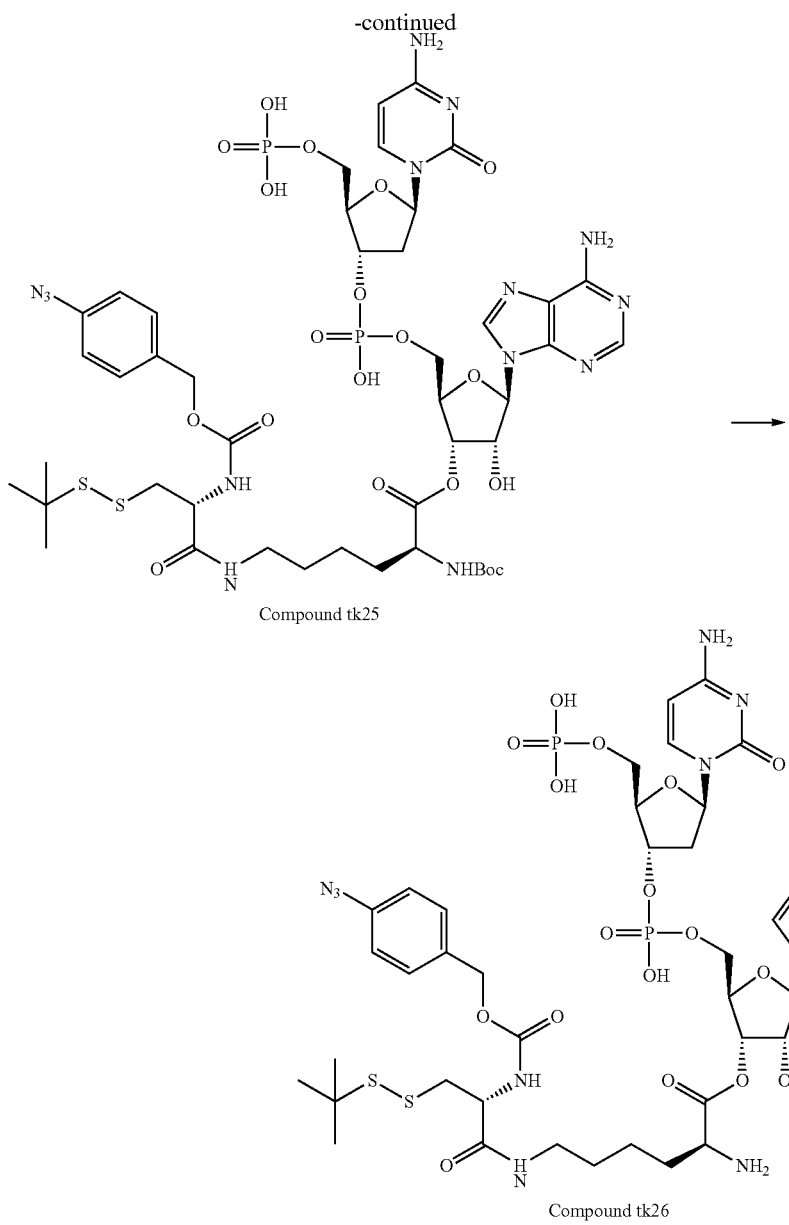
Compound tk25
Compound tk26
Synthesis of (R)-2-(((((4-azidobenzyl)oxy)carbonyl)amino)-3-(tert-butyldisulfanyl)propanoic Acid (Compound tk20)
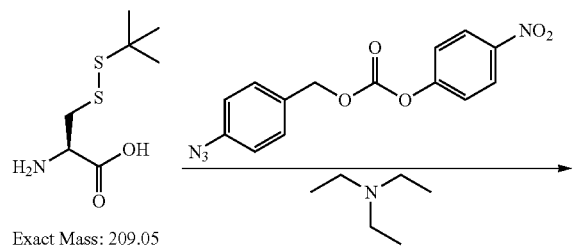
Exact Mass: 209.05
-continued
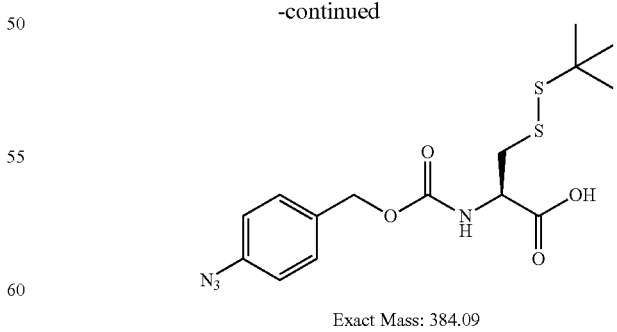
Exact Mass: 384.09
DMF (0.5 mL) was added to a mixture of S-tert-butyl-mercapto-L-cysteine (Compound tk19) (116 mg, 0.554 mmol) and 4-azidobenzyl (4-nitrophenyl) carbonate synthesized by the method described in the literature (Bioconjugate Chem. 2008, 19, 714) (209 mg, 0.665 mmol) at room temperature under a nitrogen atmosphere. The mixture was cooled in an ice bath, followed by addition of triethylamine (232 μL, 1.663 mmol). The reaction mixture was stirred at an ice-cold temperature to 25° C. for 15.5 hours and then purified by reverse-phase silica gel column chromatography (a 0.05% aqueous trifluoroacetic acid solution/0.05% trifluoroacetic acid-acetonitrile solution) to afford (R)-2-((((4-azidobenzyl)oxy)carbonyl)amino)-3-(tert-butyldisulfanyl)propanoic acid (Compound tk20) (211.4 mg, 99%).

LCMS (ESI) m/z=383 (M−H)−
Retention time: 0.84 min (analysis condition SQDFA05)

Synthesis of (1R,4'S,5S)-4'-(4-((R)-2-((((4-azidobenzyl)oxy)carbonyl)amino)-3-(tert-butyldisulfanyl)propanamide)butyl)-5'-oxospiro)-5'-bicyclo[3.3.1]nonane-9,2'-[1,3,2]oxazaborolidin-9,2'-[1,3,2]ium-11-uide (Compound tk21)

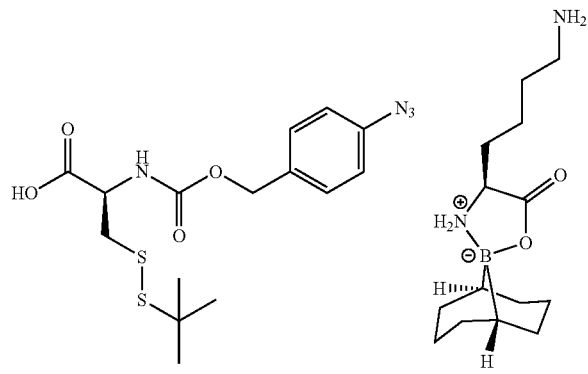

Exact Mass: 384.09     Exact Mass: 266.22

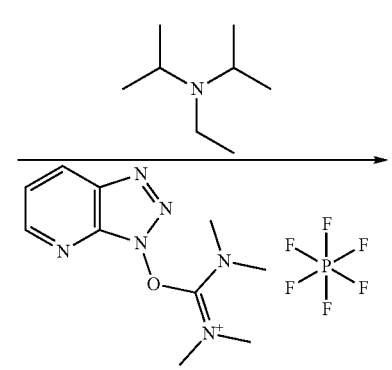

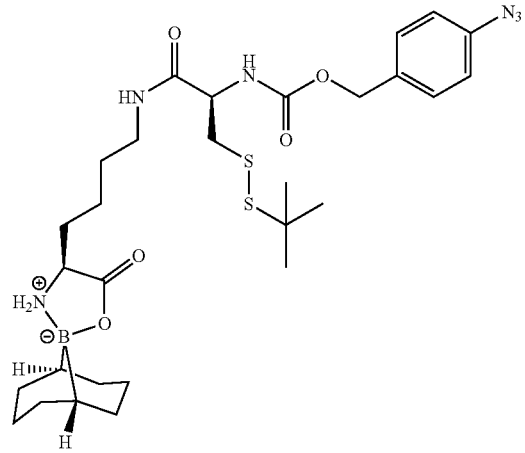

Exact Mass: 632.30

N,N-Diisopropylethylamine (136 microL, 0.781 mmol) was added to a suspension of (1R,4'S,5S)-4'-(4-aminobutyl)-5'-oxospiro[bicyclo[3.3.1]nonane-9,2'-[1,3,2]oxazaborolidin]-3'-ium-ii-uide (Compound 49) (166 mg, 0.625 mmol) and (R)-2-((((4-azidobenzyl)oxy)carbonyl)amino)-3-(tert-butyldisulfanyl)propanoic acid (Compound tk20) (200.3 mg, 0.521 mmol) in DMF (0.6 mL) with stirring at room temperature under a nitrogen atmosphere. The resulting mixture was cooled in an ice bath, followed by addition of HATU (238 mg, 0.625 mmol). The reaction mixture was stirred at room temperature for 45 minutes and then purified by reverse-phase silica gel column chromatography (0.05% aqueous trifluoroacetic acid solution/0.05% trifluoroacetic acid-acetonitrile solution) to afford (1R,4'S,5S)-4'-(4-((R)-2-((((4-azidobenzyl)oxy)carbonyl)amino)-3-(tert-butyldisulfanyl)propanamide)butyl)-5'-oxospiro)-5'-bicyclo[3.3.1]nonane-9,2'-[1,3,2]oxazaborolidin-9,2'-[1,3,2]ium-11-uide (Compound tk21) (313.1 mg, 95%).

LCMS (ESI) m/z=631.5 (M−H)−
Retention time: 1.01 min (analysis condition SQDFA05)

2405

Synthesis of (S)-2-amino-6-((R)-2-((((4-azidobenzyl)oxy)carbonyl)amino)-3-(tert-butyldisulfanyl)propanamido)hexanoic Acid (Lys(Acbz-Cys(StBu))) (Compound tk22)

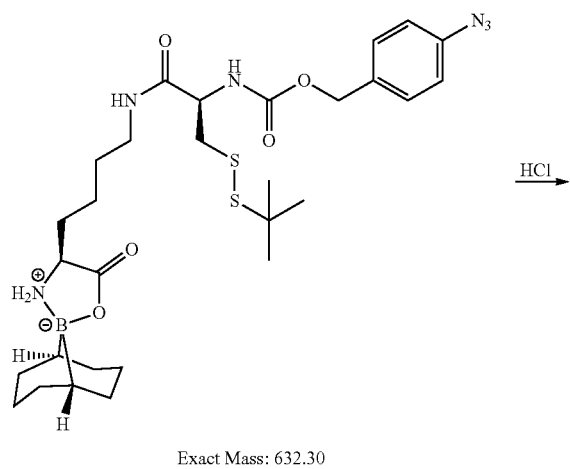

Exact Mass: 632.30

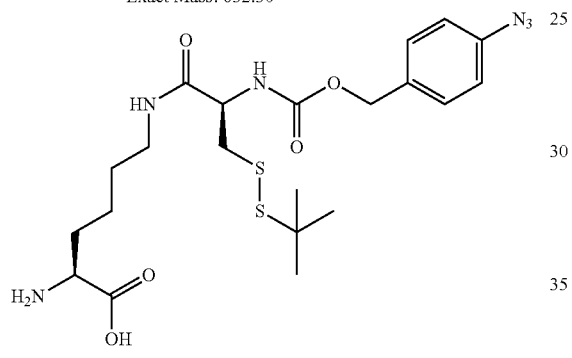

Exact Mass: 512.19

2406

Concentrated hydrochloric acid (395 μL) was added to a suspension of (1R,4'S,5S)-4'-(4-((R)-2-((((4-azidobenzyl)oxy)carbonyl)amino)-3-(tert-butyldisulfanyl)propanamide)butyl)-5'-oxospiro)-5'-bicyclo[3.3.1]nonane-9,2'-[1,3,2]oxazaborolidin-9,2'-[1,3,2]ium-11-uide (Compound tk21) (300 mg, 0.474 mmol) in 1,4-dioxane (2.4 mL) under a nitrogen atmosphere. The reaction mixture was stirred at 40 to 45° C. for 3.5 hours. The reaction mixture was cooled to room temperature and then concentrated under reduced pressure. The resulting residue was purified by reverse-phase silica gel column chromatography (a 0.05% aqueous trifluoroacetic acid solution/0.05% trifluoroacetic acid-acetonitrile solution) to afford (S)-2-amino-6-((R)-2-((((4-azidobenzyl)oxy)carbonyl)amino)-3-(tert-butyldisulfanyl)propanamido)hexanoic acid (Lys(Acbz-Cys(StBu))) (Compound tk22) (121.9 mg, 50%).

LCMS (ESI) m/z=513 (M+H)+
Retention time: 0.61 min (analysis condition SQDFA05)

Synthesis of (S)-6-((R)-2-((((4-azidobenzyl)oxy)carbonyl)amino)-3-(tert-butyldisulfanyl)propanamido)-2-((tert-butoxycarbonyl)amino)hexanoic Acid (Compound tk23)

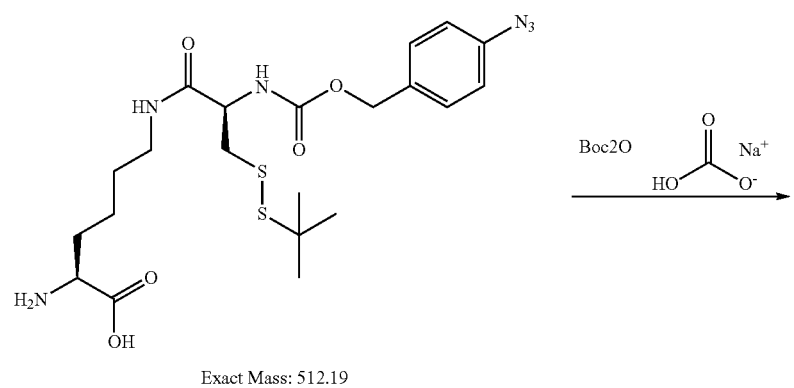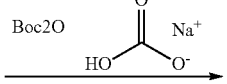

Exact Mass: 512.19

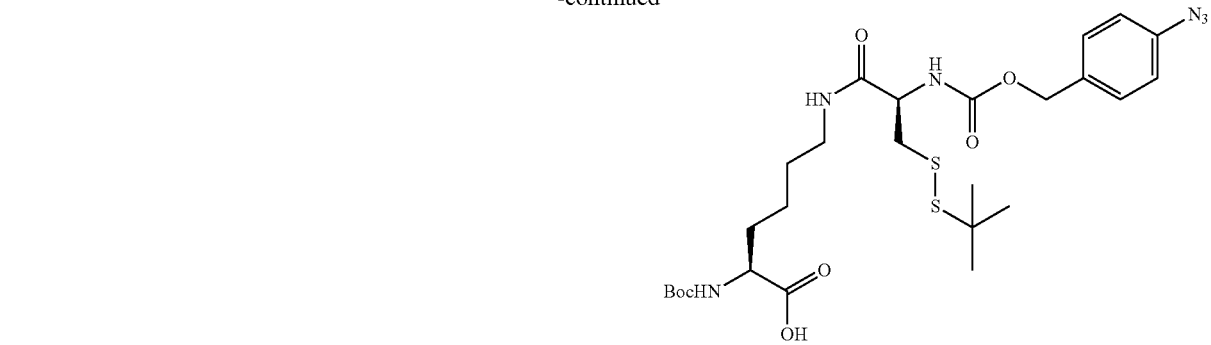

Exact Mass: 612.24

1,4-Dioxane (1 mL) and water (1 mL) were added to (S)-2-amino-6-((R)-2-((((4-azidobenzyl)oxy)carbonyl) amino)-3-(tert-butyldisulfanyl)propanamido)hexanoic acid (Lys(Acbz-Cys(StBu))) (Compound tk22) (121.9 mg, 0.238 mmol) at room temperature. The resulting mixture was cooled in an ice bath, and sodium bicarbonate (59.9 mg, 0.713 mmol) was then added, followed by addition to $Boc_2O$ (104 mg, 0.476 mmol). The resulting reaction mixture was stirred at room temperature for 21 hours and then purified by reverse-phase silica gel column chromatography (0.05% aqueous trifluoroacetic acid solution/0.05% trifluoroacetic acid-acetonitrile solution) to afford (S)-6-((R)-2-((((4-azidobenzyl)oxy)carbonyl)amino)-3-(tert-butyldisulfanyl)propanamido)-2-((tert-butoxycarbonyl)amino)hexanoic acid (Compound tk23) (111.0 mg, 76%).

LCMS (ESI) m/z=611 (M–H)–
Retention time: 0.88 min (analysis condition SQDFA05)

synthesis of (S)-cyanomethyl 6-((R)-2-((((4-azidobenzyl)oxy)carbonyl)amino)-3-(tert-butyldisulfanyl) propanamido)-2-((tert-butoxycarbonyl)amino) hexanoate (Compound tk24)

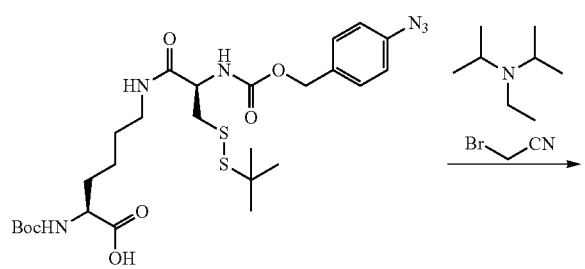

Exact Mass: 612.24

-continued

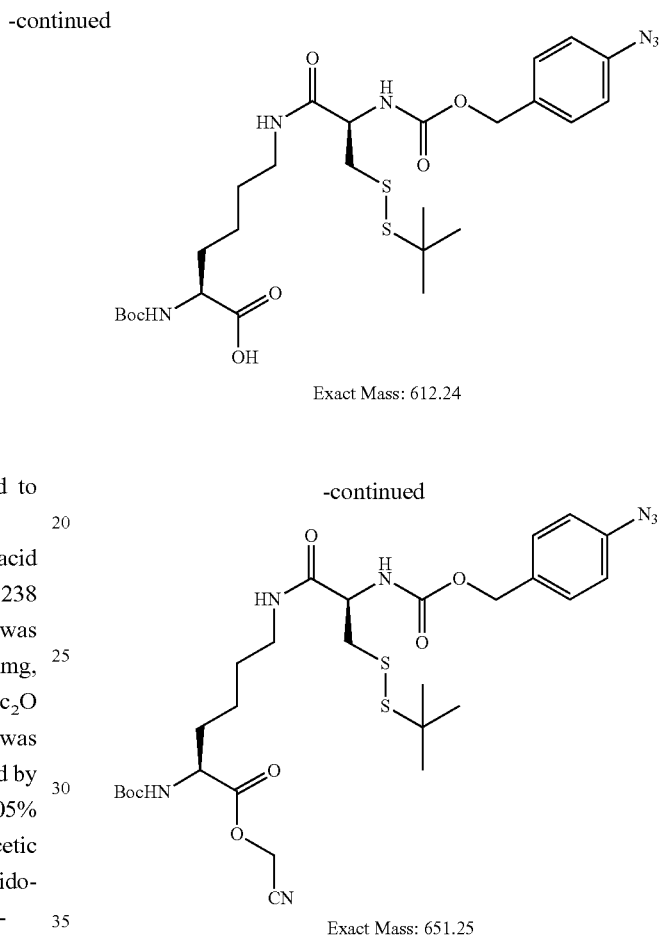

Exact Mass: 651.25

N,N-Diisopropylethylamine (34 μL, 0.197 mmol) and subsequently bromoacetonitrile (38 μL, 0.539 mmol) were added to a solution of (S)-6-((R)-2-((((4-azidobenzyl)oxy) carbonyl)amino)-3-(tert-butyldisulfanyl)propanamido)-2-((tert-butoxycarbonyl)amino)hexanoic acid (Compound tk23) (110 mg, 0.180 mmol) in acetonitrile (0.3 mL) at room temperature under a nitrogen atmosphere. The reaction mixture was stirred at the same temperature for 15.5 hours and then concentrated under reduced pressure, and the resulting crude product was purified by normal-phase silica gel column chromatography (hexane/ethyl acetate) to afford (S)-cyanomethyl 6-((R)-2-((((4-azidobenzyl)oxy)carbonyl) amino)-3-(tert-butyldisulfanyl)propanamido)-2-((tert-butoxycarbonyl)amino)hexanoate (97.3 mg, 83%).

LCMS (ESI) m/z=650.6 (M–H)–
Retention time: 0.95 min (analysis condition SQDFA05)

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-((R)-2-((((4-azidobenzyl)oxy)carbonyl)amino)-3-(tert-butyldisulfanyl)propanamido)-2-((tert-butoxycarbonyl)amino)hexanoate (Compound tk25)

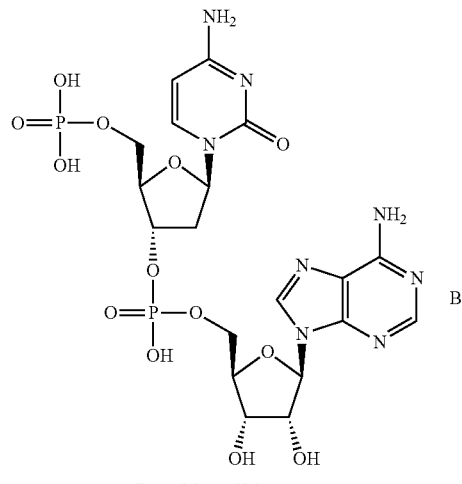

Exact Mass: 636.11

Exact Mass: 651.25

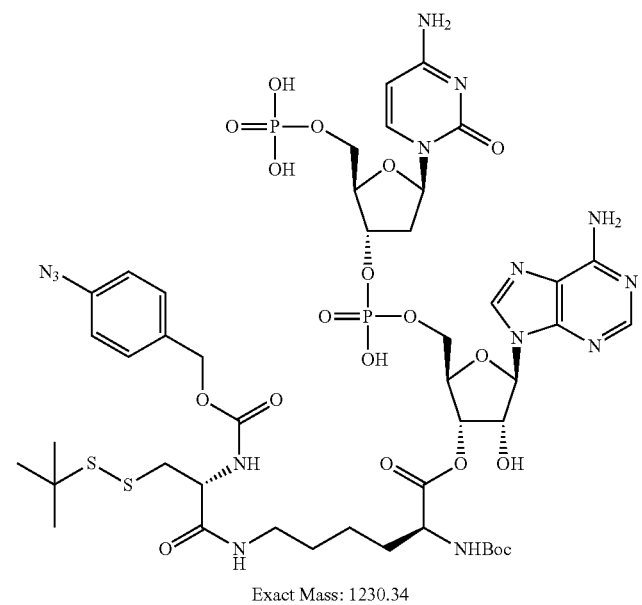

Exact Mass: 1230.34

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (30.3 mg, 0.048 mmol) in water (0.3 mL) and a solution of (S)-cyanomethyl 6-((R)-2-((((4-azidobenzyl)oxy)carbonyl)amino)-3-(tert-butyldisulfanyl)propanamido)-2-((tert-butoxycarbonyl)amino)hexanoate (Compound tk24) (93 mg, 0.143 mmol) in tetrahydrofuran (0.3 mL) were added to buffer A (9 mL), and the mixture was stirred at room temperature for 4.5 hours. Following lyophilization, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-((R)-2-((((4-azidobenzyl)oxy)carbonyl)amino)-3-(tert-butyldisulfanyl)propanamido)-2-((tert-butoxycarbonyl)amino)hexanoate (Compound tk25) (6.7 mg, 11%).

LCMS (ESI) m/z=1231.7 (M+H)+

Retention time: 0.90 min (analysis condition SQDAA05)

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-((R)-2-((((4-azidobenzyl)oxy)carbonyl)amino)-3-(tert-butyldisulfanyl)propanamido)hexanoate (Lys(Acbz-Cys(StBu))-pdCpA) (Compound tk26)

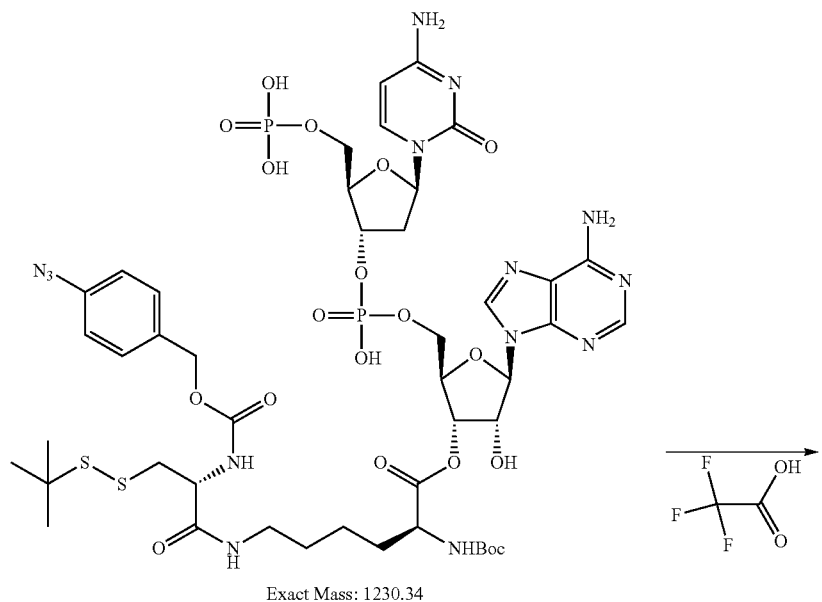

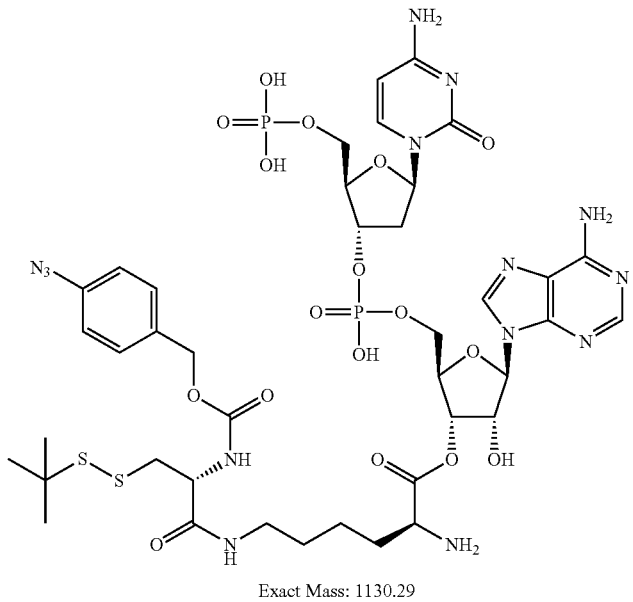

A solution of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-((R)-2-((((4-azidobenzyl)oxy)carbonyl)amino)-3-(tert-butyldisulfanyl)propanamido)-2-((tert-butoxycarbonyl)amino)hexanoate (Compound tk25) (6.7 mg, 5.44 μmol) in dichloromethane (0.4 mL) was cooled in an ice bath, after which trifluoroacetic acid (0.1 mL) was added and the mixture was stirred at room temperature for 25 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-

4-hydroxytetrahydrofuran-3-yl 2-amino-6-(((R)-2-((((4-azidobenzyl)oxy)carbonyl)amino)-3-(tert-butyldisulfanyl)propanamido)hexanoate (Lys(Acbz-Cys(StBu))-pdCpA) (Compound tk26) (1.7 mg, 28%).

LCMS (ESI) m/z=1130.1 (M−H)−

Retention time: 0.54 min (analysis condition SQDFA05)

10-1-5. Synthesis of Aminoacylated pdCpA Compound tk30

The synthesis was carried out according to the following scheme.

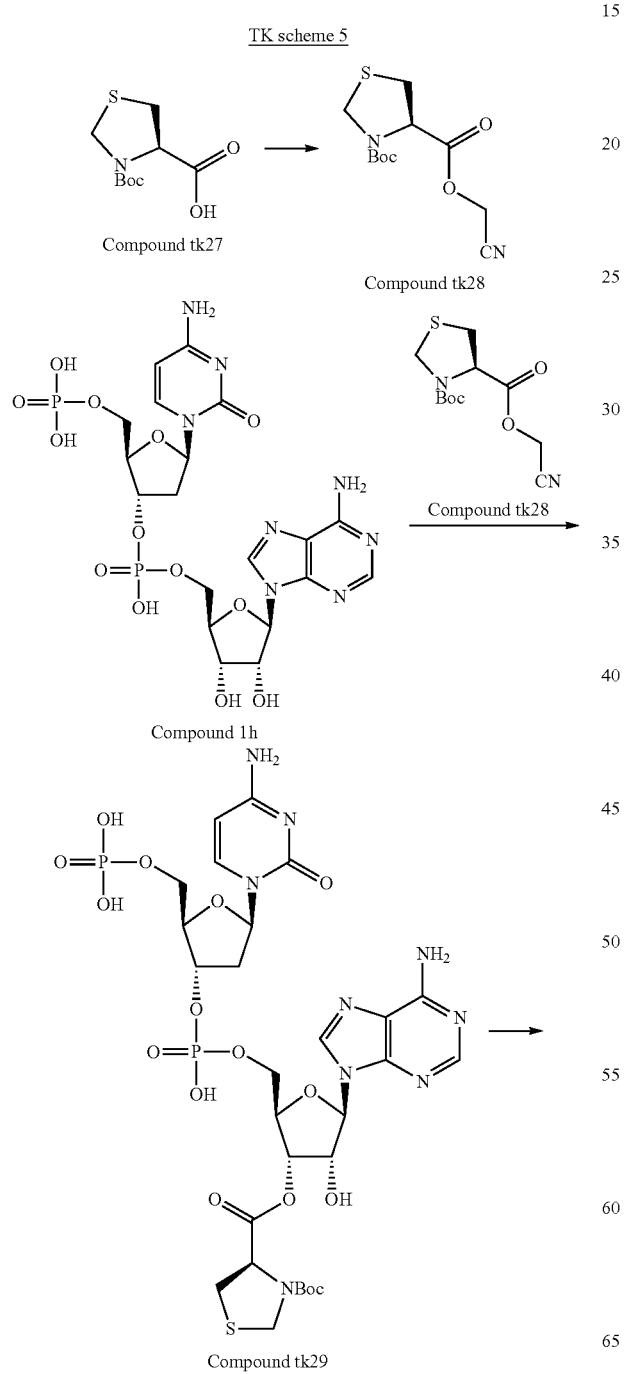

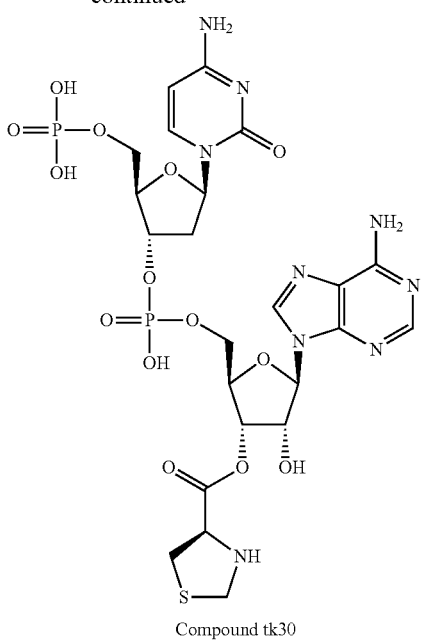

Synthesis of (R)-3-tert-butyl 4-(cyanomethyl) thiazolidine-3,4-dicarboxylate (Compound tk28)

N,N-Diisopropylethylamine (310 μL, 1.778 mmol) and subsequently bromoacetonitrile (563 μL, 8.08 mmol) were added to a solution of Boc-Thiopro-OH (Compound tk27) (377 mg, 1.616 mmol) in acetonitrile (1 mL) at room temperature under a nitrogen atmosphere. The reaction mixture was stirred at the same temperature for 2.25 hours and then concentrated under reduced pressure, and the resulting crude product was purified by normal-phase silica gel column chromatography (hexane/ethyl acetate) to afford (R)-3-tert-butyl 4-(cyanomethyl) thiazolidine-3,4-dicarboxylate (Compound tk28) (272.9 mg, 62%).

LCMS (ESI) m/z=273.3 (M+H)+

Retention time: 0.71 minute (analysis condition SQDFA05)

2415

Synthesis of (4R)-4-((2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl) 3-tert-butyl thiazolidine-3,4-dicarboxylate (Compound tk29)

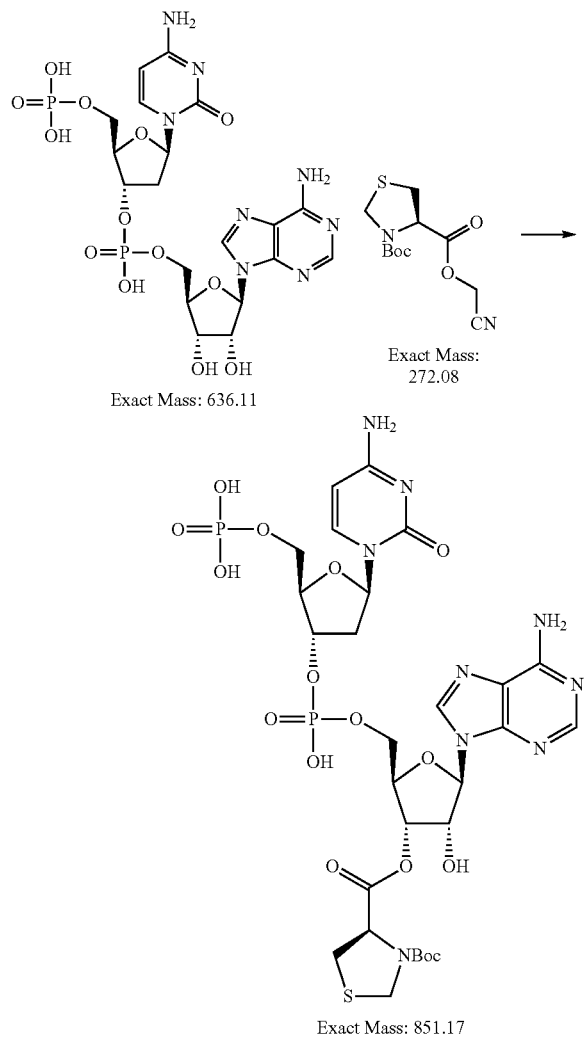

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (148 mg, 0.233 mmol) and (R)-3-tert-butyl 4-(cyanomethyl) thiazolidine-3,4-dicarboxylate (Compound tk28) (254 mg, 0.933 mmol) in acetonitrile (0.7 mL) was added to buffer A (30 mL), and the mixture was stirred at room temperature for 1.5 hours. Following lyophilization, the resulting residue was purified by reverse-phase silica gel column chromatography (0.05% aqueous trifluoroacetic acid solution/0.05% trifluoroacetic acid-acetonitrile solution) to afford (4R)-4-((2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-

2416

4-hydroxytetrahydrofuran-3-yl) 3-tert-butyl thiazolidine-3,4-dicarboxylate (Compound tk29) (64.7 mg, 33%).
LCMS (ESI) m/z=850.3 (M–H)–
Retention time: 0.41 min (analysis condition SQDFA05)

Synthesis of (4R)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl thiazolidine-4-carboxylate (Thiopro-pdCpA) (Compound tk30)

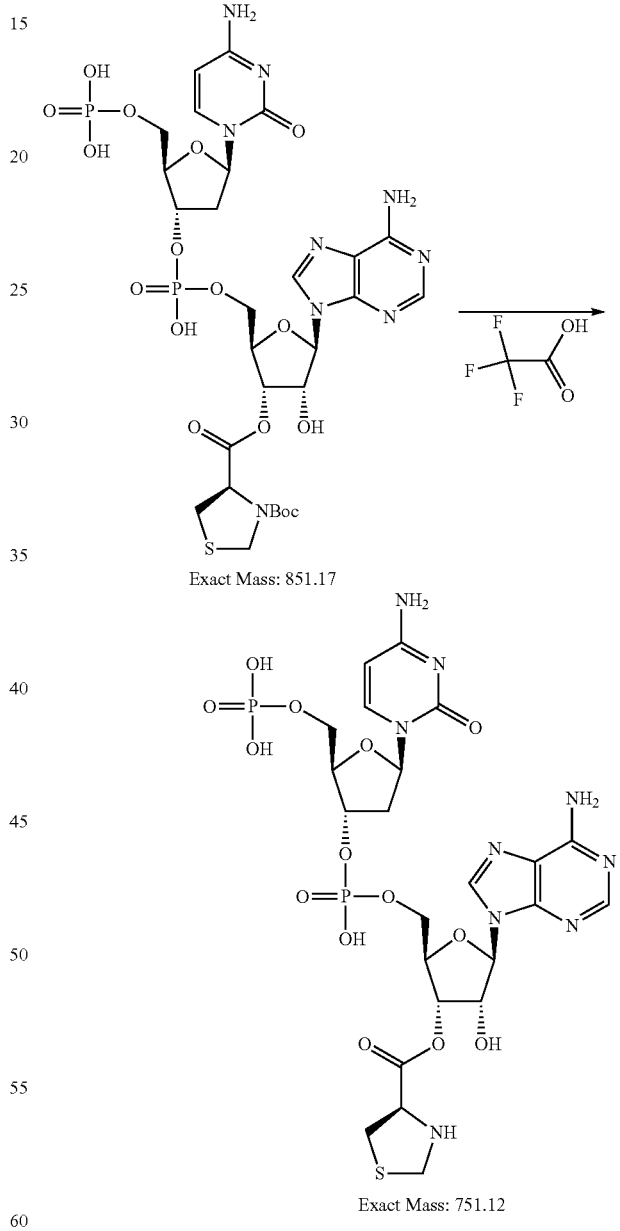

A 10% solution of trifluoroacetic acid in dichloromethane (0.4 mL) was added to a solution of (4R)-4-((2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-tert-butyl thiazolidine-3,4- dicarboxylate (Compound tk29) (19 mg, 0.022 mmol) in dichloromethane (0.4 mL), and the mixture was stirred at room temperature for 60 minutes and then concentrated under reduced pressure to afford (4R)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl thiazolidine-4-carboxylate (Thiopro-pdCpA) (Compound tk30) (25 mg, quant.).

LCMS (ESI) m/z=750.4 (M–H)–
Retention time: 0.34 min (analysis condition SQDAA05)

10-1-6. Synthesis of Aminoacylated pdCpA Compound tk38

The synthesis was carried out according to the following scheme.

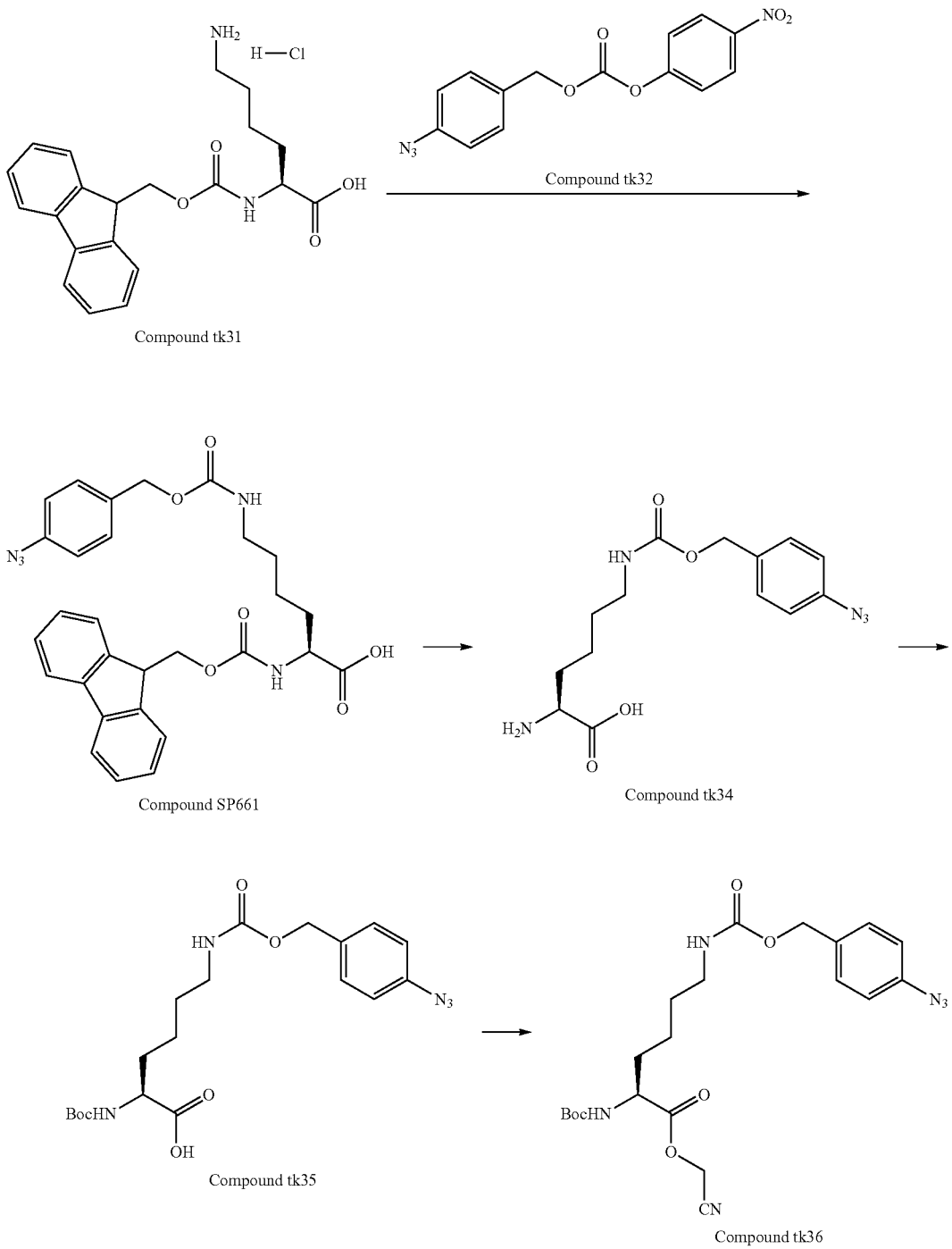

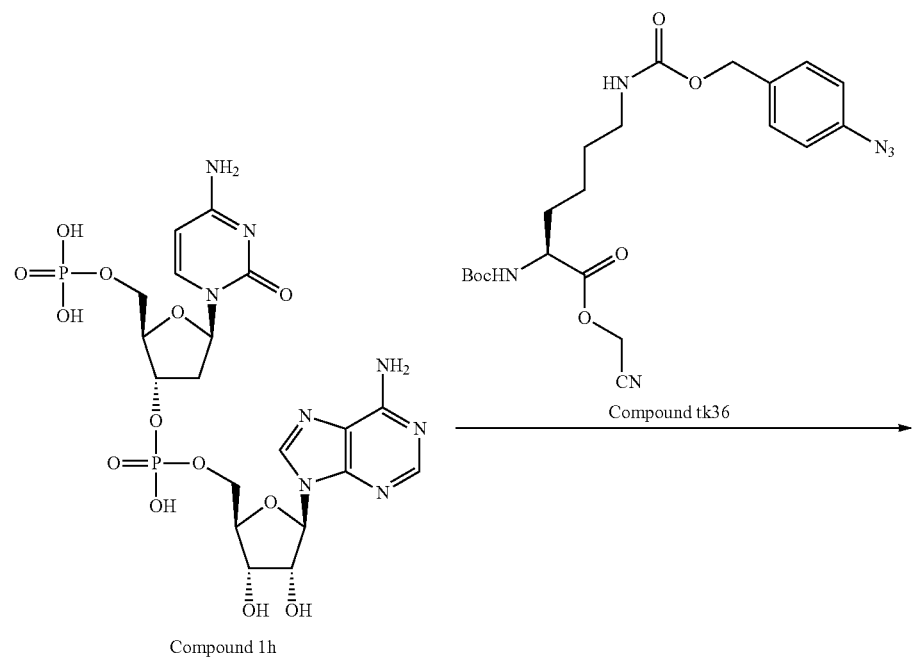
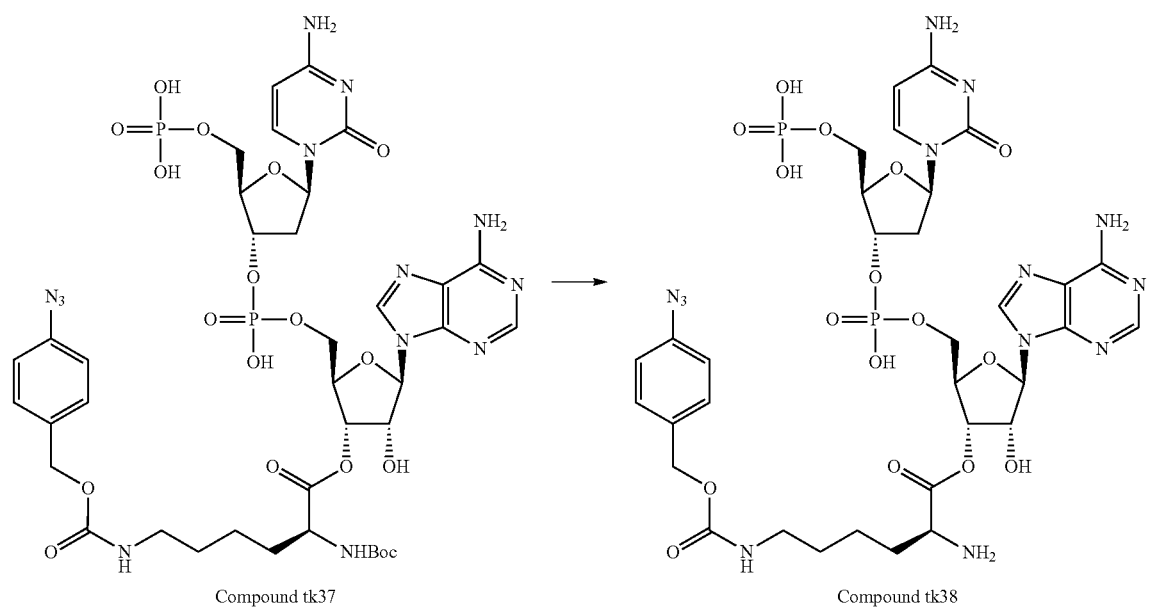

Synthesis of (S)-2-((((9H-fluoren-9-yl)methoxy) carbonyl)amino)-6-((((4-azidobenzyl)oxy)carbonyl) amino)hexanoic Acid (Compound SP661)

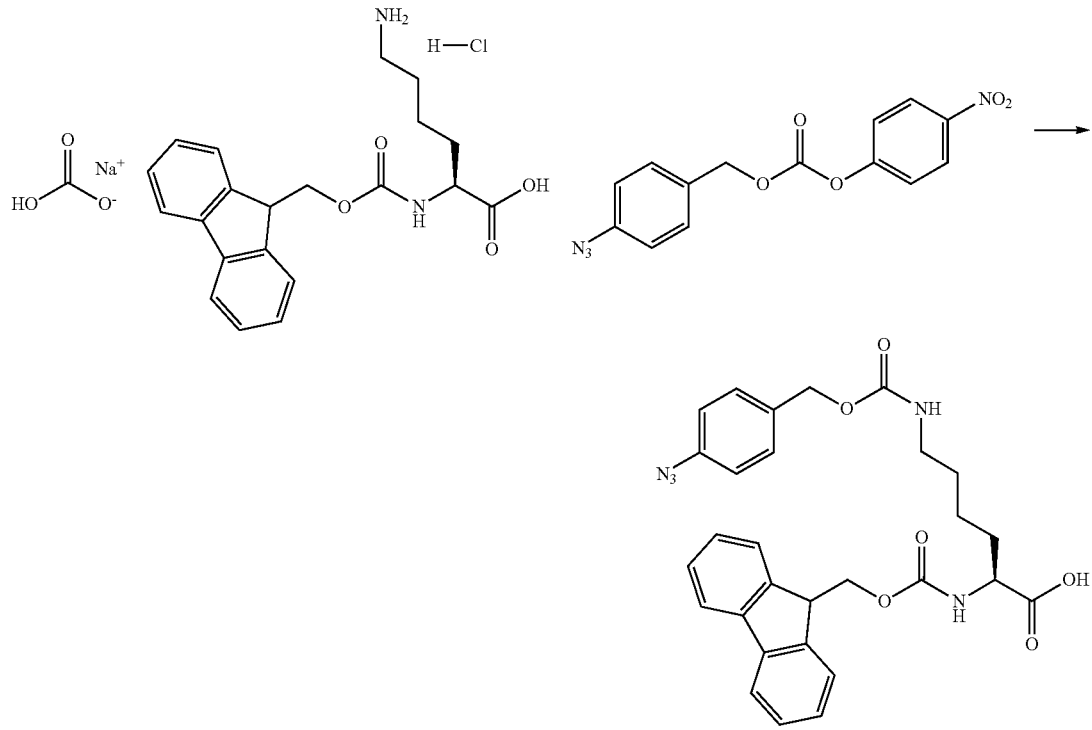

4-Azidobenzyl (4-nitrophenyl) carbonate synthesized by the method described in the literature (Bioconjugate Chem. 2008, 19, 714) (Compound tk32) (3.46 g, 11.0 mmol) was added to a suspension of Fmoc-lysine hydrochloride (Compound tk31) (4.9 g, 12.10 mmol) and sodium bicarbonate (2.77 g, 33.0 mmol) in DMF (22 mL) under ice-cooling. The reaction mixture was stirred at 25° C. for 8 hours and 1 N hydrochloric acid was then added, followed by extraction with ethyl acetate. The organic phase was washed with brine three times and dried over sodium sulfate. Following concentration under reduced pressure, the resulting residue was purified by reverse-phase silica gel column chromatography (0.1% aqueous formic acid solution/0.1% formic acid-acetonitrile solution) to afford (S)-2-((((9H-fluoren-9-yl) methoxy)carbonyl)amino)-6-((((4-azidobenzyl)oxy)carbonyl)amino)hexanoic acid (Compound SP661) (5.5 g, 92%).

LCMS (ESI) m/z=542 (M−H)−

Retention time: 0.89 min (analysis condition SQDFA05)

Synthesis of (S)-2-amino-6-((((4-azidobenzyl)oxy) carbonyl)amino)hexanoic Acid (Lys(Acbz)) (Compound tk34)

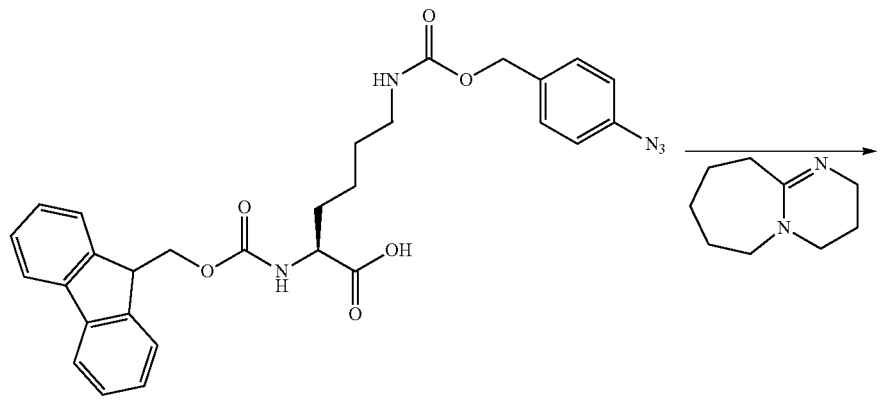

Exact Mass: 543.21

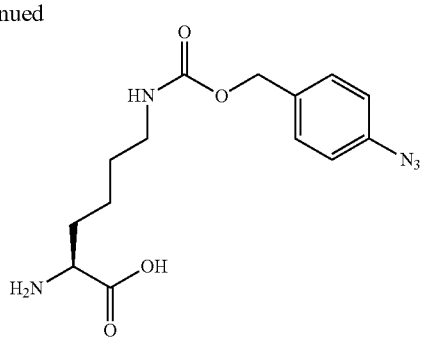

Exact Mass: 321.14

DBU (0.064 mL, 0.425 mmol) was added to a solution of (S)-2-((((9H-fluoren-9-yl)methoxy)carbonyl)amino)-6-((((4-azidobenzyl)oxy)carbonyl)amino)hexanoic acid (Compound SP661) (210 mg, 0.386 mmol) in DMF (0.7 mL) at room temperature under a nitrogen atmosphere. The resulting reaction mixture was stirred at the same temperature for 20 minutes and then purified by reverse-phase silica gel column chromatography (0.05% aqueous trifluoroacetic acid solution/0.05% trifluoroacetic acid-acetonitrile solution) to afford (S)-2-amino-6-((((4-azidobenzyl)oxy)carbonyl)amino)hexanoic acid (Lys(Acbz)) (Compound tk34) (100 mg, 81%).

LCMS (ESI) m/z=320 (M−H)−
Retention time: 0.47 min (analysis condition SQDFA05)

Synthesis of (S)-6-((((4-azidobenzyl)oxy)carbonyl)amino)-2-((tert-butoxycarbonyl)amino)hexanoic Acid (Compound tk35)

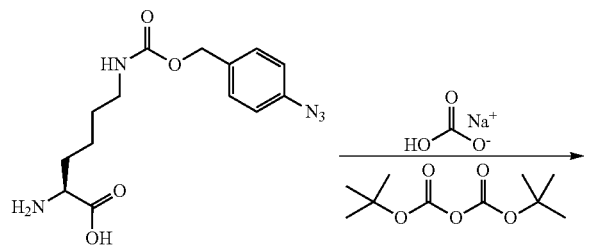

Exact Mass: 321.14

1,4-Dioxane (5 mL) and water (2 mL) were added to 2-amino-6-((((4-azidobenzyl)oxy)carbonyl)amino)hexanoic acid (Lys(Acbz)) (Compound tk34) (100 mg, 0.311 mmol) at room temperature. The resulting mixture was cooled in an ice bath, and sodium bicarbonate (78 mg, 0.934 mmol) was then added, followed by addition to Boc$_2$O (136 mg, 0.622 mmol). The resulting reaction mixture was stirred at room temperature for 2 hours and 20 minutes, followed by addition of Boc$_2$O (70 mg). After stirring at the same temperature for 40 minutes, ethyl acetate and water were added under ice-cooling. A saturated aqueous potassium bisulfate solution (0.3 mL) was added to the resulting mixture, followed by extraction with ethyl acetate twice. The organic phase was washed with water and brine and dried over sodium sulfate. Following concentration under reduced pressure, the resulting crude product was purified by normal-phase silica gel column chromatography (hexane/ethyl acetate) to afford (S)-6-((((4-azidobenzyl)oxy)carbonyl)amino)-2-((tert-butoxycarbonyl)amino)hexanoic acid (Compound tk35) (103.9 mg, 79%).

LCMS (ESI) m/z=420 (M−H)−
Retention time: 0.76 min (analysis condition SQDFA05)

Synthesis of (S)-cyanomethyl 6-((((4-azidobenzyl)oxy)carbonyl)amino)-2-((tert-butoxycarbonyl)amino)hexanoate (Compound tk36)

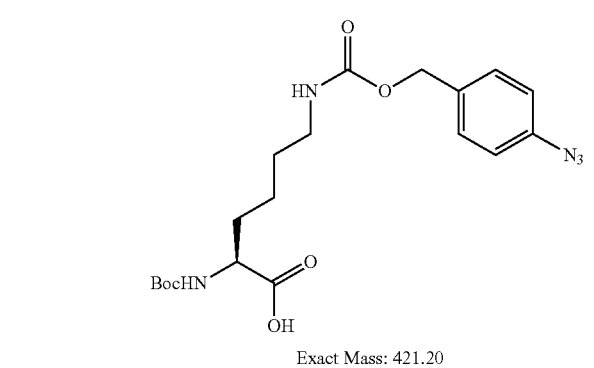

Exact Mass: 421.20

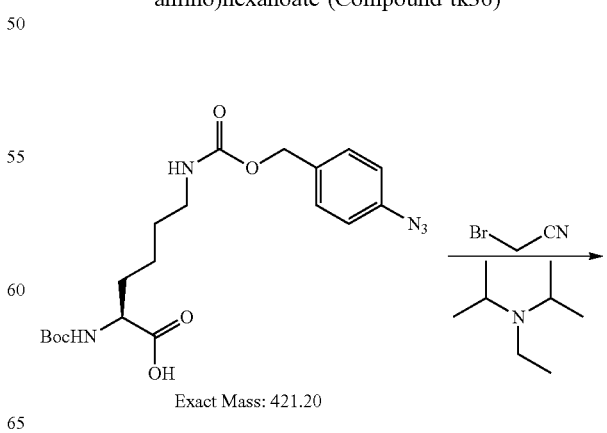

Exact Mass: 421.20

2425

-continued

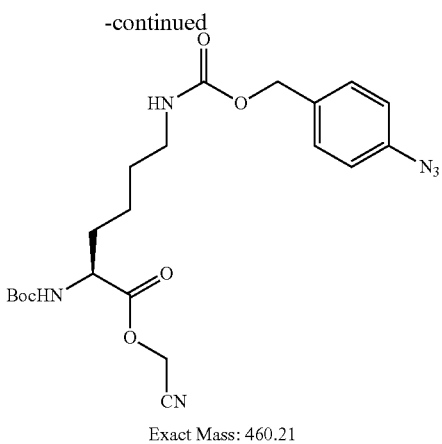

Exact Mass: 460.21

N,N-Diisopropylethylamine (46 µL, 0.263 mmol) and subsequently bromoacetonitrile (33 µL, 1.197 mmol) were added to a solution of (S)-6-((((4-azidobenzyl)oxy)carbo-

2426 nyl)amino)-2-((tert-butoxycarbonyl)amino)hexanoic acid (Compound tk35) (100.9 mg, 0.239 mmol) in acetonitrile (0.4 mL) at room temperature under a nitrogen atmosphere. The reaction mixture was stirred at the same temperature for 2.5 hours and then concentrated under reduced pressure, and the resulting crude product was purified by normal-phase silica gel column chromatography (hexane/ethyl acetate) to afford (S)-cyanomethyl 6-((((4-azidobenzyl)oxy)carbonyl)amino)-2-((tert-butoxycarbonyl)amino)hexanoate (Compound tk36) (108.5 mg, 98%).

LCMS (ESI) m/z=459 (M−H)−

Retention time: 0.84 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-((((4-azidobenzyl)oxy)carbonyl)amino)-2-((tert-butoxycarbonyl)amino)hexanoate (Compound tk37)

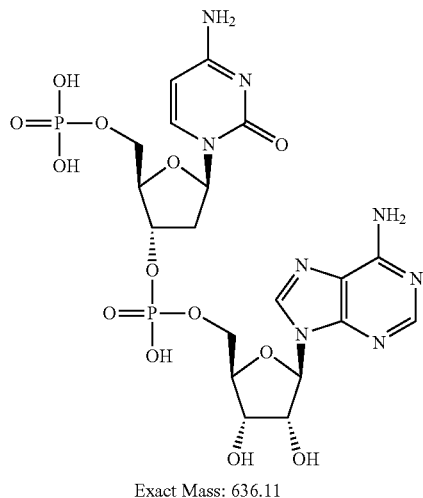

Exact Mass: 636.11

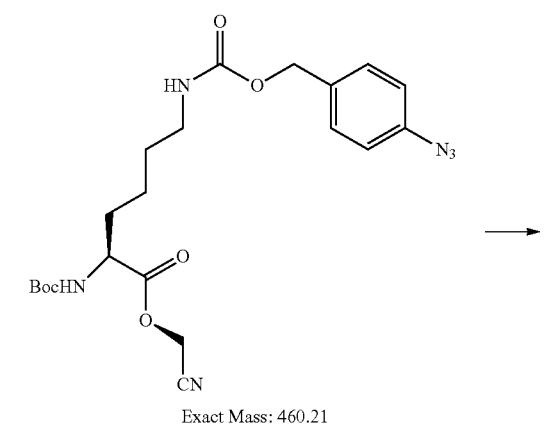

Exact Mass: 460.21

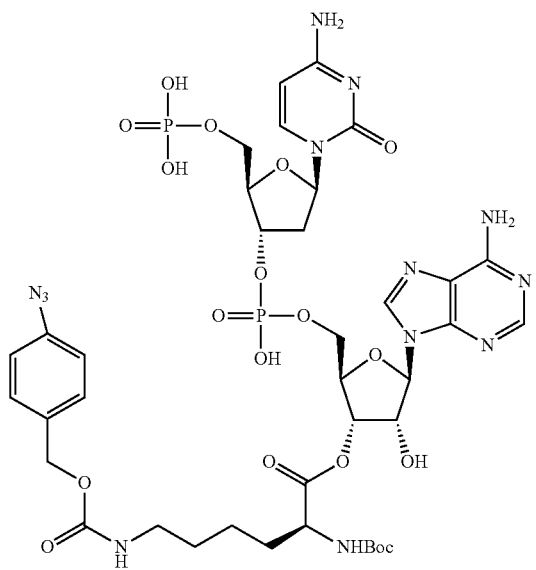

Exact Mass: 1039.30

A solution of ((2R,3S,5R)-5-(4-amino-2-oxopyrimidin-1 (2H)-yl)-3-(((((2R,3S,4R,5R)-5-(6-amino-9H-purin-9-yl)-3, 4-dihydroxytetrahydrofuran-2-yl)methoxy)(hydroxy)phosphoryl)oxy)tetrahydrofuran-2-yl)methyl dihydrogenphosphate (Compound 1h) (47.9 mg, 0.075 mmol) in water (0.3 mL) and a solution of (S)-cyanomethyl 6-((((4-azidobenzyl)oxy)carbonyl)amino)-2-((tert-butoxycarbonyl)amino) hexanoate (Compound tk36) (104 mg, 0226 mmol) in tetrahydrofuran (0.3 mL) were added to buffer A (14 mL), and the mixture was stirred at room temperature for 1.75 hours. Following lyophilization, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy) methyl)tetrahydrofuran-3-yl)oxy)(hydroxy)phosphoryl) oxy)methyl)-5-(6-amino-9H-purin-9-yl)-4-hydroxytetrahydrofuran-3-yl 6-((((4-azidobenzyl)oxy) carbonyl)amino)-2-((tert-butoxycarbonyl)amino)hexanoate (Compound tk37) (14.6 mg, 19%).

LCMS (ESI) m/z=1040.8 (M+H)+

Retention time: 0.56 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy) phosphoryl)oxy)methyl)-5-(6-amino-9H-purin-9-yl)-4-hydroxytetrahydrofuran-3-yl 2-amino-6-((((4-azidobenzyl)oxy)carbonyl)amino)hexanoate (Lys (Acbz)-pdCpA) (Compound tk38)

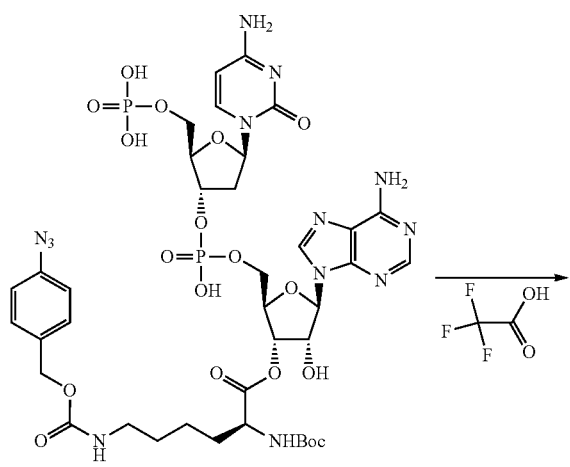

Exact Mass: 1039.30

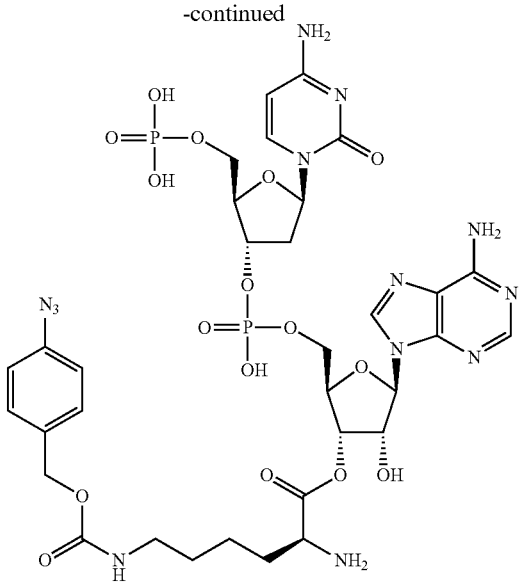

Exact Mass: 939.24

A solution of (23)-(2R,3S,4R,5R)-2-((((((2R,3S,5R)-5-(4-amino-2-oxopyrimidin-1(2H)-yl)-2-((phosphonooxy) methyl)tetrahydrofuran-3-yl)oxy)(hydroxy)phosphoryl) oxy)methyl)-5-(6-amino-9H-purin-9-yl)-4-hydroxytetrahydrofuran-3-yl 6-((((4-azidobenzyl)oxy) carbonyl)amino)-2-((tert-butoxycarbonyl)amino)hexanoate (Compound tk37) (14.6 mg, 0.014 mmol) in dichloromethane (0.4 mL) was cooled in an ice bath, after which trifluoroacetic acid (0.05 mL) was added and the mixture was stirred at room temperature for 35 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R, 3S,4R,5R)-2-((((((2R,3S,5R)-5-(4-amino-2-oxopyrimidin-1 (2H)-yl)-2-((phosphonooxy)methyl)tetrahydrofuran-3-yl) oxy)(hydroxy)phosphoryl)oxy)methyl)-5-(6-amino-9H-purin-9-yl)-4-hydroxytetrahydrofuran-3-yl 2-amino-6-((((4-azidobenzyl)oxy)carbonyl)amino)hexanoate (Lys(Acbz)-pdCpA) (Compound tk38) (1.1 mg, 8%).

LCMS (ESI) m/z=938.5 (M−H)−

Retention time: 0.39 min (analysis condition SQDFA05)

10-1-7. Synthesis of Aminoacylated pdCpA Compound tk43

The synthesis was carried out according to the following scheme.

TK scheme 7

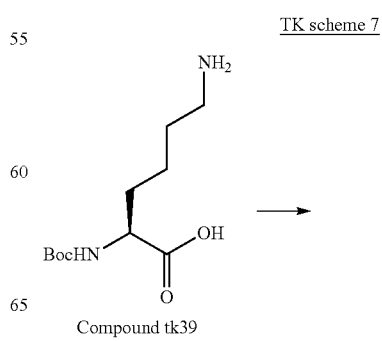

Compound tk39

2429
-continued
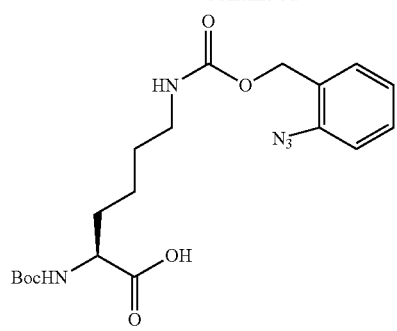
Compound tk40
2430
-continued
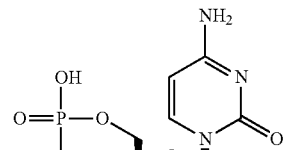
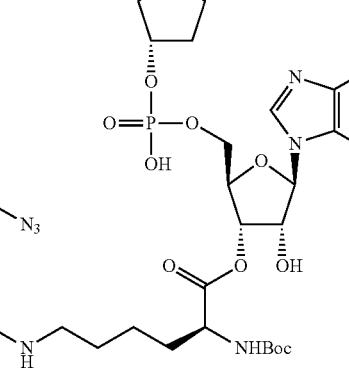
Compound tk42
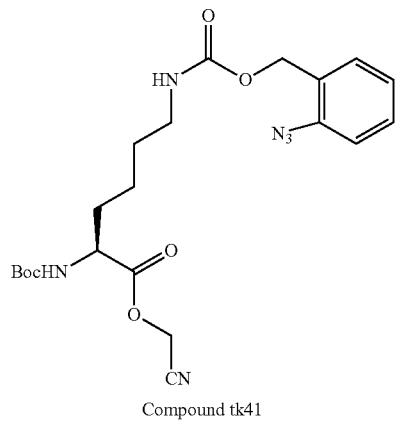
Compound tk41
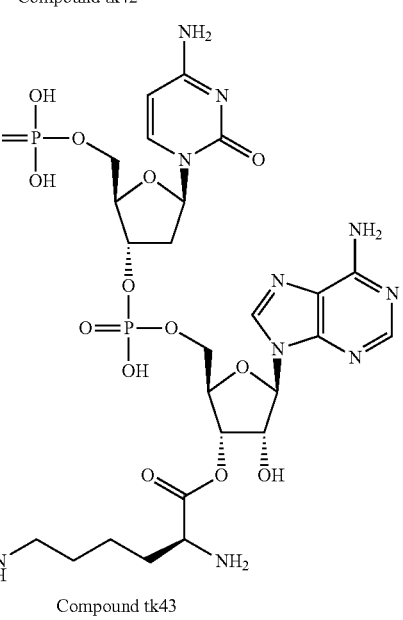
Compound tk43
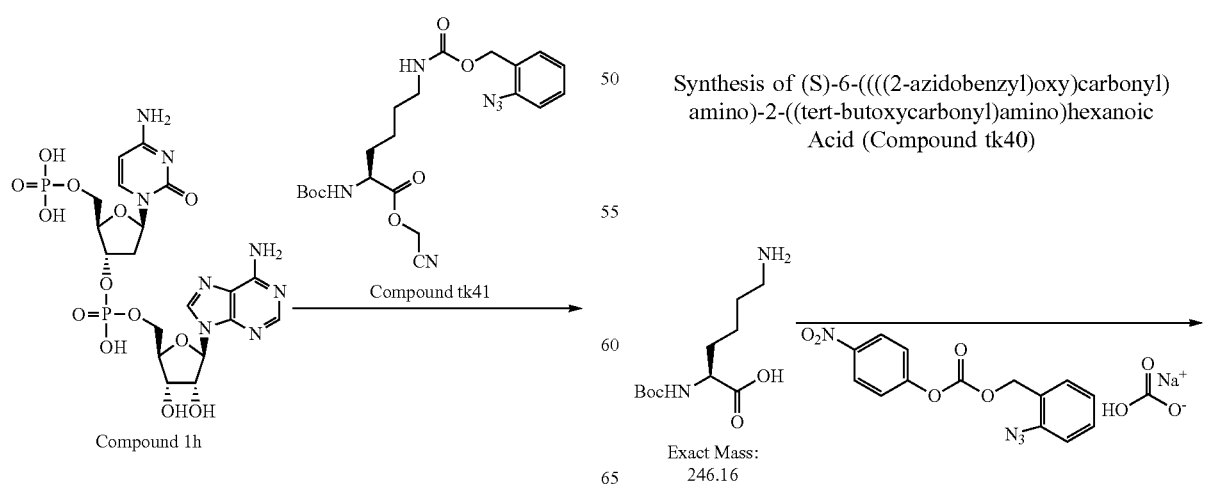
Compound 1h
Synthesis of (S)-6-((((2-azidobenzyl)oxy)carbonyl)amino)-2-((tert-butoxycarbonyl)amino)hexanoic Acid (Compound tk40)
Exact Mass: 246.16

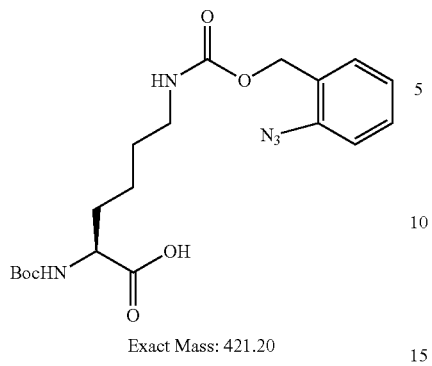

Exact Mass: 421.20

2-Azidobenzyl (4-nitrophenyl) carbonate (414 mg, 1.317 mmol) was added to a suspension of Boc-Lys-OH (Compound tk39) (295 mg, 1.198 mmol) and sodium bicarbonate (252 mg, 2.99 mmol) in 1,4-dioxane (3 mL)-water (2 mL). The reaction mixture was stirred at room temperature for 22 hours and then cooled in an ice bath and diluted with ethyl acetate and water, and a saturated aqueous potassium bisulfate solution (0.7 mL) was added to the resulting mixture. The mixture was extracted with ethyl acetate (×2), and the organic phase was washed with water (10 mL×2) and brine (10 mL) and dried over sodium sulfate. Following concentration under reduced pressure, the resulting crude product was purified by normal-phase silica gel column chromatography (hexane/ethyl acetate) to afford (S)-6-((((2-azidobenzyl)oxy)carbonyl)amino)-2-((tert-butoxycarbonyl)amino)hexanoic acid (Compound tk40) (431.5 mg, 85%).

LCMS (ESI) m/z=420 (M−H)−

Retention time: 0.76 min (analysis condition SQDFA05)

Synthesis of (S)-cyanomethyl 6-((((2-azidobenzyl) oxy)carbonyl)amino)-2-((tert-butoxycarbonyl) amino)hexanoate (Compound tk41)

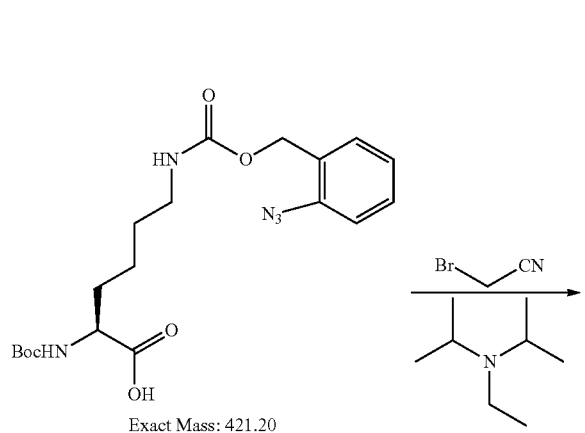

Exact Mass: 421.20

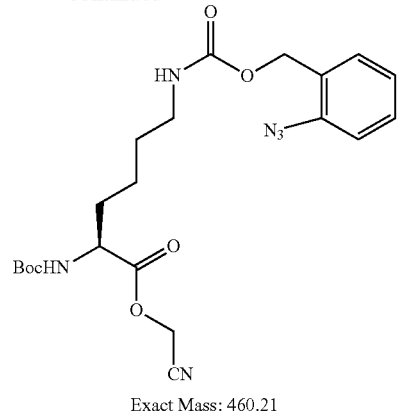

Exact Mass: 460.21

N,N-Diisopropylethylamine (52 µL, 0.298 mmol) and subsequently bromoacetonitrile (94 µL, 1.352 mmol) were added to a solution of (S)-6-((((2-azidobenzyl)oxy)carbonyl)amino)-2-((tert-butoxycarbonyl)amino)hexanoic acid (Compound tk40) (114 mg, 0.270 mmol) in acetonitrile (0.4 mL) at room temperature under a nitrogen atmosphere. The reaction mixture was stirred at the same temperature for 1.5 hours and then concentrated under reduced pressure, and the resulting crude product was purified by normal-phase silica gel column chromatography (hexane/ethyl acetate) to afford (S)-cyanomethyl 6-((((2-azidobenzyl)oxy)carbonyl)amino)-2-((tert-butoxycarbonyl)amino)hexanoate (Compound tk41) (140.2 mg, quant.).

LCMS (ESI) m/z=459.5 (M−H)−

Retention time: 0.84 minute (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-((((2-azidobenzyl)oxy)carbonyl)amino)-2-((tert-butoxycarbonyl)amino)hexanoate (Compound tk42)

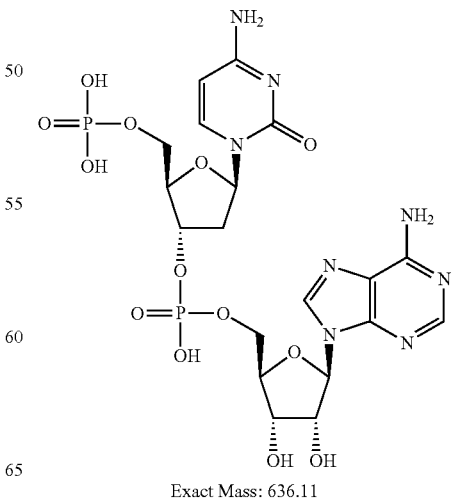

Exact Mass: 636.11

2433
-continued

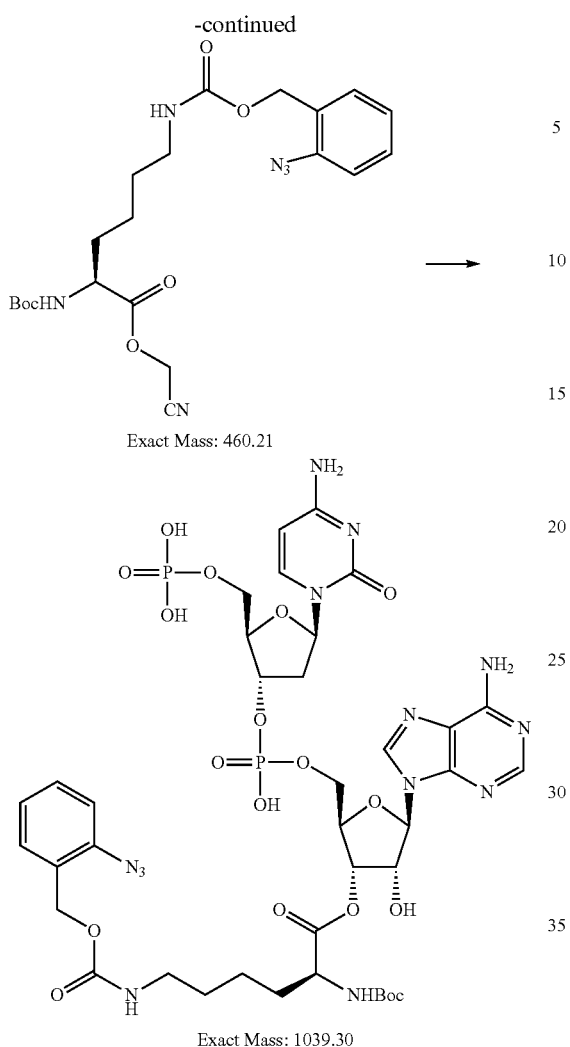

A solution of ((2R,3S,5R)-5-(4-amino-2-oxopyrimidin-1 (2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (46.3 mg, 0.073 mmol) in water (0.3 mL) and a solution of (S)-cyanomethyl 6-((((2-azidobenzyl)oxy)carbonyl)amino)-2-((tert-butoxycarbonyl)amino)hexanoate (Compound tk41) (134 mg, 0.291 mmol) in tetrahydrofuran (0.3 mL) were added to buffer A (14 mL), and the mixture was stirred at room temperature for 1.75 hours. Acetonitrile (0.6 mL) was added and the mixture was stirred at the same temperature for 1.25 hours. Following lyophilization, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-((((2-azidobenzyl)oxy)carbonyl)amino)-2-((tert-butoxycarbonyl)amino)hexanoate (Compound tk42) (11.1 mg, 15%).

LCMS (ESI) m/z=1038.6 (M–H)–

Retention time: 0.58 min (analysis condition SQDFA05)

2434

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-((((2-azidobenzyl)oxy)carbonyl)amino)hexanoate (Lys (oAcbz)-pdCpA) (Compound tk43)

Trifluoroacetic acid (0.075 mL) was added to a solution of (2,9)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (Compound tk42) (10 mg, 9.62 μmol) in dichloromethane (0.4 mL), and the mixture was stirred at room temperature for 20 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-((((2-azidobenzyl)oxy)carbonyl)amino)hexanoate (Lys(oAcbz)-pdCpA) (Compound tk43) (8.0 mg, 89%).

LCMS (ESI) m/z=938.5 (M−H)−

Retention time: 0.39 min (analysis condition SQDFA05)

10-1-8. Synthesis of Aminoacylated pdCpA Compound tk47

The synthesis was carried out according to the following scheme.

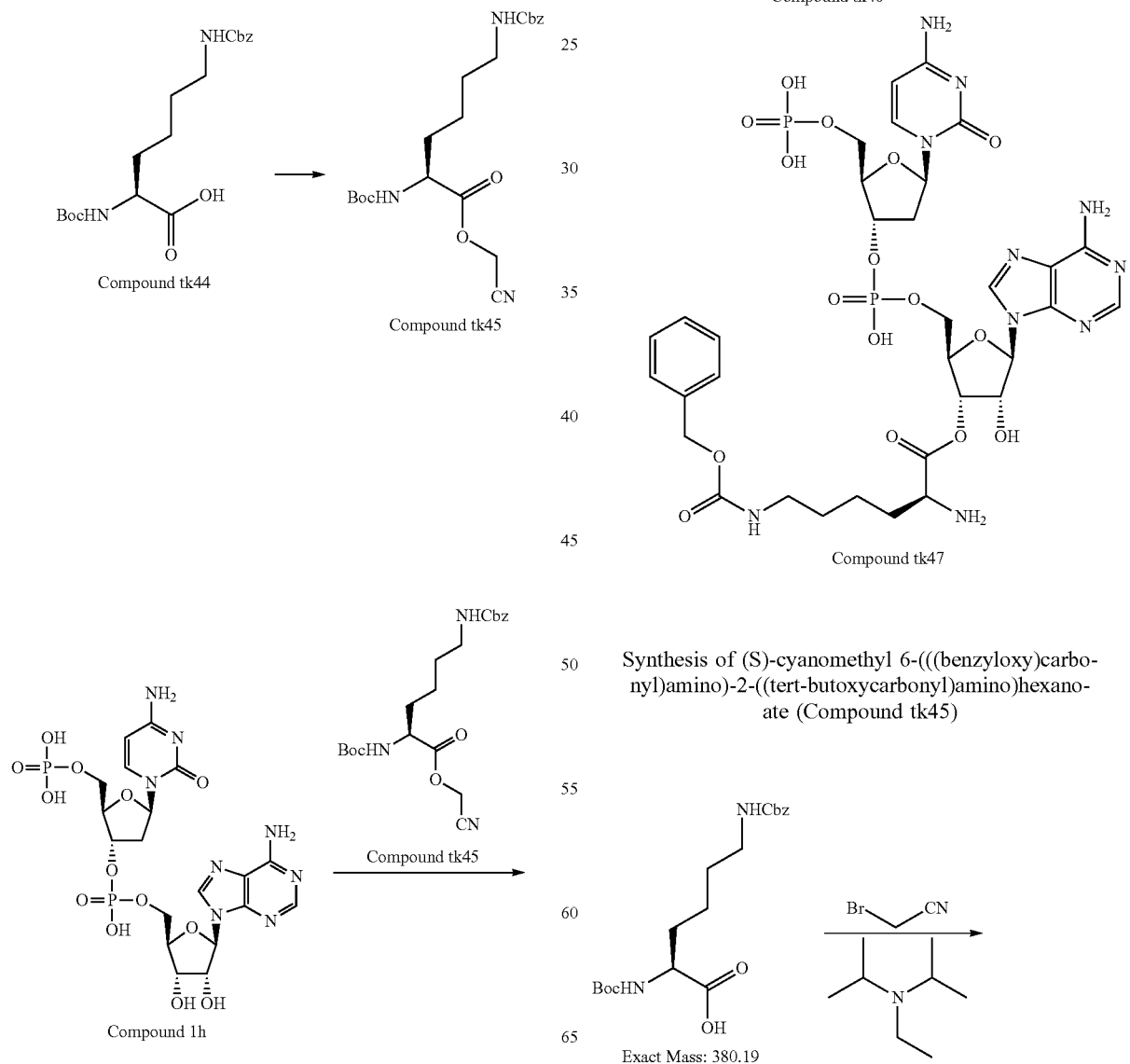

Synthesis of (S)-cyanomethyl 6-(((benzyloxy)carbonyl)amino)-2-((tert-butoxycarbonyl)amino)hexanoate (Compound tk45)

2437
-continued

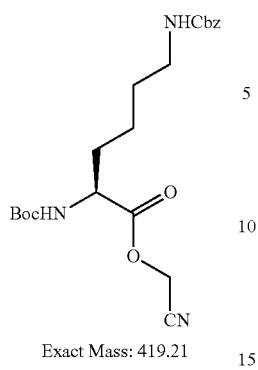

Exact Mass: 419.21

N,N-Diisopropylethylamine (81 μL, 0.463 mmol) and subsequently bromoacetonitrile (147 μL, 2.103 mmol) were added to a solution of Boc-Lys(Z)—OH (Compound tk44) (160 mg, 0.421 mmol) in acetonitrile (0.6 mL) at room temperature under a nitrogen atmosphere. The reaction mixture was stirred at the same temperature for 13 hours and then concentrated under reduced pressure, and the resulting crude product was purified by normal-phase silica gel column chromatography (hexane/ethyl acetate) to afford (S)-cyanomethyl 6-(((benzyloxy)carbonyl)amino)-2-((tert-butoxycarbonyl)amino)hexanoate (Compound tk45) (180 mg, quant.).

LCMS (ESI) m/z=418 (M−H)−

Retention time: 0.79 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-(((benzyloxy)carbonyl)amino)-2-((tert-butoxycarbonyl)amino)hexanoate (Compound tk46)

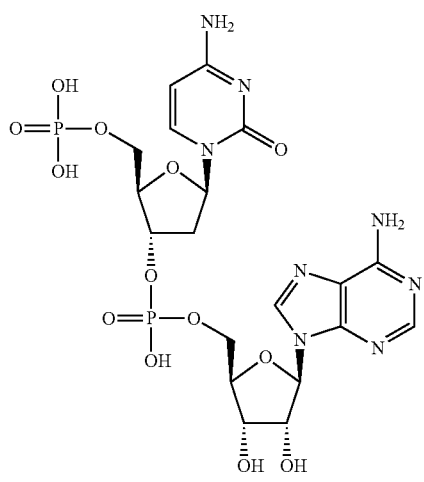

Exact Mass: 636.11

2438
-continued

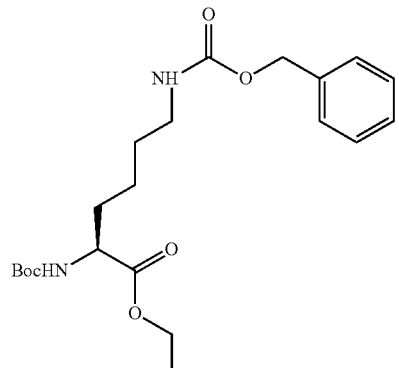

Exact Mass: 419.21

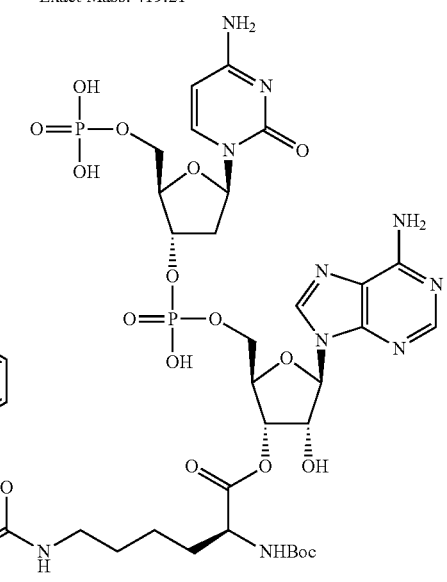

Exact Mass: 998.29

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (65.6 mg, 0.103 mmol) in water (0.3 mL) and a solution of (S)-cyanomethyl 6-(((benzyloxy)carbonyl)amino)-2-((tert-butoxycarbonyl)amino)hexanoate (Compound tk45) (173 mg, 0.412 mmol) in tetrahydrofuran (0.3 mL) were added to buffer A (18 mL), and the mixture was stirred at room temperature for 0.75 hour. Following lyophilization, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-(((benzyloxy)carbonyl)amino)-2-((tert-butoxycarbonyl)amino)hexanoate (Compound tk46) (18.6 mg, 18%).

LCMS (ESI) m/z=999.7 (M+H)+

Retention time: 0.53 min (analysis condition SQDFA05)

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-(((benzyloxy)carbonyl)amino)hexanoate (Lys(Z)-pdCpA) (Compound tk47)

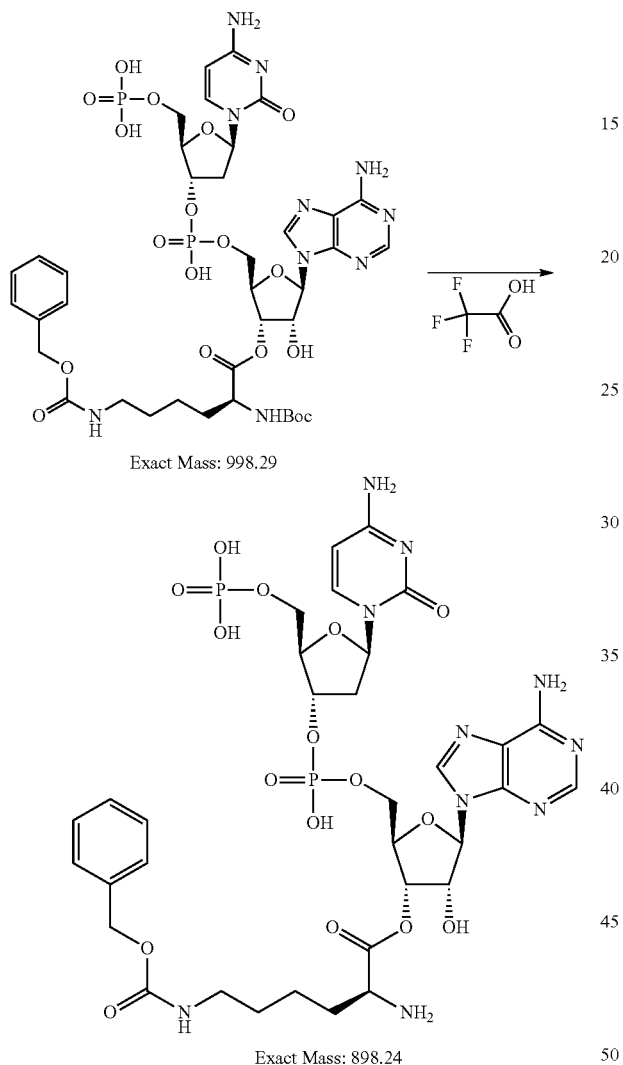

Trifluoroacetic acid (0.075 mL) was added to a solution of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-(((benzyloxy)carbonyl)amino)-2-((tert-butoxycarbonyl)amino)hexanoate (Compound tk46) (18.6 mg, 0.019 mmol) in dichloromethane (1 mL), and the mixture was stirred at room temperature for 40 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-(((benzyloxy)carbonyl)amino)hexanoate (Lys(Z)-pdCpA) (Compound tk47) (13.4 mg, 80%).

LCMS (ESI) m/z=897.4 (M–H)–

Retention time: 0.35 min (analysis condition SQDFA05)

10-1-9. Synthesis of Aminoacylated pdCpA Compound tk51

The synthesis was carried out according to the following scheme.

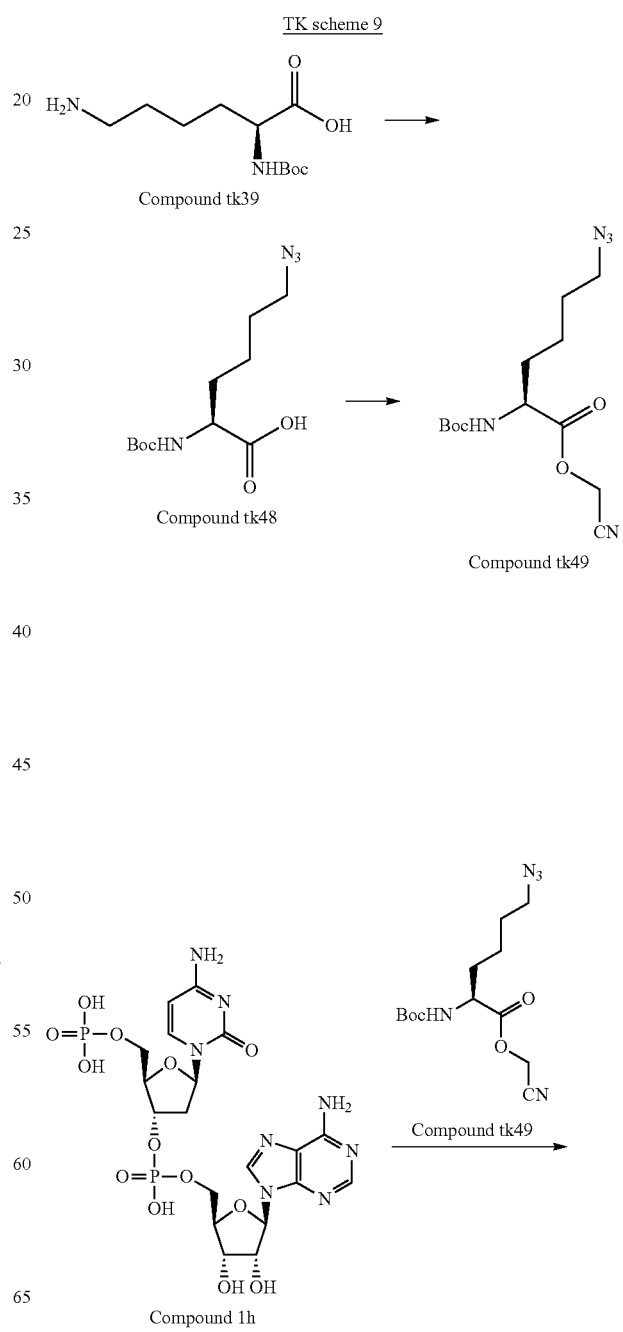

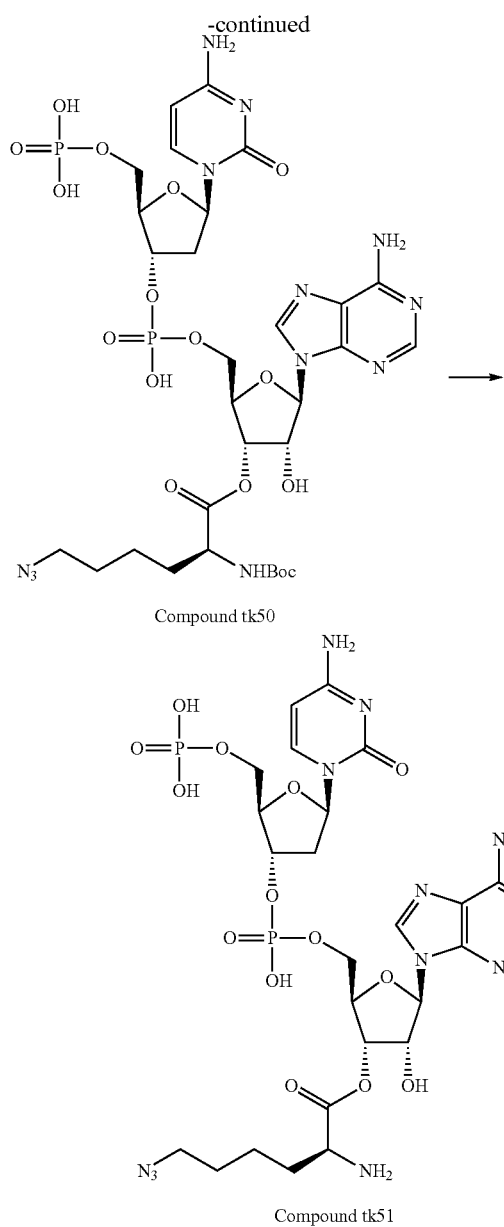

Compound tk50

Compound tk51

Synthesis of (S)-6-azido-2-((tert-butoxycarbonyl)amino)hexanoic Acid (Compound tk48)

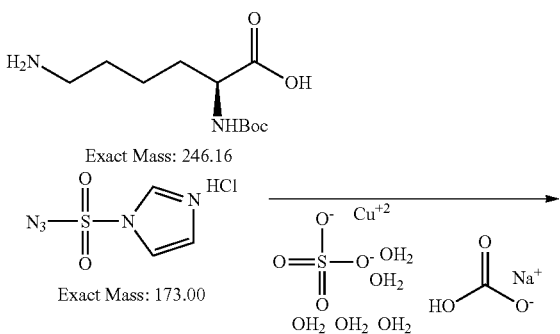

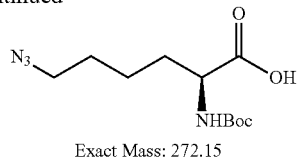

Exact Mass: 272.15

Sodium bicarbonate (0.65 g, 7.74 mmol) was added to a mixture of Boc-Lys-OH (Compound tk39) (1.0 g, 4.06 mmol) and copper sulfate pentahydrate (20 mg, 0.081 mmol) in methanol (15 mL)-water (3 mL) at room temperature, followed by addition of 1H-imidazole-1-sulfonyl azide hydrochloride synthesized by the method described in the literature (Org. Lett., 2007, 9, 3797) (1.02 g, 4.87 mmol). Sodium bicarbonate (0.65 g, 7.74 mmol) was added to the reaction mixture, followed by stirring at room temperature for 23 hours. The reaction mixture was cooled in an ice bath, followed by addition of a saturated aqueous potassium bisulfate solution (10 mL). The resulting mixture was filtered through celite and washed with ethyl acetate, and the filtrate was then concentrated under reduced pressure. The resulting residue was purified by reverse-phase silica gel column chromatography (0.05% aqueous trifluoroacetic acid solution/0.05% trifluoroacetic acid-acetonitrile solution) to afford (S)-6-azido-2-((tert-butoxycarbonyl)amino)hexanoic acid (Compound tk48) (948.7 mg, 86%).

LCMS (ESI) m/z=271 (M–H)–
Retention time: 0.66 min (analysis condition SQDFA05)

Synthesis of (S)-cyanomethyl 6-azido-2-((tert-butoxycarbonyl)amino)hexanoate (Compound tk49)

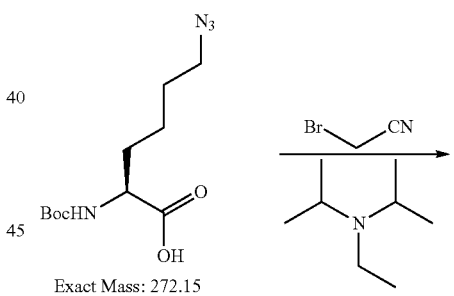

Exact Mass: 272.15

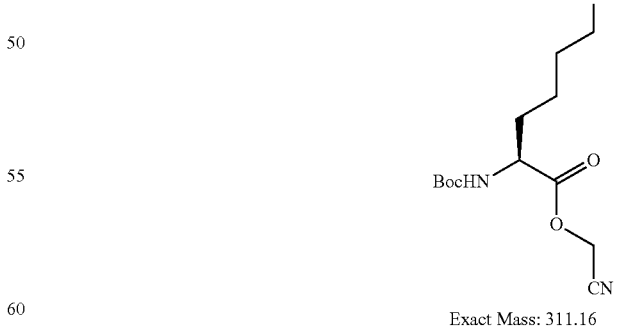

Exact Mass: 311.16

N,N-Diisopropylethylamine (99 μL, 0.566 mmol) and subsequently bromoacetonitrile (179 μL, 2.57 mmol) were added to a solution of (S)-6-azido-2-((tert-butoxycarbonyl)amino)hexanoic acid (Compound tk48) (140 mg, 0.514 mmol) in acetonitrile (0.6 mL) at room temperature under a nitrogen atmosphere. The reaction mixture was stirred at the same temperature for 3.75 hours and then concentrated under reduced pressure, and the resulting crude product was purified by normal-phase silica gel column chromatography (hexane/ethyl acetate) to afford (S)-cyanomethyl 6-azido-2-((tert-butoxycarbonyl)amino)hexanoate (Compound tk49) (175 mg, quant.).

LCMS (ESI) m/z=310 (M−H)−

Retention time: 0.77 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy) phosphoryl)oxy)methyl)-5-(6-amino-9H-purin-9-yl)-4-hydroxytetrahydrofuran-3-yl 6-azido-2-((tert-butoxycarbonyl)amino)hexanoate (Compound tk50)

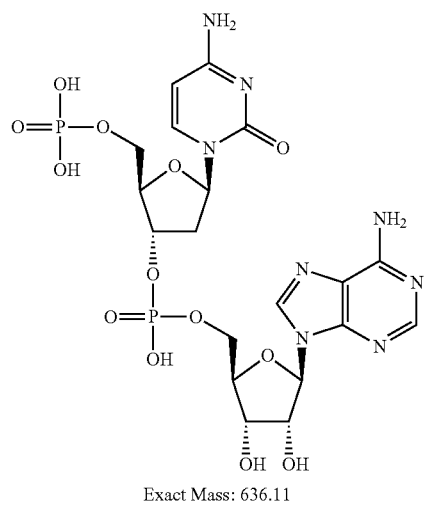

Exact Mass: 636.11

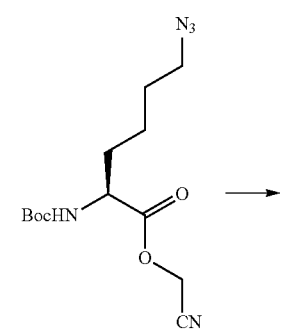

Exact Mass: 311.16

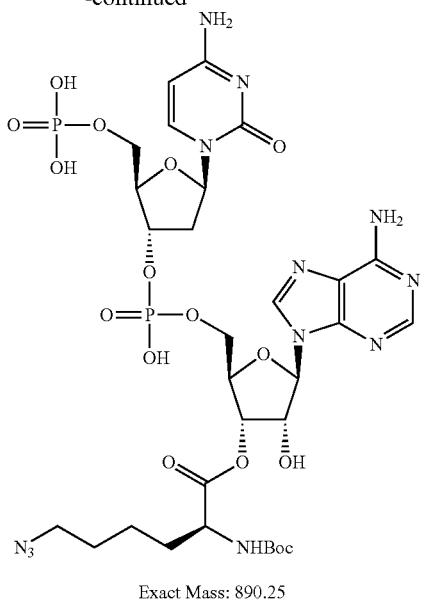

Exact Mass: 890.25

A solution of ((2R,3S,5R)-5-(4-amino-2-oxopyrimidin-1 (2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (78 mg, 0.122 mmol) in water (0.3 mL) and a solution of (S)-cyanomethyl 6-azido-2-((tert-butoxycarbonyl)amino)hexanoate (Compound tk49) (152 mg, 0.488 mmol) in tetrahydrofuran (0.3 mL) were added to buffer A (18 mL), and the mixture was stirred at room temperature for 0.75 hour. Following lyophilization, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy) phosphoryl)oxy)methyl)-5-(6-amino-9H-purin-9-yl)-4-hydroxytetrahydrofuran-3-yl 6-azido-2-((tert-butoxycarbonyl)amino)hexanoate (Compound tk50) (30.2 mg, 28%).

LCMS (ESI) m/z=889.4 (M−H)−

Retention time: 0.47 min (analysis condition SQDFA05)

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-azidohexanoate (Lys(N3)-pdCpA) (Compound tk51)

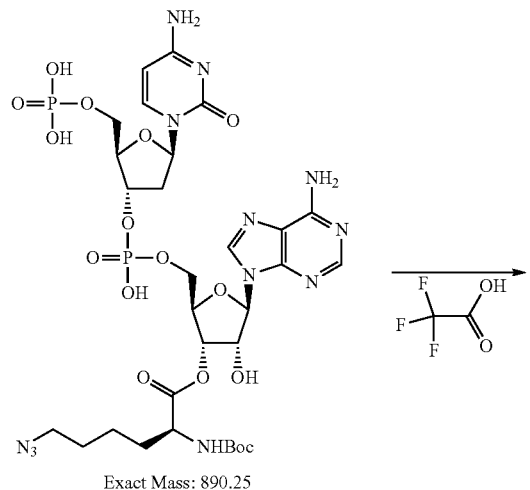

Trifluoroacetic acid (0.1 mL) was added to a solution of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 6-azido-2-((tert-butoxycarbonyl)amino)hexanoate (Compound tk50) (30.2 mg, 0.034 mmol) in dichloromethane (1.5 mL), and the mixture was stirred at room temperature for 30 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-azidohexanoate (Lys(N3)-pdCpA) (Compound tk51) (19.4 mg, 72%).

LCMS (ESI) m/z=789.4 (M−H)−

Retention time: 0.27 min (analysis condition SQDFA05)

10-1-10. Synthesis of Aminoacylated pdCpA Compound tk55

The synthesis was carried out according to the following scheme.

TK scheme 10

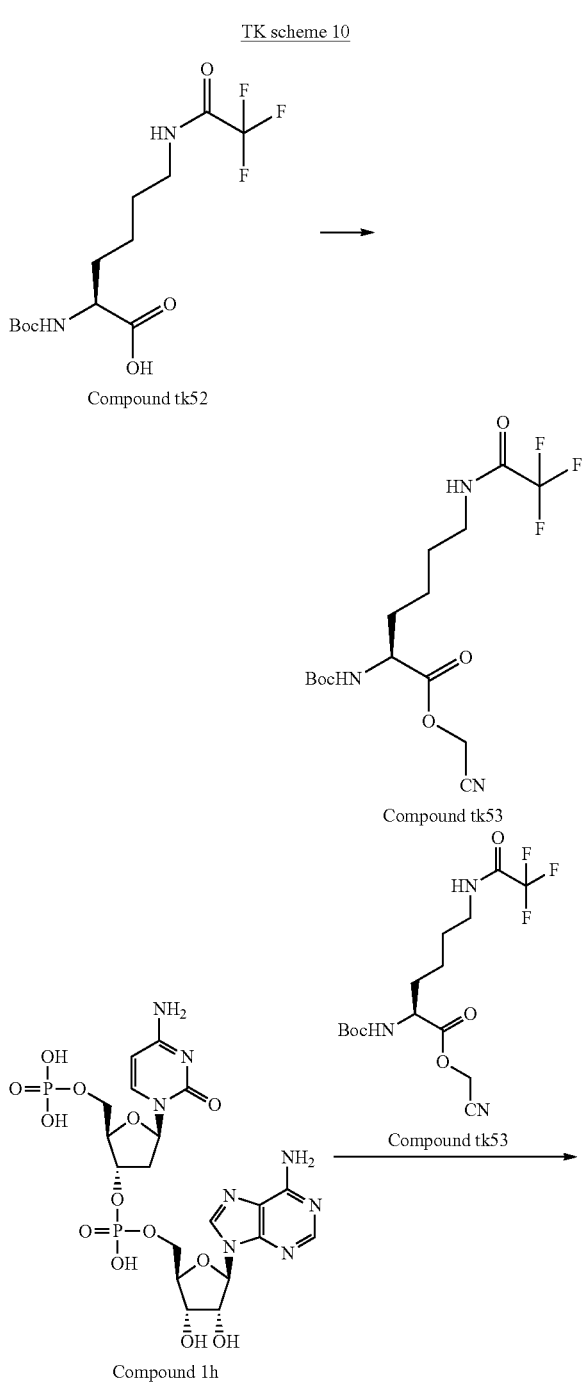

2448

Synthesis of (S)-cyanomethyl 2-((tert-butoxycarbonyl)amino)-6-(2,2,2-trifluoroacetamido)hexanoate (Compound tk53)

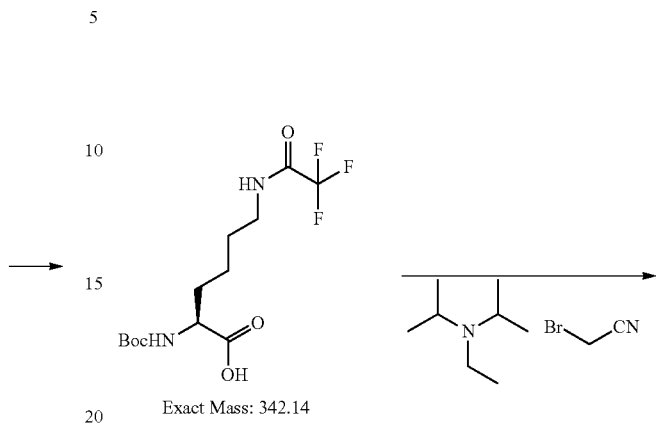

Exact Mass: 342.14

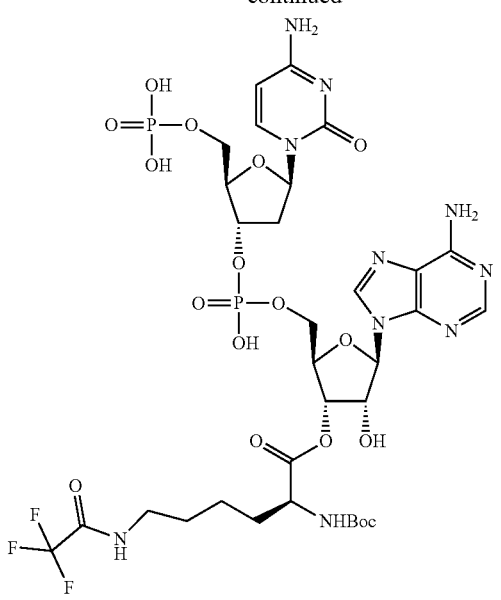

Compound tk54

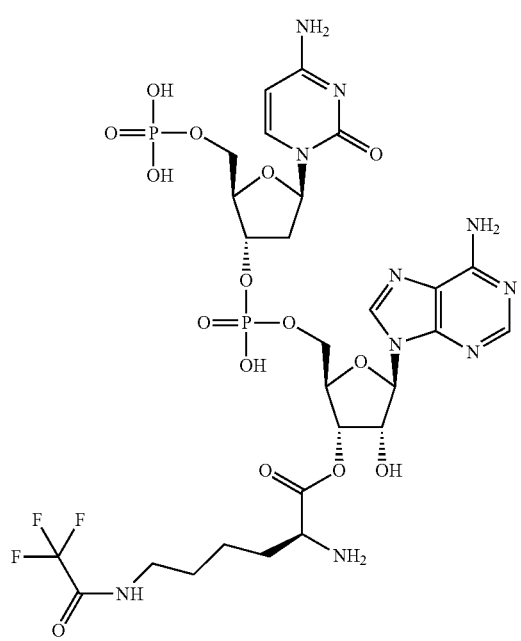

Compound tk55

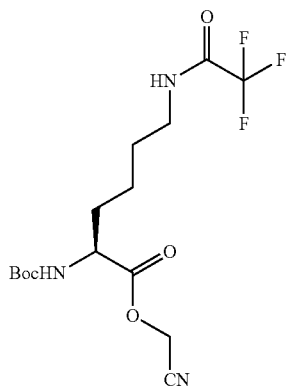

Exact Mass: 381.15

N,N-Diisopropylethylamine (102 μL, 0.585 mmol) and subsequently bromoacetonitrile (185 μL, 2.66 mmol) were added to a solution of Boc-Lys(Tfa)-OH (Compound tk52) (182 mg, 0.532 mmol) in acetonitrile (0.5 mL) at room temperature under a nitrogen atmosphere. The reaction mixture was stirred at the same temperature for 5.25 hours and then concentrated under reduced pressure, and the resulting crude product was purified by normal-phase silica gel column chromatography (hexane/ethyl acetate) to afford (S)-cyanomethyl 2-((tert-butoxycarbonyl)amino)-6-(2,2,2-trifluoroacetamido)hexanoate (Compound tk53) (200.8 mg, 99%).

LCMS (ESI) m/z=379.9 (M–H)–

Retention time: 0.70 min (analysis condition SQDFA05)

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-6-(2,2,2-trifluoroacetamido)hexanoate (Compound tk54)

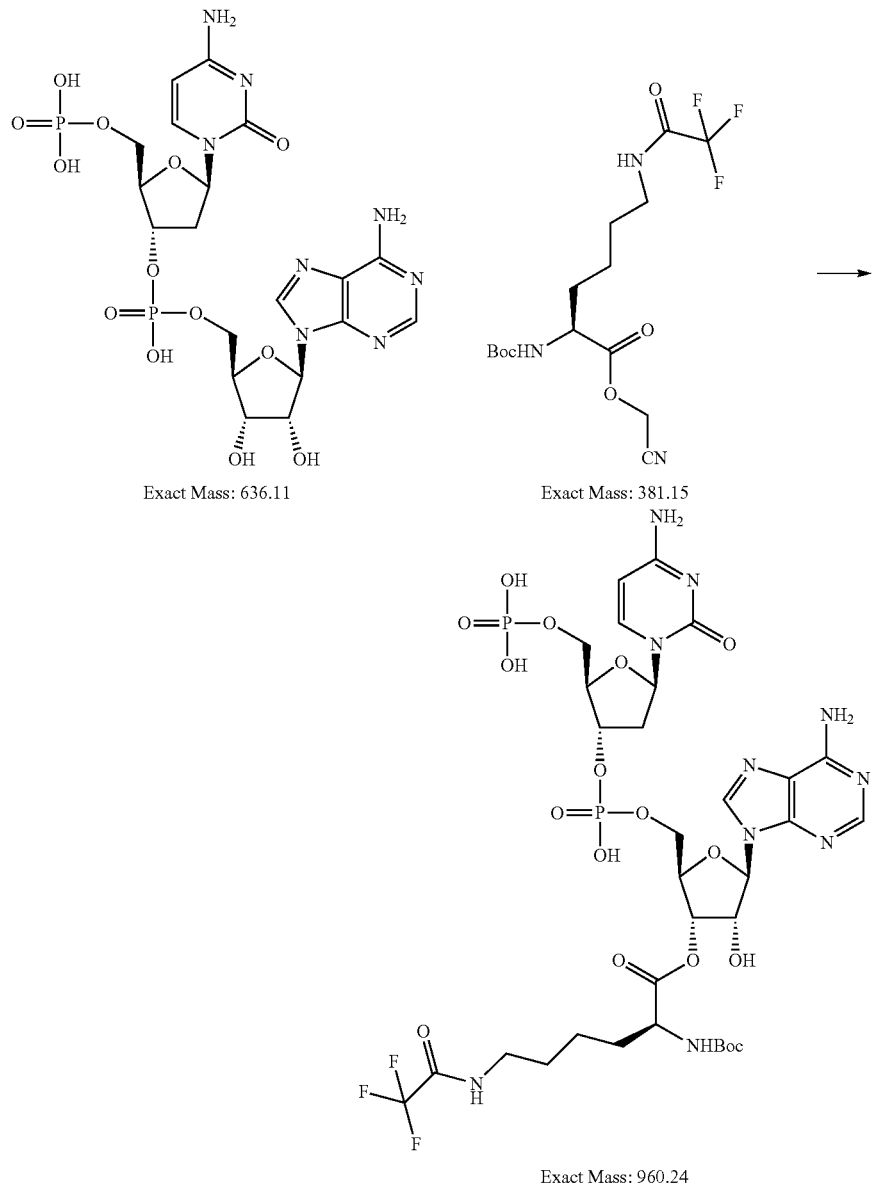

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (81 mg, 0.127 mmol) and (S)-cyanomethyl 2-((tert-butoxycarbonyl)amino)-6-(2,2,2-trifluoroacetamido)hexanoate (Compound tk53) (194 mg, 0.509 mmol) in acetonitrile (0.7 mL) was added to buffer A (20 mL), and the mixture was stirred at room temperature for 1.75 hours. Following lyophilization, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-6-(2,2,2-trifluoroacetamido)hexanoate (Compound tk54) (5.3 mg, 4%).

LCMS (ESI) m/z=959.5 (M−H)−

Retention time: 0.44 min (analysis condition SQDFA05)

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-(2,2,2-trifluoroacetamido)hexanoate (Lys(Tfa)-pdCpA) (Compound tk55)

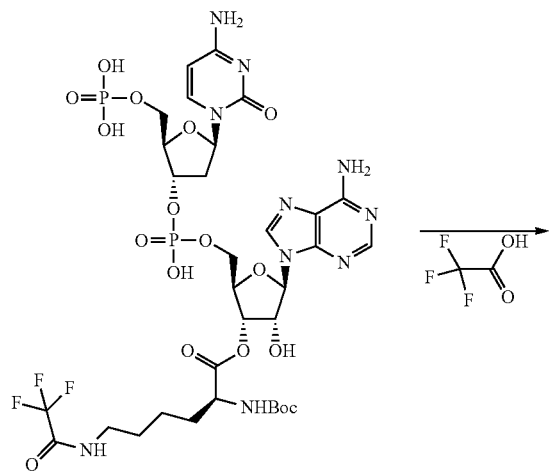

Exact Mass:

A 10% solution of trifluoroacetic acid in dichloromethane (0.21 mL) was added to a solution of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-6-(2,2,2-trifluoroacetamido)hexanoate (Compound tk54) (5.3 mg, 5.52 μmol) in dichloromethane (0.1 mL), and the mixture was stirred at room temperature for 55 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-Purin-9-yl)-4-hydroxytetrahydrofuran-3-yl 2-amino-6-(2,2,2-trifluoroacetamido)hexanoate (Lys(Tfa)-pdCpA) (Compound tk55) (4.2 mg, 88%).

LCMS (ESI) m/z=859.4 (M–H)–
Retention time: 0.26 min (analysis condition SQDFA05)

10-1-11. Synthesis of Aminoacylated pdCpA Compound tk60

The synthesis was carried out according to the following scheme.

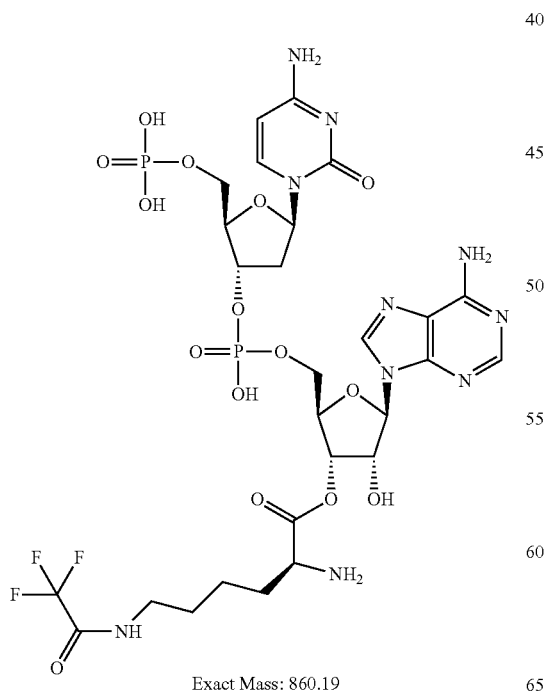

Exact Mass: 860.19

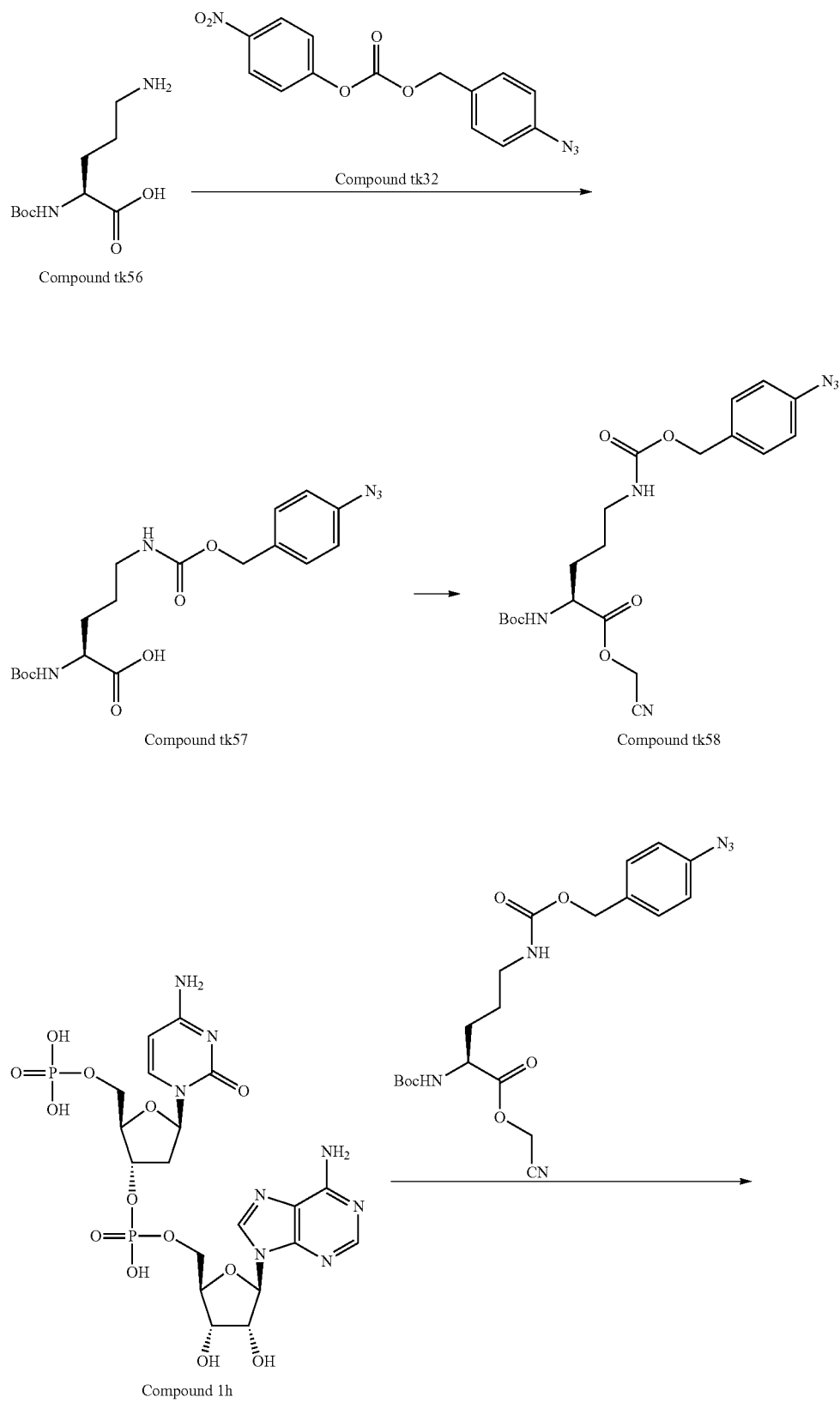

-continued
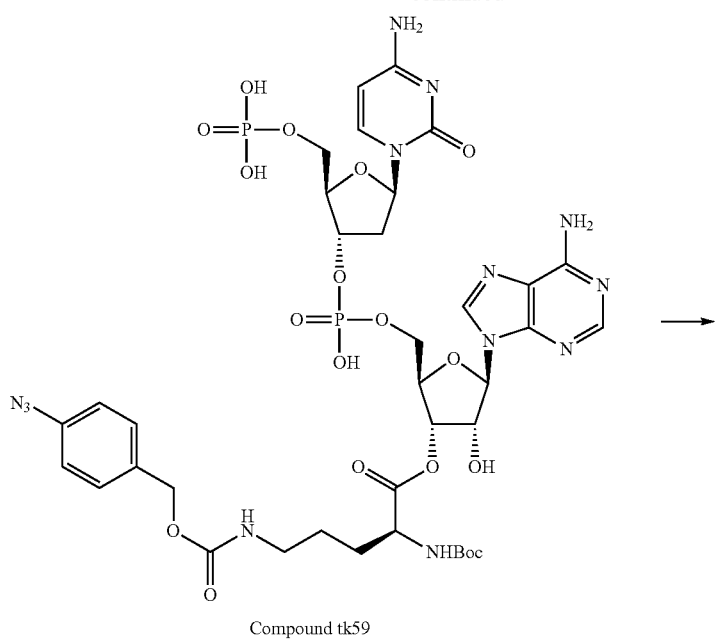
Compound tk59
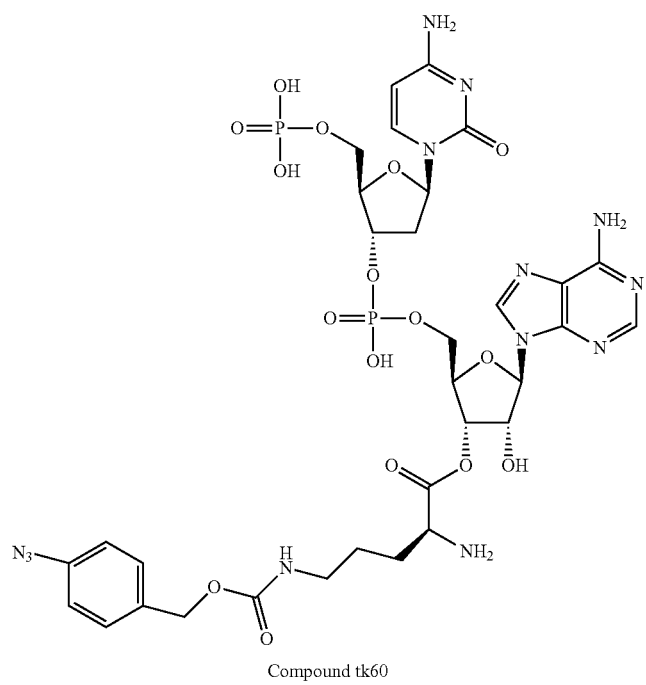
Compound tk60

Synthesis of (S)-5-((((4-azidobenzyl)oxy)carbonyl)amino)-2-((tert-butoxycarbonyl)amino)pentanoic Acid (Compound tk57)

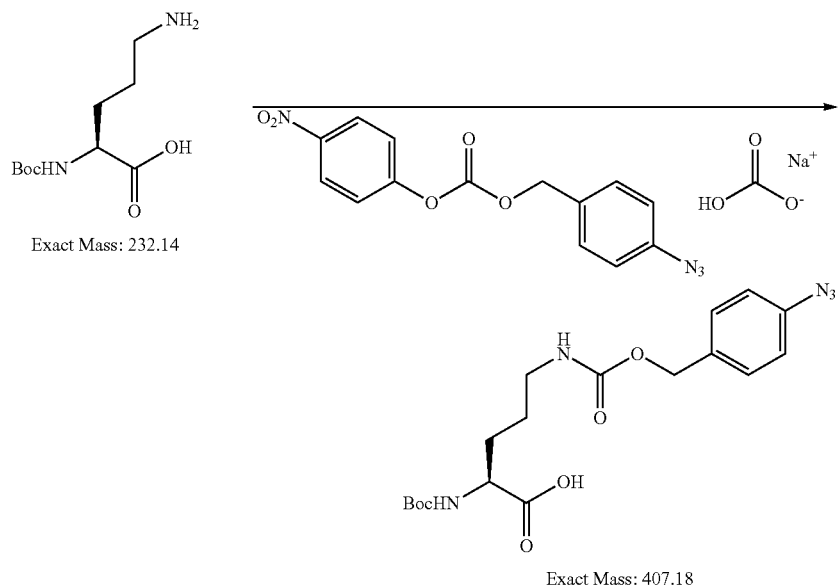

4-Azidobenzyl (4-nitrophenyl) carbonate synthesized by the method described in the literature (Bioconjugate Chem. 2008, 19, 714.) (Compound tk32) (521 mg, 1.658 mmol) was added to a suspension of Boc-Orn-OH (Compound tk56) (321 mg, 1.382 mmol) and sodium bicarbonate (290 mg, 3.45 mmol) in 1,4-dioxane (3 mL)-water (2 mL). The reaction mixture was stirred at room temperature for 23 hours and then cooled in an ice bath and diluted with ethyl acetate and water, and a saturated aqueous potassium bisulfate solution (2 mL) was added to the resulting mixture. The mixture was extracted with ethyl acetate (×2), and the organic phase was washed with water (10 mL×2) and brine (10 mL) and dried over sodium sulfate. Following concentration under reduced pressure, the resulting crude product was purified by normal-phase silica gel column chromatography (hexane/ethyl acetate) to afford ((S)-5-((((4-azidobenzyl)oxy)carbonyl)amino)-2-((tert-butoxycarbonyl)amino) pentanoic acid (Compound tk57) (501.3 mg, 89%).

LCMS (ESI) m/z=406 (M−H)−
Retention time: 0.73 min (analysis condition SQDFA05)

Synthesis of (S)-cyanomethyl 5-((((4-azidobenzyl)oxy)carbonyl)amino)-2-((tert-butoxycarbonyl)amino)pentanoate (Compound tk58)

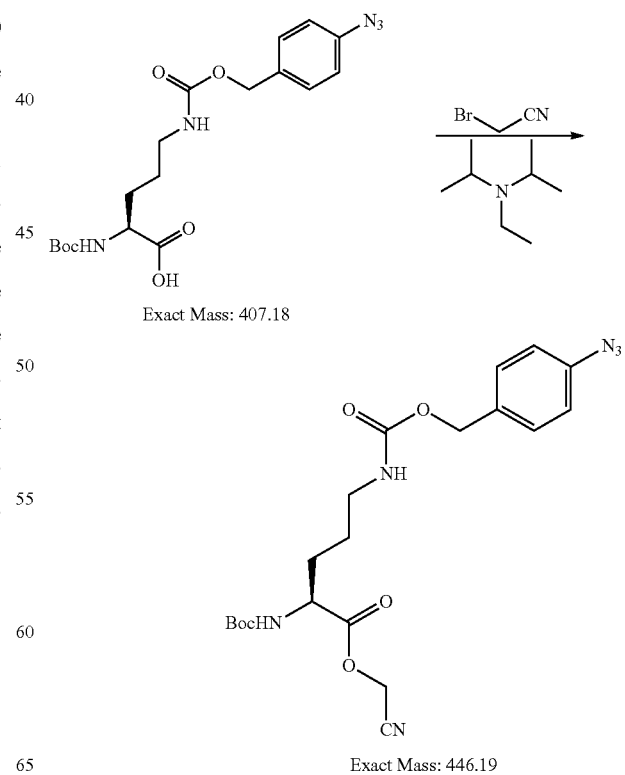

N,N-Diisopropylethylamine (173 μL, 0.991 mmol) and subsequently bromoacetonitrile (314 μL, 4.50 mmol) were added to a solution of (S)-5-((((4-azidobenzyl)oxy)carbonyl)amino)-2-((tert-butoxycarbonyl)amino)pentanoic acid (Compound tk57) (367 mg, 0.901 mmol) in acetonitrile (1 mL) at room temperature under a nitrogen atmosphere. The reaction mixture was stirred at the same temperature for 1 hour and then concentrated under reduced pressure, and the resulting crude product was purified by normal-phase silica gel column chromatography (hexane/ethyl acetate) to afford (S)-cyanomethyl 5-((((4-azidobenzyl)oxy)carbonyl)amino)-2-((tert-butoxycarbonyl)amino)pentanoate (Compound tk58) (417.2 mg, quant.).

LCMS (ESI) m/z=445 (M–H)–

Retention time: 0.82 min (analysis condition SQDFA05)

x. Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-((((4-azidobenzyl)oxy)carbonyl)amino)-2-((tert-butoxycarbonyl)amino)pentanoate (Compound tk59)

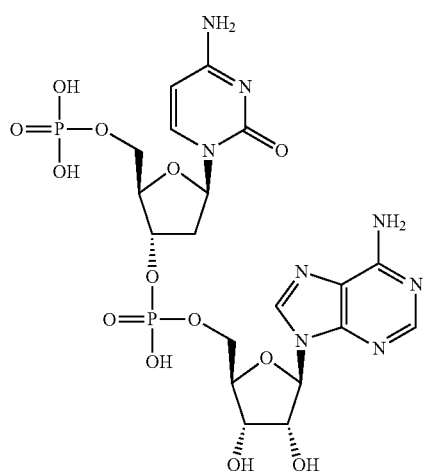

Exact Mass: 636.11

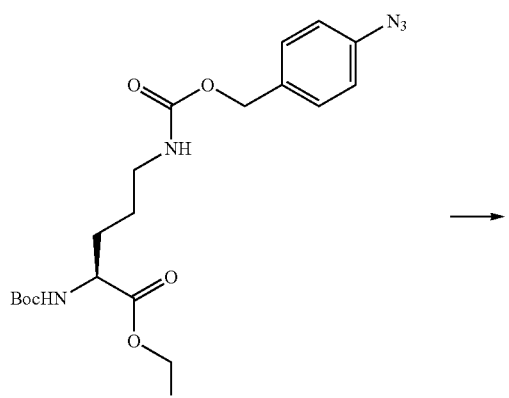

Exact Mass: 446.19

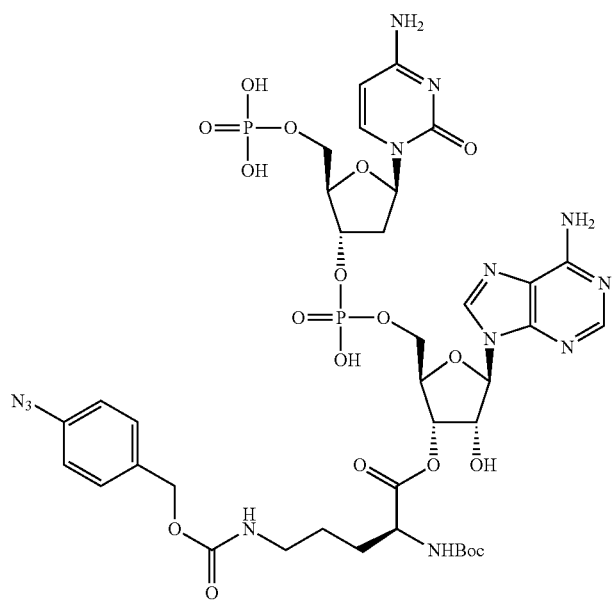

Exact Mass: 1025.28

A solution of ((2R,3S,5R)-5-(4-amino-2-oxopyrimidin-1 (2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (143 mg, 0.224 mmol) and (S)-cyanomethyl 5-((((4-azidobenzyl)oxy)carbonyl)amino)-2-((tert-butoxycarbonyl)amino)pentanoate (Compound tk58) (400 mg, 0.896 mmol) in acetonitrile (1 mL) was added to buffer A (33 mL), and the mixture was stirred at room temperature for 1.5 hours. Following lyophilization, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-((((4-azidobenzyl)oxy)carbonyl)amino)-2-((tert-butoxycarbonyl)amino)pentanoate (Compound tk59) (54.7 mg, 24%).

LCMS (ESI) m/z=1024.5 (M−H)−
Retention time: 0.54 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-((((4-azidobenzyl)oxy)carbonyl)amino)pentanoate (Orn(Acbz)-pdCpA) (Compound tk60)

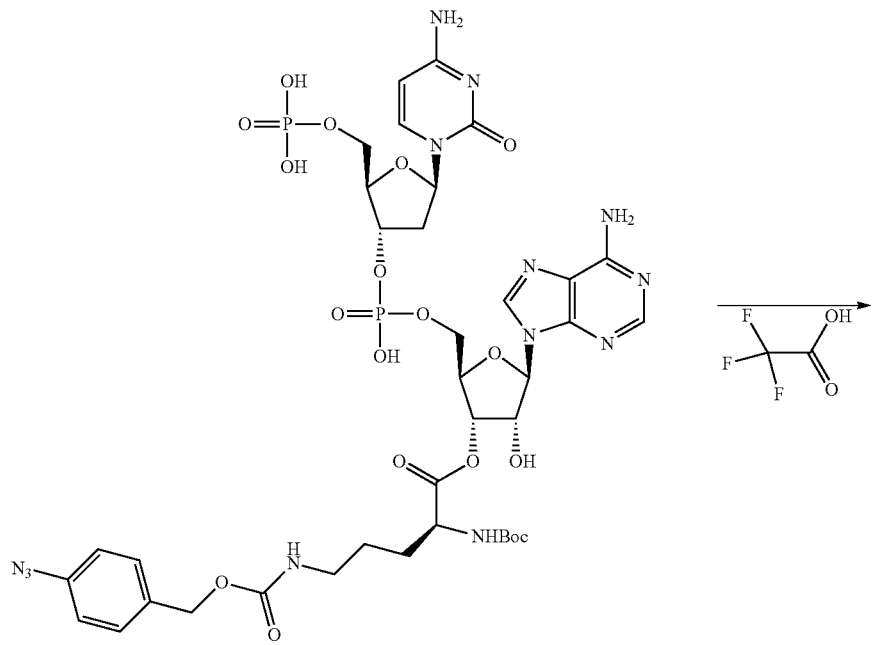

Exact Mass: 1025.28

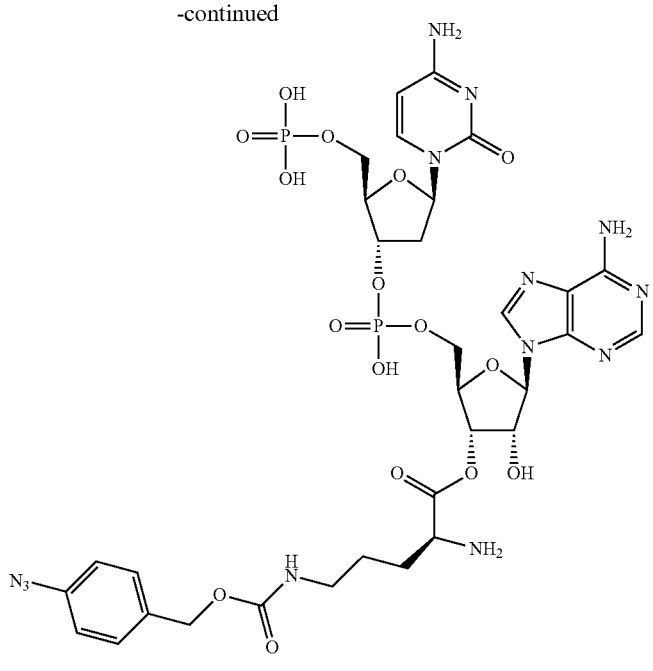

Exact Mass: 925.23

A 10% solution of trifluoroacetic acid in dichloromethane (0.4 mL) was added to a solution of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-((((4-azidobenzyl)oxy)carbonyl)amino)-2-((tert-butoxycarbonyl)amino)pentanoate (Compound tk59) (22.7 mg, 0.022 mmol) in dichloromethane (0.4 mL), and the mixture was stirred at room temperature for 20 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-((((4-azidobenzyl)oxy)carbonyl)amino)pentanoate (Orn(Acbz)-pdCpA) (Compound tk60) (4.3 mg, 21%).

LCMS (ESI) m/z=924.3 (M–H)–
Retention time: 0.37 min (analysis condition SQDFA05)

10-1-12. Synthesis of Aminoacylated pdCpA Compound tk64

The synthesis was carried out according to the following scheme.

TK scheme 12

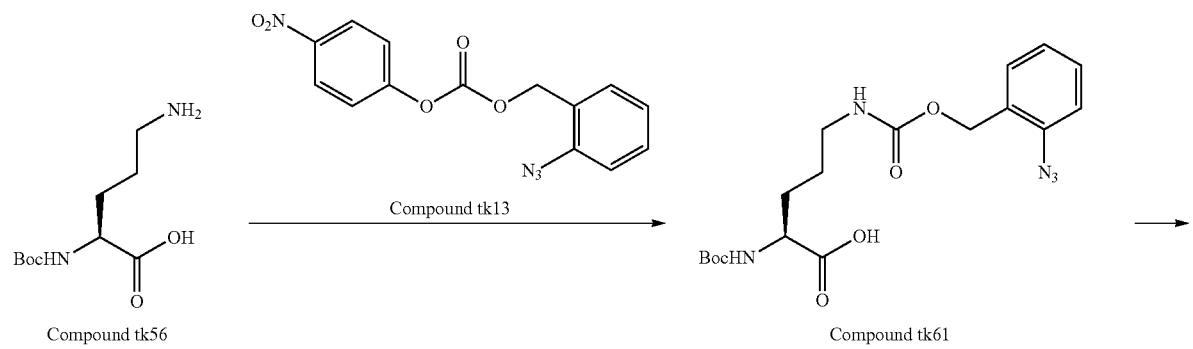

Compound tk56  Compound tk13  Compound tk61

-continued
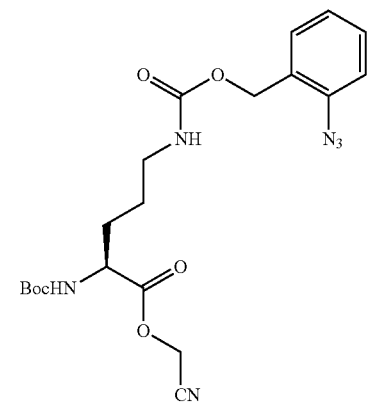
Compound tk62
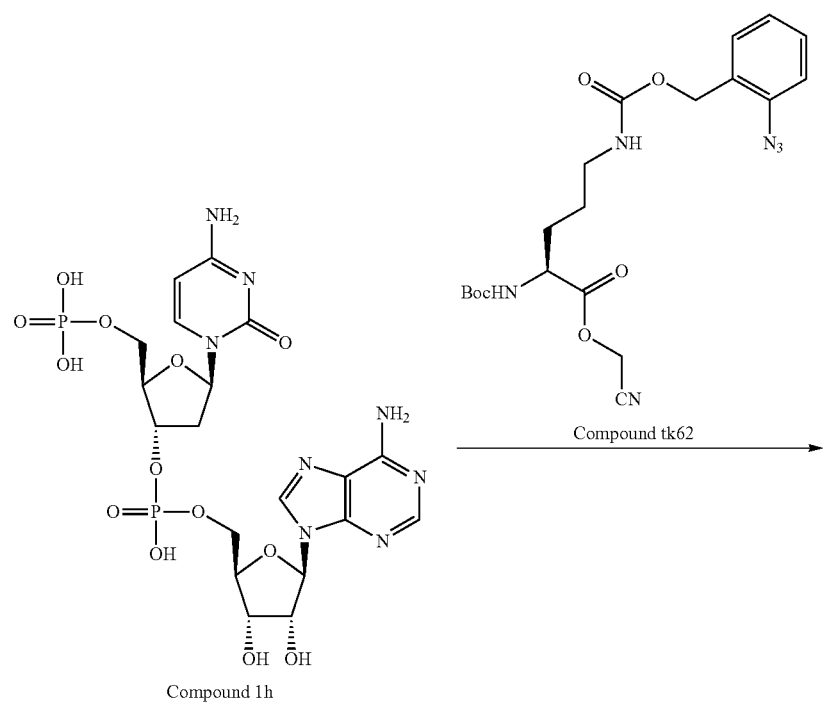

-continued
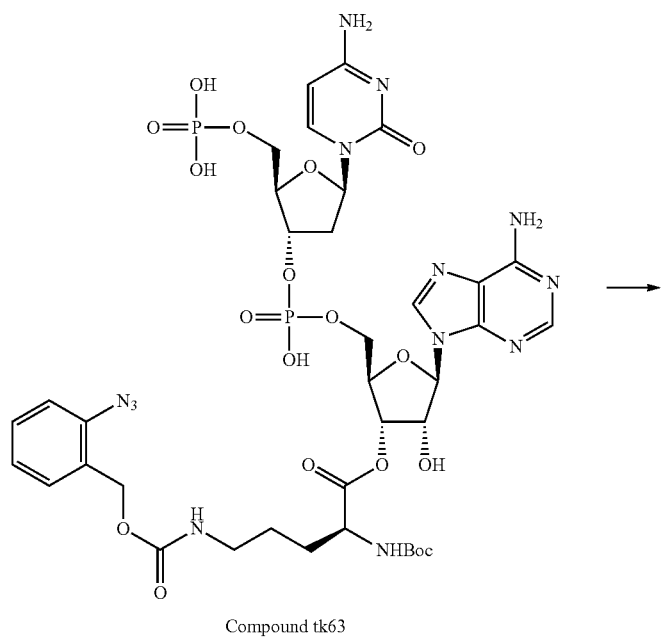
Compound tk63
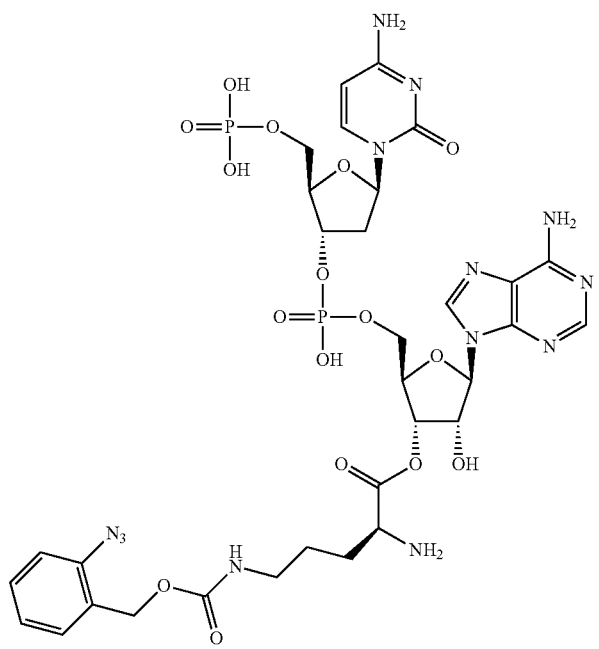
Compound tk64

Synthesis of (S)-5-((((2-azidobenzyl)oxy)carbonyl)amino)-2-((tert-butoxycarbonyl)amino)pentanoic Acid (Compound tk61)

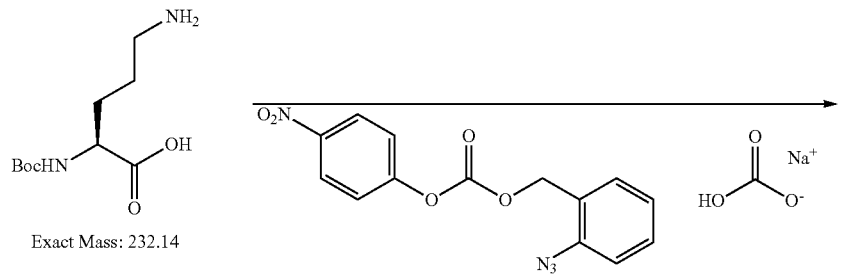

2-Azidobenzyl (4-nitrophenyl) carbonate (Compound tk13) (458 mg, 1.459 mmol) was added to a suspension of Boc-Orn-OH (Compound tk56) (308 mg, 1.326 mmol) and sodium bicarbonate (278 mg, 3.32 mmol) in 1,4-dioxane (3 mL)-water (2 mL). The reaction mixture was stirred at room temperature for 20.25 hours and then cooled in an ice bath and diluted with ethyl acetate and water, and a saturated aqueous potassium bisulfate solution (1.5 mL) was added to the resulting mixture. The mixture was extracted with ethyl acetate (×2), and the organic phase was washed with water (10 mL×2) and brine (10 mL) and dried over sodium sulfate. Following concentration under reduced pressure, the resulting crude product was purified by normal-phase silica gel column chromatography (hexane/ethyl acetate) to afford (S)-5-((((2-azidobenzyl)oxy)carbonyl)amino)-2-((tert-butoxycarbonyl)amino)pentanoic acid (Compound tk61) (556.0 mg, quant.).

LCMS (ESI) m/z=406 (M−H)−

Retention time: 0.73 min (analysis condition SQDFA05)

Synthesis of (S)-cyanomethyl 5-((((2-azidobenzyl)oxy)carbonyl)amino)-2-((tert-butoxycarbonyl)amino)pentanoate (Compound tk62)

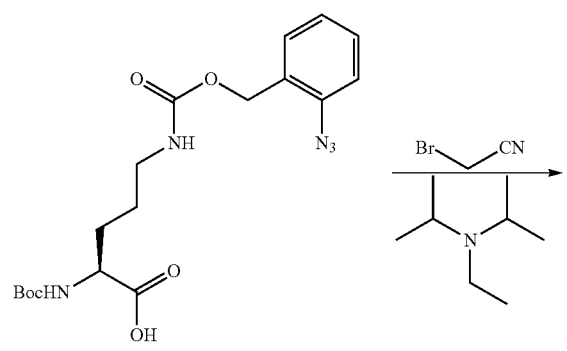

2471

-continued

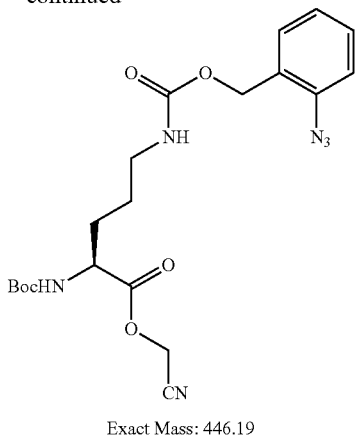

Exact Mass: 446.19

N,N-Diisopropylethylamine (205 μL, 1.176 mmol) and subsequently bromoacetonitrile (373 μL, 5.34 mmol) were

2472 added to a solution of (S)-5-((((2-azidobenzyl)oxy)carbonyl)amino)-2-((tert-butoxycarbonyl)amino)pentanoic acid (Compound tk61) (435.5 mg, 1.069 mmol) in acetonitrile (1 mL) at room temperature under a nitrogen atmosphere. The reaction mixture was stirred at the same temperature for 3.5 hours and then concentrated under reduced pressure, and the resulting crude product was purified by normal-phase silica gel column chromatography (hexane/ethyl acetate) to afford (S)-cyanomethyl 5-((((2-azidobenzyl)oxy)carbonyl)amino)-2-((tert-butoxycarbonyl)amino)pentanoate (Compound tk62) (477.2 mg, quant.).

LCMS (ESI) m/z=445.4 (M–H)–

Retention time: 0.81 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-((((2-azidobenzyl)oxy)carbonyl)amino)-2-((tert-butoxycarbonyl)amino)pentanoate (Compound tk63)

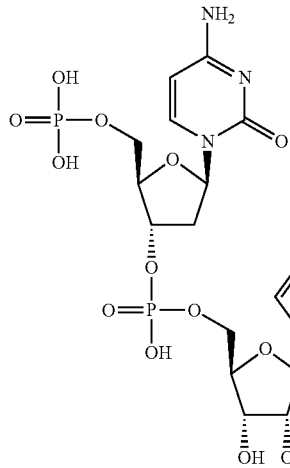

Exact Mass: 636.11

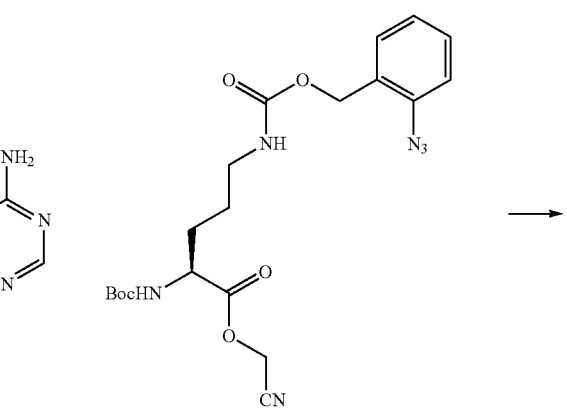

Exact Mass: 446.19

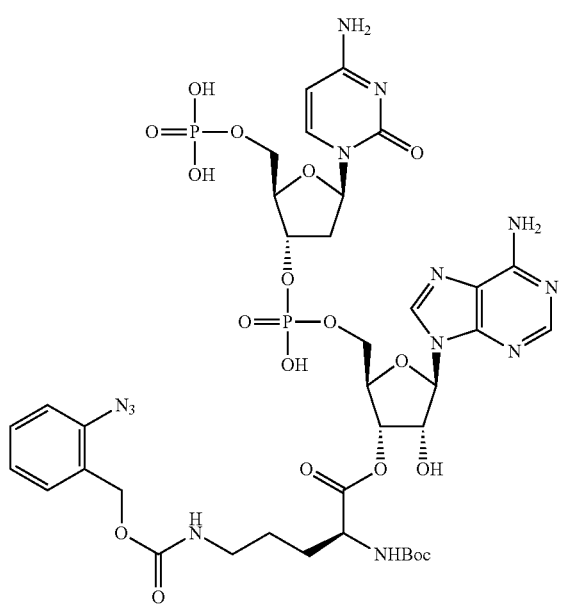

Exact Mass: 1025.28

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (160 mg, 0.252 mmol) and (S)-cyanomethyl 5-((((2-azidobenzyl)oxy)carbonyl)amino)-2-((tert-butoxycarbonyl)amino)pentanoate (Compound tk62) (450 mg, 1.008 mmol) in acetonitrile (1.5 mL) was added to buffer A (33 mL), and the mixture was stirred at room temperature for 2 hours. Following lyophilization, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy) phosphoryl)oxy)methyl)-5-(6-amino-9H-purin-9-yl)-4-hydroxytetrahydrofuran-3-yl 5-((((2-azidobenzyl)oxy)carbonyl)amino)-2-((tert-butoxycarbonyl)amino)pentanoate (Compound tk63) (51.3 mg, 20%).

LCMS (ESI) m/z=1024.5 (M–H)–

Retention time: 0.54 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy) phosphoryl)oxy)methyl)-5-(6-amino-9H-purin-9-yl)-4-hydroxytetrahydrofuran-3-yl 2-amino-5-((((2-azidobenzyl)oxy)carbonyl)amino)pentanoate (Orn (oAcbz)-pdCpA) (Compound tk64)

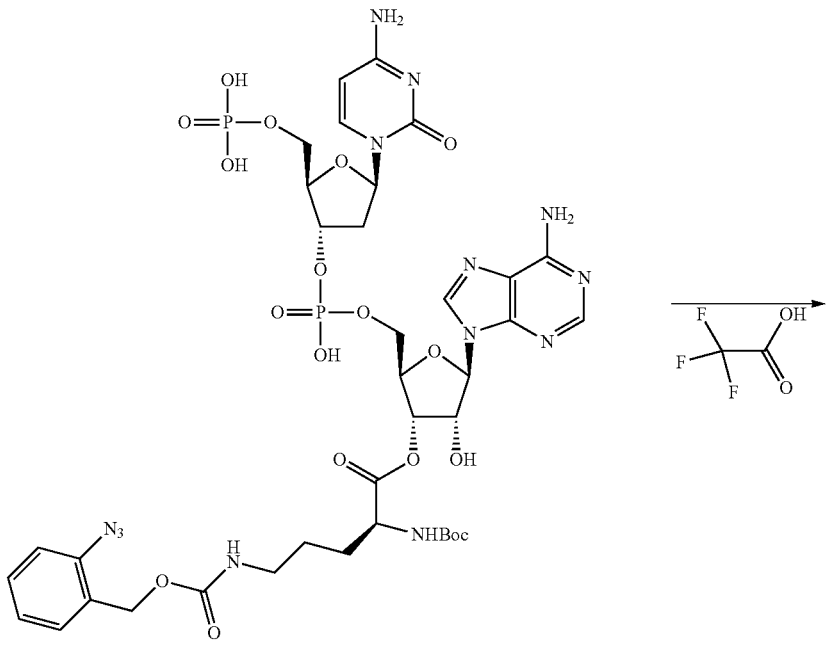

Exact Mass: 1025.28

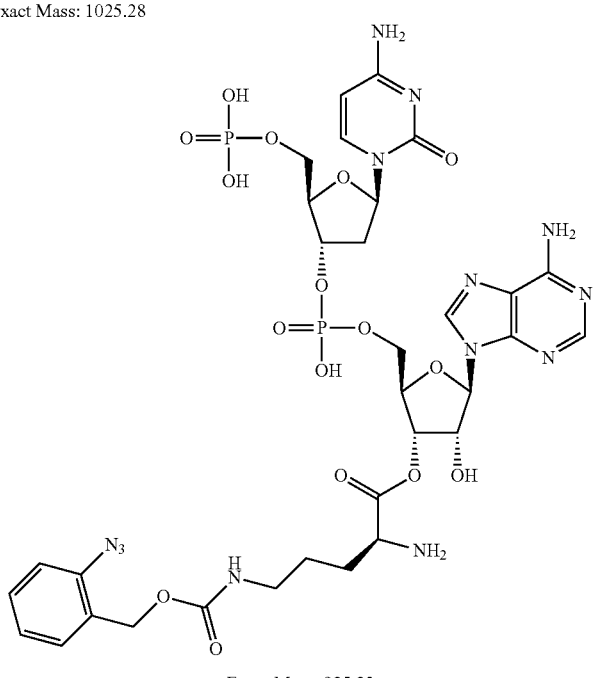

Exact Mass: 925.23

2475

A 10% solution of trifluoroacetic acid in dichloromethane (0.45 mL) was added to a solution of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-((((2-azidobenzyl)oxy)carbonyl)amino)-2-((tert-butoxycarbonyl)amino)pentanoate (Compound tk63) (51 mg, 0.050 mmol) in dichloromethane (0.45 mL), and the mixture was stirred at room temperature for 45 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-((((2-azidobenzyl)oxy)carbonyl)amino)pentanoate (Orn(oAcbz)-pdCpA) (Compound tk64) (42.6 mg, 93%).

LCMS (ESI) m/z=924.4 (M−H)−

Retention time: 0.37 min (analysis condition SQDFA05)

10-1-13. Synthesis of Aminoacylated pdCpA Compound tk68

The synthesis was carried out according to the following scheme.

TK scheme 13

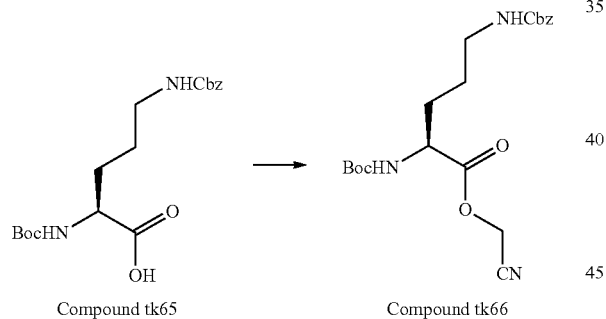

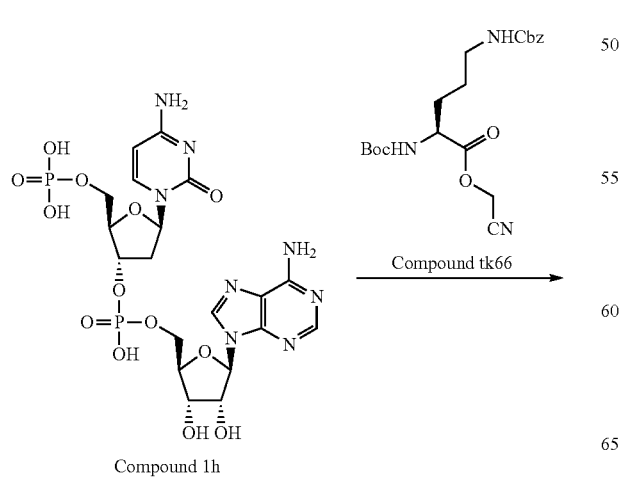

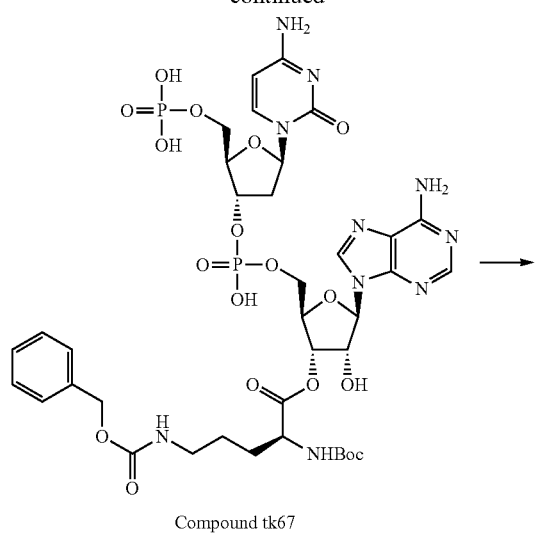

Compound tk67

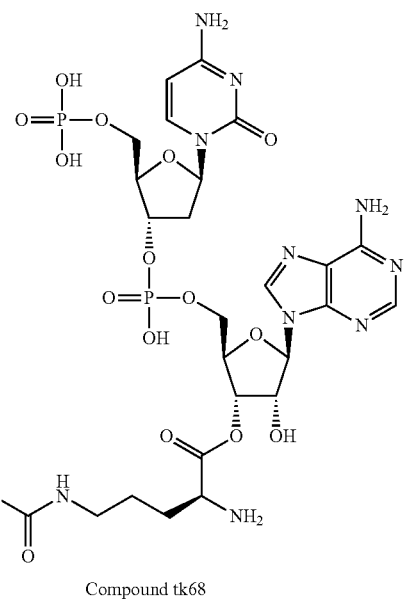

Compound tk68

Synthesis of (S)-Cyanomethyl 5-(((benzyloxy)carbonyl)amino)-2-((tert-butoxycarbonyl)amino)pentanoate (Compound tk66)

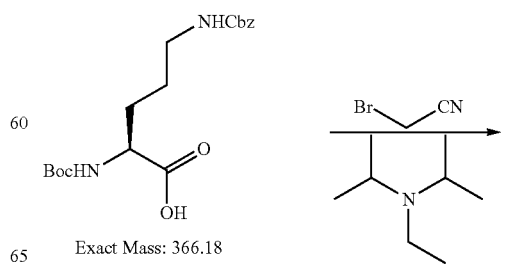

Exact Mass: 366.18

2477
-continued

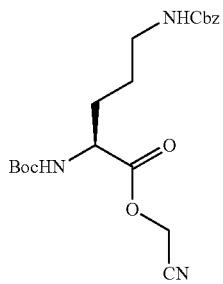

Exact Mass: 405.19

N,N-Diisopropylethylamine (84 μL, 0.480 mmol) and subsequently bromoacetonitrile (152 μL, 2.183 mmol) were added to a solution of Boc-Orn(Z)—OH (Compound tk65) (160 mg, 0.437 mmol) in acetonitrile (0.5 mL) at room temperature under a nitrogen atmosphere. The reaction mixture was stirred at the same temperature for 1 hours and then concentrated under reduced pressure, and the resulting crude product was purified by normal-phase silica gel column chromatography (hexane/ethyl acetate) to afford (S)-cyanomethyl 5-(((benzyloxy)carbonyl)amino)-2-((tert-butoxycarbonyl)amino)pentanoate (Compound tk66) (186.7 mg, quant.).

LCMS (ESI) m/z=404 (M−H)−

Retention time: 0.77 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-(((benzyloxy)carbonyl)amino)-2-((tert-butoxycarbonyl)amino) pentanoate (Compound tk67)

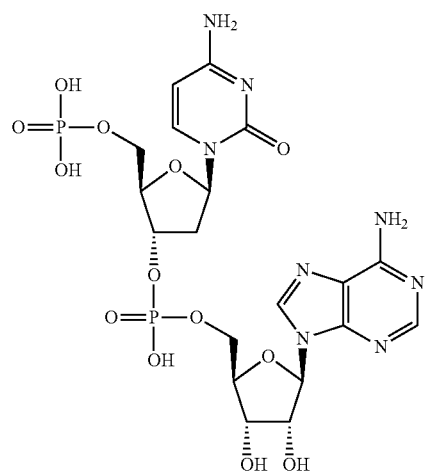

Exact Mass: 636.11

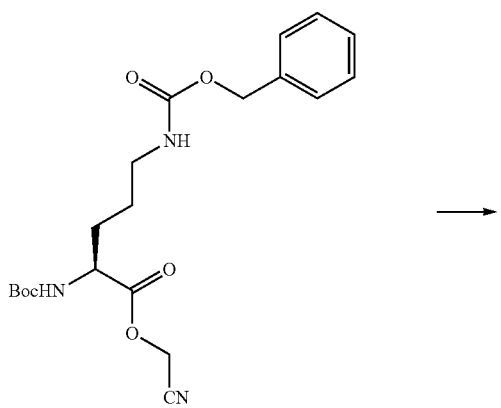

Exact Mass: 405.19

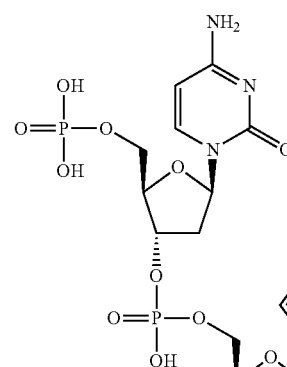

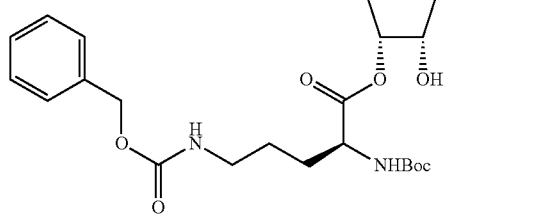

Exact Mass: 984.28

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (67.9 mg, 0.107 mmol) in water (0.3 mL) and a solution of (S)-cyanomethyl 5-(((benzyloxy)carbonyl)amino)-2-((tert-butoxycarbonyl)amino)pentanoate (Compound tk66) (173 mg, 0.427 mmol) in acetonitrile (0.3 mL) were added to buffer A (18 mL), and the mixture was stirred at room temperature for 1.25 hours. Following lyophilization, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-(((benzyloxy)carbonyl)amino)-2-((tert-butoxycarbonyl)amino)pentanoate (Compound tk67) (30.1 mg, 29%).

LCMS (ESI) m/z=983.4 (M–H)–

Retention time: 0.54 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-(((benzyloxy)carbonyl)amino)pentanoate (Orn(Z)-pdCpA) (Compound tk68)

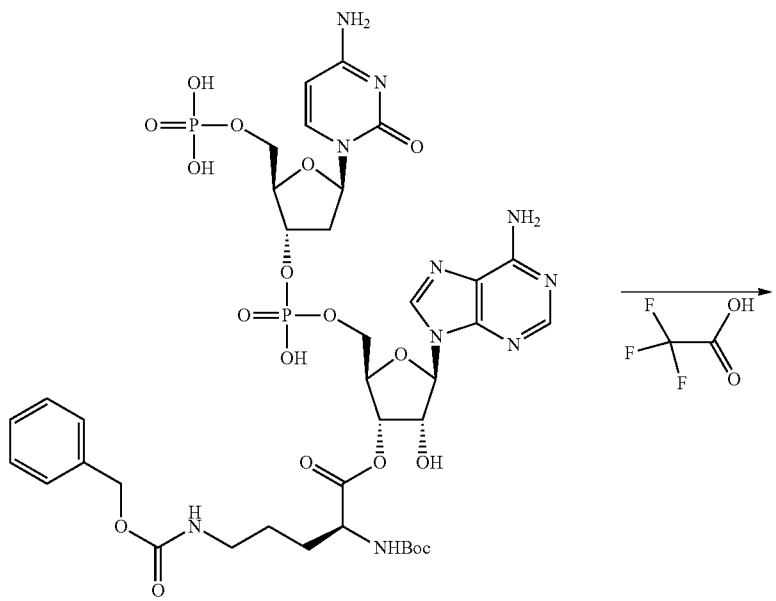

Exact Mass: 984.28

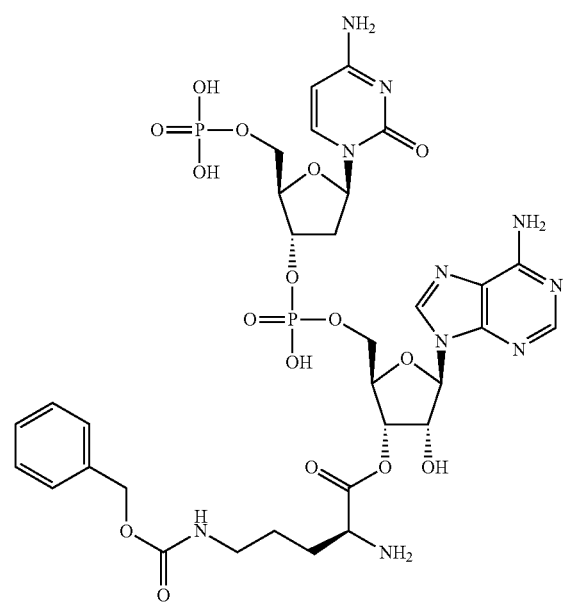

Exact Mass: 884.23

Trifluoroacetic acid (0.117 mL) was added to a solution of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-(((benzyloxy)carbonyl)amino)-2-((tert-butoxycarbonyl)amino)pentanoate (Compound tk67) (30 mg, 0.030 mmol) in dichloromethane (1.1 mL), and the mixture was stirred at room temperature for 35 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-(((benzyloxy)carbonyl)amino)pentanoate (Orn(Z)-pdCpA) (Compound tk68) (24.4 mg, 91%).

LCMS (ESI) m/z=883.3 (M−H)−

Retention time: 0.33 min (analysis condition SQDFA05)

10-1-14. Synthesis of Aminoacylated pdCpA Compound tk72

The synthesis was carried out according to the following scheme.

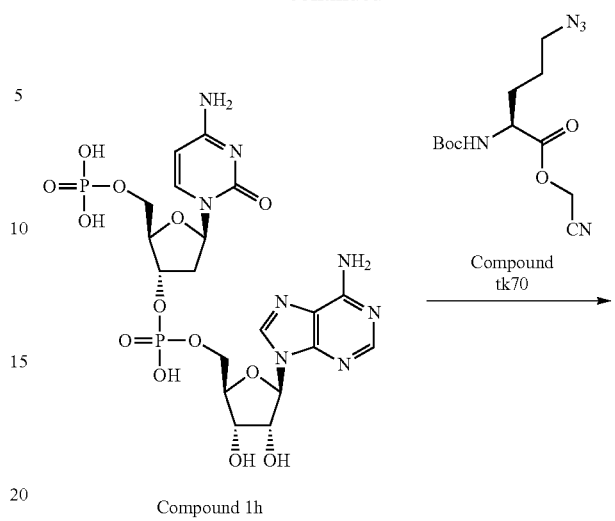

Compound 1h

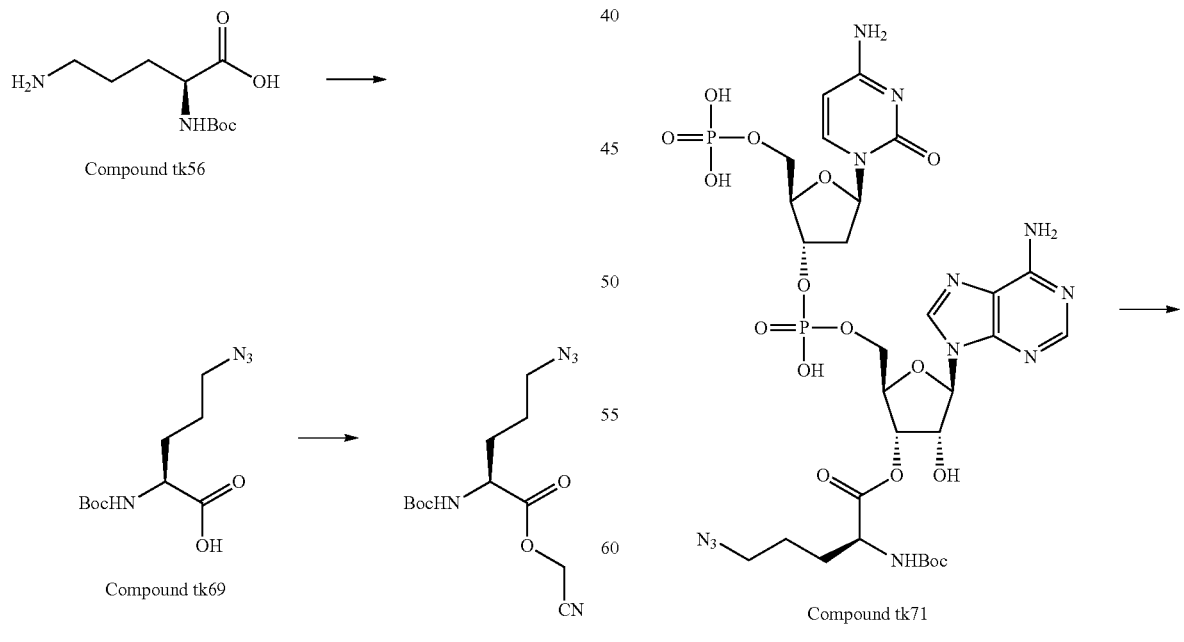

TK scheme 14

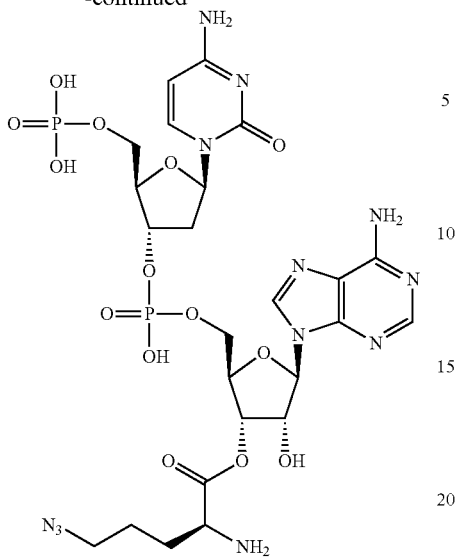

Compound tk72

Synthesis of (S)-5-azido-2-((tert-butoxycarbonyl)amino)pentanoic Acid (Compound tk69)

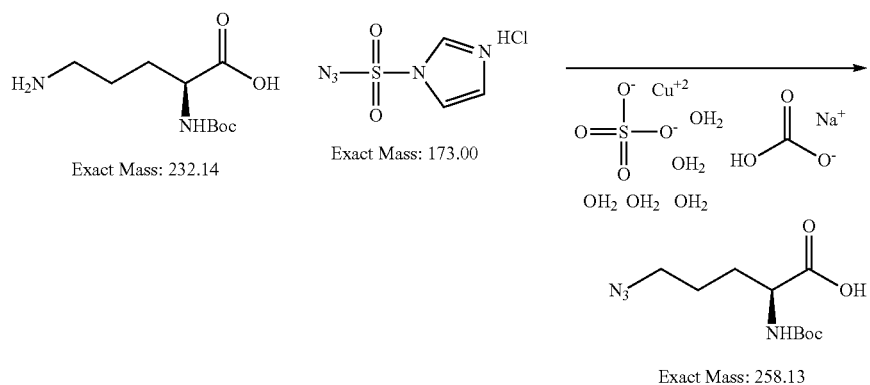

Sodium bicarbonate (1.99 g, 23.68 mmol) was added to a mixture of Boc-Orn-OH (Compound tk56) (1.0 g, 4.31 mmol) and copper sulfate pentahydrate (21 mg, 0.086 mmol) in methanol (20 mL)-water (6 mL) at room temperature, followed by addition of 1H-imidazole-1-sulfonyl azide hydrochloride synthesized by the method described in the literature (Org. Lett., 2007, 9, 3797) (1.08 g, 5.17 mmol). The reaction mixture was stirred at room temperature for 24 hours. The reaction mixture was cooled in an ice bath, followed by addition of a saturated aqueous potassium bisulfate solution (8 mL). The resulting mixture was extracted with ethyl acetate (three times), and the organic phase was concentrated under reduced pressure. The resulting residue was purified by reverse-phase silica gel column chromatography (0.05% aqueous trifluoroacetic acid solution/0.05% trifluoroacetic acid-acetonitrile solution) to afford (S)-5-azido-2-((tert-butoxycarbonyl)amino)pentanoic acid (Compound tk69) (1.19 g, quant.).

LCMS (ESI) m/z=257 (M−H)−
Retention time: 0.61 min (analysis condition SQDFA05)

Synthesis of (S)-cyanomethyl 5-azido-2-((tert-butoxycarbonyl)amino)pentanoate (Compound tk70)

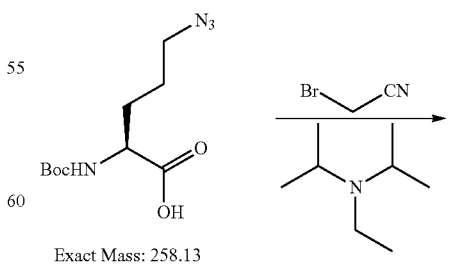

Exact Mass: 258.13

-continued

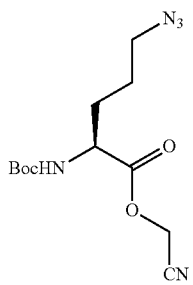

Exact Mass: 297.14

N,N-Diisopropylethylamine (111 μL, 0.639 mmol) and subsequently bromoacetonitrile (203 μL, 2.90 mmol) were added to a solution of (S)-5-azido-2-((tert-butoxycarbonyl)amino)pentanoic acid (Compound tk69) (150 mg, 0.581 mmol) in acetonitrile (0.8 mL) at room temperature under a nitrogen atmosphere. The reaction mixture was stirred at the same temperature for 4 hours and then concentrated under reduced pressure, and the resulting crude product was purified by normal-phase silica gel column chromatography (hexane/ethyl acetate) to afford (S)-cyanomethyl 5-azido-2-((tert-butoxycarbonyl)amino)pentanoate (Compound tk70) (185 mg, quant.).

LCMS (ESI) m/z=296 (M−H)−

Retention time: 0.73 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-azido-2-((tert-butoxycarbonyl)amino)pentanoate (Compound tk71)

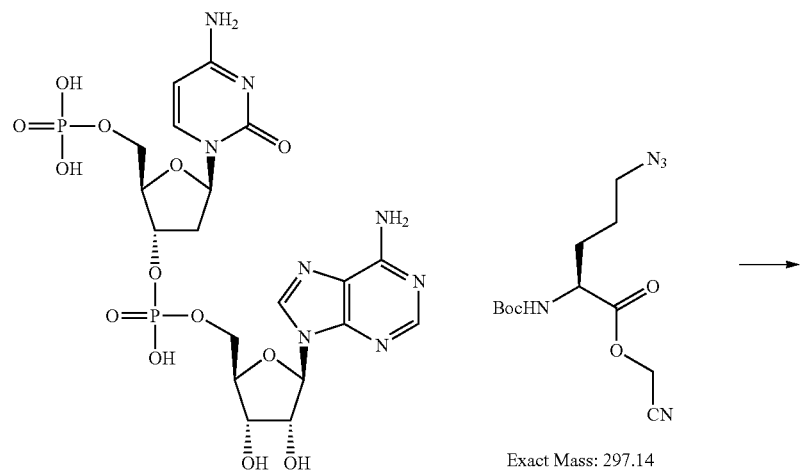

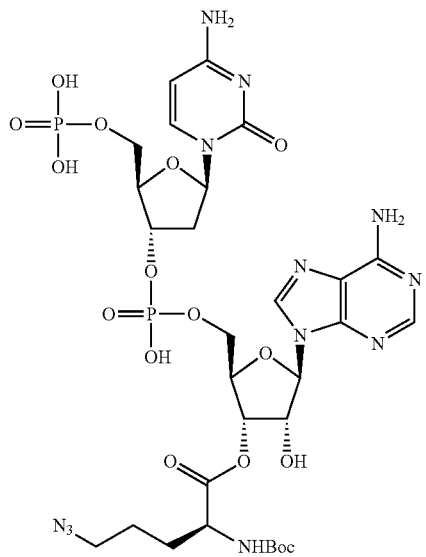

Exact Mass: 876.23

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (77 mg, 0.121 mmol) in water (0.3 mL) and a solution of (S)-cyanomethyl 5-azide-2-((tert-butoxycarbonyl)amino)pentanoate (Compound tk70) (144 mg, 0.484 mmol) in tetrahydrofuran (0.3 mL) were added to buffer A (18 mL), and the mixture was stirred at room temperature for 0.5 hour. Following lyophilization, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-azido-2-((tert-butoxycarbonyl)amino)pentanoate (Compound tk71) (24.5 mg, 23%).

LCMS (ESI) m/z=875.4 (M−H)−

Retention time: 0.44 min (analysis condition SQDFA05)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-azidopentanoate (Orn(N3)-pdCpA) (Compound tk72)

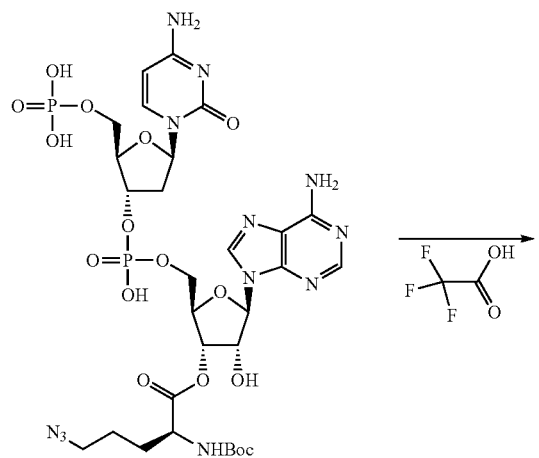

Exact Mass: 876.23

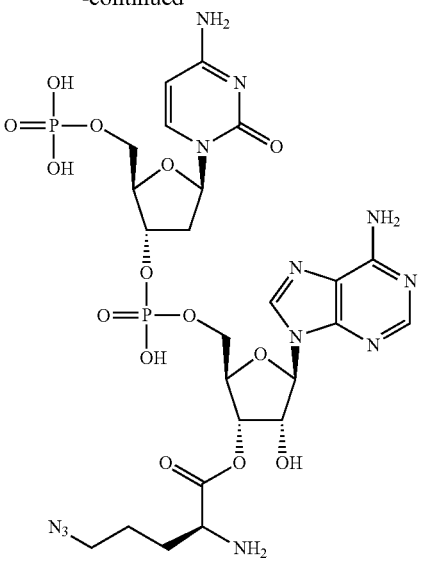

Exact Mass: 776.18

Trifluoroacetic acid (0.09 mL) was added to a solution of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 5-azido-2-((tert-butoxycarbonyl)amino)pentanoate (Compound tk71) (24.5 mg, 0.028 mmol) in dichloromethane (1 mL), and the mixture was stirred at room temperature for 25 minutes. Following concentration under reduced pressure, the resulting residue was purified by reverse-phase silica gel column chromatography (0.05% aqueous trifluoroacetic acid solution/0.05% trifluoroacetic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-5-azidopentanoate (Orn(N3)-pdCpA) (Compound tk72) (18.8 mg, 87%).

LCMS (ESI) m/z=775.4 (M−H)−

Retention time: 0.25 min (analysis condition SQDFA05)

10-1-15. Synthesis of Aminoacylated pdCpA Compound tk85

The synthesis was carried out according to the following scheme.

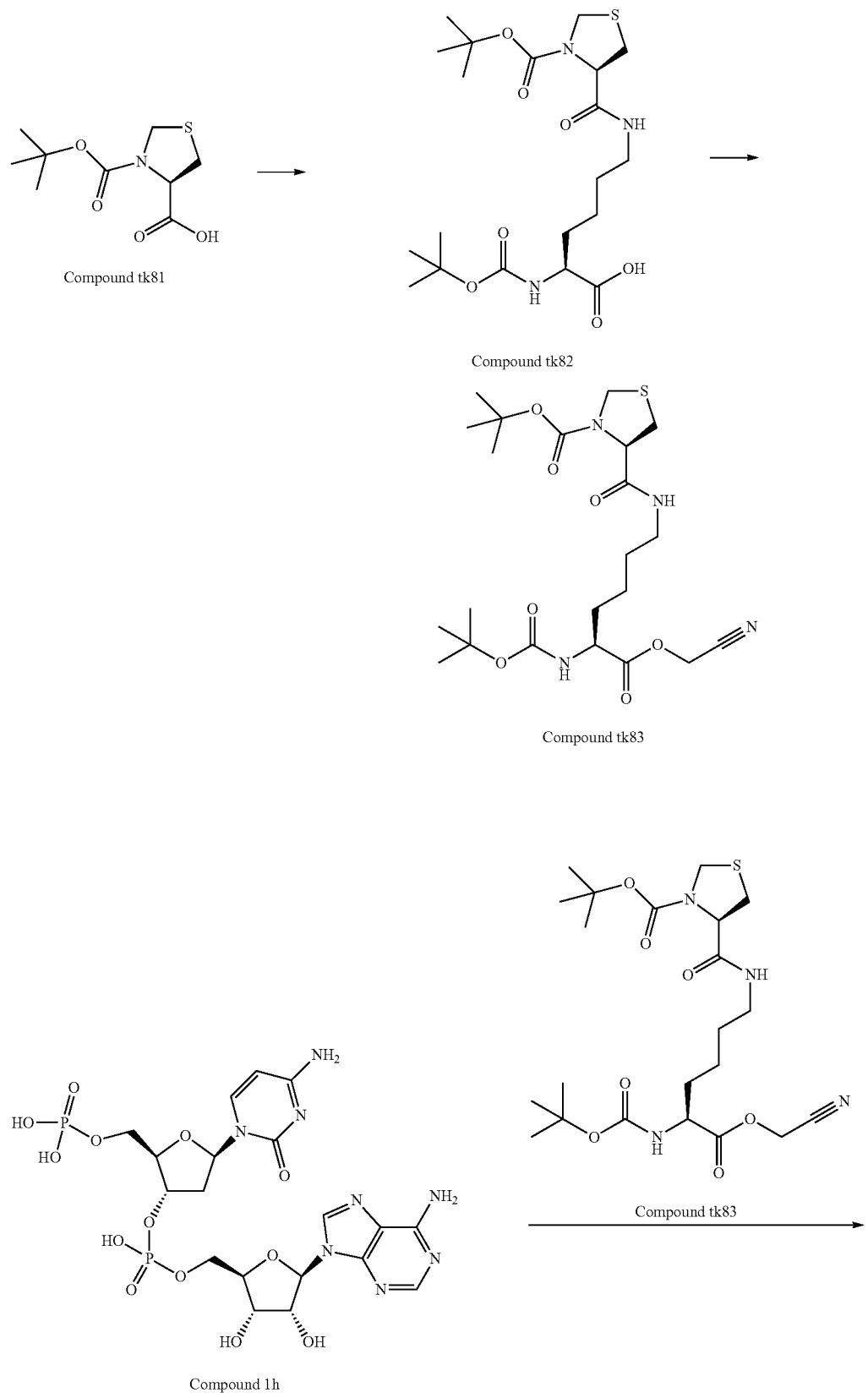

-continued
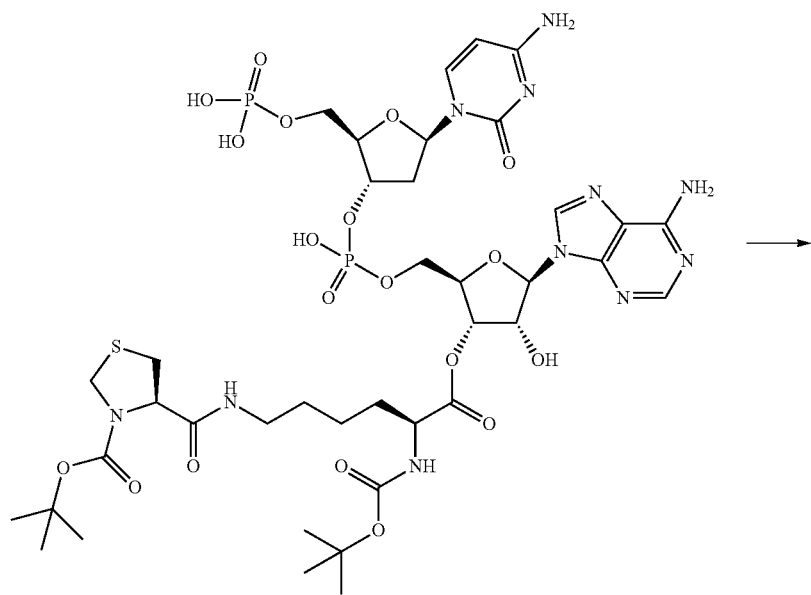
Compound tk84
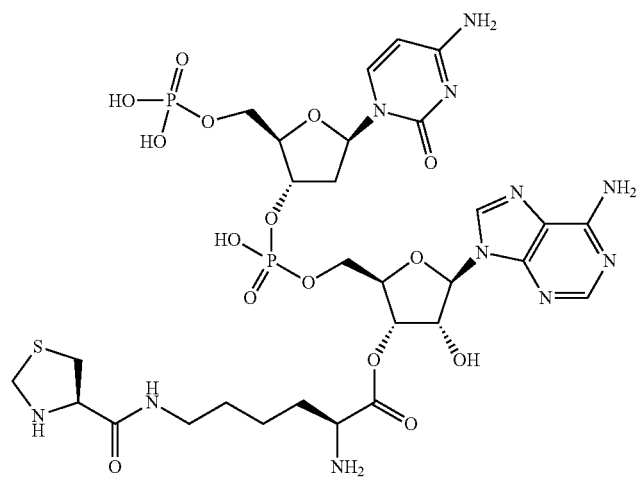
Compound tk85

Synthesis of (S)-2-((tert-butoxycarbonyl)amino)-6-((R)-3-(tert-butoxycarbonyl)thiazolidine-4-carboxamido)hexanoic Acid (Compound tk82)

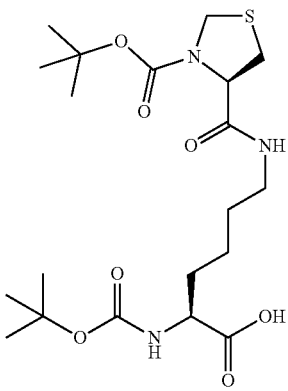 [SMILES: CC(C)(C)OC(=O)N[C@@H](CCCCNC(=O)[C@@H]1CSCN1C(=O)OC(C)(C)C)C(=O)O]

4-(4,6-Dimethoxy-1,3,5-triazin-2-yl)-4-methylmorpholinium chloride (247 mg, 0.892 mmol) was added to a solution of (R)-3-(tert-butoxycarbonyl)thiazolidine-4-carboxylic acid (Compound tk81) (208 mg, 0.892 mmol) in DMF (1 ml), and the mixture was stirred at room temperature for 30 minutes. A solution of (S)-6-amino-2-((tert-butoxycarbonyl)amino)hexanoic acid (220 mg, 0.892 mmol) in water (1 ml) was added dropwise at room temperature over 3 minutes. After completion of the dropwise addition, the mixture was stirred at room temperature for 30 minutes. The reaction solution was purified by reverse-phase silica gel column chromatography (10 mM aqueous ammonium acetate solution/methanol) to afford (S)-2-((tert-butoxycarbonyl)amino)-6-((R)-3-(tert-butoxycarbonyl)thiazolidine-4-carboxamido)hexanoic acid (Compound tk82) (156 mg, 38%).

LCMS (ESI) m/z=462 (M+H)+
Retention time: 0.66 min (analysis condition SQDFA05)

Synthesis of (R)-tert-butyl 4-(((S)-5-((tert-butoxycarbonyl)amino)-6-(cyanomethoxy)-6-oxohexyl)carbamoyl)thiazolidine-3-carboxylate (Compound tk83)

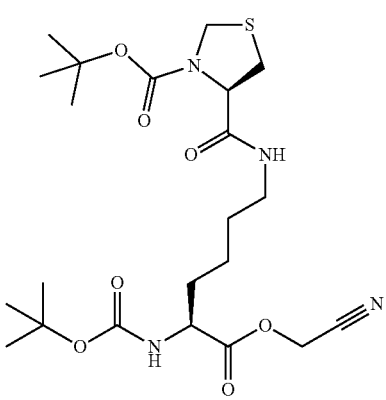 [SMILES: CC(C)(C)OC(=O)N[C@@H](CCCCNC(=O)[C@@H]1CSCN1C(=O)OC(C)(C)C)C(=O)OCC#N]

Bromoacetonitrile (57 µl, 0.845 mmol) and N,N-diisopropylethylamine (147 µl, 0.845 mmol) were added to a solution of (S)-2-((tert-butoxycarbonyl)amino)-6-((R)-3-(tert-butoxycarbonyl)thiazolidine-4-carboxamido)hexanoic acid (Compound tk82) (130 mg, 0.282 mmol) in acetonitrile (5 ml), and the reaction solution was stirred at room temperature for 3 hours. The reaction mixture was concentrated under reduced pressure using an evaporator, and the residue was purified by normal-phase silica gel column chromatography (hexane/ethyl acetate) to afford (R)-tert-butyl 4-(((S)-5-((tert-butoxycarbonyl)amino)-6-(cyanomethoxy)-6-oxohexyl)carbamoyl)thiazolidine-3-carboxylate (Compound tk83) (140 mg, 99%).

LCMS (ESI) m/z=501.5 (M+H)+
Retention time: 0.76 min (analysis condition SQDFA05)

Synthesis of (4R)-tert-butyl 4-(((5S)-6-(((2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl)oxy)-5-((tert-butoxycarbonyl)amino)-6-oxohexyl)carbamoyl)thiazolidine-3-carboxylate (Compound tk84)

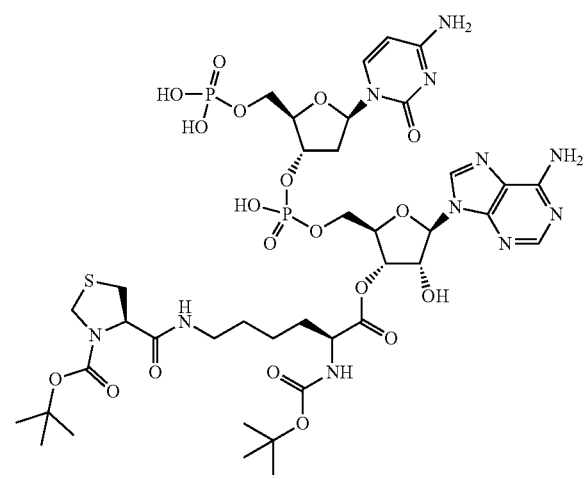 [SMILES: CC(C)(C)OC(=O)N[C@@H](CCCCNC(=O)[C@@H]1CSCN1C(=O)OC(C)(C)C)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (50 mg, 0.079 mmol) in water (0.5 mL) and a solution of (R)-tert-butyl 4-(((S)-5-((tert-butoxycarbonyl)amino)-6-(cyanomethoxy)-6-oxohexyl)carbamoyl)thiazolidine-3-carboxylate (Compound tk83) (118 mg, 0.236 mmol) in tetrahydrofuran (0.5 mL) were added to buffer A (40 mL), and the mixture was stirred at room temperature for 2 hours. Following lyophilization, the resulting residue was purified by reverse-phase silica gel column chromatography (water/acetonitrile solution) to afford a crude purified product of (4R)-tert-butyl 4-(((5S)-6-(((2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl)oxy)-5-((tert-butoxycarbonyl)amino)-6-oxohexyl)carbamoyl)thiazolidine-3-carboxylate (Compound tk84) (80 mg).

LCMS (ESI) m/z=1078 (M–H)–
Retention time: 0.55 min (analysis condition SQDFA05)

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-((r)-thiazolidine-4-carboxamido)hexanoate (Lys(Thz)-pdCpA) (Compound tk85)

The aforementioned crude purified product of (4R)-tert-butyl 4-(((5S)-6-(((2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl)oxy)-5-((tert-butoxycarbonyl)amino)-6-oxohexyl)carbamoyl)thiazolidine-3-carboxylate (Compound tk84) (20 mg) was suspended in dichloromethane (0.3 ml), trifluoroacetic acid (0.1 mL) was added at room temperature, and the mixture was stirred at the same temperature for 30 minutes. Following concentration under reduced pressure, the resulting residue was purified by reverse-phase silica gel column chromatography (water/acetonitrile solution) to afford (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-((R)-thiazolidine-4-carboxamido)hexanoate (Lys(Thz)-pdCpA) (Compound tk85) (1.6 mg, 7% in two steps).

LCMS (ESI) m/z=878 (M−H)−

Retention time: 0.17 min (analysis condition SQDFA05)

10-1-16. Synthesis of Aminoacylated pdCpA Compound tk90

The synthesis was carried out according to the following scheme.

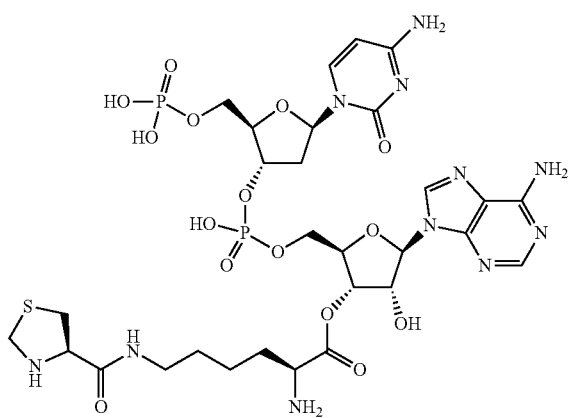 [SMILES: Nc1ccn([C@H]2C[C@H](OP(=O)(O)OC[C@H]3O[C@@H](n4cnc5c(N)ncnc54)[C@H](O)[C@@H]3OC(=O)[C@@H](N)CCCCNC(=O)[C@@H]3CSCN3)[C@@H](COP(=O)(O)O)O2)c(=O)n1]

TK scheme 16

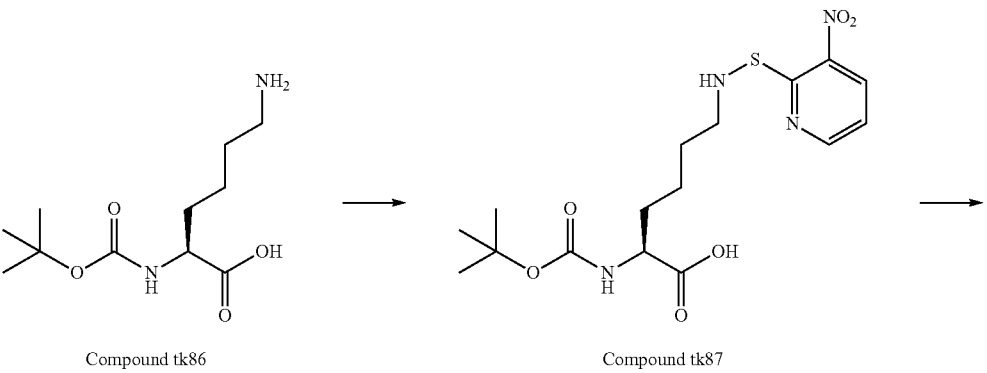

Compound tk86   Compound tk87

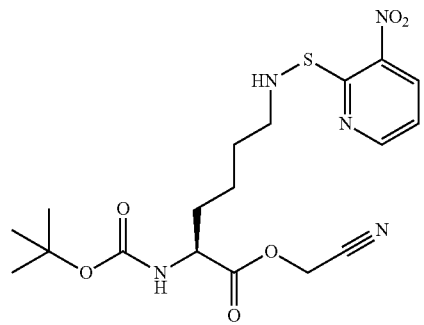

Compound tk88

2497                                   2498
-continued
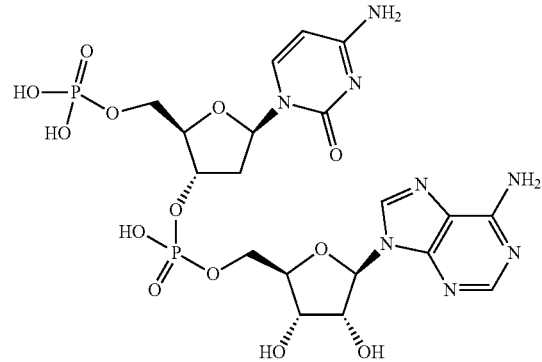
Compound 1h
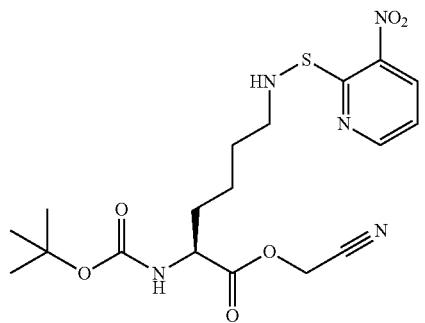 [SMILES: CC(C)(C)OC(=O)N[C@@H](CCCCNSc1ncccc1[N+](=O)[O-])C(=O)OCC#N]
Compound tk88
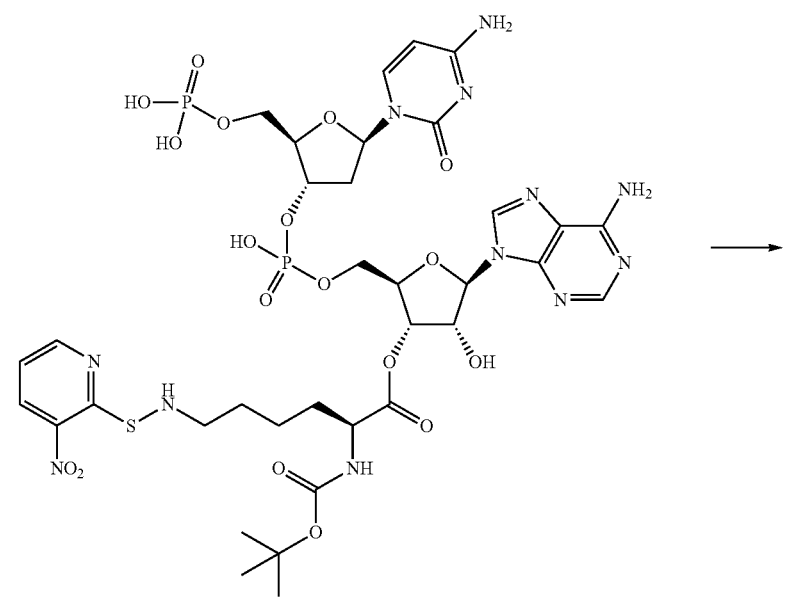
Compound tk89

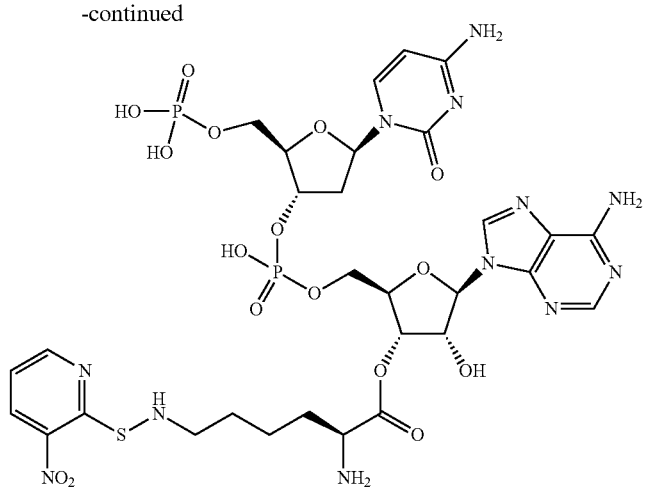

Compound tk90

Synthesis of (S)-2-((tert-butoxycarbonyl)amino)-6-(((3-nitropyridin-2-yl)thio)amino)hexanoic Acid (Compound tk87)

Synthesis of (S)-cyanomethyl 2-((tert-butoxycarbonyl)amino)-6-(((3-nitropyridin-2-yl)thio)amino)hexanoate (Compound tk88)

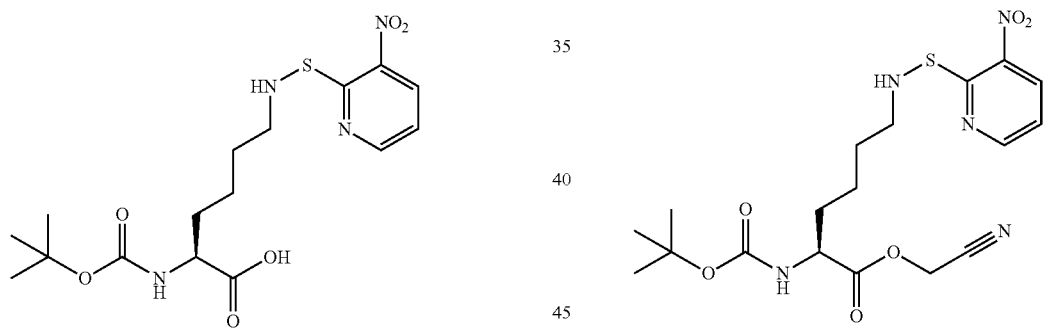

(S)-6-amino-2-((tert-butoxycarbonyl)amino)hexanoic acid (Compound tk86) (270 mg, 1.096 mmol) was added to a solution of nitro-2-pyridinesulfenyl chloride (313 mg, 1.644 mmol) in dichloromethane (30 ml), and triethylamine (1.53 ml, 10.96 mmol) was added dropwise to the suspension over 3 minutes. The reaction solution was stirred at room temperature for 3 hours and then concentrated under reduced pressure using an evaporator, and the resulting residue was purified by reverse-phase silica gel column chromatography (0.1% aqueous formic acid solution/0.1% formic acid-acetonitrile solution) to afford (S)-2-((tert-butoxycarbonyl)amino)-6-(((3-nitropyridin-2-yl)thio)amino)hexanoic acid (Compound tk87) (62 mg, 14%).

LCMS (ESI) m/z=401 (M+H)+

Retention time: 0.74 min (analysis condition SQDFA05)

Bromoacetonitrile (76 μl, 1.124 mmol) and N,N-diisopropylethylamine (196 μl, 1.124 mmol) were added to a solution of ((S)-2-((tert-butoxycarbonyl)amino)-6-(((3-nitropyridin-2-yl)thio)amino)hexanoic acid (Compound tk87) (150 mg, 0.375 mmol) in acetonitrile (6 ml), and the reaction solution was stirred at room temperature for 5 hours. Bromoacetonitrile (49 μl, 0.413 mmol) was further added and the mixture was stirred at room temperature for 1 hour to complete the reaction. The reaction mixture was concentrated under reduced pressure using an evaporator, and the residue was purified by normal-phase silica gel column chromatography (hexane/ethyl acetate) to afford (S)-cyanomethyl 2-((tert-butoxycarbonyl)amino)-6-(((3-nitropyridin-2-yl)thio)amino)hexanoate (Compound tk88) (152 mg, 92%).

LCMS (ESI) m/z=440 (M+H)+

Retention time: 0.83 min (analysis condition SQDFA05)

2501

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-6-(((3-nitropyridin-2-yl)thio)amino)hexanoate (Compound tk89)

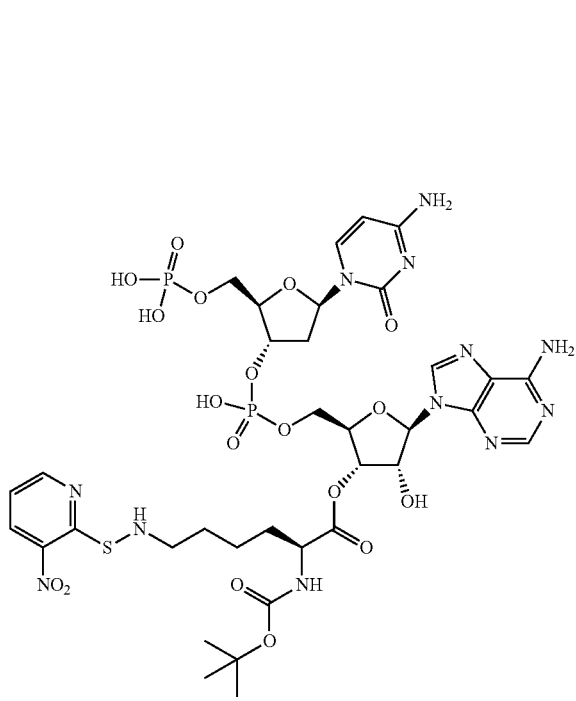 [SMILES: CC(C)(C)OC(=O)N[C@@H](CCCCNSc1ncccc1[N+](=O)[O-])C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

A solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (20 mg, 0.031 mmol) in water (0.5 mL) and a solution of (S)-cyanomethyl 2-((tert-butoxycarbonyl)amino)-6-(((3-nitropyridin-2-yl)thio)amino)hexanoate (Compound tk88) (30 mg, 0.069 mmol) in acetonitrile (0.5 ml) were added to buffer A (30 mL), and the mixture was stirred at room temperature for 2 hours. Following lyophilization, the resulting residue was purified by reverse-phase silica gel column chromatography (0.1% aqueous formic acid solution/0.1% formic acid-acetonitrile solution) to afford a crude purified product of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-6-(((3-nitropyridin-2-yl)thio)amino)hexanoate (Compound tk89) (16 mg).

LCMS (ESI) m/z=1017 (M–H)–

Retention time: 0.54 min (analysis condition SQDFA05)

2502

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-amino-6-(((3-nitropyridin-2-yl)thio)amino)hexanoate (Lys(Npys)-pdCpA) (Compound tk90)

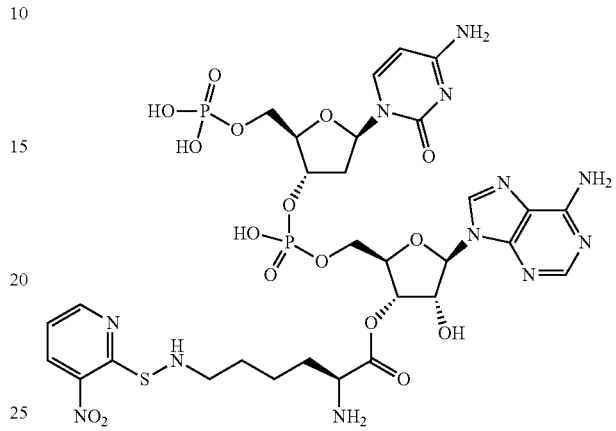

The aforementioned crude purified product of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-((tert-butoxycarbonyl)amino)-6-(((3-nitropyridin-2-yl)thio)amino)hexanoate (Compound tk89) (16 mg) was suspended in dichloromethane (1 ml), trifluoroacetic acid (0.25 mL) was added at room temperature, and the mixture was stirred at the same temperature for 15 minutes. Following concentration under reduced pressure, the resulting residue was purified by reverse-phase silica gel column chromatography (0.1% aqueous formic acid solution/0.1% formic acid-acetonitrile solution) to afford (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-Purin-9-yl)-4-hydroxytetrahydrofuran-3-yl 2-amino-6-(((3-nitropyridin-2-yl)thio)amino)hexanoate (Lys(Npys)-pdCpA) (Compound tk90) (12 mg, 42% in two steps).

LCMS (ESI) m/z=917 (M–H)–

Retention time: 0.34 min (analysis condition SQDFA05)

10-2. Confirmation of Deprotection Conditions

The following experiment was carried out in order to confirm that protecting groups for amino groups are deprotected under reaction conditions where RNA is stable or to search for alternative conditions, thus providing amino group deprotection reaction under reaction conditions where RNA stably exists.

10-2-1. Synthesis and Deprotection Reaction of Compound tk94 for Deprotection Method Evaluation The synthesis was carried out according to the following scheme.

TK scheme 17

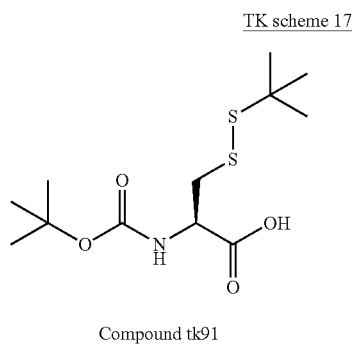

Compound tk91

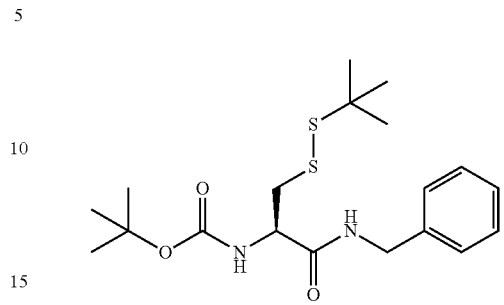

Compound tk92

Synthesis of (R)-tert-butyl (1-(benzylamino)-3-(tert-butyldisulfanyl)-1-oxopropan-2-yl)carbamate (Compound tk92)

O-(7-Azabenzotriazol-1-yl)-N,N,N',N'-tetramethyluronium hexafluorophosphate (HATU) (2.52 g, 6.62 mmol), benzylamine (0.723 ml, 6.62 mmol) and N,N-diisopropylethylamine (1.153 ml, 6.62 mmol) were added to a solution of (R)-2-((tert-butoxycarbonyl)amino)-3-(tert-butyldisulfanyl)propanoic acid (Compound tk91) (1.95 g, 6.30 mmol) in tetrahydrofuran (20 ml), and the reaction solution was stirred at room temperature for 2 hours. The reaction solution was concentrated under reduced pressure, and the resulting residue was purified by normal-phase silica gel column chromatography (hexane/ethyl acetate) to afford (R)-tert-butyl(1-(benzylamino)-3-(tert-butyldisulfanyl)-1-oxopropan-2-yl)carbamate (Compound tk92) (2.357 g, 5.91 mmol, 94%).

LCMS (ESI) m/z=399 (M+H)+

Retention time: 0.93 min (analysis condition SQDFA05)

Synthesis of (R)-2-amino-N-benzyl-3-(tert-butyldisulfanyl)propanamide (Compound tk93)

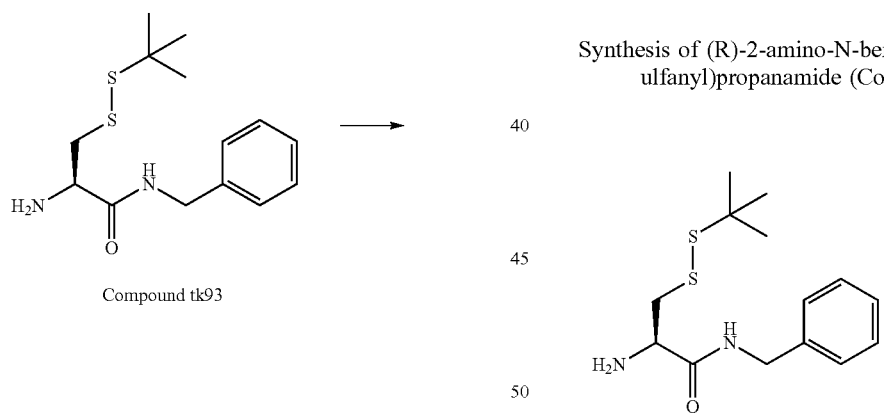

Compound tk93

Trifluoroacetic acid (3 ml) was added to a solution of (R)-tert-butyl(1-(benzylamino)-3-(tert-butyldisulfanyl)-1-oxopropan-2-yl)carbamate (Compound tk92) (1.049 g, 2.63 mmol) in dichloromethane (9 ml), and the reaction solution was stirred at room temperature for 1 hour. The reaction solution was concentrated under reduced pressure and then extracted with ethyl acetate/saturated sodium bicarbonate, and the organic layer was washed with brine. The organic layer was dried over anhydrous sodium sulfate, filtered and then concentrated under reduced pressure to afford (R)-2-amino-N-benzyl-3-(tert-butyldisulfanyl)propanamide (Compound tk93) (810 mg, 100%).

LCMS (ESI) m/z=297 (M−H)−

Retention time: 0.93 min (analysis condition SQDAA05)

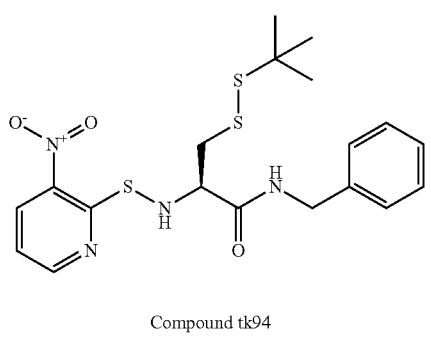

Compound tk94

Synthesis of (R)—N-benzyl-3-(tert-butyldisulfanyl)-2-(((3-nitropyridin-2-yl)thio)amino)propanamide (Compound tk94)

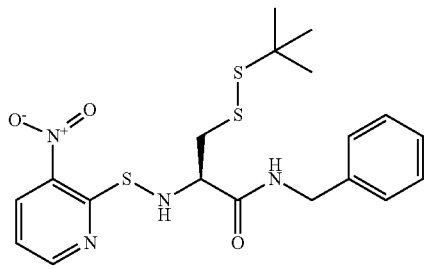 [SMILES: CC(C)(C)SSC[C@H](NSc1ncccc1[N+](=O)[O-])C(=O)NCc1ccccc1]

(R)-2-amino-N-benzyl-3-(tert-butyldisulfanyl)propanamide (Compound tk93) (60 mg, 0.201 mmol) and triethylamine (0.034 ml, 0.241 mmol) were dissolved in dichloromethane (1 ml), and the solution was cooled to 0° C. 3-Nitro-2-pyridinesulfenyl chloride (46.0 mg, 0.241 mmol) was added and the mixture was stirred at 0° C. for 2 hours. The reaction solution was concentrated under reduced pressure, and the resulting residue was purified by normal-phase silica gel column chromatography (hexane/ethyl acetate) to afford (R)—N-benzyl-3-(tert-butyldisulfanyl)-2-(((3-nitropyridin-2-yl)thio)amino)propanamide (Compound tk94) (87 mg, 96%)

LCMS (ESI) m/z=453 (M+H)+
Retention time: 1.03 min (analysis condition SQDAA05)

3-nitro-2-pyridinesulfenyl Group (Npys) Deprotection Experiment

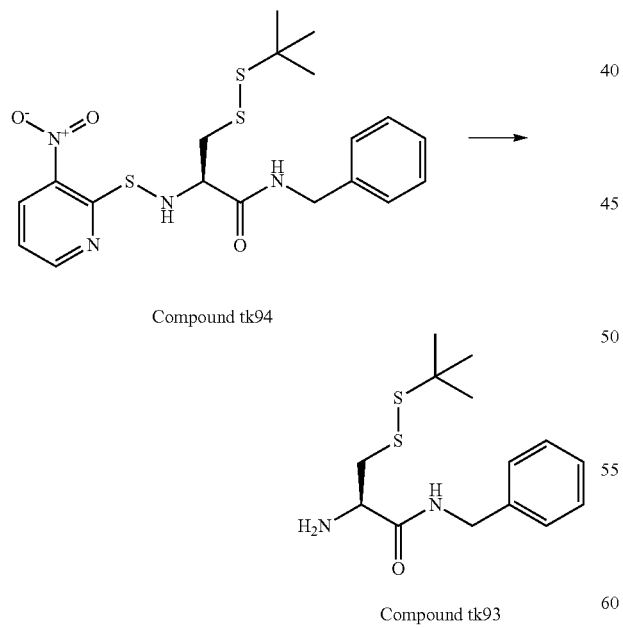

Compound tk94

Compound tk93

(R)—N-benzyl-3-(tert-butyldisulfanyl)-2-(((3-nitropyridin-2-yl)thio)amino)propanamide (Compound tk94) was dissolved in N,N-dimethylacetamide (DNA) to prepare a 50 mM DMA solution. DMA (50 μl), 100 mM HEPES buffer solution adjusted to pH 7.4 (250 μl) and a 200 mM solution of 2-mercaptopyridine in DMA (50 μl) were sequentially added to 50 μl of the DMA solution, and finally 1 M hydrochloric acid (13 μl) was added to prepare a reaction solution at pH 4.1. The reaction solution was allowed to stand at room temperature to cause deprotection reaction. For the progress of the reaction, the decrease in (R)—N-benzyl-3-(tert-butyldisulfanyl)-2-(((3-nitropyridin-2-yl)thio)amino)propanamide (Compound tk94) and the increase in the deprotected compound, (R)-2-amino-N-benzyl-3-(tert-butyldisulfanyl)propanamide (Compound tk93), were traced by LCMS. One hour after the reaction, the UV area ratio of Compound tk93 and Compound tk94 was 100:0, thus confirming completion of the deprotection reaction.

The retention time and the mass-charge ratio by LCMS of Compound tk93 are as follows.

LCMS (ESI) m/z=299 (M+H)+
Retention time: 0.90 min (analysis condition SQDAA05)

A condition under which a nucleophile 2-mercaptopyridine is used in an organic solvent and acetic acid is further added to the reaction solution to accelerate the deprotection reaction has been reported as a known Npys group deprotection method (Non patent literature, international journal of peptide and protein research, 1990, 35, 545-549). As a result of improving the conventional method, the present inventors have found a method in which Npys group deprotection reaction readily proceeds under conditions where RNA stably exists. As a result of actually subjecting RNA to the present reaction condition, the RNA was confirmed to stably exist (reaction condition E of Table 19 and lane 5 of FIG. 80), and utility of the present reaction condition was demonstrated.

10-2-2. Synthesis of and Deprotection Experiment for Compound tk95 for Deprotection Method Evaluation The synthesis was carried out according to the following scheme.

TK scheme 18

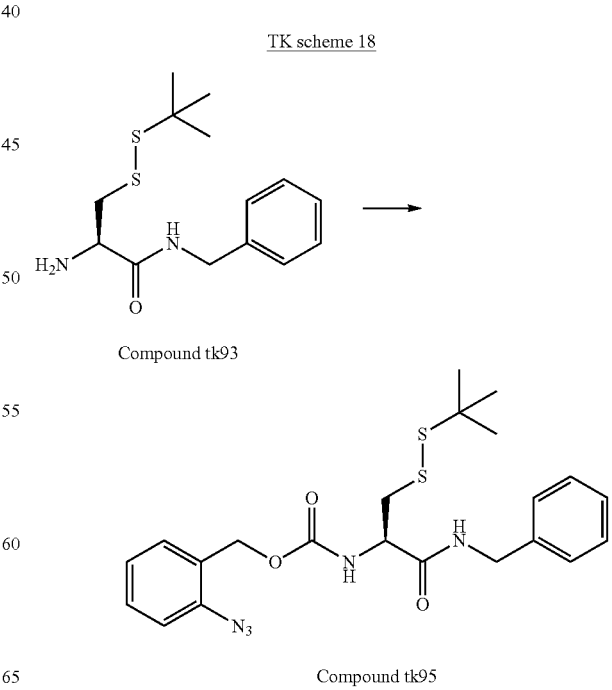

Compound tk93

Compound tk95

2507

Synthesis of (R)-4-azidobenzyl (1-(benzylamino)-3-(tert-butyldisulfanyl)-1-oxopropan-2-yl)carbamate (Compound tk95)

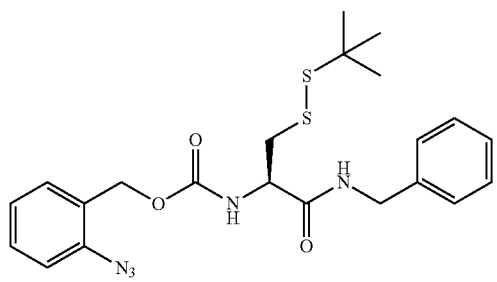 [SMILES: CC(C)(C)SSC[C@H](NC(=O)OCc1ccccc1N=[N+]=[N-])C(=O)NCc1ccccc1]

2-Azidobenzyl (4-nitrophenyl) carbonate (168 mg, 0.534 mmol) was added to a suspension of (R)-2-amino-N-benzyl-3-(tert-butyldisulfanyl)propanamide (Compound tk93) (145 mg, 0.486 mmol) and sodium bicarbonate (102 mg, 1.215 mmol) in 1,4-dioxane (2 mL) at room temperature. The reaction mixture was stirred at the same temperature for 15.5 hours, followed by addition of ethyl acetate and water. The resulting mixture was extracted with ethyl acetate, and the organic phase was washed with water (5 mL×2) and brine (5 mL) and dried over sodium sulfate. Following concentration under reduced pressure, the resulting residue was purified by normal-phase silica gel column chromatography (hexane/ethyl acetate) and then purified by reverse-phase silica gel column chromatography (0.05% aqueous trifluoroacetic-acid solution/0.05% trifluoroacetic acid-acetonitrile solution) to afford (R)-4-azidobenzyl (1-(benzylamino)-3-(tert-butyldisulfanyl)-1-oxopropan-2-yl)carbamate (Compound tk95) (148.9 mg, 65%).

LCMS (ESI) m/z=474.4 (M+H)+

Retention time: 0.97 min (analysis condition SQDFA05)

2-Azidobenzyloxycarbonyl Group (oAcbz) Deprotection Experiment

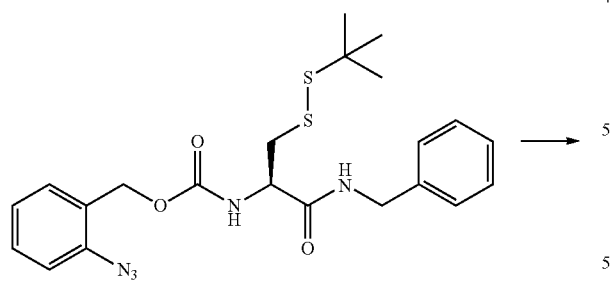

Compound tk95

Compound tk99

2508

(R)-4-azidobenzyl (1-(benzylamino)-3-(tert-butyldisulfanyl)-1-oxopropan-2-yl)carbamate (Compound tk95) was dissolved in acetonitrile to prepare a 10 mM acetonitrile solution. Acetonitrile (5 µl), 100 mM HEPES buffer adjusted to pH 7.4 (50 µl), distilled water (25 WO and a 100 mM aqueous tris(2-carboxyethyl)phosphine solution adjusted to pH 7.0 (10 µl) were sequentially added to 10 µl of the acetonitrile solution to prepare a reaction solution at pH 7.4. The reaction solution was allowed to stand at 37° C. to cause deprotection reaction. For the progress of the reaction, the decrease in Compound tk95 and the increase in the deprotected compound, (R)-2-amino-N-benzyl-3-mercaptopropanamide (Compound tk99), were traced by LCMS. 1.5 hours after the reaction, the UV area ratio of Compound tk99 and Compound tk95 was 100:0, thus confirming completion of the deprotection reaction.

The retention time and the mass-charge ratio by LCMS of Compound tk99 are as follows.

LCMS (ESI) m/z=211 (M+H)+

Retention time: 0.61 min (analysis condition SQDAA05)

Thus, it was revealed that the 2-azidobenzyloxycarbonyl group can be deprotected by addition of a reducing agent, tris(2-carboxyethyl)phosphine. The present deprotection method has been found as a condition under which RNA is stable. As a result of actually subjecting RNA to the present reaction condition, the RNA was confirmed to stably exist (reaction condition C of Table 19 and lane 3 of FIG. 80), and utility of the present reaction condition was demonstrated.

2-3. Synthesis of and Deprotection Experiment for Compound tk97 for Deprotection Method Evaluation The synthesis was carried out according to the following scheme.

TK Scheme 19

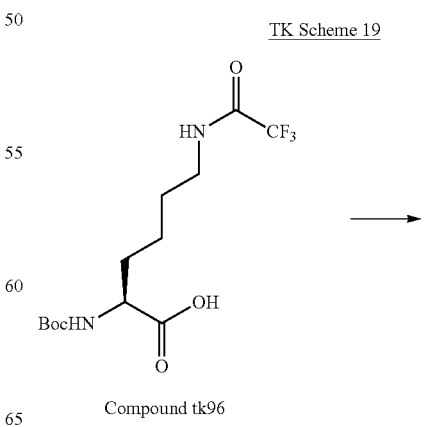

Compound tk96

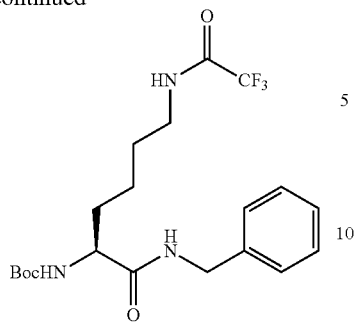

Compound tk97

Synthesis of (S)-tert-butyl (1-(benzylamino)-1-oxo-6-(2,2,2-trifluoroacetamido)hexan-2-yl)carbamate (Compound tk97)

A solution of Boc-Lys(Tfa)-OH (Compound tk96) (104 mg, 0.304 mmol) and 1H-benzo[d][1,2,3]triazol-1-ol (HOBT) (61.6 mg, 0.456 mmol) in DMF (0.5 mL) was cooled in an ice bath under a nitrogen atmosphere, followed by addition of 1-ethyl-3-(3-dimethylaminopropyl)carbodiimide hydrochloride (WSCI·HCl) (87 mg, 0.456 mmol). The reaction mixture was stirred at the same temperature for 5 minutes, followed by addition of benzylamine (40 µL, 0.365 mmol). The reaction mixture was stirred at room temperature for 17.5 hours, followed by addition of ethyl acetate, hexane and brine. The resulting mixture was extracted with ethyl acetate, and the organic phase was washed with brine (1 mL×2) and then dried over sodium sulfate. Following concentration under reduced pressure, the resulting residue was purified by normal-phase silica gel column chromatography (hexane/ethyl acetate) to afford (S)-tert-butyl (1-(benzylamino)-1-oxo-6-(2,2,2-trifluoroacetamido)hexan-2-yl)carbamate (Compound tk97) (134.4 mg, quant.).

LCMS (ESI) m/z=430.4 (M−H)−

Retention time: 0.73 min (analysis condition SQDFA05)

Trifluoroacetyl Group (Tfa) Deprotection Experiment

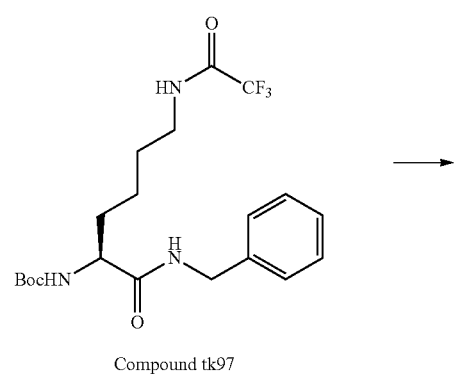

Compound tk97

⟶

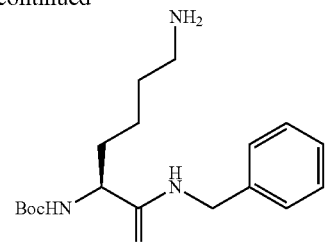

Compound tk98

(S)-tert-Butyl (1-(benzylamino)-1-oxo-6-(2,2,2-trifluoroacetamido)hexan-2-yl)carbamate (Compound tk97) was dissolved in dimethoxyethane to prepare a 20 mM dimethoxyethane solution. Dimethoxyethane (30 µl) and a 100 mM bicine buffer adjusted to pH 9.1 (210 µl) were sequentially added to the dimethoxyethane solution. A 100 mM bicine buffer (15 µl) was added to 85 µL of the solution to prepare a reaction solution at pH 9.1, and the reaction solution was allowed to stand at 37° C. to cause deprotection reaction. For the progress of the reaction, the decrease in the trifluoroacetyl-protected compound (Compound tk97) and the increase in the deprotected compound, (S)-tert-butyl (6-amino-1-(benzylamino)-1-oxohexan-2-yl)carbamate (Compound tk98), were traced by LCMS.

The UV area ratios of Compound tk98 and Compound tk97 after 17 hours and after 93.5 hours were as follows.
After 17 hours: Compound tk98:Compound tk97=19:81
After 93.5 hours: Compound tk98:Compound tk97=70:30

The retention time and the mass-charge ratio by LCMS of Compound tk98 are as follows.

LCMS (ESI) m/z=336.4 (M+H)+

Retention time: 0.74 minute (analysis condition SQDAA05)

Thus, it was revealed that the trifluoroacetyl group can be deprotected in a reaction solution at pH 9 at 37° C. The present deprotection method has been found as a condition under which RNA is stable. As a result of actually subjecting RNA to the pH and temperature under the present condition, the RNA was confirmed to stably exist (lane 7 of FIG. 83), and significance of the present reaction condition was demonstrated.

10-3-4. 4-Azidobenzyloxycarbonyl Group (Acbz) Deprotection Reaction

The reaction has been separately demonstrated in the experiment for reaction of conversion from Compound SP616 to Compound 618 as illustrated below.

2511
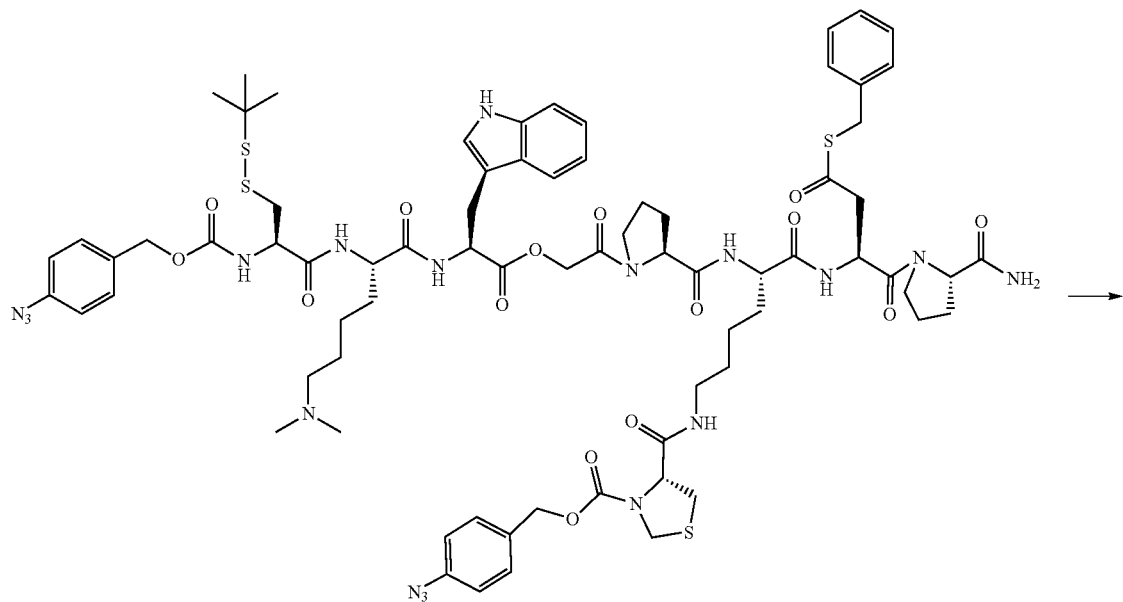
2512
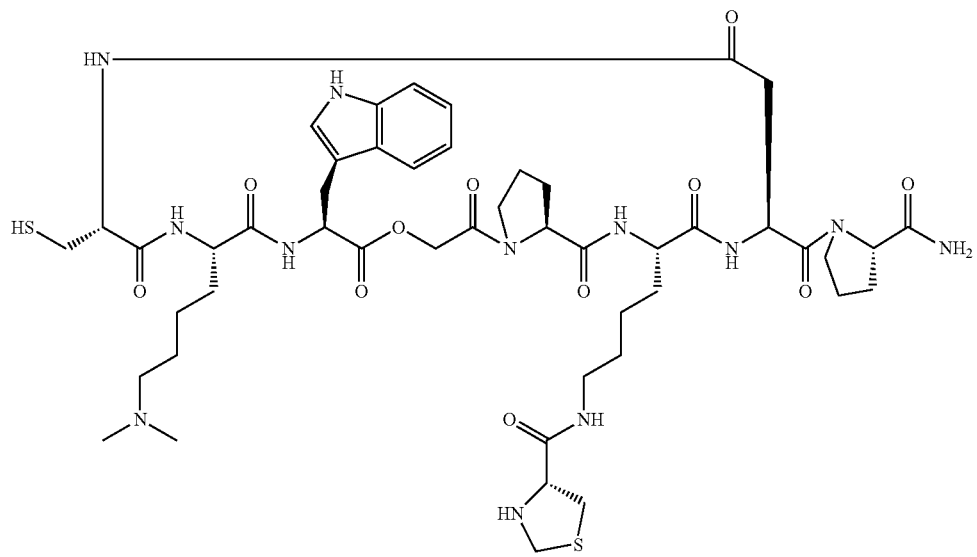
10-3-5. Thiazolidine Ring Deprotection Reaction
The reaction has been separately demonstrated in the experiment for reaction of conversion from Compound SP618 to Compound 620 as illustrated below.

2513
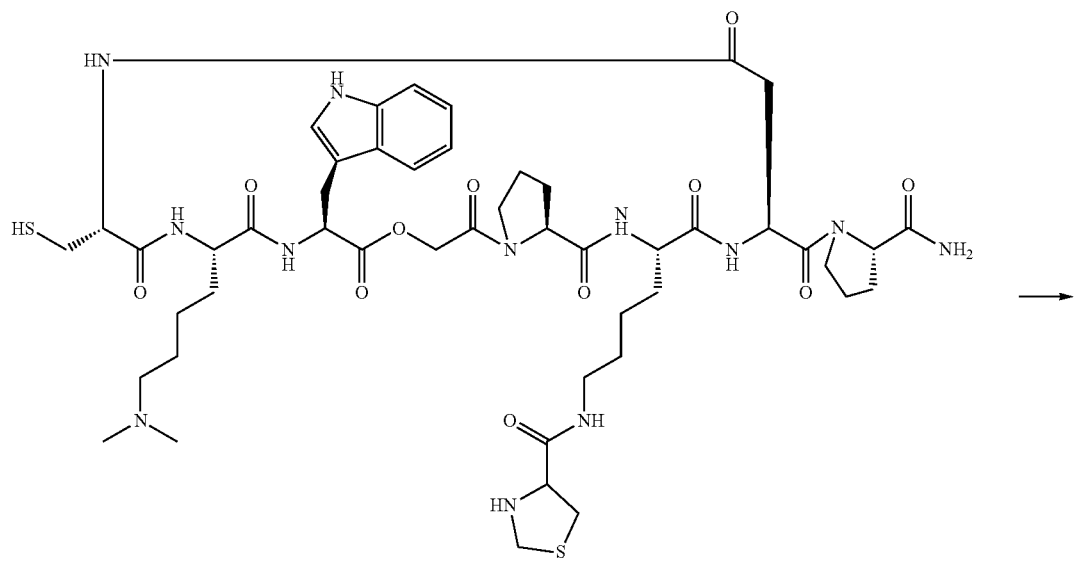
2514
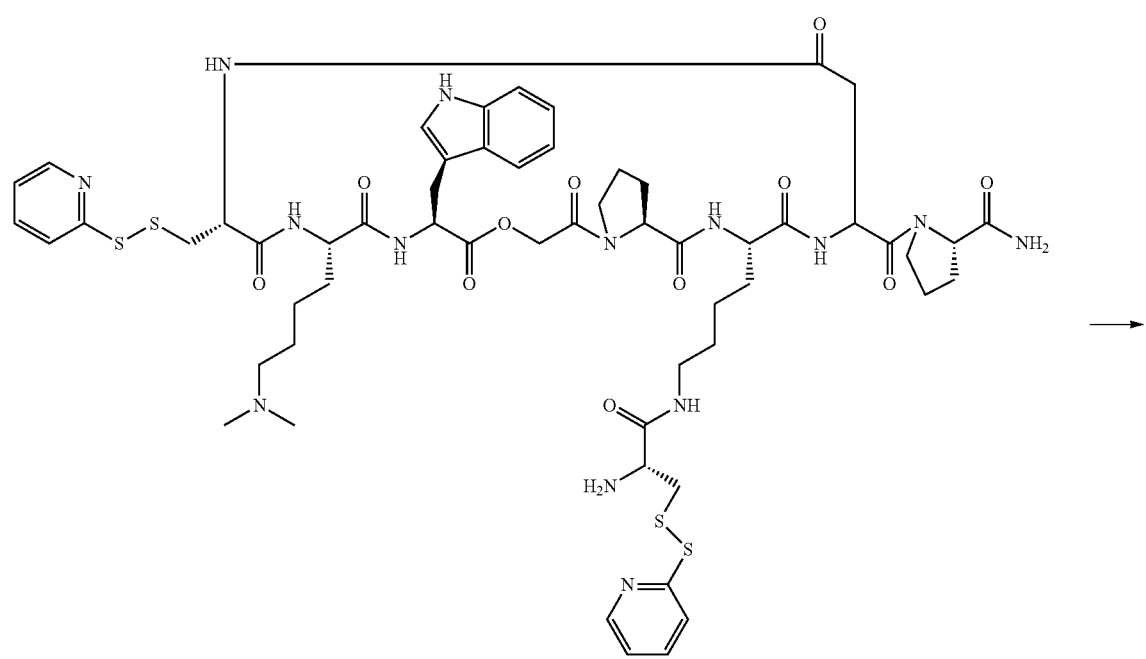

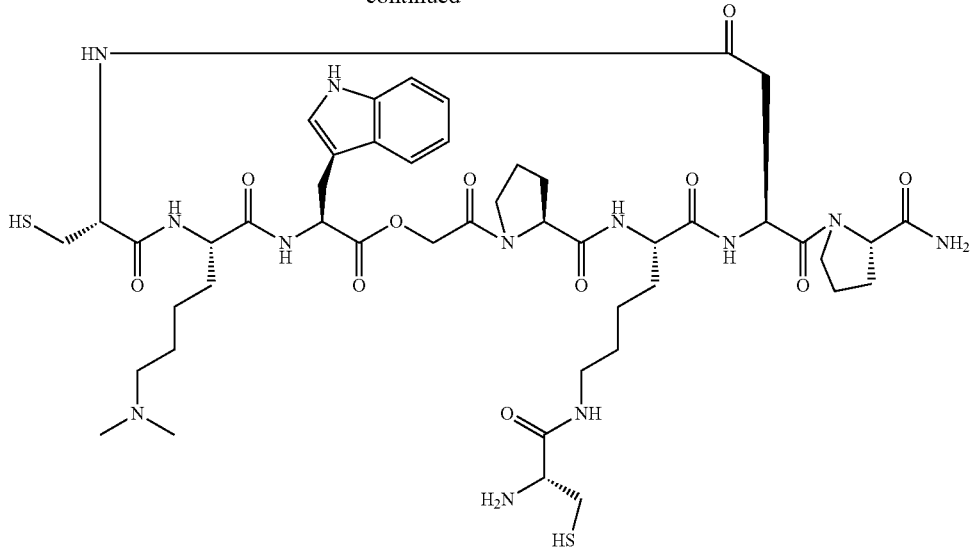

The following abbreviations or terms in Examples and other sections herein have the following meanings unless otherwise described.
  sol A: A mixture containing the following components: are 8 mM GTP, 8 mM ATP, 160 mM creatine phosphate, 400 mM HEPES-KOH pH 7.6, 800 mM potassium acetate, 48 mM magnesium acetate, 16 mM spermidine, 8 mM dithiothreitol, 0.8 mM 10-HCO—H4 folate and 12 mg/ml *E. coli* MRE600 (RNase negative)-derived tRNA (Roche).
  sol B: PURESYSTEM® classic II Sol. B (BioComber, product No. PURE2048C)
  20 natural amino acid solutions: 20 natural amino acid solutions (each 5 mM)
  $^{HO}$Gly: Glycolic acid
  Lac: L-(+)-Lactic acid
  PhLac: (S)-2-hydroxy-3-phenylpropanoic acid
  $^D$PhLac: (R)-2-hydroxy-3-phenylpropanoic acid
  $^{HO}$Gly(Me)$_2$: 2-hydroxy-2-methylpropanoic acid

3. Searching for Amino Acid Units Enlarging the Reaction of Producing Intramolecular Branched Peptides (Linear Portions 2)

Amino acids capable of strictly controlling two reactions, cyclization reaction and subsequent branched backbone production reaction, and containing side chain amino groups that can be deprotected under mild conditions were translationally introduced and analyzed by MALDI-MS.

3-1. Synthesis of tRNA (Lacking CA) by Transcription tRNAAsn-E2GUU (-CA) (SEQ ID NO: RT-H3) lacking 3'-end CA was synthesized from template DNA (SEQ ID NO: DT-H3) by in vitro transcription using RiboMAX Large Scale RNA production System T7 (Promega, P1300) and purified with RNeasy Mini kit (Qiagen).

SEQ ID NO: DT-H3
tRNAAsn-E2GUU (-CA) DNA sequence:

(SEQ ID NO: 94)
GGCGTAATACGACTCACTATAGGCTCTGTAGTTCAGTCGGTAGAACGGCG

GACTgttAATCCGTATGTCACTGGTTCGAGTCCAGTCAGAGCCGC

SEQ ID NO: RT-H3
tRNAAsn-E2GUU (-CA) RNA sequence:

(SEQ ID NO: 95)
GGCUCUGUAGUUCAGUCGGUAGAACGGCGGACUguuAAUCCGUAUGUCAC

UGGUUCGAGUCCAGUCAGAGCCGC

3-2. Synthesis of Aminoacylated tRNAs (Compounds AT-H3) by Ligation of Aminoacylated pdCpAs Having Side Chain Amino Groups Protected (Compounds tk5, tk60, tk64, tk90, tk38 and tk11) and tRNA (Lacking CA) (SEQ ID NO: RT-H3)

4 μL of 10× ligation buffer (500 mM HEPES-KOH pH 7.5, 200 mM MgCl$_2$), 4 μL of 10 mM ATP and 5.6 μL of nuclease free water were added to 20 μL of 50 μM transcribed tRNAAsn-E2GUU (-CA) (SEQ ID NO: RT-H3). The mixture was heated at 95° C. for 2 minutes and then left to stand at room temperature for 5 minutes, and the tRNA was refolded. 2.4 μL of T4 RNA ligase (New England Biolabs) and 4 μL of a 5 mM solution of aminoacylated pdCpA having a side chain amino group protected (any one of Compounds tk5, tk60, tk64, tk90, tk38 and tk11) in DMSO were added, and ligation reaction was carried out at 16° C. for 45 minutes. Aminoacylated tRNA (Compound AT-H3) was collected by phenol extraction and ethanol precipitation. Aminoacylated tRNA (Compound AT-H3) was dissolved in 1 mM sodium acetate immediately prior to addition to the translation mixture.

(SEQ ID NO: 96)

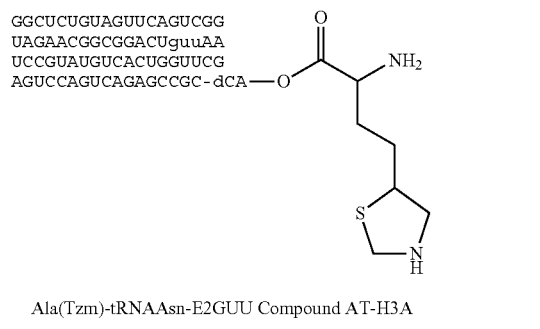

Ala(Tzm)-tRNAAsn-E2GUU Compound AT-H3A (SEQ ID NO: 96)

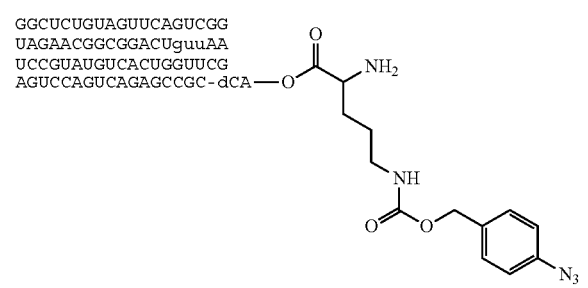

Orn(Acbz)-tRNAAsn-E2GUU Compound AT-H3B (SEQ ID NO: 96)

Orn(oAcbz)-tRNAAsn-E2GUU Compound AT-H3C (SEQ ID NO: 96)

Lys (Npys)-tRNAAsn-E2GUU Compound AT-H3D (SEQ ID NO: 96)

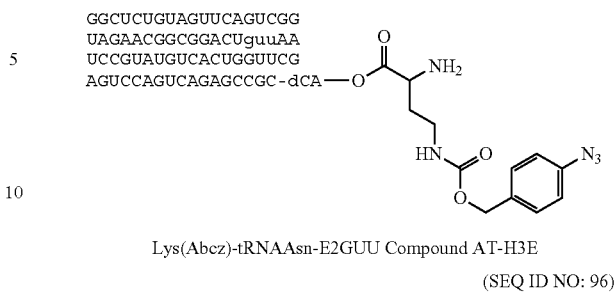

Lys(Abcz)-tRNAAsn-E2GUU Compound AT-H3E (SEQ ID NO: 96)

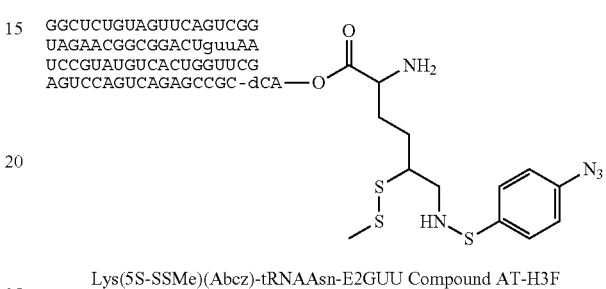

Lys(5S-SSMe)(Abcz)-tRNAAsn-E2GUU Compound AT-H3F

3-3. Translational Synthesis of Peptides Containing Protected Side Chain Amino Groups Translation synthesis of desired unnatural amino acid-containing polypeptides was carried out by adding tRNA aminoacylated by various amino acids (Compound AT-H3) to a cell-free translation system and initiating translation. The translation system used was PURE system, a prokaryote-derived reconstituted cell-free protein synthesis system. Specifically, the synthesis was carried out by adding 1 µM template RNA, 250 µM each of proteinogenic amino acids and 50 µM acylated tRNA to a transcription and translation solution (1% (v/v) RNasein Ribonuclease inhibitor (Promega, N2111), 1 mM GTP, 1 mM ATP, 20 mM creatine phosphate, 50 mM HEPES-KOH pH 7.6, 100 mM potassium acetate, 6 mM magnesium acetate, 2 mM spermidine, 0.1 mM 10-HCO—H4 folate, 1.5 mg/ml E. coli MRE600 (RNase-negative)-derived tRNA (Roche), 4 µg/mi creatine kinase, 3 µg/ml myokinase, 2 units/ml inorganic pyrophosphatase, 1.1 µg/ml nucleoside diphosphate kinase, 0.6 µM methionyl tRNA transformylase, 0.26 µM EF-G, 0.24 µM RF2, 0.17 µM RF3, 0.5 µM RRF, 2.7 µM IF1, 0.4 µM IF2, 1.5 µM IF3, 40 µM EF-Tu, 93 µM EF-Ts, 1.2 µM ribosome, 0.73 µM AlaRS, 0.03 µM ArgRS, 0.38 µM AsnRS, 0.13 µM AspRS, 0.02 µM CysRS, 0.06 µM GlnRS, 0.23 µM GluRS, 0.09 µM GlyRS, 0.4 µM IleRS, 0.04 µM LeuRS, 0.11 µM LysRS, 0.03 µM MetRS, 0.68 µM PheRS, 0.16 µM ProRS, 0.04 µM SerRS, 0.09 µM ThrRS, 0.03 µM TrpRS, 0.02 µM TyrRS, 0.02 µM ValRS (self-prepared proteins were basically prepared as His-tagged proteins)) and allowing the translation reaction mixture to stand at 37° C. for 1 hour.

3-3-1. Translation Synthesis of a Model Peptide Containing Ala(Tzm)

Figure 75:
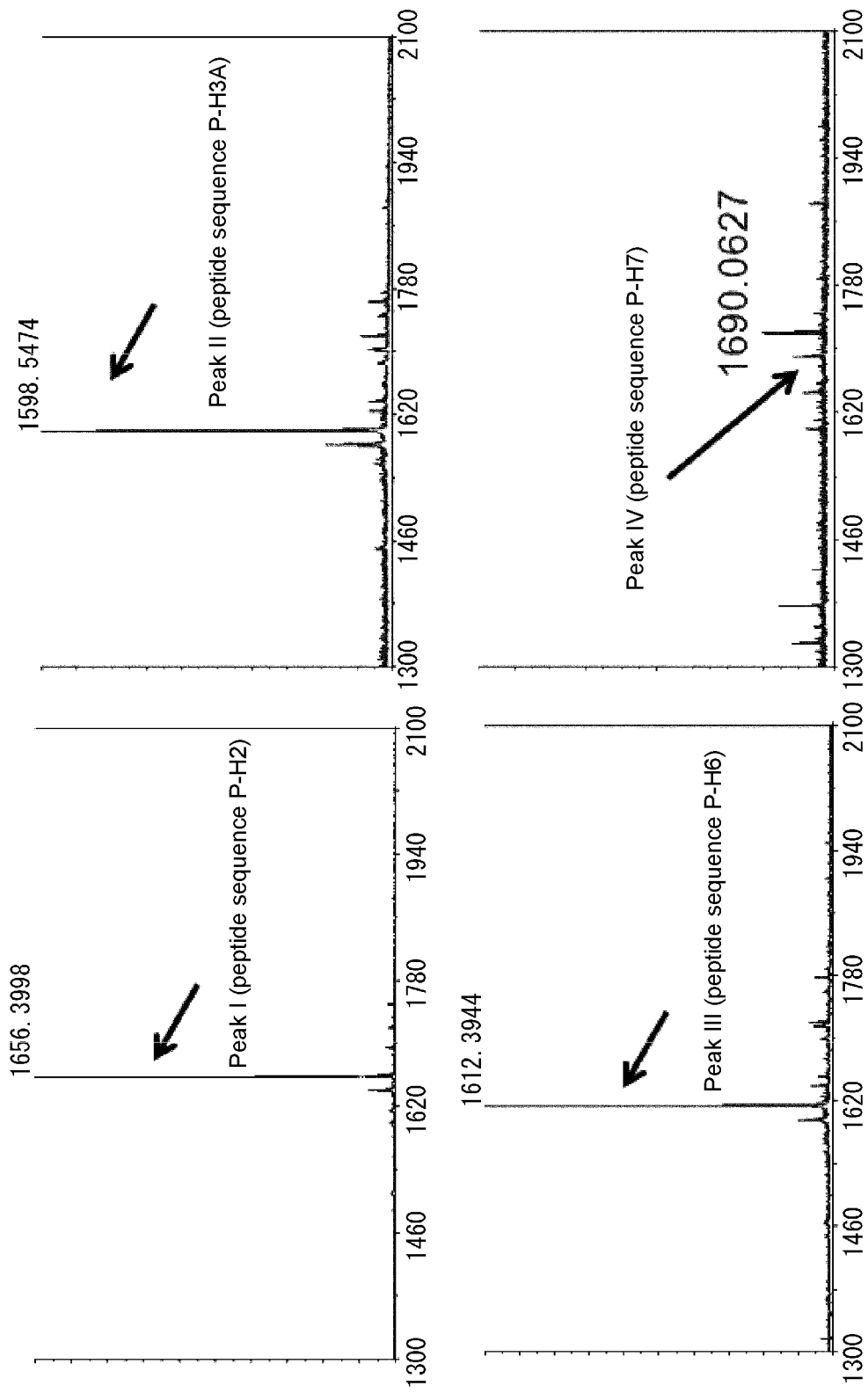
FIG. 75 is a diagram showing MALDI-MS analysis results of translation reaction products.

The aforementioned translation solution containing 1 µM Template RNA CT32 (SEQ ID NO: RM-H3), 0.25 mM Met, 0.25 mM Arg, 0.25 mM Asp, 0.25 mM Tyr, 0.25 mM Lys, 1 mM dithiothreitol and 50 µM Ala(Tzm)-tRNAAsn-E2GUU (Compound AT-H3A) was incubated at 37° C. for 60 minutes. 9 µL of 0.2% trifluoroacetic acid was added to 1 µL of the resulting translation reaction product. 1 µL of the resulting mixture was loaded on a MALDI target plate, and then blended with 1 µL of a CHCA solution (10 mg/ml α-cyano-4-hydroxycinnamic acid, 50% acetonitrile, 0.1% trifluoroacetic acid), dried on the plate. As a result of MALDI-MS analysis, a full-length peptide containing Ala (Tzm) (peptide sequence P-H2) was observed as a main product (FIG. 75, peak I).

SEQ ID NO: RM-H3
CT32 RNA sequence
(SEQ ID NO: 97)
GGGUUAACUUUAACAAGGAGAAAAACAUGCGUaacCGUGACUACAAGGAC

GACGACGACAAGUAAGCUUCG

Peptide sequence P-H2
(SEQ ID NO: 279)
fMetArg[Ala(Tzm)]ArgAspTyrLysAspAspAspAspLys MALDI-MS:
m/z: [H+M]+=1656.4 (Calc. 1656.7)

3-3-2. Translation Synthesis of Model Peptides Containing Orn(Acbz), Orn(oAcbz) and Lys(Npys)

Figure 76:
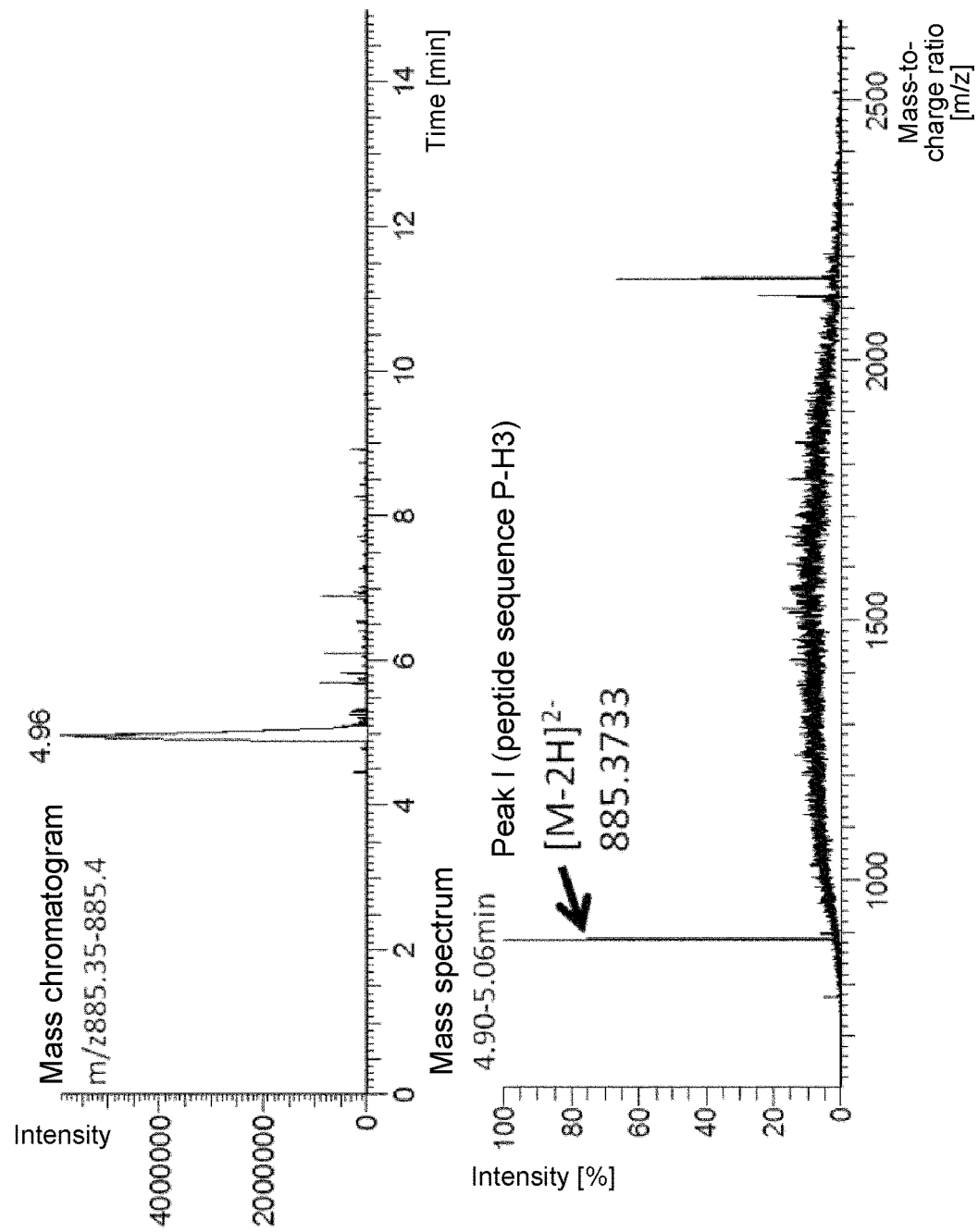
FIG. 76 is a diagram showing a mass chromatogram and mass spectrometry results of a translation reaction product.
Figure 77:
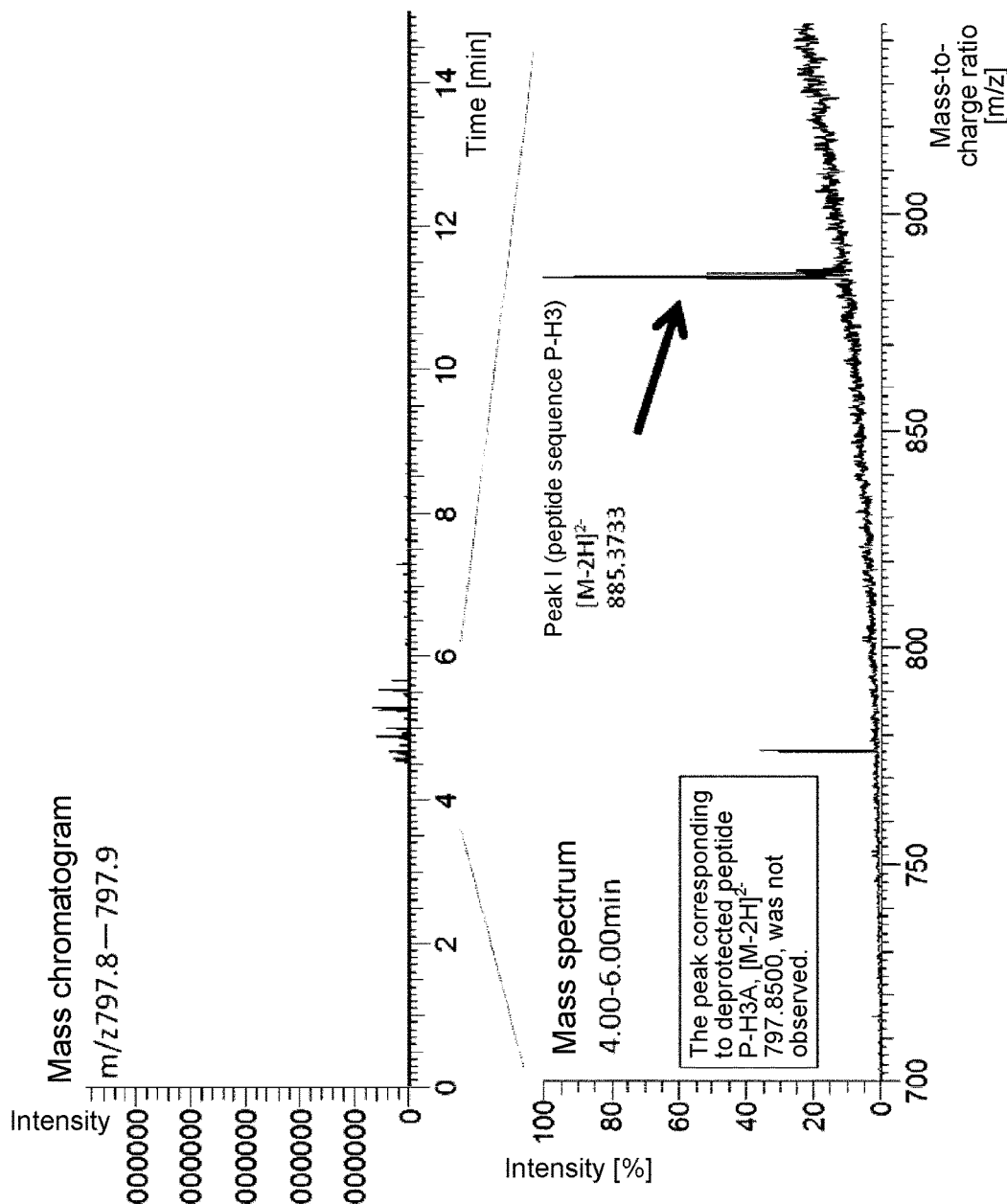
FIG. 77 is a diagram showing a mass chromatogram and mass spectrometry results of a translation reaction product.
Figure 78:
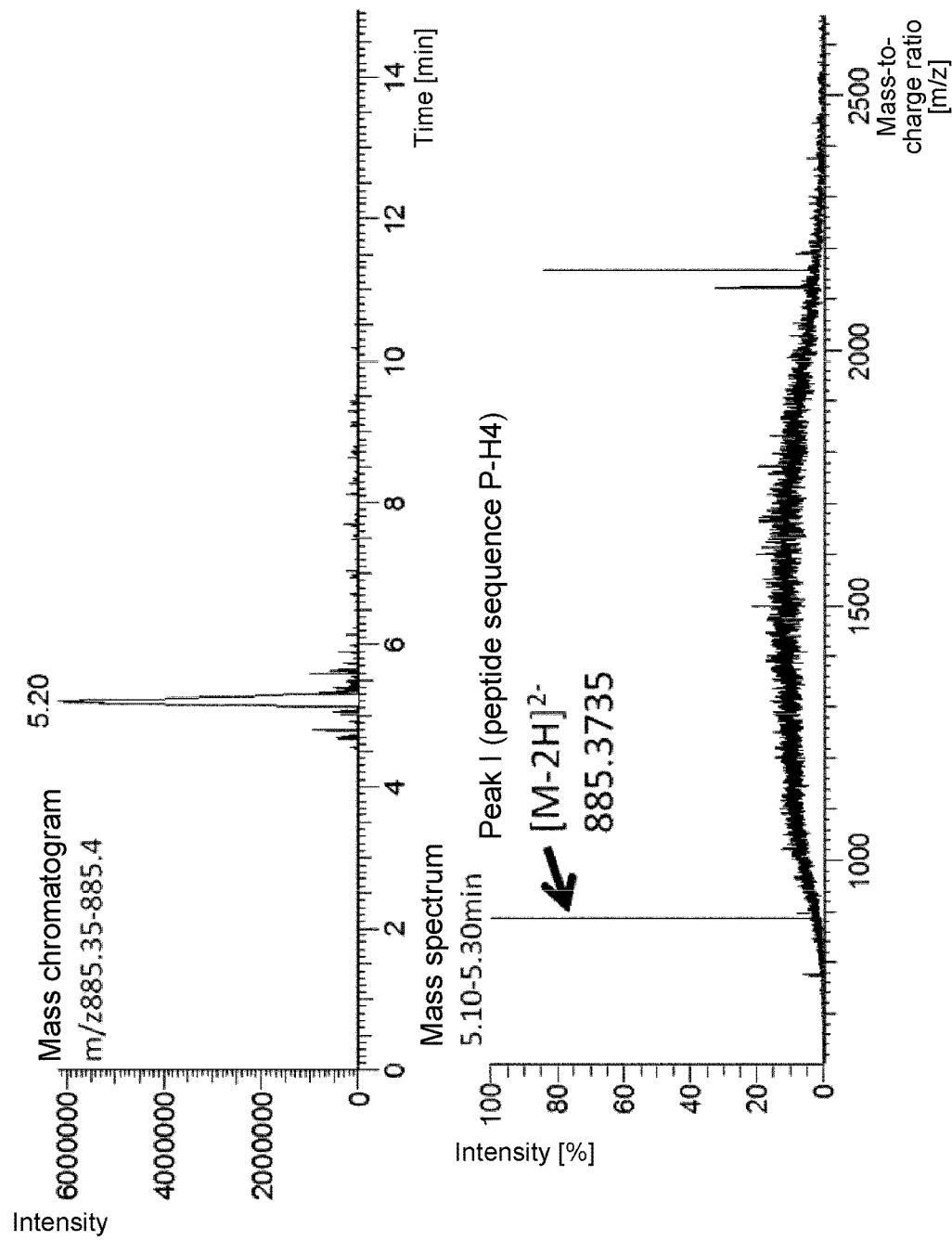
FIG. 78 is a diagram showing a mass chromatogram and mass spectrometry results of a translation reaction product.
Figure 79:
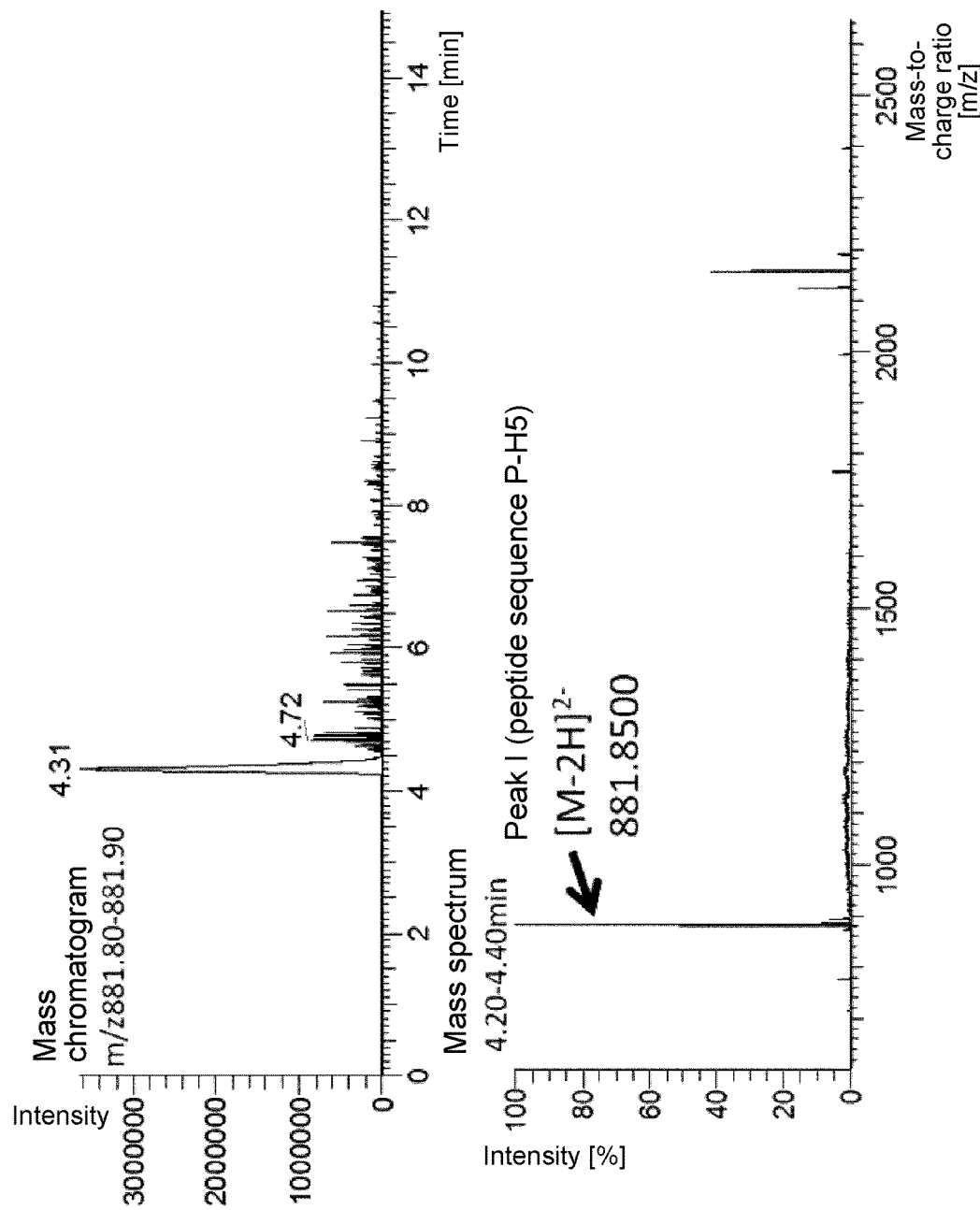
FIG. 79 is a diagram showing a mass chromatogram and mass spectrometry results of a translation reaction product.

The three aforementioned translation reaction solutions in total, each containing 1 µM template RNA CT32 (SEQ ID NO: RM-H3), 0.25 mM Met, 0.25 mM Arg, 0.25 mM Asp, 0.25 mM Tyr, 0.25 mM Lys, and either one of 50 µM Orn(Acbz)-tRNAAsn-E2GUU (Compound AT-H3B), Orn(oAcbz)-tRNAAsn-E2GUN (Compound AT-H3C) and Lys(Npys)-tRNAAsn-E2GUU (Compound AT-H3D) prepared by the above method were incubated at 37° C. for 60 minutes. For the translation sample containing Orn(Acbz)-tRNAAsn-E2GUU (Compound AT-H3B), 9 µL of 0.2% trifluoroacetic acid was added to 1 µL of the resulting translation solution, and 1 µL, of the resulting mixture was loaded on a MALDI target plate, and then blended with 1 µL of a CHCA solution (10 mg/ml α-cyano-4-hydroxycinnamic acid, 50% acetonitrile, 0.1% trifluoroacetic acid), dried on the plate and then analyzed by MALDI-MS. Consequently, a peak derived from the intended full-length peptide but a peak corresponding to peptide P-H3A having the side chain Acbz group removed was observed was observed as a main product (FIG. 75, peak II). This was considered to result from the side chain deprotection reaction by the above-described treatment before measurement or laser irradiation during measurement. Thus, the same translational product was successively analyzed by alternative measurement using LC-EST-MS. A mixture of 5 µL of the aforementioned translation solution containing Orn(Acbz)-tRNAAsn-E2GUU (Compound AT-H3B) and 5 µL of water was analyzed by LC-MS. As a result, a peak derived from the intended full-length peptide having an Acbz group (Orn (Acbz): peptide sequence P-H3) could be confirmed (FIG. 76, peak I). On the other hand, a peak derived from side chain-deprotected P-H3A was not observed. This revealed that deprotection reaction of the side chain Acbz group occurs during the treatment process before MALDI measurement or analysis as described above (FIG. 77). Similarly, the translation solutions containing Orn(oAcbz)-tRNAAsn-E2GUU (Compound AT-H3C) and Lys(Npys)-tRNAAsn-E2GUU (Compound AT-H3D) were analyzed by LC-MS. As a result, peaks corresponding to the intended Orn(oAcbz): peptide sequence P-H4 and Lys(Npys): peptide sequence P-H5 were observed (FIG. 78, peak I and FIG. 79, peak I).

Peptide sequence P-H3
(SEQ ID NO: 281)
fMetArg[Orn(Acbz)]ArgAspTyrLysAspAspAspAspLys LC-ESI-MS: m/z 885.3733 (M−2H)2−, (Calcd for $C_{72}H_{106}O_{27}N_{24}S$: 885.3695)
Retention time: 4.99 minutes (analysis condition Orbitrap HFIP-Et3N-3)

Peptide sequence P-H3A
(SEQ ID NO: 280)
fMetArgOrn ArgAspTyrLysAspAspAspAspLys

MALDI-MS:
m/z: [H+M]+=1598.5 (Calc. 1598.7)

Peptide sequence P-H4
(SEQ ID NO: 281)
fMetArg[Orn(oAcbz)] ArgAspTyrLysAspAspAspAspLys LC-ESI-MS: m/z 885.3735 (M−2H)2−, (Calcd for $C_{72}H_{106}O_{27}N_{24}S$: 885.3695)
Retention time: 5.23 min (analysis condition Orbitrap HFIP-Et3N-3)

Peptide sequence P-H5
(SEQ ID NO: 282)
fMetArg[Lys(Npys)] ArgAspTyrLysAspAspAspAspLys LC-ESI-MS: m/z 881.8500 (M−2H)2−, (Calcd for $C_{70}H_{105}O_{27}N_{23}S_2$: 881.8501)
Retention time: 4.34 minutes (analysis condition Orbitrap HFIP-Et3N-3)

3-3-3. Translation Synthesis of Model Peptides Containing Lys(Acbz) and Lys(5S-SSMe) (Acbz)

The three aforementioned translation reaction solutions in total, each containing 1 µM template RNA CT32 (SEQ ID NO: RM-H3), 0.25 mM Met, 0.25 mM Arg, 0.25 mM Asp, 0.25 mM Tyr, 0.25 mM Lys, and either one of 50 µM Lys(Acbz)-tRNAAsn-E2GUU (Compound AT-H3E) and Lys(5S-SSMe)(Acbz)-tRNAAsn-E2GUU (Compound AT-H3F) prepared by the above method were incubated at 37° C. for 60 minutes. 9 µL, of 0.2% trifluoroacetic acid was added to 1 µL of the resulting translation reaction product. 1 µL of the resulting mixture was loaded on a MALDI target plate, and then blended with 1 µL of a CHCA solution (10 mg/ml α-cyano-4-hydroxycinnamic acid, 50% acetonitrile, 0.1% trifluoroacetic acid), dried on the plate. MALDI-MS analysis resulted in observation of peptide sequences P-H6 and P-H7 derived from removal of side chain Acbz groups during MALDI measurement and during pretreatment (FIG. 75, peaks III and IV, respectively).

Peptide sequence P-H6
(SEQ ID NO: 98)
fMetArgLysArgAspTyrLysAspAspAspAspLys

MALDI-MS:

m/z: [H+M]+=1612.4 (Calc. 1612.7)

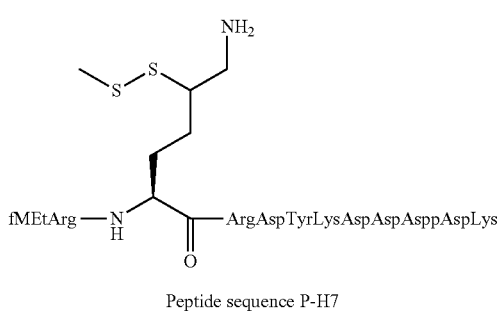

(SEQ ID NO: 283)

Peptide sequence P-H7

MALDI-MS:

m/z: [H+M]+=1690.1 (Calc. 1690.7)

3-4. Evaluation of RNA Stability Under Conditions where Side Chain Amino Groups are Deprotected In order to confirm whether or not RNA stably exists under conditions where the aforementioned protecting groups for side chain amino groups are deprotected, respectively, RNA was subjected to the respective deprotection conditions and then analyzed by gel electrophoresis.

Figure 80:
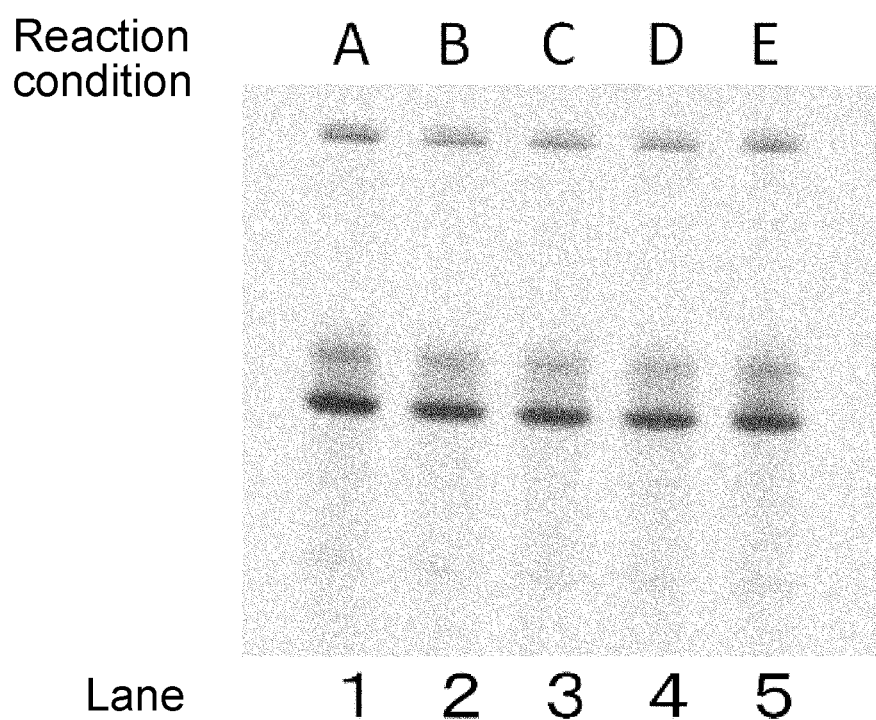
FIG. 80 is a diagram showing electrophoretic evaluation results of RNA stability under conditions where side chain amino groups are deprotected.

Each reaction solution was prepared under the reaction conditions shown in Table 19, and RNA was incubated according to the respective reaction temperature and reaction time. For each of the reaction solutions subjected to the reaction conditions B-E, RNA was then purified using RNeasy minelute (Qiagen) and eluted with 10 µL of water. 10 µL of TBE-urea sample buffer (2×) (Invitrogen) was added to 10 µL of each of these reaction solutions and the reaction solution A. 1 µL of each mixture was subjected to electrophoresis using 10% TBE-urea gel and stained with SYBR gold nucleic acid stain (Invitrogen) (FIG. 80).

As a result, no major changes in band pattern and band density were not observed between the RNA of the reaction condition A subjected to electrophoresis as a control experiment and the RNA subjected to the reaction conditions B-E (FIG. 80, lane 1 vs lanes 2-5), indicating that RNA stably exists under these reaction conditions. The conditions of B-E simulate deprotection conditions for B: 4-azidobenzyloxycarbonyl group (Acbz), C: 2-azidobenzyloxycarbonyl group (oAcbz), D: thiazolidine ring and E: 3-nitro-2-pyridinesulfenyl group (Npys), respectively.

TABLE 19

| Reaction condition | Reaction condition |
| --- | --- |
| A | 2 µM OT86b RNA (SEQ ID NO: RM-H1) (RT, 0 min, 10 µL scale) |

TABLE 19-continued

| Reaction condition | Reaction condition |
| --- | --- |
| B | 50 mM HEPES-KOH, 1 µM OT86b RNA (SEQ ID NO: RM-H1), 30% (V/V) DMA, 9.1 mM TCEP (pH 7.6, 25° C., 1 hr, 20 µL scale) |
| C | 50 mM HEPES-KOH, 1 µM OT86b RNA (SEQ ID NO: RM-H1), 15% (V/V) acetonitrile, 50 mM TCEP (pH 7.4, 37° C., 1.5 hrs, 20 µL scale) |
| D | 50 mM sodium acetate, 1 µM OT86b RNA (SEQ ID NO: RM-H1), 30% (V/V) DMA, 40 mM 2,2'-dithiodipyridine (pH 4.0, 37° C., 17 hrs, 20 µL scale) After the above reaction, 2 µL of 600 mM TCEP (pH 7.2) was added to 20 µL of the reaction solution, and the mixture was reacted at 25° C. for further one hour. |
| E | 50 mM sodium acetate, 1 µM OT86b RNA (SEQ ID NO: RM-H1), 50% (V/V) DMA, 19.5 mM 2-mercaptopyridine (pH 4.1, 25° C., 1 hr, 20 µL scale) |

Figure 83:
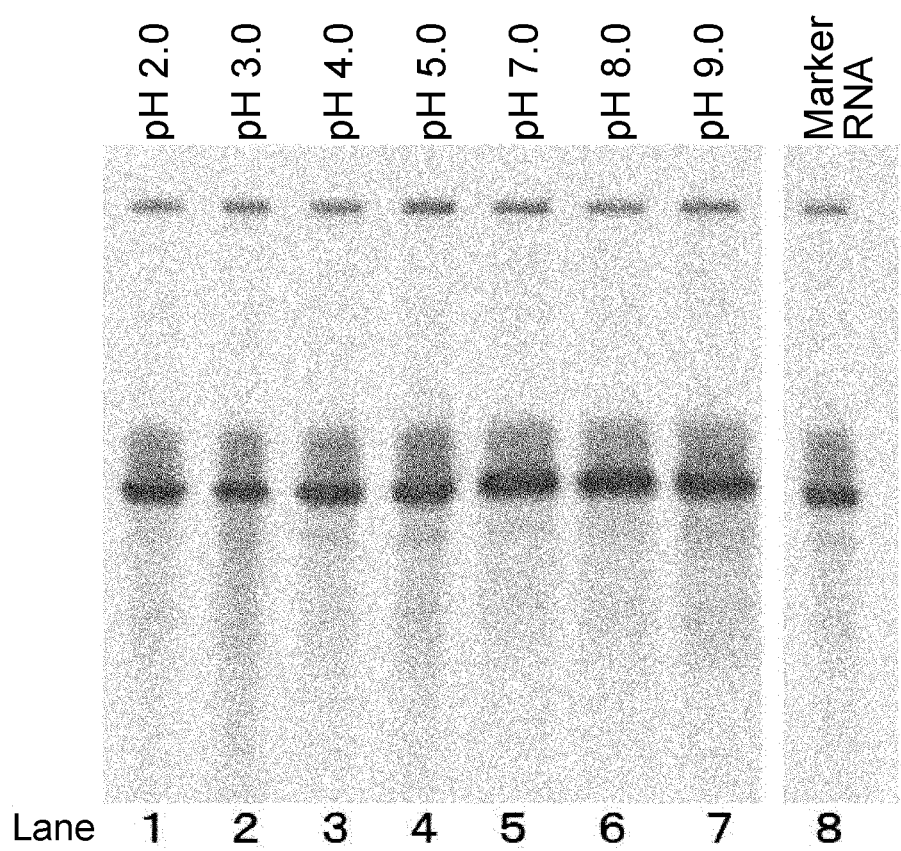
FIG. 83 is a diagram showing electrophoretic evaluation results of RNA stability under conditions where side chain amino groups are deprotected.

Subsequently, RNA stability under acidic or basic conditions was evaluated using electrophoresis. 20 µL each of 100 mM hydrochloric acid-potassium chloride buffer (pH 2.0), 100 mM sodium citrate buffer (pH 3.0), 100 mM sodium acetate buffer (pH 4.0), 100 mM sodium acetate buffer (pH 5.0), 100 mM HEPES-K buffer (pH 7.0), 100 mM Tris-hydrochloric acid buffer solution (pH 8.0) and bicine-K buffer (pH 9.0) was added to 2 µL each of RNA solutions (20 µM OT95 RNA (SEQ ID NO: RM-H4), 100 mM potassium chloride and 10 mM magnesium acetate), and each of the reaction solutions was incubated at 37° C. for 22 hours. As a control experiment, 20 µL of water was added to the above RNA solution in place of such buffers, and incubation at 37° C. was omitted to prepare a marker RNA which was used for comparison with the above reaction samples in terms of electrophoresis. Equal amounts of TEE-urea sample buffer (2×) (Invitrogen) were added to 22 µL each of the resulting reaction solutions and the marker RNA. 4 µL of each mixture was subjected to electrophoresis using 10% TBE-urea gel and stained with SYBR gold nucleic acid stain (invitrogen). As a result, no significant RNA decomposition was observed in any of the reaction samples as compared with the marker RNA (FIG. 83). This indicated that RNA stably exists under the above reaction conditions.

```
SEQ ID NO: RM-H4
OT95 RNA sequence
                                        (SEQ ID NO: 185)
GGGUUAACUUUAAGAAGGAGAUAUACAUAUGUGCACUACAACGCGUCUU

CCGUACCGUAGCGGCUCUGGCUCUGGCUCUUAGGGCGGCGGGGACAAA
```

[Example 22] Heck Reaction Using RNA-Peptide Complex Model Compounds

Compounds actually synthesized by forming display libraries are mRNA-peptide fusions having an mRNA length of about 100, and it is difficult to analyze reactions of such polymer compounds in detail. Thus, cyclization reaction conditions for mRNA-peptide fusions were specified using model compounds having an RNA structure with a length enabling molecular weight analysis in the molecule and also having a peptide structure that can undergo cyclization reaction using a metal catalyst in the molecule.

In order to apply posttranslational modification using Pd to a display library, it is necessary to allow a desired chemical modification reaction to proceed without affecting RNA. The following experiments were carried out to achieve the object. (1) Heck reaction was carried out in a system where tRNA and others exist together (PureSystem) to find reaction conditions where Heck reaction proceeds without affecting tRNA. (2) Peptide-RNA conjugates were made and then subjected to Heck reaction to find reaction conditions where Heck reaction proceeds without affecting tRNA even if peptides bind to RNAs.

The following three compounds were used as model compounds.

4-mer RNA-peptide conjugate
10-mer RNA-peptide conjugate
20-mer RNA-peptide conjugate 1-1. Synthesis of RNA-Peptide Conjugate Model Reaction Starting Materials Starting materials for carrying out model reaction were synthesized according to the following preparation method-1.

Figure 104:
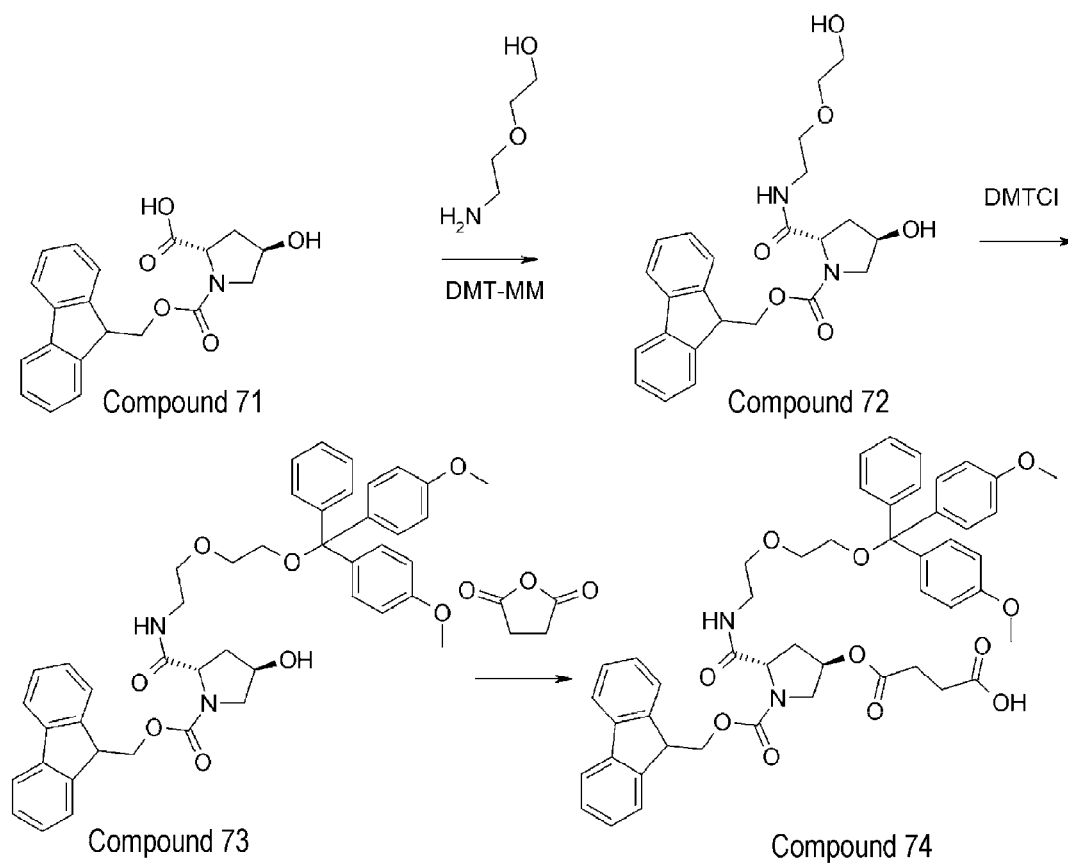
FIG. 104 is a diagram showing the synthesis of RNA-peptide conjugate model reaction starting materials (Template synthesis).
Figure 105:
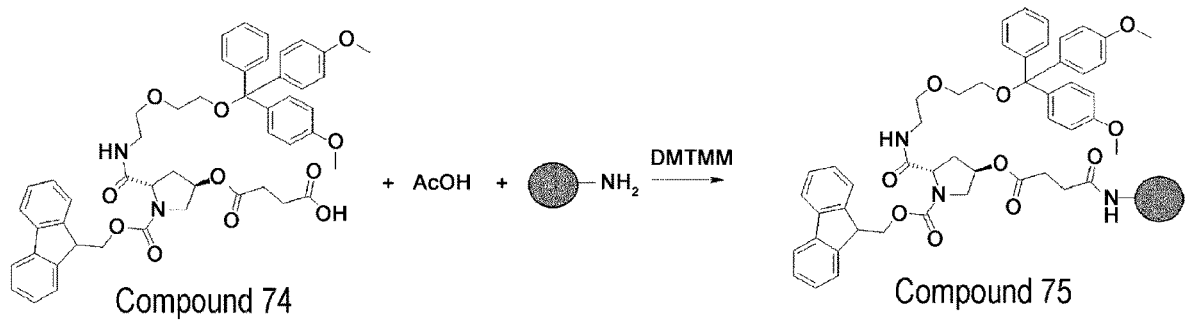
Figure 107:
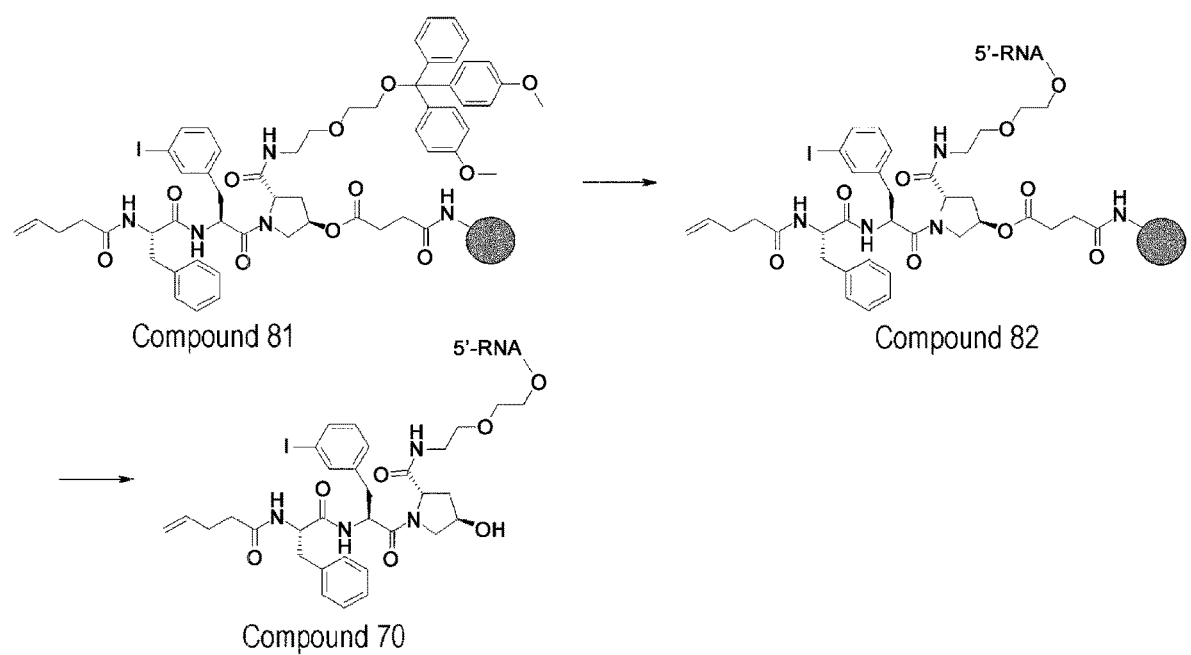

(General Preparation Method-1) Synthesis of RNA-Peptide Conjugates
Template Synthesis
See FIG. 104.
Solid Supporting
See FIG. 105.
Peptide Elongation
See FIG. 106.
RNA Synthesis and Cleavage
See FIG. 107.

1-1-1. Synthesis of 4-mer RNA-Peptide Conjugate (5'-AGCU-3'-Peptide) (Compound 70a)

Synthesis of (2S,4R)-4-hydroxy-2-[2-(2-hydroxy-ethoxy)-ethylcarbamoyl]-pyrrolidine-1-carboxylic Acid 9H-fluoren-9-ylmethyl Ester (Compound 72)

Figure 108:
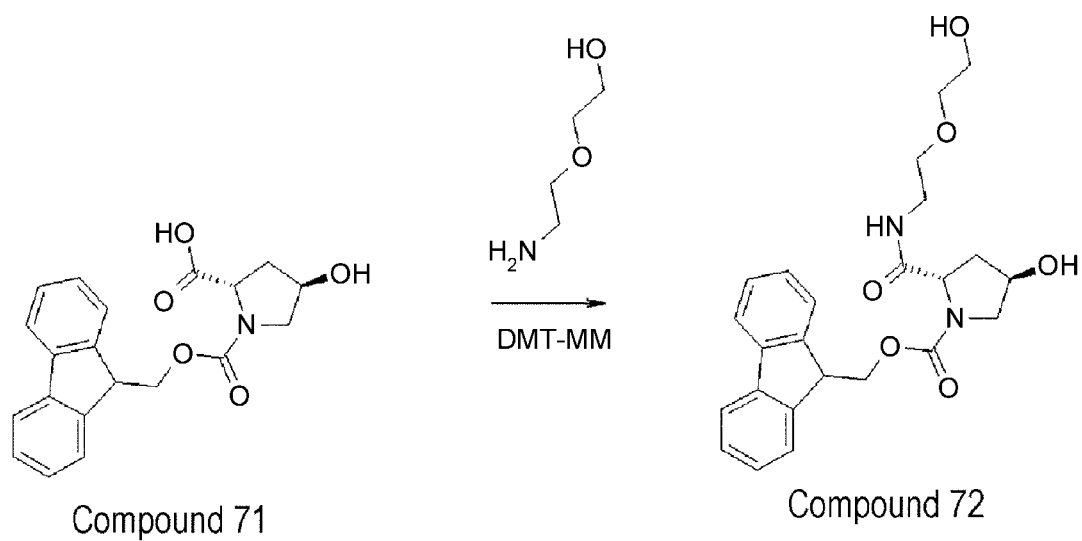

See FIG. 108.

FMOC-L-hydroxyproline (Compound 71) (2.12 g, 6.00 mmol) and 2-(2-aminoethoxy)ethanol (0.661 mg, 6.60 mmol) were dissolved in DMSO (4.0 mL), 4-(4,6-dimethoxy-1,3,5-triazin-2-yl)-4-methylmorpholinium chloride n-hydrate (1.98 g, 6.60 mmol) was added at room temperature, and the mixture was stirred for 5 hours. The reaction solution was purified by reverse-phase silica (0.1% formic acid, H2O, CH3CN, gradient) to afford the title compound (Compound 72) (1.69 g, 64%) as a pale yellow amorphous.

LCMS (ESI) 441.2 (M+H)+
Retention time: 1.57 min (analysis condition ZQAA05)

Synthesis of (2S,4R)-2-(2-(2-[bis-(4-methoxy-phenyl)-phenyl-methoxy]-ethoxyl-ethylcarbamoyl)-4-hydroxy-pyrrolidine-1-carboxylic Acid 9H-fluoren-9-ylmethyl Ester (Compound 73)

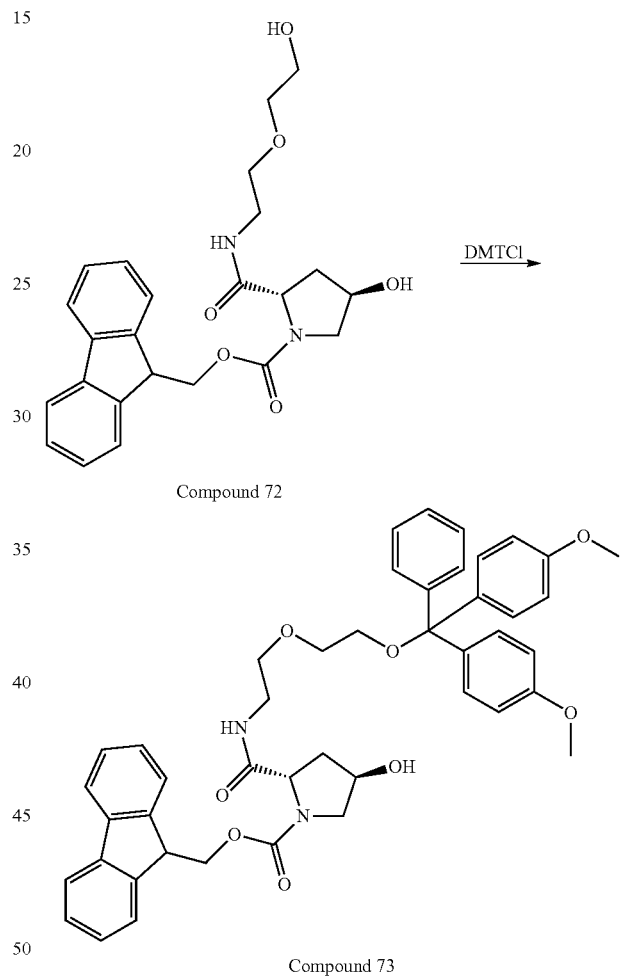

Compound 72

Compound 73

(2S,4R)-4-hydroxy-2-[2-(2-hydroxy-ethoxy)-ethylcarbamoyl]-pyrrolidine-1-carboxylic acid 9H-fluoren-9-ylmethyl ester (Compound 72) (1.69 g, 3.83 mmol) and 4,4'-dimethoxytrityl chloride (2.47 g, 7.66 mmol) were dissolved in pyridine (5.0 mL), and the mixture was stirred at room temperature for 3 hours. The reaction solution was purified by reverse-phase silica (0.1% ammonium acetate, H2O, CH$_3$OH, gradient) to afford the title compound (Compound 73) (2.24 g, 79%) as a pale yellow amorphous.

LCMS (ESI) 760.8 (M+NH4)+, 765.7 (M+Na)+
Retention time: 1.15 min (analysis condition SQDAA05)

Synthesis of Succinic Acid mono-[(3R,5S)-5-(2-{2-[bis-(4-methoxy-phenyl)-phenyl-methoxy]-ethoxy}-ethylcarbamoyl)-1-(9H-fluoren-9-ylmethoxycarbonyl)-pyrrolidin-3-yl] Ester (Compound 74)

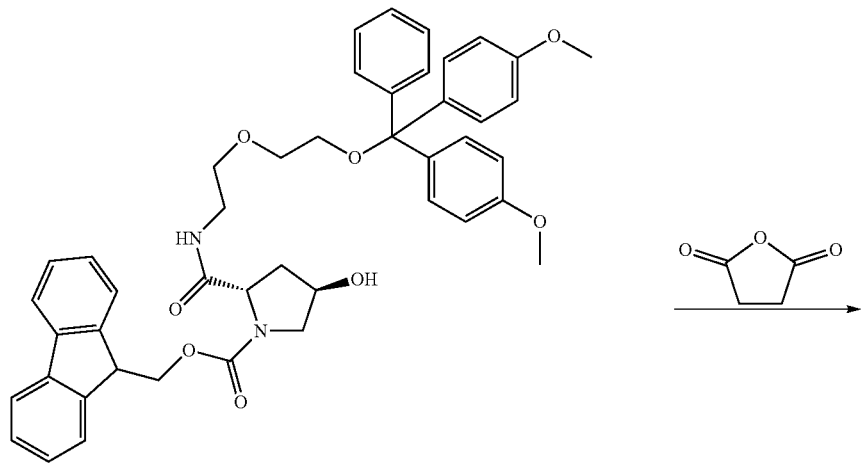

Compound 73

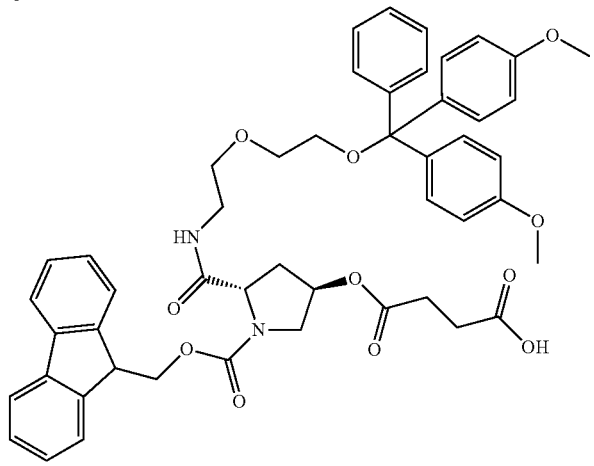

Compound 74

(2S,4R)-2-(2-(2-[Bis-(4-methoxy-phenyl)-phenyl-methoxy]-ethoxyl-ethylcarbamoyl)-4-hydroxy-pyrrolidine-1-carboxylic acid 9H-fluoren-9-ylmethyl ester (Compound 73) (1.00 g, 1.35 mmol), succinic anhydride (192 mg, 2.02 mmol) and N,N-dimethylaminopyridine (246 mg, 2.02 mmol) were dissolved in acetonitrile (3.0 mL), and the mixture was stirred at room temperature for 2.5 hours. The reaction solution was purified by reverse-phase silica (0.1% ammonium acetate, H2O, CH3OH, gradient) to afford the title compound (Compound 74) (349 mg, 31%) as a colorless amorphous.

LCMS (ESI) 860.5 (M+NH$_4$)+, 865.5 (M+Na)+
Retention time: 1.11 min (analysis condition SQDAA05)

Synthesis of a Solid-Supported FMOC-Deprotected Pyrrolidine Derivative (Compound 76)

Figure 109:
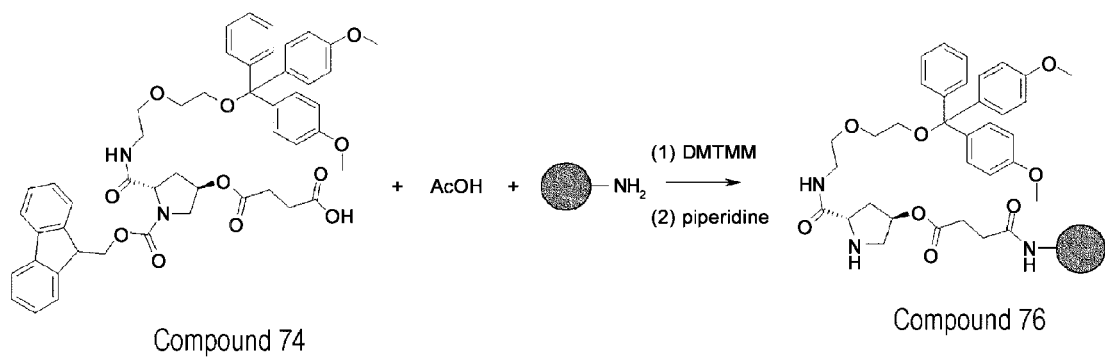

See FIG. 109.

Acetonitrile (5.0 mL) was added to succinic acid mono-[(3R,5S)-5-(2-(2-[bis-(4-methoxy-phenyl)-phenyl-methoxy]-ethoxyl-ethylcarbamoyl)-1-(9H-fluoren-9-yl-methoxycarbonyl)-pyrrolidin-3-yl]ester (Compound 74) (85.1 mg, 0.101 mmol) and Custom Primer Support 200 Amino (GE Healthcare, 1.01 g). After adding a solution of acetic acid (5.8 µL, 0.101 mmol) in acetonitrile (0.1 mL) thereto, 4-(4,6-dimethoxy-1,3,5-triazin-2-yl)-4-methylmorpholinium chloride n-hydrate (60.6 mg, 0.202 mmol) was added at room temperature, and the mixture was stirred at room temperature for 1.5 hours. 4-(4,6-Dimethoxy-1,3,5-triazin-2-yl)-4-methylmorpholinium chloride n-hydrate (300 mg, 1.01 mmol) was then added to the reaction solution, and the mixture was stirred for 15 minutes, after which a solution of acetic acid (58 µL, 1.01 mmol) in acetonitrile (0.5 mL) was added and the mixture was stirred for 1 hour. The reaction product was collected by filtration, and the resulting solid (Compound 75) was dried. A 20% solution of piperidine in DMF (10 mL) was added to the obtained solid, and the mixture was reacted for 1 hour. The reaction product was collected by filtration, washed with DMF and acetonitrile and dried under reduced pressure to afford a solid-supported FMOC-deprotected pyrrolidine derivative (Compound 76) (1.05 g).

Synthesis of a Solid-Supported Iodophenylalanine Derivative (Compound 78)

Figure 110:
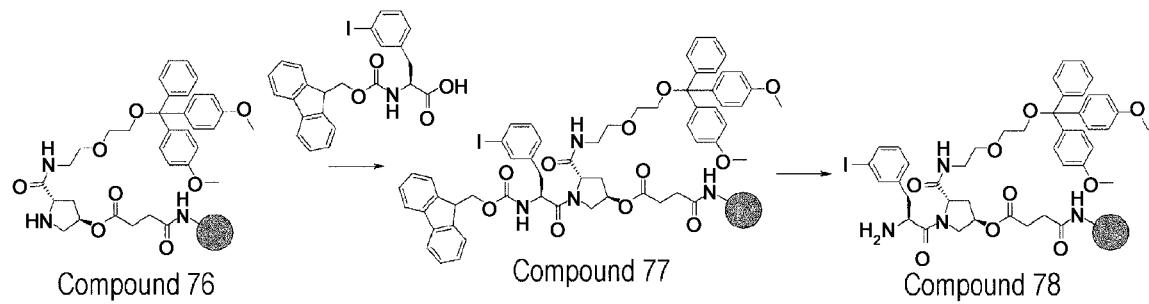

See FIG. 110.

Fmoc-3-iodo-L-phenylalanine (622 mg, 1.21), HOAt (136 mg, 0.909) and N,N'-diisopropylcarbodiimide (0.206 mL, 1.33) were dissolved in DMF (5.0 mL), followed by addition of a solid-supported FMOC-deprotected pyrrolidine derivative compound 76 (1.05 g). The mixture was stirred at room temperature for 3 hours. The resulting solid support was collected by filtration and washed with DMF (10 mL) three times, a 20% solution of piperidine in DMF (10 mL) was then added and the mixture was stirred at room temperature for 1 hour. The resulting solid support was washed with DMF (10 mL) three times and with acetonitrile (10 mL) three times and dried under reduced pressure to afford a solid-supported iodophenylalanine derivative compound 78 to which 3-iodo-L-phenylalanine binds (1.00 g).

Synthesis of a Solid-Supported Phenylalanine Derivative (Compound 80)

Figure 111:
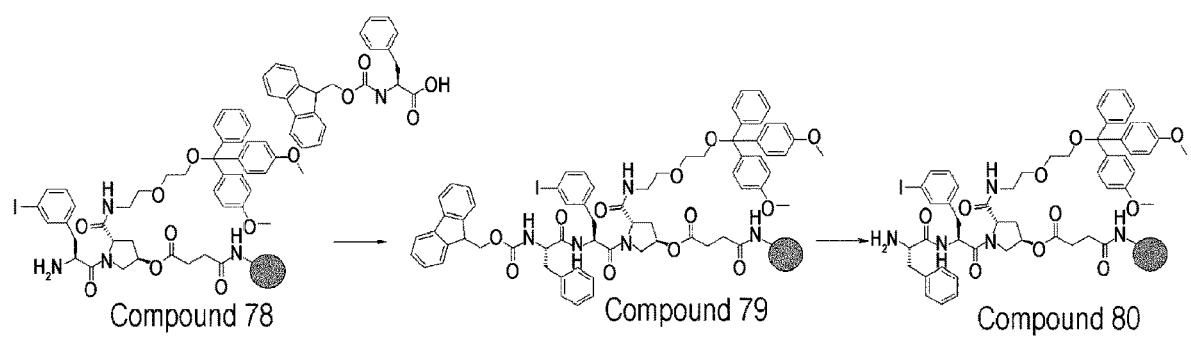

See FIG. 111.

A solid-supported phenylalanine derivative to which L-phenylalanine binds (Compound 80) (1.00 g) was obtained by the same method as the method of providing Compound 78 by condensation with a solid-supported iodophenylalanine derivative (Compound 78) (1.00 g) and Fmoc-L-phenylalanine (234 mg, 0.606) and subsequent Fmoc deprotection.

Synthesis of a Solid-Supported 4-Pentenoic Acid Derivative (Compound 81)

Figure 112:
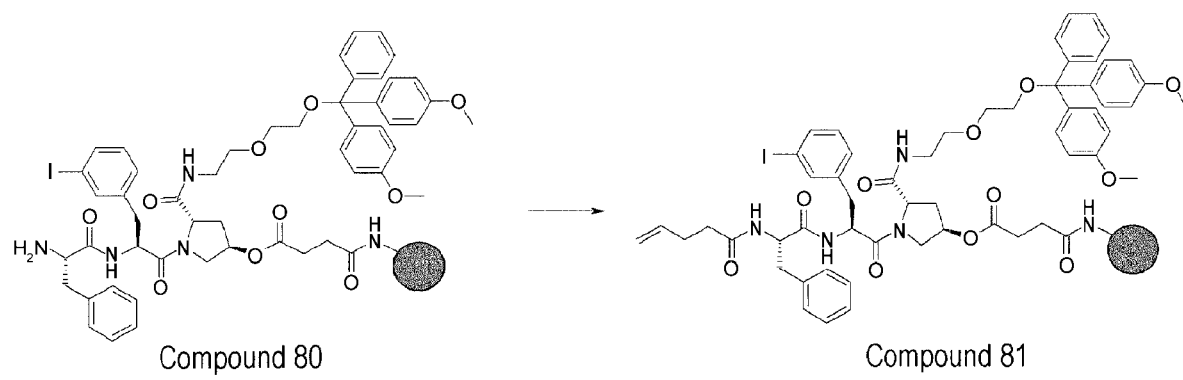

See FIG. 112.

A solid-supported 4-pentenoic acid derivative to which 4-pentenoic acid binds (Compound 81) (249 mg) was obtained by the same method as the method of providing Compound 78 by condensation of a solid-supported phenylalanine derivative to which L-phenylalanine binds (Compound 80) (250 mg) and 4-pentenoic acid (30.6 µL, 0.300 mm).

Synthesis of Compound 70a

Figure 113:
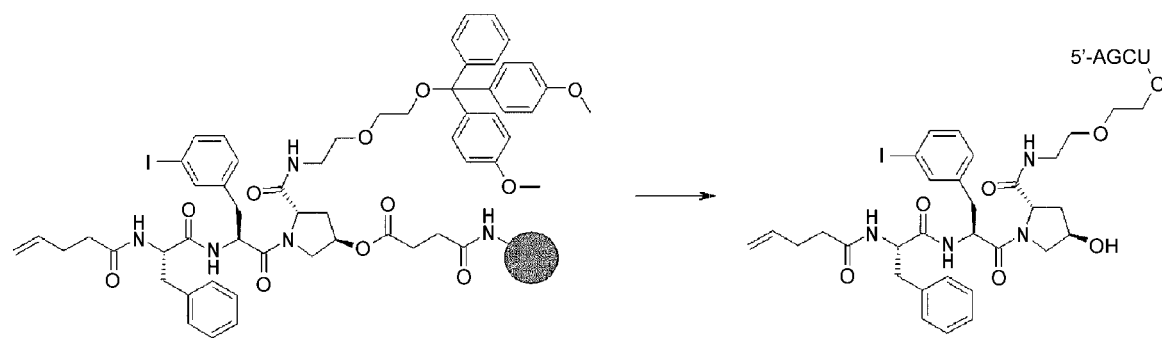

See FIG. 113.

RNA binding elongation was carried out with a DNA synthesizer using a solid-supported 4-pentenoic acid derivative (Compound 81) (8.0 mg, 0.8 µmol). Elongation reaction of A, G, C and U was carried out using A-TOM-CE phosphoramidite, G-TOM-CE phosphoramidite, C-TOM-CE phosphoramidite and U-TOM-CE phosphoramidite manufactured by Glen Research as amidite reagents and using 5-benzylthio-1H-tetrazole as a condensation activator. Following condensation, the solid support was dried, after which ethanol (0.10 mL) and a 40% aqueous methylamine solution (0.10 mL) were added and the mixture was stirred at 65° C. for 15 minutes. The solvent was evaporated under reduced pressure, tetramethylammonium fluoride hydrate (10 mg) and DMSO (0.10 mL) were added and the mixture was stirred at 65° C. for 15 minutes. A 0.1 M aqueous ammonium acetate solution was added to the reaction solution, and the mixture was purified in a reverse-phase column. Following concentration, the resulting compound was dissolved in purified water (0.50 mL) to afford an aqueous solution of 4-mer RNA-peptide conjugate (Compound 70a) (5'-AGCU-3'-Peptide). The concentration and the yield of the solution measured by an ultraviolet spectrometer were 0.736 mM and 46%, respectively.

LCMS (ESI) 668.0 (M−3H)3−, 1002.4 (M−2H)2−

Retention time: 5.15 min (analysis condition ZQHFIP-Et3N)

1-1-2. Synthesis of 10-mer RNA-Peptide Conjugate (5'-AGCUUAGUCA-3' (SEQ ID NO: 69)-Peptide) (Compound 70b)

Figure 114:
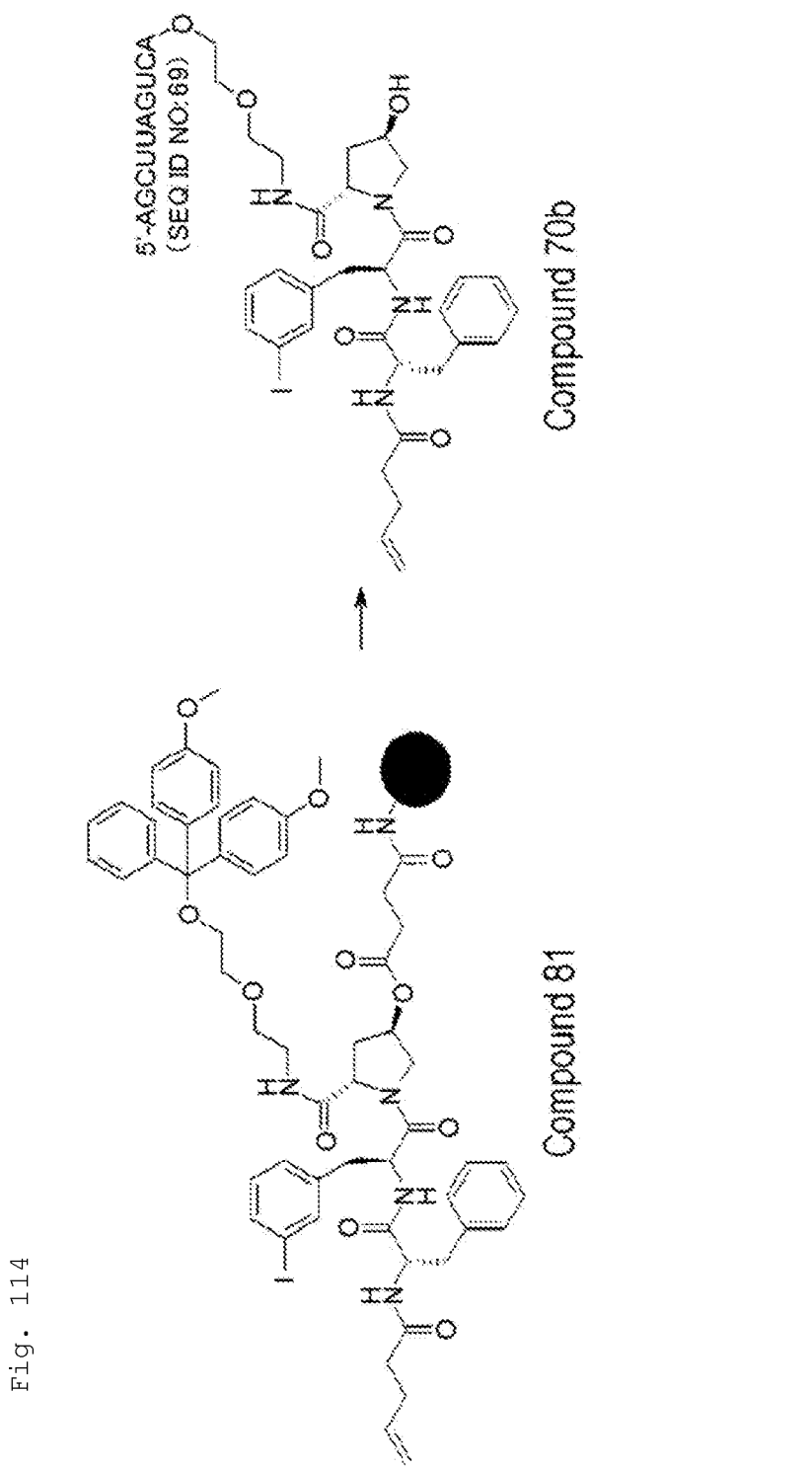

See FIG. 114.

An aqueous solution of the title compound (Compound 70b) was obtained by the same method as the method of providing Compound 70a. 0.50 mL of an aqueous solution having a concentration of 0.33 mM was obtained. The yield was 21%.

LCMS (ESI) 784.8 (M−5H)5−, 981.2 (M−4H)4−, 1308.5 (M−3H)3−

Retention time: 4.87 min (analysis condition ZQHFIP-Et3N)

1-1-3. Synthesis of 20-mer RNA-Peptide Conjugate (5'-AGCUUAGUCACCGUCAGUCA-3' (SEQ ID NO: 70)-Peptide) (Compound 70c)

Figure 115:
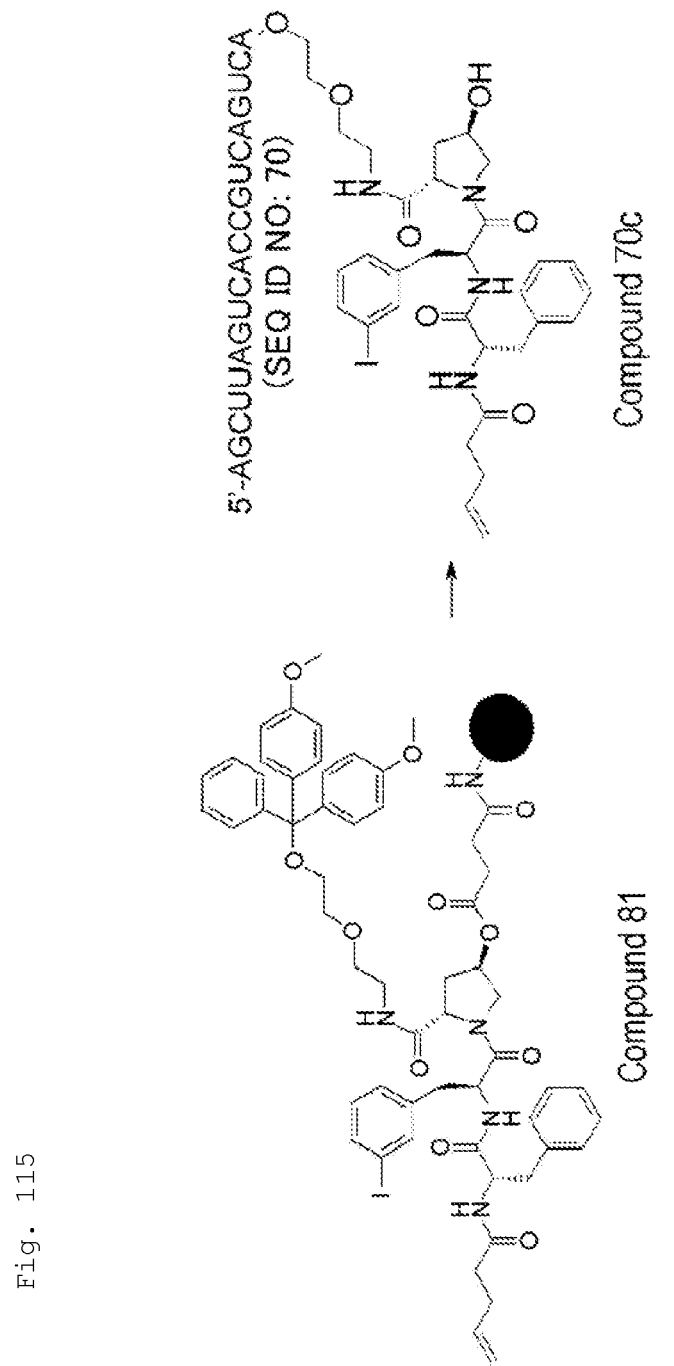

See FIG. 115.

An aqueous solution of the title compound (Compound 70c) was obtained by the same method as the method of providing Compound 70a. 0.30 mL of an aqueous solution having a concentration of 0.147 mM was obtained. The yield was 15%.

LCMS (ESI) 887.9 (M−8H)8−, 1015.0 (M−7H)7−, 1184.3 (M−6H)6−, 1421.0 (M−5H)5−, 1776.6 (M−4H)4−

Retention time: 4.60 min (analysis condition ZQHFIP-Et3N)

2-1. Cyclization Reaction of RNA-Peptide Conjugates

2-1-1. Synthesis of Heck Cyclization Reaction Product (Compound 83b) of 10-mer RNA-Peptide Conjugate (Compound 70b)

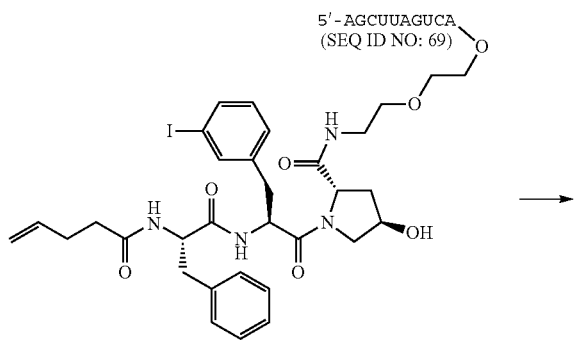

2529
-continued

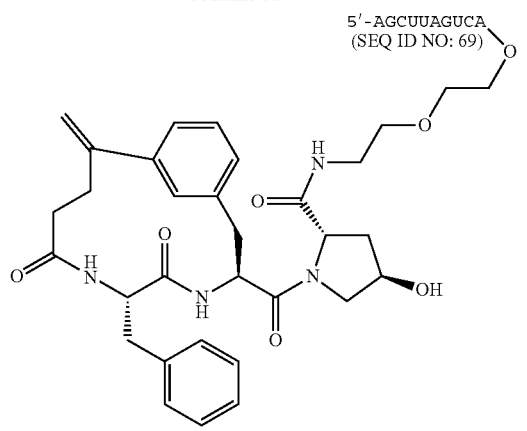
5'-AGCUUAGUCA (SEQ ID NO: 69)

10-mer RNA-peptide conjugate (Compound 70b) (0.33 mM aqueous solution, 3.7 µL, 1.2 nmol), internal standard (10 mM p-n-propylbenzoic acid-DMF solution, 3 µL, 30 nmol), phosphate buffer (10 µL of a solution of K2HPO4 (1.0 mmol) and K3PO4 (0.10 mmol) in 10 mL of water), and 5% aqueous PTS (polyoxyethanyl-α-tocopheryl sebacate) (30 µL) were mixed, and the mixture was analyzed by reverse-phase LC, followed by addition of a Pd solution (8.0 µL) obtained by dissolving PdCl2(MeCN)2 (1.0 mg, 3.9 µmol) and 2,2'-bis(diphenylphosphino)-1,1'-biphenyl (6.2 mg, 12.0 µmol) in N-methylpyrrolidinone (0.2 mL) under a nitrogen atmosphere. The mixture was stirred at 50° C. for 3 hours under a nitrogen atmosphere. A 1 M aqueous dithiothreitol solution (10.0 µL) was added to the reaction solution (5.0 µL) to prepare an LC analysis sample, and the sample was analyzed. The yield of the product (Compound 83b) was 57% based on the comparison with the LC analysis result before the reaction.

LCMS (ESI) 759.4 (M−5H)5−, 949.5 (M−4H)4−, 1265.9 (M−3H) 3−

Retention time: 3.40 min (analysis condition ZQHFIP-Me2NEt)

2-1-2. Synthesis of Heck Cyclization Reaction Product (Compound 83c) of 20-Mer RNA-Peptide Conjugate (Compound 70c)

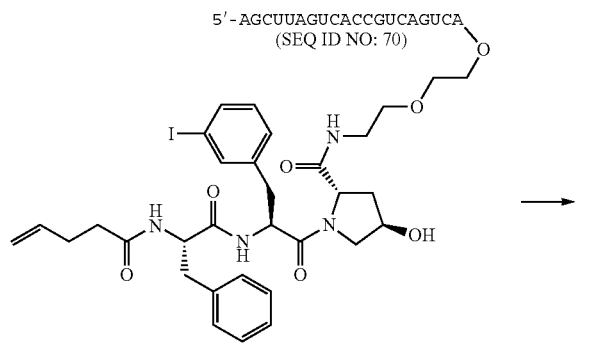
5'-AGCUUAGUCACCGUCAGUCA (SEQ ID NO: 70)

2530
-continued

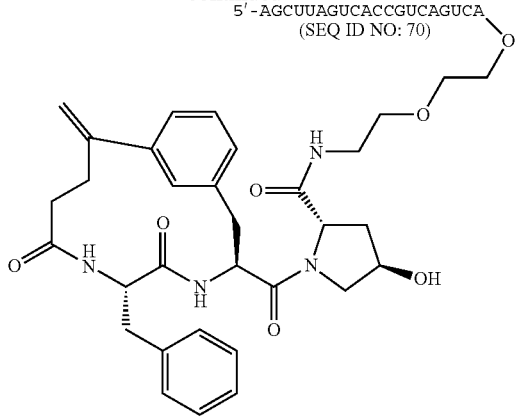
5'-AGCUUAGUCACCGUCAGUCA (SEQ ID NO: 70)

20-mer RNA-peptide conjugate (Compound 70c) (0.15 mM aqueous solution, 2.0 µL, 0.29 nmol), internal standard (10 mM p-n-butylbenzoic acid-DMF solution, 2 µL, 20 nmol), 100 mM aqueous triethylamine (5 µL, 500 mmol) and 5% aqueous PTS (polyoxyethanyl-α-tocopheryl sebacate) (30 µL) were mixed, and the mixture was analyzed by reverse-phase LC, followed by addition of a Pd solution (8.0 µL) obtained by dissolving PdCl2(MeCN)2 (0.5 mg, 1.9 µmol) and 2,2'-bis(diphenylphosphino)-1,1'-biphenyl (3.1 mg, 6.0 µmol) in N-methylpyrrolidinone (0.4 mL) under a nitrogen atmosphere. The mixture was stirred at 50° C. for 2 hours under a nitrogen atmosphere. A 0.1 M aqueous dithiothreitol solution (10.0 µL) was added to the reaction solution (5.0 µL) to prepare an LC analysis sample, and the sample was analyzed. The yield of the product (Compound 83c) was 61% based on the comparison with the LC analysis result before the reaction.

LCMS (ESI) 997.0 (M−7H)7−, 1163.0 (M−6H)6−, 1395.5 (M−5H)5−, 1745.0 (M−4H)4−

Retention time: 4.08 min (analysis condition ZQHFIP-Et3N)

[Example 23] Heck Reaction of Translated Peptides

1. Synthesis of C—C Bond Units to be Used for Translational Synthesis

1-1. Synthesis of Aminoacylated pdCpA Compound 85

1-1-1. Synthesis of Cyanomethyl but-3-enoate (Compound 86)

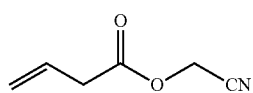

But-3-enoic acid (0.500 g, 5.81 mmol) was dissolved in acetonitrile (20 ml), and 2-bromoacetonitrile (3.33 g, 27.76 mmol) and triethylamine (1.40 g, 13.86 mmol) were slowly added at room temperature. After stirring at room temperature for 30 minutes, the reaction solution was concentrated under reduced pressure, and the resulting residue was purified by column chromatography (petroleum ether:ethyl acetate=20:1) to afford the title compound 86 (0.550 g, 75%).

¹H-NMR (Bruker, avance III, 400 MHz, CDCl₃) δ ppm 5.92 (1H, m), 5.22-5.26 (2H, m), 4.75 (2H, s), 3.21 (2H, m)

1-1-2. Synthesis of (2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl but-3-enoate (Compound 85)

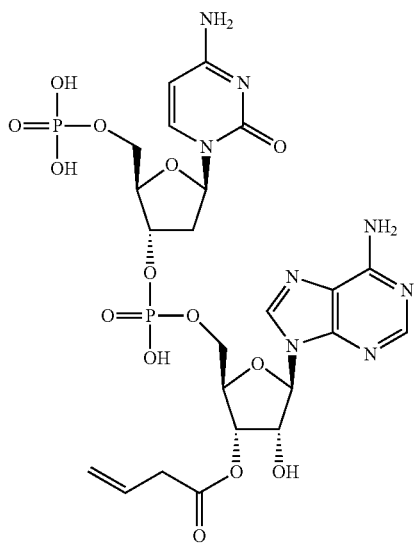 [SMILES: C=CCC(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

Cyanomethyl but-3-enoate (Compound 86) (0.050 g, 0.400 mmol) was added to a solution of ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate tetrabutylammonium salt (Compound 1h) (0.20 g, 0.150 mmol) in DMF (1.0 ml), and the mixture was stirred at room temperature for 1 hour. A 0.05% aqueous TFA solution was added to the reaction solution, the mixture was lyophilized, and the resulting residue was purified by preparative HPLC (0.05% aqueous TFA solution:acetonitrile) to prepare the title compound 85 (0.010 g, 10%).

LCMS: m/z 705 (M+H)+

Retention time: 0.461 min, 0.488 min (analysis condition SMD method 1)

1-2. Synthesis of Aminoacylated pdCpA Compound 87

1-2-1. Synthesis of Cyanomethyl pent-4-enoate (Compound 88)

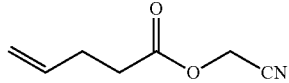

The title compound 88 (0.52 g, 75%) was obtained by the same method as in the synthesis of Compound 86 using pent-4-enoic acid (0.500 g, 4.99 mmol) in place of but-3-enoic acid as a starting material.

¹H-NMR (Broker, avance II, 300 MHz, CDCl₃) δ ppm 5.82 (1H, m), 5.04-5.32 (2H, m), 4.74 (2H, s), 2.39-2.57 (4H, m)

1-2-2. Synthesis of (2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl pent-4-enoate (Compound 87, pdCpA-PenteA)

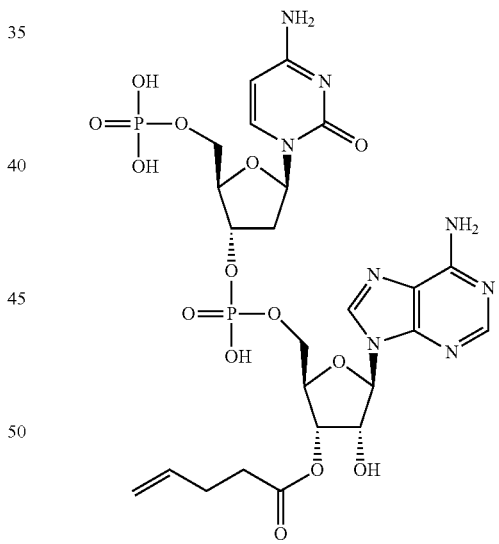

The title compound Si (0.010 g, 12%) was obtained by the same method as the method of providing Compound 85 using cyanomethyl pent-4-enoate (Compound 88) (0.066 g, 0.480 mmol) in place of cyanomethyl but-3-enoate as a starting material.

LCMS: m/z 719 (M+H)+

Retention time: 0.506 min, 0.523 min (analysis condition SMD method 1)

1-3. Synthesis of Aminoacylated pdCpA Compound 89

1-3-1. Synthesis of (2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-(allyloxy)acetate (Compound 89)

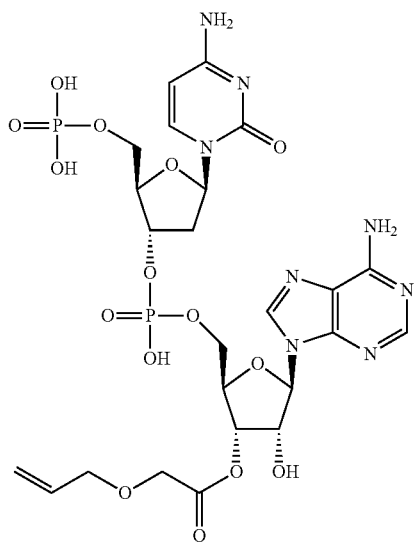 [SMILES: C=CCOCC(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

2-(Allyloxy)acetic acid (0.500 g, 4.31 mmol) was dissolved in dichloromethane (20 ml), and 2-bromoacetonitrile (2.06 g, 17.18 mmol) and triethylamine (0.87 g, 8.61 mmol) were slowly added at room temperature. After stirring at room temperature for 3 hours, the reaction solution was concentrated under reduced pressure, and the resulting residue was purified by column chromatography (petroleum ether:ethyl acetate=20:1) to afford cyanomethyl 2-(allyloxy)acetate (0.40 g, 60%).

((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (100 mg, 0.157 mmol) was added to a buffer (100 ml) in which imidazole (1.0 g, 15.7 mmol) and N,N,N-trimethylhexadecan-1-aminium chloride (1.0 g, 3.14 mmol) were dissolved and which was adjusted to pH 8 with acetic acid. A solution of cyanomethyl 2-(allyloxy)acetate obtained by the above method (93 mg, 0.628 mmol) in THF (3.0 ml) was then added and the mixture was stirred at room temperature for 30 minutes. Acetic acid was added to the reaction solution, followed by lyophilization. The resulting residue was purified by preparative HPLC (0.05% aqueous TFA solution:acetonitrile) to afford the title compound 89 (24.7 mg, 22%).

LCMS: m/z 735 (M+H)+
Retention time: 0.473 min, 0.491 min (analysis condition SMD method 1)

1-4. Synthesis of Aminoacylated pdCpA Compound 90

1-4-1. Synthesis of (S)-Cyanomethyl 2-((tert-butoxycarbonyl)amino)-3-(4-iodophenyl)propanoate (Compound 91)

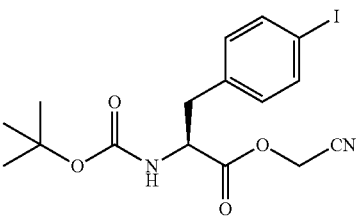 [SMILES: CC(C)(C)OC(=O)N[C@@H](Cc1ccc(I)cc1)C(=O)OCC#N]

The title compound 91 (0.40 g, 36%) was obtained by the same method as the method of providing Compound 86 using (S)-2-((tert-butoxycarbonyl)amino)-3-(4-iodophenyl)propanoic acid (1.0 g, 2.56 mmol) in place of but-3-enoic acid as a starting material.

Retention time: 1.59 min (analysis condition SMD method 4)

$^1$H-NMR (Broker, avance II, 300 MHz, CDCl$_3$) δ ppm 7.67 (2H, d, 8.1 Hz), 6.93 (2H, d, 8.1 Hz), 4.62-4.94 (4H, m), 2.98-3.14 (2H, m), 1.44 (9H, s)

1-4-2. Synthesis of (S)-cyanomethyl 3-(4-iodophenyl)-2-(pent-4-enamido)propanoate (Compound 92)

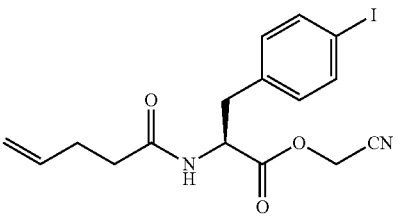 [SMILES: C=CCCC(=O)N[C@@H](Cc1ccc(I)cc1)C(=O)OCC#N]

(S)-Cyanomethyl 2-((tert-butoxycarbonyl)amino)-3-(4-iodophenyl)propanoate (Compound 91) (0.89 g, 2.07 mmol) was dissolved in diethyl ether (20.0 ml). The solution was bubbled with hydrochloric acid gas and then stirred at room temperature for 2 hours. The solid in the reaction solution was filtered off and dried under reduced pressure to afford (S)-cyanomethyl 2-amino-3-(4-iodophenyl)propanoate (0.65 g, 86%).

(S)-Cyanomethyl 2-amino-3-(4-iodophenyl)propanoate (0.65 g, 1.78 mmol) was dissolved in dichloromethane (25.0 ml) under a nitrogen atmosphere, and triethylamine (0.45 g, 4.45 mmol) was added dropwise under ice-cooling. A solution of pent-4-enoyl chloride (0.25 g, 2.14 mmol) in dichloromethane (25.0 ml) was then added dropwise under ice-cooling, and the mixture was stirred at room temperature for 2.5 hours. The reaction solution was concentrated under reduced pressure, and the resulting residue was purified by column chromatography (petroleum ether:ethyl acetate=50:50-33:67) to afford (S)-cyanomethyl 3-(4-iodophenyl)-2-(pent-4-enamido)propanoate (Compound 92) (0.57 g, 78%).

LCMS: m/z 413.2 (M+H)+
Retention time: 1.51 min (analysis condition SMD method 5)

1-4-3. Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(4-iodophenyl)-2-(pent-4-enamido)propanoate (Compound 90)

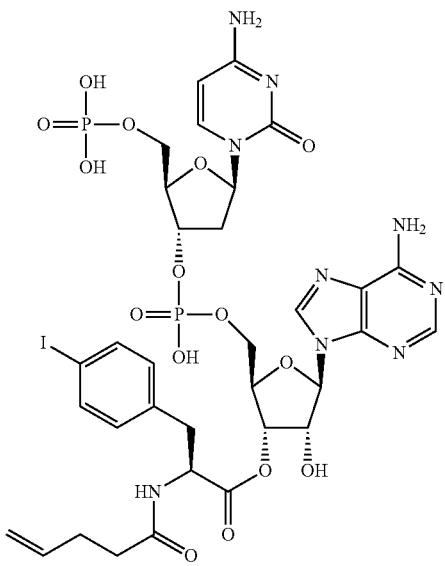 [SMILES: C=CCCC(=O)N[C@@H](Cc1ccc(I)cc1)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (96 mg, 0.150 mmol) was added to a buffer (100 ml) in which imidazole (680.8 mg, 10.00 mmol) and N,N,N-trimethylhexadecan-1-aminium chloride (640.0 mg, 2.00 mmol) were dissolved and which was adjusted to pH 8 with acetic acid. A solution of (S)-cyanomethyl 3-(4-iodophenyl)-2-(pent-4-enamido)propanoate (Compound 92) (249 mg, 0.60 mmol) in THF (1.0 ml) was then added and the mixture was stirred at room temperature for 2 hours. TFA (1.0 ml) was added to the reaction solution, followed by lyophilization. The resulting residue was purified by preparative HPLC (0.05% aqueous TFA solution:acetonitrile=80:20-60:40) to afford the title compound 90 (35 mg, 23%).

LCMS: m/z 990 (M−H)−

Retention time: 1.45 min (analysis condition ZQFA05)

1-5. Synthesis of Aminoacylated pdCpA Compound 93

1-5-1. Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(3-iodophenyl)-2-(pent-4-enamido)propanoate (Compound 93, pdCpA-Phe(3-I))

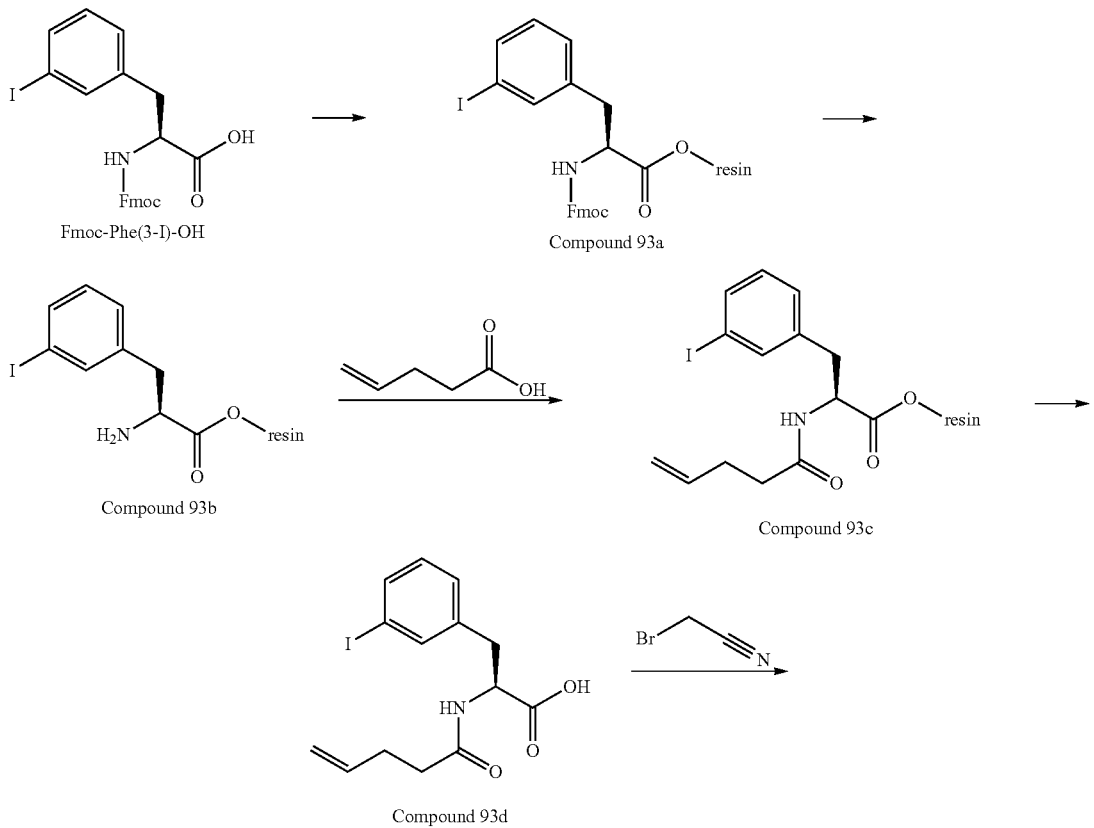

-continued

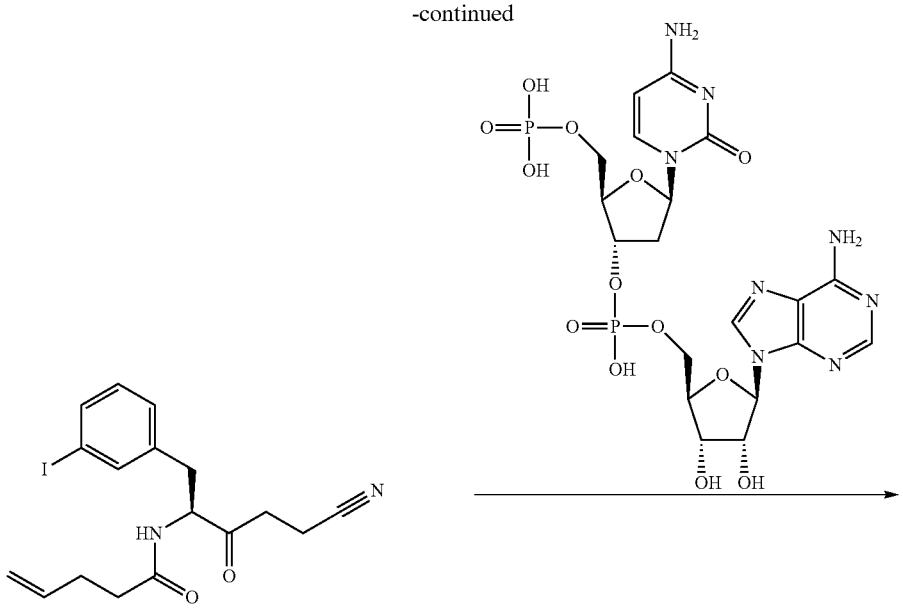

Compound 93e

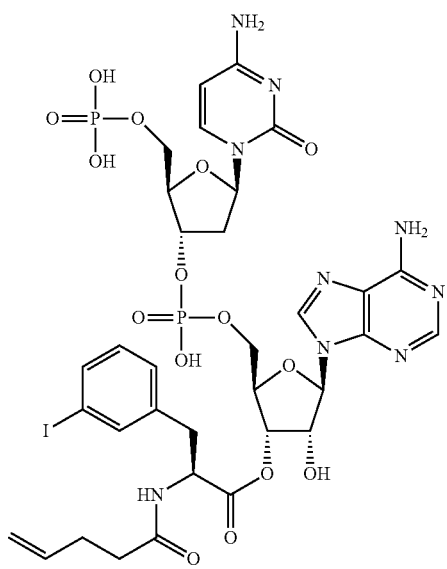

Compound 93

2-Chlorotrityl chloride resin (100-200 mesh, 1% DVB, purchased from Watanabe Chemical Industries, 2.78 g) was immersed in dichloromethane (30 ml) under a nitrogen atmosphere and was swollen by stirring at room temperature for 20 minutes. After removing dichloromethane, a solution of (S)-2-((((9H-fluoren-9-yl)methoxy)carbonyl)amino)-3-(3-iodophenyl)propanoic acid (Fmoc-Phe(3-I)—OH, 1.50 g, 2.92 mmol) and DIPEA (1.50 g, 11.7 mmol) in dichloromethane (30 ml) was added and the mixture was stirred at room temperature for 5 hours. Methanol (3 ml) was then added and the mixture was stirred for a further 1 hour. The reaction solution was removed, and the resulting resin was washed with dichloromethane (30 ml×3) and DMF (30 ml×2) to afford Compound 93a.

For the purpose of deprotection of the Fmoc group, a 20% solution of piperidine in DMF (20 ml) was added to Compound 93a, the mixture was stirred at room temperature for 2 hours, and the reaction solution was then removed. The resin was washed with DMF (30 ml×4) to afford Compound 93b.

A solution of pent-4-enoic acid (0.39 g, 3.90 mmol), DIC (0.550 g, 4.29 mmol) and HOAt (0.870 g, 4.29 mmol) in DMF (20 ml) was added to Compound 93b, and the mixture was stirred at room temperature for 5 hours. The reaction solution was removed, and the resin was washed with DMF (30 ml×4) and dichloromethane (50 ml×4) to afford Compound 93c.

A 2% solution of TFA in dichloromethane (20 ml) was added to Compound 93c, the mixture was stirred at room temperature for 1 hour, and the resin was removed by filtration. The same operation was repeated for further three times, and the obtained reaction solutions were combined and concentrated under reduced pressure. The residue was purified by column chromatography (dichloromethane:

methanol=30:1) to afford (S)-3-(3-iodophenyl)-2-(pent-4-enamido)propanoic acid (Compound 93d) (0.494 g, 68%).

Compound 93d (0.494 g, 1.324=1) was dissolved in DMF (10 ml), and 2-bromoacetonitrile (0.63 g, 5.30 mmol) and DIPEA (0.341 g, 2.65 mmol) were slowly added at room temperature. After stirring at room temperature for 30 minutes, the reaction solution was concentrated under reduced pressure, and the resulting residue was purified by column chromatography (petroleum ether:ethyl acetate=5:1) to afford (S)-3-(3-iodo-phenyl)-2-pent-4-enoylamino-propionic acid cyanomethyl ester (Compound 93e) (0.392 g, 72%).

((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h, pdCpA) (70 mg, 0.11 mmol) was added to a buffer (70 ml) in which imidazole (476.6 mg, 7.0 mmol) and N,N,N-trimethylhexadecan-1-aminium chloride (448.0 mg, 1.4 mmol) were dissolved and which was adjusted to pH 8 with acetic acid. A solution of (S)-3-(3-iodo-phenyl)-2-pent-4-enoylamino-propionic acid cyanomethyl ester (Compound 93e) (181.3 mg, 0.44 mmol) in THF (3.0 ml) was then added and the mixture was stirred at room temperature for 2 hours. TFA (1.0 ml) was added to the reaction solution, followed by lyophilization. The resulting residue was purified by preparative HPLC (0.05% aqueous TFA solution: acetonitrile=80:20-60:40) to afford the title compound 93 (17.9 mg, 16%).

LCMS: m/z 992 (M+H)+

Retention time: 0.75 min (analysis condition SQDAA05)

1-6. Synthesis of Aminoacylated pdCpA Compound 94

1-6-1. Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(2-iodophenyl)-2-(pent-4-enamido)propanoate The title compound 94 (14.2 mg, 13%) was obtained by the same method as the method of providing Compound 93 using (2S)-2-[[(9H-fluoren-9-ylmethoxy)carbonyl]amino]-3-(2-iodophenyl)propanoic acid (1.50 g, 2.92 mmol) in place of (S)-2-((((9H-fluoren-9-yl)methoxy)carbonyl)amino)-3-(3-iodophenyl)propanoic acid as a starting material.

LCMS: m/z 992 (M+H)+

Retention time: 0.71 min, 0.73 min (analysis condition SQDAA05)

2-1. Synthesis of Aminoacylated tRNA

Synthesis of Acylated tRNA (Compound AT-2-IIIA) by Ligation of pdCpA-PenteA (Compound 87) and tRNA (Lacking CA) (SEQ ID NO: R-5)

2 μL of 10× ligation buffer (500 mM HEPES-KOH pH 7.5, 200 nM MgCl$_2$, 10 mM ATP) and 4 μL of nuclease free water were added to 10 μL of 50 μM transcribed tRNAfMetCAU (-CA) (SEQ ID NO: R-5). The mixture was heated at 95° C. for 2 minutes and then left to stand at room temperature for 5 minutes, and the tRNA was refolded. 2 μL of 10 units/μL T4 RNA ligase (New England Biolabs) and 2 μL of a 5 mM solution of pdCpA-PenteA (Compound 87) in DMSO were added, and ligation reaction was carried out at 15° C. for 45 minutes. Acylated tRNA (Compound AT-2-IIIA) was collected by phenol extraction and ethanol precipitation. Acylated tRNA (Compound AT-2-IIIA) was dissolved in 1 mM sodium acetate immediately prior to addition to the translation mixture.

(SEQ ID NO: 33)

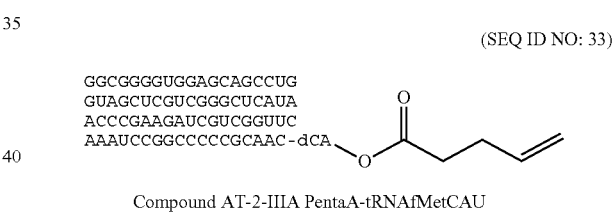

Compound AT-2-IIIA PentaA-tRNAfMetCAU

Synthesis of Aminoacylated tRNA (Compound AT-1-IIIA) by Ligation of Aminoacylated pdCpA (Compound 93) and tRNA (Lacking CA) (SEQ ID NO: R-1)

2 μL of 10× ligation buffer (500 mM HEPES-KOH pH 7.5, 200 mM MgCl$_2$, 10 mM ATP) and 4 μL of nuclease free water were added to 10 μL of 50 μM transcribed tRNAEnAsnGAG (-CA) (SEQ ID NO: R-1). The mixture was heated at 95° C. for 2 minutes and then left to stand at room temperature for 5 minutes, and the tRNA was refolded. 2 μL of 20 units/μL T4 RNA ligase (New England Biolabs) and 2 μL of a 5 mM solution of pdCpA-Phe(3-I) (Compound 93) in DMSO were added, and ligation reaction was carried out at 15° C. for 45 minutes. 4 μL of 3 M sodium acetate and 24 μL of 125 mM iodine (solution in water:THF=1:1) were added to 20 μL of the ligation reaction solution, and deprotection was carried out at room temperature for 1 hour. Aminoacylated tRNA was collected by phenol extraction and ethanol precipitation. Aminoacylated tRNA (Compound AT-1-IIIA) was dissolved in 1 mM sodium acetate immediately prior to addition to the translation mixture.

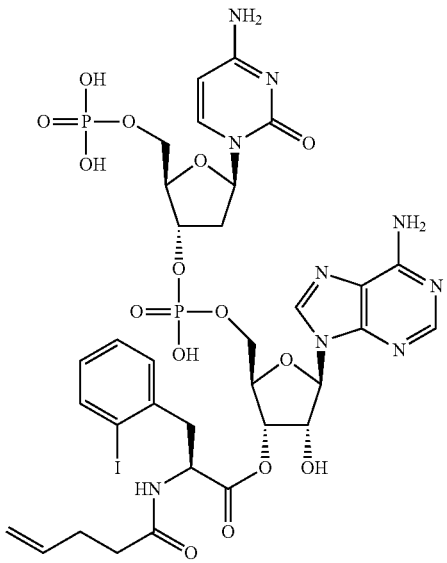 [SMILES: C=CCCC(=O)N[C@@H](Cc1ccccc1I)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

(SEQ ID NO: 33)

```
GGCUCUGUAGUUCAGUCGG
UAGAACGGCGGACUgagAA
UCCGUAUGUCACUGGUUCG
AGUCCAGUCAGAGCCGC-dCA
```

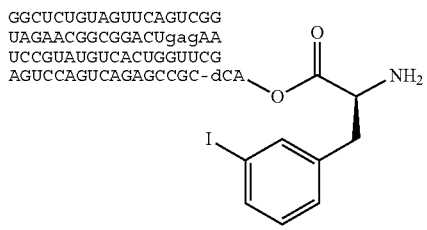

Compound AT-1-IIIA Phe (3-I)-tRNAEnAsnGAG 2-2. Translational Synthesis

```
Hc1 mRNA sequence (SEQ ID NO: R-41')
                                      (SEQ ID NO: 71)
GGGUUAACUUUAAgaaggagauauacauAUGUUUCUUCCGagcggcucu ggcucuggcucuUAGGGCGGCGGGGACAAA Hc2 mRNA sequence (SEQ ID NO: R-42)
                                      (SEQ ID NO: 72)
GGGUUAACUUUAAgaaggagauauacauAUGACUACAACGagcggcucu ggcucuUUUCUUCCGggcucuUAGGGCGGCGGGGACAAA Hc3 mRNA sequence (SEQ ID NO: R-43)
                                      (SEQ ID NO: 73)
GGGUUAACUUUAAgaaggagauauacauAUGAACAACAACAACAACACU ACAACGggcCUUCCGggcucuUAGGGCGGCGGGGACAAA Hc1 Peptide sequence P-160
                                     (SEQ ID NO: 284)
[PenteA]Phe[Phe(3-I)]ProSerGlySerGlySerGlySer Hc2 Peptide sequence P-161
                                     (SEQ ID NO: 285)
[PenteA]ThrThrThrSerGlySerGlySerPhe[Phe(3-I)]Pro GlySer Hc3 Peptide sequence P-162
                                     (SEQ ID NO: 286)
[PenteA]AsnAsnAsnAsnAsnThrThrThrGly[Phe(3-I)]Pro GlySer
```

Translational Synthesis of Peptides P-160, P-161 and P-162

1 µM template mRNA Hc1, Hc2 or Hc3 (SEQ ID NO: R-41', R-42 or R-43) was added to a translation solution containing 0.3 mM each of 18 proteinogenic amino acids excluding Met and Leu, 20 µM Phe(3-I)-tRNAEnAsnGAG (Compound AT-1-IIIA), and 20 µM PenteA-tRNAfMetCAU (Compound AT-2-IIIA), and the mixture was incubated at 37° C. for 60 minutes. Heck cyclization reaction was then carried out by the method illustrated below.

Cyclization Reaction of Hc1 (Peptide Sequence P-160)

Phosphate buffer (80 µL of a solution of K2HPO4 (1.0 mmol) and K3PO4 (0.2 mmol) in 10 mL of water) and 5% aqueous PTS (polyoxyethanyl-α-tocopheryl sebacate) (200 µL) were mixed, the translational product obtained from SEQ ID NO: R-41' (Hc1, 20 µL) was added, and the atmosphere was replaced with nitrogen. A Pd solution (60.0 µL) obtained by dissolving PdCl2(MeCN)2 (1.0 mg, 3.9 µmol) and 2,2'-diphenylphosphino-1,1'-biphenyl (6.2 mg, 12 µmol) in N-methylpyrrolidinone (0.2 mL) under a nitrogen atmosphere was added to the resulting mixture, which was then stirred at 50° C. for 12 hours under a nitrogen atmosphere. A 0.2 M aqueous thiocyanuric acid sesquipotassium salt solution (73.5 µL) was added to the reaction solution.

Water was added to the obtained reaction solution, and the resulting 2 mL was centrifuged (10000 rpm, 6 min, room temperature). The supernatant was lyophilized, and the resulting residue was redissolved in 100 µL of water:acetonitrile=9:1, and LC/MS analysis confirmed that a cyclized compound was produced.

LC-HRMS: m/z 1007.4149 (M–H)– (Calcd for $C_{46}H_{59}N_{10}O_{16}$: 1007.4116)

Retention time: 6.43 min (analysis condition Orbitrap HFIP-Et3N)

Cyclization Reaction of Hc2 (Peptide Sequence P-161)

Cyclization reaction was carried out by the same method as in the case of Hc1. The resulting product was analyzed by LC/MS by the same method as in the case of Hc1 to confirm production of two compounds indicated as cyclized compounds.

LC-HRMS: m/z 1310.5579 (M–H)– (Calcd for $C_{58}H_{80}N_{13}O_{22}$: 1310.5546)

Retention time: 4.91 min

LC-HRMS: m/z 1310.5570 (M–H)– (Calcd for $C_{58}H_{80}N_{13}O_{22}$: 1310.5546)

Retention time: 5.17 min (Analysis Condition Orbitrap HFIP-Et3N)

Cyclization Reaction of Hc3 (Peptide Sequence P-162)

Cyclization reaction was carried out by the same method as in the case of Hc1. The resulting product was analyzed by LC/MS by the same method as in the case of Hc1 to confirm production of a cyclized compound.

LC-HRMS: m/z 1415.5860 (M–H)–, Calcd for $C_{58}H_{83}N_{18}O_{24}$: 1415.5833

Retention time: 3.35 min (analysis condition Orbitrap HFIP-Et3N)

Reverse Transcription Example

An mRNA-peptide fusion was subjected to Heck cyclization reaction conditions, and the collected mRNA-peptide fusion was reverse-transcribed. It was confirmed that the reverse transcription proceeded without problems and that mRNA was stable under Heck cyclization reaction conditions.

Preparation of an mRNA-Peptide Fusion Solution mRNA was prepared by in vitro transcription using DNA (SEQ ID NO: D-50) prepared by PCR as a template, and was purified using RNeasy mini kit (Qiagen). 1.5 µM puromycin linker (Sigma) (SEQ ID NO: C-1), 1×T4 RNA ligase reaction buffer (NEB), 20% DMSO and 2 units/µl T4 RNA ligase (NEB) were added to 1 µM mRNA, ligation reaction was carried out at 37° C. for 30 minutes, and the mixture was then purified by RNeasy MiniElutekit (Qiagen). Next, RF1 was removed from the above-described cell-free translation solution, and the solution was added to 1 µM mRNA-puromycin linker conjugate (hereinafter mRNA-Pu) as a template. Translation at 37° C. for 30 minutes afforded an mRNA-peptide fusion molecule (Compound Fusion-1).

```
SEQ ID NO: D-50
KA03S2 DNA sequence:
                                      (SEQ ID NO: 74)
gtaatacgactcactataGGGTTAACTTTAAGAAGGAGATATACATatg ACTAGAACTaaggcgTACTGGAGCcttCCGggcggcAGCGGCTCTGGCT
```

```
                    -continued
CTGGCTCTTAGGGCGGCGGGGACAAA

KA03S2 mRNA sequence:
                                              (SEQ ID NO: 75)
GGGUUAACUUUAAGAAGGAGAUAUACAUaUgACUAGAACUaaggcgUAC UGGAGCcUUCCGggcggcAGCGGCUCUGGCUCUGGCUCUUAGGGCGGCG

GGGACAAA

SEQ ID C-1
S2PuFLin sequence:
                                              (SEQ ID NO: 76)
[P]CCCGTCCCCGCCGCCC[Fluorecein-dT][Spacer18]

[Spacer18][Spacer18][Spacer18][Spacer18]CC

[Puromycin] ([P]: 5'-phosphorylated)
```

Cyclization Reaction

The obtained mRNA-peptide fusion molecule (Compound Fusion-1, 11.0 µl) was mixed with 10-mer RNA-peptide conjugate (Compound 70b) (0.33 mM aqueous solution, 5.0 µL, 1.65 nmol), phosphate buffer (40 µL of a solution of K2HPO4 (1.0 mmol) and K3PO4 (0.20 mmol) in 10 mL of water) and 5% aqueous PTS (polyoxyethanyl-α-tocopheryl sebacate) (100 µL), followed by addition of a Pd solution (30.0 µL) obtained by dissolving PdCl2(MeCN)2 (1.0 mg, 3.9 µmol) and 2,2'-diphenylphosphino-1,1'-biphenyl (6.2 mg, 12 µmol) in N-methylpyrrolidinone (0.2 mL) under a nitrogen atmosphere. The mixture was stirred at 50° C. for 12 hours under a nitrogen atmosphere. A 0.2 M aqueous thiocyanuric acid sesquipotassium salt solution (37.0 µL) was added to the resulting reaction solution, and the mixture was left to stand at room temperature for 30 minutes to afford a cyclization reaction solution. The reaction solution (5.0 µL) was diluted with water (10.0 µL) to prepare an LC analysis sample, and analysis of the sample confirmed that the 10-mer RNA-peptide conjugate (Compound 70b) disappeared and a cyclized compound of the 10-mer RNA-peptide conjugate (Compound 83b) was produced.

LCMS (ESI) 1265.9 (M−3H)3−

Retention time: 3.48 min (analysis condition ZQHFIP-Me2NEt)

Confirmation of Reverse Transcription

Figure 43:
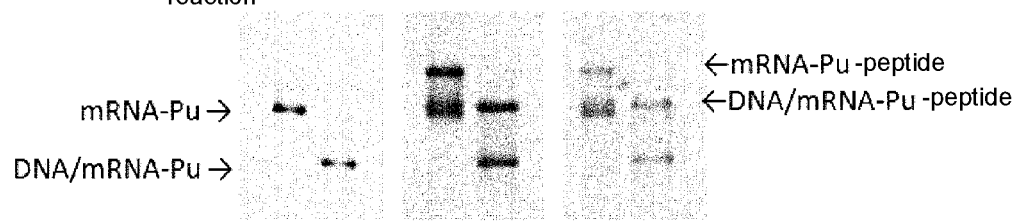
FIG. 43 is a diagram showing results of reverse transcription reaction using an mRNA-peptide fusion molecule after cyclization reaction as a template.

The mRNA-peptide fusion molecule after the cyclization reaction was purified by RNeasy MiniElute Kit (Qiagen). A reverse transcription reaction solution (1×M-MLV reverse transcription reaction buffer (Promega), 0.5 mM each of dNTP mix, 4 units/µl M-MLV reverse transcriptase RNaseH negative point mutation and 3 µM reverse transcription primer (SEQ ID NO: C-2) were added to 0.5 µM of the mRNA-peptide fusion molecule as a template, and reverse-transcription reaction was carried out at 42° C. for 20 minutes. The reaction product was subjected to electrophoresis using TGX gel anykD (Biorad), and fluorescence of the fluorescein added to the puromycin linker was detected. As a result, it was confirmed that reverse transcription reaction efficiently proceeded regardless of the presence or absence of cyclization reaction. The result is shown in FIG. 43.

```
SEQ ID NO: C-2
Reverse transcription primer
                                              (SEQ ID NO: 77)
TTTGTCCCCGCCGCCCTAAGAGCCAGAGCCAGAGCCGCT
```

Example 24

Heck Reaction of an RNA Complex
Preparation of an mRNA-Peptide Complex Solution

9 µM puromycin linker (Sigma) (SEQ ID NO: C-1), 1×T4 RNA ligase reaction buffer (New England Biolabs, catalog No. M0204L), 10% DMSO and 0.63 unit/µl T4 RNA ligase (New England Biolabs, catalog No. M0204L) were added to 6 µM mRNA (Hc1 mRNA sequence (SEQ ID NO: R-41)), ligation reaction was carried out at 37° C. for 30 minutes, and purification by RNeasy MiniElutekit (Qiagen) afforded an mRNA-Puromycin linker conjugate (hereinafter mRNA-Pu). A cell-free translation solution (1 mM GTP, 1 mM ATP, 20 mM creatine phosphate, 50 mM HEPES-KOH pH 7.6, 100 mM potassium acetate, 9 mM magnesium acetate, 2 mM spermidine, 1 mM dithiothreitol, 0.5 mg/ml E. coli MRE600 (RNase-negative)-derived tRNA (Roche), 4 µg/ml creatine kinase, 3 µg/ml myokinase, 2 units/ml inorganic pyrophosphatase, 1.1 µg/ml nucleoside diphosphate kinase, 0.6 µM methionyl tRNA transformylase, 0.26 µM EF-G, 0.24 µM RF2, 0.17 µM RF3, 0.5 µM RRF, 2.7 µM IF1, 0.4 µM IF2, 1.5 µM IF3, 40 µM EF-Tu, 84 µM EF-Ts, 1.2 µM ribosome, 0.73 µM AlaRS, 0.03 µM ArgRS, 0.38 µM AsnRS, 0.13 µM AspRS, 0.02 µM CysRS, 0.06 µM GlnRS, 0.23 µM GluRS, 0.09 µM GlyRS, 0.02 µM HisRS, 0.4 µM IleRS, 0.04 µM LeuRS, 0.11 µM LysRS, 0.03 µM MetRS, 0.68 µM PheRS, 0.16 µM ProRS, 0.04 µM SerRS, 0.09 µM ThrRS, 0.03 µM TrpRS, 0.02 µM TyrRS, 0.02 µM ValRS (self-prepared proteins were basically prepared as His-tagged proteins), and 300 µM each of proteinogenic amino acids excluding methionine and leucine), 20 µM Compound AT-1-IIIA and 20 µM 4-PenteA-tRNAfMetCAU (Compound AT-2-IIIA) were added to 1 µM of the purified mRNA-Pu as a template, followed by translation at 37° C. for 30 minutes. 18 mM EDTA pH 8.0 was added to provide an mRNA-peptide complex.

Cyclization Reaction

The obtained mRNA-peptide complex (20.0 µL) was mixed with phosphate buffer (120 µL of a solution of K2HPO4 (1.0 mmol) and K3PO4 (0.40 mmol) in 10 mL of water) and 15% PTS (polyoxyethanyl-α-tocopheryl sebacate) (200 µL), followed by addition of a Pd solution (60.0 µL) obtained by dissolving PdCl2(MeCN)2 (4.0 mg, 15.4 µmol) and 2,2'-diphenylphosphino-1,1'-biphenyl (24.8 mg, 47.5 µmol) in N-methylpyrrolidinone (0.8 mL) under a nitrogen atmosphere. The mixture was stirred at 50° C. for 24 hours under a nitrogen atmosphere. A 0.2 M aqueous thiocyanuric acid sesquipotassium salt solution (73.5 µL) was added to the resulting reaction solution, and the mixture was left to stand at room temperature for 30 minutes to afford a cyclization reaction solution.

RNase Treatment

The above cyclization reaction solution was centrifuged using a tabletop centrifuge, and the supernatant was purified with RNeasy miniElute Cleanup kit (Qiagen, Catalog No. 74204) and eluted with RNase free water. The eluate was reacted with 1×Reaction buffer (Promega, Catalog No. M217A, 10 mM Tris-HCl pH 7.5, 5 mM EDTA, 0.2 M AcONa), 0.5 unit/µl RNaseONE ribonuclease (Promega, Catalog No. M425A) and 0.1 unit/µl RNaseH (LifeTechnologies, Catalog No. 18021-014) at 37° C. for 3 hours to afford the following compound (Compound Fusion-2).

Compound Fusion-2
(SEQ ID NO: 76)
HO-CCCGTCCCCGCCGCCC[Fluorescein-dT][Spacer18][Spacer18][Spacer18][Spacer18][Spacer18]CC[Puromycin]
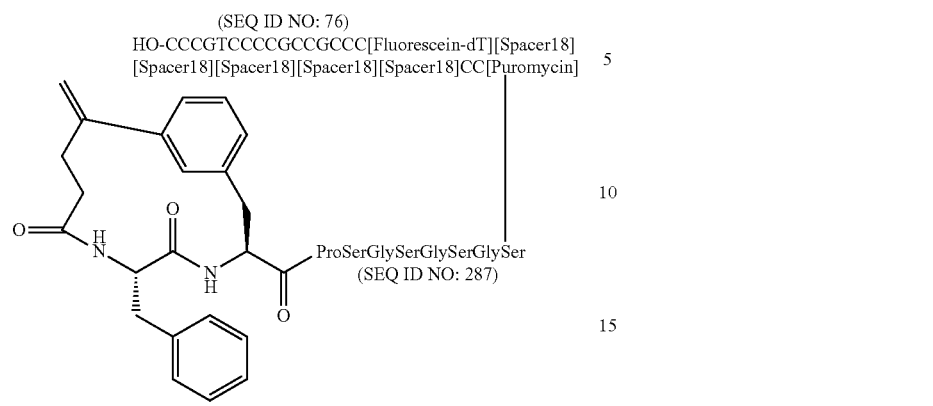
ProSerGlySerGlySerGlySer
(SEQ ID NO: 287)
The detailed partial structure is as follows.
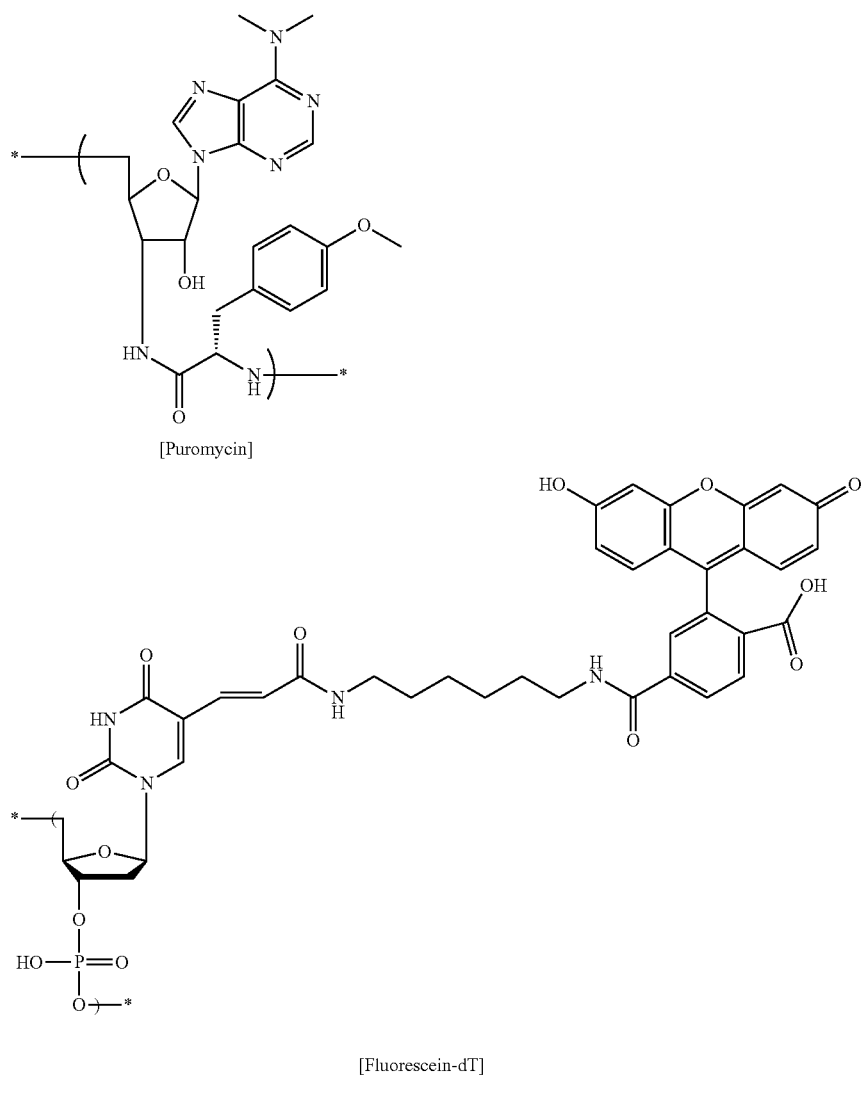
[Puromycin]
[Fluorescein-dT]

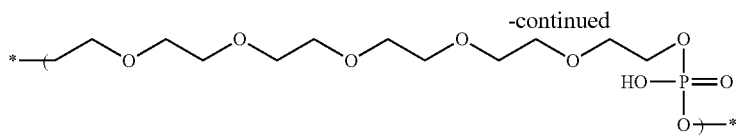

[Spacer18]

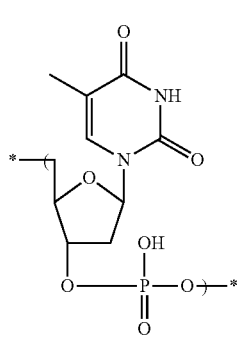

T

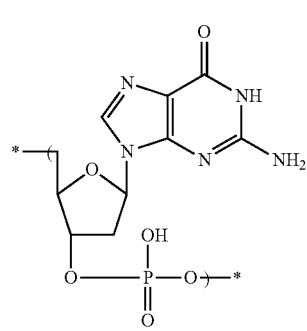

G

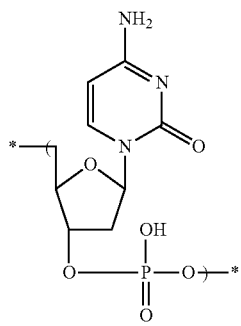

C

LC Analysis

Figure 81:
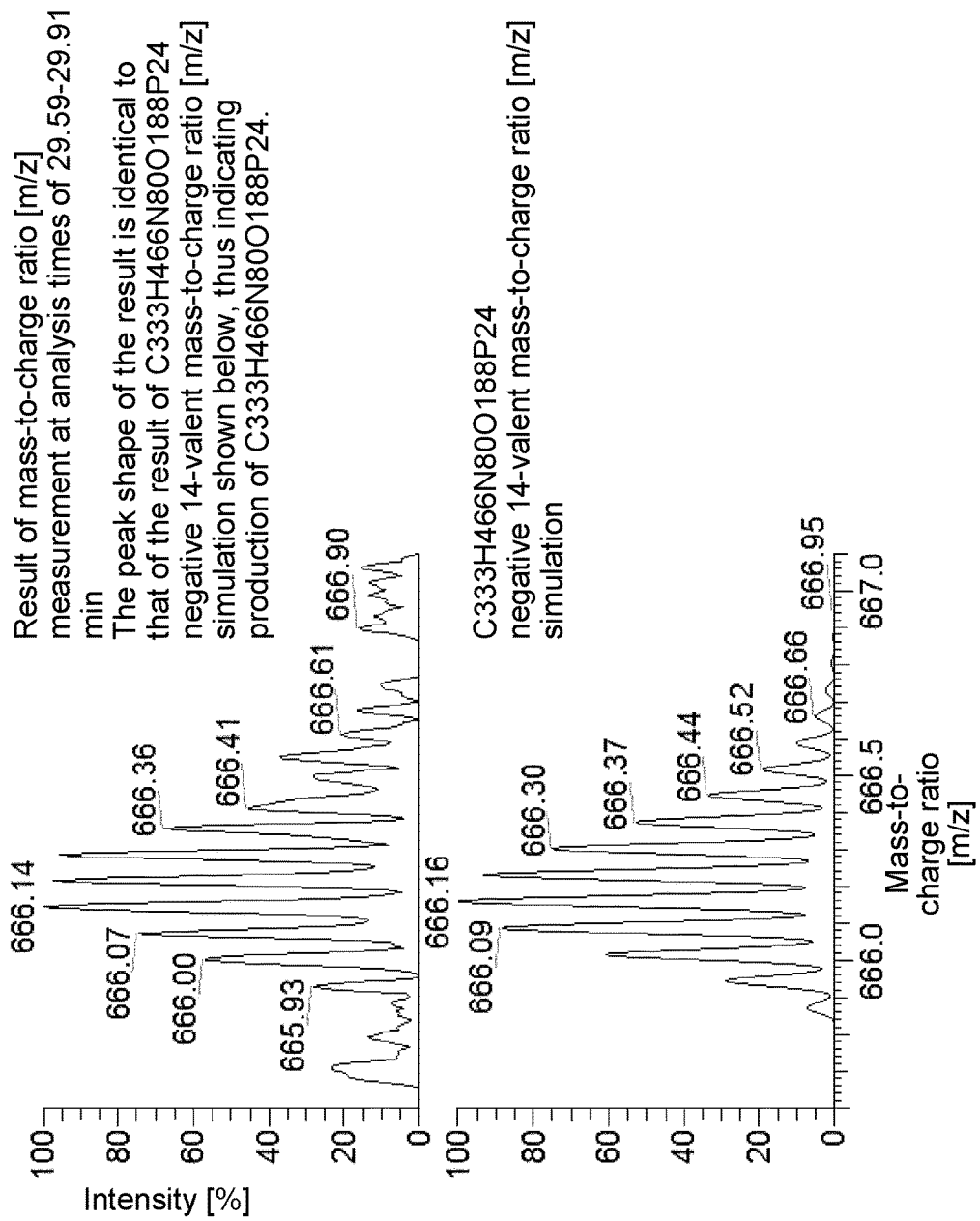
FIG. 81 is a diagram showing LC/MS analysis results of a sample obtained by treating an RNase-treated sample.

90 µL of an aqueous solution of 400 mM HFIP and 15 mM triethylamine was added to the RNase-treated sample (10 µL), followed by solid-phase extraction using Oasis HLB µElution (Waters). The 50% acetonitrile-eluted fraction was lyophilized and redissolved in water, and the resulting sample was subjected to LC/MS analysis to confirm production of a peptide fusion cyclization product (FIG. 81).

LC-HRMS: m/z 666.2124 (M−14H)14−, 621.7293 (M−15H)15−, 582.8100 (M−16H) 16− (Calcd for $C_{333}H_{466}N_{80}O_{188}P_{24}$: Molecular Weight 9341)

Retention time: 29.74 min (analysis condition Orbitrap HFIP-Et3N-2)

[Example 25] Implementation of a Display Library by Amide Cyclization

Unnatural amino acids were prepared which were introduced by synthesis of pdCpA-amino acids and subsequent synthesis of tRNA-amino acid complexes without use of ARS. Next, highly diverse random DNAs were prepared. RNA-cyclized peptide complexes were made by transcription, translation and chemical modification, and panning was then carried out to perform an experiment to provide peptides binding to TNFα, TNFR1 and IL-6R.

1. Synthesis of pdCpA-Amino Acids to Construct a Display Library

Conjugate synthesis of pdCpA and an amino acid (pdCpA-amino acid) was carried out to translationally incorporate the following unnatural amino acids (MeGly, Phg, Phe(4-CF3), Met(O2), βAla, MeAla(4-Thz), MePhe(3-Cl), PrGly, MeSer and Hyp(Et)). Specifically, Compound SP705 (Pen-MeGly-pdCpA), Compound SP710 (Pen-Phg-pdCpA), Compound SP715 (Pen-Phe(4-CF3)-pdCpA), Compound SP720 (Pen-Net(O2)-pdCpA), Compound SP725 (Pen-βAla-pdCpA), Compound SP731 (Pen-MeAla(4-Thz)-pdCpA), Compound SP737 (Pen-MePhe(3-Cl)-pdCpA), Compound SP742 (Pen-nPrGly-pdCpA) and Compound SP754 (Pen-Hyp(Et)-pdCpA) were synthesized according to the following scheme. Synthesis of Compound 6i-C (tBuS-SEtGABA) and Compound 1i-IA has been previously described.

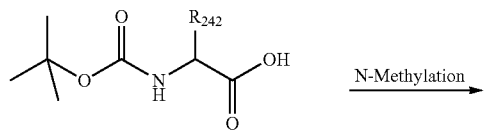 →N-Methylation→ 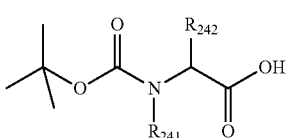 →Cyanomethylation→

SP726 (R242 = CH2 4-thiazolyl, for MeAla(4-Thz))
SP732 (R242 = CH2 Phe(3-Cl), for MePhe(3-Cl))

SP701(R241 = Me, R242 = H, for MeGly)
SP706(R241 = H, R242 = Phe, for Phg)
SP711(R241 = H, R242 = CH2 Phe(4-CF3), for Phe(4-CF3))
SP716(R241 = H, R242 = CH2 CH2 S(O)2 CH3, for Met (O2))
SP721 for βAla
SP727 (R241 = Me, R242 = CH2 4-thiazolyl, for MeAla(4-Thz))
SP733 (R241 = Me, R242 = CH2 Phe(3-Cl), for MePhe(3-Cl))
SP738 (R241 = nPr, R242 = H, for nPrGly)
SP750 for Hyp(Et)

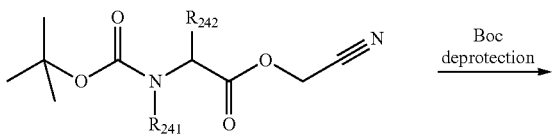 →Boc deprotection→ 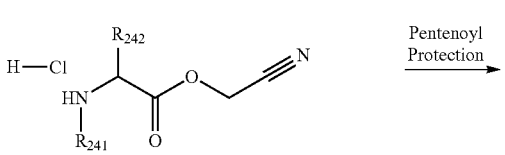 →Pentenoyl Protection→

SP702(R241 = Me, R242 = H, for MeGly)
SP707(R241 = H, R242 = Phe, for Phg)
SP712(R241 = H, R242 = CH2 Phe(4-CF3), for Phe(4-CF3))
SP717(R241 = H, R242 = CH2 CH2 S(O)2 CH3, for Met (O2))
SP722 for βAla
SP728 (R241 = Me, R242 = CH2 4-thiazolyl, for MeAla(4-Thz))
SP734 (R241 = Me, R242 = CH2 Phe(3-Cl), for MePhe(3-Cl))
SP739 (R241 = nPr, R242 = H, for nPrGly)
SP751 for Hyp(Et)

SP703(R241 = Me, R242 = H, for MeGly)
SP708(R241 = H, R242 = Phe, for Phg)
SP713(R241 = H, R242 = CH2 Phe(4-CF3), for Phe(4-CF3))
SP718(R241 = H, R242 = CH2 CH2 S(O)2 CH3, for Met (O2))
SP723 for βAla
SP729 (R241 = Me, R242 = CH2 4-thiazolyl, for MeAla(4-Thz))
SP735 (R241 = Me, R242 = CH2 Phe(3-Cl), for MePhe(3-Cl))
SP740 (R241 = nPr, R242 = H, for nPrGly)
SP752 for Hyp(Et)

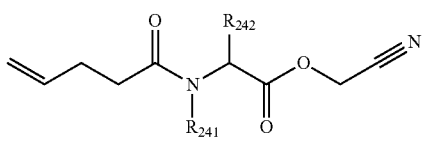

SP704(R241 = Me, R242 = H, for MeGly)
SP709(R241 = H, R242 = Phe, for Phg)
SP714(R241 = H, R242 = CH2 Phe(4-CF3), for Phe(4-CF3))
SP719(R241 = H, R242 = CH2 CH2 S(O)2 CH3, for Met (O2))
SP724 for βAla
SP730 (R241 = Me, R242 = CH2 4-thiazolyl, for MeAla(4-Thz))
SP736 (R241 = Me, R242 = CH2 Phe(3-Cl), for MePhe(3-Cl))
SP741 (R241 = nPr, R242 = H, for nPrGly)
SP753 for Hyp(Et)

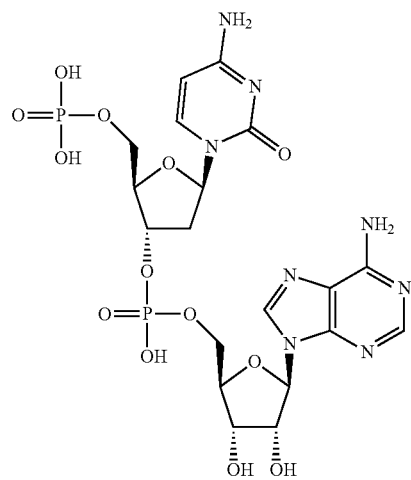

1h →

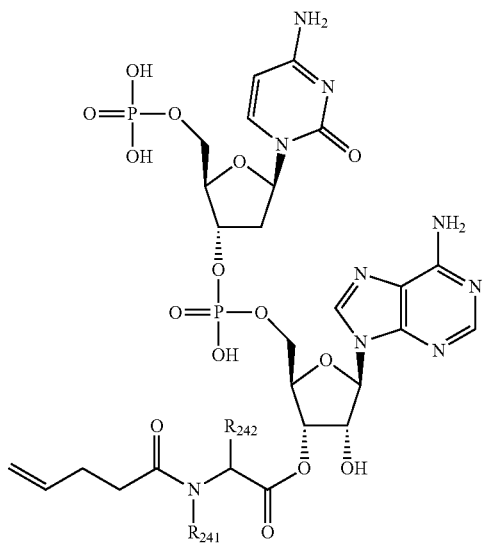
SP705(R241 = Me, R242 = H, for MeGly)
SP710(R241 = H, R242 = Phe, for Phg)
SP715(R241 = H, R242 = CH2 Phe(4-CF3), for Phe(4-CF3))
SP720 (R241 = H, R242 = CH2 CH2 S(O)2 CH3, for Met (O2))
SP725 for βAla
SP731 (R241 = Me, R242 = CH2 4-thiazolyl, for MeAla(4-Thz))
SP737 (R241 = Me, R242 = CH2 Phe(3-Cl), for MePhe(3-Cl))
SP742 (R241 = nPr, R242 = H, for nPrGly)
SP754 for Hyp(Et)
Compound SP749 (Pen-MeSer-pdCpA) was synthesized according to the following scheme.
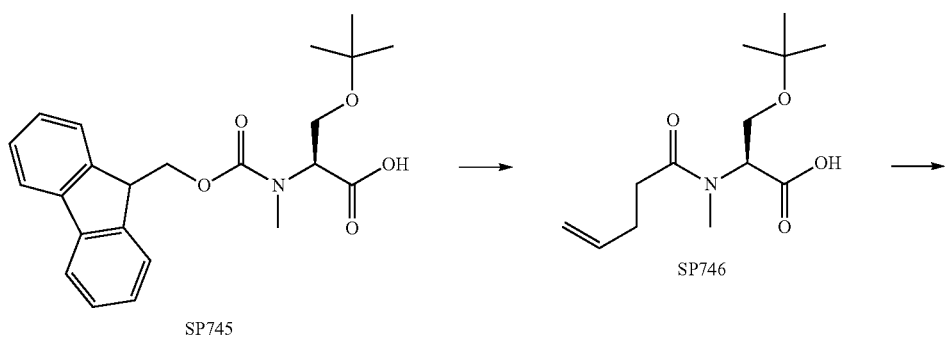

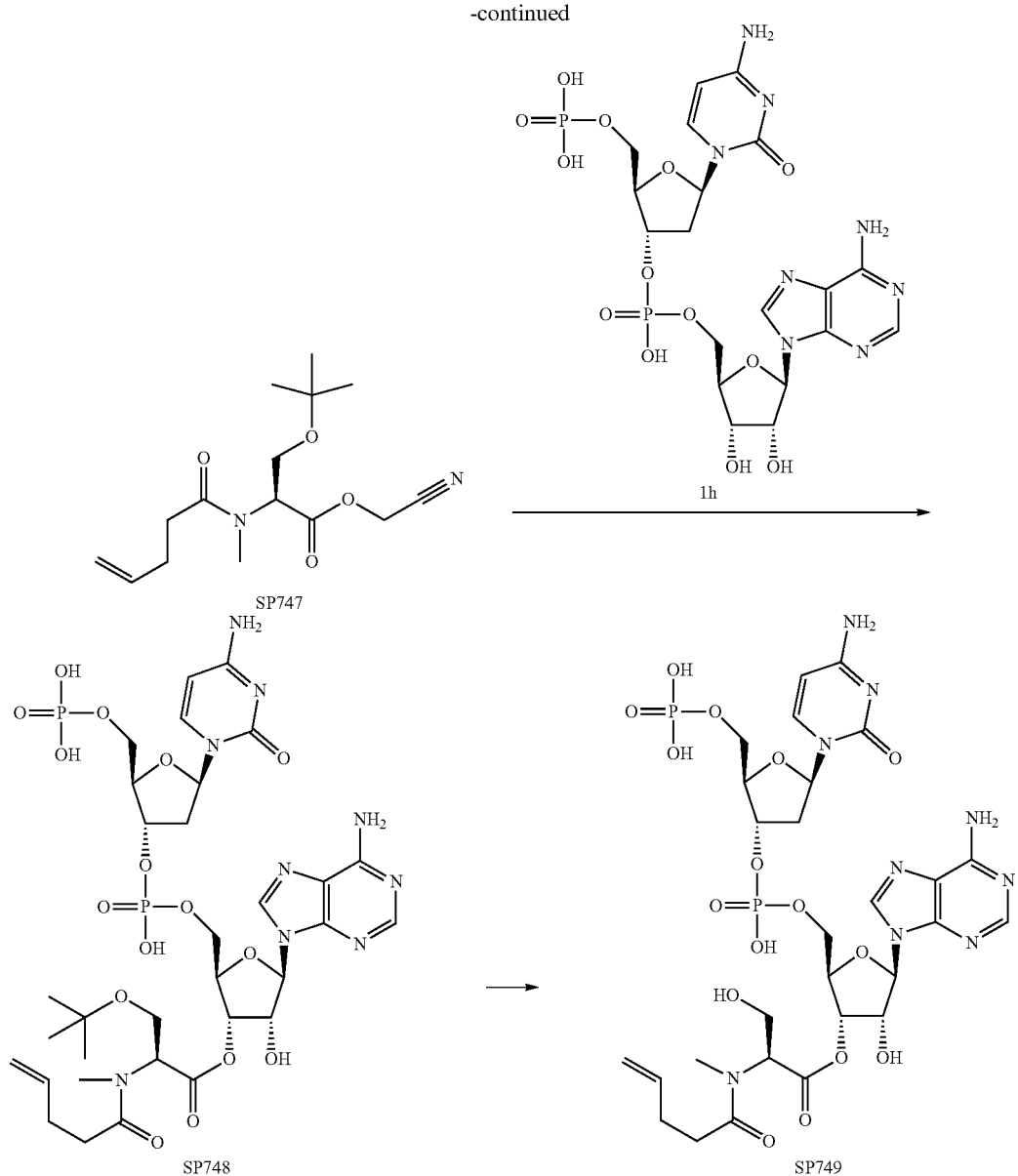

SP747, SP748, SP749, 1h

Synthesis of Cyanomethyl 2(-((tert-butoxycarbonyl)(methyl)amino)acetate (Compound SP702)

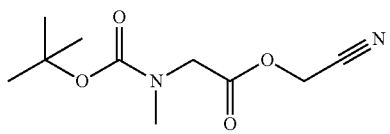 [SMILES: CN(CC(=O)OCC#N)C(=O)OC(C)(C)C]

2(-((tert-Butoxycarbonyl)(methyl)amino)acetic acid (Compound SP701) (10.0 g, 52.9 mmol) and N-ethyl-isopropylpropan-2-amine (DIPEA) (18.9 mL, 108 mmol) were dissolved in dichloromethane (100 ml) under a nitrogen atmosphere, 2-bromoacetonitrile (26.0 g, 217 mmol) was added and the mixture was stirred at room temperature for 1 hour. The reaction solution was concentrated under reduced pressure, and the residue was purified by column chromatography (ethyl acetate:petroleum ether=1:10→1:4) to afford cyanomethyl 2(-((tert-butoxycarbonyl)(methyl)amino)acetate (Compound SP702) (4.80 g, 80%).

LCMS (ESI) m/z=251 (M+Na)+

Retention time: 1.82 min (analysis condition SMD-method6)

Synthesis of Cyanomethyl 2-(methylamino)acetate Hydrochloride (Compound SP703)

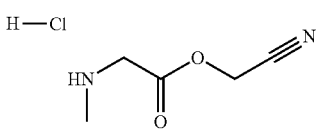

Cyanomethyl 2(-((tert-butoxycarbonyl)(methyl)amino) acetate (Compound SP702) (4.80 g, 21.0 mmol) was dissolved in diethyl ether (50 ml), and the solution was bubbled with hydrochloric acid gas and stirred at room temperature for 2 hours. The precipitated solid was collected by filtration and dried under reduced pressure to afford cyano methyl 2-(methylamino)acetate hydrochloride (Compound SP703) (3.00 g, 87%) as a crude product which was directly used for the next reaction.

Synthesis of Cyanomethyl 2-(N-methylpent-4-enamido)acetate (Pen-MeGly-OCH$_2$CN) (Compound SP704)

In the present specification, a 4-pentenoyl group was abbreviated to Pen, and a cyanomethyl group was described as CH$_2$CN.

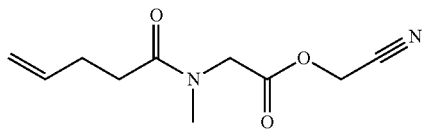

Cyanomethyl 2-(methylamino)acetate hydrochloride (Compound SP703) (3.00 g, 18.3 mmol) and triethylamine (6.34 ml, 45.5 mmol) were dissolved in dichloromethane (30 ml) under a nitrogen atmosphere, and pent-4-enoyl chloride (2.60 g, 22.0 mmol) was added dropwise at 0° C. The reaction solution was stirred at room temperature for 2 hours and 30 minutes and then concentrated under reduced pressure. The resulting residue was dissolved in ethyl acetate, and the solid was removed by filtration. The solution was concentrated under reduced pressure and purified by column chromatography (ethyl acetate:petroleum ether=1:10→2:7) to afford cyanomethyl 2-(N-methylpent-4-enamido)acetate (Compound SP704) (3.40 g, 88%).

LCMS (ESI) m/z=211 (M+H)+
Retention time: 1.50 min (analysis condition SMD-method6)

Synthesis of (2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-(N-methylpent-4-enamido)acetate (Pen-MeGly-pdCpA) (Compound SP705)

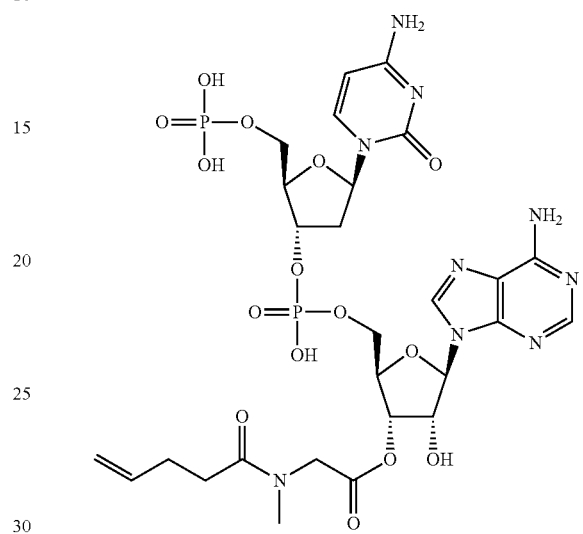

((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl) oxy)tetrahydrofuran-2-yl)methyl dihydrogenphosphate (Compound 1h) (Compound 1h) (1.00 g, 1.57 mmol) was dissolved in buffer A (1 l), a solution of cyanomethyl 2-(N-methylpent-4-enamido)acetate (Compound SP704) (2.00 g, 9.51 mmol) in tetrahydrofuran (5 ml) was added and the mixture was stirred at room temperature for 30 minutes. The reaction solution was lyophilized, and the resulting residue was purified by reverse-phase silica gel column chromatography (0.5% aqueous trifluoroacetic acid solution/acetonitrile) to afford the title compound (Compound SP705) (139 mg, 11%).

LCMS (ESI) m/z=790.5 (M+H)+
Retention time: 0.46 min (analysis condition SQDAA05)

Synthesis of (S)-cyanomethyl 2-((tert-butoxycarbonyl)amino)-2-phenylacetate (Compound SP707)

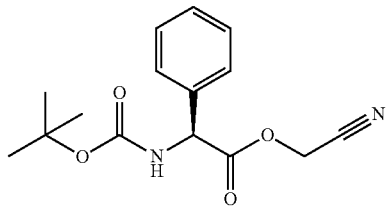 [SMILES: CC(C)(C)OC(=O)N[C@H](C(=O)OCC#N)c1ccccc1]

(S)-Cyanomethyl 2-((tert-butoxycarbonyl)amino)-2-phenylacetate (Compound SP707) (1.02 g, 88%) was obtained using (S)-2-((tert-butoxycarbonyl)amino)-2-phenylacetic acid (Compound SP706) (1.00 g, 3.98 mmol) in place of 2(-((tert-butoxycarbonyl)(methyl)amino)acetic acid (Compound SP701) under the same conditions as in the preparation example for Compound SP702.

Synthesis of (S)-cyanomethyl 2-amino-2-phenylacetate Hydrochloride (Compound SP708)

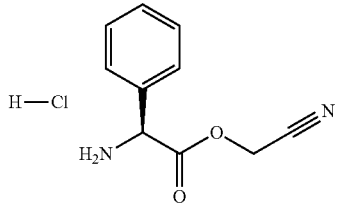

(S)-Cyanomethyl 2-amino-2-phenylacetate hydrochloride (Compound SP708) (2.80 g, 80%) was obtained as a crude product using (S)-cyanomethyl 2-((tert-butoxycarbonyl)amino)-2-phenylacetate (Compound SP707) (4.50 g, 15.5 mmol) in place of cyanomethyl 2-(-((tert-butoxycarbonyl)(methyl)amino)acetate (Compound SP702) under the same conditions as in the preparation example for Compound SP703. The crude product was directly used for the next reaction.

Synthesis of (S)-cyanomethyl 2-(pent-4-enamido)-2-phenylacetate (Pen-Phg-OCH₂CN) (Compound SP709)

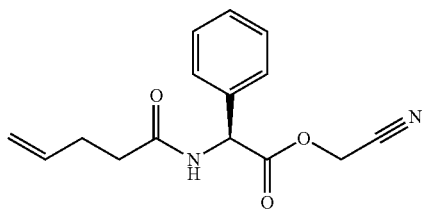 [SMILES: C=CCCC(=O)N[C@H](C(=O)OCC#N)c1ccccc1]

(S)-Cyanomethyl 2-(pent-4-enamido)-2-phenylacetate (Compound SP709) (1.90 g, 56%) was obtained using (S)-cyanomethyl 2-amino-2-phenylacetate hydrochloride (Compound SP708) (2.80 g, 12.4 mmol) in place of cyanomethyl 2-(methylamino)acetate hydrochloride (Compound SP703) under the same conditions as in the preparation example for Compound SP704.

LCMS (ESI) m/z=273 (M+H)+

Retention time: 1.88 min (analysis condition SMD-method7)

Synthesis of (2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-(pent-4-enamido)-2-phenylacetate (Pen-Phg-pdCpA) (Compound SP710)

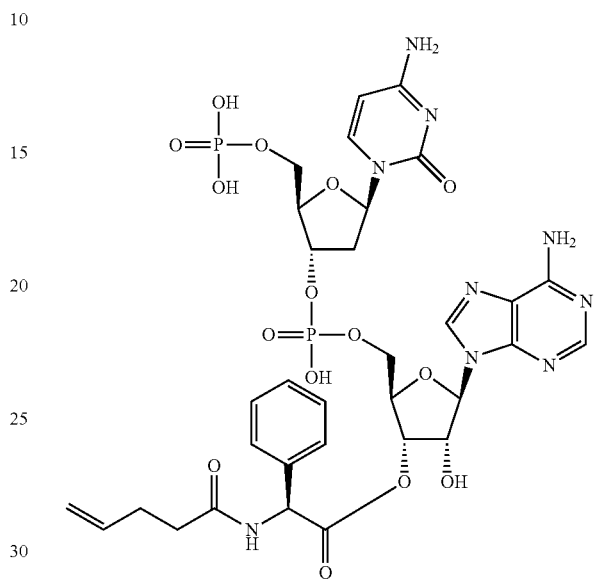

The title compound (Compound SP710) (79.7 mg, 8.5%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (700 mg, 1.10 mmol) and using (S)-cyanomethyl 2-(pent-4-enamido)-2-phenylacetate (Compound SP709) in place of cyanomethyl 2-(N-methylpent-4-enamido)acetate (Compound SP704) under the same conditions as in the preparation example for Compound SP705.

LCMS (ESI) m/z=852.5 (M+H)+

Retention time: 0.42 min (analysis condition SQDFA05)

Synthesis of (S)-cyanomethyl 2-((tert-butoxycarbonyl)amino)-3-(4-(trifluoromethyl)phenyl)propanoate (Compound SP712)

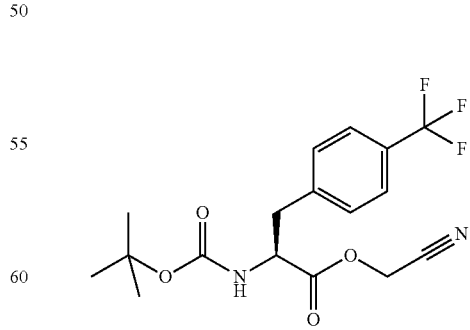

(S)-Cyanomethyl 2-((tert-butoxycarbonyl)amino)-3-(4-(trifluoromethyl)phenyl)propanoate (Compound SP712) (1.01 g, 90%) was obtained using (S)-2-((tert-butoxycarbonyl)amino)-3-(4-(trifluoromethyl)phenyl)propanoic acid (Compound SP711) (1.00 g, 3.00 mmol) in place of 2(-((tert-butoxycarbonyl)(methyl)amino)acetic acid (Compound SP701) under the same conditions as in the preparation example for Compound SP702.

Synthesis of (S)-cyanomethyl 2-amino-3-(4-(trifluoromethyl)phenyl)propanoate Hydrochloride (Compound SP713)

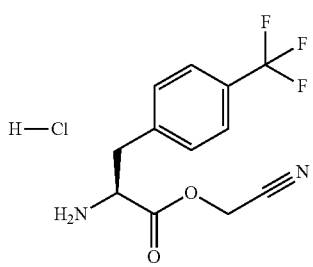 [SMILES: Cl ; N#CCOC(=O)[C@@H](N)Cc1ccc(C(F)(F)F)cc1]

(S)-Cyanomethyl 2-amino-3-(4-(trifluoromethyl)phenyl)propanoate hydrochloride (Compound SP713) (7.00 g, 91%) was obtained as a crude product using (S)-cyanomethyl 2-((tert-butoxycarbonyl)amino)-3-(4-(trifluoromethyl)phenyl)propanoate (Compound SP712) (9.30 g, 25.0 mmol) in place of cyanomethyl 2(-((tert-butoxycarbonyl)(methyl)amino)acetate (Compound SP702) under the same conditions as in the preparation example for Compound SP703. The crude product was directly used for the next reaction.

Synthesis of (S)-cyanomethyl 2-(pent-4-enamido)-3-(4-(trifluoromethyl)phenyl)propanoate (Pen-Phe(4-CF3)-OCH$_2$CN) (Compound SP714)

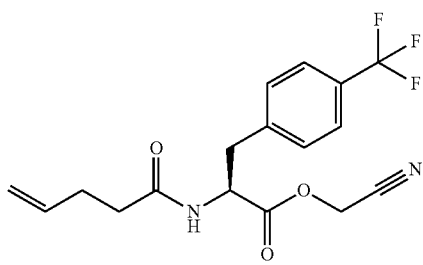 [SMILES: C=CCCC(=O)N[C@@H](Cc1ccc(C(F)(F)F)cc1)C(=O)OCC#N]

The title compound (Compound SP714) (3.50 g, 44%) was obtained using (S)-cyanomethyl 2-amino-3-(4-(trifluoromethyl)phenyl)propanoate hydrochloride (Compound SP713) (7.00 g, 22.7 mmol) in place of cyanomethyl 2-(methylamino)acetate hydrochloride (Compound SP703) under the same conditions as in the preparation example for Compound SP704.

LCMS (ESI) m/z=355 (M+H)+

Retention time: 1.47 min (analysis condition SMD-method7)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-(pent-4-enamido)-3-(4-(trifluoromethyl)phenyl)propanoate (Pen-Phe(4-CF$_3$)-pdCpA) (Compound SP715)

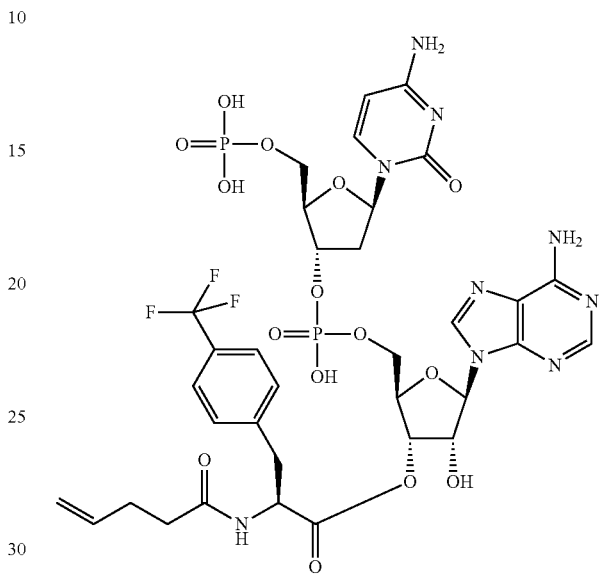

The title compound (Compound SP715) (258 mg, 18%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (1.00 g, 1.57 mmol) and using (S)-cyanomethyl 2-(pent-4-enamido)-3-(4-(trifluoromethyl)phenyl)propanoate (Compound SP714) in place of cyanomethyl 2-(N-methylpent-4-enamido)acetate (Compound SP704) under the same conditions as in the preparation example for Compound SP705.

LCMS (ESI) m/z=934.6 (M+H)+

Retention time: 0.73 min (analysis condition SQDAA05)

Synthesis of (S)-cyanomethyl 2-((tert-butoxycarbonyl)amino)-4-(methylsulfonyl)butanoate (Compound SP717)

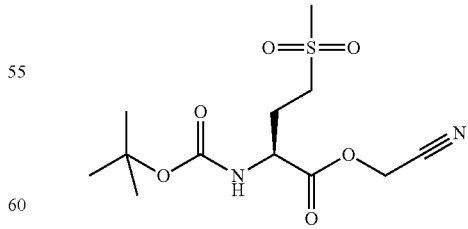

(S)-Cyanomethyl 2-((tert-butoxycarbonyl)amino)-4-(methylsulfonyl)butanoate (Compound SP717) (4.50 g, 79%) was obtained using (S)-2-((tert-butoxycarbonyl)amino)-4-(methylsulfonyl)butanoic acid (Compound SP716) (5.00 g, 17.8 mmol) in place of 2(-((tert-butoxycarbonyl)(methyl)amino)acetic acid (Compound SP701) under the same conditions as in the preparation example for Compound SP702.

Synthesis of (S)-cyanomethyl 2-amino-4-(methylsulfonyl)butanoate hydrochloride (Compound SP718)

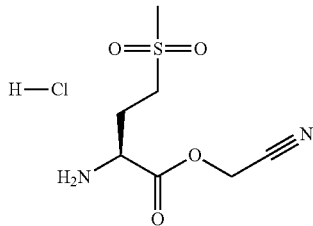

(S)-Cyanomethyl 2-amino-4-(methylsulfonyl)butanoate hydrochloride (Compound SP718) (3.50 g, 98%) was obtained as a crude product using (S)-cyanomethyl 2-((tert-butoxycarbonyl)amino)-4-(methylsulfonyl)butanoate (Compound SP717) (4.50 g, 14.0 mmol) in place of cyanomethyl 2(-((tert-butoxycarbonyl)(methyl)amino)acetate (Compound SP702) under the same conditions as in the preparation example for Compound SP703. The crude product was directly used for the next reaction.

Synthesis of (S)-cyanomethyl 4-(methylsulfonyl)-2-(pent-4-enamido)butanoate (Pen-Met(O₂)—OCH₂CN) (Compound SP719)

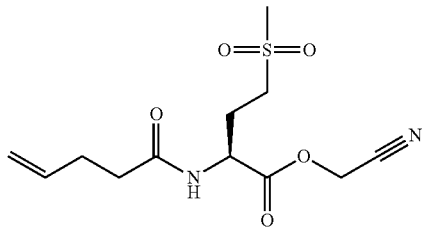 [SMILES: C=CCCC(=O)N[C@@H](CCS(C)(=O)=O)C(=O)OCC#N]

(S)-Cyanomethyl 4-(methylsulfonyl)-2-(pent-4-enamido)butanoate (Compound SP719) (2.00 g, 48%) was obtained using (S)-cyanomethyl 2-amino-4-(methylsulfonyl)butanoate hydrochloride (Compound SP718) (3.50 g, 13.7 mmol) in place of cyanomethyl 2-(methylamino)acetate hydrochloride (Compound SP703) under the same conditions as in the preparation example for Compound SP704.

LCMS (ESI) m/z=303 (M+H)+

Retention time: 1.28 min (analysis condition SMD-method7)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy) phosphoryl)oxy)methyl)-5-(6-amino-9H-purin-9-yl)-4-hydroxytetrahydrofuran-3-yl 4-(methylsulfonyl)-2-(pent-4-enamido)butanoate (Pen-Met(O₂)-pdCpA) (Compound SP720)

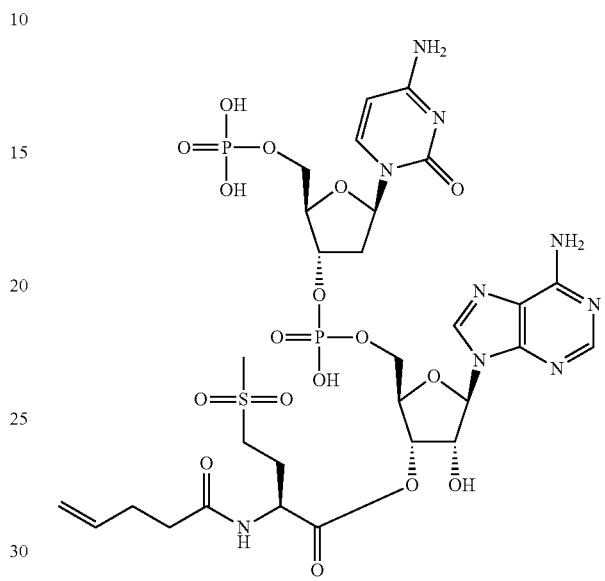

The title compound (Compound SP720) (153 mg, 11%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy) phosphoryl)oxy)tetrahydrofuran-2-yl)methyl dihydrogenphosphate (Compound 1h) (1.00 g, 1.57 mmol) and using (S)-cyanomethyl 4-(methylsulfonyl)-2-(pent-4-enamido)butanoate (Compound SP719) in place of cyanomethyl 2-(N-methylpent-4-enamido)acetate (Compound SP704) under the same conditions as in the preparation example for Compound SP705.

LCMS (ESI) m/z=882.3 (M+H)+

Retention time: 0.40 min (analysis condition SQDAA05)

Synthesis of Cyanomethyl 3-((tert-butoxycarbonyl)amino)propanoate (Compound SP722)

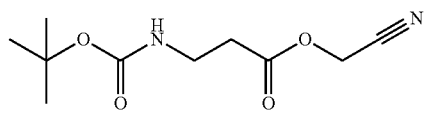 [SMILES: CC(C)(C)OC(=O)NCCC(=O)OCC#N]

Cyanomethyl 3-((tert-butoxycarbonyl)amino)propanoate (Compound SP722) (4.70 g, 78%) was obtained using 3-((tert-butoxycarbonyl)amino)propanoic acid (Compound SP721) (5.00 g, 26.4 mmol) in place of 2(-((tert-butoxycarbonyl)(methyl)amino)acetic acid (Compound SP701) under the same conditions as in the preparation example for Compound SP702.

2563
Synthesis of Cyanomethyl 3-aminopropanoate Hydrochloride (Compound SP723)

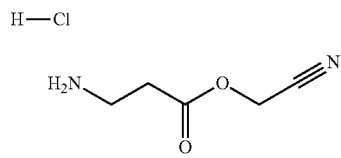

Cyanomethyl 3-aminopropanoate hydrochloride (Compound SP723) (3.00 g, 88%) was obtained as a crude product using cyanomethyl 3-((tert-butoxycarbonyl)amino)propanoate (Compound SP722) (4.70 g, 20.6 mmol) in place of cyanomethyl 2(-((tert-butoxycarbonyl)(methyl)amino)acetate (Compound SP702) under the same conditions as in the preparation example for Compound SP703. The crude product was directly used for the next reaction.

Synthesis of Cyanomethyl 3-(pent-4-enamido)propanoate (Compound SP724)

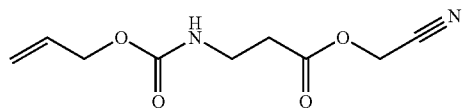

Cyanomethyl 3-(pent-4-enamido)propanoate (Compound SP724) (2.80 g, 73%) was obtained using cyanomethyl 3-aminopropanoate hydrochloride (Compound SP723) (3.00 g, 18.2 mmol) in place of cyanomethyl 2-(methylamino)acetate hydrochloride (Compound SP703) under the same conditions as in the preparation example for Compound SP704.

LCMS (ESI) m/z=211 (M+H)+
Retention time: 1.37 min (analysis condition SMD-method8)

2564
Synthesis of (2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(pent-4-enamido)propanoate (Pen-(3Ala-pdCpA) (Compound SP725)

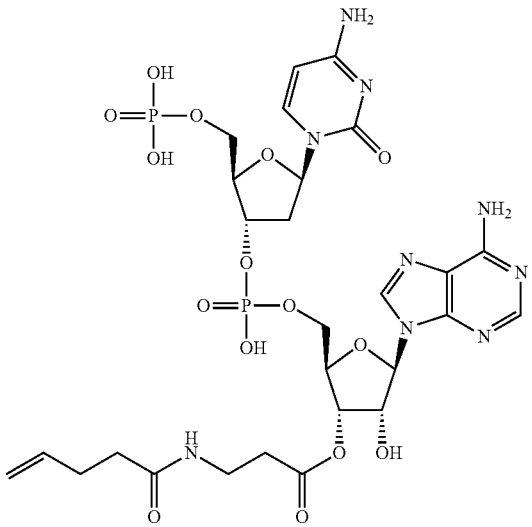 [SMILES: C=CCCC(=O)NCCC(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

The title compound (Compound SP725) (134 mg, 15%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (700 mg, 1.10 mmol) and using cyanomethyl 3-(pent-4-enamido)propanoate (Compound SP724) in place of cyanomethyl 2-(N-methyl-pent-4-enamido)acetate (Compound SP704) under the same conditions as in the preparation example for Compound SP705.

LCMS (ESI) m/z=790.6 (M+H)+
Retention time: 0.41 min (analysis condition SQDAA05)

Synthesis of (S)-2-((tert-butoxycarbonyl)(methyl)amino)-3-(thiazol-4-yl)propanoic Acid (Compound SP727)

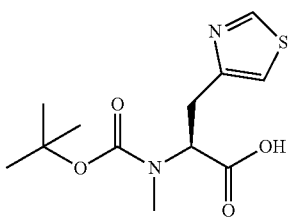 [SMILES: CN(C(=O)OC(C)(C)C)[C@@H](Cc1cscn1)C(=O)O]

A solution of (S)-2-((tert-butoxycarbonyl)amino)-3-(thiazol-4-yl)propanoic acid (Compound SP726) (800 mg, 2.94 mmol) in tetrahydrofuran (20 ml) was added dropwise to a suspension of sodium hydride (470 mg, 11.8 mmol, 60%) in tetrahydrofuran (30 ml) under a nitrogen atmosphere. Subsequently, iodomethane (1.67 g, 11.8 mmol) was added and the mixture was stirred at room temperature for 18 hours.

The reaction solution was adjusted to pH 4 with 6 mol/l aqueous hydrochloric acid and extracted with ethyl acetate. The organic extract was dried over sodium sulfate and then concentrated under reduced pressure, and the residue was purified by column chromatography (ethyl acetate) to afford (S)-2-((tert-butoxycarbonyl)(methyl)amino)-3-(thiazol-4-yl)propanoic acid (Compound SP727) (560 mg, 67%).

LCMS (ESI) m/z=287 (M+H)+

Retention time: 1.24 min (analysis condition SMD-method7)

Synthesis of (S)-cyanomethyl 2-((tert-butoxycarbonyl)(methyl)amino)-3-(thiazol-4-yl)propanoate (Compound SP728)

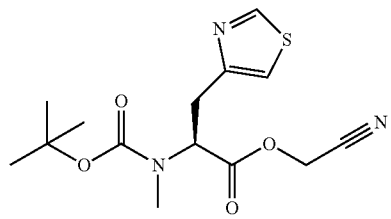 [SMILES: CN(C(=O)OC(C)(C)C)[C@@H](Cc1cscn1)C(=O)OCC#N]

(S)-Cyanomethyl 2-((tert-butoxycarbonyl)(methyl)amino)-3-(thiazol-4-yl)propanoate (Compound SP728) (3.04 g, 68%) was obtained using (S)-2-((tert-butoxycarbonyl)(methyl)amino)-3-(thiazol-4-yl)propanoic acid (Compound SP727) (3.94 g, 13.8 mmol) in place of 2(-((tert-butoxycarbonyl)(methyl)amino)acetic acid (Compound SP701) under the same conditions as in the preparation example for Compound SP702.

Synthesis of (S)-cyanomethyl 2-(methylamino)-3-(thiazol-4-yl)propanoate Hydrochloride (Compound SP729)

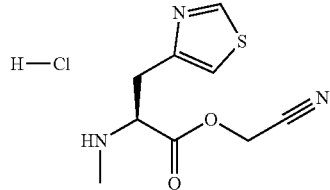

(S)-Cyanomethyl 2-(methylamino)-3-(thiazol-4-yl)propanoate hydrochloride (Compound SP729) (1.85 g, 76%) was obtained as a crude product using (S)-cyanomethyl 2-((tert-butoxycarbonyl)(methyl)amino)-3-(thiazol-4-yl)propanoate (Compound SP728) (3.04 g, 9.34 mmol) in place of cyanomethyl 2(-((tert-butoxycarbonyl)(methyl)amino)acetate (Compound SP702) under the same conditions as in the preparation example for Compound SP703. The crude product was directly used for the next reaction.

Synthesis of (S)-cyanomethyl 2-(N-methylpent-4-enamido)-3-(thiazol-4-yl)propanoate (Compound SP730)

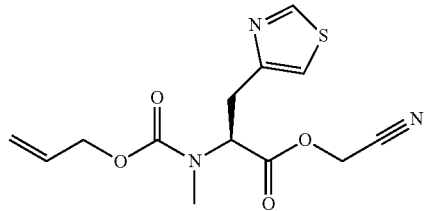 [SMILES: C=CCOC(=O)N(C)[C@@H](Cc1cscn1)C(=O)OCC#N]

The title compound (Compound SP730) (1.48 g, 68%) was obtained using (S)-cyanomethyl 2-(methylamino)-3-(thiazol-4-yl)propanoate hydrochloride (Compound SP729) (1.85 g, 7.07 mmol) in place of cyanomethyl 2-(methylamino)acetate hydrochloride (Compound SP703) under the same conditions as in the preparation example for Compound SP704.

LCMS (ESI) m/z=308 (M+H)+

Retention time: 1.28 min (analysis condition SMD-method7)

Synthesis of (2S)-(2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-(N-methylpent-4-enamido)-3-(thiazol-4-yl)propanoate (Pen-MeAla(4-Thz)-pdCpA) (Compound SP731)

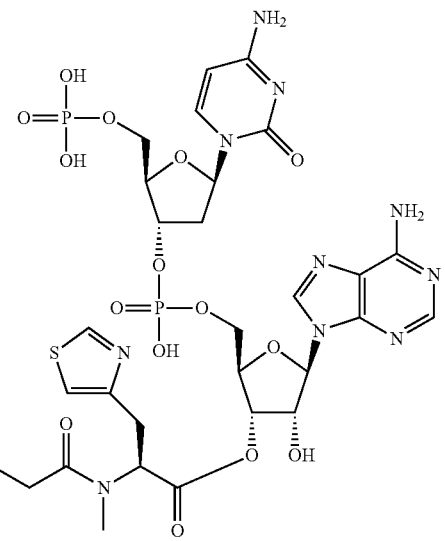

The title compound (Compound SP731) (60.9 mg, 6%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (700 mg, 1.10 mmol) and using (S)-cyanomethyl 2-(N-methylpent-4-enamido)-3-(thiazol-4-yl)propanoate (Compound SP730) in place of cyanomethyl 2-(N-methylpent-4-enamido)acetate (Compound SP704) under the same conditions as in the preparation example for Compound SP705.

LCMS (ESI) m/z=887.4 (M+H)+

Retention time: 0.40 min (analysis condition SQDFA05)

Synthesis of (S)-2-((tert-butoxycarbonyl)(methyl) amino)-3-(3-chlorophenyl)propanoic Acid (Compound SP733)

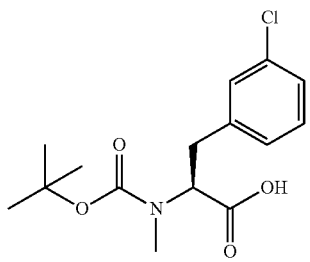 [SMILES: CN(C(=O)OC(C)(C)C)[C@@H](Cc1cccc(Cl)c1)C(=O)O]

(S)-2-((tert-Butoxycarbonyl)(methyl)amino)-3-(3-chlorophenyl)propanoic acid (Compound SP733) (5.10 g, 97%) was obtained using (S)-2-((tert-butoxycarbonyl)amino)-3-(3-chlorophenyl)propanoic acid (Compound SP732) (5.00 g, 16.7 mmol) in place of (S)-2-((tert-butoxycarbonyl)amino)-3-(thiazol-4-yl)propanoic acid (Compound SP726) under the same conditions as in the preparation example for Compound SP727.

Synthesis of (S)-cyanomethyl 2-((tert-butoxycarbonyl)(methyl)amino)-3-(3-chlorophenyl)propanoate (Compound SP734)

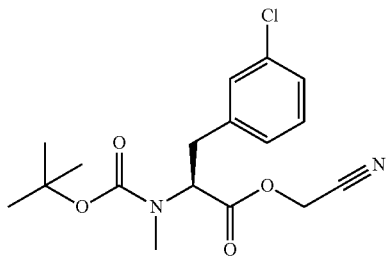 [SMILES: CN(C(=O)OC(C)(C)C)[C@@H](Cc1cccc(Cl)c1)C(=O)OCC#N]

(S)-Cyanomethyl 2-((tert-butoxycarbonyl)(methyl) amino)-3-(3-chlorophenyl)propanoate (Compound SP734) (4.75 g, 83%) was obtained using (S)-2-((tert-butoxycarbonyl)(methyl)amino)-3-(3-chlorophenyl)propanoic acid (Compound SP733) (5.10 g, 16.3 mmol) in place of 2-(((tert-butoxycarbonyl)(methyl)amino)acetic acid (Compound SP701) under the same conditions as in the preparation example for Compound SP702.

Synthesis of (S)-cyanomethyl 3-(3-chlorophenyl)-2-(methylamino)propanoate Hydrochloride (Compound SP735)

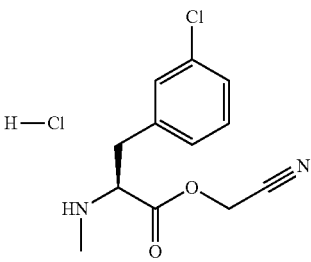 [SMILES: Cl ; CN[C@@H](Cc1cccc(Cl)c1)C(=O)OCC#N]

(S)-Cyanomethyl 3-(3-chlorophenyl)-2-(methylamino) propanoate hydrochloride (Compound SP735) (3.31 g, 84%) was obtained as a crude product using (S)-cyanomethyl 2-((tert-butoxycarbonyl)(methyl)amino)-3-(3-chlorophenyl) propanoate (Compound SP734) (4.75 g, 13.5 mmol) in place of cyanomethyl 2 (-((tert-butoxycarbonyl)(methyl)amino) acetate (Compound SP702) under the same conditions as in the preparation example for Compound SP703. The crude product was directly used for the next reaction.

Synthesis of (S)-cyanomethyl 3-(3-chlorophenyl)-2-(N-methylpent-4-enamido) Propanoate (Compound SP736, Pen-MePhe (3-Cl)—OCH₂CN)

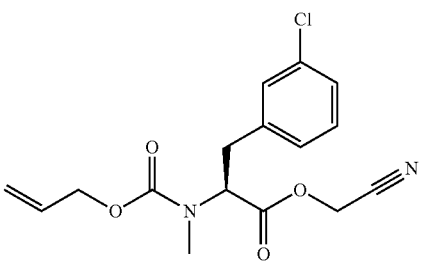 [SMILES: C=CCOC(=O)N(C)[C@@H](Cc1cccc(Cl)c1)C(=O)OCC#N]

(S)-Cyanomethyl 3-(3-chlorophenyl)-2-(N-methylpent-4-enamido)propanoate (Compound SP736) (2.72 g, 71%) was obtained using (S)-cyanomethyl 3-(3-chlorophenyl)-2-(methylamino)propanoate hydrochloride (Compound SP735) (3.31 g, 11.4 mmol) in place of cyanomethyl 2-(methylamino)acetate hydrochloride (Compound SP703) under the same conditions as in the preparation example for Compound SP704.

LCMS (ESI) m/z=335 (M+H)+

Retention time: 1.67 min (analysis condition SMD-method4)

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(3-chlorophenyl)-2-(N-methylpent-4-enamido)propanoate (PenMePhe(3-Cl)-pdCpA) (Compound SP737)

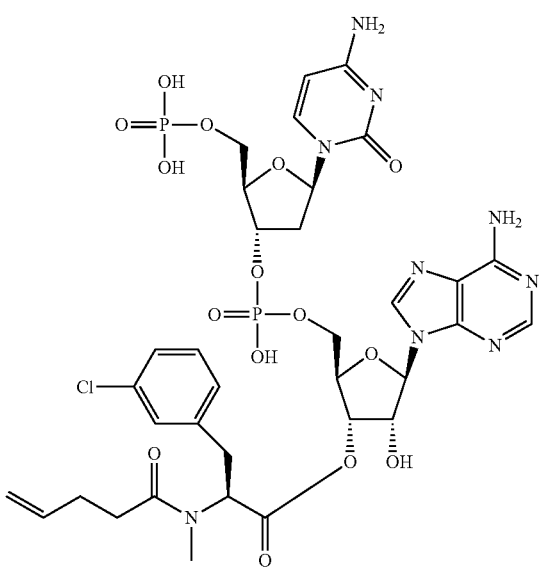 [SMILES: C=CCCC(=O)N(C)[C@@H](Cc1cccc(Cl)c1)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

The title compound (Compound SP737) (389 mg, 27%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (1.00 g, 1.57 mmol) and using (S)-cyanomethyl 3-(3-chlorophenyl)-2-(N-methylpent-4-enamido)propanoate (Compound SP736) in place of cyanomethyl 2-(N-methylpent-4-enamido)acetate (Compound SP704) under the same conditions as in the preparation example for Compound SP705.

LCMS (ESI) m/z=914.6 (M+H)+
Retention time: 0.75 min (analysis condition SQDAA05)

Synthesis of Cyanomethyl 2-((tert-butoxycarbonyl)(propyl)amino)acetate (Compound SP739)

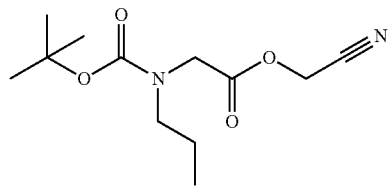 [SMILES: CCCN(CC(=O)OCC#N)C(=O)OC(C)(C)C]

Cyanomethyl 2-((tert-butoxycarbonyl)(propyl)amino)acetate (Compound SP739) (4.20 g, 71%) was obtained using 2-((tert-butoxycarbonyl) (propyl)amino)acetic acid (Compound SP738) (5.00 g, 23.0 mmol) in place of 2(-((tert-butoxycarbonyl)(methyl)amino)acetic acid (Compound SP701) under the same conditions as in the preparation example for Compound SP702.

Synthesis of Cyanomethyl 2-(propylamino)acetate Hydrochloride (Compound SP740)

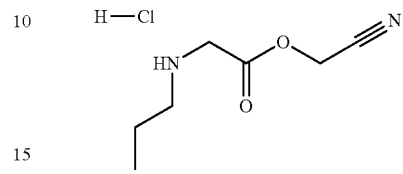

Cyanomethyl 2-(propylamino)acetate hydrochloride (Compound SP740) (2.50 g, 79%) was obtained as a crude product using cyanomethyl 2-((tert-butoxycarbonyl) (propyl)amino)acetate (Compound SP739) (4.20 g, 16.4 mmol) in place of cyanomethyl 2(-((tert-butoxycarbonyl)(methyl)amino)acetate (Compound SP702) under the same conditions as in the preparation example for Compound SP703. The crude product was directly used for the next reaction.

Synthesis of Cyanomethyl 2-(N-propylpent-4-enamido)acetate (Compound SP741, Pen-nPrGly-OCH$_2$CN)

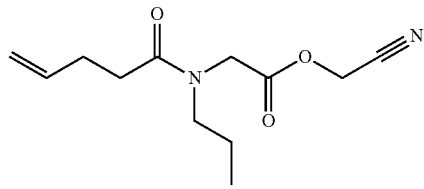 [SMILES: C=CCCC(=O)N(CCC)CC(=O)OCC#N]

Cyanomethyl 2-(N-propylpent-4-enamido)acetate (Compound SP741) (2.10 g, 67%) was obtained using cyanomethyl 2-(propylamino)acetate hydrochloride (Compound SP740) (2.55 g, 13.2 mmol) in place of cyanomethyl 2-(methylamino)acetate hydrochloride (Compound SP703) under the same conditions as in the preparation example for Compound SP704.

$^1$H-NMR (Bruker AVANCE II, 300 MHz, CDCl$_3$) δ ppm 6.19-6.32 (1H, m), 5.38-5.49 (2H, m), 5.17-5.22 (2H, m), 4.49-4.55 (2H, m), 3.70-3.78 (2H, m), 2.78-2.90 (4H, m), 1.84-2.07 (2H, m), 1.34 (3H, t, J=8.1 Hz)

Synthesis of (2R,3S,4R,5R)-2-((((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 2-(N-propylpent-4-enamido)acetate (Pen-nPrGly-pdCpA) (Compound SP742)

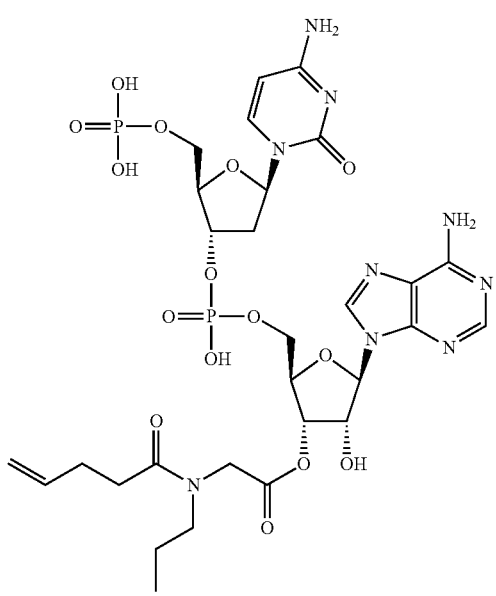 [SMILES: C=CCCC(=O)N(CCC)CC(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

The title compound (Compound SP742) (314 mg, 24%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (1.00 g, 1.57 mmol) and using cyanomethyl 2-(N-propylpent-4-enamido)acetate (Compound SP741) in place of cyanomethyl 2-(N-methylpent-4-enamido)acetate (Compound SP704) under the same conditions as in the preparation example for Compound SP705.

LCMS (ESI) m/z=818.4 (M+H)+
Retention time: 0.57 min (analysis condition SQDAA05)

Synthesis of (2S,4R)-1-tert-butyl 2-(cyanomethyl) 4-ethoxypyrrolidine-1,2-dicarboxylate (Compound SP751)

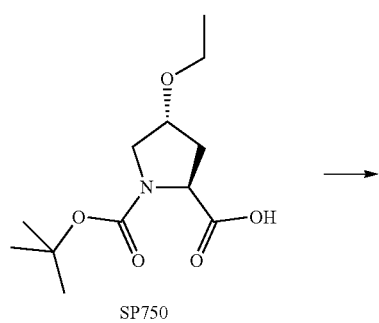

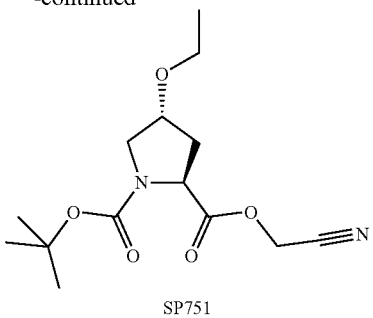

(2S,4R)-1-tert-Butyl 2-(cyanomethyl) 4-ethoxypyrrolidine-1,2-dicarboxylate (Compound SP751) (5.00 g, 91%) was obtained using (2S,4R)-1-(tert-butoxycarbonyl)-4-ethoxypyrrolidine-2-carboxylic acid (Compound SP750) (4.75 g, 18.3 mmol) in place of 2-(-((tert-butoxycarbonyl)(methyl)amino)acetic acid (Compound SP701) under the same conditions as in the preparation example for Compound SP702.

Synthesis of (2S,4R)-cyanomethyl 4-ethoxypyrrolidine-2-carboxylate Hydrochloride (Compound SP752)

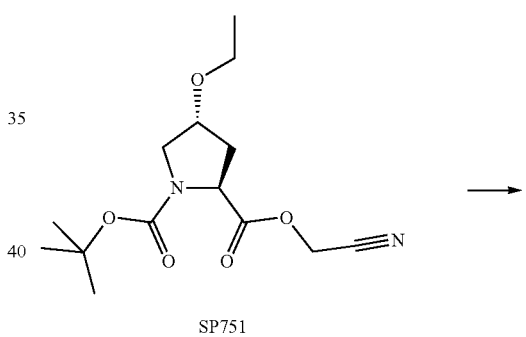

(2S,4R)-Cyanomethyl 4-ethoxypyrrolidine-2-carboxylate hydrochloride (Compound SP752) (3.25 g, 83%) was obtained using (2S,4R)-1-tert-butyl 2-(cyanomethyl) 4-ethoxypyrrolidine-1,2-dicarboxylate (Compound SP751) (5.00 g, 16.8 mmol) in place of cyanomethyl 2(-((tert-butoxycarbonyl)(methyl)amino)acetate (Compound SP702) under the same conditions as in the preparation example for Compound SP703.

2573

Synthesis of (2S,4R)-cyanomethyl 4-ethoxy-1-(pent-4-enoyl)pyrrolidine-2-carboxylate (Pen-Hyp(Et)-OCH₂CN) (Compound SP753)

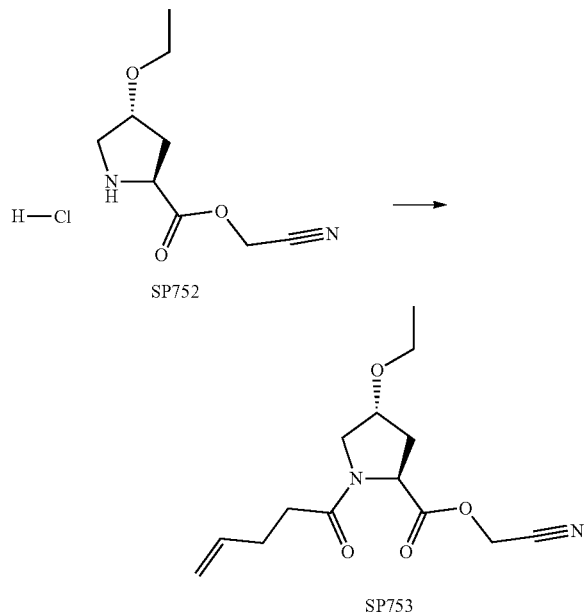

2574

(2S,4R)-Cyanomethyl 4-ethoxy-1-(pent-4-enoyl)pyrrolidine-2-carboxylate (Compound SP753) (2.75 g, 77%) was obtained using (2S,4R)-cyanomethyl 4-ethoxypyrrolidine-2-carboxylate hydrochloride (Compound SP752) (3.00 g, 12.8 mmol) in place of cyanomethyl 2-(methylamino)acetate hydrochloride (Compound SP703) under the same conditions as in the preparation example for Compound SP704.

LCMS (ESI) m/z=281 (M+H)+
Retention time: 1.45 minutes (analysis condition SMD-method4)

Synthesis of (2S,4R)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 4-ethoxy-1-(pent-4-enoyl)pyrrolidine-2-carboxylate (Pen-Hyp(Et)-pdCpA) (Compound SP754)

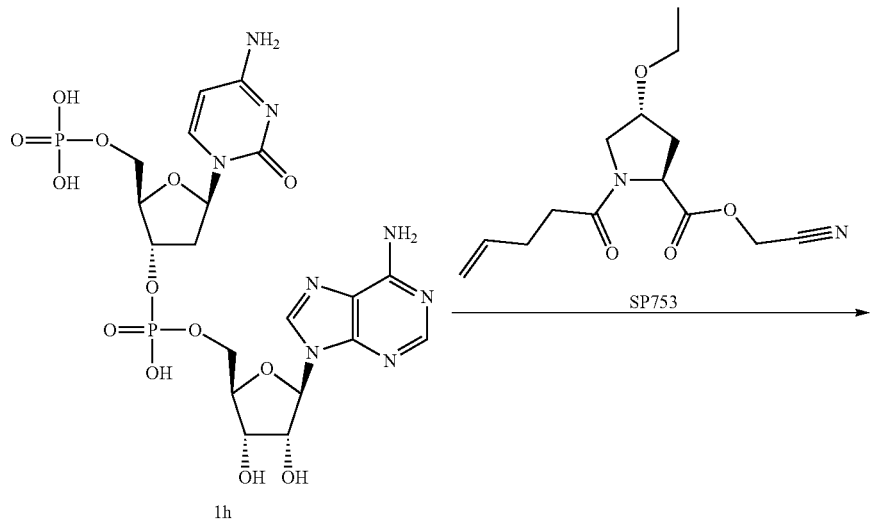

1h

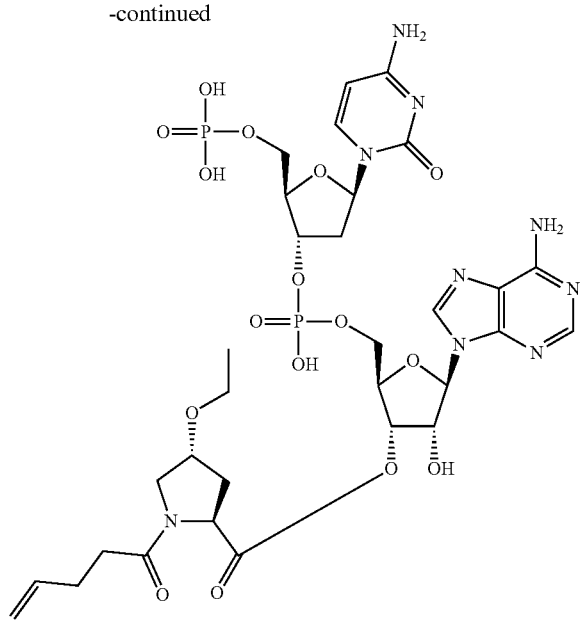

The title compound (Compound SP754) (154 mg, 11%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (1.00 g, 1.57 mmol) and using (2S,4R)-cyanomethyl 4-ethoxy-1-(pent-4-enoyl)pyrrolidine-2-carboxylate (Compound SP753) in place of cyanomethyl 2-(N-methylpent-4-enamido)acetate (Compound SP704) under the same conditions as in the preparation example for Compound SP705.

LCMS (ESI) m/z=860.4 (M+H)+

Retention time: 0.55 min (analysis condition SQDAA05)

Synthesis of (S)-3-(tert-butoxy)-2-(N-methylpent-4-enamido)propanoic Acid (Compound SP746)

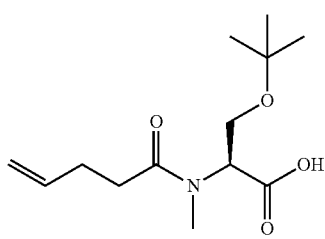 [SMILES: C=CCCC(=O)N(C)[C@@H](COC(C)(C)C)C(=O)O]

(S)-2-(3-(9H-fluoren-9-yl)-N-methylpropanamido)-8-(tert-butoxy)propanoic acid (Compound SP745) (4.35 g, 11.0 mmol) and diisopropylethylamine (EtN(iPr) 2) (10.4 mL, 60.0 mmol) were dissolved in dehydrated dichloromethane (46 ml), to the solution above, 2-chlorotrityl chloride resin (100-200 mesh, 1% DVB, purchased from Watanabe Chemical Industries, 4.65 g, 7.30 mmol) was added, and the amino acid was supported on the resin by shaking at room temperature for 60 minutes. The reaction solution was removed, and the resin was washed with dehydrated dichloromethane (46 ml) four times. A 20% solution of piperidine in N,N-dimethylformamide (15 ml) was added to the resin, and the Fmoc group was deprotected by shaking for 90 minutes. The reaction solution was removed, and the resin was washed with N,N-dimethylformamide (15 ml) three times. Subsequently, pent-4-enoic acid (2.3 ml, 21.9 mmol), 3H-(1,2,3)triazolo(4,5-b)pyridin-3-ol (HOAt) (1.99 g, 14.6 mmol) and N,N'-methanediylidenebis(propan-2-amine) (DIC, 3.71 ml, 24.1 mmol) were dissolved in N,N-dimethylformamide (15 ml), the solution was added to the resin, and the mixture was shaken at room temperature for 60 minutes for pentenoylation. The reaction solution was removed, and the resin was washed with N,N-dimethylformamide (15 ml) three times and then further washed with dichloromethane (15 ml) three times. Subsequently, a 1% solution of trifluoroacetic acid in dichloromethane (1% TFA in CH$_2$Cl$_2$) (40 ml) was added to the aforementioned resin, and the amino acid was cleaved from the resin by shaking for 30 minutes. The reaction solution was collected, and the resin was washed with dichloromethane (40 ml) three times. The collected reaction solution was concentrated under reduced pressure, and the residue was purified by reverse-phase silica gel column chromatography (10 mM aqueous ammonium acetate solution/methanol solution) to afford (S)-3-(tert-butoxy)-2-(N-methylpent-4-enamido)propanoic acid (Compound SP746) (1.02 g, 54%). Dichloromethane and N,N-dimethylformamide used for this synthesis were special grade solvents for peptide synthesis. (purchased from Watanabe Chemical Industries).

LCMS (ESI) m/z=258 (M+H)+

Retention time: 0.71 min (analysis condition SQDAA05)

Synthesis of (S)-cyanomethyl 3-(tert-butoxy)-2-(N-methylpent-4-enamido)propanoate (Compound SP747)

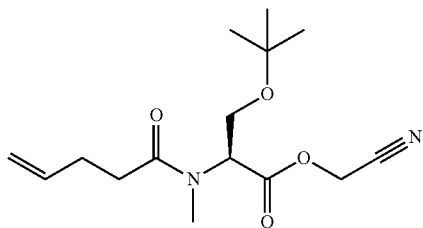 [SMILES: C=CCCC(=O)N(C)[C@@H](COC(C)(C)C)C(=O)OCC#N]

(S)-3-(tert-butoxy)-2-(N-methylpent-4-enamido)propanoic acid (Compound SP746) (1.01 g, 3.92 mmol) and N-ethylisopropylpropan-2-amine (EtN(iPr) 2, 1.37 mL, 7.85 mmol) were dissolved in N,N-dimethylformamide (3.92 ml) under a nitrogen atmosphere, 2-bromoacetonitrile (0.82 ml, 11.8 mmol) was added and the mixture was stirred at room temperature for 45 minutes. 50 ml of ethyl acetate was added to the reaction solution, and the organic layer was separated by 50 ml of a saturated aqueous ammonium chloride solution and 50 ml of brine. The organic layer was collected and concentrated under reduced pressure, and the residue was purified by reverse-phase silica gel column chromatography (10 mM aqueous ammonium acetate solution/methanol solution) to afford (S)-cyanomethyl 3-(tert-butoxy)-2-(N-methylpent-4-enamido)propanoate (Compound SP747) (1.00 g, 86%).

LCMS (ESI) m/z=297.6 (M+H)+
Retention time: 0.77 min (analysis condition SQDFA05)

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-(tert-butoxy)-2-(N-methylpent-4-enamido)propanoate (Compound SP748, Pen-MeSer(tBu)-pdCpA)

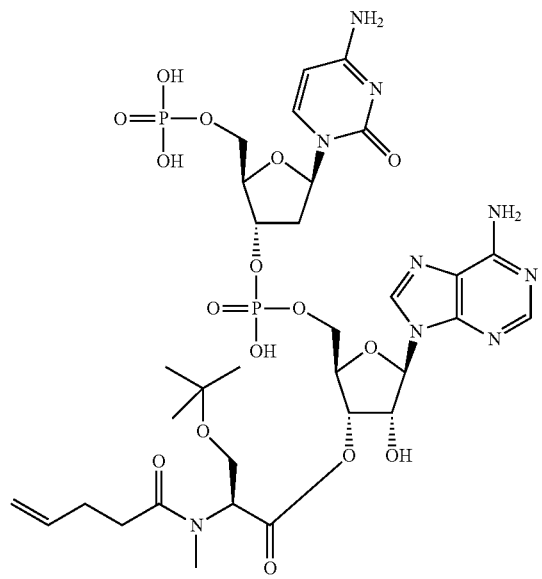 [SMILES: C=CCCC(=O)N(C)[C@@H](COC(C)(C)C)C(=O)O[C@H]1[C@@H](O)[C@H](n2cnc3c(N)ncnc32)O[C@@H]1COP(=O)(O)O[C@H]1C[C@H](n2ccc(N)nc2=O)O[C@@H]1COP(=O)(O)O]

The title compound (Compound SP748) (300 mg, 42%) was obtained using ((2R,3S,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)tetrahydrofuran-2-yl)methyl dihydrogenphosphate (Compound 1h) (519 mg, 0.816 mmol) and using (S)-cyanomethyl 3-(tert-butoxy)-2-(N-methylpent-4-enamido)propanoate (Compound SP747) in place of cyanomethyl 2-(methylamino)acetate hydrochloride (Compound SP704) under the same conditions as in the preparation example for Compound SP705.

LCMS (ESI) m/z=876.7 (M+H)+
Retention time: 0.47 min (analysis condition SQDFA05)

Synthesis of (2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-hydroxy-2-(N-methylpent-4-enamido)propanoate (Pen-MeSer-pdCpA) (Compound SP749)

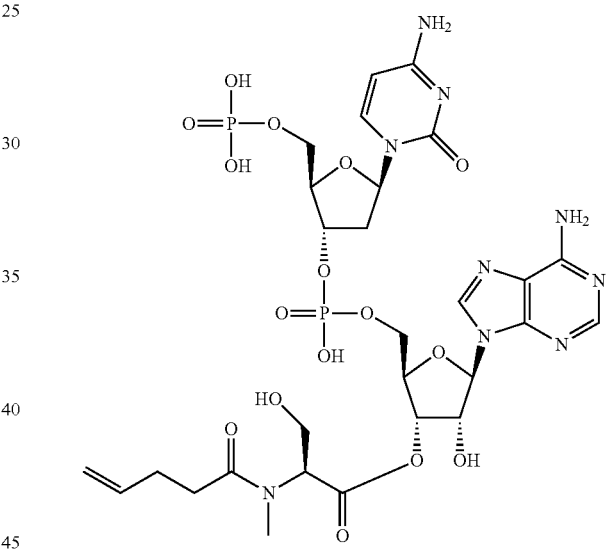

(2S)-(2R,3S,4R,5R)-2-(((((2R,3S,5R)-5-(4-amino-2-oxopyrimidin-1(2H)-yl)-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (Compound SP748) (299 mg, 0.341 mmol) was dissolved in trifluoroacetic acid (3.38 ml, 43.9 mmol), and the mixture was stirred for 30 minutes. The reaction solution was concentrated under reduced pressure, and the residue was purified by reverse-phase silica gel column chromatography (0.1% formic acid aqueous solution/acetonitrile solution) to afford the title compound (Compound SP749) (144 mg, 52%).

LCMS (ESI) m/z=820.5 (M+H)+
Retention time: 0.31 min (analysis condition SQDFA05)

2. Synthesis of Transcribed tRNAs and Transcribed tRNAs (Lacking CA) for Constructing a Display Library Transcribed tRNAs and transcribed tRNAs (lacking CA) used for panning were prepared as follows.

tRNAs (-CA) (SEQ ID NO: MTL-1 to 12) lacking 3'-end CA and transcribed tRNAs (SEQ ID NO: NTL-13 to 14) were synthesized from template DNAs (SEQ ID NO: DTL-1 to 14) by in vitro transcription using RiboNAX Large Scale RNA production System T7 (Promega, P1300) and purified with RNeasy Maxi kit (Qiagen). The in vitro transcription was carried out under conditions where the GTP concentration was reduced to 3.75 mM and GMP was additionally used at 7.5 mM in the standard protocol of Promega. ATP, CTP and UTP were used at 7.5 mM each in accordance with the standard protocol.

SEQ ID NO: DTL-1
tRNAGluCUG (-CA) CAG DNA sequence:
(SEQ ID NO: 99)
GGCGTAATACGACTCACTATAGTCCCCTTCGTCTAGAGGCCCAGGACAC CGCCCTctgACGGCGGTAACAGGGGTTCGAATCCCCTAGGGGACGC SEQ ID NO: DTL-2
tRNAGluACG (-CA) CGU DNA sequence:
(SEQ ID NO: 100)
GGCGTAATACGACTCACTATAGTCCCCTTCGTCTAGAGGCCCAGGACAC CGCCCTacgACGGCGGTAACAGGGGTTCGAATCCCCTAGGGGACGC SEQ ID NO: DTL-3
tRNAGluUUC (-CA) GAA DNA sequence:
(SEQ ID NO: 101)
GGCGTAATACGACTCACTATAGTCCCCTTCGTCTAGAGGCCCAGGACAC CGCCCTttcACGGCGGTAACAGGGGTTCGAATCCCCTAGGGGACGC SEQ ID NO: DTL-4
tRNAGluCCU (-CA) AGG DNA sequence:
(SEQ ID NO: 102)
GGCGTAATACGACTCACTATAGTCCCCTTCGTCTAGAGGCCCAGGACAC CGCCCTcctACGGCGGTAACAGGGGTTCGAATCCCCTAGGGGACGC SEQ ID NO: DTL-5
tRNAGluCAA (-CA) UUG DNA sequence:
(SEQ ID NO: 103)
GGCGTAATACGACTCACTATAGTCCCCTTCGTCTAGAGGCCCAGGACAC CGCCCTcaaACGGCGGTAACAGGGGTTCGAATCCCCTAGGGGACGC SEQ ID NO: DTL-6
tRNAGluUAG (-CA) CUA DNA sequence:
(SEQ ID NO: 104)
GGCGTAATACGACTCACTATAGTCCCCTTCGTCTAGAGGCCCAGGACAC CGCCCTtagACGGCGGTAACAGGGGTTCGAATCCCCTAGGGGACGC SEQ ID NO: DTL-7
tRNAGluCUA (-CA) UAG DNA sequence:
(SEQ ID NO: 105)
GGCGTAATACGACTCACTATAGTCCCCTTCGTCTAGAGGCCCAGGACAC CGCCCTctaACGGCGGTAACAGGGGTTCGAATCCCCTAGGGGACGC SEQ ID NO: DTL-8
tRNAGluCCG (-CA) CGG DNA sequence:
(SEQ ID NO: 106)
GGCGTAATACGACTCACTATAGTCCCCTTCGTCTAGAGGCCCAGGACAC CGCCCTccgACGGCGGTAACAGGGGTTCGAATCCCCTAGGGGACGC SEQ ID NO: DTL-9
tRNAGluAAG (-CA) CUU DNA sequence:
(SEQ ID NO: 107)
GGCGTAATACGACTCACTATAGTCCCCTTCGTCTAGAGGCCCAGGACAC CGCCCTaagACGGCGGTAACAGGGGTTCGAATCCCCTAGGGGACGC SEQ ID NO: DTL-10
tRNAGluGCA (-CA) UGC DNA sequence:
(SEQ ID NO: 108)
GGCGTAATACGACTCACTATAGTCCCCTTCGTCTAGAGGCCCAGGACAC CGCCCTgcaACGGCGGTAACAGGGGTTCGAATCCCCTAGGGGACGC SEQ ID NO: DTL-11
tRNAGluCAU (-CA) AUG DNA sequence:
(SEQ ID NO: 109)
GGCGTAATACGACTCACTATAGTCCCCTTCGTCTAGAGGCCCAGGACAC CGCCCTcatACGGCGGTAACAGGGGTTCGAATCCCCTAGGGGACGC SEQ ID NO: DTL-12
tRNAAsn-E2GUU (-CA) AAC DNA sequence:
(SEQ ID NO: 110)
GGCGTAATACGACTCACTATAGGCTCTGTAGTTCAGTCGGTAGAACGGC GGACTgttAATCCGTATGTCACTGGTTCGAGTCCAGTCAGAGCCGC SEQ ID NO: DTL-13
tRNAAla1B DNA sequence:
(SEQ ID NO: 111)
GGCGTAATACGACTCACTATAGGGGCTATAGCTCAGCTGGGAGAGCGCC

TGCTTAGCACGCAGGAGGTCTGCGGTTCGATCCCGCATAGCTCCACCA

SEQ ID NO: DTL-14
tRNATyr1 DNA sequence:
(SEQ ID NO: 112)
GGCGTAATACGACTCACTATAGGTGGGGTTCCCGAGCGGCCAAAGGGAG

CAGACTGTAAATCTGCCGTCATCGACTTCGAAGGTTCGAATCCTTCCCC

CACCACCA

SEQ ID MTL-1
tRNAGluCUG (-CA) RNA sequence:
(SEQ ID NO: 113)
GUCCCCUUCGUCUAGAGGCCCAGGACACCGCCCUcugACGGCGGUAACA

GGGGUUCGAAUCCCCUAGGGGACGC

SEQ ID MTL-2
tRNAGluACG (-CA) RNA sequence:
(SEQ ID NO: 114)
GUCCCCUUCGUCUAGAGGCCCAGGACACCGCCCUacgACGGCGGUAACA

GGGGUUCGAAUCCCCUAGGGGACGC

SEQ ID MTL-3
tRNAGluUUC (-CA) RNA sequence:
(SEQ ID NO: 115)
GUCCCCUUCGUCUAGAGGCCCAGGACACCGCCCUuucACGGCGGUAACA

GGGGUUCGAAUCCCCUAGGGGACGC

SEQ ID MTL-4
tRNAGluCCU (-CA) RNA sequence:
(SEQ ID NO: 116)
GUCCCCUUCGUCUAGAGGCCCAGGACACCGCCCUccuACGGCGGUAACA

GGGGUUCGAAUCCCCUAGGGGACGC

SEQ ID MTL-5
tRNAGluCAA (-CA) RNA sequence:
(SEQ ID NO: 117)
GUCCCCUUCGUCUAGAGGCCCAGGACACCGCCCUcaaACGGCGGUAACA

GGGGUUCGAAUCCCCUAGGGGACGC

SEQ ID MTL-6
tRNAGluUAG (-CA) RNA sequence:
(SEQ ID NO: 118)
GUCCCCUUCGUCUAGAGGCCCAGGACACCGCCCUuagACGGCGGUAACA

GGGGUUCGAAUCCCCUAGGGGACGC

SEQ ID MTL-7
tRNAGluCUA (-CA) RNA sequence:

-continued

SEQ ID MTL-7 (continued)
(SEQ ID NO: 119)
GUCCCCUUCGUCUAGAGGCCCAGGACACCGCCCUcuaACGGCGGUAACA

GGGGUUCGAAUCCCCUAGGGGACGC

SEQ ID MTL-8
tRNAGluCCG (-CA) RNA sequence:
(SEQ ID NO: 120)
GUCCCCUUCGUCUAGAGGCCCAGGACACCGCCCUccgACGGCGGUAACA

GGGGUUCGAAUCCCCUAGGGGACGC

SEQ ID MTL-9
tRNAGluAAG (-CA) RNA sequence:
(SEQ ID NO: 121)
GUCCCCUUCGUCUAGAGGCCCAGGACACCGCCCUaagACGGCGGUAACA

GGGGUUCGAAUCCCCUAGGGGACGC

SEQ ID MTL-10
tRNAGluGCA (-CA) RNA sequence:
(SEQ ID NO: 122)
GUCCCCUUCGUCUAGAGGCCCAGGACACCGCCCUgcaACGGCGGUAACA

GGGGUUCGAAUCCCCUAGGGGACGC

SEQ ID MTL-11
tRNAGluCAU (-CA) RNA sequence:
(SEQ ID NO: 123)
GUCCCCUUCGUCUAGAGGCCCAGGACACCGCCCUcauACGGCGGUAACA

GGGGUUCGAAUCCCCUAGGGGACGC

SEQ ID MTL-12
tRNAAsn-E2GUU (-CA) RNA sequence:
(SEQ ID NO: 124)
GGCUCUGUAGUUCAGUCGGUAGAACGGCGGACUguuAAUCCGUAUGUCA

CUGGUUCGAGUCCAGUCAGAGCCGC

SEQ ID MTL-13
tRNAAla1B RNA sequence:
(SEQ ID NO: 125)
GGGGCUAUAGCUCAGCUGGGAGAGCGCCUGCUUAGCACGCAGGAGGUCU

GCGGUUCGAUCCCGCAUAGCUCCACCA

SEQ ID MTL-14
tRNATyr1 RNA sequence:
(SEQ ID NO: 126)
GGUGGGGUUCCCGAGCGGCCAAAGGGAGCAGACUGUAAAUCUGCCGUCA

UCGACUUCGAAGGUUCGAAUCCUUCCCCCACCACCA

3. Synthesis of tRNA-Amino Acid Complexes by Reaction of tRNAs (Lacking CA) and pdCpA-Amino Acids Synthesis of Aminoacylated tRNAs for Panning (Compounds ATL-1 to 13) by Ligation of Aminoacylated pdCpAs and Transcribed tRNAs (Lacking CA), and Preparation of Aminoacylated tRNA Mixtures First, aminoacylated tRNAs (Compounds ATL-1 to 13) were individually prepared. Ligation was carried out with ligation buffer (50 mM HEPES-KOH pH 7.5, 20 mM MgCl2, 1 mM ATP) containing 25 μM transcribed tRNA (-CA) (SEQ ID NO: MTL-1 to 12, R-5), 0.6 U/μl T4 RNA ligase (New England Biolabs) and 0.5 mM aminoacylated pdCpA. 25 μM transcribed tRNAs (-CA) and corresponding 0.5 mM aminoacylated pdCpAs were illustrated in the following Tables 20 to 22.

Prior to ligation, a mixture of ligation buffer, transcribed tRNA (-CA) (SEQ ID NO: MIL-1 to 12, R-5) and nuclease free water was heated at 95° C. for 2 minutes and then allowed to stand at room temperature for 5 minutes to refold tRNA. A solution of T4 RNA ligase and aminoacylated pdCpA in DMSO was then added as described above, and ligation reaction was carried out at 15° C. for 45 minutes.

0.3 M sodium acetate and 62.5 mM iodine (water:THF=1:1 solution) were added to the ligation reaction solution, and the pentenoyl group was deprotected at room temperature for 1 hour (at room temperature for 5 minutes when Compound SP749 was used) to afford Compounds ATL-1 to 12. When Compound 6i-C not having a pentenoyl group was used, the ligation reaction was carried out without deprotection to afford Compound ATL-13.

Next, an aminoacylated tRNA mixture for Translation Solution S (used for initiation suppression translation), initiator aminoacylated tRNA for Translation Solution S (used for initiation suppression translation), and an aminoacylated tRNA mixture for Translation Solution T (used for read through translation) were prepared. The obtained Compounds ATL-1 to 13 were mixed at mixing ratios as shown in Tables 20 to 22, extracted with phenol as an aminoacylated tRNA mixture for Translation Solution S, initiator aminoacylated tRNA for Translation Solution S and an aminoacylated tRNA mixture for Translation Solution T, and then collected by ethanol precipitation. The prepared aminoacylated tRNAs were dissolved in 1 mM sodium acetate immediately prior to addition to the translation solutions. Hereinafter, translation solutions were prepared at final concentrations as shown in Tables 20 to 22 when they were used for translation.

TABLE 20

Correspondence table for aminoacylated tRNA synthesis
(aminoacylated tRNA mixture for Translation Solution S)

| Transcribed tRNA (-CA) SEQ ID NO: | Aminoacylated pdCpA | Aminoacylated tRNA | Mixing ratio | Final concentration in the translation solution (μM) |
|---|---|---|---|---|
| MTL-1 | Compound SP725 | Compound ATL-1 | 2 | 20 |
| MTL-2 | Compound 1i-IA | Compound ATL-2 | 2 | 20 |
| MTL-3 | Compound SP731 | Compound ATL-3 | 1 | 10 |
| MTL-4 | Compound SP737 | Compound ATL-4 | 1 | 10 |
| MTL-5 | Compound SP705 | Compound ATL-5 | 1 | 10 |
| MTL-6 | Compound SP715 | Compound ATL-6 | 1 | 10 |
| MTL-7 | Compound SP754 | Compound ATL-7 | 1 | 10 |
| MTL-8 | Compound SP749 | Compound ATL-8 | 1 | 10 |
| MTL-9 | Compound SP710 | Compound ATL-9 | 2 | 20 |
| MTL-10 | Compound SP720 | Compound ATL-10 | 1 | 10 |
| MTL-12 | Compound SP742 | Compound ATL-12 | 1 | 10 |

TABLE 21

Correspondence table for aminoacylated tRNA synthesis (aminoacylated initiator tRNA for Translation Solution S)

| Transcribed tRNA (-CA) SEQ ID NO: | Aminoacylated pdCpA | Aminoacylated tRNA | Final concentration in the translation solution (μM) |
|---|---|---|---|
| R-5 | Compound 6i-C | Compound ATL-13 | 25 |

TABLE 22

Correspondence table for aminoacylated tRNA synthesis (aminoacylated tRNA mixture for Translation Solution T)

| Transcribed tRNA (-CA) SEQ ID NO: | Aminoacylated pdCpA | Aminoacylated tRNA | Mixing ratio | Final concentration in the translation solution (μM) |
|---|---|---|---|---|
| MTL-1 | Compound SP725 | Compound ATL-1 | 2 | 20 |
| MTL-2 | Compound 1i-IA | Compound ATL-2 | 2 | 20 |
| MTL-3 | Compound SP731 | Compound ATL-3 | 1 | 10 |
| MTL-4 | Compound SP737 | Compound ATL-4 | 1 | 10 |
| MTL-5 | Compound SP705 | Compound ATL-5 | 1 | 10 |
| MTL-6 | Compound SP715 | Compound ATL-6 | 1 | 10 |
| MTL-7 | Compound SP754 | Compound ATL-7 | 1 | 10 |
| MTL-8 | Compound SP749 | Compound ATL-8 | 1 | 10 |
| MTL-9 | Compound SP710 | Compound ATL-9 | 2 | 20 |
| MTL-11 | Compound SP720 | Compound ATL-11 | 1 | 10 |
| MTL-12 | Compound SP742 | Compound ATL-12 | 1 | 10 |

(SEQ ID NO: 127)

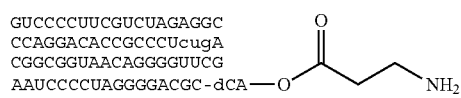

```
GUCCCCUUCGUCUAGAGGC
CCAGGACACCGCCCUcugA
CGGCGGUAACAGGGGUUCG
AAUCCCCUAGGGGACGC-dCA
```

Compound ATL-1 βAla-tRNAGluCUG (-CA)

(SEQ ID NO: 128)

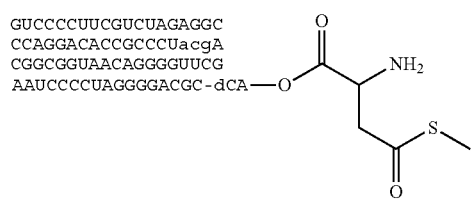

```
GUCCCCUUCGUCUAGAGGC
CCAGGACACCGCCCUacgA
CGGCGGUAACAGGGGUUCG
AAUCCCCUAGGGGACGC-dCA
```

Compound ATL-2 Asp(SMe)-tRNAGluACG (-CA)

(SEQ ID NO: 129)

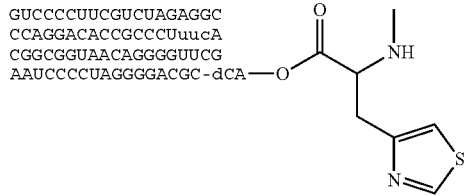

```
GUCCCCUUCGUCUAGAGGC
CCAGGACACCGCCCUuucA
CGGCGGUAACAGGGGUUCG
AAUCCCCUAGGGGACGC-dCA
```

Compound ATL-3 MeAla(4-Thz)-tRNAGluUUC (-CA)

(SEQ ID NO: 130)

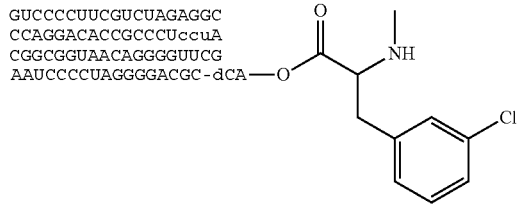

```
GUCCCCUUCGUCUAGAGGC
CCAGGACACCGCCCUccuA
CGGCGGUAACAGGGGUUCG
AAUCCCCUAGGGGACGC-dCA
```

Compound ATL-4 MePhe(3-Cl)-tRNAGluCCU (-CA)

(SEQ ID NO: 131)

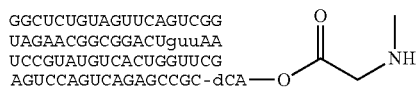

```
GGCUCUGUAGUUCAGUCGG
UAGAACGGCGGACUguuAA
UCCGUAUGUCACUGGUUCG
AGUCCAGUCAGAGCCGC-dCA
```

Compound ATL-5 MeGly-tRNAGluCAA (-CA)

(SEQ ID NO: 132)

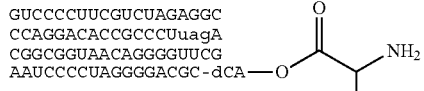

```
GUCCCCUUCGUCUAGAGGC
CCAGGACACCGCCCUuagA
CGGCGGUAACAGGGGUUCG
AAUCCCCUAGGGGACGC-dCA
```

Compound ATL-6 Phe(4-CF3)-tRNAGluUAG (-CA)

(SEQ ID NO: 133)

```
GUCCCCUUCGUCUAGAGGC
CCAGGACACCGCCCUuagA
CGGCGGUAACAGGGGUUCG
AAUCCCCUAGGGGACGC-dCA
```
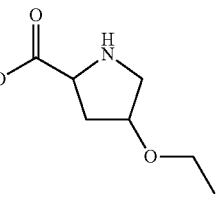

Compound ATL-7 Hyp(Et)-tRNAGluCUA (-CA)

(SEQ ID NO: 134)

```
GUCCCCUUCGUCUAGAGGC
CCAGGACACCGCCCUccgA
CGGCGGUAACAGGGGUUCG
AAUCCCCUAGGGGACGC-dCA
```
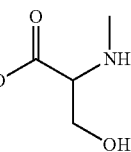

Compound ATL-8 MeSer-tRNAGluCCG (-CA)

(SEQ ID NO: 135)

```
GUCCCCUUCGUCUAGAGGC
CCAGGACACCGCCCUaagA
CGGCGGUAACAGGGGUUCG
AAUCCCCUAGGGGACGC-dCA
```
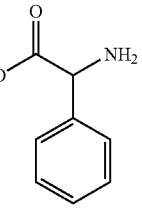

Compound ATL-9 Phg-tRNAGluAAG (-CA)

(SEQ ID NO: 136)

```
GUCCCCUUCGUCUAGAGGC
CCAGGACACCGCCCUgcaA
CGGCGGUAACAGGGGUUCG
AAUCCCCUAGGGGACGC-dCA
```
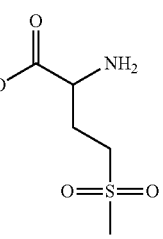

Compound ATL-10 Met(O2)-tRNAGluGCA (-CA)

(SEQ ID NO: 137)

```
GUCCCCUUCGUCUAGAGGC
CCAGGACACCGCCCUcauA
CGGCGGUAACAGGGGUUCG
AAUCCCCUAGGGGACGC-dCA
```
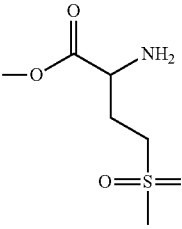

Compound ATL-11 Met(O2)-tRNAGluCAU (-CA)

(SEQ ID NO: 138)

```
GUCCCCUUCGUCUAGAGGC
CCAGGACACCGCCCUcauA
CGGCGGUAACAGGGGUUCG
AAUCCCCUAGGGGACGC-dCA
```
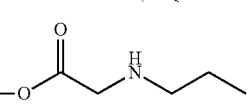

Compound ATL-12 nPrGly-tRNAAsn-E2GUU (-CA)

(SEQ ID NO: 139)

```
GGCGGGGUGGAGCAGCCUG
GUAGCUCGUCGGGCUcauA
ACCCGAAGAUCGUCGGUUC
AAAUCCGGCCCCCGCAAC-dCA
```
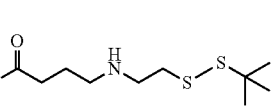

Compound ATL-13 tBuSSEtGABA-tRNAfMetCAU (-CA)

4. Synthesis of Codon Units for Constructing Random DNAs to Construct a Display Library ATG, GTT, CCG, ACT, GCT, CAT, TGG, GGT, TAC, CAG, AAC, TGC and GAA units were purchased from Glen Research, respectively. TTT (Compound SP779), ATT (Compound SP780), AGT (Compound SP768), CGG (Compound SP781), AGG (Compound SP782), TTG (Compound SP775), CTT (Compound SP776), CTA (Compound SP777) and TAG (Compound SP778) trimer phosphoramidite units were synthesized according to the following scheme, respectively. The above compounds can also be synthesized by the synthetic method in the literature, Yagodkin, A.; Azhayev, A.; Roivainen, J.: Antopolsky, M.; Kayushin, A.; Korosteleva, M.; Miroshnikov, A.; Randolph, J.; and Mackie, H. Nucleosides, Nucleotides, and Nucleic Acids 2007, 26, 473-497. Codon units are herein defined as compounds formed by DNA-like trinucleotides linked by phosphodiester bonds, the compounds that can be applied to chemical DNA synthesis. For example, the CAG unit is a compound having a hydroxyl group at the 5'-position that is protected by a 4,4'-dimethoxytrityl group (DMT) and a phosphate is protected by a 2-chlorophenyl group, having amino group-protected nucleobases defined by the following scheme (C(Bz), A(Bz) and G(iBu)) continuously from the 5'-side, and having a N,N'-diisopropylaminophosphoramidite group that is protected by a cyanoethyl group at the 3'-end.

2587 2588
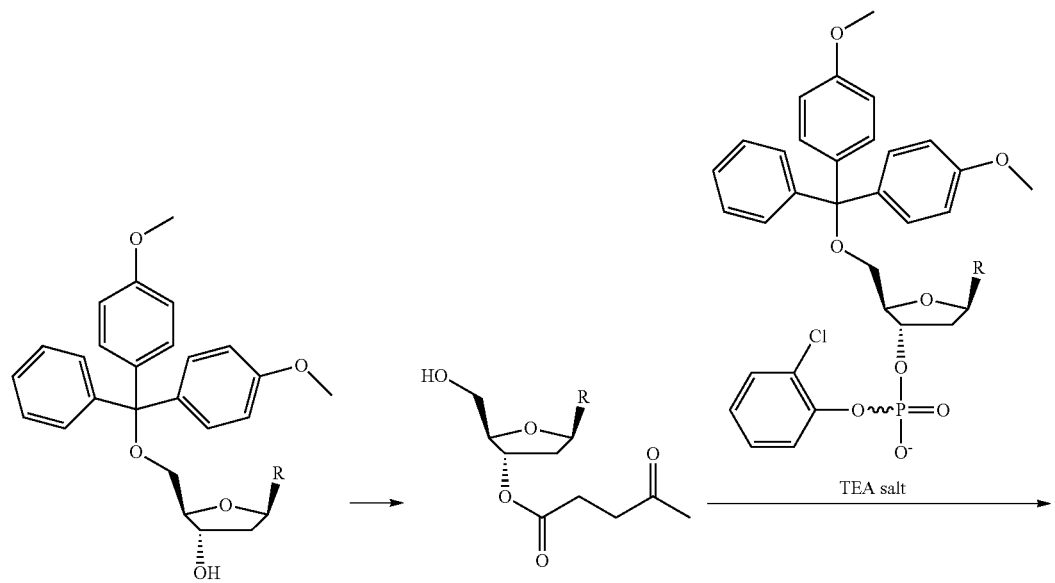
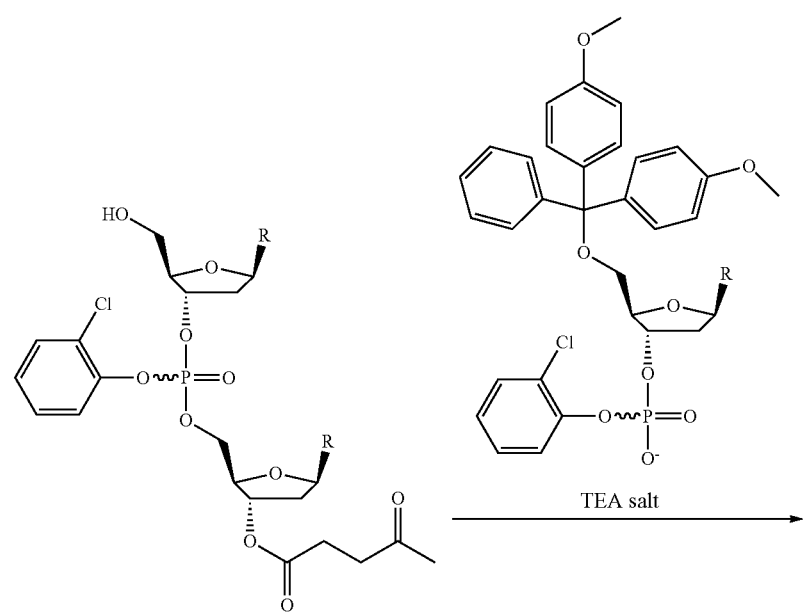

2589

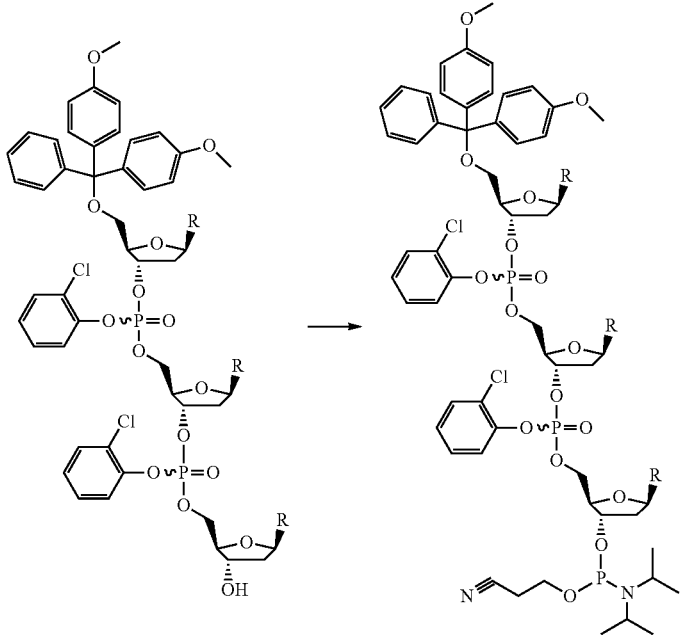

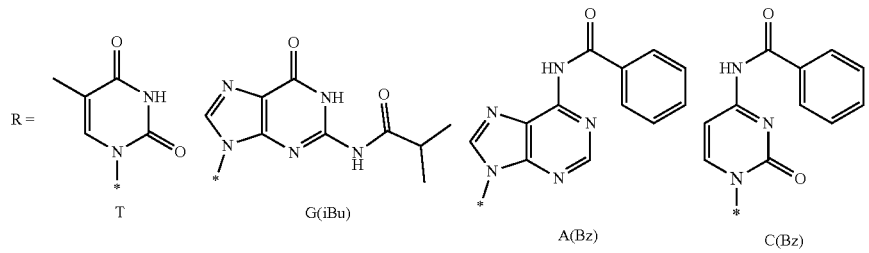

Synthesis of [(2R,3S,5R)-2-(hydroxymethyl)-5-(5-methyl-2,4-dioxopyrimidin-1-yl)oxolan-3-yl] 4-oxo-pentanoate (Compound SP762)

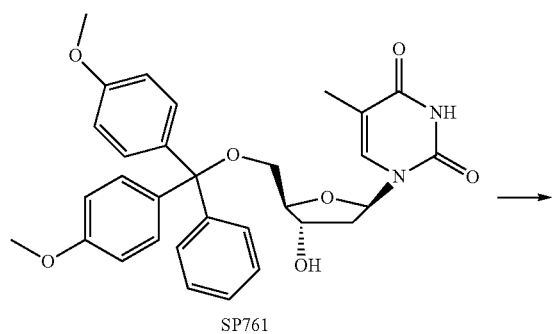

-continued

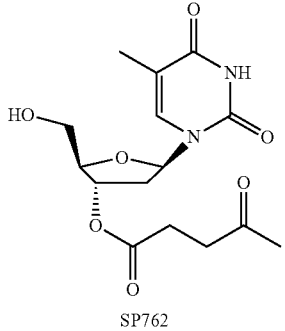

1-[(2R,4S,5R)-5-[[bis(4-methoxyphenyl)-phenyl-methoxy]methyl]-4-hydroxyoxolan-2-yl]-5-methylpyrimidine-2,4-dione (Compound SP761) (1.09 g, 2 mmol), levulinic acid (0.29 ml, 2.8 mmol), N,N-dimethyl-4-aminopyridine (DMAP) (73 mg, 0.6 mmol) and 1-ethyl-3-(3-dimethylaminopropyl)carbodiimide hydrochloride (EDC·HCl, 538 mg, 2.8 mmol) were dissolved in dichloromethane (2 ml) under a nitrogen atmosphere, and the mixture was stirred at room temperature for 15 minutes. 0.6 ml of methanol was added to the reaction solution, then p-toluenesulfonic acid (532 mg, 2.8 mmol) was added and the mixture was stirred at room temperature for 1 minute. 3 ml of phosphate buffer (pH=6, 1 M) was added to the above reaction solution, and the mixture was stirred for 2 minutes. 10 ml of a dichloromethane/ethanol solution (5:1) was added to the reaction solution, and the mixture was separated by 7 ml of phosphate buffer (pH=6, 1 M). The organic layer was collected, the aqueous layer was separated by 15 ml of a dichloromethane/ethanol solution (5:1) twice, and the organic layers were collected. The collected organic layers were combined, and sodium sulfate was added for drying. Sodium sulfate was then removed by filtration, the filtrate was concentrated under reduced pressure, and the residue was purified by silica gel column chromatography (ethyl acetate:hexane=65:35→100:0) to afford the desired compound (Compound SP762) (632.5 mg, 93%).

LCMS (ESI) m/z=341.3 (M+H)+

Retention time: 0.52 min (analysis condition SQDAA05)

Synthesis of [(2R,3S,5R)-2-[[(2-chlorophenoxy)-[(2R,3S,5R)-2-(hydroxymethyl)-5-[2-(2-methylpropanoylamino)-6-oxo-1H-purin-9-yl]oxolan-3-yl]oxyphosphoryl]oxymethyl]-5-(5-methyl-2,4-dioxopyrimidin-1-yl)oxolan-3-yl]4-oxopentanoate (Compound SP764)

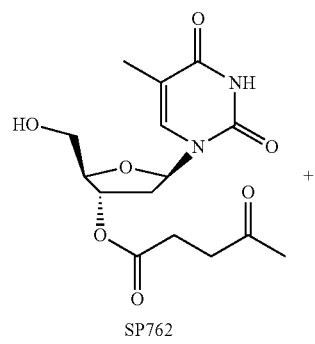

SP762

+

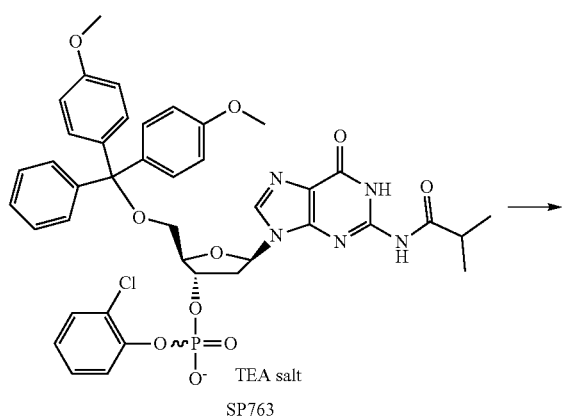

SP763

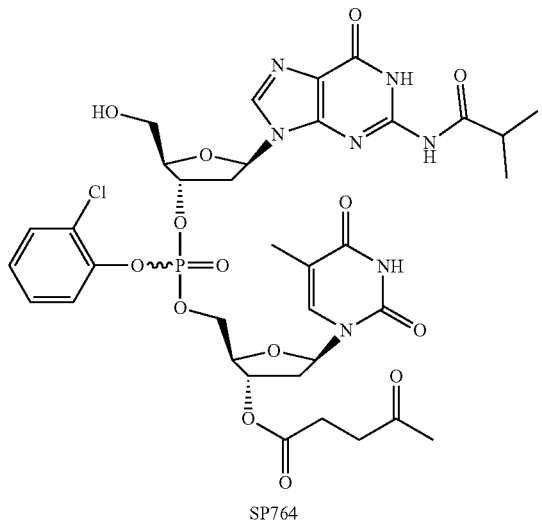

SP764

Compound SP763 (328 mg, 0.97 mmol) and Compound SP762 (862 mg, 0.92 mmol) were dissolved in dehydrated pyridine (2.5 ml) under a nitrogen atmosphere. A solution of 1-(2-mesitylenesulfonyl)-3-nitro-1H-1,2,4-triazole (MSNT) (681 mg, 2.3 mmol) in dehydrated pyridine (2.5 ml) was added dropwise to the above reaction solution over 10 minutes, and the mixture was stirred at room temperature for 2 hours. The reaction solution was concentrated under reduced pressure, the residue was dissolved in 6 ml of dichloromethane/methanol (5:1), p-toluenesulfonic acid (350 mg, 1.84 mmol) was added and the mixture was stirred at room temperature for 1 minute. 8 ml of phosphate buffer (pH=6, 1 M) was added to the above reaction solution, and the mixture was stirred for 2 minutes. 10 ml of a dichloromethane/ethanol solution (5:1) was added to the reaction solution, and the mixture was separated. The organic layer was collected, the aqueous layer was further separated by 10 ml of a dichloromethane/ethanol solution (5:1) twice, and the organic layers were collected. The collected organic layers were combined, and sodium sulfate was added for drying. Sodium sulfate was then removed by filtration, the organic layer was concentrated under reduced pressure, and the residue was purified by silica gel column chromatography (ethyl acetate:hexane=50:50→100:0) to afford the desired compound (Compound SP764) (725.4 mg, 93%).

LCMS (ESI) m/z=850.4 (M+H)+

Retention time: 0.62 min (analysis condition SQDFA05)

Synthesis of [(2R,3S,5R)-5-(6-benzamidopurin-9-yl)-2-[[bis(4-methoxyphenyl)-phenylmethoxy]methyl]oxolan-3-yl][(2R,3S,5R)-3-[(2-chlorophenoxy)-[[(2R,3S,5R)-3-hydroxy-5-(5-methyl-2,4-dioxopyrimidin-1-yl)oxolan-2-yl]methoxy]phosphoryl]oxy-5-[2-(2-methylpropancylamino)-6-oxo-1H-purin-9-yl]oxolan-2-yl]methyl (2-chlorophenyl) Phosphate (Compound SP766)

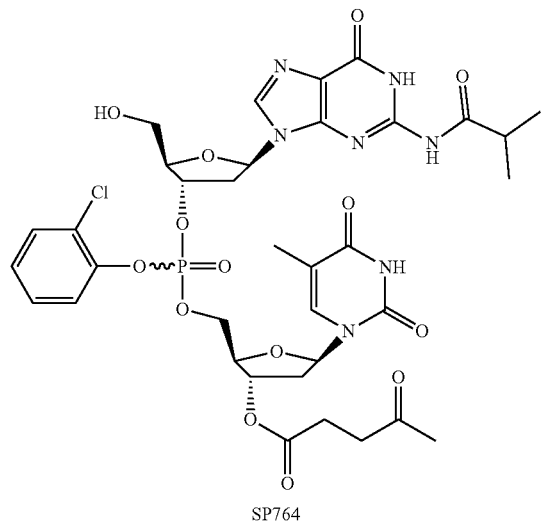

SP764

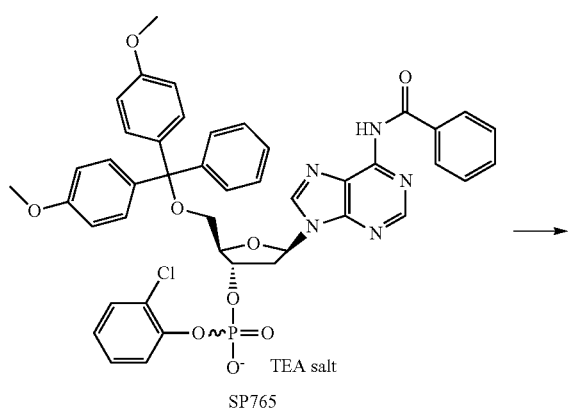

SP765

+

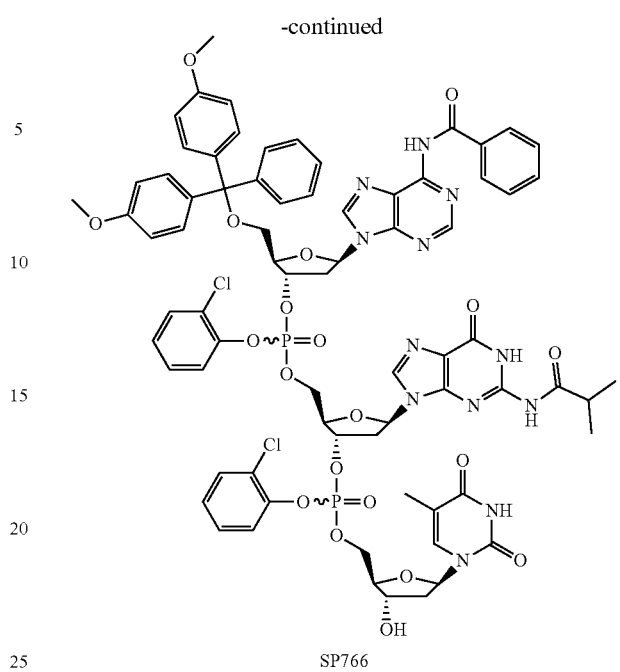

SP766

Compound SP765 (1.0 g, 1.05 mmol) and Compound SP764 (850 mg, 1.0 mmol) were dissolved in dehydrated pyridine (2.5 ml) under a nitrogen atmosphere. A solution of 1-(2-mesitylenesulfonyl)-3-nitro-1H-1,2,4-triazole (MSNT) (740 mg, 2.5 mmol) in dehydrated pyridine (2.5 ml) was added dropwise to the above reaction solution over 10 minutes, and the mixture was stirred at room temperature for 2 hours. The reaction solution was cooled to 0° C., and acetic acid (1.0 ml) was added dropwise. Hydrazine monohydrate (0.24 ml, 5.0 mmol) was added to the reaction solution, and the mixture was stirred for 5 minutes. 10 ml of phosphate buffer (pH=6, 1 M) and dichloromethane (5 ml) were added to the above reaction solution, and the mixture was stirred for 1 minute. The reaction solution was separated by 10 ml of a dichloromethane/ethanol solution (10:1) three times, and the organic layers were collected. Sodium sulfate was added to the collected organic layers for drying. Sodium sulfate was removed by filtration, the organic layer was concentrated under reduced pressure, and the residue was purified by reverse-phase silica gel column chromatography (10 mM aqueous ammonium acetate solution/methanol) to afford the desired compound (Compound SP766) (1.22 g, 77%).

LCMS (ESI) m/z=1581.8 (M+H)+
Retention time: 1.11 min (analysis condition SQDAA05)

2595

Synthesis of [(2R,3S,5R)-5-(6-benzamido-1,6-dihydropurin-9-yl)-2-[[bis(4-methoxyphenyl)-phenylmethoxy]methyl]oxolan-3-yl][(2R,3S,5R)-3-[(2-Chlorophenoxy)-[[(2R,3S,5R)-3-[2-cyanoethoxy-[di(propan-2-yl)amino]phosphanyl]oxy-5-(5-methyl-2,4-dioxopyrimidin-1-yl)oxolan-2-yl]methoxy]phosphoryl]oxy-5-[2-(2-methylpropanoylamino)-6-oxo-1H-purin-9-yl]oxolan-2-yl]methyl (2-chlorophenyl) Phosphate (Compound SP768, AGT Unit)

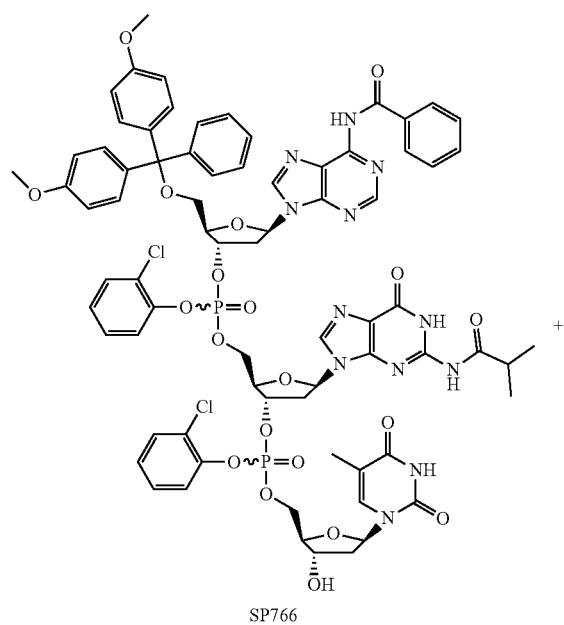

SP766

+

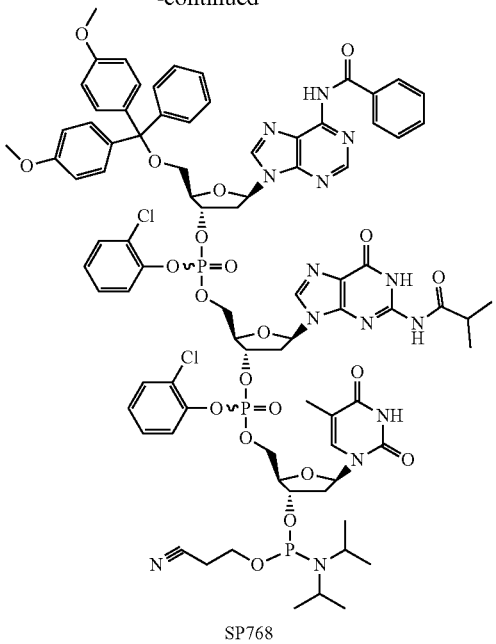

SP767

-continued

SP768

Compound 766 (2.5 g, 1.71 mmol) and 5-ethylthio-1H-tetrazole (667 mg, 5.13 mmol) were dissolved in dichloromethane (17 ml) under a nitrogen atmosphere, 2-cyanoethyl-N,N,N',NT-tetraisopropyl phosphorodiamidite (Compound 767) (5.43 ml, 17.1 mmol) was added and the mixture was stirred at room temperature for 15 minutes. Triethylamine (0.71 ml, 5.13 mmol) was added to the reaction solution, and then, the resulting reaction mixture was concentrated under reduced pressure. The residue was purified by reverse-phase silica gel column chromatography (aqueous acetonitrile solution) to afford the desired compound (Compound 768, AGT unit) (1.84 g, 60%).

The AGT unit is herein defined as a compound having an AGT unit, having a hydroxyl group at the 5'-position is protected by a 4,4'-dimethoxytrityl group (DMT) and a phosphate is protected by a 2-chlorophenyl group as in the above compound (SP768), having amino group-protected nucleobases (A(Bz), G(iBu) and T) continuously from the 5'-side, and having a N,N'-diisopropylaminophosphoramidite group that is protected by a cyanoethyl group at the 3'-end. Hereinafter, units with other names such as the TTT unit are also defined as compounds having a TTT unit, having a protected nucleic acid portion and having a N,N'-diisopropylaminophosphoramidite group. LCMS (ESI) m/z=1781.8 (M+H)+

Retention time: 1.17 min (analysis condition SQDAA05)

Synthesis of [(2R,3S,5R)-2-(hydroxymethyl)-5-[2-(2-methylpropanoylamino)-6-oxo-1H-purin-9-yl]oxolan-3-yl]4-oxopentanoate (Compound SP770)

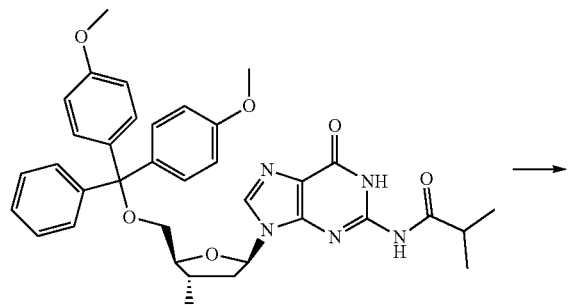

SP769

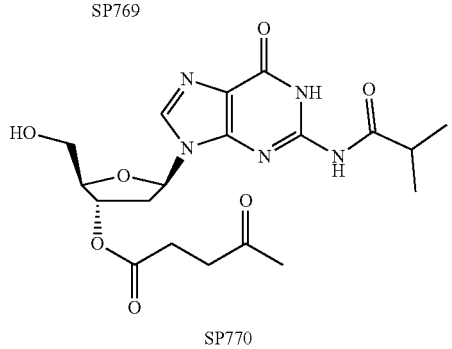

SP770

[(2R,3S,5R)-2-(Hydroxymethyl)-5-[2-(2-methylpropanoylamino)-6-oxo-1H-purin-9-yl]oxolan-3-yl]4-oxopentanoate (Compound SP770) (2.9 g, 85%) was obtained using N-[9-[(2R,4S,5R)-5-[[bis(4-methoxyphenyl)-phenylmethoxy]methyl]-4-hydroxyoxolan-2-yl]-6-oxo-1H-purin-2-yl]-2-methylpropanamide (Compound 769) in place of 1-[(2R,4S,5R)-5-[[bis(4-methoxyphenyl)-phenylmethoxy]methyl]-4-hydroxyoxolan-2-yl]-5-methylpyrimidine-2,4-dione (Compound 761) under the same conditions as in the preparation example for Compound SP762.

LCMS (ESI) m/z=435.9 (M+H)+

Retention time: 1.205 min (analysis condition SMD Method 9)

Synthesis of [(2R,3S,5R)-5-(6-benzamidopurin-9-yl)-2-(hydroxymethyl)oxolan-3-yl]4-oxopentanoate (Compound SP772)

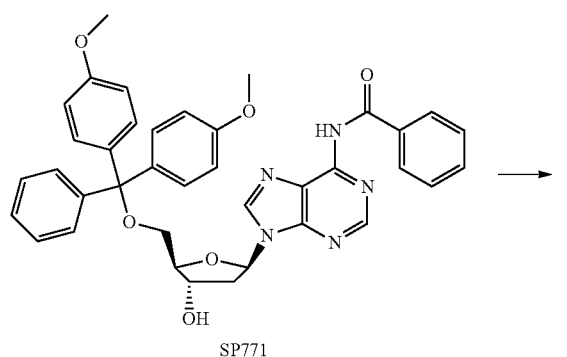

SP771

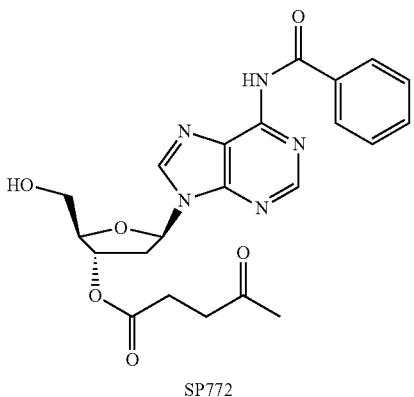

SP772

[(2R,3S,5R)-5-(6-Benzamidopurin-9-yl)-2-(hydroxymethyl)oxolan-3-yl]4-oxopentanoate (Compound SP772) (50.0 g, 56%) was obtained using N-[9-[(2R,4S,5R)-5-[[bis(4-methoxyphenyl)-phenylmethoxy]methyl]-4-hydroxyoxolan-2-yl]purin-6-yl]benzamide (Compound SP771) in place of 1-[(2R,4S,5R)-5-[[bis(4-methoxyphenyl)-phenylmethoxy]methyl]-4-hydroxyoxolan-2-yl]-5-methylpyrimidine-2,4-dione (Compound SP761) under the same conditions as in the preparation example for (Compound SP762).

LCMS (ESI) m/z=454.2 (M+H)+

Retention time: 1.177 min (analysis condition SMD Method 4)

Synthesis of [(2R,3S,5R)-5-(4-benzamido-2-oxopyrimidin-1-yl)-2-(hydroxymethyl)oxolan-3-yl]4-oxopentanoate (Compound SP774)

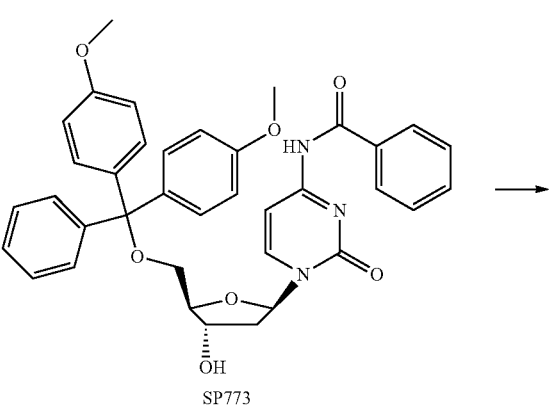

SP773

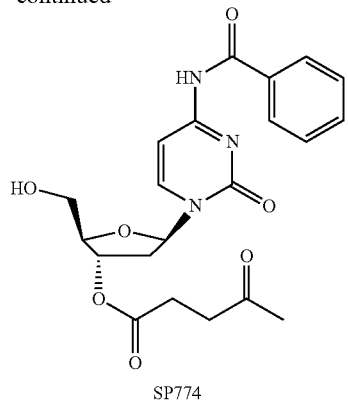

SP774

[(2R,3S,5R)-5-(4-Benzamido-2-oxopyrimidin-1-yl)-2-(hydroxymethyl)oxolan-3-yl]4-oxopentanoate (Compound SP774) (2.4 g, 89%) was obtained using N-[1-[(2R,4S,5R)-5-[[bis(4-methoxyphenyl)-phenylmethoxy]methyl]-4-hydroxyoxolan-2-yl]-2-oxopyrimidin-4-yl]benzamide (Compound SP773) in place of 1-[(2R,4S,5R)-5-[[bis(4-methoxyphenyl)-phenylmethoxy]methyl]-4-hydroxyoxolan-2-yl]-5-methylpyrimidine-2,4-dione (Compound SP761) under the same conditions as in the preparation example for (Compound SP762).

LCMS (ESI) m/z=430.2 (M+H)+

Retention time: 3.193 min (analysis condition SMD Method 10)

Synthesis of [(2R,3S,5R)-2-[[bis(4-methoxyphenyl)-phenylmethoxy]methyl]-5-(5-methyl-2,4-dioxopyrimidin-1-yl)oxolan-3-yl][(2R,3S,5R)-3-[(2-chlorophenoxy)-[[(2R,3S,5R)-3-[2-cyanoethoxy-[di(propan-2-yl)amino]phosphanyl]oxy-5-[2-(2-methylpropancylamino)-6-oxo-1H-purin-9-yl]oxolan-2-yl]methoxy]phosphoryl]oxy-5-(5-methyl-2,4-dioxopyrimidin-1-yl)oxolan-2-yl]methyl (2-chlorophenyl) Phosphate (Compound SP775, TTG Unit)

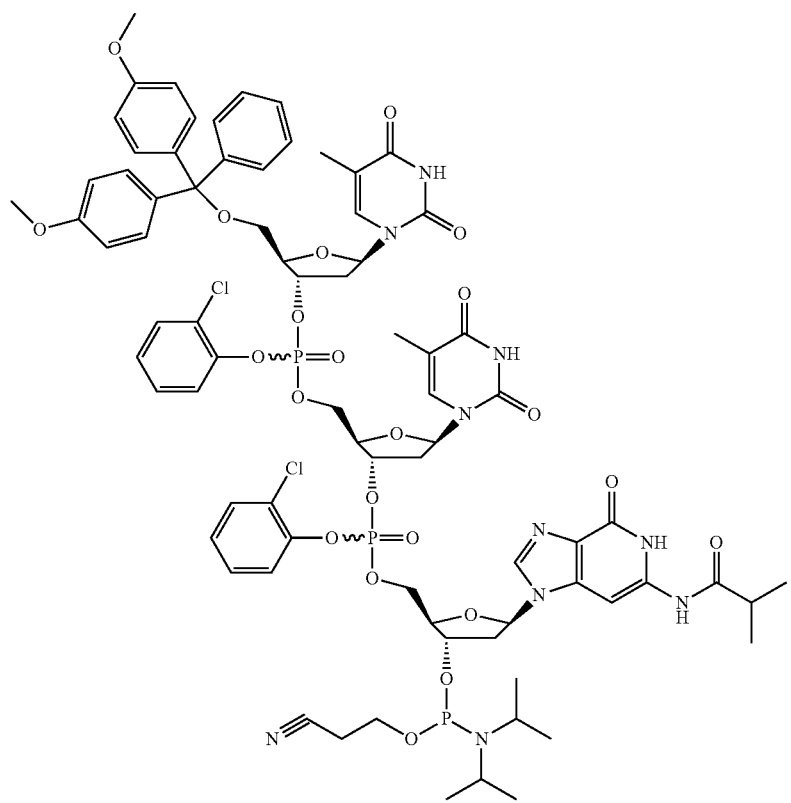

SP775

[(2R,3S,5R)-2-[[Bis(4-methoxyphenyl)-phenylmethoxy]methyl]-5-(5-methyl-2,4-dioxopyrimidin-1-yl)oxolan-3-yl][(2R,3S,5R)-3-[(2-chlorophenoxy)-[[(2R,3S,5R)-3-[2-cyanoethoxy-[di(propan-2-yl)amino]phosphanyl]oxy-5-[2-(2-methylpropancylamino)-6-oxo-1H-purin-9-yl]oxolan-2-yl]methoxy]phosphoryl]oxy-5-(5-methyl-2,4-dioxopyrimidin-1-yl)oxolan-2-yl]methyl (2-chlorophenyl) phosphate (Compound SP775, TTG unit) was obtained under the same conditions as in the preparation examples for Compounds SP761 to SP768.

LCMS (ESI) m/z=1668.8 (M+H)+

Retention time: 1.15 min (analysis condition SQDAA05)

2601

Synthesis of [(2R,3S,5R)-5-(4-benzamido-2-oxopyrimidin-1-yl)-2-[[bis(4-methoxyphenyl)-phenylmethoxy]methyl]oxolan-3-yl][(2R,3S,5R)-3-[(2-chlorophenoxy)-[[(2R,3S,5R)-3-[2-cyanoethoxy-[di(propan-2-yl)amino]phosphanyl]oxy-5-(5-methyl-2,4-dioxopyrimidin-1-yl)oxolan-2-yl]methoxy]phosphoryl]oxy-5-(5-methyl-2,4-dioxopyrimidin-1-yl)oxolan-2-yl]methyl (2-chlorophenyl) Phosphate (Compound SP776, CTT Unit)

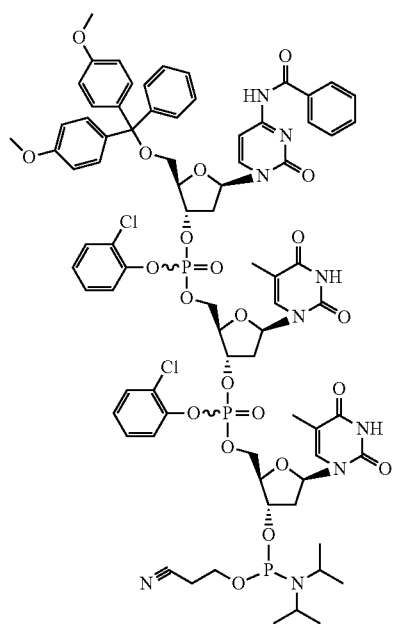

SP776

[(2R,3S,5R)-5-(4-Benzamido-2-oxopyrimidin-1-yl)-2-[[bis(4-methoxyphenyl)-phenylmethoxy]methyl]oxolan-3-yl][(2R,3S,5R)-3-[(2-chlorophenoxy)-[[(2R,3S,5R)-3-[2-cyanoethoxy-[di(propan-2-yl)amino]phosphanyl]oxy-5-(5-methyl-2,4-dioxopyrimidin-1-yl)oxolan-2-yl]methoxy]phosphoryl]oxy-5-(5-methyl-2,4-dioxopyrimidin-1-yl)oxolan-2-yl]methyl (2-chlorophenyl) phosphate (Compound SP776, CTT unit) was obtained under the same conditions as in the preparation examples for Compounds SP761 to SP768.

LCMS (ESI) m/z=1662.4 (M+H)+

Retention time: 1.18 min (analysis condition SQDAA05)

2602

Synthesis of [(2R,3S,5R)-5-(4-benzamido-2-oxopyrimidin-1-yl)-2-[[bis(4-methoxyphenyl)-phenylmethoxy]methyl]oxolan-3-yl][(2R,3S,5R)-3-[[(2R,3S,5R)-5-(6-benzamidopurin-9-yl)-3-[2-cyanoethoxy-[di(propan-2-yl)amino]phosphanyl]oxyoxolan-2-yl]methoxy-(2-chlorophenoxy)phosphoryl]oxy-5-(5-methyl-2,4-dioxopyrimidin-1-yl)oxolan-2-yl]methyl (2-chlorophenyl) Phosphate (Compound SP777, CTA Unit)

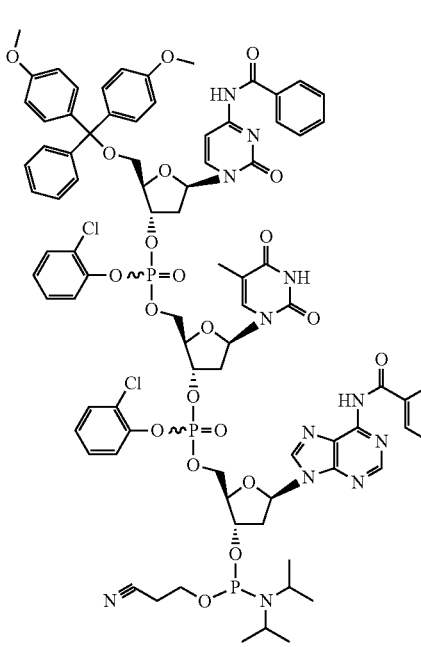

SP777

[(2R,3S,5R)-5-(4-Benzamido-2-oxopyrimidin-1-yl)-2-[[bis(4-methoxyphenyl)-phenylmethoxy]methyl]oxolan-3-yl][(2R,3S,5R)-3-[[(2R,3S,5R)-5-(6-benzamidopurin-9-yl)-3-[2-cyanoethoxy-[di(propan-2-yl)amino]phosphanyl]oxyoxolan-2-yl]methoxy-(2-chlorophenoxy)phosphoryl]oxy-5-(5-methyl-2,4-dioxopyrimidin-1-yl)oxolan-2-yl]methyl (2-chlorophenyl) phosphate (Compound SP777, CTA unit) was obtained under the same conditions as in the preparation examples for Compounds SP761 to SP768.

LCMS (EST) m/z=1775.9 (M+H)+

Retention time: 1.20 min (analysis condition SQDAA05)

2603

Synthesis of [(2R,3S,5R)-5-(6-benzamidopurin-9-yl)-2-[[[(2R,3S,5R)-2-[[bis(4-methoxyphenyl)-phenylmethoxy]methyl]-5-(5-methyl-2,4-dioxopyrimidin-1-yl)oxolan-3-yl]oxy-(2-chlorophenoxy) phosphoryl]oxymethyl]oxolan-3-yl](2-chlorophenyl) [(2R,3S,5R)-3-[2-cyanoethoxy-[di(propan-2-yl)amino]phosphanyl]oxy-5-[2-(2-methylpropanoylamino)-6-oxo-1H-purin-9-yl]oxolan-2-yl]methyl Phosphate (Compound SP778, TAG Unit)

2604

Synthesis of [(2R,3S,5R)-2-[[bis(4-methoxyphenyl)-phenylmethoxy]methyl]-5-(5-methyl-2,4-dioxopyrimidin-1-yl)oxolan-3-yl][(2R,3S,5R)-3-[(2-chlorophenoxy)-[[(2R,3S,5R)-3-[2-cyanoethoxy-[di(propan-2-yl)amino]phosphanyl]oxy-5-(5-methyl-2,4-dioxopyrimidin-1-yl)oxolan-2-yl]methoxy]phosphoryl]oxy-5-(5-methyl-2,4-dioxopyrimidin-1-yl)oxolan-2-yl]methyl (2-chlorophenyl) Phosphate (Compound SP779, TTT Unit)

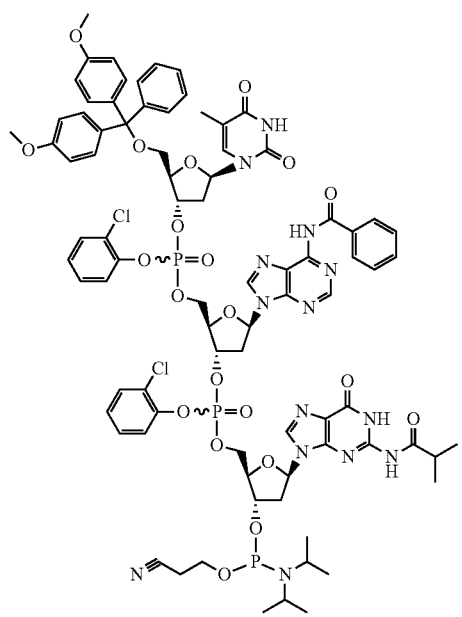

SP778

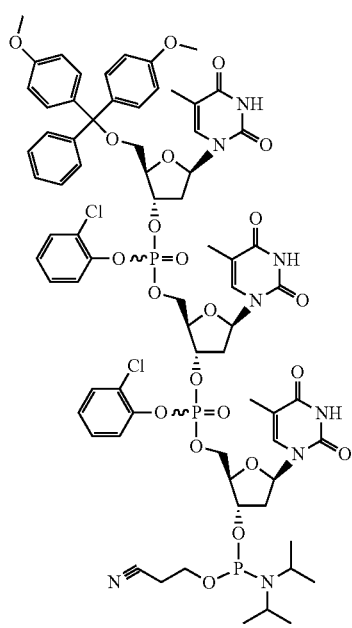

SP779

[(2R,3S,5R)-5-(6-Benzamidopurin-9-yl)-2-[[[(2R,3S,5R)-2-[[bis(4-methoxyphenyl)-phenylmethoxy]methyl]-5-(5-methyl-2,4-dioxopyrimidin-1-yl)oxolan-3-yl]oxy-(2-chlorophenoxy)phosphoryl]oxymethyl]oxolan-3-yl](2-chlorophenyl) [(2R,3S,5R)-3-[2-cyanoethoxy-[di(propan-2-yl)amino]phosphanyl]oxy-5-[2-(2-methylpropancylamino)-6-oxo-1H-purin-9-yl]oxolan-2-yl]methyl phosphate (Compound SP778, TAG unit) was obtained under the same conditions as in the preparation examples for Compounds SP761 to SP768.

LCMS (ESI) m/z=1781.9 (M+H)+

Retention time: 1.17 min (analysis condition SQDAA05)

[(2R,3S,5R)-2-[[Bis(4-methoxyphenyl)-phenylmethoxy]methyl]-5-(5-methyl-2,4-dioxopyrimidin-1-yl)oxolan-3-yl][(2R,3S,5R)-3-[(2-chlorophenoxy)-[[(2R,3S,5R)-3-[2-cyanoethoxy-[di(propan-2-yl)amino]phosphanyl]oxy-5-(5-methyl-2,4-dioxopyrimidin-1-yl)oxolan-2-yl]methoxy]phosphoryl]oxy-5-(5-methyl-2,4-dioxopyrimidin-1-yl)oxolan-2-yl]methyl (2-chlorophenyl) phosphate (Compound SP779, TTT unit) was obtained under the same conditions as in the preparation examples for Compounds SP761 to SP768.

LCMS (ESI) m/z=1573.8 (M+H)+

Retention time: 1.15 min (analysis condition SQDAA05)

2605

Synthesis of [(2R,3S,5R)-5-(6-benzamidopurin-9-yl)-2-[[bis(4-methoxyphenyl)-phenylmethoxy]methyl]oxolan-3-yl][(2R,3S,5R)-3-[(2-chlorophenoxy)-[[(2R,3S,5R)-3-[2-cyanoethoxy-[di(propan-2-yl)amino]phosphanyl]oxy-5-(5-methyl-2,4-dioxopyrimidin-1-yl)oxolan-2-yl]methoxy]phosphoryl]oxy-5-(5-methyl-2,4-dioxopyrimidin-1-yl)oxolan-2-yl]methyl (2-chlorophenyl) Phosphate (Compound SP780, ATT Unit)

2606

Synthesis of [(2R,3S,5R)-5-(4-benzamido-2-oxopyrimidin-1-yl)-2-[[bis(4-methoxyphenyl)-phenylmethoxy]methyl]oxolan-3-yl][(2R,3S,5R)-3-[(2-chlorophenoxy)-[[(2R,3S,5R)-3-[2-cyanoethoxy-[di(propan-2-yl)amino]phosphanyl]oxy-5-[2-(2-methylpropanoylamino)-6-oxo-1H-purin-9-yl]oxolan-2-yl]methoxy]phosphoryl]oxy-5-[2-(2-methylpropanoylamino)-6-oxo-1H-purin-9-yl]oxolan-2-yl]methyl (2-chlorophenyl) Phosphate (Compound SP781, CGG Unit)

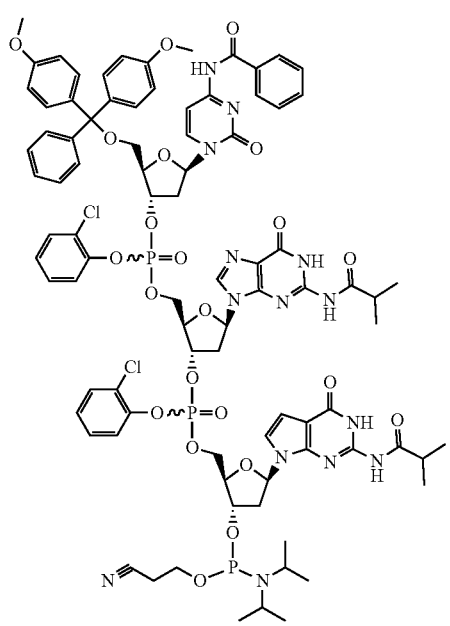

[(2R,3S,5R)-5-(6-Benzamidopurin-9-yl)-2-[[bis(4-methoxyphenyl)-phenylmethoxy]methyl]oxolan-3-yl][(2R,3S,5R)-3-[(2-chlorophenoxy)-[[(2R,3S,5R)-3-[2-cyanoethoxy-[di(propan-2-yl)amino]phosphanyl]oxy-5-(5-methyl-2,4-dioxopyrimidin-1-yl)oxolan-2-yl]methoxy]phosphoryl]oxy-5-(5-methyl-2,4-dioxopyrimidin-1-yl)oxolan-2-yl] methyl (2-chlorophenyl) phosphate (Compound SP780, ATT unit) was obtained under the same conditions as in the preparation examples for Compounds SP761 to SP768.

LCMS (ESI) m/z=1686.4 (M+H)+

Retention time: 1.16 min (analysis condition SQDAA05)

[(2R,3S,5R)-5-(4-Benzamido-2-oxopyrimidin-1-yl)-2-[[bis(4-methoxyphenyl)-phenylmethoxy]methyl]oxolan-3-yl][(2R,3S,5R)-3-[(2-chlorophenoxy)-[[(2R,3S,5R)-3-[2-cyanoethoxy-[di(propan-2-yl)amino]phosphanyl]oxy-5-[2-(2-methylpropanoylamino)-6-oxo-1H-purin-9-yl]oxolan-2-yl]methoxy]phosphoryl]oxy-5-[2-(2-methylpropancylamino)-6-oxo-1H-purin-9-yl]oxolan-2-yl] methyl (2-chlorophenyl) phosphate (Compound SP781, CGG unit) was obtained under the same conditions as in the preparation examples for Compounds SP761 to SP768.

LCMS (ESI) m/z=1852.5 (M+H)+

Retention time: 0.87 min (analysis condition SQDAA50)

Synthesis of [(2R,3S,5R)-5-(6-benzamidopurin-9-yl)-2-[[bis(4-methoxyphenyl)-phenylmethoxy]methyl]oxolan-3-yl][(2R,3S,5R)-3-[(2-chlorophenoxy)-[[(2R,3S,5R)-3-[2-cyanoethoxy-[di(propan-2-yl)amino]phosphanyl]oxy-5-[2-(2-methylpropanoylamino)-6-oxo-1H-purin-9-yl]oxolan-2-yl]methoxy]phosphoryl]oxy-5-[2-(2-methylpropanoylamino)-6-oxo-1H-purin-9-yl]oxolan-2-yl]methyl (2-chlorophenyl) Phosphate (Compound SP782, AGG Unit)

SP782

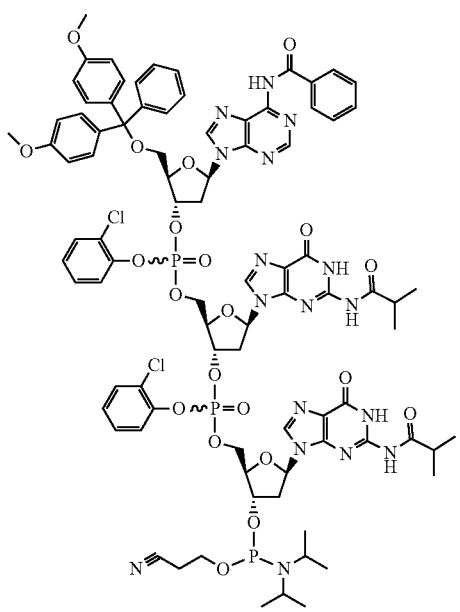

[(2R,3S,5R)-5-(6-Benzamidopurin-9-yl)-2-[[bis(4-methoxyphenyl)-phenylmethoxy]methyl]oxolan-3-yl][(2R,3S,5R)-3-[(2-chlorophenoxy)-[[(2R,3S,5R)-3-[2-cyanoethoxy-[di(propan-2-yl)amino]phosphanyl]oxy-5-[2-(2-methylpropanoylamino)-6-oxo-1H-purin-9-yl]oxolan-2-yl]methoxy]phosphoryl]oxy-5-[2-(2-methylpropanoylamino)-6-oxo-1H-purin-9-yl]oxolan-2-yl]methyl (2-chlorophenyl) phosphate (Compound SP782, AGG unit) was obtained under the same conditions as in the preparation examples for Compounds SP761 to SP768.

LCMS (ESI) m/z=1876.5 (M+H)+
Retention time: 0.84 min (analysis condition SQDAA50)

5. Chemical Synthesis of Randomized DNA Parts Used for a Display Library

Randomized highly diverse DNAs were synthesized by the following method using codon units obtained by the above-described method or purchased.
Compound SP791
  5T-GAA GGA GAT ATA CAT ATG (PPP)7 CGT (XXX) (PPP) AGC GGC TCT GGC TCT GGC TCT-3' (SEQ ID NO: 140)
Random DNAs were synthesized by the phosphoramidite method using a DNA/RNA synthesizer (NTS H-6, manufactured by Nihon Techno Service Co., Ltd.). Dehydrated acetonitrile and deblocking solution-1 (3 w/v % trichloroacetic acid-dichloromethane solution) were purchased from Wako Pure Chemical Industries, and phosphoramidite reagents (dA, dC, dG and dT-CE phosphoramidites), Cap Mix A (THF/pyridine/acetic anhydride), Cap Mix B (16% 1-Me-Imidazole/THF), Oxidizing Solution (0.02 M 12 in THF/Pyridine/H2O), Activator (5-benzylthio-1H-tetrazole in MeCN) and trimer phosphoramidite reagents (GTT, CCG, ACT, ATG, GCT, CAT, TGG, GGT, TAC, CAG, AAC, TGC and GAA trimer phosphoramidites) were purchased from Glen Research. Trimer phosphoramidite reagents (TTT (Compound SP779), ATT (Compound SP780), AGT (Compound SP768), CGG (Compound SP781), AGG (Compound SP782), TTG (Compound SP775), CTT (Compound SP776), CTA (Compound SP777) and TAG (Compound SP778) trimer phosphoramidites) used were those synthesized as described above.

Mixtures of trimer phosphoramidite reagents (TTT, ATT, GTT, AGT, CCG, ACT, GCT, CAT, TGG, GGT, TAC, CAG, AAC, CGG, AGG, TTG, CTT, CTA, TAG, TGC and GAA trimer phosphoramidites) were applied to sites indicated as (PPP) in the sequences, and mixtures of trimer phosphoramidite reagents (TTT, CCG, GCT, CAT, AAC, CGG, AGG, TTG, TAG and GAA trimer phosphoramidites) were applied to sites indicated as (XXX). Accordingly, PPP refers to not only TTT but also ATT, TAC and the like. (PPP)7 refers to any PPPs bound to each other seven times, and does not only refer to (ATT)7 but schematically illustrates that $21^7$ diverse reagent mixtures are possible when each PPP is selected from 21 reagents, for example.

The detailed operational procedure was in accordance with the manual attached to the synthesizer.

A reaction vessel equipped with a filter was packed with Glen UnySupport CPG (1000 Å, 44 µmol/g, 5.2 mg, 0.229 µmol) and placed in the synthesizer, and DNA was solid-phase synthesized. Elongation reaction using the synthesizer was completed at this point without deprotecting the protecting group for the 5'-terminal hydroxyl group (DMT: a 4,4'-dimethoxytrityl group).

After completion of the elongation reaction, the solid support was transferred to a screw-capped glass tube, followed by addition of a 30% aqueous ammonia solution (0.4 ml). DNA cleavage from CPG and deprotection were carried out by stirring at 60° C. for 6 hours, and the reaction mixture was purified by preparative HPLC (analysis condition LC05). The HPLC fraction was lyophilized, the resulting residue was dissolved in water (0.8 ml), acetic acid (3 ml) was added thereto, and the mixture was stirred at room temperature for 10 minutes to deprotect the DMT group for the 5'-terminal hydroxyl group. The reaction solution was diluted with water (10 ml) and extracted with ethyl acetate (10 ml) five times, and the resulting aqueous layers were then lyophilized to afford the intended randomized DNA (Compound SP791) (6.7%). The yield was calculated from the absorbance at 260 nm.

Retention time: 8.55 min (analysis condition LC04)

(SEQ ID NO: 141)
Compound SP792
5'-GAA GGA GAT ATA CAT ATG (PPP)8 CGT (XXX)

(PPP) AGC GGC TCT GGC TCT GGC TCT-3'

The intended randomized DNA (Compound SP792) (7.6) was obtained by the same method as for Compound SP791.

Retention time: 8.71 min (analysis condition LC04)

Compound SP793

(SEQ ID NO: 142)
5'-GAA GGA GAT ATA CAT ATG (PPP)9 CGT (XXX) (PPP)
AGC GGC TCT GGC TCT GGC TCT-3'

The intended randomized DNA (Compound SP793) (5.8%) was obtained by the same method as for Compound SP791.

Retention time: 8.67 min (analysis condition LC04)

Compound SP794

(SEQ ID NO: 143)
5'-GAA GGA GAT ATA CAT ATG TGC (QQQ)7 CGT (QQQ)2
AGC GGC TCT GGC TCT GGC TCT-3'

The intended randomized DNA (Compound SP794) (6.5%) was obtained by the same method as for Compound SP791. Mixtures of trimer phosphoramidite reagents (TTT, ATT, ATG, GTT, AGT, CCG, ACT, GCT, CAT, TGG, GGT, TAC, CAG, AAC, CGG, AGG, TTG, CTT, CTA, TAG and GAA trimer phosphoramidites) were applied to sites indicated as (QQQ) in the sequences. Accordingly, QQQ refers to not only TTT but also ATT, TAC and the like. (QQQ)7 refers to any QQQs bound to each other seven times, and does not only refer to (ATT)7 but schematically illustrates that $21^7$ diverse reagent mixtures are possible when each PPP is selected from 21 reagents, for example.

Retention time: 8.56 min (analysis condition LC04)

Compound SP795

(SEQ ID NO: 144)
5'-GAA GGA GAT ATA CAT ATG TGC (QQQ)8 CGT (QQQ)2
AGC GGC TCT GGC TCT GGC TCT-3'

The intended randomized DNA (Compound SP795) (6.0%) was obtained by the same method as for Compound SP791.

Retention time: 8.54 min (analysis condition LC04)

Compound SP796

(SEQ ID NO: 145)
5'-GAA GGA GAT ATA CAT ATG TGC (QQQ)9 CGT (QQQ)2
AGC GGC TCT GGC TCT GGC TCT-3'

The intended randomized DNA (Compound SP796) (4.5%) was obtained by the same method as for Compound SP791.

Retention time: 8.80 min (analysis condition LC04)

6. Preparation of a DNA Library Used for a Display Library

Extention reaction of synthetic oligodeoxynucleotides (Compounds SP791, SP792, SP793, SP794, SP795 and SP796) and a synthetic oligodeoxynucleotide (SEQ ID NO: DOL-1) was carried out with ExTaq (Takara). After denaturation at 95° C. for 2 minutes, a cycle of one minute at 50° C. and one minute at 72° C. was repeated 5 to 10 times. Subsequently, PCR amplification with a synthetic oligodeoxynucleotide (SEQ ID NO: DOL-1) and a synthetic oligodeoxynucleotide (SEQ ID NO: DOL-2) was carried out with ExTaq (Takara) using this extention reaction product as a template. After denaturation at 95° C. for 2 minutes, a cycle of one minute at 95° C., one minute at 50° C. and one minute at 72° C. was repeated 5 to 10 times to construct a DNA library (SEQ ID NO: DML-1 to DML-6).

Sites indicated as (PPP) in the sequences refer to randomly occurring TTT, ATT, GTT, AGT, CCG, ACT, GCT, CAT, TGG, GGT, TAC, CAG, AAC, CGG, AGG, TTG, CTT, CTA, TAG, TGC and GAA. Sites indicated as (XXX) refer to randomly occurring TTT, CCG, GCT, CAT, AAC, CGG, AGG, TTG, TAG and GAA. Sites indicated as (QQQ) refer to randomly occurring TTT, ATT, ATG, GTT, AGT, CCG, ACT, GCT, CAT, TGG, GGT, TAC, CAG, AAC, CGG, AGG, TTG, CTT, CTA, TAG and GAA.

SEQ ID NO: DOL-1

(SEQ ID NO: 146)
TTTGTCCCCGCCGCCCTAAGAGCCAGAGCCAGAGCCGCT

SEQ ID NO: DOL-2

(SEQ ID NO: 147)
GTAATACGACTCACTATAGGGTTAACTTTAAGAAGGAGATATACATATG

SEQ ID NO: DML-1

(SEQ ID NO: 148)
GTAATACGACTCACTATAGGGTTAACTTTAAGAAGGAGATATACATATG (PPP)7CGT(XXX)(PPP)AGCGGCTCTGGCTCTGGCTCTTAGGGCGGC

GGGGACAAA

SEQ ID NO: DML-2

(SEQ ID NO: 149)
GTAATACGACTCACTATAGGGTTAACTTTAAGAAGGAGATATACATATG (PPP)8CGT(XXX)(PPP)AGCGGCTCTGGCTCTGGCTCTTAGGGCGGC

GGGGACAAA

TABLE 23

| Analysis condition | Instrument | Column (I.D. × length) (mm) | Mobile phase | Gradient (A/B) | Flow rate (mL/min) | Column temperature (° C.) | Wavelength |
|---|---|---|---|---|---|---|---|
| LC04 | SHIMADZU LIQUID CHROMATOGRAPH LC-10AD VP | YMC-Pack ODS-A (4.6 × 150) | A) 100 mM AcOH-TEA, H2O B) MeCN | 95/5 => 50/50 (20 min) | 1.0 | 40 | 260 nm |
| LC05 | Preparative HPLC system with injection/ fractionation function (Gilson, Inc. Middleton, WI, USA) | YMC-Actus ODS-A (20 × 100) | A) 100 mM AcOH-TEA, H2O B) MeCN | 85/15 => 65/35 (20 min) | 20 | 50 | 260 nm |

```
SEQ ID NO: DML-3
                                        (SEQ ID NO: 150)
GTAATACGACTCACTATAGGGTTAACTTTAAGAAGGAGATATACATATG (PPP)₉CGT(XXX)(PPP)AGCGGCTCTGGCTCTGGCTCTTAGGGCGGC

GGGGACAAA

SEQ ID NO: DML-4
                                        (SEQ ID NO: 151)
GTAATACGACTCACTATAGGGTTAACTTTAAGAAGGAGATATACATATG

TGC(QQQ)₇CGT(QQQ)₂AGCGGCTCTGGCTCTGGCTCTTAGGGCGGCGG

GGACAAA

SEQ ID NO: DML-5
                                        (SEQ ID NO: 152)
GTAATACGACTCACTATAGGGTTAACTTTAAGAAGGAGATATACATATG

TGC(QQQ)₈CGT(QQQ)₂AGCGGCTCTGGCTCTGGCTCTTAGGGCGGCGG

GGACAAA

SEQ ID NO: DML-6
                                        (SEQ ID NO: 153)
GTAATACGACTCACTATAGGGTTAACTTTAAGAAGGAGATATACATATG

TGC(QQQ)₉CGT(QQQ)₂AGCGGCTCTGGCTCTGGCTCTTAGGGCGGCGG

GGACAAA
```

7. Preparation of mRNA-Puromycin Linker Ligation Products

The following mRNAs (SEQ ID NO: MML-1 to MML-3 (for initiation suppression translation) and SEQ ID NO: MML-4 to MML-6 (for read through translation)) were prepared by in vitro transcription using a DNA library prepared by PCR (SEQ ID NO: DML-1 to DML-3 (for initiation suppression translation) and DML-4 to DML-6 (for read through translation)) as templates, and were purified using RNeasy mini kit (Qiagen). 15 µM puromycin linker (Sigma) (SEQ ID NO: C-1), 1×T4 RNA ligase reaction buffer (New England Biolabs), 1 mM ATP, 10% DMSO and 0.625 unit/µl T4 RNA ligase (New England Biolabs) were added to 10 µM mRNA, ligation reaction was carried out at 37° C. for 30 minutes, and the mixture was then purified by RNeasy Mini kit (Qiagen). SEQ ID NO: MML-1 and MML-4 were ligated and purified on 30 µl scale, SEQ ID NO: MML-2 and MML-5 were ligated and purified on 60 µl scale, and SEQ ID NO: MML-3 and MML-6 were ligated and purified on 240 µl scale. MML-1, MML-2 and MML-3 linked to puromycin linker (SEQ ID NO: C-1) were mixed at a molar ratio of 1:21:441, and MML-4, MML-5 and MML-6 linked to puromycin linker (SEQ ID NO: C-1) were mixed at a molar ratio of 1:21:441 to provide the former mixture as an mRNA-puromycin linker ligation product mixture for initiation suppression translation and the latter mixture as an mRNA-puromycin linker ligation product mixture for initiation read through translation.

Sites indicated as (RRR) in the sequences refer to randomly occurring UUU, AUU, GUU, AGU, CCG, ACU, GCU, CAU, UGG, GGU, UAC, CAG, AAC, CGG, AGG, UUG, CUU, CUA, UAG, UGC and GAA. Sites indicated as (YYY) refer to randomly occurring UUU, CCG, GCU, CAU, AAC, CGG, AGG, UUG, UAG and GAA. Sites indicated as (SSS) refer to randomly occurring UUU, AUU, AUG, GUU, AGU, CCG, ACU, GCU, CAU, UGG, GGU, UAC, CAG, AAC, CGG, AGG, UUG, CUU, CUA, UAG and GAA.

```
SEQ ID MML-1
                                        (SEQ ID NO: 154)
GGGUUAACUUUAAGAAGGAGAUAUACAUAUG(RRR)₇CGU(YYY)(RRR)

AGCGGCUCUGGCUCUGGCUCUUAGGGCGGCGGGGACAAA

SEQ ID MML-2
                                        (SEQ ID NO: 155)
GGGUUAACUUUAAGAAGGAGAUAUACAUAUG(RRR)₈CGU(YYY)(RRR)

AGCGGCUCUGGCUCUGGCUCUUAGGGCGGCGGGGACAAA

SEQ ID MML-3
                                        (SEQ ID NO: 156)
GGGUUAACUUUAAGAAGGAGAUAUACAUAUG(RRR)₉CGU(YYY)(RRR)

AGCGGCUCUGGCUCUGGCUCUUAGGGCGGCGGGGACAAA

SEQ ID MML-4
                                        (SEQ ID NO: 157)
GGGUUAACUUUAAGAAGGAGAUAUACAUAUGUGC(SSS)₇CGU(SSS)₂

AGCGGCUCUGGCUCUGGCUCUUAGGGCGGCGGGGACAAA

SEQ ID MML-5
                                        (SEQ ID NO: 158)
GGGUUAACUUUAAGAAGGAGAUAUACAUAUGUGC(SSS)₈CGU(SSS)₂

AGCGGCUCUGGCUCUGGCUCUUAGGGCGGCGGGGACAAA

SEQ ID MML-6
                                        (SEQ ID NO: 159)
GGGUUAACUUUAAGAAGGAGAUAUACAUAUGUGC(SSS)₉CGU(SSS)₂

AGCGGCUCUGGCUCUGGCUCUUAGGGCGGCGGGGACAAA
```

Preparation of Biotinylated Target Proteins

Interleukin-6 receptor (IL-6R), tumor necrosis factor-α (TNFα) and tumor necrosis factor receptor 1 (TNFR1) were used as target proteins used for panning. IL-6R was biotinylated using the method of the Non patent literature BMC biotechnology, 2008, 8, 41 and the Non patent literature Protein Science, 1999, 8, 921-929. IL-6R was prepared according to the Non patent literature J Biochem. 1990; 108(4):673-6. TNFα was purchased from Prospec as Recombinant Human Tumor Necrosis Factor-alpha (Catalog Number #CYT-223), and TNFR1 was purchased from Sino-Biological as Recombinant Human TNFR1/Fc Chimera (Catalog Number 10872-H03H). They are biotinylated using EZ-Link NHS-PEG4-Biotin of Thermo scientific (Catalog Number 21329), respectively.

Definition of the Translation Solutions Used for Panning

Translation Solution S used for panning is composed of the following components: 1 mM GTP, 1 mM ATP, 20 mM creatine phosphate, 50 mM HEPES-KOH pH 7.6, 100 mM potassium acetate, 10 mM magnesium acetate, 2 mM spermidine, 1 mM dithiothreitol, 0.5 mg/ml E. coli MRE600 (RNase-negative)-derived tRNA (Roche), 4 µg/ml creatine kinase, 3 µg/ml myokinase, 2 units/ml inorganic pyrophosphatase, 1.1 µg/ml nucleoside diphosphate kinase, 0.26 µM EF-G, 2.7 µM IF1, 0.4 µM IF2, 1.5 µM IF3, 40 µM EF-Tu, 84 µM EF-Ts, 1.2 µM ribosome, 2.73 µM AlaRS, 0.09 µM GlyRS, 0.4 µM IleRS, 0.68 µM PheRS, 0.16 µM ProRS, 0.04 µM SerRS, 0.09 µM ThrRS, 0.03 µM TrpRS, 0.22 µM TyrRS, 0.02 µM ValRS, 3 µM transcribed tRNA Ala1B (SEQ ID NO: MTL-13), 3 µM transcribed tRNA Tyr1 (SEQ ID NO: MTL-14), 250 µM glycine, 250 µM isoleucine, 250 µM proline, 250 µM threonine, 250 µM tryptophan, 250 µM valine, 100 µM serine, 5 mM N-methylalanine, 5 mM N-methylphenylalanine and 2 mM D-tyrosine. The translation solution was prepared by further adding the aminoacylated tRNA mixture for Translation Solution S and the initiator aminoacylated tRNA for Translation Solution S.

Translation Solution T was prepared by adding 0.02 µM CysRS, 250 µM cysteine and the aminoacylated tRNA mixture for Translation Solution T to Translation Solution S not containing the aminoacylated tRNA mixture for Translation Solution S and the initiator aminoacylated tRNA for Translation Solution S described above.

Translation, Cyclization, Desulfurization, Reverse Transcription Reaction, Binding to Proteins and PCR for Round 1 Panning 2 ml each of the aforementioned Translation Solutions S and T containing 1 µM of the mRNA-puromycin linker ligation product mixture for initiation suppression translation or read through translation was prepared, incubated at 37° C. for 120 minutes and then allowed to stand at room temperature for 12 minutes. 200 µl of a 200 mM EDTA solution (pH 8.0, Nacalai, 14362-24) and 100 µl of a 200 mM TCEP solution (pH 7.0) were added to the translation mixture, and the mixture was incubated at 37° C. for 120 minutes for cyclization reaction. 260 µl of a 250 mM Cys solution and 4000 µl of a 400 mM TCEP solution (pH 7.0) were then added to the translation mixture, and the mixture was incubated at 40° C. for 5 minutes. Subsequently, 1600 µl of 1 M VA-044 (Wako, CAS No. 27776-21-2) was added and desulfurization reaction was carried out at 40° C. for 1 hour. 1 ml of a peptide-mRNA complex solution was then purified with RNeasy mini kit (Qiagen). 3 µM primer (SEQ ID NO: DOL-3), M-MLV reverse transcriptase reaction buffer (Promega, M368B), 0.5 mM dGTP, 0.5 mM dATP, 0.5 mM dCTP, 0.5 mM dTTP and 8 U 1/µl M-MLV Reverse transcriptase (H—) (Promega, M368B) were added to the solution, and the mixture was diluted to 2 ml with nuclease free water and incubated at 42° C. for 1 hour as reverse transcription reaction. An equal amount of a blocking agent SuperBlock T20 (Pierce, 37516) was added to the reverse transcription solution to 4 ml of a peptide-mRNA complex solution.

Biotinylation target protein was added at 200 nM to the above solution, and rotary mixing was carried out at 4° C. for 30 minutes. Dynabeads M-270 streptavidin (Invitrogen, 653-05) was then added and rotary mixing was carried out at 4° C. for 5 minutes. The supernatant was removed, followed by washing with 1×TBST (Nacalai) twice. A PCR solution not containing DNA polymerase and containing 0.5 µM primer (SEQ ID NO: DOL-4) and 0.5 µM primer (SEQ ID NO: DOL-5) was added to Dynabeads, heating and elution were performed at 95° C. for 10 minutes, and the supernatant was collected. DNA polymerase Ex Taq (Takara, RR001A-24) was added to the supernatant, cDNA was amplified by PCR, and DNA was then purified with QIAquick PCR purification kit (Qiagen).

```
SEQ ID NO: DOL-3
                                          (SEQ ID NO: 160)
TTTGTCCCCGCCGCCCTAAGAGCCAGAGCCAGAGCCGCT

SEQ ID NO: DOL-4
                                          (SEQ ID NO: 161)
GTAATACGACTCACTATAGGGTTAACTTTAAGAAGGAGA

SEQ ID NO: DOL-5
                                          (SEQ ID NO: 162)
TTTGTCCCCGCCGCCcta
```

Transcription, Ligation, Translation, Cyclization, Desulfurization and Reverse Transcription Reaction for Round 2 Panning→Panning Operation→PCR mRNA was synthesized from the cDNA amplified in round 1 using RiboMAX Express Large Scale RNA Production System (Promega, P1320), and was purified with RNeasy MinElute kit (Qiagen). mRNA was then linked to puromycin linker using T4 RNA ligase (NEB, M0204L) and purified with RNeasy MinElute kit (Qiagen). 100 µl of the aforementioned translation solution containing 1 µM of the mRNA-puromycin linker ligation product was prepared, incubated at 37° C. for 60 minutes and then allowed to stand at room temperature for 12 minutes. 10 µl of a 200 mM EDTA solution (pH 8.0, Nacalai, 14362-24) and 5 µl of a 200 mM TCEP solution (pH 7.0) were added to the translation mixture for cyclization reaction, and the mixture was incubated at 37° C. for 120 minutes. The Translation Solution S was adjusted to pH 10 by adding 0.5 M KOH thereto and then incubated at 42° C. for 30 minutes. The mixture was then adjusted to pH 7 by adding 0.5 M HCl thereto. 13 µl of a 250 mM Cys solution and 200 µl of a 400 mM TCEP solution (pH 7.0) were then added to each of the translation mixtures, and the mixture was incubated at 40° C. for 1 minute. Subsequently, 80 µl of 1 M VA-044 (Wako, CAS No. 27776-21-2) was added and desulfurization reaction was carried out at 40° C. for 1 hour. 100 µl of a peptide-mRNA complex solution was then prepared by purification with RNeasy MinElute kit (Qiagen). 3 µM primer (SEQ ID NO: DOL-3), M-MLV reverse transcriptase reaction buffer (Promega, M368B), 0.5 mM dGTP, 0.5 mM dATP, 0.5 mM dCTP, 0.5 mM dTTP and 8 U/µl M-MLV Reverse transcriptase (H—) (Promega, M368B) were added to the solution, the mixture was diluted with nuclease free water, and the resulting 200 µl solution was incubated at 42° C. for 15 minutes to cause reverse transcription reaction. An equal amount of a blocking agent SuperBlock T20 (Pierce, 37516) was added to the reverse transcription solution to 400 µl of a peptide-mRNA complex solution.

Dynabeads M-270 streptavidin was added to the above solution, rotary mixing was carried out at 4° C. for 5 minutes, and the supernatant was collected. Biotinylation target protein was added at 200 nM to the supernatant, and rotary mixing was carried out at 4° C. for 30 minutes. Dynabeads M-270 streptavidin was then added and rotary mixing was carried out at 4° C. for 5 minutes. The supernatant was removed, followed by washing with 1×TEST (Nacalai) three times. A PCR solution not containing DNA polymerase and containing 0.5 µM primer (SEQ ID NO: DOL-4) and 0.5 µM primer (SEQ ID NO: DOL-5) was added to Dynabeads, heating and elution were performed at 95° C. for 10 minutes, and the supernatant was collected. DNA polymerase Ex Taq (Takara, RR001A-24) was added to the supernatant, cDNA was amplified by PCR, and DNA was then purified with QIAquick PCR purification kit (Qiagen).

Transcription, Ligation, Translation, Cyclization, Desulfurization and Reverse Transcription Reaction for Round 3 Panning→Panning Operation→PCR mRNA was synthesized from the cDNA amplified in round 2 using RiboMAX Express Large Scale RNA Production System (Promega, P1320), and was purified with RNeasy MinElute kit (Qiagen). mRNA was then linked to puromycin linker using T4 RNA ligase (NEB, M0204L) and purified with RNeasy MinElute kit (Qiagen). 10 µl of the aforementioned translation solution containing 1 µM of the mRNA-puromycin linker ligation product was prepared, incubated at 37° C. for 60 minutes and then allowed to stand at room temperature for 12 minutes. 1 µl of a 200 mM EDTA solution (pH 8.0, Nacalai, 14362-24) and 0.5 µl of a 200 mM TCEP solution (pH 7.0) were added to the translation mixture for cyclization reaction, and the mixture was incubated at 37° C. for 120 minutes. The Translation Solution S was adjusted to pH 10 by adding 0.5 M KOH thereto and then incubated at 42° C. for 30 minutes. The mixture was then adjusted to pH 7 by adding 0.5 M HCl thereto. 1.3 µl of a 250 mM Cys solution and 20 µl of a 400 mM TCEP solution (pH 7.0) were then added to each of the translation mixtures, and the mixture was incubated at 40° C. for 1 minute. Subsequently, 8 µl of 1 M $V_A$-044 (Wako, CAS No. 27776-21-2) was added and desulfurization reaction was carried out at 40° C. for 1 hour. 10 µl of a peptide-mRNA complex solution was then prepared by purification with RNeasy MinElute kit (Qiagen). 3 µM primer (SEQ ID NO: DOL-3), M-MLV reverse transcriptase reaction buffer (Promega, M368B), 0.5 mM dGTP, 0.5 mM dATP, 0.5 mM dCTP, 0.5 mM dTTP and 8 U/µl M-MLV Reverse transcriptase (H—) (Promega, M368B) were added to the solution, the mixture was diluted to 200 µl with nuclease free water, and the resulting solution was incubated at 42° C. for 15 minutes to cause reverse transcription reaction. An equal amount of a blocking agent SuperBlock T20 (Pierce, 37516) was added to the reverse transcription solution to 40 µl of a peptide-mRNA complex solution.

Dynabeads M-270 streptavidin was added to 10 µl of the above solution, rotary mixing was carried out at 4° C. for 5 minutes, and the supernatant was collected. This operation was repeated for three times in total, after which biotinylated target protein was added at 200 nM to the supernatant, and rotary mixing was carried out at 4° C. for 30 minutes. Dynabeads M-270 streptavidin was then added and rotary mixing was carried out at 4° C. for 5 minutes. The supernatant was removed, followed by washing with 1×TEST (Nacalai) three times. A PCR solution not containing DNA polymerase and containing 0.5 µM primer (SEQ ID NO: DOL-4) and 0.5 µM primer (SEQ ID NO: DOL-5) was added to Dynabeads, heating and elution were performed at 95° C. for 10 minutes, and the supernatant was collected. DNA polymerase Ex Taq (Takara, RR001A-24) was added to the supernatant, cDNA was amplified by PCR, and DNA was then purified with QIAquick PCR purification kit (Qiagen).

The same operation as in round 3 was carried out in rounds 4 to 6 to concentrate cDNA specifically binding to the target protein. The base sequence of the concentrated DNA pool was analyzed to identify the concentrated peptide sequence.

Estimation of the Mean Values and the Distributions of the CLOGP Values, the Numbers of NMe Amino Acids and the Molecular Weights by a Virtual Library Utilizing Simulation by a Computer (FIGS. 66 and 67)

The degree of drug-likeness of the display library designed this time was evaluated. Specifically, the distributions of the CLogP values and the numbers of NMe amino acids contained in one peptide in the case where selected amino acids are evenly and randomly displayed were simulated by computation.

An actual display library has $10^{12}$ peptides or more, and it is difficult to generate such a comprehensive library even as a virtual library on a computer. Accordingly, 50,000 peptides were randomly generated as peptides translationally synthesized in the display library, and the distributions and the mean values of the CLOGPs, the numbers of NMe amino acids, and the molecular weights were approximately estimated.

Random peptide structures were programmed and output in SMILES format. Here, the C-terminal structure was piperidine. The distribution and mean value for each parameter were determined from the output peptide structure file using CLOGP (Daylight) and Pipeline Pilot (Accelrys). In the computation of CLOGP values, about 6.5% of the peptides could not be computed due to the limitation of the molecular size, and the values were provided after excluding such peptides (93.5% of the total peptides were effective).

[Example 26] Screening of Translational Products Utilizing Electrochemiluminescence (ECL)

Immunoassay of some of the clones enriched by panning was carried out using translational product peptides of the respective clones. In the immunoassay, an electrochemiluminescence (ECL) measuring instrument (SECTOR Imager 2400) was utilized to detect low-concentration peptide products with high sensitivity. Consequently, peptides binding to IL-6R, TNFα and TNFR1 were identified.

1. Synthesis of F1(Urea)-dC-Puromycin (Compound SP806) Synthesis of dC-Puromycin CPG (Compound SP802)

Figure 116:
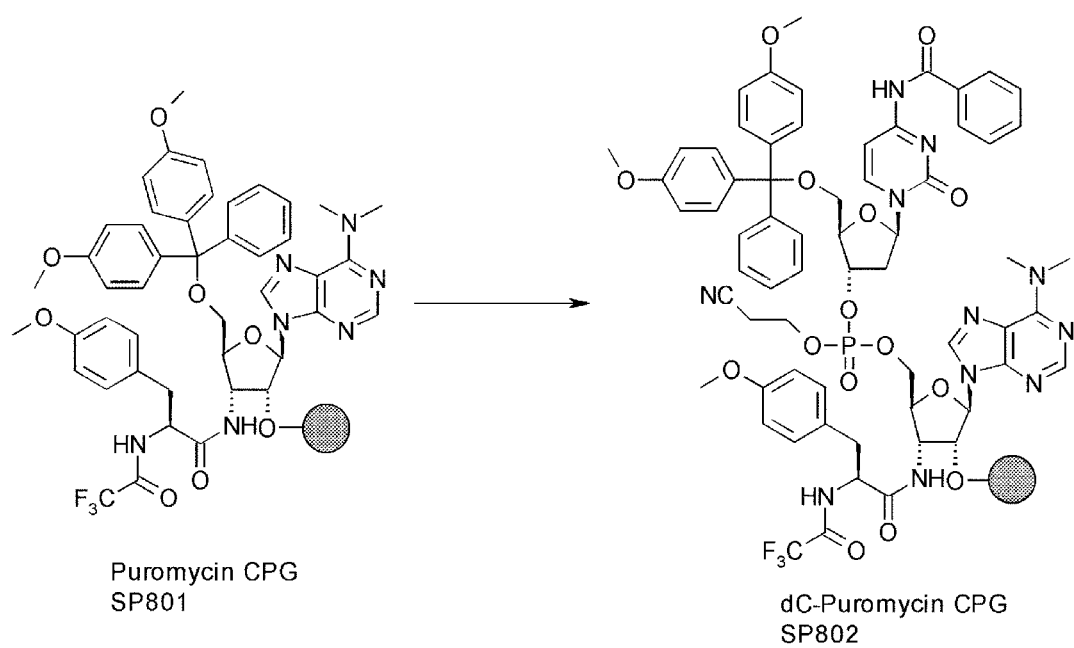

See FIG. 116.

Puromycin CPG (Compound SP801) (manufactured by Glen Research, 44 µmol/g, 450 mg) was treated with Deblocking Mix (manufactured by Glen Research, 3% trichloroacetic acid/DCM) (3 ml×4) and washed with acetonitrile (3 ml×4).

A solution of dC-CE Phosphoramidite (manufactured by Glen Research, 250 mg, 0.300 mmol) in acetonitrile (3.0 ml), and Activator (manufactured by Glen Research, 5-benzylthio-1H-tetrazole in acetonitrile, 3 ml) were added to the resulting CPG support, and the mixture was shaken at room temperature for 10 minutes, after which the reaction solution was removed, and the CPG support was washed with acetonitrile (3 ml×4) and dried.

Oxidizing Solution (manufactured by Glen Research, 0.02 M iodine in THF/pyridine/water, 3 ml) was then added and the mixture was shaken at room temperature, after which the reaction solution was removed. The support was washed with acetonitrile (3 ml×4) and then dried to afford the title dC-Puromycin CPG (Compound SP802) (450 mg).

A small amount of dC-Puromycin CPG was treated with 25% aqueous ammonia solution at 60° C. for 1.5 hours. The reaction solution was analyzed by LC/MS to confirm that the reaction proceeded and dC-Puromycin (Compound SP803) was produced. See FIG. 117.

LCMS (ESI) m/z=1061.4 (M−H)−
Retention time: 0.53 min (analysis condition SQDAA50)

Synthesis of F1-dC-Puromycin CPG (Compound SP804)

See FIG. 118.

dC-Puromycin CPG (Compound SP802) (44 µmol/g, 450 mg) was treated with Deblocking Mix (manufactured by Glen Research, 3% trichloroacetic acid/DCM) and then washed with acetonitrile.

A solution of Fluorescein Phosphoramidite (manufactured by Glen Research, 125 mg, 0.104 mmol) in acetonitrile (1.0 ml), and Activator (manufactured by Glen Research, 5-benzylthio-1H-tetrazole in acetonitrile, 1.0 ml) were added to the resulting CPG support, and the mixture was shaken at room temperature for 30 minutes, after which the reaction solution was removed, and the CPG support was washed with acetonitrile and dried.

Oxidizing Solution (manufactured by Glen Research, 0.02 M iodine in THF/pyridine/water, 3 ml) was then added and the mixture was shaken at room temperature, after which the reaction solution was removed. The CPG support was washed with acetonitrile and then dried to afford the title F1-dC-Puromycin CPG (450 mg).

A small amount of F1-dC-Puromycin CPG was treated with 25% aqueous ammonia solution at 60° C. for 1.5 hours. The reaction solution was analyzed by LC/MS to confirm that the reaction proceeded and F1-dC-Puromycin (Compound SP805) was produced.

See FIG. 119.

LCMS (ESI) m/z=1659.2 (M–H)–
Retention time: 0.94 min (analysis condition SQDAA05)

Synthesis of 5-(3-(6-(((((2R,3S,5R)-5-(4-amino-2-oxopyrimidin-1(2H)-yl)-3-(((((2S,3S,4R,5R)-3-((S)-2-amino-3-(4-methoxyphenyl)propanamido)-5-(6-(dimethylamino)-9H-purin-9-yl)-4-hydroxytetrahydrofuran-2-yl)methoxy)(hydroxy)phosphoryl)oxy)tetrahydrofuran-2-yl)methoxy)(hydroxy)phosphoryl)oxy)-7-hydroxyheptyl)ureido)-2-(6-hydroxy-3-oxo-3H-xanthen-9-yl)benzoic Acid (Compound SP806) (F1(Urea)-dC-Puromycin)

See FIG. 120.

Oxidizing Solution (manufactured by Glen Research, 0.02 M iodine in THF/pyridine/water, 3 ml) was added to F1-dC-Puromycin CPG (Compound SP304) (44 µmol/g, 105 mg), and the mixture was shaken at room temperature for 16 hours. The reaction solution was removed, after which the CPG support was washed with acetonitrile and dried.

Afterwards, the CPG support was treated with Deblocking Mix (manufactured by Glen Research, 3% trichloroacetic acid/DCM) (3 ml×4), and then washed with dichloromethane and dried.

A 25% aqueous-ammonia solution (1.0 ml) was then added to the CPG support, followed by stirring at 60° C. for 1.5 hours. The reaction solution was left to cool and then purified by column chromatography (0.1% aqueous formic acid solution/0.1% formic acid-acetonitrile solution) to afford the title compound (Compound SP806) (2.1 mg, 33.8%) as a yellow solid.

LCMS (ESI) m/z=1341.8 (M–H)–
Retention time: 0.44 min (analysis condition SQDFA05)

2. Analysis of Concentrated Sequences

Template DNAs indicated by SEQ ID NO: From DME-2 to DME-11 and from DME-13 to DME-15 were synthesized based on the sequence analysis results. These DNAs were added to an ECL transcription and translation solution, and peptide synthesis was carried out by translation. The ECL transcription and translation solution has the following composition: 5% (v/v) T7 RNA polymerase RiboMAX Enzyme Mix (Promega, P1300), 2 mM GTP, 2 mM ATP, 1 mM CTP, 1 mM UTP, 20 mM creatine phosphate, 50 mM HEPES-KOH pH7.6, 100 mM potassium acetate, 15 mM magnesium acetate, 2 mM spermidine, 1 mM dithiothreitol, 0.5 mg/ml E. coli MRE600 (RNase-negative)-derived tRNA (Roche), 3 µM transcribed tRNA Ala1B (SEQ ID NO: MIL-13), 3 µM transcribed tRNA Tyr1 (SEQ ID NO: MTL-14), 4 µg/ml creatine kinase, 3 µg/ml myokinase, 2 units/ml inorganic pyrophosphatase, 1.1 µg/ml nucleoside diphosphate kinase, 0.26 µM EF-G, 0.24 µM RF2, 0.17 µM RF3, 0.5 µM RRF, 2.7 µM IF1, 0.4 µM IF2, 1.5 µM IF3, 53 µM EF-Tu, 112 µM EF-Ts, 1.2 µM ribosome, 2.73 µM AlaRS, 0.09 µM GlyRS, 0.4 µM IleRS, 0.68 µM PheRS, 0.16 µM ProRS, 0.04 µM SerRS, 0.09 µM ThrRS, 0.03 µM TrpRS, 0.22 µM TyrRS, 0.02 µM ValRS, 250 µM glycine, 250 µM isoleucine, 250 µM proline, 250 µM threonine, 250 µM tryptophan, 250 µM valine, 100 µM serine, 5 mM N-methylalanine, 5 mM N-methylphenylalanine, 2 mM D-tyrosine, and the ECL transcription and translation solution S was prepared by further adding the aminoacylated tRNA mixture for Translation Solution S and the initiator aminoacylated tRNA for Translation Solution S to the above composition, and the ECL transcription and translation solution T was prepared by further adding 0.02 µM CysRS, 250 µM cysteine and the aminoacylated tRNA mixture for Translation Solution T to the above composition.

0.05 µM template DNA and 12.5 µM F1Pu(urea) (Compound SP806) were added to the ECL transcription and translation solution, and the mixture was left to stand at 37° C. for 1 hour and at room temperature for 12 minutes to synthesize a peptide labeled with F1Pu(urea) at the C-terminal. Nuclease free water was added in place of template DNA to a sample used as a negative control. 0.5 µl of a 200 mM EDTA solution (pH 8.0, Nacalai, 14362-24) and 0.5 µl of a 100 mM TCEP solution (pH 6.6) were added to 5 µL of the translation mixture, and the mixture was incubated at 37° C. for 120 minutes to cause cyclization reaction. 11 µL of desulfurization buffer (15 mM cysteine, 36 mM TCEP) was added to the cyclization product, and the mixture was incubated at 42° C. for 1 minutes, after which 4 µL of 1 M VA-044 (Wako, CAS No. 27776-21-2) was added and the mixture was allowed to stand at 42° C. for 1 hour. 3 µL of 125 mM cysteine was added and the mixture was further allowed to stand at 42° C. for 1 hour to inactivate unreacted TCEP, after which 1 µL of 0.5 M Tris and 6 µL of SuperBlock T20 (Pierce, 37516) were added to prepare a peptide solution for ECL assay.

Immunoassay was carried out using the above peptide solution for ECL assay. 500 nM biotinylated target protein was added at 10 µL per well to MSD Streptavidin MULTI-ARRAY 384-well plate (Meso Scale Discovery, L25SB-1), and reaction was conducted at room temperature for 1 hour with shaking at 500 rpm to immobilize the target protein. 2% skim milk PBS was added at 50 µL per well, and blocking was carried out by allowing to stand at room temperature for 2 hours. The reaction solution was removed and the plate was washed with PBS containing 0.05% Tween 20 (PBST) three times, after which 10 µL of the peptide solution for ECL assay was added and the plate was shaken at room temperature for 50 minutes at 500 rpm. The reaction solution was removed and the plate was washed with PBST three times, after which 10 µL of IgG Fraction Monoclonal Mouse Anti-Fluorescein (Jackson ImmunoResearch, 200-002-037) diluted to 0.5 µg/mL with 2% skim milk PBS was added, and reaction was conducted at room temperature for 50 minutes with shaking at 500 rpm. The reaction solution was removed and the plate was washed with PBST three times, after which 10 µL of SULFO-TAG Anti-Mouse Antibody (Meso Scale Discovery, R32AC-5) diluted to 1 µg/mL with 2% skim milk PBS was added, and reaction was conducted at room temperature for 50 minutes with shaking at 500 rpm. The reaction solution was removed and the plate was washed with PBST three times, after which 35 µL of 2×Read Buffer T (Meso Scale Discovery, R92TC-3) was added and measurement was carried out using SECTOR Imager 2400 (Meso Scale Discovery).

Measurements of the samples are shown in Table 24, respectively.

TABLE 24

Screening results by ECL

| Template DNA SEQ ID NO: | Transcription and translation solution for ECL | Target protein | ECL signal |
|---|---|---|---|
| DME-2 | Translation Solution T | IL-6R | 307204 |
| DME-3 | Translation Solution T | IL-6R | 69961 |
| DME-4 | Translation Solution T | TNFR1 | 32050 |
| DME-5 | Translation Solution T | TNFR1 | 3762 |
| DME-6 | Translation Solution T | TNFR1 | 3613 |
| DME-7 | Translation Solution S | TNFα | 8324 |
| DME-8 | Translation Solution T | TNFα | 73257 |
| DME-9 | Translation Solution T | TNFα | 264265 |
| DME-10 | Translation Solution T | TNFα | 50669 |
| DME-11 | Translation Solution T | TNFα | 149328 |
| DME-13 | Translation Solution T | IL-6R | 537113 |
| DME-14 | Translation Solution T | IL-6R | 45610 |
| DME-15 | Translation Solution S | IL-6R | 538876 |
| Negative control | Translation Solution T | TNFα | 232 |
| Negative control | Translation Solution S | TNFα | 238 |
| Negative control | Translation Solution T | TNFR1 | 293 |
| Negative control | Translation Solution S | TNFR1 | 330 |
| Negative control | Translation Solution T | IL-6R | 177 |
| Negative control | Translation Solution S | IL-6R | 197 |

[ECL Template DNA Sequences]

SEQ ID NO: DME-2
(IL-6R binder) DNA sequence
(SEQ ID NO: 164)
GTAATACGACTCACTATAGGGTTAACTTTAAGAAGGAGATATACATATG

TGCCCGATTATTTTTATGCCGAGGTACGTTCGTAGTACTAGCGGCTCTG

GCTCTGGCTCT

SEQ ID NO: DME-3
(IL-6R binder) DNA sequence
(SEQ ID NO: 165)
GTAATACGACTCACTATAGGGTTAACTTTAAGAAGGAGATATACATATG

TGCCCGATTATTTGGAGGATGCCGAGGTACCGTGTTTACAGCGGCTCTG

GCTCTGGCTCT

SEQ ID NO: DME-4
(TNFR1 binder) DNA sequence
(SEQ ID NO: 166)
GTAATACGACTCACTATAGGGTTAACTTTAAGAAGGAGATATACATATG

TGCTACATTTGGATGAGTATGAGGGTTTTCGTACTAGGAGCGGCTCTG

GCTCTGGCTCT

SEQ ID NO: DME-5
(TNFR1 binder) DNA sequence
(SEQ ID NO: 167)
GTAATACGACTCACTATAGGGTTAACTTTAAGAAGGAGATATACATATG

TGCCCGTTGATTATTGTTAGTCGGCTTCTTCGTGAAACTAGCGGCTCTG

GCTCTGGCTCT

SEQ ID NO: DME-6
(TNFR1 binder) DNA sequence
(SEQ ID NO: 168)
GTAATACGACTCACTATAGGGTTAACTTTAAGAAGGAGATATACATATG

TGCCCGTTGGTTATTACTGTTCGGCTTAGTCGTGCTAGGAGCGGCTCTG

GCTCTGGCTCT

SEQ ID NO: DME-7
TNFα binder DNA sequence
(SEQ ID NO: 169)
GTAATACGACTCACTATAGGGTTAACTTTAAGAAGGAGATATACATATG

ACTCTTATTGAATGGTGGCTATACAGGCGTCCGTTGAGCGGCTCTGGCT

CTGGCTCT

SEQ ID NO: DME-8
TNFα binder DNA sequence
(SEQ ID NO: 170)
GTAATACGACTCACTATAGGGTTAACTTTAAGAAGGAGATATACATATG

TGCCTATGGTGGGTTTTGGGTCCGTAGAGTCGTCGGATGAGCGGCTCTG

GCTCTGGCTCT

SEQ ID NO: DME-9
TNFα binder DNA sequence
(SEQ ID NO: 171)
GTAATACGACTCACTATAGGGTTAACTTTAAGAAGGAGATATACATATG

TGCGAAATTCCGGTTTGGTGGCTAATGGTTCGTTGGGAAAGCGGCTCTG

GCTCTGGCTCT

SEQ ID NO: DME-10
TNFα binder DNA sequence
(SEQ ID NO: 172)
GTAATACGACTCACTATAGGGTTAACTTTAAGAAGGAGATATACATATG

TGCACTATTCCGTACTGGTGGCTAATGGTTCGTTGGGAAAGCGGCTCTG

GCTCTGGCTCT

SEQ ID NO: DME-11
TNFα binder DNA sequence
(SEQ ID NO: 173)
GTAATACGACTCACTATAGGGTTAACTTTAAGAAGGAGATATACATATG

TGCACTTGGATTTTTCTTTGGCAGCTACTTCGTGTTACTAGCGGCTCTG

GCTCTGGCTCT

SEQ ID NO: DME-13
IL-6R binder DNA sequence
(SEQ ID NO: 175)
GTAATACGACTCACTATAGGGTTAACTTTAAGAAGGAGATATACATATG

TGCCCGGTTATTTTTATGCCGAGGGTTATGCGTCCGTTGAGCGGCTCTG

GCTCTGGCTCT

SEQ ID NO: DME-14
IL-6R binder DNA sequence
(SEQ ID NO: 176)
GTAATACGACTCACTATAGGGTTAACTTTAAGAAGGAGATATACATATG

TGCATTATTGAATGGCCGAGGATGTACCAGCGTCCGAGGAGCGGCTCTG

GCTCTGGCTCT

SEQ ID NO: DME-15
IL-6R binder DNA sequence
(SEQ ID NO: 177)
GTAATACGACTCACTATAGGGTTAACTTTAAGAAGGAGATATACATATG

ATTGTTTGGAGGTGCCCGAGGTACTGCCGTGAAGCTAGCGGCTCTGGCT

CTGGCTCT

[ECL Peptide Sequences]

All peptides shown below are cyclic peptides having peptide bonds formed between the N-terminal amino group and side chain carboxylic acid of 11th aspartic acid. Abbreviations are as described in conventional documents or the product catalog of Watanabe Chemical Industries, and are shown in detail below.

MeAla(4-Thz): (S)-2-(Methylamino)-3-(thiazol-4-yl)propanoic acid
MePhe(3-Cl): (S)-3-(3-Chlorophenyl)-2-(methylamino)propanoic acid
Hyp(Et): (2S,4R)-4-Ethoxypyrrolidine-2-carboxylic acid γEtAbu: 4-(Ethylamino)butanoic acid
nPrGly: 2-(Propylamino)acetic acid
MePhe: (S)-2-(Methylamino)-3-phenylpropanoic acid
MeAla: (S)-2-(Methylamino)propanoic acid
MeGly: 2-(Methylamino)acetic acid
Pro: (S)-Pyrrolidine-2-carboxylic acid
Thr: (2S,3R)-2-amino-3-hydroxybutanoic acid
Phg: (S)-2-amino-2-phenylacetic acid
Ile: (2S,3S)-2-amino-3-methylpentanoic acid
Val: (S)-2-Amino 3-methylbutanoic acid
Asp: (S)-2-Aminosuccinic acid Trp: (S)-2-amino-3-(1H-indol-3-yl)propanoic acid
DTyr: (R)-2-amino-3-(4-hydroxyphenyl)propanoic acid
Phe (4-CF3): (S)-2-amino-3-(4-(trifluoromethyl)phenyl) propanoic acid
Ser: (S)-2-amino-3-hydroxypropanoic acid
Met(O2): (S)-2-amino-4-(methylsulfonyl)butanoic acid
βAla: 3-Aminopropanoic acid
Ala: (S)-2-Aminopropanoic acid
Gly: 2-Aminoacetic acid
MeSer: (S)-3-hydroxy-2-(methylamino)propanoic acid
F1Pu(urea): Compound SP806

SEQ ID NO: PE-2
(IL-6R binder) Peptide sequence
(SEQ ID NO: 288)
Ala-Pro-Ile-Ile-MePhe-Met(O2)-Pro-MePhe(3-Cl)-

DTyr-Val-Asp-Ser-Thr-Ser-Gly-Ser-Gly-Ser-Gly-Ser-

F1Pu(urea)

SEQ ID NO: PE-3
(IL-6R binder) Peptide sequence
(SEQ ID NO: 289)
Ala-Pro-Ile-Ile-Trp-MePhe(3-Cl)-Met(O2)-Pro- MePhe(3-Cl)-DTyr-Asp-Val-DTyr-Ser-Gly-Ser-Gly-Ser- Gly-Ser-F1Pu(urea)

SEQ ID NO: PE-4
(TNFR1 binder) Peptide sequence
(SEQ ID NO: 290)
Ala-DTyr-Ile-Trp-Met(O2)-Ser-Met(O2)-MePhe(3-Cl)-

Val-MePhe-Asp-Thr-MePhe(3-Cl)-Ser-Gly-Ser-Gly-Ser-

Gly-Ser-F1Pu(urea)

SEQ ID NO: PE-5
(TNFR1 binder) Peptide sequence
(SEQ ID NO: 291)
Ala-Pro-MeGly-Ile-Ile-Val-Ser-MeSer-Phg-Phg-Asp- MeAla(4-Thz)-Thr-Ser-Gly-Ser-Gly-Ser-Gly-Ser- F1Pu(urea)

SEQ ID NO: PE-6
(TNFR1 binder) Peptide sequence
(SEQ ID NO: 292)
Ala-Pro-MeGly-Val-Ile-Thr-Val-MeSer-Phg-Ser-Asp- MeAla-MePhe(3-Cl)-Ser-Gly-Ser-Gly-Ser-Gly-Ser- F1Pu(urea)

SEQ ID NO: PE-7
(TNFα binder) Peptide sequence
(SEQ ID NO: 293)
γEtAbu-Thr-Phg-Ile-MeAla(4-Thz)-Trp-Trp-Phe(4-

CF3)-DTyr-MePhe(3-Cl)-Asp-Pro-MeGly-Ser-Gly-Ser-

Gly-Ser-Gly-Ser-F1Pu(urea)

SEQ ID NO: PE-8
(TNFα binder) Peptide sequence
(SEQ ID NO: 294)
Ala-Phe(4-CF3)-Trp-Trp-Val-MeGly-Gly-Pro-Hyp(Et)-

Ser-Asp-MeSer-Met(O2)-Ser-Gly-Ser-Gly-Ser-Gly-Ser-

F1Pu(urea)

-continued

SEQ ID NO: PE-9
(TNFα binder) Peptide sequence
(SEQ ID NO: 295)
Ala-MeAla(4-Thz)-Ile-Pro-Val-Trp-Trp-Phe(4-CF3)-

Met(O2)-Val-Asp-Trp-MeAla(4-Thz)-Ser-Gly-Ser-Gly-

Ser-Gly-Ser-FlPu(urea)

SEQ ID NO: PE-10
(TNFα binder) Peptide sequence
(SEQ ID NO: 296)
Ala-Thr-Ile-Pro-DTyr-Trp-Trp-Phe(4-CF3)-Met(O2)-

Val-Asp-Trp-MeAla(4-Thz)-Ser-Gly-Ser-Gly-Ser-Gly-

Ser-FlPu(urea)

SEQ ID NO: PE-11
(TNFα binder) Peptide sequence
(SEQ ID NO: 297)
Ala-Thr-Trp-Ile-MePhe-Phg-Trp-βAla-Phe(4-CF3)-Phg- Asp-Val-Thr-Ser-Gly-Ser-Gly-Ser-Gly-Ser-FlPu(urea)

SEQ ID NO: PE-13
(IL-6R binder) Peptide sequence
(SEQ ID NO: 298)
Ala-Pro-Val-Ile-MePhe-Met(O2)-Pro-MePhe(3-Cl)-Val- Met(O2)-Asp-Pro-MeGly-Ser-Gly-Ser-Gly-Ser-Gly-Ser- FlPu(urea)

SEQ ID NO: PE-14
(IL-6R binder) Peptide sequence
(SEQ ID NO: 299)
Ala-Ile-Ile-MeAla(4-Thz)-Trp-Pro-MePhe(3-Cl)-

Met(O2)-DTyr-βAla-Asp-Pro-MePhe(3-Cl-Ser-Gly-Ser-

Gly-Ser-Gly-Ser-FlPu(urea)

SEQ ID NO: PE-15
(IL-6R binder) Peptide sequence
(SEQ ID NO: 300)
γEtAbu-Ile-Val-Trp-MePhe(3-Cl)-Met(O2)-Pro- MePhe(3-Cl)-DTyr-Met(O2)-Asp-MeAla(4-Thz)-MeAla- Ser-Gly-Ser-Gly-Ser-Gly-Ser-FlPu(urea)

Characteristics of the peptides indicated by SEQ ID NO: PE-2 to PE-11 and PE-13 to PE-15 are shown below.

The common sequence, a sequence excluding Ser-Gly-Ser-Gly-Ser-Gly-Ser-FlPu(urea) (SEQ ID NO: 301), is constituted by 13 amino acids, where 11 amino acids constitute a cyclic peptide site and 2 amino acids constitute a linear site. The amino acids contained are α-, β- and γ-amino acids, and the amino acid side chain is formed by an alkyl group, a cycloalkyl group, an ether group-substituted cycloalkyl group, a hydroxyl group (—OH)-substituted alkyl group, a sulfone group (—SO₂—R)-substituted alkyl group, an aryl group, an aralkyl group, a hydroxyl group (—OH)-substituted aralkyl group, a halogen group-substituted aralkyl group, or a heteroaryl group. These facts are preferred for drug-like peptide compounds.

Table 25 shows SEQ ID NO:, the numbers of N-alkylamino acids contained, and the clogP values of compounds excluding the common region Ser-Gly-Ser-Gly-Ser-Gly-Ser-FlPu(urea) (SEQ ID NO: 301) and having piperidine amides at the C-terminals.

TABLE 25

| SEQ ID NO: // | Number of N-alkylamino acids | clogP value |
| --- | --- | --- |
| 288 // PE-2 | 4 | 7.2 |
| 289 // PE-3 | 4 | 11.3 |
| 290 // PE-4 | 3 | 6.5 |
| 291 // PE-5 | 4 | 5.5 |
| 292 // PE-6 | 5 | 6.5 |
| 293 // PE-7 | 5 | 12.0* |
| 294 // PE-8 | 4 | 3.7 |
| 295 // PE-9 | 3 | 9.1* |
| 296 // PE-10 | 2 | 7.8* |
| 297 // PE-11 | 1 | 9.9 |
| 298 // PE-13 | 6 | 6.0 |
| 299 // PE-14 | 5 | 9.4 |
| 300 // PE-15 | 6 | 7.3 |

*cLogP values were determined by the sum of individually calculated cLogP values of the main chain, the side chain and the linear site.

Among PE-2 to PE-11 and PE13 to PE-15, 10 peptide sequences have both at least two N-alkylamino acids and a cLogP of 6 or more, and 3 peptide sequences have either at least two N-alkylamino acids or a cLogP of 6 or more. These target-bound peptides are compounds sufficiently expected to have drug-likeness.

3. Chemical Synthesis of Peptide Sequences Concentrated and Confirmed by ECL for Binding Peptide synthesis was carried out according to the Fmoc solid-phase peptide synthesis method shown in Scheme J-1. Abbreviations for amino acids in Examples are as described in conventional documents, the product catalog (Watanabe Chemical Industries) or the like, and are shown in detail below.

MeAla(4-Thz): (S)-2-(Methylamino)-3-(thiazol-4-yl)propanoic acid
MePhe(3-Cl): (S)-3-(3-Chlorophenyl)-2-(methylamino)propanoic acid
Hyp(Et): (2S,4R)-4-Ethoxypyrrolidine-2-carboxylic acid
γEtAbu: 4-(Ethylamino)butanoic acid
nPrGly: 2-(Propylamino)acetic acid
MePhe: (S)-2-(Methylamino)-3-phenylpropanoic acid
MeAla: (S)-2-(Methylamino)propanoic acid
MeGly: 2-(Methylamino)acetic acid
Pro: (S)-Pyrrolidine-2-carboxylic acid
Thr: (2S,3R)-2-amino-3-hydroxybutanoic acid
Phg: (S)-2-amino-2-phenylacetic acid
Ile: (2S,3S)-2-amino-3-methylpentanoic acid
Val: (S)-2-Amino 3-methylbutanoic acid
Asp: (S)-2-Aminosuccinic acid
Trp: (S)-2-amino-3-(1H-indol-3-yl)propanoic acid
DTyr: (R)-2-amino-3-(4-hydroxyphenyl)propanoic acid
Phe (4-CF3): (S)-2-amino-3-(4-(trifluoromethyl)phenyl)propanoic acid
Ser: (S)-2-amino-3-hydroxypropanoic acid
Met(O2): (S)-2-amino-4-(methylsulfonyl)butanoic acid
βAla: 3-Aminopropanoic acid
Ala: (S)-2-Aminopropanoic acid
Gly: 2-Aminoacetic acid
MeSer: (S)-3-hydroxy-2-(methylamino)propanoic acid Scheme J-1

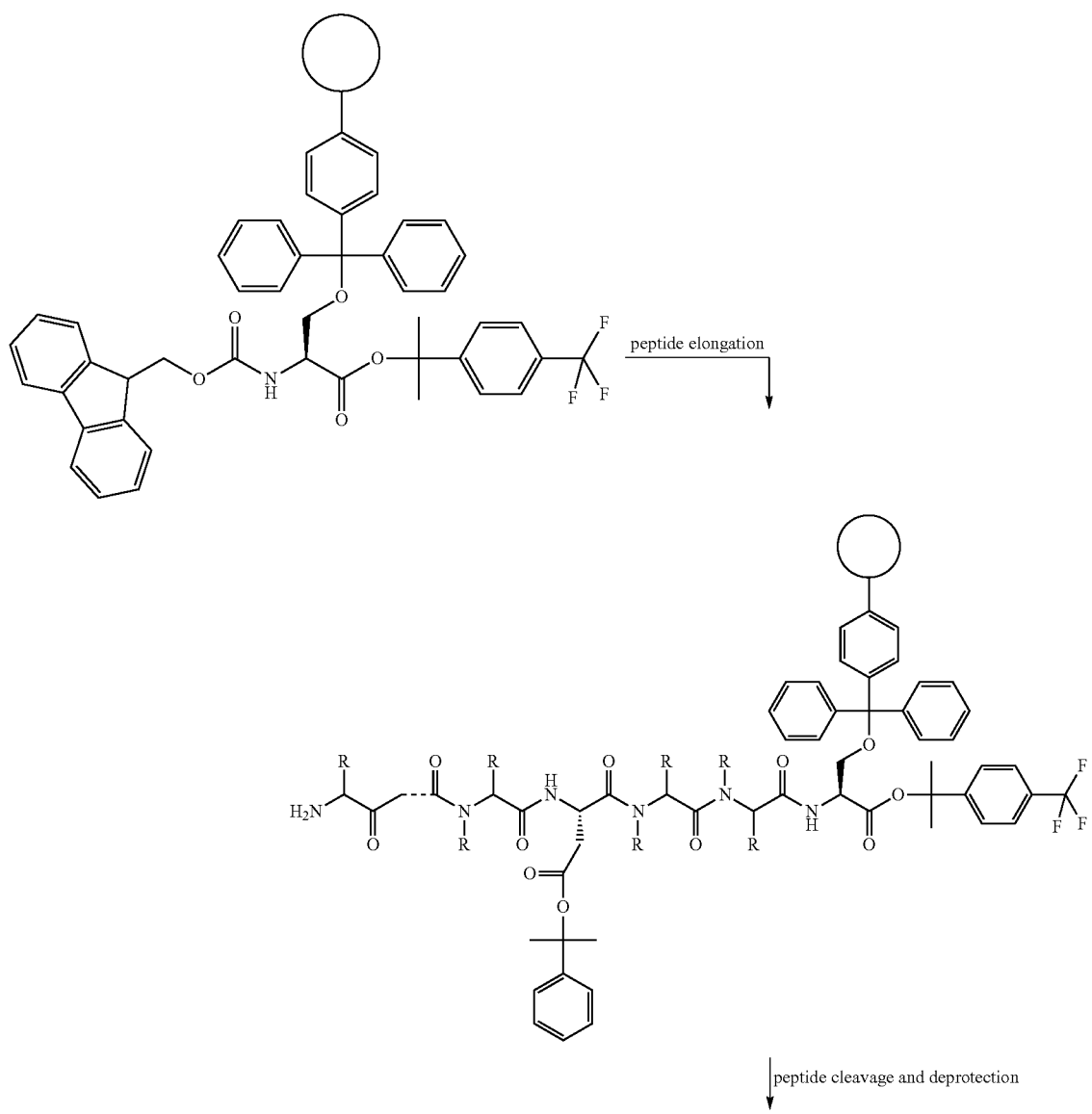

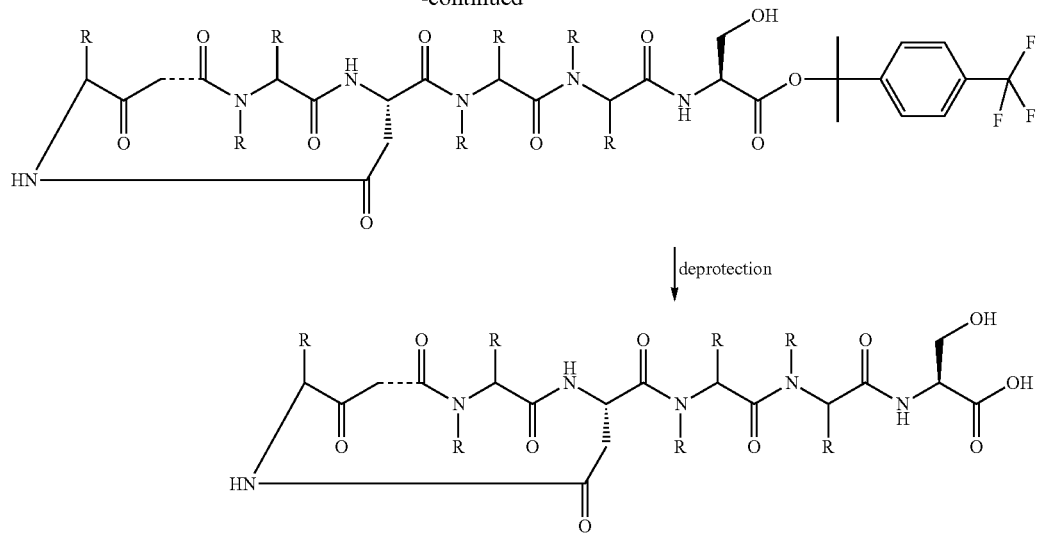

The structures of protecting groups for Fmoc amino acids in Examples are shown below. The following structures bind to polar groups of Fmoc amino acids at * sites, respectively.

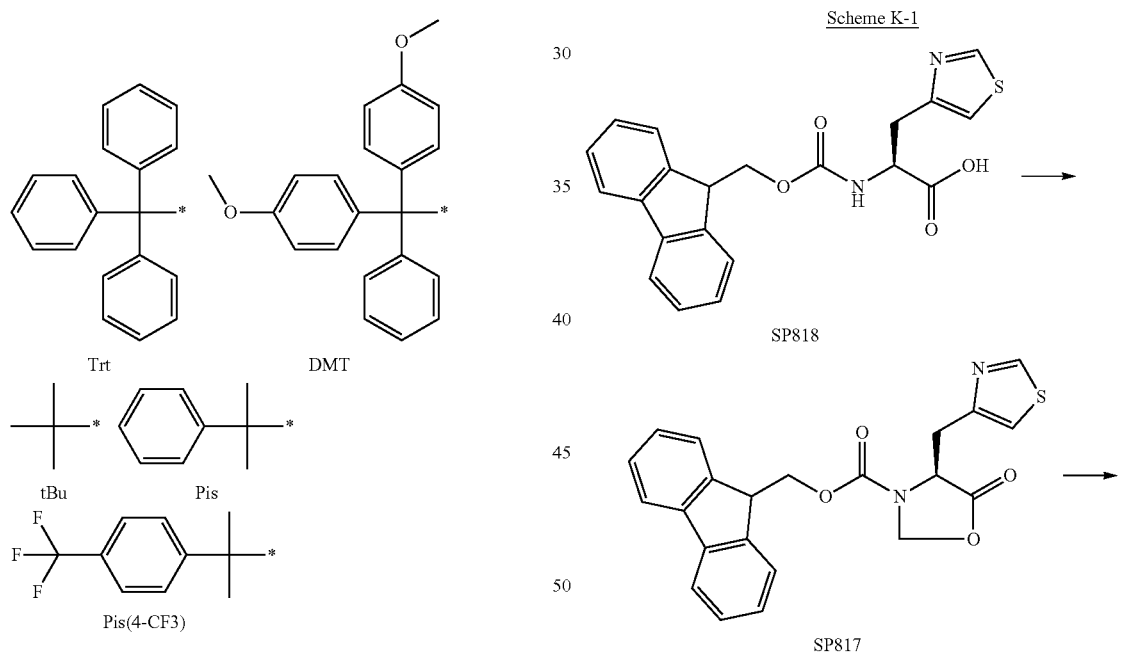

Fmoc amino acids used for peptide elongation, Fmoc-MePhe-OH, Fmoc-MeAla-OH, Fmoc-MeGly-OH, Fmoc-Pro-OH, Fmoc-Thr(Trt)-OH, Fmoc-Ph-OH, Fmoc-Ile-OH, Fmoc-Val-OH, Fmoc-Asp(OPis)-OH, Fmoc-Trp-OH, Fmoc-DTyr(tBu)-OH, Fmoc-Phe(4-CF3)-OH, Fmoc-Ser(Trt)-OH, Fmoc-Met(O2)-OH, Fmoc-βAla-OH, Fmoc-Ala-OH and Fmoc-Gly-OH, were purchased from Watanabe Chemical Industries, Chempep, U.S., or Chem-Impex, U.S.

Fmoc-MeAla(4-Thz)-OH (Compound SP811) and Fmoc-MePhe(3-Cl)—OH (Compound SP812) were synthesized according to the scheme shown in Scheme K-1. Fmoc-Hyp(Et)-OH (Compound SP813), Fmoc-γEtAbu-OH (Compound SP814) and Fmoc-nPrGly-OH (Compound SP815) were synthesized according to the scheme shown in Scheme K-2. Fmoc-MeSer(DMT)-OH (Compound SP816) was synthesized according to the scheme shown in Scheme K-3.

2629 -continued
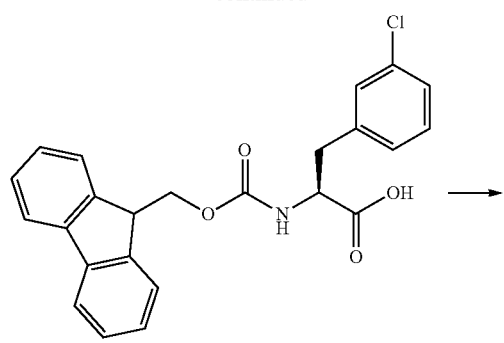
SP851
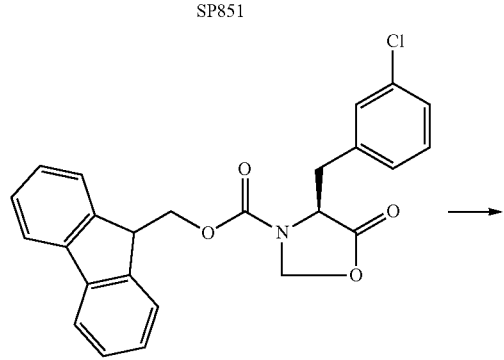
SP819
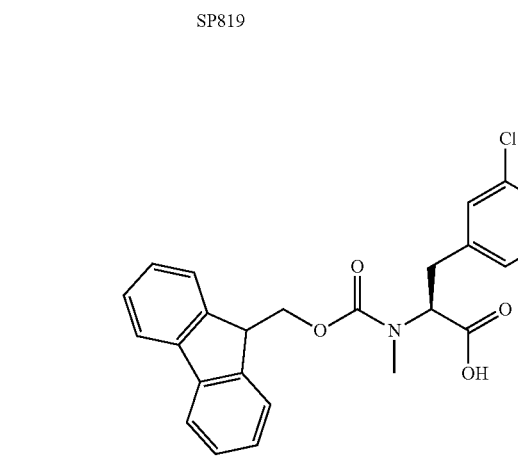
SP812
Scheme K-2
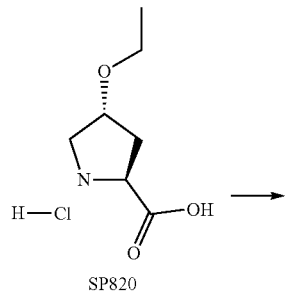
SP820
2630 -continued
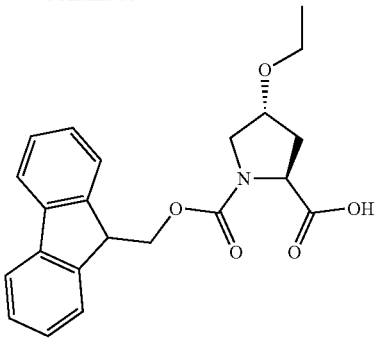
SP813
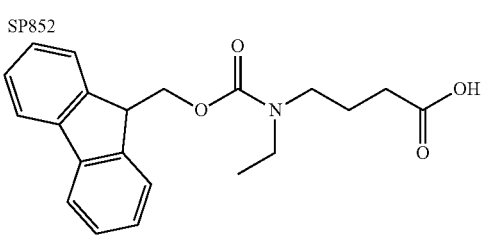
SP852 → SP814
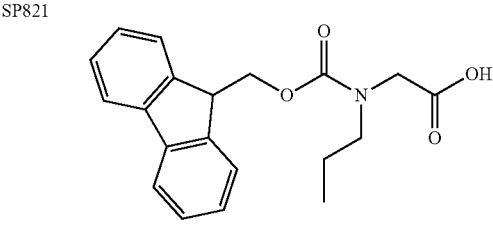
SP821 → SP815
Scheme K-3
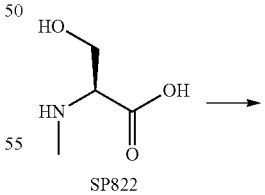
SP822
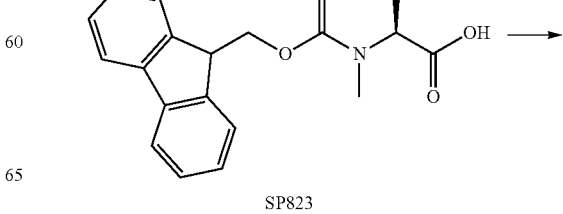
SP823

-continued

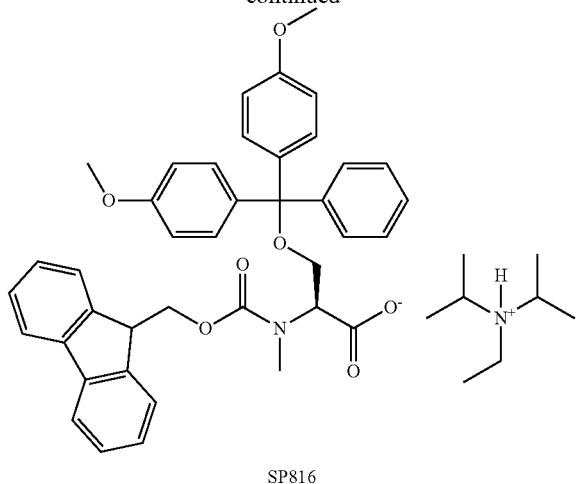

SP816

Synthesis of (S)-(9H-fluoren-9-yl)methyl 5-oxo-4-(thiazol-4-ylmethyl)oxazolidine-3-carboxylate (Compound SP817)

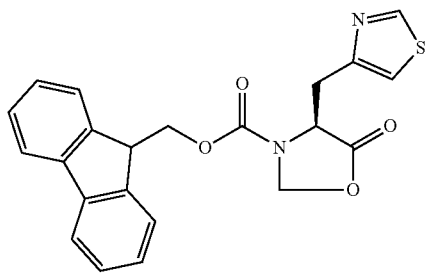 [SMILES: O=C1OCN(C(=O)OCC2c3ccccc3-c3ccccc32)[C@H]1Cc1cscn1]

(S)-2-((((9H-Fluoren-9-yl)methoxy)carbonyl)amino)-3-(thiazol-4-yl)propanoic acid (Fmoc-Ala(4-Thz)-OH, Compound SP818) (50 g, 127 mmol), camphorsulfonic acid (2.10 g, 9.04 mmol) and paraformaldehyde (110 g, 3.66 mol) were dissolved in toluene (2 l) under a nitrogen atmosphere, and the mixture was stirred at 80° C. for two days. The reaction solution was diluted with diethyl ether and sequentially washed with an aqueous sodium bicarbonate solution and brine. The resulting organic extract was dried over sodium sulfate and then concentrated under reduced pressure to afford (S)-(9H-fluoren-9-yl)methyl 5-oxo-4-(thiazol-4-ylmethyl)oxazolidine-3-carboxylate (Compound SP817) (40.0 g, 98%) as a crude product.

Synthesis of (S)-2-((((9H-fluoren-9-yl)methoxy)carbonyl)(methyl)amino)-3-(thiazol-4-yl)propanoic Acid (Compound SP811, Fmoc-MeAla(4-Thz)-OH)

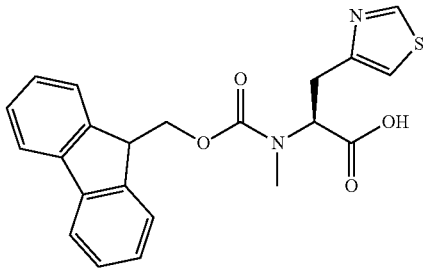 [SMILES: CN(C(=O)OCC1c2ccccc2-c2ccccc21)[C@@H](Cc1cscn1)C(=O)O]

(S)-(9H-fluoren-9-yl)methyl 5-oxo-4-(thiazol-4-ylmethyl)oxazolidine-3-carboxylate (Compound SP817) (40.0 g, 98.4 mmol), trifluoroacetic acid (245 ml, 3.18 mol) and triethylsilane (160 ml, 1.00 mol) were dissolved in dichloromethane (1 l) under a nitrogen atmosphere, and the mixture was stirred at 35° C. for two days. The reaction solution was concentrated under reduced pressure and then dissolved in diethyl ether, and the organic layer was washed with an aqueous sodium bicarbonate solution. The aqueous layer was adjusted to pH 3 with a aqueous potassium bisulfate solution and extracted with dichloromethane. All organic extracts obtained were washed with brine, dried over sodium sulfate and then concentrated under reduced pressure to afford (S)-2-((((9H-fluoren-9-yl)methoxy)carbonyl)(methyl)amino)-3-(thiazol-4-yl)propanoic acid (Compound SP811, Fmoc-MeAla(4-Thz)-OH) (35 g, 87%).

LCMS (ESI) m/z=409 (M+H)+

Retention time: 0.44 min (analysis condition SQDAA50)

Synthesis of (S)-(9H-fluoren-9-yl)methyl 4-(3-chlorobenzyl)-5-oxooxazolidine-3-carboxylate (Compound SP819)

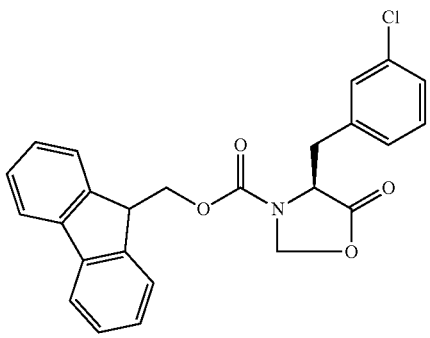 [SMILES: O=C1OCN(C(=O)OCC2c3ccccc3-c3ccccc32)[C@H]1Cc1cccc(Cl)c1]

(S)-(9H-fluoren-9-yl)methyl 4-(3-chlorobenzyl)-5-oxooxazolidine-3-carboxylate (Compound SP819) (39.0 g, 63%) was obtained using (S)-2-((((9H-fluoren-9-yl)methoxy)carbonyl)amino)-3-(3-chlorophenyl)propanoic acid (Compound SP851) (60.0 g, 142 mmol) in place of (S)-2-((((9H-fluoren-9-yl)methoxy)carbonyl)amino)-3-(thiazol-4-yl)propanoic acid (Compound SP818) under the same conditions as in the preparation example for Compound SP817.

Synthesis of (S)-2-((((9H-fluoren-9-yl)methoxy)carbonyl)(methyl)amino)-3-(3-chlorophenyl)propanoic Acid (Compound SP812, Fmoc-MePhe(3-Cl)—OH)

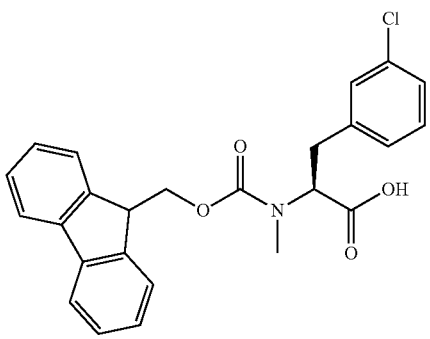 [SMILES: CN(C(=O)OCC1c2ccccc2-c2ccccc21)[C@@H](Cc1cccc(Cl)c1)C(=O)O]

(S)-2-((((9H-fluoren-9-yl)methoxy)carbonyl)(methyl)amino)-3-(3-chlorophenyl)propanoic acid (Compound SP812) (17.0 g, 85%) was obtained using (S)-(9H-fluoren-9-yl)methyl 4-(3-chlorobenzyl)-5-oxooxazolidine-3-carboxylate (Compound SP819) (20.0 g, 46.1 mmol) in place of (S)-(9H-fluoren-9-yl)methyl 5-oxo-4-(thiazol-4-ylmethyl)oxazolidine-3-carboxylate (Compound SP817) under the same conditions as in the preparation example for Compound SP811.

LCMS (ESI) m/z=436 (M+H)+

Retention time: 0.66 min (analysis condition SQDAA50)

Synthesis of (2S,4R)-1-(((9H-fluoren-9-yl)methoxy)carbonyl)-4-ethoxypyrrolidine-2-carboxylic Acid (Compound SP813, Fmoc-Hyp(Et)-OH)

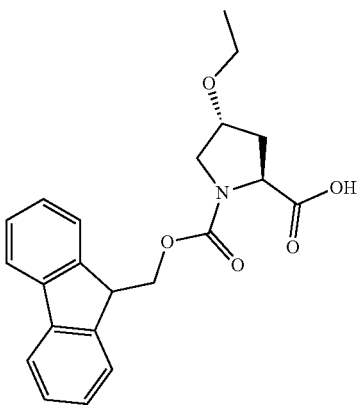 [SMILES: CCO[C@@H]1C[C@@H](C(=O)O)N(C(=O)OCC2c3ccccc3-c3ccccc32)C1]

(2S,4R)-4-Ethoxypyrrolidine-2-carboxylic acid hydrochloride (Compound SP820) (45 g, 230 mmol) was dissolved in a mixture of 1,4-dioxane (500 ml) and water (500 ml), potassium carbonate (79.4 g, 574 mmol) and (9H-fluoren-9-yl)methyl (2,5-dioxopyrrolidin-1-yl) carbonate (Fmoc-OSu, 69.8 g, 207 mmol) were added, and the mixture was stirred at room temperature for 2 hours. The reaction solution was washed with diethyl ether, and the aqueous layer was adjusted to pH 3 with an aqueous potassium bisulfate solution and extracted with ethyl acetate. The resulting organic extract was washed with brine, dried over sodium sulfate and then concentrated under reduced pressure to afford (2S,4R)-1-(((9H-fluoren-9-yl)methoxy)carbonyl)-4-ethoxypyrrolidine-2-carboxylic acid (Compound SP813, Fmoc-Hyp(Et)-OH) (90.7 g, 103%).

LCMS (ESI) m/z=382 (M+H)+

Retention time: 0.92 min (analysis condition SQDAA05)

Synthesis of 4-((((9H-fluoren-9-yl)methoxy)carbonyl)(ethyl)amino)butanoic Acid (Compound SP814, Fmoc-γEtAbu-OH)

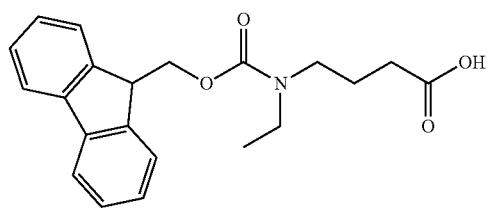 [SMILES: CCN(CCCC(=O)O)C(=O)OCC1c2ccccc2-c2ccccc21]

4-((((9H-fluoren-9-yl)methoxy)carbonyl)(ethyl)amino)butanoic acid (Compound SP814, Fmoc-γEtAbu-OH) (9.60 g, 65%) was obtained using 4-(ethylamino)butanoic acid hydrochloride (Compound SP852) (7.00 g, 41.8 mmol) in place of (2S,4R)-4-ethoxypyrrolidine-2-carboxylic acid (Compound SP820) under the same conditions as in the preparation example for Compound SP813.

LCMS (ESI) m/z=354 (M+H)+

Retention time: 0.93 min (analysis condition SQDAA05)

Synthesis of (2-((((9H-fluoren-9-yl)methoxy)carbonyl)(propyl)amino)acetic Acid (Compound SP815)

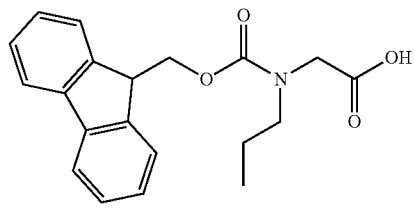 [SMILES: CCCN(CC(=O)O)C(=O)OCC1c2ccccc2-c2ccccc21]

(2-((((9H-fluoren-9-yl)methoxy)carbonyl)(propyl)amino)acetic acid (Compound SP815, Fmoc-nPrGly-OH) (215 g, 93%) was obtained using 2-(propylamino)acetic acid hydrochloride (Compound SP821) (105 g, 684 mmol) in place of (2S,4R)-4-ethoxypyrrolidine-2-carboxylic acid (Compound SP820) under the same conditions as in the preparation example for Compound SP813.

LCMS (ESI) m/z=340 (M+H)+

Retention time: 0.94 min (analysis condition SQDAA05)

Synthesis of (2S)-2-[9H-fluoren-9-ylmethoxycarbonyl(methyl)amino]-3-hydroxypropanoic Acid (Compound SP823)

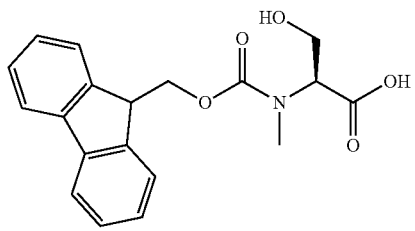 [SMILES: CN(C(=O)OCC1c2ccccc2-c2ccccc21)[C@@H](CO)C(=O)O]

A solution of FmocCl (1.35 g, 5.21 mmol) in tetrahydrofuran (5 mL) was added to a solution of N-methyl-L-serine (Compound SP822) (621 mg, 5.21 mmol) and sodium carbonate (580 mg, 5.47 mmol) in tetrahydrofuran (15 mL)-water (20 mL) at room temperature under a nitrogen atmosphere. The reaction mixture was stirred at the same temperature for 20 minutes, followed by addition of diethyl ether (10 mL) and hexane (5 mL). The resulting mixture was extracted with water, and the aqueous layer was washed with ether (15 mL), followed by addition of concentrated hydrochloric acid (1 mL). The resulting mixture was extracted with ethyl acetate three times, and the organic layer was dried over sodium sulfate and then concentrated under reduced pressure. The resulting crude product was purified by reverse-phase silica gel column chromatography (0.05% aqueous trifluoroacetic acid solution/0.05% trifluoroacetic acid-acetonitrile solution) to afford (Compound SP823) (1.49 g, 84%).

LCMS (ESI) m/z=342 (M+H)+

Retention time: 0.67 min (analysis condition SQDFA05)

Synthesis of N-ethyl-N-isopropylpropan-2-aminium (S)-2-((((9H-fluoren-9-yl)methoxy)carbonyl)(methyl)amino)-3-(bis(4-methoxyphenyl)(phenyl)methoxy)propanoate (Compound SP816)

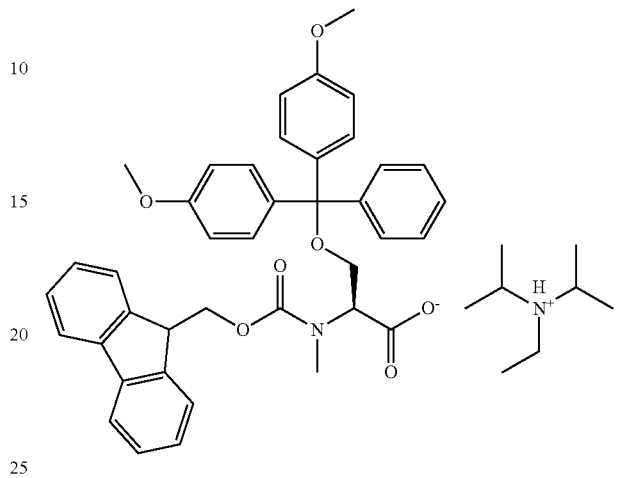

(2S)-2-[9H-Fluoren-9-ylmethoxycarbonyl(methyl)amino]-3-hydroxypropanoic acid (Compound SP823) (920 mg, 2.70 mmol) was dissolved in dehydrated pyridine (2.5 mL), and the reaction solution was concentrated under reduced pressure. This operation was repeated twice, after which the reaction solution was dissolved in dehydrated pyridine (2.5 mL) under a nitrogen atmosphere, and 4,4'-dimethoxytrityl chloride (931 mg, 2.75 mmol) was added at room temperature. The reaction mixture was stirred at the same temperature for 13 hours and then concentrated under reduced pressure. The resulting residue was dissolved in chloroform (15 mL) and washed with saturated sodium bicarbonate (5 mL). The organic layer was dried over sodium sulfate and then concentrated under reduced pressure, and the resulting crude product was purified by normal-phase silica gel column chromatography (1% diisopropylethylamine-containing dichloromethane/methanol) to afford N-ethyl-N-isopropylpropan-2-aminium (S)-2-((((9H-fluoren-9-yl)methoxy)carbonyl)(methyl)amino)-3-(bis(4-methoxyphenyl)(phenyl)methoxy)propanoate (Compound SP816) (1.92 g, 92%).

LCMS (ESI) m/z=642 (M−H)−

Retention time: 0.72 min (analysis condition SQDAA50)

Ser having a carboxylic acid protected by a 1-isopropyl-4-(trifluoromethyl)benzene group (Pis(4-CF3) group) and an amino group protected by an Fmoc group was supported on a resin, and the resulting resin was used as a starting material for peptide synthesis. Synthesis of the resin is illustrated below.

Fmoc amino acid was supported on a resin according to the scheme shown in Scheme L, and the resin was used for peptide synthesis.

Scheme L

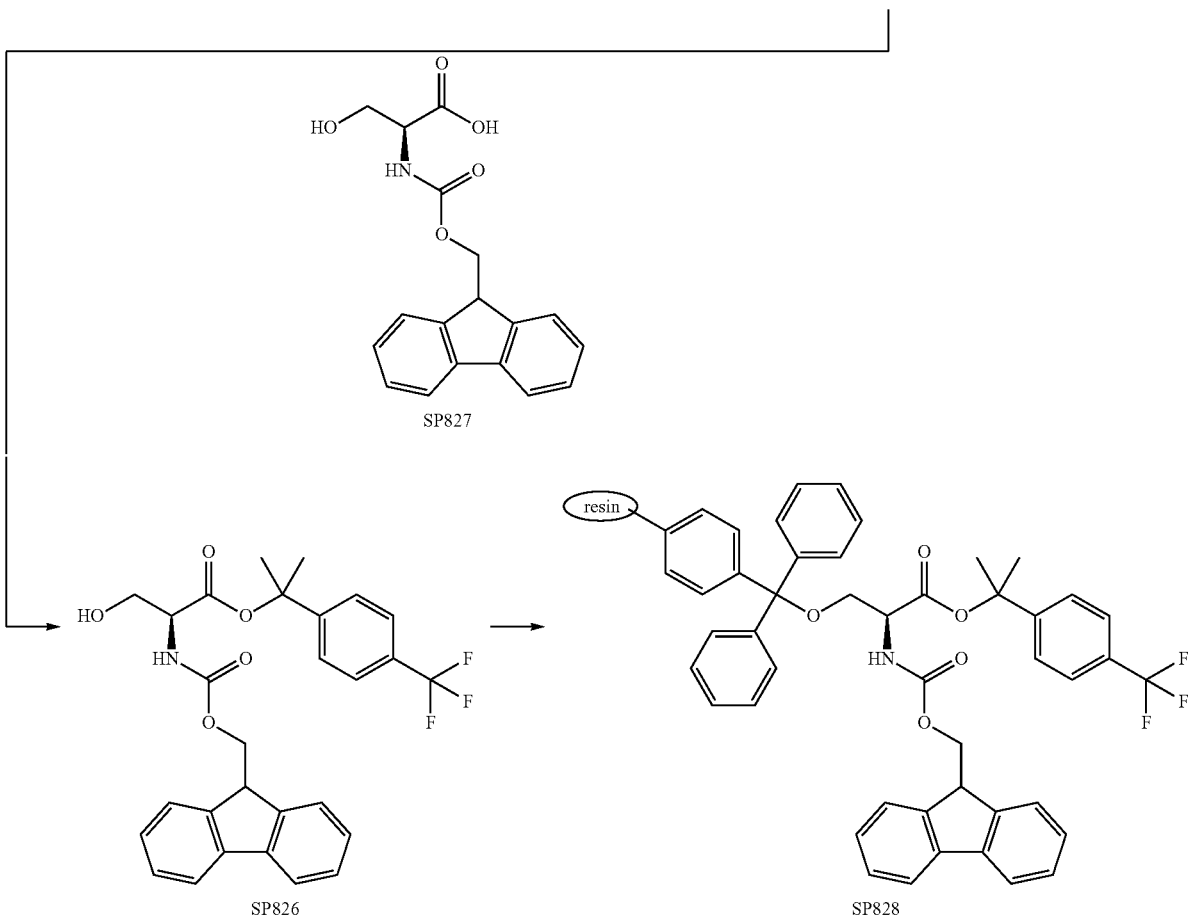

Synthesis of 2-[4-(trifluoromethyl)phenyl]propan-2-ol (Compound SP824)

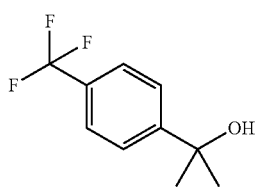

Methyl 4-(trifluoromethyl)benzoate (Compound SP825) (37.1 g, 181 mmol) was dissolved in dehydrated THF (90 ml) under a nitrogen atmosphere, a solution of methyl lithium in diethyl ether (1.5 M, 360 ml, 544 mmol) was added dropwise at 0° C. over 2 hours, and the mixture was stirred at room temperature for 30 minutes. A 50% aqueous ammonium chloride solution was slowly added, followed by extraction with ethyl acetate (200 ml×2). This was dried over sodium sulfate and then concentrated under reduced pressure, and the resulting residue was purified by Silica gel column chromatography (hexane/DCM=100/0→25/75) to afford 2-[4-(trifluoromethyl)phenyl]propan-2-ol (Compound SP824) (84%, 31.0 g).

Retention time: 0.73 min (analysis condition SQDFA05)

$^1$H-NMR (Varian 400-MR, 400 MHz, DMSO-D$_6$) δ ppm 7.69 (2H, d, 8.7 Hz), 7.65 (2H, 8.7 Hz), 5.24 (1H, s), 1.45 (6H, s)

Synthesis of 2-(4-(trifluoromethyl)phenyl)propan-2-yl 2,2,2-trichloroacetimidate (Compound SP853)

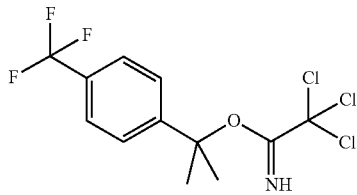 [SMILES: CC(C)(OC(=N)C(Cl)(Cl)Cl)c1ccc(C(F)(F)F)cc1]

2-[4-(Trifluoromethyl)phenyl]propan-2-ol (Compound SP824) (27.0 g, 132 mmol) was azeotropically distilled with THF (54 ml) three times. This was dissolved in dehydrated THF (270 ml) under a nitrogen atmosphere, a solution of sodium bis(trimethylsilyl)amide in dehydrated THF (1.9 M, 13.9 ml, 26.4 mmol) was added and the mixture was stirred at room temperature for 30 minutes. Trichloroacetonitrile (13.3 ml, 132 mmol) was added thereto at 0° C., followed by stirring for 30 minutes. The reaction mixture was concentrated under reduced pressure, and the resulting residue was purified by amino silica gel column chromatography (hexane) to afford 2-(4-(trifluoromethyl)phenyl)propan-2-yl 2,2,2-trichloroacetimidate (Compound SP853) (86%, 39.7g).

Retention time: 0.75 min (analysis condition SQDAA50)
$^1$H-NMR (Varian 400-MR, 400 MHz, DMSO-$D_6$) δ ppm 9.17 (1H, s), 7.73 (2H, d, 8.5 Hz), 7.63 (2H, d, 8.5 Hz), 1.84 (6H, s)

Synthesis of (S)-2-(4-(trifluoromethyl)phenyl)propan-2-yl 2-((((9H-fluoren-9-yl)methoxy)carbonyl)amino)-3-hydroxypropanoate (Compound SP826, Fmoc-Ser-OPis(4-CF3))

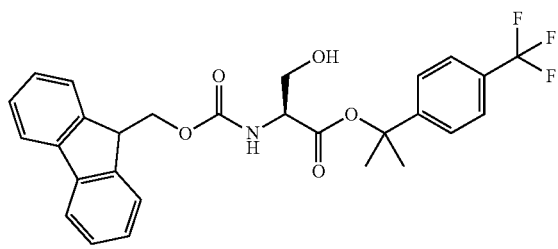

(S)-2-((((9H-Fluoren-9-yl)methoxy)carbonyl)amino)-3-hydroxypropanoic acid (Compound SP827, Fmoc-Ser-OH) (96.0 g, 292 mmol) was azeotropically distilled with THF (100 ml) eight times. This was dissolved in dehydrated THF (200 ml) under a nitrogen atmosphere, 2-(4-(trifluoromethyl)phenyl)propan-2-yl 2,2,2-trichloroacetimidate (Compound SP853) (67.9 g, 195 mmol) was added and the mixture was stirred at room temperature for 3 hours. The reaction mixture was directly purified by amino silica gel column chromatography (DCM) and concentrated under reduced pressure. The residue was further purified by reverse-phase silica gel column chromatography (10 mM aqueous ammonium acetate solution/methanol=95/5→0/100) to afford (S)-2-(4-(trifluoromethyl)phenyl)propan-2-yl 2-((((9H-fluoren-9-yl)methoxy)carbonyl)amino)-3-hydroxypropanoate (Compound SP826, Fmoc-Ser-OPis(4-CF3)) (38%, 38.4g).

LCMS (ESI) m/z=536 (M+Na)+
Retention time: 0.72 min (analysis condition SQDAA50)

Synthesis of (S)-2-(4-(trifluoromethyl)phenyl)propan-2-yl 2-((((9H-fluoren-9-yl)methoxy)carbonyl)amino)-3-hydroxypropanoate-trityl Resin (Compound SP828, Fmoc-Ser(Trt-Resin)-OPis(4-CF3))

In the present specification, when a polymer (such as a resin) is bound to a compound, the polymer portion may be indicated as "○" in a structural formula. A reactive functional group possessed by "○" (a trityl group in the following case) may be indicated to make the reaction point between a polymer and a compound easily recognized. In the following example, an ether bond site between the trityl group of a resin and serine were described, because the trityl group of the resin was bonded to the hydroxyl group of the serine through the ether bond.

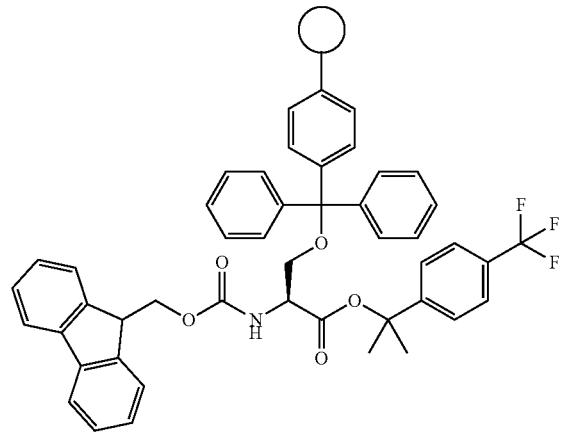

Trityl chloride resin (100-200 mesh, purchased from ChemPep, 23.0 g, 25.3 mmol) and dehydrated dichloromethane (200 ml) were placed in a reaction vessel equipped with a filter, and the vessel was shaken at room temperature for 10 minutes. Dichloromethane was removed by applying nitrogen pressure, after which DIPEA (11.0 ml) was added to a solution of (S)-2-(4-(trifluoromethyl)phenyl)propan-2-yl 2-((((9H-fluoren-9-yl)methoxy)carbonyl)amino)-3-hydroxypropanoate (Compound SP826) (6.49 g) in dehydrated dichloromethane (150 ml), the mixture was added to the reaction vessel, and the vessel was shaken for 3 hours. The reaction solution was removed by applying nitrogen pressure, after which dehydrated methanol (30.0 ml) and diisopropylethylamine (11 ml) were added to dehydrated dichloromethane (300 ml), the mixture was added to the reaction vessel, and the vessel was shaken for 90 minutes. The reaction solution was removed by applying nitrogen pressure, after which dichloromethane (300 ml) was placed and the vessel was shaken for 5 minutes. The reaction solution was removed by applying nitrogen pressure, after which dichloromethane (300 ml) was placed again and the vessel was shaken for 5 minutes. The reaction solution was removed by applying nitrogen pressure, after which the resin was dried under reduced pressure overnight to afford (S)-2-(4-(trifluoromethyl)phenyl)propan-2-yl 2-((((9H-fluoren-9-yl)methoxy)carbonyl)amino)-3-hydroxypropanoate-trityl resin (Compound SP828, Fmoc-Ser(Trt-Resin)-OPis(CF3)) (25.7 g, loading rate: 0.347 mmol, 34.7%).

Synthesis of (S)-3-((((9H-fluoren-9-yl)methoxy) carbonyl)amino)-4-(tert-butoxy)-4-oxobutanoic Acid 2-chlorotrityl Resin (Compound SP864)

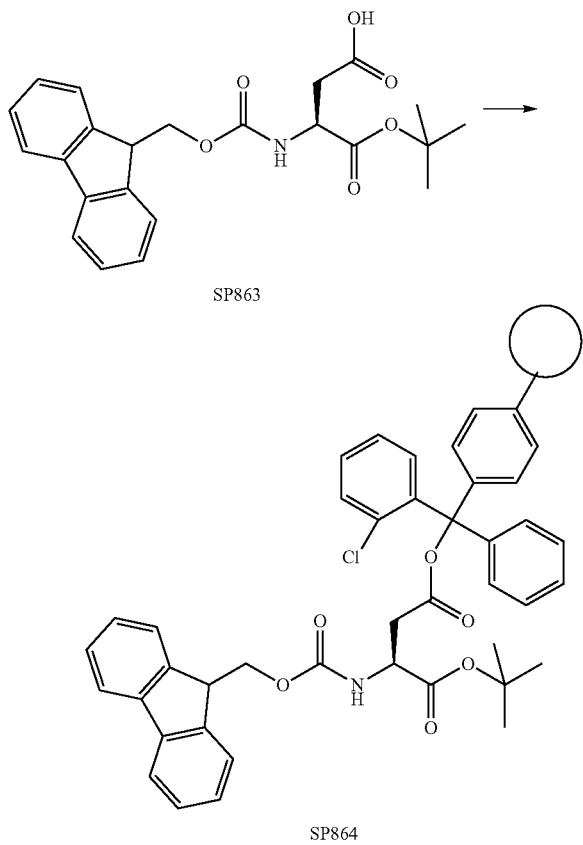

(S)-3-((((9H-Fluoren-9-yl)methoxy)carbonyl)amino)-4-(tert-butoxy)-4-oxobutanoic acid 2-chlorotrityl resin (Compound SP864) was obtained using (S)-3-((((9H-fluoren-9-yl)methoxy)carbonyl)amino)-4-(tert-butoxy)-4-oxobutanoic acid (Compound SP863) in place of (S)-3-((((9H-fluoren-9-yl)methoxy)carbonyl)amino)-4-oxo-4-(piperidin-1-yl)butanoic acid (Compound SP401) under the same conditions as in the preparation example for Compound SP402.

Synthesis of Compounds SP842, SP844, SP845, SP846, SP848, SP854, SP855 and SP856

Compounds having the structures of SEQ ID NO: PE-2 to SEQ ID NO: PE-15 where C-terminal Ser was added to 13th residues in the random region (peptides of 14 residues in total) were synthesized in order to confirm that the target-binding compounds could be obtained. For several compounds, 11-residue peptides having a portion corresponding to a linear portion 1 deleted were further synthesized.

Synthesis was carried out using polystyrene resin (Compound SP828) and using Fmoc-MeAla(4-Thz)-OH (Compound SP811), Fmoc-MePhe(3-Cl)—OH (Compound SP812), Fmoc-MePhe-OH, Fmoc-MeSer(DMT)-OH (Compound SP816), Fmoc-MeAla-OH, Fmoc-nPrGly-OH (Compound SP815), Fmoc-MeGly-OH, Fmoc-Hyp(Et)-OH (Compound SP813), Fmoc-Pro-OH, Fmoc-Thr(Trt)-OH, Fmoc-Phg-OH, Fmoc-Ile-OH, Fmoc-Val-OH, Fmoc-Asp (Pis)-OH, Fmoc-Trp-OH, Fmoc-DTyr(tBu)-OH, Fmoc-Phe (4-CF3)-OH, Fmoc-Ser(Trt)-OH, Fmoc-Met(O2)-OH, Fmoc-γEtAbu-OH (Compound SP814), Fmoc-βAla-OH, Fmoc-Ala-OH and Fmoc-Gly-OH as Fmoc amino acids.

Peptide chain elongation was carried out using diisopropylcarbodiimide and 1-hydroxy-7-azabenzotriazole (HOAt) or ethyl (hydroxyimino)cyanoacetate (Oxyma) as condensing agents, a 20% solution of piperidine in dimethylformamide containing 5% urea as an Fmoc deprotecting agent, and dimethylformamide containing 5% urea as a washing solvent. After the peptide elongation, the N-terminal Fmoc group was deprotected, and the resin was sequentially washed with dimethylformamide, trifluoroethanol and dichloromethane. The peptide was cleaved from the resin with hydrochloric acid (10 equivalents relative to the peptide) in triisopropyisilane/dichloroethane (=5/95, v/v). After completion of the reaction, the solution in the tube was filtered through a synthesis column to remove the resin. The reaction solution was mixed with diisopropylethylamine (10 equivalents relative to the peptide), and hydrochloric acid was neutralized. The resin was washed with dimethylformamide, and all solutions were mixed.

O-(7-Aza-1H-benzotriazol-1-yl)-N,N,N,N-tetramethyl-uronium hexafluorophosphate (HATU) and diisopropylethylamine were added to the resulting solution to cyclize the peptide. After completion of the reaction, the solvent was evaporated under reduced pressure.

The resulting residue was dissolved in dichloroethane, t-butyl methyl ether was added, and the peptide was precipitated. The supernatant was removed by centrifugation, trifluoroacetic acid/triisopropylsilane/dichloroethane (=5/5/90) were added to the residue, and the side chain protecting group containing Pis(4-CF3) was deprotected. The solvent was evaporated under reduced pressure, and the resulting crude product was purified by high-performance reverse-phase chromatography (HPLC).

Compound SP842

Peptide derived from SEQ ID NO: PE-7 (SEQ ID NO: 302) γEtAbu*-Thr-Phg-Ile-MeAla(4-Thz)-Trp-Trp-Phe(4-CF3)-DTyr-MePhe(3-Cl)-Asp*-Pro-MeGly-Ser-OH (cyclized at two * sites)

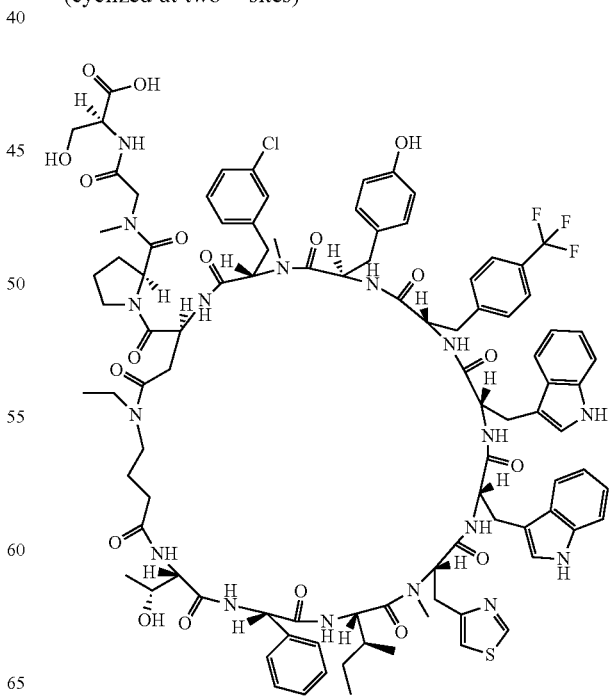

LCMS (ESI) m/z=1945 (M+H)+
Retention time: 0.81 min (analysis condition SQDFA05)

Compound SP844

Peptide derived from SEQ ID NO: PE-8 (SEQ ID NO: 303) Ala*-Phe(4-CF3)-Trp-Trp-Val-MeGly-Gly-Pro-Hyp(Et)-Ser-Asp*-MeSer-Met(O2)-Ser-OH
(cyclized at two * sites)

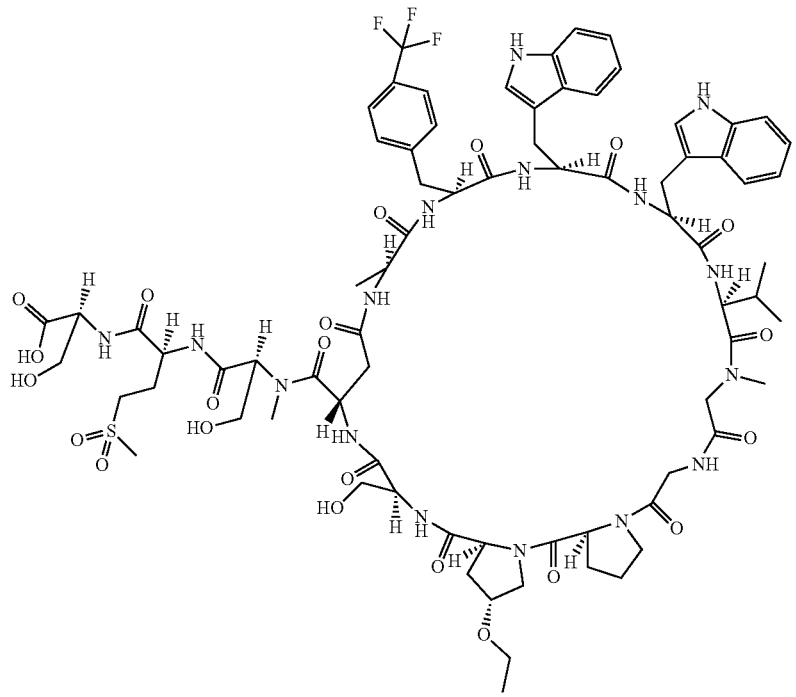 [SMILES: CCO[C@@H]1C[C@H]2C(=O)N[C@@H](CO)C(=O)N[C@H](C(=O)N(C)[C@@H](CO)C(=O)N[C@@H](CCS(C)(=O)=O)C(=O)N[C@@H](CO)C(=O)O)CC(=O)N[C@@H](C)C(=O)N[C@@H](Cc3ccc(C(F)(F)F)cc3)C(=O)N[C@@H](Cc3c[nH]c4ccccc34)C(=O)N[C@@H](Cc3c[nH]c4ccccc34)C(=O)N[C@@H](C(C)C)C(=O)N(C)CC(=O)NCC(=O)N3CCC[C@H]3C(=O)N2C1]

LCMS (ESI) m/z=1678 (M+H)+
Retention time: 0.64 min (analysis condition SQDFA05)

Compound SP845

Peptide derived from SEQ ID NO: PE-9 (SEQ ID NO: 304) Ala*-MeAla(4-Thz)-Ile-Pro-Val-Trp-Trp-Phe(4-CF3)-Met(O2)-Val-Asp*-Trp-MeAla(4-Thz)-Ser-OH (cyclized at two * sites)

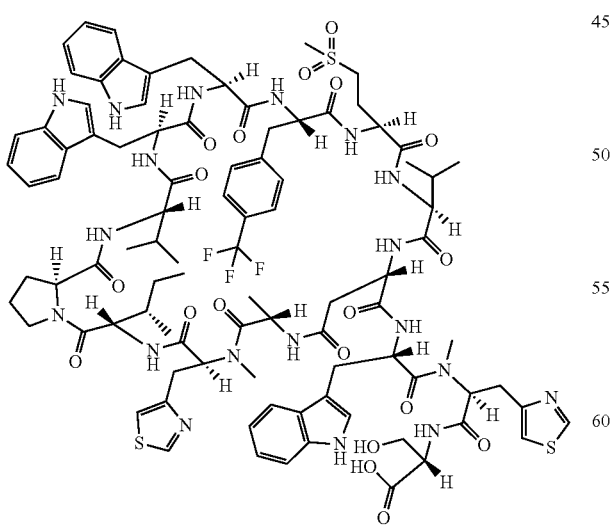

LCMS (ESI) m/z=1955 (M+H)+
Retention time: 0.82 min (analysis condition SQDFA05)

Compound SP846
Peptide derived from SEQ ID NO: PE-10 (SEQ ID NO: 305) Ala*-Thr-Ile-Pro-DTyr-Trp-Trp-Phe(4-CF3)-Met(O2)-Val-Asp*-Trp-MeAla(4-Thz)-Ser-OH
(cyclized at two * sites)
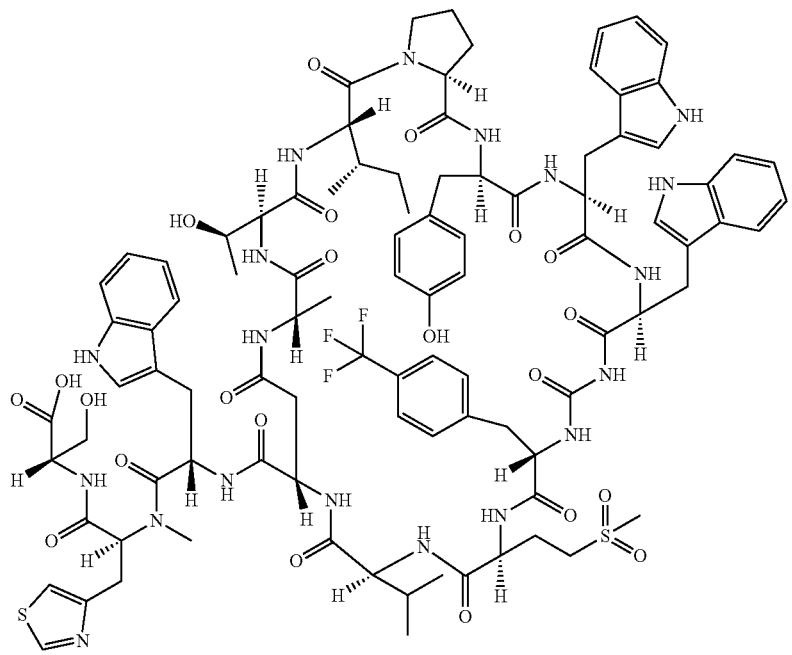 [SMILES: CC[C@H](C)[C@@H]1NC(=O)[C@H]([C@@H](C)O)NC(=O)[C@H](C)NC(=O)C[C@@H](C(=O)N[C@@H](Cc2c[nH]c3ccccc23)C(=O)N(C)[C@@H](Cc2cscn2)C(=O)N[C@@H](CO)C(=O)O)NC(=O)[C@H](C(C)C)NC(=O)[C@H](CCS(C)(=O)=O)NC(=O)[C@H](Cc2ccc(C(F)(F)F)cc2)NC(=O)NC(=O)[C@H](Cc2c[nH]c3ccccc23)NC(=O)[C@H](Cc2c[nH]c3ccccc23)NC(=O)[C@@H](Cc2ccc(O)cc2)NC(=O)[C@@H]2CCCN2C1=O]
LCMS (ESI) m/z=1952 (M+H)+
Retention time: 0.75 min (analysis condition SQDFA05)
Compound SP848
Peptide derived from SEQ ID NO: PE-11 (SEQ ID NO: 306) Ala*-Thr-Trp-Ile-MePhe-Phg-Trp-βAla-Phe(4-CF3)-Phg-Asp*-Val-Thr-Ser-OH
(cyclized at two * sites)
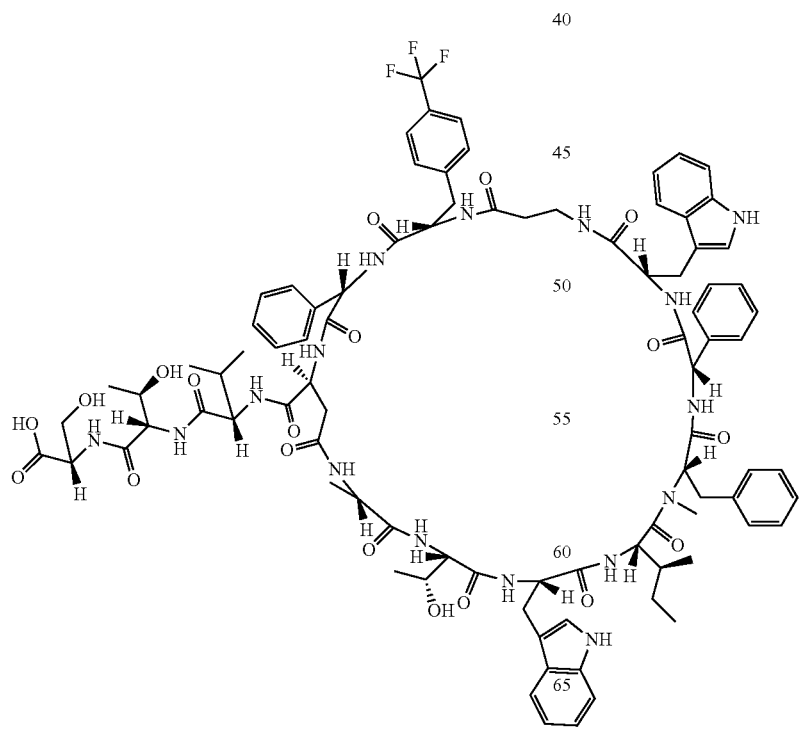

LCMS (ESI) m/z=1774 (M+H)+

Retention time: 0.81 min (analysis condition SQDFA05)

Compound SP854

Peptide derived from SEQ ID NO: PE-13 (SEQ ID NO: 307) Ala*-Pro-Val-Ile-MePhe-Met(O2)-Pro-MePhe(3-Cl)-Val-Met(O2)-Asp*-Pro-MeGly-Ser-OH (cyclized at two * sites)

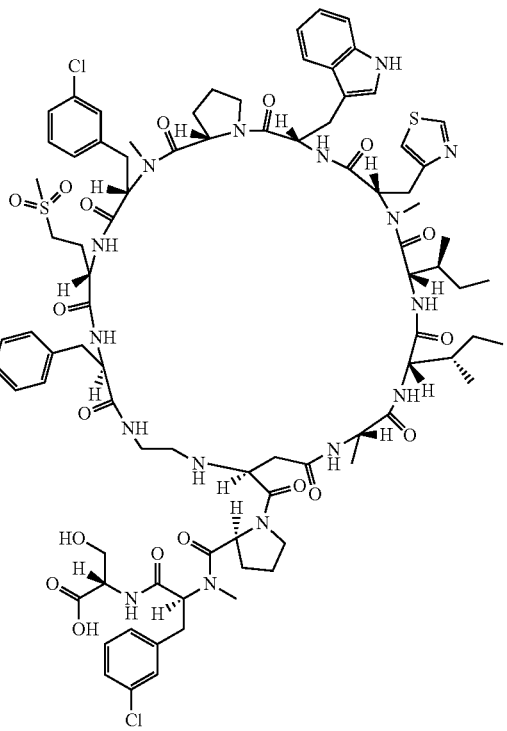

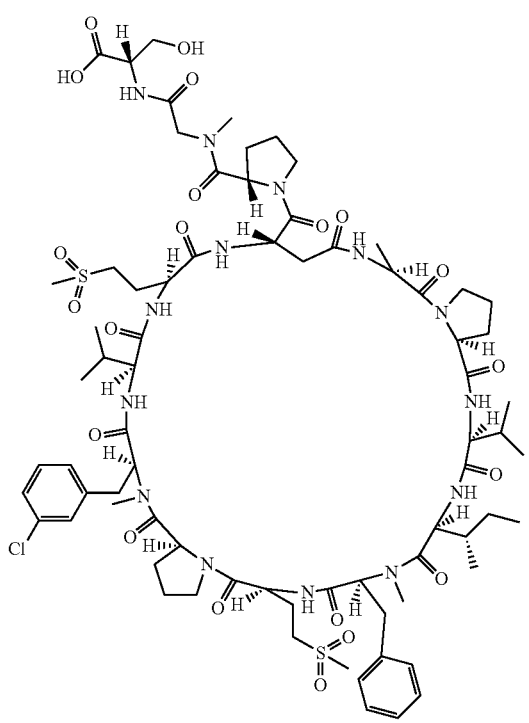 [SMILES: CC[C@H](C)[C@@H]1NC(=O)[C@H](C(C)C)NC(=O)[C@@H]2CCCN2C(=O)[C@H](C)NC(=O)C[C@@H](C(=O)N2CCC[C@H]2C(=O)N(C)CC(=O)N[C@@H](CO)C(=O)O)NC(=O)[C@H](CCS(C)(=O)=O)NC(=O)[C@H](C(C)C)NC(=O)[C@H](Cc2cccc(Cl)c2)N(C)C(=O)[C@@H]2CCCN2C(=O)[C@H](CCS(C)(=O)=O)NC(=O)[C@H](Cc2ccccc2)N(C)C1=O]

LCMS (ESI) m/z=1836 (M+H)+
Retention time: 0.80 min (analysis condition SQDFA05)
Compound SP856
Peptide derived from SEQ ID NO: PE-15 (SEQ ID NO: 309) γEtAbu*-Ile-Val-Trp-MePhe(3-Cl)-Met(O2)-Pro-MePhe(3-Cl)-DTyr-Met(O2)-Asp*-MeAla(4-Thz)-MeAla-Ser-OH (cyclized at two * sites)

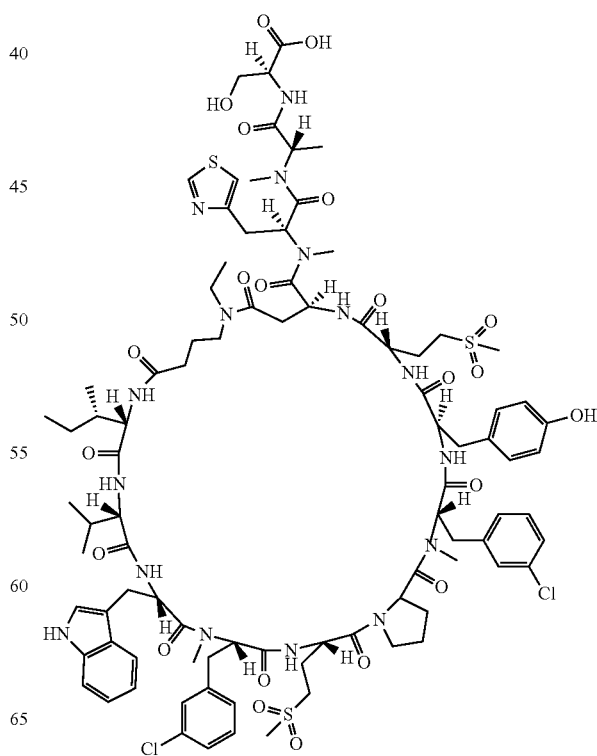

LCMS (ESI) m/z=1630 (M+H)+

Retention time: 0.70 min (analysis condition SQDFA05)

Compound SP855

Peptide derived from SEQ ID NO: PE-14 (SEQ ID NO: 308) Ala*-Ile-Ile-MeAla(4-Thz)-Trp-Pro-MePhe(3-Cl)-Met(O2)-DTyr-βAla-Asp*-Pro-MePhe(3-Cl)-Ser-OH (cyclized at two * sites)

LCMS (ESI) m/z=1944 (M+H)+
Retention time: 0.76 min (analysis condition SQDFA05)

Synthesis of Compound SP859

Ala*-Pro-Val-Ile-MePhe-Met(O2)-Pro-MePhe(3-Cl)-Val-Met(O2)-Asp*-Pro-MeGly-Ser-NH(CH$_2$)$_2$NMe$_2$ (SEQ ID NO: 310)
(cyclized at two * sites)

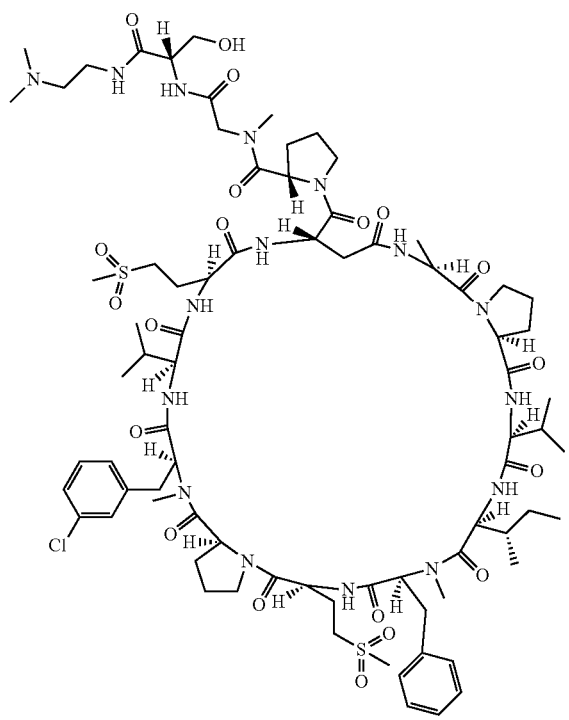 [SMILES: CC[C@H](C)[C@@H]1NC(=O)[C@H](C(C)C)NC(=O)[C@@H]2CCCN2C(=O)[C@H](C)NC(=O)C[C@@H](C(=O)N2CCC[C@H]2C(=O)N(C)CC(=O)N[C@@H](CO)C(=O)NCCN(C)C)NC(=O)[C@H](CCS(C)(=O)=O)NC(=O)[C@H](C(C)C)NC(=O)[C@H](Cc2cccc(Cl)c2)N(C)C(=O)[C@@H]2CCCN2C(=O)[C@H](CCS(C)(=O)=O)NC(=O)[C@H](Cc2ccccc2)N(C)C1=O]

SP854 (Ala*-Pro-Val-Ile-MePhe-Met(O2)-Pro-MePhe(3-Cl)-Val-Met(O2)-Asp*-Pro-MeGly-Ser-OH) (SEQ ID NO: 311) was dissolved in DMF (200 µl), and a solution of N1,N1-dimethylethane-1,2-diamine (1.43 µl, 13.0 mmol), diisopropylethylamine (3.82 µl, 22.0 µmol) and O-(7-aza-1H-benzotriazol-1-yl)-N,N,N,N-tetramethyluronium hexafluorophosphate (HATU) (5.00 mg, 13.0 µmol) in dimethylsulfoxide (10.0 µl) was added, followed by stirring for 30 minutes. The resulting residue was purified by reverse-phase silica gel column chromatography (10 mM aqueous ammonium acetate solution/methanol) to afford Compound SP859 (Ala-Pro-Val-Ile-MePhe-Met(O2)-Pro-MePhe(3-Cl)-Val-Met(O2)-Asp*-Pro-MeGly-Ser-NH(CHA 2 NMe 2) (SEQ ID NC: 310) (6.8 mg, 91%)
LCMS (ESI) m/z=1698 (M−H)−
Retention time: 0.59 min (analysis condition SQDFA05)

4. Evaluation of Binding of Synthetic Peptides to Target Proteins Utilizing Surface Plasmon Resonance (SPR)

4-1. Evaluation of Binding to TNFα

The following reagents were used: dimethylsulfoxyde (DMSO) and phosphate buffered saline (Sigma-Aldrich Co. LLC.), and surfactant P-20 (GE healthcare).

An SPR experiment for analyzing the interaction between synthetic peptides and TNFα was conducted using Biacore T200 (GE healthcare) at 20° C. Synthetic peptides were added to the immobilized protein, and the interaction was evaluated.

Surfactant P-20 and DMSO were added to the above phosphate buffered saline at final concentrations of 0.01 vol % and 5 vol %, respectively, and the resulting mixture was used as running buffer. CAP reagent was immobilized on a Biacore sensor chip, Series S sensor chip CAP (GE healthcare), according to the instructions, and biotinylated TNF was immobilized. Each synthetic peptide was added at multiple concentrations, and sensorgrams for binding to the immobilized TNFα were provided to measure dissociation constants ($K_D$).

The obtained sensorgrams were analyzed using 7200 evaluation software (GE healthcare) or Scrubber2 (Biologic software). First, solvent correction for DMSO and double reference (correction by subtracting sensorgrams of flow cells where TNFα was not immobilized and sensorgrams in the case where the buffer was added) were carried out. Second, binding rate constants ($k_{on}$) and dissociation rate constants ($k_{off}$) were calculated from curve fitting to the corrected sensorgrams, and $K_D$s were determined by the relational expression $K_D=k_{off}/k_{on}$.

The $K_D$s obtained by analyzing in the above manner are shown in the following Table 26.

TABLE 26

| Name of synthetic peptide | Target protein | $K_D$ [M] |
|---|---|---|
| Compound SP842 | TNFα | 1.6E−07 |
| Compound SP844 | TNFα | 2.0E−08 |
| Compound SP845 | TNFα | 9.4E−07 |
| Compound SP846 | TNFα | 2.0E−06 |
| Compound SP848 | TNFα | 2.5E−07 |

4-2. Evaluation of Binding to IL-6R

The following reagents were used: dimethylsulfoxyde (DMSO) (Sigma-Aldrich Co. LLC.), and HBS-EP and Surfactant P-20 (GE healthcare).

An SPR experiment for analyzing the interaction between synthetic peptides and IL-6R was conducted using Biacore T200 (GE healthcare) at 20° C. Synthetic peptides were added to the immobilized IL-6R, and the interaction was evaluated.

Surfactant P-20 and DMSO were added to the above HBS-EP at final concentrations of 0.01 vol % and 1 vol %, respectively, and the resulting mixture was used as running buffer.

CAP reagent was immobilized on a Biacore sensor chip, Series S sensor chip CAP (GE healthcare), according to the instructions, and biotinylated IL-6R was further immobilized.

Each synthetic peptide was added at multiple concentrations, and sensorgrams for binding to the immobilized IL-6R were provided to measure dissociation constants ($K_D$).

The obtained sensorgrams were analyzed using 7200 evaluation software (GE healthcare) or Scrubber2 (Biologic software). First, solvent correction for DMSO and double reference (correction by subtracting sensorgrams of flow cells where IL-6R was not immobilized and sensorgrams in the case where the buffer was added) were carried out. Second, binding rate constants ($k_{on}$) and dissociation rate constants ($k_{off}$) were calculated from curve fitting to the corrected sensorgrams, and $K_D$s were determined by the relational expression $K_D=k_{off}/k_{on}$.

The $K_D$s obtained by analyzing in the above manner are shown in the following Table 27.

TABLE 27

| Name of synthetic peptide | Target protein | $K_D$ [M] |
| --- | --- | --- |
| Compound SP856 | IL-6R | 1.3E−05 |
| Compound SP855 | IL-6R | 5.3E−06 |
| Compound SP854 | IL-6R | 1.8E−06 |
| Compound SP859 | IL-6R | 5.5E−07 |

5. IL-6R Inhibition Experiment Using Cells

[Example 27] Evaluation of Neutralization Activity of Synthetic Peptides Using Ba/F3 Cells Expressing Human gp130

Inhibitory activity of synthetic peptides having human IL-6 receptor (hIL-6R) binding activity confirmed in Example 26 was evaluated using a Ba/F3 cell line showing hIL-6 and soluble hIL-6R (shIL-6R) dose-dependent growth by introduction of human gp130 cDNA and forced expression (gp130 Ba/F3 cells). The influence of synthetic peptides on the mouse IL-3 (mIL-3) dose-dependent growth of gp130 Ba/F3 cells was evaluated as counter assay.

First, gp130 Ba/F3 cells were prepared at 1.5×10 5 cells/mL in a culture medium (RPMI 1640 (GIBCO) containing 10% FBS (Moregate Biotech), 100 units/mL penicillin and 100 µg/mL streptomycin (GIBCO)) and 50 µL, per well was plated in a 96-well flat bottom plate (CORNING). Second, a culture medium containing 60 ng/mL hIL-6 (Kamakura Techno-Science) and shIL-6R (Chugai Pharmaceutical Co., Ltd.) or 100 µg/mL mIL-3 (R&D Systems) was added at 25 µL per well. Third, a synthetic peptide selected and synthesized in Example 26 was two-fold serially diluted six times using DMSO and media (final conc.; 100 µmol/L). The prepared synthetic peptide was added at 25 µL per well at a final DMSO concentration of 0.25%, and incubated at 37° C. in a 5% CO2 incubator for three days. After completion of the incubation, 20 µL of a solution obtained by mixing equal amounts of Cell Counting Kit-8 (DOJINDO) and PBS(−) was added to each well, and the absorbance (450 nm/620 nm) was measured by a microplate reader (Bio-Rad Laboratories, Inc.) (former value). After 3 to 4 hours, the absorbance was measured again using the plate reader (latter value). The inhibition rate was calculated using the value obtained by subtracting the former value from the latter value as a calculated cell growth value.

The inhibition rate of the synthetic peptide was calculated from the calculated cell growth value (C) in the presence of hIL-6 and shIL-6R or mIL-3 and in the presence of the synthetic peptide, using the mean calculated cell growth value (A) in the absence of hIL-6, shIL-6R and mIL-3 and in the absence of the synthetic peptide as 100% inhibition and the mean calculated cell growth value (B) in the presence of hIL-6 and shIL-6R or mIL-3 and in the absence of the synthetic peptide as 0% inhibition.

$$\text{Inhibition} = (B-C)/(B-A) \times 100$$

Figure 73:
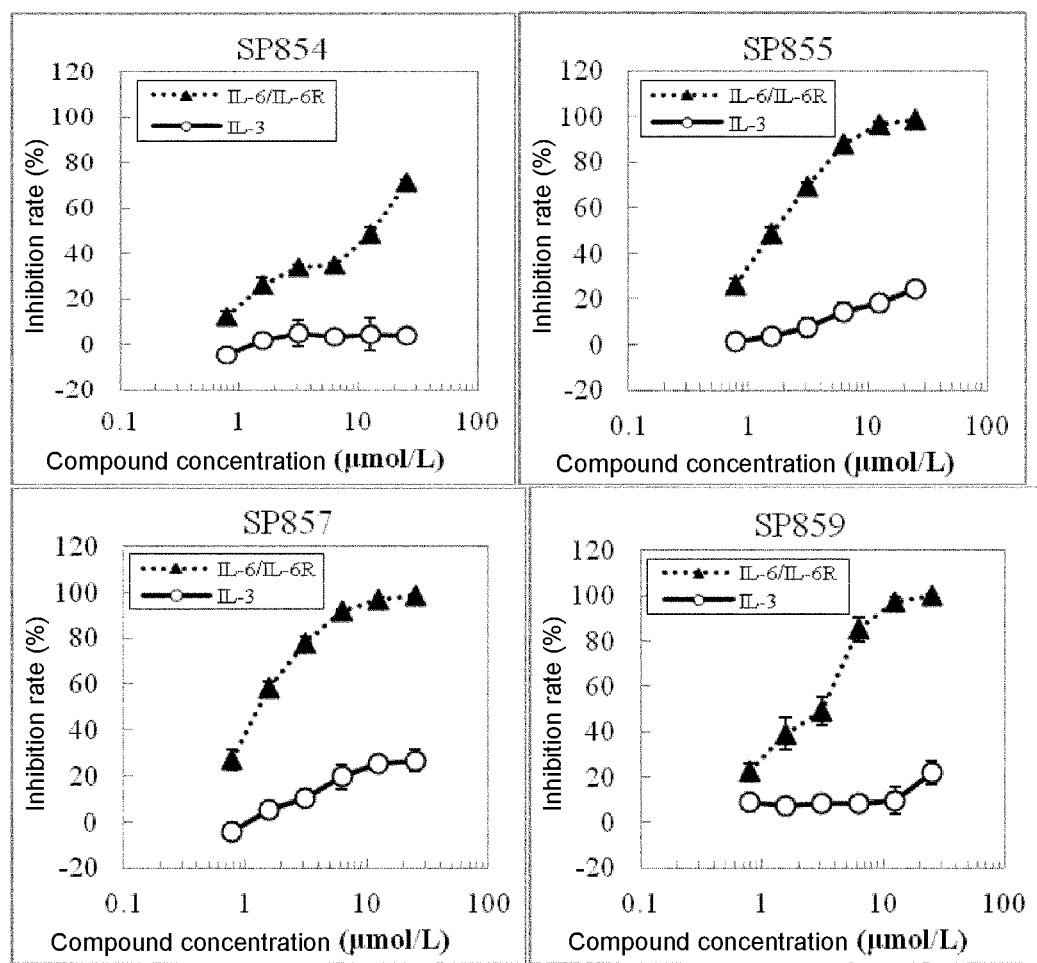
FIG. 73 is a diagram showing the inhibition activity of compounds (SP854, SP855, SP857 and SP859) obtained in Example 26 against cell growth by hIL-6 and shIL-6R.

The results indicated that the synthetic peptides selected and synthesized in Example 26 concentration-dependently inhibit the growth of gp130 Ba/F3 cells by hIL-6 and shIL-6R and have inhibitory activity specific to human IL-6 signaling (FIG. 73).

---

The invention claimed is:

1. A peptide compound-nucleic acid complex, wherein:
   (i) the peptide compound contains a cyclic portion composed of 5 to 12 amino acids and amino acid analog residues in total,
   (ii) the peptide compound contains at least three N-alkylated amino acids, wherein the N-alkylated amino acids are N-methylated amino acids,
   (iii) the peptide compound has at least one amide bond formed between a side chain of an amino acid or an amino acid analog and a nitrogen atom of the main chain of another amino acid or amino acid analog,
   (iv) the nucleic acid has a spacer at the 3'-end,
   and wherein the C-terminal of the peptide compound forms a complex with the nucleic acid through the spacer.

2. The peptide compound-nucleic acid complex according to claim 1, wherein the spacer is a peptide, RNA, DNA or hexaethylene glycol polymer.

3. The peptide compound-nucleic acid complex according to claim 1, wherein the peptide compound is produced by a method comprising the steps of:
   (a) translationally synthesizing a noncyclic peptide compound having 9 to 13 amino acids and amino acid analogs in total to form a noncyclic peptide compound, wherein the noncyclic peptide forms a complex with the nucleic acid through a linker, wherein the nucleic acid has a sequence encoding the noncyclic peptide compound; and
   (b) cyclizing the noncyclic peptide compound of the complex translationally synthesized in Step (a) by an amide bond or a carbon-carbon bond to form the peptide compound having the cyclic portion composed of 5 to 12 amino acid and amino acid analog residues in total, thereby obtaining the peptide compound-nucleic acid complex.

4. A library comprising the peptide compound-nucleic acid complex according to claim 1.

5. The library according to claim 4, wherein the library is a display library.

6. The library according to claim 5, wherein the display library is an mRNA display library.

7. A library comprising the peptide compound-nucleic acid complex according to claim 2.

8. The library according to claim 7, wherein the library is a display library.

9. The library according to claim 8, wherein the display library is an mRNA display library.

10. A library comprising the peptide compound-nucleic acid complex according to claim 3.

11. The library according to claim 10, wherein the library is a display library.

12. The library according to claim 11, wherein the display library is an mRNA display library.

13. A method for selecting a peptide compound having binding activity to a biomolecule, comprising bringing the library according to claim 4 into contact with a biomolecule to select a peptide compound having binding activity to the biomolecule.

14. A method for selecting a peptide compound having binding activity to a biomolecule, comprising bringing the library according to claim 7 into contact with a biomolecule to select a peptide compound having binding activity to the biomolecule.

15. A method for selecting a peptide compound having binding activity to a biomolecule, comprising bringing the library according to claim 10 into contact with a biomolecule to select a peptide compound having binding activity to the biomolecule.

16. A peptide compound-nucleic acid complex produced by a process comprising the steps of:
  (a) translationally synthesizing a noncyclic peptide compound having 9 to 13 amino acids and amino acid analogs in total to form a noncyclic peptide compound-nucleic acid complex in which the noncyclic peptide compound links to a nucleic acid sequence encoding the noncyclic peptide compound through a linker; and
  (b) cyclizing the noncyclic peptide compound of the complex translationally synthesized in Step (a) by an amide bond or a carbon-carbon bond to form a cyclic compound having a cyclic portion with 5 to 12 amino acid and amino acid analog residues in total,
  wherein the nucleic acid sequence has a spacer at the 3'-end,
  wherein the C-terminal of the noncyclic peptide compound forms a complex with the nucleic acid sequence through the spacer.

17. The peptide compound-nucleic acid complex according to claim 16, wherein the spacer is a peptide, RNA, DNA or hexaethylene glycol polymer.

18. A library comprising the peptide compound-nucleic acid complex according to claim 17.

19. The library according to claim 18, wherein the library is a display library.

20. The library according to claim 19, wherein the display library is an mRNA display library.

21. A method for selecting a peptide compound having binding activity to a biomolecule, comprising bringing the library according to claim 18 into contact with a biomolecule to select a peptide compound having binding activity to the biomolecule.

* * * * *